(12) United States Patent
Miller et al.

(10) Patent No.: US 12,168,009 B2
(45) Date of Patent: Dec. 17, 2024

(54) MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Mark Thomas Miller, San Diego, CA (US); Corey Anderson, San Diego, CA (US); Vijayalaksmi Arumugam, San Marcos, CA (US); Brian Richard Bear, Carlsbad, CA (US); Hayley Marie Binch, Encinitas, CA (US); Jeremy J. Clemens, San Diego, CA (US); Thomas Cleveland, San Diego, CA (US); Erica Conroy, Columbus, OH (US); Timothy Richard Coon, Carlsbad, CA (US); Bryan A. Frieman, La Jolla, CA (US); Peter Diederik Jan Grootenhuis, San Diego, CA (US); Raymond Stanley Gross, Poway, CA (US); Sara Sabina Hadida-Ruah, La Jolla, CA (US); Haripada Khatuya, San Diego, CA (US); Pramod Virupax Joshi, San Diego, CA (US); Paul John Krenitsky, San Diego, CA (US); Chun-Chieh Lin, San Diego, CA (US); Gulin Erdogan Marelius, San Diego, CA (US); Vito Melillo, Escondido, CA (US); Jason McCartney, Cardiff by the Sea, CA (US); Georgia McGaughey Nicholls, Winchester, MA (US); Fabrice Jean Denis Pierre, La Jolla, CA (US); Alina Silina, San Diego, CA (US); Andreas P. Termin, Encinitas, CA (US); Johnny Uy, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 17/865,220

(22) Filed: Jul. 14, 2022

(65) Prior Publication Data
US 2023/0233560 A1    Jul. 27, 2023

Related U.S. Application Data

(60) Continuation of application No. 16/836,155, filed on Mar. 31, 2020, now Pat. No. 11,426,407, which is a
(Continued)

(51) Int. Cl.
*A61K 31/506*    (2006.01)
*A61J 1/03*    (2023.01)
(Continued)

(52) U.S. Cl.
CPC ............. *A61K 31/506* (2013.01); *A61J 1/035* (2013.01); *A61K 31/404* (2013.01); *A61K 31/415* (2013.01); *A61K 31/44* (2013.01); *A61K 31/4418* (2013.01); *A61K 31/4439* (2013.01); *A61K 31/444* (2013.01); *A61K 31/4525* (2013.01); *A61K 31/4545* (2013.01);
(Continued)

(58) Field of Classification Search
CPC .................................................. A61K 31/506
USPC ..................................................... 514/253.09
See application file for complete search history.

(56) References Cited

U.S. PATENT DOCUMENTS

| 5,410,061 A | 4/1995 | Gilmore et al. |
| 6,441,004 B1 | 8/2002 | Faull et al. |
(Continued)

FOREIGN PATENT DOCUMENTS

| AU | 2013231151 A1 | 10/2013 |
| AU | 2013270464 A1 | 1/2014 |
(Continued)

OTHER PUBLICATIONS

Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.
(Continued)

*Primary Examiner* — Niloofar Rahmani
(74) *Attorney, Agent, or Firm* — Finnegan, Henderson, Farabow, Garrett & Dunner LLP

(57) ABSTRACT

The present invention features a compound of formula I:

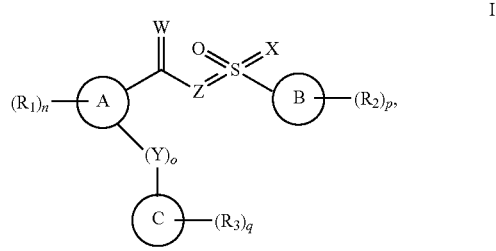

or a pharmaceutically acceptable salt thereof, where $R_1$, $R_2$, $R_3$, W, X, Y, Z, n, o, p, and q are defined herein, for the treatment of CFTR mediated diseases, such as cystic fibrosis. The present invention also features pharmaceutical compositions, method of treating, and kits thereof.

46 Claims, 6 Drawing Sheets

Related U.S. Application Data division of application No. 16/258,024, filed on Jan. 25, 2019, now Pat. No. 10,758,534, which is a continuation of application No. 15/675,000, filed on Aug. 11, 2017, now Pat. No. 10,258,624, which is a division of application No. 14/876,525, filed on Oct. 6, 2015, now Pat. No. 9,782,408.

(60) Provisional application No. 62/153,120, filed on Apr. 27, 2015, provisional application No. 62/114,767, filed on Feb. 11, 2015, provisional application No. 62/060,182, filed on Oct. 6, 2014.

(51) Int. Cl.

| | | |
|---|---|---|
| *A61K 31/404* | (2006.01) | |
| *A61K 31/415* | (2006.01) | |
| *A61K 31/44* | (2006.01) | |
| *A61K 31/4418* | (2006.01) | |
| *A61K 31/4439* | (2006.01) | |
| *A61K 31/444* | (2006.01) | |
| *A61K 31/4525* | (2006.01) | |
| *A61K 31/4545* | (2006.01) | |
| *A61K 31/4709* | (2006.01) | |
| *A61K 31/496* | (2006.01) | |
| *A61K 31/497* | (2006.01) | |
| *C07D 209/18* | (2006.01) | |
| *C07D 209/42* | (2006.01) | |
| *C07D 209/49* | (2006.01) | |
| *C07D 213/64* | (2006.01) | |
| *C07D 213/73* | (2006.01) | |
| *C07D 213/82* | (2006.01) | |
| *C07D 213/84* | (2006.01) | |
| *C07D 231/12* | (2006.01) | |
| *C07D 231/14* | (2006.01) | |
| *C07D 231/20* | (2006.01) | |
| *C07D 235/24* | (2006.01) | |
| *C07D 239/34* | (2006.01) | |
| *C07D 401/04* | (2006.01) | |
| *C07D 401/12* | (2006.01) | |
| *C07D 401/14* | (2006.01) | |
| *C07D 403/10* | (2006.01) | |
| *C07D 403/12* | (2006.01) | |
| *C07D 405/14* | (2006.01) | |
| *C07D 407/12* | (2006.01) | |
| *C07D 413/14* | (2006.01) | |
| *C07D 417/12* | (2006.01) | |

(52) U.S. Cl.
CPC ........ *A61K 31/4709* (2013.01); *A61K 31/496* (2013.01); *A61K 31/497* (2013.01); *C07D 209/18* (2013.01); *C07D 209/42* (2013.01); *C07D 209/49* (2013.01); *C07D 213/64* (2013.01); *C07D 213/73* (2013.01); *C07D 213/82* (2013.01); *C07D 213/84* (2013.01); *C07D 231/12* (2013.01); *C07D 231/14* (2013.01); *C07D 231/20* (2013.01); *C07D 235/24* (2013.01); *C07D 239/34* (2013.01); *C07D 401/04* (2013.01); *C07D 401/12* (2013.01); *C07D 401/14* (2013.01); *C07D 403/10* (2013.01); *C07D 403/12* (2013.01); *C07D 405/14* (2013.01); *C07D 407/12* (2013.01); *C07D 413/14* (2013.01); *C07D 417/12* (2013.01)

(56) References Cited

U.S. PATENT DOCUMENTS

| 6,787,651 B2 | 9/2004 | Stolle et al. |
|---|---|---|
| 6,949,572 B2 | 9/2005 | Bertinato et al. |
| 6,979,692 B2 | 12/2005 | Bertinato et al. |
| 7,368,573 B2 | 5/2008 | Bertinato et al. |
| 8,058,299 B2 | 11/2011 | Bolin et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 10,570,115 B2 | 2/2020 | Alcacio et al. |
| 10,654,829 B2 | 5/2020 | Dhamankar et al. |
| 10,758,534 B2 | 9/2020 | Miller et al. |
| 10,793,547 B2 | 10/2020 | Abela et al. |
| 11,155,533 B2 | 10/2021 | Dhamankar et al. |
| 11,179,367 B2 | 11/2021 | Chu et al. |
| 11,186,566 B2 | 11/2021 | Alcacio et al. |
| 11,253,509 B2 | 2/2022 | Chen et al. |
| 11,414,439 B2 | 8/2022 | Abela et al. |
| 11,426,407 B2 | 8/2022 | Miller et al. |
| 11,434,201 B2 | 9/2022 | Angell et al. |
| 11,453,655 B2 | 9/2022 | Abela et al. |
| 11,465,985 B2 | 10/2022 | Angell et al. |
| 11,517,564 B2 | 12/2022 | Chen et al. |
| 2002/0055631 A1 | 5/2002 | Augeri et al. |
| 2002/0086887 A1 | 7/2002 | Augeri et al. |
| 2004/0006237 A1 | 1/2004 | Dolitzky et al. |
| 2005/0171185 A1 | 8/2005 | Yamasaki et al. |
| 2005/0197376 A1 | 9/2005 | Kayakiri et al. |
| 2007/0105833 A1 | 5/2007 | Ruah et al. |
| 2010/0160322 A1 | 6/2010 | Bruncko et al. |
| 2010/0227888 A1 | 9/2010 | Hadida Ruah et al. |
| 2011/0165118 A1 | 7/2011 | Chan et al. |
| 2013/0072483 A1 | 3/2013 | Zhong et al. |
| 2013/0267493 A1 | 10/2013 | Bhattacharya et al. |
| 2013/0317000 A1 | 11/2013 | Chowdhury et al. |
| 2013/0317001 A1 | 11/2013 | Andrez et al. |
| 2014/0080825 A1 | 3/2014 | Hadida-Ruah et al. |
| 2014/0296200 A1 | 10/2014 | Brown et al. |
| 2015/0320736 A1 | 11/2015 | Phenix et al. |
| 2015/0322002 A1 | 11/2015 | Dehnhardt et al. |
| 2016/0095858 A1* | 4/2016 | Miller .................. C07D 231/12 546/261 |
| 2016/0098585 A1 | 4/2016 | Sempere et al. |
| 2018/0099932 A1 | 4/2018 | Altenbach et al. |
| 2018/0141954 A1 | 5/2018 | Strohbach et al. |
| 2018/0170938 A1 | 6/2018 | Strohbach et al. |
| 2018/0244611 A1 | 8/2018 | Altenbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0153000 A1 | 5/2019 | Munoz et al. |
| 2019/0240197 A1 | 8/2019 | Chu et al. |
| 2019/0269683 A1 | 9/2019 | Miller et al. |
| 2020/0171015 A1 | 6/2020 | Haseltine et al. |
| 2021/0032272 A1 | 2/2021 | Abela et al. |
| 2021/0069174 A1 | 3/2021 | Chu et al. |
| 2021/0113547 A1 | 4/2021 | Chen et al. |
| 2021/0139514 A1 | 5/2021 | Abela et al. |
| 2021/0228489 A1 | 7/2021 | Dokou et al. |
| 2022/0257564 A1 | 8/2022 | Chu et al. |
| 2022/0306606 A1 | 9/2022 | Alcacio et al. |
| 2023/0241045 A1 | 8/2023 | Chen et al. |
| 2023/0357191 A1 | 11/2023 | Abela et al. |
| 2024/0025877 A1 | 1/2024 | Angell et al. |

FOREIGN PATENT DOCUMENTS

| CA | 2145473 A1 | 9/1995 |
|---|---|---|
| CN | 101087781 A | 12/2007 |
| CN | 102458122 A | 5/2012 |

(56) References Cited

FOREIGN PATENT DOCUMENTS

| | | |
|---|---|---|
| CN | 103946221 A | 7/2014 |
| EA | 011074 B1 | 12/2008 |
| EA | 28378 B1 | 11/2017 |
| EP | 0 194 599 A2 | 9/1986 |
| EP | 0 673 930 A1 | 9/1995 |
| EP | 1 318 978 B1 | 2/2006 |
| GB | 967177 A | 8/1964 |
| JP | 10-114654 A | 5/1998 |
| JP | 2007-511530 A | 5/2007 |
| JP | 2008-524233 A | 7/2008 |
| JP | 2011-520785 A | 7/2011 |
| KR | 10-2005-0061501 A | 6/2005 |
| RU | 2463303 C2 | 10/2012 |
| RU | 2608610 C2 | 1/2017 |
| WO | 9115479 * | 10/1991 |
| WO | WO-9115479 A * | 10/1991 ........... C07D 231/14 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/08818 A1 | 3/1998 |
| WO | WO 98/31226 A1 | 7/1998 |
| WO | WO 99/07351 A2 | 2/1999 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2004/111014 A1 | 12/2004 |
| WO | WO 2005/049018 A1 | 6/2005 |
| WO | WO 2005/054191 A1 | 6/2005 |
| WO | WO 2005/070006 A2 | 8/2005 |
| WO | WO 2005/075435 A1 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/002421 A2 | 1/2006 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/113327 A2 | 10/2007 |
| WO | WO 2007/117715 A2 | 10/2007 |
| WO | WO 2007/134279 A2 | 11/2007 |
| WO | WO 2008/005457 A2 | 1/2008 |
| WO | WO 2008/100867 A2 | 8/2008 |
| WO | WO 2008/127399 A2 | 10/2008 |
| WO | WO 2008/141385 A1 | 11/2008 |
| WO | WO 2009/006315 A1 | 1/2009 |
| WO | WO 2009/027730 A1 | 3/2009 |
| WO | WO 2009/032116 A1 | 3/2009 |
| WO | WO 2009/038683 A2 | 3/2009 |
| WO | WO 2009/064848 A1 | 5/2009 |
| WO | WO 2009/071947 A2 | 6/2009 |
| WO | WO 2009/073757 A1 | 6/2009 |
| WO | WO 2009/076142 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/019239 A2 | 2/2010 |
| WO | WO 2010/022307 A2 | 2/2010 |
| WO | WO 2010/025295 A2 | 3/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/065824 A2 | 6/2010 |
| WO | WO 2010/078103 A1 | 7/2010 |
| WO | WO 2010/083441 A2 | 7/2010 |
| WO | WO 2010/102758 A2 | 9/2010 |
| WO | WO 2010/108155 A1 | 9/2010 |
| WO | WO 2010/108162 A1 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A1 | 2/2011 |
| WO | WO 2011/068560 A1 | 6/2011 |
| WO | WO 2011/072241 A1 | 6/2011 |
| WO | WO 2011/102514 A1 | 8/2011 |
| WO | 2011/113894 A1 | 9/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/128251 A1 | 10/2011 |
| WO | WO 2011/133751 A2 | 10/2011 |
| WO | WO 2011/133951 A1 | 10/2011 |
| WO | WO 2011/150016 A1 | 12/2011 |
| WO | WO 2012/027247 A2 | 3/2012 |
| WO | WO 2012/027731 A2 | 3/2012 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2012/170061 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/070961 A1 | 5/2013 |
| WO | WO 2013/082102 A1 | 6/2013 |
| WO | WO 2013/112804 A1 | 8/2013 |
| WO | WO 2013/118805 A1 | 8/2013 |
| WO | WO 2013/130669 A1 | 9/2013 |
| WO | WO 2013/158121 A1 | 10/2013 |
| WO | WO 2013/177224 A1 | 11/2013 |
| WO | WO 2013/185112 A1 | 12/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 | 3/2014 |
| WO | WO 2014/047427 A2 | 3/2014 |
| WO | WO 2014/071122 A1 | 5/2014 |

(56) References Cited

FOREIGN PATENT DOCUMENTS

| | | |
|---|---|---|
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/105484 A1 | 6/2016 |
| WO | WO 2016/105485 A2 | 6/2016 |
| WO | WO 2016/128529 A1 | 8/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/026075 A1 | 10/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |

OTHER PUBLICATIONS

Atzrodt J, Derdau V, Fey T, Zimmermann J. "The Renaissance of H/D Exchange" Angew. Chem. Int. Ed. 2007: 46, 7744-7765.
Atzrodt J, Derdau V, Kerr W, Reid M. "C-H functionalization for hydrogen isotope exchange" Angew. Chem. Int. Ed. 2018: 57, 3022-3047.
Belikov, V.G., (2007) *Farmatsevticheskaya khimiya* (*Pharmaceutical Chemistry*), Moscow: MEDpress-inform, pp. 27-29.
Bhattacharya, S. et al. (2009) Polymorphism in Pharmaceutical Solids: Thermoanalytical and Crystallographic Methods (Brittain H. ed., 2d ed. Informa Healthcare USA, Inc. 2009) 318-335.
Borhade, S.R. et al. (2013) "Synthesis of Novel Aryl and Heteroaryl Acyl Sulfonimidamides via Pd-Catalyzed Carbonylation Using a Nongaseous Precursor" Organic Lett, 15(5):1056-1059.
Boyle, M. "A CFTR corrector (lumacaftor) and a CFTR potentiator (ivacaftor) for treatment of patients with cystic fibrosis who have a phe508del CFTR mutation: a phase 2 randomised controlled trial," The Lancet Respiratory Medicine (Jul. 1, 2014) Retrieved from the Internet: https://www-clinicalkeycom-ez03.infotrieve.com/#!/content/playContent/1-s2.0S2213260014701328?returnurl=null&referrer=null.
Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.
Brown et al. (2006) "On scaffolds and hopping in medicinal Chemistry," Mini-reviews in medicinal chemistry, vol. 6, 11(13), 1217-1229.
Byrn, S. et al. (1995) "Pharmaceutical solids: A strategic approach to regulatory considerations," (12): 945-954.
Caira, M. R. (1998) "Crystalline Polymorphism of Organic Compounds," *Topics in Current Chemistry*, 163-208.
Cargnin S, Serafini M, Pirali T. "A primer of deuterium in drug design" Future Med. Chem. 2019; 11(16):2039-2042.
Chemical Abstracts Service, CAS Registry No. 204017-11-8. CA Index Name: 1H-Indole-2-carboxamide, 1-[[2,4-bis(trifluoromethyl)phenyl]methyl]-2,3-dihydro-N-(phenylsulfonyl)-. Entered STN: Apr. 12, 1998.
Chemical Abstracts Service, CAS Registry No. 220678-97-7. CA Index Name: 1H-Indole-2-carboxamide, 1-[(3,4-dichlorophenyl)methyl]-N-(phenylsulfonyl)-. Entered STN: Mar. 24, 1999.
Chemical Abstracts Service, CAS Registry No. 220678-99-9. CA Index Name: 1H-Indole-2-carboxamide, 1-[(3,4-dichlorophenyl)methyl]-N-[(3,5-dimethyl-4-isoxazolyl)sulfonyl]-. Entered STN: Mar. 24, 1999.
Chemical Abstracts Service, CAS Registry No. 412005-98-2. CA Index Name: 1H-Indole-2-carboxamide, 3-(4-methoxyphenyl)-N-(phenylsulfonyl)-1-[[3-(trifluoromethyl)phenyl]methyl]-. Entered STN: May 7, 2002.
Chemical Abstracts Service, CAS Registry No. 895575-67-4. CA Index Name: 1H-Indole-2-carboxamide, 1-[(3-chlorophenyl) methyl]-4-nitro-N-(2-thienylsulfonyl)-. Jun. 30, 2006.
Chemical Abstracts Service, CAS Registry No. 895575-68-5. CA Index Name: 1H-Indole-2-carboxamide, 4-amino-1-[(3-chlorophenyl)methyl]-N-(2-thienylsulfonyl)-. Jul. 23, 2006.
Chen, Y. (Jan. 2, 20166) "N-Monoacylation of Sulfonimidamides" *Synthesis*, 48(7):1019-1028.
Czeskis B, Elmore, CS, Haight A, Hesk D, Maxwell BD, Miller SA, Raglione T, Schildknegt K, Traverse JF, Wang P. "Deuterated active pharmaceutical ingredients: A science-based proposal for synthesis, analysis, and control. Part 1: Framing the problem" J. Label. Compd. Radiopharm. 2019, 62: 690-694. DOI: 10.1002/jlcr.3743.
Dao HT, Li C, Michaudel Q, Maxwell BD, Baran PS. J. Am. Chem. Soc. 2015; 137, 8046-8049.
Database Caplus, Accession No. 1965:51408. Abstract of French Patent No. FR M2868, filed Nov. 23, 1964, by Roussel-UCLAF [online]. Retrieved Jan. 6, 2017 (1 page).
Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database ChemSpider, CSID:17283620 (CAS: RN 1026625-71-7), http://www.chemspider.com/Chemical-Structure.17283620.html (accessed 16:40, Mar. 30, 2023).
Database Pubchem, CID: 44419393. Compound Summary, CHEMBL374189. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database Pubchem, CID: 49774135. Compound Summary, SCHEMBL13395127. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).

(56) References Cited

OTHER PUBLICATIONS

Database Pubchem, CID: 58132855. Compound Summary, SCHEMBL831192. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).

Database Pubchem, CID: 20050716. Compound Summary, 1-[2-[[2-[(2-Amino-3-methylbutanoyl)amino]-3-methylpentanoyl]amino]-3-phenylpropanoyl]pyrrolidine-2-carboxylic acid. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).

Database Pubchem, CID: 20091118. Compound Summary, [4-(5-Hexylpyrimidin-2-yl)phenyl] 2-methoxypropanoate. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).

Database Pubchem, CID: 20120819. Compound Summary, 4-(Cyclopentyloxy)-3-fluorobenzene-1-sulfonyl chloride. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).

Database Pubchem, CID: 2545578. Compound Summary, T5339296. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).

Dorwald, F. A. (2006) "Side Reactions in Organic Synthesis" Wiley: VCH, Weinheim p. IX of Preface p. 1-15.

European Patent Application No. 15849396.5 (Patent No. 3203840): Notice of Opposition by Elkington and Fife, LLP, May 5, 2021 (19 pages).

Gant TG. "Using Deuterium in Drug Discovery: Leaving the Label in the Drug" J Med. Chem. 2014; 57(9):3595-3611.

Garg, V. et al. "Pharmacokinetic and Drug-Drug Interaction Profiles of the Combination of Tezacaftor/Ivacaftor", Clinical and Translational Science—CTS, vol. 12, No. 3, Jan. 29, 2019 (Jan. 29, 2019), pp. 267-275, XP055719490, US ISSN: 1752-8054, DOI: 10.1111/cts.12610.

Ghose et al. (1999) Knowledge-based approach in designing combinatorial or medicinal chemistry libraries for drug discovery—qualitive and quantitative characterization of known drug databases, J. Comb. Chem. 1(1), 55-68.

Halford B. "The deuterium switcheroo" Chemical & Engineering News 2016; 94(27), 32-36.

Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.

International Patent Application No. PCT/US2015/54316: International Search Report and Written Opinion, mailed Feb. 5, 2016 (11 pages).

International Patent Application No. PCT/US2017/025381: International Search Report and Written Opinion, mailed Jun. 6, 2017 (11 pages).

International Patent Application No. PCT/US2017/054611: International Search Report and Written Opinion, mailed Jan. 3, 2018 (10 pages).

International Patent Application No. PCT/US2017/065425: International Search Report and Written Opinion, mailed Feb. 27, 2018 (10 pages).

International Patent Application No. PCT/US2018/036610: International Search Report and Written Opinion, mailed Sep. 19, 2018 (9 pages).

International Patent Application No. PCT/US2018/040427: International Search Report and Written Opinion, mailed Oct. 9, 2018 (15 pages).

International Patent Application No. PCT/US2018/042415: International Search Report and Written Opinion, mailed Oct. 31, 2018 (12 pages).

International Patent Application No. PCT/US2018/042486: International Search Report and Written Opinion, mailed Nov. 7, 2018 (13 pages).

International Patent Application No. PCT/US2018/044963: International Search Report and Written Opinion, mailed Sep. 25, 2018 (15 pages).

International Patent Application No. PCT/US2018/056772: International Search Report and Written Opinion, mailed Jan. 29, 2019 (13 pages).

International Patent Application No. PCT/US2018/063871: International Search Report and Written Opinion, mailed Feb. 25, 2019 (16 pages).

International Patent Application No. PCT/US2018/064522: International Search Report and Written Opinion, mailed Jun. 25, 2019 (21 pages).

International Patent Application No. PCT/US2019/016537: International Search Report and Written Opinion, mailed Apr. 23, 2019 (13 pages).

International Patent Application No. PCT/US2019/018042: International Search Report and Written Opinion, mailed Apr. 17, 2019 (10 pages).

International Patent Application No. PCT/US2019/024890: International Search Report and Written Opinion, mailed Jun. 17, 2019 (13 pages).

International Patent Application No. PCT/US2019/026075: International Search Report and Written Opinion, mailed Jun. 17, 2019 (13 pages).

International Patent Application No. PCT/US2019/027202: International Search Report and Written Opinion, mailed Jun. 17, 2019 (10 pages).

International Patent Application No. PCT/US2020/028699: International Search Report and Written Opinion, mailed Jul. 20, 2020 (9 pages).

International Patent Application No. PCT/US2020/034199: International Search Report and Written Opinion, mailed Aug. 11, 2020 (15 pages).

Ivanisevic, I. (2011) "Uses of X-Ray Powder Diffraction in the Pharmaceutical Industry," Pharm. Form. Qual. 30-33.

Jain, B.C. et al. (1947) "Studies in Sulphanilamides. Part XIII. Reaction With Dicarboxylic Acids. Some New N1- and N4-Acyl and Heterocyclic Derivatives" *Journal of the Indian Chemical Society*, 24:173-176.

Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.

Kieltsch, I. et al. Laureates: Awards and Honors Scs Fall Meeting 2007 260 Recent Advances in Electrophilic CF 3-Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.

Kholodov, L.E. et al., Klinicheskaya farmakokinetika (Clinical Pharmacokinetics), M., Meditsina, 1985, pp. 83-98, 134-138, 160, 378-380.

Kola et al. (2004) "Can the pharmaceutical industry reduce attrition rates?" Nature Reviews Drug Discovery, 3(8), 711-715.

Kratkiy kurs molekulyarnoy biologii (A Concise Course in Molecular Biology), edited by P.V. Sergeev, M., 1975, p. 10.

Lai, J.T. et al. (1980) "Rearrangement of 2,2,6,6-tetramethyl-4-piperidone in phase-transfer catalyzed reactions," *Journal of Organic Chemistry*, 45(8):1513-1514.

Liu, J. F. et al. "CTP-354: A Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.

Matter, H. et al. (2002) "Design and Quantitative Structure-Activity Relationship of 3-Amidinobenzyl-1H-indole-2-carboxamides as Potent,

(56) References Cited

OTHER PUBLICATIONS

Nonchiral, and Selective Inhibitors of Blood Coagulation Factor Xa" Journal of Medicinal Chemistry, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].
NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.
Norman, P. (2014) "Novel picolinamide-based cystic fibrosis transmembrane regulator modulators: evaluation of WO2013038373, WO2013038376, WO2013038381, WO2013038386, and WO2013038390," Expert Opinion on Therapeutic Patents, 24(7):829-837.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.
Passarella, D. et al. (2001) "Cyclodimerization of indol-2-ylacetylenes. An example of intermolecular enyne-alkyne cycloaddition" Journal of the Chemical Society, Perkin Transactions 1, 127-129.
Pham, P. et al. (2011) "Photoredox Catalysis: A Mild, Operationally Simple Approach to the Synthesis of alpha-Trifluoromethyl Carbonyl Compounds" Angew. Chem. Int. Ed. 2011:50 6119-6122.
Pirali T, Serafini M, Cargnin S, Genazzani AA. "Applications of Deuterium in Medicinal Chemistry" J Med. Chem. 2019; 62(11): 5276-5297.
Qun, C. et al. "Synthesis of 3,3,3-trifluoro-2,2-dimethylpropionic acid", Huaxue Shiji—Chemical Reagents, Beijing : Huaxue Huaxue Shiji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.
Rosebraugh, C.J. (2015) "Highlights of Prescribing Information for Orkambi," [online] Retrieved from the Internet: https://www.accessdata.fda.gov/drugsatfda_docs/label/2015/206038Orig1s000lbl.pdf, on Aug. 24, 2017.
Rossiiskii terapeuticheskii spravochnik [Russian therapeutic reference book], second edition, ed. Acad. RAMS A.G. Chuchalina, M. 2008, p. 144.
Schmidt C. "First deuterated drug approved" Nat. Biotechnol. 2017, 35, 493-494.
Shih et al. (2010) "Pyrazole compound BPR1P0034 with potent and selective anti-influenza virus activity" Journal of Biomedical Science, 17:13.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" Journal für Pracktische Chemie, 331(3):503-506.
Soloducho, J. et al. "Synthesis of Some Pyrido[3,2g][1,2,5]triazocine Derivatives," Polish Journal of Chemistry, vol. 59, No. 10-12, Jan. 1, 1985, pp. 1115-1120.
Table 2 : List of the mutations or SNP tested in this study (https://www.jmdjournal.org/cms/10.2353/jmoldx.2008.080056/attachment/2286a276-d0b2-4a8a-83f8-8273bef9a761/mmc1.doc). Accessed Jan. 25, 2021.
Tsong-Long H. et al. "Synthesis and pharmacological characterization of 2-aminobenzaldehyde oxime analogs as dual inhibitors of neutrophil elastase and proteinase 3", Bioorganic & Medicinal Chemistry, vol. 23, No. 5, Jan. 16, 2015, pp. 1123-1134, XP029199003.

Tullis, E. et al. (2018) "Preliminary safety and efficacy of triple-combination CFTR modulator regimens," Respirology, 23(51):33.
U.S. Appl. No. 17/880,720, filed Aug. 4, 2022, by Abela et al.
U.S. Appl. No. 17/899,860, filed Aug. 31, 2022, by Chen et al.
U.S. Appl. No. 17/899,672, filed Aug. 31, 2022, by Angell et al.
Uttamsingh, V. et al. (2016) "WS13.6 CTP-656 tablet confirmed superiority of pharmacokinetic profile relative to Kalydeco in Phase I clinical studies" Journal of Cystic Fibrosis, 15:S22.
Venkatesh, S. et al. (2000) "Role of the development scientist in compound lead selection and optimization" J. Pharm. Sci. 89(2), 145-154.
Verado, G. et al. (1999) "Reductive One Batch Synthesis of N-Substituted Pyrrolidines from Primary Amines and 2,5-Dimethoxytetrahydrofuran" Synthesis, (1):74-79.
Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].
Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.
Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.
"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.
Vodak, D. (2014) "Design and Development of HPMCAS-Based Spray-Dried Dispersions," 303-322.
Wainwright, C.E. et al. (2015) "Lumacaftor-Ivacaftor in Patients with Cystic Fibrosis Homozygous for Phe508del CFTR," The New England Journal of Medicine, 373(3):220-231.
Walters et al. (2002) "Prediction of 'drug-likeness'," Advanced Drug Delivery Reviews, 54(3), 255-271.
Willson T. M. et al. (1996) "Bone targeted drugs 2. Synthesis of estrogens with hydroxyapatite affinity," Bioorg. & Med. Chem. Lett., (6):1047-1050.
Winn, M. et al. (1993) "2-(Alkylamino) nicotinic Acid and Analogs. Potent Angiotensin II Antagonists" Journal of Medicinal Chemistry, 36(18):2676-2688.
Yarnell AT. "Heavy-Hydrogen Drugs Turn Heads, Again" Chemical & Engineering News 2009; 87(25), 36-39.
Anonymous: "Highlights of Prescribing Information—TRIKAFTA," Jun. 1, 2021, pp. 1-18, Retrieved from the internet: URL:https://www.accessdata.fda.gov/drugsat fda_docs/label/2021/212273s004lbl.pdf [retrieved on Nov. 13, 2023].
Bartlett, P.A. and Enteroth, M. (2006) "Exploiting Chemical Diversity for Drug Discovery," The Royal Society of Chemistry, pp. 113-118.
Bhujbal, Sonal et al. (2021) "Pharmaceutical amorphous solid dispersion: A review of manufacturing strategies," Acta Pharmaceutica Sinica B, vol. 11, No. 8, pp. 2505-2536.
Chou, Ting-Chao, Drug Combination Studies and Their Synergy Quantification Using the Chou-Talalay Method, Cancer Res; 70(2), 2010, pp. 440-446).
"Find ETDs Home » Thesis Resources » Find ETDs" Online: "https://ndltd.org/thesis-resources/find-etds/" Accessed Jan. 31, 2023.
Grootenhuis et al. Vertex Pharmaceuticals Incorporated, Boston, MA, USA, Discovery and Biological Profile of Next-Generation CFTR Correctors, 188, Pediatr Pulmonol. Oct. 2016; 51 (Suppl 45):S194-S485, Published online Sep. 21, 2016. doi: https://www.ncbi.nlm.nih.gov/pmc/articles/PMC7159391/.

(56) References Cited

OTHER PUBLICATIONS

International Patent Application No. PCT/US2023/071721: International Search Report and Written Opinion, mailed Dec. 6, 2023 (17 pages).
Irwin, J. J. and Shoichet, B. K. (2005) "ZINC—A Free Database of Commercially Available Compounds for Virtual Screening," *J. Chem. Inf. Model.* 45, 177-182.
Patel, Kaushika et al. (2022) "Solid dispersion technology as a formulation strategy for the fabrication of modified release dosage forms: A comprehensive review," Daru Journal of Pharmaceutical Sciences, Biomed Central Ltd, London, UK, vol. 30, No. 1, pp. 165-189.
Kharkevich, D.A. Farmakologiya (Pharmacology)/ Textbook, 10th edition, pp. 72-82).
Kim, S. et al. (2021) "PubChem in 2021: new data content and improved web interfaces," Nucleic Acids Research, 49, D1388-D1395.
Meoli, A. et al., State of the Art on Approved Cystic Fibrosis Transmembrane Conductance Regulator (CFTR) Modulators and Triple-Combination Therapy, Pharmaceuticals 2021, 14(9), 928; https://doi.org/10.3390/ph14090928, Published: Sep. 15, 2021, https://www.mdpi.com/1424-8247/14/9/928#sec4-pharmaceuticals-14-00928.

\* cited by examiner

Figure 1

| Mutation cDNA Name | Mutation Protein Name | Mutation Legacy Name |
|---|---|---|
| c.1A>G | p.? (unknown) | M1V |
| c.54-5940_273+10250del21kb | p.Ser18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67Leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATinsG | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |
| c.489+1G>T | No protein name | 621+1G->T |

Figure 1 Continued

| Mutation cDNA Name | Mutation Protein Name | Mutation Legacy Name |
|---|---|---|
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| c.595C>T | p.His199Tyr | H199Y |
| c.613C>T | p.Pro205Ser | P205S |
| c.617T>G | p.Leu206Trp | L206W |
| c.658C>T | p.Gln220X | Q220X |
| c.680T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A;1079C>A] | p.[Gln359Lys;Thr360Lys] | Q359K/T360K |

Figure 1 Continued

| Mutation cDNA Name | Mutation Protein Name | Mutation Legacy Name |
|---|---|---|
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |
| c.1202G>A or c.1203G>A | p.Trp401X | W401X |
| c.1209+1G>A | No protein name | 1341+1G->A |
| c.1210-12[5] | No protein name | 5T |
| c.1210-12[7] | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1647T>G | p.Ser549Arg | S549R |

Figure 1 Continued

| Mutation cDNA Name | Mutation Protein Name | Mutation Legacy Name |
|---|---|---|
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9insA | p.Ser641ArgfsX5 | 2055del9->A |

Figure 1 Continued

| Mutation cDNA Name | Mutation Protein Name | Mutation Legacy Name |
|---|---|---|
| c.1973_1985del13insAGAAA | p.Arg658LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G* |
| c.2051_2052delAAinsG | p.Lys684SerfsX38 | 2183delAA->G* |
| c.2052_2053insA | p.Gln685ThrfsX4 | 2184insA |
| c.2052delA | p.Lys684AsnfsX38 | 2184delA |
| c.2125C>T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547C>A | p.Tyr849X | Y849X |
| c.2551C>T | p.Arg851X | R851X |
| c.2583delT | p.Phe861LeufsX3 | 2711delT |

Figure 1 Continued

| Mutation cDNA Name | Mutation Protein Name | Mutation Legacy Name |
|---|---|---|
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG | | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |

MODULATORS OF CYSTIC FIBROSIS TRANSMEMBRANE CONDUCTANCE REGULATOR

CROSS REFERENCE TO RELATED APPLICATIONS

This application claims the benefit of priority under 35 U.S.C. § 119 to United States provisional patent application Ser. Nos. 62/060,182, filed Oct. 6, 2014; 62/114,767, filed Feb. 11, 2015; and 62/153,120, filed Apr. 27, 2015, the entire contents of all applications are incorporated herein by reference.

TECHNICAL FIELD OF THE INVENTION

The present invention features modulators of Cystic Fibrosis Transmembrane Conductance Regulator (CFTR), pharmaceutical compositions, methods of treatment, and kits thereof.

BACKGROUND OF THE INVENTION

Cystic fibrosis (CF) is a recessive genetic disease that affects approximately 30,000 children and adults in the United States and approximately 30,000 children and adults in Europe. Despite progress in the treatment of CF, there is no cure.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease causing mutations in the CF gene have been identified (http://cftr2.org). The most prevalent mutation is a deletion of phenylalanine at position 508 of the CFTR amino acid sequence, and is commonly referred to as F508del. This mutation occurs in approximately 70% of the cases of cystic fibrosis and is associated with a severe disease.

The deletion of residue 508 in F508del prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of F508del in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

Accordingly, there is a need for novel treatments of CFTR mediated diseases.

SUMMARY OF THE INVENTION

The invention features a compound of formula I:

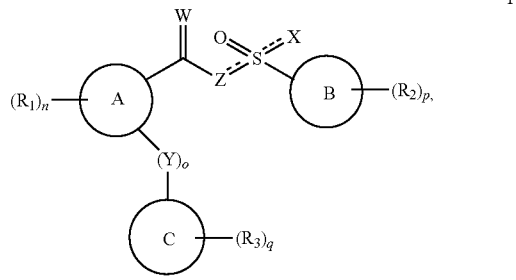

or a pharmaceutically acceptable salt thereof, wherein, independently for each occurrence:

Ring A is a C6-C10 aryl ring; C3-C10 cycloalkyl ring; or a C3-C14 heteroaryl or heterocyclic ring wherein anywhere from 1 to 4 ring atoms are independently O, S, N, or NR;

Ring B is a C3-C10 cycloalkyl ring; a C6-C10 aryl ring; or a C4-C10 heteroaryl or heterocyclic ring wherein anywhere from 1 to 4 ring atoms are independently O, S, N, or NR;

Ring C is a C6-C10 aryl ring; a C3-C14 heteroaryl or heterocyclic ring wherein anywhere from 1 to 4 ring atoms are independently N, NR, O, or S; or a C3-C10 cycloalkyl ring;

W is O, NR, or S;

X is O or NR;

Y is independently CRR, CO, O, S, SO, $SO_2$, S(O)NH or NR;

Z is NR or CHR;

$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are optionally and independently replaced with O, CO, S, SO, $SO_2$ or NR;

or two $R_2$ groups taken together may form a $=CH_2$ or $=O$ group;

$R_3$ is halo; CN; OH; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR; or two $R_3$ groups taken together may form a $=CH_2$ or $=O$ group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;
o is 0, 1, 2, 3, 4, or 5;
p is 0, 1, 2, or 3; and
q is 0, 1, 2, 3, 4, or 5;
---- is a single bond or a double bond;

provided that the moieties containing ring B and ring C are substituted at adjacent positions on ring A.

The present invention also features pharmaceutical compositions thereof, which may include additional agents, and methods of treating CFTR mediated diseases, such as cystic fibrosis, comprising administering compounds of formula I to a subject in need thereof. The present invention also features kits comprising compounds of formula I.

BRIEF DESCRIPTION OF DRAWINGS

FIG. 1 discloses a list of CFTR mutations by name, protein name, and legacy name that in one aspect of the invention a patient may possess and be treatable by the compounds and compositions of the present invention.

DETAILED DESCRIPTION OF THE INVENTION

Definitions

As used herein, "CFTR" stands for cystic fibrosis transmembrane conductance regulator.

As used herein, "mutations" can refer to mutations in the CFTR gene or the CFTR protein. A "CFTR mutation" refers to a mutation in the CFTR gene, and a "CFTR mutation" refers to a mutation in the CFTR protein. A genetic defect or mutation, or a change in the nucleotides in a gene in general results in a mutation in the CFTR protein translated from that gene.

As used herein, a "F508del mutation" or "F508del" is a specific mutation within the CFTR protein. The mutation is a deletion of the three nucleotides that comprise the codon for amino acid phenylalanine at position 508, resulting in CFTR protein that lacks this phenylalanine residue.

The term "CFTR gating mutation" as used herein means a CFTR mutation that results in the production of a CFTR protein for which the predominant defect is a low channel open probability compared to normal CFTR (Van Goor, F., Hadida S. and Grootenhuis P., "Pharmacological Rescue of Mutant CFTR function for the Treatment of Cystic Fibrosis", Top. Med. Chem. 3: 91-120 (2008)). Gating mutations include, but are not limited to, G551D, G178R, S549N, S549R, G551S, G970R, G1244E, S1251N, S1255P, and G1349D.

As used herein, a patient who is "homozygous" for a particular mutation, e.g. F508del, has the same mutation on each allele.

As used herein, a patient who is "heterozygous" for a particular mutation, e.g. F508del, has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator may be through a corrector mechanism or a potentiator mechanism as described below.

As used herein, the term "CFTR corrector" refers to a compound that increases the amount of functional CFTR protein to the cell surface, resulting in enhanced ion transport.

As used herein, the term "CFTR potentiator" refers to a compound that increases the channel activity of CFTR protein located at the cell surface, resulting in enhanced ion transport.

As used herein, the term "inducing," as in inducing CFTR activity, refers to increasing CFTR activity, whether by the corrector, potentiator, or other mechanism.

As used herein, the term "active pharmaceutical ingredient" or "API" refers to a biologically active compound.

A "patient," "subject" or "individual" are used interchangeably and refer to either a human or non-human animal. The term includes mammals such as humans.

The terms "effective dose" or "effective amount" are used interchangeably herein and refer to that amount that produces the desired effect for which it is administered (e.g., improvement in CF or a symptom of CF or lessening the severity of CF or a symptom of CF). The exact amount will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduced cases of chest infections, and/or reduced instances of coughing or shortness of breath. Improvements in or lessening the severity of any of these conditions can be readily assessed according to standard methods and techniques known in the art.

As used herein, the term "in combination with" when referring to two or more compounds or agents means that the order of administration includes the compounds or agents being administered prior to, concurrent with, or subsequent to each other to the patient.

As used herein, the phrase "optionally substituted" is used interchangeably with the phrase "substituted or unsubstituted."

As described herein, compounds within the compositions of the invention can optionally be substituted with one or more substituents, such as are illustrated generally above, or as exemplified by particular classes, subclasses, and species of the invention (such as the compounds listed in Table 1). As described herein in formulae I-Id-ii, the variables $R_1$-$R_4$ in formulae I-Id-ii encompass specific groups, such as, for example, alkyl, alkenyl, alkynyl, alkoxy, heteroaryl, heterocyclic, cycloalkyl, and aryl, etc. Unless otherwise noted, each of the specific groups for the variables $R_1$-$R_4$ can be optionally substituted with one or more group selected from halo, phospho, OH, cycloalkyl, heterocycloalkyl, aryl, heteroaryl, fluoroalkyl, alkyl, alkenyl, alkynyl, nitro, CN, hydroxyl, and (C1-C9alkylene)-E wherein up to 4 $CH_2$ units are independently replaced with O, S, $SO_2$, SO, CO, NH, N-alkyl, N-alkenyl, or N-alkynyl, and E is H, aryl, cycloalkyl, heterocycloalkyl, heteroaryl, alkoxy, CN, or $CF_3$, further wherein each of the aryl, cycloalkyl, heterocycloalkyl, and heteroaryl is optionally substituted with one or more group selected from halo, alkyl, amino, CN, alkenyl, alkynyl, and alkoxy.

As one of ordinary skill in the art will recognize, combinations of substituents envisioned by this invention are those combinations that result in the formation of stable or chemically feasible compounds. The term "stable", as used herein, refers to compounds that are not substantially altered, when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

As disclosed herein, substituents or variables (such as R and $R_1$-$R_4$ in formula I-Id-ii) can be selected from more than one specific group. To the extent that one specific group for a variable may include or overlap with another specific group for the same variable, the narrower specific group is provisioned out from the broader specific group. In other words, double inclusion cannot exist.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

The term "adjacent" as used herein refers to positions on the ring wherein the two ring atoms are bonded to each other. Two ring atoms with an intervening ring atom are not considered adjacent even when that intervening atom does not allow substitution due to valency.

The term "aliphatic", "aliphatic group," as used herein, means a straight-chain (i.e., unbranched) or branched hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups.

The term "spiro" as used herein, means a two-ring system wherein both rings share only one common atom.

The term "cycloaliphatic" or "cycloalkyl" mean a monocyclic, bicyclic (fused or spiro), tricyclic (fused or spiro), or propellane hydrocarbon that has a single point of attachment to the rest of the molecule, and that is completely saturated or contains one or more units of unsaturation, but none of the individual rings in the monocyclic, bicyclic, or tricyclic hydrocarbon is aromatic. The single point of attachment can be on the saturated or unsaturated carbon. In some embodiments, "cycloaliphatic" or "cycloalkyl" refers to a monocyclic $C_3$-$C_8$ hydrocarbon or bicyclic $C_8$-$C_{12}$ hydrocarbon that is completely saturated or that contains one or more units of unsaturation, but none of the individual ring in the monocyclic $C_3$-$C_8$ hydrocarbon or fused bicyclic $C_5$-$C_{12}$ hydrocarbon is aromatic, and that has a single point of attachment to the rest of the molecule wherein any individual ring in said bicyclic ring system has 3-7 members.

As used herein, an "alkyl" group refers to a saturated hydrocarbon group containing 1-20 (e.g., 1-6 or 1-12) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl.

As used herein, an "alkenyl" group refers to a hydrocarbon group that contains 2-20 (e.g., 2-12, 2-6, or 2-4) carbon atoms and at least one double bond. Like an alkyl group, an alkenyl group can be straight or branched. The point of attachment can be on a saturated carbon or unsaturated carbon. Examples of an alkenyl group include, but are not limited to allyl, isoprenyl, 2-butenyl, and 2-hexenyl.

As used herein, an "alkynyl" group refers to a hydrocarbon group that contains 2-20 (e.g., 2-12, 2-6, or 2-4) carbon atoms and has at least one triple bond. An alkynyl group can be straight or branched. The point of attachment can be on a saturated carbon or unsaturated carbon. Examples of an alkynyl group include, but are not limited to, propargyl and butynyl.

As used herein, an "alkoxy" group refers to —O-alkyl, O-alkenyl, or O-alknyl, wherein alkyl, alkenyl, and alkynyl are as defined above.

As used herein, "fluoroalkyl" or "fluoroalkoxy" refers to alkyl or alkoxy wherein one or more hydrogen is substituted with a fluoro.

As used herein, an "amino" refers to NH₂ which is optionally substituted with one or two groups independently selected from alkyl, cycloalkyl, and heterocycloalkyl.

The term "electron withdrawing group", as used herein means an atom or a group that is electronegative relative to hydrogen. See, e.g., "Advanced Organic Chemistry: Reactions, Mechanisms, and Structure," Jerry March, 4$^{th}$ Ed., John Wiley & Sons (1992), e.g., pp. 14-16, 18-19, etc. Exemplary such substituents include halo such as Cl, Br, or F, CN, COOH, CF₃, etc.

Unless otherwise specified, the term "heterocycle", "heterocyclyl", "heterocycloaliphatic", "heterocycloalkyl" or "heterocyclic" as used herein means monocyclic, bicyclic (fused or spiro), tricyclic (fused or spiro), or propellane ring systems in which one or more ring atoms in one or more ring members is an independently selected heteroatom and none of the individual rings in the system is aromatic. Heterocyclic rings can be saturated or can contain one or more unsaturated bonds. In some embodiments, the "heterocycle", "heterocyclyl", "heterocycloaliphatic", "heterocycloalkyl" or "heterocyclic" group has three to fourteen ring members in which one or more ring members is a heteroatom independently selected from oxygen, sulfur, nitrogen, or phosphorus, and each ring in the ring system contains 3 to 7 ring members. The point of attachment can be on the carbon or heteroatom.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic (fused), and tricyclic (fused or spiro) hydrocarbon ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic (fused), and tricyclic (fused or spiro) ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylene" refers to a straight or branched hydrocarbon chain that may be fully saturated or have one or more units of unsaturation and has two points of attachment to the rest of the molecule.

The term "prodrug," as used herein, represents a compound that is transformed in vivo into a compound according to any one of the formulae listed herein. Such a transformation can be affected, for example, by hydrolysis in blood or enzymatic transformation of the prodrug form to the parent form in blood or tissue. Prodrugs of the compounds of the invention may be, for example, amides. Amides that may be utilized as prodrugs in the present invention are phenyl amides, aliphatic (C1-C24) amids, acyloxymethyl amides, ureas, carbamates, and amino acid amides. For example, a compound of the invention that contains an NH group may be acylated at this position in its prodrug form. Other prodrug forms include esters, such as, for example phenyl esters, aliphatic (C1-C24) esters, acyloxymethyl esters, carbonates, carbamates, and amino acid esters. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated in its entirety herein by reference. In some embodiments, the present invention features a prodrug of any one of the formulas or compounds listed herein.

The term "isosteres" or "bioisosteres," as used herein, refers to compounds resulting from the exchange of an atom or group of atoms to create a new compound with similar biological properties to the parent compound. The bioisosteric replacement may be physicochemically or topologically based. For example, an isosteric replacement for a carboxylic acid is CONHSO₂(alkyl or aryl)) such as CONHSO₂Me. A further discussion of isosterism is provided in R. Silverman, The Organic Chemistry of Drug Design and Drug Action, second edition, Elsevier Academic Press, 2004, incorporated in its entirety herein by reference. In some embodiments, the present invention features a isostere of any one of the formulas or compounds listed herein.

In the formulas and drawings, a line transversing a ring and bonded to an R group such as, for example, R₂ in the following formula

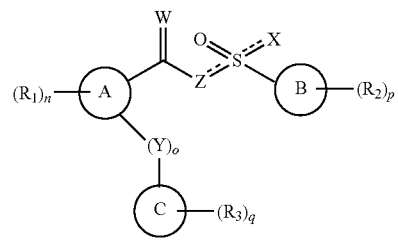

means that the R group can be bonded to any carbon, or if applicable, heteroatom such as N, of that ring, including any fused ring, as valency allows.

Within a term definition as, for example, R₁ through R₃ when a CH₂ unit or, interchangeably, a methylene unit may be replaced by O, CO, S, SO, SO₂, or NR; it is meant to include any CH₂ unit, including a CH₂ within a terminal methyl or methylene group. For example, —CH₂CH₂CH₂SH is within the definition of C1-C9 alkylene-R₄ wherein up to four CH₂ units are independently replaced by O, CO, S, SO, SO₂, or NR because the CH₂ unit of the terminal methyl group has been replaced by S. The analogous applies to such definitions as —CH₂CH₂OH, —CH₂CH₂CN, or —CH₂CH₂NH₂.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Where the enantiomers of a racemic mixture have been separated, but the absolute chemistry has not yet been determined, the compound's structure is depicted with a wavy line.

Unless otherwise stated, all tautomeric forms of the compounds of the invention are within the scope of the invention. Thus, included within the scope of the invention are tautomers of compounds of formulas I to Id-ii.

To the extent that a definition in the present application differs from any definition in an application incorporated by reference, the definition in the present application supercedes.

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

In patients with cystic fibrosis, mutations in endogenously expressed CFTR lead to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea-perhaps explaining the relatively high frequency of the CF gene within the population.

Sequence analysis of the CFTR gene of CF chromosomes has revealed a variety of disease-causing mutations (Cutting, G. R. et al. (1990) Nature 346:366-369; Dean, M. et al. (1990) Cell 61:863-870; and Kerem, B-S. et al. (1989) Science 245:1073-1080; Kerem, B-S et al. (1990) Proc. Natl. Acad. Sci. USA 87:8447-8451). To date, greater than 1000 disease-causing mutations in the CF gene have been identified as reported by the scientific and medical literature. The most prevalent mutation is a deletion of phenylalanine at position 508 of the CFTR amino acid sequence, and is commonly referred to as F508del. This mutation occurs in approximately 70 percent of the cases of cystic fibrosis and is associated with a severe disease. A more complete list of identified mutations can be found at www.cftr2.org.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl⁻ channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Compounds of Formula I

In some embodiments the present invention features a compound of formula I:

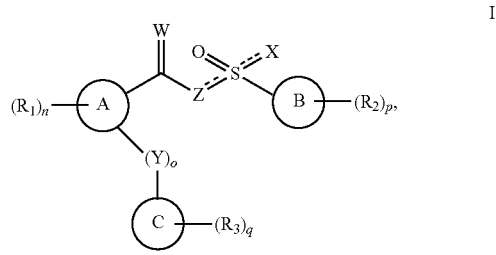

or a pharmaceutically acceptable salt thereof, wherein, independently for each occurrence:

Ring A is a C6-C10 aryl ring; C3-C10 cycloalkyl ring; or a C3-C14 heteroaryl or heterocyclic ring wherein anywhere from 1 to 4 ring atoms are independently O, S, N, or NR;

Ring B is a C3-C10 cycloalkyl ring; a C6-C10 aryl ring; or a C4-C10 heteroaryl or heterocyclic ring wherein anywhere from 1 to 4 ring atoms are independently O, S, N, or NR;

Ring C is a C6-C10 aryl ring; a C3-C14 heteroaryl or heterocyclic ring wherein anywhere from 1 to 4 ring atoms are independently N, NR, O, or S; or a C3-C10 cycloalkyl ring;

W is 0, NR, or S;

X is O or NR;

Y is independently CRR, CO, O, S, SO, $SO_2$, S(O)NH or NR;

Z is NR or CHR;

$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR; or two $R_2$ groups taken together may form a =$CH_2$ or =O group;

$R_3$ is halo; CN; OH; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a =$CH_2$ or =O group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2C1$-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;

o is 0, 1, 2, 3, 4, or 5;

p is 0, 1, 2, or 3; and q is 0, 1, 2, 3, 4, or 5;

---- is a single bond or a double bond;

provided that the moieties containing ring B and ring C are substituted at adjacent positions on ring A.

In another embodiment, the compounds of the invention are of formula I and the attendant definitions, provided that: i) when ring A is indole, n is not zero and rings B and C are aryl unsubstituted by $CF_3$ or halo; ii) when ring A is pyrazole, n is not zero; iii) when ring A is pyridyl, ring B and ring C moieties are substituted at the 2- and 3-positions of the pyridyl ring, interchangeably; and iv) when ring A is imidazole, the ring B moiety is substituted at the 2-position of the imidazole ring.

In some embodiments, the compounds of the present inventions are in the form of a pharmaceutically acceptable prodrug.

In some embodiments, ring A is a C6-C10 aryl ring, such as a phenyl, indane, 1,2,3,4-tetrahydronaphthalene, or naphthalene. In some embodiments, ring A is a C3-C11 heteroaryl or heterocyclic ring wherein anywhere from 1 to 4 ring atoms are independently O, S, N, or NR, such as pyridyl, indole, indoline, isoindoline, pyrazole, pyrimidine, 1,2,3,4-tetrahydroquinoline, quinoline, 5,6,7,8-tetrahydroquinoline, 1,2,3,4-tetrahydroisoquinoline, pyrrolodine, azaindole, pyrrole, oxazole, pyrazine, triazole, indazole, 2,3,4,5-tetrahydro-1H-benzo[d]azepine, 1H-benzo[d]imidazole, or imidazole ring.

In some embodiments, ring A is a group represented by the corresponding moieties shown in the compounds of Table 1. For example, ring A is N

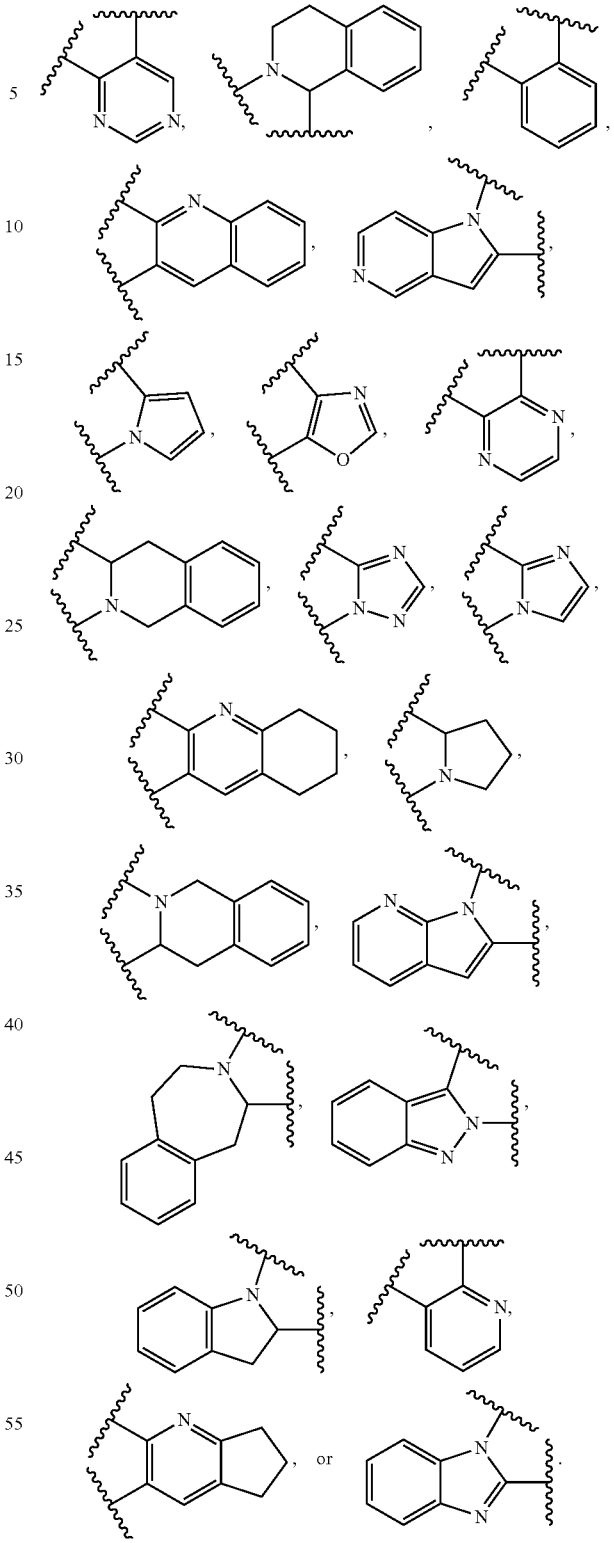

In some embodiments, ring B is a cycloalkyl ring, such as a cyclopropane, cyclobutane, cyclopentane, or cyclohexane. In some embodiments, ring B is a C6-C10 aryl ring, such as a phenyl. In some embodiments, ring B is a heroaryl or heterocyclic ring wherein anywhere from 1 to 4 ring atoms are independently O, S, N, or NR, such as pyridyl, pyridine-2 (1H)-one, pyrazole, indole, indoline, thiophene, dihydrobenzofuran, tetrahydrofuran, furan, pyrazine, indazole, thiazole, pyridine-4 (1H)-one, pyrrolidinone, 3-azabicyclo[3.1.0]hexane, (1R,4R)-2-oxa-5-azabicyclo[2.2.1]heptane, pyrrolidine, azetidine, piperidine, piperazine, or quinoline.

In some embodiments, ring B is a group represented by the corresponding moieties shown in the compounds of Table 1. For example, ring B is

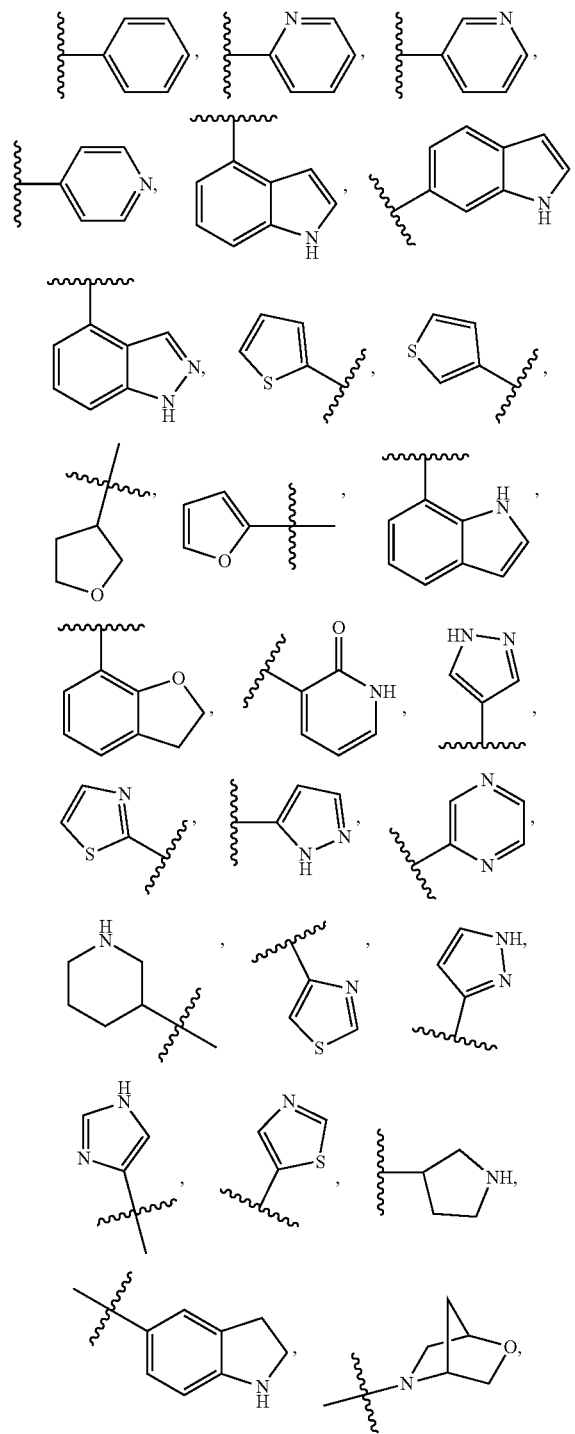

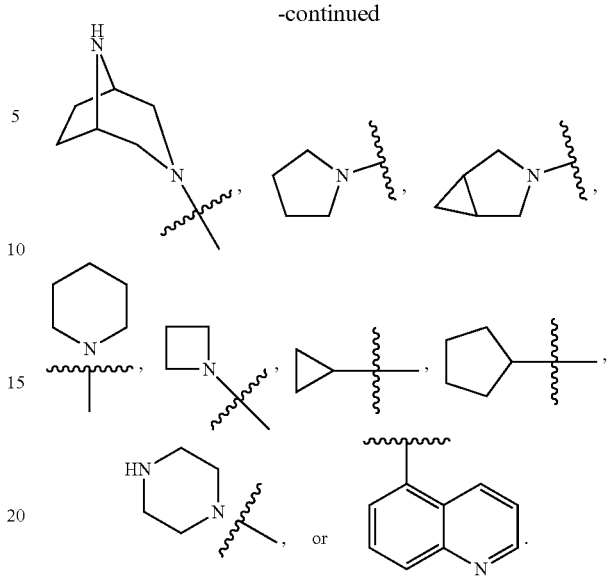

In some embodiments, ring C is a C6-C10 aryl ring, such as a phenyl, indane, or naphthalene. In some embodiments, ring C is a C3-C10 cycloalkyl ring, such as a cyclopropane, cyclobutane, cyclopentane, cyclopentene, cyclohexane, cyclohexene, cycloheptane, or (1s,4s)-bicyclo[2.2.1]heptane. In some embodiments, ring C is a C3-C10 heteroaryl or heterocyclic ring wherein anywhere from 1 to 4 ring atoms are independently N, NR, O, or S, such as indole, isoindoline, indoline, pyridyl, pyrrolidine, 2,5-dihydro-1H-pyrrole, morpholine, tetrahydro-2H-pyran, tetrahydrofuran, oxetane, piperidine, piperazine, azepane, azetidine, octahydrocyclopenta[c]pyrrole, octahydrocyclopenta[b]pyrrole, octahydro-1H-indole, octahydro-1H-cyclopenta[b]pyridine, (1s,4s)-7-azabicyclo[2.2.1]heptane, 2-azabicyclo[4.1.0]heptane, (1S,4R)-2-azabicyclo[2.2.1]heptane, (1R,5S)-8-azabicyclo[3.2.1]octane, 3,6-dihydro-2H-pyran, or (1R,5S)-3-azabicyclo[3.2.1]octane.

In some embodiments, ring C is a group represented by the corresponding moieties shown in the compounds of Table 1. For example, Ring C is

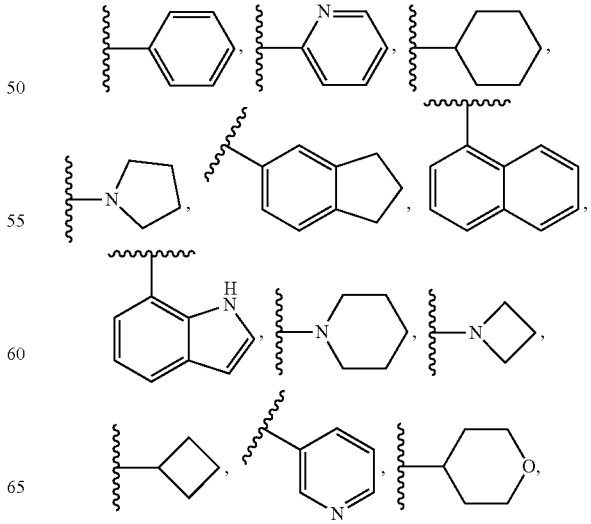

-continued
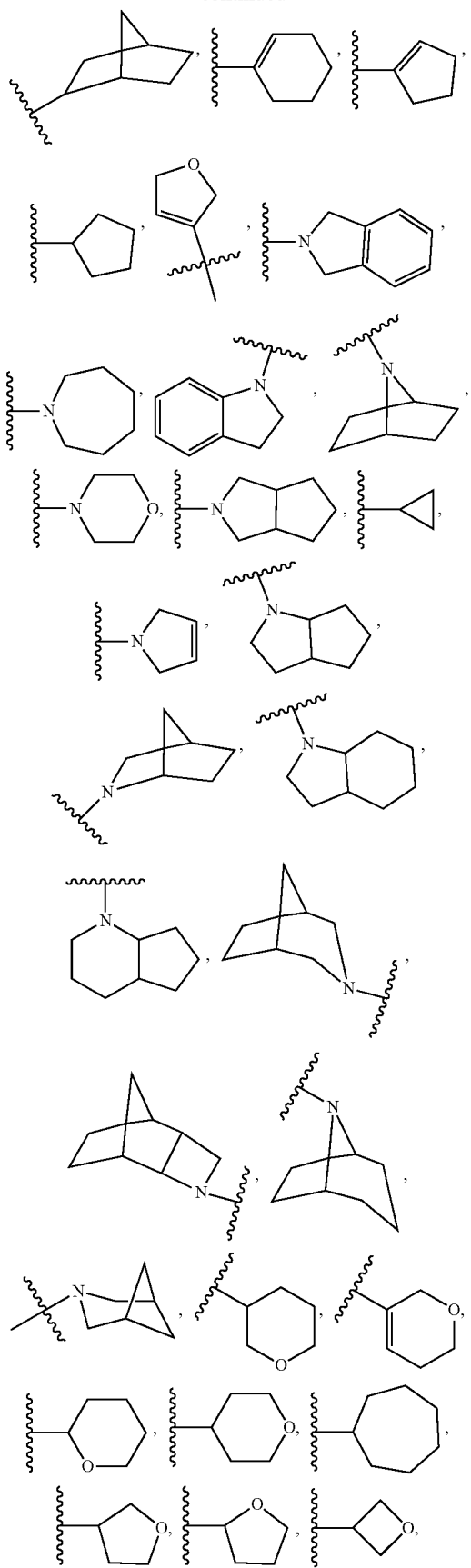
-continued
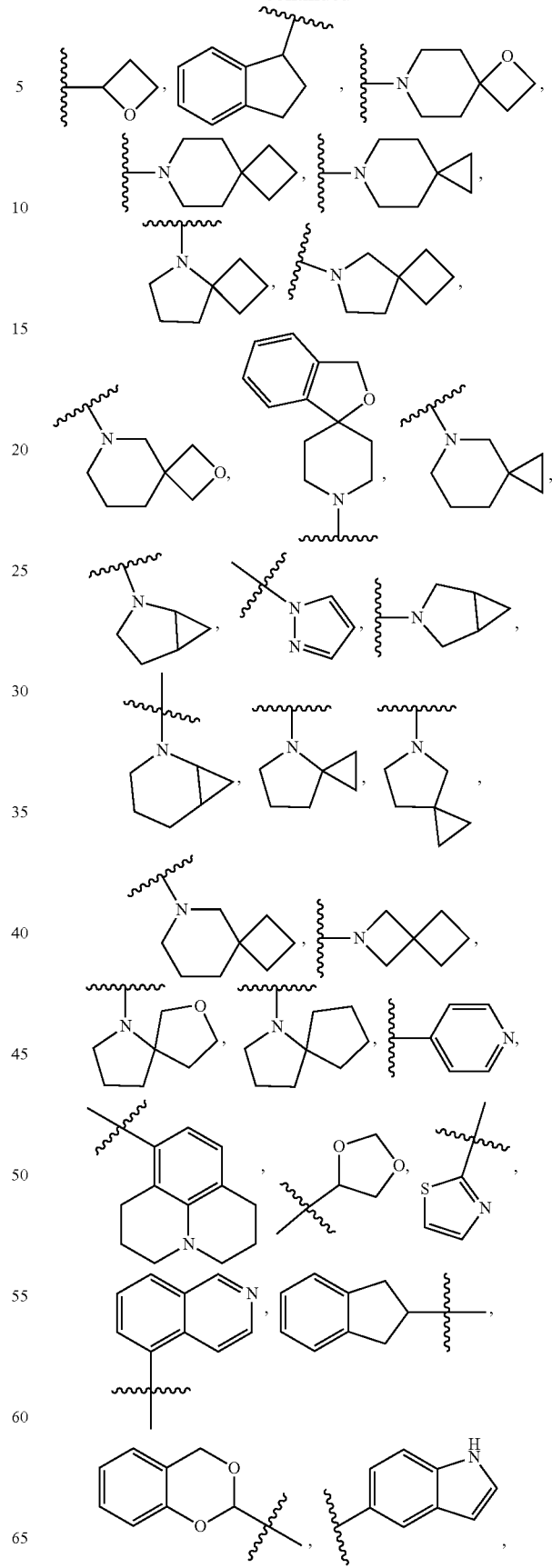

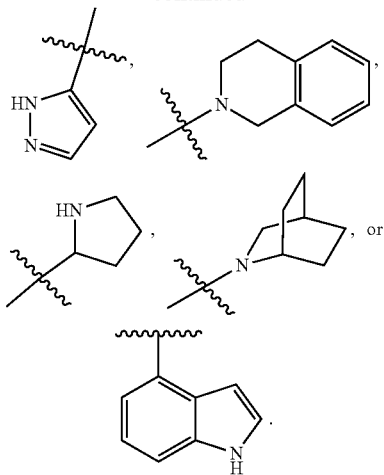

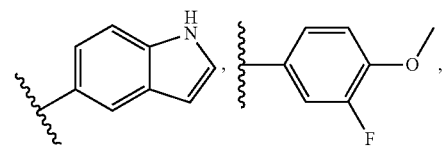
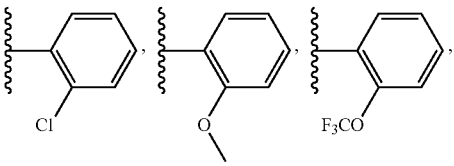
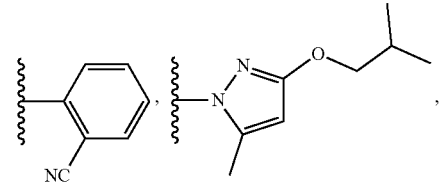
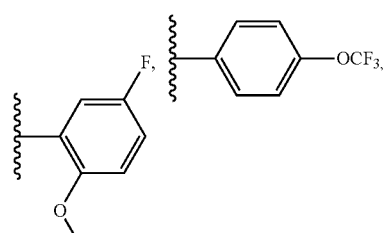
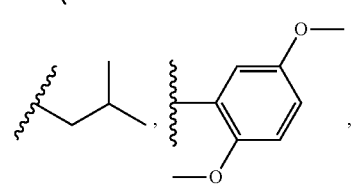
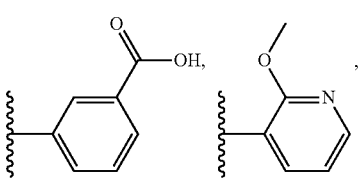
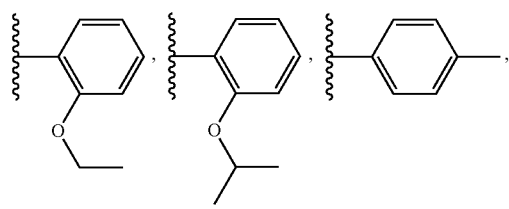

In some embodiments, X is O. In some embodiments, X is NR. In some embodiments, X is NH.

In In some embodiments, Y is O. In some embodiments, Y is CRR, such as CH$_2$, CH(C1-C6 alkyl), CH(CH$_3$), or CH(CH$_2$CH$_3$). In some embodiments, Y is NR, such as NH, N(C1-C6 alkynyl), or N(C1-C6 alkyl). In some embodiments, (Y)$_o$ is a bond, O, NH, (CH$_2$)$_m$, O—(CH$_2$)$_m$, where m=1-4, CH(CH$_3$), O—CH(CH$_3$), O—CH(CH$_2$CH$_3$), O—CH(CH$_3$)CH$_2$, O—C(CH$_3$)$_2$CH$_2$, O—CH$_2$CH$_2$CH(CH$_3$), N(CH$_3$), NH—CH$_2$, N(CH$_3$)—CH$_2$, NCH(CH$_3$)$_2$—CH$_2$, N(CH$_2$CH$_2$CH$_3$)—CH$_2$, NH—CH(CH$_3$), N(CH$_3$)—CH(CH$_3$), or N(CH$_2$CCH)—CH$_2$CH$_2$.

In some embodiments, R$_1$ is halo, CN, C1-C6 alkyl, C1-C6 alkoxy, C3-C8 cycloalkyl, or a phenyl, pyridyl, pyrimidine, indole, aza-indole, azetidine, pyrazole, or thiophene ring, or a (C1-C9 alkylene)-R$_4$ wherein up to four CH$_2$ units are independently replaced with O, CO, S, SO, SO$_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, CH$_2$OH, CH$_2$OCH$_3$, CN, CO$_2$H, amino, amido, C3-C10 heteroaryl, and C3-C10 heterocycloalkyl.

In some embodiments, R$_1$ is a group represented by the corresponding moieties shown in the compounds of Table 1. For example R$_1$ is CH$_3$, Cl, F, CN, OCH$_3$, CF$_3$, CH$_2$CH$_3$, tBu, CH(CH$_3$)$_2$, OCH$_2$CH$_2$OCH$_2$CH$_3$,

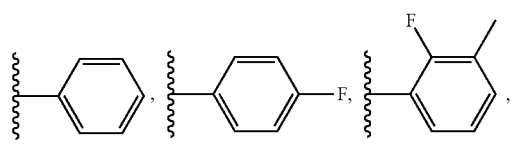

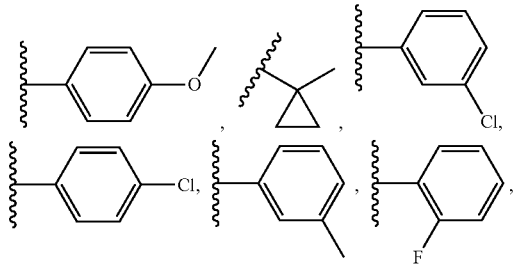

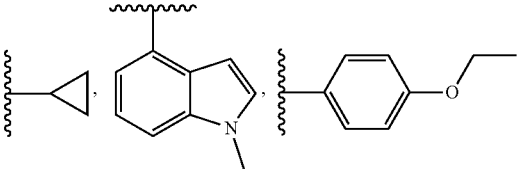

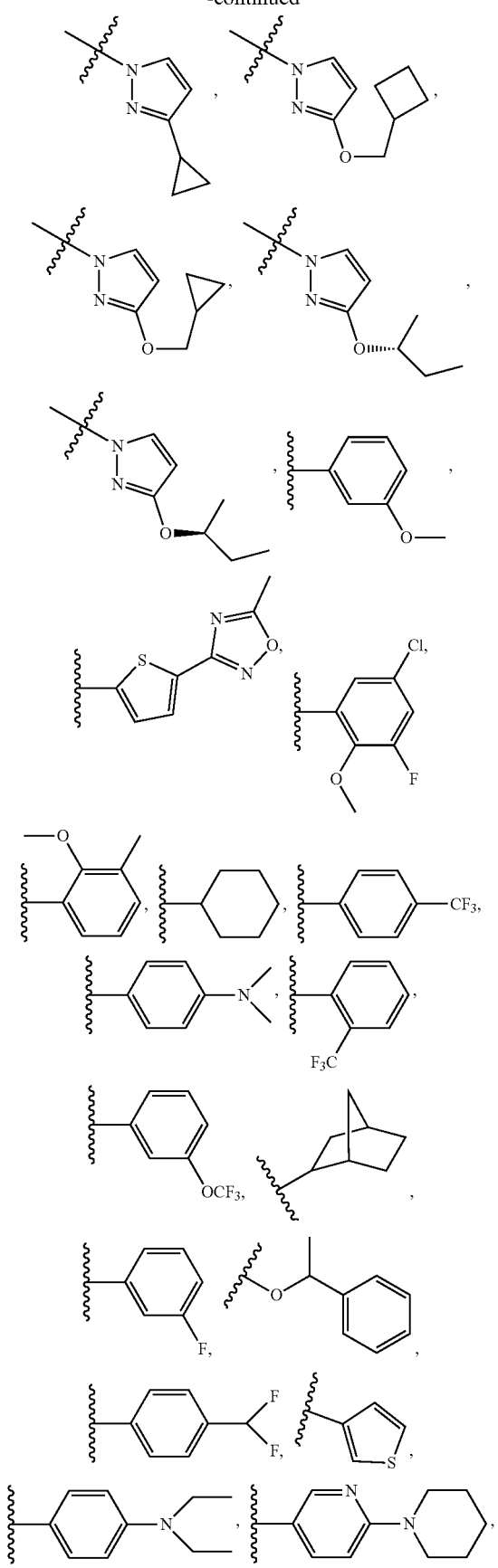
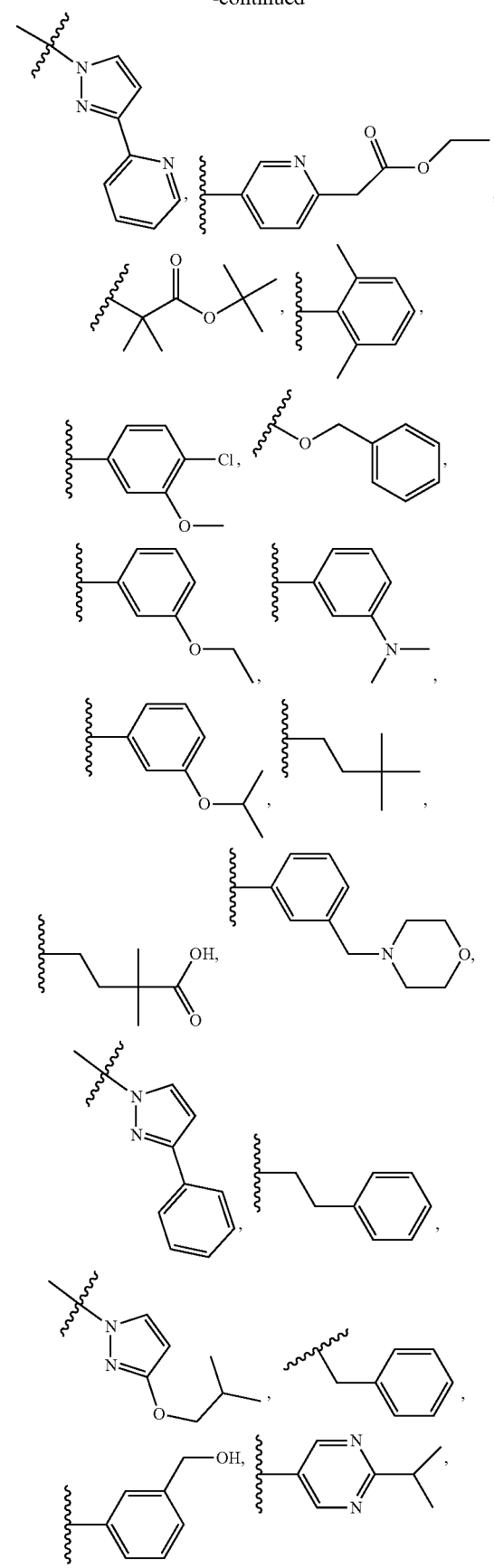

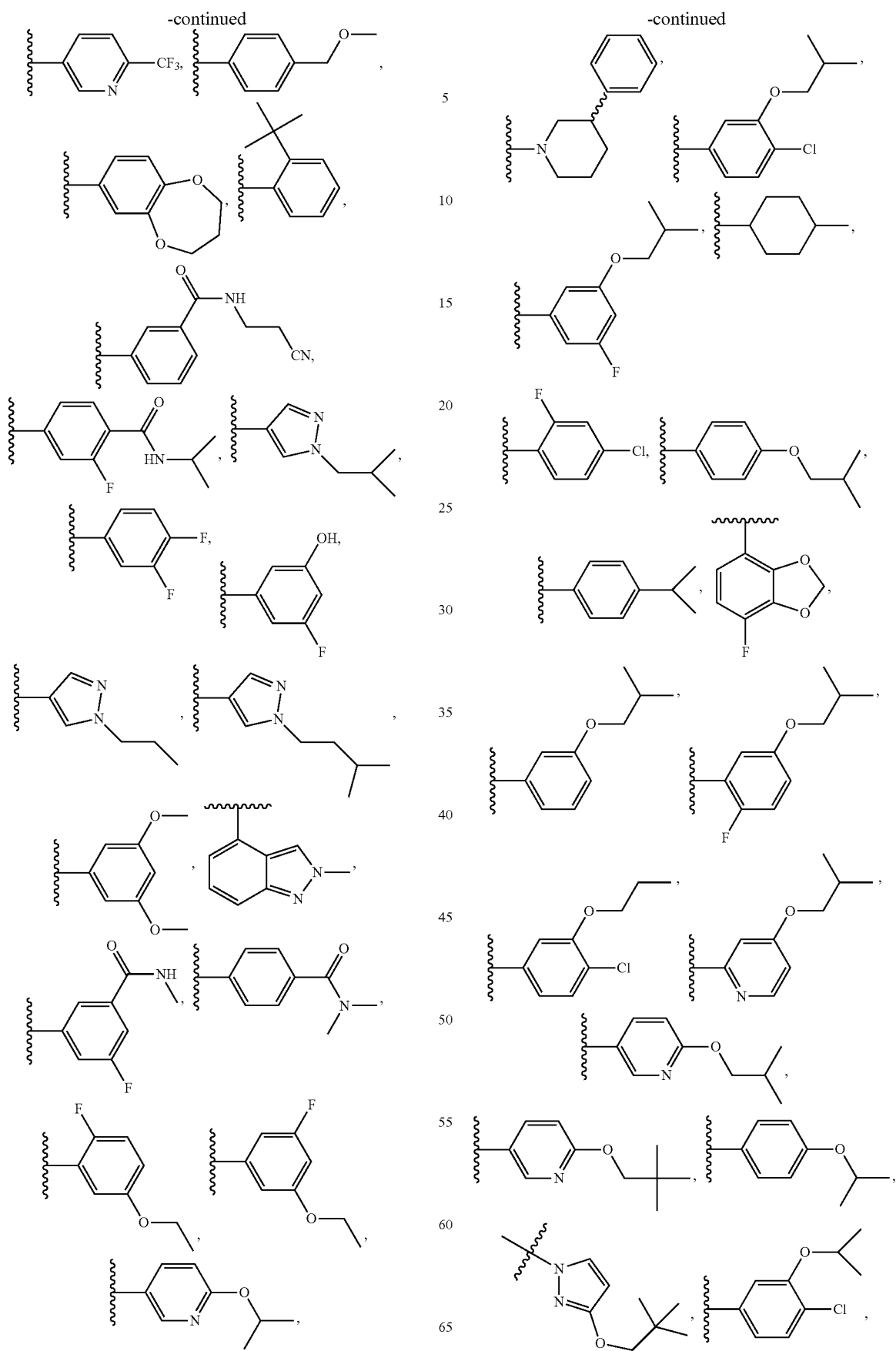

-continued

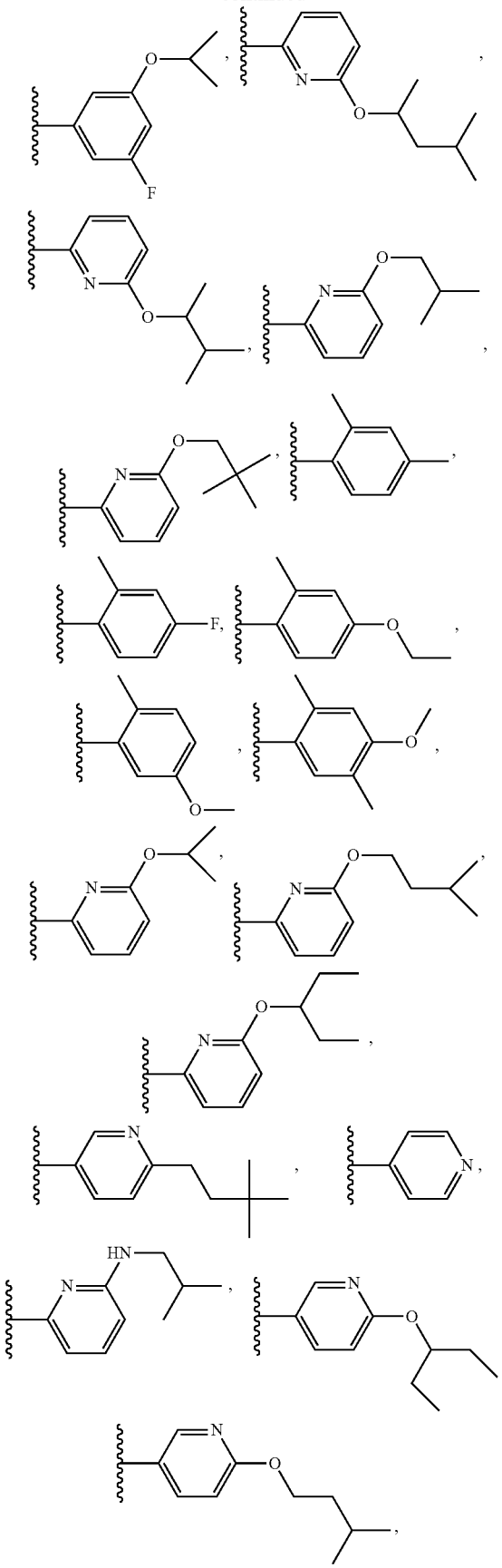

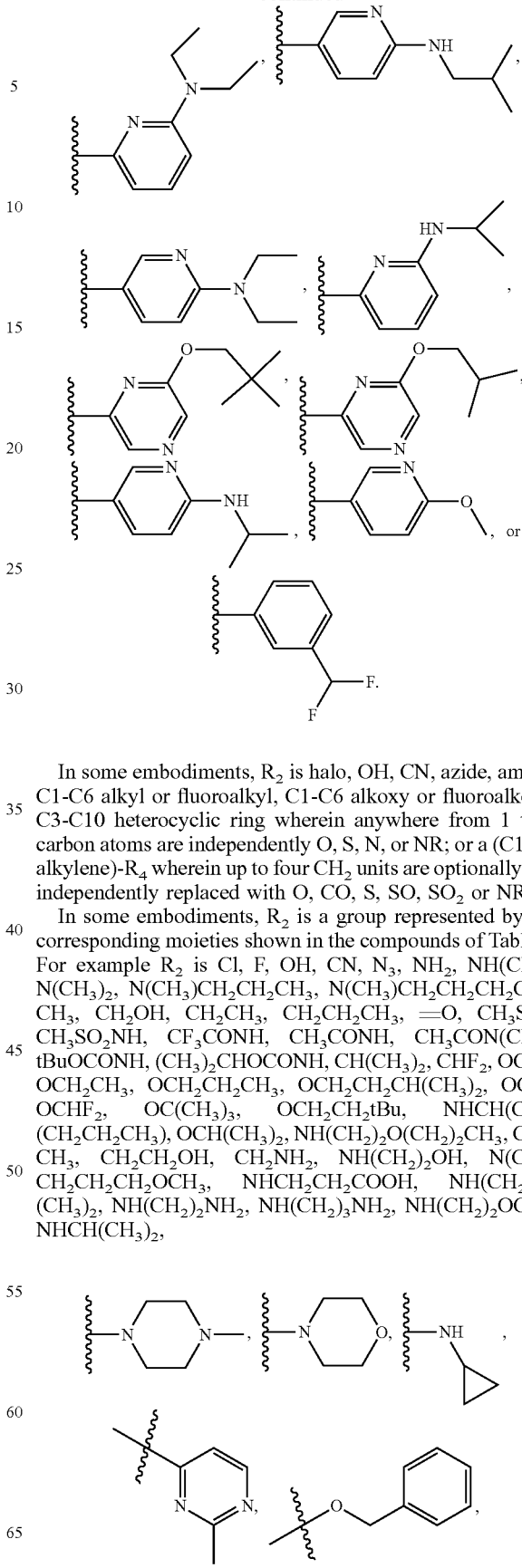

In some embodiments, $R_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 carbon atoms are independently O, S, N, or NR; or a (C1-C9 alkylene)-$R_4$ wherein up to four $CH_2$ units are optionally and independently replaced with O, CO, S, SO, $SO_2$ or NR.

In some embodiments, $R_2$ is a group represented by the corresponding moieties shown in the compounds of Table 1. For example $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)$ $(CH_2CH_2CH_3)$, $OCH(CH_3)_2$, $NH(CH_2)_2O(CH_2)_2CH_3$, C(O) $CH_3$, $CH_2CH_2OH$, $CH_2NH_2$, $NH(CH_2)_2OH$, $N(CH_3)$ $CH_2CH_2CH_2OCH_3$, $NHCH_2CH_2COOH$, $NH(CH_2)_2N$ $(CH_3)_2$, $NH(CH_2)_2NH_2$, $NH(CH_2)_3NH_2$, $NH(CH_2)_2OCH_3$, $NHCH(CH_3)_2$,

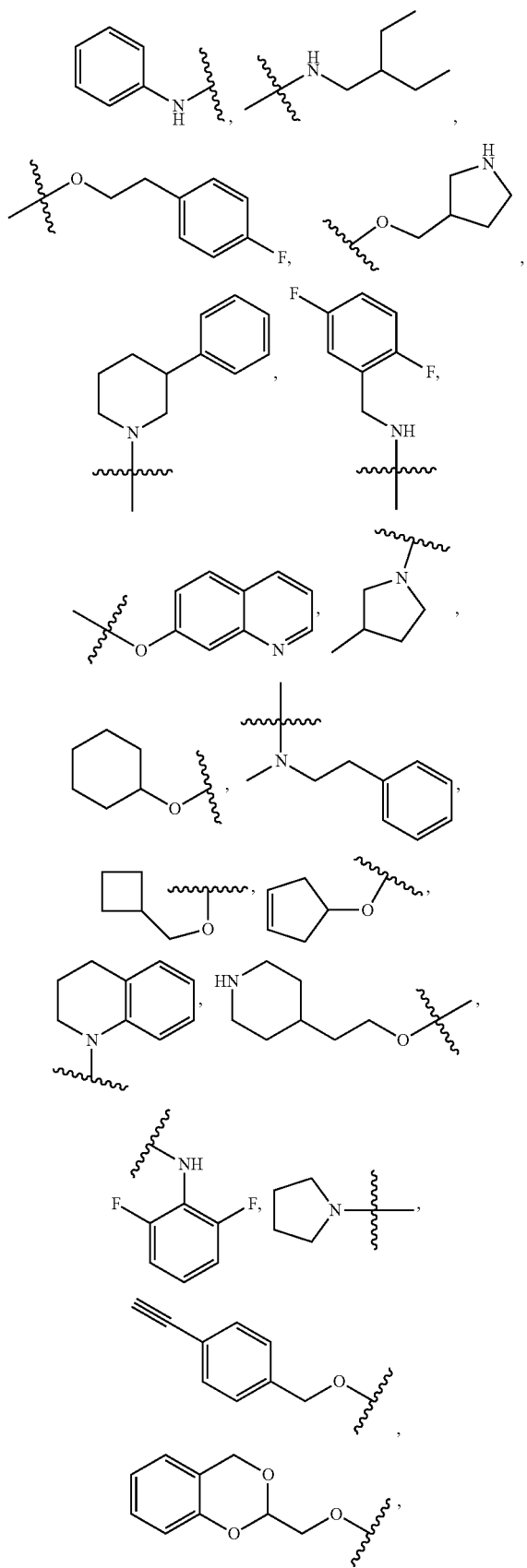

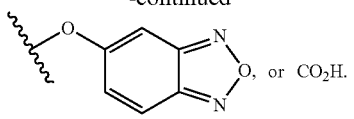, or CO₂H.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

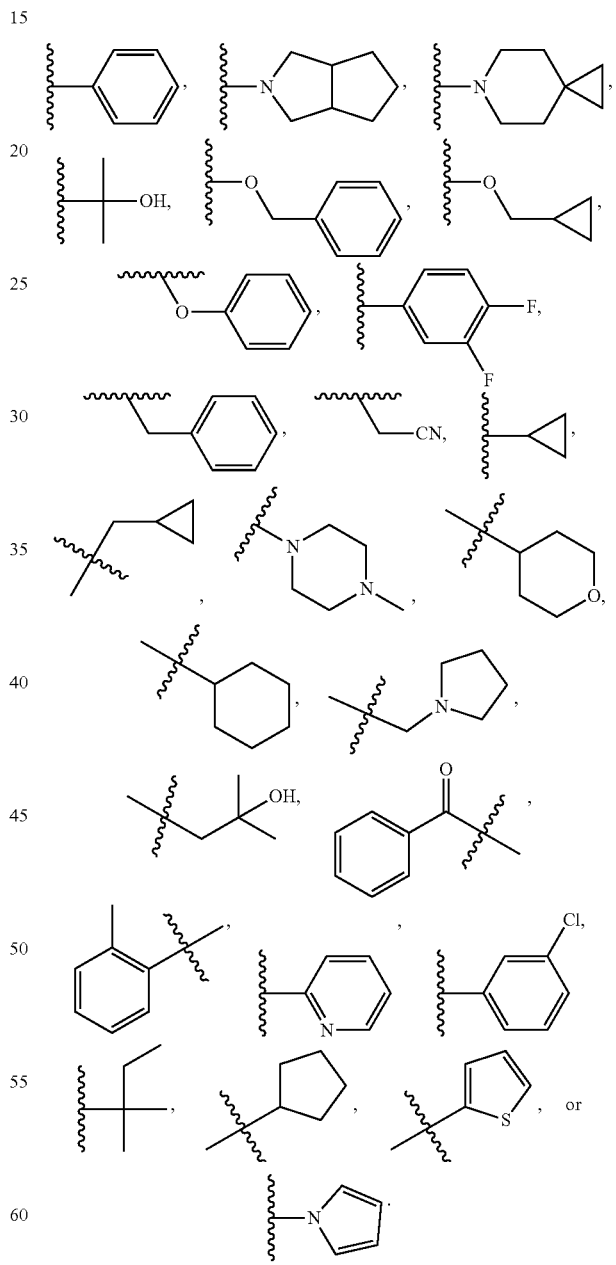

In some embodiments, o is 0. In some embodiments, o is 1. In some embodiments, o is 2.

In some embodiments, n is 0. In some embodiments, n is 1. In some embodiments, n is 2.

In some embodiments, p is 0. In some embodiments, p is 1. In some embodiments, p is 2.

In some embodiments, ring A is

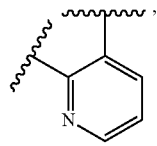 [SMILES: *c1cccnc1*]

and n is 1. In some embodiments, ring A is

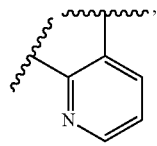 [SMILES: *c1cccnc1*]

n is 1, and $R_1$ is tBu. In some embodiments, ring A is

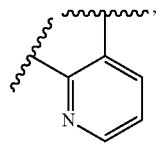 [SMILES: *c1cccnc1*]

n is 1, and $R_1$ is phenyl. In some embodiments, ring A is

n is 1, $R_1$ is phenyl, and Y is O. In some embodiments, ring A is

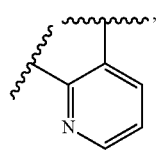 [SMILES: *c1cccnc1*]

n is 1, $R_1$ is tBu, and Y is O. In some embodiments, ring A is

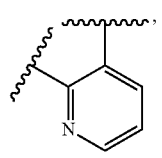 [SMILES: *c1cccnc1*]

ring B is pyridyl, and ring C is phenyl. In some embodiments, $R_1$ is phenyl, $R_2$ is amino, and $R_3$ is $CH_3$.

In some embodiments, ring A is

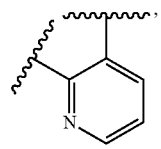 [SMILES: *c1cccnc1*]

n is 1, and $R_1$ is pyridyl. In some embodiments, ring A is

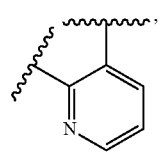

n is 1, $R_1$ is pyridyl, and o is 0. In some embodiment, ring A is

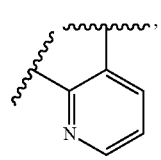

ring B is pyridyl, and ring C is pyrrolidine.

In some embodiments, ring A is

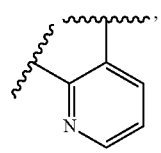 [SMILES: *c1cccnc1*]

n is 1, and $R_1$ is pyrazole. In some embodiments, ring A is

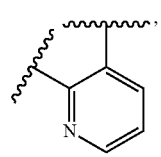 [SMILES: *c1cccnc1*]

n is 1, $R_1$ is pyrazole, and o is 0.

In some embodiments, ring A is

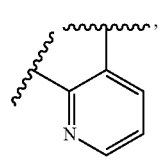

n is 1, and $R_1$ is cycloalkyl. In some embodiments, ring A is

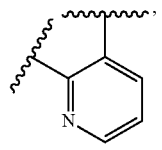

n is 1, $R_1$ is cycloalkyl, and Y is O. In some embodiments, ring A is

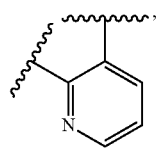 [SMILES: *c1cccnc1*]

ring B is pyridyl, and ring C is cycloalkyl. In some embodiments, $R_1$ is cycloalkyl, $R_2$ is alkoxy, and $R_3$ is $CH_3$.

In some embodiments, ring A is

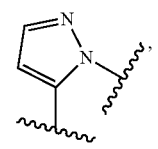 [SMILES: *c1ccnn1*]

and n is 1. In some embodiments, ring A is

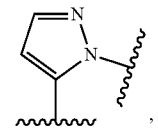

n is 1, and $R_1$ is phenyl. In some embodiments, ring A is

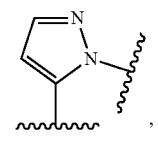

n is 1, and $R_1$ is tBu. In some embodiments, ring A is

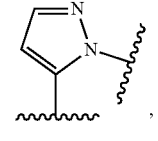

n is 1, $R_1$ is phenyl, and Y is O. In some embodiments, ring A is

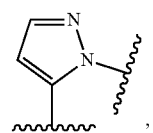

n is 1, $R_1$ is tBu, and Y is O. In one embodiment, ring A is

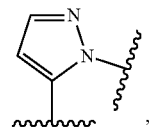

ring B is pyridyl, and ring C is phenyl.
In some embodiments, ring A is

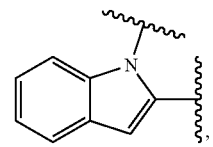 [SMILES: *c1cc2ccccc2n1*]

and n is 1. In some embodiments, ring A is

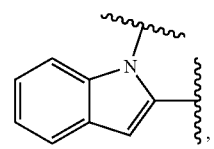 [SMILES: *c1cc2ccccc2n1*]

n is 1, and $R_1$ is phenyl. In some embodiments, ring A is

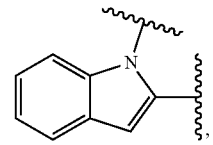

n is 1, and $R_1$ is tBu. In some embodiments, ring A is

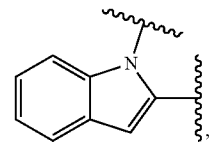 [SMILES: *c1cc2ccccc2n1*]

n is 1, $R_1$ is phenyl, and Y is O. In some embodiments, ring A is

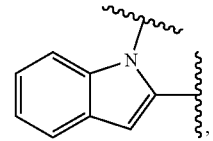 [SMILES: *c1cc2ccccc2n1*]

n is 1, R$_1$ is tBu, and Y is O. In some embodiment, ring A is

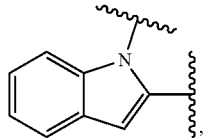

ring B is pyridyl, and ring C is phenyl.

In some embodiments, ring A is

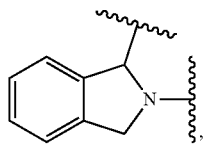 [SMILES: *C1c2ccccc2CN1*]

and n is 1. In some embodiments, ring A is

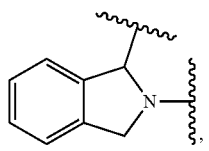 [SMILES: *C1c2ccccc2CN1*]

n is 1, and R$_1$ is phenyl. In some embodiments, ring A is

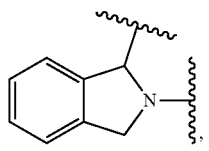 [SMILES: *C1c2ccccc2CN1*]

n is 1, and R$_1$ is tBu. In some embodiments, ring A is

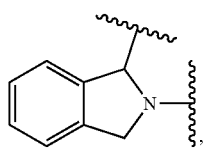 [SMILES: *C1c2ccccc2CN1*]

n is 1, R$_1$ is phenyl, and Y is O. In some embodiments, ring A is

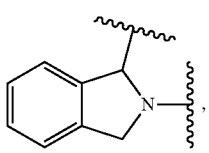 [SMILES: *C1c2ccccc2CN1*]

n is 1, R$_1$ is tBu, and Y is O. In one embodiment, ring A is

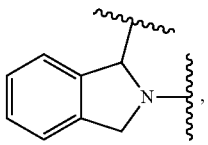 [SMILES: *C1c2ccccc2CN1*]

ring B is pyridyl, and ring C is phenyl.

In some embodiments, the present invention features a compound of formula I-i:

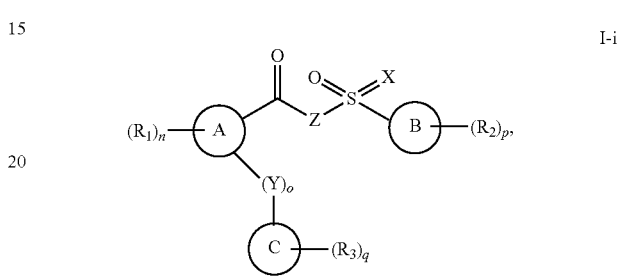

I-i or a pharmaceutically acceptable salt thereof, wherein, independently for each occurrence:

Ring A is a C3-C14 heteroaryl or heterocyclic ring wherein anywhere from 1 to 4 ring atoms are independently O, S, N, or NR;

Ring B is a C3-C10 heteroaryl ring wherein anywhere from 1 to 4 ring atoms are independently O, S, N, or NR;

Ring C is a C6-C10 aryl ring, C3-C14 heteroaryl or heterocyclic ring wherein anywhere from 1 to 4 ring atoms are optionally N, O, or S, or a C3-C10 cycloalkyl ring;

X is O or NR;

Y is CRR, CO, O, S, SO, SO$_2$, S(O)NH or NR;

Z is NR or CHR;

R$_1$ is halo; CN; F$_3$S; SiR$_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-R$_4$ wherein up to four CH$_2$ units are independently replaced with O, CO, S, SO, SO$_2$ or NR; C6-C10 aryl; C3-C10 heteroaryl or heterocyclic ring wherein anywhere from 1 to 4 ring atoms are independently O, S, N, or NR; or C3-C10 cycloalkyl;

R$_2$ is halo; OH; NRR; azide; CN; CO$_2$R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R$_4$ wherein up to four CH$_2$ units are independently replaced with O, CO, S, SO, SO$_2$ or NR;

or two R$_2$ groups taken together may form a =CH$_2$ or =O group;

R$_3$ is halo; CN; CO$_2$R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R$_4$ wherein up to four CH$_2$ units are independently replaced with O, CO, S, SO, SO$_2$ or NR;

or two R$_3$ groups taken together may form a =CH$_2$ or =O group;

R$_4$ is H; azide; CF$_3$; CHF$_2$; OR; CCH; CO$_2$R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO$_2$R;

R is independently H; OH; CO$_2$H; CO$_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;

o is 0, 1, 2, 3, 4, or 5;

p is 0, 1, 2, or 3; and q is 0, 1, 2, 3, 4, or 5;

provided that the moieties containing ring B and ring C are substituted at adjacent positions on ring A.

In some embodiments, the compound of formula I-i exists as a pharmaceutically acceptable prodrug.

In some embodiments, ring A is a pyridyl, indole, indoline, isoindoline, pyrazole, pyrimidine, quinoline, 5,6,7,8-tetrahydroquinoline, 1,2,3,4-tetrahydroisoquinoline, pyrrolodine, aza-indole, pyrrole, oxazole, pyrazine, triazole, indazole, or imidazole ring.

In some embodiments, ring A is a group represented by the corresponding moieties shown in the compounds of Table 1. For example, ring A is

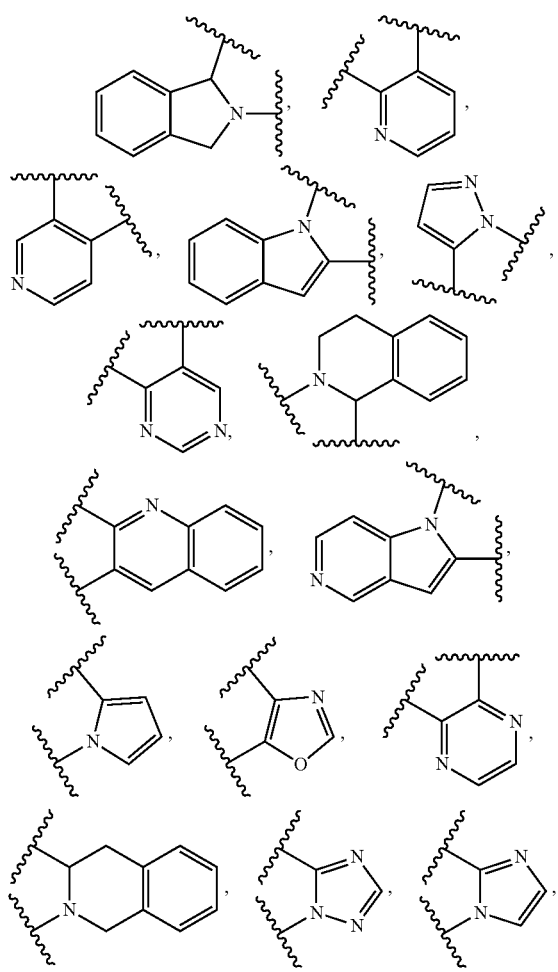

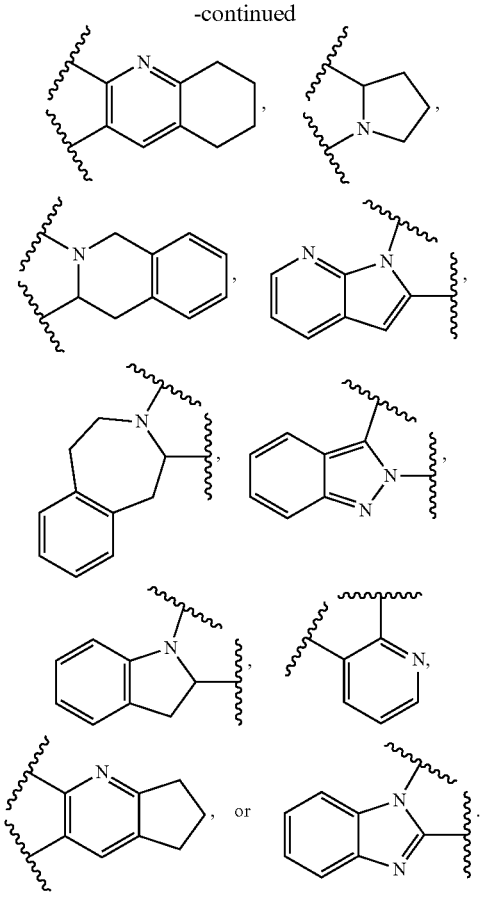

In some embodiments, ring B is pyridyl, pyridine-2(1H)-one, pyrazole, indole, aza-indole, thiophene, dihydrobenzofuran, thiazole, pyrrolidinone, or quinoline.

In some embodiments, ring B is a group represented by the corresponding moieties shown in the compounds of Table 1. For example, ring B is

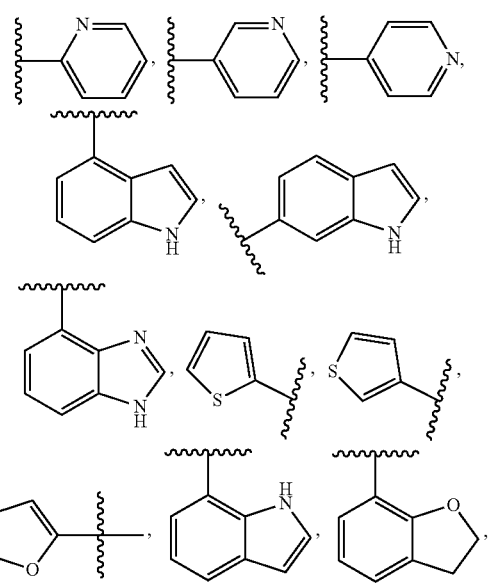

-continued
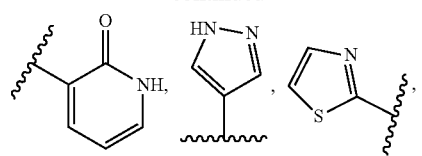
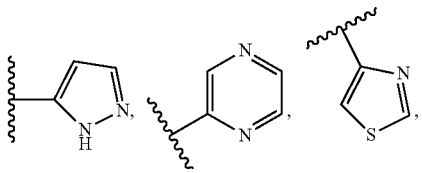
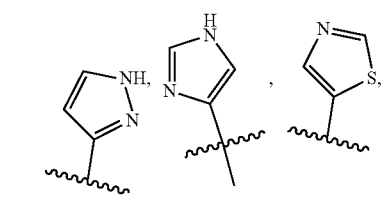
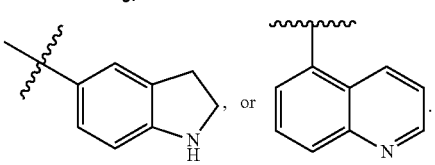
In some embodiments, ring C is phenyl, indole, cycloalkyl, pyridyl, tetrahydro-2H-pyran, azepane, tetrahydrofuran, pyrrolidine, naphthalene, piperidine, azetidine, or dihydroindene.
In some embodiments, ring C is a group represented by the corresponding moieties shown in the compounds of Table 1. For example, ring C is
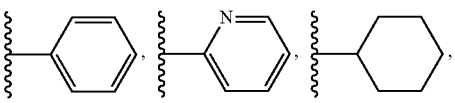
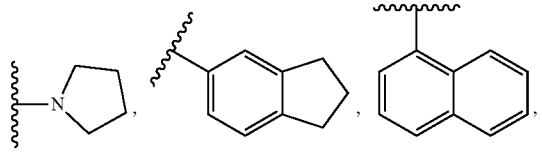
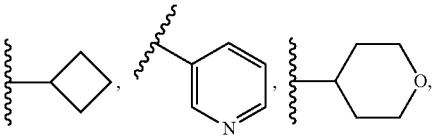
-continued
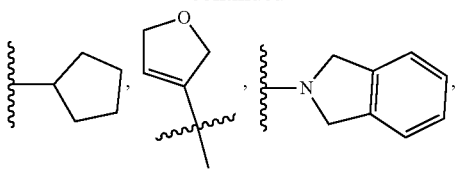
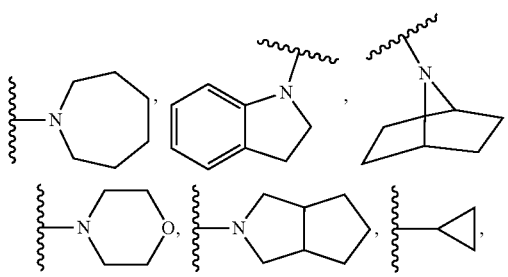
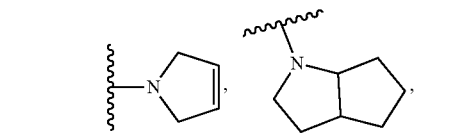
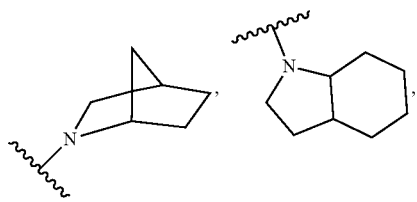
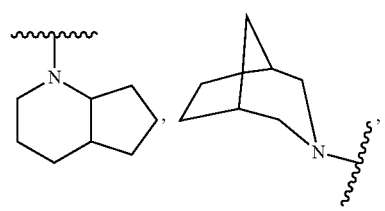
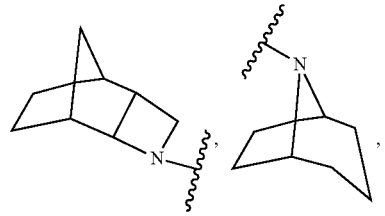
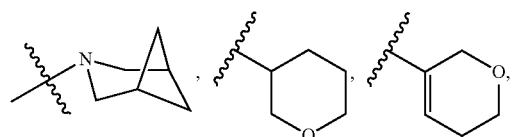
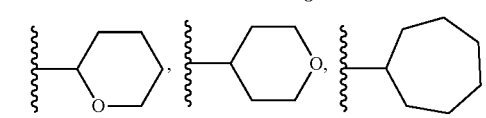
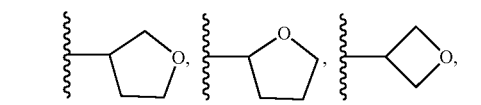
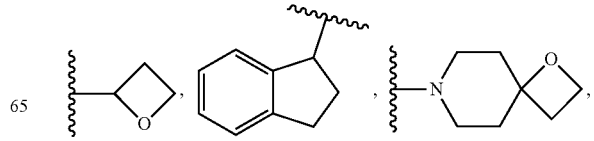

-continued

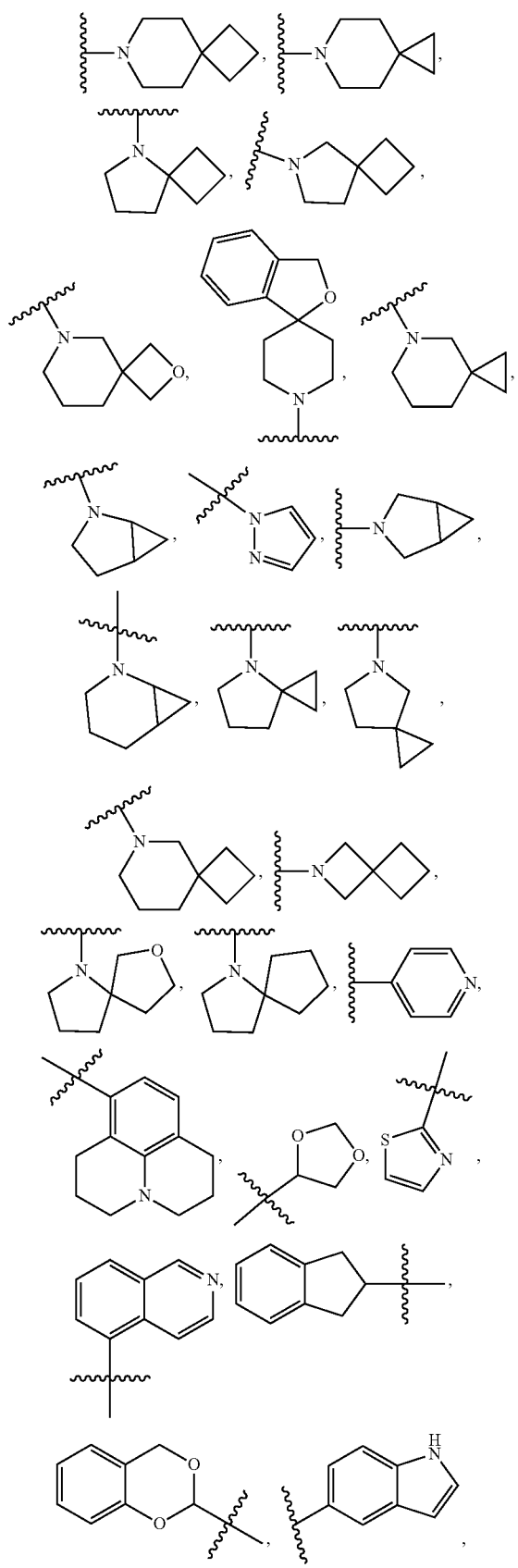

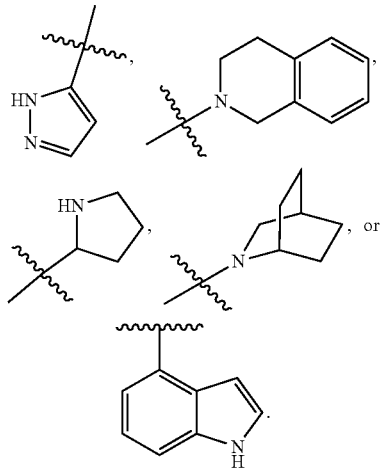

In some embodiments, X is O. In some embodiments, X is NR. In some embodiments, X is NH.

In some embodiments, Y is O. In some embodiments, Y is CH₂. In some embodiments, Y is CH(C1-C6 alkyl). In some embodiments, Y is CH(CH₃). In some embodiments, Y is CH(CH₂CH₃). In some embodiments, Y is NR, such as NH, N(C1-C6alkynyl), or N(C1-C6 alkyl).

In some embodiments, R₁ is halo, CN, C1-C6 alkyl, C1-C6 alkoxy, C3-C8 cycloalkyl, or a phenyl, pyridyl, pyrimidine, indole, aza-indole, azetidine, pyrazole, or thiophene ring, or a (C1-C9 alkylene)-R₄ wherein up to four CH₂ units are independently replaced with O, CO, S, SO, SO₂ or NR, wherein all rings are optionally substituted with one or more groups selected from halo, C1-C6 alkyl, C1-C6 alkoxy, C1-C6 fluoroalkyl, C1-C6 fluoroalkoxy, OH, CH₂OH, CH₂OCH₃, CN, CO₂H, amino, amido, C3-C10 heteroaryl, and C3-C10 heterocycloalkyl.

In some embodiments, R₁ is a group represented by the corresponding moieties shown in the compounds of Table 1. For example, R₁ is CH₃, Cl, F, CN, OCH₃, CF₃, CH₂CH₃, tBu, CH(CH₃)₂, OCH₂CH₂OCH₂CH₃,

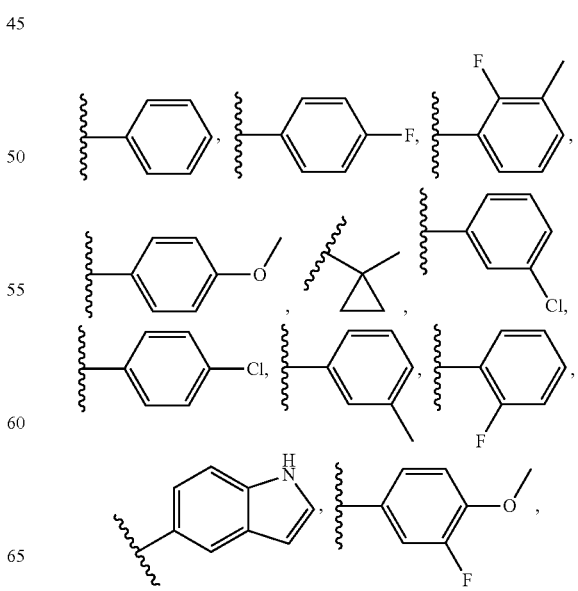

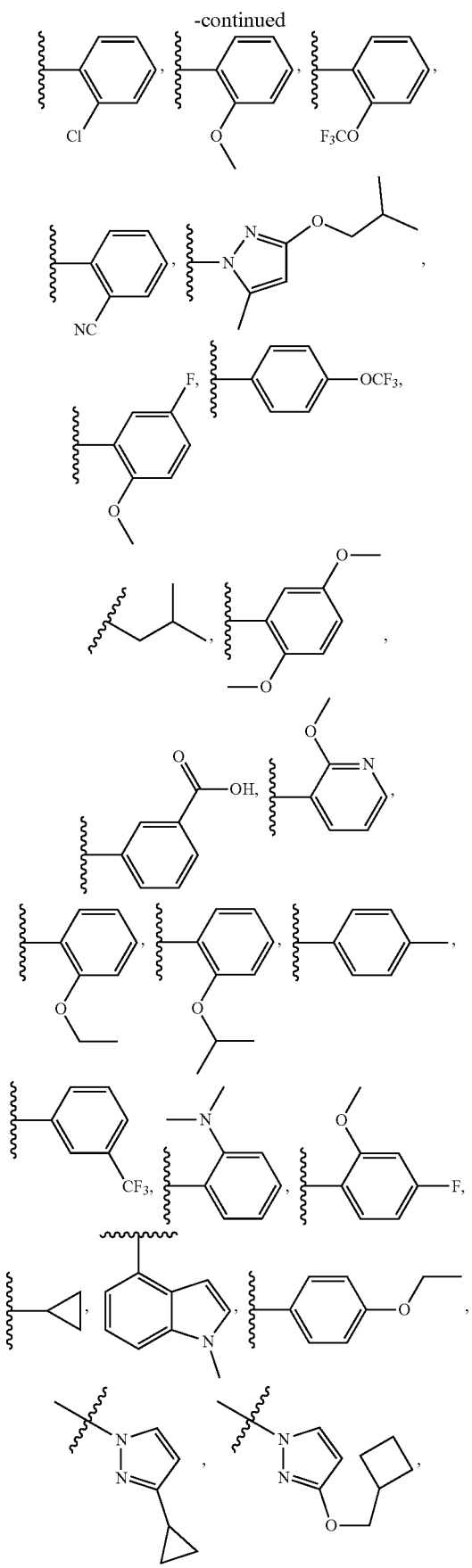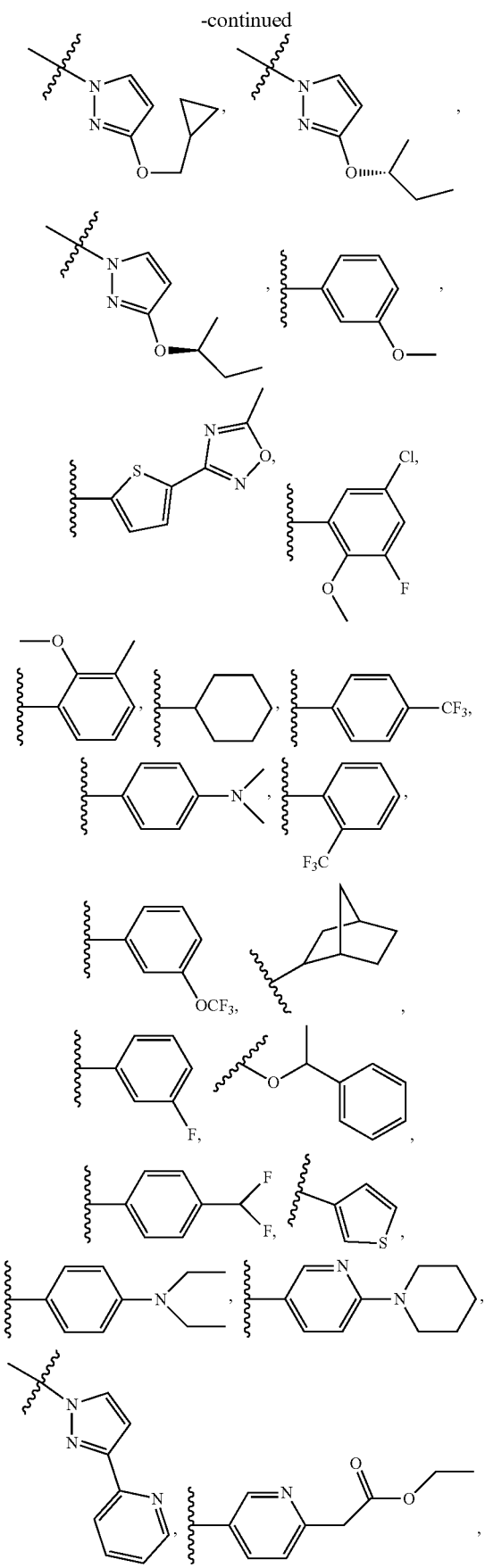

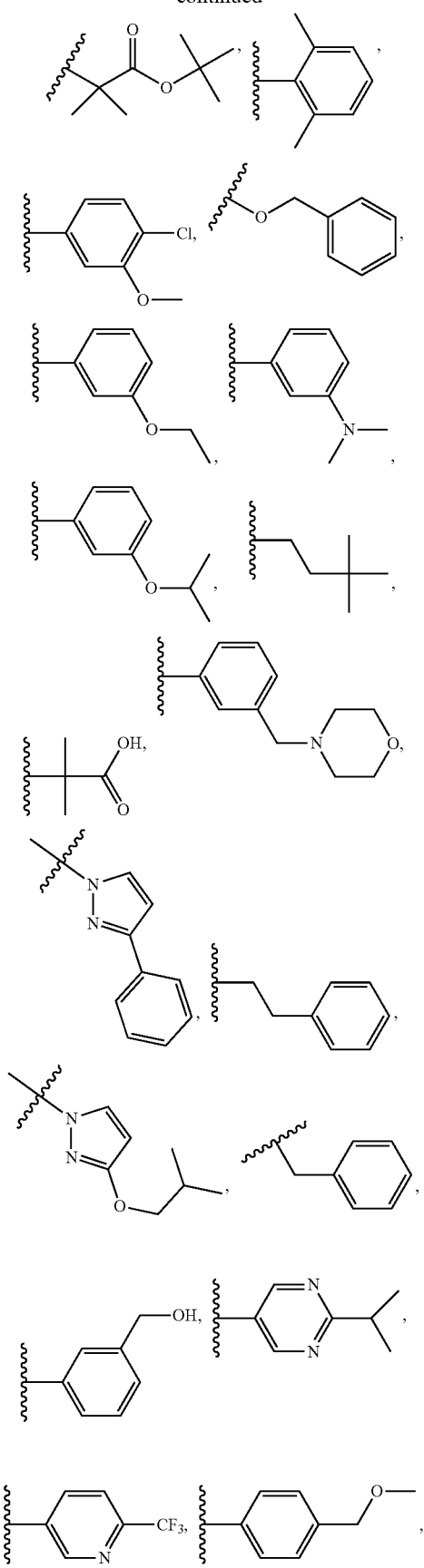
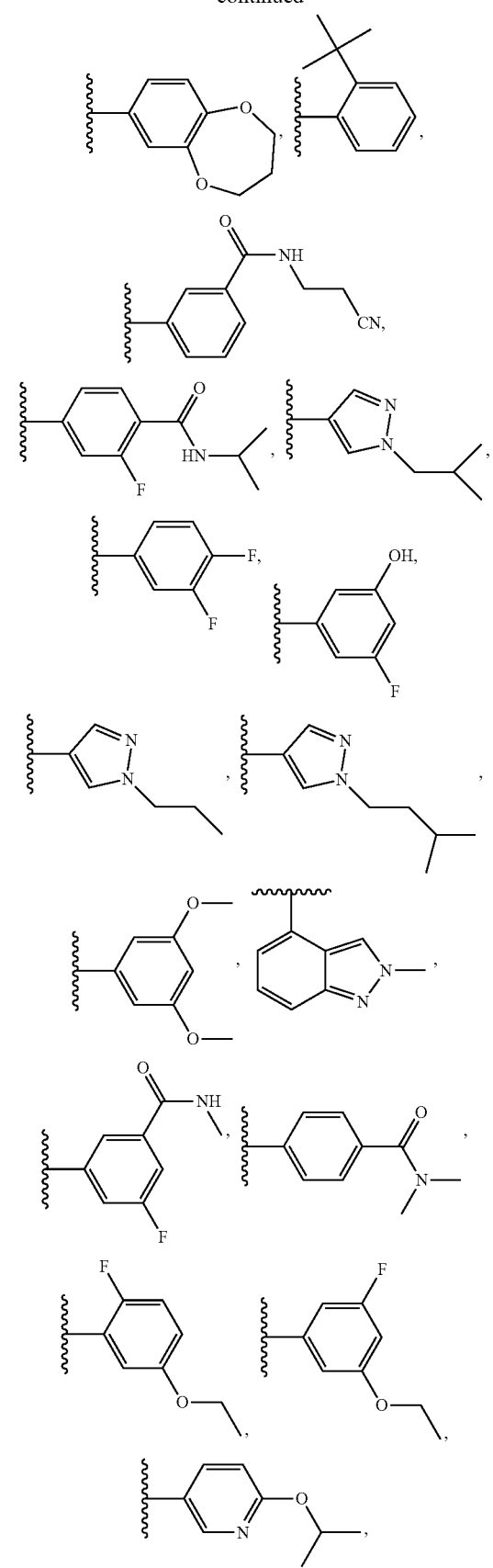

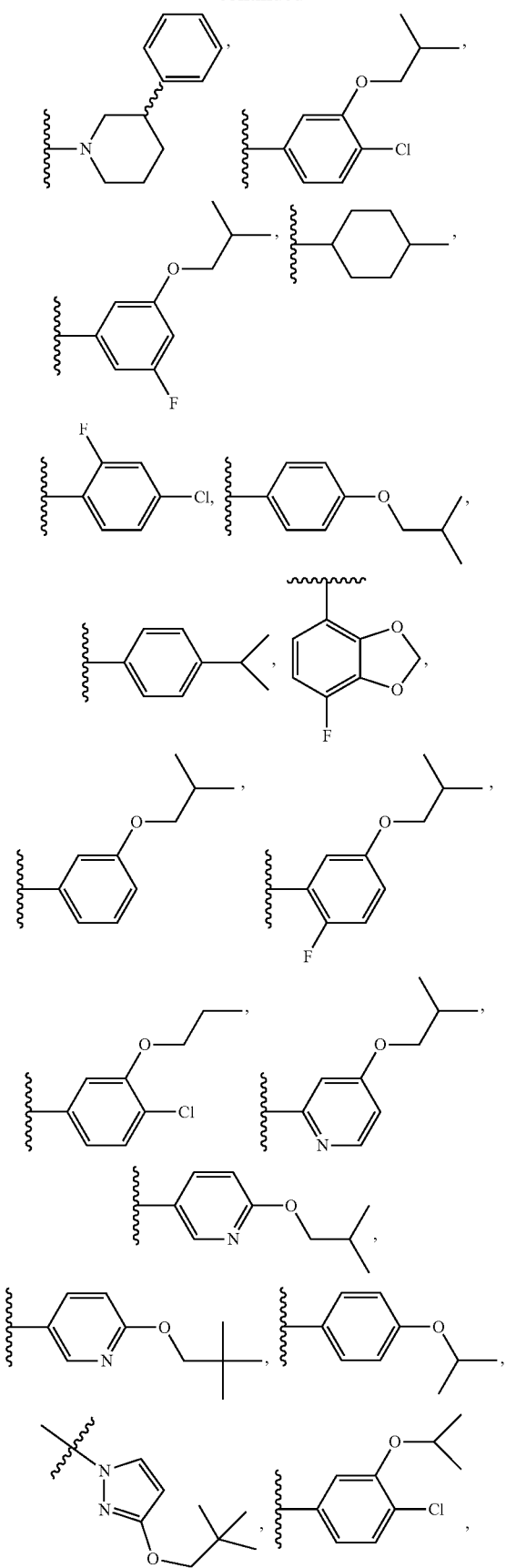
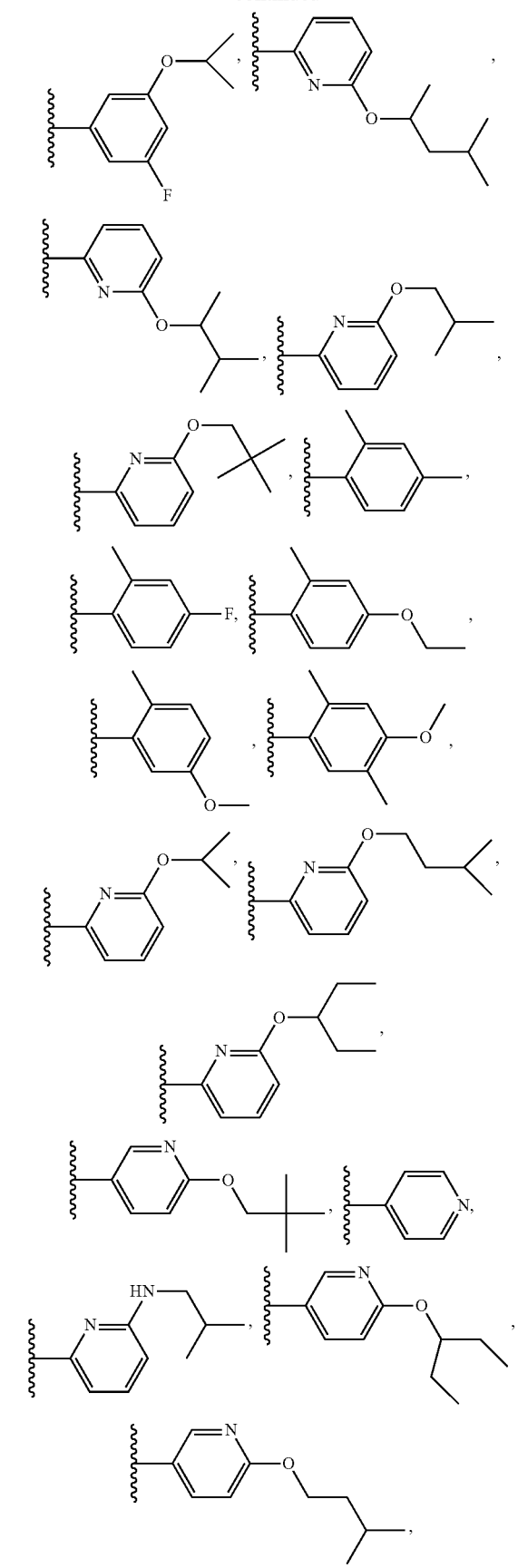

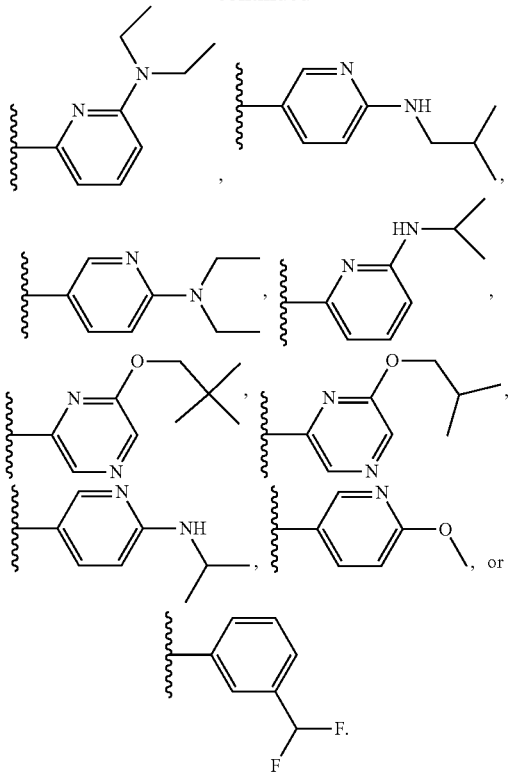

In some embodiments, $R_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are optionally O, S, N, or NR; and a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)$ $(CH_2CH_2CH_3)$, $OCH(CH_3)_2$, $NH(CH_2)_2O(CH_2)_2CH_3$, $C(O)$ $CH_3$, $CH_2CH_2OH$, $CH_2NH_2$, $NH(CH_2)_2OH$, $N(CH_3)$ $CH_2CH_2CH_2OCH_3$, $NHCH_2CH_2COOH$, $NH(CH_2)_2N$ $(CH_3)_2$, $NH(CH_2)_2NH_2$, $NH(CH_2)_3NH_2$, $NH(CH_2)_2OCH_3$, $NHCH(CH_3)_2$,

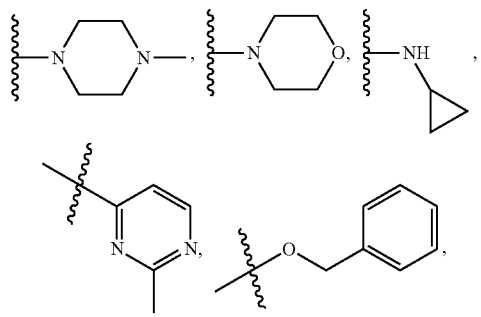

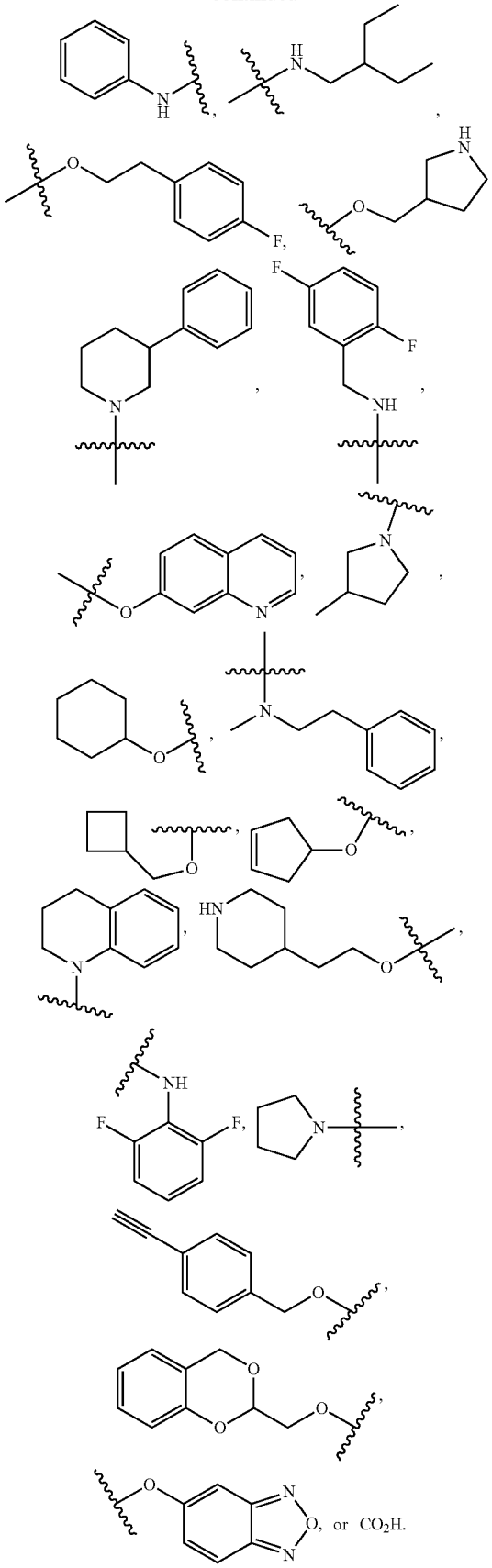

, or $CO_2H$.

In some embodiments, R₃ is halo, CN, C1-C6 alkyl or fluoroalkyl, C1-C6 alkoxy, C6-C10 aryl, or C3-C10 heteroaryl or heterocycloalkyl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

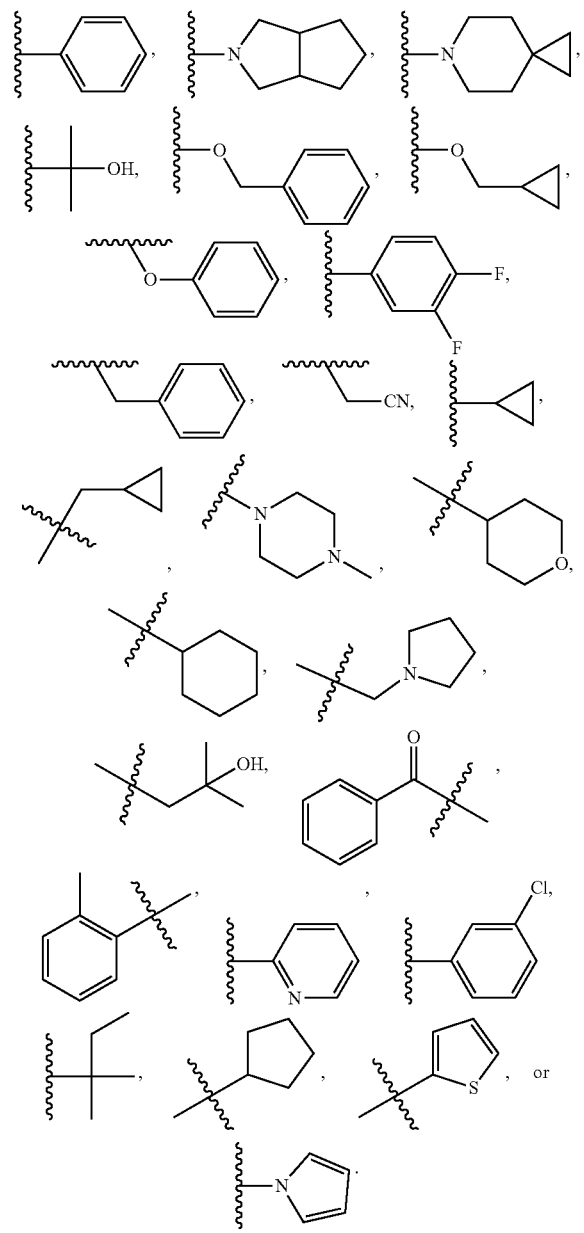

In some embodiments, o is 0. In some embodiments, o is 1. In some embodiments, o is 2.
In some embodiments, n is 0. In some embodiments, n is 1. In some embodiments, n is 2.
In some embodiments, p is 0. In some embodiments, p is 1. In some embodiments, p is 2.

In some embodiments, the compound of formula I is a compound of formula I-ii:

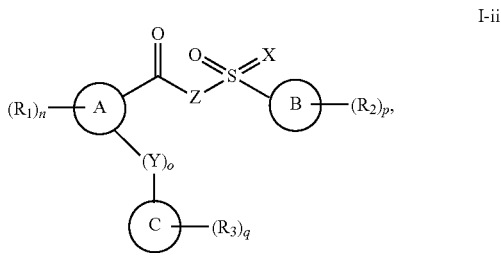

or a pharmaceutically acceptable salt thereof, wherein, independently for each occurrence:
Ring A is a C3-C14 heteroaryl or heterocyclic ring wherein anywhere from 1 to 4 ring atoms are independently O, S, N, or NR;
Ring B is a C6-C10 aryl ring;
Ring C is a C6-C10 aryl ring, C3-C14 heteroaryl or heterocyclic ring wherein anywhere from 1 to 4 ring atoms are optionally N, O, or S, or a C3-C10 cycloalkyl ring;
X is O or NR;
Y is CRR, CO, O, S, SO, SO₂, S(O)NH or NR;
Z is NR or CHR;
R₁ is halo; CN; F₃S; SiR₃; OH; NRR; C1-C6 alkyl or fluoroalkyl; C1-C6 alkoxy or fluoroalkoxy; C1-C6 alkenyl; C1-C6 alkynyl; (C1-C9 alkylene)-R₄ wherein up to four CH₂ units are independently replaced with O, CO, S, SO, SO₂ or NR; C6-C10 aryl; C3-C10 heteroaryl or heterocyclic ring wherein anywhere from 1 to 4 ring atoms are independently O, S, N, or NR; or C3-C10 cycloalkyl;
R₂ is halo; OH; NRR; azide; CN; CO₂R; C1-C6 alkyl or fluoroalkyl; CL-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₂ groups taken together may form a =CH₂ or =O group;
R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₃ groups taken together may form a =CH₂ or =O group;
R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;
R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl; n is 0, 1, 2 or 3;
o is 0, 1, 2, 3, 4, or 5;
p is 0, 1, 2, or 3; and
q is 0, 1, 2, 3, 4, or 5;

provided that the moieties containing ring B and ring C are substituted at adjacent positions on ring A.

In some embodiments, the compound of formula I-ii exists as a pharmaceutically acceptable prodrug.

In some embodiments, ring A is a pyridyl, indole, indoline, isoindoline, pyrazole, pyrimidine, quinoline, 5,6,7,8-tetrahydroquinoline, 1,2,3,4-tetrahydroisoquinoline, pyrrolodine, aza-indole, pyrrole, oxazole, pyrazine, triazole, indazole, or imidazole ring.

In some embodiments, ring A is a group represented by the corresponding moieties shown in the compounds of Table 1. For example, ring A is

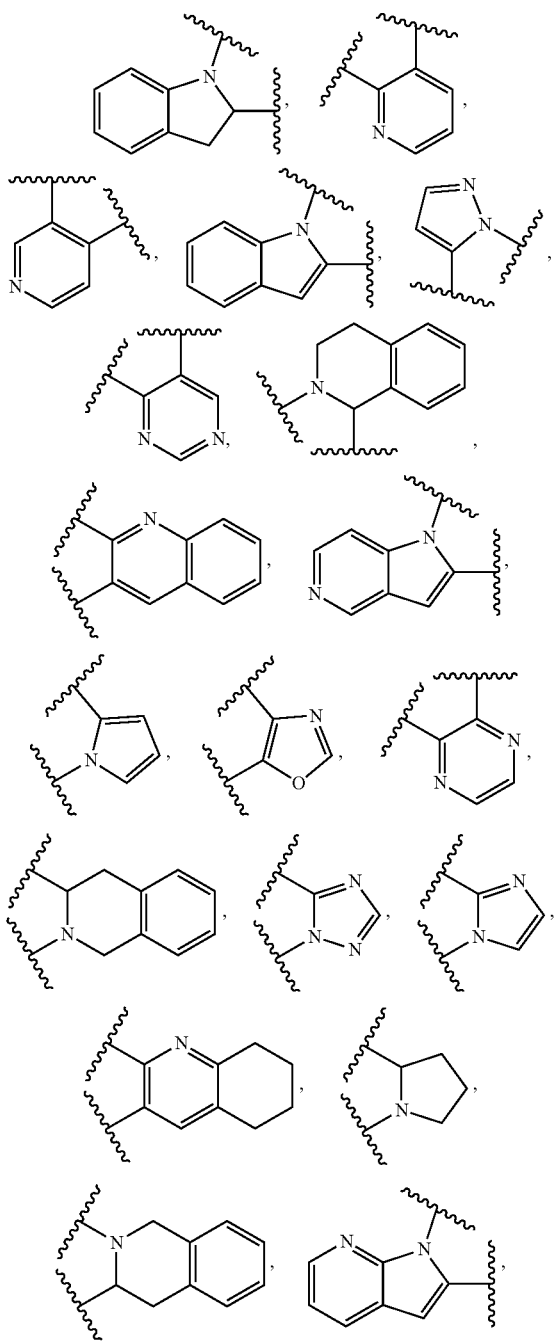

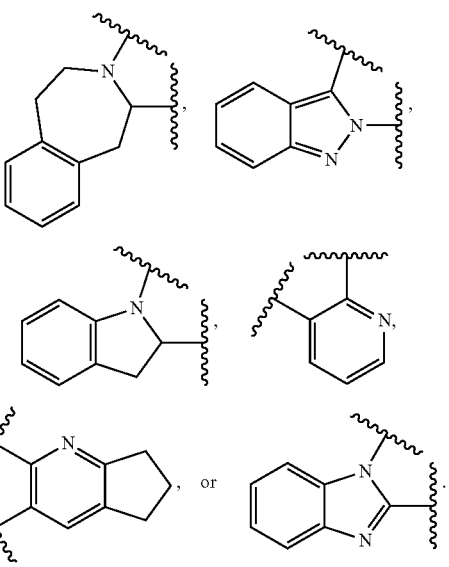

In some embodiments, ring B is phenyl or naphthalene.

In some embodiments, ring C is phenyl, indole, cycloalkyl, pyridyl, pyrrolidine, naphthalene, piperidine, azetidine, or dihydroindene.

In some embodiments, ring C is a group represented by the corresponding moieties shown in the compounds of Table 1. For example, ring C is

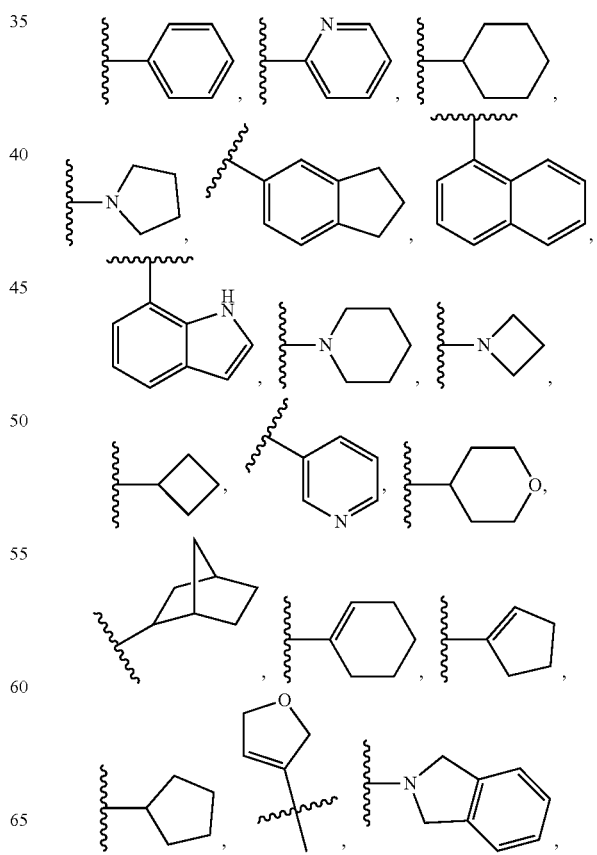

-continued
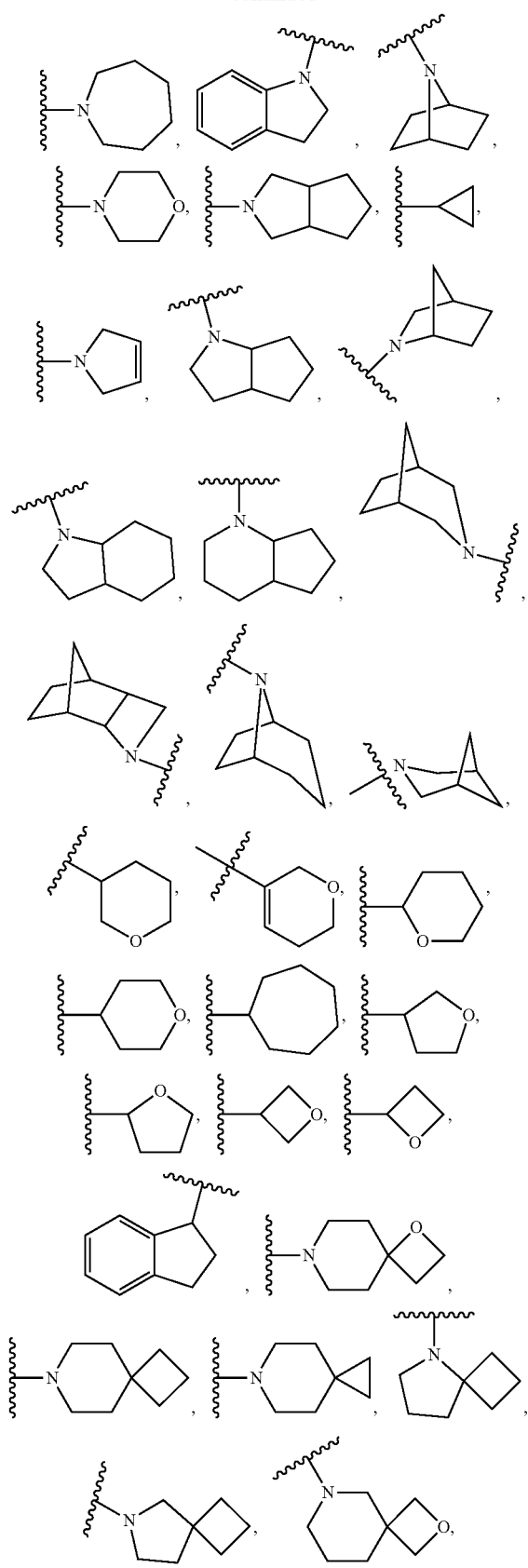
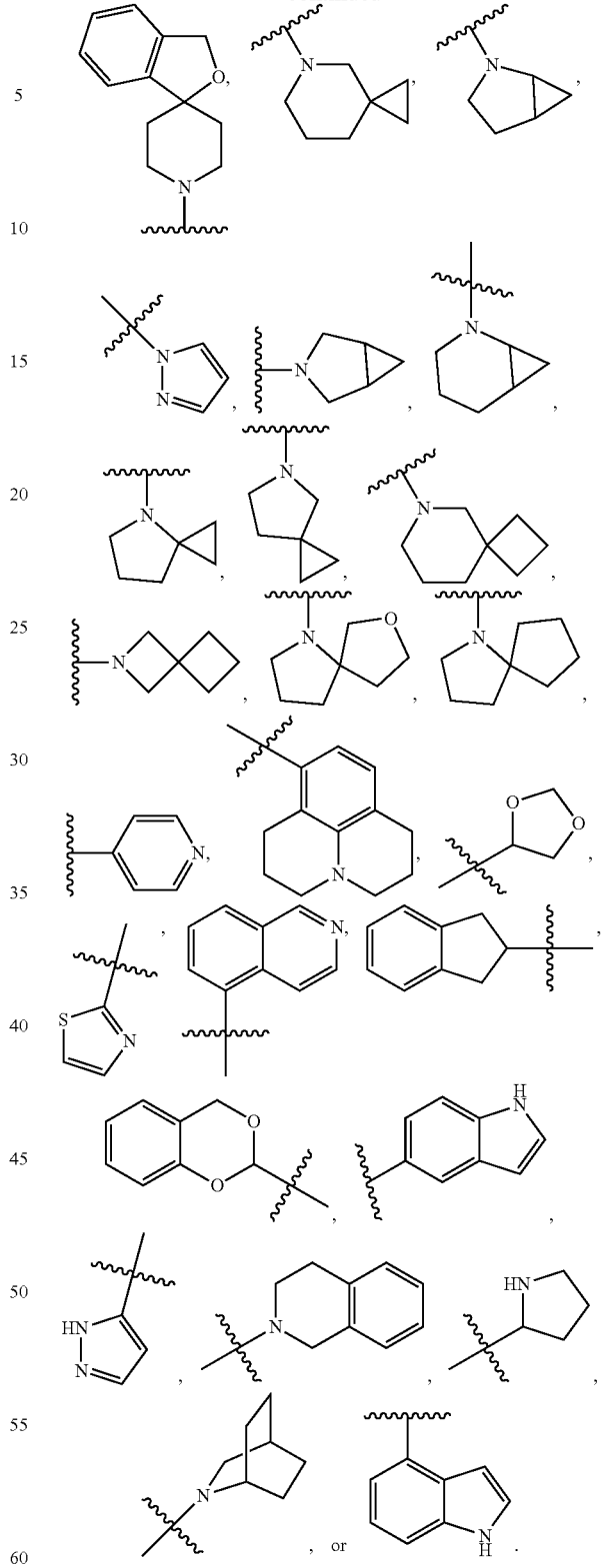
In some embodiments, X is O. In another embodiment, X is NR. In some embodiments, X is NH.
In some embodiments, Y is O. In some embodiments, Y is $CH_2$. In some embodiments, Y is CH(C1-C6 alkyl). In some embodiments, Y is $CH(CH_3)$. In some embodiments, Y is CH(CH$_2$CH$_3$). In some embodiments, Y is NR, such as NH, N(C1-C6 alkynyl), or N(C1-C6 alkyl).

In some embodiments, R$_1$ is halo, CN, C1-C6 alkyl, C1-C6 alkoxy, C3-C8 cycloalkyl, or a phenyl, pyridyl, pyrimidine, indole, aza-indole, azetidine, pyrazole, or thiophene ring, or a (C1-C9 alkylene)-R$_4$ wherein up to four CH$_2$ units are independently replaced with O, CO, S, SO, SO$_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, CH$_2$OH, CH$_2$OCH$_3$, CN, CO$_2$H, amino, amido, C3-C10 heteroaryl, and C3-C10 heterocycloalkyl.

In some embodiments, R$_1$ is a group represented by the corresponding moieties shown in the compounds of Table 1. For example, R$_1$ is CH$_3$, Cl, F, CN, OCH$_3$, CF$_3$, CH$_2$CH$_3$, tBu, CH(CH$_3$)$_2$, OCH$_2$CH$_2$OCH$_2$CH$_3$,

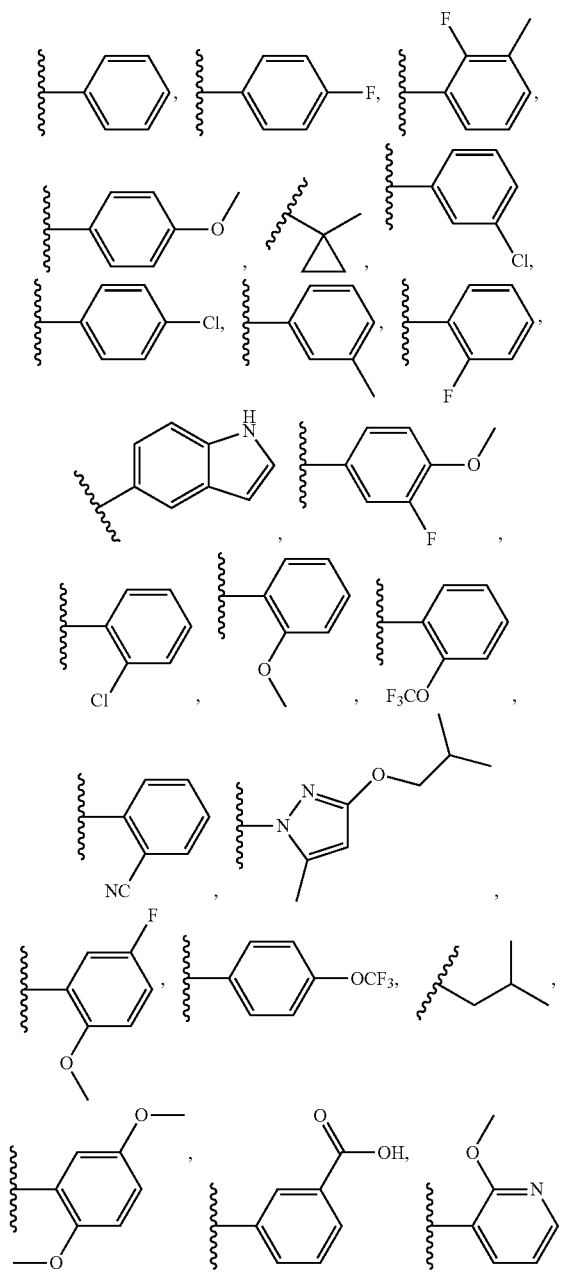

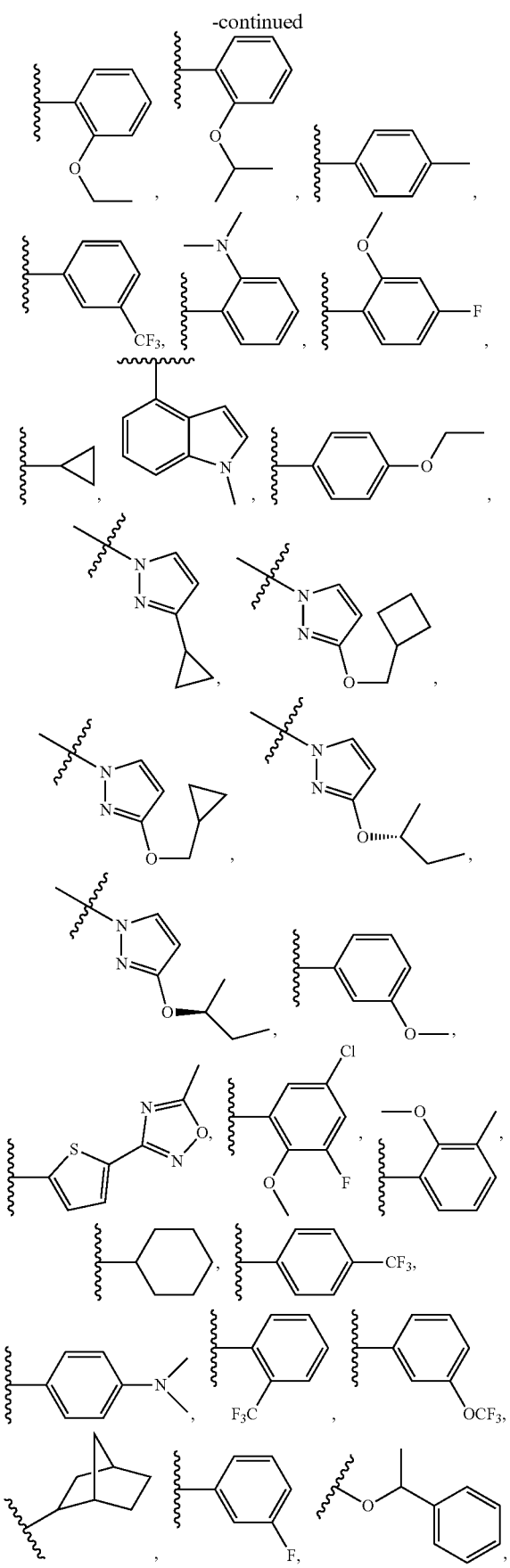

-continued
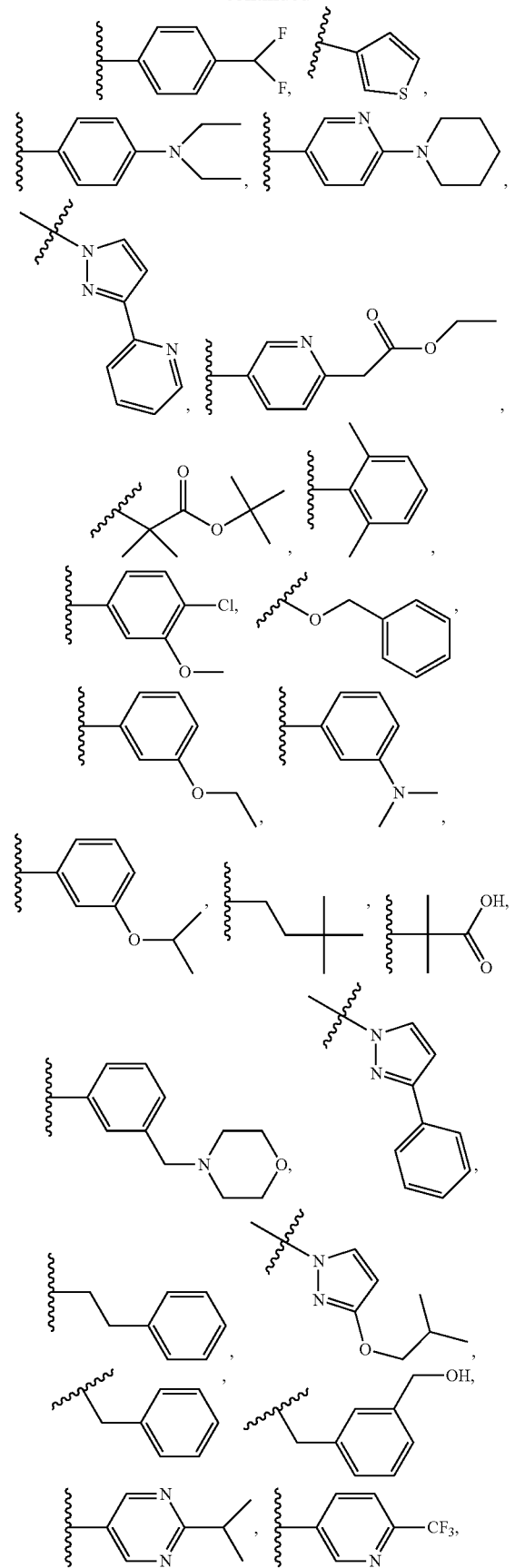
-continued
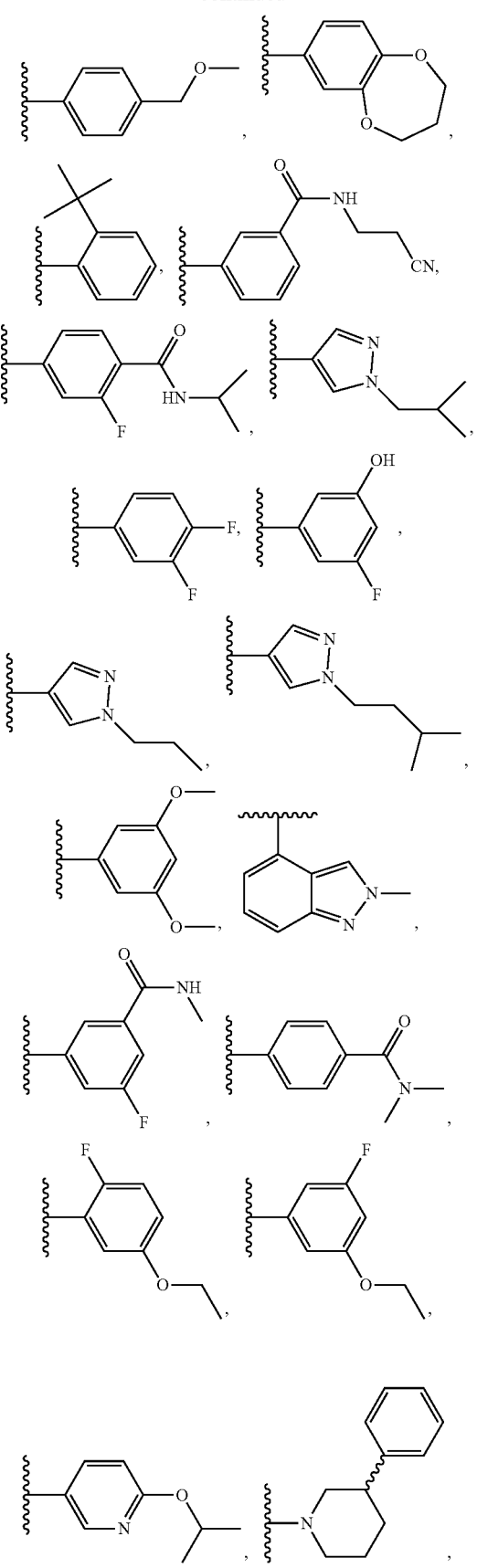

-continued
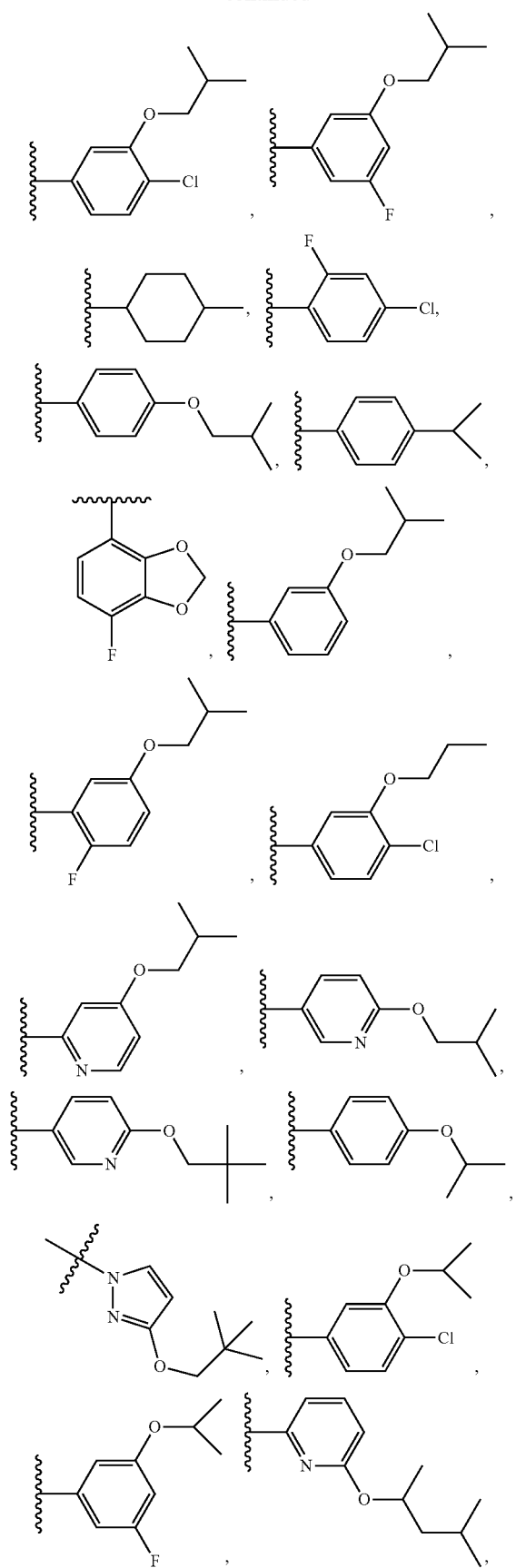
-continued
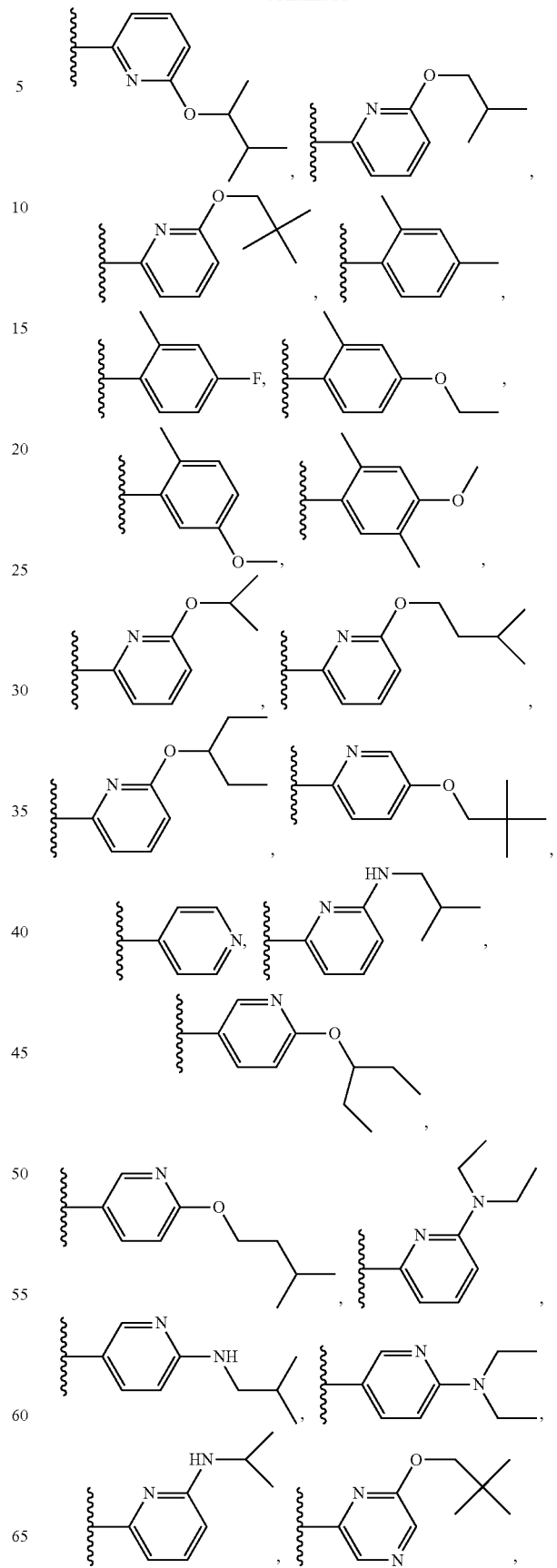

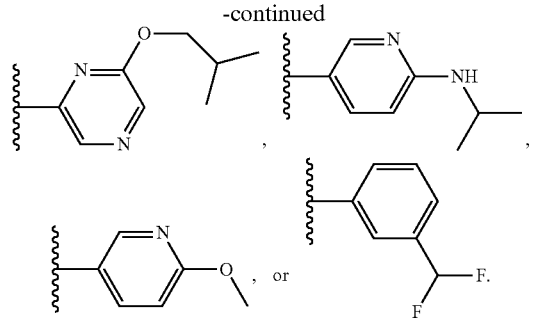

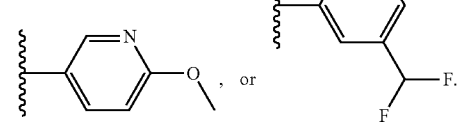

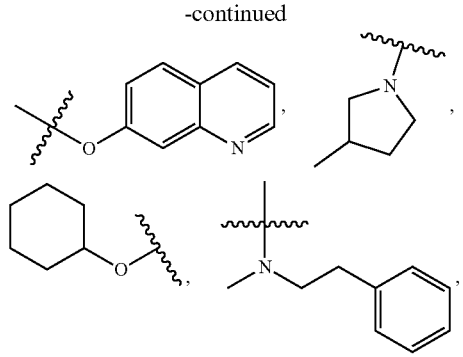

In some embodiments, R₂ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9alkylene)-R₄ wherein up to four CH₂ units are independently replaced with O, CO, S, SO, SO₂ or NR.

In some embodiments, R₂ is a group represented by the corresponding moieties shown in the compounds of Table 1. For example, R₂ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

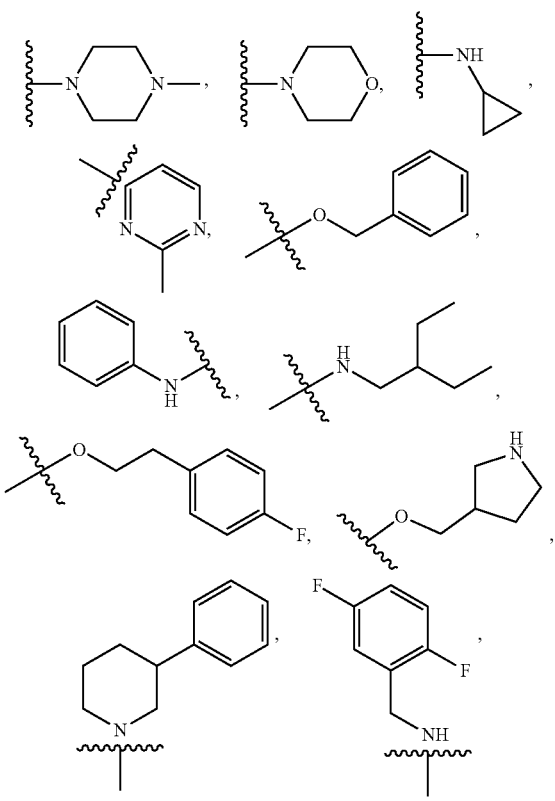

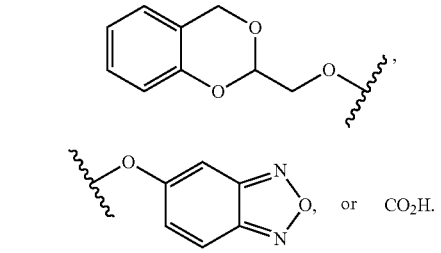

In some embodiments, R₃ is halo, CN, C1-C6 alkyl or fluoroalkyl, C1-C6 alkoxy, C6-C10 aryl, or C3-C10 heteroaryl or heterocycloalkyl wherein anywhere from 1 to 4 ring atoms are independently O, S, N, or NR.

In some embodiments, R₃ is a group represented by the corresponding moieties shown in the compounds of Table 1. R₃ is Cl, I, deuterium, F, CN, CH₃, OH, OCH₃, CF₃, CH₂CH₃; CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

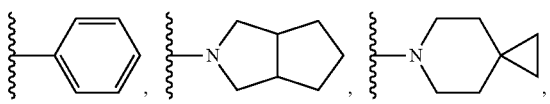

-continued

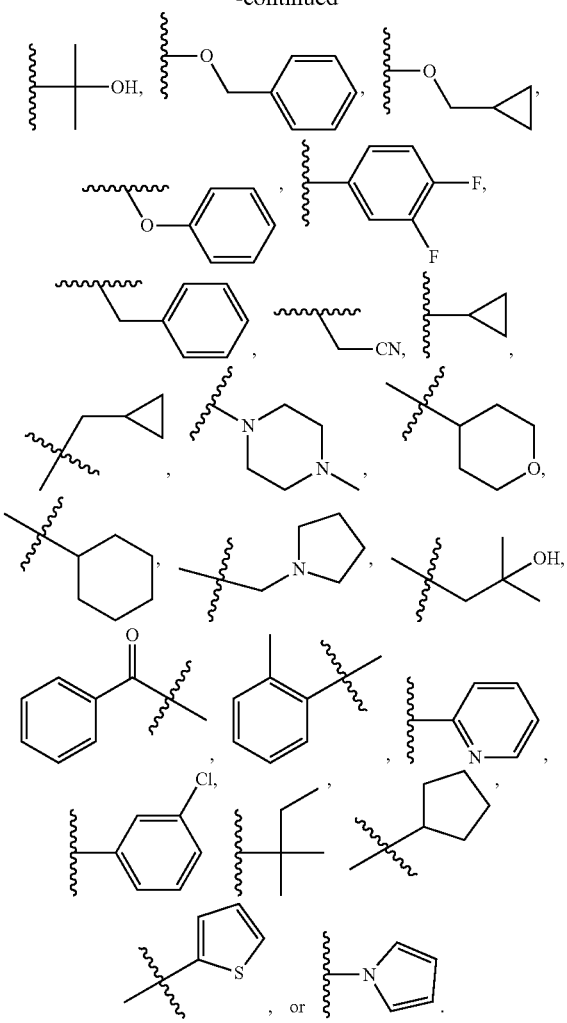

In some embodiments, o is 0. In some embodiments, o is 1. In some embodiments, o is 2.

In some embodiments, n is 0. In some embodiments, n is 1. In some embodiments, n is 2.

In some embodiments, p is 0. In some embodiments, p is 1. In some embodiments, p is 2.

In some embodiments, the invention features a compound of formula Ia:

Ia or a pharmaceutically acceptable salt thereof, wherein, independently for each occurrence:

Ring B is a C6-C10 aryl ring or C3-C10 heteroaryl or heterocyclic ring wherein anywhere from 1 to 4 ring atoms are independently O, S, N, or NR;

Ring C is a C6-C10 aryl ring, C3-C14 heteroaryl or heterocyclic ring wherein anywhere from 1 to 4 ring atoms are independently N, O, or S, or a C3-C10 cycloalkyl ring;

X is O or NR;

Y is CRR, CO, O, S, SO, $SO_2$, S(O)NH or NR;

$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a $=CH_2$ or $=O$ group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a $=CH_2$ or $=O$ group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, or 2;

o is 0, 1, 2, 3, 4, or 5;

p is 0, 1, 2, or 3; and q is 0, 1, 2, 3, 4, or 5.

In some embodiments, the compound of formula Ia exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

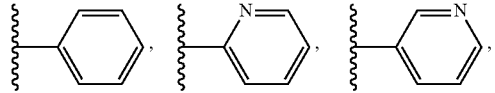

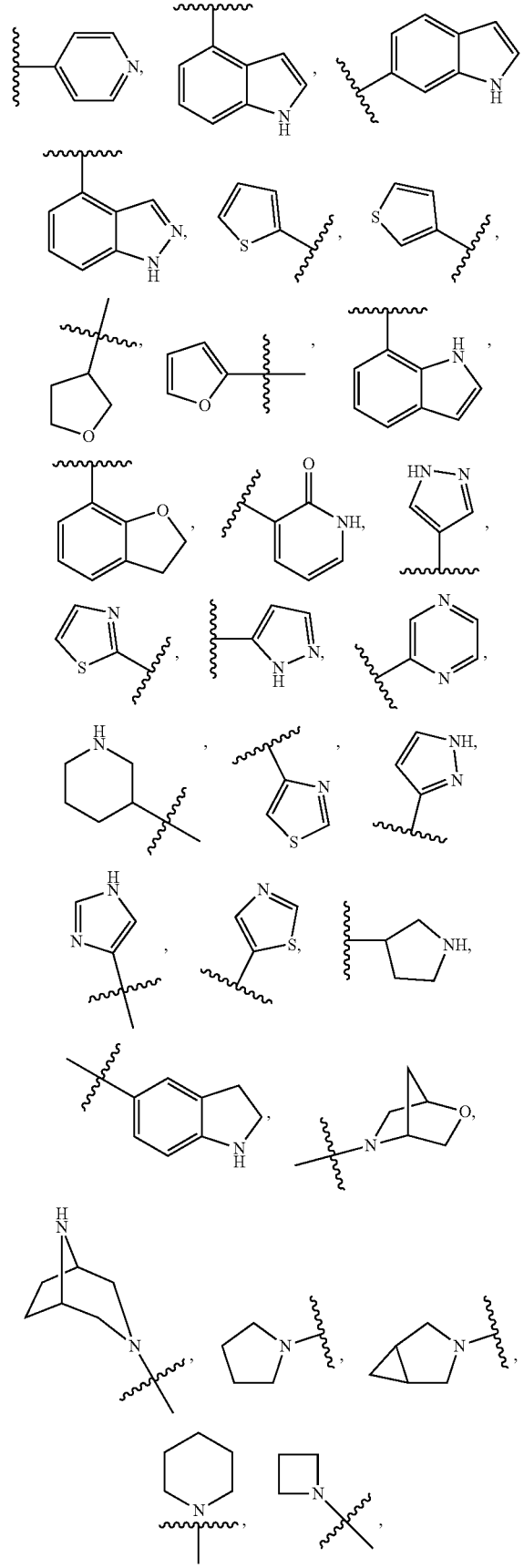
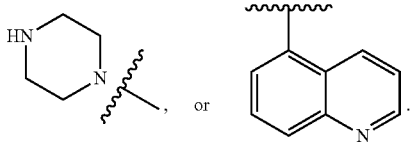
In some embodiments, ring C is phenyl, indole, cycloalkyl, pyridyl, pyrrolidine, naphthalene, piperidine, or dihydroindene.
In some embodiments, ring C is is a group represented by the corresponding moieties shown in the compounds of Table 1. For example, ring C is
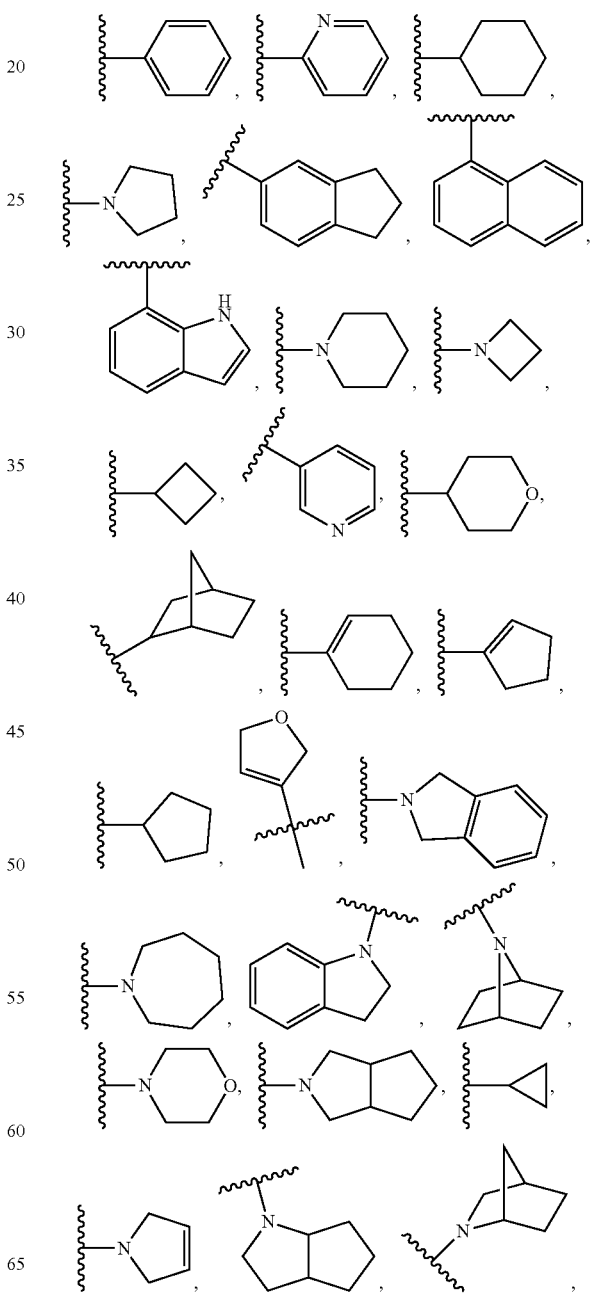

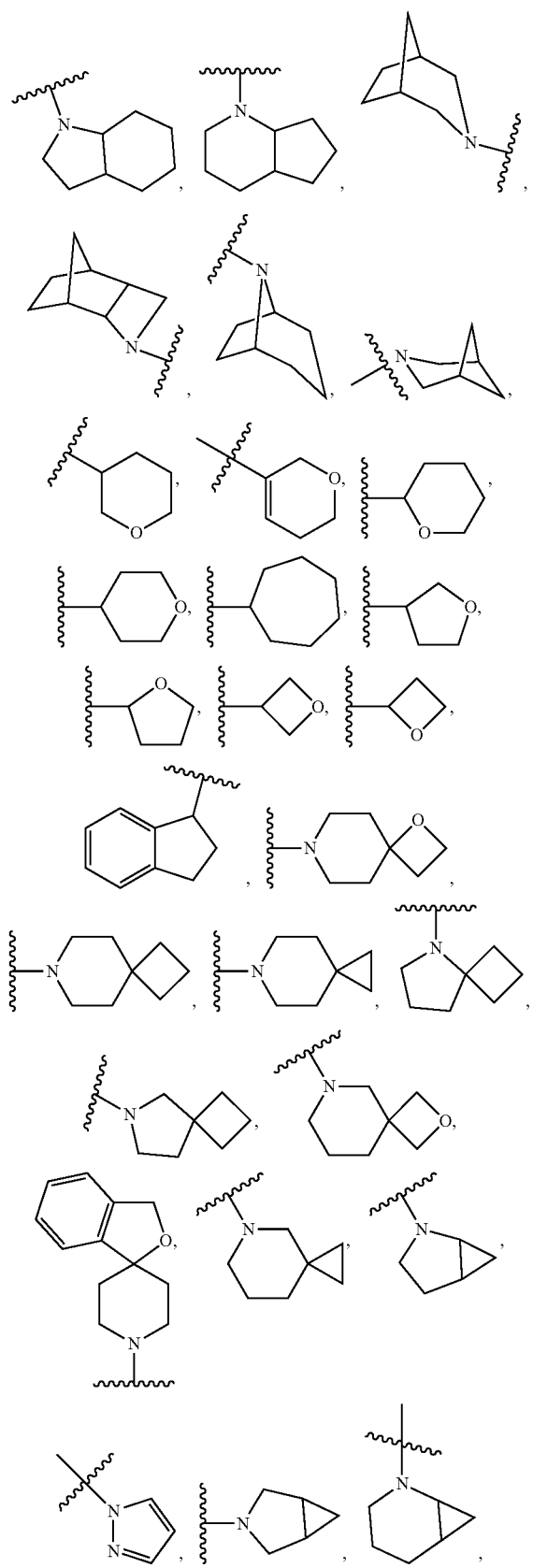

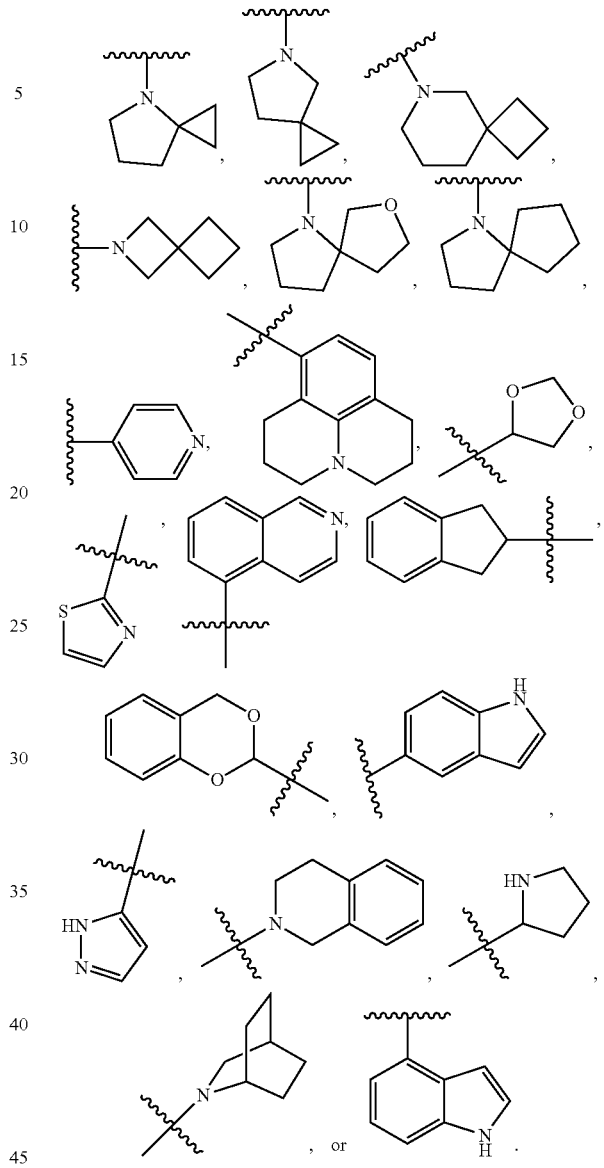

In some embodiments, Y is O. In some embodiments, Y is $CH_2$. In some embodiments, Y is $CH(C1-C6$ alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

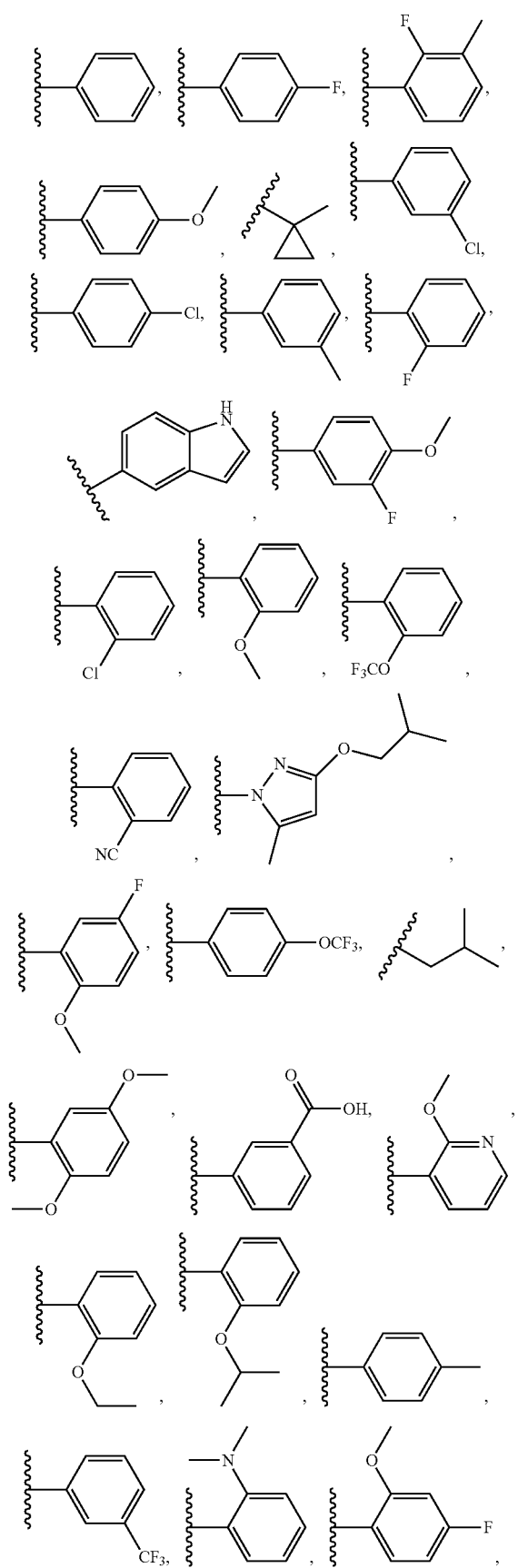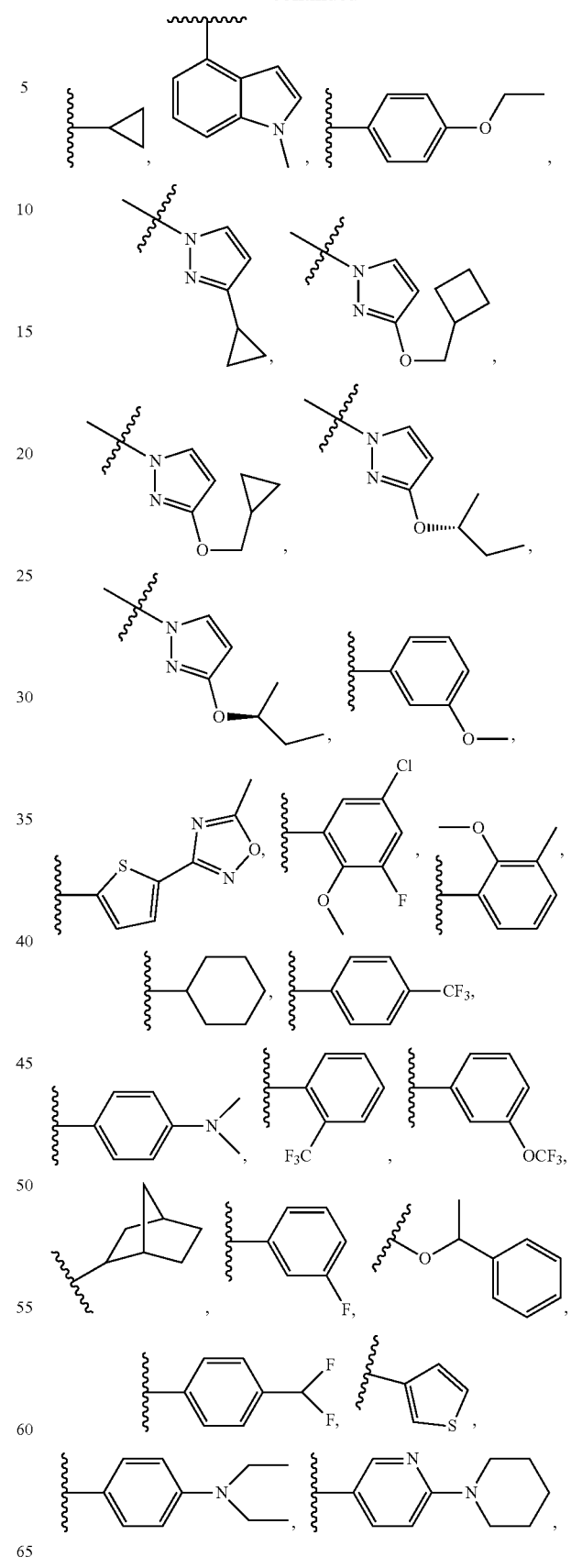

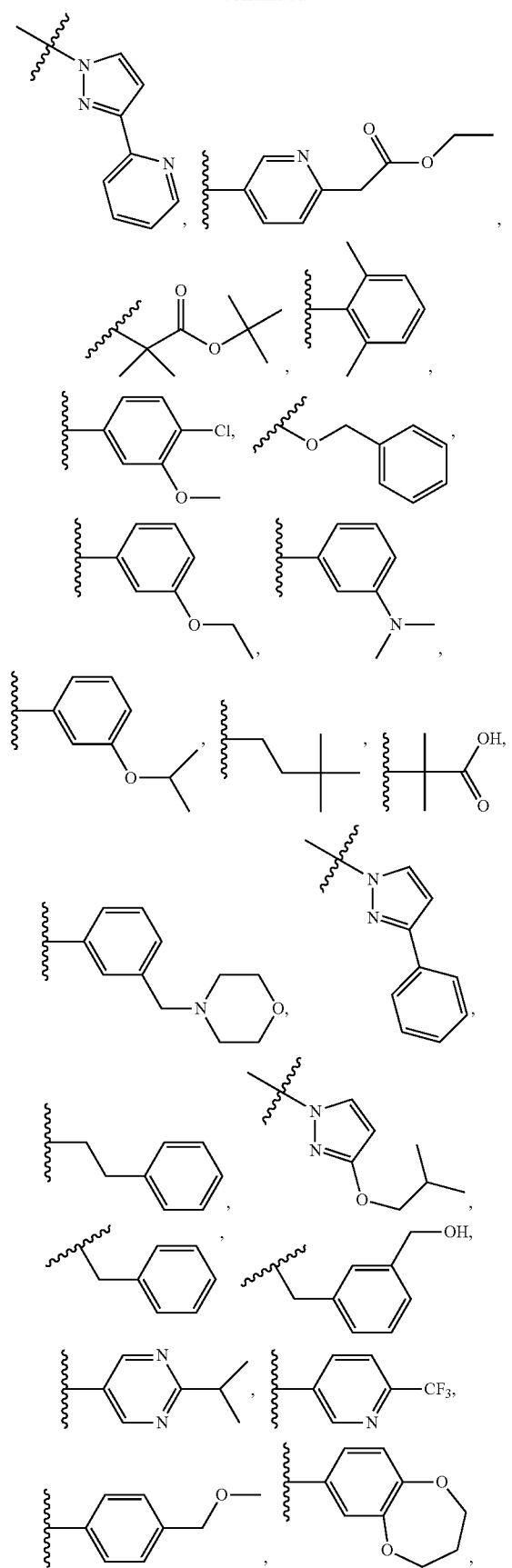
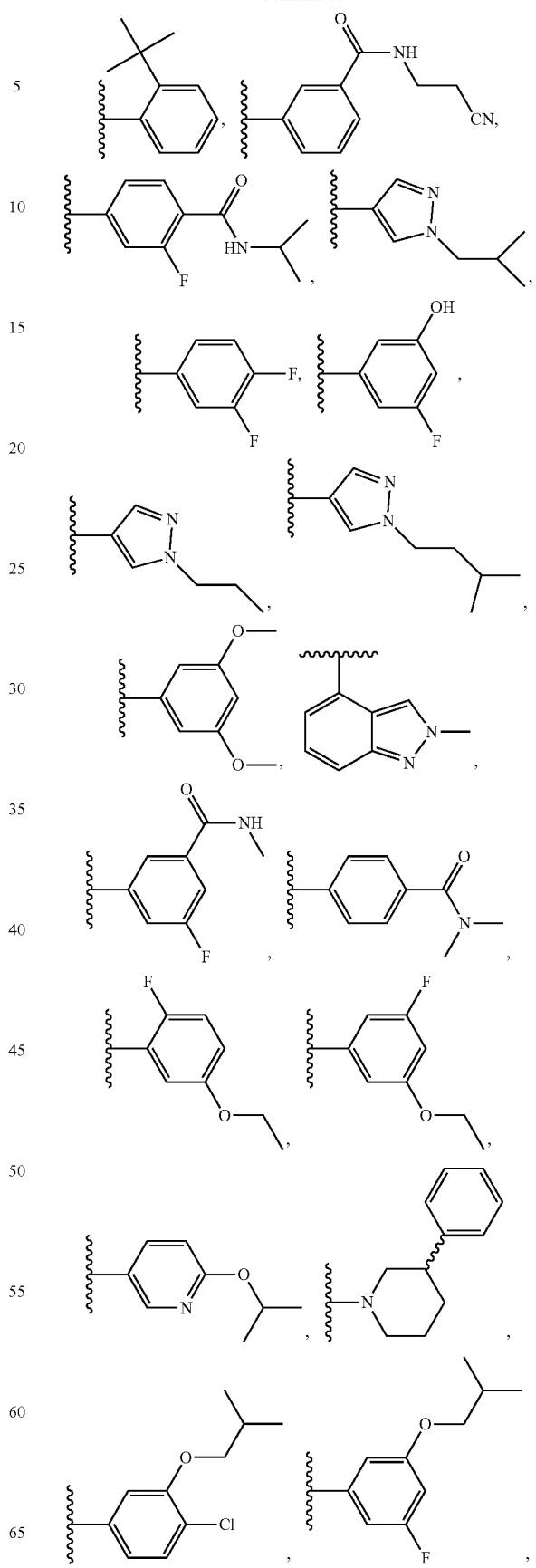

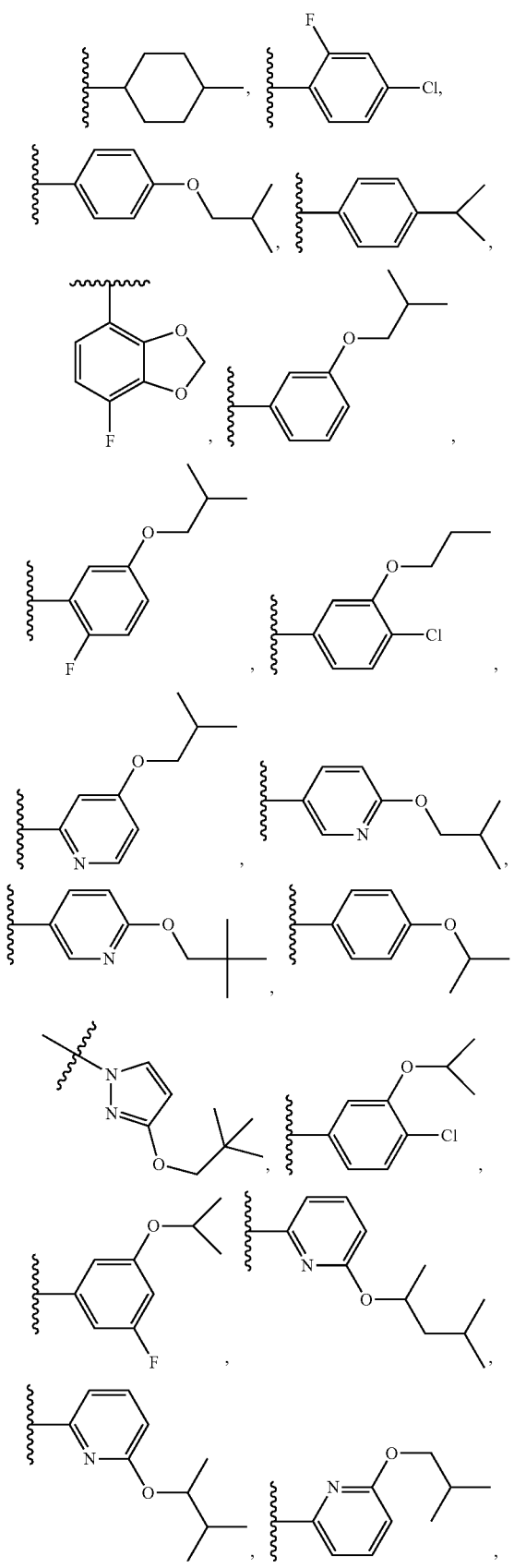
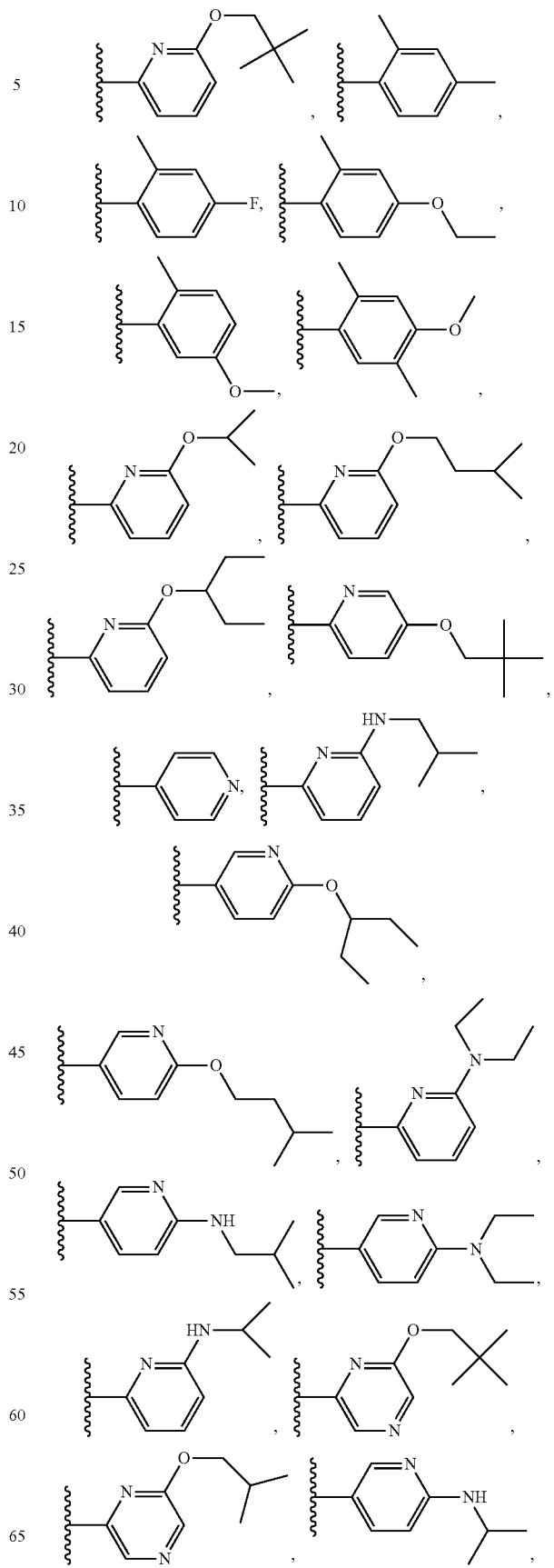

-continued

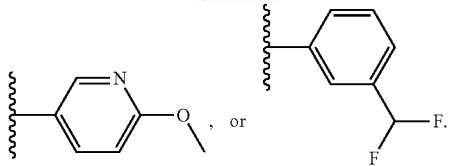, or

In some embodiments, R$_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-R$_4$ wherein up to four CH$_2$ units are independently replaced with O, CO, S, SO, SO$_2$ or NR.

In some embodiments, R$_2$ is a group represented by the corresponding moieties shown in the compounds of Table 1. For example, R$_2$ is Cl, F, OH, CN, N$_3$, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, CH$_3$, CH$_2$OH, CH$_2$CH$_3$, CH$_2$CH$_2$CH$_3$, =O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

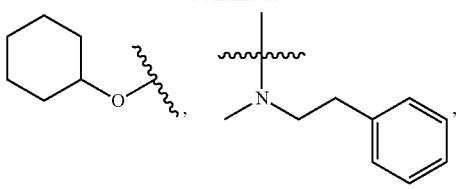

-continued

, or CO$_2$H.

In some embodiments, R$_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R$_3$ is a group represented by the corresponding moieties shown in the compounds of Table 1. For example, R$_3$ is Cl, I, deuterium, F, CN, CH$_3$, OH, OCH$_3$, CF$_3$, CH$_2$CH$_3$, CH$_2$CF$_3$, CH$_2$CH$_2$CH$_3$, OCH$_2$CH(CH$_3$)$_2$, OCH(CH$_3$)$_2$, CO$_2$H, CO$_2$NH$_2$, OCH$_2$CH$_3$, CH$_2$OCH$_3$, CH(CH$_3$)$_2$, CCH, CH$_2$CONH$_2$, CO$_2$CH$_3$, —CH$_2$N(CH$_3$)$_2$, CO$_2$tBu, tBu, =CH$_2$, =O,

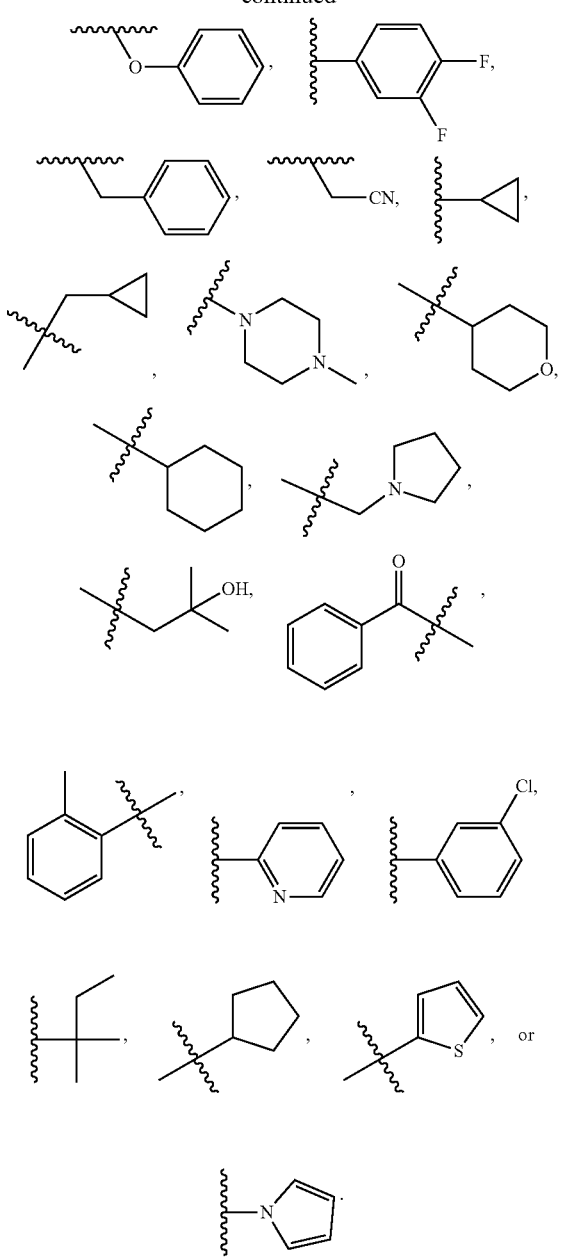

In some embodiments, o is 0. In some embodiments, o is 1. In some embodiments, o is 2.

In some embodiments, n is 0. In some embodiments, o is 1. In some embodiments, o is 2.

In some embodiments, p is 0. In some embodiments, p is 1. In some embodiments, p is 2.

In some embodiments, ring B is phenyl. In some embodiments, ring B and ring C are phenyl. In some embodiments, $R_1$ is tBu. In some embodiments, ring B and ring C are phenyl and $R_1$ is tBu. In some embodiments, Y is $CH_2$. In some embodiments, ring B and ring C are phenyl, $R_1$ is tBu, and Y is $CH_2$. In some embodiments, ring B, ring C, and $R_1$ are phenyl and Y is $CH_2$.

In some embodiments, the invention features a compound of formula Ia-i:

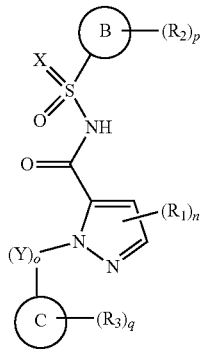

Ia-i or a pharmaceutically acceptable salt thereof, wherein, independently for each occurrence:

Ring B is a C3-C10 heteroaryl ring wherein anywhere from 1 to 4 ring atoms are independently O, S, N, or NR;

Ring C is a C6-C10 aryl ring, C3-C14 heteroaryl or heterocyclic ring wherein anywhere from 1 to 4 ring atoms are independently N, O, or S, or a C3-C10 cycloalkyl ring;

X is O or NR;

Y is CRR, CO, O, S, SO, $SO_2$, S(O)NH or NR;

$R_1$ is halo; CN; $F_3$S; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a =$CH_2$ or =O group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a =$CH_2$ or =O group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, or 2;

o is 0, 1, 2, 3, 4, or 5;

p is 0, 1, 2, or 3; and q is 0, 1, 2, 3, 4, or 5.

In some embodiments, the compound of formula Ia-i exists as a pharmaceutically acceptable prodrug.

In some embodiments, ring B is pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is,

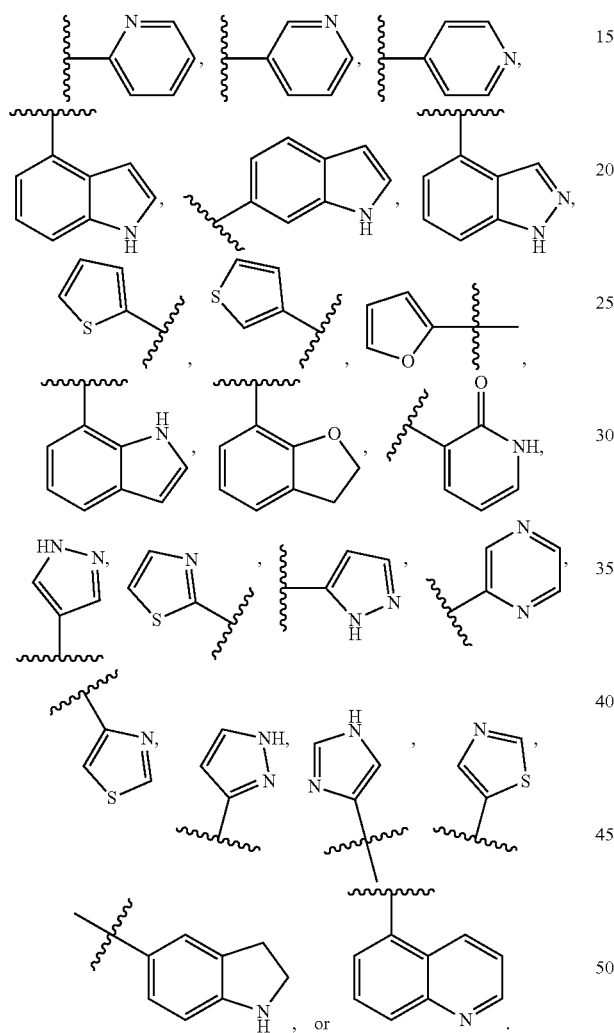

In some embodiments, ring C is phenyl, indole, cycloalkyl, pyridyl, pyrrolidine, naphthalene, piperidine, or dihydroindene.

In some embodiments, ring C is a group represented by the corresponding moieties shown in the compounds of Table 1. For example, ring C is

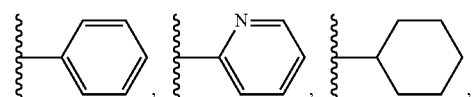

-continued

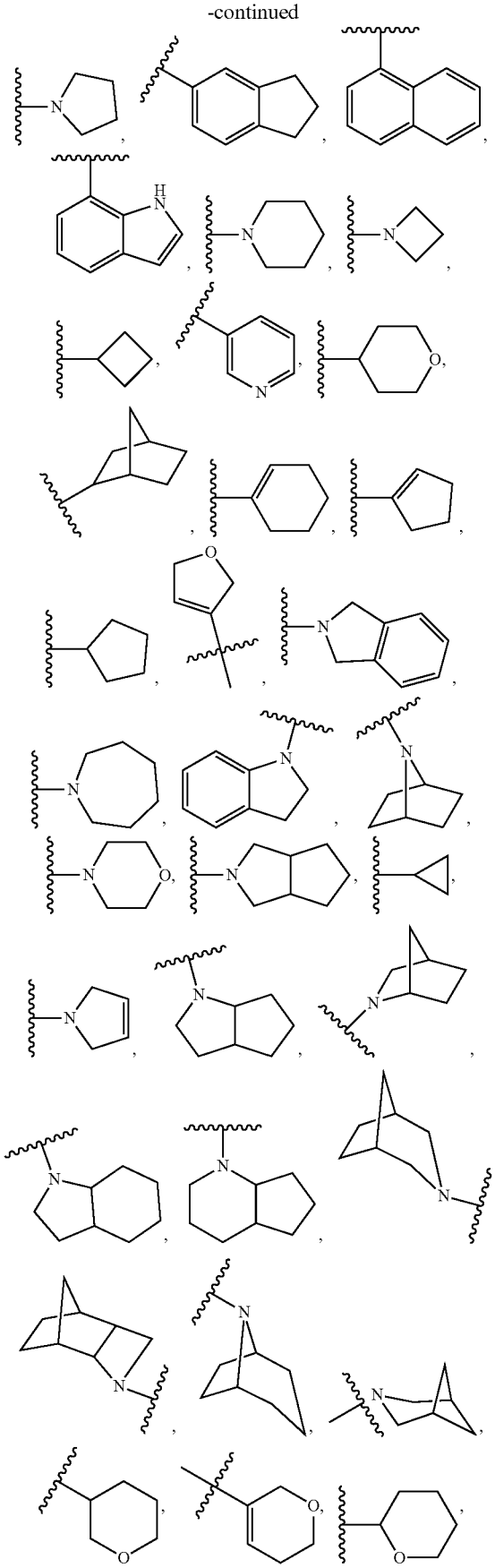

-continued

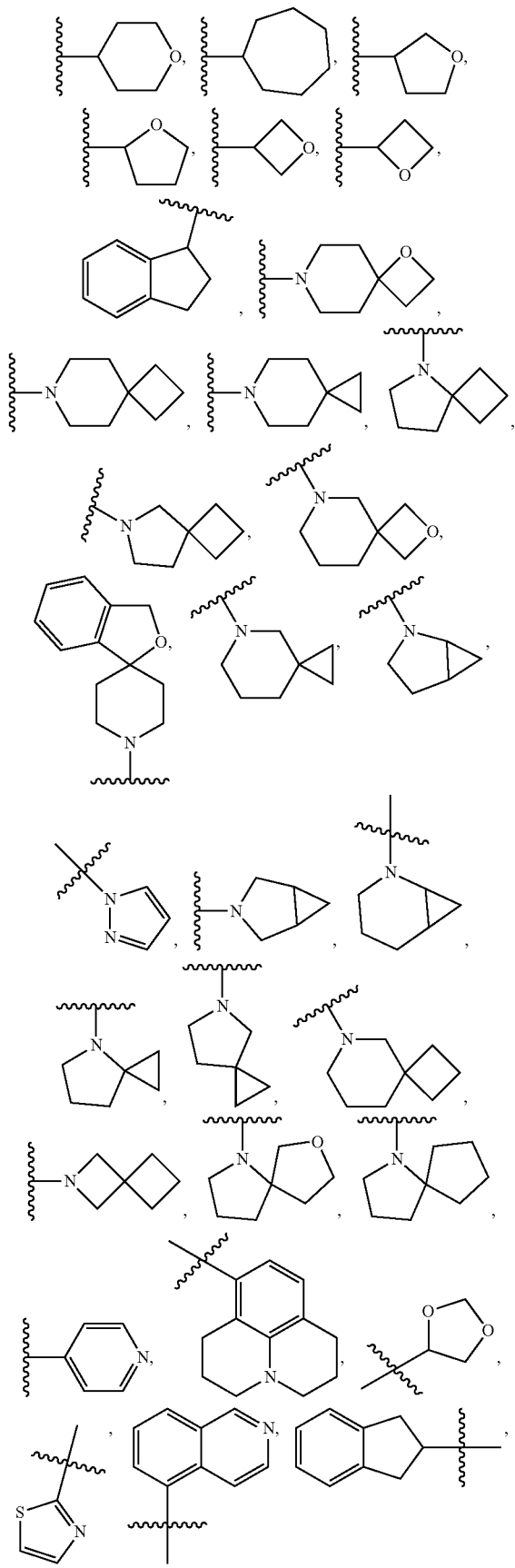

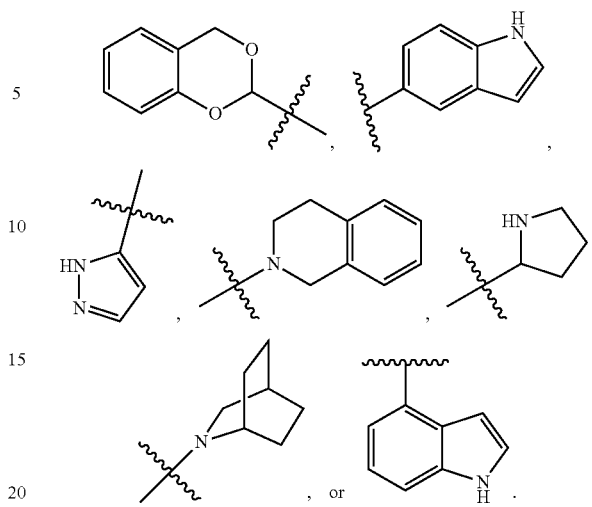

In some embodiments, Y is O. In some embodiments, Y is $CH_2$. In some embodiments, Y is $CH(C1-C6\ alkyl)$. In some embodiments, Y is $CH(CH_3)$. In some embodiments, Y is $CH(CH_2CH_3)$. In some embodiments, Y is NR, such as NH, $N(C1-C6alkynyl)$, or $N(C1-C6\ alkyl)$.

In some embodiments, R is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

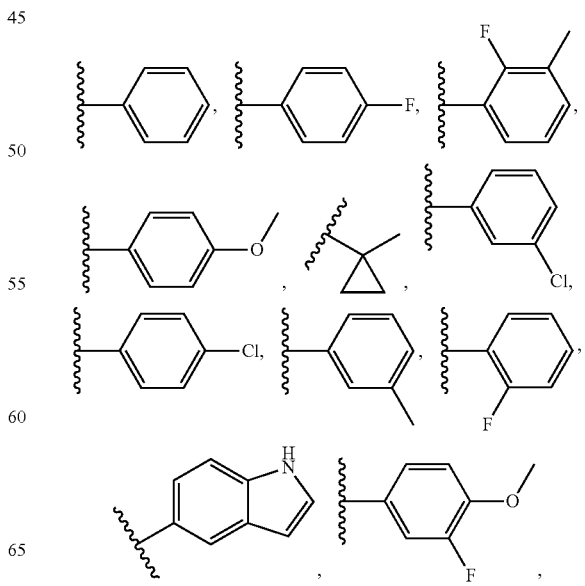

81
-continued
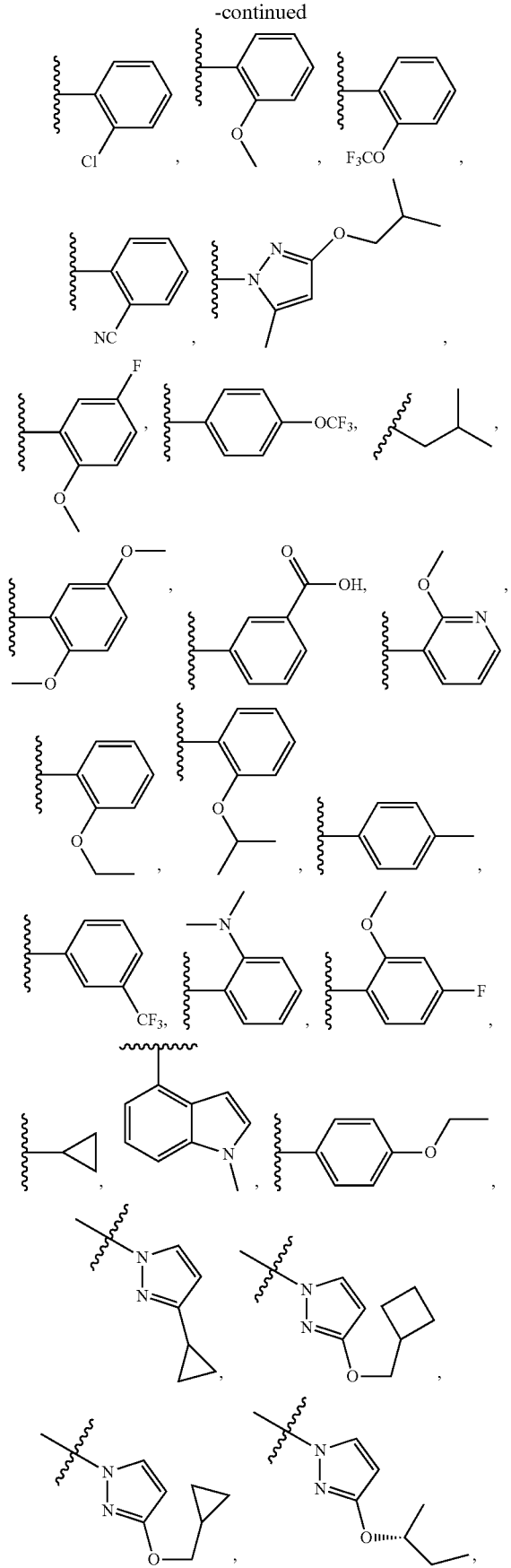
82
-continued
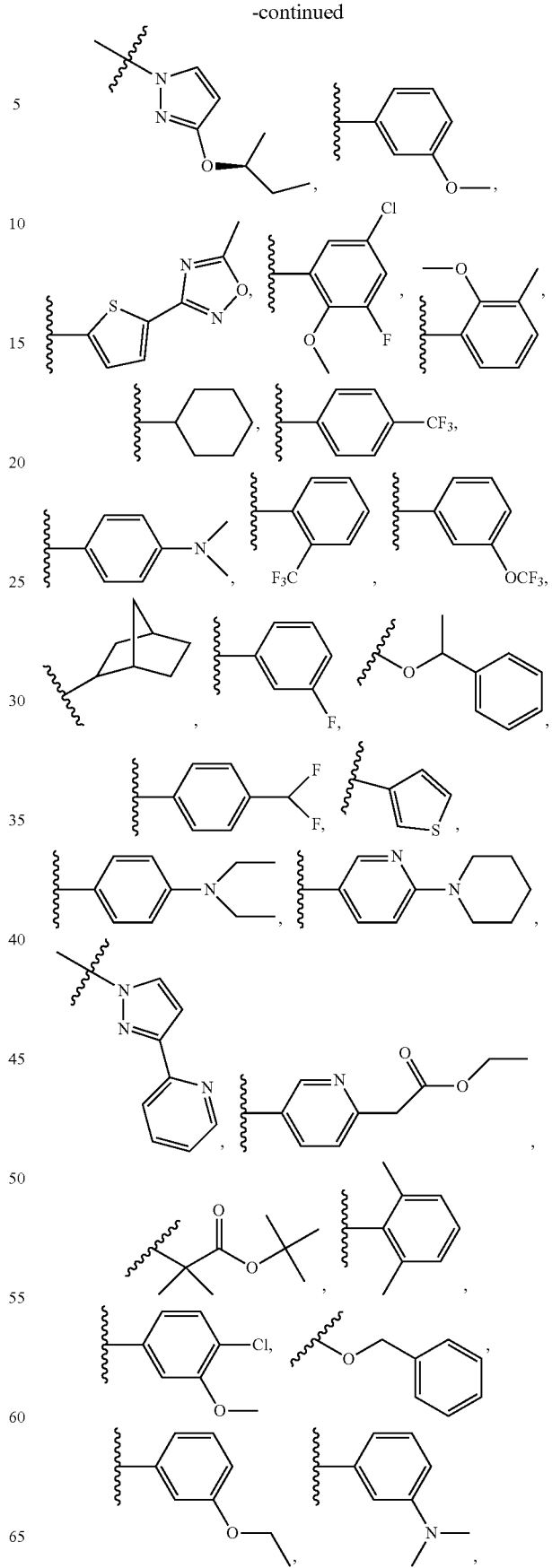

-continued
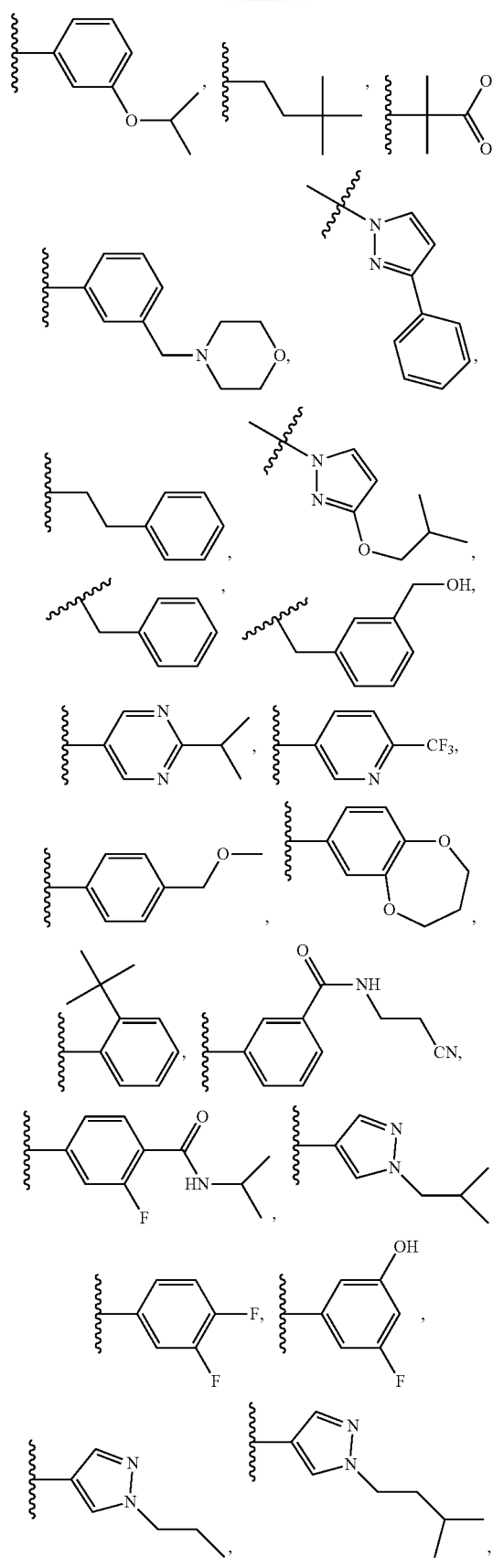
-continued
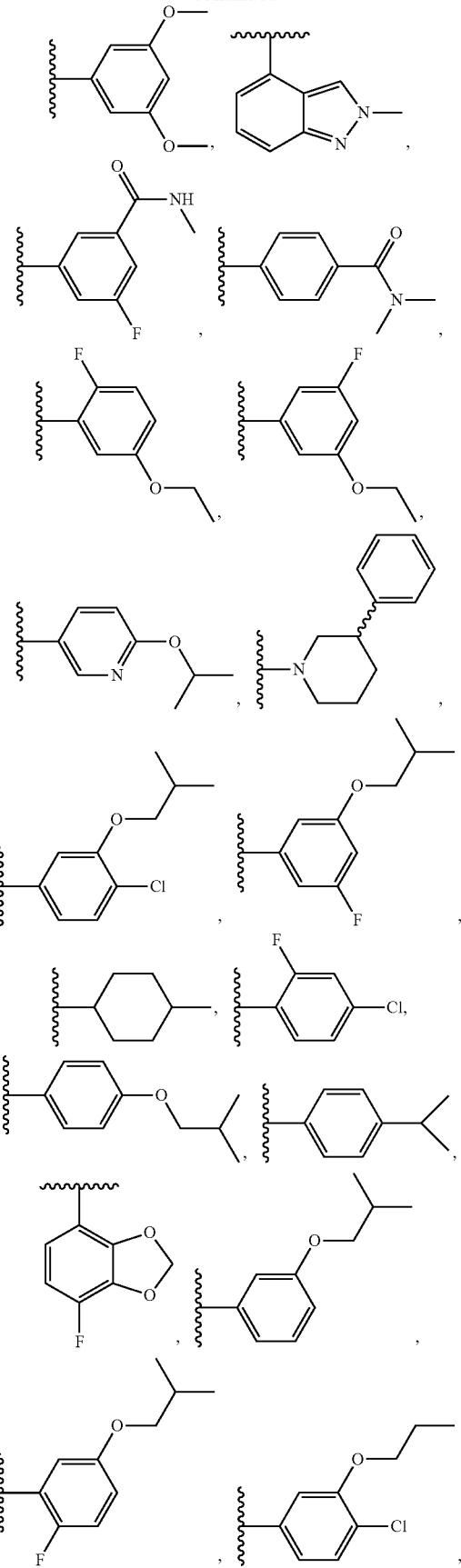

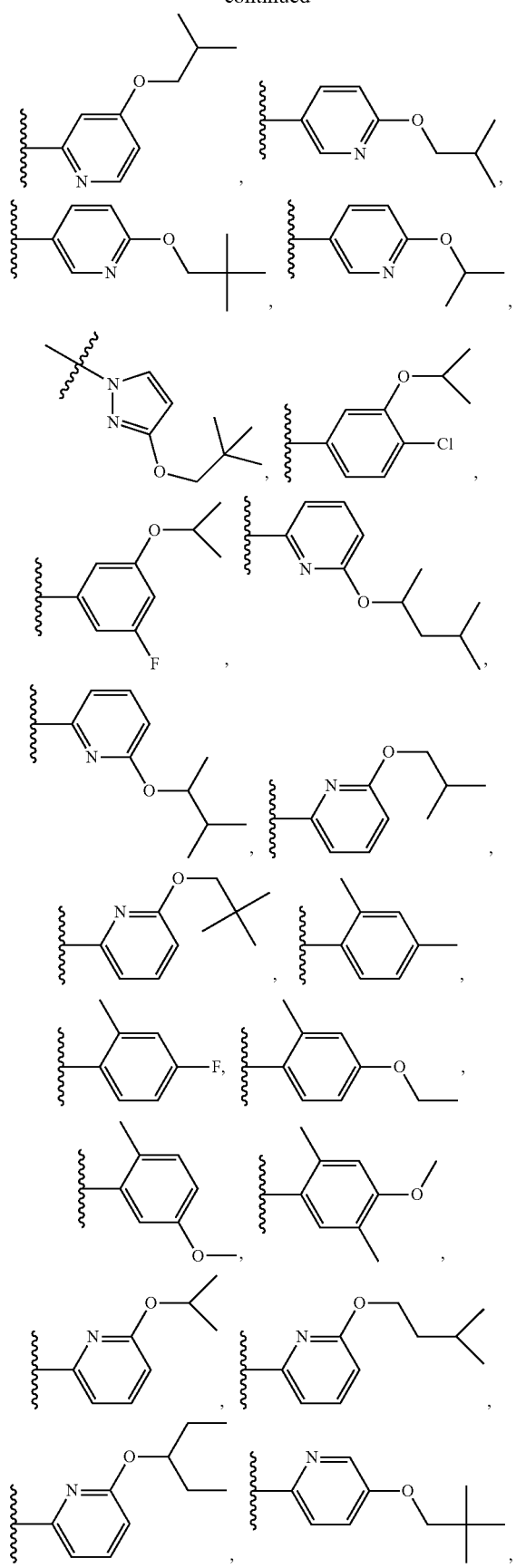
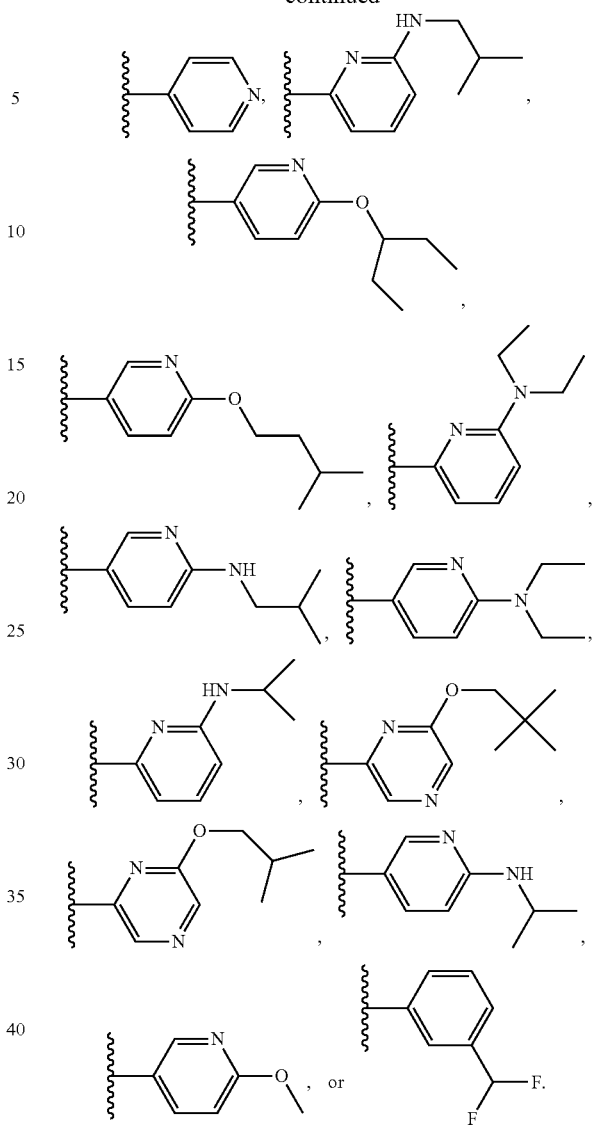

In some embodiments, R$_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-R$_4$ wherein up to four CH$_2$ units are independently replaced with O, CO, S, SO, SO$_2$ or NR.

In some embodiments, R$_2$ is a group represented by the corresponding moieties shown in the compounds of Table 1. For example, R$_2$ is Cl, F, OH, CN, N$_3$, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, CH$_3$, CH$_2$OH, CH$_2$CH$_3$, CH$_2$CH$_2$CH$_3$, =O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

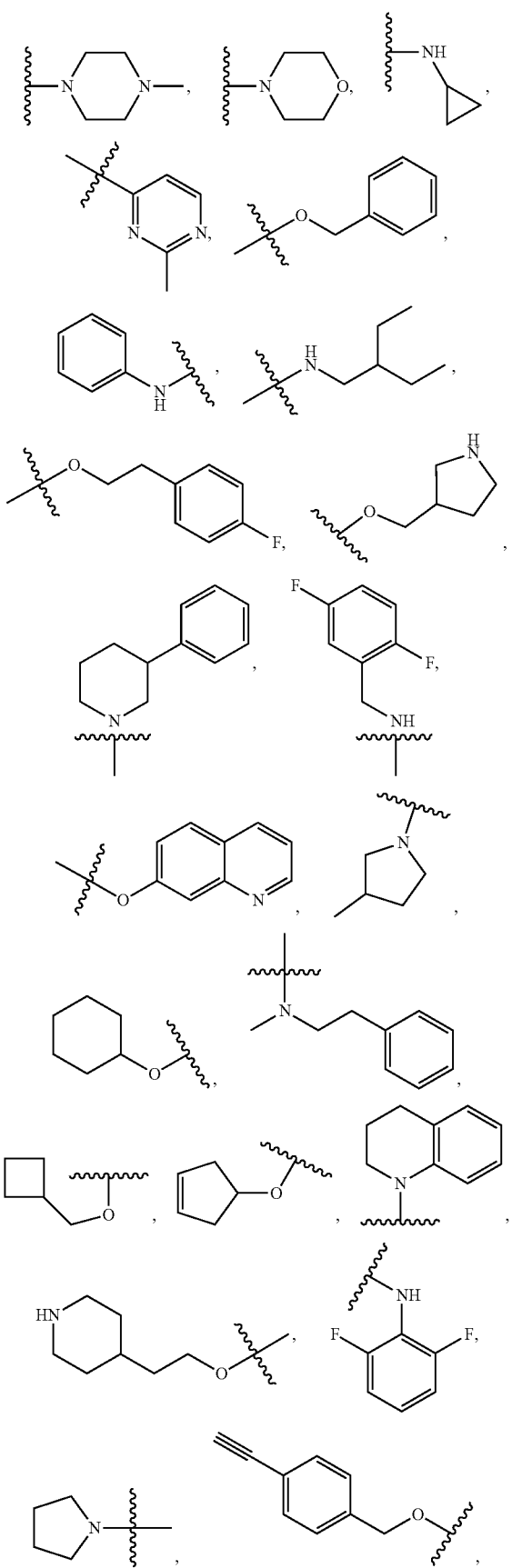
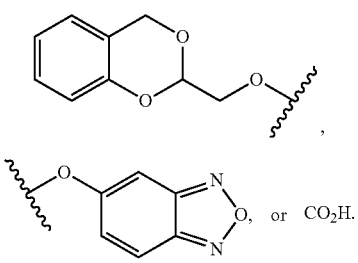
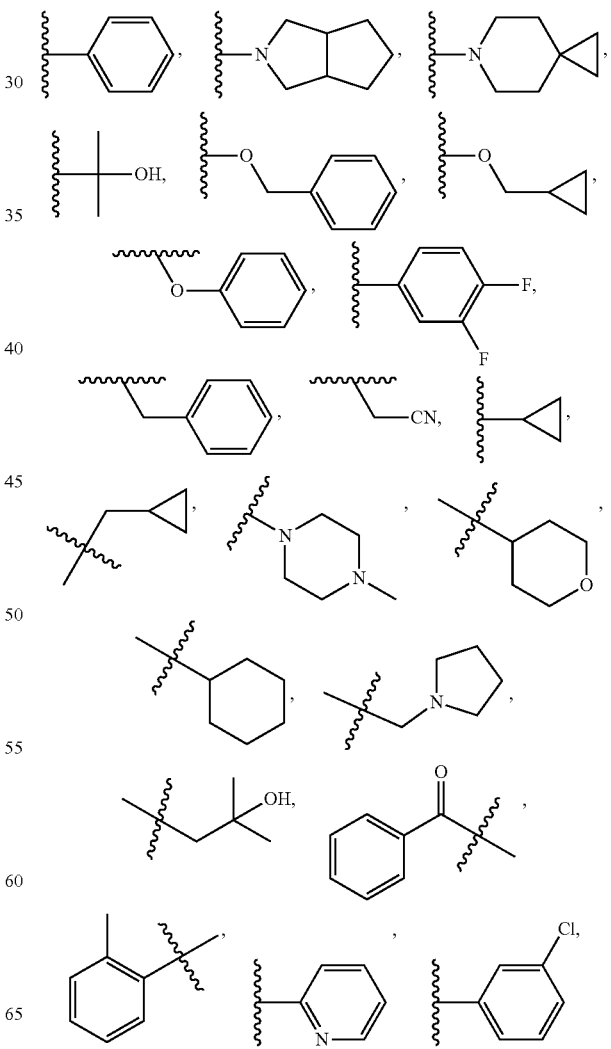

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

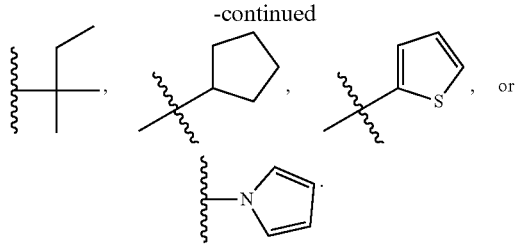

In some embodiments, o is 0. In some embodiments, o is 1. In some embodiments, o is 2.

In some embodiments, n is 0. In some embodiments, o is 1. In some embodiments, o is 2.

In some embodiments, p is 0. In some embodiments, p is 1. In some embodiments, p is 2.

In some embodiments, the invention features a compound of formula Ia-ii:

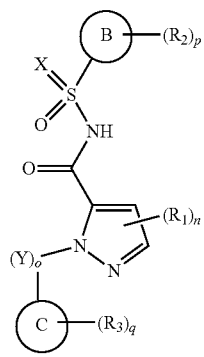

Ia-ii or a pharmaceutically acceptable salt thereof, wherein, independently for each occurrence:

Ring B is a C6-C10 aryl ring;

Ring C is a C6-C10 aryl ring, C3-C14 heteroaryl or heterocyclic ring wherein anywhere from 1 to 4 ring atoms are independently N, O, or S, or a C3-C10 cycloalkyl ring;

X is O or NR;

Y is CRR, CO, O, S, SO, $SO_2$, S(O)NH or NR;

$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a $=CH_2$ or $=O$ group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a $=CH_2$ or $=O$ group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, or 2;

o is 0, 1, 2, 3, 4, or 5;

p is 0, 1, 2, or 3; and q is 0, 1, 2, 3, 4, or 5.

In some embodiments, the compound of formula Ia-ii exists as a pharmaceutically acceptable prodrug.

In some embodiments, ring B is phenyl or naphthalene.

In some embodiments, ring C is phenyl, indole, cycloalkyl, pyridyl, pyrrolidine, naphthalene, piperidine, or dihydroindene.

In some embodiments, ring C is a group represented by the corresponding moieties shown in the compounds of Table 1. For example, ring C is

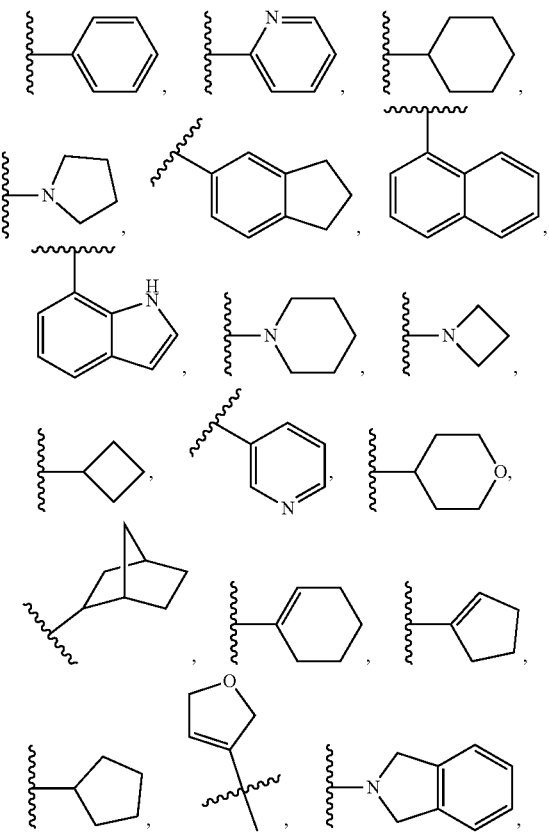

-continued

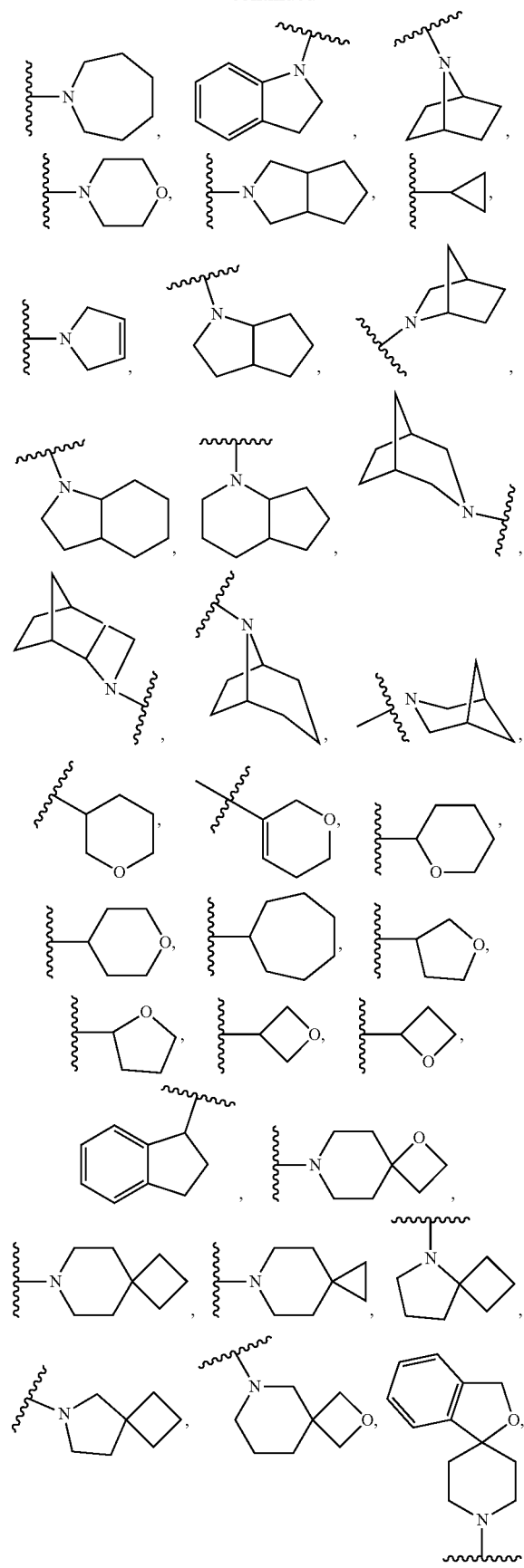

-continued

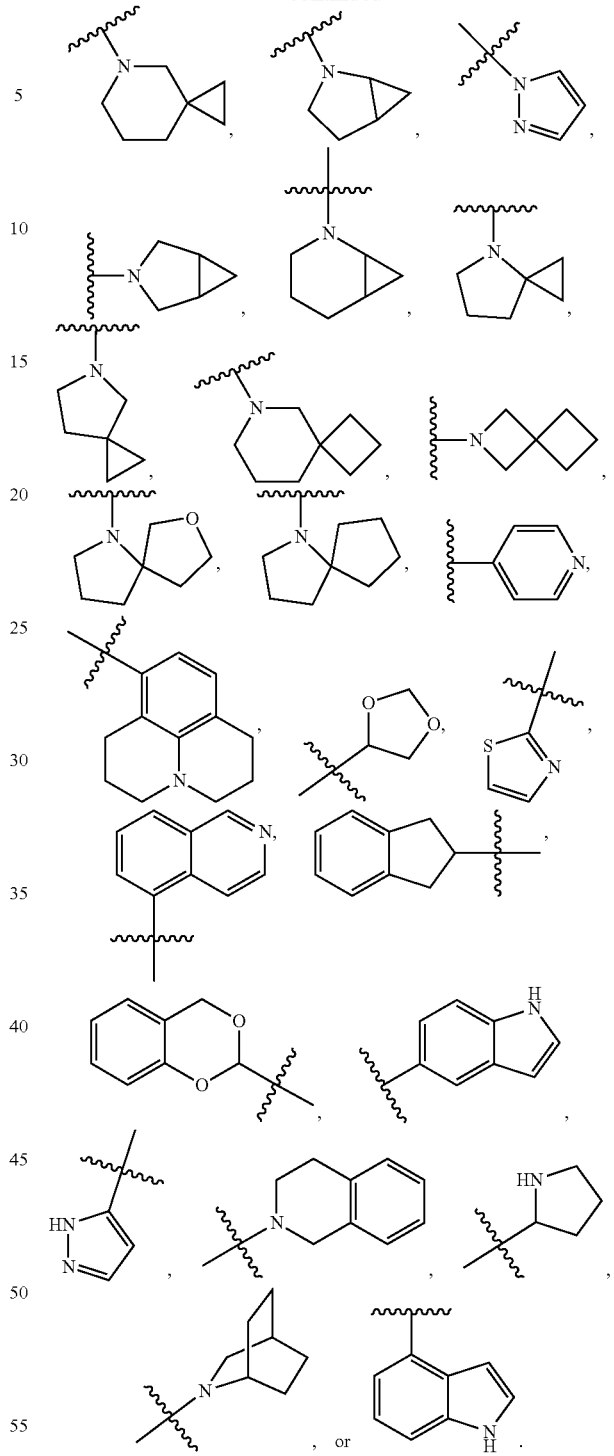

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, CH$_2$OH, CH$_2$OCH$_3$, CN, CO$_2$H, amino, amido, C3-C10 heteroaryl, and C3-C10 heterocycloalkyl.

In some embodiments, R$_1$ is a group represented by the corresponding moieties shown in the compounds of Table 1. For example, R$_1$ is CH$_3$, Cl, F, CN, OCH$_3$, CF$_3$, CH$_2$CH$_3$, tBu, CH(CH$_3$)$_2$, OCH$_2$CH$_2$OCH$_2$CH$_3$,

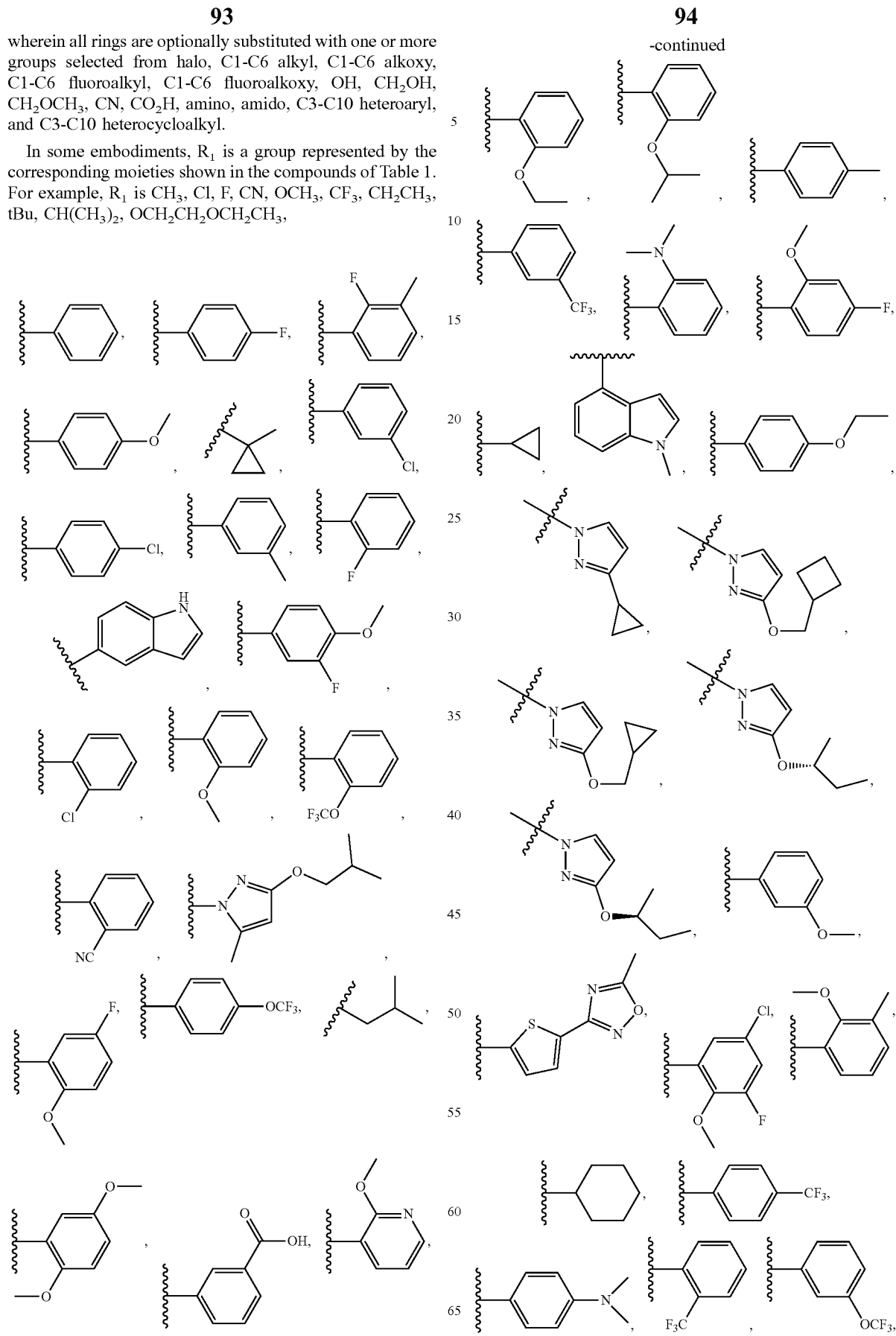

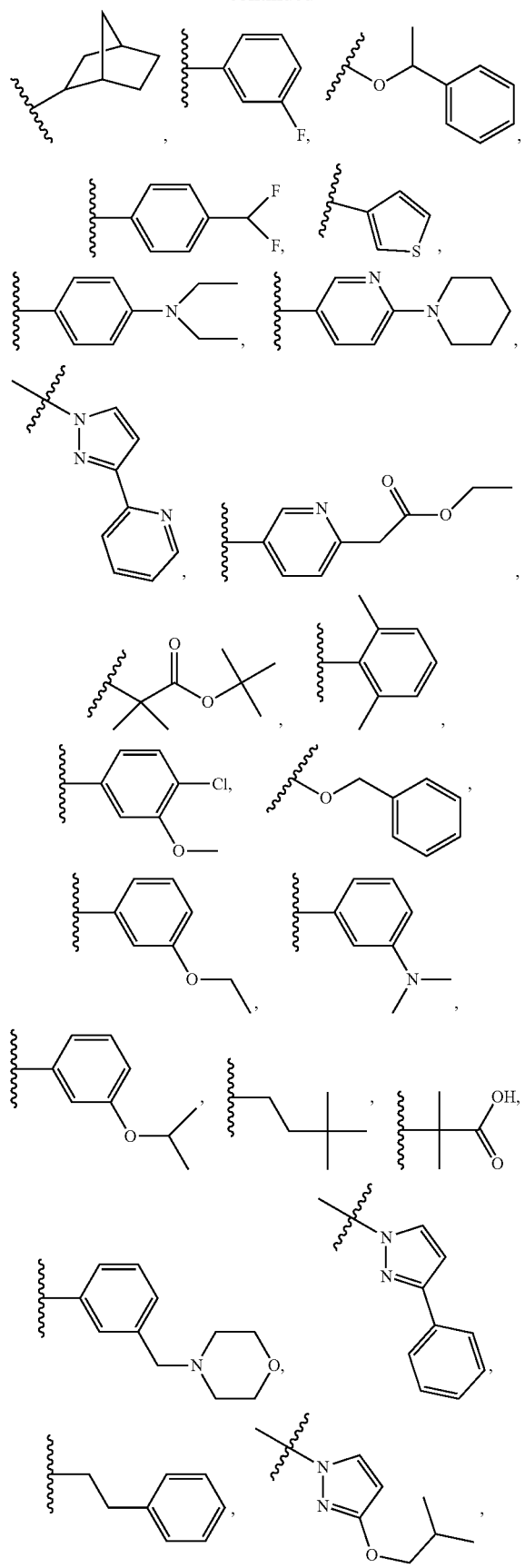
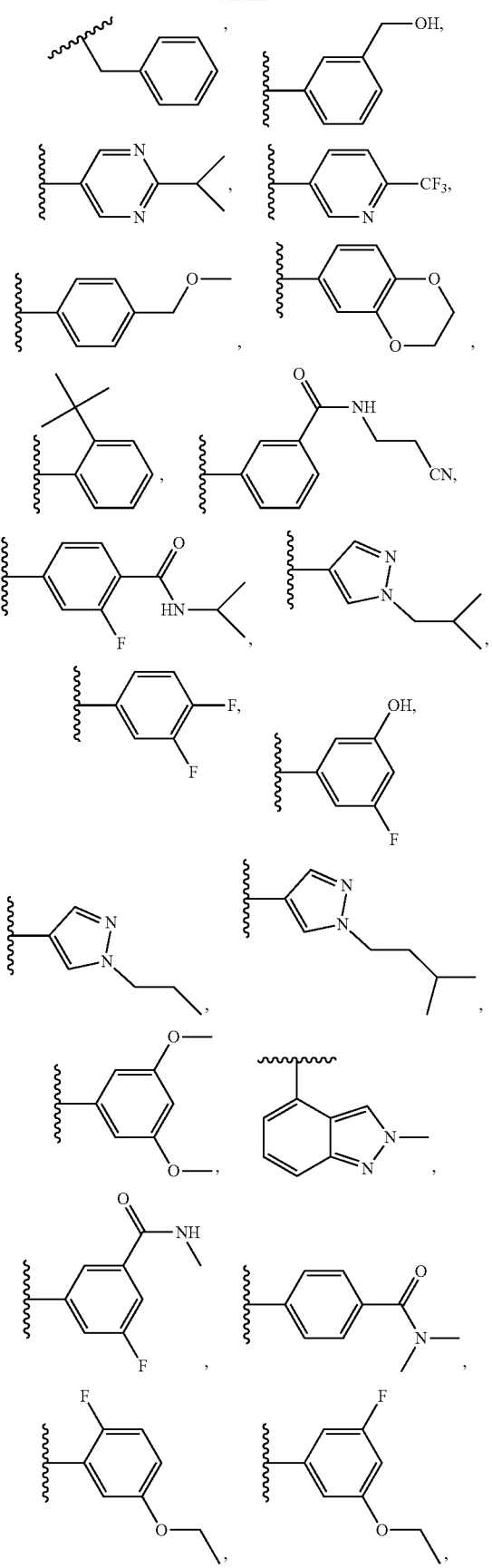

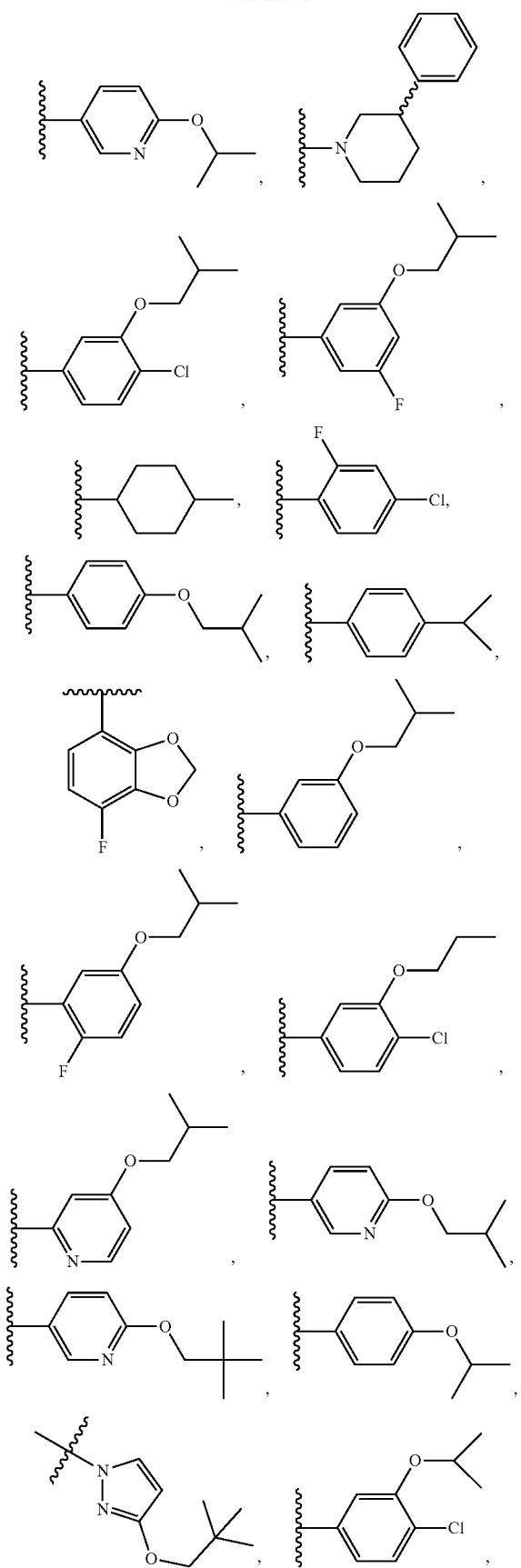
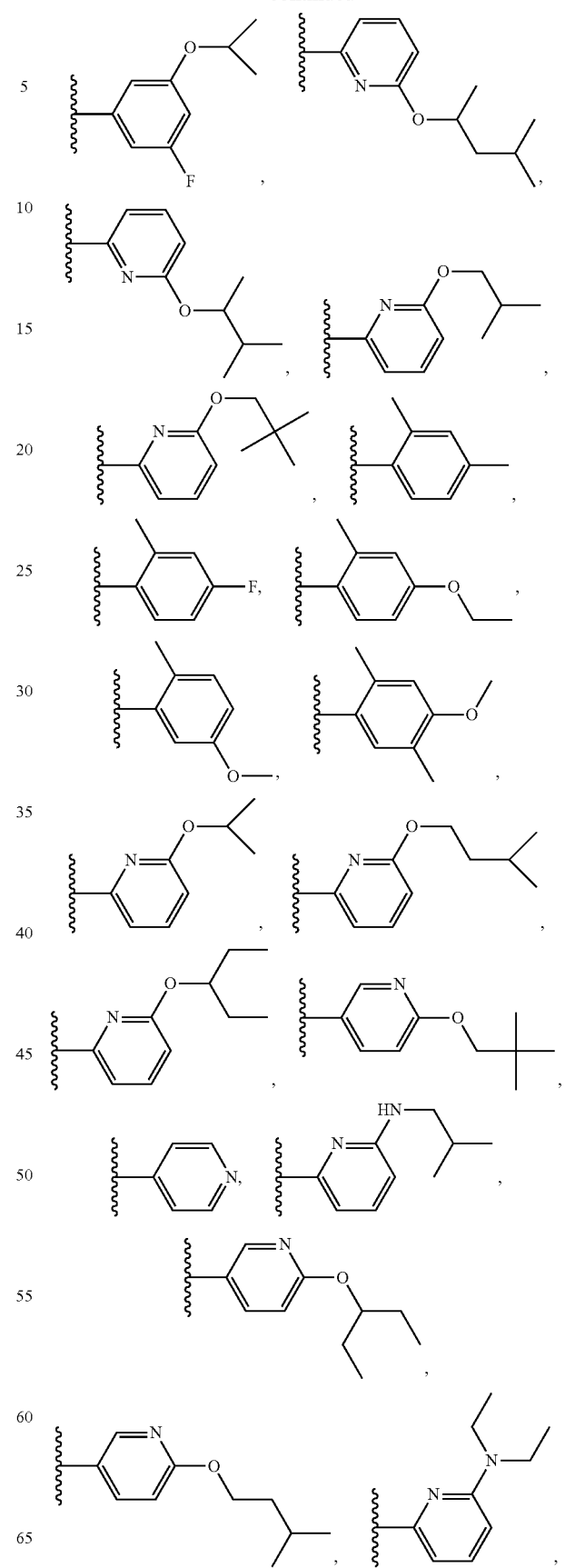

-continued

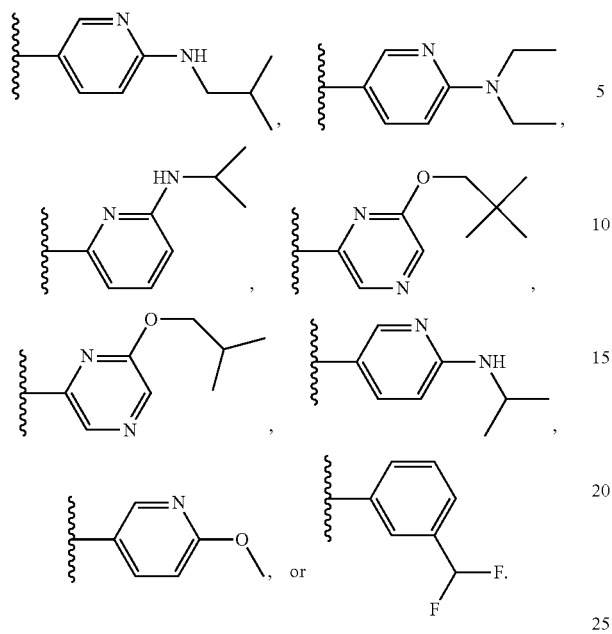

In some embodiments, R$_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-R$_4$ wherein up to four CH$_2$ units are independently replaced with O, CO, S, SO, SO$_2$ or NR.

In some embodiments, R$_2$ is a group represented by the corresponding moieties shown in the compounds of Table 1. For example, R$_2$ is Cl, F, OH, CN, N$_3$, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, CH$_3$, CH$_2$OH, CH$_2$CH$_3$, CH$_2$CH$_2$CH$_3$, =O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

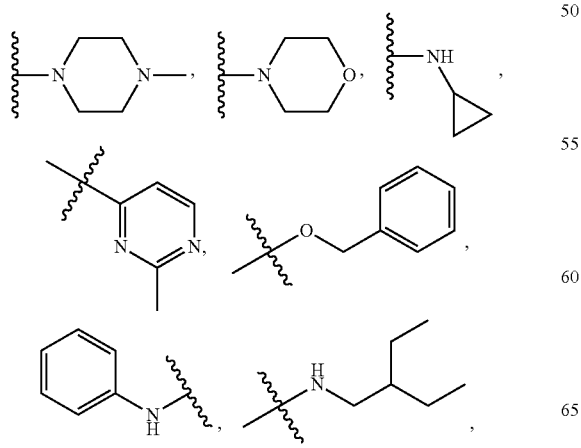

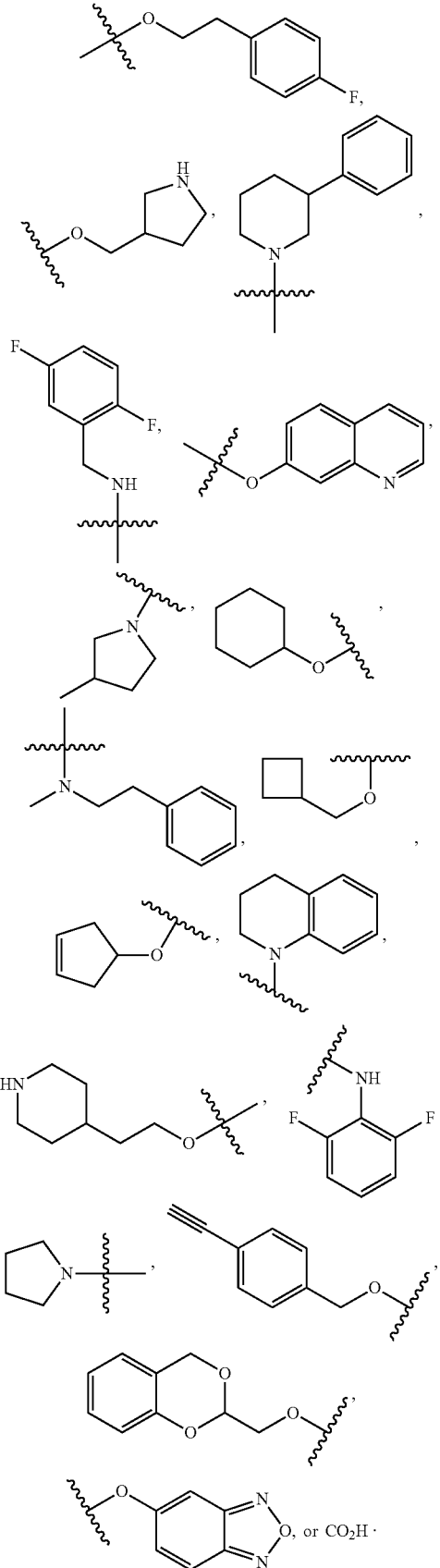

or CO$_2$H.

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

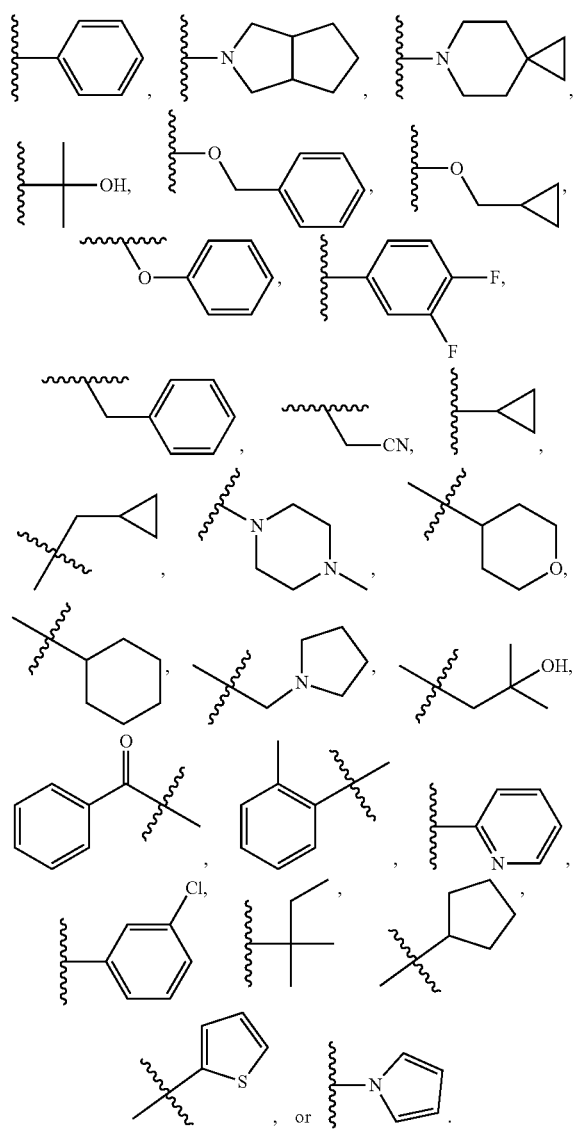

In some embodiments, o is 0. In some embodiments, o is 1. In some embodiments, o is 2.

In some embodiments, n is 0. In some embodiments, o is 1. In some embodiments, o is 2.

In some embodiments, p is 0. In some embodiments, p is 1. In some embodiments, p is 2.

In some embodiments, the compound of formula I is a compound of formula Ib:

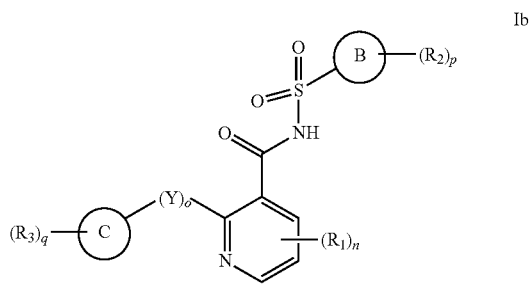

or a pharmaceutically acceptable salt thereof, wherein, independently for each occurrence:

Ring B is a C6-C10 aryl ring or C3-C10 heteroaryl or heterocyclic ring wherein anywhere from 1 to 4 ring atoms are independently O, S, N, or NR;

Ring C is a C6-C10 aryl ring, C3-C14 heteroaryl or heterocyclic ring wherein anywhere from 1 to 4 ring atoms are independently N, O, or S, or a C3-C10 mono- or bicyclic cycloalkyl ring;

Y is CRR, CO, O, S, SO, SO₂, S(O)NH or NR;

R₁ is halo; CN; F₃S; SiR₃; OH; NRR; C1-C6 alkyl or fluoroalkyl; C1-C6 alkoxy or fluoroalkoxy; C1-C6 alkenyl; C1-C6 alkynyl; (C1-C9 alkylene)-R₄ wherein up to four CH₂ units are independently replaced with O, CO, S, SO, SO₂ or NR; C6-C10 aryl; C3-C10 heteroaryl or heterocyclic ring wherein anywhere from 1 to 4 ring atoms are independently O, S, N, or NR; or C3-C10 cycloalkyl;

R₂ is halo; OH; NRR; azide; CN; CO₂R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;

or two R₂ groups taken together may form a =CH₂ or =O group;

R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;

or two R₃ groups taken together may form a =CH₂ or =O group;

R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;

R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;
o is 0, 1, 2, 3, 4, or 5;
p is 0, 1, 2, or 3; and
q is 0, 1, 2, 3, 4, or 5.

In some embodiments, the compound of formula Ib exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

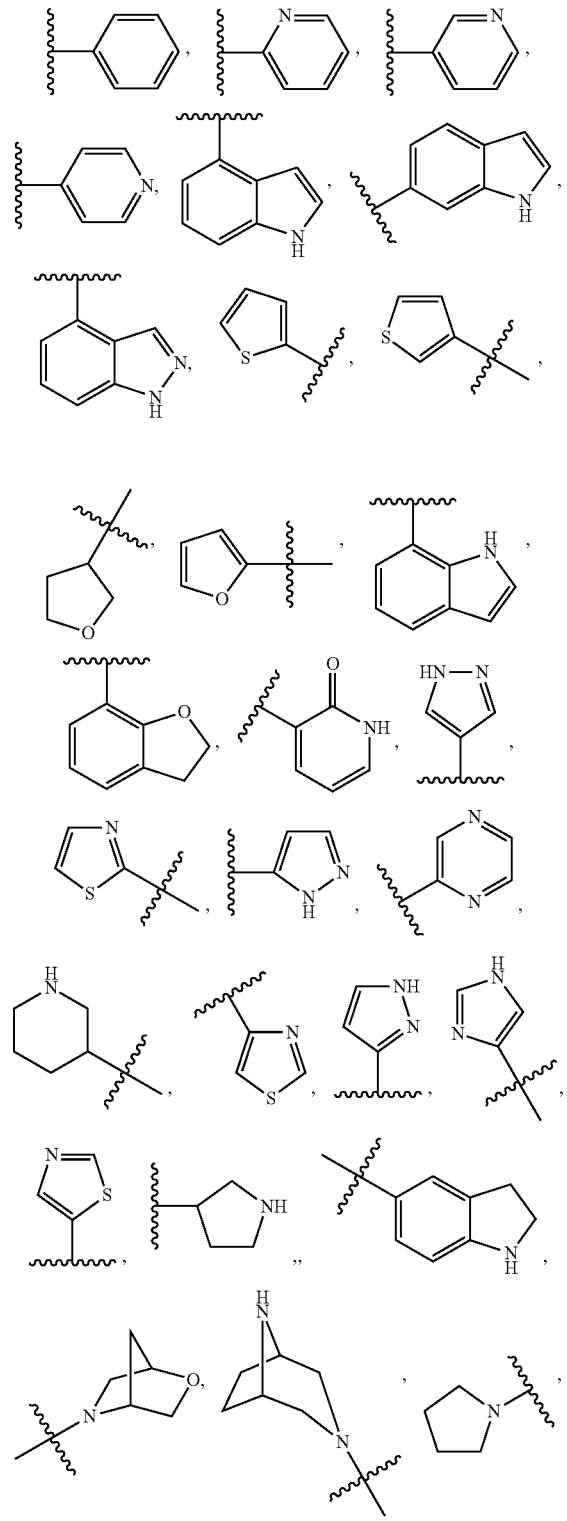

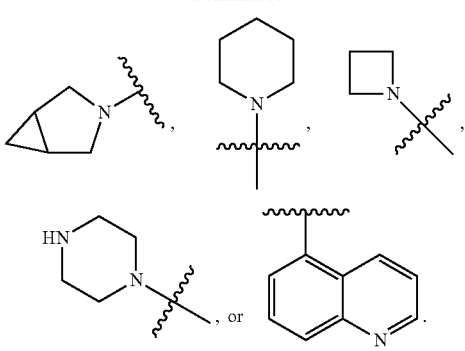

In some embodiments, ring C is phenyl, indole, cycloalkyl, pyridyl, naphthalene, pyrrolidine, or dihydroindene.

In some embodiments, ring C is a group represented by the corresponding moieties shown in the compounds of Table 1. For example, ring C is

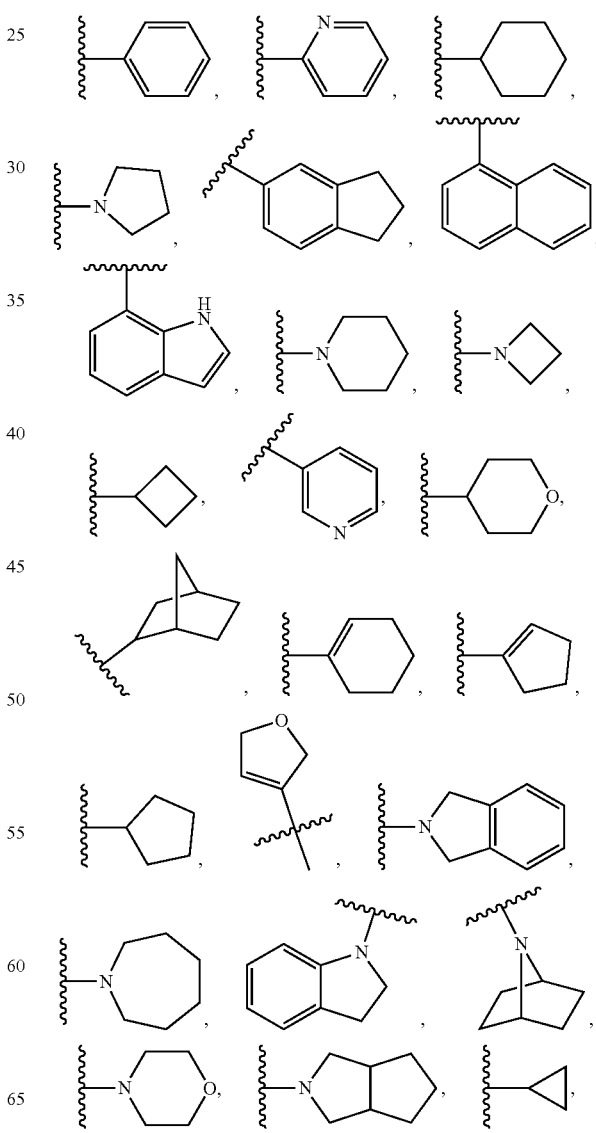

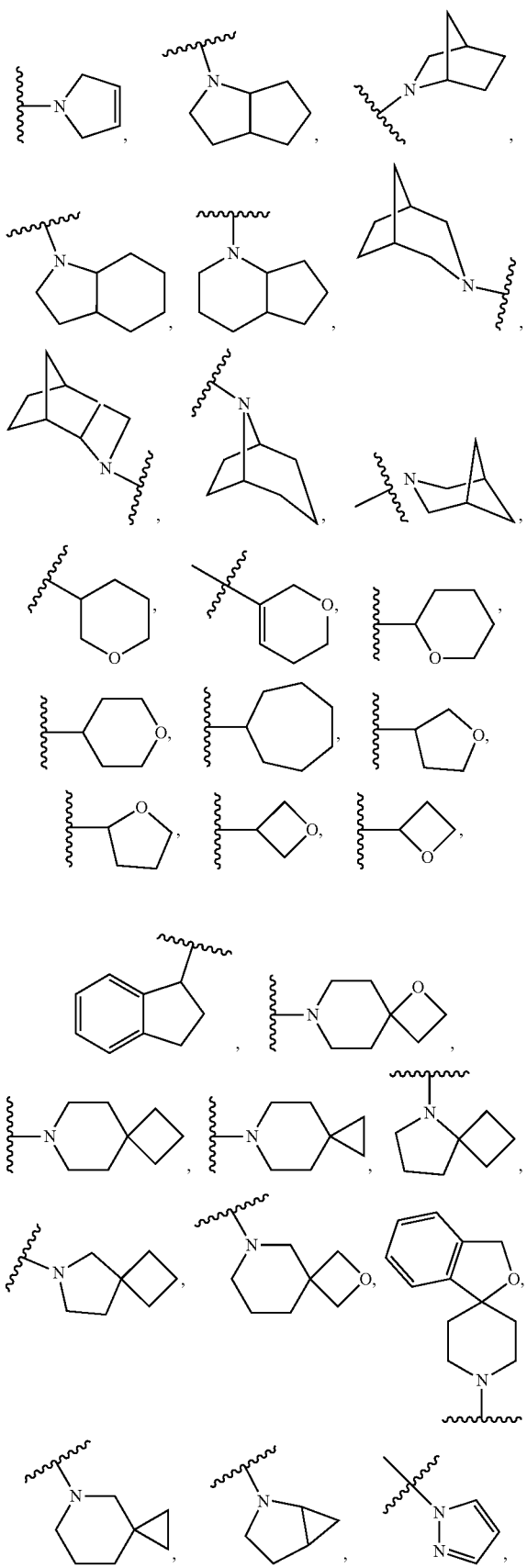
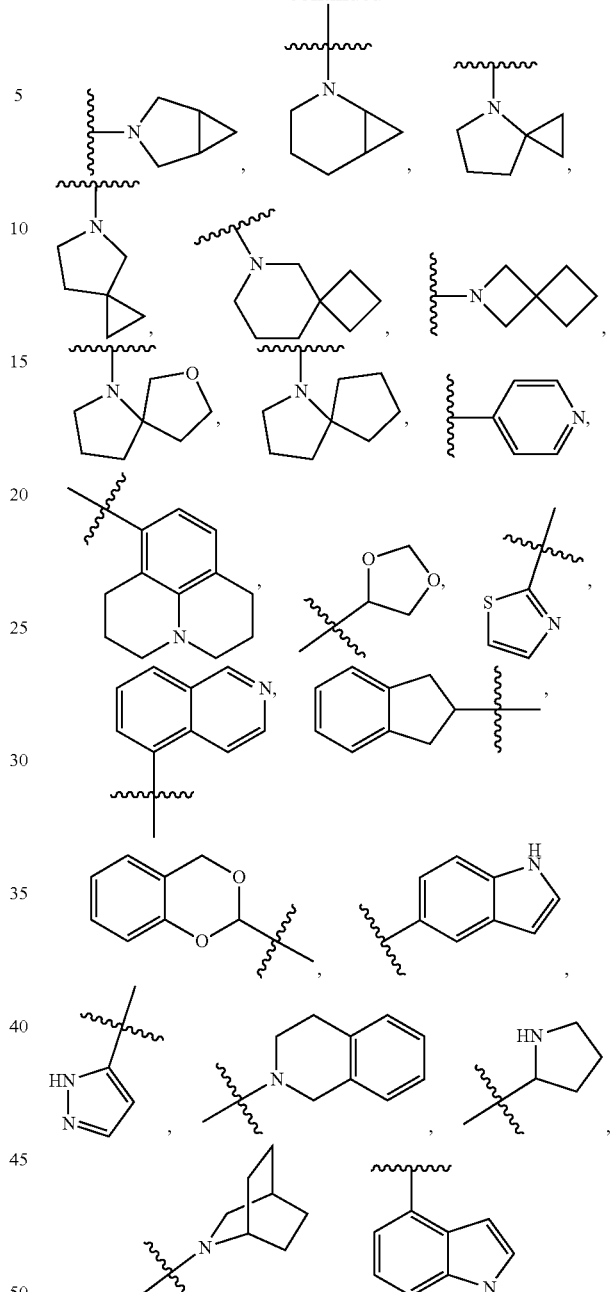

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, R₁ is a group represented by the corresponding moieties shown in the compounds of Table 1. For example, R₁ is CH₃, Cl, F, CN, OCH₃, CF₃, CH₂CH₃, tBu, CH(CH₃)₂, OCH₂CH₂OCH₂CH₃,
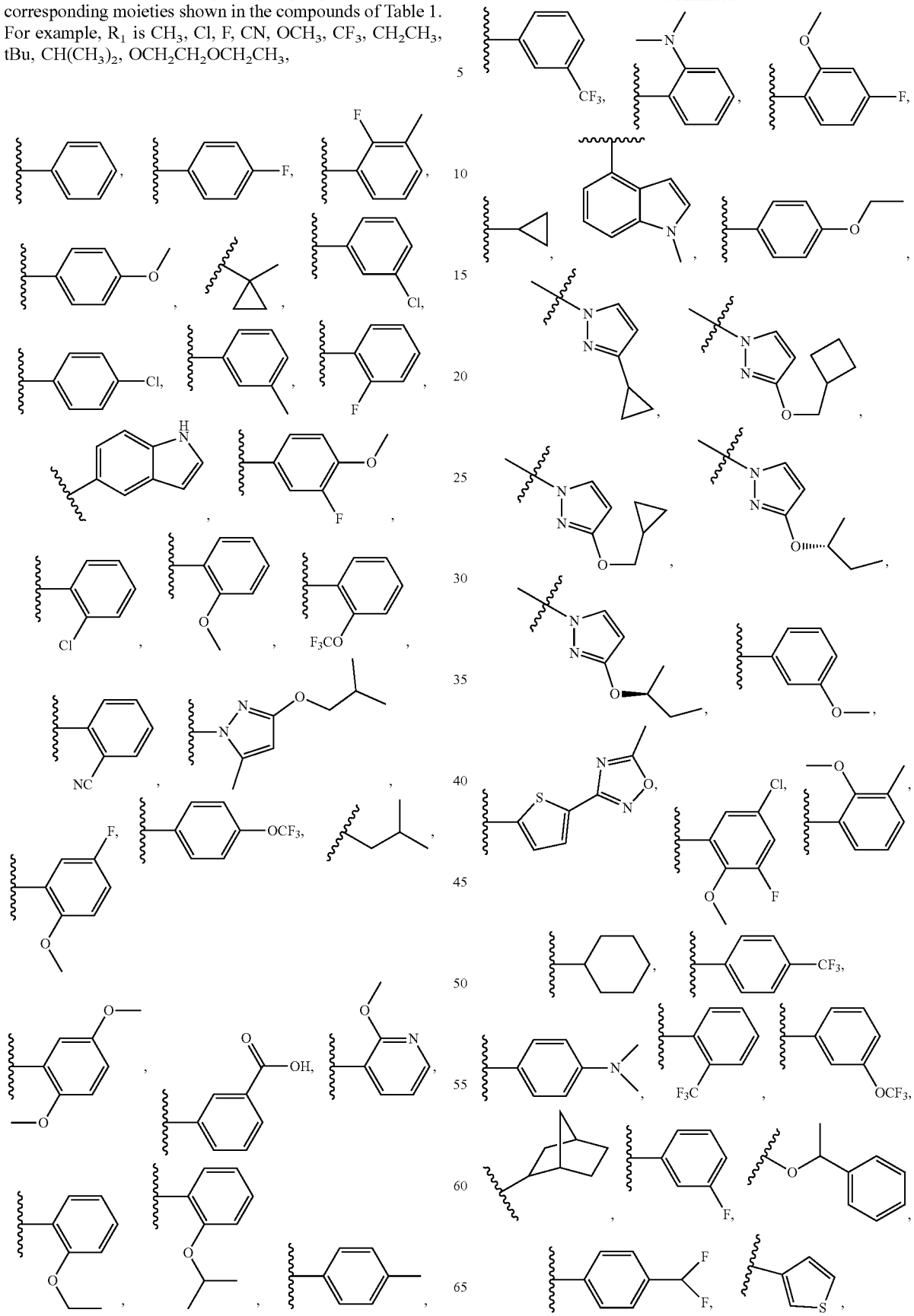

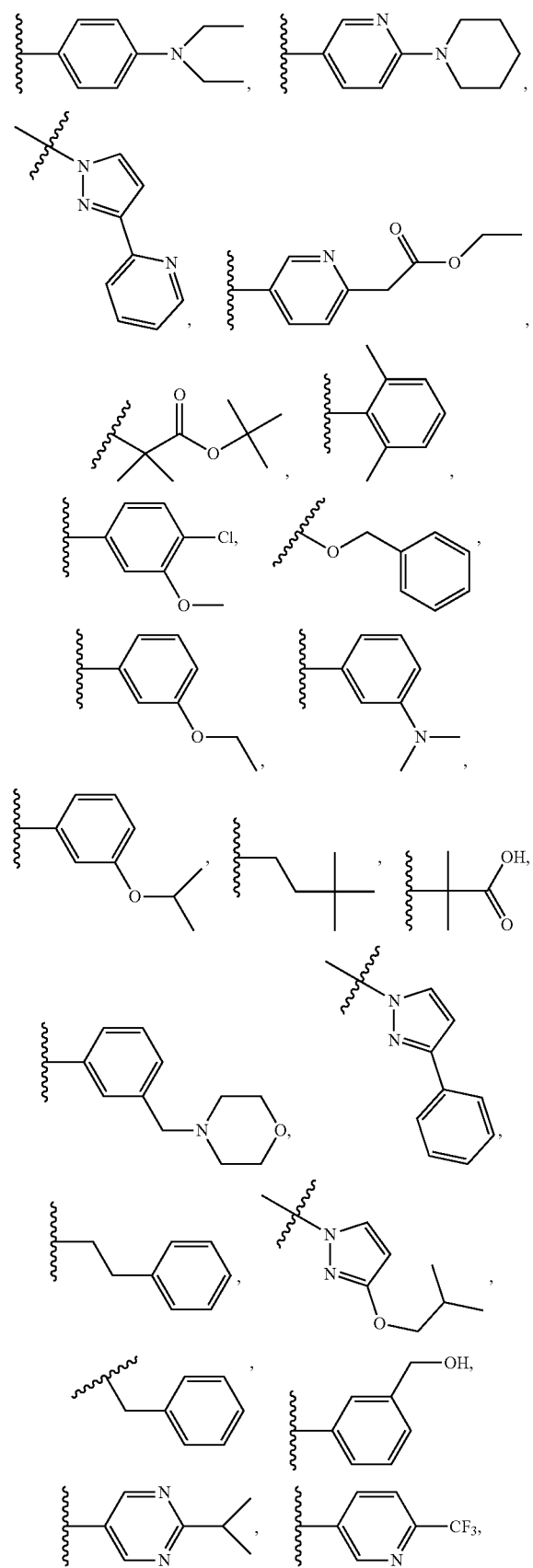
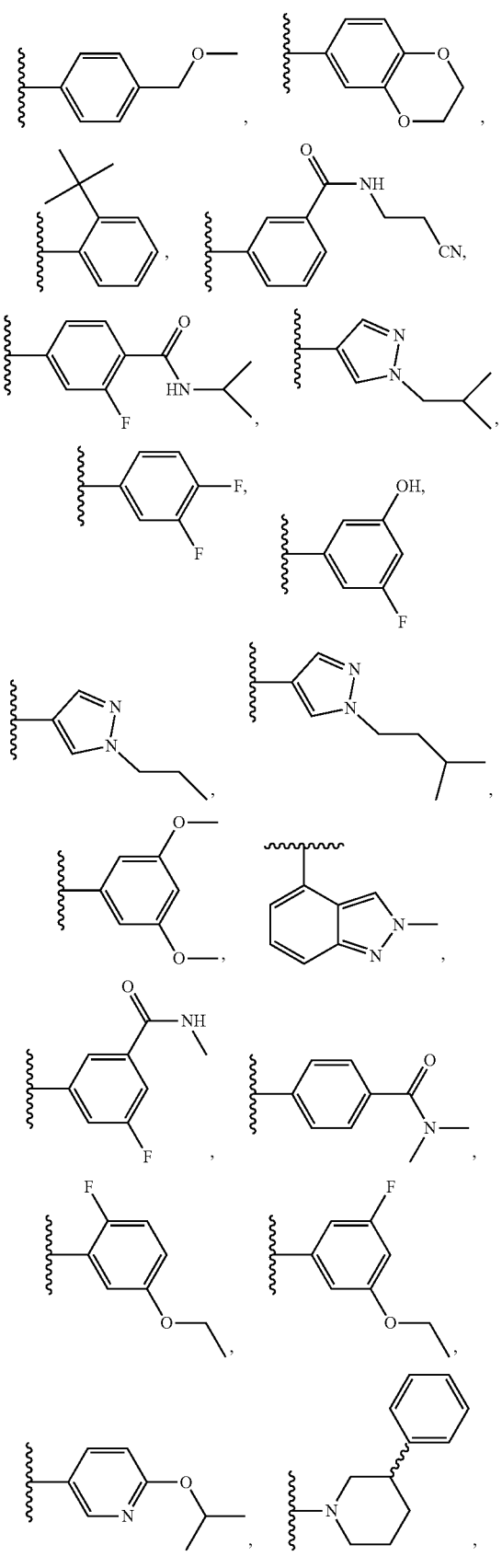

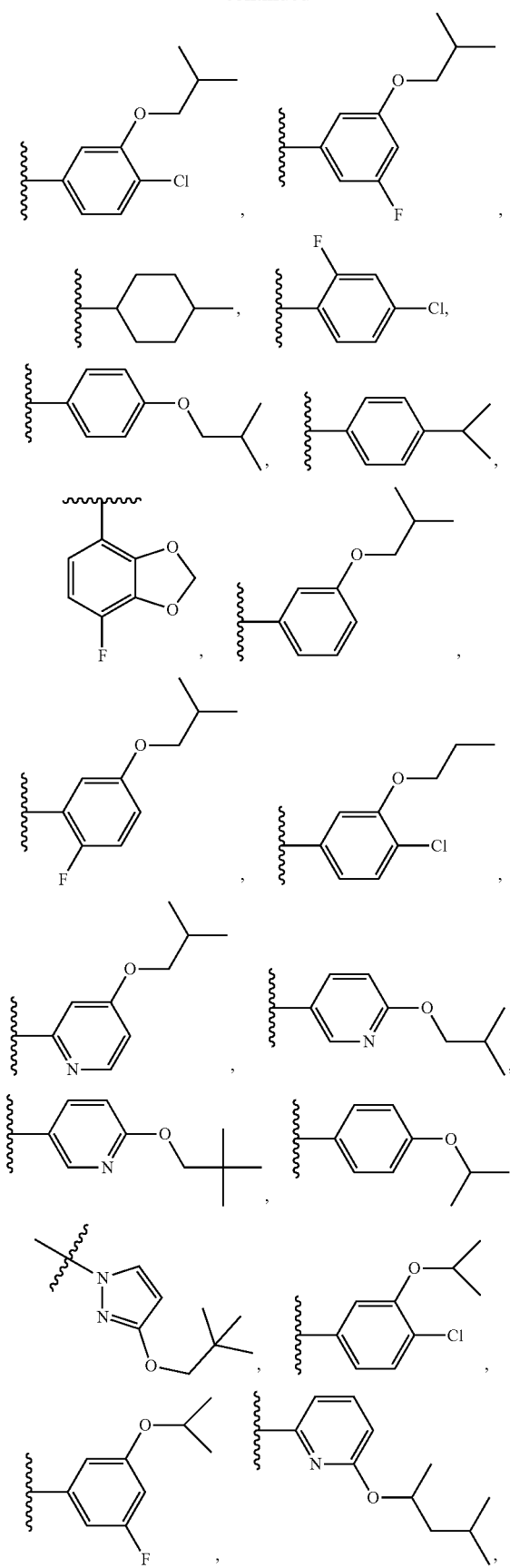
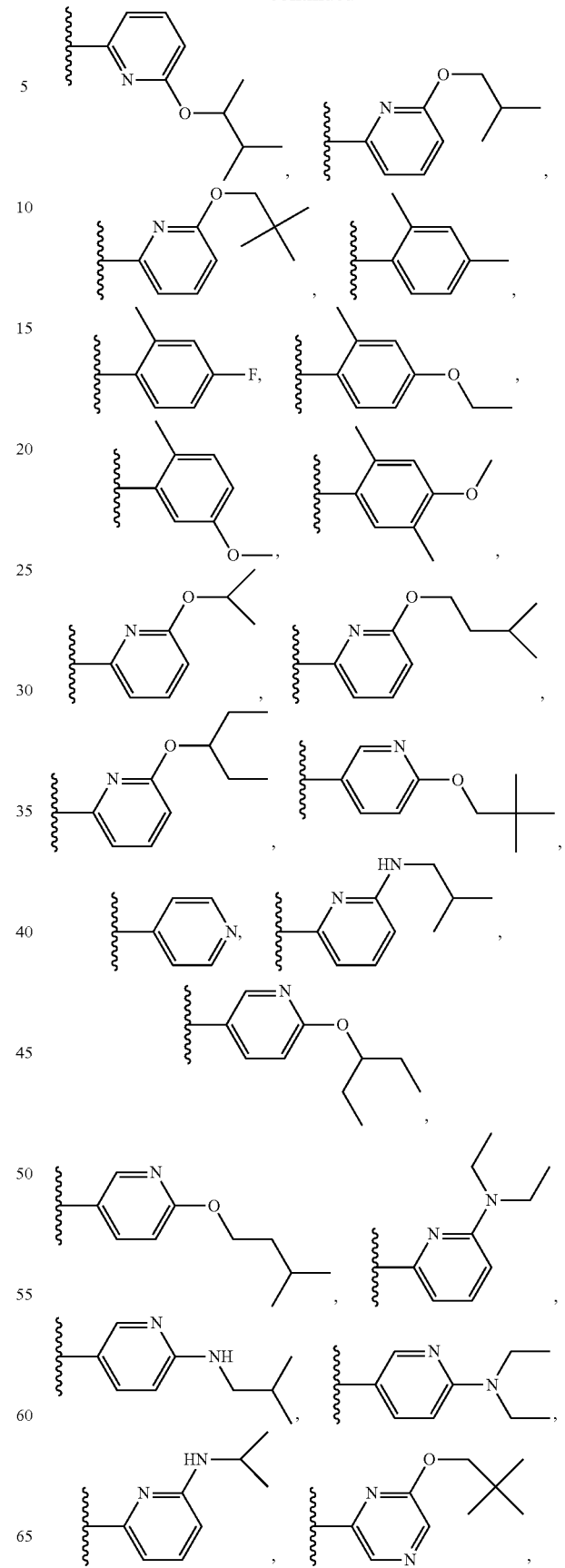

113

-continued

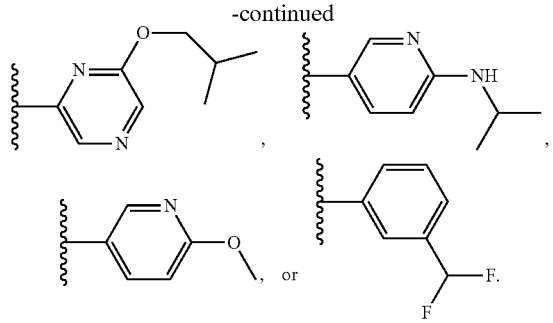

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

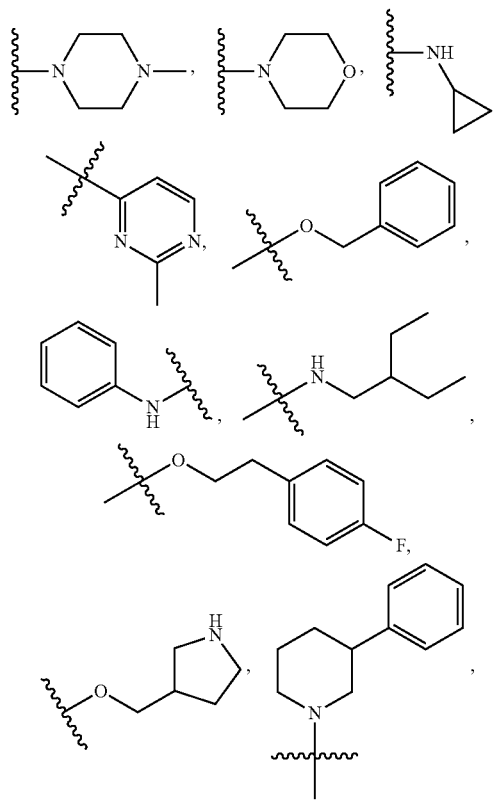

114

-continued

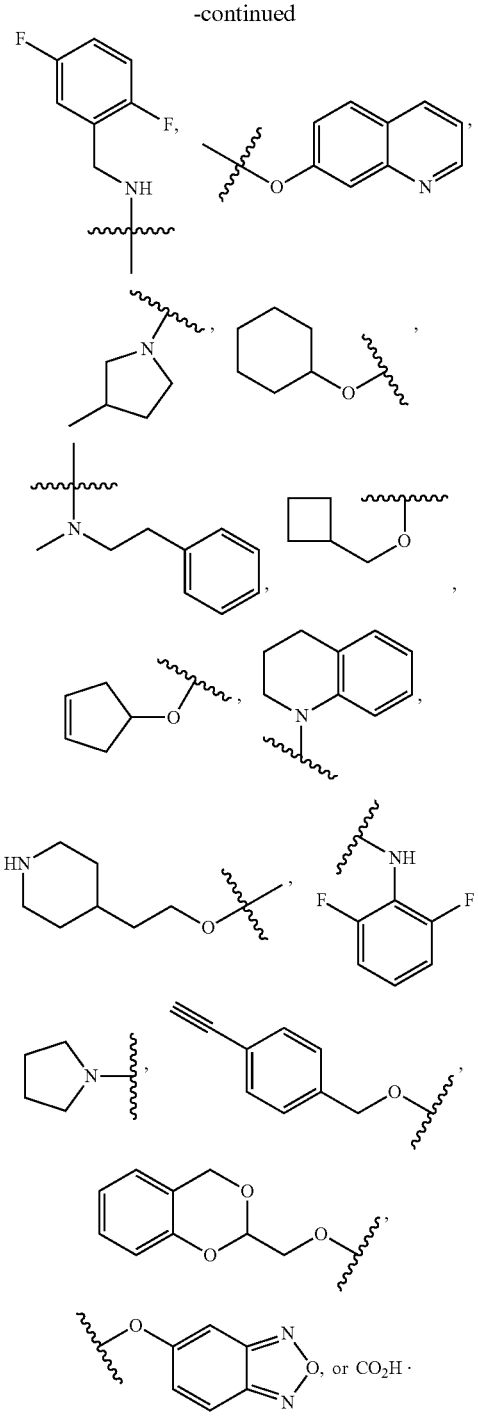

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

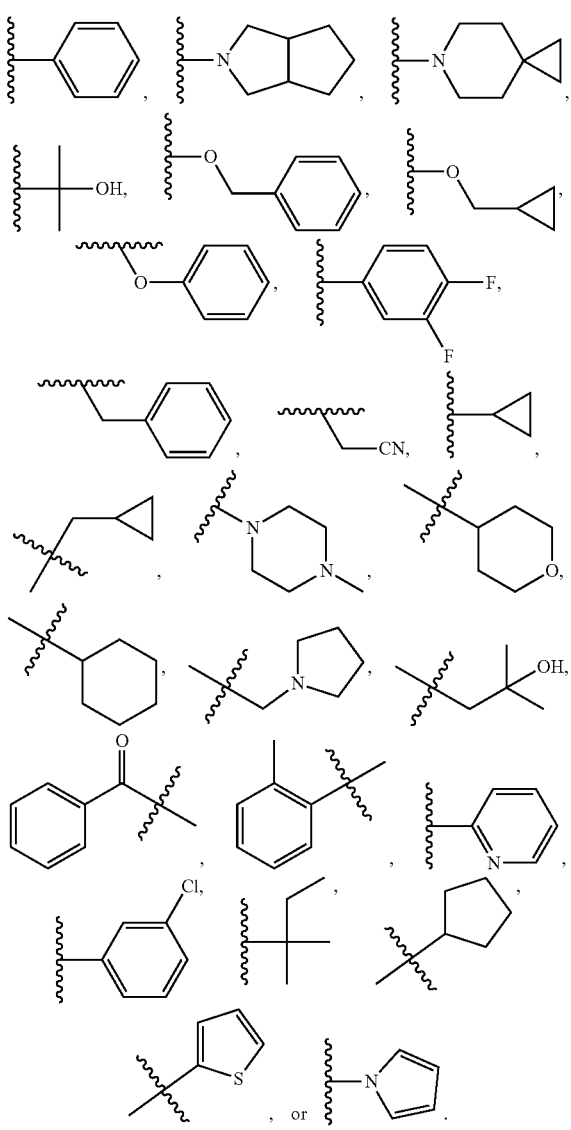

In some embodiments, o is 0. In some embodiments, o is 1. In some embodiments, o is 2.

In some embodiments, n is 0. In some embodiments, n is 1. In some embodiments, n is 2.

In some embodiments, p is 0. In some embodiments, p is 1. In some embodiments, p is 2.

In some embodiments, ring B is pyridyl. In some embodiments, ring B is phenyl. In some embodiments, ring B and ring C are phenyl. In some embodiments, ring B is pyridyl and ring C is phenyl. In some embodiments, Y is $CH_2$. In some embodiments, Y is O.

In some embodiments, $R_1$ is aryl. In some embodiments, ring B, ring C, and $R_1$ are phenyl. In some embodiments, ring B is pyridyl, ring C is phenyl, and $R_1$ is phenyl. In some embodiments, ring B, ring C, and $R_1$ are phenyl, and Y is $CH_2$. In some embodiments, ring B, ring C, and $R_1$ are phenyl, and Y is O. In some embodiments, ring B is pyridyl, ring C is phenyl, $R_1$ is phenyl, and Y is $CH_2$. In some embodiments, ring B is pyridyl, ring C is phenyl, $R_1$ is phenyl, and Y is O.

In some embodiments, ring C is heterocyclic. In some embodiments, ring C is pyrrolodine. In some embodiments, ring C is piperidine. In some embodiments, ring B is pyridyl, ring C is heterocyclic. In some embodiments, ring B is pyridyl, ring C is heterocycloalkyl, and $R_1$ is phenyl. In some embodiments, ring B is phenyl, ring C is heterocycloalkyl, and $R_1$ is phenyl.

In some embodiments, $R_1$ is heteroaryl. In some embodiments, ring C is pyrrolidine and $R_1$ is heteroaryl. In some embodiments, ring C is pyrrolidine and $R_1$ is pyrrozole. In some embodiments, ring B is pyridyl, ring C is pyrrolidine, and $R_1$ is heteroaryl. In some embodiments, ring B is pyridyl, ring C is heterocycloalkyl, and $R_1$ is pyridyl.

In some embodiments, $R_1$ is cycloalkyl. In some embodiments, ring B is pyridyl and $R_1$ is cycloalkyl.

In some embodiments, the invention features a compound of formula Ib-i:

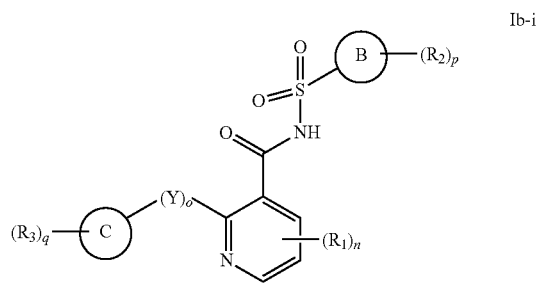

Ib-i or a pharmaceutically acceptable salt thereof, wherein, independently for each occurrence:

Ring B is a C3-C10 heteroaryl ring wherein anywhere from 1 to 4 ring atoms are independently O, S, N, or NR;

Ring C is a C6-C10 aryl ring, C3-C14 heteroaryl or heterocyclic ring wherein anywhere from 1 to 4 ring atoms are independently N, O, or S, or a C3-C10 cycloalkyl ring;

Y is CRR, CO, O, S, SO, $SO_2$, S(O)NH or NR;

$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a =$CH_2$ or =O group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4-ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a =$CH_2$ or =O group;

R$_4$ is H; azide; CF$_3$; CHF$_2$; OR; CCH; CO$_2$R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO$_2$R;

R is independently H; OH; CO$_2$H; CO$_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;

o is 0, 1, 2, 3, 4, or 5;

p is 0, 1, 2, or 3; and q is 0, 1, 2, 3, 4, or 5.

In some embodiments, the compound of formula Ib-i exists as a pharmaceutically acceptable prodrug.

In some embodiments, ring B is pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

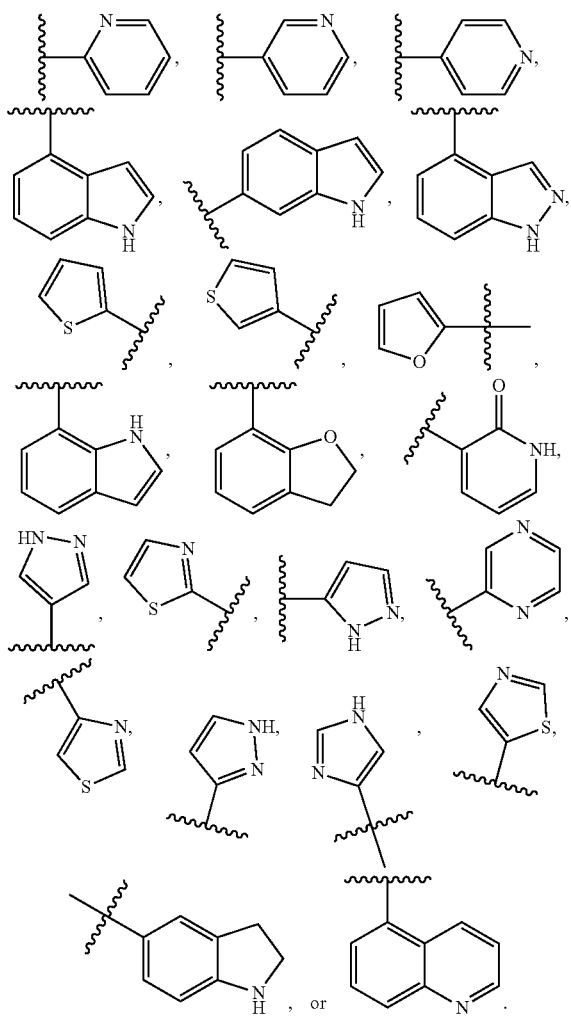

In some embodiments, ring C is phenyl, indole, cycloalkyl, pyridyl, naphthalene, pyrrolidine, or dihydroindene.

In some embodiments, ring C is a group represented by the corresponding moieties shown in the compounds of Table 1. For example, ring C is

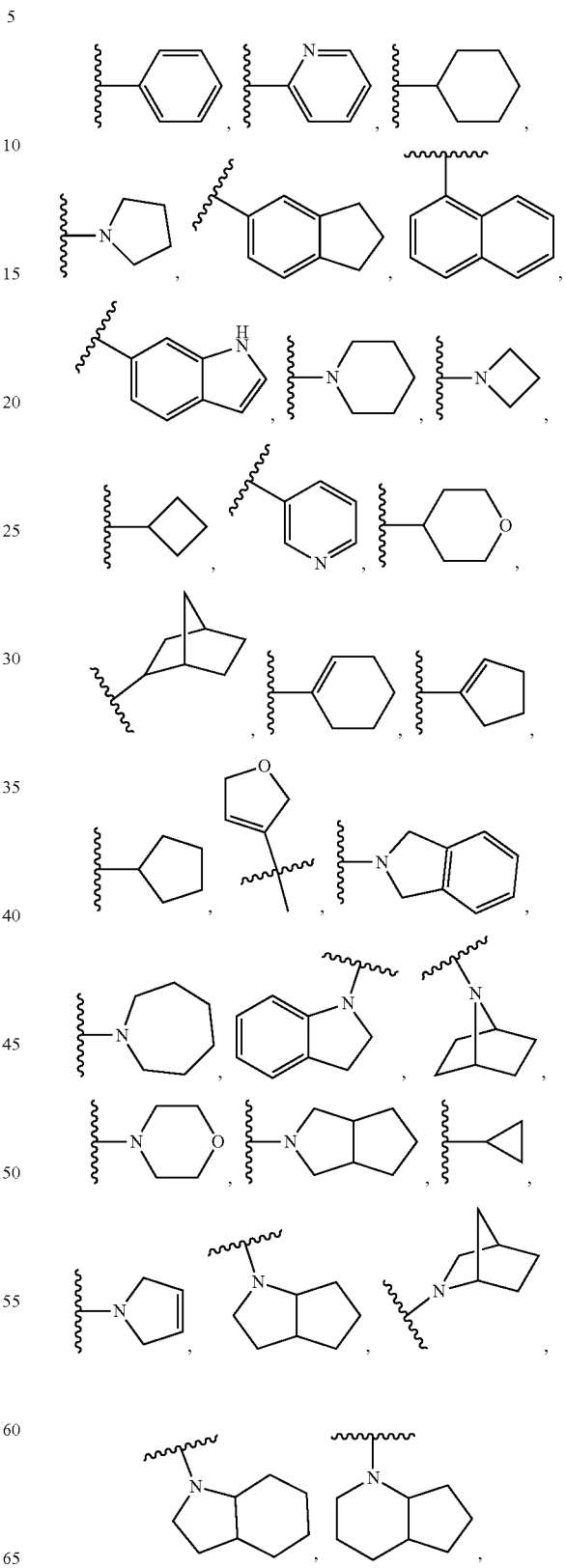

-continued

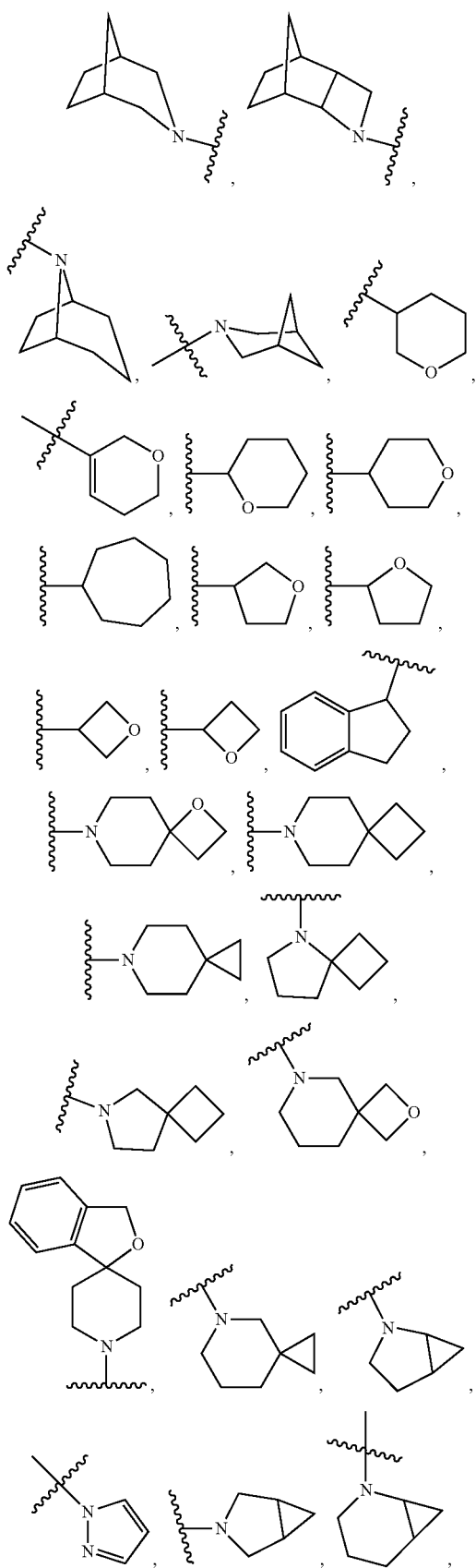

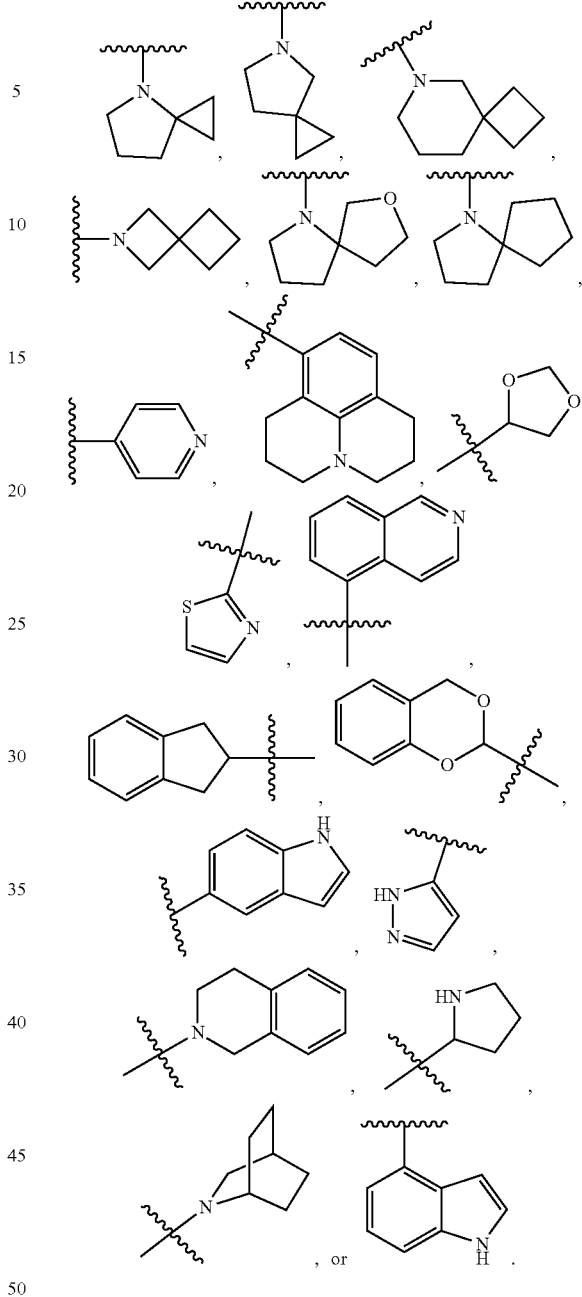

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1.

For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,
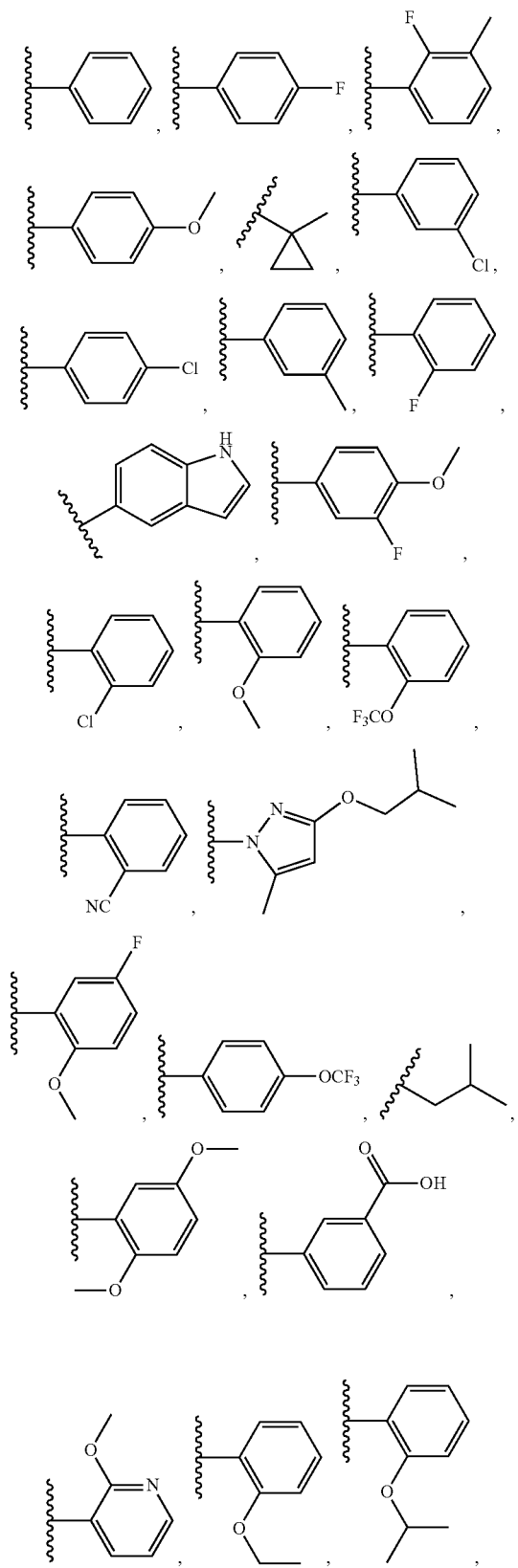
-continued
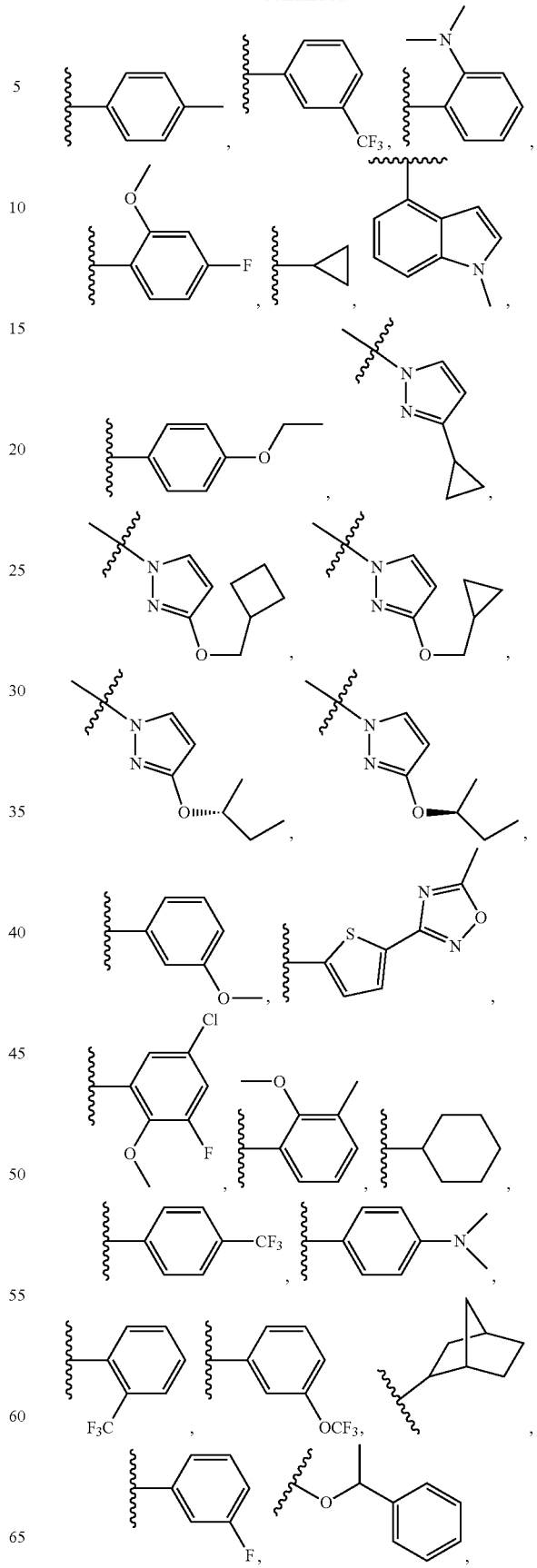

-continued
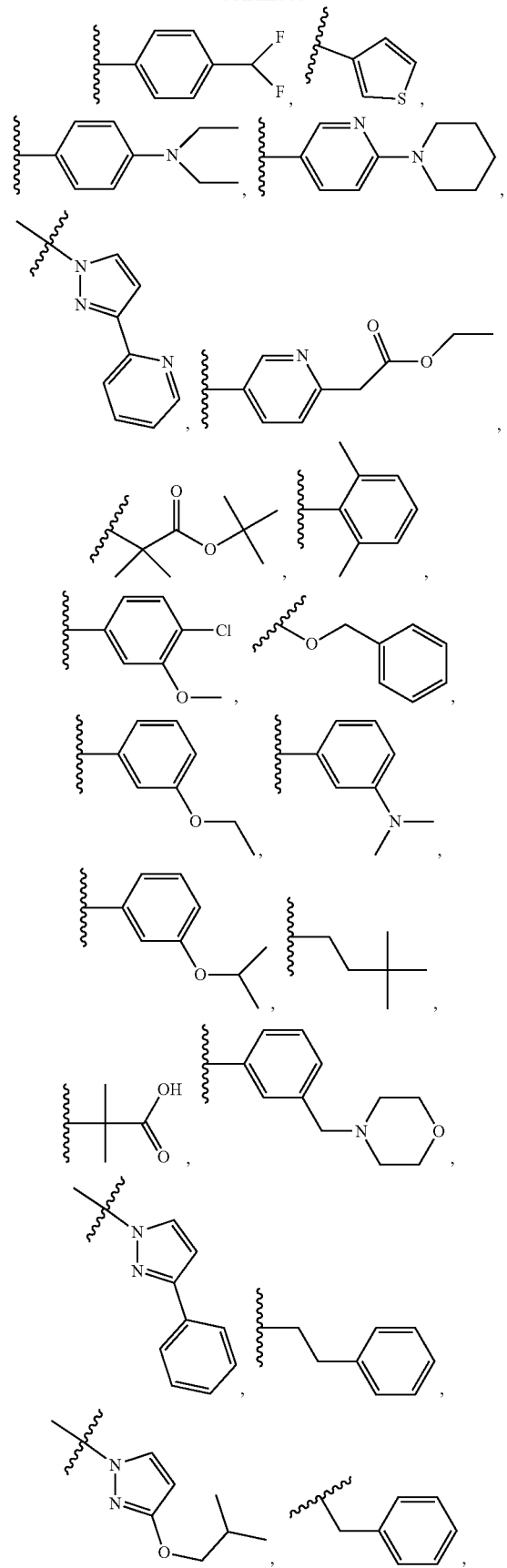
-continued
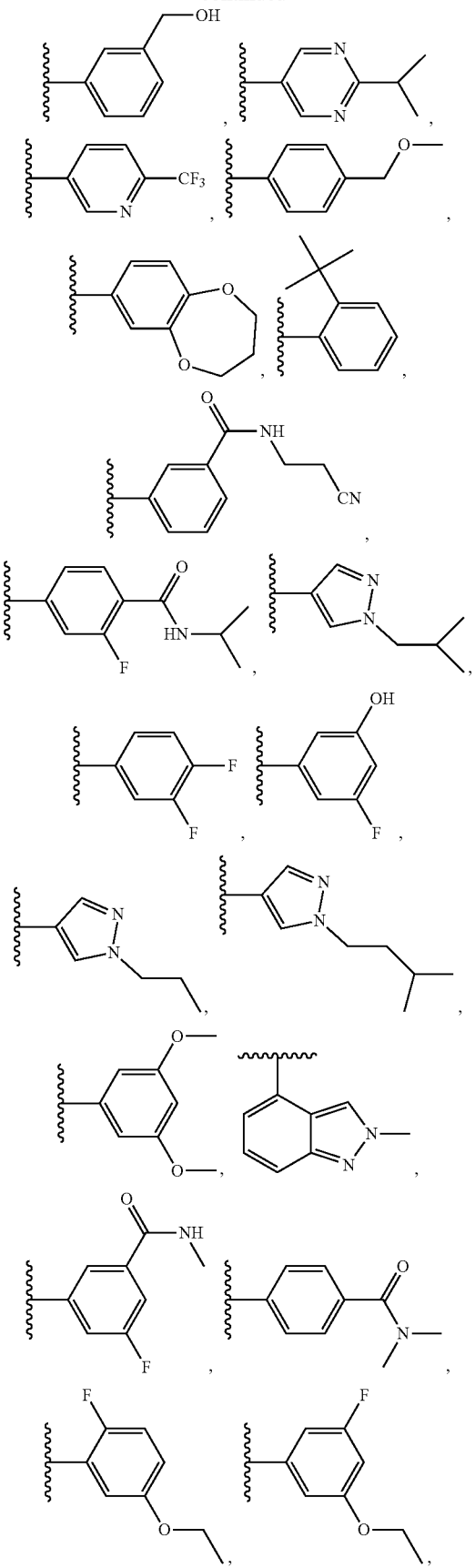

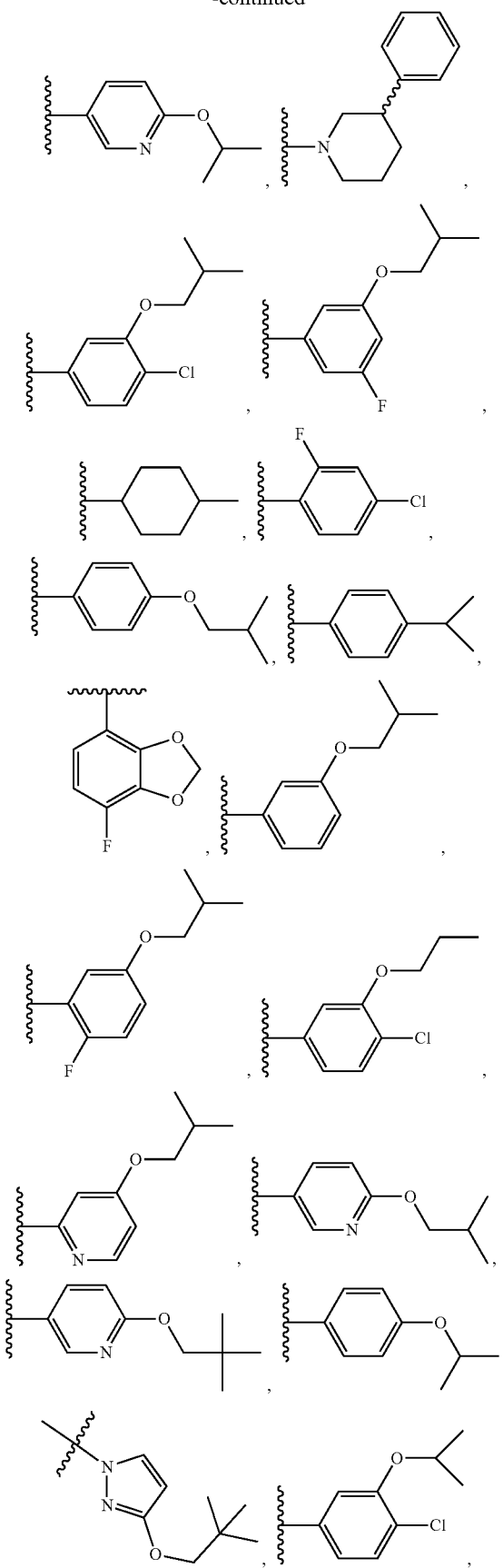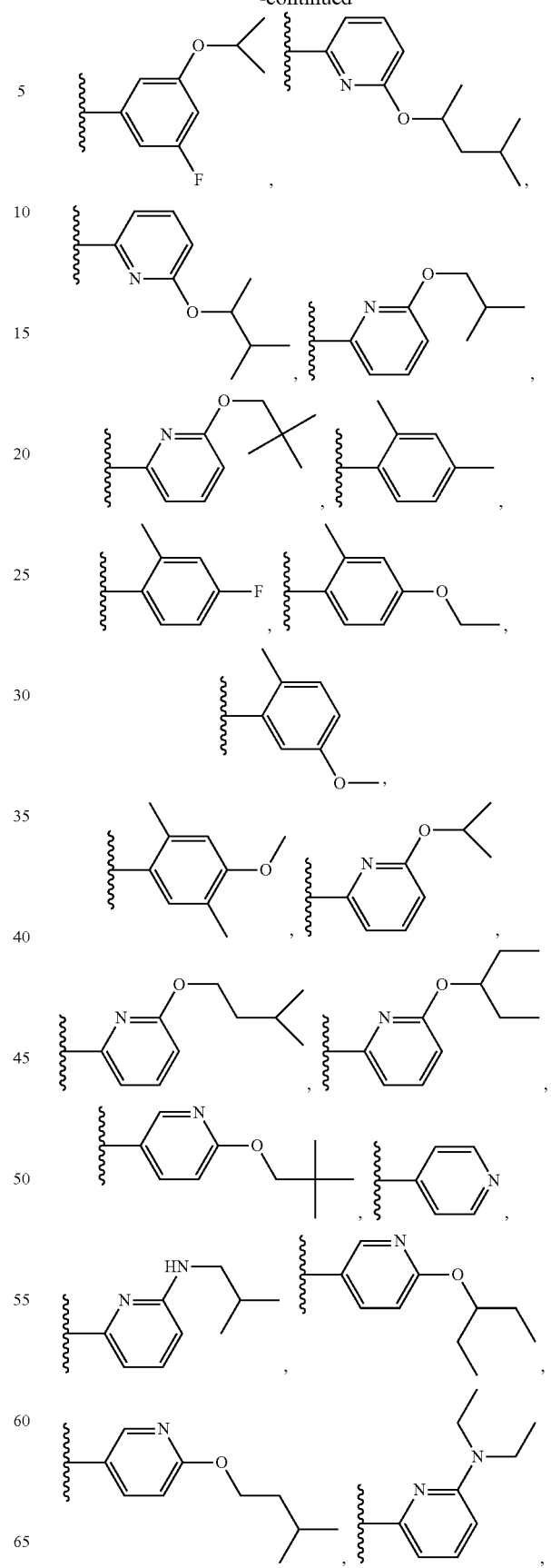

-continued

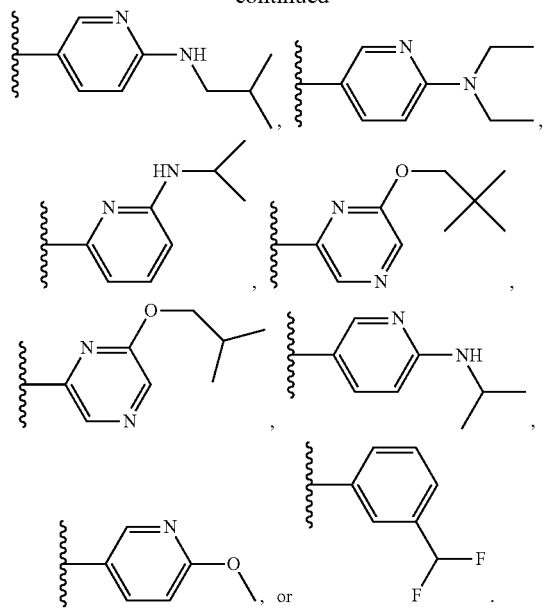

In some embodiments, R₂ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-R₄ wherein up to four CH₂ units are independently replaced with O, CO, S, SO, SO₂ or NR.

In some embodiments, R₂ is a group represented by the corresponding moieties shown in the compounds of Table 1. For example, R₂ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

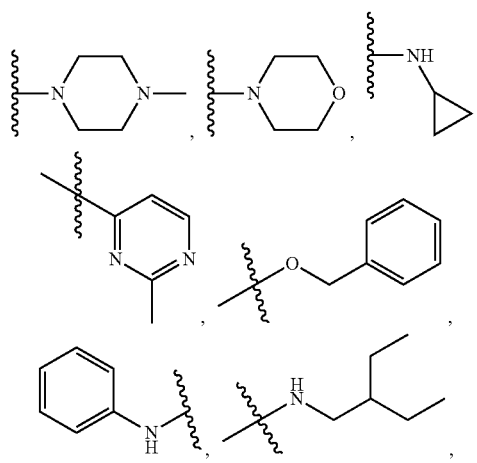

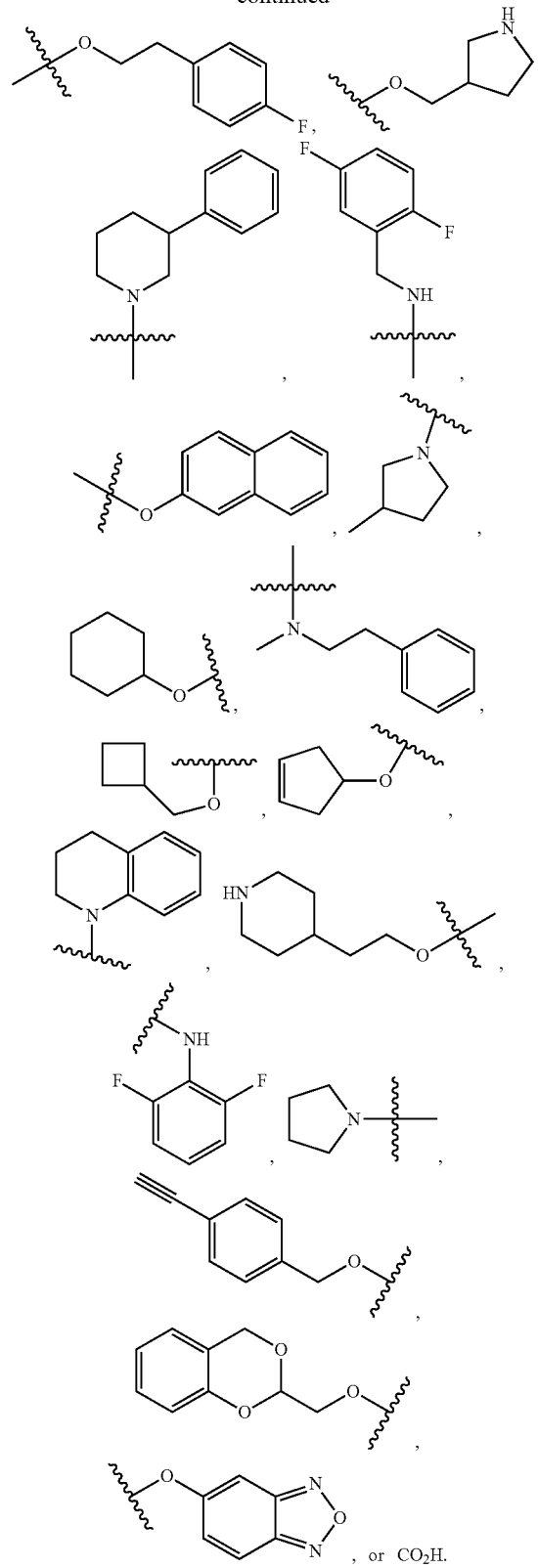

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

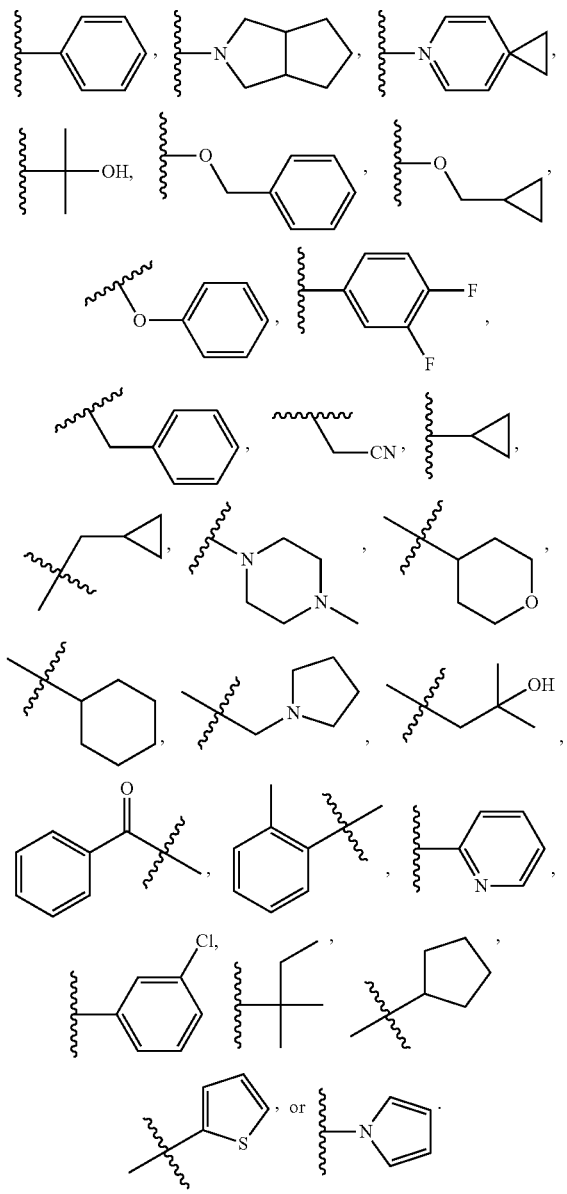

In some embodiments, o is 0. In some embodiments, o is 1. In some embodiments, o is 2.

In some embodiments, n is 0. In some embodiments, n is 1. In some embodiments, n is 2.

In some embodiments, p is 0. In some embodiments, p is 1. In some embodiments, p is 2.

In some embodiments, the invention features a compound of formula Ib-ii:

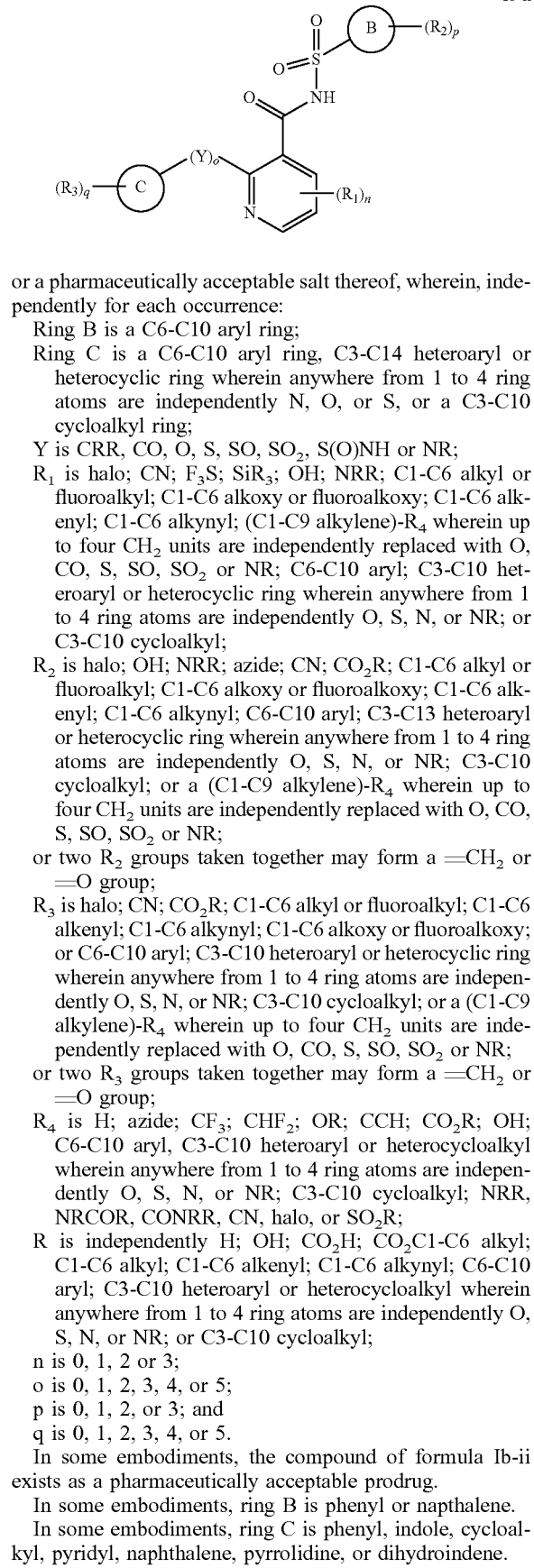

or a pharmaceutically acceptable salt thereof, wherein, independently for each occurrence:

Ring B is a C6-C10 aryl ring;

Ring C is a C6-C10 aryl ring, C3-C14 heteroaryl or heterocyclic ring wherein anywhere from 1 to 4 ring atoms are independently N, O, or S, or a C3-C10 cycloalkyl ring;

Y is CRR, CO, O, S, SO, $SO_2$, S(O)NH or NR;

$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a =$CH_2$ or =O group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a =$CH_2$ or =O group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;
o is 0, 1, 2, 3, 4, or 5;
p is 0, 1, 2, or 3; and
q is 0, 1, 2, 3, 4, or 5.

In some embodiments, the compound of formula Ib-ii exists as a pharmaceutically acceptable prodrug.

In some embodiments, ring B is phenyl or napthalene.

In some embodiments, ring C is phenyl, indole, cycloalkyl, pyridyl, naphthalene, pyrrolidine, or dihydroindene.

In some embodiments, ring C is a group represented by the corresponding moieties shown in the compounds of Table 1. For example, ring C is
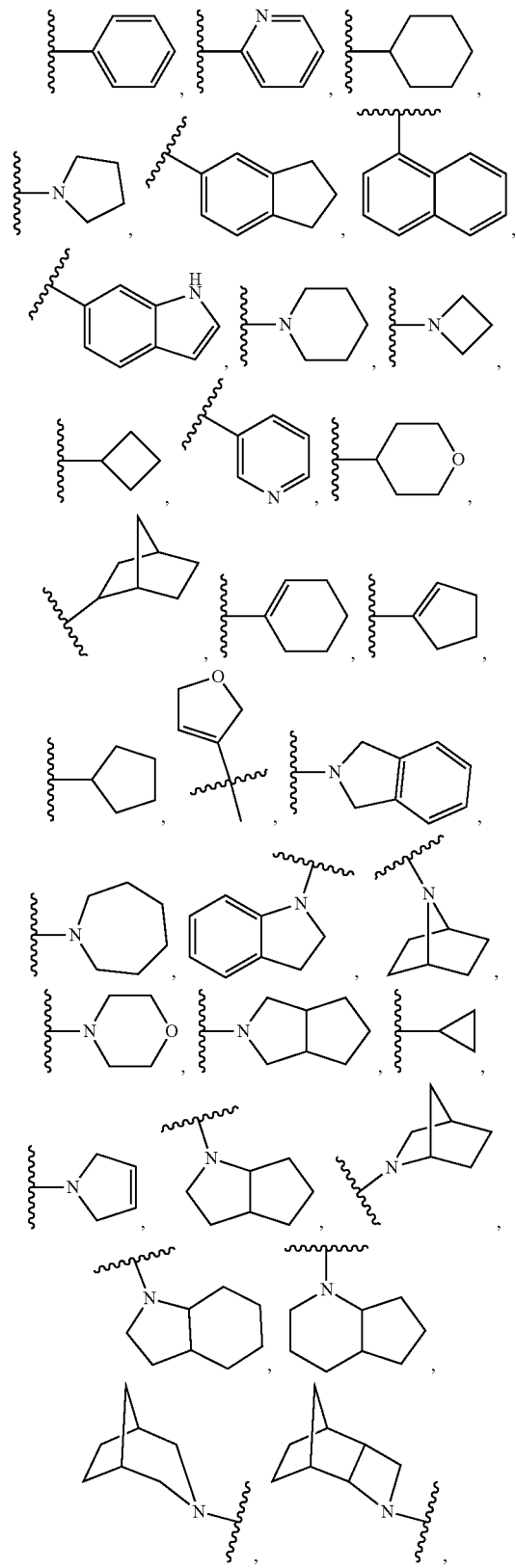
-continued
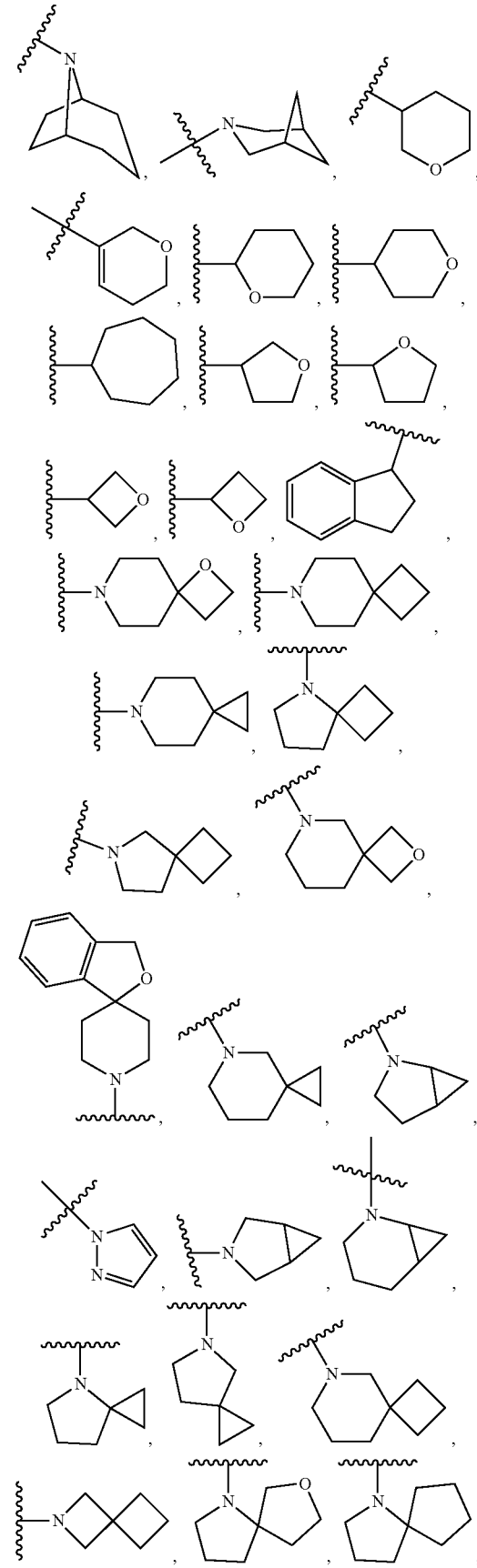

-continued

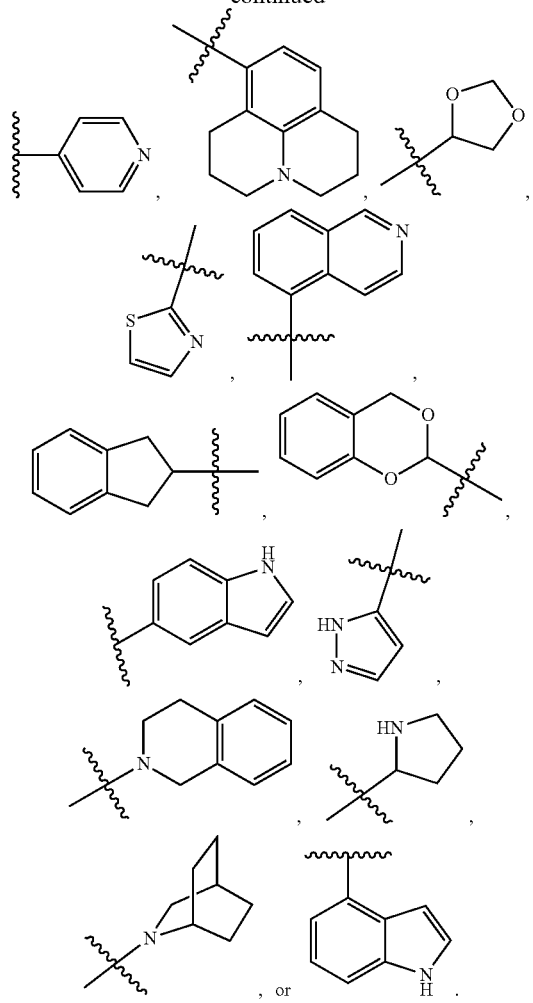

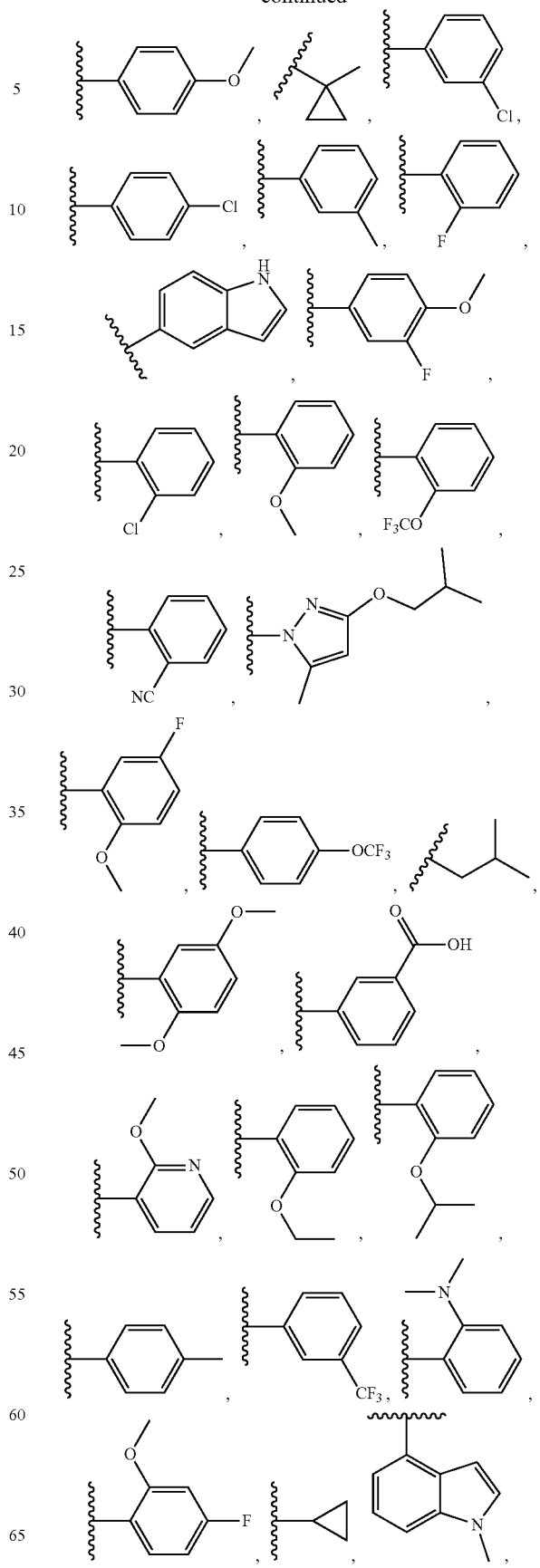

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

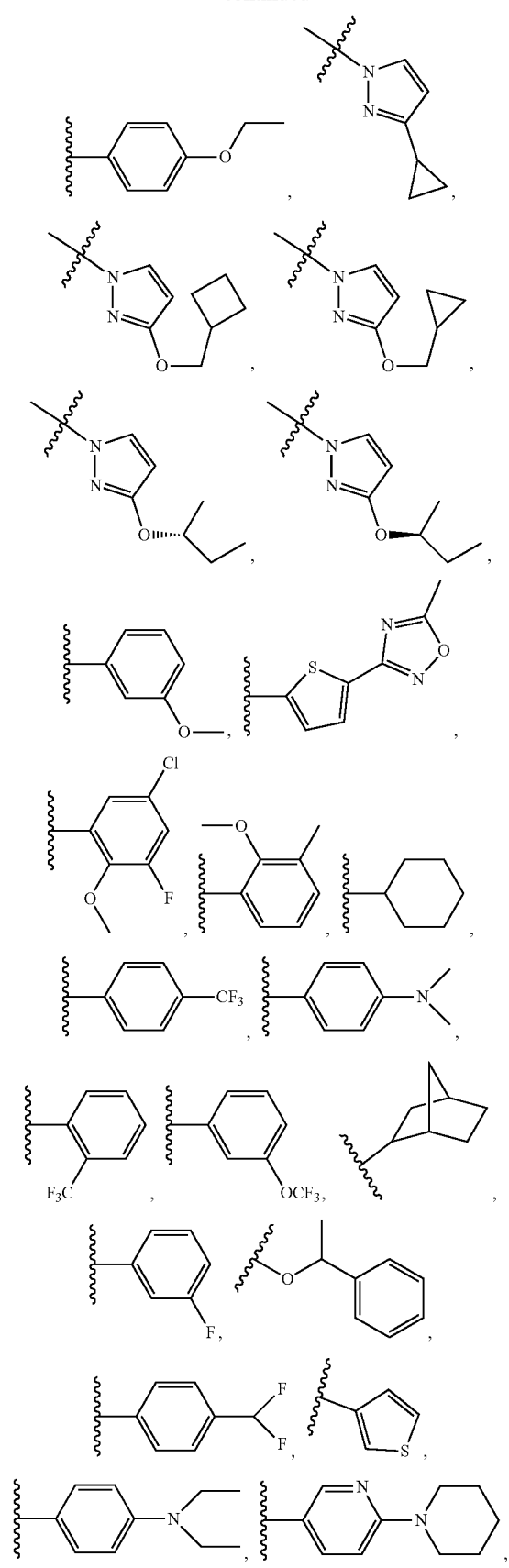
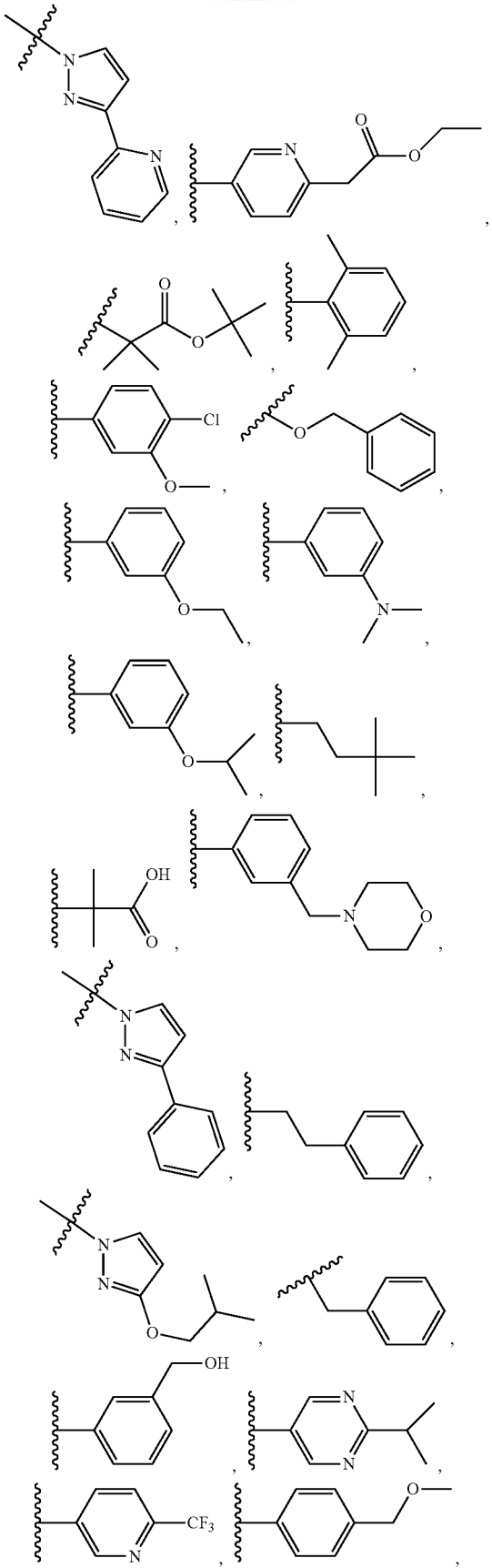

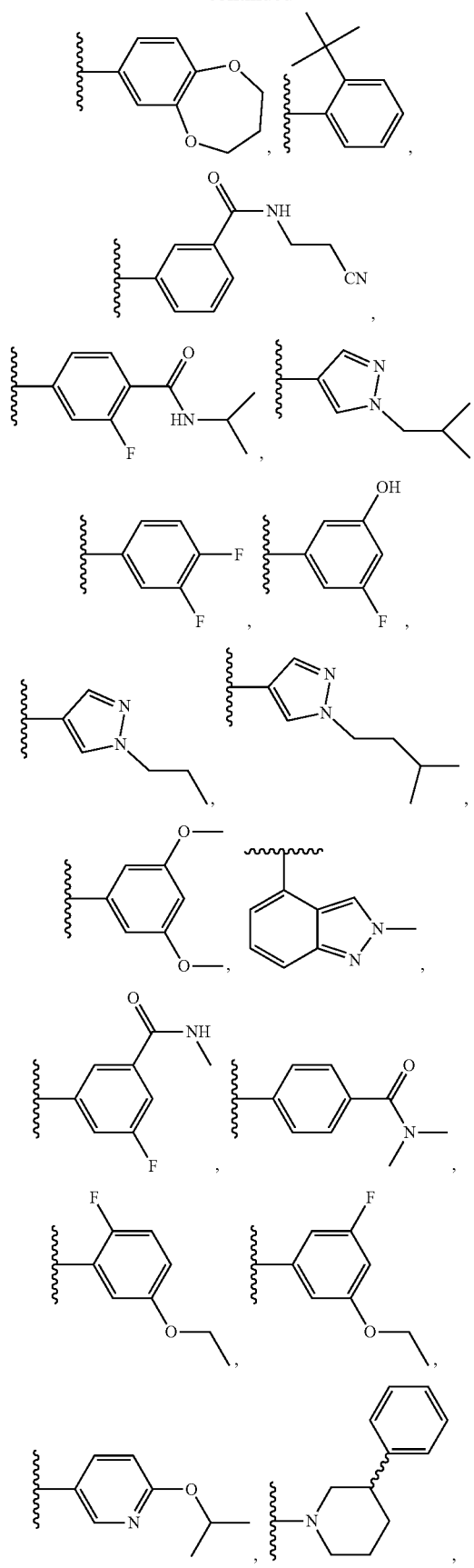
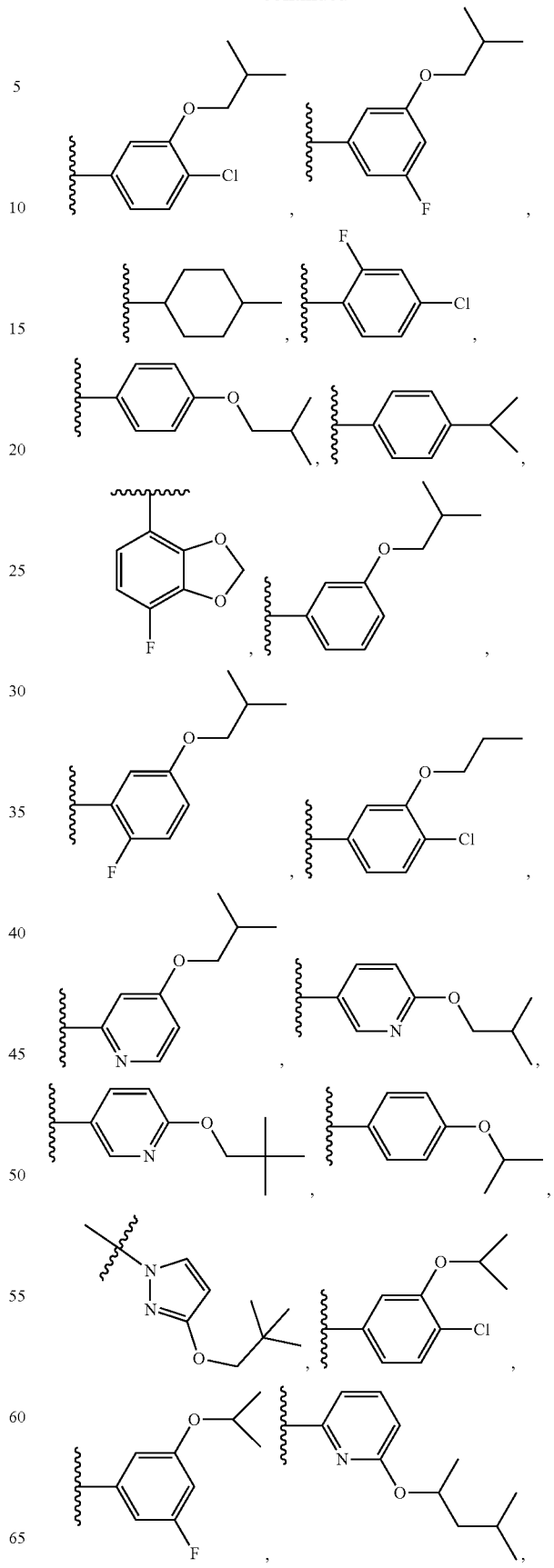

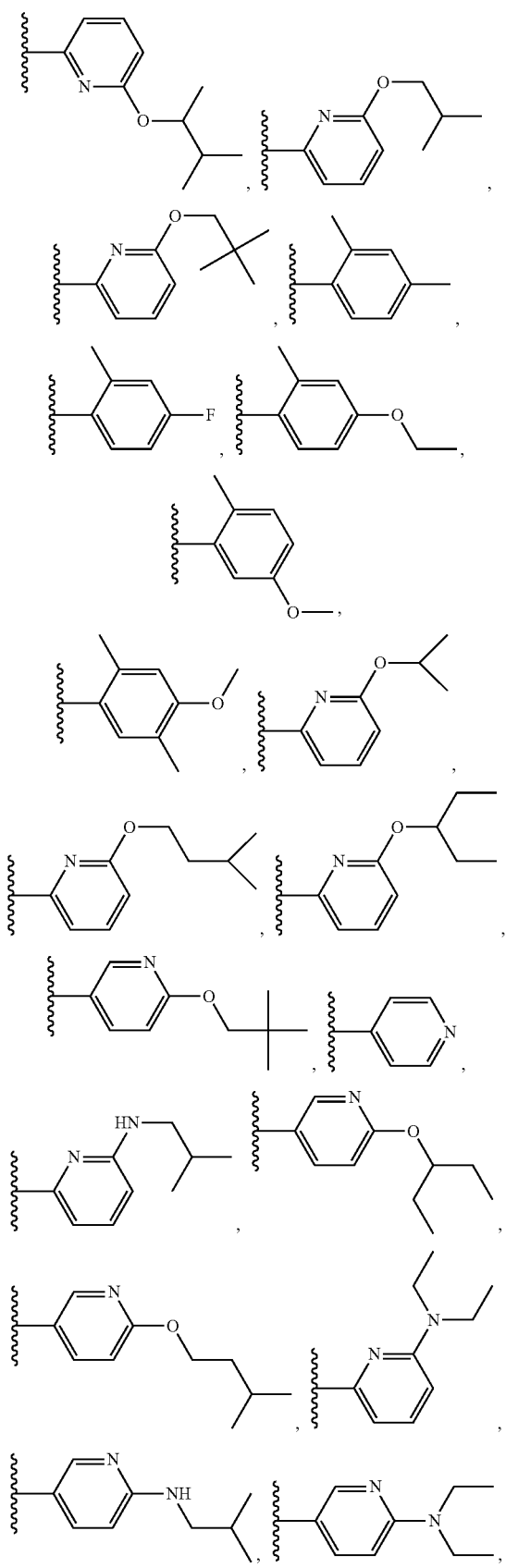

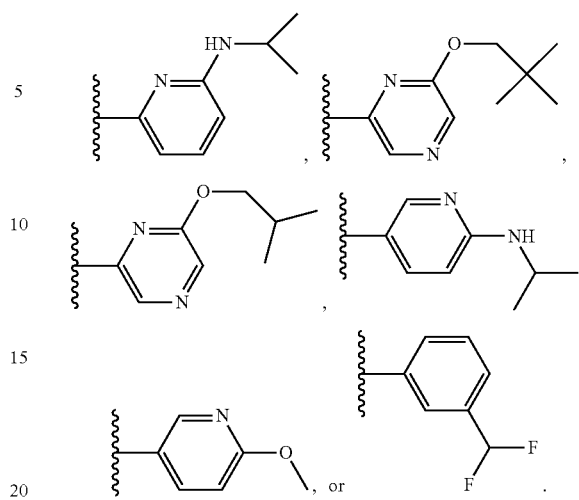

In some embodiments, $R_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

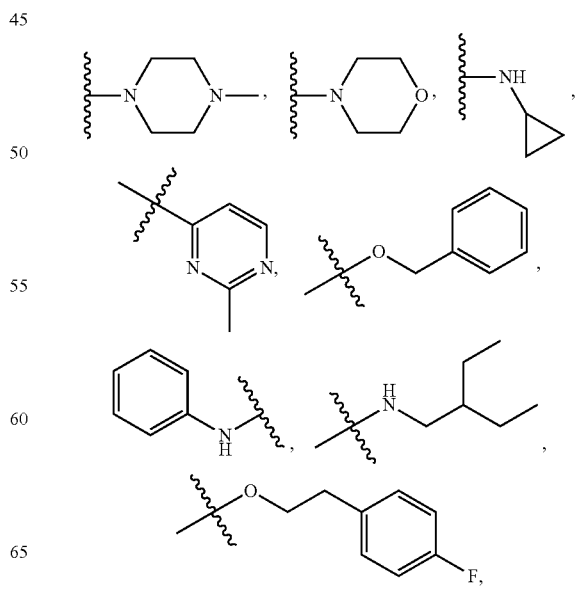

-continued

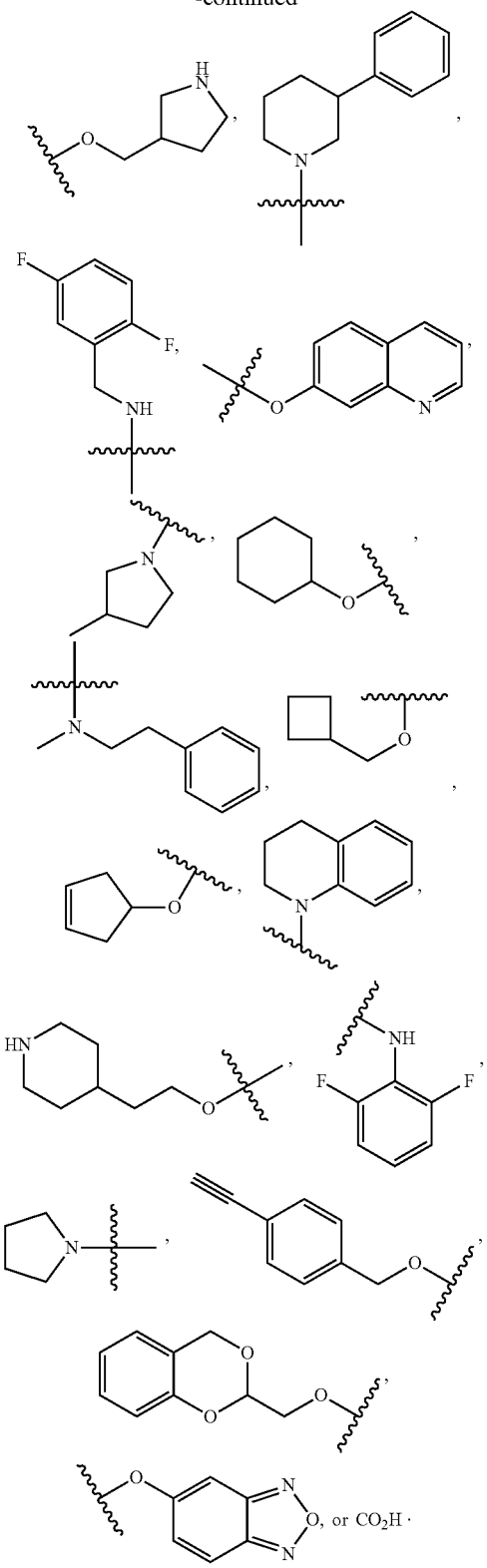

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1.

For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

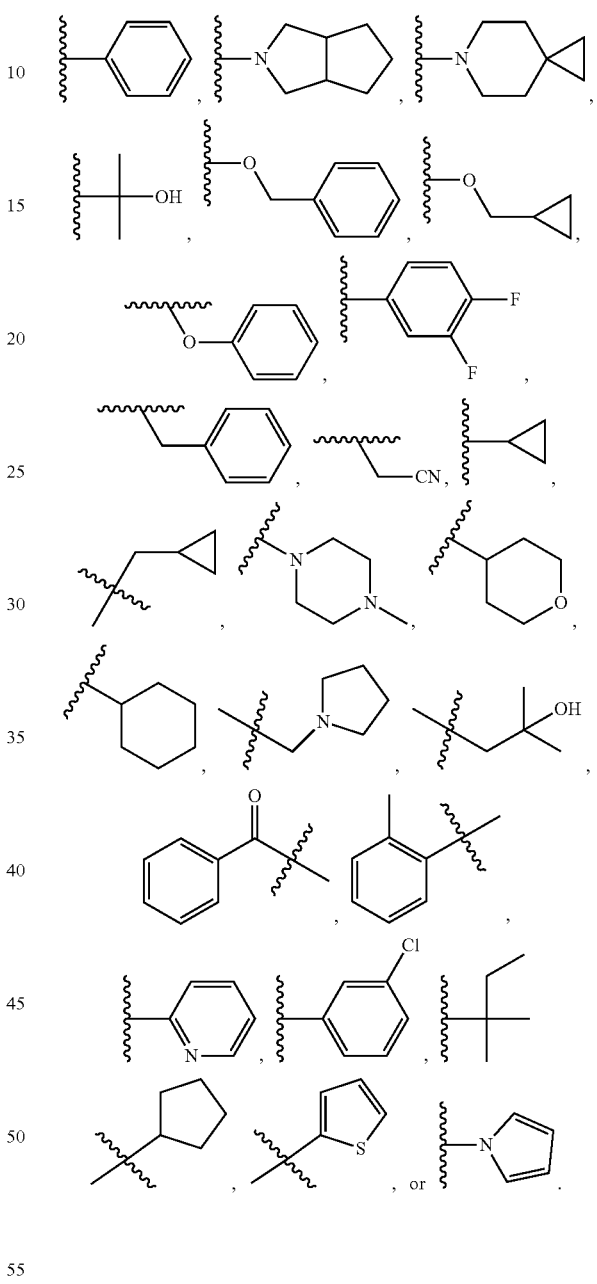

In some embodiments, o is 0. In some embodiments, o is 1. In some embodiments, o is 2.

In some embodiments, n is 0. In some embodiments, n is 1. In some embodiments, n is 2.

In some embodiments, p is 0. In some embodiments, p is 1. In some embodiments, p is 2.

In some embodiments, the invention features a compound of formula Ib-iii:

Ib-iii

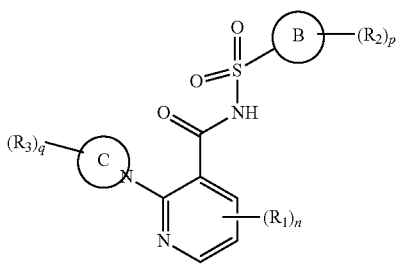

or a pharmaceutically acceptable salt thereof, wherein, independently for each occurrence:
  Ring B is a C6-C10 aryl ring or C3-C10 heteroaryl or heterocyclic ring wherein anywhere from 1 to 4 ring atoms are independently O, S, N, or NR;
  Ring C is a C3-C14 heteroaryl or heterocyclic ring wherein anywhere from 1 to 4 ring atoms are independently N, O, or S, and wherein one nitrogen on Ring C is the point of attachment to the pyridine ring;
  $R_1$ is halo; CN; F5S; SiR$_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four CH$_2$ units are independently replaced with O, CO, S, SO, SO$_2$ or NR; C6-C10 aryl; C3-C10 heteroaryl or heterocyclic ring wherein anywhere from 1 to 4 ring atoms are independently O, S, N, or NR; or C3-C10 cycloalkyl;
  $R_2$ is halo; OH; NRR; azide; CN; CO$_2$R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four CH$_2$ units are independently replaced with O, CO, S, SO, SO$_2$ or NR;
    or two $R_2$ groups taken together may form a =CH$_2$ or =O group;
  $R_3$ is halo; CN; CO$_2$R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four CH$_2$ units are independently replaced with O, CO, S, SO, SO$_2$ or NR;
    or two $R_3$ groups taken together may form a =CH$_2$ or =O group;
  $R_4$ is H; azide; CF$_3$; CHF$_2$; OR; CCH; CO$_2$R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO$_2$R;
  R is independently H; OH; CO$_2$H; CO$_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
  n is 0, 1, 2 or 3;
  p is 0, 1, 2, or 3; and
  q is 0, 1, 2, 3, 4, or 5.
In some embodiments, the compound of formula Ib-iii exists as a pharmaceutically acceptable prodrug.
In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

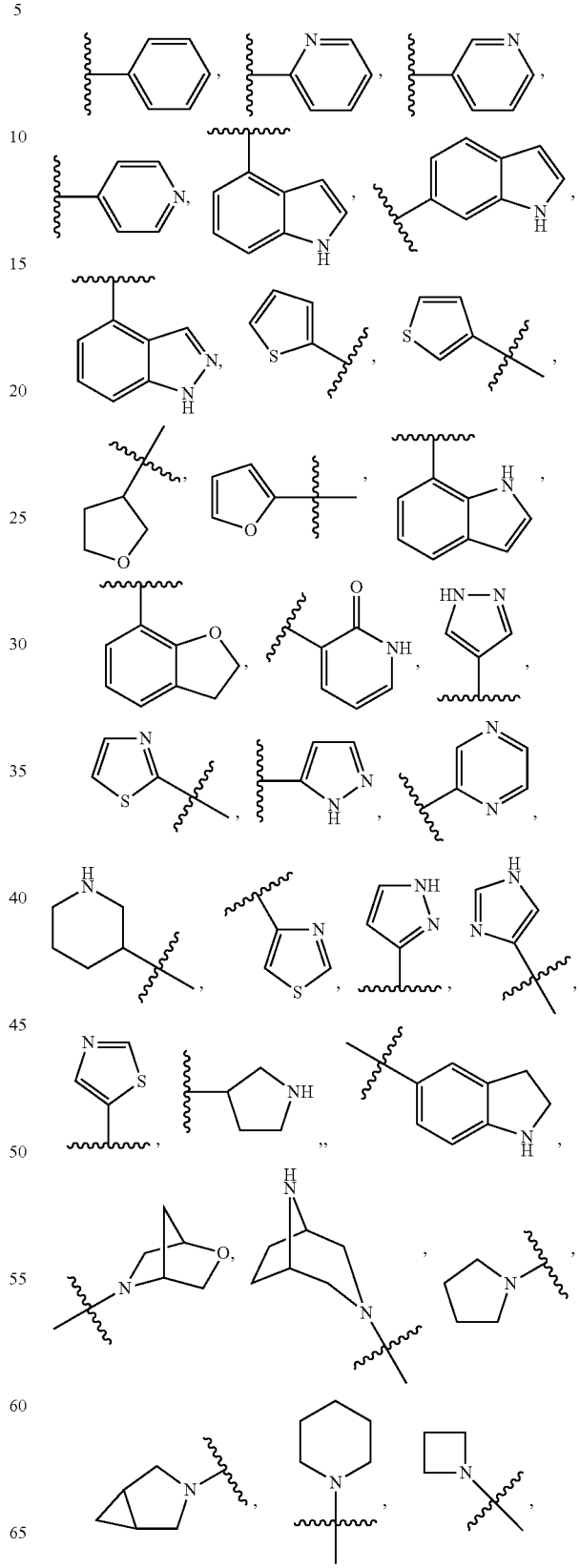

-continued

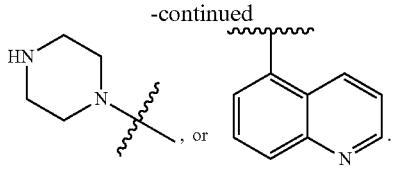, or

In some embodiments, ring C is indole, piperidine, azepane, azetadine, indoline, isoindoline, or pyrrolidine.

In some embodiments, ring C is a group represented by the corresponding moieties shown in the compounds of Table 1. For example, ring C is

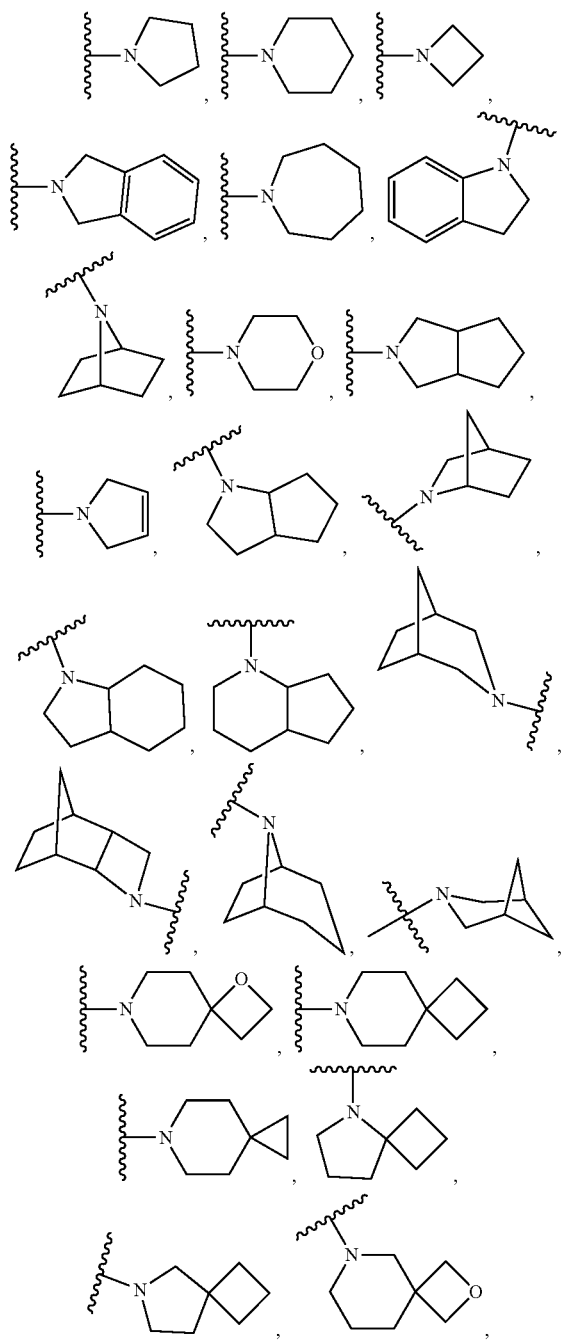

-continued

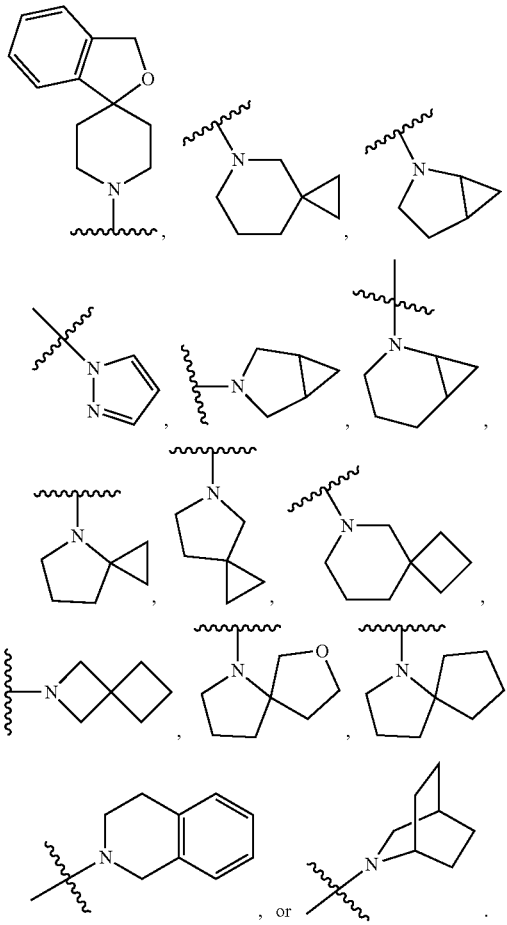

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

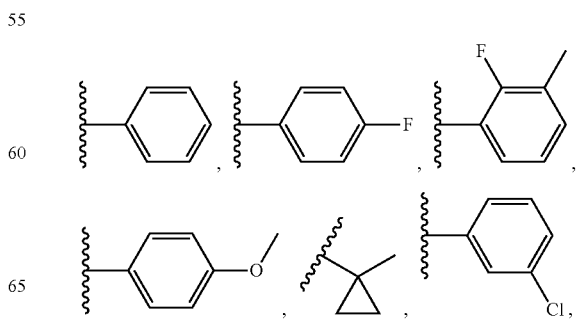

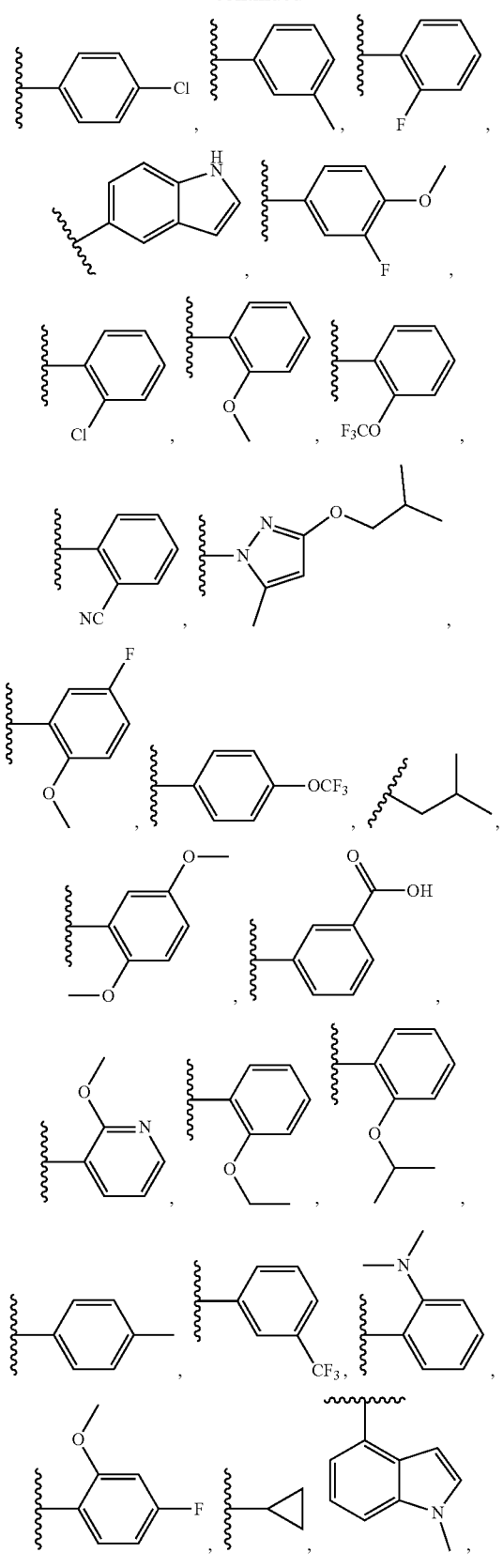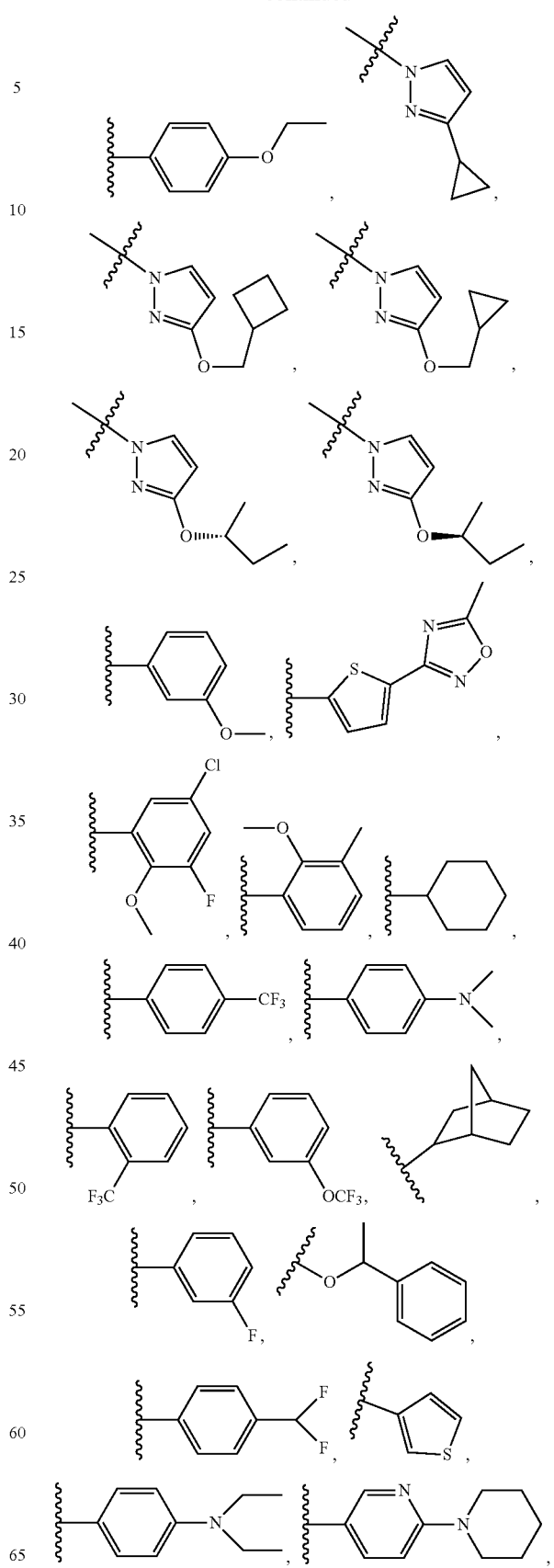

149
-continued
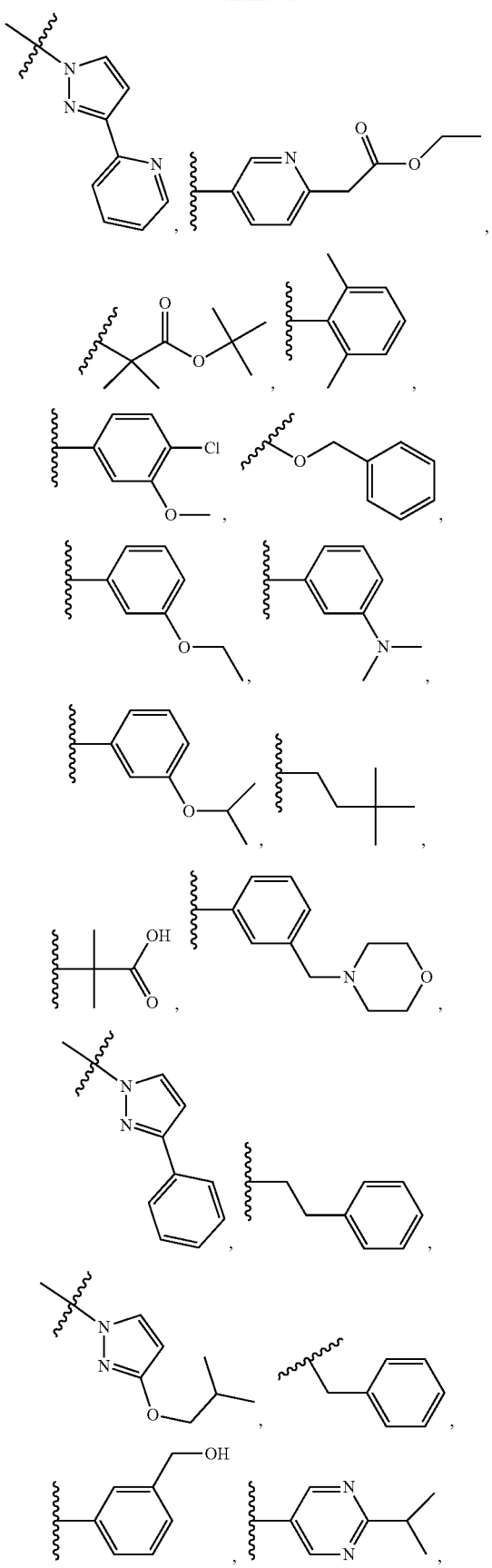
150
-continued
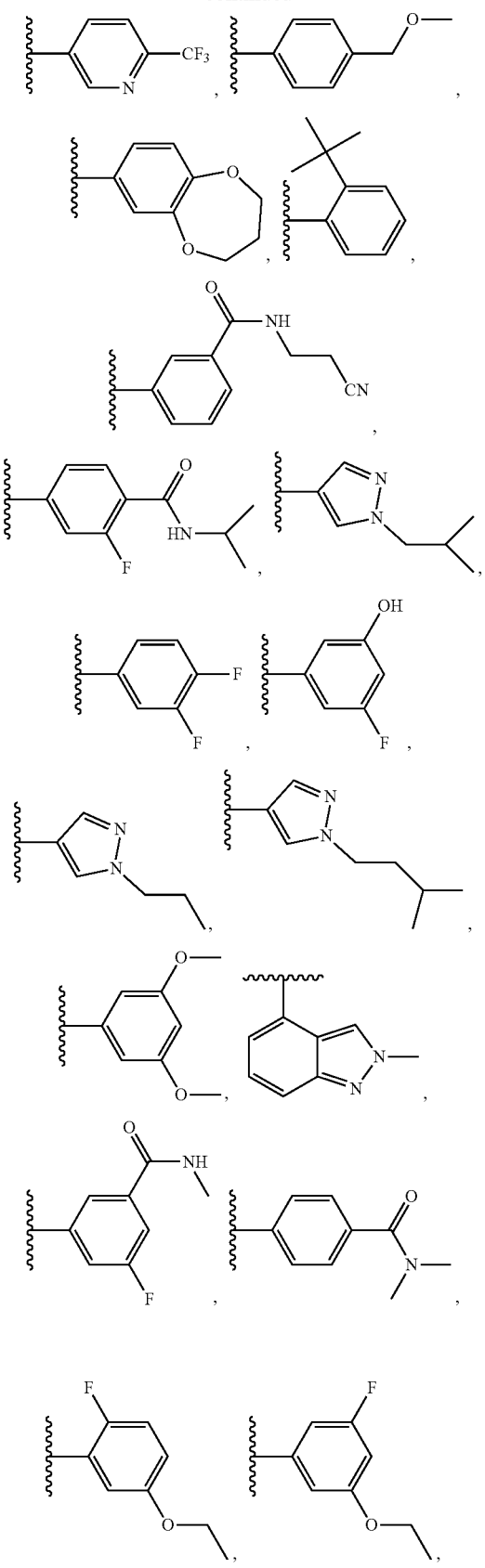

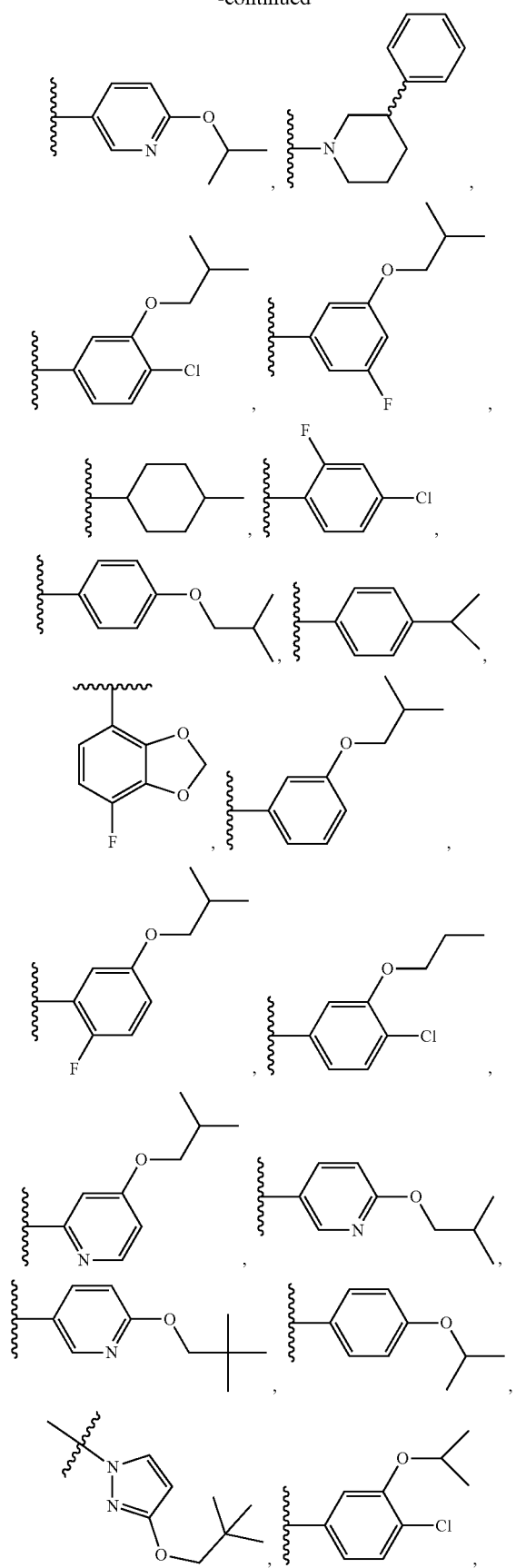
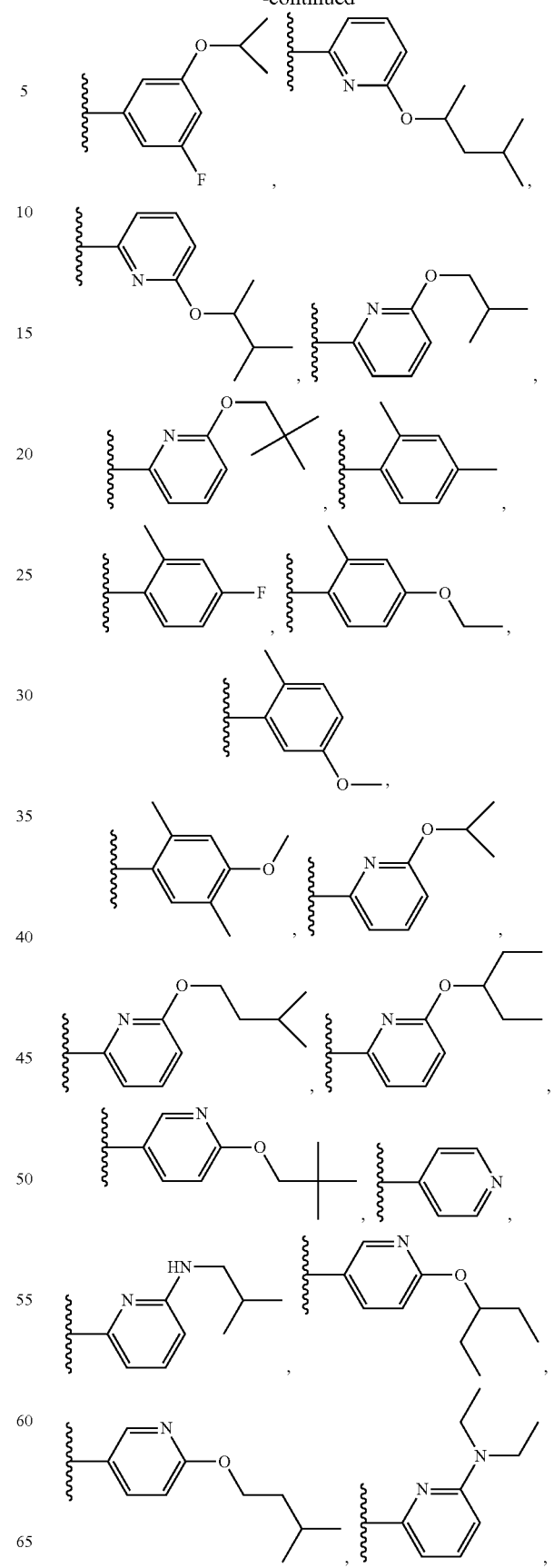

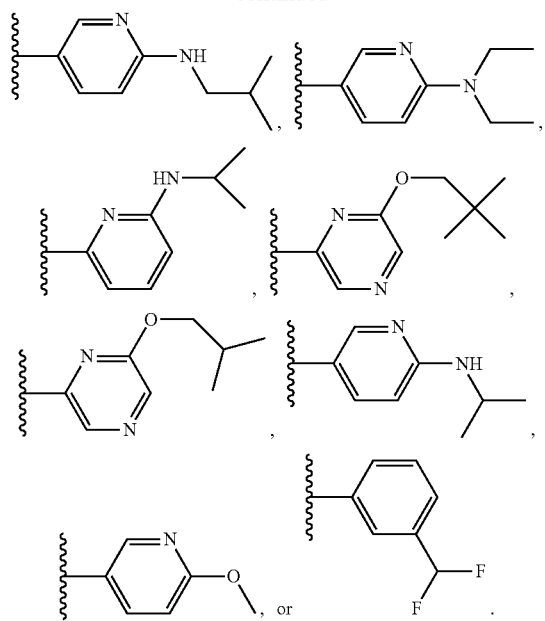

In some embodiments, R$_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-R$_4$ wherein up to four CH$_2$ units are independently replaced with O, CO, S, SO, SO$_2$ or NR.

In some embodiments, R$_2$ is a group represented by the corresponding moieties shown in the compounds of Table 1. For example, R$_2$ is Cl, F, OH, CN, N$_3$, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, CH$_3$, CH$_2$OH, CH$_2$CH$_3$, CH$_2$CH$_2$CH$_3$, =O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

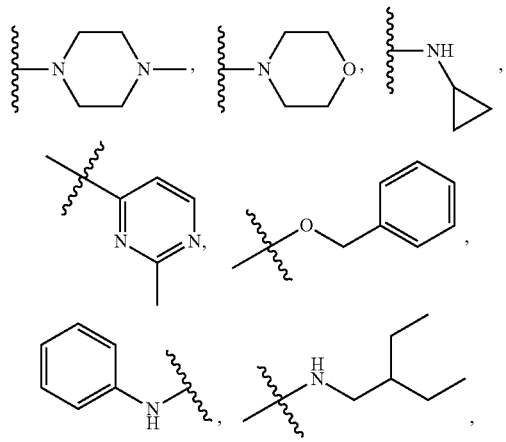

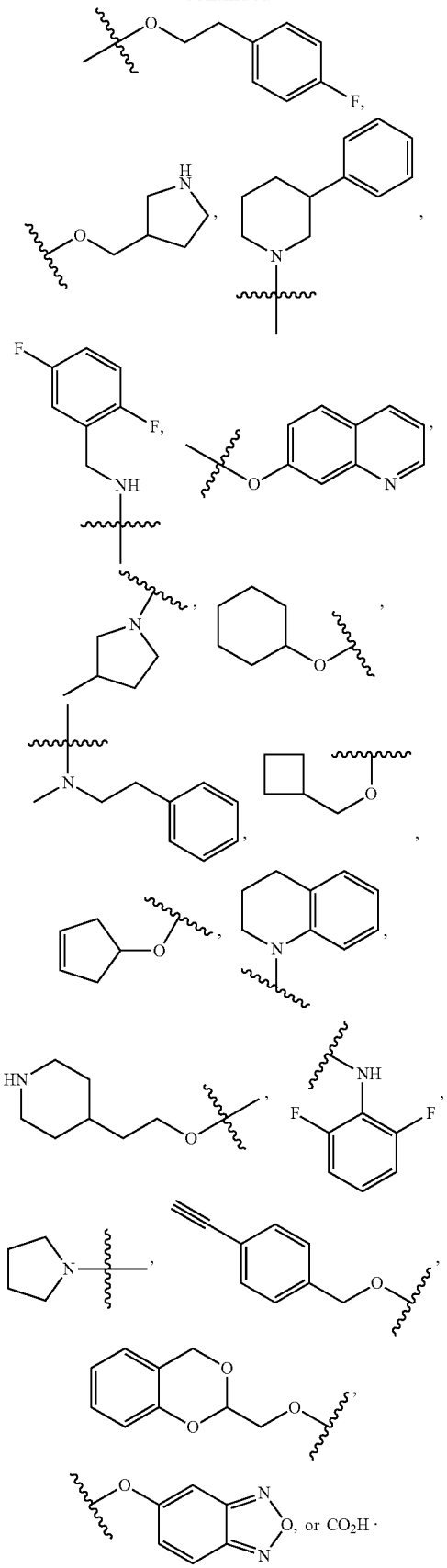

, or CO$_2$H.

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu,

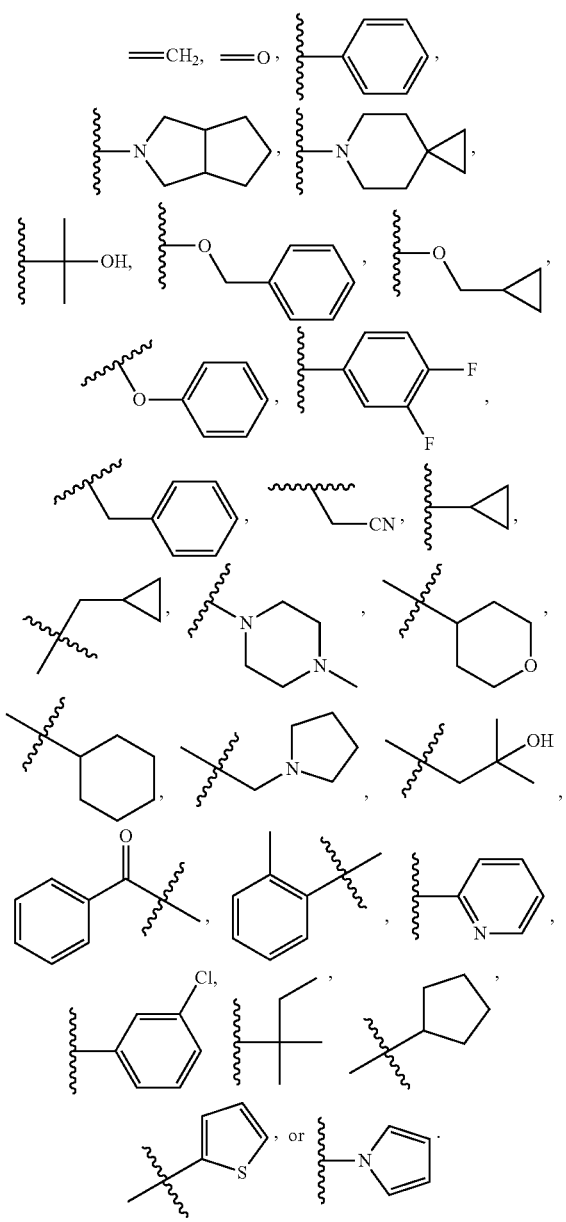

In some embodiments, n is 0. In some embodiments, n is 1. In some embodiments, n is 2.

In some embodiments, p is 0. In some embodiments, p is 1. In some embodiments, p is 2.

In some embodiments, $R_1$ is phenyl, pyridine, or pyrazole, and n is 1. In some embodiments, $R_1$ is phenyl, pyridine, or pyrazole, n is 1, $R_2$ is amino or alkyl, and p is 0 or 1. In some embodiments, $R_1$ is phenyl, pyridine, or pyrazole, n is 1, $R_3$ is alkyl, such as methyl, and q is 1, 2, 3, or 4.

In some embodiments, the invention features a compound of formula Ib-iii-1:

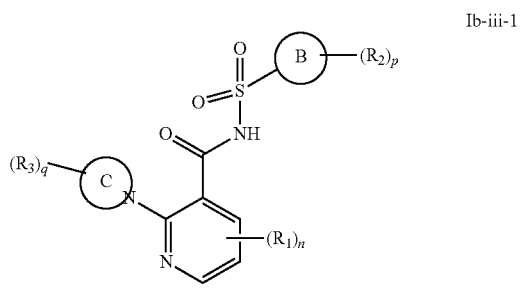

Ib-iii-1 or a pharmaceutically acceptable salt thereof, wherein, independently for each occurrence:

Ring B is a C3-C10 heteroaryl ring wherein anywhere from 1 to 4 ring atoms are independently O, S, N, or NR;

Ring C is a C3-C14 heteroaryl or heterocyclic ring wherein anywhere from 1 to 4 ring atoms are independently N, O, or S, and wherein one nitrogen on Ring C is the point of attachment to the pyridine ring;

$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a =$CH_2$ or =O group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a =$CH_2$ or =O group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;
o is 0, 1, 2, 3, 4, or 5;
p is 0, 1, 2, or 3; and
q is 0, 1, 2, 3, 4, or 5.

In some embodiments, the compound of formula Ib-iii-1 exists as a pharmaceutically acceptable prodrug.

In some embodiments, ring B is pyridyl, pyridine-2(1H)-one, pyrazole, indole, aza-indole, thiophene, dihydrobenzofuran, or quinoline.

In some embodiments, ring B is a group represented by the corresponding moieties shown in the compounds of Table 1. For example, ring B is

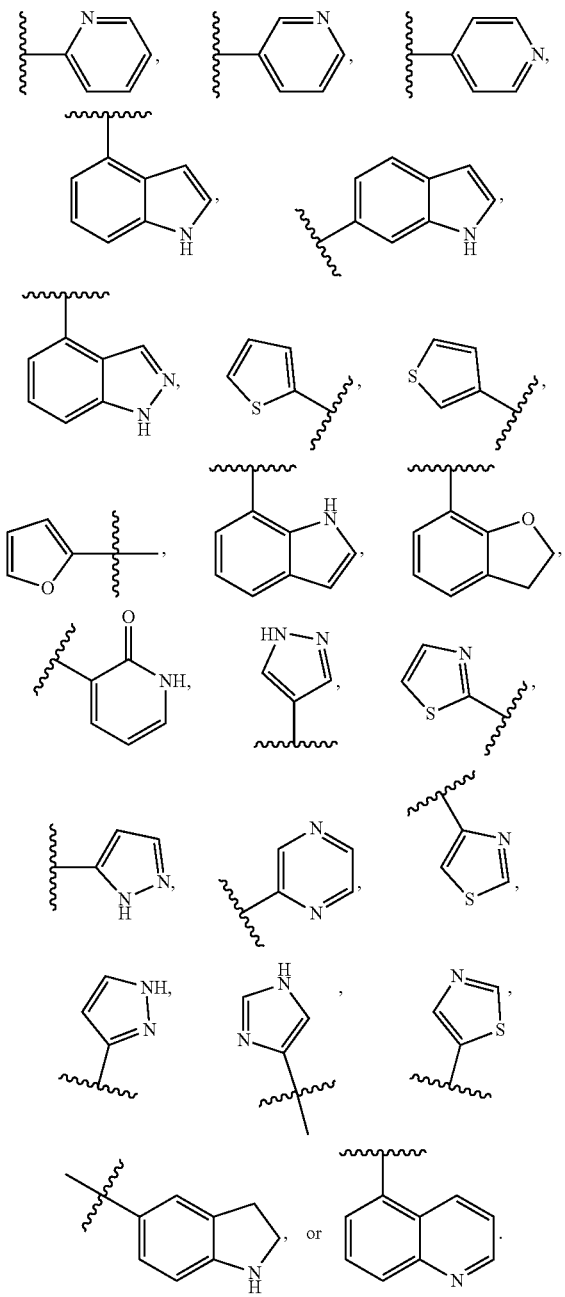

In some embodiments, ring C is indole, piperidine, azepane, azetadine, indoline, isoindoline, or pyrrolidine.

In some embodiments, ring C is a group represented by the corresponding moieties shown in the compounds of Table 1. For example, ring C is

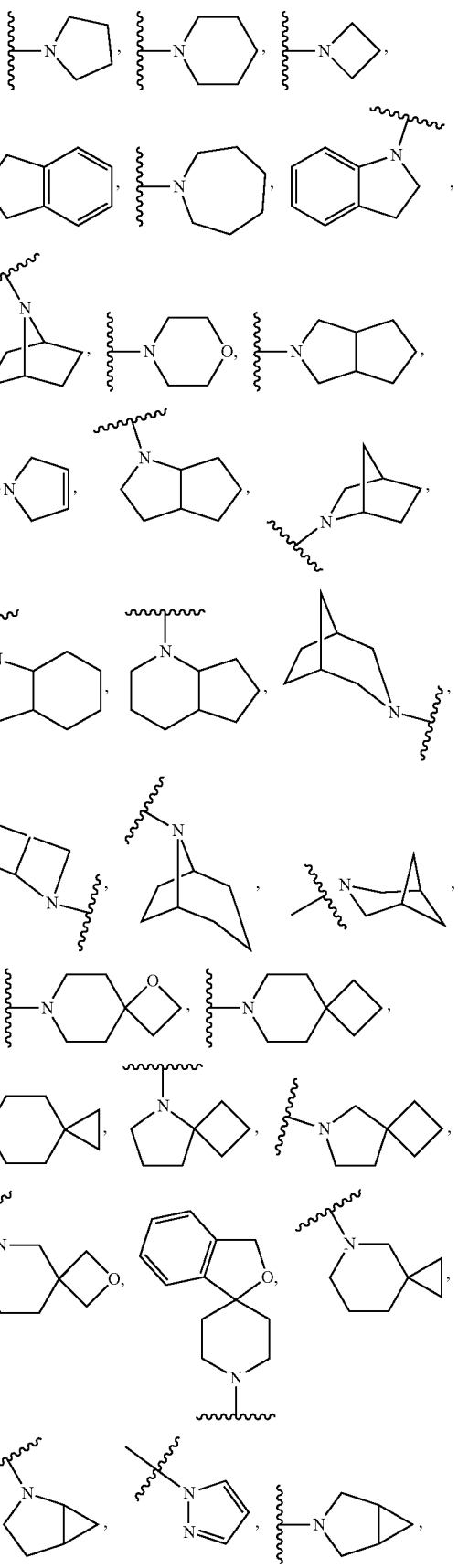

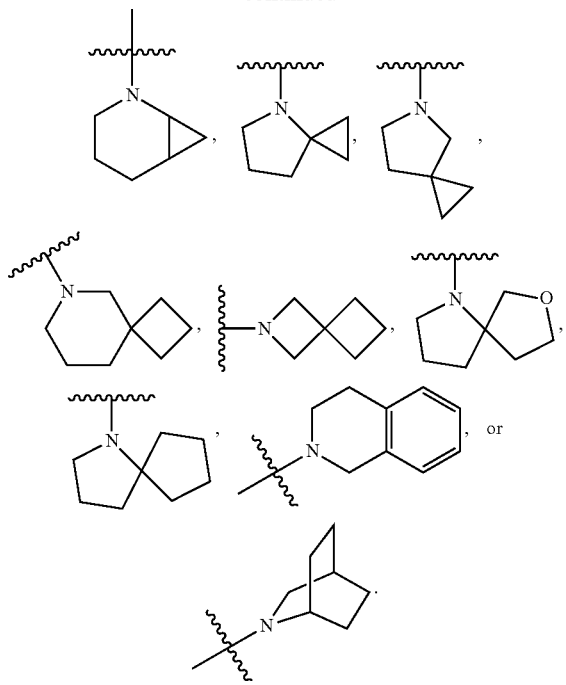

In some embodiments, R₁ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-R₄ wherein up to four CH₂ units are independently replaced with O, CO, S, SO, SO₂ or NR, wherein all rings are optionally substituted with one or more groups selected from halo, C1-C6 alkyl, C1-C6 alkoxy, C1-C6 fluoroalkyl, C1-C6 fluoroalkoxy, OH, CH₂OH, CH₂OCH₃, CN, CO₂H, amino, amido, C3-C10 heteroaryl, and C3-C10 heterocycloalkyl.

In some embodiments, R₁ is a group represented by the corresponding moieties shown in the compounds of Table 1. For example, R₁ is CH₃, Cl, F, CN, OCH₃, CF₃, CH₂CH₃, tBu, CH(CH₃)₂, OCH₂CH₂OCH₂CH₃,

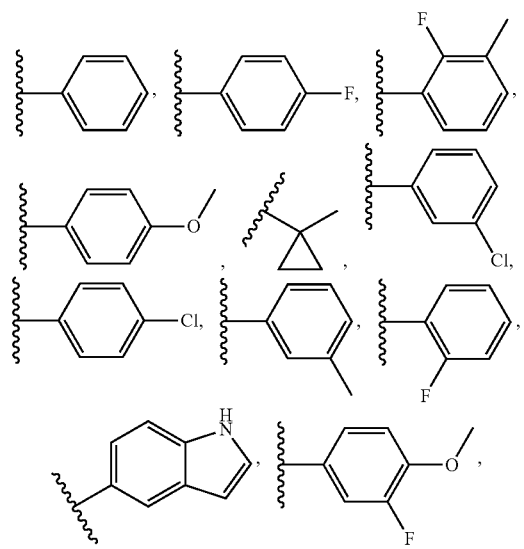

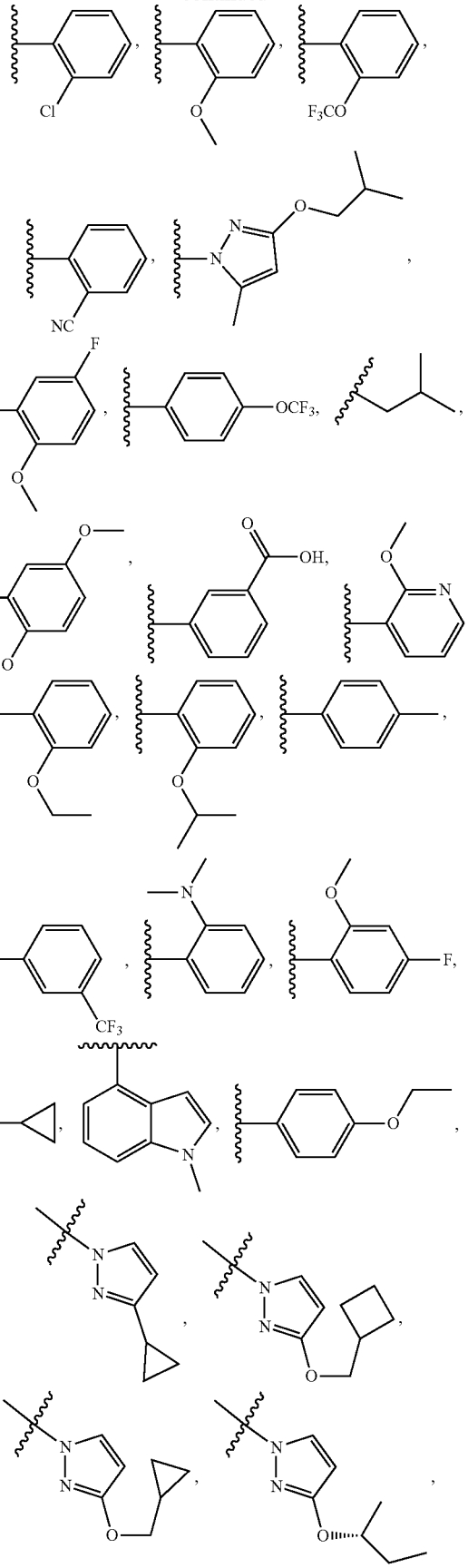

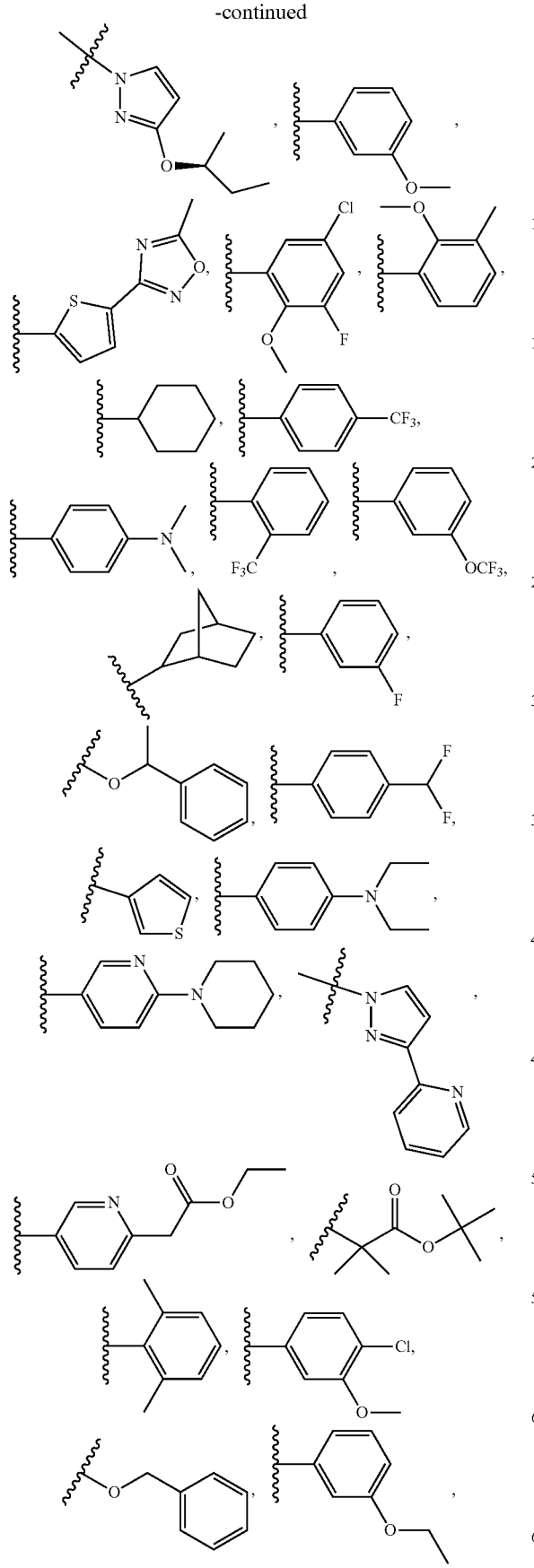
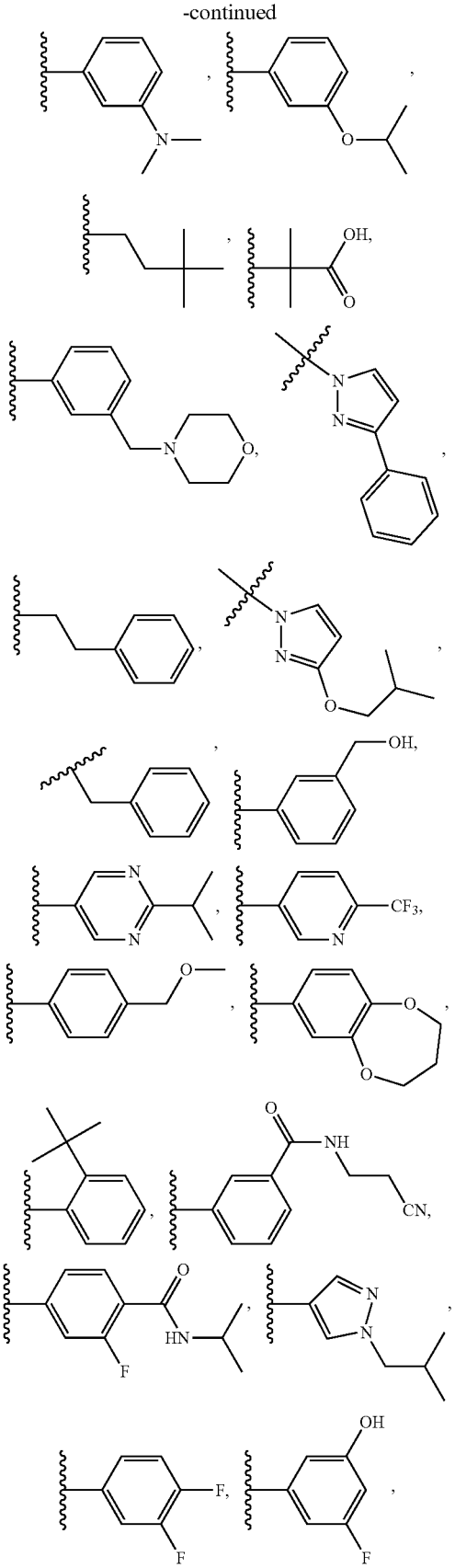

163
-continued
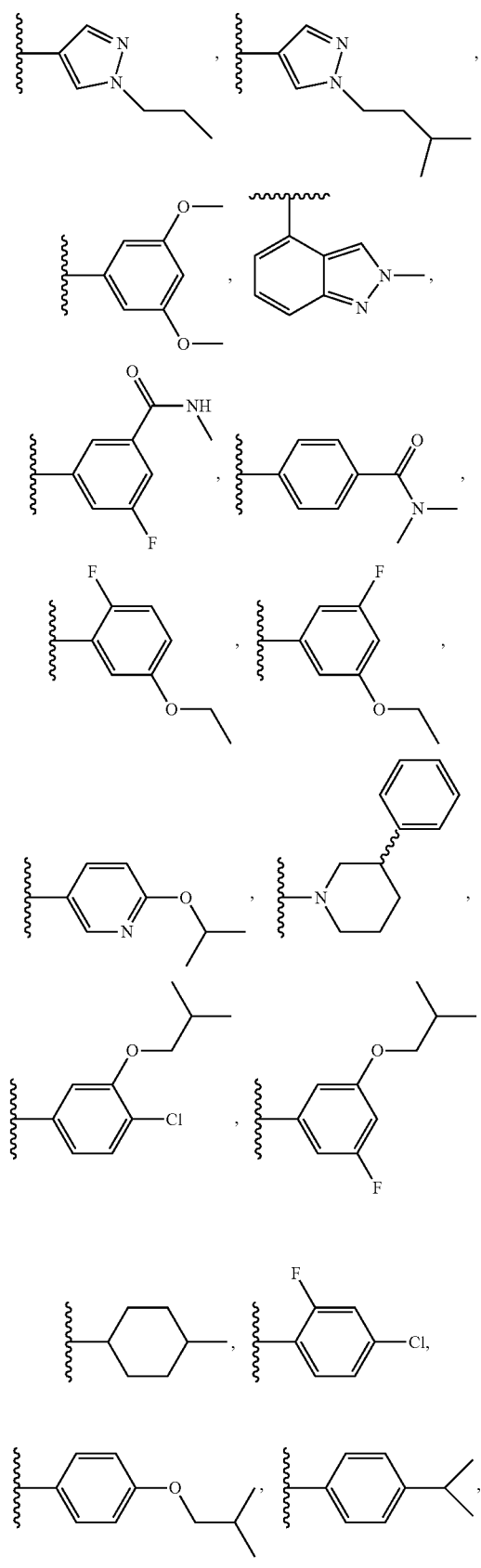
164
-continued
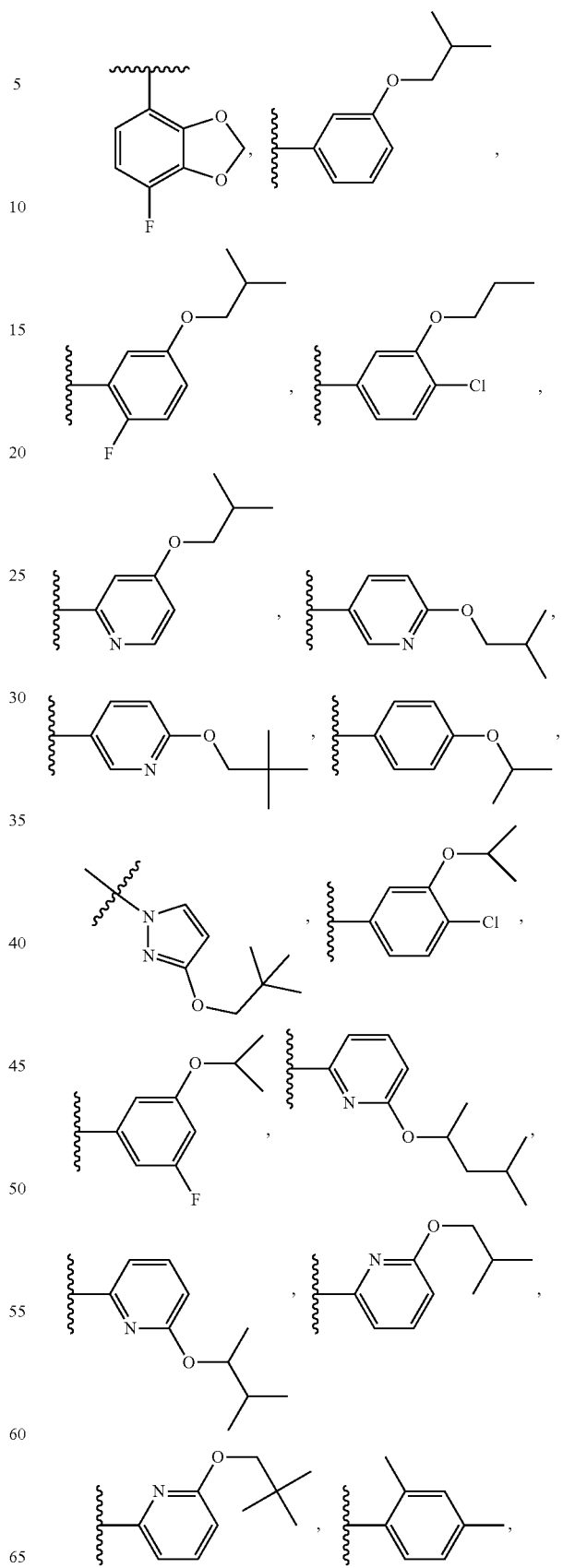

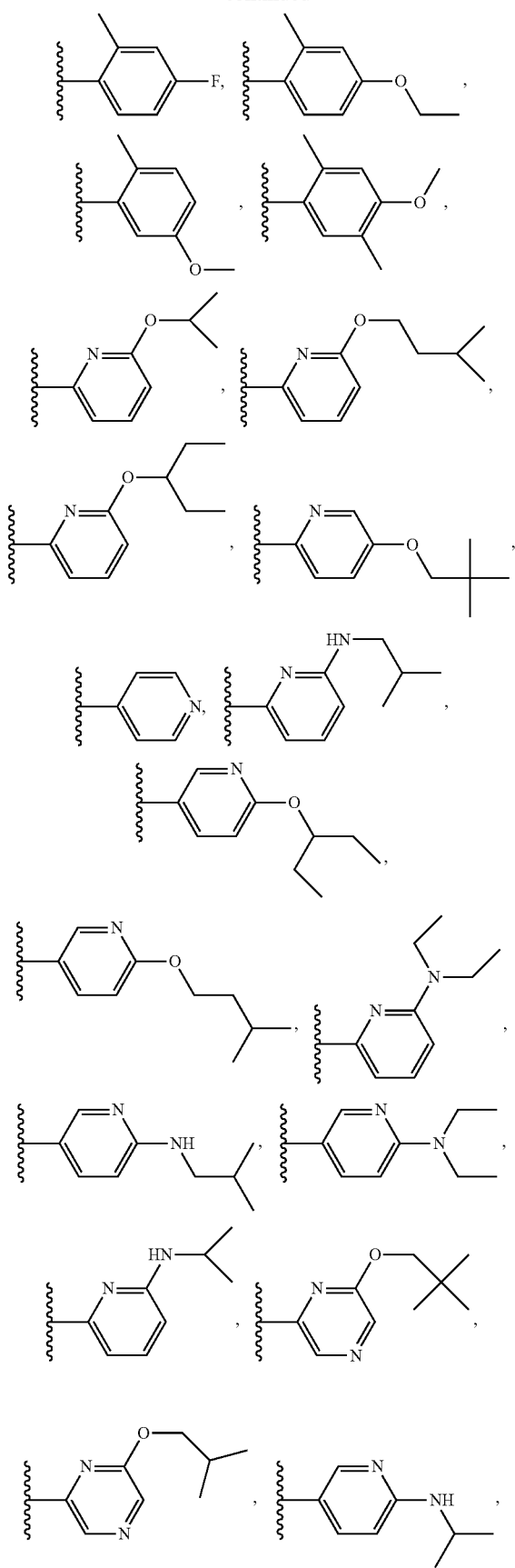

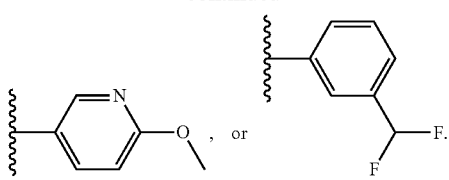

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

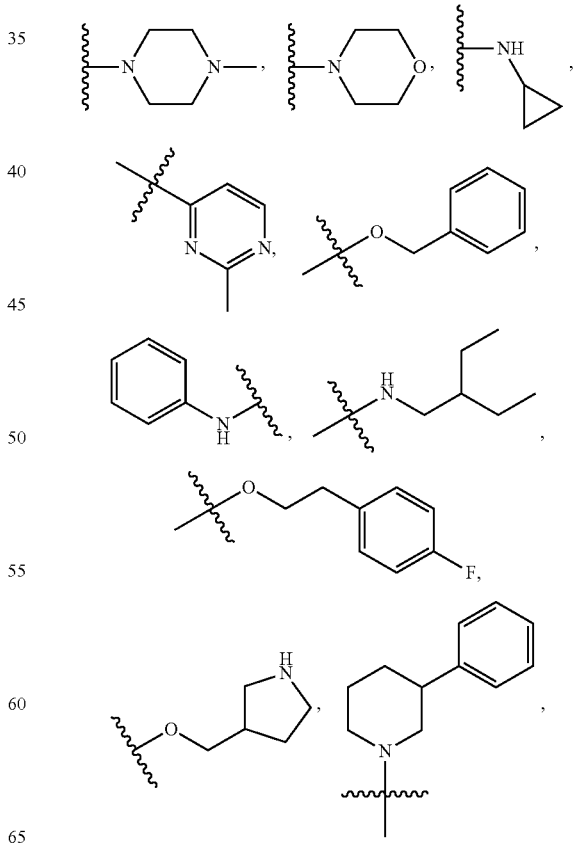

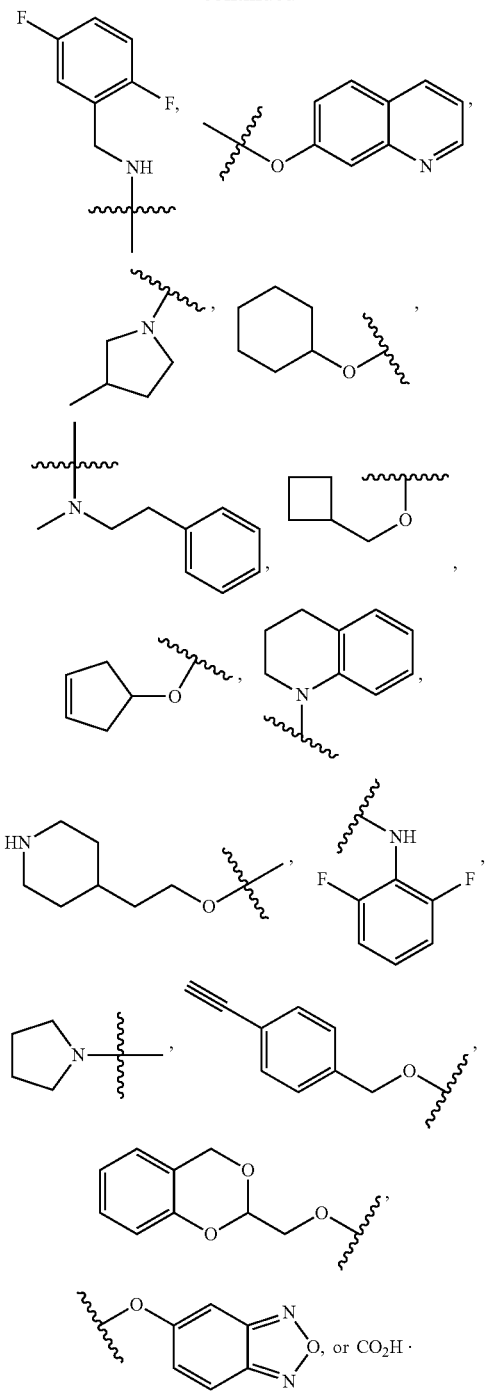

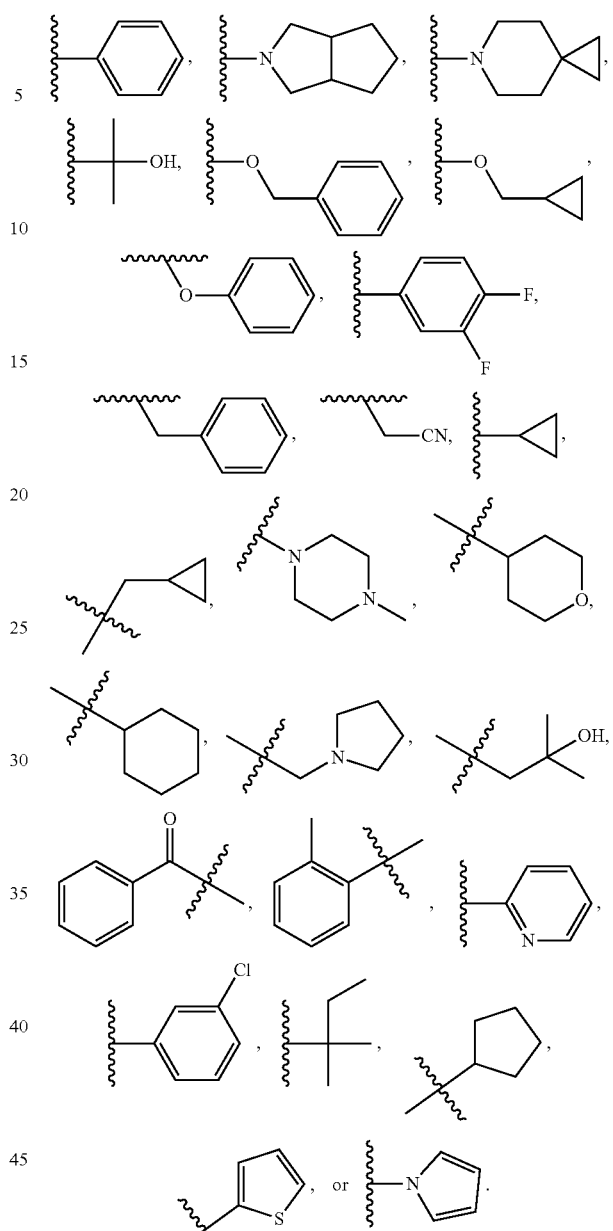

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, $—CH_2N(CH_3)_2$, $CO_2tBu$, tBu, $=CH_2$, $=O$, In some embodiments, n is 0. In some embodiments, n is 1. In some embodiments, n is 2.

In some embodiments, p is 0. In some embodiments, p is 1. In some embodiments, p is 2.

In some embodiments, $R_1$ is phenyl, pyridine, or pyrazole, and n is 1. In some embodiments, $R_1$ is phenyl, pyridine, or pyrazole, n is 1, $R_2$ is amino or alkyl, and p is 0 or 1. In some embodiments, $R_1$ is phenyl, pyridine, or pyrazole, n is 1, $R_3$ is alkyl, such as methyl, and q is 1, 2, 3, or 4.

In some embodiments, the invention features a compound of formula Ib-iii-2:

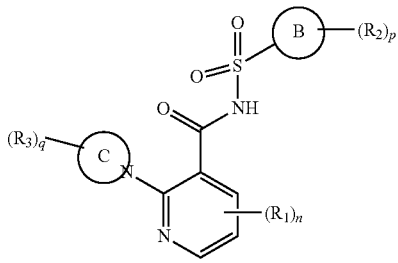

Ib-iii-2 or a pharmaceutically acceptable salt thereof, wherein, independently for each occurrence:

Ring B is a C6-C10 aryl ring;
Ring C is a C3-C14 heteroaryl or heterocyclic ring wherein anywhere from 1 to 4 ring atoms are independently N, O, or S, and wherein one nitrogen on Ring C is the point of attachment to the pyridine ring;
$R_1$ is halo; CN; F5S; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;
$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_2$ groups taken together may form a =$CH_2$ or =O group;
$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_3$ groups taken together may form a =$CH_2$ or =O group;
$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;
R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
n is 0, 1, 2 or 3;
is 0, 1, 2, 3, 4, or 5;
p is 0, 1, 2, or 3; and
q is 0, 1, 2, 3, 4, or 5.

In some embodiments, the compound of formula Ib-iii-2 exists as a pharmaceutically acceptable prodrug.

In some embodiments, ring B is phenyl or naphthalene.

In some embodiments, ring C is indole, piperidine, azepane, azetadine, indoline, isoindoline, or pyrrolidine.

In some embodiments, ring C is a group represented by the corresponding moieties shown in the compounds of Table 1. For example, ring C is

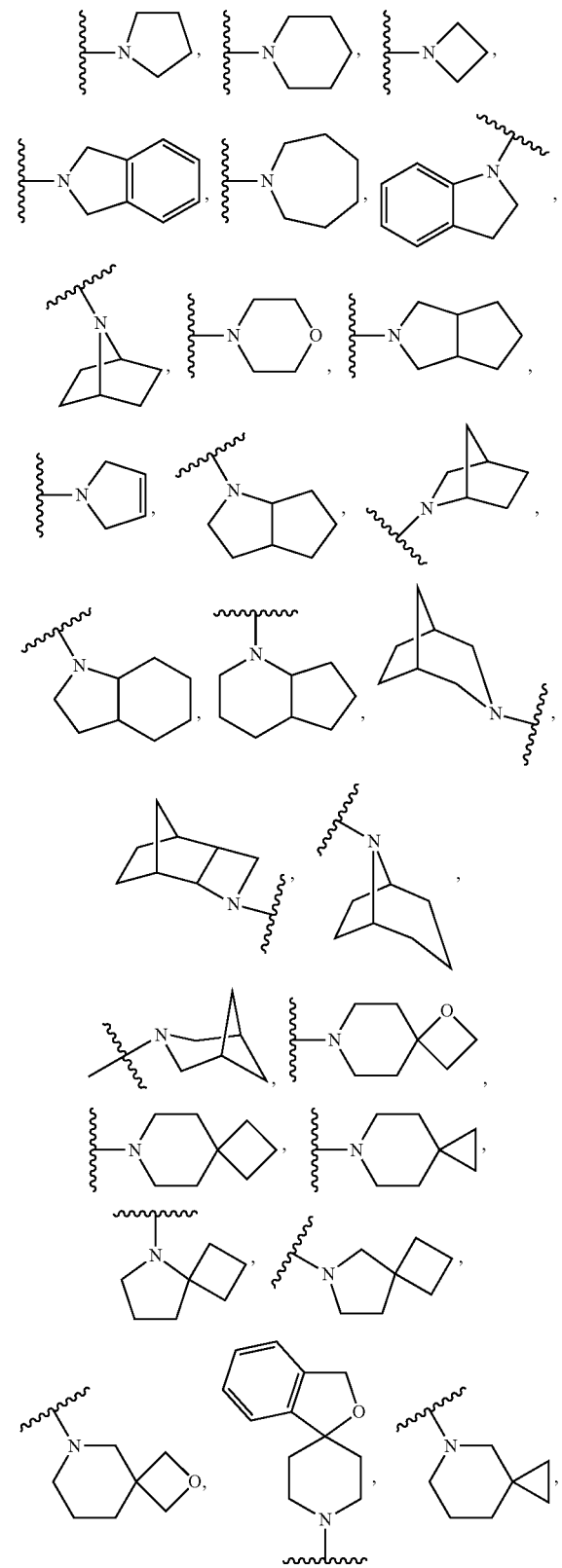

-continued

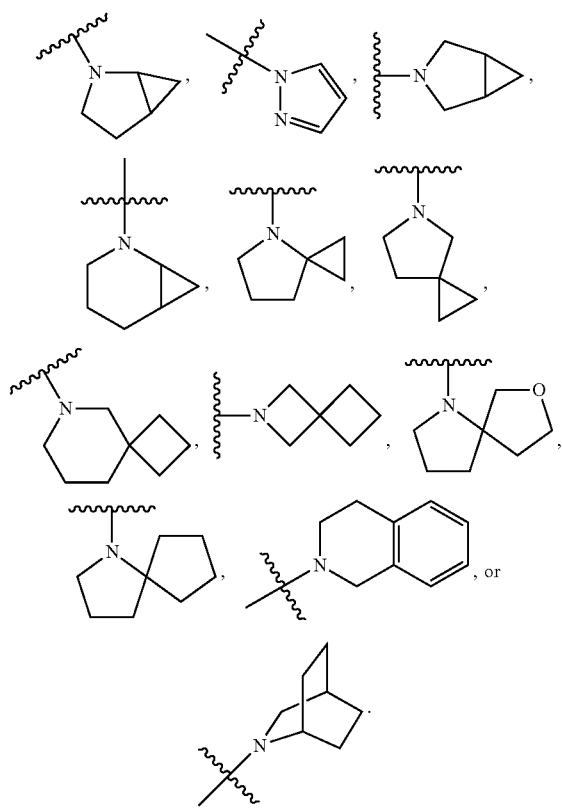

In some embodiments, R₁ is halo, CN, C1-C6 alkyl, C1-C6 alkoxy, C3-C8 cycloalkyl, or a phenyl, pyridyl, pyrimidine, indole, aza-indole, azetidine, pyrazole, or thiophene ring, or a (C1-C9 alkylene)-R₄ wherein up to four CH₂ units are independently replaced with O, CO, S, SO, SO₂ or NR, wherein all rings are optionally substituted with one or more groups selected from halo, C1-C6 alkyl, C1-C6 alkoxy, C1-C6 fluoroalkyl, C1-C6 fluoroalkoxy, OH, CH₂OH, CH₂OCH₃, CN, CO₂H, amino, amido, C3-C10 heteroaryl, and C3-C10 heterocycloalkyl.

In some embodiments, R₁ is a group represented by the corresponding moieties shown in the compounds of Table 1. For example, R₁ is CH₃, Cl, F, CN, OCH₃, CF₃, CH₂CH₃, tBu, CH(CH₃)₂, OCH₂CH₂OCH₂CH₃,

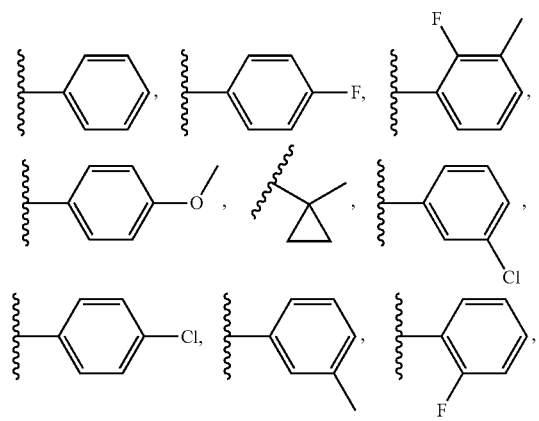

-continued

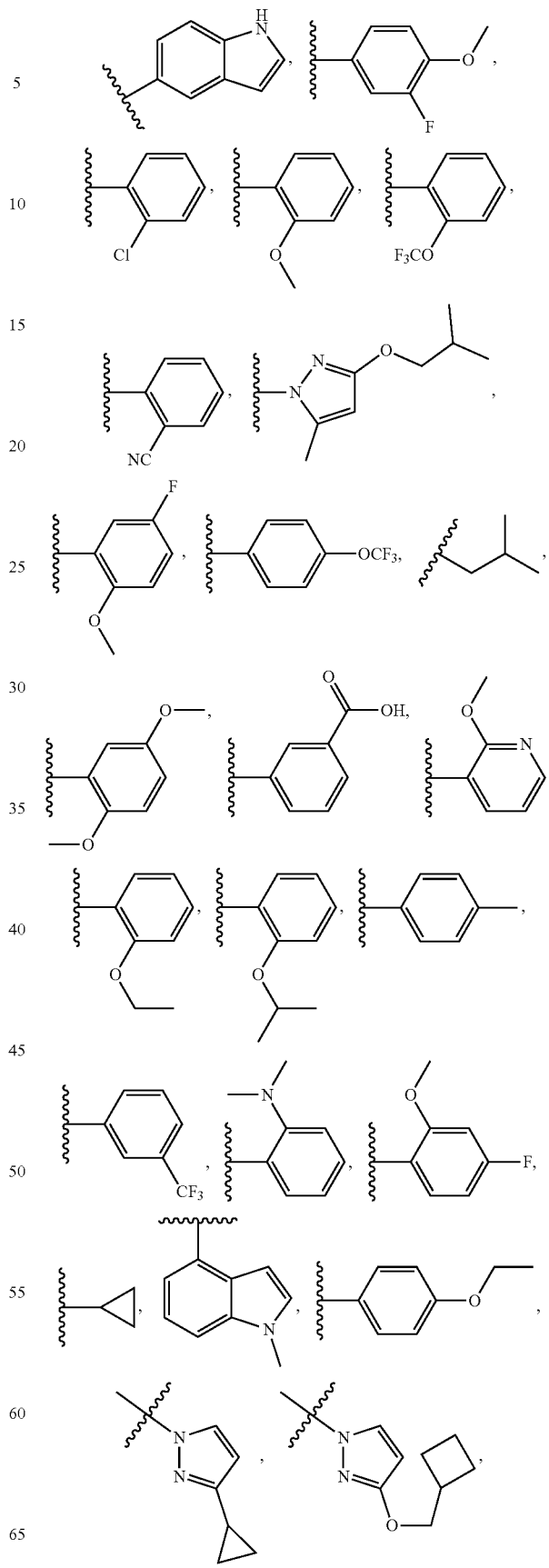

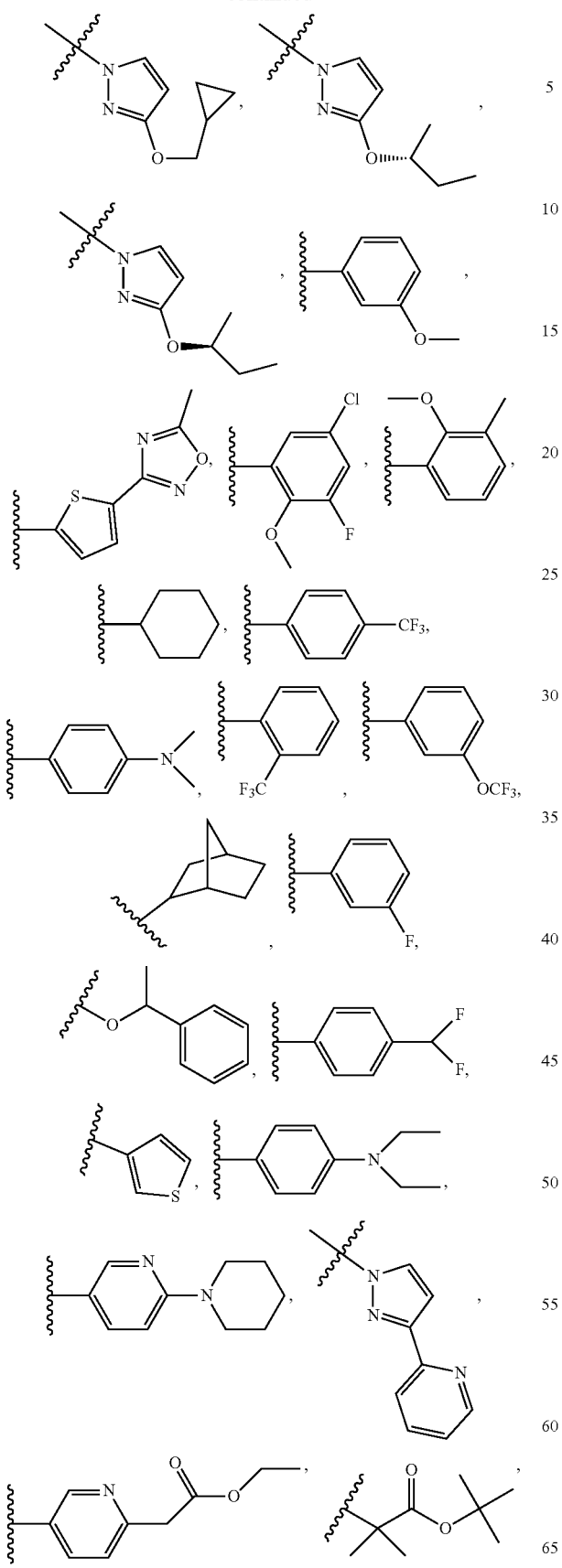
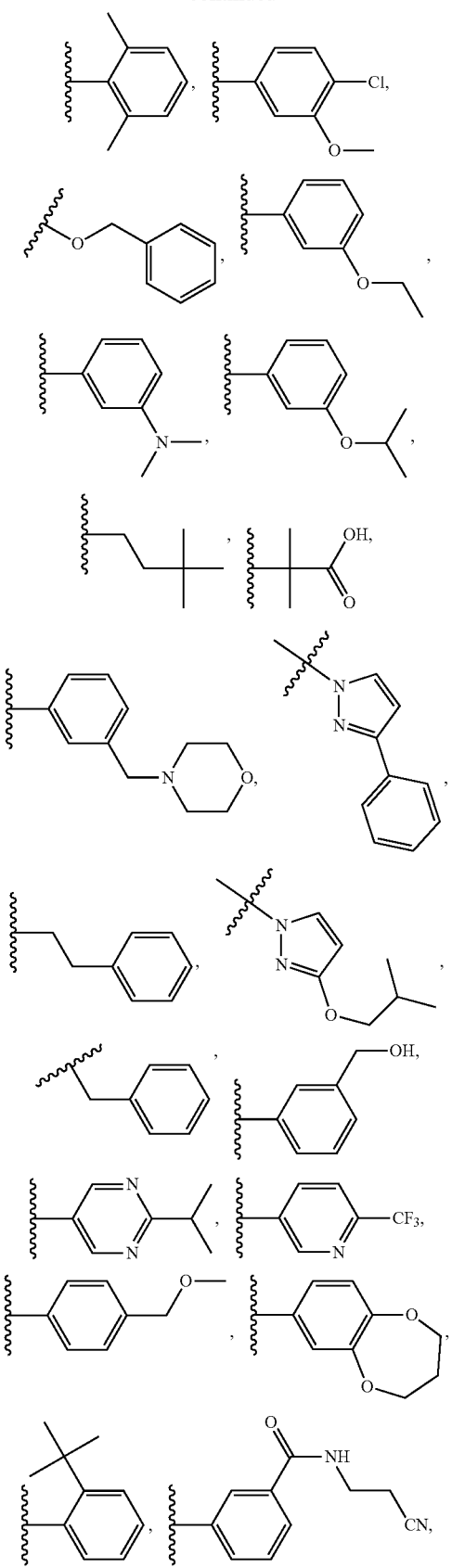

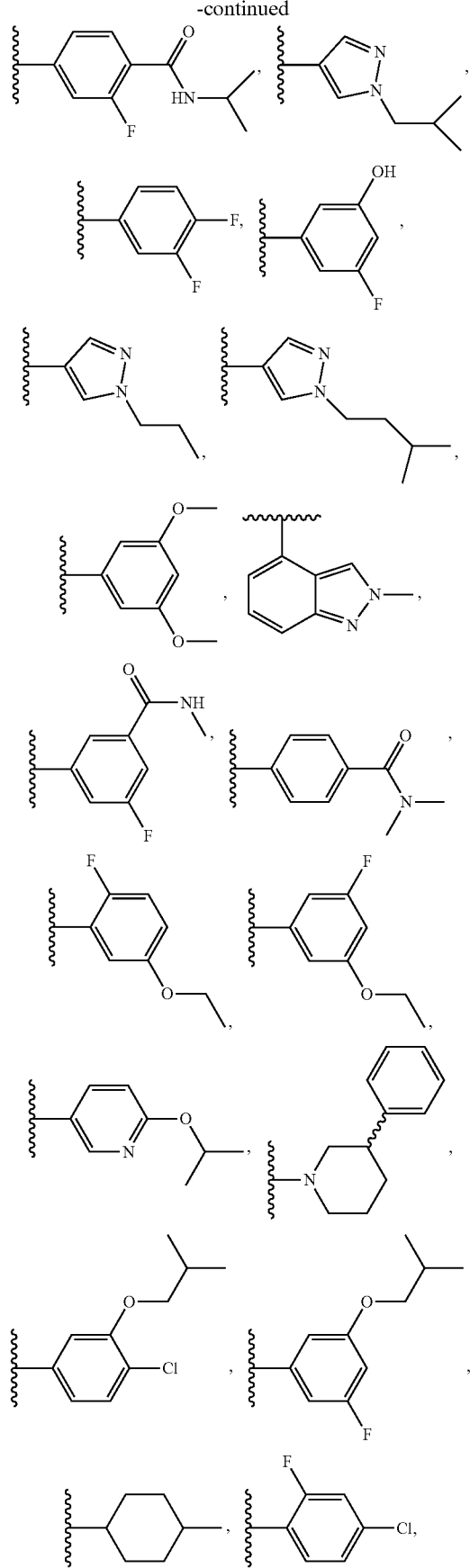
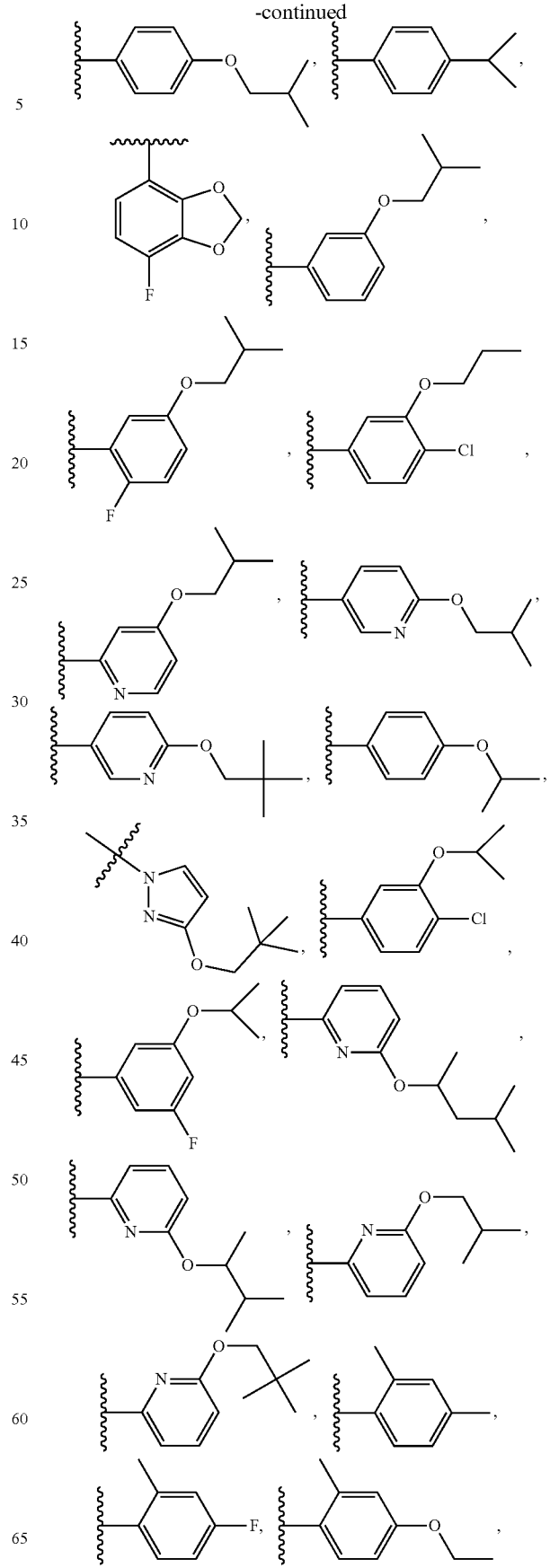

-continued

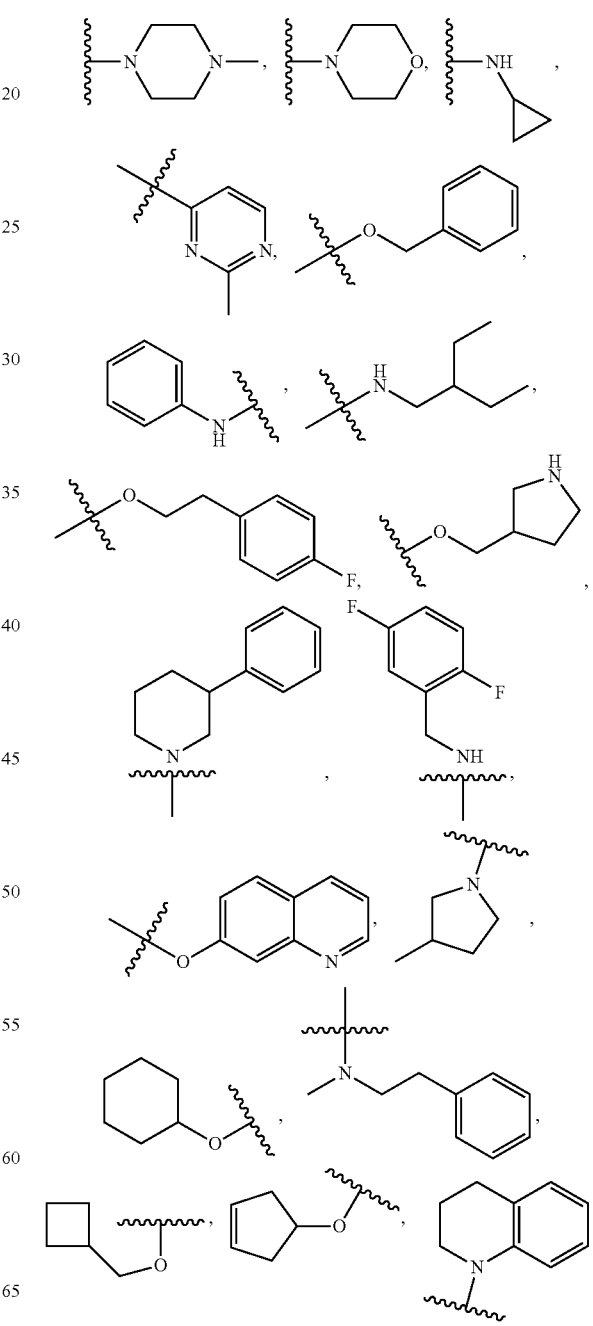

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)$ $(CH_2CH_2CH_3)$, $OCH(CH_3)_2$, $NH(CH_2)_2O(CH_2)_2CH_3$, $C(O)$ $CH_3$, $CH_2CH_2OH$, $CH_2NH_2$, $NH(CH_2)_2OH$, $N(CH_3)$ $CH_2CH_2CH_2OCH_3$, $NHCH_2CH_2COOH$, $NH(CH_2)_2N$ $(CH_3)_2$, $NH(CH_2)_2NH_2$, $NH(CH_2)_3NH_2$, $NH(CH_2)_2OCH_3$, $NHCH(CH_3)_2$, -continued

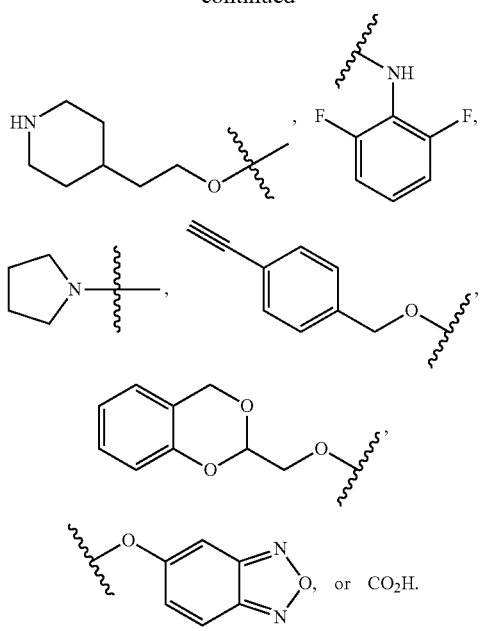

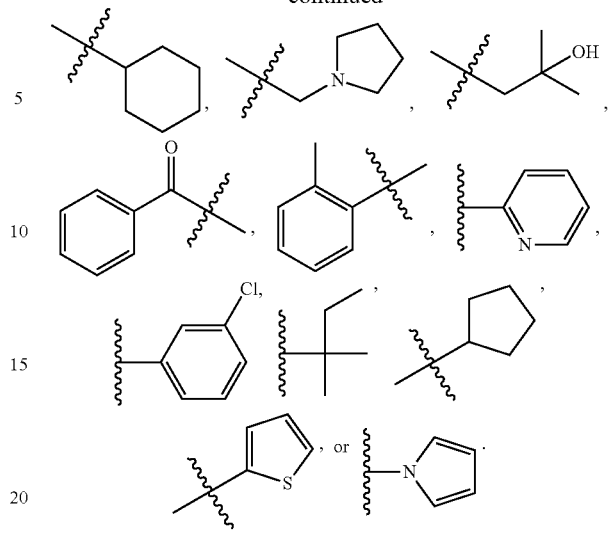

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

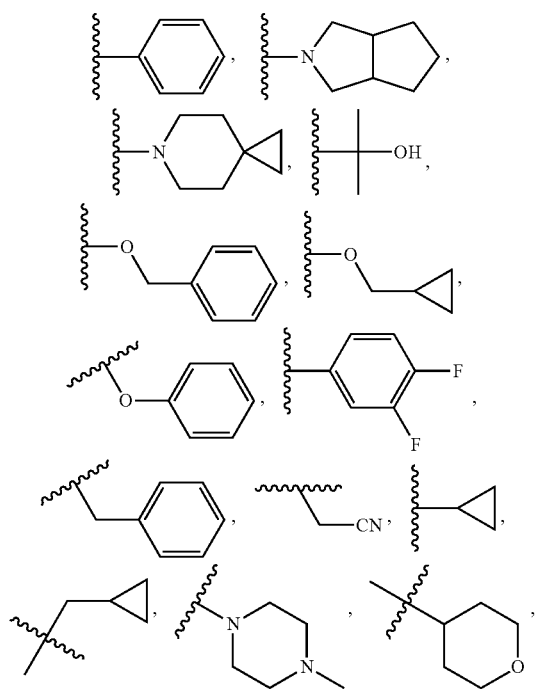

In some embodiments, n is 0. In some embodiments, n is 1. In some embodiments, n is 2.

In some embodiments, p is 0. In some embodiments, p is 1. In some embodiments, p is 2.

In some embodiments, $R_1$ is phenyl, pyridine, or pyrazole, and n is 1. In some embodiments, $R_1$ is phenyl, pyridine, or pyrazole, n is 1, $R_2$ is amino or alkyl, and p is 0 or 1. In some embodiments, $R_1$ is phenyl, pyridine, or pyrazole, n is 1, $R_3$ is alkyl, such as methyl, and q is 1, 2, 3, or 4.

In some embodiments, the invention features a compound of formula Ib-iv:

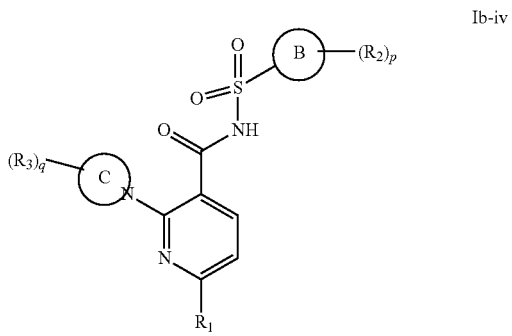

Ib-iv or a pharmaceutically acceptable salt thereof, wherein, independently for each occurrence:
  Ring B is a C6-C10 aryl ring or C3-C10 heteroaryl or heterocyclic ring wherein anywhere from 1 to 4 ring atoms are independently O, S, N, or NR;
  Ring C is a C3-C14 heteroaryl or heterocyclic ring wherein anywhere from 1 to 4 ring atoms are independently N, O, or S, and wherein one nitrogen on Ring C is the point of attachment to the pyridine ring;
  $R_1$ is C6-C10 aryl or C3-C10 heteroaryl wherein anywhere from 1 to 4 ring atoms are independently O, S, N, or NR;
  $R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₂ groups taken together may form a =CH₂ or =O group;

R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₃ groups taken together may form a =CH₂ or =O group;

R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;

R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

p is 0, 1, 2, or 3; and
q is 0, 1, 2, 3, 4, or 5.

In some embodiments, the compound of formula Ib-iv exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

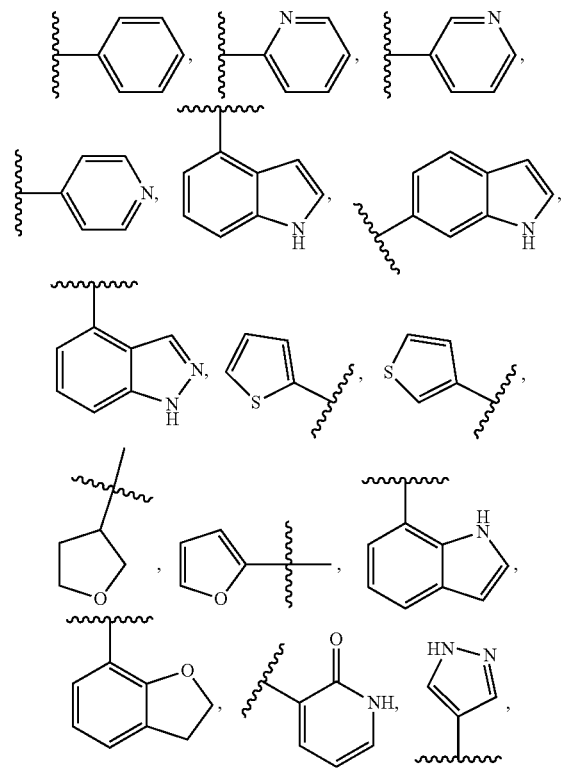

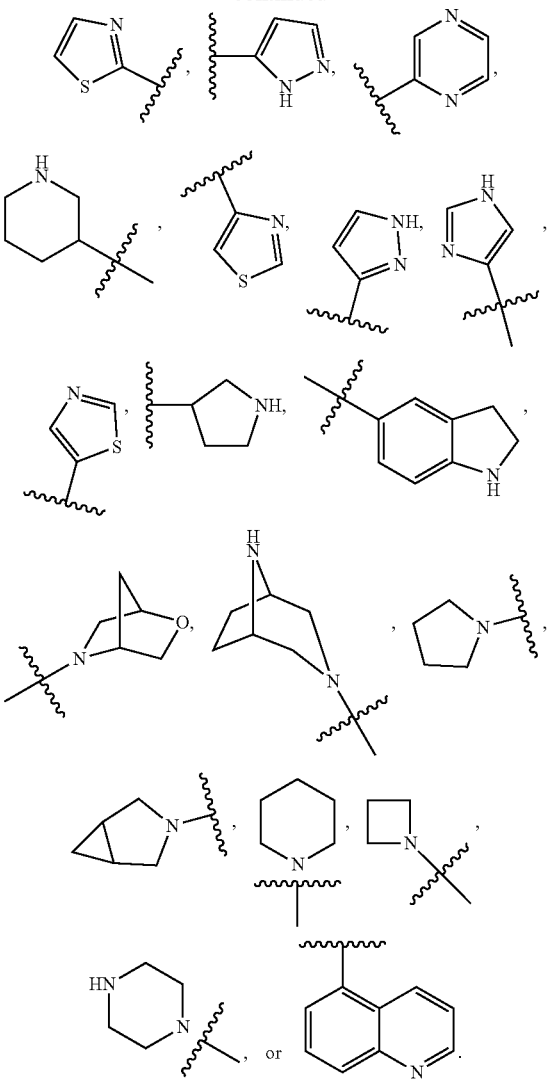

In some embodiments, ring C is indole, piperidine, azepane, azetadine, indoline, isoindoline, or pyrrolidine.

In some embodiments, ring C is a group represented by the corresponding moieties shown in the compounds of Table 1. For example, ring C is

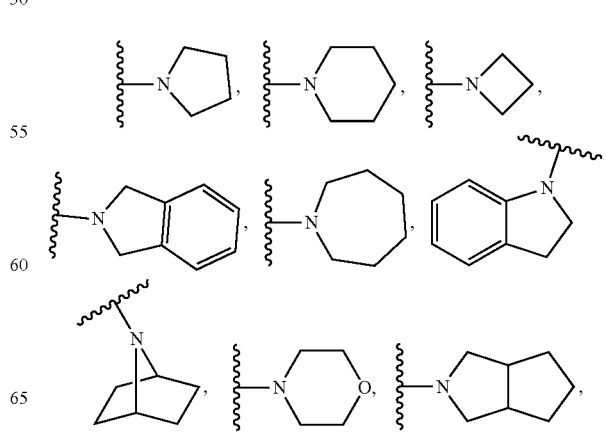

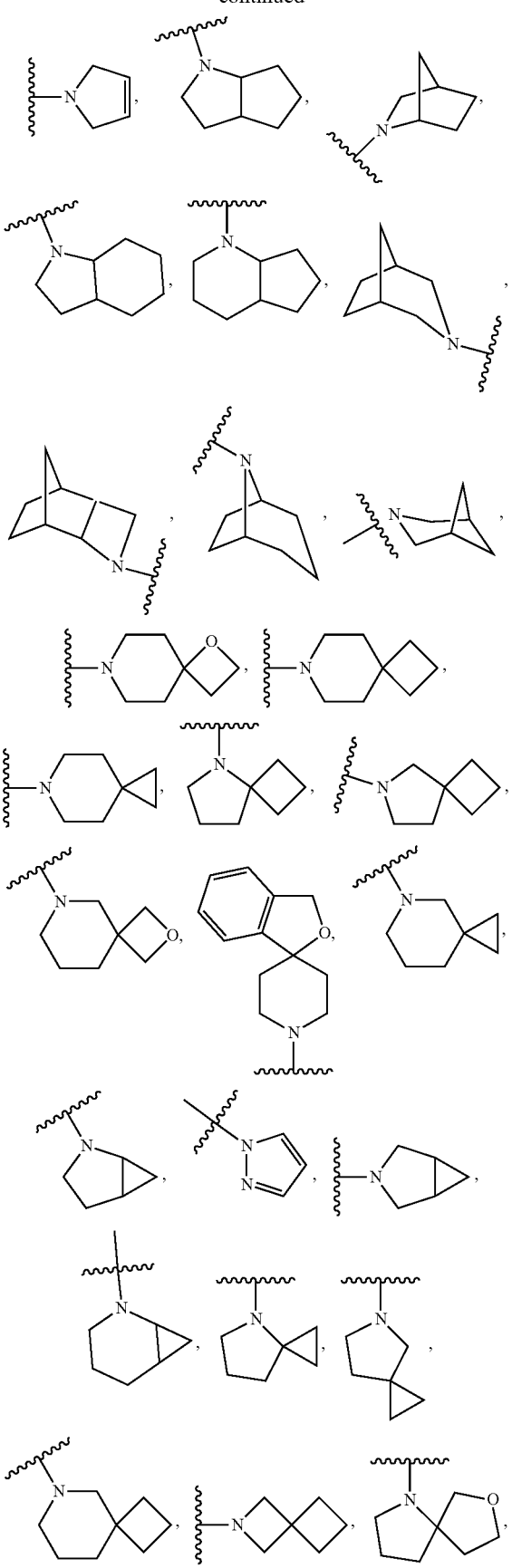
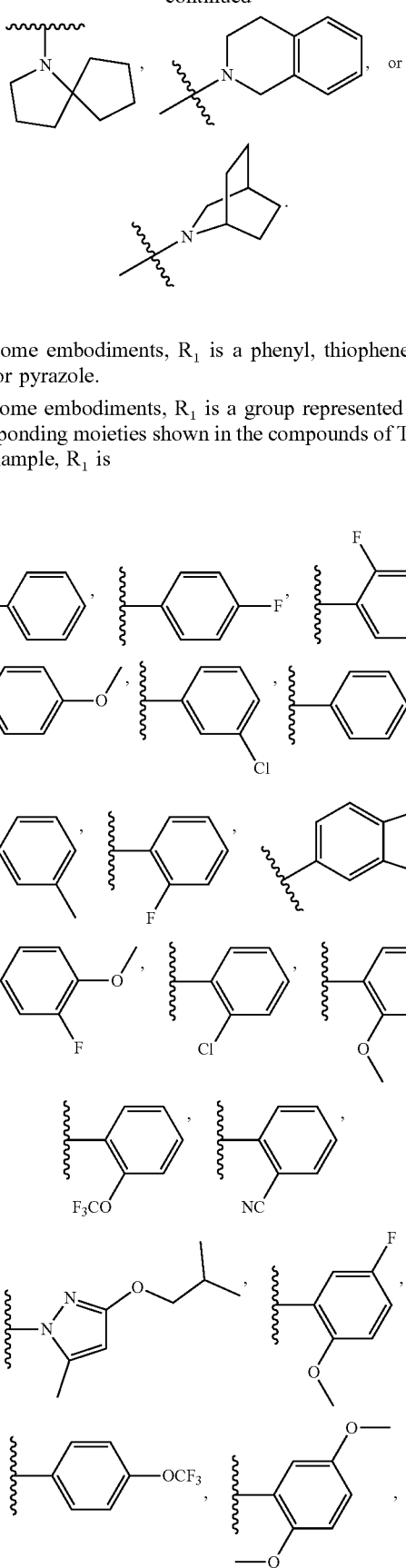
In some embodiments, $R_1$ is a phenyl, thiophene, pyridine, or pyrazole.
In some embodiments, $R_1$ is a group represented by the corresponding moieties shown in the compounds of Table 1. For example, $R_1$ is 185
-continued
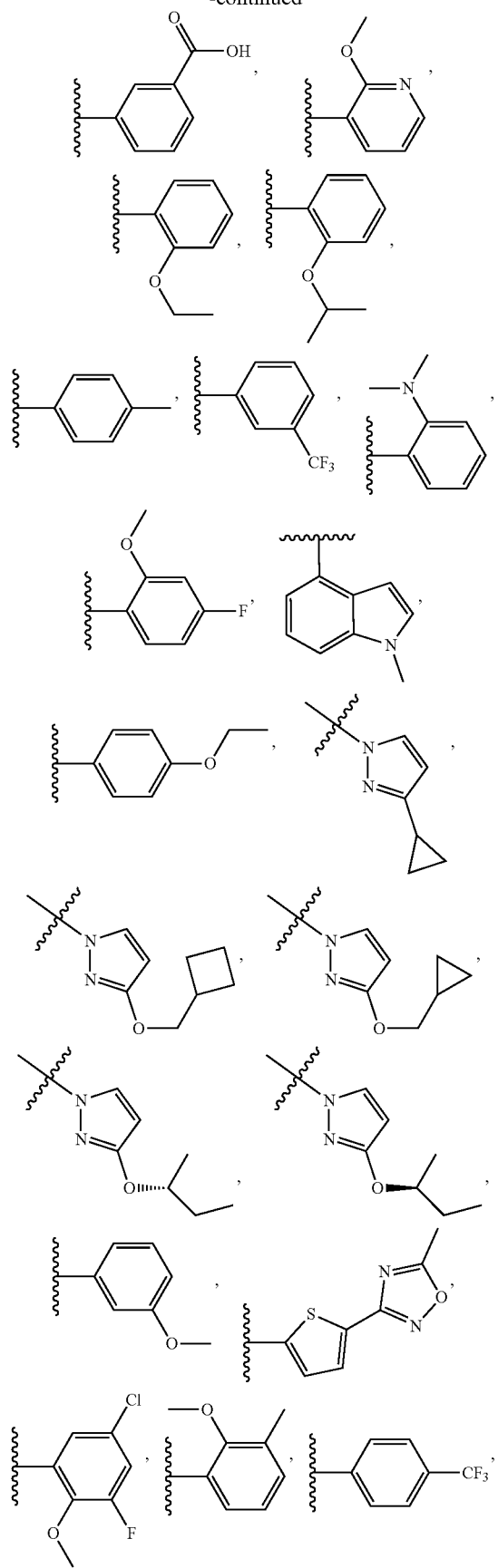
186
-continued
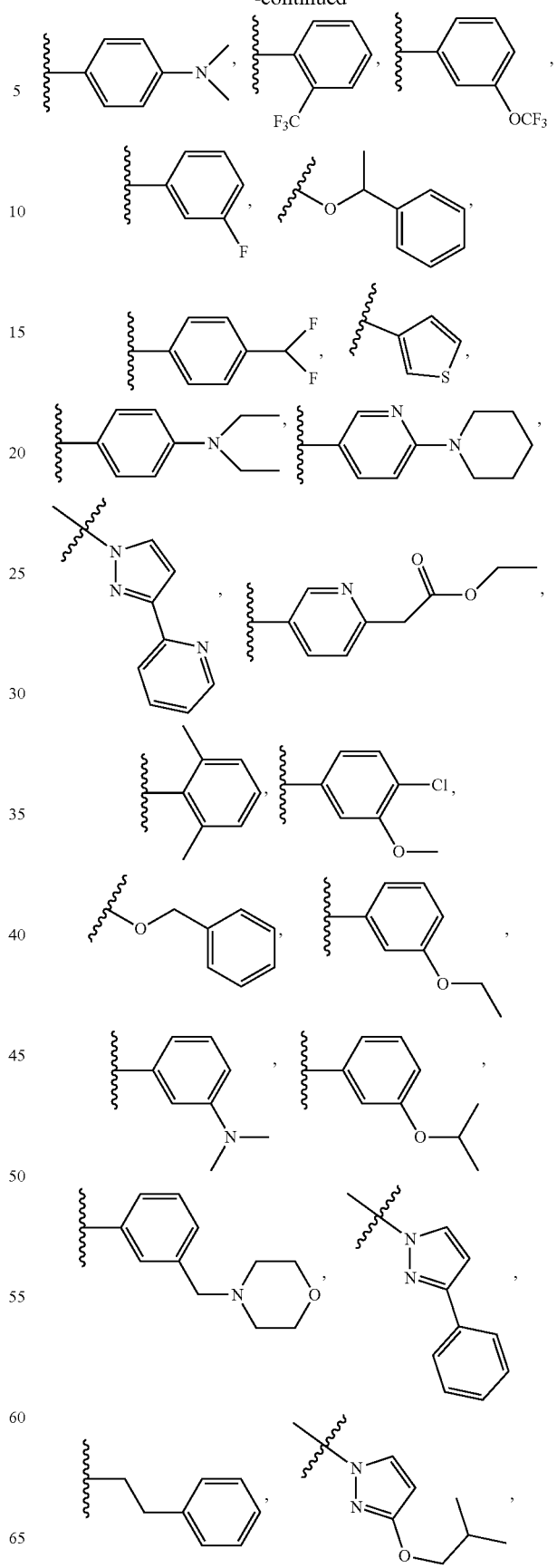

187
-continued
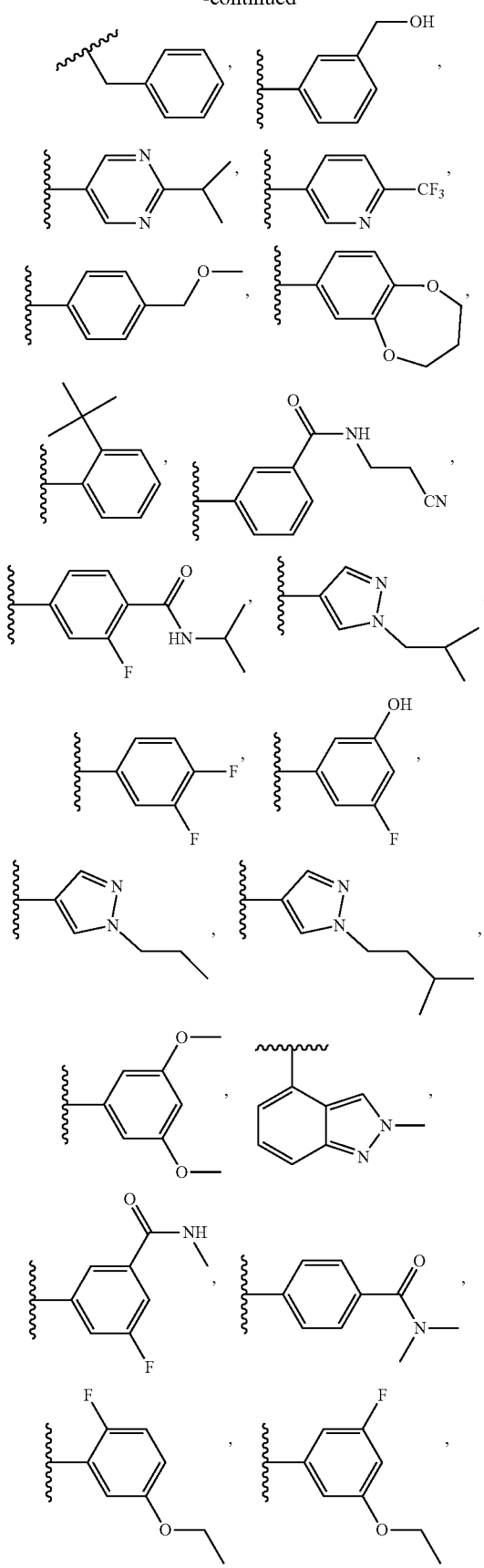
188
-continued
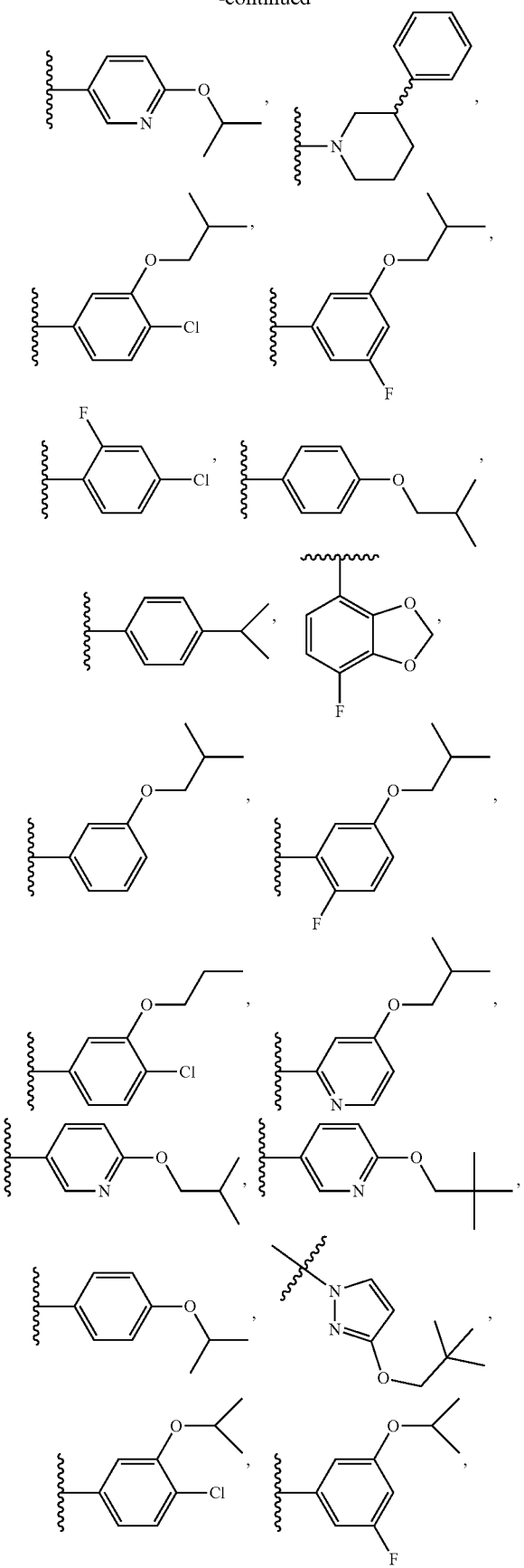

-continued

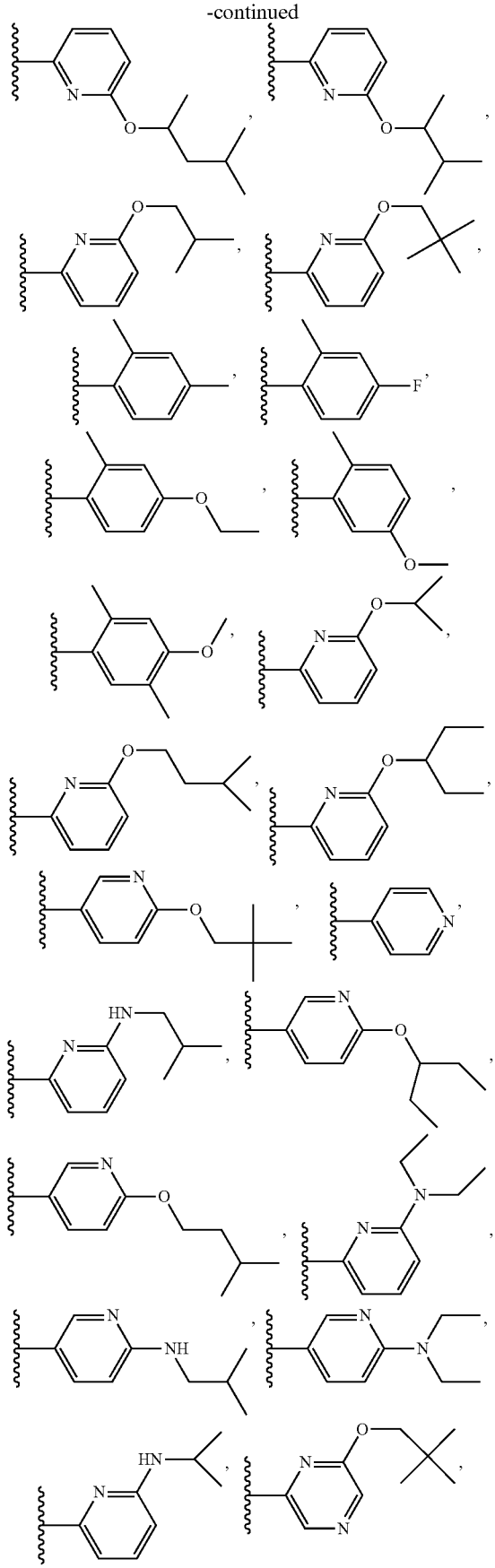

-continued

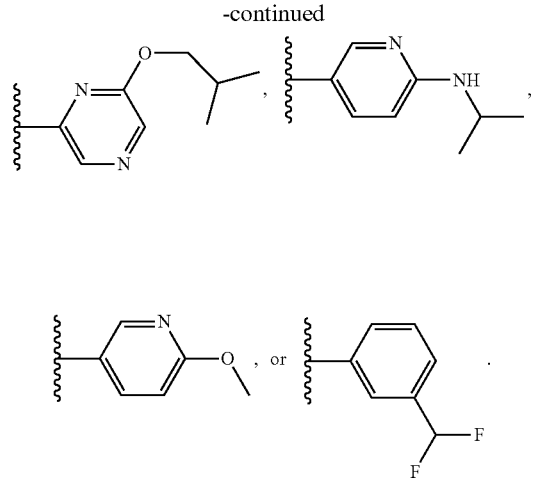

In some embodiments, R₂ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-R₄ wherein up to four CH₂ units are independently replaced with O, CO, S, SO, SO₂ or NR.

In some embodiments, R₂ is a group represented by the corresponding moieties shown in the compounds of Table 1. For example, R₂ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

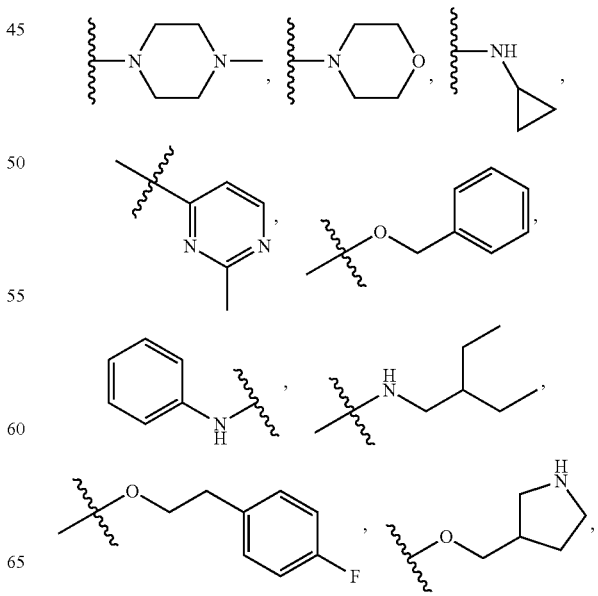

191

-continued

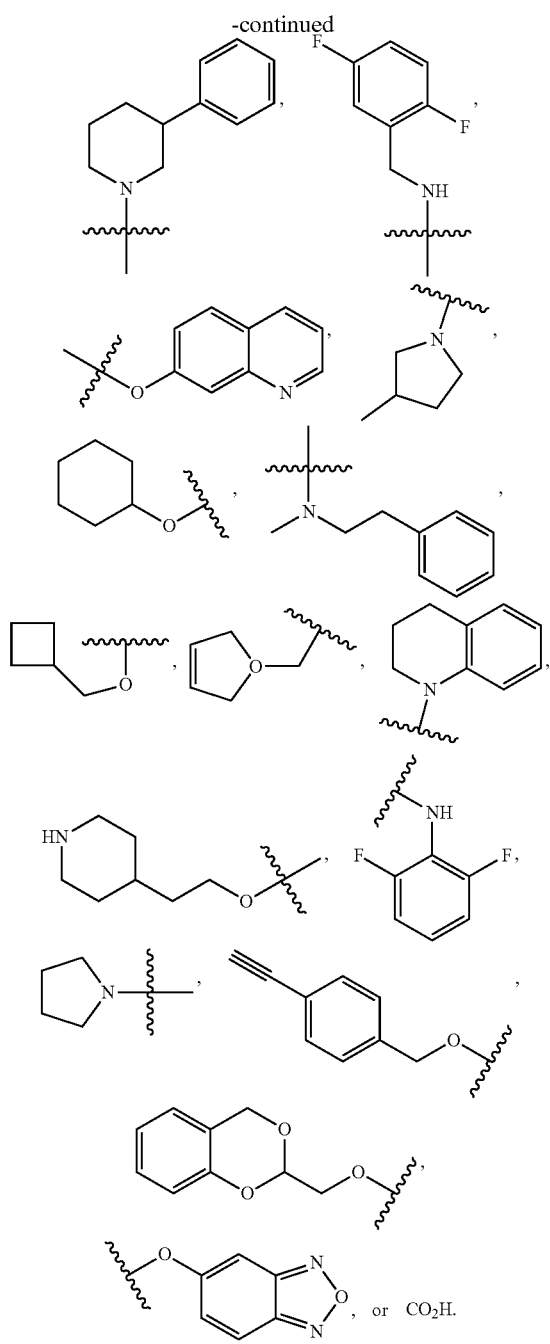

192

-continued

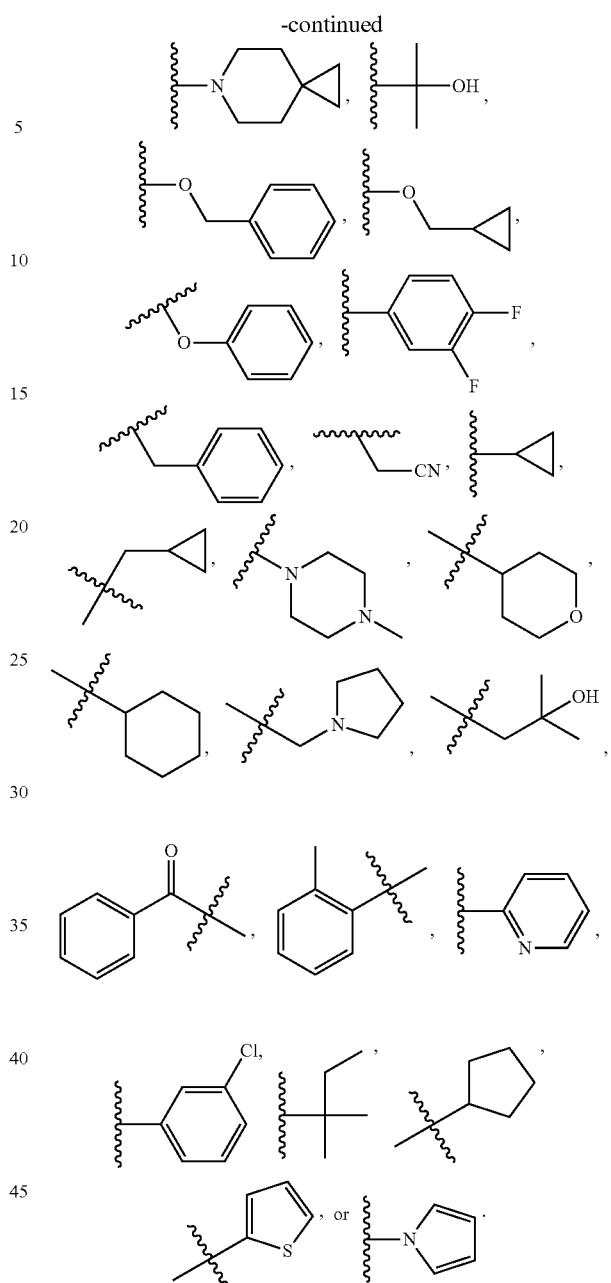

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$,

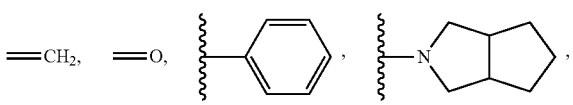

In some embodiments, p is 0. In some embodiments, p is 1. In some embodiments, p is 2.

In some embodiments, $R_1$ is phenyl, pyridine, or pyrazole. In some embodiments, $R_1$ is phenyl, pyridine, or pyrazole, $R_2$ is amino or alkyl, and p is 0 or 1. In some embodiments, $R_1$ is phenyl, pyridine, or pyrazole, $R_3$ is alkyl, such as methyl, and q is 1, 2, 3, or 4.

In some embodiments, the invention features a compound of formula Ib-iv-1:

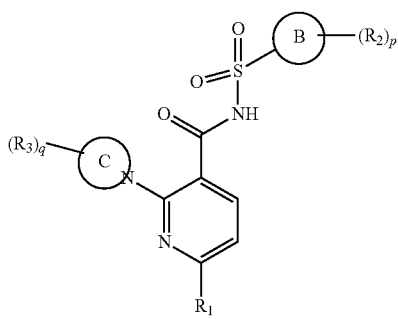

Ib-iv-1 or a pharmaceutically acceptable salt thereof, wherein, independently for each occurrence:

Ring B is a C3-C10 heteroaryl ring wherein anywhere from 1 to 4 ring atoms are independently O, S, N, or NR;

Ring C is a C3-C14 heteroaryl or heterocyclic ring wherein anywhere from 1 to 4 ring atoms are independently N, O, or S, and wherein one nitrogen on Ring C is the point of attachment to the pyridine ring;

$R_1$ is C6-C10 aryl or C3-C10 heteroaryl wherein anywhere from 1 to 4 ring atoms are independently O, S, N, or NR;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a $=CH_2$ or $=O$ group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a $=CH_2$ or $=O$ group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR; NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

p is 0, 1, 2, or 3; and q is 0, 1, 2, 3, 4, or 5.

In some embodiments, ring B is pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

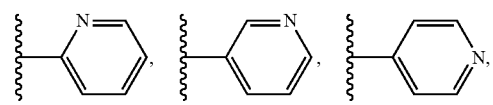

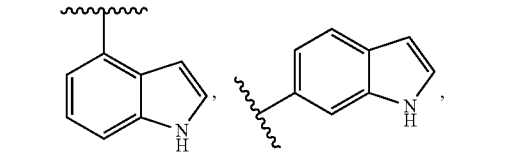

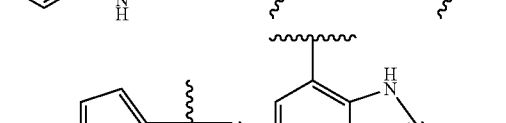

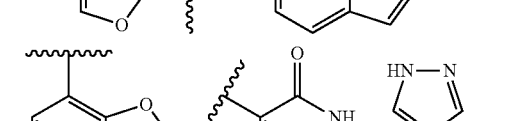

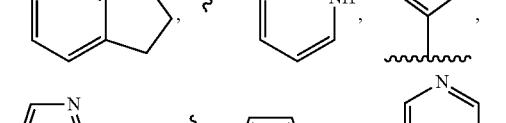

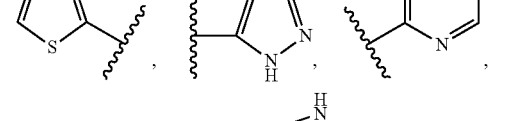

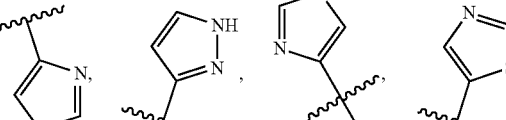

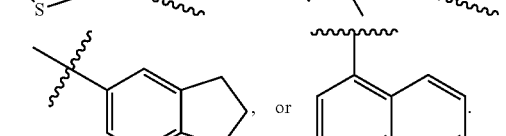

In some embodiments, the compound of formula Ib-iv-1 exists as a pharmaceutically acceptable prodrug.

In some embodiments, ring C is indole, piperidine, azepane, azetadine, indoline, isoindoline, or pyrrolidine.

In some embodiments, ring C is a group represented by the corresponding moieties shown in the compounds of Table 1. For example, ring C is

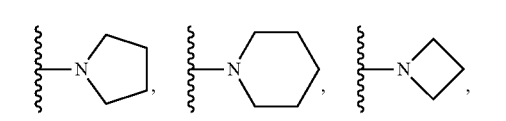

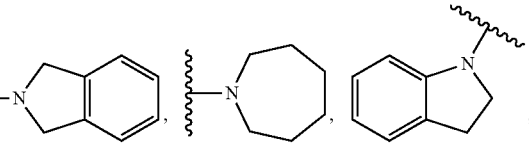

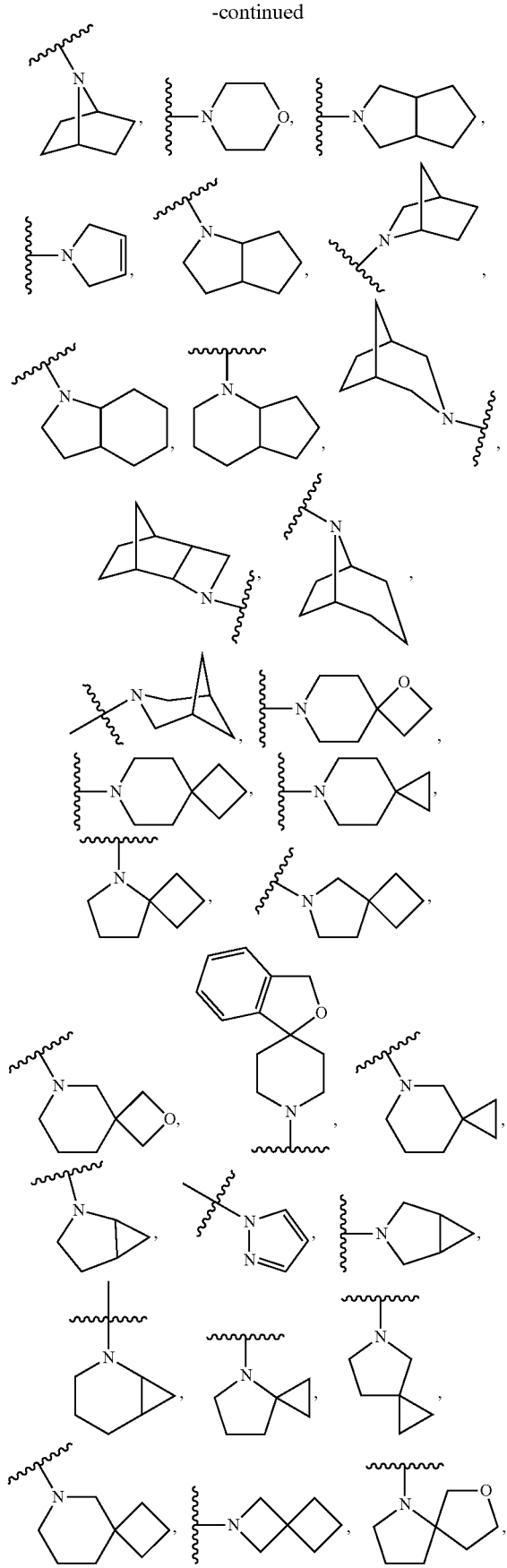
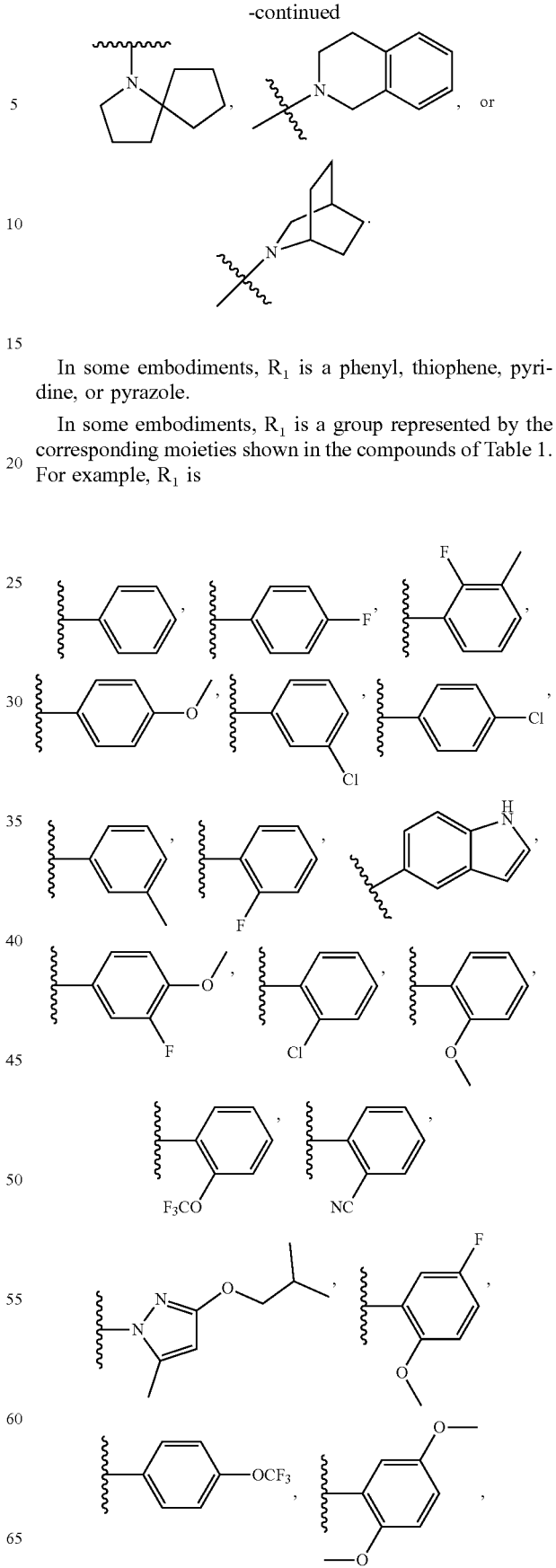
In some embodiments, $R_1$ is a phenyl, thiophene, pyridine, or pyrazole.
In some embodiments, $R_1$ is a group represented by the corresponding moieties shown in the compounds of Table 1. For example, $R_1$ is

197
-continued
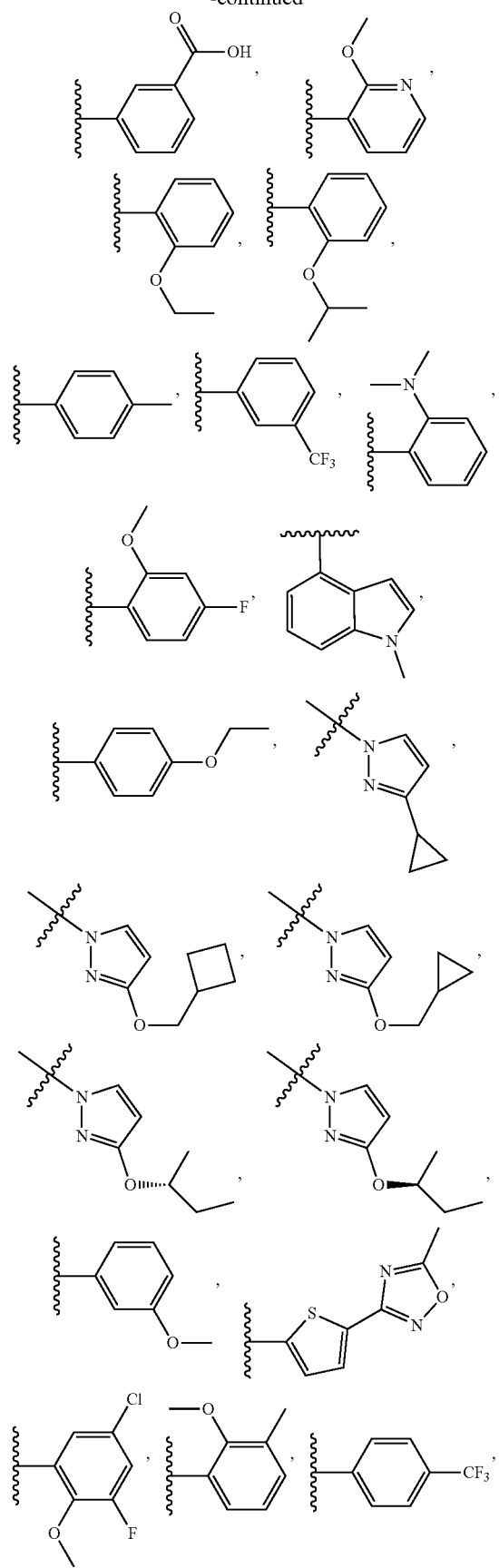
198
-continued
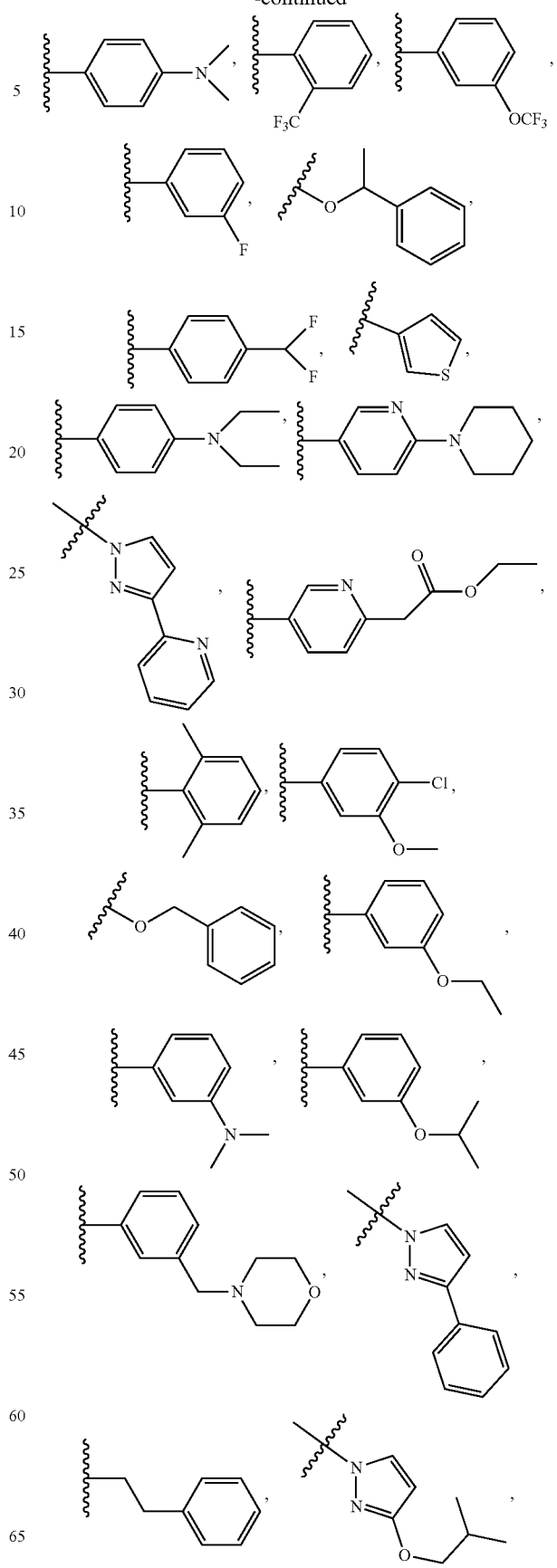

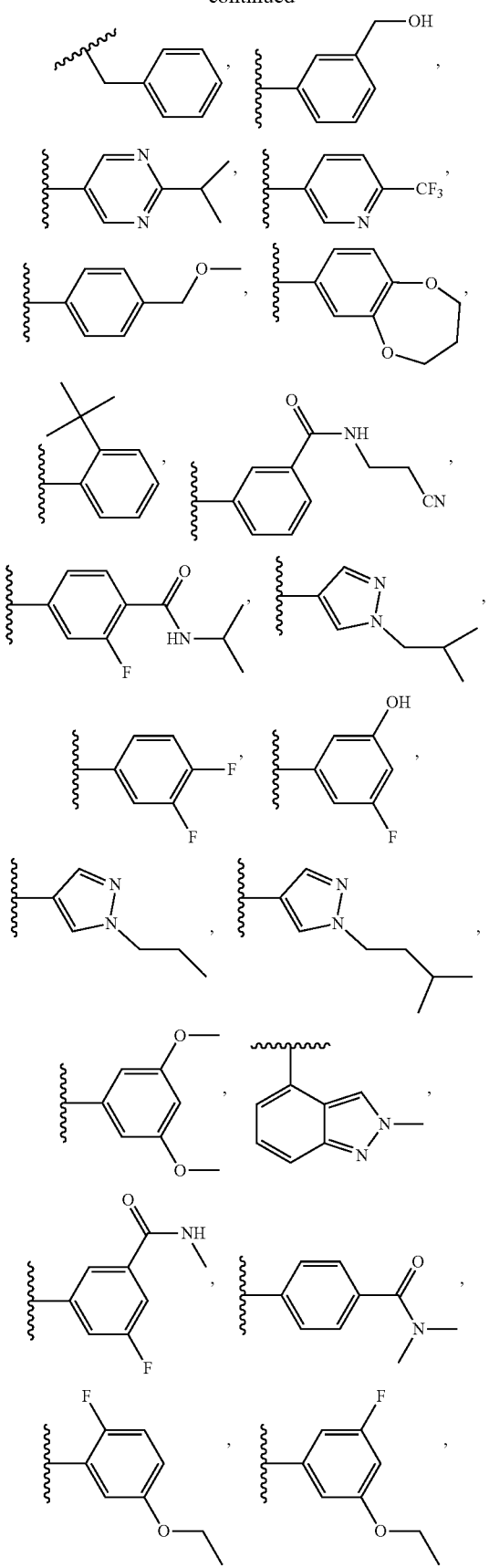
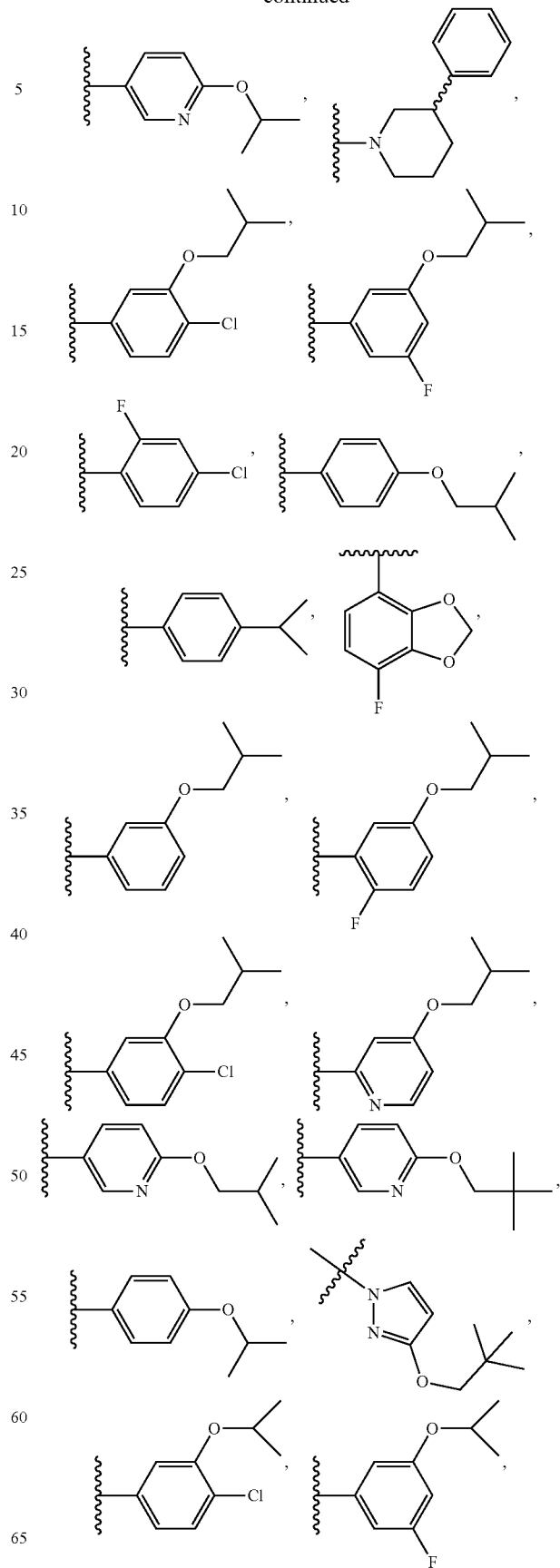

-continued

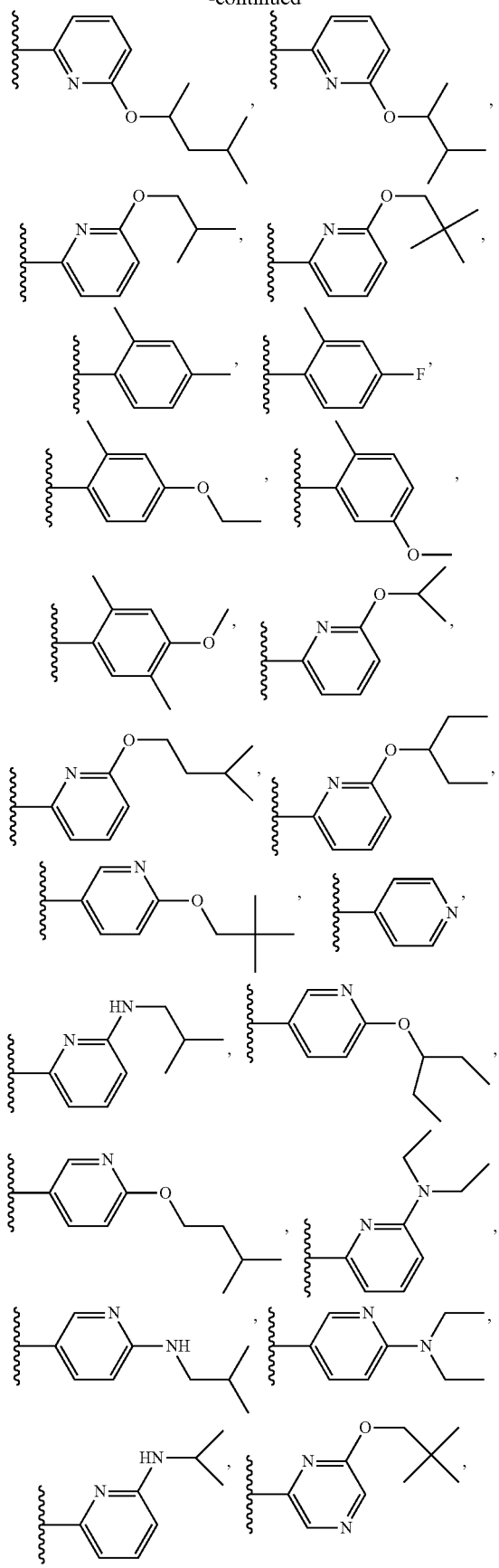

-continued

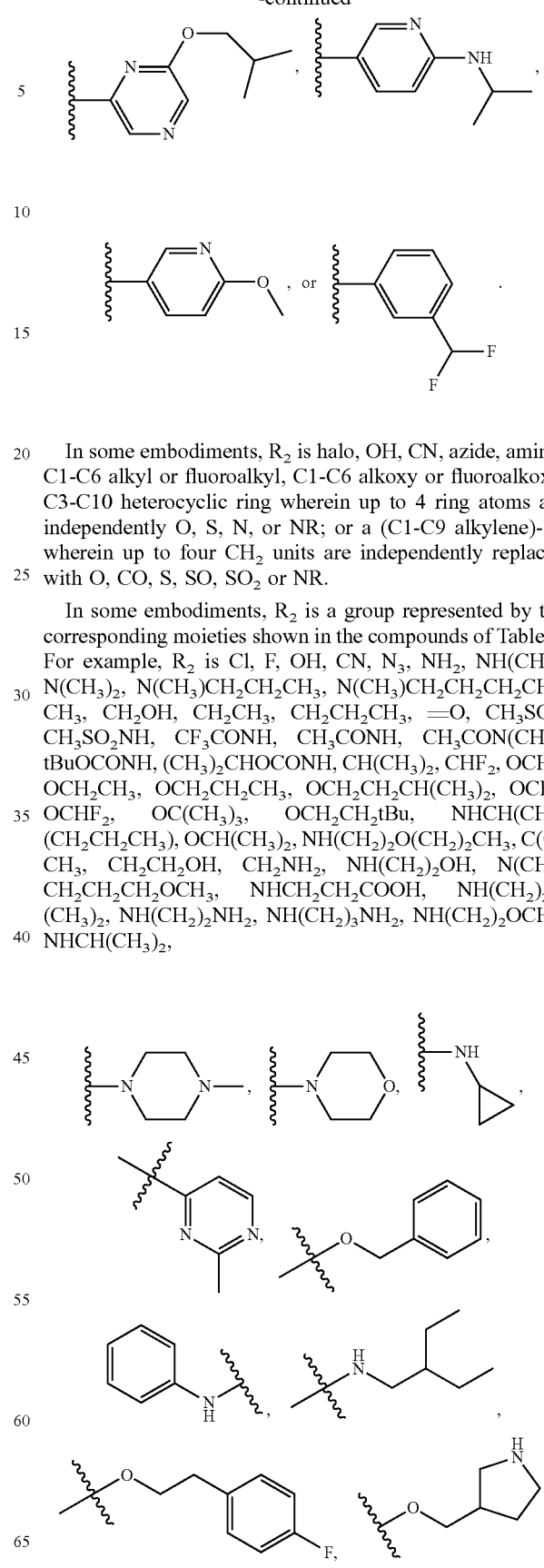

In some embodiments, R$_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-R$_4$ wherein up to four CH$_2$ units are independently replaced with O, CO, S, SO, SO$_2$ or NR.

In some embodiments, R$_2$ is a group represented by the corresponding moieties shown in the compounds of Table 1. For example, R$_2$ is Cl, F, OH, CN, N$_3$, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, CH$_3$, CH$_2$OH, CH$_2$CH$_3$, CH$_2$CH$_2$CH$_3$, =O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$, -continued

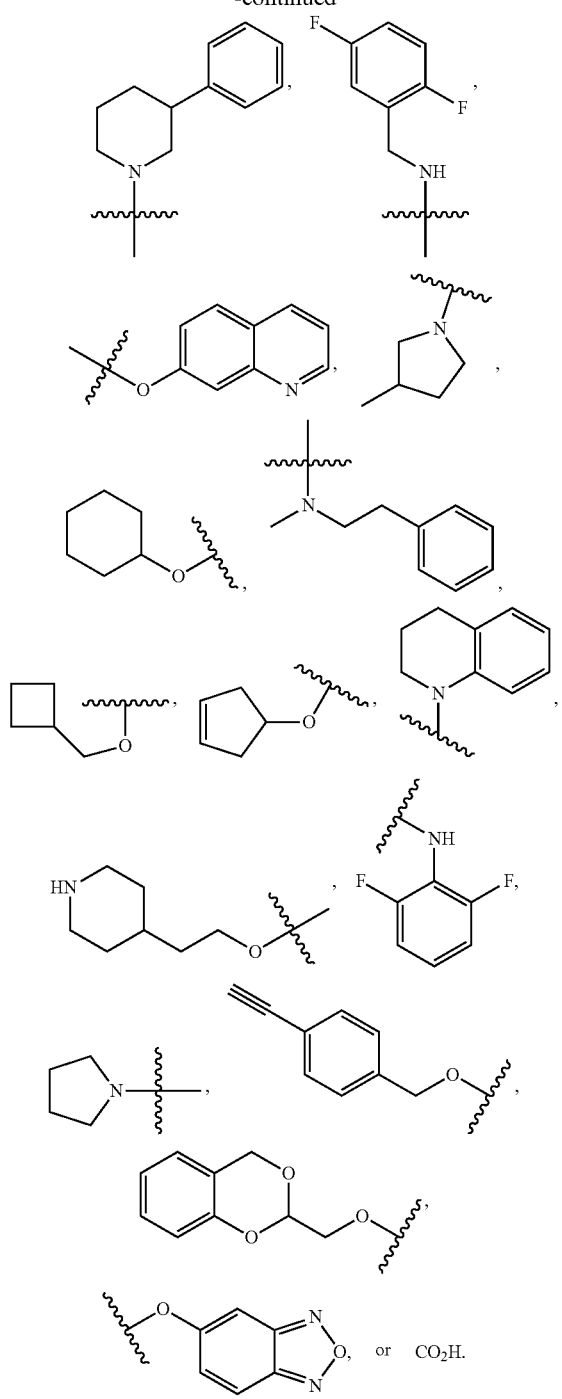

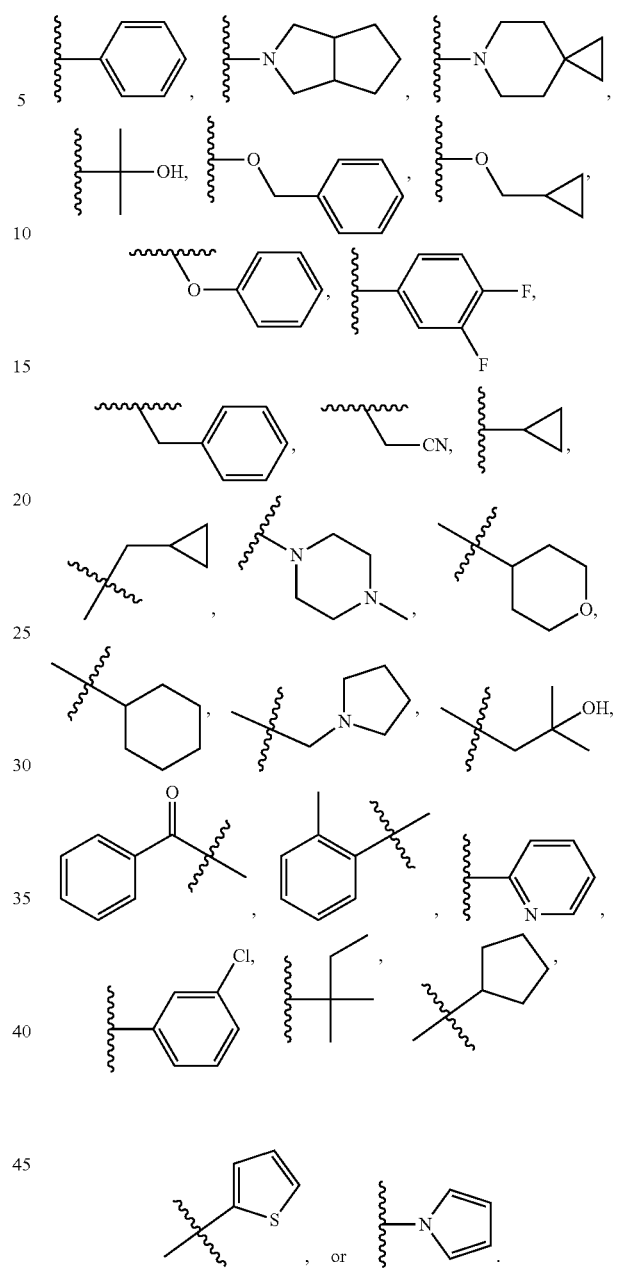

, or CO₂H.

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O, In some embodiments, p is 0. In some embodiments, p is 1. In some embodiments, p is 2.

In some embodiments, $R_1$ is phenyl, pyridine, or pyrazole. In some embodiments, $R_1$ is phenyl, pyridine, or pyrazole, $R_2$ is amino or alkyl, and p is 0 or 1. In some embodiments, $R_1$ is phenyl, pyridine, or pyrazole, $R_3$ is alkyl, such as methyl, and q is 1, 2, 3, or 4.

In some embodiments, the invention features a compound of formula Ib-iv-2:

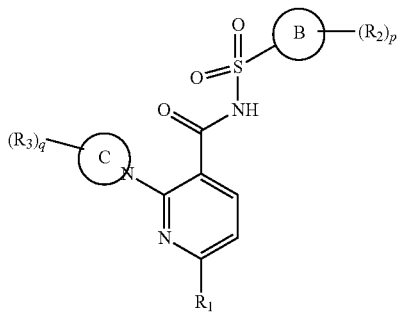

Ib-iv-2

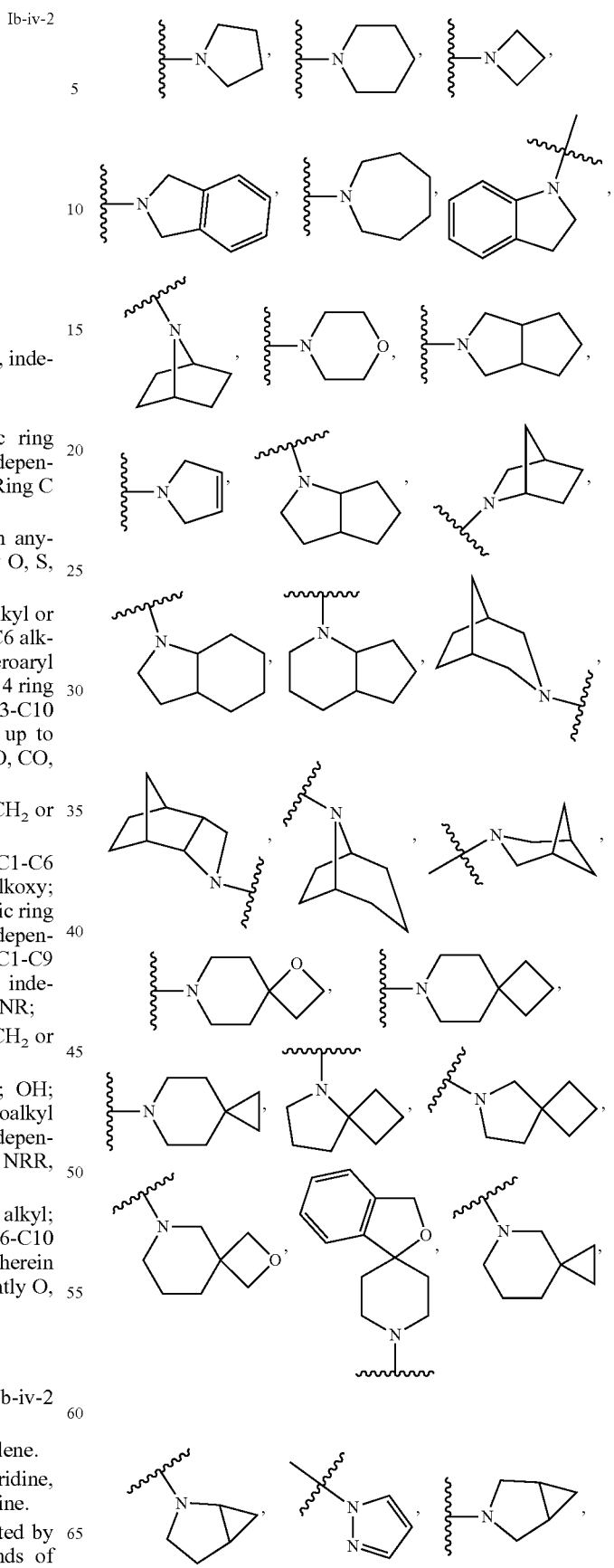

or a pharmaceutically acceptable salt thereof, wherein, independently for each occurrence:

Ring B is a C6-C10 aryl ring;

Ring C is a C3-C14 heteroaryl or heterocyclic ring wherein anywhere from 1 to 4 ring atoms are independently N, O, or S, and wherein one nitrogen on Ring C is the point of attachment to the pyridine ring;

$R_1$ is C6-C10 aryl or C3-C10 heteroaryl wherein anywhere from 1 to 4 ring atoms are independently O, S, N, or NR;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a =$CH_2$ or =O group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a =$CH_2$ or =O group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

p is 0, 1, 2, or 3; and q is 0, 1, 2, 3, 4, or 5.

In some embodiments, the compound of formula Ib-iv-2 exists as a pharmaceutically acceptable prodrug.

In some embodiments, ring B is phenyl or napthalene.

In some embodiments, ring C is indole, piperidine, azepane, azetadine, indoline, isoindoline, or pyrrolidine.

In some embodiments, ring C is a group represented by the corresponding moieties shown in the compounds of Table 1. For example, ring C is 207
-continued
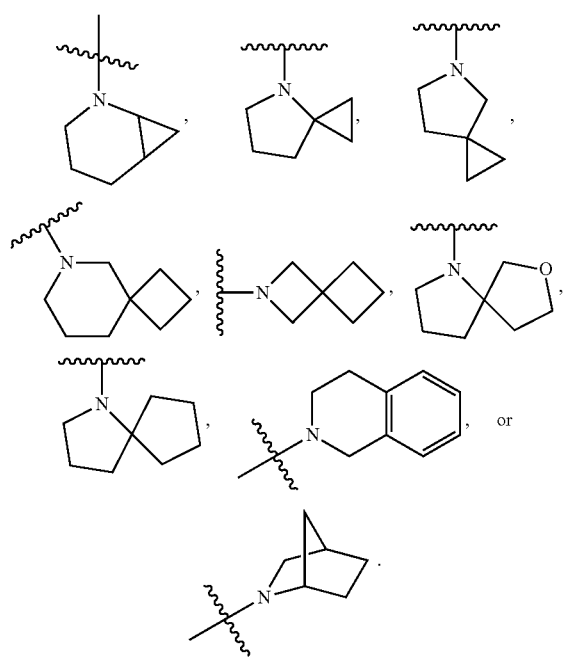
In some embodiments, R₁ is a phenyl, thiophene, pyridine, or pyrazole.
In some embodiments, R₁ is a group represented by the corresponding moieties shown in the compounds of Table 1. For example, R₁ is
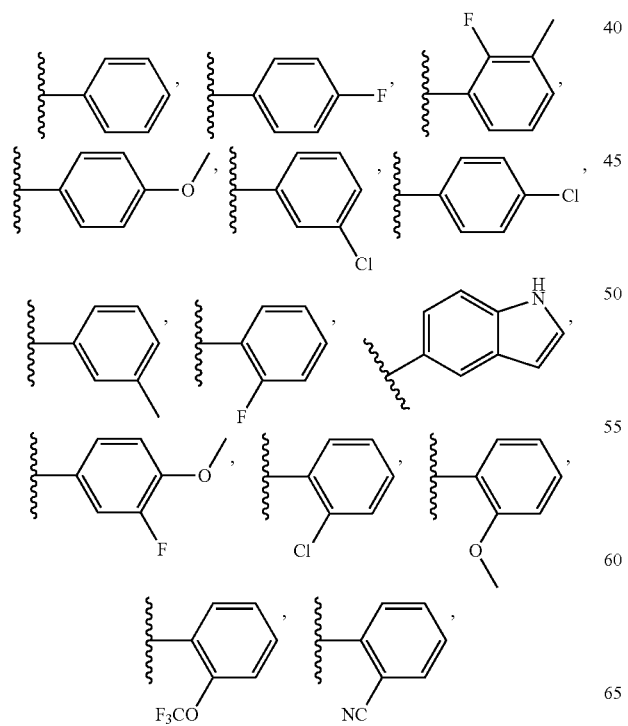
208
-continued
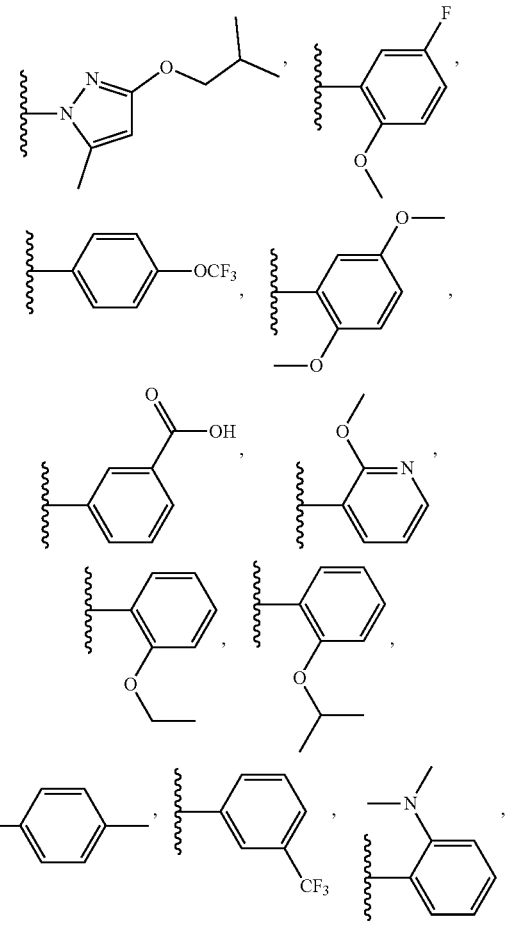
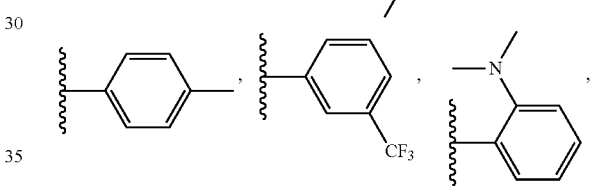
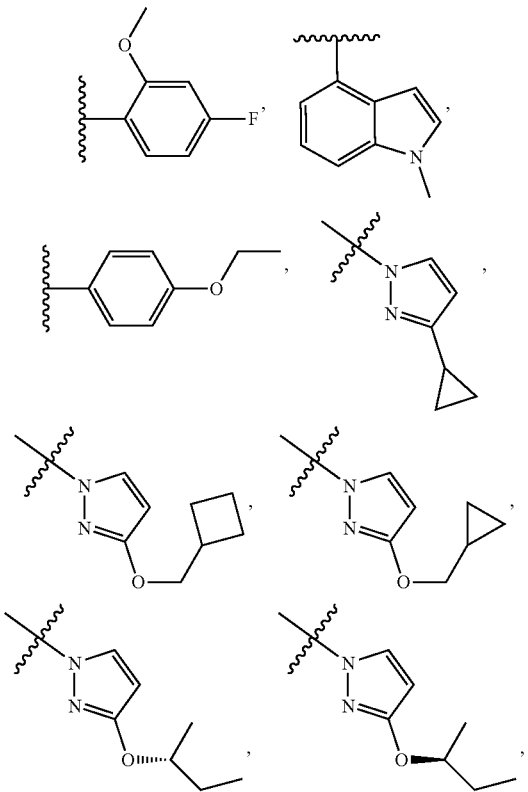

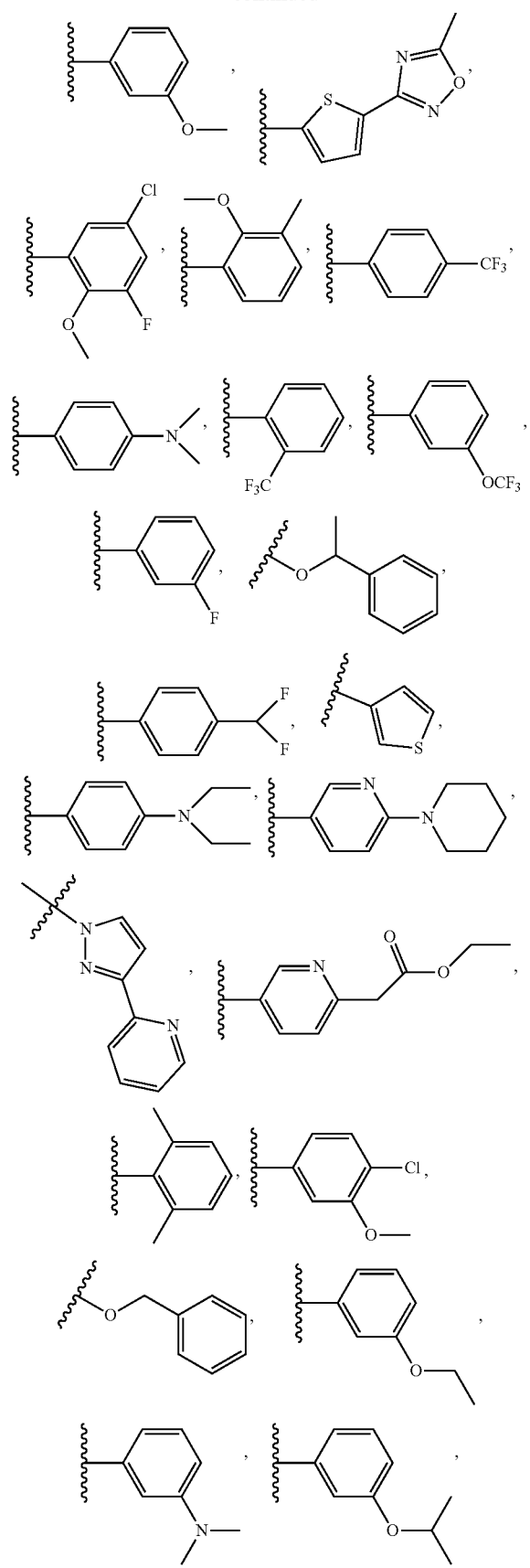
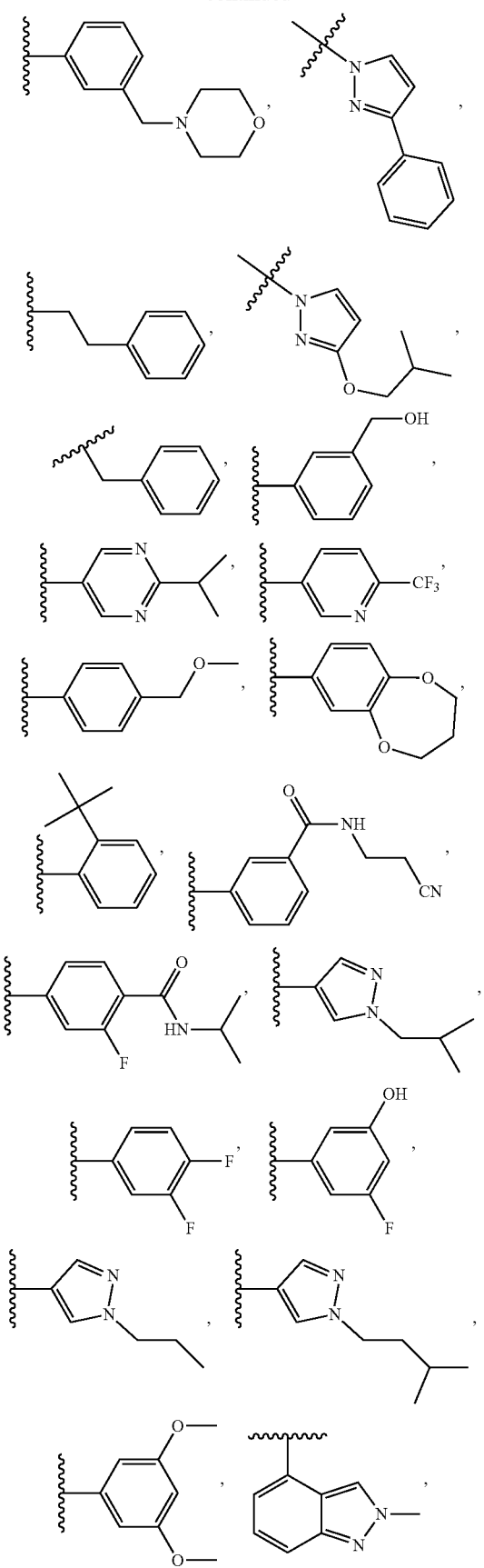

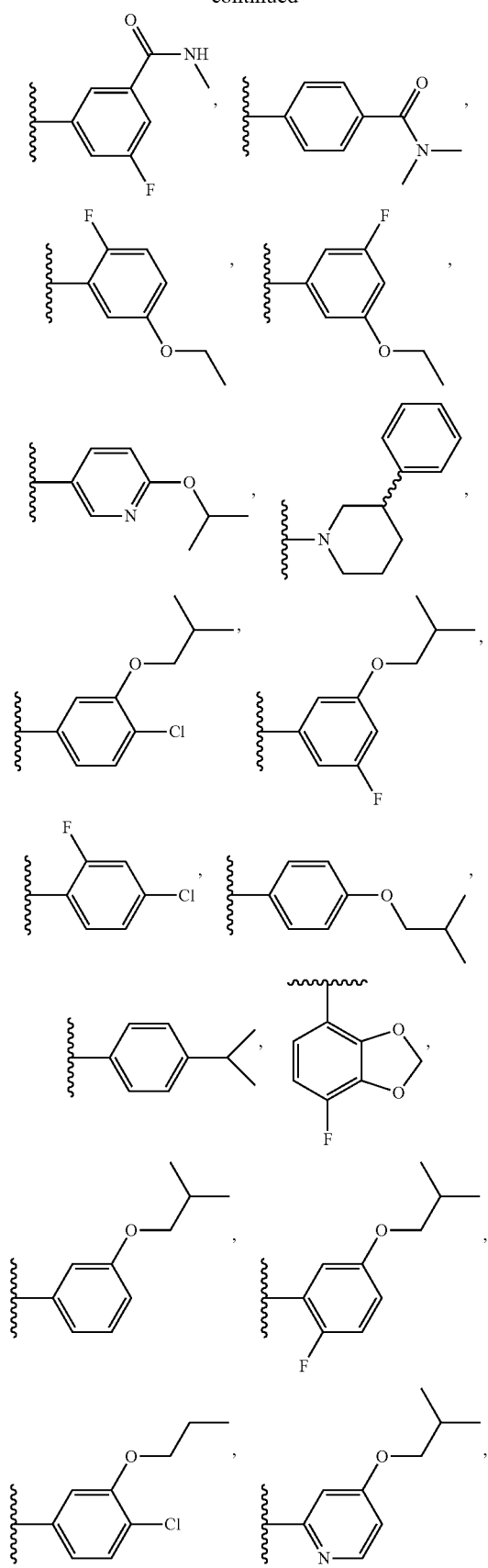
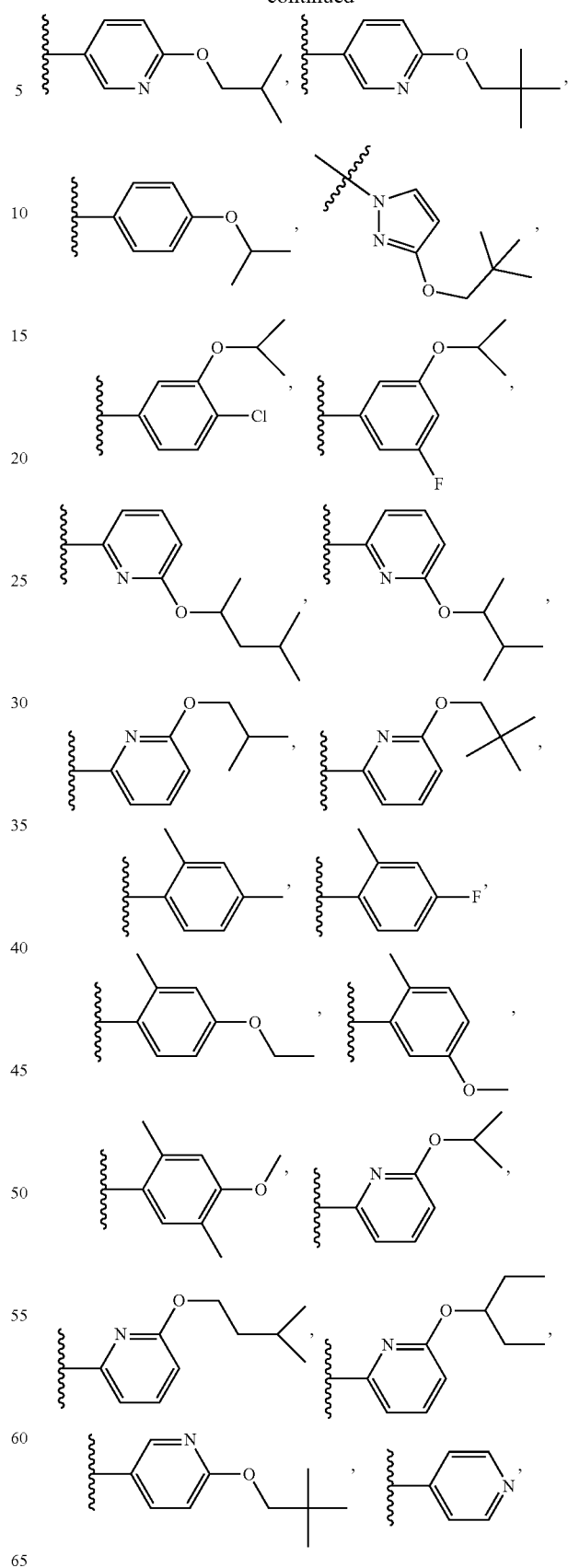

-continued

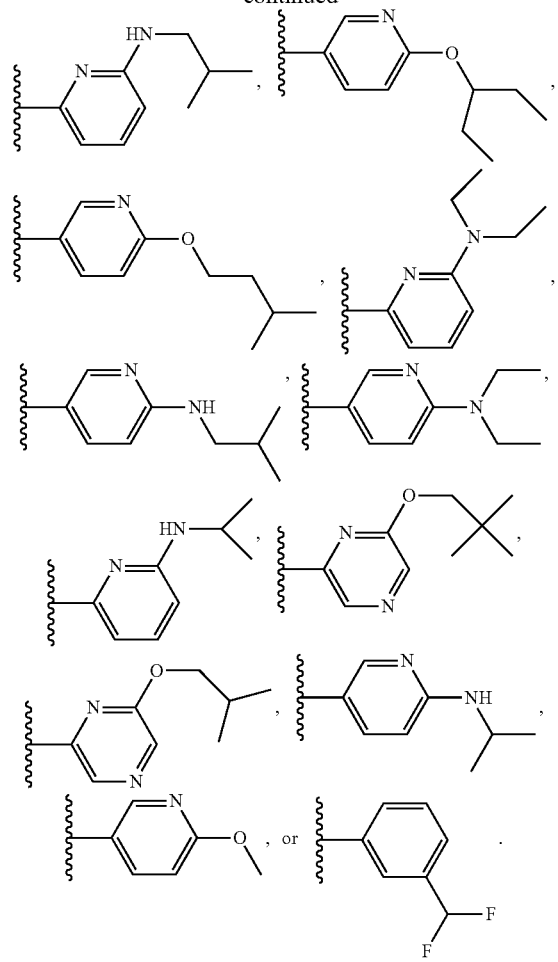

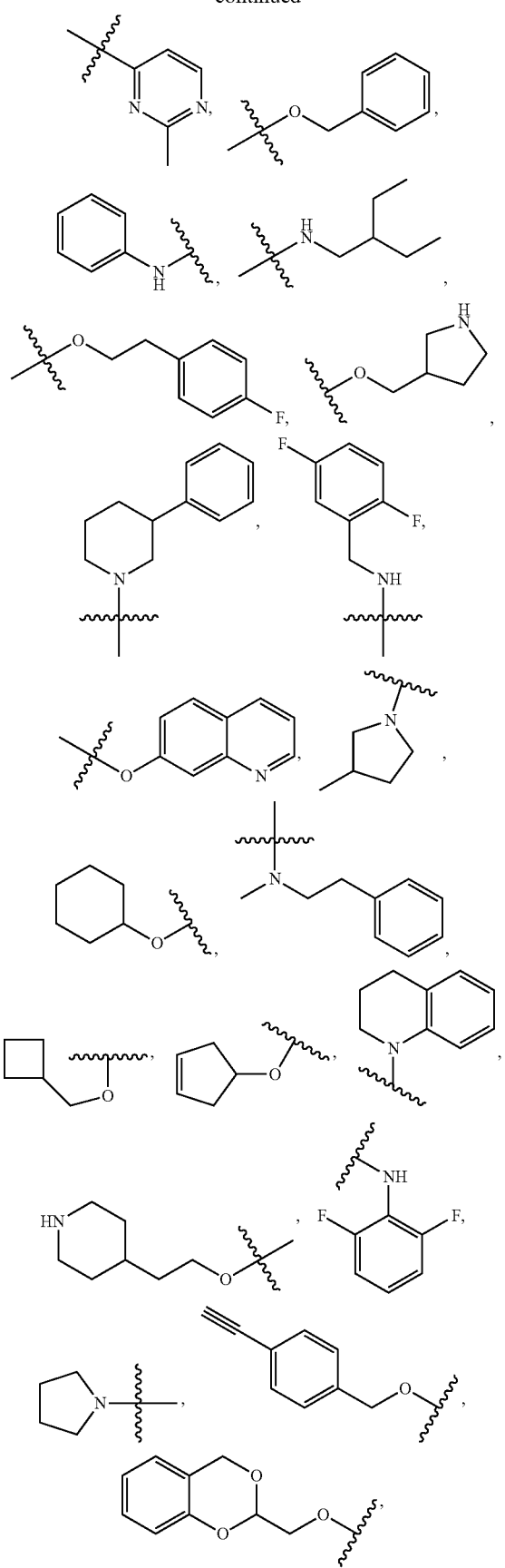

In some embodiments, R₂ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-R₄ wherein up to four CH₂ units are independently replaced with O, CO, S, SO, SO₂ or NR.

In some embodiments, R₂ is a group represented by the corresponding moieties shown in the compounds of Table 1. For example, R₂ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃) (CH₂CH₂CH₃), OCH(CH₃)₂, NH(CH₂)₂O(CH₂)₂CH₃, C(O) CH₃, CH₂CH₂OH, CH₂NH₂, NH(CH₂)₂OH, N(CH₃) CH₂CH₂CH₂OCH₃, NHCH₂CH₂COOH, NH(CH₂)₂N (CH₃)₂, NH(CH₂)₂NH₂, NH(CH₂)₃NH₂, NH(CH₂)₂OCH₃, NHCH(CH₃)₂,

215

-continued

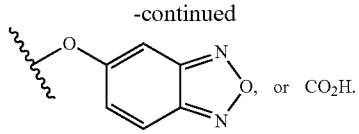, or CO₂H.

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

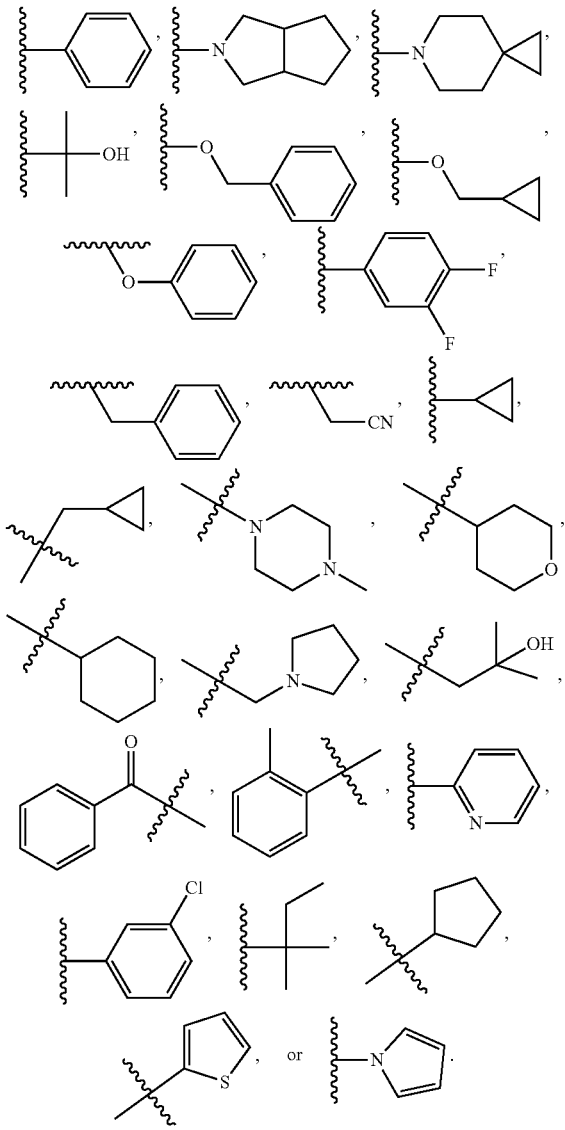

In some embodiments, p is 0. In some embodiments, p is 1. In some embodiments, p is 2.

In some embodiments, R₁ is phenyl, pyridine, or pyrazole. In some embodiments, R₁ is phenyl, pyridine, or pyrazole,

216

R₂ is amino or alkyl, and p is 0 or 1. In some embodiments, R₁ is phenyl, pyridine, or pyrazole, R₃ is alkyl, such as methyl, and q is 1, 2, 3, or 4.

In some embodiments, the invention features a compound of formula Ib-v:

Ib-v

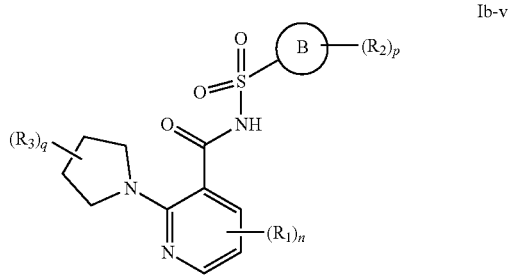

or a pharmaceutically acceptable salt thereof, wherein, independently for each occurrence:
  Ring B is a C6-C10 aryl ring or C3-C10 heteroaryl or heterocyclic ring wherein anywhere from 1 to 4 ring atoms are independently O, S, N, or NR;
  R₁ is halo; CN; F₃S; SiR₃; OH; NRR; C1-C6 alkyl or fluoroalkyl; C1-C6 alkoxy or fluoroalkoxy; C1-C6 alkenyl; C1-C6 alkynyl; (C1-C9 alkylene)-R₄ wherein up to four CH₂ units are independently replaced with O, CO, S, SO, SO₂ or NR; C6-C10 aryl; C3-C10 heteroaryl or heterocyclic ring wherein anywhere from 1 to 4 ring atoms are independently O, S, N, or NR; or C3-C10 cycloalkyl;
  R₂ is halo; OH; NRR; azide; CN; CO₂R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
  or two R₂ groups taken together may form a =CH₂ or =O group;
  R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
  or two R₃ groups taken together may form a =CH₂ or =O group;
  R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;
  R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
  n is 0, 1, 2 or 3;
  p is 0, 1, 2, or 3; and
  q is 0, 1, 2, 3, 4, or 5.
In some embodiments, the compound of formula Ib-v exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

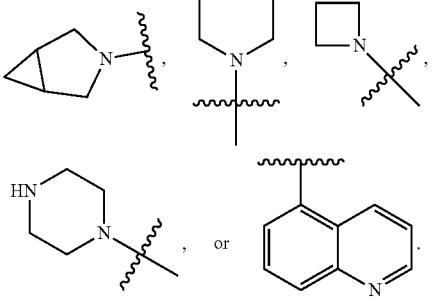

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

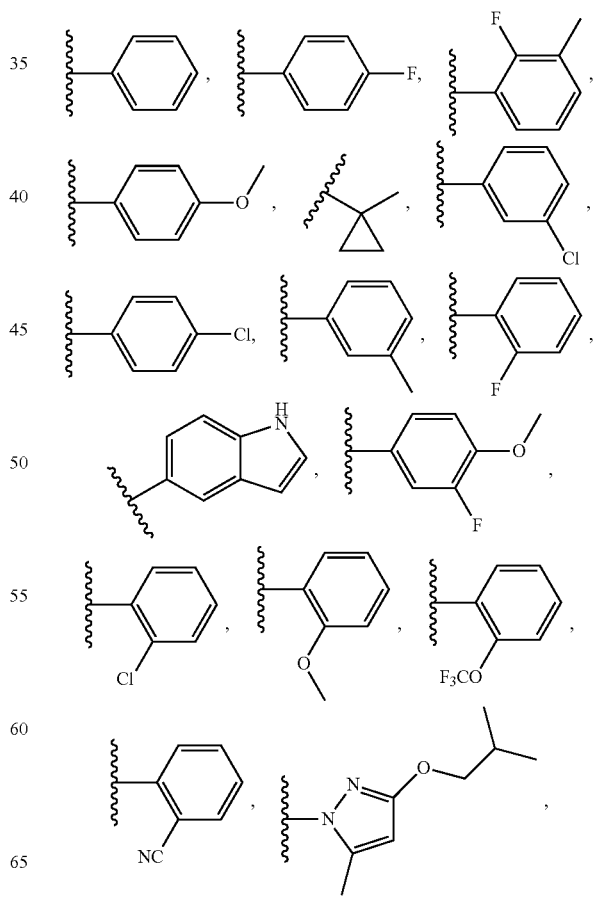

219
-continued
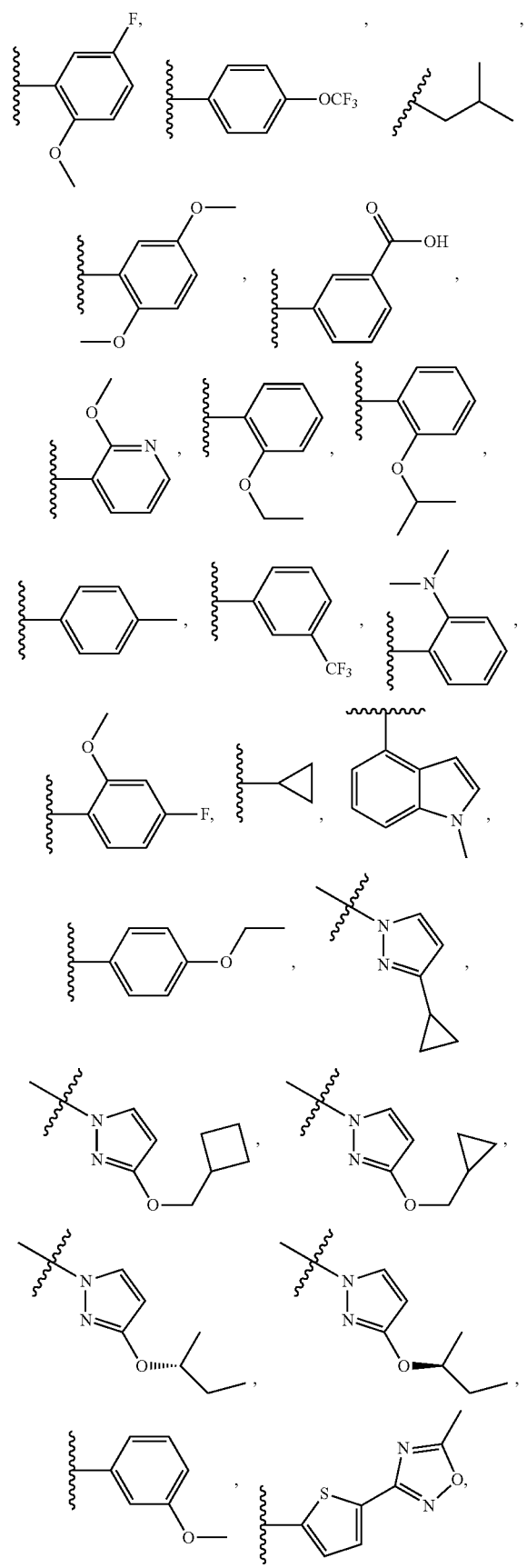
220
-continued
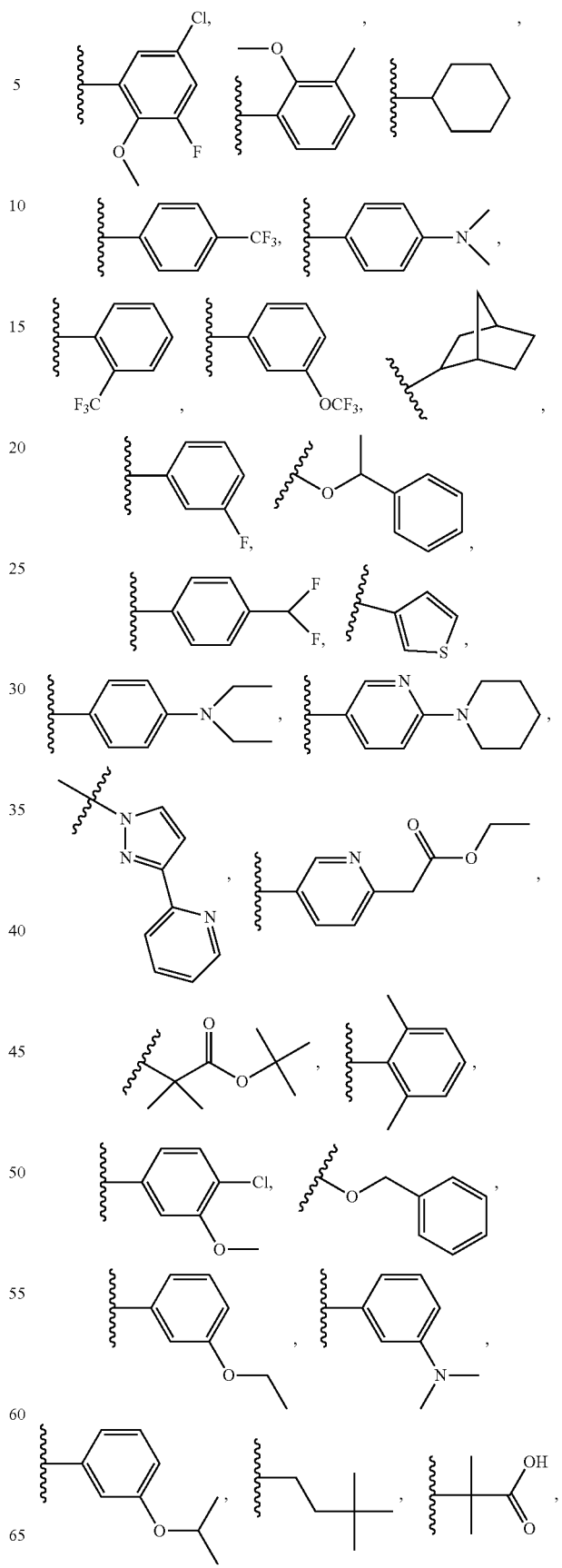

221
-continued
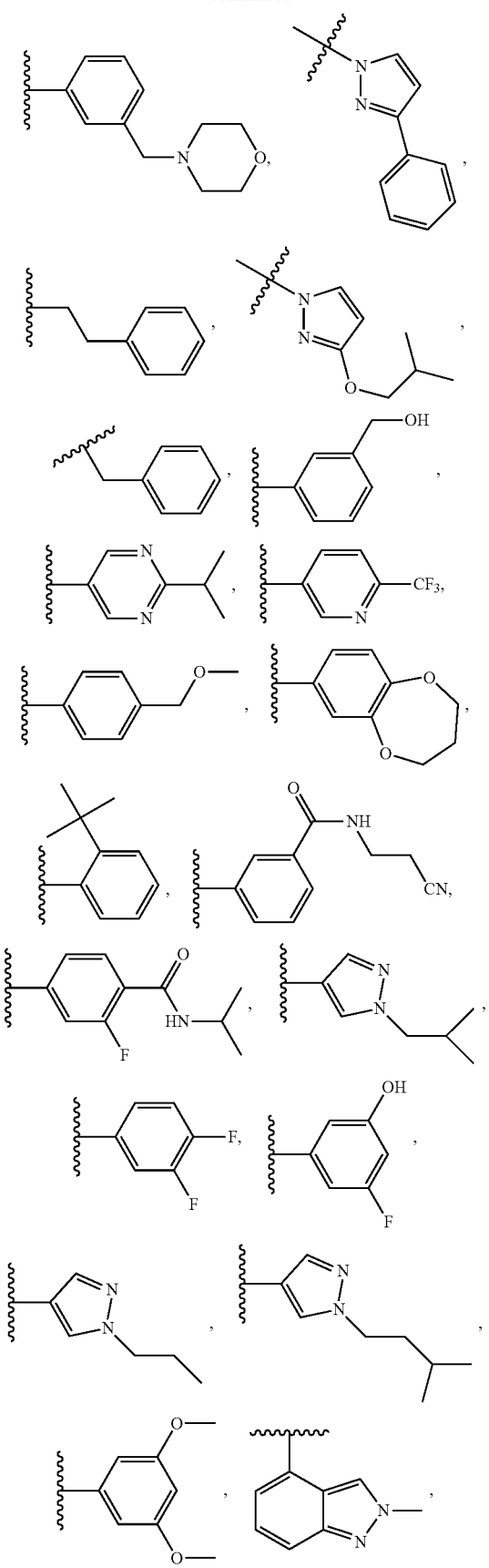
222
-continued
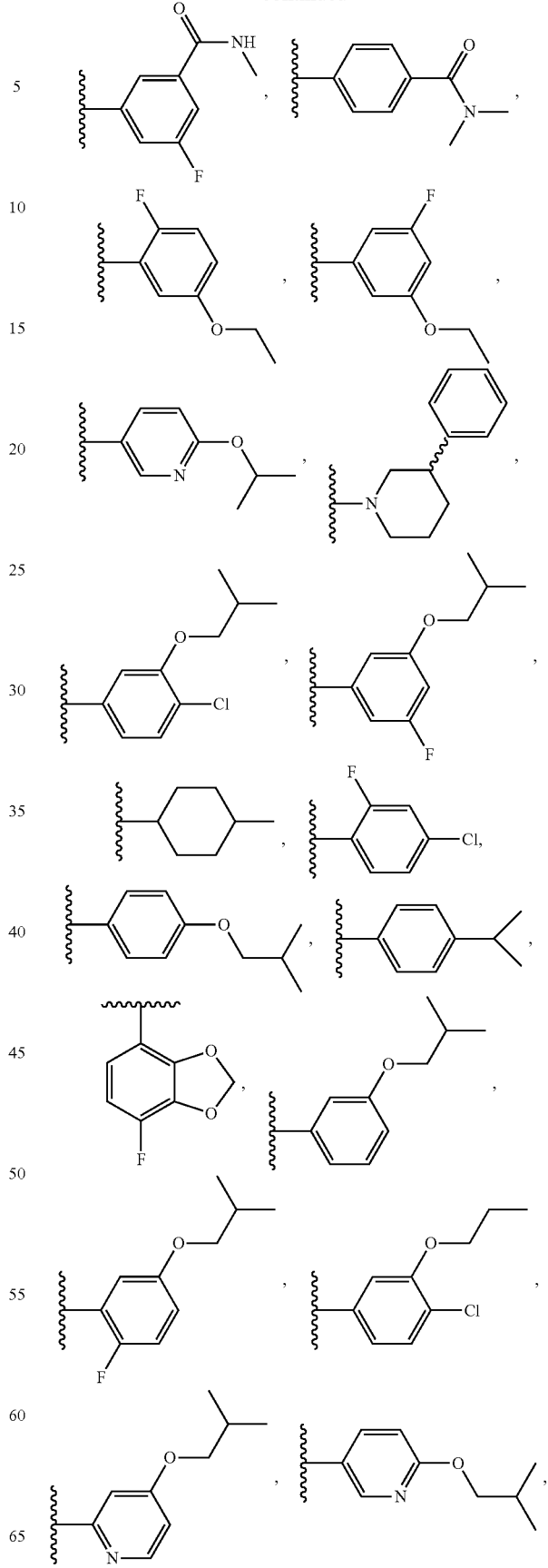

In some embodiments, R₂ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-R₄ wherein up to four CH₂ units are independently replaced with O, CO, S, SO, SO₂ or NR.

In some embodiments, R₂ is a group represented by the corresponding moieties shown in the compounds of Table 1. For example, R₂ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

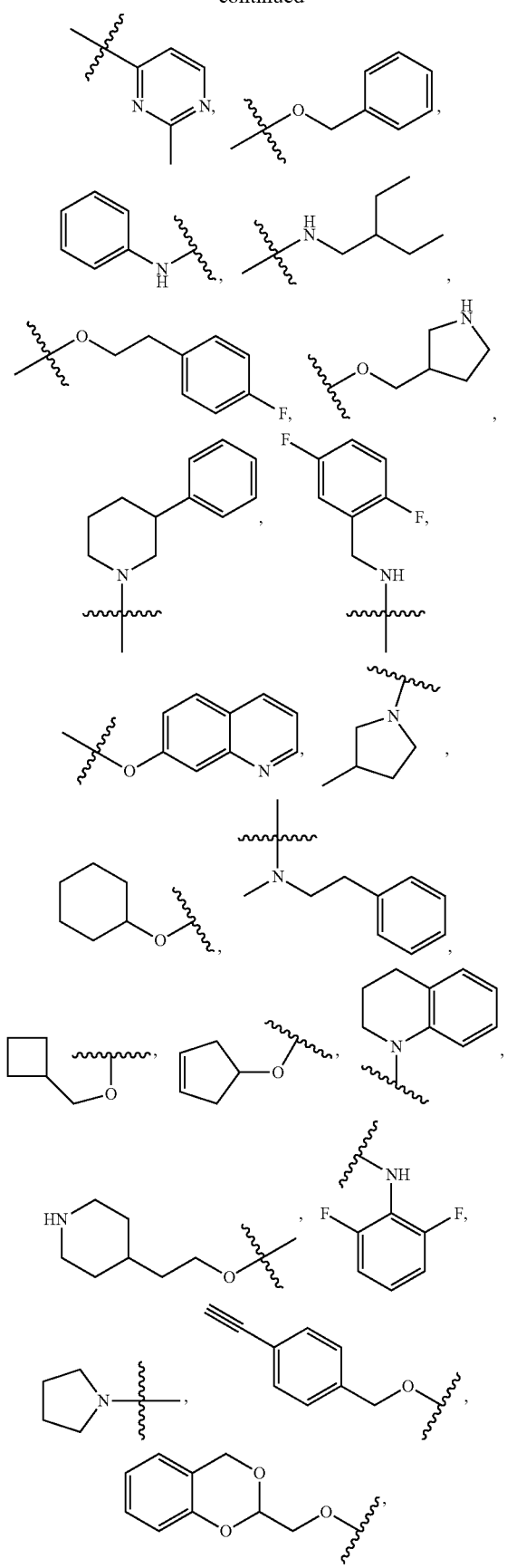

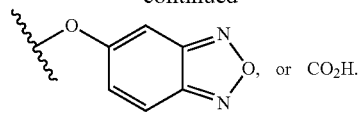, or $CO_2H$.

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

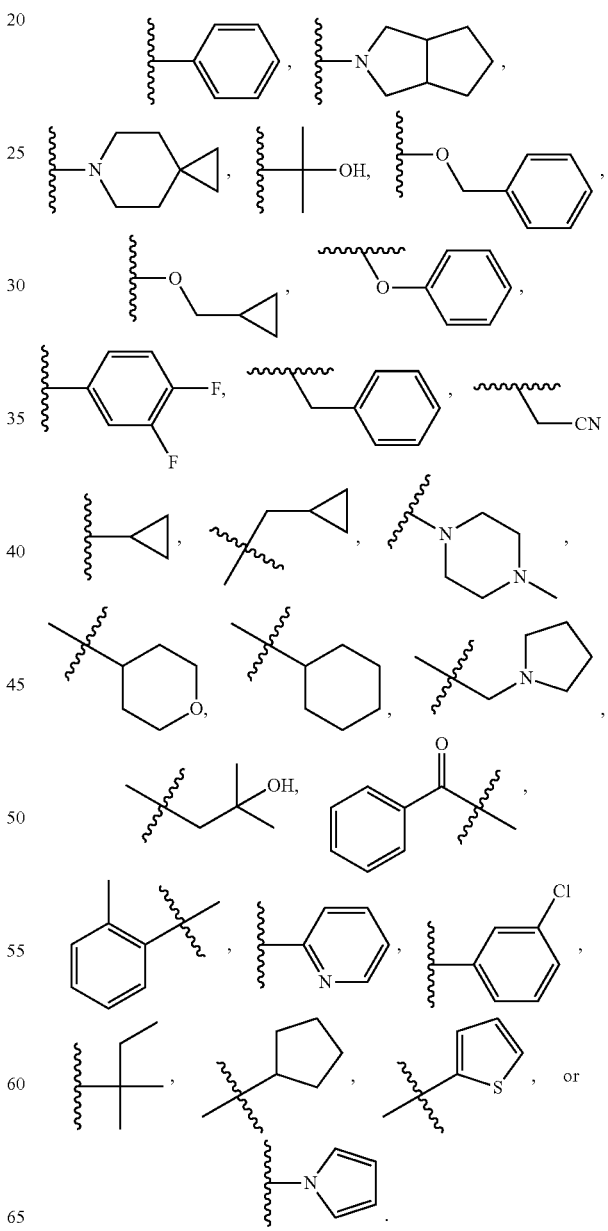

In some embodiments, n is 0. In some embodiments, n is 1. In some embodiments, n is 2.

In some embodiments, p is 0. In some embodiments, p is 1. In some embodiments, p is 2.

In some embodiments, $R_1$ is phenyl, pyridine, or pyrazole, and n is 1. In some embodiments, $R_1$ is phenyl, pyridine, or pyrazole, n is 1, $R_2$ is amino or alkyl, and p is 0 or 1. In some embodiments, $R_1$ is phenyl, pyridine, or pyrazole, n is 1, $R_3$ is alkyl, such as methyl, and q is 1, 2, 3, or 4.

In some embodiments, the invention features a compound of formula Ib-v-1:

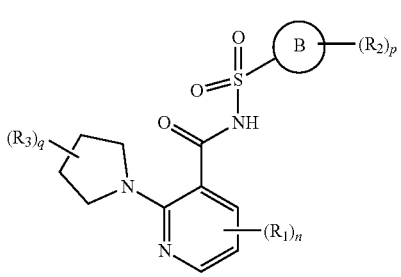

Ib-v-1 or a pharmaceutically acceptable salt thereof, wherein, independently for each occurrence:
Ring B is a C3-C10 heteroaryl ring wherein anywhere from 1 to 4 ring atoms are independently O, S, N, or NR;
$R_1$ is halo; CN; F5S; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;
$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_2$ groups taken together may form a =$CH_2$ or =O group;
$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_3$ groups taken together may form a =$CH_2$ or =O group;
$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;
R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;
p is 0, 1, 2, or 3; and
q is 0, 1, 2, 3, 4, or 5.

In some embodiments, the compound of formula Ib-v-1 exists as a pharmaceutically acceptable prodrug.

In some embodiments, ring B is pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

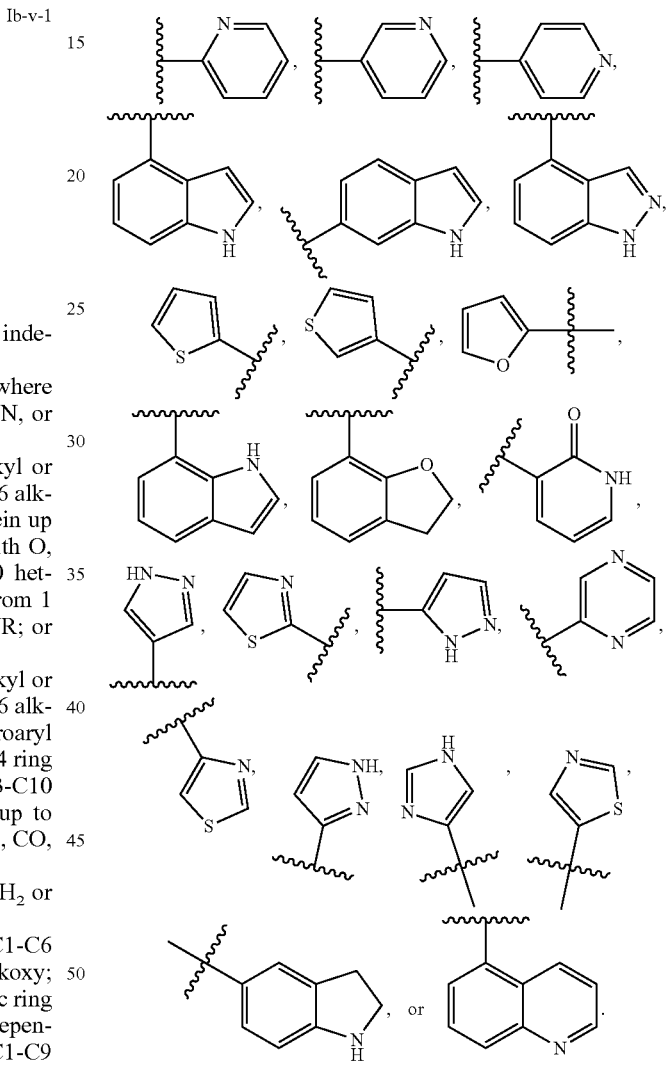

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1.

For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,
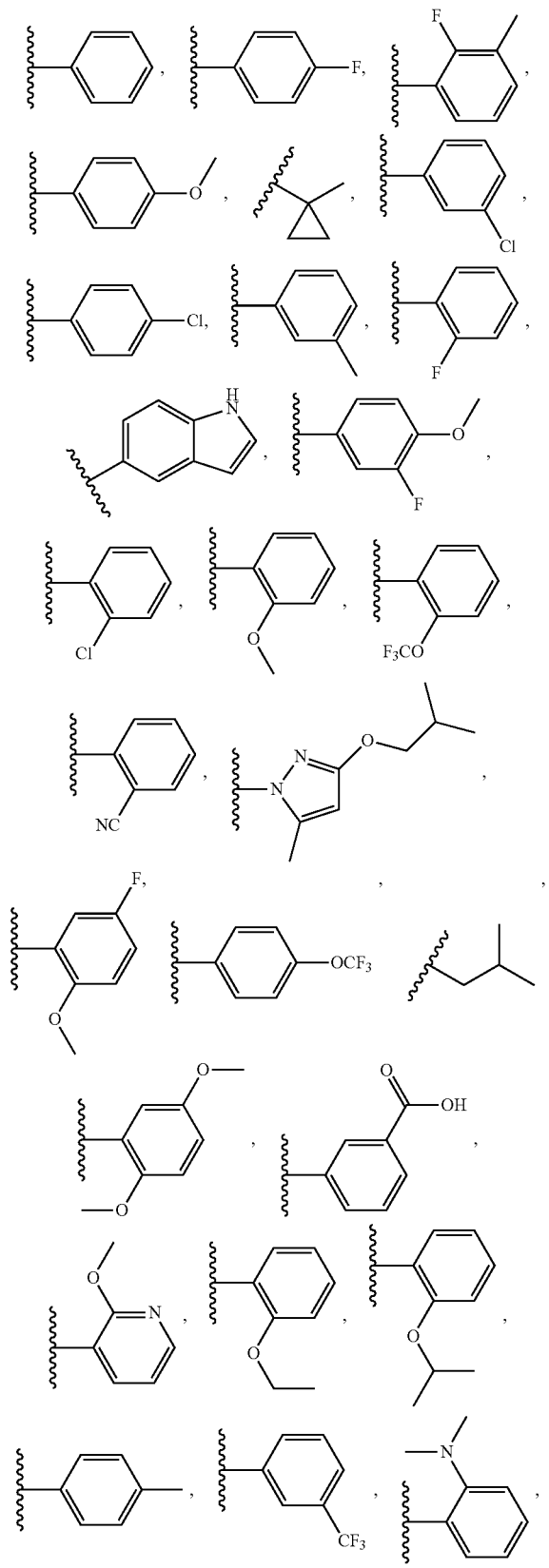
-continued
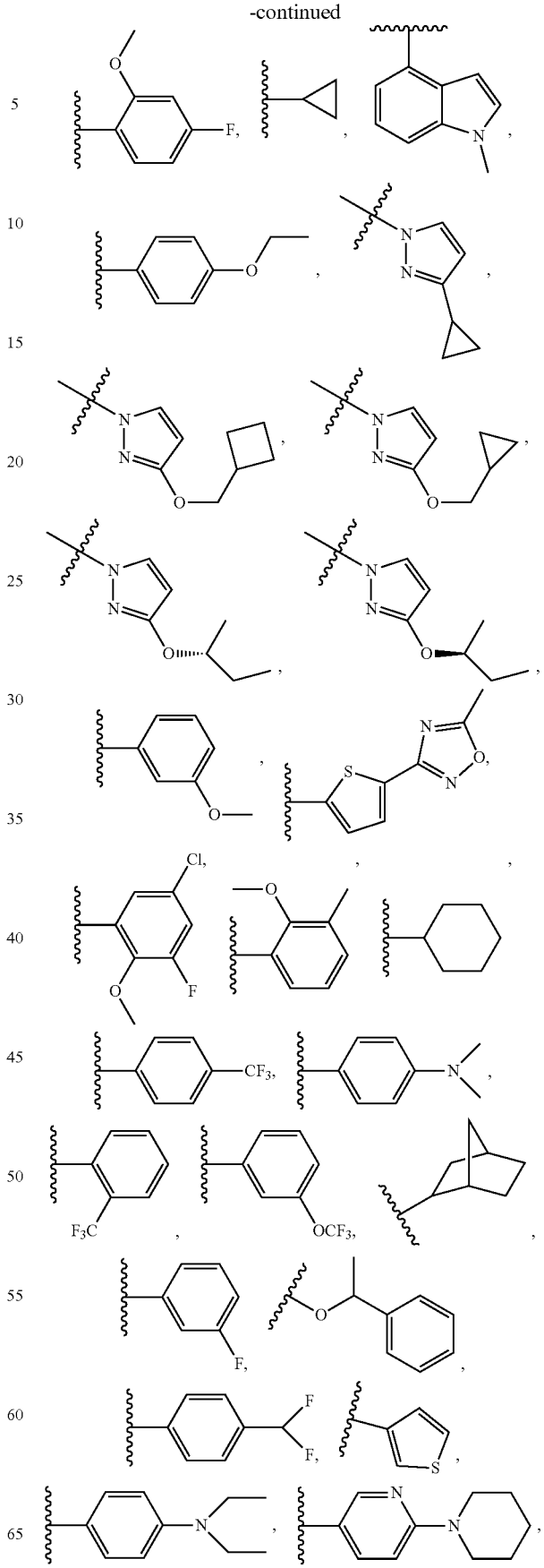

231
-continued
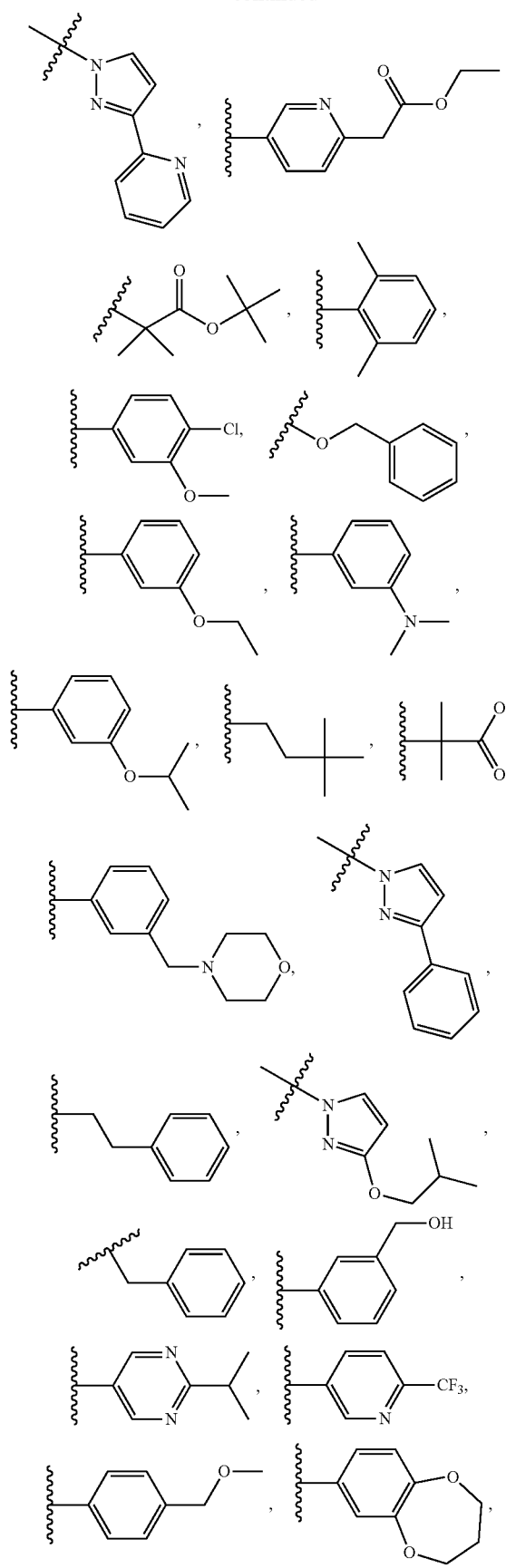
232
-continued
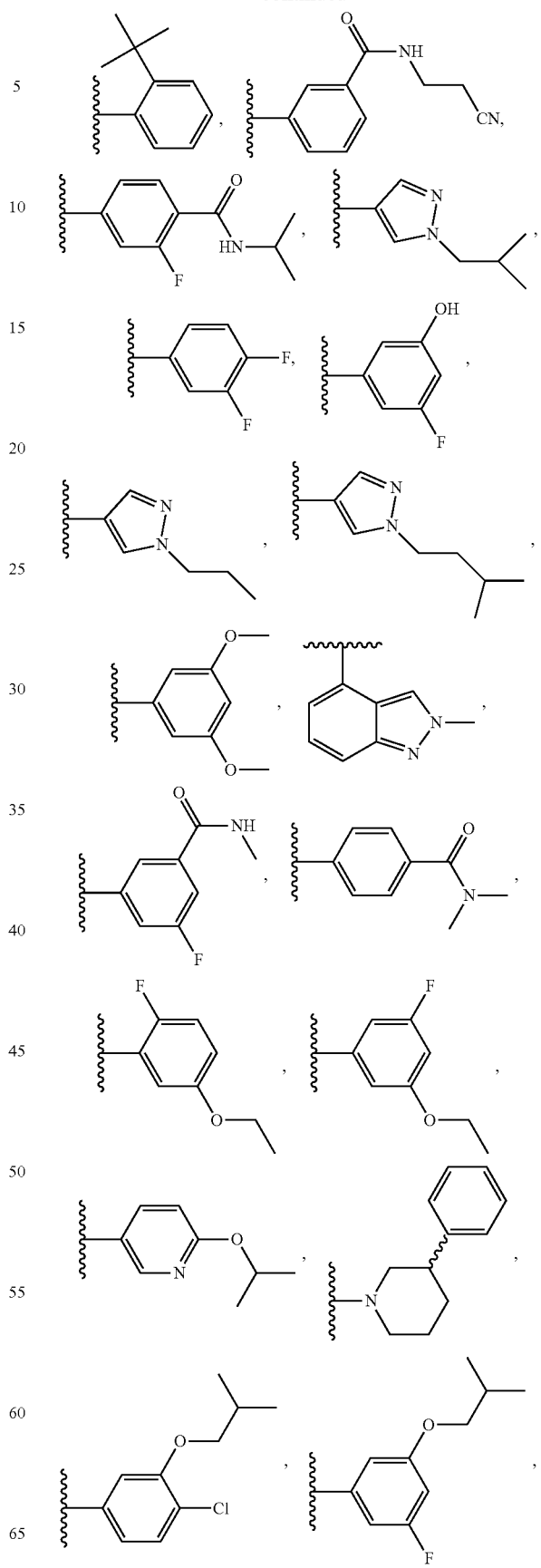

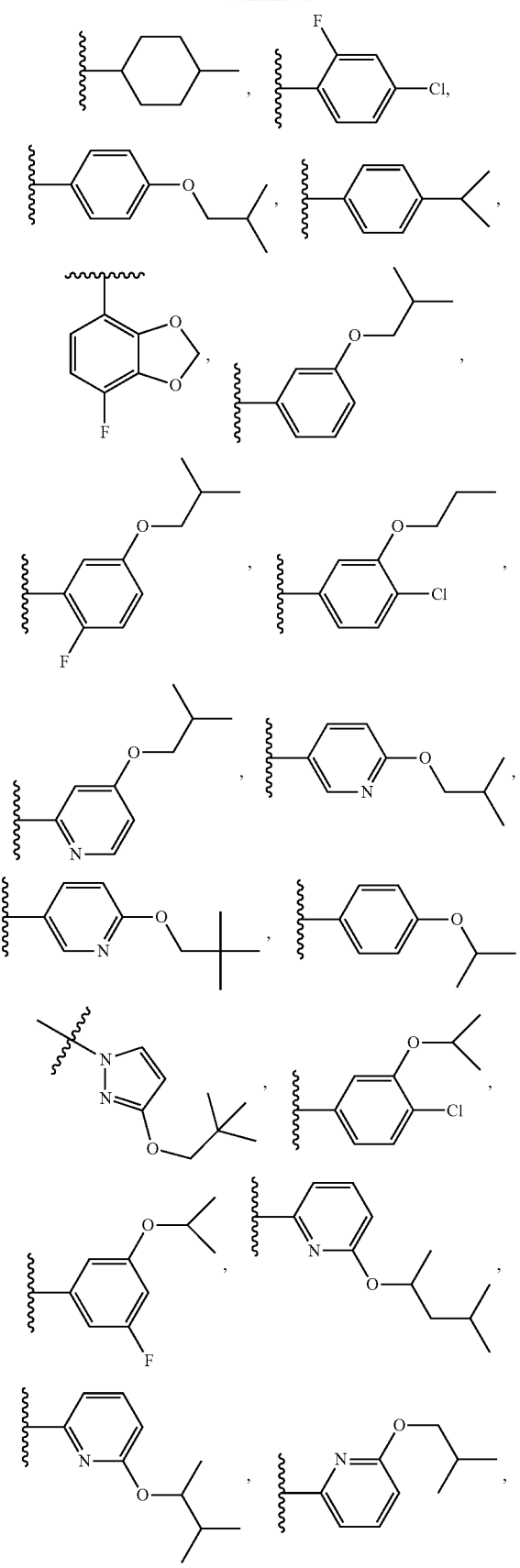
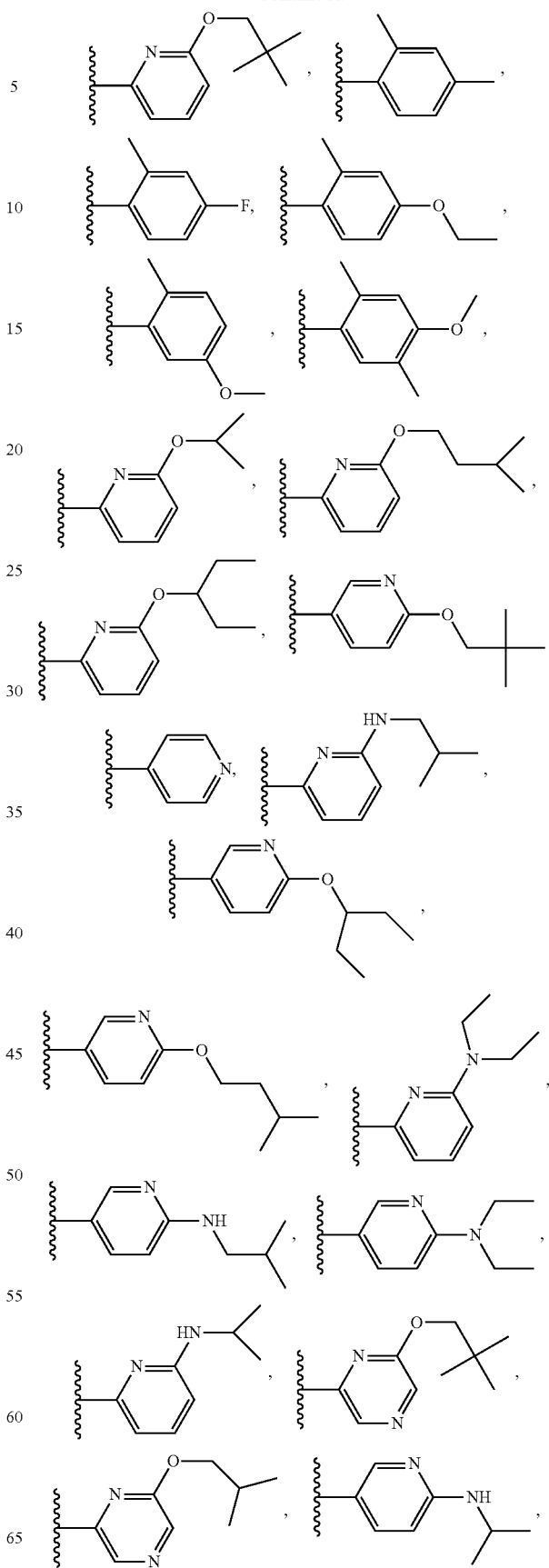

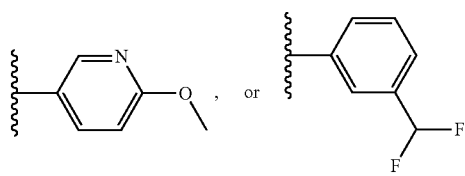

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

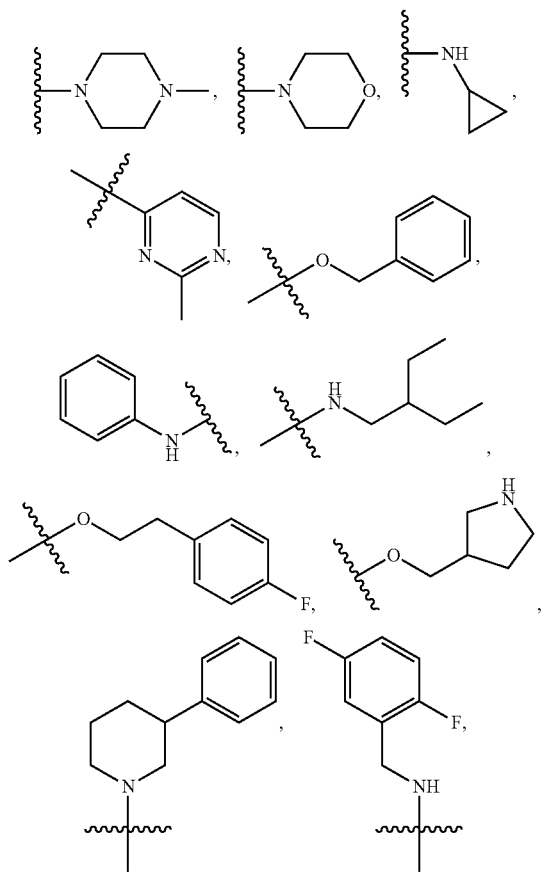

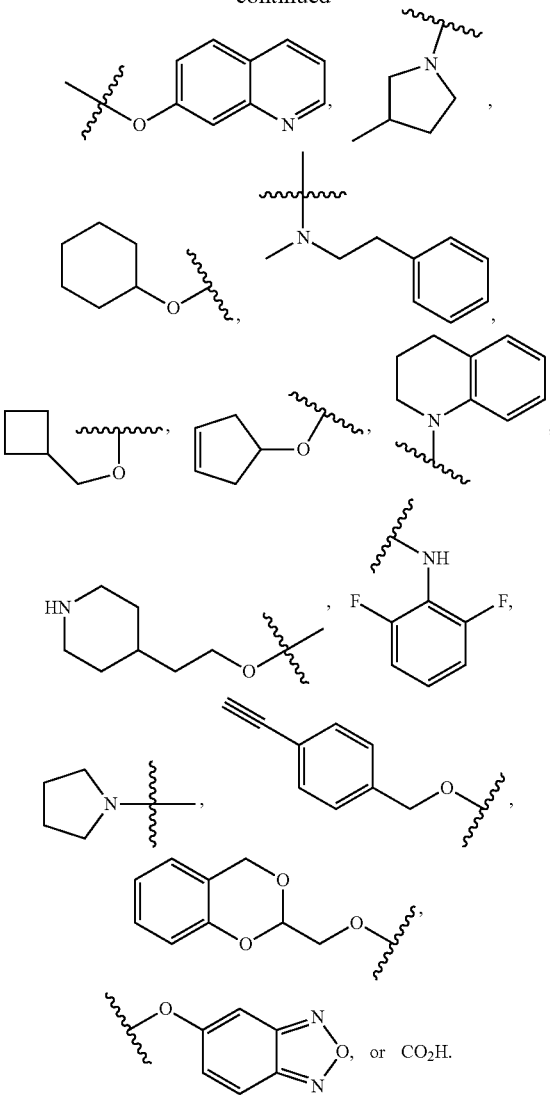

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

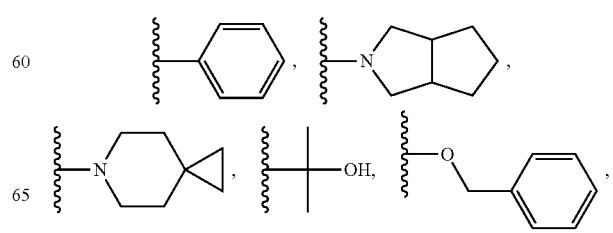

-continued

In some embodiments, n is 0. In some embodiments, n is 1. In some embodiments, n is 2.

In some embodiments, p is 0. In some embodiments, p is 1. In some embodiments, p is 2.

In some embodiments, $R_1$ is phenyl, pyridine, or pyrazole, and n is 1. In some embodiments, $R_1$ is phenyl, pyridine, or pyrazole, n is 1, $R_2$ is amino or alkyl, and p is 0 or 1. In some embodiments, $R_1$ is phenyl, pyridine, or pyrazole, n is 1, $R_3$ is alkyl, such as methyl, and q is 1, 2, 3, or 4.

In some embodiments, the invention features a compound of formula Ib-v-2:

Ib-v-2 or a pharmaceutically acceptable salt thereof, wherein, independently for each occurrence:

Ring B is a C6-C10 aryl ring;
$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;
$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_2$ groups taken together may form a $=CH_2$ or $=O$ group;
$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_3$ groups taken together may form a $=CH_2$ or $=O$ group;
$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;
R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
n is 0, 1, 2 or 3;
p is 0, 1, 2, or 3; and
q is 0, 1, 2, 3, 4, or 5.

In some embodiments, the compound of formula Ib-v-2 exists as a pharmaceutically acceptable prodrug.

In some embodiments, ring B is phenyl or napthalene.

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

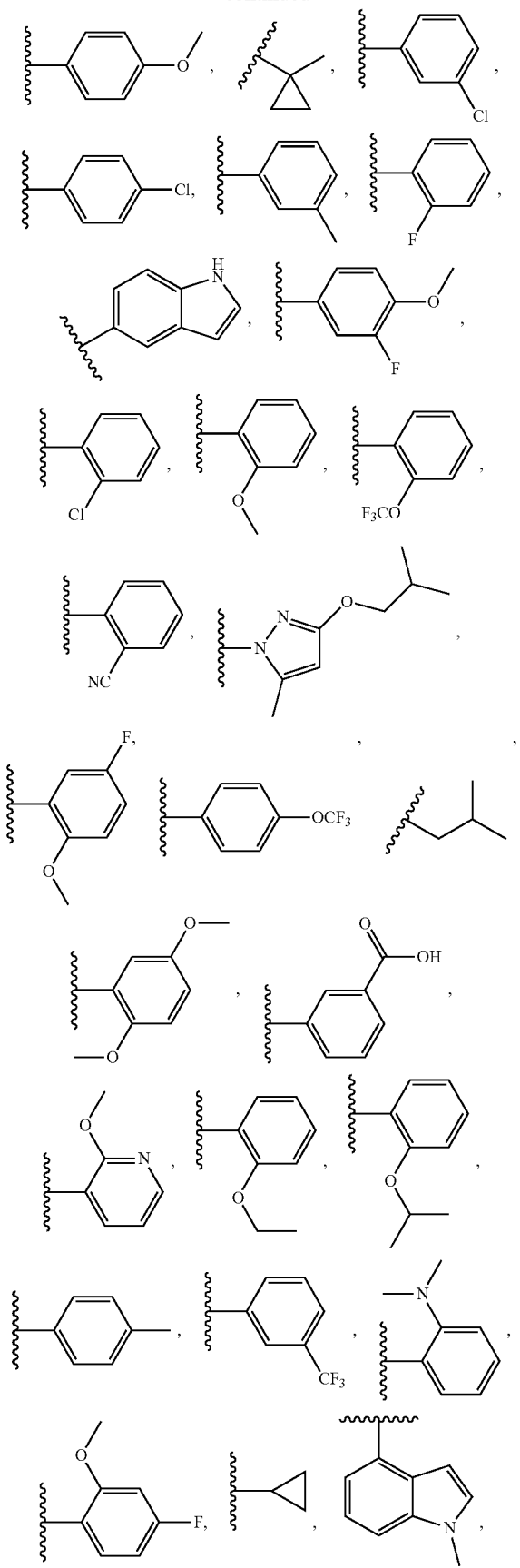
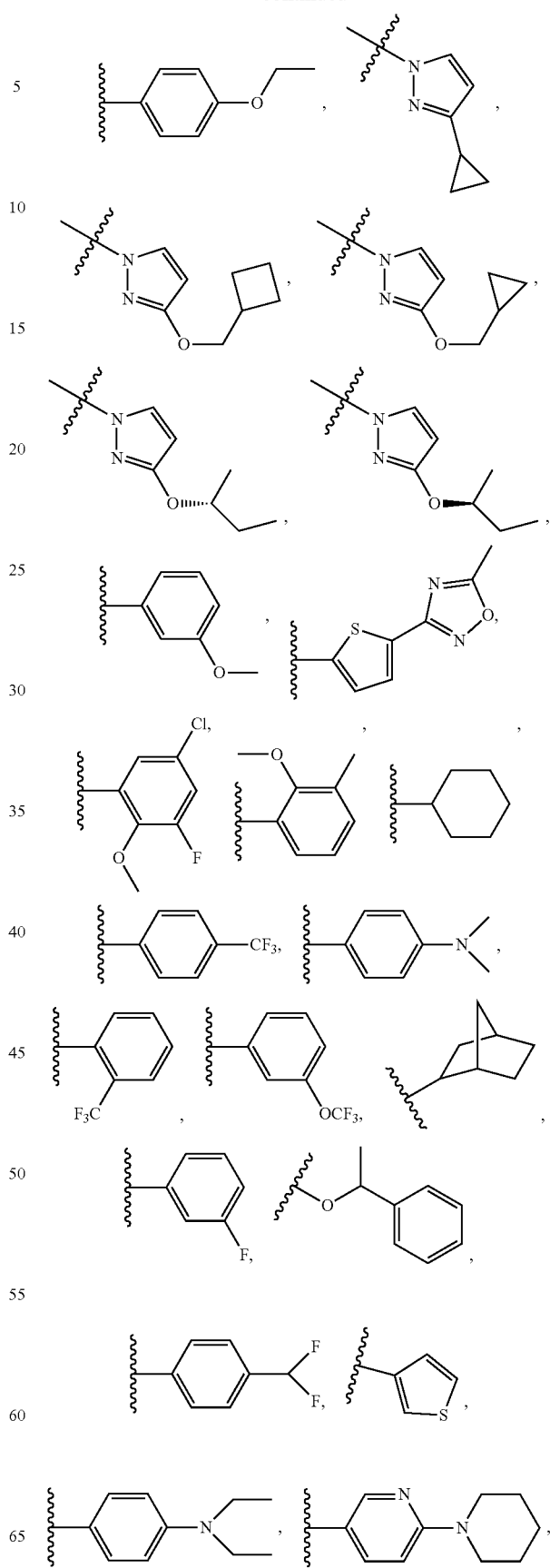

241
-continued
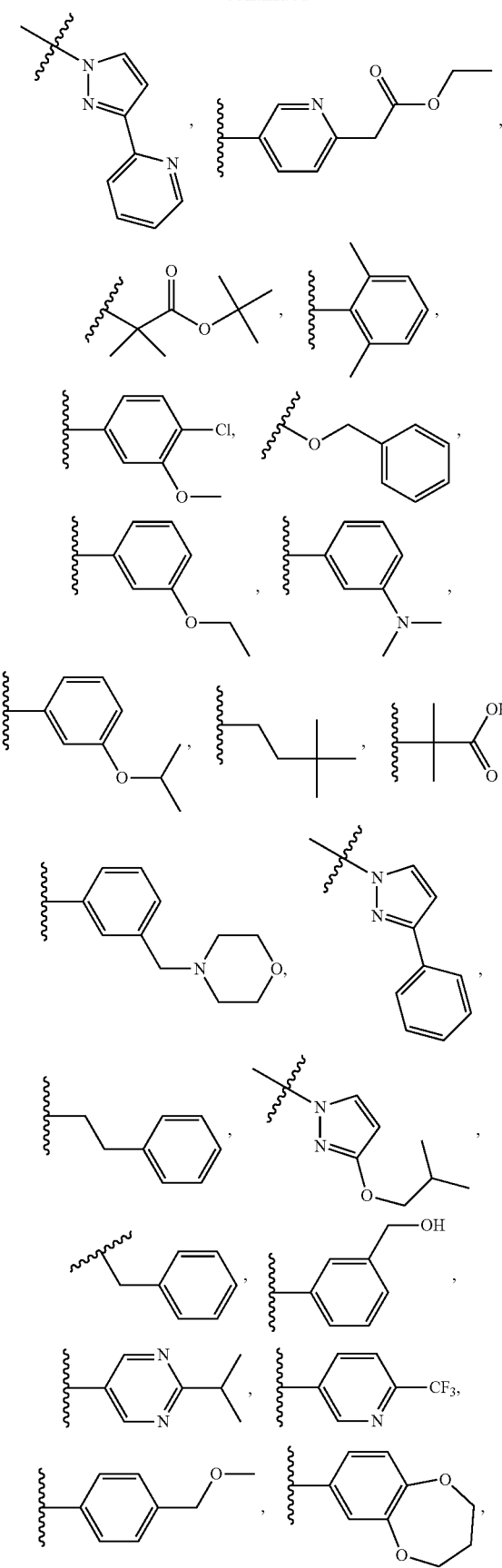
242
-continued
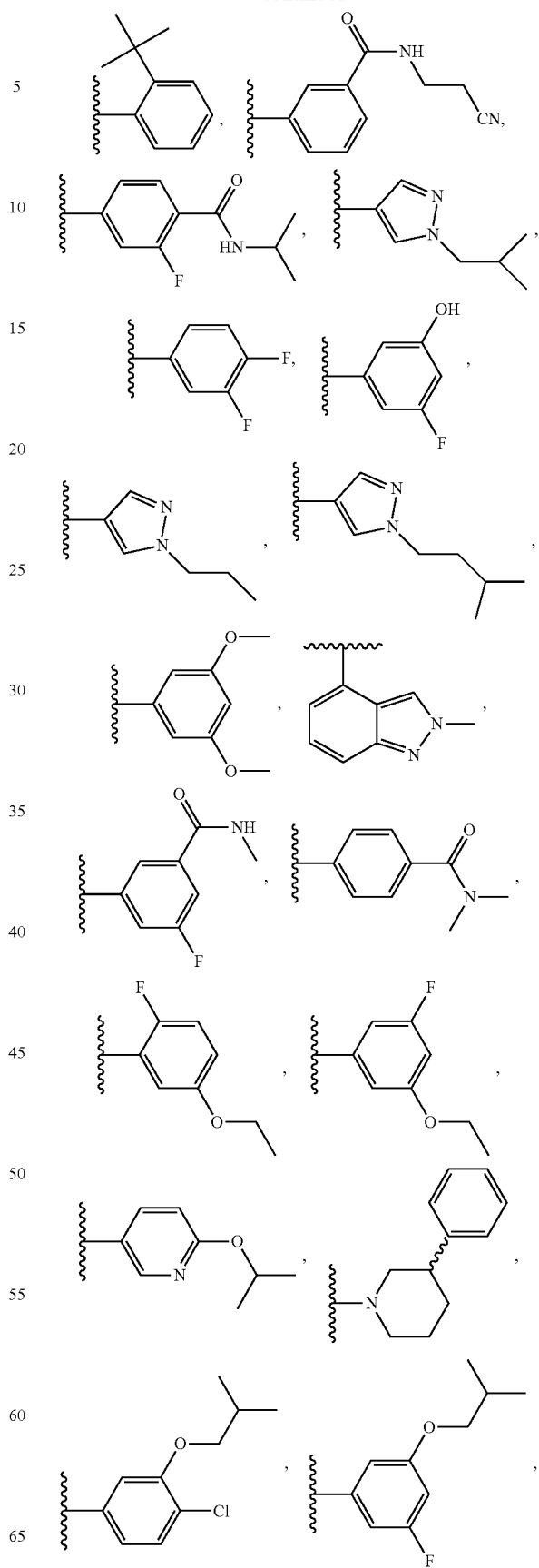

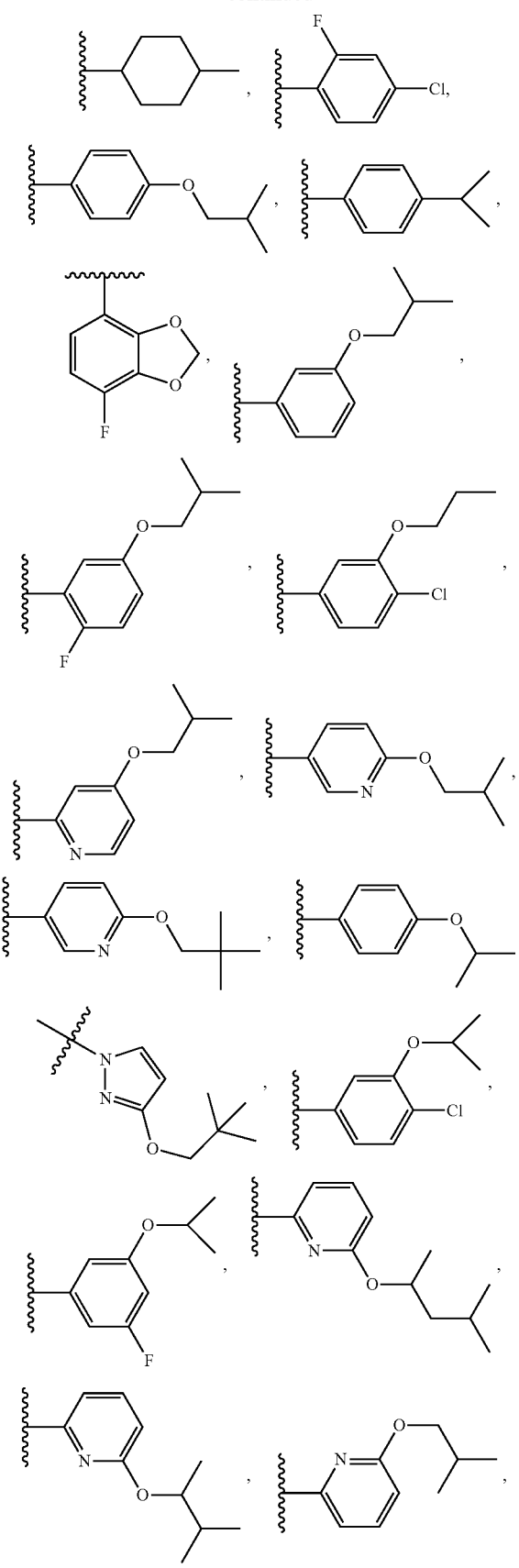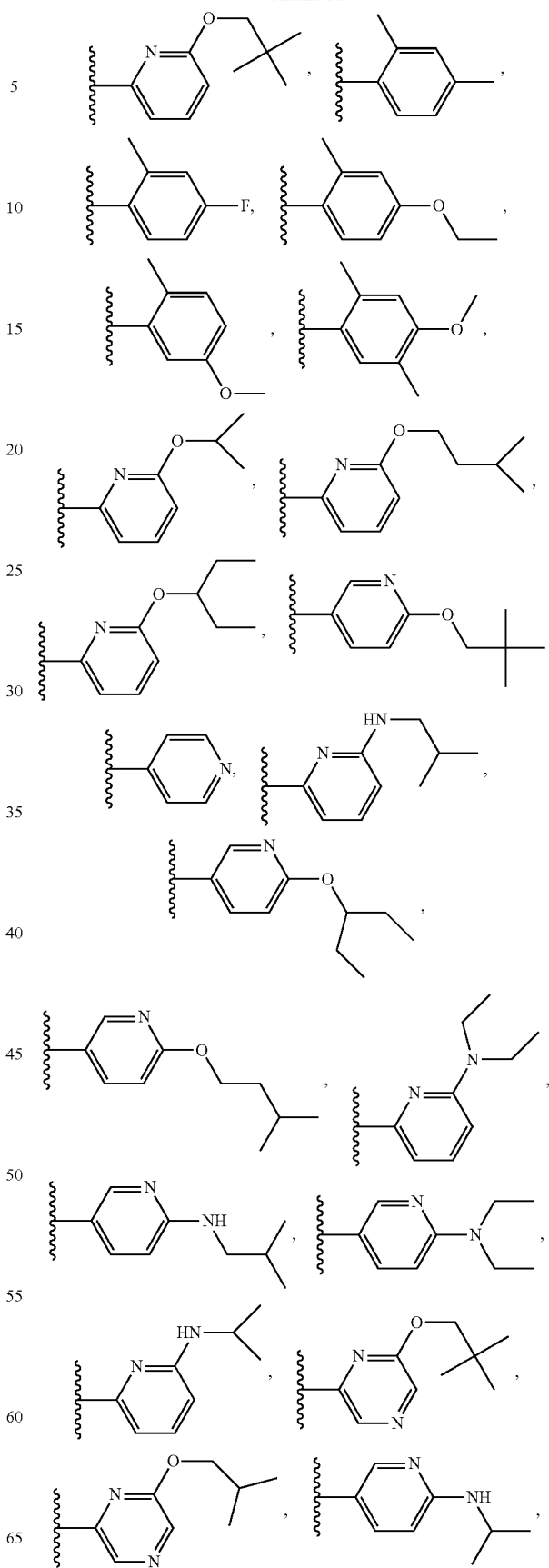

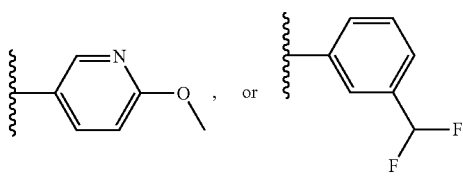

In some embodiments, R₂ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-R₄ wherein up to four CH₂ units are independently replaced with O, CO, S, SO, SO₂ or NR.

In some embodiments, R₂ is a group represented by the corresponding moieties shown in the compounds of Table 1. For example, R₂ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

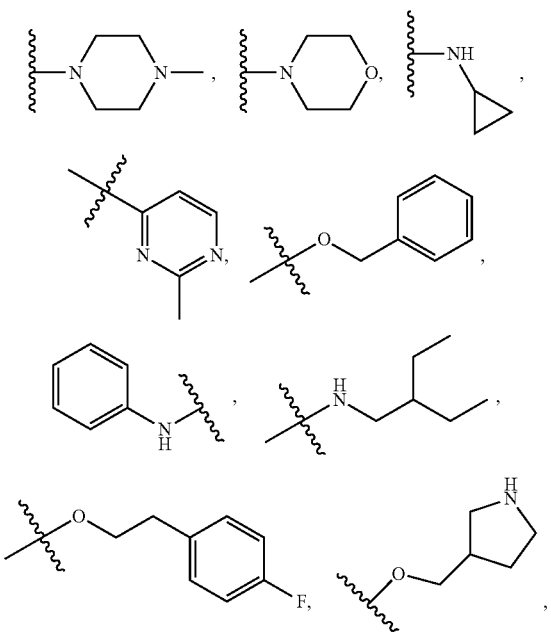

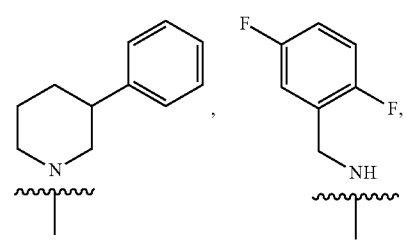

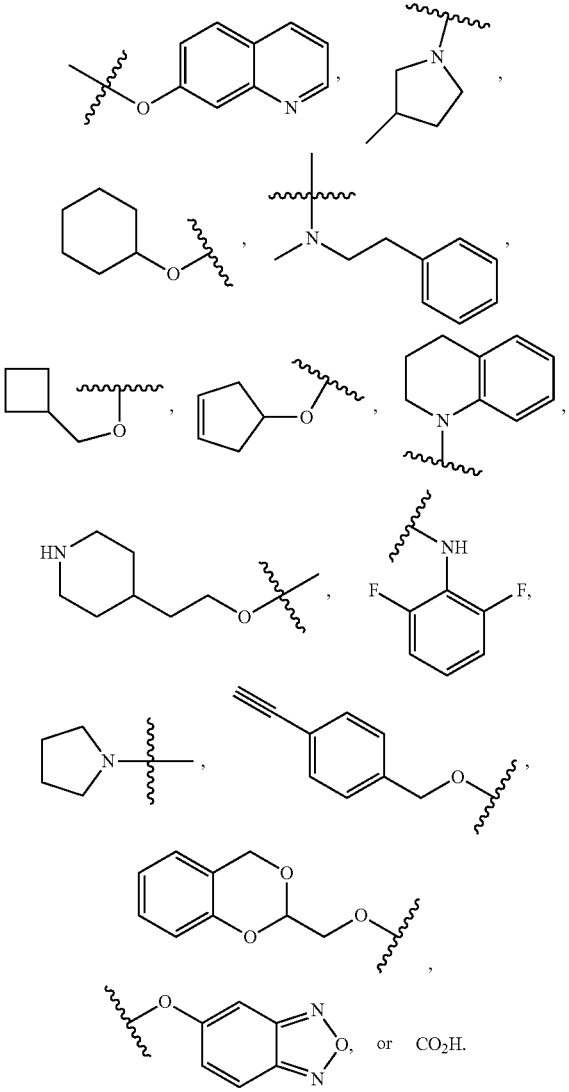

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

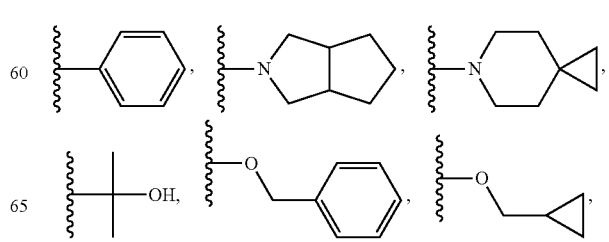

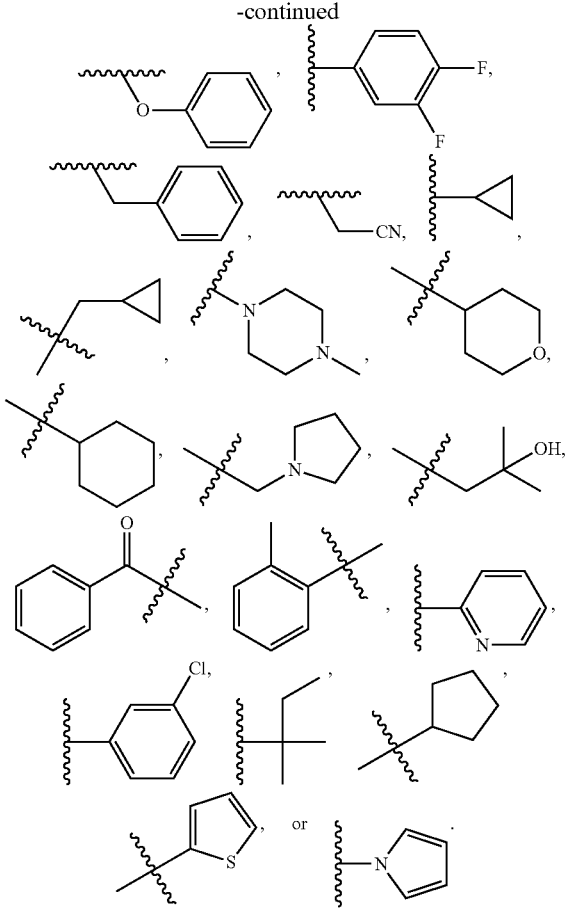

In some embodiments, n is 0. In some embodiments, n is 1. In some embodiments, n is 2.

In some embodiments, p is 0. In some embodiments, p is 1. In some embodiments, p is 2.

In some embodiments, $R_1$ is phenyl, pyridine, or pyrazole, and n is 1. In some embodiments, $R_1$ is phenyl, pyridine, or pyrazole, n is 1, $R_2$ is amino or alkyl, and p is 0 or 1. In some embodiments, $R_1$ is phenyl, pyridine, or pyrazole, n is 1, $R_3$ is alkyl, such as methyl, and q is 1, 2, 3, or 4.

In some embodiments, the invention features a compound of formula Ib-vi:

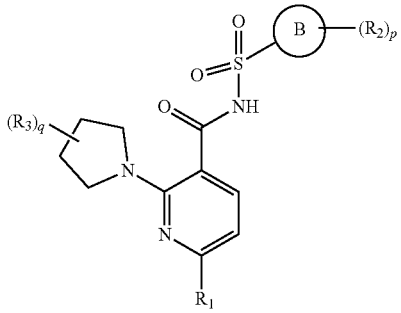

Ib-vi or a pharmaceutically acceptable salt thereof, wherein, independently for each occurrence:

Ring B is a C6-C10 aryl ring or C3-C10 heteroaryl or heterocyclic ring wherein anywhere from 1 to 4 ring atoms are independently O, S, N, or NR;

$R_1$ is C6-C10 aryl or C3-C10 heteroaryl wherein anywhere from 1 to 4 ring atoms are independently O, S, N, or NR;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a $=CH_2$ or $=O$ group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a $=CH_2$ or $=O$ group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

p is 0, 1, 2, or 3; and q is 0, 1, 2, 3, 4, or 5.

In some embodiments, the compound of formula Ib-vi exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

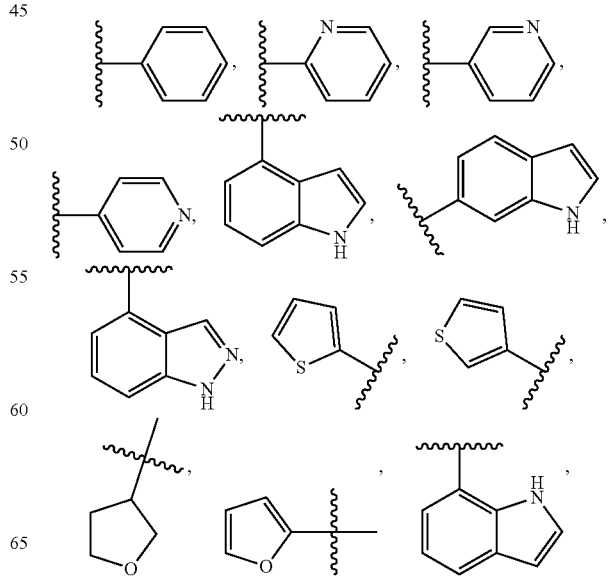

249
-continued
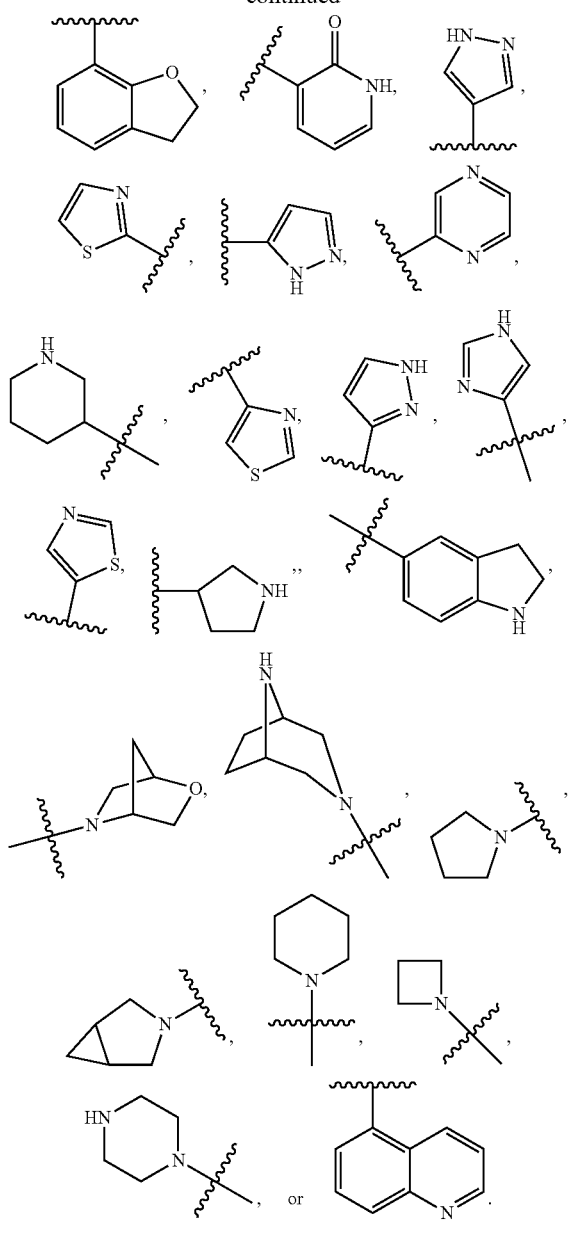
250
-continued
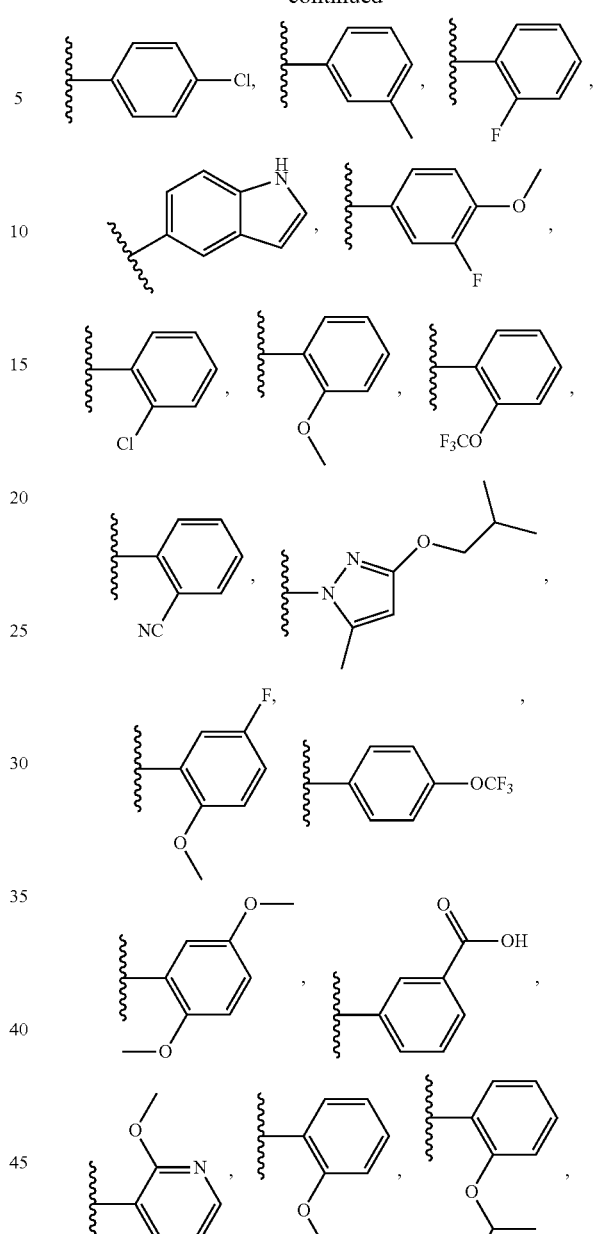
In some embodiments, R₁ is a phenyl, thiophene, pyridine, or pyrazole.
In some embodiments, R₁ is a group represented by the corresponding moieties shown in the compounds of Table 1. For example, R₁ is
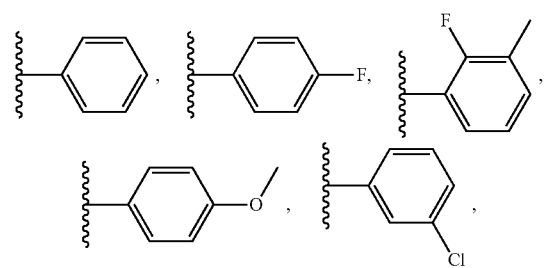
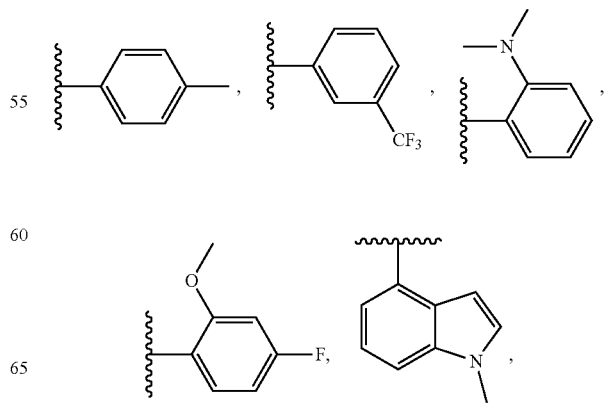

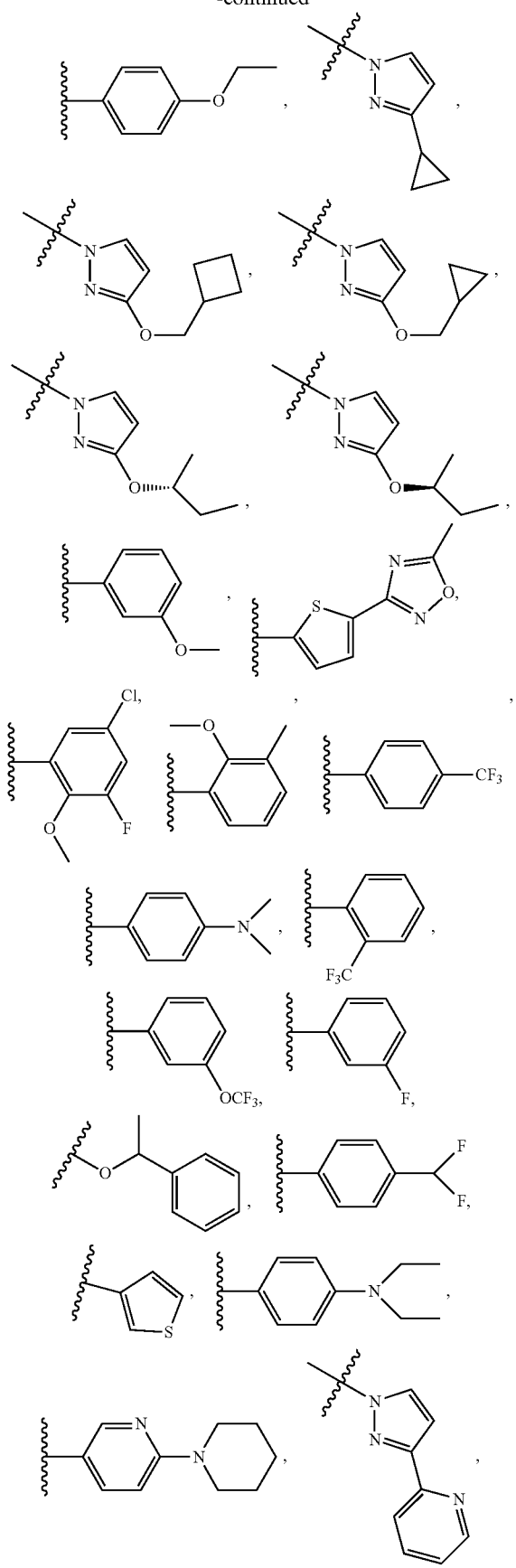
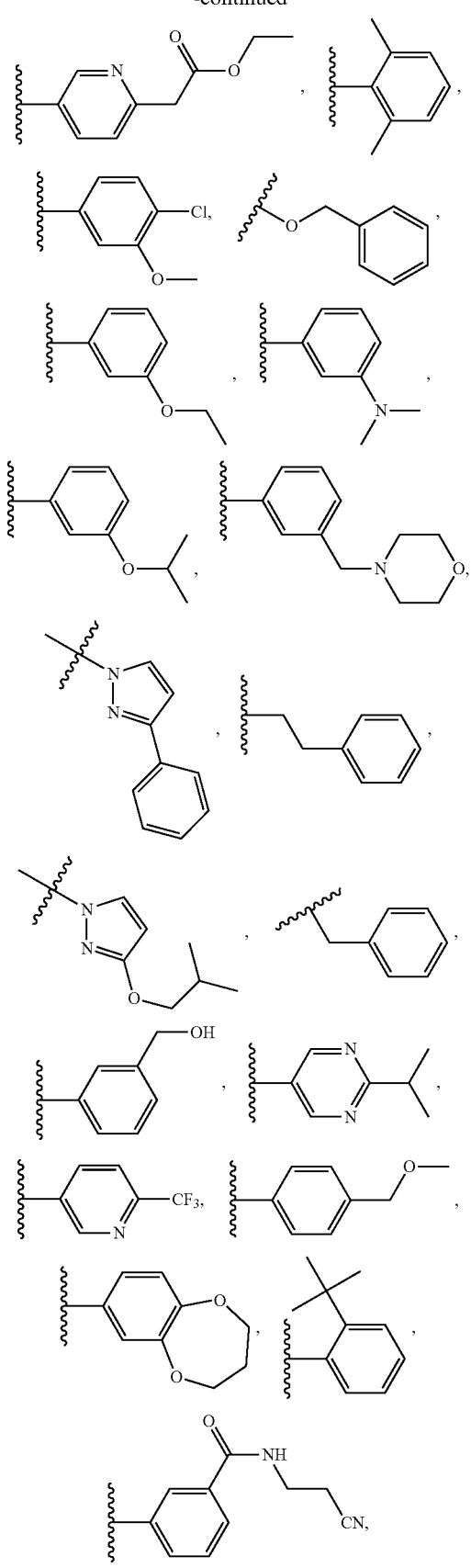

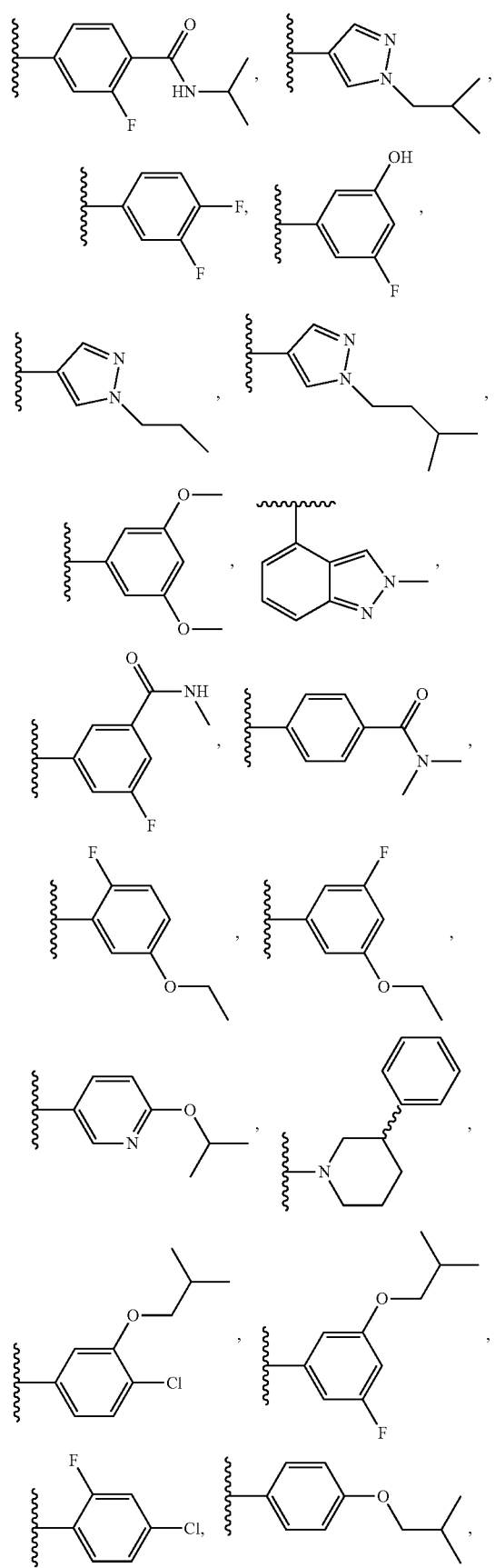
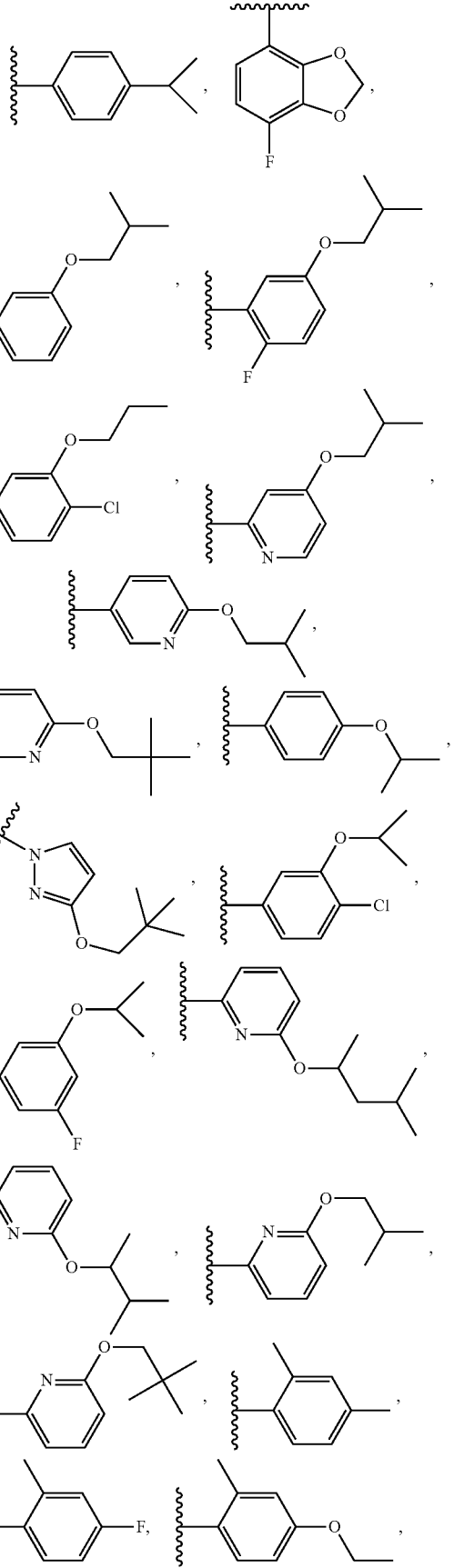

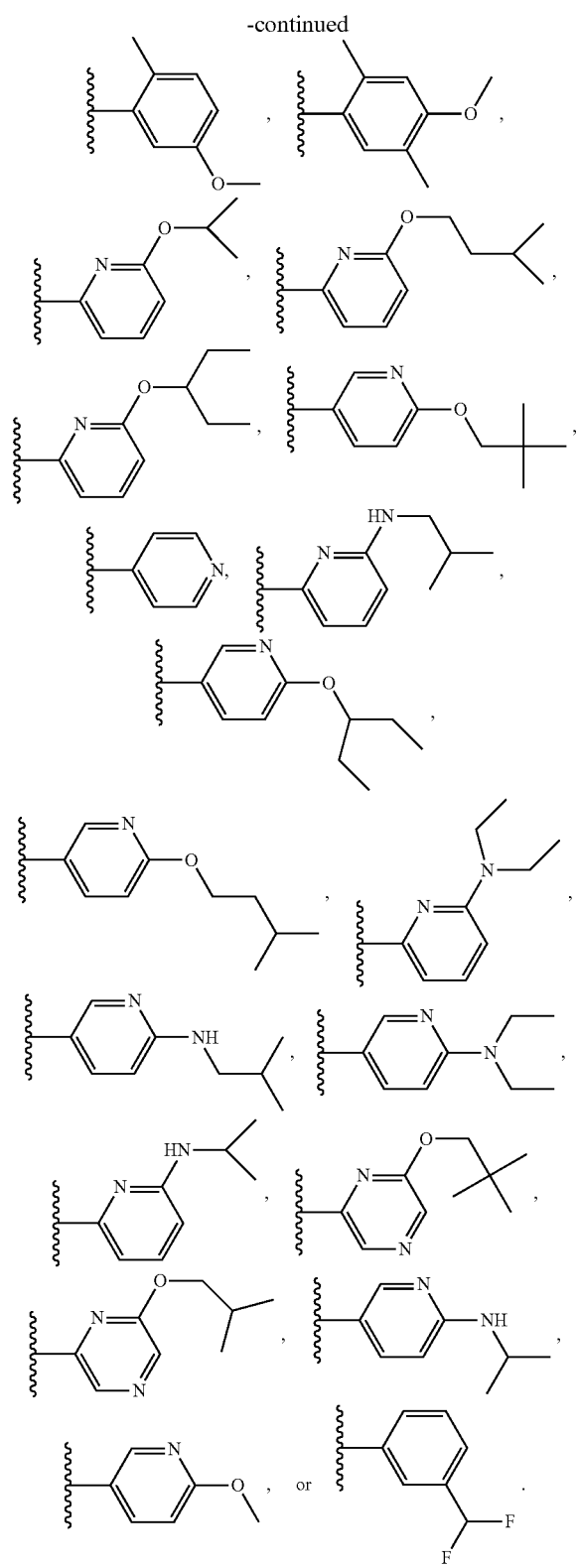

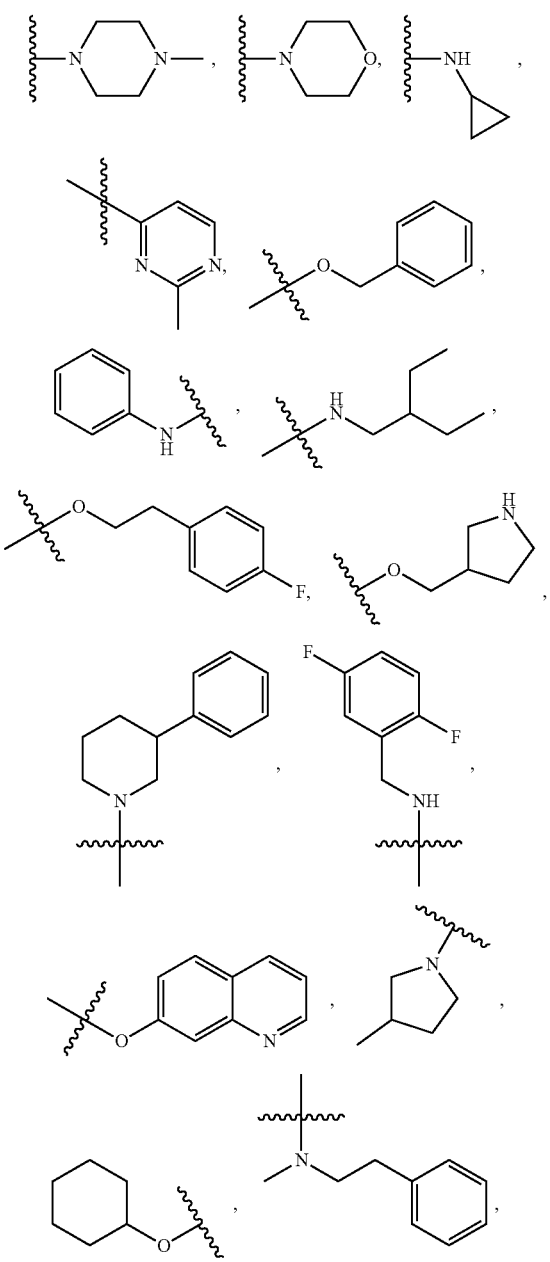

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, C(O)$CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$, In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

257

-continued

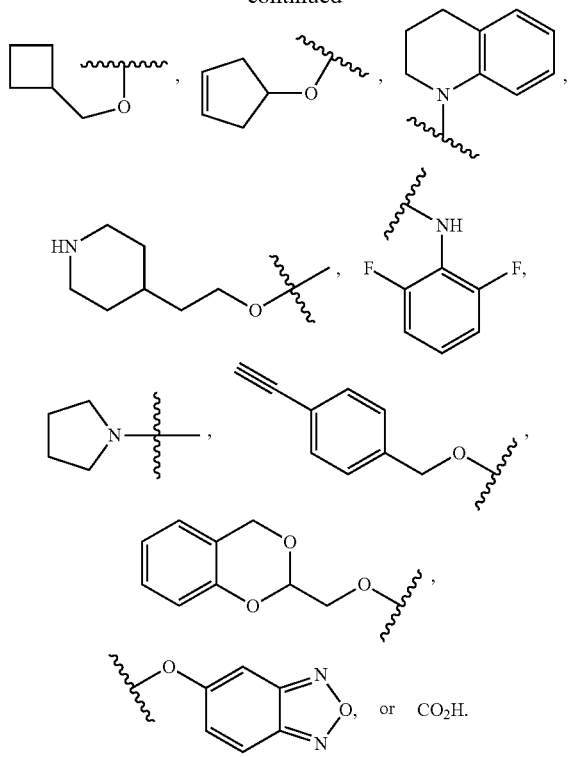

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, $—CH_2N(CH_3)_2$, $CO_2tBu$, tBu, $=CH_2$, $=O$,

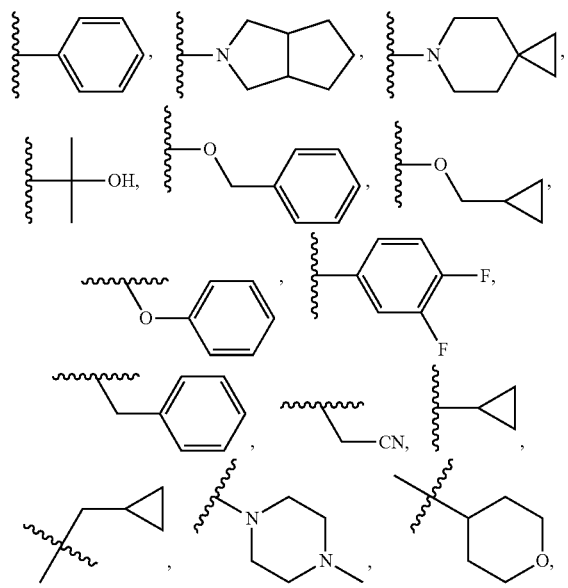

258

-continued

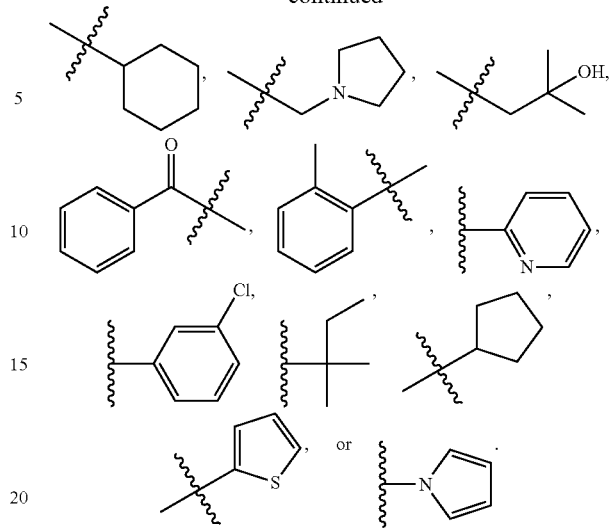

In some embodiments, p is 0. In some embodiments, p is 1. In some embodiments, p is 2.

In some embodiments, $R_1$ is phenyl, pyridine, or pyrazole. In some embodiments, $R_1$ is phenyl, pyridine, orpyrazole, $R_2$ is amino or alkyl, and p is 0 or 1. In some embodiments, $R_1$ is phenyl, pyridine, or pyrazole, $R_3$ is alkyl, such as methyl, and q is 1, 2, 3, or 4.

In some embodiments, the invention features a compound of formula Ib-vi-1:

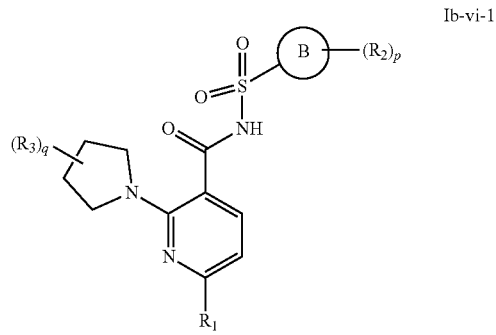

Ib-vi-1 or a pharmaceutically acceptable salt thereof, wherein, independently for each occurrence:
  Ring B is a C3-C10 heteroaryl ring wherein anywhere from 1 to 4 ring atoms are independently O, S, N, or NR;
  $R_1$ is C6-C10 aryl or C3-C10 heteroaryl wherein anywhere from 1 to 4 ring atoms are independently O, S, N, or NR;
  $R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
  or two $R_2$ groups taken together may form a $=CH_2$ or $=O$ group;
  $R_3$ is halo; CN; $CO_2R$; C1-C6 alkyl or fluoroalkyl; C1-C6 alkenyl; C1-C6 alkynyl; C1-C6 alkoxy or fluoroalkoxy;

or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR; or two R₃ groups taken together may form a =CH₂ or =O group;

R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;

R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

p is 0, 1, 2, or 3; and q is 0, 1, 2, 3, 4, or 5.

In some embodiments, the compound of formula Ib-vi-1 exists as a pharmaceutically acceptable prodrug.

In some embodiments, ring B is pyridyl, pyridine-2(1H)-one, pyrazole, indole, aza-indole, thiophene, dihydrobenzofuran, or quinoline.

In some embodiments, ring B is a group represented by the corresponding moieties shown in the compounds of Table 1. For example, ring B is

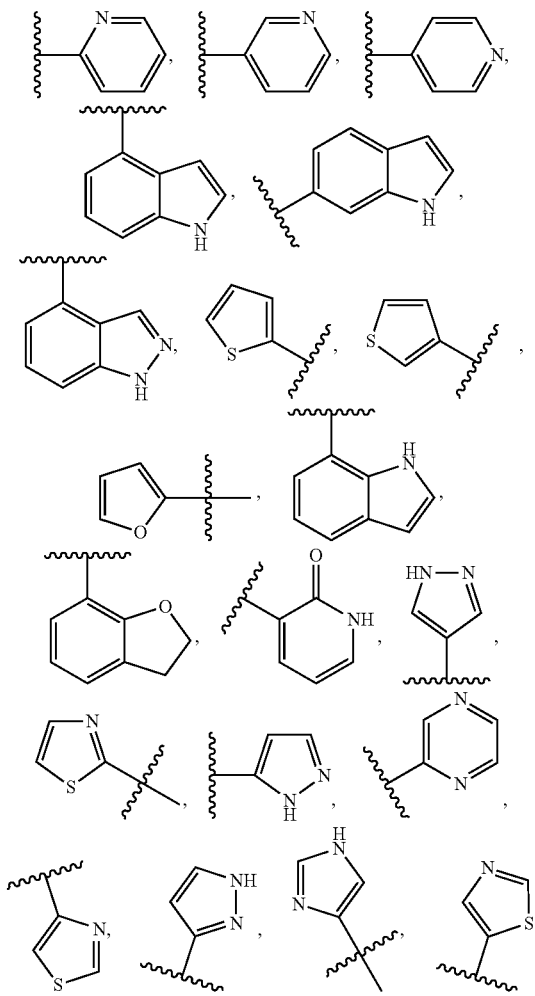

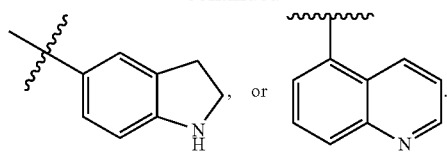

In some embodiments, R₁ is a phenyl, thiophene, pyridine, or pyrazole.

In some embodiments, R₁ is a group represented by the corresponding moieties shown in the compounds of Table 1. For example, R₁ is

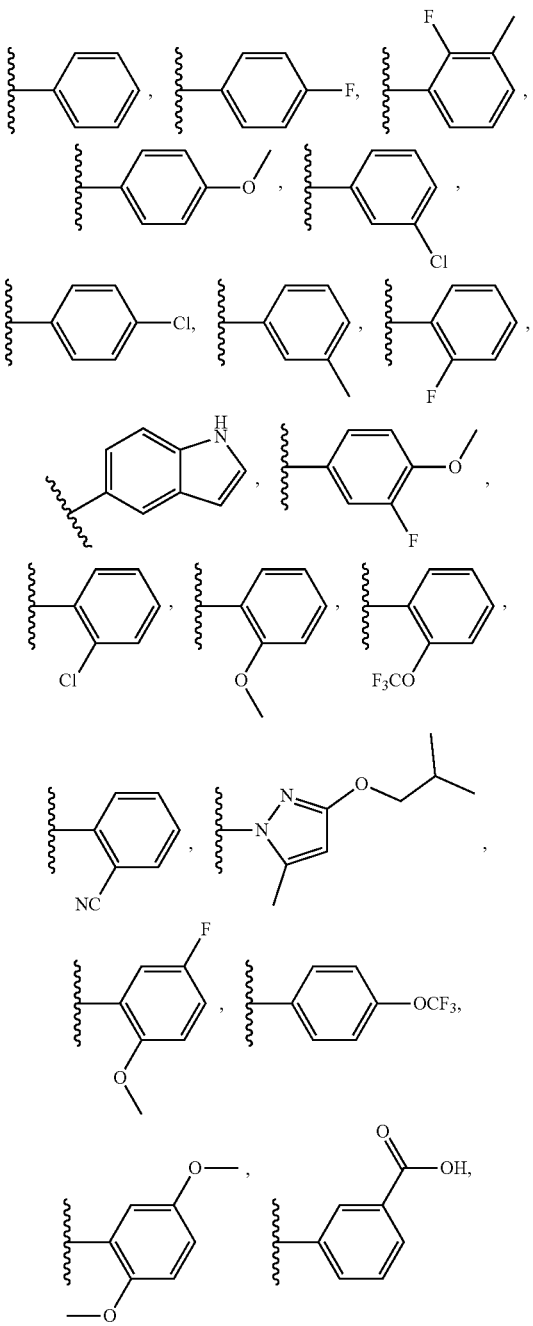

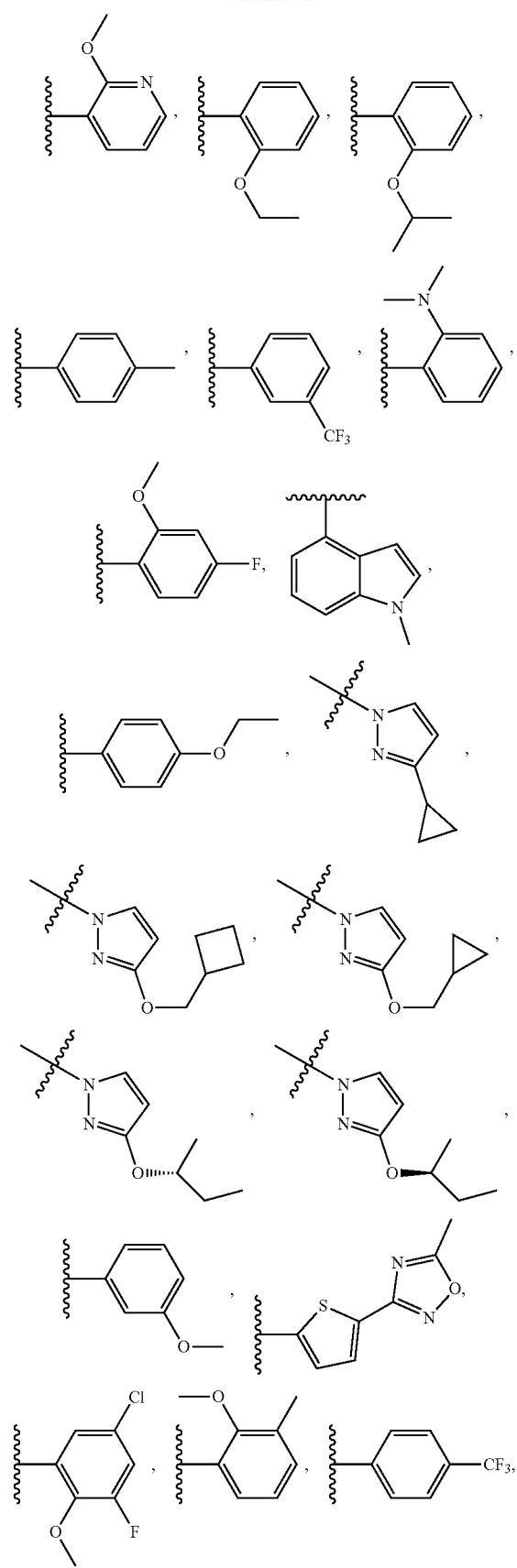
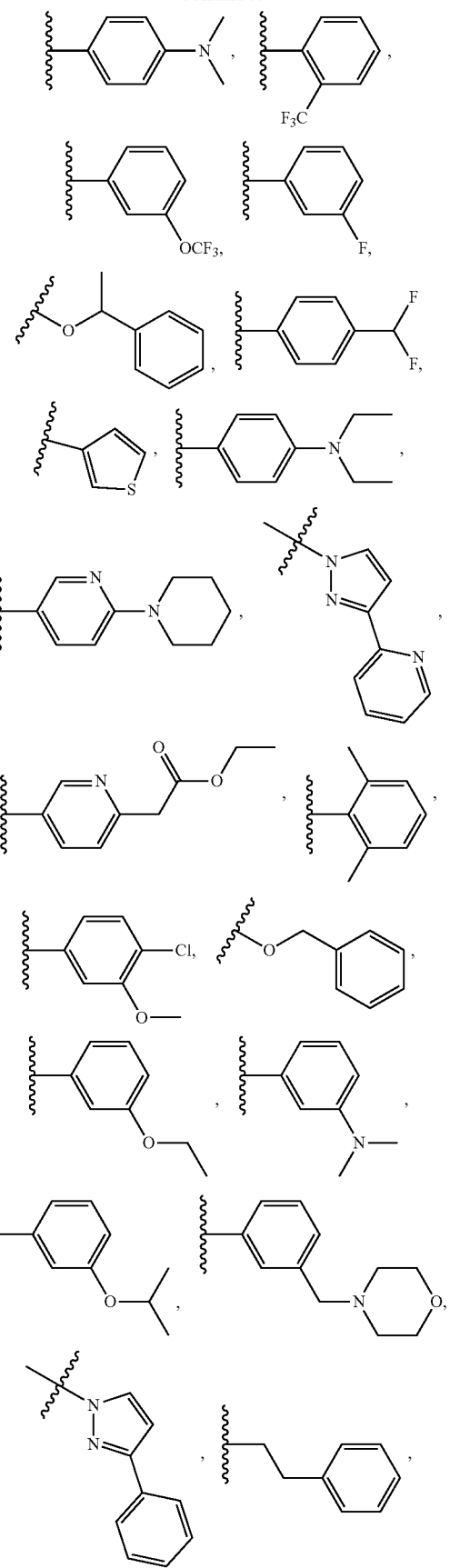

263
-continued
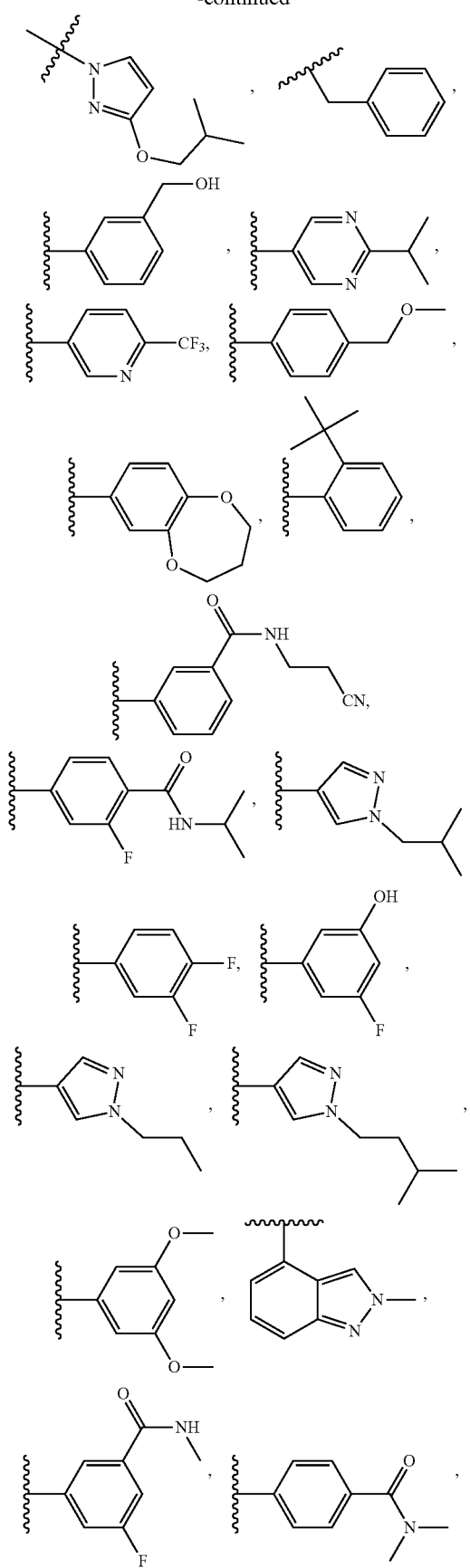
264
-continued
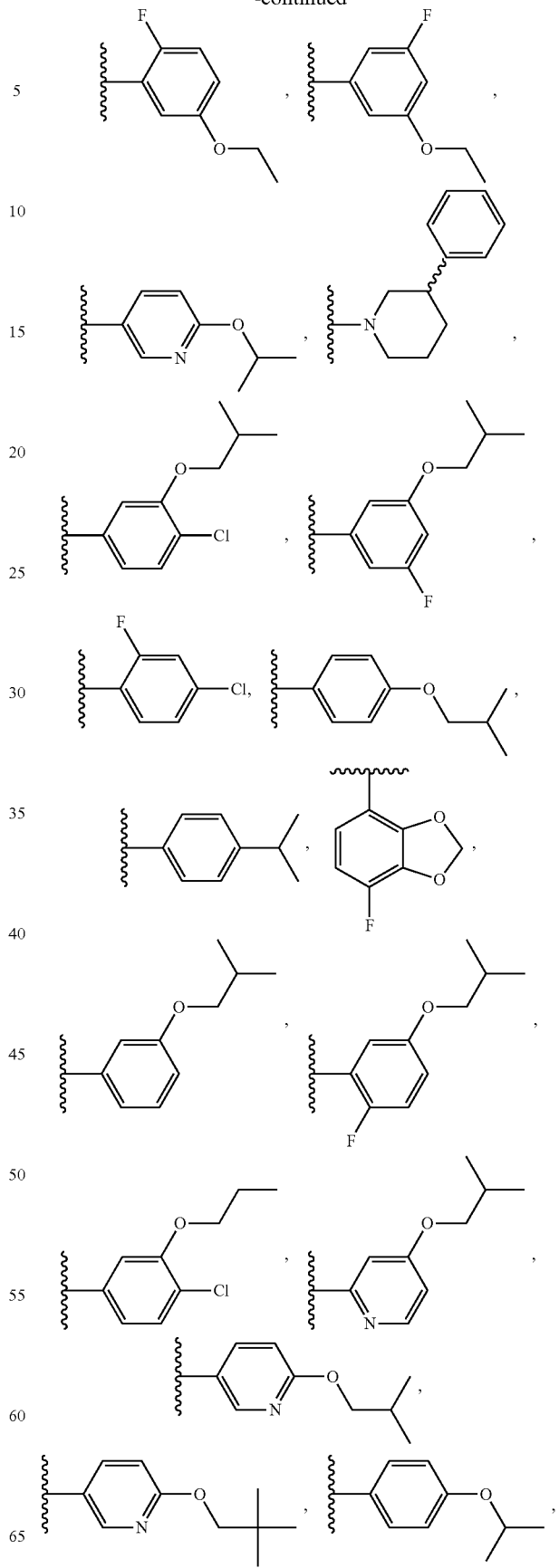

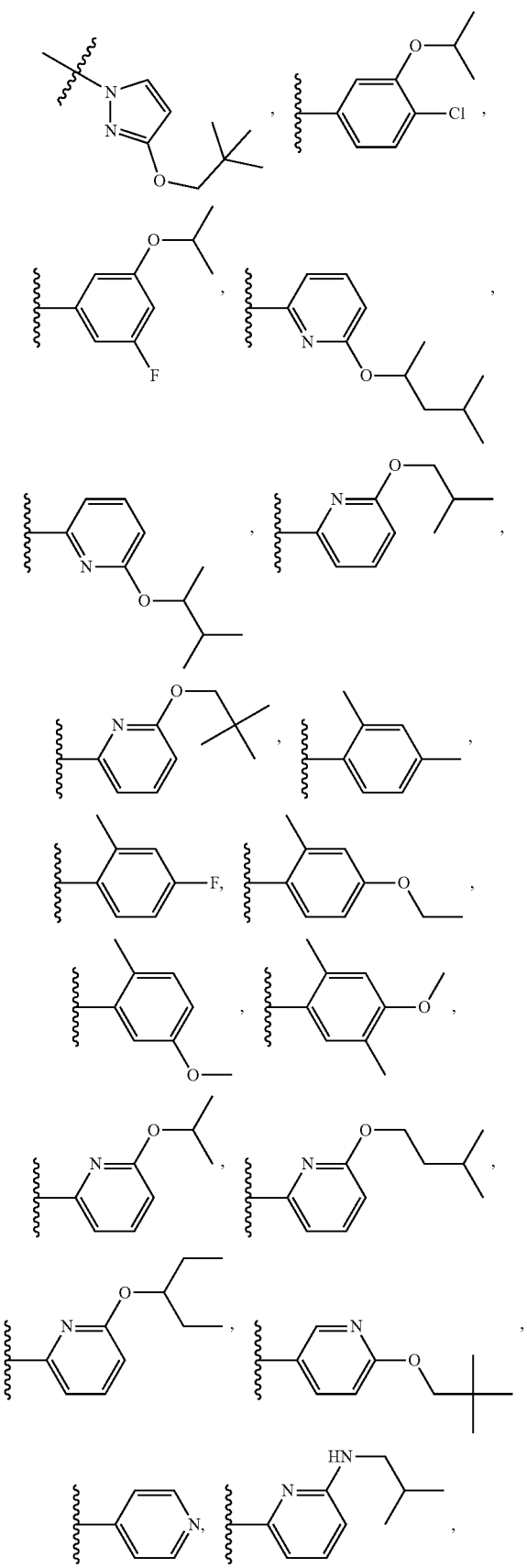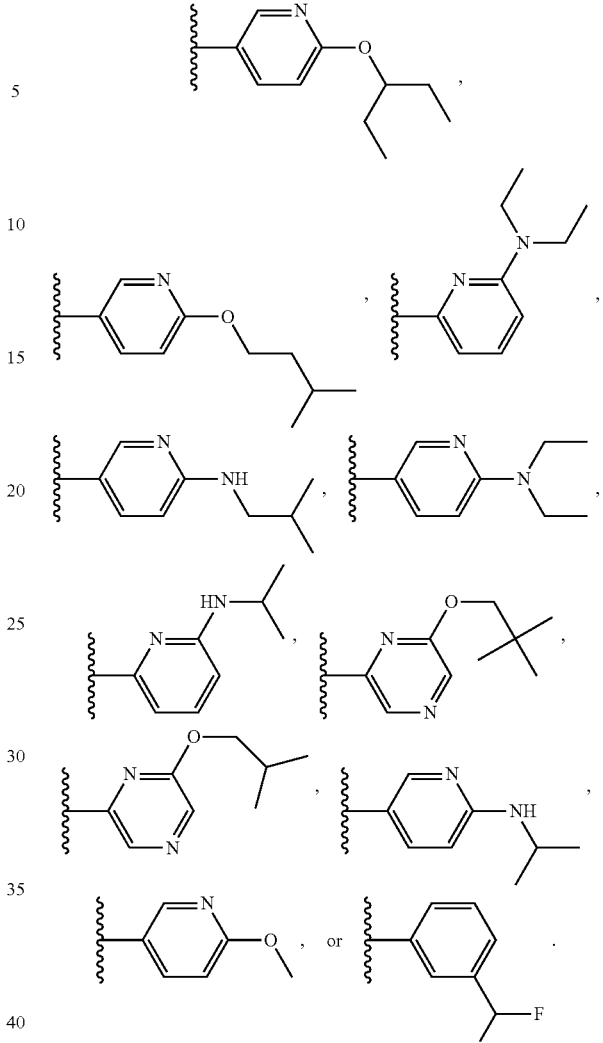

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)$ $(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$, In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, $=CH_2$, $=O$,

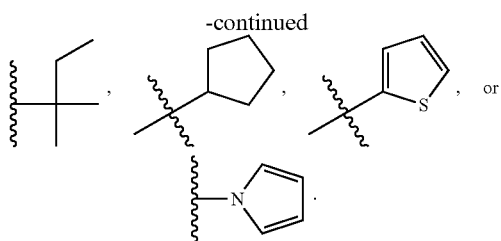

In some embodiments, p is 0. In some embodiments, p is 1. In some embodiments, p is 2.

In some embodiments, R₁ is phenyl, pyridine, or pyrazole. In some embodiments, R₁ is phenyl, pyridine, or pyrazole, R₂ is amino or alkyl, and p is 0 or 1. In some embodiments, R₁ is phenyl, pyridine, or pyrazole, R₃ is alkyl, such as methyl, and q is 1, 2, 3, or 4.

In some embodiments, the invention features a compound of formula Ib-vi-2:

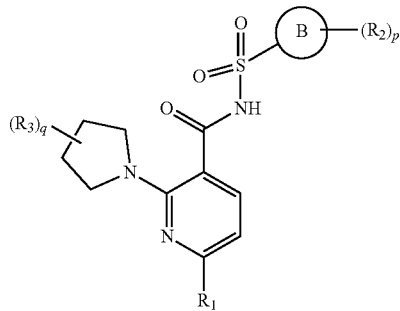

Ib-vi-2 or a pharmaceutically acceptable salt thereof, wherein, independently for each occurrence:
Ring B is a C6-C10 aryl ring;
R₁ is C6-C10 aryl or C3-C10 heteroaryl wherein anywhere from 1 to 4 ring atoms are independently O, S, N, or NR;
R₂ is halo; OH; NRR; azide; CN; CO₂R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₂ groups taken together may form a =CH₂ or =O group;
R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₃ groups taken together may form a =CH₂ or =O group;
R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;

R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
p is 0, 1, 2, or 3; and
q is 0, 1, 2, 3, 4, or 5.

In some embodiments, the compound of formula Ib-vi-2 exists as a pharmaceutically acceptable prodrug.

In some embodiments, ring B is phenyl or napthalene.

In some embodiments, R₁ is a phenyl, thiophene, pyridine, or pyrazole.

In some embodiments, R₁ is a group represented by the corresponding moieties shown in the compounds of Table 1. For example, R₁ is

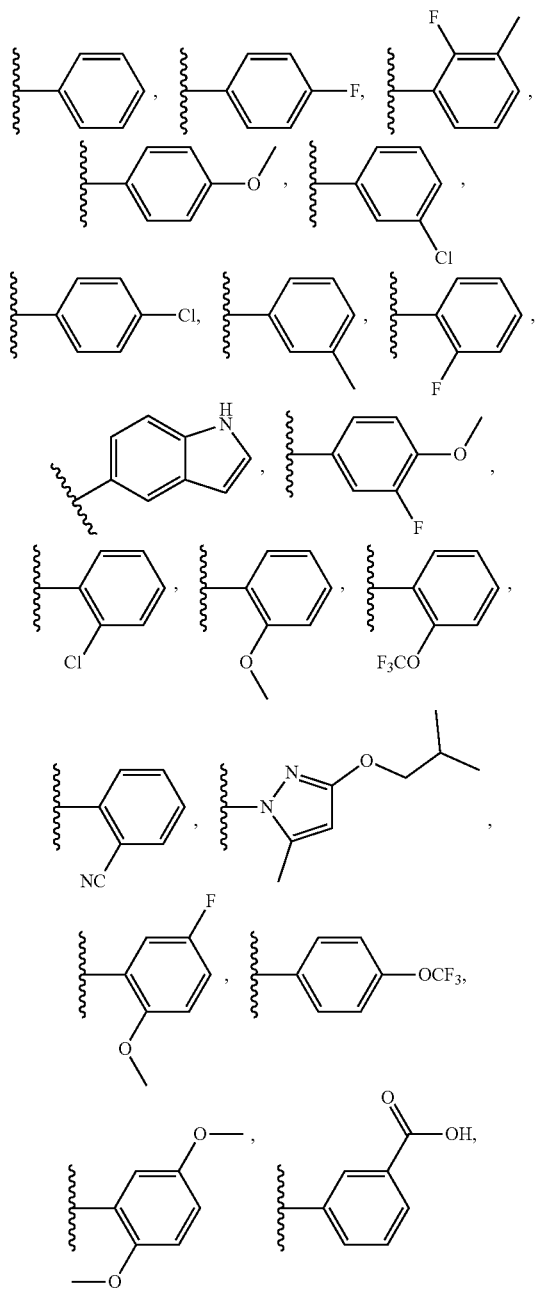

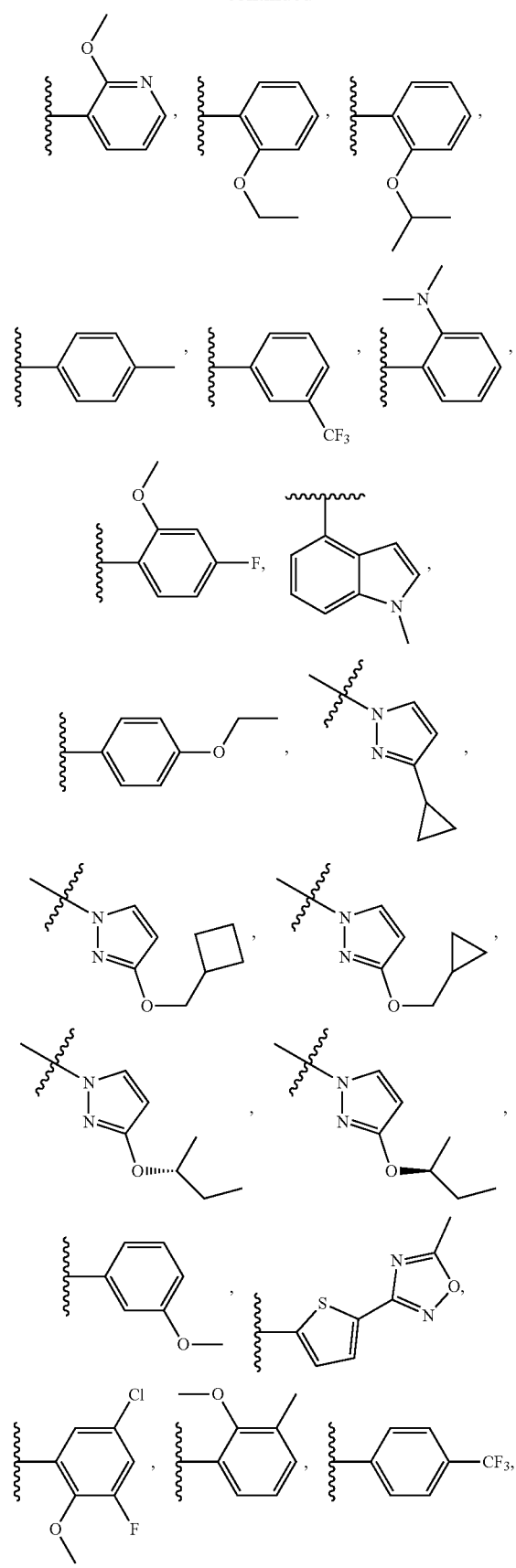
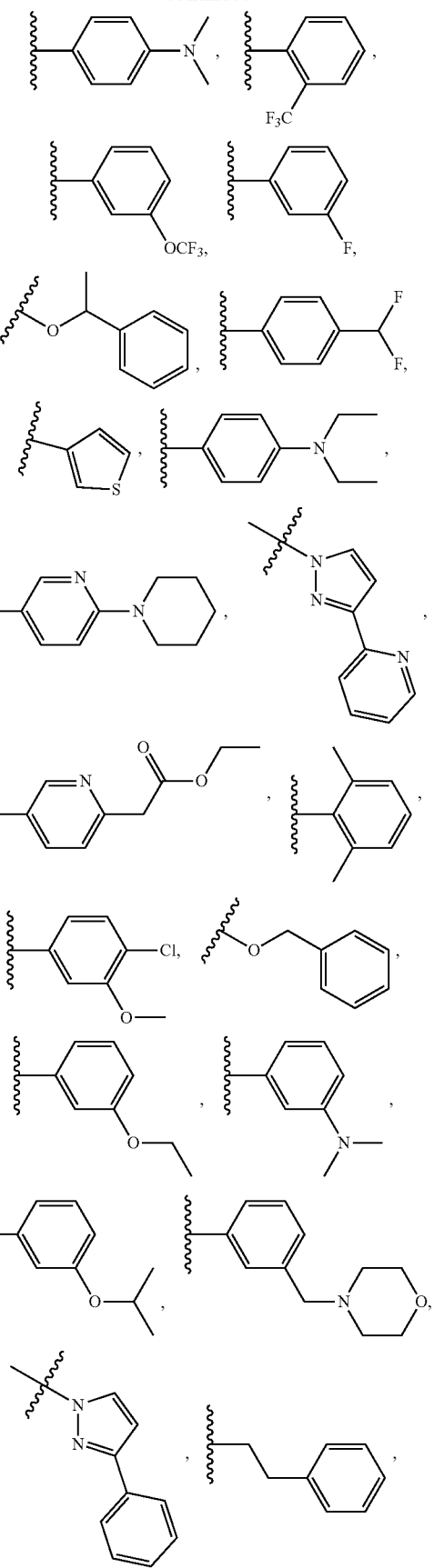

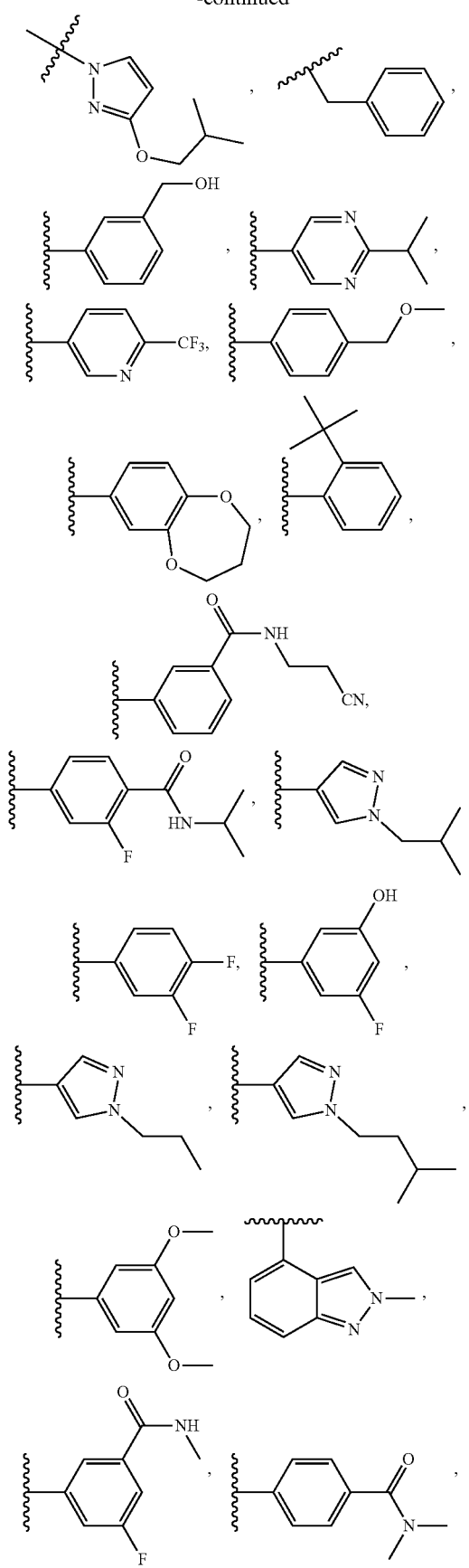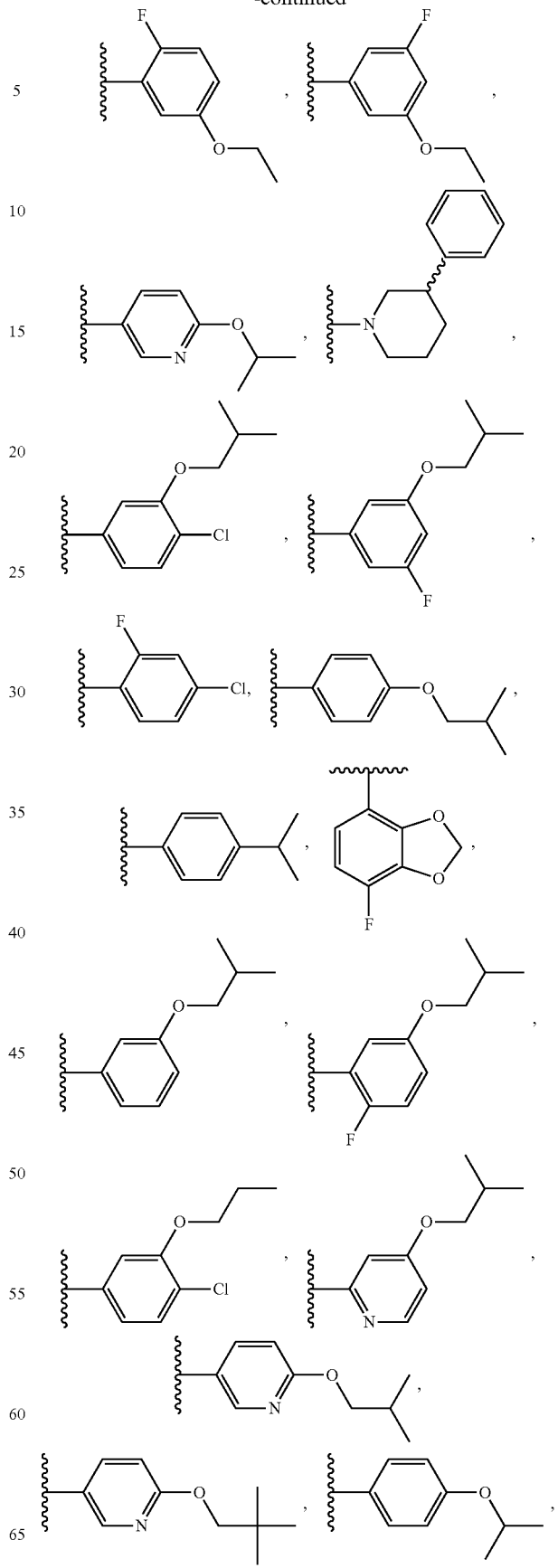

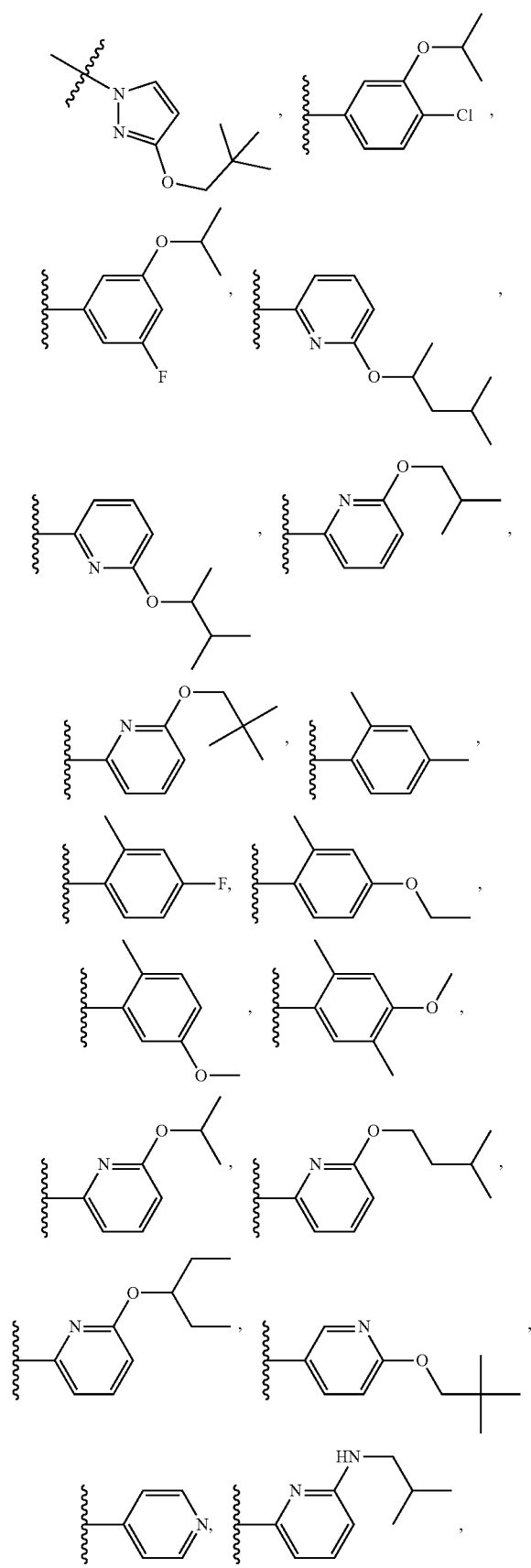

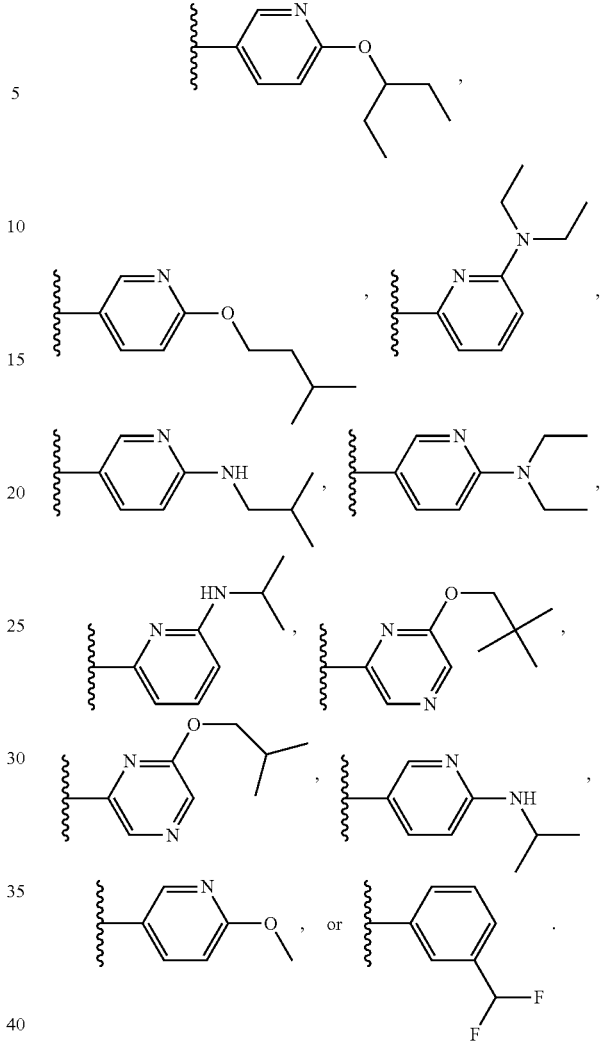

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

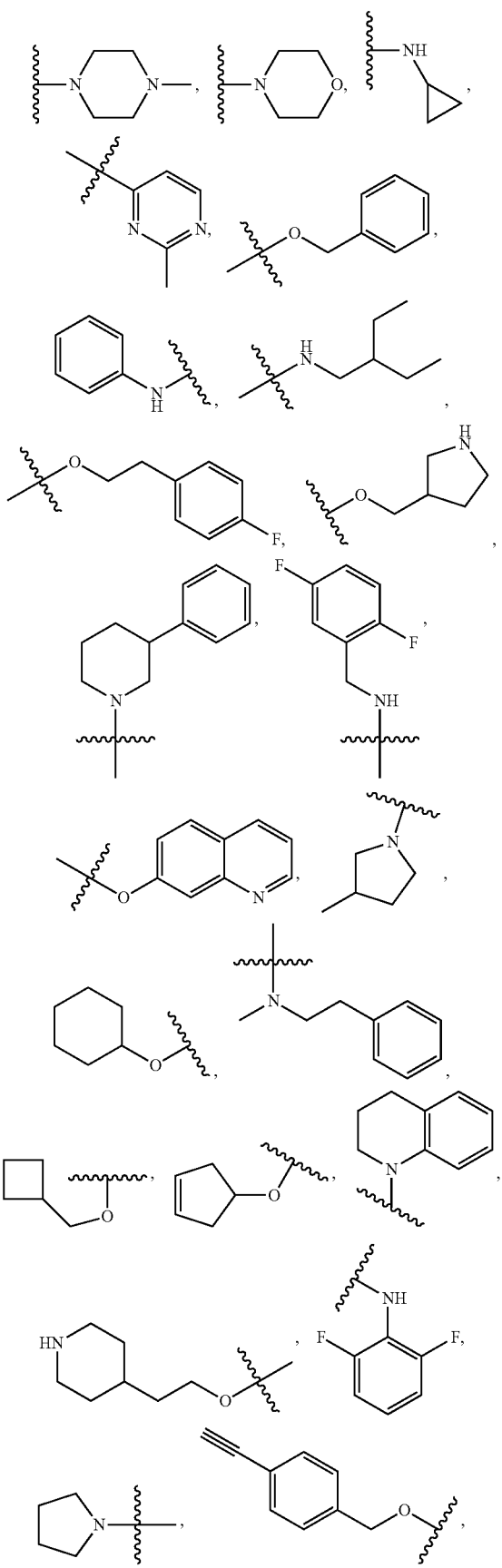

-continued

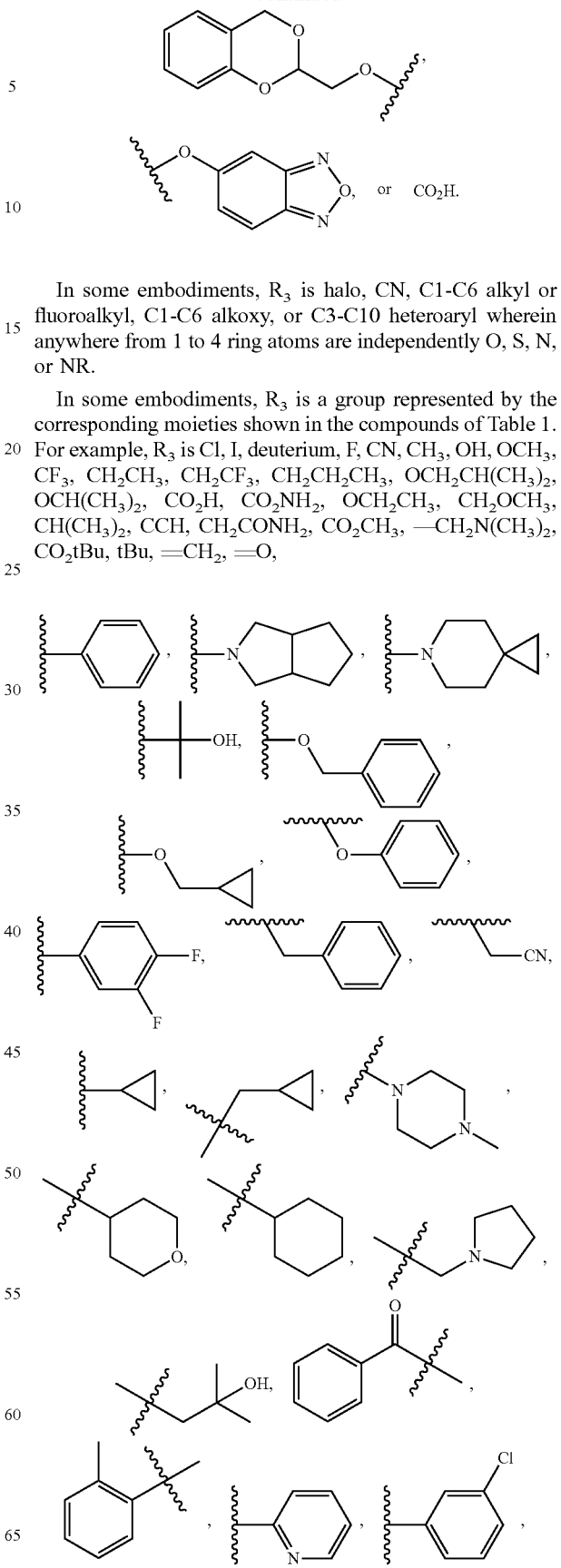

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

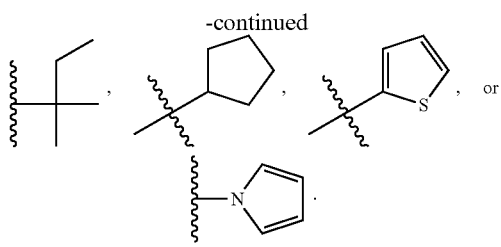

In some embodiments, p is 0. In some embodiments, p is 1. In some embodiments, p is 2.

In some embodiments, $R_1$ is phenyl, pyridine, or pyrazole. In some embodiments, $R_1$ is phenyl, pyridine, or pyrazole, $R_2$ is amino or alkyl, and p is 0 or 1. In some embodiments, $R_1$ is phenyl, pyridine, or pyrazole, $R_3$ is alkyl, such as methyl, and q is 1, 2, 3, or 4.

In some embodiments, the invention features a compound of formula Ib-vii:

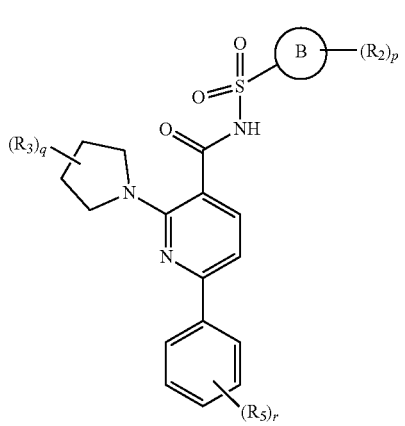

Ib-vii or a pharmaceutically acceptable salt thereof, wherein, independently for each occurrence:

Ring B is a C6-C10 aryl ring or C3-C10 heteroaryl or heterocyclic ring wherein anywhere from 1 to 4 ring atoms are independently O, S, N, or NR;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a $=CH_2$ or $=O$ group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a $=CH_2$ or $=O$ group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

$R_5$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

p is 0, 1, 2, or 3;

g is 0, 1, 2, 3, 4, or 5; and r is 0, 1, 2, 3, 4, or 5.

In some embodiments, the compound of formula Ib-vii exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

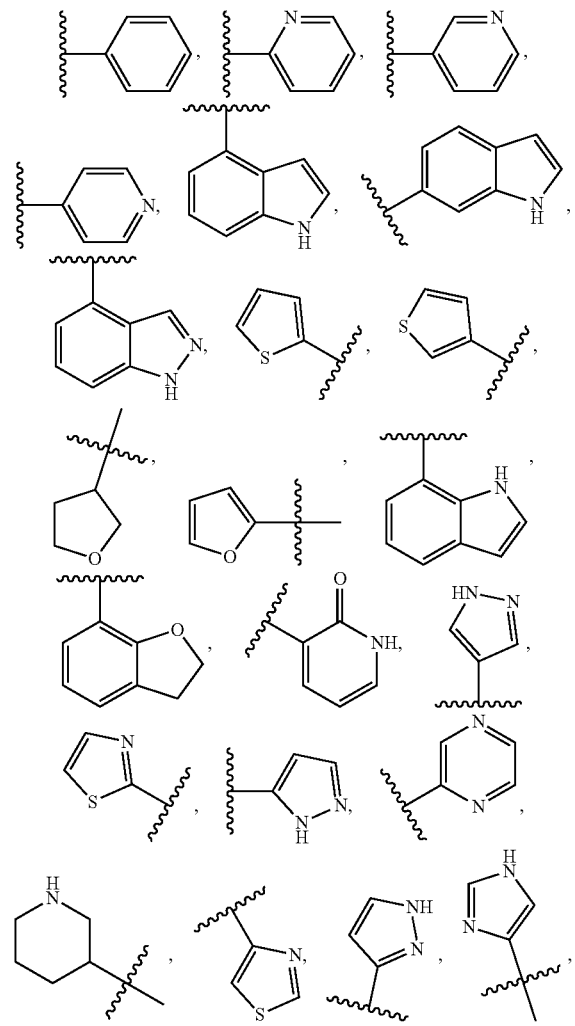

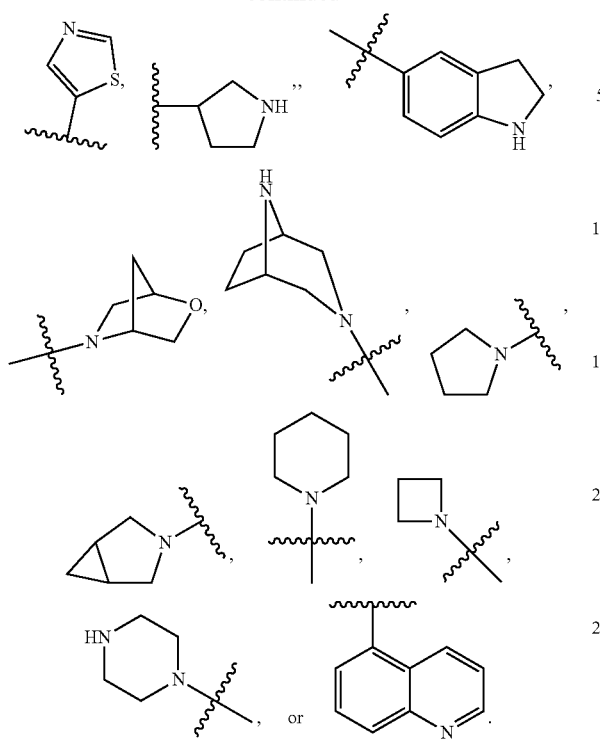

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)$ $(CH_2CH_2CH_3)$, $OCH(CH_3)_2$, $NH(CH_2)_2O(CH_2)_2CH_3$, $C(O)$ $CH_3$, $CH_2CH_2OH$, $CH_2NH_2$, $NH(CH_2)_2OH$, $N(CH_3)$ $CH_2CH_2CH_2OCH_3$, $NHCH_2CH_2COOH$, $NH(CH_2)_2N$ $(CH_3)_2$, $NH(CH_2)_2NH_2$, $NH(CH_2)_3NH_2$, $NH(CH_2)_2OCH_3$, $NHCH(CH_3)_2$,

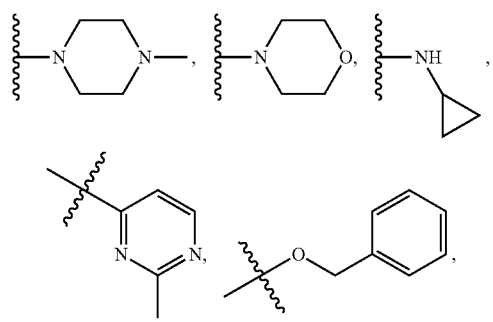

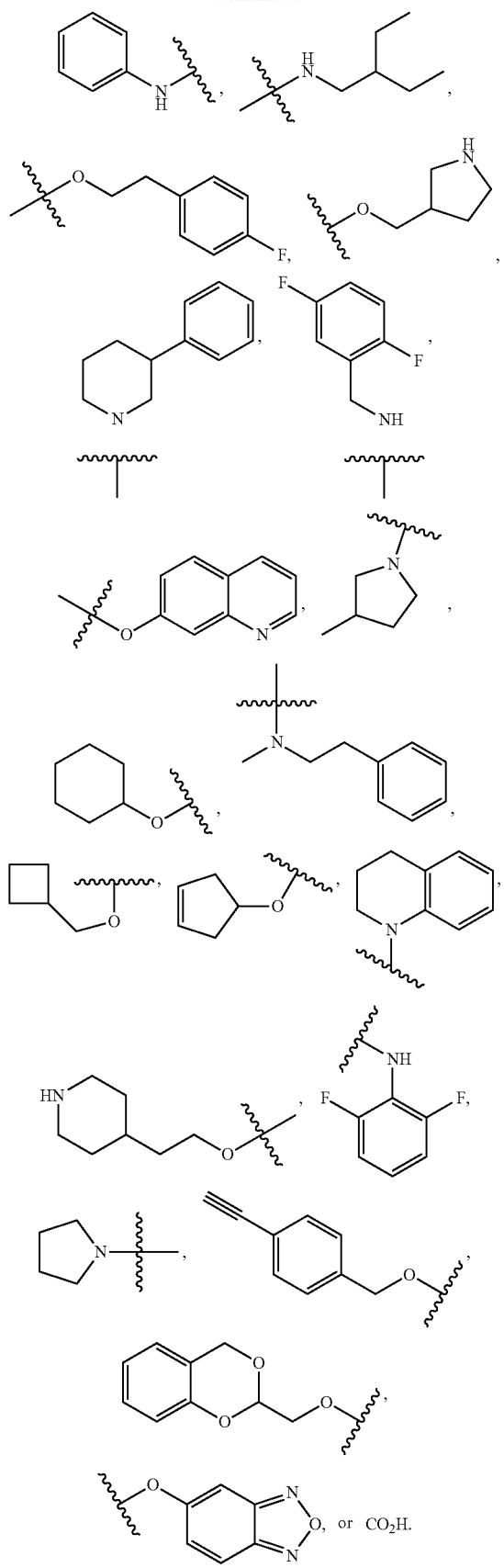

or $CO_2H$.

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O, In some embodiments, p is 0. In some embodiments, p is 1. In some embodiments, p is 2.

In some embodiments, $R_5$ is a group represented by the corresponding moieties shown in the compounds of Table 1. For example, $R_5$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH_2C(CH_3)_3OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

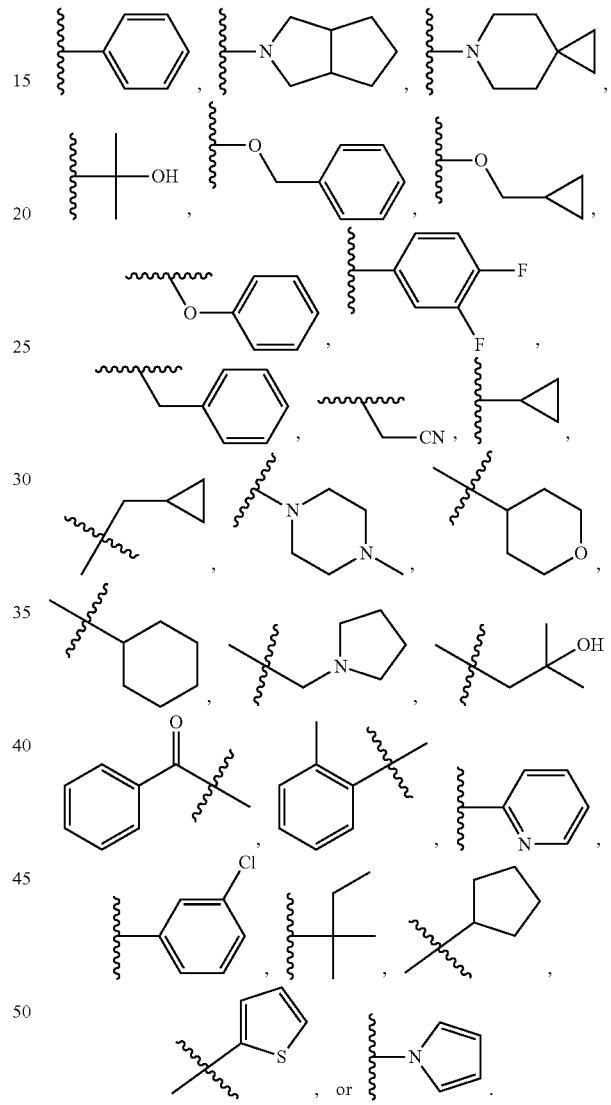

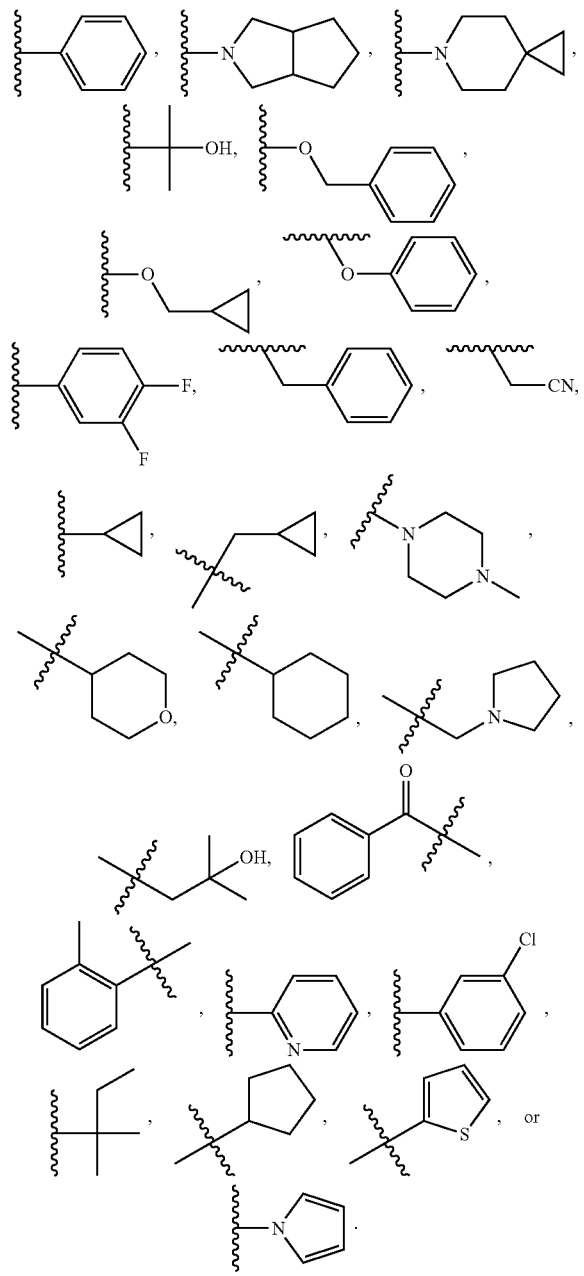

In some embodiments, r is 0. In some embodiments, r is 1. In some embodiments, r is 2. In some embodiments, r is 3. In some embodiments, r is 4. In some embodiments, r is 5.

In some embodiments, $R_5$ is halo or alkoxy. In some embodiments, $R_2$ is amino or alkyl, $R_5$ is halo or alkoxy, r is 1 or 2, and p is 0 or 1. In some embodiments, $R_5$ is halo or alkoxy, $R_3$ is alkyl, such as methyl, r is 1 or 2, and q is 1, 2, 3, or 4.

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, the invention features a compound of formula Ib-viii:

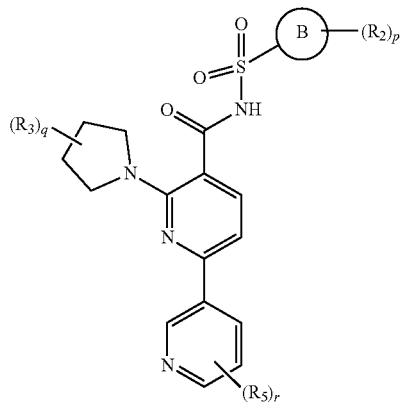

Ib-viii or a pharmaceutically acceptable salt thereof, wherein, independently for each occurrence:

Ring B is a C6-C10 aryl ring or C3-C10 heteroaryl or heterocyclic ring wherein anywhere from 1 to 4 ring atoms are independently O, S, N, or NR;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a $=CH_2$ or $=O$ group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a $=CH_2$ or $=O$ group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

$R_5$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

p is 0, 1, 2, or 3;

q is 0, 1, 2, 3, 4, or 5; and r is 0, 1, 2, 3, 4, or 5.

In some embodiments, the compound of formula Ib-viii exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

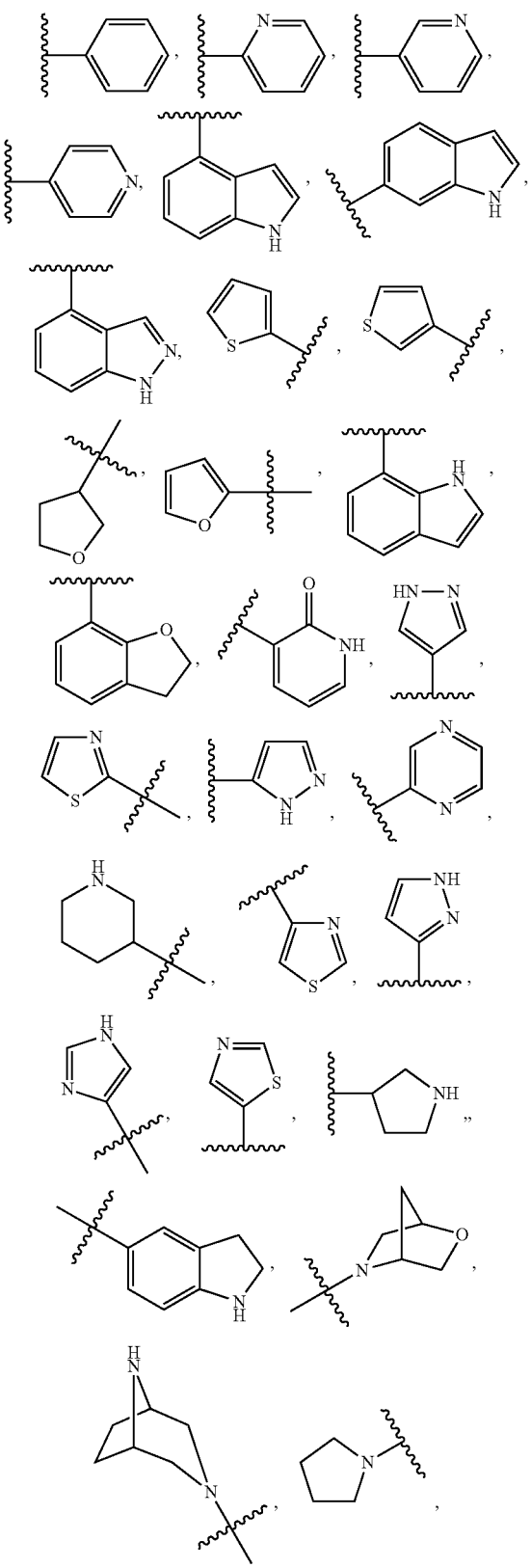

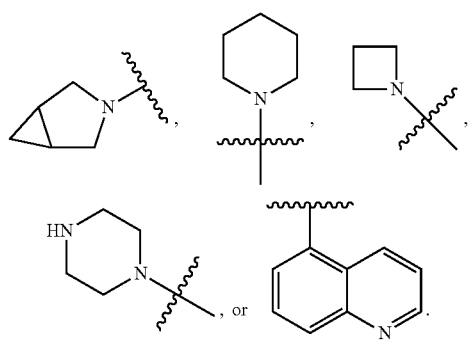

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$; $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

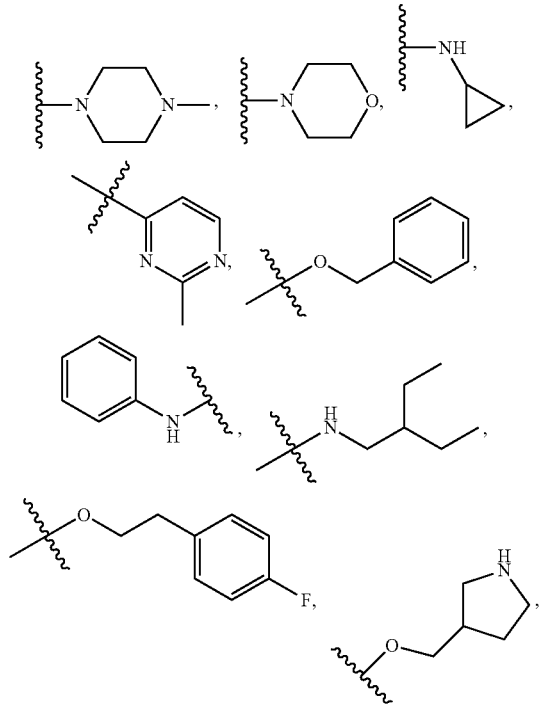

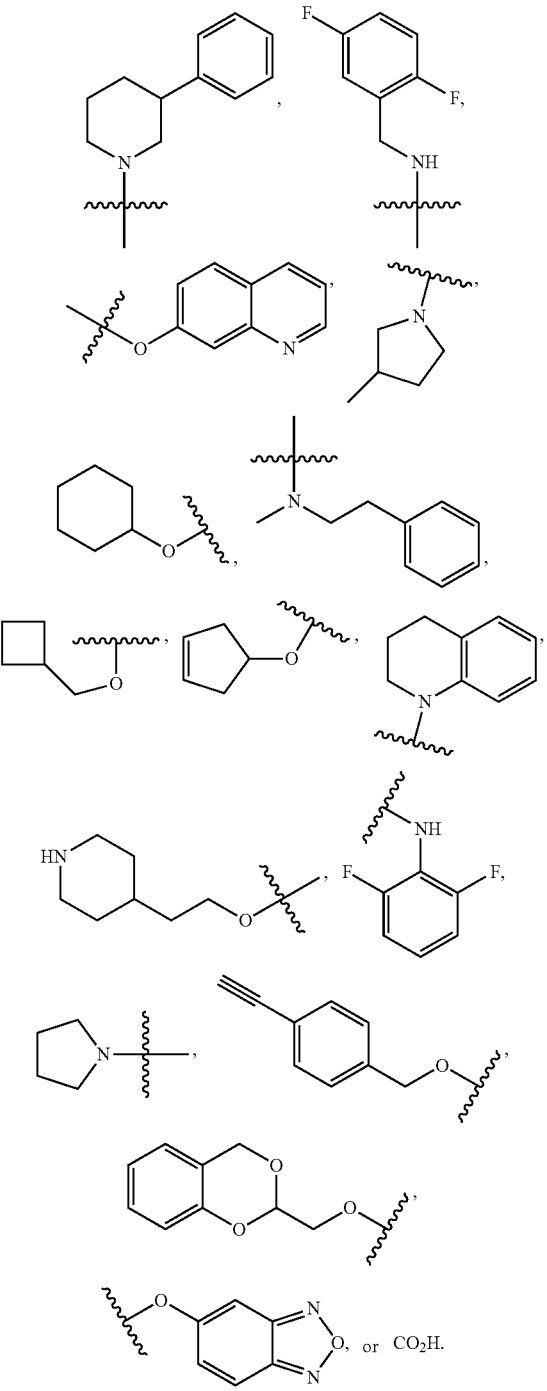

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

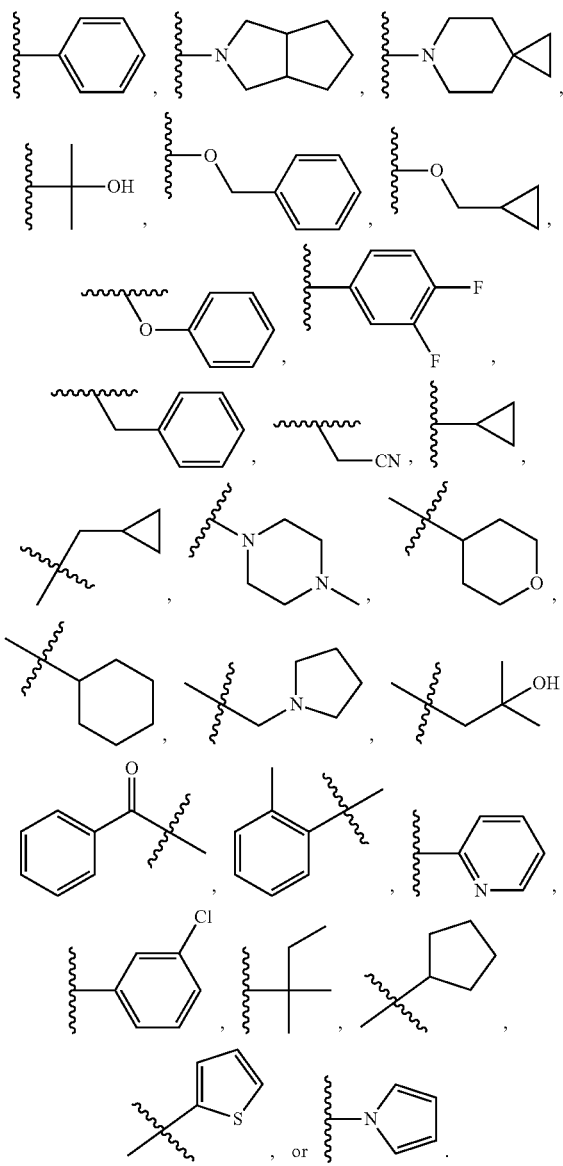

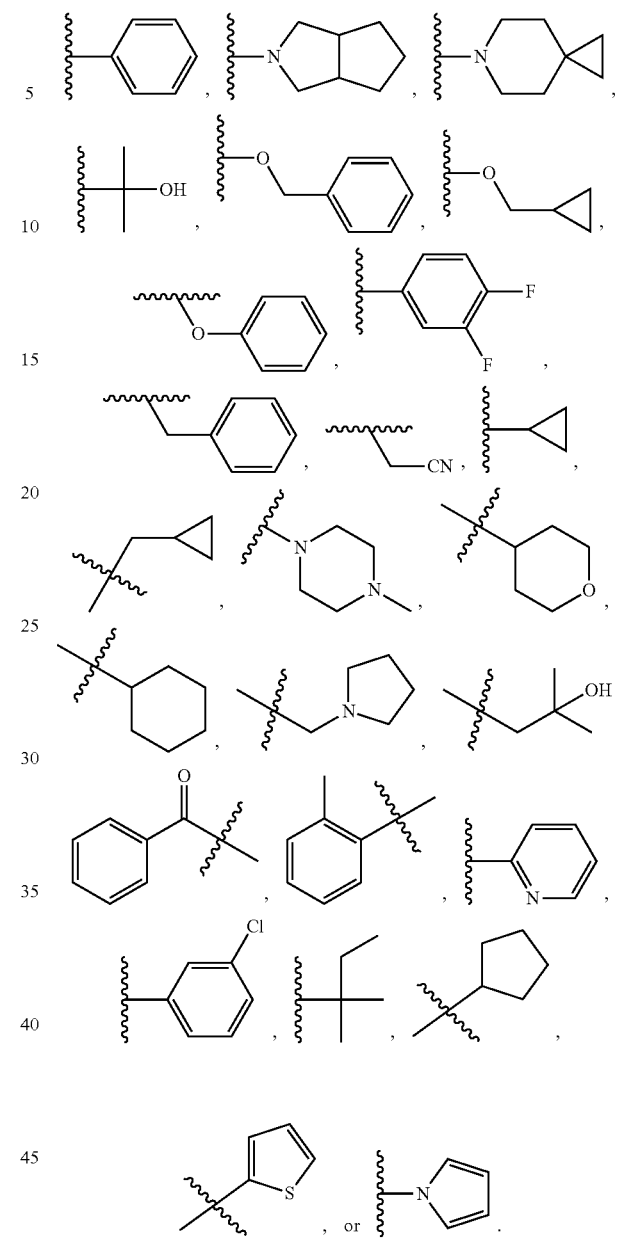

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, p is 0. In some embodiments, p is 1. In some embodiments, p is 2.

In some embodiments, $R_5$ is a group represented by the corresponding moieties shown in the compounds of Table 1. For example, $R_5$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH_2C(CH_3)_3$ $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, $-CH_2N(CH_3)_2$, $CO_2tBu$, tBu, $=CH_2$, $=O$, In some embodiments, r is 0. In some embodiments, r is 1. In some embodiments, r is 2. In some embodiments, r is 3. In some embodiments, r is 4. In some embodiments, r is 5.

In some embodiments, $R_5$ is halo or alkoxy. In some embodiments, $R_2$ is amino or alkyl, $R_5$ is halo or alkoxy, r is 1 or 2, and p is 0 or 1. In some embodiments, $R_5$ is halo or alkoxy, $R_3$ is alkyl, such as methyl, r is 1 or 2, and q is 1, 2, 3, or 4.

In some embodiments, the invention features a compound of formula Ib-ix:

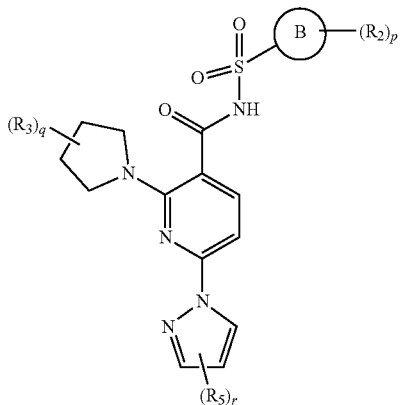

or a pharmaceutically acceptable salt thereof, wherein, independently for each occurrence:
  Ring B is a C6-C10 aryl ring or C3-C10 heteroaryl or heterocyclic ring wherein anywhere from 1 to 4 ring atoms are independently O, S, N, or NR;
  $R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
  or two $R_2$ groups taken together may form a $=CH_2$ or $=O$ group;
  $R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
  or two $R_3$ groups taken together may form a $=CH_2$ or $=O$ group;
  $R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;
  R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl; $R_5$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
  p is 0, 1, 2, or 3;
  q is 0, 1, 2, 3, 4, or 5; and
  r is 0, 1, 2, 3, 4, or 5.

In some embodiments, the compound of formula Ib-ix exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

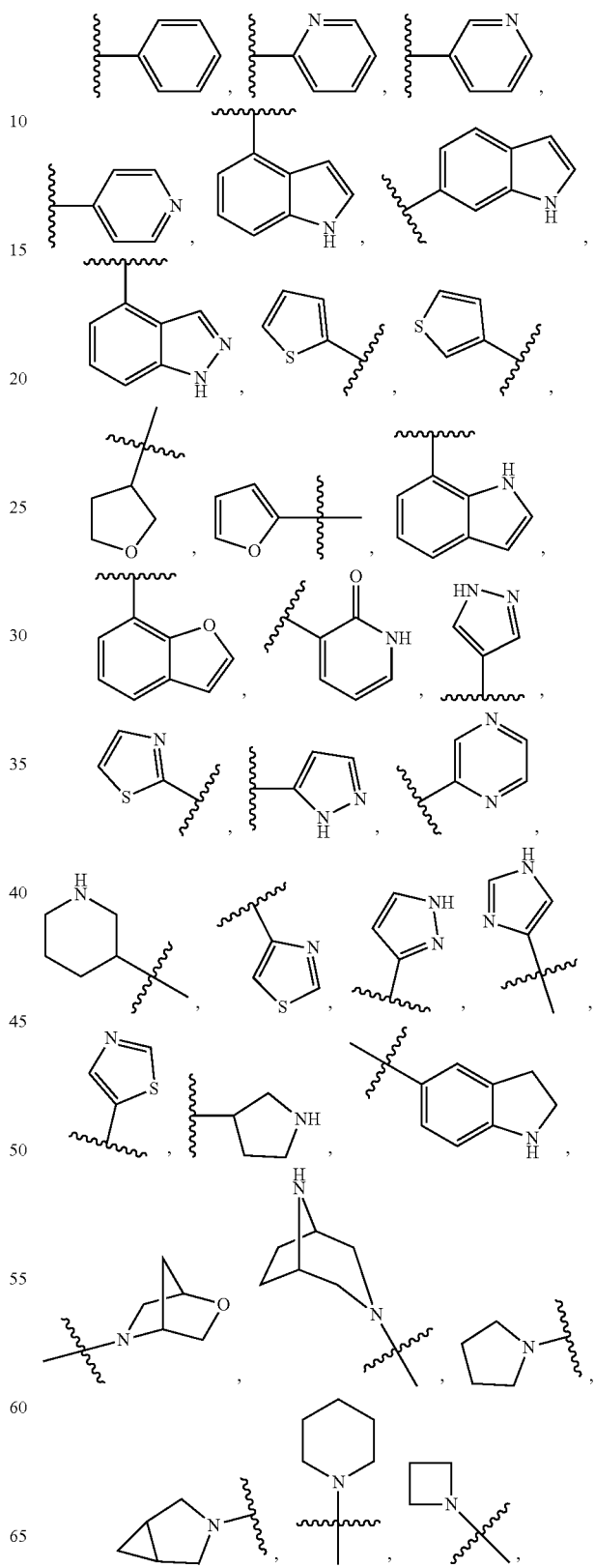

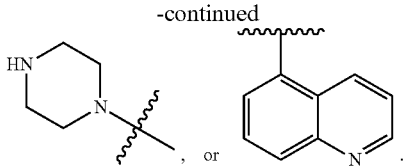

In some embodiments, $R_2$ is halo, OH, CN, azide, amino, C1-C6 alkyl or fluoroalkyl, C1-C6 alkoxy or fluoroalkoxy, C3-C10 heterocyclic ring wherein up to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

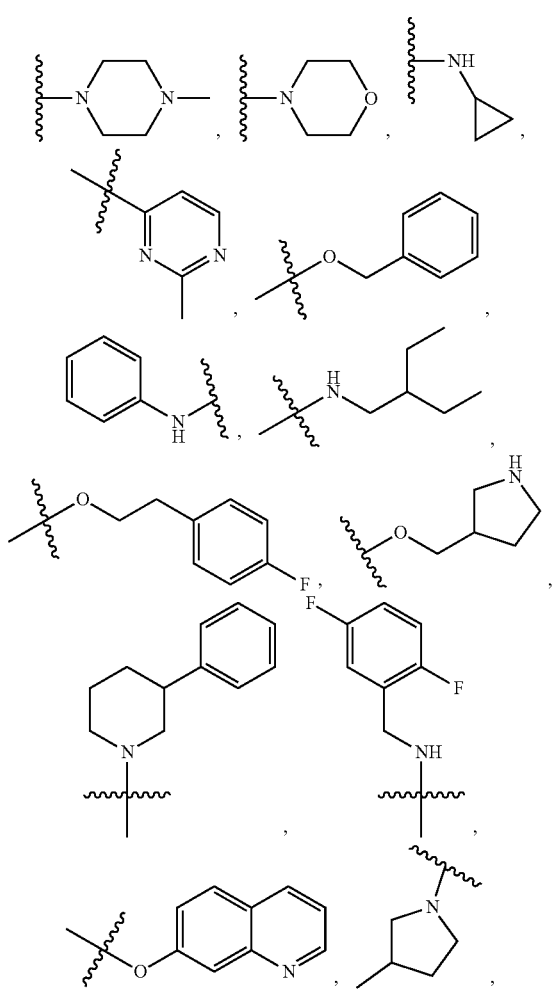

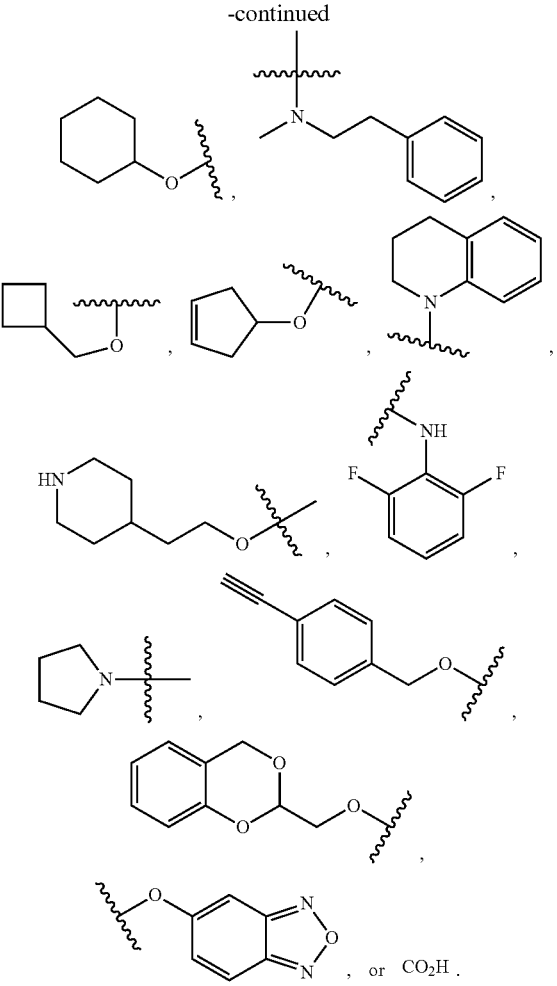

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, $-CH_2N(CH_3)_2$, $CO_2tBu$, tBu, $=CH_2$, $=O$,

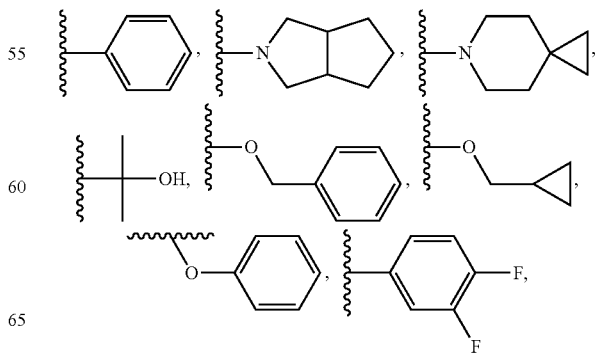

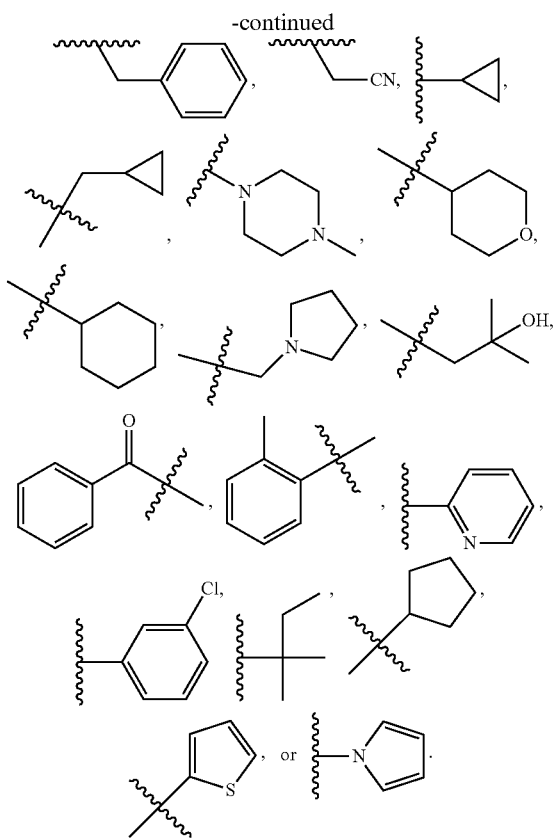

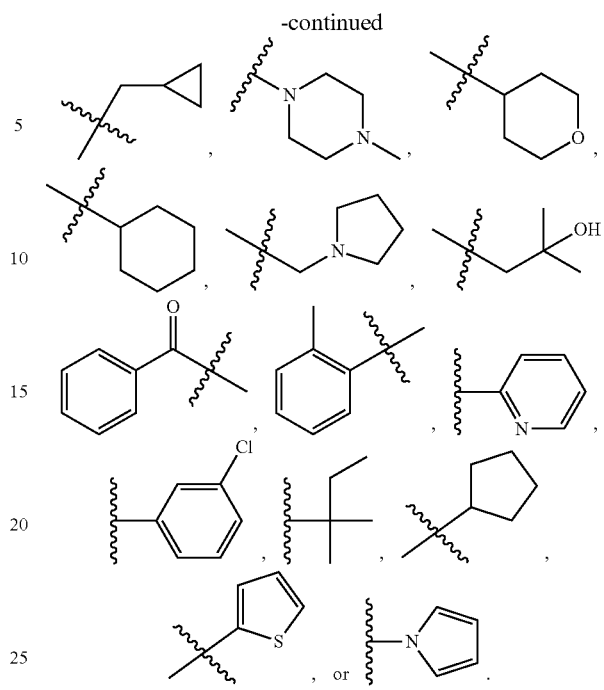

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, p is 0. In some embodiments, p is 1. In some embodiments, p is 2.

In some embodiments, $R_5$ is a group represented by the corresponding moieties shown in the compounds of Table 1. For example, $R_5$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH_2C(CH_3)_3OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

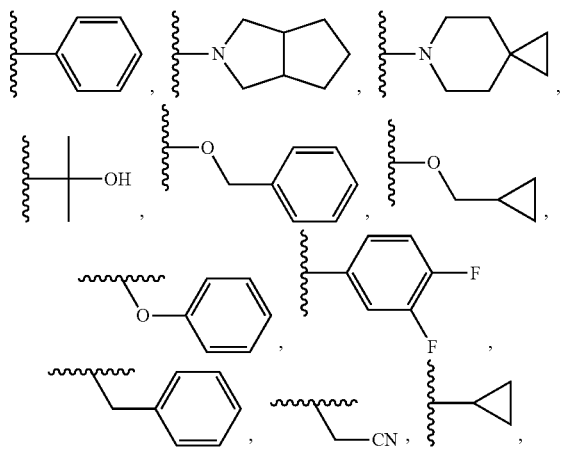

In some embodiments, r is 0. In some embodiments, r is 1. In some embodiments, r is 2. In some embodiments, r is 3. In some embodiments, r is 4. In some embodiments, r is 5.

In some embodiments, $R_5$ is halo or alkoxy. In some embodiments, $R_2$ is amino or alkyl, $R_5$ is halo or alkoxy, r is 1 or 2, and p is 0 or 1. In some embodiments, $R_5$ is halo or alkoxy, $R_3$ is alkyl, such as methyl, r is 1 or 2, and q is 1, 2, 3, or 4.

In some embodiments, the invention features a compound of formula Ic:

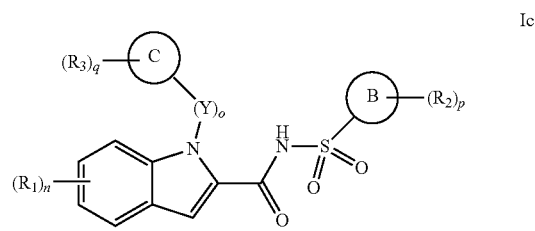

Ic or a pharmaceutically acceptable salt thereof, wherein, independently for each occurrence:
  Ring B is a C6-C10 aryl ring or C3-C10 heteroaryl or heterocyclic ring wherein anywhere from 1 to 4 ring atoms are independently O, S, N, or NR;
  Ring C is a C6-C10 aryl ring, C3-C14 heteroaryl or heterocyclic ring wherein anywhere from 1 to 4 ring atoms are independently N, O, or S, or a C3-C10 cycloalkyl ring;
  Y is CRR, CO, O, S, SO, $SO_2$, S(O)NH or NR;
  $R_1$ is halo; CN; F5S; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

R$_2$ is halo; OH; NRR; azide; CN; CO$_2$R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R$_4$ wherein up to four CH$_2$ units are independently replaced with O, CO, S, SO, SO$_2$ or NR;
  or two R$_2$ groups taken together may form a =CH$_2$ or =O group;

R$_3$ is halo; CN; CO$_2$R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R$_4$ wherein up to four CH$_2$ units are independently replaced with O, CO, S, SO, SO$_2$ or NR;
  or two R$_3$ groups taken together may form a =CH$_2$ or =O group;

R$_4$ is H; azide; CF$_3$; CHF$_2$; OR; CCH; CO$_2$R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO$_2$R;

R is independently H; OH; CO$_2$H; CO$_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;
o is 0, 1, 2, 3, 4, or 5;
p is 0, 1, 2, or 3; and
q is 0, 1, 2, 3, 4, or 5.

In some embodiments, the compound of formula Ic exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

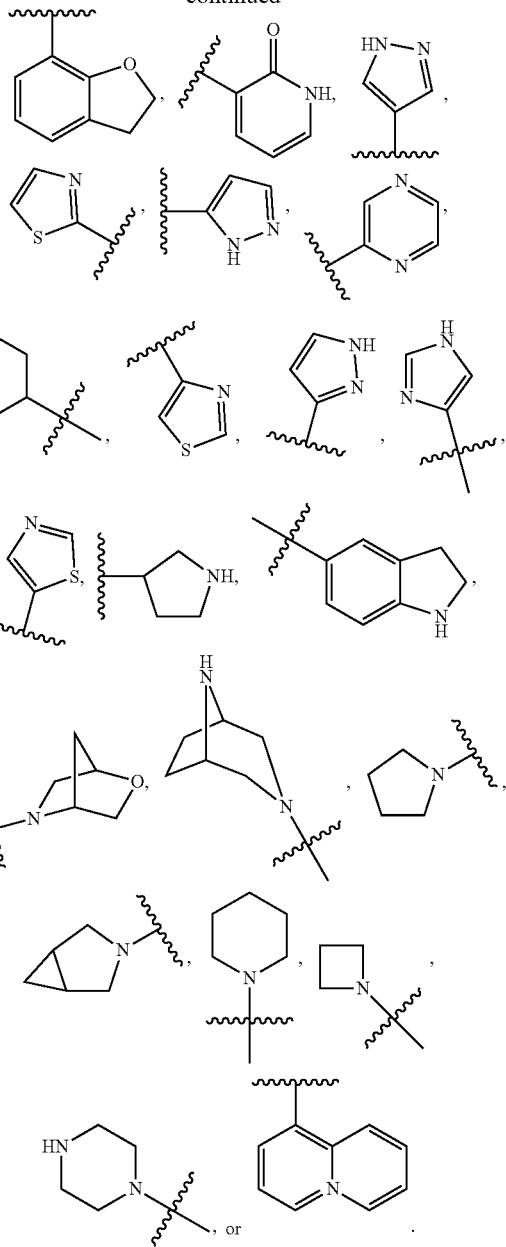

In some embodiments, ring C is phenyl, indole, cycloalkyl, pyridyl, pyrrolidine, naphthalene, or dihydroindene.

In some embodiments, ring C a group represented by the corresponding moieties shown in the compounds of Table 1. For example, ring C is

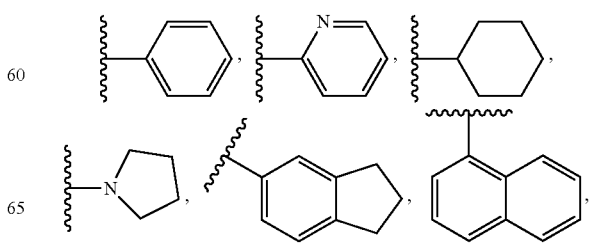

299
-continued
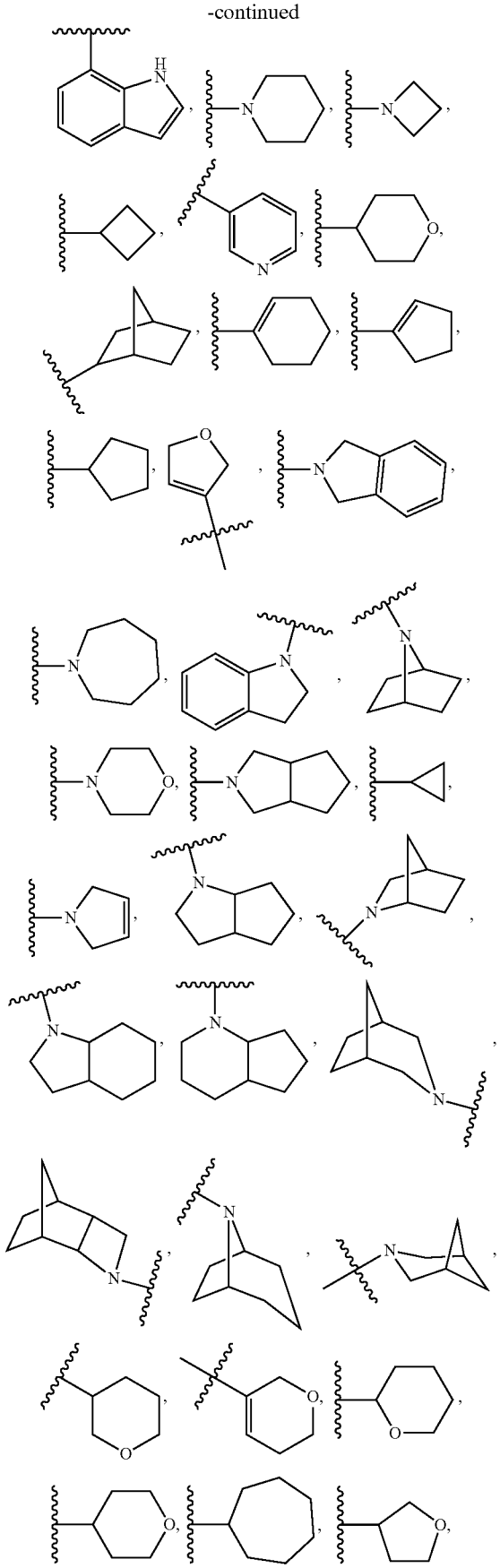
300
-continued
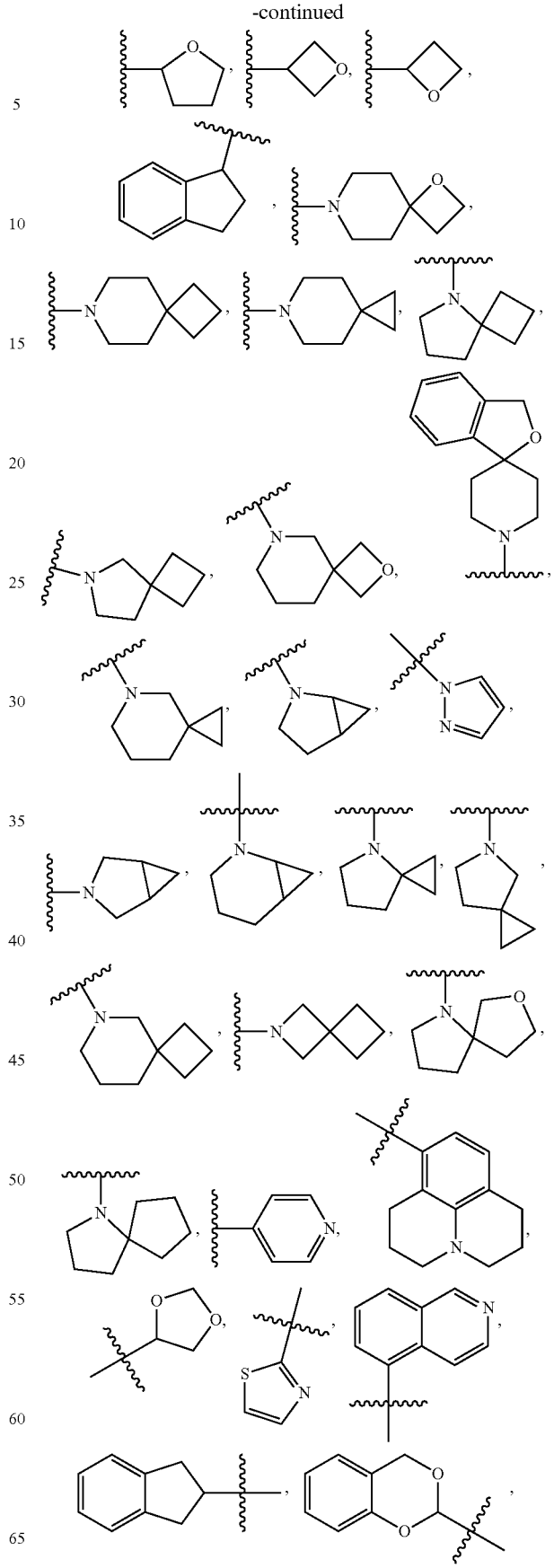

-continued

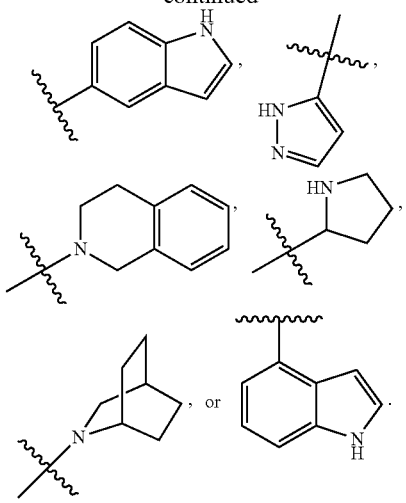

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

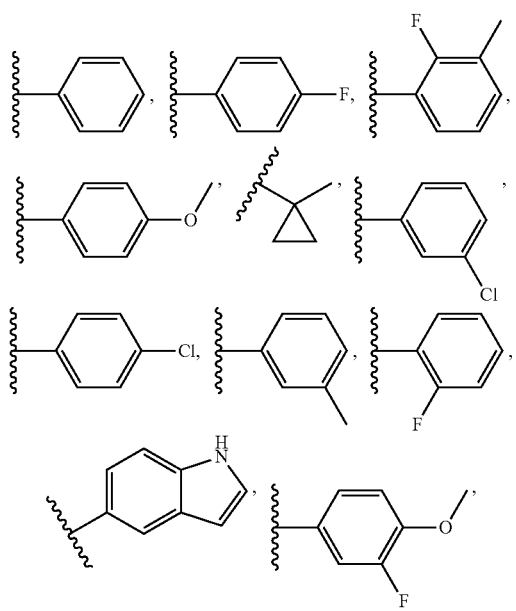

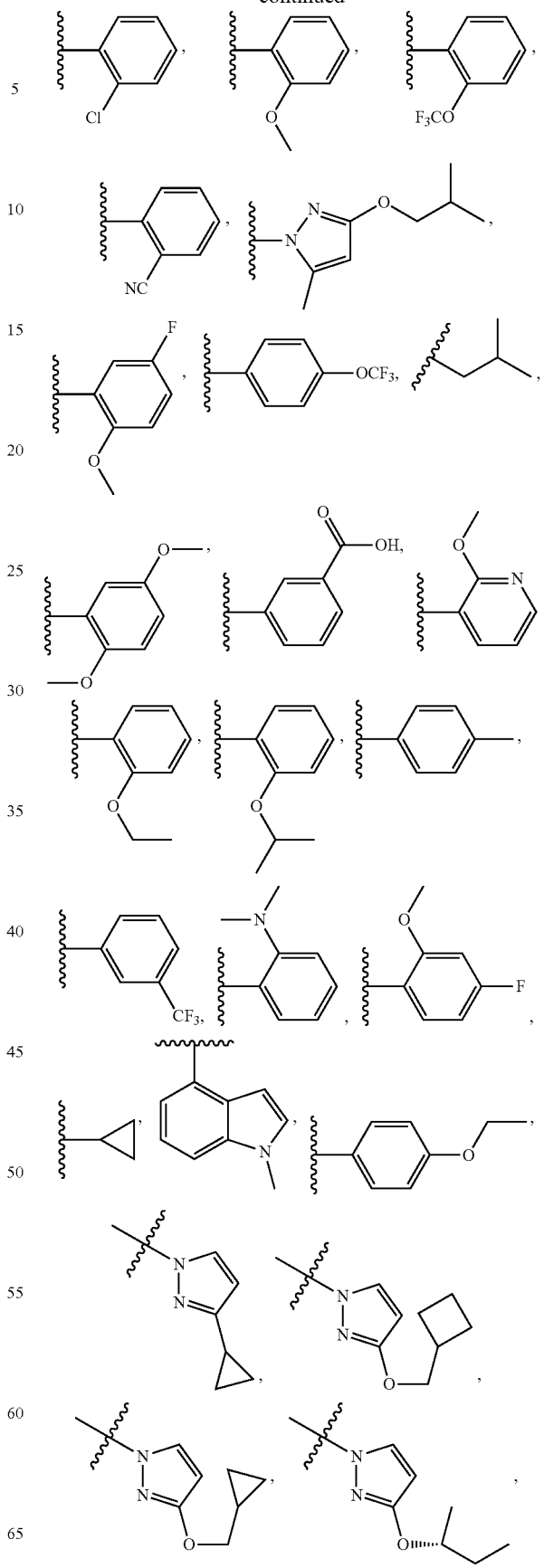

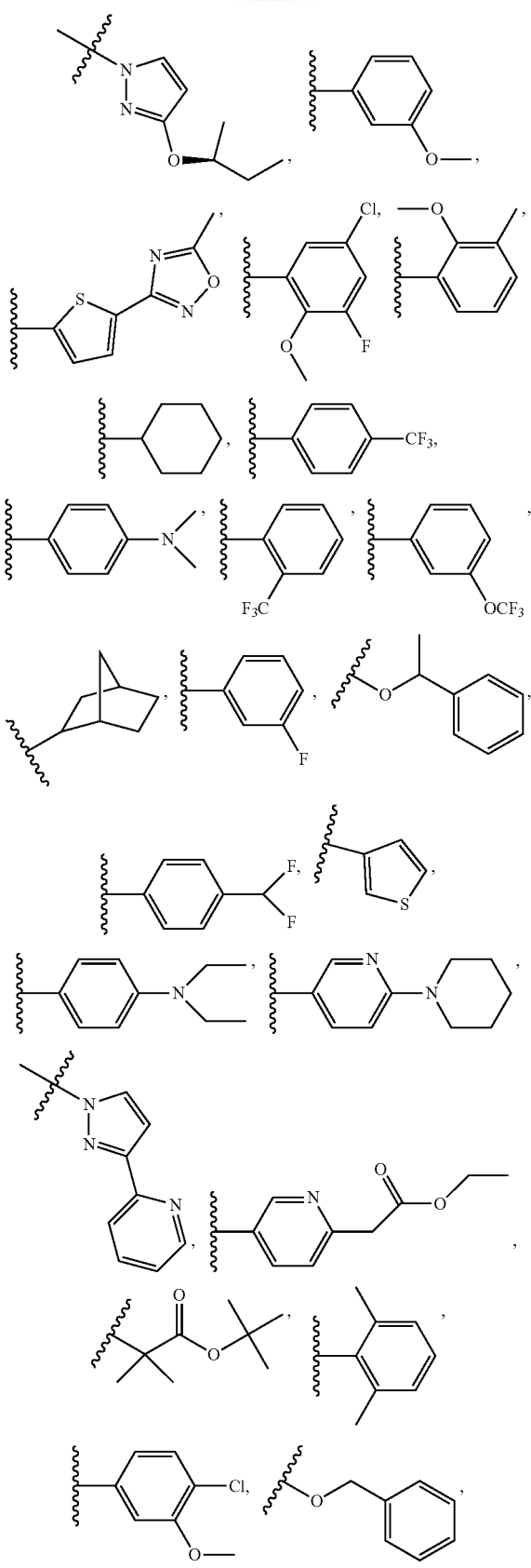
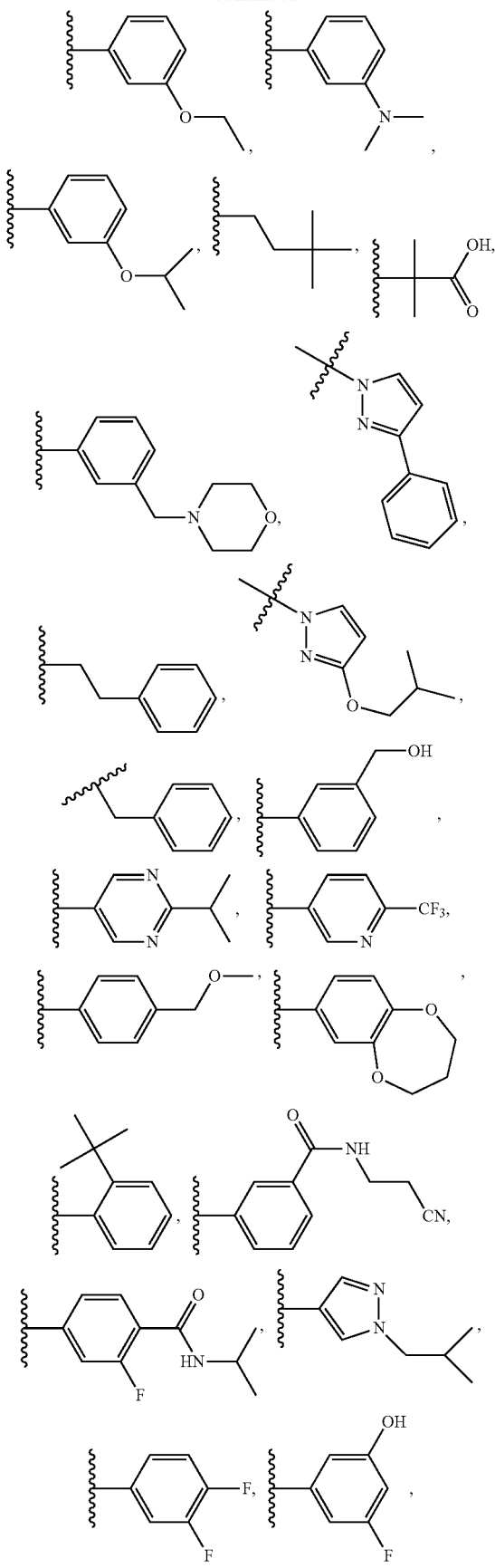

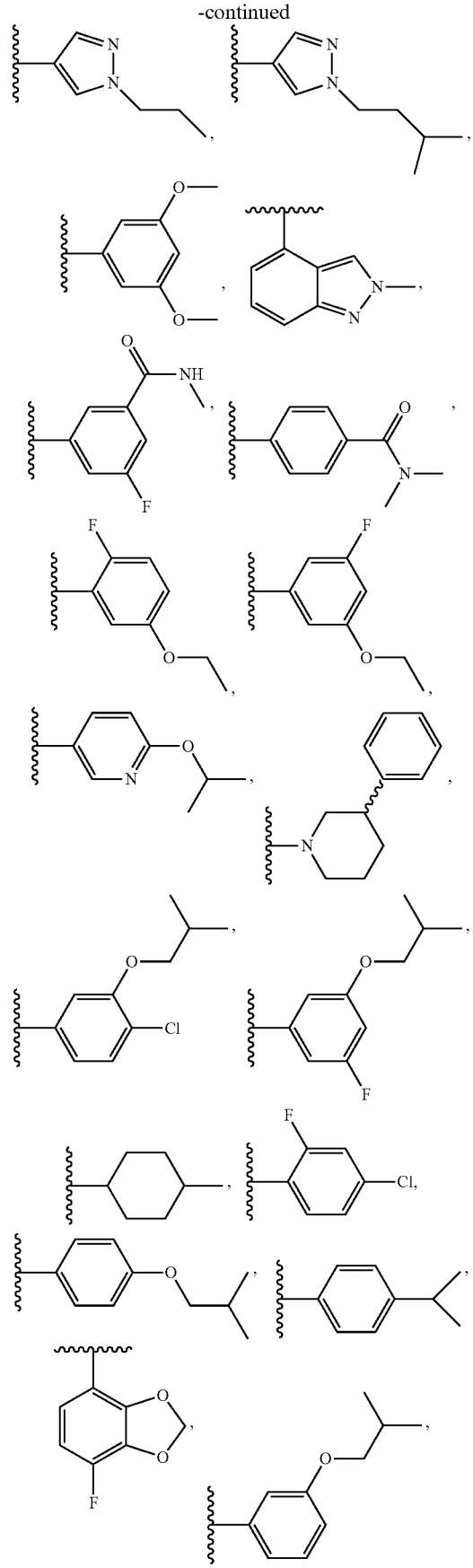
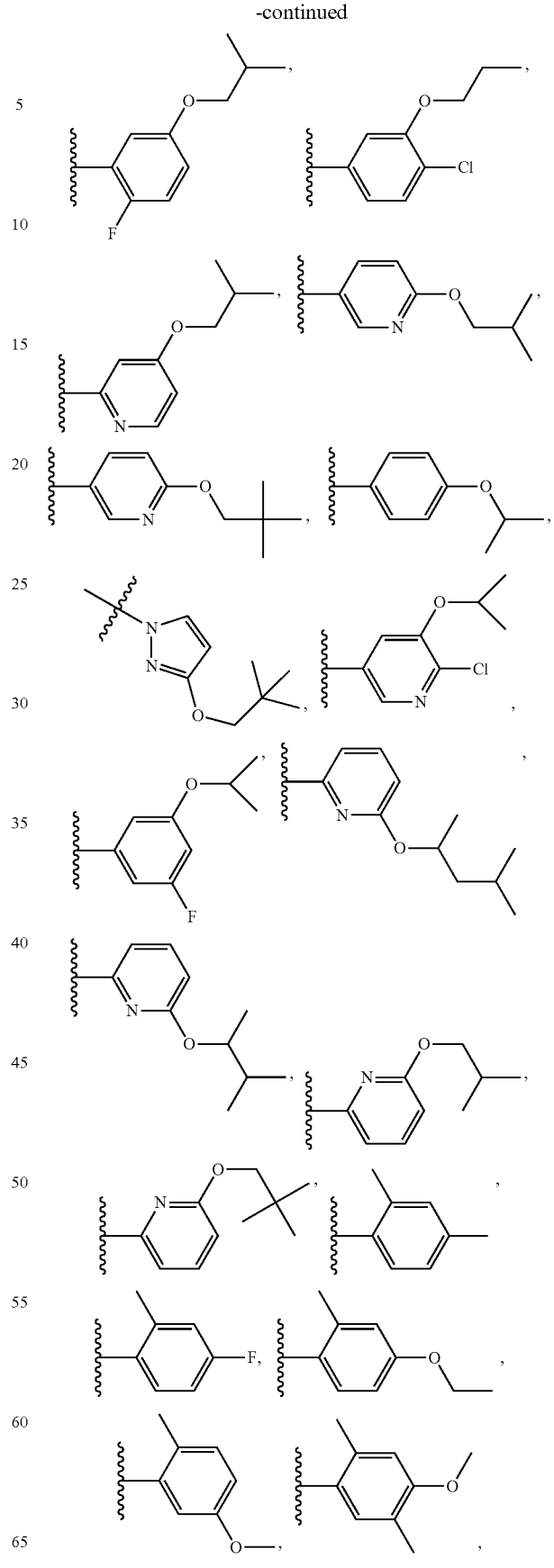

-continued

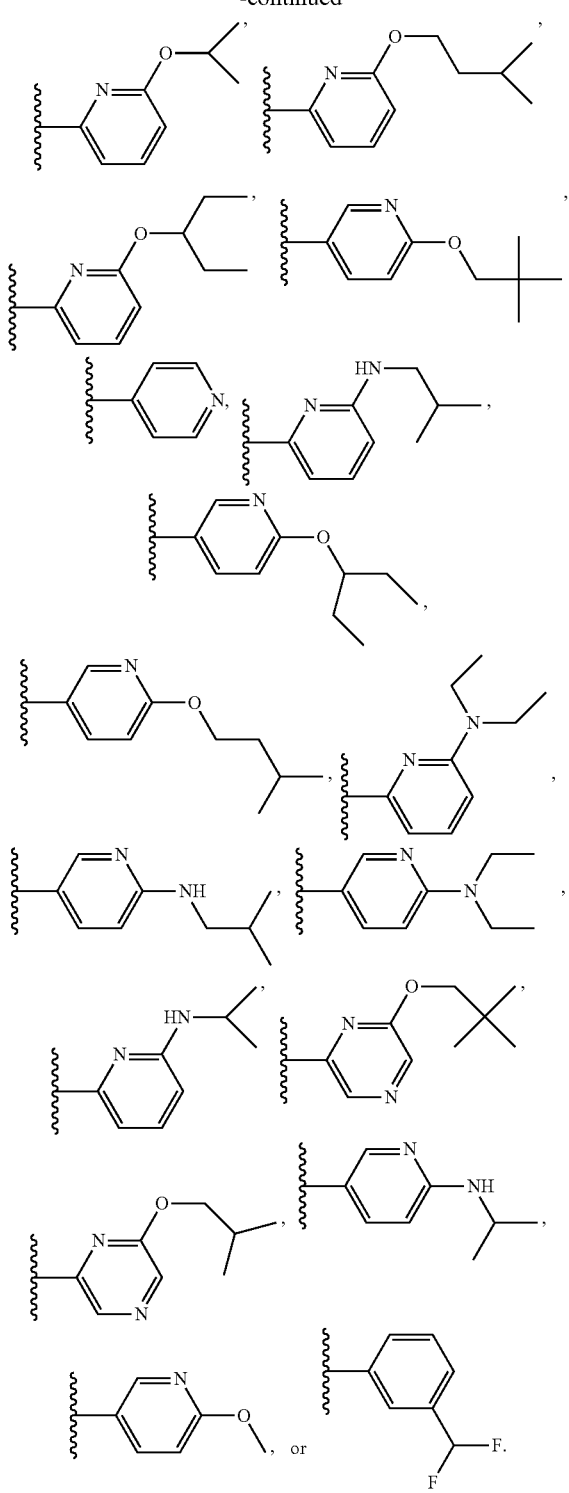

In some embodiments, $R_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)$ $(CH_2CH_2CH_3)$, $OCH(CH_3)_2$, $NH(CH_2)_2O(CH_2)_2CH_3$, $C(O)$ $CH_3$, $CH_2CH_2OH$, $CH_2NH_2$, $NH(CH_2)_2OH$, $N(CH_3)$ $CH_2CH_2CH_2OCH_3$, $NHCH_2CH_2COOH$, $NH(CH_2)_2N$ $(CH_3)_2$, $NH(CH_2)_2NH_2$, $NH(CH_2)_3NH_2$, $NH(CH_2)_2OCH_3$, $NHCH(CH_3)_2$,

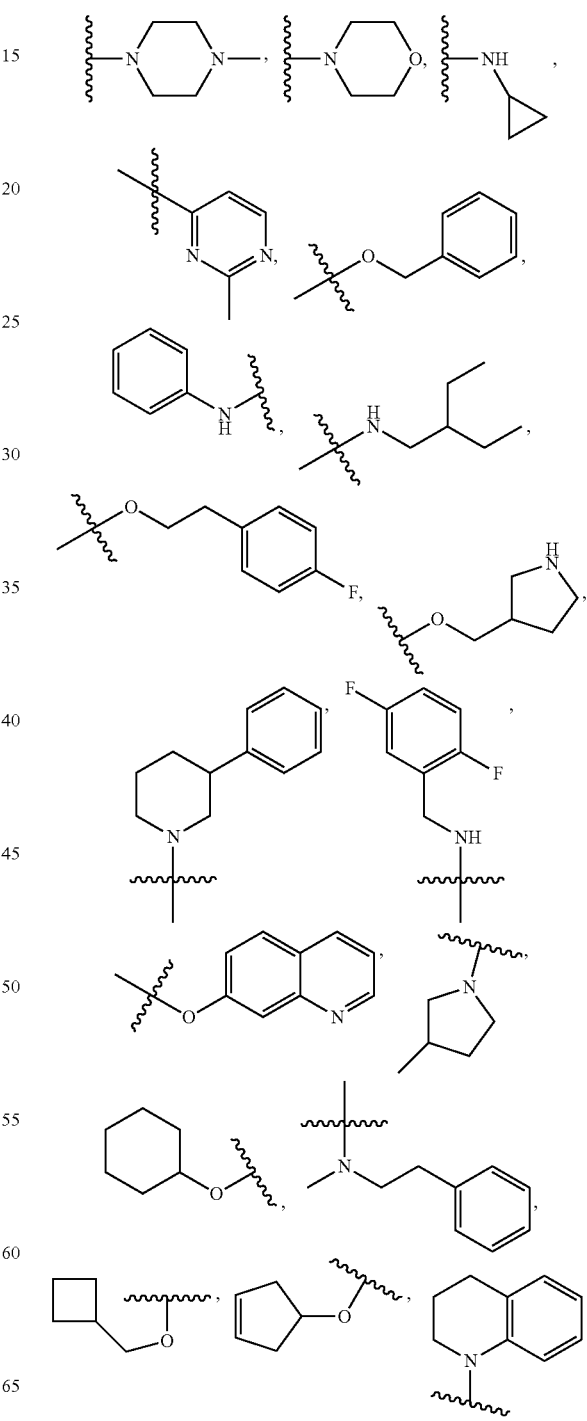

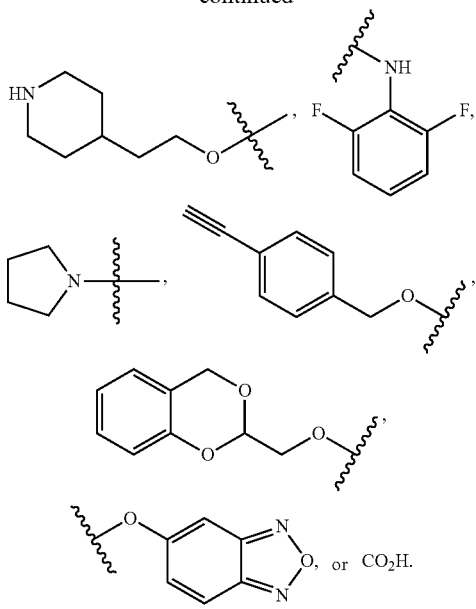

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

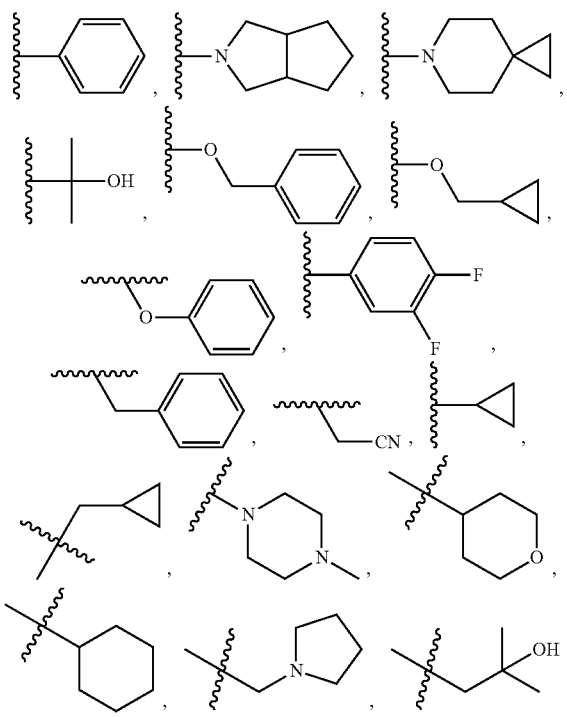

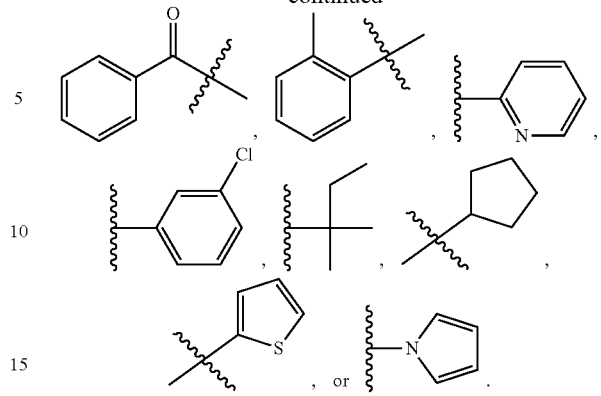

In some embodiments, o is 0. In some embodiments, o is 1. In some embodiments, o is 2.
In some embodiments, n is 0. In some embodiments, o is 1. In some embodiments, o is 2.
In some embodiments, p is 0. In some embodiments, p is 1. In some embodiments, p is 2.
In some embodiments, ring B is phenyl. In some embodiments, ring C is phenyl. In some embodiments, ring B and ring C are phenyl. In some embodiments, R₁ is halo. In some embodiments, R₁ is F. In some embodiments, R₁ is OCH₃. In some embodiments R₂ is amino. In some embodiments, R₃ is CH₃. In some embodiments, R₂ is amino and R₃ is CH₃. In some embodiments, Y is CH₃. In some embodiments, Y is O. In some embodiments, R₁ is F, R₂ is amino, R₃ is CH₃, and Y is CH₂. In some embodiments, Y is O. In some embodiments, R₁ is F, R₂ is amino, R₃ is CH₃, and Y is O.

In some embodiments, the invention features a compound of formula Ic-i:

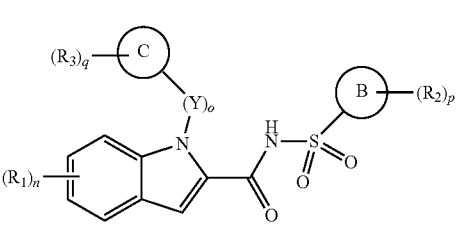

Ic-i or a pharmaceutically acceptable salt thereof, wherein, independently for each occurrence:
  Ring B is a C3-C10 heteroaryl ring wherein anywhere from 1 to 4 ring atoms are independently O, S, N, or NR;
  Ring C is a C6-C10 aryl ring, C3-C14 heteroaryl or heterocyclic ring wherein anywhere from 1 to 4 ring atoms are independently N, O, or S, or a C3-C10 cycloalkyl ring;
  Y is CRR, CO, O, S, SO, SO₂, S(O)NH or NR;
  R₁ is halo; CN; F₃S; SiR₃; OH; NRR; C1-C6 alkyl or fluoroalkyl; C1-C6 alkoxy or fluoroalkoxy; C1-C6 alkenyl; C1-C6 alkynyl; (C1-C9 alkylene)-R₄ wherein up to four CH₂ units are independently replaced with O, CO, S, SO, SO₂ or NR; C6-C10 aryl; C3-C10 heteroaryl or heterocyclic ring wherein anywhere from 1 to 4 ring atoms are independently O, S, N, or NR; or C3-C10 cycloalkyl;

R₂ is halo; OH; NRR; azide; CN; CO₂R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;

or two R₂ groups taken together may form a =CH₂ or =O group;

R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;

or two R₃ groups taken together may form a =CH₂ or =O group;

R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;

R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;

is 0, 1, 2, 3, 4, or 5;

p is 0, 1, 2, or 3; and q is 0, 1, 2, 3, 4, or 5.

In some embodiments, the compound of formula Ic-i exists as a pharmaceutically acceptable prodrug.

In some embodiments, ring B is pyridyl, pyridine-2(1H)-one, pyrazole, indole, aza-indole, thiophene, dihydrobenzofuran, or quinoline.

In some embodiments, ring B is a group represented by the corresponding moieties shown in the compounds of Table 1. For example, ring B is,

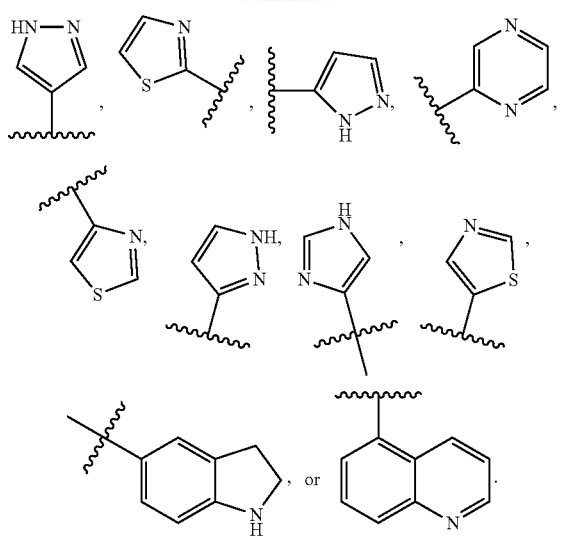

In some embodiments, ring C is phenyl, indole, cycloalkyl, pyridyl, pyrrolidine, naphthalene, or dihydroindene.

In some embodiments, ring C is is a group represented by the corresponding moieties shown in the compounds of Table 1. For example, ring C is

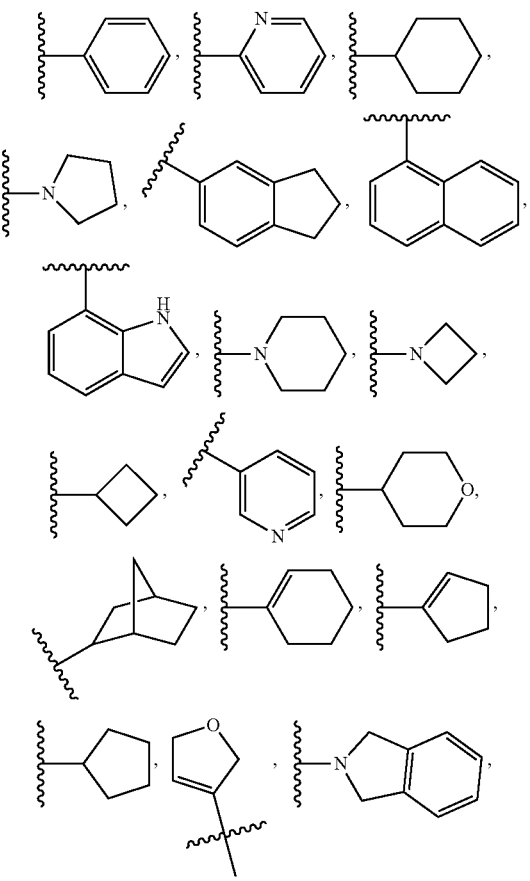

313
-continued

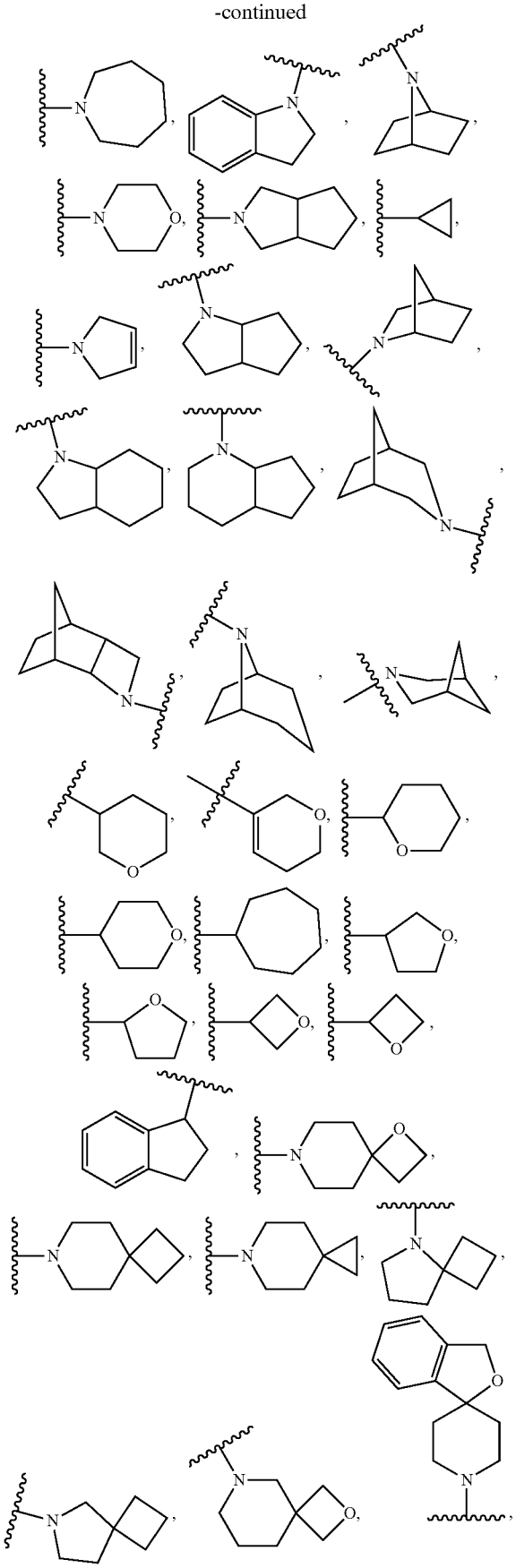

314
-continued

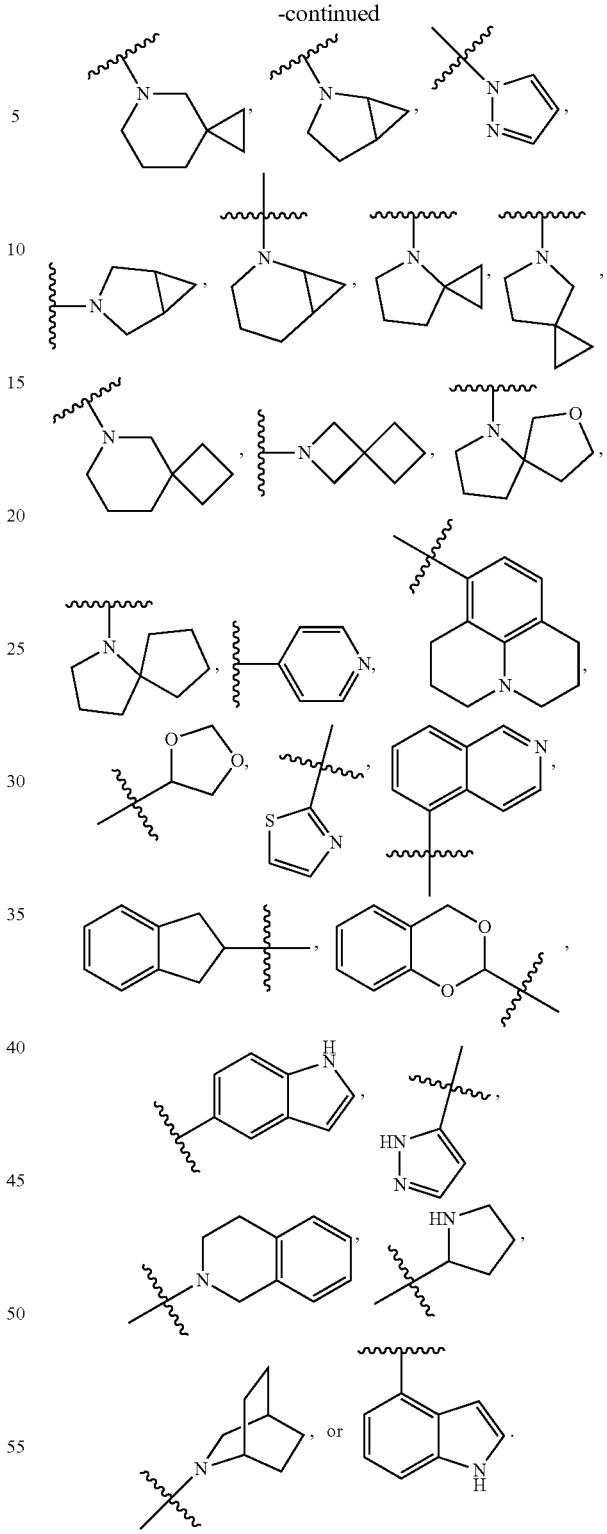

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-R$_4$ wherein up to four CH$_2$ units are independently replaced with O, CO, S, SO, SO$_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, CH$_2$OH, CH$_2$OCH$_3$, CN, CO$_2$H, amino, amido, C3-C10 heteroaryl, and C3-C10 heterocycloalkyl.

In some embodiments, R$_1$ is is a group represented by the corresponding moieties shown in the compounds of Table 1. For example, R$_1$ is CH$_3$, Cl, F, CN, OCH$_3$, CF$_3$, CH$_2$CH$_3$, tBu, CH(CH$_3$)$_2$, OCH$_2$CH$_2$OCH$_2$CH$_3$,

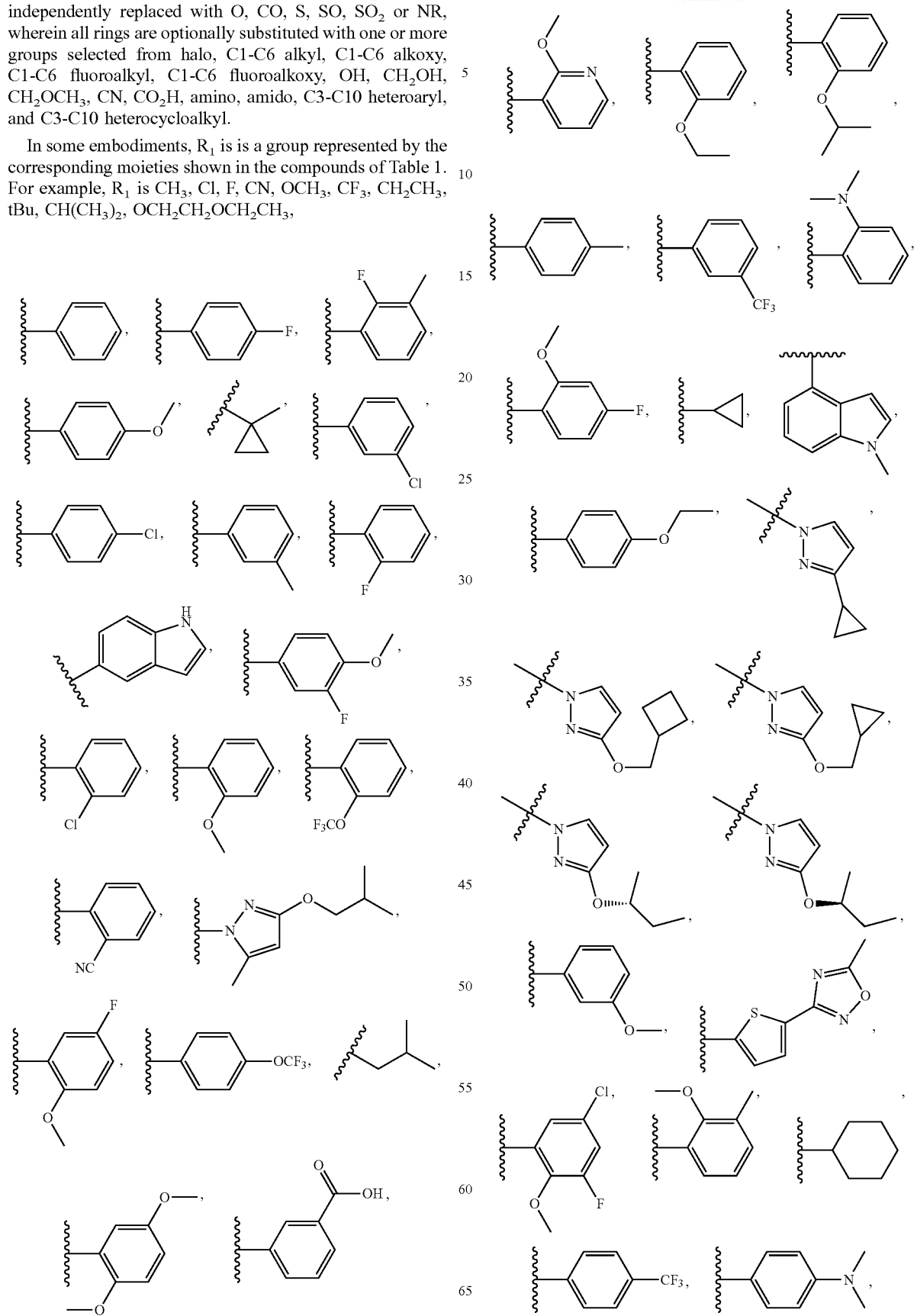

317
-continued
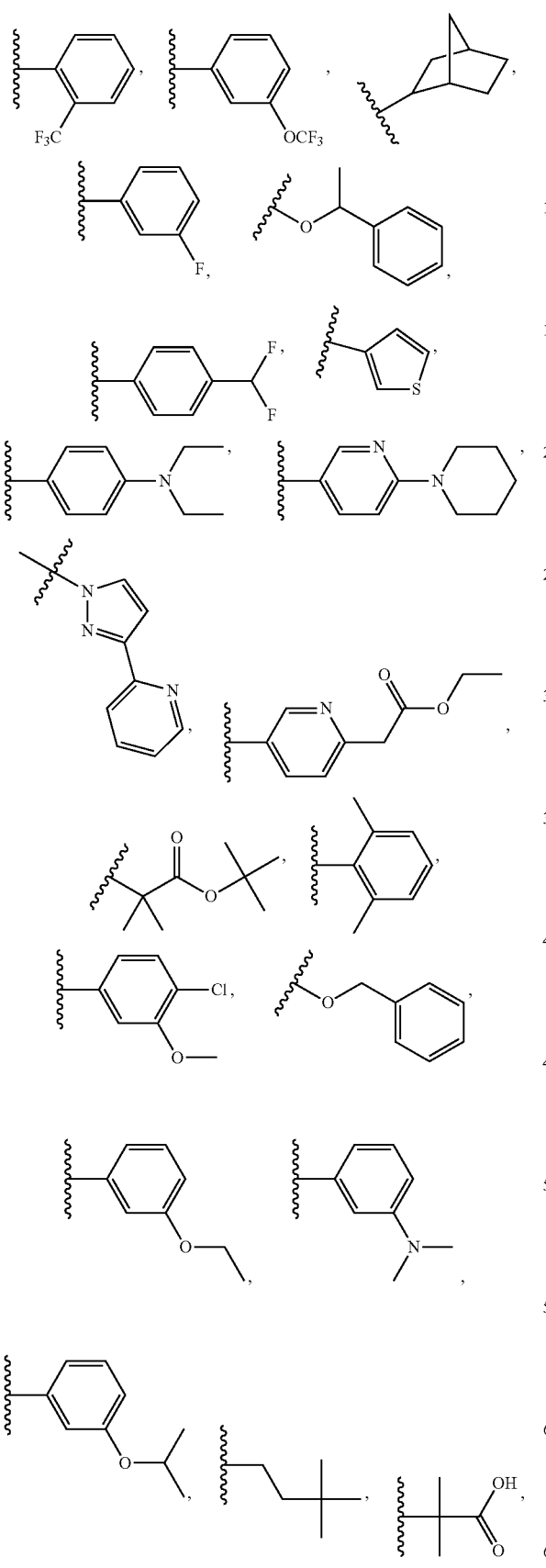
318
-continued
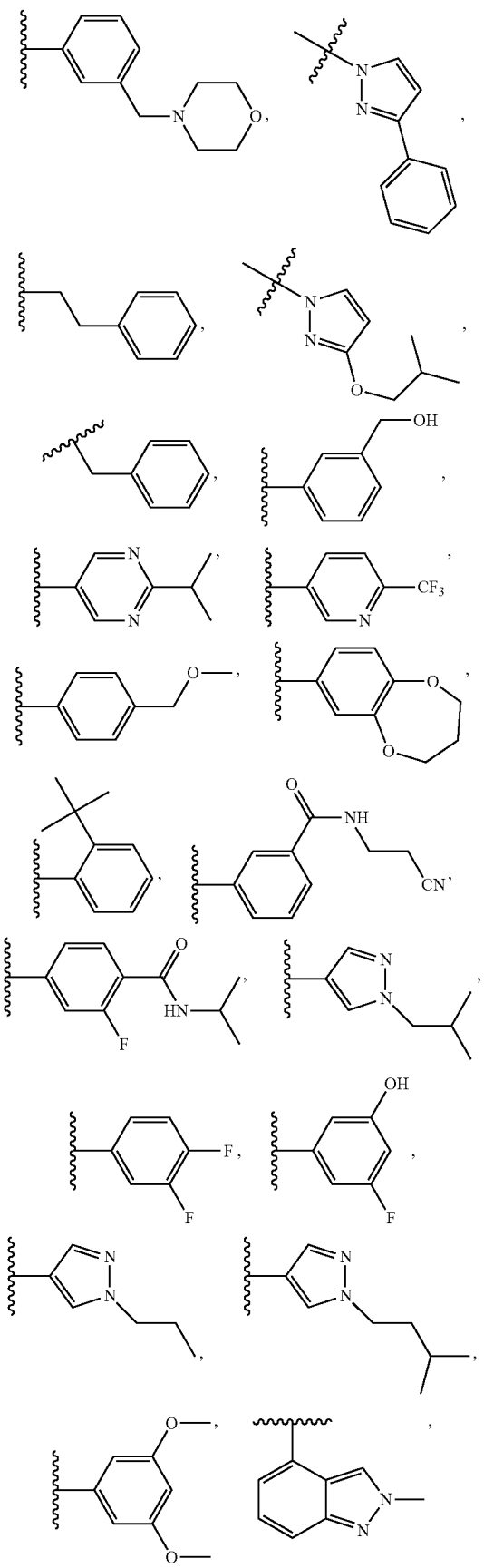

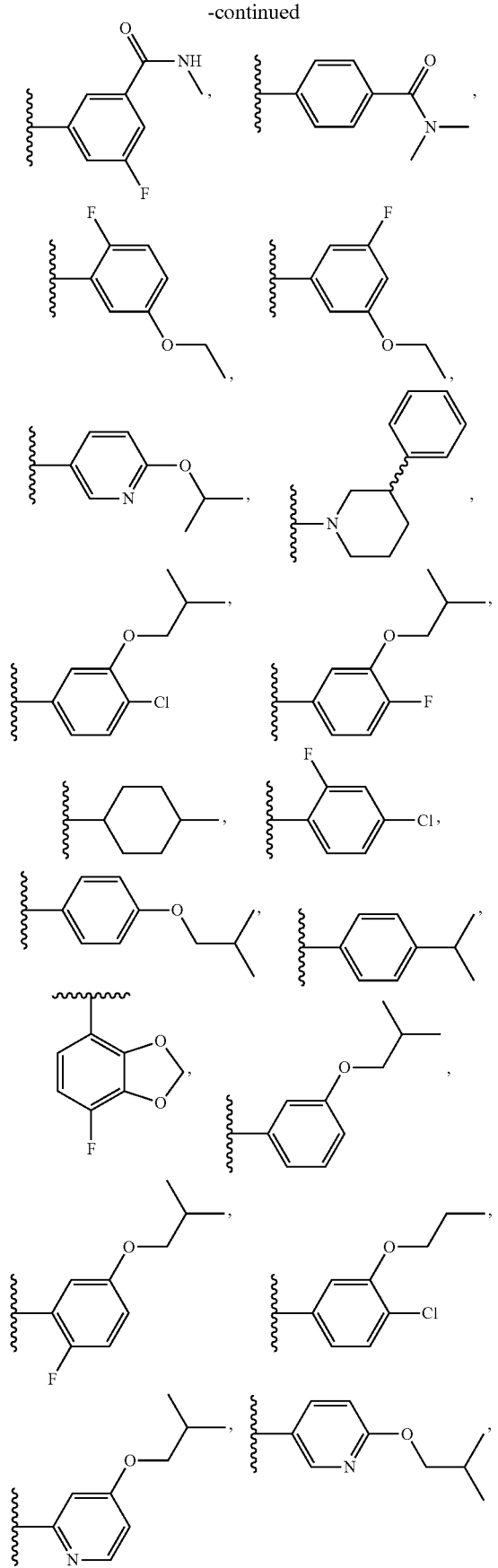
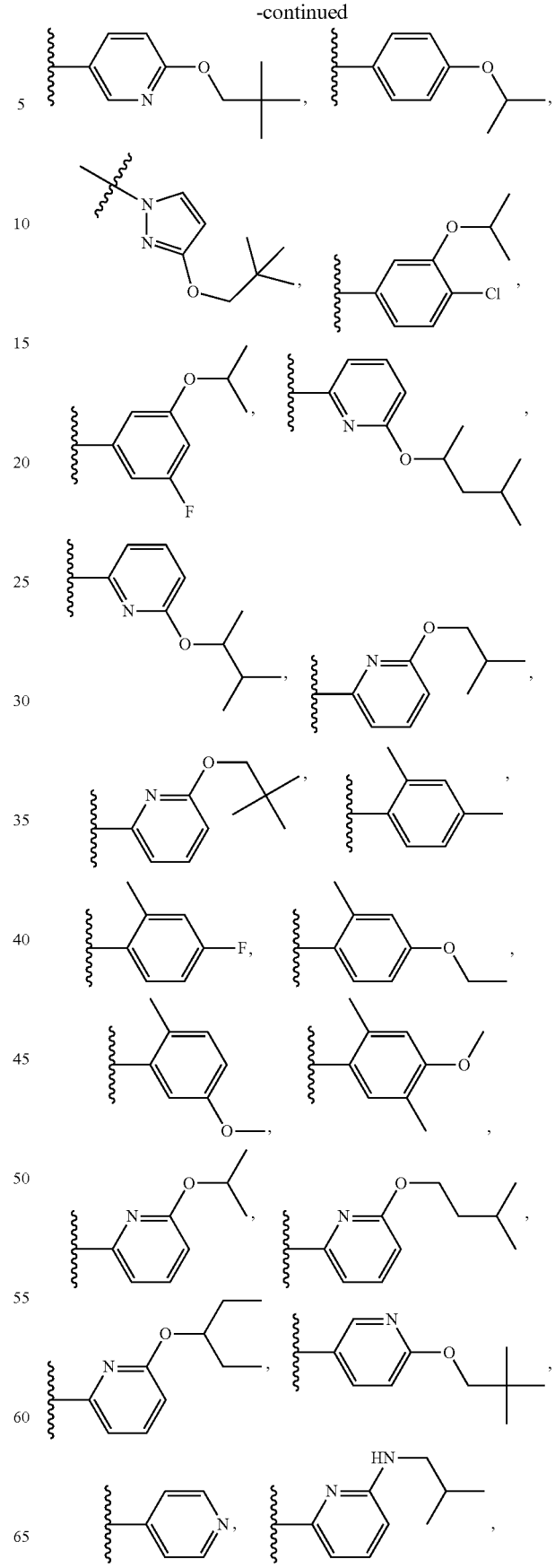

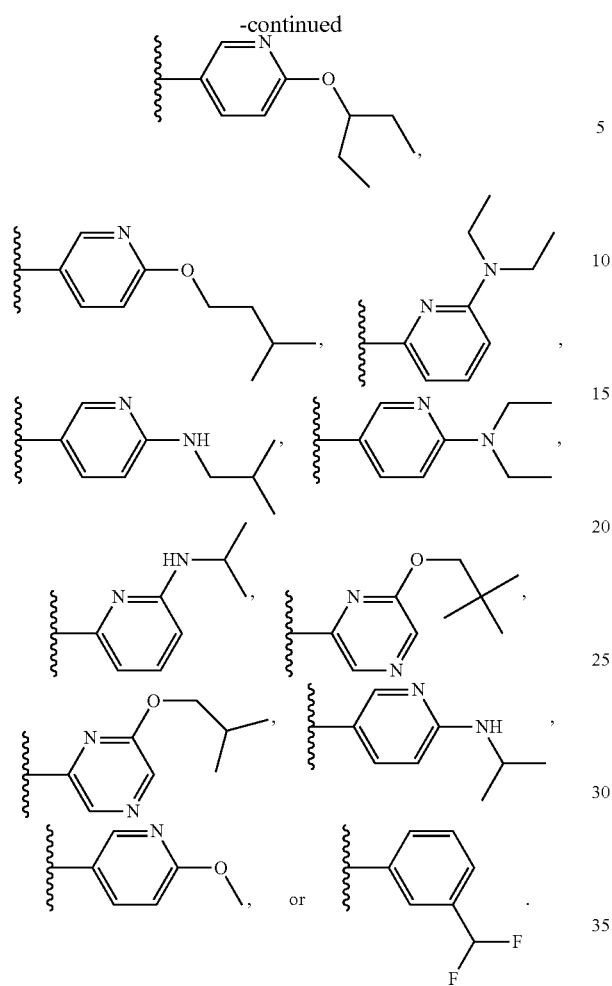

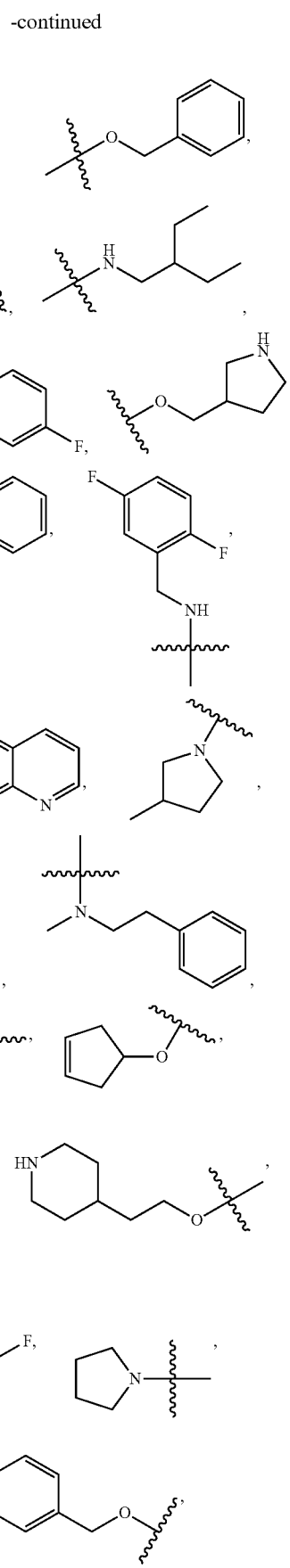

In some embodiments, $R_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

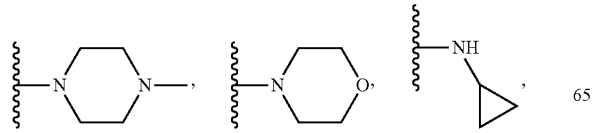

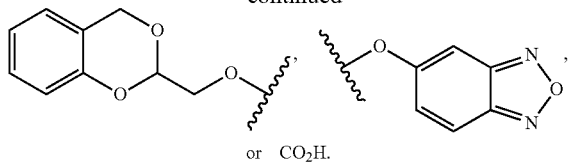

or CO₂H.

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

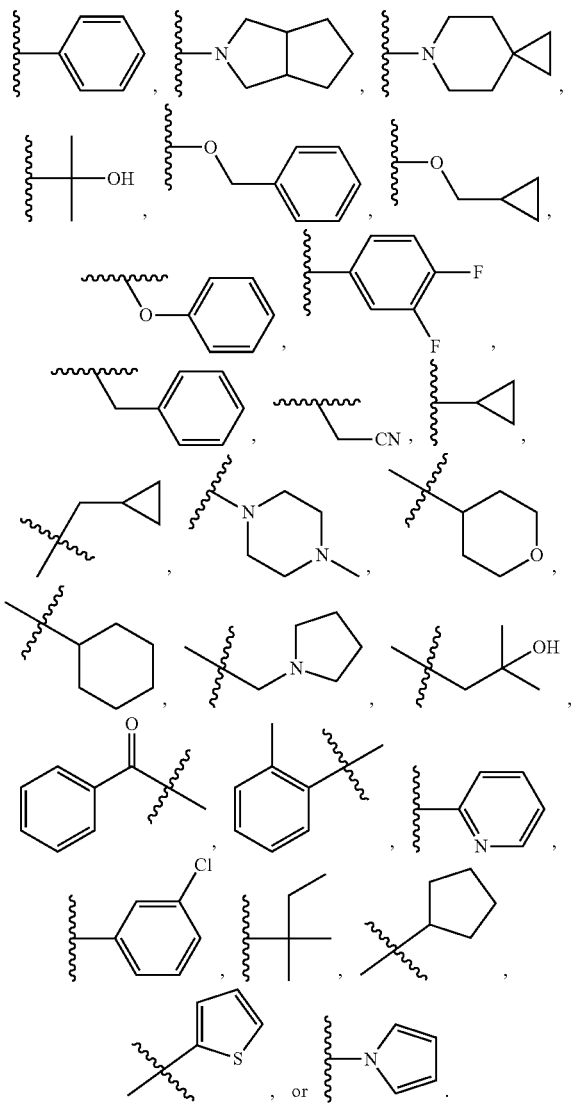

In some embodiments, o is 0. In some embodiments, o is 1. In some embodiments, o is 2.

In some embodiments, n is 0. In some embodiments, o is 1. In some embodiments, o is 2.

In some embodiments, p is 0. In some embodiments, p is 1. In some embodiments, p is 2.

In other embodiments, the invention features a compound of formula Ic-ii:

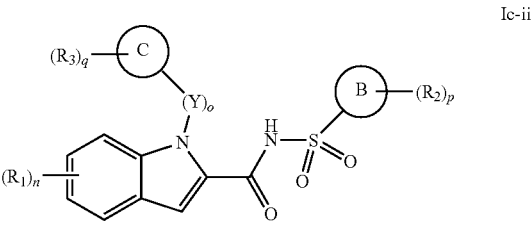

Ic-ii or a pharmaceutically acceptable salt thereof, wherein, independently for each occurrence:
Ring B is a C6-C10 aryl ring;
Ring C is a C6-C10 aryl ring, C3-C14 heteroaryl or heterocyclic ring wherein anywhere from 1 to 4 ring atoms are independently N, O, or S, or a C3-C10 cycloalkyl ring;
Y is CRR, CO, O, S, SO, SO₂, S(O)NH or NR;
R₁ is halo; CN; F5S; SiR₃; OH; NRR; C1-C6 alkyl or fluoroalkyl; C1-C6 alkoxy or fluoroalkoxy; C1-C6 alkenyl; C1-C6 alkynyl; (C1-C9 alkylene)-R₄ wherein up to four CH₂ units are independently replaced with O, CO, S, SO, SO₂ or NR; C6-C10 aryl; C3-C10 heteroaryl or heterocyclic ring wherein anywhere from 1 to 4 ring atoms are independently O, S, N, or NR; or C3-C10 cycloalkyl;
R₂ is halo; OH; NRR; azide; CN; CO₂R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₂ groups taken together may form a =CH₂ or =O group;
R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₃ groups taken together may form a =CH₂ or =O group;
R₄ is H; azide; CF₃; CHF₂; OR; CCH; CO₂R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO₂R;
R is independently H; OH; CO₂H; CO₂C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
n is 0, 1, 2 or 3;
o is 0, 1, 2, 3, 4, or 5;
p is 0, 1, 2, or 3; and
q is 0, 1, 2, 3, 4, or 5.

In some embodiments, the compound of formula Ic-ii exists as a pharmaceutically acceptable prodrug.

In some embodiments, ring B is phenyl or napthalene.

In some embodiments, ring C is phenyl, indole, cycloalkyl, pyridyl, pyrrolidine, naphthalene, or dihydroindene.

In some embodiments, ring C is a group represented by the corresponding moieties shown in the compounds of Table 1. For example, ring C is

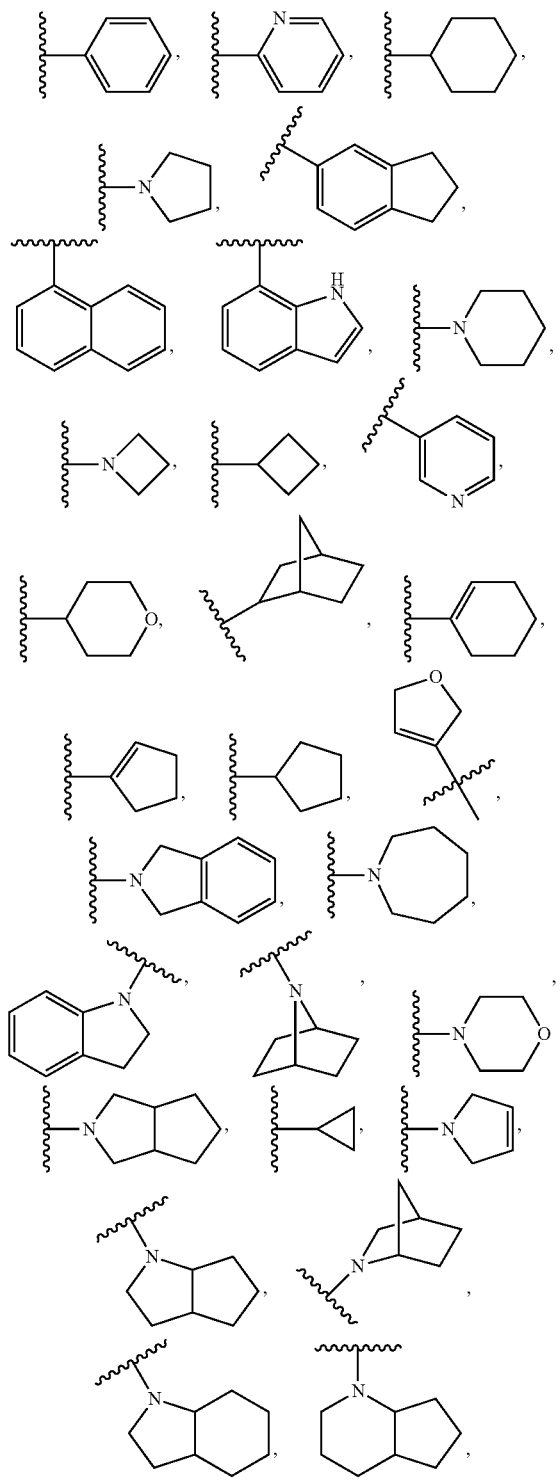

-continued

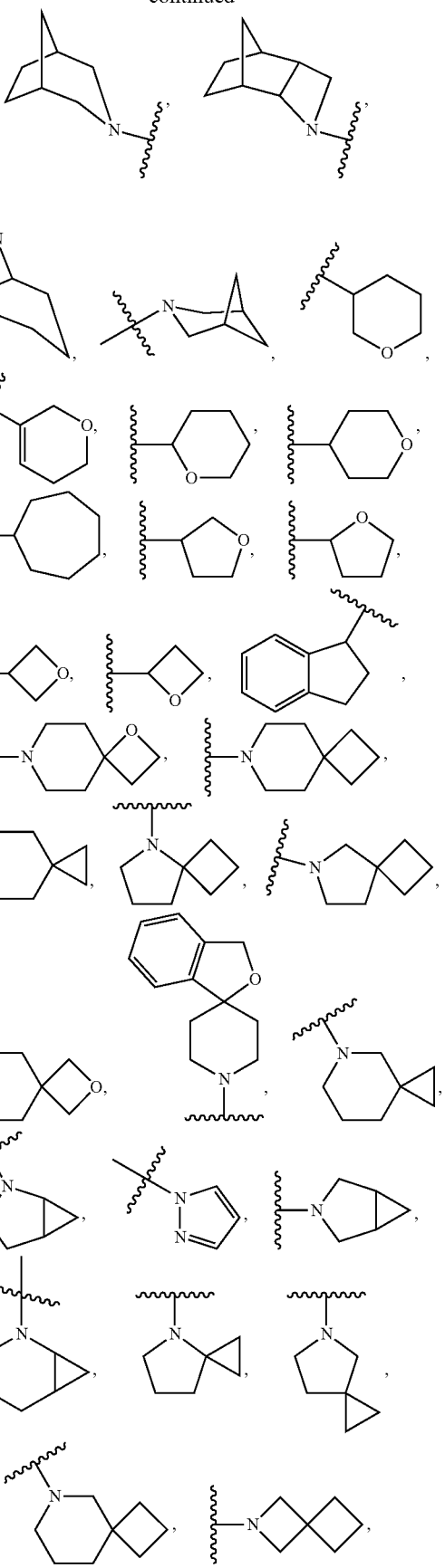

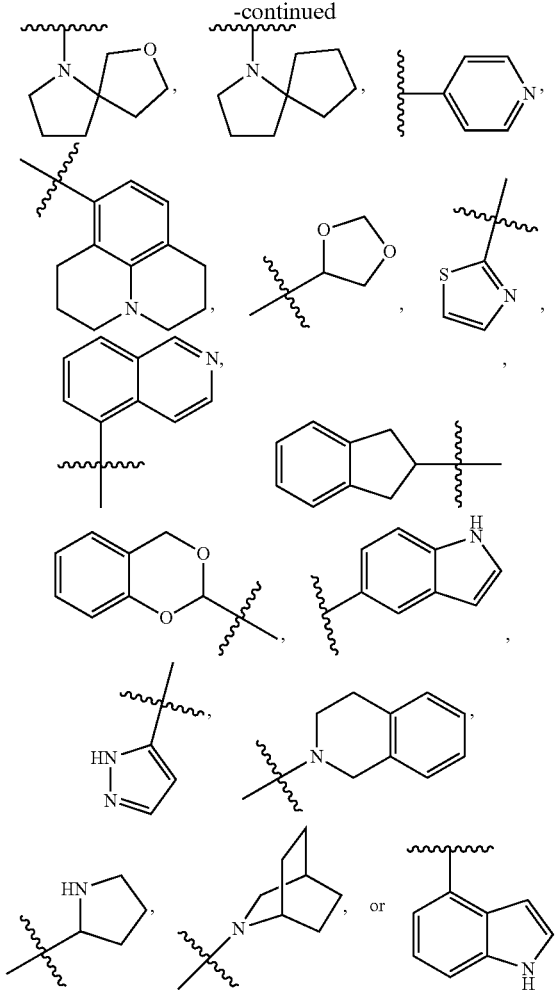

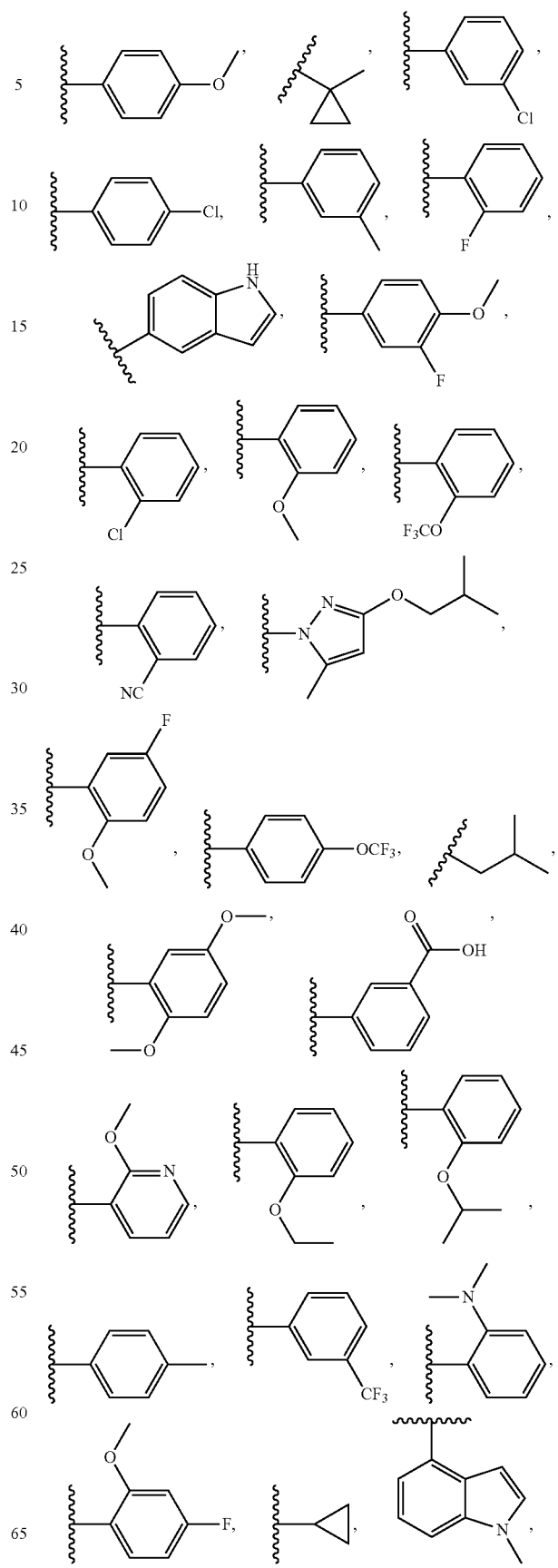

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $R_1$ is $CH_3$, Cl, F, CN, $OCH_3$, $CF_3$, $CH_2CH_3$, tBu, $CH(CH_3)_2$, $OCH_2CH_2OCH_2CH_3$, 329
-continued
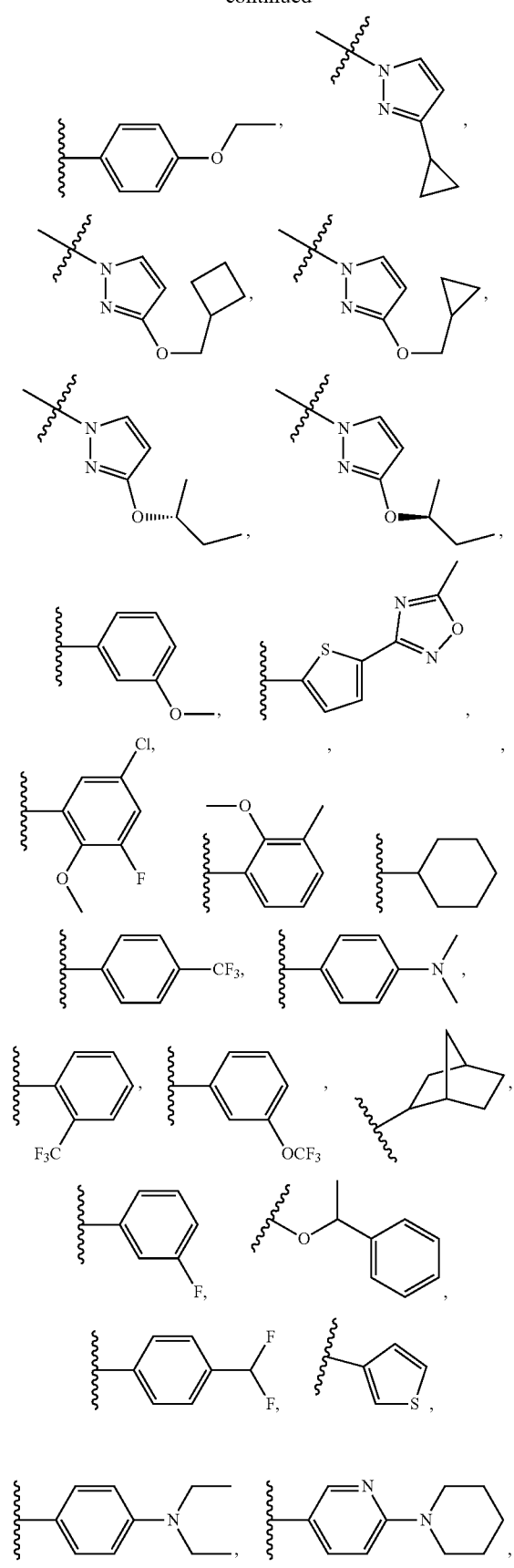
330
-continued
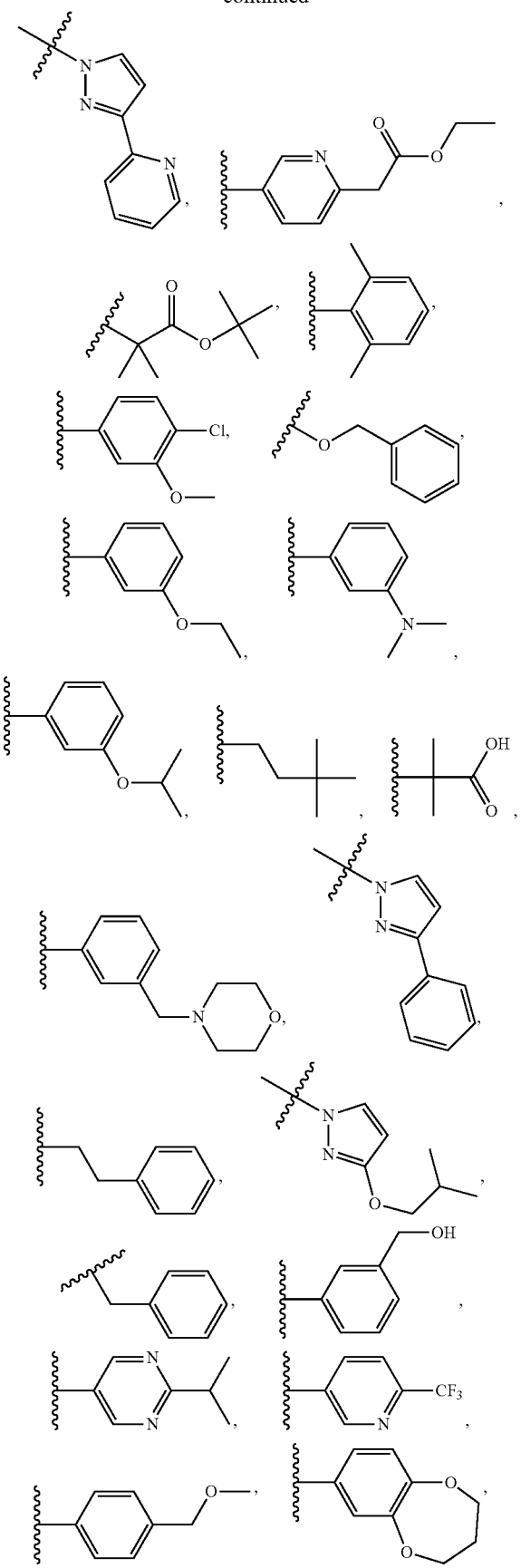

331
-continued
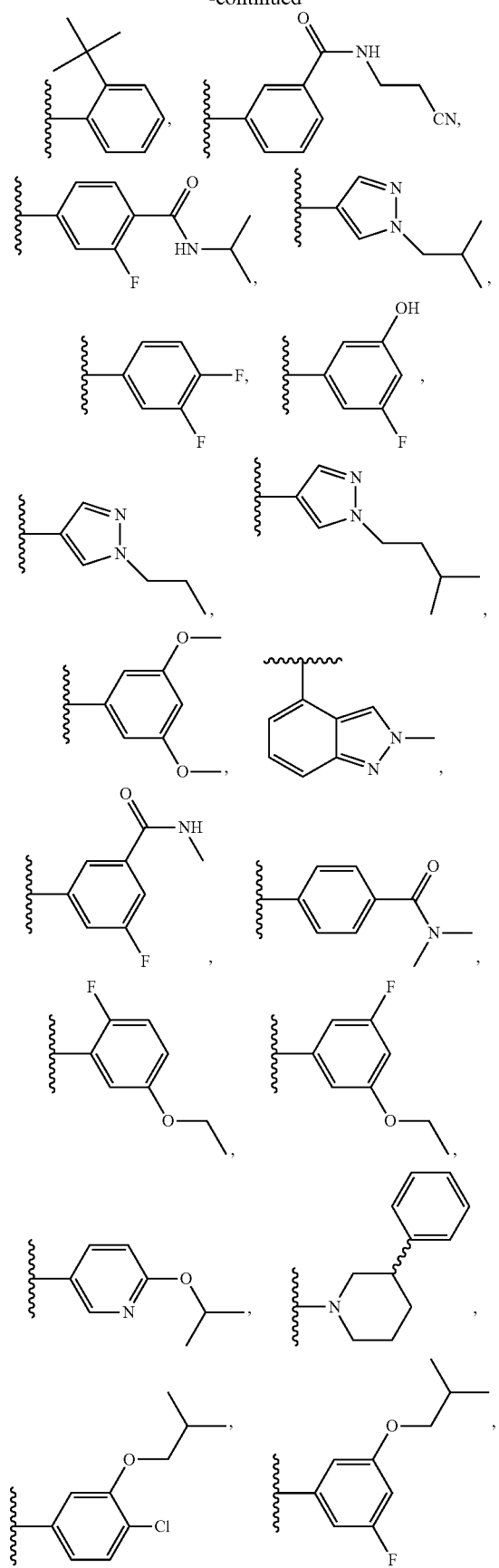
332
-continued
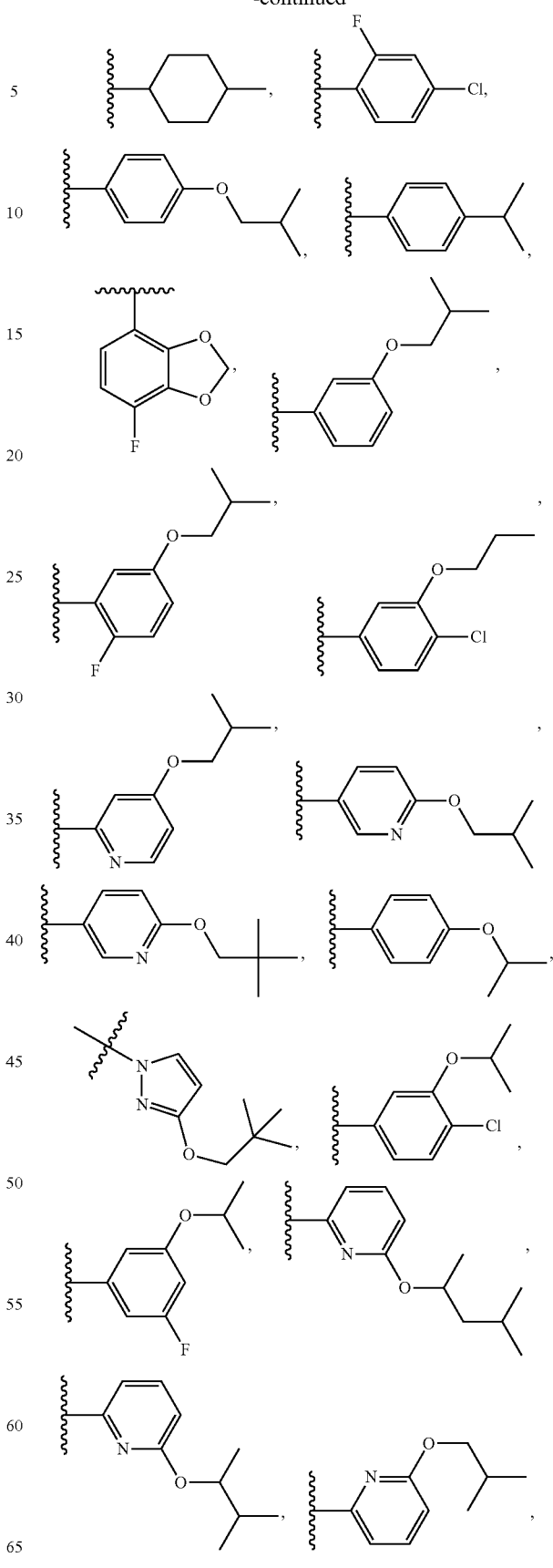

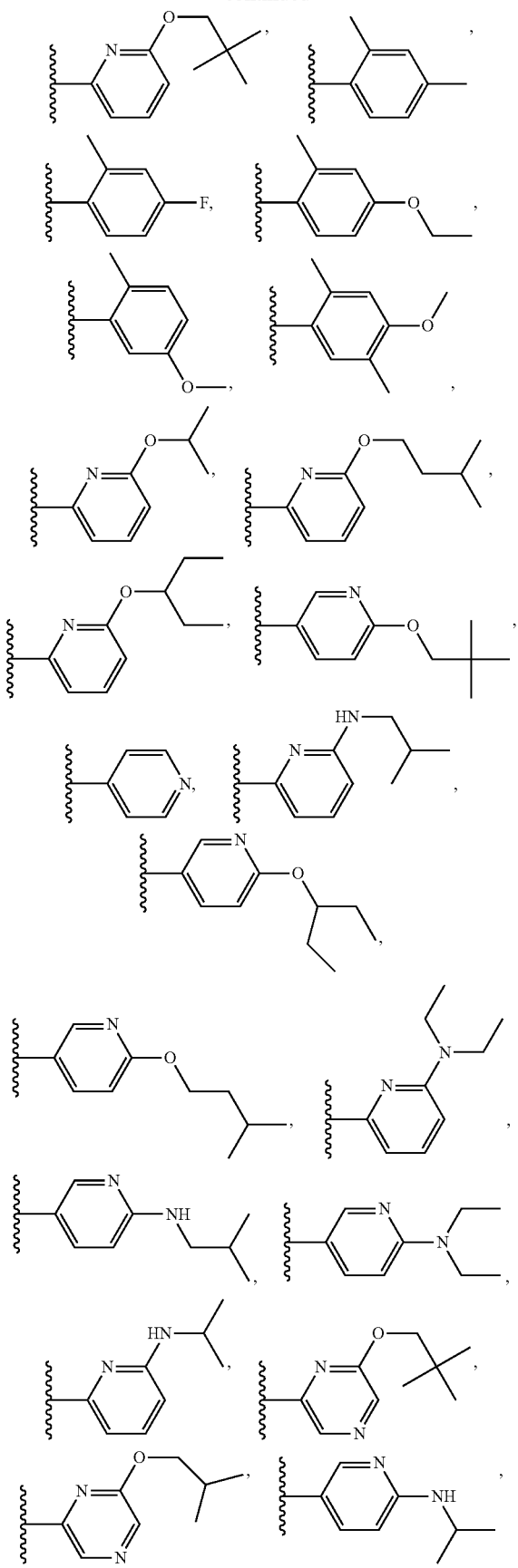

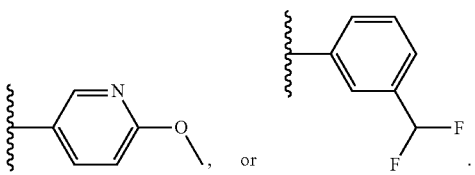

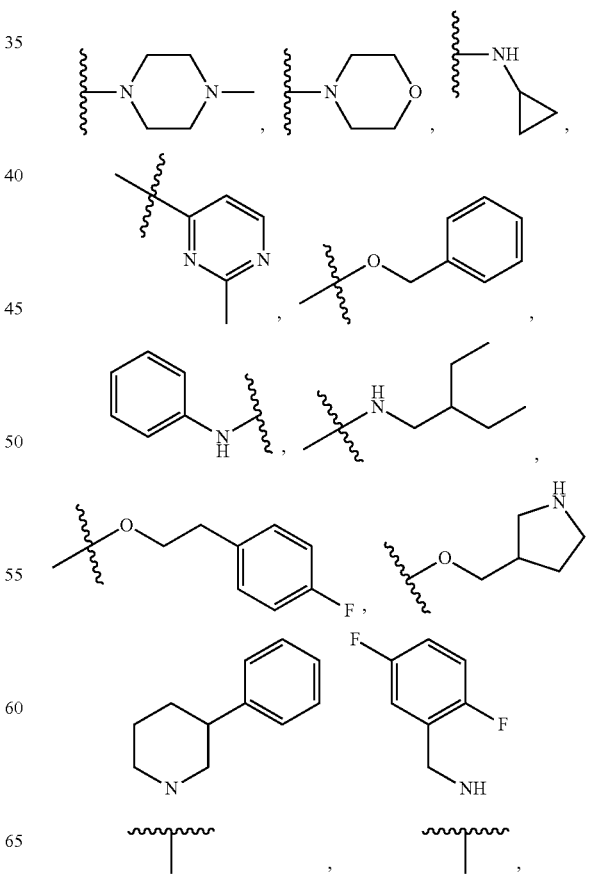

In some embodiments, $R_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-$R_4$ wherein up to four $CH_2$ units are independently replaced with O, CO, S, SO, $SO_2$ or NR.

In some embodiments, $R_2$ is a group represented by the corresponding moieties shown in the compounds of Table 1. For example, $R_2$ is Cl, F, OH, CN, $N_3$, $NH_2$, $NH(CH_3)$, $N(CH_3)_2$, $N(CH_3)CH_2CH_2CH_3$, $N(CH_3)CH_2CH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)$ $(CH_2CH_2CH_3)$, $OCH(CH_3)_2$, $NH(CH_2)_2O(CH_2)_2CH_3$, $C(O)$ $CH_3$, $CH_2CH_2OH$, $CH_2NH_2$, $NH(CH_2)_2OH$, $N(CH_3)$ $CH_2CH_2CH_2OCH_3$, $NHCH_2CH_2COOH$, $NH(CH_2)_2N$ $(CH_3)_2$, $NH(CH_2)_2NH_2$, $NH(CH_2)_3NH_2$, $NH(CH_2)_2OCH_3$, $NHCH(CH_3)_2$,

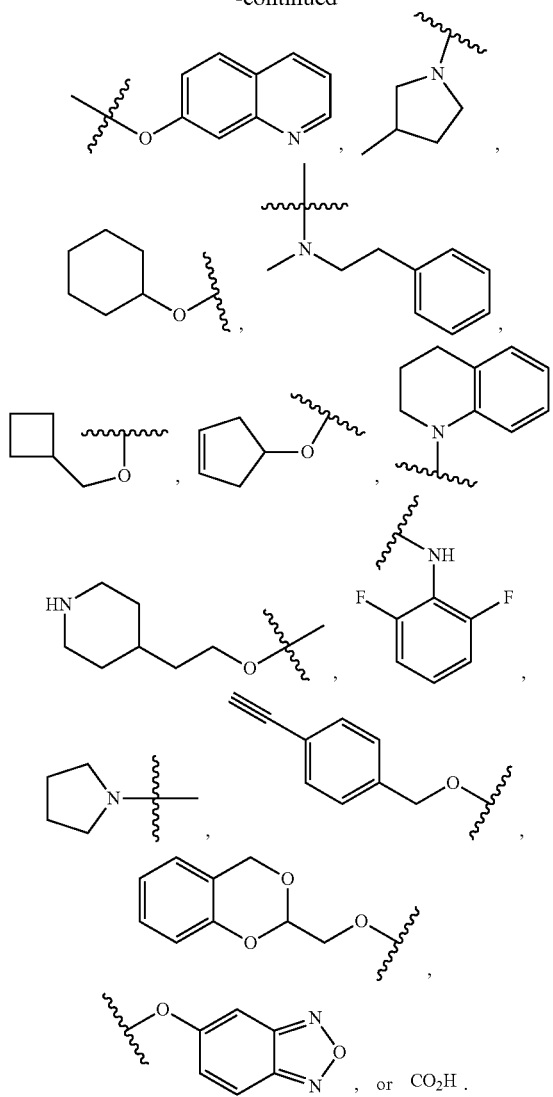

, or CO₂H.

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

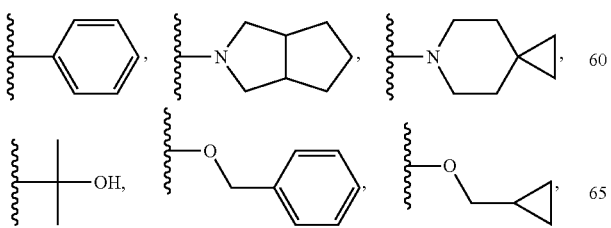

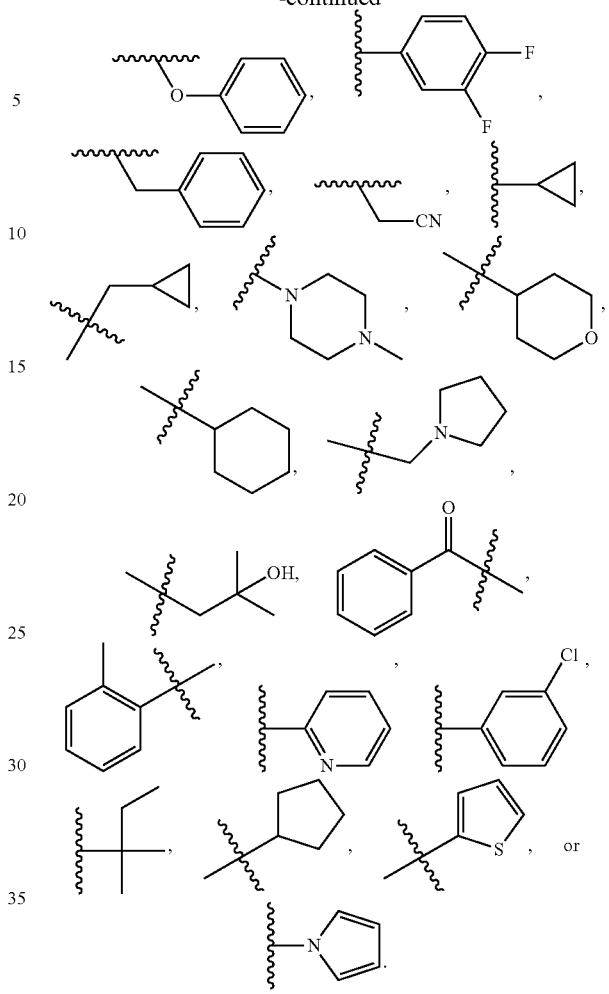

In some embodiments, o is 0. In some embodiments, o is 1. In some embodiments, o is 2.

In some embodiments, n is 0. In some embodiments, o is 1. In some embodiments, o is 2.

In some embodiments, p is 0. In some embodiments, p is 1. In some embodiments, p is 2.

In some embodiments, the invention features a compound of formula Id:

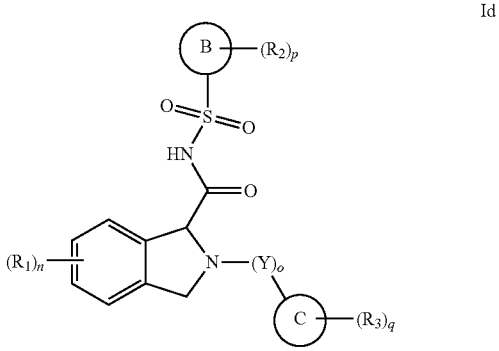

or a pharmaceutically acceptable salt thereof, wherein, independently for each occurrence:

Ring B is a C6-C10 aryl ring or C3-C10 heteroaryl or heterocyclic ring wherein anywhere from 1 to 4 ring atoms are independently O, S, N, or NR;

Ring C is a C6-C10 aryl ring, C3-C14 heteroaryl or heterocyclic ring wherein anywhere from 1 to 4 ring atoms are independently N, O, or S, or a C3-C10 cycloalkyl ring;

Y is CRR, CO, O, S, SO, $SO_2$, S(O)NH or NR;

$R_1$ is halo; CN; F5S; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;

$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_2$ groups taken together may form a =$CH_2$ or =O group;

$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;

or two $R_3$ groups taken together may form a =$CH_2$ or =O group;

$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;

R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;

o is 0, 1, 2, 3, 4, or 5;

p is 0, 1, 2, or 3; and q is 0, 1, 2, 3, 4, or 5.

In some embodiments, the compound of formula Id exists as a pharmaceutically acceptable prodrug.

In some embodiments, ring B is phenyl, pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

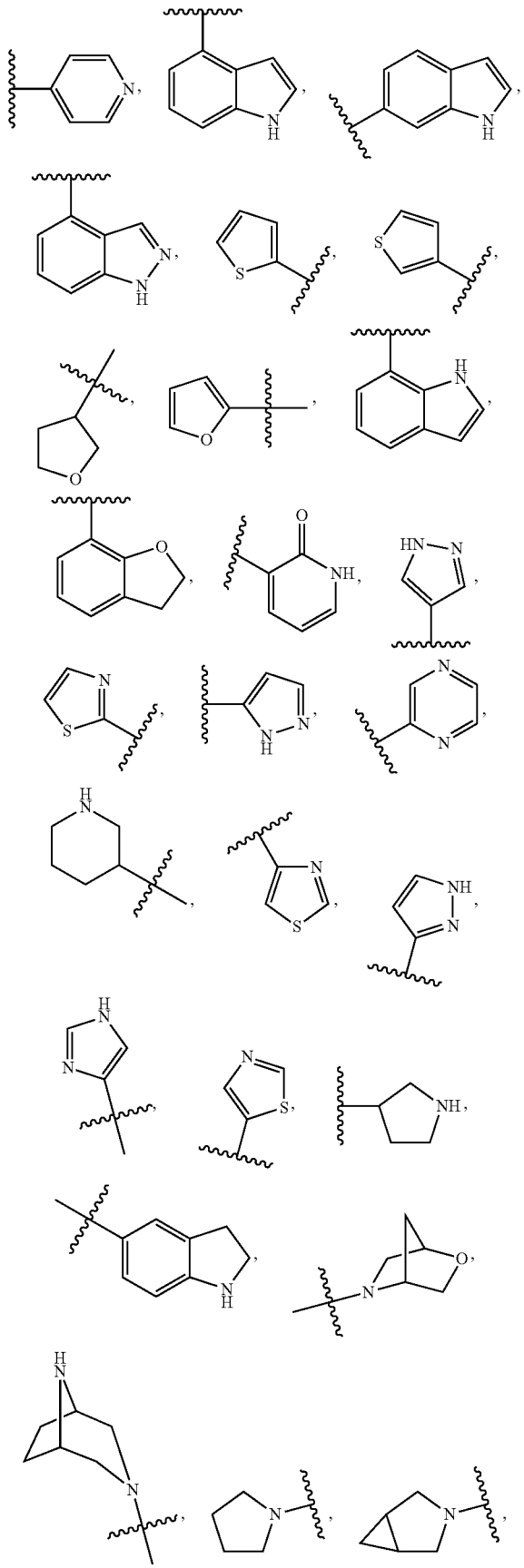

-continued

-continued
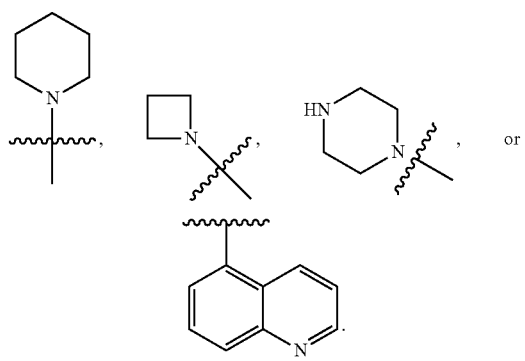
In some embodiments, ring C is phenyl, indole, cycloalkyl, pyridyl, pyrrolidine, naphthalene, or dihydroindene.
In some embodiments, ring C is is a group represented by the corresponding moieties shown in the compounds of Table 1. For example, ring C is
-continued
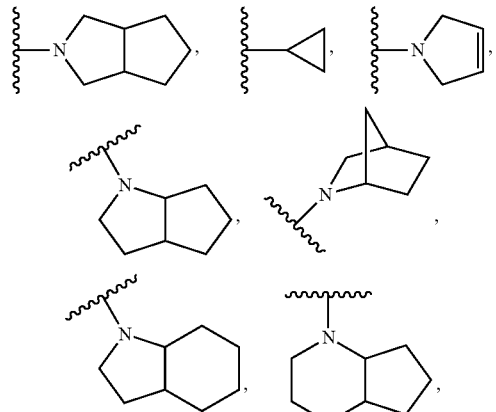
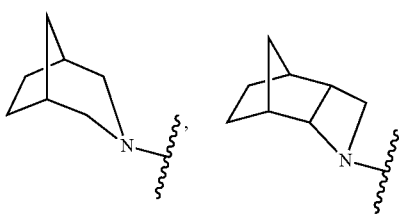
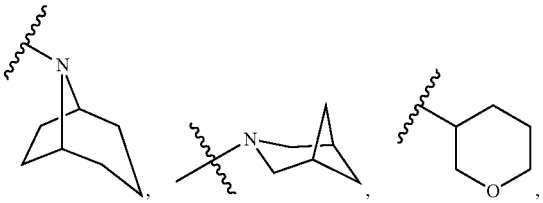
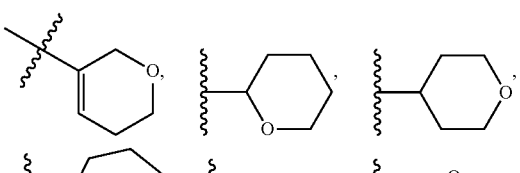
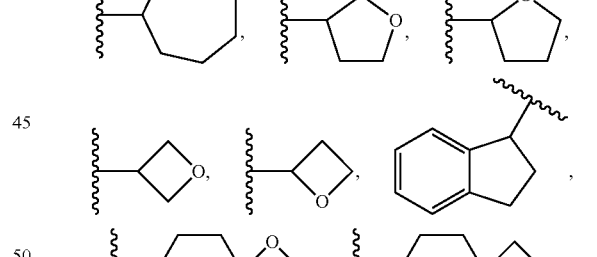
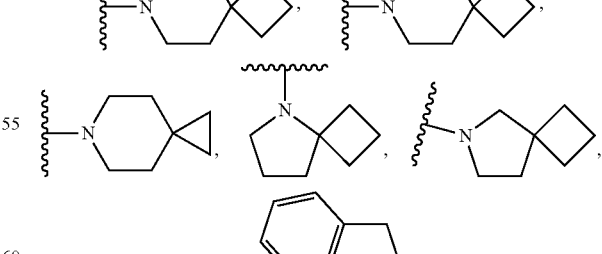
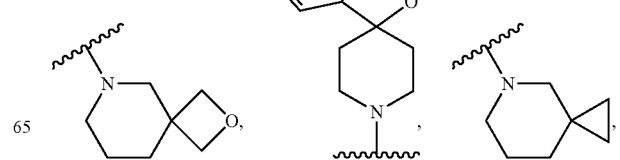

-continued

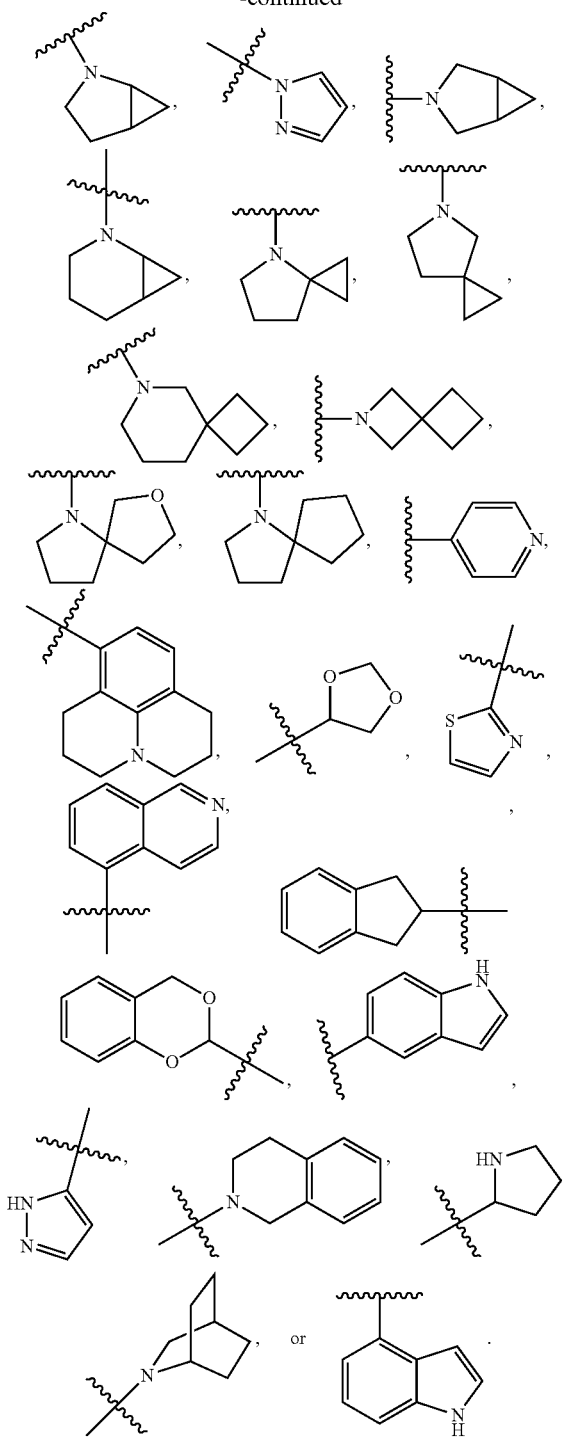

In some embodiments, Y is O. In some embodiments, Y is $CH_2$. In some embodiments, Y is $CH(C1-C6$ alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

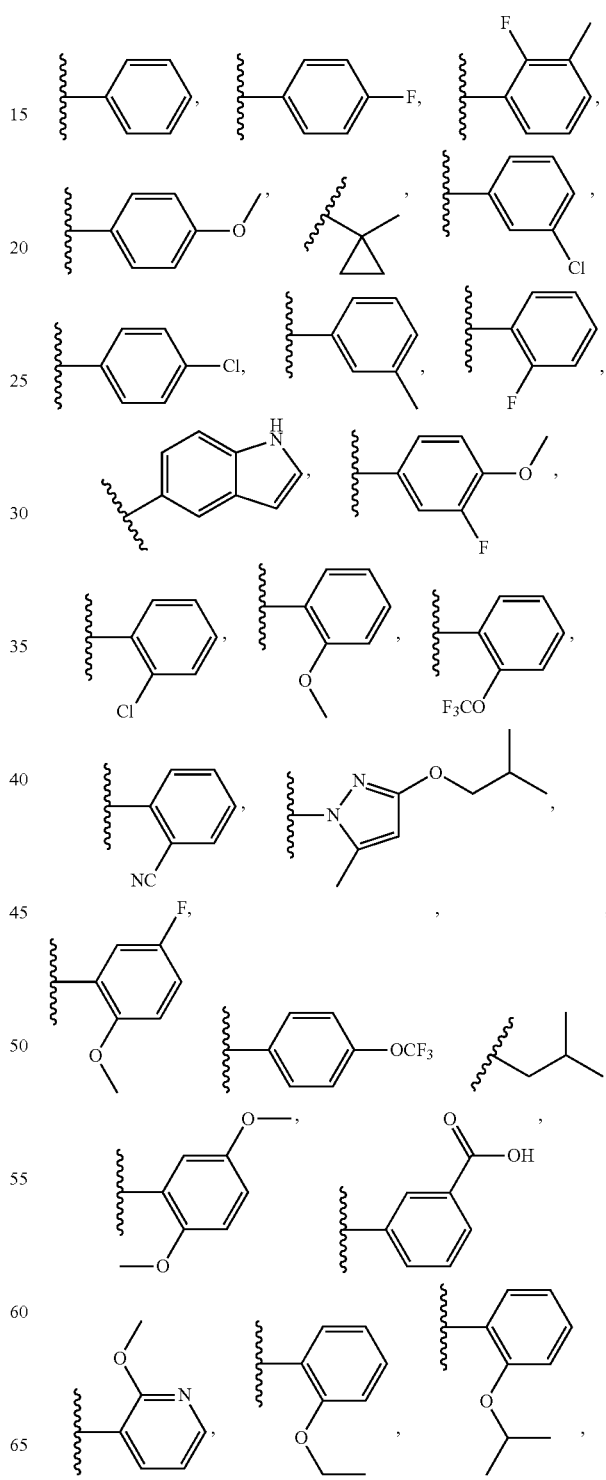

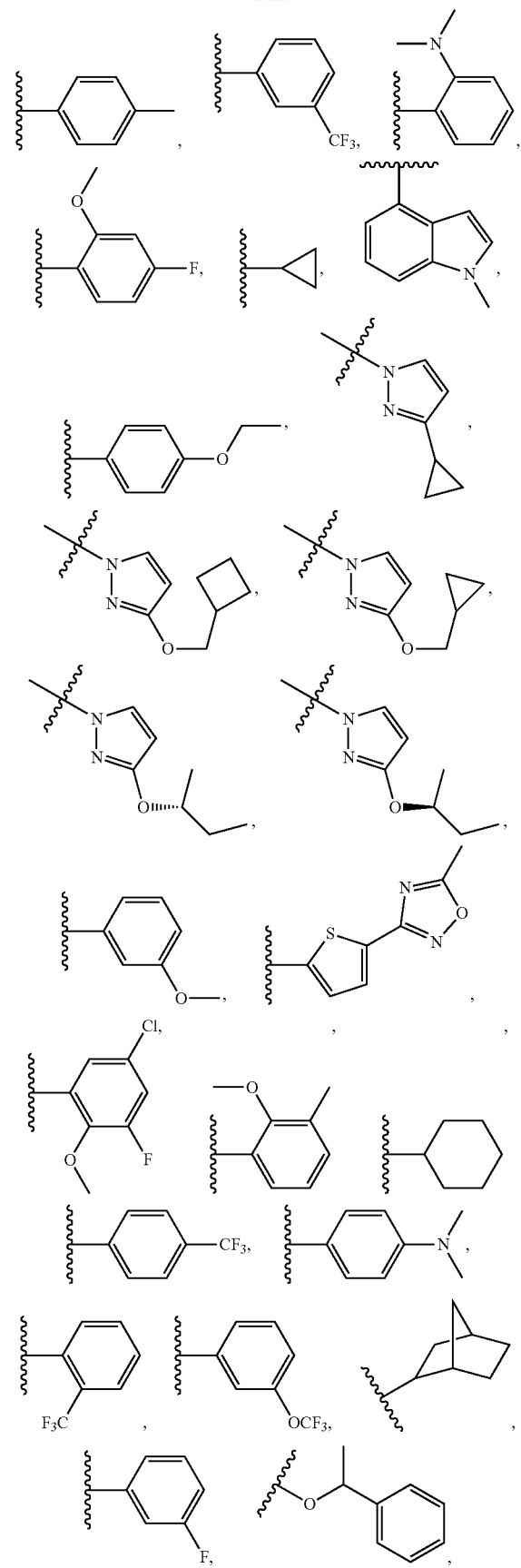
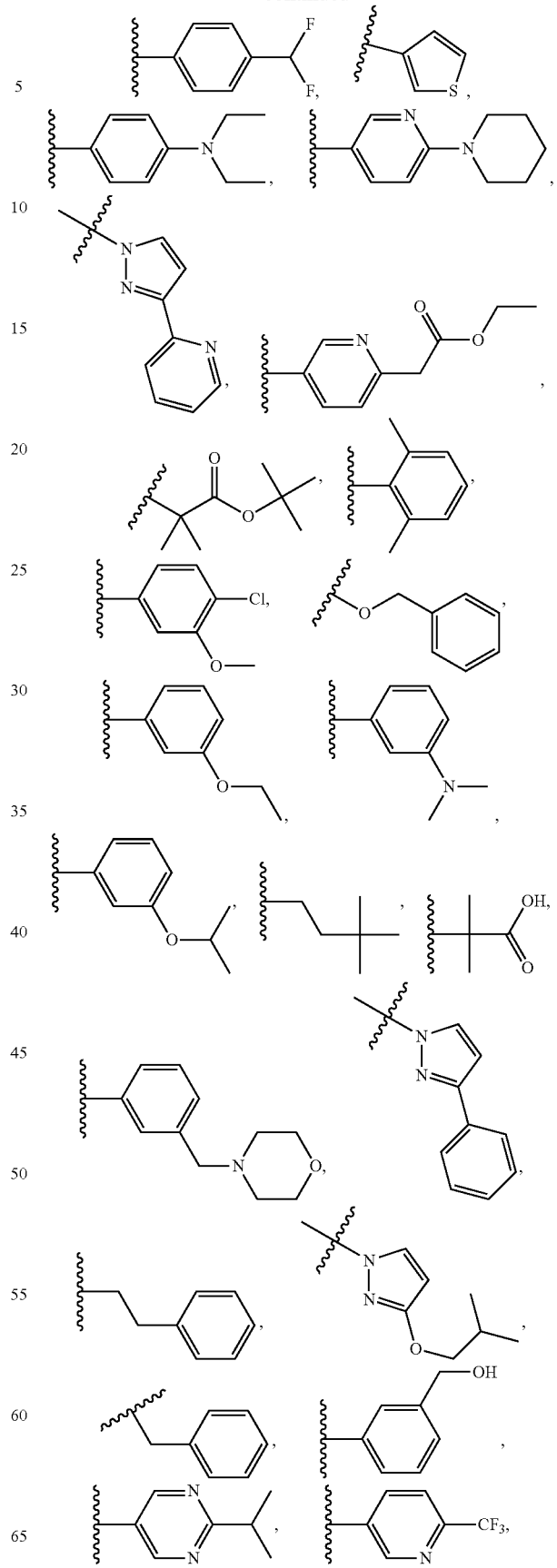

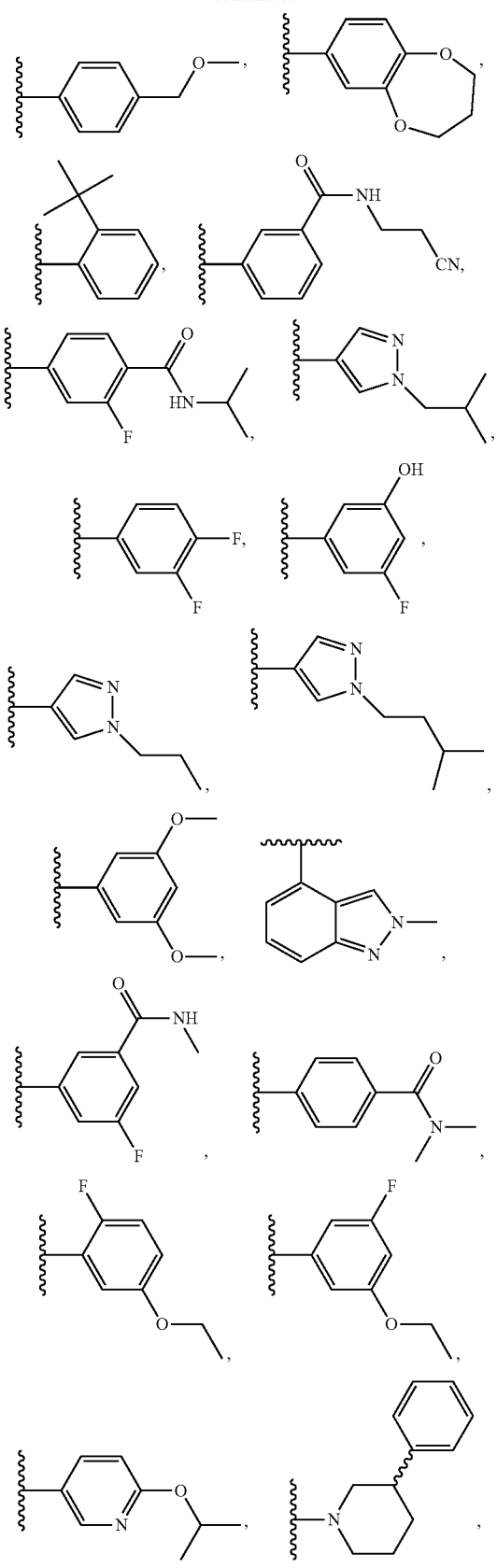
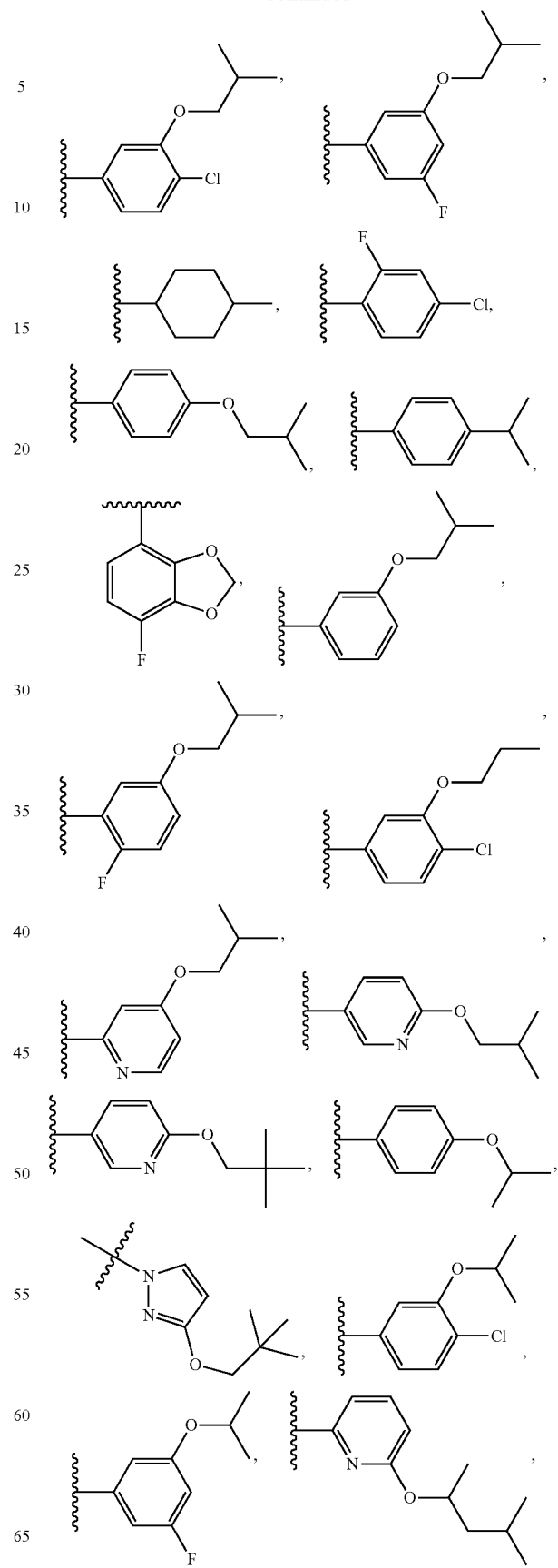

-continued

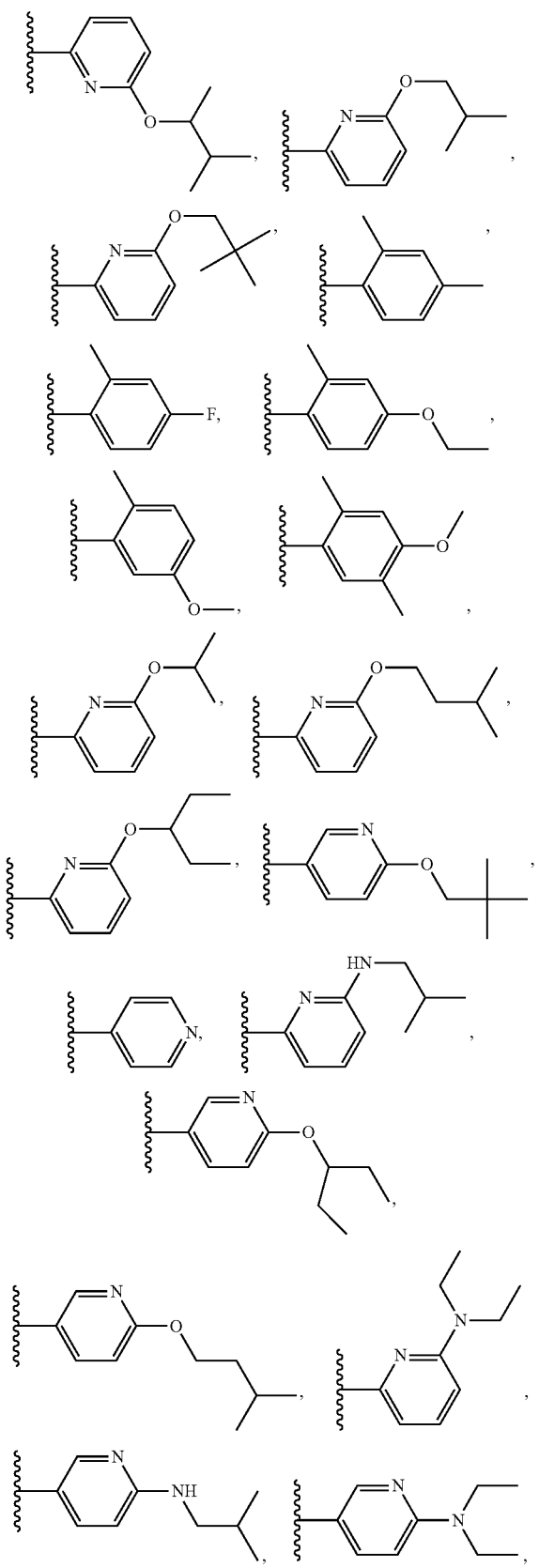

-continued

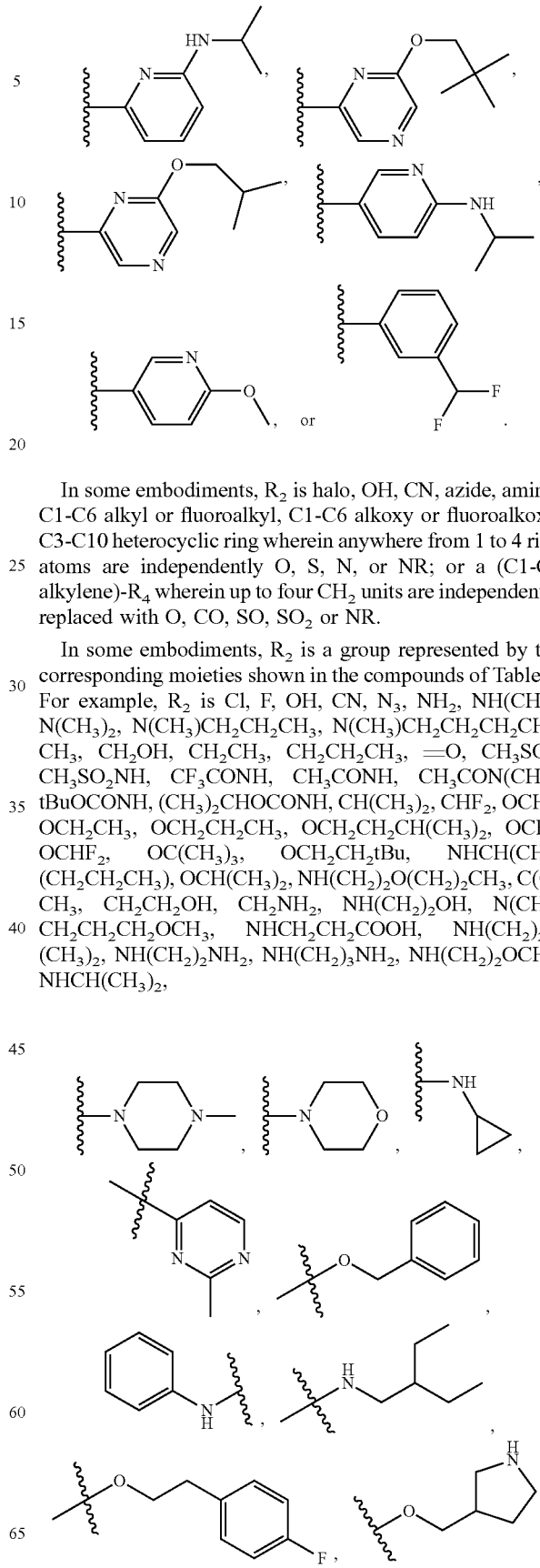

In some embodiments, R₂ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-R₄ wherein up to four CH₂ units are independently replaced with O, CO, SO, SO₂ or NR.

In some embodiments, R₂ is a group represented by the corresponding moieties shown in the compounds of Table 1. For example, R₂ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂, -continued

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₄₂, CO₂CH₃, —CH₂N(CH₃)₂, CO₂tBu, tBu, =CH₂, =O,

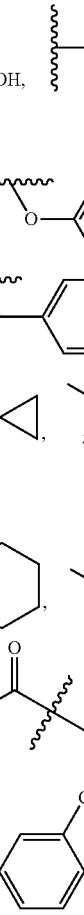

In some embodiments, o is 0. In some embodiments, o is 1. In some embodiments, o is 2.

In some embodiments, n is 0. In some embodiments, o is 1. In some embodiments, o is 2.

In some embodiments, p is 0. In some embodiments, p is 1. In some embodiments, p is 2.

In some embodiments, ring B is phenyl. In some embodiments, ring B is pyridyl. In some embodiments, ring C is phenyl. In some embodiments, ring B and ring C are phenyl. In some embodiments, ring B is pyridyl and ring C is phenyl. In some embodiments, Y is CH₂. In some embodiments, Y is O. In some embodiments, R₂ is amino. In some embodiments, R₂ is OH. In some embodiments, R₂ is OCH₃. In some embodiments, R₃ is CH₃. In some embodiments, R₂ is amino and R₃ is CH₃. In some embodiments, ring B is pyridyl, ring C is phenyl, and Y is CH₂. In some embodiments, ring B is pyridyl, ring C is phenyl, and Y is O.

In some embodiments, the invention features a compound of formula Id-i:

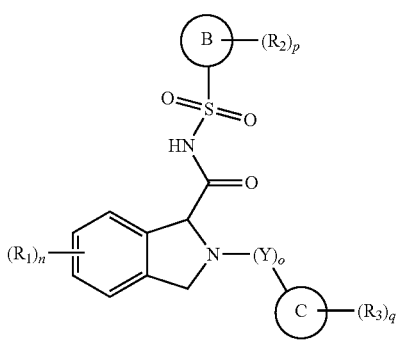

Id-i or a pharmaceutically acceptable salt thereof, wherein, independently for each occurrence:
Ring B is a C3-C10 heteroaryl ring wherein anywhere from 1 to 4 ring atoms are independently O, S, N, or NR;
Ring C is a C6-C10 aryl ring, C3-C14 heteroaryl or heterocyclic ring wherein anywhere from 1 to 4 ring atoms are independently N, O, or S, or a C3-C10 cycloalkyl ring;
Y is CRR, CO, O, S, SO, $SO_2$, S(O)NH or NR;
$R_1$ is halo; CN; $F_3S$; $SiR_3$; OH; NRR; C1-C6 alkyl or fluoroalkyl; C1-C6 alkoxy or fluoroalkoxy; C1-C6 alkenyl; C1-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;
$R_2$ is halo; OH; NRR; azide; CN; $CO_2R$; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_2$ groups taken together may form a =$CH_2$ or =O group;
$R_3$ is halo; CN; $CO_2R$; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR;
or two $R_3$ groups taken together may form a =$CH_2$ or =O group;
$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or $SO_2R$;
R is independently H; OH; $CO_2H$; $CO_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
n is 0, 1, 2 or 3;
o is 0, 1, 2, 3, 4, or 5;
p is 0, 1, 2, or 3; and
q is 0, 1, 2, 3, 4, or 5.

In some embodiments, the compound of formula Id-i exists as a pharmaceutically acceptable prodrug.

In some embodiments, ring B is pyridyl, pyridine-2 (1H)-one, pyrazole, indole, aza-indole, thiophene, dihydrobenzofuran, or quinoline.

In some embodiments, ring B is a group represented by the corresponding moieties shown in the compounds of Table 1. For example, ring B is

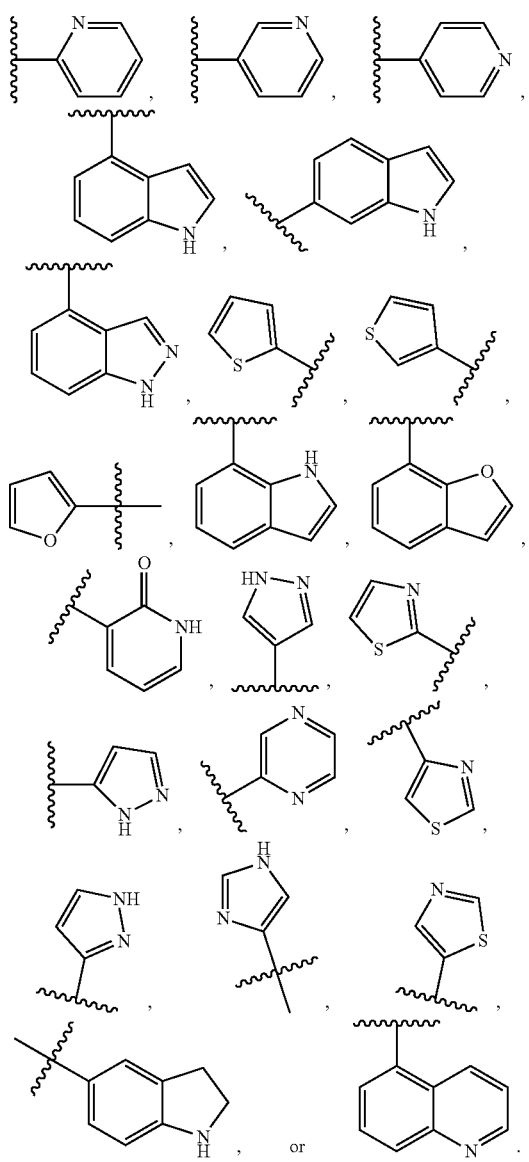

In some embodiments, ring C is phenyl, indole, cycloalkyl, pyridyl, pyrrolidine, naphthalene, or dihydroindene.

In some embodiments, ring C is a group represented by the corresponding moieties shown in the compounds of Table 1. For example, ring C is

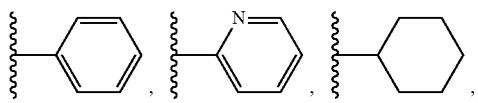

353
-continued
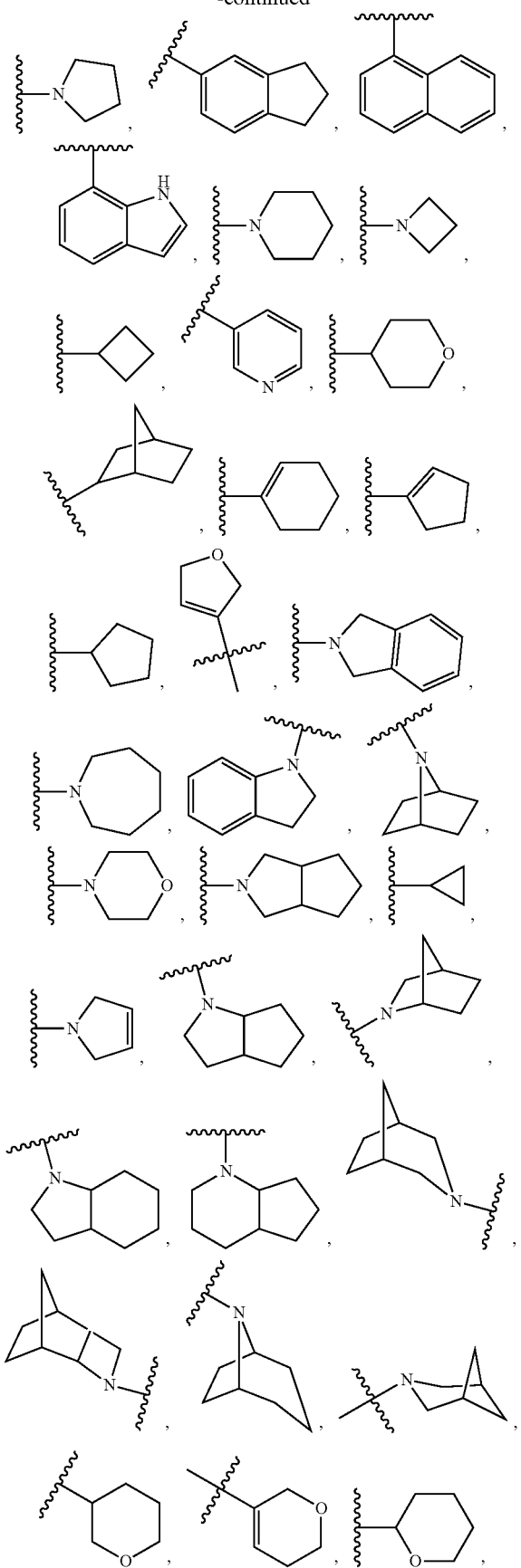
354
-continued
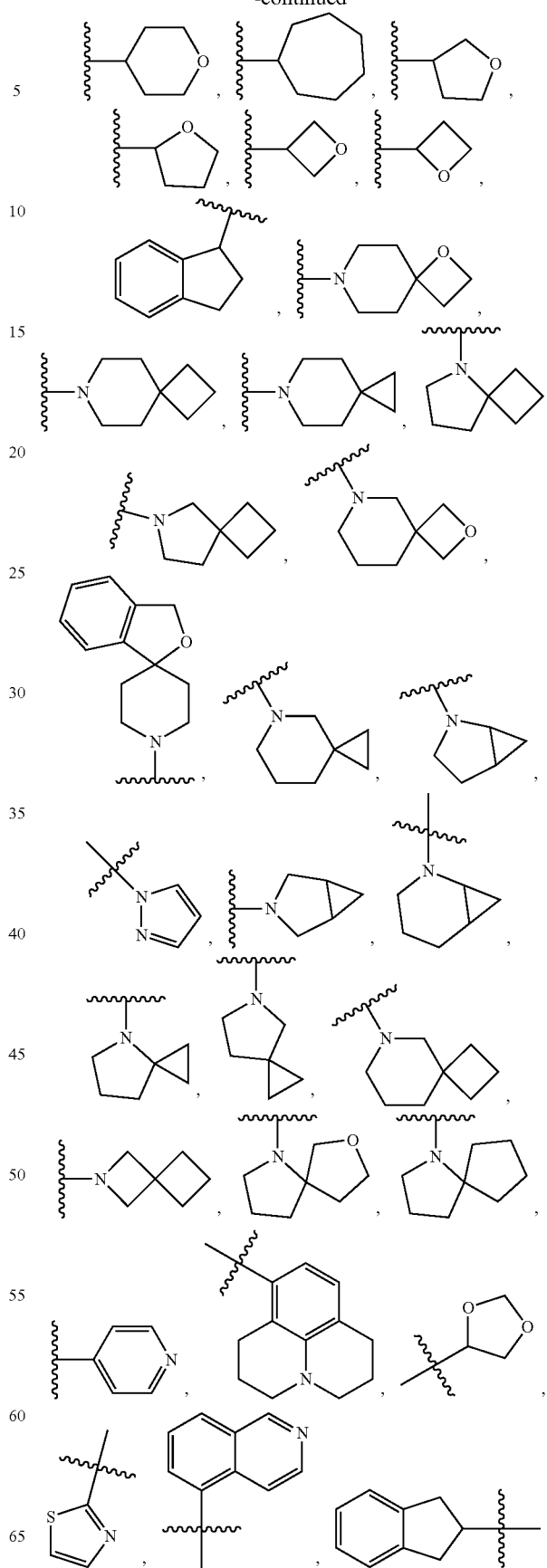

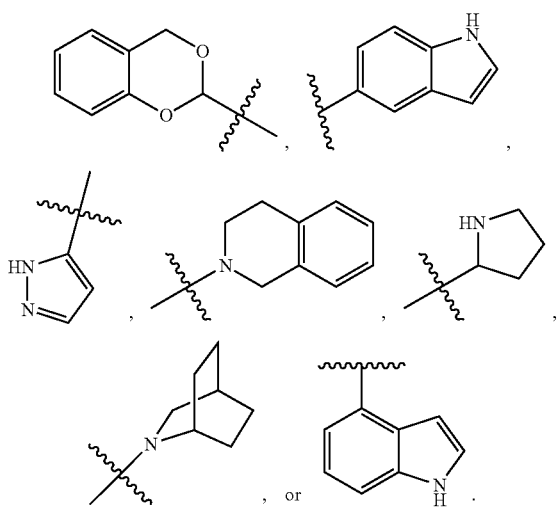

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2CH_2CH_3$,

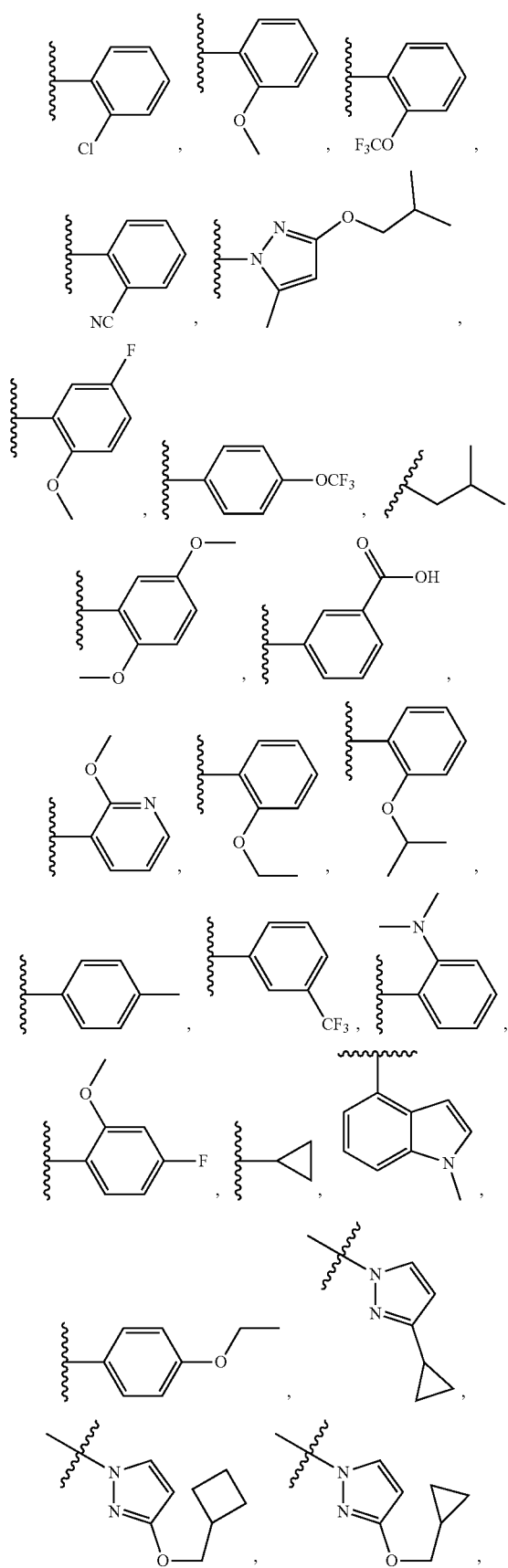

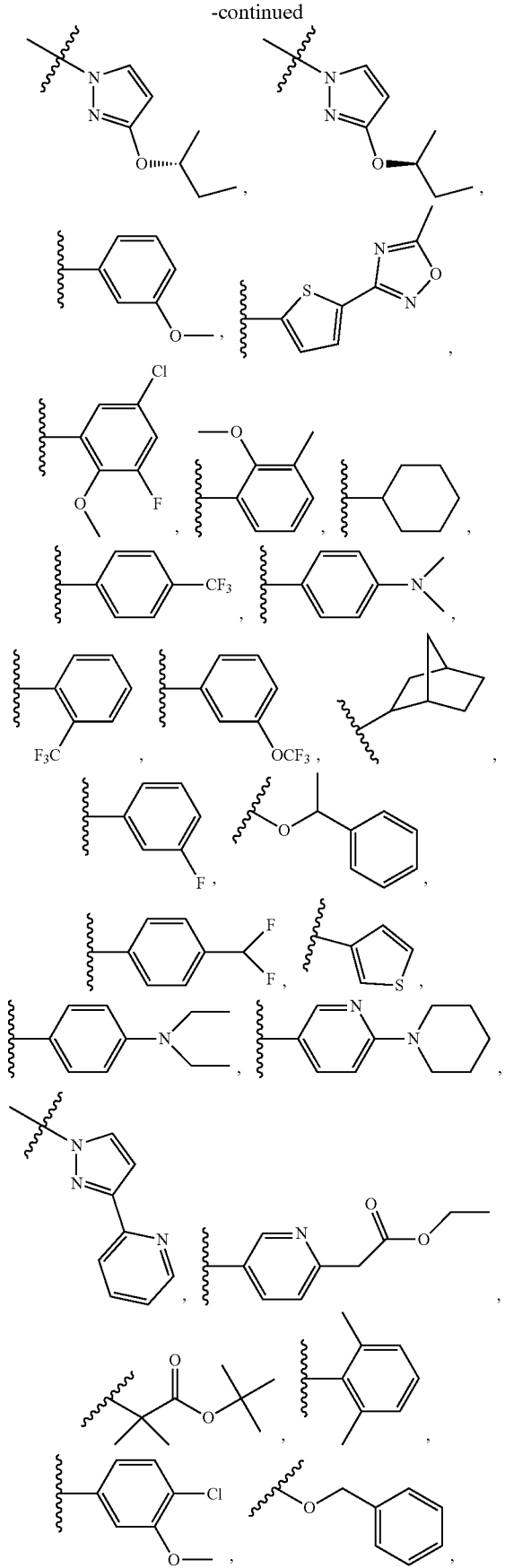
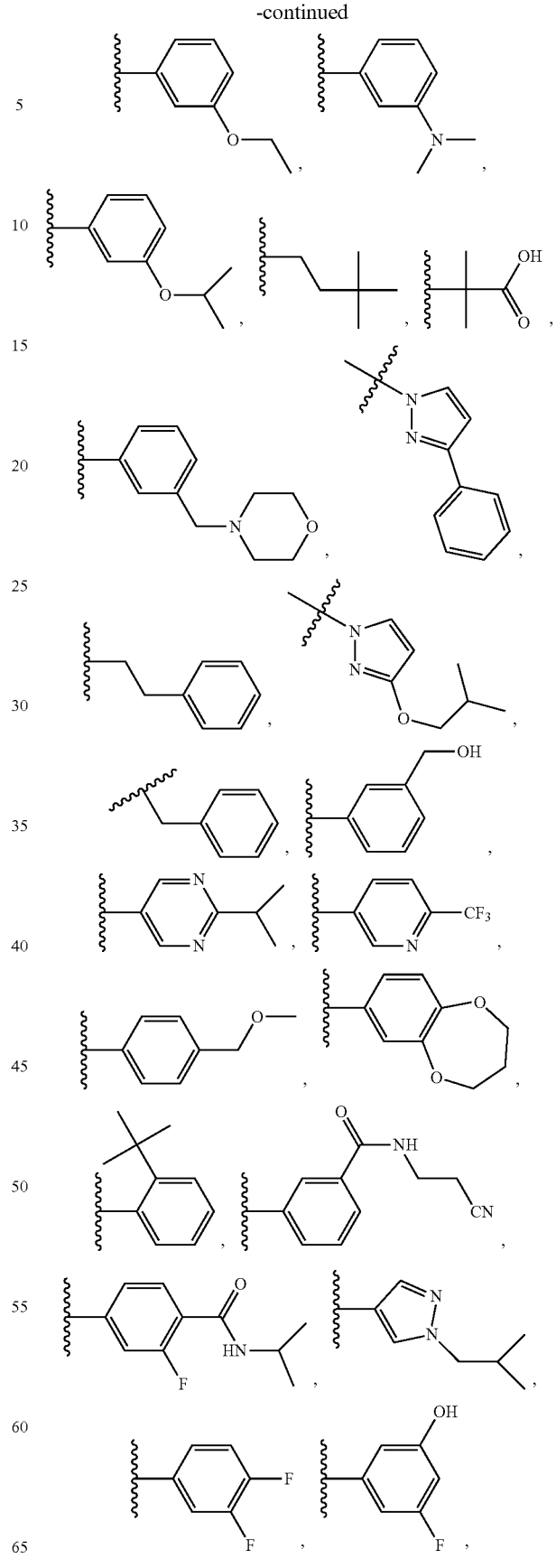

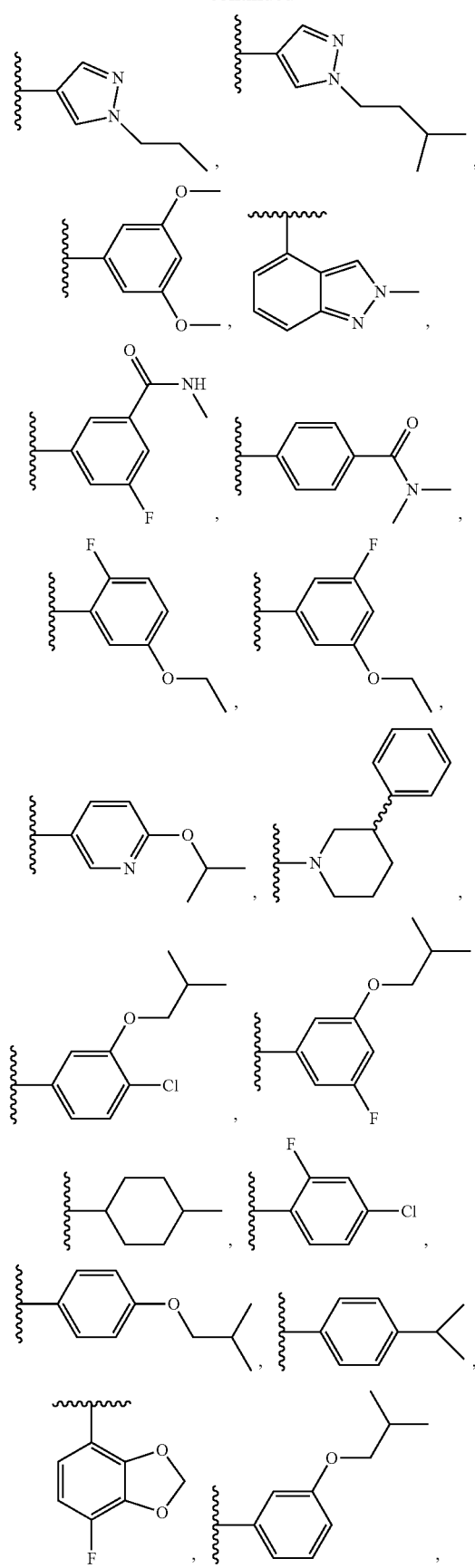
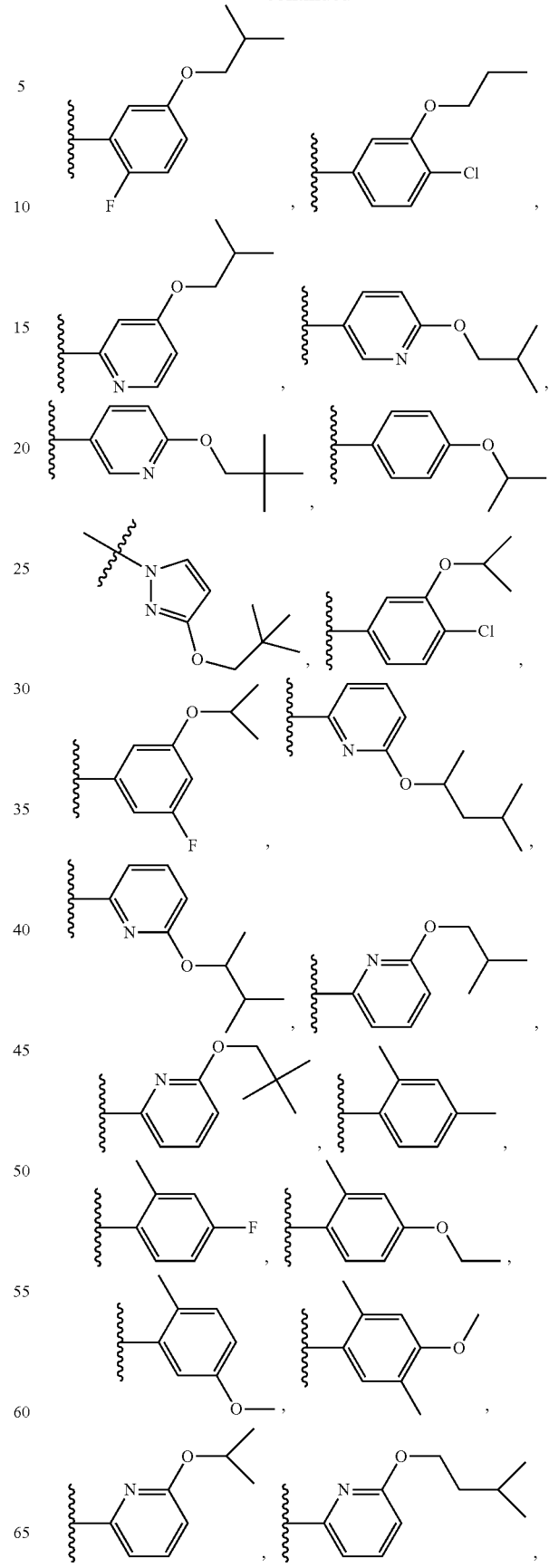

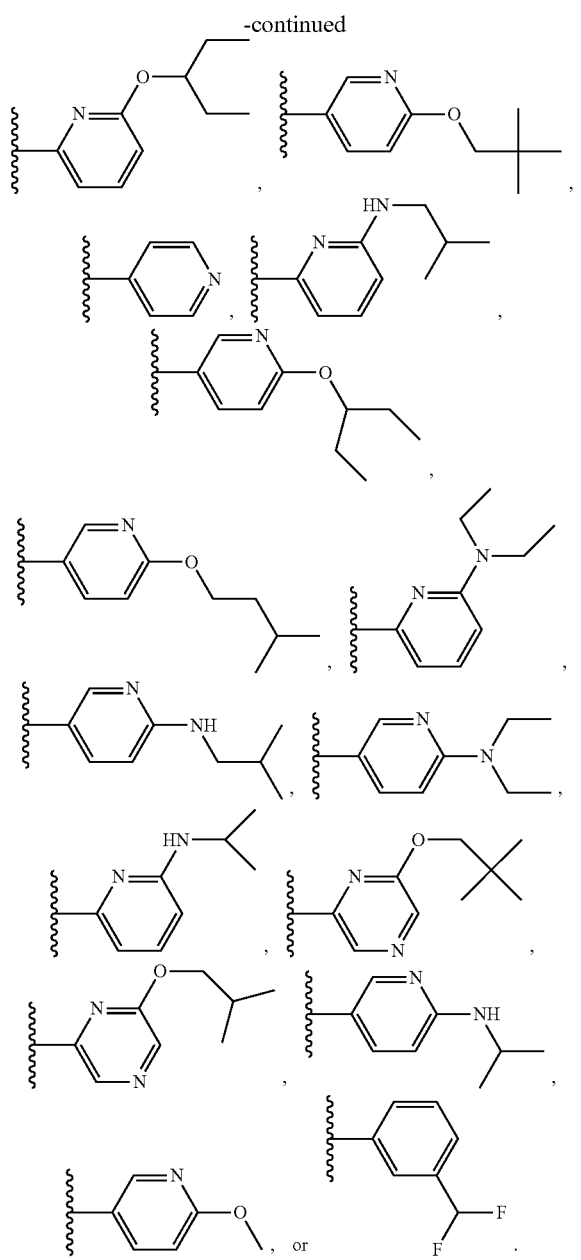

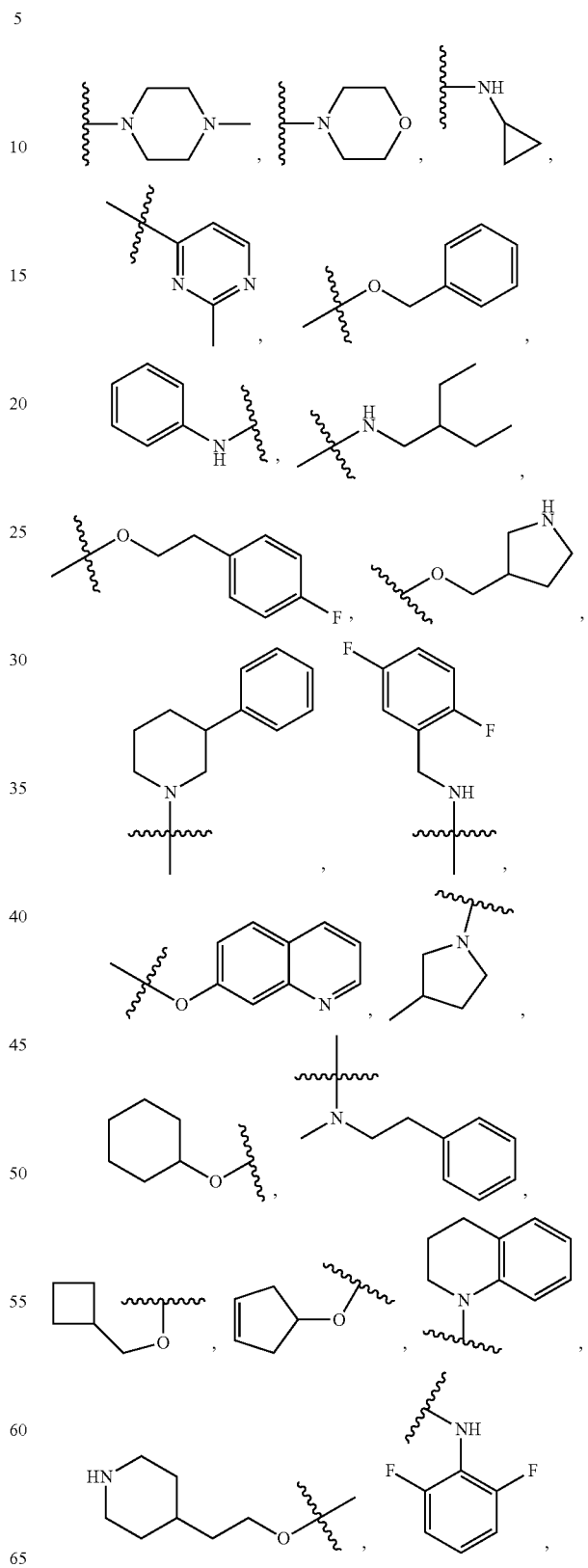

CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

In some embodiments, $R_2$ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-$R_4$ wherein up to four CH₂ units are independently replaced with O, CO, S, SO, SO₂ or NR.

In some embodiments, $R_2$ is a group represented by the corresponding moieties shown in the compounds of Table 1. For example, $R_2$ is Cl, F, OH, CN, N₃, NH₂, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)

-continued

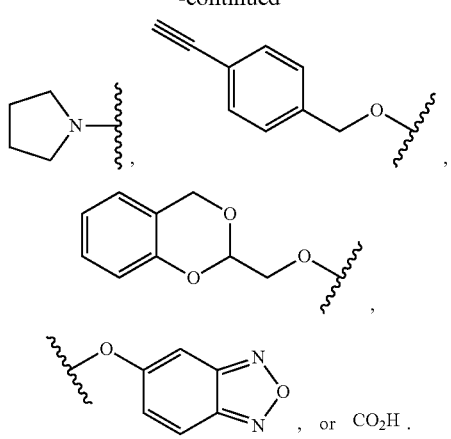

, or CO₂H .

In some embodiments, R₃ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, R₃ is a group represented by the corresponding moieties shown in the compounds of Table 1. For example, R₃ is Cl, I, deuterium, F, CN, CH₃, OH, OCH₃, CF₃, CH₂CH₃, CH₂CF₃, CH₂CH₂CH₃, OCH₂CH(CH₃)₂, OCH(CH₃)₂, CO₂H, CO₂NH₂, OCH₂CH₃, CH₂OCH₃, CH(CH₃)₂, CCH, CH₂CONH₂, CO₂CH₃, —CH₂N(CH₃)₂, CO₂tBu, tBu, =CH₂, =O,

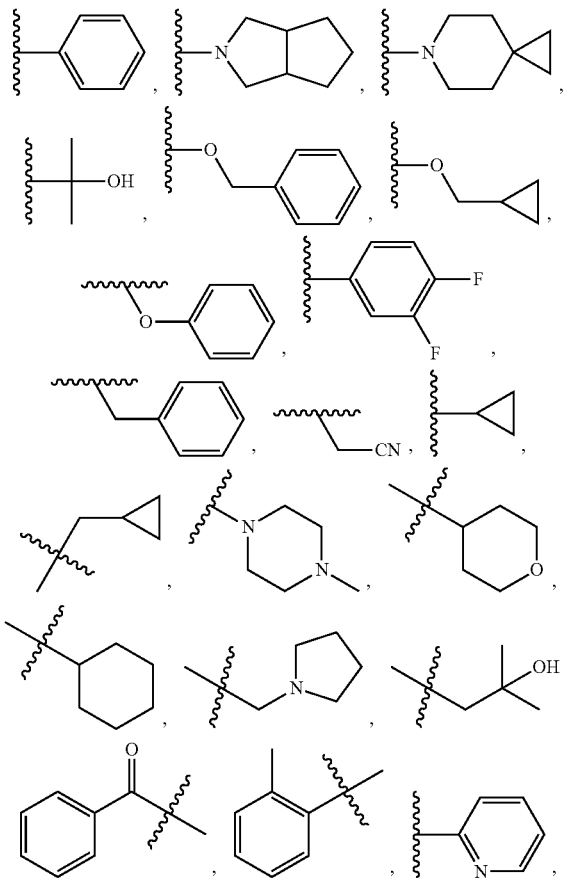

-continued

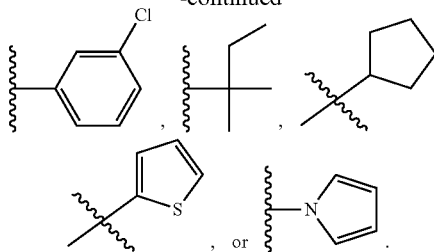

, or

In some embodiments, o is 0. In some embodiments, o is 1. In some embodiments, o is 2.
In some embodiments, n is 0. In some embodiments, o is 1. In some embodiments, o is 2.
In some embodiments, p is 0. In some embodiments, p is 1. In some embodiments, p is 2.
In some embodiments, the invention features a compound of formula Id-ii:

Id-ii

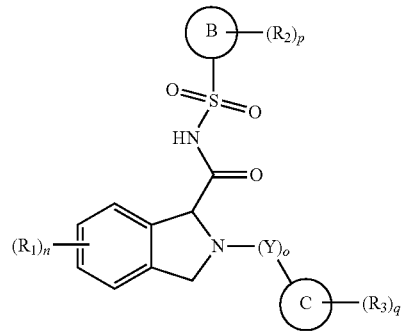

or a pharmaceutically acceptable salt thereof, wherein, independently for each occurrence:
Ring B is a C6-C10 aryl ring;
Ring C is a C6-C10 aryl ring, C3-C14 heteroaryl or heterocyclic ring wherein anywhere from 1 to 4 ring atoms are independently N, O, or S, or a C3-C10 cycloalkyl ring;
Y is CRR, CO, O, S, SO, SO₂, S(O)NH or NR;
R₁ is halo; CN; F5S; SiR₃; OH; NRR; C1-C6 alkyl or fluoroalkyl; C1-C6 alkoxy or fluoroalkoxy; C1-C6 alkenyl; C1-C6 alkynyl; (C1-C9 alkylene)-R₄ wherein up to four CH₂ units are independently replaced with O, CO, S, SO, SO₂ or NR; C6-C10 aryl; C3-C10 heteroaryl or heterocyclic ring wherein anywhere from 1 to 4 ring atoms are independently O, S, N, or NR; or C3-C10 cycloalkyl;
R₂ is halo; OH; NRR; azide; CN; CO₂R; C1-C6 alkyl or fluoroalkyl; C1-C6 alkoxy or fluoroalkoxy; C1-C6 alkenyl; C1-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-R₄ wherein up to four CH₂ units are independently replaced with O, CO, S, SO, SO₂ or NR;
or two R₂ groups taken together may form a =CH₂ or =O group;
R₃ is halo; CN; CO₂R; C1-C6 alkyl or fluoroalkyl; C1-C6 alkenyl; C1-C6 alkynyl; C1-C6 alkoxy or fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-R$_4$ wherein up to four CH$_2$ units are independently replaced with O, CO, S, SO, SO$_2$ or NR; or two R$_3$ groups taken together may form a =CH$_2$ or =O group;

R$_4$ is H; azide; CF$_3$; CHF$_2$; OR; CCH; CO$_2$R; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, halo, or SO$_2$R;

R is independently H; OH; CO$_2$H; CO$_2$C1-C6 alkyl; C1-C6 alkyl; C1-C6 alkenyl; C1-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;

n is 0, 1, 2 or 3;
o is 0, 1, 2, 3, 4, or 5;
p is 0, 1, 2, or 3; and
q is 0, 1, 2, 3, 4, or 5.

In some embodiments, the compound of formula Id-ii exists as a pharmaceutically acceptable prodrug.

In some embodiments, ring B is phenyl or napthalene.

In some embodiments, ring C is phenyl, indole, cycloalkyl, pyridyl, pyrrolidine, naphthalene, or dihydroindene.

In some embodiments, ring C is is a group represented by the corresponding moieties shown in the compounds of Table 1. For example, ring C is

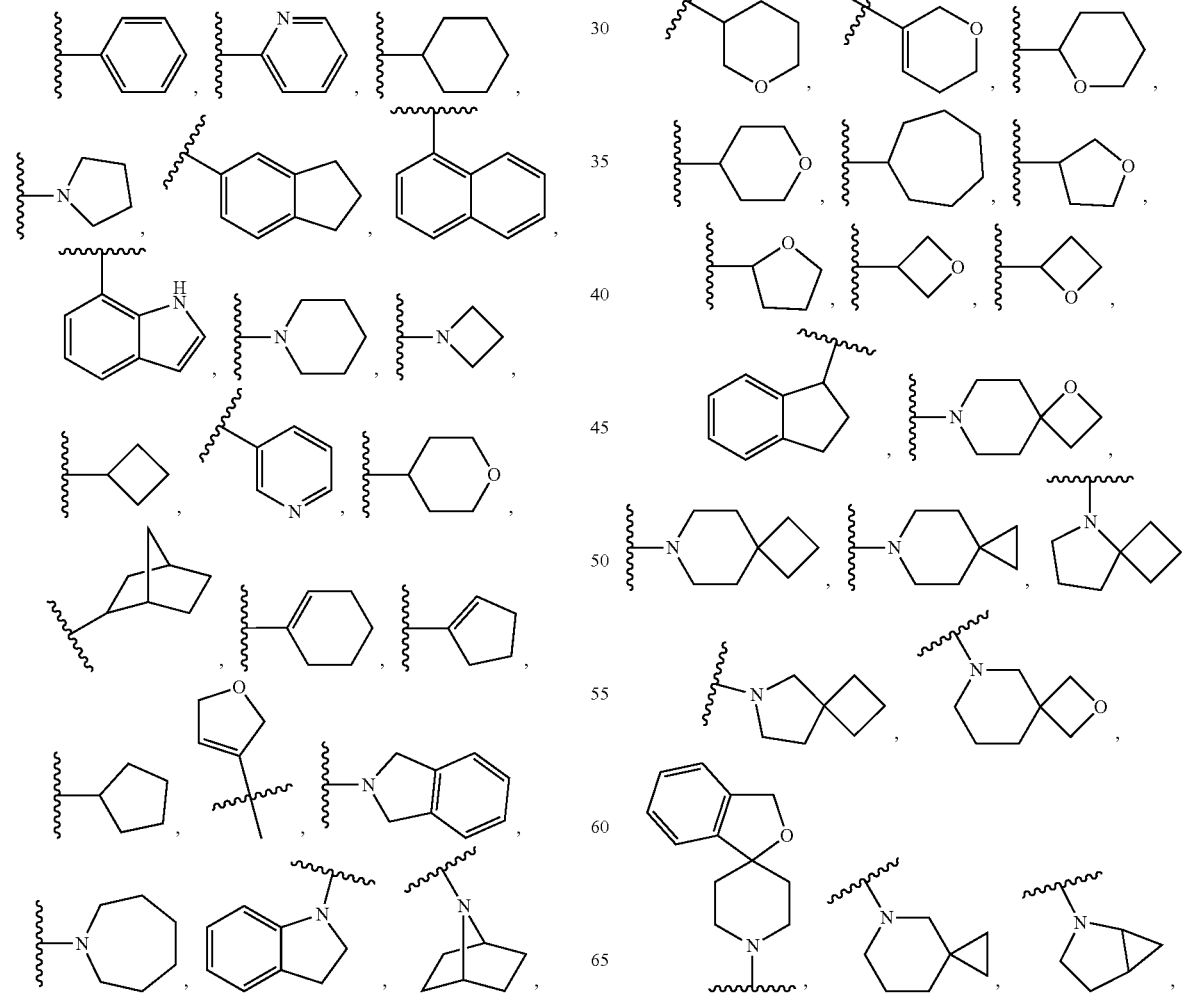

-continued

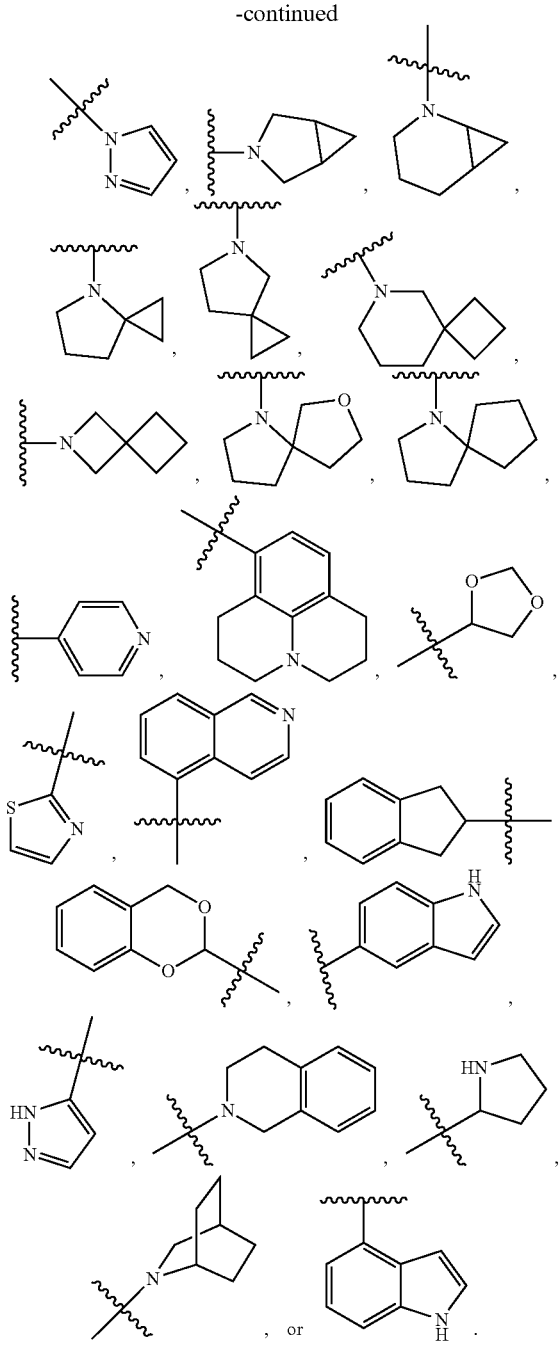

In some embodiments, Y is O. In some embodiments, Y is $CH_2$. In some embodiments, Y is CH(C1-C6 alkyl). In some embodiments, Y is $CH(CH_3)$. In some embodiments, Y is $CH(CH_2CH_3)$. In some embodiments, Y is NR, such as NH, N(C1-C6alkynyl), or N(C1-C6 alkyl).

In some embodiments, $R_1$ is halo, CN, C1-C6 alkyl, C1-C6 alkoxy, C3-C8 cycloalkyl, or a phenyl, pyridyl, pyrimidine, indole, aza-indole, pyrazole, or thiophene ring, or a (C1-C9 alkylene)-$R_4$ wherein up to four $CH_2$ units are independently replaced with O, CO, S, SO, $SO_2$ or NR, wherein all rings are optionally substituted with one or more groups selected from halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, and C3-C10 heterocycloalkyl.

In some embodiments, $R_1$ is is a group represented by the corresponding moieties shown in the compounds of Table 1. For example, $R_1$ is $CH_3$, Cl, F, CN, $OCH_3$, $CF_3$, $CH_2CH_3$, tBu, $CH(CH_3)_2$, $OCH_2CH_2OCH_2CH_3$,

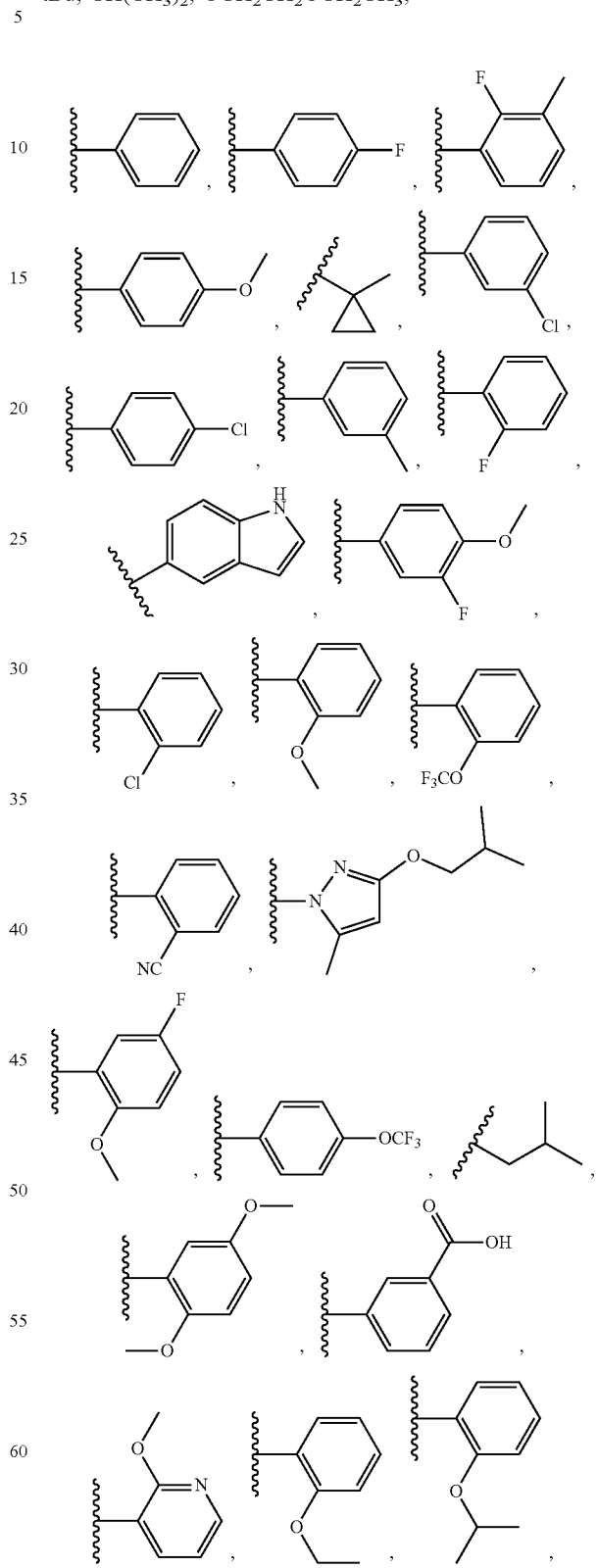

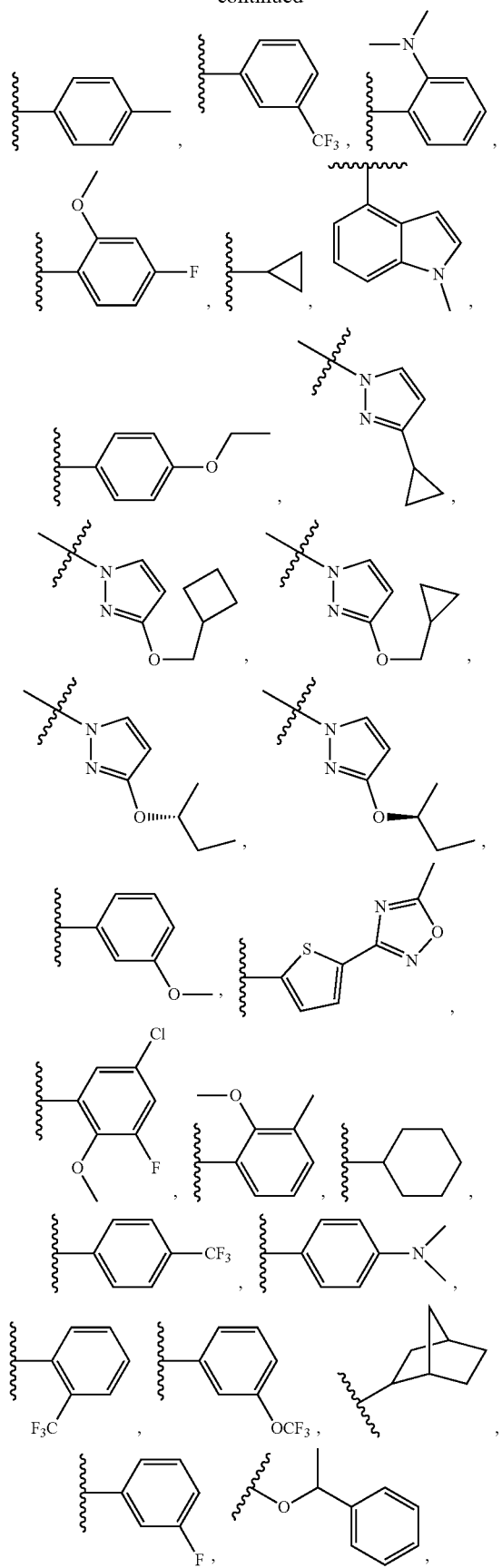
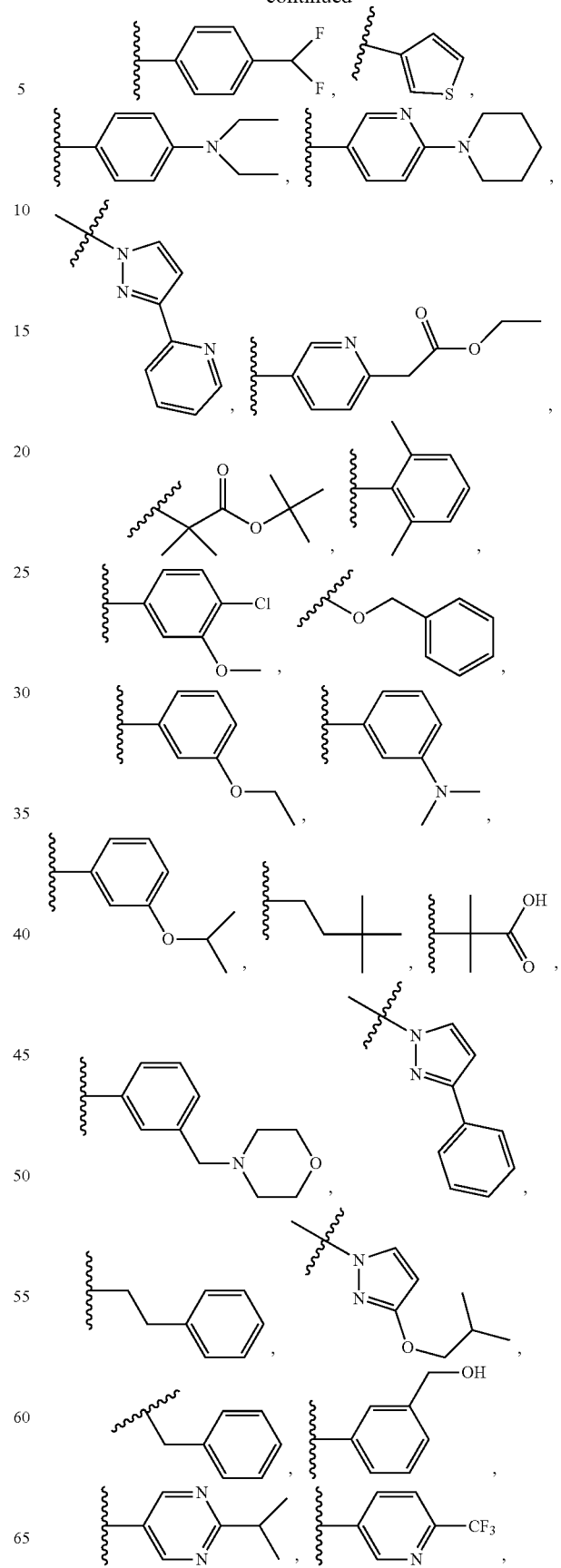

371
-continued
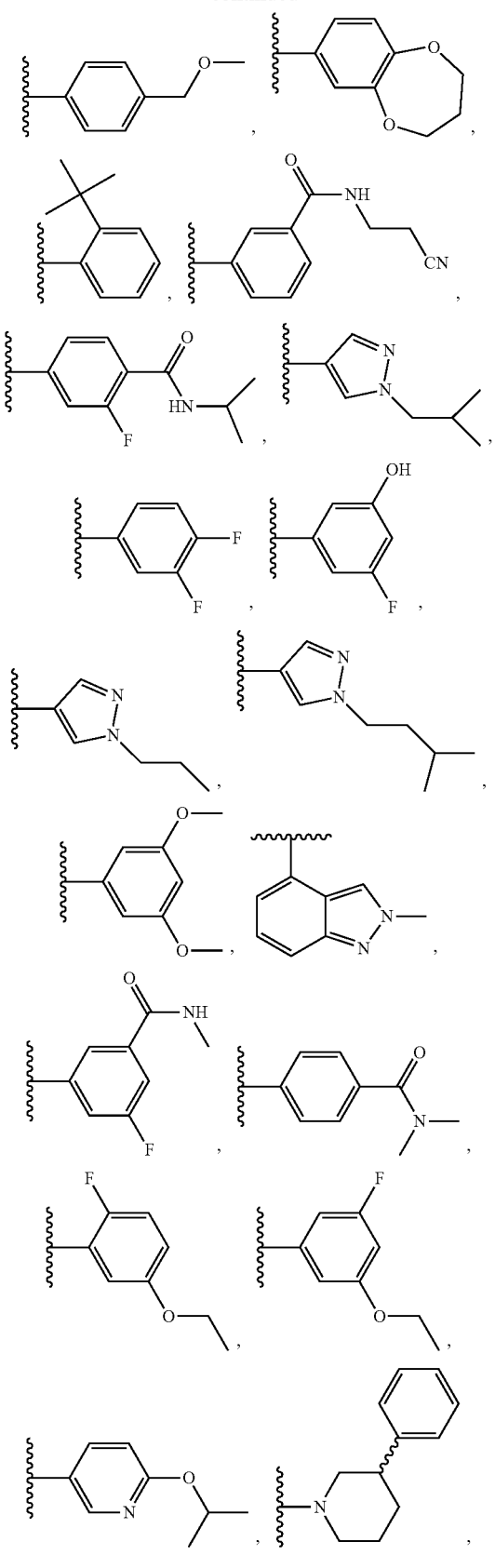
372
-continued
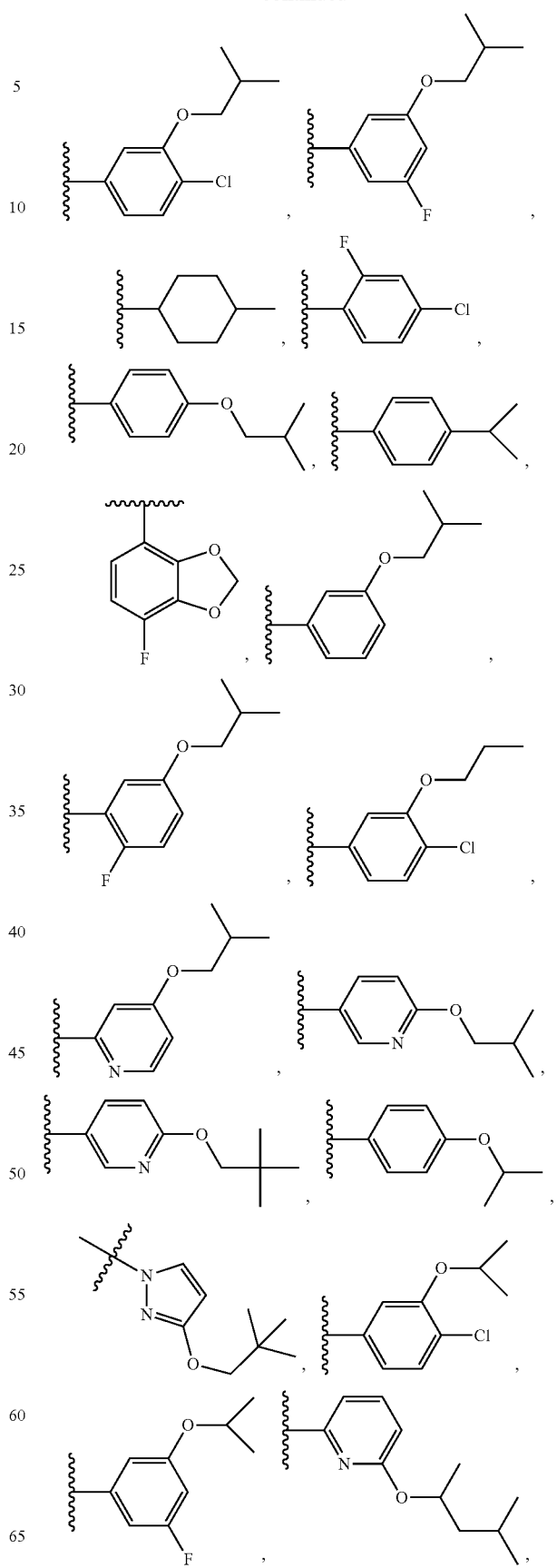

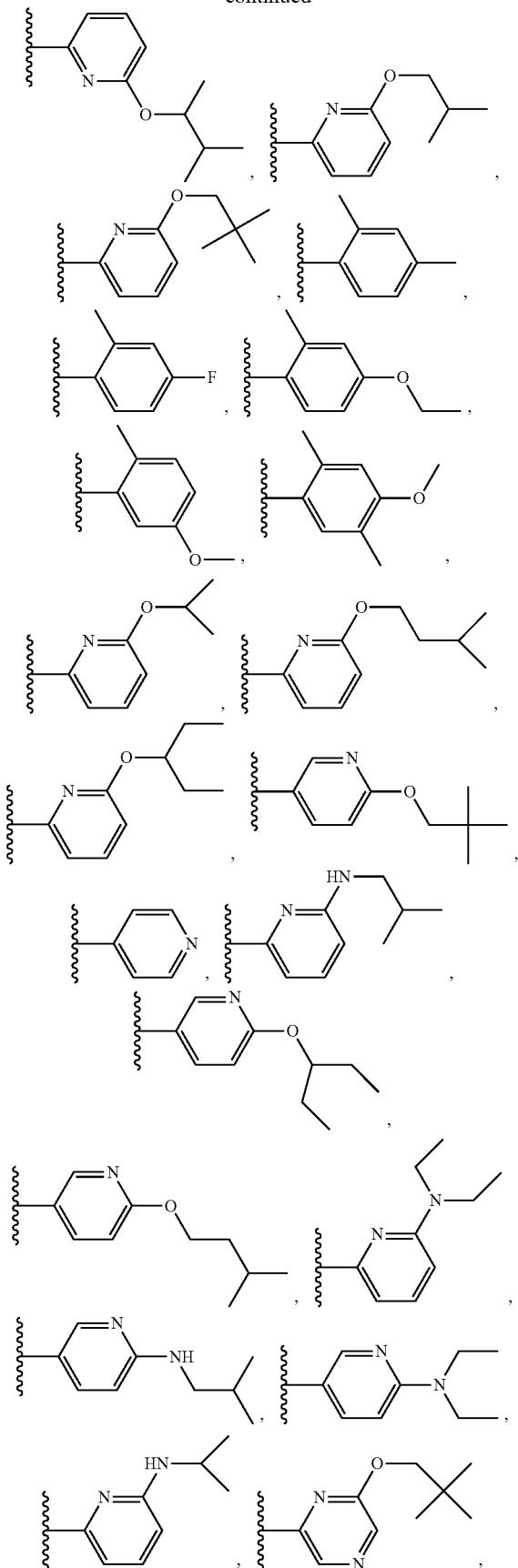

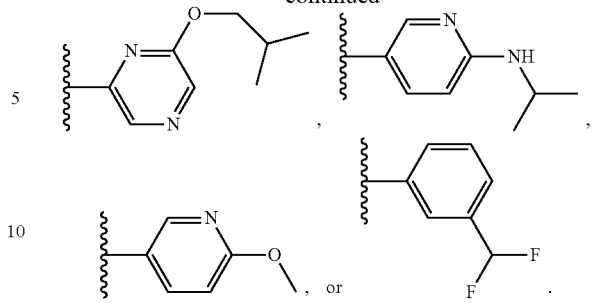

In some embodiments, R₂ is halo, OH, CN, azide, amino, C1-C6 alkyl or fluoroalkyl, C1-C6 alkoxy or fluoroalkoxy, C3-C10 heterocyclic ring wherein anywhere from 1 to 4 ring atoms are independently O, S, N, or NR; or a (C1-C9 alkylene)-R₄ wherein up to four CH₂ units are independently replaced with O, CO, S, SO, SO₂ or NR.

In some embodiments, R₂ is a group represented by the corresponding moieties shown in the compounds of Table 1. For example, R₂ is Cl, F, OH, CN, N₃, NH, NH(CH₃), N(CH₃)₂, N(CH₃)CH₂CH₂CH₃, N(CH₃)CH₂CH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃) (CH₂CH₂CH₃), OCH(CH₃)₂, NH(CH₂)₂O(CH₂)₂CH₃, C(O) CH₃, CH₂CH₂OH, CH₂NH₂, NH(CH₂)₂OH, N(CH₃) CH₂CH₂CH₂OCH₃, NHCH₂CH₂COOH, NH(CH₂)₂N (CH₃)₂, NH(CH₂)₂NH₂, NH(CH₂)₃NH₂, NH(CH₂)₂OCH₃, NHCH(CH₃)₂,

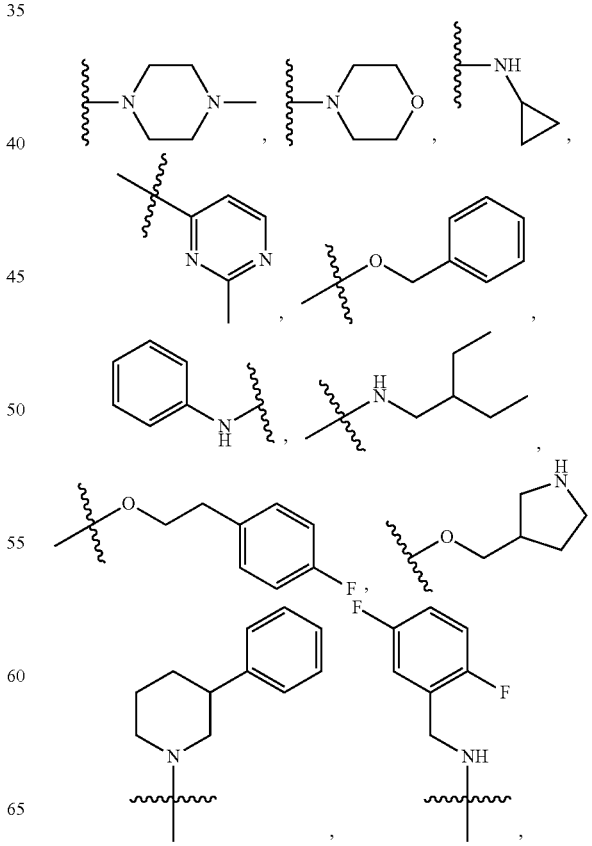

-continued

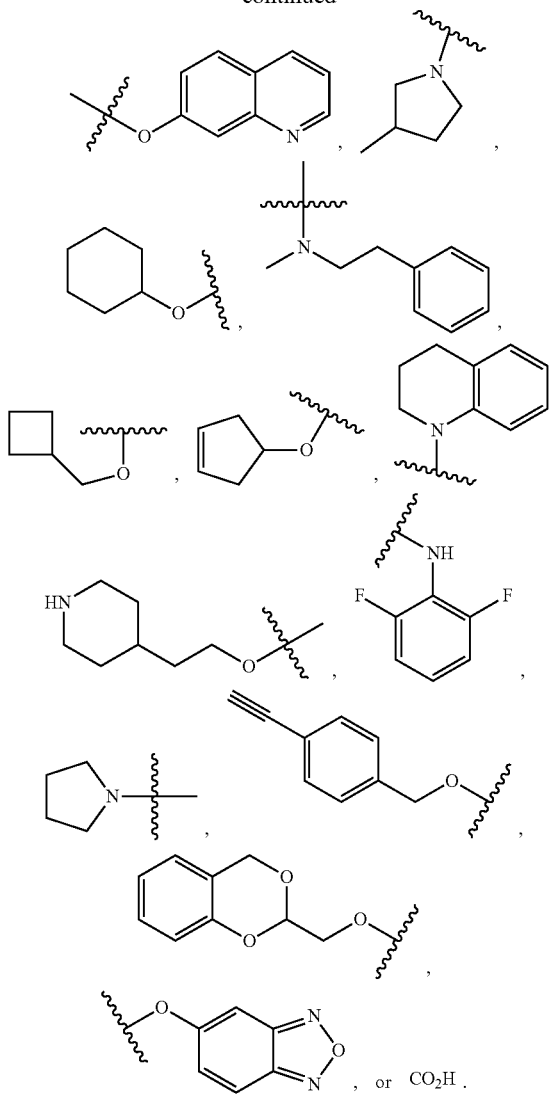

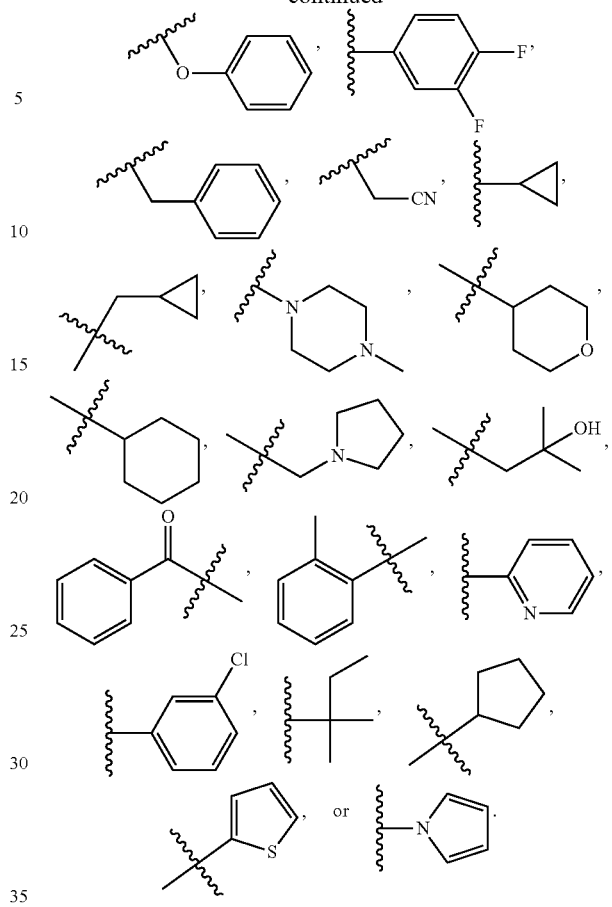

In some embodiments, o is 0. In some embodiments, o is 1. In some embodiments, o is 2.

In some embodiments, n is 0. In some embodiments, o is 1. In some embodiments, o is 2.

In some embodiments, p is 0. In some embodiments, p is 1. In some embodiments, p is 2.

In another embodiment, the present invention provides compounds of formulas I to Id-ii that contain isotope-labelled forms thereof. An isotope-labelled form of a compound of formulas I to Id-ii is identical to this compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound of formulas I to Id-ii by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of formulas I to Id-ii, a prodrug thereof, or a pharmaceutically acceptable salt of either which contains one or more of the above-mentioned isotopes and/or other iso-topes of other atoms is intended to be part of the present invention. An isotope-labelled compound of formulas I to In-i can be used in a number of beneficial ways. For example, an isotope-labelled compound of formula I to In-i into which, for example, a radioisotope, such as $^{3}H$ or $^{14}C$, has been incorporated is suitable for medicament and/or substrate tissue distribution assays. These radioisotopes, i.e.

In some embodiments, $R_3$ is halo, CN, C1-C6 alkyl or fluoroalkyl, C1-C6 alkoxy, or C3-C10 heteroaryl wherein anywhere from 1 to 4 ring atoms are independently O, S, N, or NR.

In some embodiments, $R_3$ is a group represented by the corresponding moieties shown in the compounds of Table 1. For example, $R_3$ is Cl, I, deuterium, F, CN, $CH_3$, OH, $OCH_3$, $CF_3$, $CH_2CH_3$, $CH_2CF_3$, $CH_2CH_2CH_3$, $OCH_2CH(CH_3)_2$, $OCH(CH_3)_2$, $CO_2H$, $CO_2NH_2$, $OCH_2CH_3$, $CH_2OCH_3$, $CH(CH_3)_2$, CCH, $CH_2CONH_2$, $CO_2CH_3$, —$CH_2N(CH_3)_2$, $CO_2tBu$, tBu, =$CH_2$, =O,

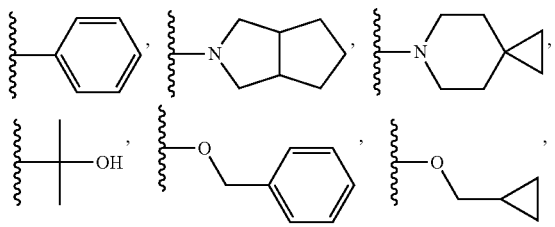

tritium ($^3$H) and carbon-14 ($^{14}$C), are particularly preferred owing to simple preparation and excellent detectability. Incorporation of heavier isotopes, for example deuterium ($^2$H), into a compound of formulas I to Id-ii has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of formulas I to Id-ii can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2$H) can also be incorporated into a compound of formulas I to Id-ii for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of formulas I to Id-ii that is susceptible to oxidation, the profile of this compound in vivo can be drastically modified and result in improved pharmacokinetic properties. For a further discussion, see S. L. Harbeson and R. D. Tung, *Deuterium In Drug Discovery and Development*, Ann. Rep. Med. Chem. 2011, 46, 403-417, incorporated in its entirety herein by reference.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of formulas I to Id-ii with improved stability through resistance to such oxidative metabolism. Significant improvements in the pharmacokinetic profiles of compounds of formulas I to Id-ii are thereby obtained, and can be expressed quantitatively in terms of increases in the in vivo half-life (ti/2), concentration at maximum therapeutic effect (Cmax), area under the dose response curve (AUC), and bioavailability; and in terms of reduced clearance, dose and materials costs.

The following is intended to illustrate the above: a compound of formulas I to Id-ii which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of formulas I to Id-ii can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33 (10) 2927-2937, 1994, and Jarman et al. Carcinogenesis 16(4), 683-688, 1993.

In some embodiments, the compound of formula I is selected from Table 1:

TABLE 1

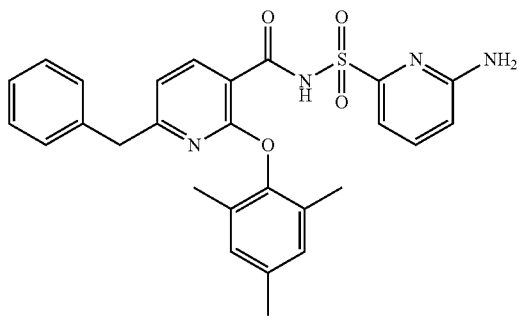

1

TABLE 1-continued
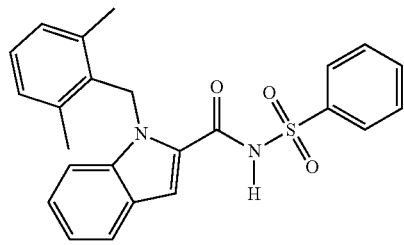 [SMILES: Cc1cccc(C)c1Cn1c(C(=O)NS(=O)(=O)c2ccccc2)cc2ccccc21]
2
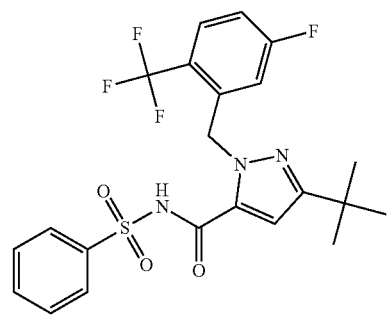
3
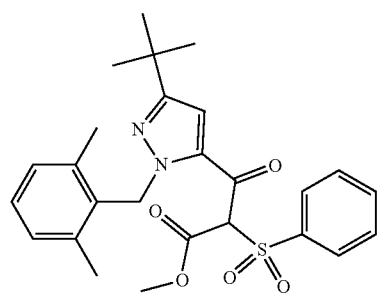 [SMILES: COC(=O)C(C(=O)c1cc(C(C)(C)C)nn1Cc1c(C)cccc1C)S(=O)(=O)c1ccccc1]
4
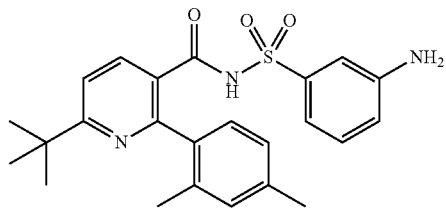
5
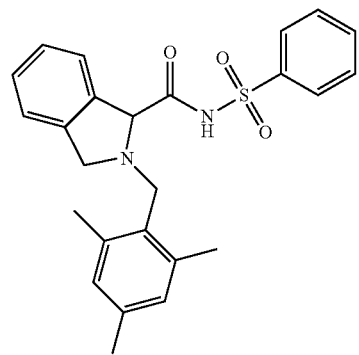
6

TABLE 1-continued
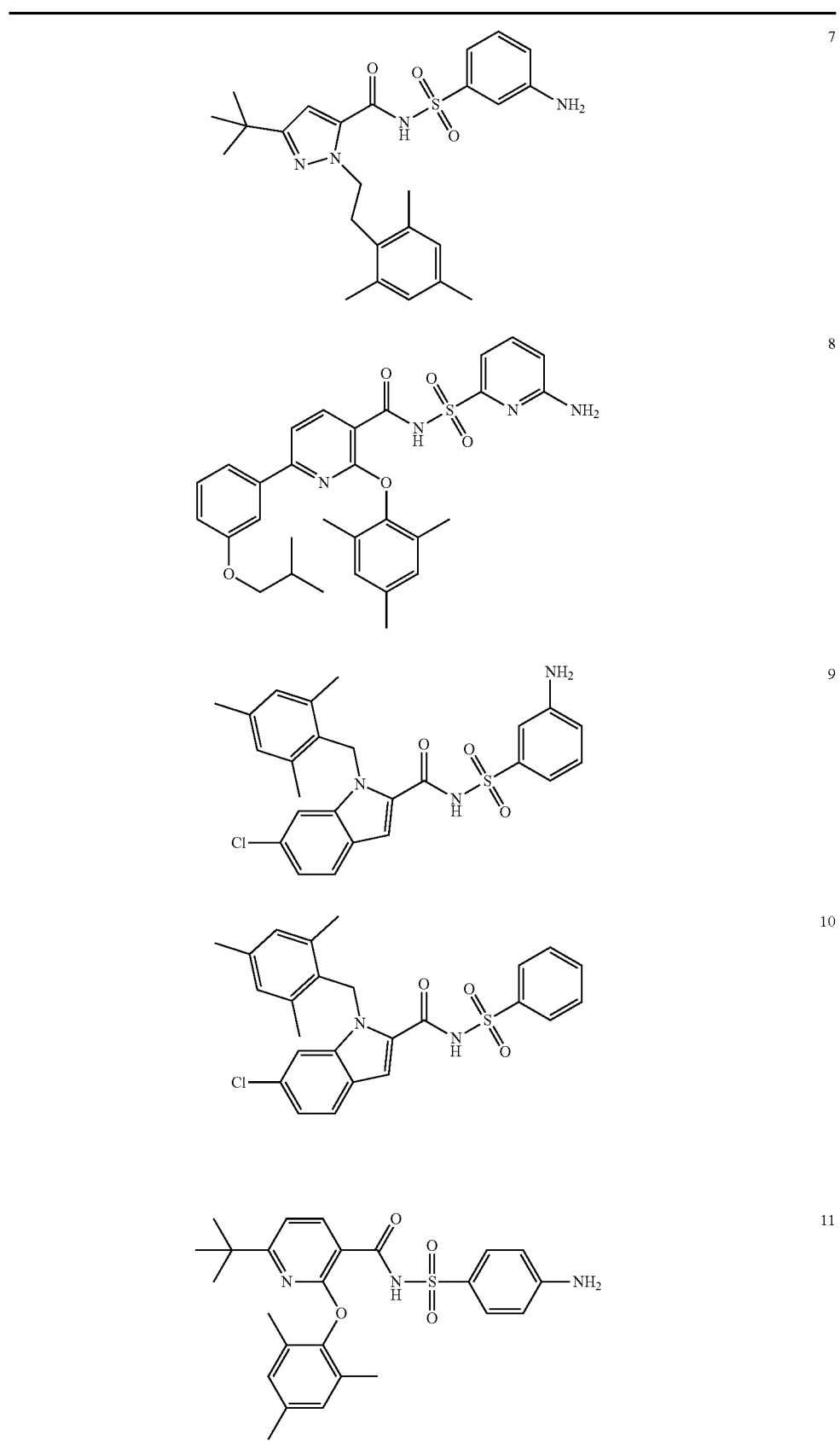

TABLE 1-continued
| | |
|---|---|
| 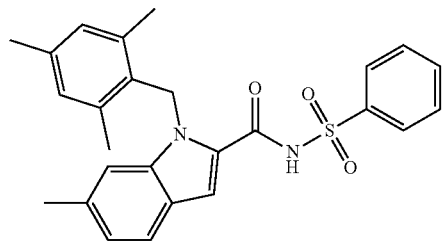 | 12 |
| 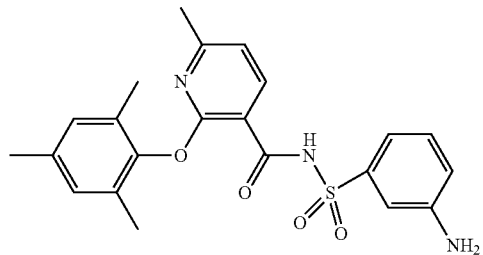 | 13 |
| 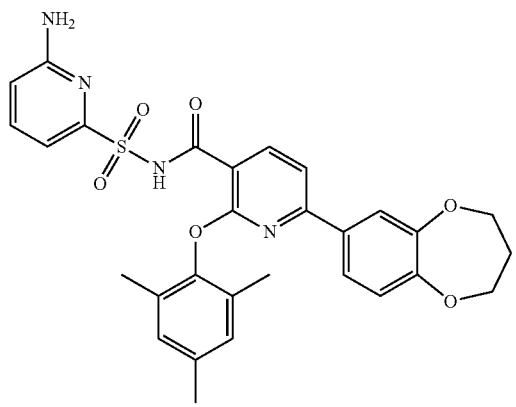 | 14 |
| 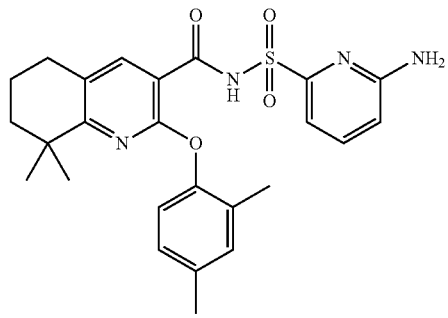 | 15 |
| 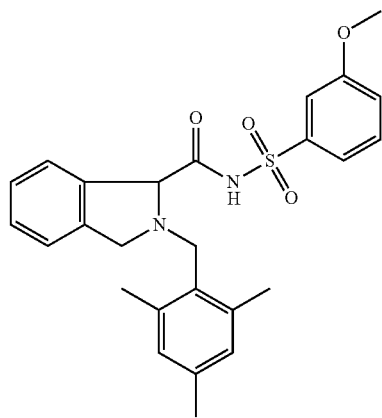 | 16 |

TABLE 1-continued
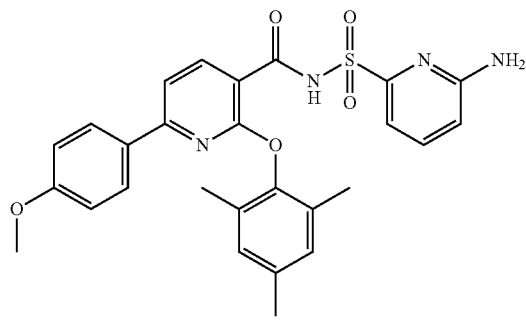 17
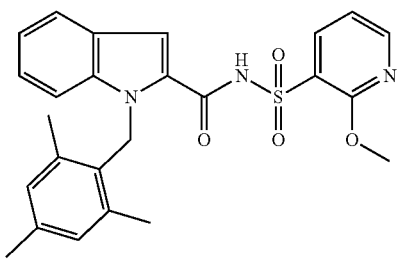 18
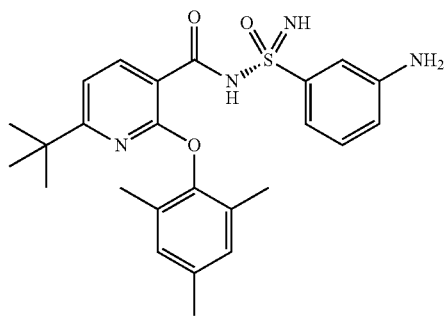 19
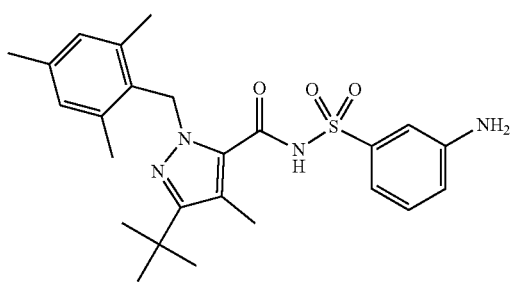 20

TABLE 1-continued
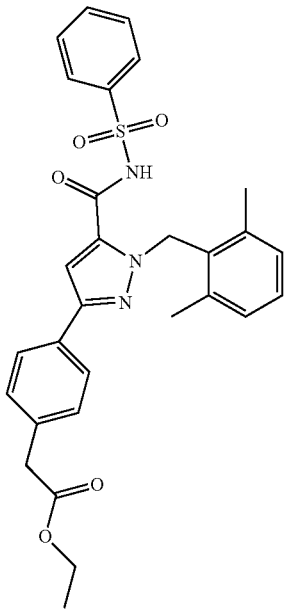 [SMILES: CCOC(=O)Cc1ccc(-c2cc(C(=O)NS(=O)(=O)c3ccccc3)n(Cc3c(C)cccc3C)n2)cc1] 21
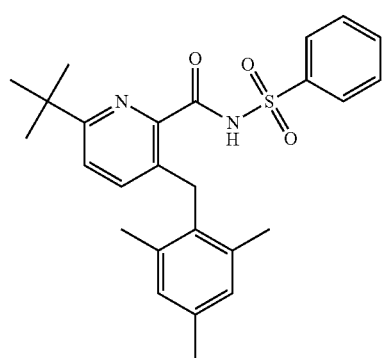 22
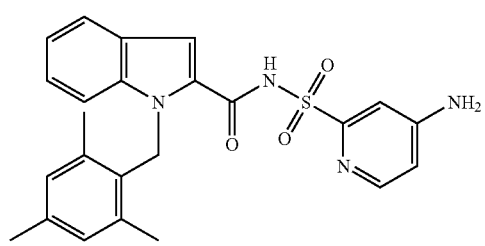 23
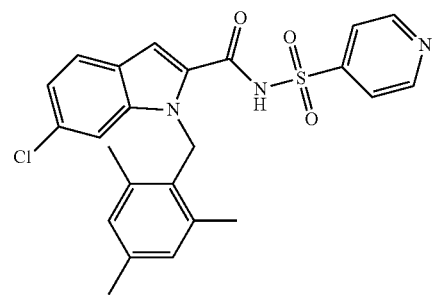 24

TABLE 1-continued
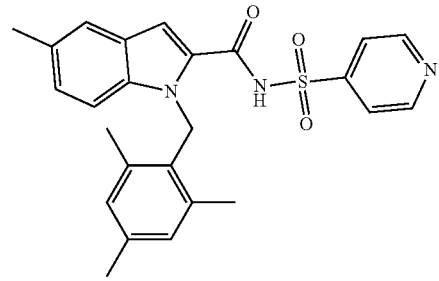 25
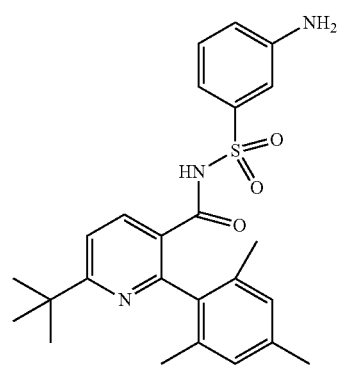 [SMILES: Cc1cc(C)c(-c2nc(C(C)(C)C)ccc2C(=O)NS(=O)(=O)c2cccc(N)c2)c(C)c1] 26
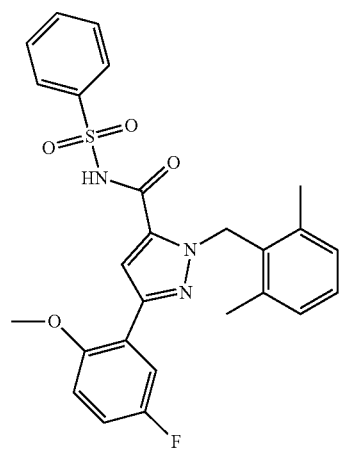 [SMILES: COc1ccc(F)cc1-c1cc(C(=O)NS(=O)(=O)c2ccccc2)n(Cc2c(C)cccc2C)n1] 27
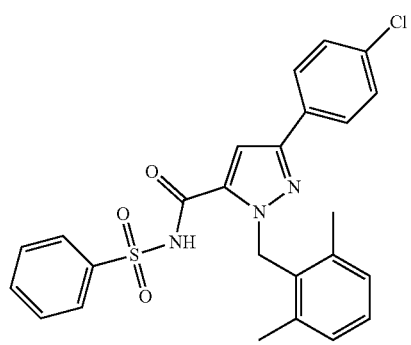 [SMILES: Cc1cccc(C)c1Cn1nc(-c2ccc(Cl)cc2)cc1C(=O)NS(=O)(=O)c1ccccc1] 28

TABLE 1-continued
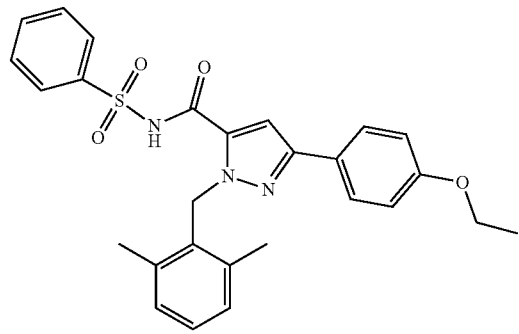
29
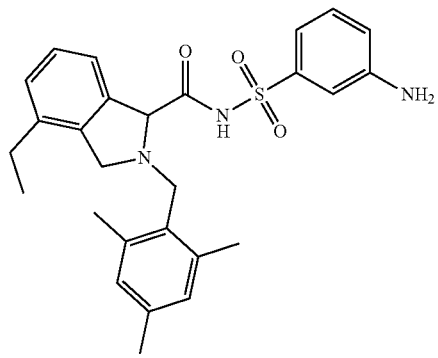
30
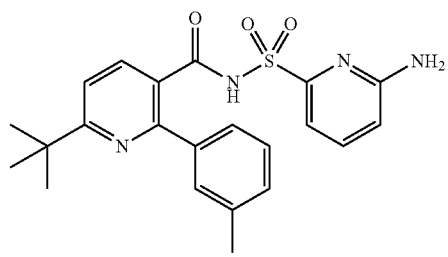
31
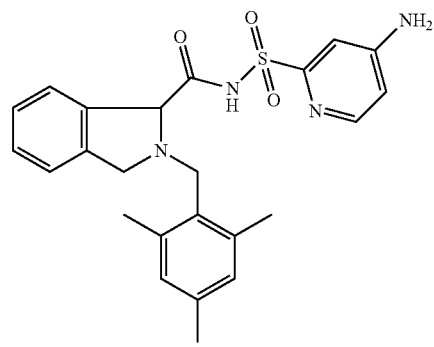
32
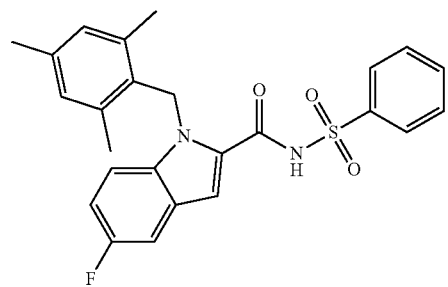
33

TABLE 1-continued
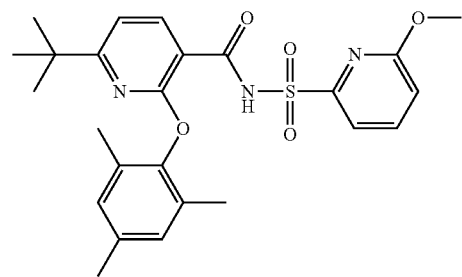 34
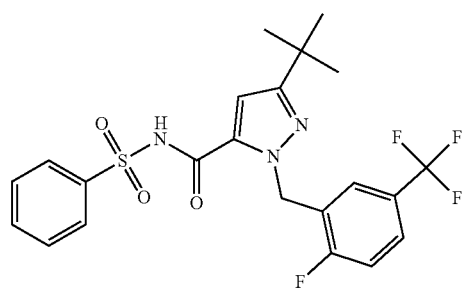 35
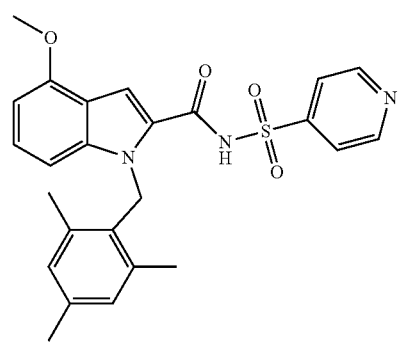 36
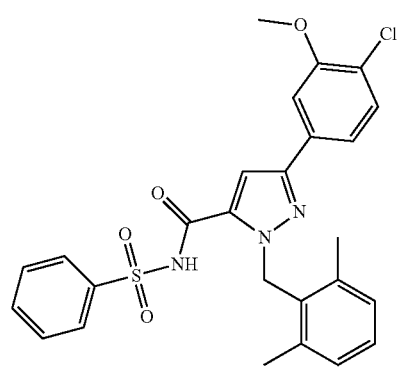 [SMILES: COc1cc(-c2cc(C(=O)NS(=O)(=O)c3ccccc3)n(Cc3c(C)cccc3C)n2)ccc1Cl] 37
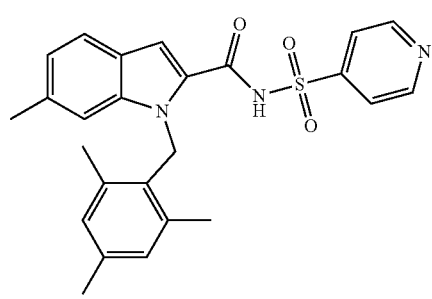 38

TABLE 1-continued
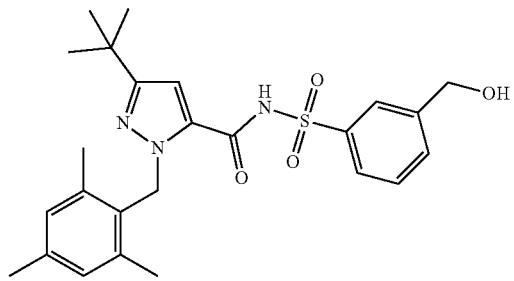 39
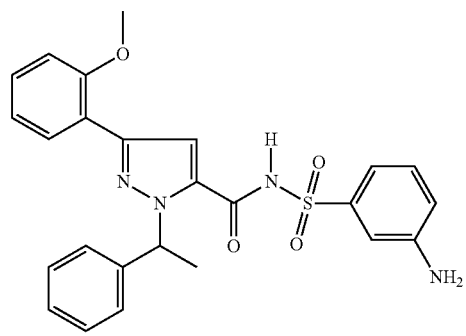 [SMILES: COc1ccccc1-c1cc(C(=O)NS(=O)(=O)c2cccc(N)c2)n(C(C)c2ccccc2)n1] 40
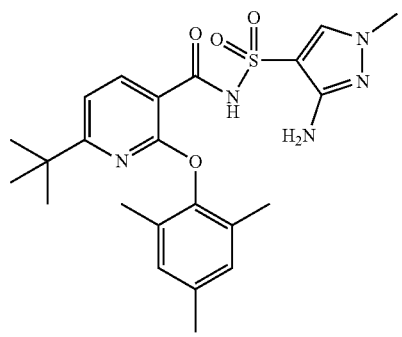 41
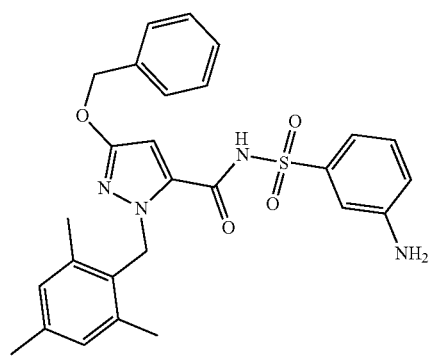 42

TABLE 1-continued
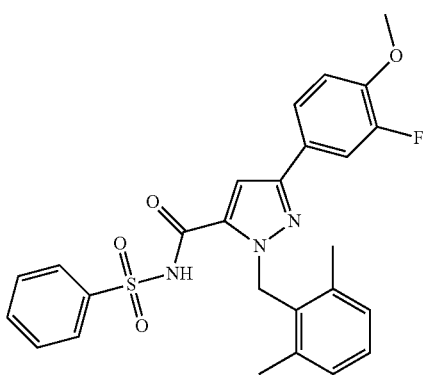 [SMILES: COc1ccc(-c2cc(C(=O)NS(=O)(=O)c3ccccc3)n(Cc3c(C)cccc3C)n2)cc1F]
43
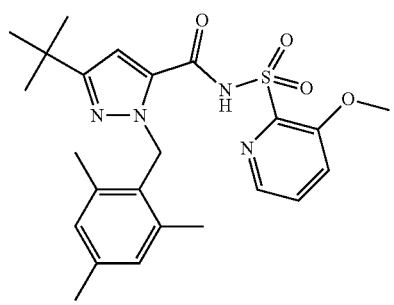
44
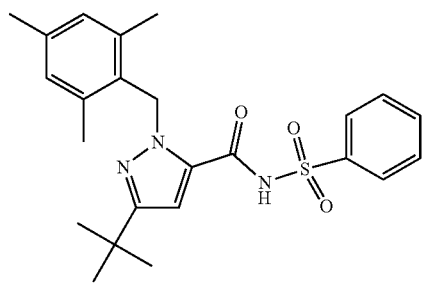
45
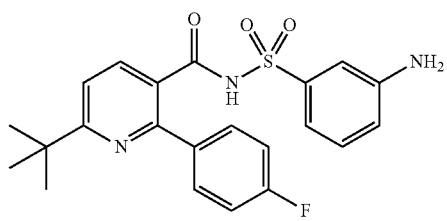
46
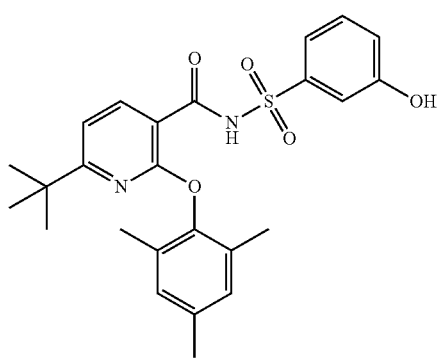
47

TABLE 1-continued
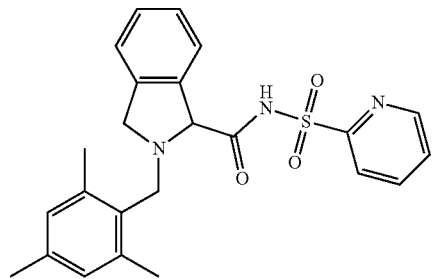
48
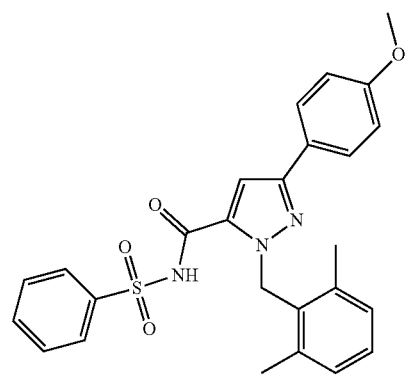 [SMILES: COc1ccc(-c2cc(C(=O)NS(=O)(=O)c3ccccc3)n(Cc3c(C)cccc3C)n2)cc1]
49
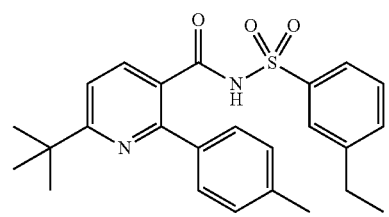
50
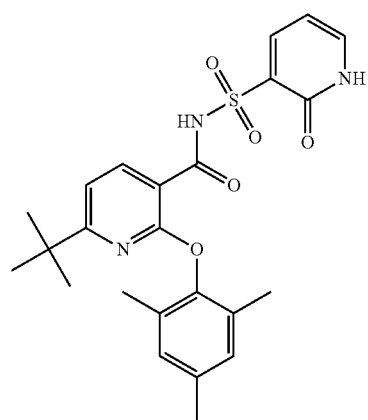 [SMILES: Cc1cc(C)c(Oc2nc(C(C)(C)C)ccc2C(=O)NS(=O)(=O)c2ccc[nH]c2=O)c(C)c1]
51
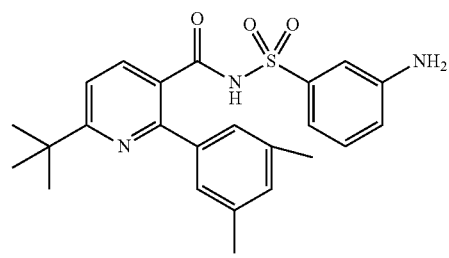
52

TABLE 1-continued

| | 53 |
| | 54 |
| | 55 |
| | 56 |
| | 57 |

TABLE 1-continued
| | |
|---|---|
| 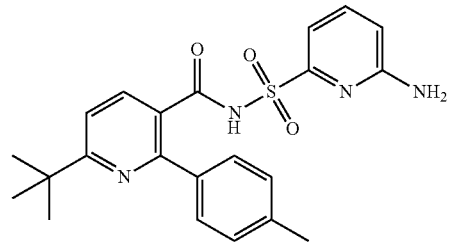 | 58 |
| 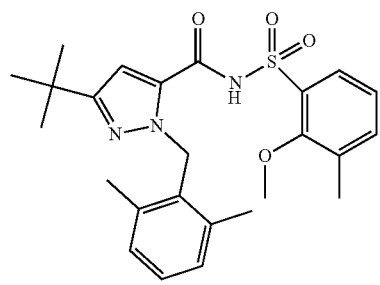 | 59 |
| 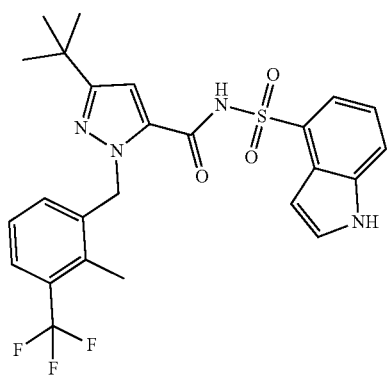 | 60 |
| 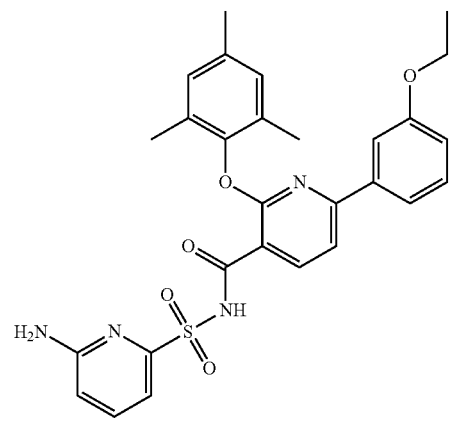 [SMILES: CCOc1cccc(-c2ccc(C(=O)NS(=O)(=O)c3cccc(N)n3)c(Oc3c(C)cc(C)cc3C)n2)c1] | 61 |
| 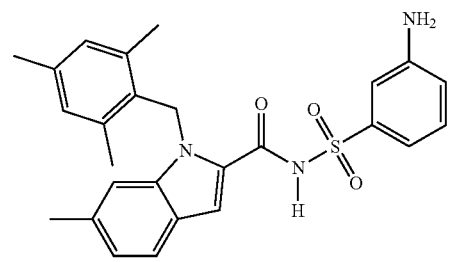 [SMILES: Cc1cc(C)c(Cn2c(C(=O)NS(=O)(=O)c3cccc(N)c3)cc3ccc(C)cc32)c(C)c1] | 62 |

TABLE 1-continued

| | |
|---|---|
| (structure) | 63 |
| (structure) | 64 |
| (structure) | 65 |
| (structure) | 66 |

TABLE 1-continued
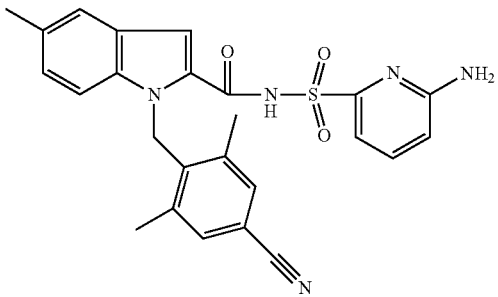
67
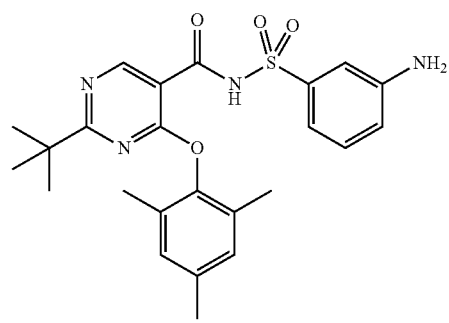
68
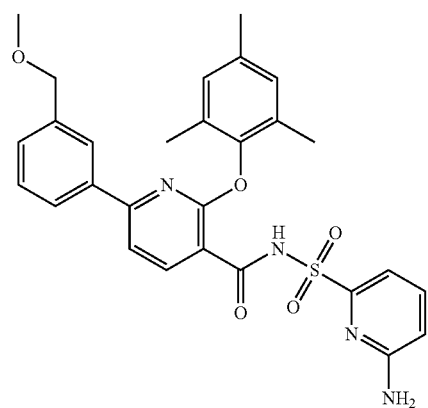
69
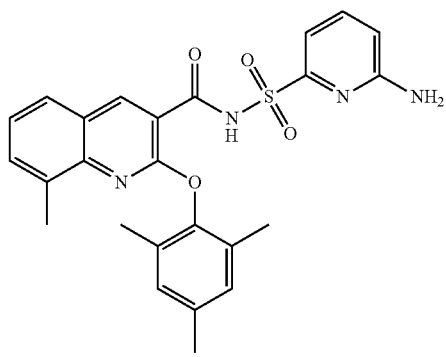
70
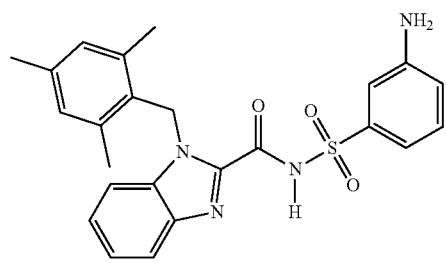 [SMILES: Cc1cc(C)c(Cn2c(C(=O)NS(=O)(=O)c3cccc(N)c3)nc3ccccc32)c(C)c1]
71

TABLE 1-continued
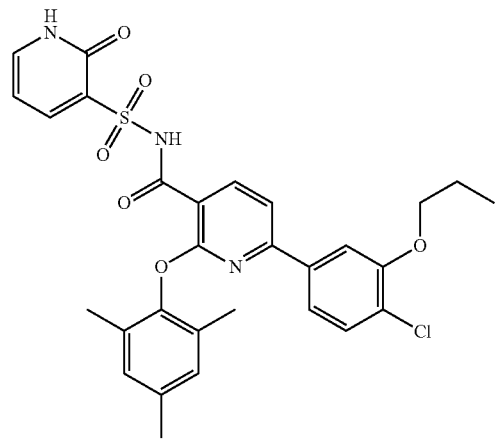 72
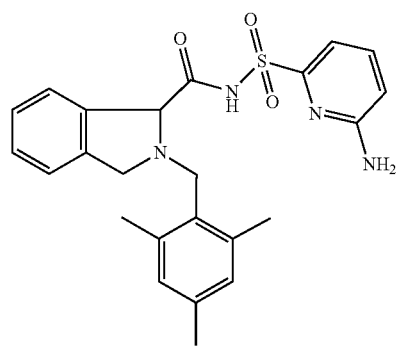 [SMILES: Cc1cc(C)c(CN2Cc3ccccc3C2C(=O)NS(=O)(=O)c2cccc(N)n2)c(C)c1] 73
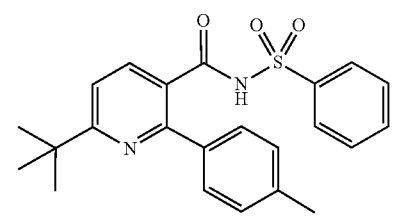 [SMILES: Cc1ccc(-c2nc(C(C)(C)C)ccc2C(=O)NS(=O)(=O)c2ccccc2)cc1] 74
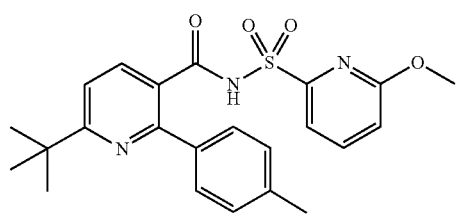 [SMILES: COc1cccc(S(=O)(=O)NC(=O)c2ccc(C(C)(C)C)nc2-c2ccc(C)cc2)n1] 75
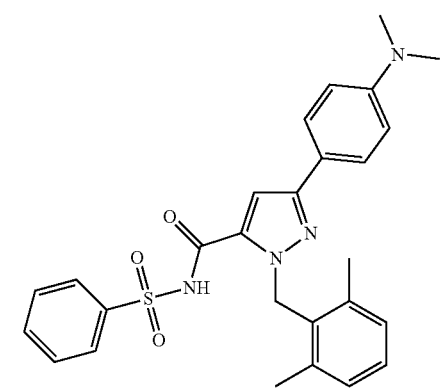 [SMILES: Cc1cccc(C)c1Cn1nc(-c2ccc(N(C)C)cc2)cc1C(=O)NS(=O)(=O)c1ccccc1] 76

TABLE 1-continued
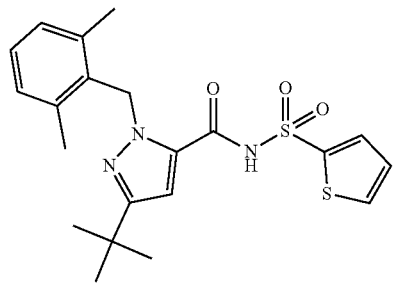 [SMILES: Cc1cccc(C)c1Cn1nc(C(C)(C)C)cc1C(=O)NS(=O)(=O)c1cccs1]
77
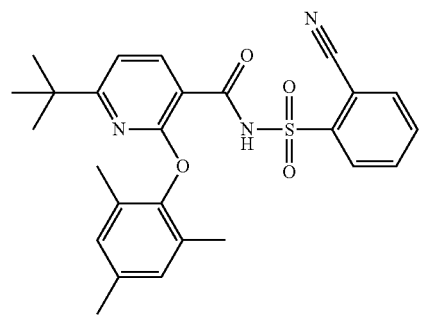 [SMILES: Cc1cc(C)c(Oc2nc(C(C)(C)C)ccc2C(=O)NS(=O)(=O)c2ccccc2C#N)c(C)c1]
78
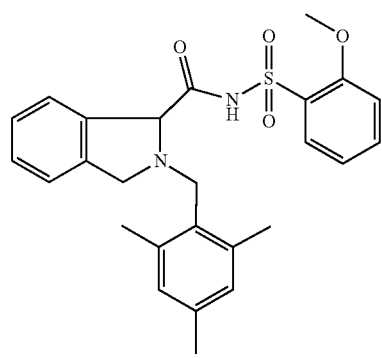 [SMILES: COc1ccccc1S(=O)(=O)NC(=O)C1c2ccccc2CN1Cc1c(C)cc(C)cc1C]
79
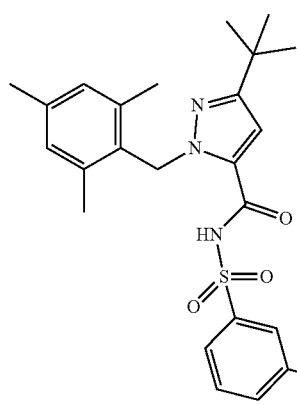
80
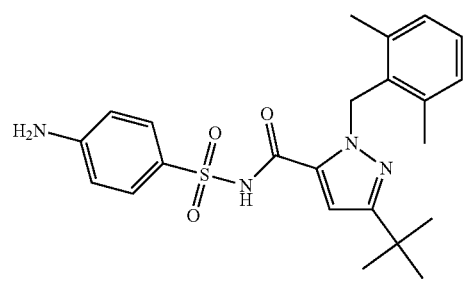 [SMILES: Cc1cccc(C)c1Cn1nc(C(C)(C)C)cc1C(=O)NS(=O)(=O)c1ccc(N)cc1]
81

TABLE 1-continued
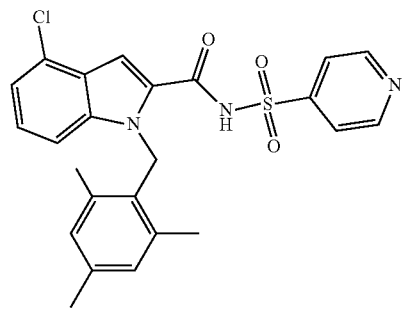 [SMILES: Cc1cc(C)c(Cn2c(C(=O)NS(=O)(=O)c3ccncc3)cc3c(Cl)cccc32)c(C)c1]
82
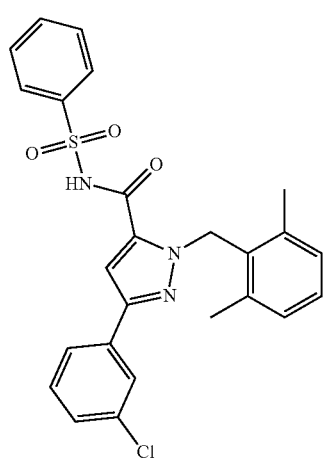
83
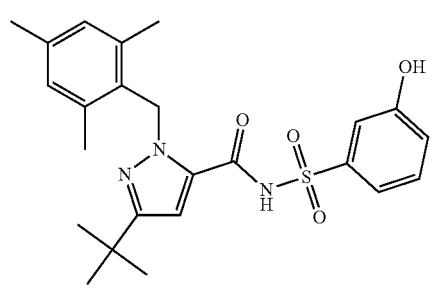 [SMILES: Cc1cc(C)c(Cn2nc(C(C)(C)C)cc2C(=O)NS(=O)(=O)c2cccc(O)c2)c(C)c1]
84
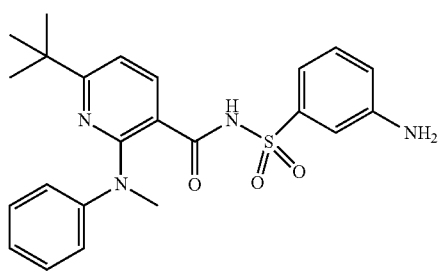 [SMILES: CN(c1ccccc1)c1nc(C(C)(C)C)ccc1C(=O)NS(=O)(=O)c1cccc(N)c1]
85

TABLE 1-continued
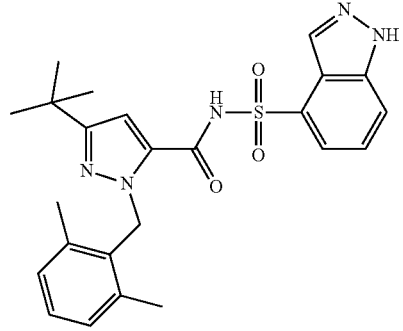 [SMILES: Cc1cccc(C)c1Cn1nc(C(C)(C)C)cc1C(=O)NS(=O)(=O)c1cccc2[nH]ncc12] 86
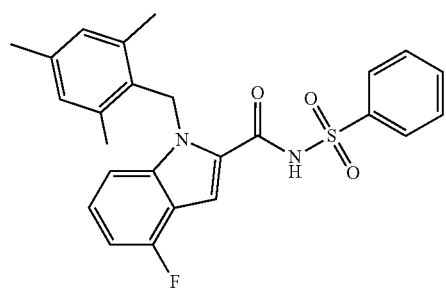 [SMILES: Cc1cc(C)c(Cn2c(C(=O)NS(=O)(=O)c3ccccc3)cc3c(F)cccc32)c(C)c1] 87
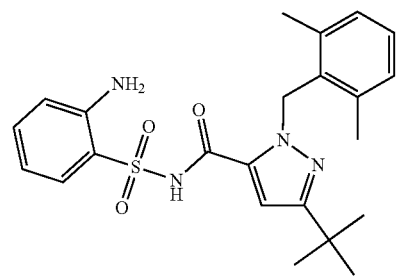 [SMILES: Cc1cccc(C)c1Cn1nc(C(C)(C)C)cc1C(=O)NS(=O)(=O)c1ccccc1N] 88
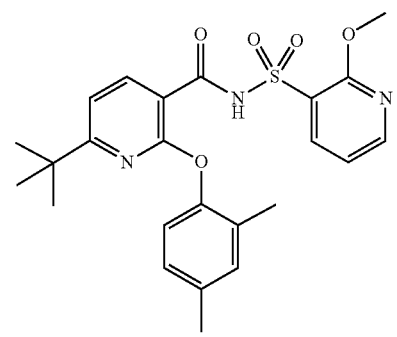 [SMILES: COc1ncccc1S(=O)(=O)NC(=O)c1ccc(C(C)(C)C)nc1Oc1ccc(C)cc1C] 89
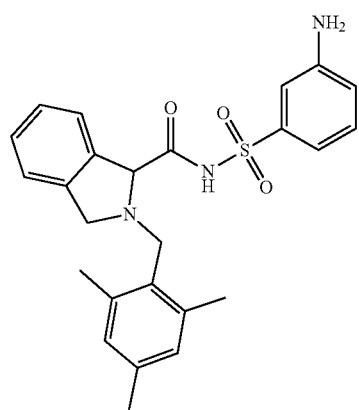 [SMILES: Cc1cc(C)c(CN2Cc3ccccc3C2C(=O)NS(=O)(=O)c2cccc(N)c2)c(C)c1] 90

TABLE 1-continued
 91
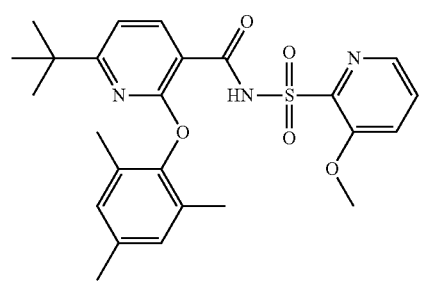 [SMILES: COc1cccnc1S(=O)(=O)NC(=O)c1ccc(C(C)(C)C)nc1Oc1c(C)cc(C)cc1C] 92
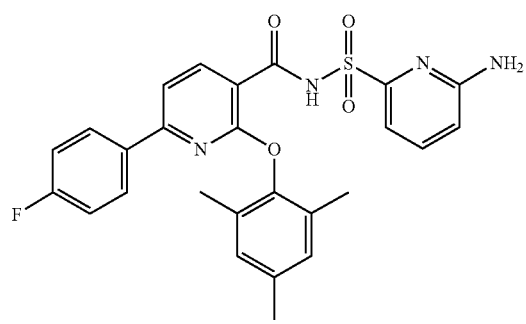 [SMILES: Cc1cc(C)c(Oc2nc(-c3ccc(F)cc3)ccc2C(=O)NS(=O)(=O)c2cccc(N)n2)c(C)c1] 93
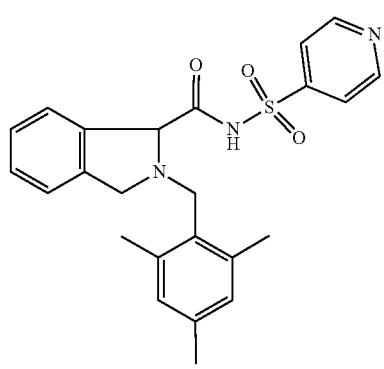 [SMILES: Cc1cc(C)c(CN2Cc3ccccc3C2C(=O)NS(=O)(=O)c2ccncc2)c(C)c1] 94
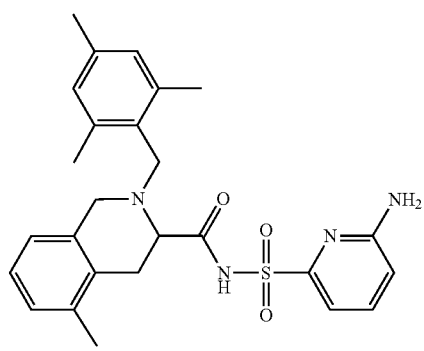 [SMILES: Cc1cc(C)c(CN2Cc3cccc(C)c3CC2C(=O)NS(=O)(=O)c2cccc(N)n2)c(C)c1] 95

TABLE 1-continued
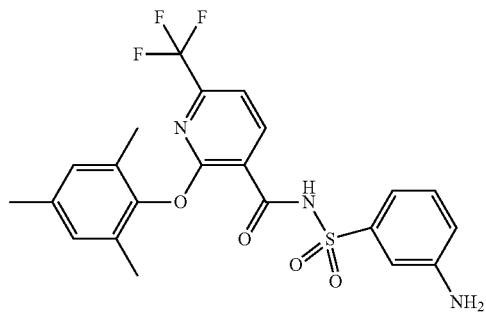 [SMILES: Cc1cc(C)c(Oc2nc(C(F)(F)F)ccc2C(=O)NS(=O)(=O)c2cccc(N)c2)c(C)c1] 96
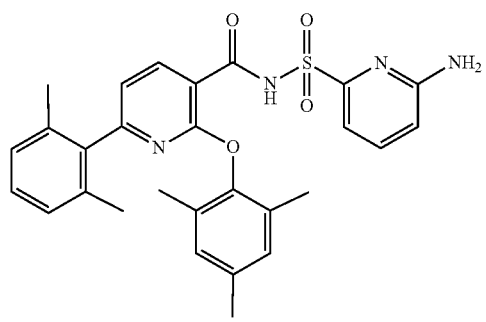 [SMILES: Cc1cc(C)c(Oc2nc(-c3c(C)cccc3C)ccc2C(=O)NS(=O)(=O)c2cccc(N)n2)c(C)c1] 97
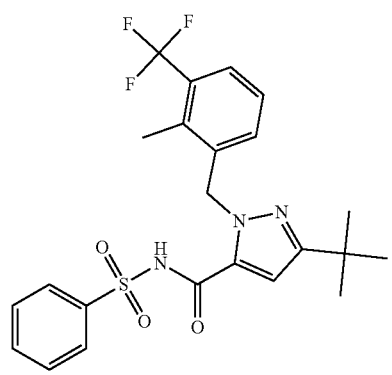 [SMILES: Cc1c(Cn2nc(C(C)(C)C)cc2C(=O)NS(=O)(=O)c2ccccc2)cccc1C(F)(F)F] 98
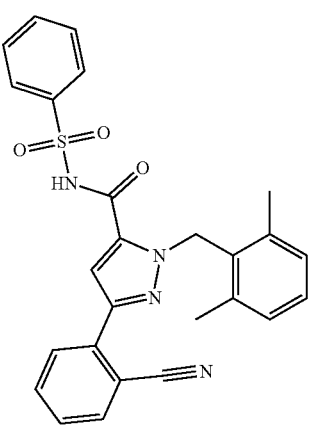 [SMILES: Cc1cccc(C)c1Cn1nc(-c2ccccc2C#N)cc1C(=O)NS(=O)(=O)c1ccccc1] 99

TABLE 1-continued
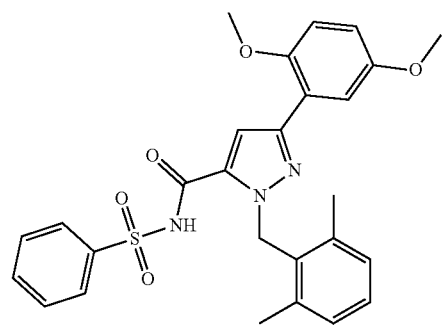
100
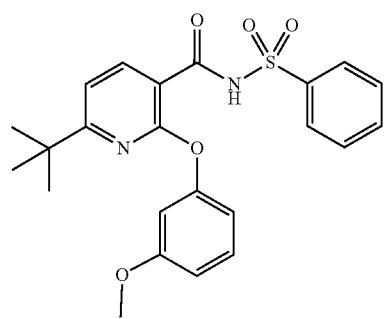
101
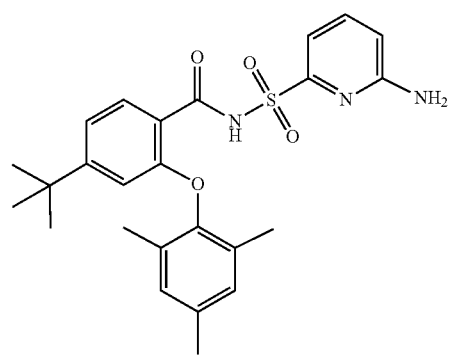 [SMILES: Cc1cc(C)c(Oc2cc(C(C)(C)C)ccc2C(=O)NS(=O)(=O)c2cccc(N)n2)c(C)c1]
102
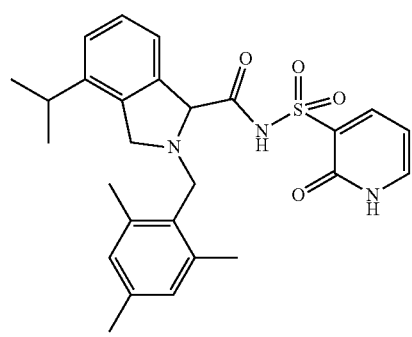 [SMILES: Cc1cc(C)c(CN2Cc3c(C(C)C)cccc3C2C(=O)NS(=O)(=O)c2ccc[nH]c2=O)c(C)c1]
103
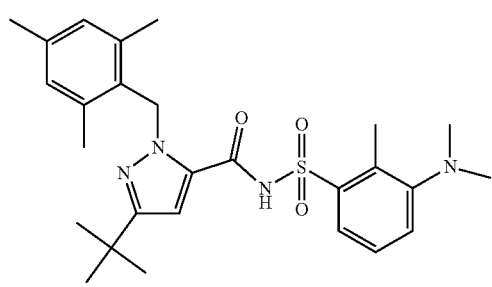
104

TABLE 1-continued
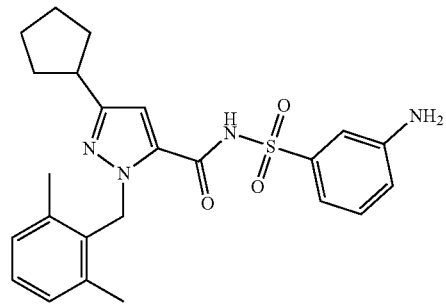 [SMILES: Cc1cccc(C)c1Cn1nc(C2CCCC2)cc1C(=O)NS(=O)(=O)c1cccc(N)c1]
105
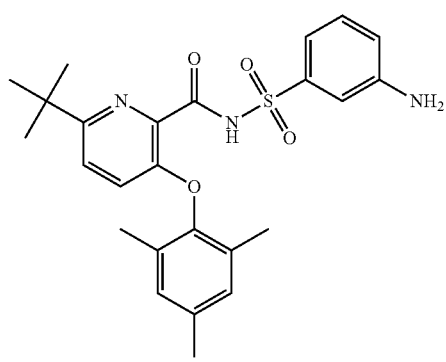 [SMILES: Cc1cc(C)c(Oc2ccc(C(C)(C)C)nc2C(=O)NS(=O)(=O)c2cccc(N)c2)c(C)c1]
106
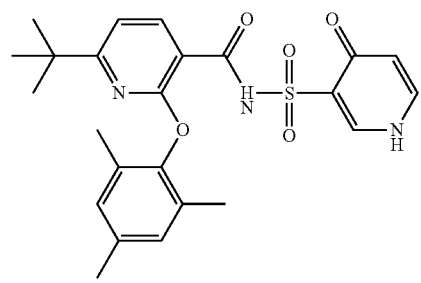 [SMILES: Cc1cc(C)c(Oc2nc(C(C)(C)C)ccc2C(=O)NS(=O)(=O)c2c[nH]ccc2=O)c(C)c1]
107
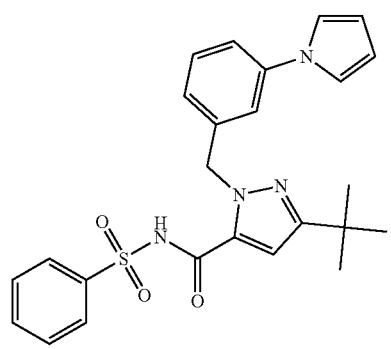 [SMILES: CC(C)(C)c1cc(C(=O)NS(=O)(=O)c2ccccc2)n(Cc2cccc(-n3cccc3)c2)n1]
108

TABLE 1-continued
| | |
|---|---|
| 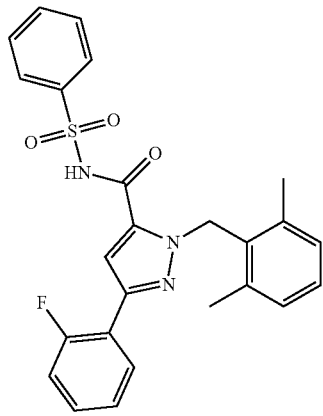 [SMILES: Cc1cccc(C)c1Cn1nc(-c2ccccc2F)cc1C(=O)NS(=O)(=O)c1ccccc1] | 109 |
| 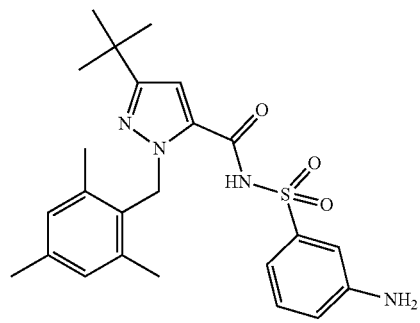 [SMILES: Cc1cc(C)c(Cn2nc(C(C)(C)C)cc2C(=O)NS(=O)(=O)c2cccc(N)c2)c(C)c1] | 110 |
| 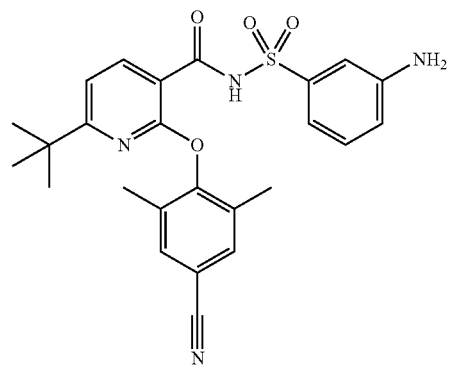 [SMILES: Cc1cc(C#N)cc(C)c1Oc1nc(C(C)(C)C)ccc1C(=O)NS(=O)(=O)c1cccc(N)c1] | 111 |
| 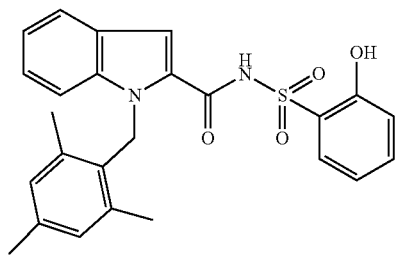 [SMILES: Cc1cc(C)c(Cn2c(C(=O)NS(=O)(=O)c3ccccc3O)cc3ccccc32)c(C)c1] | 112 |
| 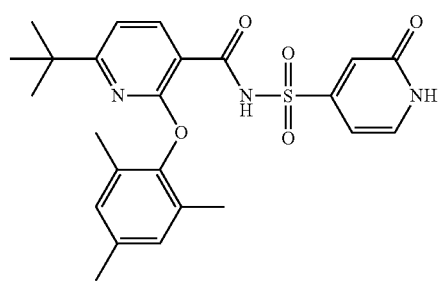 [SMILES: Cc1cc(C)c(Oc2nc(C(C)(C)C)ccc2C(=O)NS(=O)(=O)c2cc[nH]c(=O)c2)c(C)c1] | 113 |

TABLE 1-continued
| | |
|---|---|
| 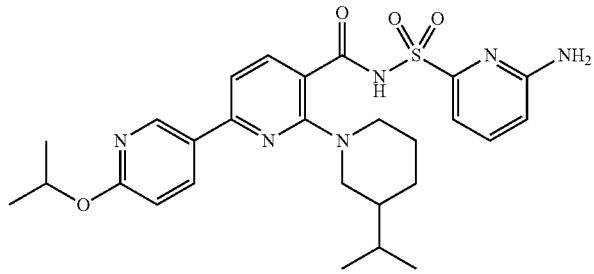 [SMILES: CC(C)Oc1ccc(-c2ccc(C(=O)NS(=O)(=O)c3cccc(N)n3)c(N3CCCC(C(C)C)C3)n2)cn1] | 114 |
| 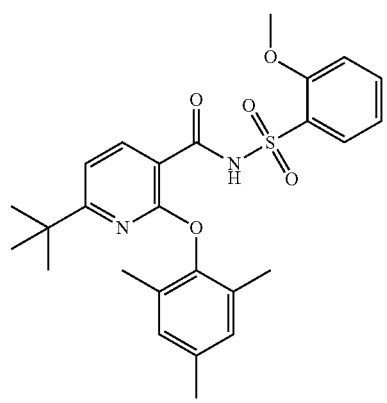 [SMILES: COc1ccccc1S(=O)(=O)NC(=O)c1ccc(C(C)(C)C)nc1Oc1c(C)cc(C)cc1C] | 115 |
| 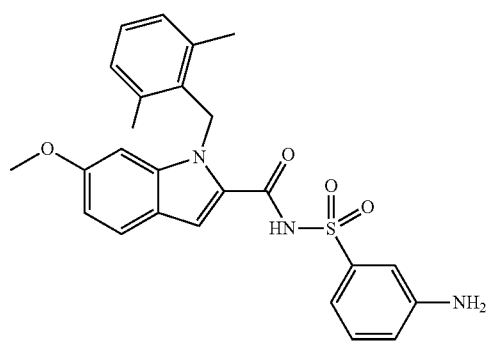 [SMILES: COc1ccc2cc(C(=O)NS(=O)(=O)c3cccc(N)c3)n(Cc3c(C)cccc3C)c2c1] | 116 |
| 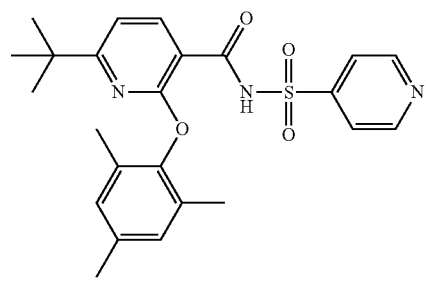 [SMILES: Cc1cc(C)c(Oc2nc(C(C)(C)C)ccc2C(=O)NS(=O)(=O)c2ccncc2)c(C)c1] | 117 |
| 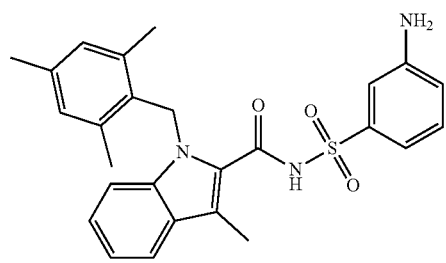 [SMILES: Cc1cc(C)c(Cn2c(C(=O)NS(=O)(=O)c3cccc(N)c3)c(C)c3ccccc32)c(C)c1] | 118 |

TABLE 1-continued
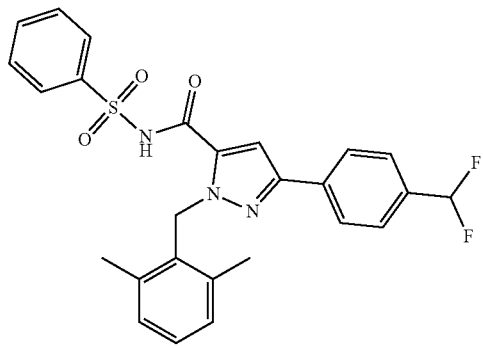 [SMILES: Cc1cccc(C)c1Cn1nc(-c2ccc(C(F)F)cc2)cc1C(=O)NS(=O)(=O)c1ccccc1] 119
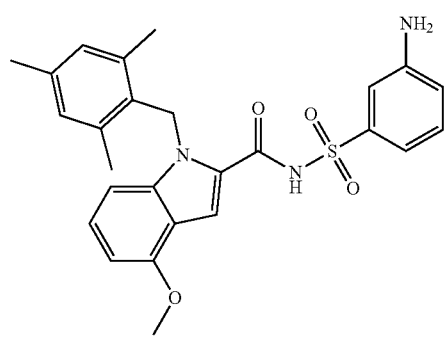 [SMILES: COc1cccc2c1cc(C(=O)NS(=O)(=O)c1cccc(N)c1)n2Cc1c(C)cc(C)cc1C] 120
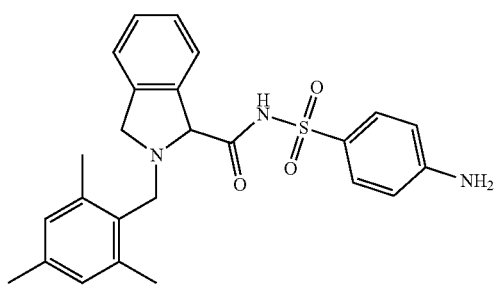 [SMILES: Cc1cc(C)c(CN2Cc3ccccc3C2C(=O)NS(=O)(=O)c2ccc(N)cc2)c(C)c1] 121
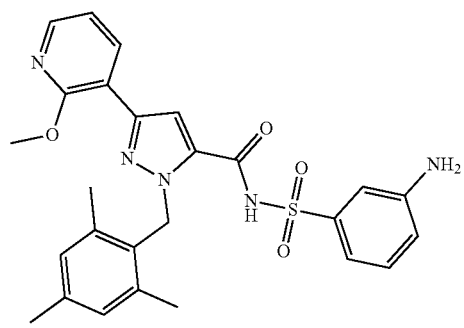 [SMILES: COc1ncccc1-c1cc(C(=O)NS(=O)(=O)c2cccc(N)c2)n(Cc2c(C)cc(C)cc2C)n1] 122

TABLE 1-continued
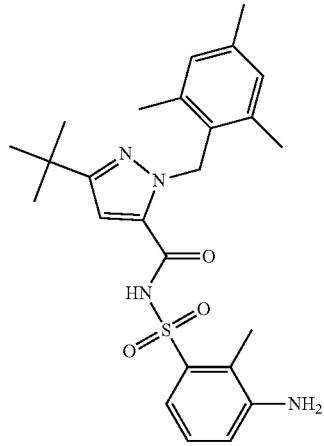 [SMILES: Cc1cc(C)c(Cn2nc(C(C)(C)C)cc2C(=O)NS(=O)(=O)c2cccc(N)c2C)c(C)c1]
123
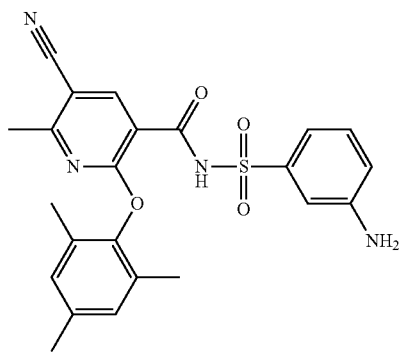 [SMILES: Cc1cc(C)c(Oc2nc(C)c(C#N)cc2C(=O)NS(=O)(=O)c2cccc(N)c2)c(C)c1]
124
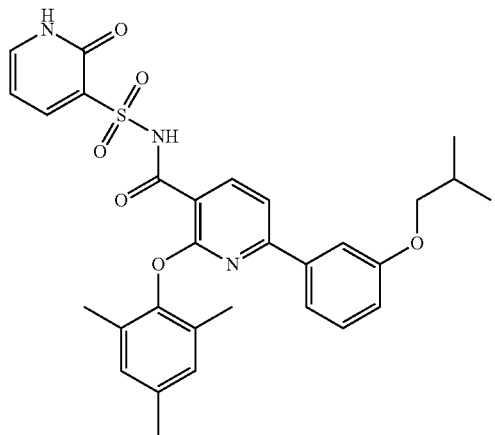 [SMILES: Cc1cc(C)c(Oc2nc(-c3cccc(OCC(C)C)c3)ccc2C(=O)NS(=O)(=O)c2ccc[nH]c2=O)c(C)c1]
125

TABLE 1-continued
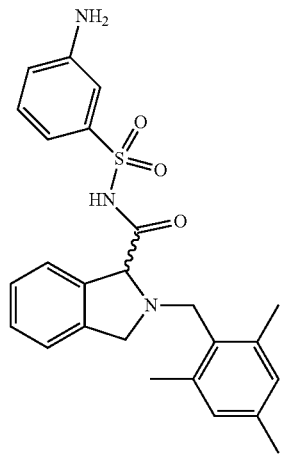 [SMILES: Cc1cc(C)c(CN2Cc3ccccc3C2C(=O)NS(=O)(=O)c2cccc(N)c2)c(C)c1]
126
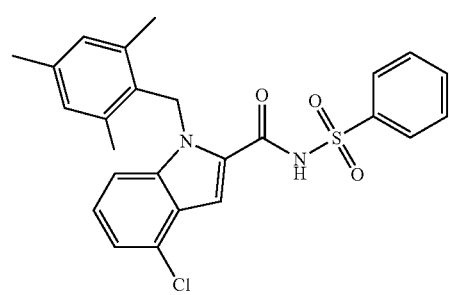 [SMILES: Cc1cc(C)c(Cn2c(C(=O)NS(=O)(=O)c3ccccc3)cc3c(Cl)cccc32)c(C)c1]
127
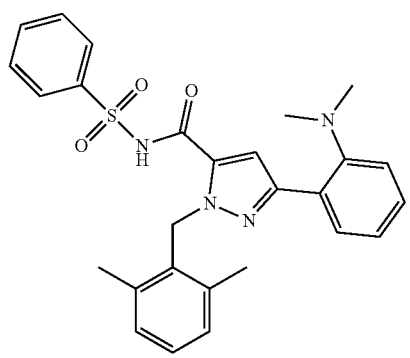 [SMILES: Cc1cccc(C)c1Cn1nc(-c2ccccc2N(C)C)cc1C(=O)NS(=O)(=O)c1ccccc1]
128
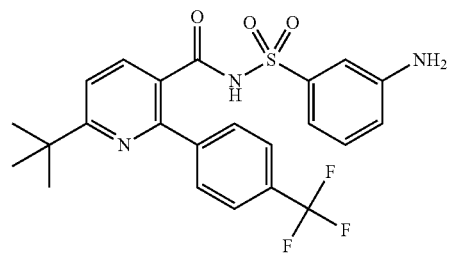 [SMILES: CC(C)(C)c1ccc(C(=O)NS(=O)(=O)c2cccc(N)c2)c(-c2ccc(C(F)(F)F)cc2)n1]
129
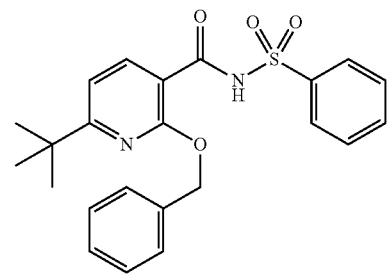 [SMILES: CC(C)(C)c1ccc(C(=O)NS(=O)(=O)c2ccccc2)c(OCc2ccccc2)n1]
130

TABLE 1-continued
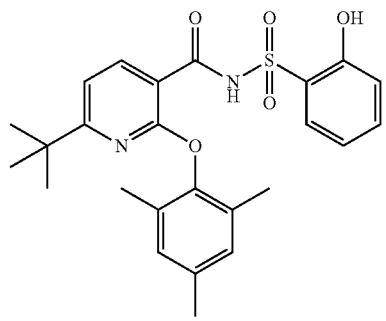 [SMILES: Cc1cc(C)c(Oc2nc(C(C)(C)C)ccc2C(=O)NS(=O)(=O)c2ccccc2O)c(C)c1]
131
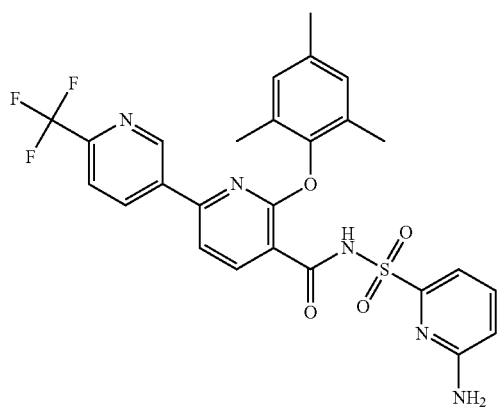 [SMILES: Cc1cc(C)c(Oc2nc(-c3ccc(C(F)(F)F)nc3)ccc2C(=O)NS(=O)(=O)c2cccc(N)n2)c(C)c1]
132
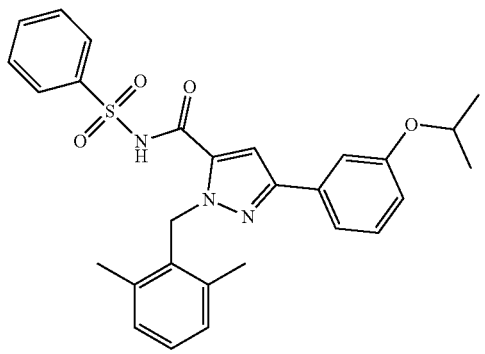 [SMILES: Cc1cccc(C)c1Cn1nc(-c2cccc(OC(C)C)c2)cc1C(=O)NS(=O)(=O)c1ccccc1]
133
134

TABLE 1-continued
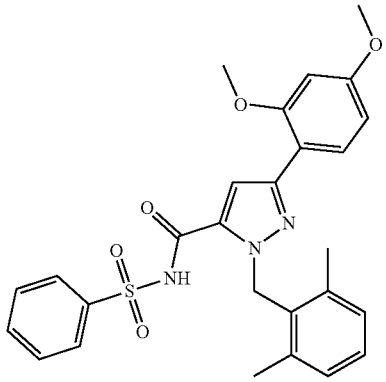 [SMILES: COc1ccc(-c2cc(C(=O)NS(=O)(=O)c3ccccc3)n(Cc3c(C)cccc3C)n2)c(OC)c1]
135
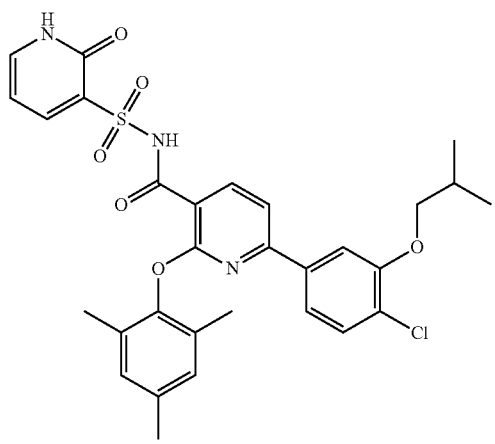 [SMILES: Cc1cc(C)c(Oc2nc(-c3ccc(Cl)c(OCC(C)C)c3)ccc2C(=O)NS(=O)(=O)c2ccc[nH]c2=O)c(C)c1]
136
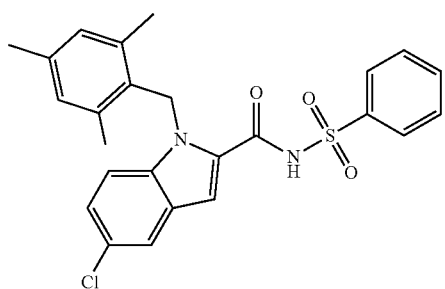
137
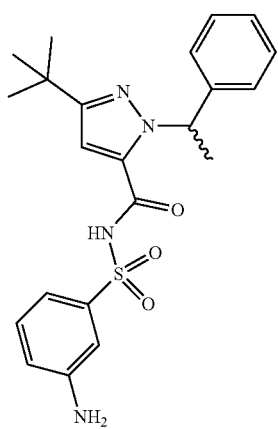 [SMILES: CC(c1ccccc1)n1nc(C(C)(C)C)cc1C(=O)NS(=O)(=O)c1cccc(N)c1]
138

TABLE 1-continued
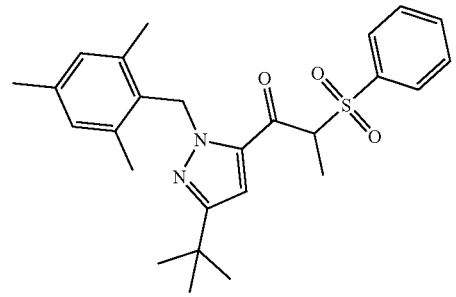 [SMILES: Cc1cc(C)c(Cn2nc(C(C)(C)C)cc2C(=O)C(C)S(=O)(=O)c2ccccc2)c(C)c1]
139
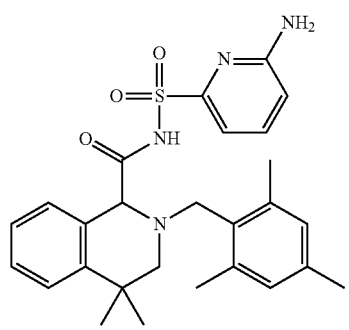 [SMILES: Cc1cc(C)c(CN2CC(C)(C)c3ccccc3C2C(=O)NS(=O)(=O)c2cccc(N)n2)c(C)c1]
140
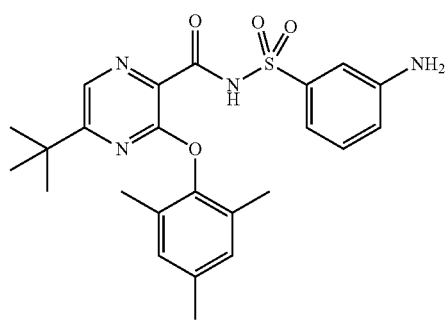
141
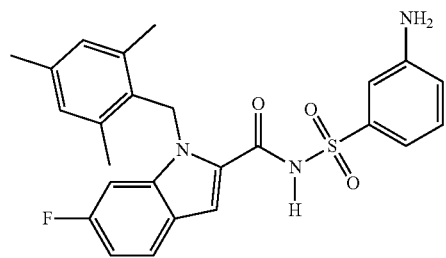
142
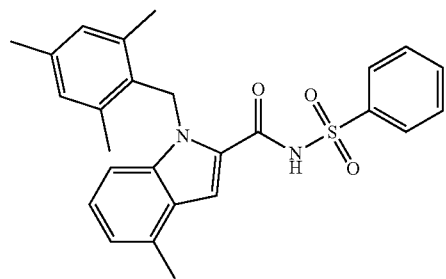 [SMILES: Cc1cc(C)c(Cn2c(C(=O)NS(=O)(=O)c3ccccc3)cc3c(C)cccc32)c(C)c1]
143

TABLE 1-continued
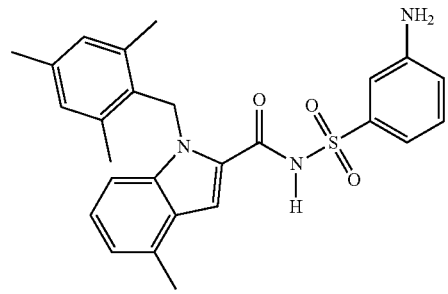 [SMILES: Cc1cc(C)c(Cn2c(C(=O)NS(=O)(=O)c3cccc(N)c3)cc3c(C)cccc32)c(C)c1] 144
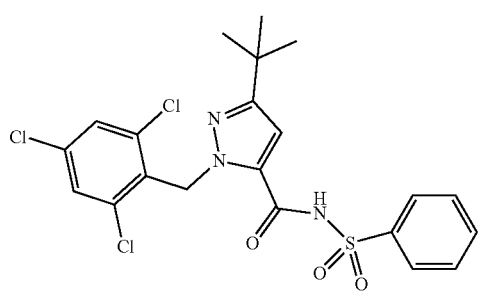 [SMILES: CC(C)(C)c1cc(C(=O)NS(=O)(=O)c2ccccc2)n(Cc2c(Cl)cc(Cl)cc2Cl)n1] 145
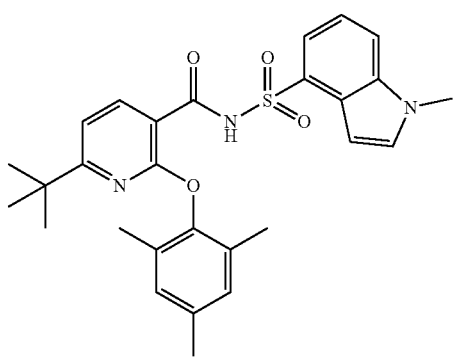 [SMILES: Cc1cc(C)c(Oc2nc(C(C)(C)C)ccc2C(=O)NS(=O)(=O)c2cccc3c2ccn3C)c(C)c1] 146
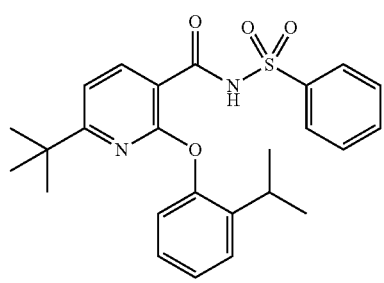 [SMILES: CC(C)c1ccccc1Oc1nc(C(C)(C)C)ccc1C(=O)NS(=O)(=O)c1ccccc1] 147
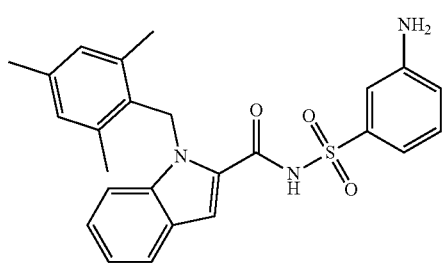 [SMILES: Cc1cc(C)c(Cn2c(C(=O)NS(=O)(=O)c3cccc(N)c3)cc3ccccc32)c(C)c1] 148

TABLE 1-continued
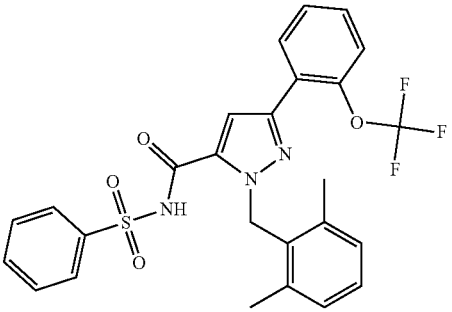 [SMILES: Cc1cccc(C)c1Cn1nc(-c2ccccc2OC(F)(F)F)cc1C(=O)NS(=O)(=O)c1ccccc1]
149
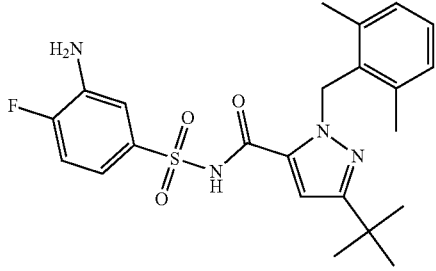 [SMILES: Cc1cccc(C)c1Cn1nc(C(C)(C)C)cc1C(=O)NS(=O)(=O)c1ccc(F)c(N)c1]
150
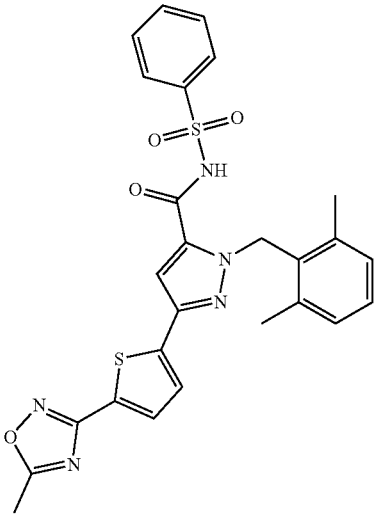 [SMILES: Cc1nc(-c2ccc(-c3cc(C(=O)NS(=O)(=O)c4ccccc4)n(Cc4c(C)cccc4C)n3)s2)no1]
151
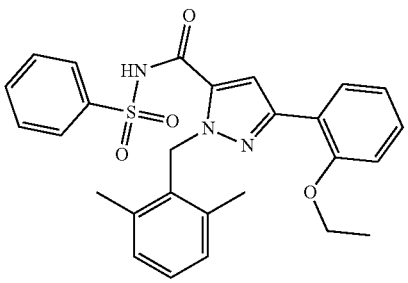 [SMILES: CCOc1ccccc1-c1cc(C(=O)NS(=O)(=O)c2ccccc2)n(Cc2c(C)cccc2C)n1]
152

TABLE 1-continued
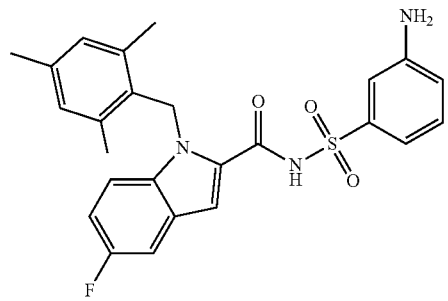 [SMILES: Cc1cc(C)c(Cn2c(C(=O)NS(=O)(=O)c3cccc(N)c3)cc3cc(F)ccc32)c(C)c1]
153
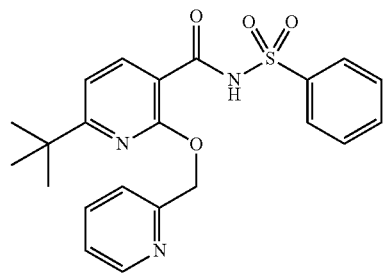 [SMILES: CC(C)(C)c1ccc(C(=O)NS(=O)(=O)c2ccccc2)c(OCc2ccccn2)n1]
154
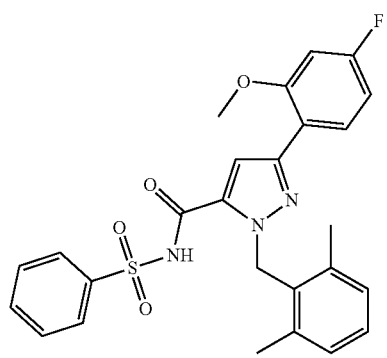 [SMILES: COc1cc(F)ccc1-c1cc(C(=O)NS(=O)(=O)c2ccccc2)n(Cc2c(C)cccc2C)n1]
155
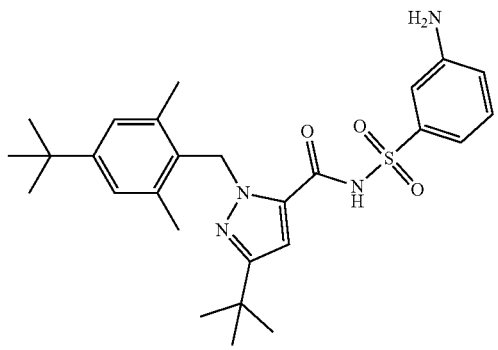 [SMILES: Cc1cc(C(C)(C)C)cc(C)c1Cn1nc(C(C)(C)C)cc1C(=O)NS(=O)(=O)c1cccc(N)c1]
156
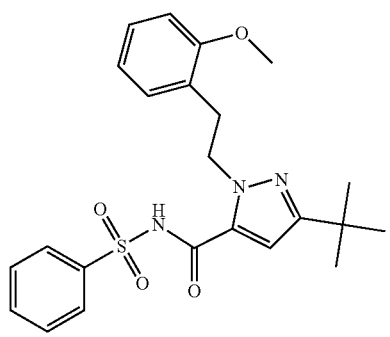 [SMILES: COc1ccccc1CCn1nc(C(C)(C)C)cc1C(=O)NS(=O)(=O)c1ccccc1]
157

TABLE 1-continued
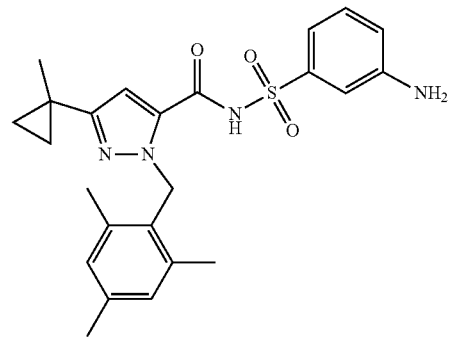 [SMILES: Cc1cc(C)c(Cn2nc(C3(C)CC3)cc2C(=O)NS(=O)(=O)c2cccc(N)c2)c(C)c1]
158
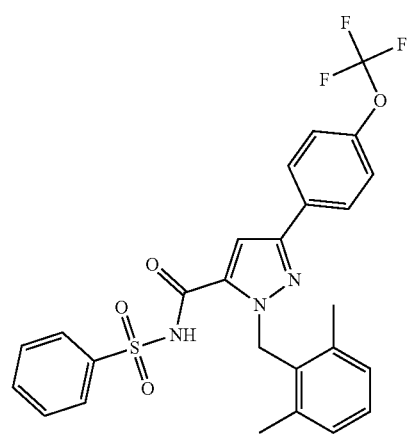 [SMILES: Cc1cccc(C)c1Cn1nc(-c2ccc(OC(F)(F)F)cc2)cc1C(=O)NS(=O)(=O)c1ccccc1]
159
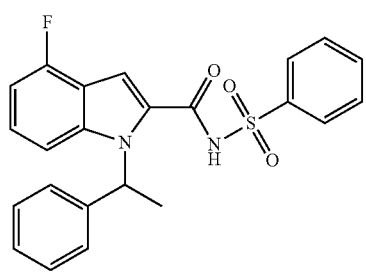 [SMILES: CC(c1ccccc1)n1c(C(=O)NS(=O)(=O)c2ccccc2)cc2c(F)cccc21]
160
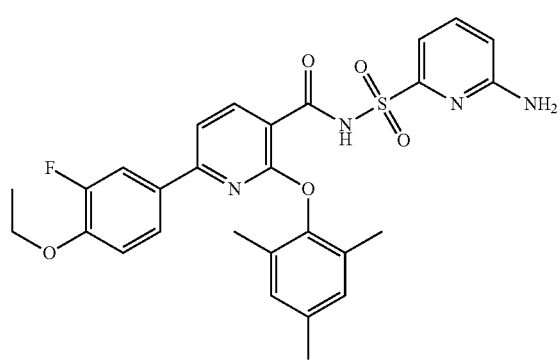 [SMILES: CCOc1ccc(-c2ccc(C(=O)NS(=O)(=O)c3cccc(N)n3)c(Oc3c(C)cc(C)cc3C)n2)cc1F]
161

TABLE 1-continued
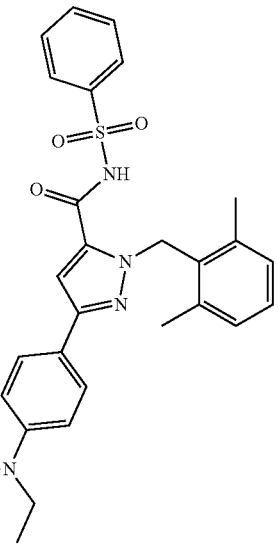
162
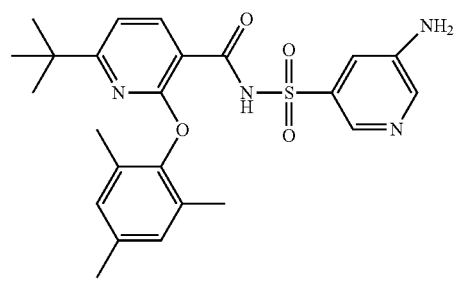 [SMILES: Cc1cc(C)c(Oc2nc(C(C)(C)C)ccc2C(=O)NS(=O)(=O)c2cncc(N)c2)c(C)c1]
163
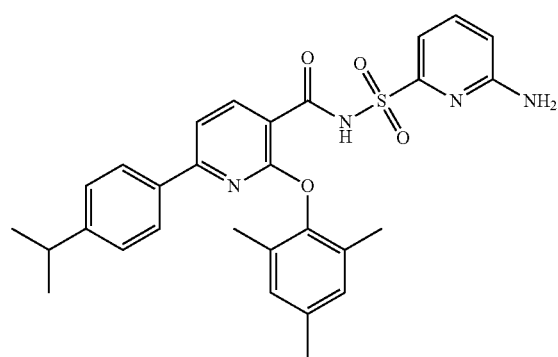 [SMILES: Cc1cc(C)c(Oc2nc(-c3ccc(C(C)C)cc3)ccc2C(=O)NS(=O)(=O)c2cccc(N)n2)c(C)c1]
164
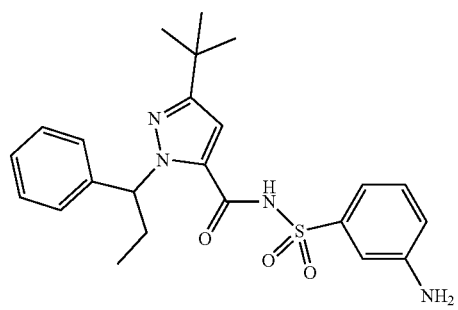 [SMILES: CCC(c1ccccc1)n1nc(C(C)(C)C)cc1C(=O)NS(=O)(=O)c1cccc(N)c1]
165

TABLE 1-continued
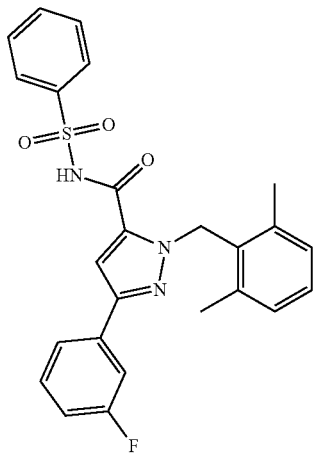 [SMILES: Cc1cccc(C)c1Cn1nc(-c2cccc(F)c2)cc1C(=O)NS(=O)(=O)c1ccccc1]
166
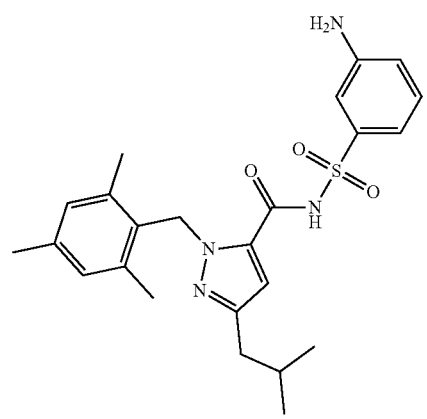 [SMILES: Cc1cc(C)c(Cn2nc(CC(C)C)cc2C(=O)NS(=O)(=O)c2cccc(N)c2)c(C)c1]
167
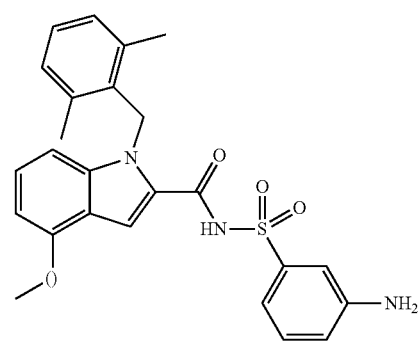
168
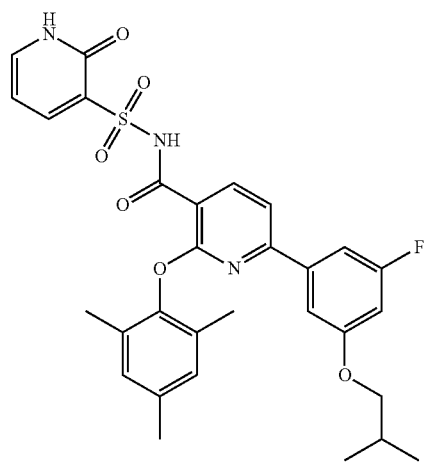 [SMILES: Cc1cc(C)c(Oc2nc(-c3cc(F)cc(OCC(C)C)c3)ccc2C(=O)NS(=O)(=O)c2ccc[nH]c2=O)c(C)c1]
169

TABLE 1-continued
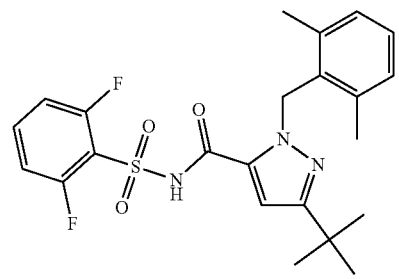 [SMILES: Cc1cccc(C)c1Cn1nc(C(C)(C)C)cc1C(=O)NS(=O)(=O)c1c(F)cccc1F]
170
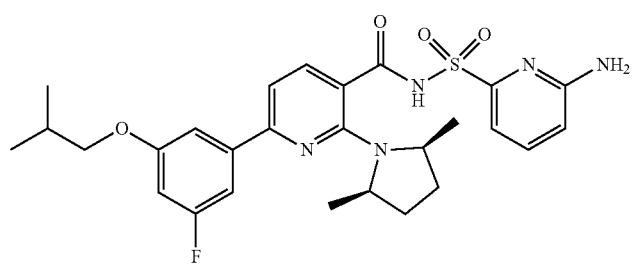 [SMILES: CC(C)COc1cc(F)cc(-c2ccc(C(=O)NS(=O)(=O)c3cccc(N)n3)c(N3[C@H](C)CC[C@@H]3C)n2)c1]
171
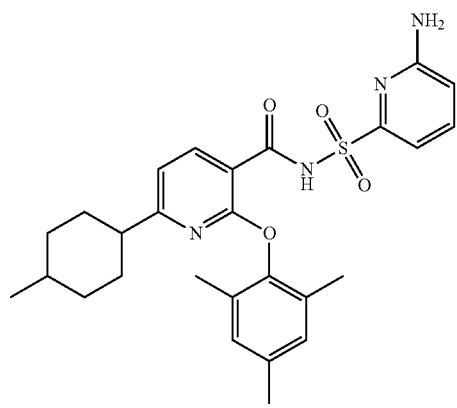 [SMILES: Cc1cc(C)c(Oc2nc(C3CCC(C)CC3)ccc2C(=O)NS(=O)(=O)c2cccc(N)n2)c(C)c1]
172
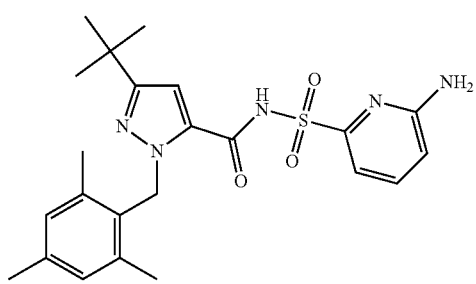 [SMILES: Cc1cc(C)c(Cn2nc(C(C)(C)C)cc2C(=O)NS(=O)(=O)c2cccc(N)n2)c(C)c1]
173
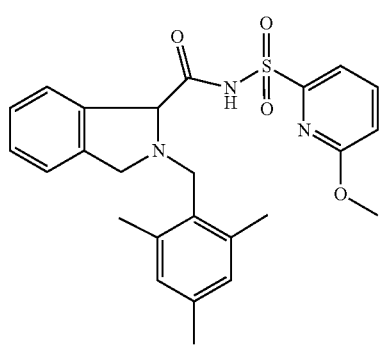 [SMILES: COc1cccc(S(=O)(=O)NC(=O)C2c3ccccc3CN2Cc2c(C)cc(C)cc2C)n1]
174

TABLE 1-continued
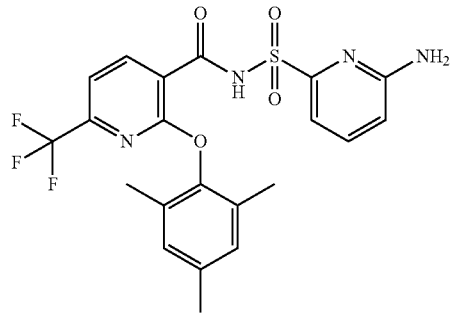 [SMILES: Cc1cc(C)c(Oc2nc(C(F)(F)F)ccc2C(=O)NS(=O)(=O)c2cccc(N)n2)c(C)c1]
175
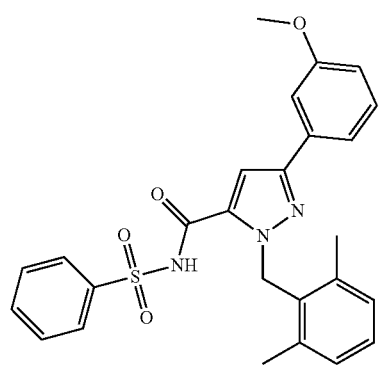 [SMILES: COc1cccc(-c2cc(C(=O)NS(=O)(=O)c3ccccc3)n(Cc3c(C)cccc3C)n2)c1]
176
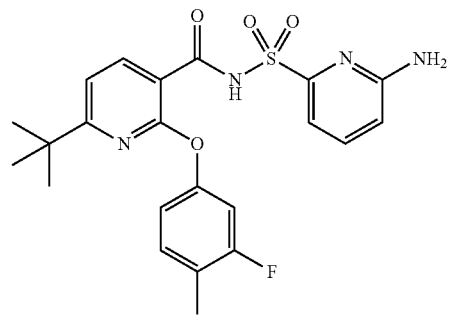 [SMILES: Cc1ccc(Oc2nc(C(C)(C)C)ccc2C(=O)NS(=O)(=O)c2cccc(N)n2)cc1F]
177
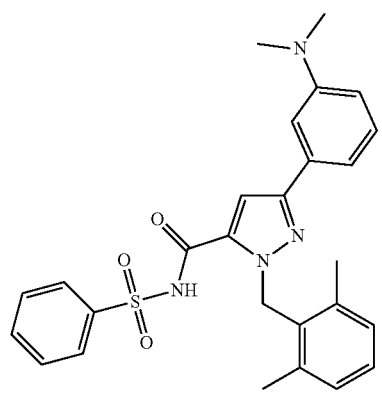 [SMILES: Cc1cccc(C)c1Cn1nc(-c2cccc(N(C)C)c2)cc1C(=O)NS(=O)(=O)c1ccccc1]
178

TABLE 1-continued
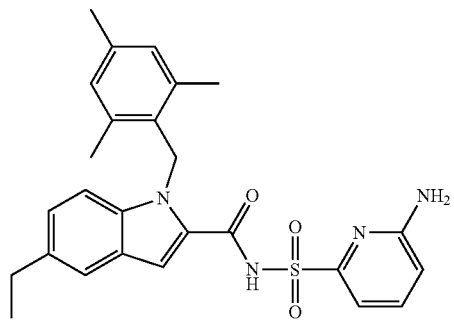 [SMILES: CCc1ccc2c(c1)cc(C(=O)NS(=O)(=O)c1cccc(N)n1)n2Cc1c(C)cc(C)cc1C] 179
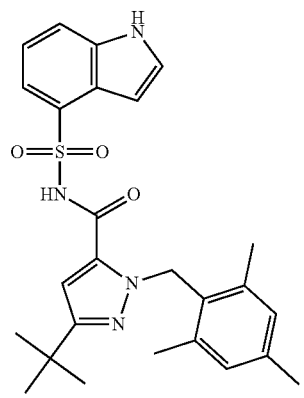 [SMILES: Cc1cc(C)c(Cn2nc(C(C)(C)C)cc2C(=O)NS(=O)(=O)c2cccc3[nH]ccc23)c(C)c1] 180
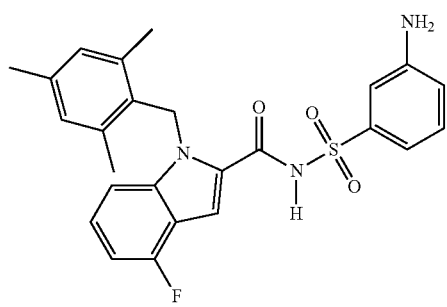 [SMILES: Cc1cc(C)c(Cn2c(C(=O)NS(=O)(=O)c3cccc(N)c3)cc3c(F)cccc32)c(C)c1] 181
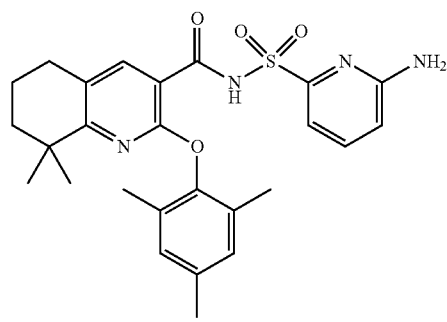 [SMILES: Cc1cc(C)c(Oc2nc3c(cc2C(=O)NS(=O)(=O)c2cccc(N)n2)CCCC3(C)C)c(C)c1] 182
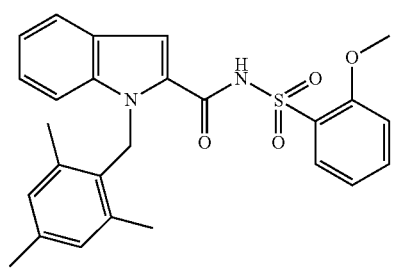 183

TABLE 1-continued
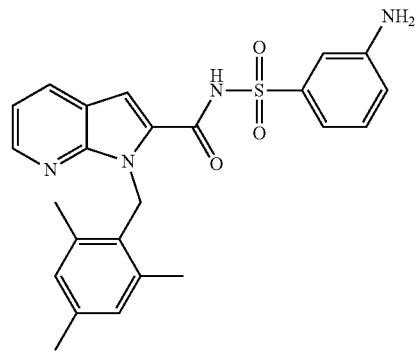 [SMILES: Cc1cc(C)c(Cn2c(C(=O)NS(=O)(=O)c3cccc(N)c3)cc3cccnc32)c(C)c1] 184
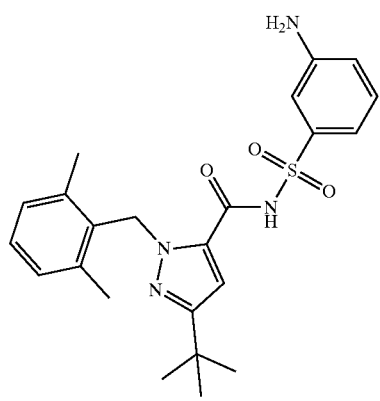 [SMILES: Cc1cccc(C)c1Cn1nc(C(C)(C)C)cc1C(=O)NS(=O)(=O)c1cccc(N)c1] 185
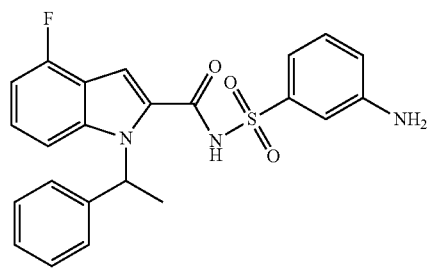 [SMILES: CC(c1ccccc1)n1c(C(=O)NS(=O)(=O)c2cccc(N)c2)cc2c(F)cccc21] 186
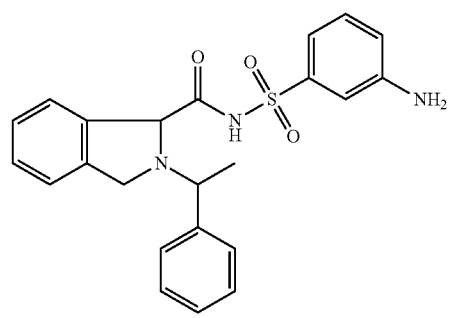 [SMILES: CC(c1ccccc1)N1Cc2ccccc2C1C(=O)NS(=O)(=O)c1cccc(N)c1] 187

TABLE 1-continued
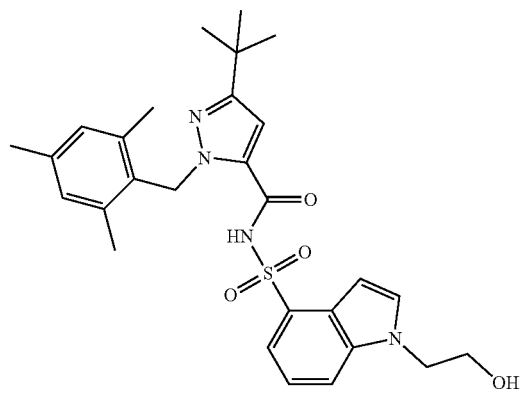 [SMILES: Cc1cc(C)c(Cn2nc(C(C)(C)C)cc2C(=O)NS(=O)(=O)c2cccc3c2ccn3CCO)c(C)c1]
188
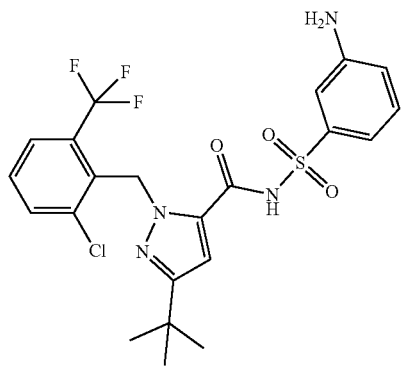 [SMILES: CC(C)(C)c1cc(C(=O)NS(=O)(=O)c2cccc(N)c2)n(Cc2c(Cl)cccc2C(F)(F)F)n1]
189
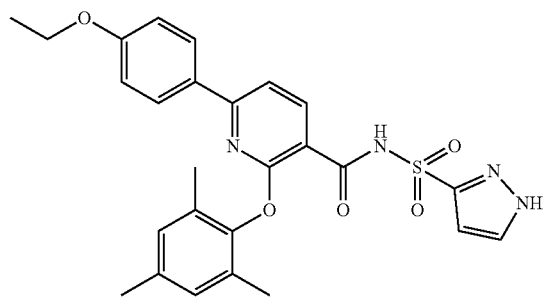 [SMILES: CCOc1ccc(-c2ccc(C(=O)NS(=O)(=O)c3cc[nH]n3)c(Oc3c(C)cc(C)cc3C)n2)cc1]
190
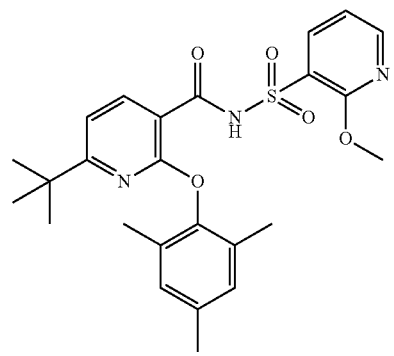 [SMILES: COc1ncccc1S(=O)(=O)NC(=O)c1ccc(C(C)(C)C)nc1Oc1c(C)cc(C)cc1C]
191

TABLE 1-continued
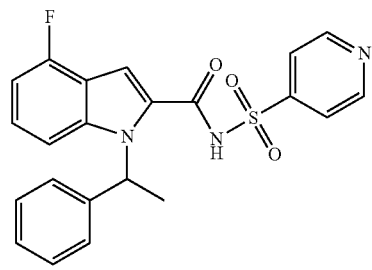 [SMILES: CC(c1ccccc1)n1c(C(=O)NS(=O)(=O)c2ccncc2)cc2c(F)cccc21] 192
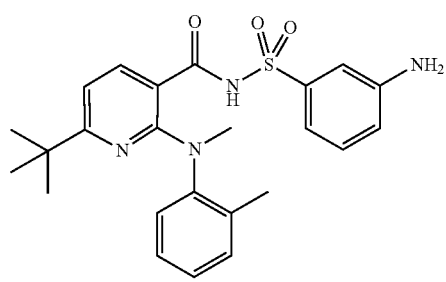 [SMILES: Cc1ccccc1N(C)c1nc(C(C)(C)C)ccc1C(=O)NS(=O)(=O)c1cccc(N)c1] 193
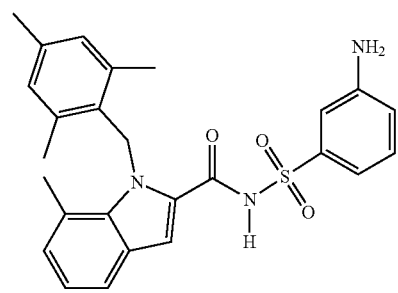 [SMILES: Cc1cc(C)c(Cn2c(C(=O)NS(=O)(=O)c3cccc(N)c3)cc3cccc(C)c32)c(C)c1] 194
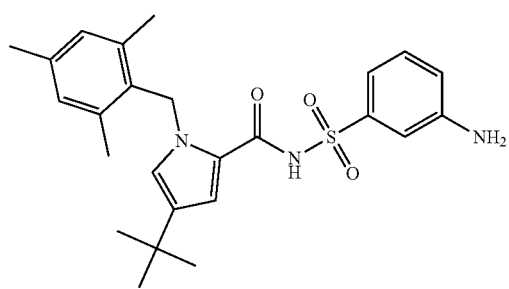 [SMILES: Cc1cc(C)c(Cn2cc(C(C)(C)C)cc2C(=O)NS(=O)(=O)c2cccc(N)c2)c(C)c1] 195
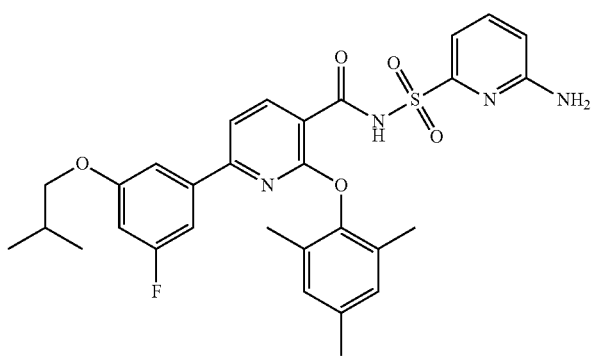 [SMILES: Cc1cc(C)c(Oc2nc(-c3cc(F)cc(OCC(C)C)c3)ccc2C(=O)NS(=O)(=O)c2cccc(N)n2)c(C)c1] 196

TABLE 1-continued
| | |
|---|---|
| 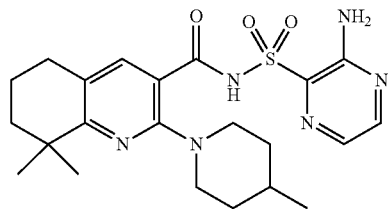 [SMILES: CC1CCN(c2nc3c(cc2C(=O)NS(=O)(=O)c2nccnc2N)CCCC3(C)C)CC1] | 197 |
| 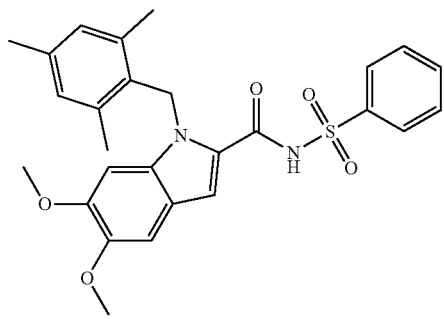 [SMILES: COc1cc2cc(C(=O)NS(=O)(=O)c3ccccc3)n(Cc3c(C)cc(C)cc3C)c2cc1OC] | 198 |
| 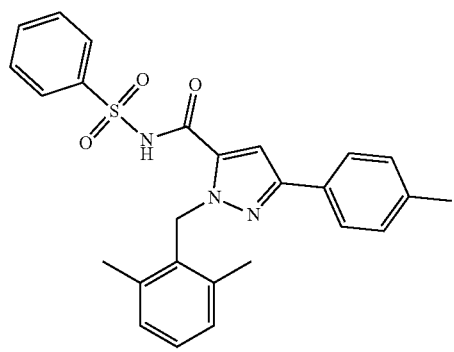 [SMILES: Cc1ccc(-c2cc(C(=O)NS(=O)(=O)c3ccccc3)n(Cc3c(C)cccc3C)n2)cc1] | 199 |
| 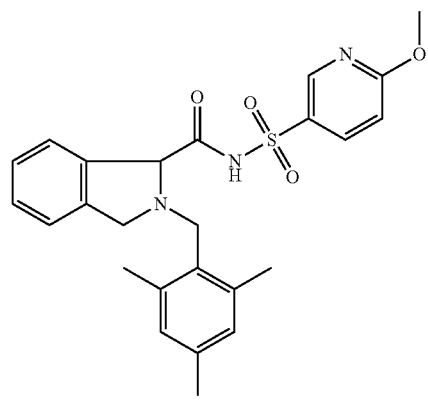 [SMILES: COc1ccc(S(=O)(=O)NC(=O)C2c3ccccc3CN2Cc2c(C)cc(C)cc2C)cn1] | 200 |
| 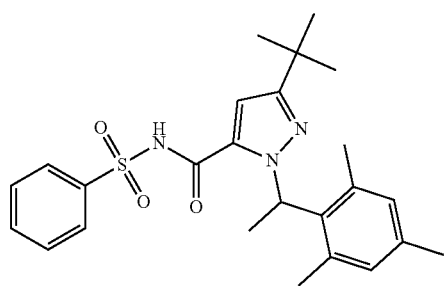 [SMILES: Cc1cc(C)c(C(C)n2nc(C(C)(C)C)cc2C(=O)NS(=O)(=O)c2ccccc2)c(C)c1] | 201 |

TABLE 1-continued
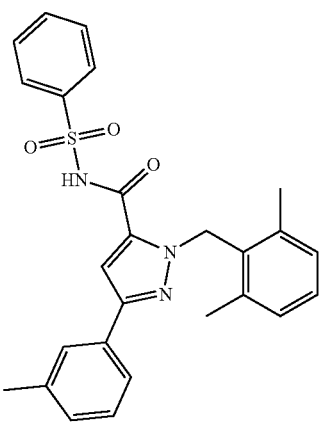 [SMILES: Cc1cccc(-c2cc(C(=O)NS(=O)(=O)c3ccccc3)n(Cc3c(C)cccc3C)n2)c1]
202
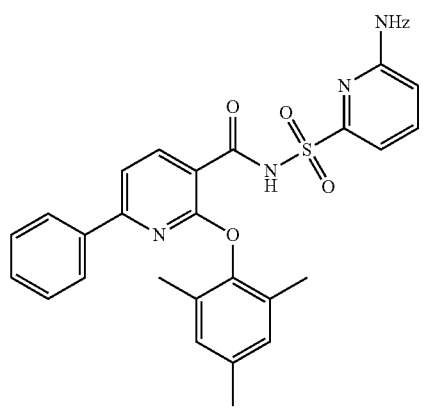
203
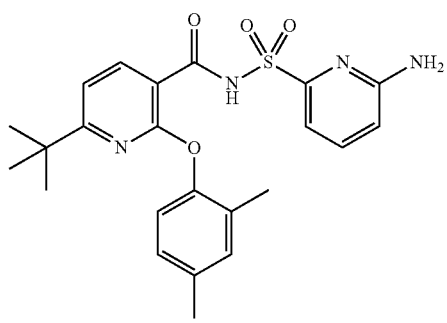 [SMILES: Cc1ccc(Oc2nc(C(C)(C)C)ccc2C(=O)NS(=O)(=O)c2cccc(N)n2)c(C)c1]
204
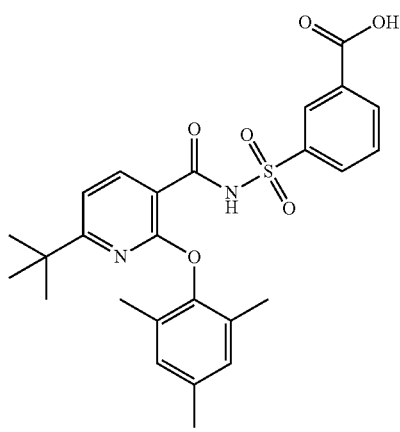 [SMILES: Cc1cc(C)c(Oc2nc(C(C)(C)C)ccc2C(=O)NS(=O)(=O)c2cccc(C(=O)O)c2)c(C)c1]
205

TABLE 1-continued
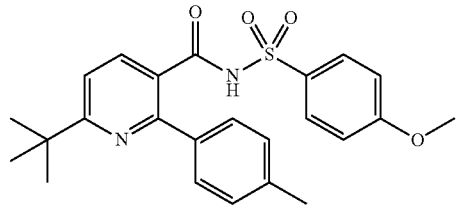 [SMILES: COc1ccc(S(=O)(=O)NC(=O)c2ccc(C(C)(C)C)nc2-c2ccc(C)cc2)cc1]
206
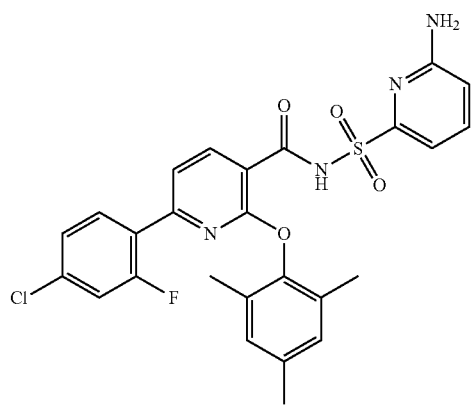 [SMILES: Cc1cc(C)c(Oc2nc(-c3ccc(Cl)cc3F)ccc2C(=O)NS(=O)(=O)c2cccc(N)n2)c(C)c1]
207
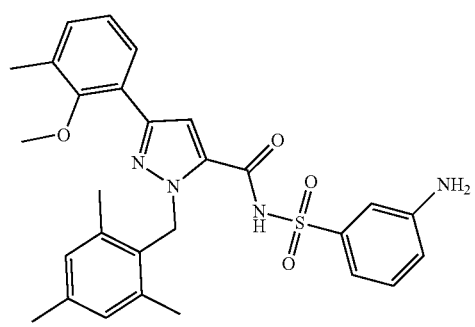 [SMILES: COc1c(C)cccc1-c1cc(C(=O)NS(=O)(=O)c2cccc(N)c2)n(Cc2c(C)cc(C)cc2C)n1]
208
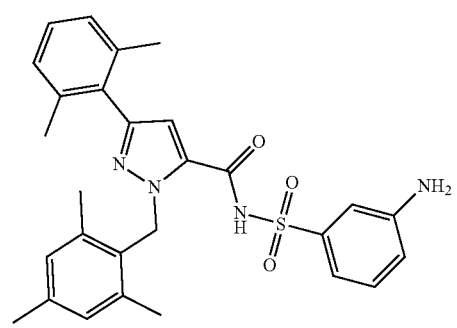 [SMILES: Cc1cc(C)c(Cn2nc(-c3c(C)cccc3C)cc2C(=O)NS(=O)(=O)c2cccc(N)c2)c(C)c1]
209

TABLE 1-continued
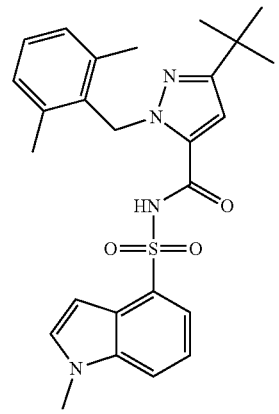 [SMILES: Cc1cccc(C)c1Cn1nc(C(C)(C)C)cc1C(=O)NS(=O)(=O)c1cccc2c1ccn2C]
210
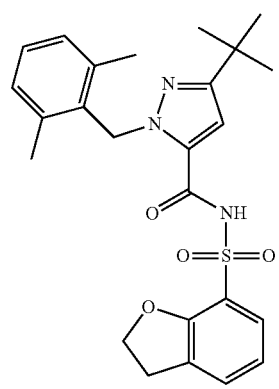 [SMILES: Cc1cccc(C)c1Cn1nc(C(C)(C)C)cc1C(=O)NS(=O)(=O)c1cccc2c1OCC2]
211
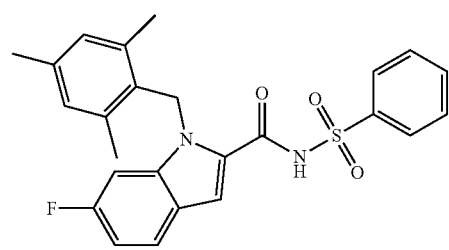 [SMILES: Cc1cc(C)c(Cn2c(C(=O)NS(=O)(=O)c3ccccc3)cc3ccc(F)cc32)c(C)c1]
212
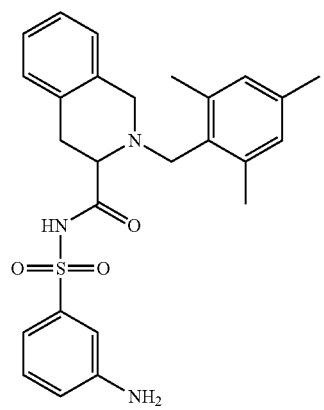 [SMILES: Cc1cc(C)c(CN2Cc3ccccc3CC2C(=O)NS(=O)(=O)c2cccc(N)c2)c(C)c1]
213

TABLE 1-continued
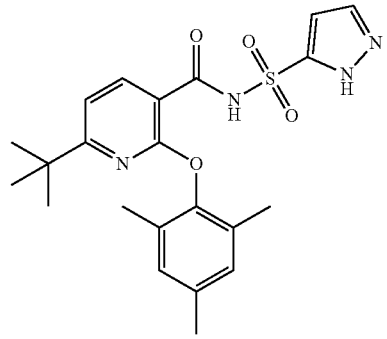 [SMILES: Cc1cc(C)c(Oc2nc(C(C)(C)C)ccc2C(=O)NS(=O)(=O)c2ccn[nH]2)c(C)c1]
214
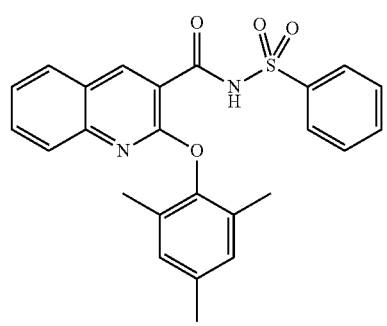 [SMILES: Cc1cc(C)c(Oc2nc3ccccc3cc2C(=O)NS(=O)(=O)c2ccccc2)c(C)c1]
215
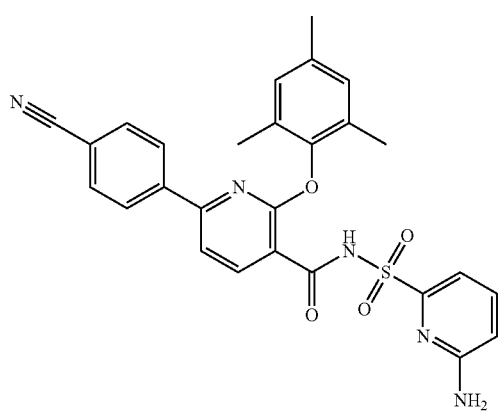 [SMILES: Cc1cc(C)c(Oc2nc(-c3ccc(C#N)cc3)ccc2C(=O)NS(=O)(=O)c2cccc(N)n2)c(C)c1]
216
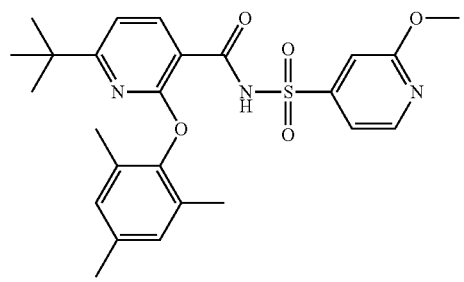 [SMILES: COc1cc(S(=O)(=O)NC(=O)c2ccc(C(C)(C)C)nc2Oc2c(C)cc(C)cc2C)ccn1]
217

TABLE 1-continued
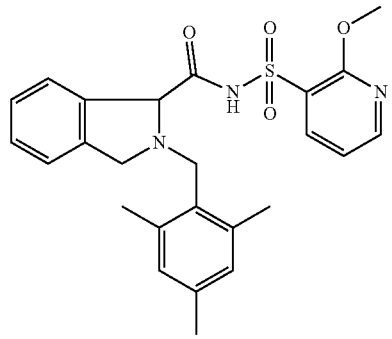 [SMILES: COc1ncccc1S(=O)(=O)NC(=O)C1c2ccccc2CN1Cc1c(C)cc(C)cc1C] 218
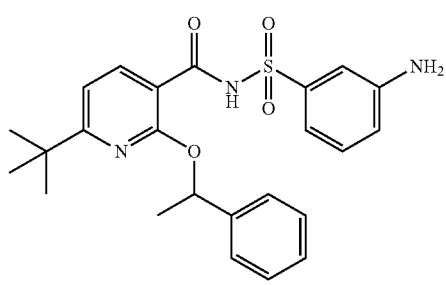 [SMILES: CC(Oc1nc(C(C)(C)C)ccc1C(=O)NS(=O)(=O)c1cccc(N)c1)c1ccccc1] 219
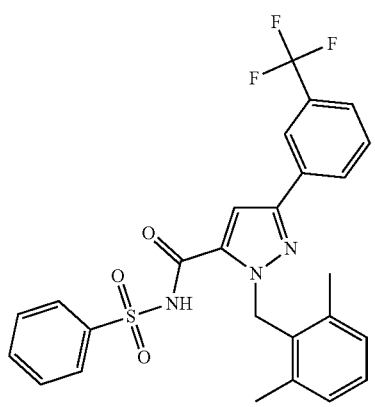 [SMILES: Cc1cccc(C)c1Cn1nc(-c2cccc(C(F)(F)F)c2)cc1C(=O)NS(=O)(=O)c1ccccc1] 220
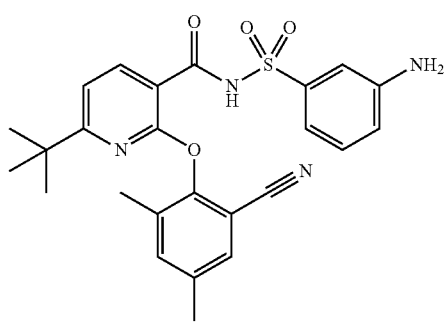 [SMILES: Cc1cc(C)c(Oc2nc(C(C)(C)C)ccc2C(=O)NS(=O)(=O)c2cccc(N)c2)c(C#N)c1] 221
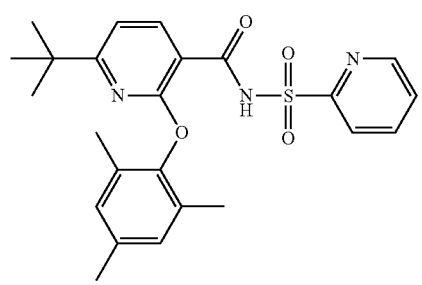 [SMILES: Cc1cc(C)c(Oc2nc(C(C)(C)C)ccc2C(=O)NS(=O)(=O)c2ccccn2)c(C)c1] 222

TABLE 1-continued
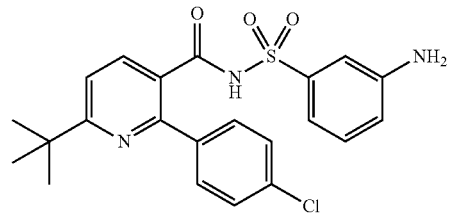 [SMILES: CC(C)(C)c1ccc(C(=O)NS(=O)(=O)c2cccc(N)c2)c(-c2ccc(Cl)cc2)n1]
223
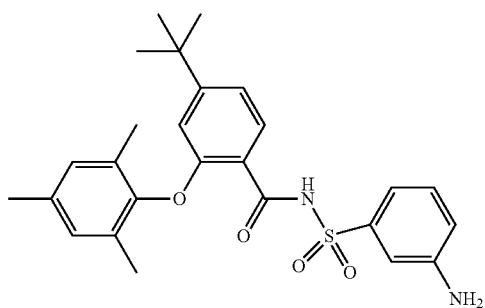 [SMILES: Cc1cc(C)c(Oc2cc(C(C)(C)C)ccc2C(=O)NS(=O)(=O)c2cccc(N)c2)c(C)c1]
224
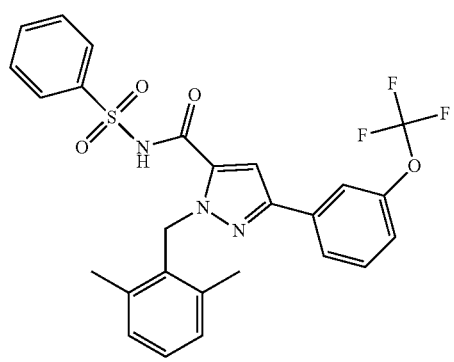 [SMILES: Cc1cccc(C)c1Cn1nc(-c2cccc(OC(F)(F)F)c2)cc1C(=O)NS(=O)(=O)c1ccccc1]
225
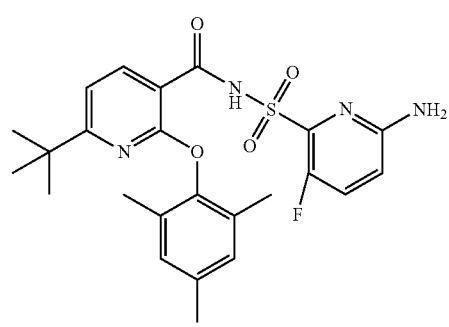 [SMILES: Cc1cc(C)c(Oc2nc(C(C)(C)C)ccc2C(=O)NS(=O)(=O)c2nc(N)ccc2F)c(C)c1]
226
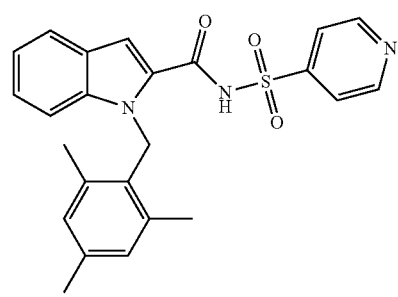 [SMILES: Cc1cc(C)c(Cn2c(C(=O)NS(=O)(=O)c3ccncc3)cc3ccccc32)c(C)c1]
227

TABLE 1-continued
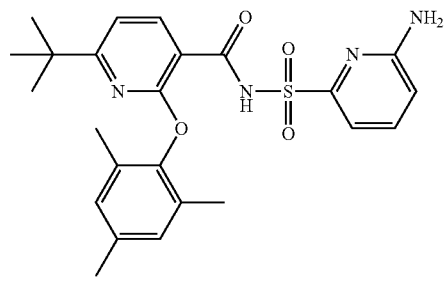 [SMILES: Cc1cc(C)c(Oc2nc(C(C)(C)C)ccc2C(=O)NS(=O)(=O)c2cccc(N)n2)c(C)c1] 228
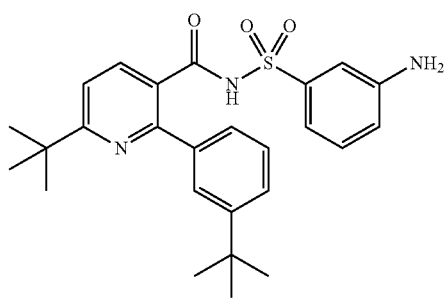 [SMILES: CC(C)(C)c1cccc(-c2nc(C(C)(C)C)ccc2C(=O)NS(=O)(=O)c2cccc(N)c2)c1] 229
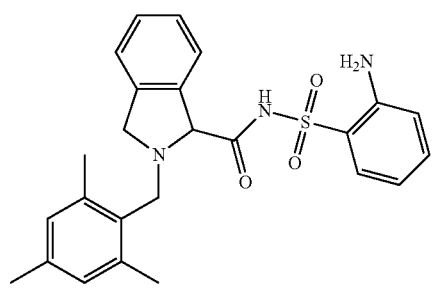 [SMILES: Cc1cc(C)c(CN2Cc3ccccc3C2C(=O)NS(=O)(=O)c2ccccc2N)c(C)c1] 230
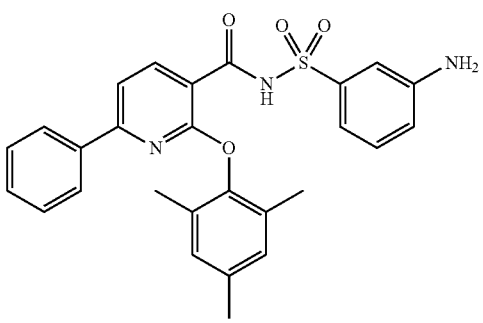 [SMILES: Cc1cc(C)c(Oc2nc(-c3ccccc3)ccc2C(=O)NS(=O)(=O)c2cccc(N)c2)c(C)c1] 231
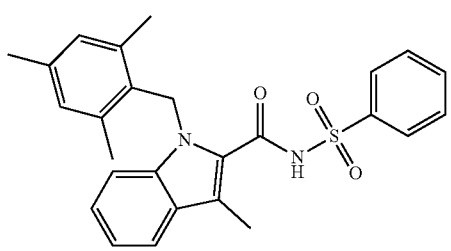 [SMILES: Cc1cc(C)c(Cn2c(C(=O)NS(=O)(=O)c3ccccc3)c(C)c3ccccc32)c(C)c1] 232

TABLE 1-continued
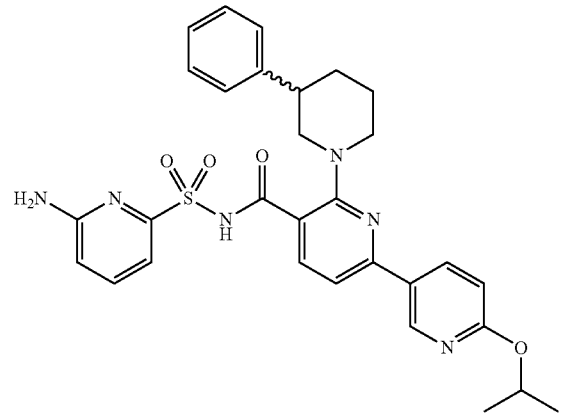 [SMILES: CC(C)Oc1ccc(-c2ccc(C(=O)NS(=O)(=O)c3cccc(N)n3)c(N3CCCC(c4ccccc4)C3)n2)cn1]
233
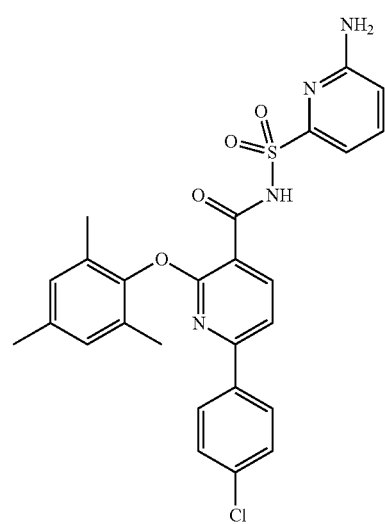 [SMILES: Cc1cc(C)c(Oc2nc(-c3ccc(Cl)cc3)ccc2C(=O)NS(=O)(=O)c2cccc(N)n2)c(C)c1]
234
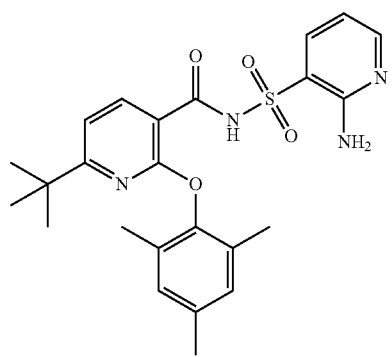 [SMILES: Cc1cc(C)c(Oc2nc(C(C)(C)C)ccc2C(=O)NS(=O)(=O)c2cccnc2N)c(C)c1]
235

TABLE 1-continued
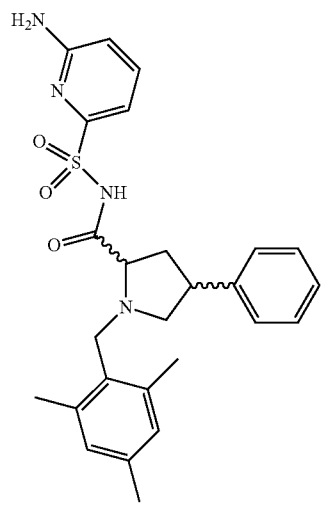 [SMILES: Cc1cc(C)c(CN2CC(c3ccccc3)CC2C(=O)NS(=O)(=O)c2cccc(N)n2)c(C)c1]
236
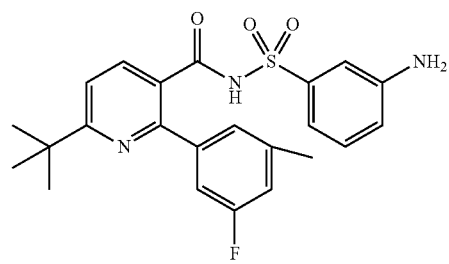 [SMILES: Cc1cc(F)cc(-c2nc(C(C)(C)C)ccc2C(=O)NS(=O)(=O)c2cccc(N)c2)c1]
237
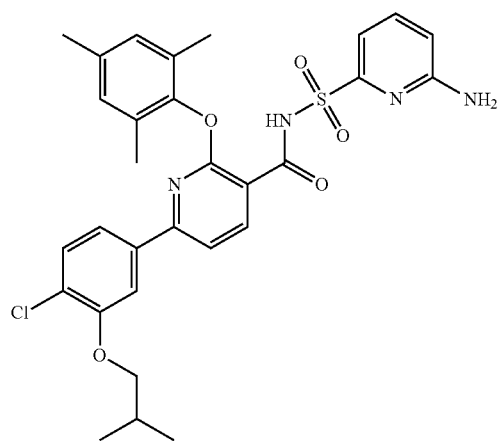 [SMILES: Cc1cc(C)c(Oc2nc(-c3ccc(Cl)c(OCC(C)C)c3)ccc2C(=O)NS(=O)(=O)c2cccc(N)n2)c(C)c1]
238
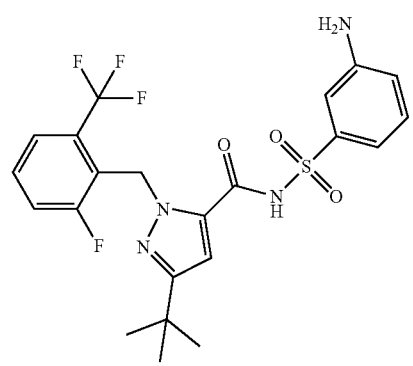 [SMILES: CC(C)(C)c1cc(C(=O)NS(=O)(=O)c2cccc(N)c2)n(Cc2c(F)cccc2C(F)(F)F)n1]
239

TABLE 1-continued
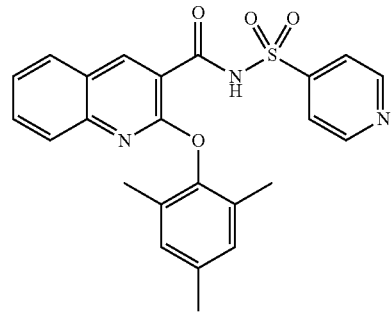 [SMILES: Cc1cc(C)c(Oc2nc3ccccc3cc2C(=O)NS(=O)(=O)c2ccncc2)c(C)c1]
240
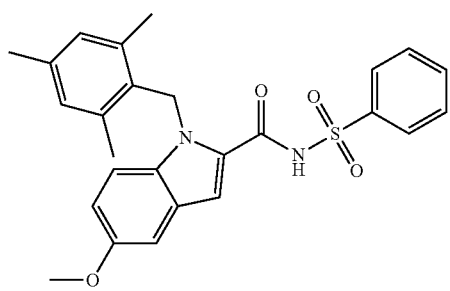 [SMILES: COc1ccc2c(c1)cc(C(=O)NS(=O)(=O)c1ccccc1)n2Cc1c(C)cc(C)cc1C]
241
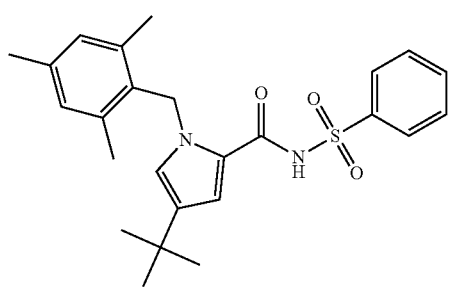 [SMILES: Cc1cc(C)c(Cn2cc(C(C)(C)C)cc2C(=O)NS(=O)(=O)c2ccccc2)c(C)c1]
242
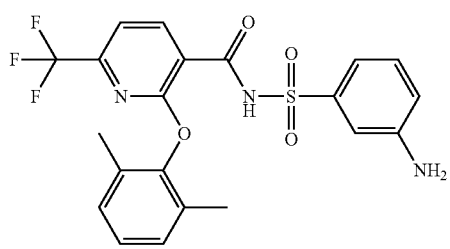 [SMILES: Cc1cccc(C)c1Oc1nc(C(F)(F)F)ccc1C(=O)NS(=O)(=O)c1cccc(N)c1]
243
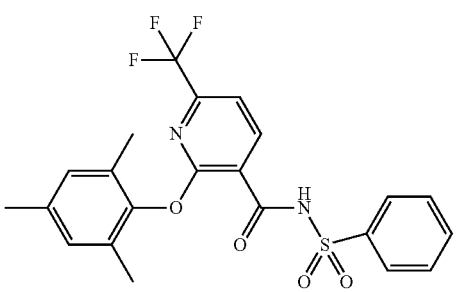 [SMILES: Cc1cc(C)c(Oc2nc(C(F)(F)F)ccc2C(=O)NS(=O)(=O)c2ccccc2)c(C)c1]
244

TABLE 1-continued
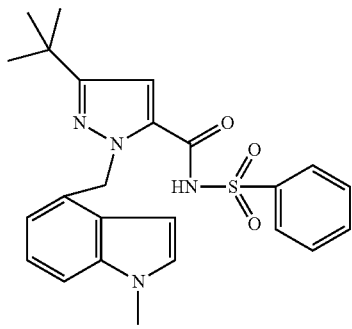 [SMILES: Cn1ccc2c(Cn3nc(C(C)(C)C)cc3C(=O)NS(=O)(=O)c3ccccc3)cccc21]
245
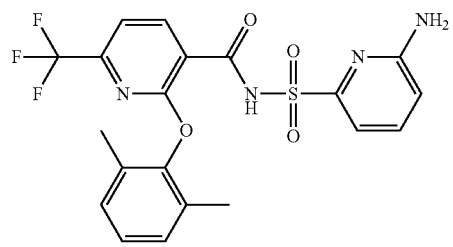 [SMILES: Cc1cccc(C)c1Oc1nc(C(F)(F)F)ccc1C(=O)NS(=O)(=O)c1cccc(N)n1]
246
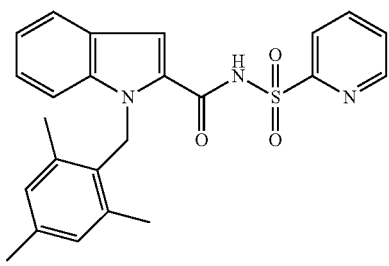 [SMILES: Cc1cc(C)c(Cn2c(C(=O)NS(=O)(=O)c3ccccn3)cc3ccccc32)c(C)c1]
247
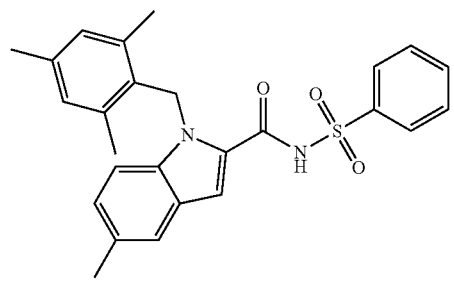 [SMILES: Cc1cc(C)c(Cn2c(C(=O)NS(=O)(=O)c3ccccc3)cc3cc(C)ccc32)c(C)c1]
248
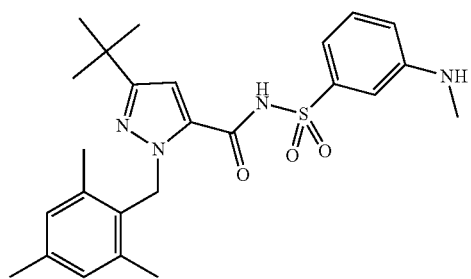
249

TABLE 1-continued
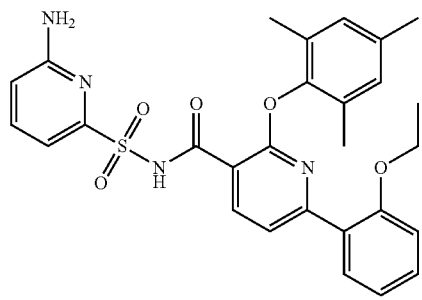 [SMILES: CCOc1ccccc1-c1ccc(C(=O)NS(=O)(=O)c2cccc(N)n2)c(Oc2c(C)cc(C)cc2C)n1]
250
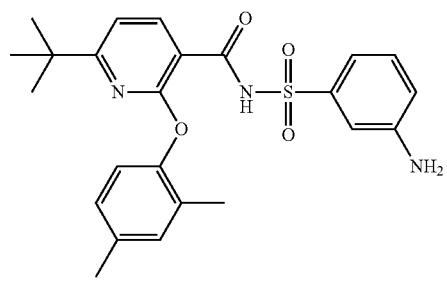 [SMILES: Cc1ccc(Oc2nc(C(C)(C)C)ccc2C(=O)NS(=O)(=O)c2cccc(N)c2)c(C)c1]
251
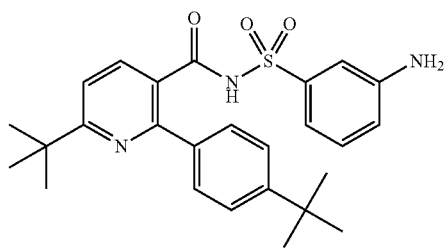 [SMILES: CC(C)(C)c1ccc(-c2nc(C(C)(C)C)ccc2C(=O)NS(=O)(=O)c2cccc(N)c2)cc1]
252
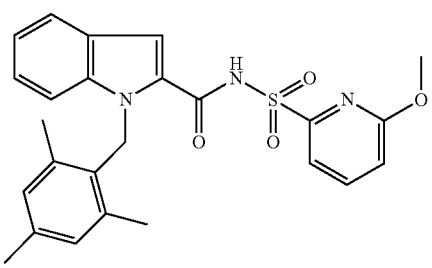
253
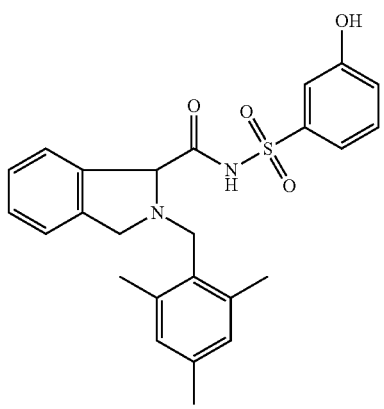 [SMILES: Cc1cc(C)c(CN2Cc3ccccc3C2C(=O)NS(=O)(=O)c2cccc(O)c2)c(C)c1]
254

TABLE 1-continued
| | |
|---|---|
| 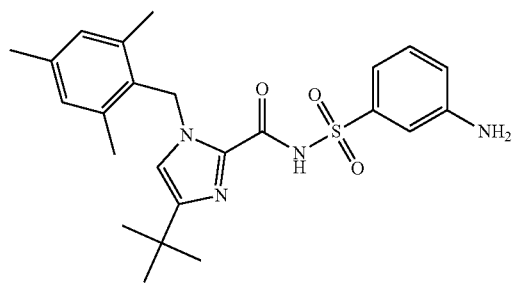 [SMILES: Cc1cc(C)c(Cn2cc(C(C)(C)C)nc2C(=O)NS(=O)(=O)c2cccc(N)c2)c(C)c1] | 255 |
| 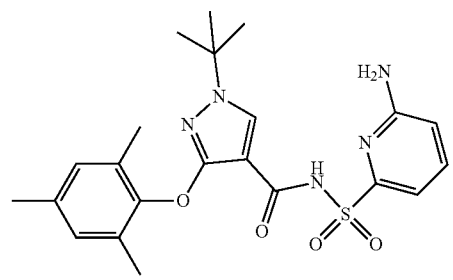 [SMILES: Cc1cc(C)c(Oc2nn(C(C)(C)C)cc2C(=O)NS(=O)(=O)c2cccc(N)n2)c(C)c1] | 256 |
| 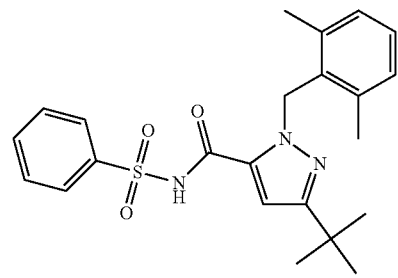 [SMILES: Cc1cccc(C)c1Cn1nc(C(C)(C)C)cc1C(=O)NS(=O)(=O)c1ccccc1] | 257 |
| 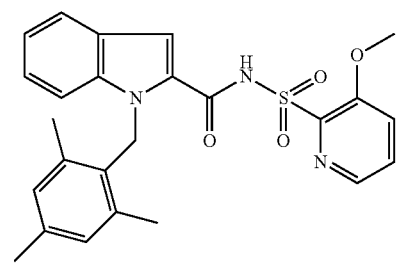 | 258 |
| 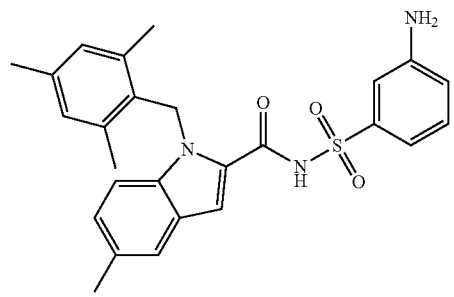 [SMILES: Cc1cc(C)c(Cn2c(C(=O)NS(=O)(=O)c3cccc(N)c3)cc3cc(C)ccc32)c(C)c1] | 259 |

TABLE 1-continued
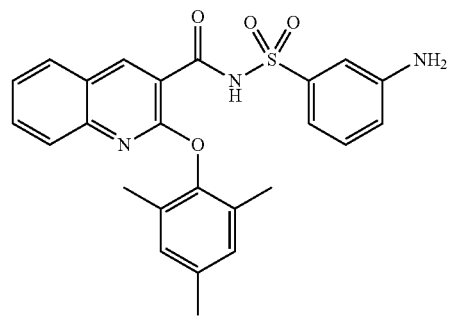 [SMILES: Cc1cc(C)c(Oc2nc3ccccc3cc2C(=O)NS(=O)(=O)c2cccc(N)c2)c(C)c1] 260
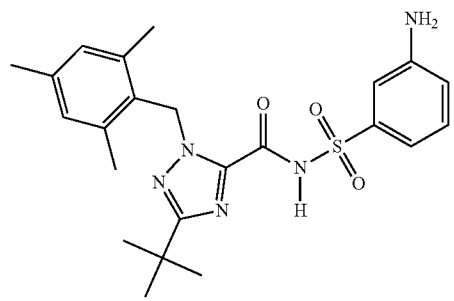 [SMILES: Cc1cc(C)c(Cn2nc(C(C)(C)C)nc2C(=O)NS(=O)(=O)c2cccc(N)c2)c(C)c1] 261
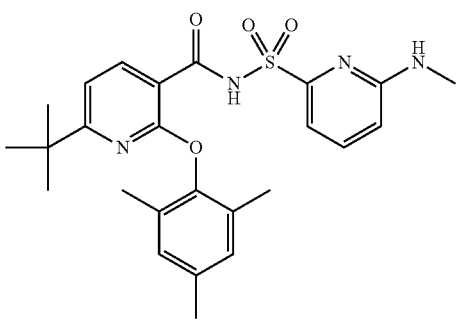 [SMILES: CNc1cccc(S(=O)(=O)NC(=O)c2ccc(C(C)(C)C)nc2Oc2c(C)cc(C)cc2C)n1] 262
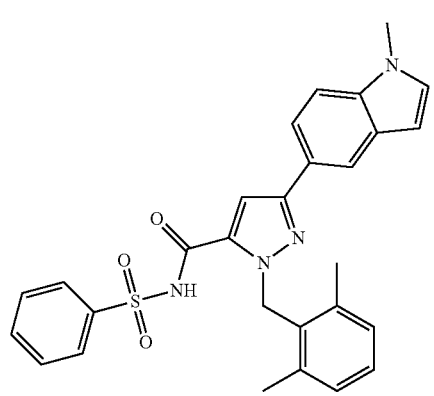 [SMILES: Cc1cccc(C)c1Cn1nc(-c2ccc3c(ccn3C)c2)cc1C(=O)NS(=O)(=O)c1ccccc1] 263
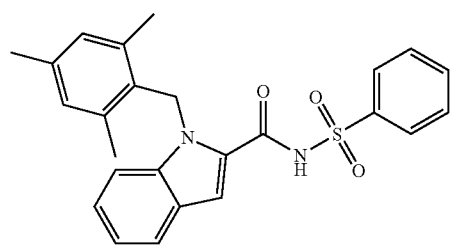 [SMILES: Cc1cc(C)c(Cn2c(C(=O)NS(=O)(=O)c3ccccc3)cc3ccccc32)c(C)c1] 264

TABLE 1-continued
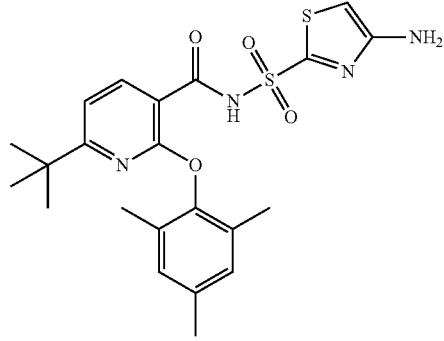 [SMILES: Cc1cc(C)c(Oc2nc(C(C)(C)C)ccc2C(=O)NS(=O)(=O)c2nc(N)cs2)c(C)c1] 265
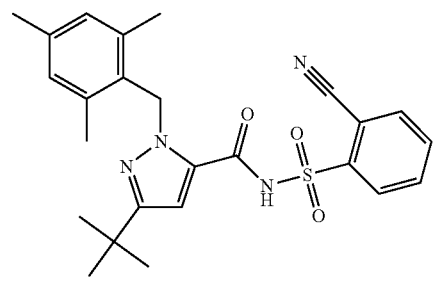 [SMILES: Cc1cc(C)c(Cn2nc(C(C)(C)C)cc2C(=O)NS(=O)(=O)c2ccccc2C#N)c(C)c1] 266
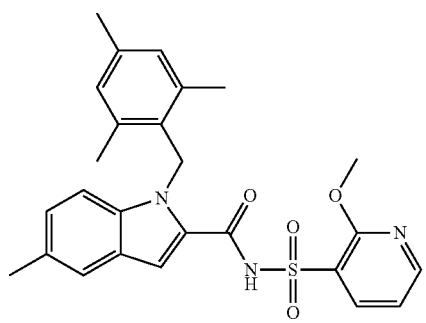 [SMILES: COc1ncccc1S(=O)(=O)NC(=O)c1cc2cc(C)ccc2n1Cc1c(C)cc(C)cc1C] 267
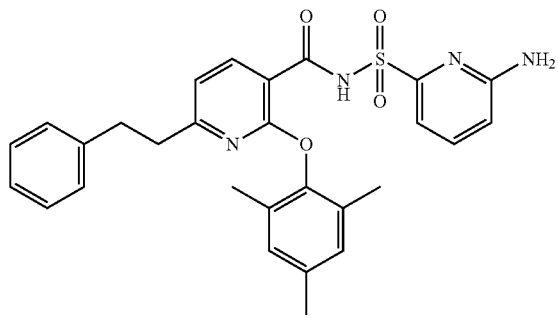 [SMILES: Cc1cc(C)c(Oc2nc(CCc3ccccc3)ccc2C(=O)NS(=O)(=O)c2cccc(N)n2)c(C)c1] 268
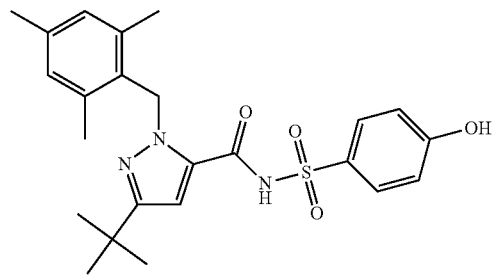 [SMILES: Cc1cc(C)c(Cn2nc(C(C)(C)C)cc2C(=O)NS(=O)(=O)c2ccc(O)cc2)c(C)c1] 269

TABLE 1-continued
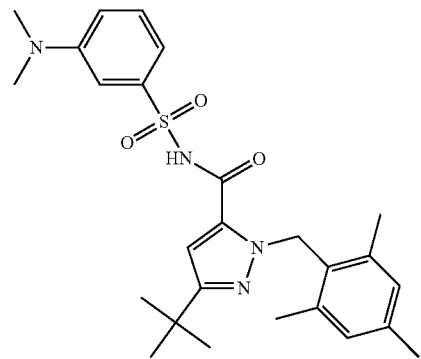 270
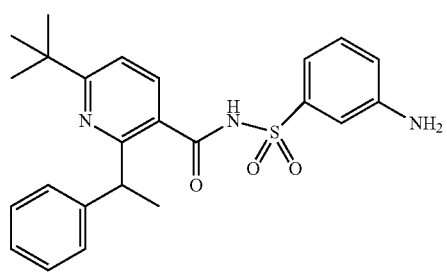 [SMILES: CC(c1ccccc1)c1nc(C(C)(C)C)ccc1C(=O)NS(=O)(=O)c1cccc(N)c1] 271
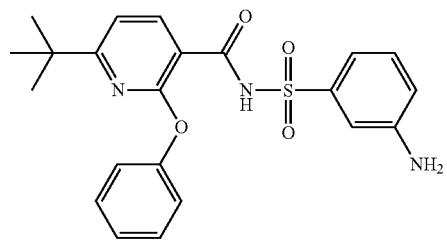 [SMILES: CC(C)(C)c1ccc(C(=O)NS(=O)(=O)c2cccc(N)c2)c(Oc2ccccc2)n1] 272
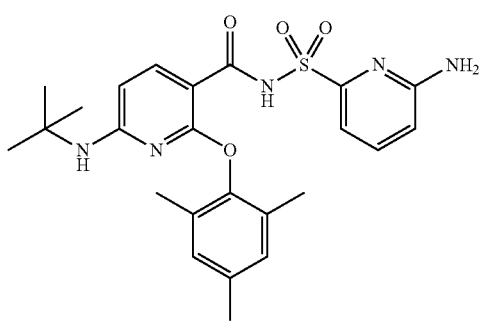 273
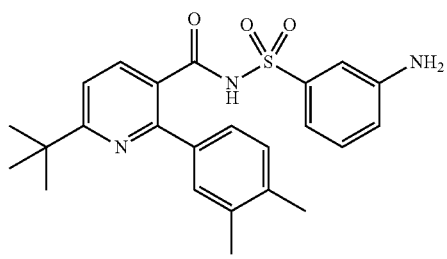 [SMILES: Cc1ccc(-c2nc(C(C)(C)C)ccc2C(=O)NS(=O)(=O)c2cccc(N)c2)cc1C] 274

TABLE 1-continued

| | |
|---|---|
| (structure) | 275 |
| (structure) | 276 |
| (structure) | 277 |
| (structure) | 278 |

TABLE 1-continued
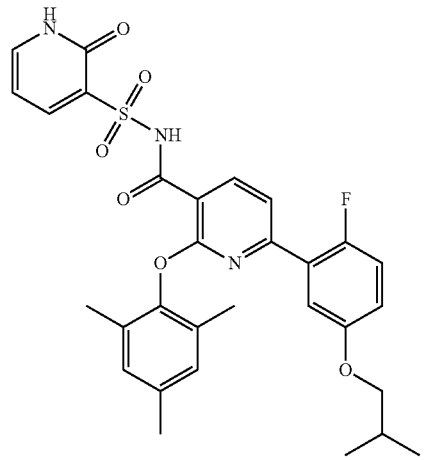 [SMILES: Cc1cc(C)c(Oc2nc(-c3cc(OCC(C)C)ccc3F)ccc2C(=O)NS(=O)(=O)c2ccc[nH]c2=O)c(C)c1]
279
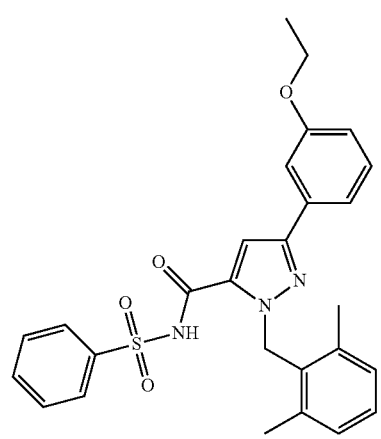 [SMILES: CCOc1cccc(-c2cc(C(=O)NS(=O)(=O)c3ccccc3)n(Cc3c(C)cccc3C)n2)c1]
280
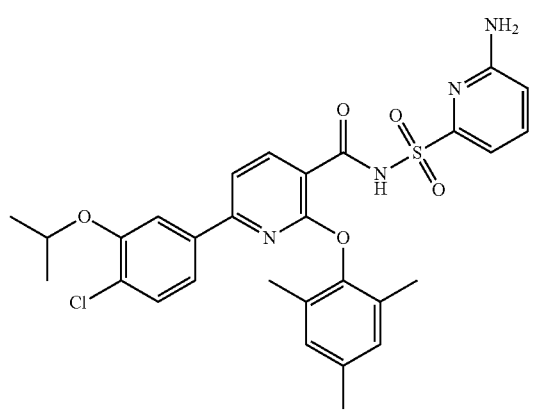 [SMILES: Cc1cc(C)c(Oc2nc(-c3ccc(Cl)c(OC(C)C)c3)ccc2C(=O)NS(=O)(=O)c2cccc(N)n2)c(C)c1]
281
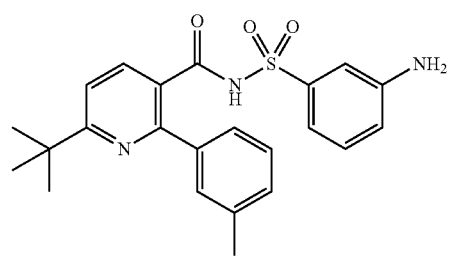 [SMILES: Cc1cccc(-c2nc(C(C)(C)C)ccc2C(=O)NS(=O)(=O)c2cccc(N)c2)c1]
282

TABLE 1-continued
| | |
|---|---|
| 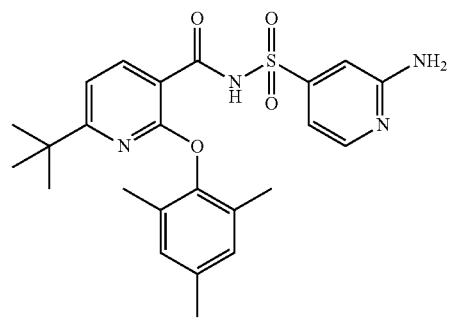 [SMILES: Cc1cc(C)c(Oc2nc(C(C)(C)C)ccc2C(=O)NS(=O)(=O)c2ccnc(N)c2)c(C)c1] | 283 |
| 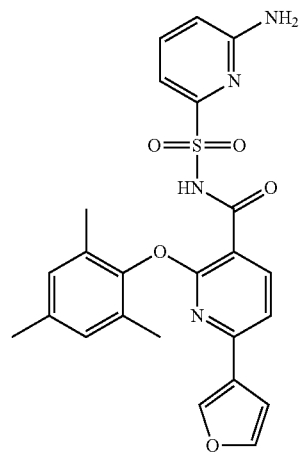 [SMILES: Cc1cc(C)c(Oc2nc(-c3ccoc3)ccc2C(=O)NS(=O)(=O)c2cccc(N)n2)c(C)c1] | 284 |
| 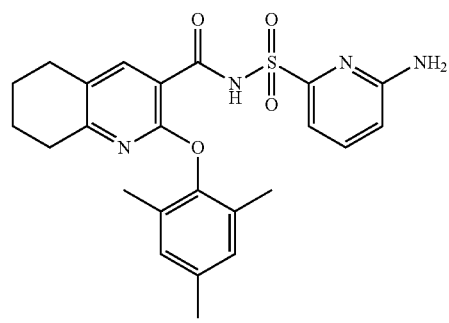 [SMILES: Cc1cc(C)c(Oc2nc3c(cc2C(=O)NS(=O)(=O)c2cccc(N)n2)CCCC3)c(C)c1] | 285 |
| 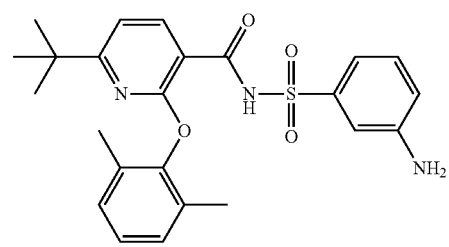 [SMILES: Cc1cccc(C)c1Oc1nc(C(C)(C)C)ccc1C(=O)NS(=O)(=O)c1cccc(N)c1] | 286 |
| 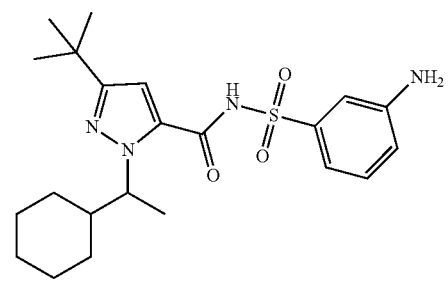 [SMILES: CC(C1CCCCC1)n1nc(C(C)(C)C)cc1C(=O)NS(=O)(=O)c1cccc(N)c1] | 287 |

TABLE 1-continued
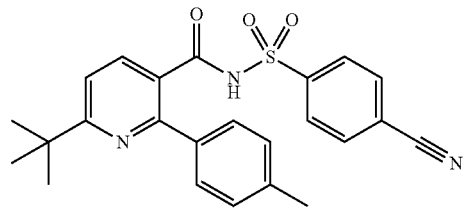 [SMILES: Cc1ccc(-c2nc(C(C)(C)C)ccc2C(=O)NS(=O)(=O)c2ccc(C#N)cc2)cc1]
288
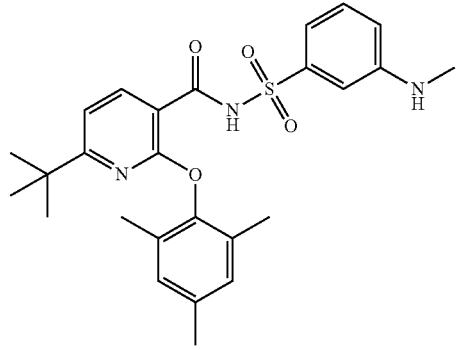 [SMILES: CNc1cccc(S(=O)(=O)NC(=O)c2ccc(C(C)(C)C)nc2Oc2c(C)cc(C)cc2C)c1]
289
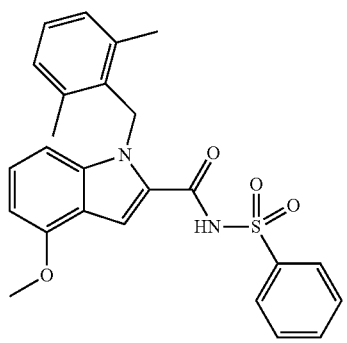 [SMILES: COc1cccc2c1cc(C(=O)NS(=O)(=O)c1ccccc1)n2Cc1c(C)cccc1C]
290
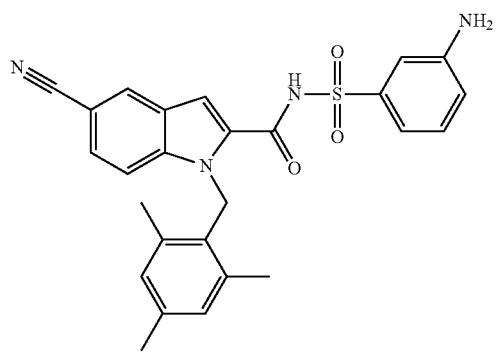 [SMILES: Cc1cc(C)c(Cn2c(C(=O)NS(=O)(=O)c3cccc(N)c3)cc3cc(C#N)ccc32)c(C)c1]
291
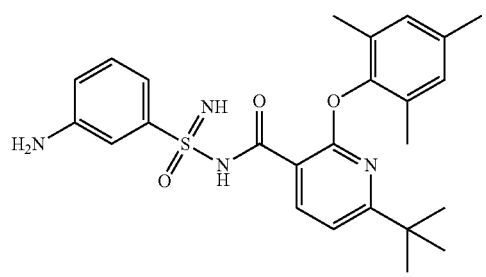 [SMILES: Cc1cc(C)c(Oc2nc(C(C)(C)C)ccc2C(=O)NS(=N)(=O)c2cccc(N)c2)c(C)c1]
292

TABLE 1-continued
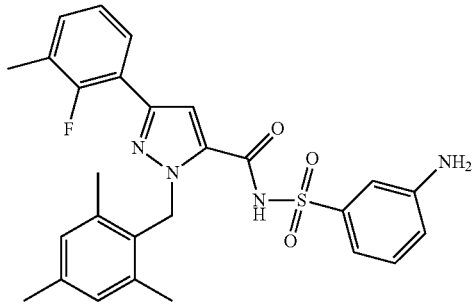 [SMILES: Cc1cc(C)c(Cn2nc(-c3cccc(C)c3F)cc2C(=O)NS(=O)(=O)c2cccc(N)c2)c(C)c1]
293
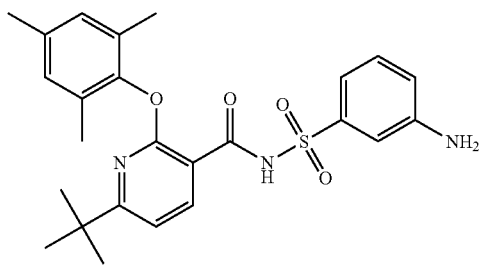 [SMILES: Cc1cc(C)c(Oc2nc(C(C)(C)C)ccc2C(=O)NS(=O)(=O)c2cccc(N)c2)c(C)c1]
294
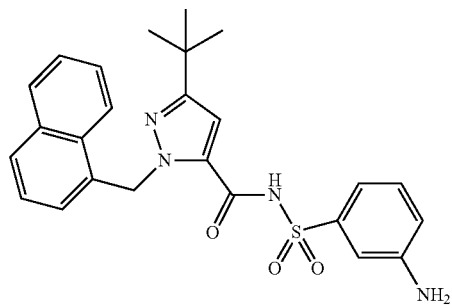 [SMILES: CC(C)(C)c1cc(C(=O)NS(=O)(=O)c2cccc(N)c2)n(Cc2cccc3ccccc23)n1]
295
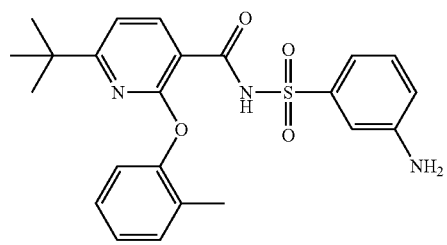 [SMILES: Cc1ccccc1Oc1nc(C(C)(C)C)ccc1C(=O)NS(=O)(=O)c1cccc(N)c1]
296
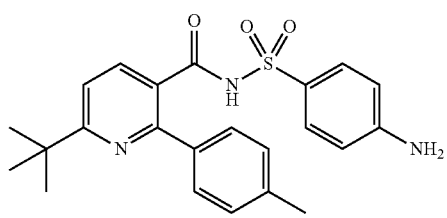 [SMILES: Cc1ccc(-c2nc(C(C)(C)C)ccc2C(=O)NS(=O)(=O)c2ccc(N)cc2)cc1]
297

TABLE 1-continued
| | |
|---|---|
| 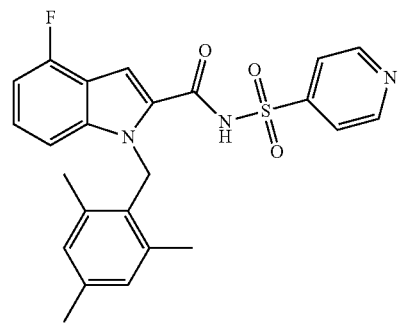 [SMILES: Cc1cc(C)c(Cn2c(C(=O)NS(=O)(=O)c3ccncc3)cc3c(F)cccc32)c(C)c1] | 298 |
| 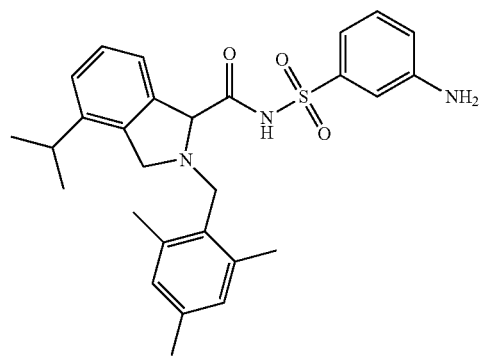 [SMILES: Cc1cc(C)c(CN2Cc3c(C(C)C)cccc3C2C(=O)NS(=O)(=O)c2cccc(N)c2)c(C)c1] | 299 |
| 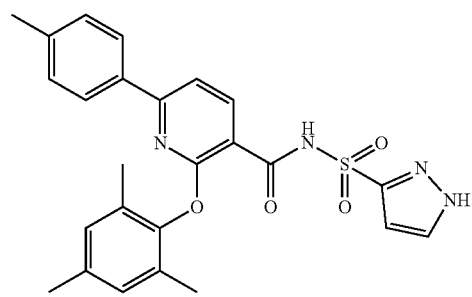 [SMILES: Cc1ccc(-c2ccc(C(=O)NS(=O)(=O)c3cc[nH]n3)c(Oc3c(C)cc(C)cc3C)n2)cc1] | 300 |
| 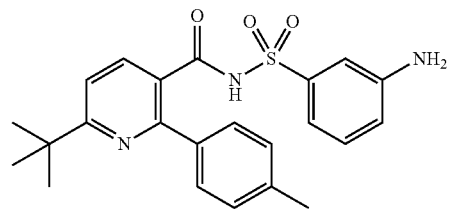 [SMILES: Cc1ccc(-c2nc(C(C)(C)C)ccc2C(=O)NS(=O)(=O)c2cccc(N)c2)cc1] | 301 |
| 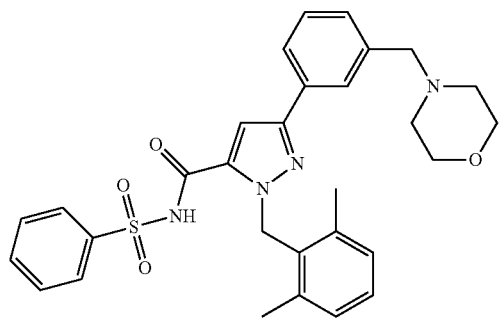 [SMILES: Cc1cccc(C)c1Cn1nc(-c2cccc(CN3CCOCC3)c2)cc1C(=O)NS(=O)(=O)c1ccccc1] | 302 |

TABLE 1-continued
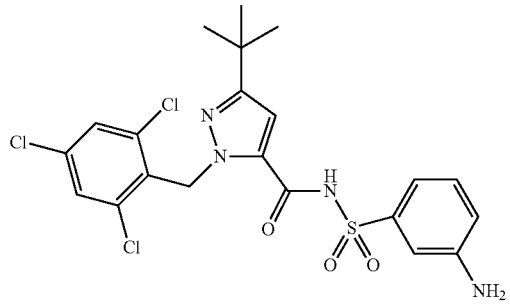 [SMILES: CC(C)(C)c1cc(C(=O)NS(=O)(=O)c2cccc(N)c2)n(Cc2c(Cl)cc(Cl)cc2Cl)n1]
303
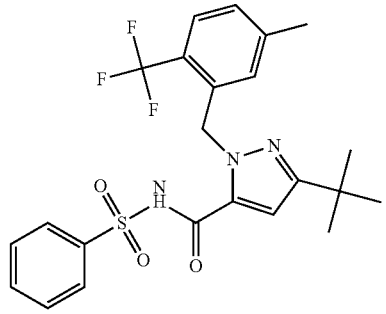 [SMILES: Cc1ccc(C(F)(F)F)c(Cn2nc(C(C)(C)C)cc2C(=O)NS(=O)(=O)c2ccccc2)c1]
304
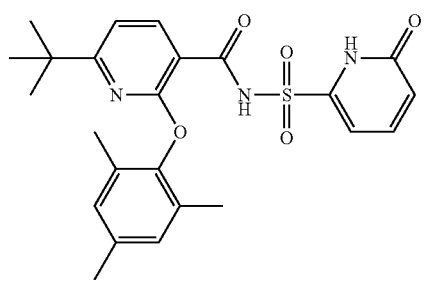 [SMILES: Cc1cc(C)c(Oc2nc(C(C)(C)C)ccc2C(=O)NS(=O)(=O)c2cccc(=O)[nH]2)c(C)c1]
305
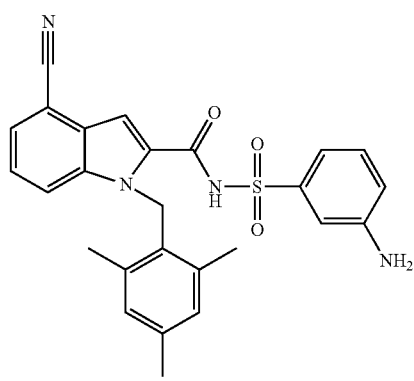 [SMILES: Cc1cc(C)c(Cn2c(C(=O)NS(=O)(=O)c3cccc(N)c3)cc3c(C#N)cccc32)c(C)c1]
306
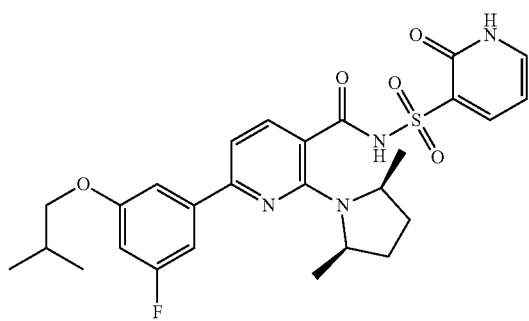 [SMILES: CC(C)COc1cc(F)cc(-c2ccc(C(=O)NS(=O)(=O)c3ccc[nH]c3=O)c(N3[C@H](C)CC[C@@H]3C)n2)c1]
307

TABLE 1-continued
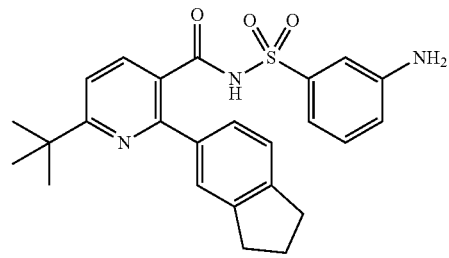 [SMILES: CC(C)(C)c1ccc(C(=O)NS(=O)(=O)c2cccc(N)c2)c(-c2ccc3c(c2)CCC3)n1]
308
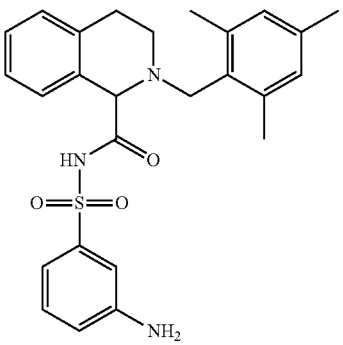 [SMILES: Cc1cc(C)c(CN2CCc3ccccc3C2C(=O)NS(=O)(=O)c2cccc(N)c2)c(C)c1]
309
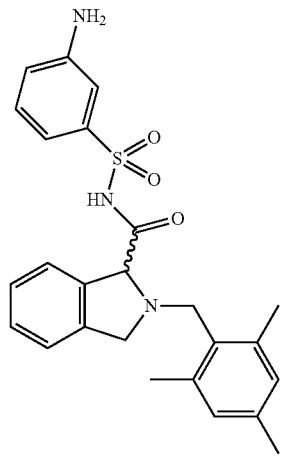 [SMILES: Cc1cc(C)c(CN2Cc3ccccc3C2C(=O)NS(=O)(=O)c2cccc(N)c2)c(C)c1]
310
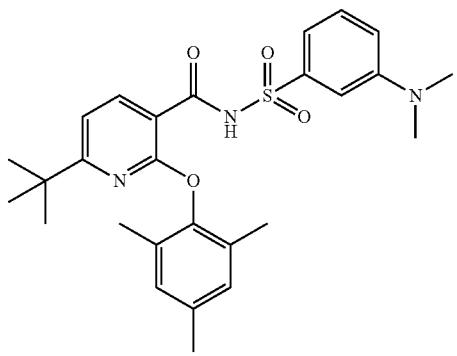 [SMILES: Cc1cc(C)c(Oc2nc(C(C)(C)C)ccc2C(=O)NS(=O)(=O)c2cccc(N(C)C)c2)c(C)c1]
311

TABLE 1-continued
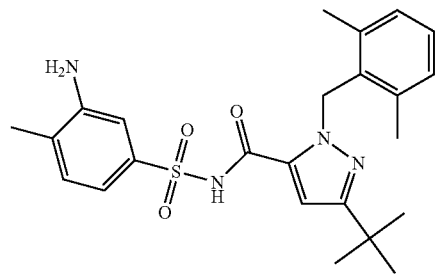 [SMILES: Cc1ccc(S(=O)(=O)NC(=O)c2cc(C(C)(C)C)nn2Cc2c(C)cccc2C)cc1N] 312
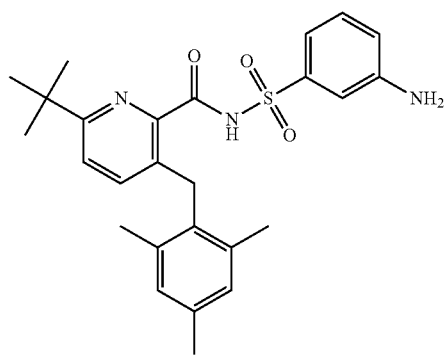 [SMILES: Cc1cc(C)c(Cc2ccc(C(C)(C)C)nc2C(=O)NS(=O)(=O)c2cccc(N)c2)c(C)c1] 313
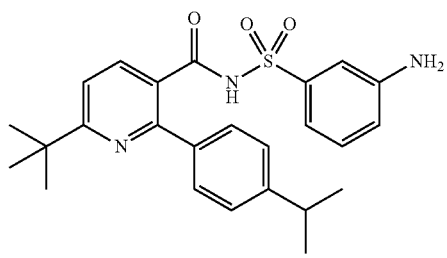 [SMILES: CC(C)c1ccc(-c2nc(C(C)(C)C)ccc2C(=O)NS(=O)(=O)c2cccc(N)c2)cc1] 314
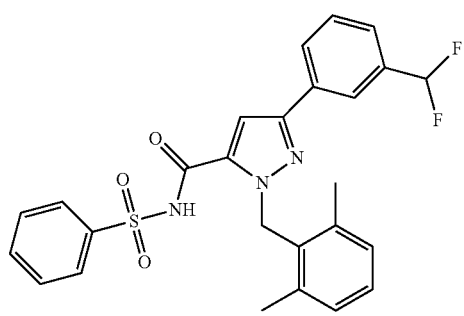 [SMILES: Cc1cccc(C)c1Cn1nc(-c2cccc(C(F)F)c2)cc1C(=O)NS(=O)(=O)c1ccccc1] 315
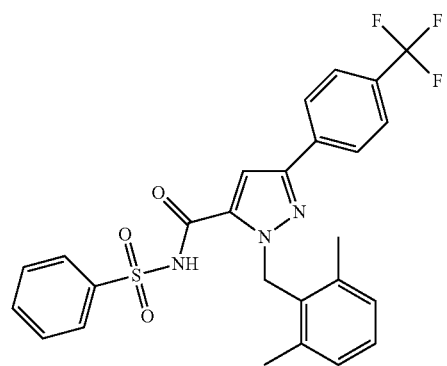 [SMILES: Cc1cccc(C)c1Cn1nc(-c2ccc(C(F)(F)F)cc2)cc1C(=O)NS(=O)(=O)c1ccccc1] 316

| | |
|---|---|
| 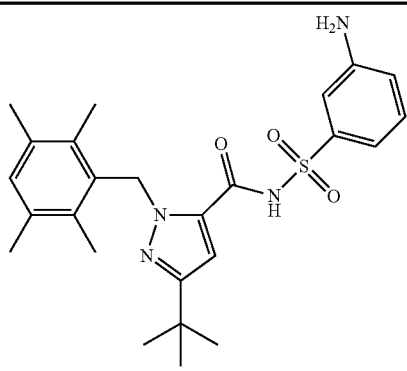 | 317 |
| 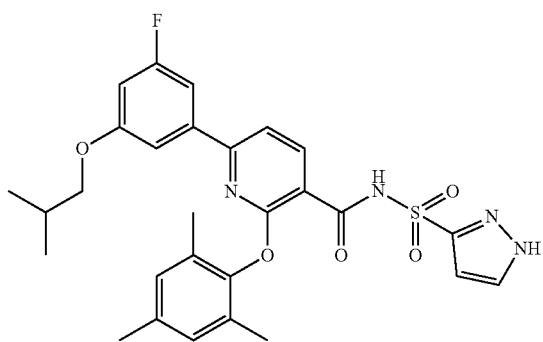 [SMILES: Cc1cc(C)c(Oc2nc(-c3cc(F)cc(OCC(C)C)c3)ccc2C(=O)NS(=O)(=O)c2cc[nH]n2)c(C)c1] | 318 |
| 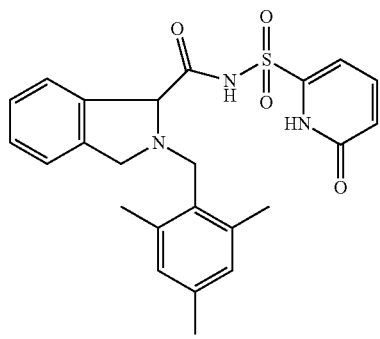 [SMILES: Cc1cc(C)c(CN2Cc3ccccc3C2C(=O)NS(=O)(=O)c2cccc(=O)[nH]2)c(C)c1] | 319 |
| 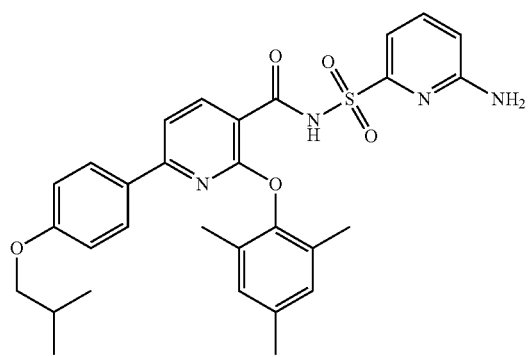 [SMILES: Cc1cc(C)c(Oc2nc(-c3ccc(OCC(C)C)cc3)ccc2C(=O)NS(=O)(=O)c2cccc(N)n2)c(C)c1] | 320 |
| 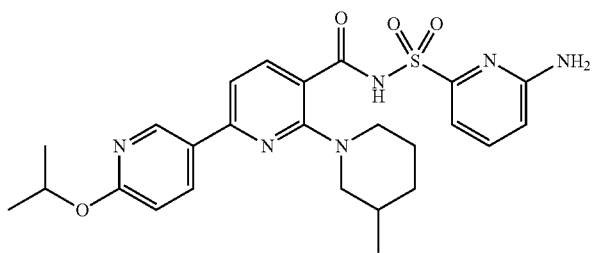 [SMILES: CC1CCCN(c2nc(-c3ccc(OC(C)C)nc3)ccc2C(=O)NS(=O)(=O)c2cccc(N)n2)C1] | 321 |

TABLE 1-continued
| | |
|---|---|
| 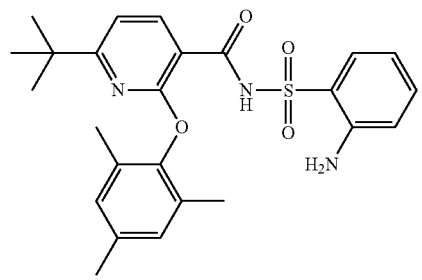 [SMILES: Cc1cc(C)c(Oc2nc(C(C)(C)C)ccc2C(=O)NS(=O)(=O)c2ccccc2N)c(C)c1] | 322 |
| 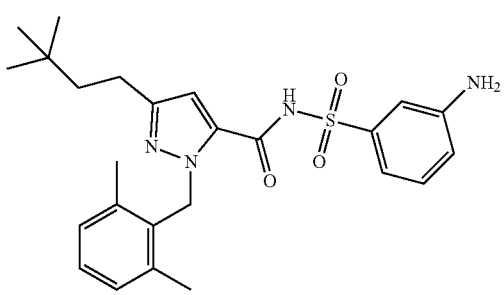 [SMILES: Cc1cccc(C)c1Cn1nc(CCC(C)(C)C)cc1C(=O)NS(=O)(=O)c1cccc(N)c1] | 323 |
| 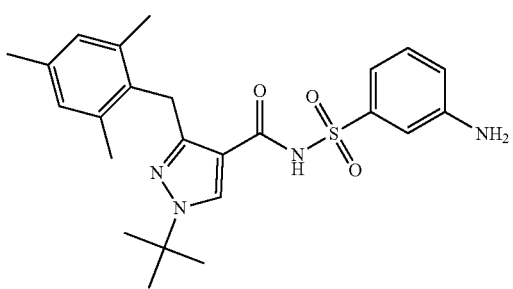 [SMILES: Cc1cc(C)c(Cc2nn(C(C)(C)C)cc2C(=O)NS(=O)(=O)c2cccc(N)c2)c(C)c1] | 324 |
| 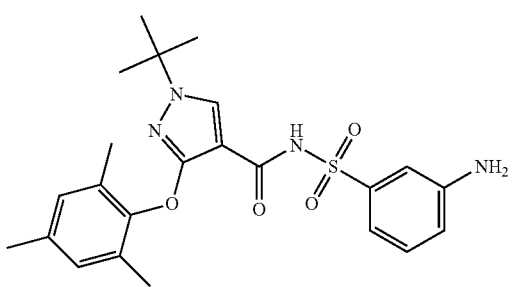 [SMILES: Cc1cc(C)c(Oc2nn(C(C)(C)C)cc2C(=O)NS(=O)(=O)c2cccc(N)c2)c(C)c1] | 325 |
| 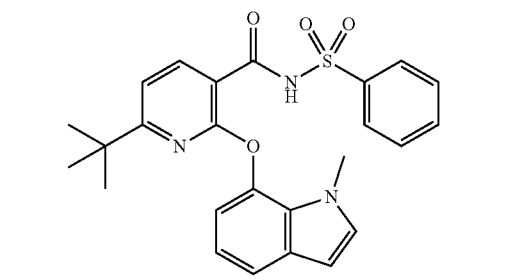 [SMILES: Cn1ccc2cccc(Oc3nc(C(C)(C)C)ccc3C(=O)NS(=O)(=O)c3ccccc3)c21] | 326 |

TABLE 1-continued
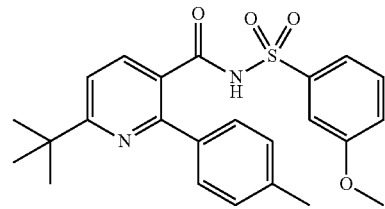 [SMILES: COc1cccc(S(=O)(=O)NC(=O)c2ccc(C(C)(C)C)nc2-c2ccc(C)cc2)c1]
327
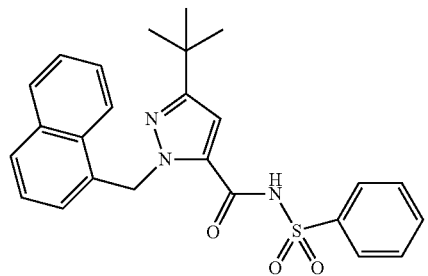 [SMILES: CC(C)(C)c1cc(C(=O)NS(=O)(=O)c2ccccc2)n(Cc2cccc3ccccc23)n1]
328
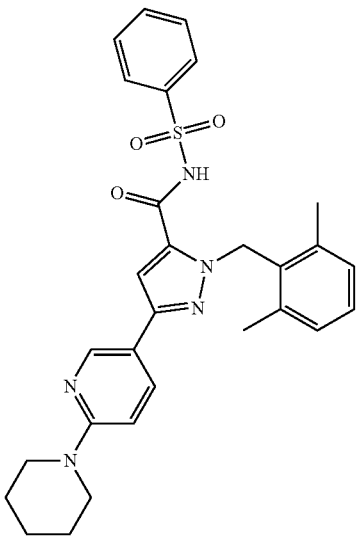 [SMILES: Cc1cccc(C)c1Cn1nc(-c2ccc(N3CCCCC3)nc2)cc1C(=O)NS(=O)(=O)c1ccccc1]
329
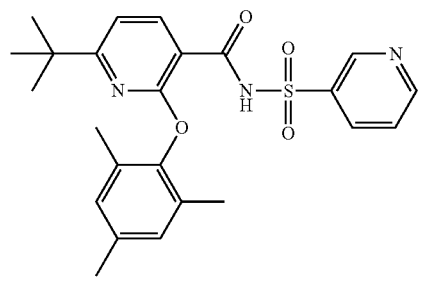 [SMILES: Cc1cc(C)c(Oc2nc(C(C)(C)C)ccc2C(=O)NS(=O)(=O)c2cccnc2)c(C)c1]
330
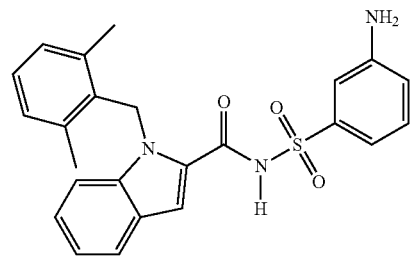 [SMILES: Cc1cccc(C)c1Cn1c(C(=O)NS(=O)(=O)c2cccc(N)c2)cc2ccccc21]
331

TABLE 1-continued
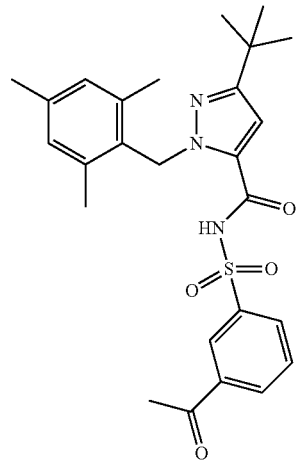 [SMILES: CC(=O)c1cccc(S(=O)(=O)NC(=O)c2cc(C(C)(C)C)nn2Cc2c(C)cc(C)cc2C)c1]
332
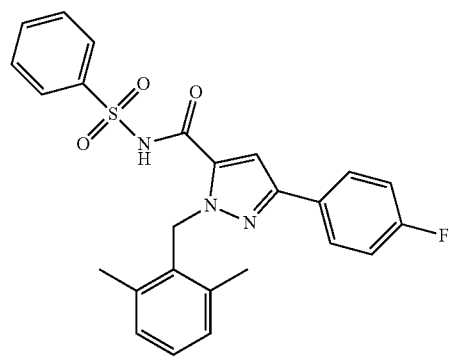 [SMILES: Cc1cccc(C)c1Cn1nc(-c2ccc(F)cc2)cc1C(=O)NS(=O)(=O)c1ccccc1]
333
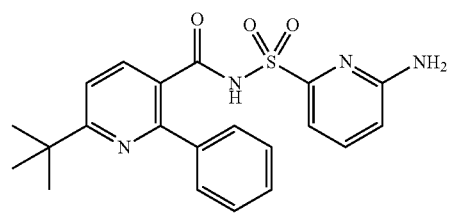 [SMILES: CC(C)(C)c1ccc(C(=O)NS(=O)(=O)c2cccc(N)n2)c(-c2ccccc2)n1]
334
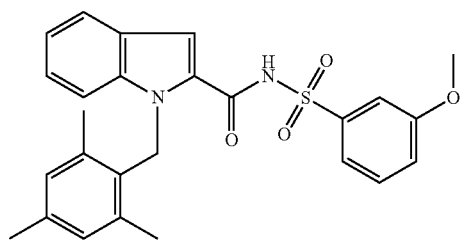
335
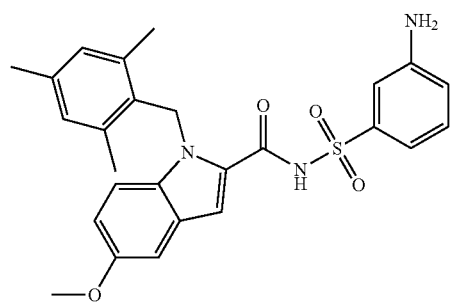 [SMILES: COc1ccc2c(c1)cc(C(=O)NS(=O)(=O)c1cccc(N)c1)n2Cc1c(C)cc(C)cc1C]
336

TABLE 1-continued
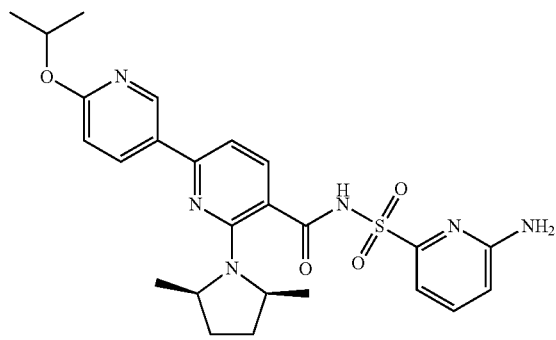 [SMILES: CC(C)Oc1ccc(-c2ccc(C(=O)NS(=O)(=O)c3cccc(N)n3)c(N3[C@H](C)CC[C@@H]3C)n2)cn1]
337
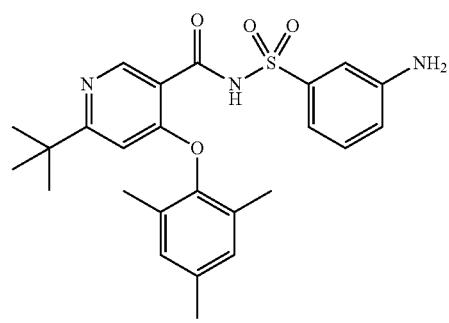 [SMILES: Cc1cc(C)c(Oc2cc(C(C)(C)C)ncc2C(=O)NS(=O)(=O)c2cccc(N)c2)c(C)c1]
338
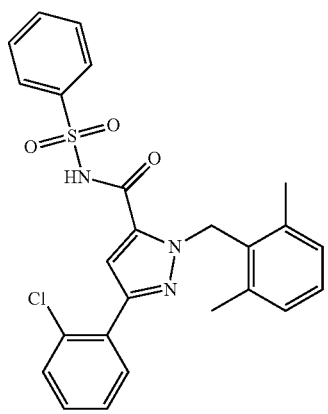 [SMILES: Cc1cccc(C)c1Cn1nc(-c2ccccc2Cl)cc1C(=O)NS(=O)(=O)c1ccccc1]
339
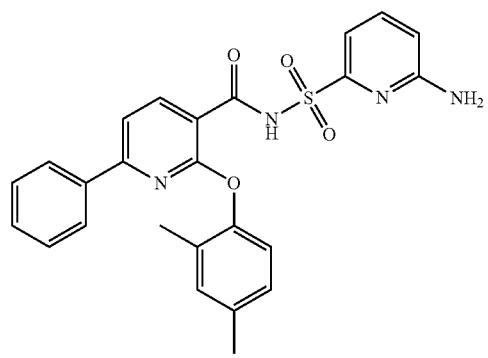 [SMILES: Cc1ccc(Oc2nc(-c3ccccc3)ccc2C(=O)NS(=O)(=O)c2cccc(N)n2)c(C)c1]
340

TABLE 1-continued
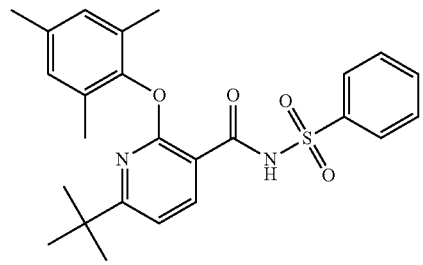 [SMILES: Cc1cc(C)c(Oc2nc(C(C)(C)C)ccc2C(=O)NS(=O)(=O)c2ccccc2)c(C)c1]
341
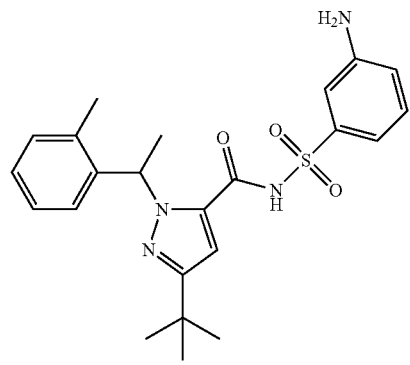 [SMILES: Cc1ccccc1C(C)n1nc(C(C)(C)C)cc1C(=O)NS(=O)(=O)c1cccc(N)c1]
342
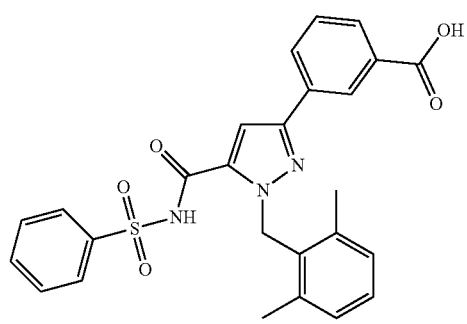 [SMILES: Cc1cccc(C)c1Cn1nc(-c2cccc(C(=O)O)c2)cc1C(=O)NS(=O)(=O)c1ccccc1]
343
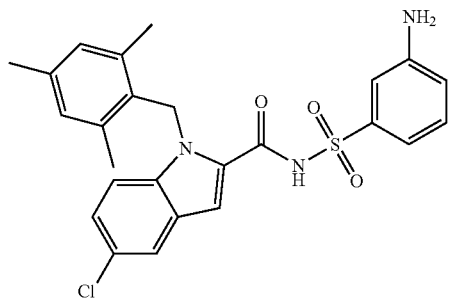 [SMILES: Cc1cc(C)c(Cn2c(C(=O)NS(=O)(=O)c3cccc(N)c3)cc3cc(Cl)ccc32)c(C)c1]
344
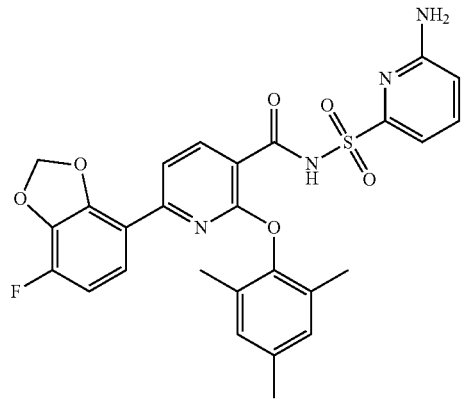 [SMILES: Cc1cc(C)c(Oc2nc(-c3ccc(F)c4c3OCO4)ccc2C(=O)NS(=O)(=O)c2cccc(N)n2)c(C)c1]
345

TABLE 1-continued
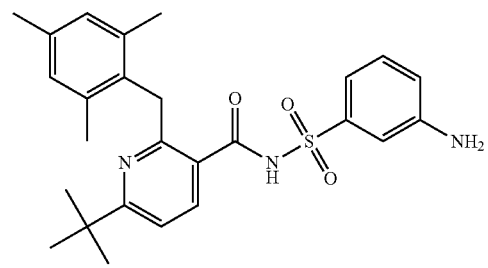 [SMILES: Cc1cc(C)c(Cc2nc(C(C)(C)C)ccc2C(=O)NS(=O)(=O)c2cccc(N)c2)c(C)c1] 346
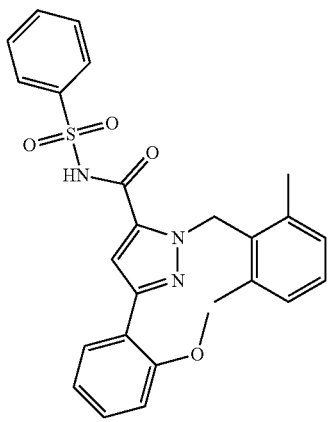 [SMILES: COc1ccccc1-c1cc(C(=O)NS(=O)(=O)c2ccccc2)n(Cc2c(C)cccc2C)n1] 347
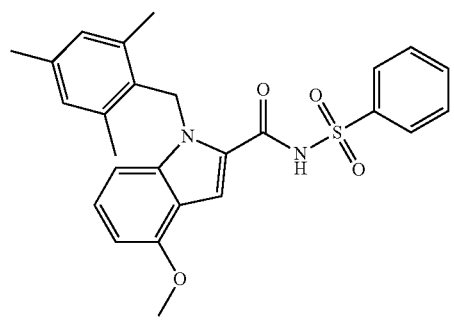 [SMILES: COc1cccc2c1cc(C(=O)NS(=O)(=O)c1ccccc1)n2Cc1c(C)cc(C)cc1C] 348
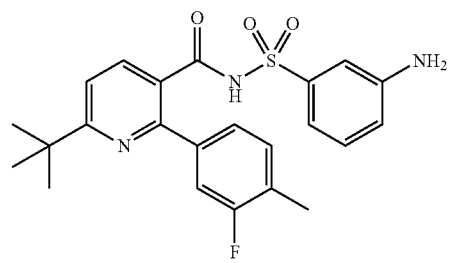 [SMILES: Cc1ccc(-c2nc(C(C)(C)C)ccc2C(=O)NS(=O)(=O)c2cccc(N)c2)cc1F] 349
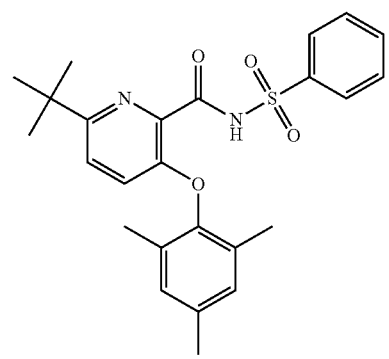 [SMILES: Cc1cc(C)c(Oc2ccc(C(C)(C)C)nc2C(=O)NS(=O)(=O)c2ccccc2)c(C)c1] 350

TABLE 1-continued
| | |
|---|---|
| 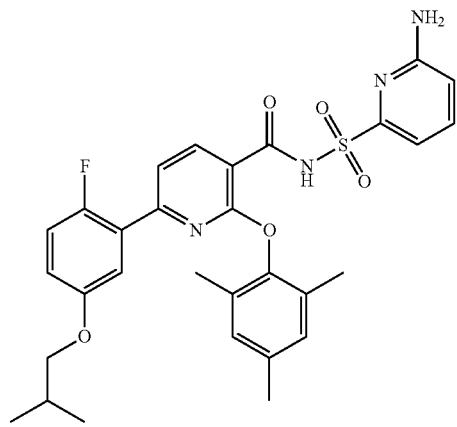 [SMILES: Cc1cc(C)c(Oc2nc(-c3cc(OCC(C)C)ccc3F)ccc2C(=O)NS(=O)(=O)c2cccc(N)n2)c(C)c1] | 351 |
| 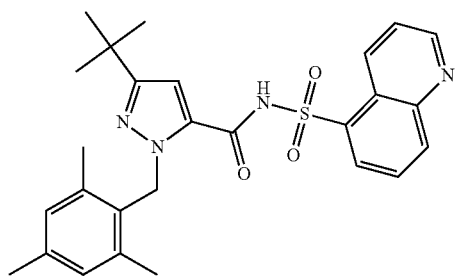 [SMILES: Cc1cc(C)c(Cn2nc(C(C)(C)C)cc2C(=O)NS(=O)(=O)c2cccc3ncccc23)c(C)c1] | 352 |
| 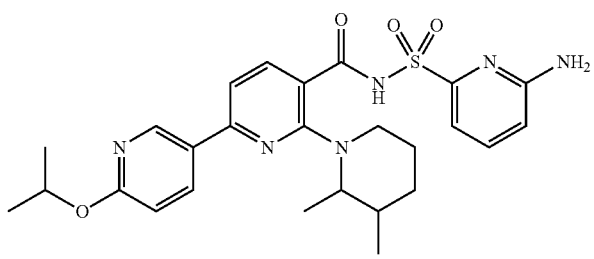 [SMILES: CC(C)Oc1ccc(-c2ccc(C(=O)NS(=O)(=O)c3cccc(N)n3)c(N3CCCC(C)C3C)n2)cn1] | 353 |
| 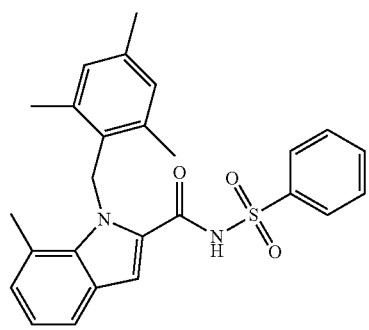 [SMILES: Cc1cc(C)c(Cn2c(C(=O)NS(=O)(=O)c3ccccc3)cc3cccc(C)c32)c(C)c1] | 354 |
| 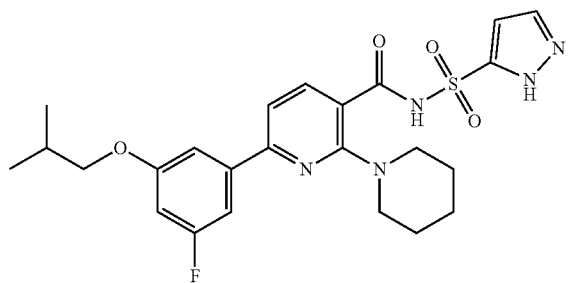 [SMILES: CC(C)COc1cc(F)cc(-c2ccc(C(=O)NS(=O)(=O)c3ccn[nH]3)c(N3CCCCC3)n2)c1] | 355 |

TABLE 1-continued
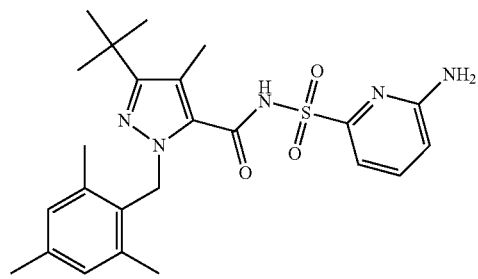 [SMILES: Cc1cc(C)c(Cn2nc(C(C)(C)C)c(C)c2C(=O)NS(=O)(=O)c2cccc(N)n2)c(C)c1]
356
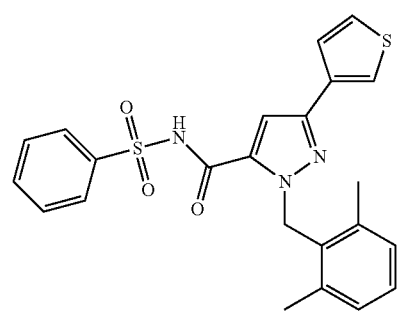 [SMILES: Cc1cccc(C)c1Cn1nc(-c2ccsc2)cc1C(=O)NS(=O)(=O)c1ccccc1]
357
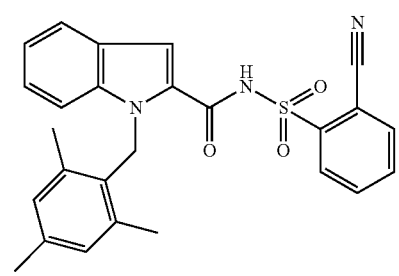 [SMILES: Cc1cc(C)c(Cn2c(C(=O)NS(=O)(=O)c3ccccc3C#N)cc3ccccc32)c(C)c1]
358
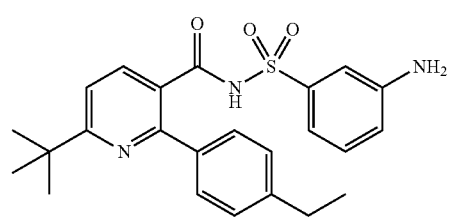 [SMILES: CCc1ccc(-c2nc(C(C)(C)C)ccc2C(=O)NS(=O)(=O)c2cccc(N)c2)cc1]
359
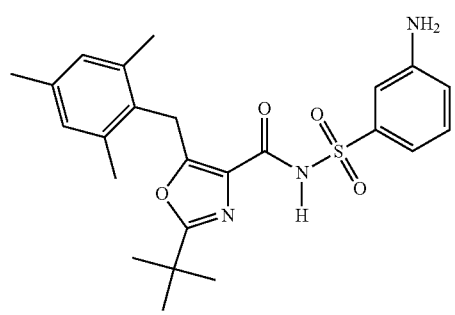 [SMILES: Cc1cc(C)c(Cc2oc(C(C)(C)C)nc2C(=O)NS(=O)(=O)c2cccc(N)c2)c(C)c1]
360

TABLE 1-continued
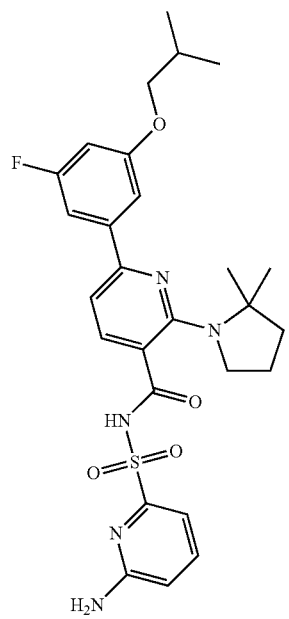 [SMILES: CC(C)COc1cc(F)cc(-c2ccc(C(=O)NS(=O)(=O)c3cccc(N)n3)c(N3CCCC3(C)C)n2)c1]
361
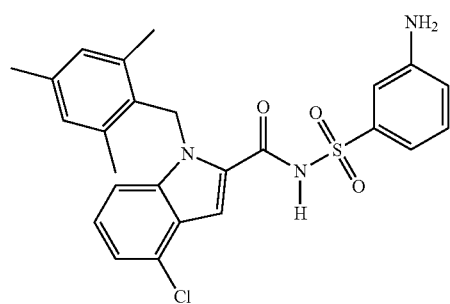 [SMILES: Cc1cc(C)c(Cn2c(C(=O)NS(=O)(=O)c3cccc(N)c3)cc3c(Cl)cccc32)c(C)c1]
362
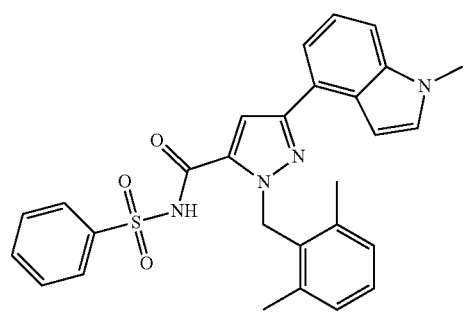 [SMILES: Cc1cccc(C)c1Cn1nc(-c2cccc3c2ccn3C)cc1C(=O)NS(=O)(=O)c1ccccc1]
363
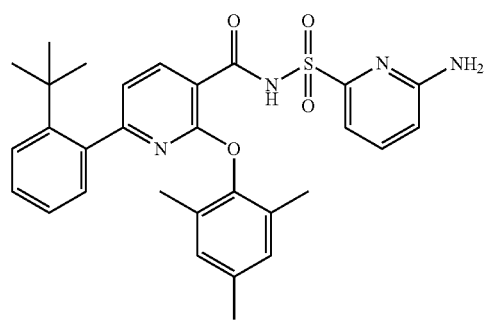 [SMILES: Cc1cc(C)c(Oc2nc(-c3ccccc3C(C)(C)C)ccc2C(=O)NS(=O)(=O)c2cccc(N)n2)c(C)c1]
364

TABLE 1-continued
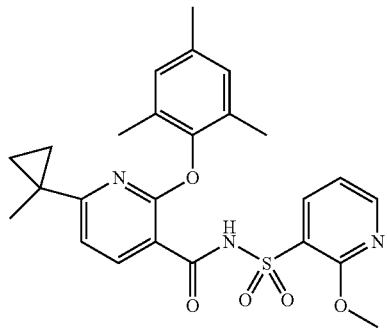 [SMILES: COc1ncccc1S(=O)(=O)NC(=O)c1ccc(C2(C)CC2)nc1Oc1c(C)cc(C)cc1C]
365
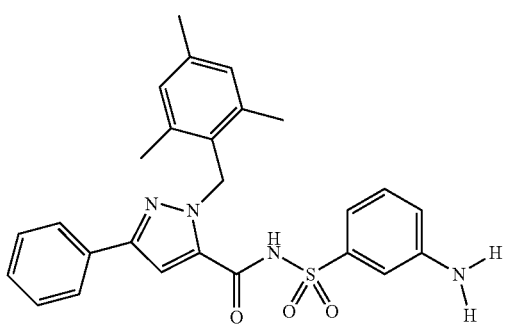 [SMILES: Cc1cc(C)c(Cn2nc(-c3ccccc3)cc2C(=O)NS(=O)(=O)c2cccc(N)c2)c(C)c1]
366
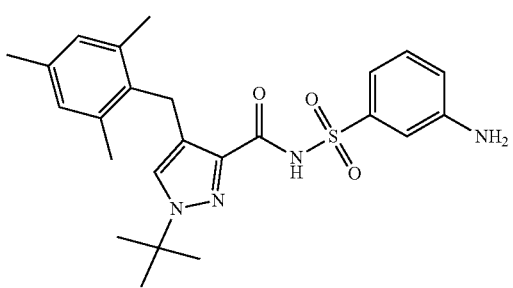 [SMILES: Cc1cc(C)c(Cc2cn(C(C)(C)C)nc2C(=O)NS(=O)(=O)c2cccc(N)c2)c(C)c1]
367
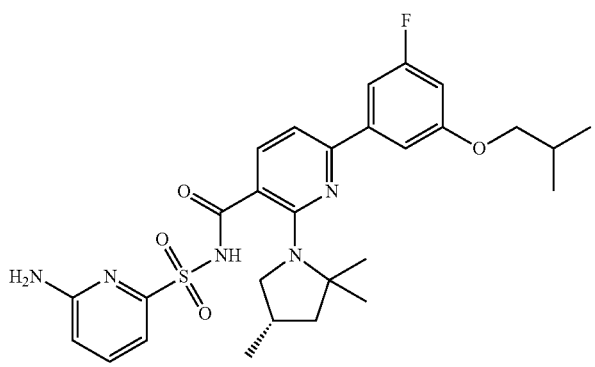 [SMILES: CC(C)COc1cc(F)cc(-c2ccc(C(=O)NS(=O)(=O)c3cccc(N)n3)c(N3C[C@@H](C)CC3(C)C)n2)c1]
368

TABLE 1-continued
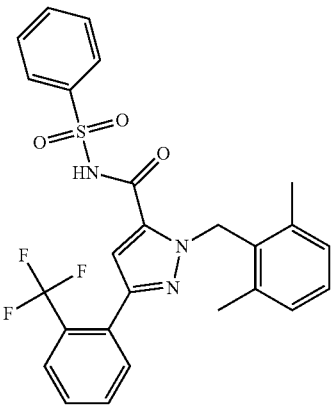 [SMILES: Cc1cccc(C)c1Cn1nc(-c2ccccc2C(F)(F)F)cc1C(=O)NS(=O)(=O)c1ccccc1] 369
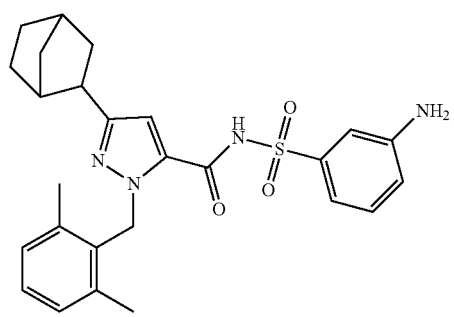 [SMILES: Cc1cccc(C)c1Cn1nc(C2CC3CCC2C3)cc1C(=O)NS(=O)(=O)c1cccc(N)c1] 370
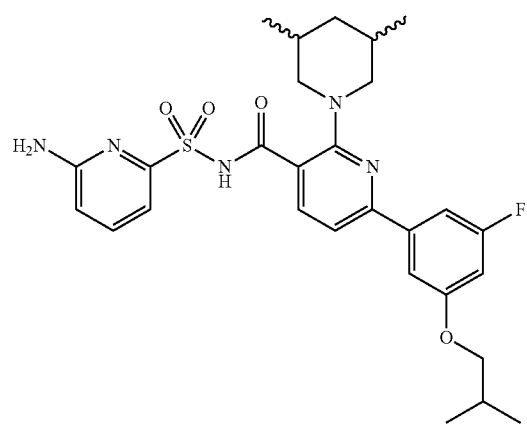 371
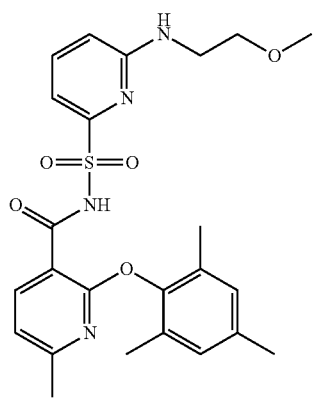 [SMILES: COCCNc1cccc(S(=O)(=O)NC(=O)c2ccc(C)nc2Oc2c(C)cc(C)cc2C)n1] 372

TABLE 1-continued
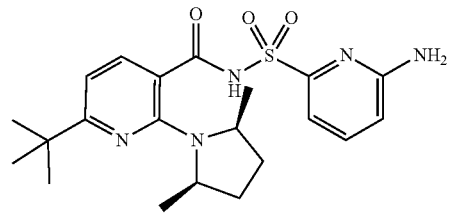 [SMILES: C[C@@H]1CC[C@H](C)N1c1nc(C(C)(C)C)ccc1C(=O)NS(=O)(=O)c1cccc(N)n1] 373
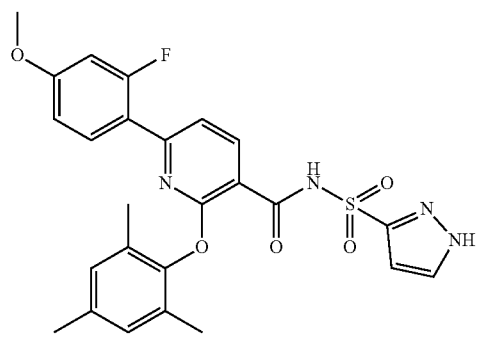 [SMILES: COc1ccc(-c2ccc(C(=O)NS(=O)(=O)c3cc[nH]n3)c(Oc3c(C)cc(C)cc3C)n2)c(F)c1] 374
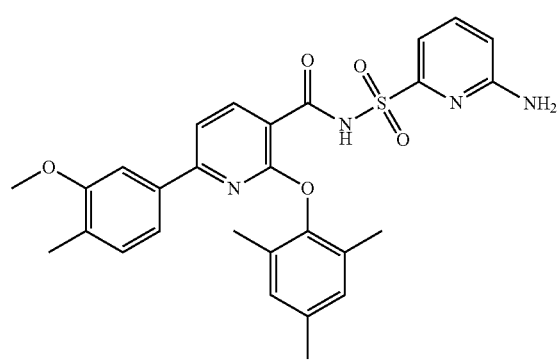 [SMILES: COc1cc(-c2ccc(C(=O)NS(=O)(=O)c3cccc(N)n3)c(Oc3c(C)cc(C)cc3C)n2)ccc1C] 375
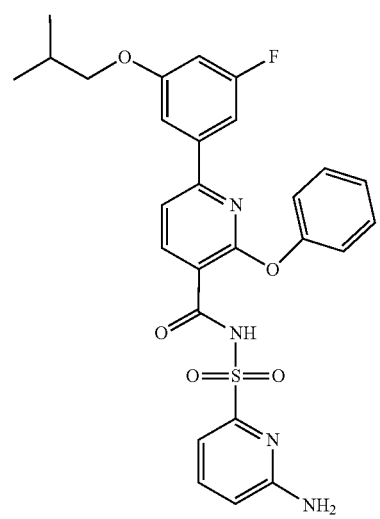 [SMILES: CC(C)COc1cc(F)cc(-c2ccc(C(=O)NS(=O)(=O)c3cccc(N)n3)c(Oc3ccccc3)n2)c1] 376

TABLE 1-continued
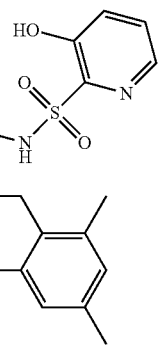
377
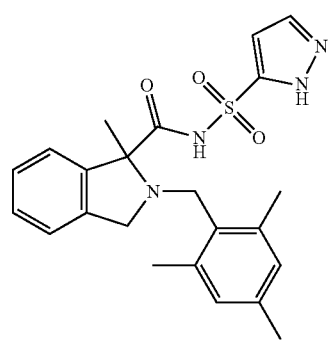 [SMILES: Cc1cc(C)c(CN2Cc3ccccc3C2(C)C(=O)NS(=O)(=O)c2ccn[nH]2)c(C)c1]
378
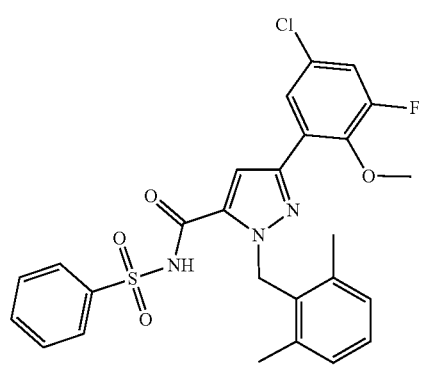 [SMILES: COc1c(F)cc(Cl)cc1-c1cc(C(=O)NS(=O)(=O)c2ccccc2)n(Cc2c(C)cccc2C)n1]
379
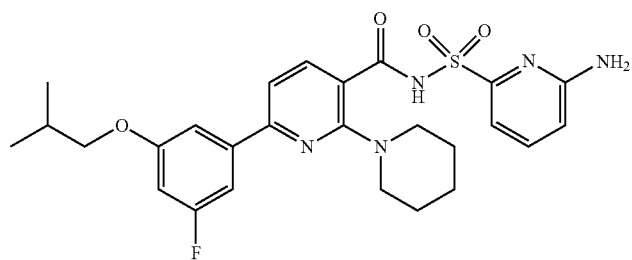 [SMILES: CC(C)COc1cc(F)cc(-c2ccc(C(=O)NS(=O)(=O)c3cccc(N)n3)c(N3CCCCC3)n2)c1]
380

TABLE 1-continued
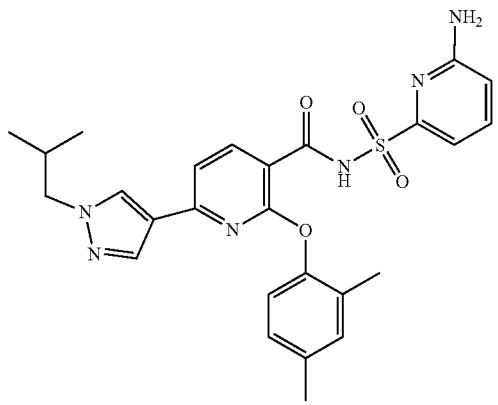
381
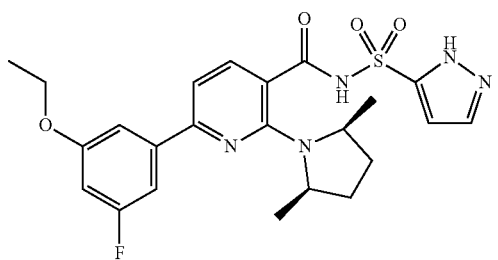 [SMILES: CCOc1cc(F)cc(-c2ccc(C(=O)NS(=O)(=O)c3ccn[nH]3)c(N3[C@H](C)CC[C@@H]3C)n2)c1]
382
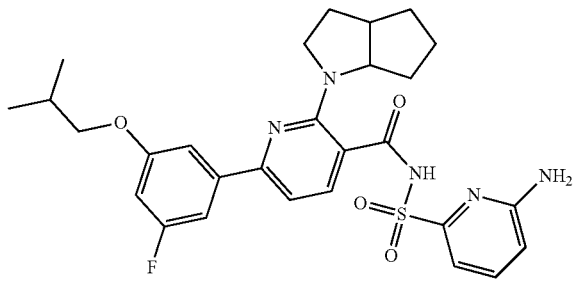 [SMILES: CC(C)COc1cc(F)cc(-c2ccc(C(=O)NS(=O)(=O)c3cccc(N)n3)c(N3CCC4CCCC43)n2)c1]
383
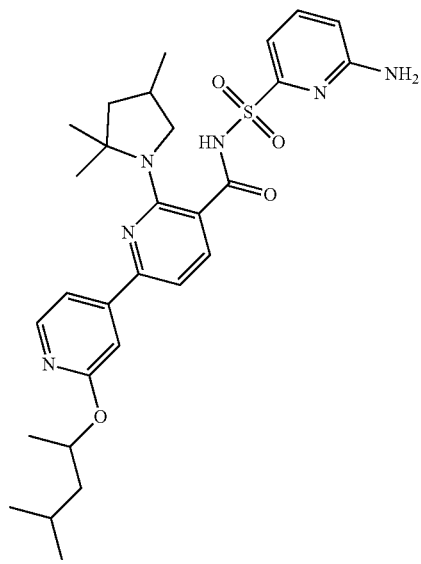 [SMILES: CC(C)CC(C)Oc1cc(-c2ccc(C(=O)NS(=O)(=O)c3cccc(N)n3)c(N3CC(C)CC3(C)C)n2)ccn1]
384

TABLE 1-continued
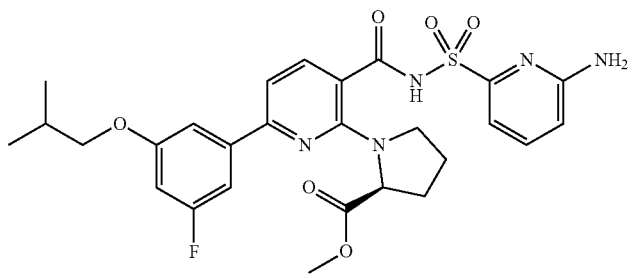 [SMILES: COC(=O)[C@@H]1CCCN1c1nc(-c2cc(F)cc(OCC(C)C)c2)ccc1C(=O)NS(=O)(=O)c1cccc(N)n1]
385
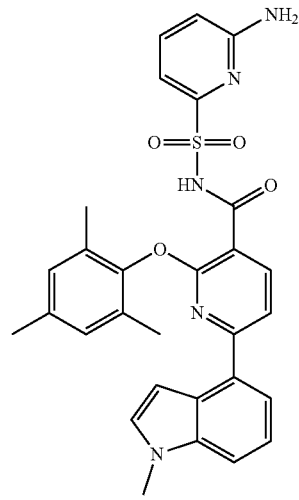 [SMILES: Cc1cc(C)c(Oc2nc(-c3cccc4c3ccn4C)ccc2C(=O)NS(=O)(=O)c2cccc(N)n2)c(C)c1]
386
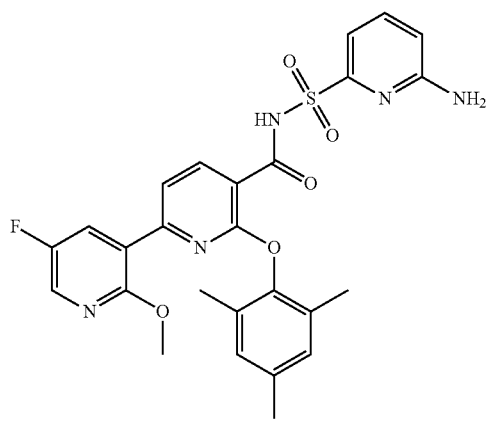 [SMILES: COc1ncc(F)cc1-c1ccc(C(=O)NS(=O)(=O)c2cccc(N)n2)c(Oc2c(C)cc(C)cc2C)n1]
387
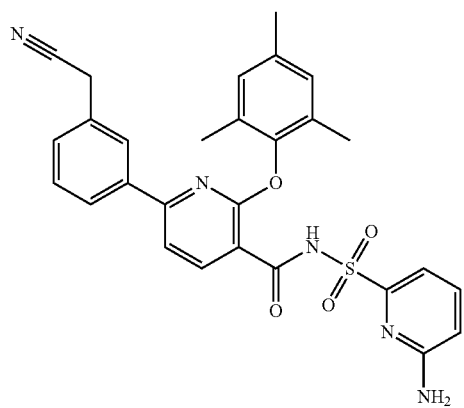 [SMILES: Cc1cc(C)c(Oc2nc(-c3cccc(CC#N)c3)ccc2C(=O)NS(=O)(=O)c2cccc(N)n2)c(C)c1]
388

TABLE 1-continued
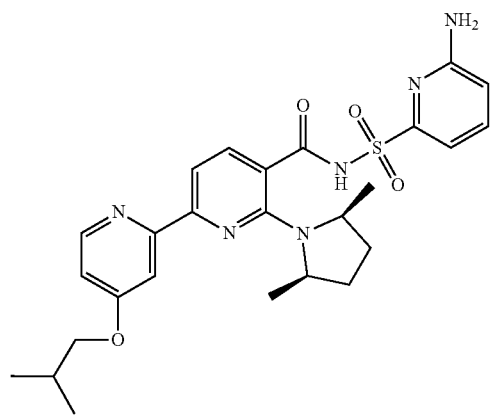 [SMILES: CC(C)COc1ccnc(-c2ccc(C(=O)NS(=O)(=O)c3cccc(N)n3)c(N3[C@H](C)CC[C@@H]3C)n2)c1]
389
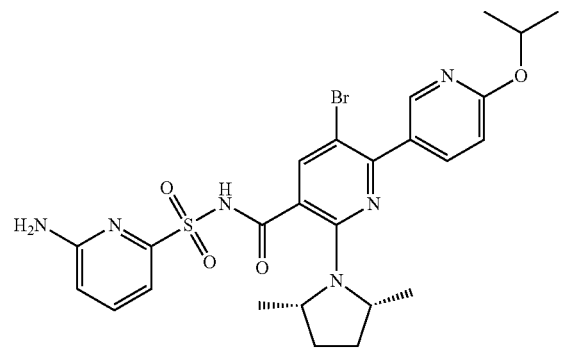 [SMILES: CC(C)Oc1ccc(-c2nc(N3[C@H](C)CC[C@@H]3C)c(C(=O)NS(=O)(=O)c3cccc(N)n3)cc2Br)cn1]
390
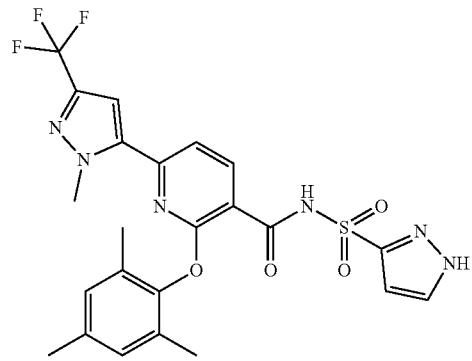 [SMILES: Cc1cc(C)c(Oc2nc(-c3cc(C(F)(F)F)nn3C)ccc2C(=O)NS(=O)(=O)c2cc[nH]n2)c(C)c1]
391
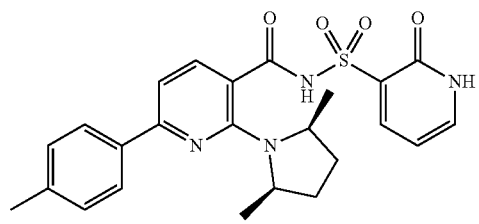 [SMILES: Cc1ccc(-c2ccc(C(=O)NS(=O)(=O)c3ccc[nH]c3=O)c(N3[C@H](C)CC[C@@H]3C)n2)cc1]
392

TABLE 1-continued
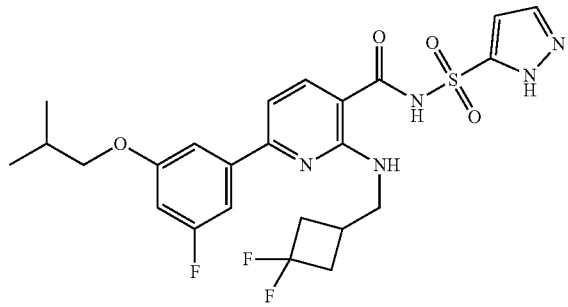 [SMILES: CC(C)COc1cc(F)cc(-c2ccc(C(=O)NS(=O)(=O)c3ccn[nH]3)c(NCC3CC(F)(F)C3)n2)c1]
393
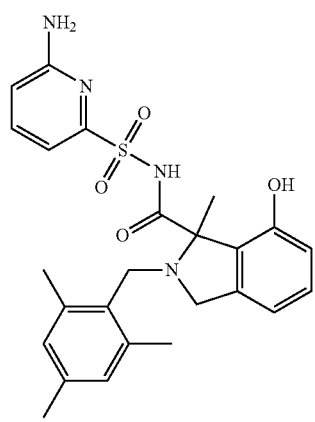 [SMILES: Cc1cc(C)c(CN2Cc3cccc(O)c3C2(C)C(=O)NS(=O)(=O)c2cccc(N)n2)c(C)c1]
394
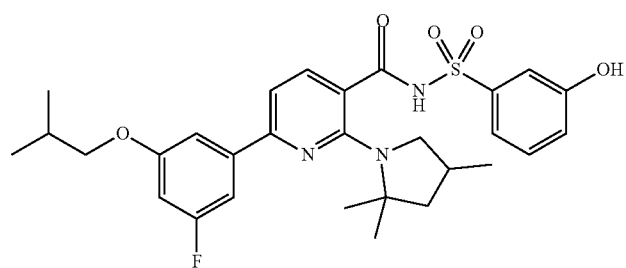
395
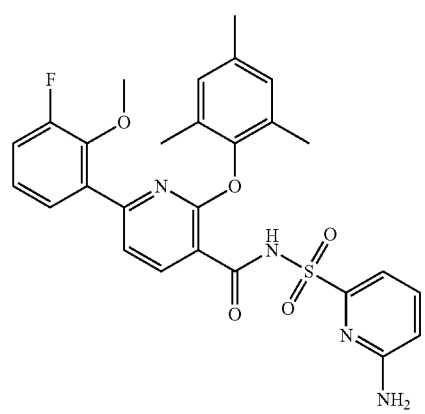 [SMILES: COc1c(F)cccc1-c1ccc(C(=O)NS(=O)(=O)c2cccc(N)n2)c(Oc2c(C)cc(C)cc2C)n1]
396

TABLE 1-continued
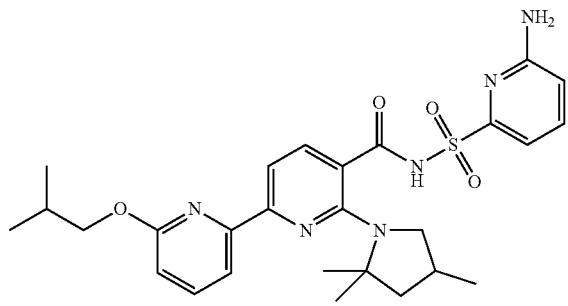 [SMILES: CC(C)COc1cccc(-c2ccc(C(=O)NS(=O)(=O)c3cccc(N)n3)c(N3CC(C)CC3(C)C)n2)n1]
397
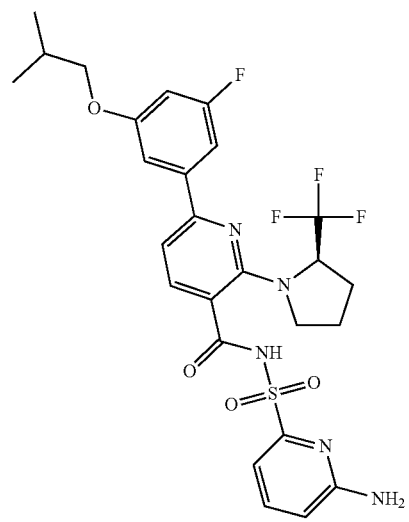 [SMILES: CC(C)COc1cc(F)cc(-c2ccc(C(=O)NS(=O)(=O)c3cccc(N)n3)c(N3CCC[C@@H]3C(F)(F)F)n2)c1]
398
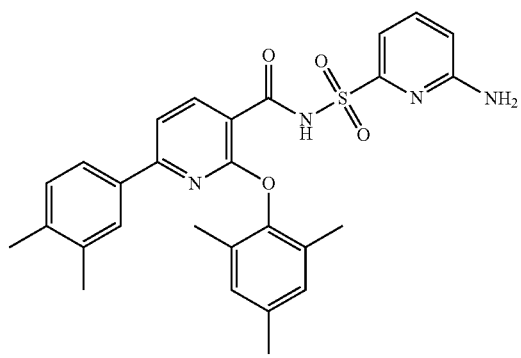
399
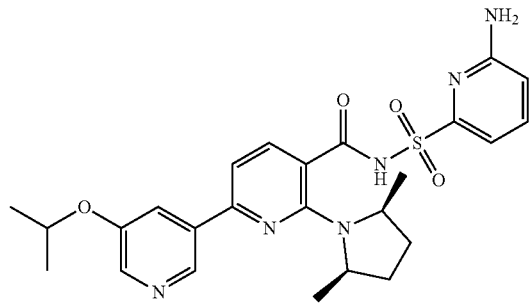 [SMILES: CC(C)Oc1cncc(-c2ccc(C(=O)NS(=O)(=O)c3cccc(N)n3)c(N3[C@H](C)CC[C@@H]3C)n2)c1]
400

TABLE 1-continued
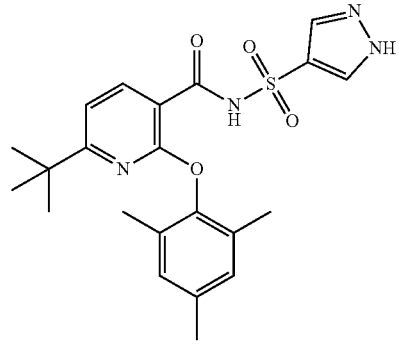 [SMILES: Cc1cc(C)c(Oc2nc(C(C)(C)C)ccc2C(=O)NS(=O)(=O)c2cn[nH]c2)c(C)c1]
401
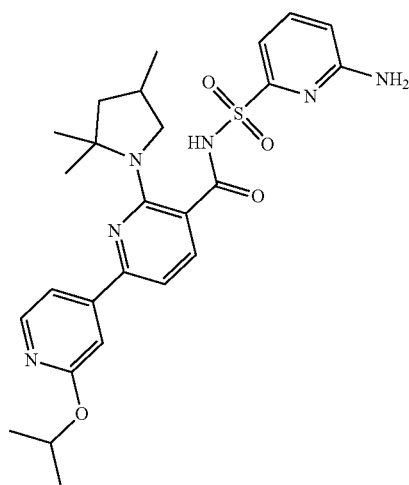 [SMILES: CC1CN(c2nc(-c3ccnc(OC(C)C)c3)ccc2C(=O)NS(=O)(=O)c2cccc(N)n2)C(C)(C)C1]
402
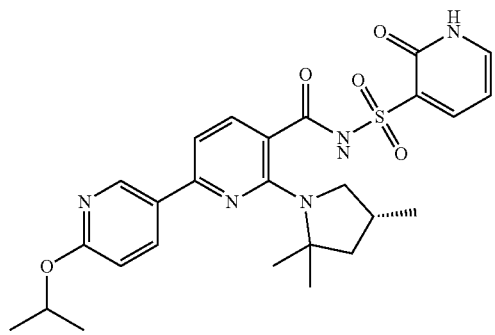
403
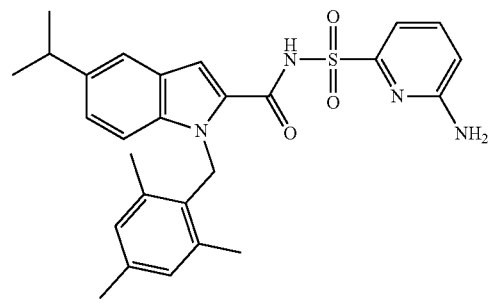 [SMILES: Cc1cc(C)c(Cn2c(C(=O)NS(=O)(=O)c3cccc(N)n3)cc3cc(C(C)C)ccc32)c(C)c1]
404

TABLE 1-continued
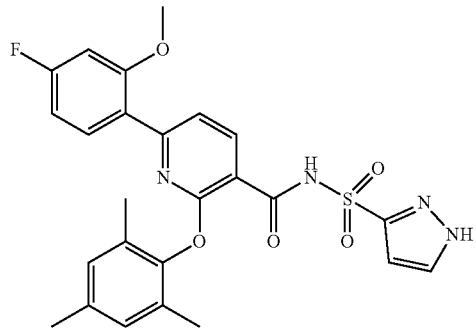 [SMILES: COc1cc(F)ccc1-c1ccc(C(=O)NS(=O)(=O)c2cc[nH]n2)c(Oc2c(C)cc(C)cc2C)n1]
405
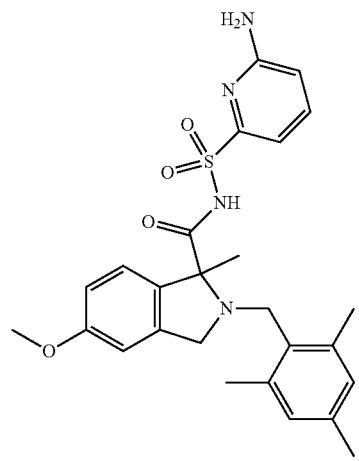
406
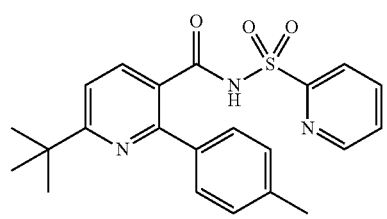 [SMILES: Cc1ccc(-c2nc(C(C)(C)C)ccc2C(=O)NS(=O)(=O)c2ccccn2)cc1]
407
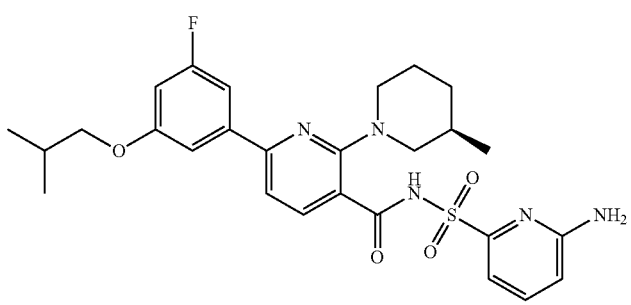 [SMILES: CC(C)COc1cc(F)cc(-c2ccc(C(=O)NS(=O)(=O)c3cccc(N)n3)c(N3CCC[C@@H](C)C3)n2)c1]
408
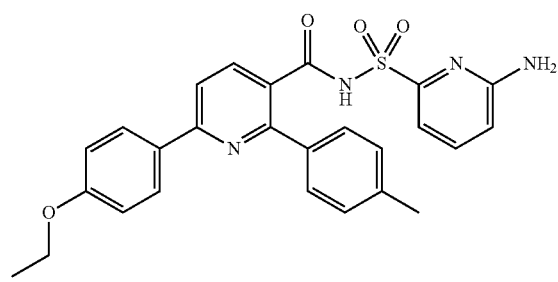 [SMILES: CCOc1ccc(-c2ccc(C(=O)NS(=O)(=O)c3cccc(N)n3)c(-c3ccc(C)cc3)n2)cc1]
409

TABLE 1-continued
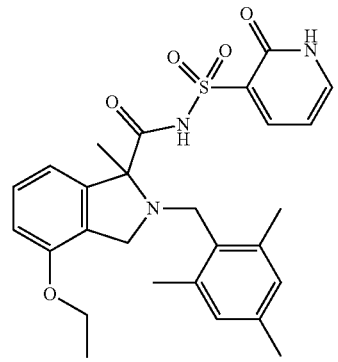 [SMILES: CCOc1cccc2c1CN(Cc1c(C)cc(C)cc1C)C2(C)C(=O)NS(=O)(=O)c1ccc[nH]c1=O]
410
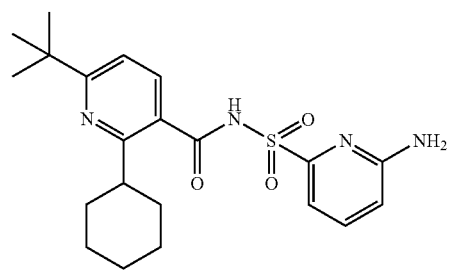 [SMILES: CC(C)(C)c1ccc(C(=O)NS(=O)(=O)c2cccc(N)n2)c(C2CCCCC2)n1]
411
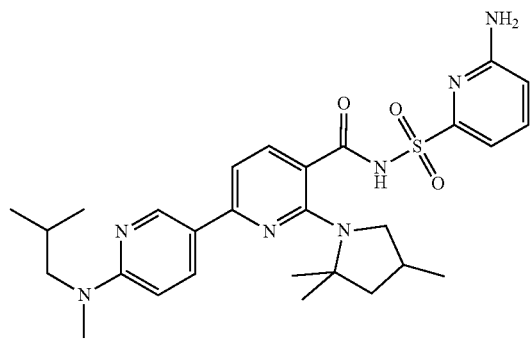 [SMILES: CC(C)CN(C)c1ccc(-c2ccc(C(=O)NS(=O)(=O)c3cccc(N)n3)c(N3CC(C)CC3(C)C)n2)cn1]
412
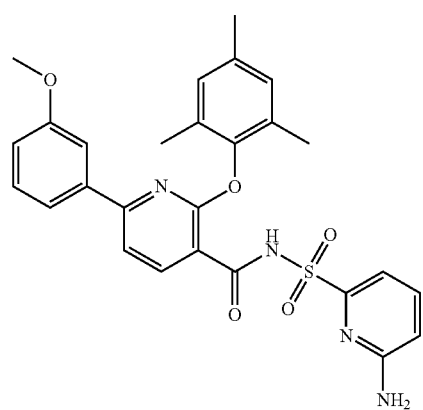 [SMILES: COc1cccc(-c2ccc(C(=O)NS(=O)(=O)c3cccc(N)n3)c(Oc3c(C)cc(C)cc3C)n2)c1]
413
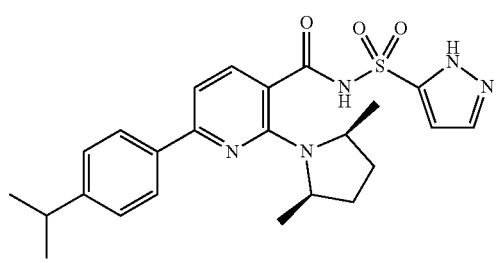 [SMILES: CC(C)c1ccc(-c2ccc(C(=O)NS(=O)(=O)c3ccn[nH]3)c(N3[C@H](C)CC[C@@H]3C)n2)cc1]
414

TABLE 1-continued
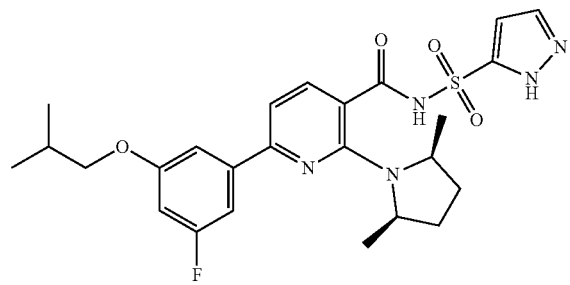 [SMILES: CC(C)COc1cc(F)cc(-c2ccc(C(=O)NS(=O)(=O)c3ccn[nH]3)c(N3[C@H](C)CC[C@@H]3C)n2)c1]
415
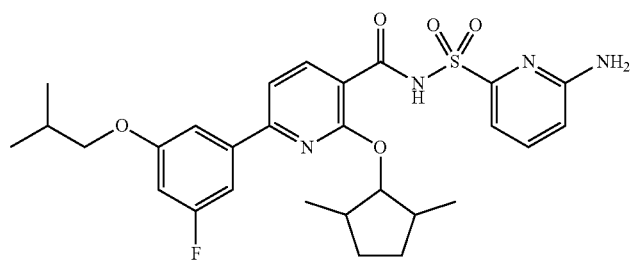 [SMILES: CC(C)COc1cc(F)cc(-c2ccc(C(=O)NS(=O)(=O)c3cccc(N)n3)c(OC3C(C)CCC3C)n2)c1]
416
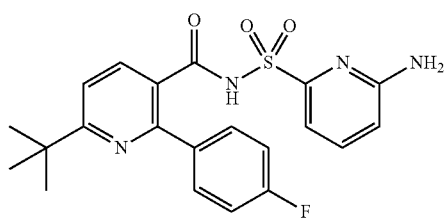 [SMILES: CC(C)(C)c1ccc(C(=O)NS(=O)(=O)c2cccc(N)n2)c(-c2ccc(F)cc2)n1]
417
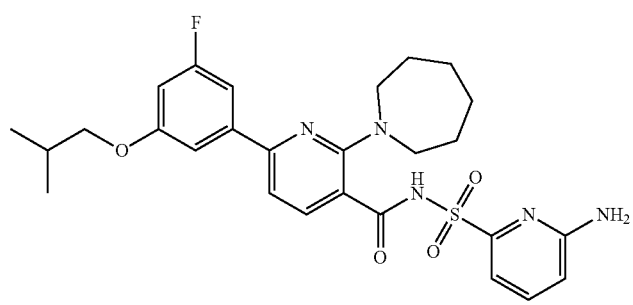 [SMILES: CC(C)COc1cc(F)cc(-c2ccc(C(=O)NS(=O)(=O)c3cccc(N)n3)c(N3CCCCCC3)n2)c1]
418
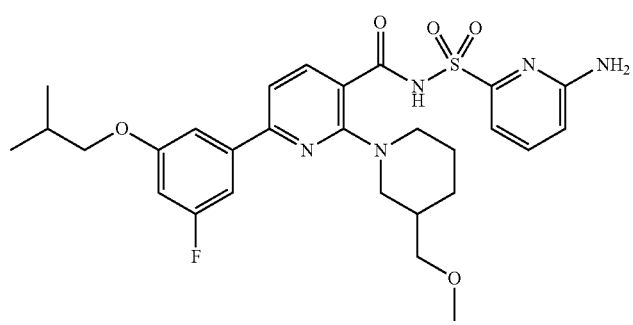 [SMILES: COCC1CCCN(c2nc(-c3cc(F)cc(OCC(C)C)c3)ccc2C(=O)NS(=O)(=O)c2cccc(N)n2)C1]
419

TABLE 1-continued
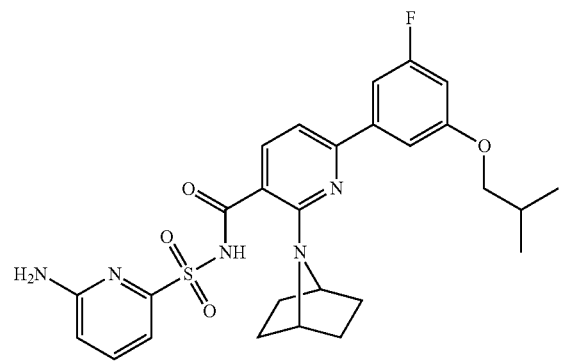 [SMILES: CC(C)COc1cc(F)cc(-c2ccc(C(=O)NS(=O)(=O)c3cccc(N)n3)c(N3C4CCC3CC4)n2)c1]
420
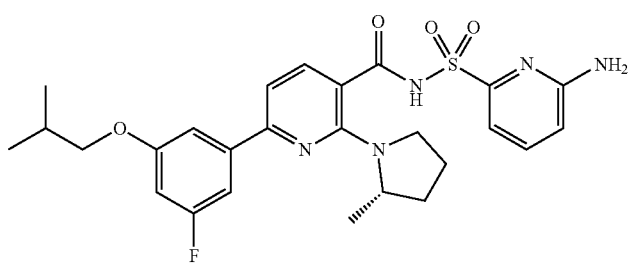 [SMILES: CC(C)COc1cc(F)cc(-c2ccc(C(=O)NS(=O)(=O)c3cccc(N)n3)c(N3CCC[C@@H]3C)n2)c1]
421
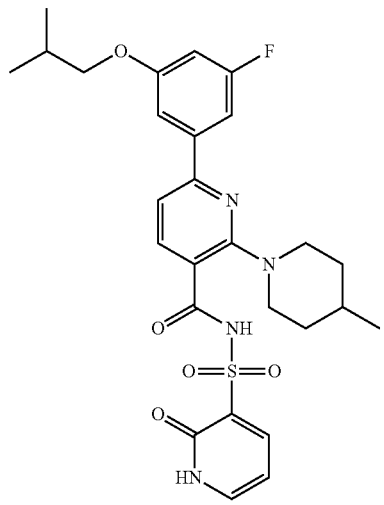 [SMILES: CC(C)COc1cc(F)cc(-c2ccc(C(=O)NS(=O)(=O)c3ccc[nH]c3=O)c(N3CCC(C)CC3)n2)c1]
422
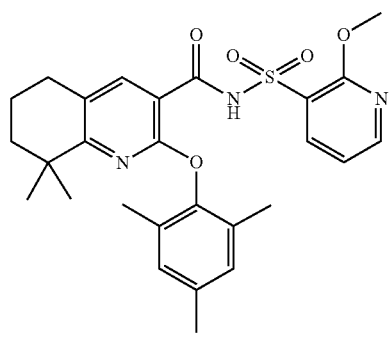 [SMILES: COc1ncccc1S(=O)(=O)NC(=O)c1cc2c(nc1Oc1c(C)cc(C)cc1C)C(C)(C)CCC2]
423

TABLE 1-continued

424

425

426

427

TABLE 1-continued
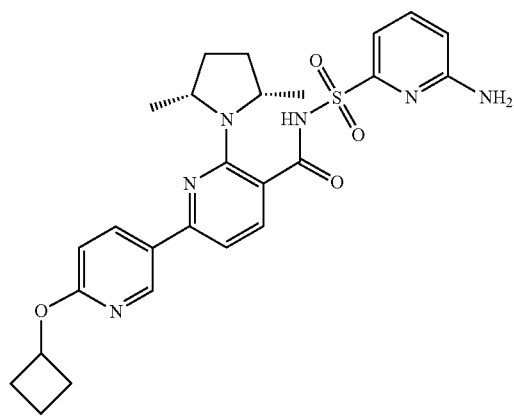 [SMILES: C[C@@H]1CC[C@H](C)N1c1nc(-c2ccc(OC3CCC3)nc2)ccc1C(=O)NS(=O)(=O)c1cccc(N)n1]
428
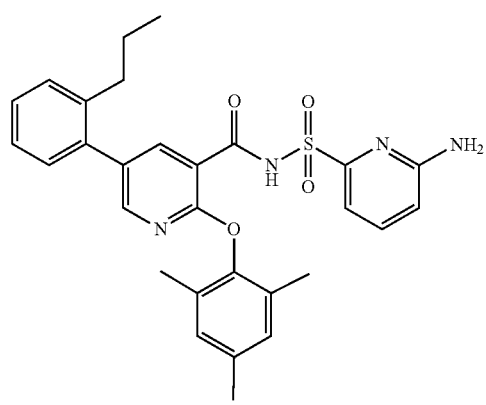 [SMILES: CCCc1ccccc1-c1cnc(Oc2c(C)cc(C)cc2C)c(C(=O)NS(=O)(=O)c2cccc(N)n2)c1]
429
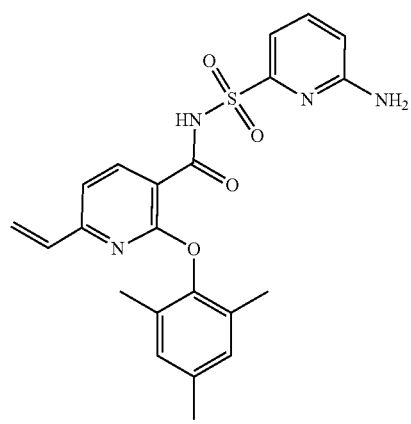
430
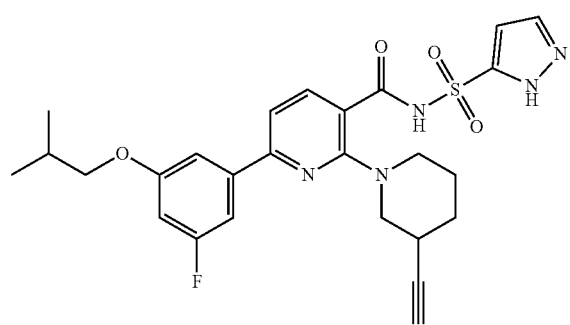 [SMILES: C#CC1CCCN(c2nc(-c3cc(F)cc(OCC(C)C)c3)ccc2C(=O)NS(=O)(=O)c2ccn[nH]2)C1]
431

TABLE 1-continued
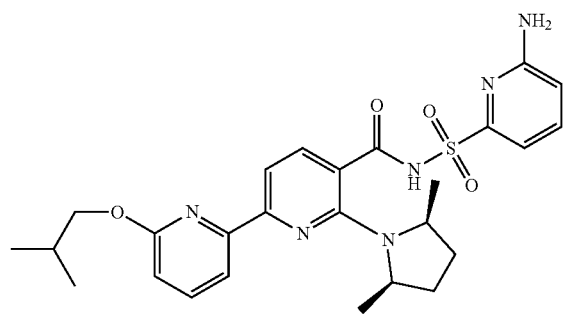 [SMILES: CC(C)COc1cccc(-c2ccc(C(=O)NS(=O)(=O)c3cccc(N)n3)c(N3[C@H](C)CC[C@@H]3C)n2)n1]
432
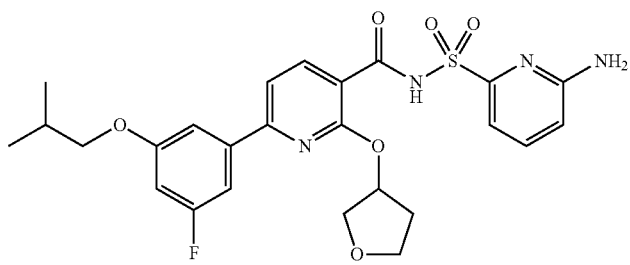
433
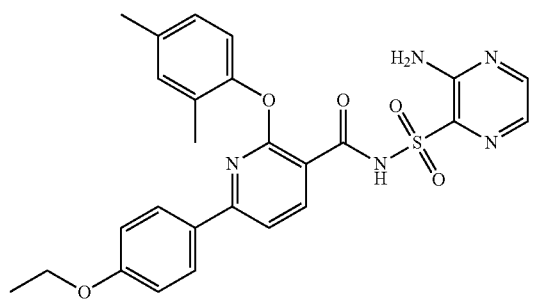 [SMILES: CCOc1ccc(-c2ccc(C(=O)NS(=O)(=O)c3nccnc3N)c(Oc3ccc(C)cc3C)n2)cc1]
434
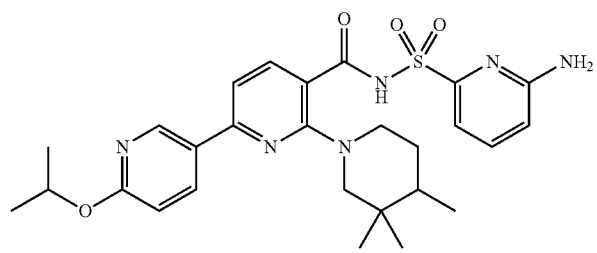 [SMILES: CC(C)Oc1ccc(-c2ccc(C(=O)NS(=O)(=O)c3cccc(N)n3)c(N3CCC(C)C(C)(C)C3)n2)cn1]
435
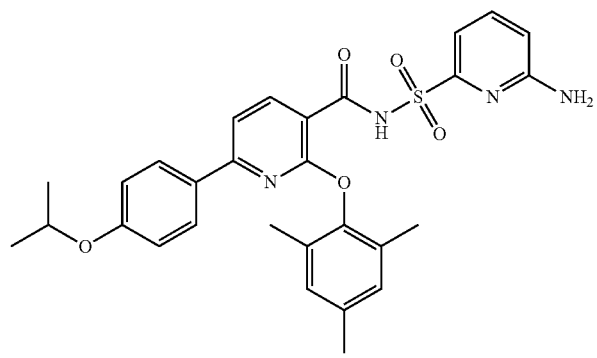 [SMILES: Cc1cc(C)c(Oc2nc(-c3ccc(OC(C)C)cc3)ccc2C(=O)NS(=O)(=O)c2cccc(N)n2)c(C)c1]
436

TABLE 1-continued
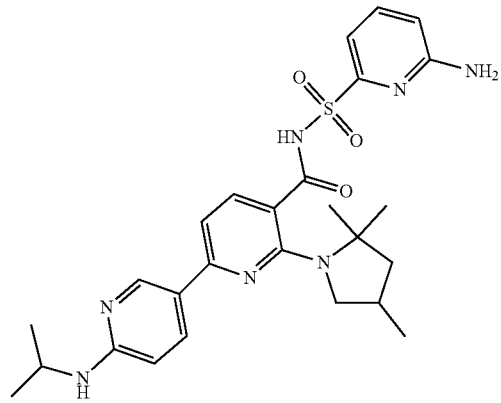 [SMILES: CC1CN(c2nc(-c3ccc(NC(C)C)nc3)ccc2C(=O)NS(=O)(=O)c2cccc(N)n2)C(C)(C)C1]
437
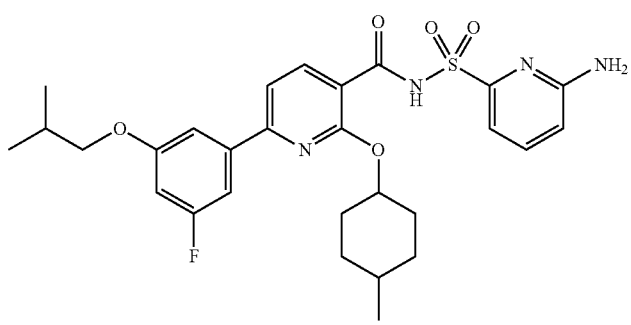 [SMILES: CC(C)COc1cc(F)cc(-c2ccc(C(=O)NS(=O)(=O)c3cccc(N)n3)c(OC3CCC(C)CC3)n2)c1]
438
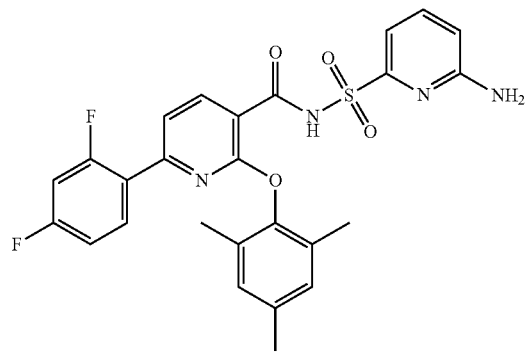 [SMILES: Cc1cc(C)c(Oc2nc(-c3ccc(F)cc3F)ccc2C(=O)NS(=O)(=O)c2cccc(N)n2)c(C)c1]
439
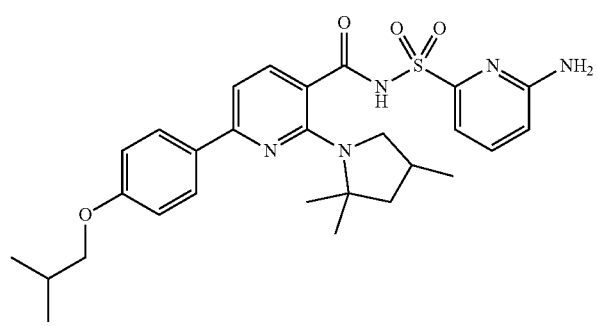 [SMILES: CC(C)COc1ccc(-c2ccc(C(=O)NS(=O)(=O)c3cccc(N)n3)c(N3CC(C)CC3(C)C)n2)cc1]
440

TABLE 1-continued
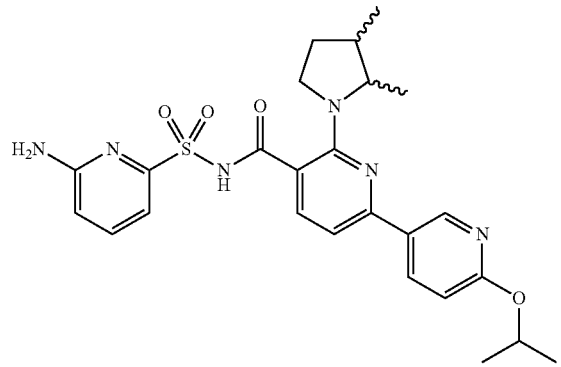 441
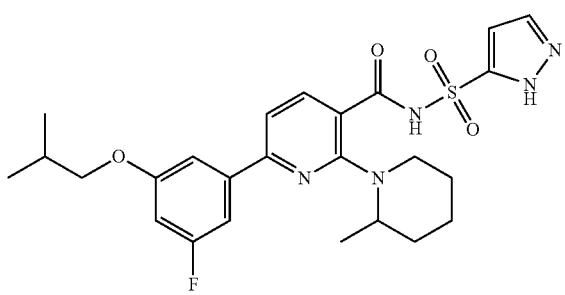 [SMILES: CC(C)COc1cc(F)cc(-c2ccc(C(=O)NS(=O)(=O)c3ccn[nH]3)c(N3CCCCC3C)n2)c1] 442
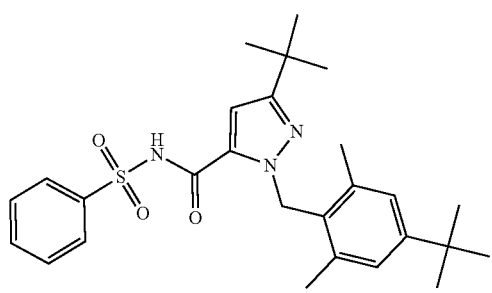 [SMILES: Cc1cc(C(C)(C)C)cc(C)c1Cn1nc(C(C)(C)C)cc1C(=O)NS(=O)(=O)c1ccccc1] 443
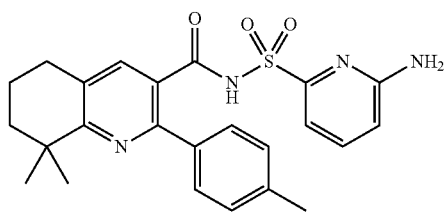 [SMILES: Cc1ccc(-c2nc3c(cc2C(=O)NS(=O)(=O)c2cccc(N)n2)CCCC3(C)C)cc1] 444
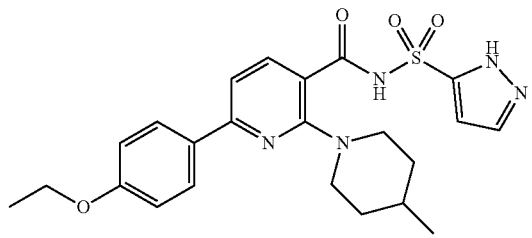 [SMILES: CCOc1ccc(-c2ccc(C(=O)NS(=O)(=O)c3ccn[nH]3)c(N3CCC(C)CC3)n2)cc1] 445

TABLE 1-continued

446

447

448

TABLE 1-continued
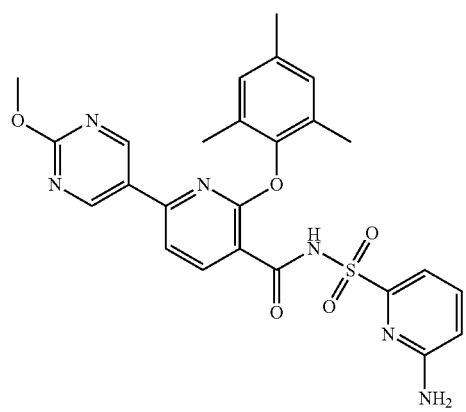 [SMILES: COc1ncc(-c2ccc(C(=O)NS(=O)(=O)c3cccc(N)n3)c(Oc3c(C)cc(C)cc3C)n2)cn1]
449
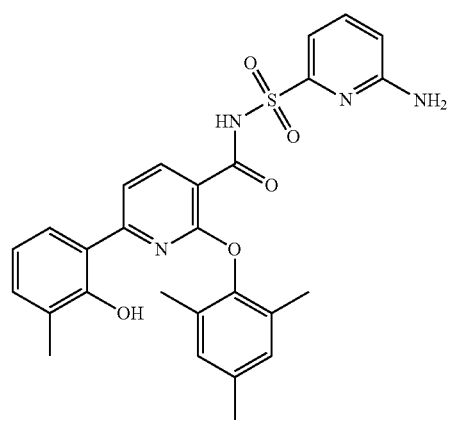 [SMILES: Cc1cc(C)c(Oc2nc(-c3cccc(C)c3O)ccc2C(=O)NS(=O)(=O)c2cccc(N)n2)c(C)c1]
450
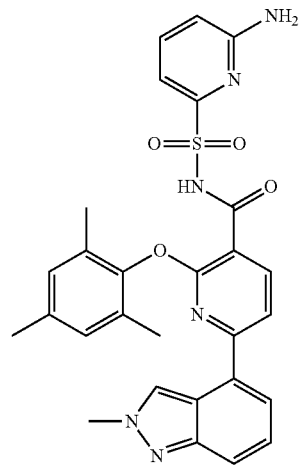 [SMILES: Cc1cc(C)c(Oc2nc(-c3cccc4nn(C)cc34)ccc2C(=O)NS(=O)(=O)c2cccc(N)n2)c(C)c1]
451
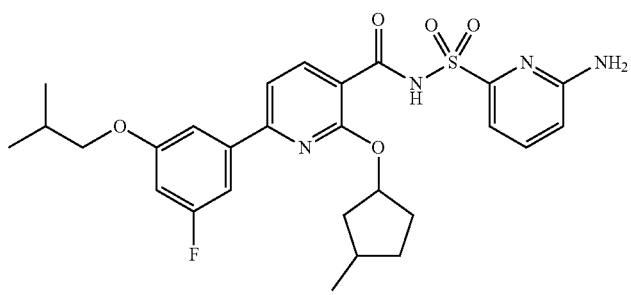 [SMILES: CC(C)COc1cc(F)cc(-c2ccc(C(=O)NS(=O)(=O)c3cccc(N)n3)c(OC3CCC(C)C3)n2)c1]
452

TABLE 1-continued
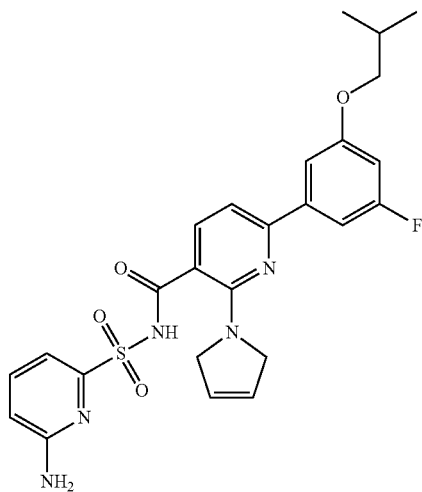 [SMILES: CC(C)COc1cc(F)cc(-c2ccc(C(=O)NS(=O)(=O)c3cccc(N)n3)c(N3CC=CC3)n2)c1]
453
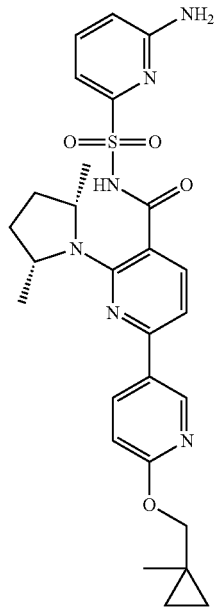 [SMILES: C[C@@H]1CC[C@H](C)N1c1nc(-c2ccc(OCC3(C)CC3)nc2)ccc1C(=O)NS(=O)(=O)c1cccc(N)n1]
454
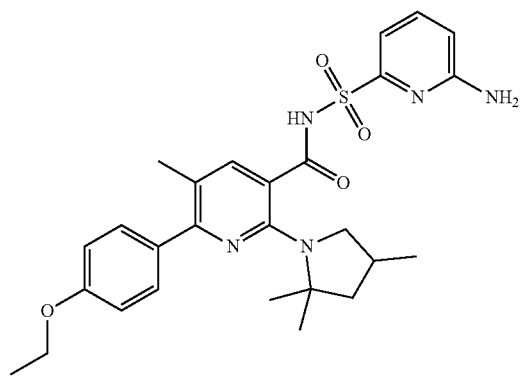 [SMILES: CCOc1ccc(-c2nc(N3CC(C)CC3(C)C)c(C(=O)NS(=O)(=O)c3cccc(N)n3)cc2C)cc1]
455

TABLE 1-continued
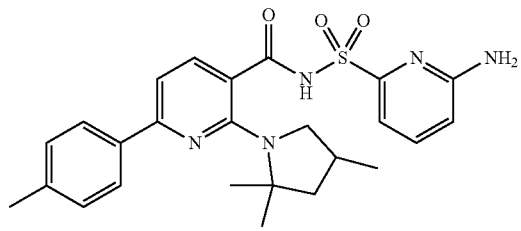 [SMILES: Cc1ccc(-c2ccc(C(=O)NS(=O)(=O)c3cccc(N)n3)c(N3CC(C)CC3(C)C)n2)cc1]
456
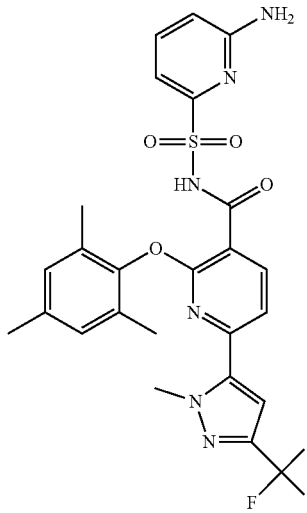
457
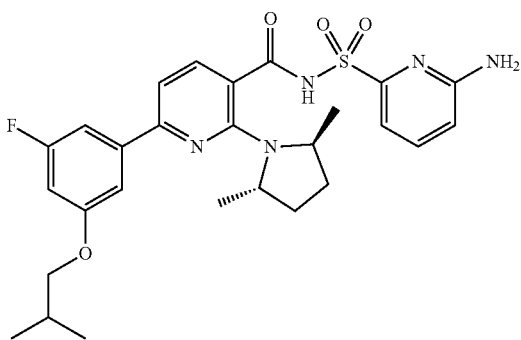 [SMILES: CC(C)COc1cc(F)cc(-c2ccc(C(=O)NS(=O)(=O)c3cccc(N)n3)c(N3[C@@H](C)CC[C@@H]3C)n2)c1]
458
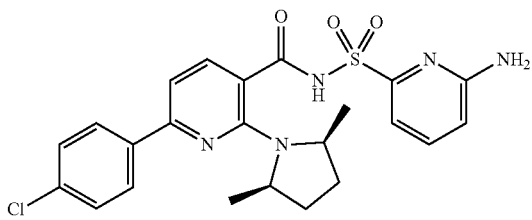 [SMILES: C[C@@H]1CC[C@H](C)N1c1nc(-c2ccc(Cl)cc2)ccc1C(=O)NS(=O)(=O)c1cccc(N)n1]
459
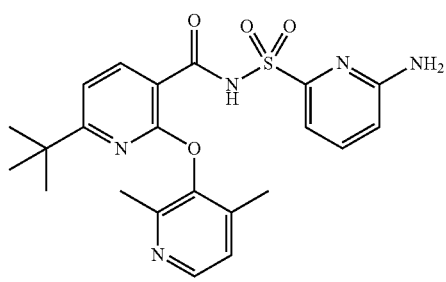 [SMILES: Cc1ccnc(C)c1Oc1nc(C(C)(C)C)ccc1C(=O)NS(=O)(=O)c1cccc(N)n1]
460

TABLE 1-continued
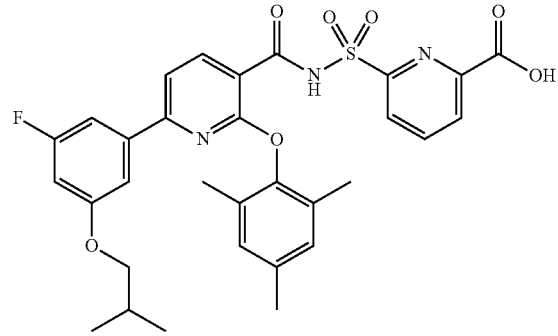 [SMILES: Cc1cc(C)c(Oc2nc(-c3cc(F)cc(OCC(C)C)c3)ccc2C(=O)NS(=O)(=O)c2cccc(C(=O)O)n2)c(C)c1]
461
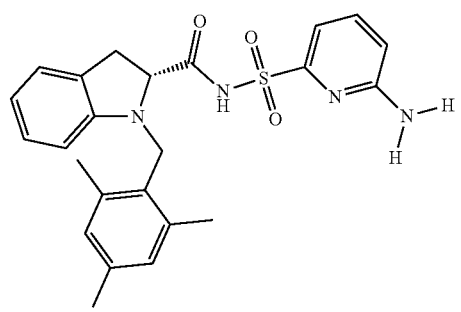 [SMILES: Cc1cc(C)c(CN2c3ccccc3C[C@@H]2C(=O)NS(=O)(=O)c2cccc(N)n2)c(C)c1]
462
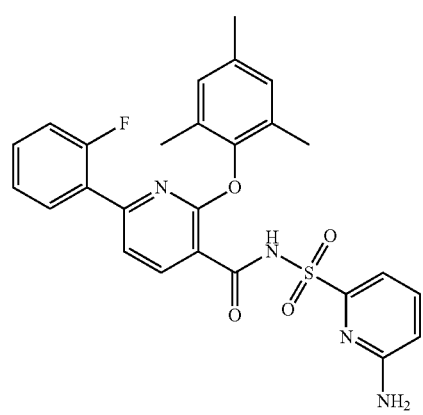 [SMILES: Cc1cc(C)c(Oc2nc(-c3ccccc3F)ccc2C(=O)NS(=O)(=O)c2cccc(N)n2)c(C)c1]
463
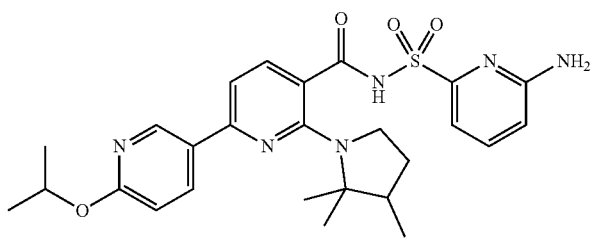 [SMILES: CC(C)Oc1ccc(-c2ccc(C(=O)NS(=O)(=O)c3cccc(N)n3)c(N3CCC(C)C3(C)C)n2)cn1]
464

TABLE 1-continued
| | |
|---|---|
| 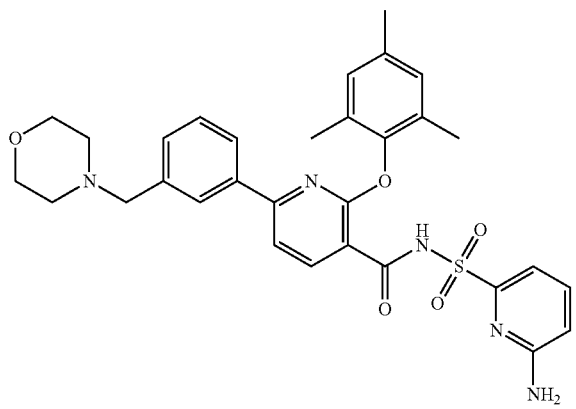 [SMILES: Cc1cc(C)c(Oc2nc(-c3cccc(CN4CCOCC4)c3)ccc2C(=O)NS(=O)(=O)c2cccc(N)n2)c(C)c1] | 465 |
| 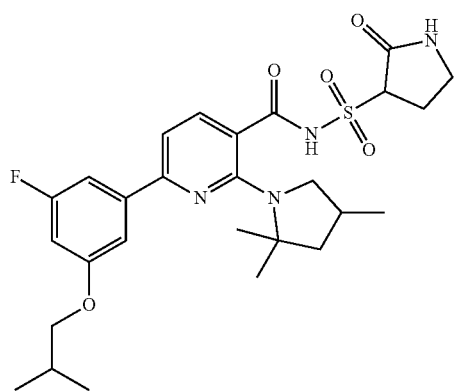 [SMILES: CC(C)COc1cc(F)cc(-c2ccc(C(=O)NS(=O)(=O)C3CCNC3=O)c(N3CC(C)CC3(C)C)n2)c1] | 466 |
| 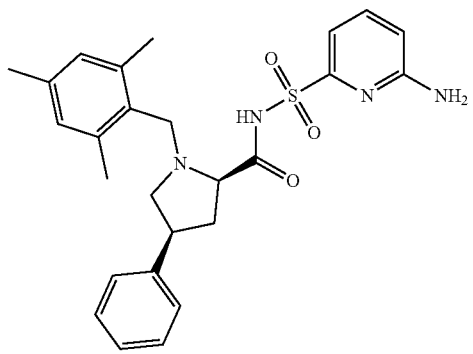 [SMILES: Cc1cc(C)c(CN2C[C@H](c3ccccc3)C[C@@H]2C(=O)NS(=O)(=O)c2cccc(N)n2)c(C)c1] | 467 |
| 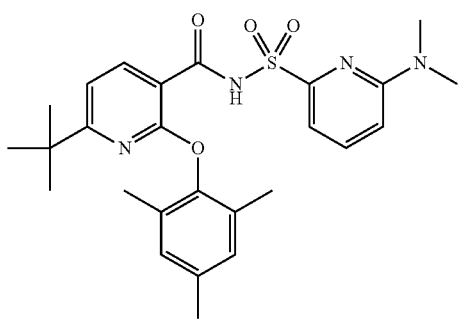 [SMILES: Cc1cc(C)c(Oc2nc(C(C)(C)C)ccc2C(=O)NS(=O)(=O)c2cccc(N(C)C)n2)c(C)c1] | 468 |

TABLE 1-continued
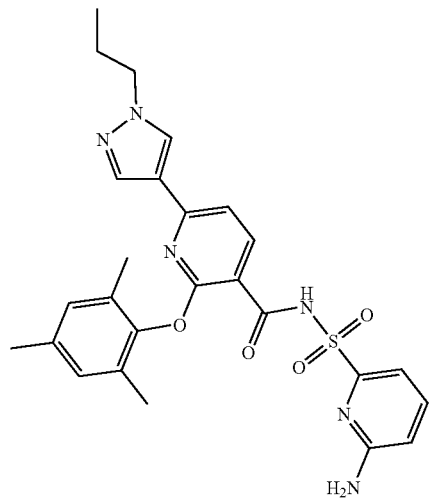 [SMILES: CCCn1cc(-c2ccc(C(=O)NS(=O)(=O)c3cccc(N)n3)c(Oc3c(C)cc(C)cc3C)n2)cn1]
469
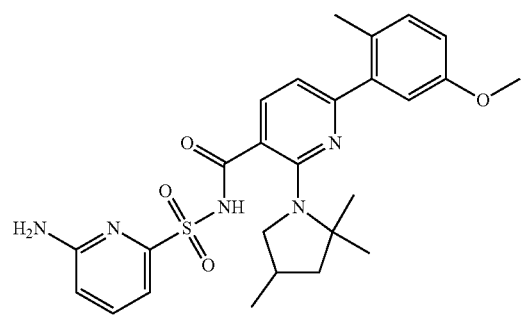 [SMILES: COc1ccc(C)c(-c2ccc(C(=O)NS(=O)(=O)c3cccc(N)n3)c(N3CC(C)CC3(C)C)n2)c1]
470
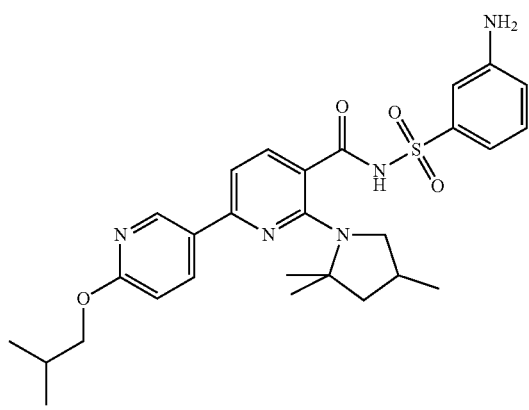 [SMILES: CC(C)COc1ccc(-c2ccc(C(=O)NS(=O)(=O)c3cccc(N)c3)c(N3CC(C)CC3(C)C)n2)cn1]
471
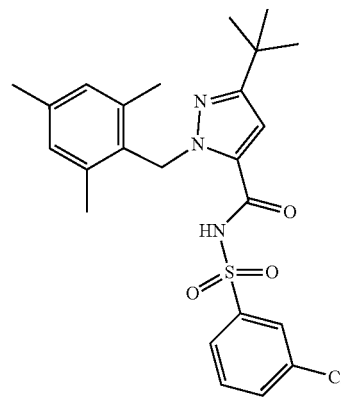
472

US 12,168,009 B2
589	590
TABLE 1-continued
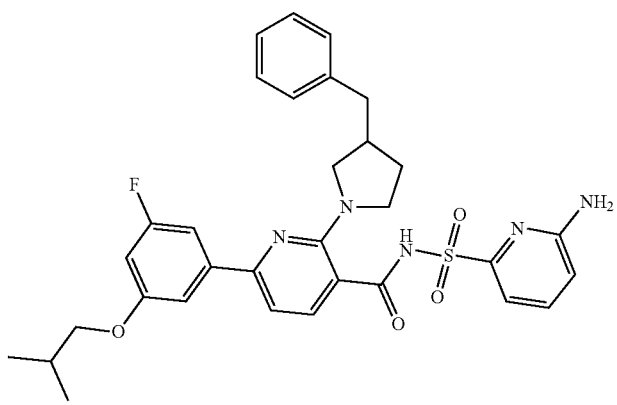 [SMILES: CC(C)COc1cc(F)cc(-c2ccc(C(=O)NS(=O)(=O)c3cccc(N)n3)c(N3CCC(Cc4ccccc4)C3)n2)c1]
473
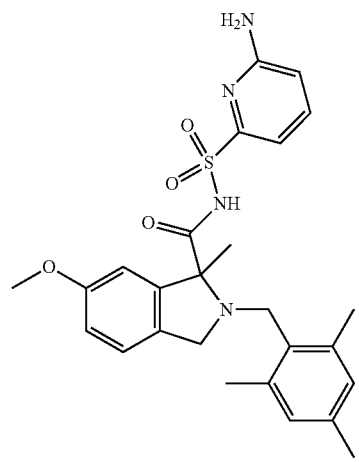
474
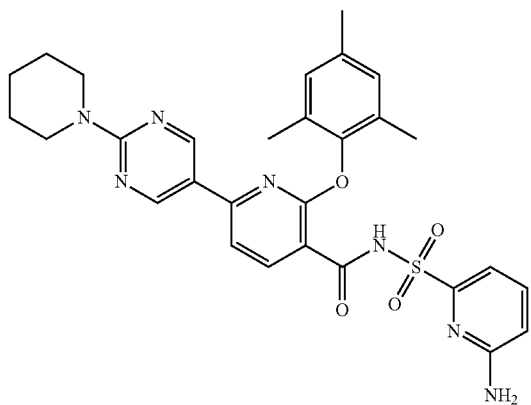 [SMILES: Cc1cc(C)c(Oc2nc(-c3cnc(N4CCCCC4)nc3)ccc2C(=O)NS(=O)(=O)c2cccc(N)n2)c(C)c1]
475
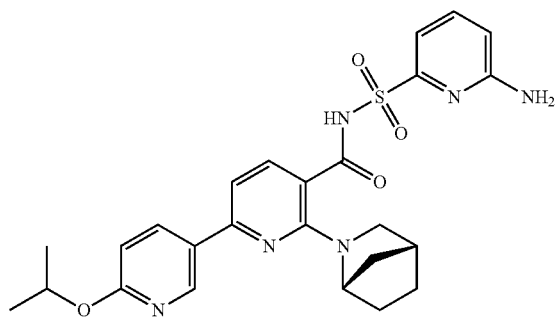 [SMILES: CC(C)Oc1ccc(-c2ccc(C(=O)NS(=O)(=O)c3cccc(N)n3)c(N3C[C@@H]4CC[C@H]3C4)n2)cn1]
476

TABLE 1-continued
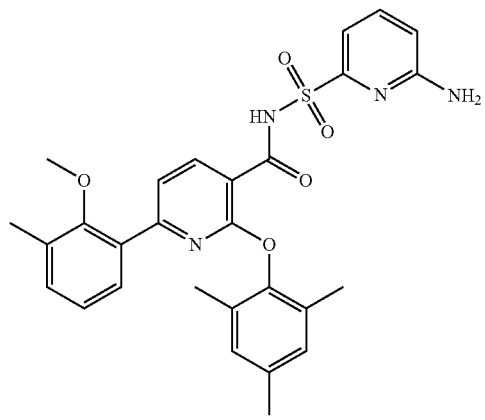 [SMILES: COc1c(C)cccc1-c1ccc(C(=O)NS(=O)(=O)c2cccc(N)n2)c(Oc2c(C)cc(C)cc2C)n1]
477
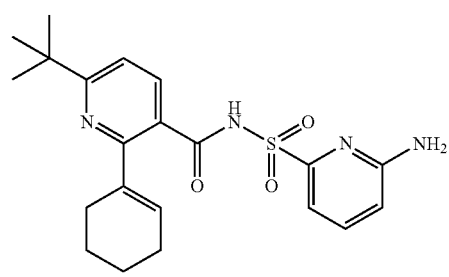 [SMILES: CC(C)(C)c1ccc(C(=O)NS(=O)(=O)c2cccc(N)n2)c(C2=CCCCC2)n1]
478
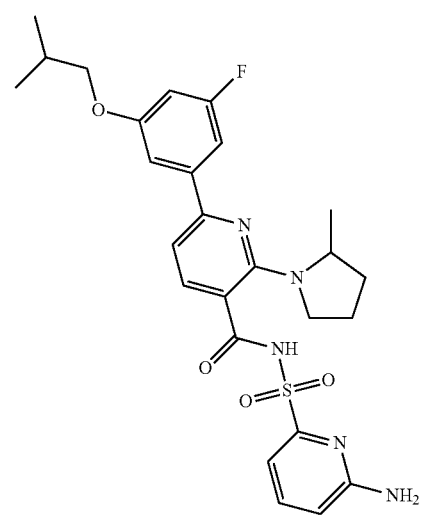 [SMILES: CC(C)COc1cc(F)cc(-c2ccc(C(=O)NS(=O)(=O)c3cccc(N)n3)c(N3CCCC3C)n2)c1]
479
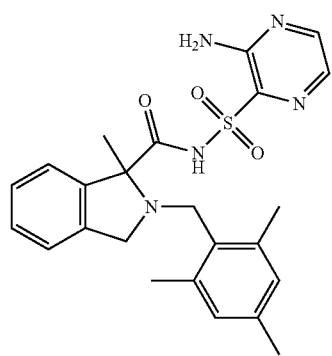 [SMILES: Cc1cc(C)c(CN2Cc3ccccc3C2(C)C(=O)NS(=O)(=O)c2nccnc2N)c(C)c1]
480

TABLE 1-continued
481
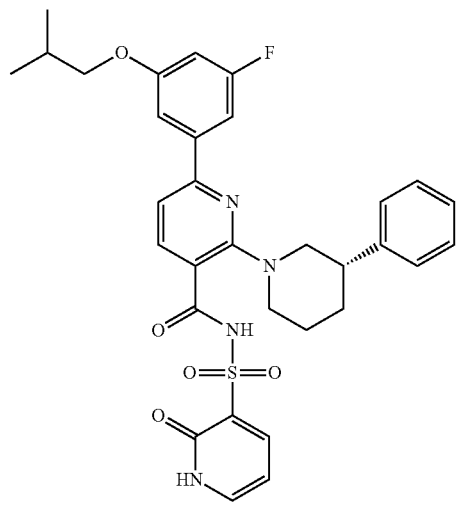 [SMILES: CC(C)COc1cc(F)cc(-c2ccc(C(=O)NS(=O)(=O)c3ccc[nH]c3=O)c(N3CCC[C@@H](c4ccccc4)C3)n2)c1]
482
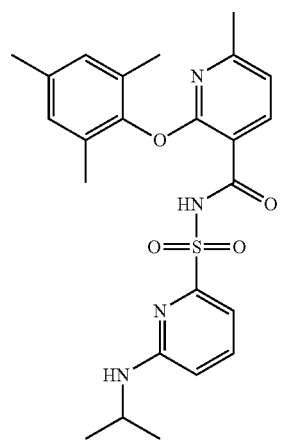 [SMILES: Cc1cc(C)c(Oc2nc(C)ccc2C(=O)NS(=O)(=O)c2cccc(NC(C)C)n2)c(C)c1]
483
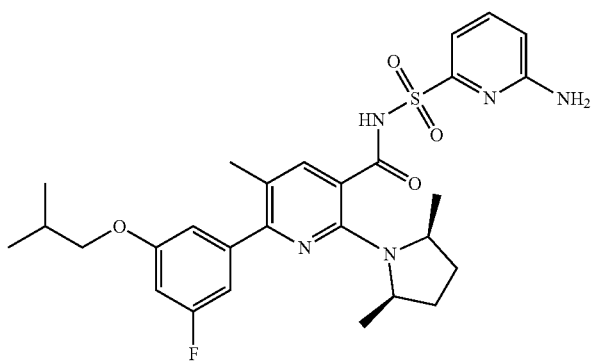 [SMILES: Cc1cc(C(=O)NS(=O)(=O)c2cccc(N)n2)c(N2[C@H](C)CC[C@@H]2C)nc1-c1cc(F)cc(OCC(C)C)c1]
484
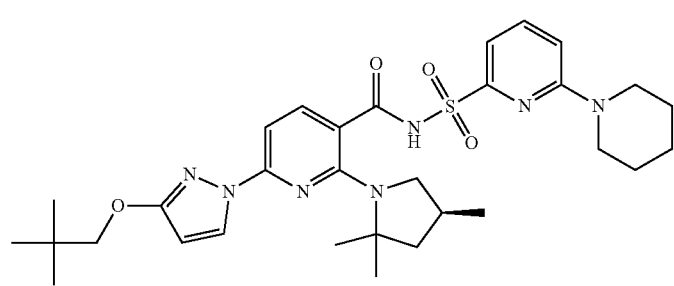 [SMILES: C[C@@H]1CN(c2nc(-n3ccc(OCC(C)(C)C)n3)ccc2C(=O)NS(=O)(=O)c2cccc(N3CCCCC3)n2)C(C)(C)C1]

TABLE 1-continued
| | |
|---|---|
| 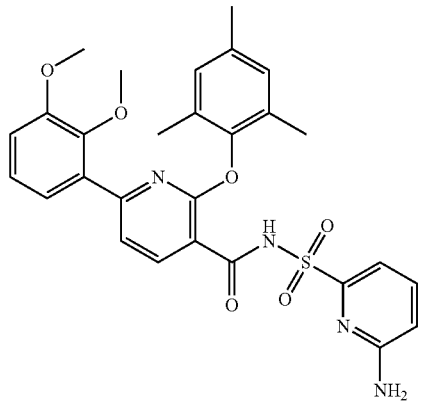 [SMILES: COc1cccc(-c2ccc(C(=O)NS(=O)(=O)c3cccc(N)n3)c(Oc3c(C)cc(C)cc3C)n2)c1OC] | 485 |
| 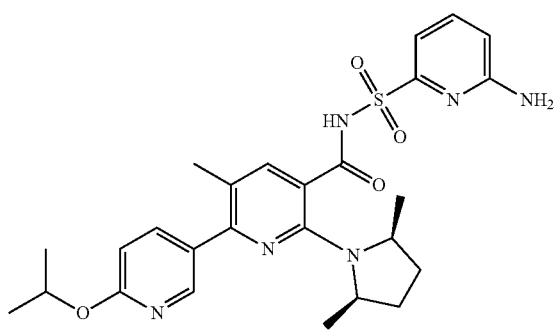 [SMILES: Cc1cc(C(=O)NS(=O)(=O)c2cccc(N)n2)c(N2[C@H](C)CC[C@@H]2C)nc1-c1ccc(OC(C)C)nc1] | 486 |
| 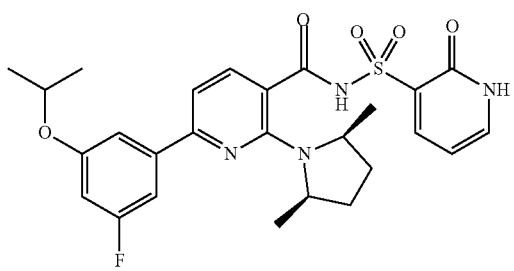 | 487 |
| 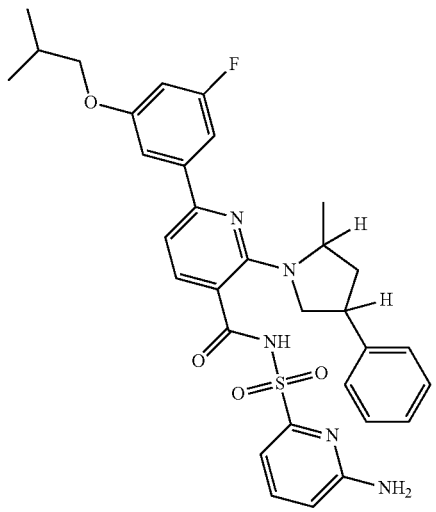 [SMILES: CC(C)COc1cc(F)cc(-c2ccc(C(=O)NS(=O)(=O)c3cccc(N)n3)c(N3CC(c4ccccc4)CC3C)n2)c1] | 488 |

TABLE 1-continued
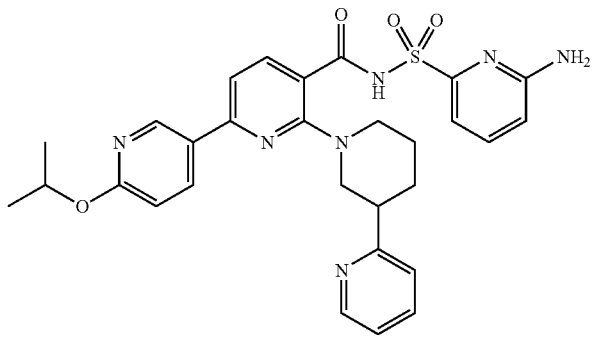 [SMILES: CC(C)Oc1ccc(-c2ccc(C(=O)NS(=O)(=O)c3cccc(N)n3)c(N3CCCC(c4ccccn4)C3)n2)cn1]
489
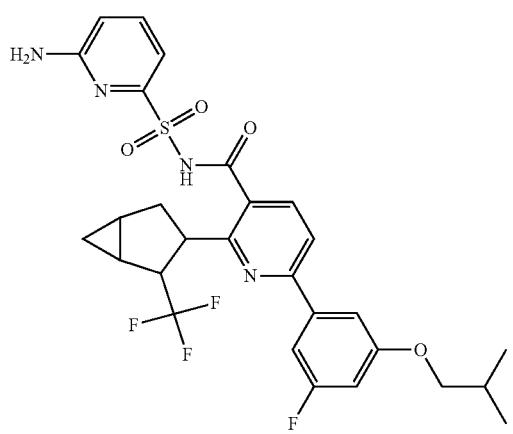 [SMILES: CC(C)COc1cc(F)cc(-c2ccc(C(=O)NS(=O)(=O)c3cccc(N)n3)c(C3CC4CC4C3C(F)(F)F)n2)c1]
490
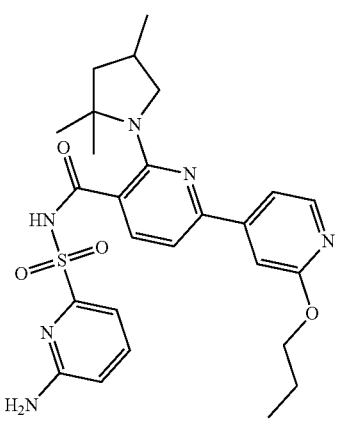 [SMILES: CCCOc1cc(-c2ccc(C(=O)NS(=O)(=O)c3cccc(N)n3)c(N3CC(C)CC3(C)C)n2)ccn1]
491
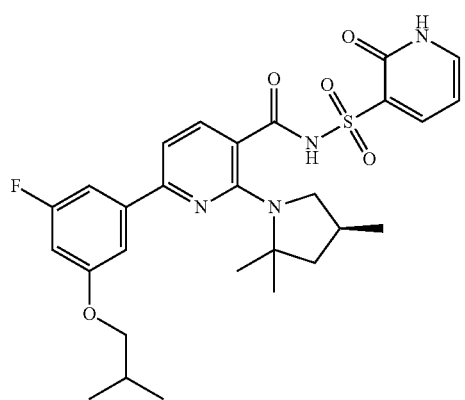 [SMILES: CC(C)COc1cc(F)cc(-c2ccc(C(=O)NS(=O)(=O)c3ccc[nH]c3=O)c(N3C[C@@H](C)CC3(C)C)n2)c1]
492

TABLE 1-continued

| | |
|---|---|
| (structure) | 493 |
| (structure) | 494 |
| (structure) | 495 |
| (structure) | 496 |

TABLE 1-continued
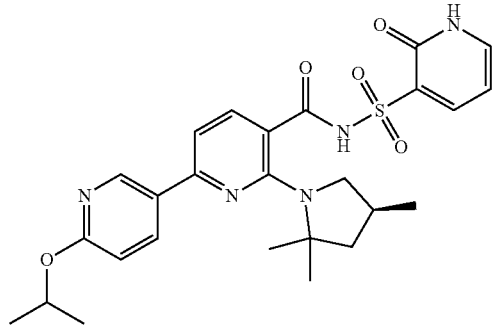 [SMILES: CC(C)Oc1ccc(-c2ccc(C(=O)NS(=O)(=O)c3ccc[nH]c3=O)c(N3C[C@@H](C)CC3(C)C)n2)cn1]
497
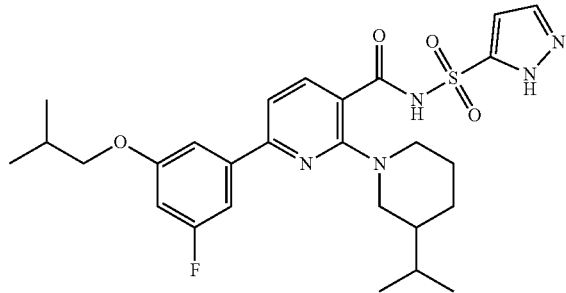 [SMILES: CC(C)COc1cc(F)cc(-c2ccc(C(=O)NS(=O)(=O)c3ccn[nH]3)c(N3CCCC(C(C)C)C3)n2)c1]
498
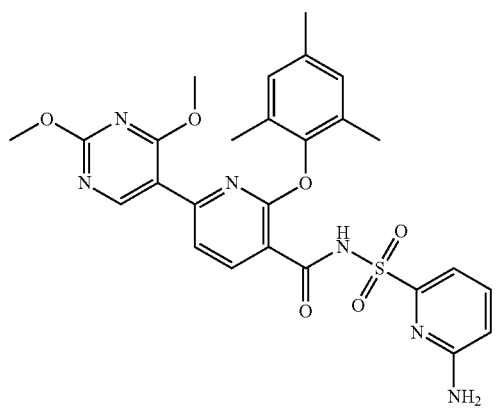 [SMILES: COc1ncc(-c2ccc(C(=O)NS(=O)(=O)c3cccc(N)n3)c(Oc3c(C)cc(C)cc3C)n2)c(OC)n1]
499
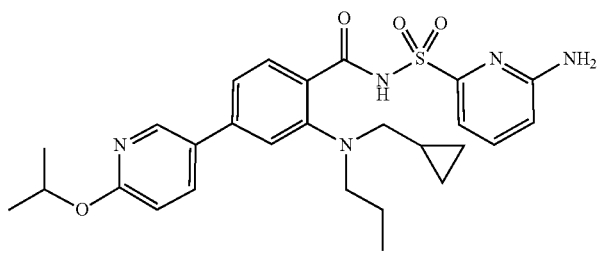 [SMILES: CCCN(CC1CC1)c1cc(-c2ccc(OC(C)C)nc2)ccc1C(=O)NS(=O)(=O)c1cccc(N)n1]
500
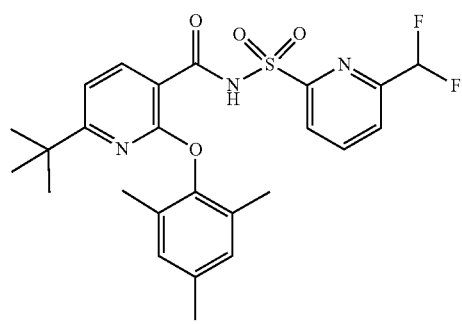 [SMILES: Cc1cc(C)c(Oc2nc(C(C)(C)C)ccc2C(=O)NS(=O)(=O)c2cccc(C(F)F)n2)c(C)c1]
501

TABLE 1-continued
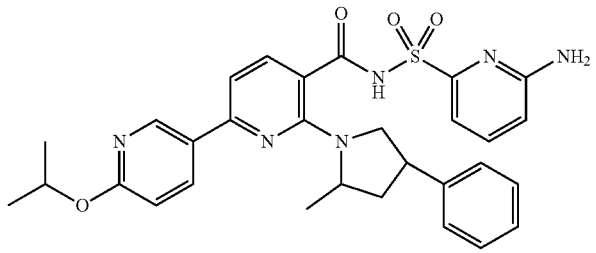 [SMILES: CC(C)Oc1ccc(-c2ccc(C(=O)NS(=O)(=O)c3cccc(N)n3)c(N3CC(c4ccccc4)CC3C)n2)cn1]
502
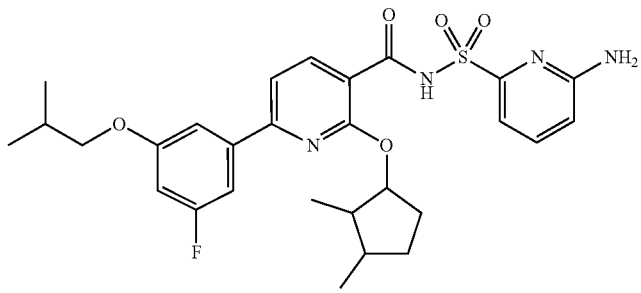
503
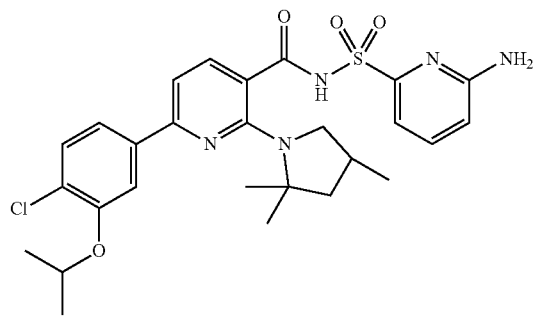 [SMILES: CC1CN(c2nc(-c3ccc(Cl)c(OC(C)C)c3)ccc2C(=O)NS(=O)(=O)c2cccc(N)n2)C(C)(C)C1]
504
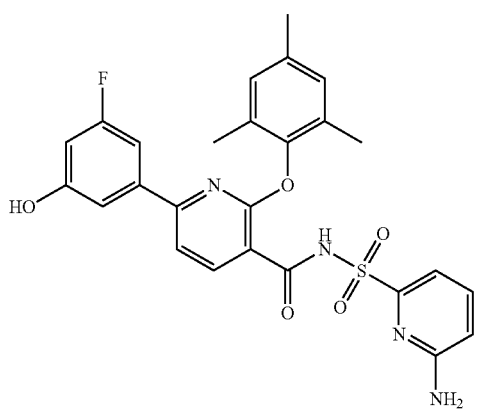 [SMILES: Cc1cc(C)c(Oc2nc(-c3cc(O)cc(F)c3)ccc2C(=O)NS(=O)(=O)c2cccc(N)n2)c(C)c1]
505
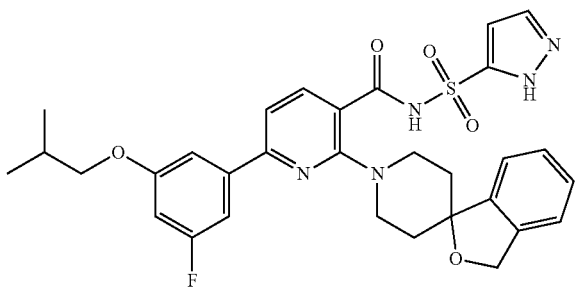 [SMILES: CC(C)COc1cc(F)cc(-c2ccc(C(=O)NS(=O)(=O)c3ccn[nH]3)c(N3CCC4(CC3)OCc3ccccc34)n2)c1]
506

TABLE 1-continued
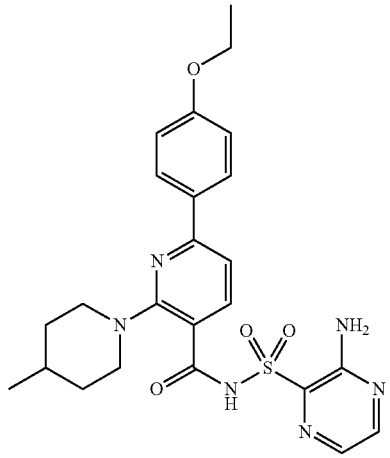 [SMILES: CCOc1ccc(-c2ccc(C(=O)NS(=O)(=O)c3nccnc3N)c(N3CCC(C)CC3)n2)cc1]
507
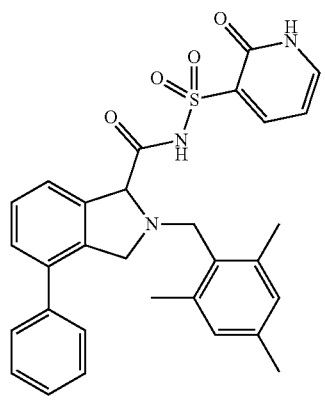 [SMILES: Cc1cc(C)c(CN2Cc3c(-c4ccccc4)cccc3C2C(=O)NS(=O)(=O)c2ccc[nH]c2=O)c(C)c1]
508
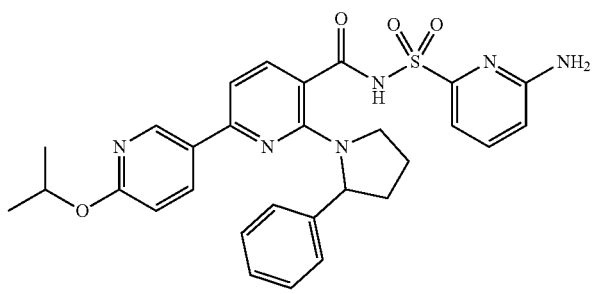 [SMILES: CC(C)Oc1ccc(-c2ccc(C(=O)NS(=O)(=O)c3cccc(N)n3)c(N3CCCC3c3ccccc3)n2)cn1]
509
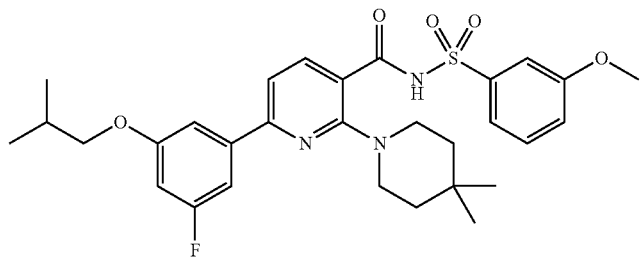 [SMILES: COc1cccc(S(=O)(=O)NC(=O)c2ccc(-c3cc(F)cc(OCC(C)C)c3)nc2N2CCC(C)(C)CC2)c1]
510

TABLE 1-continued
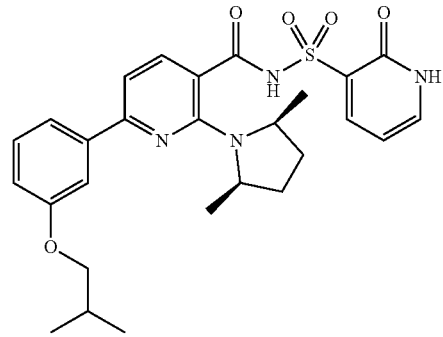 [SMILES: CC(C)COc1cccc(-c2ccc(C(=O)NS(=O)(=O)c3ccc[nH]c3=O)c(N3[C@H](C)CC[C@@H]3C)n2)c1] 511
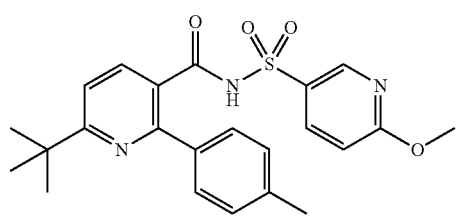 [SMILES: COc1ccc(S(=O)(=O)NC(=O)c2ccc(C(C)(C)C)nc2-c2ccc(C)cc2)cn1] 512
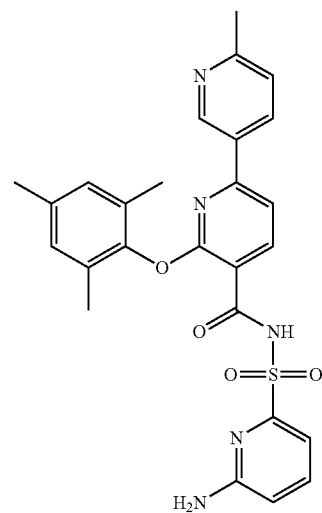 [SMILES: Cc1cc(C)c(Oc2nc(-c3ccc(C)nc3)ccc2C(=O)NS(=O)(=O)c2cccc(N)n2)c(C)c1] 513
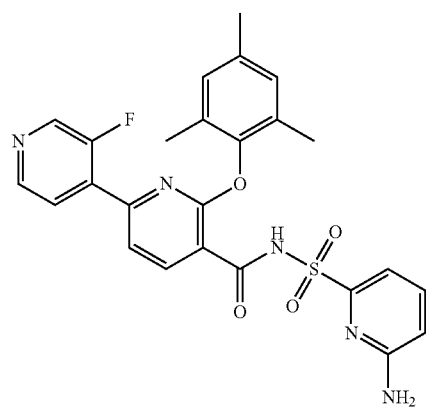 [SMILES: Cc1cc(C)c(Oc2nc(-c3ccncc3F)ccc2C(=O)NS(=O)(=O)c2cccc(N)n2)c(C)c1] 514

TABLE 1-continued
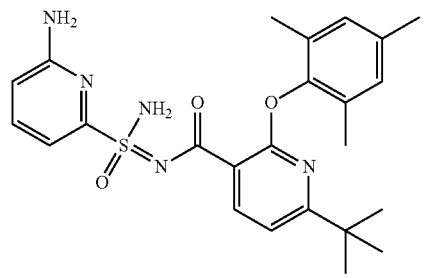 [SMILES: Cc1cc(C)c(Oc2nc(C(C)(C)C)ccc2C(=O)N=S(N)(=O)c2cccc(N)n2)c(C)c1]
515
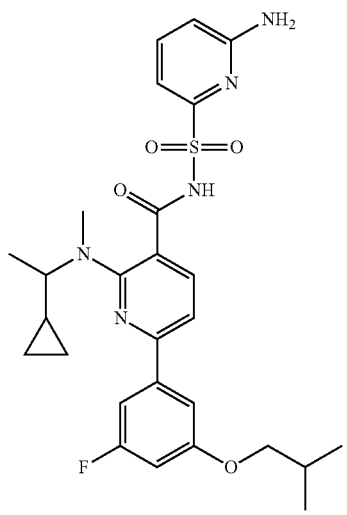 [SMILES: CC(C)COc1cc(F)cc(-c2ccc(C(=O)NS(=O)(=O)c3cccc(N)n3)c(N(C)C(C)C3CC3)n2)c1]
516
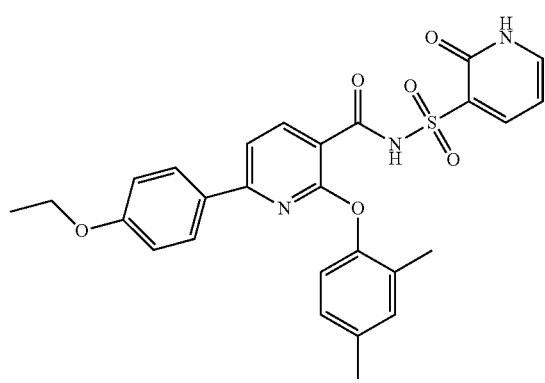 [SMILES: CCOc1ccc(-c2ccc(C(=O)NS(=O)(=O)c3ccc[nH]c3=O)c(Oc3ccc(C)cc3C)n2)cc1]
517
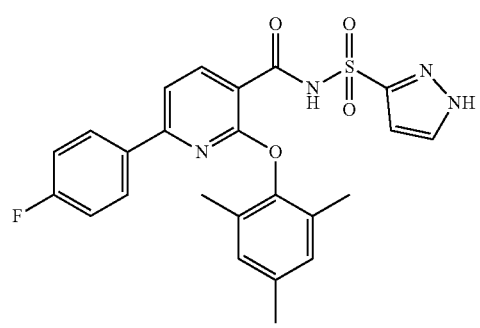 [SMILES: Cc1cc(C)c(Oc2nc(-c3ccc(F)cc3)ccc2C(=O)NS(=O)(=O)c2cc[nH]n2)c(C)c1]
518

TABLE 1-continued
| | |
|---|---|
| 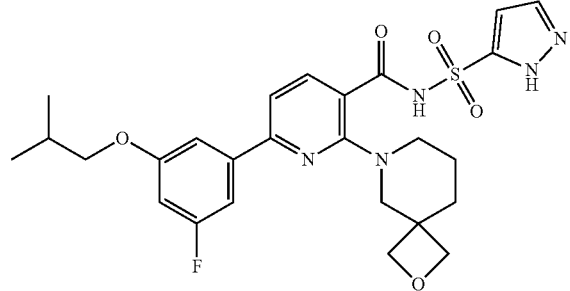 [SMILES: CC(C)COc1cc(F)cc(-c2ccc(C(=O)NS(=O)(=O)c3ccn[nH]3)c(N3CCCC4(COC4)C3)n2)c1] | 519 |
| 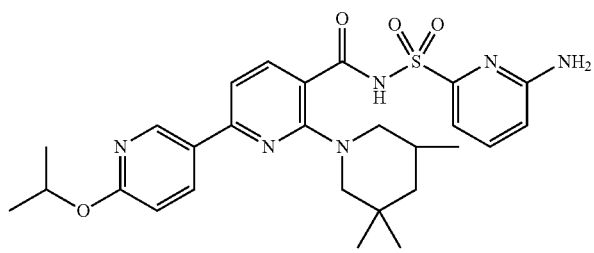 [SMILES: CC1CN(c2nc(-c3ccc(OC(C)C)nc3)ccc2C(=O)NS(=O)(=O)c2cccc(N)n2)CC(C)(C)C1] | 520 |
| 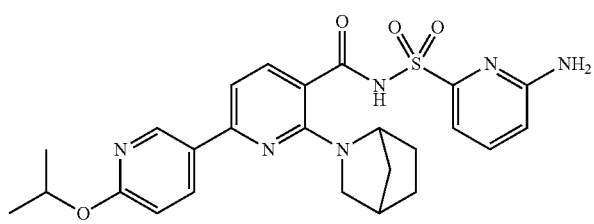 [SMILES: CC(C)Oc1ccc(-c2ccc(C(=O)NS(=O)(=O)c3cccc(N)n3)c(N3CC4CCC3C4)n2)cn1] | 521 |
| 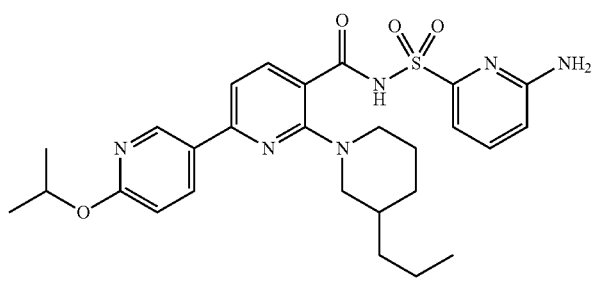 [SMILES: CCCC1CCCN(c2nc(-c3ccc(OC(C)C)nc3)ccc2C(=O)NS(=O)(=O)c2cccc(N)n2)C1] | 522 |
| 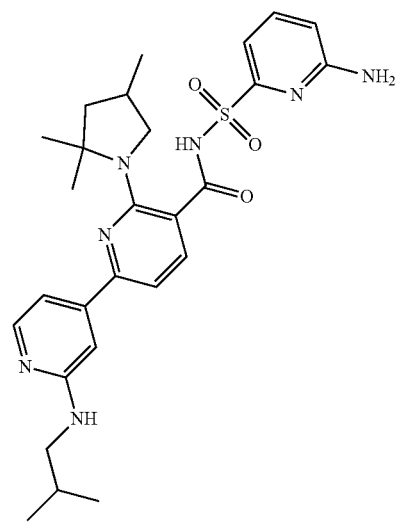 | 523 |

TABLE 1-continued
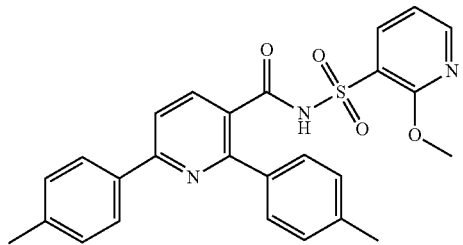
524
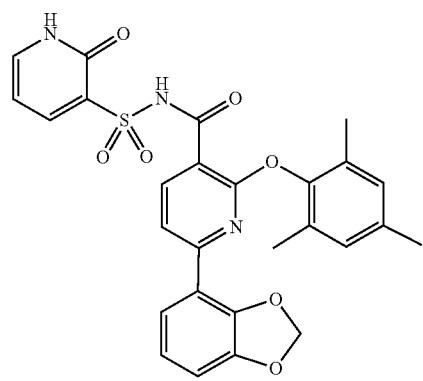 [SMILES: Cc1cc(C)c(Oc2nc(-c3cccc4c3OCO4)ccc2C(=O)NS(=O)(=O)c2ccc[nH]c2=O)c(C)c1]
525
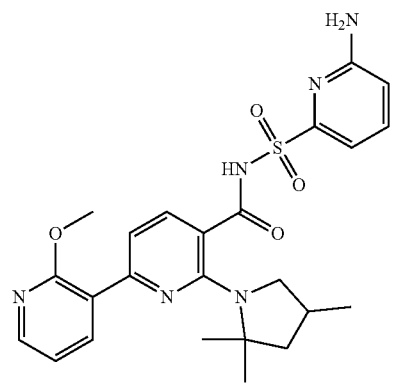 [SMILES: COc1ncccc1-c1ccc(C(=O)NS(=O)(=O)c2cccc(N)n2)c(N2CC(C)CC2(C)C)n1]
526
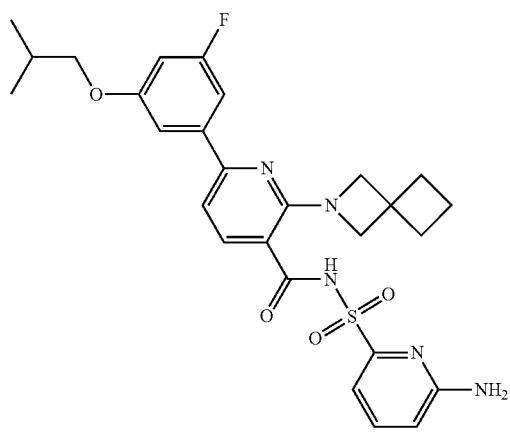
527

TABLE 1-continued
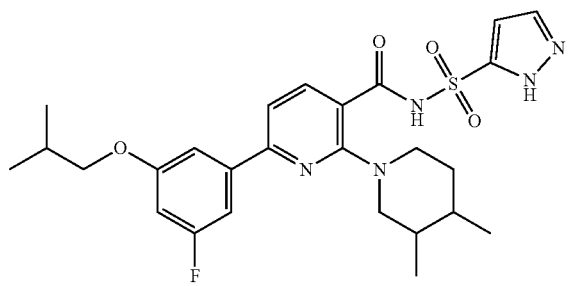 [SMILES: CC(C)COc1cc(F)cc(-c2ccc(C(=O)NS(=O)(=O)c3ccn[nH]3)c(N3CCC(C)C(C)C3)n2)c1]
528
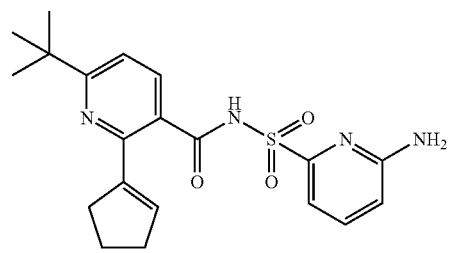 [SMILES: CC(C)(C)c1ccc(C(=O)NS(=O)(=O)c2cccc(N)n2)c(C2=CCCC2)n1]
529
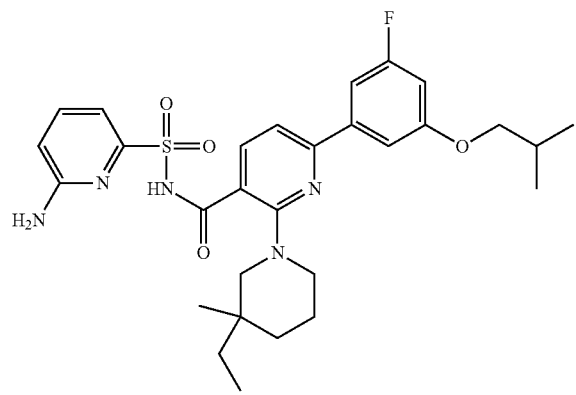 [SMILES: CCC1(C)CCCN(c2nc(-c3cc(F)cc(OCC(C)C)c3)ccc2C(=O)NS(=O)(=O)c2cccc(N)n2)C1]
530
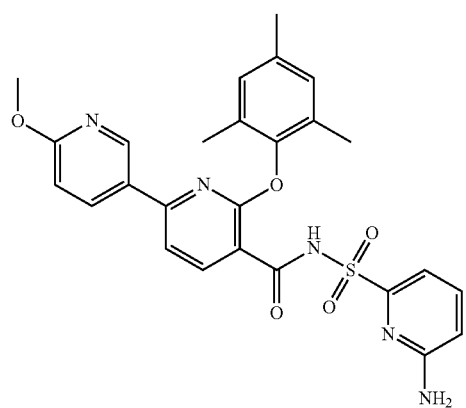
531

TABLE 1-continued
532
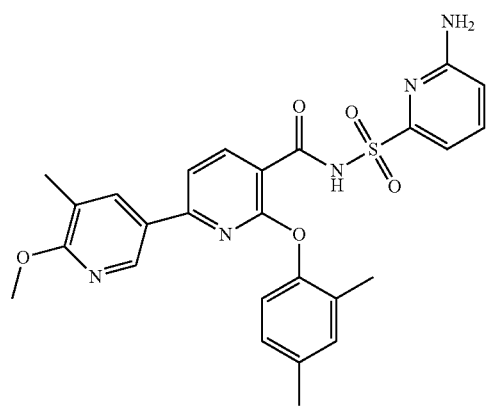 [SMILES: COc1ncc(-c2ccc(C(=O)NS(=O)(=O)c3cccc(N)n3)c(Oc3ccc(C)cc3C)n2)cc1C]
533
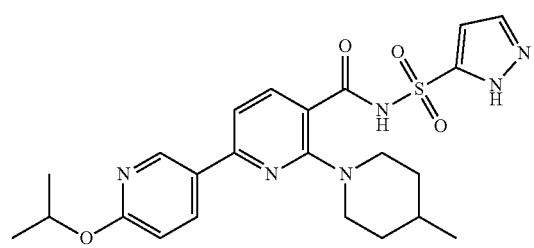 [SMILES: CC1CCN(c2nc(-c3ccc(OC(C)C)nc3)ccc2C(=O)NS(=O)(=O)c2ccn[nH]2)CC1]
534
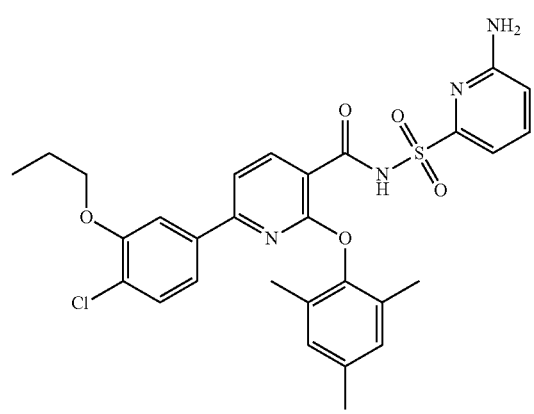 [SMILES: CCCOc1cc(-c2ccc(C(=O)NS(=O)(=O)c3cccc(N)n3)c(Oc3c(C)cc(C)cc3C)n2)ccc1Cl]
535

TABLE 1-continued
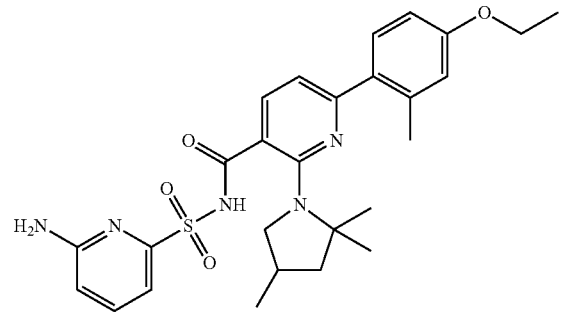 [SMILES: CCOc1ccc(-c2ccc(C(=O)NS(=O)(=O)c3cccc(N)n3)c(N3CC(C)CC3(C)C)n2)c(C)c1]
536
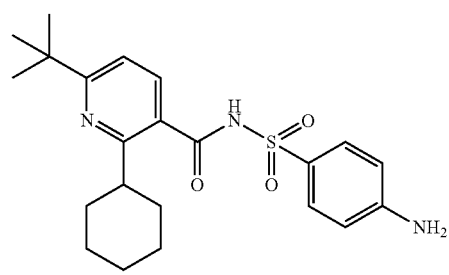
537
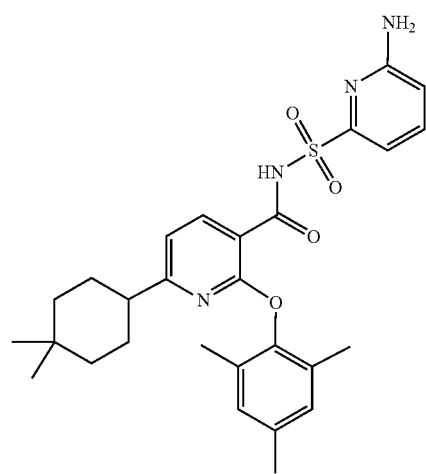
538
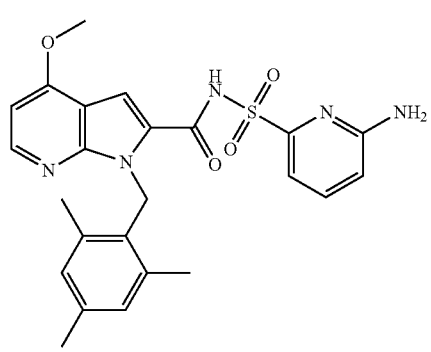 [SMILES: COc1ccnc2c1cc(C(=O)NS(=O)(=O)c1cccc(N)n1)n2Cc1c(C)cc(C)cc1C]
539

TABLE 1-continued
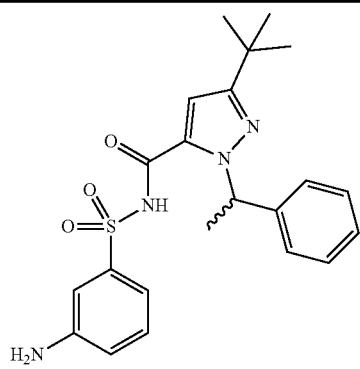
540
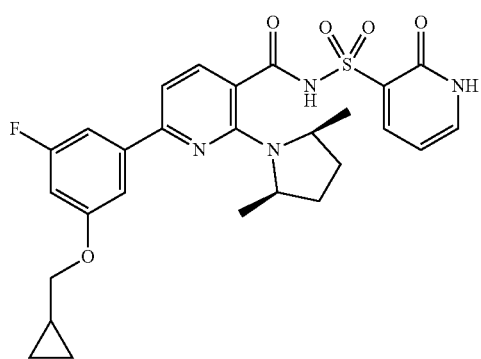 [SMILES: C[C@@H]1CC[C@H](C)N1c1nc(-c2cc(F)cc(OCC3CC3)c2)ccc1C(=O)NS(=O)(=O)c1ccc[nH]c1=O]
541
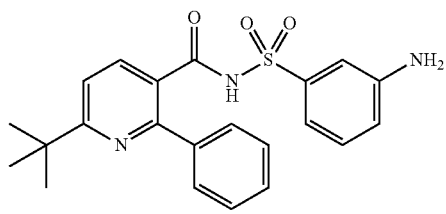 [SMILES: CC(C)(C)c1ccc(C(=O)NS(=O)(=O)c2cccc(N)c2)c(-c2ccccc2)n1]
542
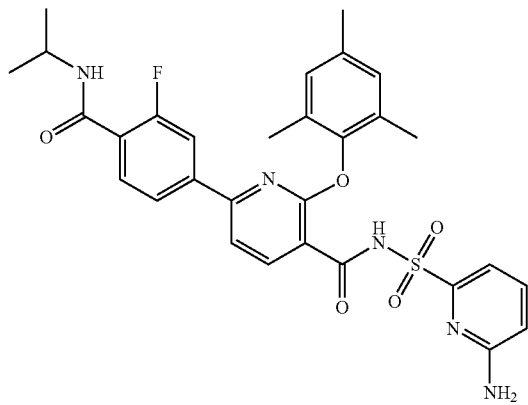 [SMILES: Cc1cc(C)c(Oc2nc(-c3ccc(C(=O)NC(C)C)c(F)c3)ccc2C(=O)NS(=O)(=O)c2cccc(N)n2)c(C)c1]
543
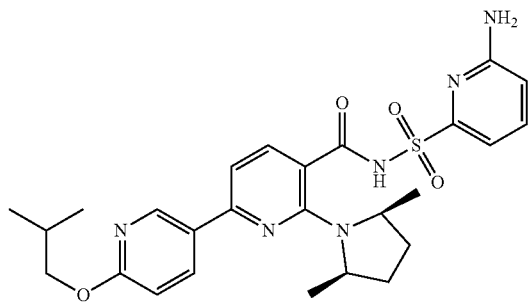 [SMILES: CC(C)COc1ccc(-c2ccc(C(=O)NS(=O)(=O)c3cccc(N)n3)c(N3[C@H](C)CC[C@@H]3C)n2)cn1]
544

TABLE 1-continued
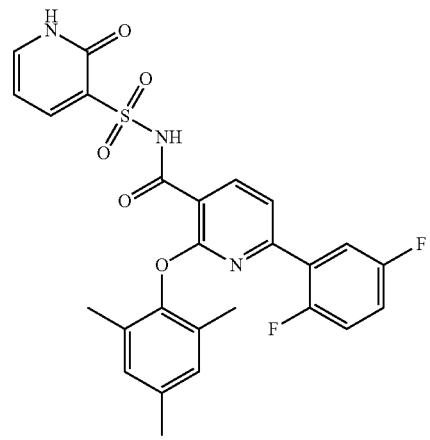 [SMILES: Cc1cc(C)c(Oc2nc(-c3cc(F)ccc3F)ccc2C(=O)NS(=O)(=O)c2ccc[nH]c2=O)c(C)c1]
545
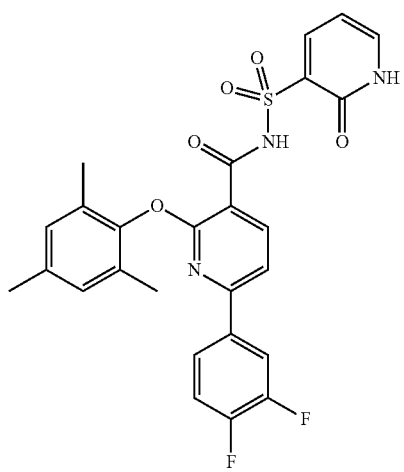 [SMILES: Cc1cc(C)c(Oc2nc(-c3ccc(F)c(F)c3)ccc2C(=O)NS(=O)(=O)c2ccc[nH]c2=O)c(C)c1]
546
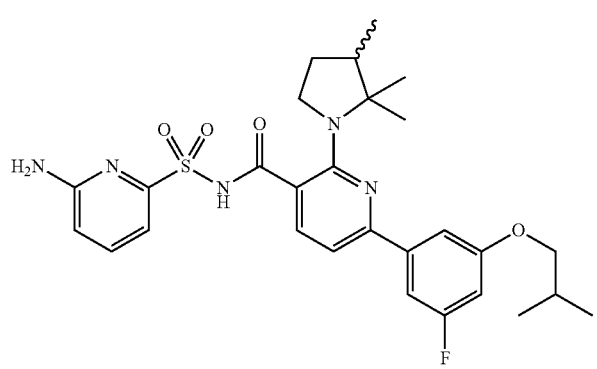 [SMILES: CC(C)COc1cc(F)cc(-c2ccc(C(=O)NS(=O)(=O)c3cccc(N)n3)c(N3CCC(C)C3(C)C)n2)c1]
547
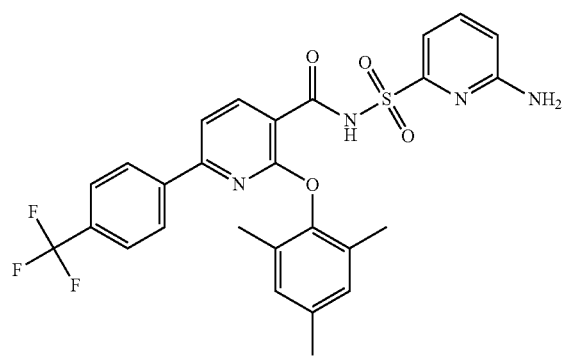 [SMILES: Cc1cc(C)c(Oc2nc(-c3ccc(C(F)(F)F)cc3)ccc2C(=O)NS(=O)(=O)c2cccc(N)n2)c(C)c1]
548

TABLE 1-continued
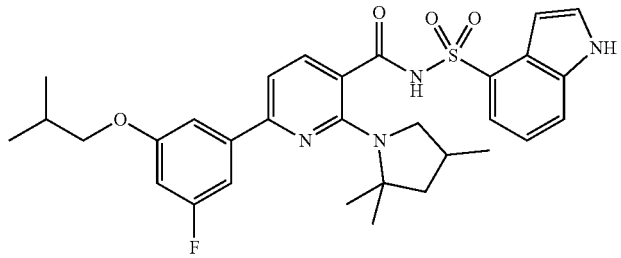 [SMILES: CC(C)COc1cc(F)cc(-c2ccc(C(=O)NS(=O)(=O)c3cccc4[nH]ccc34)c(N3CC(C)CC3(C)C)n2)c1] 549
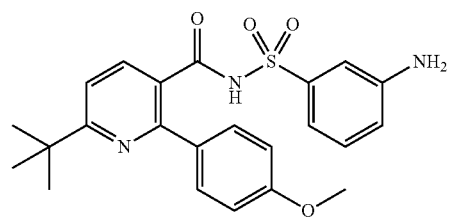 [SMILES: COc1ccc(-c2nc(C(C)(C)C)ccc2C(=O)NS(=O)(=O)c2cccc(N)c2)cc1] 550
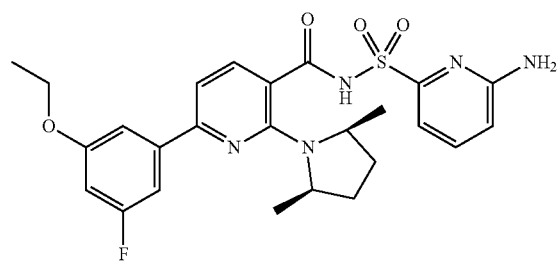 [SMILES: CCOc1cc(F)cc(-c2ccc(C(=O)NS(=O)(=O)c3cccc(N)n3)c(N3[C@H](C)CC[C@@H]3C)n2)c1] 551
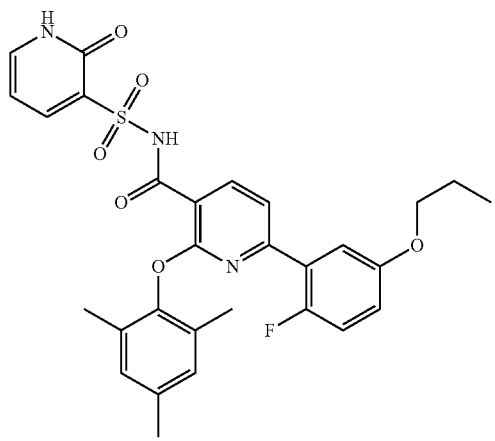 [SMILES: CCCOc1ccc(F)c(-c2ccc(C(=O)NS(=O)(=O)c3ccc[nH]c3=O)c(Oc3c(C)cc(C)cc3C)n2)c1] 552
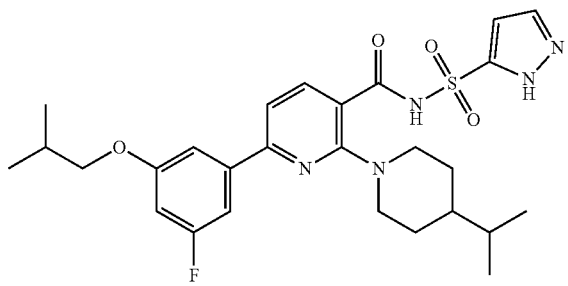 [SMILES: CC(C)COc1cc(F)cc(-c2ccc(C(=O)NS(=O)(=O)c3ccn[nH]3)c(N3CCC(C(C)C)CC3)n2)c1] 553

TABLE 1-continued
| | |
|---|---|
| 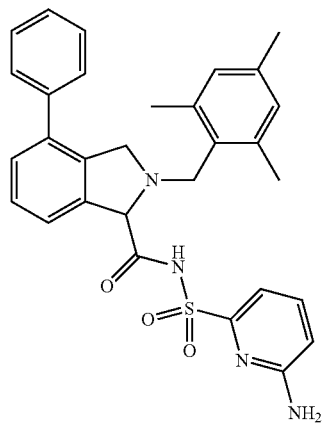 [SMILES: Cc1cc(C)c(CN2Cc3c(-c4ccccc4)cccc3C2C(=O)NS(=O)(=O)c2cccc(N)n2)c(C)c1] | 554 |
| 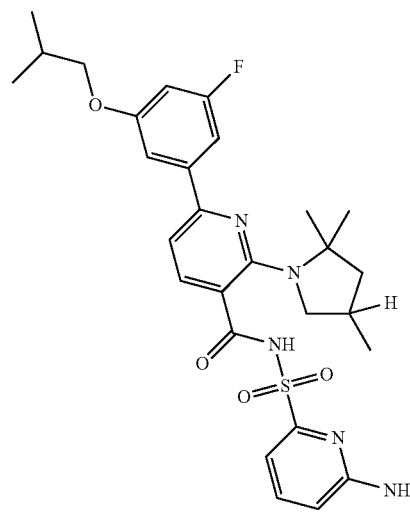 | 555 |
|  | 556 |
| 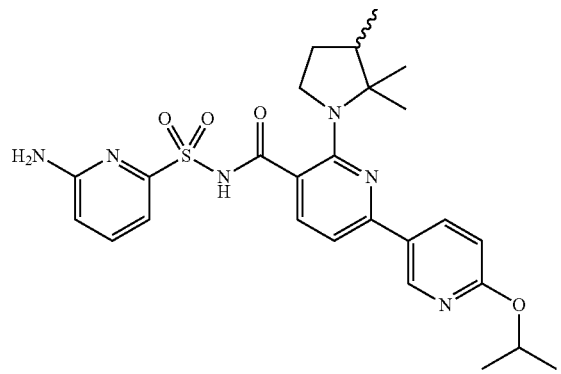 [SMILES: CC(C)Oc1ccc(-c2ccc(C(=O)NS(=O)(=O)c3cccc(N)n3)c(N3CCC(C)C3(C)C)n2)cn1] | 557 |

TABLE 1-continued
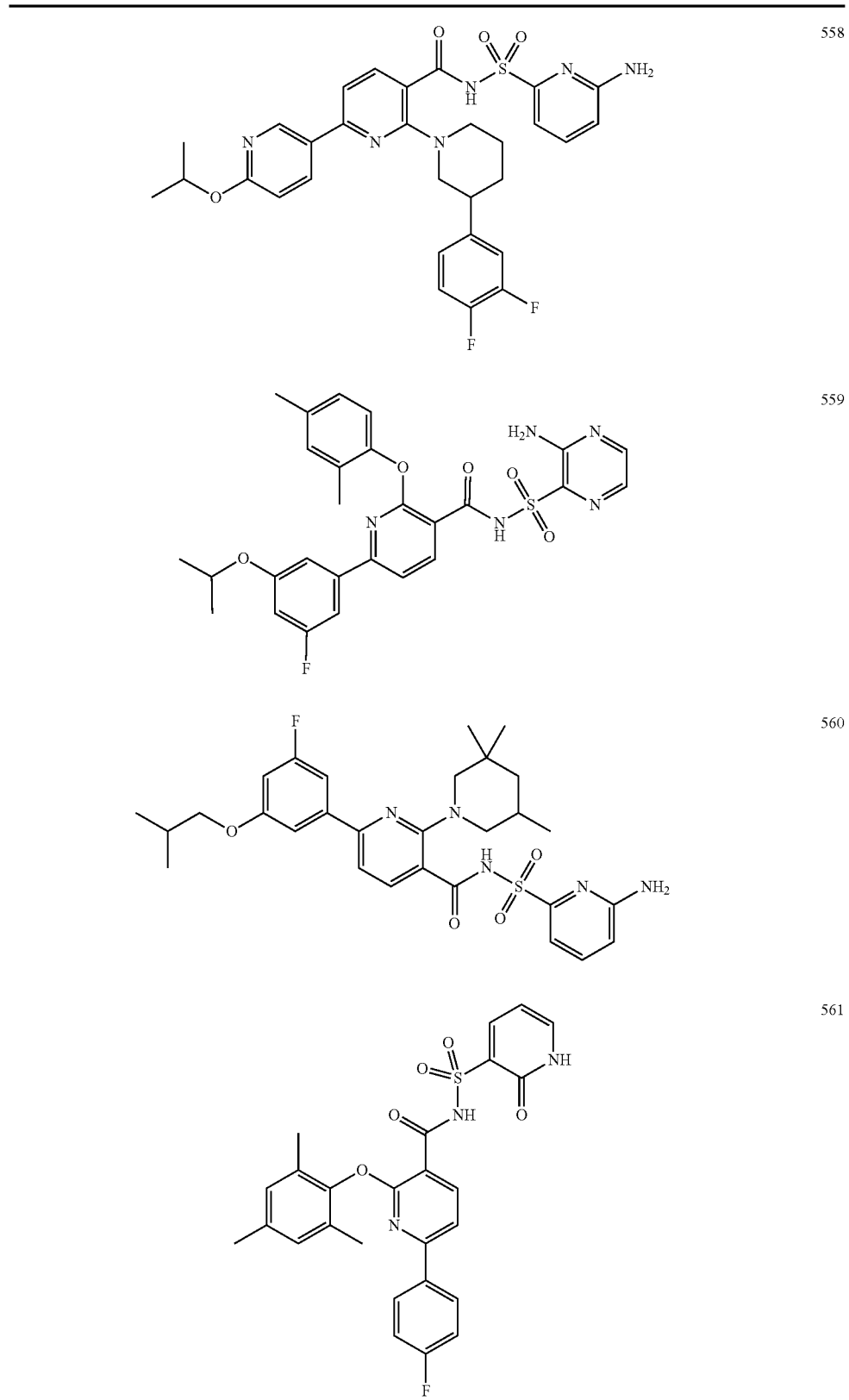
558
559
560
561

TABLE 1-continued
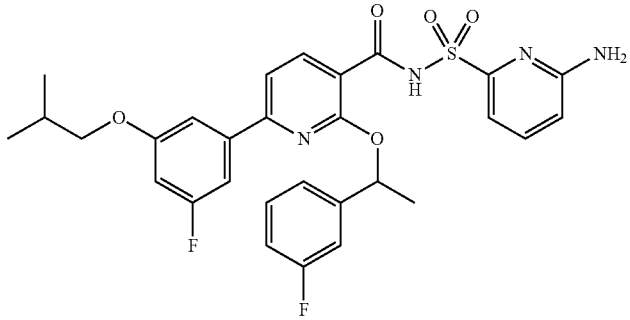 [SMILES: CC(C)COc1cc(F)cc(-c2ccc(C(=O)NS(=O)(=O)c3cccc(N)n3)c(OC(C)c3cccc(F)c3)n2)c1] 562
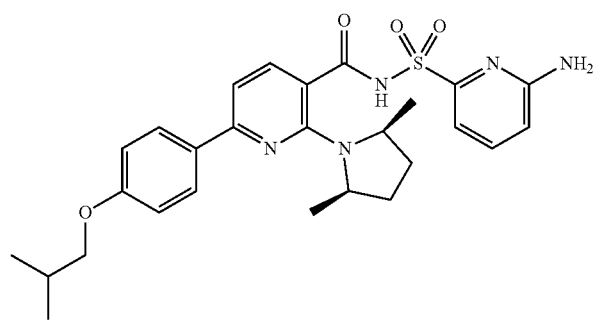 [SMILES: CC(C)COc1ccc(-c2ccc(C(=O)NS(=O)(=O)c3cccc(N)n3)c(N3[C@H](C)CC[C@@H]3C)n2)cc1] 563
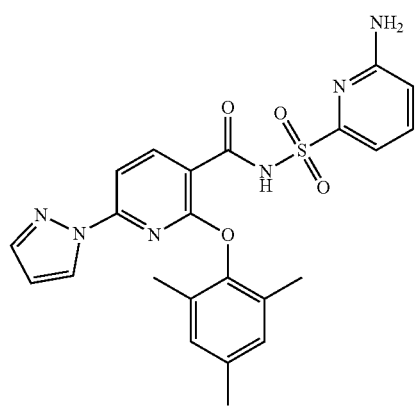 [SMILES: Cc1cc(C)c(Oc2nc(-n3cccn3)ccc2C(=O)NS(=O)(=O)c2cccc(N)n2)c(C)c1] 564
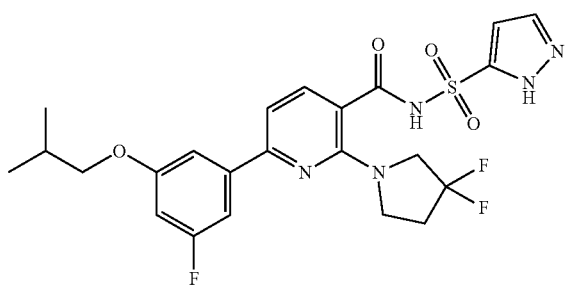 [SMILES: CC(C)COc1cc(F)cc(-c2ccc(C(=O)NS(=O)(=O)c3ccn[nH]3)c(N3CCC(F)(F)C3)n2)c1] 565

TABLE 1-continued
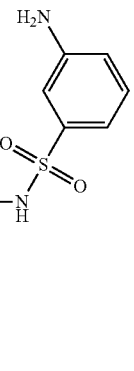
566
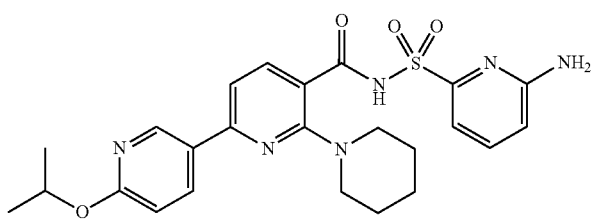 [SMILES: CC(C)Oc1ccc(-c2ccc(C(=O)NS(=O)(=O)c3cccc(N)n3)c(N3CCCCC3)n2)cn1]
567
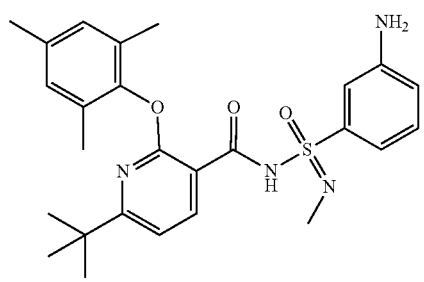 [SMILES: CN=S(=O)(NC(=O)c1ccc(C(C)(C)C)nc1Oc1c(C)cc(C)cc1C)c1cccc(N)c1]
568
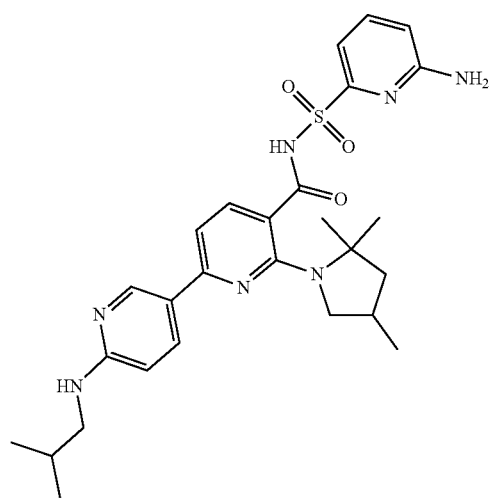 [SMILES: CC(C)CNc1ccc(-c2ccc(C(=O)NS(=O)(=O)c3cccc(N)n3)c(N3CC(C)CC3(C)C)n2)cn1]
569

TABLE 1-continued
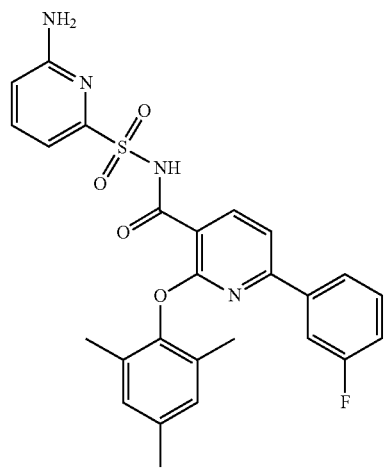 [SMILES: Cc1cc(C)c(Oc2nc(-c3cccc(F)c3)ccc2C(=O)NS(=O)(=O)c2cccc(N)n2)c(C)c1]
570
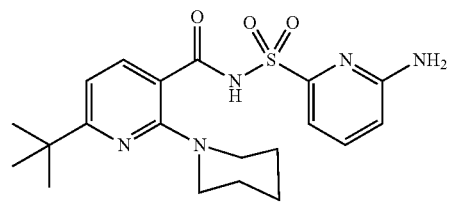 [SMILES: CC(C)(C)c1ccc(C(=O)NS(=O)(=O)c2cccc(N)n2)c(N2CCCCC2)n1]
571
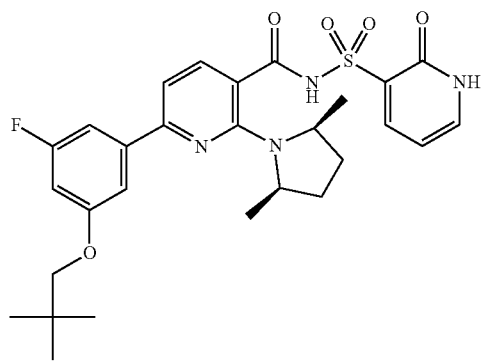 [SMILES: C[C@@H]1CC[C@H](C)N1c1nc(-c2cc(F)cc(OCC(C)(C)C)c2)ccc1C(=O)NS(=O)(=O)c1ccc[nH]c1=O]
572
573

TABLE 1-continued
| | |
|---|---|
| 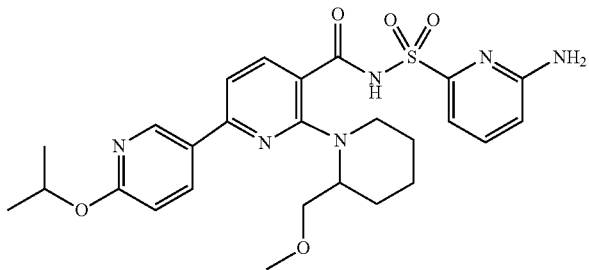 [SMILES: COCC1CCCCN1c1nc(-c2ccc(OC(C)C)nc2)ccc1C(=O)NS(=O)(=O)c1cccc(N)n1] | 574 |
| 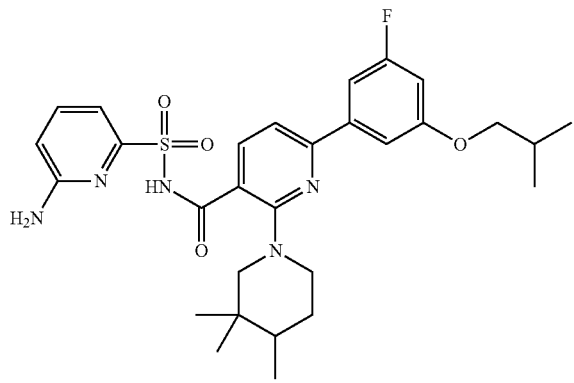 [SMILES: CC(C)COc1cc(F)cc(-c2ccc(C(=O)NS(=O)(=O)c3cccc(N)n3)c(N3CCC(C)C(C)(C)C3)n2)c1] | 575 |
| 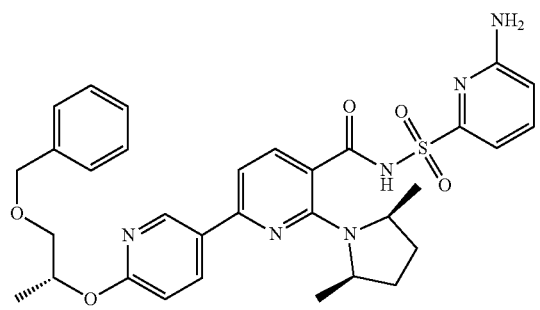 [SMILES: C[C@H](COCc1ccccc1)Oc1ccc(-c2ccc(C(=O)NS(=O)(=O)c3cccc(N)n3)c(N3[C@H](C)CC[C@@H]3C)n2)cn1] | 576 |
| 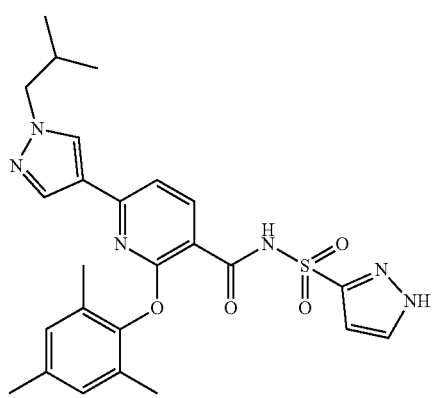 [SMILES: Cc1cc(C)c(Oc2nc(-c3cnn(CC(C)C)c3)ccc2C(=O)NS(=O)(=O)c2cc[nH]n2)c(C)c1] | 577 |
| 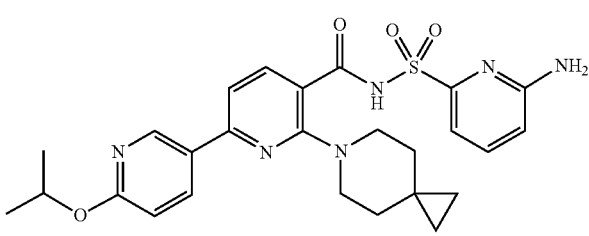 [SMILES: CC(C)Oc1ccc(-c2ccc(C(=O)NS(=O)(=O)c3cccc(N)n3)c(N3CCC4(CC3)CC4)n2)cn1] | 578 |

TABLE 1-continued
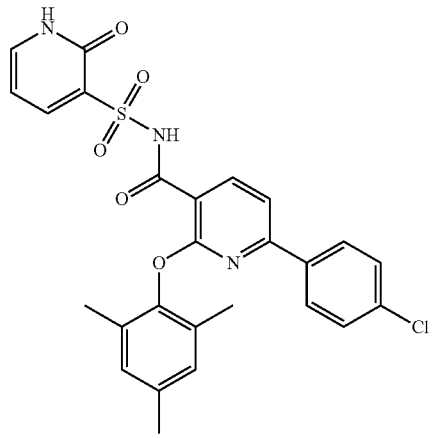 [SMILES: Cc1cc(C)c(Oc2nc(-c3ccc(Cl)cc3)ccc2C(=O)NS(=O)(=O)c2ccc[nH]c2=O)c(C)c1]
579
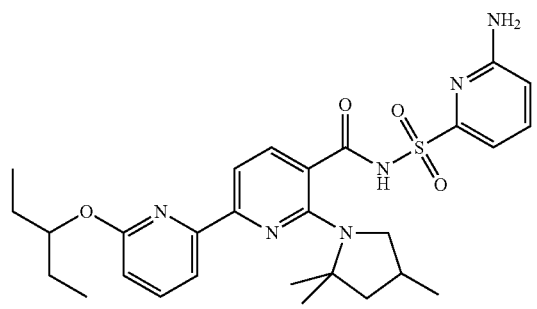 [SMILES: CCC(CC)Oc1cccc(-c2ccc(C(=O)NS(=O)(=O)c3cccc(N)n3)c(N3CC(C)CC3(C)C)n2)n1]
580
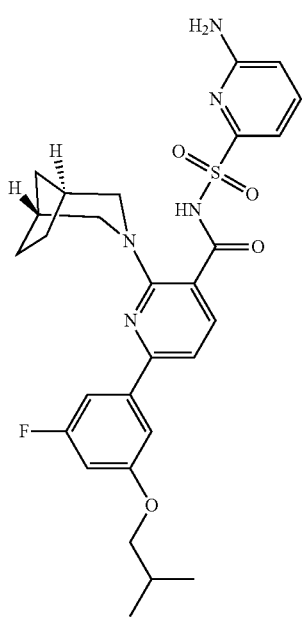 [SMILES: CC(C)COc1cc(F)cc(-c2ccc(C(=O)NS(=O)(=O)c3cccc(N)n3)c(N3C[C@@H]4CC[C@@H](C4)C3)n2)c1]
581

TABLE 1-continued
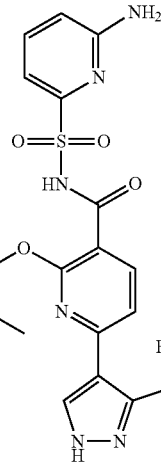
582
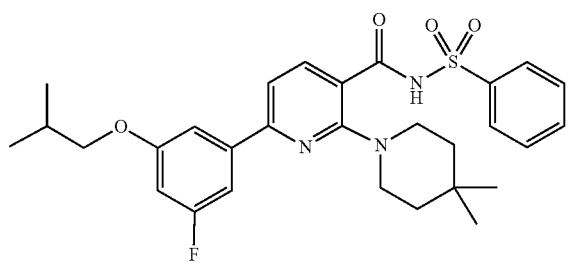 [SMILES: CC(C)COc1cc(F)cc(-c2ccc(C(=O)NS(=O)(=O)c3ccccc3)c(N3CCC(C)(C)CC3)n2)c1]
583
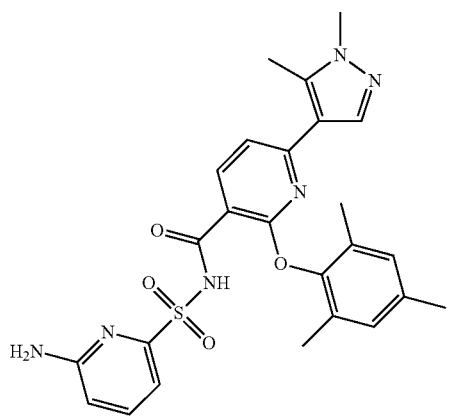 [SMILES: Cc1cc(C)c(Oc2nc(-c3cnn(C)c3C)ccc2C(=O)NS(=O)(=O)c2cccc(N)n2)c(C)c1]
584
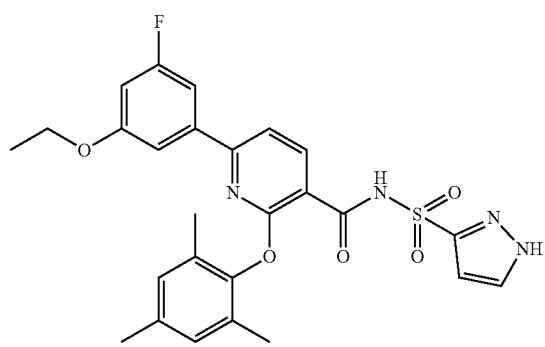 [SMILES: CCOc1cc(F)cc(-c2ccc(C(=O)NS(=O)(=O)c3cc[nH]n3)c(Oc3c(C)cc(C)cc3C)n2)c1]
585

TABLE 1-continued
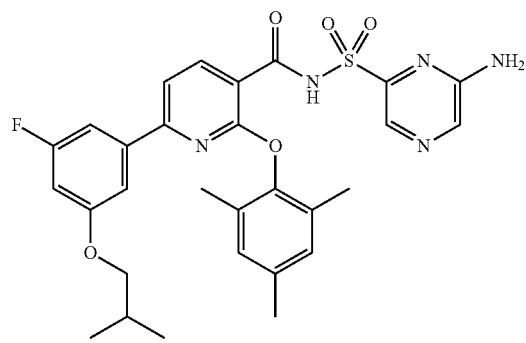 [SMILES: Cc1cc(C)c(Oc2nc(-c3cc(F)cc(OCC(C)C)c3)ccc2C(=O)NS(=O)(=O)c2cncc(N)n2)c(C)c1]
586
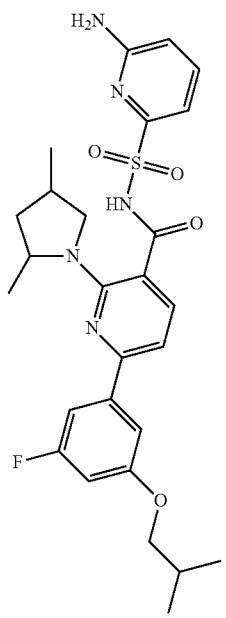 [SMILES: CC(C)COc1cc(F)cc(-c2ccc(C(=O)NS(=O)(=O)c3cccc(N)n3)c(N3CC(C)CC3C)n2)c1]
587
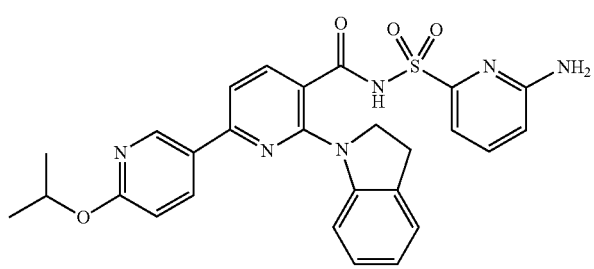 [SMILES: CC(C)Oc1ccc(-c2ccc(C(=O)NS(=O)(=O)c3cccc(N)n3)c(N3CCc4ccccc43)n2)cn1]
588
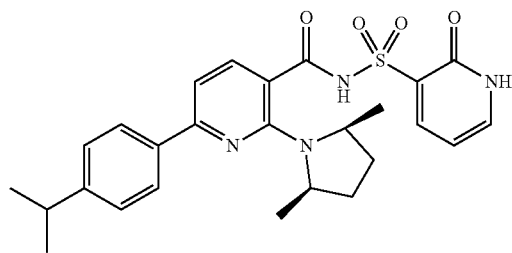 [SMILES: CC(C)c1ccc(-c2ccc(C(=O)NS(=O)(=O)c3ccc[nH]c3=O)c(N3[C@H](C)CC[C@@H]3C)n2)cc1]
589

TABLE 1-continued
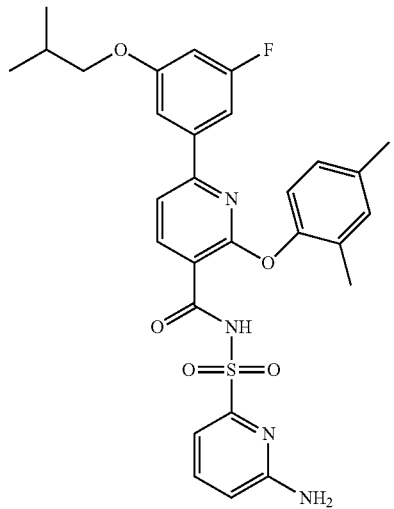 [SMILES: Cc1ccc(Oc2nc(-c3cc(F)cc(OCC(C)C)c3)ccc2C(=O)NS(=O)(=O)c2cccc(N)n2)c(C)c1]
590
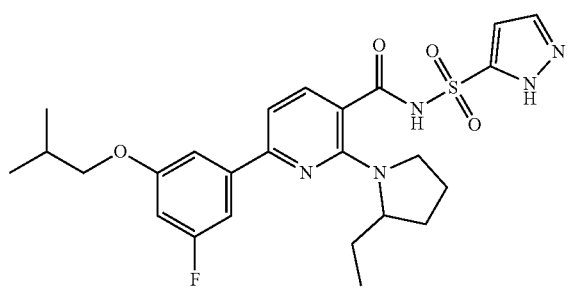 [SMILES: CCC1CCCN1c1nc(-c2cc(F)cc(OCC(C)C)c2)ccc1C(=O)NS(=O)(=O)c1ccn[nH]1]
591
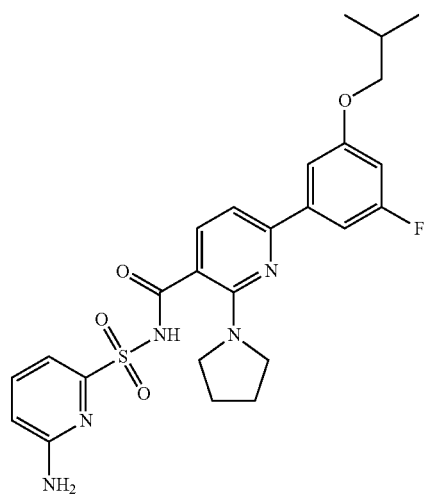 [SMILES: CC(C)COc1cc(F)cc(-c2ccc(C(=O)NS(=O)(=O)c3cccc(N)n3)c(N3CCCC3)n2)c1]
592

TABLE 1-continued
| | |
|---|---|
| 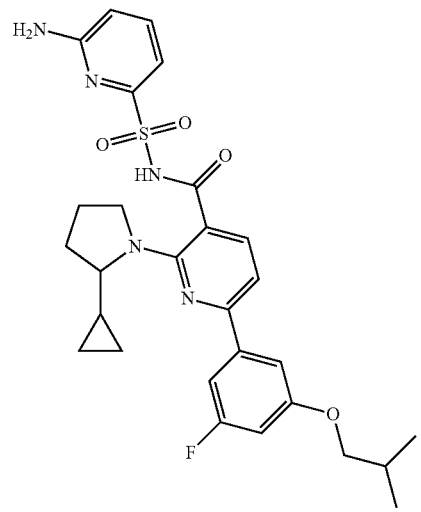 [SMILES: CC(C)COc1cc(F)cc(-c2ccc(C(=O)NS(=O)(=O)c3cccc(N)n3)c(N3CCCC3C3CC3)n2)c1] | 593 |
| 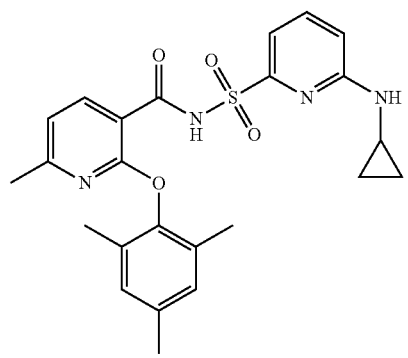 [SMILES: Cc1cc(C)c(Oc2nc(C)ccc2C(=O)NS(=O)(=O)c2cccc(NC3CC3)n2)c(C)c1] | 594 |
| 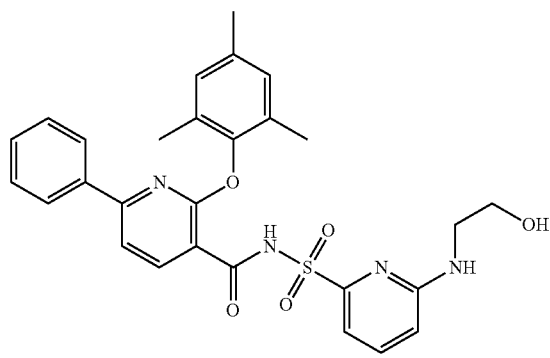 [SMILES: Cc1cc(C)c(Oc2nc(-c3ccccc3)ccc2C(=O)NS(=O)(=O)c2cccc(NCCO)n2)c(C)c1] | 595 |
| 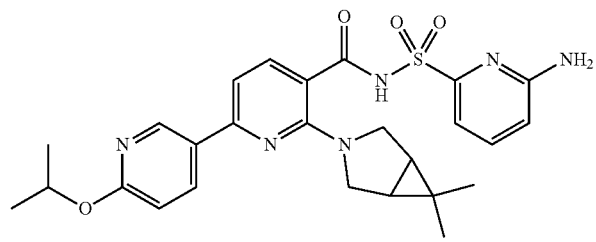 [SMILES: CC(C)Oc1ccc(-c2ccc(C(=O)NS(=O)(=O)c3cccc(N)n3)c(N3CC4C(C3)C4(C)C)n2)cn1] | 596 |

TABLE 1-continued
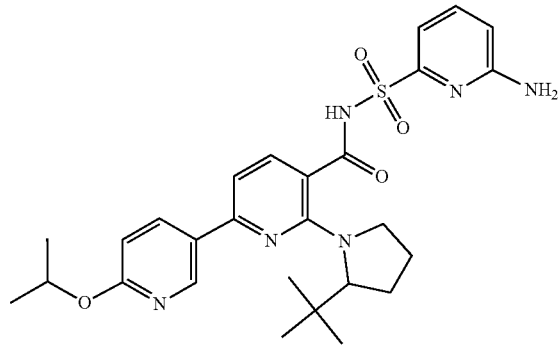 [SMILES: CC(C)Oc1ccc(-c2ccc(C(=O)NS(=O)(=O)c3cccc(N)n3)c(N3CCCC3C(C)(C)C)n2)cn1]
597
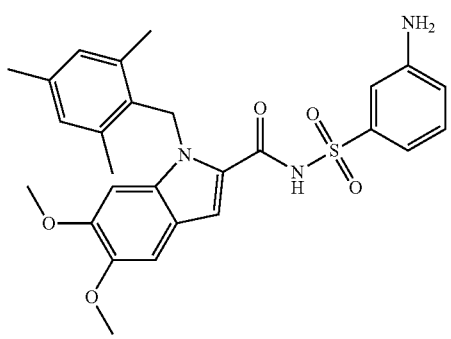 [SMILES: COc1cc2cc(C(=O)NS(=O)(=O)c3cccc(N)c3)n(Cc3c(C)cc(C)cc3C)c2cc1OC]
598
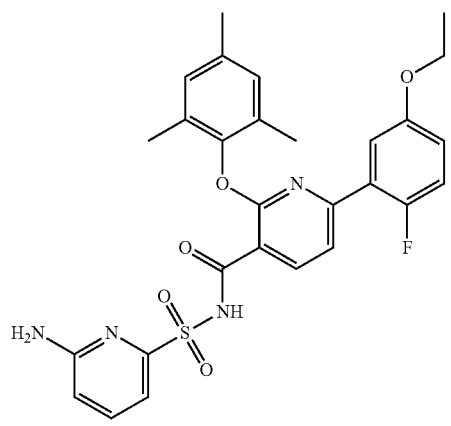 [SMILES: CCOc1ccc(F)c(-c2ccc(C(=O)NS(=O)(=O)c3cccc(N)n3)c(Oc3c(C)cc(C)cc3C)n2)c1]
599
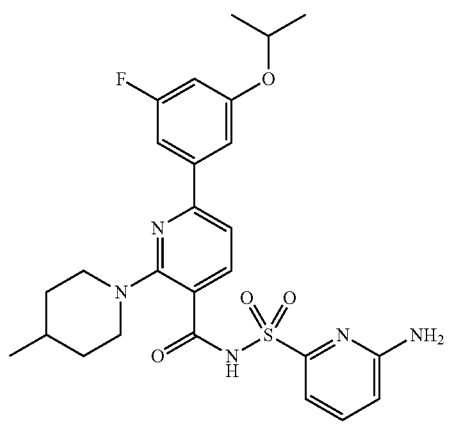 [SMILES: CC1CCN(c2nc(-c3cc(F)cc(OC(C)C)c3)ccc2C(=O)NS(=O)(=O)c2cccc(N)n2)CC1]
600

TABLE 1-continued
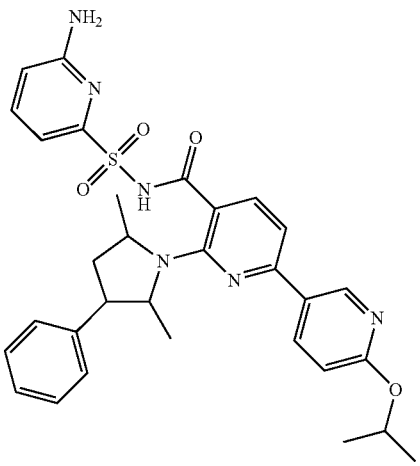 [SMILES: CC(C)Oc1ccc(-c2ccc(C(=O)NS(=O)(=O)c3cccc(N)n3)c(N3C(C)CC(c4ccccc4)C3C)n2)cn1]
601
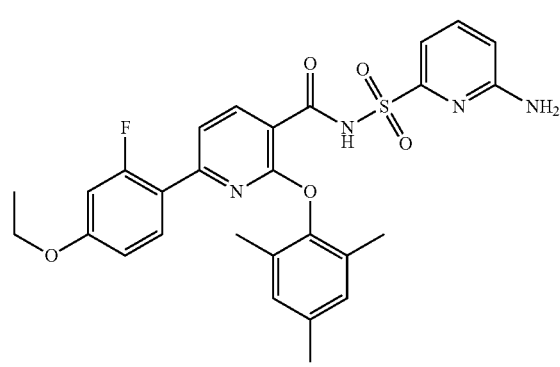 [SMILES: CCOc1ccc(-c2ccc(C(=O)NS(=O)(=O)c3cccc(N)n3)c(Oc3c(C)cc(C)cc3C)n2)c(F)c1]
602
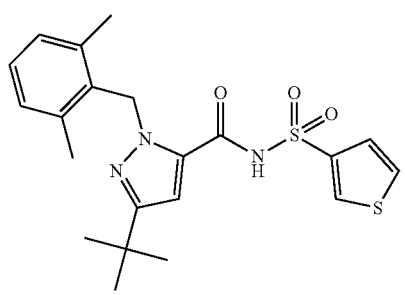 [SMILES: Cc1cccc(C)c1Cn1nc(C(C)(C)C)cc1C(=O)NS(=O)(=O)c1ccsc1]
603
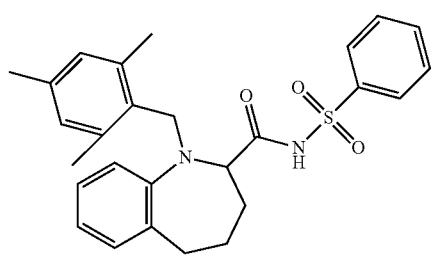 [SMILES: Cc1cc(C)c(CN2c3ccccc3CCCC2C(=O)NS(=O)(=O)c2ccccc2)c(C)c1]
604

TABLE 1-continued
| | |
|---|---|
| 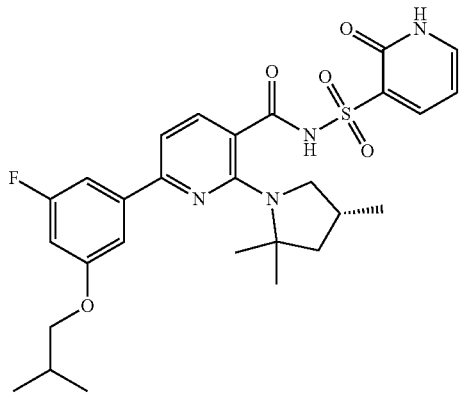 [SMILES: CC(C)COc1cc(F)cc(-c2ccc(C(=O)NS(=O)(=O)c3ccc[nH]c3=O)c(N3C[C@H](C)CC3(C)C)n2)c1] | 605 |
| 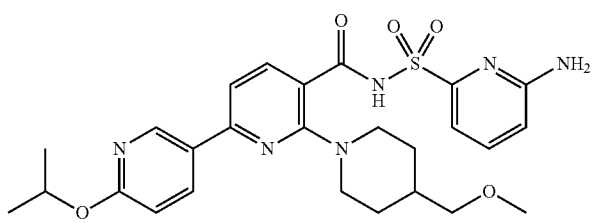 [SMILES: COCC1CCN(c2nc(-c3ccc(OC(C)C)nc3)ccc2C(=O)NS(=O)(=O)c2cccc(N)n2)CC1] | 606 |
| 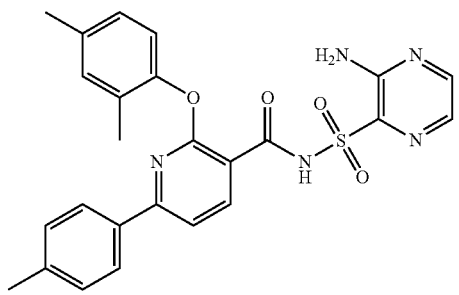 [SMILES: Cc1ccc(-c2ccc(C(=O)NS(=O)(=O)c3nccnc3N)c(Oc3ccc(C)cc3C)n2)cc1] | 607 |
| 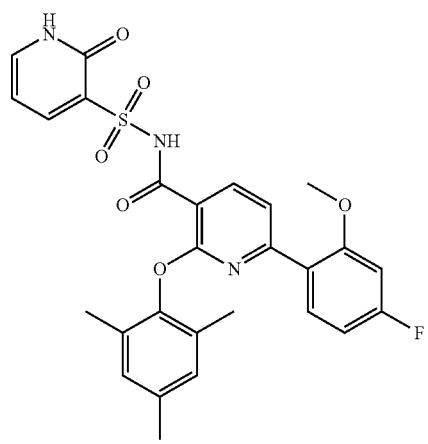 [SMILES: COc1cc(F)ccc1-c1ccc(C(=O)NS(=O)(=O)c2ccc[nH]c2=O)c(Oc2c(C)cc(C)cc2C)n1] | 608 |

TABLE 1-continued
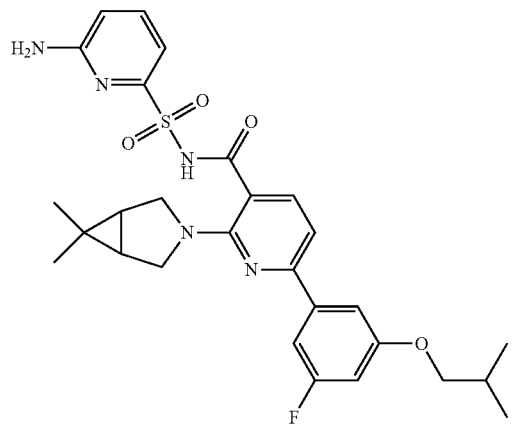 [SMILES: CC(C)COc1cc(F)cc(-c2ccc(C(=O)NS(=O)(=O)c3cccc(N)n3)c(N3CC4C(C3)C4(C)C)n2)c1]
609
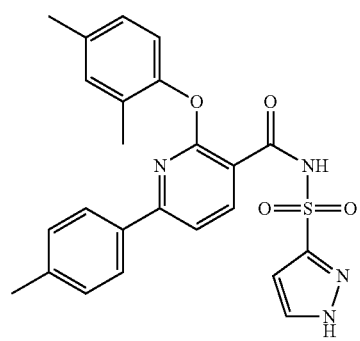 [SMILES: Cc1ccc(-c2ccc(C(=O)NS(=O)(=O)c3cc[nH]n3)c(Oc3ccc(C)cc3C)n2)cc1]
610
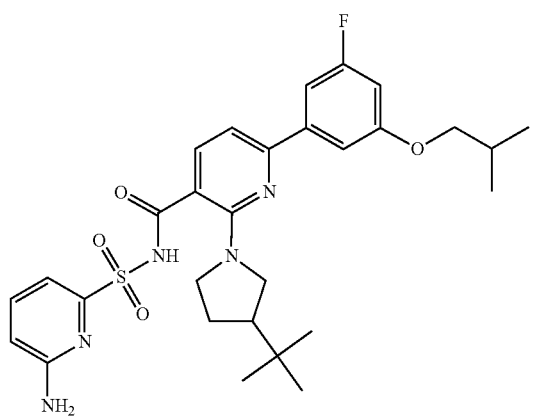 [SMILES: CC(C)COc1cc(F)cc(-c2ccc(C(=O)NS(=O)(=O)c3cccc(N)n3)c(N3CCC(C(C)(C)C)C3)n2)c1]
611
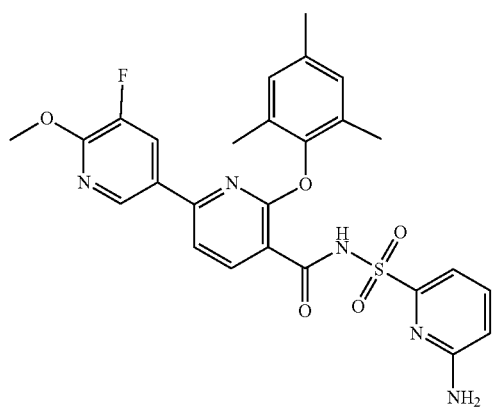
612

TABLE 1-continued
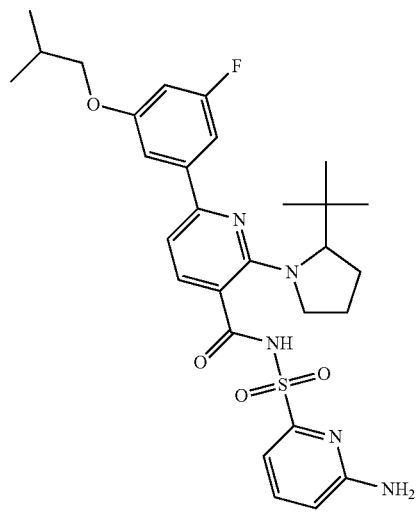 [SMILES: CC(C)COc1cc(F)cc(-c2ccc(C(=O)NS(=O)(=O)c3cccc(N)n3)c(N3CCCC3C(C)(C)C)n2)c1]
613
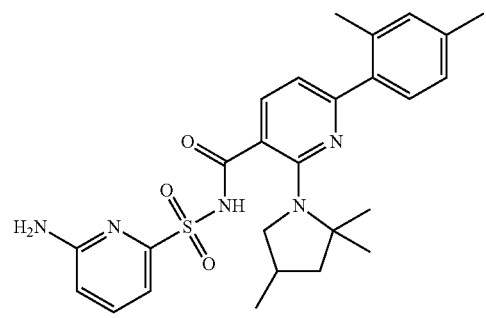 [SMILES: Cc1ccc(-c2ccc(C(=O)NS(=O)(=O)c3cccc(N)n3)c(N3CC(C)CC3(C)C)n2)c(C)c1]
614
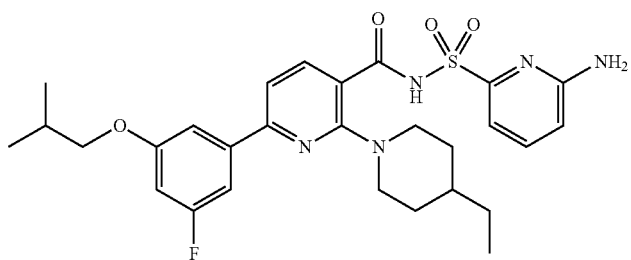 [SMILES: CCC1CCN(c2nc(-c3cc(F)cc(OCC(C)C)c3)ccc2C(=O)NS(=O)(=O)c2cccc(N)n2)CC1]
615
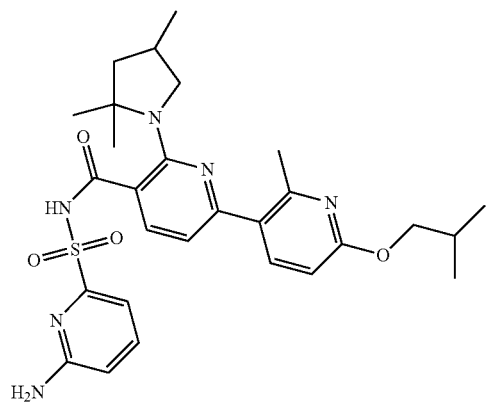 [SMILES: Cc1nc(OCC(C)C)ccc1-c1ccc(C(=O)NS(=O)(=O)c2cccc(N)n2)c(N2CC(C)CC2(C)C)n1]
616

TABLE 1-continued
| | |
|---|---|
| 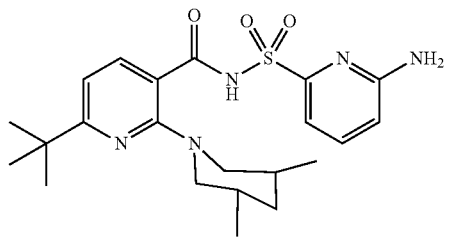 [SMILES: CC1CC(C)CN(c2nc(C(C)(C)C)ccc2C(=O)NS(=O)(=O)c2cccc(N)n2)C1] | 617 |
| 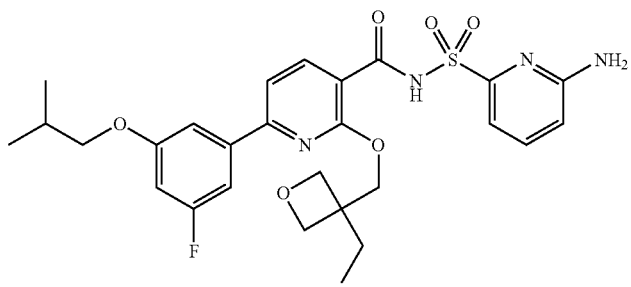 [SMILES: CCC1(COc2nc(-c3cc(F)cc(OCC(C)C)c3)ccc2C(=O)NS(=O)(=O)c2cccc(N)n2)COC1] | 618 |
| 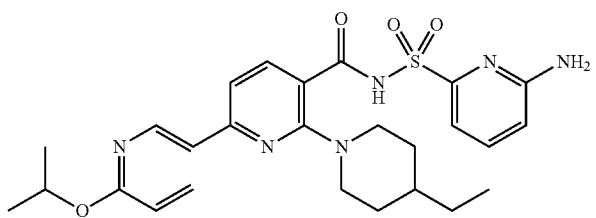 [SMILES: C=C/C(=N\C=C\c1ccc(C(=O)NS(=O)(=O)c2cccc(N)n2)c(N2CCC(CC)CC2)n1)OC(C)C] | 619 |
| 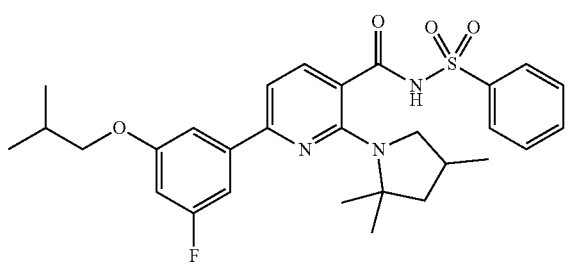 [SMILES: CC(C)COc1cc(F)cc(-c2ccc(C(=O)NS(=O)(=O)c3ccccc3)c(N3CC(C)CC3(C)C)n2)c1] | 620 |
| 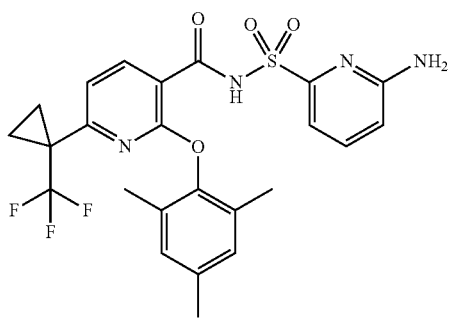 [SMILES: Cc1cc(C)c(Oc2nc(C3(C(F)(F)F)CC3)ccc2C(=O)NS(=O)(=O)c2cccc(N)n2)c(C)c1] | 621 |

TABLE 1-continued
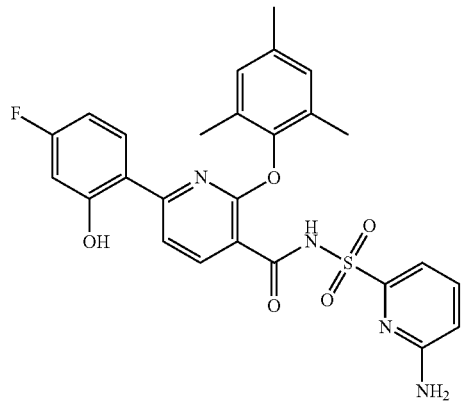 [SMILES: Cc1cc(C)c(Oc2nc(-c3ccc(F)cc3O)ccc2C(=O)NS(=O)(=O)c2cccc(N)n2)c(C)c1]
622
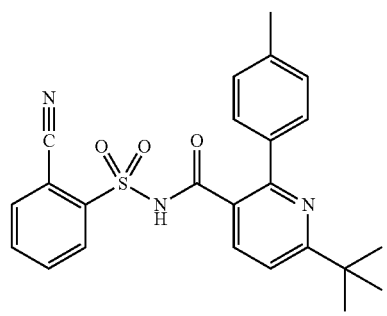 [SMILES: Cc1ccc(-c2nc(C(C)(C)C)ccc2C(=O)NS(=O)(=O)c2ccccc2C#N)cc1]
623
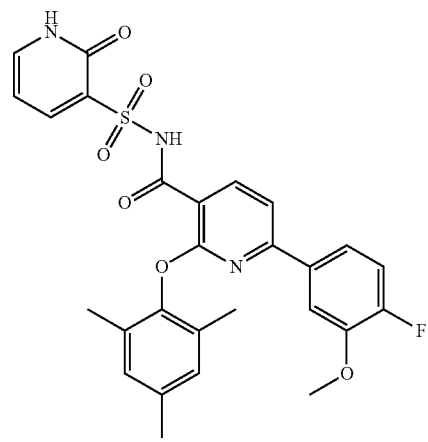 [SMILES: COc1cc(-c2ccc(C(=O)NS(=O)(=O)c3ccc[nH]c3=O)c(Oc3c(C)cc(C)cc3C)n2)ccc1F]
624
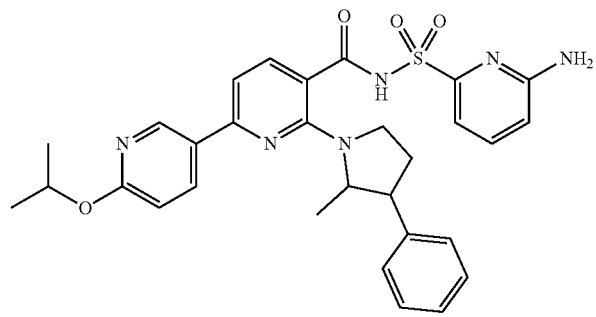 [SMILES: CC(C)Oc1ccc(-c2ccc(C(=O)NS(=O)(=O)c3cccc(N)n3)c(N3CCC(c4ccccc4)C3C)n2)cn1]
625

TABLE 1-continued
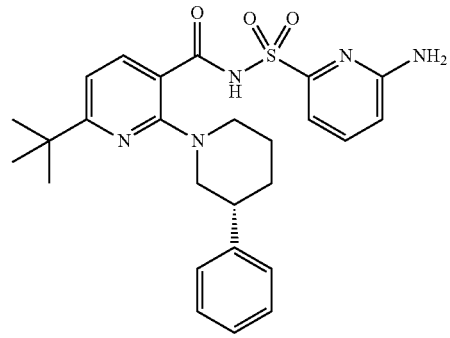 [SMILES: CC(C)(C)c1ccc(C(=O)NS(=O)(=O)c2cccc(N)n2)c(N2CCC[C@H](c3ccccc3)C2)n1] 626
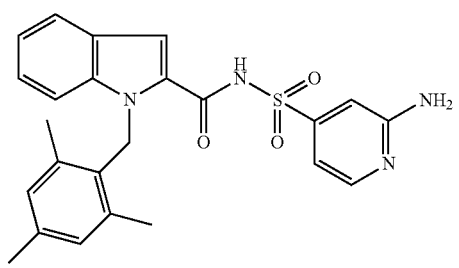 [SMILES: Cc1cc(C)c(Cn2c(C(=O)NS(=O)(=O)c3ccnc(N)c3)cc3ccccc32)c(C)c1] 627
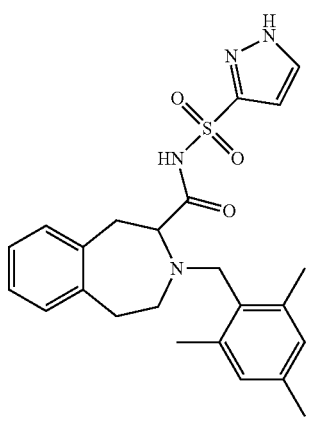 [SMILES: Cc1cc(C)c(CN2CCc3ccccc3CC2C(=O)NS(=O)(=O)c2cc[nH]n2)c(C)c1] 628
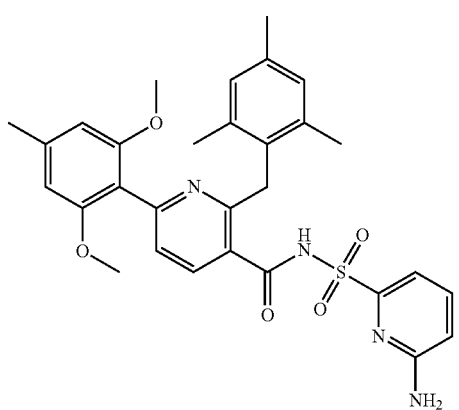 [SMILES: COc1cc(C)cc(OC)c1-c1ccc(C(=O)NS(=O)(=O)c2cccc(N)n2)c(Cc2c(C)cc(C)cc2C)n1] 629

TABLE 1-continued
| | |
|---|---|
| 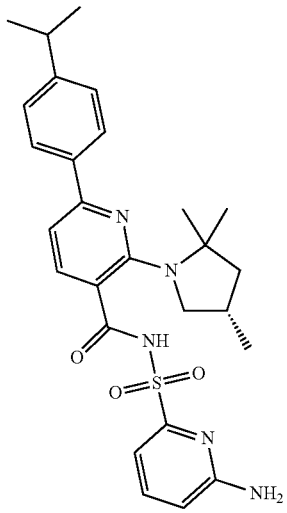 [SMILES: CC(C)c1ccc(-c2ccc(C(=O)NS(=O)(=O)c3cccc(N)n3)c(N3C[C@@H](C)CC3(C)C)n2)cc1] | 630 |
| 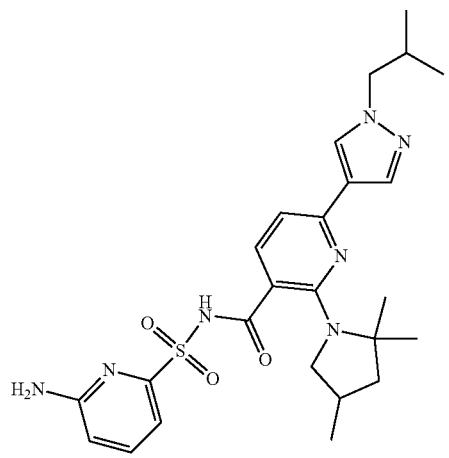 [SMILES: CC(C)Cn1cc(-c2ccc(C(=O)NS(=O)(=O)c3cccc(N)n3)c(N3CC(C)CC3(C)C)n2)cn1] | 631 |
| 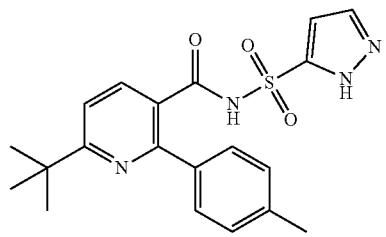 [SMILES: Cc1ccc(-c2nc(C(C)(C)C)ccc2C(=O)NS(=O)(=O)c2ccn[nH]2)cc1] | 632 |
| 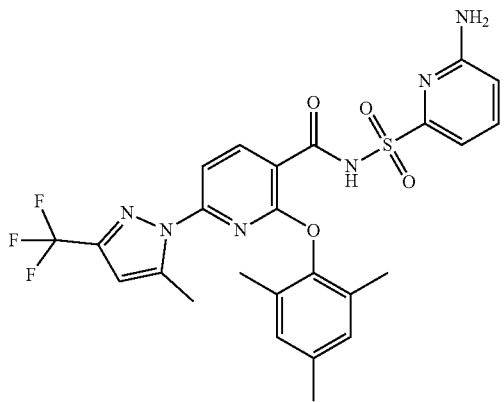 [SMILES: Cc1cc(C)c(Oc2nc(-n3nc(C(F)(F)F)cc3C)ccc2C(=O)NS(=O)(=O)c2cccc(N)n2)c(C)c1] | 633 |

TABLE 1-continued

| | |
|---|---|
| (structure) | 634 |
| (structure) | 635 |
| (structure) | 636 |
| (structure) | 637 |
| (structure) | 638 |

TABLE 1-continued
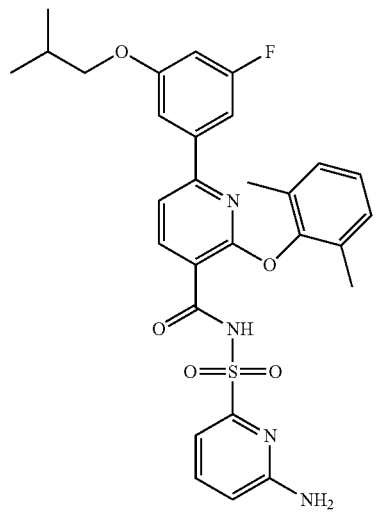 [SMILES: Cc1cccc(C)c1Oc1nc(-c2cc(F)cc(OCC(C)C)c2)ccc1C(=O)NS(=O)(=O)c1cccc(N)n1]
639
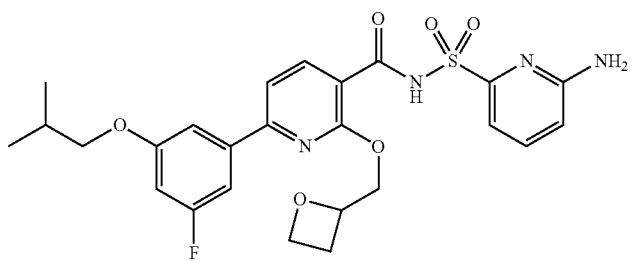 [SMILES: CC(C)COc1cc(F)cc(-c2ccc(C(=O)NS(=O)(=O)c3cccc(N)n3)c(OCC3CCO3)n2)c1]
640
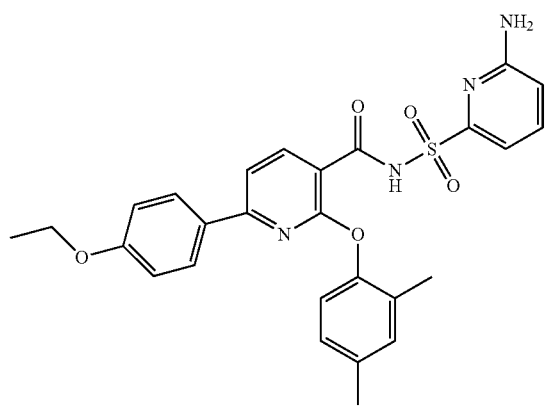 [SMILES: CCOc1ccc(-c2ccc(C(=O)NS(=O)(=O)c3cccc(N)n3)c(Oc3ccc(C)cc3C)n2)cc1]
641
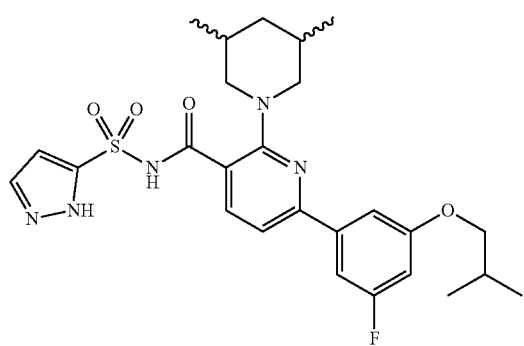
642

TABLE 1-continued
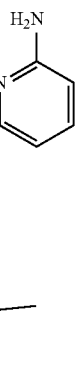
643
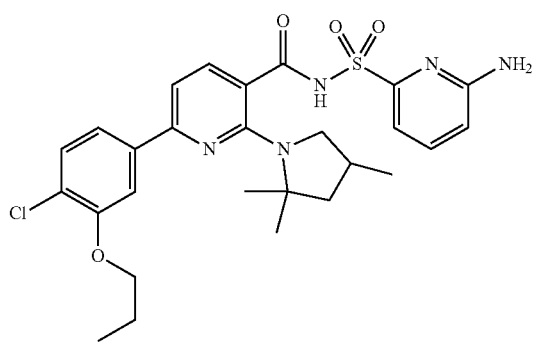
644
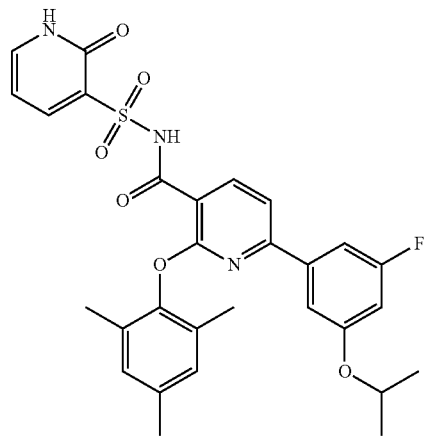 [SMILES: Cc1cc(C)c(Oc2nc(-c3cc(F)cc(OC(C)C)c3)ccc2C(=O)NS(=O)(=O)c2ccc[nH]c2=O)c(C)c1]
645
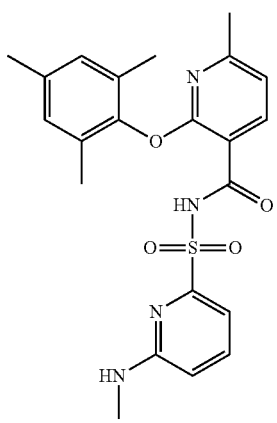 [SMILES: CNc1cccc(S(=O)(=O)NC(=O)c2ccc(C)nc2Oc2c(C)cc(C)cc2C)n1]
646

TABLE 1-continued
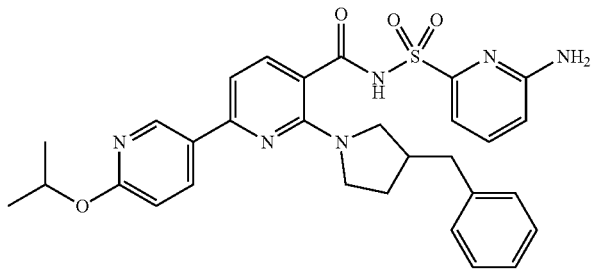 [SMILES: CC(C)Oc1ccc(-c2ccc(C(=O)NS(=O)(=O)c3cccc(N)n3)c(N3CCC(Cc4ccccc4)C3)n2)cn1]
647
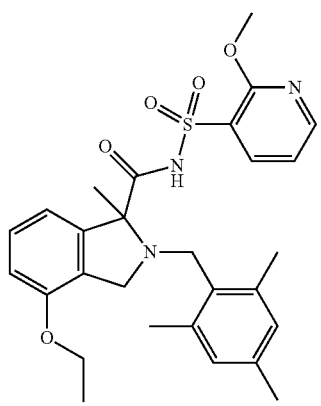 [SMILES: CCOc1cccc2c1CN(Cc1c(C)cc(C)cc1C)C2(C)C(=O)NS(=O)(=O)c1cccnc1OC]
648
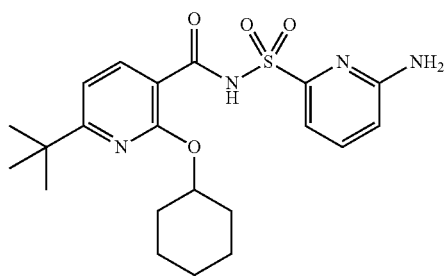 [SMILES: CC(C)(C)c1ccc(C(=O)NS(=O)(=O)c2cccc(N)n2)c(OC2CCCCC2)n1]
649
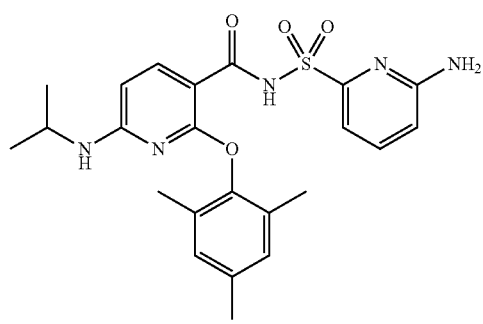 [SMILES: Cc1cc(C)c(Oc2nc(NC(C)C)ccc2C(=O)NS(=O)(=O)c2cccc(N)n2)c(C)c1]
650
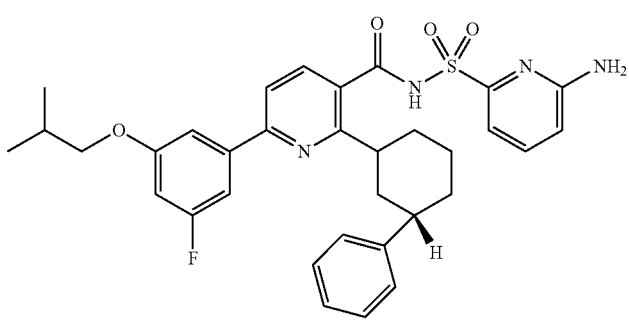 [SMILES: CC(C)COc1cc(F)cc(-c2ccc(C(=O)NS(=O)(=O)c3cccc(N)n3)c(C3CCC[C@H](c4ccccc4)C3)n2)c1]
651

TABLE 1-continued
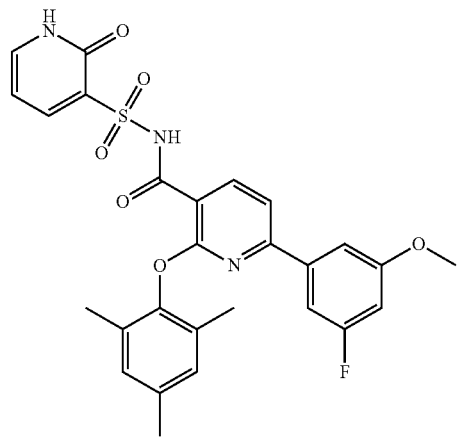 [SMILES: COc1cc(F)cc(-c2ccc(C(=O)NS(=O)(=O)c3ccc[nH]c3=O)c(Oc3c(C)cc(C)cc3C)n2)c1]
652
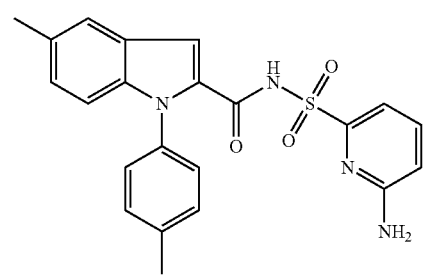 [SMILES: Cc1ccc(-n2c(C(=O)NS(=O)(=O)c3cccc(N)n3)cc3cc(C)ccc32)cc1]
653
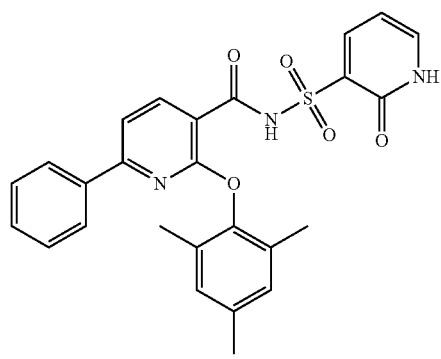 [SMILES: Cc1cc(C)c(Oc2nc(-c3ccccc3)ccc2C(=O)NS(=O)(=O)c2ccc[nH]c2=O)c(C)c1]
654
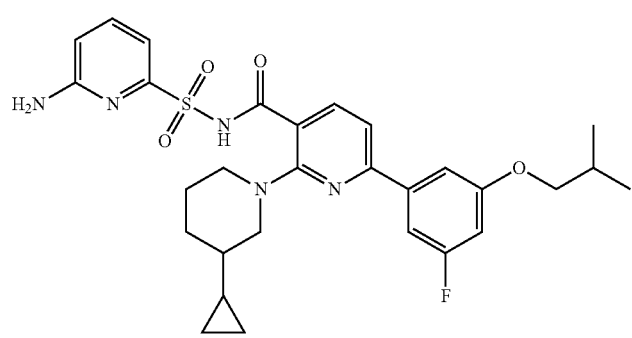 [SMILES: CC(C)COc1cc(F)cc(-c2ccc(C(=O)NS(=O)(=O)c3cccc(N)n3)c(N3CCCC(C4CC4)C3)n2)c1]
655

TABLE 1-continued
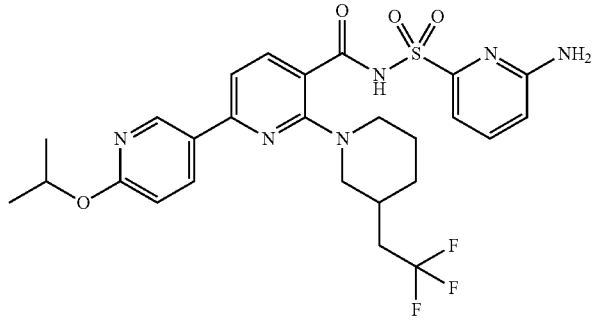 [SMILES: CC(C)Oc1ccc(-c2ccc(C(=O)NS(=O)(=O)c3cccc(N)n3)c(N3CCCC(CC(F)(F)F)C3)n2)cn1]
656
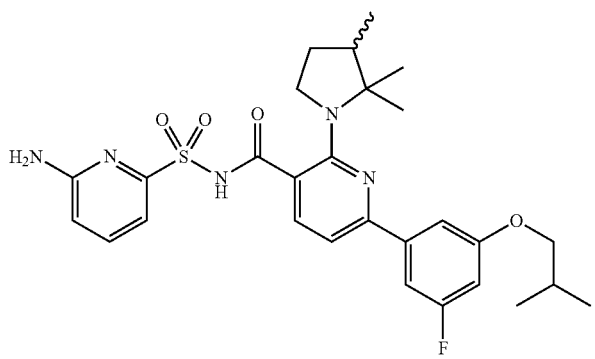 [SMILES: CC(C)COc1cc(F)cc(-c2ccc(C(=O)NS(=O)(=O)c3cccc(N)n3)c(N3CCC(C)C3(C)C)n2)c1]
657
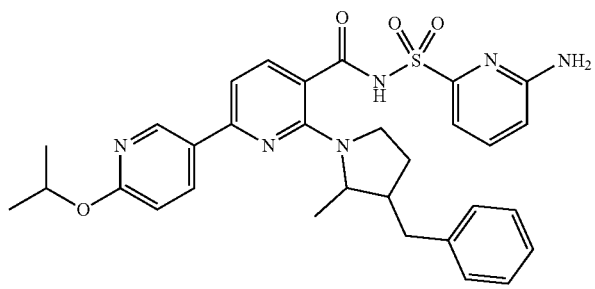 [SMILES: CC(C)Oc1ccc(-c2ccc(C(=O)NS(=O)(=O)c3cccc(N)n3)c(N3CCC(Cc4ccccc4)C3C)n2)cn1]
658
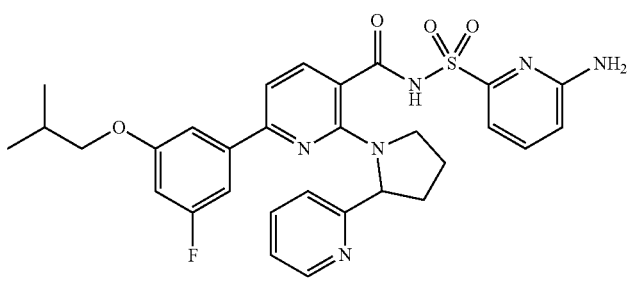 [SMILES: CC(C)COc1cc(F)cc(-c2ccc(C(=O)NS(=O)(=O)c3cccc(N)n3)c(N3CCCC3c3ccccn3)n2)c1]
659
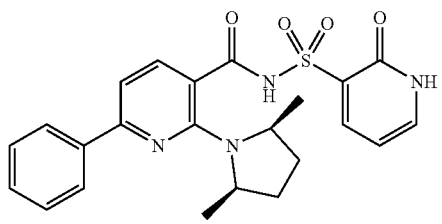 [SMILES: C[C@@H]1CC[C@H](C)N1c1nc(-c2ccccc2)ccc1C(=O)NS(=O)(=O)c1ccc[nH]c1=O]
660

TABLE 1-continued
| | |
|---|---|
| 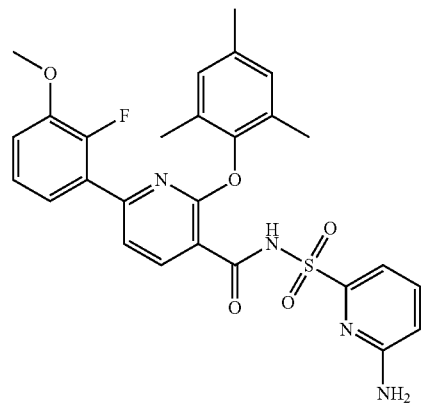 [SMILES: COc1cccc(-c2ccc(C(=O)NS(=O)(=O)c3cccc(N)n3)c(Oc3c(C)cc(C)cc3C)n2)c1F] | 661 |
| 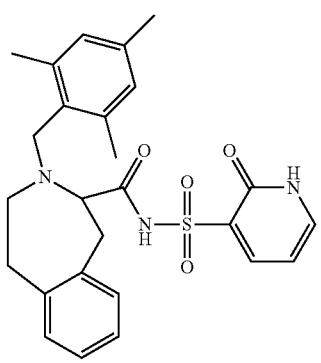 [SMILES: Cc1cc(C)c(CN2CCc3ccccc3CC2C(=O)NS(=O)(=O)c2ccc[nH]c2=O)c(C)c1] | 662 |
| 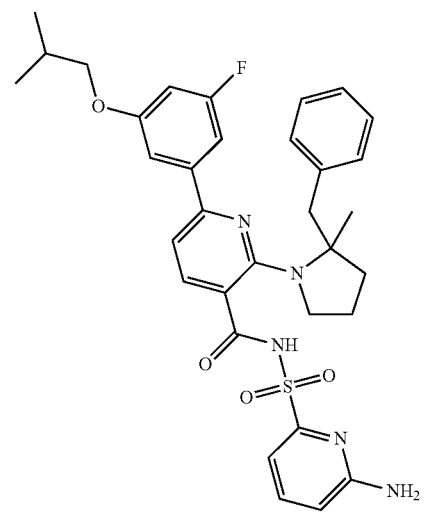 [SMILES: CC(C)COc1cc(F)cc(-c2ccc(C(=O)NS(=O)(=O)c3cccc(N)n3)c(N3CCCC3(C)Cc3ccccc3)n2)c1] | 663 |
| 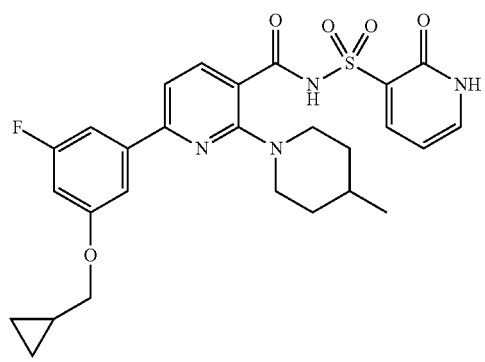 [SMILES: CC1CCN(c2nc(-c3cc(F)cc(OCC4CC4)c3)ccc2C(=O)NS(=O)(=O)c2ccc[nH]c2=O)CC1] | 664 |

TABLE 1-continued
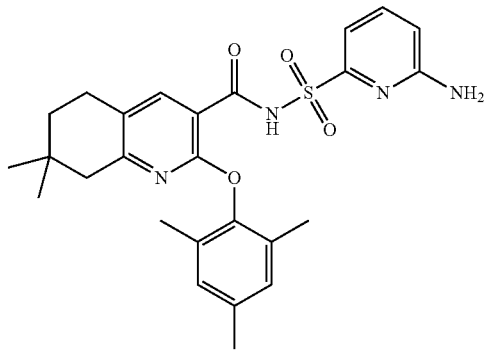 [SMILES: Cc1cc(C)c(Oc2nc3c(cc2C(=O)NS(=O)(=O)c2cccc(N)n2)CCC(C)(C)C3)c(C)c1]
665
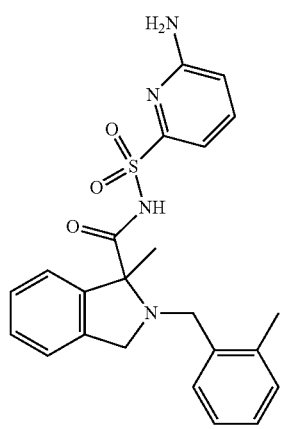 [SMILES: Cc1ccccc1CN1Cc2ccccc2C1(C)C(=O)NS(=O)(=O)c1cccc(N)n1]
666
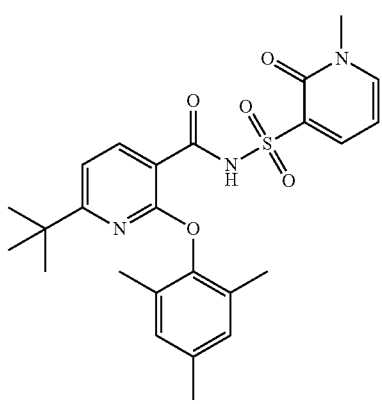 [SMILES: Cc1cc(C)c(Oc2nc(C(C)(C)C)ccc2C(=O)NS(=O)(=O)c2cccn(C)c2=O)c(C)c1]
667
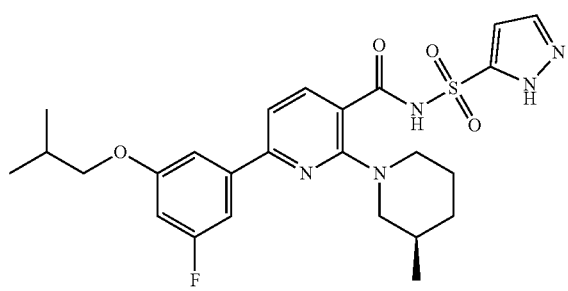 [SMILES: CC(C)COc1cc(F)cc(-c2ccc(C(=O)NS(=O)(=O)c3ccn[nH]3)c(N3CCC[C@@H](C)C3)n2)c1]
668

TABLE 1-continued
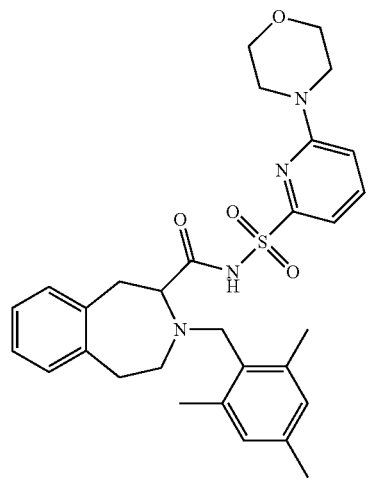 [SMILES: Cc1cc(C)c(CN2CCc3ccccc3CC2C(=O)NS(=O)(=O)c2cccc(N3CCOCC3)n2)c(C)c1]
669
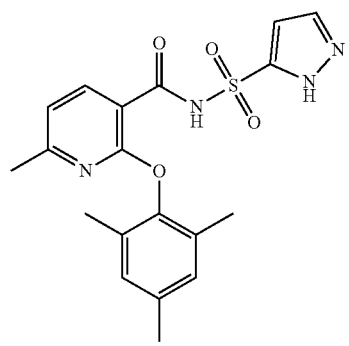 [SMILES: Cc1cc(C)c(Oc2nc(C)ccc2C(=O)NS(=O)(=O)c2ccn[nH]2)c(C)c1]
670
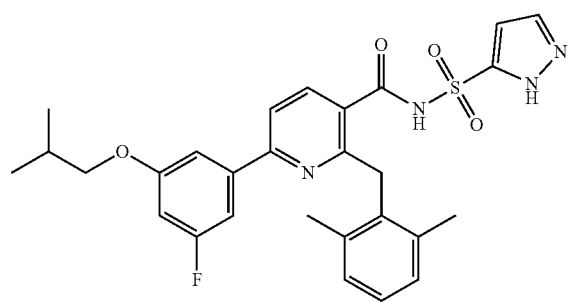 [SMILES: Cc1cccc(C)c1Cc1nc(-c2cc(F)cc(OCC(C)C)c2)ccc1C(=O)NS(=O)(=O)c1ccn[nH]1]
671
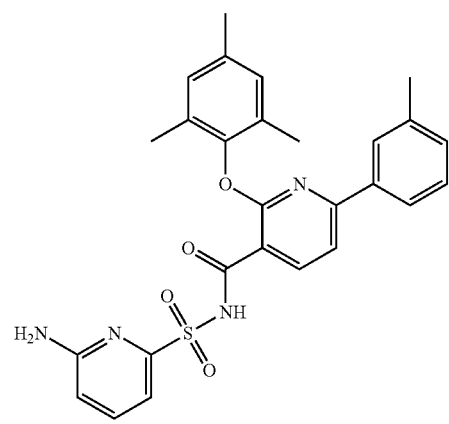 [SMILES: Cc1cccc(-c2ccc(C(=O)NS(=O)(=O)c3cccc(N)n3)c(Oc3c(C)cc(C)cc3C)n2)c1]
672

TABLE 1-continued
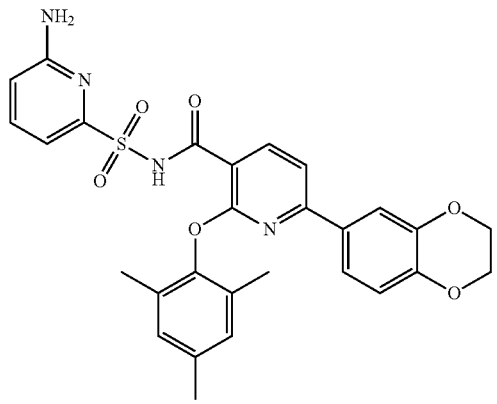 [SMILES: Cc1cc(C)c(Oc2nc(-c3ccc4c(c3)OCCO4)ccc2C(=O)NS(=O)(=O)c2cccc(N)n2)c(C)c1]
673
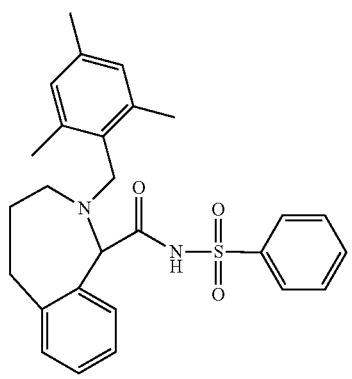 [SMILES: Cc1cc(C)c(CN2CCCc3ccccc3C2C(=O)NS(=O)(=O)c2ccccc2)c(C)c1]
674
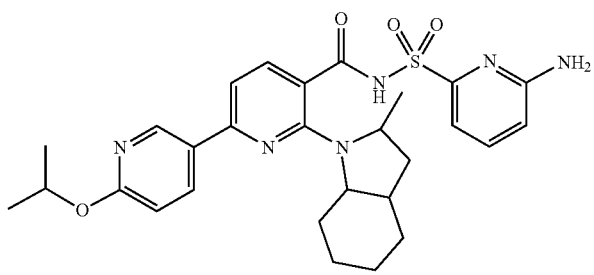 [SMILES: CC(C)Oc1ccc(-c2ccc(C(=O)NS(=O)(=O)c3cccc(N)n3)c(N3C(C)CC4CCCCC43)n2)cn1]
675
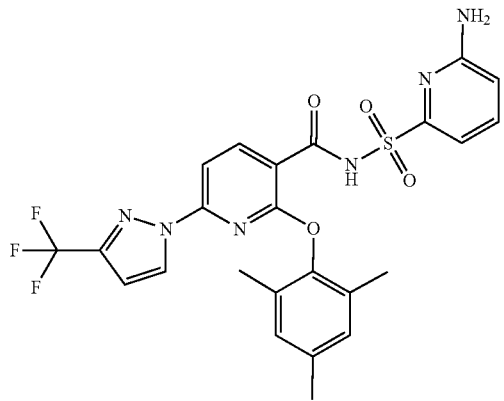 [SMILES: Cc1cc(C)c(Oc2nc(-n3ccc(C(F)(F)F)n3)ccc2C(=O)NS(=O)(=O)c2cccc(N)n2)c(C)c1]
676

TABLE 1-continued
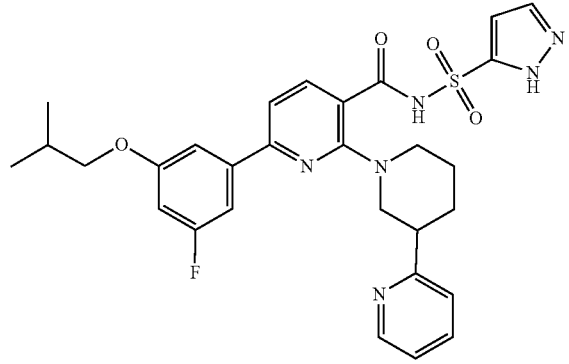 [SMILES: CC(C)COc1cc(F)cc(-c2ccc(C(=O)NS(=O)(=O)c3ccn[nH]3)c(N3CCCC(c4ccccn4)C3)n2)c1] 677
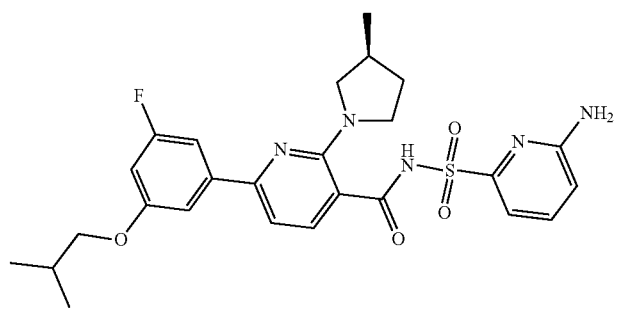 [SMILES: CC(C)COc1cc(F)cc(-c2ccc(C(=O)NS(=O)(=O)c3cccc(N)n3)c(N3CC[C@H](C)C3)n2)c1] 678
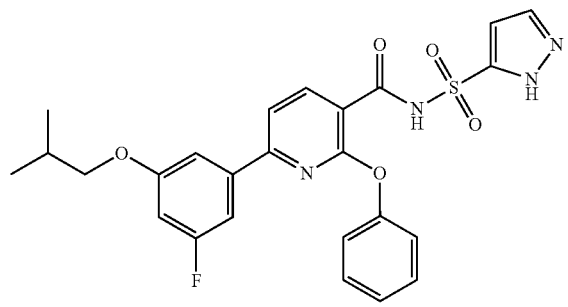 [SMILES: CC(C)COc1cc(F)cc(-c2ccc(C(=O)NS(=O)(=O)c3ccn[nH]3)c(Oc3ccccc3)n2)c1] 679
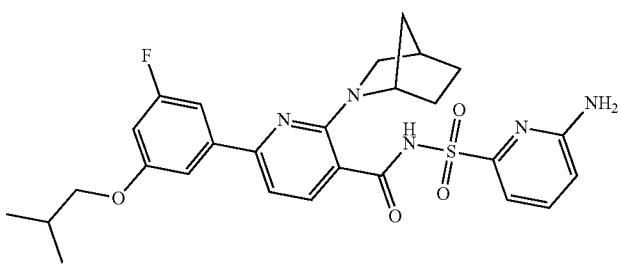 [SMILES: CC(C)COc1cc(F)cc(-c2ccc(C(=O)NS(=O)(=O)c3cccc(N)n3)c(N3CC4CCC3C4)n2)c1] 680
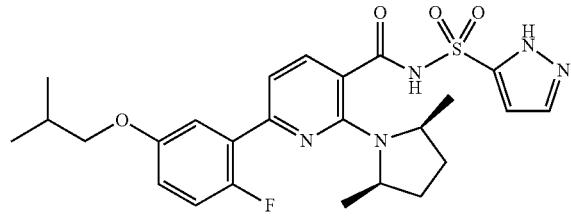 [SMILES: CC(C)COc1ccc(F)c(-c2ccc(C(=O)NS(=O)(=O)c3ccn[nH]3)c(N3[C@H](C)CC[C@@H]3C)n2)c1] 681

TABLE 1-continued
| | |
|---|---|
| 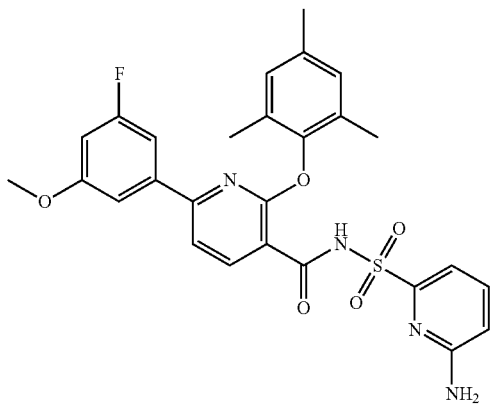 | 682 |
| 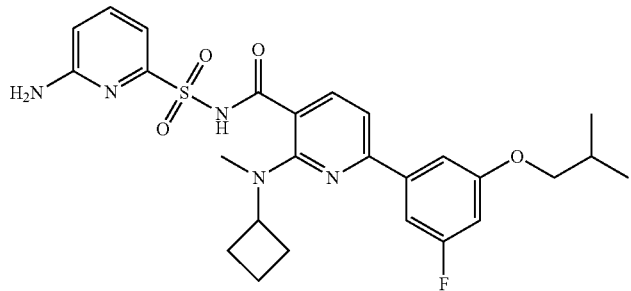 [SMILES: CC(C)COc1cc(F)cc(-c2ccc(C(=O)NS(=O)(=O)c3cccc(N)n3)c(N(C)C3CCC3)n2)c1] | 683 |
| 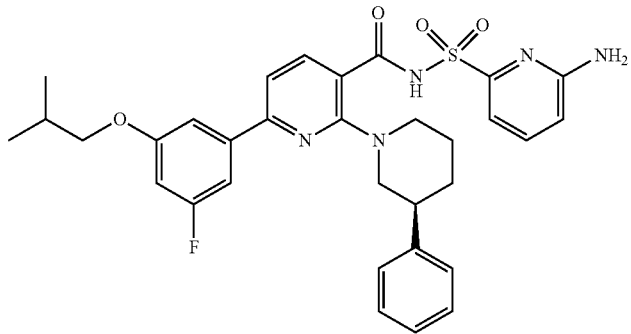 [SMILES: CC(C)COc1cc(F)cc(-c2ccc(C(=O)NS(=O)(=O)c3cccc(N)n3)c(N3CCC[C@@H](c4ccccc4)C3)n2)c1] | 684 |
| 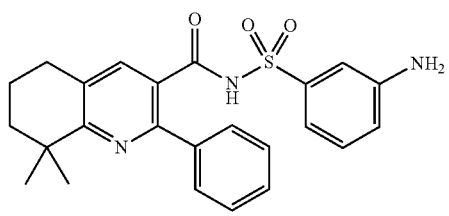 [SMILES: CC1(C)CCCc2cc(C(=O)NS(=O)(=O)c3cccc(N)c3)c(-c3ccccc3)nc21] | 685 |

TABLE 1-continued
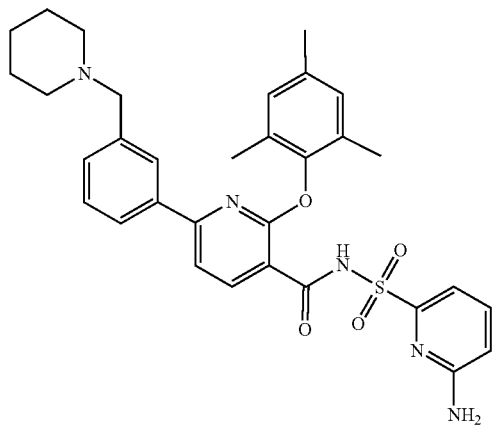 [SMILES: Cc1cc(C)c(Oc2nc(-c3cccc(CN4CCCCC4)c3)ccc2C(=O)NS(=O)(=O)c2cccc(N)n2)c(C)c1]
686
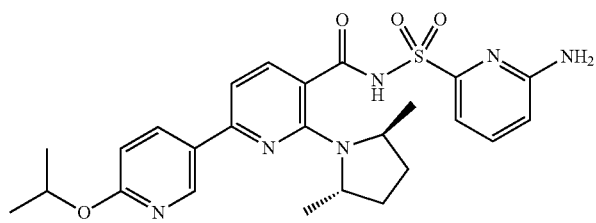 [SMILES: CC(C)Oc1ccc(-c2ccc(C(=O)NS(=O)(=O)c3cccc(N)n3)c(N3[C@@H](C)CC[C@@H]3C)n2)cn1]
687
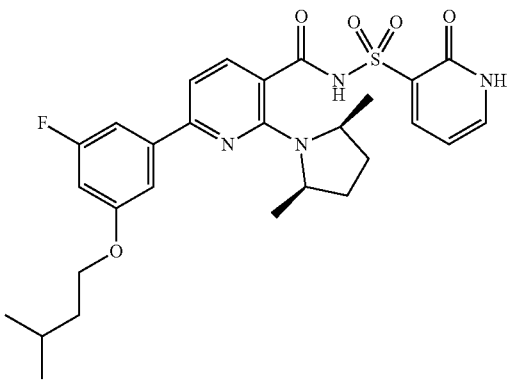 [SMILES: CC(C)CCOc1cc(F)cc(-c2ccc(C(=O)NS(=O)(=O)c3ccc[nH]c3=O)c(N3[C@H](C)CC[C@@H]3C)n2)c1]
688
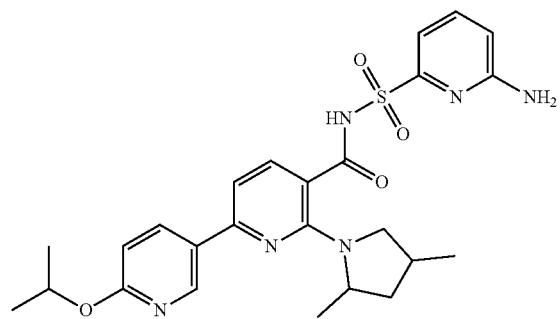 [SMILES: CC1CC(C)N(c2nc(-c3ccc(OC(C)C)nc3)ccc2C(=O)NS(=O)(=O)c2cccc(N)n2)C1]
689

TABLE 1-continued
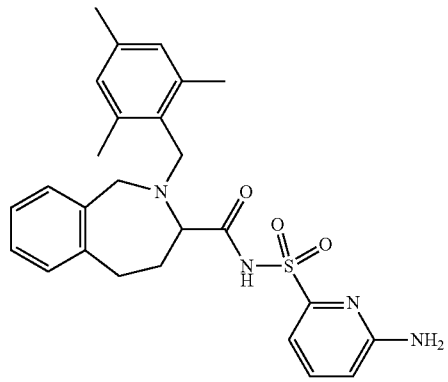 [SMILES: Cc1cc(C)c(CN2Cc3ccccc3CCC2C(=O)NS(=O)(=O)c2cccc(N)n2)c(C)c1]
690
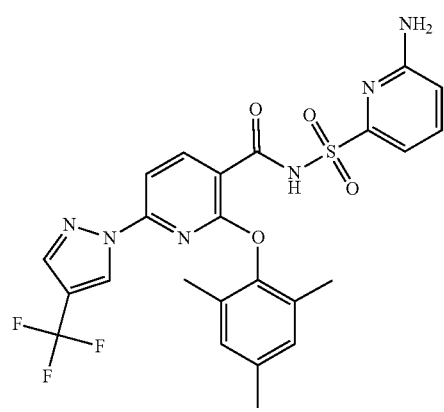 [SMILES: Cc1cc(C)c(Oc2nc(-n3cc(C(F)(F)F)cn3)ccc2C(=O)NS(=O)(=O)c2cccc(N)n2)c(C)c1]
691
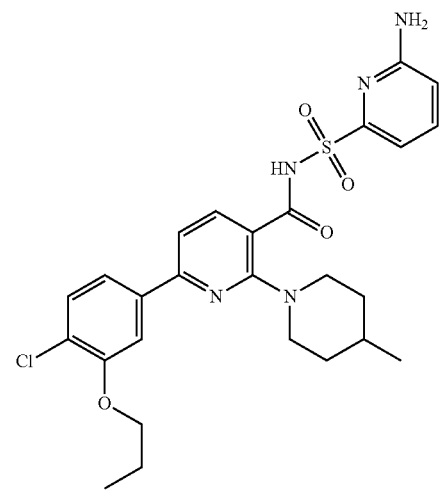 [SMILES: CCCOc1cc(-c2ccc(C(=O)NS(=O)(=O)c3cccc(N)n3)c(N3CCC(C)CC3)n2)ccc1Cl]
692
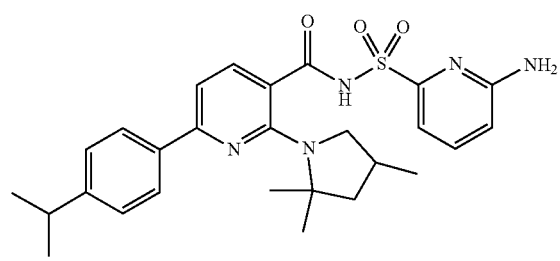 [SMILES: CC1CN(c2nc(-c3ccc(C(C)C)cc3)ccc2C(=O)NS(=O)(=O)c2cccc(N)n2)C(C)(C)C1]
693

TABLE 1-continued
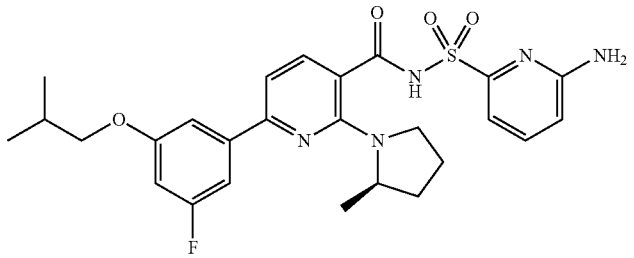 [SMILES: CC(C)COc1cc(F)cc(-c2ccc(C(=O)NS(=O)(=O)c3cccc(N)n3)c(N3CCC[C@H]3C)n2)c1] 694
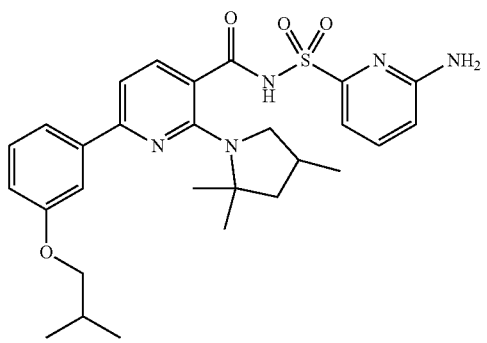 [SMILES: CC(C)COc1cccc(-c2ccc(C(=O)NS(=O)(=O)c3cccc(N)n3)c(N3CC(C)CC3(C)C)n2)c1] 695
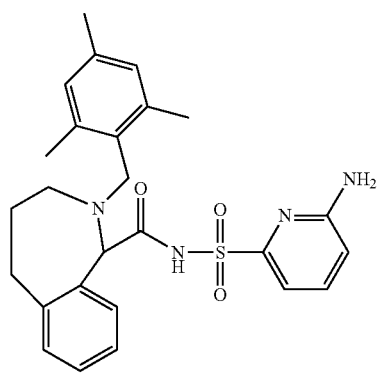 [SMILES: Cc1cc(C)c(CN2CCCc3ccccc3C2C(=O)NS(=O)(=O)c2cccc(N)n2)c(C)c1] 696
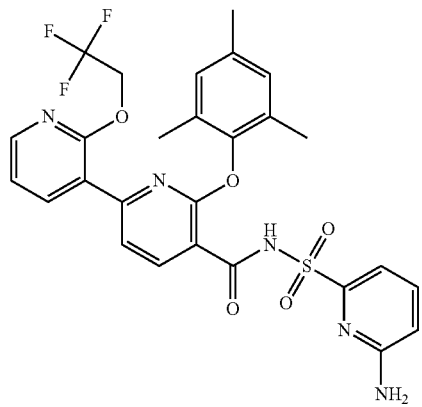 [SMILES: Cc1cc(C)c(Oc2nc(-c3cccnc3OCC(F)(F)F)ccc2C(=O)NS(=O)(=O)c2cccc(N)n2)c(C)c1] 697

TABLE 1-continued
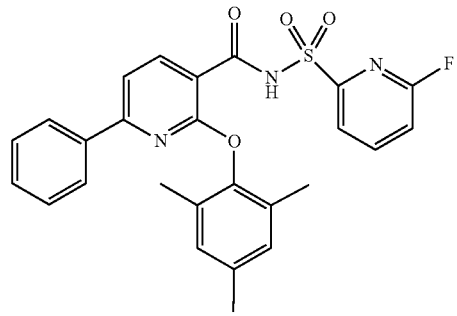 [SMILES: Cc1cc(C)c(Oc2nc(-c3ccccc3)ccc2C(=O)NS(=O)(=O)c2cccc(F)n2)c(C)c1]
698
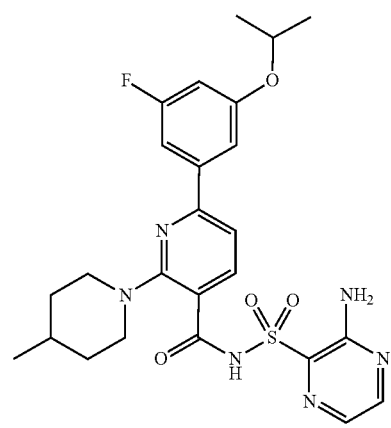 [SMILES: CC1CCN(c2nc(-c3cc(F)cc(OC(C)C)c3)ccc2C(=O)NS(=O)(=O)c2nccnc2N)CC1]
699
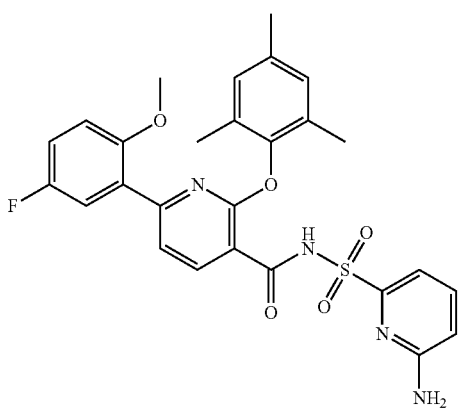 [SMILES: COc1ccc(F)cc1-c1ccc(C(=O)NS(=O)(=O)c2cccc(N)n2)c(Oc2c(C)cc(C)cc2C)n1]
700
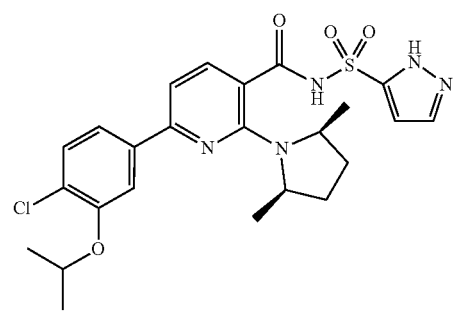 [SMILES: CC(C)Oc1cc(-c2ccc(C(=O)NS(=O)(=O)c3ccn[nH]3)c(N3[C@H](C)CC[C@@H]3C)n2)ccc1Cl]
701

TABLE 1-continued
| | |
|---|---|
| 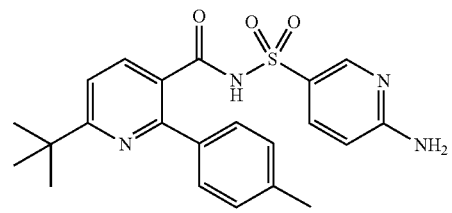 [SMILES: Cc1ccc(-c2nc(C(C)(C)C)ccc2C(=O)NS(=O)(=O)c2ccc(N)nc2)cc1] | 702 |
| 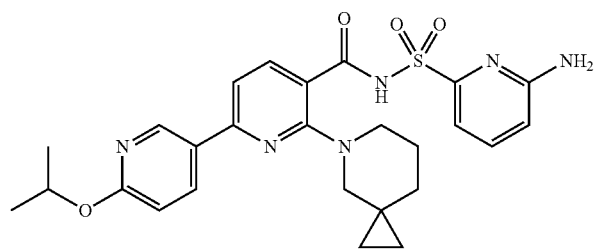 [SMILES: CC(C)Oc1ccc(-c2ccc(C(=O)NS(=O)(=O)c3cccc(N)n3)c(N3CCCC4(CC4)C3)n2)cn1] | 703 |
| 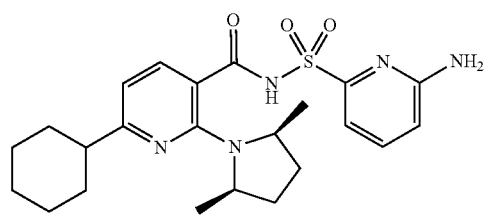 [SMILES: C[C@@H]1CC[C@H](C)N1c1nc(C2CCCCC2)ccc1C(=O)NS(=O)(=O)c1cccc(N)n1] | 704 |
| 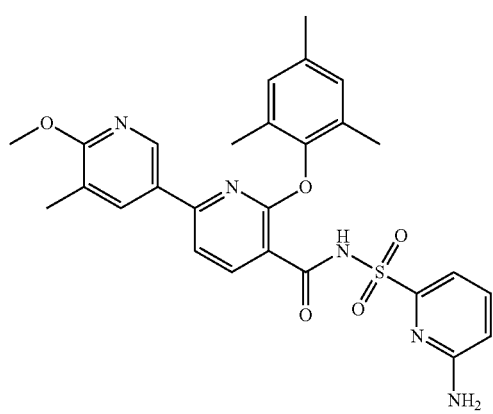 [SMILES: COc1ncc(-c2ccc(C(=O)NS(=O)(=O)c3cccc(N)n3)c(Oc3c(C)cc(C)cc3C)n2)cc1C] | 705 |
| 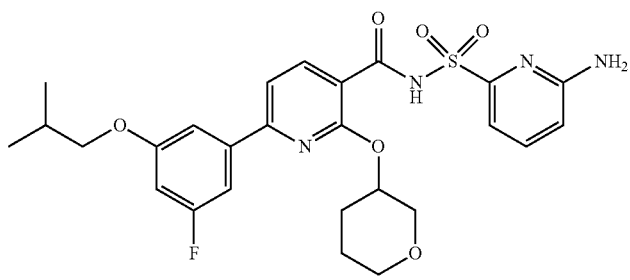 [SMILES: CC(C)COc1cc(F)cc(-c2ccc(C(=O)NS(=O)(=O)c3cccc(N)n3)c(OC3CCCOC3)n2)c1] | 706 |
| 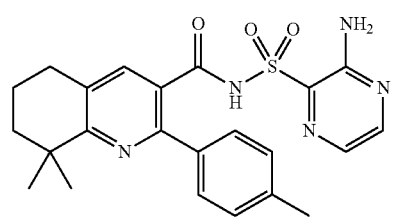 [SMILES: Cc1ccc(-c2nc3c(cc2C(=O)NS(=O)(=O)c2nccnc2N)CCCC3(C)C)cc1] | 707 |

TABLE 1-continued
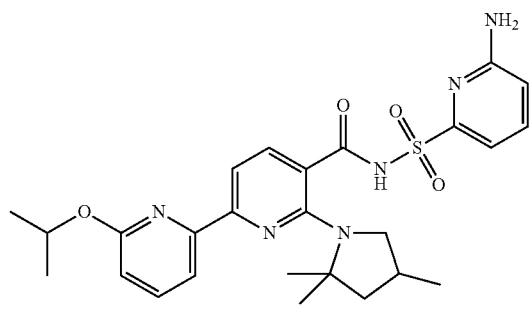 [SMILES: CC1CN(c2nc(-c3cccc(OC(C)C)n3)ccc2C(=O)NS(=O)(=O)c2cccc(N)n2)C(C)(C)C1]
708
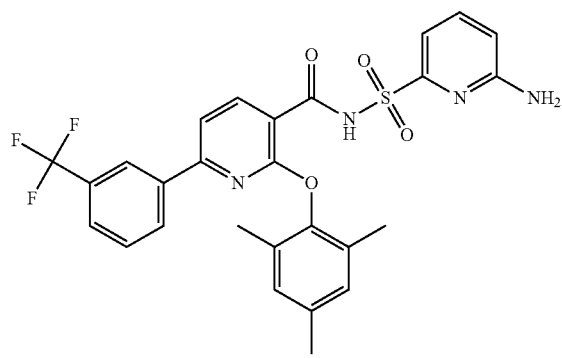 [SMILES: Cc1cc(C)c(Oc2nc(-c3cccc(C(F)(F)F)c3)ccc2C(=O)NS(=O)(=O)c2cccc(N)n2)c(C)c1]
709
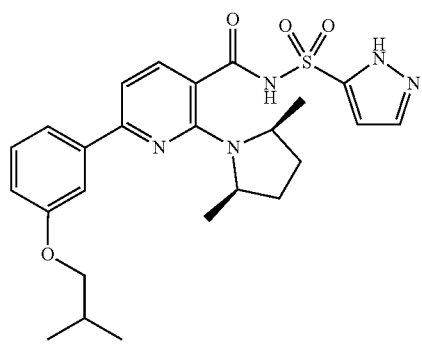 [SMILES: CC(C)COc1cccc(-c2ccc(C(=O)NS(=O)(=O)c3ccn[nH]3)c(N3[C@H](C)CC[C@@H]3C)n2)c1]
710
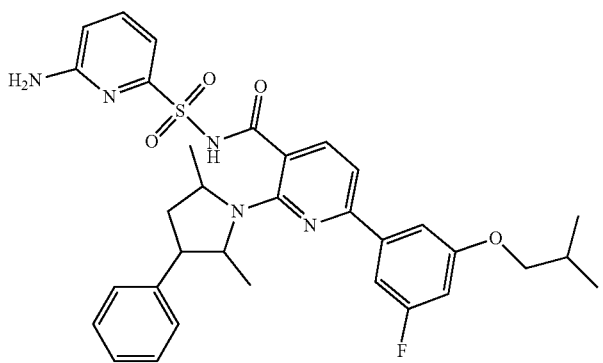
711
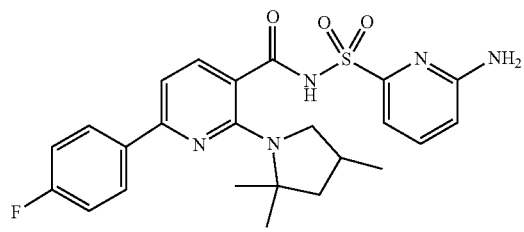 [SMILES: CC1CN(c2nc(-c3ccc(F)cc3)ccc2C(=O)NS(=O)(=O)c2cccc(N)n2)C(C)(C)C1]
712

TABLE 1-continued
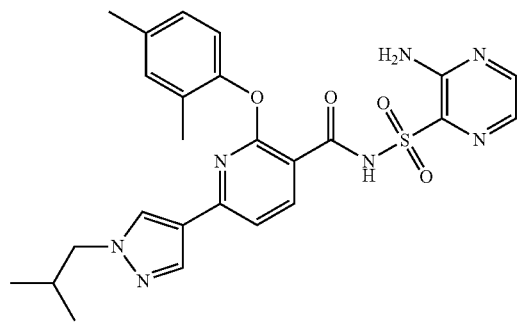 [SMILES: Cc1ccc(Oc2nc(-c3cnn(CC(C)C)c3)ccc2C(=O)NS(=O)(=O)c2nccnc2N)c(C)c1]
713
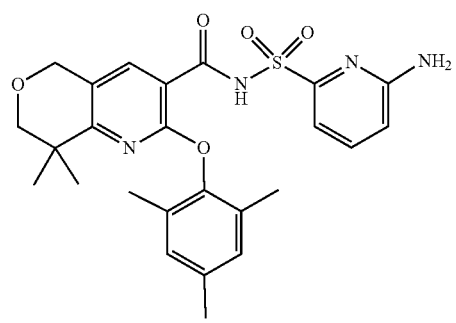 [SMILES: Cc1cc(C)c(Oc2nc3c(cc2C(=O)NS(=O)(=O)c2cccc(N)n2)COCC3(C)C)c(C)c1]
714
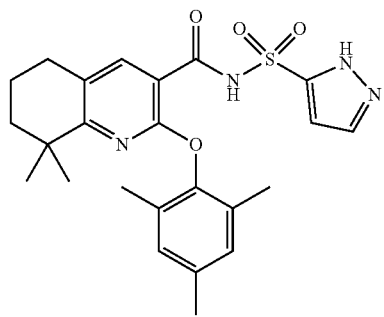 [SMILES: Cc1cc(C)c(Oc2nc3c(cc2C(=O)NS(=O)(=O)c2ccn[nH]2)CCCC3(C)C)c(C)c1]
715
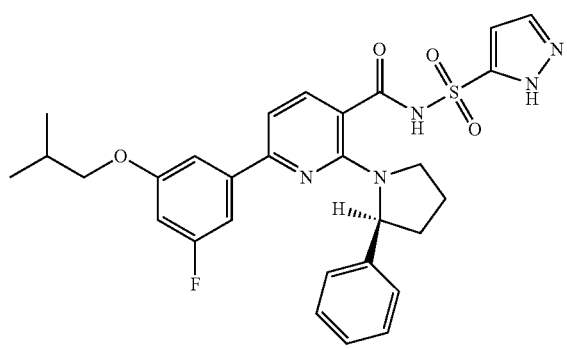 [SMILES: CC(C)COc1cc(F)cc(-c2ccc(C(=O)NS(=O)(=O)c3ccn[nH]3)c(N3CCC[C@H]3c3ccccc3)n2)c1]
716

TABLE 1-continued
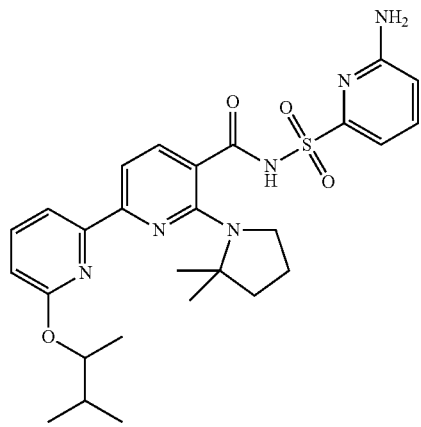 [SMILES: CC(C)C(C)Oc1cccc(-c2ccc(C(=O)NS(=O)(=O)c3cccc(N)n3)c(N3CCCC3(C)C)n2)n1]
717
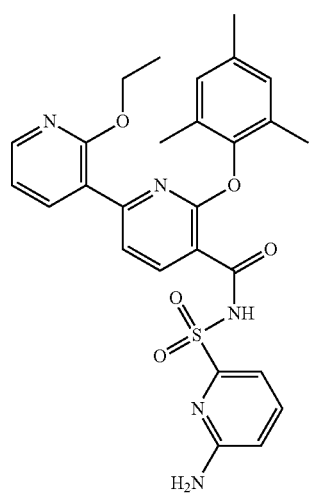 [SMILES: CCOc1ncccc1-c1ccc(C(=O)NS(=O)(=O)c2cccc(N)n2)c(Oc2c(C)cc(C)cc2C)n1]
718
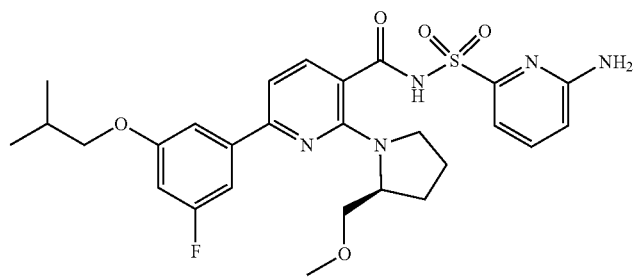 [SMILES: COC[C@@H]1CCCN1c1nc(-c2cc(F)cc(OCC(C)C)c2)ccc1C(=O)NS(=O)(=O)c1cccc(N)n1]
719

TABLE 1-continued
| | |
|---|---|
| 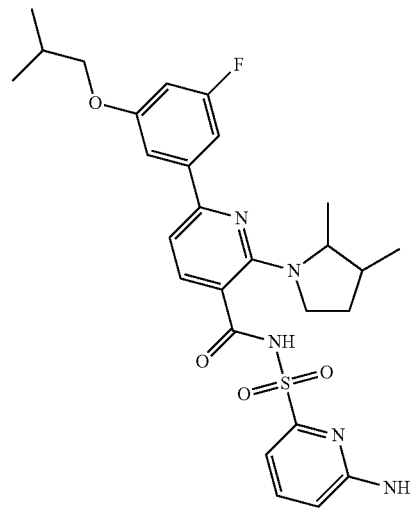 | 720 |
| 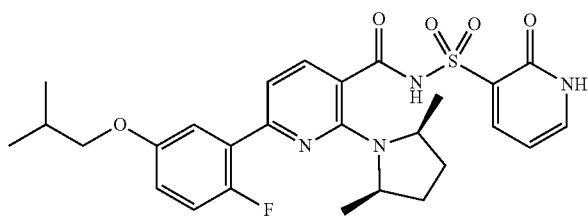 [SMILES: CC(C)COc1ccc(F)c(-c2ccc(C(=O)NS(=O)(=O)c3ccc[nH]c3=O)c(N3[C@H](C)CC[C@@H]3C)n2)c1] | 721 |
| 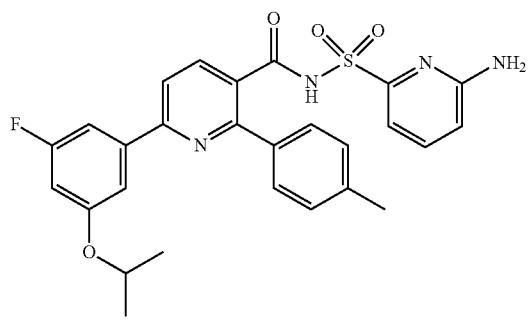 [SMILES: Cc1ccc(-c2nc(-c3cc(F)cc(OC(C)C)c3)ccc2C(=O)NS(=O)(=O)c2cccc(N)n2)cc1] | 722 |
| 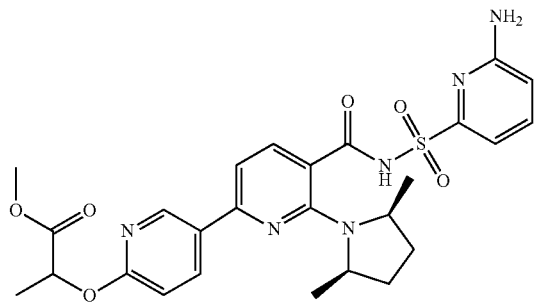 [SMILES: COC(=O)C(C)Oc1ccc(-c2ccc(C(=O)NS(=O)(=O)c3cccc(N)n3)c(N3[C@H](C)CC[C@@H]3C)n2)cn1] | 723 |
| 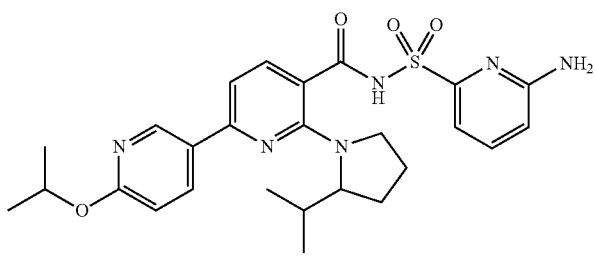 [SMILES: CC(C)Oc1ccc(-c2ccc(C(=O)NS(=O)(=O)c3cccc(N)n3)c(N3CCCC3C(C)C)n2)cn1] | 724 |

TABLE 1-continued
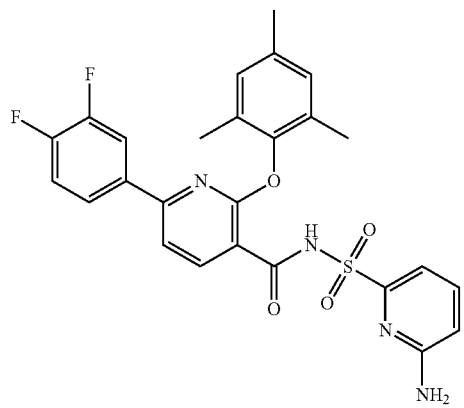 [SMILES: Cc1cc(C)c(Oc2nc(-c3ccc(F)c(F)c3)ccc2C(=O)NS(=O)(=O)c2cccc(N)n2)c(C)c1]
725
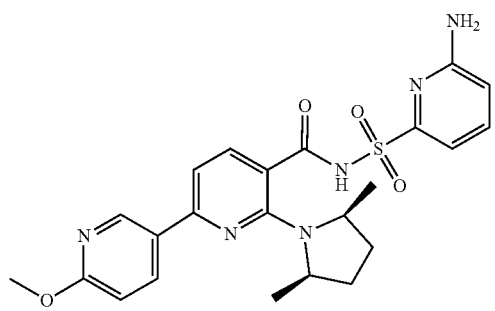 [SMILES: COc1ccc(-c2ccc(C(=O)NS(=O)(=O)c3cccc(N)n3)c(N3[C@H](C)CC[C@@H]3C)n2)cn1]
726
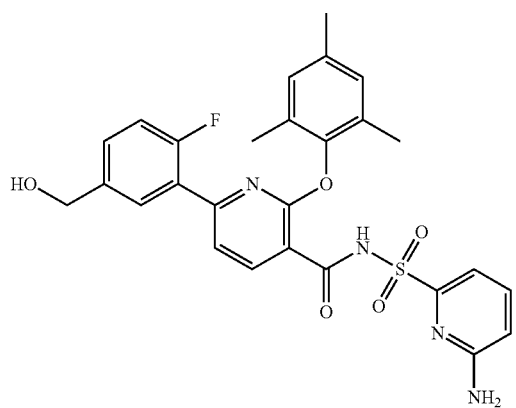 [SMILES: Cc1cc(C)c(Oc2nc(-c3cc(CO)ccc3F)ccc2C(=O)NS(=O)(=O)c2cccc(N)n2)c(C)c1]
727
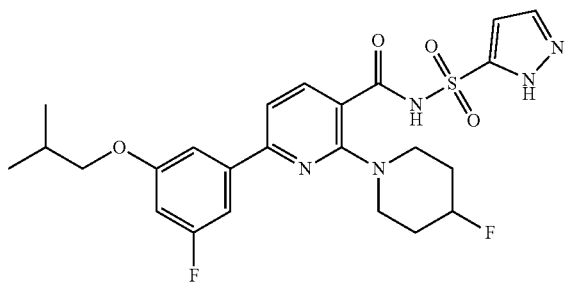 [SMILES: CC(C)COc1cc(F)cc(-c2ccc(C(=O)NS(=O)(=O)c3ccn[nH]3)c(N3CCC(F)CC3)n2)c1]
728
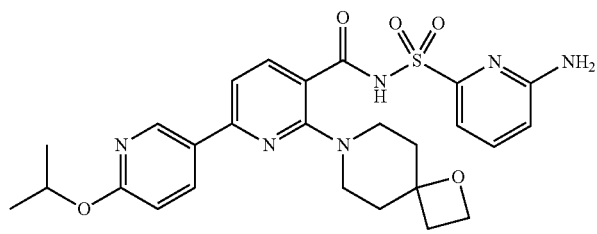 [SMILES: CC(C)Oc1ccc(-c2ccc(C(=O)NS(=O)(=O)c3cccc(N)n3)c(N3CCC4(CCO4)CC3)n2)cn1]
729

TABLE 1-continued
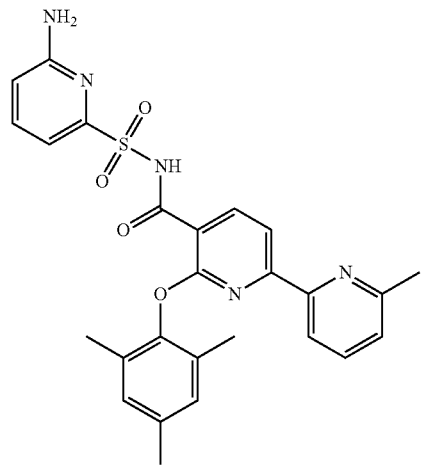 [SMILES: Cc1cc(C)c(Oc2nc(-c3cccc(C)n3)ccc2C(=O)NS(=O)(=O)c2cccc(N)n2)c(C)c1]
730
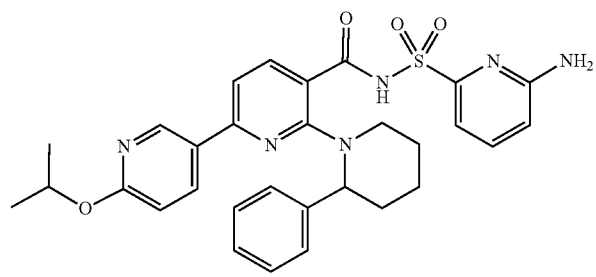 [SMILES: CC(C)Oc1ccc(-c2ccc(C(=O)NS(=O)(=O)c3cccc(N)n3)c(N3CCCCC3c3ccccc3)n2)cn1]
731
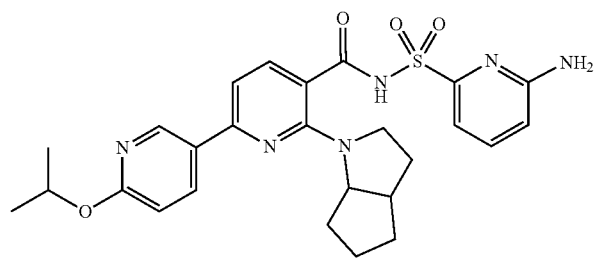 [SMILES: CC(C)Oc1ccc(-c2ccc(C(=O)NS(=O)(=O)c3cccc(N)n3)c(N3CCC4CCCC43)n2)cn1]
732
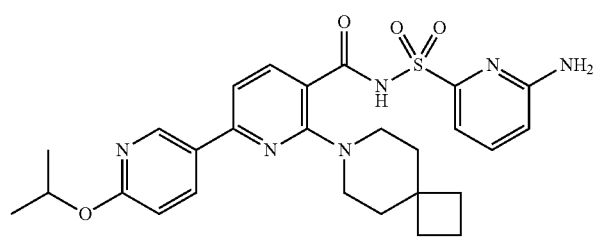 [SMILES: CC(C)Oc1ccc(-c2ccc(C(=O)NS(=O)(=O)c3cccc(N)n3)c(N3CCC4(CCC4)CC3)n2)cn1]
733
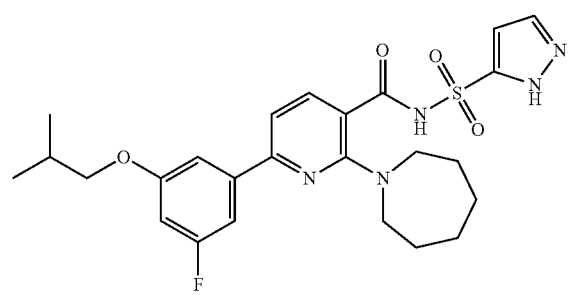 [SMILES: CC(C)COc1cc(F)cc(-c2ccc(C(=O)NS(=O)(=O)c3ccn[nH]3)c(N3CCCCCC3)n2)c1]
734

TABLE 1-continued
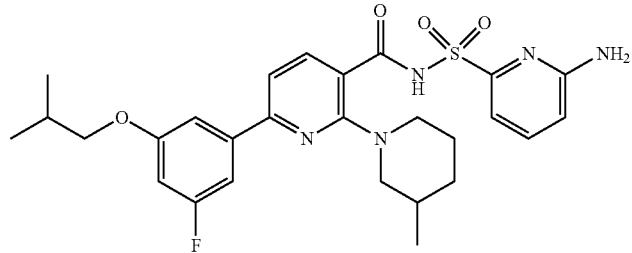 [SMILES: CC(C)COc1cc(F)cc(-c2ccc(C(=O)NS(=O)(=O)c3cccc(N)n3)c(N3CCCC(C)C3)n2)c1]
735
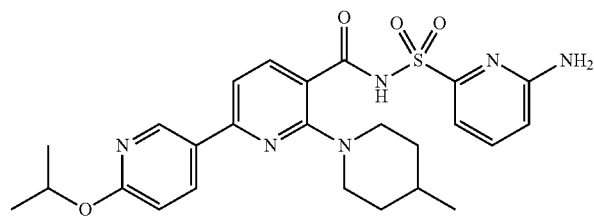 [SMILES: CC1CCN(c2nc(-c3ccc(OC(C)C)nc3)ccc2C(=O)NS(=O)(=O)c2cccc(N)n2)CC1]
736
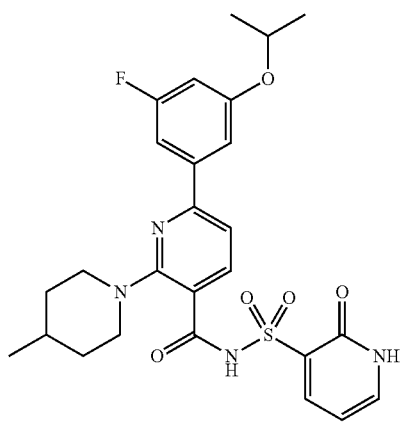 [SMILES: CC1CCN(c2nc(-c3cc(F)cc(OC(C)C)c3)ccc2C(=O)NS(=O)(=O)c2ccc[nH]c2=O)CC1]
737
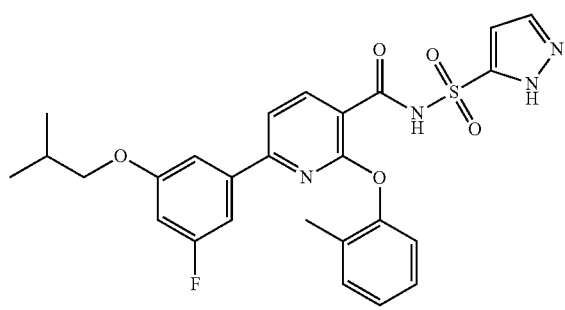 [SMILES: Cc1ccccc1Oc1nc(-c2cc(F)cc(OCC(C)C)c2)ccc1C(=O)NS(=O)(=O)c1ccn[nH]1]
738
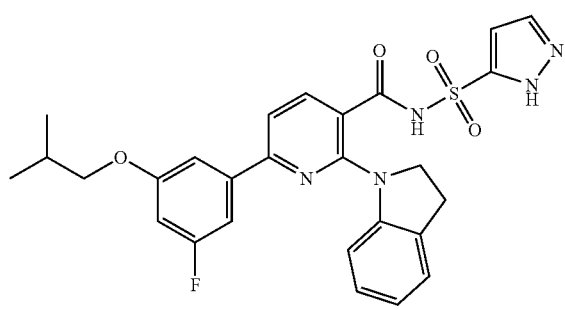 [SMILES: CC(C)COc1cc(F)cc(-c2ccc(C(=O)NS(=O)(=O)c3ccn[nH]3)c(N3CCc4ccccc43)n2)c1]
739

TABLE 1-continued
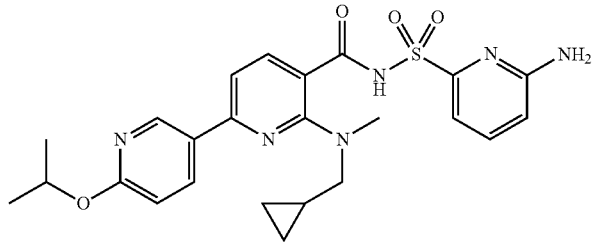 [SMILES: CC(C)Oc1ccc(-c2ccc(C(=O)NS(=O)(=O)c3cccc(N)n3)c(N(C)CC3CC3)n2)cn1]
740
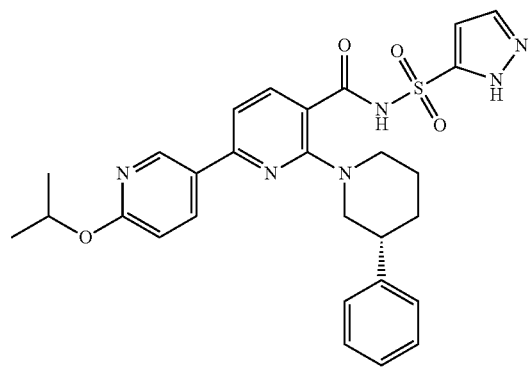 [SMILES: CC(C)Oc1ccc(-c2ccc(C(=O)NS(=O)(=O)c3ccn[nH]3)c(N3CCC[C@H](c4ccccc4)C3)n2)cn1]
741
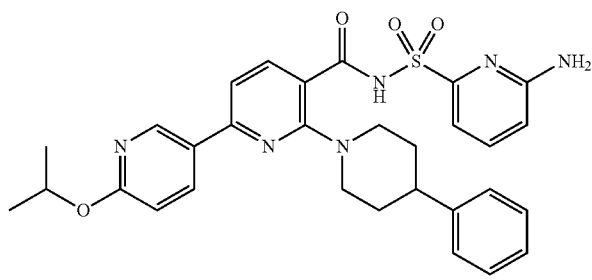 [SMILES: CC(C)Oc1ccc(-c2ccc(C(=O)NS(=O)(=O)c3cccc(N)n3)c(N3CCC(c4ccccc4)CC3)n2)cn1]
742
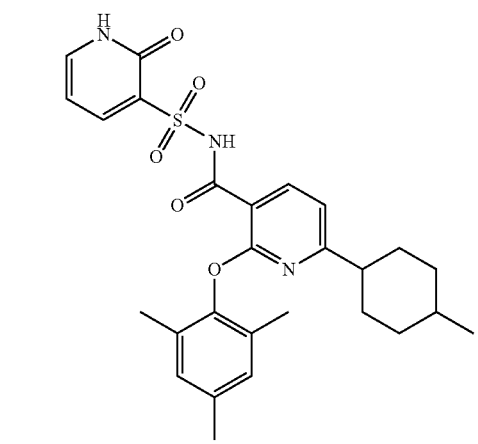 [SMILES: Cc1cc(C)c(Oc2nc(C3CCC(C)CC3)ccc2C(=O)NS(=O)(=O)c2ccc[nH]c2=O)c(C)c1]
743

TABLE 1-continued
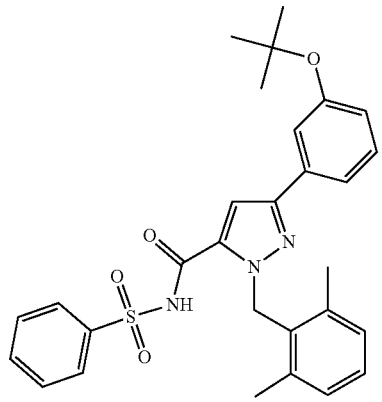 [SMILES: Cc1cccc(C)c1Cn1nc(-c2cccc(OC(C)(C)C)c2)cc1C(=O)NS(=O)(=O)c1ccccc1]
744
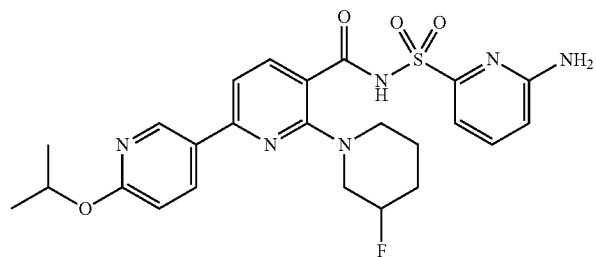 [SMILES: CC(C)Oc1ccc(-c2ccc(C(=O)NS(=O)(=O)c3cccc(N)n3)c(N3CCCC(F)C3)n2)cn1]
745
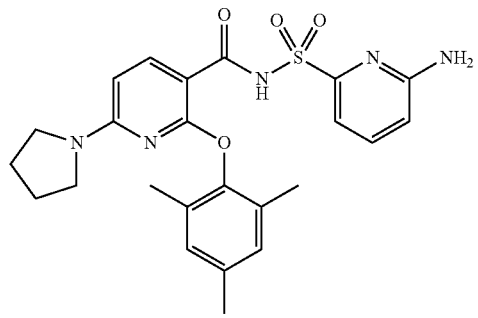 [SMILES: Cc1cc(C)c(Oc2nc(N3CCCC3)ccc2C(=O)NS(=O)(=O)c2cccc(N)n2)c(C)c1]
746
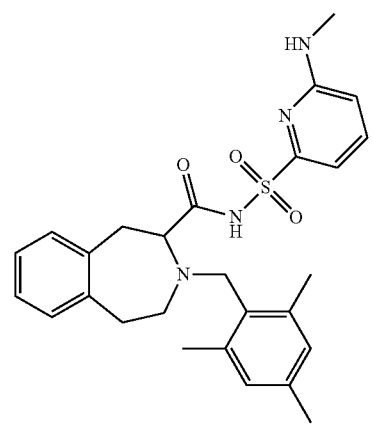 [SMILES: CNc1cccc(S(=O)(=O)NC(=O)C2Cc3ccccc3CCN2Cc2c(C)cc(C)cc2C)n1]
747

TABLE 1-continued
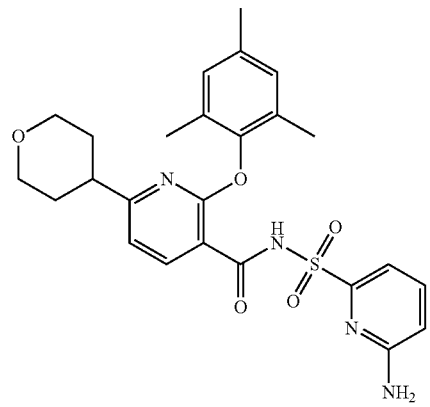 [SMILES: Cc1cc(C)c(Oc2nc(C3CCOCC3)ccc2C(=O)NS(=O)(=O)c2cccc(N)n2)c(C)c1]
748
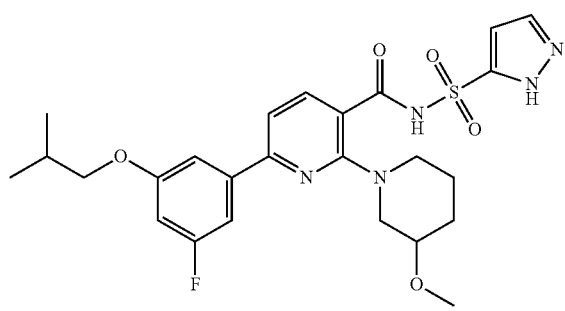 [SMILES: COC1CCCN(c2nc(-c3cc(F)cc(OCC(C)C)c3)ccc2C(=O)NS(=O)(=O)c2ccn[nH]2)C1]
749
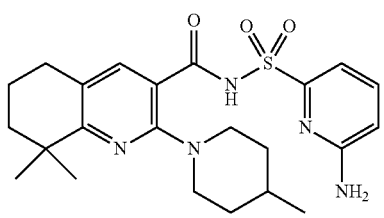 [SMILES: CC1CCN(c2nc3c(cc2C(=O)NS(=O)(=O)c2cccc(N)n2)CCCC3(C)C)CC1]
750
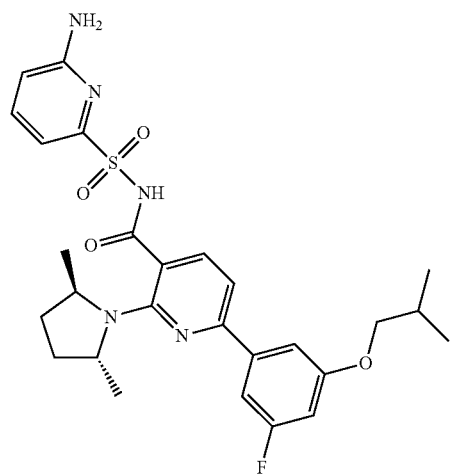 [SMILES: CC(C)COc1cc(F)cc(-c2ccc(C(=O)NS(=O)(=O)c3cccc(N)n3)c(N3[C@H](C)CC[C@H]3C)n2)c1]
751

TABLE 1-continued
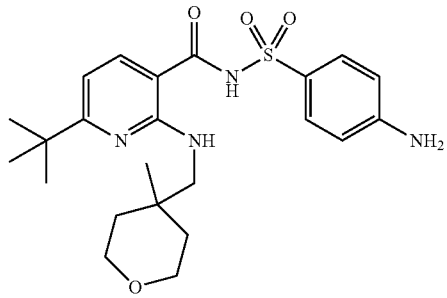 [SMILES: CC1(CNc2nc(C(C)(C)C)ccc2C(=O)NS(=O)(=O)c2ccc(N)cc2)CCOCC1]
752
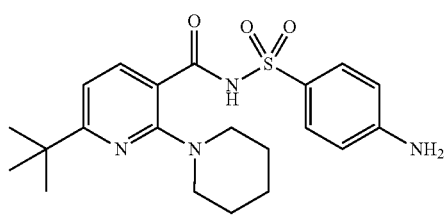 [SMILES: CC(C)(C)c1ccc(C(=O)NS(=O)(=O)c2ccc(N)cc2)c(N2CCCCC2)n1]
753
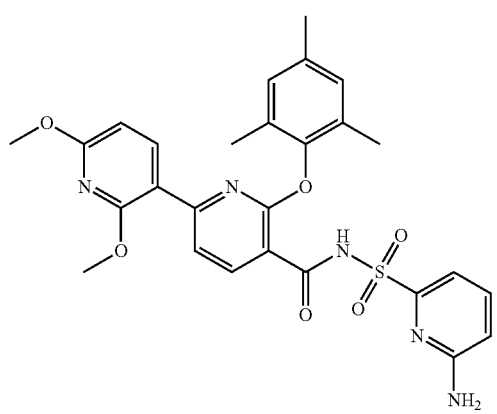 [SMILES: COc1ccc(-c2ccc(C(=O)NS(=O)(=O)c3cccc(N)n3)c(Oc3c(C)cc(C)cc3C)n2)c(OC)n1]
754
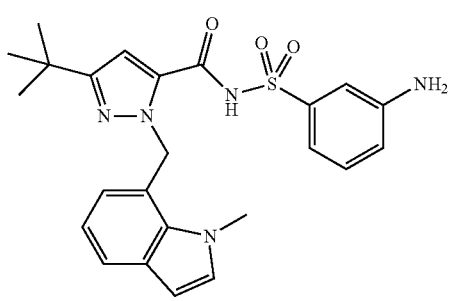 [SMILES: Cn1ccc2cccc(Cn3nc(C(C)(C)C)cc3C(=O)NS(=O)(=O)c3cccc(N)c3)c21]
755
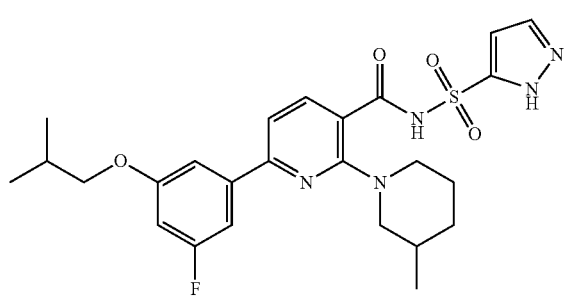
756

TABLE 1-continued
| | |
|---|---|
| 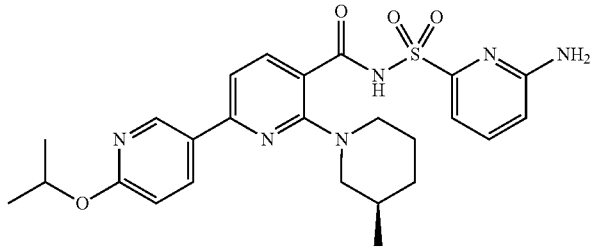 [SMILES: CC(C)Oc1ccc(-c2ccc(C(=O)NS(=O)(=O)c3cccc(N)n3)c(N3CCC[C@@H](C)C3)n2)cn1] | 757 |
| 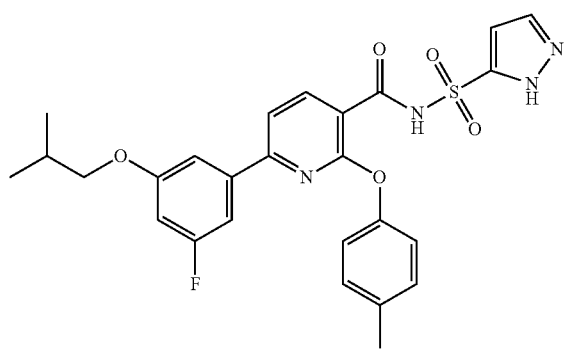 [SMILES: Cc1ccc(Oc2nc(-c3cc(F)cc(OCC(C)C)c3)ccc2C(=O)NS(=O)(=O)c2ccn[nH]2)cc1] | 758 |
| 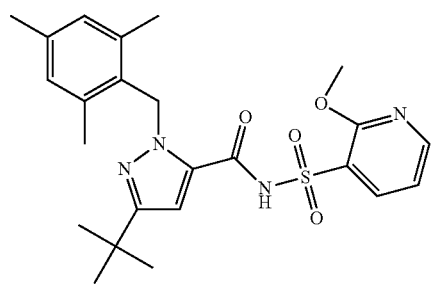 [SMILES: COc1ncccc1S(=O)(=O)NC(=O)c1cc(C(C)(C)C)nn1Cc1c(C)cc(C)cc1C] | 759 |
| 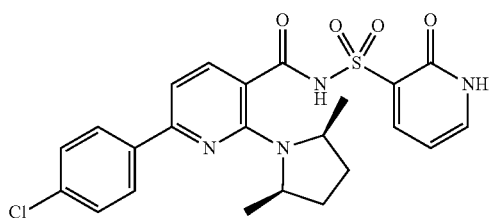 [SMILES: C[C@@H]1CC[C@H](C)N1c1nc(-c2ccc(Cl)cc2)ccc1C(=O)NS(=O)(=O)c1ccc[nH]c1=O] | 760 |
| 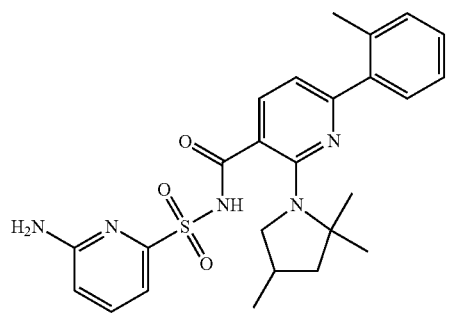 [SMILES: Cc1ccccc1-c1ccc(C(=O)NS(=O)(=O)c2cccc(N)n2)c(N2CC(C)CC2(C)C)n1] | 761 |

TABLE 1-continued
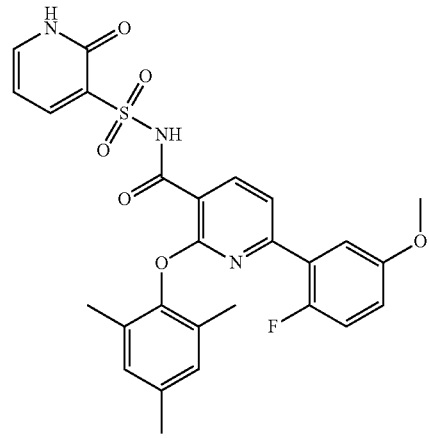 [SMILES: COc1ccc(F)c(-c2ccc(C(=O)NS(=O)(=O)c3ccc[nH]c3=O)c(Oc3c(C)cc(C)cc3C)n2)c1]
762
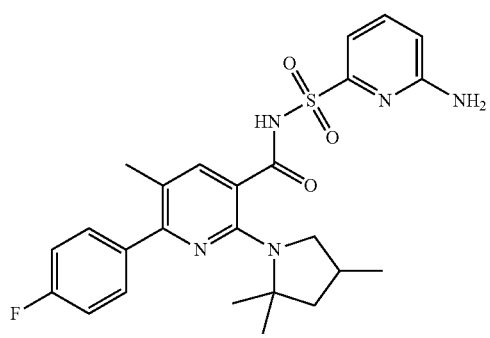 [SMILES: Cc1cc(C(=O)NS(=O)(=O)c2cccc(N)n2)c(N2CC(C)CC2(C)C)nc1-c1ccc(F)cc1]
763
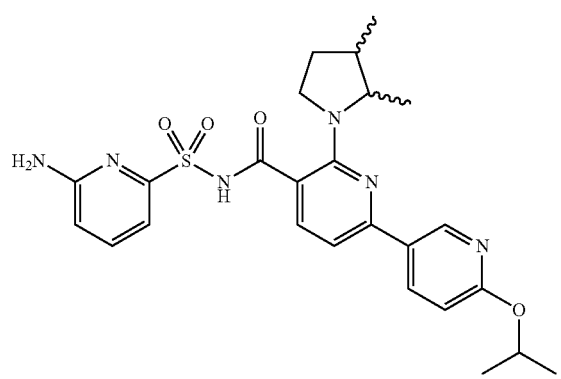
764
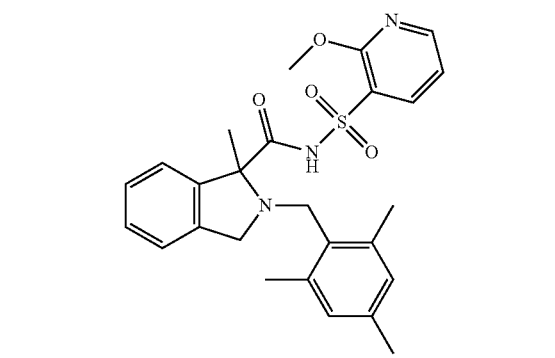 [SMILES: COc1ncccc1S(=O)(=O)NC(=O)C1(C)c2ccccc2CN1Cc1c(C)cc(C)cc1C]
765

TABLE 1-continued
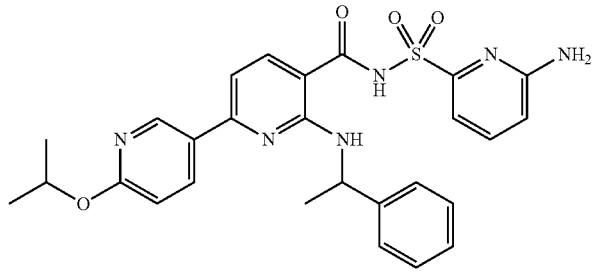 [SMILES: CC(C)Oc1ccc(-c2ccc(C(=O)NS(=O)(=O)c3cccc(N)n3)c(NC(C)c3ccccc3)n2)cn1]
766
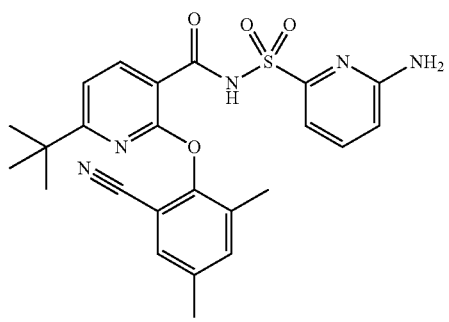 [SMILES: Cc1cc(C)c(Oc2nc(C(C)(C)C)ccc2C(=O)NS(=O)(=O)c2cccc(N)n2)c(C#N)c1]
767
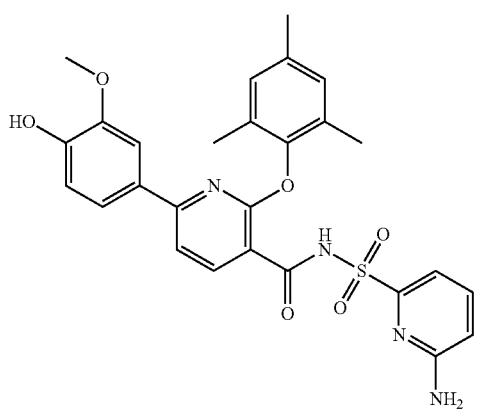 [SMILES: COc1cc(-c2ccc(C(=O)NS(=O)(=O)c3cccc(N)n3)c(Oc3c(C)cc(C)cc3C)n2)ccc1O]
768
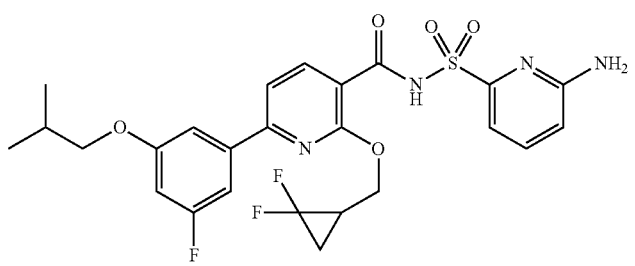 [SMILES: CC(C)COc1cc(F)cc(-c2ccc(C(=O)NS(=O)(=O)c3cccc(N)n3)c(OCC3CC3(F)F)n2)c1]
769
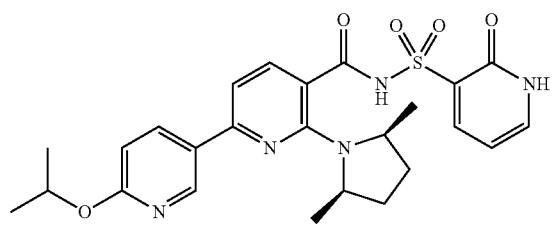 [SMILES: CC(C)Oc1ccc(-c2ccc(C(=O)NS(=O)(=O)c3ccc[nH]c3=O)c(N3[C@H](C)CC[C@@H]3C)n2)cn1]
770

TABLE 1-continued
| | |
|---|---|
| 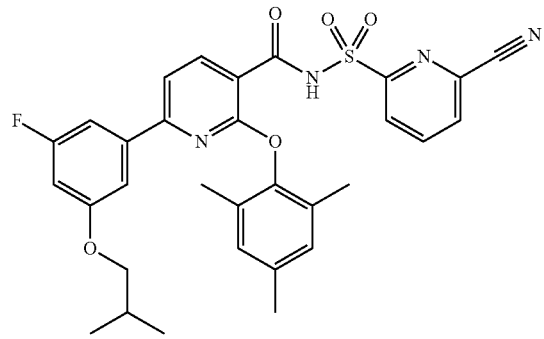 [SMILES: Cc1cc(C)c(Oc2nc(-c3cc(F)cc(OCC(C)C)c3)ccc2C(=O)NS(=O)(=O)c2cccc(C#N)n2)c(C)c1] | 771 |
| 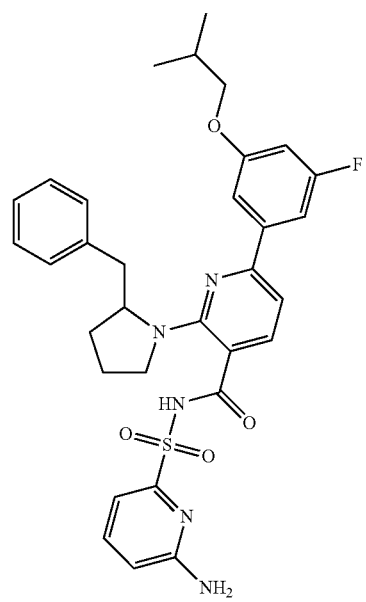 [SMILES: CC(C)COc1cc(F)cc(-c2ccc(C(=O)NS(=O)(=O)c3cccc(N)n3)c(N3CCCC3Cc3ccccc3)n2)c1] | 772 |
| 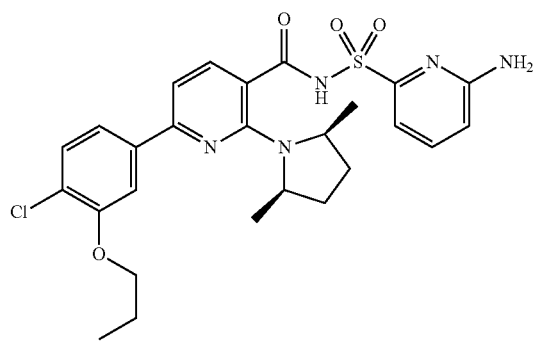 [SMILES: CCCOc1cc(-c2ccc(C(=O)NS(=O)(=O)c3cccc(N)n3)c(N3[C@H](C)CC[C@@H]3C)n2)ccc1Cl] | 773 |
| 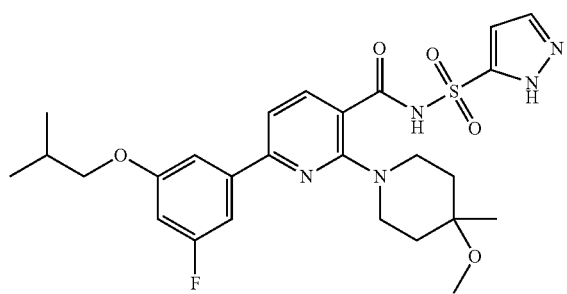 [SMILES: COC1(C)CCN(c2nc(-c3cc(F)cc(OCC(C)C)c3)ccc2C(=O)NS(=O)(=O)c2ccn[nH]2)CC1] | 774 |

TABLE 1-continued
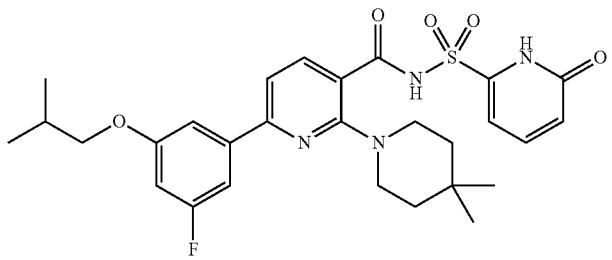 [SMILES: CC(C)COc1cc(F)cc(-c2ccc(C(=O)NS(=O)(=O)c3cccc(=O)[nH]3)c(N3CCC(C)(C)CC3)n2)c1]
775
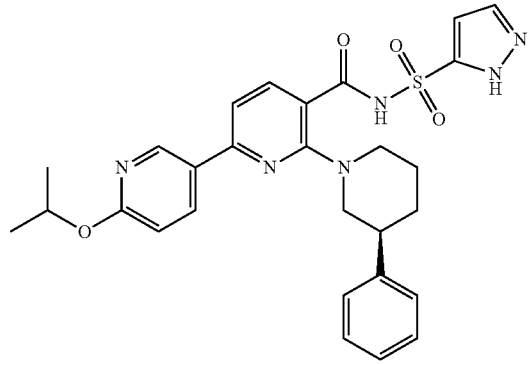 [SMILES: CC(C)Oc1ccc(-c2ccc(C(=O)NS(=O)(=O)c3ccn[nH]3)c(N3CCC[C@@H](c4ccccc4)C3)n2)cn1]
776
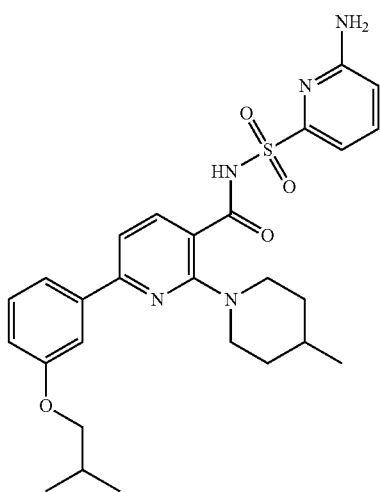 [SMILES: CC(C)COc1cccc(-c2ccc(C(=O)NS(=O)(=O)c3cccc(N)n3)c(N3CCC(C)CC3)n2)c1]
777
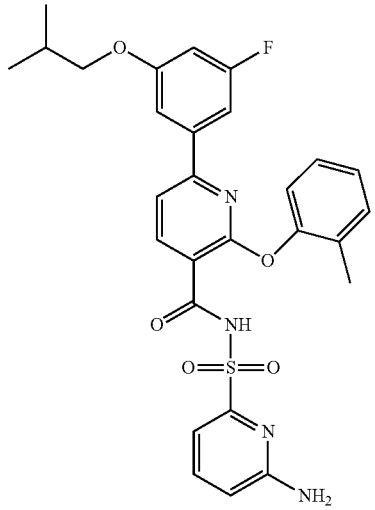 [SMILES: Cc1ccccc1Oc1nc(-c2cc(F)cc(OCC(C)C)c2)ccc1C(=O)NS(=O)(=O)c1cccc(N)n1]
778

| | |
|---|---|
| 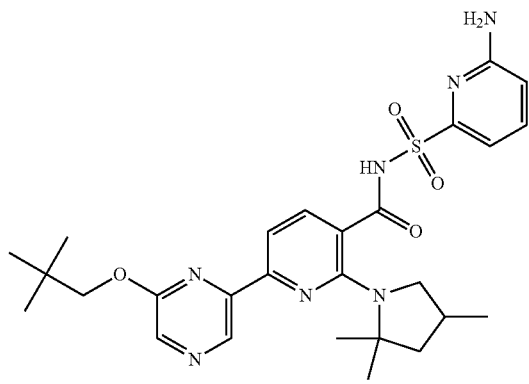 [SMILES: CC1CN(c2nc(-c3cncc(OCC(C)(C)C)n3)ccc2C(=O)NS(=O)(=O)c2cccc(N)n2)C(C)(C)C1] | 779 |
| 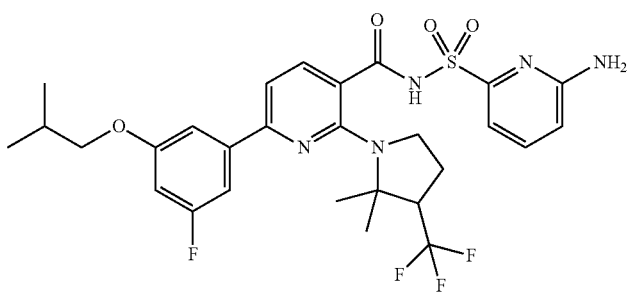 [SMILES: CC(C)COc1cc(F)cc(-c2ccc(C(=O)NS(=O)(=O)c3cccc(N)n3)c(N3CCC(C(F)(F)F)C3(C)C)n2)c1] | 780 |
| 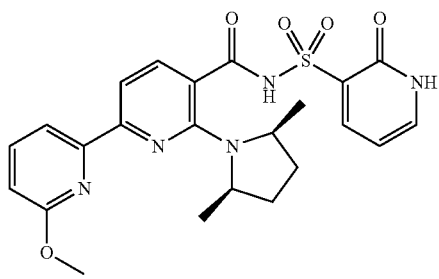 [SMILES: COc1cccc(-c2ccc(C(=O)NS(=O)(=O)c3ccc[nH]c3=O)c(N3[C@H](C)CC[C@@H]3C)n2)n1] | 781 |
| 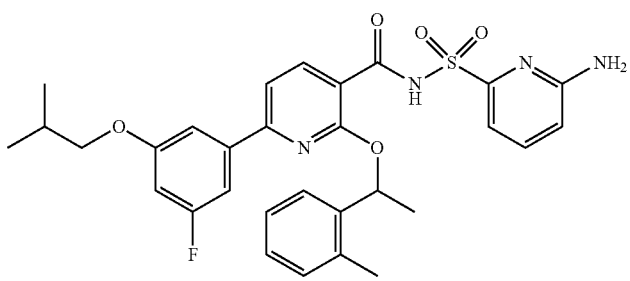 [SMILES: Cc1ccccc1C(C)Oc1nc(-c2cc(F)cc(OCC(C)C)c2)ccc1C(=O)NS(=O)(=O)c1cccc(N)n1] | 782 |
| 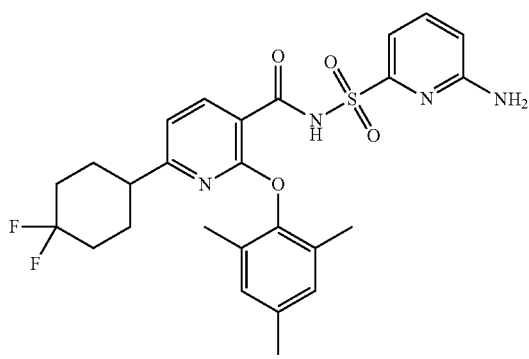 [SMILES: Cc1cc(C)c(Oc2nc(C3CCC(F)(F)CC3)ccc2C(=O)NS(=O)(=O)c2cccc(N)n2)c(C)c1] | 783 |

TABLE 1-continued
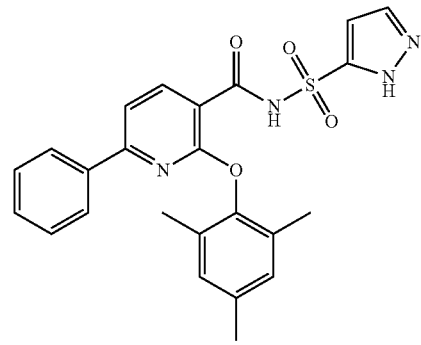 [SMILES: Cc1cc(C)c(Oc2nc(-c3ccccc3)ccc2C(=O)NS(=O)(=O)c2ccn[nH]2)c(C)c1]
784
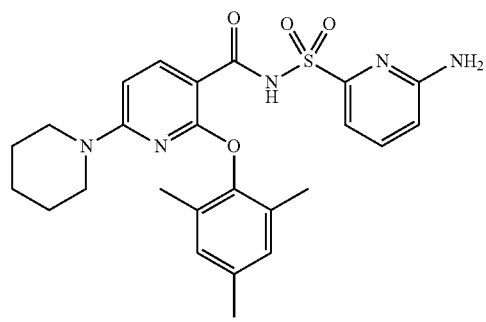 [SMILES: Cc1cc(C)c(Oc2nc(N3CCCCC3)ccc2C(=O)NS(=O)(=O)c2cccc(N)n2)c(C)c1]
785
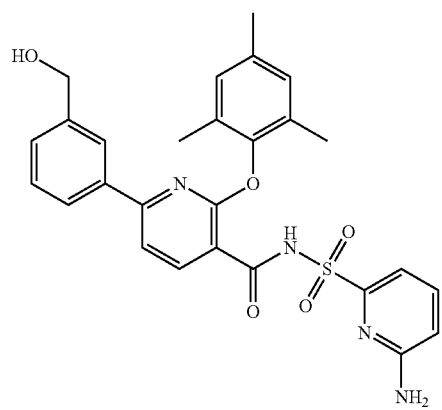 [SMILES: Cc1cc(C)c(Oc2nc(-c3cccc(CO)c3)ccc2C(=O)NS(=O)(=O)c2cccc(N)n2)c(C)c1]
786
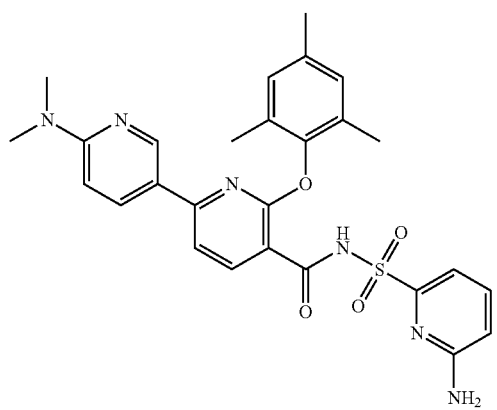
787

TABLE 1-continued
| | |
|---|---|
| 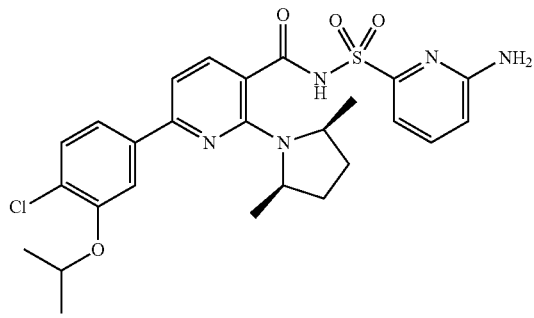 [SMILES: CC(C)Oc1cc(-c2ccc(C(=O)NS(=O)(=O)c3cccc(N)n3)c(N3[C@H](C)CC[C@@H]3C)n2)ccc1Cl] | 788 |
| 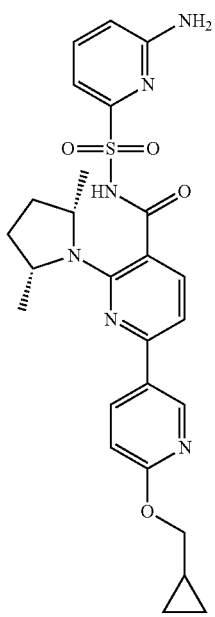 [SMILES: C[C@@H]1CC[C@H](C)N1c1nc(-c2ccc(OCC3CC3)nc2)ccc1C(=O)NS(=O)(=O)c1cccc(N)n1] | 789 |
| 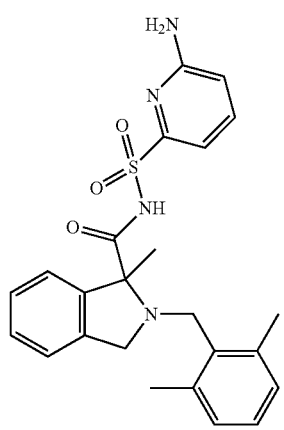 [SMILES: Cc1cccc(C)c1CN1Cc2ccccc2C1(C)C(=O)NS(=O)(=O)c1cccc(N)n1] | 790 |
| 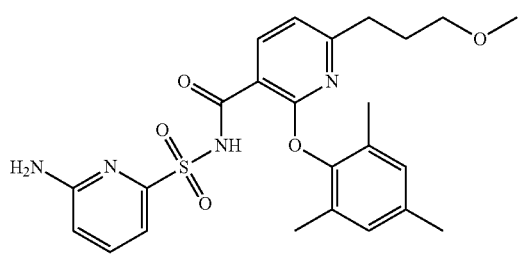 [SMILES: COCCCc1ccc(C(=O)NS(=O)(=O)c2cccc(N)n2)c(Oc2c(C)cc(C)cc2C)n1] | 791 |

TABLE 1-continued
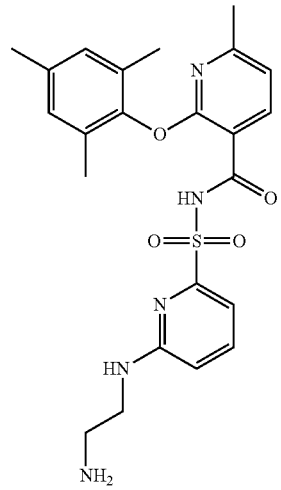 [SMILES: Cc1cc(C)c(Oc2nc(C)ccc2C(=O)NS(=O)(=O)c2cccc(NCCN)n2)c(C)c1]
792
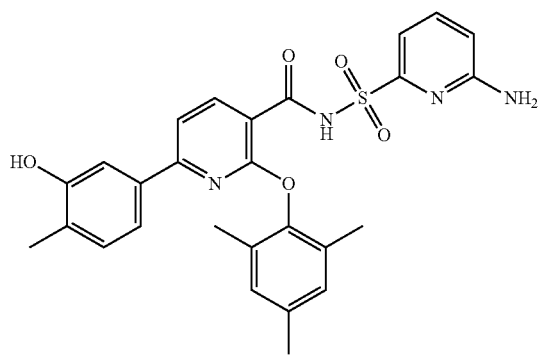 [SMILES: Cc1cc(C)c(Oc2nc(-c3ccc(C)c(O)c3)ccc2C(=O)NS(=O)(=O)c2cccc(N)n2)c(C)c1]
793
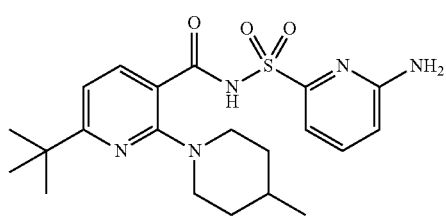 [SMILES: CC1CCN(c2nc(C(C)(C)C)ccc2C(=O)NS(=O)(=O)c2cccc(N)n2)CC1]
794
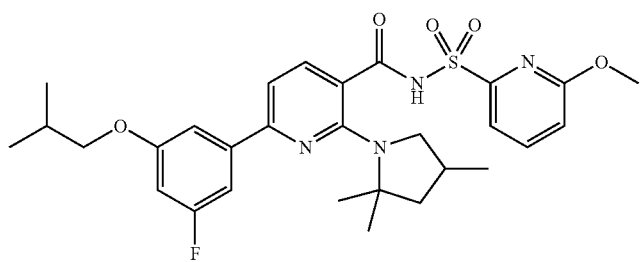 [SMILES: COc1cccc(S(=O)(=O)NC(=O)c2ccc(-c3cc(F)cc(OCC(C)C)c3)nc2N2CC(C)CC2(C)C)n1]
795

TABLE 1-continued
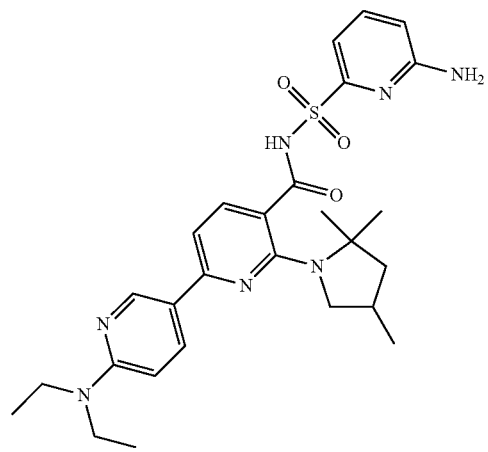 [SMILES: CCN(CC)c1ccc(-c2ccc(C(=O)NS(=O)(=O)c3cccc(N)n3)c(N3CC(C)CC3(C)C)n2)cn1] 796
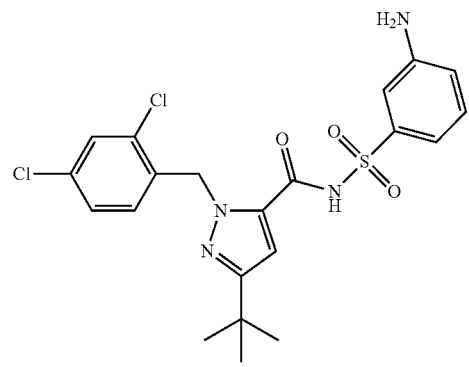 [SMILES: CC(C)(C)c1cc(C(=O)NS(=O)(=O)c2cccc(N)c2)n(Cc2ccc(Cl)cc2Cl)n1] 797
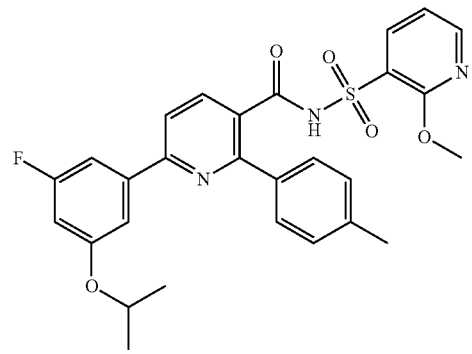 [SMILES: COc1ncccc1S(=O)(=O)NC(=O)c1ccc(-c2cc(F)cc(OC(C)C)c2)nc1-c1ccc(C)cc1] 798
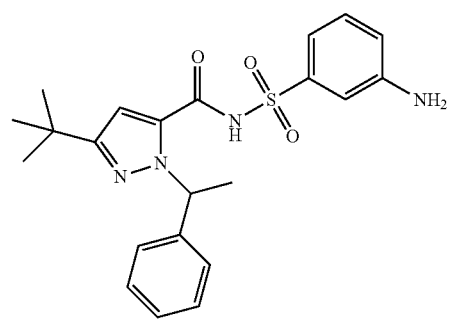 [SMILES: CC(c1ccccc1)n1nc(C(C)(C)C)cc1C(=O)NS(=O)(=O)c1cccc(N)c1] 799

TABLE 1-continued
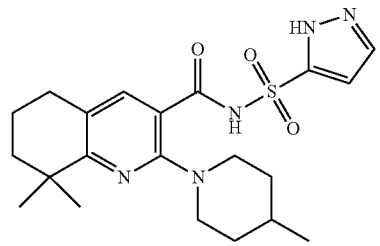 [SMILES: CC1CCN(c2nc3c(cc2C(=O)NS(=O)(=O)c2ccn[nH]2)CCCC3(C)C)CC1]
800
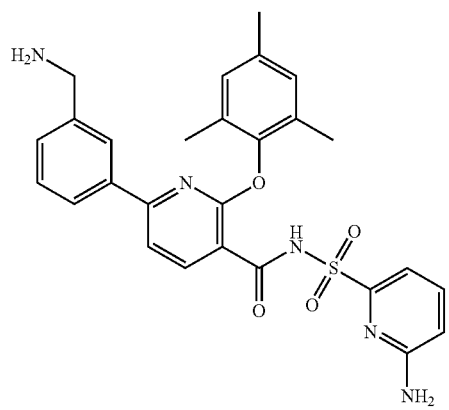 [SMILES: Cc1cc(C)c(Oc2nc(-c3cccc(CN)c3)ccc2C(=O)NS(=O)(=O)c2cccc(N)n2)c(C)c1]
801
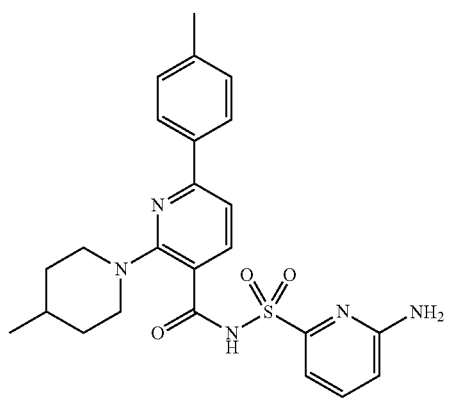 [SMILES: Cc1ccc(-c2ccc(C(=O)NS(=O)(=O)c3cccc(N)n3)c(N3CCC(C)CC3)n2)cc1]
802
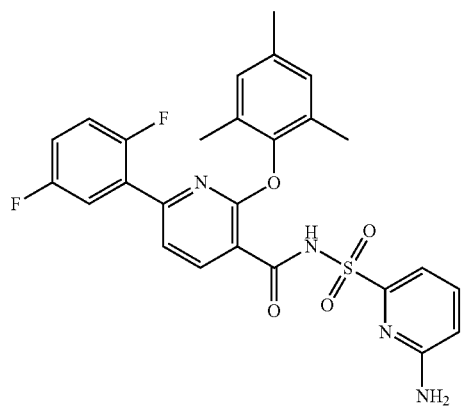 [SMILES: Cc1cc(C)c(Oc2nc(-c3cc(F)ccc3F)ccc2C(=O)NS(=O)(=O)c2cccc(N)n2)c(C)c1]
803

TABLE 1-continued

| | |
|---|---|
| [Structure] | 804 |
| [Structure] | 805 |
| [Structure] | 806 |
| [Structure] | 807 |

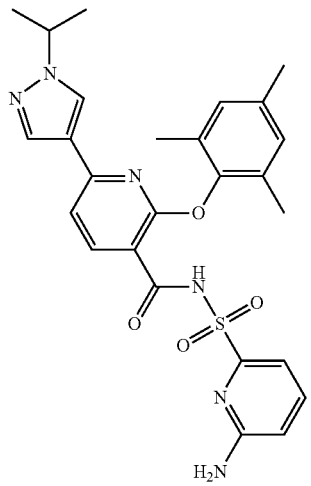 [SMILES: Cc1cc(C)c(Oc2nc(-c3cnn(C(C)C)c3)ccc2C(=O)NS(=O)(=O)c2cccc(N)n2)c(C)c1]
808
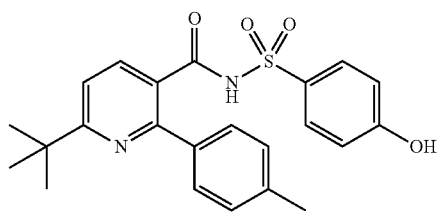 [SMILES: Cc1ccc(-c2nc(C(C)(C)C)ccc2C(=O)NS(=O)(=O)c2ccc(O)cc2)cc1]
809
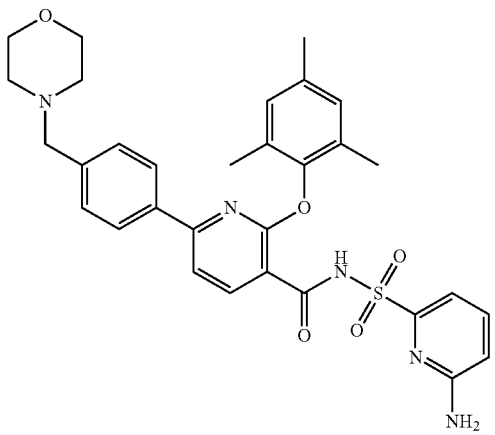 [SMILES: Cc1cc(C)c(Oc2nc(-c3ccc(CN4CCOCC4)cc3)ccc2C(=O)NS(=O)(=O)c2cccc(N)n2)c(C)c1]
810
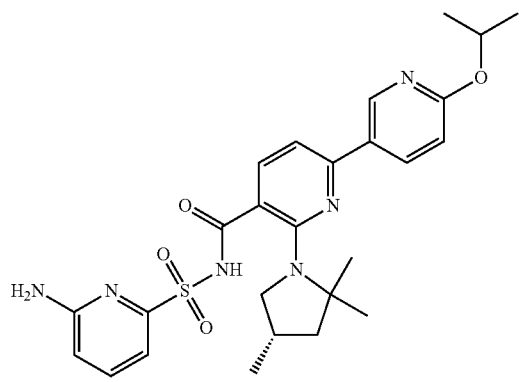 [SMILES: CC(C)Oc1ccc(-c2ccc(C(=O)NS(=O)(=O)c3cccc(N)n3)c(N3C[C@@H](C)CC3(C)C)n2)cn1]
811

TABLE 1-continued
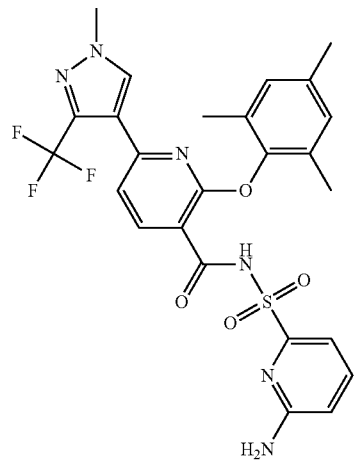 [SMILES: Cc1cc(C)c(Oc2nc(-c3cn(C)nc3C(F)(F)F)ccc2C(=O)NS(=O)(=O)c2cccc(N)n2)c(C)c1]
812
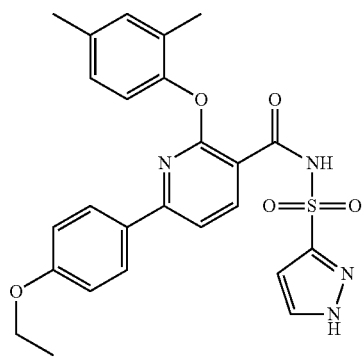 [SMILES: CCOc1ccc(-c2ccc(C(=O)NS(=O)(=O)c3cc[nH]n3)c(Oc3ccc(C)cc3C)n2)cc1]
813
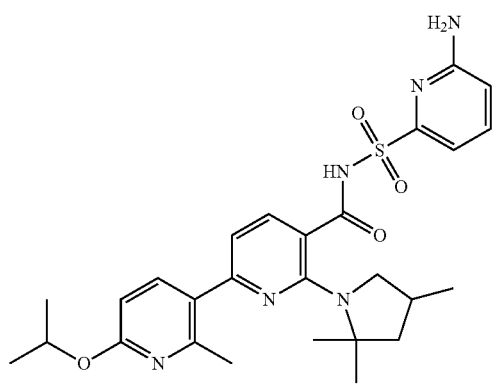 [SMILES: Cc1nc(OC(C)C)ccc1-c1ccc(C(=O)NS(=O)(=O)c2cccc(N)n2)c(N2CC(C)CC2(C)C)n1]
814
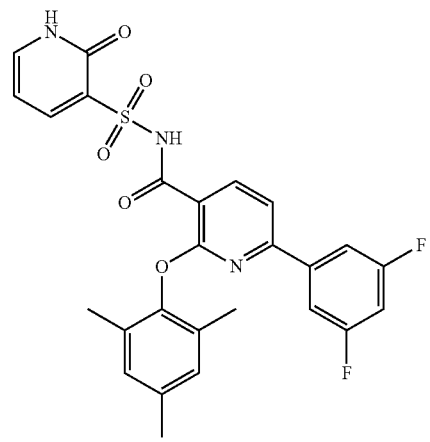 [SMILES: Cc1cc(C)c(Oc2nc(-c3cc(F)cc(F)c3)ccc2C(=O)NS(=O)(=O)c2ccc[nH]c2=O)c(C)c1]
815

TABLE 1-continued
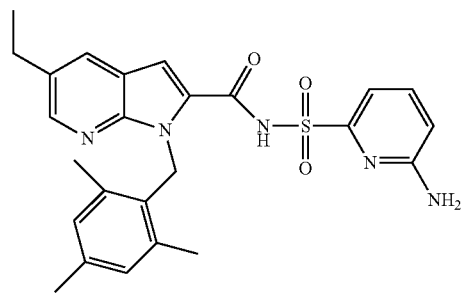 [SMILES: CCc1cnc2c(c1)cc(C(=O)NS(=O)(=O)c1cccc(N)n1)n2Cc1c(C)cc(C)cc1C]
816
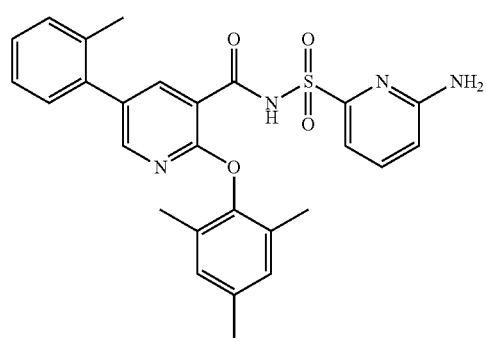 [SMILES: Cc1cc(C)c(Oc2ncc(-c3ccccc3C)cc2C(=O)NS(=O)(=O)c2cccc(N)n2)c(C)c1]
817
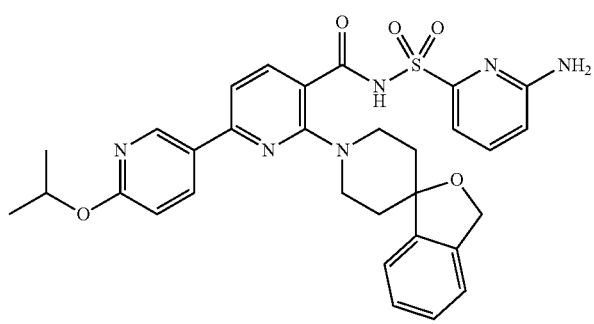 [SMILES: CC(C)Oc1ccc(-c2ccc(C(=O)NS(=O)(=O)c3cccc(N)n3)c(N3CCC4(CC3)OCc3ccccc34)n2)cn1]
818
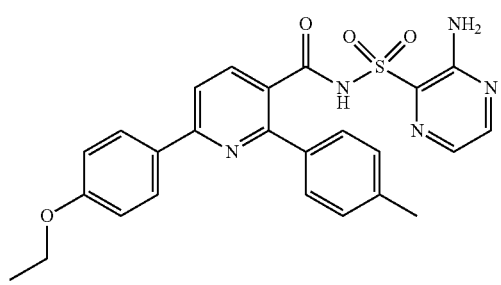 [SMILES: CCOc1ccc(-c2ccc(C(=O)NS(=O)(=O)c3nccnc3N)c(-c3ccc(C)cc3)n2)cc1]
819
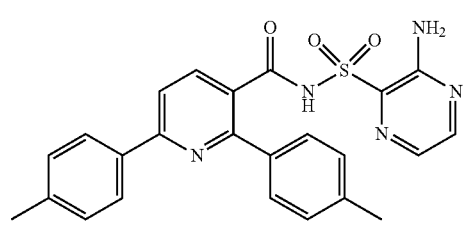 [SMILES: Cc1ccc(-c2ccc(C(=O)NS(=O)(=O)c3nccnc3N)c(-c3ccc(C)cc3)n2)cc1]
820

TABLE 1-continued
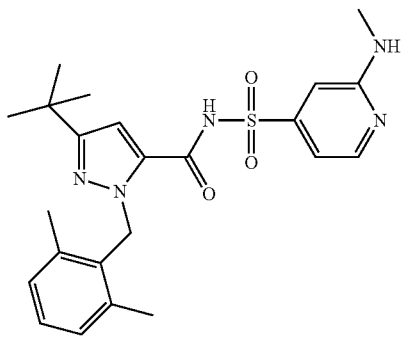 [SMILES: CNc1cc(S(=O)(=O)NC(=O)c2cc(C(C)(C)C)nn2Cc2c(C)cccc2C)ccn1] 821
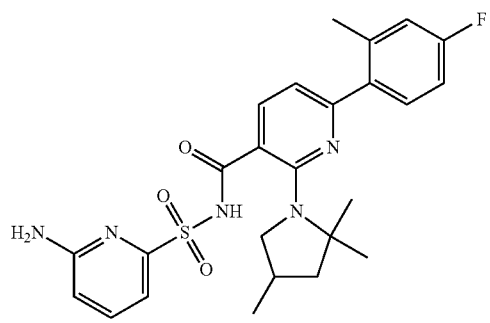 [SMILES: Cc1cc(F)ccc1-c1ccc(C(=O)NS(=O)(=O)c2cccc(N)n2)c(N2CC(C)CC2(C)C)n1] 822
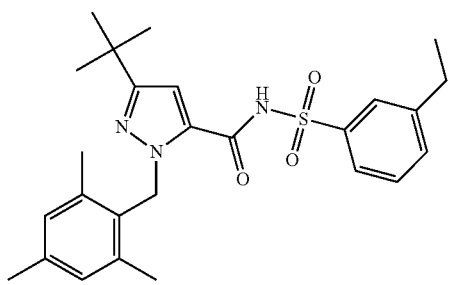 [SMILES: CCc1cccc(S(=O)(=O)NC(=O)c2cc(C(C)(C)C)nn2Cc2c(C)cc(C)cc2C)c1] 823
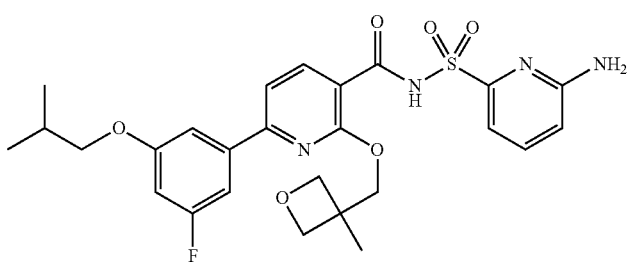 824
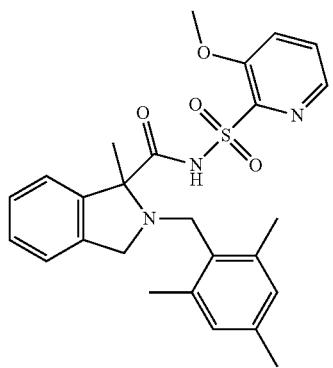 825

TABLE 1-continued
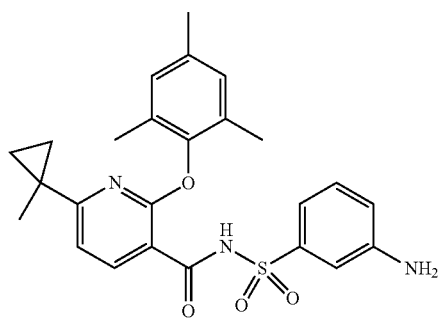
826
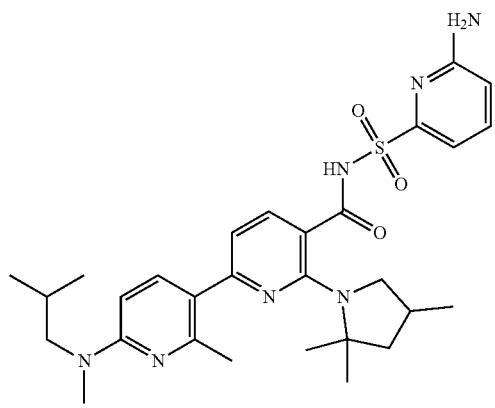 [SMILES: Cc1nc(N(C)CC(C)C)ccc1-c1ccc(C(=O)NS(=O)(=O)c2cccc(N)n2)c(N2CC(C)CC2(C)C)n1]
827
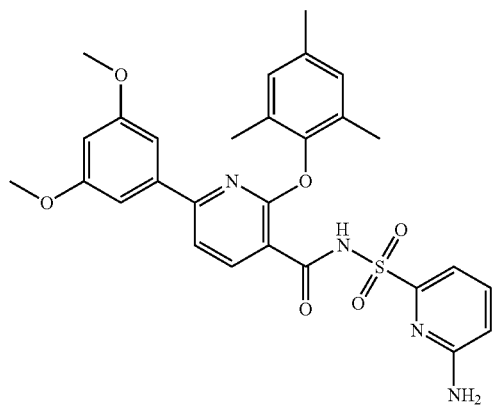
828
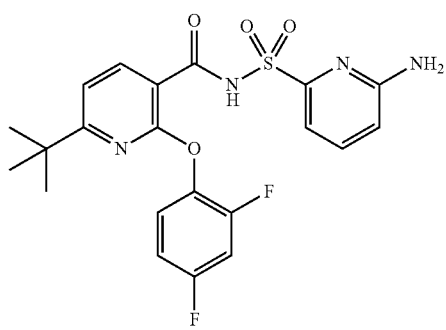
829

TABLE 1-continued
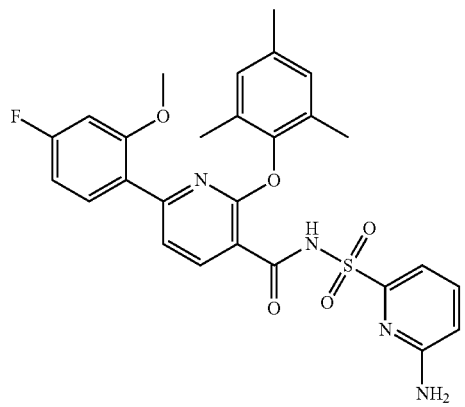
830
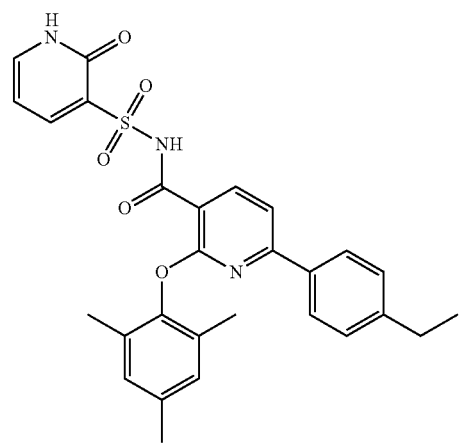
831
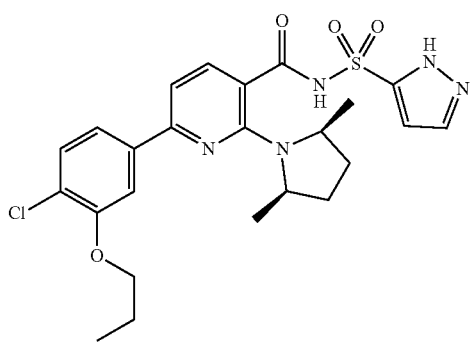
832
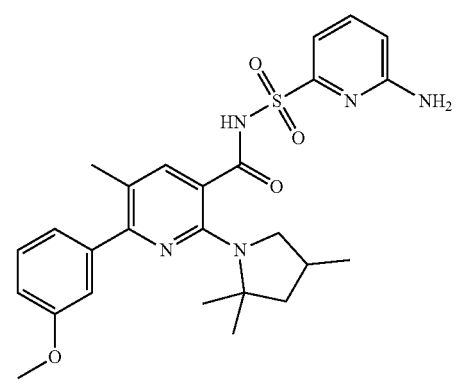 [SMILES: COc1cccc(-c2nc(N3CC(C)CC3(C)C)c(C(=O)NS(=O)(=O)c3cccc(N)n3)cc2C)c1]
833

TABLE 1-continued
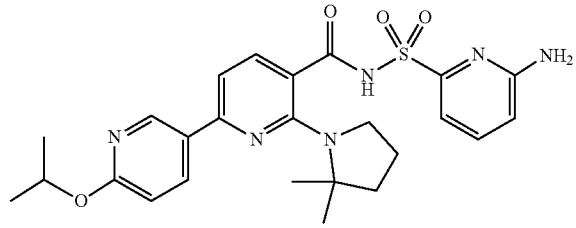
834
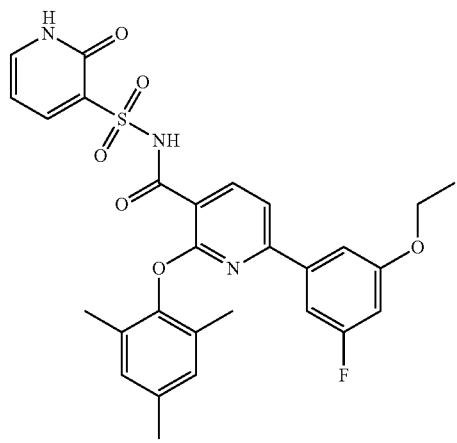
835
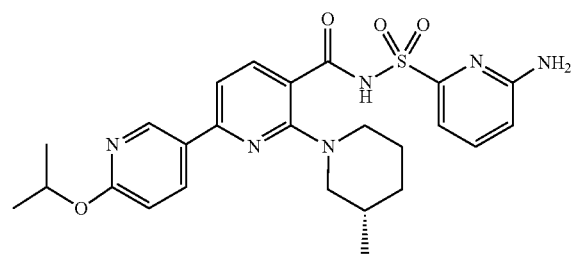
836
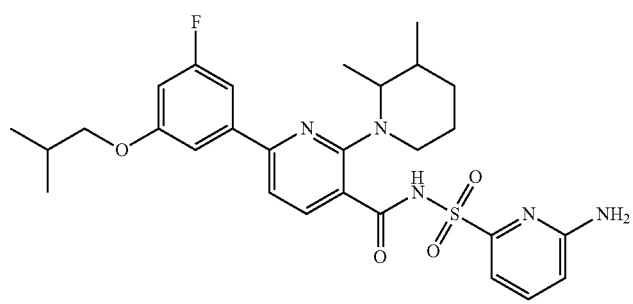
837

TABLE 1-continued
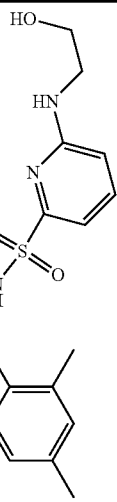 838
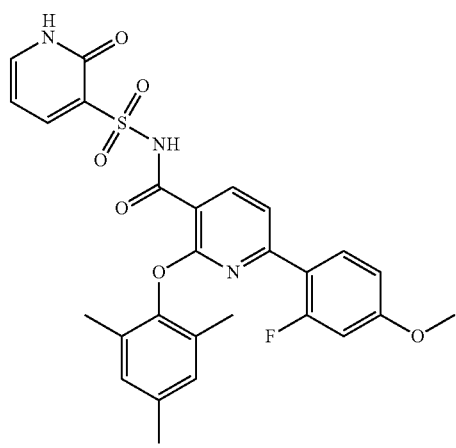 839
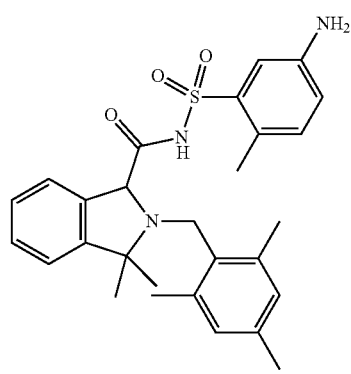 840
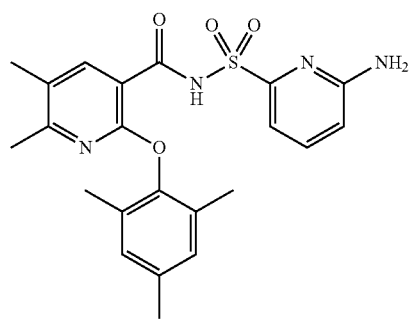 841

TABLE 1-continued
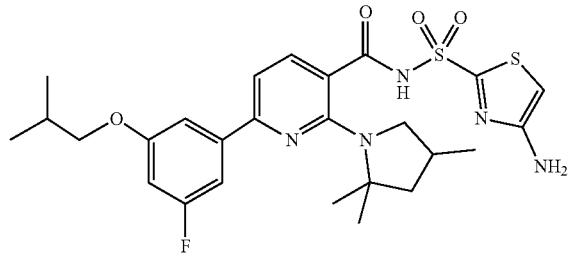
842
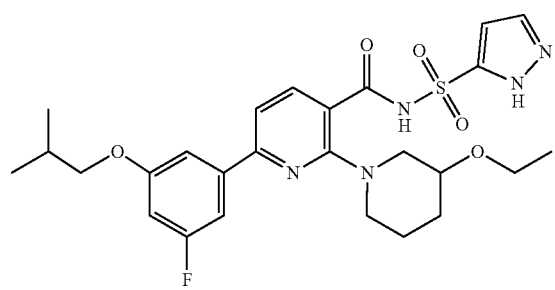
843
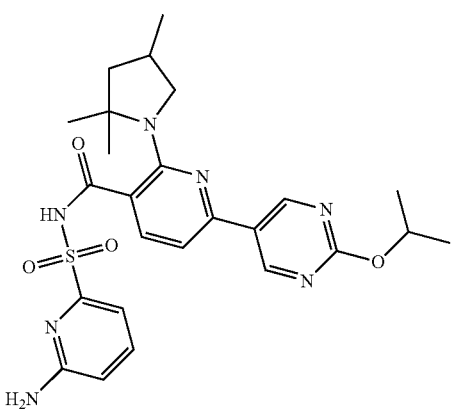 [SMILES: CC1CN(c2nc(-c3cnc(OC(C)C)nc3)ccc2C(=O)NS(=O)(=O)c2cccc(N)n2)C(C)(C)C1]
844
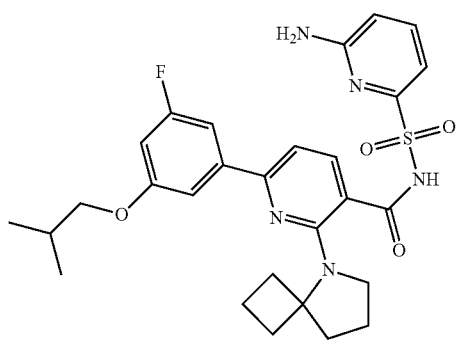 [SMILES: CC(C)COc1cc(F)cc(-c2ccc(C(=O)NS(=O)(=O)c3cccc(N)n3)c(N3CCCC34CCC4)n2)c1]
845

TABLE 1-continued
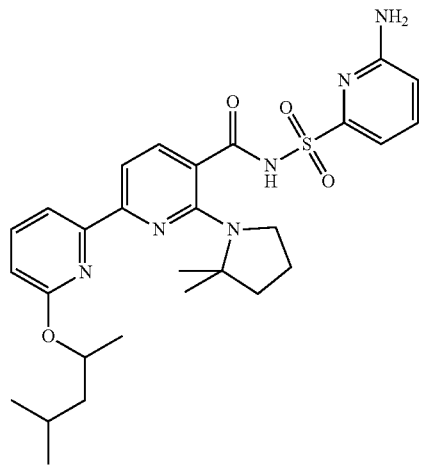
846
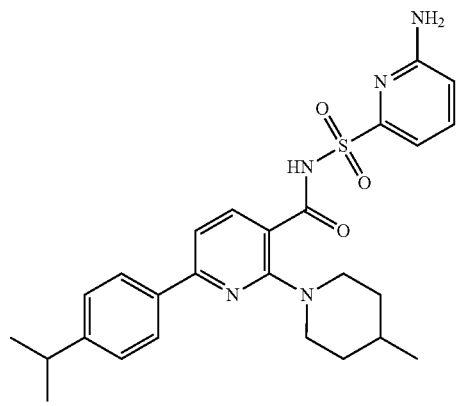 [SMILES: CC1CCN(c2nc(-c3ccc(C(C)C)cc3)ccc2C(=O)NS(=O)(=O)c2cccc(N)n2)CC1]
847
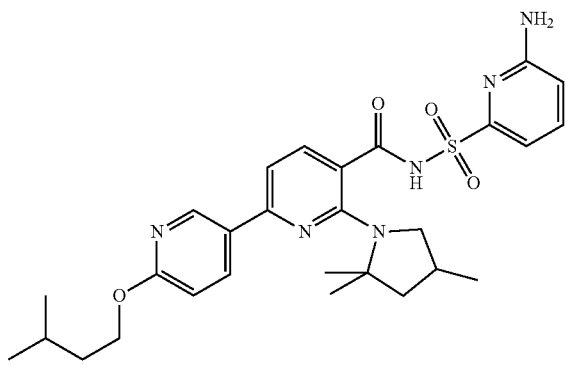
848
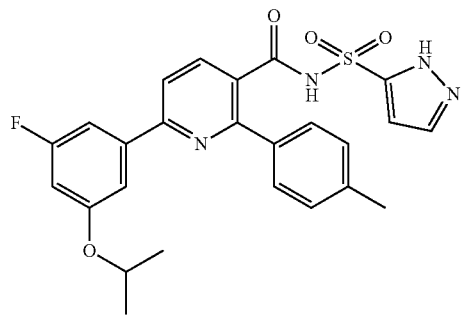
849

TABLE 1-continued
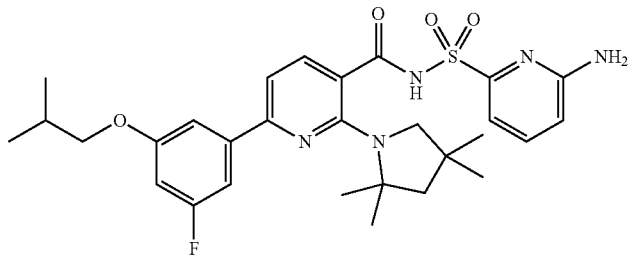
850
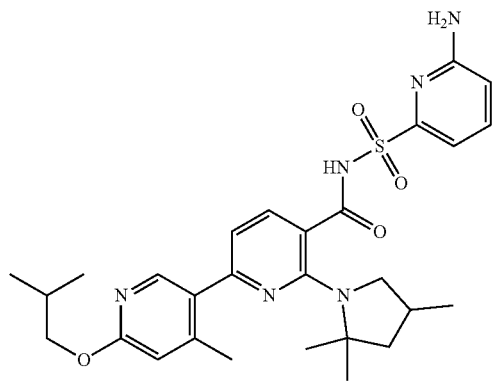 [SMILES: Cc1cc(OCC(C)C)ncc1-c1ccc(C(=O)NS(=O)(=O)c2cccc(N)n2)c(N2CC(C)CC2(C)C)n1]
851
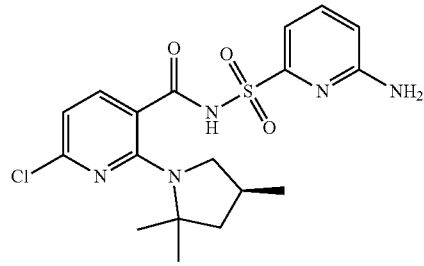
852
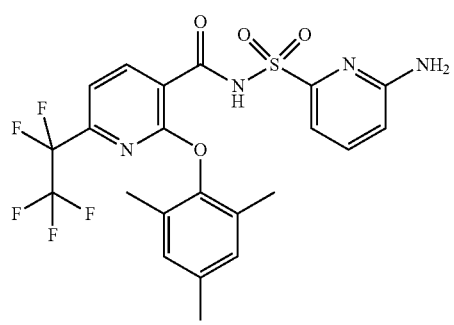
853
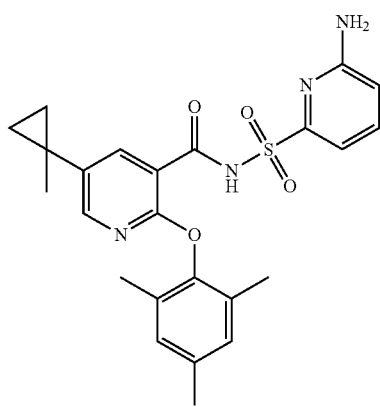
854

TABLE 1-continued
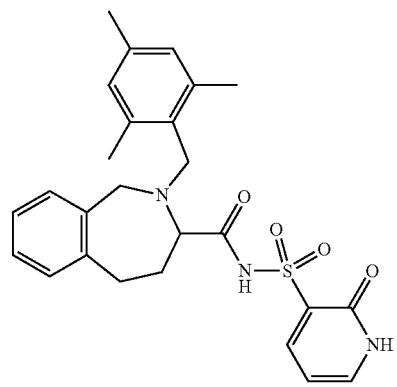 855
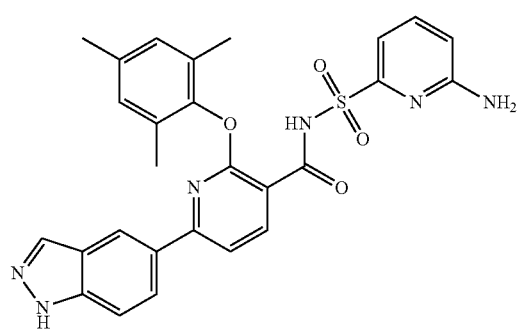 856
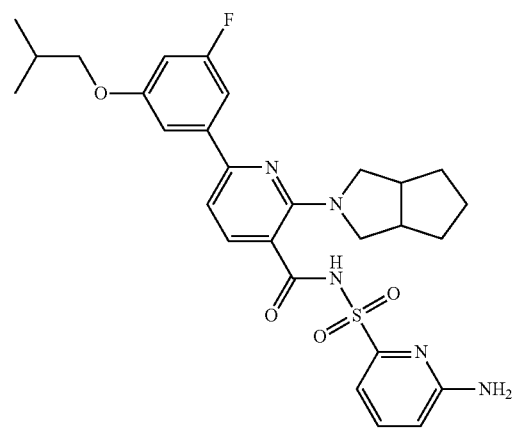 857
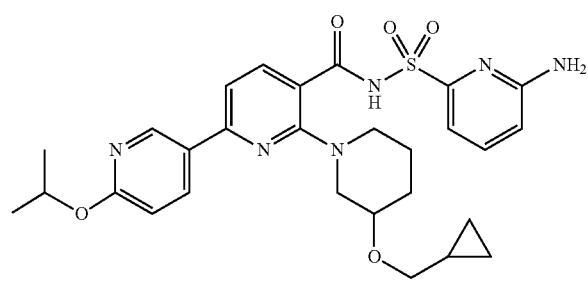 858

TABLE 1-continued
| | |
|---|---|
| 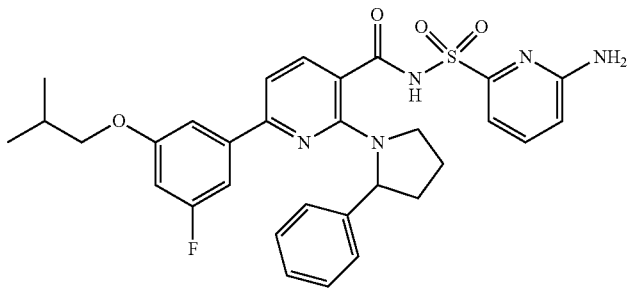 | 859 |
| 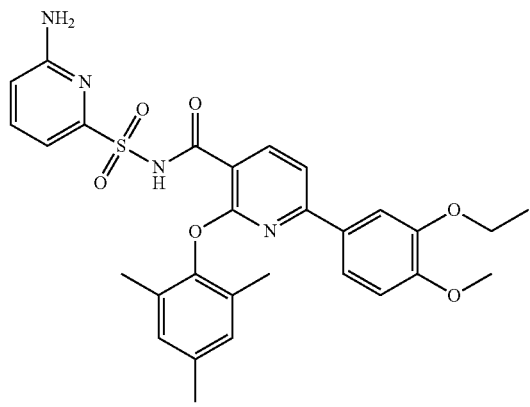 | 860 |
| 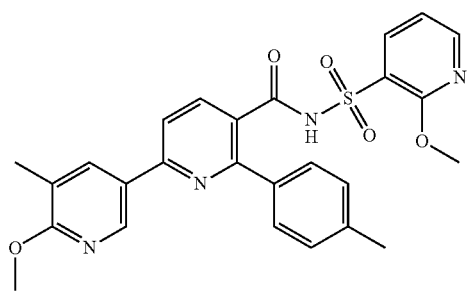 | 861 |
| 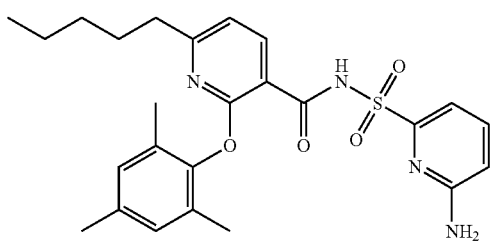 | 862 |
| 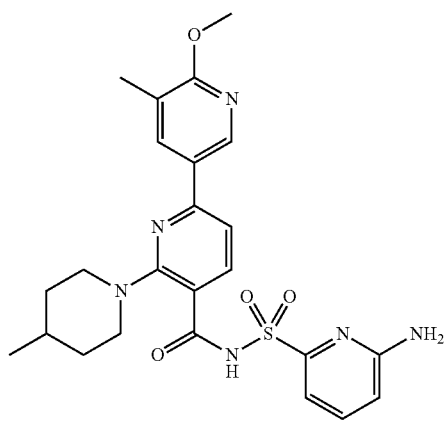 | 863 |

TABLE 1-continued
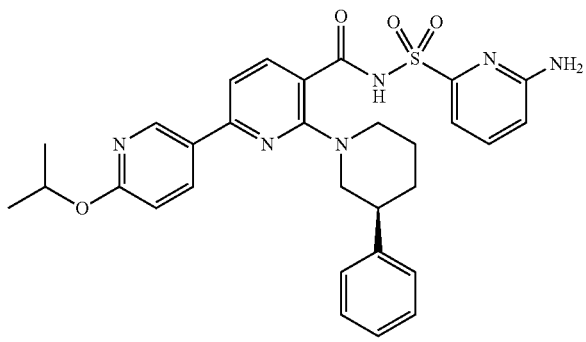
864
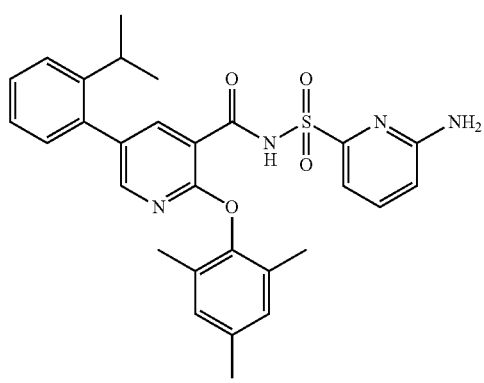
865
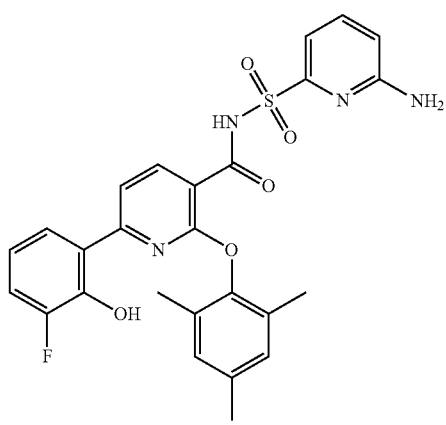 [SMILES: Cc1cc(C)c(Oc2nc(-c3cccc(F)c3O)ccc2C(=O)NS(=O)(=O)c2cccc(N)n2)c(C)c1]
866
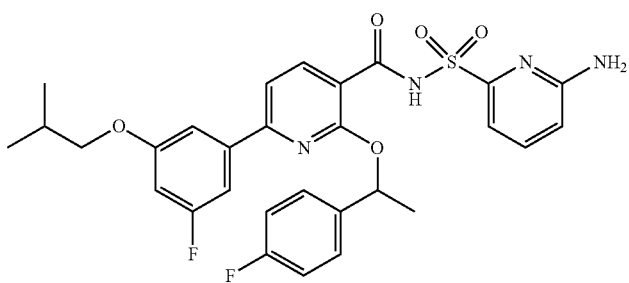
867

TABLE 1-continued
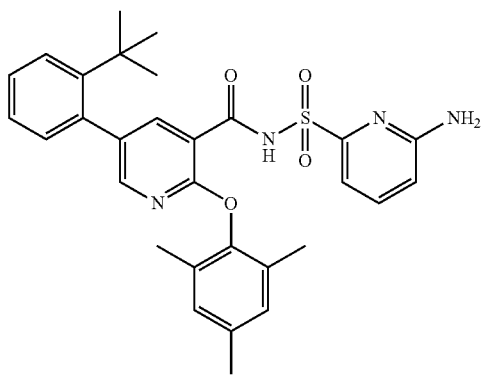
868
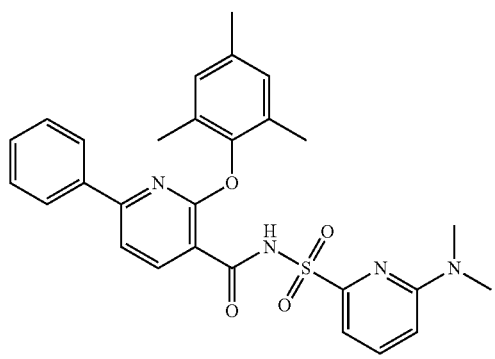
869
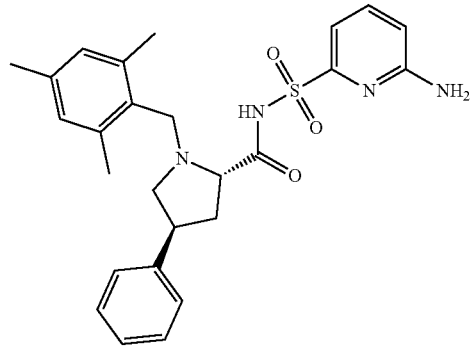 [SMILES: Cc1cc(C)c(CN2C[C@H](c3ccccc3)C[C@H]2C(=O)NS(=O)(=O)c2cccc(N)n2)c(C)c1]
870
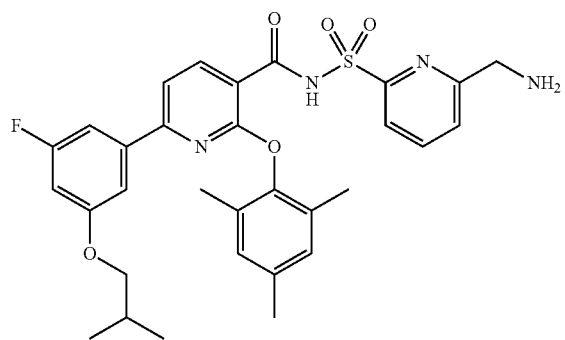
871

TABLE 1-continued
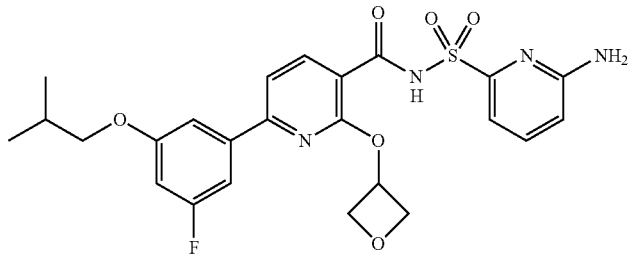
872
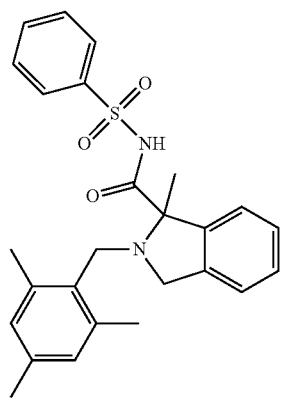 [SMILES: Cc1cc(C)c(CN2Cc3ccccc3C2(C)C(=O)NS(=O)(=O)c2ccccc2)c(C)c1]
873
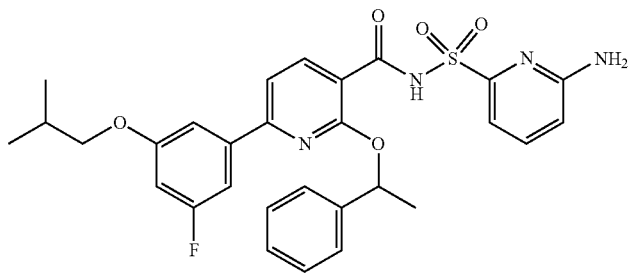
874
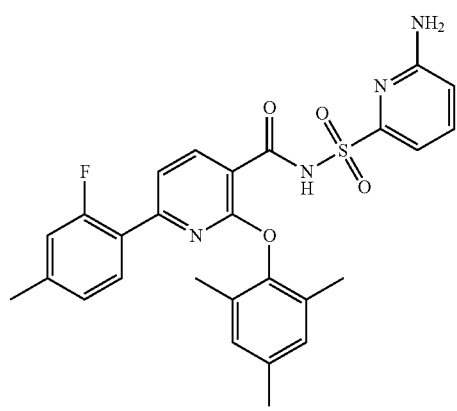
875

TABLE 1-continued
| | |
|---|---|
| 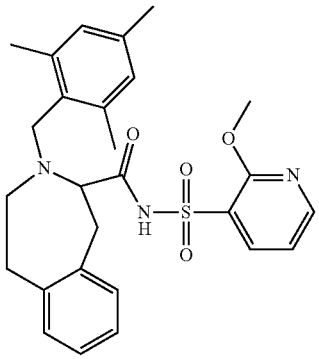 | 876 |
| 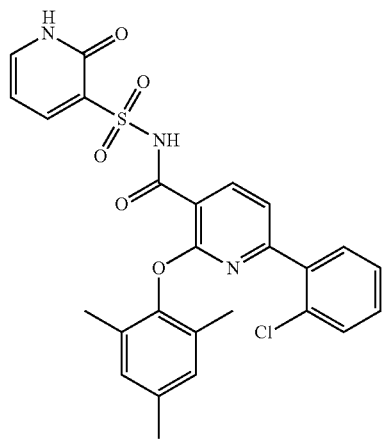 | 877 |
| 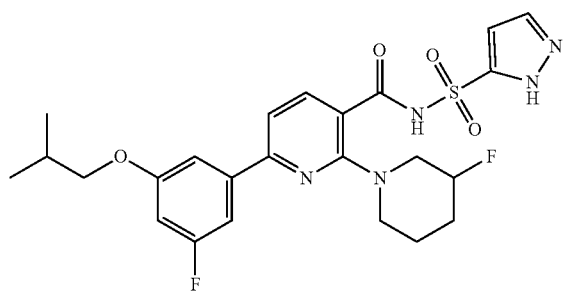 | 878 |
| 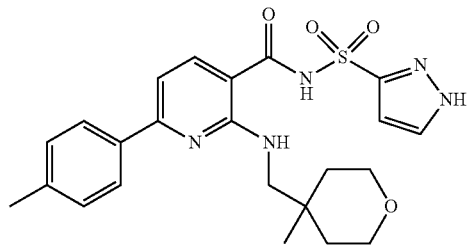 | 879 |
| 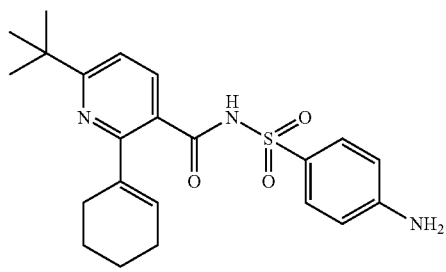 | 880 |

TABLE 1-continued
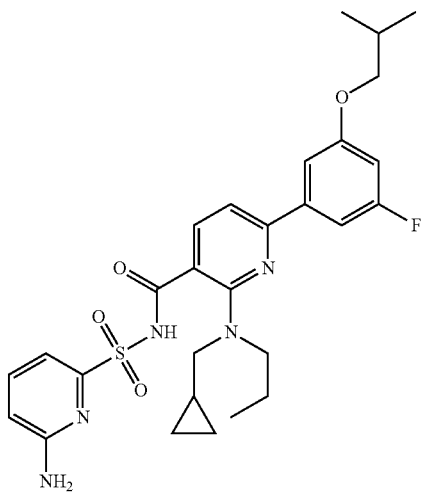 [SMILES: CCCN(CC1CC1)c1nc(-c2cc(F)cc(OCC(C)C)c2)ccc1C(=O)NS(=O)(=O)c1cccc(N)n1]
881
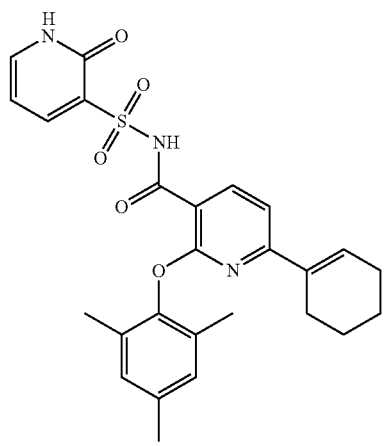
882
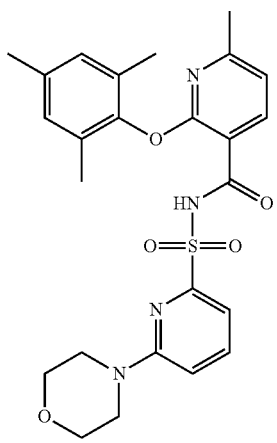 [SMILES: Cc1cc(C)c(Oc2nc(C)ccc2C(=O)NS(=O)(=O)c2cccc(N3CCOCC3)n2)c(C)c1]
883
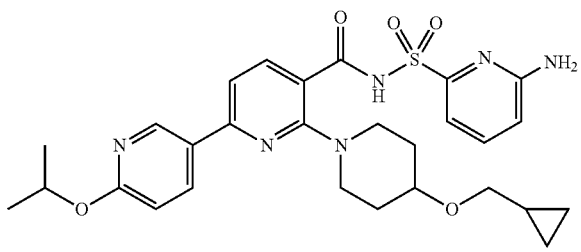
884

TABLE 1-continued
| | |
|---|---|
| 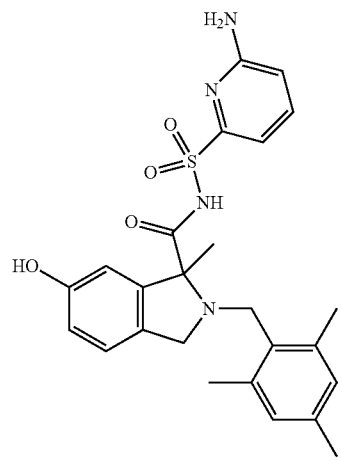 [SMILES: Cc1cc(C)c(CN2Cc3ccc(O)cc3C2(C)C(=O)NS(=O)(=O)c2cccc(N)n2)c(C)c1] | 885 |
| 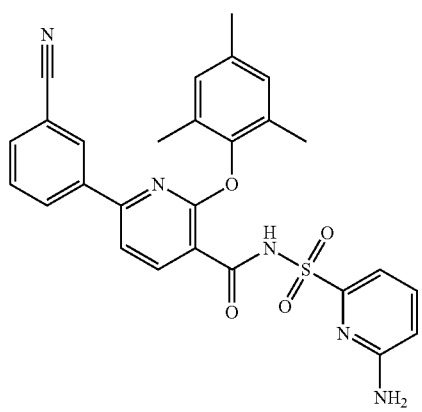 | 886 |
| 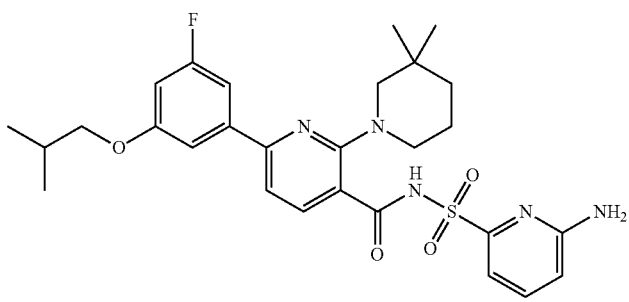 | 887 |
| 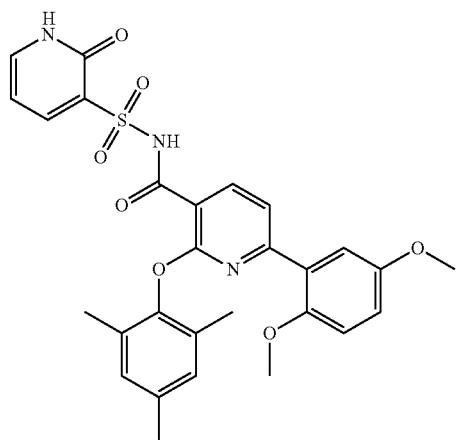 | 888 |

TABLE 1-continued
| | |
|---|---|
| 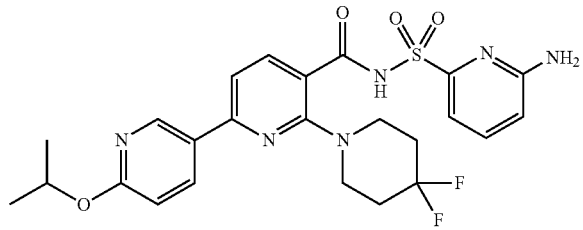 | 889 |
| 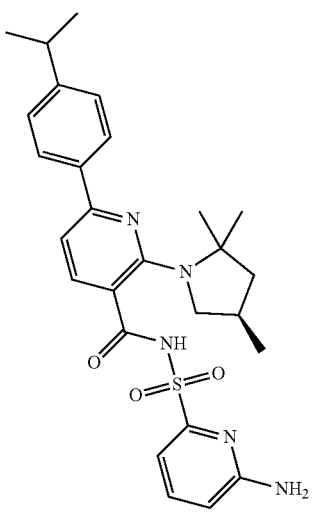 [SMILES: CC(C)c1ccc(-c2ccc(C(=O)NS(=O)(=O)c3cccc(N)n3)c(N3C[C@H](C)CC3(C)C)n2)cc1] | 890 |
| 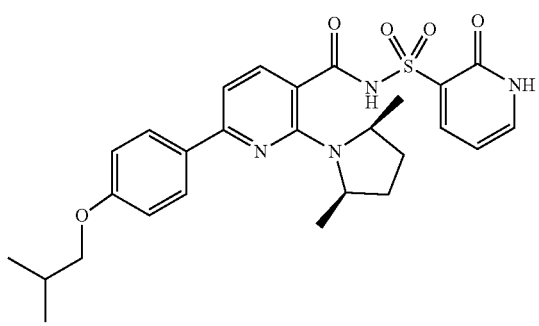 | 891 |
| 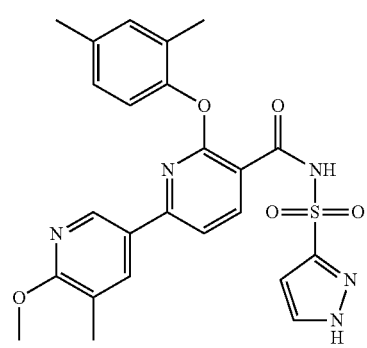 | 892 |

TABLE 1-continued
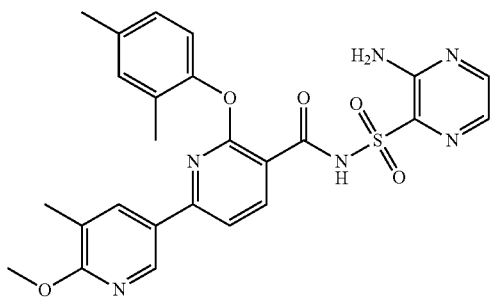 893
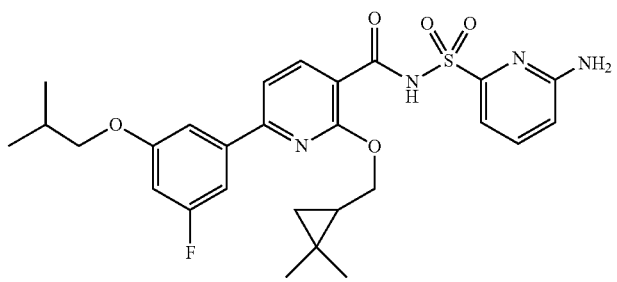 894
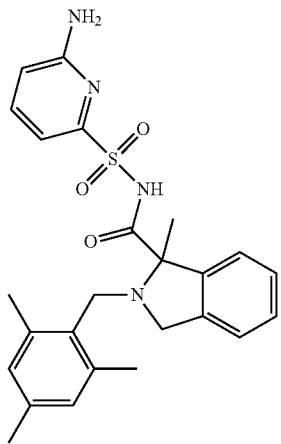 895
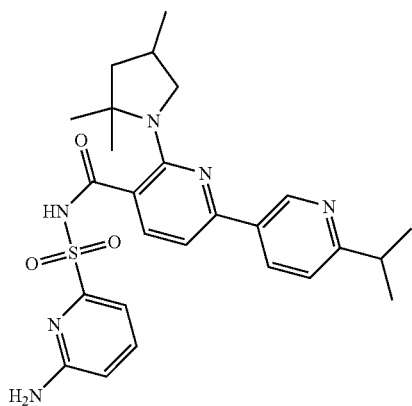 [SMILES: CC1CN(c2nc(-c3ccc(C(C)C)nc3)ccc2C(=O)NS(=O)(=O)c2cccc(N)n2)C(C)(C)C1] 896

TABLE 1-continued
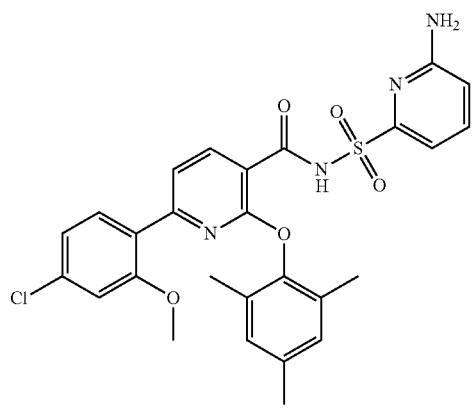
897
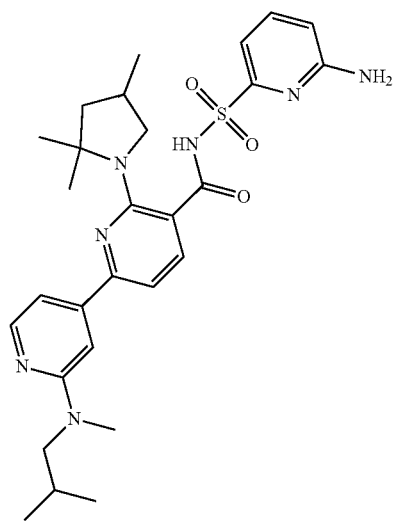
898
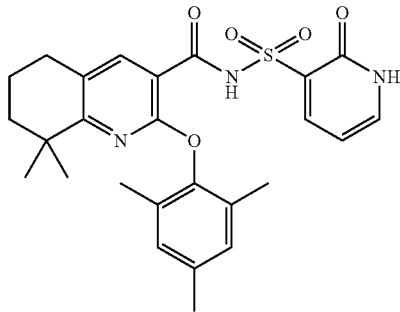
899
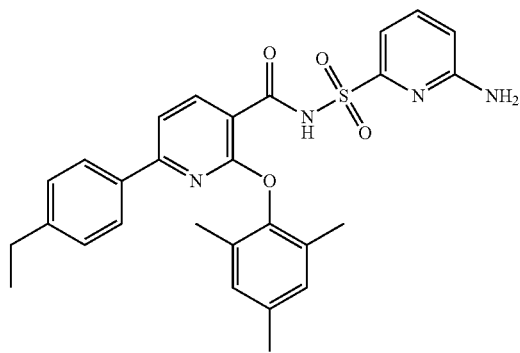
900

TABLE 1-continued
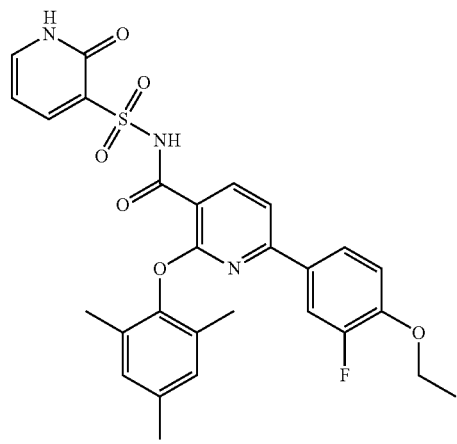
901
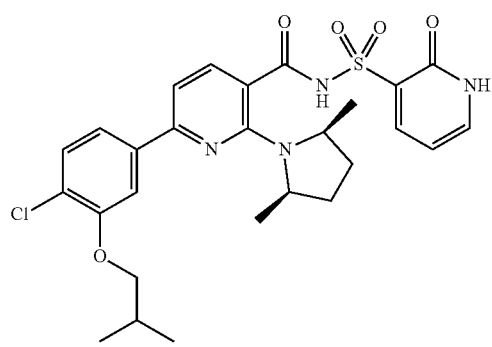
902
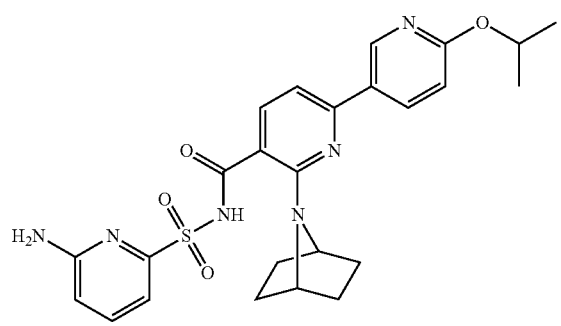 [SMILES: CC(C)Oc1ccc(-c2ccc(C(=O)NS(=O)(=O)c3cccc(N)n3)c(N3C4CCC3CC4)n2)cn1]
903
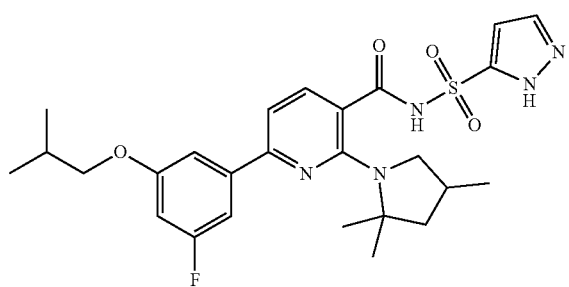
904

TABLE 1-continued
| | |
|---|---|
| 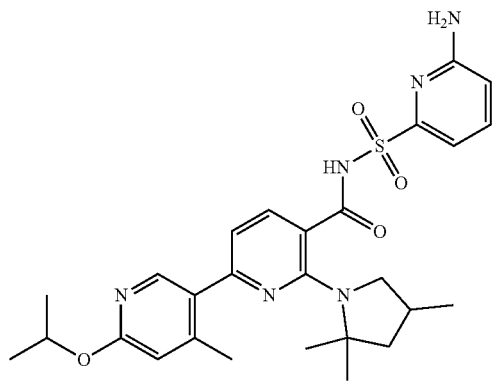 [SMILES: Cc1cc(OC(C)C)ncc1-c1ccc(C(=O)NS(=O)(=O)c2cccc(N)n2)c(N2CC(C)CC2(C)C)n1] | 905 |
| 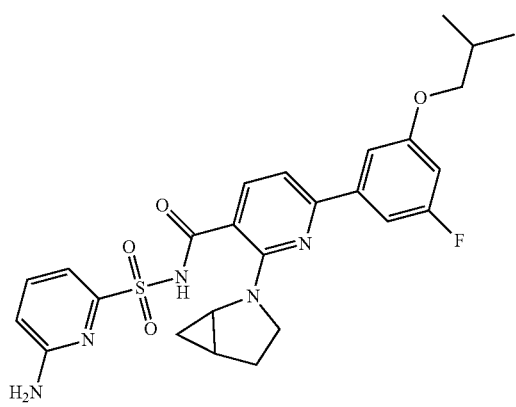 | 906 |
| 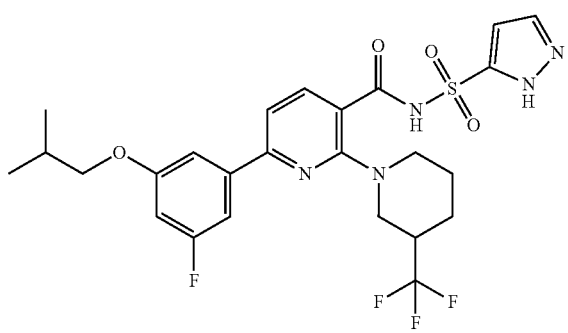 | 907 |
| 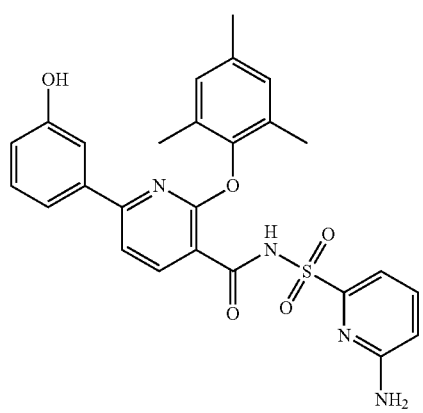 | 908 |

TABLE 1-continued
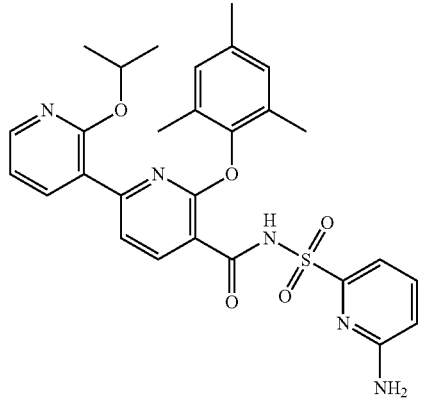
909
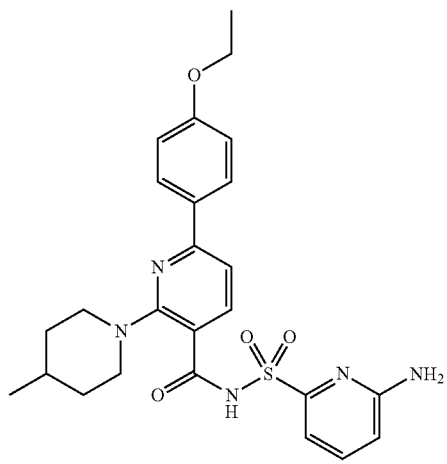
910
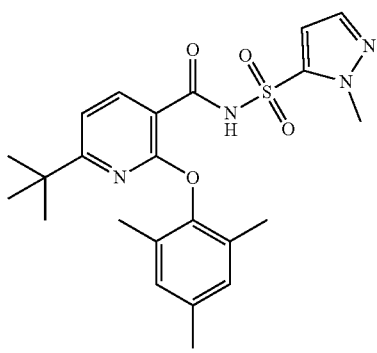
911
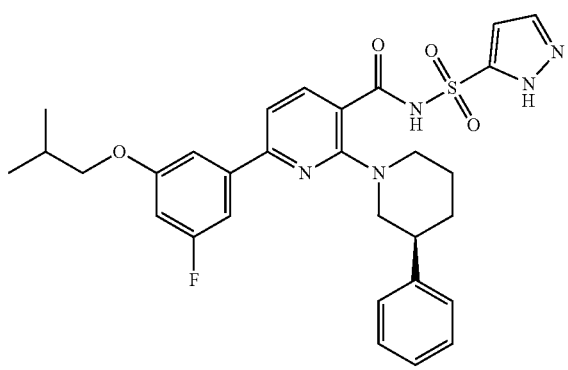
912

TABLE 1-continued
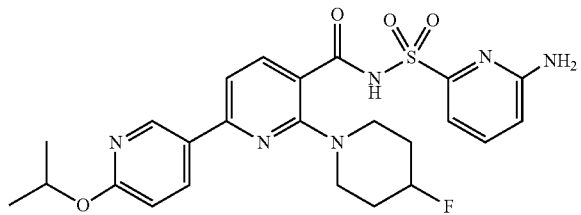
913
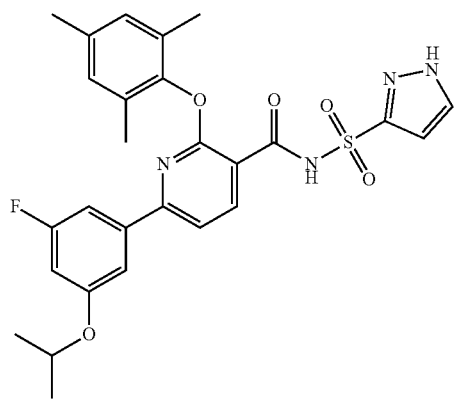
914
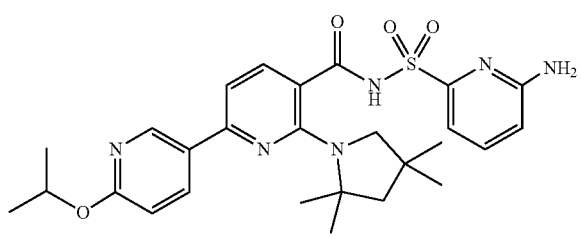
915
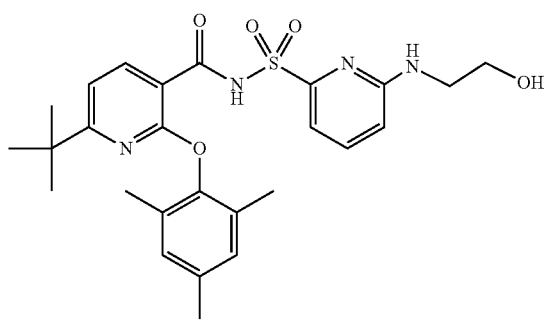
916
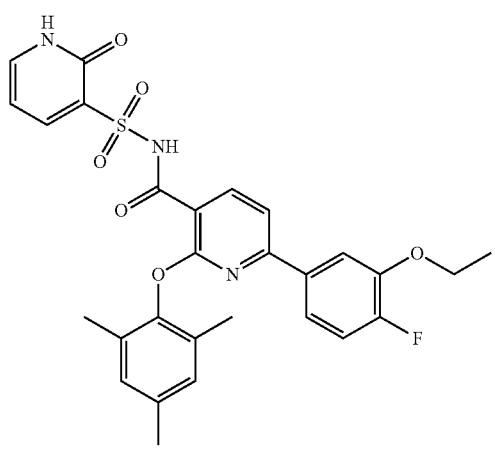
917

TABLE 1-continued
| | |
|---|---|
| 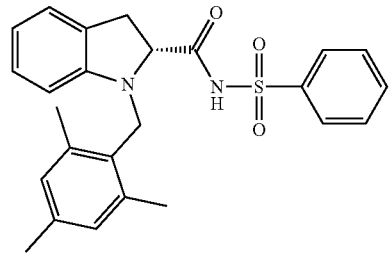 | 918 |
| 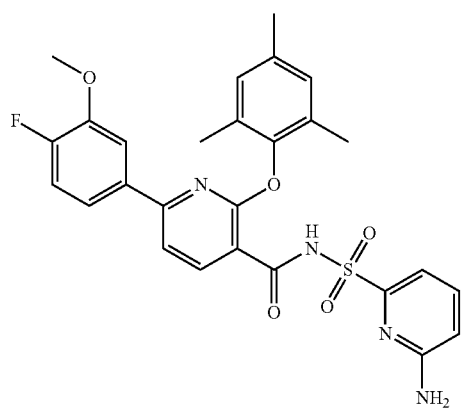 | 919 |
| 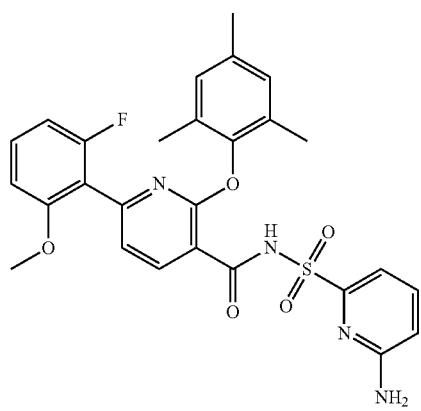 | 920 |
| 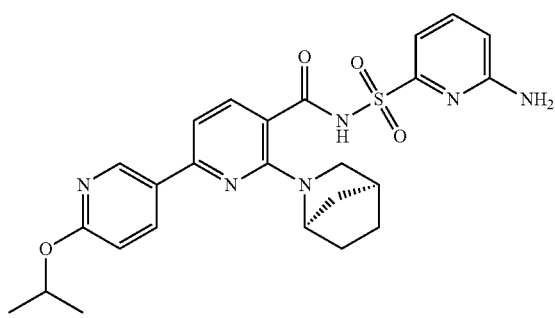 | 921 |

TABLE 1-continued
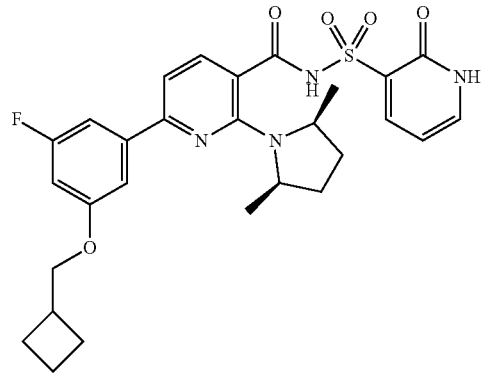 922
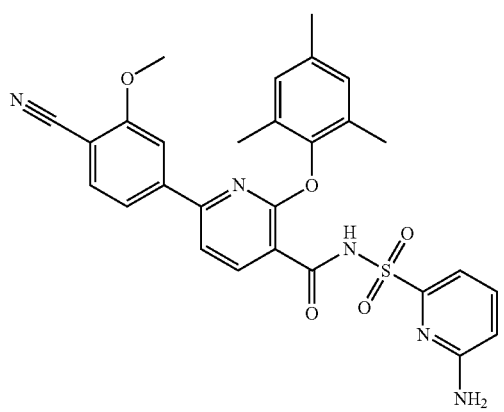 923
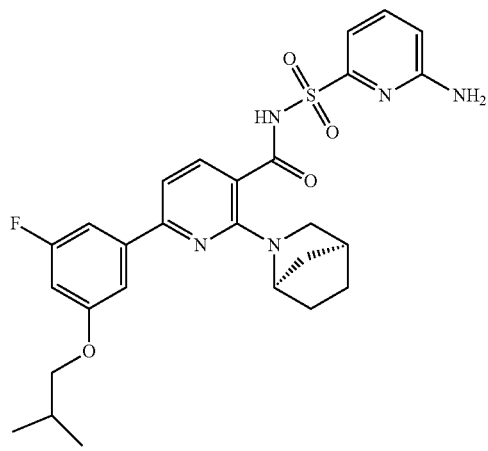 [SMILES: CC(C)COc1cc(F)cc(-c2ccc(C(=O)NS(=O)(=O)c3cccc(N)n3)c(N3C[C@H]4CC[C@@H]3C4)n2)c1] 924
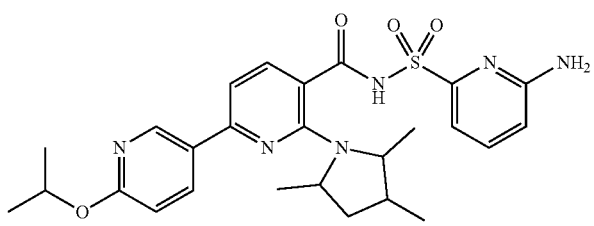 925

TABLE 1-continued
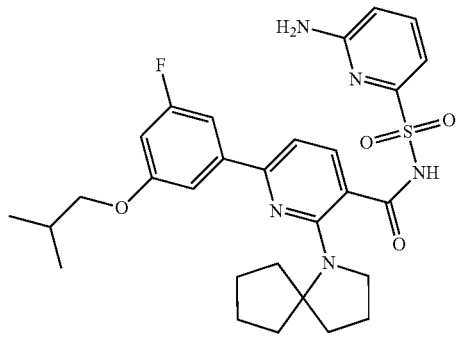 [SMILES: CC(C)COc1cc(F)cc(-c2ccc(C(=O)NS(=O)(=O)c3cccc(N)n3)c(N3CCCC34CCCC4)n2)c1]
926
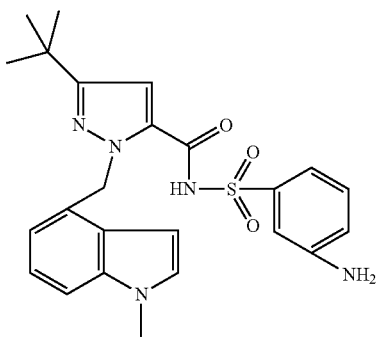 [SMILES: Cn1ccc2c(Cn3nc(C(C)(C)C)cc3C(=O)NS(=O)(=O)c3cccc(N)c3)cccc21]
927
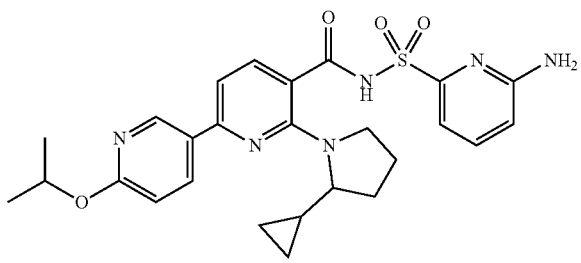
928
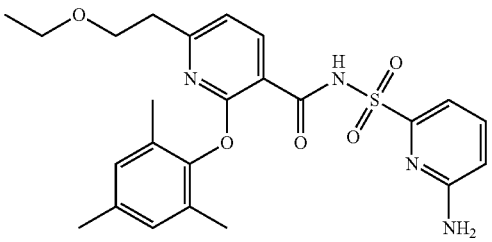
929
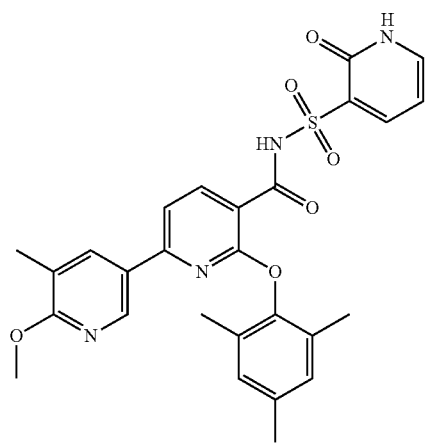
930

TABLE 1-continued

931

932

933

TABLE 1-continued
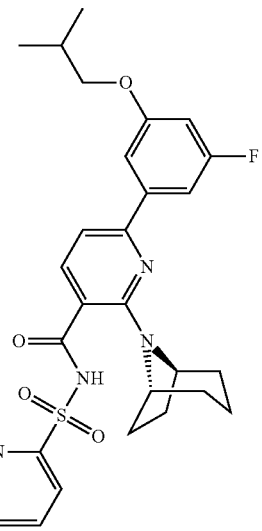
934
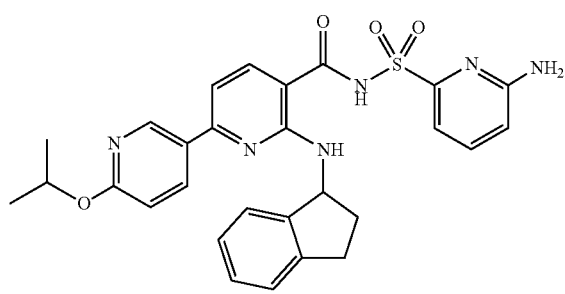
935
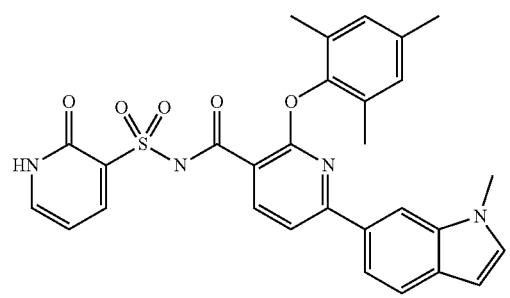 [SMILES: Cc1cc(C)c(Oc2nc(-c3ccc4ccn(C)c4c3)ccc2C(=O)NS(=O)(=O)c2ccc[nH]c2=O)c(C)c1]
936
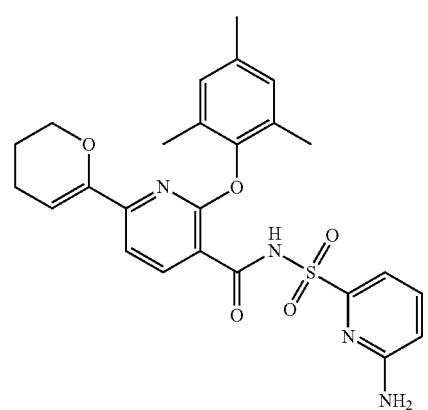
937

TABLE 1-continued
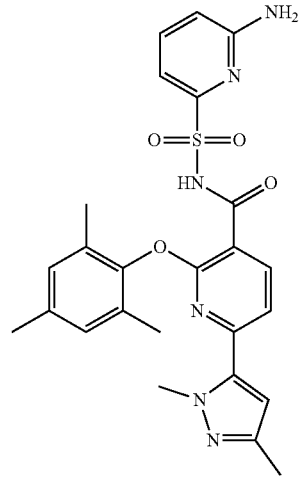
938
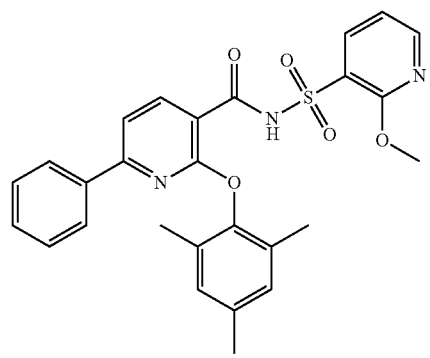
939
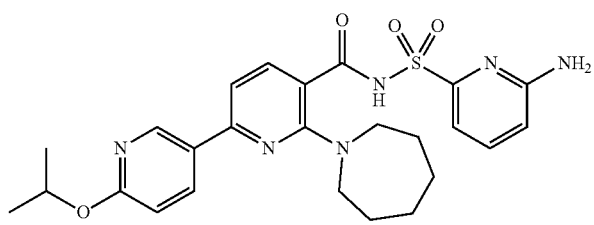
940
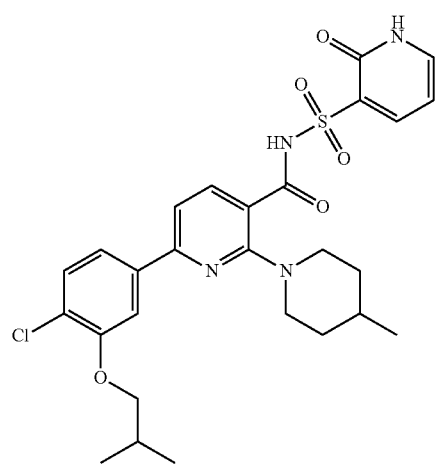
941

TABLE 1-continued
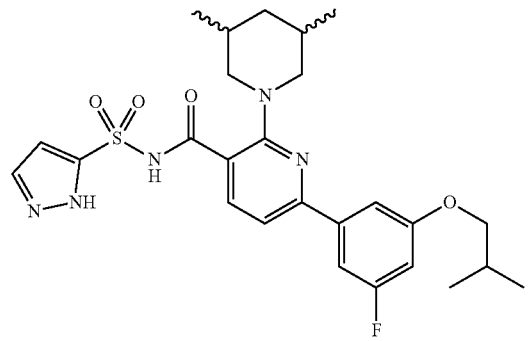
942
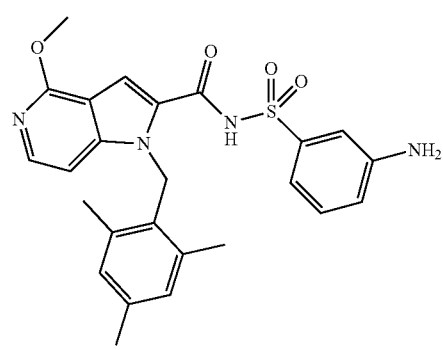
943
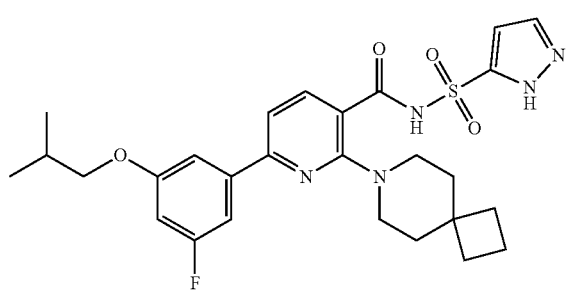
944
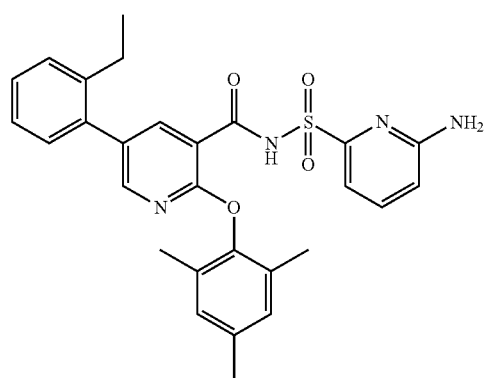
945

TABLE 1-continued
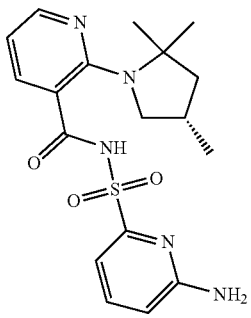 [SMILES: C[C@@H]1CN(c2ncccc2C(=O)NS(=O)(=O)c2cccc(N)n2)C(C)(C)C1]
946
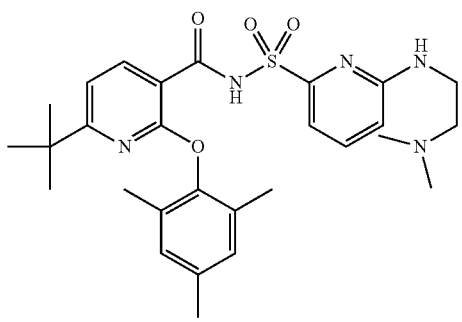
947
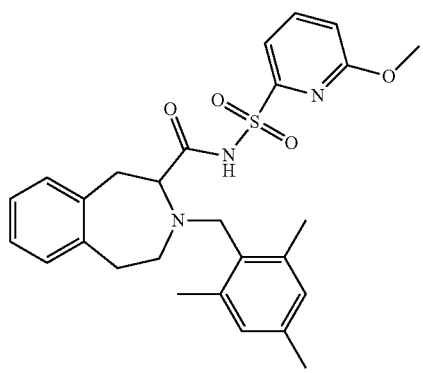
948
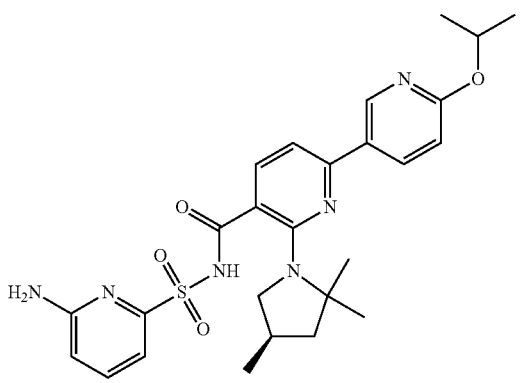 [SMILES: CC(C)Oc1ccc(-c2ccc(C(=O)NS(=O)(=O)c3cccc(N)n3)c(N3C[C@H](C)CC3(C)C)n2)cn1]
949

TABLE 1-continued
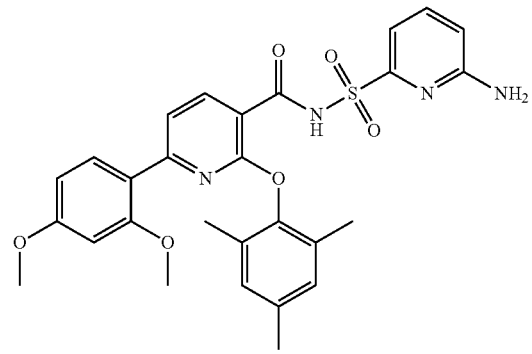
950
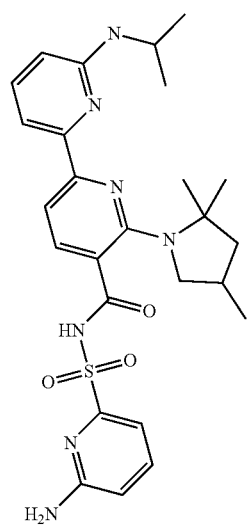 [SMILES: CC1CN(c2nc(-c3cccc(NC(C)C)n3)ccc2C(=O)NS(=O)(=O)c2cccc(N)n2)C(C)(C)C1]
951
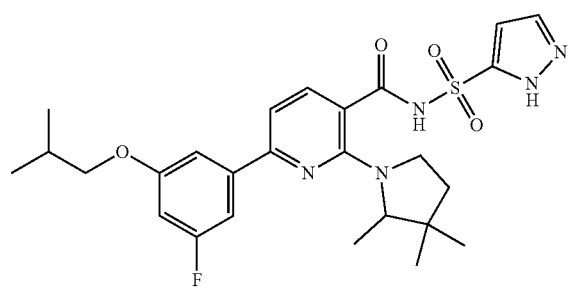
952

TABLE 1-continued
953
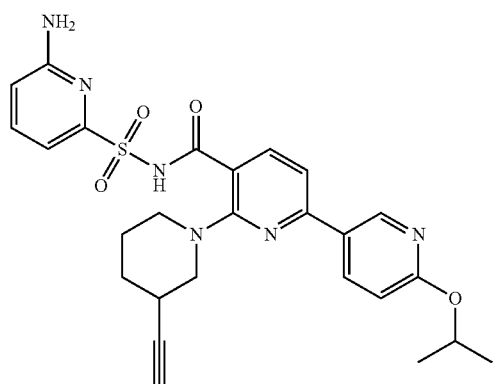
954
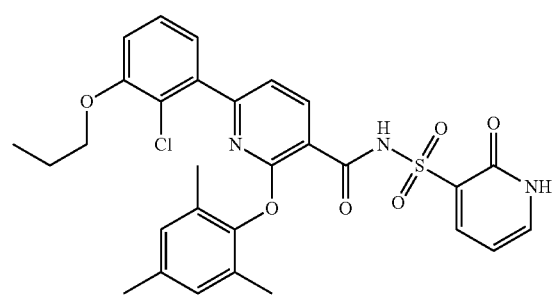
955

TABLE 1-continued
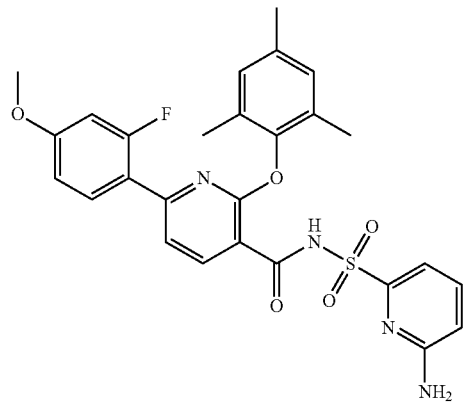
956
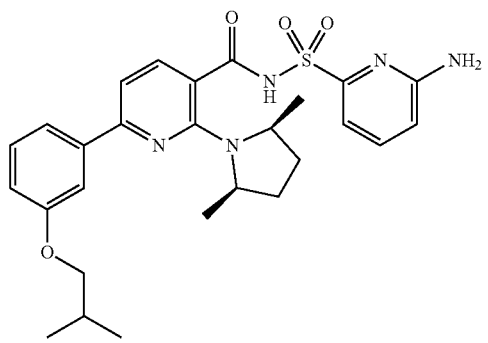
957
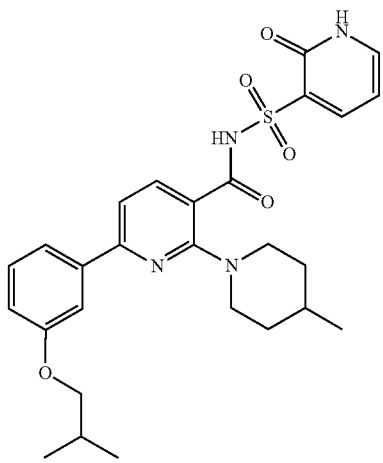 [SMILES: CC(C)COc1cccc(-c2ccc(C(=O)NS(=O)(=O)c3ccc[nH]c3=O)c(N3CCC(C)CC3)n2)c1]
958
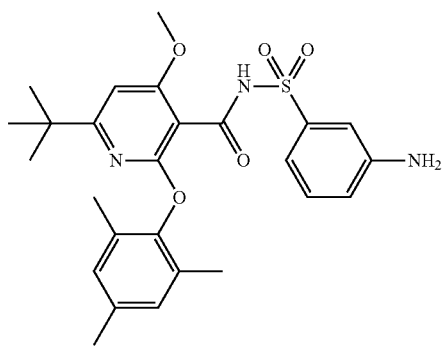
959

TABLE 1-continued
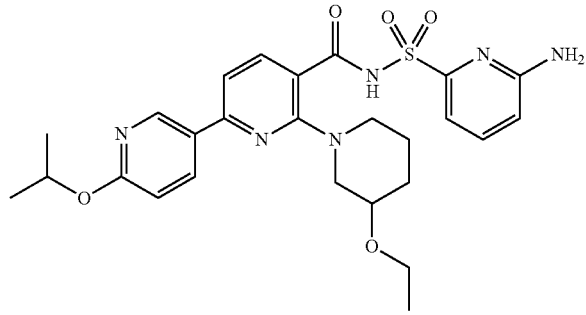 960
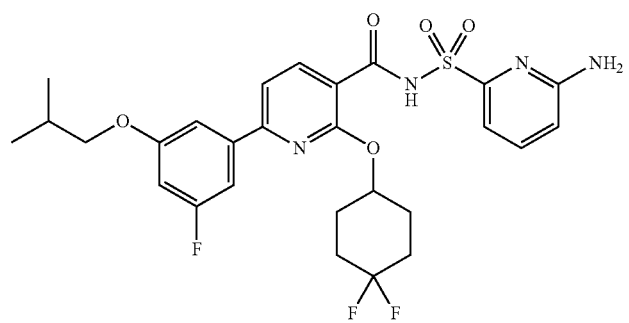 961
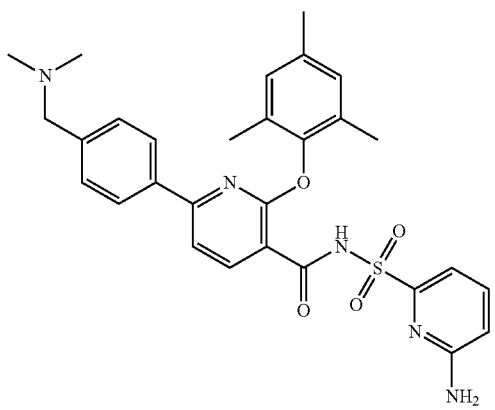 962
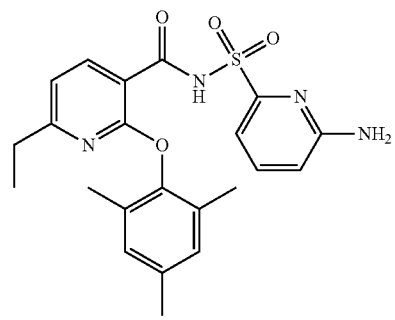 963

TABLE 1-continued
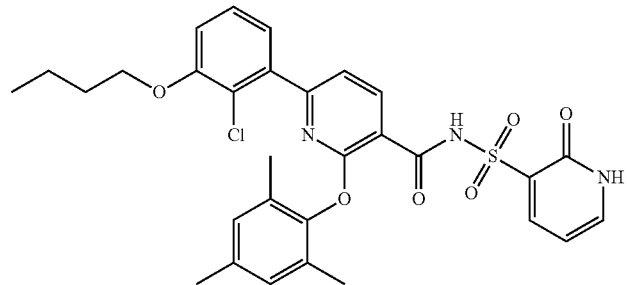
964
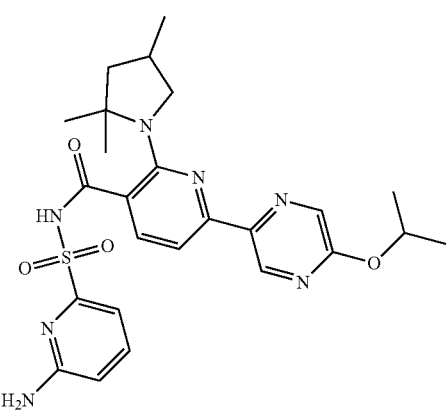 [SMILES: CC1CN(c2nc(-c3cnc(OC(C)C)cn3)ccc2C(=O)NS(=O)(=O)c2cccc(N)n2)C(C)(C)C1]
965
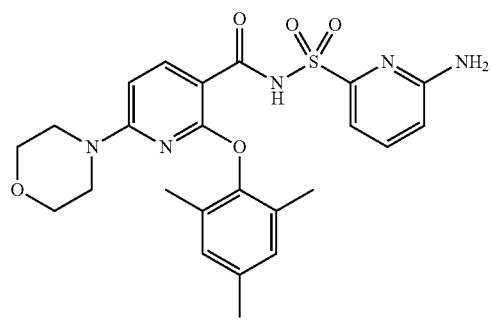
966
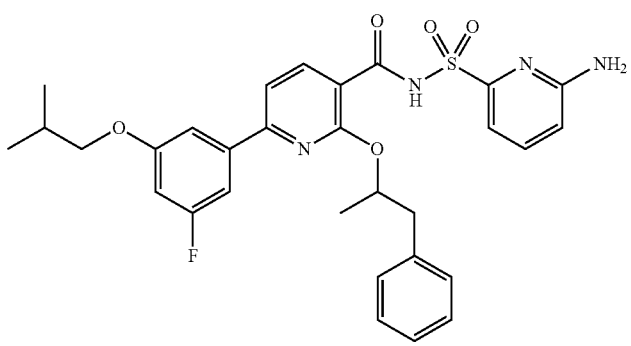
967

TABLE 1-continued
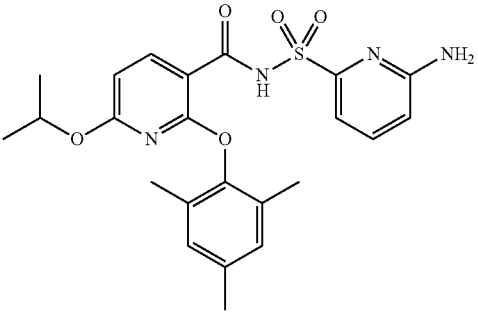
968
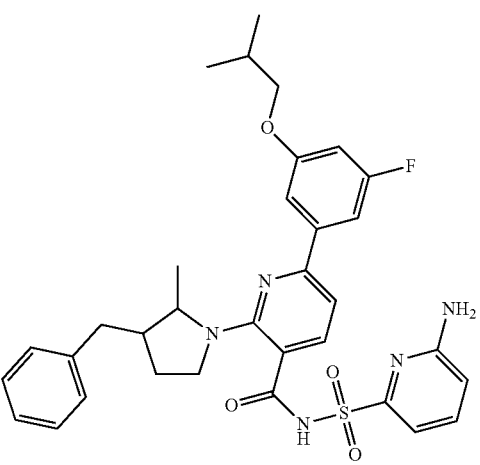 [SMILES: CC(C)COc1cc(F)cc(-c2ccc(C(=O)NS(=O)(=O)c3cccc(N)n3)c(N3CCC(Cc4ccccc4)C3C)n2)c1]
969
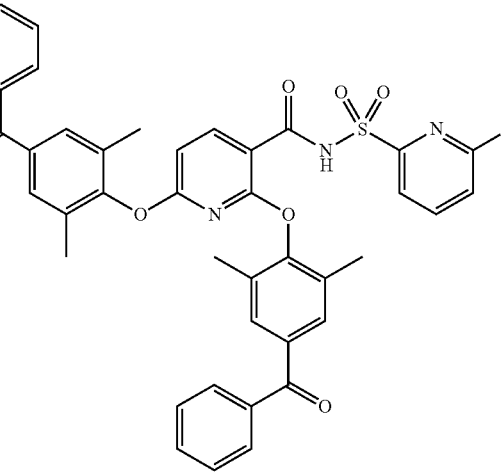
970
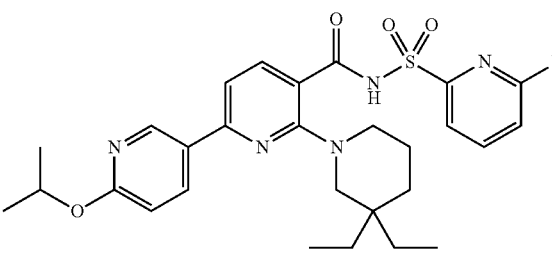
971

TABLE 1-continued
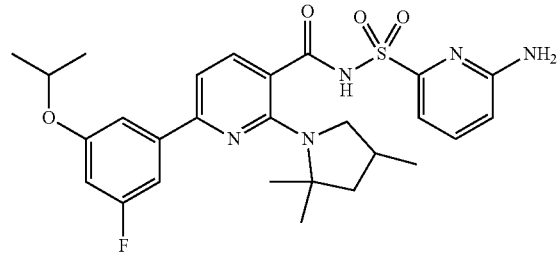 972
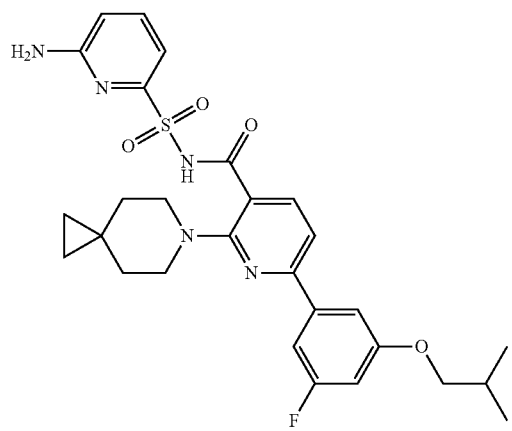 [SMILES: CC(C)COc1cc(F)cc(-c2ccc(C(=O)NS(=O)(=O)c3cccc(N)n3)c(N3CCC4(CC3)CC4)n2)c1] 973
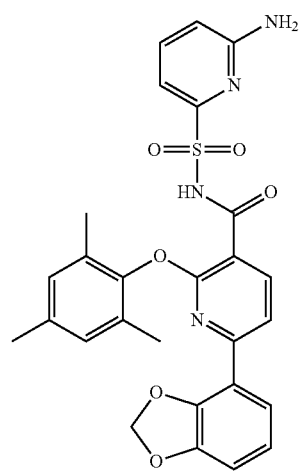 [SMILES: Cc1cc(C)c(Oc2nc(-c3cccc4c3OCO4)ccc2C(=O)NS(=O)(=O)c2cccc(N)n2)c(C)c1] 974
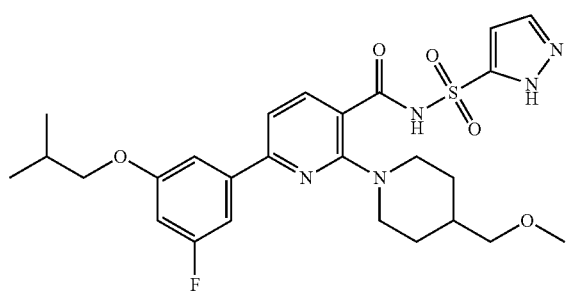 [SMILES: COCC1CCN(c2nc(-c3cc(F)cc(OCC(C)C)c3)ccc2C(=O)NS(=O)(=O)c2ccn[nH]2)CC1] 975

TABLE 1-continued
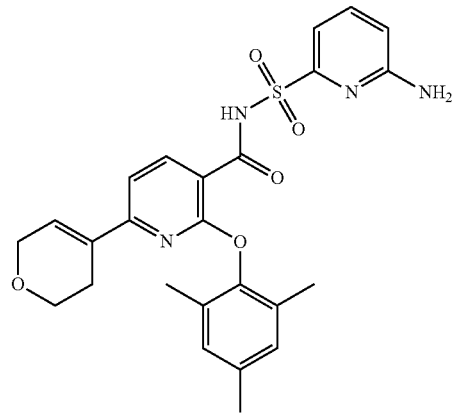 [SMILES: Cc1cc(C)c(Oc2nc(C3=CCOCC3)ccc2C(=O)NS(=O)(=O)c2cccc(N)n2)c(C)c1]
976
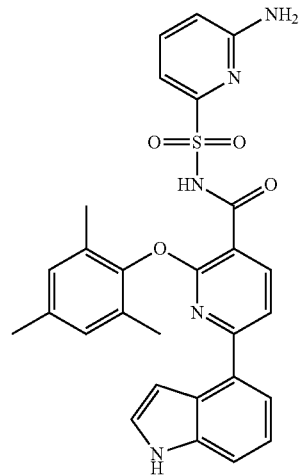 [SMILES: Cc1cc(C)c(Oc2nc(-c3cccc4[nH]ccc34)ccc2C(=O)NS(=O)(=O)c2cccc(N)n2)c(C)c1]
977
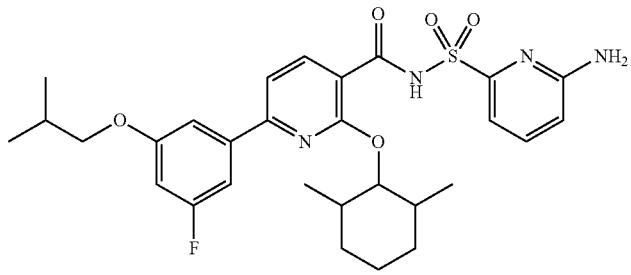 [SMILES: CC(C)COc1cc(F)cc(-c2ccc(C(=O)NS(=O)(=O)c3cccc(N)n3)c(OC3C(C)CCCC3C)n2)c1]
978
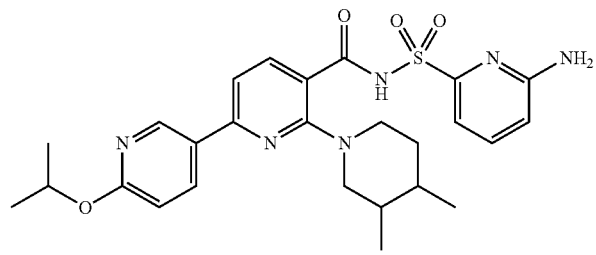 [SMILES: CC(C)Oc1ccc(-c2ccc(C(=O)NS(=O)(=O)c3cccc(N)n3)c(N3CCC(C)C(C)C3)n2)cn1]
979

TABLE 1-continued
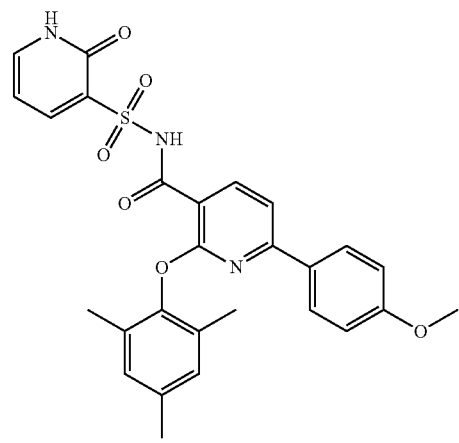 [SMILES: COc1ccc(-c2ccc(C(=O)NS(=O)(=O)c3ccc[nH]c3=O)c(Oc3c(C)cc(C)cc3C)n2)cc1]
980
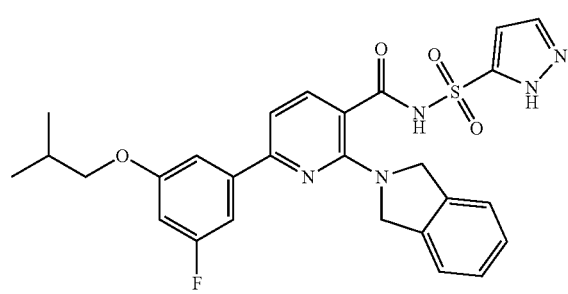 [SMILES: CC(C)COc1cc(F)cc(-c2ccc(C(=O)NS(=O)(=O)c3ccn[nH]3)c(N3Cc4ccccc4C3)n2)c1]
981
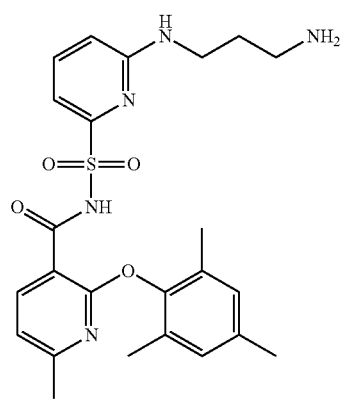 [SMILES: Cc1cc(C)c(Oc2nc(C)ccc2C(=O)NS(=O)(=O)c2cccc(NCCCN)n2)c(C)c1]
982
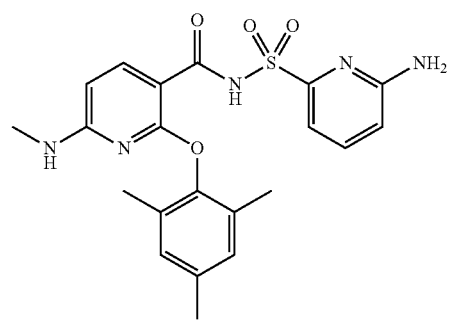
983

TABLE 1-continued
| | |
|---|---|
| 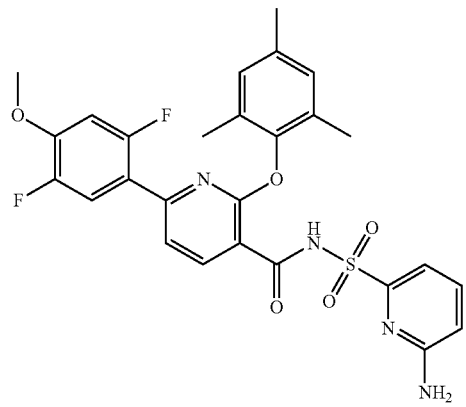 | 984 |
| 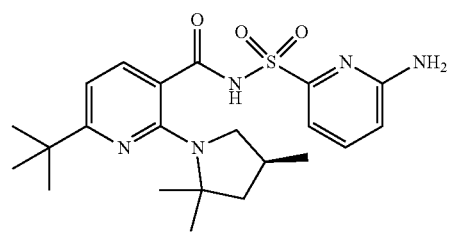 [SMILES: C[C@@H]1CN(c2nc(C(C)(C)C)ccc2C(=O)NS(=O)(=O)c2cccc(N)n2)C(C)(C)C1] | 985 |
| 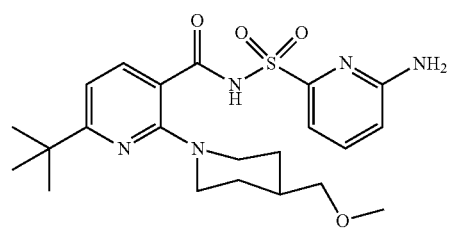 [SMILES: COCC1CCN(c2nc(C(C)(C)C)ccc2C(=O)NS(=O)(=O)c2cccc(N)n2)CC1] | 986 |
| 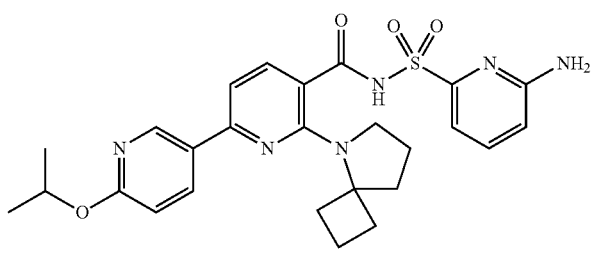 [SMILES: CC(C)Oc1ccc(-c2ccc(C(=O)NS(=O)(=O)c3cccc(N)n3)c(N3CCCC34CCC4)n2)cn1] | 987 |
| 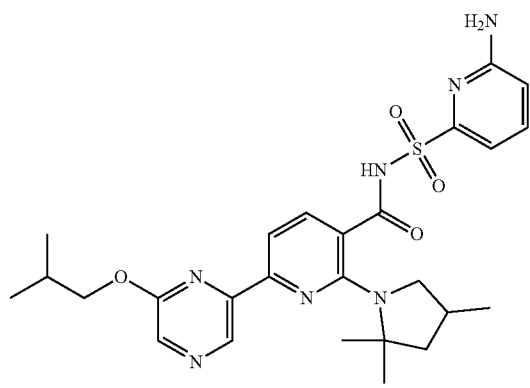 [SMILES: CC(C)COc1cncc(-c2ccc(C(=O)NS(=O)(=O)c3cccc(N)n3)c(N3CC(C)CC3(C)C)n2)n1] | 988 |

TABLE 1-continued
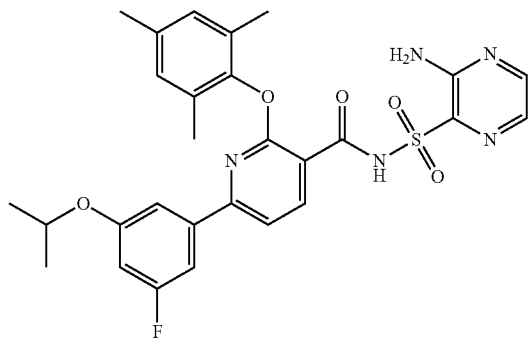 [SMILES: Cc1cc(C)c(Oc2nc(-c3cc(F)cc(OC(C)C)c3)ccc2C(=O)NS(=O)(=O)c2nccnc2N)c(C)c1]
989
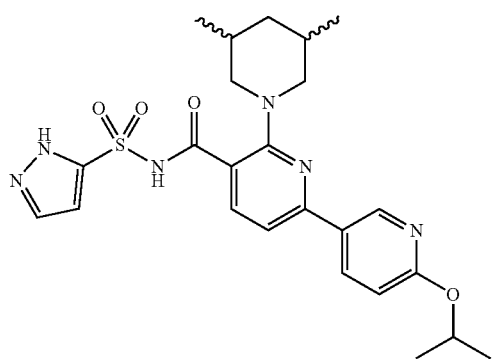
990
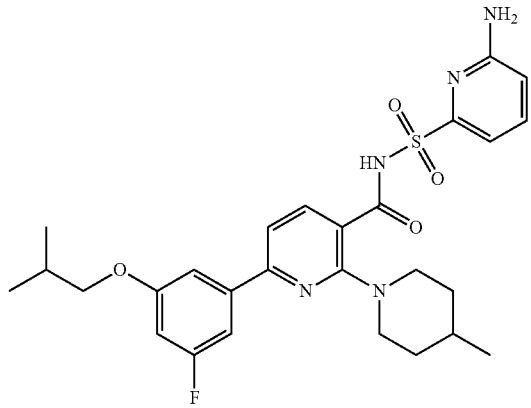 [SMILES: CC(C)COc1cc(F)cc(-c2ccc(C(=O)NS(=O)(=O)c3cccc(N)n3)c(N3CCC(C)CC3)n2)c1]
991
992

TABLE 1-continued
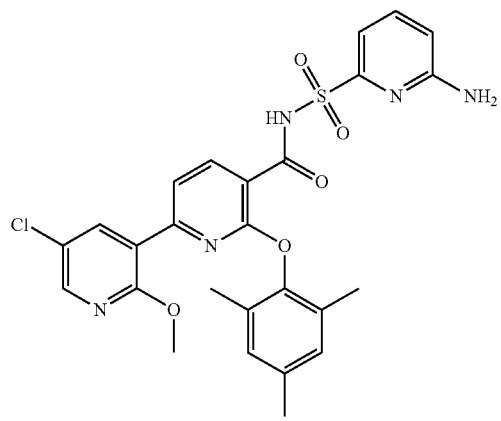 [SMILES: COc1ncc(Cl)cc1-c1ccc(C(=O)NS(=O)(=O)c2cccc(N)n2)c(Oc2c(C)cc(C)cc2C)n1]
993
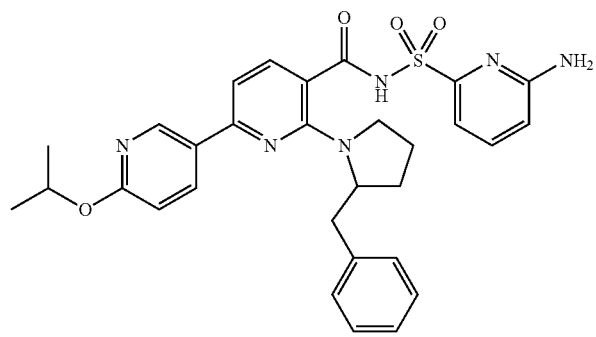 [SMILES: CC(C)Oc1ccc(-c2ccc(C(=O)NS(=O)(=O)c3cccc(N)n3)c(N3CCCC3Cc3ccccc3)n2)cn1]
994
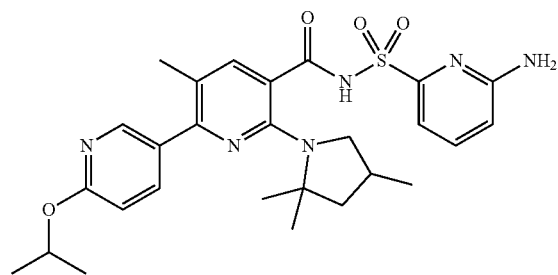 [SMILES: Cc1cc(C(=O)NS(=O)(=O)c2cccc(N)n2)c(N2CC(C)CC2(C)C)nc1-c1ccc(OC(C)C)nc1]
995
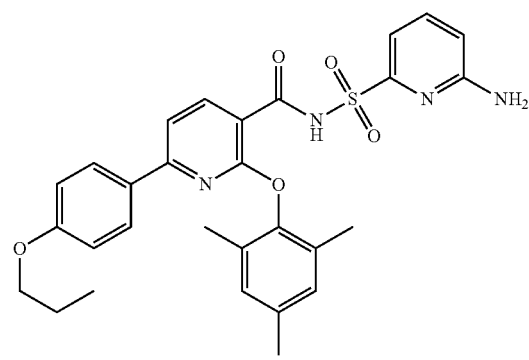 [SMILES: CCCOc1ccc(-c2ccc(C(=O)NS(=O)(=O)c3cccc(N)n3)c(Oc3c(C)cc(C)cc3C)n2)cc1]
996

TABLE 1-continued
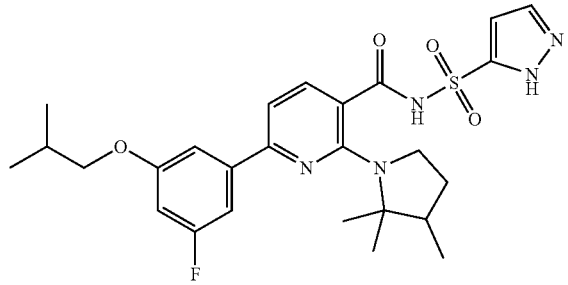 [SMILES: CC(C)COc1cc(F)cc(-c2ccc(C(=O)NS(=O)(=O)c3ccn[nH]3)c(N3CCC(C)C3(C)C)n2)c1]
997
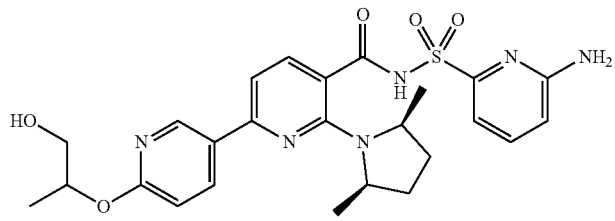 [SMILES: CC(CO)Oc1ccc(-c2ccc(C(=O)NS(=O)(=O)c3cccc(N)n3)c(N3[C@H](C)CC[C@@H]3C)n2)cn1]
998
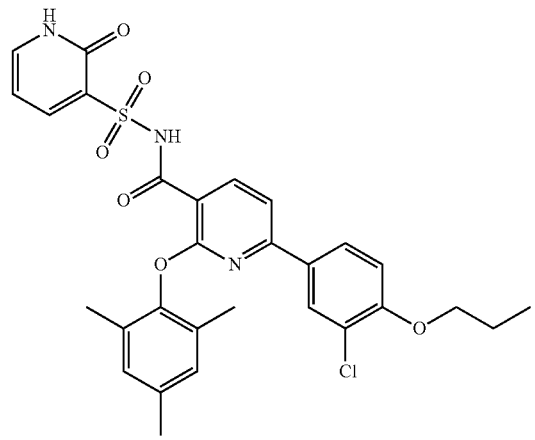 [SMILES: CCCOc1ccc(-c2ccc(C(=O)NS(=O)(=O)c3ccc[nH]c3=O)c(Oc3c(C)cc(C)cc3C)n2)cc1Cl]
999
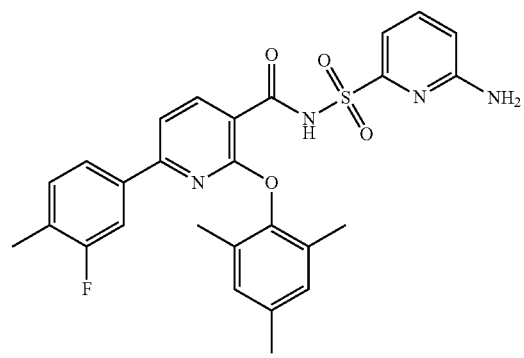
1000
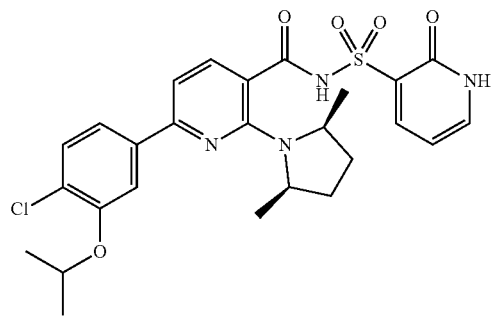 [SMILES: CC(C)Oc1cc(-c2ccc(C(=O)NS(=O)(=O)c3ccc[nH]c3=O)c(N3[C@H](C)CC[C@@H]3C)n2)ccc1Cl]
1001

TABLE 1-continued
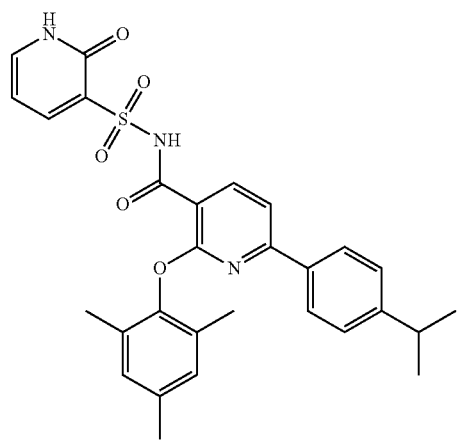 1002
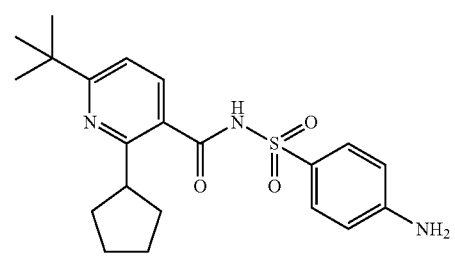 [SMILES: CC(C)(C)c1ccc(C(=O)NS(=O)(=O)c2ccc(N)cc2)c(C2CCCC2)n1] 1003
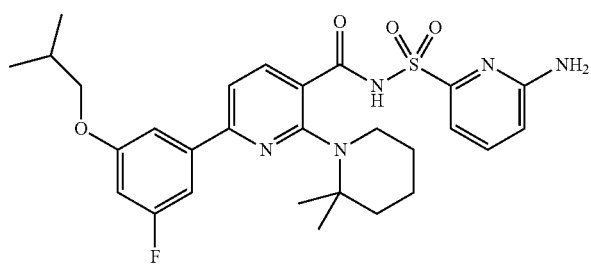 [SMILES: CC(C)COc1cc(F)cc(-c2ccc(C(=O)NS(=O)(=O)c3cccc(N)n3)c(N3CCCCC3(C)C)n2)c1] 1004
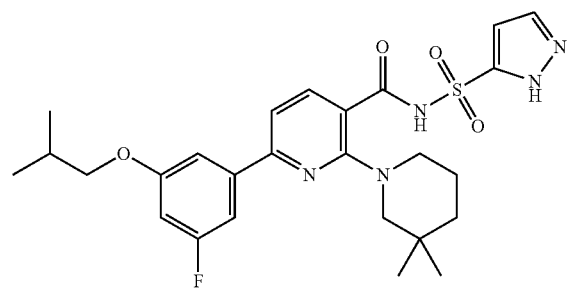 [SMILES: CC(C)COc1cc(F)cc(-c2ccc(C(=O)NS(=O)(=O)c3ccn[nH]3)c(N3CCCC(C)(C)C3)n2)c1] 1005
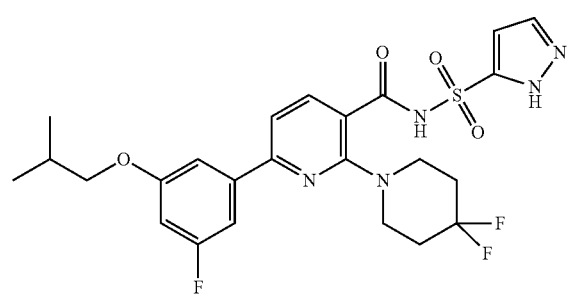 [SMILES: CC(C)COc1cc(F)cc(-c2ccc(C(=O)NS(=O)(=O)c3ccn[nH]3)c(N3CCC(F)(F)CC3)n2)c1] 1006

TABLE 1-continued
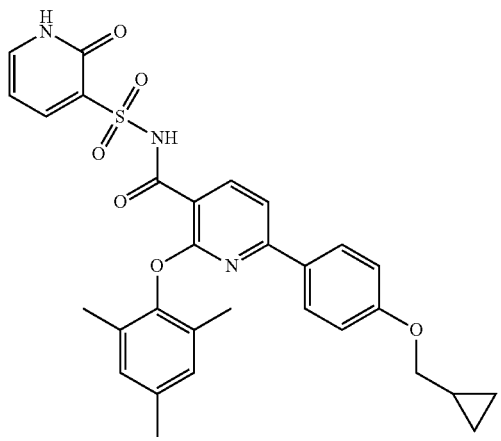 [SMILES: Cc1cc(C)c(Oc2nc(-c3ccc(OCC4CC4)cc3)ccc2C(=O)NS(=O)(=O)c2ccc[nH]c2=O)c(C)c1]
1007
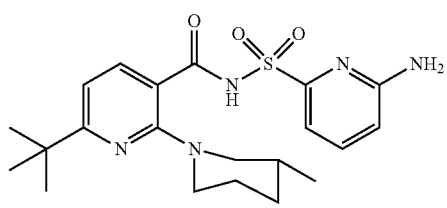 [SMILES: CC1CCCN(c2nc(C(C)(C)C)ccc2C(=O)NS(=O)(=O)c2cccc(N)n2)C1]
1008
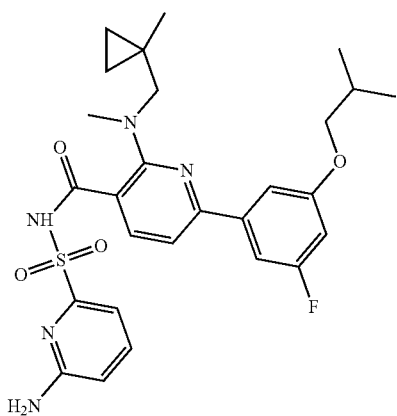 [SMILES: CC(C)COc1cc(F)cc(-c2ccc(C(=O)NS(=O)(=O)c3cccc(N)n3)c(N(C)CC3(C)CC3)n2)c1]
1009
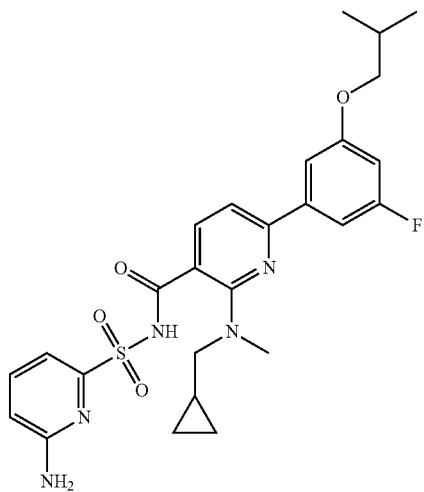
1010

TABLE 1-continued
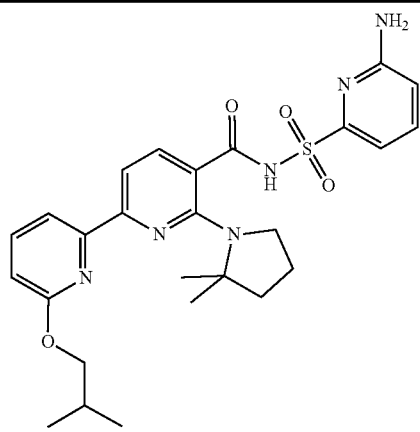
1011
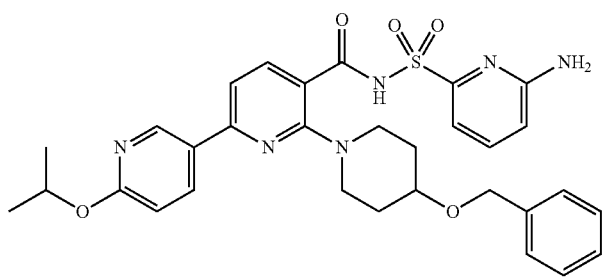 [SMILES: CC(C)Oc1ccc(-c2ccc(C(=O)NS(=O)(=O)c3cccc(N)n3)c(N3CCC(OCc4ccccc4)CC3)n2)cn1]
1012
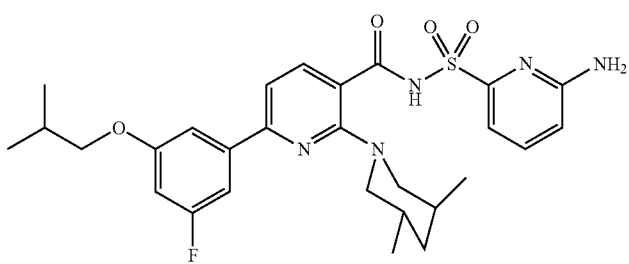 [SMILES: CC(C)COc1cc(F)cc(-c2ccc(C(=O)NS(=O)(=O)c3cccc(N)n3)c(N3CC(C)CC(C)C3)n2)c1]
1013
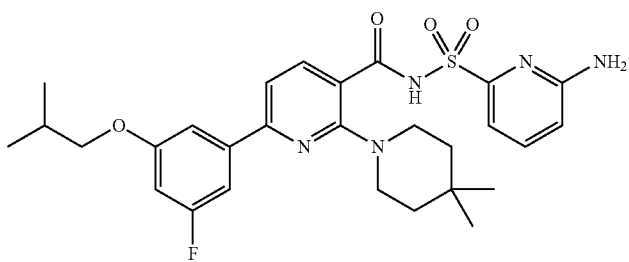 [SMILES: CC(C)COc1cc(F)cc(-c2ccc(C(=O)NS(=O)(=O)c3cccc(N)n3)c(N3CCC(C)(C)CC3)n2)c1]
1014
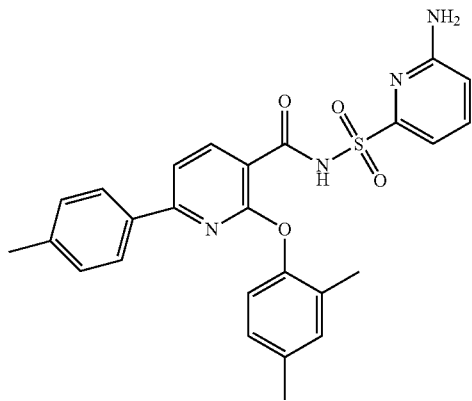 [SMILES: Cc1ccc(-c2ccc(C(=O)NS(=O)(=O)c3cccc(N)n3)c(Oc3ccc(C)cc3C)n2)cc1]
1015

TABLE 1-continued
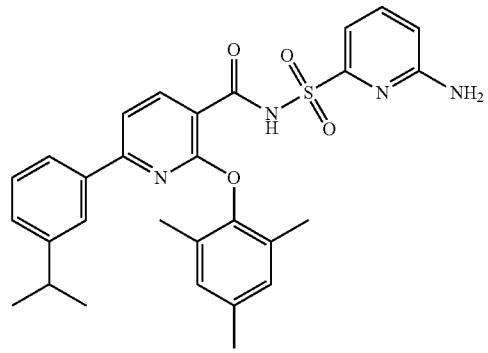 [SMILES: Cc1cc(C)c(Oc2nc(-c3cccc(C(C)C)c3)ccc2C(=O)NS(=O)(=O)c2cccc(N)n2)c(C)c1]
1016
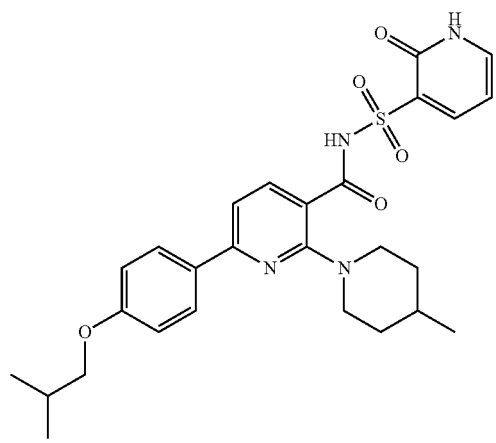 [SMILES: CC(C)COc1ccc(-c2ccc(C(=O)NS(=O)(=O)c3ccc[nH]c3=O)c(N3CCC(C)CC3)n2)cc1]
1017
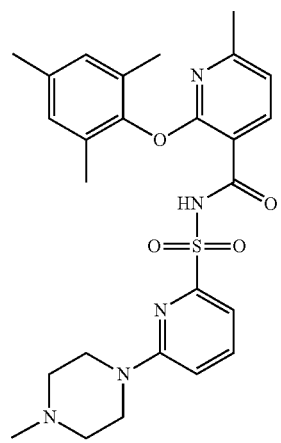 [SMILES: Cc1cc(C)c(Oc2nc(C)ccc2C(=O)NS(=O)(=O)c2cccc(N3CCN(C)CC3)n2)c(C)c1]
1018
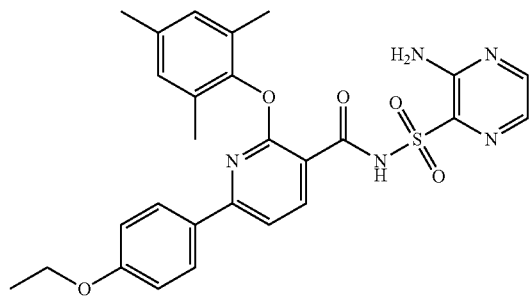 [SMILES: CCOc1ccc(-c2ccc(C(=O)NS(=O)(=O)c3nccnc3N)c(Oc3c(C)cc(C)cc3C)n2)cc1]
1019

TABLE 1-continued
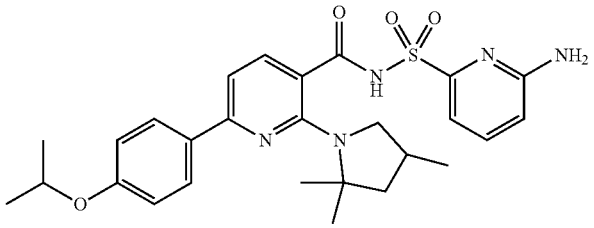 [SMILES: CC1CN(c2nc(-c3ccc(OC(C)C)cc3)ccc2C(=O)NS(=O)(=O)c2cccc(N)n2)C(C)(C)C1]
1020
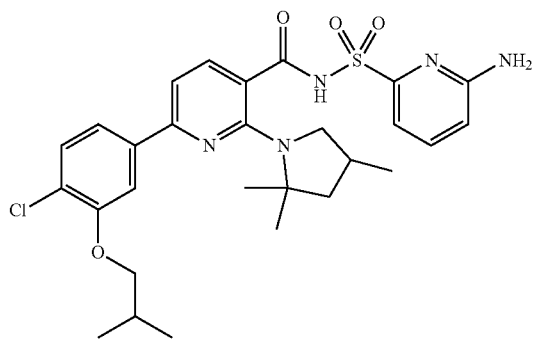 [SMILES: CC(C)COc1cc(-c2ccc(C(=O)NS(=O)(=O)c3cccc(N)n3)c(N3CC(C)CC3(C)C)n2)ccc1Cl]
1021
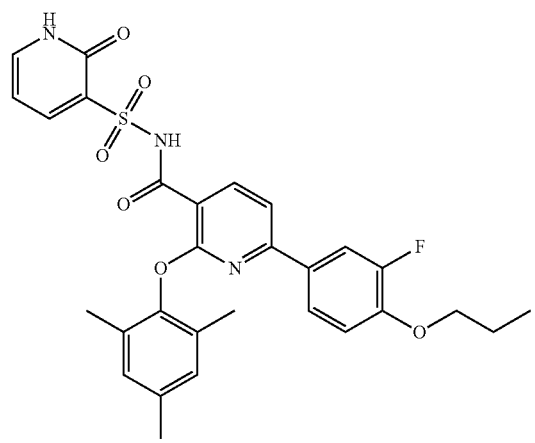 [SMILES: CCCOc1ccc(-c2ccc(C(=O)NS(=O)(=O)c3ccc[nH]c3=O)c(Oc3c(C)cc(C)cc3C)n2)cc1F]
1022
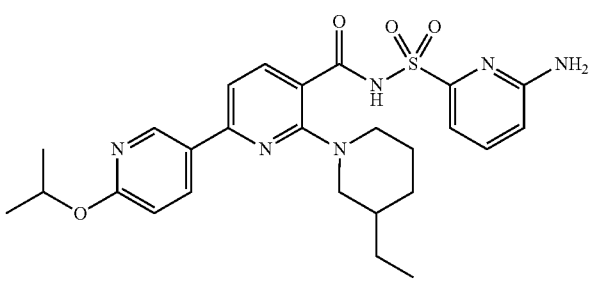 [SMILES: CCC1CCCN(c2nc(-c3ccc(OC(C)C)nc3)ccc2C(=O)NS(=O)(=O)c2cccc(N)n2)C1]
1023
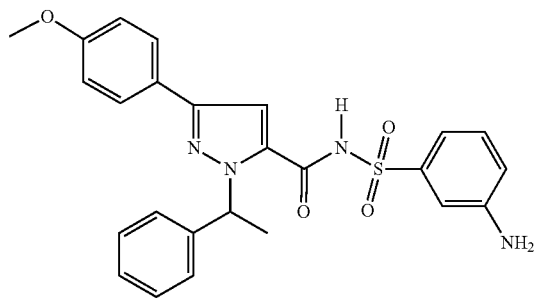 [SMILES: COc1ccc(-c2cc(C(=O)NS(=O)(=O)c3cccc(N)c3)n(C(C)c3ccccc3)n2)cc1]
1024

TABLE 1-continued
| | |
|---|---|
| 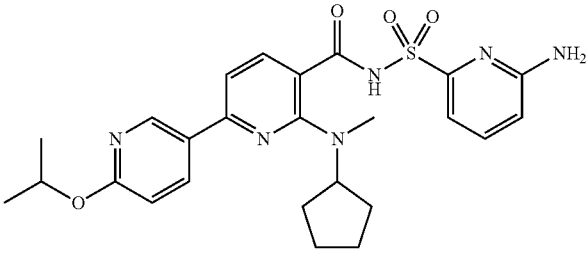 [SMILES: CC(C)Oc1ccc(-c2ccc(C(=O)NS(=O)(=O)c3cccc(N)n3)c(N(C)C3CCCC3)n2)cn1] | 1025 |
| 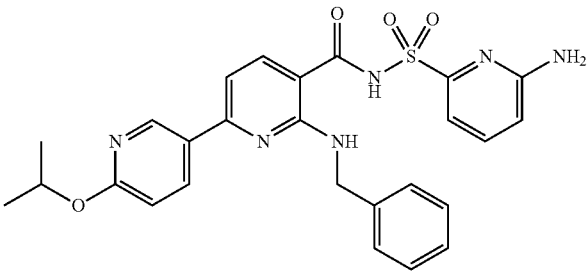 [SMILES: CC(C)Oc1ccc(-c2ccc(C(=O)NS(=O)(=O)c3cccc(N)n3)c(NCc3ccccc3)n2)cn1] | 1026 |
| 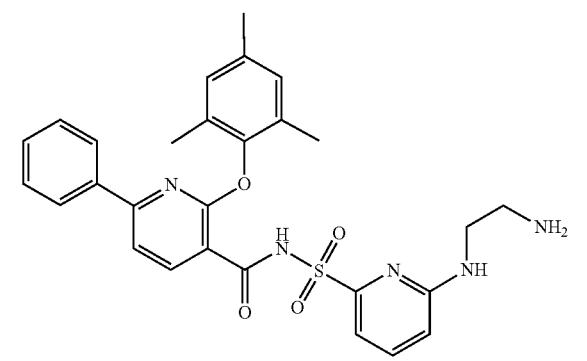 [SMILES: Cc1cc(C)c(Oc2nc(-c3ccccc3)ccc2C(=O)NS(=O)(=O)c2cccc(NCCN)n2)c(C)c1] | 1027 |
| 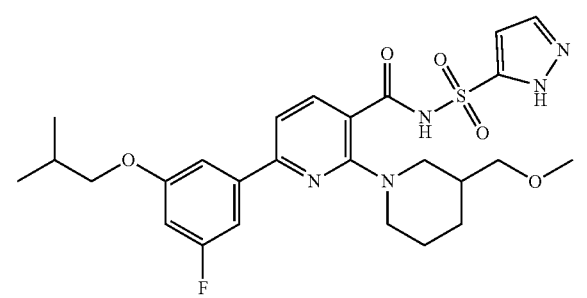 [SMILES: COCC1CCCN(c2nc(-c3cc(F)cc(OCC(C)C)c3)ccc2C(=O)NS(=O)(=O)c2ccn[nH]2)C1] | 1028 |
| 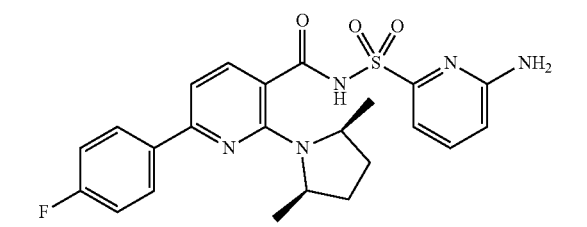 [SMILES: C[C@@H]1CC[C@H](C)N1c1nc(-c2ccc(F)cc2)ccc1C(=O)NS(=O)(=O)c1cccc(N)n1] | 1029 |

TABLE 1-continued
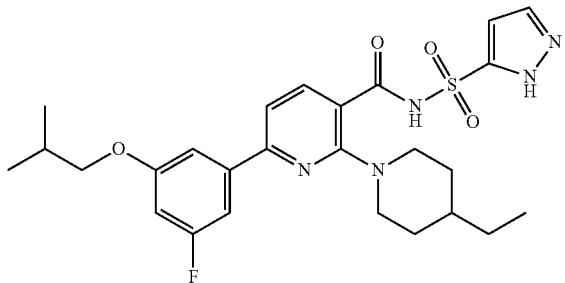 [SMILES: CCC1CCN(c2nc(-c3cc(F)cc(OCC(C)C)c3)ccc2C(=O)NS(=O)(=O)c2ccn[nH]2)CC1]
1030
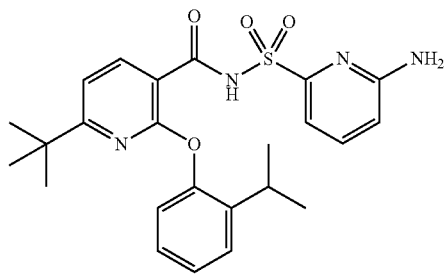 [SMILES: CC(C)c1ccccc1Oc1nc(C(C)(C)C)ccc1C(=O)NS(=O)(=O)c1cccc(N)n1]
1031
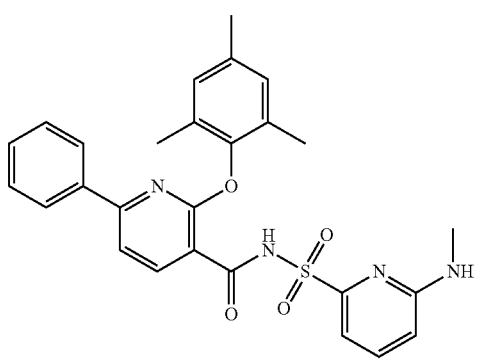 [SMILES: CNc1cccc(S(=O)(=O)NC(=O)c2ccc(-c3ccccc3)nc2Oc2c(C)cc(C)cc2C)n1]
1032
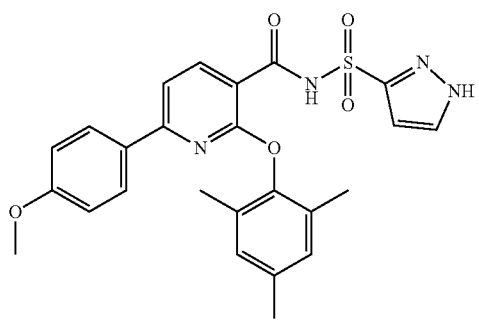 [SMILES: COc1ccc(-c2ccc(C(=O)NS(=O)(=O)c3cc[nH]n3)c(Oc3c(C)cc(C)cc3C)n2)cc1]
1033
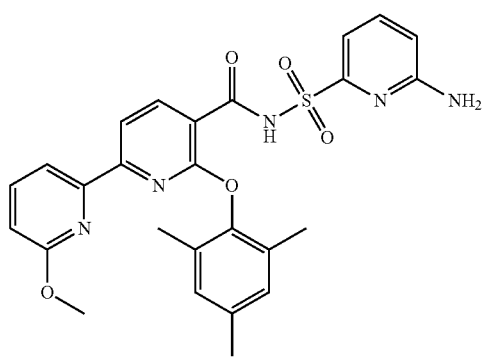 [SMILES: COc1cccc(-c2ccc(C(=O)NS(=O)(=O)c3cccc(N)n3)c(Oc3c(C)cc(C)cc3C)n2)n1]
1034

TABLE 1-continued
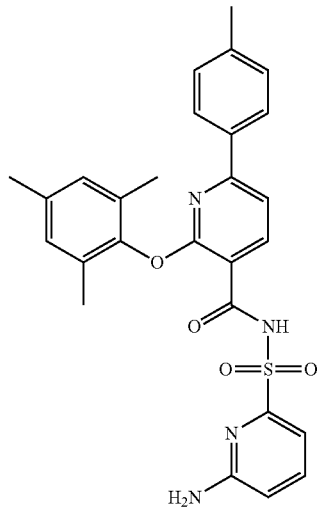 [SMILES: Cc1ccc(-c2ccc(C(=O)NS(=O)(=O)c3cccc(N)n3)c(Oc3c(C)cc(C)cc3C)n2)cc1]
1035
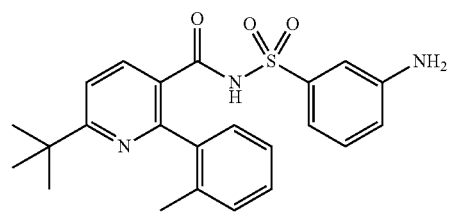 [SMILES: Cc1ccccc1-c1nc(C(C)(C)C)ccc1C(=O)NS(=O)(=O)c1cccc(N)c1]
1036
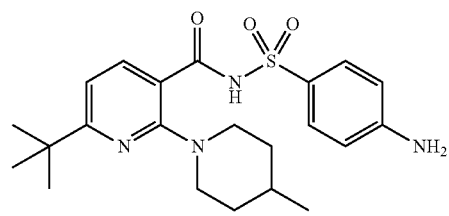 [SMILES: CC1CCN(c2nc(C(C)(C)C)ccc2C(=O)NS(=O)(=O)c2ccc(N)cc2)CC1]
1037
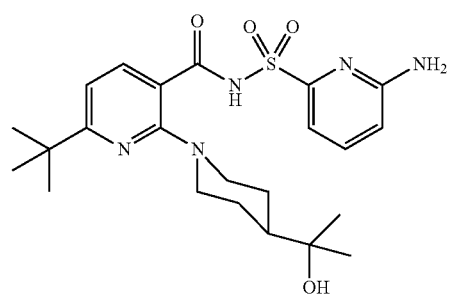 [SMILES: CC(C)(C)c1ccc(C(=O)NS(=O)(=O)c2cccc(N)n2)c(N2CCC(C(C)(C)O)CC2)n1]
1038
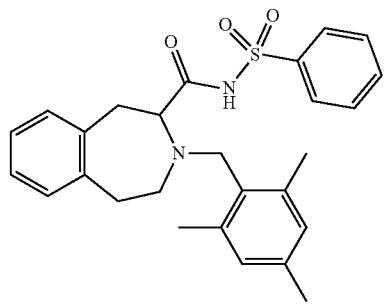 [SMILES: Cc1cc(C)c(CN2CCc3ccccc3CC2C(=O)NS(=O)(=O)c2ccccc2)c(C)c1]
1039

TABLE 1-continued
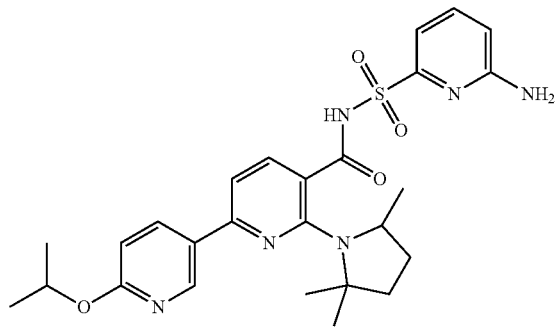 [SMILES: CC(C)Oc1ccc(-c2ccc(C(=O)NS(=O)(=O)c3cccc(N)n3)c(N3C(C)CCC3(C)C)n2)cn1]
1040
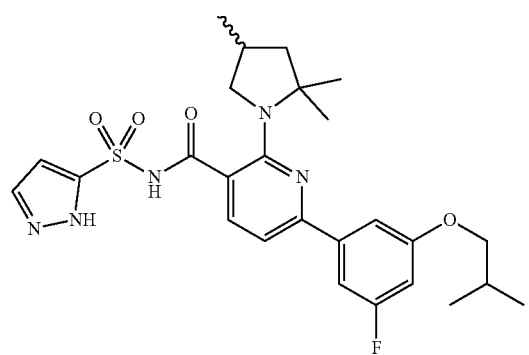 [SMILES: CC(C)COc1cc(F)cc(-c2ccc(C(=O)NS(=O)(=O)c3ccn[nH]3)c(N3CC(C)CC3(C)C)n2)c1]
1041
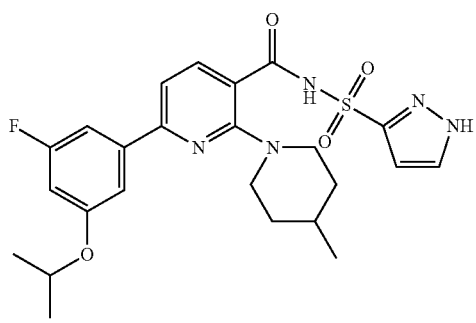 [SMILES: CC1CCN(c2nc(-c3cc(F)cc(OC(C)C)c3)ccc2C(=O)NS(=O)(=O)c2cc[nH]n2)CC1]
1042
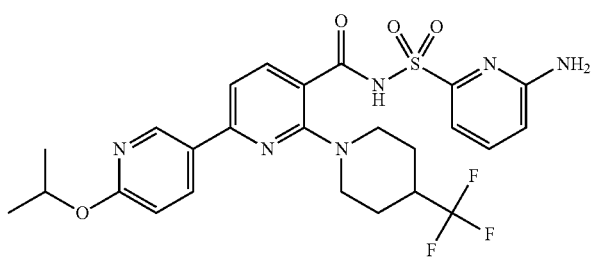 [SMILES: CC(C)Oc1ccc(-c2ccc(C(=O)NS(=O)(=O)c3cccc(N)n3)c(N3CCC(C(F)(F)F)CC3)n2)cn1]
1043
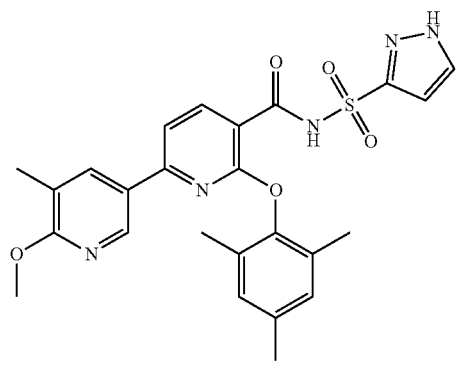 [SMILES: COc1ncc(-c2ccc(C(=O)NS(=O)(=O)c3cc[nH]n3)c(Oc3c(C)cc(C)cc3C)n2)cc1C]
1044

TABLE 1-continued
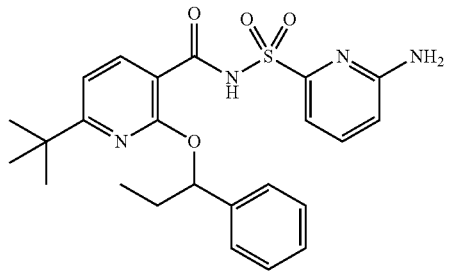 [SMILES: CCC(Oc1nc(C(C)(C)C)ccc1C(=O)NS(=O)(=O)c1cccc(N)n1)c1ccccc1]
1045
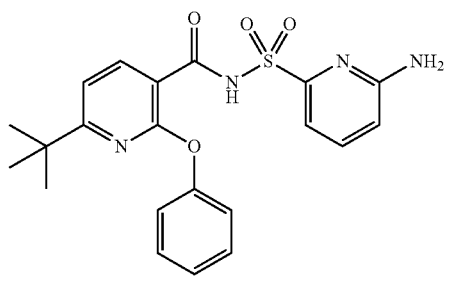 [SMILES: CC(C)(C)c1ccc(C(=O)NS(=O)(=O)c2cccc(N)n2)c(Oc2ccccc2)n1]
1046
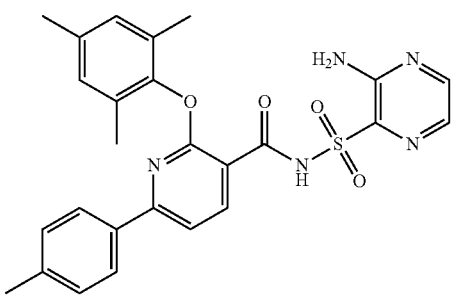 [SMILES: Cc1ccc(-c2ccc(C(=O)NS(=O)(=O)c3nccnc3N)c(Oc3c(C)cc(C)cc3C)n2)cc1]
1047
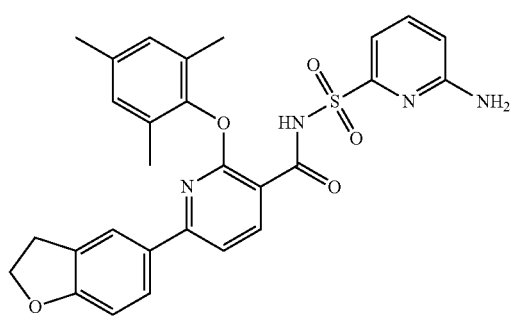 [SMILES: Cc1cc(C)c(Oc2nc(-c3ccc4c(c3)CCO4)ccc2C(=O)NS(=O)(=O)c2cccc(N)n2)c(C)c1]
1048
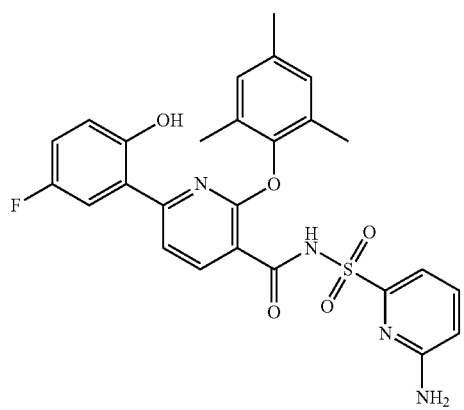 [SMILES: Cc1cc(C)c(Oc2nc(-c3cc(F)ccc3O)ccc2C(=O)NS(=O)(=O)c2cccc(N)n2)c(C)c1]
1049

TABLE 1-continued
| | |
|---|---|
| 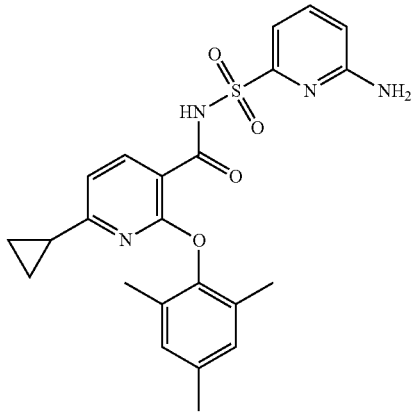 [SMILES: Cc1cc(C)c(Oc2nc(C3CC3)ccc2C(=O)NS(=O)(=O)c2cccc(N)n2)c(C)c1] | 1050 |
| 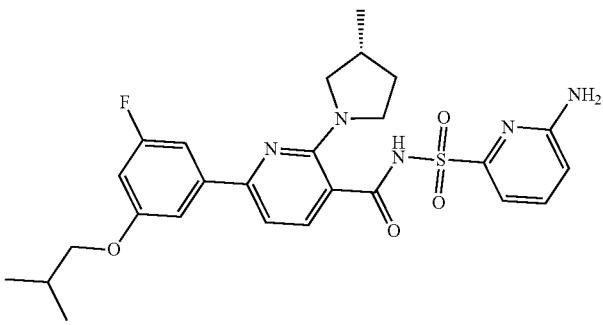 [SMILES: CC(C)COc1cc(F)cc(-c2ccc(C(=O)NS(=O)(=O)c3cccc(N)n3)c(N3CC[C@@H](C)C3)n2)c1] | 1051 |
| 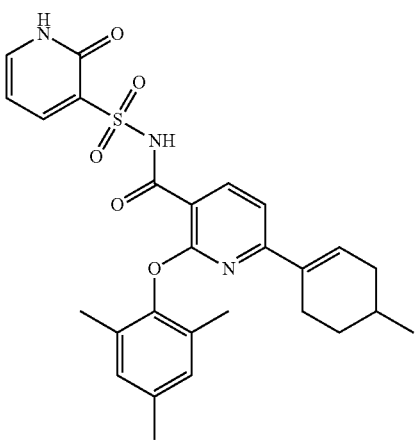 [SMILES: Cc1cc(C)c(Oc2nc(C3=CCC(C)CC3)ccc2C(=O)NS(=O)(=O)c2ccc[nH]c2=O)c(C)c1] | 1052 |
| 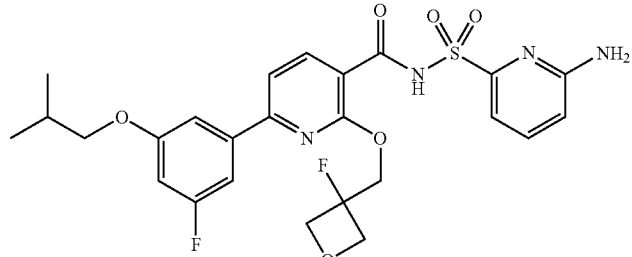 | 1053 |

TABLE 1-continued
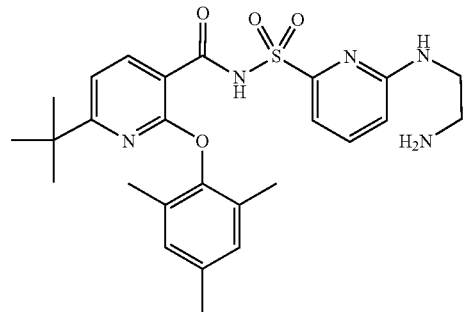 [SMILES: Cc1cc(C)c(Oc2nc(C(C)(C)C)ccc2C(=O)NS(=O)(=O)c2cccc(NCCN)n2)c(C)c1]
1054
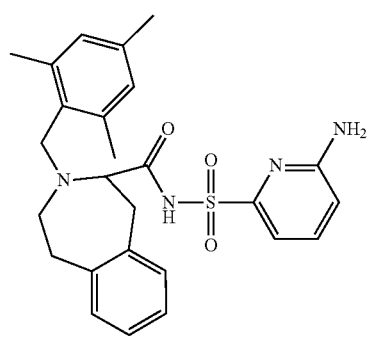 [SMILES: Cc1cc(C)c(CN2CCc3ccccc3CC2C(=O)NS(=O)(=O)c2cccc(N)n2)c(C)c1]
1055
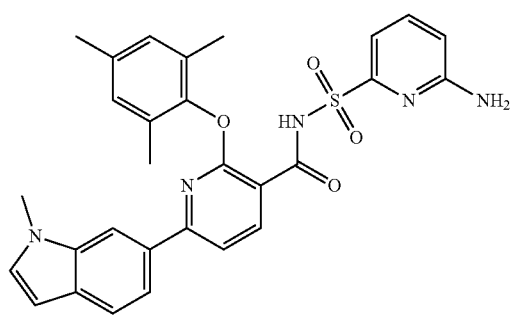 [SMILES: Cc1cc(C)c(Oc2nc(-c3ccc4ccn(C)c4c3)ccc2C(=O)NS(=O)(=O)c2cccc(N)n2)c(C)c1]
1056
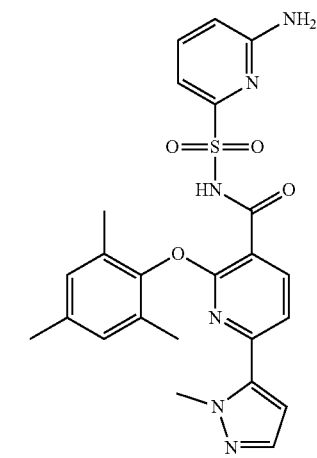 [SMILES: Cc1cc(C)c(Oc2nc(-c3ccnn3C)ccc2C(=O)NS(=O)(=O)c2cccc(N)n2)c(C)c1]
1057

TABLE 1-continued
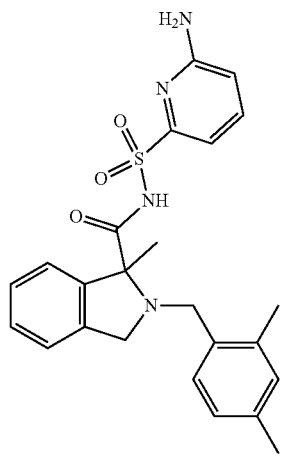 [SMILES: Cc1ccc(CN2Cc3ccccc3C2(C)C(=O)NS(=O)(=O)c2cccc(N)n2)c(C)c1]
1058
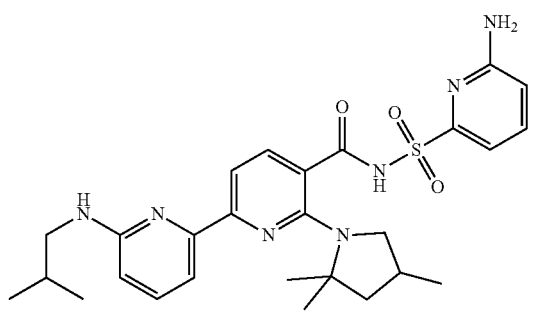 [SMILES: CC(C)CNc1cccc(-c2ccc(C(=O)NS(=O)(=O)c3cccc(N)n3)c(N3CC(C)CC3(C)C)n2)n1]
1059
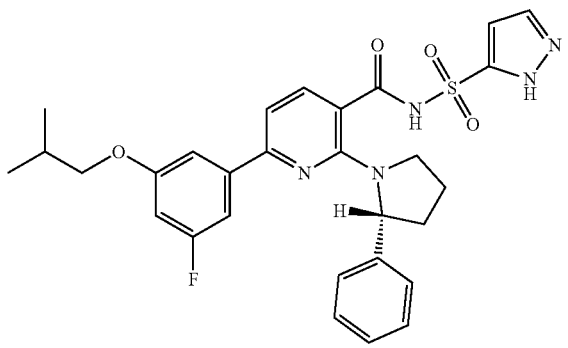 [SMILES: CC(C)COc1cc(F)cc(-c2ccc(C(=O)NS(=O)(=O)c3ccn[nH]3)c(N3CCC[C@@H]3c3ccccc3)n2)c1]
1060
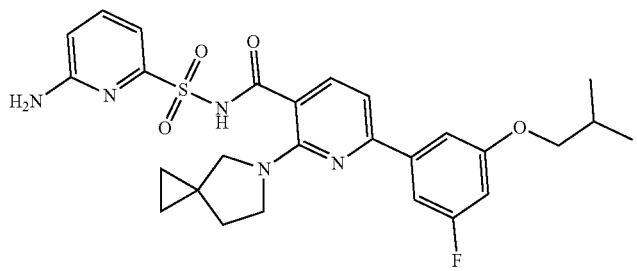 [SMILES: CC(C)COc1cc(F)cc(-c2ccc(C(=O)NS(=O)(=O)c3cccc(N)n3)c(N3CCC4(CC4)C3)n2)c1]
1061

TABLE 1-continued
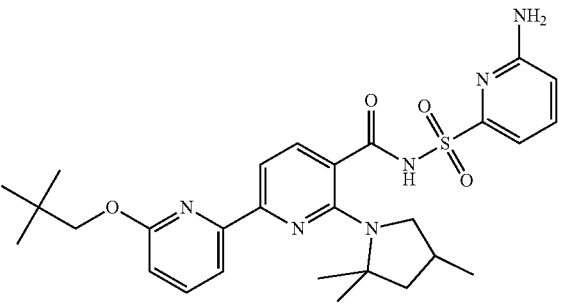 [SMILES: CC1CN(c2nc(-c3cccc(OCC(C)(C)C)n3)ccc2C(=O)NS(=O)(=O)c2cccc(N)n2)C(C)(C)C1] 1062
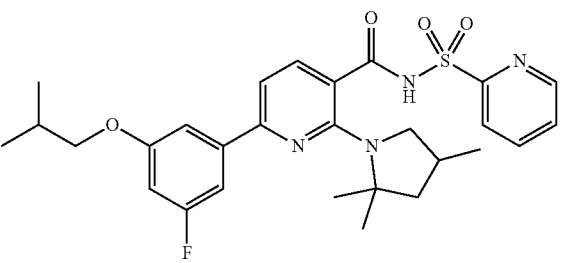 [SMILES: CC(C)COc1cc(F)cc(-c2ccc(C(=O)NS(=O)(=O)c3ccccn3)c(N3CC(C)CC3(C)C)n2)c1] 1063
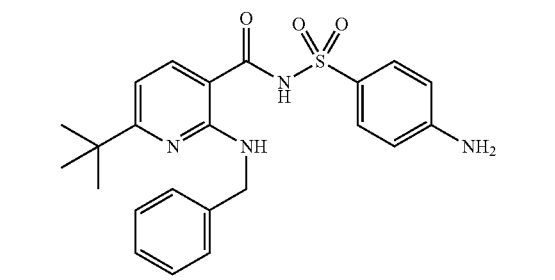 [SMILES: CC(C)(C)c1ccc(C(=O)NS(=O)(=O)c2ccc(N)cc2)c(NCc2ccccc2)n1] 1064
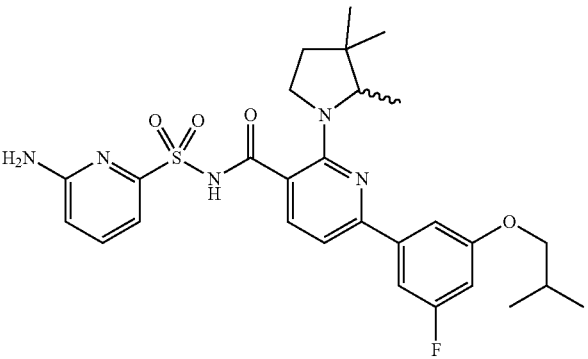 [SMILES: CC(C)COc1cc(F)cc(-c2ccc(C(=O)NS(=O)(=O)c3cccc(N)n3)c(N3CCC(C)(C)C3C)n2)c1] 1065
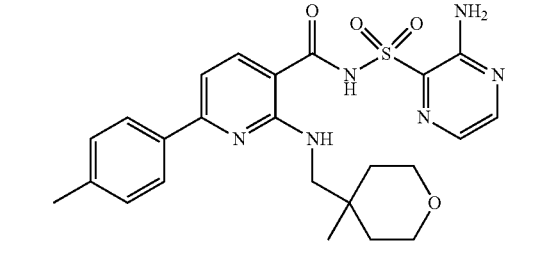 [SMILES: Cc1ccc(-c2ccc(C(=O)NS(=O)(=O)c3nccnc3N)c(NCC3(C)CCOCC3)n2)cc1] 1066

TABLE 1-continued
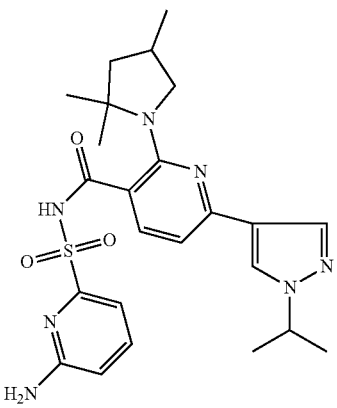 [SMILES: CC1CN(c2nc(-c3cnn(C(C)C)c3)ccc2C(=O)NS(=O)(=O)c2cccc(N)n2)C(C)(C)C1]
1067
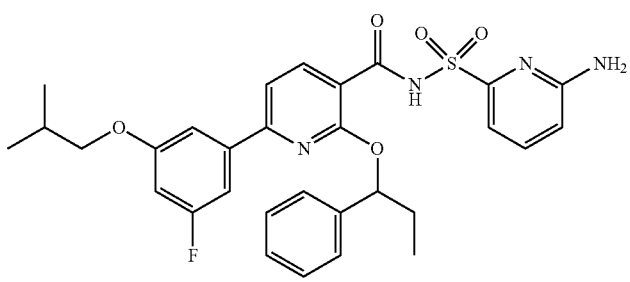 [SMILES: CCC(Oc1nc(-c2cc(F)cc(OCC(C)C)c2)ccc1C(=O)NS(=O)(=O)c1cccc(N)n1)c1ccccc1]
1068
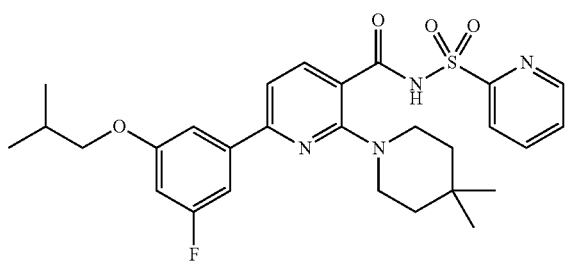 [SMILES: CC(C)COc1cc(F)cc(-c2ccc(C(=O)NS(=O)(=O)c3ccccn3)c(N3CCC(C)(C)CC3)n2)c1]
1069
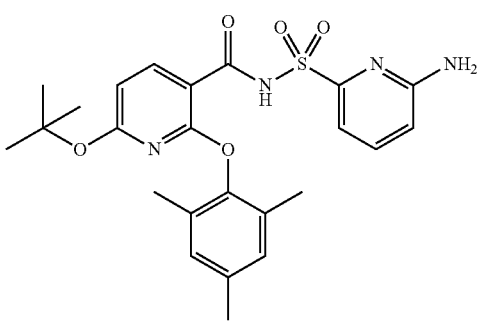 [SMILES: Cc1cc(C)c(Oc2nc(OC(C)(C)C)ccc2C(=O)NS(=O)(=O)c2cccc(N)n2)c(C)c1]
1070
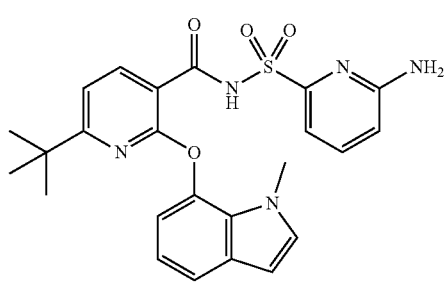 [SMILES: Cn1ccc2cccc(Oc3nc(C(C)(C)C)ccc3C(=O)NS(=O)(=O)c3cccc(N)n3)c21]
1071

TABLE 1-continued
| | |
|---|---|
| 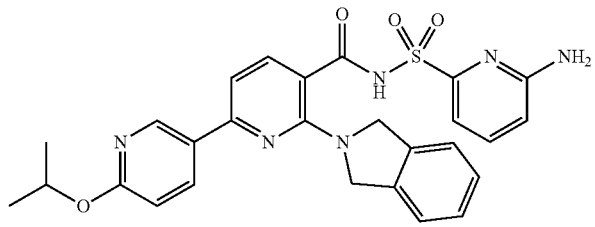 [SMILES: CC(C)Oc1ccc(-c2ccc(C(=O)NS(=O)(=O)c3cccc(N)n3)c(N3Cc4ccccc4C3)n2)cn1] | 1072 |
| 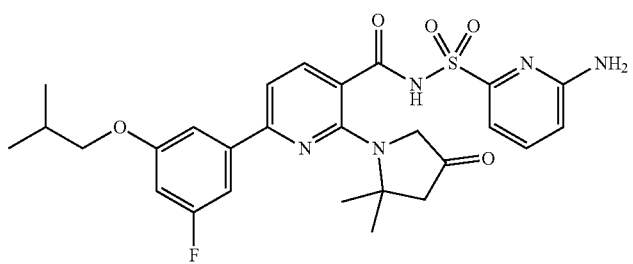 [SMILES: CC(C)COc1cc(F)cc(-c2ccc(C(=O)NS(=O)(=O)c3cccc(N)n3)c(N3CC(=O)CC3(C)C)n2)c1] | 1073 |
| 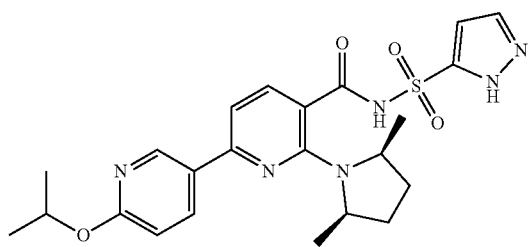 [SMILES: CC(C)Oc1ccc(-c2ccc(C(=O)NS(=O)(=O)c3ccn[nH]3)c(N3[C@H](C)CC[C@@H]3C)n2)cn1] | 1074 |
| 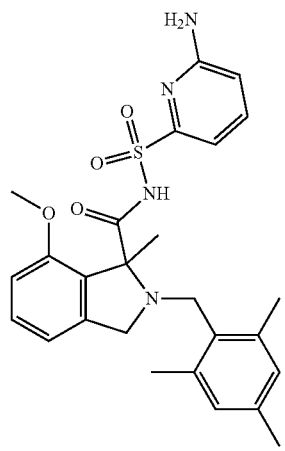 | 1075 |
| 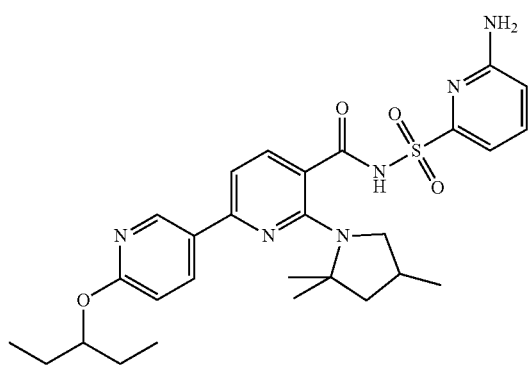 [SMILES: CCC(CC)Oc1ccc(-c2ccc(C(=O)NS(=O)(=O)c3cccc(N)n3)c(N3CC(C)CC3(C)C)n2)cn1] | 1076 |

TABLE 1-continued
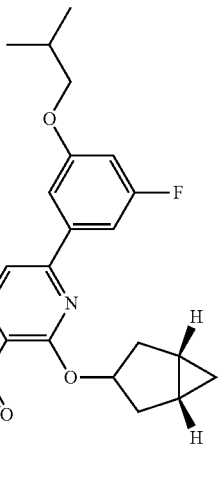
1077
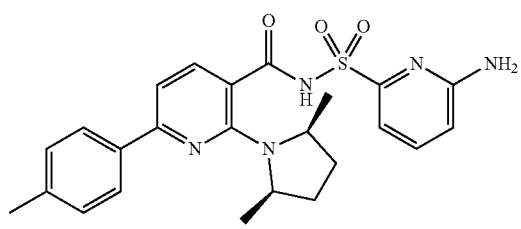 [SMILES: Cc1ccc(-c2ccc(C(=O)NS(=O)(=O)c3cccc(N)n3)c(N3[C@H](C)CC[C@@H]3C)n2)cc1]
1078
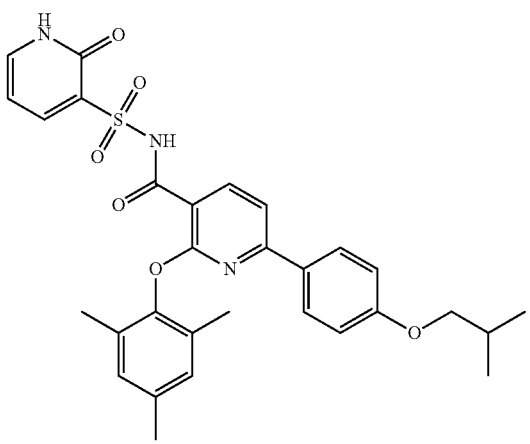 [SMILES: Cc1cc(C)c(Oc2nc(-c3ccc(OCC(C)C)cc3)ccc2C(=O)NS(=O)(=O)c2ccc[nH]c2=O)c(C)c1]
1079
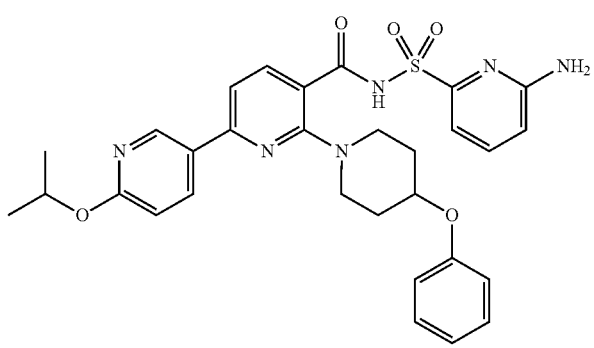 [SMILES: CC(C)Oc1ccc(-c2ccc(C(=O)NS(=O)(=O)c3cccc(N)n3)c(N3CCC(Oc4ccccc4)CC3)n2)cn1]
1080

TABLE 1-continued
| | |
|---|---|
| 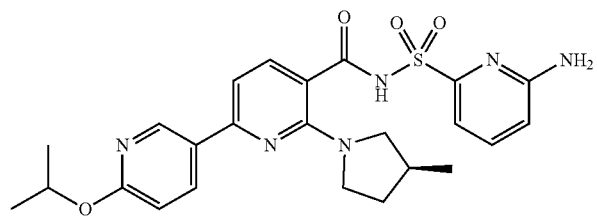 [SMILES: CC(C)Oc1ccc(-c2ccc(C(=O)NS(=O)(=O)c3cccc(N)n3)c(N3CC[C@H](C)C3)n2)cn1] | 1081 |
| 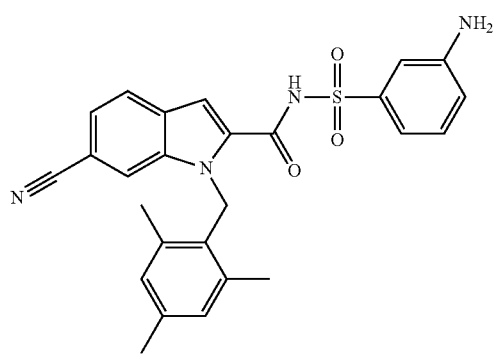 [SMILES: Cc1cc(C)c(Cn2c(C(=O)NS(=O)(=O)c3cccc(N)c3)cc3ccc(C#N)cc32)c(C)c1] | 1082 |
| 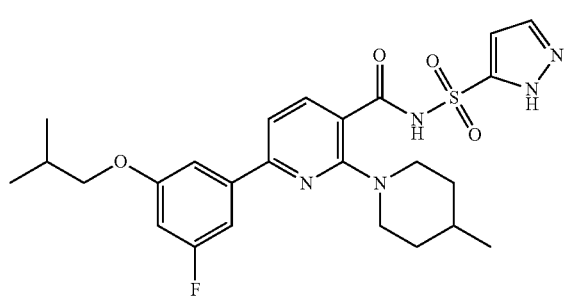 [SMILES: CC(C)COc1cc(F)cc(-c2ccc(C(=O)NS(=O)(=O)c3ccn[nH]3)c(N3CCC(C)CC3)n2)c1] | 1083 |
| 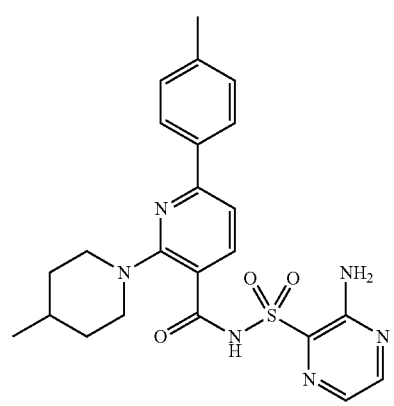 [SMILES: Cc1ccc(-c2ccc(C(=O)NS(=O)(=O)c3nccnc3N)c(N3CCC(C)CC3)n2)cc1] | 1084 |
| 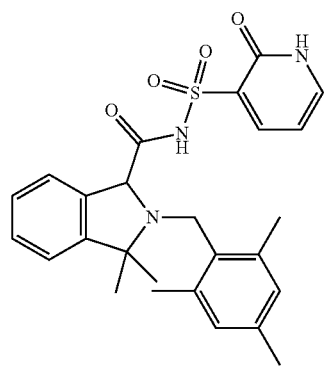 [SMILES: Cc1cc(C)c(CN2C(C(=O)NS(=O)(=O)c3ccc[nH]c3=O)c3ccccc3C2(C)C)c(C)c1] | 1085 |

TABLE 1-continued
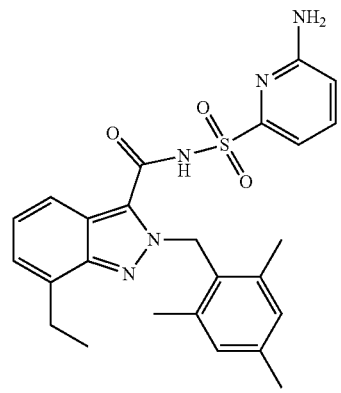 [SMILES: CCc1cccc2c(C(=O)NS(=O)(=O)c3cccc(N)n3)n(Cc3c(C)cc(C)cc3C)nc12]
1086
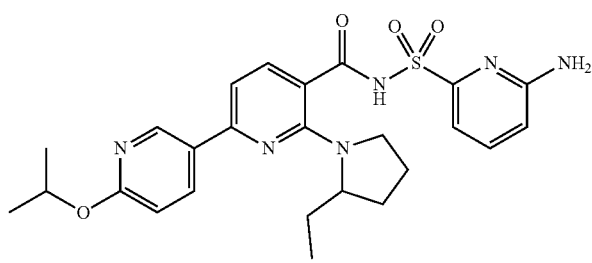 [SMILES: CCC1CCCN1c1nc(-c2ccc(OC(C)C)nc2)ccc1C(=O)NS(=O)(=O)c1cccc(N)n1]
1087
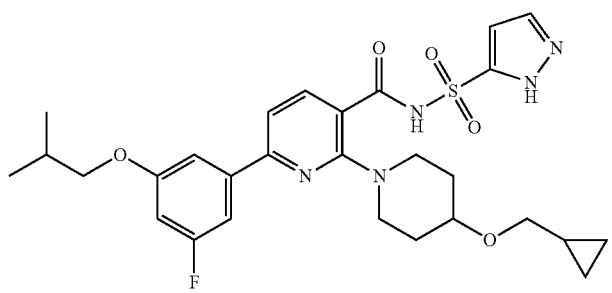 [SMILES: CC(C)COc1cc(F)cc(-c2ccc(C(=O)NS(=O)(=O)c3ccn[nH]3)c(N3CCC(OCC4CC4)CC3)n2)c1]
1088
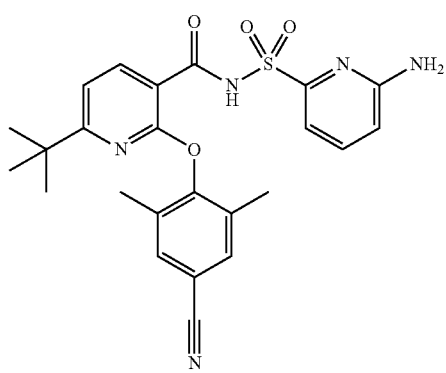 [SMILES: Cc1cc(C#N)cc(C)c1Oc1nc(C(C)(C)C)ccc1C(=O)NS(=O)(=O)c1cccc(N)n1]
1089
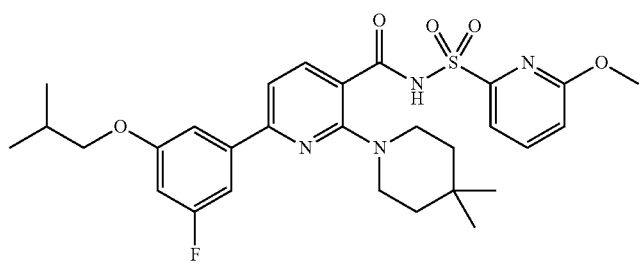 [SMILES: COc1cccc(S(=O)(=O)NC(=O)c2ccc(-c3cc(F)cc(OCC(C)C)c3)nc2N2CCC(C)(C)CC2)n1]
1090

TABLE 1-continued
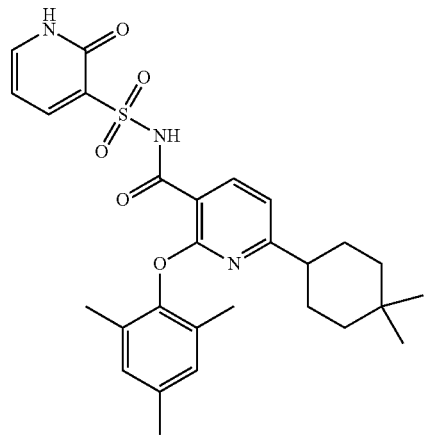 [SMILES: Cc1cc(C)c(Oc2nc(C3CCC(C)(C)CC3)ccc2C(=O)NS(=O)(=O)c2ccc[nH]c2=O)c(C)c1]
1091
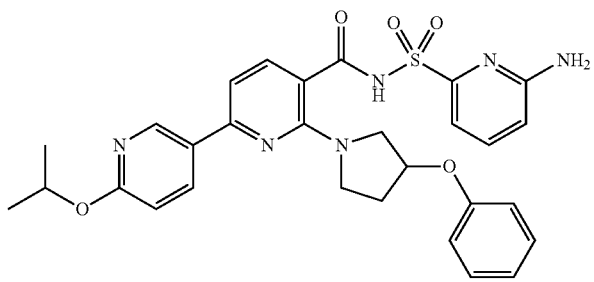 [SMILES: CC(C)Oc1ccc(-c2ccc(C(=O)NS(=O)(=O)c3cccc(N)n3)c(N3CCC(Oc4ccccc4)C3)n2)cn1]
1092
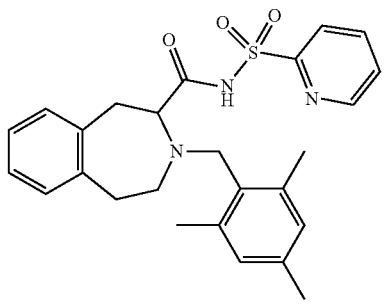 [SMILES: Cc1cc(C)c(CN2CCc3ccccc3CC2C(=O)NS(=O)(=O)c2ccccn2)c(C)c1]
1093
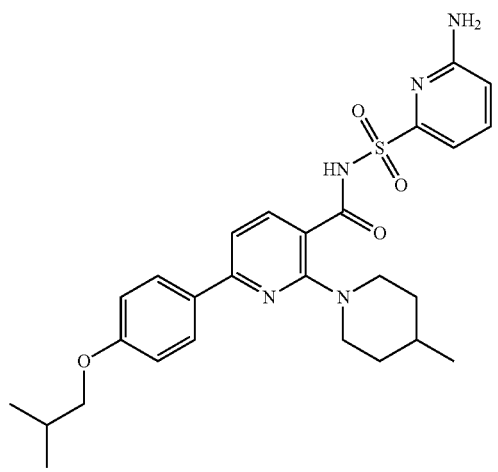 [SMILES: CC(C)COc1ccc(-c2ccc(C(=O)NS(=O)(=O)c3cccc(N)n3)c(N3CCC(C)CC3)n2)cc1]
1094

TABLE 1-continued
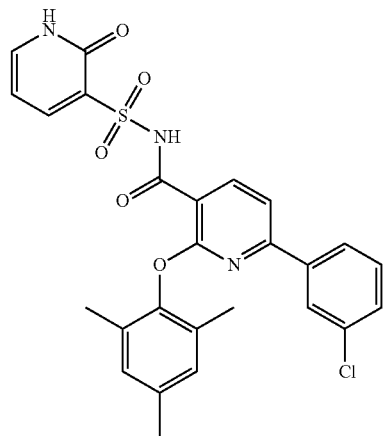 [SMILES: Cc1cc(C)c(Oc2nc(-c3cccc(Cl)c3)ccc2C(=O)NS(=O)(=O)c2ccc[nH]c2=O)c(C)c1]
1095
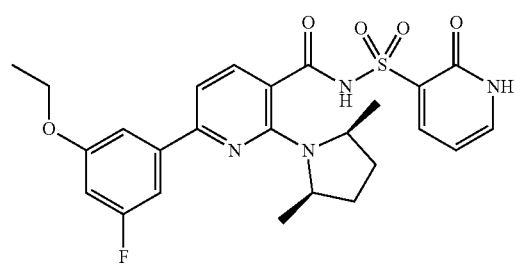 [SMILES: CCOc1cc(F)cc(-c2ccc(C(=O)NS(=O)(=O)c3ccc[nH]c3=O)c(N3[C@H](C)CC[C@@H]3C)n2)c1]
1096
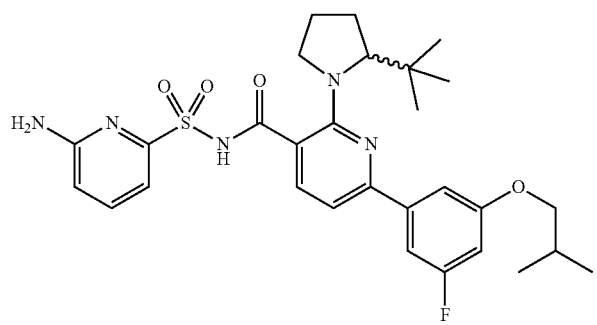 [SMILES: CC(C)COc1cc(F)cc(-c2ccc(C(=O)NS(=O)(=O)c3cccc(N)n3)c(N3CCCC3C(C)(C)C)n2)c1]
1097
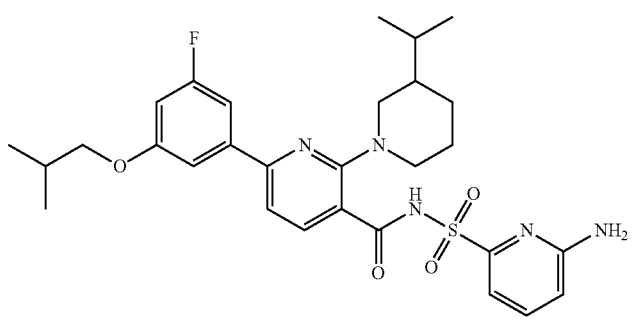 [SMILES: CC(C)COc1cc(F)cc(-c2ccc(C(=O)NS(=O)(=O)c3cccc(N)n3)c(N3CCCC(C(C)C)C3)n2)c1]
1098
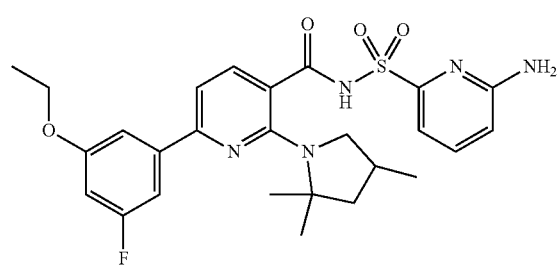 [SMILES: CCOc1cc(F)cc(-c2ccc(C(=O)NS(=O)(=O)c3cccc(N)n3)c(N3CC(C)CC3(C)C)n2)c1]
1099

TABLE 1-continued
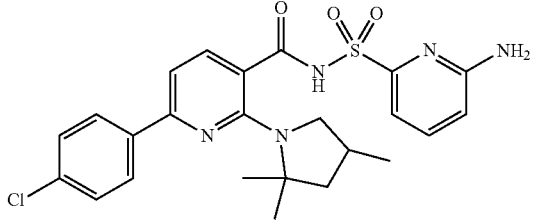 [SMILES: CC1CN(c2nc(-c3ccc(Cl)cc3)ccc2C(=O)NS(=O)(=O)c2cccc(N)n2)C(C)(C)C1]
1100
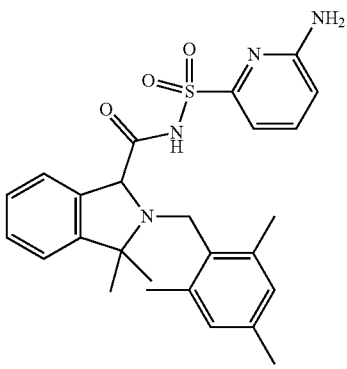 [SMILES: Cc1cc(C)c(CN2C(C(=O)NS(=O)(=O)c3cccc(N)n3)c3ccccc3C2(C)C)c(C)c1]
1101
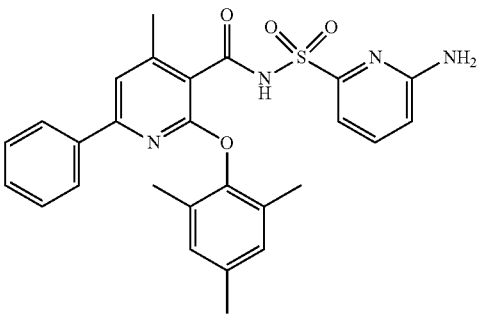 [SMILES: Cc1cc(C)c(Oc2nc(-c3ccccc3)cc(C)c2C(=O)NS(=O)(=O)c2cccc(N)n2)c(C)c1]
1102
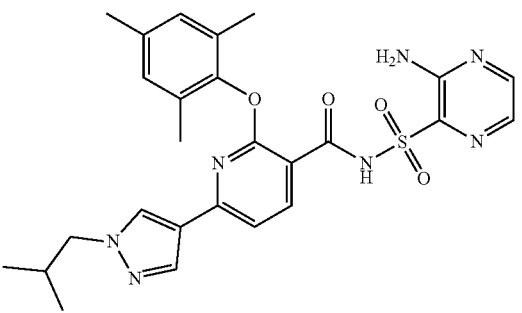 [SMILES: Cc1cc(C)c(Oc2nc(-c3cnn(CC(C)C)c3)ccc2C(=O)NS(=O)(=O)c2nccnc2N)c(C)c1]
1103
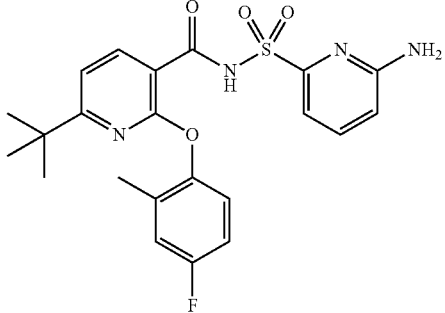 [SMILES: Cc1cc(F)ccc1Oc1nc(C(C)(C)C)ccc1C(=O)NS(=O)(=O)c1cccc(N)n1]
1104

TABLE 1-continued
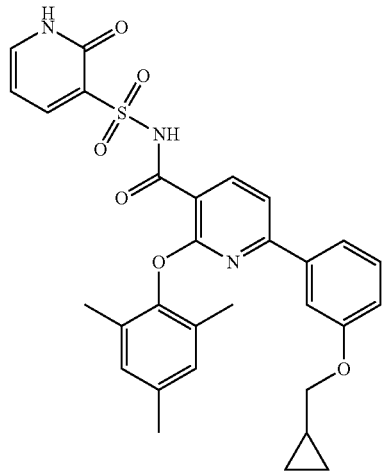 [SMILES: Cc1cc(C)c(Oc2nc(-c3cccc(OCC4CC4)c3)ccc2C(=O)NS(=O)(=O)c2ccc[nH]c2=O)c(C)c1]
1105
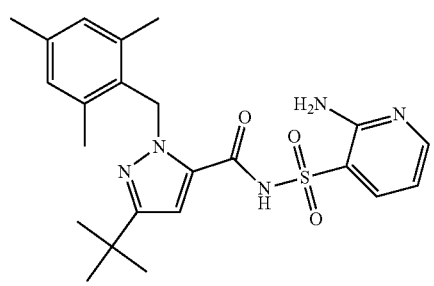 [SMILES: Cc1cc(C)c(Cn2nc(C(C)(C)C)cc2C(=O)NS(=O)(=O)c2cccnc2N)c(C)c1]
1106
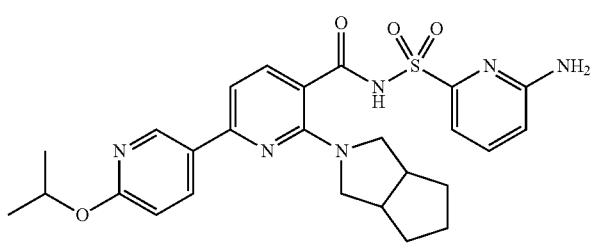 [SMILES: CC(C)Oc1ccc(-c2ccc(C(=O)NS(=O)(=O)c3cccc(N)n3)c(N3CC4CCCC4C3)n2)cn1]
1107
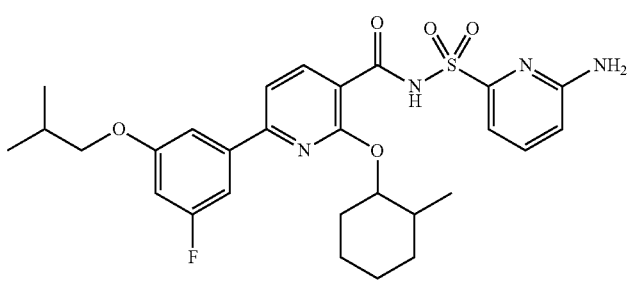 [SMILES: CC(C)COc1cc(F)cc(-c2ccc(C(=O)NS(=O)(=O)c3cccc(N)n3)c(OC3CCCCC3C)n2)c1]
1108
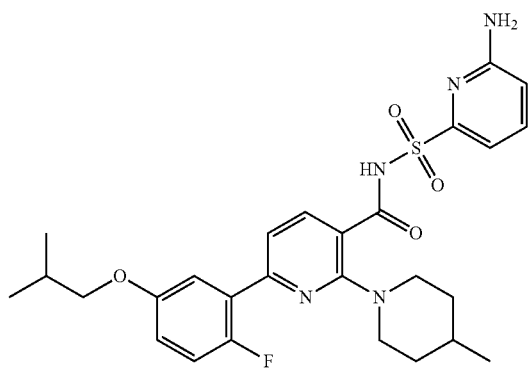 [SMILES: CC(C)COc1ccc(F)c(-c2ccc(C(=O)NS(=O)(=O)c3cccc(N)n3)c(N3CCC(C)CC3)n2)c1]
1109

TABLE 1-continued
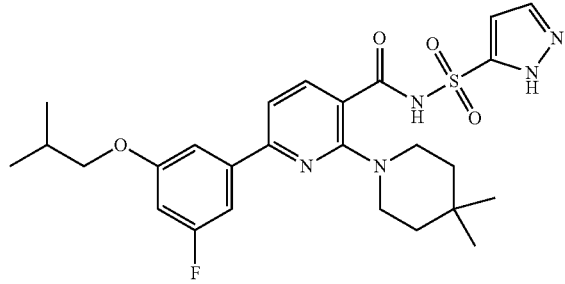 [SMILES: CC(C)COc1cc(F)cc(-c2ccc(C(=O)NS(=O)(=O)c3ccn[nH]3)c(N3CCC(C)(C)CC3)n2)c1] 1110
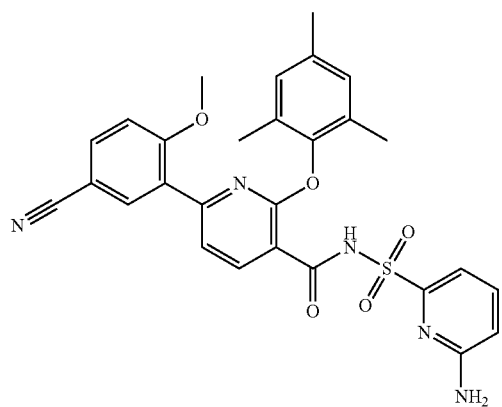 [SMILES: COc1ccc(C#N)cc1-c1ccc(C(=O)NS(=O)(=O)c2cccc(N)n2)c(Oc2c(C)cc(C)cc2C)n1] 1111
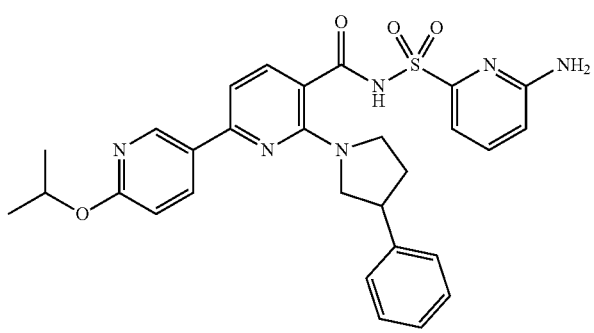 [SMILES: CC(C)Oc1ccc(-c2ccc(C(=O)NS(=O)(=O)c3cccc(N)n3)c(N3CCC(c4ccccc4)C3)n2)cn1] 1112
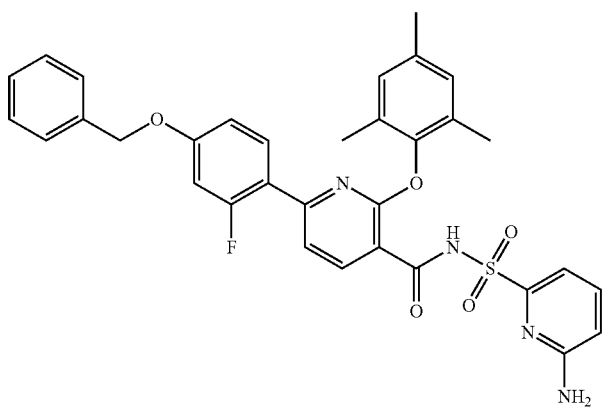 [SMILES: Cc1cc(C)c(Oc2nc(-c3ccc(OCc4ccccc4)cc3F)ccc2C(=O)NS(=O)(=O)c2cccc(N)n2)c(C)c1] 1113

TABLE 1-continued
| | |
|---|---|
| 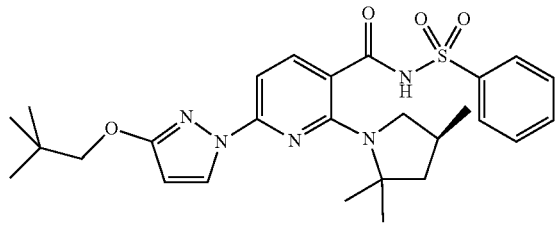 [SMILES: C[C@@H]1CN(c2nc(-n3ccc(OCC(C)(C)C)n3)ccc2C(=O)NS(=O)(=O)c2ccccc2)C(C)(C)C1] | 1114 |
| 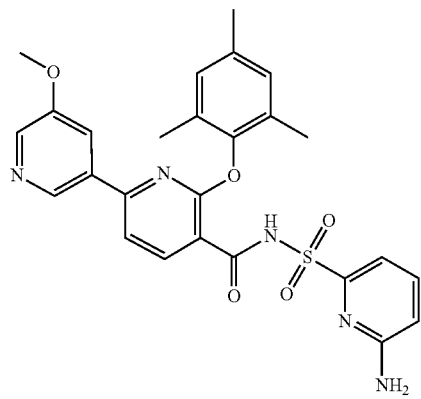 [SMILES: COc1cncc(-c2ccc(C(=O)NS(=O)(=O)c3cccc(N)n3)c(Oc3c(C)cc(C)cc3C)n2)c1] | 1115 |
| 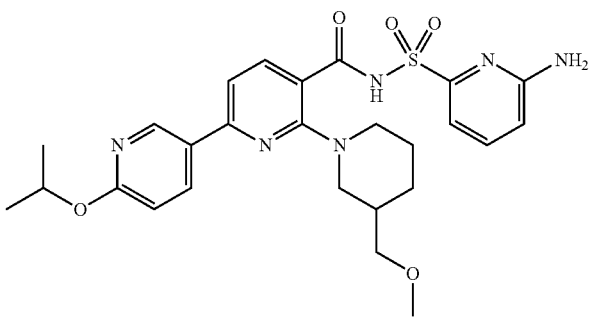 [SMILES: COCC1CCCN(c2nc(-c3ccc(OC(C)C)nc3)ccc2C(=O)NS(=O)(=O)c2cccc(N)n2)C1] | 1116 |
| 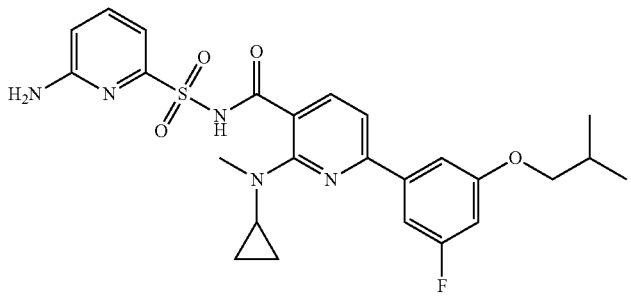 | 1117 |
| 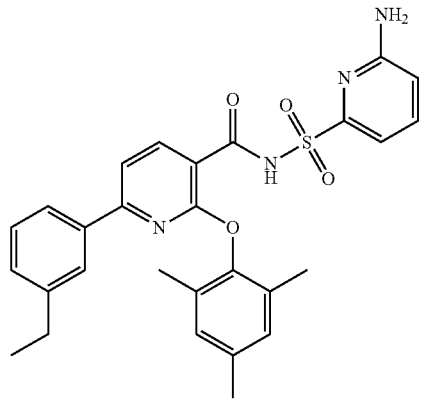 [SMILES: CCc1cccc(-c2ccc(C(=O)NS(=O)(=O)c3cccc(N)n3)c(Oc3c(C)cc(C)cc3C)n2)c1] | 1118 |

TABLE 1-continued
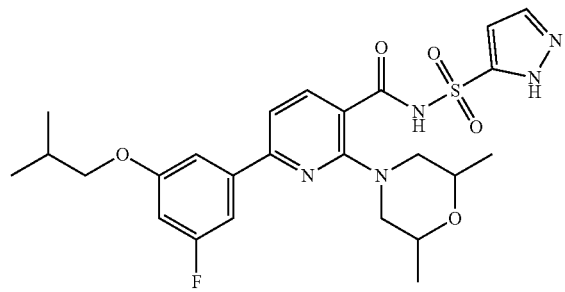 [SMILES: CC(C)COc1cc(F)cc(-c2ccc(C(=O)NS(=O)(=O)c3ccn[nH]3)c(N3CC(C)OC(C)C3)n2)c1] 1119
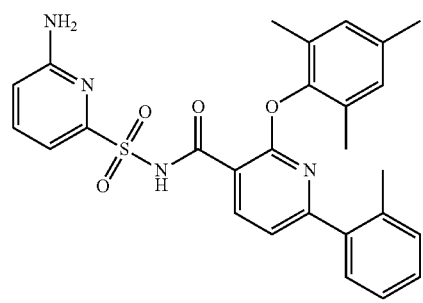 [SMILES: Cc1cc(C)c(Oc2nc(-c3ccccc3C)ccc2C(=O)NS(=O)(=O)c2cccc(N)n2)c(C)c1] 1120
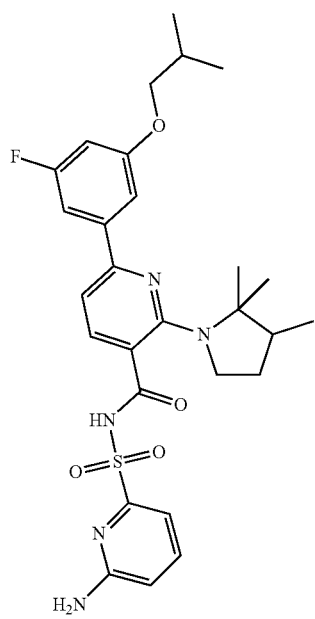 [SMILES: CC(C)COc1cc(F)cc(-c2ccc(C(=O)NS(=O)(=O)c3cccc(N)n3)c(N3CCC(C)C3(C)C)n2)c1] 1121
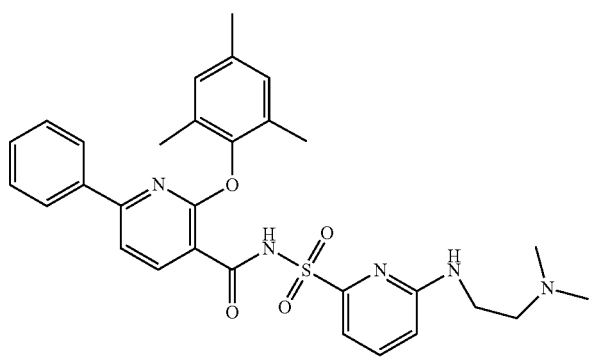 [SMILES: Cc1cc(C)c(Oc2nc(-c3ccccc3)ccc2C(=O)NS(=O)(=O)c2cccc(NCCN(C)C)n2)c(C)c1] 1122

TABLE 1-continued
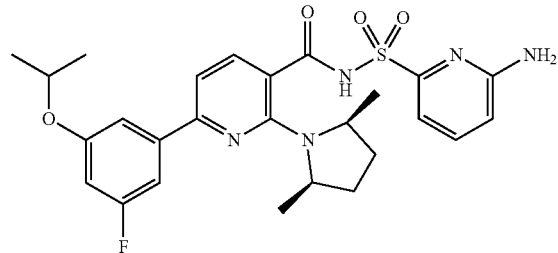 [SMILES: CC(C)Oc1cc(F)cc(-c2ccc(C(=O)NS(=O)(=O)c3cccc(N)n3)c(N3[C@H](C)CC[C@@H]3C)n2)c1]
1123
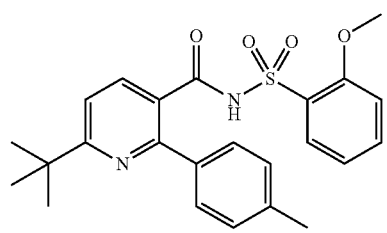 [SMILES: COc1ccccc1S(=O)(=O)NC(=O)c1ccc(C(C)(C)C)nc1-c1ccc(C)cc1]
1124
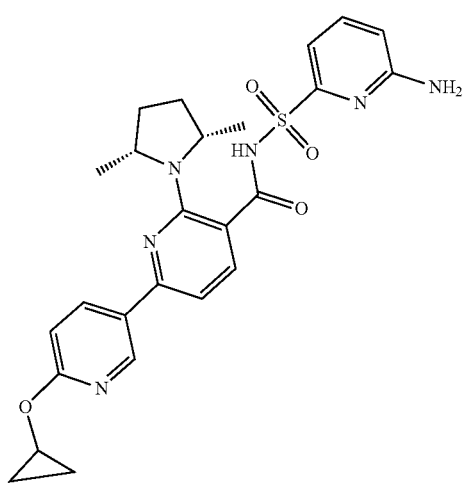 [SMILES: C[C@@H]1CC[C@H](C)N1c1nc(-c2ccc(OC3CC3)nc2)ccc1C(=O)NS(=O)(=O)c1cccc(N)n1]
1125
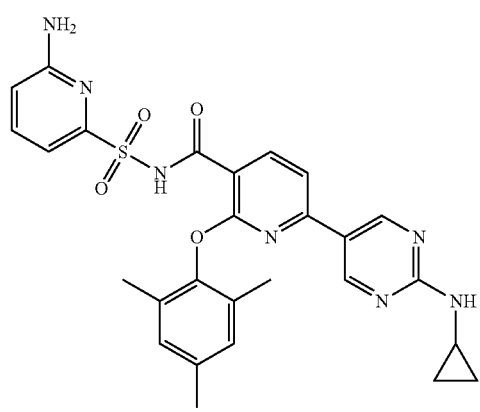 [SMILES: Cc1cc(C)c(Oc2nc(-c3cnc(NC4CC4)nc3)ccc2C(=O)NS(=O)(=O)c2cccc(N)n2)c(C)c1]
1126

TABLE 1-continued
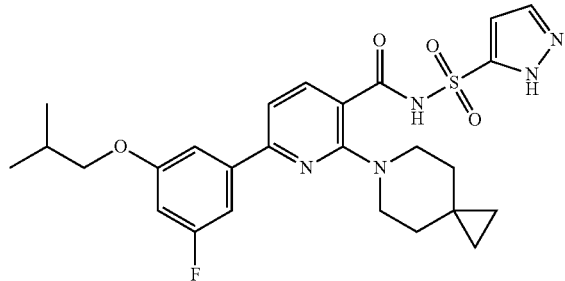 [SMILES: CC(C)COc1cc(F)cc(-c2ccc(C(=O)NS(=O)(=O)c3ccn[nH]3)c(N3CCC4(CC3)CC4)n2)c1]
1127
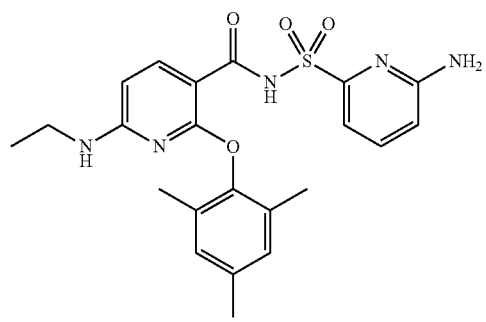 [SMILES: CCNc1ccc(C(=O)NS(=O)(=O)c2cccc(N)n2)c(Oc2c(C)cc(C)cc2C)n1]
1128
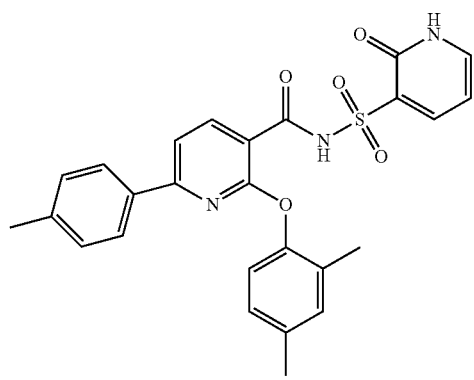 [SMILES: Cc1ccc(-c2ccc(C(=O)NS(=O)(=O)c3ccc[nH]c3=O)c(Oc3ccc(C)cc3C)n2)cc1]
1129
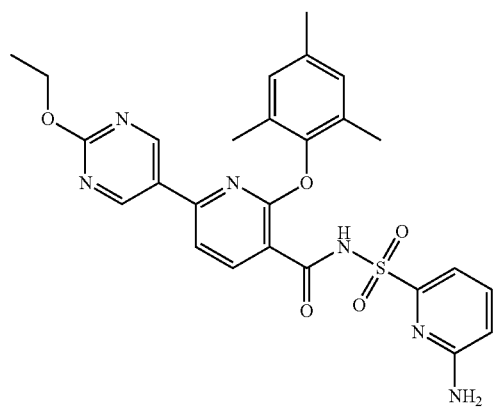 [SMILES: CCOc1ncc(-c2ccc(C(=O)NS(=O)(=O)c3cccc(N)n3)c(Oc3c(C)cc(C)cc3C)n2)cn1]
1130

TABLE 1-continued
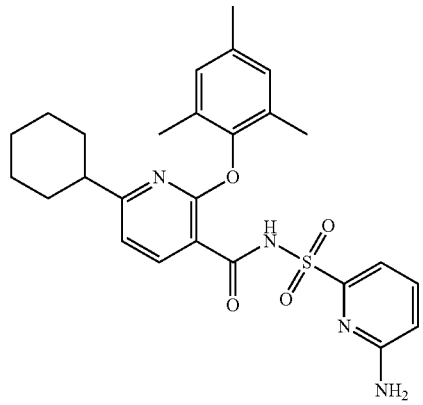 [SMILES: Cc1cc(C)c(Oc2nc(C3CCCCC3)ccc2C(=O)NS(=O)(=O)c2cccc(N)n2)c(C)c1]
1131
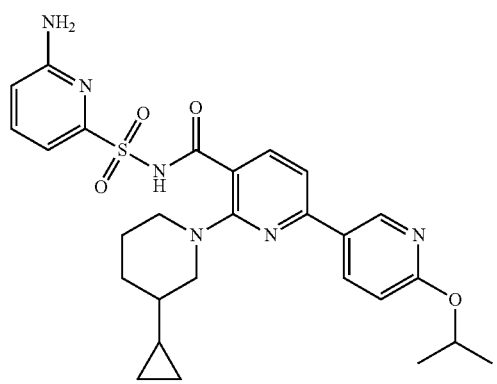 [SMILES: CC(C)Oc1ccc(-c2ccc(C(=O)NS(=O)(=O)c3cccc(N)n3)c(N3CCCC(C4CC4)C3)n2)cn1]
1132
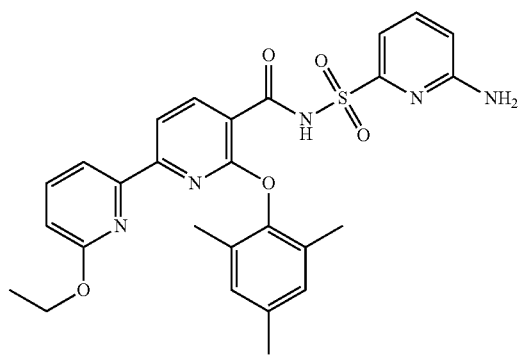 [SMILES: CCOc1cccc(-c2ccc(C(=O)NS(=O)(=O)c3cccc(N)n3)c(Oc3c(C)cc(C)cc3C)n2)n1]
1133
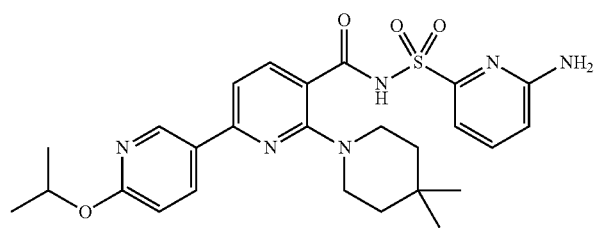 [SMILES: CC(C)Oc1ccc(-c2ccc(C(=O)NS(=O)(=O)c3cccc(N)n3)c(N3CCC(C)(C)CC3)n2)cn1]
1134

TABLE 1-continued
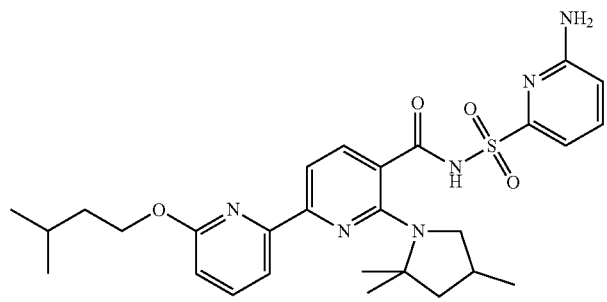 [SMILES: CC(C)CCOc1cccc(-c2ccc(C(=O)NS(=O)(=O)c3cccc(N)n3)c(N3CC(C)CC3(C)C)n2)n1]
1135
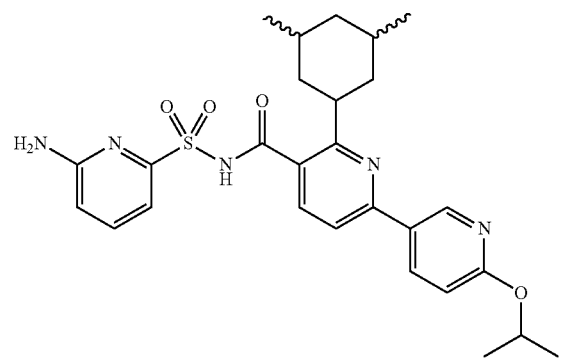
1136
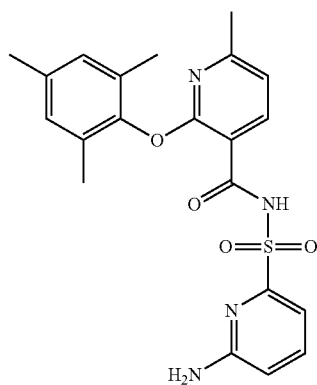 [SMILES: Cc1cc(C)c(Oc2nc(C)ccc2C(=O)NS(=O)(=O)c2cccc(N)n2)c(C)c1]
1137
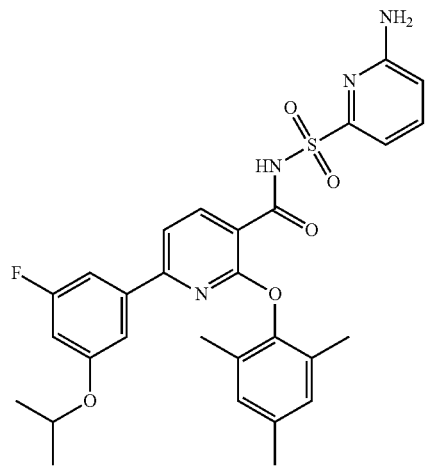 [SMILES: Cc1cc(C)c(Oc2nc(-c3cc(F)cc(OC(C)C)c3)ccc2C(=O)NS(=O)(=O)c2cccc(N)n2)c(C)c1]
1138

TABLE 1-continued
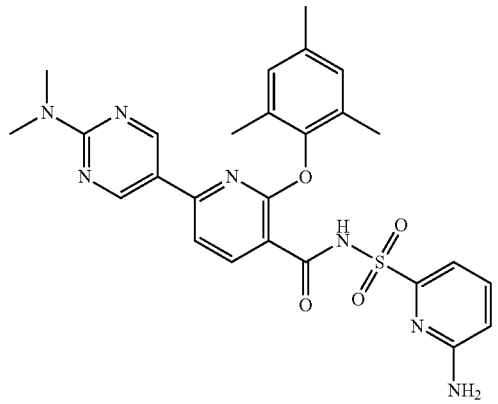 [SMILES: Cc1cc(C)c(Oc2nc(-c3cnc(N(C)C)nc3)ccc2C(=O)NS(=O)(=O)c2cccc(N)n2)c(C)c1]
1139
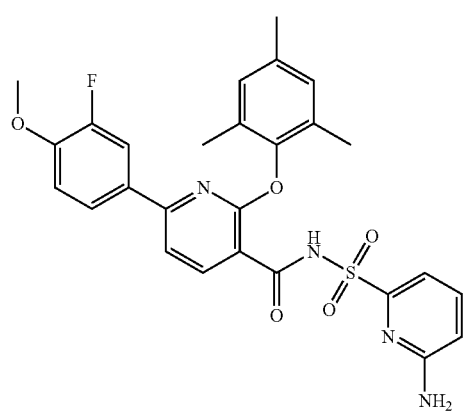
1140
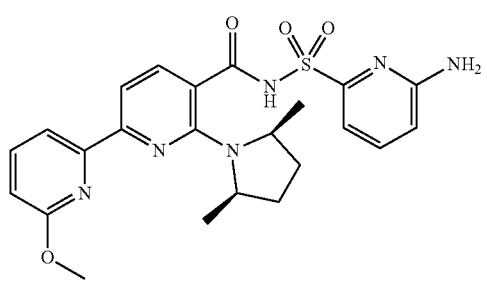 [SMILES: COc1cccc(-c2ccc(C(=O)NS(=O)(=O)c3cccc(N)n3)c(N3[C@H](C)CC[C@@H]3C)n2)n1]
1141
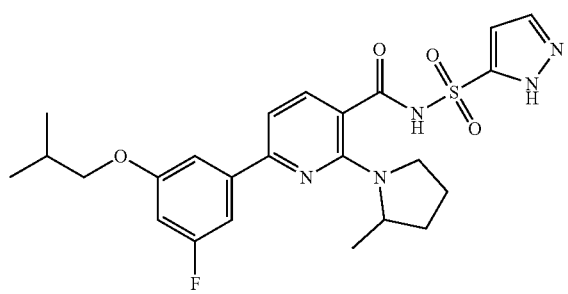 [SMILES: CC(C)COc1cc(F)cc(-c2ccc(C(=O)NS(=O)(=O)c3ccn[nH]3)c(N3CCCC3C)n2)c1]
1142

TABLE 1-continued
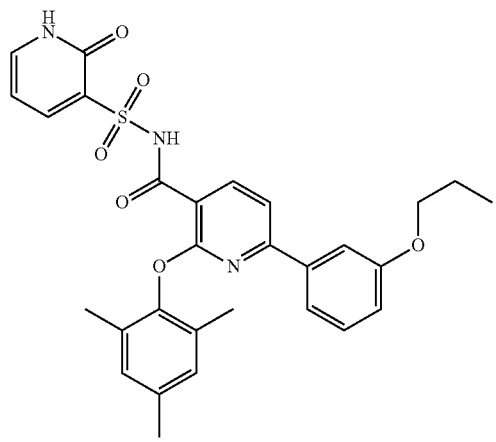 [SMILES: CCCOc1cccc(-c2ccc(C(=O)NS(=O)(=O)c3ccc[nH]c3=O)c(Oc3c(C)cc(C)cc3C)n2)c1]
1143
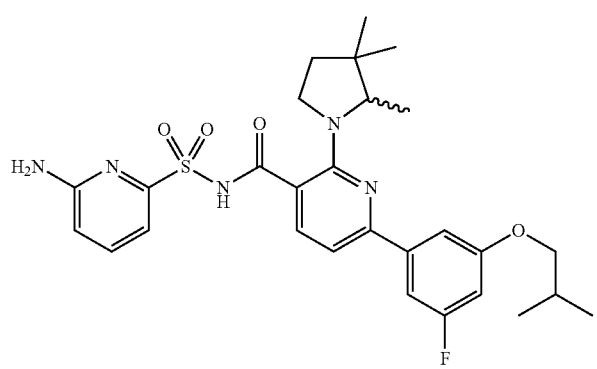 [SMILES: CC(C)COc1cc(F)cc(-c2ccc(C(=O)NS(=O)(=O)c3cccc(N)n3)c(N3CCC(C)(C)C3C)n2)c1]
1144
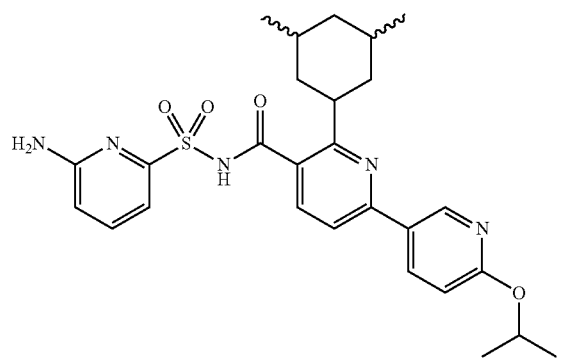
1145
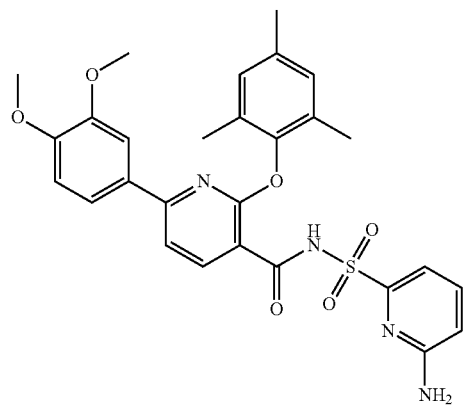 [SMILES: COc1ccc(-c2ccc(C(=O)NS(=O)(=O)c3cccc(N)n3)c(Oc3c(C)cc(C)cc3C)n2)cc1OC]
1146

TABLE 1-continued
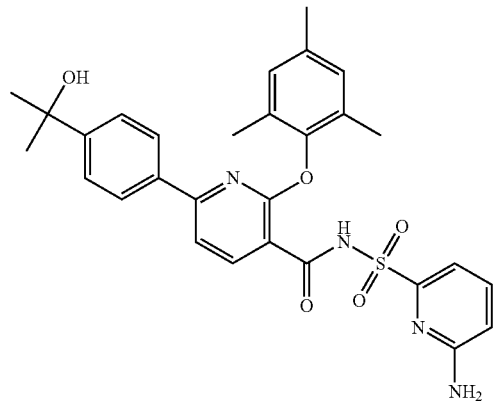 [SMILES: Cc1cc(C)c(Oc2nc(-c3ccc(C(C)(C)O)cc3)ccc2C(=O)NS(=O)(=O)c2cccc(N)n2)c(C)c1]
1147
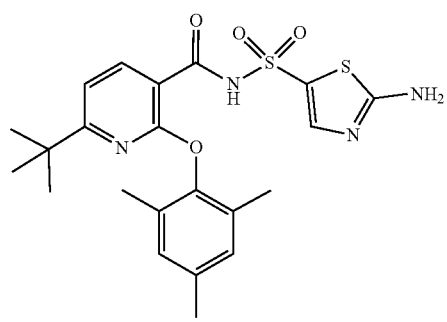 [SMILES: Cc1cc(C)c(Oc2nc(C(C)(C)C)ccc2C(=O)NS(=O)(=O)c2cnc(N)s2)c(C)c1]
1148
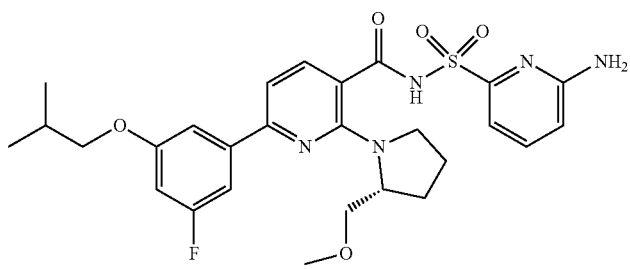 [SMILES: COC[C@H]1CCCN1c1nc(-c2cc(F)cc(OCC(C)C)c2)ccc1C(=O)NS(=O)(=O)c1cccc(N)n1]
1149
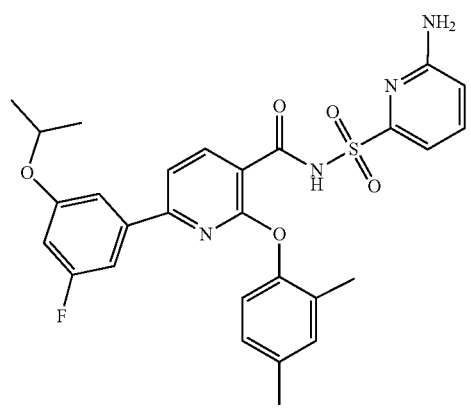 [SMILES: Cc1ccc(Oc2nc(-c3cc(F)cc(OC(C)C)c3)ccc2C(=O)NS(=O)(=O)c2cccc(N)n2)c(C)c1]
1150

TABLE 1-continued
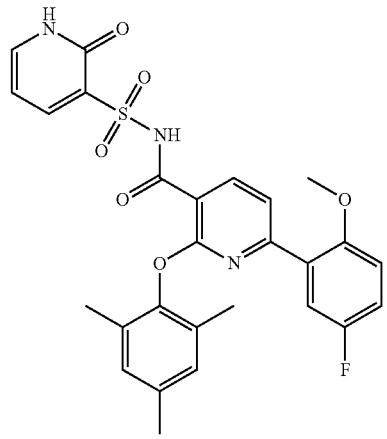 [SMILES: COc1ccc(F)cc1-c1ccc(C(=O)NS(=O)(=O)c2ccc[nH]c2=O)c(Oc2c(C)cc(C)cc2C)n1]
1151
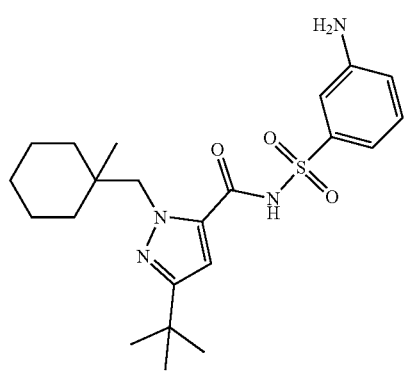 [SMILES: CC1(Cn2nc(C(C)(C)C)cc2C(=O)NS(=O)(=O)c2cccc(N)c2)CCCCC1]
1152
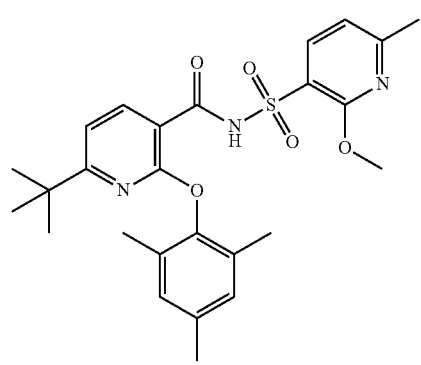 [SMILES: COc1nc(C)ccc1S(=O)(=O)NC(=O)c1ccc(C(C)(C)C)nc1Oc1c(C)cc(C)cc1C]
1153
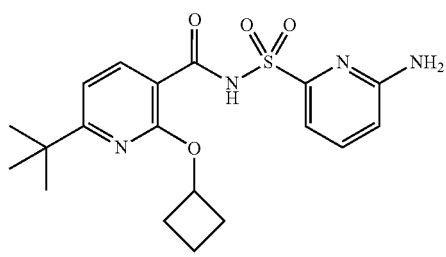 [SMILES: CC(C)(C)c1ccc(C(=O)NS(=O)(=O)c2cccc(N)n2)c(OC2CCC2)n1]
1154

TABLE 1-continued
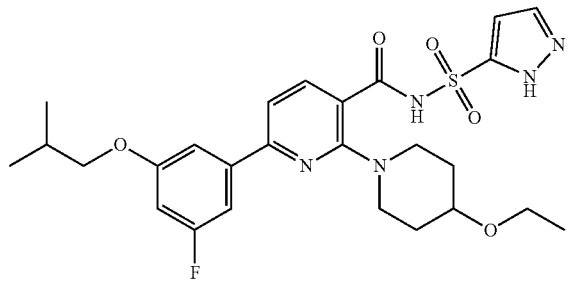 [SMILES: CCOC1CCN(c2nc(-c3cc(F)cc(OCC(C)C)c3)ccc2C(=O)NS(=O)(=O)c2ccn[nH]2)CC1]
1155
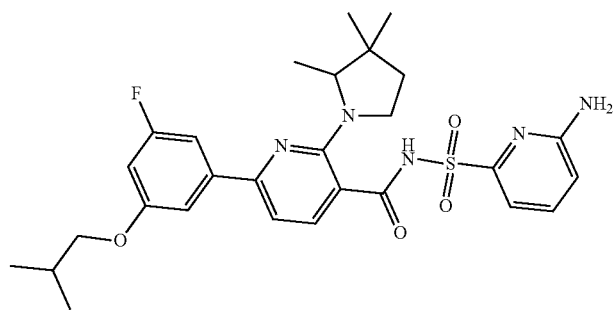 [SMILES: CC(C)COc1cc(F)cc(-c2ccc(C(=O)NS(=O)(=O)c3cccc(N)n3)c(N3CCC(C)(C)C3C)n2)c1]
1156
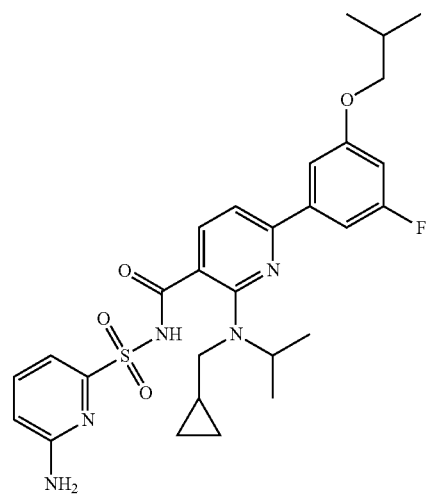
1157
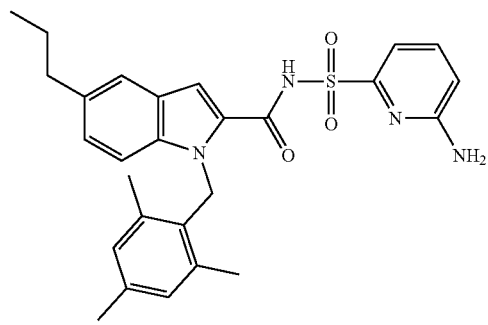 [SMILES: CCCc1ccc2c(c1)cc(C(=O)NS(=O)(=O)c1cccc(N)n1)n2Cc1c(C)cc(C)cc1C]
1158

TABLE 1-continued
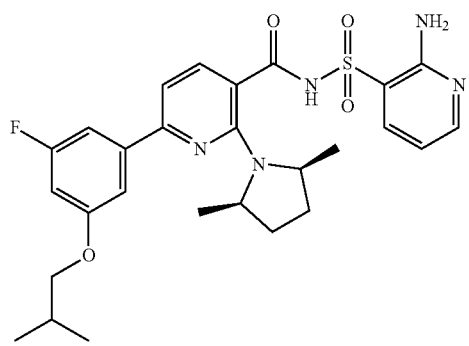 [SMILES: CC(C)COc1cc(F)cc(-c2ccc(C(=O)NS(=O)(=O)c3cccnc3N)c(N3[C@H](C)CC[C@@H]3C)n2)c1]
1159
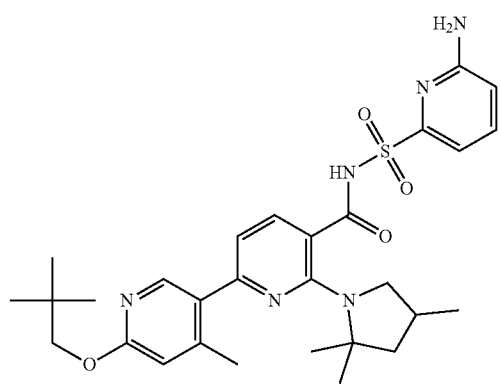 [SMILES: Cc1cc(OCC(C)(C)C)ncc1-c1ccc(C(=O)NS(=O)(=O)c2cccc(N)n2)c(N2CC(C)CC2(C)C)n1]
1160
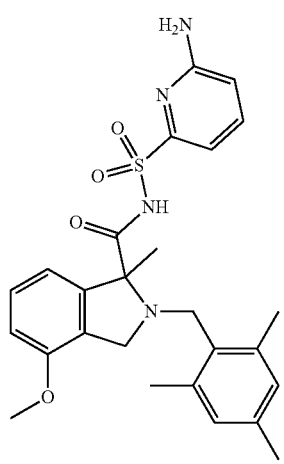
1161
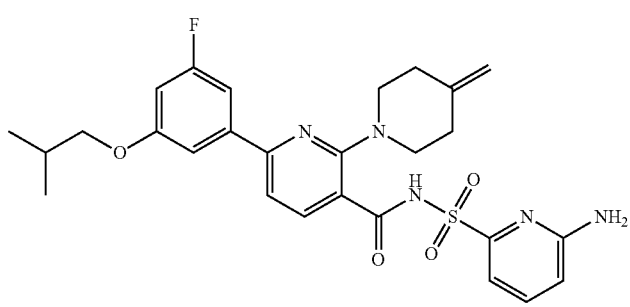 [SMILES: C=C1CCN(c2nc(-c3cc(F)cc(OCC(C)C)c3)ccc2C(=O)NS(=O)(=O)c2cccc(N)n2)CC1]
1162

| | |
|---|---|
| 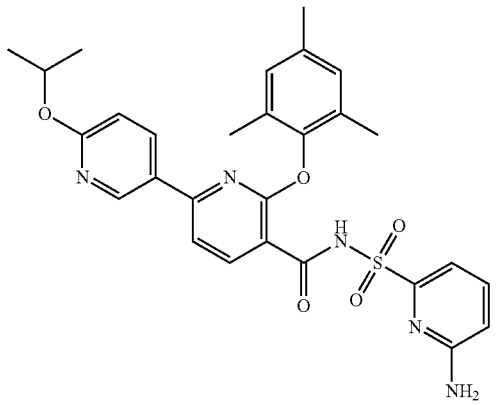 | 1163 |
| 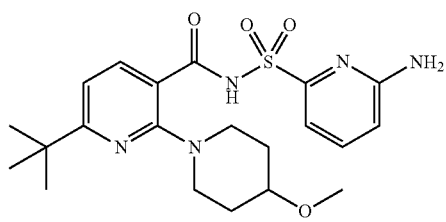 [SMILES: COC1CCN(c2nc(C(C)(C)C)ccc2C(=O)NS(=O)(=O)c2cccc(N)n2)CC1] | 1164 |
| 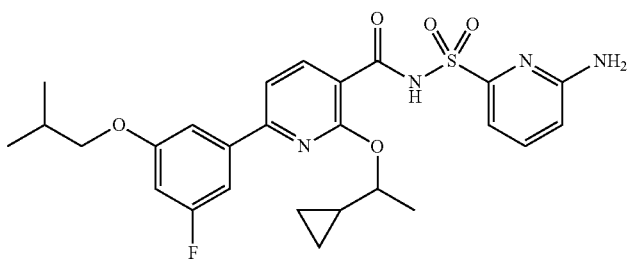 | 1165 |
| 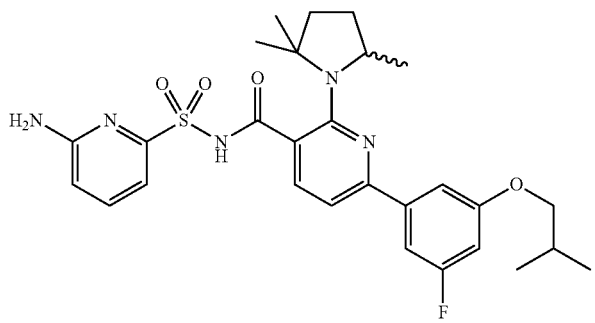 [SMILES: CC(C)COc1cc(F)cc(-c2ccc(C(=O)NS(=O)(=O)c3cccc(N)n3)c(N3C(C)CCC3(C)C)n2)c1] | 1166 |
| 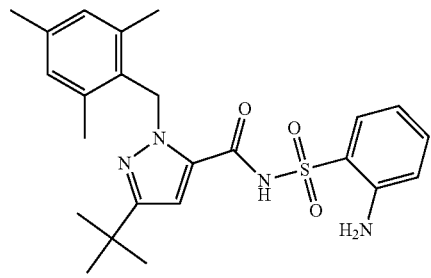 [SMILES: Cc1cc(C)c(Cn2nc(C(C)(C)C)cc2C(=O)NS(=O)(=O)c2ccccc2N)c(C)c1] | 1167 |

TABLE 1-continued
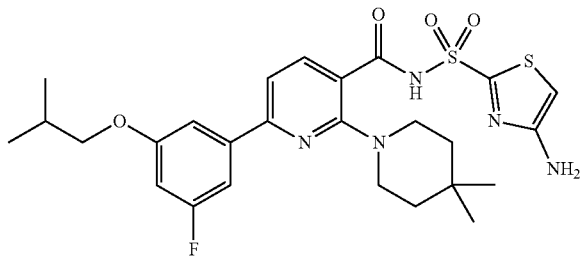 [SMILES: CC(C)COc1cc(F)cc(-c2ccc(C(=O)NS(=O)(=O)c3nc(N)cs3)c(N3CCC(C)(C)CC3)n2)c1]
1168
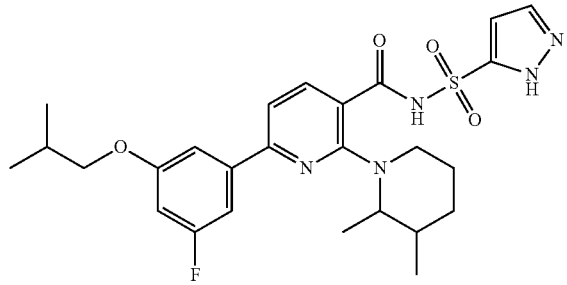 [SMILES: CC(C)COc1cc(F)cc(-c2ccc(C(=O)NS(=O)(=O)c3ccn[nH]3)c(N3CCCC(C)C3C)n2)c1]
1169
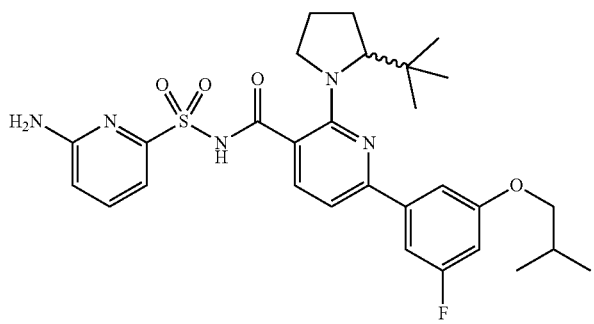 [SMILES: CC(C)COc1cc(F)cc(-c2ccc(C(=O)NS(=O)(=O)c3cccc(N)n3)c(N3CCCC3C(C)(C)C)n2)c1]
1170
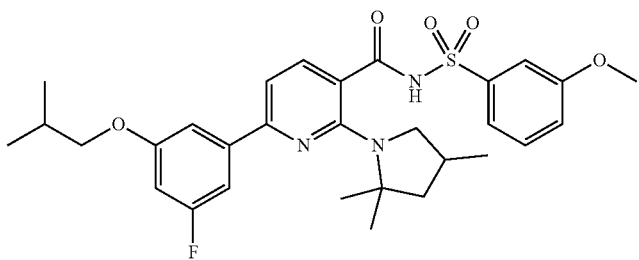 [SMILES: COc1cccc(S(=O)(=O)NC(=O)c2ccc(-c3cc(F)cc(OCC(C)C)c3)nc2N2CC(C)CC2(C)C)c1]
1171
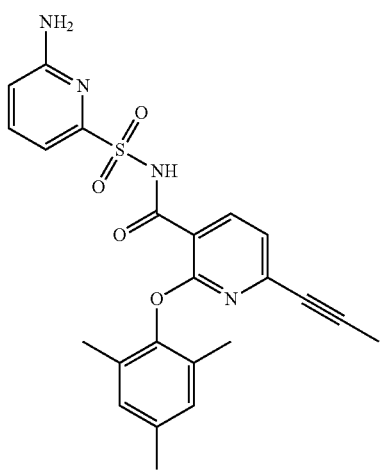 [SMILES: CC#Cc1ccc(C(=O)NS(=O)(=O)c2cccc(N)n2)c(Oc2c(C)cc(C)cc2C)n1]
1172

TABLE 1-continued
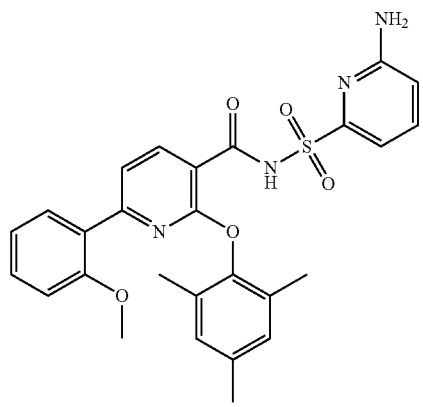 [SMILES: COc1ccccc1-c1ccc(C(=O)NS(=O)(=O)c2cccc(N)n2)c(Oc2c(C)cc(C)cc2C)n1]
1173
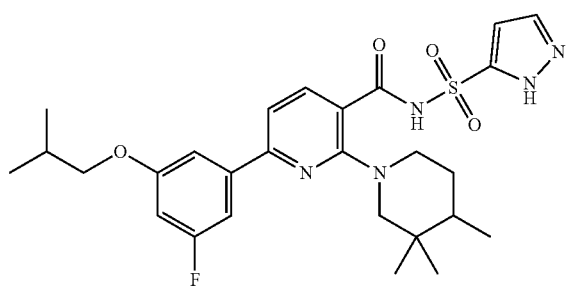 [SMILES: CC(C)COc1cc(F)cc(-c2ccc(C(=O)NS(=O)(=O)c3ccn[nH]3)c(N3CCC(C)C(C)(C)C3)n2)c1]
1174
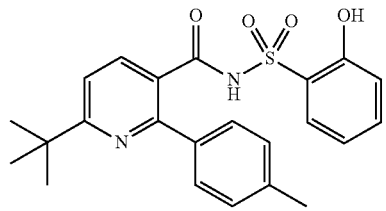
1175
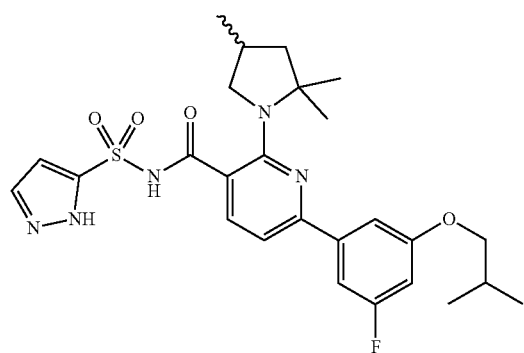 [SMILES: CC(C)COc1cc(F)cc(-c2ccc(C(=O)NS(=O)(=O)c3ccn[nH]3)c(N3CC(C)CC3(C)C)n2)c1]
1176

TABLE 1-continued
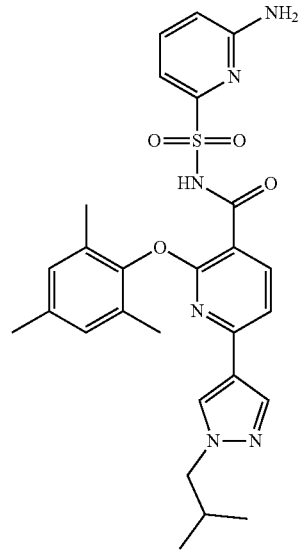 [SMILES: Cc1cc(C)c(Oc2nc(-c3cnn(CC(C)C)c3)ccc2C(=O)NS(=O)(=O)c2cccc(N)n2)c(C)c1]
1177
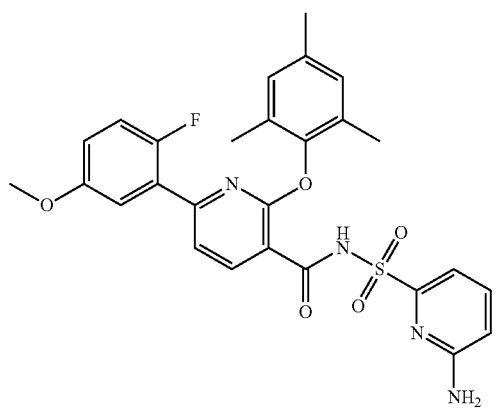 [SMILES: COc1ccc(F)c(-c2ccc(C(=O)NS(=O)(=O)c3cccc(N)n3)c(Oc3c(C)cc(C)cc3C)n2)c1]
1178
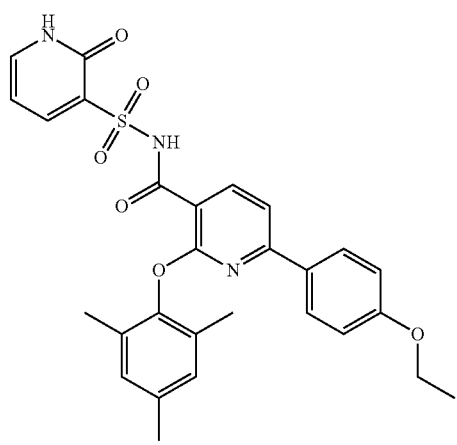 [SMILES: CCOc1ccc(-c2ccc(C(=O)NS(=O)(=O)c3ccc[nH]c3=O)c(Oc3c(C)cc(C)cc3C)n2)cc1]
1179

TABLE 1-continued
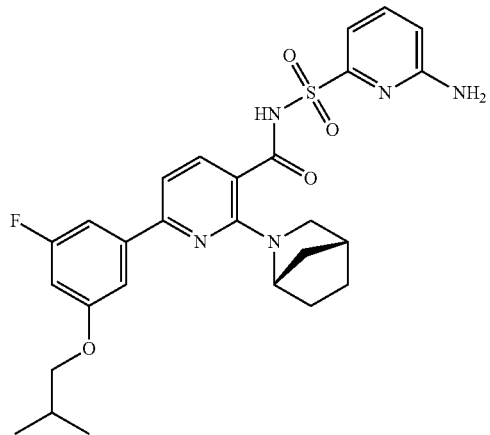 [SMILES: CC(C)COc1cc(F)cc(-c2ccc(C(=O)NS(=O)(=O)c3cccc(N)n3)c(N3C[C@@H]4CC[C@H]3C4)n2)c1]
1180
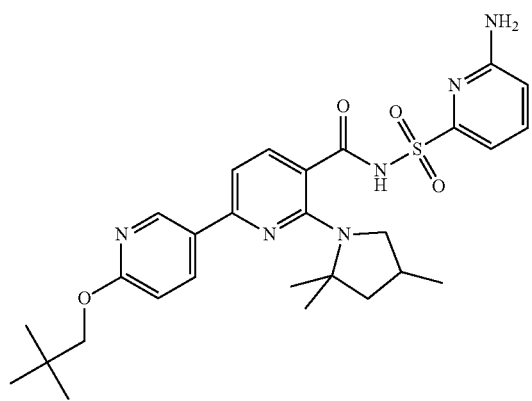 [SMILES: CC1CN(c2nc(-c3ccc(OCC(C)(C)C)nc3)ccc2C(=O)NS(=O)(=O)c2cccc(N)n2)C(C)(C)C1]
1181
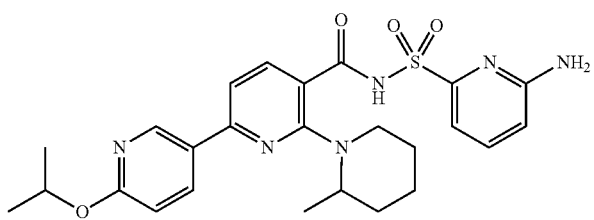 [SMILES: CC(C)Oc1ccc(-c2ccc(C(=O)NS(=O)(=O)c3cccc(N)n3)c(N3CCCCC3C)n2)cn1]
1182
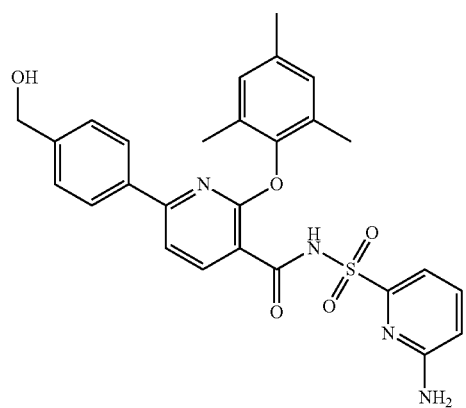 [SMILES: Cc1cc(C)c(Oc2nc(-c3ccc(CO)cc3)ccc2C(=O)NS(=O)(=O)c2cccc(N)n2)c(C)c1]
1183

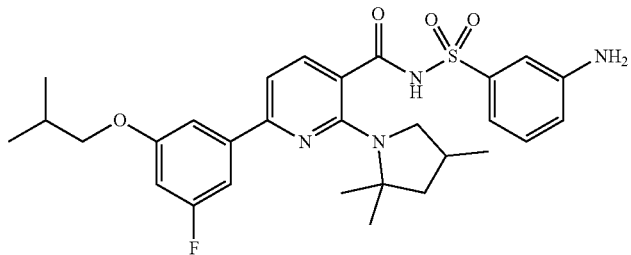 [SMILES: CC(C)COc1cc(F)cc(-c2ccc(C(=O)NS(=O)(=O)c3cccc(N)c3)c(N3CC(C)CC3(C)C)n2)c1]
1184
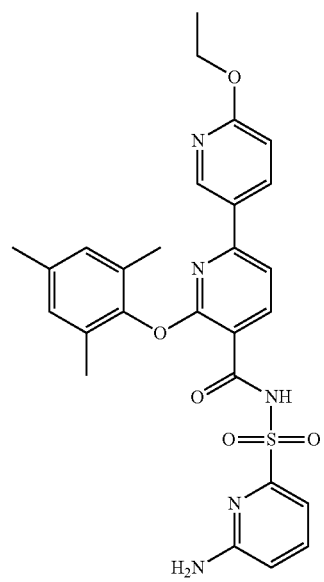 [SMILES: CCOc1ccc(-c2ccc(C(=O)NS(=O)(=O)c3cccc(N)n3)c(Oc3c(C)cc(C)cc3C)n2)cn1]
1185
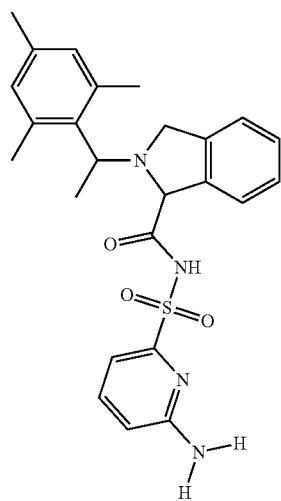
1186

TABLE 1-continued
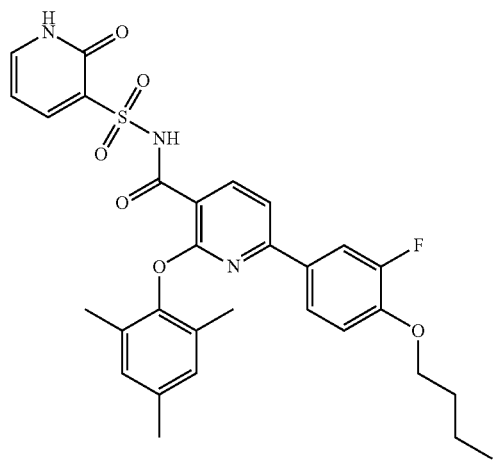 [SMILES: CCCCOc1ccc(-c2ccc(C(=O)NS(=O)(=O)c3ccc[nH]c3=O)c(Oc3c(C)cc(C)cc3C)n2)cc1F]
1187
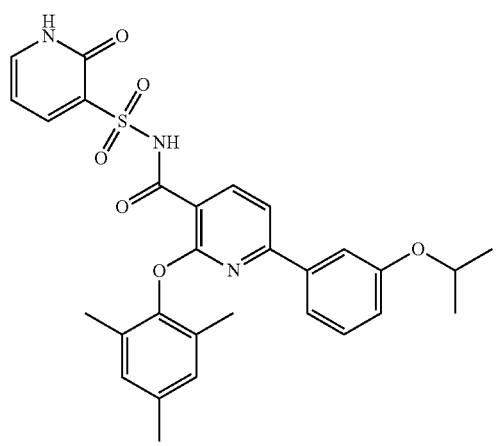 [SMILES: Cc1cc(C)c(Oc2nc(-c3cccc(OC(C)C)c3)ccc2C(=O)NS(=O)(=O)c2ccc[nH]c2=O)c(C)c1]
1188
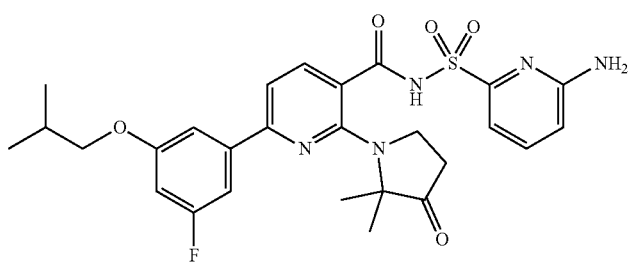 [SMILES: CC(C)COc1cc(F)cc(-c2ccc(C(=O)NS(=O)(=O)c3cccc(N)n3)c(N3CCC(=O)C3(C)C)n2)c1]
1189
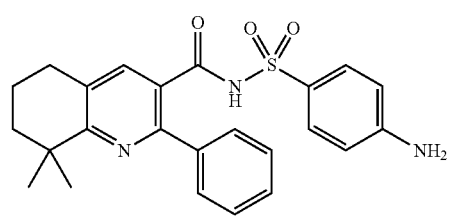 [SMILES: CC1(C)CCCc2cc(C(=O)NS(=O)(=O)c3ccc(N)cc3)c(-c3ccccc3)nc21]
1190

TABLE 1-continued

1191

1192

1193

TABLE 1-continued

| | |
|---|---|
| (structure) | 1194 |
| (structure) | 1195 |
| (structure) | 1196 |
| (structure) | 1197 |
| (structure) | 1198 |

TABLE 1-continued
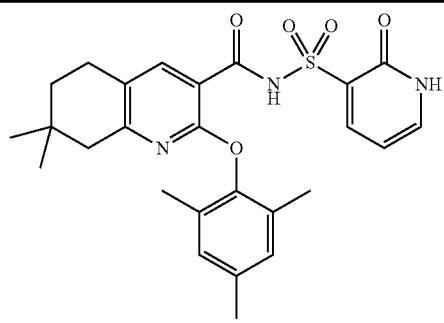
1199
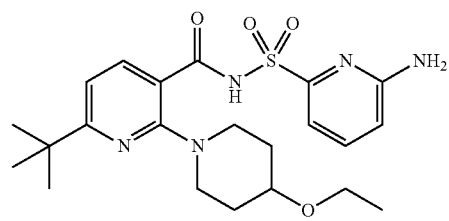
1200
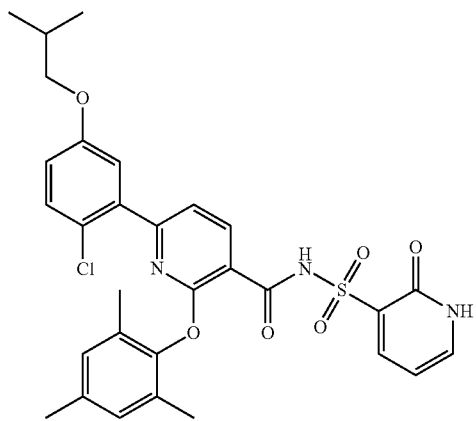 [SMILES: Cc1cc(C)c(Oc2nc(-c3cc(OCC(C)C)ccc3Cl)ccc2C(=O)NS(=O)(=O)c2ccc[nH]c2=O)c(C)c1]
1201
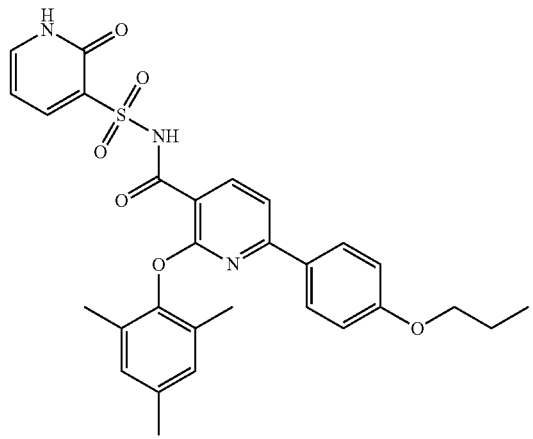 [SMILES: CCCOc1ccc(-c2ccc(C(=O)NS(=O)(=O)c3ccc[nH]c3=O)c(Oc3c(C)cc(C)cc3C)n2)cc1]
1202
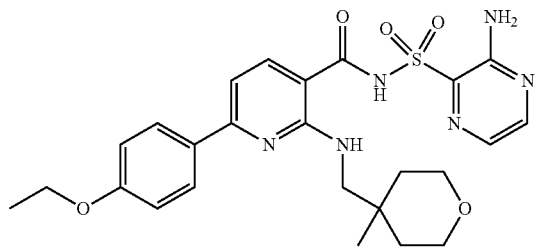 [SMILES: CCOc1ccc(-c2ccc(C(=O)NS(=O)(=O)c3nccnc3N)c(NCC3(C)CCOCC3)n2)cc1]
1203

TABLE 1-continued
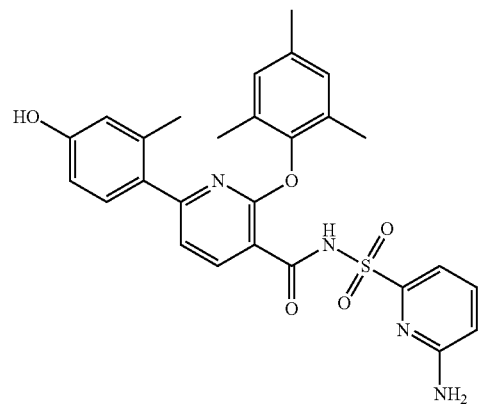
1204
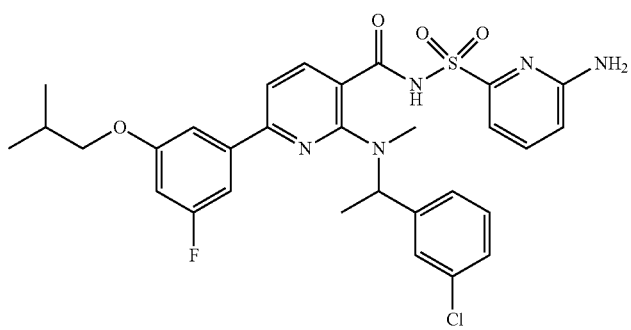 [SMILES: CC(C)COc1cc(F)cc(-c2ccc(C(=O)NS(=O)(=O)c3cccc(N)n3)c(N(C)C(C)c3cccc(Cl)c3)n2)c1]
1205
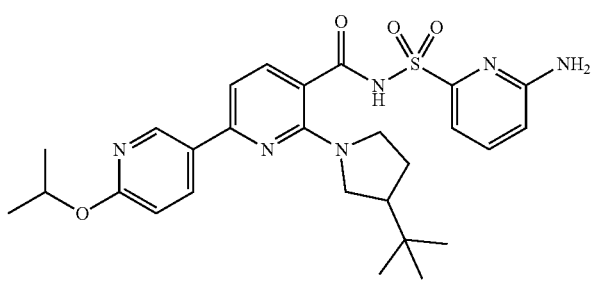 [SMILES: CC(C)Oc1ccc(-c2ccc(C(=O)NS(=O)(=O)c3cccc(N)n3)c(N3CCC(C(C)(C)C)C3)n2)cn1]
1206
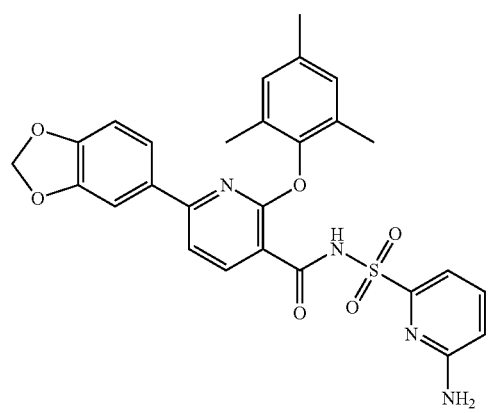 [SMILES: Cc1cc(C)c(Oc2nc(-c3ccc4c(c3)OCO4)ccc2C(=O)NS(=O)(=O)c2cccc(N)n2)c(C)c1]
1207

TABLE 1-continued
| | |
|---|---|
| 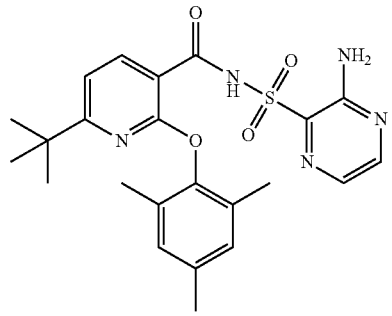 [SMILES: Cc1cc(C)c(Oc2nc(C(C)(C)C)ccc2C(=O)NS(=O)(=O)c2nccnc2N)c(C)c1] | 1208 |
| 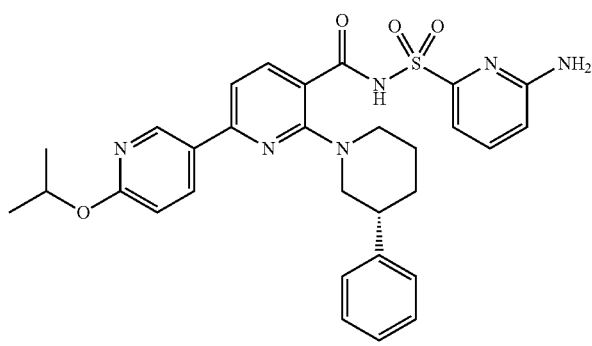 [SMILES: CC(C)Oc1ccc(-c2ccc(C(=O)NS(=O)(=O)c3cccc(N)n3)c(N3CCC[C@H](c4ccccc4)C3)n2)cn1] | 1209 |
| 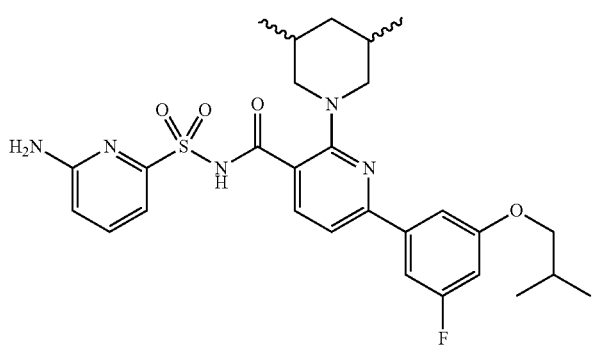 | 1210 |
| 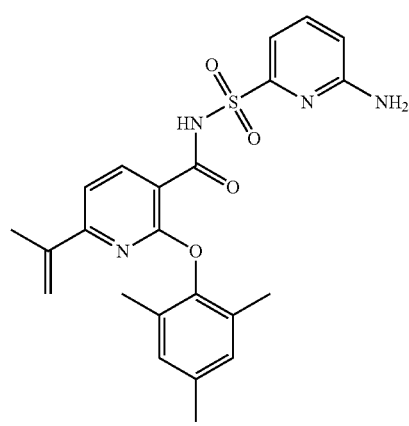 [SMILES: C=C(C)c1ccc(C(=O)NS(=O)(=O)c2cccc(N)n2)c(Oc2c(C)cc(C)cc2C)n1] | 1211 |

TABLE 1-continued
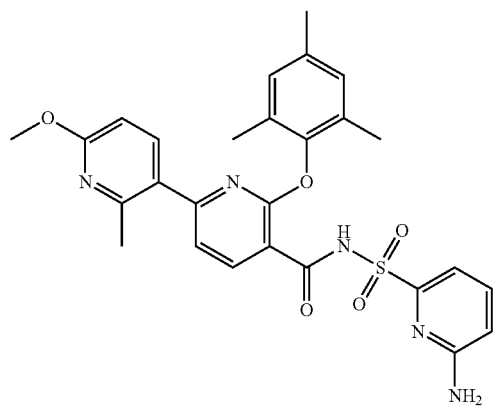 [SMILES: COc1ccc(-c2ccc(C(=O)NS(=O)(=O)c3cccc(N)n3)c(Oc3c(C)cc(C)cc3C)n2)c(C)n1]
1212
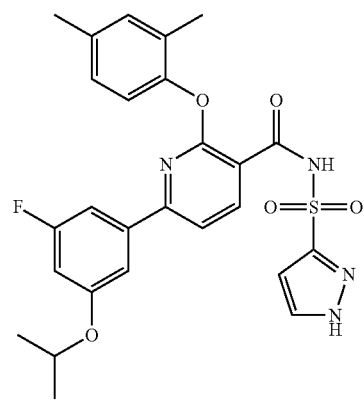 [SMILES: Cc1ccc(Oc2nc(-c3cc(F)cc(OC(C)C)c3)ccc2C(=O)NS(=O)(=O)c2cc[nH]n2)c(C)c1]
1213
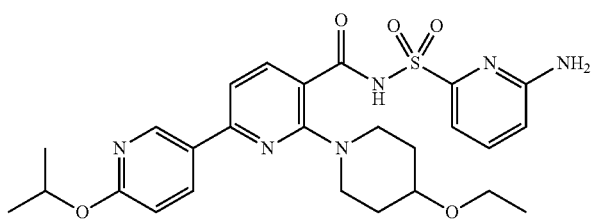 [SMILES: CCOC1CCN(c2nc(-c3ccc(OC(C)C)nc3)ccc2C(=O)NS(=O)(=O)c2cccc(N)n2)CC1]
1214
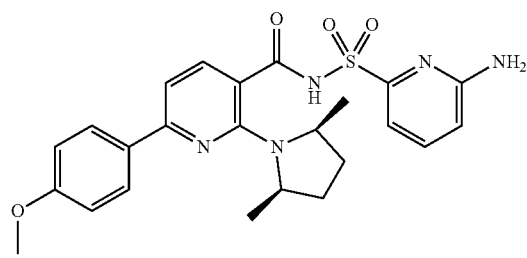 [SMILES: COc1ccc(-c2ccc(C(=O)NS(=O)(=O)c3cccc(N)n3)c(N3[C@H](C)CC[C@@H]3C)n2)cc1]
1215
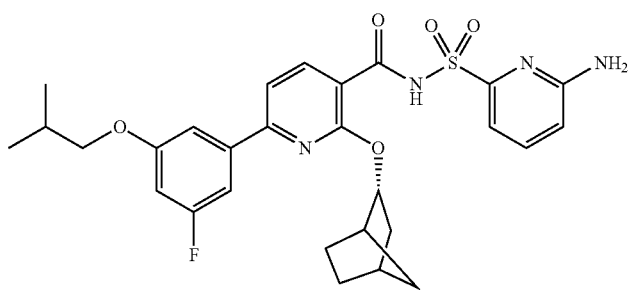 [SMILES: CC(C)COc1cc(F)cc(-c2ccc(C(=O)NS(=O)(=O)c3cccc(N)n3)c(O[C@@H]3CC4CCC3C4)n2)c1]
1216

TABLE 1-continued
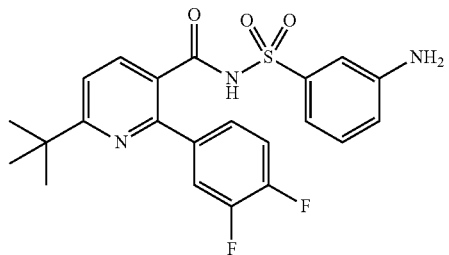
1217
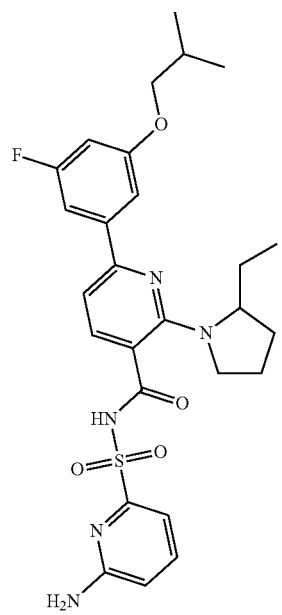 [SMILES: CCC1CCCN1c1nc(-c2cc(F)cc(OCC(C)C)c2)ccc1C(=O)NS(=O)(=O)c1cccc(N)n1]
1218
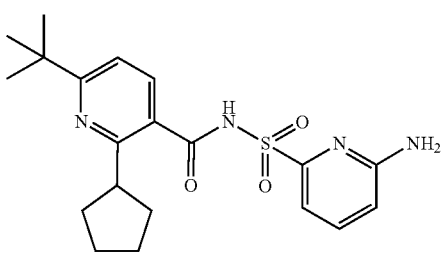 [SMILES: CC(C)(C)c1ccc(C(=O)NS(=O)(=O)c2cccc(N)n2)c(C2CCCC2)n1]
1219
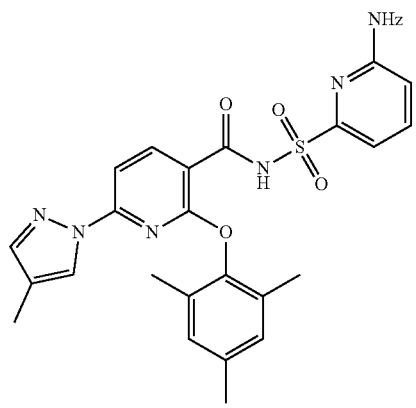
1220

TABLE 1-continued
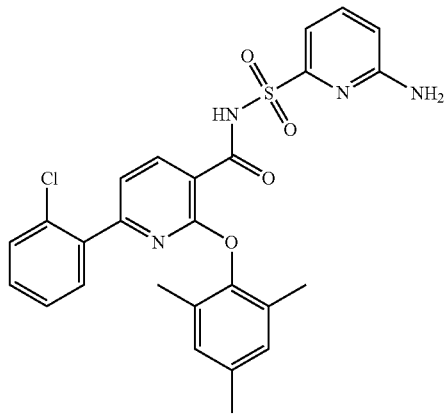 [SMILES: Cc1cc(C)c(Oc2nc(-c3ccccc3Cl)ccc2C(=O)NS(=O)(=O)c2cccc(N)n2)c(C)c1]
1221
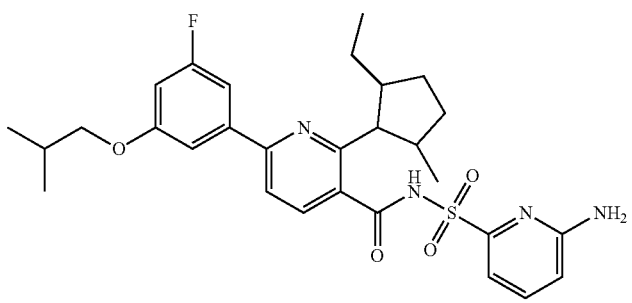 [SMILES: CCC1CCC(C)C1c1nc(-c2cc(F)cc(OCC(C)C)c2)ccc1C(=O)NS(=O)(=O)c1cccc(N)n1]
1222
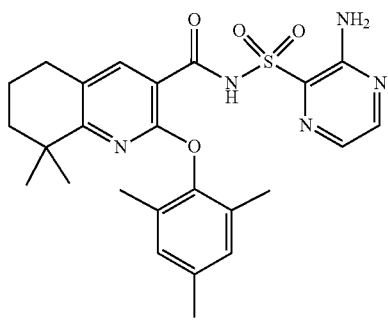 [SMILES: Cc1cc(C)c(Oc2nc3c(cc2C(=O)NS(=O)(=O)c2nccnc2N)CCCC3(C)C)c(C)c1]
1223
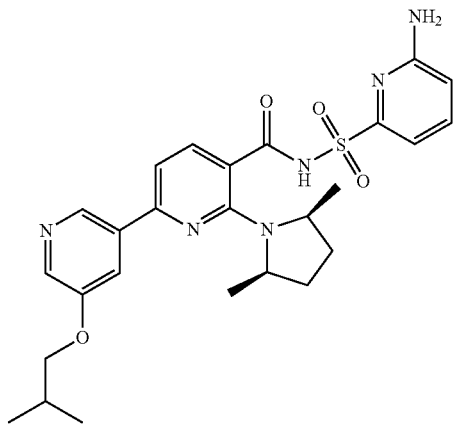 [SMILES: CC(C)COc1cncc(-c2ccc(C(=O)NS(=O)(=O)c3cccc(N)n3)c(N3[C@H](C)CC[C@@H]3C)n2)c1]
1224

TABLE 1-continued
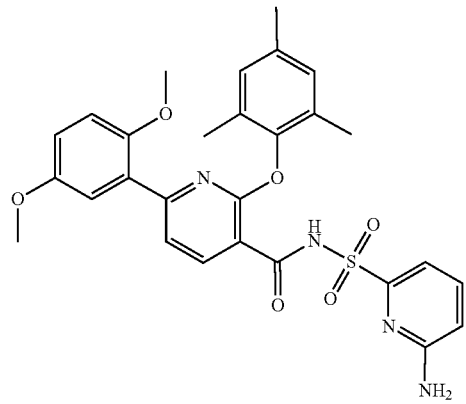 [SMILES: COc1ccc(OC)c(-c2ccc(C(=O)NS(=O)(=O)c3cccc(N)n3)c(Oc3c(C)cc(C)cc3C)n2)c1]
1225
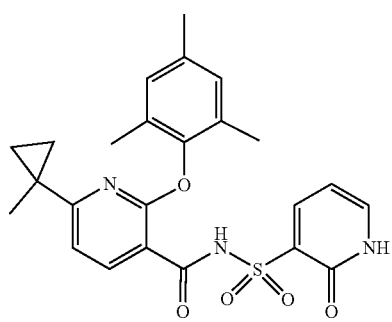 [SMILES: Cc1cc(C)c(Oc2nc(C3(C)CC3)ccc2C(=O)NS(=O)(=O)c2ccc[nH]c2=O)c(C)c1]
1226
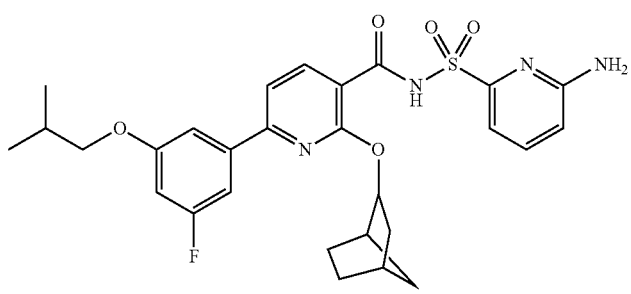 [SMILES: CC(C)COc1cc(F)cc(-c2ccc(C(=O)NS(=O)(=O)c3cccc(N)n3)c(OC3CC4CCC3C4)n2)c1]
1227
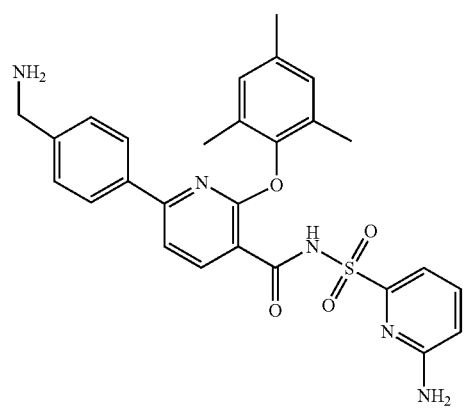 [SMILES: Cc1cc(C)c(Oc2nc(-c3ccc(CN)cc3)ccc2C(=O)NS(=O)(=O)c2cccc(N)n2)c(C)c1]
1228

TABLE 1-continued
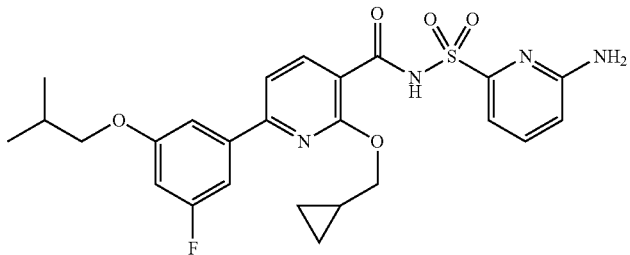 [SMILES: CC(C)COc1cc(F)cc(-c2ccc(C(=O)NS(=O)(=O)c3cccc(N)n3)c(OCC3CC3)n2)c1] 1229
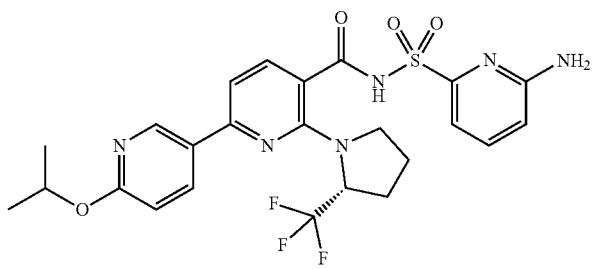 [SMILES: CC(C)Oc1ccc(-c2ccc(C(=O)NS(=O)(=O)c3cccc(N)n3)c(N3CCC[C@@H]3C(F)(F)F)n2)cn1] 1230
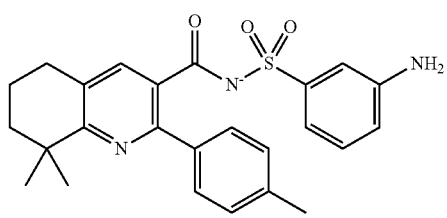 [SMILES: Cc1ccc(-c2nc3c(cc2C(=O)[N-]S(=O)(=O)c2cccc(N)c2)CCCC3(C)C)cc1] 1231
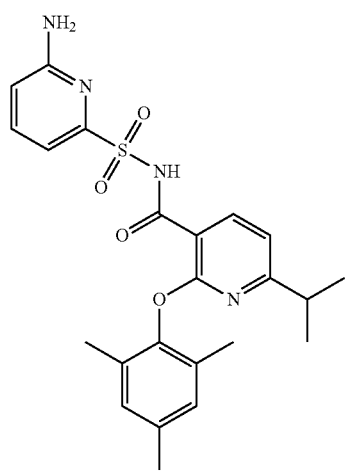 1232
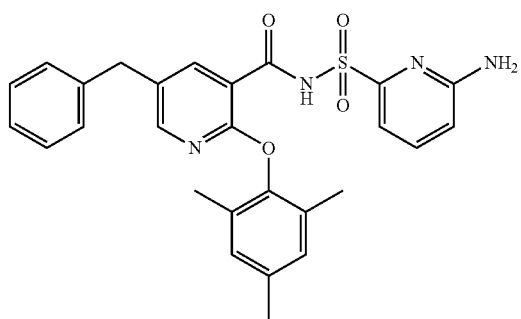 [SMILES: Cc1cc(C)c(Oc2ncc(Cc3ccccc3)cc2C(=O)NS(=O)(=O)c2cccc(N)n2)c(C)c1] 1233

TABLE 1-continued
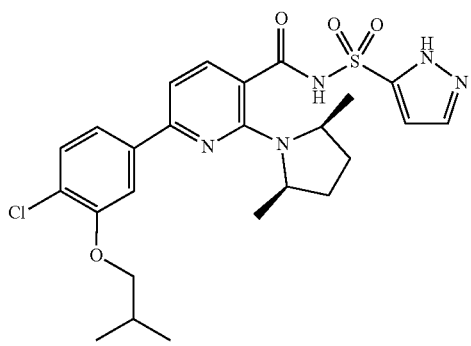 [SMILES: CC(C)COc1cc(-c2ccc(C(=O)NS(=O)(=O)c3ccn[nH]3)c(N3[C@H](C)CC[C@@H]3C)n2)ccc1Cl]
1234
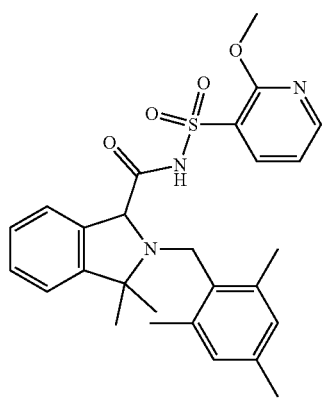 [SMILES: COc1ncccc1S(=O)(=O)NC(=O)C1c2ccccc2C(C)(C)N1Cc1c(C)cc(C)cc1C]
1235
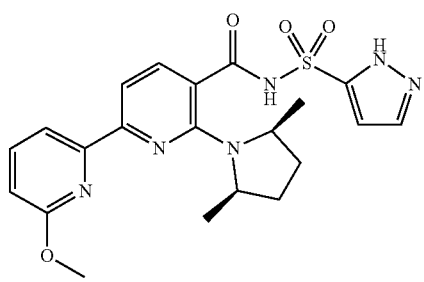 [SMILES: COc1cccc(-c2ccc(C(=O)NS(=O)(=O)c3ccn[nH]3)c(N3[C@H](C)CC[C@@H]3C)n2)n1]
1236
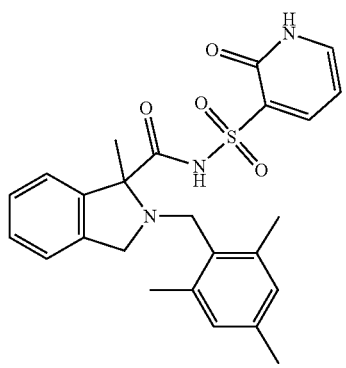 [SMILES: Cc1cc(C)c(CN2Cc3ccccc3C2(C)C(=O)NS(=O)(=O)c2ccc[nH]c2=O)c(C)c1]
1237
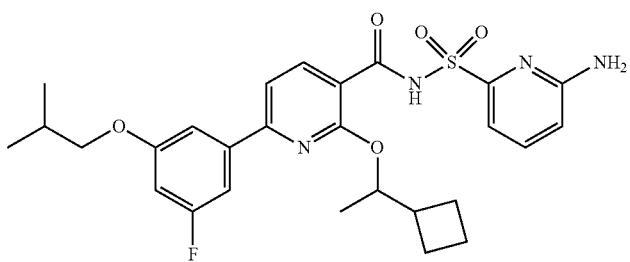 [SMILES: CC(C)COc1cc(F)cc(-c2ccc(C(=O)NS(=O)(=O)c3cccc(N)n3)c(OC(C)C3CCC3)n2)c1]
1238

TABLE 1-continued
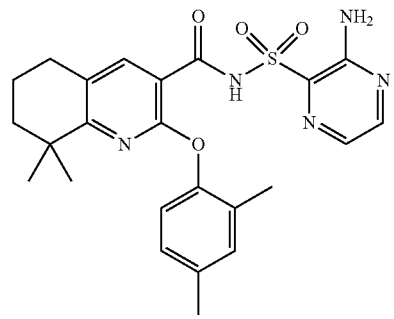 [SMILES: Cc1ccc(Oc2nc3c(cc2C(=O)NS(=O)(=O)c2nccnc2N)CCCC3(C)C)c(C)c1] 1239
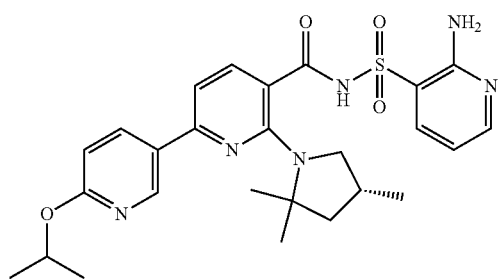 [SMILES: CC(C)Oc1ccc(-c2ccc(C(=O)NS(=O)(=O)c3cccnc3N)c(N3C[C@H](C)CC3(C)C)n2)cn1] 1240
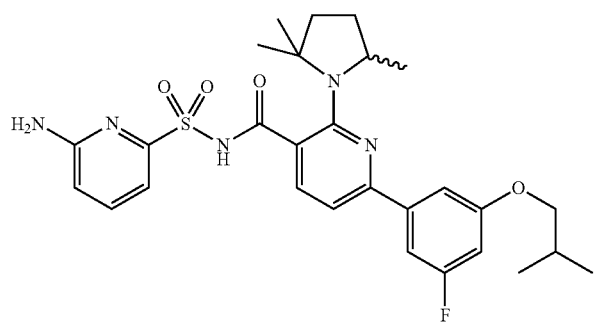 [SMILES: CC(C)COc1cc(F)cc(-c2ccc(C(=O)NS(=O)(=O)c3cccc(N)n3)c(N3C(C)CCC3(C)C)n2)c1] 1241
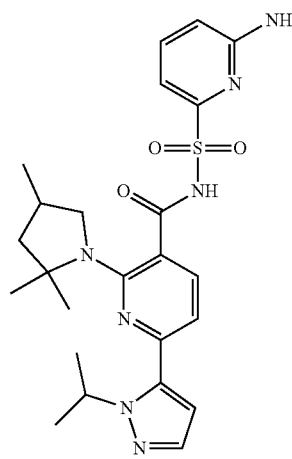 1242

TABLE 1-continued
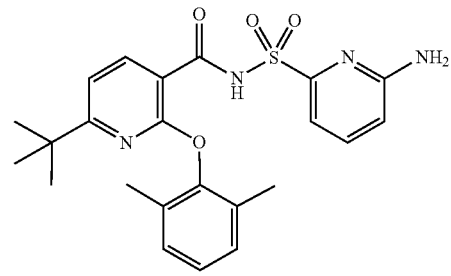 [SMILES: Cc1cccc(C)c1Oc1nc(C(C)(C)C)ccc1C(=O)NS(=O)(=O)c1cccc(N)n1]
1243
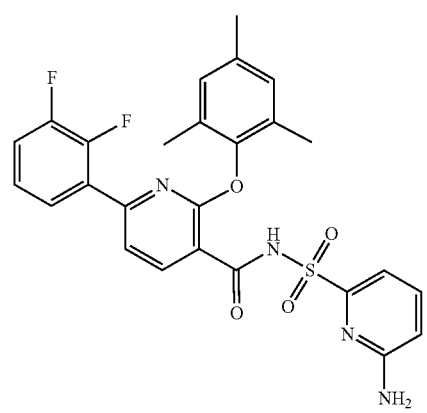 [SMILES: Cc1cc(C)c(Oc2nc(-c3cccc(F)c3F)ccc2C(=O)NS(=O)(=O)c2cccc(N)n2)c(C)c1]
1244
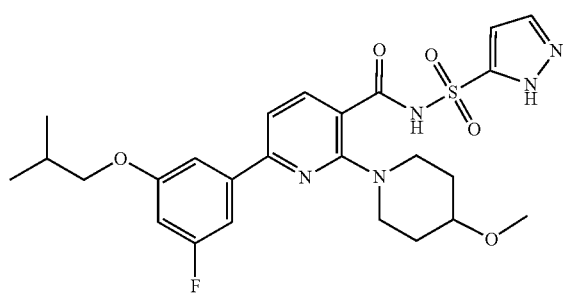 [SMILES: COC1CCN(c2nc(-c3cc(F)cc(OCC(C)C)c3)ccc2C(=O)NS(=O)(=O)c2ccn[nH]2)CC1]
1245
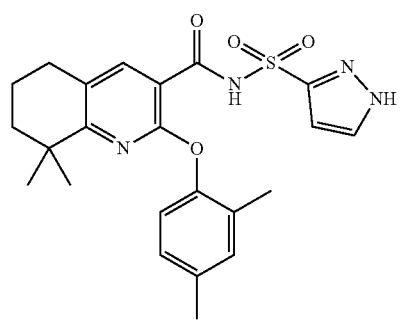 [SMILES: Cc1ccc(Oc2nc3c(cc2C(=O)NS(=O)(=O)c2cc[nH]n2)CCCC3(C)C)c(C)c1]
1246
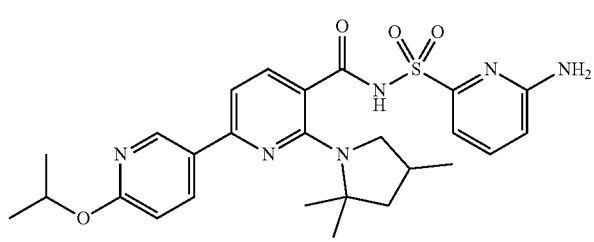 [SMILES: CC1CN(c2nc(-c3ccc(OC(C)C)nc3)ccc2C(=O)NS(=O)(=O)c2cccc(N)n2)C(C)(C)C1]
1247

TABLE 1-continued
| | |
|---|---|
| 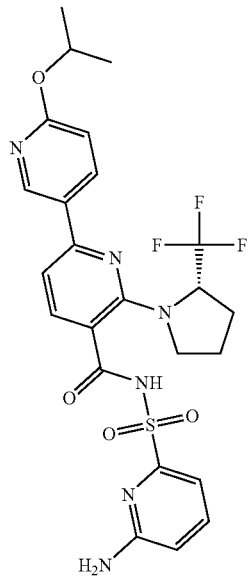 [SMILES: CC(C)Oc1ccc(-c2ccc(C(=O)NS(=O)(=O)c3cccc(N)n3)c(N3CCC[C@H]3C(F)(F)F)n2)cn1] | 1248 |
| 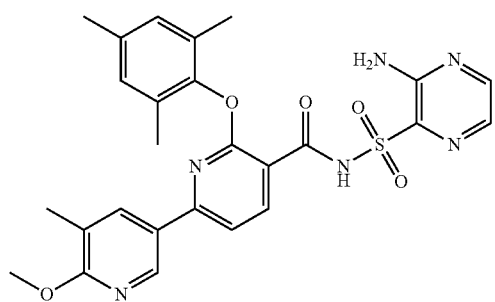 [SMILES: COc1ncc(-c2ccc(C(=O)NS(=O)(=O)c3nccnc3N)c(Oc3c(C)cc(C)cc3C)n2)cc1C] | 1249 |
| 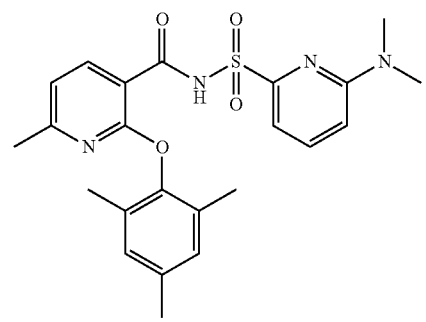 | 1250 |
| 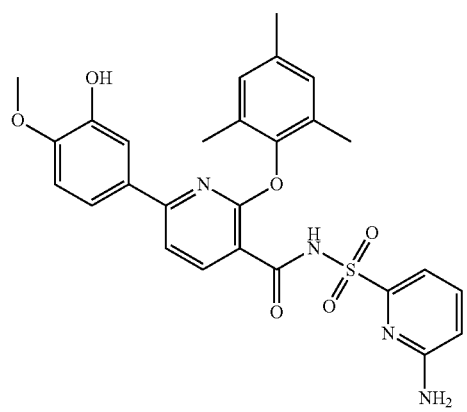 [SMILES: COc1ccc(-c2ccc(C(=O)NS(=O)(=O)c3cccc(N)n3)c(Oc3c(C)cc(C)cc3C)n2)cc1O] | 1251 |

TABLE 1-continued
| | |
|---|---|
| 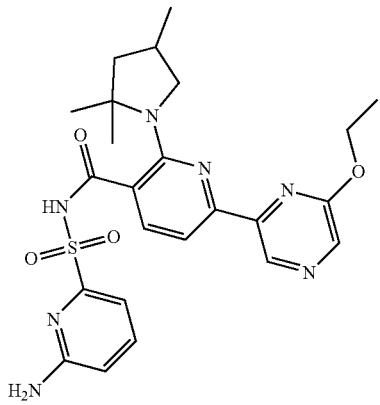 [SMILES: CCOc1cncc(-c2ccc(C(=O)NS(=O)(=O)c3cccc(N)n3)c(N3CC(C)CC3(C)C)n2)n1] | 1252 |
| 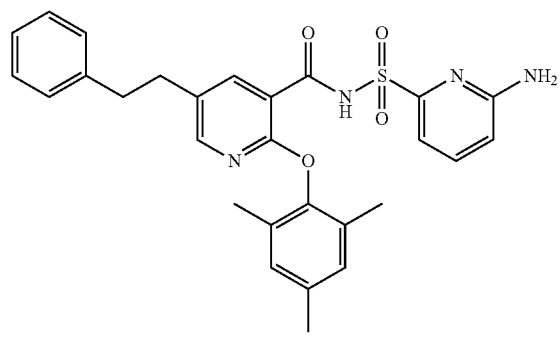 [SMILES: Cc1cc(C)c(Oc2ncc(CCc3ccccc3)cc2C(=O)NS(=O)(=O)c2cccc(N)n2)c(C)c1] | 1253 |
| 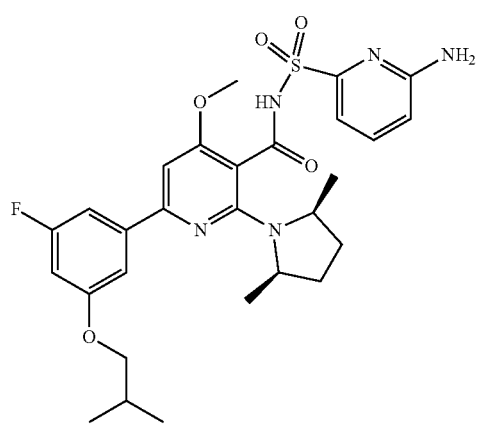 [SMILES: COc1cc(-c2cc(F)cc(OCC(C)C)c2)nc(N2[C@H](C)CC[C@@H]2C)c1C(=O)NS(=O)(=O)c1cccc(N)n1] | 1254 |
| 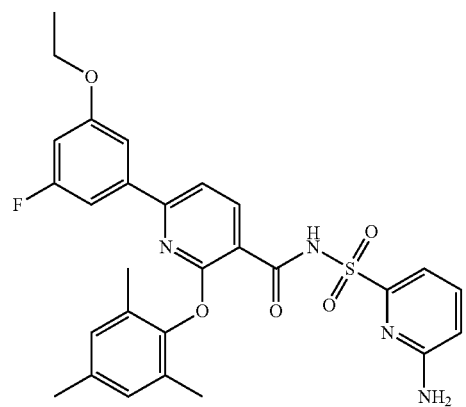 [SMILES: CCOc1cc(F)cc(-c2ccc(C(=O)NS(=O)(=O)c3cccc(N)n3)c(Oc3c(C)cc(C)cc3C)n2)c1] | 1255 |

TABLE 1-continued
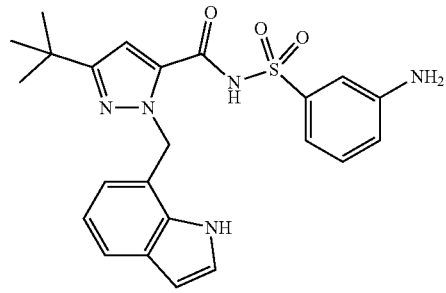 [SMILES: CC(C)(C)c1cc(C(=O)NS(=O)(=O)c2cccc(N)c2)n(Cc2cccc3cc[nH]c23)n1]
1256
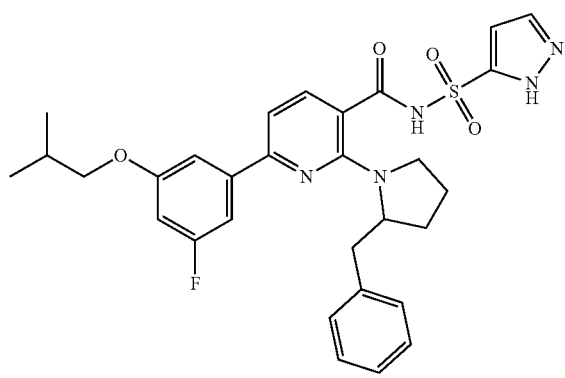 [SMILES: CC(C)COc1cc(F)cc(-c2ccc(C(=O)NS(=O)(=O)c3ccn[nH]3)c(N3CCCC3Cc3ccccc3)n2)c1]
1257
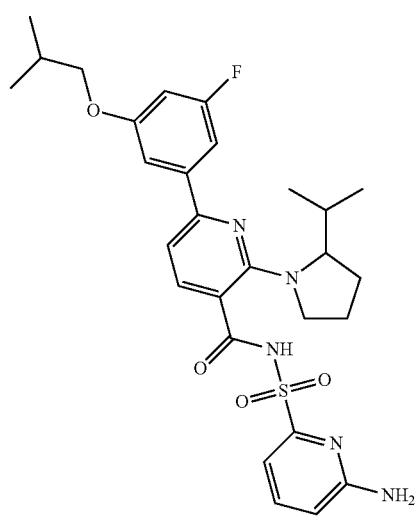 [SMILES: CC(C)COc1cc(F)cc(-c2ccc(C(=O)NS(=O)(=O)c3cccc(N)n3)c(N3CCCC3C(C)C)n2)c1]
1258
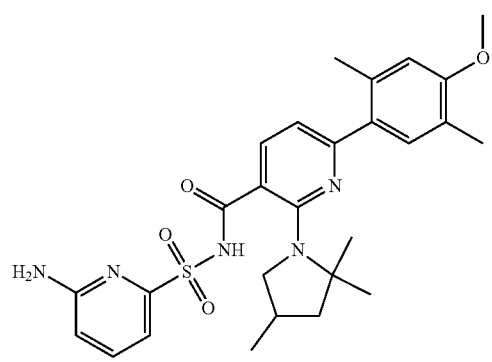 [SMILES: COc1cc(C)c(-c2ccc(C(=O)NS(=O)(=O)c3cccc(N)n3)c(N3CC(C)CC3(C)C)n2)cc1C]
1259

TABLE 1-continued
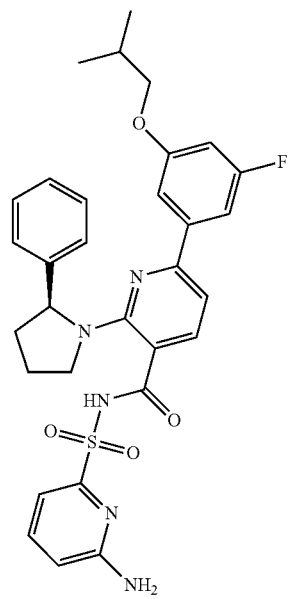 [SMILES: CC(C)COc1cc(F)cc(-c2ccc(C(=O)NS(=O)(=O)c3cccc(N)n3)c(N3CCC[C@H]3c3ccccc3)n2)c1]
1260
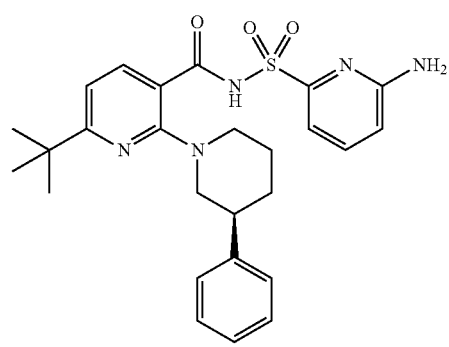 [SMILES: CC(C)(C)c1ccc(C(=O)NS(=O)(=O)c2cccc(N)n2)c(N2CCC[C@@H](c3ccccc3)C2)n1]
1261
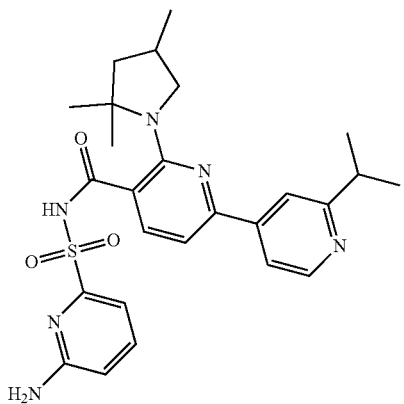 [SMILES: CC1CN(c2nc(-c3ccnc(C(C)C)c3)ccc2C(=O)NS(=O)(=O)c2cccc(N)n2)C(C)(C)C1]
1262
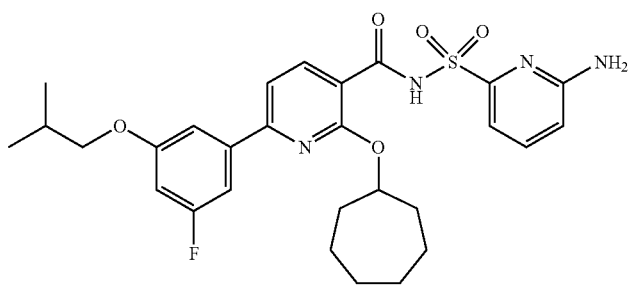 [SMILES: CC(C)COc1cc(F)cc(-c2ccc(C(=O)NS(=O)(=O)c3cccc(N)n3)c(OC3CCCCCC3)n2)c1]
1263

TABLE 1-continued
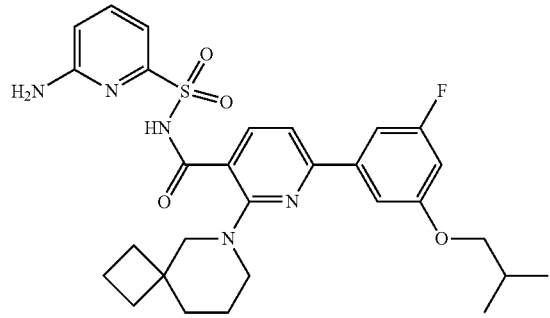 [SMILES: CC(C)COc1cc(F)cc(-c2ccc(C(=O)NS(=O)(=O)c3cccc(N)n3)c(N3CCCC4(CCC4)C3)n2)c1]
1264
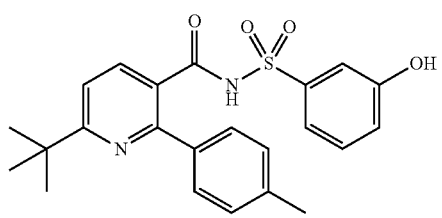 [SMILES: Cc1ccc(-c2nc(C(C)(C)C)ccc2C(=O)NS(=O)(=O)c2cccc(O)c2)cc1]
1265
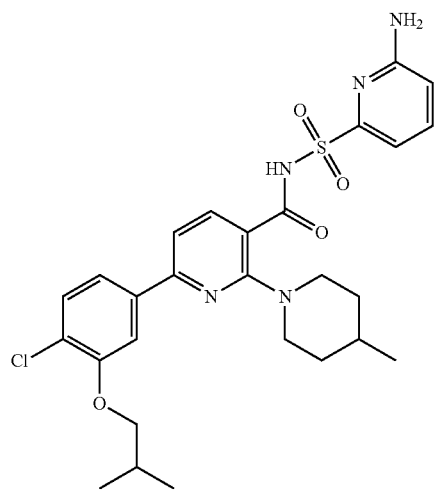 [SMILES: CC(C)COc1cc(-c2ccc(C(=O)NS(=O)(=O)c3cccc(N)n3)c(N3CCC(C)CC3)n2)ccc1Cl]
1266
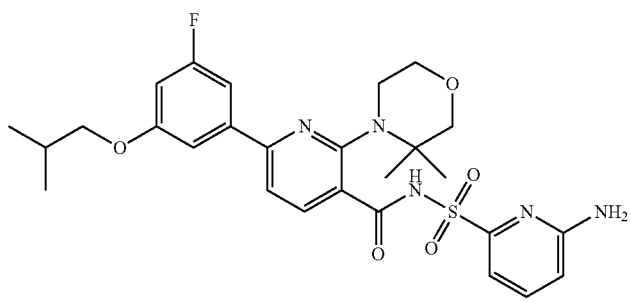 [SMILES: CC(C)COc1cc(F)cc(-c2ccc(C(=O)NS(=O)(=O)c3cccc(N)n3)c(N3CCOCC3(C)C)n2)c1]
1267

TABLE 1-continued
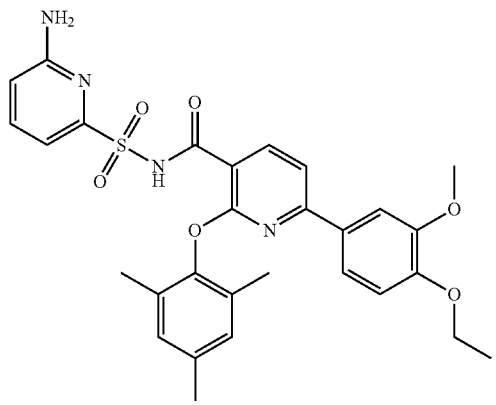 [SMILES: CCOc1ccc(-c2ccc(C(=O)NS(=O)(=O)c3cccc(N)n3)c(Oc3c(C)cc(C)cc3C)n2)cc1OC]
1268
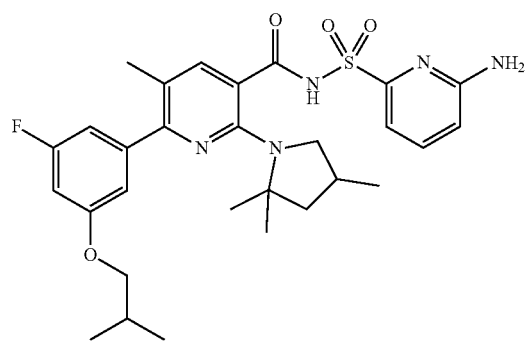 [SMILES: Cc1cc(C(=O)NS(=O)(=O)c2cccc(N)n2)c(N2CC(C)CC2(C)C)nc1-c1cc(F)cc(OCC(C)C)c1]
1269
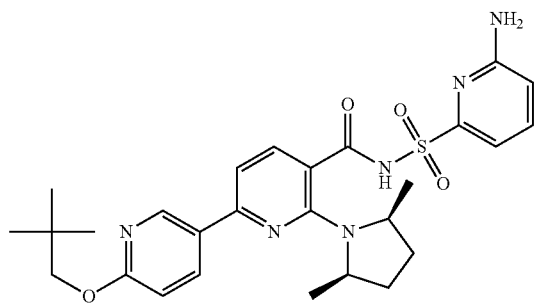 [SMILES: C[C@@H]1CC[C@H](C)N1c1nc(-c2ccc(OCC(C)(C)C)nc2)ccc1C(=O)NS(=O)(=O)c1cccc(N)n1]
1270
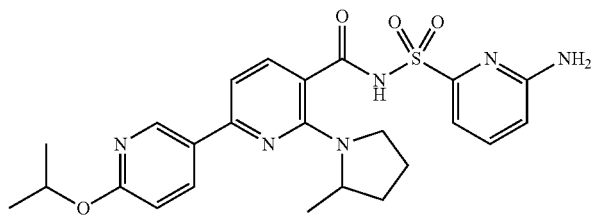 [SMILES: CC(C)Oc1ccc(-c2ccc(C(=O)NS(=O)(=O)c3cccc(N)n3)c(N3CCCC3C)n2)cn1]
1271

TABLE 1-continued
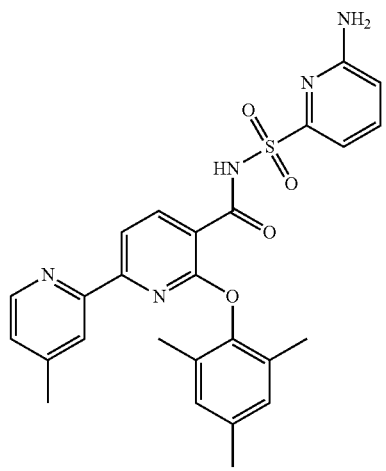 [SMILES: Cc1ccnc(-c2ccc(C(=O)NS(=O)(=O)c3cccc(N)n3)c(Oc3c(C)cc(C)cc3C)n2)c1]
1272
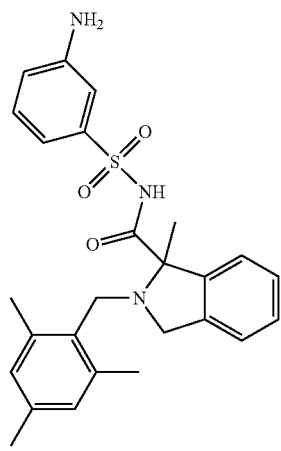 [SMILES: Cc1cc(C)c(CN2Cc3ccccc3C2(C)C(=O)NS(=O)(=O)c2cccc(N)c2)c(C)c1]
1273
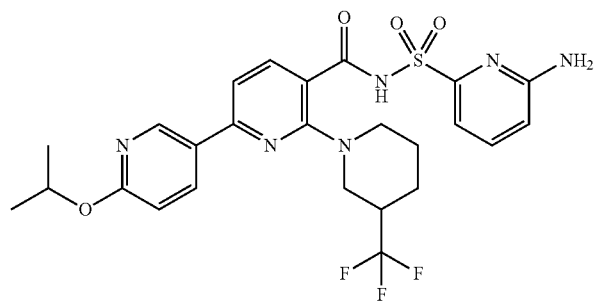 [SMILES: CC(C)Oc1ccc(-c2ccc(C(=O)NS(=O)(=O)c3cccc(N)n3)c(N3CCCC(C(F)(F)F)C3)n2)cn1]
1274

TABLE 1-continued
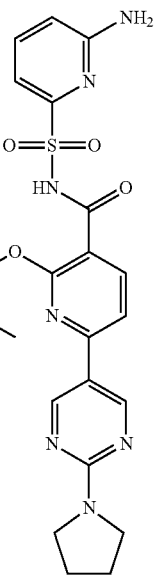 1275
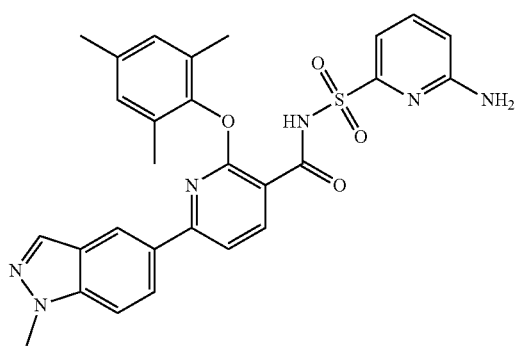 [SMILES: Cc1cc(C)c(Oc2nc(-c3ccc4c(cnn4C)c3)ccc2C(=O)NS(=O)(=O)c2cccc(N)n2)c(C)c1] 1276
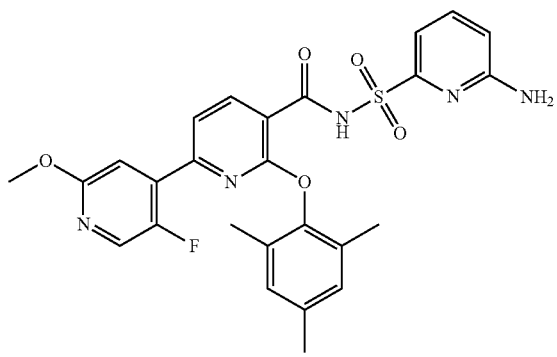 [SMILES: COc1cc(-c2ccc(C(=O)NS(=O)(=O)c3cccc(N)n3)c(Oc3c(C)cc(C)cc3C)n2)c(F)cn1] 1277
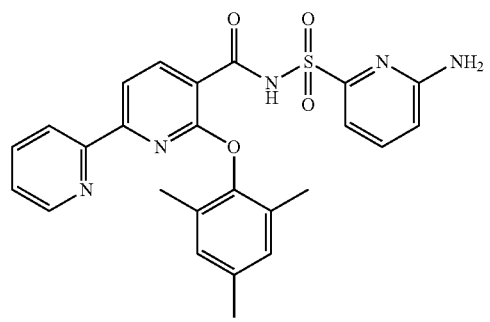 [SMILES: Cc1cc(C)c(Oc2nc(-c3ccccn3)ccc2C(=O)NS(=O)(=O)c2cccc(N)n2)c(C)c1] 1278

TABLE 1-continued
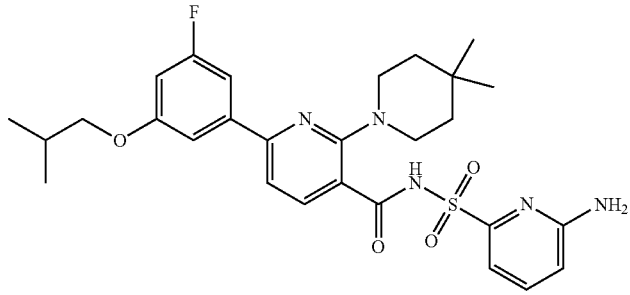 [SMILES: CC(C)COc1cc(F)cc(-c2ccc(C(=O)NS(=O)(=O)c3cccc(N)n3)c(N3CCC(C)(C)CC3)n2)c1]
1279
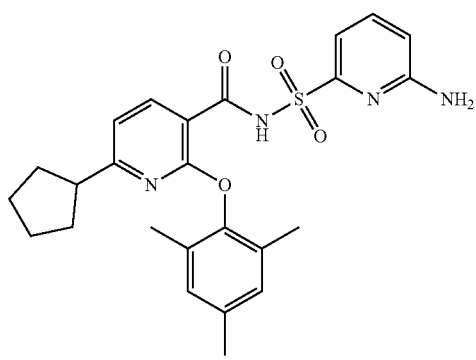 [SMILES: Cc1cc(C)c(Oc2nc(C3CCCC3)ccc2C(=O)NS(=O)(=O)c2cccc(N)n2)c(C)c1]
1280
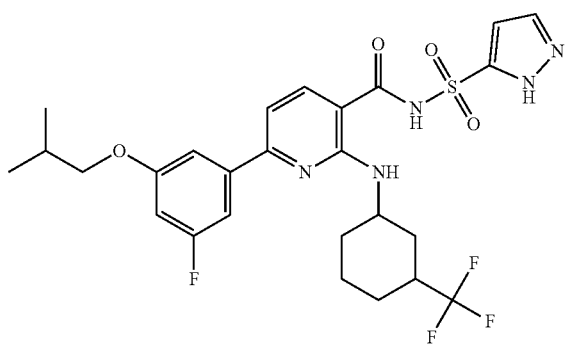
1281
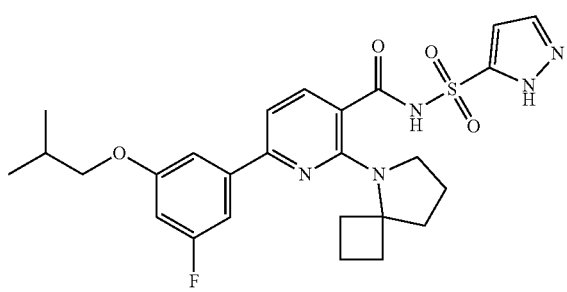
1282

TABLE 1-continued
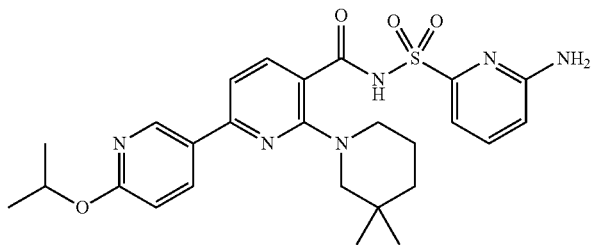 [SMILES: CC(C)Oc1ccc(-c2ccc(C(=O)NS(=O)(=O)c3cccc(N)n3)c(N3CCCC(C)(C)C3)n2)cn1]
1283
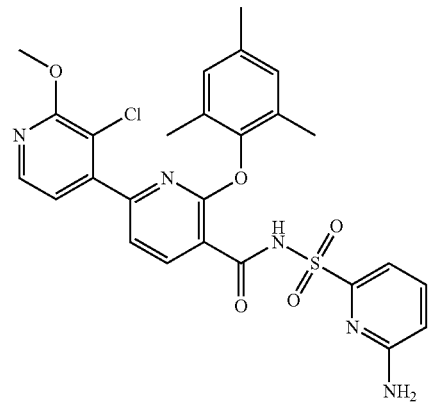 [SMILES: COc1nccc(-c2ccc(C(=O)NS(=O)(=O)c3cccc(N)n3)c(Oc3c(C)cc(C)cc3C)n2)c1Cl]
1284
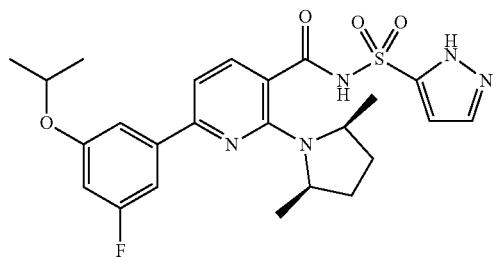 [SMILES: CC(C)Oc1cc(F)cc(-c2ccc(C(=O)NS(=O)(=O)c3ccn[nH]3)c(N3[C@H](C)CC[C@@H]3C)n2)c1]
1285
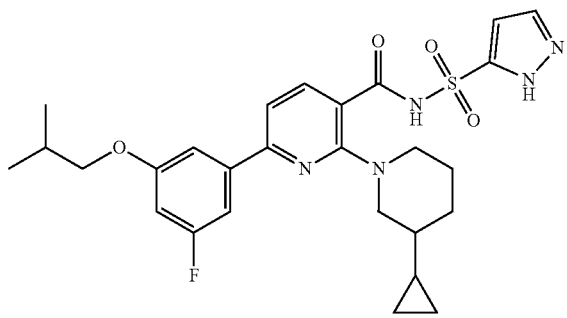 [SMILES: CC(C)COc1cc(F)cc(-c2ccc(C(=O)NS(=O)(=O)c3ccn[nH]3)c(N3CCCC(C4CC4)C3)n2)c1]
1286
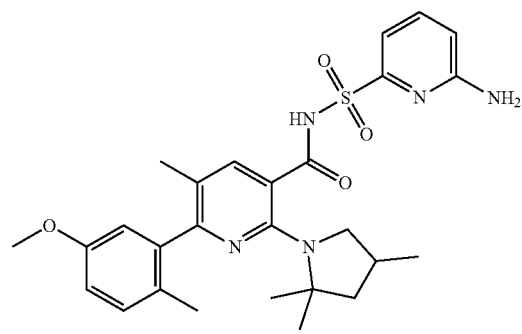 [SMILES: COc1ccc(C)c(-c2nc(N3CC(C)CC3(C)C)c(C(=O)NS(=O)(=O)c3cccc(N)n3)cc2C)c1]
1287

TABLE 1-continued
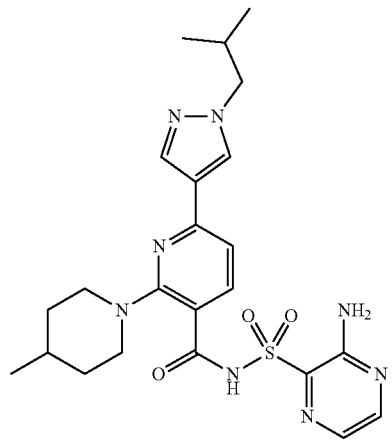 [SMILES: CC(C)Cn1cc(-c2ccc(C(=O)NS(=O)(=O)c3nccnc3N)c(N3CCC(C)CC3)n2)cn1]
1288
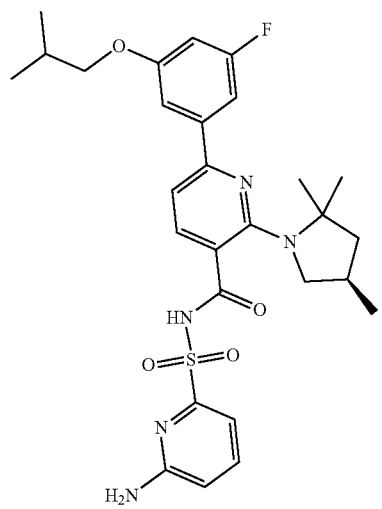 [SMILES: CC(C)COc1cc(F)cc(-c2ccc(C(=O)NS(=O)(=O)c3cccc(N)n3)c(N3C[C@H](C)CC3(C)C)n2)c1]
1289
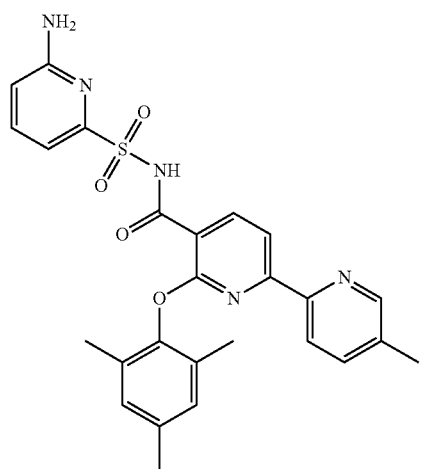 [SMILES: Cc1ccc(-c2ccc(C(=O)NS(=O)(=O)c3cccc(N)n3)c(Oc3c(C)cc(C)cc3C)n2)nc1]
1290
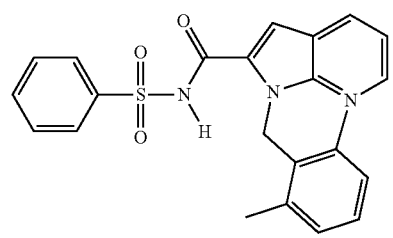
1291

TABLE 1-continued
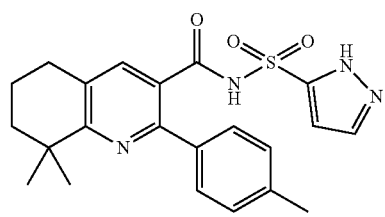 [SMILES: Cc1ccc(-c2nc3c(cc2C(=O)NS(=O)(=O)c2ccn[nH]2)CCCC3(C)C)cc1] 1292
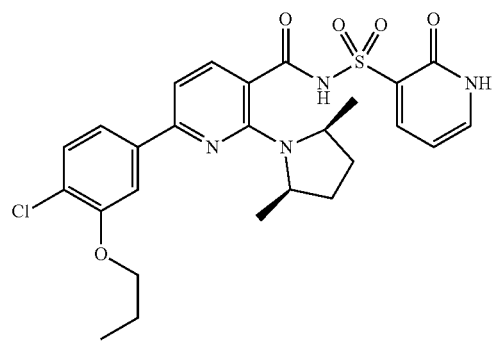 [SMILES: CCCOc1cc(-c2ccc(C(=O)NS(=O)(=O)c3ccc[nH]c3=O)c(N3[C@H](C)CC[C@@H]3C)n2)ccc1Cl] 1293
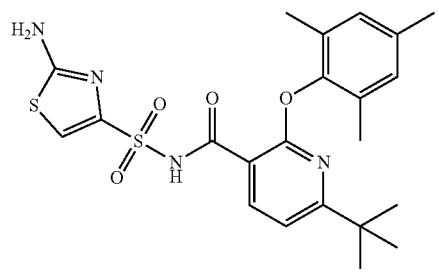 [SMILES: Cc1cc(C)c(Oc2nc(C(C)(C)C)ccc2C(=O)NS(=O)(=O)c2csc(N)n2)c(C)c1] 1294
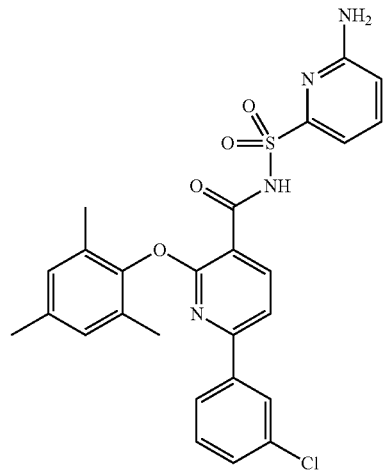 [SMILES: Cc1cc(C)c(Oc2nc(-c3cccc(Cl)c3)ccc2C(=O)NS(=O)(=O)c2cccc(N)n2)c(C)c1] 1295

TABLE 1-continued
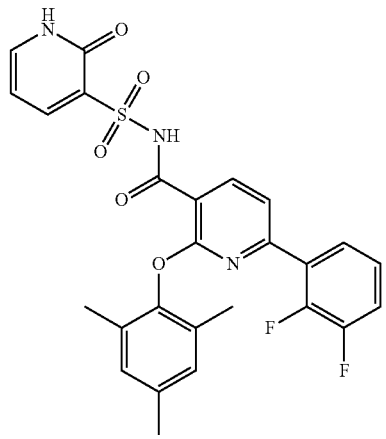 [SMILES: Cc1cc(C)c(Oc2nc(-c3cccc(F)c3F)ccc2C(=O)NS(=O)(=O)c2ccc[nH]c2=O)c(C)c1]
1296
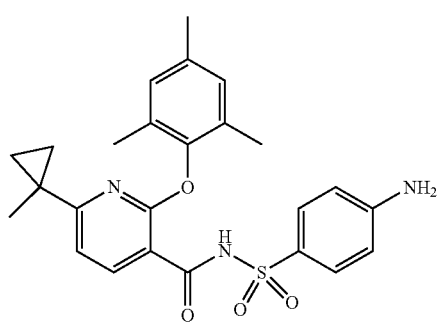 [SMILES: Cc1cc(C)c(Oc2nc(C3(C)CC3)ccc2C(=O)NS(=O)(=O)c2ccc(N)cc2)c(C)c1]
1297
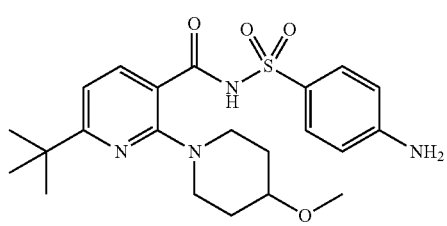 [SMILES: COC1CCN(c2nc(C(C)(C)C)ccc2C(=O)NS(=O)(=O)c2ccc(N)cc2)CC1]
1298
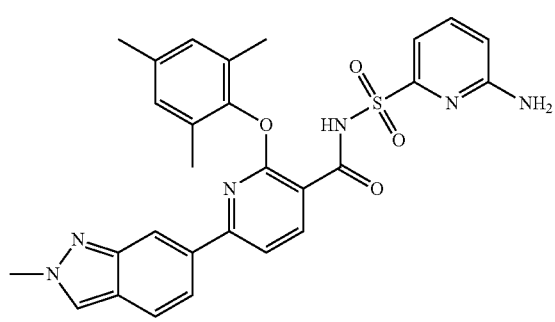 [SMILES: Cc1cc(C)c(Oc2nc(-c3ccc4cn(C)nc4c3)ccc2C(=O)NS(=O)(=O)c2cccc(N)n2)c(C)c1]
1299

TABLE 1-continued
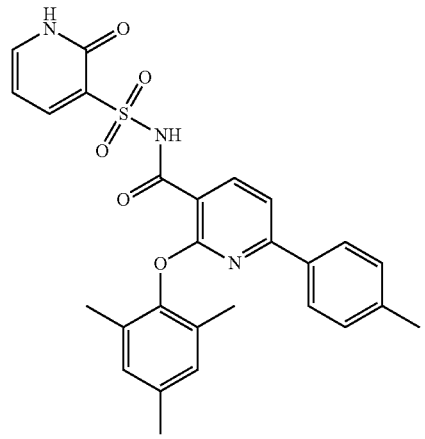 [SMILES: Cc1ccc(-c2ccc(C(=O)NS(=O)(=O)c3ccc[nH]c3=O)c(Oc3c(C)cc(C)cc3C)n2)cc1]
1300
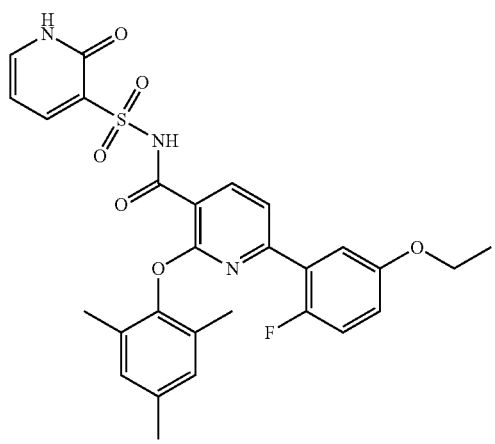 [SMILES: CCOc1ccc(F)c(-c2ccc(C(=O)NS(=O)(=O)c3ccc[nH]c3=O)c(Oc3c(C)cc(C)cc3C)n2)c1]
1301
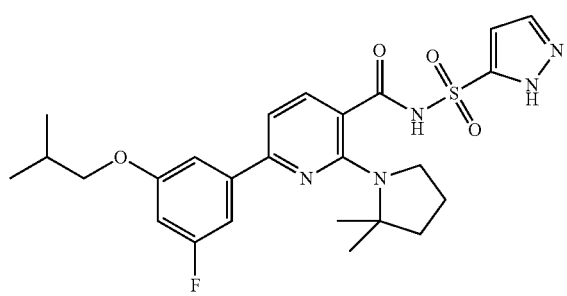 [SMILES: CC(C)COc1cc(F)cc(-c2ccc(C(=O)NS(=O)(=O)c3ccn[nH]3)c(N3CCCC3(C)C)n2)c1]
1302
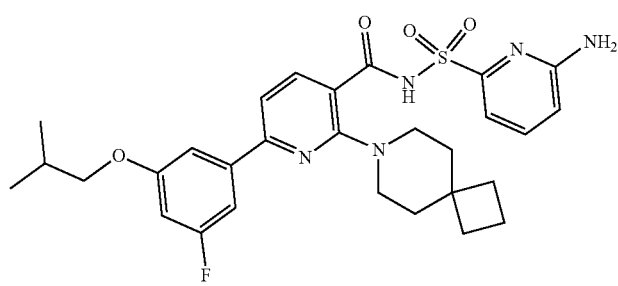
1303

TABLE 1-continued
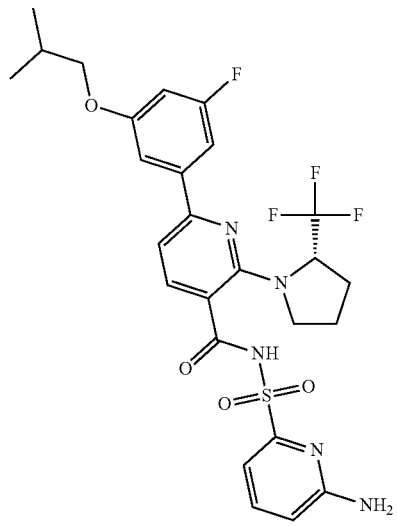 [SMILES: CC(C)COc1cc(F)cc(-c2ccc(C(=O)NS(=O)(=O)c3cccc(N)n3)c(N3CCC[C@H]3C(F)(F)F)n2)c1]
1304
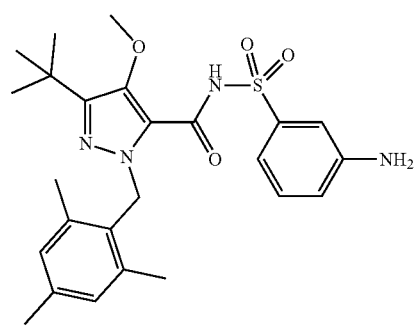 [SMILES: COc1c(C(C)(C)C)nn(Cc2c(C)cc(C)cc2C)c1C(=O)NS(=O)(=O)c1cccc(N)c1]
1305
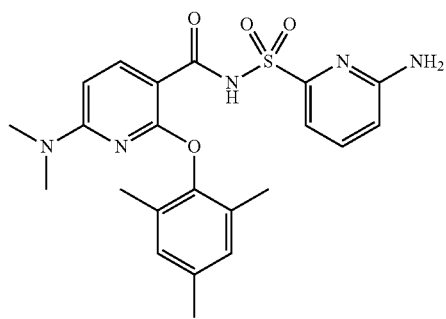 [SMILES: Cc1cc(C)c(Oc2nc(N(C)C)ccc2C(=O)NS(=O)(=O)c2cccc(N)n2)c(C)c1]
1306
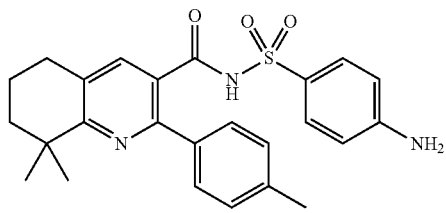 [SMILES: Cc1ccc(-c2nc3c(cc2C(=O)NS(=O)(=O)c2ccc(N)cc2)CCCC3(C)C)cc1]
1307
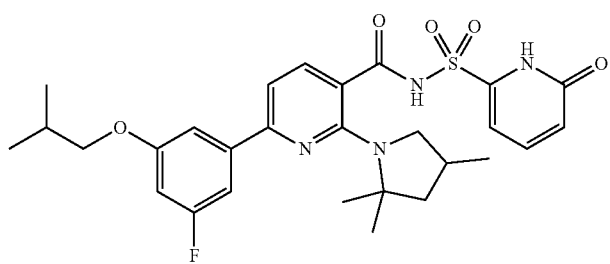
1308

TABLE 1-continued
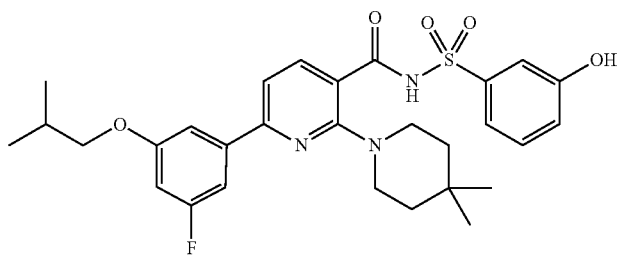 [SMILES: CC(C)COc1cc(F)cc(-c2ccc(C(=O)NS(=O)(=O)c3cccc(O)c3)c(N3CCC(C)(C)CC3)n2)c1] 1309
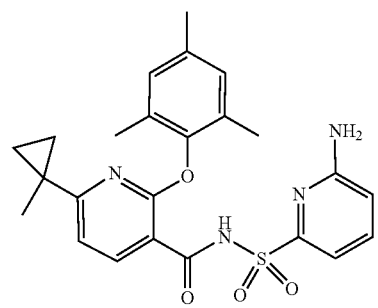 1310
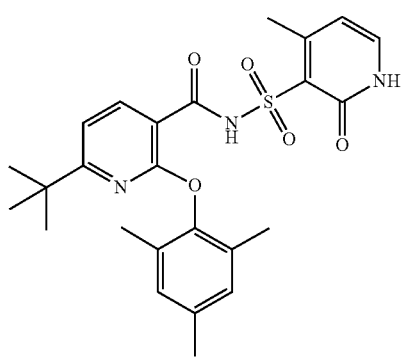 [SMILES: Cc1cc(C)c(Oc2nc(C(C)(C)C)ccc2C(=O)NS(=O)(=O)c2c(C)cc[nH]c2=O)c(C)c1] 1311
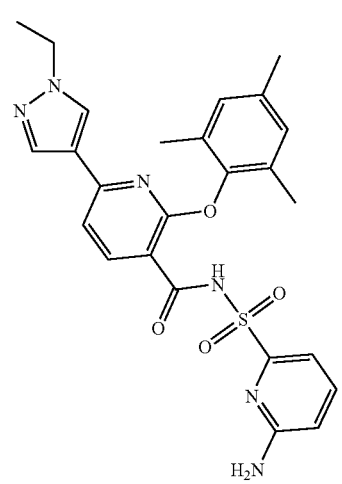 1312

TABLE 1-continued
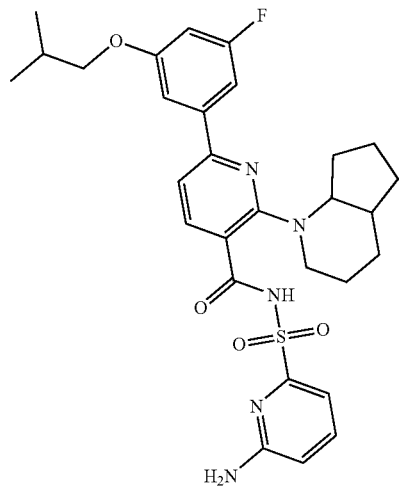 [SMILES: CC(C)COc1cc(F)cc(-c2ccc(C(=O)NS(=O)(=O)c3cccc(N)n3)c(N3CCCC4CCCC43)n2)c1]
1313
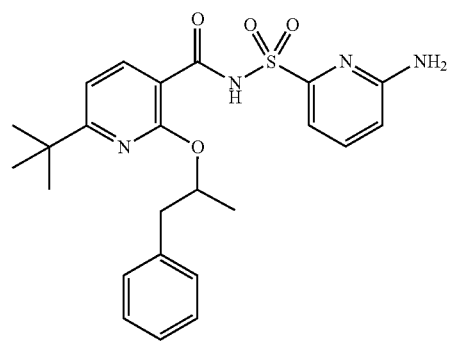 [SMILES: CC(Cc1ccccc1)Oc1nc(C(C)(C)C)ccc1C(=O)NS(=O)(=O)c1cccc(N)n1]
1314
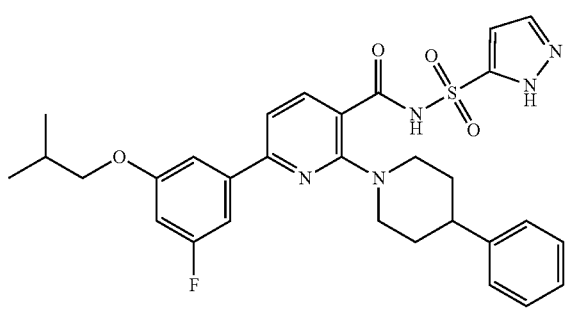 [SMILES: CC(C)COc1cc(F)cc(-c2ccc(C(=O)NS(=O)(=O)c3ccn[nH]3)c(N3CCC(c4ccccc4)CC3)n2)c1]
1315
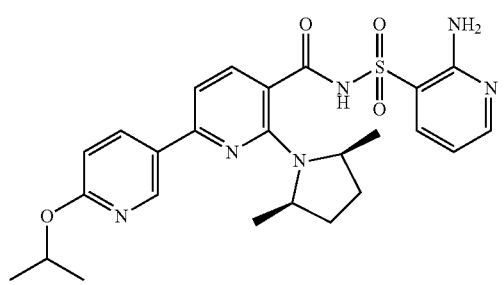 [SMILES: CC(C)Oc1ccc(-c2ccc(C(=O)NS(=O)(=O)c3cccnc3N)c(N3[C@H](C)CC[C@@H]3C)n2)cn1]
1316

TABLE 1-continued
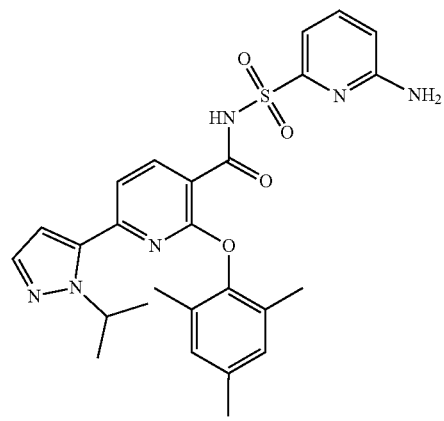 [SMILES: Cc1cc(C)c(Oc2nc(-c3ccnn3C(C)C)ccc2C(=O)NS(=O)(=O)c2cccc(N)n2)c(C)c1] 1317
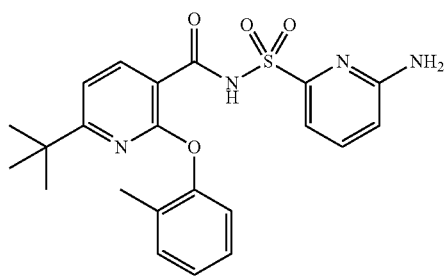 [SMILES: Cc1ccccc1Oc1nc(C(C)(C)C)ccc1C(=O)NS(=O)(=O)c1cccc(N)n1] 1318
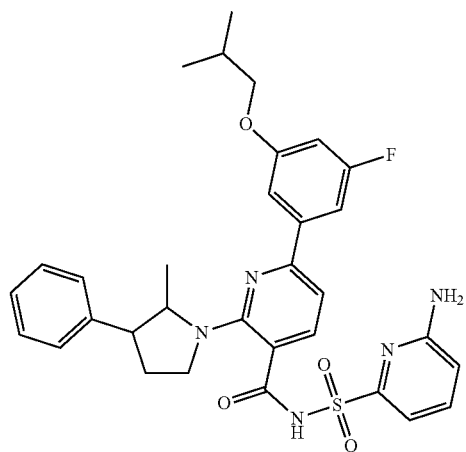 [SMILES: CC(C)COc1cc(F)cc(-c2ccc(C(=O)NS(=O)(=O)c3cccc(N)n3)c(N3CCC(c4ccccc4)C3C)n2)c1] 1319
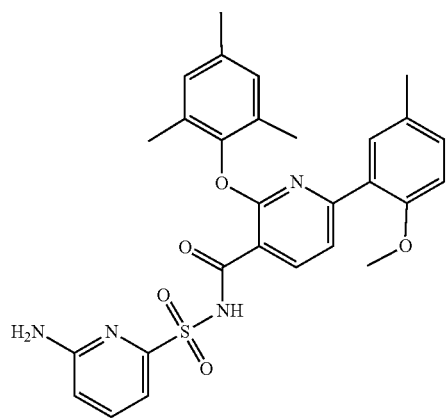 [SMILES: COc1ccc(C)cc1-c1ccc(C(=O)NS(=O)(=O)c2cccc(N)n2)c(Oc2c(C)cc(C)cc2C)n1] 1320

TABLE 1-continued
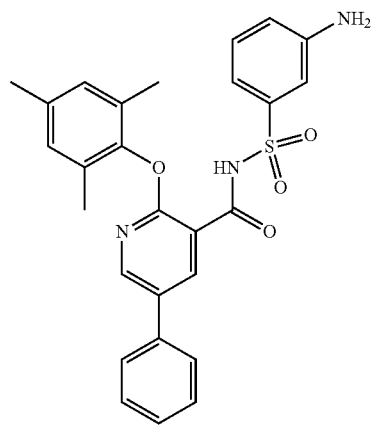 [SMILES: Cc1cc(C)c(Oc2ncc(-c3ccccc3)cc2C(=O)NS(=O)(=O)c2cccc(N)c2)c(C)c1] 1321
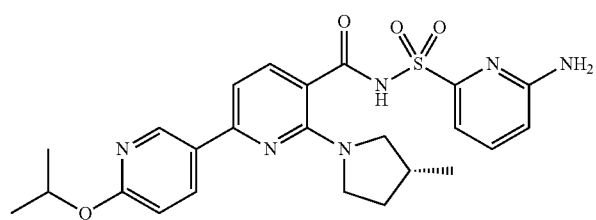 [SMILES: CC(C)Oc1ccc(-c2ccc(C(=O)NS(=O)(=O)c3cccc(N)n3)c(N3CC[C@@H](C)C3)n2)cn1] 1322
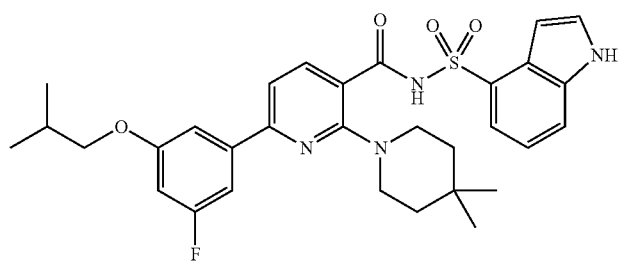 [SMILES: CC(C)COc1cc(F)cc(-c2ccc(C(=O)NS(=O)(=O)c3cccc4[nH]ccc34)c(N3CCC(C)(C)CC3)n2)c1] 1323
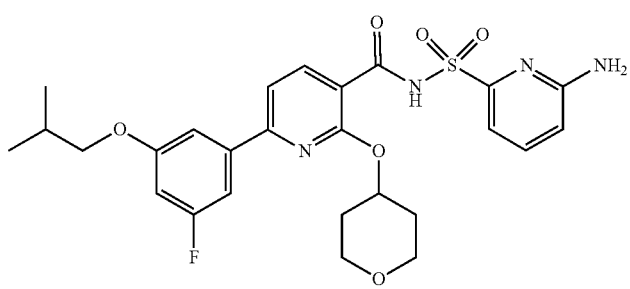 1324
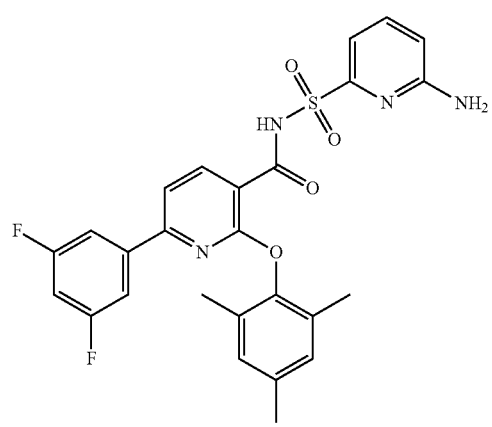 [SMILES: Cc1cc(C)c(Oc2nc(-c3cc(F)cc(F)c3)ccc2C(=O)NS(=O)(=O)c2cccc(N)n2)c(C)c1] 1325

TABLE 1-continued
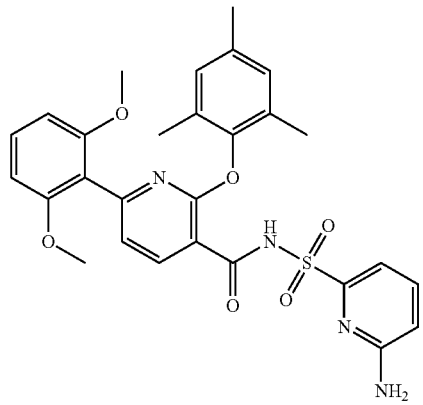 [SMILES: COc1cccc(OC)c1-c1ccc(C(=O)NS(=O)(=O)c2cccc(N)n2)c(Oc2c(C)cc(C)cc2C)n1]
1326
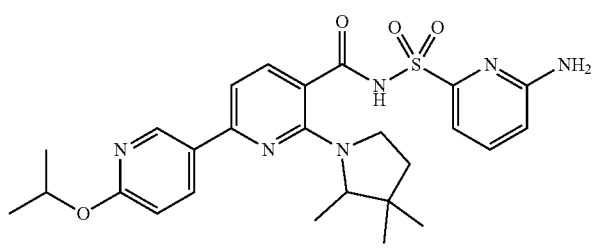 [SMILES: CC(C)Oc1ccc(-c2ccc(C(=O)NS(=O)(=O)c3cccc(N)n3)c(N3CCC(C)(C)C3C)n2)cn1]
1327
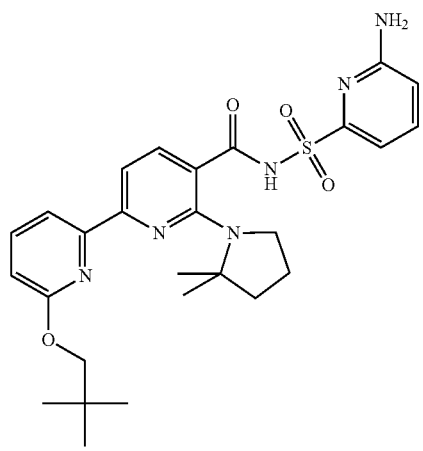
1328
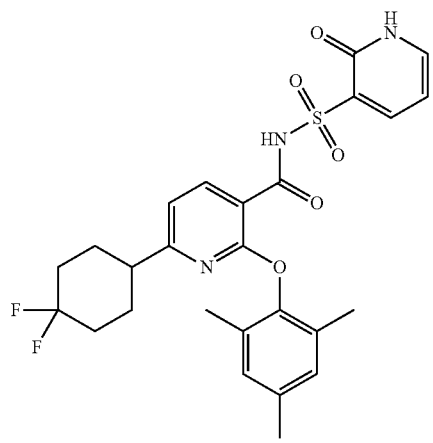 [SMILES: Cc1cc(C)c(Oc2nc(C3CCC(F)(F)CC3)ccc2C(=O)NS(=O)(=O)c2ccc[nH]c2=O)c(C)c1]
1329

TABLE 1-continued
| | |
|---|---|
| 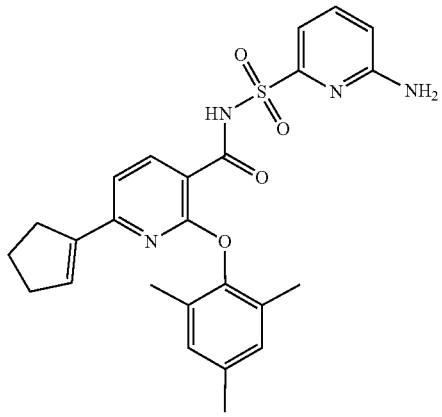 | 1330 |
| 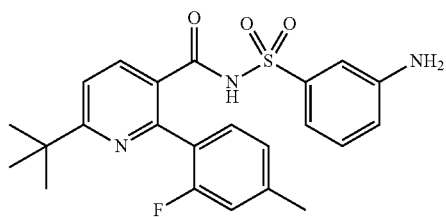 [SMILES: Cc1ccc(-c2nc(C(C)(C)C)ccc2C(=O)NS(=O)(=O)c2cccc(N)c2)c(F)c1] | 1331 |
| 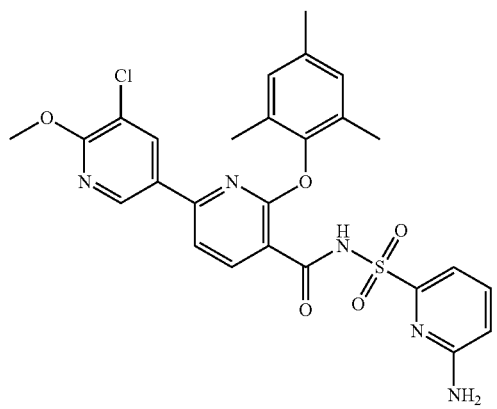 [SMILES: COc1ncc(-c2ccc(C(=O)NS(=O)(=O)c3cccc(N)n3)c(Oc3c(C)cc(C)cc3C)n2)cc1Cl] | 1332 |
| 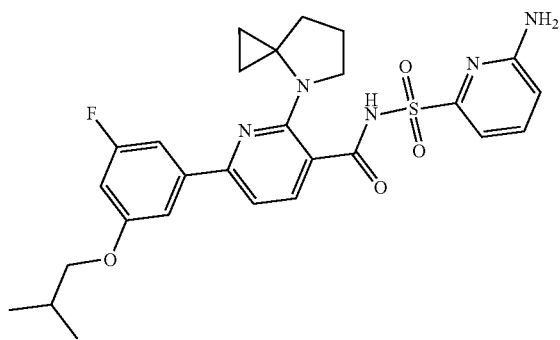 [SMILES: CC(C)COc1cc(F)cc(-c2ccc(C(=O)NS(=O)(=O)c3cccc(N)n3)c(N3CCCC34CC4)n2)c1] | 1333 |
| 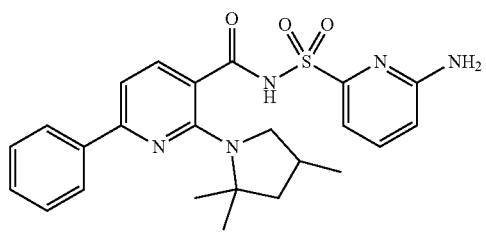 | 1334 |

TABLE 1-continued
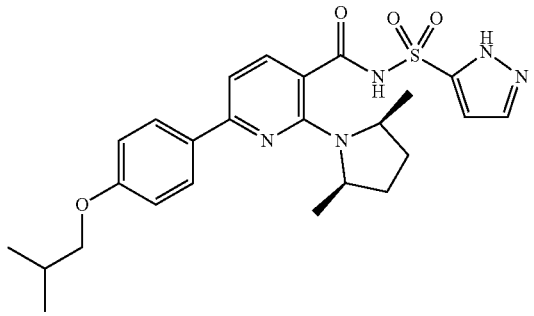
1335
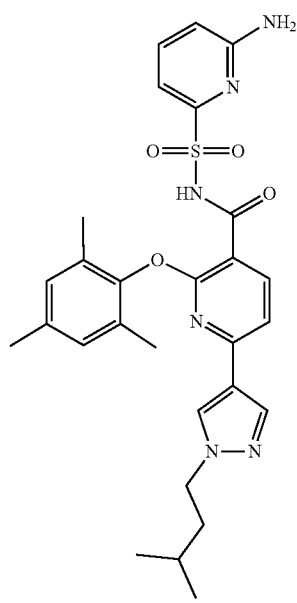 [SMILES: Cc1cc(C)c(Oc2nc(-c3cnn(CCC(C)C)c3)ccc2C(=O)NS(=O)(=O)c2cccc(N)n2)c(C)c1]
1336
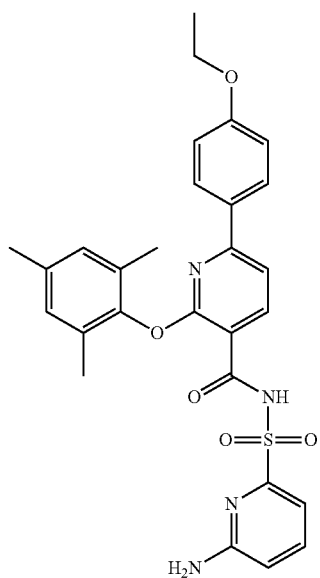
1337

TABLE 1-continued
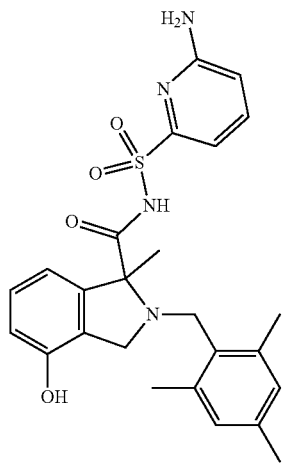 [SMILES: Cc1cc(C)c(CN2Cc3c(O)cccc3C2(C)C(=O)NS(=O)(=O)c2cccc(N)n2)c(C)c1]
1338
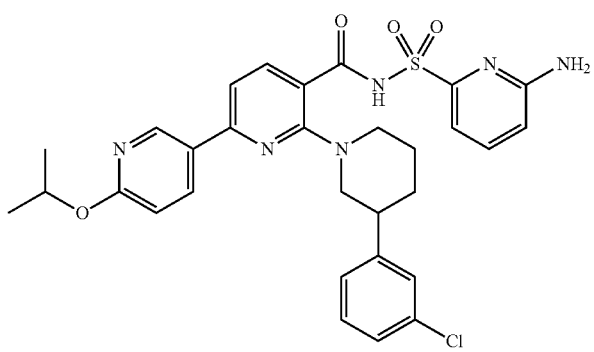 [SMILES: CC(C)Oc1ccc(-c2ccc(C(=O)NS(=O)(=O)c3cccc(N)n3)c(N3CCCC(c4cccc(Cl)c4)C3)n2)cn1]
1339
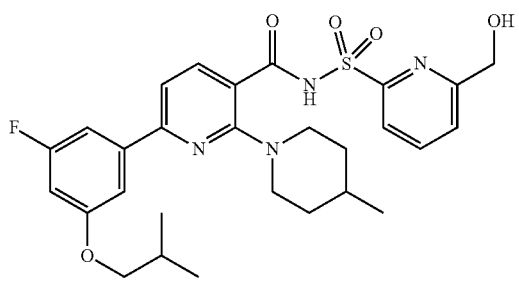 [SMILES: CC(C)COc1cc(F)cc(-c2ccc(C(=O)NS(=O)(=O)c3cccc(CO)n3)c(N3CCC(C)CC3)n2)c1]
1340
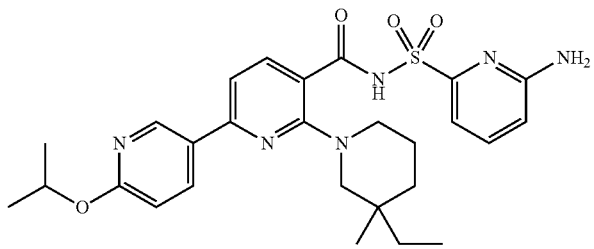 [SMILES: CCC1(C)CCCN(c2nc(-c3ccc(OC(C)C)nc3)ccc2C(=O)NS(=O)(=O)c2cccc(N)n2)C1]
1341

TABLE 1-continued
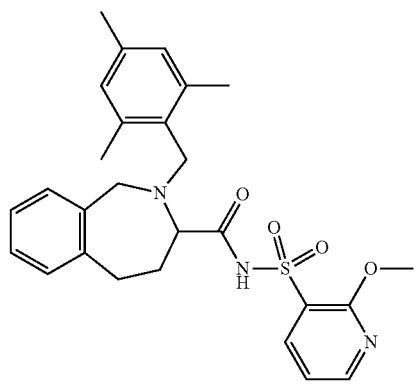 [SMILES: COc1ncccc1S(=O)(=O)NC(=O)C1CCc2ccccc2CN1Cc1c(C)cc(C)cc1C] 1342
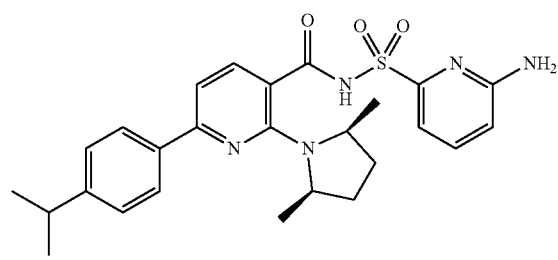 [SMILES: CC(C)c1ccc(-c2ccc(C(=O)NS(=O)(=O)c3cccc(N)n3)c(N3[C@H](C)CC[C@@H]3C)n2)cc1] 1343
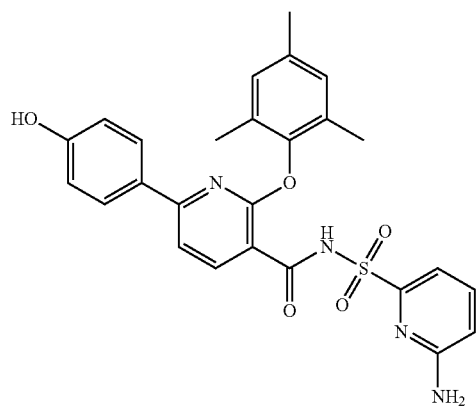 [SMILES: Cc1cc(C)c(Oc2nc(-c3ccc(O)cc3)ccc2C(=O)NS(=O)(=O)c2cccc(N)n2)c(C)c1] 1344
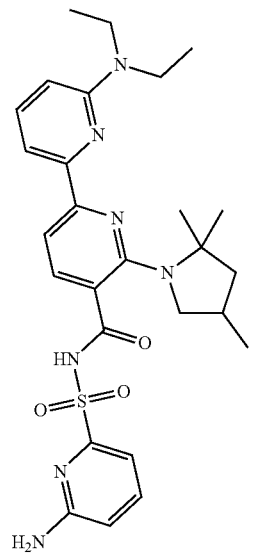 1345

TABLE 1-continued
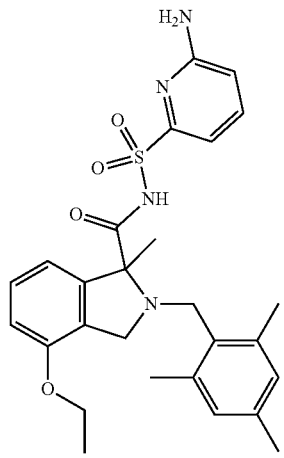
1346
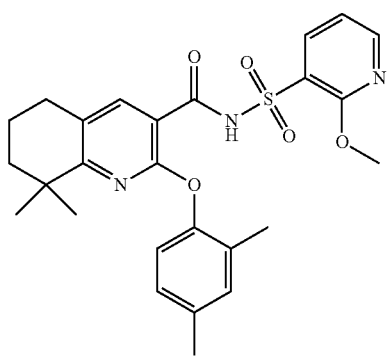 [SMILES: COc1ncccc1S(=O)(=O)NC(=O)c1cc2c(nc1Oc1ccc(C)cc1C)C(C)(C)CCC2]
1347
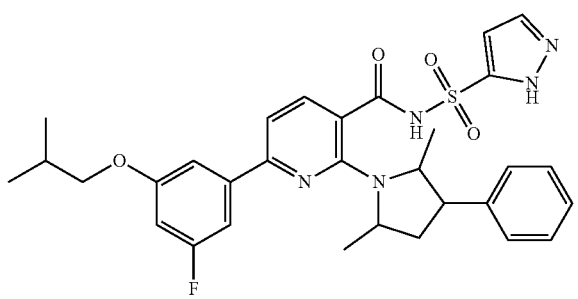 [SMILES: CC(C)COc1cc(F)cc(-c2ccc(C(=O)NS(=O)(=O)c3ccn[nH]3)c(N3C(C)CC(c4ccccc4)C3C)n2)c1]
1348
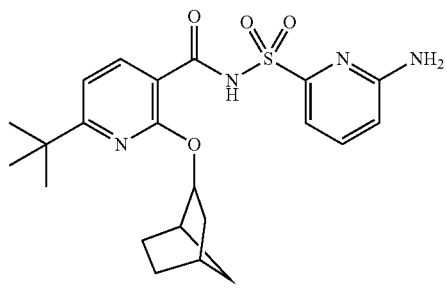 [SMILES: CC(C)(C)c1ccc(C(=O)NS(=O)(=O)c2cccc(N)n2)c(OC2CC3CCC2C3)n1]
1349
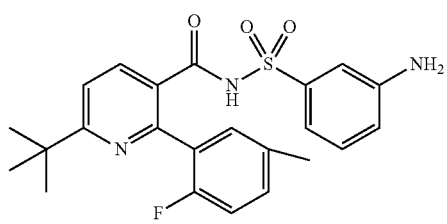 [SMILES: Cc1ccc(F)c(-c2nc(C(C)(C)C)ccc2C(=O)NS(=O)(=O)c2cccc(N)c2)c1]
1350

TABLE 1-continued
| | |
|---|---|
| 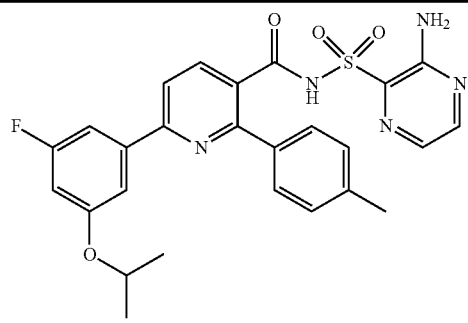 | 1351 |
| 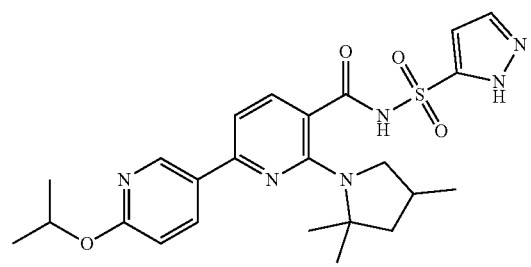 [SMILES: CC1CN(c2nc(-c3ccc(OC(C)C)nc3)ccc2C(=O)NS(=O)(=O)c2ccn[nH]2)C(C)(C)C1] | 1352 |
| 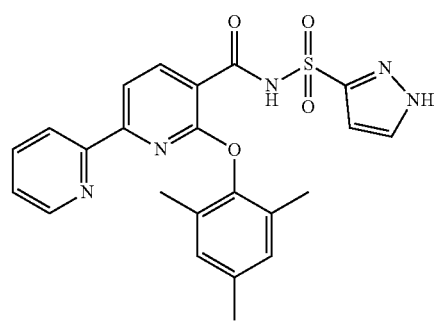 [SMILES: Cc1cc(C)c(Oc2nc(-c3ccccn3)ccc2C(=O)NS(=O)(=O)c2cc[nH]n2)c(C)c1] | 1353 |
| 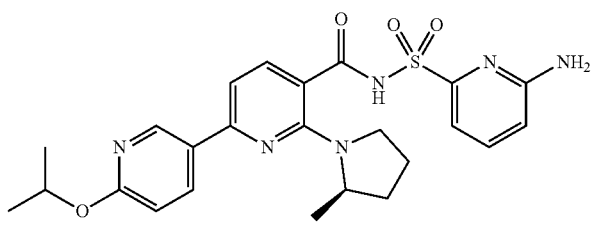 [SMILES: CC(C)Oc1ccc(-c2ccc(C(=O)NS(=O)(=O)c3cccc(N)n3)c(N3CCC[C@H]3C)n2)cn1] | 1354 |
| 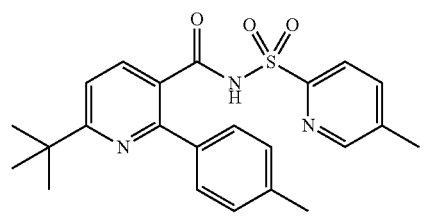 [SMILES: Cc1ccc(-c2nc(C(C)(C)C)ccc2C(=O)NS(=O)(=O)c2ccc(C)cn2)cc1] | 1355 |
| 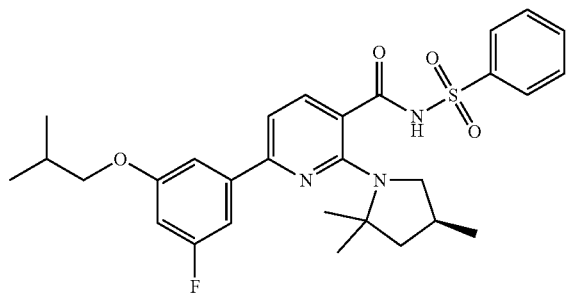 [SMILES: CC(C)COc1cc(F)cc(-c2ccc(C(=O)NS(=O)(=O)c3ccccc3)c(N3C[C@@H](C)CC3(C)C)n2)c1] | 1356 |

TABLE 1-continued
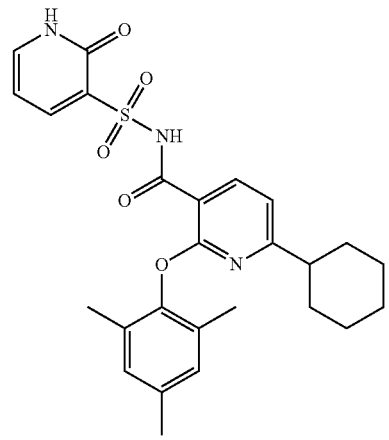 [SMILES: Cc1cc(C)c(Oc2nc(C3CCCCC3)ccc2C(=O)NS(=O)(=O)c2ccc[nH]c2=O)c(C)c1]
1357
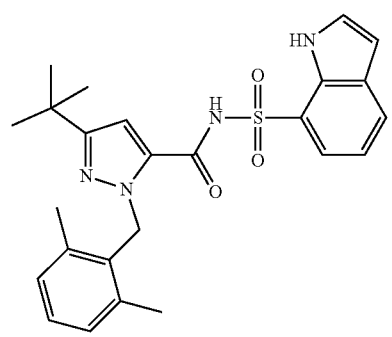 [SMILES: Cc1cccc(C)c1Cn1nc(C(C)(C)C)cc1C(=O)NS(=O)(=O)c1cccc2cc[nH]c12]
1358
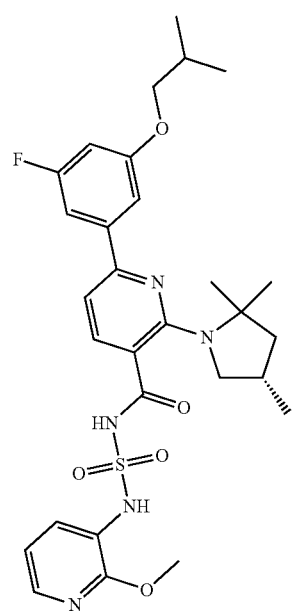 [SMILES: COc1ncccc1NS(=O)(=O)NC(=O)c1ccc(-c2cc(F)cc(OCC(C)C)c2)nc1N1C[C@@H](C)CC1(C)C]
1359

TABLE 1-continued
| | |
|---|---|
| 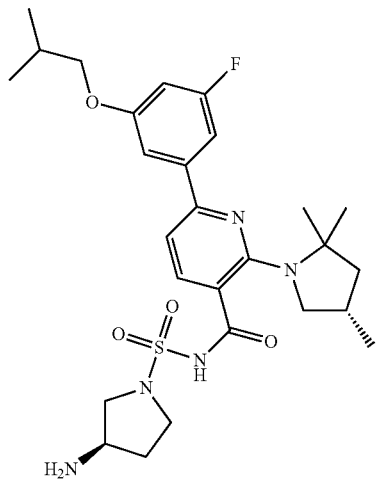 [SMILES: CC(C)COc1cc(F)cc(-c2ccc(C(=O)NS(=O)(=O)N3CC[C@@H](N)C3)c(N3C[C@@H](C)CC3(C)C)n2)c1] | 1360 |
| 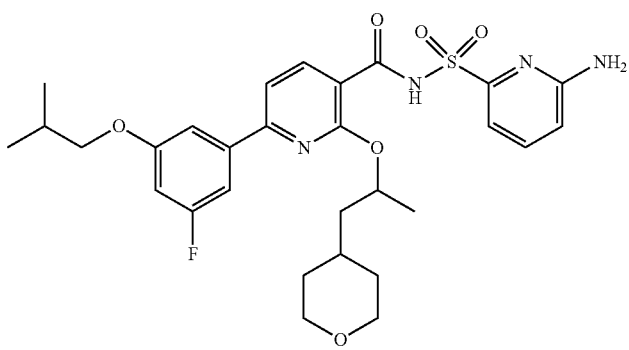 [SMILES: CC(C)COc1cc(F)cc(-c2ccc(C(=O)NS(=O)(=O)c3cccc(N)n3)c(OC(C)CC3CCOCC3)n2)c1] | 1361 |
| 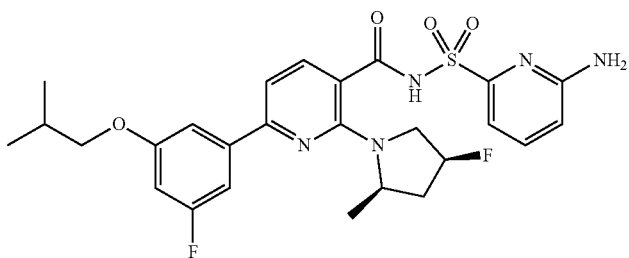 [SMILES: CC(C)COc1cc(F)cc(-c2ccc(C(=O)NS(=O)(=O)c3cccc(N)n3)c(N3C[C@@H](F)C[C@H]3C)n2)c1] | 1362 |
| 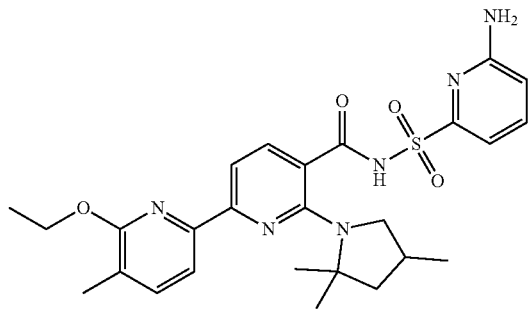 [SMILES: CCOc1nc(-c2ccc(C(=O)NS(=O)(=O)c3cccc(N)n3)c(N3CC(C)CC3(C)C)n2)ccc1C] | 1363 |
| 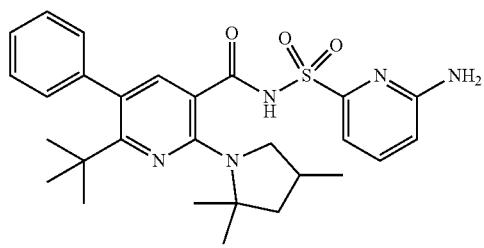 [SMILES: CC1CN(c2nc(C(C)(C)C)c(-c3ccccc3)cc2C(=O)NS(=O)(=O)c2cccc(N)n2)C(C)(C)C1] | 1364 |

TABLE 1-continued
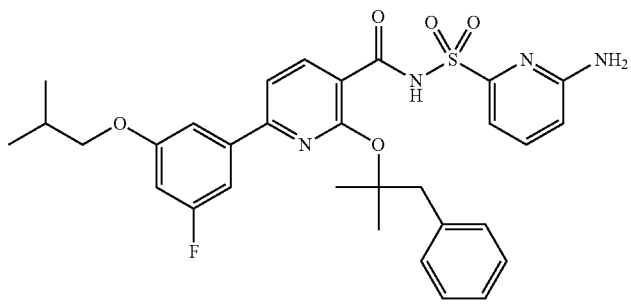 [SMILES: CC(C)COc1cc(F)cc(-c2ccc(C(=O)NS(=O)(=O)c3cccc(N)n3)c(OC(C)(C)Cc3ccccc3)n2)c1]
1365
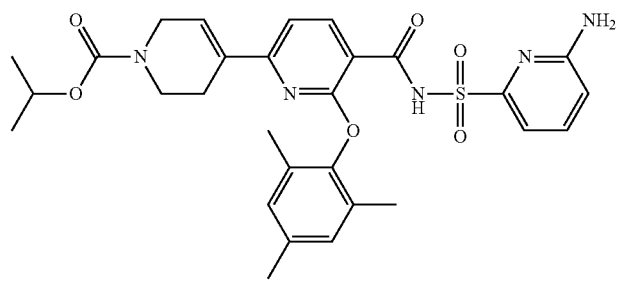 [SMILES: Cc1cc(C)c(Oc2nc(C3=CCN(C(=O)OC(C)C)CC3)ccc2C(=O)NS(=O)(=O)c2cccc(N)n2)c(C)c1]
1366
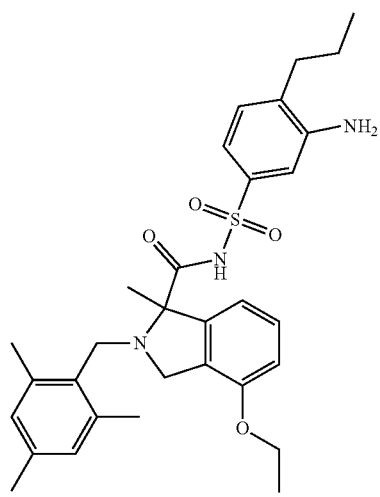 [SMILES: CCCc1ccc(S(=O)(=O)NC(=O)C2(C)c3cccc(OCC)c3CN2Cc2c(C)cc(C)cc2C)cc1N]
1367
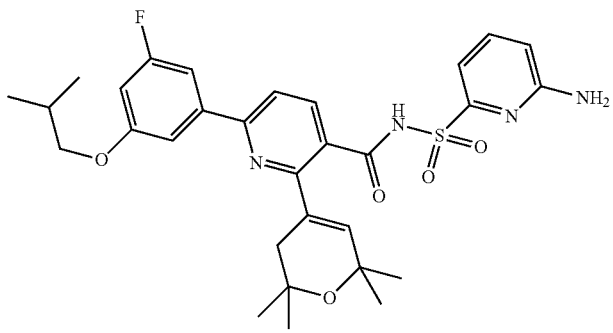
1368
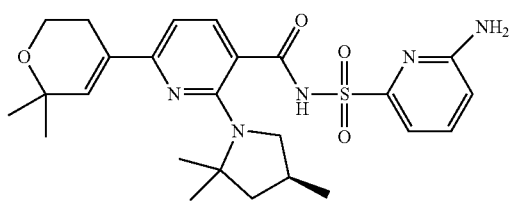 [SMILES: C[C@@H]1CN(c2nc(C3=CC(C)(C)OCC3)ccc2C(=O)NS(=O)(=O)c2cccc(N)n2)C(C)(C)C1]
1369

TABLE 1-continued
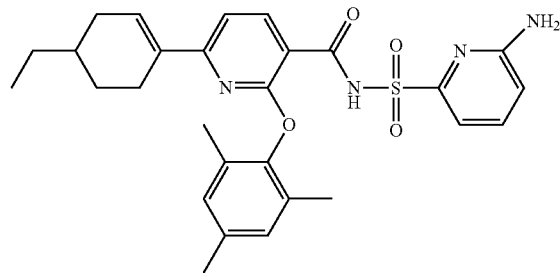 [SMILES: CCC1CC=C(c2ccc(C(=O)NS(=O)(=O)c3cccc(N)n3)c(Oc3c(C)cc(C)cc3C)n2)CC1]
1370
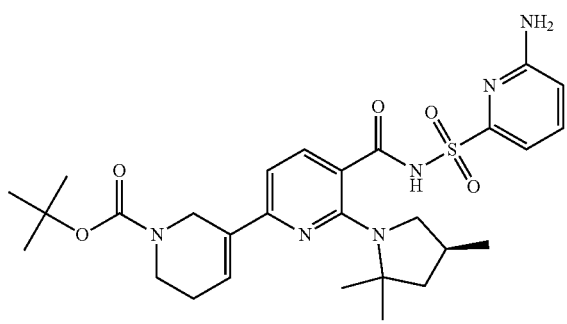 [SMILES: C[C@@H]1CN(c2nc(C3=CCCN(C(=O)OC(C)(C)C)C3)ccc2C(=O)NS(=O)(=O)c2cccc(N)n2)C(C)(C)C1]
1371
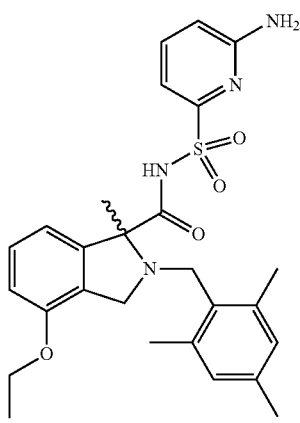 [SMILES: CCOc1cccc2c1CN(Cc1c(C)cc(C)cc1C)C2(C)C(=O)NS(=O)(=O)c1cccc(N)n1]
1372
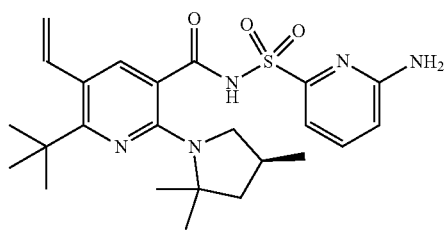 [SMILES: C=Cc1cc(C(=O)NS(=O)(=O)c2cccc(N)n2)c(N2C[C@@H](C)CC2(C)C)nc1C(C)(C)C]
1373
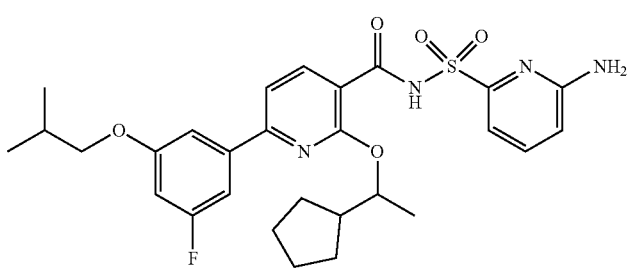 [SMILES: CC(C)COc1cc(F)cc(-c2ccc(C(=O)NS(=O)(=O)c3cccc(N)n3)c(OC(C)C3CCCC3)n2)c1]
1374

TABLE 1-continued
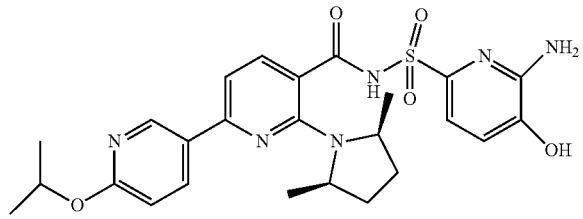 [SMILES: CC(C)Oc1ccc(-c2ccc(C(=O)NS(=O)(=O)c3ccc(O)c(N)n3)c(N3[C@H](C)CC[C@@H]3C)n2)cn1]
1375
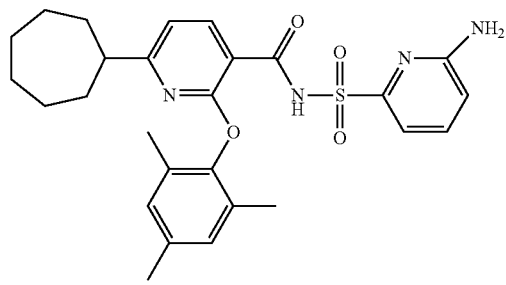 [SMILES: Cc1cc(C)c(Oc2nc(C3CCCCCC3)ccc2C(=O)NS(=O)(=O)c2cccc(N)n2)c(C)c1]
1376
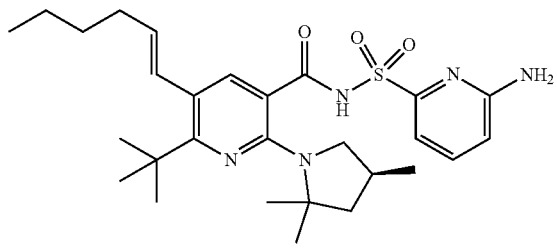 [SMILES: CCCC/C=C/c1cc(C(=O)NS(=O)(=O)c2cccc(N)n2)c(N2C[C@@H](C)CC2(C)C)nc1C(C)(C)C]
1377
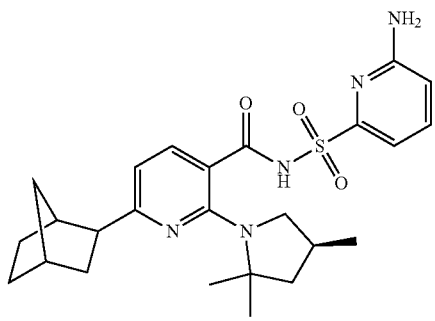 [SMILES: C[C@@H]1CN(c2nc(C3CC4CCC3C4)ccc2C(=O)NS(=O)(=O)c2cccc(N)n2)C(C)(C)C1]
1378
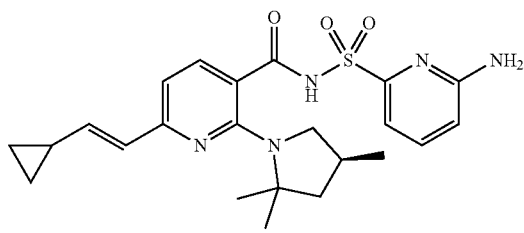 [SMILES: C[C@@H]1CN(c2nc(/C=C/C3CC3)ccc2C(=O)NS(=O)(=O)c2cccc(N)n2)C(C)(C)C1]
1379
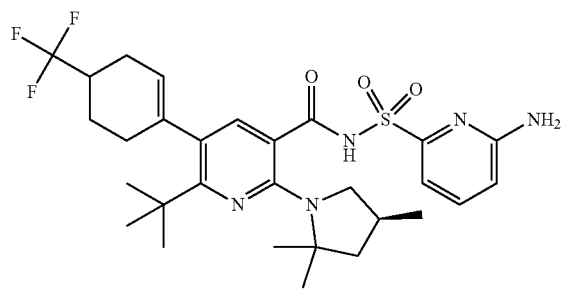 [SMILES: C[C@@H]1CN(c2nc(C(C)(C)C)c(C3=CCC(C(F)(F)F)CC3)cc2C(=O)NS(=O)(=O)c2cccc(N)n2)C(C)(C)C1]
1380

TABLE 1-continued
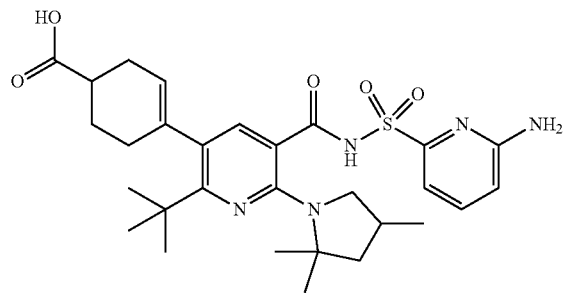 [SMILES: CC1CN(c2nc(C(C)(C)C)c(C3=CCC(C(=O)O)CC3)cc2C(=O)NS(=O)(=O)c2cccc(N)n2)C(C)(C)C1]
1381
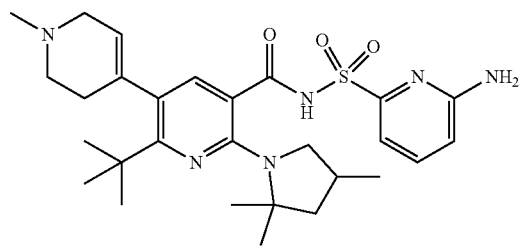 [SMILES: CC1CN(c2nc(C(C)(C)C)c(C3=CCN(C)CC3)cc2C(=O)NS(=O)(=O)c2cccc(N)n2)C(C)(C)C1]
1382
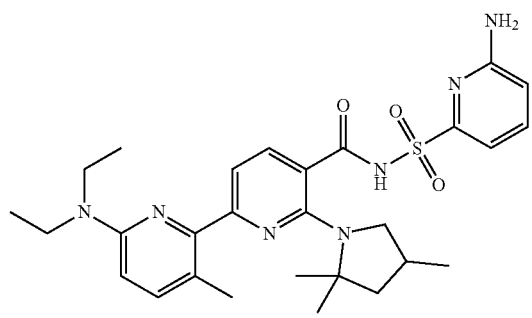 [SMILES: CCN(CC)c1ccc(C)c(-c2ccc(C(=O)NS(=O)(=O)c3cccc(N)n3)c(N3CC(C)CC3(C)C)n2)n1]
1383
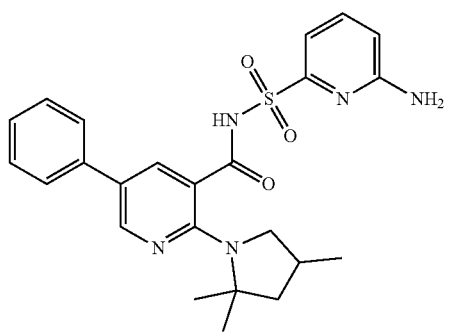 [SMILES: CC1CN(c2ncc(-c3ccccc3)cc2C(=O)NS(=O)(=O)c2cccc(N)n2)C(C)(C)C1]
1384
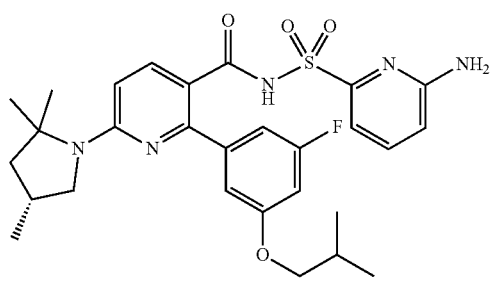 [SMILES: CC(C)COc1cc(F)cc(-c2nc(N3C[C@H](C)CC3(C)C)ccc2C(=O)NS(=O)(=O)c2cccc(N)n2)c1]
1385

TABLE 1-continued
1386
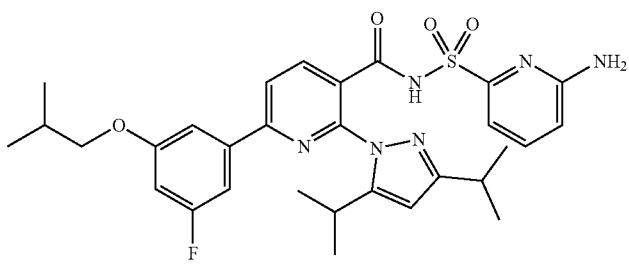 [SMILES: CC(C)COc1cc(F)cc(-c2ccc(C(=O)NS(=O)(=O)c3cccc(N)n3)c(-n3nc(C(C)C)cc3C(C)C)n2)c1]
1387
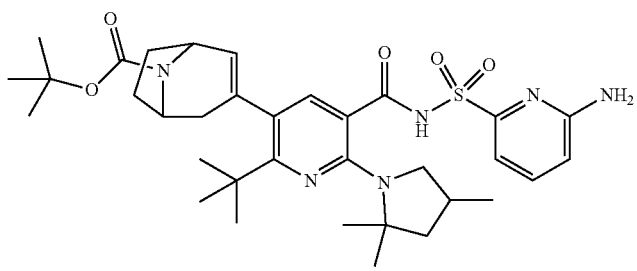 [SMILES: CC1CN(c2nc(C(C)(C)C)c(C3=CC4CCC(C3)N4C(=O)OC(C)(C)C)cc2C(=O)NS(=O)(=O)c2cccc(N)n2)C(C)(C)C1]
1388
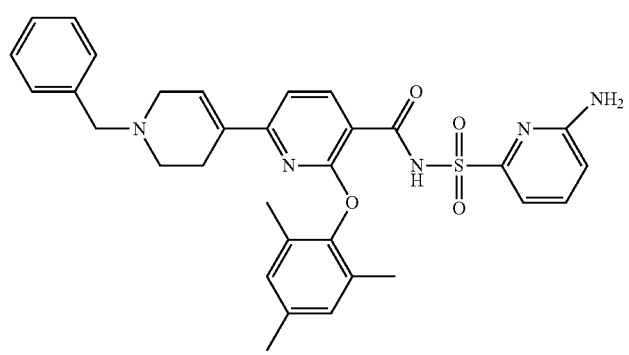 [SMILES: Cc1cc(C)c(Oc2nc(C3=CCN(Cc4ccccc4)CC3)ccc2C(=O)NS(=O)(=O)c2cccc(N)n2)c(C)c1]
1389
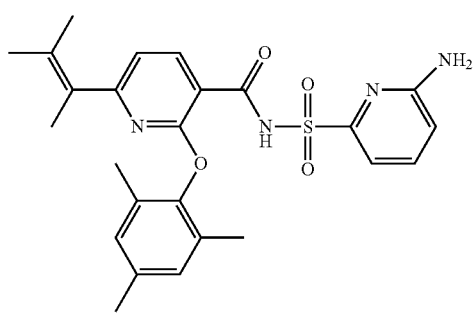 [SMILES: CC(C)=C(C)c1ccc(C(=O)NS(=O)(=O)c2cccc(N)n2)c(Oc2c(C)cc(C)cc2C)n1]
1390

TABLE 1-continued
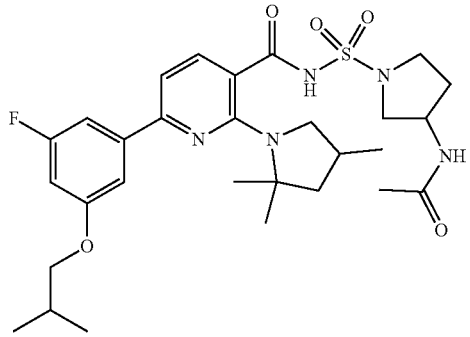 [SMILES: CC(=O)NC1CCN(S(=O)(=O)NC(=O)c2ccc(-c3cc(F)cc(OCC(C)C)c3)nc2N2CC(C)CC2(C)C)C1]
1391
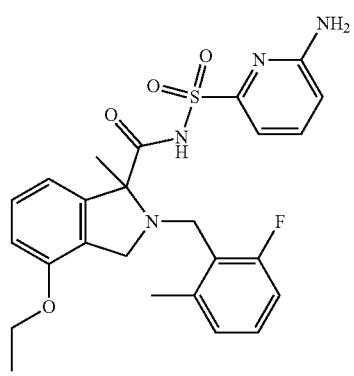 [SMILES: CCOc1cccc2c1CN(Cc1c(C)cccc1F)C2(C)C(=O)NS(=O)(=O)c1cccc(N)n1]
1392
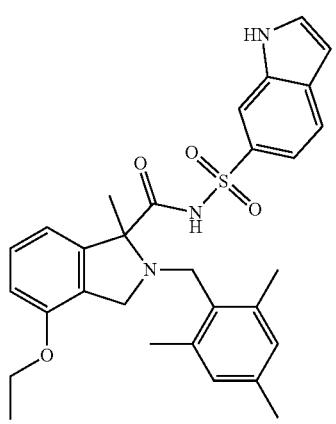 [SMILES: CCOc1cccc2c1CN(Cc1c(C)cc(C)cc1C)C2(C)C(=O)NS(=O)(=O)c1ccc2cc[nH]c2c1]
1393
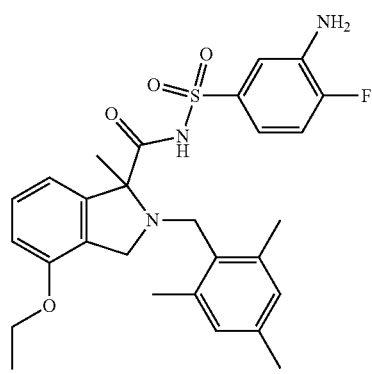 [SMILES: CCOc1cccc2c1CN(Cc1c(C)cc(C)cc1C)C2(C)C(=O)NS(=O)(=O)c1ccc(F)c(N)c1]
1394

TABLE 1-continued
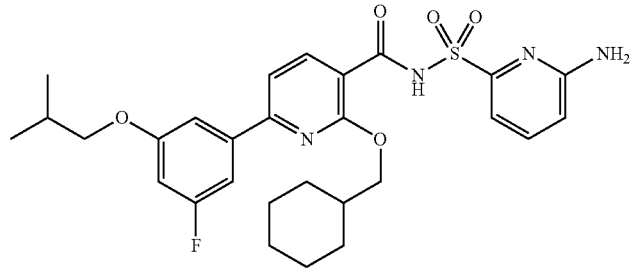 [SMILES: CC(C)COc1cc(F)cc(-c2ccc(C(=O)NS(=O)(=O)c3cccc(N)n3)c(OCC3CCCCC3)n2)c1]
1395
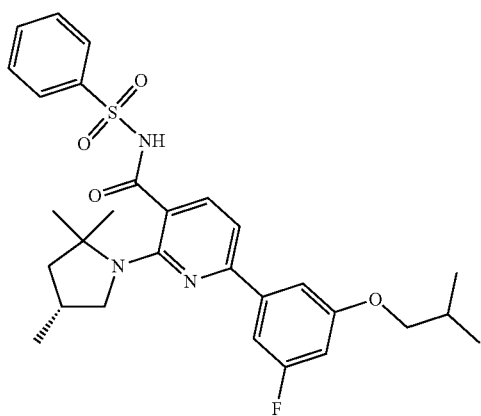 [SMILES: CC(C)COc1cc(F)cc(-c2ccc(C(=O)NS(=O)(=O)c3ccccc3)c(N3C[C@H](C)CC3(C)C)n2)c1]
1396
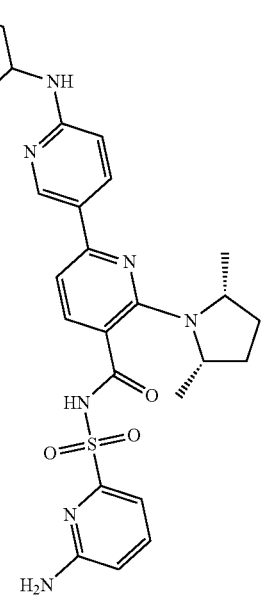
1397

TABLE 1-continued
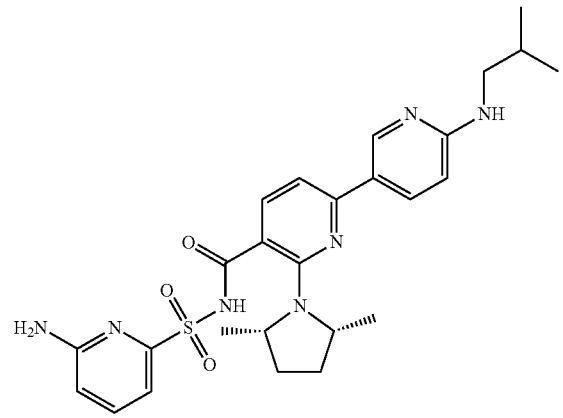 [SMILES: CC(C)CNc1ccc(-c2ccc(C(=O)NS(=O)(=O)c3cccc(N)n3)c(N3[C@H](C)CC[C@@H]3C)n2)cn1]
1398
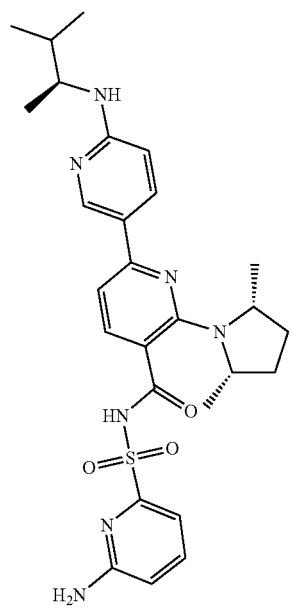 [SMILES: CC(C)[C@H](C)Nc1ccc(-c2ccc(C(=O)NS(=O)(=O)c3cccc(N)n3)c(N3[C@H](C)CC[C@@H]3C)n2)cn1]
1399
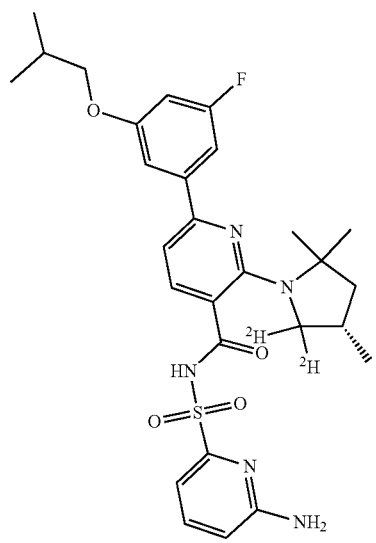 [SMILES: [2H]C1([2H])[C@@H](C)CC(C)(C)N1c1nc(-c2cc(F)cc(OCC(C)C)c2)ccc1C(=O)NS(=O)(=O)c1cccc(N)n1]
1400

TABLE 1-continued
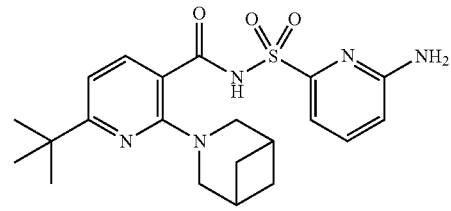 [SMILES: CC(C)(C)c1ccc(C(=O)NS(=O)(=O)c2cccc(N)n2)c(N2CC3CC(C3)C2)n1]
1401
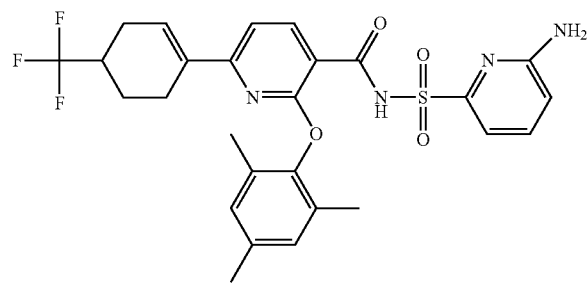 [SMILES: Cc1cc(C)c(Oc2nc(C3=CCC(C(F)(F)F)CC3)ccc2C(=O)NS(=O)(=O)c2cccc(N)n2)c(C)c1]
1402
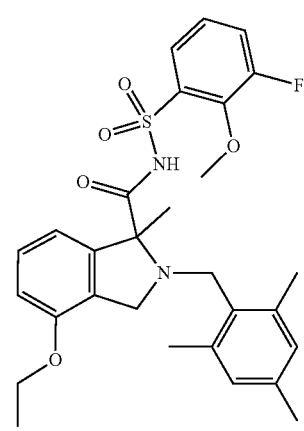
1403
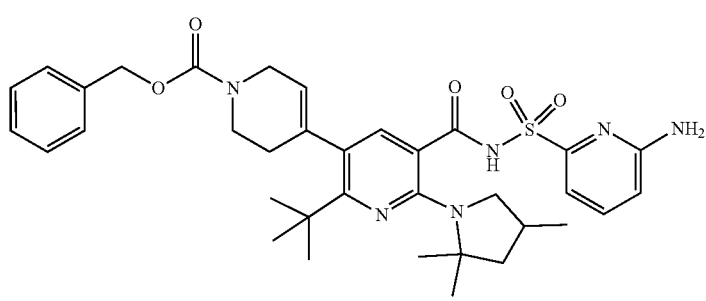 [SMILES: CC1CN(c2nc(C(C)(C)C)c(C3=CCN(C(=O)OCc4ccccc4)CC3)cc2C(=O)NS(=O)(=O)c2cccc(N)n2)C(C)(C)C1]
1404
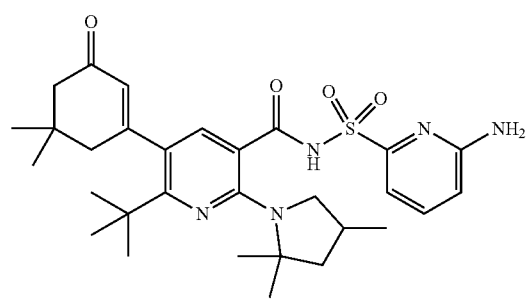 [SMILES: CC1CN(c2nc(C(C)(C)C)c(C3=CC(=O)CC(C)(C)C3)cc2C(=O)NS(=O)(=O)c2cccc(N)n2)C(C)(C)C1]
1405

TABLE 1-continued
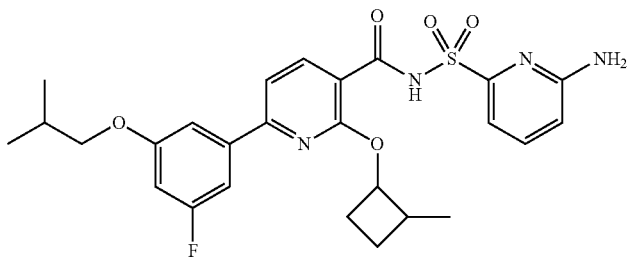 [SMILES: CC(C)COc1cc(F)cc(-c2ccc(C(=O)NS(=O)(=O)c3cccc(N)n3)c(OC3CCC3C)n2)c1]
1406
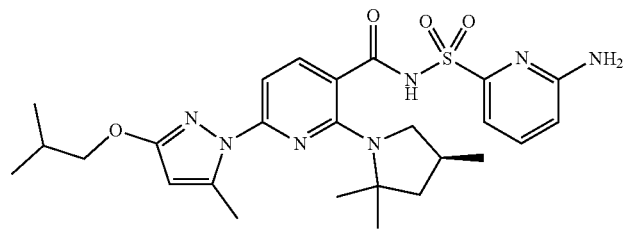 [SMILES: Cc1cc(OCC(C)C)nn1-c1ccc(C(=O)NS(=O)(=O)c2cccc(N)n2)c(N2C[C@@H](C)CC2(C)C)n1]
1407
1408
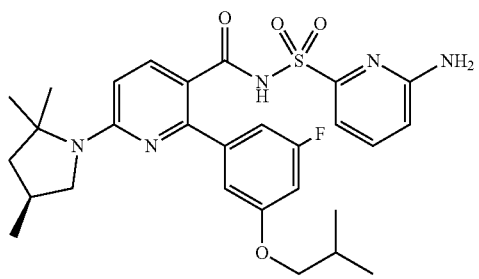 [SMILES: CC(C)COc1cc(F)cc(-c2nc(N3C[C@@H](C)CC3(C)C)ccc2C(=O)NS(=O)(=O)c2cccc(N)n2)c1]
1409
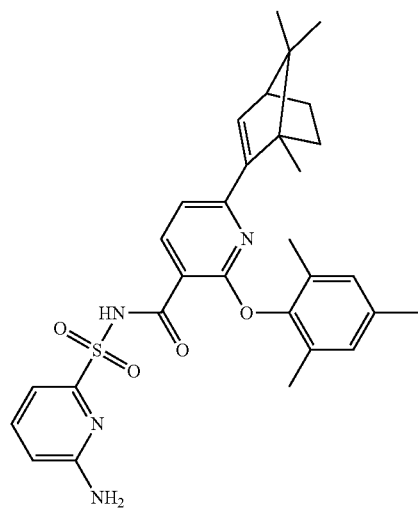 [SMILES: Cc1cc(C)c(Oc2nc(C3=CC4CCC3(C)C4(C)C)ccc2C(=O)NS(=O)(=O)c2cccc(N)n2)c(C)c1]
1410

TABLE 1-continued
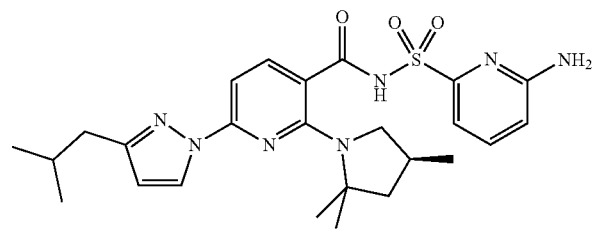 [SMILES: CC(C)Cc1ccn(-c2ccc(C(=O)NS(=O)(=O)c3cccc(N)n3)c(N3C[C@@H](C)CC3(C)C)n2)n1]
1411
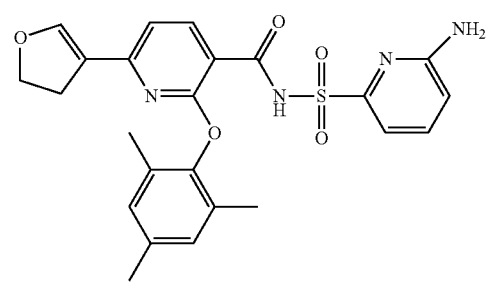 [SMILES: Cc1cc(C)c(Oc2nc(C3=COCC3)ccc2C(=O)NS(=O)(=O)c2cccc(N)n2)c(C)c1]
1412
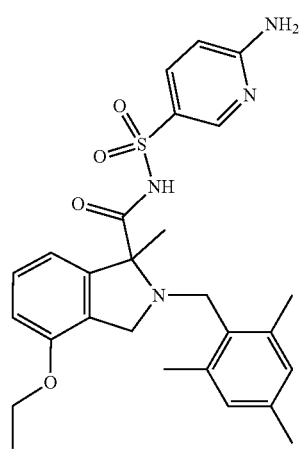
1413
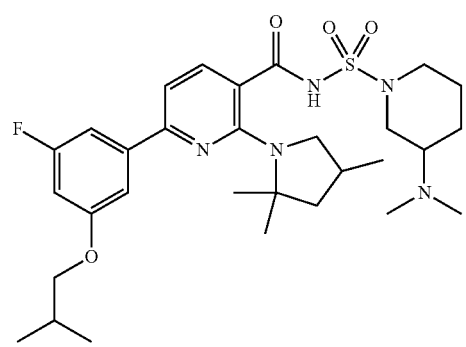 [SMILES: CC(C)COc1cc(F)cc(-c2ccc(C(=O)NS(=O)(=O)N3CCCC(N(C)C)C3)c(N3CC(C)CC3(C)C)n2)c1]
1414

TABLE 1-continued
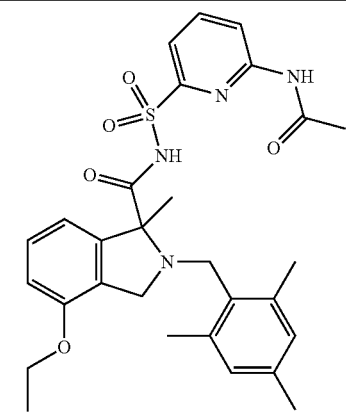
1415
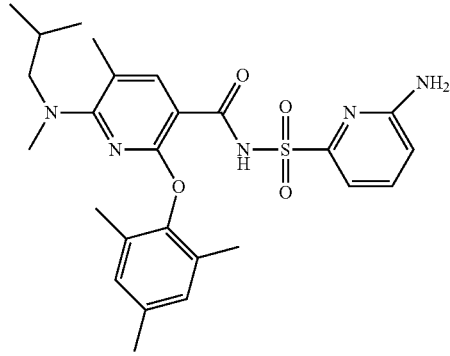 [SMILES: Cc1cc(C)c(Oc2nc(N(C)CC(C)C)c(C)cc2C(=O)NS(=O)(=O)c2cccc(N)n2)c(C)c1]
1416
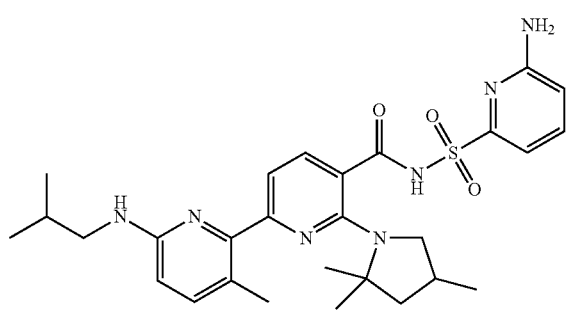 [SMILES: Cc1ccc(NCC(C)C)nc1-c1ccc(C(=O)NS(=O)(=O)c2cccc(N)n2)c(N2CC(C)CC2(C)C)n1]
1417
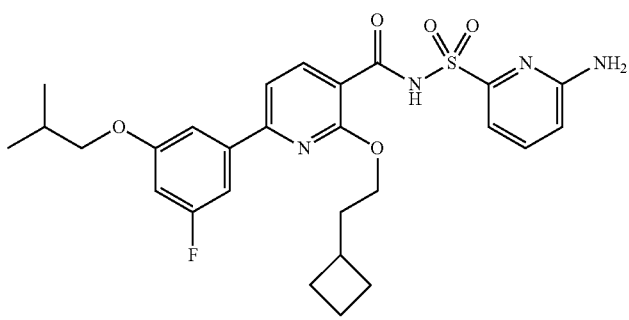 [SMILES: CC(C)COc1cc(F)cc(-c2ccc(C(=O)NS(=O)(=O)c3cccc(N)n3)c(OCCC3CCC3)n2)c1]
1418
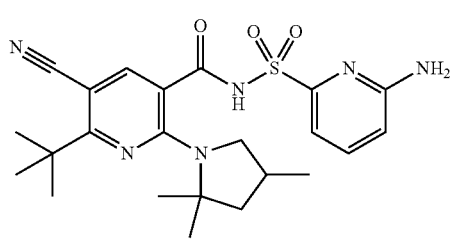 [SMILES: CC1CN(c2nc(C(C)(C)C)c(C#N)cc2C(=O)NS(=O)(=O)c2cccc(N)n2)C(C)(C)C1]
1419

TABLE 1-continued
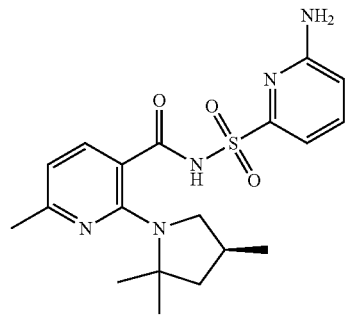 [SMILES: Cc1ccc(C(=O)NS(=O)(=O)c2cccc(N)n2)c(N2C[C@@H](C)CC2(C)C)n1]
1420
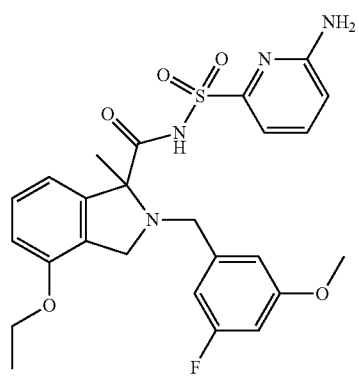 [SMILES: CCOc1cccc2c1CN(Cc1cc(F)cc(OC)c1)C2(C)C(=O)NS(=O)(=O)c1cccc(N)n1]
1421
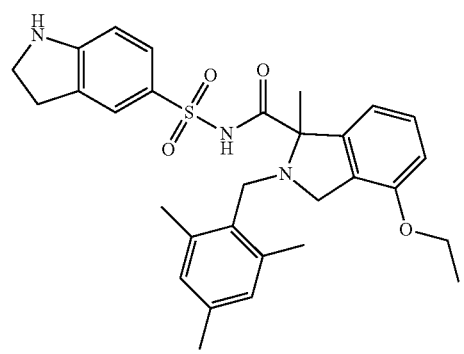 [SMILES: CCOc1cccc2c1CN(Cc1c(C)cc(C)cc1C)C2(C)C(=O)NS(=O)(=O)c1ccc2c(c1)CCN2]
1422
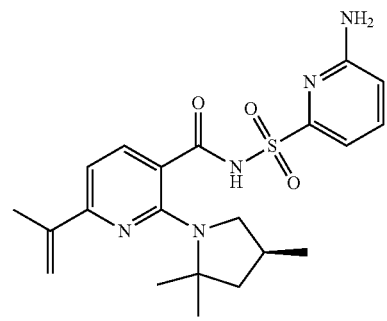 [SMILES: C=C(C)c1ccc(C(=O)NS(=O)(=O)c2cccc(N)n2)c(N2C[C@@H](C)CC2(C)C)n1]
1423

TABLE 1-continued
| | |
|---|---|
| 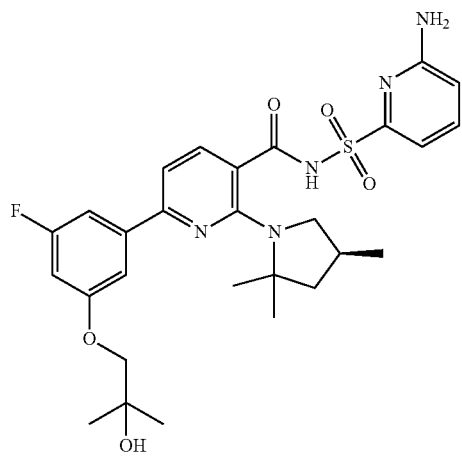 [SMILES: C[C@@H]1CN(c2nc(-c3cc(F)cc(OCC(C)(C)O)c3)ccc2C(=O)NS(=O)(=O)c2cccc(N)n2)C(C)(C)C1] | 1424 |
| 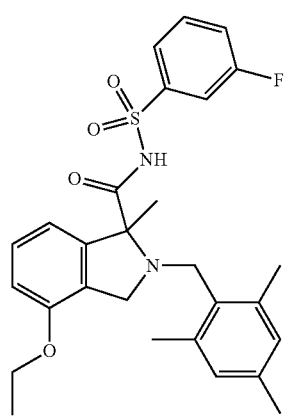 [SMILES: CCOc1cccc2c1CN(Cc1c(C)cc(C)cc1C)C2(C)C(=O)NS(=O)(=O)c1cccc(F)c1] | 1425 |
| 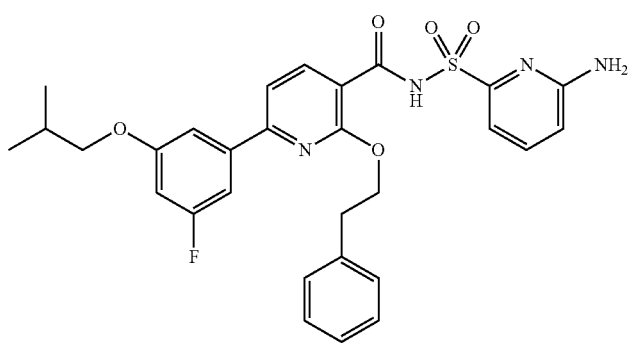 [SMILES: CC(C)COc1cc(F)cc(-c2ccc(C(=O)NS(=O)(=O)c3cccc(N)n3)c(OCCc3ccccc3)n2)c1] | 1426 |
|  | 1427 |

TABLE 1-continued
| | |
|---|---|
| 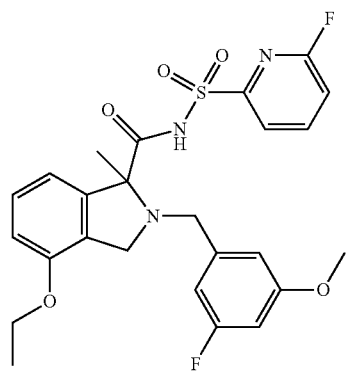 [SMILES: CCOc1cccc2c1CN(Cc1cc(F)cc(OC)c1)C2(C)C(=O)NS(=O)(=O)c1cccc(F)n1] | 1428 |
| 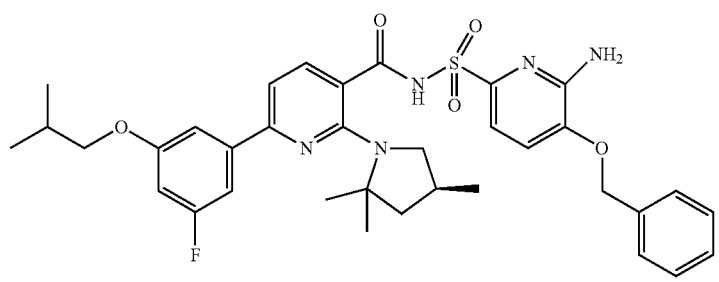 [SMILES: CC(C)COc1cc(F)cc(-c2ccc(C(=O)NS(=O)(=O)c3ccc(OCc4ccccc4)c(N)n3)c(N3C[C@@H](C)CC3(C)C)n2)c1] | 1429 |
| 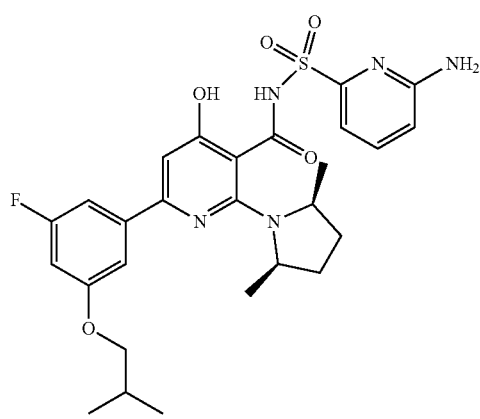 [SMILES: CC(C)COc1cc(F)cc(-c2cc(O)c(C(=O)NS(=O)(=O)c3cccc(N)n3)c(N3[C@H](C)CC[C@@H]3C)n2)c1] | 1430 |
| 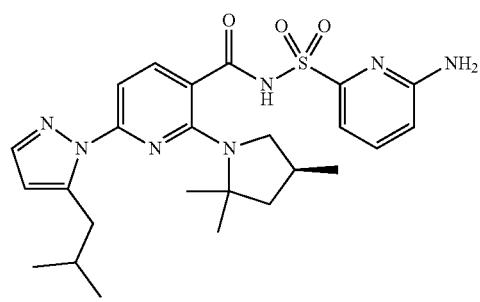 [SMILES: CC(C)Cc1ccnn1-c1ccc(C(=O)NS(=O)(=O)c2cccc(N)n2)c(N2C[C@@H](C)CC2(C)C)n1] | 1431 |
| 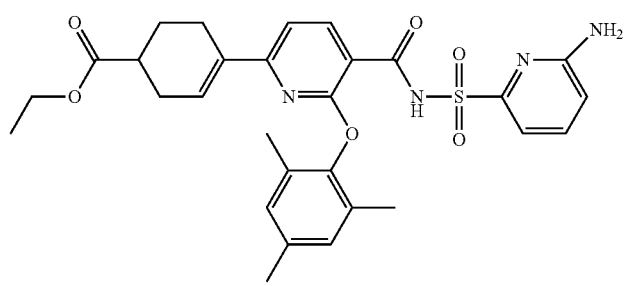 [SMILES: CCOC(=O)C1CC=C(c2ccc(C(=O)NS(=O)(=O)c3cccc(N)n3)c(Oc3c(C)cc(C)cc3C)n2)CC1] | 1432 |

TABLE 1-continued
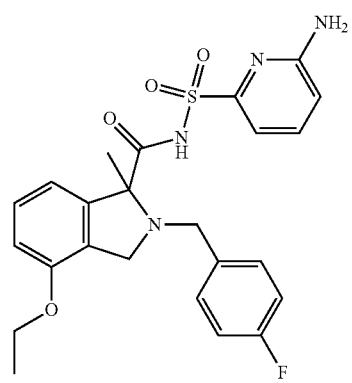 [SMILES: CCOc1cccc2c1CN(Cc1ccc(F)cc1)C2(C)C(=O)NS(=O)(=O)c1cccc(N)n1]
1433
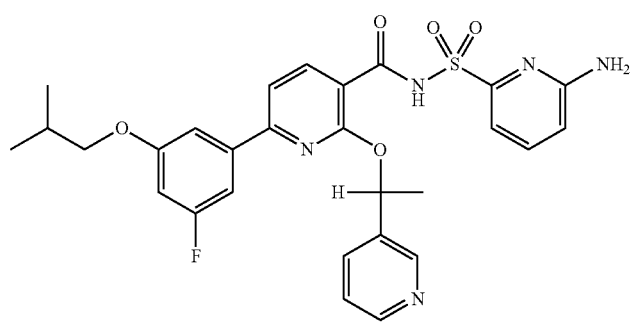 [SMILES: CC(C)COc1cc(F)cc(-c2ccc(C(=O)NS(=O)(=O)c3cccc(N)n3)c(OC(C)c3cccnc3)n2)c1]
1434
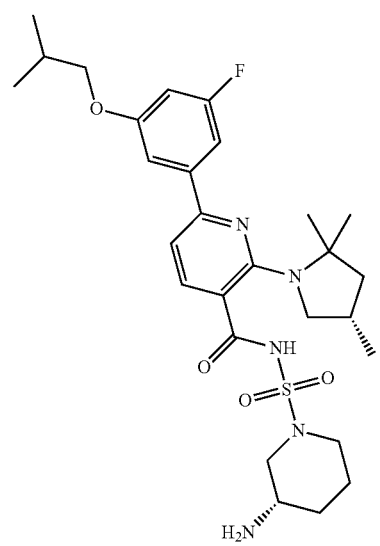 [SMILES: CC(C)COc1cc(F)cc(-c2ccc(C(=O)NS(=O)(=O)N3CCC[C@H](N)C3)c(N3C[C@@H](C)CC3(C)C)n2)c1]
1435
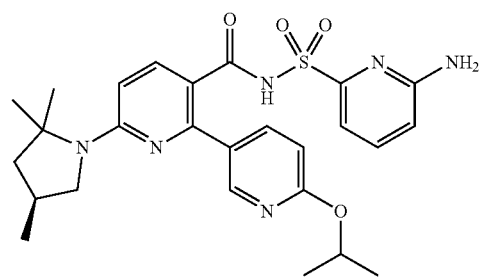 [SMILES: CC(C)Oc1ccc(-c2nc(N3C[C@@H](C)CC3(C)C)ccc2C(=O)NS(=O)(=O)c2cccc(N)n2)cn1]
1436

TABLE 1-continued
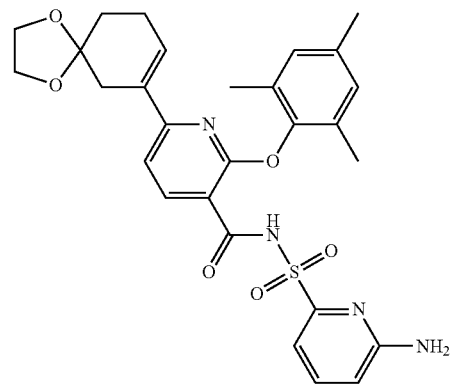 [SMILES: Cc1cc(C)c(Oc2nc(C3=CCCC4(C3)OCCO4)ccc2C(=O)NS(=O)(=O)c2cccc(N)n2)c(C)c1]
1437
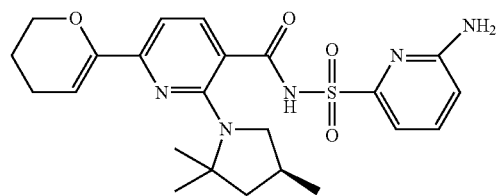 [SMILES: C[C@@H]1CN(c2nc(C3=CCCCO3)ccc2C(=O)NS(=O)(=O)c2cccc(N)n2)C(C)(C)C1]
1438
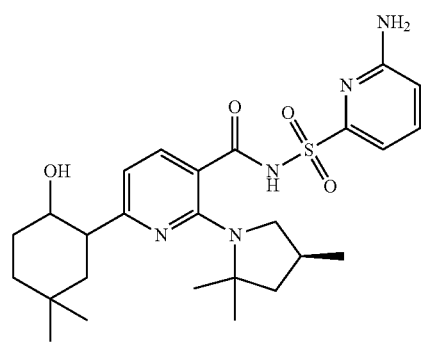 [SMILES: C[C@@H]1CN(c2nc(C3CC(C)(C)CCC3O)ccc2C(=O)NS(=O)(=O)c2cccc(N)n2)C(C)(C)C1]
1439
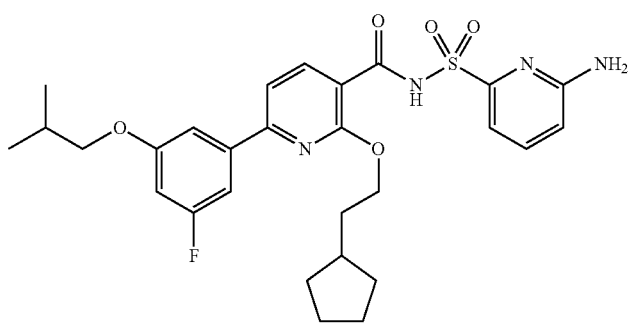
1440
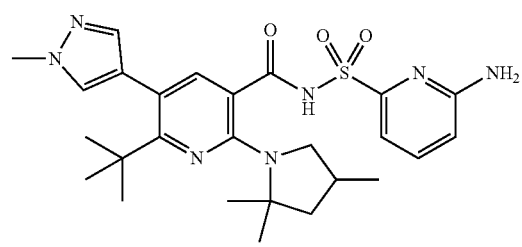 [SMILES: CC1CN(c2nc(C(C)(C)C)c(-c3cnn(C)c3)cc2C(=O)NS(=O)(=O)c2cccc(N)n2)C(C)(C)C1]
1441

TABLE 1-continued
| | |
|---|---|
| 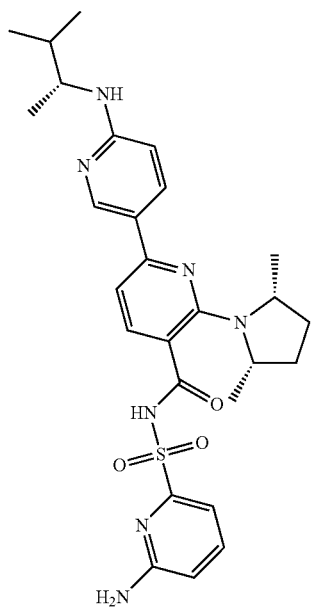 [SMILES: CC(C)[C@@H](C)Nc1ccc(-c2ccc(C(=O)NS(=O)(=O)c3cccc(N)n3)c(N3[C@H](C)CC[C@@H]3C)n2)cn1] | 1442 |
| 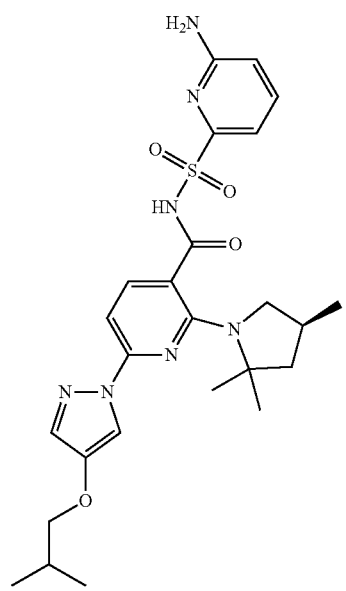 [SMILES: CC(C)COc1cnn(-c2ccc(C(=O)NS(=O)(=O)c3cccc(N)n3)c(N3C[C@@H](C)CC3(C)C)n2)c1] | 1443 |
| 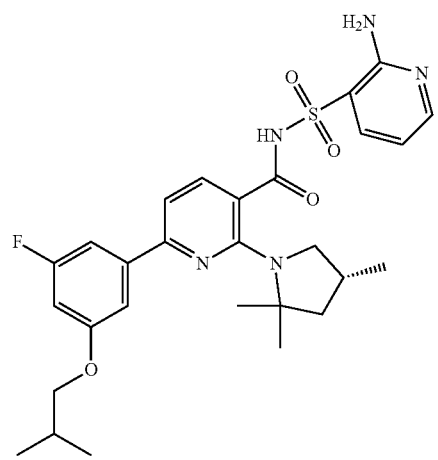 [SMILES: CC(C)COc1cc(F)cc(-c2ccc(C(=O)NS(=O)(=O)c3cccnc3N)c(N3C[C@H](C)CC3(C)C)n2)c1] | 1444 |

TABLE 1-continued
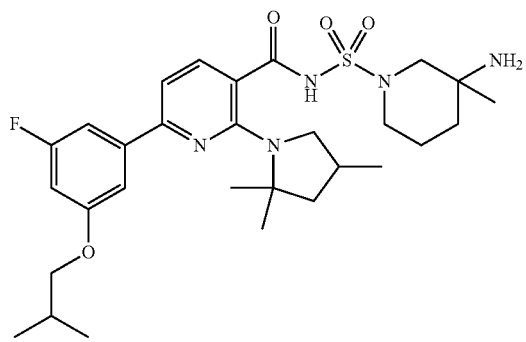 [SMILES: CC(C)COc1cc(F)cc(-c2ccc(C(=O)NS(=O)(=O)N3CCCC(C)(N)C3)c(N3CC(C)CC3(C)C)n2)c1]
1445
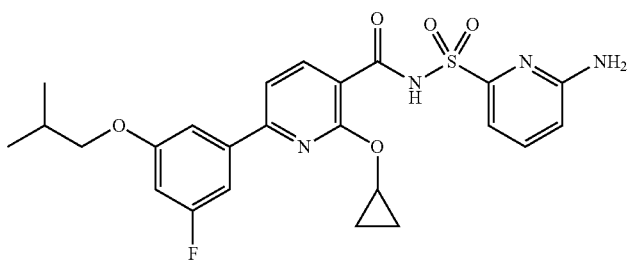 [SMILES: CC(C)COc1cc(F)cc(-c2ccc(C(=O)NS(=O)(=O)c3cccc(N)n3)c(OC3CC3)n2)c1]
1446
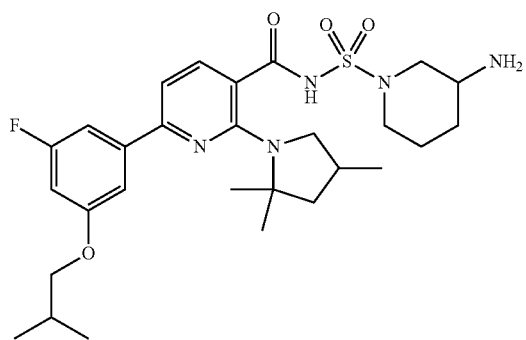 [SMILES: CC(C)COc1cc(F)cc(-c2ccc(C(=O)NS(=O)(=O)N3CCCC(N)C3)c(N3CC(C)CC3(C)C)n2)c1]
1447
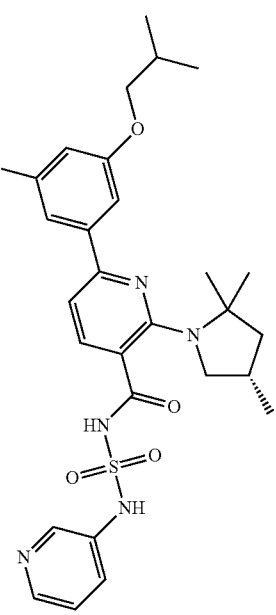
1448

TABLE 1-continued
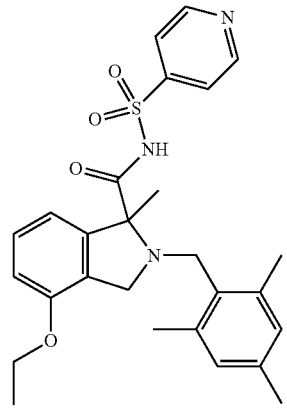 [SMILES: CCOc1cccc2c1CN(Cc1c(C)cc(C)cc1C)C2(C)C(=O)NS(=O)(=O)c1ccncc1]
1449
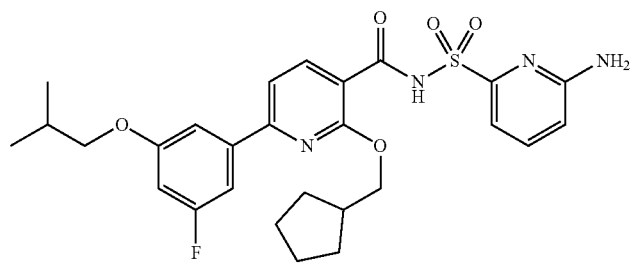 [SMILES: CC(C)COc1cc(F)cc(-c2ccc(C(=O)NS(=O)(=O)c3cccc(N)n3)c(OCC3CCCC3)n2)c1]
1450
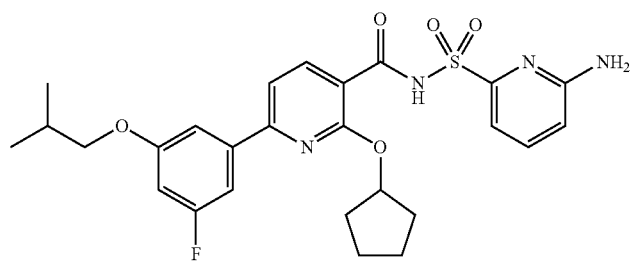 [SMILES: CC(C)COc1cc(F)cc(-c2ccc(C(=O)NS(=O)(=O)c3cccc(N)n3)c(OC3CCCC3)n2)c1]
1451
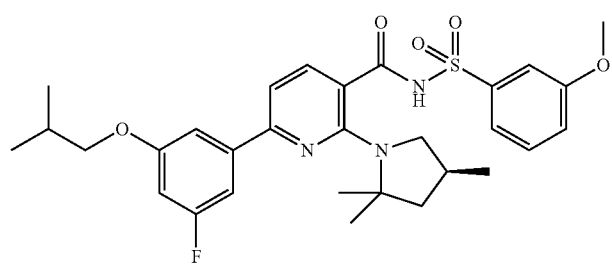 [SMILES: COc1cccc(S(=O)(=O)NC(=O)c2ccc(-c3cc(F)cc(OCC(C)C)c3)nc2N2C[C@@H](C)CC2(C)C)c1]
1452
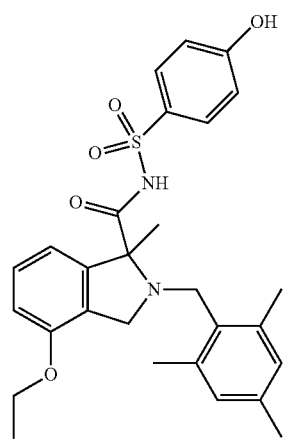 [SMILES: CCOc1cccc2c1CN(Cc1c(C)cc(C)cc1C)C2(C)C(=O)NS(=O)(=O)c1ccc(O)cc1]
1453

TABLE 1-continued
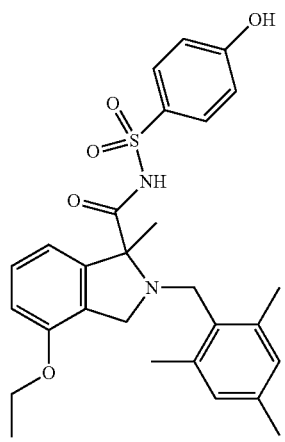 [SMILES: CCOc1cccc2c1CN(Cc1c(C)cc(C)cc1C)C2(C)C(=O)NS(=O)(=O)c1ccc(O)cc1]
1454
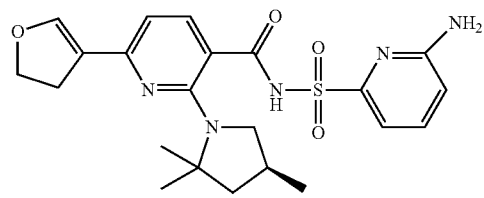 [SMILES: C[C@@H]1CN(c2nc(C3=COCC3)ccc2C(=O)NS(=O)(=O)c2cccc(N)n2)C(C)(C)C1]
1455
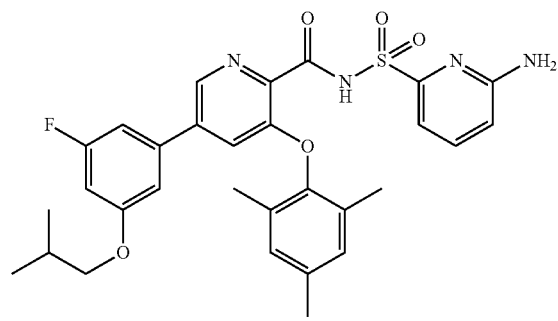 [SMILES: Cc1cc(C)c(Oc2cc(-c3cc(F)cc(OCC(C)C)c3)cnc2C(=O)NS(=O)(=O)c2cccc(N)n2)c(C)c1]
1456
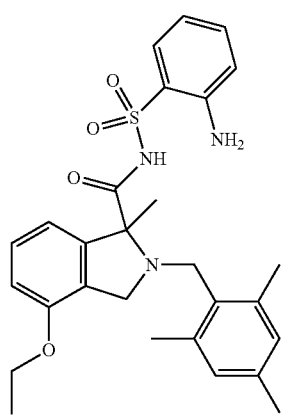 [SMILES: CCOc1cccc2c1CN(Cc1c(C)cc(C)cc1C)C2(C)C(=O)NS(=O)(=O)c1ccccc1N]
1457

TABLE 1-continued
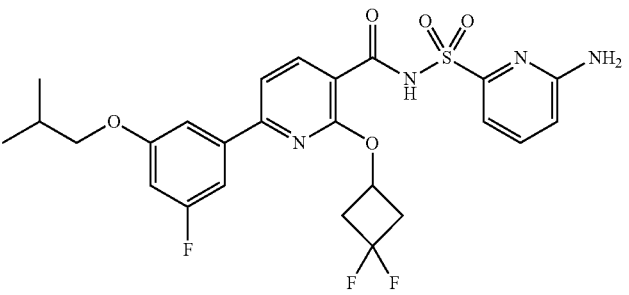 [SMILES: CC(C)COc1cc(F)cc(-c2ccc(C(=O)NS(=O)(=O)c3cccc(N)n3)c(OC3CC(F)(F)C3)n2)c1]
1458
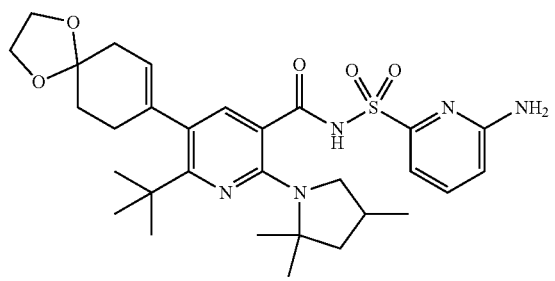 [SMILES: CC1CN(c2nc(C(C)(C)C)c(C3=CCC4(CC3)OCCO4)cc2C(=O)NS(=O)(=O)c2cccc(N)n2)C(C)(C)C1]
1459
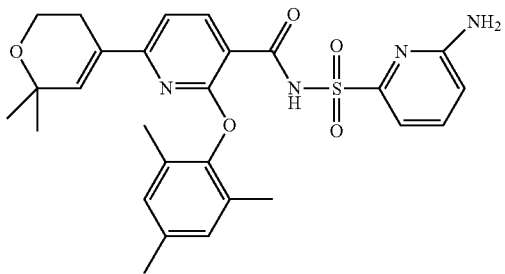 [SMILES: Cc1cc(C)c(Oc2nc(C3=CC(C)(C)OCC3)ccc2C(=O)NS(=O)(=O)c2cccc(N)n2)c(C)c1]
1460
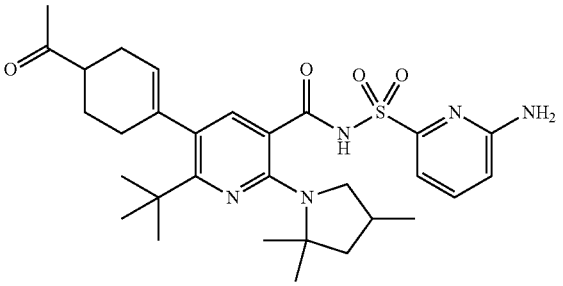 [SMILES: CC(=O)C1CC=C(c2cc(C(=O)NS(=O)(=O)c3cccc(N)n3)c(N3CC(C)CC3(C)C)nc2C(C)(C)C)CC1]
1461
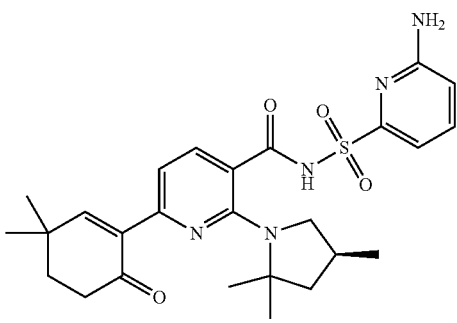 [SMILES: C[C@@H]1CN(c2nc(C3=CC(C)(C)CCC3=O)ccc2C(=O)NS(=O)(=O)c2cccc(N)n2)C(C)(C)C1]
1462

TABLE 1-continued
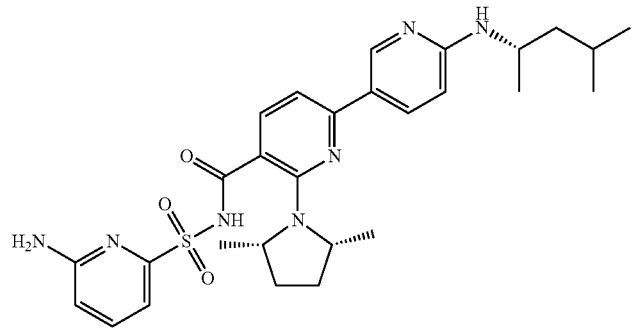 [SMILES: CC(C)C[C@H](C)Nc1ccc(-c2ccc(C(=O)NS(=O)(=O)c3cccc(N)n3)c(N3[C@H](C)CC[C@@H]3C)n2)cn1]
1463
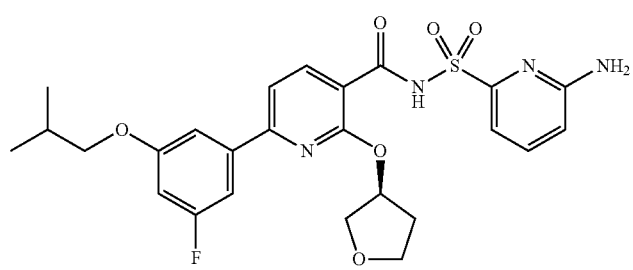 [SMILES: CC(C)COc1cc(F)cc(-c2ccc(C(=O)NS(=O)(=O)c3cccc(N)n3)c(O[C@H]3CCOC3)n2)c1]
1464
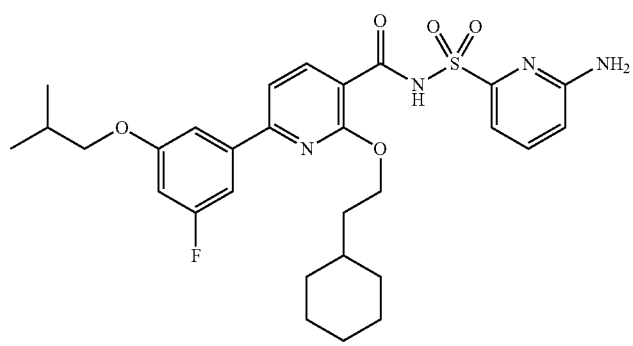
1465
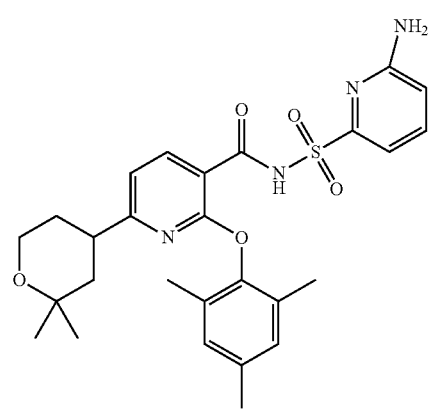 [SMILES: Cc1cc(C)c(Oc2nc(C3CCOC(C)(C)C3)ccc2C(=O)NS(=O)(=O)c2cccc(N)n2)c(C)c1]
1466

TABLE 1-continued
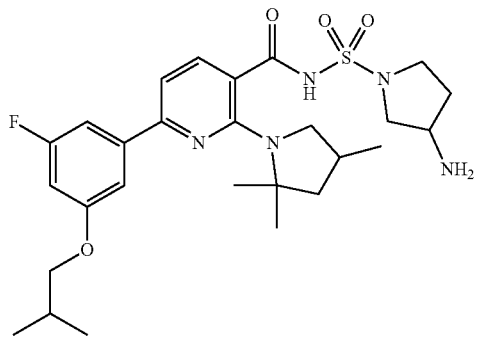 [SMILES: CC(C)COc1cc(F)cc(-c2ccc(C(=O)NS(=O)(=O)N3CCC(N)C3)c(N3CC(C)CC3(C)C)n2)c1]
1467
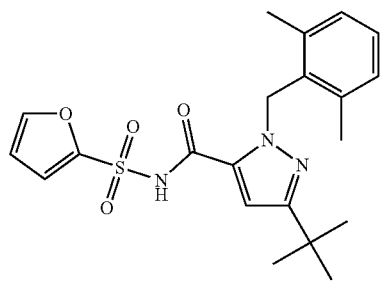 [SMILES: Cc1cccc(C)c1Cn1nc(C(C)(C)C)cc1C(=O)NS(=O)(=O)c1ccco1]
1468
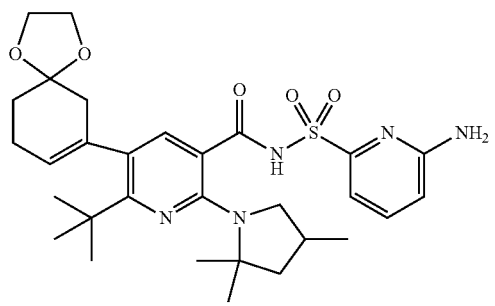 [SMILES: CC1CN(c2nc(C(C)(C)C)c(C3=CCCC4(C3)OCCO4)cc2C(=O)NS(=O)(=O)c2cccc(N)n2)C(C)(C)C1]
1469
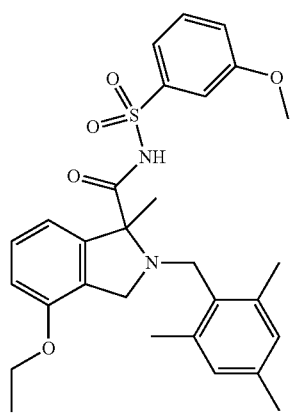 [SMILES: CCOc1cccc2c1CN(Cc1c(C)cc(C)cc1C)C2(C)C(=O)NS(=O)(=O)c1cccc(OC)c1]
1470
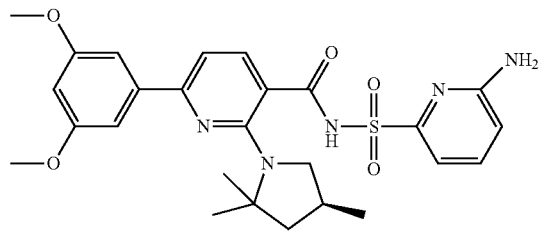 [SMILES: COc1cc(OC)cc(-c2ccc(C(=O)NS(=O)(=O)c3cccc(N)n3)c(N3C[C@@H](C)CC3(C)C)n2)c1]
1471

TABLE 1-continued
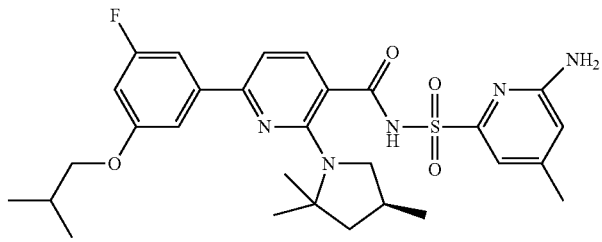 [SMILES: Cc1cc(N)nc(S(=O)(=O)NC(=O)c2ccc(-c3cc(F)cc(OCC(C)C)c3)nc2N2C[C@@H](C)CC2(C)C)c1]
1472
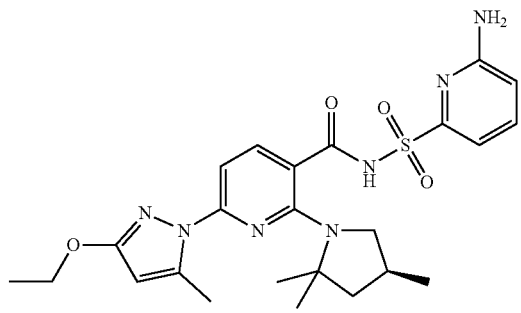 [SMILES: CCOc1cc(C)n(-c2ccc(C(=O)NS(=O)(=O)c3cccc(N)n3)c(N3C[C@@H](C)CC3(C)C)n2)n1]
1473
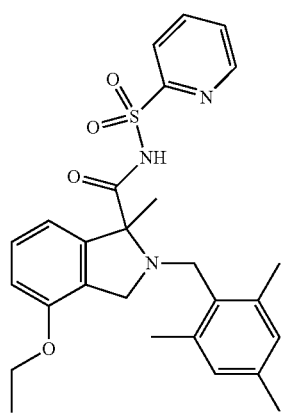 [SMILES: CCOc1cccc2c1CN(Cc1c(C)cc(C)cc1C)C2(C)C(=O)NS(=O)(=O)c1ccccn1]
1474
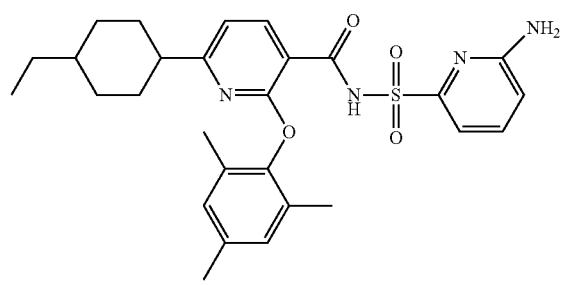 [SMILES: CCC1CCC(c2ccc(C(=O)NS(=O)(=O)c3cccc(N)n3)c(Oc3c(C)cc(C)cc3C)n2)CC1]
1475

TABLE 1-continued
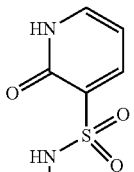
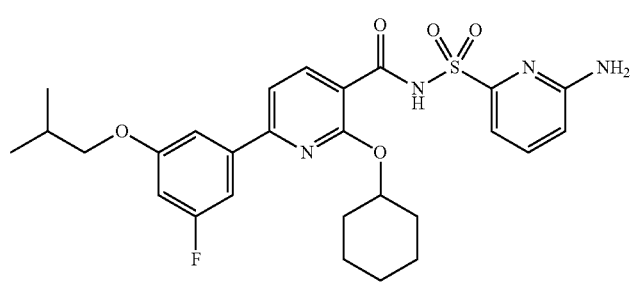 [SMILES: CC(C)COc1cc(F)cc(-c2ccc(C(=O)NS(=O)(=O)c3cccc(N)n3)c(OC3CCCCC3)n2)c1]
1476
1477
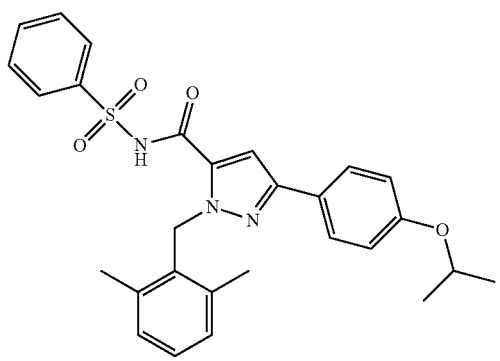 [SMILES: Cc1cccc(C)c1Cn1nc(-c2ccc(OC(C)C)cc2)cc1C(=O)NS(=O)(=O)c1ccccc1]
1478
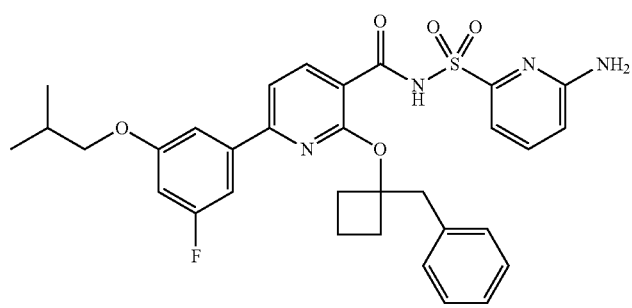 [SMILES: CC(C)COc1cc(F)cc(-c2ccc(C(=O)NS(=O)(=O)c3cccc(N)n3)c(OC3(Cc4ccccc4)CCC3)n2)c1]
1479

TABLE 1-continued
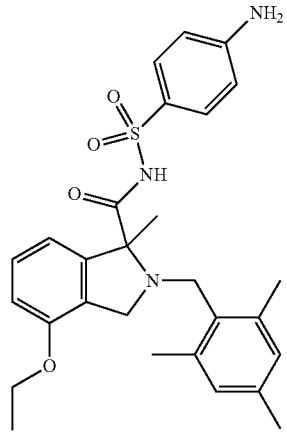 [SMILES: CCOc1cccc2c1CN(Cc1c(C)cc(C)cc1C)C2(C)C(=O)NS(=O)(=O)c1ccc(N)cc1]
1480
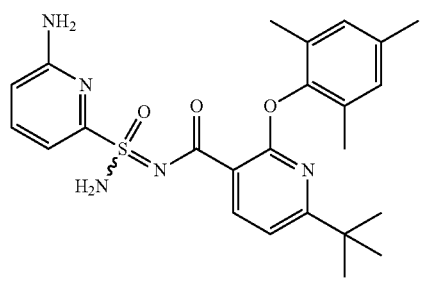 [SMILES: Cc1cc(C)c(Oc2nc(C(C)(C)C)ccc2C(=O)N=S(N)(=O)c2cccc(N)n2)c(C)c1]
1481
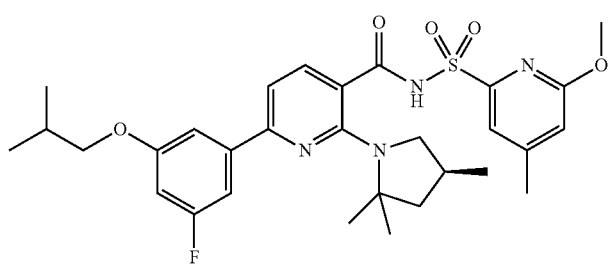 [SMILES: COc1cc(C)cc(S(=O)(=O)NC(=O)c2ccc(-c3cc(F)cc(OCC(C)C)c3)nc2N2C[C@@H](C)CC2(C)C)n1]
1482
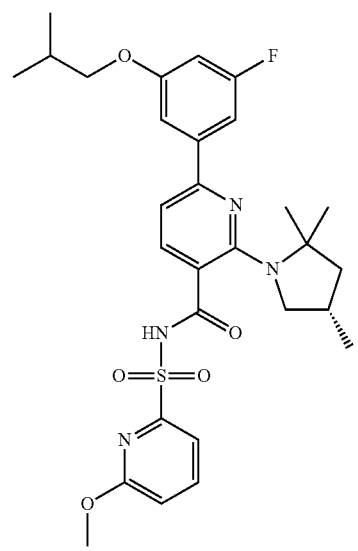 [SMILES: COc1cccc(S(=O)(=O)NC(=O)c2ccc(-c3cc(F)cc(OCC(C)C)c3)nc2N2C[C@@H](C)CC2(C)C)n1]
1483

TABLE 1-continued
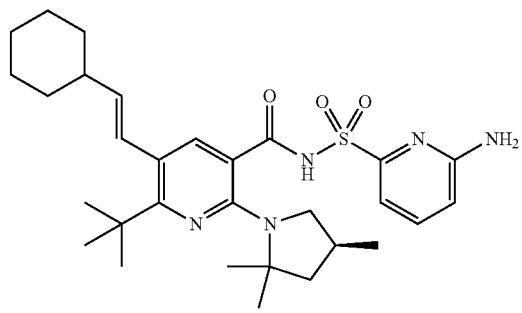 [SMILES: C[C@@H]1CN(c2nc(C(C)(C)C)c(/C=C/C3CCCCC3)cc2C(=O)NS(=O)(=O)c2cccc(N)n2)C(C)(C)C1]
1484
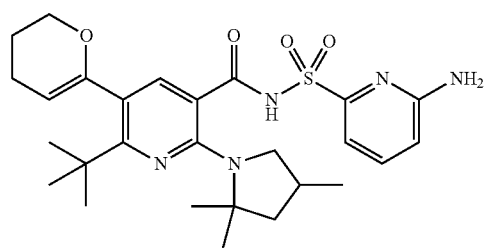 [SMILES: CC1CN(c2nc(C(C)(C)C)c(C3=CCCCO3)cc2C(=O)NS(=O)(=O)c2cccc(N)n2)C(C)(C)C1]
1485
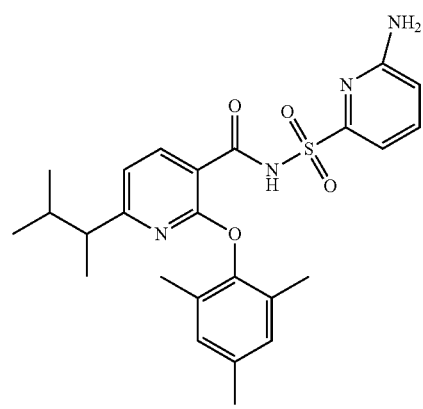 [SMILES: Cc1cc(C)c(Oc2nc(C(C)C(C)C)ccc2C(=O)NS(=O)(=O)c2cccc(N)n2)c(C)c1]
1486
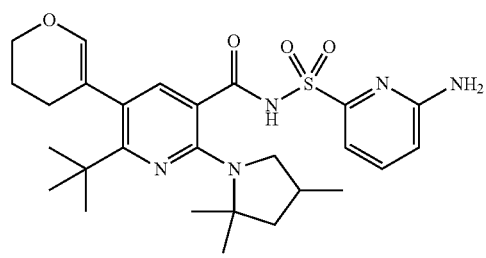 [SMILES: CC1CN(c2nc(C(C)(C)C)c(C3=COCCC3)cc2C(=O)NS(=O)(=O)c2cccc(N)n2)C(C)(C)C1]
1487

TABLE 1-continued
| | |
|---|---|
| 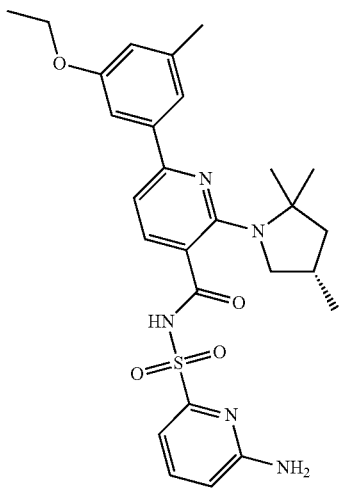 [SMILES: CCOc1cc(C)cc(-c2ccc(C(=O)NS(=O)(=O)c3cccc(N)n3)c(N3C[C@@H](C)CC3(C)C)n2)c1] | 1488 |
| 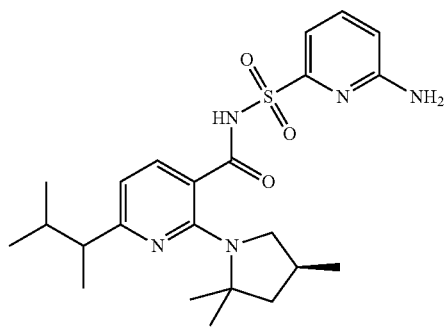 [SMILES: CC(C)C(C)c1ccc(C(=O)NS(=O)(=O)c2cccc(N)n2)c(N2C[C@@H](C)CC2(C)C)n1] | 1489 |
| 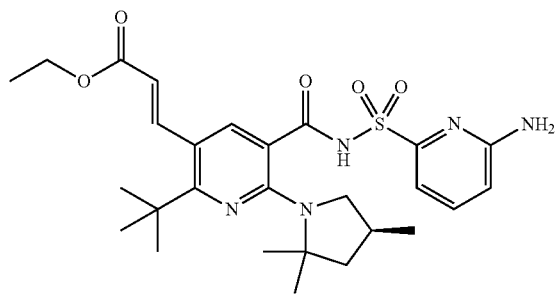 [SMILES: CCOC(=O)/C=C/c1cc(C(=O)NS(=O)(=O)c2cccc(N)n2)c(N2C[C@@H](C)CC2(C)C)nc1C(C)(C)C] | 1490 |
| 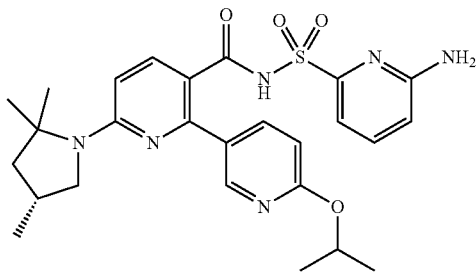 [SMILES: CC(C)Oc1ccc(-c2nc(N3C[C@H](C)CC3(C)C)ccc2C(=O)NS(=O)(=O)c2cccc(N)n2)cn1] | 1491 |

TABLE 1-continued
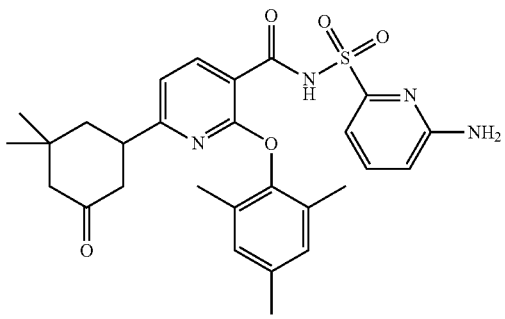 [SMILES: Cc1cc(C)c(Oc2nc(C3CC(=O)CC(C)(C)C3)ccc2C(=O)NS(=O)(=O)c2cccc(N)n2)c(C)c1]
1492
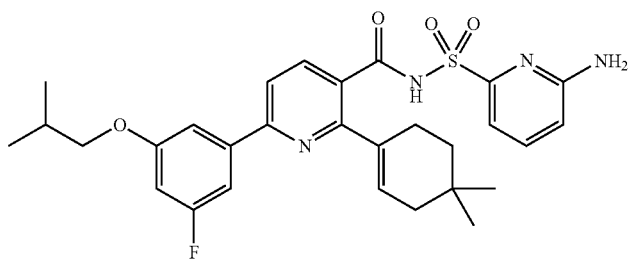 [SMILES: CC(C)COc1cc(F)cc(-c2ccc(C(=O)NS(=O)(=O)c3cccc(N)n3)c(C3=CCC(C)(C)CC3)n2)c1]
1493
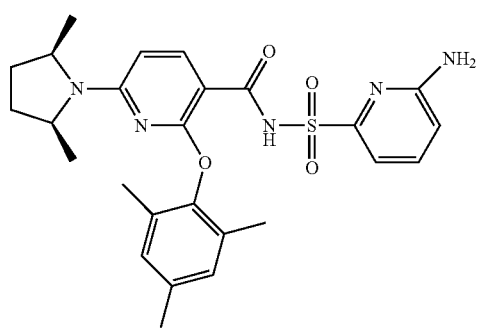 [SMILES: Cc1cc(C)c(Oc2nc(N3[C@H](C)CC[C@@H]3C)ccc2C(=O)NS(=O)(=O)c2cccc(N)n2)c(C)c1]
1494
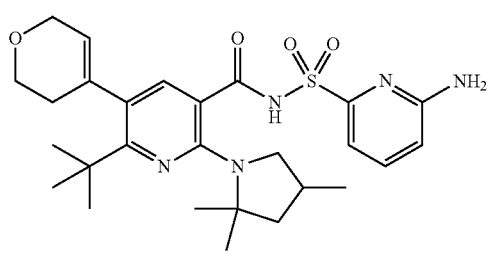 [SMILES: CC1CN(c2nc(C(C)(C)C)c(C3=CCOCC3)cc2C(=O)NS(=O)(=O)c2cccc(N)n2)C(C)(C)C1]
1495
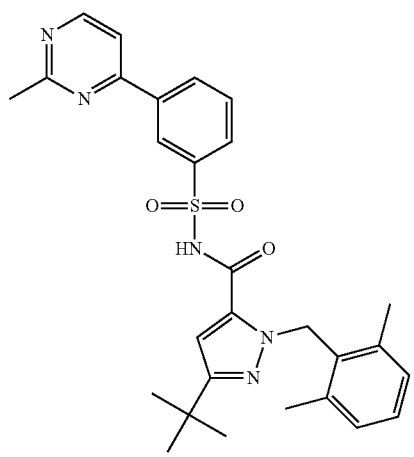 [SMILES: Cc1nccc(-c2cccc(S(=O)(=O)NC(=O)c3cc(C(C)(C)C)nn3Cc3c(C)cccc3C)c2)n1]
1496

TABLE 1-continued
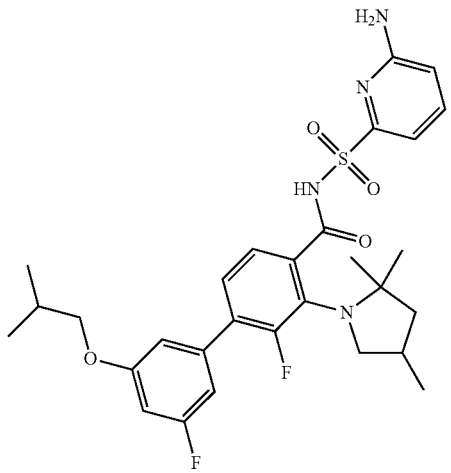 [SMILES: CC(C)COc1cc(F)cc(-c2ccc(C(=O)NS(=O)(=O)c3cccc(N)n3)c(N3CC(C)CC3(C)C)c2F)c1]
1497
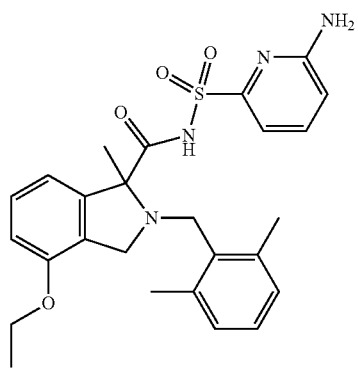 [SMILES: CCOc1cccc2c1CN(Cc1c(C)cccc1C)C2(C)C(=O)NS(=O)(=O)c1cccc(N)n1]
1498
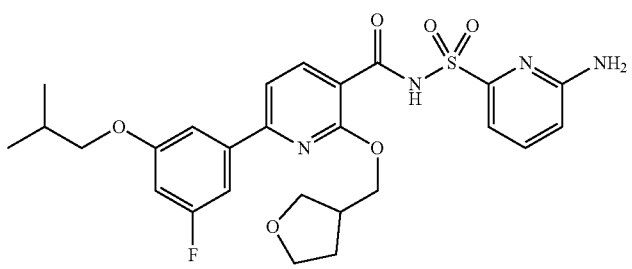
1499
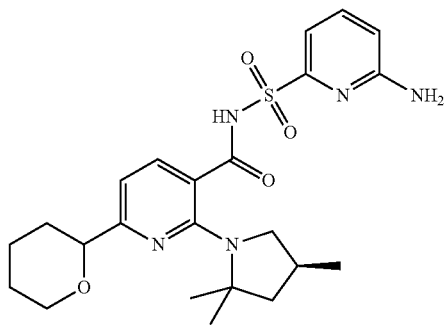 [SMILES: C[C@@H]1CN(c2nc(C3CCCCO3)ccc2C(=O)NS(=O)(=O)c2cccc(N)n2)C(C)(C)C1]
1500

TABLE 1-continued
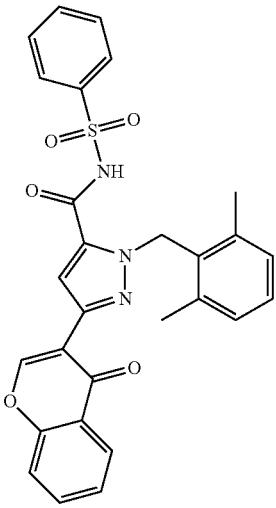 [SMILES: Cc1cccc(C)c1Cn1nc(-c2coc3ccccc3c2=O)cc1C(=O)NS(=O)(=O)c1ccccc1]
1501
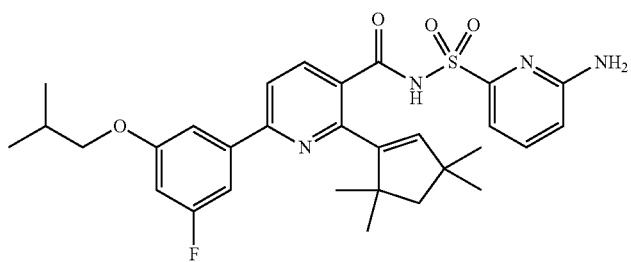 [SMILES: CC(C)COc1cc(F)cc(-c2ccc(C(=O)NS(=O)(=O)c3cccc(N)n3)c(C3=CC(C)(C)CC3(C)C)n2)c1]
1502
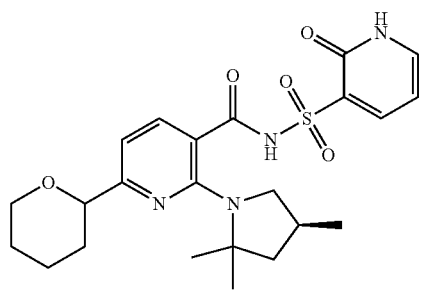 [SMILES: C[C@@H]1CN(c2nc(C3CCCCO3)ccc2C(=O)NS(=O)(=O)c2ccc[nH]c2=O)C(C)(C)C1]
1503
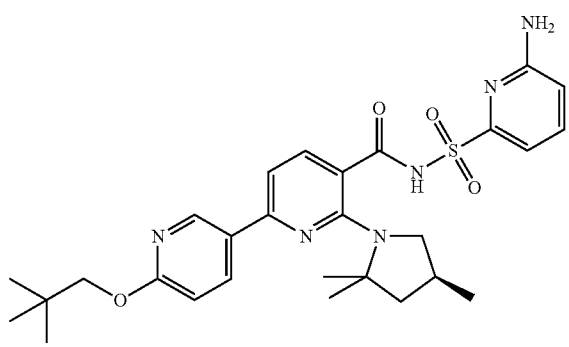 [SMILES: C[C@@H]1CN(c2nc(-c3ccc(OCC(C)(C)C)nc3)ccc2C(=O)NS(=O)(=O)c2cccc(N)n2)C(C)(C)C1]
1504

TABLE 1-continued
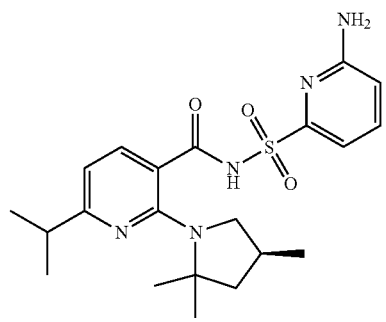 [SMILES: CC(C)c1ccc(C(=O)NS(=O)(=O)c2cccc(N)n2)c(N2C[C@@H](C)CC2(C)C)n1]
1505
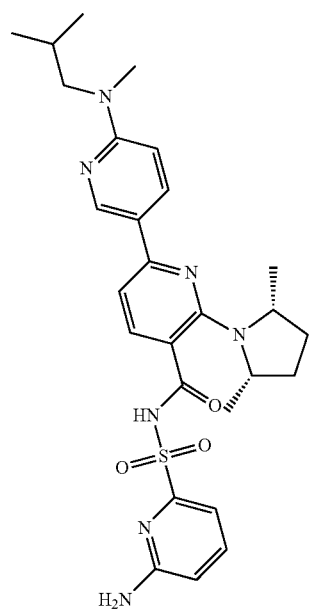 [SMILES: CC(C)CN(C)c1ccc(-c2ccc(C(=O)NS(=O)(=O)c3cccc(N)n3)c(N3[C@H](C)CC[C@@H]3C)n2)cn1]
1506
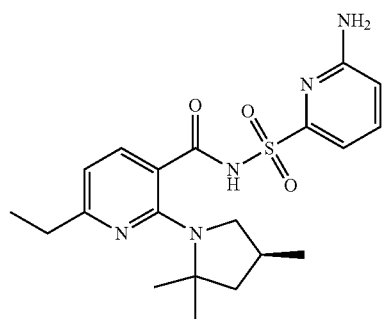 [SMILES: CCc1ccc(C(=O)NS(=O)(=O)c2cccc(N)n2)c(N2C[C@@H](C)CC2(C)C)n1]
1507
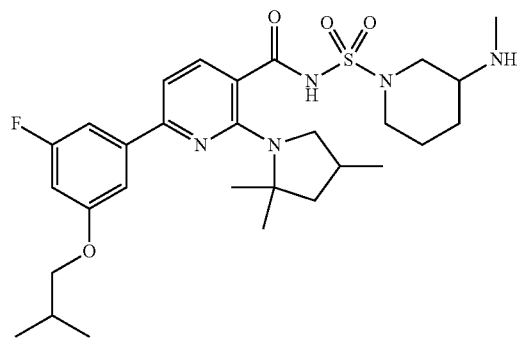 [SMILES: CNC1CCCN(S(=O)(=O)NC(=O)c2ccc(-c3cc(F)cc(OCC(C)C)c3)nc2N2CC(C)CC2(C)C)C1]
1508

TABLE 1-continued
| | |
|---|---|
| 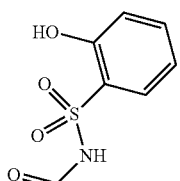 | 1509 |
| 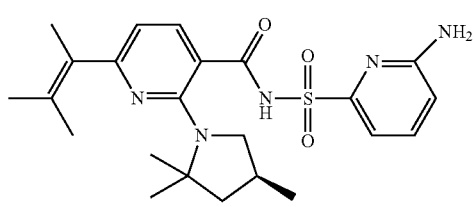 [SMILES: CC(C)=C(C)c1ccc(C(=O)NS(=O)(=O)c2cccc(N)n2)c(N2C[C@@H](C)CC2(C)C)n1] | 1510 |
| 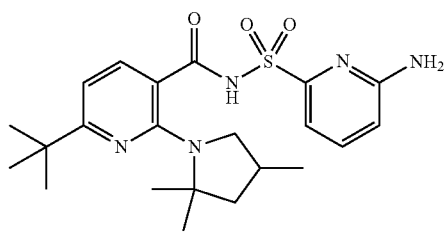 [SMILES: CC1CN(c2nc(C(C)(C)C)ccc2C(=O)NS(=O)(=O)c2cccc(N)n2)C(C)(C)C1] | 1511 |
| 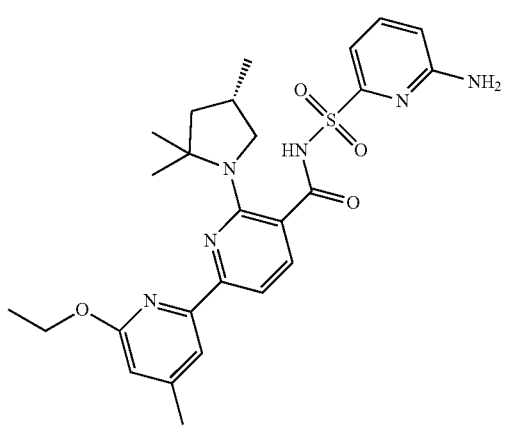 [SMILES: CCOc1cc(C)cc(-c2ccc(C(=O)NS(=O)(=O)c3cccc(N)n3)c(N3C[C@@H](C)CC3(C)C)n2)n1] | 1512 |
| 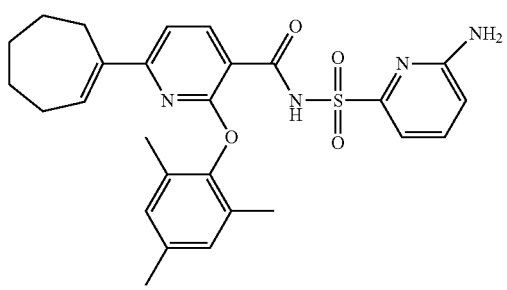 [SMILES: Cc1cc(C)c(Oc2nc(C3=CCCCCC3)ccc2C(=O)NS(=O)(=O)c2cccc(N)n2)c(C)c1] | 1513 |

TABLE 1-continued
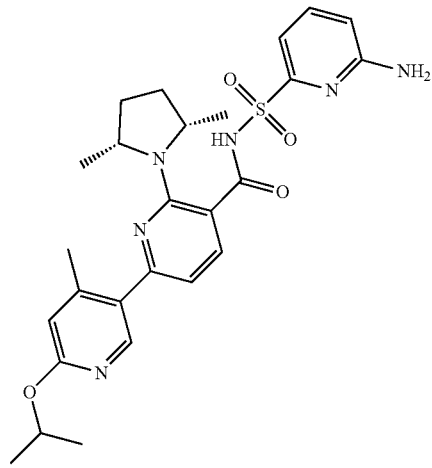 [SMILES: Cc1cc(OC(C)C)ncc1-c1ccc(C(=O)NS(=O)(=O)c2cccc(N)n2)c(N2[C@H](C)CC[C@@H]2C)n1]
1514
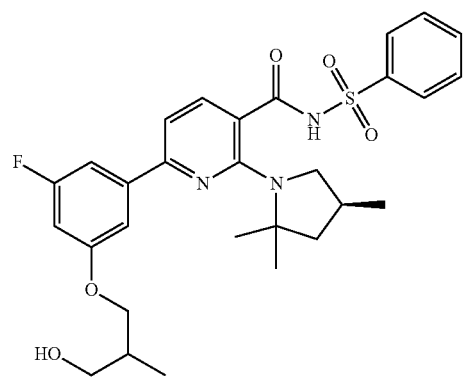 [SMILES: CC(CO)COc1cc(F)cc(-c2ccc(C(=O)NS(=O)(=O)c3ccccc3)c(N3C[C@@H](C)CC3(C)C)n2)c1]
1515
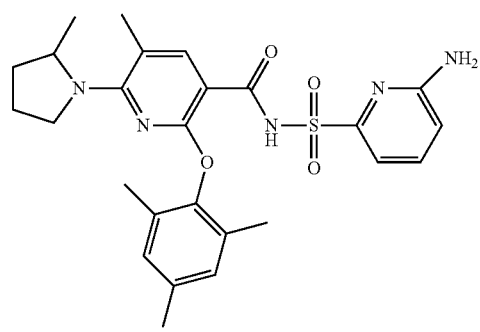 [SMILES: Cc1cc(C)c(Oc2nc(N3CCCC3C)c(C)cc2C(=O)NS(=O)(=O)c2cccc(N)n2)c(C)c1]
1516
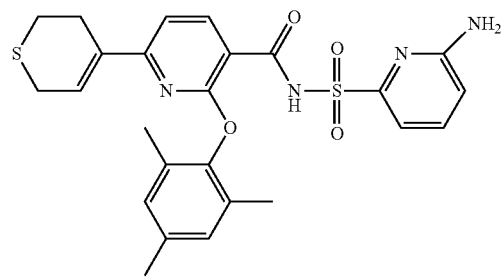 [SMILES: Cc1cc(C)c(Oc2nc(C3=CCSCC3)ccc2C(=O)NS(=O)(=O)c2cccc(N)n2)c(C)c1]
1517

TABLE 1-continued
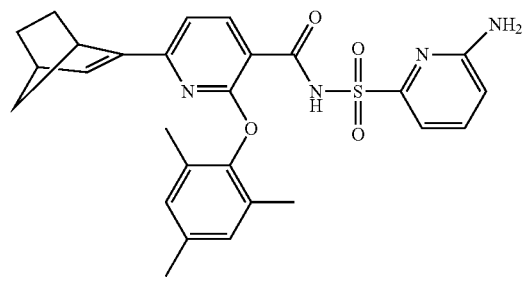 [SMILES: Cc1cc(C)c(Oc2nc(C3=CC4CCC3C4)ccc2C(=O)NS(=O)(=O)c2cccc(N)n2)c(C)c1]
1518
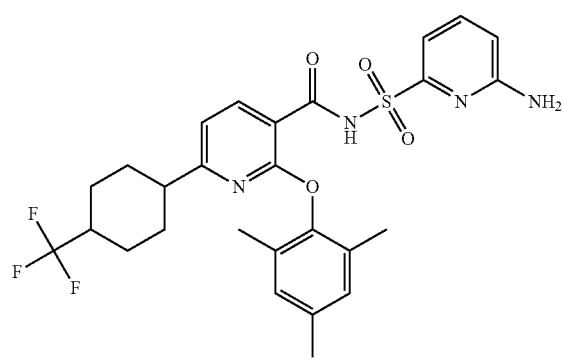 [SMILES: Cc1cc(C)c(Oc2nc(C3CCC(C(F)(F)F)CC3)ccc2C(=O)NS(=O)(=O)c2cccc(N)n2)c(C)c1]
1519
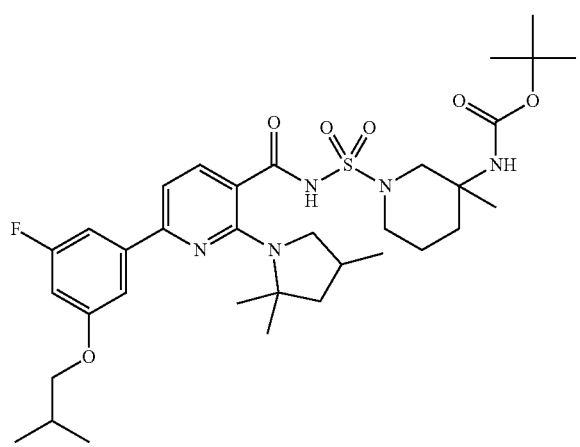 [SMILES: CC(C)COc1cc(F)cc(-c2ccc(C(=O)NS(=O)(=O)N3CCCC(C)(NC(=O)OC(C)(C)C)C3)c(N3CC(C)CC3(C)C)n2)c1]
1520
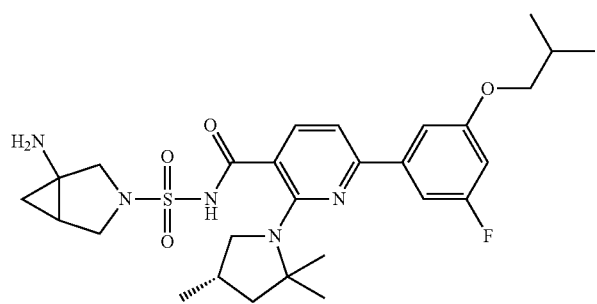 [SMILES: CC(C)COc1cc(F)cc(-c2ccc(C(=O)NS(=O)(=O)N3CC4CC4(N)C3)c(N3C[C@@H](C)CC3(C)C)n2)c1]
1521

TABLE 1-continued
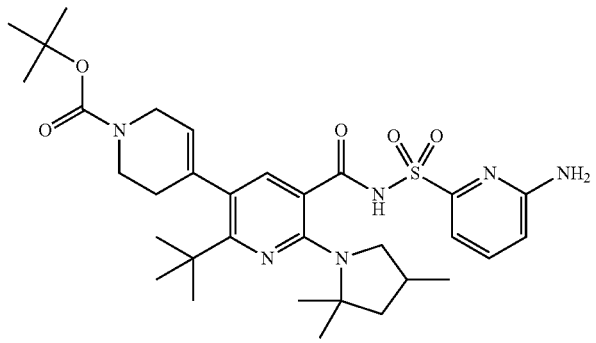 [SMILES: CC1CN(c2nc(C(C)(C)C)c(C3=CCN(C(=O)OC(C)(C)C)CC3)cc2C(=O)NS(=O)(=O)c2cccc(N)n2)C(C)(C)C1]
1522
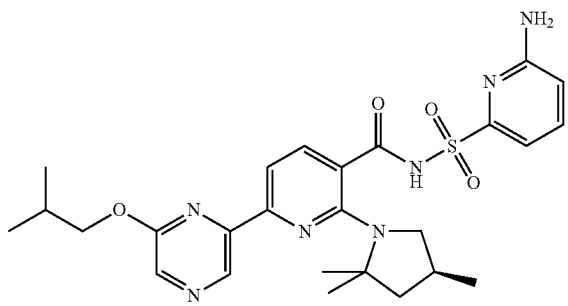 [SMILES: CC(C)COc1cncc(-c2ccc(C(=O)NS(=O)(=O)c3cccc(N)n3)c(N3C[C@@H](C)CC3(C)C)n2)n1]
1523
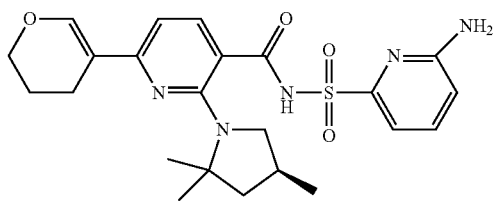 [SMILES: C[C@@H]1CN(c2nc(C3=COCCC3)ccc2C(=O)NS(=O)(=O)c2cccc(N)n2)C(C)(C)C1]
1524
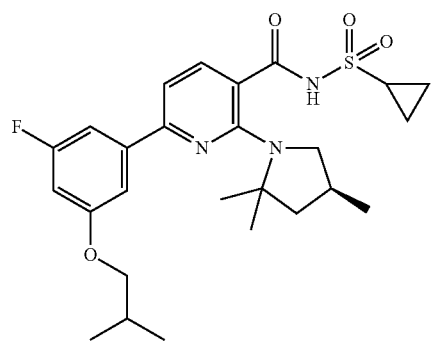 [SMILES: CC(C)COc1cc(F)cc(-c2ccc(C(=O)NS(=O)(=O)C3CC3)c(N3C[C@@H](C)CC3(C)C)n2)c1]
1525
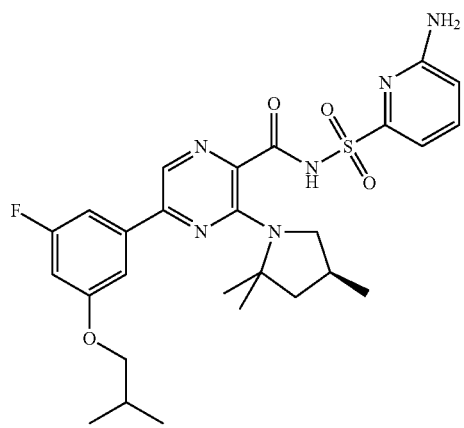 [SMILES: CC(C)COc1cc(F)cc(-c2cnc(C(=O)NS(=O)(=O)c3cccc(N)n3)c(N3C[C@@H](C)CC3(C)C)n2)c1]
1526

TABLE 1-continued
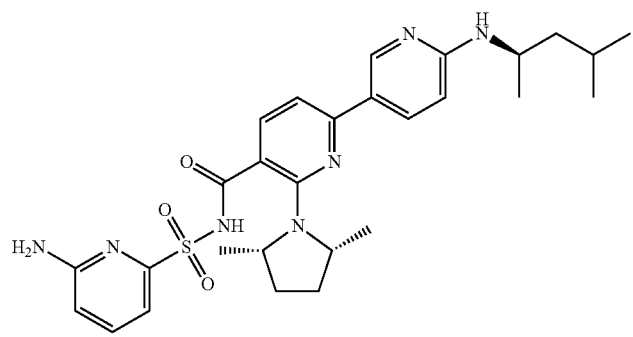 [SMILES: CC(C)C[C@@H](C)Nc1ccc(-c2ccc(C(=O)NS(=O)(=O)c3cccc(N)n3)c(N3[C@H](C)CC[C@@H]3C)n2)cn1]
1527
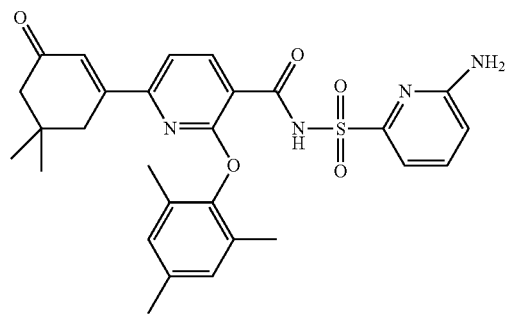 [SMILES: Cc1cc(C)c(Oc2nc(C3=CC(=O)CC(C)(C)C3)ccc2C(=O)NS(=O)(=O)c2cccc(N)n2)c(C)c1]
1528
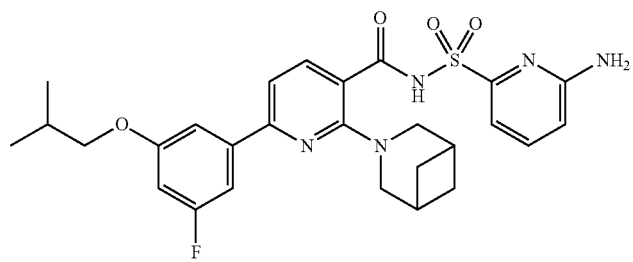 [SMILES: CC(C)COc1cc(F)cc(-c2ccc(C(=O)NS(=O)(=O)c3cccc(N)n3)c(N3CC4CC(C4)C3)n2)c1]
1529
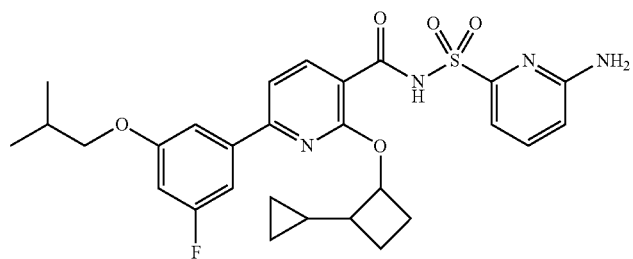 [SMILES: CC(C)COc1cc(F)cc(-c2ccc(C(=O)NS(=O)(=O)c3cccc(N)n3)c(OC3CCC3C3CC3)n2)c1]
1530
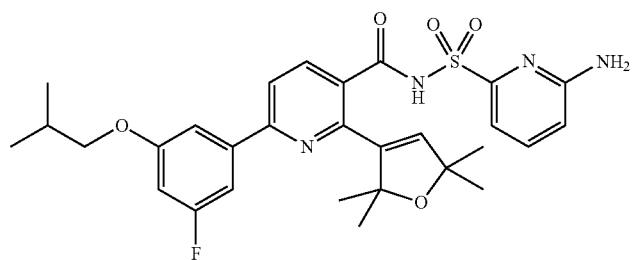 [SMILES: CC(C)COc1cc(F)cc(-c2ccc(C(=O)NS(=O)(=O)c3cccc(N)n3)c(C3=CC(C)(C)OC3(C)C)n2)c1]
1531

TABLE 1-continued
| | |
|---|---|
| 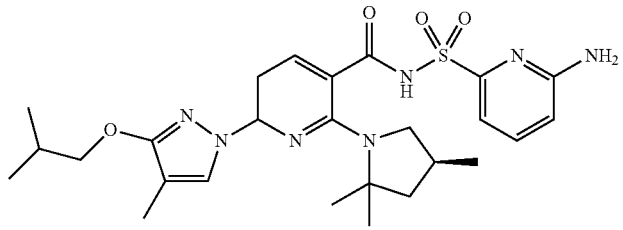 [SMILES: Cc1cn(C2CC=C(C(=O)NS(=O)(=O)c3cccc(N)n3)C(N3C[C@@H](C)CC3(C)C)=N2)nc1OCC(C)C] | 1532 |
| 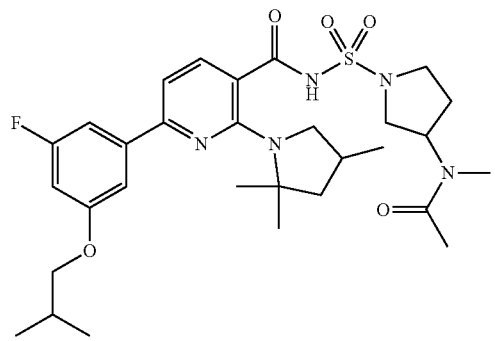 [SMILES: CC(=O)N(C)C1CCN(S(=O)(=O)NC(=O)c2ccc(-c3cc(F)cc(OCC(C)C)c3)nc2N2CC(C)CC2(C)C)C1] | 1533 |
| 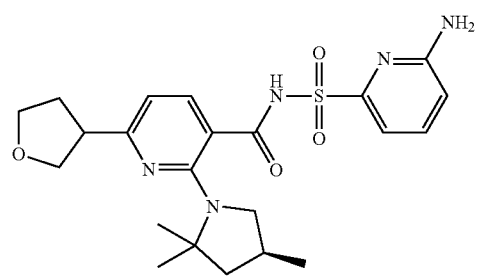 [SMILES: C[C@@H]1CN(c2nc(C3CCOC3)ccc2C(=O)NS(=O)(=O)c2cccc(N)n2)C(C)(C)C1] | 1534 |
| 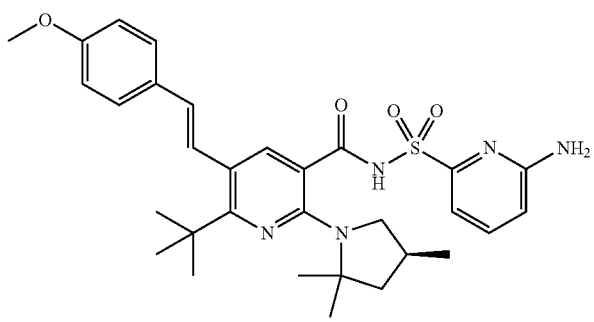 [SMILES: COc1ccc(/C=C/c2cc(C(=O)NS(=O)(=O)c3cccc(N)n3)c(N3C[C@@H](C)CC3(C)C)nc2C(C)(C)C)cc1] | 1535 |
| 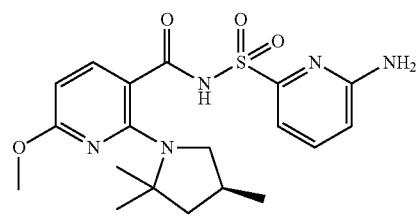 [SMILES: COc1ccc(C(=O)NS(=O)(=O)c2cccc(N)n2)c(N2C[C@@H](C)CC2(C)C)n1] | 1536 |

TABLE 1-continued
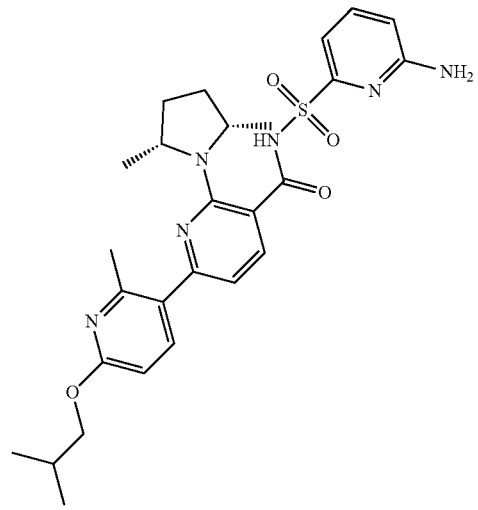 [SMILES: Cc1nc(OCC(C)C)ccc1-c1ccc(C(=O)NS(=O)(=O)c2cccc(N)n2)c(N2[C@H](C)CC[C@@H]2C)n1]
1537
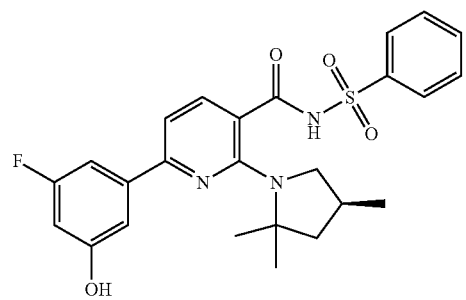 [SMILES: C[C@@H]1CN(c2nc(-c3cc(O)cc(F)c3)ccc2C(=O)NS(=O)(=O)c2ccccc2)C(C)(C)C1]
1538
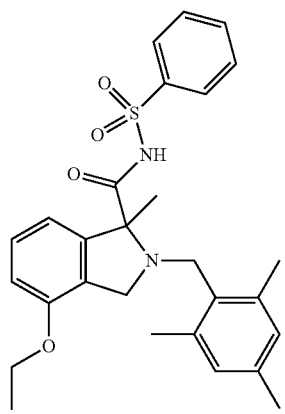 [SMILES: CCOc1cccc2c1CN(Cc1c(C)cc(C)cc1C)C2(C)C(=O)NS(=O)(=O)c1ccccc1]
1539
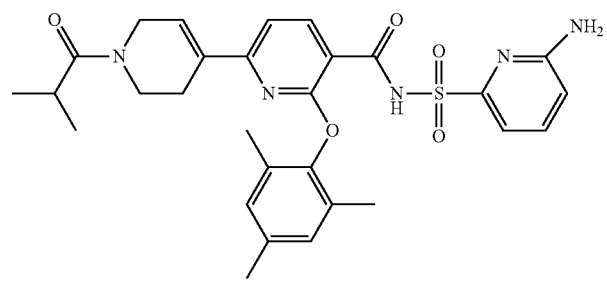 [SMILES: Cc1cc(C)c(Oc2nc(C3=CCN(C(=O)C(C)C)CC3)ccc2C(=O)NS(=O)(=O)c2cccc(N)n2)c(C)c1]
1540

TABLE 1-continued
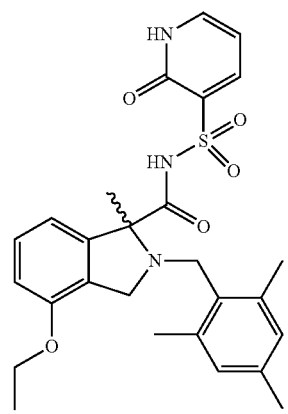 [SMILES: CCOc1cccc2c1CN(Cc1c(C)cc(C)cc1C)C2(C)C(=O)NS(=O)(=O)c1ccc[nH]c1=O]
1541
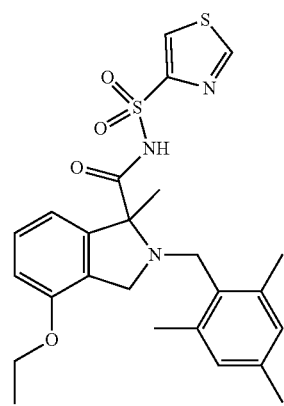 [SMILES: CCOc1cccc2c1CN(Cc1c(C)cc(C)cc1C)C2(C)C(=O)NS(=O)(=O)c1cscn1]
1542
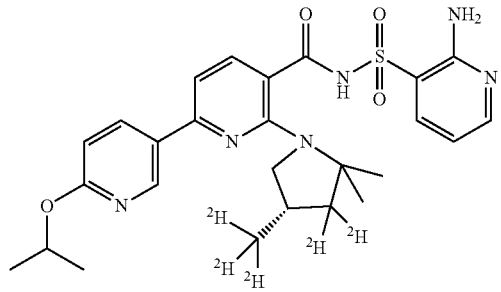 [SMILES: [2H]C([2H])([2H])[C@@H]1CN(c2nc(-c3ccc(OC(C)C)nc3)ccc2C(=O)NS(=O)(=O)c2cccnc2N)C(C)(C)C1([2H])[2H]]
1543
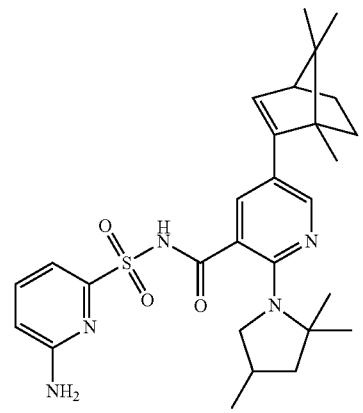 [SMILES: CC1CN(c2ncc(C3=CC4CCC3(C)C4(C)C)cc2C(=O)NS(=O)(=O)c2cccc(N)n2)C(C)(C)C1]
1544

TABLE 1-continued
| | |
|---|---|
| 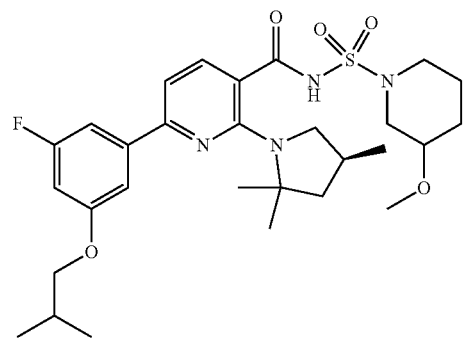 [SMILES: COC1CCCN(S(=O)(=O)NC(=O)c2ccc(-c3cc(F)cc(OCC(C)C)c3)nc2N2C[C@@H](C)CC2(C)C)C1] | 1545 |
| 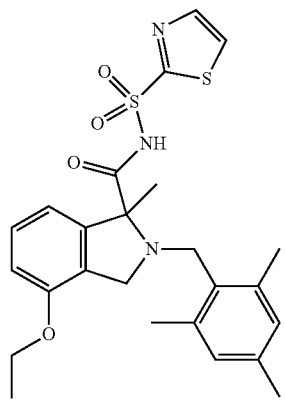 [SMILES: CCOc1cccc2c1CN(Cc1c(C)cc(C)cc1C)C2(C)C(=O)NS(=O)(=O)c1nccs1] | 1546 |
| 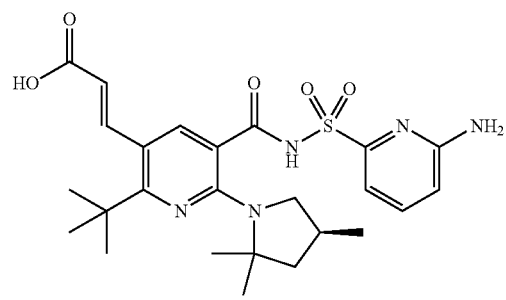 [SMILES: C[C@@H]1CN(c2nc(C(C)(C)C)c(/C=C/C(=O)O)cc2C(=O)NS(=O)(=O)c2cccc(N)n2)C(C)(C)C1] | 1547 |
| 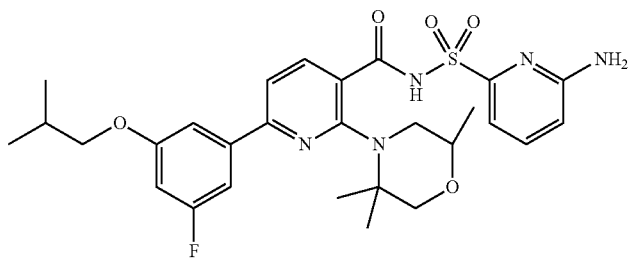 [SMILES: CC(C)COc1cc(F)cc(-c2ccc(C(=O)NS(=O)(=O)c3cccc(N)n3)c(N3CC(C)OCC3(C)C)n2)c1] | 1548 |
| 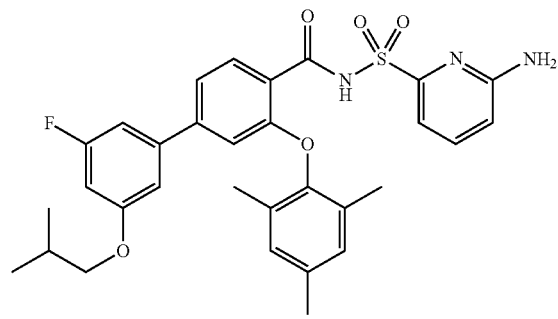 [SMILES: Cc1cc(C)c(Oc2cc(-c3cc(F)cc(OCC(C)C)c3)ccc2C(=O)NS(=O)(=O)c2cccc(N)n2)c(C)c1] | 1549 |

TABLE 1-continued
| | |
|---|---|
| 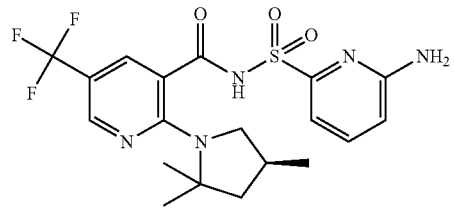 [SMILES: C[C@@H]1CN(c2ncc(C(F)(F)F)cc2C(=O)NS(=O)(=O)c2cccc(N)n2)C(C)(C)C1] | 1550 |
| 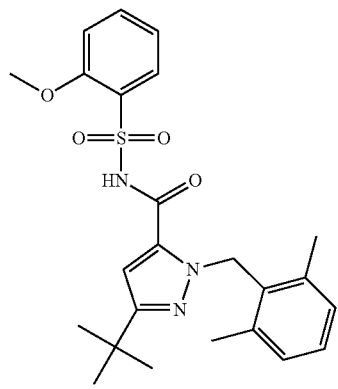 [SMILES: COc1ccccc1S(=O)(=O)NC(=O)c1cc(C(C)(C)C)nn1Cc1c(C)cccc1C] | 1551 |
| 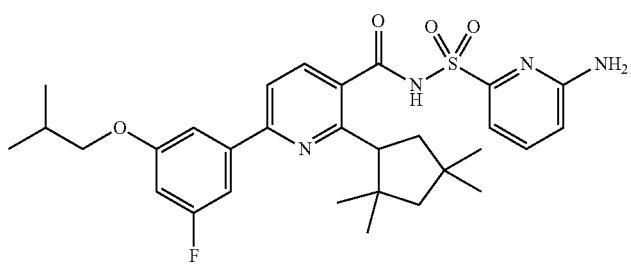 [SMILES: CC(C)COc1cc(F)cc(-c2ccc(C(=O)NS(=O)(=O)c3cccc(N)n3)c(C3CC(C)(C)CC3(C)C)n2)c1] | 1552 |
| 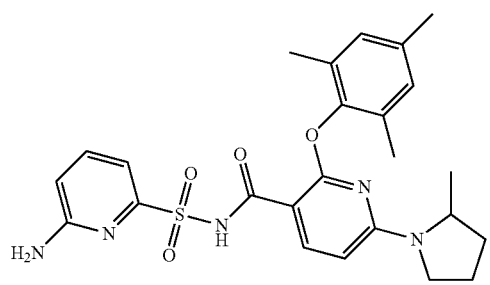 [SMILES: Cc1cc(C)c(Oc2nc(N3CCCC3C)ccc2C(=O)NS(=O)(=O)c2cccc(N)n2)c(C)c1] | 1553 |
| 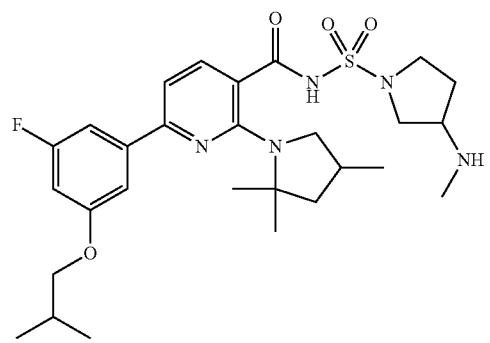 [SMILES: CNC1CCN(S(=O)(=O)NC(=O)c2ccc(-c3cc(F)cc(OCC(C)C)c3)nc2N2CC(C)CC2(C)C)C1] | 1554 |

TABLE 1-continued
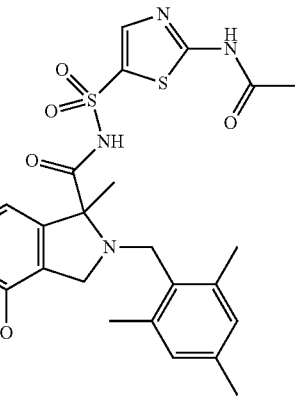
1555
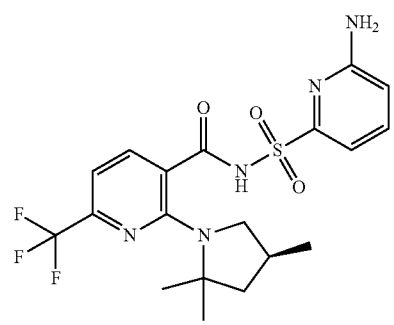 [SMILES: C[C@@H]1CN(c2nc(C(F)(F)F)ccc2C(=O)NS(=O)(=O)c2cccc(N)n2)C(C)(C)C1]
1556
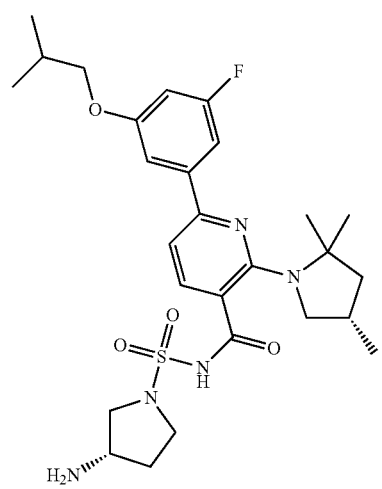 [SMILES: CC(C)COc1cc(F)cc(-c2ccc(C(=O)NS(=O)(=O)N3CC[C@H](N)C3)c(N3C[C@@H](C)CC3(C)C)n2)c1]
1557
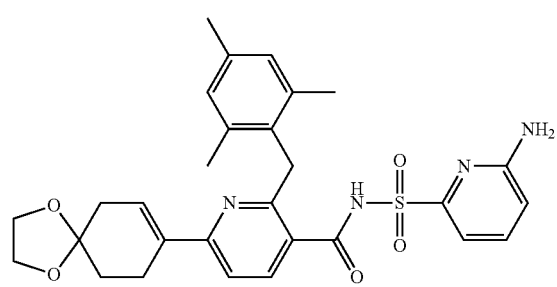 [SMILES: Cc1cc(C)c(Cc2nc(C3=CCC4(CC3)OCCO4)ccc2C(=O)NS(=O)(=O)c2cccc(N)n2)c(C)c1]
1558

TABLE 1-continued
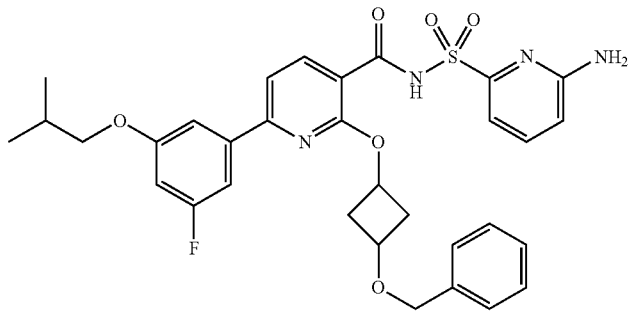 [SMILES: CC(C)COc1cc(F)cc(-c2ccc(C(=O)NS(=O)(=O)c3cccc(N)n3)c(OC3CC(OCc4ccccc4)C3)n2)c1]
1559
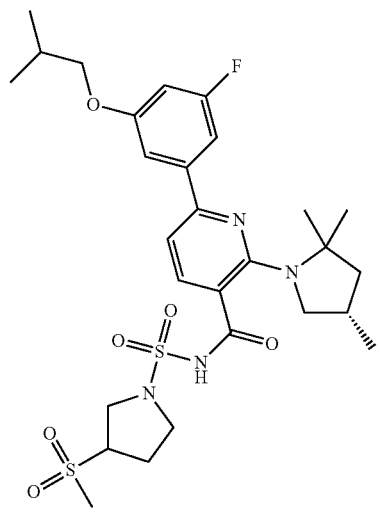 [SMILES: CC(C)COc1cc(F)cc(-c2ccc(C(=O)NS(=O)(=O)N3CCC(S(C)(=O)=O)C3)c(N3C[C@@H](C)CC3(C)C)n2)c1]
1560
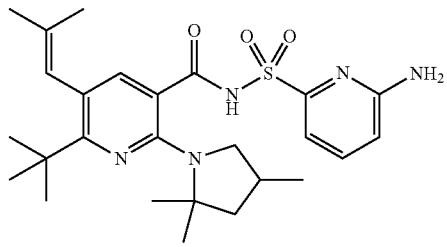 [SMILES: CC(C)=Cc1cc(C(=O)NS(=O)(=O)c2cccc(N)n2)c(N2CC(C)CC2(C)C)nc1C(C)(C)C]
1561
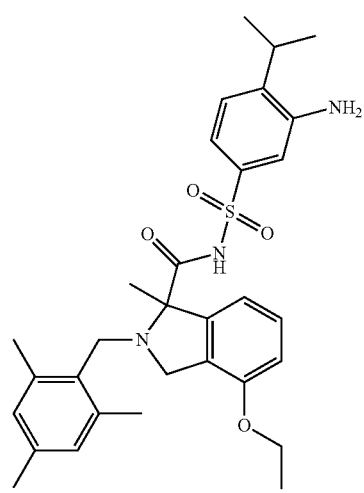 [SMILES: CCOc1cccc2c1CN(Cc1c(C)cc(C)cc1C)C2(C)C(=O)NS(=O)(=O)c1ccc(C(C)C)c(N)c1]
1562

TABLE 1-continued

1563

1564

1565

1566

TABLE 1-continued
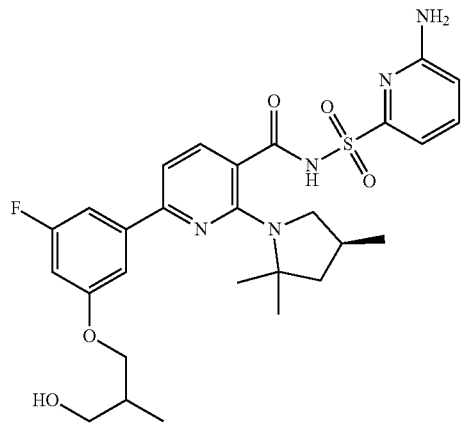 [SMILES: CC(CO)COc1cc(F)cc(-c2ccc(C(=O)NS(=O)(=O)c3cccc(N)n3)c(N3C[C@@H](C)CC3(C)C)n2)c1]
1567
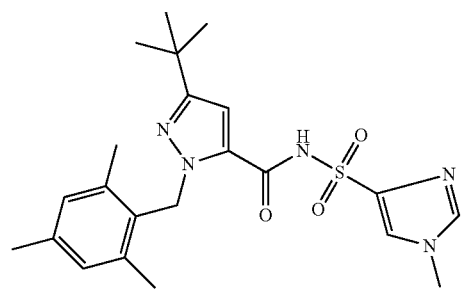 [SMILES: Cc1cc(C)c(Cn2nc(C(C)(C)C)cc2C(=O)NS(=O)(=O)c2cn(C)cn2)c(C)c1]
1568
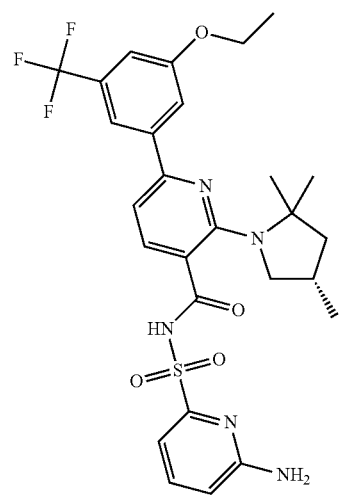 [SMILES: CCOc1cc(-c2ccc(C(=O)NS(=O)(=O)c3cccc(N)n3)c(N3C[C@@H](C)CC3(C)C)n2)cc(C(F)(F)F)c1]
1569
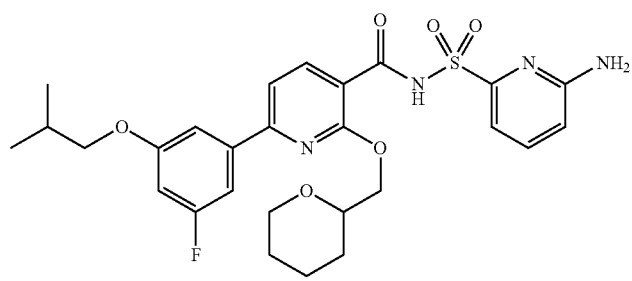 [SMILES: CC(C)COc1cc(F)cc(-c2ccc(C(=O)NS(=O)(=O)c3cccc(N)n3)c(OCC3CCCCO3)n2)c1]
1570

TABLE 1-continued
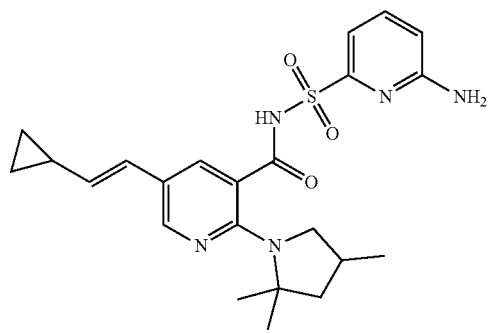 [SMILES: CC1CN(c2ncc(/C=C/C3CC3)cc2C(=O)NS(=O)(=O)c2cccc(N)n2)C(C)(C)C1]
1571
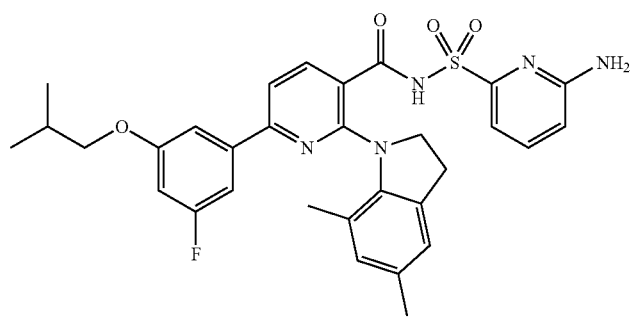 [SMILES: Cc1cc(C)c2c(c1)CCN2c1nc(-c2cc(F)cc(OCC(C)C)c2)ccc1C(=O)NS(=O)(=O)c1cccc(N)n1]
1572
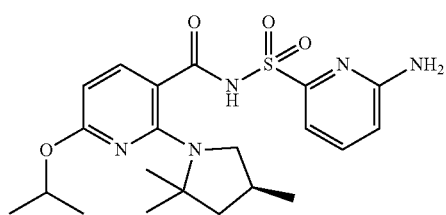 [SMILES: CC(C)Oc1ccc(C(=O)NS(=O)(=O)c2cccc(N)n2)c(N2C[C@@H](C)CC2(C)C)n1]
1573
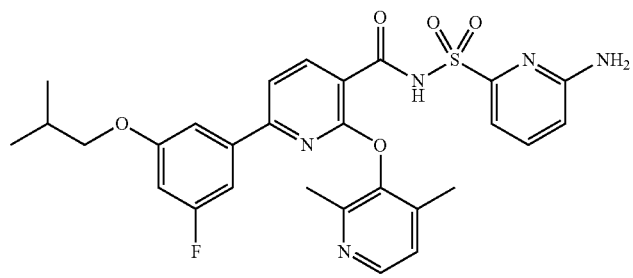 [SMILES: Cc1ccnc(C)c1Oc1nc(-c2cc(F)cc(OCC(C)C)c2)ccc1C(=O)NS(=O)(=O)c1cccc(N)n1]
1574
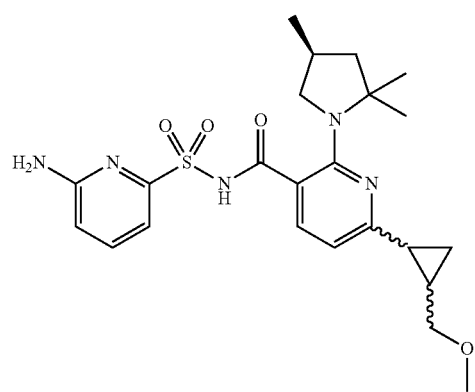 [SMILES: COCC1CC1c1ccc(C(=O)NS(=O)(=O)c2cccc(N)n2)c(N2C[C@@H](C)CC2(C)C)n1]
1575

TABLE 1-continued
| | |
|---|---|
| 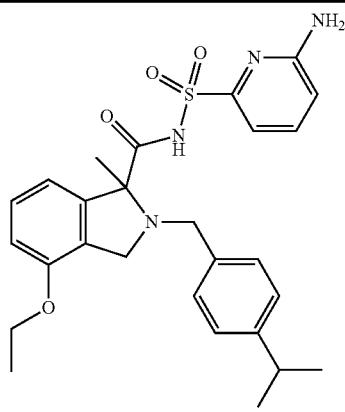 | 1576 |
| 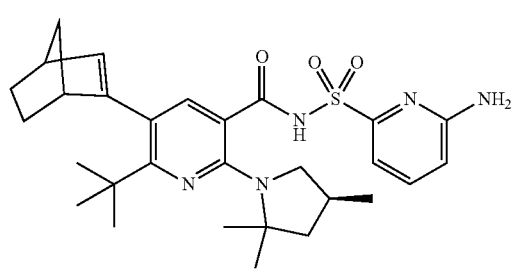 [SMILES: C[C@@H]1CN(c2nc(C(C)(C)C)c(C3=CC45CC4CCC35)cc2C(=O)NS(=O)(=O)c2cccc(N)n2)C(C)(C)C1] | 1577 |
| 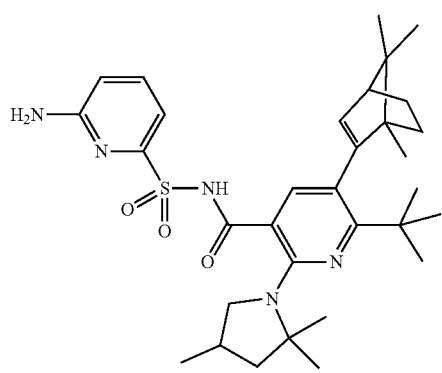 [SMILES: CC1CN(c2nc(C(C)(C)C)c(C3=CC4CCC3(C)C4(C)C)cc2C(=O)NS(=O)(=O)c2cccc(N)n2)C(C)(C)C1] | 1578 |
| 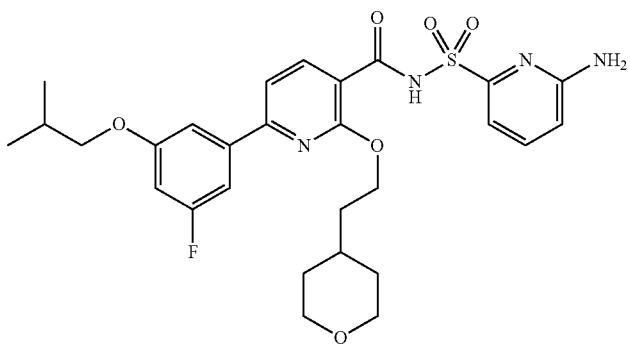 [SMILES: CC(C)COc1cc(F)cc(-c2ccc(C(=O)NS(=O)(=O)c3cccc(N)n3)c(OCCC3CCOCC3)n2)c1] | 1579 |
| 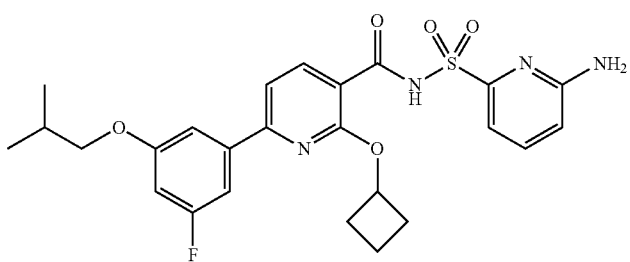 [SMILES: CC(C)COc1cc(F)cc(-c2ccc(C(=O)NS(=O)(=O)c3cccc(N)n3)c(OC3CCC3)n2)c1] | 1580 |

TABLE 1-continued
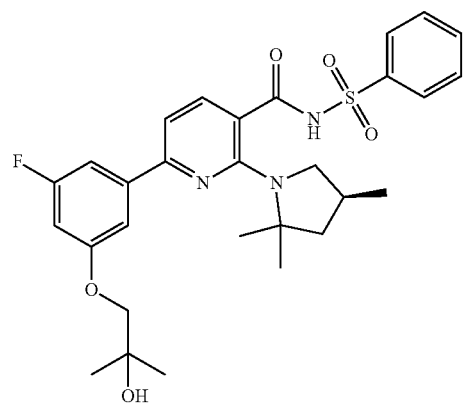 [SMILES: C[C@@H]1CN(c2nc(-c3cc(F)cc(OCC(C)(C)O)c3)ccc2C(=O)NS(=O)(=O)c2ccccc2)C(C)(C)C1]
1581
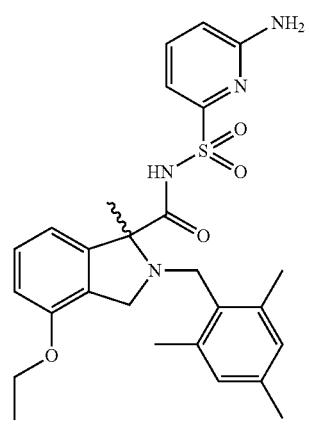 [SMILES: CCOc1cccc2c1CN(Cc1c(C)cc(C)cc1C)C2(C)C(=O)NS(=O)(=O)c1cccc(N)n1]
1582
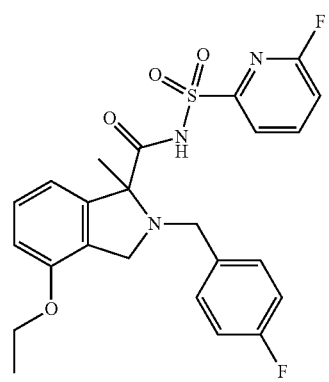 [SMILES: CCOc1cccc2c1CN(Cc1ccc(F)cc1)C2(C)C(=O)NS(=O)(=O)c1cccc(F)n1]
1583

TABLE 1-continued
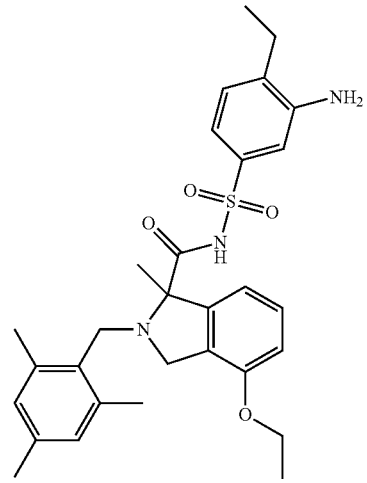 [SMILES: CCOc1cccc2c1CN(Cc1c(C)cc(C)cc1C)C2(C)C(=O)NS(=O)(=O)c1ccc(CC)c(N)c1]
1584
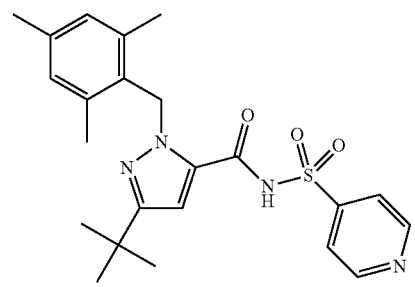 [SMILES: Cc1cc(C)c(Cn2nc(C(C)(C)C)cc2C(=O)NS(=O)(=O)c2ccncc2)c(C)c1]
1585
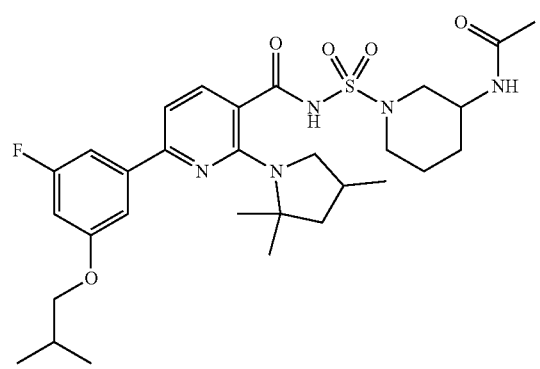 [SMILES: CC(=O)NC1CCCN(S(=O)(=O)NC(=O)c2ccc(-c3cc(F)cc(OCC(C)C)c3)nc2N2CC(C)CC2(C)C)C1]
1586
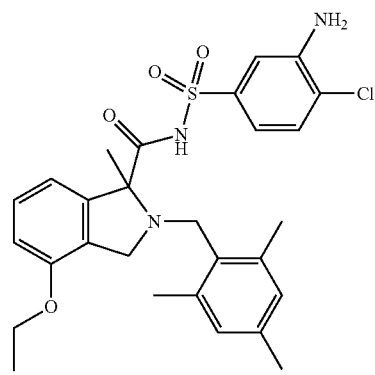 [SMILES: CCOc1cccc2c1CN(Cc1c(C)cc(C)cc1C)C2(C)C(=O)NS(=O)(=O)c1ccc(Cl)c(N)c1]
1587

TABLE 1-continued
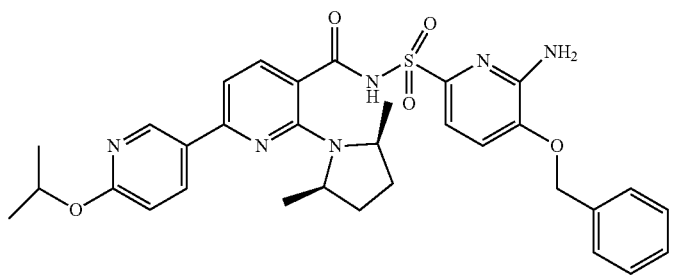 [SMILES: CC(C)Oc1ccc(-c2ccc(C(=O)NS(=O)(=O)c3ccc(OCc4ccccc4)c(N)n3)c(N3[C@H](C)CC[C@@H]3C)n2)cn1]
1588
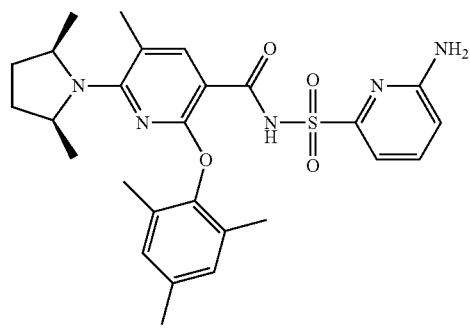 [SMILES: Cc1cc(C)c(Oc2nc(N3[C@H](C)CC[C@@H]3C)c(C)cc2C(=O)NS(=O)(=O)c2cccc(N)n2)c(C)c1]
1589
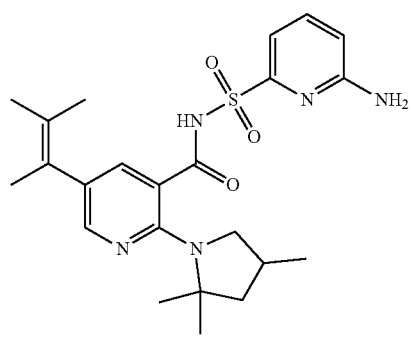 [SMILES: CC(C)=C(C)c1cnc(N2CC(C)CC2(C)C)c(C(=O)NS(=O)(=O)c2cccc(N)n2)c1]
1590
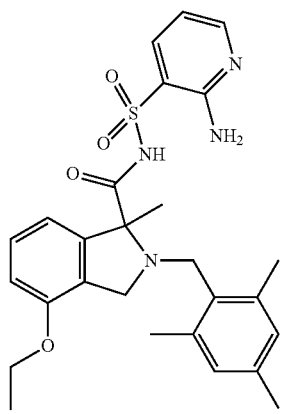 [SMILES: CCOc1cccc2c1CN(Cc1c(C)cc(C)cc1C)C2(C)C(=O)NS(=O)(=O)c1cccnc1N]
1591
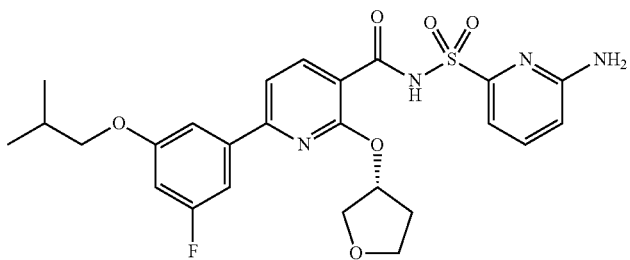 [SMILES: CC(C)COc1cc(F)cc(-c2ccc(C(=O)NS(=O)(=O)c3cccc(N)n3)c(O[C@@H]3CCOC3)n2)c1]
1592

TABLE 1-continued
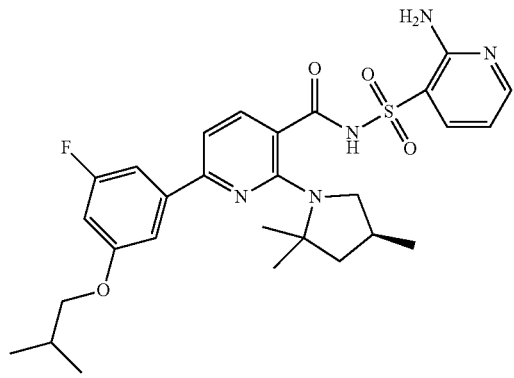 [SMILES: CC(C)COc1cc(F)cc(-c2ccc(C(=O)NS(=O)(=O)c3cccnc3N)c(N3C[C@@H](C)CC3(C)C)n2)c1] 1593
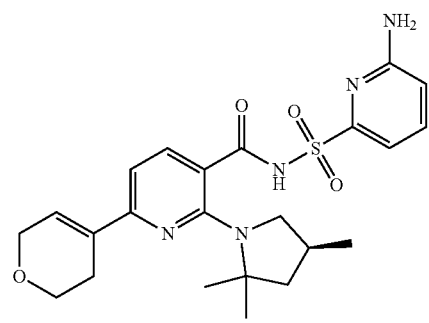 [SMILES: C[C@@H]1CN(c2nc(C3=CCOCC3)ccc2C(=O)NS(=O)(=O)c2cccc(N)n2)C(C)(C)C1] 1594
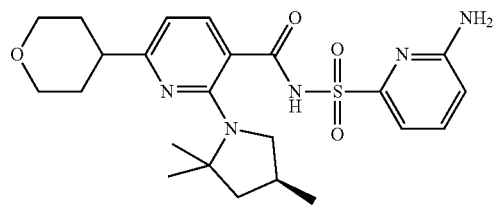 [SMILES: C[C@@H]1CN(c2nc(C3CCOCC3)ccc2C(=O)NS(=O)(=O)c2cccc(N)n2)C(C)(C)C1] 1595
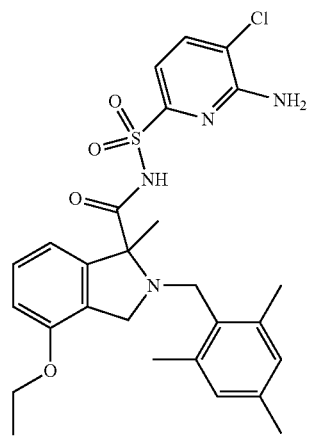 [SMILES: CCOc1cccc2c1CN(Cc1c(C)cc(C)cc1C)C2(C)C(=O)NS(=O)(=O)c1ccc(Cl)c(N)n1] 1596

TABLE 1-continued
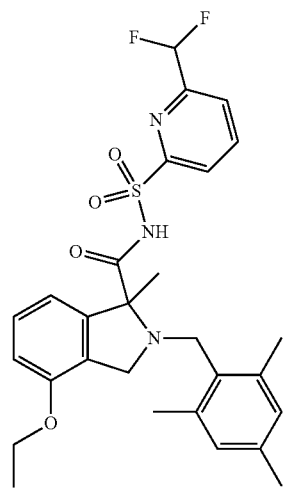 [SMILES: CCOc1cccc2c1CN(Cc1c(C)cc(C)cc1C)C2(C)C(=O)NS(=O)(=O)c1cccc(C(F)F)n1]
1597
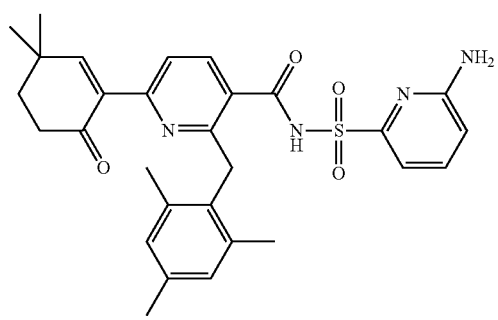 [SMILES: Cc1cc(C)c(Cc2nc(C3=CC(C)(C)CCC3=O)ccc2C(=O)NS(=O)(=O)c2cccc(N)n2)c(C)c1]
1598
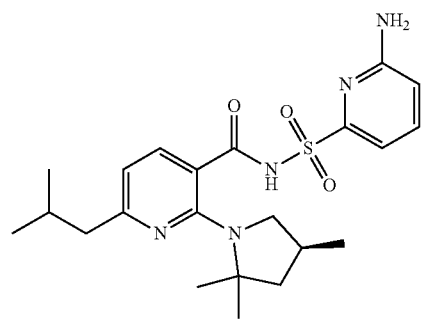 [SMILES: CC(C)Cc1ccc(C(=O)NS(=O)(=O)c2cccc(N)n2)c(N2C[C@@H](C)CC2(C)C)n1]
1599
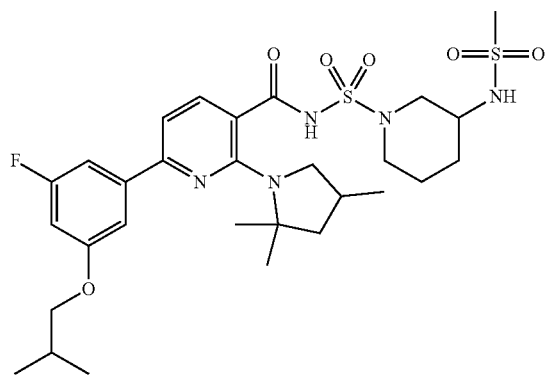 [SMILES: CC(C)COc1cc(F)cc(-c2ccc(C(=O)NS(=O)(=O)N3CCCC(NS(C)(=O)=O)C3)c(N3CC(C)CC3(C)C)n2)c1]
1600

TABLE 1-continued
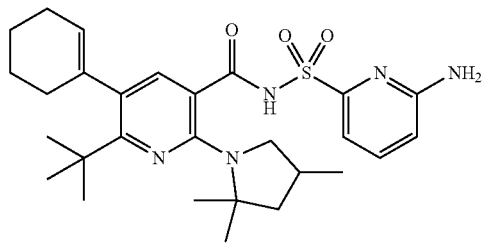 [SMILES: CC1CN(c2nc(C(C)(C)C)c(C3=CCCCC3)cc2C(=O)NS(=O)(=O)c2cccc(N)n2)C(C)(C)C1]
1601
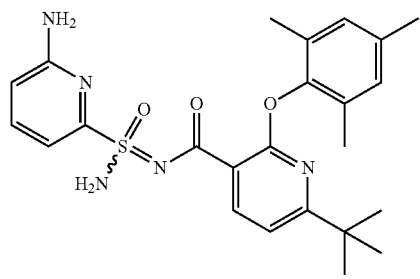 [SMILES: Cc1cc(C)c(Oc2nc(C(C)(C)C)ccc2C(=O)N=S(N)(=O)c2cccc(N)n2)c(C)c1]
1602
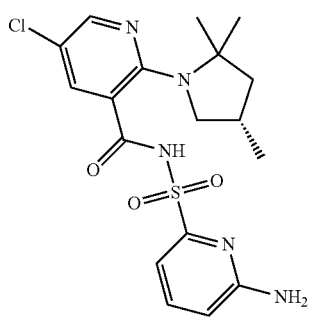 [SMILES: C[C@@H]1CN(c2ncc(Cl)cc2C(=O)NS(=O)(=O)c2cccc(N)n2)C(C)(C)C1]
1603
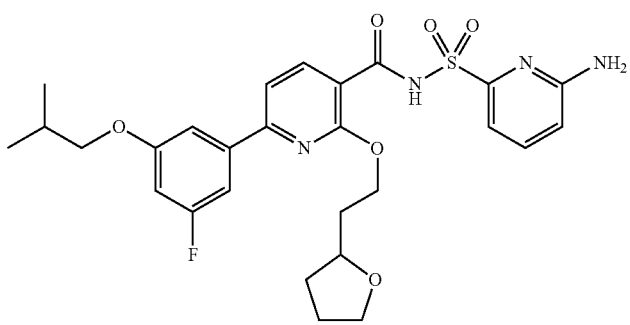 [SMILES: CC(C)COc1cc(F)cc(-c2ccc(C(=O)NS(=O)(=O)c3cccc(N)n3)c(OCCC3CCCO3)n2)c1]
1604
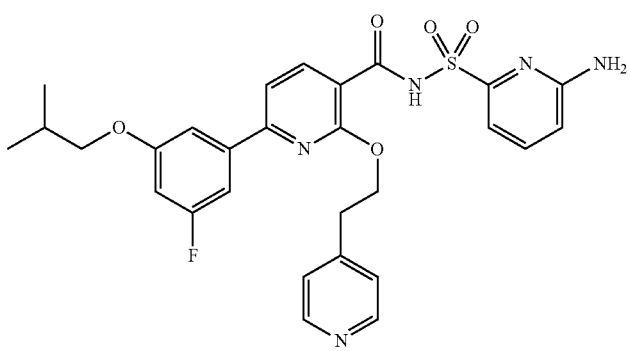 [SMILES: CC(C)COc1cc(F)cc(-c2ccc(C(=O)NS(=O)(=O)c3cccc(N)n3)c(OCCc3ccncc3)n2)c1]
1605

TABLE 1-continued
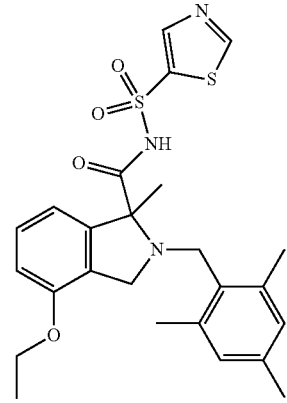 [SMILES: CCOc1cccc2c1CN(Cc1c(C)cc(C)cc1C)C2(C)C(=O)NS(=O)(=O)c1cncs1]
1606
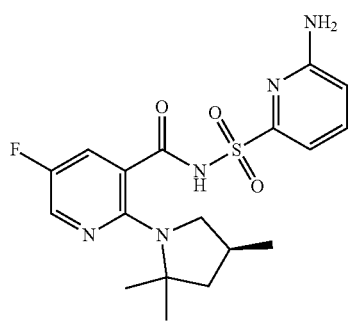 [SMILES: C[C@@H]1CN(c2ncc(F)cc2C(=O)NS(=O)(=O)c2cccc(N)n2)C(C)(C)C1]
1607
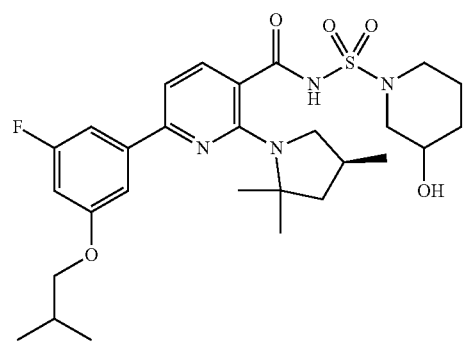 [SMILES: CC(C)COc1cc(F)cc(-c2ccc(C(=O)NS(=O)(=O)N3CCCC(O)C3)c(N3C[C@@H](C)CC3(C)C)n2)c1]
1608
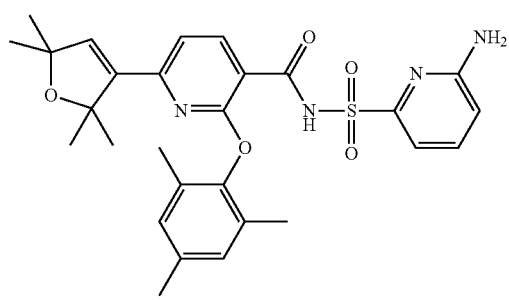 [SMILES: Cc1cc(C)c(Oc2nc(C3=CC(C)(C)OC3(C)C)ccc2C(=O)NS(=O)(=O)c2cccc(N)n2)c(C)c1]
1609

TABLE 1-continued
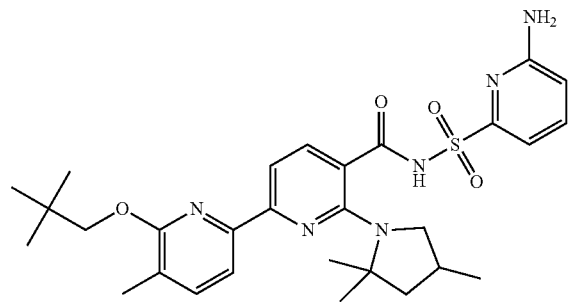 [SMILES: Cc1ccc(-c2ccc(C(=O)NS(=O)(=O)c3cccc(N)n3)c(N3CC(C)CC3(C)C)n2)nc1OCC(C)(C)C]
1610
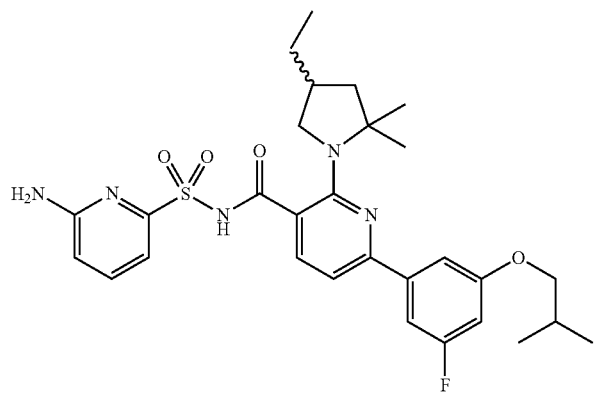 [SMILES: CCC1CN(c2nc(-c3cc(F)cc(OCC(C)C)c3)ccc2C(=O)NS(=O)(=O)c2cccc(N)n2)C(C)(C)C1]
1611
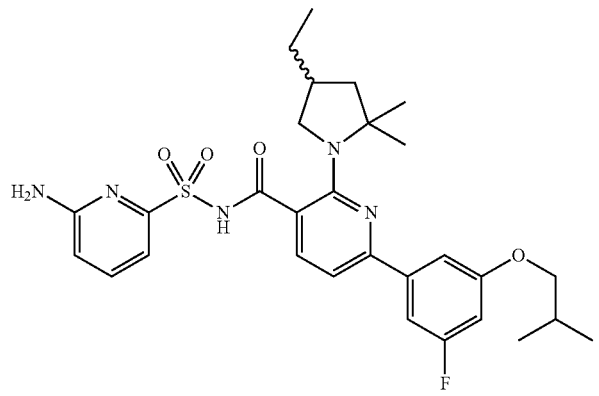 [SMILES: CCC1CN(c2nc(-c3cc(F)cc(OCC(C)C)c3)ccc2C(=O)NS(=O)(=O)c2cccc(N)n2)C(C)(C)C1]
1612
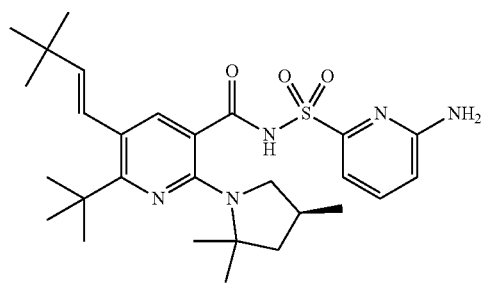 [SMILES: C[C@@H]1CN(c2nc(C(C)(C)C)c(/C=C/C(C)(C)C)cc2C(=O)NS(=O)(=O)c2cccc(N)n2)C(C)(C)C1]
1613

TABLE 1-continued
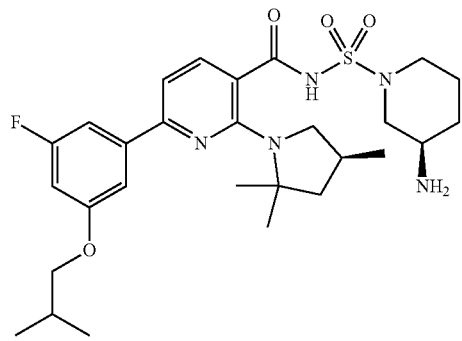 [SMILES: CC(C)COc1cc(F)cc(-c2ccc(C(=O)NS(=O)(=O)N3CCC[C@@H](N)C3)c(N3C[C@@H](C)CC3(C)C)n2)c1]
1614
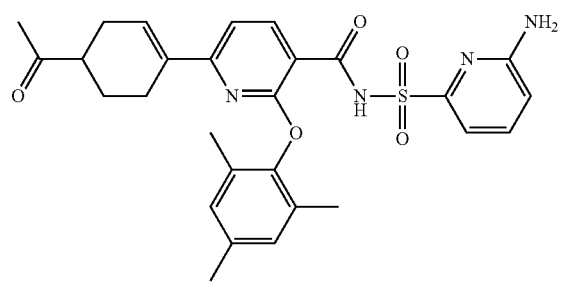 [SMILES: CC(=O)C1CC=C(c2ccc(C(=O)NS(=O)(=O)c3cccc(N)n3)c(Oc3c(C)cc(C)cc3C)n2)CC1]
1615
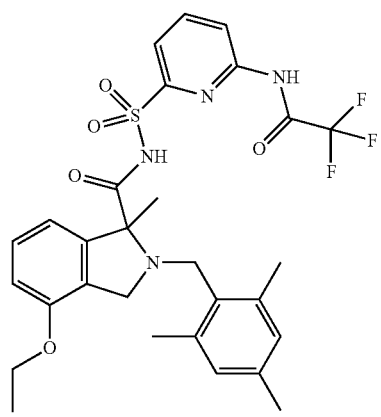 [SMILES: CCOc1cccc2c1CN(Cc1c(C)cc(C)cc1C)C2(C)C(=O)NS(=O)(=O)c1cccc(NC(=O)C(F)(F)F)n1]
1616
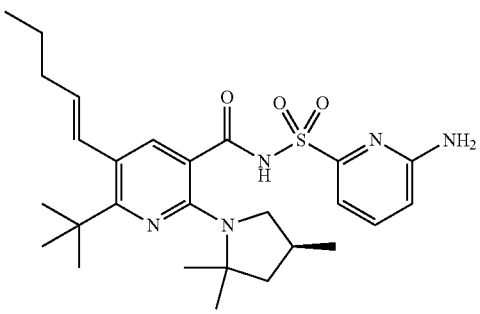 [SMILES: CCC/C=C/c1cc(C(=O)NS(=O)(=O)c2cccc(N)n2)c(N2C[C@@H](C)CC2(C)C)nc1C(C)(C)C]
1617
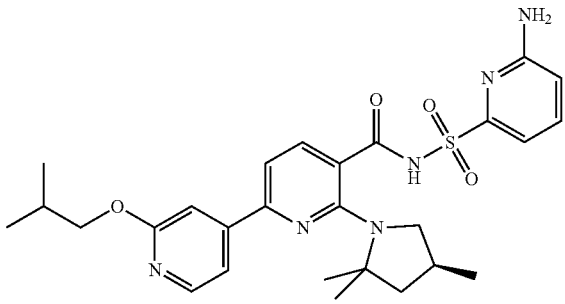 [SMILES: CC(C)COc1cc(-c2ccc(C(=O)NS(=O)(=O)c3cccc(N)n3)c(N3C[C@@H](C)CC3(C)C)n2)ccn1]
1618

TABLE 1-continued
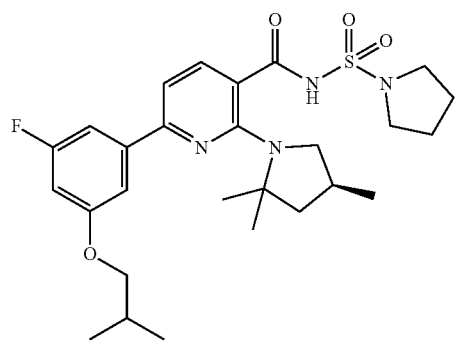 [SMILES: CC(C)COc1cc(F)cc(-c2ccc(C(=O)NS(=O)(=O)N3CCCC3)c(N3C[C@@H](C)CC3(C)C)n2)c1]
1619
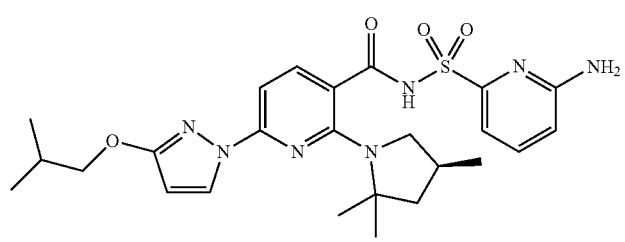 [SMILES: CC(C)COc1ccn(-c2ccc(C(=O)NS(=O)(=O)c3cccc(N)n3)c(N3C[C@@H](C)CC3(C)C)n2)n1]
1620
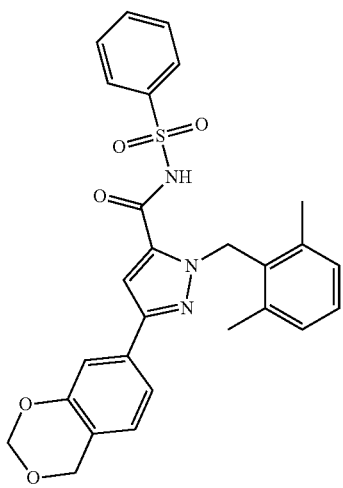 [SMILES: Cc1cccc(C)c1Cn1nc(-c2ccc3c(c2)OCOC3)cc1C(=O)NS(=O)(=O)c1ccccc1]
1621
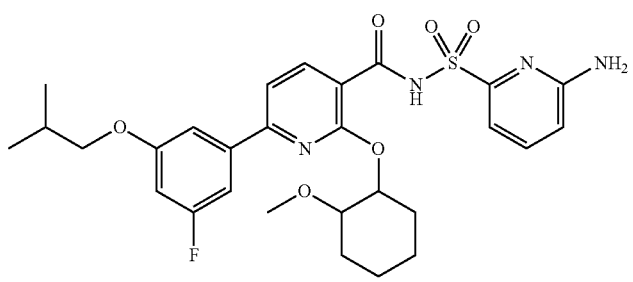 [SMILES: COC1CCCCC1Oc1nc(-c2cc(F)cc(OCC(C)C)c2)ccc1C(=O)NS(=O)(=O)c1cccc(N)n1]
1622

TABLE 1-continued
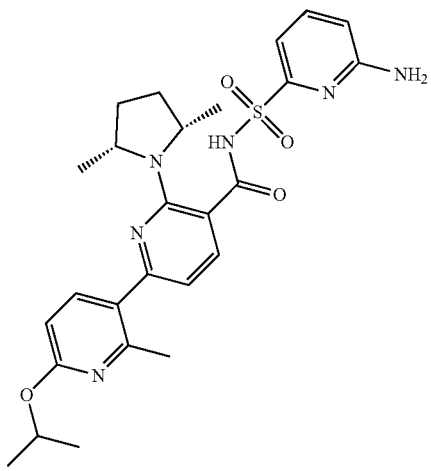 [SMILES: Cc1nc(OC(C)C)ccc1-c1ccc(C(=O)NS(=O)(=O)c2cccc(N)n2)c(N2[C@H](C)CC[C@@H]2C)n1]
1623
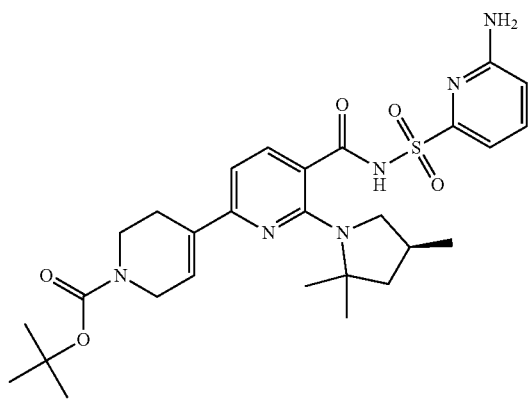 [SMILES: C[C@@H]1CN(c2nc(C3=CCN(C(=O)OC(C)(C)C)CC3)ccc2C(=O)NS(=O)(=O)c2cccc(N)n2)C(C)(C)C1]
1624
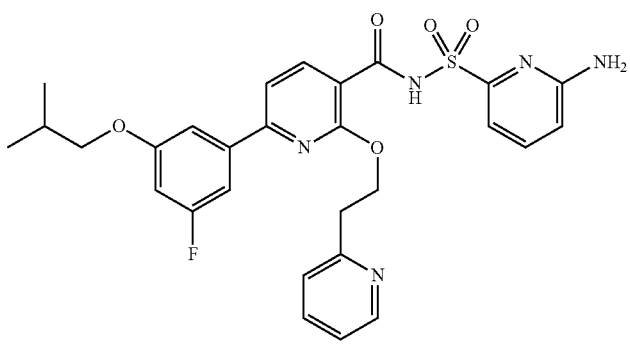 [SMILES: CC(C)COc1cc(F)cc(-c2ccc(C(=O)NS(=O)(=O)c3cccc(N)n3)c(OCCc3ccccn3)n2)c1]
1625
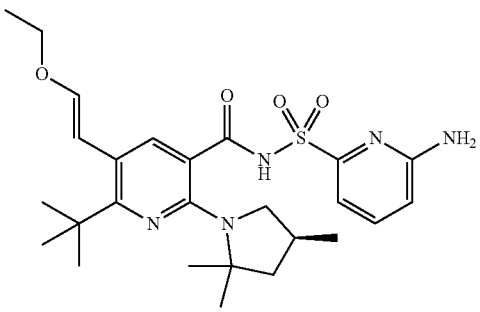 [SMILES: CCO/C=C/c1cc(C(=O)NS(=O)(=O)c2cccc(N)n2)c(N2C[C@@H](C)CC2(C)C)nc1C(C)(C)C]
1626

TABLE 1-continued
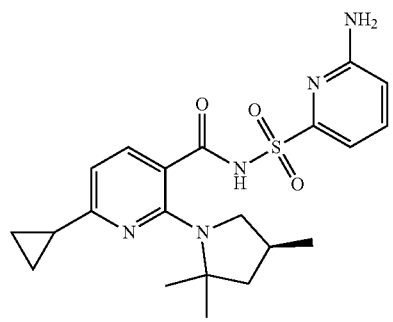 [SMILES: C[C@@H]1CN(c2nc(C3CC3)ccc2C(=O)NS(=O)(=O)c2cccc(N)n2)C(C)(C)C1] 1627
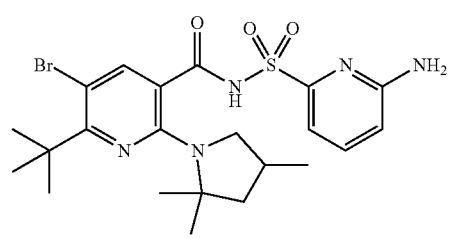 [SMILES: CC1CN(c2nc(C(C)(C)C)c(Br)cc2C(=O)NS(=O)(=O)c2cccc(N)n2)C(C)(C)C1] 1628
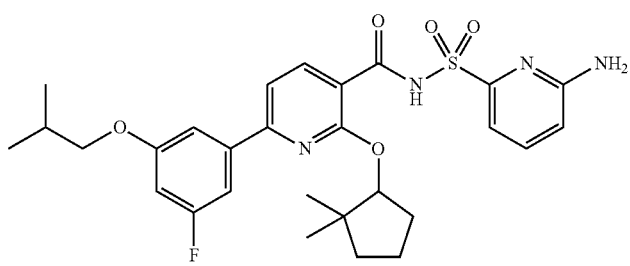 [SMILES: CC(C)COc1cc(F)cc(-c2ccc(C(=O)NS(=O)(=O)c3cccc(N)n3)c(OC3CCCC3(C)C)n2)c1] 1629
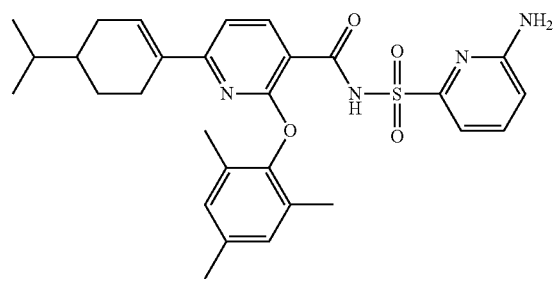 [SMILES: Cc1cc(C)c(Oc2nc(C3=CCC(C(C)C)CC3)ccc2C(=O)NS(=O)(=O)c2cccc(N)n2)c(C)c1] 1630
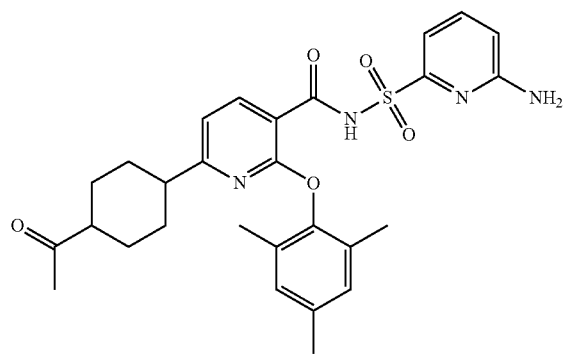 [SMILES: CC(=O)C1CCC(c2ccc(C(=O)NS(=O)(=O)c3cccc(N)n3)c(Oc3c(C)cc(C)cc3C)n2)CC1] 1631

TABLE 1-continued
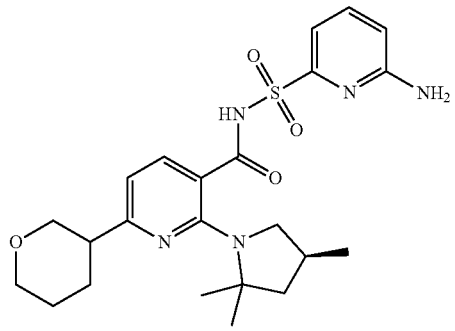 [SMILES: C[C@@H]1CN(c2nc(C3CCCOC3)ccc2C(=O)NS(=O)(=O)c2cccc(N)n2)C(C)(C)C1]
1632
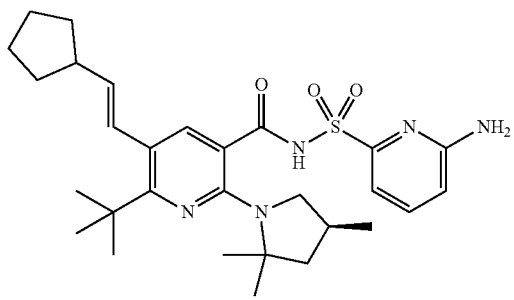 [SMILES: C[C@@H]1CN(c2nc(C(C)(C)C)c(/C=C/C3CCCC3)cc2C(=O)NS(=O)(=O)c2cccc(N)n2)C(C)(C)C1]
1633
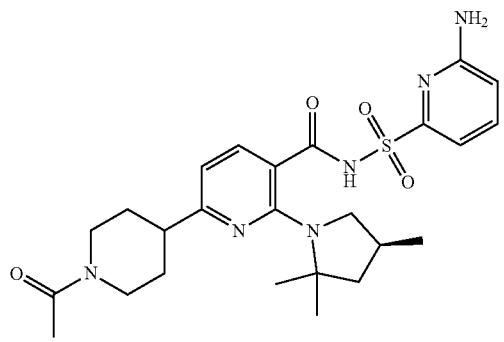 [SMILES: CC(=O)N1CCC(c2ccc(C(=O)NS(=O)(=O)c3cccc(N)n3)c(N3C[C@@H](C)CC3(C)C)n2)CC1]
1634
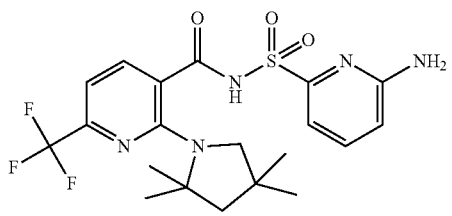 [SMILES: CC1(C)CN(c2nc(C(F)(F)F)ccc2C(=O)NS(=O)(=O)c2cccc(N)n2)C(C)(C)C1]
1635
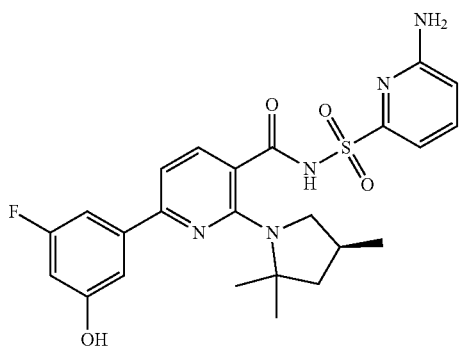 [SMILES: C[C@@H]1CN(c2nc(-c3cc(O)cc(F)c3)ccc2C(=O)NS(=O)(=O)c2cccc(N)n2)C(C)(C)C1]
1636

TABLE 1-continued
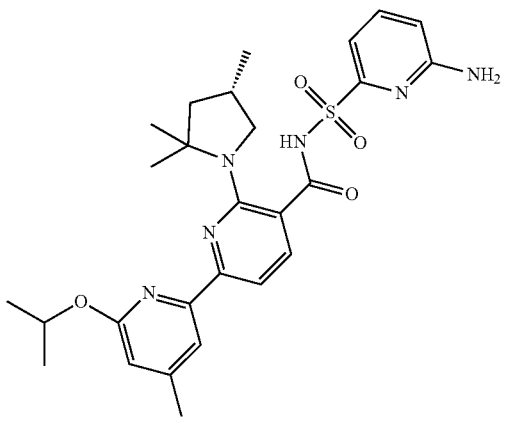 [SMILES: Cc1cc(OC(C)C)nc(-c2ccc(C(=O)NS(=O)(=O)c3cccc(N)n3)c(N3C[C@@H](C)CC3(C)C)n2)c1]
1637
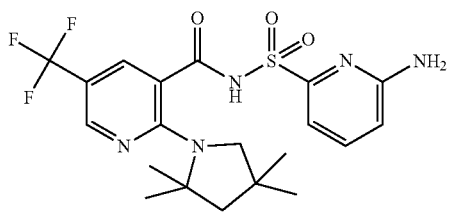 [SMILES: CC1(C)CN(c2ncc(C(F)(F)F)cc2C(=O)NS(=O)(=O)c2cccc(N)n2)C(C)(C)C1]
1638
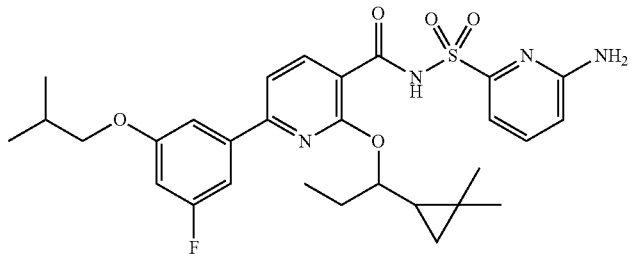 [SMILES: CCC(Oc1nc(-c2cc(F)cc(OCC(C)C)c2)ccc1C(=O)NS(=O)(=O)c1cccc(N)n1)C1CC1(C)C]
1639
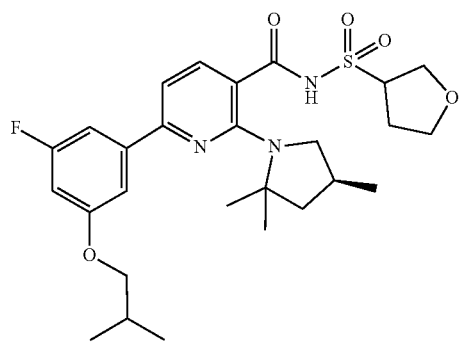 [SMILES: CC(C)COc1cc(F)cc(-c2ccc(C(=O)NS(=O)(=O)C3CCOC3)c(N3C[C@@H](C)CC3(C)C)n2)c1]
1640

TABLE 1-continued
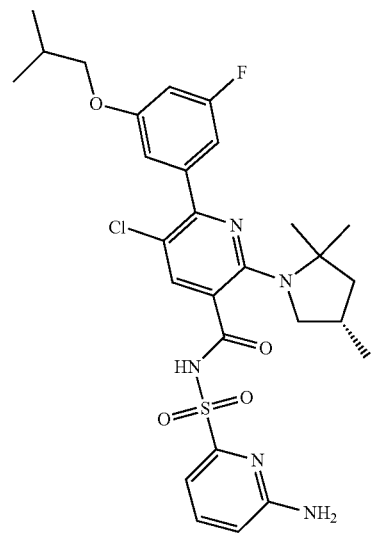 [SMILES: CC(C)COc1cc(F)cc(-c2nc(N3C[C@@H](C)CC3(C)C)c(C(=O)NS(=O)(=O)c3cccc(N)n3)cc2Cl)c1]
1641
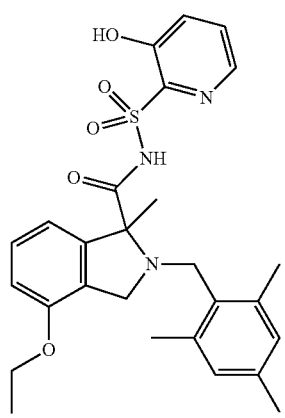 [SMILES: CCOc1cccc2c1CN(Cc1c(C)cc(C)cc1C)C2(C)C(=O)NS(=O)(=O)c1ncccc1O]
1642
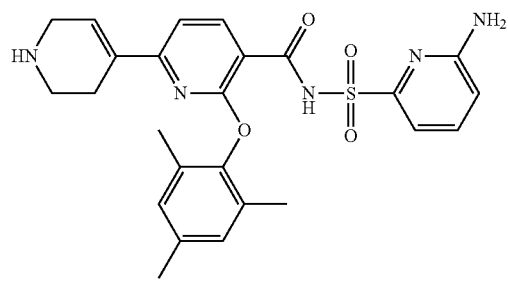 [SMILES: Cc1cc(C)c(Oc2nc(C3=CCNCC3)ccc2C(=O)NS(=O)(=O)c2cccc(N)n2)c(C)c1]
1643
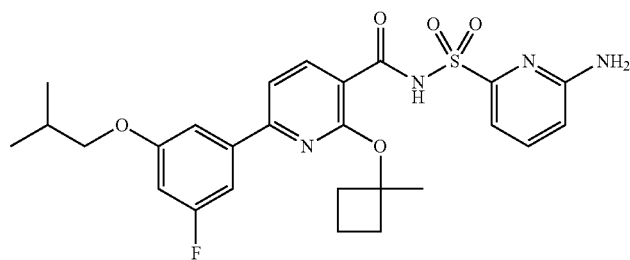 [SMILES: CC(C)COc1cc(F)cc(-c2ccc(C(=O)NS(=O)(=O)c3cccc(N)n3)c(OC3(C)CCC3)n2)c1]
1644

TABLE 1-continued
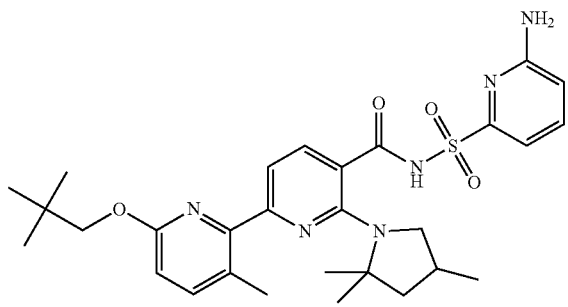 [SMILES: Cc1ccc(OCC(C)(C)C)nc1-c1ccc(C(=O)NS(=O)(=O)c2cccc(N)n2)c(N2CC(C)CC2(C)C)n1]
1645
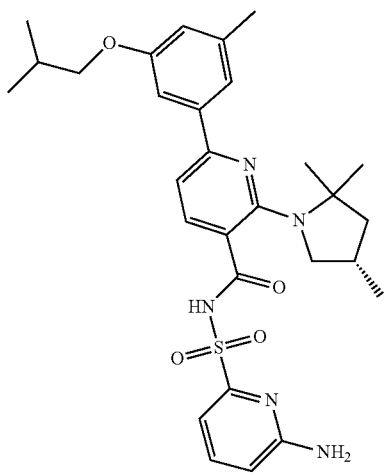 [SMILES: Cc1cc(OCC(C)C)cc(-c2ccc(C(=O)NS(=O)(=O)c3cccc(N)n3)c(N3C[C@@H](C)CC3(C)C)n2)c1]
1646
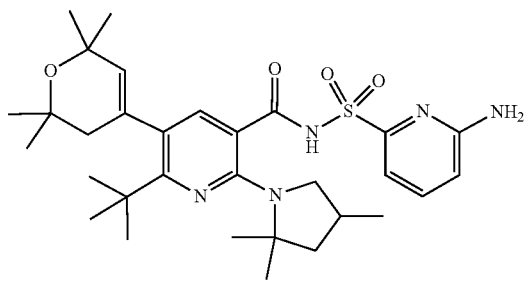 [SMILES: CC1CN(c2nc(C(C)(C)C)c(C3=CC(C)(C)OC(C)(C)C3)cc2C(=O)NS(=O)(=O)c2cccc(N)n2)C(C)(C)C1]
1647
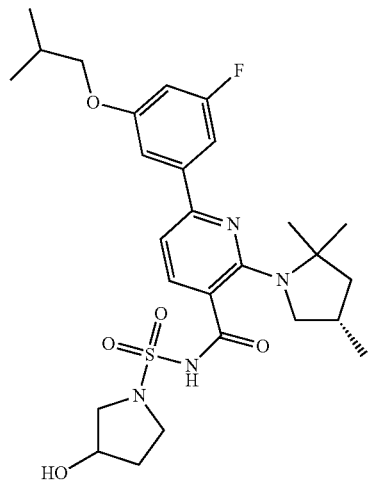 [SMILES: CC(C)COc1cc(F)cc(-c2ccc(C(=O)NS(=O)(=O)N3CCC(O)C3)c(N3C[C@@H](C)CC3(C)C)n2)c1]
1648

TABLE 1-continued
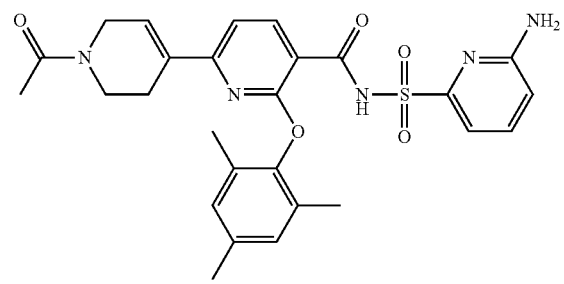 [SMILES: CC(=O)N1CC=C(c2ccc(C(=O)NS(=O)(=O)c3cccc(N)n3)c(Oc3c(C)cc(C)cc3C)n2)CC1] 1649
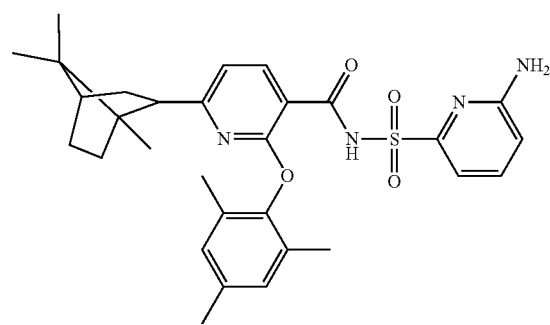 [SMILES: Cc1cc(C)c(Oc2nc(C3CC4CCC3(C)C4(C)C)ccc2C(=O)NS(=O)(=O)c2cccc(N)n2)c(C)c1] 1650
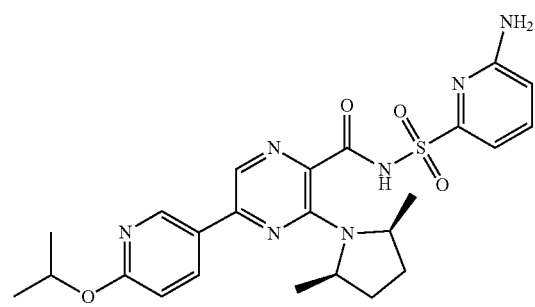 [SMILES: CC(C)Oc1ccc(-c2cnc(C(=O)NS(=O)(=O)c3cccc(N)n3)c(N3[C@H](C)CC[C@@H]3C)n2)cn1] 1651
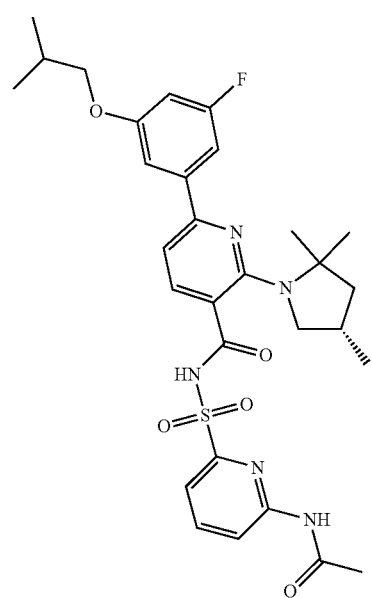 [SMILES: CC(=O)Nc1cccc(S(=O)(=O)NC(=O)c2ccc(-c3cc(F)cc(OCC(C)C)c3)nc2N2C[C@@H](C)CC2(C)C)n1] 1652

TABLE 1-continued
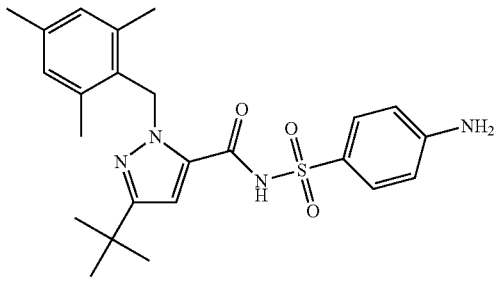 [SMILES: Cc1cc(C)c(Cn2nc(C(C)(C)C)cc2C(=O)NS(=O)(=O)c2ccc(N)cc2)c(C)c1]
1653
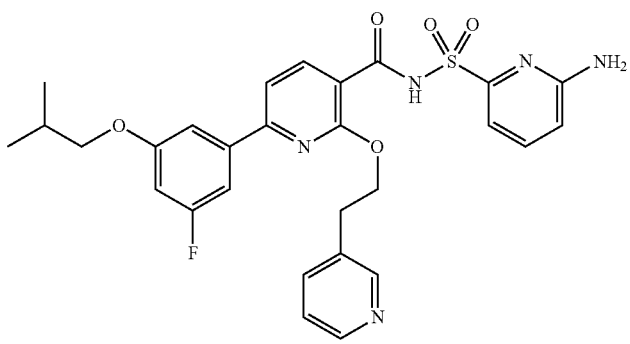
1654
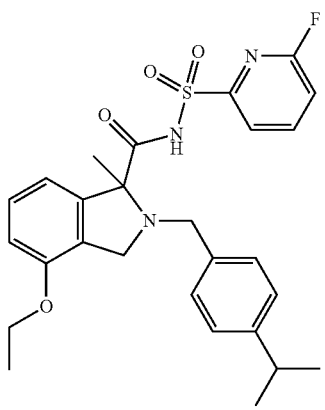 [SMILES: CCOc1cccc2c1CN(Cc1ccc(C(C)C)cc1)C2(C)C(=O)NS(=O)(=O)c1cccc(F)n1]
1655
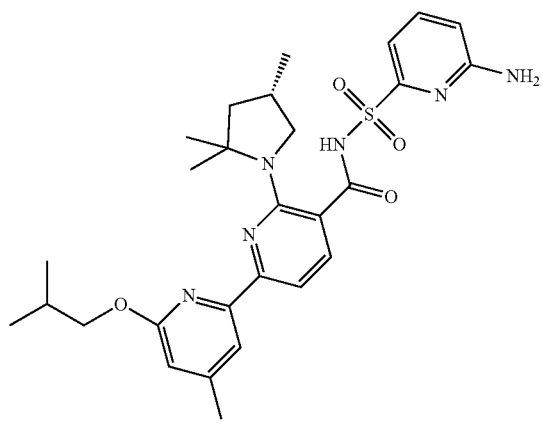 [SMILES: Cc1cc(OCC(C)C)nc(-c2ccc(C(=O)NS(=O)(=O)c3cccc(N)n3)c(N3C[C@@H](C)CC3(C)C)n2)c1]
1656

TABLE 1-continued
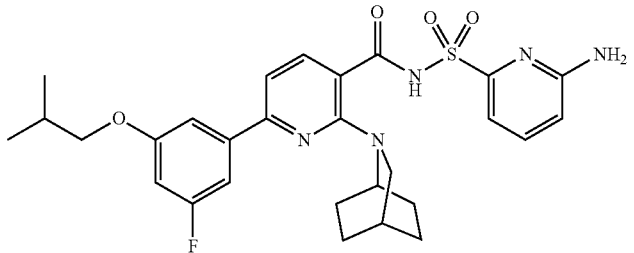 [SMILES: CC(C)COc1cc(F)cc(-c2ccc(C(=O)NS(=O)(=O)c3cccc(N)n3)c(N3CC4CCC3CC4)n2)c1]
1657
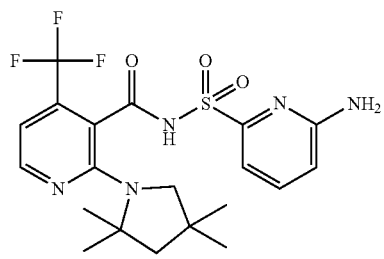 [SMILES: CC1(C)CN(c2nccc(C(F)(F)F)c2C(=O)NS(=O)(=O)c2cccc(N)n2)C(C)(C)C1]
1658
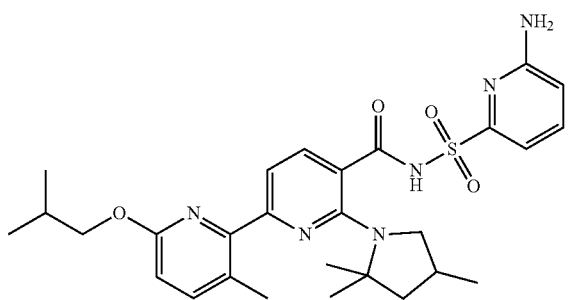 [SMILES: Cc1ccc(OCC(C)C)nc1-c1ccc(C(=O)NS(=O)(=O)c2cccc(N)n2)c(N2CC(C)CC2(C)C)n1]
1659
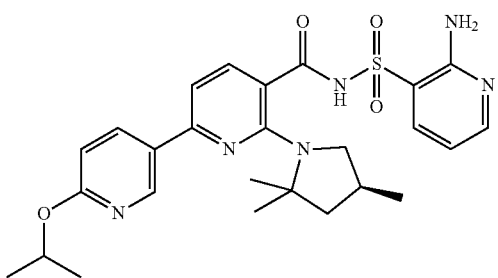 [SMILES: CC(C)Oc1ccc(-c2ccc(C(=O)NS(=O)(=O)c3cccnc3N)c(N3C[C@@H](C)CC3(C)C)n2)cn1]
1660
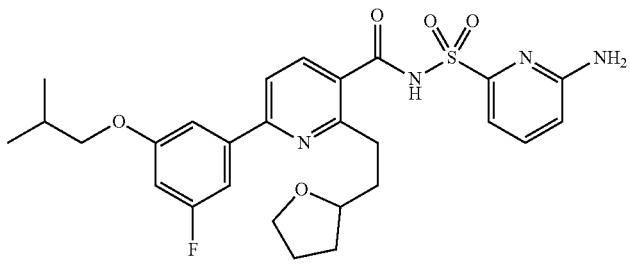 [SMILES: CC(C)COc1cc(F)cc(-c2ccc(C(=O)NS(=O)(=O)c3cccc(N)n3)c(CCC3CCCO3)n2)c1]
1661

TABLE 1-continued
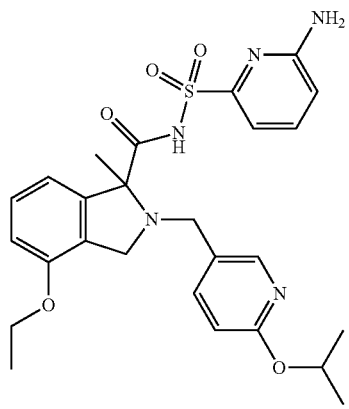 [SMILES: CCOc1cccc2c1CN(Cc1ccc(OC(C)C)nc1)C2(C)C(=O)NS(=O)(=O)c1cccc(N)n1]
1662
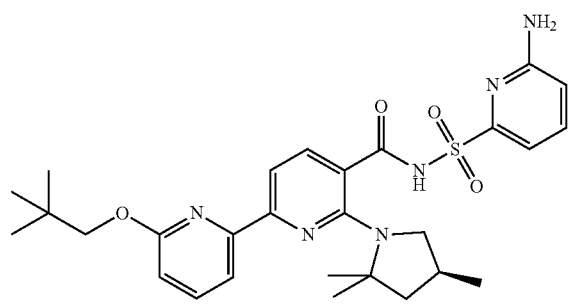 [SMILES: C[C@@H]1CN(c2nc(-c3cccc(OCC(C)(C)C)n3)ccc2C(=O)NS(=O)(=O)c2cccc(N)n2)C(C)(C)C1]
1663
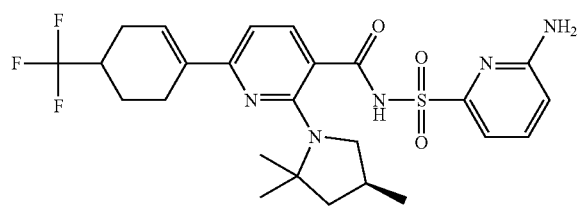 [SMILES: C[C@@H]1CN(c2nc(C3=CCC(C(F)(F)F)CC3)ccc2C(=O)NS(=O)(=O)c2cccc(N)n2)C(C)(C)C1]
1664
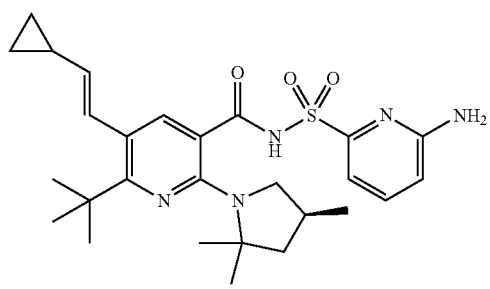 [SMILES: C[C@@H]1CN(c2nc(C(C)(C)C)c(/C=C/C3CC3)cc2C(=O)NS(=O)(=O)c2cccc(N)n2)C(C)(C)C1]
1665
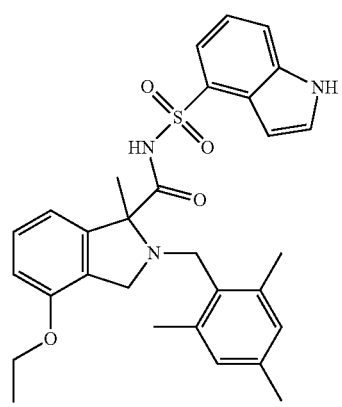 [SMILES: CCOc1cccc2c1CN(Cc1c(C)cc(C)cc1C)C2(C)C(=O)NS(=O)(=O)c1cccc2[nH]ccc12]
1666

TABLE 1-continued
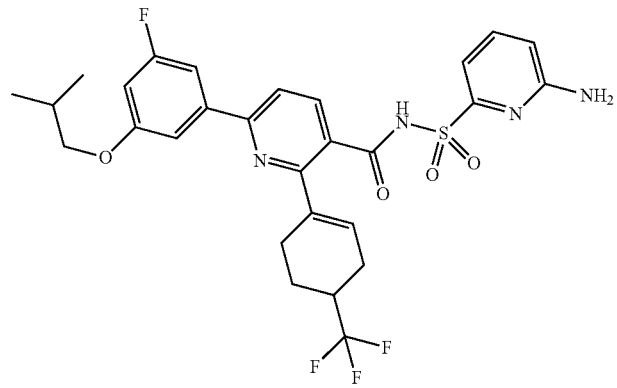 [SMILES: CC(C)COc1cc(F)cc(-c2ccc(C(=O)NS(=O)(=O)c3cccc(N)n3)c(C3=CCC(C(F)(F)F)CC3)n2)c1]
1667
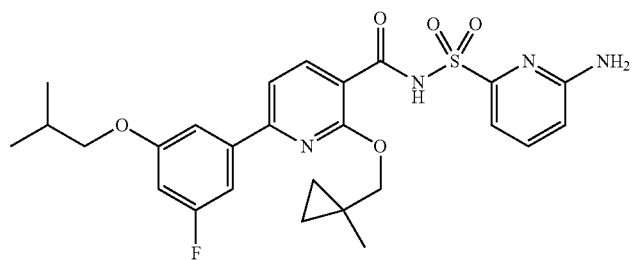 [SMILES: CC(C)COc1cc(F)cc(-c2ccc(C(=O)NS(=O)(=O)c3cccc(N)n3)c(OCC3(C)CC3)n2)c1]
1668
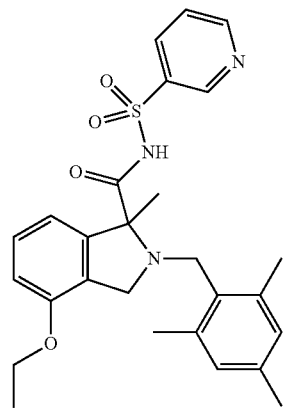 [SMILES: CCOc1cccc2c1CN(Cc1c(C)cc(C)cc1C)C2(C)C(=O)NS(=O)(=O)c1cccnc1]
1669
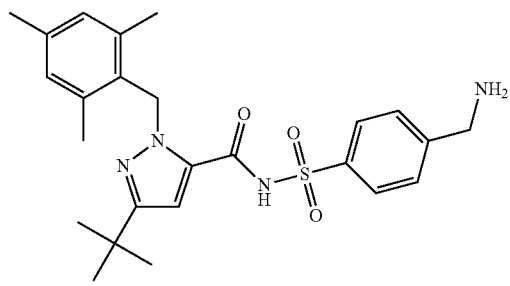 [SMILES: Cc1cc(C)c(Cn2nc(C(C)(C)C)cc2C(=O)NS(=O)(=O)c2ccc(CN)cc2)c(C)c1]
1670

TABLE 1-continued
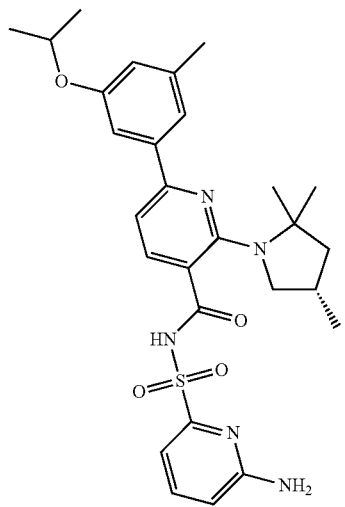 [SMILES: Cc1cc(OC(C)C)cc(-c2ccc(C(=O)NS(=O)(=O)c3cccc(N)n3)c(N3C[C@@H](C)CC3(C)C)n2)c1]
1671
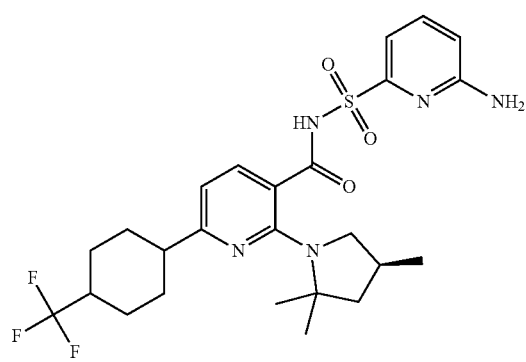 [SMILES: C[C@@H]1CN(c2nc(C3CCC(C(F)(F)F)CC3)ccc2C(=O)NS(=O)(=O)c2cccc(N)n2)C(C)(C)C1]
1672
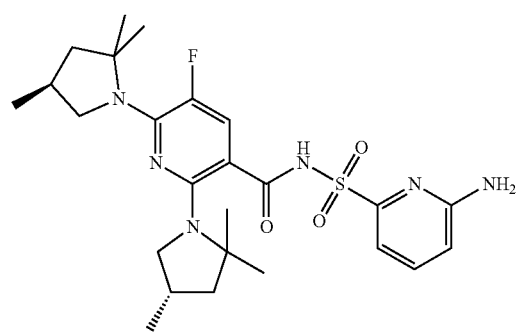 [SMILES: C[C@@H]1CN(c2nc(N3C[C@@H](C)CC3(C)C)c(C(=O)NS(=O)(=O)c3cccc(N)n3)cc2F)C(C)(C)C1]
1673

TABLE 1-continued
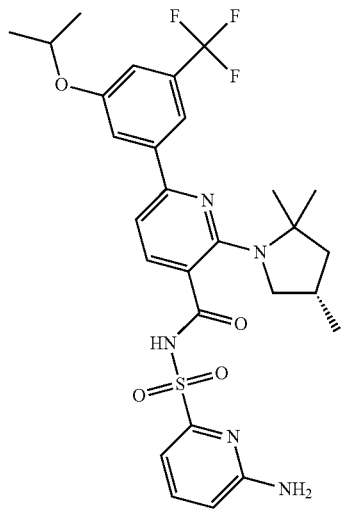 [SMILES: CC(C)Oc1cc(-c2ccc(C(=O)NS(=O)(=O)c3cccc(N)n3)c(N3C[C@@H](C)CC3(C)C)n2)cc(C(F)(F)F)c1]
1674
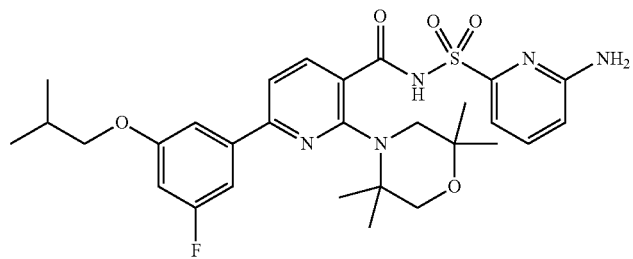 [SMILES: CC(C)COc1cc(F)cc(-c2ccc(C(=O)NS(=O)(=O)c3cccc(N)n3)c(N3CC(C)(C)OCC3(C)C)n2)c1]
1675
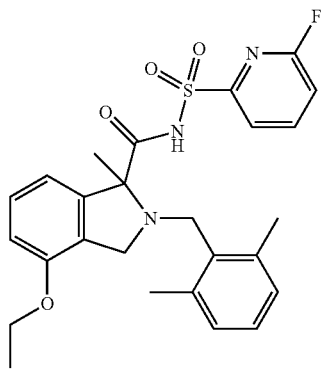 [SMILES: CCOc1cccc2c1CN(Cc1c(C)cccc1C)C2(C)C(=O)NS(=O)(=O)c1cccc(F)n1]
1676
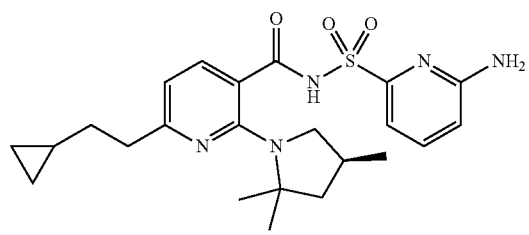 [SMILES: C[C@@H]1CN(c2nc(CCC3CC3)ccc2C(=O)NS(=O)(=O)c2cccc(N)n2)C(C)(C)C1]
1677

TABLE 1-continued
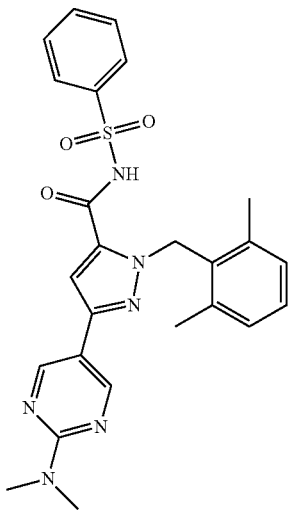 [SMILES: Cc1cccc(C)c1Cn1nc(-c2cnc(N(C)C)nc2)cc1C(=O)NS(=O)(=O)c1ccccc1]
1678
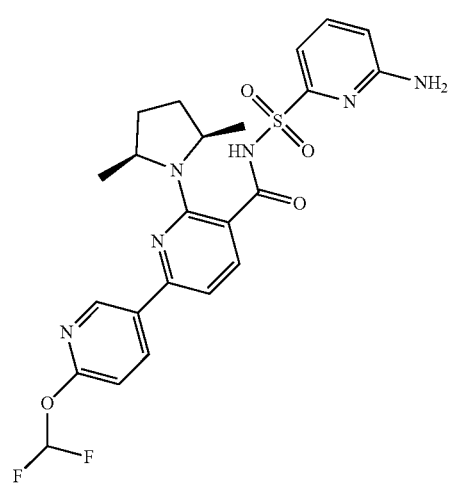 [SMILES: C[C@@H]1CC[C@H](C)N1c1nc(-c2ccc(OC(F)F)nc2)ccc1C(=O)NS(=O)(=O)c1cccc(N)n1]
1679
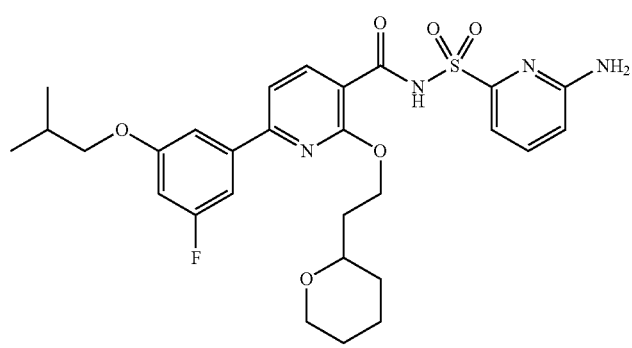 [SMILES: CC(C)COc1cc(F)cc(-c2ccc(C(=O)NS(=O)(=O)c3cccc(N)n3)c(OCCC3CCCCO3)n2)c1]
1680

TABLE 1-continued
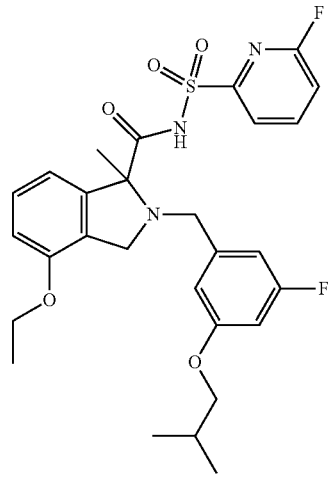 [SMILES: CCOc1cccc2c1CN(Cc1cc(F)cc(OCC(C)C)c1)C2(C)C(=O)NS(=O)(=O)c1cccc(F)n1]
1681
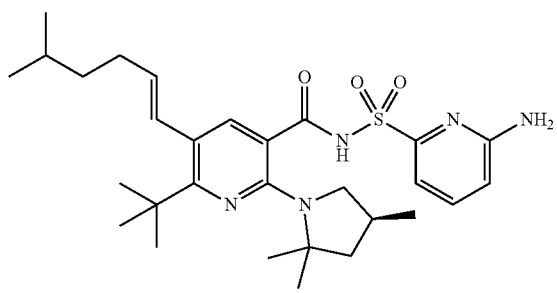 [SMILES: CC(C)CC/C=C/c1cc(C(=O)NS(=O)(=O)c2cccc(N)n2)c(N2C[C@@H](C)CC2(C)C)nc1C(C)(C)C]
1682
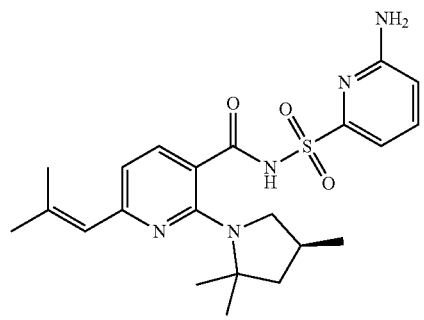 [SMILES: CC(C)=Cc1ccc(C(=O)NS(=O)(=O)c2cccc(N)n2)c(N2C[C@@H](C)CC2(C)C)n1]
1683
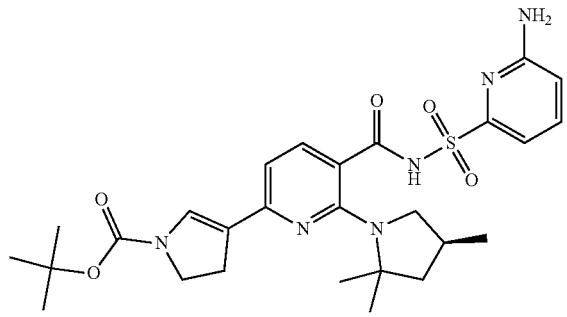 [SMILES: C[C@@H]1CN(c2nc(C3=CN(C(=O)OC(C)(C)C)CC3)ccc2C(=O)NS(=O)(=O)c2cccc(N)n2)C(C)(C)C1]
1684

TABLE 1-continued
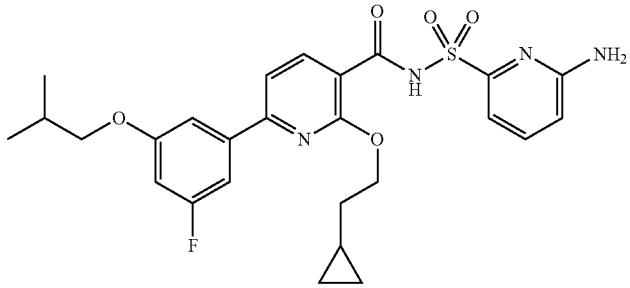 [SMILES: CC(C)COc1cc(F)cc(-c2ccc(C(=O)NS(=O)(=O)c3cccc(N)n3)c(OCCC3CC3)n2)c1] 1685
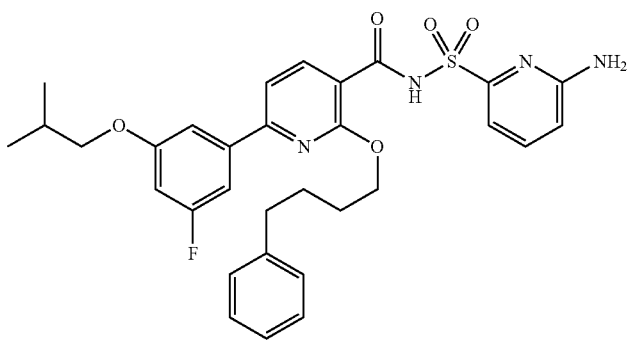 [SMILES: CC(C)COc1cc(F)cc(-c2ccc(C(=O)NS(=O)(=O)c3cccc(N)n3)c(OCCCCc3ccccc3)n2)c1] 1686
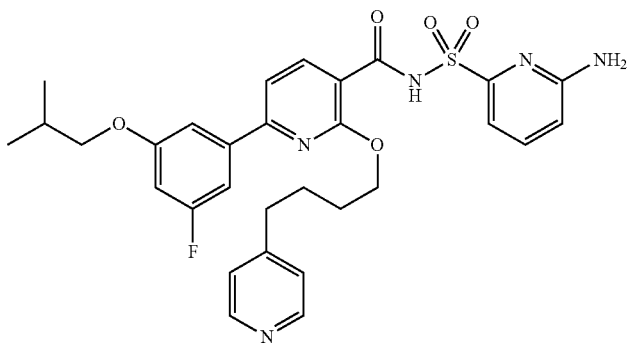 [SMILES: CC(C)COc1cc(F)cc(-c2ccc(C(=O)NS(=O)(=O)c3cccc(N)n3)c(OCCCCc3ccncc3)n2)c1] 1687
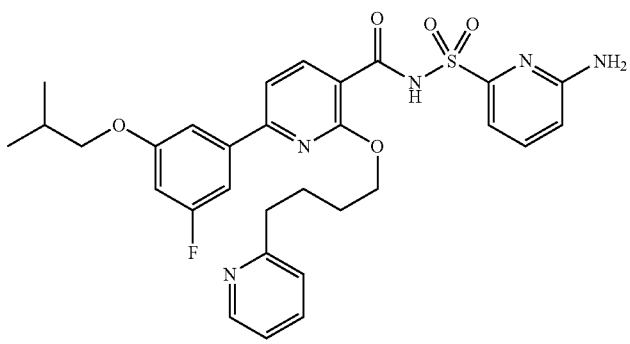 [SMILES: CC(C)COc1cc(F)cc(-c2ccc(C(=O)NS(=O)(=O)c3cccc(N)n3)c(OCCCCc3ccccn3)n2)c1] 1688

TABLE 1-continued
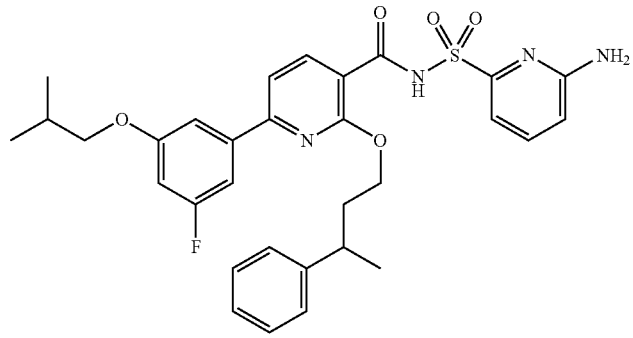 [SMILES: CC(C)COc1cc(F)cc(-c2ccc(C(=O)NS(=O)(=O)c3cccc(N)n3)c(OCCC(C)c3ccccc3)n2)c1]
1689
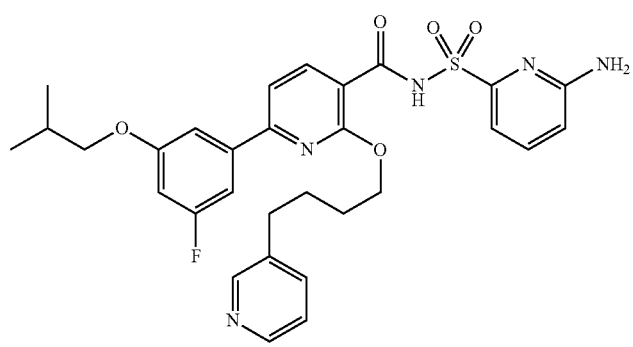 [SMILES: CC(C)COc1cc(F)cc(-c2ccc(C(=O)NS(=O)(=O)c3cccc(N)n3)c(OCCCCc3cccnc3)n2)c1]
1690
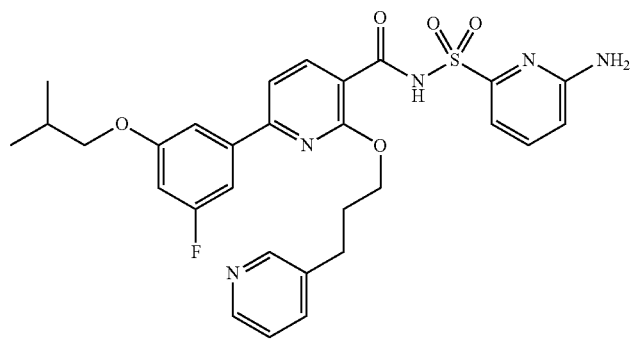
1691
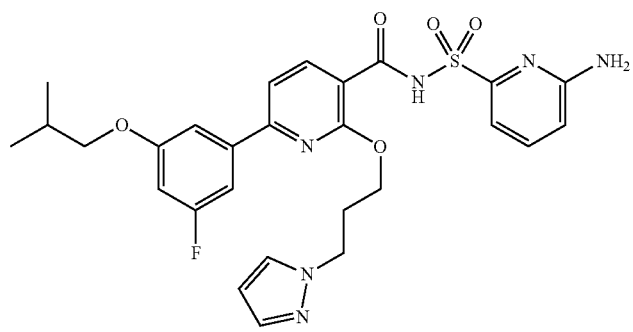 [SMILES: CC(C)COc1cc(F)cc(-c2ccc(C(=O)NS(=O)(=O)c3cccc(N)n3)c(OCCCn3cccn3)n2)c1]
1692

TABLE 1-continued
| | |
|---|---|
| 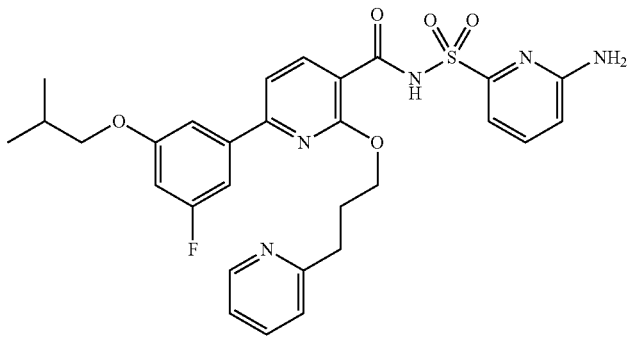 [SMILES: CC(C)COc1cc(F)cc(-c2ccc(C(=O)NS(=O)(=O)c3cccc(N)n3)c(OCCCc3ccccn3)n2)c1] | 1693 |
| 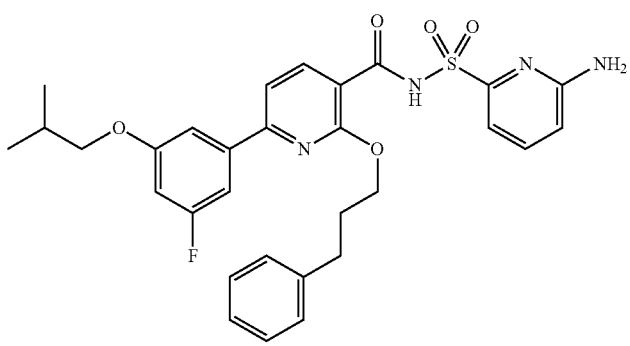 [SMILES: CC(C)COc1cc(F)cc(-c2ccc(C(=O)NS(=O)(=O)c3cccc(N)n3)c(OCCCc3ccccc3)n2)c1] | 1694 |
| 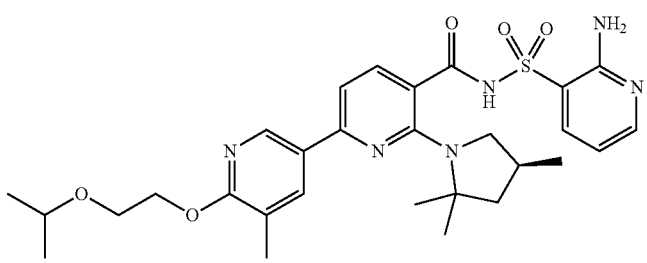 [SMILES: Cc1cc(-c2ccc(C(=O)NS(=O)(=O)c3cccnc3N)c(N3C[C@@H](C)CC3(C)C)n2)cnc1OCCOC(C)C] | 1695 |
| 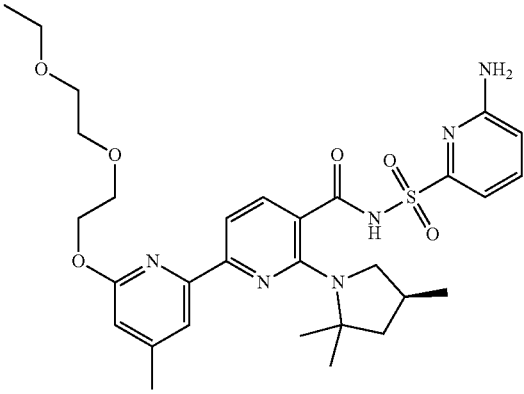 [SMILES: CCOCCOCCOc1cc(C)cc(-c2ccc(C(=O)NS(=O)(=O)c3cccc(N)n3)c(N3C[C@@H](C)CC3(C)C)n2)n1] | 1696 |
| 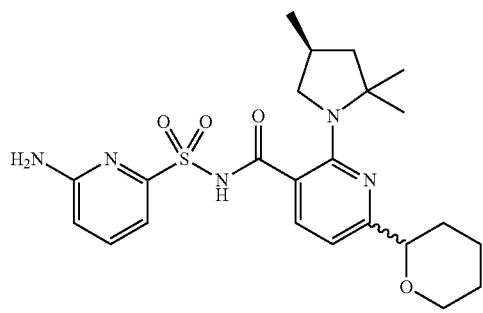 [SMILES: C[C@@H]1CN(c2nc(C3CCCCO3)ccc2C(=O)NS(=O)(=O)c2cccc(N)n2)C(C)(C)C1] | 1697 |

TABLE 1-continued
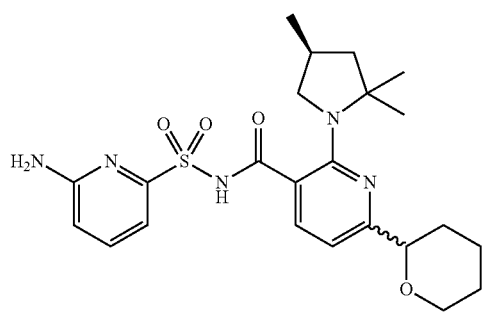 [SMILES: C[C@@H]1CN(c2nc(C3CCCCO3)ccc2C(=O)NS(=O)(=O)c2cccc(N)n2)C(C)(C)C1]
1698
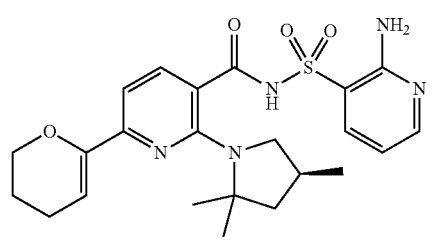 [SMILES: C[C@@H]1CN(c2nc(C3=CCCCO3)ccc2C(=O)NS(=O)(=O)c2cccnc2N)C(C)(C)C1]
1699
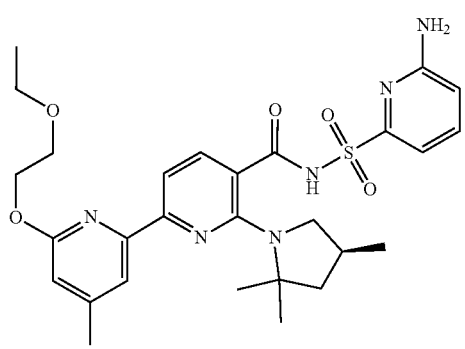 [SMILES: CCOCCOc1cc(C)cc(-c2ccc(C(=O)NS(=O)(=O)c3cccc(N)n3)c(N3C[C@@H](C)CC3(C)C)n2)n1]
1700
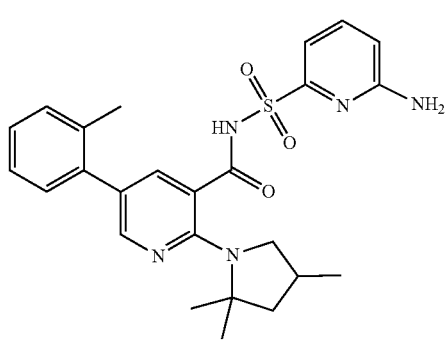 [SMILES: Cc1ccccc1-c1cnc(N2CC(C)CC2(C)C)c(C(=O)NS(=O)(=O)c2cccc(N)n2)c1]
1701
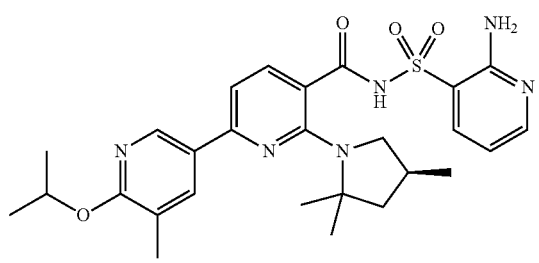 [SMILES: Cc1cc(-c2ccc(C(=O)NS(=O)(=O)c3cccnc3N)c(N3C[C@@H](C)CC3(C)C)n2)cnc1OC(C)C]
1702

TABLE 1-continued
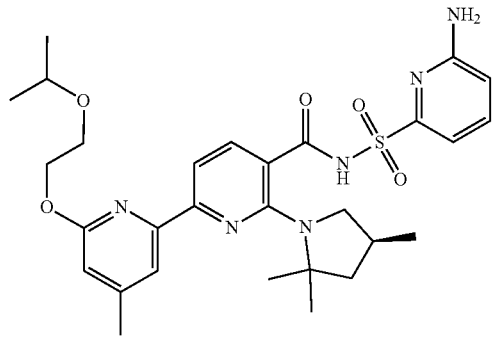 [SMILES: Cc1cc(OCCOC(C)C)nc(-c2ccc(C(=O)NS(=O)(=O)c3cccc(N)n3)c(N3C[C@@H](C)CC3(C)C)n2)c1]
1703
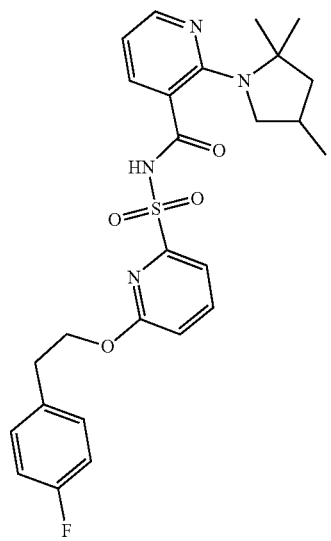 [SMILES: CC1CN(c2ncccc2C(=O)NS(=O)(=O)c2cccc(OCCc3ccc(F)cc3)n2)C(C)(C)C1]
1704
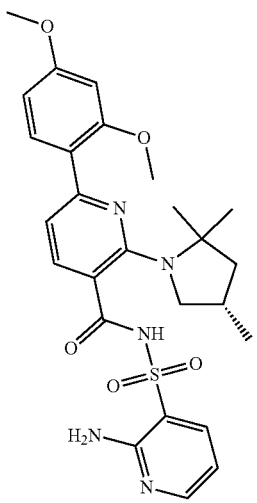
1705
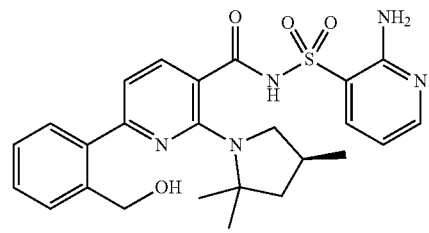 [SMILES: C[C@@H]1CN(c2nc(-c3ccccc3CO)ccc2C(=O)NS(=O)(=O)c2cccnc2N)C(C)(C)C1]
1706

TABLE 1-continued
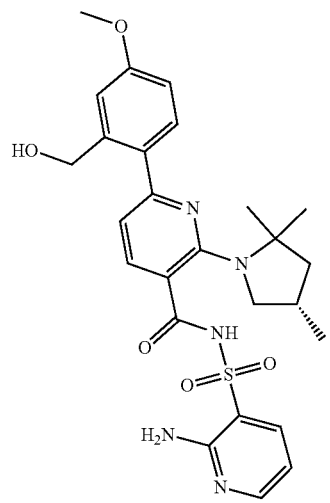 [SMILES: COc1ccc(-c2ccc(C(=O)NS(=O)(=O)c3cccnc3N)c(N3C[C@@H](C)CC3(C)C)n2)c(CO)c1]
1707
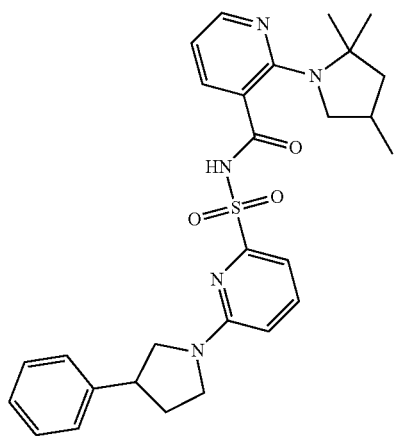 [SMILES: CC1CN(c2ncccc2C(=O)NS(=O)(=O)c2cccc(N3CCC(c4ccccc4)C3)n2)C(C)(C)C1]
1708
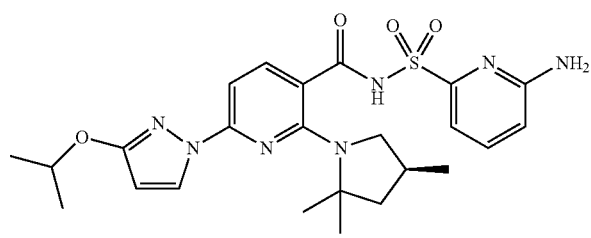 [SMILES: CC(C)Oc1ccn(-c2ccc(C(=O)NS(=O)(=O)c3cccc(N)n3)c(N3C[C@@H](C)CC3(C)C)n2)n1]
1709
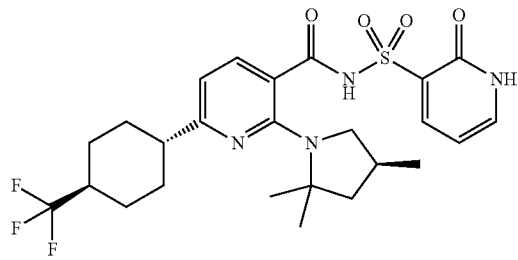 [SMILES: C[C@@H]1CN(c2nc([C@H]3CC[C@H](C(F)(F)F)CC3)ccc2C(=O)NS(=O)(=O)c2ccc[nH]c2=O)C(C)(C)C1]
1710

TABLE 1-continued
| | |
|---|---|
| 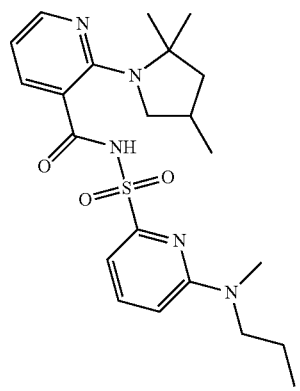 [SMILES: CCCN(C)c1cccc(S(=O)(=O)NC(=O)c2cccnc2N2CC(C)CC2(C)C)n1] | 1711 |
| 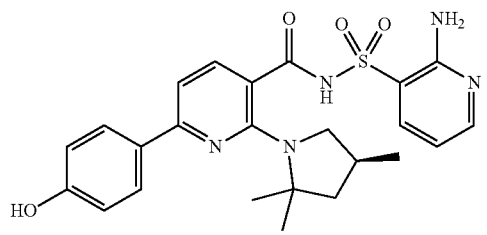 [SMILES: C[C@@H]1CN(c2nc(-c3ccc(O)cc3)ccc2C(=O)NS(=O)(=O)c2cccnc2N)C(C)(C)C1] | 1712 |
| 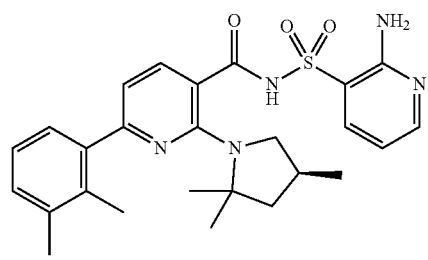 [SMILES: Cc1cccc(-c2ccc(C(=O)NS(=O)(=O)c3cccnc3N)c(N3C[C@@H](C)CC3(C)C)n2)c1C] | 1713 |
| 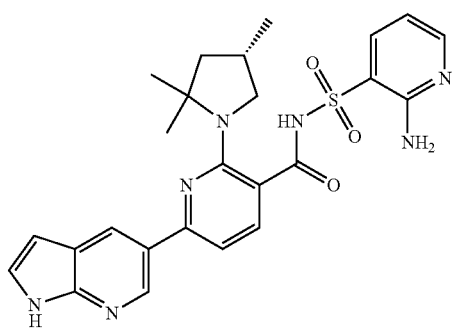 | 1714 |
| 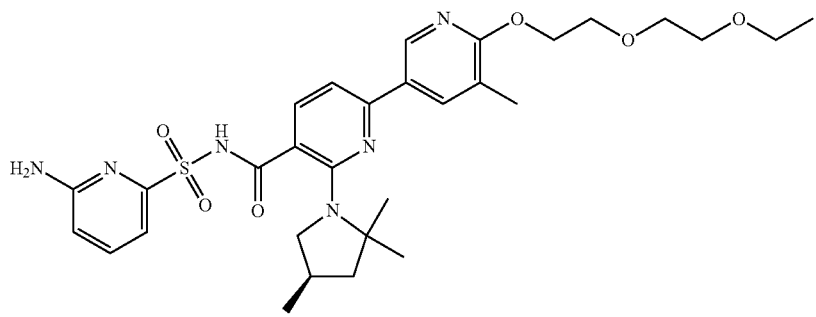 | 1715 |

TABLE 1-continued
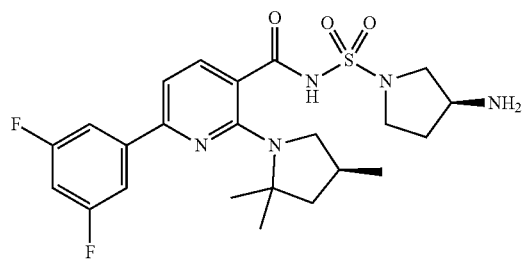
1716
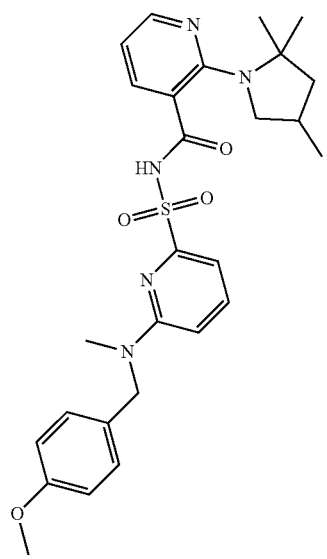 [SMILES: COc1ccc(CN(C)c2cccc(S(=O)(=O)NC(=O)c3cccnc3N3CC(C)CC3(C)C)n2)cc1]
1717
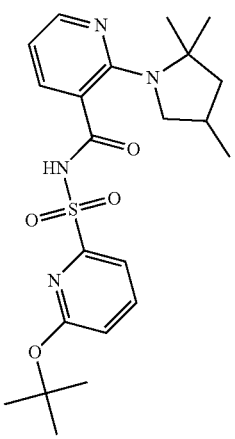 [SMILES: CC1CN(c2ncccc2C(=O)NS(=O)(=O)c2cccc(OC(C)(C)C)n2)C(C)(C)C1]
1718
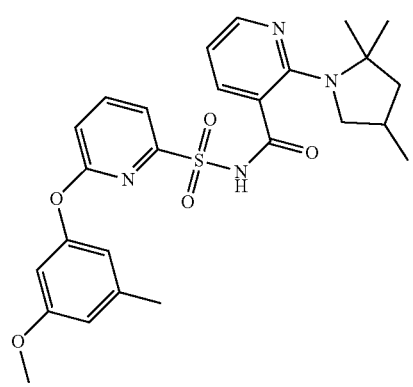
1719

TABLE 1-continued
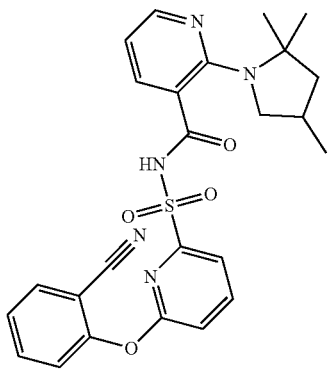 [SMILES: CC1CN(c2ncccc2C(=O)NS(=O)(=O)c2cccc(Oc3ccccc3C#N)n2)C(C)(C)C1]
1720
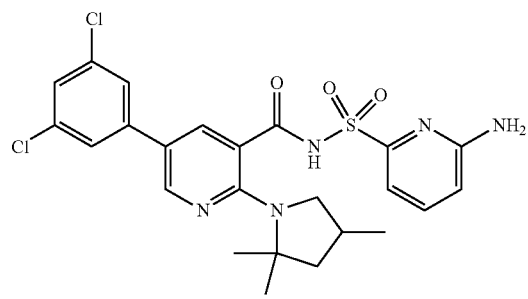
1721
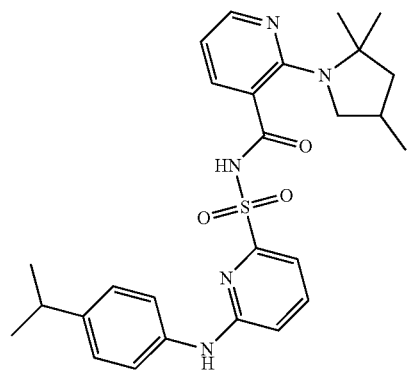
1722
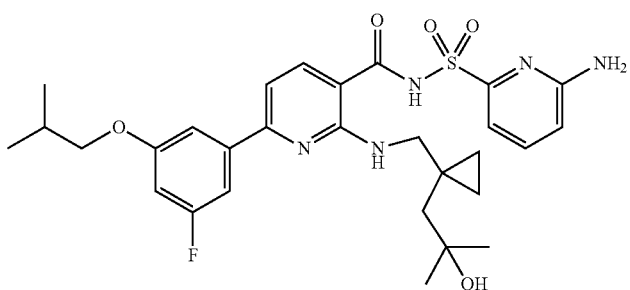
1723
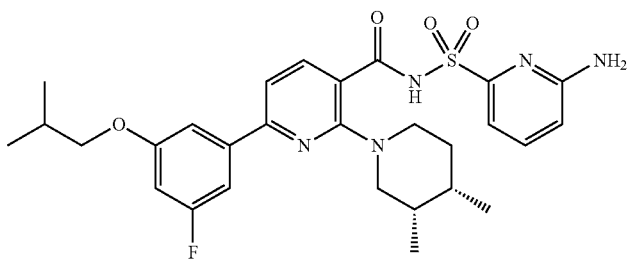
1724

TABLE 1-continued
| | |
|---|---|
| 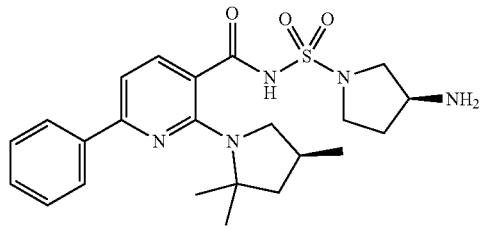 | 1725 |
| 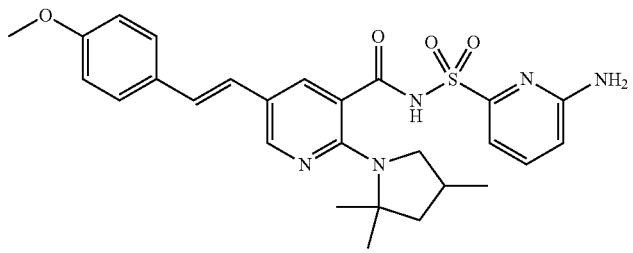 | 1726 |
| 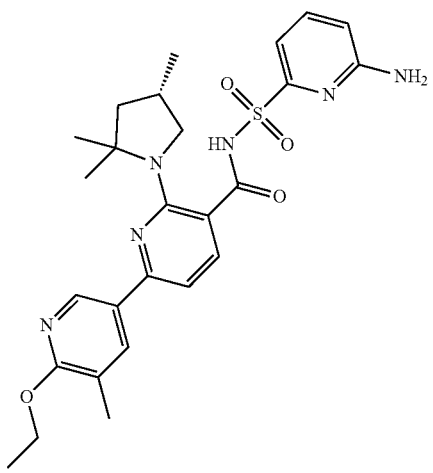 [SMILES: CCOc1ncc(-c2ccc(C(=O)NS(=O)(=O)c3cccc(N)n3)c(N3C[C@@H](C)CC3(C)C)n2)cc1C] | 1727 |
| 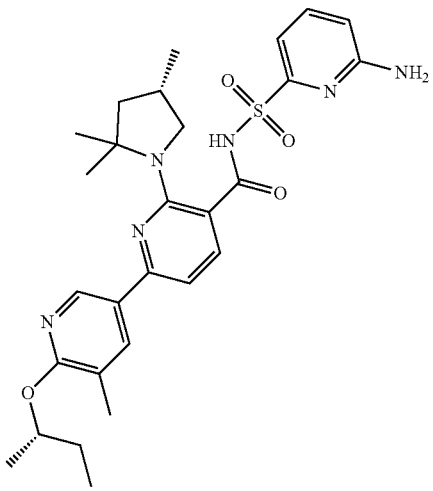 [SMILES: CC[C@H](C)Oc1ncc(-c2ccc(C(=O)NS(=O)(=O)c3cccc(N)n3)c(N3C[C@@H](C)CC3(C)C)n2)cc1C] | 1728 |

TABLE 1-continued
| | |
|---|---|
| 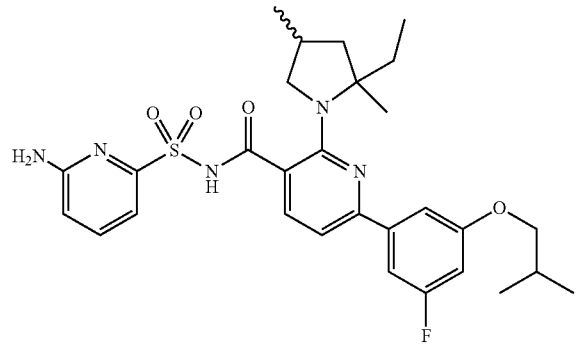 | 1729 |
| 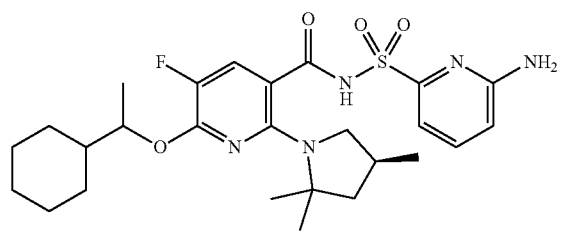 | 1730 |
| 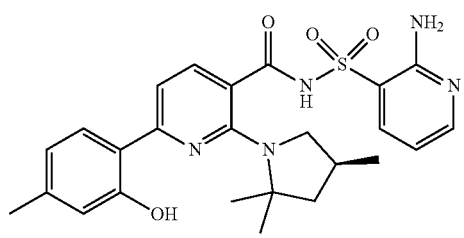 | 1731 |
| 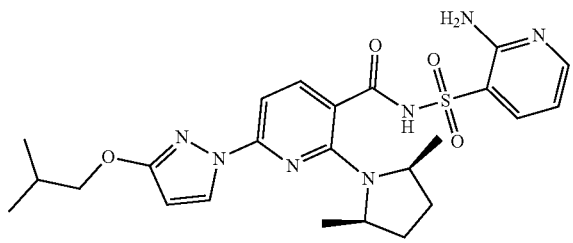 | 1732 |
| 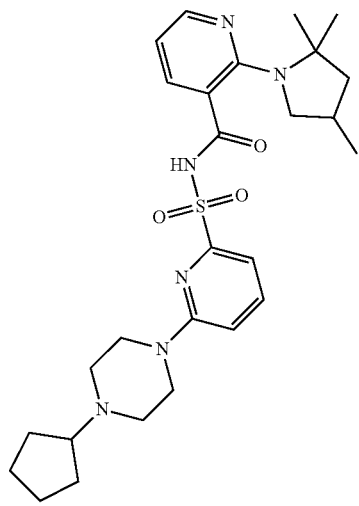 [SMILES: CC1CN(c2ncccc2C(=O)NS(=O)(=O)c2cccc(N3CCN(C4CCCC4)CC3)n2)C(C)(C)C1] | 1733 |

TABLE 1-continued
| | |
|---|---|
| 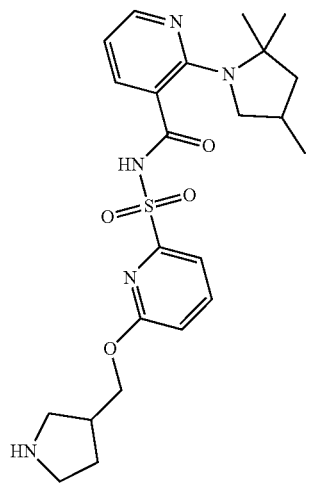 [SMILES: CC1CN(c2ncccc2C(=O)NS(=O)(=O)c2cccc(OCC3CCNC3)n2)C(C)(C)C1] | 1734 |
| 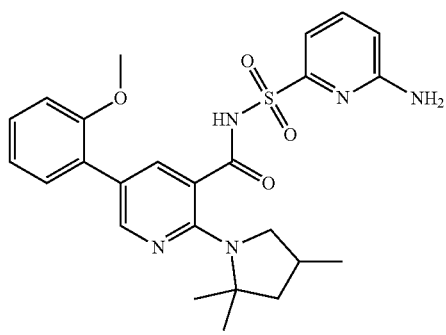 [SMILES: COc1ccccc1-c1cnc(N2CC(C)CC2(C)C)c(C(=O)NS(=O)(=O)c2cccc(N)n2)c1] | 1735 |
| 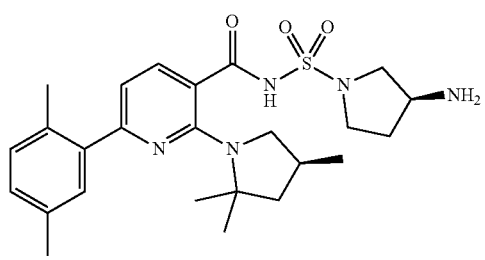 | 1736 |
| 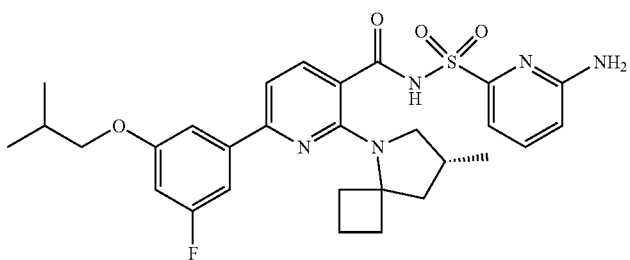 | 1737 |
| 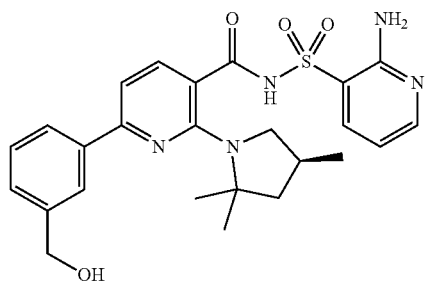 | 1738 |

TABLE 1-continued
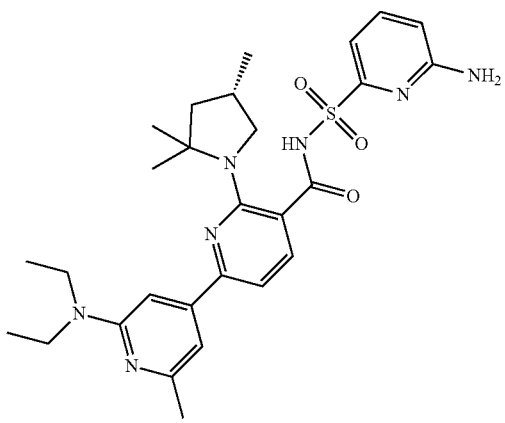 [SMILES: CCN(CC)c1cc(-c2ccc(C(=O)NS(=O)(=O)c3cccc(N)n3)c(N3C[C@@H](C)CC3(C)C)n2)cc(C)n1]
1739
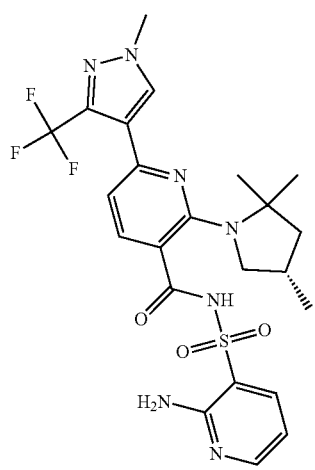 [SMILES: C[C@@H]1CN(c2nc(-c3cn(C)nc3C(F)(F)F)ccc2C(=O)NS(=O)(=O)c2cccnc2N)C(C)(C)C1]
1740
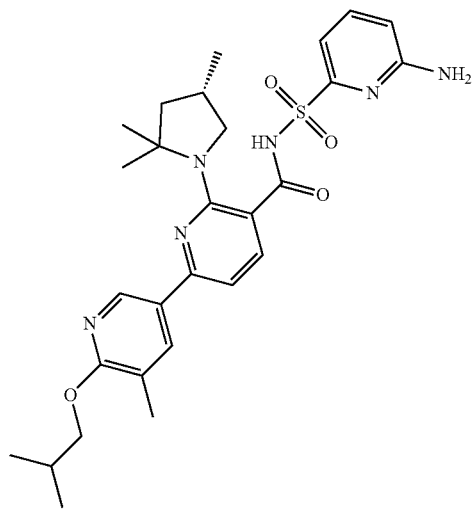 [SMILES: Cc1cc(-c2ccc(C(=O)NS(=O)(=O)c3cccc(N)n3)c(N3C[C@@H](C)CC3(C)C)n2)cnc1OCC(C)C]
1741
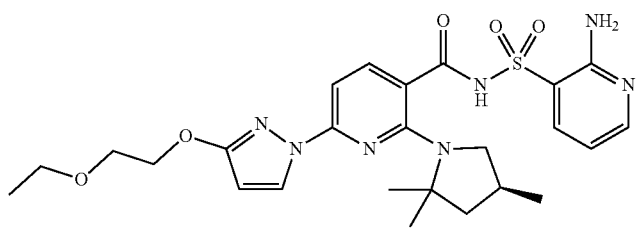
1742

TABLE 1-continued
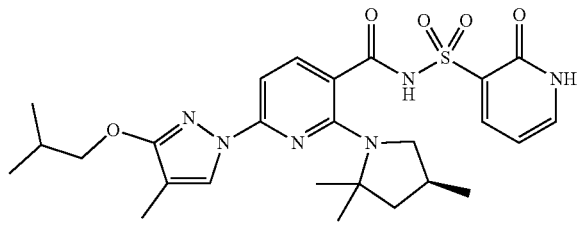
1743
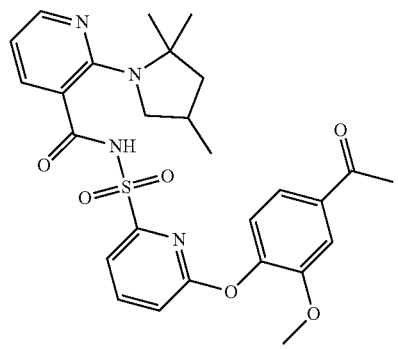 [SMILES: COc1cc(C(C)=O)ccc1Oc1cccc(S(=O)(=O)NC(=O)c2cccnc2N2CC(C)CC2(C)C)n1]
1744
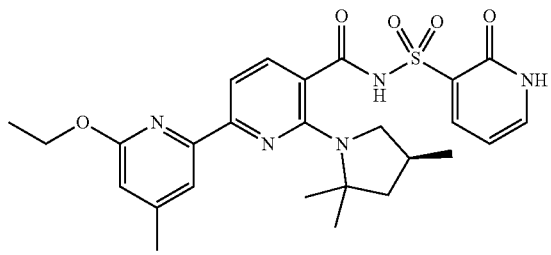
1745
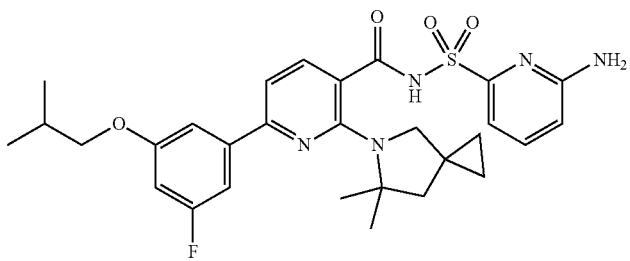
1746
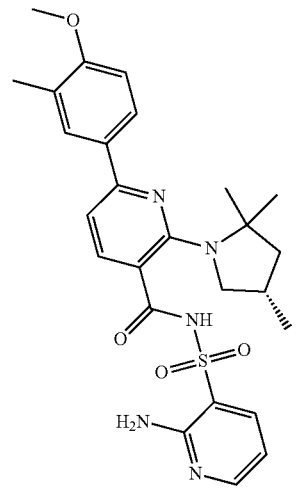
1747

TABLE 1-continued
| | |
|---|---|
| 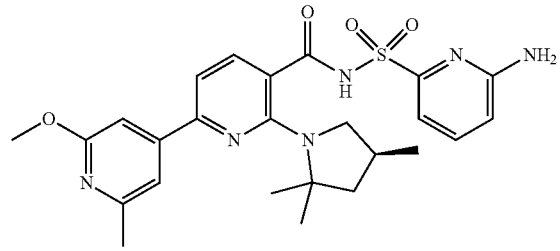 | 1748 |
| 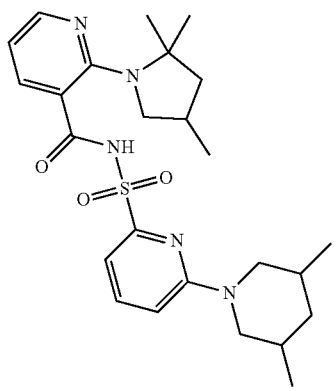 [SMILES: CC1CC(C)CN(c2cccc(S(=O)(=O)NC(=O)c3cccnc3N3CC(C)CC3(C)C)n2)C1] | 1749 |
| 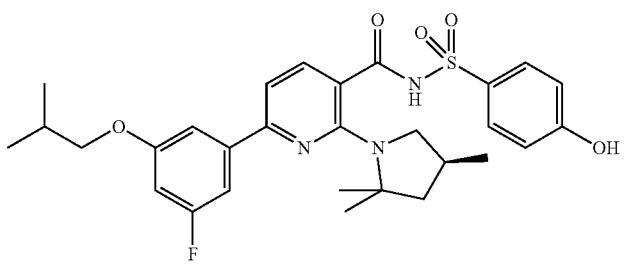 | 1750 |
| 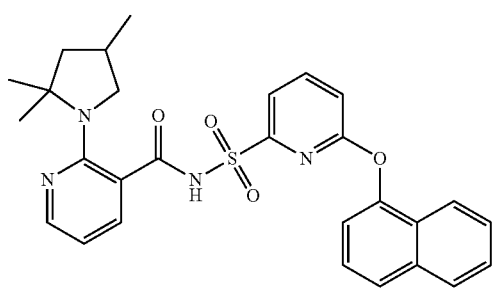 | 1751 |
| 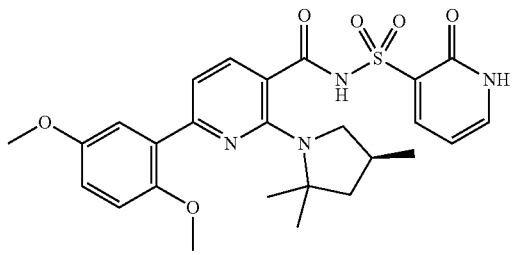 | 1752 |

TABLE 1-continued
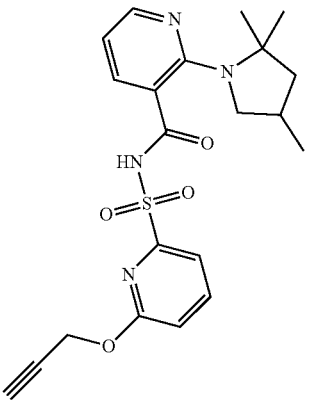 [SMILES: C#CCOc1cccc(S(=O)(=O)NC(=O)c2cccnc2N2CC(C)CC2(C)C)n1]
1753
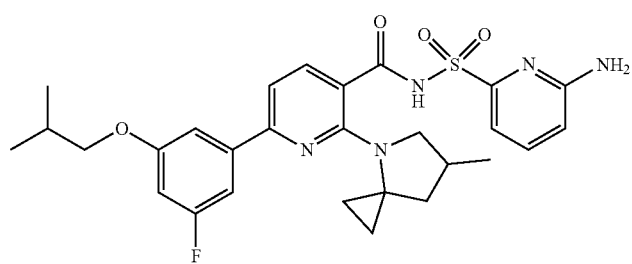
1754
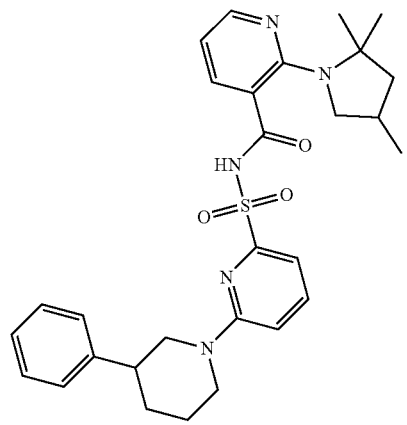 [SMILES: CC1CN(c2ncccc2C(=O)NS(=O)(=O)c2cccc(N3CCCC(c4ccccc4)C3)n2)C(C)(C)C1]
1755
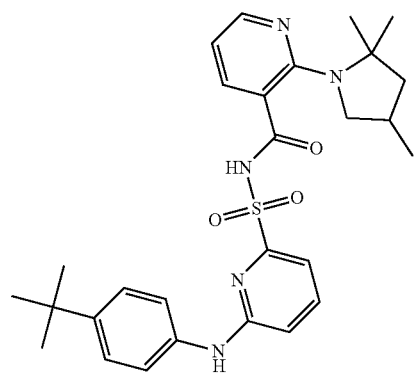
1756

TABLE 1-continued
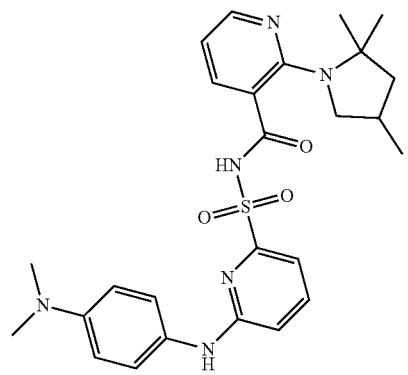
1757
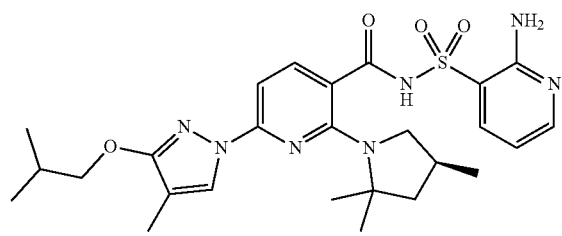
1758
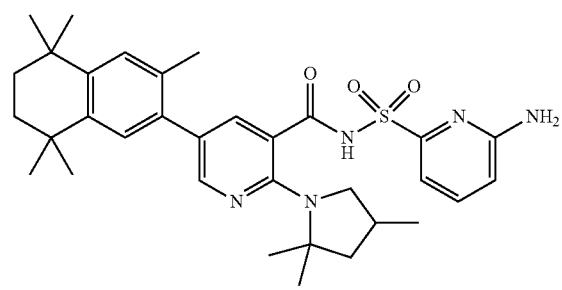
1759
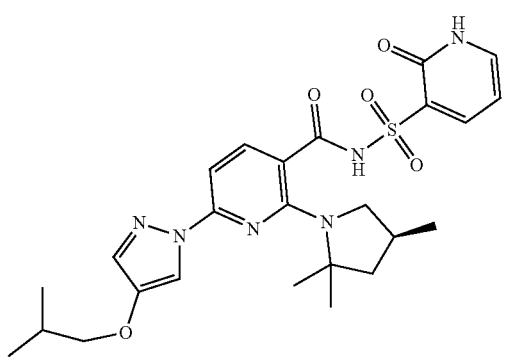
1760
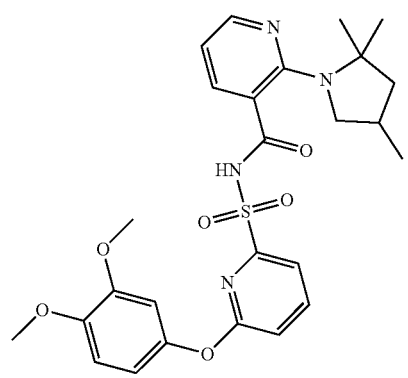
1761

TABLE 1-continued
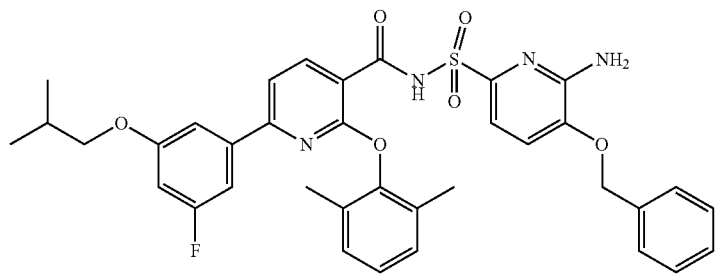
1762
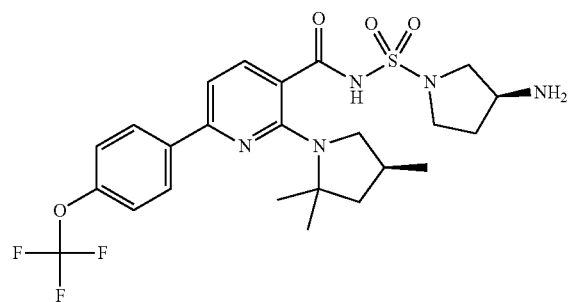
1763
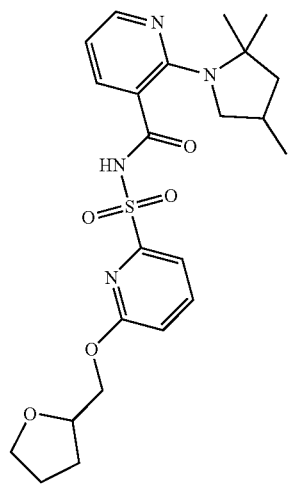 [SMILES: CC1CN(c2ncccc2C(=O)NS(=O)(=O)c2cccc(OCC3CCCO3)n2)C(C)(C)C1]
1764
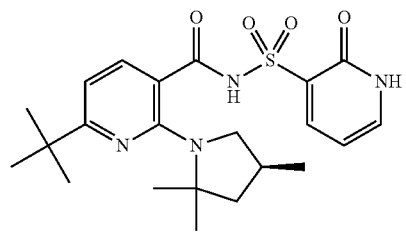
1765
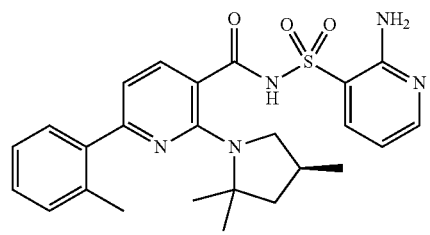
1766

TABLE 1-continued
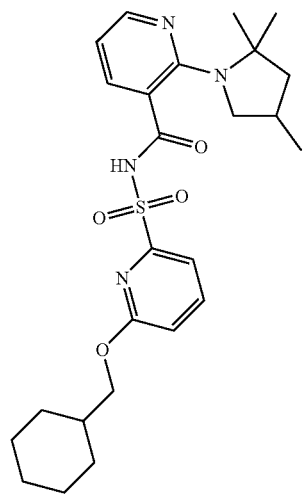 [SMILES: CC1CN(c2ncccc2C(=O)NS(=O)(=O)c2cccc(OCC3CCCCC3)n2)C(C)(C)C1]
1767
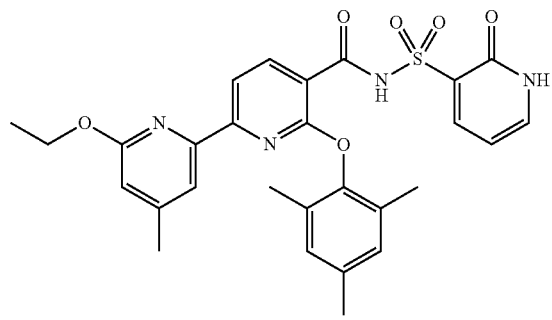
1768
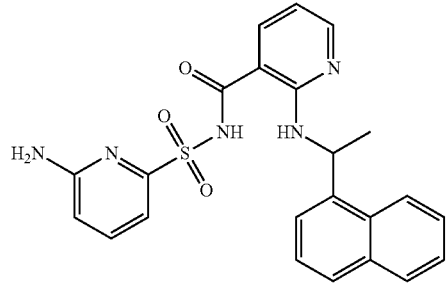 [SMILES: CC(Nc1ncccc1C(=O)NS(=O)(=O)c1cccc(N)n1)c1cccc2ccccc12]
1769
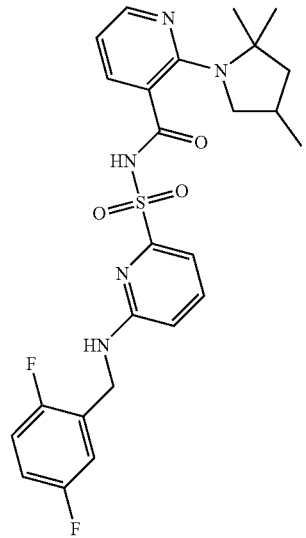 [SMILES: CC1CN(c2ncccc2C(=O)NS(=O)(=O)c2cccc(NCc3cc(F)ccc3F)n2)C(C)(C)C1]
1770

TABLE 1-continued
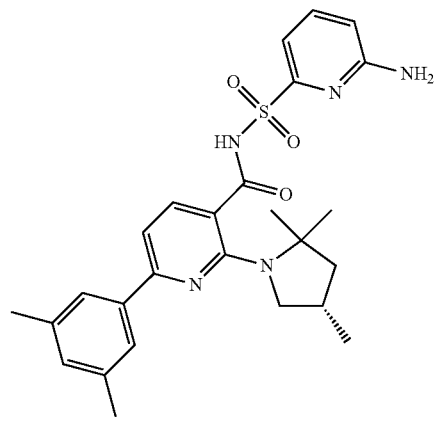 [SMILES: Cc1cc(C)cc(-c2ccc(C(=O)NS(=O)(=O)c3cccc(N)n3)c(N3C[C@@H](C)CC3(C)C)n2)c1]
1771
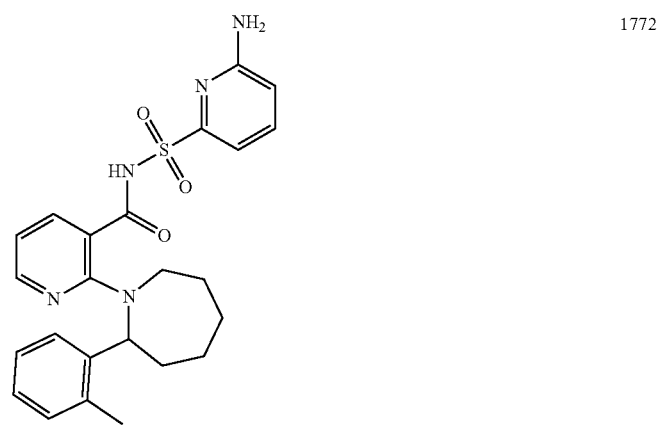
1772
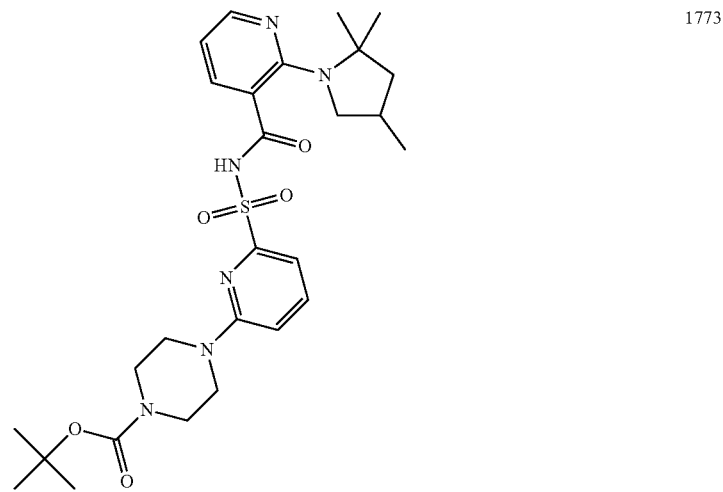
1773
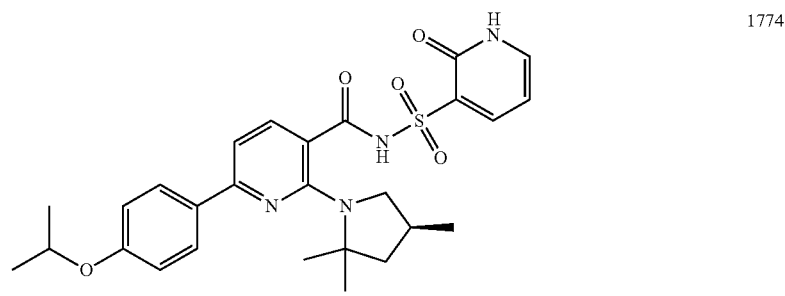
1774

| | |
|---|---|
| 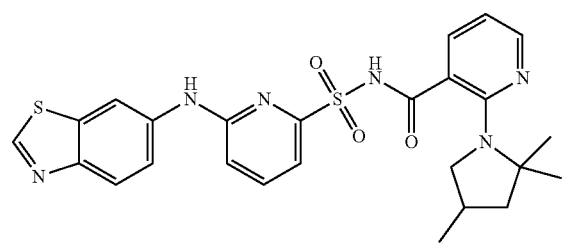 | 1775 |
| 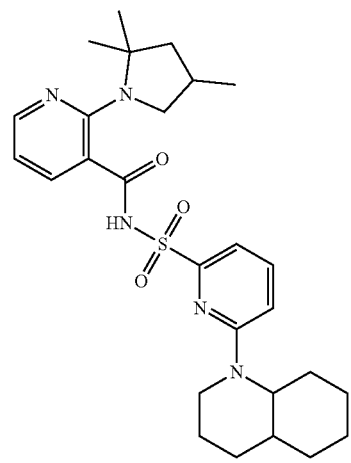 [SMILES: CC1CN(c2ncccc2C(=O)NS(=O)(=O)c2cccc(N3CCCC4CCCCC43)n2)C(C)(C)C1] | 1776 |
| 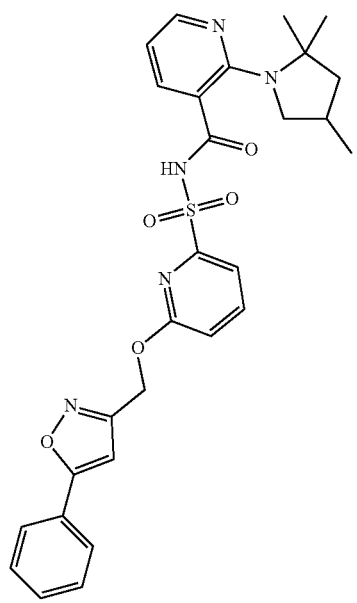 [SMILES: CC1CN(c2ncccc2C(=O)NS(=O)(=O)c2cccc(OCc3cc(-c4ccccc4)on3)n2)C(C)(C)C1] | 1777 |

TABLE 1-continued
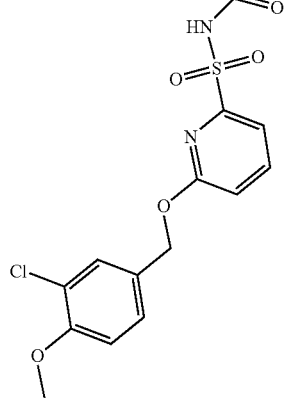 1778
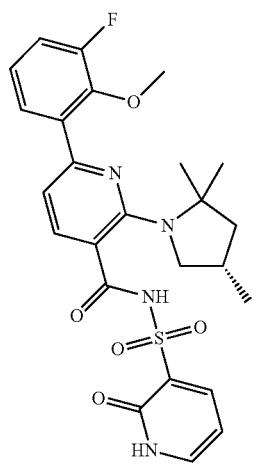 [SMILES: COc1c(F)cccc1-c1ccc(C(=O)NS(=O)(=O)c2ccc[nH]c2=O)c(N2C[C@@H](C)CC2(C)C)n1] 1779
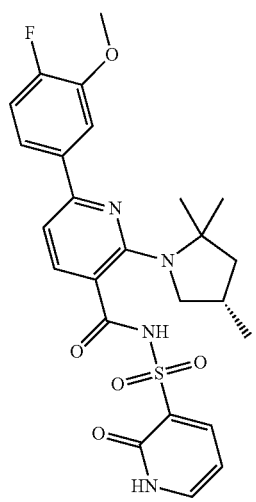 [SMILES: COc1cc(-c2ccc(C(=O)NS(=O)(=O)c3ccc[nH]c3=O)c(N3C[C@@H](C)CC3(C)C)n2)ccc1F] 1780

TABLE 1-continued
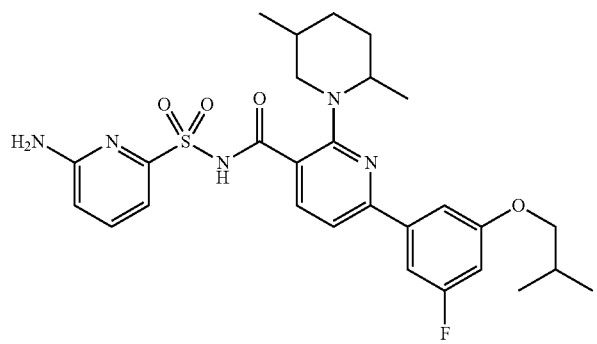
1781
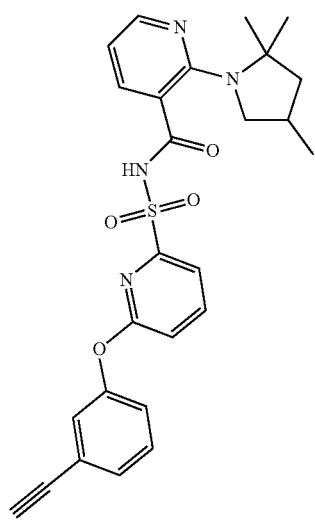 [SMILES: C#Cc1cccc(Oc2cccc(S(=O)(=O)NC(=O)c3cccnc3N3CC(C)CC3(C)C)n2)c1]
1782
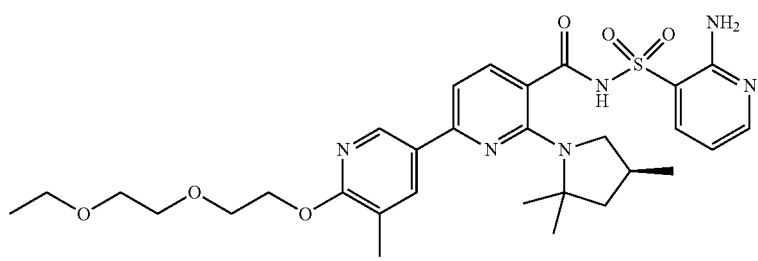
1783
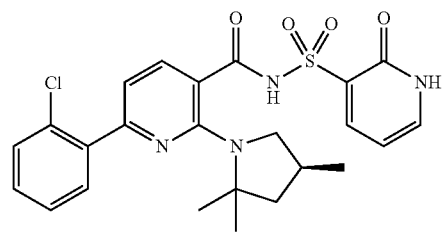
1784

TABLE 1-continued
| | |
|---|---|
| 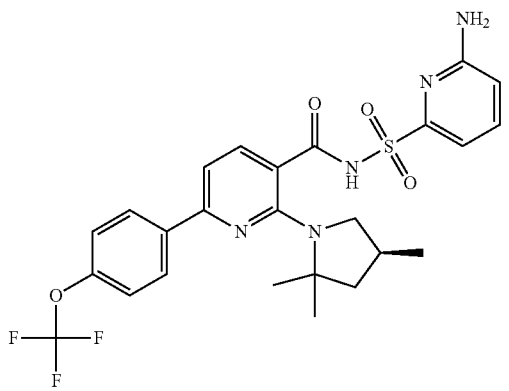 | 1785 |
| 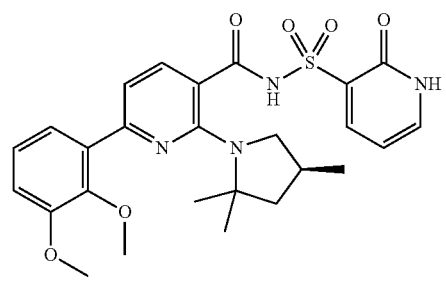 | 1786 |
| 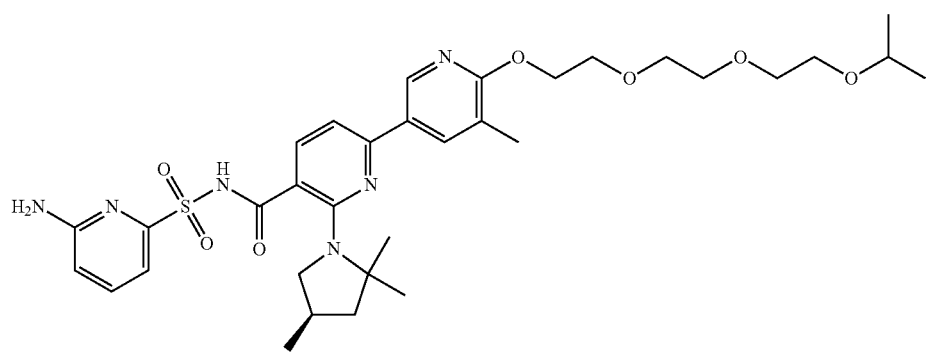 | 1787 |
| 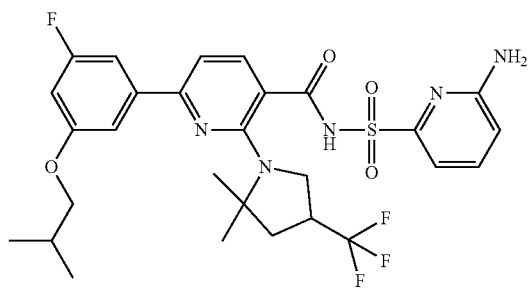 | 1788 |
| 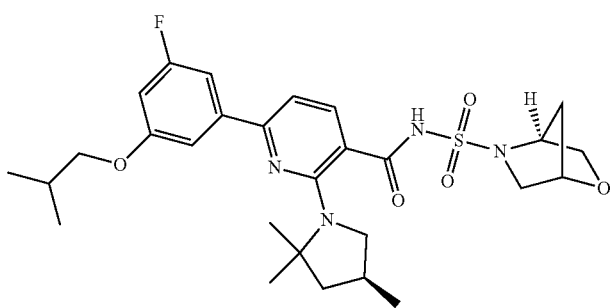 [SMILES: CC(C)COc1cc(F)cc(-c2ccc(C(=O)NS(=O)(=O)N3CC4C[C@H]3CO4)c(N3C[C@@H](C)CC3(C)C)n2)c1] | 1789 |

TABLE 1-continued
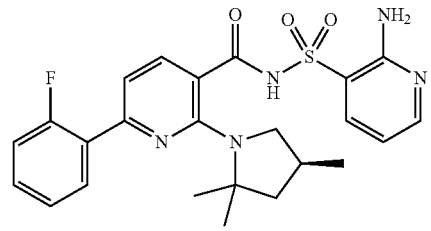 [SMILES: C[C@@H]1CN(c2nc(-c3ccccc3F)ccc2C(=O)NS(=O)(=O)c2cccnc2N)C(C)(C)C1]
1790
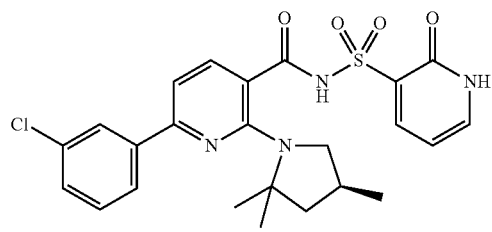 [SMILES: C[C@@H]1CN(c2nc(-c3cccc(Cl)c3)ccc2C(=O)NS(=O)(=O)c2ccc[nH]c2=O)C(C)(C)C1]
1791
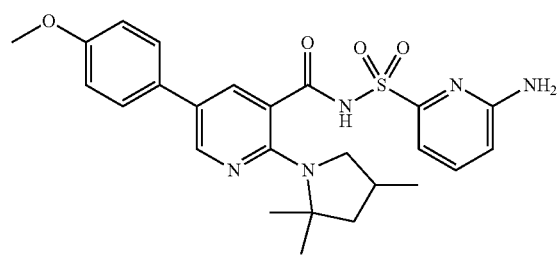 [SMILES: COc1ccc(-c2cnc(N3CC(C)CC3(C)C)c(C(=O)NS(=O)(=O)c3cccc(N)n3)c2)cc1]
1792
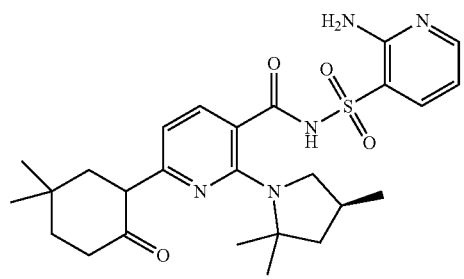 [SMILES: C[C@@H]1CN(c2nc(C3CC(C)(C)CCC3=O)ccc2C(=O)NS(=O)(=O)c2cccnc2N)C(C)(C)C1]
1793
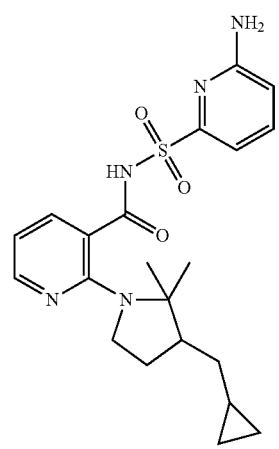 [SMILES: CC1(C)C(CC2CC2)CCN1c1ncccc1C(=O)NS(=O)(=O)c1cccc(N)n1]
1794

TABLE 1-continued
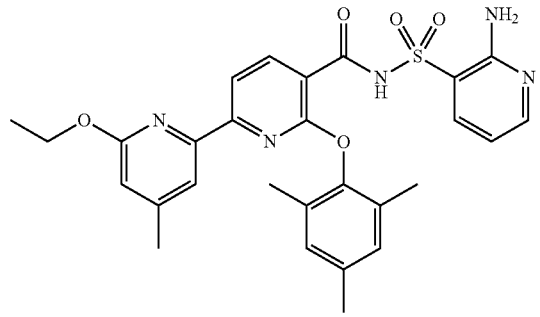 [SMILES: CCOc1cc(C)cc(-c2ccc(C(=O)NS(=O)(=O)c3cccnc3N)c(Oc3c(C)cc(C)cc3C)n2)n1]
1795
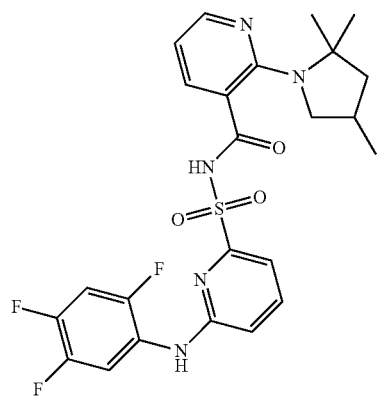 [SMILES: CC1CN(c2ncccc2C(=O)NS(=O)(=O)c2cccc(Nc3cc(F)c(F)cc3F)n2)C(C)(C)C1]
1796
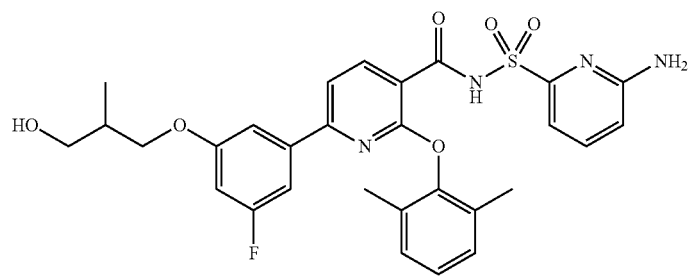 [SMILES: Cc1cccc(C)c1Oc1nc(-c2cc(F)cc(OCC(C)CO)c2)ccc1C(=O)NS(=O)(=O)c1cccc(N)n1]
1797
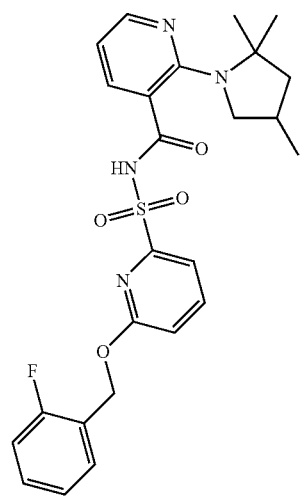 [SMILES: CC1CN(c2ncccc2C(=O)NS(=O)(=O)c2cccc(OCc3ccccc3F)n2)C(C)(C)C1]
1798

TABLE 1-continued
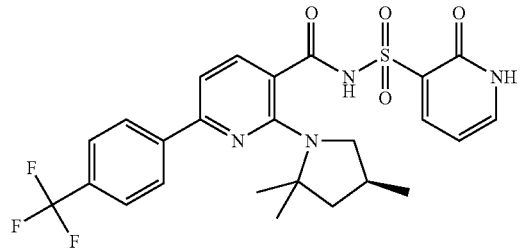 [SMILES: C[C@@H]1CN(c2nc(-c3ccc(C(F)(F)F)cc3)ccc2C(=O)NS(=O)(=O)c2ccc[nH]c2=O)C(C)(C)C1]
1799
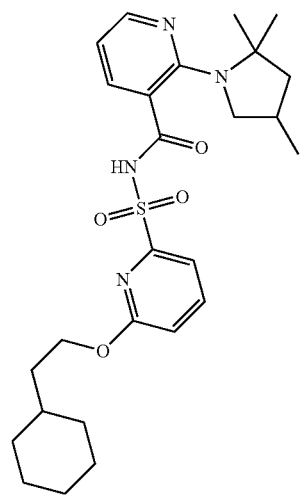 [SMILES: CC1CN(c2ncccc2C(=O)NS(=O)(=O)c2cccc(OCCC3CCCCC3)n2)C(C)(C)C1]
1800
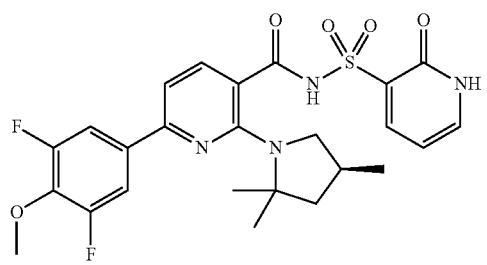 [SMILES: COc1c(F)cc(-c2ccc(C(=O)NS(=O)(=O)c3ccc[nH]c3=O)c(N3C[C@@H](C)CC3(C)C)n2)cc1F]
1801
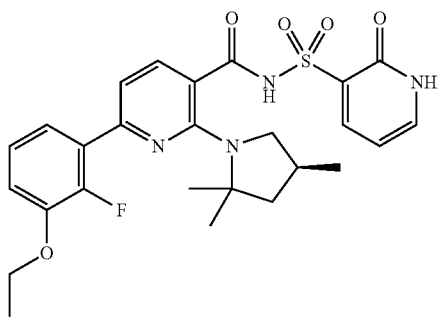 [SMILES: CCOc1cccc(-c2ccc(C(=O)NS(=O)(=O)c3ccc[nH]c3=O)c(N3C[C@@H](C)CC3(C)C)n2)c1F]
1802
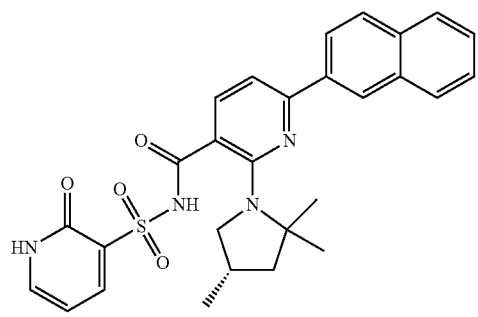 [SMILES: C[C@@H]1CN(c2nc(-c3ccc4ccccc4c3)ccc2C(=O)NS(=O)(=O)c2ccc[nH]c2=O)C(C)(C)C1]
1803

TABLE 1-continued
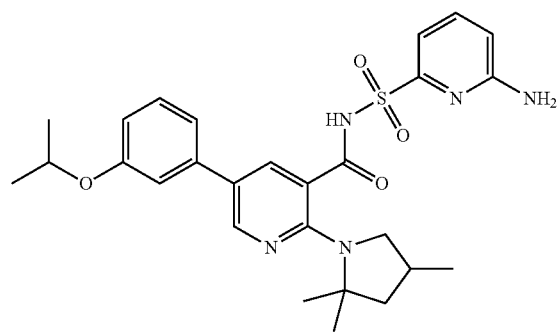 [SMILES: CC1CN(c2ncc(-c3cccc(OC(C)C)c3)cc2C(=O)NS(=O)(=O)c2cccc(N)n2)C(C)(C)C1] 1804
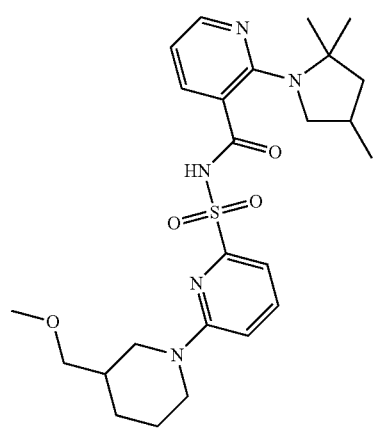 1805
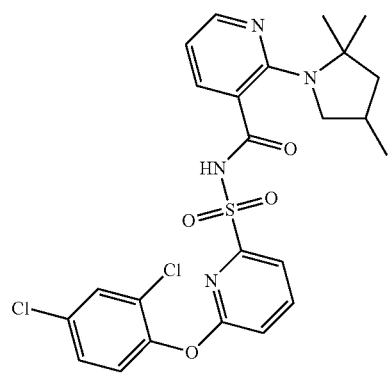 [SMILES: CC1CN(c2ncccc2C(=O)NS(=O)(=O)c2cccc(Oc3ccc(Cl)cc3Cl)n2)C(C)(C)C1] 1806
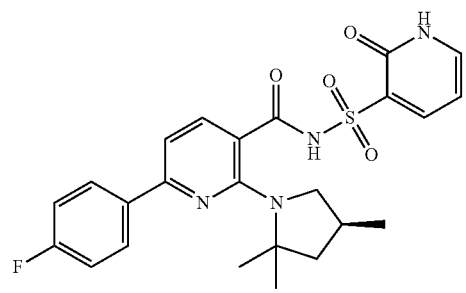 [SMILES: C[C@@H]1CN(c2nc(-c3ccc(F)cc3)ccc2C(=O)NS(=O)(=O)c2ccc[nH]c2=O)C(C)(C)C1] 1807

TABLE 1-continued
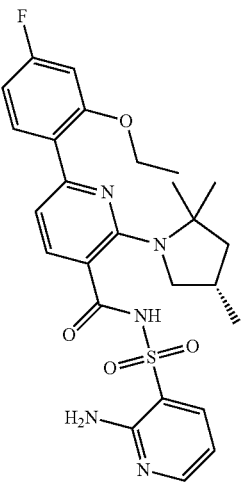 [SMILES: CCOc1cc(F)ccc1-c1ccc(C(=O)NS(=O)(=O)c2cccnc2N)c(N2C[C@@H](C)CC2(C)C)n1]
1808
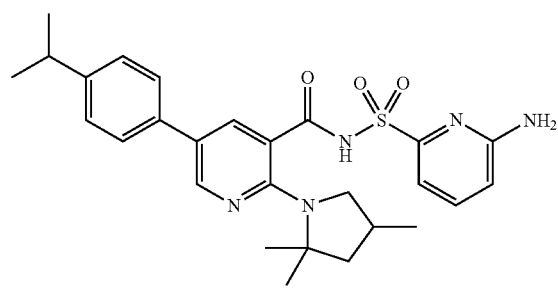 [SMILES: CC1CN(c2ncc(-c3ccc(C(C)C)cc3)cc2C(=O)NS(=O)(=O)c2cccc(N)n2)C(C)(C)C1]
1809
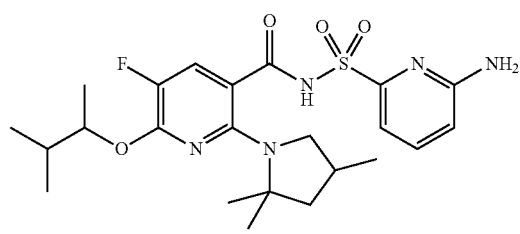 [SMILES: CC1CN(c2nc(OC(C)C(C)C)c(F)cc2C(=O)NS(=O)(=O)c2cccc(N)n2)C(C)(C)C1]
1810
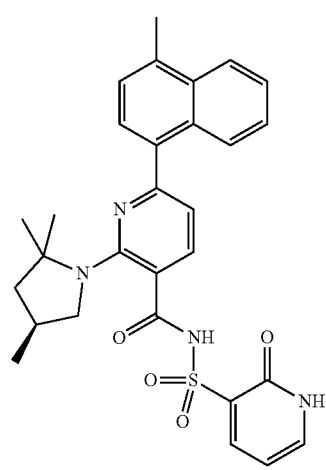 [SMILES: Cc1ccc(-c2ccc(C(=O)NS(=O)(=O)c3ccc[nH]c3=O)c(N3C[C@@H](C)CC3(C)C)n2)c2ccccc12]
1811

TABLE 1-continued
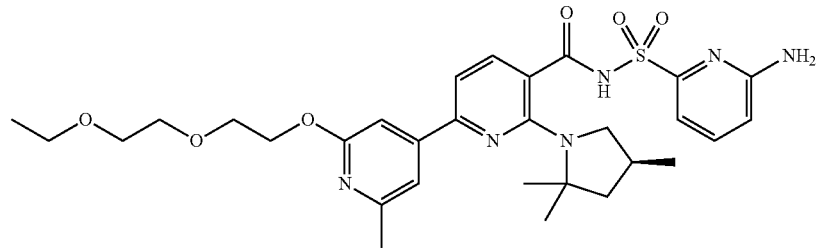 [SMILES: CCOCCOCCOc1cc(-c2ccc(C(=O)NS(=O)(=O)c3cccc(N)n3)c(N3C[C@@H](C)CC3(C)C)n2)cc(C)n1]
1812
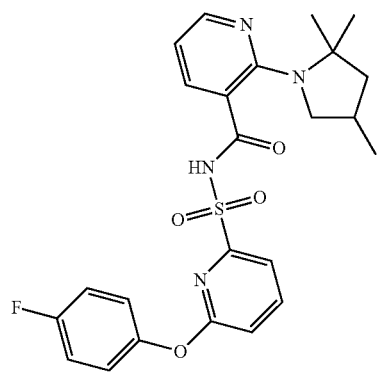 [SMILES: CC1CN(c2ncccc2C(=O)NS(=O)(=O)c2cccc(Oc3ccc(F)cc3)n2)C(C)(C)C1]
1813
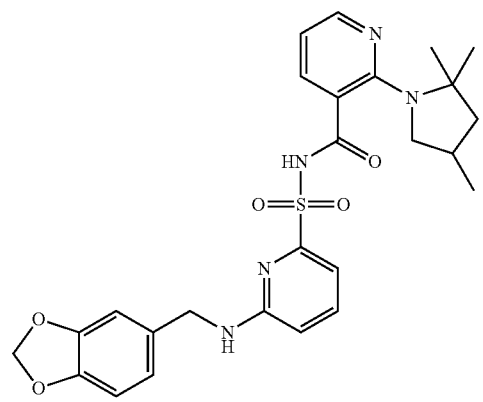 [SMILES: CC1CN(c2ncccc2C(=O)NS(=O)(=O)c2cccc(NCc3ccc4c(c3)OCO4)n2)C(C)(C)C1]
1814
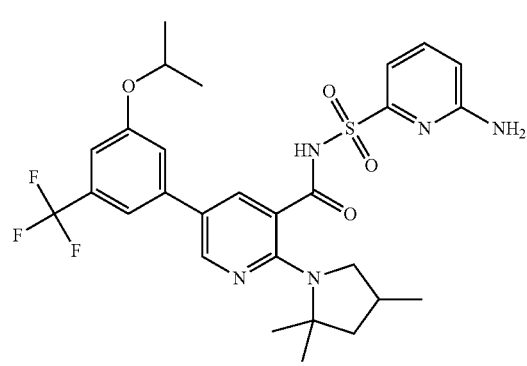 [SMILES: CC1CN(c2ncc(-c3cc(OC(C)C)cc(C(F)(F)F)c3)cc2C(=O)NS(=O)(=O)c2cccc(N)n2)C(C)(C)C1]
1815

TABLE 1-continued
1816
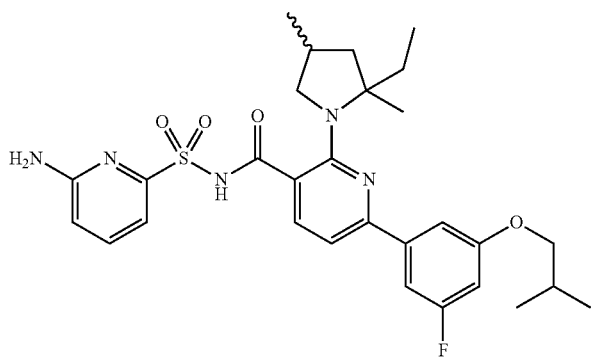 [SMILES: CCC1(C)CC(C)CN1c1nc(-c2cc(F)cc(OCC(C)C)c2)ccc1C(=O)NS(=O)(=O)c1cccc(N)n1]
1817
1818
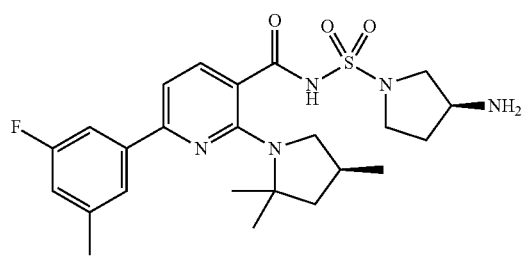 [SMILES: Cc1cc(F)cc(-c2ccc(C(=O)NS(=O)(=O)N3CC[C@H](N)C3)c(N3C[C@@H](C)CC3(C)C)n2)c1]
1819

TABLE 1-continued
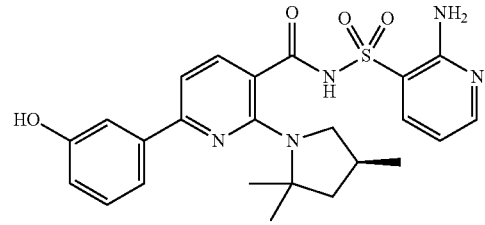 [SMILES: C[C@@H]1CN(c2nc(-c3cccc(O)c3)ccc2C(=O)NS(=O)(=O)c2cccnc2N)C(C)(C)C1]
1820
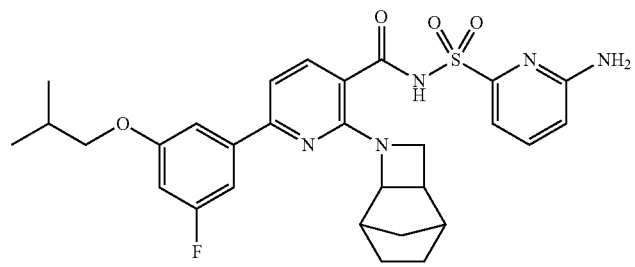 [SMILES: CC(C)COc1cc(F)cc(-c2ccc(C(=O)NS(=O)(=O)c3cccc(N)n3)c(N3CC4C5CCC(C5)C43)n2)c1]
1821
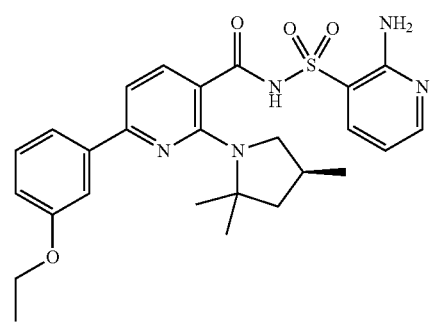 [SMILES: CCOc1cccc(-c2ccc(C(=O)NS(=O)(=O)c3cccnc3N)c(N3C[C@@H](C)CC3(C)C)n2)c1]
1822
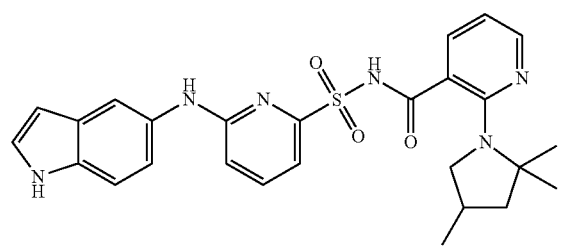 [SMILES: CC1CN(c2ncccc2C(=O)NS(=O)(=O)c2cccc(Nc3ccc4[nH]ccc4c3)n2)C(C)(C)C1]
1823
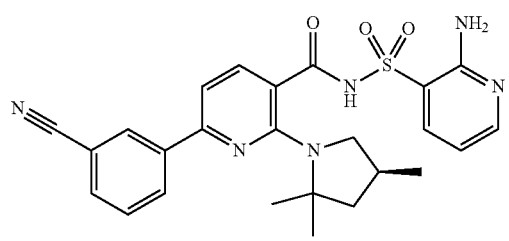 [SMILES: C[C@@H]1CN(c2nc(-c3cccc(C#N)c3)ccc2C(=O)NS(=O)(=O)c2cccnc2N)C(C)(C)C1]
1824

TABLE 1-continued
| | |
|---|---|
| 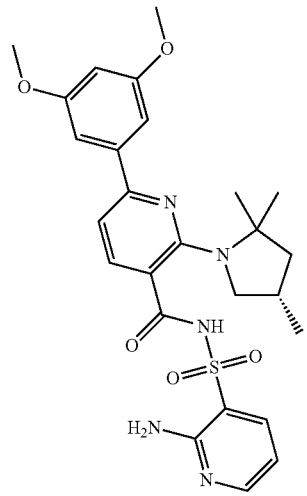 | 1825 |
| 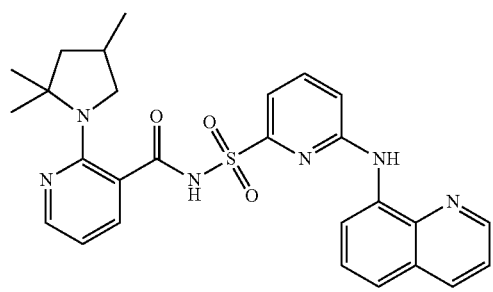 [SMILES: CC1CN(c2ncccc2C(=O)NS(=O)(=O)c2cccc(Nc3cccc4cccnc34)n2)C(C)(C)C1] | 1826 |
| 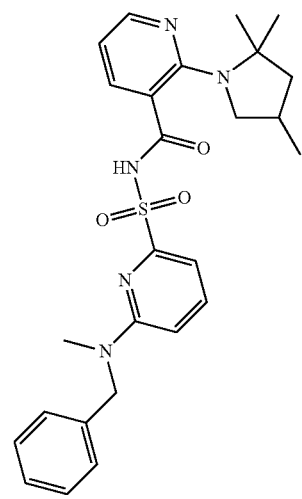 [SMILES: CC1CN(c2ncccc2C(=O)NS(=O)(=O)c2cccc(N(C)Cc3ccccc3)n2)C(C)(C)C1] | 1827 |

TABLE 1-continued
| | |
|---|---|
| 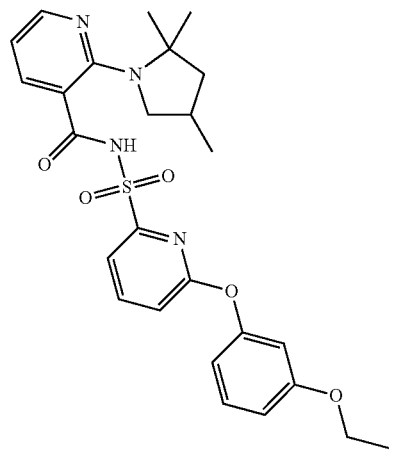 [SMILES: CCOc1cccc(Oc2cccc(S(=O)(=O)NC(=O)c3cccnc3N3CC(C)CC3(C)C)n2)c1] | 1828 |
| 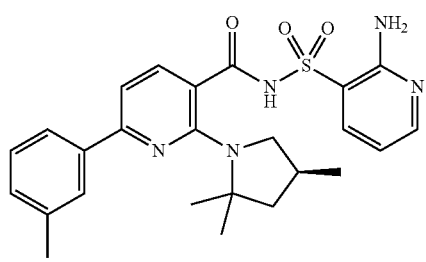 [SMILES: Cc1cccc(-c2ccc(C(=O)NS(=O)(=O)c3cccnc3N)c(N3C[C@@H](C)CC3(C)C)n2)c1] | 1829 |
| 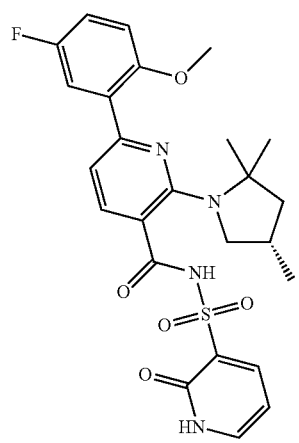 [SMILES: COc1ccc(F)cc1-c1ccc(C(=O)NS(=O)(=O)c2ccc[nH]c2=O)c(N2C[C@@H](C)CC2(C)C)n1] | 1830 |
| 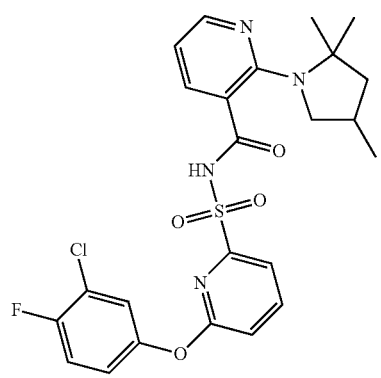 [SMILES: CC1CN(c2ncccc2C(=O)NS(=O)(=O)c2cccc(Oc3ccc(F)c(Cl)c3)n2)C(C)(C)C1] | 1831 |

TABLE 1-continued
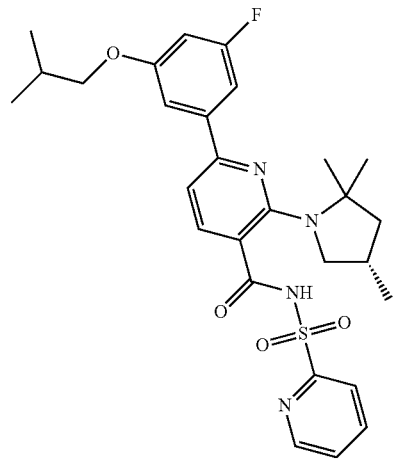 [SMILES: CC(C)COc1cc(F)cc(-c2ccc(C(=O)NS(=O)(=O)c3ccccn3)c(N3C[C@@H](C)CC3(C)C)n2)c1]
1832
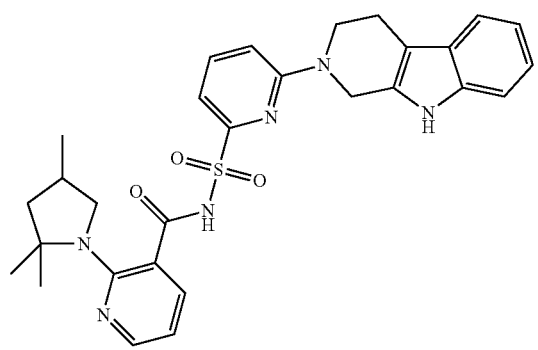 [SMILES: CC1CN(c2ncccc2C(=O)NS(=O)(=O)c2cccc(N3CCc4c([nH]c5ccccc45)C3)n2)C(C)(C)C1]
1833
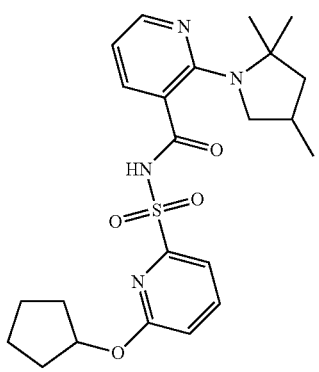 [SMILES: CC1CN(c2ncccc2C(=O)NS(=O)(=O)c2cccc(OC3CCCC3)n2)C(C)(C)C1]
1834
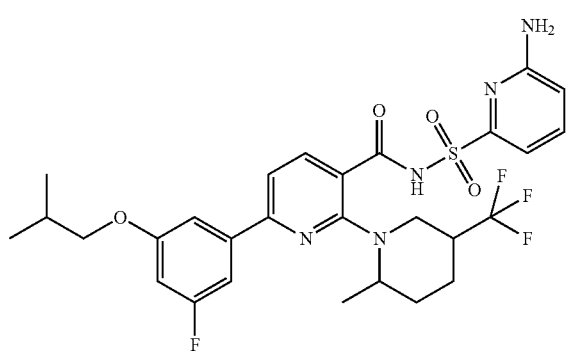 [SMILES: CC(C)COc1cc(F)cc(-c2ccc(C(=O)NS(=O)(=O)c3cccc(N)n3)c(N3CC(C(F)(F)F)CCC3C)n2)c1]
1835

TABLE 1-continued
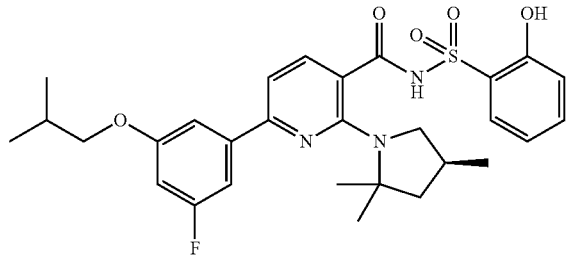 [SMILES: CC(C)COc1cc(F)cc(-c2ccc(C(=O)NS(=O)(=O)c3ccccc3O)c(N3C[C@@H](C)CC3(C)C)n2)c1]
1836
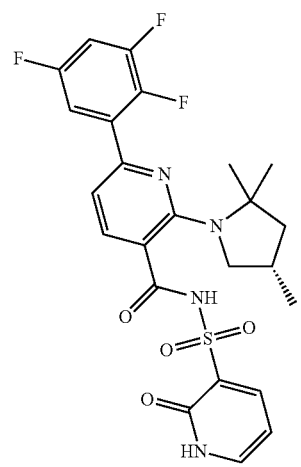 [SMILES: C[C@@H]1CN(c2nc(-c3cc(F)cc(F)c3F)ccc2C(=O)NS(=O)(=O)c2ccc[nH]c2=O)C(C)(C)C1]
1837
1838
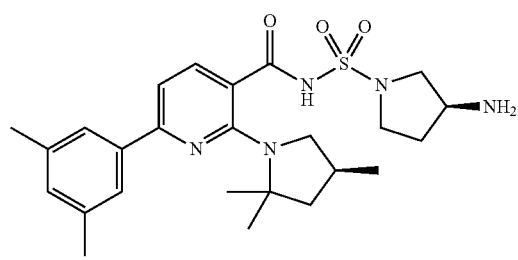 [SMILES: Cc1cc(C)cc(-c2ccc(C(=O)NS(=O)(=O)N3CC[C@H](N)C3)c(N3C[C@@H](C)CC3(C)C)n2)c1]
1839

TABLE 1-continued
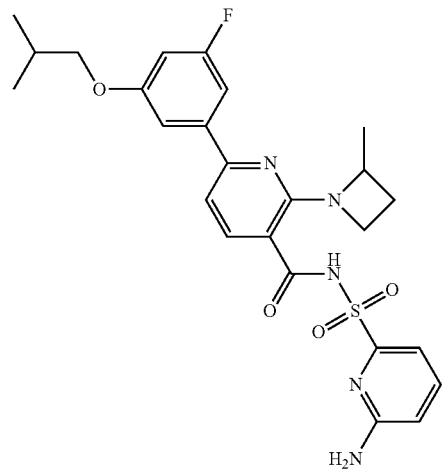 [SMILES: CC(C)COc1cc(F)cc(-c2ccc(C(=O)NS(=O)(=O)c3cccc(N)n3)c(N3CCC3C)n2)c1]
1840
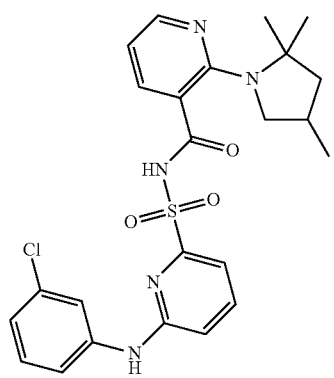 [SMILES: CC1CN(c2ncccc2C(=O)NS(=O)(=O)c2cccc(Nc3cccc(Cl)c3)n2)C(C)(C)C1]
1841
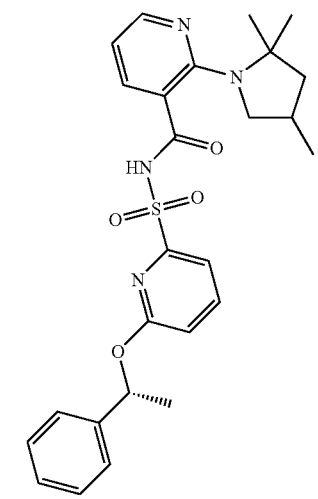 [SMILES: CC1CN(c2ncccc2C(=O)NS(=O)(=O)c2cccc(O[C@H](C)c3ccccc3)n2)C(C)(C)C1]
1842
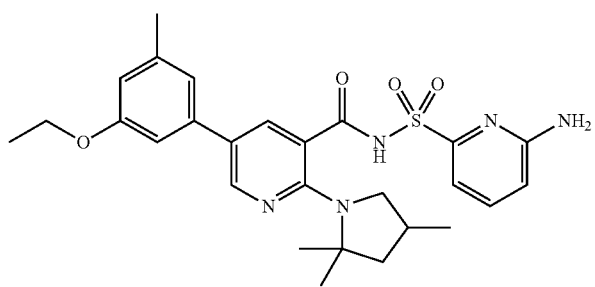 [SMILES: CCOc1cc(C)cc(-c2cnc(N3CC(C)CC3(C)C)c(C(=O)NS(=O)(=O)c3cccc(N)n3)c2)c1]
1843

TABLE 1-continued
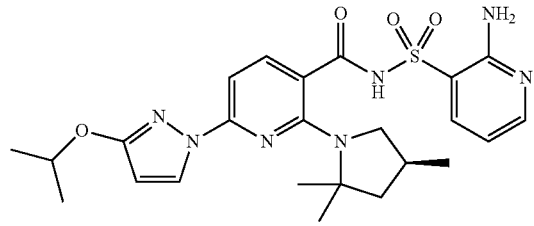 [SMILES: CC(C)Oc1ccn(-c2ccc(C(=O)NS(=O)(=O)c3cccnc3N)c(N3C[C@@H](C)CC3(C)C)n2)n1]
1844
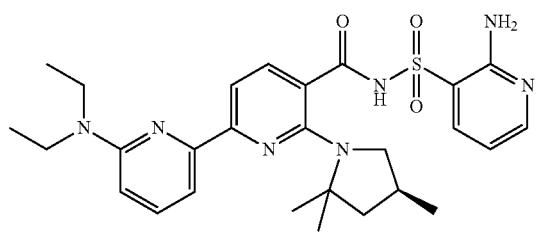 [SMILES: CCN(CC)c1cccc(-c2ccc(C(=O)NS(=O)(=O)c3cccnc3N)c(N3C[C@@H](C)CC3(C)C)n2)n1]
1845
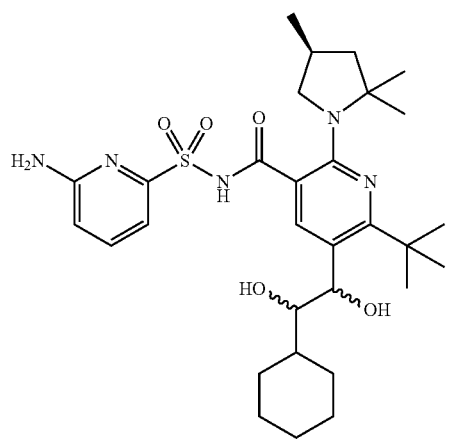 [SMILES: C[C@@H]1CN(c2nc(C(C)(C)C)c(C(O)C(O)C3CCCCC3)cc2C(=O)NS(=O)(=O)c2cccc(N)n2)C(C)(C)C1]
1846
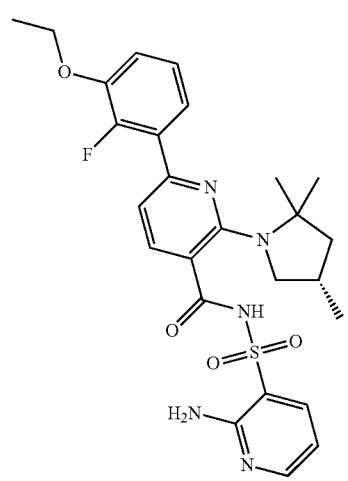 [SMILES: CCOc1cccc(-c2ccc(C(=O)NS(=O)(=O)c3cccnc3N)c(N3C[C@@H](C)CC3(C)C)n2)c1F]
1847

TABLE 1-continued
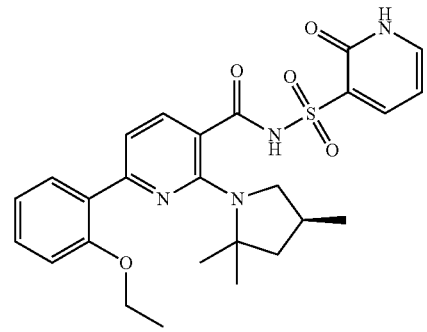 [SMILES: CCOc1ccccc1-c1ccc(C(=O)NS(=O)(=O)c2ccc[nH]c2=O)c(N2C[C@@H](C)CC2(C)C)n1]
1848
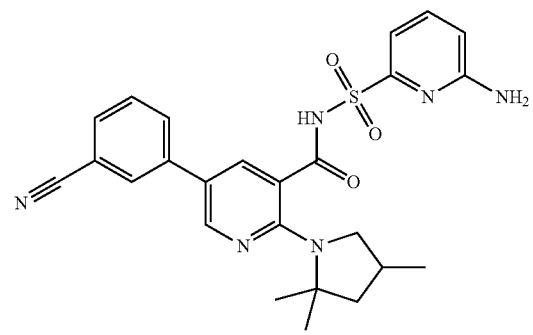 [SMILES: CC1CN(c2ncc(-c3cccc(C#N)c3)cc2C(=O)NS(=O)(=O)c2cccc(N)n2)C(C)(C)C1]
1849
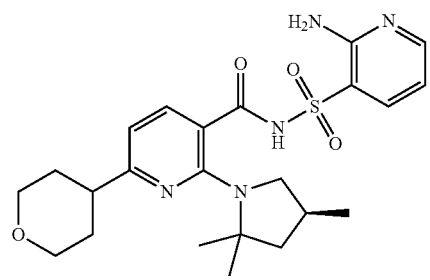 [SMILES: C[C@@H]1CN(c2nc(C3CCOCC3)ccc2C(=O)NS(=O)(=O)c2cccnc2N)C(C)(C)C1]
1850
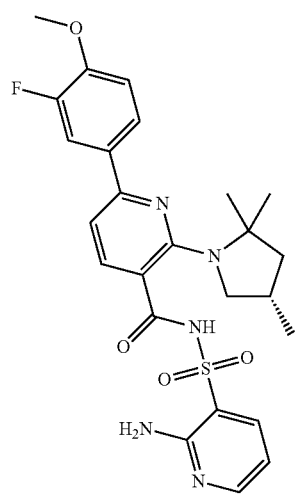 [SMILES: COc1ccc(-c2ccc(C(=O)NS(=O)(=O)c3cccnc3N)c(N3C[C@@H](C)CC3(C)C)n2)cc1F]
1851

TABLE 1-continued
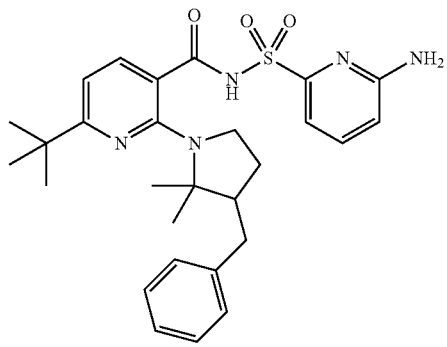 [SMILES: CC(C)(C)c1ccc(C(=O)NS(=O)(=O)c2cccc(N)n2)c(N2CCC(Cc3ccccc3)C2(C)C)n1]
1852
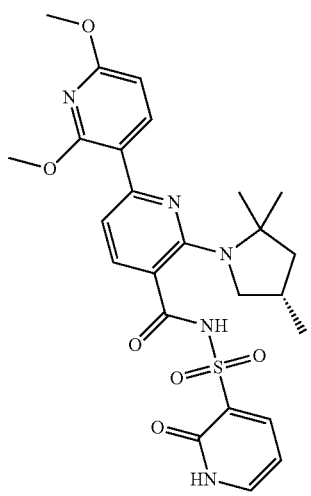
1853
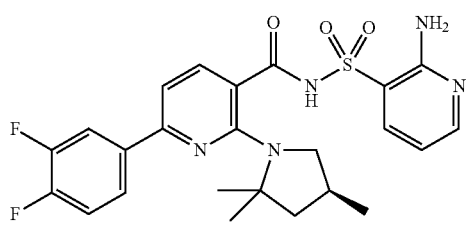 [SMILES: C[C@@H]1CN(c2nc(-c3ccc(F)c(F)c3)ccc2C(=O)NS(=O)(=O)c2cccnc2N)C(C)(C)C1]
1854
1855
1856

TABLE 1-continued
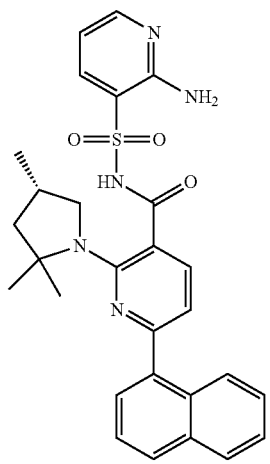 [SMILES: C[C@@H]1CN(c2nc(-c3cccc4ccccc34)ccc2C(=O)NS(=O)(=O)c2cccnc2N)C(C)(C)C1]
1857
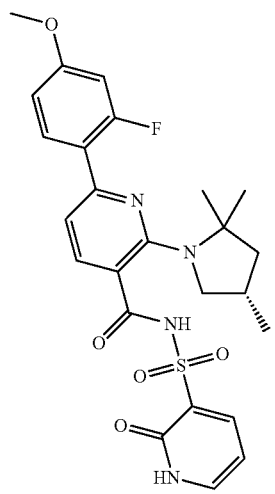
1858
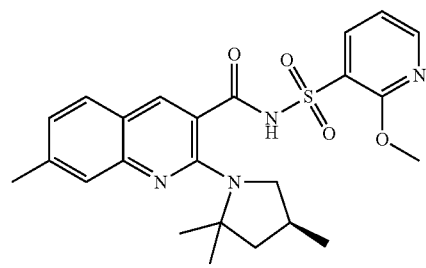
1859

US 12,168,009 B2
TABLE 1-continued
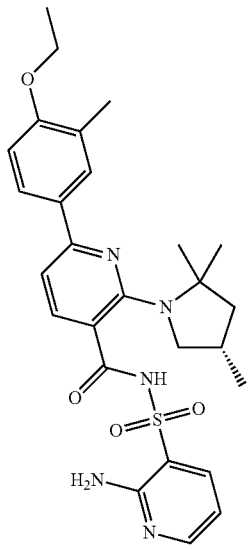 [SMILES: CCOc1ccc(-c2ccc(C(=O)NS(=O)(=O)c3cccnc3N)c(N3C[C@@H](C)CC3(C)C)n2)cc1C]
1860
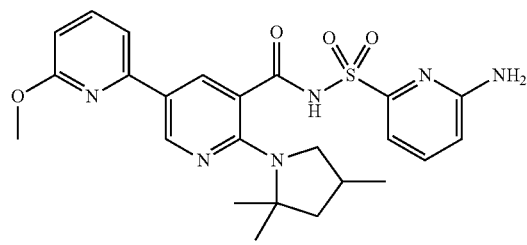 [SMILES: COc1cccc(-c2cnc(N3CC(C)CC3(C)C)c(C(=O)NS(=O)(=O)c3cccc(N)n3)c2)n1]
1861
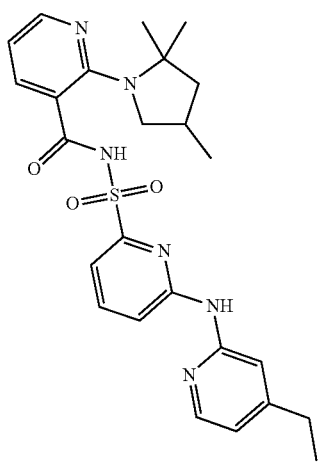 [SMILES: CCc1ccnc(Nc2cccc(S(=O)(=O)NC(=O)c3cccnc3N3CC(C)CC3(C)C)n2)c1]
1862
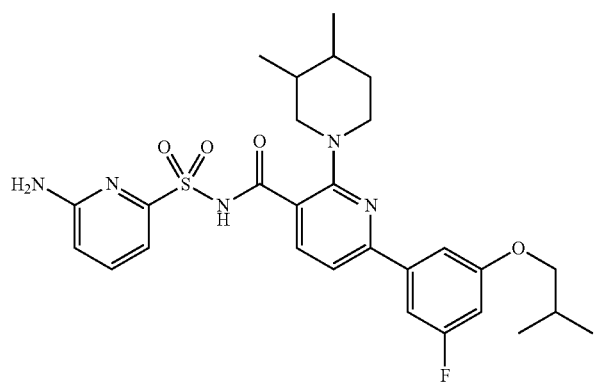
1863

TABLE 1-continued
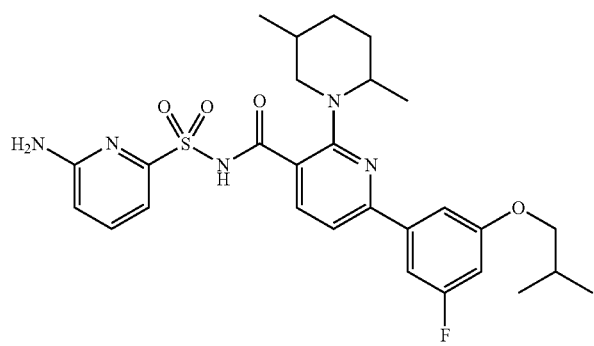 [SMILES: CC(C)COc1cc(F)cc(-c2ccc(C(=O)NS(=O)(=O)c3cccc(N)n3)c(N3CC(C)CCC3C)n2)c1]
1864
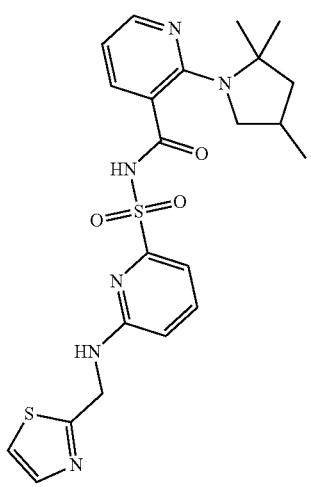 [SMILES: CC1CN(c2ncccc2C(=O)NS(=O)(=O)c2cccc(NCc3nccs3)n2)C(C)(C)C1]
1865
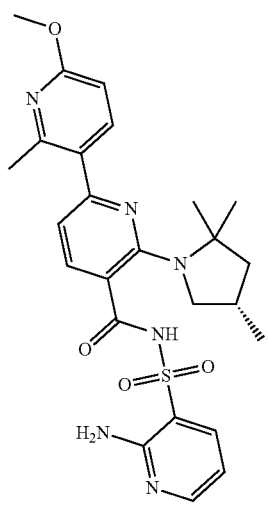
1866
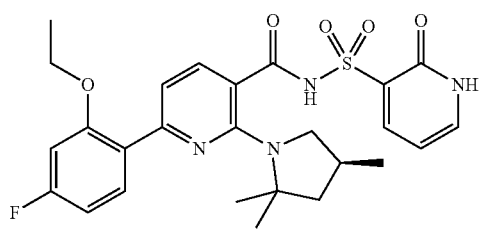 [SMILES: CCOc1cc(F)ccc1-c1ccc(C(=O)NS(=O)(=O)c2ccc[nH]c2=O)c(N2C[C@@H](C)CC2(C)C)n1]
1867

TABLE 1-continued
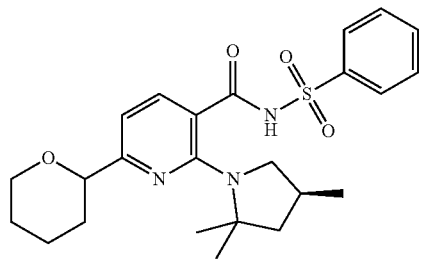 [SMILES: C[C@@H]1CN(c2nc(C3CCCCO3)ccc2C(=O)NS(=O)(=O)c2ccccc2)C(C)(C)C1]
1868
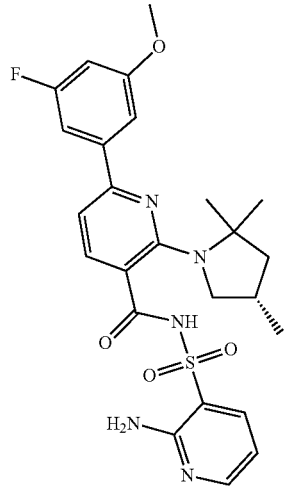 [SMILES: COc1cc(F)cc(-c2ccc(C(=O)NS(=O)(=O)c3cccnc3N)c(N3C[C@@H](C)CC3(C)C)n2)c1]
1869
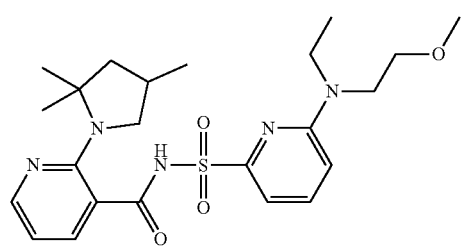 [SMILES: CCN(CCOC)c1cccc(S(=O)(=O)NC(=O)c2cccnc2N2CC(C)CC2(C)C)n1]
1870
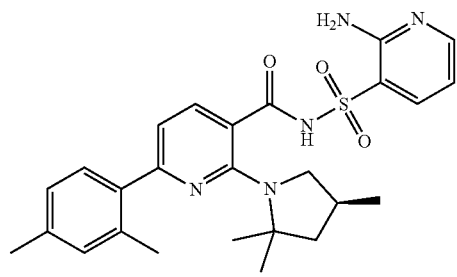 [SMILES: Cc1ccc(-c2ccc(C(=O)NS(=O)(=O)c3cccnc3N)c(N3C[C@@H](C)CC3(C)C)n2)c(C)c1]
1871
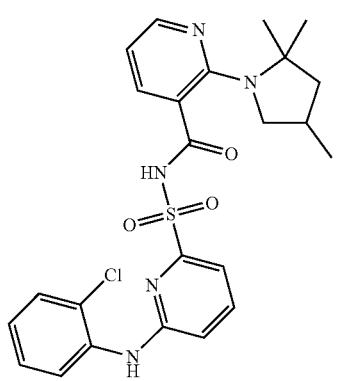 [SMILES: CC1CN(c2ncccc2C(=O)NS(=O)(=O)c2cccc(Nc3ccccc3Cl)n2)C(C)(C)C1]
1872

TABLE 1-continued
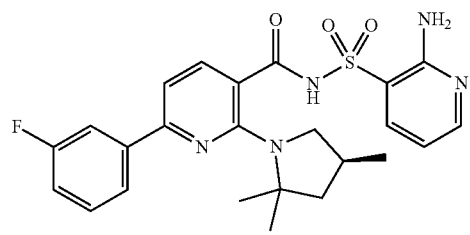 [SMILES: C[C@@H]1CN(c2nc(-c3cccc(F)c3)ccc2C(=O)NS(=O)(=O)c2cccnc2N)C(C)(C)C1]
1873
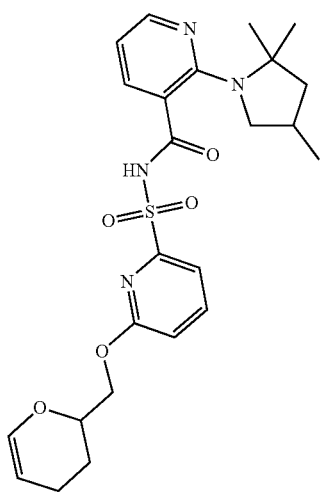 [SMILES: CC1CN(c2ncccc2C(=O)NS(=O)(=O)c2cccc(OCC3CCC=CO3)n2)C(C)(C)C1]
1874
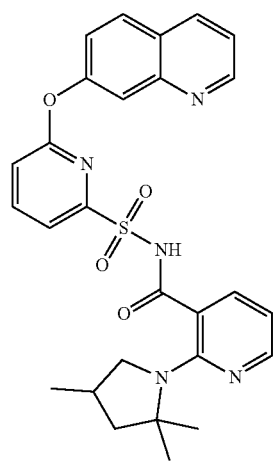 [SMILES: CC1CN(c2ncccc2C(=O)NS(=O)(=O)c2cccc(Oc3ccc4cccnc4c3)n2)C(C)(C)C1]
1875
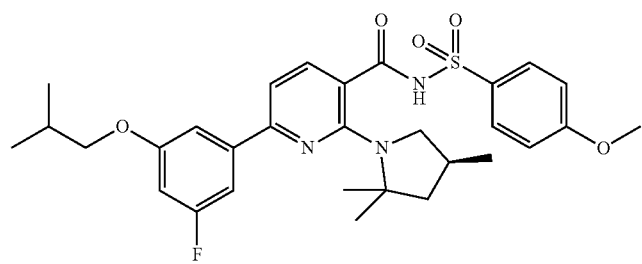 [SMILES: COc1ccc(S(=O)(=O)NC(=O)c2ccc(-c3cc(F)cc(OCC(C)C)c3)nc2N2C[C@@H](C)CC2(C)C)cc1]
1876

TABLE 1-continued
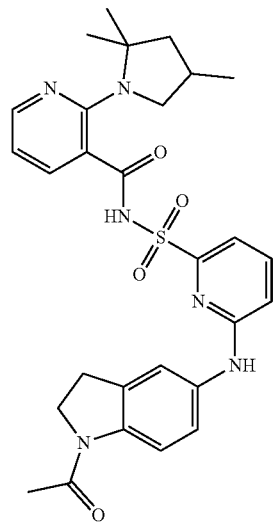 [SMILES: CC(=O)N1CCc2cc(Nc3cccc(S(=O)(=O)NC(=O)c4cccnc4N4CC(C)CC4(C)C)n3)ccc21]
1877
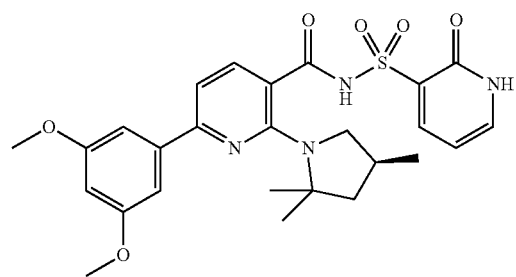 [SMILES: COc1cc(OC)cc(-c2ccc(C(=O)NS(=O)(=O)c3ccc[nH]c3=O)c(N3C[C@@H](C)CC3(C)C)n2)c1]
1878
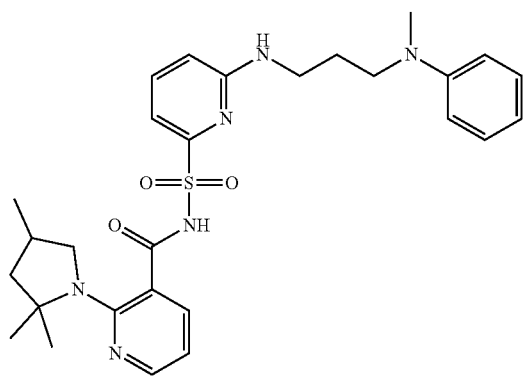 [SMILES: CC1CN(c2ncccc2C(=O)NS(=O)(=O)c2cccc(NCCCN(C)c3ccccc3)n2)C(C)(C)C1]
1879
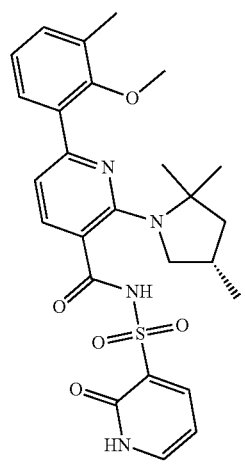 [SMILES: COc1c(C)cccc1-c1ccc(C(=O)NS(=O)(=O)c2ccc[nH]c2=O)c(N2C[C@@H](C)CC2(C)C)n1]
1880

TABLE 1-continued
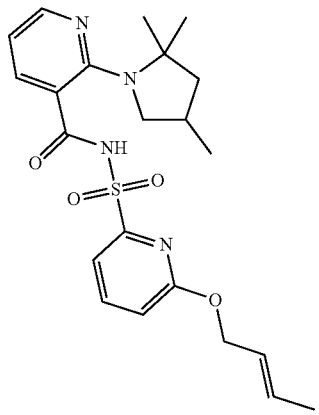 [SMILES: C/C=C/COc1cccc(S(=O)(=O)NC(=O)c2cccnc2N2CC(C)CC2(C)C)n1]
1881
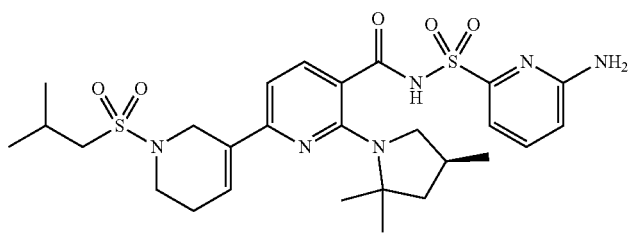 [SMILES: CC(C)CS(=O)(=O)N1CCC=C(c2ccc(C(=O)NS(=O)(=O)c3cccc(N)n3)c(N3C[C@@H](C)CC3(C)C)n2)C1]
1882
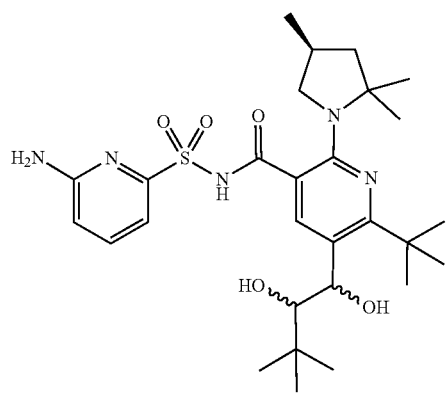 [SMILES: C[C@@H]1CN(c2nc(C(C)(C)C)c(C(O)C(O)C(C)(C)C)cc2C(=O)NS(=O)(=O)c2cccc(N)n2)C(C)(C)C1]
1883
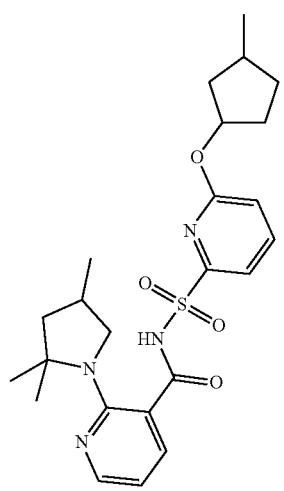 [SMILES: CC1CCC(Oc2cccc(S(=O)(=O)NC(=O)c3cccnc3N3CC(C)CC3(C)C)n2)C1]
1884

TABLE 1-continued
| | |
|---|---|
| 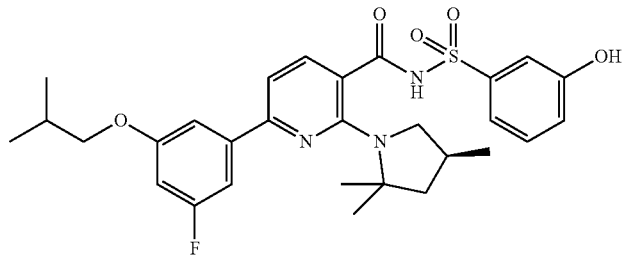 [SMILES: CC(C)COc1cc(F)cc(-c2ccc(C(=O)NS(=O)(=O)c3cccc(O)c3)c(N3C[C@@H](C)CC3(C)C)n2)c1] | 1885 |
| 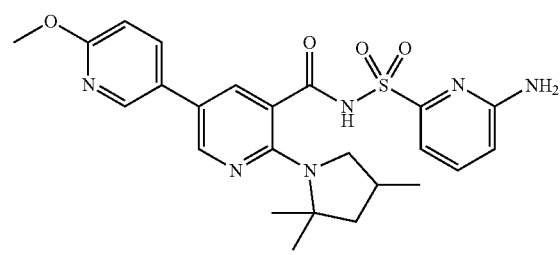 [SMILES: COc1ccc(-c2cnc(N3CC(C)CC3(C)C)c(C(=O)NS(=O)(=O)c3cccc(N)n3)c2)cn1] | 1886 |
| 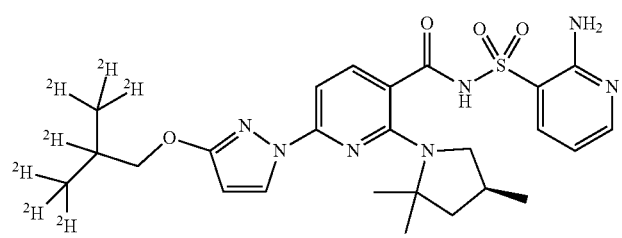 [SMILES: [2H]C([2H])([2H])C([2H])(COc1ccn(-c2ccc(C(=O)NS(=O)(=O)c3cccnc3N)c(N3C[C@@H](C)CC3(C)C)n2)n1)C([2H])([2H])[2H]] | 1887 |
| 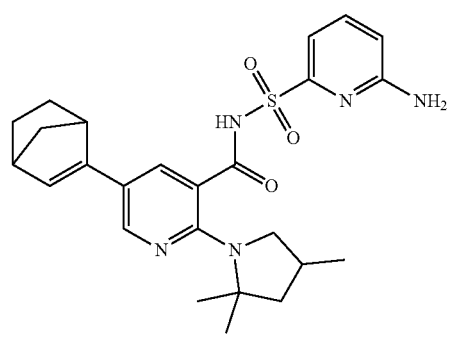 [SMILES: CC1CN(c2ncc(C3=CC4CCC3C4)cc2C(=O)NS(=O)(=O)c2cccc(N)n2)C(C)(C)C1] | 1888 |
| 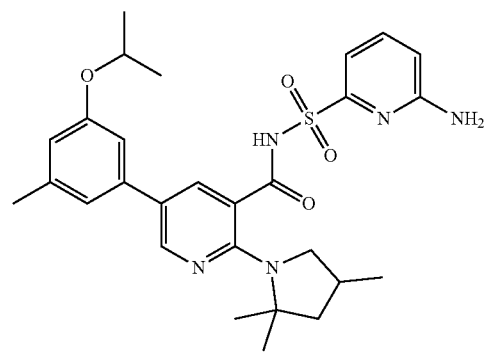 [SMILES: Cc1cc(OC(C)C)cc(-c2cnc(N3CC(C)CC3(C)C)c(C(=O)NS(=O)(=O)c3cccc(N)n3)c2)c1] | 1889 |

TABLE 1-continued
| | |
|---|---|
| 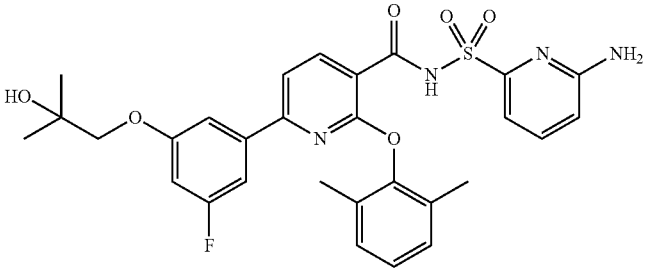 [SMILES: Cc1cccc(C)c1Oc1nc(-c2cc(F)cc(OCC(C)(C)O)c2)ccc1C(=O)NS(=O)(=O)c1cccc(N)n1] | 1890 |
| 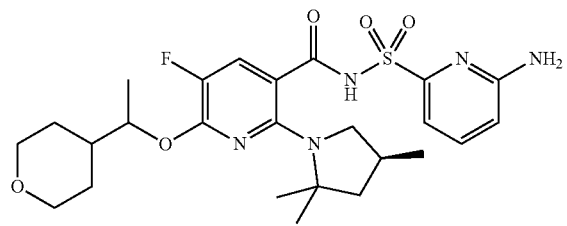 [SMILES: CC(Oc1nc(N2C[C@@H](C)CC2(C)C)c(C(=O)NS(=O)(=O)c2cccc(N)n2)cc1F)C1CCOCC1] | 1891 |
| 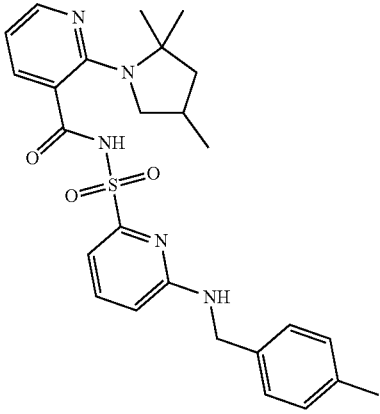 [SMILES: Cc1ccc(CNc2cccc(S(=O)(=O)NC(=O)c3cccnc3N3CC(C)CC3(C)C)n2)cc1] | 1892 |
| 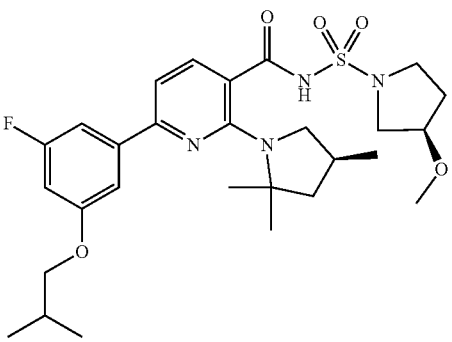 [SMILES: CO[C@@H]1CCN(S(=O)(=O)NC(=O)c2ccc(-c3cc(F)cc(OCC(C)C)c3)nc2N2C[C@@H](C)CC2(C)C)C1] | 1893 |
| 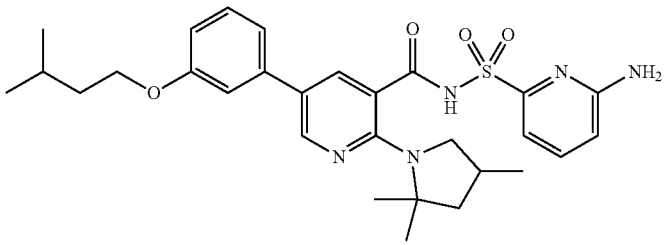 [SMILES: CC(C)CCOc1cccc(-c2cnc(N3CC(C)CC3(C)C)c(C(=O)NS(=O)(=O)c3cccc(N)n3)c2)c1] | 1894 |

TABLE 1-continued
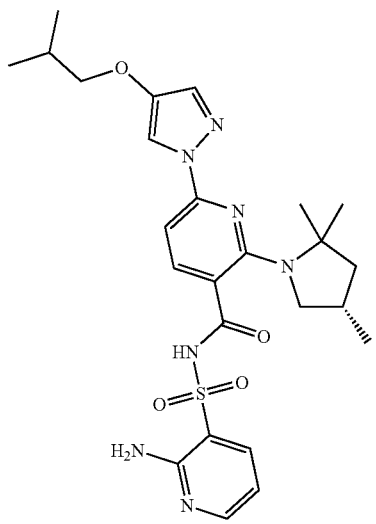 [SMILES: CC(C)COc1cnn(-c2ccc(C(=O)NS(=O)(=O)c3cccnc3N)c(N3C[C@@H](C)CC3(C)C)n2)c1]
1895
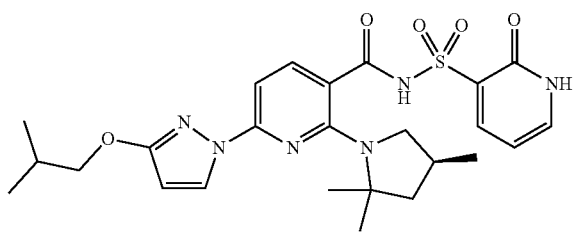 [SMILES: CC(C)COc1ccn(-c2ccc(C(=O)NS(=O)(=O)c3ccc[nH]c3=O)c(N3C[C@@H](C)CC3(C)C)n2)n1]
1896
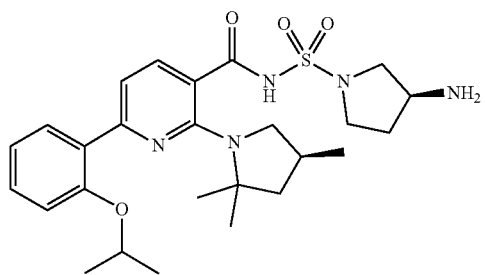 [SMILES: CC(C)Oc1ccccc1-c1ccc(C(=O)NS(=O)(=O)N2CC[C@H](N)C2)c(N2C[C@@H](C)CC2(C)C)n1]
1897
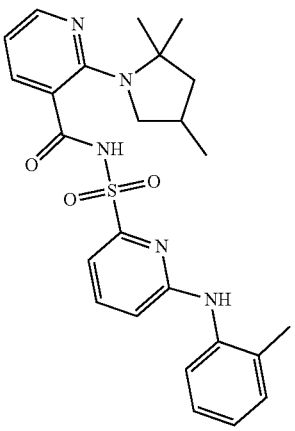 [SMILES: Cc1ccccc1Nc1cccc(S(=O)(=O)NC(=O)c2cccnc2N2CC(C)CC2(C)C)n1]
1898

TABLE 1-continued
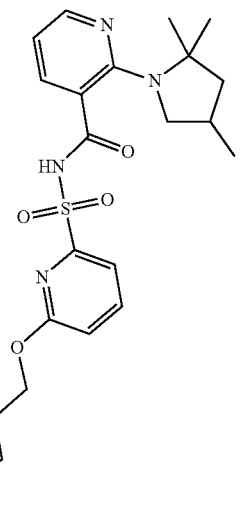
1899
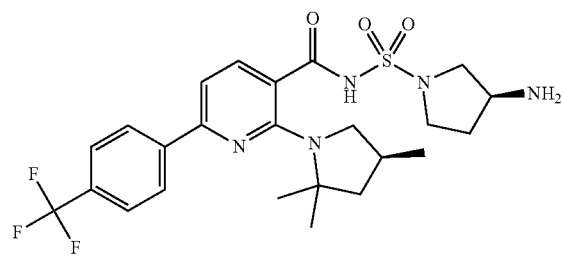 [SMILES: C[C@@H]1CN(c2nc(-c3ccc(C(F)(F)F)cc3)ccc2C(=O)NS(=O)(=O)N2CC[C@H](N)C2)C(C)(C)C1]
1900
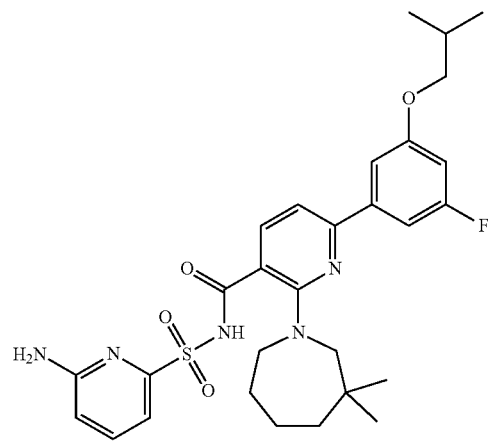 [SMILES: CC(C)COc1cc(F)cc(-c2ccc(C(=O)NS(=O)(=O)c3cccc(N)n3)c(N3CCCCC(C)(C)C3)n2)c1]
1901
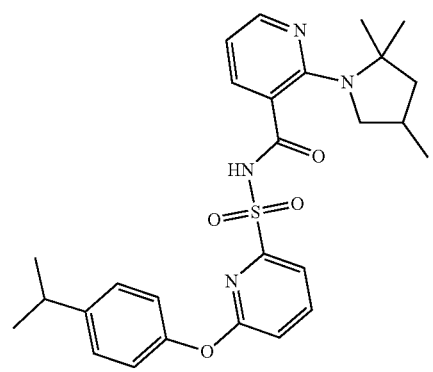 [SMILES: CC1CN(c2ncccc2C(=O)NS(=O)(=O)c2cccc(Oc3ccc(C(C)C)cc3)n2)C(C)(C)C1]
1902

TABLE 1-continued
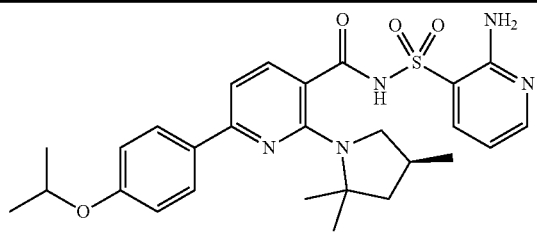
1903
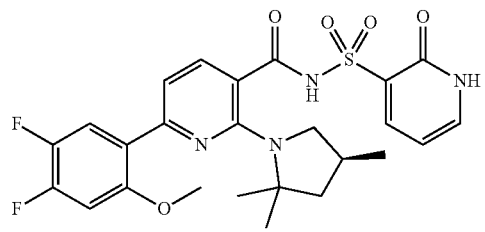 [SMILES: COc1cc(F)c(F)cc1-c1ccc(C(=O)NS(=O)(=O)c2ccc[nH]c2=O)c(N2C[C@@H](C)CC2(C)C)n1]
1904
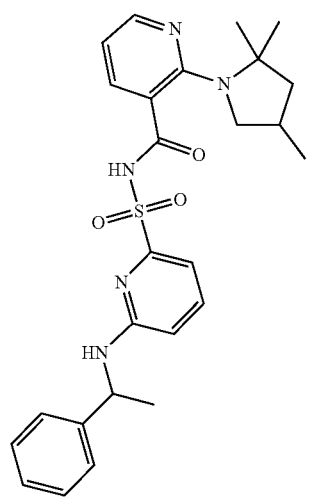 [SMILES: CC1CN(c2ncccc2C(=O)NS(=O)(=O)c2cccc(NC(C)c3ccccc3)n2)C(C)(C)C1]
1905
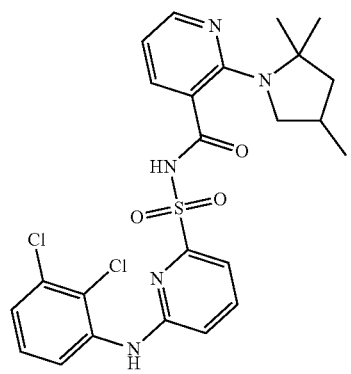 [SMILES: CC1CN(c2ncccc2C(=O)NS(=O)(=O)c2cccc(Nc3cccc(Cl)c3Cl)n2)C(C)(C)C1]
1906
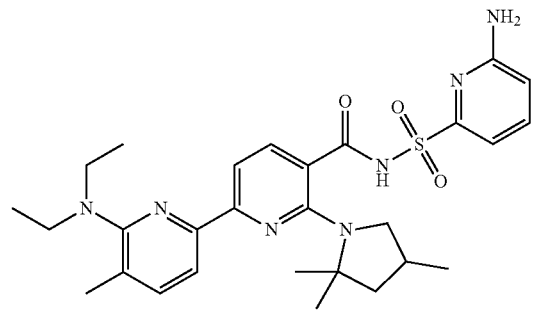 [SMILES: CCN(CC)c1nc(-c2ccc(C(=O)NS(=O)(=O)c3cccc(N)n3)c(N3CC(C)CC3(C)C)n2)ccc1C]
1907

TABLE 1-continued
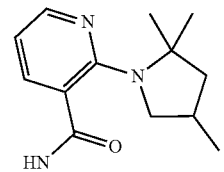
1908
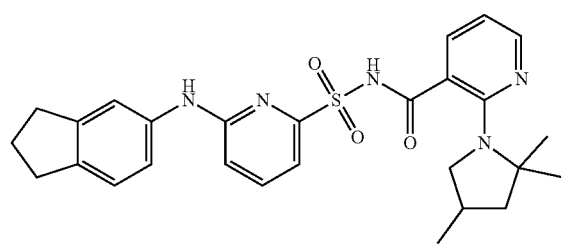 [SMILES: CC1CN(c2ncccc2C(=O)NS(=O)(=O)c2cccc(Nc3ccc4c(c3)CCC4)n2)C(C)(C)C1]
1909
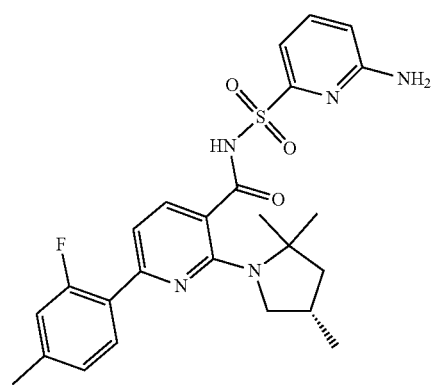 [SMILES: Cc1ccc(-c2ccc(C(=O)NS(=O)(=O)c3cccc(N)n3)c(N3C[C@@H](C)CC3(C)C)n2)c(F)c1]
1910
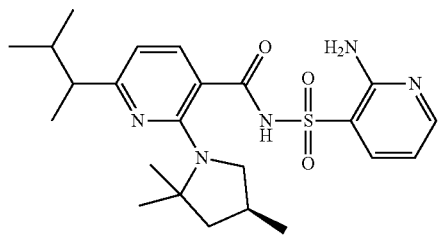 [SMILES: CC(C)C(C)c1ccc(C(=O)NS(=O)(=O)c2cccnc2N)c(N2C[C@@H](C)CC2(C)C)n1]
1911
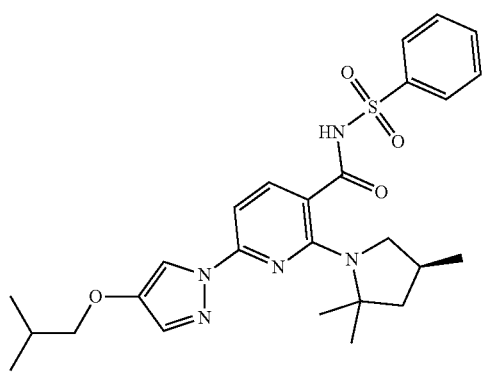 [SMILES: CC(C)COc1cnn(-c2ccc(C(=O)NS(=O)(=O)c3ccccc3)c(N3C[C@@H](C)CC3(C)C)n2)c1]
1912

TABLE 1-continued
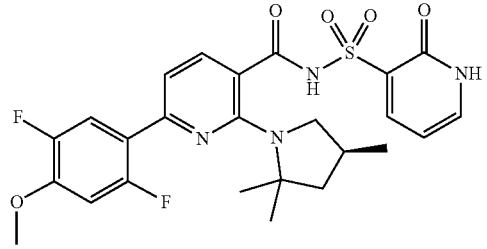 [SMILES: COc1cc(F)c(-c2ccc(C(=O)NS(=O)(=O)c3ccc[nH]c3=O)c(N3C[C@@H](C)CC3(C)C)n2)cc1F]
1913
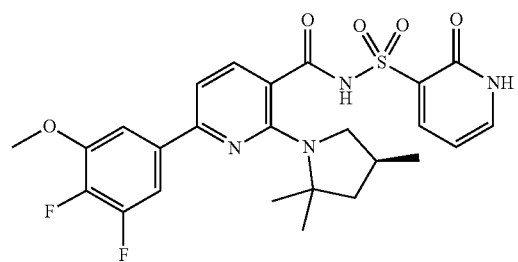 [SMILES: COc1cc(-c2ccc(C(=O)NS(=O)(=O)c3ccc[nH]c3=O)c(N3C[C@@H](C)CC3(C)C)n2)cc(F)c1F]
1914
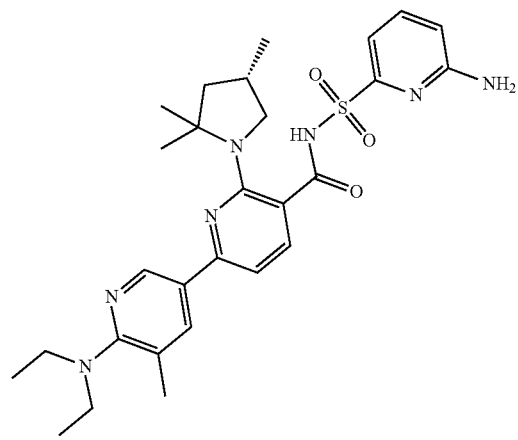 [SMILES: CCN(CC)c1ncc(-c2ccc(C(=O)NS(=O)(=O)c3cccc(N)n3)c(N3C[C@@H](C)CC3(C)C)n2)cc1C]
1915
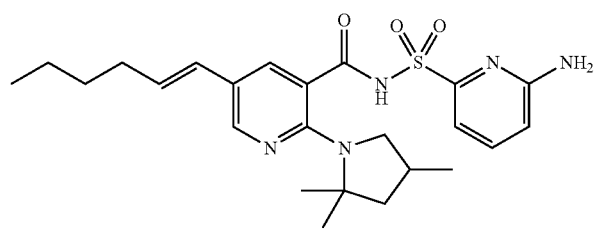 [SMILES: CCCC/C=C/c1cnc(N2CC(C)CC2(C)C)c(C(=O)NS(=O)(=O)c2cccc(N)n2)c1]
1916

TABLE 1-continued
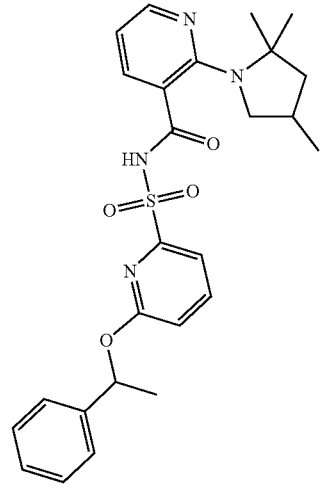 [SMILES: CC1CN(c2ncccc2C(=O)NS(=O)(=O)c2cccc(OC(C)c3ccccc3)n2)C(C)(C)C1]
1917
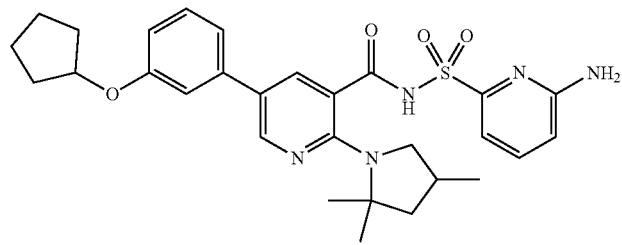 [SMILES: CC1CN(c2ncc(-c3cccc(OC4CCCC4)c3)cc2C(=O)NS(=O)(=O)c2cccc(N)n2)C(C)(C)C1]
1918
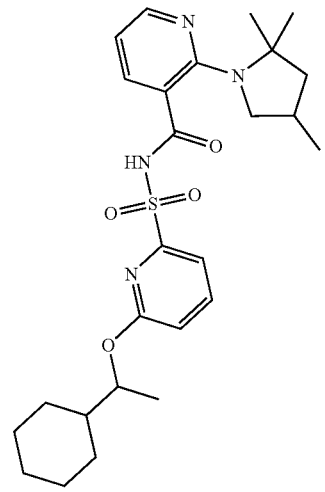 [SMILES: CC1CN(c2ncccc2C(=O)NS(=O)(=O)c2cccc(OC(C)C3CCCCC3)n2)C(C)(C)C1]
1919
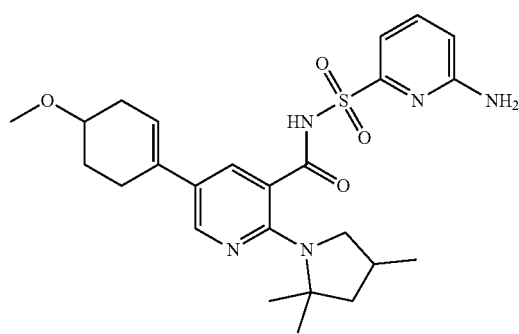 [SMILES: COC1CC=C(c2cnc(N3CC(C)CC3(C)C)c(C(=O)NS(=O)(=O)c3cccc(N)n3)c2)CC1]
1920

TABLE 1-continued
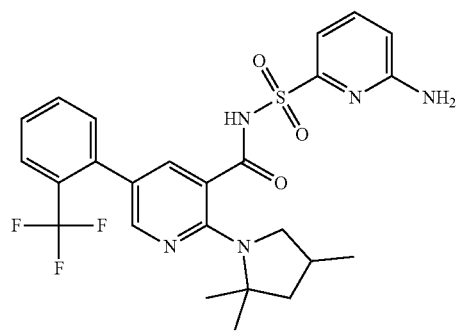 [SMILES: CC1CN(c2ncc(-c3ccccc3C(F)(F)F)cc2C(=O)NS(=O)(=O)c2cccc(N)n2)C(C)(C)C1]
1921
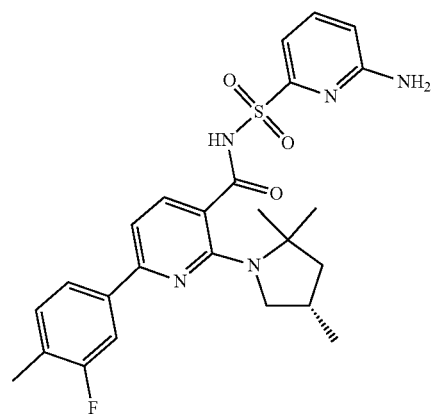 [SMILES: Cc1ccc(-c2ccc(C(=O)NS(=O)(=O)c3cccc(N)n3)c(N3C[C@@H](C)CC3(C)C)n2)cc1F]
1922
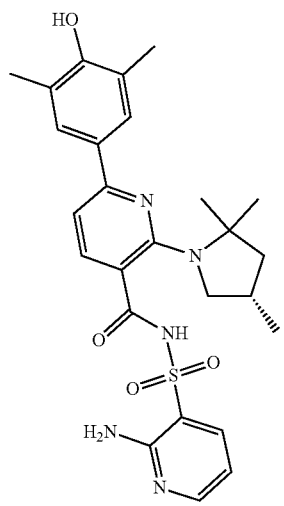
1923

TABLE 1-continued
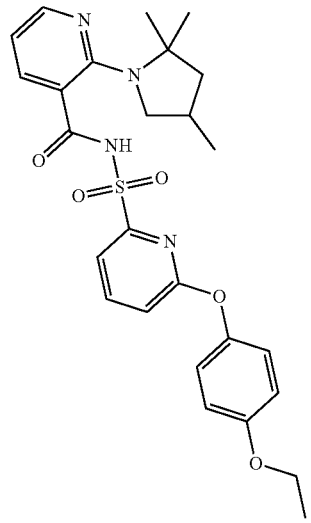 [SMILES: CCOc1ccc(Oc2cccc(S(=O)(=O)NC(=O)c3cccnc3N3CC(C)CC3(C)C)n2)cc1]
1924
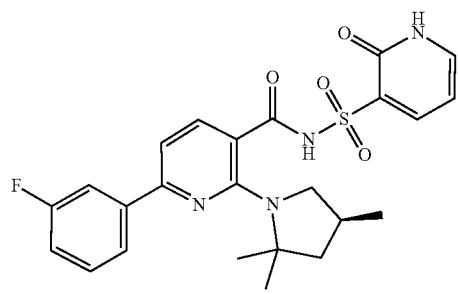 [SMILES: C[C@@H]1CN(c2nc(-c3cccc(F)c3)ccc2C(=O)NS(=O)(=O)c2ccc[nH]c2=O)C(C)(C)C1]
1925
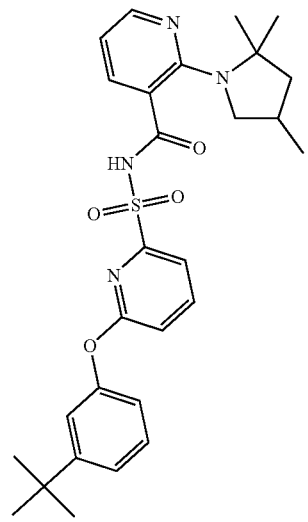 [SMILES: CC1CN(c2ncccc2C(=O)NS(=O)(=O)c2cccc(Oc3cccc(C(C)(C)C)c3)n2)C(C)(C)C1]
1926
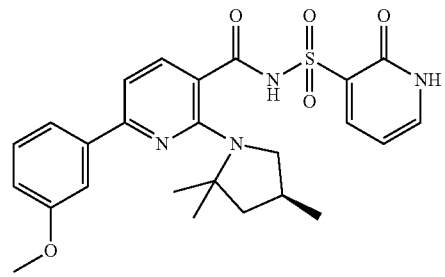 [SMILES: COc1cccc(-c2ccc(C(=O)NS(=O)(=O)c3ccc[nH]c3=O)c(N3C[C@@H](C)CC3(C)C)n2)c1]
1927

TABLE 1-continued
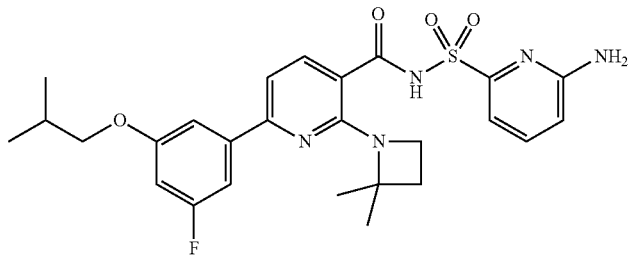 [SMILES: CC(C)COc1cc(F)cc(-c2ccc(C(=O)NS(=O)(=O)c3cccc(N)n3)c(N3CCC3(C)C)n2)c1]
1928
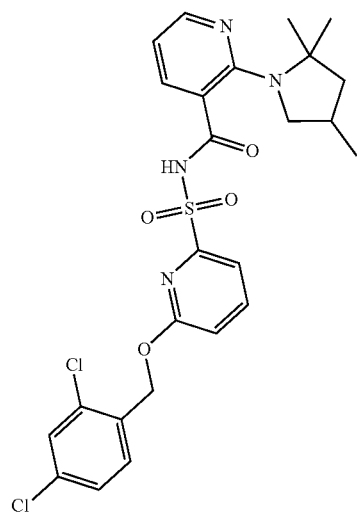 [SMILES: CC1CN(c2ncccc2C(=O)NS(=O)(=O)c2cccc(OCc3ccc(Cl)cc3Cl)n2)C(C)(C)C1]
1929
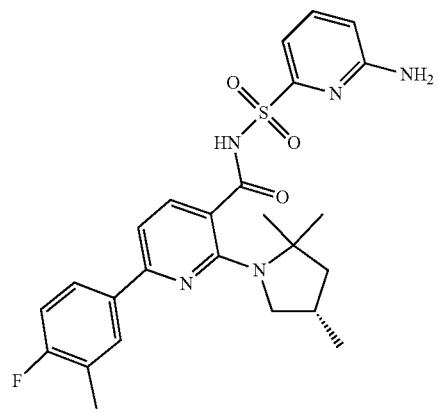 [SMILES: Cc1cc(-c2ccc(C(=O)NS(=O)(=O)c3cccc(N)n3)c(N3C[C@@H](C)CC3(C)C)n2)ccc1F]
1930

TABLE 1-continued
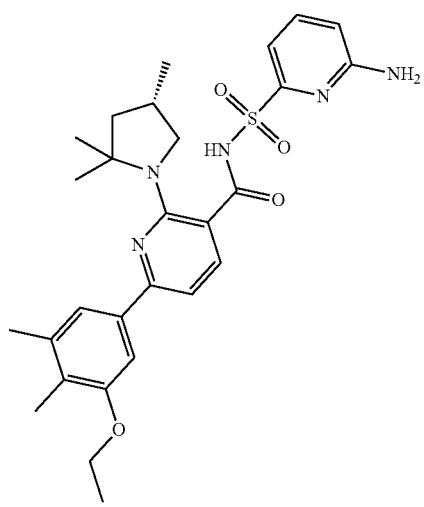 [SMILES: CCOc1cc(-c2ccc(C(=O)NS(=O)(=O)c3cccc(N)n3)c(N3C[C@@H](C)CC3(C)C)n2)cc(C)c1C]
1931
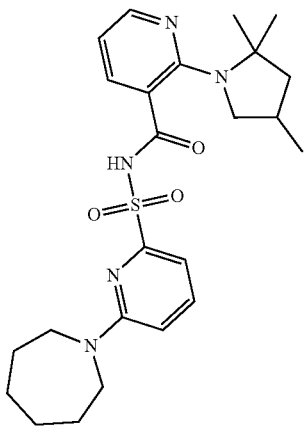 [SMILES: CC1CN(c2ncccc2C(=O)NS(=O)(=O)c2cccc(N3CCCCCC3)n2)C(C)(C)C1]
1932
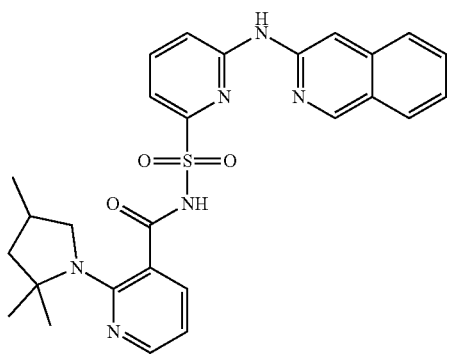
1933
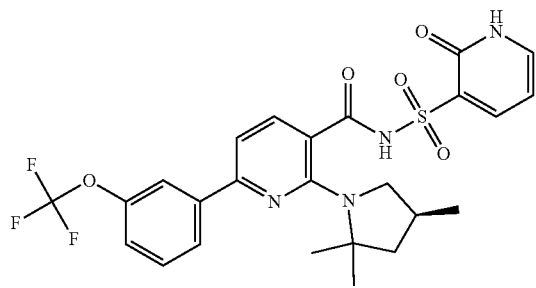 [SMILES: C[C@@H]1CN(c2nc(-c3cccc(OC(F)(F)F)c3)ccc2C(=O)NS(=O)(=O)c2ccc[nH]c2=O)C(C)(C)C1]
1934

TABLE 1-continued
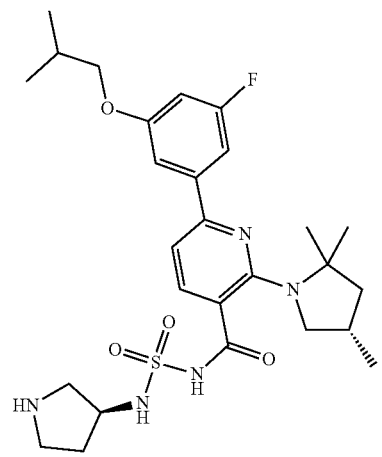 [SMILES: CC(C)COc1cc(F)cc(-c2ccc(C(=O)NS(=O)(=O)N[C@H]3CCNC3)c(N3C[C@@H](C)CC3(C)C)n2)c1]
1935
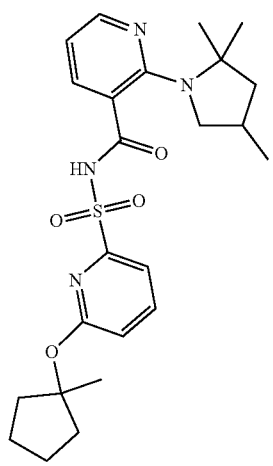 [SMILES: CC1CN(c2ncccc2C(=O)NS(=O)(=O)c2cccc(OC3(C)CCCC3)n2)C(C)(C)C1]
1936
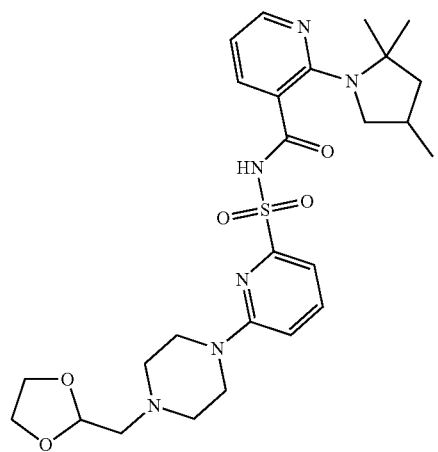 [SMILES: CC1CN(c2ncccc2C(=O)NS(=O)(=O)c2cccc(N3CCN(CC4OCCO4)CC3)n2)C(C)(C)C1]
1937

TABLE 1-continued
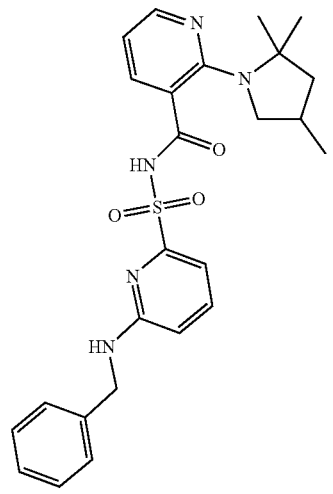 [SMILES: CC1CN(c2ncccc2C(=O)NS(=O)(=O)c2cccc(NCc3ccccc3)n2)C(C)(C)C1]
1938
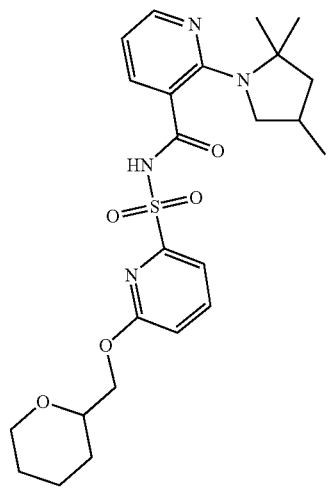 [SMILES: CC1CN(c2ncccc2C(=O)NS(=O)(=O)c2cccc(OCC3CCCCO3)n2)C(C)(C)C1]
1939
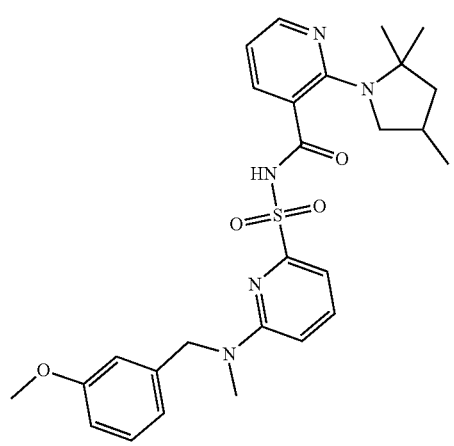
1940

TABLE 1-continued
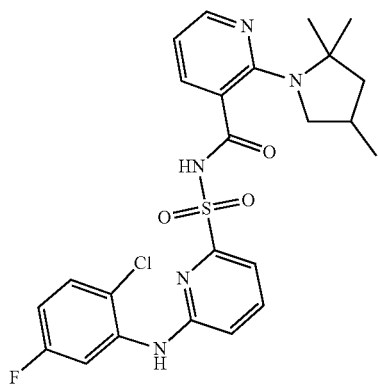 [SMILES: CC1CN(c2ncccc2C(=O)NS(=O)(=O)c2cccc(Nc3cc(F)ccc3Cl)n2)C(C)(C)C1]
1941
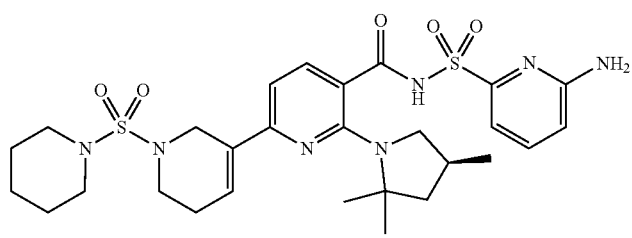 [SMILES: C[C@@H]1CN(c2nc(C3=CCCN(S(=O)(=O)N4CCCCC4)C3)ccc2C(=O)NS(=O)(=O)c2cccc(N)n2)C(C)(C)C1]
1942
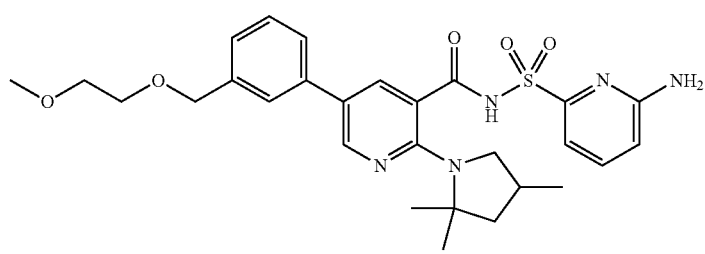 [SMILES: COCCOCc1cccc(-c2cnc(N3CC(C)CC3(C)C)c(C(=O)NS(=O)(=O)c3cccc(N)n3)c2)c1]
1943
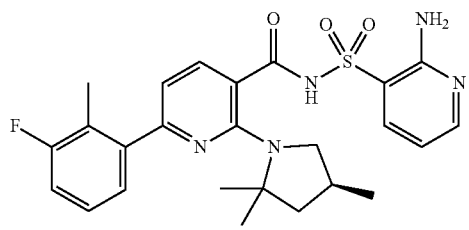 [SMILES: Cc1c(F)cccc1-c1ccc(C(=O)NS(=O)(=O)c2cccnc2N)c(N2C[C@@H](C)CC2(C)C)n1]
1944
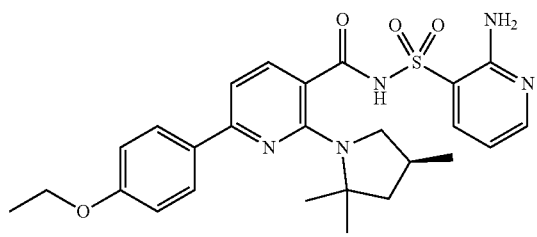 [SMILES: CCOc1ccc(-c2ccc(C(=O)NS(=O)(=O)c3cccnc3N)c(N3C[C@@H](C)CC3(C)C)n2)cc1]
1945
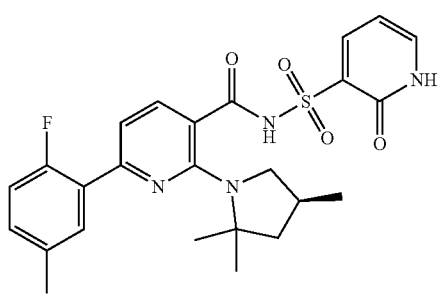 [SMILES: Cc1ccc(F)c(-c2ccc(C(=O)NS(=O)(=O)c3ccc[nH]c3=O)c(N3C[C@@H](C)CC3(C)C)n2)c1]
1946

TABLE 1-continued
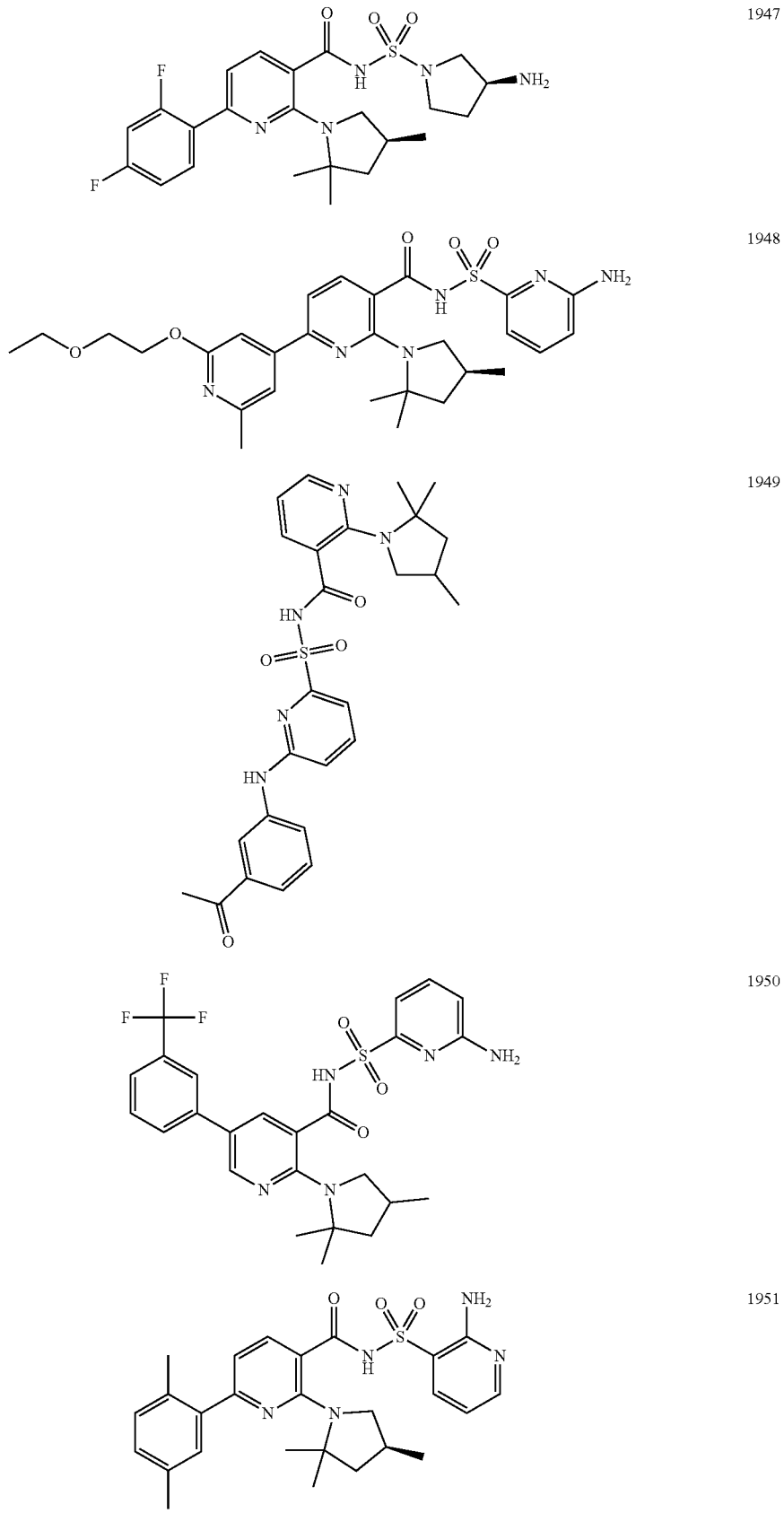
1947
1948
1949
1950
1951

TABLE 1-continued
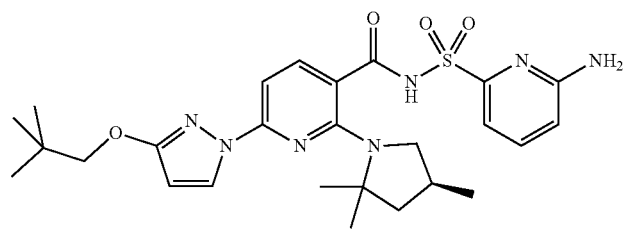 [SMILES: C[C@@H]1CN(c2nc(-n3ccc(OCC(C)(C)C)n3)ccc2C(=O)NS(=O)(=O)c2cccc(N)n2)C(C)(C)C1]
1952
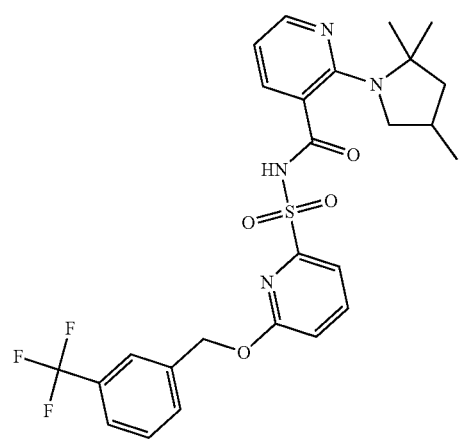 [SMILES: CC1CN(c2ncccc2C(=O)NS(=O)(=O)c2cccc(OCc3cccc(C(F)(F)F)c3)n2)C(C)(C)C1]
1953
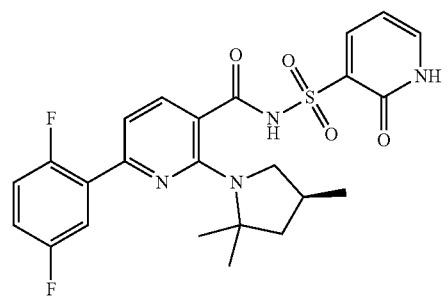 [SMILES: C[C@@H]1CN(c2nc(-c3cc(F)ccc3F)ccc2C(=O)NS(=O)(=O)c2ccc[nH]c2=O)C(C)(C)C1]
1954
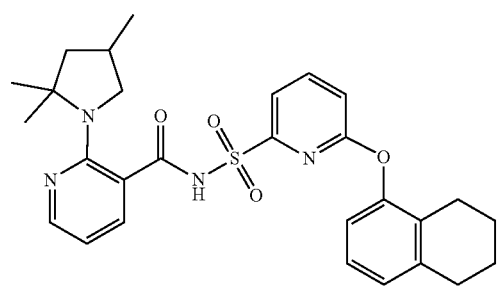 [SMILES: CC1CN(c2ncccc2C(=O)NS(=O)(=O)c2cccc(Oc3cccc4c3CCCC4)n2)C(C)(C)C1]
1955

TABLE 1-continued
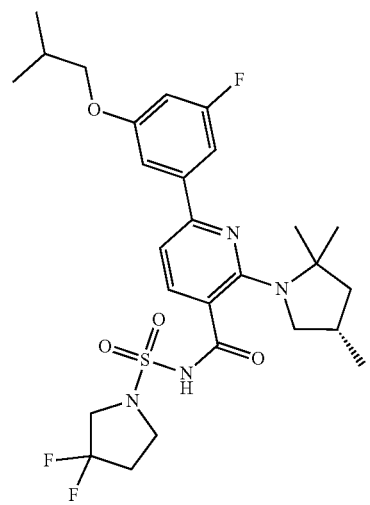 [SMILES: CC(C)COc1cc(F)cc(-c2ccc(C(=O)NS(=O)(=O)N3CCC(F)(F)C3)c(N3C[C@@H](C)CC3(C)C)n2)c1]
1956
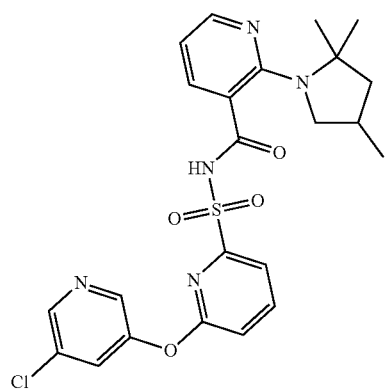 [SMILES: CC1CN(c2ncccc2C(=O)NS(=O)(=O)c2cccc(Oc3cncc(Cl)c3)n2)C(C)(C)C1]
1957
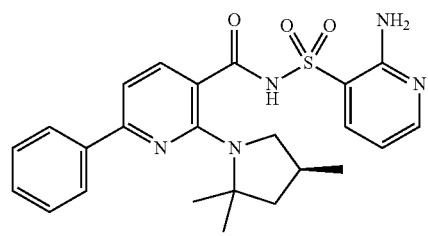 [SMILES: C[C@@H]1CN(c2nc(-c3ccccc3)ccc2C(=O)NS(=O)(=O)c2cccnc2N)C(C)(C)C1]
1958
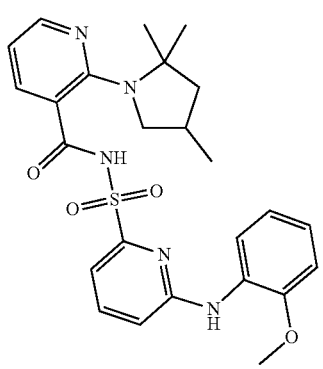 [SMILES: COc1ccccc1Nc1cccc(S(=O)(=O)NC(=O)c2cccnc2N2CC(C)CC2(C)C)n1]
1959

TABLE 1-continued
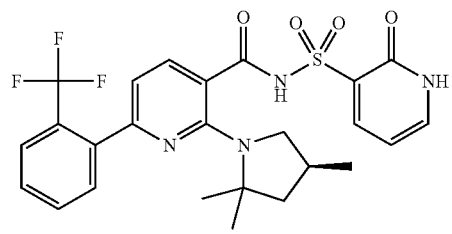 [SMILES: C[C@@H]1CN(c2nc(-c3ccccc3C(F)(F)F)ccc2C(=O)NS(=O)(=O)c2ccc[nH]c2=O)C(C)(C)C1]
1960
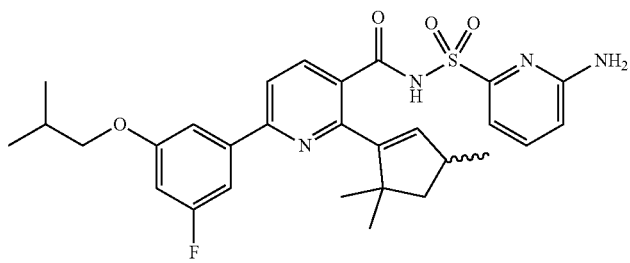 [SMILES: CC(C)COc1cc(F)cc(-c2ccc(C(=O)NS(=O)(=O)c3cccc(N)n3)c(C3=CC(C)CC3(C)C)n2)c1]
1961
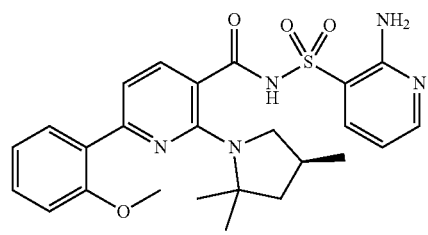 [SMILES: COc1ccccc1-c1ccc(C(=O)NS(=O)(=O)c2cccnc2N)c(N2C[C@@H](C)CC2(C)C)n1]
1962
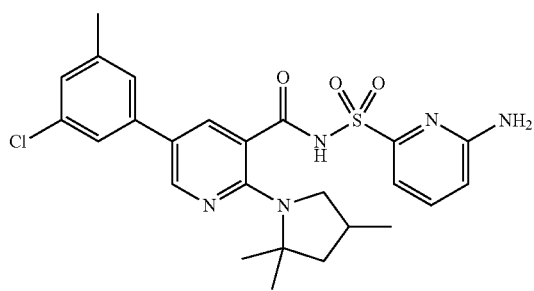 [SMILES: Cc1cc(Cl)cc(-c2cnc(N3CC(C)CC3(C)C)c(C(=O)NS(=O)(=O)c3cccc(N)n3)c2)c1]
1963
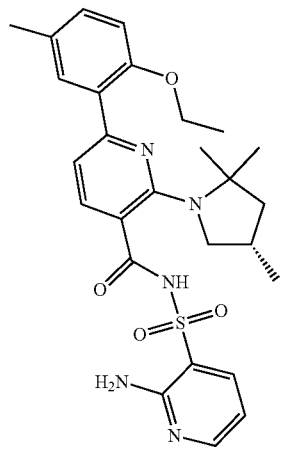
1964

TABLE 1-continued
| | |
|---|---|
| 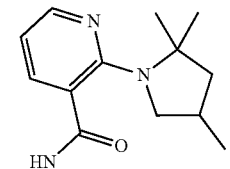 | 1965 |
| 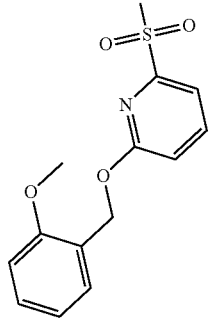 | 1966 |
| 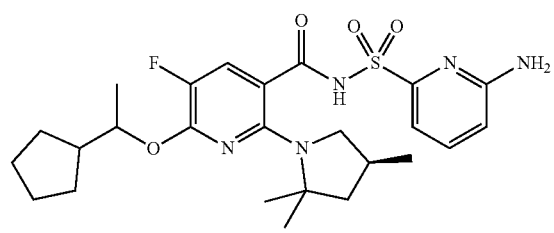 [SMILES: CC(Oc1nc(N2C[C@@H](C)CC2(C)C)c(C(=O)NS(=O)(=O)c2cccc(N)n2)cc1F)C1CCCC1] | 1967 |
| 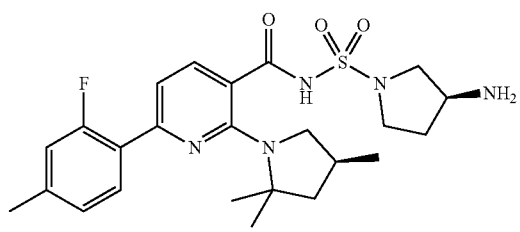 [SMILES: Cc1ccc(-c2ccc(C(=O)NS(=O)(=O)N3CC[C@H](N)C3)c(N3C[C@@H](C)CC3(C)C)n2)c(F)c1] | 1968 |
| 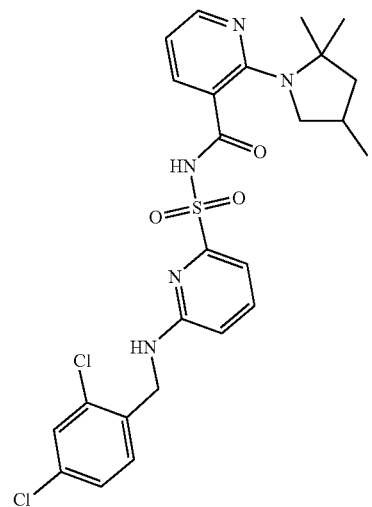 [SMILES: CC1CN(c2ncccc2C(=O)NS(=O)(=O)c2cccc(NCc3ccc(Cl)cc3Cl)n2)C(C)(C)C1] | |

TABLE 1-continued
| | |
|---|---|
| 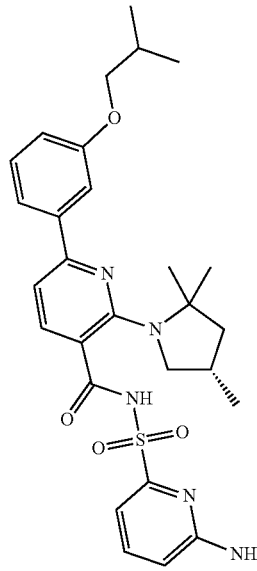 | 1969 |
| 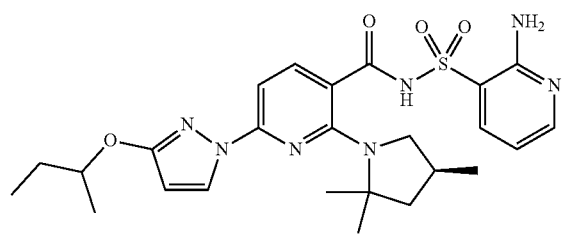 [SMILES: CCC(C)Oc1ccn(-c2ccc(C(=O)NS(=O)(=O)c3cccnc3N)c(N3C[C@@H](C)CC3(C)C)n2)n1] | 1970 |
| 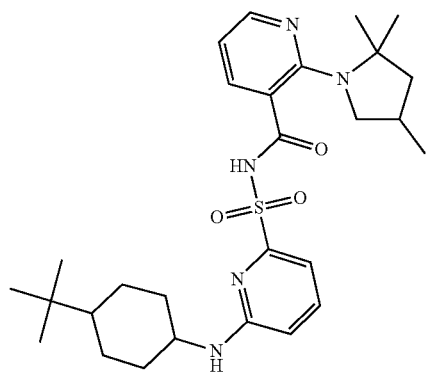 [SMILES: CC1CN(c2ncccc2C(=O)NS(=O)(=O)c2cccc(NC3CCC(C(C)(C)C)CC3)n2)C(C)(C)C1] | 1971 |
| 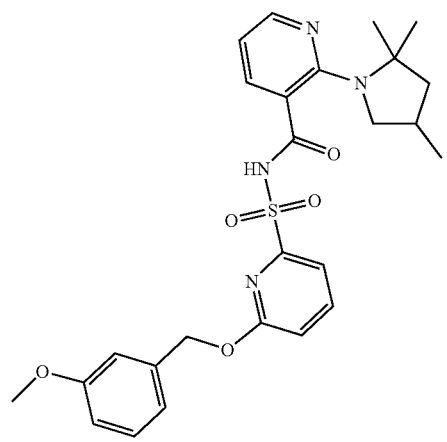 | 1972 |

TABLE 1-continued
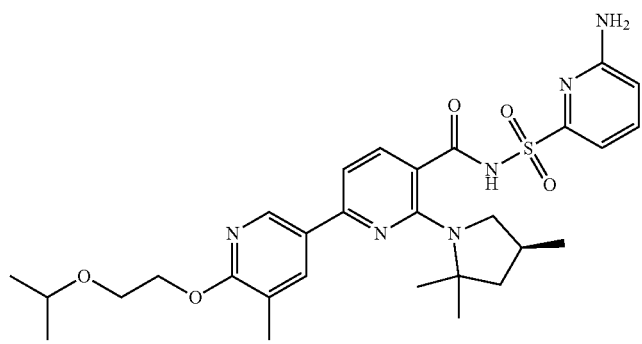 [SMILES: Cc1cc(-c2ccc(C(=O)NS(=O)(=O)c3cccc(N)n3)c(N3C[C@@H](C)CC3(C)C)n2)cnc1OCCOC(C)C]
1973
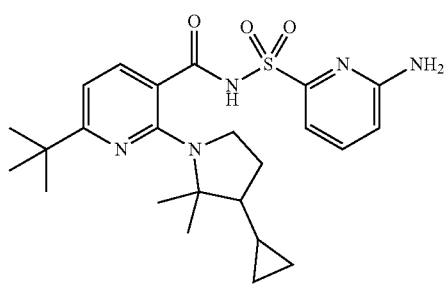 [SMILES: CC(C)(C)c1ccc(C(=O)NS(=O)(=O)c2cccc(N)n2)c(N2CCC(C3CC3)C2(C)C)n1]
1974
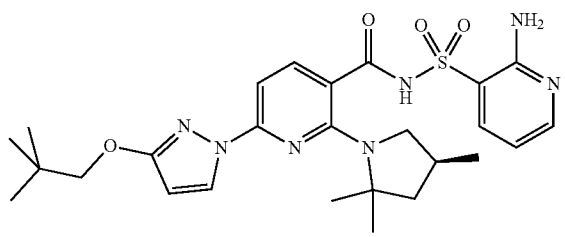 [SMILES: C[C@@H]1CN(c2nc(-n3ccc(OCC(C)(C)C)n3)ccc2C(=O)NS(=O)(=O)c2cccnc2N)C(C)(C)C1]
1975
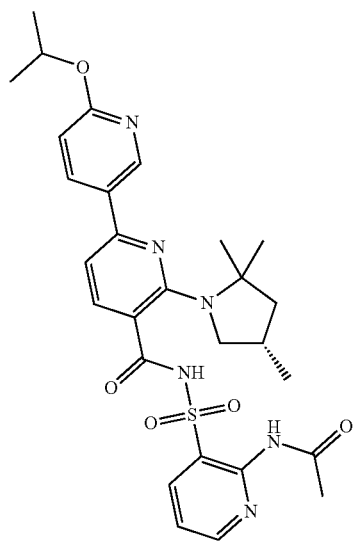 [SMILES: CC(=O)Nc1ncccc1S(=O)(=O)NC(=O)c1ccc(-c2ccc(OC(C)C)nc2)nc1N1C[C@@H](C)CC1(C)C]
1976

TABLE 1-continued
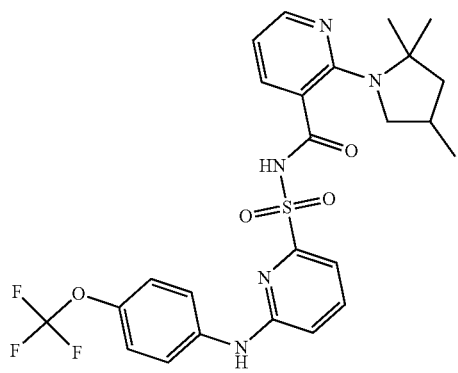 [SMILES: CC1CN(c2ncccc2C(=O)NS(=O)(=O)c2cccc(Nc3ccc(OC(F)(F)F)cc3)n2)C(C)(C)C1]
1977
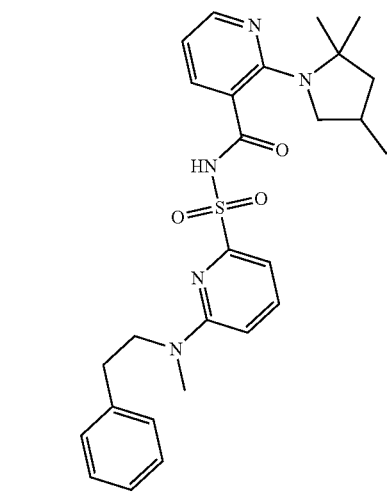 [SMILES: CC1CN(c2ncccc2C(=O)NS(=O)(=O)c2cccc(N(C)CCc3ccccc3)n2)C(C)(C)C1]
1978
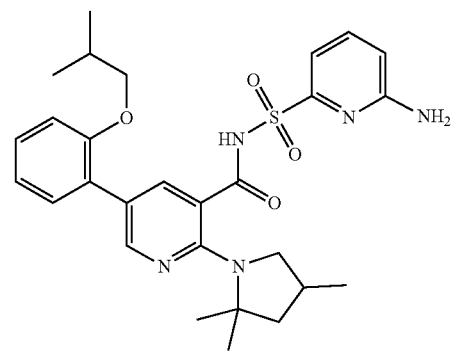 [SMILES: CC(C)COc1ccccc1-c1cnc(N2CC(C)CC2(C)C)c(C(=O)NS(=O)(=O)c2cccc(N)n2)c1]
1979
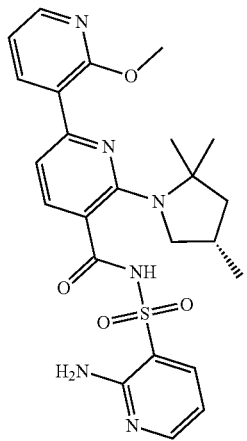 [SMILES: COc1ncccc1-c1ccc(C(=O)NS(=O)(=O)c2cccnc2N)c(N2C[C@@H](C)CC2(C)C)n1]
1980

TABLE 1-continued

| | |
|---|---|
| (structure) | 1981 |
| (structure) | 1982 |
| (structure) | 1983 |
| (structure) | 1984 |

TABLE 1-continued
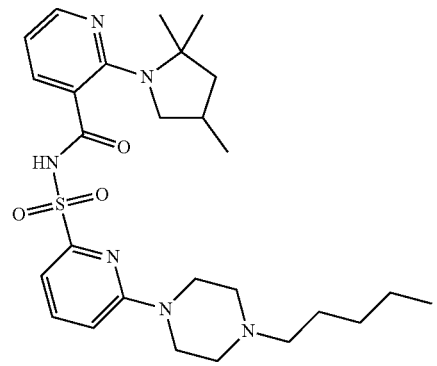 [SMILES: CCCCCN1CCN(c2cccc(S(=O)(=O)NC(=O)c3cccnc3N3CC(C)CC3(C)C)n2)CC1]
1985
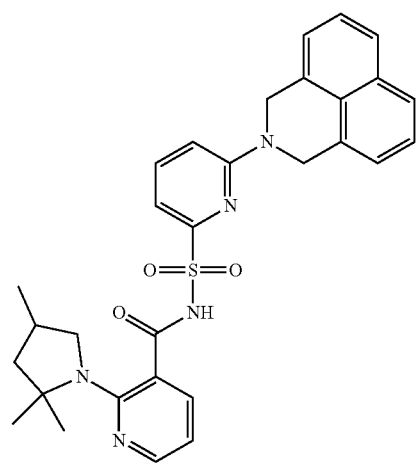 [SMILES: CC1CN(c2ncccc2C(=O)NS(=O)(=O)c2cccc(N3Cc4cccc5cccc(c45)C3)n2)C(C)(C)C1]
1986
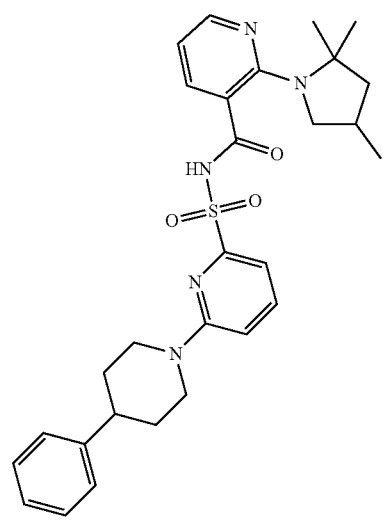 [SMILES: CC1CN(c2ncccc2C(=O)NS(=O)(=O)c2cccc(N3CCC(c4ccccc4)CC3)n2)C(C)(C)C1]
1987

TABLE 1-continued
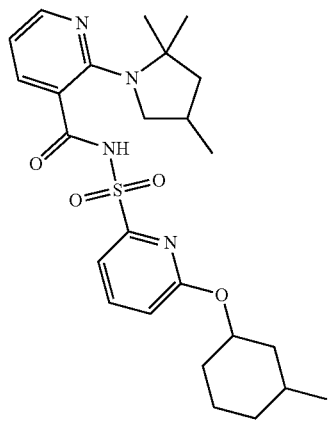 [SMILES: CC1CCCC(Oc2cccc(S(=O)(=O)NC(=O)c3cccnc3N3CC(C)CC3(C)C)n2)C1]
1988
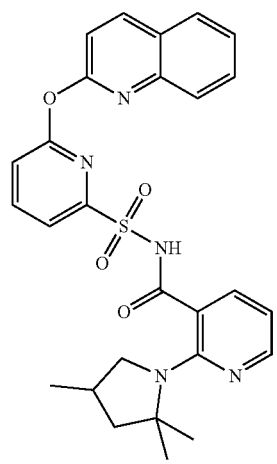 [SMILES: CC1CN(c2ncccc2C(=O)NS(=O)(=O)c2cccc(Oc3ccc4ccccc4n3)n2)C(C)(C)C1]
1989
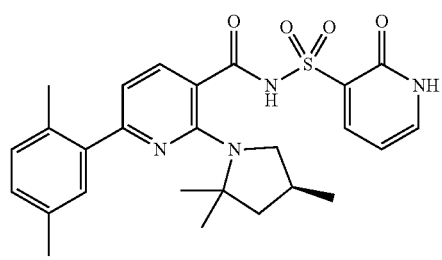 [SMILES: Cc1ccc(C)c(-c2ccc(C(=O)NS(=O)(=O)c3ccc[nH]c3=O)c(N3C[C@@H](C)CC3(C)C)n2)c1]
1990
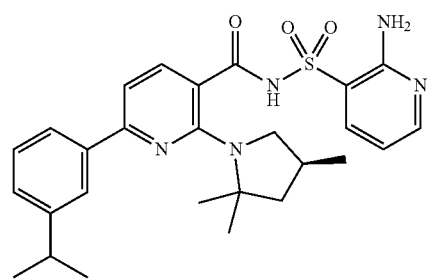 [SMILES: CC(C)c1cccc(-c2ccc(C(=O)NS(=O)(=O)c3cccnc3N)c(N3C[C@@H](C)CC3(C)C)n2)c1]
1991

| | |
|---|---|
| 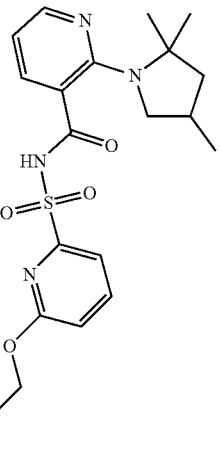 | 1992 |
| 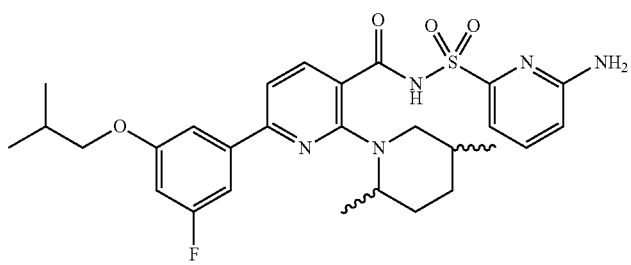 | 1993 |
| 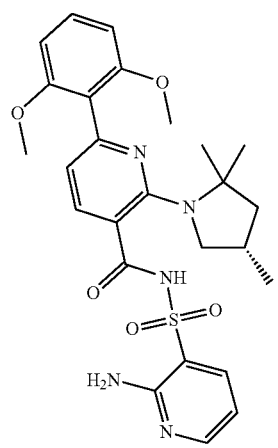 [SMILES: COc1cccc(OC)c1-c1ccc(C(=O)NS(=O)(=O)c2cccnc2N)c(N2C[C@@H](C)CC2(C)C)n1] | 1994 |
| 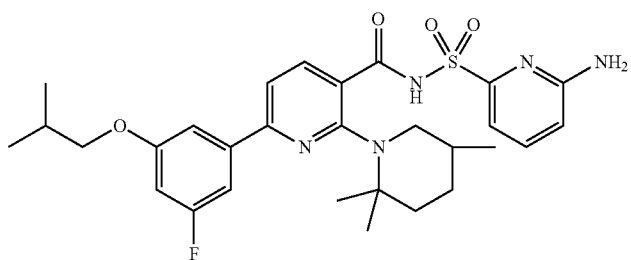 [SMILES: CC(C)COc1cc(F)cc(-c2ccc(C(=O)NS(=O)(=O)c3cccc(N)n3)c(N3CC(C)CCC3(C)C)n2)c1] | 1995 |

TABLE 1-continued
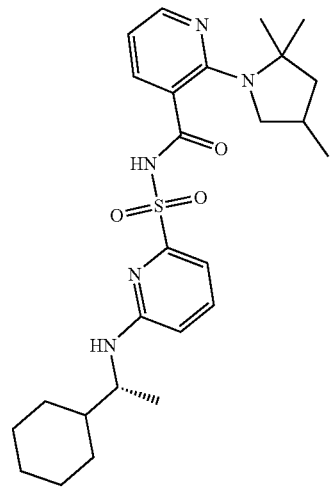 [SMILES: CC1CN(c2ncccc2C(=O)NS(=O)(=O)c2cccc(N[C@H](C)C3CCCCC3)n2)C(C)(C)C1]
1996
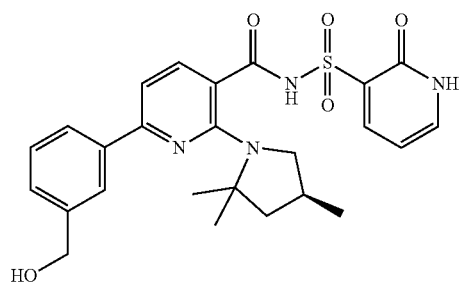 [SMILES: C[C@@H]1CN(c2nc(-c3cccc(CO)c3)ccc2C(=O)NS(=O)(=O)c2ccc[nH]c2=O)C(C)(C)C1]
1997
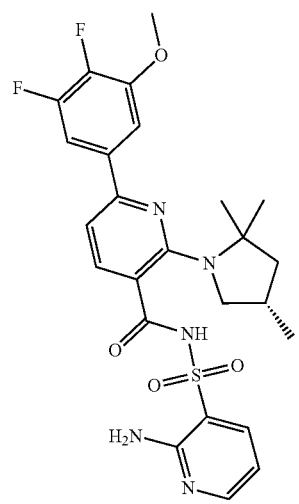 [SMILES: COc1cc(-c2ccc(C(=O)NS(=O)(=O)c3cccnc3N)c(N3C[C@@H](C)CC3(C)C)n2)cc(F)c1F]
1998

TABLE 1-continued
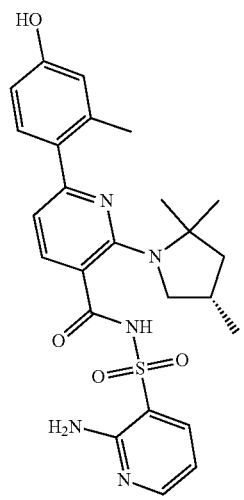 [SMILES: Cc1cc(O)ccc1-c1ccc(C(=O)NS(=O)(=O)c2cccnc2N)c(N2C[C@@H](C)CC2(C)C)n1]
1999
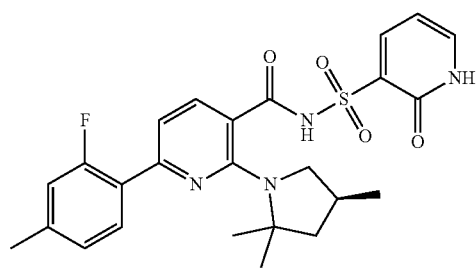 [SMILES: Cc1ccc(-c2ccc(C(=O)NS(=O)(=O)c3ccc[nH]c3=O)c(N3C[C@@H](C)CC3(C)C)n2)c(F)c1]
2000
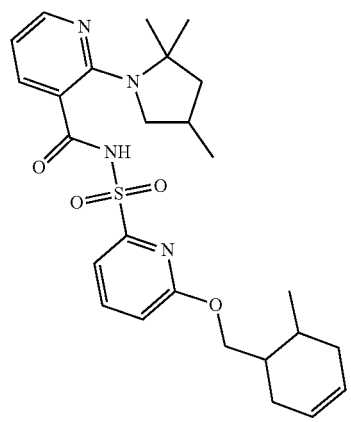 [SMILES: CC1CN(c2ncccc2C(=O)NS(=O)(=O)c2cccc(OCC3CC=CCC3C)n2)C(C)(C)C1]
2001
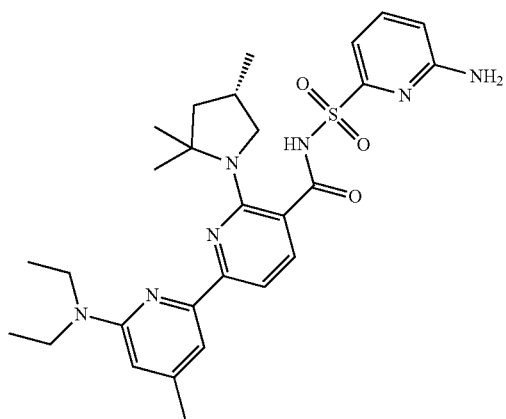 [SMILES: CCN(CC)c1cc(C)cc(-c2ccc(C(=O)NS(=O)(=O)c3cccc(N)n3)c(N3C[C@@H](C)CC3(C)C)n2)n1]
2002

TABLE 1-continued
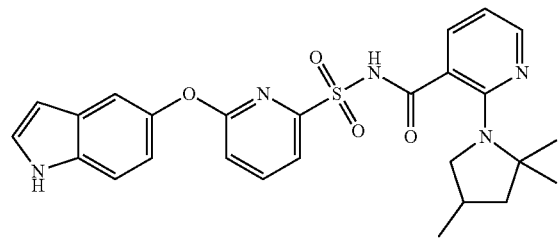 [SMILES: CC1CN(c2ncccc2C(=O)NS(=O)(=O)c2cccc(Oc3ccc4[nH]ccc4c3)n2)C(C)(C)C1]
2003
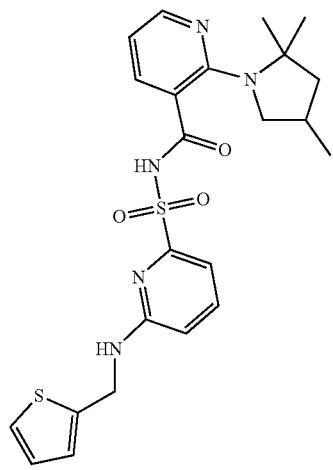 [SMILES: CC1CN(c2ncccc2C(=O)NS(=O)(=O)c2cccc(NCc3cccs3)n2)C(C)(C)C1]
2004
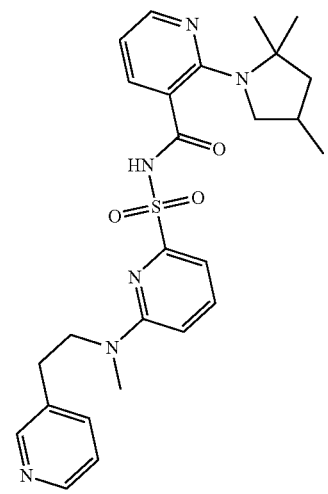 [SMILES: CC1CN(c2ncccc2C(=O)NS(=O)(=O)c2cccc(N(C)CCc3cccnc3)n2)C(C)(C)C1]
2005
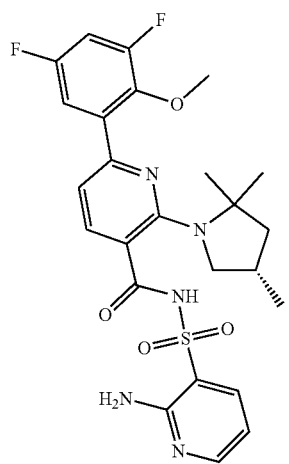 [SMILES: COc1c(F)cc(F)cc1-c1ccc(C(=O)NS(=O)(=O)c2cccnc2N)c(N2C[C@@H](C)CC2(C)C)n1]
2006

| | |
|---|---|
| 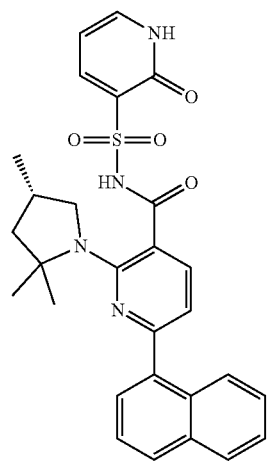 [SMILES: C[C@@H]1CN(c2nc(-c3cccc4ccccc34)ccc2C(=O)NS(=O)(=O)c2ccc[nH]c2=O)C(C)(C)C1] | 2007 |
| 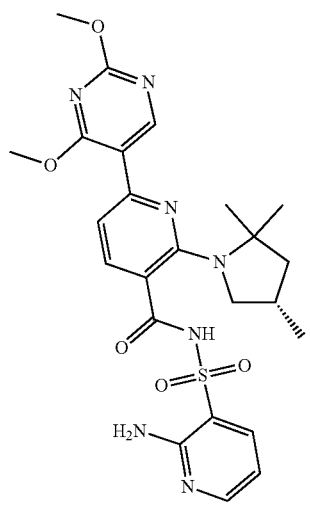 | 2008 |
| 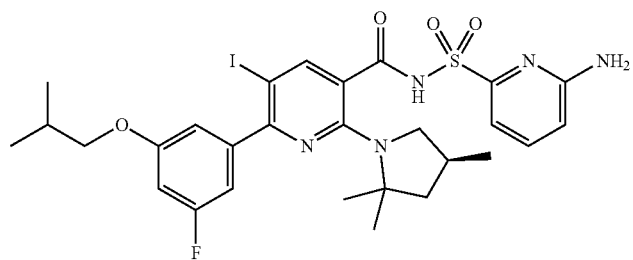 [SMILES: CC(C)COc1cc(F)cc(-c2nc(N3C[C@@H](C)CC3(C)C)c(C(=O)NS(=O)(=O)c3cccc(N)n3)cc2I)c1] | 2009 |

TABLE 1-continued
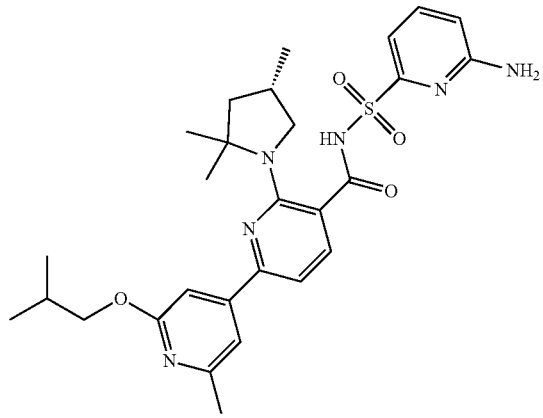 [SMILES: Cc1cc(-c2ccc(C(=O)NS(=O)(=O)c3cccc(N)n3)c(N3C[C@@H](C)CC3(C)C)n2)cc(OCC(C)C)n1] 2010
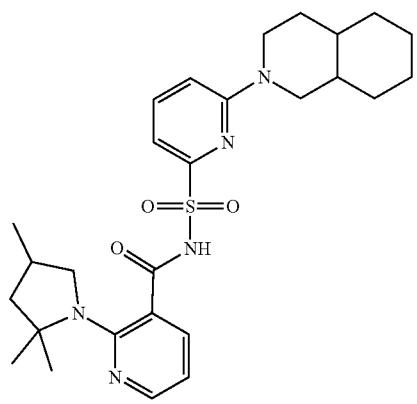 [SMILES: CC1CN(c2ncccc2C(=O)NS(=O)(=O)c2cccc(N3CCC4CCCCC4C3)n2)C(C)(C)C1] 2011
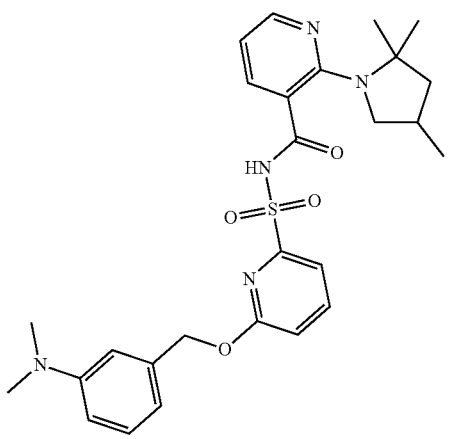 2012
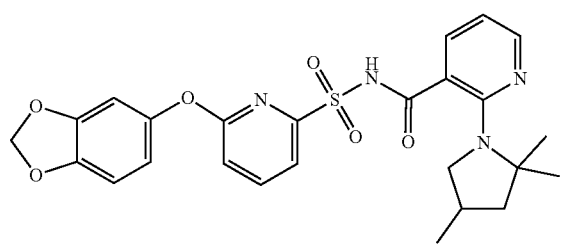 [SMILES: CC1CN(c2ncccc2C(=O)NS(=O)(=O)c2cccc(Oc3ccc4c(c3)OCO4)n2)C(C)(C)C1] 2013

TABLE 1-continued
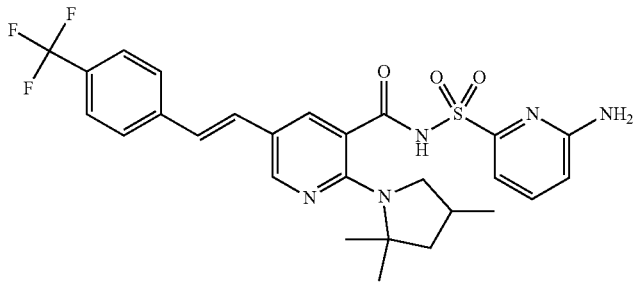 [SMILES: CC1CN(c2ncc(/C=C/c3ccc(C(F)(F)F)cc3)cc2C(=O)NS(=O)(=O)c2cccc(N)n2)C(C)(C)C1]
2014
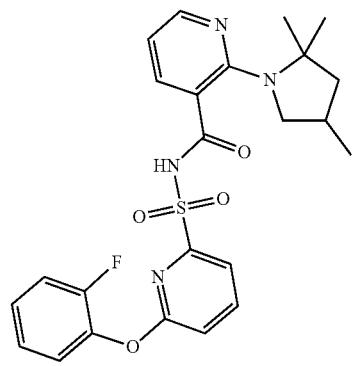 [SMILES: CC1CN(c2ncccc2C(=O)NS(=O)(=O)c2cccc(Oc3ccccc3F)n2)C(C)(C)C1]
2015
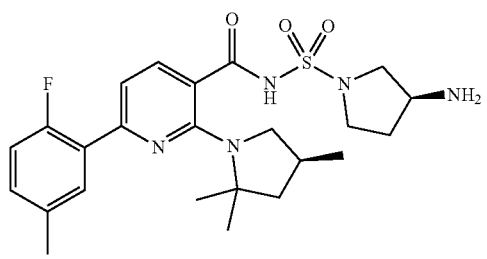 [SMILES: Cc1ccc(F)c(-c2ccc(C(=O)NS(=O)(=O)N3CC[C@H](N)C3)c(N3C[C@@H](C)CC3(C)C)n2)c1]
2016
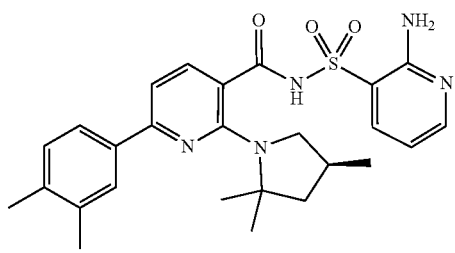 [SMILES: Cc1ccc(-c2ccc(C(=O)NS(=O)(=O)c3cccnc3N)c(N3C[C@@H](C)CC3(C)C)n2)cc1C]
2017
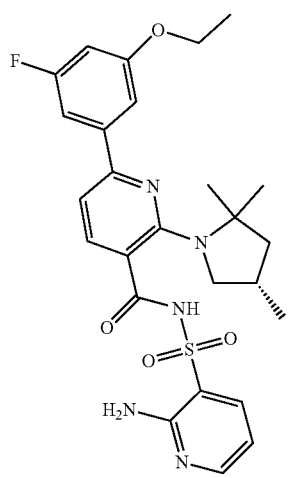 [SMILES: CCOc1cc(F)cc(-c2ccc(C(=O)NS(=O)(=O)c3cccnc3N)c(N3C[C@@H](C)CC3(C)C)n2)c1]
2018

TABLE 1-continued
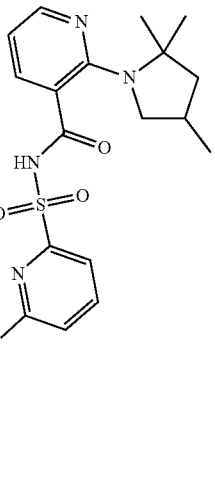
2019
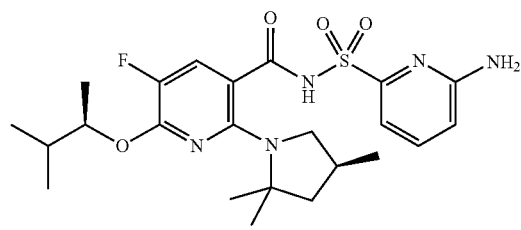 [SMILES: CC(C)[C@@H](C)Oc1nc(N2C[C@@H](C)CC2(C)C)c(C(=O)NS(=O)(=O)c2cccc(N)n2)cc1F]
2020
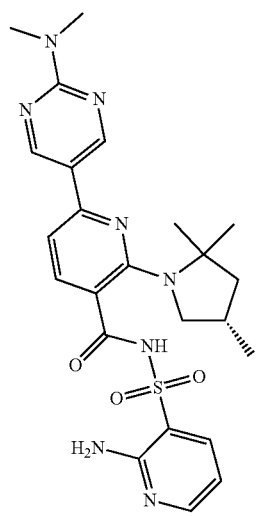
2021
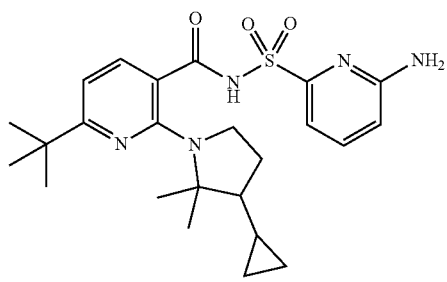 [SMILES: CC(C)(C)c1ccc(C(=O)NS(=O)(=O)c2cccc(N)n2)c(N2CCC(C3CC3)C2(C)C)n1]
2022

TABLE 1-continued
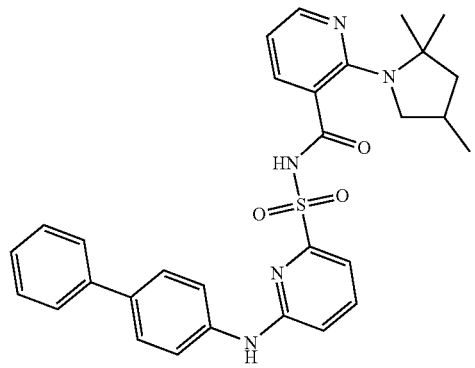 [SMILES: CC1CN(c2ncccc2C(=O)NS(=O)(=O)c2cccc(Nc3ccc(-c4ccccc4)cc3)n2)C(C)(C)C1]
2023
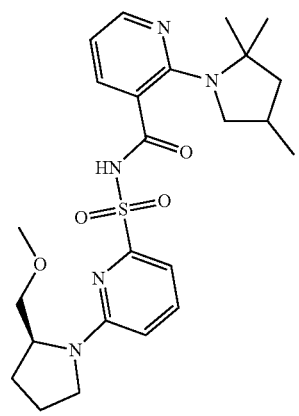 [SMILES: COC[C@@H]1CCCN1c1cccc(S(=O)(=O)NC(=O)c2cccnc2N2CC(C)CC2(C)C)n1]
2024
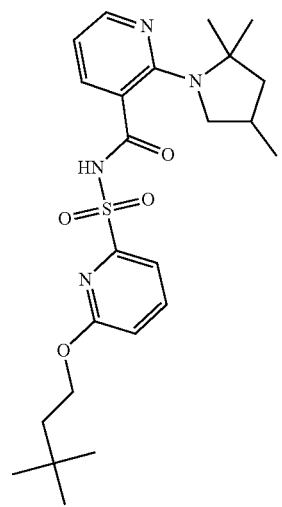 [SMILES: CC1CN(c2ncccc2C(=O)NS(=O)(=O)c2cccc(OCCC(C)(C)C)n2)C(C)(C)C1]
2025

| | |
|---|---|
| 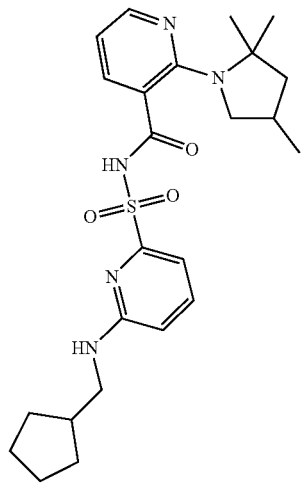 [SMILES: CC1CN(c2ncccc2C(=O)NS(=O)(=O)c2cccc(NCC3CCCC3)n2)C(C)(C)C1] | 2026 |
| 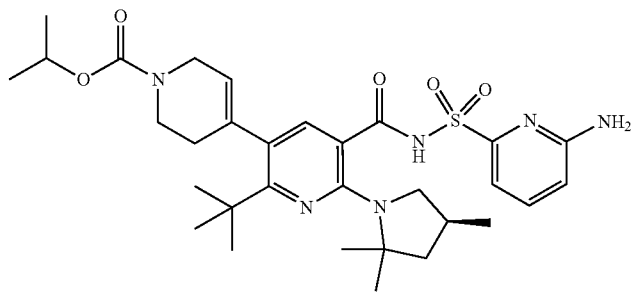 [SMILES: CC(C)OC(=O)N1CC=C(c2cc(C(=O)NS(=O)(=O)c3cccc(N)n3)c(N3C[C@@H](C)CC3(C)C)nc2C(C)(C)C)CC1] | 2027 |
| 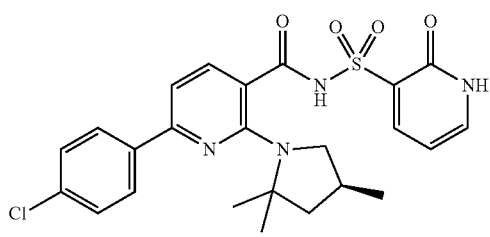 [SMILES: C[C@@H]1CN(c2nc(-c3ccc(Cl)cc3)ccc2C(=O)NS(=O)(=O)c2ccc[nH]c2=O)C(C)(C)C1] | 2028 |
| 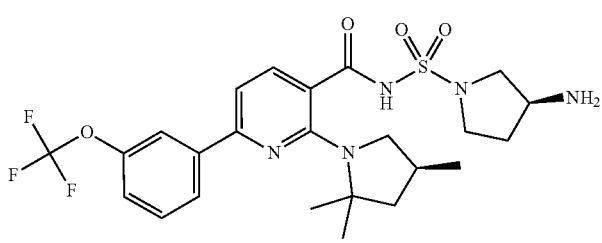 [SMILES: C[C@@H]1CN(c2nc(-c3cccc(OC(F)(F)F)c3)ccc2C(=O)NS(=O)(=O)N2CC[C@H](N)C2)C(C)(C)C1] | 2029 |
| 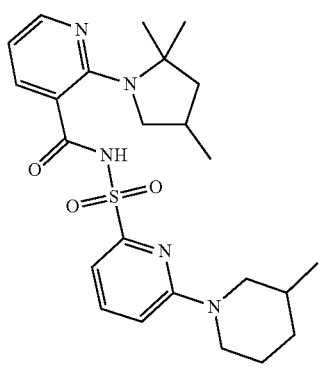 [SMILES: CC1CCCN(c2cccc(S(=O)(=O)NC(=O)c3cccnc3N3CC(C)CC3(C)C)n2)C1] | 2030 |

TABLE 1-continued
| | |
|---|---|
| 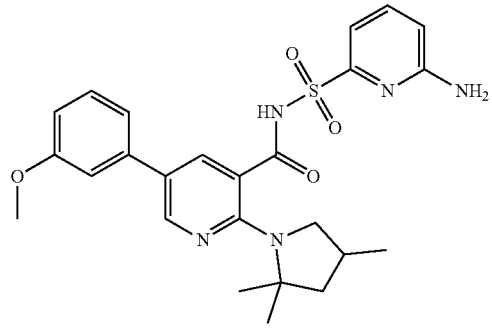 [SMILES: COc1cccc(-c2cnc(N3CC(C)CC3(C)C)c(C(=O)NS(=O)(=O)c3cccc(N)n3)c2)c1] | 2031 |
| 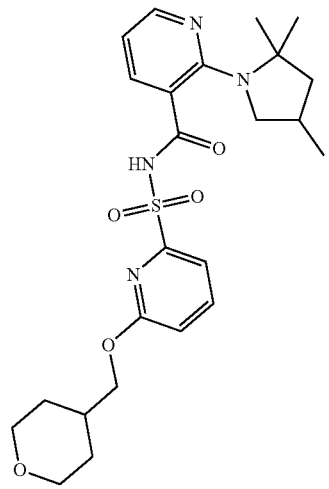 [SMILES: CC1CN(c2ncccc2C(=O)NS(=O)(=O)c2cccc(OCC3CCOCC3)n2)C(C)(C)C1] | 2032 |
| 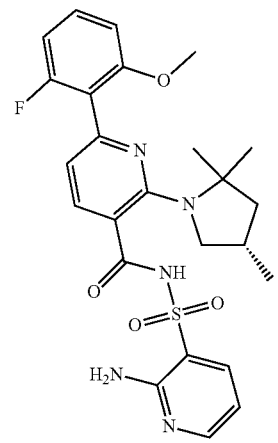 [SMILES: COc1cccc(F)c1-c1ccc(C(=O)NS(=O)(=O)c2cccnc2N)c(N2C[C@@H](C)CC2(C)C)n1] | 2033 |
| 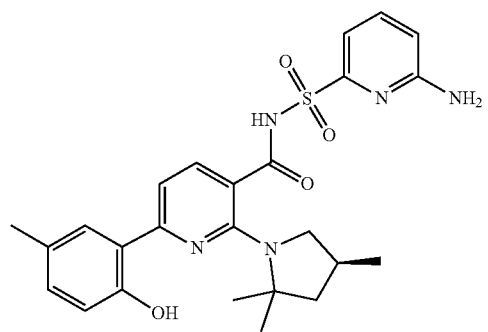 [SMILES: Cc1ccc(O)c(-c2ccc(C(=O)NS(=O)(=O)c3cccc(N)n3)c(N3C[C@@H](C)CC3(C)C)n2)c1] | 2034 |

TABLE 1-continued
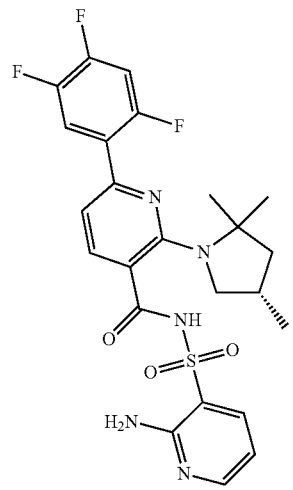 [SMILES: C[C@@H]1CN(c2nc(-c3cc(F)c(F)cc3F)ccc2C(=O)NS(=O)(=O)c2cccnc2N)C(C)(C)C1]
2035
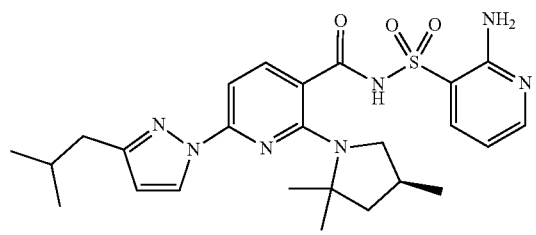 [SMILES: CC(C)Cc1ccn(-c2ccc(C(=O)NS(=O)(=O)c3cccnc3N)c(N3C[C@@H](C)CC3(C)C)n2)n1]
2036
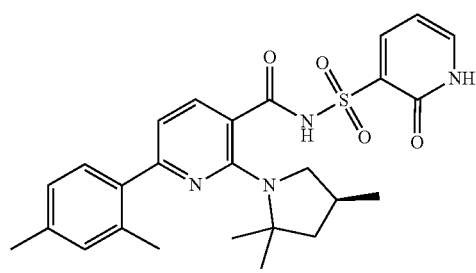
2037
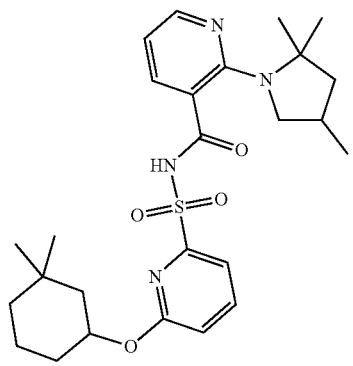 [SMILES: CC1CN(c2ncccc2C(=O)NS(=O)(=O)c2cccc(OC3CCCC(C)(C)C3)n2)C(C)(C)C1]
2038
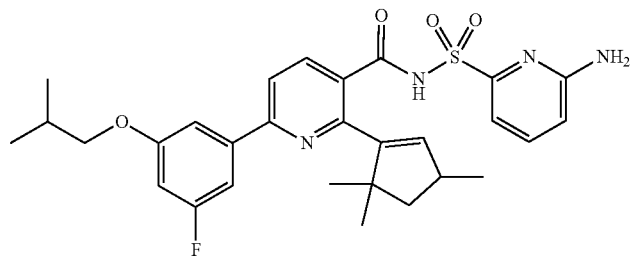 [SMILES: CC(C)COc1cc(F)cc(-c2ccc(C(=O)NS(=O)(=O)c3cccc(N)n3)c(C3=CC(C)CC3(C)C)n2)c1]
2039

TABLE 1-continued
| | |
|---|---|
| 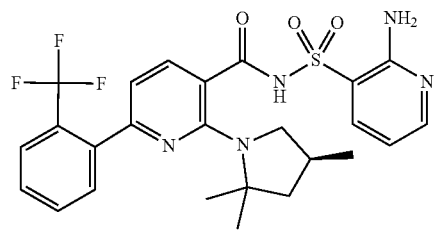 [SMILES: C[C@@H]1CN(c2nc(-c3ccccc3C(F)(F)F)ccc2C(=O)NS(=O)(=O)c2cccnc2N)C(C)(C)C1] | 2040 |
| 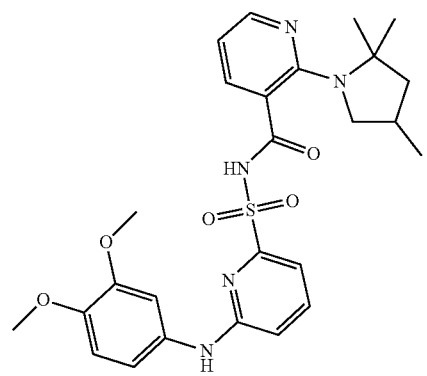 | 2041 |
| 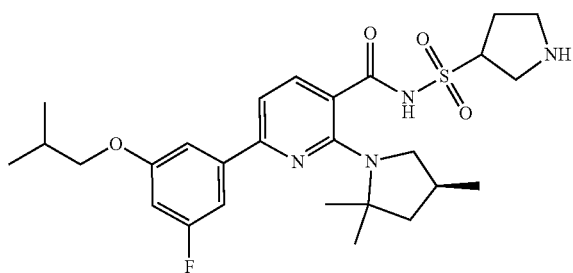 [SMILES: CC(C)COc1cc(F)cc(-c2ccc(C(=O)NS(=O)(=O)C3CCNC3)c(N3C[C@@H](C)CC3(C)C)n2)c1] | 2042 |
| 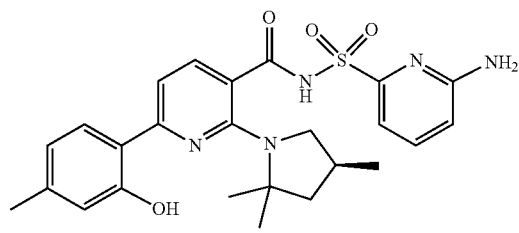 [SMILES: Cc1ccc(-c2ccc(C(=O)NS(=O)(=O)c3cccc(N)n3)c(N3C[C@@H](C)CC3(C)C)n2)c(O)c1] | 2043 |
| 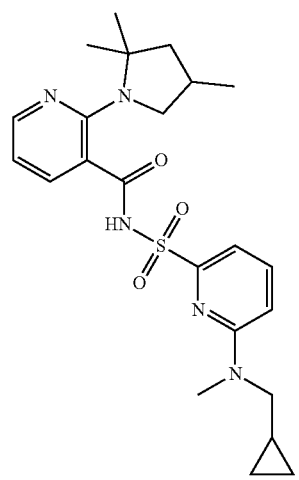 [SMILES: CC1CN(c2ncccc2C(=O)NS(=O)(=O)c2cccc(N(C)CC3CC3)n2)C(C)(C)C1] | 2044 |

TABLE 1-continued
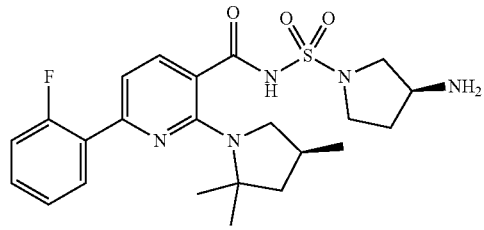 [SMILES: C[C@@H]1CN(c2nc(-c3ccccc3F)ccc2C(=O)NS(=O)(=O)N2CC[C@H](N)C2)C(C)(C)C1]
2045
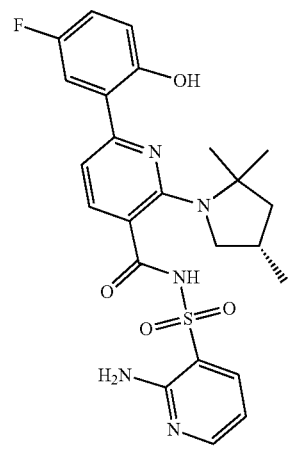 [SMILES: C[C@@H]1CN(c2nc(-c3cc(F)ccc3O)ccc2C(=O)NS(=O)(=O)c2cccnc2N)C(C)(C)C1]
2046
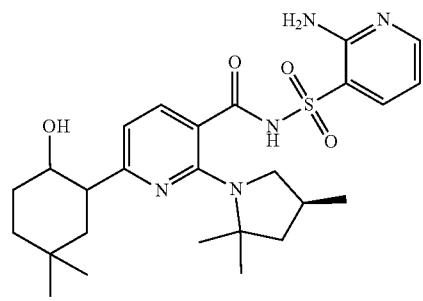 [SMILES: C[C@@H]1CN(c2nc(C3CC(C)(C)CCC3O)ccc2C(=O)NS(=O)(=O)c2cccnc2N)C(C)(C)C1]
2047
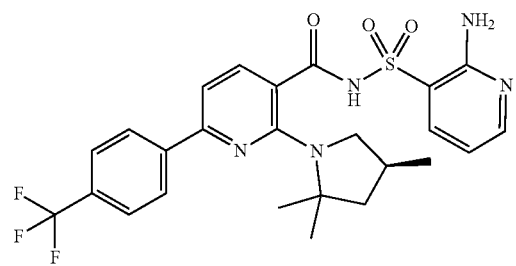 [SMILES: C[C@@H]1CN(c2nc(-c3ccc(C(F)(F)F)cc3)ccc2C(=O)NS(=O)(=O)c2cccnc2N)C(C)(C)C1]
2048

TABLE 1-continued
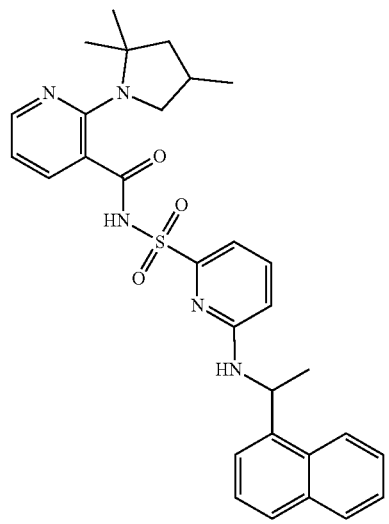 [SMILES: CC1CN(c2ncccc2C(=O)NS(=O)(=O)c2cccc(NC(C)c3cccc4ccccc34)n2)C(C)(C)C1]
2049
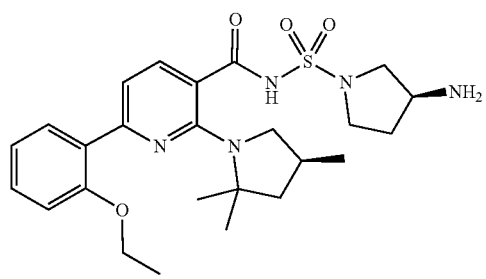 [SMILES: CCOc1ccccc1-c1ccc(C(=O)NS(=O)(=O)N2CC[C@H](N)C2)c(N2C[C@@H](C)CC2(C)C)n1]
2050
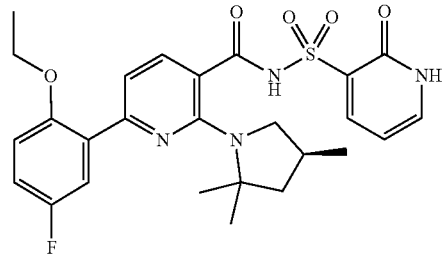 [SMILES: CCOc1ccc(F)cc1-c1ccc(C(=O)NS(=O)(=O)c2ccc[nH]c2=O)c(N2C[C@@H](C)CC2(C)C)n1]
2051
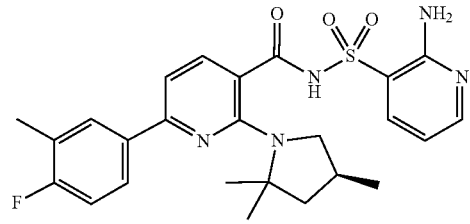 [SMILES: Cc1cc(-c2ccc(C(=O)NS(=O)(=O)c3cccnc3N)c(N3C[C@@H](C)CC3(C)C)n2)ccc1F]
2052

TABLE 1-continued
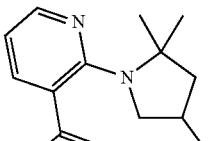
2053
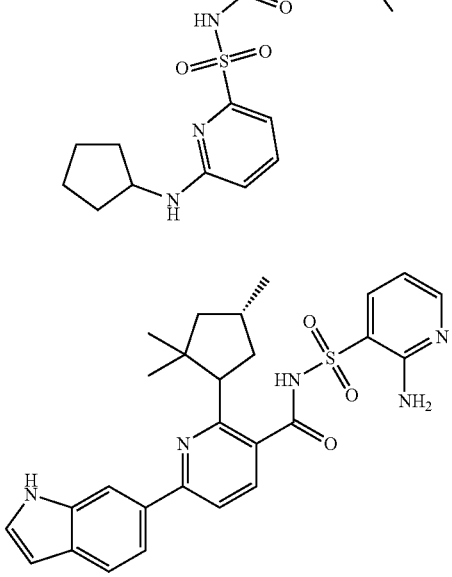
2054
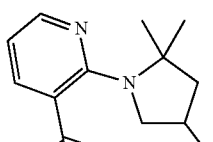
2055
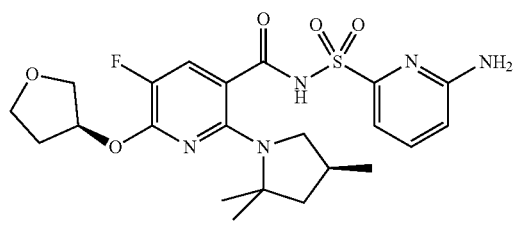 [SMILES: C[C@@H]1CN(c2nc(O[C@H]3CCOC3)c(F)cc2C(=O)NS(=O)(=O)c2cccc(N)n2)C(C)(C)C1]
2056

TABLE 1-continued
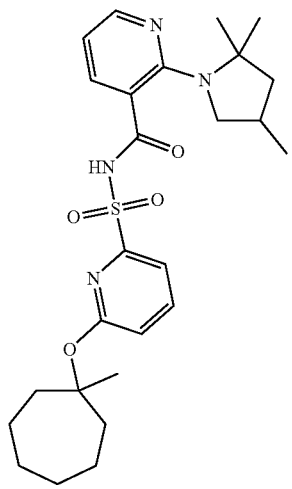 [SMILES: CC1CN(c2ncccc2C(=O)NS(=O)(=O)c2cccc(OC3(C)CCCCCC3)n2)C(C)(C)C1]
2057
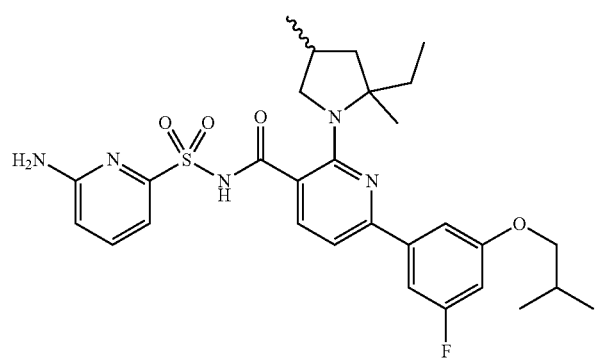 [SMILES: CCC1(C)CC(C)CN1c1nc(-c2cc(F)cc(OCC(C)C)c2)ccc1C(=O)NS(=O)(=O)c1cccc(N)n1]
2058
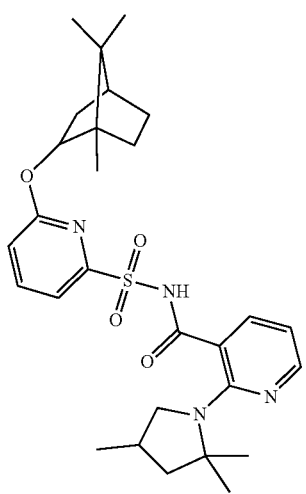 [SMILES: CC1CN(c2ncccc2C(=O)NS(=O)(=O)c2cccc(OC3CC4CCC3(C)C4(C)C)n2)C(C)(C)C1]
2059

TABLE 1-continued
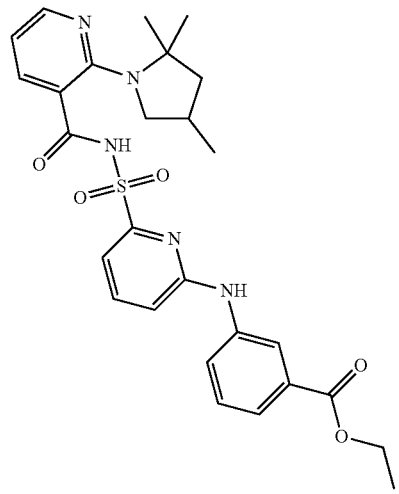 [SMILES: CCOC(=O)c1cccc(Nc2cccc(S(=O)(=O)NC(=O)c3cccnc3N3CC(C)CC3(C)C)n2)c1]
2060
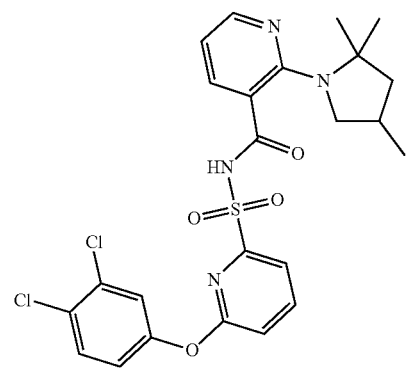 [SMILES: CC1CN(c2ncccc2C(=O)NS(=O)(=O)c2cccc(Oc3ccc(Cl)c(Cl)c3)n2)C(C)(C)C1]
2061
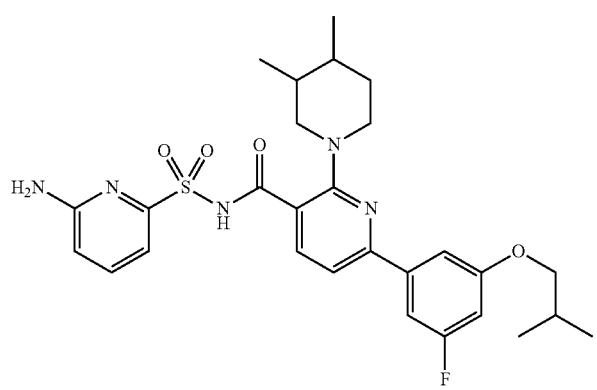
2062
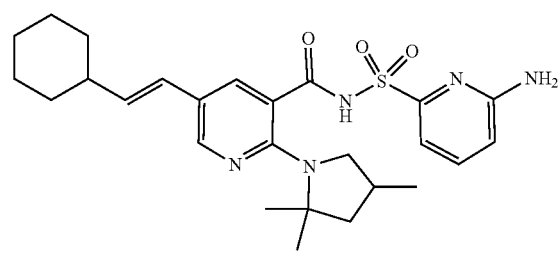 [SMILES: CC1CN(c2ncc(/C=C/C3CCCCC3)cc2C(=O)NS(=O)(=O)c2cccc(N)n2)C(C)(C)C1]
2063

TABLE 1-continued
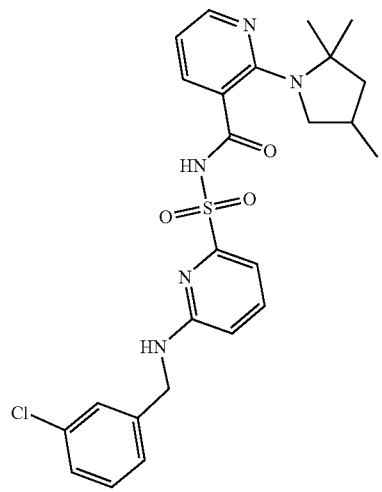 [SMILES: CC1CN(c2ncccc2C(=O)NS(=O)(=O)c2cccc(NCc3cccc(Cl)c3)n2)C(C)(C)C1]
2064
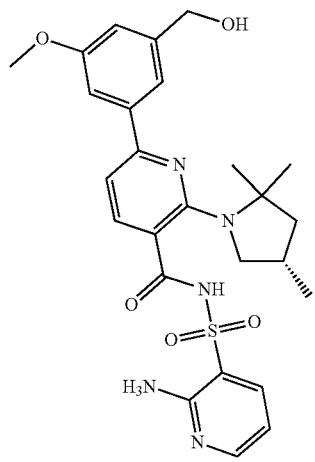
2065
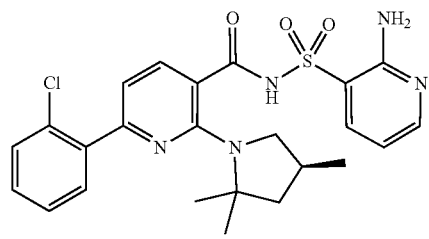 [SMILES: C[C@@H]1CN(c2nc(-c3ccccc3Cl)ccc2C(=O)NS(=O)(=O)c2cccnc2N)C(C)(C)C1]
2066
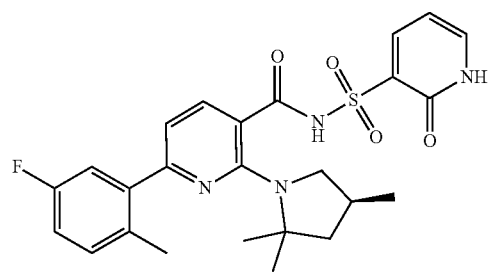 [SMILES: Cc1ccc(F)cc1-c1ccc(C(=O)NS(=O)(=O)c2ccc[nH]c2=O)c(N2C[C@@H](C)CC2(C)C)n1]
2067

TABLE 1-continued
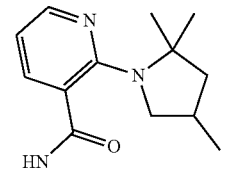
2068
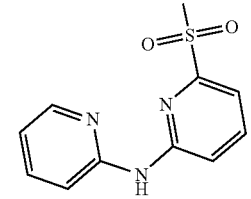
2069
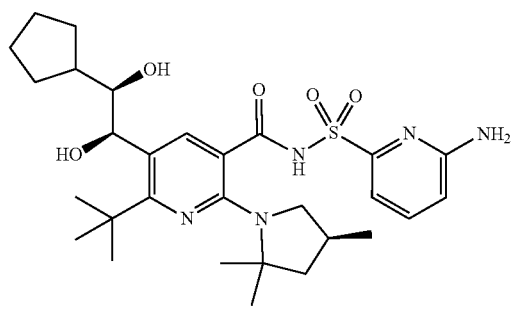 [SMILES: C[C@@H]1CN(c2nc(C(C)(C)C)c([C@@H](O)[C@H](O)C3CCCC3)cc2C(=O)NS(=O)(=O)c2cccc(N)n2)C(C)(C)C1]
2070
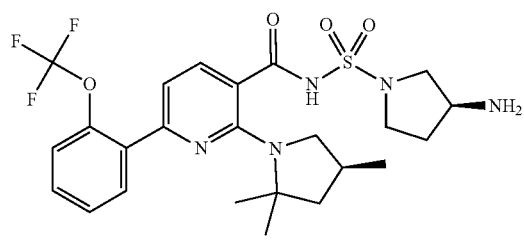 [SMILES: C[C@@H]1CN(c2nc(-c3ccccc3OC(F)(F)F)ccc2C(=O)NS(=O)(=O)N2CC[C@H](N)C2)C(C)(C)C1]
2071
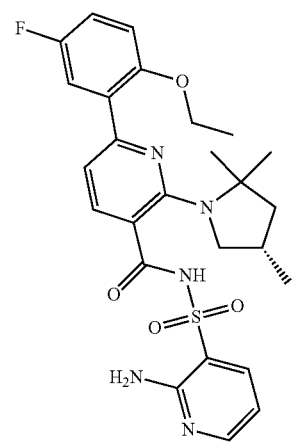 [SMILES: CCOc1ccc(F)cc1-c1ccc(C(=O)NS(=O)(=O)c2cccnc2N)c(N2C[C@@H](C)CC2(C)C)n1]

TABLE 1-continued
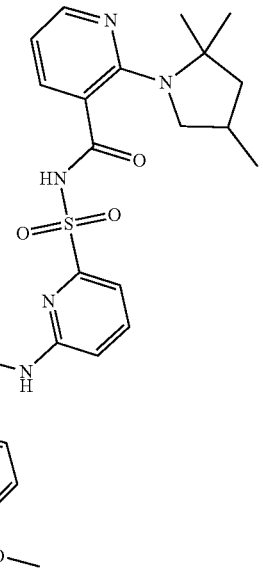
2072
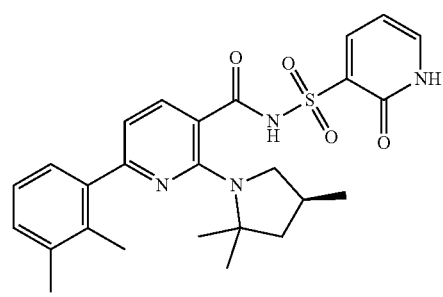 [SMILES: Cc1cccc(-c2ccc(C(=O)NS(=O)(=O)c3ccc[nH]c3=O)c(N3C[C@@H](C)CC3(C)C)n2)c1C]
2073
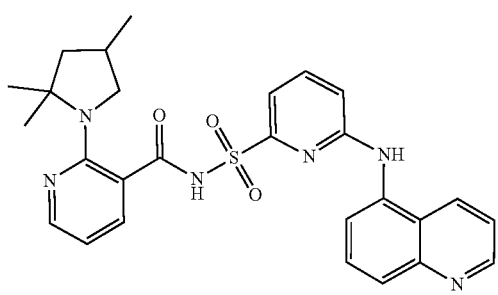 [SMILES: CC1CN(c2ncccc2C(=O)NS(=O)(=O)c2cccc(Nc3cccc4ncccc34)n2)C(C)(C)C1]
2074
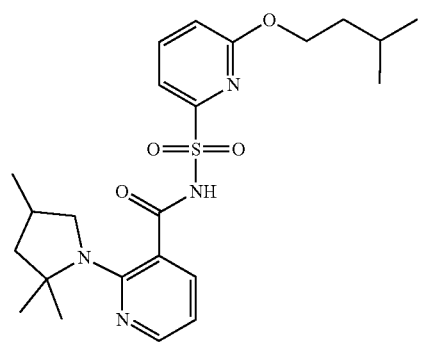 [SMILES: CC(C)CCOc1cccc(S(=O)(=O)NC(=O)c2cccnc2N2CC(C)CC2(C)C)n1]
2075

TABLE 1-continued
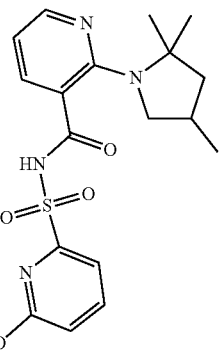
2076
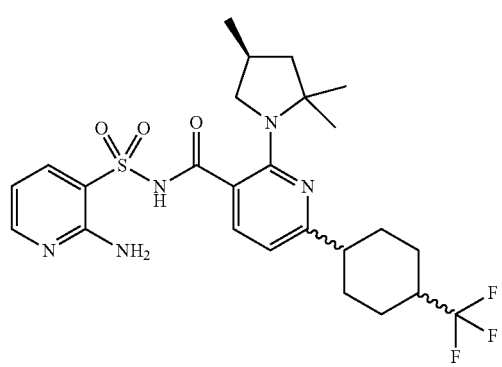 [SMILES: C[C@@H]1CN(c2nc(C3CCC(C(F)(F)F)CC3)ccc2C(=O)NS(=O)(=O)c2cccnc2N)C(C)(C)C1]
2077
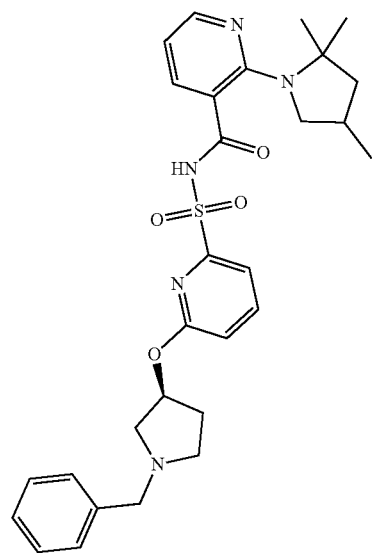 [SMILES: CC1CN(c2ncccc2C(=O)NS(=O)(=O)c2cccc(O[C@H]3CCN(Cc4ccccc4)C3)n2)C(C)(C)C1]
2078
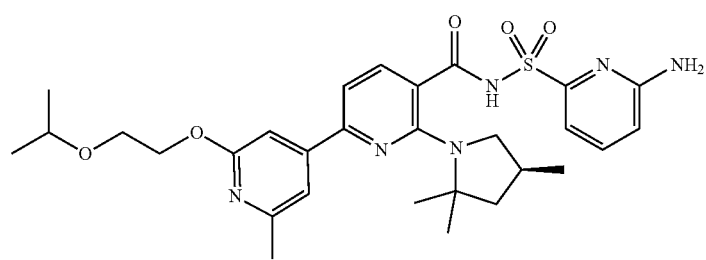 [SMILES: Cc1cc(-c2ccc(C(=O)NS(=O)(=O)c3cccc(N)n3)c(N3C[C@@H](C)CC3(C)C)n2)cc(OCCOC(C)C)n1]
2079

TABLE 1-continued
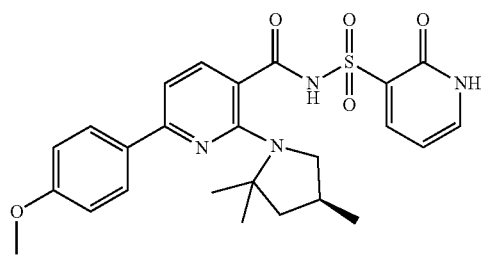 [SMILES: COc1ccc(-c2ccc(C(=O)NS(=O)(=O)c3ccc[nH]c3=O)c(N3C[C@@H](C)CC3(C)C)n2)cc1]
2080
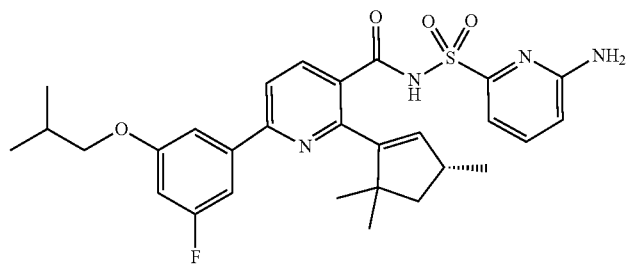 [SMILES: CC(C)COc1cc(F)cc(-c2ccc(C(=O)NS(=O)(=O)c3cccc(N)n3)c(C3=C[C@H](C)CC3(C)C)n2)c1]
2081
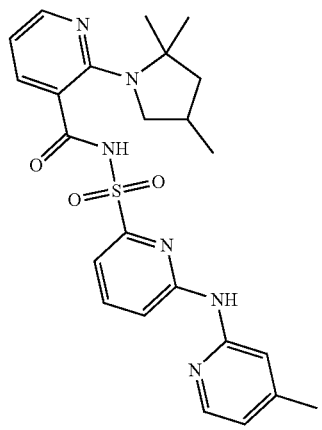 [SMILES: Cc1ccnc(Nc2cccc(S(=O)(=O)NC(=O)c3cccnc3N3CC(C)CC3(C)C)n2)c1]
2082
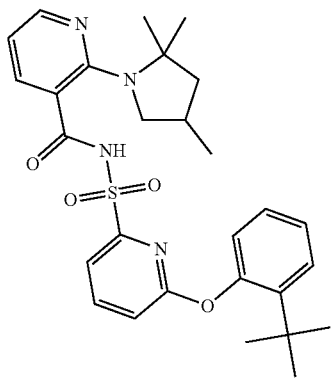 [SMILES: CC1CN(c2ncccc2C(=O)NS(=O)(=O)c2cccc(Oc3ccccc3C(C)(C)C)n2)C(C)(C)C1]
2083
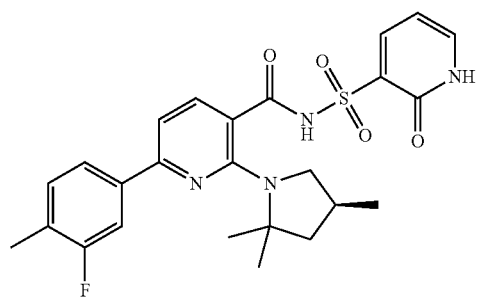 [SMILES: Cc1ccc(-c2ccc(C(=O)NS(=O)(=O)c3ccc[nH]c3=O)c(N3C[C@@H](C)CC3(C)C)n2)cc1F]
2084

TABLE 1-continued
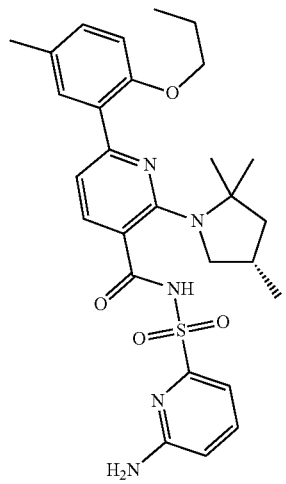
2085
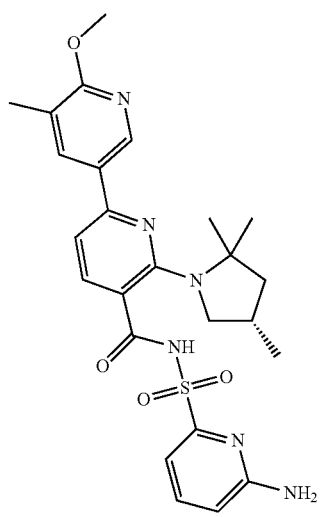 [SMILES: COc1ncc(-c2ccc(C(=O)NS(=O)(=O)c3cccc(N)n3)c(N3C[C@@H](C)CC3(C)C)n2)cc1C]
2086
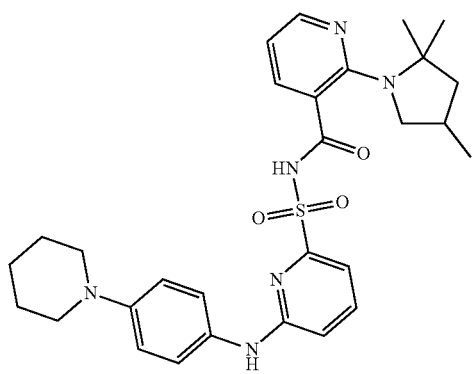 [SMILES: CC1CN(c2ncccc2C(=O)NS(=O)(=O)c2cccc(Nc3ccc(N4CCCCC4)cc3)n2)C(C)(C)C1]
2087
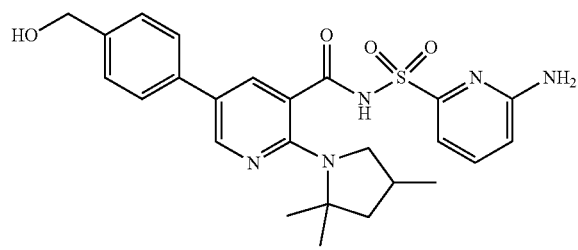
2088

TABLE 1-continued
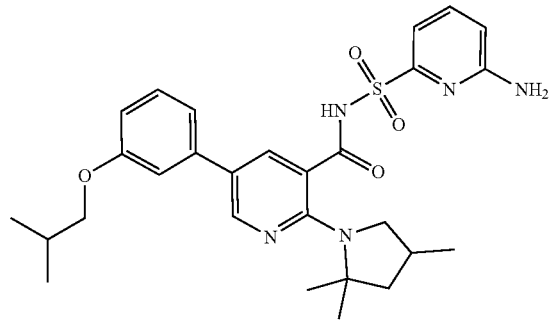 [SMILES: CC(C)COc1cccc(-c2cnc(N3CC(C)CC3(C)C)c(C(=O)NS(=O)(=O)c3cccc(N)n3)c2)c1] 2089
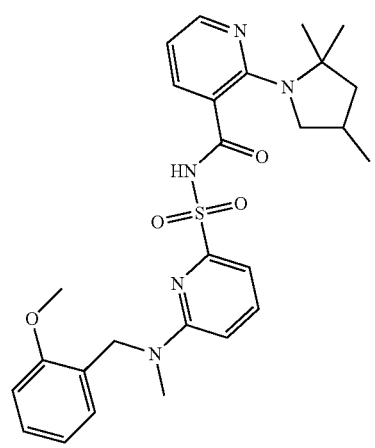 [SMILES: COc1ccccc1CN(C)c1cccc(S(=O)(=O)NC(=O)c2cccnc2N2CC(C)CC2(C)C)n1] 2090
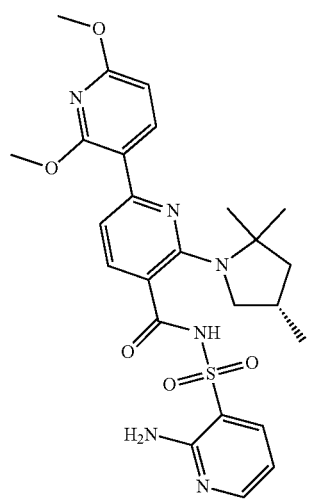 2091
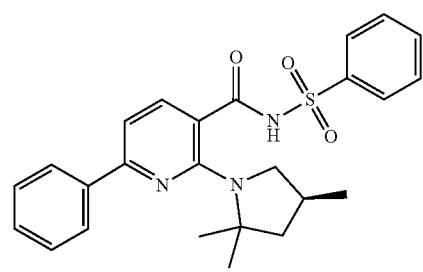 [SMILES: C[C@@H]1CN(c2nc(-c3ccccc3)ccc2C(=O)NS(=O)(=O)c2ccccc2)C(C)(C)C1] 2092

TABLE 1-continued
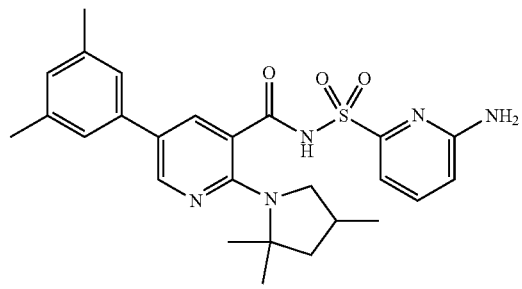
2093
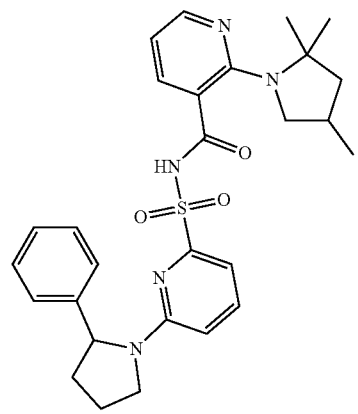 [SMILES: CC1CN(c2ncccc2C(=O)NS(=O)(=O)c2cccc(N3CCCC3c3ccccc3)n2)C(C)(C)C1]
2094
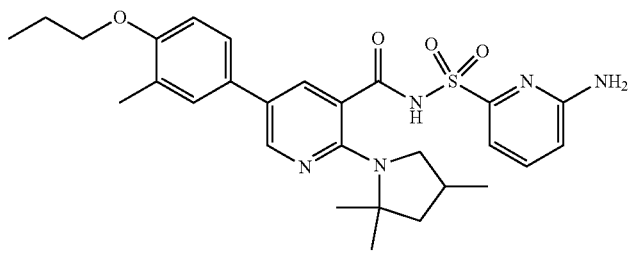
2095
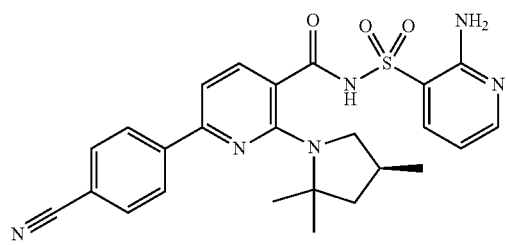 [SMILES: C[C@@H]1CN(c2nc(-c3ccc(C#N)cc3)ccc2C(=O)NS(=O)(=O)c2cccnc2N)C(C)(C)C1]
2096
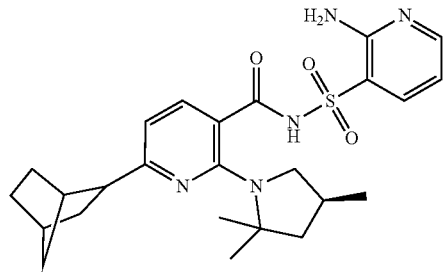 [SMILES: C[C@@H]1CN(c2nc(C3CC4CCC3C4)ccc2C(=O)NS(=O)(=O)c2cccnc2N)C(C)(C)C1]
2097

TABLE 1-continued
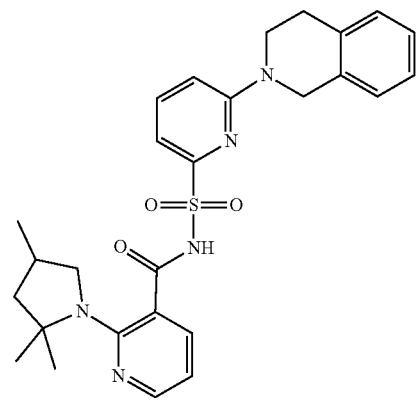 [SMILES: CC1CN(c2ncccc2C(=O)NS(=O)(=O)c2cccc(N3CCc4ccccc4C3)n2)C(C)(C)C1]
2098
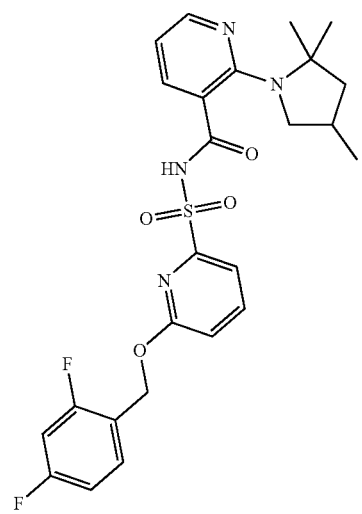 [SMILES: CC1CN(c2ncccc2C(=O)NS(=O)(=O)c2cccc(OCc3ccc(F)cc3F)n2)C(C)(C)C1]
2099
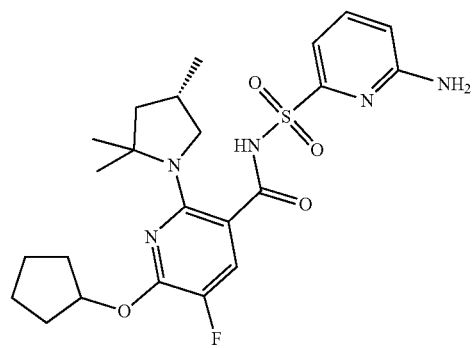 [SMILES: C[C@@H]1CN(c2nc(OC3CCCC3)c(F)cc2C(=O)NS(=O)(=O)c2cccc(N)n2)C(C)(C)C1]
2100

TABLE 1-continued
| | |
|---|---|
| 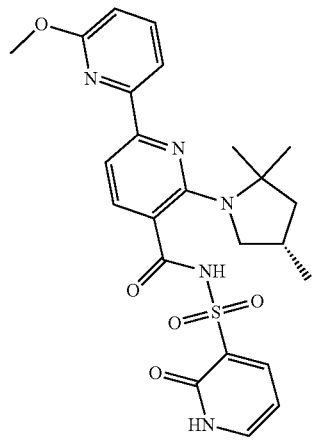 | 2101 |
| 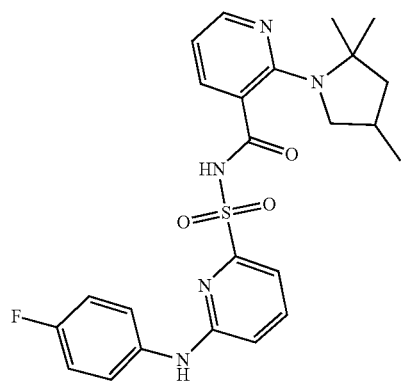 [SMILES: CC1CN(c2ncccc2C(=O)NS(=O)(=O)c2cccc(Nc3ccc(F)cc3)n2)C(C)(C)C1] | 2102 |
| 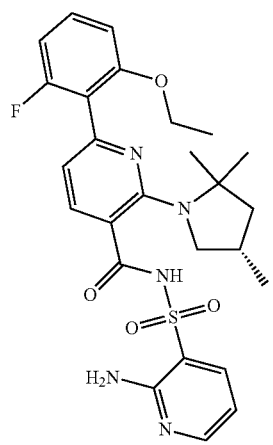 [SMILES: CCOc1cccc(F)c1-c1ccc(C(=O)NS(=O)(=O)c2cccnc2N)c(N2C[C@@H](C)CC2(C)C)n1] | 2103 |
| 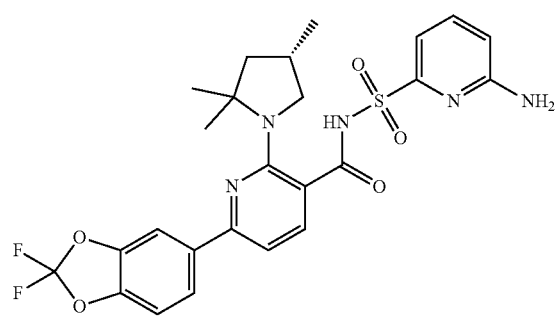 [SMILES: C[C@@H]1CN(c2nc(-c3ccc4c(c3)OC(F)(F)O4)ccc2C(=O)NS(=O)(=O)c2cccc(N)n2)C(C)(C)C1] | 2104 |

TABLE 1-continued
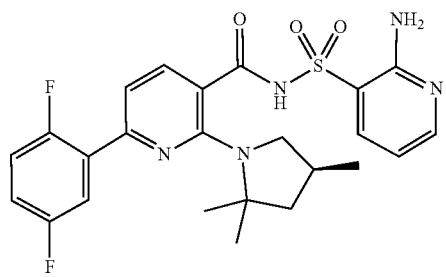 [SMILES: C[C@@H]1CN(c2nc(-c3cc(F)ccc3F)ccc2C(=O)NS(=O)(=O)c2cccnc2N)C(C)(C)C1]
2105
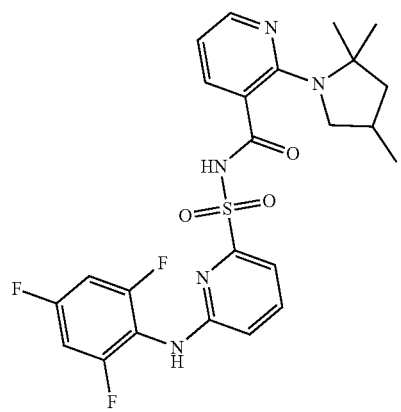 [SMILES: CC1CN(c2ncccc2C(=O)NS(=O)(=O)c2cccc(Nc3c(F)cc(F)cc3F)n2)C(C)(C)C1]
2106
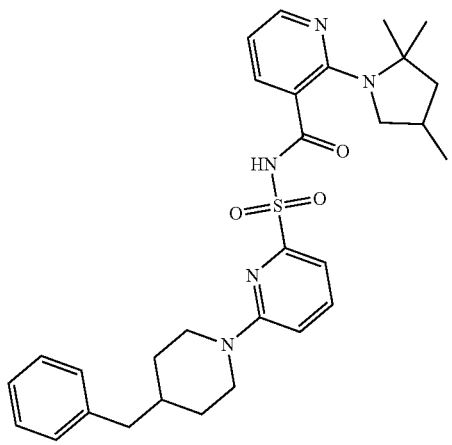 [SMILES: CC1CN(c2ncccc2C(=O)NS(=O)(=O)c2cccc(N3CCC(Cc4ccccc4)CC3)n2)C(C)(C)C1]
2107
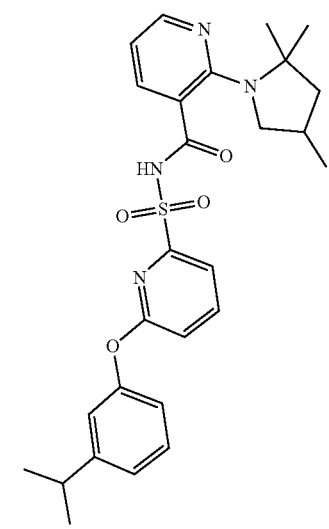 [SMILES: CC1CN(c2ncccc2C(=O)NS(=O)(=O)c2cccc(Oc3cccc(C(C)C)c3)n2)C(C)(C)C1]
2108

TABLE 1-continued
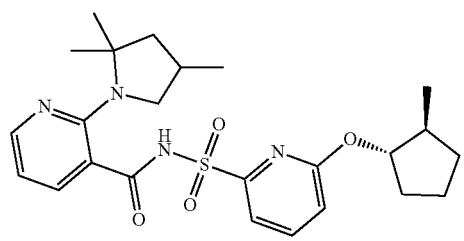 [SMILES: CC1CN(c2ncccc2C(=O)NS(=O)(=O)c2cccc(O[C@H]3CCC[C@@H]3C)n2)C(C)(C)C1] 2109
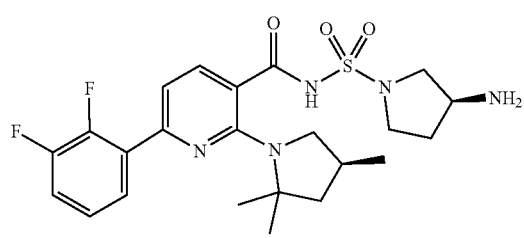 [SMILES: C[C@@H]1CN(c2nc(-c3cccc(F)c3F)ccc2C(=O)NS(=O)(=O)N2CC[C@H](N)C2)C(C)(C)C1] 2110
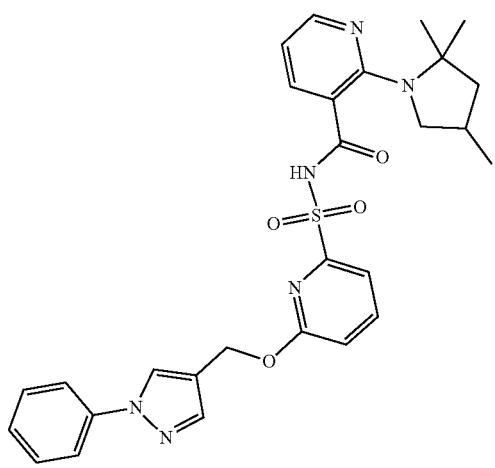 [SMILES: CC1CN(c2ncccc2C(=O)NS(=O)(=O)c2cccc(OCc3cnn(-c4ccccc4)c3)n2)C(C)(C)C1] 2111
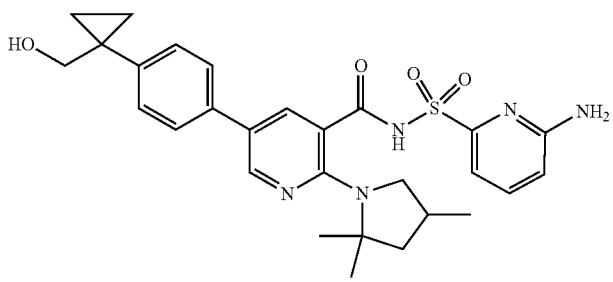 [SMILES: CC1CN(c2ncc(-c3ccc(C4(CO)CC4)cc3)cc2C(=O)NS(=O)(=O)c2cccc(N)n2)C(C)(C)C1] 2112
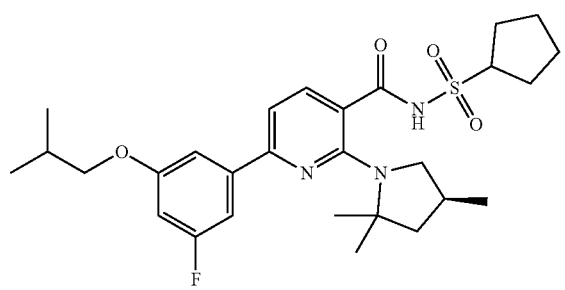 [SMILES: CC(C)COc1cc(F)cc(-c2ccc(C(=O)NS(=O)(=O)C3CCCC3)c(N3C[C@@H](C)CC3(C)C)n2)c1] 2113

TABLE 1-continued

| | |
|---|---|
| | 2114 |
| | 2115 |
| | 2116 |
| | 2117 |

TABLE 1-continued
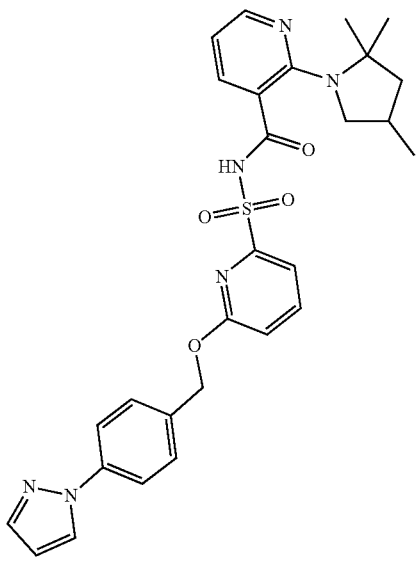 [SMILES: CC1CN(c2ncccc2C(=O)NS(=O)(=O)c2cccc(OCc3ccc(-n4cccn4)cc3)n2)C(C)(C)C1]
2118
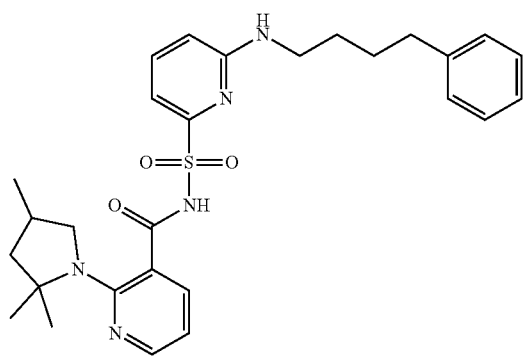 [SMILES: CC1CN(c2ncccc2C(=O)NS(=O)(=O)c2cccc(NCCCCc3ccccc3)n2)C(C)(C)C1]
2119
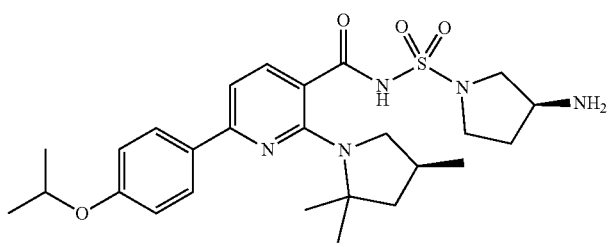 [SMILES: CC(C)Oc1ccc(-c2ccc(C(=O)NS(=O)(=O)N3CC[C@H](N)C3)c(N3C[C@@H](C)CC3(C)C)n2)cc1]
2120
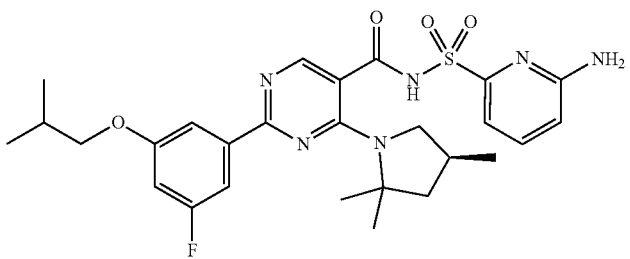 [SMILES: CC(C)COc1cc(F)cc(-c2ncc(C(=O)NS(=O)(=O)c3cccc(N)n3)c(N3C[C@@H](C)CC3(C)C)n2)c1]
2121

TABLE 1-continued
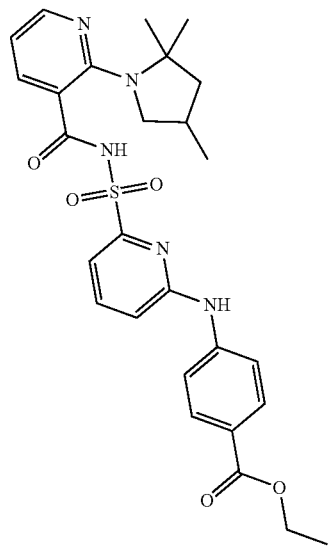 [SMILES: CCOC(=O)c1ccc(Nc2cccc(S(=O)(=O)NC(=O)c3cccnc3N3CC(C)CC3(C)C)n2)cc1]
2122
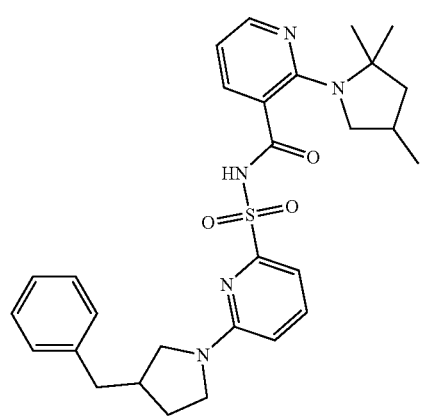 [SMILES: CC1CN(c2ncccc2C(=O)NS(=O)(=O)c2cccc(N3CCC(Cc4ccccc4)C3)n2)C(C)(C)C1]
2123
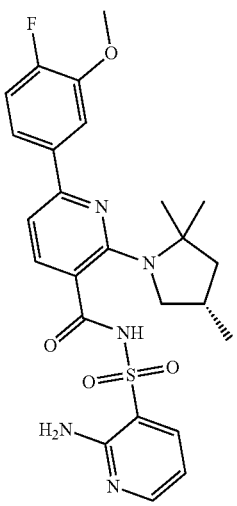 [SMILES: COc1cc(-c2ccc(C(=O)NS(=O)(=O)c3cccnc3N)c(N3C[C@@H](C)CC3(C)C)n2)ccc1F]
2124

TABLE 1-continued
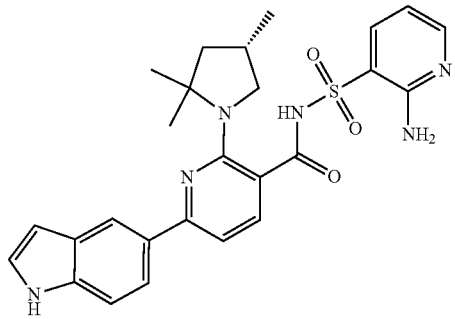
2125
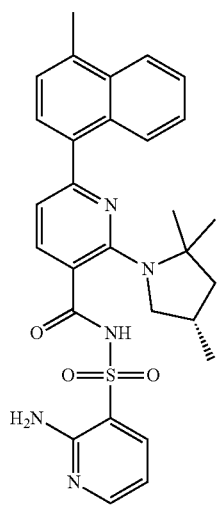 [SMILES: Cc1ccc(-c2ccc(C(=O)NS(=O)(=O)c3cccnc3N)c(N3C[C@@H](C)CC3(C)C)n2)c2ccccc12]
2126
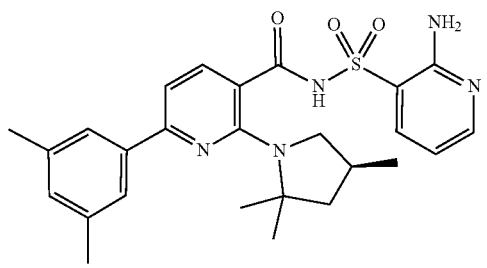 [SMILES: Cc1cc(C)cc(-c2ccc(C(=O)NS(=O)(=O)c3cccnc3N)c(N3C[C@@H](C)CC3(C)C)n2)c1]
2127
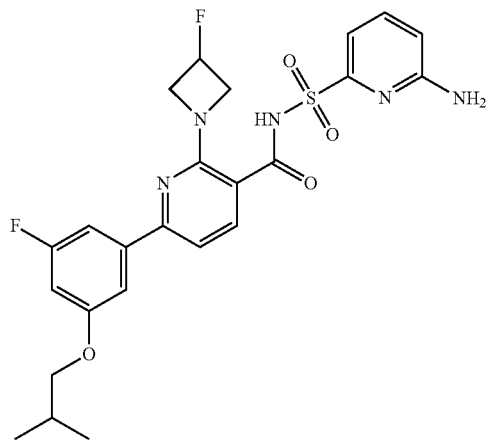 [SMILES: CC(C)COc1cc(F)cc(-c2ccc(C(=O)NS(=O)(=O)c3cccc(N)n3)c(N3CC(F)C3)n2)c1]
2128

TABLE 1-continued
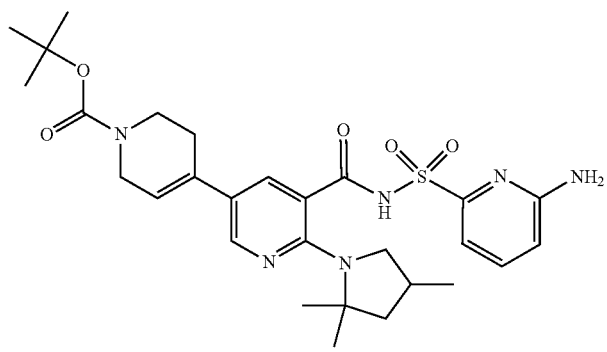 [SMILES: CC1CN(c2ncc(C3=CCN(C(=O)OC(C)(C)C)CC3)cc2C(=O)NS(=O)(=O)c2cccc(N)n2)C(C)(C)C1] 2129
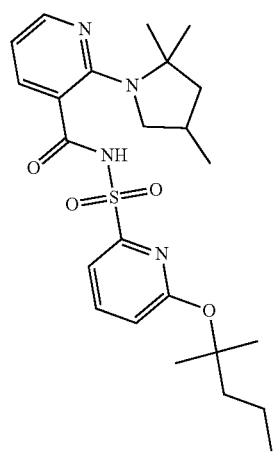 [SMILES: CCCC(C)(C)Oc1cccc(S(=O)(=O)NC(=O)c2cccnc2N2CC(C)CC2(C)C)n1] 2130
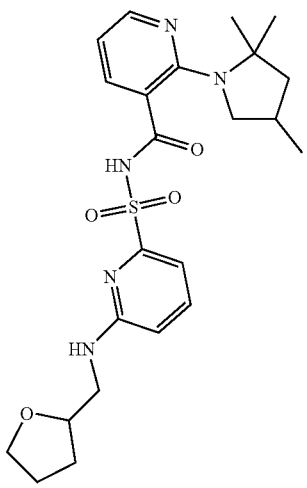 [SMILES: CC1CN(c2ncccc2C(=O)NS(=O)(=O)c2cccc(NCC3CCCO3)n2)C(C)(C)C1] 2131
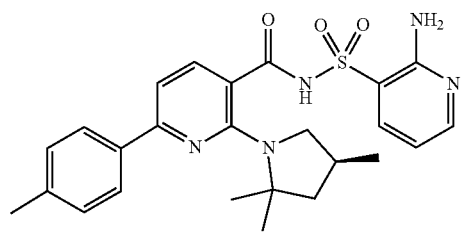 [SMILES: Cc1ccc(-c2ccc(C(=O)NS(=O)(=O)c3cccnc3N)c(N3C[C@@H](C)CC3(C)C)n2)cc1] 2132

TABLE 1-continued
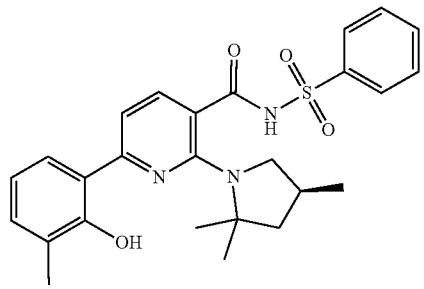 [SMILES: Cc1cccc(-c2ccc(C(=O)NS(=O)(=O)c3ccccc3)c(N3C[C@@H](C)CC3(C)C)n2)c1O]
2133
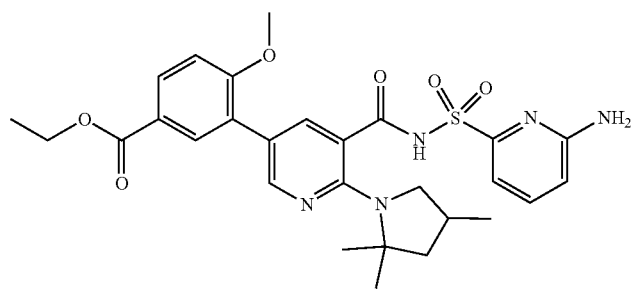 [SMILES: CCOC(=O)c1ccc(OC)c(-c2cnc(N3CC(C)CC3(C)C)c(C(=O)NS(=O)(=O)c3cccc(N)n3)c2)c1]
2134
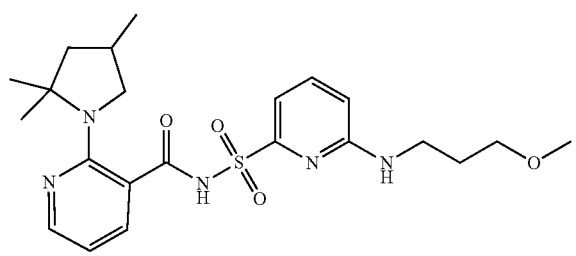
2135
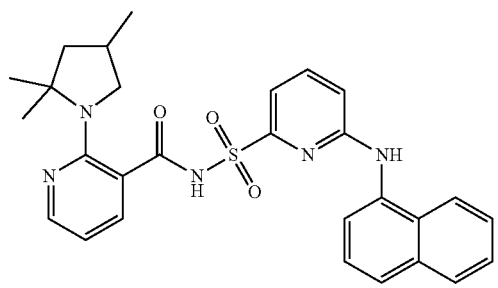 [SMILES: CC1CN(c2ncccc2C(=O)NS(=O)(=O)c2cccc(Nc3cccc4ccccc34)n2)C(C)(C)C1]
2136
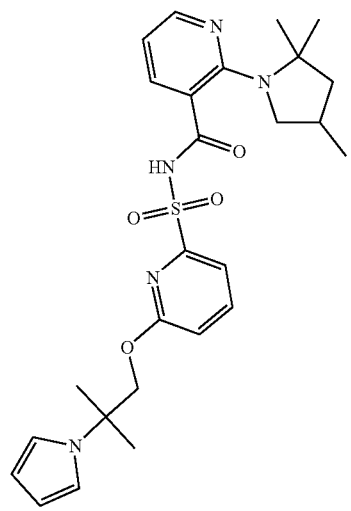 [SMILES: CC1CN(c2ncccc2C(=O)NS(=O)(=O)c2cccc(OCC(C)(C)n3cccc3)n2)C(C)(C)C1]
2137

TABLE 1-continued
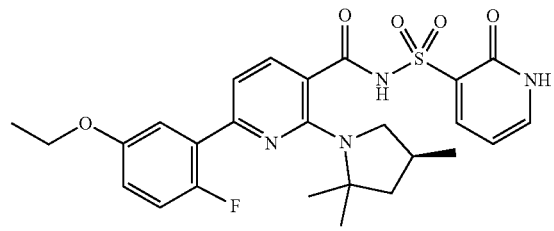 [SMILES: CCOc1ccc(F)c(-c2ccc(C(=O)NS(=O)(=O)c3ccc[nH]c3=O)c(N3C[C@@H](C)CC3(C)C)n2)c1]
2138
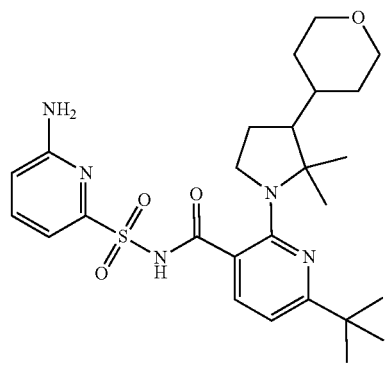 [SMILES: CC(C)(C)c1ccc(C(=O)NS(=O)(=O)c2cccc(N)n2)c(N2CCC(C3CCOCC3)C2(C)C)n1]
2139
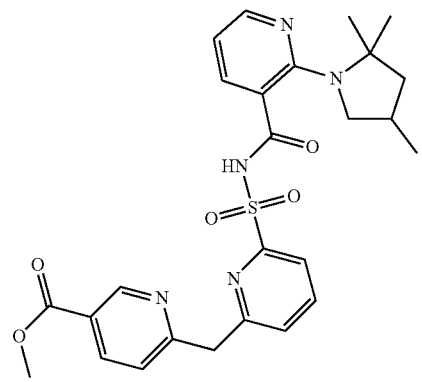 [SMILES: COC(=O)c1ccc(Cc2cccc(S(=O)(=O)NC(=O)c3cccnc3N3CC(C)CC3(C)C)n2)nc1]
2140
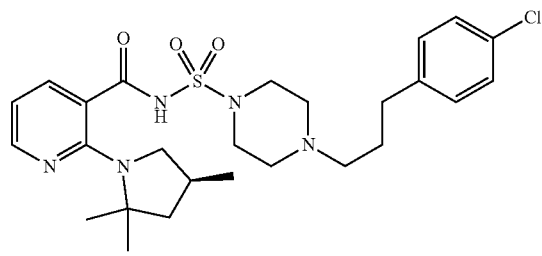 [SMILES: C[C@@H]1CN(c2ncccc2C(=O)NS(=O)(=O)N2CCN(CCCc3ccc(Cl)cc3)CC2)C(C)(C)C1]
2141

TABLE 1-continued
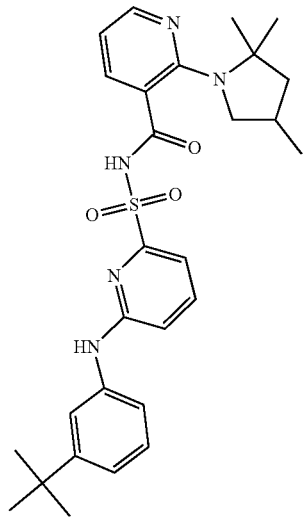 [SMILES: CC1CN(c2ncccc2C(=O)NS(=O)(=O)c2cccc(Nc3cccc(C(C)(C)C)c3)n2)C(C)(C)C1]
2142
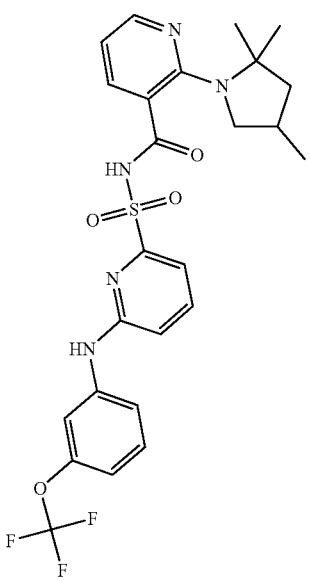 [SMILES: CC1CN(c2ncccc2C(=O)NS(=O)(=O)c2cccc(Nc3cccc(OC(F)(F)F)c3)n2)C(C)(C)C1]
2143
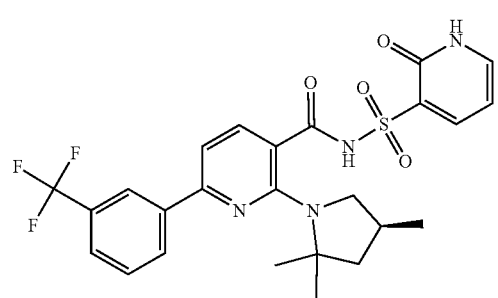 [SMILES: C[C@@H]1CN(c2nc(-c3cccc(C(F)(F)F)c3)ccc2C(=O)NS(=O)(=O)c2ccc[nH]c2=O)C(C)(C)C1]
2144

TABLE 1-continued
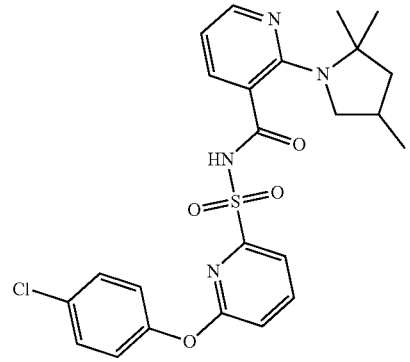 [SMILES: CC1CN(c2ncccc2C(=O)NS(=O)(=O)c2cccc(Oc3ccc(Cl)cc3)n2)C(C)(C)C1]
2145
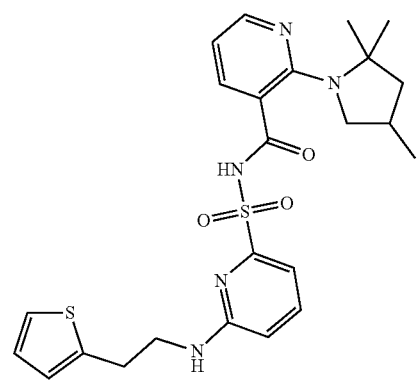 [SMILES: CC1CN(c2ncccc2C(=O)NS(=O)(=O)c2cccc(NCCc3cccs3)n2)C(C)(C)C1]
2146
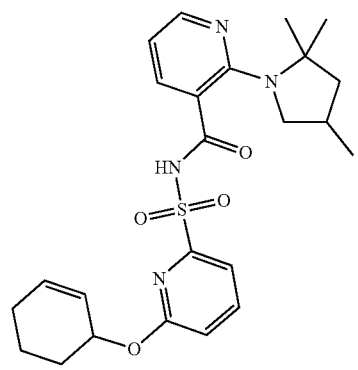 [SMILES: CC1CN(c2ncccc2C(=O)NS(=O)(=O)c2cccc(OC3C=CCCC3)n2)C(C)(C)C1]
2147
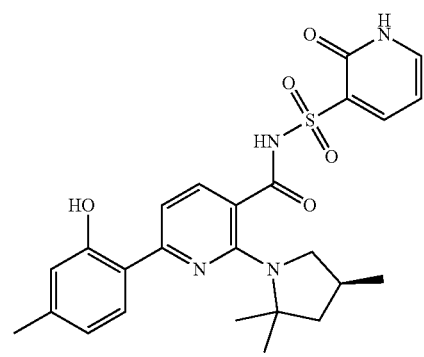 [SMILES: Cc1ccc(-c2ccc(C(=O)NS(=O)(=O)c3ccc[nH]c3=O)c(N3C[C@@H](C)CC3(C)C)n2)c(O)c1]
2148

TABLE 1-continued
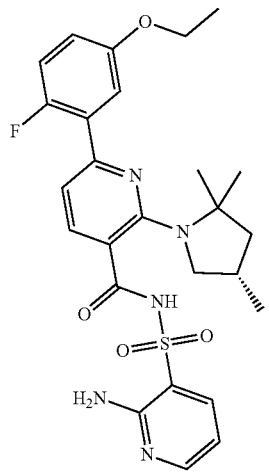 [SMILES: CCOc1ccc(F)c(-c2ccc(C(=O)NS(=O)(=O)c3cccnc3N)c(N3C[C@@H](C)CC3(C)C)n2)c1]
2149
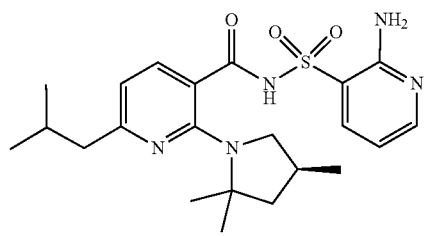 [SMILES: CC(C)Cc1ccc(C(=O)NS(=O)(=O)c2cccnc2N)c(N2C[C@@H](C)CC2(C)C)n1]
2150
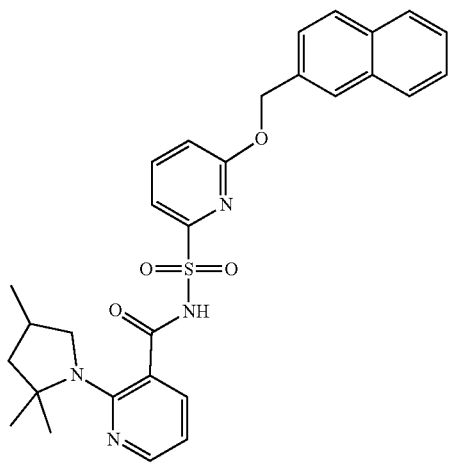 [SMILES: CC1CN(c2ncccc2C(=O)NS(=O)(=O)c2cccc(OCc3ccc4ccccc4c3)n2)C(C)(C)C1]
2151
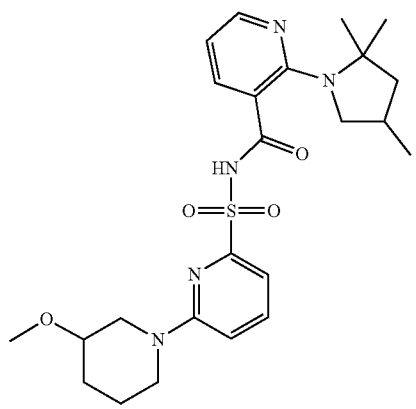
2152

TABLE 1-continued
| | |
|---|---|
| 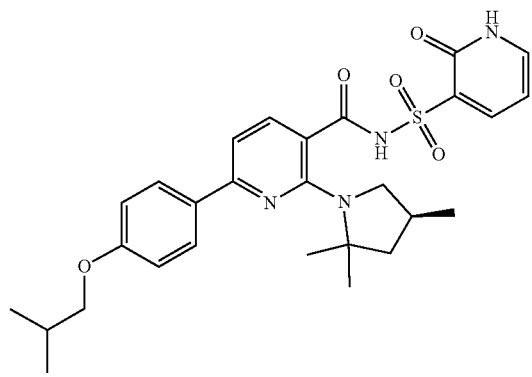 [SMILES: CC(C)COc1ccc(-c2ccc(C(=O)NS(=O)(=O)c3ccc[nH]c3=O)c(N3C[C@@H](C)CC3(C)C)n2)cc1] | 2153 |
| 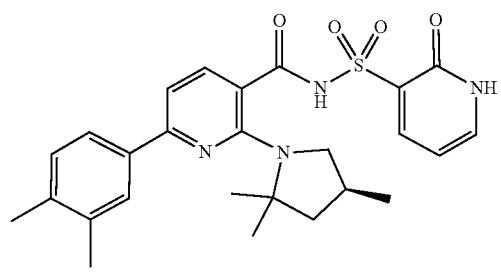 [SMILES: Cc1ccc(-c2ccc(C(=O)NS(=O)(=O)c3ccc[nH]c3=O)c(N3C[C@@H](C)CC3(C)C)n2)cc1C] | 2154 |
| 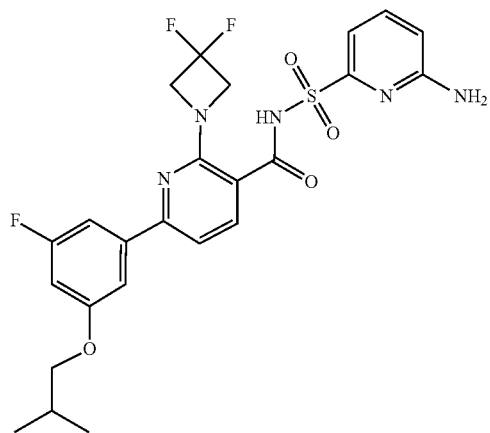 [SMILES: CC(C)COc1cc(F)cc(-c2ccc(C(=O)NS(=O)(=O)c3cccc(N)n3)c(N3CC(F)(F)C3)n2)c1] | 2155 |
| 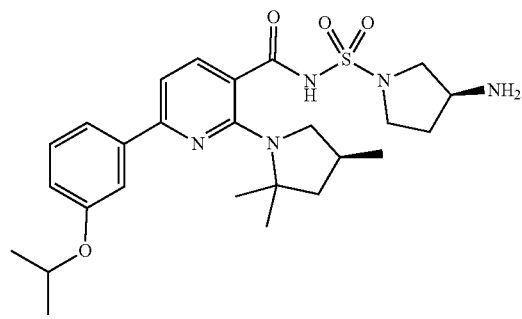 [SMILES: CC(C)Oc1cccc(-c2ccc(C(=O)NS(=O)(=O)N3CC[C@H](N)C3)c(N3C[C@@H](C)CC3(C)C)n2)c1] | 2156 |

TABLE 1-continued
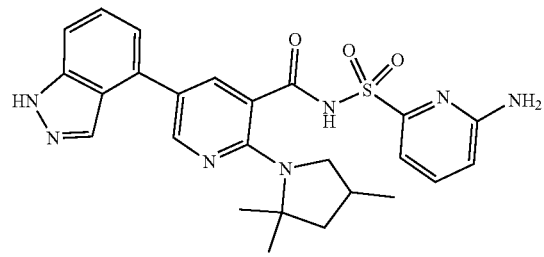 2157
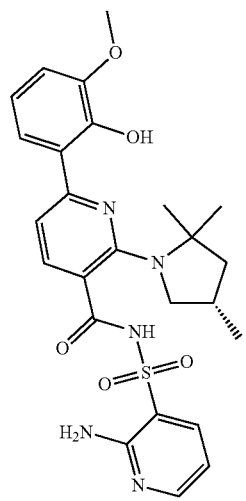 [SMILES: COc1cccc(-c2ccc(C(=O)NS(=O)(=O)c3cccnc3N)c(N3C[C@@H](C)CC3(C)C)n2)c1O] 2158
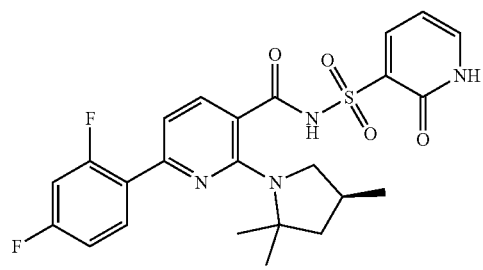 [SMILES: C[C@@H]1CN(c2nc(-c3ccc(F)cc3F)ccc2C(=O)NS(=O)(=O)c2ccc[nH]c2=O)C(C)(C)C1] 2159
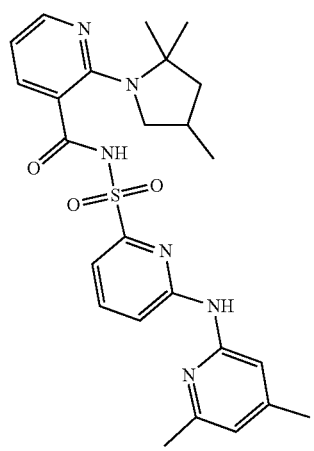 [SMILES: Cc1cc(C)nc(Nc2cccc(S(=O)(=O)NC(=O)c3cccnc3N3CC(C)CC3(C)C)n2)c1] 2160

TABLE 1-continued
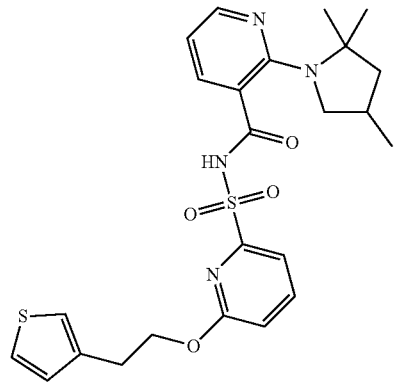 [SMILES: CC1CN(c2ncccc2C(=O)NS(=O)(=O)c2cccc(OCCc3ccsc3)n2)C(C)(C)C1]
2161
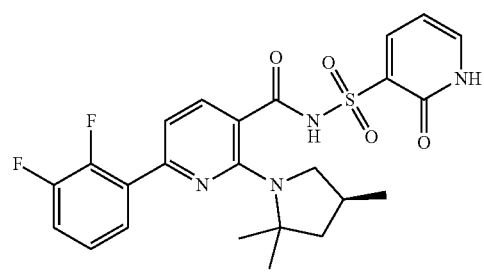
2162
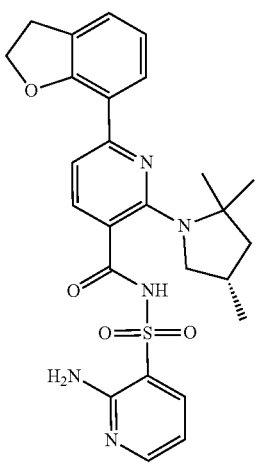 [SMILES: C[C@@H]1CN(c2nc(-c3cccc4c3OCC4)ccc2C(=O)NS(=O)(=O)c2cccnc2N)C(C)(C)C1]
2163
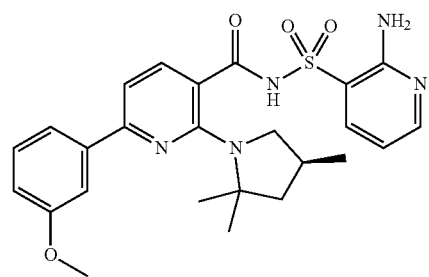
2164

TABLE 1-continued
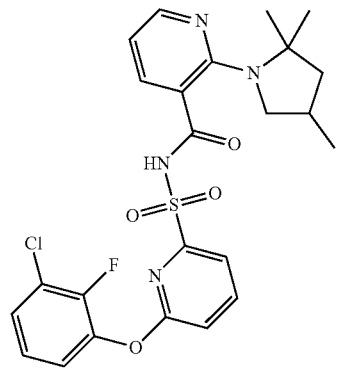 [SMILES: CC1CN(c2ncccc2C(=O)NS(=O)(=O)c2cccc(Oc3cccc(Cl)c3F)n2)C(C)(C)C1]
2165
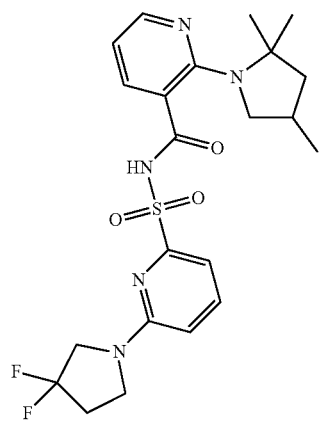 [SMILES: CC1CN(c2ncccc2C(=O)NS(=O)(=O)c2cccc(N3CCC(F)(F)C3)n2)C(C)(C)C1]
2166
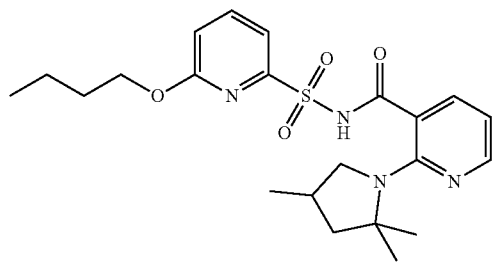
2167
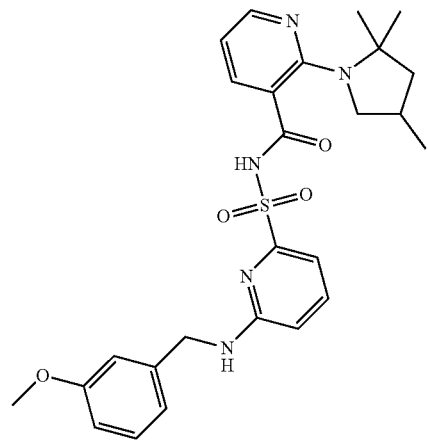
2168

TABLE 1-continued
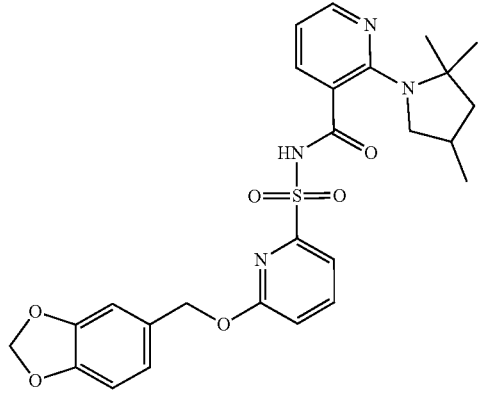 [SMILES: CC1CN(c2ncccc2C(=O)NS(=O)(=O)c2cccc(OCc3ccc4c(c3)OCO4)n2)C(C)(C)C1]
2169
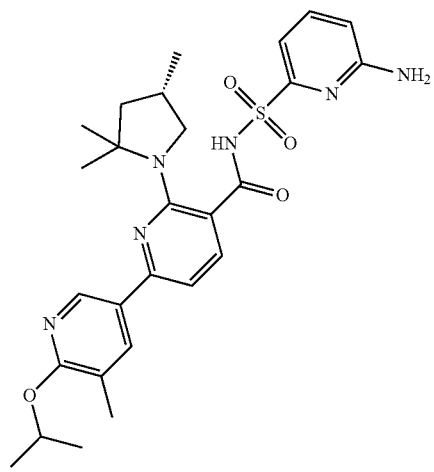 [SMILES: Cc1cc(-c2ccc(C(=O)NS(=O)(=O)c3cccc(N)n3)c(N3C[C@@H](C)CC3(C)C)n2)cnc1OC(C)C]
2170
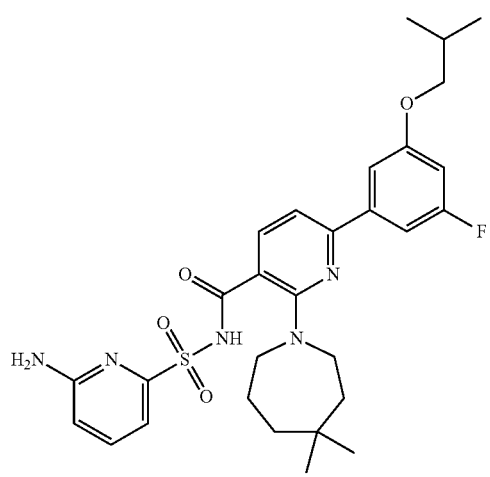 [SMILES: CC(C)COc1cc(F)cc(-c2ccc(C(=O)NS(=O)(=O)c3cccc(N)n3)c(N3CCCC(C)(C)CC3)n2)c1]
2171
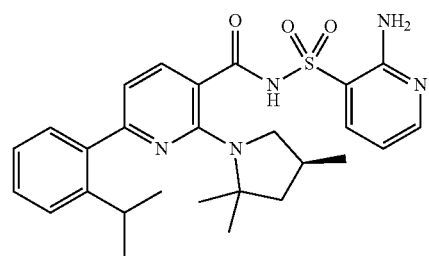
2172

TABLE 1-continued
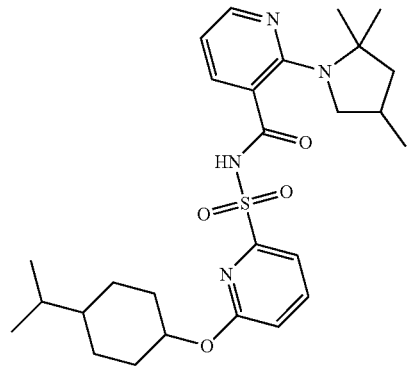 [SMILES: CC1CN(c2ncccc2C(=O)NS(=O)(=O)c2cccc(OC3CCC(C(C)C)CC3)n2)C(C)(C)C1] 2173
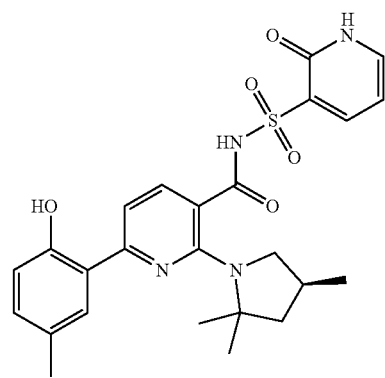 2174
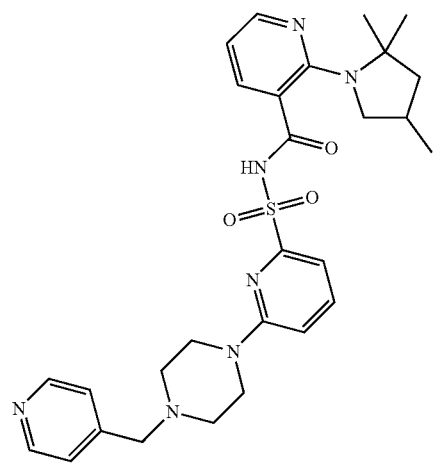 [SMILES: CC1CN(c2ncccc2C(=O)NS(=O)(=O)c2cccc(N3CCN(Cc4ccncc4)CC3)n2)C(C)(C)C1] 2175
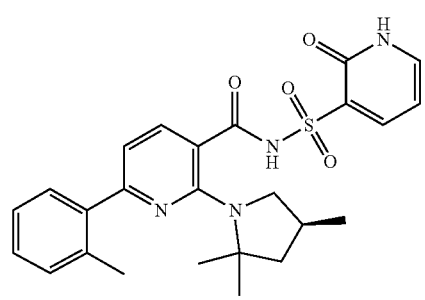 2176

TABLE 1-continued
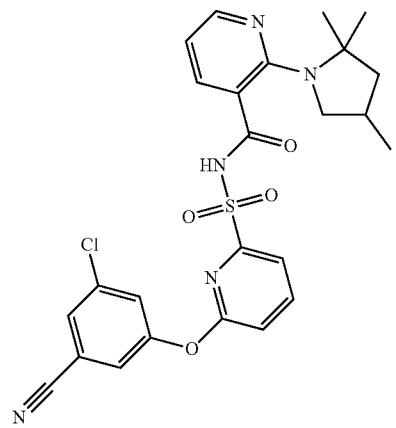 [SMILES: CC1CN(c2ncccc2C(=O)NS(=O)(=O)c2cccc(Oc3cc(Cl)cc(C#N)c3)n2)C(C)(C)C1]
2177
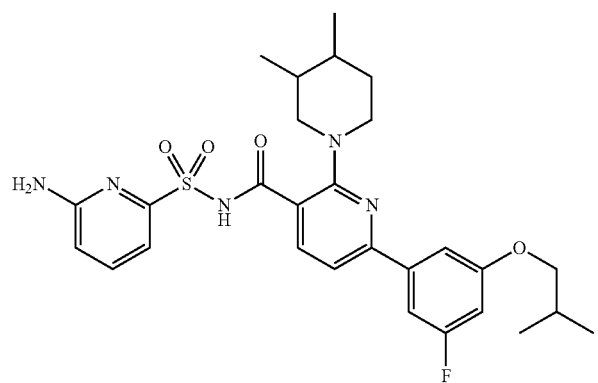
2178
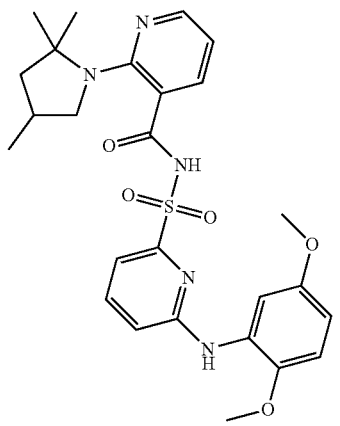
2179
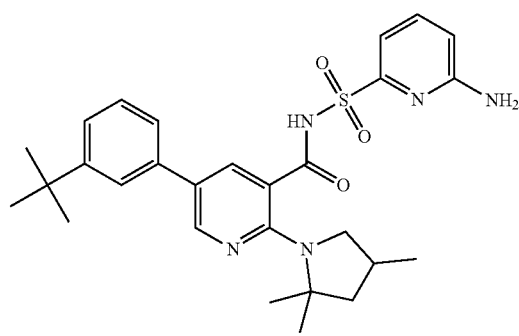 [SMILES: CC1CN(c2ncc(-c3cccc(C(C)(C)C)c3)cc2C(=O)NS(=O)(=O)c2cccc(N)n2)C(C)(C)C1]
2180

TABLE 1-continued
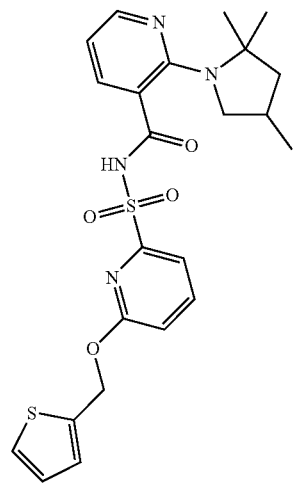 [SMILES: CC1CN(c2ncccc2C(=O)NS(=O)(=O)c2cccc(OCc3cccs3)n2)C(C)(C)C1]
2181
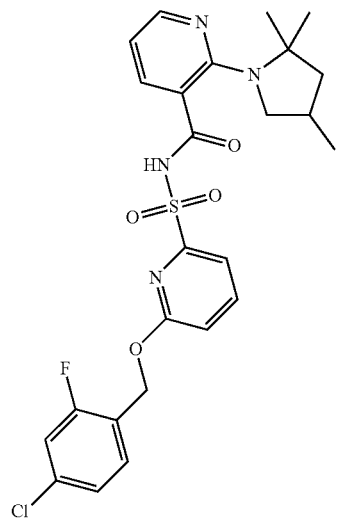 [SMILES: CC1CN(c2ncccc2C(=O)NS(=O)(=O)c2cccc(OCc3ccc(Cl)cc3F)n2)C(C)(C)C1]
2182
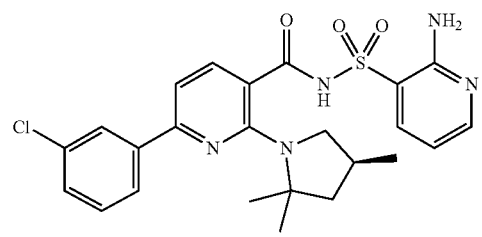
2183
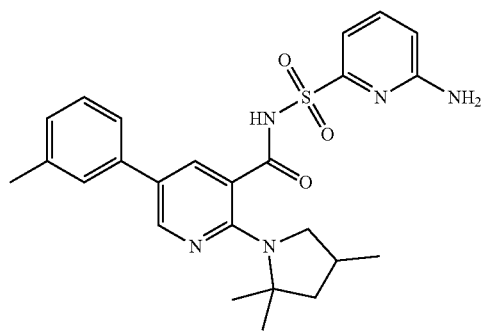 [SMILES: Cc1cccc(-c2cnc(N3CC(C)CC3(C)C)c(C(=O)NS(=O)(=O)c3cccc(N)n3)c2)c1]
2184

TABLE 1-continued
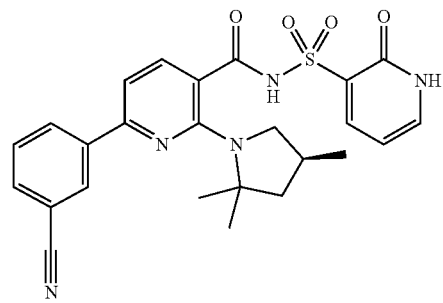
2185
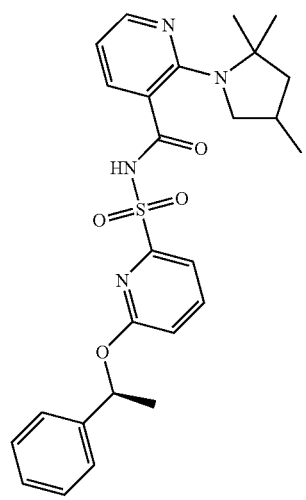 [SMILES: CC1CN(c2ncccc2C(=O)NS(=O)(=O)c2cccc(O[C@@H](C)c3ccccc3)n2)C(C)(C)C1]
2186
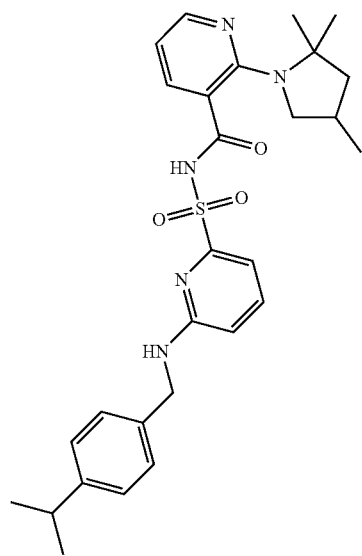 [SMILES: CC1CN(c2ncccc2C(=O)NS(=O)(=O)c2cccc(NCc3ccc(C(C)C)cc3)n2)C(C)(C)C1]
2187

TABLE 1-continued
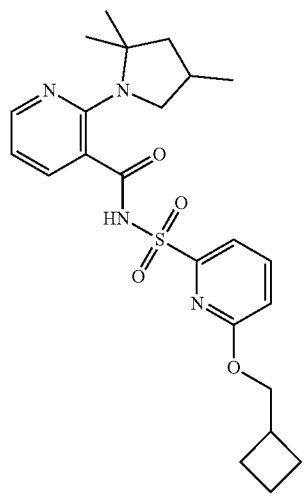 [SMILES: CC1CN(c2ncccc2C(=O)NS(=O)(=O)c2cccc(OCC3CCC3)n2)C(C)(C)C1] 2188
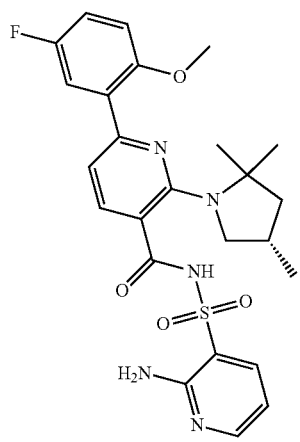 [SMILES: COc1ccc(F)cc1-c1ccc(C(=O)NS(=O)(=O)c2cccnc2N)c(N2C[C@@H](C)CC2(C)C)n1] 2189
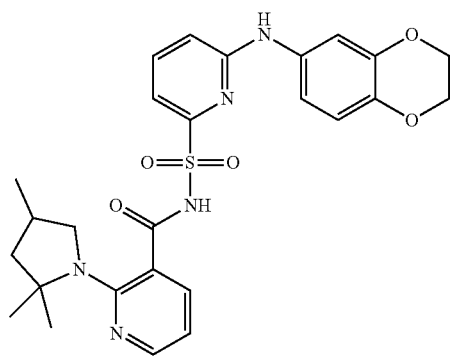 2190
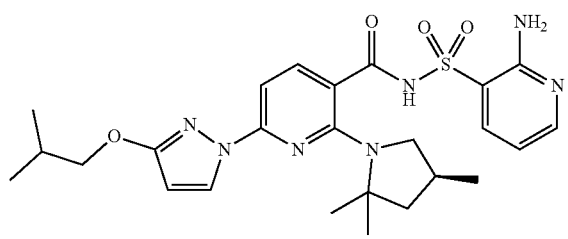 2191

TABLE 1-continued
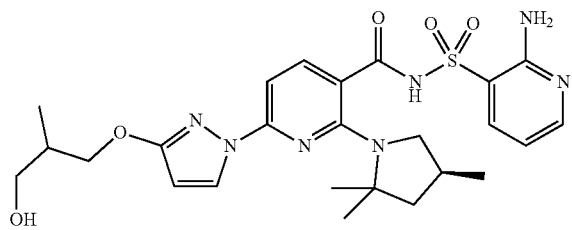
2192
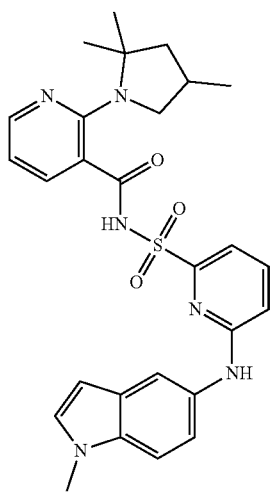 [SMILES: CC1CN(c2ncccc2C(=O)NS(=O)(=O)c2cccc(Nc3ccc4c(ccn4C)c3)n2)C(C)(C)C1]
2193
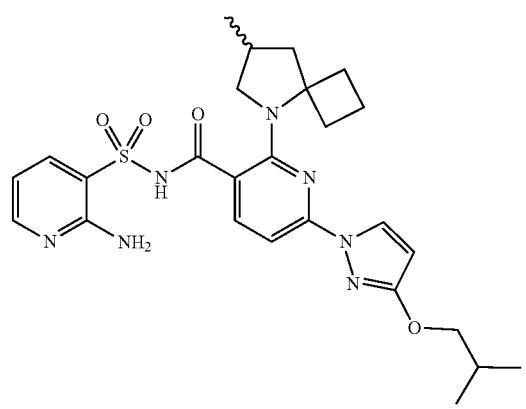
2194
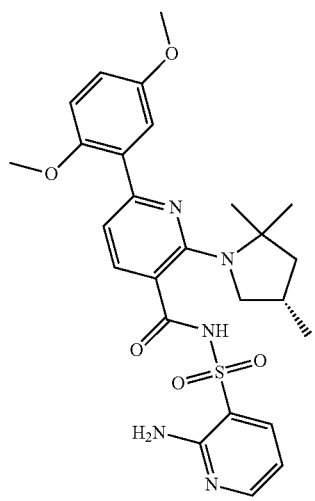
2195

TABLE 1-continued
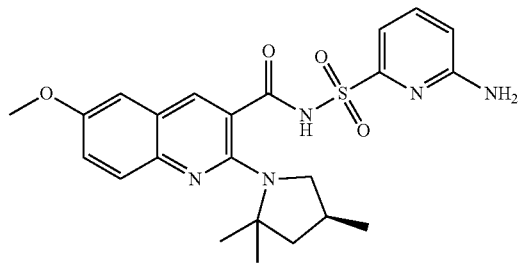
2196
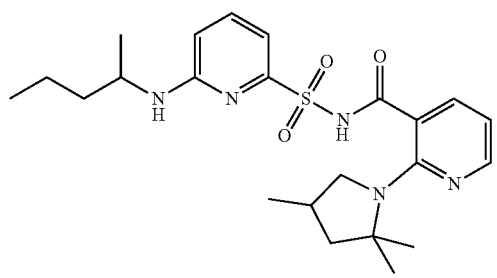
2197
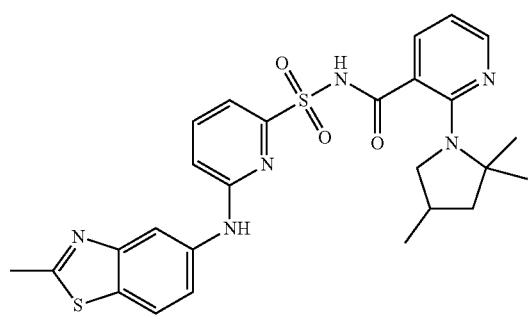
2198
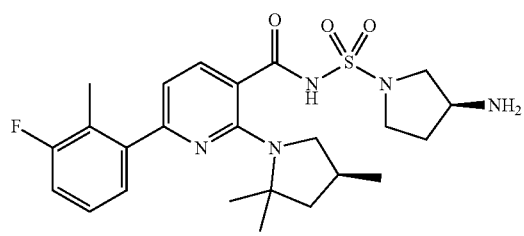
2199
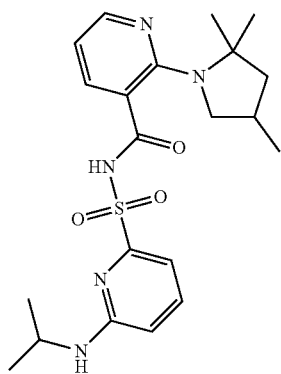
2200

TABLE 1-continued
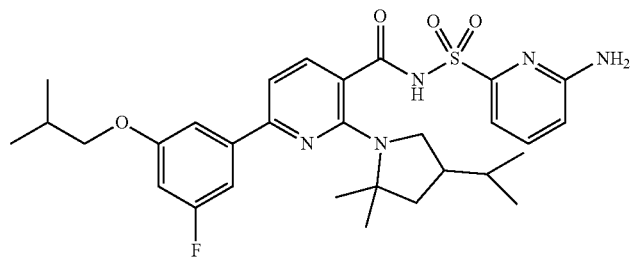
2201
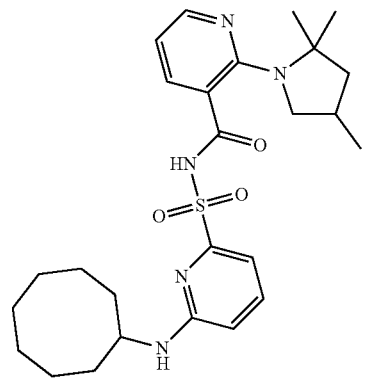
2202
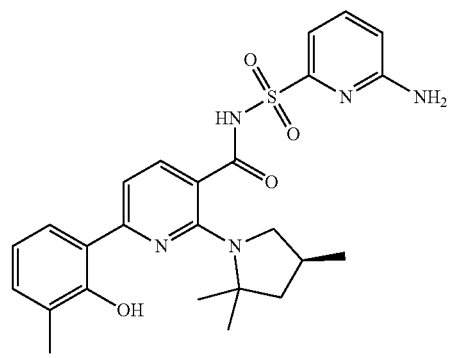 [SMILES: Cc1cccc(-c2ccc(C(=O)NS(=O)(=O)c3cccc(N)n3)c(N3C[C@@H](C)CC3(C)C)n2)c1O]
2203
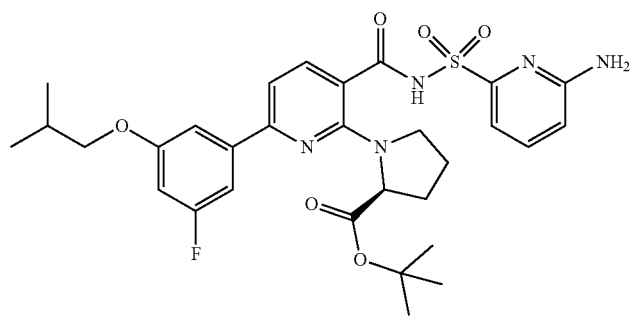
2204
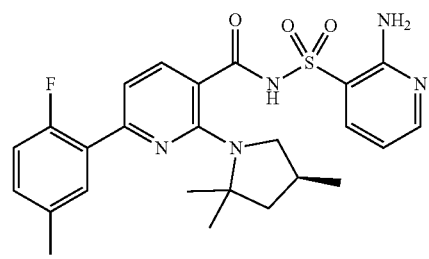
2205

TABLE 1-continued
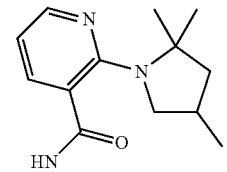
2206
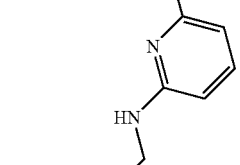
2207
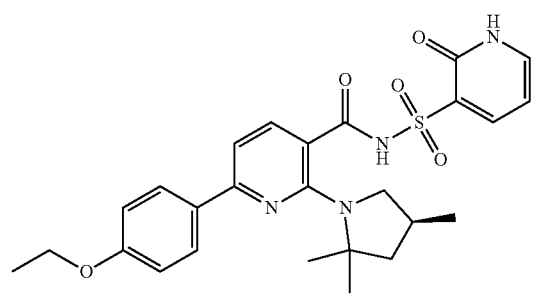
2208

TABLE 1-continued
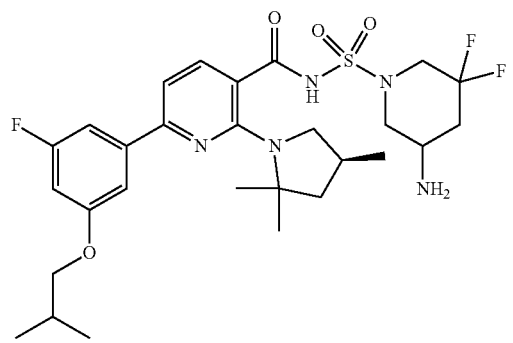
2209
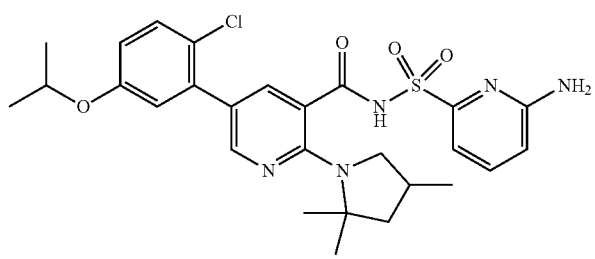
2210
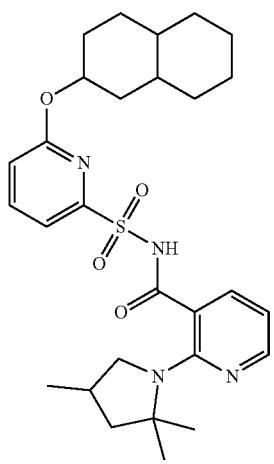 [SMILES: CC1CN(c2ncccc2C(=O)NS(=O)(=O)c2cccc(OC3CCC4CCCCC4C3)n2)C(C)(C)C1]
2211
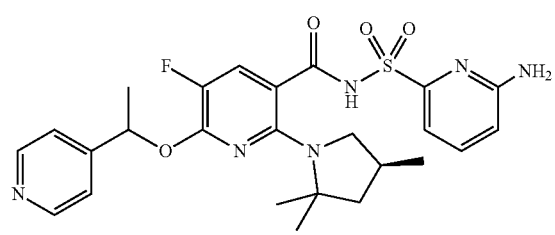
2212
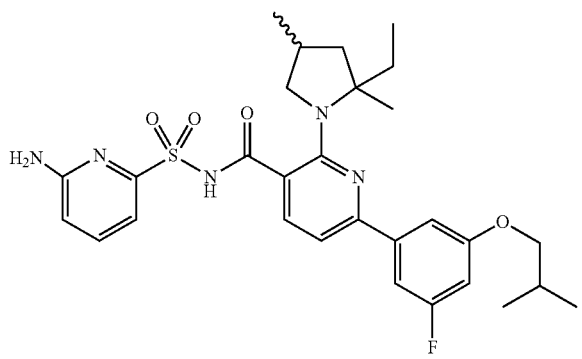
2213

TABLE 1-continued
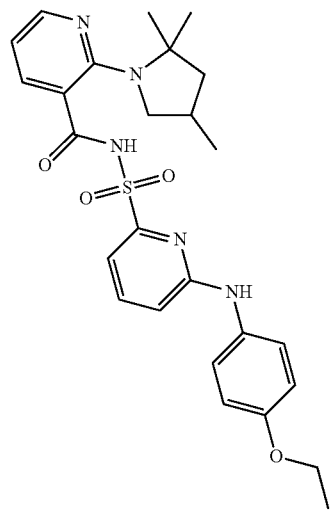 [SMILES: CCOc1ccc(Nc2cccc(S(=O)(=O)NC(=O)c3cccnc3N3CC(C)CC3(C)C)n2)cc1]
2214
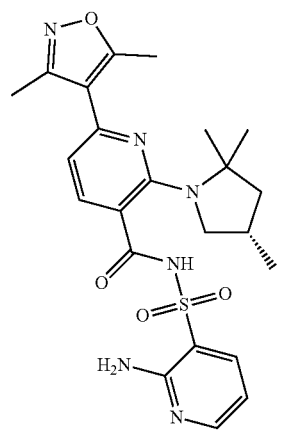
2215
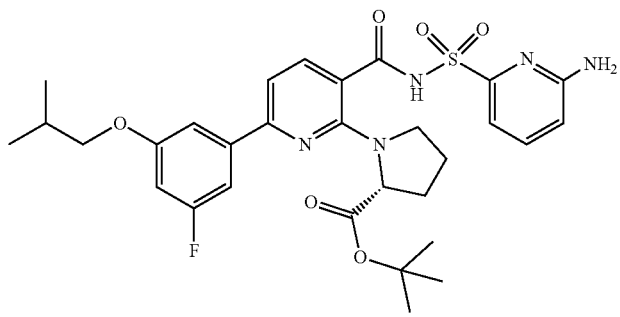
2216
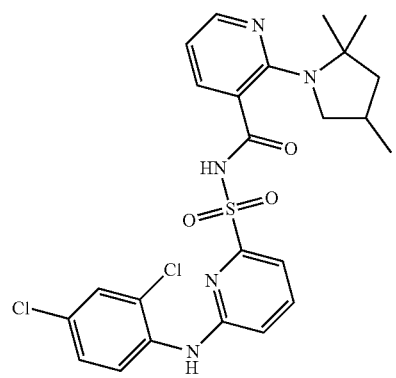
2217

TABLE 1-continued
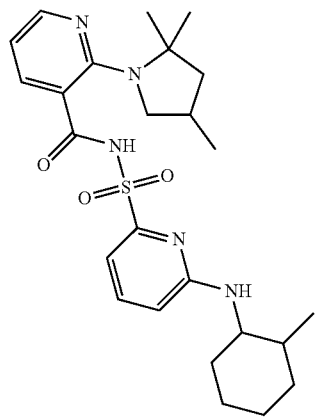 [SMILES: CC1CN(c2ncccc2C(=O)NS(=O)(=O)c2cccc(NC3CCCCC3C)n2)C(C)(C)C1] 2218
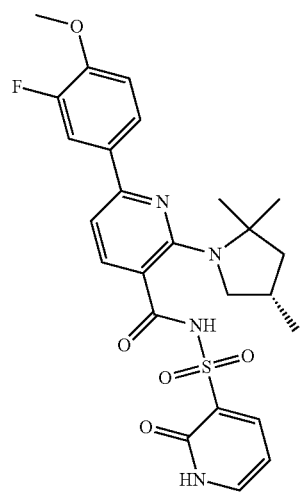 [SMILES: COc1ccc(-c2ccc(C(=O)NS(=O)(=O)c3ccc[nH]c3=O)c(N3C[C@@H](C)CC3(C)C)n2)cc1F] 2219
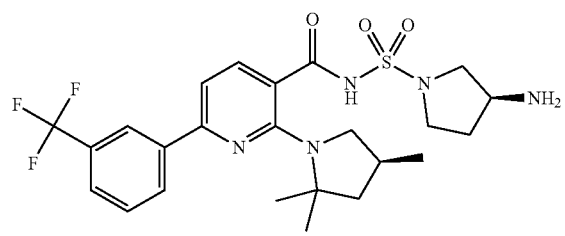 2220
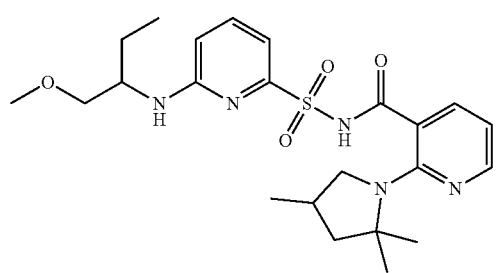 2221

TABLE 1-continued
| | |
|---|---|
|  | 2222 |
| 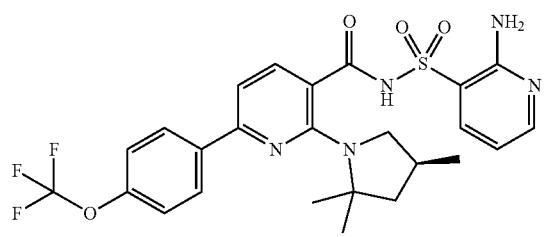 | 2223 |
| 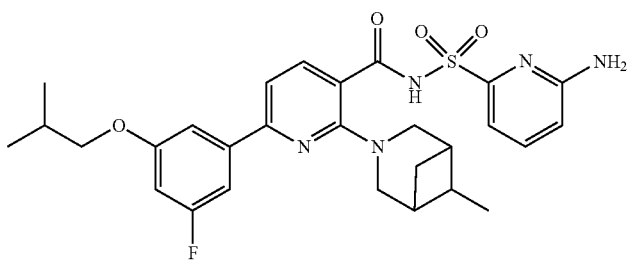 | 2224 |
| 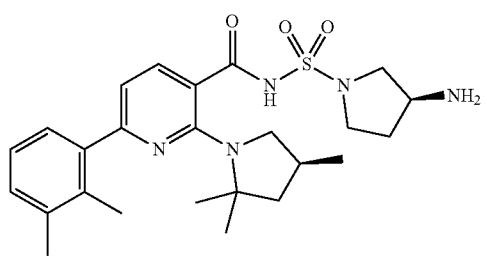 | 2225 |
| 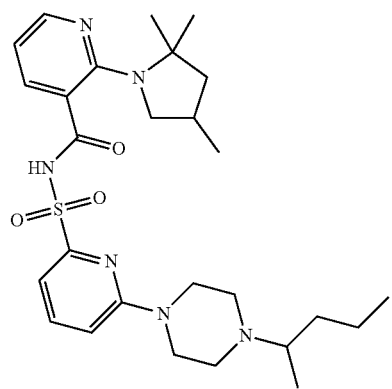 [SMILES: CCCC(C)N1CCN(c2cccc(S(=O)(=O)NC(=O)c3cccnc3N3CC(C)CC3(C)C)n2)CC1] | 2226 |

TABLE 1-continued
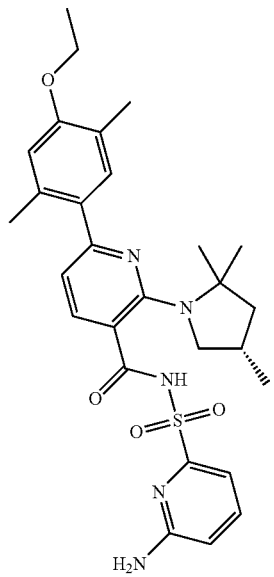
2227
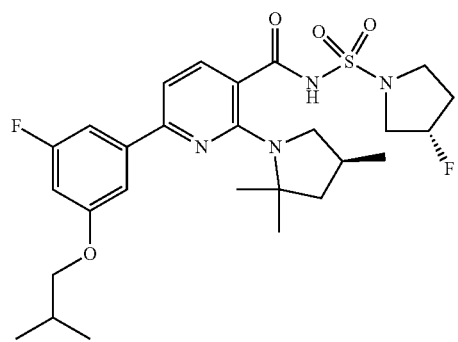
2228
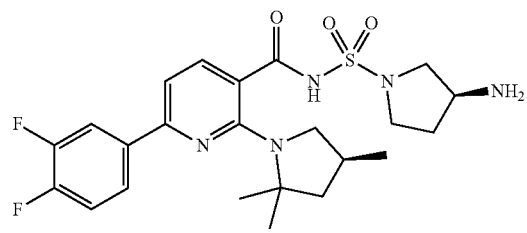
2229
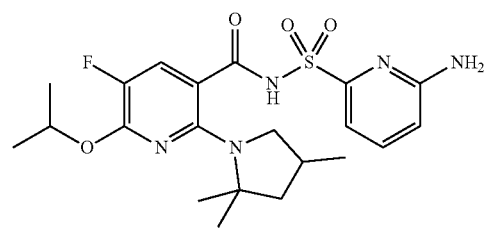
2230

TABLE 1-continued
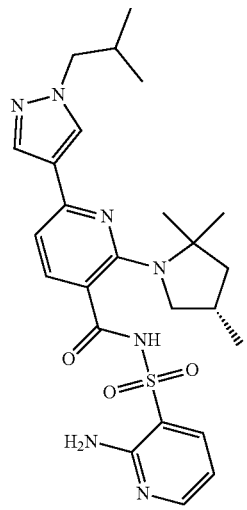 [SMILES: CC(C)Cn1cc(-c2ccc(C(=O)NS(=O)(=O)c3cccnc3N)c(N3C[C@@H](C)CC3(C)C)n2)cn1]
2231
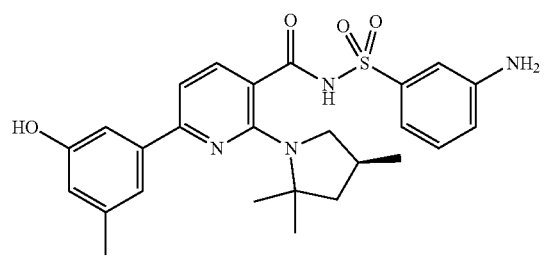
2232
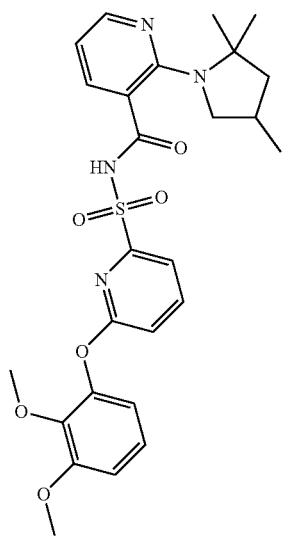
2233
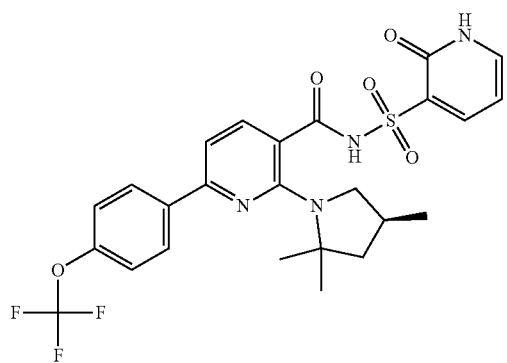
2234

TABLE 1-continued
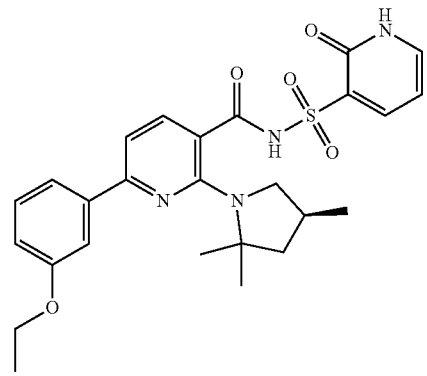
2235
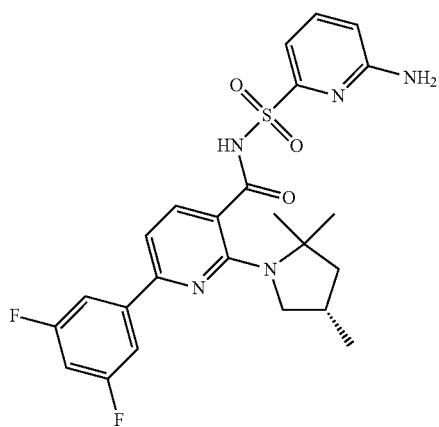 [SMILES: C[C@@H]1CN(c2nc(-c3cc(F)cc(F)c3)ccc2C(=O)NS(=O)(=O)c2cccc(N)n2)C(C)(C)C1]
2236
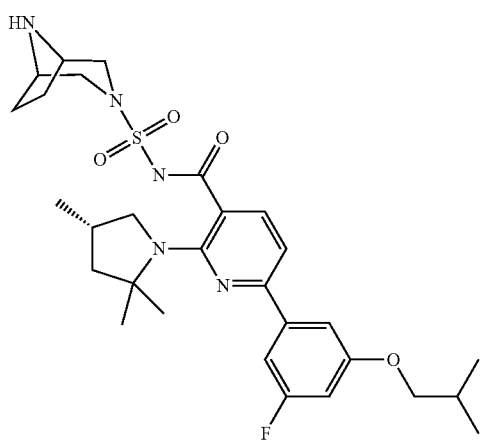 [SMILES: CC(C)COc1cc(F)cc(-c2ccc(C(=O)NS(=O)(=O)N3CC4CCC(C3)N4)c(N3C[C@@H](C)CC3(C)C)n2)c1]
2237
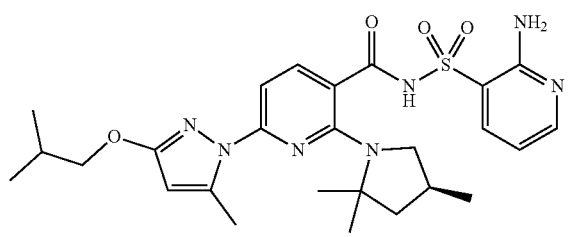
2238

TABLE 1-continued
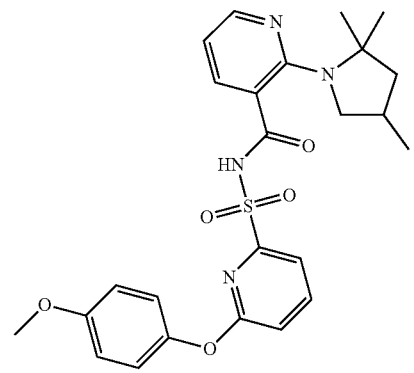
2239
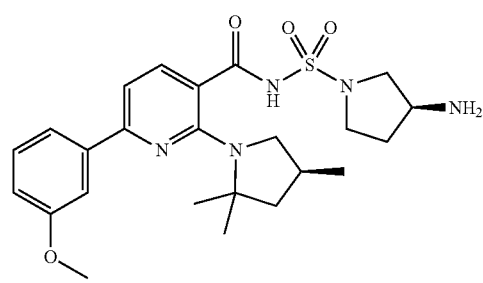
2240
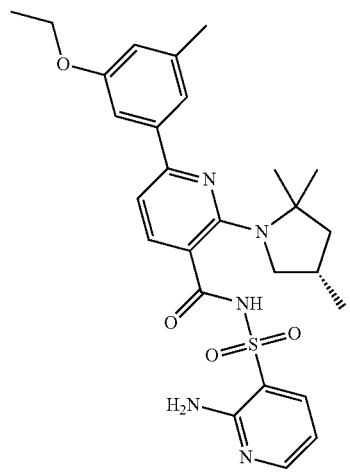 [SMILES: CCOc1cc(C)cc(-c2ccc(C(=O)NS(=O)(=O)c3cccnc3N)c(N3C[C@@H](C)CC3(C)C)n2)c1]
2241
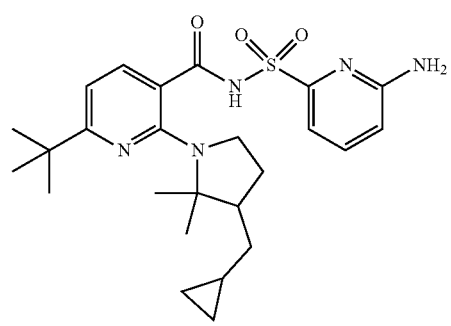
2242

TABLE 1-continued
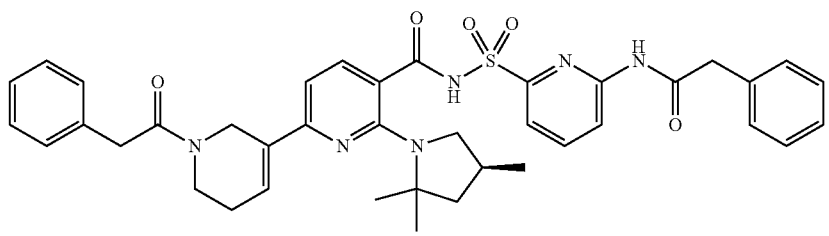
2243
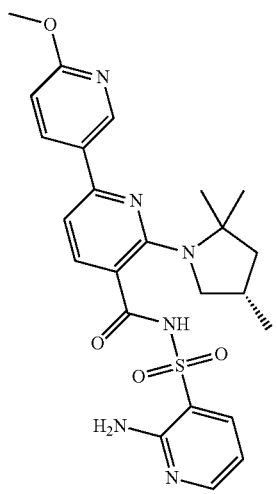
2244
2245
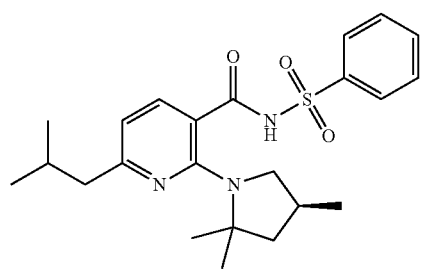
2246
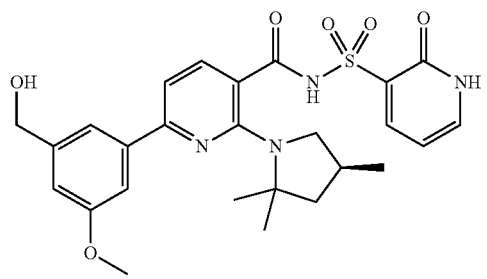
2247

TABLE 1-continued
| | |
|---|---|
| 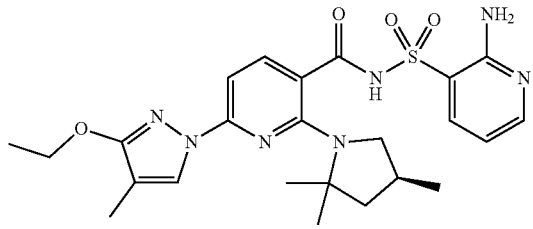 | 2248 |
| 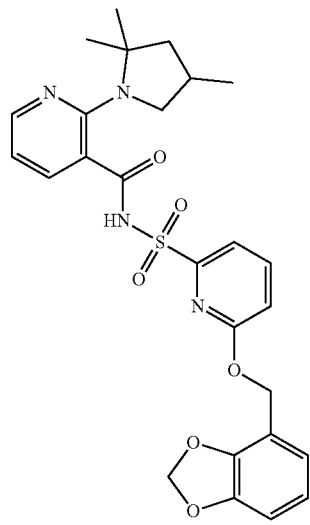 [SMILES: CC1CN(c2ncccc2C(=O)NS(=O)(=O)c2cccc(OCc3cccc4c3OCO4)n2)C(C)(C)C1] | 2249 |
| 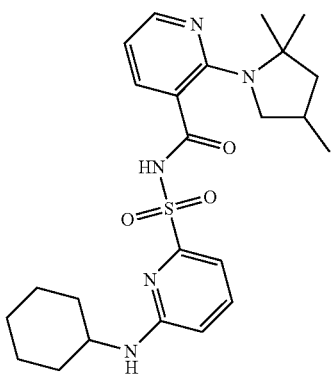 | 2250 |
| 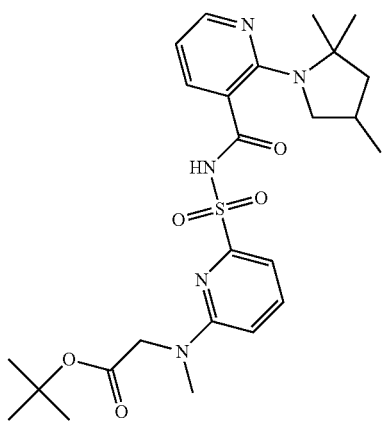 [SMILES: CC1CN(c2ncccc2C(=O)NS(=O)(=O)c2cccc(N(C)CC(=O)OC(C)(C)C)n2)C(C)(C)C1] | 2251 |

TABLE 1-continued
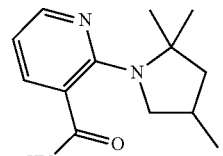
2252
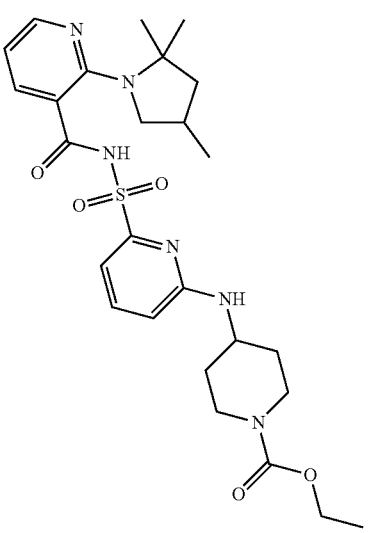 [SMILES: CCOC(=O)N1CCC(Nc2cccc(S(=O)(=O)NC(=O)c3cccnc3N3CC(C)CC3(C)C)n2)CC1]
2253
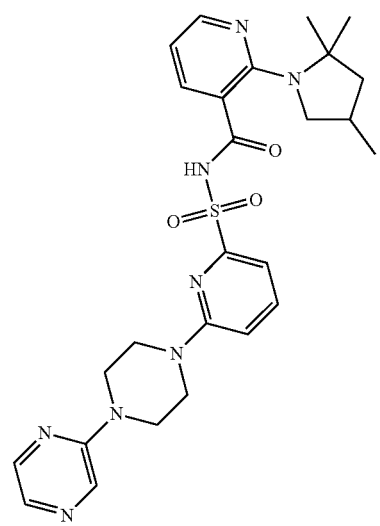 [SMILES: CC1CN(c2ncccc2C(=O)NS(=O)(=O)c2cccc(N3CCN(c4cnccn4)CC3)n2)C(C)(C)C1]
2254

TABLE 1-continued
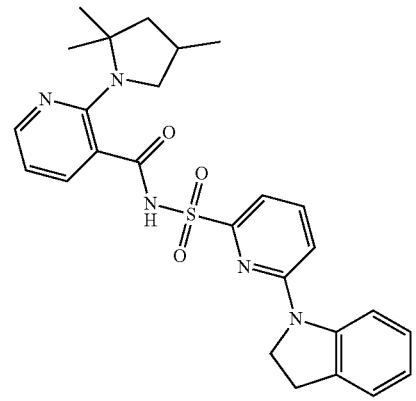 2255
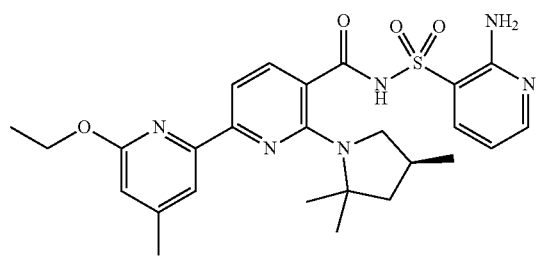 2256
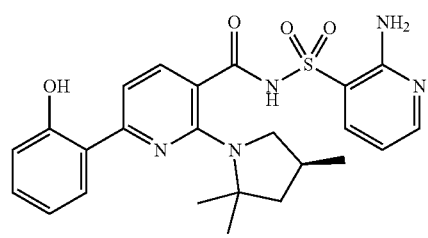 2257
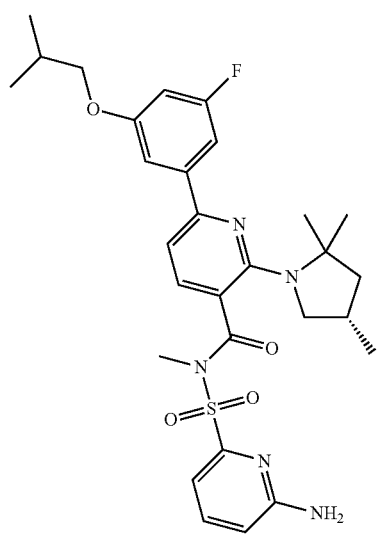 [SMILES: CC(C)COc1cc(F)cc(-c2ccc(C(=O)N(C)S(=O)(=O)c3cccc(N)n3)c(N3C[C@@H](C)CC3(C)C)n2)c1] 2258

TABLE 1-continued

| | |
|---|---|
| (structure) | 2259 |
| (structure) | 2260 |
| (structure) | 2261 |

TABLE 1-continued
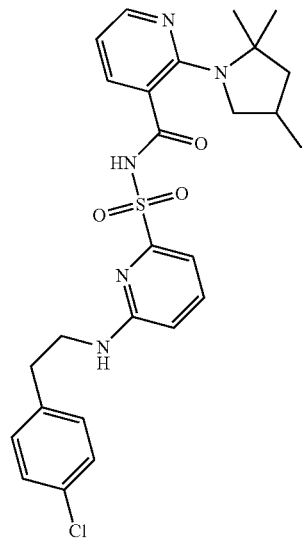
2262
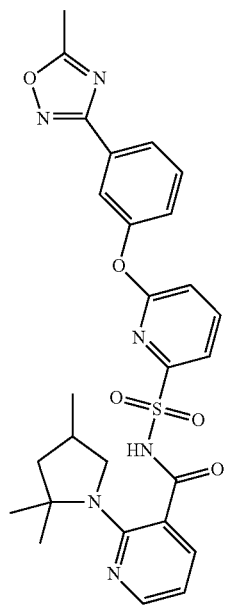 [SMILES: Cc1nc(-c2cccc(Oc3cccc(S(=O)(=O)NC(=O)c4cccnc4N4CC(C)CC4(C)C)n3)c2)no1]
2263
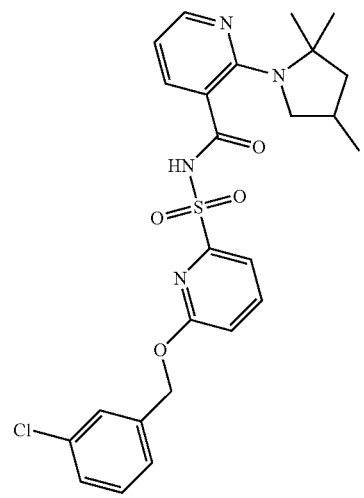 [SMILES: CC1CN(c2ncccc2C(=O)NS(=O)(=O)c2cccc(OCc3cccc(Cl)c3)n2)C(C)(C)C1]
2264

TABLE 1-continued
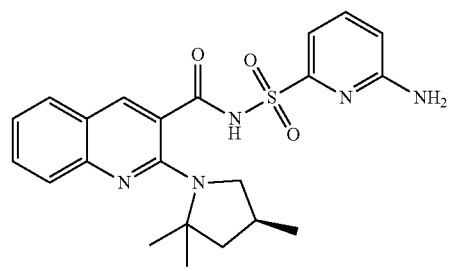
2265
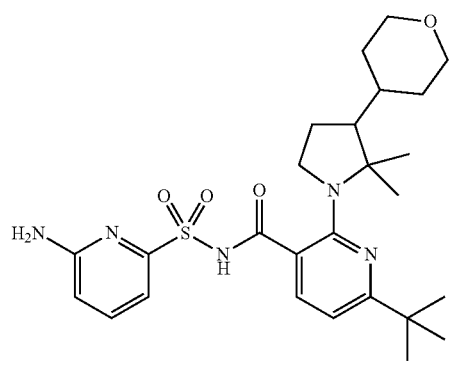
2266
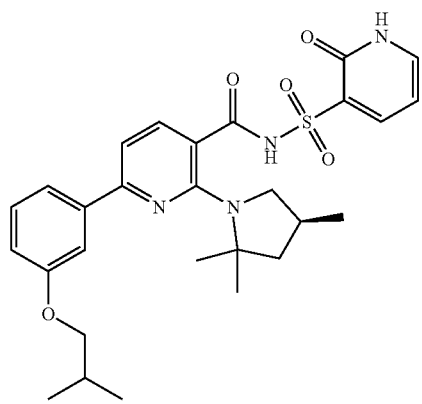
2267
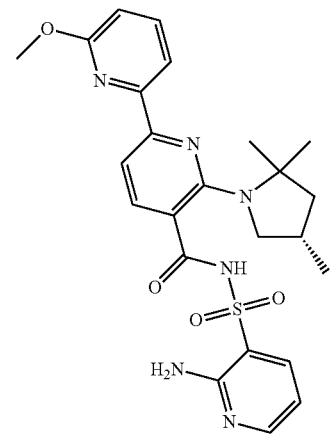
2268

| | |
|---|---|
| 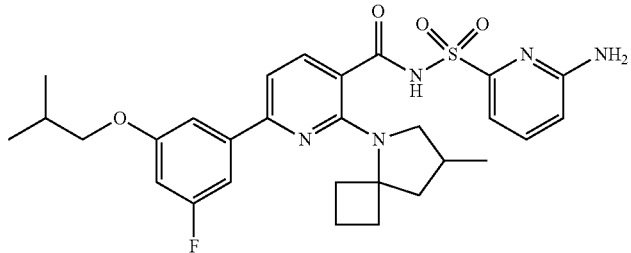 | 2269 |
| 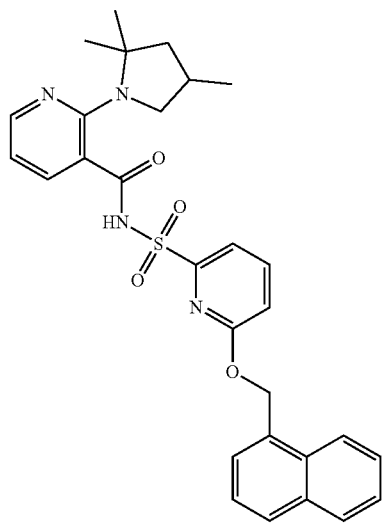 [SMILES: CC1CN(c2ncccc2C(=O)NS(=O)(=O)c2cccc(OCc3cccc4ccccc34)n2)C(C)(C)C1] | 2270 |
| 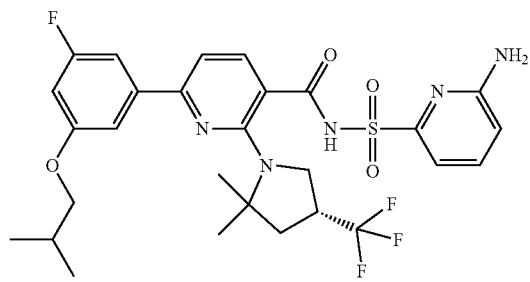 | 2271 |
| 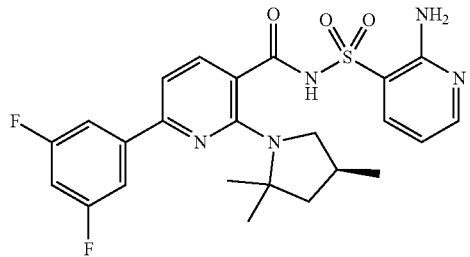 | 2272 |

TABLE 1-continued
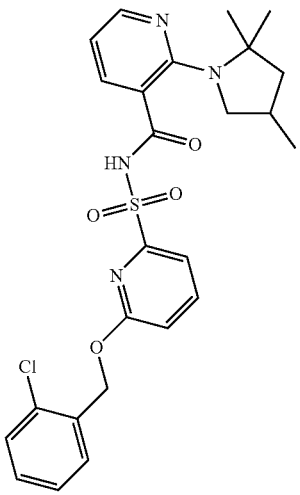 [SMILES: CC1CN(c2ncccc2C(=O)NS(=O)(=O)c2cccc(OCc3ccccc3Cl)n2)C(C)(C)C1]
2273
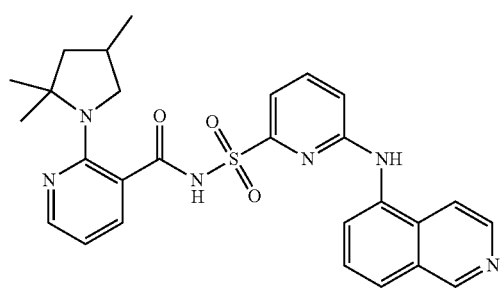
2274
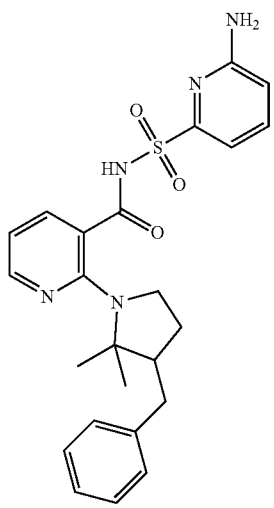 [SMILES: CC1(C)C(Cc2ccccc2)CCN1c1ncccc1C(=O)NS(=O)(=O)c1cccc(N)n1]
2275
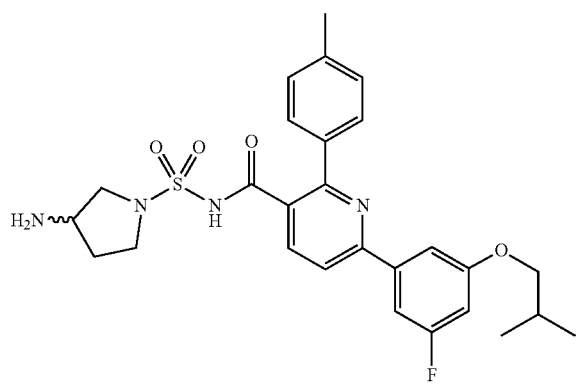
2276

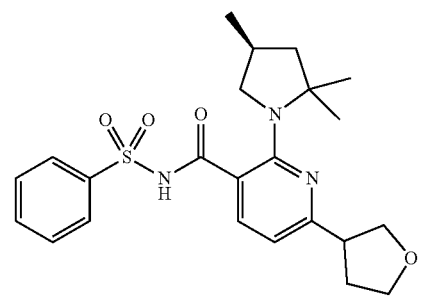 2277
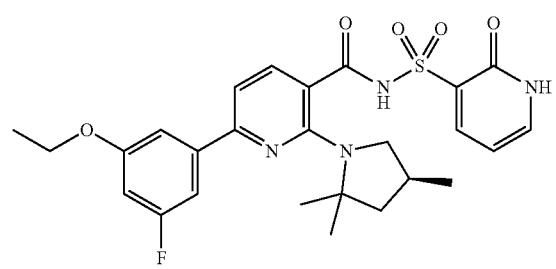 2278
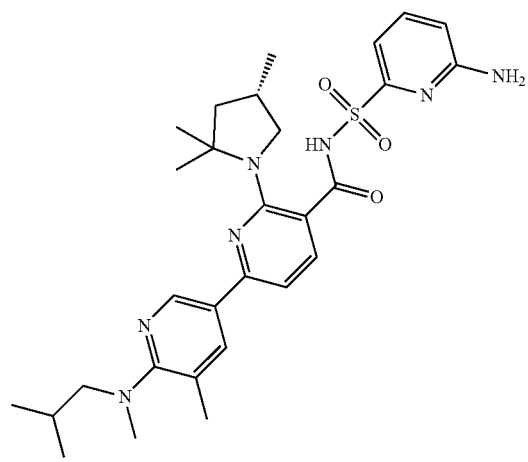 [SMILES: Cc1cc(-c2ccc(C(=O)NS(=O)(=O)c3cccc(N)n3)c(N3C[C@@H](C)CC3(C)C)n2)cnc1N(C)CC(C)C] 2279
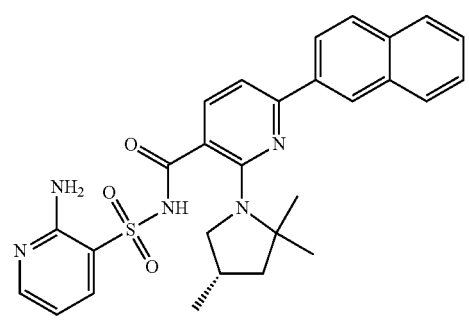 [SMILES: C[C@@H]1CN(c2nc(-c3ccc4ccccc4c3)ccc2C(=O)NS(=O)(=O)c2cccnc2N)C(C)(C)C1] 2280
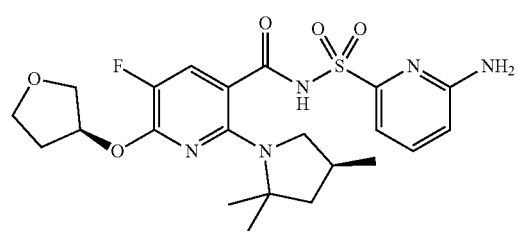 2281

TABLE 1-continued
| | |
|---|---|
| 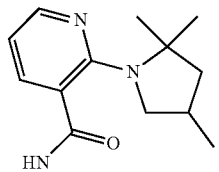 | 2282 |
| 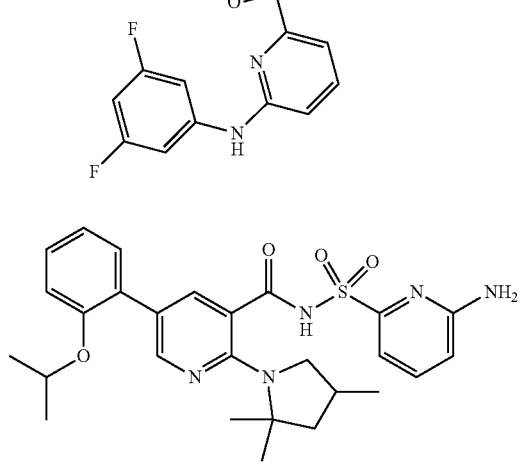 | 2283 |
| 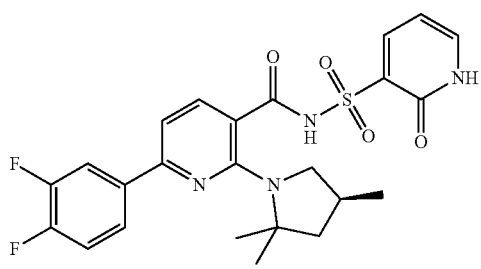 | 2284 |
| 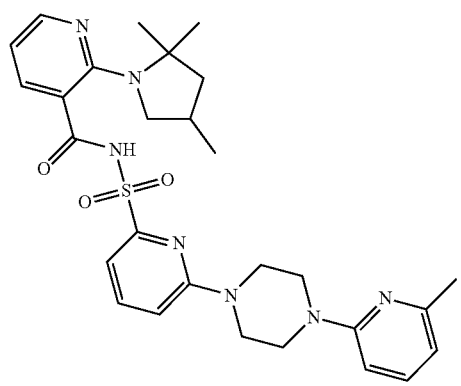 [SMILES: Cc1cccc(N2CCN(c3cccc(S(=O)(=O)NC(=O)c4cccnc4N4CC(C)CC4(C)C)n3)CC2)n1] | 2285 |

TABLE 1-continued
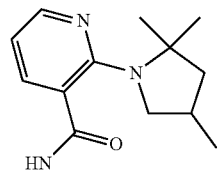
2286
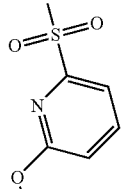
2287
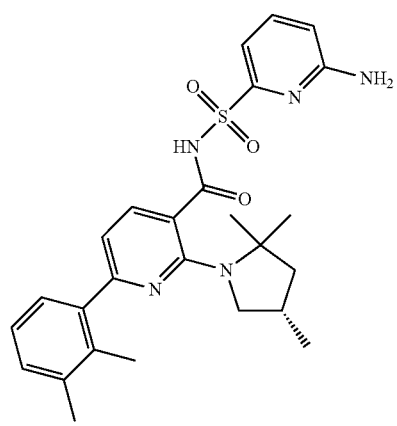 [SMILES: Cc1cccc(-c2ccc(C(=O)NS(=O)(=O)c3cccc(N)n3)c(N3C[C@@H](C)CC3(C)C)n2)c1C]
2288
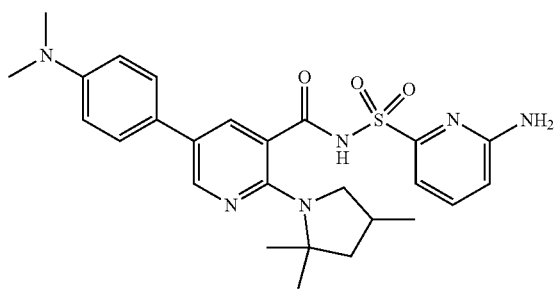
2289

TABLE 1-continued
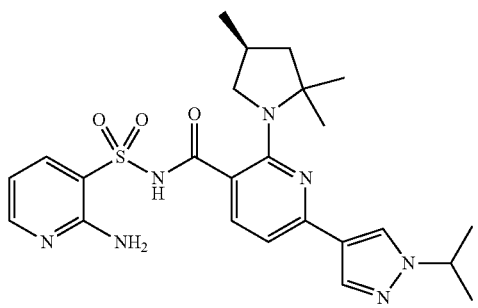
2290
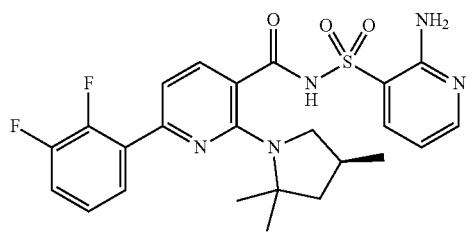
2291
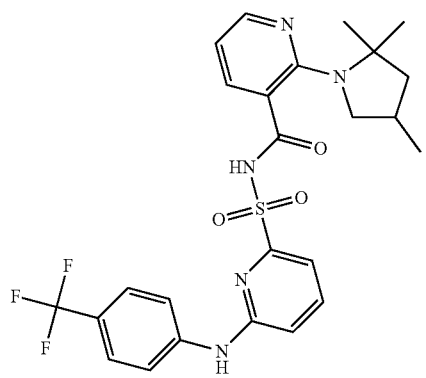
2292
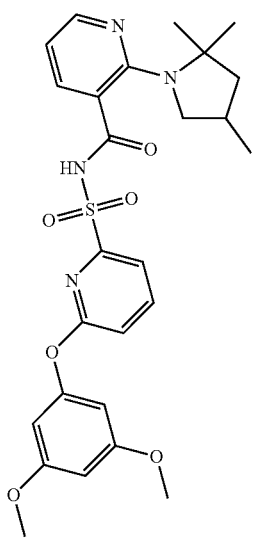 [SMILES: COc1cc(OC)cc(Oc2cccc(S(=O)(=O)NC(=O)c3cccnc3N3CC(C)CC3(C)C)n2)c1]
2293

TABLE 1-continued
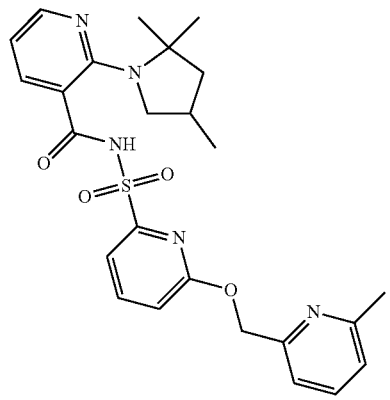 [SMILES: Cc1cccc(COc2cccc(S(=O)(=O)NC(=O)c3cccnc3N3CC(C)CC3(C)C)n2)n1]
2294
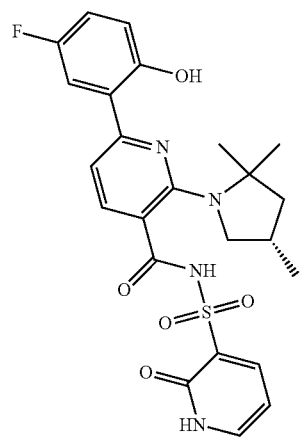 [SMILES: C[C@@H]1CN(c2nc(-c3cc(F)ccc3O)ccc2C(=O)NS(=O)(=O)c2ccc[nH]c2=O)C(C)(C)C1]
2295
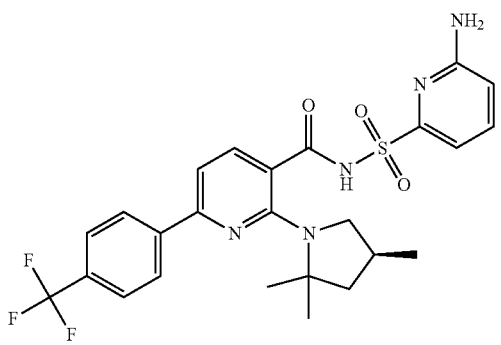
2296
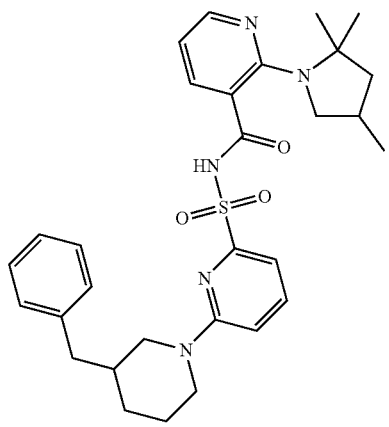 [SMILES: CC1CN(c2ncccc2C(=O)NS(=O)(=O)c2cccc(N3CCCC(Cc4ccccc4)C3)n2)C(C)(C)C1]
2297

TABLE 1-continued
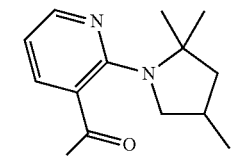
2298
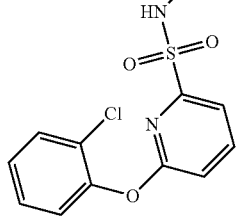
2299
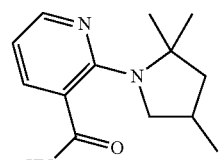
2300
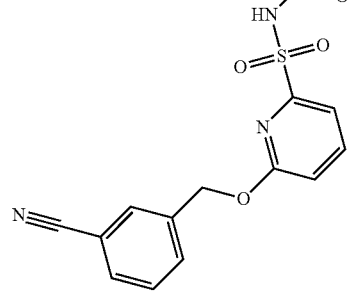
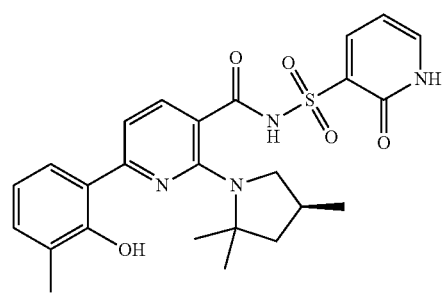
2301
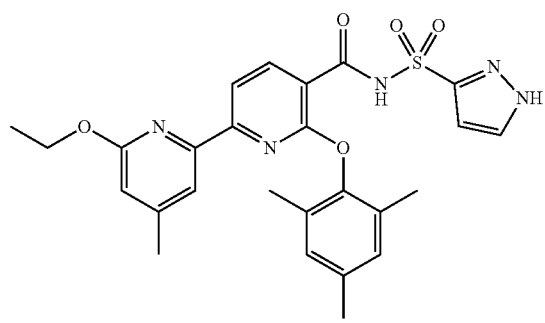

TABLE 1-continued
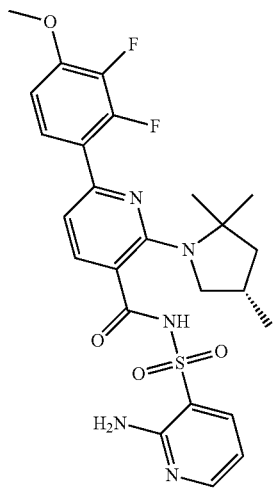 2302
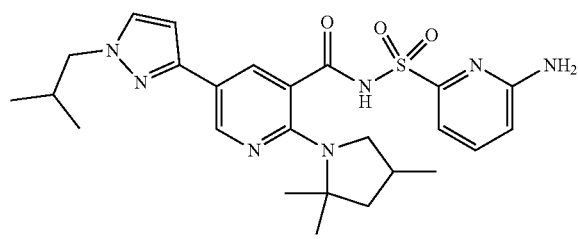 2303
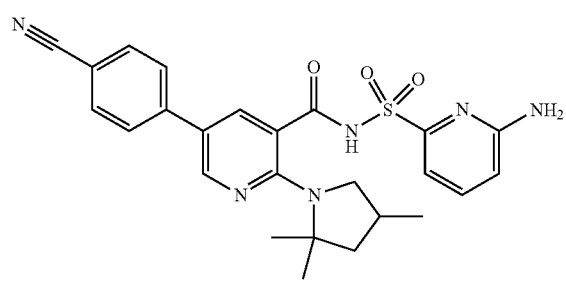 2304
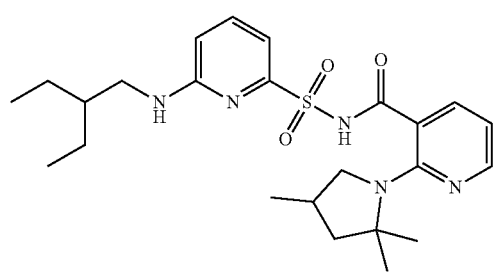 2305

TABLE 1-continued
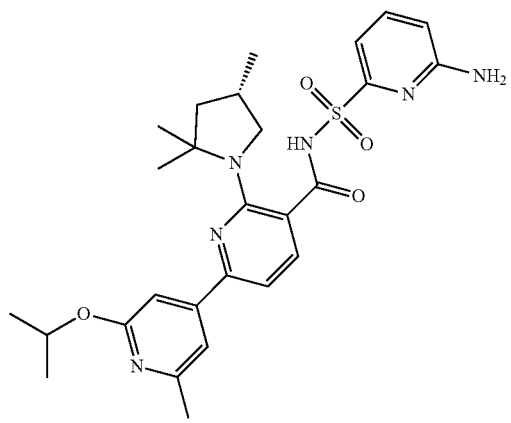 [SMILES: Cc1cc(-c2ccc(C(=O)NS(=O)(=O)c3cccc(N)n3)c(N3C[C@@H](C)CC3(C)C)n2)cc(OC(C)C)n1]
2306
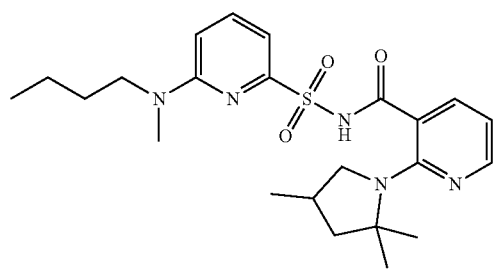
2307
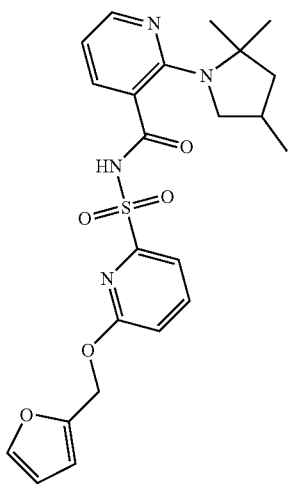 [SMILES: CC1CN(c2ncccc2C(=O)NS(=O)(=O)c2cccc(OCc3ccco3)n2)C(C)(C)C1]
2308
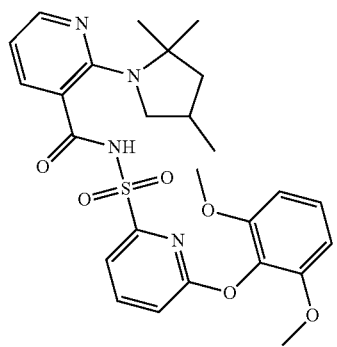 [SMILES: COc1cccc(OC)c1Oc1cccc(S(=O)(=O)NC(=O)c2cccnc2N2CC(C)CC2(C)C)n1]
2309

| | |
|---|---|
| 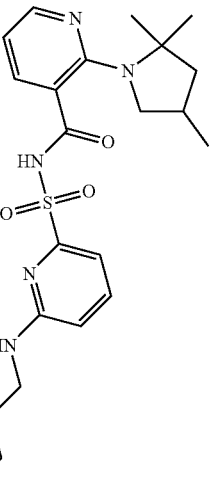 | 2310 |
| 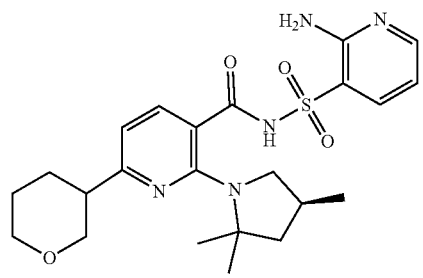 [SMILES: C[C@@H]1CN(c2nc(C3CCCOC3)ccc2C(=O)NS(=O)(=O)c2cccnc2N)C(C)(C)C1] | 2311 |
| 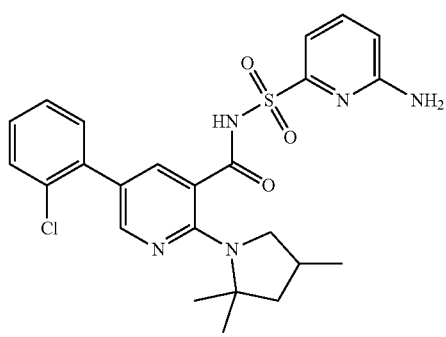 [SMILES: CC1CN(c2ncc(-c3ccccc3Cl)cc2C(=O)NS(=O)(=O)c2cccc(N)n2)C(C)(C)C1] | 2312 |
| 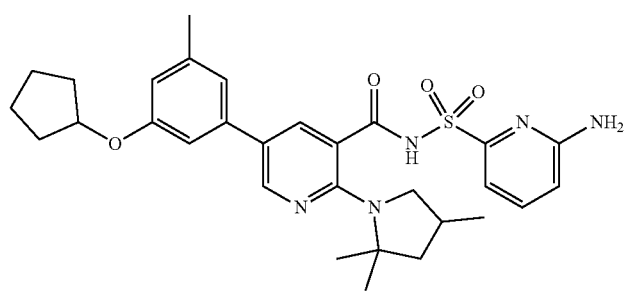 [SMILES: Cc1cc(OC2CCCC2)cc(-c2cnc(N3CC(C)CC3(C)C)c(C(=O)NS(=O)(=O)c3cccc(N)n3)c2)c1] | 2313 |

TABLE 1-continued
| | |
|---|---|
| 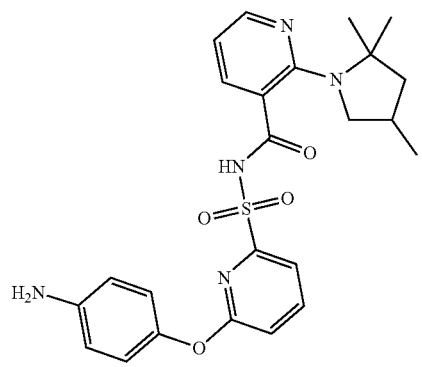 [SMILES: CC1CN(c2ncccc2C(=O)NS(=O)(=O)c2cccc(Oc3ccc(N)cc3)n2)C(C)(C)C1] | 2314 |
| 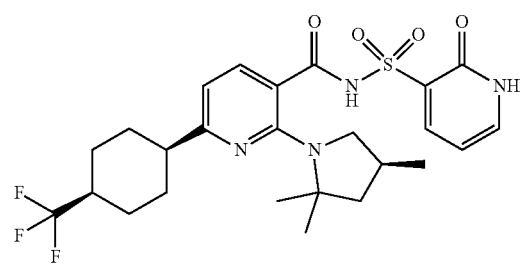 [SMILES: C[C@@H]1CN(c2nc([C@H]3CC[C@@H](C(F)(F)F)CC3)ccc2C(=O)NS(=O)(=O)c2ccc[nH]c2=O)C(C)(C)C1] | 2315 |
| 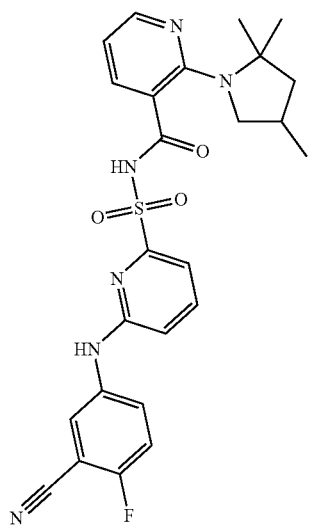 [SMILES: CC1CN(c2ncccc2C(=O)NS(=O)(=O)c2cccc(Nc3ccc(F)c(C#N)c3)n2)C(C)(C)C1] | 2316 |
| 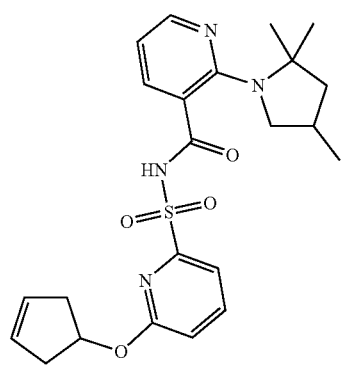 [SMILES: CC1CN(c2ncccc2C(=O)NS(=O)(=O)c2cccc(OC3CC=CC3)n2)C(C)(C)C1] | 2317 |

TABLE 1-continued
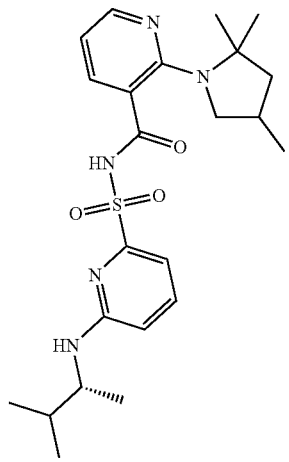 [SMILES: CC1CN(c2ncccc2C(=O)NS(=O)(=O)c2cccc(N[C@H](C)C(C)C)n2)C(C)(C)C1]
2318
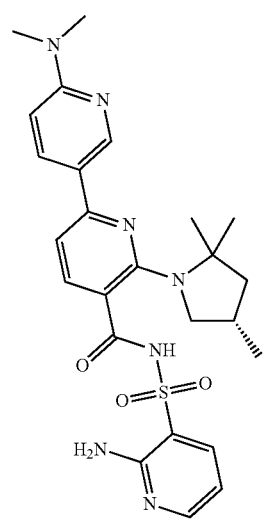
2319
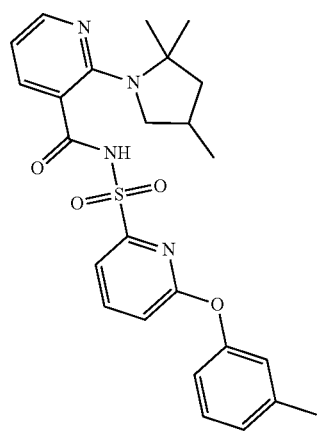 [SMILES: Cc1cccc(Oc2cccc(S(=O)(=O)NC(=O)c3cccnc3N3CC(C)CC3(C)C)n2)c1]
2320

TABLE 1-continued
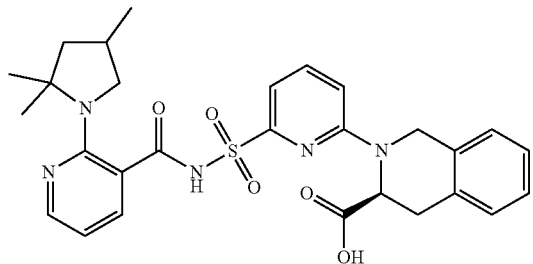
2321
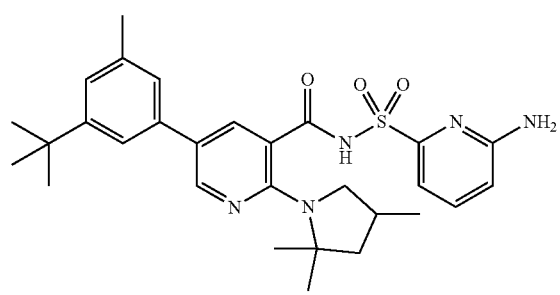 [SMILES: Cc1cc(-c2cnc(N3CC(C)CC3(C)C)c(C(=O)NS(=O)(=O)c3cccc(N)n3)c2)cc(C(C)(C)C)c1]
2322
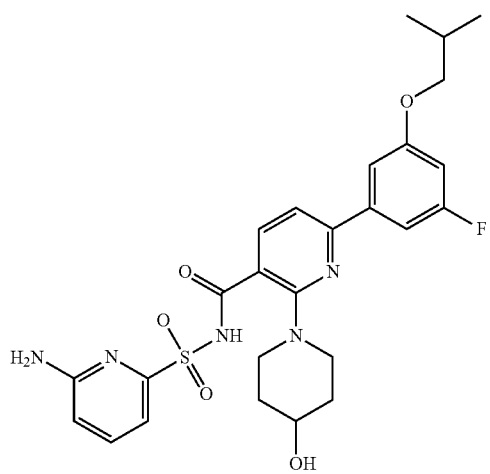
2323
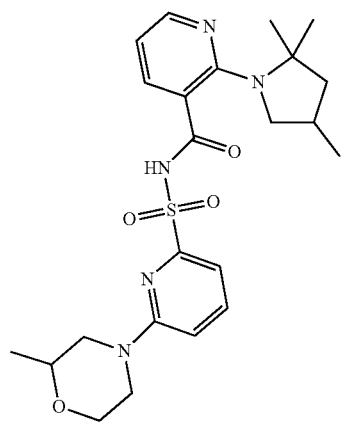
2324

TABLE 1-continued
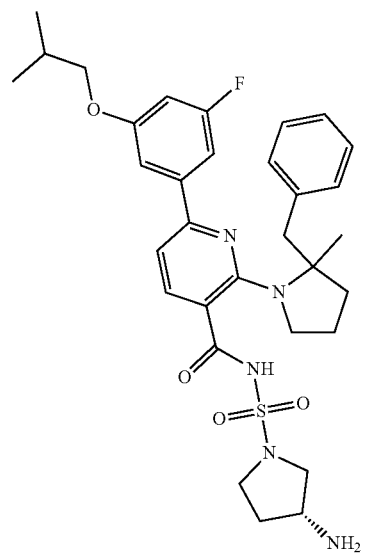 [SMILES: CC(C)COc1cc(F)cc(-c2ccc(C(=O)NS(=O)(=O)N3CC[C@@H](N)C3)c(N3CCCC3(C)Cc3ccccc3)n2)c1]
2325
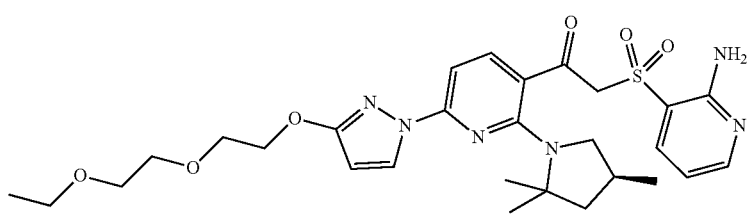 [SMILES: CCOCCOCCOc1ccn(-c2ccc(C(=O)CS(=O)(=O)c3cccnc3N)c(N3C[C@@H](C)CC3(C)C)n2)n1]
2326
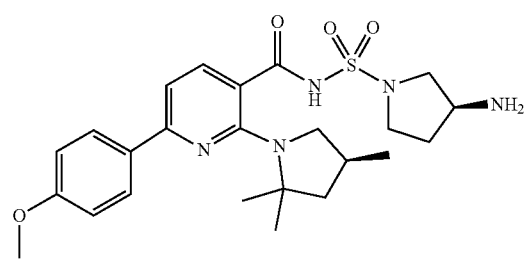 [SMILES: COc1ccc(-c2ccc(C(=O)NS(=O)(=O)N3CC[C@H](N)C3)c(N3C[C@@H](C)CC3(C)C)n2)cc1]
2327
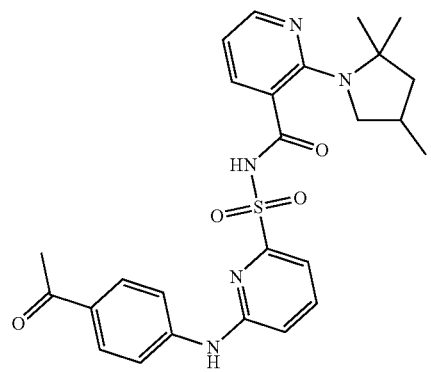 [SMILES: CC(=O)c1ccc(Nc2cccc(S(=O)(=O)NC(=O)c3cccnc3N3CC(C)CC3(C)C)n2)cc1]
2328

TABLE 1-continued
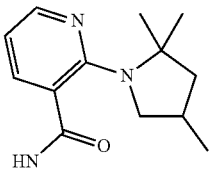  2329
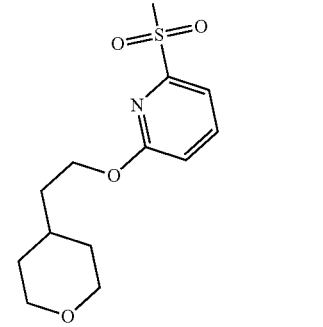  2330
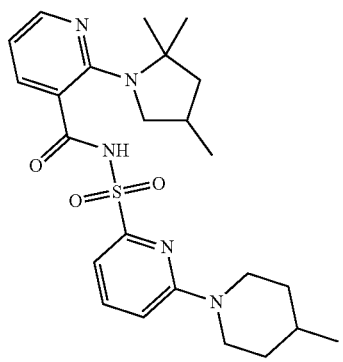 [SMILES: CC1CCN(c2cccc(S(=O)(=O)NC(=O)c3cccnc3N3CC(C)CC3(C)C)n2)CC1]  2331
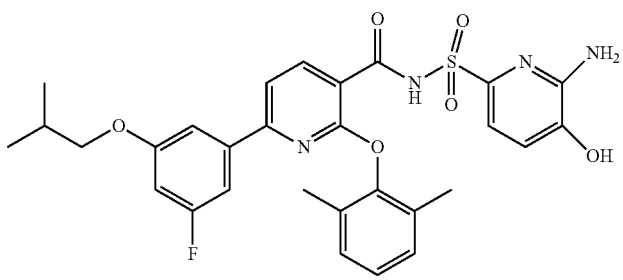 [SMILES: Cc1cccc(C)c1Oc1nc(-c2cc(F)cc(OCC(C)C)c2)ccc1C(=O)NS(=O)(=O)c1ccc(O)c(N)n1]  2332
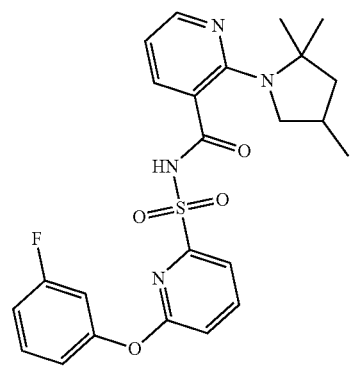 [SMILES: CC1CN(c2ncccc2C(=O)NS(=O)(=O)c2cccc(Oc3cccc(F)c3)n2)C(C)(C)C1]

TABLE 1-continued
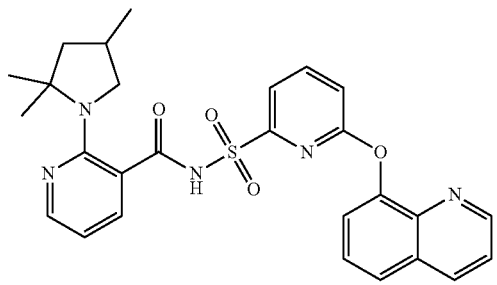 [SMILES: CC1CN(c2ncccc2C(=O)NS(=O)(=O)c2cccc(Oc3cccc4cccnc34)n2)C(C)(C)C1]
2333
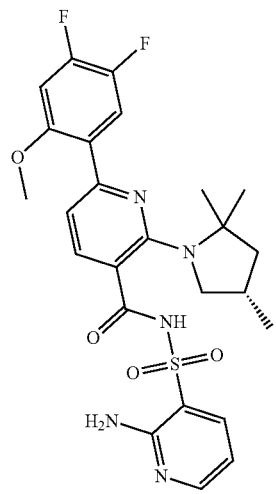 [SMILES: COc1cc(F)c(F)cc1-c1ccc(C(=O)NS(=O)(=O)c2cccnc2N)c(N2C[C@@H](C)CC2(C)C)n1]
2334
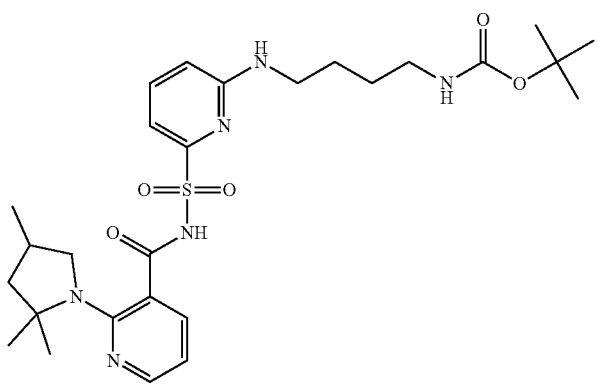 [SMILES: CC1CN(c2ncccc2C(=O)NS(=O)(=O)c2cccc(NCCCCNC(=O)OC(C)(C)C)n2)C(C)(C)C1]
2335
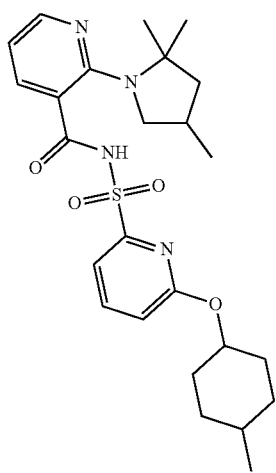 [SMILES: CC1CCC(Oc2cccc(S(=O)(=O)NC(=O)c3cccnc3N3CC(C)CC3(C)C)n2)CC1]
2336

TABLE 1-continued

| | |
|---|---|
| (structure) | 2337 |
| (structure) | 2338 |
| (structure) | 2339 |
| (structure) | 2340 |
| (structure) | 2341 |

TABLE 1-continued
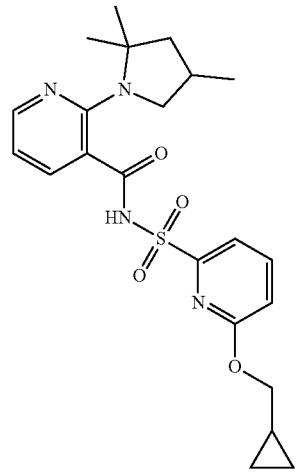 [SMILES: CC1CN(c2ncccc2C(=O)NS(=O)(=O)c2cccc(OCC3CC3)n2)C(C)(C)C1]
2342
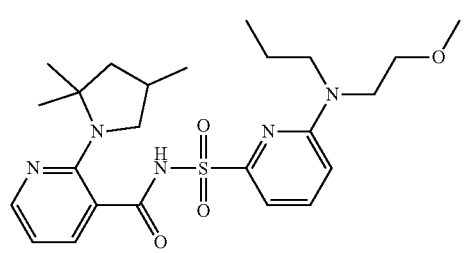 [SMILES: CCCN(CCOC)c1cccc(S(=O)(=O)NC(=O)c2cccnc2N2CC(C)CC2(C)C)n1]
2343
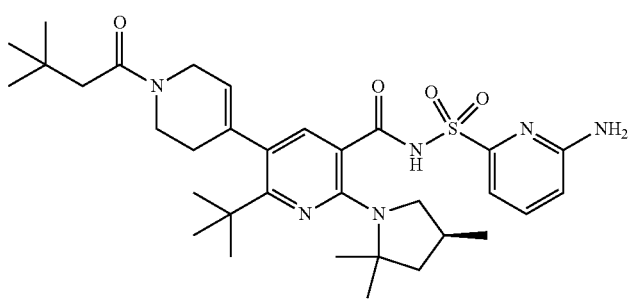 [SMILES: C[C@@H]1CN(c2nc(C(C)(C)C)c(C3=CCN(C(=O)CC(C)(C)C)CC3)cc2C(=O)NS(=O)(=O)c2cccc(N)n2)C(C)(C)C1]
2344
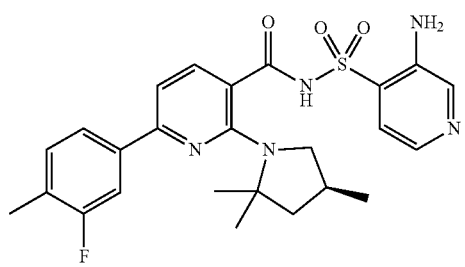 [SMILES: Cc1ccc(-c2ccc(C(=O)NS(=O)(=O)c3ccncc3N)c(N3C[C@@H](C)CC3(C)C)n2)cc1F]
2345
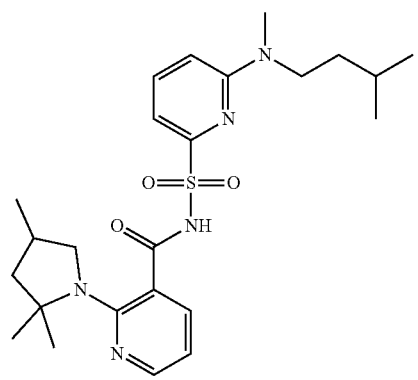 [SMILES: CC(C)CCN(C)c1cccc(S(=O)(=O)NC(=O)c2cccnc2N2CC(C)CC2(C)C)n1]
2346

TABLE 1-continued
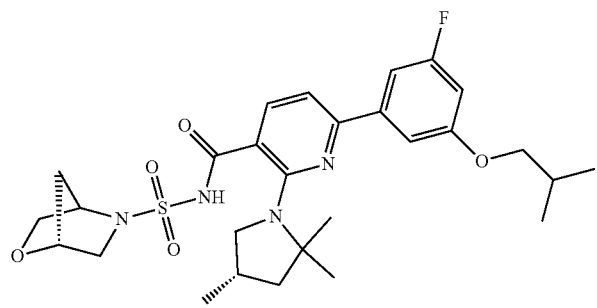 [SMILES: CC(C)COc1cc(F)cc(-c2ccc(C(=O)NS(=O)(=O)N3C[C@H]4CC3CO4)c(N3C[C@@H](C)CC3(C)C)n2)c1] 2347
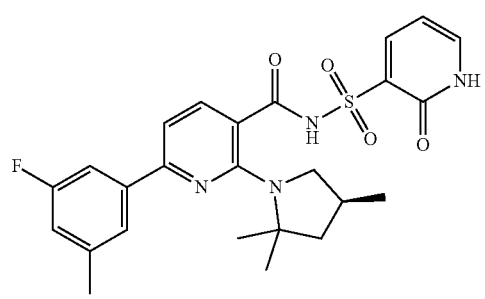 [SMILES: Cc1cc(F)cc(-c2ccc(C(=O)NS(=O)(=O)c3ccc[nH]c3=O)c(N3C[C@@H](C)CC3(C)C)n2)c1] 2348
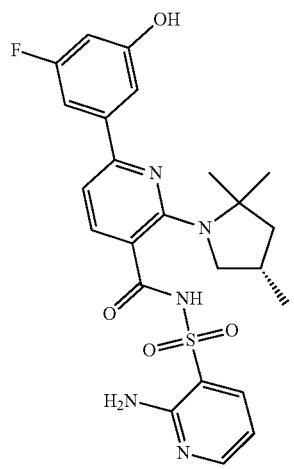 [SMILES: C[C@@H]1CN(c2nc(-c3cc(O)cc(F)c3)ccc2C(=O)NS(=O)(=O)c2cccnc2N)C(C)(C)C1] 2349
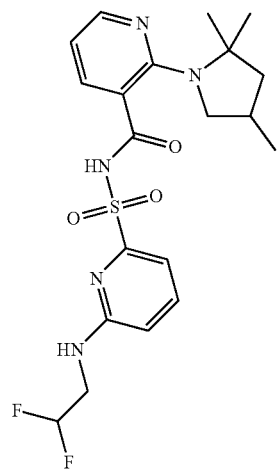 [SMILES: CC1CN(c2ncccc2C(=O)NS(=O)(=O)c2cccc(NCC(F)F)n2)C(C)(C)C1] 2350

TABLE 1-continued
| | |
|---|---|
| 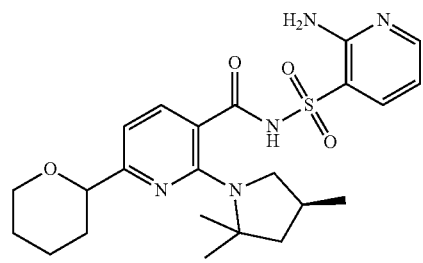 [SMILES: C[C@@H]1CN(c2nc(C3CCCCO3)ccc2C(=O)NS(=O)(=O)c2cccnc2N)C(C)(C)C1] | 2351 |
| 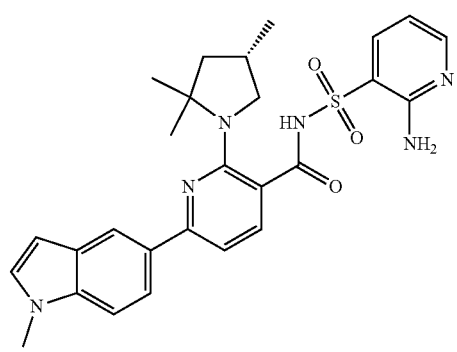 [SMILES: C[C@@H]1CN(c2nc(-c3ccc4c(ccn4C)c3)ccc2C(=O)NS(=O)(=O)c2cccnc2N)C(C)(C)C1] | 2352 |
| 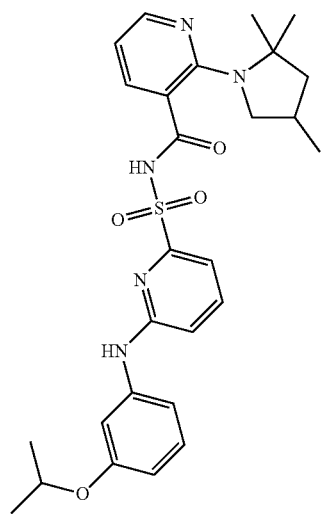 [SMILES: CC1CN(c2ncccc2C(=O)NS(=O)(=O)c2cccc(Nc3cccc(OC(C)C)c3)n2)C(C)(C)C1] | 2353 |
| 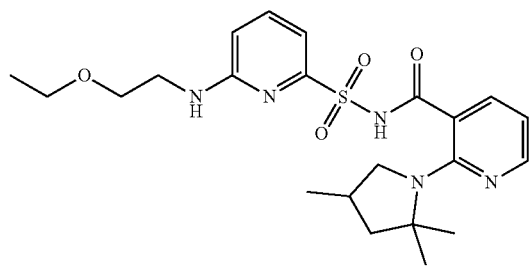 [SMILES: CCOCCNc1cccc(S(=O)(=O)NC(=O)c2cccnc2N2CC(C)CC2(C)C)n1] | 2354 |

TABLE 1-continued
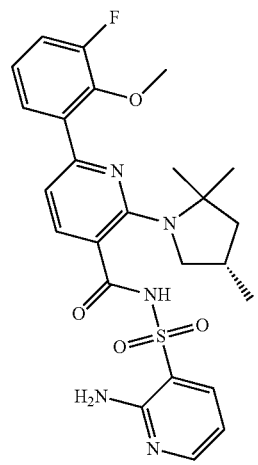 [SMILES: COc1c(F)cccc1-c1ccc(C(=O)NS(=O)(=O)c2cccnc2N)c(N2C[C@@H](C)CC2(C)C)n1]
2355
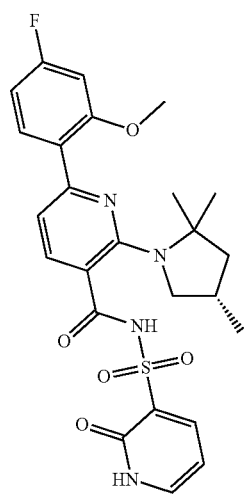 [SMILES: COc1cc(F)ccc1-c1ccc(C(=O)NS(=O)(=O)c2ccc[nH]c2=O)c(N2C[C@@H](C)CC2(C)C)n1]
2356
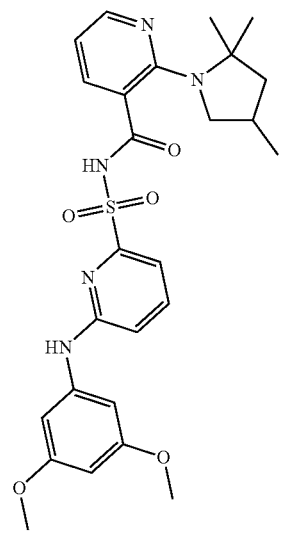 [SMILES: COc1cc(Nc2cccc(S(=O)(=O)NC(=O)c3cccnc3N3CC(C)CC3(C)C)n2)cc(OC)c1]
2357

| | |
|---|---|
| 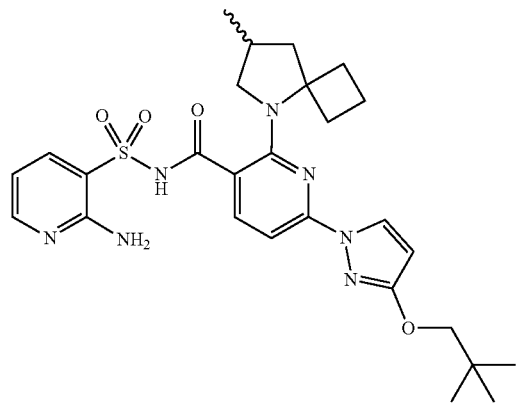 [SMILES: CC1CN(c2nc(-n3ccc(OCC(C)(C)C)n3)ccc2C(=O)NS(=O)(=O)c2cccnc2N)C2(CCC2)C1] | 2358 |
| 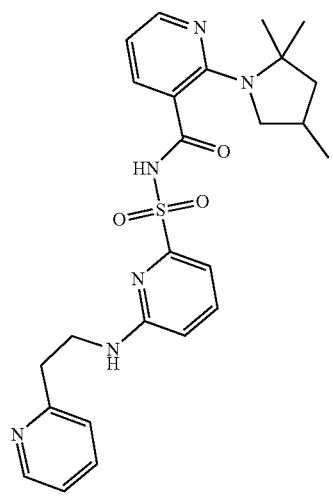 [SMILES: CC1CN(c2ncccc2C(=O)NS(=O)(=O)c2cccc(NCCc3ccccn3)n2)C(C)(C)C1] | 2359 |
| 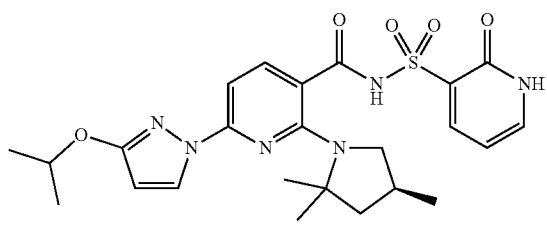 [SMILES: CC(C)Oc1ccn(-c2ccc(C(=O)NS(=O)(=O)c3ccc[nH]c3=O)c(N3C[C@@H](C)CC3(C)C)n2)n1] | 2360 |
| 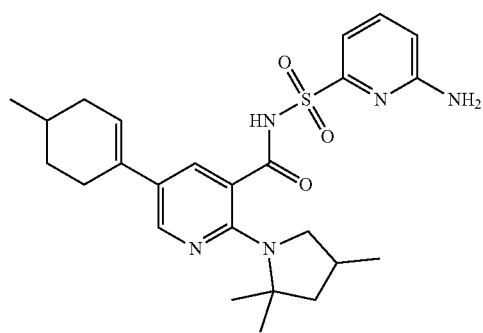 [SMILES: CC1CC=C(c2cnc(N3CC(C)CC3(C)C)c(C(=O)NS(=O)(=O)c3cccc(N)n3)c2)CC1] | 2361 |

TABLE 1-continued
| | |
|---|---|
| 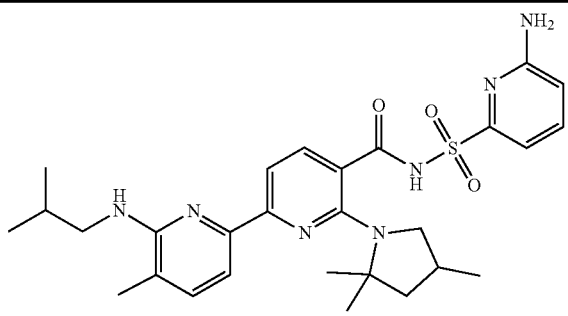 | 2362 |
| 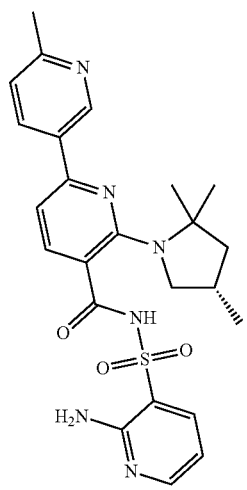 [SMILES: Cc1ccc(-c2ccc(C(=O)NS(=O)(=O)c3cccnc3N)c(N3C[C@@H](C)CC3(C)C)n2)cn1] | 2363 |
| 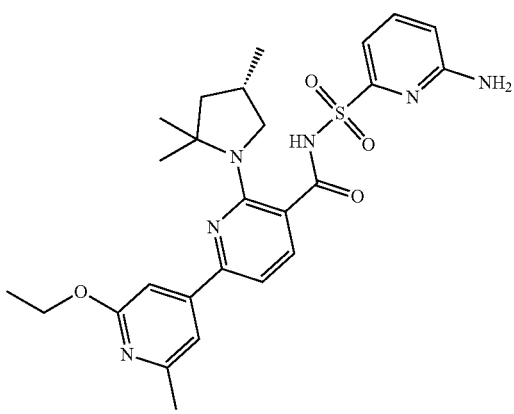 [SMILES: CCOc1cc(-c2ccc(C(=O)NS(=O)(=O)c3cccc(N)n3)c(N3C[C@@H](C)CC3(C)C)n2)cc(C)n1] | 2364 |
| 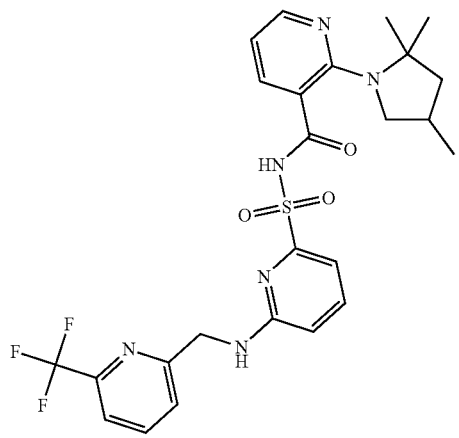 [SMILES: CC1CN(c2ncccc2C(=O)NS(=O)(=O)c2cccc(NCc3cccc(C(F)(F)F)n3)n2)C(C)(C)C1] | 2365 |

TABLE 1-continued
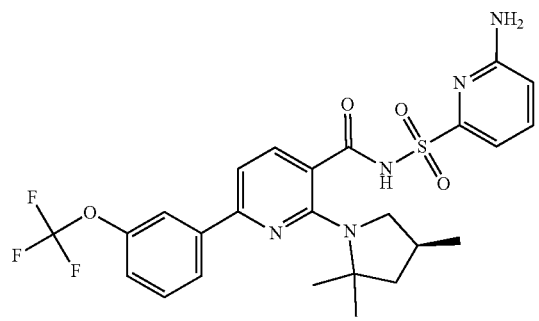 [SMILES: C[C@@H]1CN(c2nc(-c3cccc(OC(F)(F)F)c3)ccc2C(=O)NS(=O)(=O)c2cccc(N)n2)C(C)(C)C1] 2366
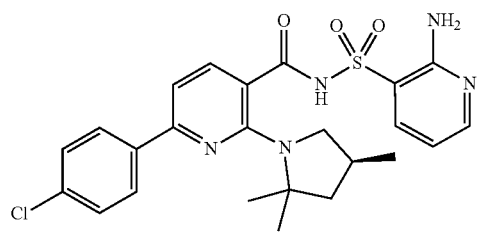 [SMILES: C[C@@H]1CN(c2nc(-c3ccc(Cl)cc3)ccc2C(=O)NS(=O)(=O)c2cccnc2N)C(C)(C)C1] 2367
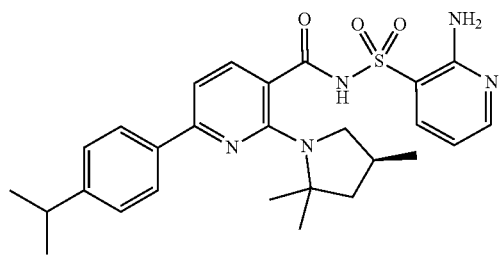 [SMILES: CC(C)c1ccc(-c2ccc(C(=O)NS(=O)(=O)c3cccnc3N)c(N3C[C@@H](C)CC3(C)C)n2)cc1] 2368
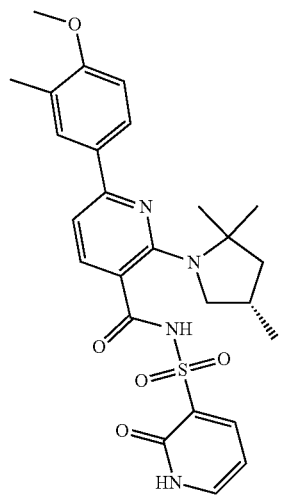 2369

| | |
|---|---|
| 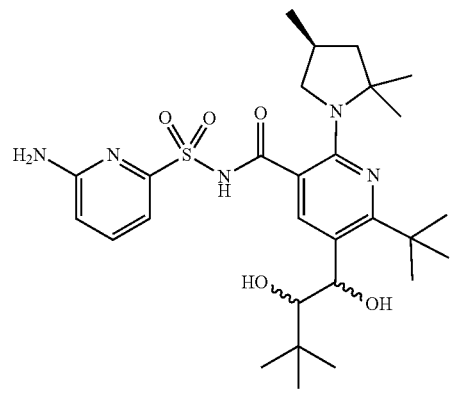 [SMILES: C[C@@H]1CN(c2nc(C(C)(C)C)c(C(O)C(O)C(C)(C)C)cc2C(=O)NS(=O)(=O)c2cccc(N)n2)C(C)(C)C1] | 2370 |
| 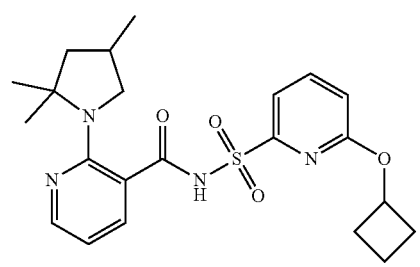 | 2371 |
| 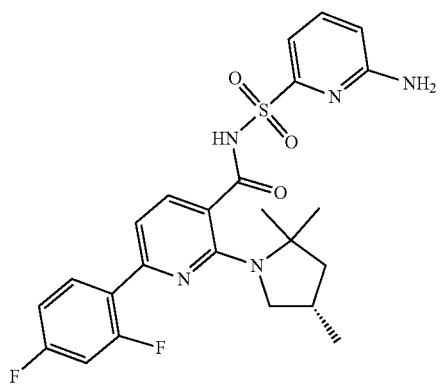 [SMILES: C[C@@H]1CN(c2nc(-c3ccc(F)cc3F)ccc2C(=O)NS(=O)(=O)c2cccc(N)n2)C(C)(C)C1] | 2372 |
| 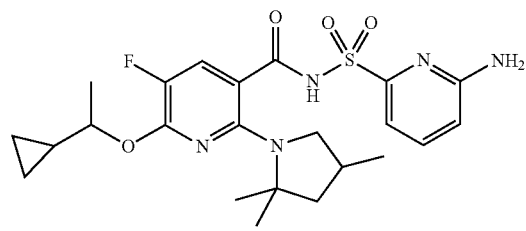 [SMILES: CC1CN(c2nc(OC(C)C3CC3)c(F)cc2C(=O)NS(=O)(=O)c2cccc(N)n2)C(C)(C)C1] | 2373 |
| 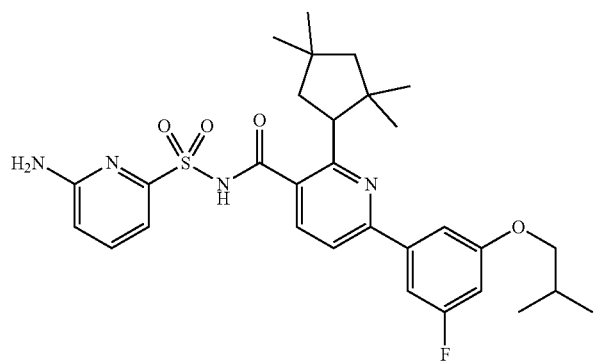 [SMILES: CC(C)COc1cc(F)cc(-c2ccc(C(=O)NS(=O)(=O)c3cccc(N)n3)c(C3CC(C)(C)CC3(C)C)n2)c1] | 2374 |

TABLE 1-continued
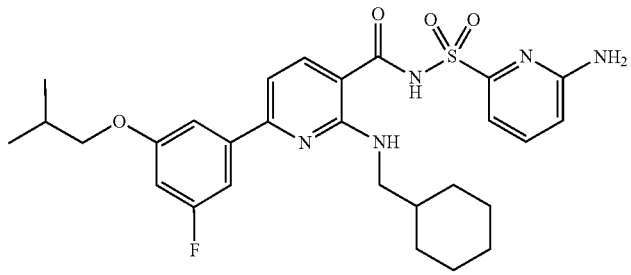 [SMILES: CC(C)COc1cc(F)cc(-c2ccc(C(=O)NS(=O)(=O)c3cccc(N)n3)c(NCC3CCCCC3)n2)c1]
2375
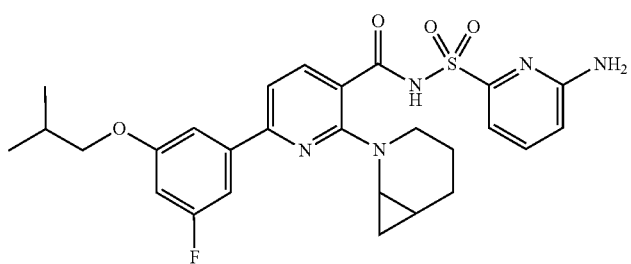 [SMILES: CC(C)COc1cc(F)cc(-c2ccc(C(=O)NS(=O)(=O)c3cccc(N)n3)c(N3CCCC4CC43)n2)c1]
2376
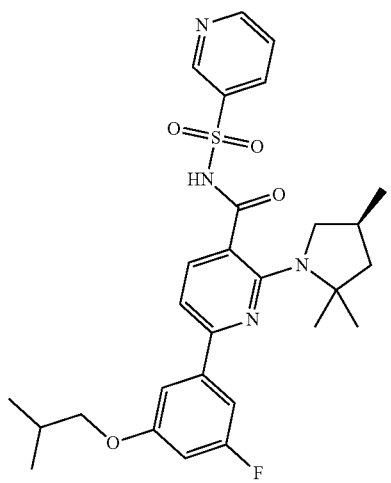 [SMILES: CC(C)COc1cc(F)cc(-c2ccc(C(=O)NS(=O)(=O)c3cccnc3)c(N3C[C@@H](C)CC3(C)C)n2)c1]
2377
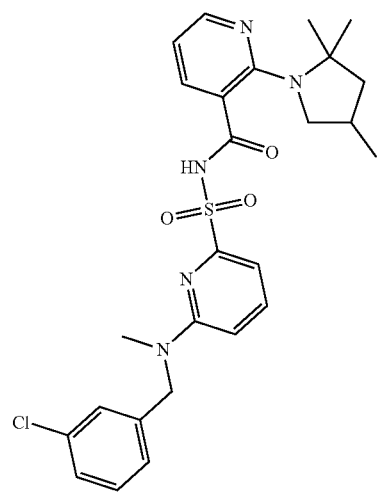 [SMILES: CC1CN(c2ncccc2C(=O)NS(=O)(=O)c2cccc(N(C)Cc3cccc(Cl)c3)n2)C(C)(C)C1]
2378

TABLE 1-continued
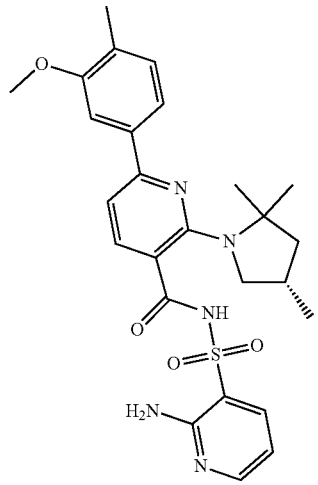
2379
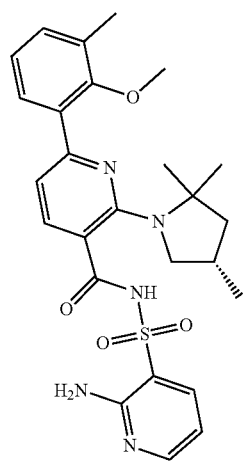 [SMILES: COc1c(C)cccc1-c1ccc(C(=O)NS(=O)(=O)c2cccnc2N)c(N2C[C@@H](C)CC2(C)C)n1]
2380
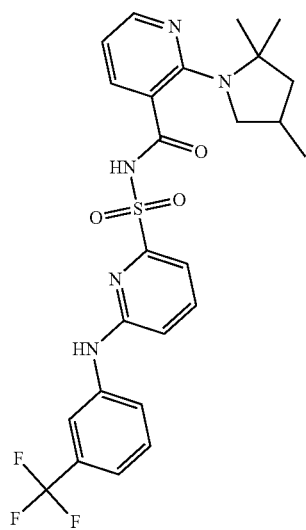 [SMILES: CC1CN(c2ncccc2C(=O)NS(=O)(=O)c2cccc(Nc3cccc(C(F)(F)F)c3)n2)C(C)(C)C1]
2381

TABLE 1-continued
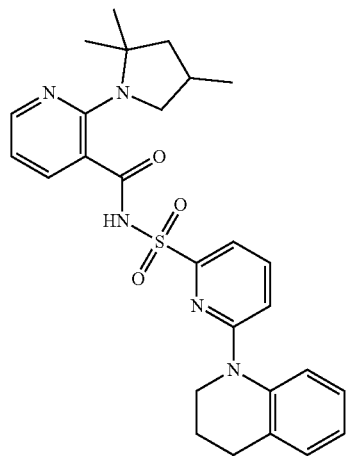 [SMILES: CC1CN(c2ncccc2C(=O)NS(=O)(=O)c2cccc(N3CCCc4ccccc43)n2)C(C)(C)C1]
2382
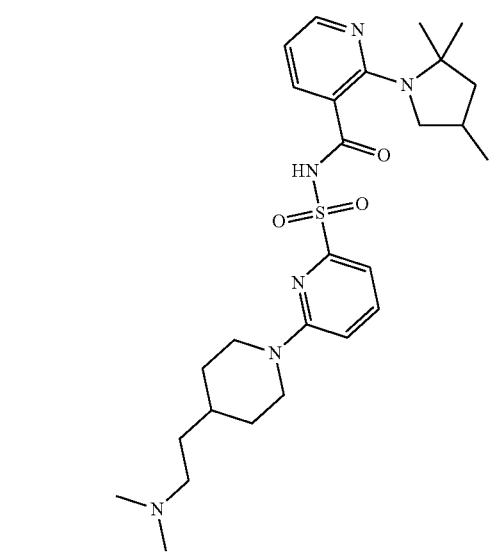
2383
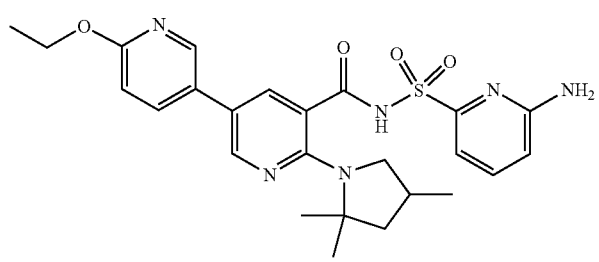 [SMILES: CCOc1ccc(-c2cnc(N3CC(C)CC3(C)C)c(C(=O)NS(=O)(=O)c3cccc(N)n3)c2)cn1]
2384
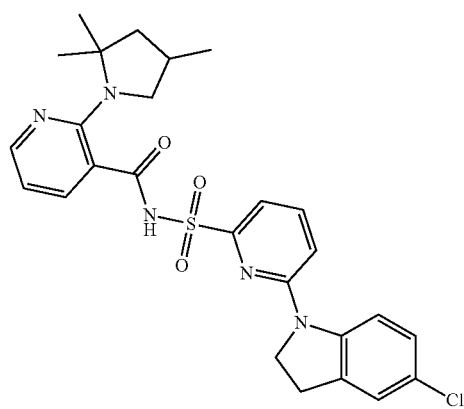 [SMILES: CC1CN(c2ncccc2C(=O)NS(=O)(=O)c2cccc(N3CCc4cc(Cl)ccc43)n2)C(C)(C)C1]
2385

TABLE 1-continued
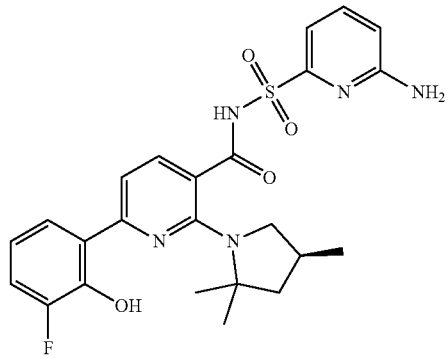 [SMILES: C[C@@H]1CN(c2nc(-c3cccc(F)c3O)ccc2C(=O)NS(=O)(=O)c2cccc(N)n2)C(C)(C)C1]
2386
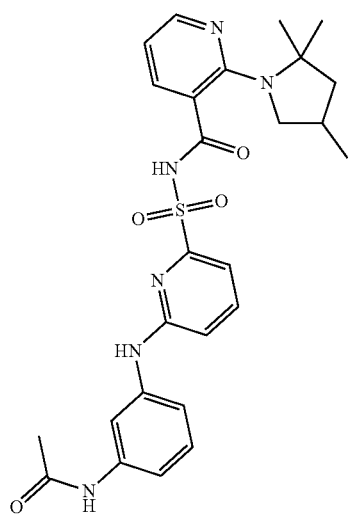 [SMILES: CC(=O)Nc1cccc(Nc2cccc(S(=O)(=O)NC(=O)c3cccnc3N3CC(C)CC3(C)C)n2)c1]
2387
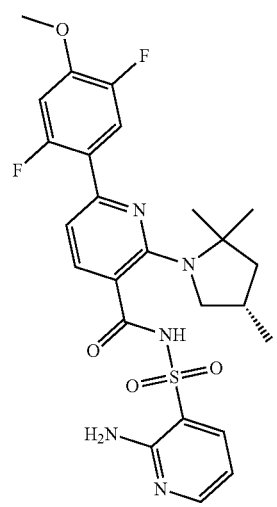 [SMILES: COc1cc(F)c(-c2ccc(C(=O)NS(=O)(=O)c3cccnc3N)c(N3C[C@@H](C)CC3(C)C)n2)cc1F]
2388
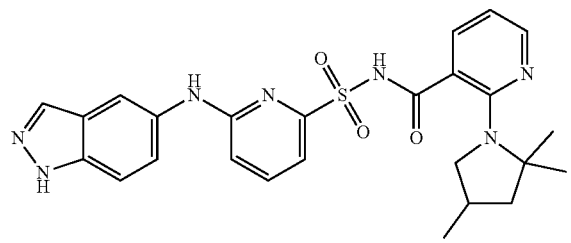 [SMILES: CC1CN(c2ncccc2C(=O)NS(=O)(=O)c2cccc(Nc3ccc4[nH]ncc4c3)n2)C(C)(C)C1]
2389

TABLE 1-continued
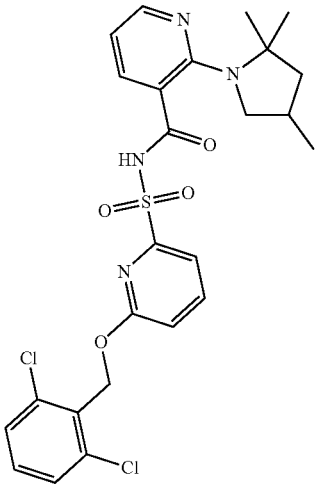 [SMILES: CC1CN(c2ncccc2C(=O)NS(=O)(=O)c2cccc(OCc3c(Cl)cccc3Cl)n2)C(C)(C)C1]
2390
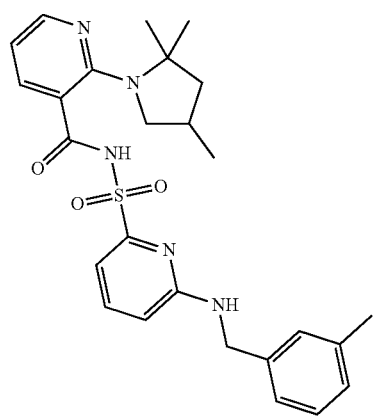 [SMILES: Cc1cccc(CNc2cccc(S(=O)(=O)NC(=O)c3cccnc3N3CC(C)CC3(C)C)n2)c1]
2391
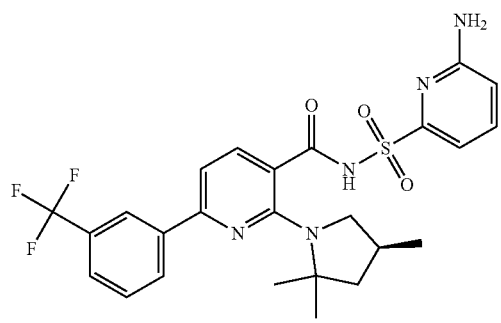 [SMILES: C[C@@H]1CN(c2nc(-c3cccc(C(F)(F)F)c3)ccc2C(=O)NS(=O)(=O)c2cccc(N)n2)C(C)(C)C1]
2392
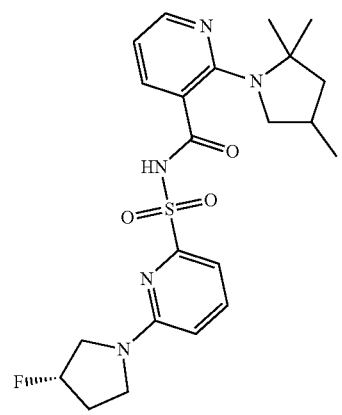 [SMILES: CC1CN(c2ncccc2C(=O)NS(=O)(=O)c2cccc(N3CC[C@H](F)C3)n2)C(C)(C)C1]
2393

TABLE 1-continued
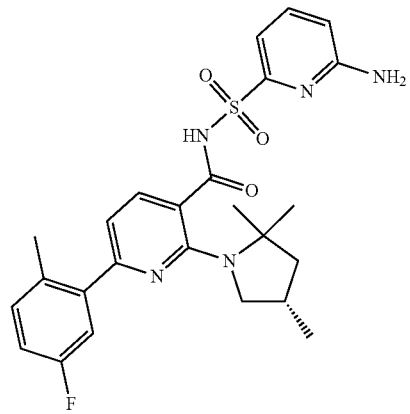 [SMILES: Cc1ccc(F)cc1-c1ccc(C(=O)NS(=O)(=O)c2cccc(N)n2)c(N2C[C@@H](C)CC2(C)C)n1]
2394
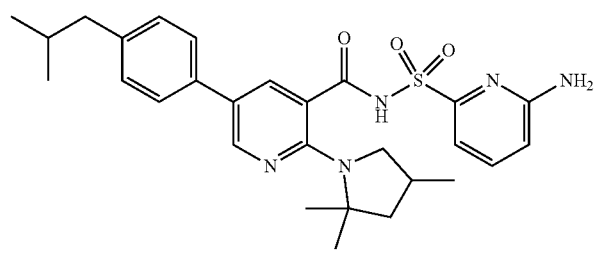 [SMILES: CC(C)Cc1ccc(-c2cnc(N3CC(C)CC3(C)C)c(C(=O)NS(=O)(=O)c3cccc(N)n3)c2)cc1]
2395
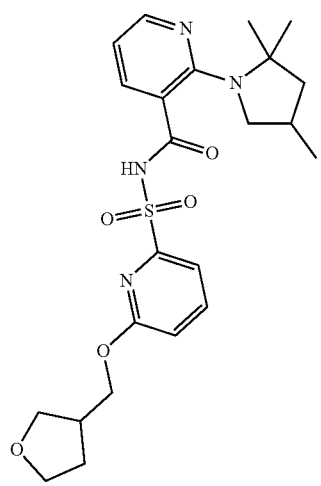 [SMILES: CC1CN(c2ncccc2C(=O)NS(=O)(=O)c2cccc(OCC3CCOC3)n2)C(C)(C)C1]
2396
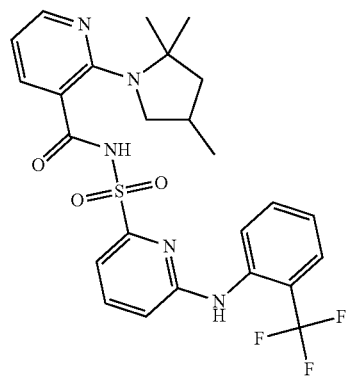 [SMILES: CC1CN(c2ncccc2C(=O)NS(=O)(=O)c2cccc(Nc3ccccc3C(F)(F)F)n2)C(C)(C)C1]
2397

TABLE 1-continued
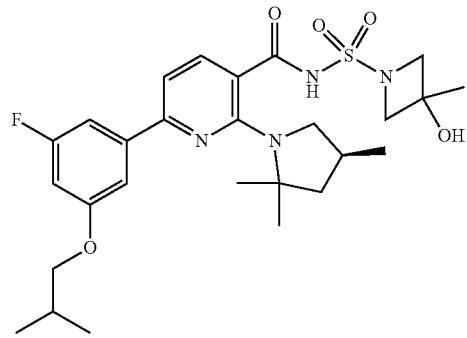 [SMILES: CC(C)COc1cc(F)cc(-c2ccc(C(=O)NS(=O)(=O)N3CC(C)(O)C3)c(N3C[C@@H](C)CC3(C)C)n2)c1]  2398
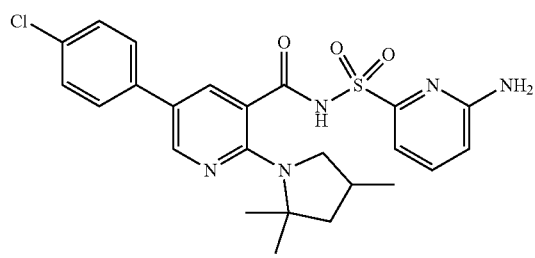 [SMILES: CC1CN(c2ncc(-c3ccc(Cl)cc3)cc2C(=O)NS(=O)(=O)c2cccc(N)n2)C(C)(C)C1]  2399
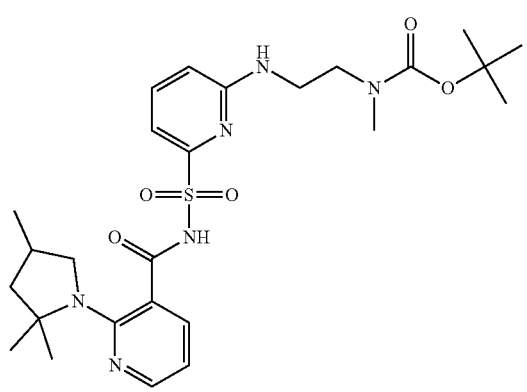 [SMILES: CC1CN(c2ncccc2C(=O)NS(=O)(=O)c2cccc(NCCN(C)C(=O)OC(C)(C)C)n2)C(C)(C)C1]  2400
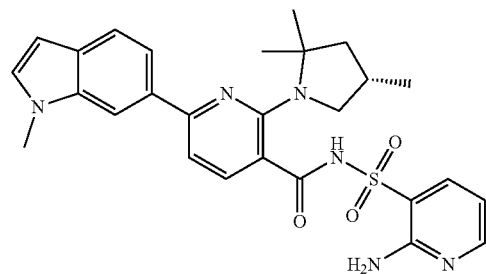 [SMILES: C[C@@H]1CN(c2nc(-c3ccc4ccn(C)c4c3)ccc2C(=O)NS(=O)(=O)c2cccnc2N)C(C)(C)C1]  2401

TABLE 1-continued
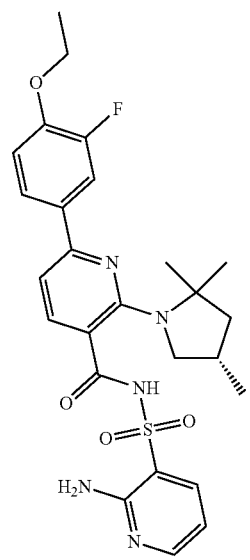 [SMILES: CCOc1ccc(-c2ccc(C(=O)NS(=O)(=O)c3cccnc3N)c(N3C[C@@H](C)CC3(C)C)n2)cc1F]
2402
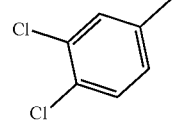
2403
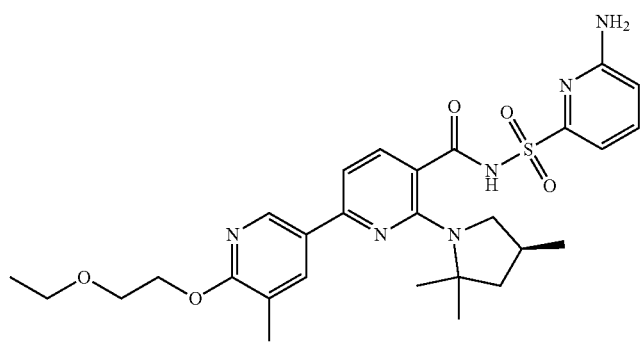 [SMILES: CCOCCOc1ncc(-c2ccc(C(=O)NS(=O)(=O)c3cccc(N)n3)c(N3C[C@@H](C)CC3(C)C)n2)cc1C]
2404

TABLE 1-continued
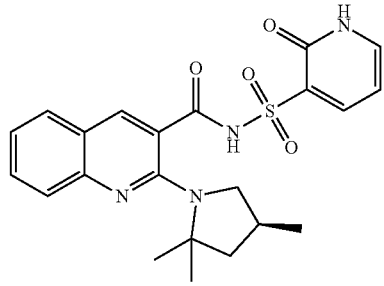 [SMILES: C[C@@H]1CN(c2nc3ccccc3cc2C(=O)NS(=O)(=O)c2ccc[nH]c2=O)C(C)(C)C1]
2405
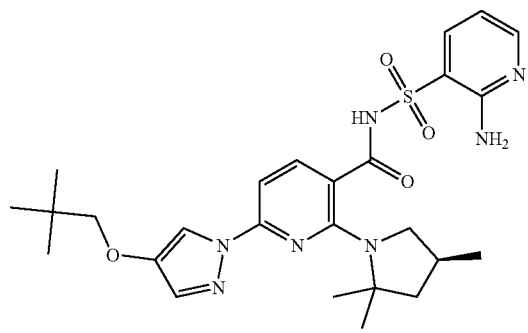 [SMILES: C[C@@H]1CN(c2nc(-n3cc(OCC(C)(C)C)cn3)ccc2C(=O)NS(=O)(=O)c2cccnc2N)C(C)(C)C1]
2406
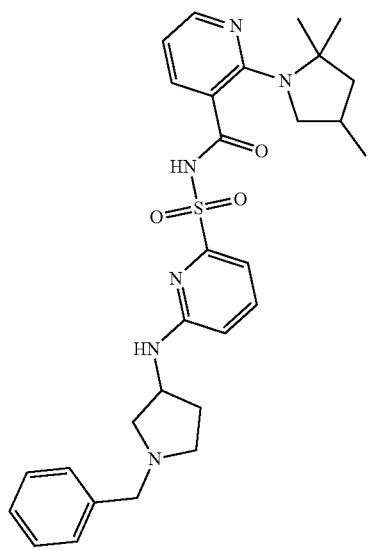 [SMILES: CC1CN(c2ncccc2C(=O)NS(=O)(=O)c2cccc(NC3CCN(Cc4ccccc4)C3)n2)C(C)(C)C1]
2407
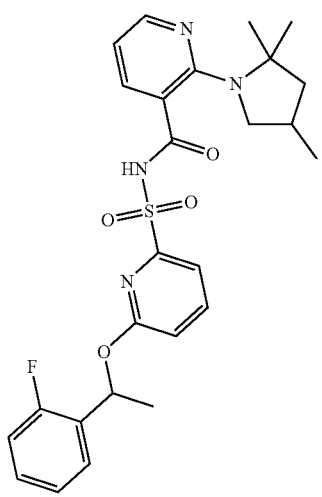 [SMILES: CC1CN(c2ncccc2C(=O)NS(=O)(=O)c2cccc(OC(C)c3ccccc3F)n2)C(C)(C)C1]
2408

TABLE 1-continued
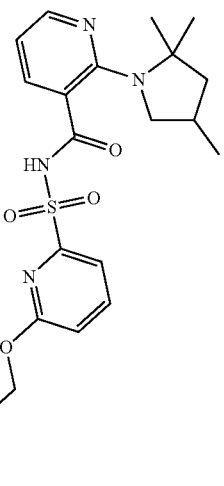
2409
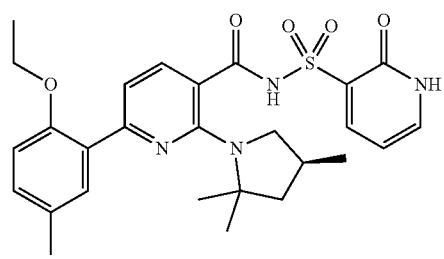 [SMILES: CCOc1ccc(C)cc1-c1ccc(C(=O)NS(=O)(=O)c2ccc[nH]c2=O)c(N2C[C@@H](C)CC2(C)C)n1]
2410
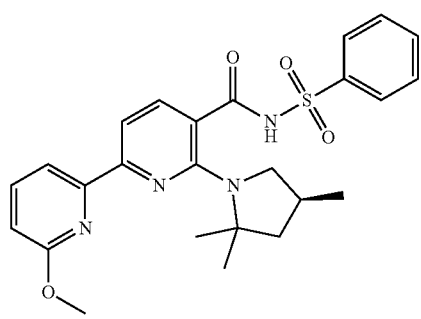 [SMILES: COc1cccc(-c2ccc(C(=O)NS(=O)(=O)c3ccccc3)c(N3C[C@@H](C)CC3(C)C)n2)n1]
2411
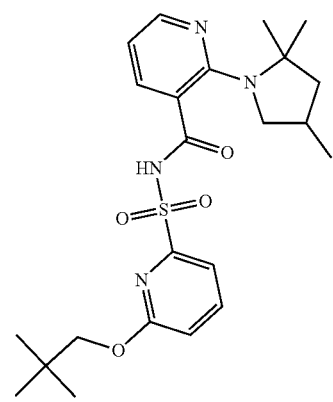 [SMILES: CC1CN(c2ncccc2C(=O)NS(=O)(=O)c2cccc(OCC(C)(C)C)n2)C(C)(C)C1]
2412

TABLE 1-continued
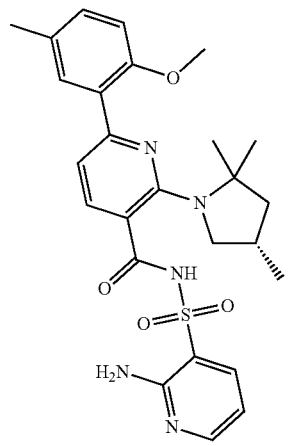
2413
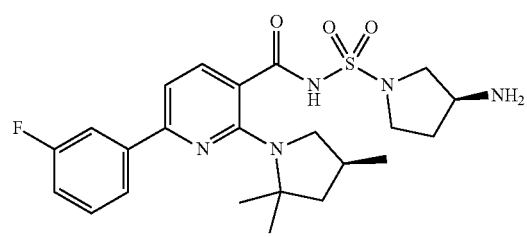 [SMILES: C[C@@H]1CN(c2nc(-c3cccc(F)c3)ccc2C(=O)NS(=O)(=O)N2CC[C@H](N)C2)C(C)(C)C1]
2414
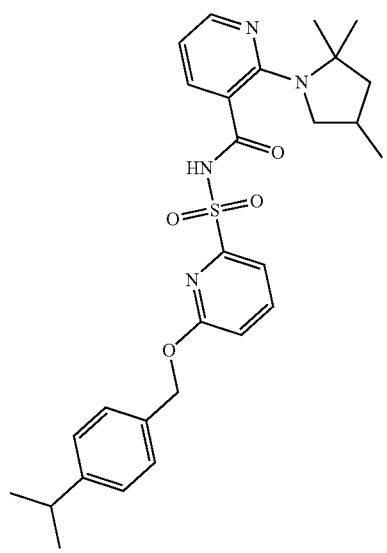 [SMILES: CC1CN(c2ncccc2C(=O)NS(=O)(=O)c2cccc(OCc3ccc(C(C)C)cc3)n2)C(C)(C)C1]
2415

TABLE 1-continued
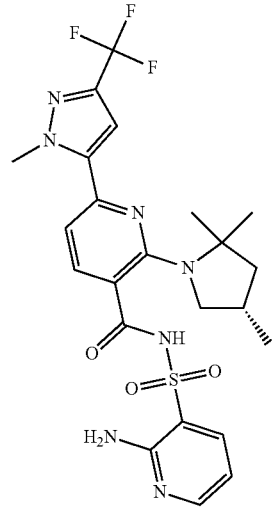
2416
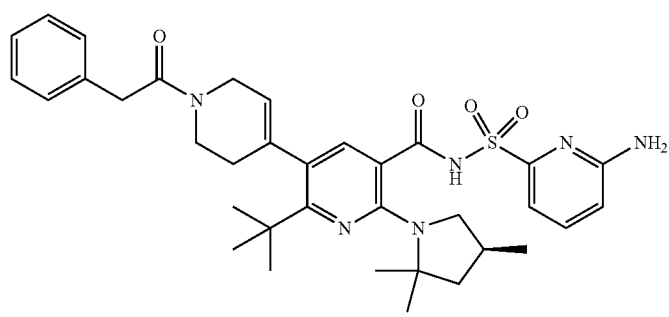 [SMILES: C[C@@H]1CN(c2nc(C(C)(C)C)c(C3=CCN(C(=O)Cc4ccccc4)CC3)cc2C(=O)NS(=O)(=O)c2cccc(N)n2)C(C)(C)C1]
2417
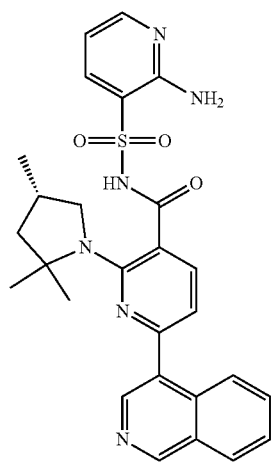 [SMILES: C[C@@H]1CN(c2nc(-c3cncc4ccccc34)ccc2C(=O)NS(=O)(=O)c2cccnc2N)C(C)(C)C1]
2418
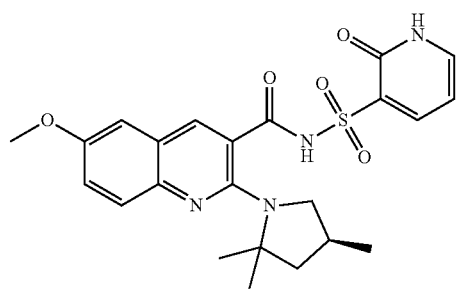 [SMILES: COc1ccc2nc(N3C[C@@H](C)CC3(C)C)c(C(=O)NS(=O)(=O)c3ccc[nH]c3=O)cc2c1]
2419

TABLE 1-continued
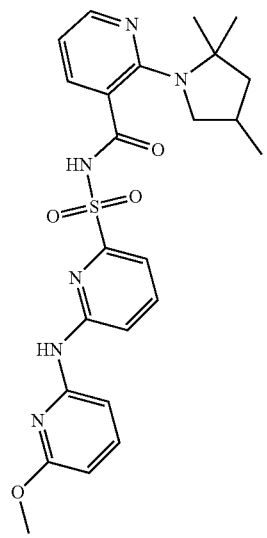 [SMILES: COc1cccc(Nc2cccc(S(=O)(=O)NC(=O)c3cccnc3N3CC(C)CC3(C)C)n2)n1]
2420
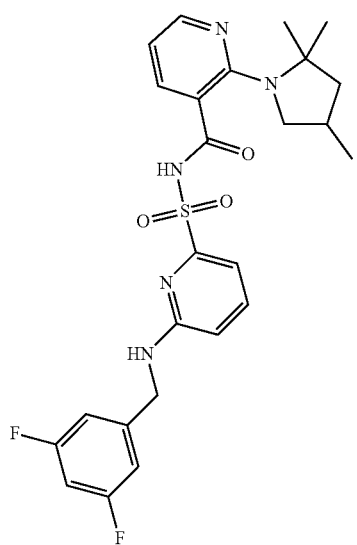 [SMILES: CC1CN(c2ncccc2C(=O)NS(=O)(=O)c2cccc(NCc3cc(F)cc(F)c3)n2)C(C)(C)C1]
2421
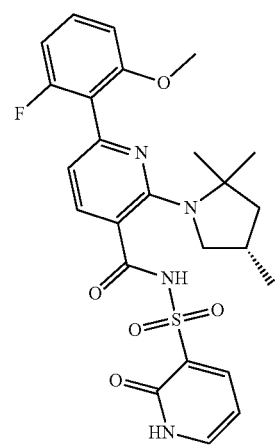 [SMILES: COc1cccc(F)c1-c1ccc(C(=O)NS(=O)(=O)c2ccc[nH]c2=O)c(N2C[C@@H](C)CC2(C)C)n1]
2422

TABLE 1-continued
| | |
|---|---|
| 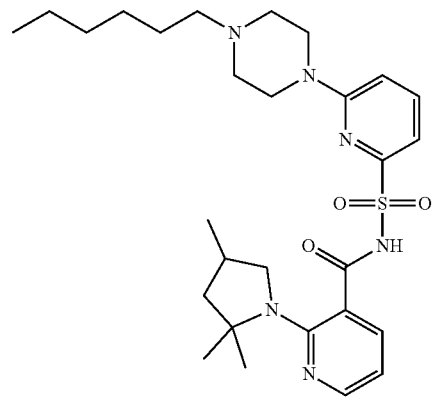 [SMILES: CCCCCCN1CCN(c2cccc(S(=O)(=O)NC(=O)c3cccnc3N3CC(C)CC3(C)C)n2)CC1] | 2423 |
| 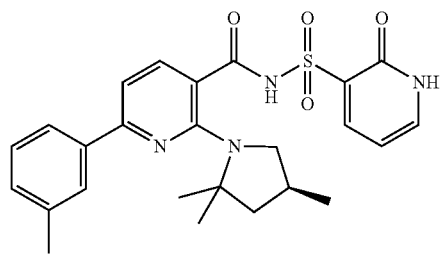 [SMILES: Cc1cccc(-c2ccc(C(=O)NS(=O)(=O)c3ccc[nH]c3=O)c(N3C[C@@H](C)CC3(C)C)n2)c1] | 2424 |
| 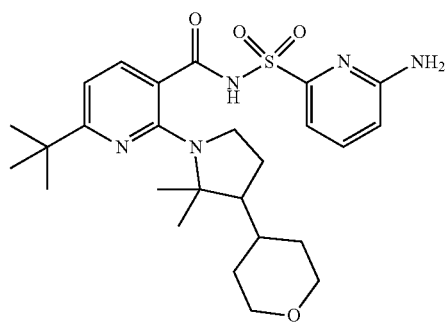 [SMILES: CC(C)(C)c1ccc(C(=O)NS(=O)(=O)c2cccc(N)n2)c(N2CCC(C3CCOCC3)C2(C)C)n1] | 2425 |
| 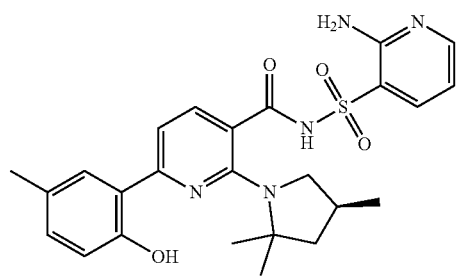 [SMILES: Cc1ccc(O)c(-c2ccc(C(=O)NS(=O)(=O)c3cccnc3N)c(N3C[C@@H](C)CC3(C)C)n2)c1] | 2426 |
| 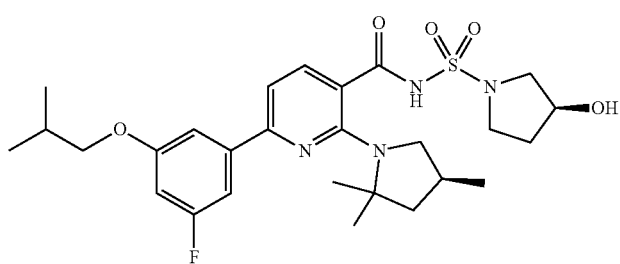 [SMILES: CC(C)COc1cc(F)cc(-c2ccc(C(=O)NS(=O)(=O)N3CC[C@H](O)C3)c(N3C[C@@H](C)CC3(C)C)n2)c1] | 2427 |

TABLE 1-continued
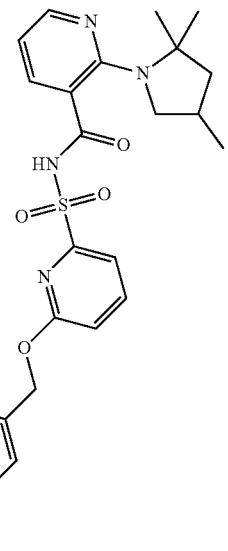
2428
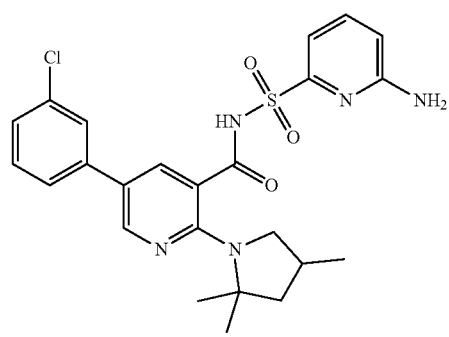
2429
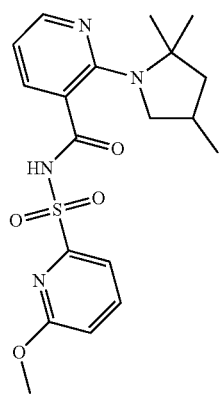 [SMILES: COc1cccc(S(=O)(=O)NC(=O)c2cccnc2N2CC(C)CC2(C)C)n1]
2430
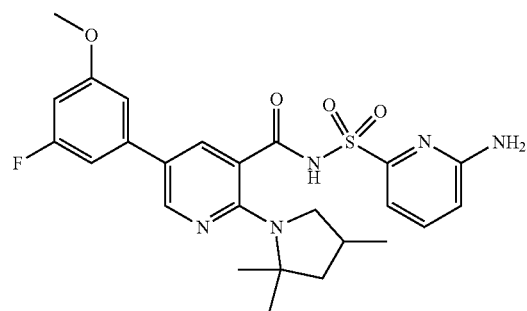 [SMILES: COc1cc(F)cc(-c2cnc(N3CC(C)CC3(C)C)c(C(=O)NS(=O)(=O)c3cccc(N)n3)c2)c1]
2431

TABLE 1-continued
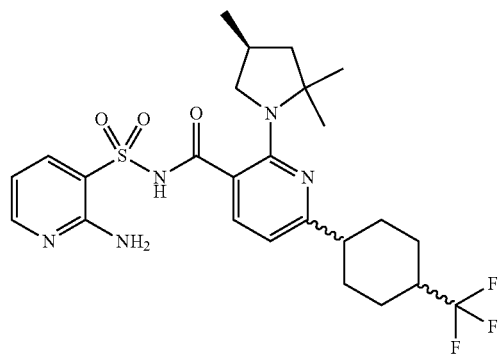 [SMILES: C[C@@H]1CN(c2nc(C3CCC(C(F)(F)F)CC3)ccc2C(=O)NS(=O)(=O)c2cccnc2N)C(C)(C)C1]
2432
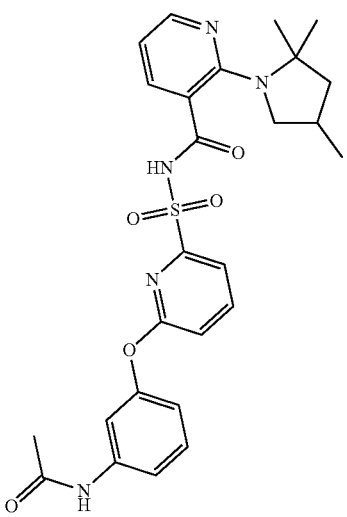 [SMILES: CC(=O)Nc1cccc(Oc2cccc(S(=O)(=O)NC(=O)c3cccnc3N3CC(C)CC3(C)C)n2)c1]
2433
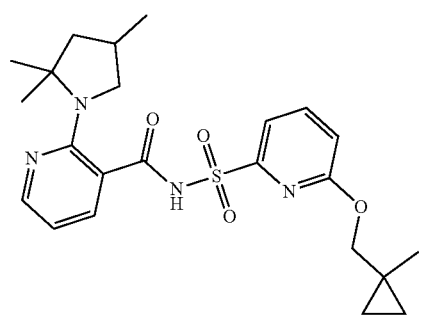
2434
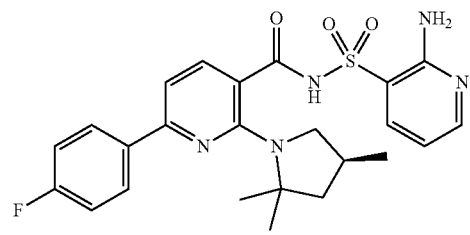 [SMILES: C[C@@H]1CN(c2nc(-c3ccc(F)cc3)ccc2C(=O)NS(=O)(=O)c2cccnc2N)C(C)(C)C1]
2435

TABLE 1-continued
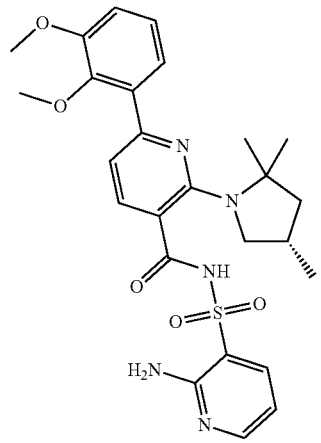 2436
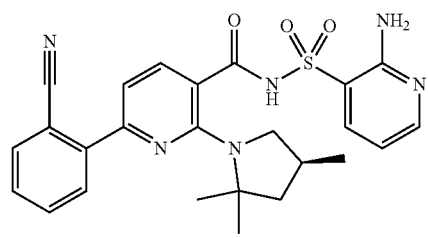 [SMILES: C[C@@H]1CN(c2nc(-c3ccccc3C#N)ccc2C(=O)NS(=O)(=O)c2cccnc2N)C(C)(C)C1] 2437
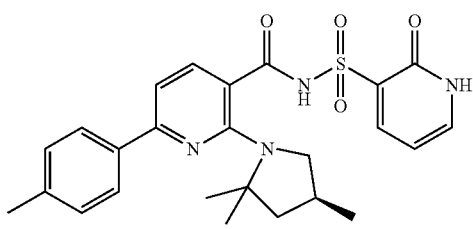 [SMILES: Cc1ccc(-c2ccc(C(=O)NS(=O)(=O)c3ccc[nH]c3=O)c(N3C[C@@H](C)CC3(C)C)n2)cc1] 2438
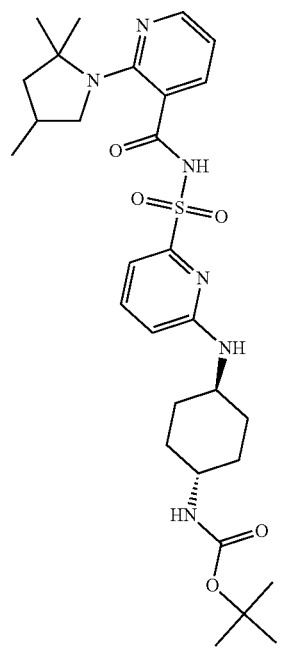 [SMILES: CC1CN(c2ncccc2C(=O)NS(=O)(=O)c2cccc(N[C@H]3CC[C@H](NC(=O)OC(C)(C)C)CC3)n2)C(C)(C)C1] 2439

TABLE 1-continued
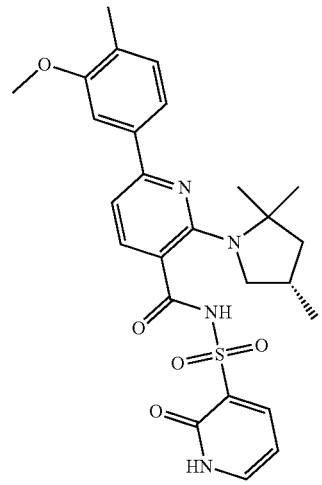
2440
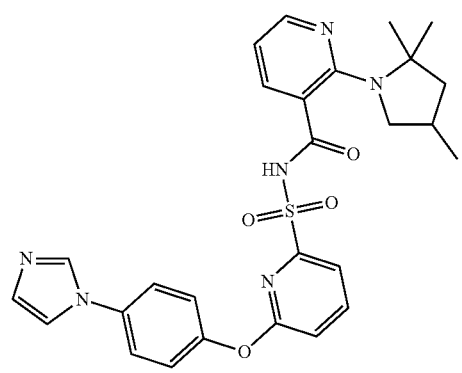 [SMILES: CC1CN(c2ncccc2C(=O)NS(=O)(=O)c2cccc(Oc3ccc(-n4ccnc4)cc3)n2)C(C)(C)C1]
2441
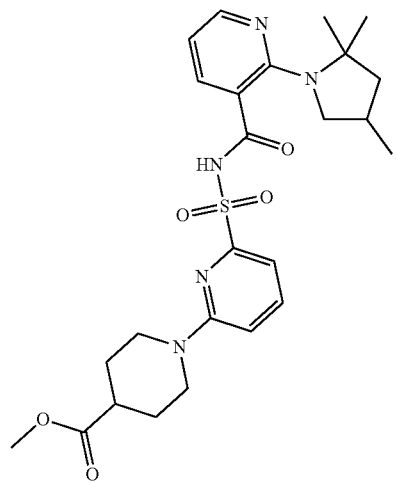
2442

TABLE 1-continued
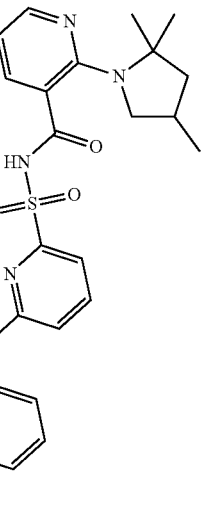
2443
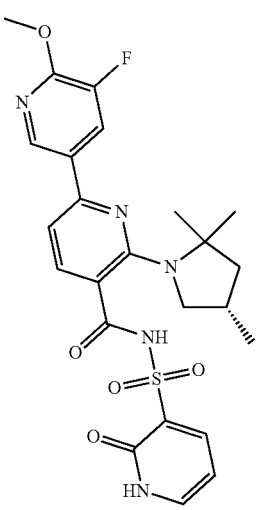
2444
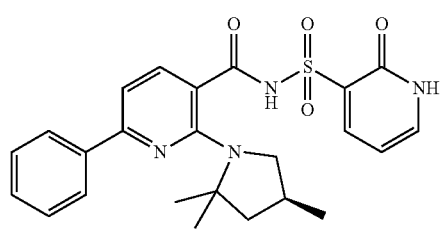 [SMILES: C[C@@H]1CN(c2nc(-c3ccccc3)ccc2C(=O)NS(=O)(=O)c2ccc[nH]c2=O)C(C)(C)C1]
2445
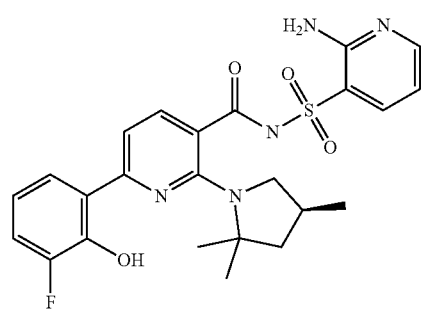 [SMILES: C[C@@H]1CN(c2nc(-c3cccc(F)c3O)ccc2C(=O)NS(=O)(=O)c2cccnc2N)C(C)(C)C1]
2446

TABLE 1-continued
| | |
|---|---|
| 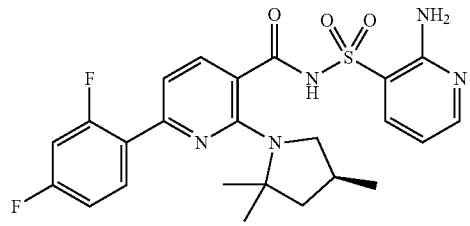 [SMILES: C[C@@H]1CN(c2nc(-c3ccc(F)cc3F)ccc2C(=O)NS(=O)(=O)c2cccnc2N)C(C)(C)C1] | 2447 |
| 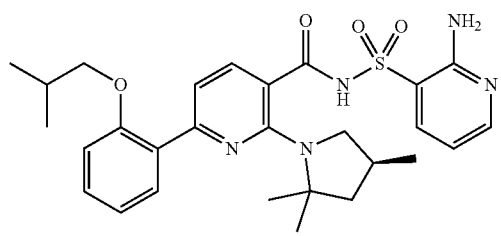 [SMILES: CC(C)COc1ccccc1-c1ccc(C(=O)NS(=O)(=O)c2cccnc2N)c(N2C[C@@H](C)CC2(C)C)n1] | 2448 |
| 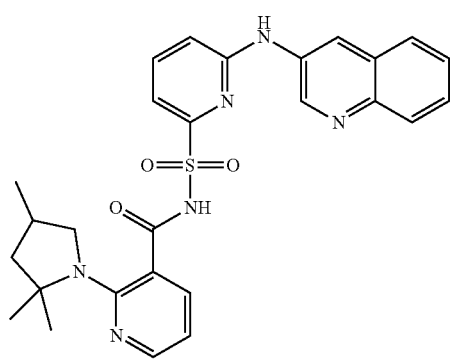 [SMILES: CC1CN(c2ncccc2C(=O)NS(=O)(=O)c2cccc(Nc3cnc4ccccc4c3)n2)C(C)(C)C1] | 2449 |
| 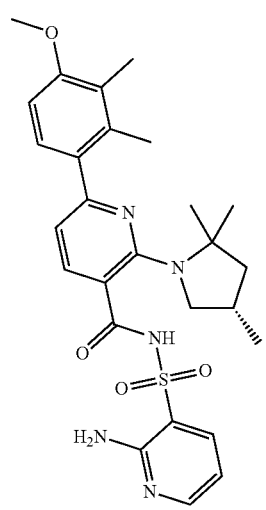 | 2450 |

TABLE 1-continued
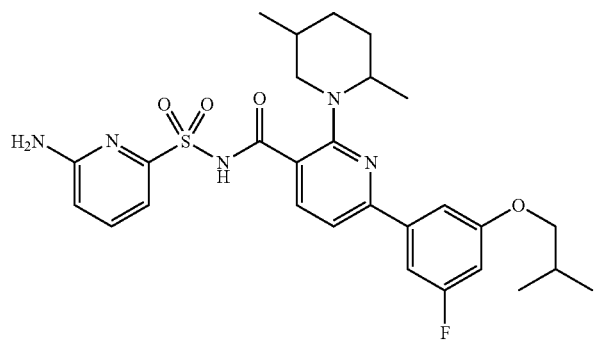 [SMILES: CC(C)COc1cc(F)cc(-c2ccc(C(=O)NS(=O)(=O)c3cccc(N)n3)c(N3CC(C)CCC3C)n2)c1]
2451
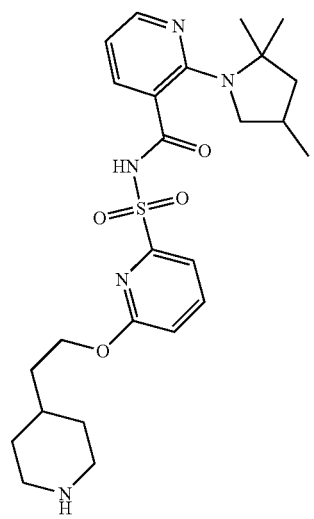 [SMILES: CC1CN(c2ncccc2C(=O)NS(=O)(=O)c2cccc(OCCC3CCNCC3)n2)C(C)(C)C1]
2452
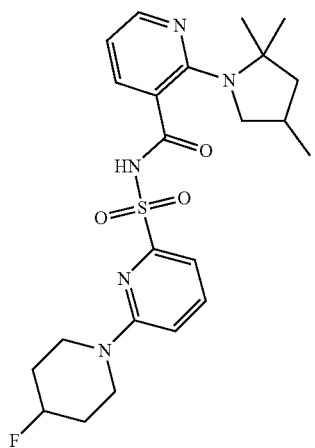 [SMILES: CC1CN(c2ncccc2C(=O)NS(=O)(=O)c2cccc(N3CCC(F)CC3)n2)C(C)(C)C1]
2453

TABLE 1-continued
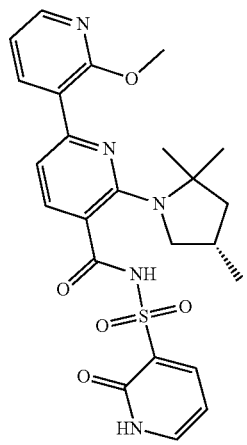 [SMILES: COc1ncccc1-c1ccc(C(=O)NS(=O)(=O)c2ccc[nH]c2=O)c(N2C[C@@H](C)CC2(C)C)n1]
2454
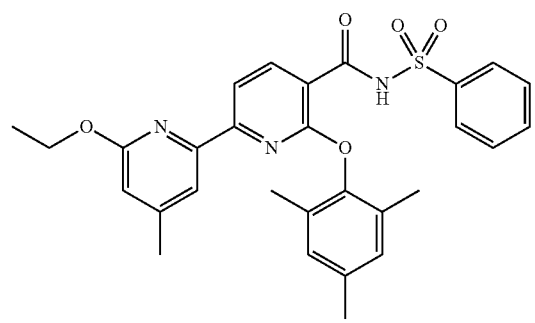 [SMILES: CCOc1cc(C)cc(-c2ccc(C(=O)NS(=O)(=O)c3ccccc3)c(Oc3c(C)cc(C)cc3C)n2)n1]
2455
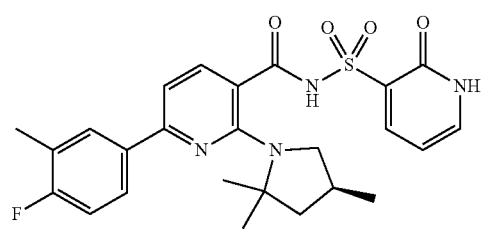 [SMILES: Cc1cc(-c2ccc(C(=O)NS(=O)(=O)c3ccc[nH]c3=O)c(N3C[C@@H](C)CC3(C)C)n2)ccc1F]
2456
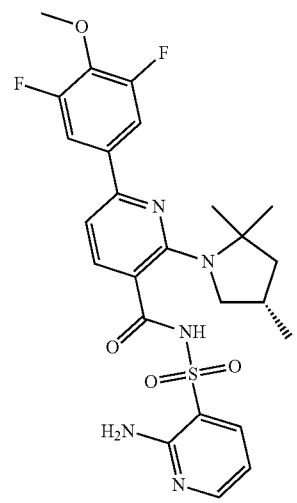 [SMILES: COc1c(F)cc(-c2ccc(C(=O)NS(=O)(=O)c3cccnc3N)c(N3C[C@@H](C)CC3(C)C)n2)cc1F]
2457

TABLE 1-continued
| | |
|---|---|
| 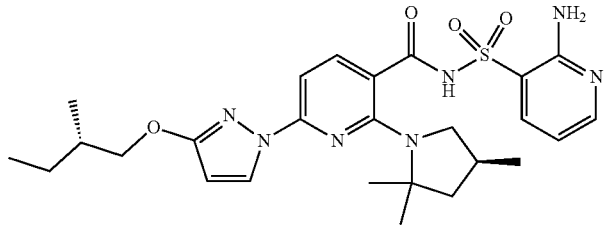 [SMILES: CC[C@H](C)COc1ccn(-c2ccc(C(=O)NS(=O)(=O)c3cccnc3N)c(N3C[C@@H](C)CC3(C)C)n2)n1] | 2458 |
| 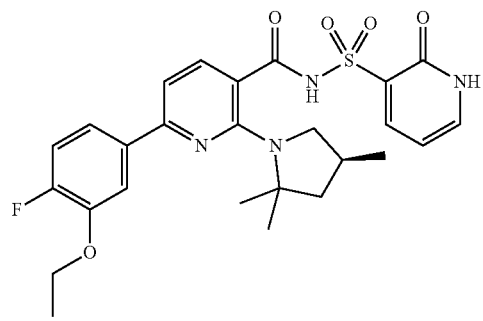 [SMILES: CCOc1cc(-c2ccc(C(=O)NS(=O)(=O)c3ccc[nH]c3=O)c(N3C[C@@H](C)CC3(C)C)n2)ccc1F] | 2459 |
| 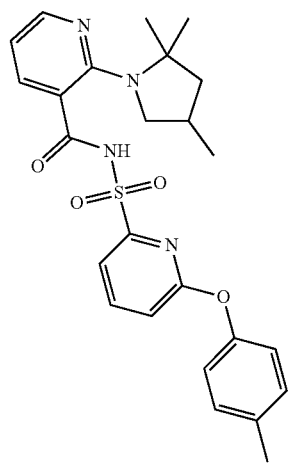 [SMILES: Cc1ccc(Oc2cccc(S(=O)(=O)NC(=O)c3cccnc3N3CC(C)CC3(C)C)n2)cc1] | 2460 |
| 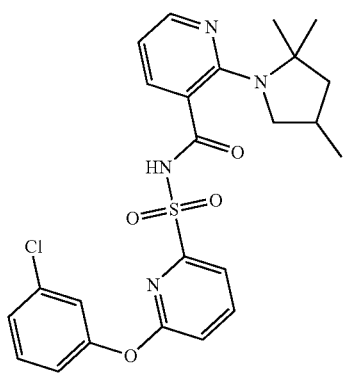 [SMILES: CC1CN(c2ncccc2C(=O)NS(=O)(=O)c2cccc(Oc3cccc(Cl)c3)n2)C(C)(C)C1] | 2461 |

TABLE 1-continued
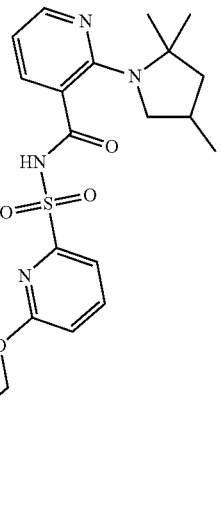 2462
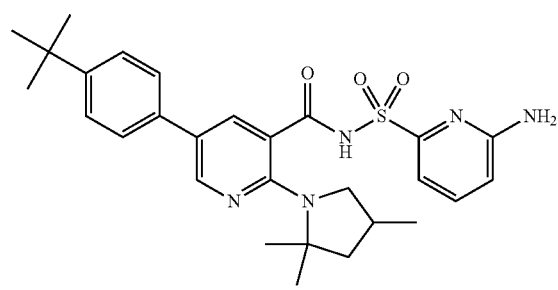 [SMILES: CC1CN(c2ncc(-c3ccc(C(C)(C)C)cc3)cc2C(=O)NS(=O)(=O)c2cccc(N)n2)C(C)(C)C1] 2463
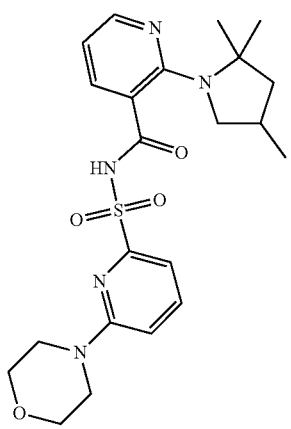 [SMILES: CC1CN(c2ncccc2C(=O)NS(=O)(=O)c2cccc(N3CCOCC3)n2)C(C)(C)C1] 2464

TABLE 1-continued
| | |
|---|---|
| 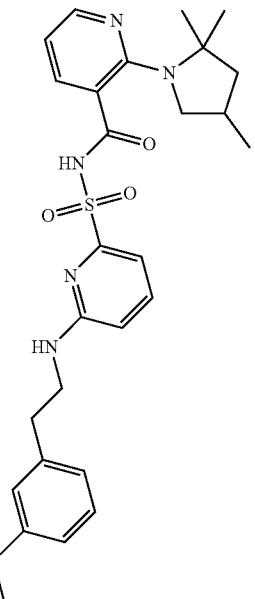 | 2465 |
| 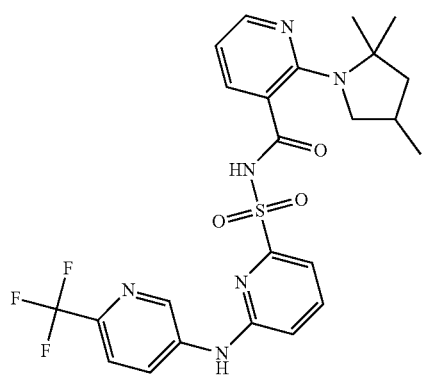 [SMILES: CC1CN(c2ncccc2C(=O)NS(=O)(=O)c2cccc(Nc3ccc(C(F)(F)F)nc3)n2)C(C)(C)C1] | 2466 |
| 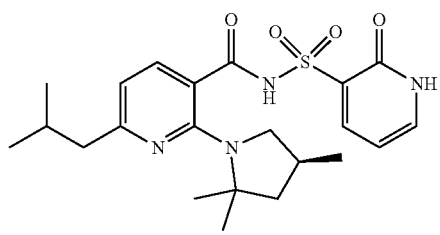 [SMILES: CC(C)Cc1ccc(C(=O)NS(=O)(=O)c2ccc[nH]c2=O)c(N2C[C@@H](C)CC2(C)C)n1] | 2467 |
| 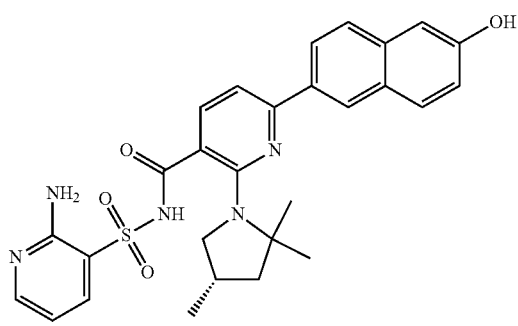 [SMILES: C[C@@H]1CN(c2nc(-c3ccc4cc(O)ccc4c3)ccc2C(=O)NS(=O)(=O)c2cccnc2N)C(C)(C)C1] | 2468 |

TABLE 1-continued
| | |
|---|---|
| 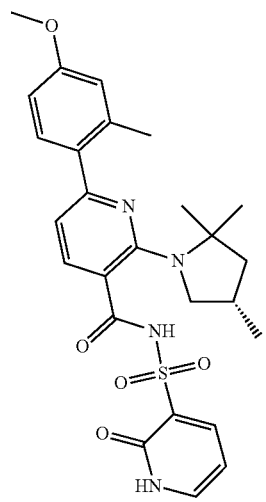 | 2469 |
| 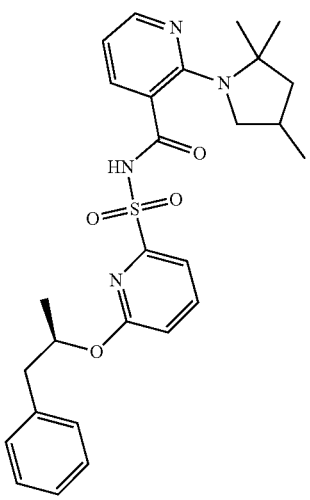 [SMILES: CC1CN(c2ncccc2C(=O)NS(=O)(=O)c2cccc(O[C@H](C)Cc3ccccc3)n2)C(C)(C)C1] | 2470 |
| 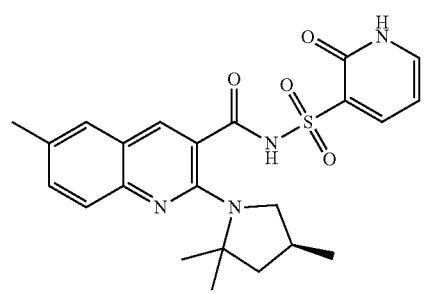 [SMILES: Cc1ccc2nc(N3C[C@@H](C)CC3(C)C)c(C(=O)NS(=O)(=O)c3ccc[nH]c3=O)cc2c1] | 2471 |
| 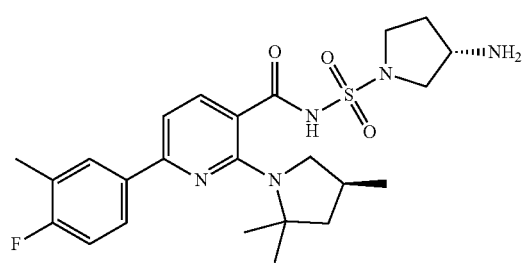 [SMILES: Cc1cc(-c2ccc(C(=O)NS(=O)(=O)N3CC[C@H](N)C3)c(N3C[C@@H](C)CC3(C)C)n2)ccc1F] | 2472 |

TABLE 1-continued
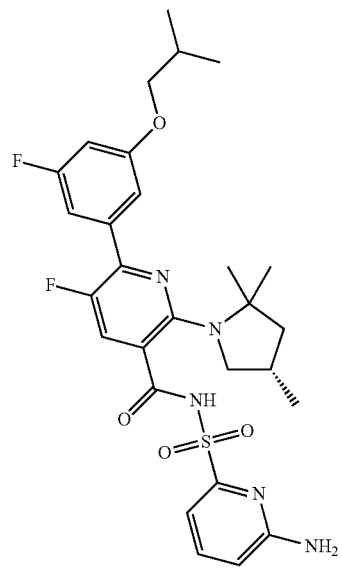 [SMILES: CC(C)COc1cc(F)cc(-c2nc(N3C[C@@H](C)CC3(C)C)c(C(=O)NS(=O)(=O)c3cccc(N)n3)cc2F)c1]
2473
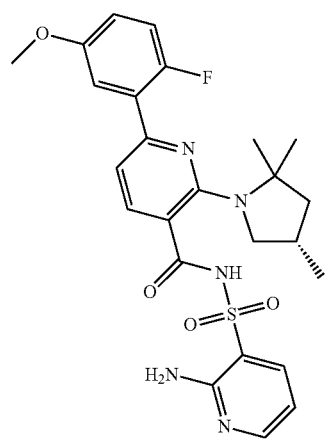
2474
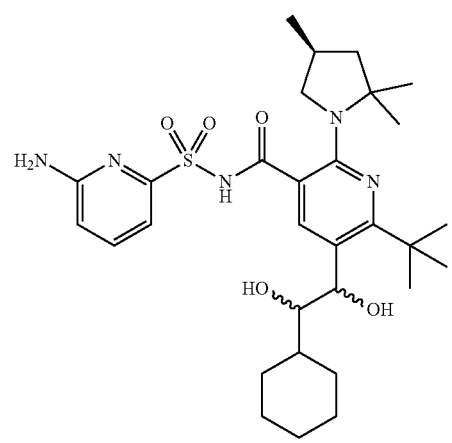 [SMILES: C[C@@H]1CN(c2nc(C(C)(C)C)c(C(O)C(O)C3CCCCC3)cc2C(=O)NS(=O)(=O)c2cccc(N)n2)C(C)(C)C1]
2475

TABLE 1-continued
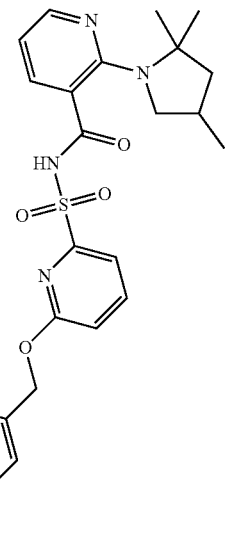
2476
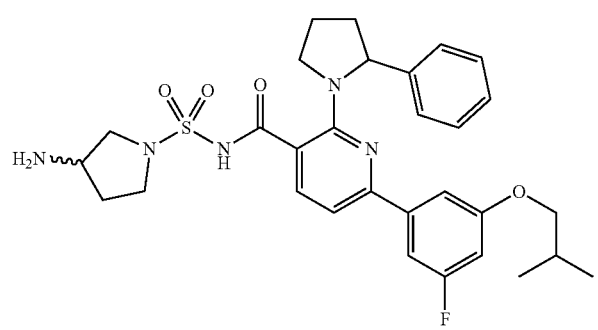 [SMILES: CC(C)COc1cc(F)cc(-c2ccc(C(=O)NS(=O)(=O)N3CCC(N)C3)c(N3CCCC3c3ccccc3)n2)c1]
2477
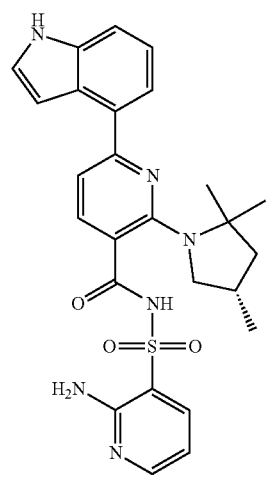 [SMILES: C[C@@H]1CN(c2nc(-c3cccc4[nH]ccc34)ccc2C(=O)NS(=O)(=O)c2cccnc2N)C(C)(C)C1]
2478

TABLE 1-continued
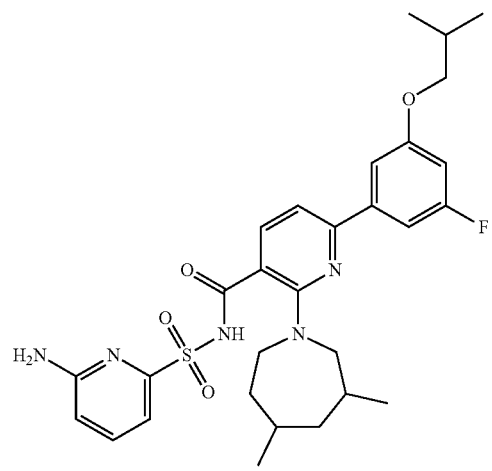 [SMILES: CC(C)COc1cc(F)cc(-c2ccc(C(=O)NS(=O)(=O)c3cccc(N)n3)c(N3CCC(C)CC(C)C3)n2)c1]
2479
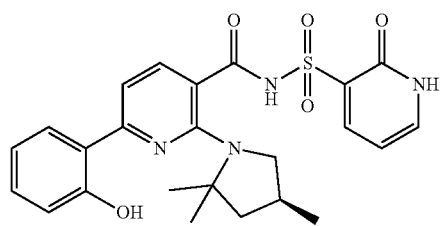 [SMILES: C[C@@H]1CN(c2nc(-c3ccccc3O)ccc2C(=O)NS(=O)(=O)c2ccc[nH]c2=O)C(C)(C)C1]
2480
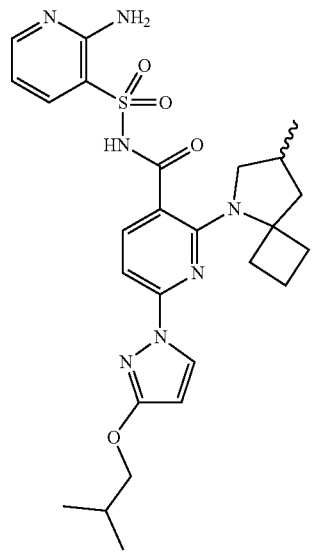 [SMILES: CC(C)COc1ccn(-c2ccc(C(=O)NS(=O)(=O)c3cccnc3N)c(N3CC(C)CC34CCC4)n2)n1]
2481

TABLE 1-continued
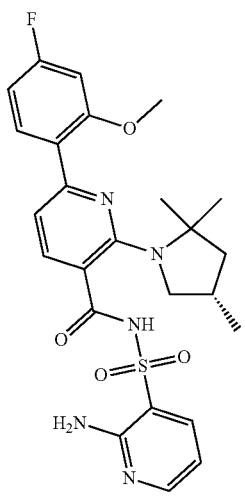 [SMILES: COc1cc(F)ccc1-c1ccc(C(=O)NS(=O)(=O)c2cccnc2N)c(N2C[C@@H](C)CC2(C)C)n1]
2482
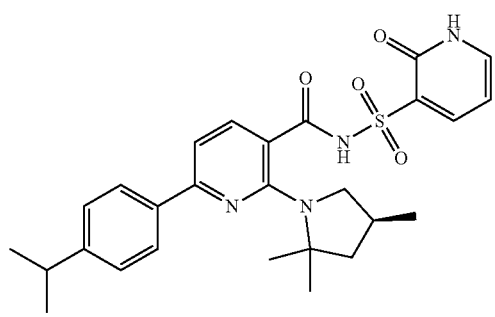 [SMILES: CC(C)c1ccc(-c2ccc(C(=O)NS(=O)(=O)c3ccc[nH]c3=O)c(N3C[C@@H](C)CC3(C)C)n2)cc1]
2483
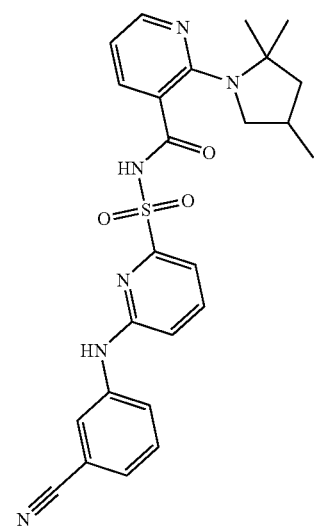 [SMILES: CC1CN(c2ncccc2C(=O)NS(=O)(=O)c2cccc(Nc3cccc(C#N)c3)n2)C(C)(C)C1]
2484
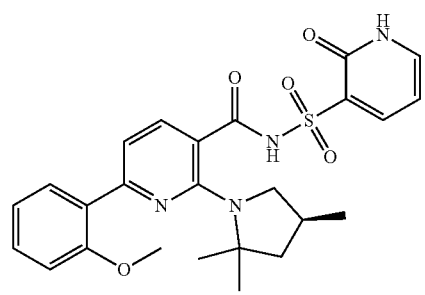 [SMILES: COc1ccccc1-c1ccc(C(=O)NS(=O)(=O)c2ccc[nH]c2=O)c(N2C[C@@H](C)CC2(C)C)n1]
2485

TABLE 1-continued
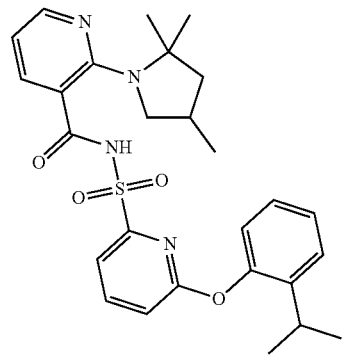 [SMILES: CC1CN(c2ncccc2C(=O)NS(=O)(=O)c2cccc(Oc3ccccc3C(C)C)n2)C(C)(C)C1]
2486
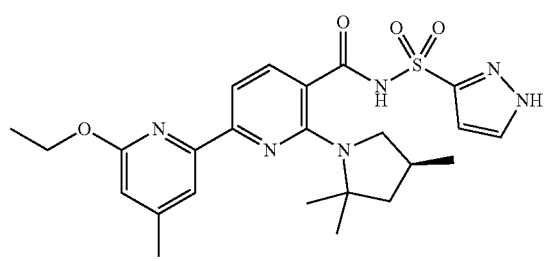 [SMILES: CCOc1cc(C)cc(-c2ccc(C(=O)NS(=O)(=O)c3cc[nH]n3)c(N3C[C@@H](C)CC3(C)C)n2)n1]
2487
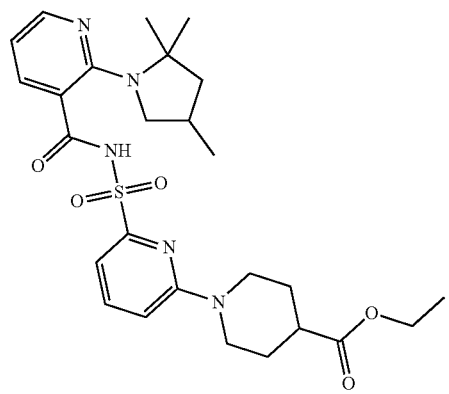 [SMILES: CCOC(=O)C1CCN(c2cccc(S(=O)(=O)NC(=O)c3cccnc3N3CC(C)CC3(C)C)n2)CC1]
2488
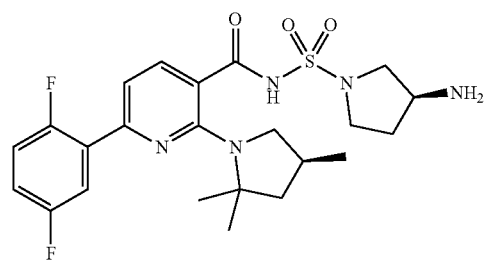 [SMILES: C[C@@H]1CN(c2nc(-c3cc(F)ccc3F)ccc2C(=O)NS(=O)(=O)N2CC[C@H](N)C2)C(C)(C)C1]
2489
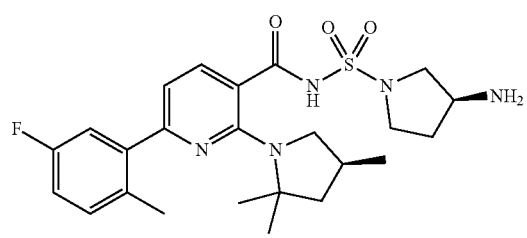 [SMILES: Cc1ccc(F)cc1-c1ccc(C(=O)NS(=O)(=O)N2CC[C@H](N)C2)c(N2C[C@@H](C)CC2(C)C)n1]
2490

TABLE 1-continued
| | |
|---|---|
| 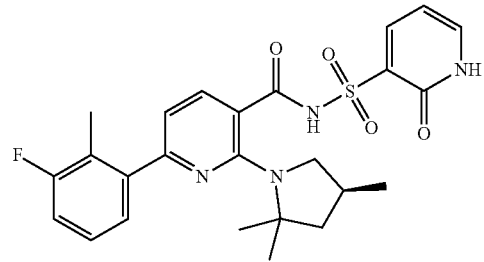 [SMILES: Cc1c(F)cccc1-c1ccc(C(=O)NS(=O)(=O)c2ccc[nH]c2=O)c(N2C[C@@H](C)CC2(C)C)n1] | 2491 |
| 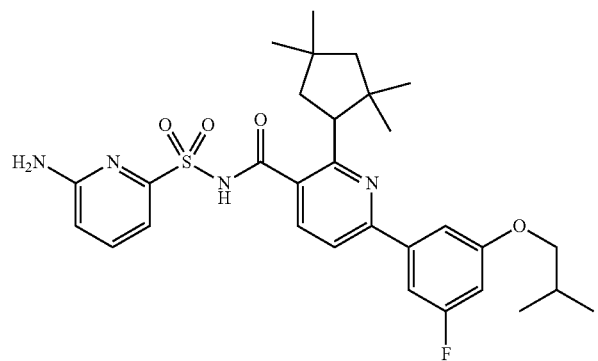 [SMILES: CC(C)COc1cc(F)cc(-c2ccc(C(=O)NS(=O)(=O)c3cccc(N)n3)c(C3CC(C)(C)CC3(C)C)n2)c1] | 2492 |
| 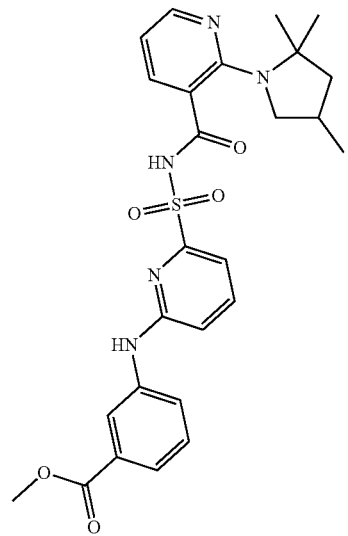 | 2493 |

TABLE 1-continued
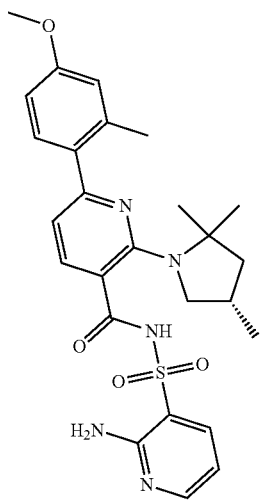
2494
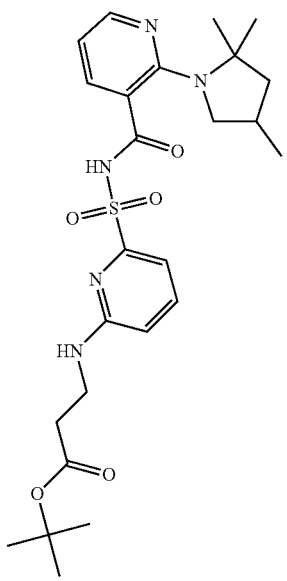 [SMILES: CC1CN(c2ncccc2C(=O)NS(=O)(=O)c2cccc(NCCC(=O)OC(C)(C)C)n2)C(C)(C)C1]
2495
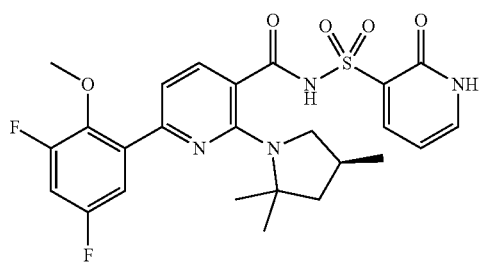 [SMILES: COc1c(F)cc(F)cc1-c1ccc(C(=O)NS(=O)(=O)c2ccc[nH]c2=O)c(N2C[C@@H](C)CC2(C)C)n1]
2496
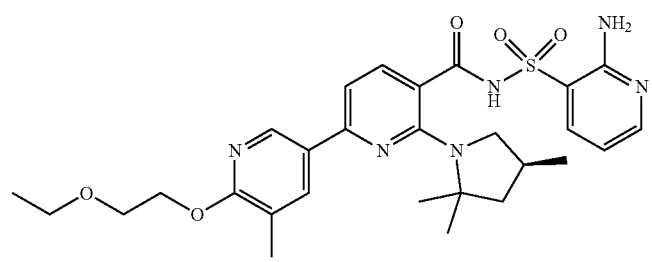 [SMILES: CCOCCOc1ncc(-c2ccc(C(=O)NS(=O)(=O)c3cccnc3N)c(N3C[C@@H](C)CC3(C)C)n2)cc1C]
2497

TABLE 1-continued
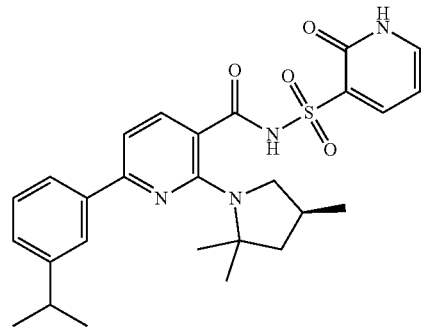 [SMILES: CC(C)c1cccc(-c2ccc(C(=O)NS(=O)(=O)c3ccc[nH]c3=O)c(N3C[C@@H](C)CC3(C)C)n2)c1]
2498
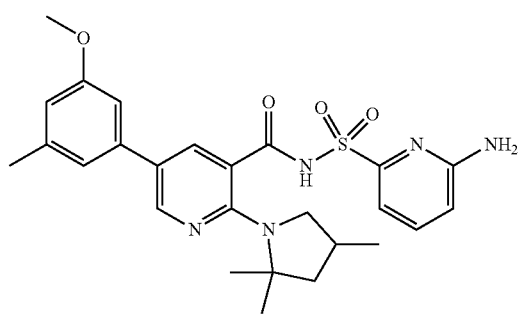 [SMILES: COc1cc(C)cc(-c2cnc(N3CC(C)CC3(C)C)c(C(=O)NS(=O)(=O)c3cccc(N)n3)c2)c1]
2499
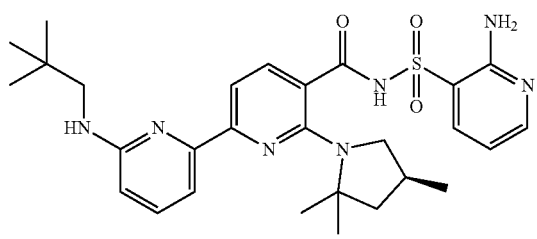 [SMILES: C[C@@H]1CN(c2nc(-c3cccc(NCC(C)(C)C)n3)ccc2C(=O)NS(=O)(=O)c2cccnc2N)C(C)(C)C1]
2500
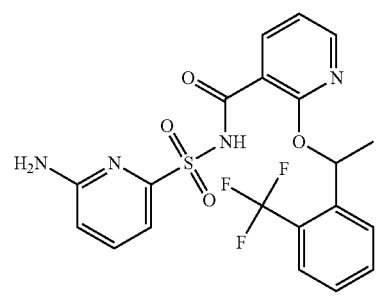 [SMILES: CC(Oc1ncccc1C(=O)NS(=O)(=O)c1cccc(N)n1)c1ccccc1C(F)(F)F]
2501

TABLE 1-continued
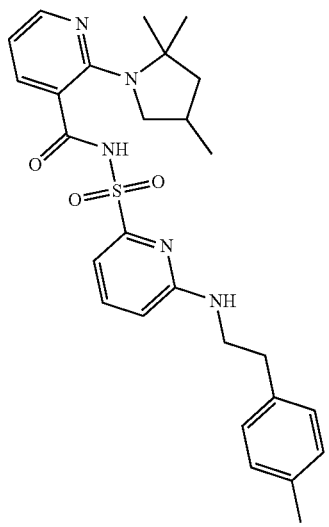 [SMILES: Cc1ccc(CCNc2cccc(S(=O)(=O)NC(=O)c3cccnc3N3CC(C)CC3(C)C)n2)cc1] 2502
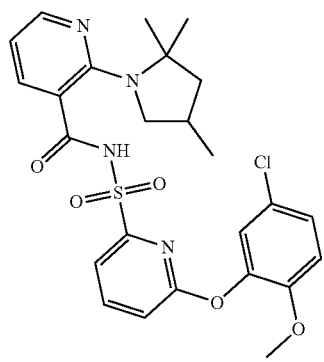 [SMILES: COc1ccc(Cl)cc1Oc1cccc(S(=O)(=O)NC(=O)c2cccnc2N2CC(C)CC2(C)C)n1] 2503
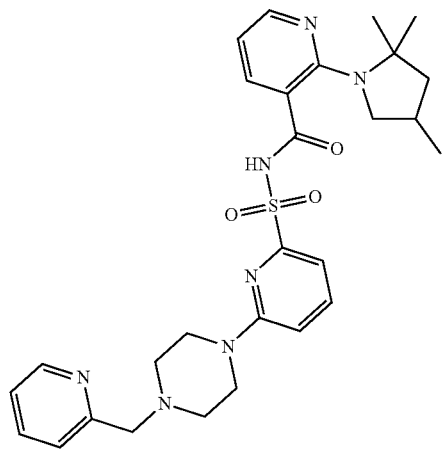 [SMILES: CC1CN(c2ncccc2C(=O)NS(=O)(=O)c2cccc(N3CCN(Cc4ccccn4)CC3)n2)C(C)(C)C1] 2504
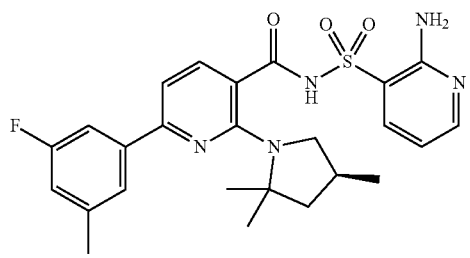 [SMILES: Cc1cc(F)cc(-c2ccc(C(=O)NS(=O)(=O)c3cccnc3N)c(N3C[C@@H](C)CC3(C)C)n2)c1] 2505

TABLE 1-continued
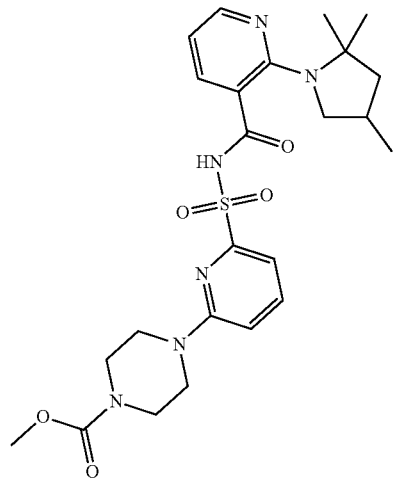
2506
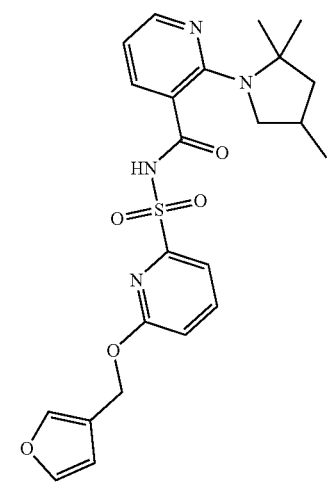 [SMILES: CC1CN(c2ncccc2C(=O)NS(=O)(=O)c2cccc(OCc3ccoc3)n2)C(C)(C)C1]
2507
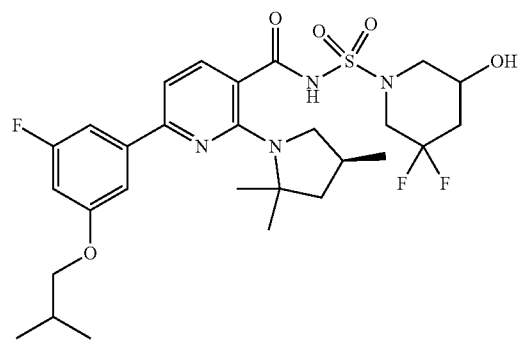 [SMILES: CC(C)COc1cc(F)cc(-c2ccc(C(=O)NS(=O)(=O)N3CC(O)CC(F)(F)C3)c(N3C[C@@H](C)CC3(C)C)n2)c1]
2508

TABLE 1-continued
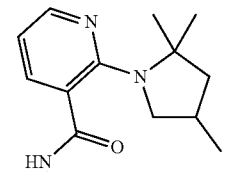
2509
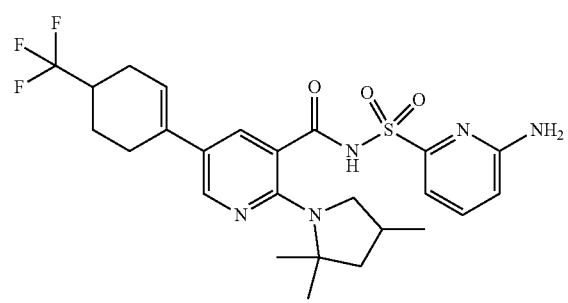 [SMILES: CC1CN(c2ncc(C3=CCC(C(F)(F)F)CC3)cc2C(=O)NS(=O)(=O)c2cccc(N)n2)C(C)(C)C1]
2510
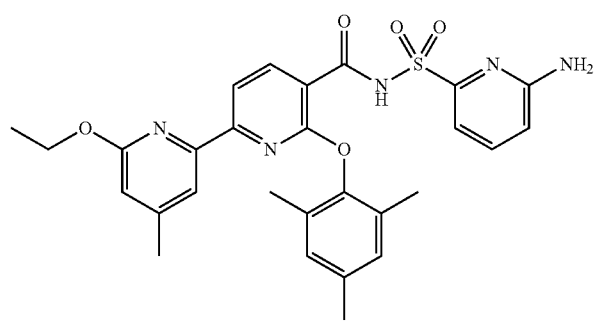 [SMILES: CCOc1cc(C)cc(-c2ccc(C(=O)NS(=O)(=O)c3cccc(N)n3)c(Oc3c(C)cc(C)cc3C)n2)n1]
2511
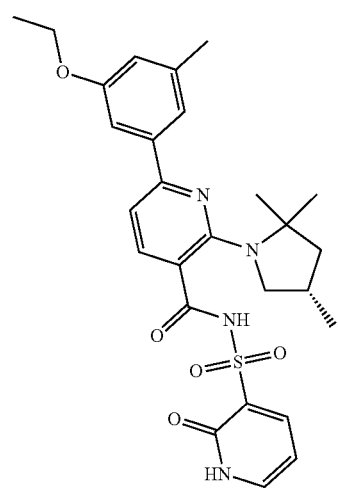 [SMILES: CCOc1cc(C)cc(-c2ccc(C(=O)NS(=O)(=O)c3ccc[nH]c3=O)c(N3C[C@@H](C)CC3(C)C)n2)c1]
2512

TABLE 1-continued
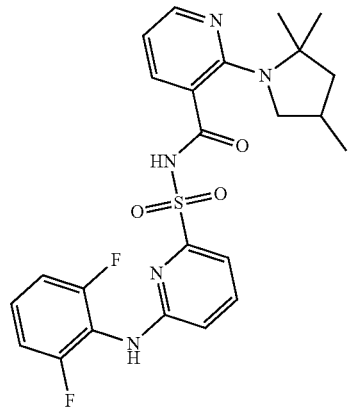 [SMILES: CC1CN(c2ncccc2C(=O)NS(=O)(=O)c2cccc(Nc3c(F)cccc3F)n2)C(C)(C)C1]
2513
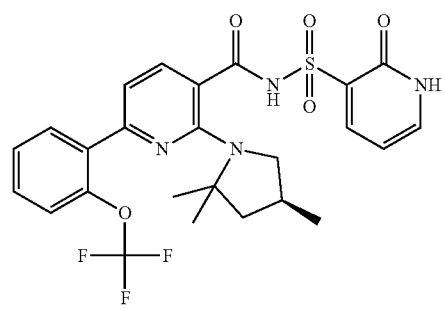 [SMILES: C[C@@H]1CN(c2nc(-c3ccccc3OC(F)(F)F)ccc2C(=O)NS(=O)(=O)c2ccc[nH]c2=O)C(C)(C)C1]
2514
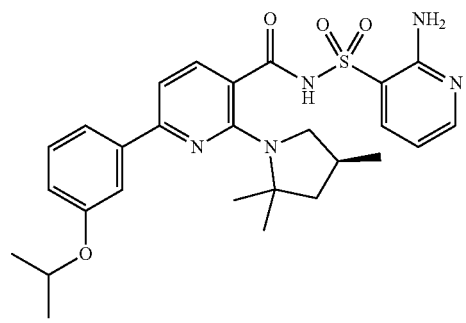 [SMILES: CC(C)Oc1cccc(-c2ccc(C(=O)NS(=O)(=O)c3cccnc3N)c(N3C[C@@H](C)CC3(C)C)n2)c1]
2515
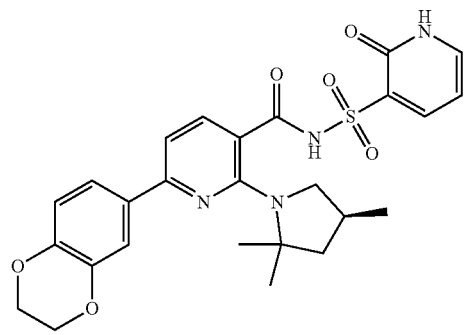 [SMILES: C[C@@H]1CN(c2nc(-c3ccc4c(c3)OCCO4)ccc2C(=O)NS(=O)(=O)c2ccc[nH]c2=O)C(C)(C)C1]
2516

TABLE 1-continued
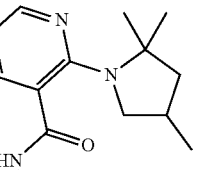
2517
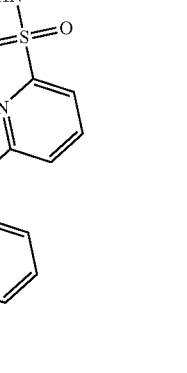
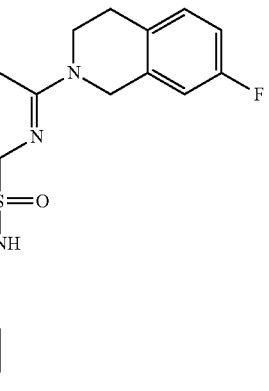
2518
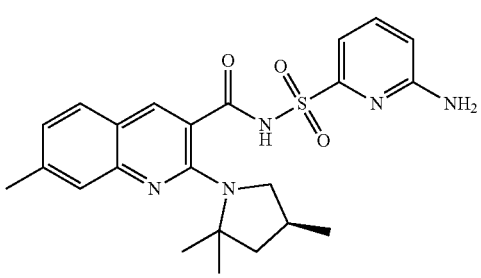 [SMILES: Cc1ccc2cc(C(=O)NS(=O)(=O)c3cccc(N)n3)c(N3C[C@@H](C)CC3(C)C)nc2c1]
2519
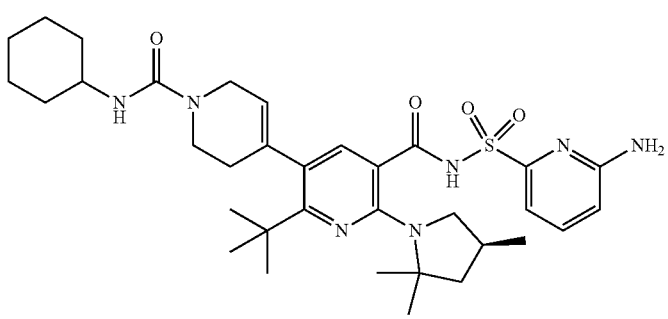 [SMILES: C[C@@H]1CN(c2nc(C(C)(C)C)c(C3=CCN(C(=O)NC4CCCCC4)CC3)cc2C(=O)NS(=O)(=O)c2cccc(N)n2)C(C)(C)C1]
2520

TABLE 1-continued
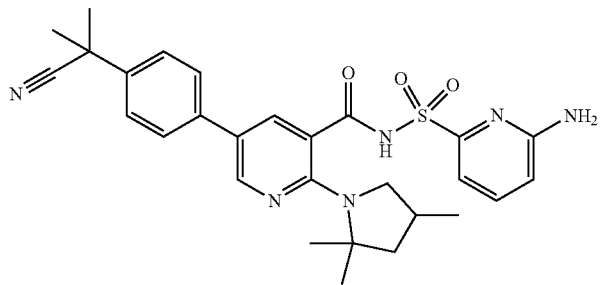 [SMILES: CC1CN(c2ncc(-c3ccc(C(C)(C)C#N)cc3)cc2C(=O)NS(=O)(=O)c2cccc(N)n2)C(C)(C)C1]
2521
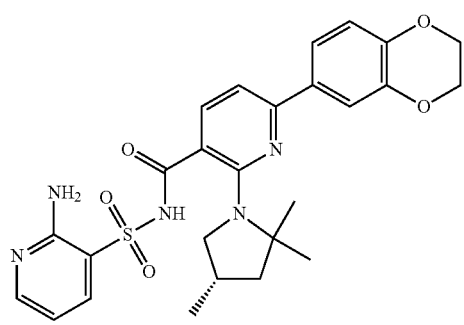 [SMILES: C[C@@H]1CN(c2nc(-c3ccc4c(c3)OCCO4)ccc2C(=O)NS(=O)(=O)c2cccnc2N)C(C)(C)C1]
2522
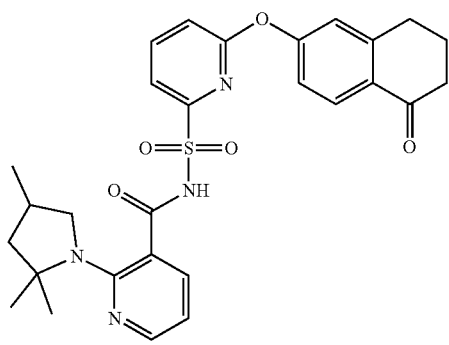 [SMILES: CC1CN(c2ncccc2C(=O)NS(=O)(=O)c2cccc(Oc3ccc4c(c3)CCCC4=O)n2)C(C)(C)C1]
2523
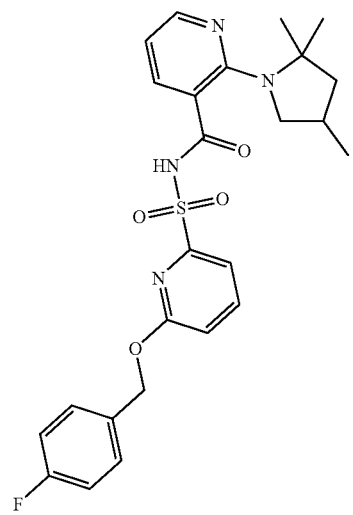 [SMILES: CC1CN(c2ncccc2C(=O)NS(=O)(=O)c2cccc(OCc3ccc(F)cc3)n2)C(C)(C)C1]
2524

TABLE 1-continued
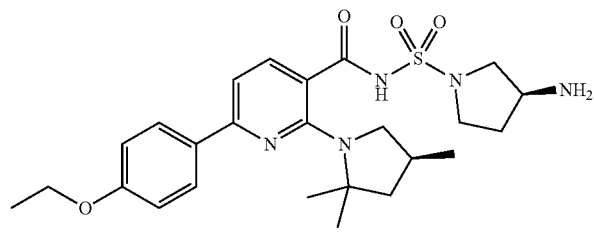 [SMILES: CCOc1ccc(-c2ccc(C(=O)NS(=O)(=O)N3CC[C@H](N)C3)c(N3C[C@@H](C)CC3(C)C)n2)cc1]
2525
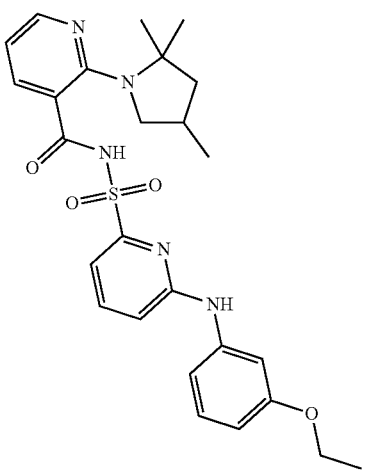 [SMILES: CCOc1cccc(Nc2cccc(S(=O)(=O)NC(=O)c3cccnc3N3CC(C)CC3(C)C)n2)c1]
2526
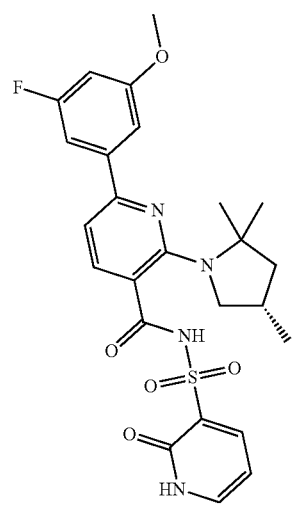 [SMILES: COc1cc(F)cc(-c2ccc(C(=O)NS(=O)(=O)c3ccc[nH]c3=O)c(N3C[C@@H](C)CC3(C)C)n2)c1]
2527
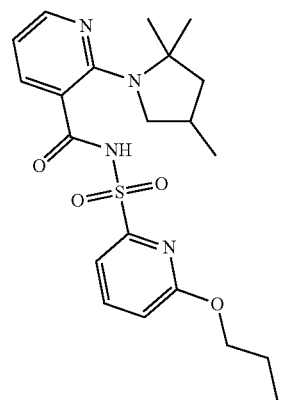 [SMILES: CCCOc1cccc(S(=O)(=O)NC(=O)c2cccnc2N2CC(C)CC2(C)C)n1]
2528

TABLE 1-continued
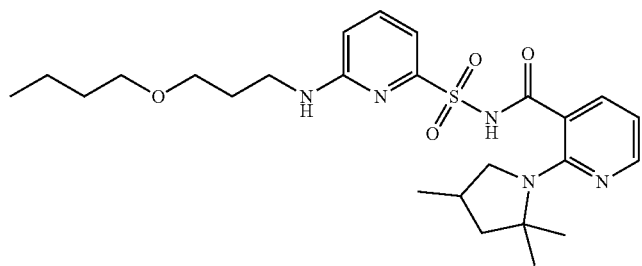 [SMILES: CCCCOCCCNc1cccc(S(=O)(=O)NC(=O)c2cccnc2N2CC(C)CC2(C)C)n1]
2529
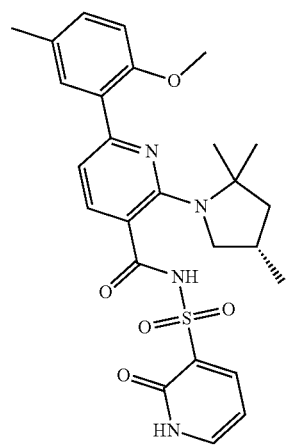
2530
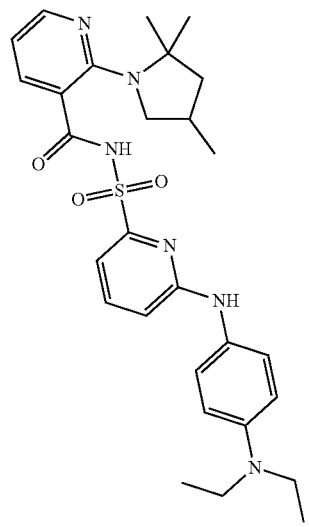 [SMILES: CCN(CC)c1ccc(Nc2cccc(S(=O)(=O)NC(=O)c3cccnc3N3CC(C)CC3(C)C)n2)cc1]
2531
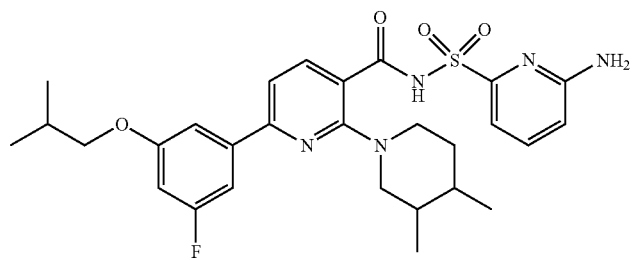 [SMILES: CC(C)COc1cc(F)cc(-c2ccc(C(=O)NS(=O)(=O)c3cccc(N)n3)c(N3CCC(C)C(C)C3)n2)c1]
2532

TABLE 1-continued
| | |
|---|---|
| 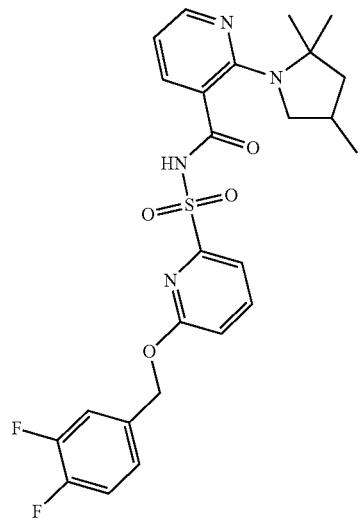 [SMILES: CC1CN(c2ncccc2C(=O)NS(=O)(=O)c2cccc(OCc3ccc(F)c(F)c3)n2)C(C)(C)C1] | 2533 |
| 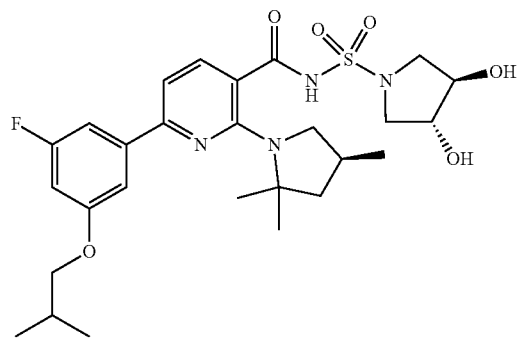 [SMILES: CC(C)COc1cc(F)cc(-c2ccc(C(=O)NS(=O)(=O)N3C[C@@H](O)[C@H](O)C3)c(N3C[C@@H](C)CC3(C)C)n2)c1] | 2534 |
| 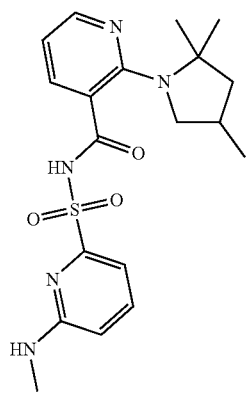 [SMILES: CNc1cccc(S(=O)(=O)NC(=O)c2cccnc2N2CC(C)CC2(C)C)n1] | 2535 |
| 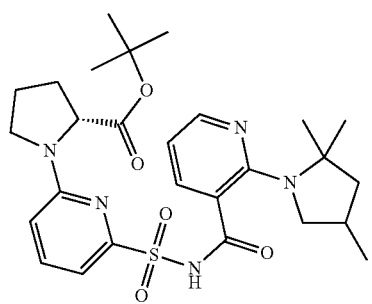 [SMILES: CC1CN(c2ncccc2C(=O)NS(=O)(=O)c2cccc(N3CCC[C@@H]3C(=O)OC(C)(C)C)n2)C(C)(C)C1] | 2536 |

TABLE 1-continued
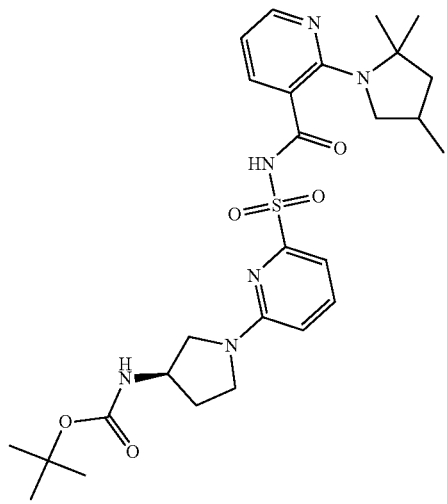 [SMILES: CC1CN(c2ncccc2C(=O)NS(=O)(=O)c2cccc(N3CC[C@@H](NC(=O)OC(C)(C)C)C3)n2)C(C)(C)C1]
2537
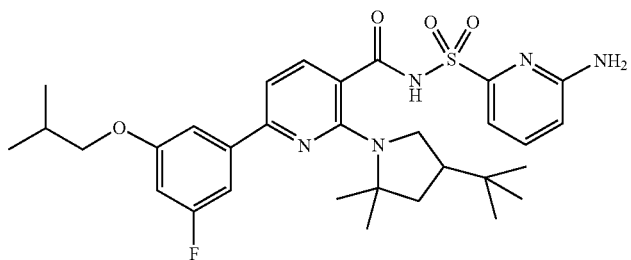 [SMILES: CC(C)COc1cc(F)cc(-c2ccc(C(=O)NS(=O)(=O)c3cccc(N)n3)c(N3CC(C(C)(C)C)CC3(C)C)n2)c1]
2538
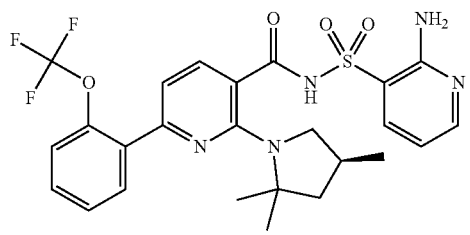 [SMILES: C[C@@H]1CN(c2nc(-c3ccccc3OC(F)(F)F)ccc2C(=O)NS(=O)(=O)c2cccnc2N)C(C)(C)C1]
2539
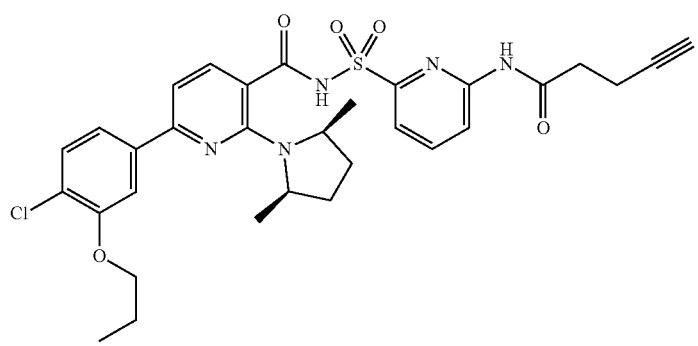 [SMILES: C#CCCC(=O)Nc1cccc(S(=O)(=O)NC(=O)c2ccc(-c3ccc(Cl)c(OCCC)c3)nc2N2[C@H](C)CC[C@@H]2C)n1]
2540
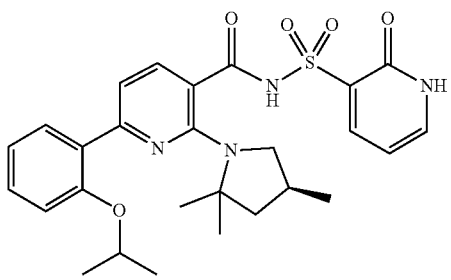 [SMILES: CC(C)Oc1ccccc1-c1ccc(C(=O)NS(=O)(=O)c2ccc[nH]c2=O)c(N2C[C@@H](C)CC2(C)C)n1]
2541

TABLE 1-continued
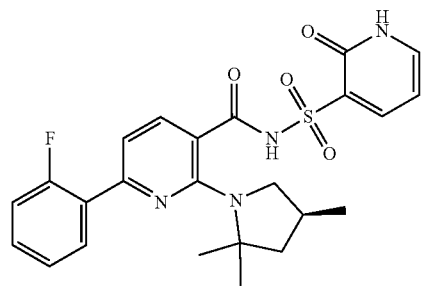
2542
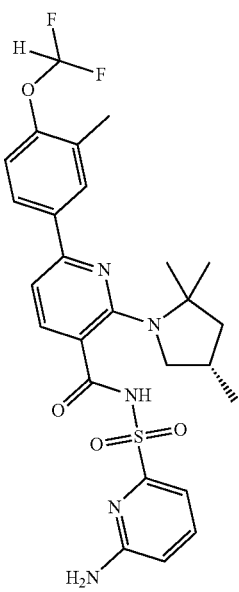 [SMILES: Cc1cc(-c2ccc(C(=O)NS(=O)(=O)c3cccc(N)n3)c(N3C[C@@H](C)CC3(C)C)n2)ccc1OC(F)F]
2543
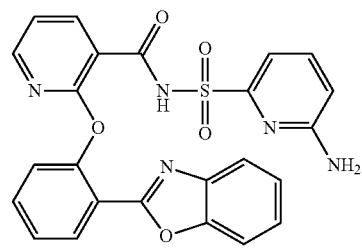 [SMILES: Nc1cccc(S(=O)(=O)NC(=O)c2cccnc2Oc2ccccc2-c2nc3ccccc3o2)n1]
2544
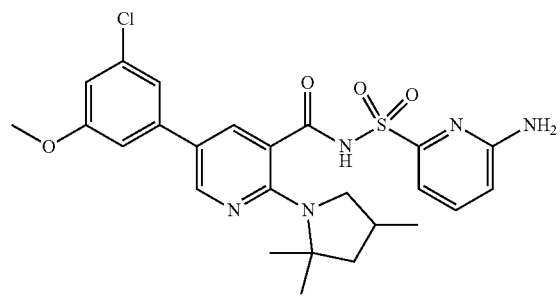 [SMILES: COc1cc(Cl)cc(-c2cnc(N3CC(C)CC3(C)C)c(C(=O)NS(=O)(=O)c3cccc(N)n3)c2)c1]
2545

TABLE 1-continued
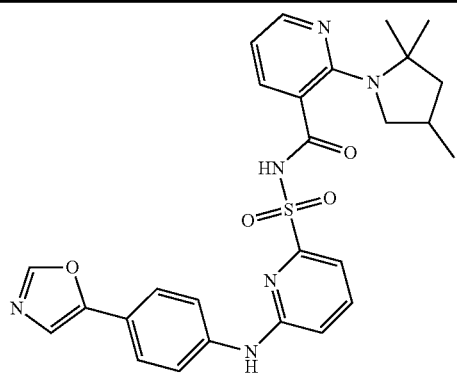
2546
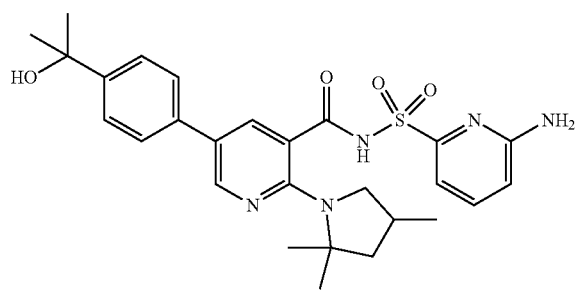 [SMILES: CC1CN(c2ncc(-c3ccc(C(C)(C)O)cc3)cc2C(=O)NS(=O)(=O)c2cccc(N)n2)C(C)(C)C1]
2547
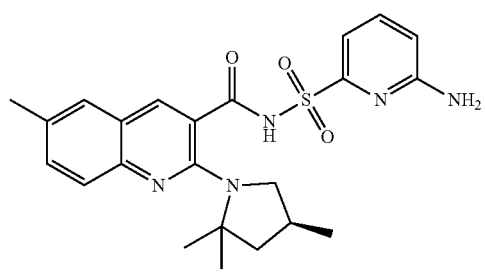 [SMILES: Cc1ccc2nc(N3C[C@@H](C)CC3(C)C)c(C(=O)NS(=O)(=O)c3cccc(N)n3)cc2c1]
2548
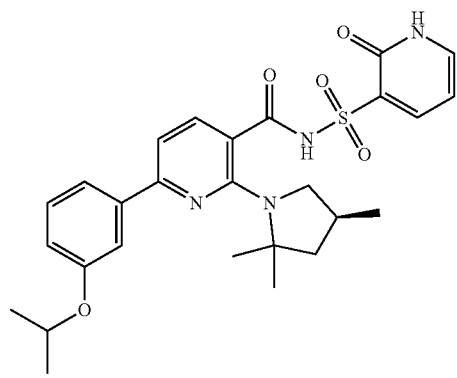 [SMILES: CC(C)Oc1cccc(-c2ccc(C(=O)NS(=O)(=O)c3ccc[nH]c3=O)c(N3C[C@@H](C)CC3(C)C)n2)c1]
2549
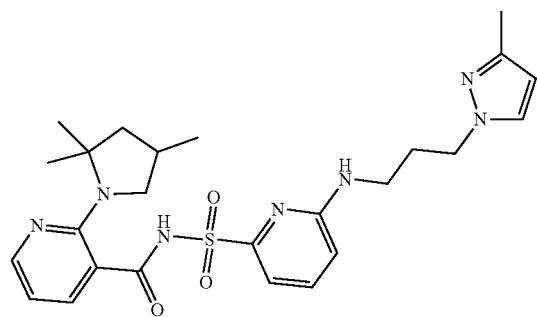 [SMILES: Cc1ccn(CCCNc2cccc(S(=O)(=O)NC(=O)c3cccnc3N3CC(C)CC3(C)C)n2)n1]
2550

TABLE 1-continued
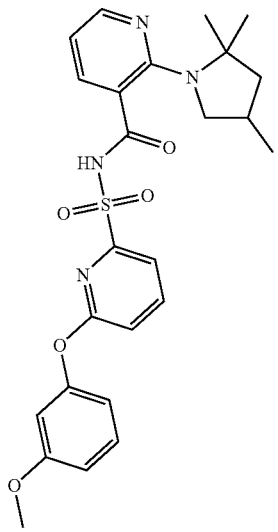 [SMILES: COc1cccc(Oc2cccc(S(=O)(=O)NC(=O)c3cccnc3N3CC(C)CC3(C)C)n2)c1]
2551
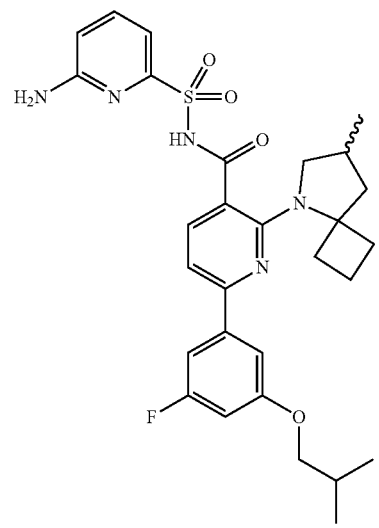 [SMILES: CC(C)COc1cc(F)cc(-c2ccc(C(=O)NS(=O)(=O)c3cccc(N)n3)c(N3CC(C)CC34CCC4)n2)c1]
2552
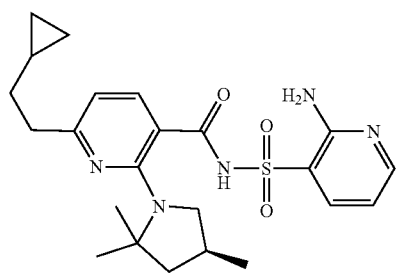 [SMILES: C[C@@H]1CN(c2nc(CCC3CC3)ccc2C(=O)NS(=O)(=O)c2cccnc2N)C(C)(C)C1]
2553
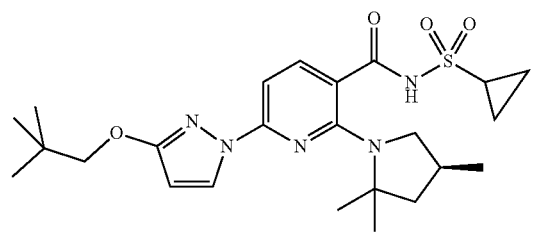 [SMILES: C[C@@H]1CN(c2nc(-n3ccc(OCC(C)(C)C)n3)ccc2C(=O)NS(=O)(=O)C2CC2)C(C)(C)C1]
2554

TABLE 1-continued
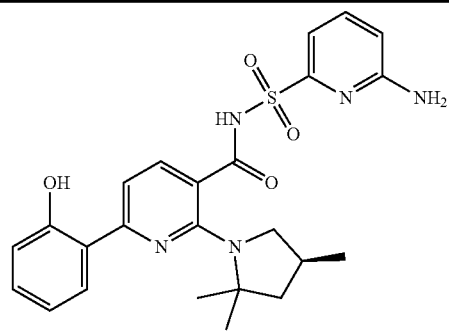
2555
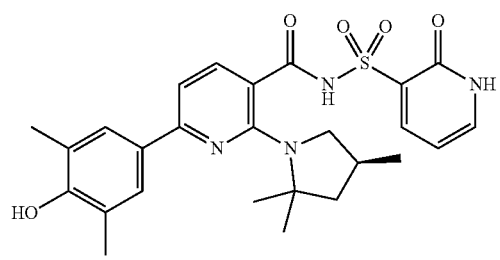 [SMILES: Cc1cc(-c2ccc(C(=O)NS(=O)(=O)c3ccc[nH]c3=O)c(N3C[C@@H](C)CC3(C)C)n2)cc(C)c1O]
2556
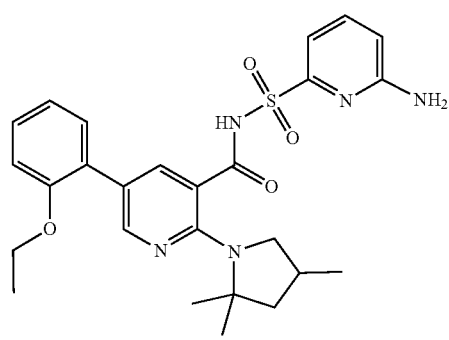 [SMILES: CCOc1ccccc1-c1cnc(N2CC(C)CC2(C)C)c(C(=O)NS(=O)(=O)c2cccc(N)n2)c1]
2557
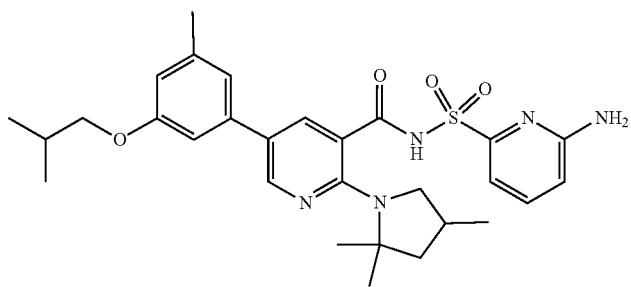 [SMILES: Cc1cc(OCC(C)C)cc(-c2cnc(N3CC(C)CC3(C)C)c(C(=O)NS(=O)(=O)c3cccc(N)n3)c2)c1]
2558
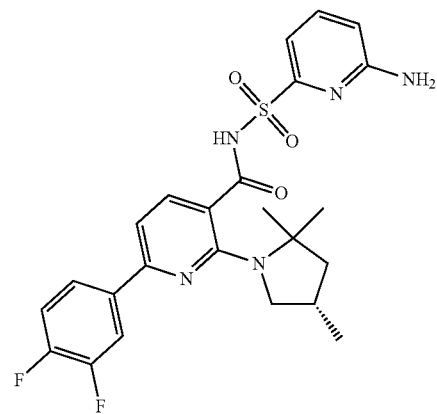 [SMILES: C[C@@H]1CN(c2nc(-c3ccc(F)c(F)c3)ccc2C(=O)NS(=O)(=O)c2cccc(N)n2)C(C)(C)C1]
2559

TABLE 1-continued
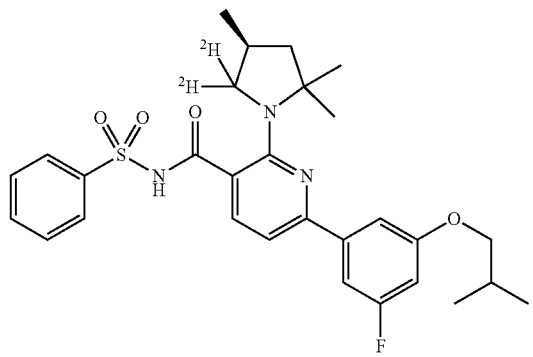 [SMILES: [2H]C1([2H])[C@@H](C)CC(C)(C)N1c1nc(-c2cc(F)cc(OCC(C)C)c2)ccc1C(=O)NS(=O)(=O)c1ccccc1]
2560
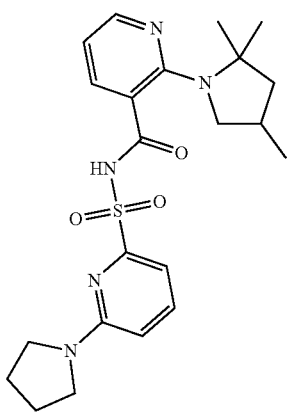 [SMILES: CC1CN(c2ncccc2C(=O)NS(=O)(=O)c2cccc(N3CCCC3)n2)C(C)(C)C1]
2561
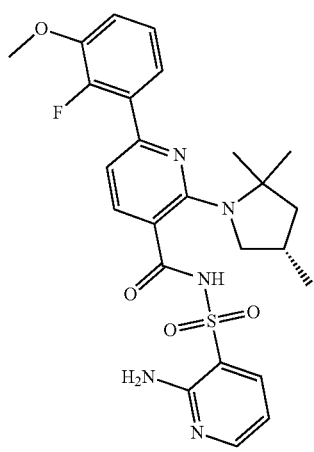
2562
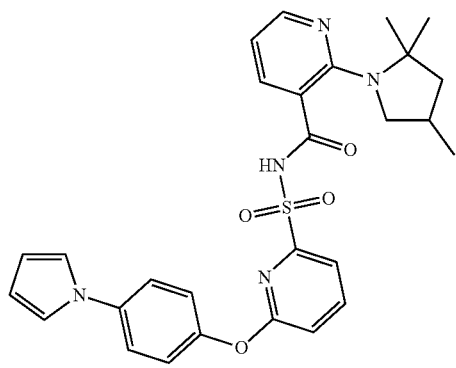 [SMILES: CC1CN(c2ncccc2C(=O)NS(=O)(=O)c2cccc(Oc3ccc(-n4cccc4)cc3)n2)C(C)(C)C1]
2563

TABLE 1-continued
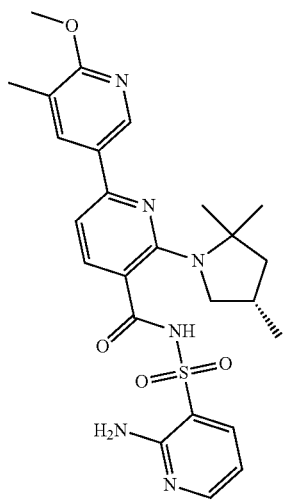
2564
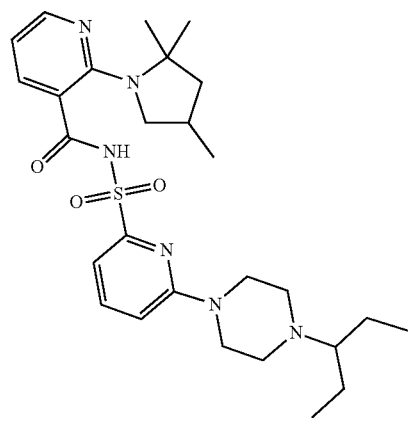 [SMILES: CCC(CC)N1CCN(c2cccc(S(=O)(=O)NC(=O)c3cccnc3N3CC(C)CC3(C)C)n2)CC1]
2565
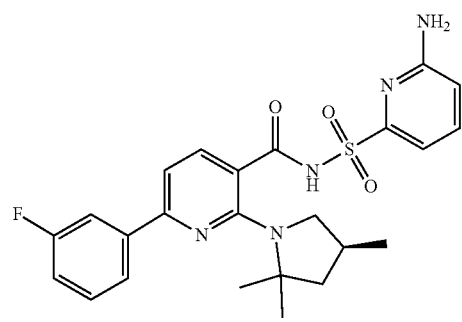 [SMILES: C[C@@H]1CN(c2nc(-c3cccc(F)c3)ccc2C(=O)NS(=O)(=O)c2cccc(N)n2)C(C)(C)C1]
2566
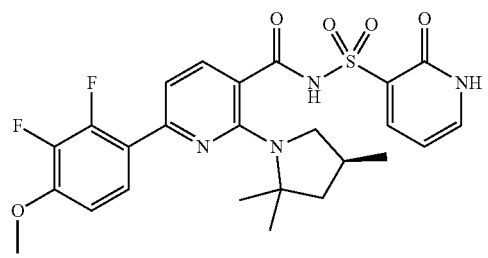 [SMILES: COc1ccc(-c2ccc(C(=O)NS(=O)(=O)c3ccc[nH]c3=O)c(N3C[C@@H](C)CC3(C)C)n2)c(F)c1F]
2567

TABLE 1-continued
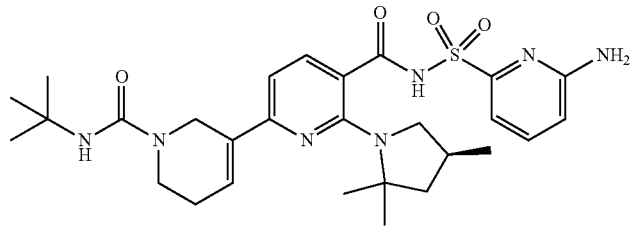 [SMILES: C[C@@H]1CN(c2nc(C3=CCCN(C(=O)NC(C)(C)C)C3)ccc2C(=O)NS(=O)(=O)c2cccc(N)n2)C(C)(C)C1]
2568
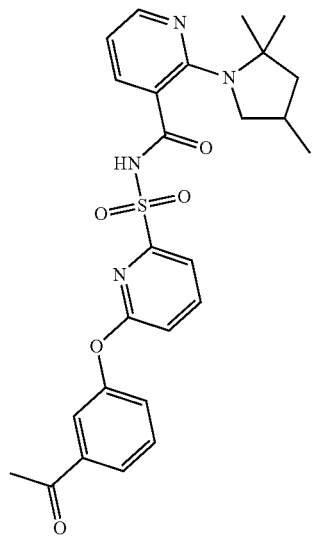 [SMILES: CC(=O)c1cccc(Oc2cccc(S(=O)(=O)NC(=O)c3cccnc3N3CC(C)CC3(C)C)n2)c1]
2569
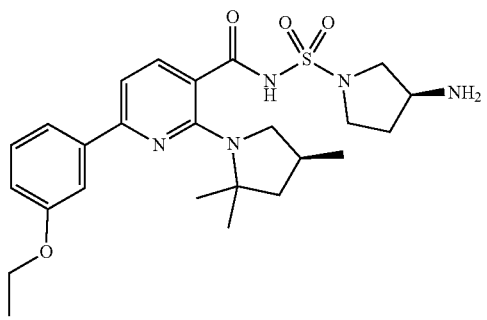 [SMILES: CCOc1cccc(-c2ccc(C(=O)NS(=O)(=O)N3CC[C@H](N)C3)c(N3C[C@@H](C)CC3(C)C)n2)c1]
2570
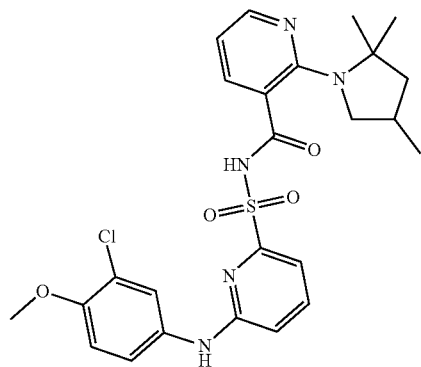
2571

TABLE 1-continued
| | |
|---|---|
| 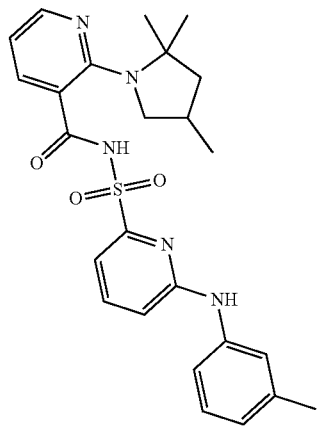 [SMILES: Cc1cccc(Nc2cccc(S(=O)(=O)NC(=O)c3cccnc3N3CC(C)CC3(C)C)n2)c1] | 2572 |
| 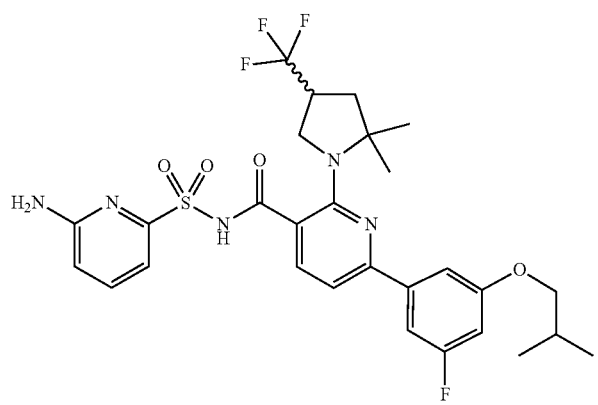 [SMILES: CC(C)COc1cc(F)cc(-c2ccc(C(=O)NS(=O)(=O)c3cccc(N)n3)c(N3CC(C(F)(F)F)CC3(C)C)n2)c1] | 2573 |
| 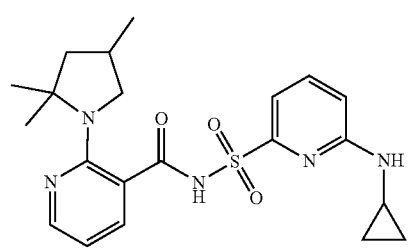 [SMILES: CC1CN(c2ncccc2C(=O)NS(=O)(=O)c2cccc(NC3CC3)n2)C(C)(C)C1] | 2574 |
| 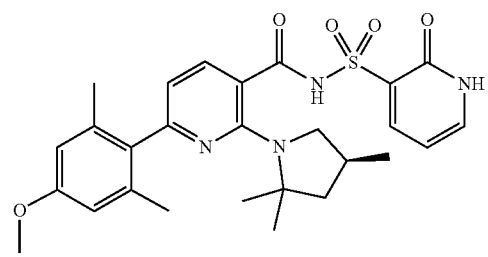 [SMILES: COc1cc(C)c(-c2ccc(C(=O)NS(=O)(=O)c3ccc[nH]c3=O)c(N3C[C@@H](C)CC3(C)C)n2)c(C)c1] | 2575 |

TABLE 1-continued
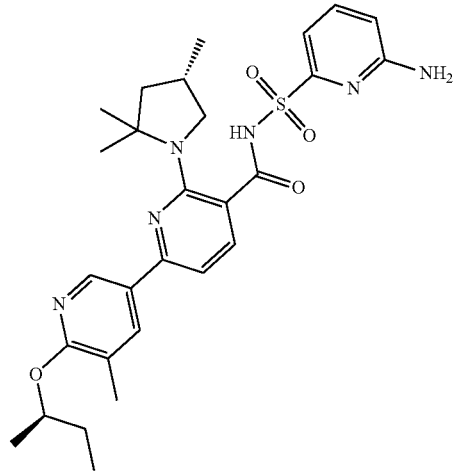 [SMILES: CC[C@@H](C)Oc1ncc(-c2ccc(C(=O)NS(=O)(=O)c3cccc(N)n3)c(N3C[C@@H](C)CC3(C)C)n2)cc1C]
2576
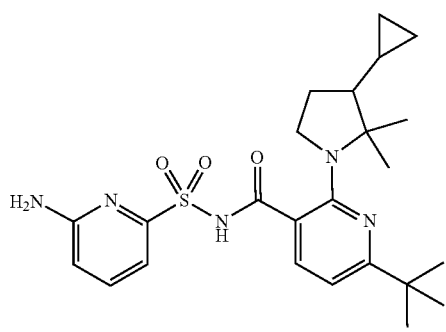
2577
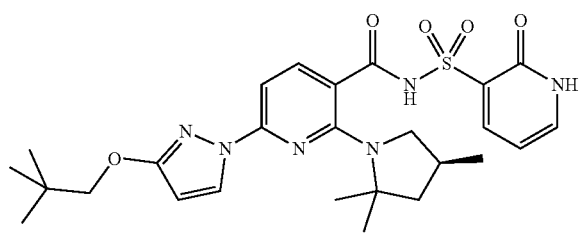
2578
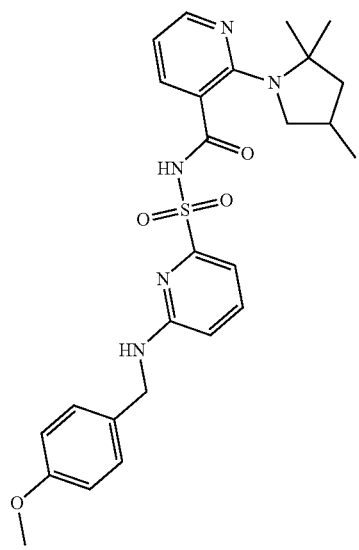 [SMILES: COc1ccc(CNc2cccc(S(=O)(=O)NC(=O)c3cccnc3N3CC(C)CC3(C)C)n2)cc1]
2579

TABLE 1-continued
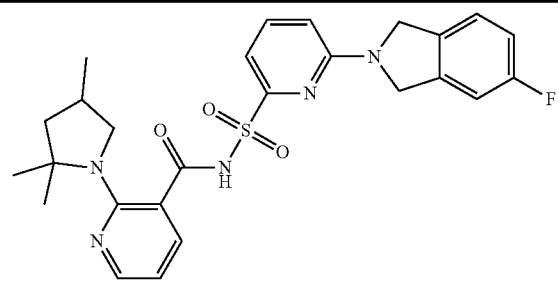
2580
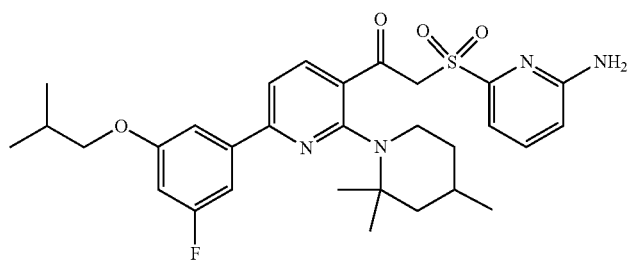 [SMILES: CC(C)COc1cc(F)cc(-c2ccc(C(=O)CS(=O)(=O)c3cccc(N)n3)c(N3CCC(C)CC3(C)C)n2)c1]
2581
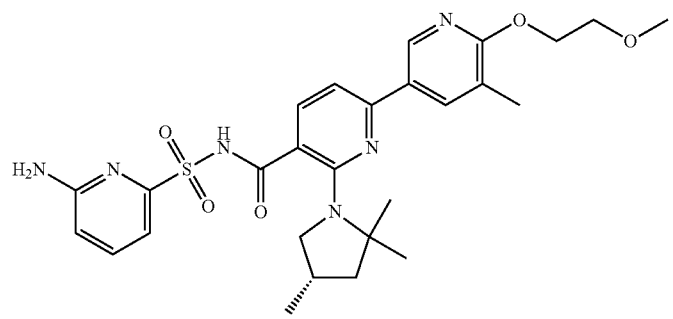 [SMILES: COCCOc1ncc(-c2ccc(C(=O)NS(=O)(=O)c3cccc(N)n3)c(N3C[C@@H](C)CC3(C)C)n2)cc1C]
2582
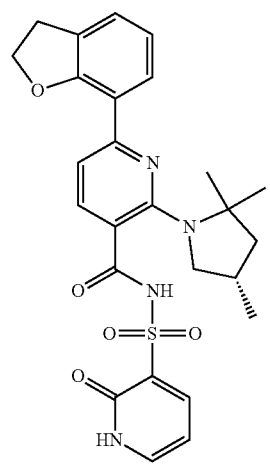 [SMILES: C[C@@H]1CN(c2nc(-c3cccc4c3OCC4)ccc2C(=O)NS(=O)(=O)c2ccc[nH]c2=O)C(C)(C)C1]
2583
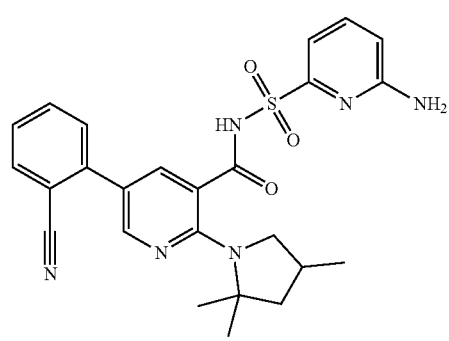 [SMILES: CC1CN(c2ncc(-c3ccccc3C#N)cc2C(=O)NS(=O)(=O)c2cccc(N)n2)C(C)(C)C1]
2584

TABLE 1-continued
| | |
|---|---|
| 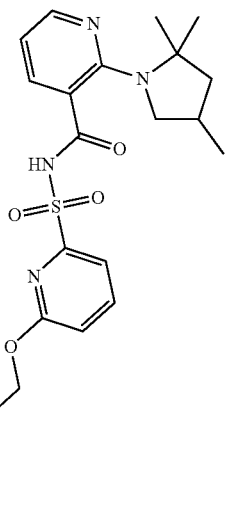 | 2585 |
| 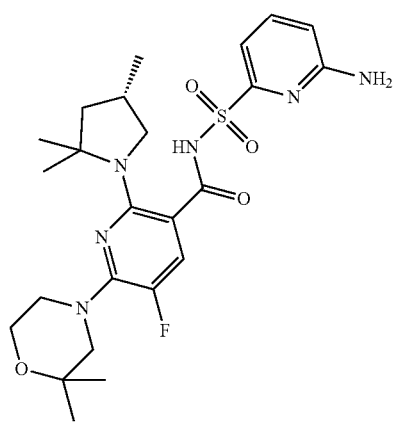 [SMILES: C[C@@H]1CN(c2nc(N3CCOC(C)(C)C3)c(F)cc2C(=O)NS(=O)(=O)c2cccc(N)n2)C(C)(C)C1] | 2586 |
| 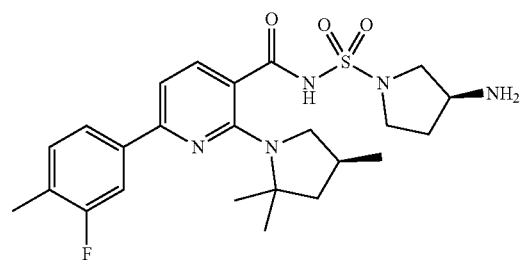 [SMILES: Cc1ccc(-c2ccc(C(=O)NS(=O)(=O)N3CC[C@H](N)C3)c(N3C[C@@H](C)CC3(C)C)n2)cc1F] | 2587 |
| 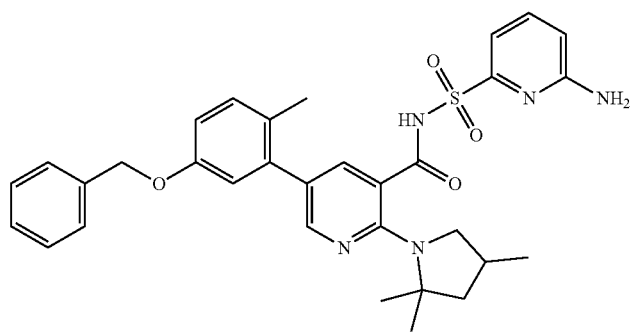 [SMILES: Cc1ccc(OCc2ccccc2)cc1-c1cnc(N2CC(C)CC2(C)C)c(C(=O)NS(=O)(=O)c2cccc(N)n2)c1] | 2588 |

TABLE 1-continued
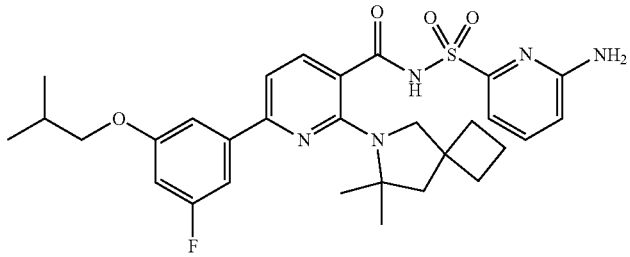 [SMILES: CC(C)COc1cc(F)cc(-c2ccc(C(=O)NS(=O)(=O)c3cccc(N)n3)c(N3CC4(CCC4)CC3(C)C)n2)c1]
2589
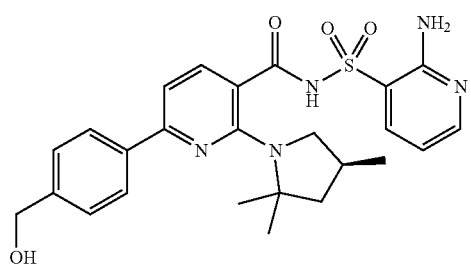 [SMILES: C[C@@H]1CN(c2nc(-c3ccc(CO)cc3)ccc2C(=O)NS(=O)(=O)c2cccnc2N)C(C)(C)C1]
2590
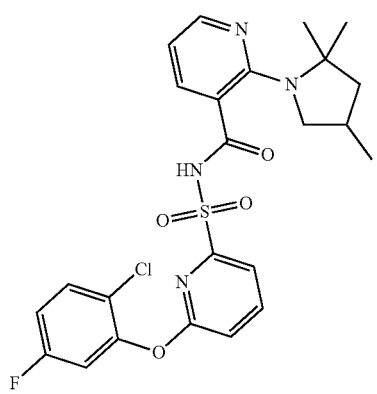 [SMILES: CC1CN(c2ncccc2C(=O)NS(=O)(=O)c2cccc(Oc3cc(F)ccc3Cl)n2)C(C)(C)C1]
2591
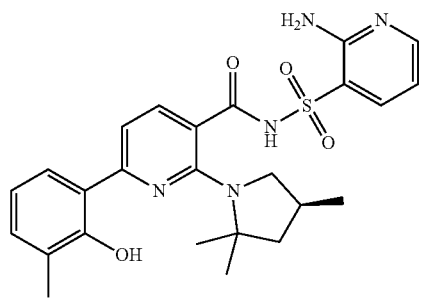 [SMILES: Cc1cccc(-c2ccc(C(=O)NS(=O)(=O)c3cccnc3N)c(N3C[C@@H](C)CC3(C)C)n2)c1O]
2592
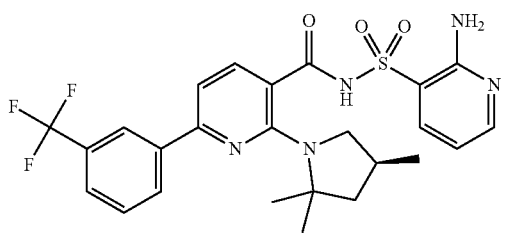 [SMILES: C[C@@H]1CN(c2nc(-c3cccc(C(F)(F)F)c3)ccc2C(=O)NS(=O)(=O)c2cccnc2N)C(C)(C)C1]
2593

TABLE 1-continued
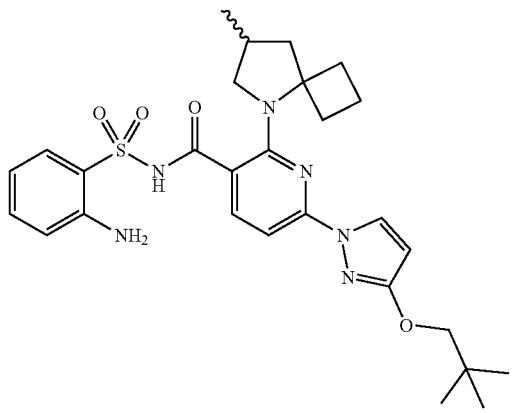 [SMILES: CC1CN(c2nc(-n3ccc(OCC(C)(C)C)n3)ccc2C(=O)NS(=O)(=O)c2ccccc2N)C2(CCC2)C1]
2594
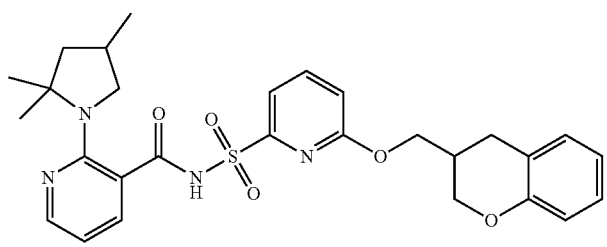 [SMILES: CC1CN(c2ncccc2C(=O)NS(=O)(=O)c2cccc(OCC3COc4ccccc4C3)n2)C(C)(C)C1]
2595
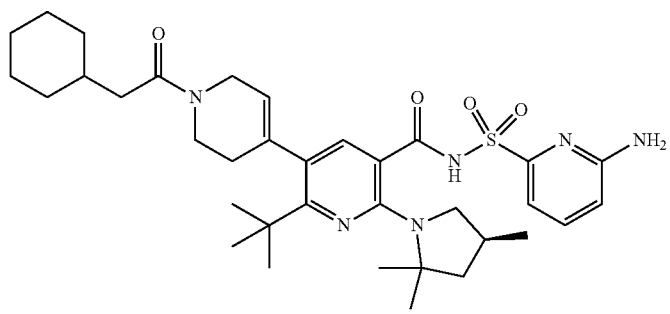 [SMILES: C[C@@H]1CN(c2nc(C(C)(C)C)c(C3=CCN(C(=O)CC4CCCCC4)CC3)cc2C(=O)NS(=O)(=O)c2cccc(N)n2)C(C)(C)C1]
2596
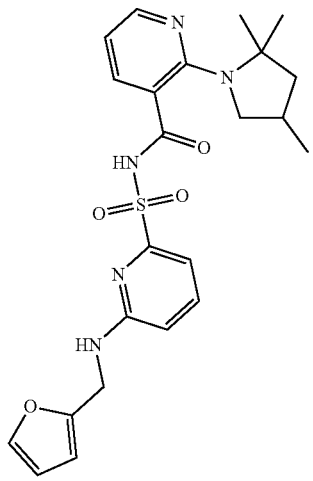 [SMILES: CC1CN(c2ncccc2C(=O)NS(=O)(=O)c2cccc(NCc3ccco3)n2)C(C)(C)C1]
2597

TABLE 1-continued
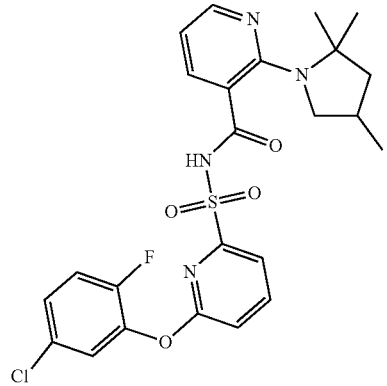 [SMILES: CC1CN(c2ncccc2C(=O)NS(=O)(=O)c2cccc(Oc3cc(Cl)ccc3F)n2)C(C)(C)C1]
2598
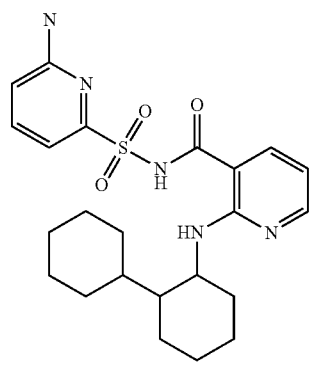
2599
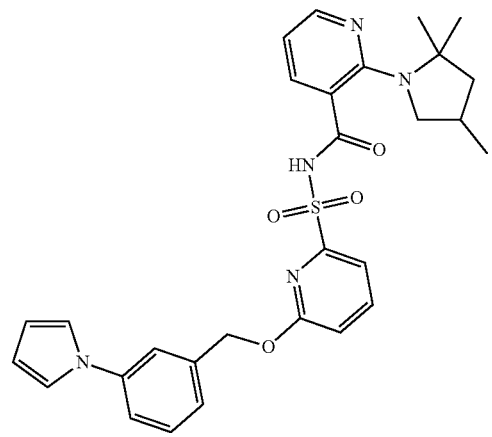 [SMILES: CC1CN(c2ncccc2C(=O)NS(=O)(=O)c2cccc(OCc3cccc(-n4cccc4)c3)n2)C(C)(C)C1]
2600

TABLE 1-continued
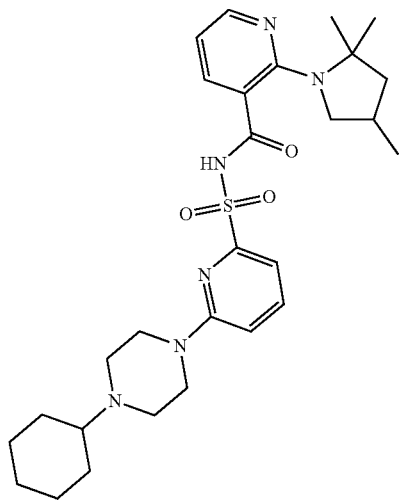 [SMILES: CC1CN(c2ncccc2C(=O)NS(=O)(=O)c2cccc(N3CCN(C4CCCCC4)CC3)n2)C(C)(C)C1] 2601
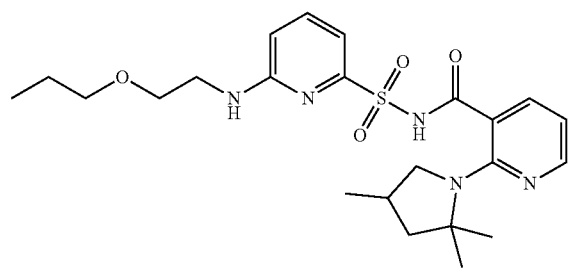 [SMILES: CCCOCCNc1cccc(S(=O)(=O)NC(=O)c2cccnc2N2CC(C)CC2(C)C)n1] 2602
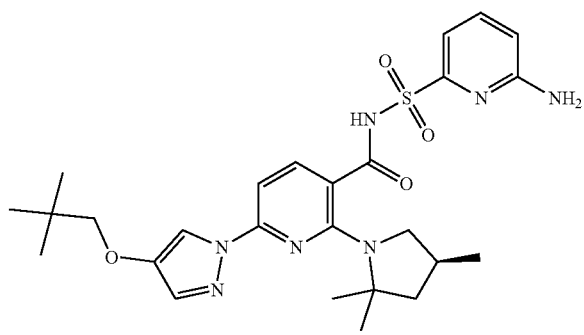 [SMILES: C[C@@H]1CN(c2nc(-n3cc(OCC(C)(C)C)cn3)ccc2C(=O)NS(=O)(=O)c2cccc(N)n2)C(C)(C)C1] 2603
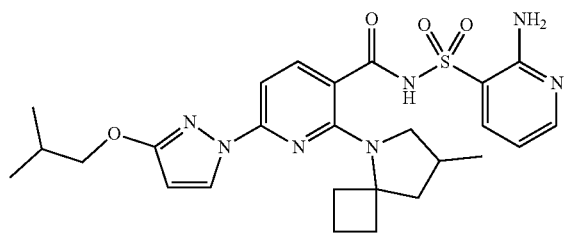 [SMILES: CC(C)COc1ccn(-c2ccc(C(=O)NS(=O)(=O)c3cccnc3N)c(N3CC(C)CC34CCC4)n2)n1] 2604
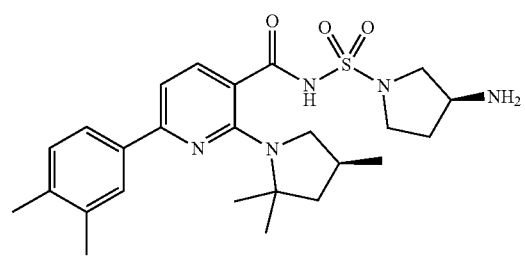 [SMILES: Cc1ccc(-c2ccc(C(=O)NS(=O)(=O)N3CC[C@H](N)C3)c(N3C[C@@H](C)CC3(C)C)n2)cc1C] 2605

TABLE 1-continued
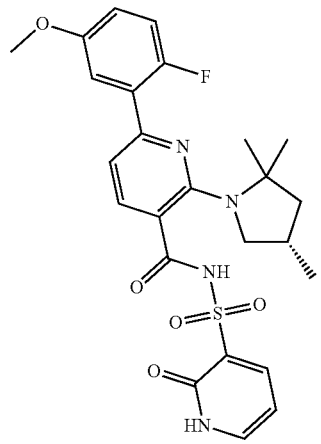
2606
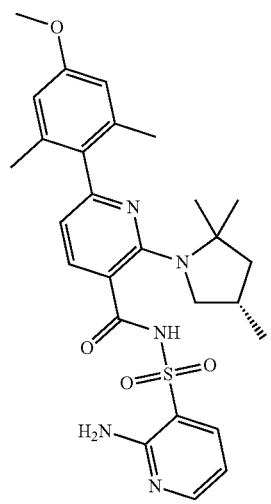
2607
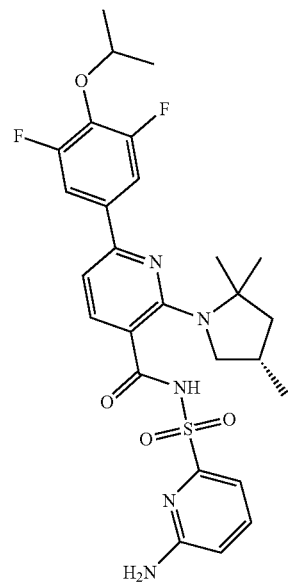 [SMILES: CC(C)Oc1c(F)cc(-c2ccc(C(=O)NS(=O)(=O)c3cccc(N)n3)c(N3C[C@@H](C)CC3(C)C)n2)cc1F]
2608

TABLE 1-continued
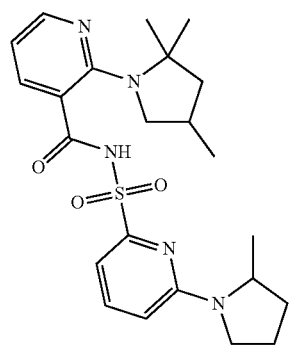 [SMILES: CC1CN(c2ncccc2C(=O)NS(=O)(=O)c2cccc(N3CCCC3C)n2)C(C)(C)C1]
2609
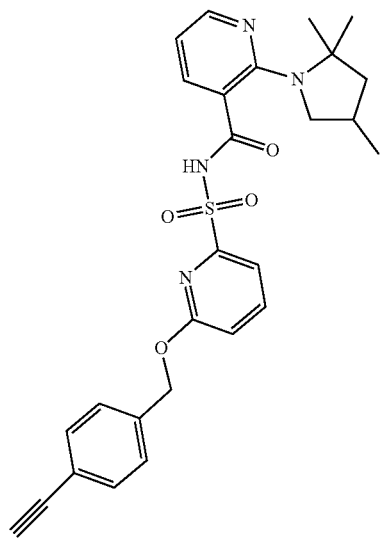 [SMILES: C#Cc1ccc(COc2cccc(S(=O)(=O)NC(=O)c3cccnc3N3CC(C)CC3(C)C)n2)cc1]
2610
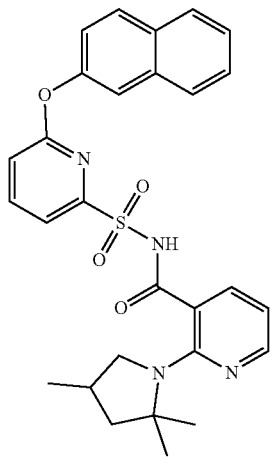 [SMILES: CC1CN(c2ncccc2C(=O)NS(=O)(=O)c2cccc(Oc3ccc4ccccc4c3)n2)C(C)(C)C1]
2611
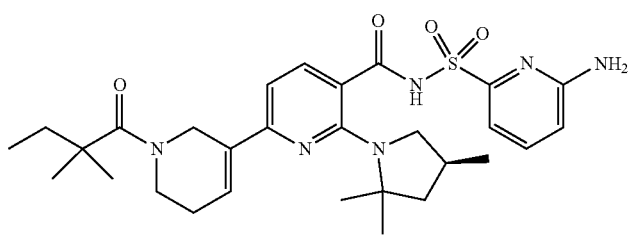 [SMILES: CCC(C)(C)C(=O)N1CCC=C(c2ccc(C(=O)NS(=O)(=O)c3cccc(N)n3)c(N3C[C@@H](C)CC3(C)C)n2)C1]
2612

TABLE 1-continued
| | |
|---|---|
| 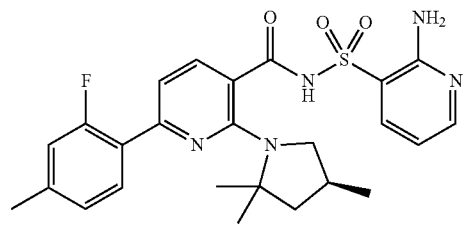 [SMILES: Cc1ccc(-c2ccc(C(=O)NS(=O)(=O)c3cccnc3N)c(N3C[C@@H](C)CC3(C)C)n2)c(F)c1] | 2613 |
| 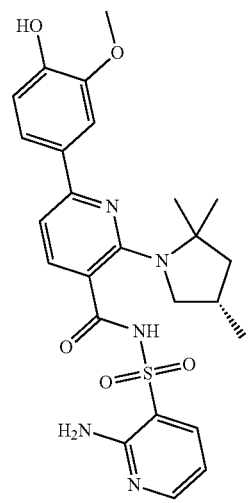 | 2614 |
| 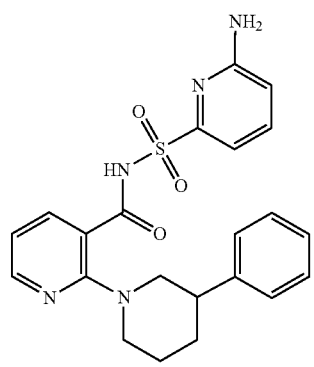 [SMILES: Nc1cccc(S(=O)(=O)NC(=O)c2cccnc2N2CCCC(c3ccccc3)C2)n1] | 2615 |
| 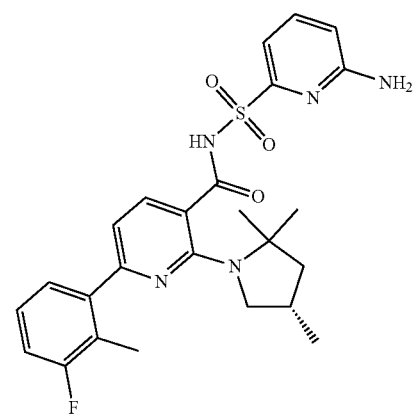 [SMILES: Cc1c(F)cccc1-c1ccc(C(=O)NS(=O)(=O)c2cccc(N)n2)c(N2C[C@@H](C)CC2(C)C)n1] | 2616 |

TABLE 1-continued
2617
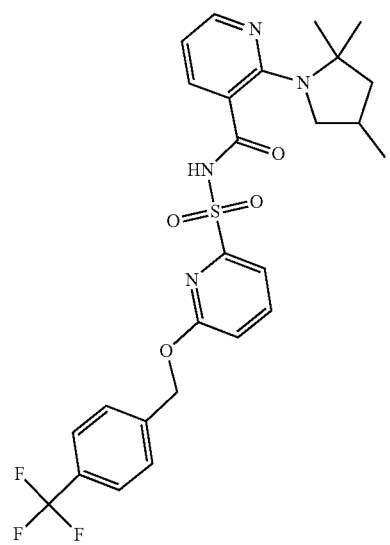 [SMILES: CC1CN(c2ncccc2C(=O)NS(=O)(=O)c2cccc(OCc3ccc(C(F)(F)F)cc3)n2)C(C)(C)C1]
2618
2619

TABLE 1-continued
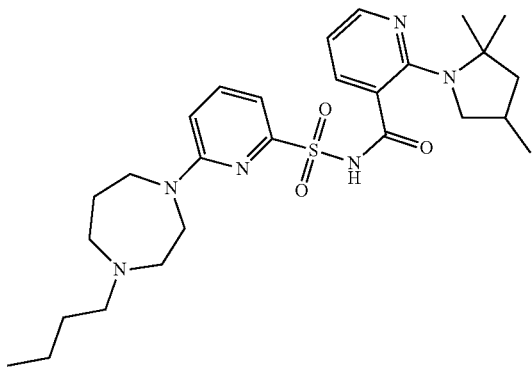 [SMILES: CCCCN1CCCN(c2cccc(S(=O)(=O)NC(=O)c3cccnc3N3CC(C)CC3(C)C)n2)CC1] 2620
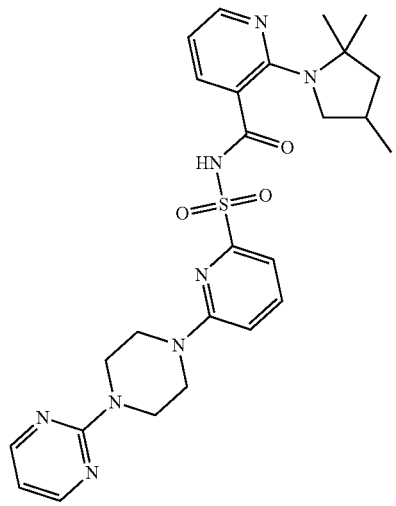 [SMILES: CC1CN(c2ncccc2C(=O)NS(=O)(=O)c2cccc(N3CCN(c4ncccn4)CC3)n2)C(C)(C)C1] 2621
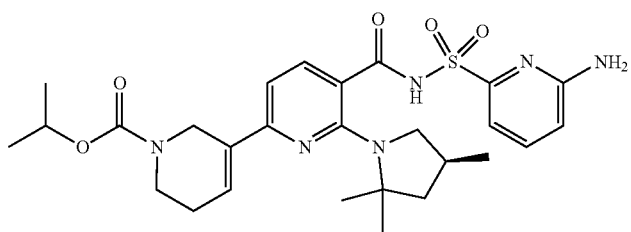 [SMILES: CC(C)OC(=O)N1CCC=C(c2ccc(C(=O)NS(=O)(=O)c3cccc(N)n3)c(N3C[C@@H](C)CC3(C)C)n2)C1] 2622
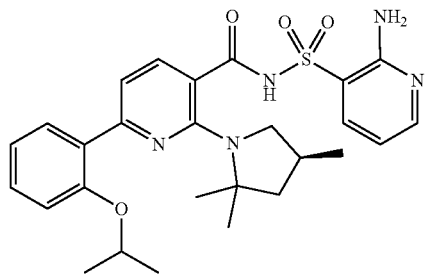 [SMILES: CC(C)Oc1ccccc1-c1ccc(C(=O)NS(=O)(=O)c2cccnc2N)c(N2C[C@@H](C)CC2(C)C)n1] 2623
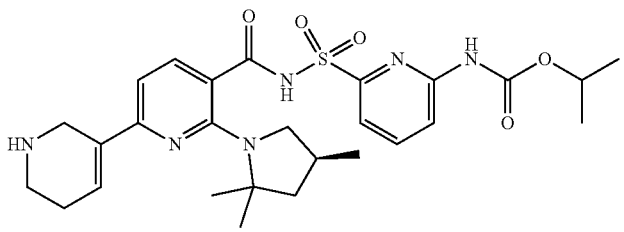 [SMILES: CC(C)OC(=O)Nc1cccc(S(=O)(=O)NC(=O)c2ccc(C3=CCCNC3)nc2N2C[C@@H](C)CC2(C)C)n1] 2624

TABLE 1-continued
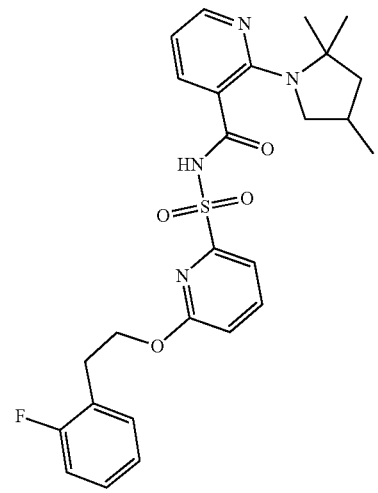 [SMILES: CC1CN(c2ncccc2C(=O)NS(=O)(=O)c2cccc(OCCc3ccccc3F)n2)C(C)(C)C1]
2625
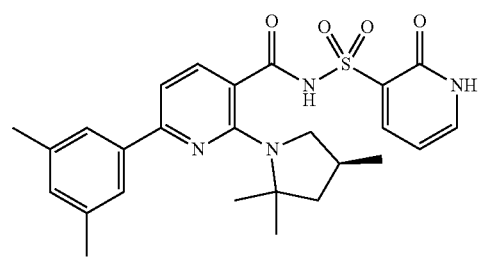 [SMILES: Cc1cc(C)cc(-c2ccc(C(=O)NS(=O)(=O)c3ccc[nH]c3=O)c(N3C[C@@H](C)CC3(C)C)n2)c1]
2626
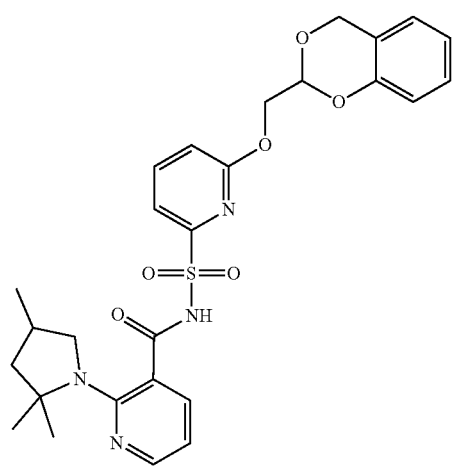 [SMILES: CC1CN(c2ncccc2C(=O)NS(=O)(=O)c2cccc(OCC3OCc4ccccc4O3)n2)C(C)(C)C1]
2627

TABLE 1-continued
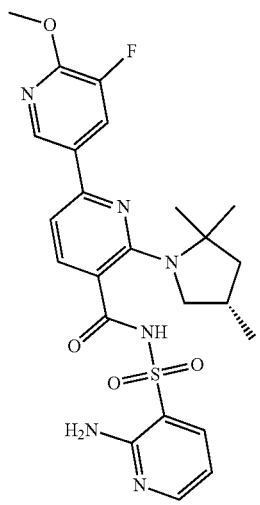 2628
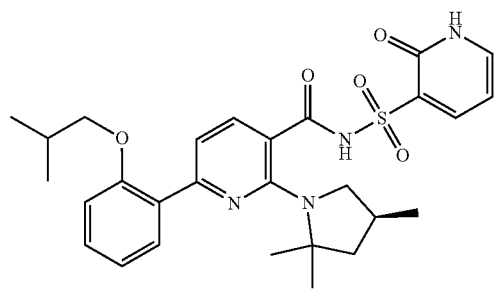 [SMILES: CC(C)COc1ccccc1-c1ccc(C(=O)NS(=O)(=O)c2ccc[nH]c2=O)c(N2C[C@@H](C)CC2(C)C)n1] 2629
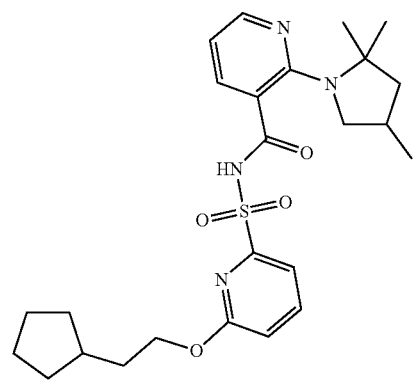 [SMILES: CC1CN(c2ncccc2C(=O)NS(=O)(=O)c2cccc(OCCC3CCCC3)n2)C(C)(C)C1] 2630
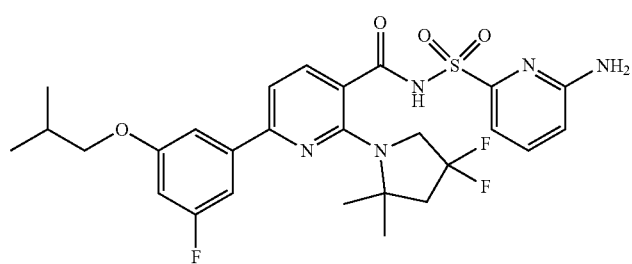 [SMILES: CC(C)COc1cc(F)cc(-c2ccc(C(=O)NS(=O)(=O)c3cccc(N)n3)c(N3CC(F)(F)CC3(C)C)n2)c1] 2631

TABLE 1-continued
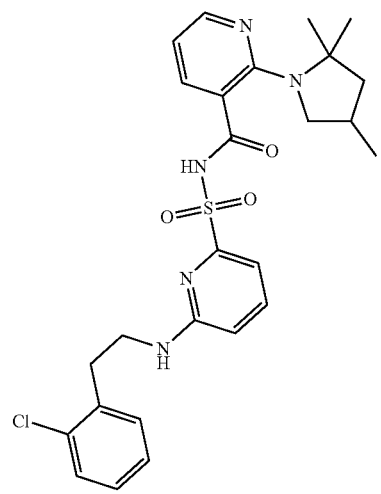 [SMILES: CC1CN(c2ncccc2C(=O)NS(=O)(=O)c2cccc(NCCc3ccccc3Cl)n2)C(C)(C)C1]
2632
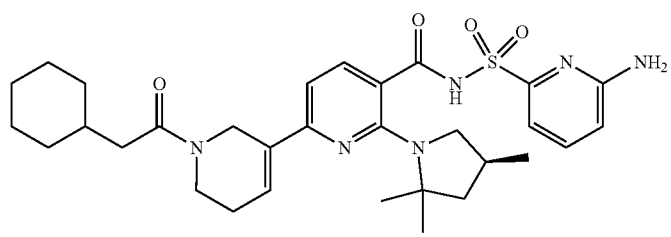 [SMILES: C[C@@H]1CN(c2nc(C3=CCCN(C(=O)CC4CCCCC4)C3)ccc2C(=O)NS(=O)(=O)c2cccc(N)n2)C(C)(C)C1]
2633
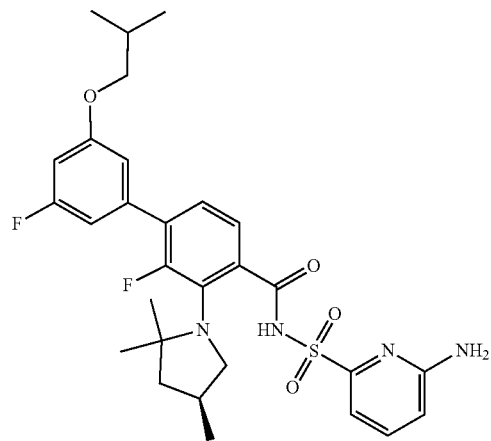 [SMILES: CC(C)COc1cc(F)cc(-c2ccc(C(=O)NS(=O)(=O)c3cccc(N)n3)c(N3C[C@@H](C)CC3(C)C)c2F)c1]
2634
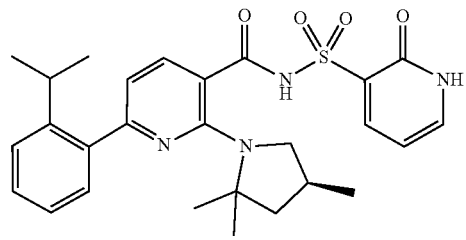 [SMILES: CC(C)c1ccccc1-c1ccc(C(=O)NS(=O)(=O)c2ccc[nH]c2=O)c(N2C[C@@H](C)CC2(C)C)n1]
2635

TABLE 1-continued
| | |
|---|---|
| 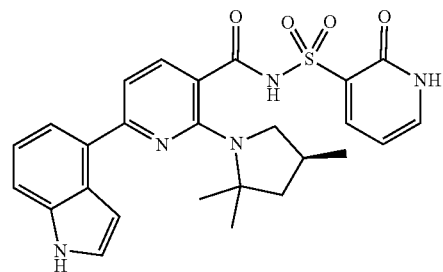 [SMILES: C[C@@H]1CN(c2nc(-c3cccc4[nH]ccc34)ccc2C(=O)NS(=O)(=O)c2ccc[nH]c2=O)C(C)(C)C1] | 2636 |
| 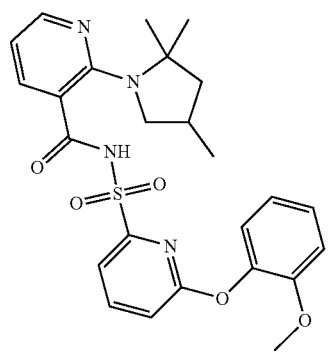 [SMILES: COc1ccccc1Oc1cccc(S(=O)(=O)NC(=O)c2cccnc2N2CC(C)CC2(C)C)n1] | 2637 |
|  | 2638 |
| 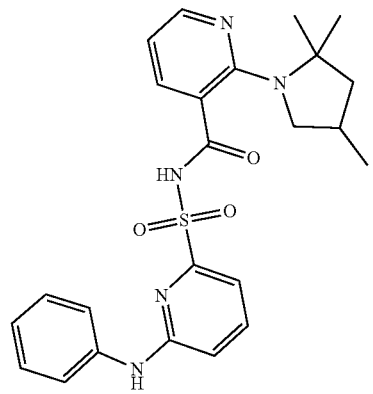 [SMILES: CC1CN(c2ncccc2C(=O)NS(=O)(=O)c2cccc(Nc3ccccc3)n2)C(C)(C)C1] | 2639 |

TABLE 1-continued
| | |
|---|---|
| 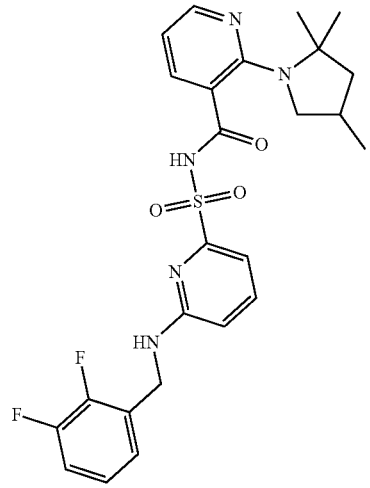 [SMILES: CC1CN(c2ncccc2C(=O)NS(=O)(=O)c2cccc(NCc3cccc(F)c3F)n2)C(C)(C)C1] | 2640 |
| 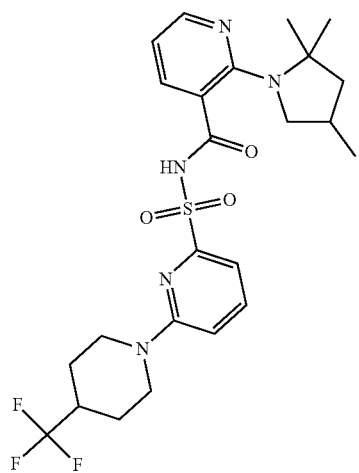 [SMILES: CC1CN(c2ncccc2C(=O)NS(=O)(=O)c2cccc(N3CCC(C(F)(F)F)CC3)n2)C(C)(C)C1] | 2641 |
| 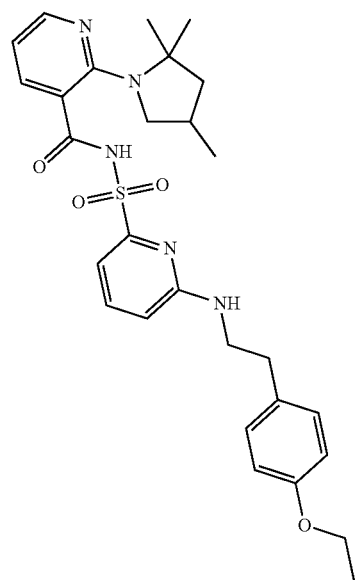 [SMILES: CCOc1ccc(CCNc2cccc(S(=O)(=O)NC(=O)c3cccnc3N3CC(C)CC3(C)C)n2)cc1] | 2642 |

TABLE 1-continued
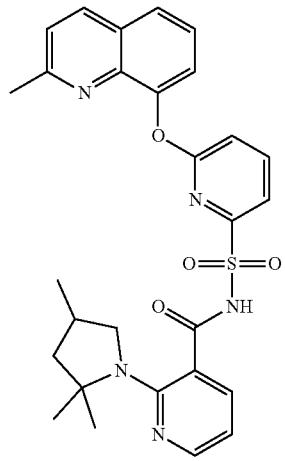 [SMILES: Cc1ccc2cccc(Oc3cccc(S(=O)(=O)NC(=O)c4cccnc4N4CC(C)CC4(C)C)n3)c2n1]
2643
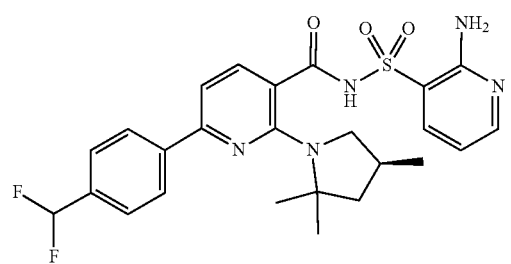 [SMILES: C[C@@H]1CN(c2nc(-c3ccc(C(F)F)cc3)ccc2C(=O)NS(=O)(=O)c2cccnc2N)C(C)(C)C1]
2644
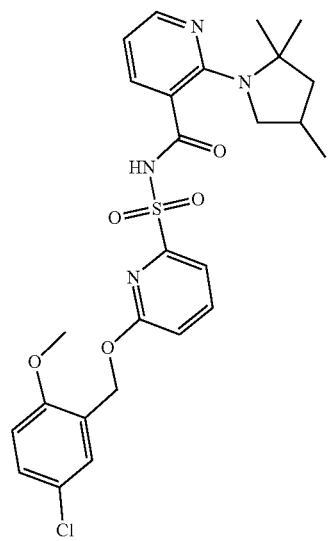 [SMILES: COc1ccc(Cl)cc1COc1cccc(S(=O)(=O)NC(=O)c2cccnc2N2CC(C)CC2(C)C)n1]
2645

TABLE 1-continued
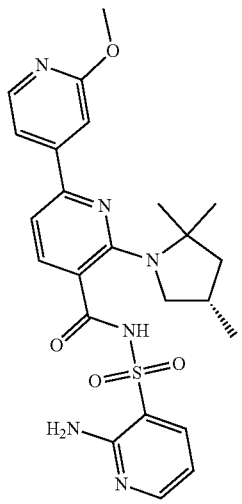 [SMILES: COc1cc(-c2ccc(C(=O)NS(=O)(=O)c3cccnc3N)c(N3C[C@@H](C)CC3(C)C)n2)ccn1]
2646
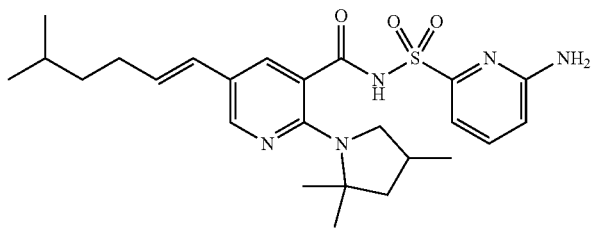 [SMILES: CC(C)CC/C=C/c1cnc(N2CC(C)CC2(C)C)c(C(=O)NS(=O)(=O)c2cccc(N)n2)c1]
2647
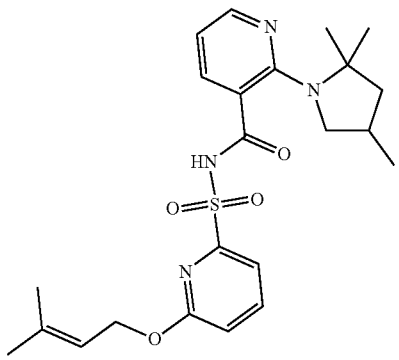 [SMILES: CC(C)=CCOc1cccc(S(=O)(=O)NC(=O)c2cccnc2N2CC(C)CC2(C)C)n1]
2648
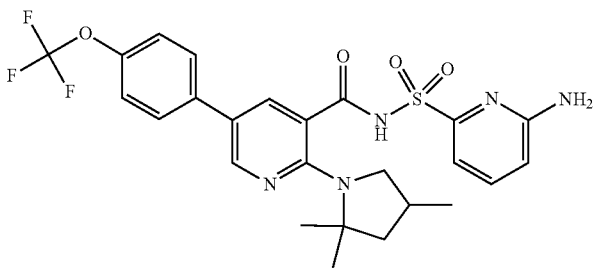 [SMILES: CC1CN(c2ncc(-c3ccc(OC(F)(F)F)cc3)cc2C(=O)NS(=O)(=O)c2cccc(N)n2)C(C)(C)C1]
2649
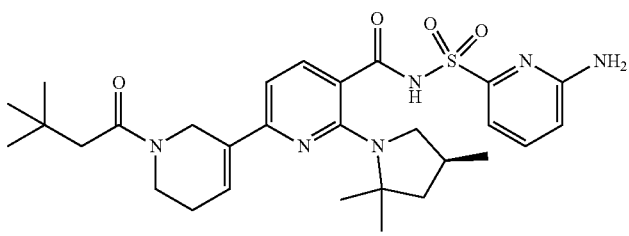 [SMILES: C[C@@H]1CN(c2nc(C3=CCCN(C(=O)CC(C)(C)C)C3)ccc2C(=O)NS(=O)(=O)c2cccc(N)n2)C(C)(C)C1]
2650

TABLE 1-continued
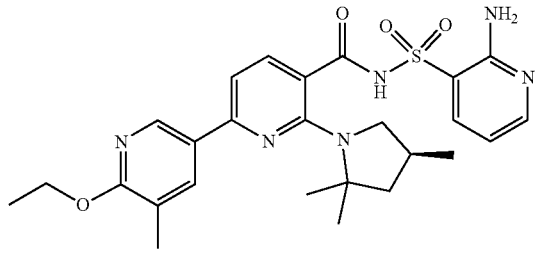 [SMILES: CCOc1ncc(-c2ccc(C(=O)NS(=O)(=O)c3cccnc3N)c(N3C[C@@H](C)CC3(C)C)n2)cc1C]
2651
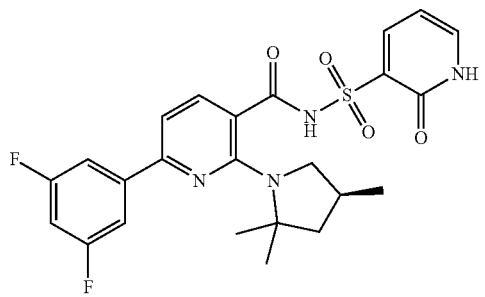 [SMILES: C[C@@H]1CN(c2nc(-c3cc(F)cc(F)c3)ccc2C(=O)NS(=O)(=O)c2ccc[nH]c2=O)C(C)(C)C1]
2652
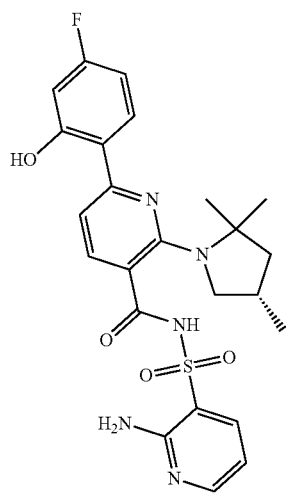 [SMILES: C[C@@H]1CN(c2nc(-c3ccc(F)cc3O)ccc2C(=O)NS(=O)(=O)c2cccnc2N)C(C)(C)C1]
2653
2654

TABLE 1-continued
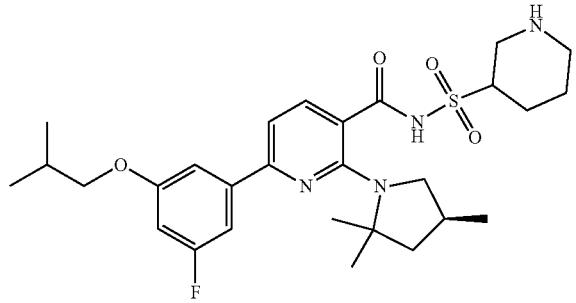 [SMILES: CC(C)COc1cc(F)cc(-c2ccc(C(=O)NS(=O)(=O)C3CCCNC3)c(N3C[C@@H](C)CC3(C)C)n2)c1]
2655
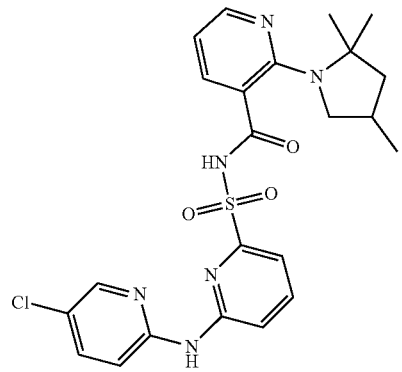 [SMILES: CC1CN(c2ncccc2C(=O)NS(=O)(=O)c2cccc(Nc3ccc(Cl)cn3)n2)C(C)(C)C1]
2656
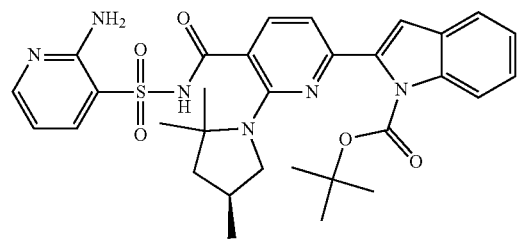 [SMILES: C[C@@H]1CN(c2nc(-c3cc4ccccc4n3C(=O)OC(C)(C)C)ccc2C(=O)NS(=O)(=O)c2cccnc2N)C(C)(C)C1]
2657
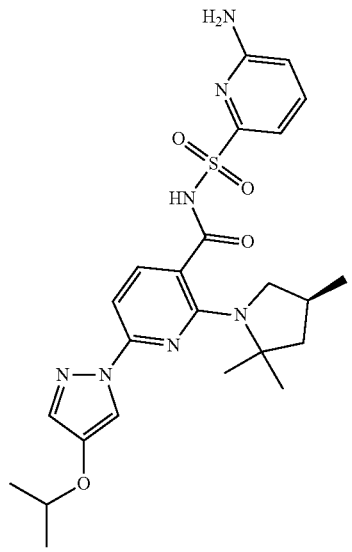 [SMILES: CC(C)Oc1cnn(-c2ccc(C(=O)NS(=O)(=O)c3cccc(N)n3)c(N3C[C@@H](C)CC3(C)C)n2)c1]
2658

TABLE 1-continued
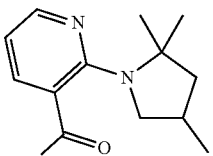
2659
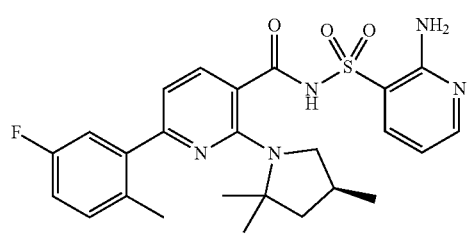 [SMILES: Cc1ccc(F)cc1-c1ccc(C(=O)NS(=O)(=O)c2cccnc2N)c(N2C[C@@H](C)CC2(C)C)n1]
2660
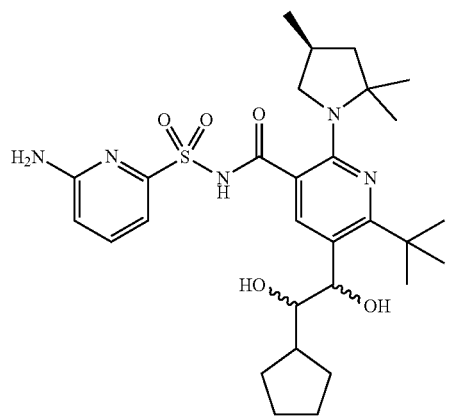 [SMILES: C[C@@H]1CN(c2nc(C(C)(C)C)c(C(O)C(O)C3CCCC3)cc2C(=O)NS(=O)(=O)c2cccc(N)n2)C(C)(C)C1]
2661
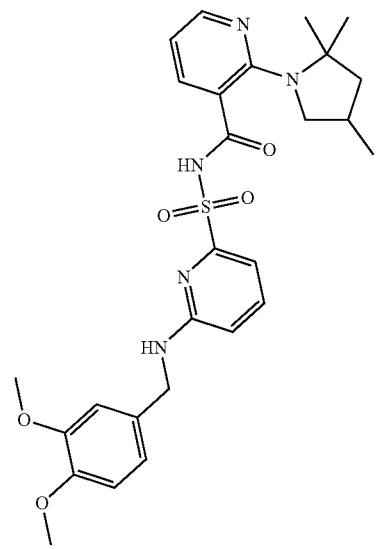
2662

| | |
|---|---|
| 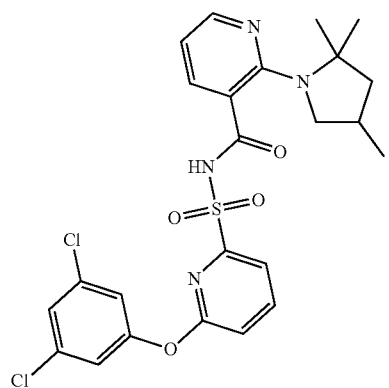 [SMILES: CC1CN(c2ncccc2C(=O)NS(=O)(=O)c2cccc(Oc3cc(Cl)cc(Cl)c3)n2)C(C)(C)C1] | 2663 |
| 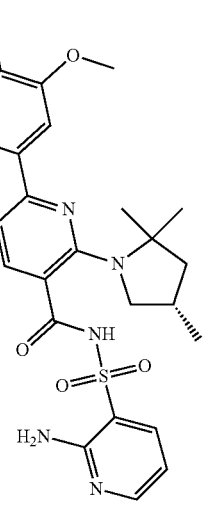 | 2664 |
| 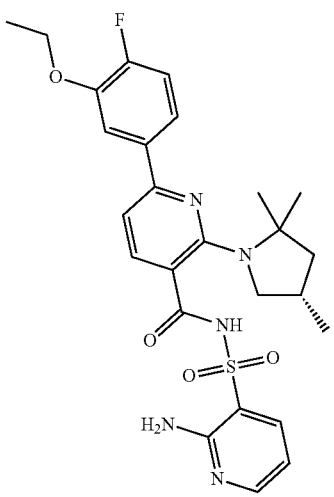 [SMILES: CCOc1cc(-c2ccc(C(=O)NS(=O)(=O)c3cccnc3N)c(N3C[C@@H](C)CC3(C)C)n2)ccc1F] | 2665 |
| 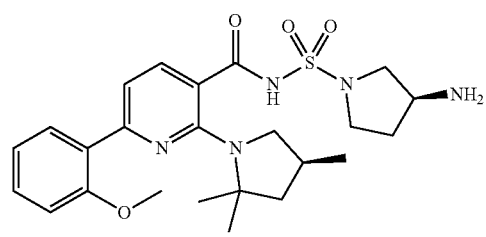 [SMILES: COc1ccccc1-c1ccc(C(=O)NS(=O)(=O)N2CC[C@H](N)C2)c(N2C[C@@H](C)CC2(C)C)n1] | 2666 |

TABLE 1-continued
| | |
|---|---|
| 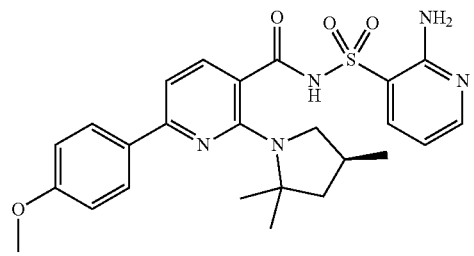 [SMILES: COc1ccc(-c2ccc(C(=O)NS(=O)(=O)c3cccnc3N)c(N3C[C@@H](C)CC3(C)C)n2)cc1] | 2667 |
| 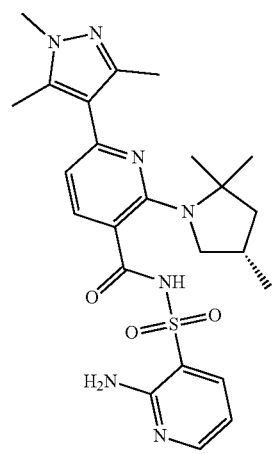 | 2668 |
| 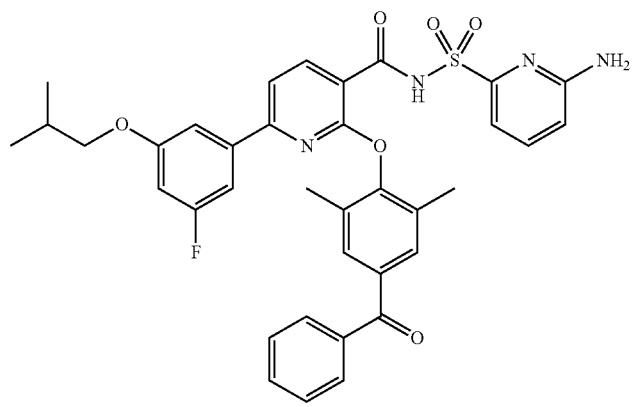 [SMILES: Cc1cc(C(=O)c2ccccc2)cc(C)c1Oc1nc(-c2cc(F)cc(OCC(C)C)c2)ccc1C(=O)NS(=O)(=O)c1cccc(N)n1] | 2669 |
| 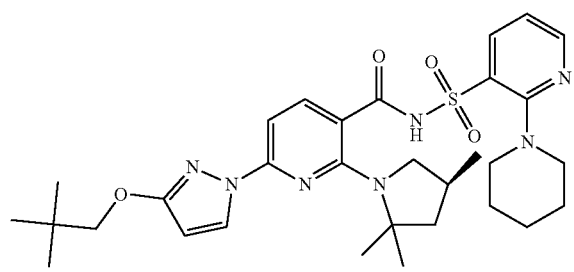 [SMILES: C[C@@H]1CN(c2nc(-n3ccc(OCC(C)(C)C)n3)ccc2C(=O)NS(=O)(=O)c2cccnc2N2CCCCC2)C(C)(C)C1] | 2670 |

TABLE 1-continued
| | |
|---|---|
| 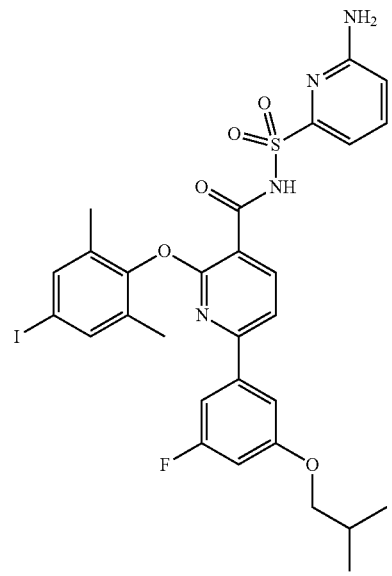 [SMILES: Cc1cc(I)cc(C)c1Oc1nc(-c2cc(F)cc(OCC(C)C)c2)ccc1C(=O)NS(=O)(=O)c1cccc(N)n1] | 2671 |
| 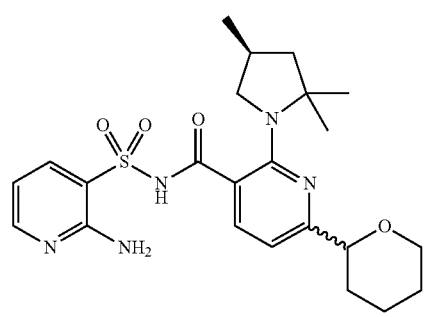 [SMILES: C[C@@H]1CN(c2nc(C3CCCCO3)ccc2C(=O)NS(=O)(=O)c2cccnc2N)C(C)(C)C1] | 2672 |
| 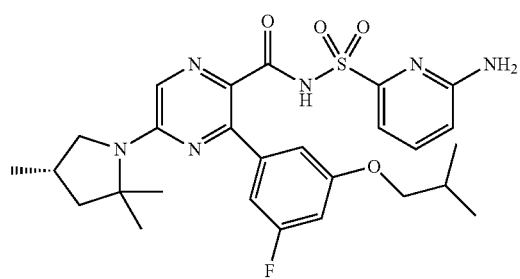 [SMILES: CC(C)COc1cc(F)cc(-c2nc(N3C[C@@H](C)CC3(C)C)cnc2C(=O)NS(=O)(=O)c2cccc(N)n2)c1] | 2673 |
| 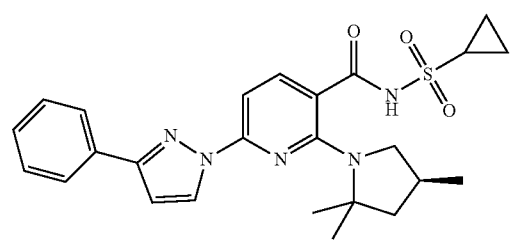 [SMILES: C[C@@H]1CN(c2nc(-n3ccc(-c4ccccc4)n3)ccc2C(=O)NS(=O)(=O)C2CC2)C(C)(C)C1] | 2674 |

TABLE 1-continued
| | |
|---|---|
| 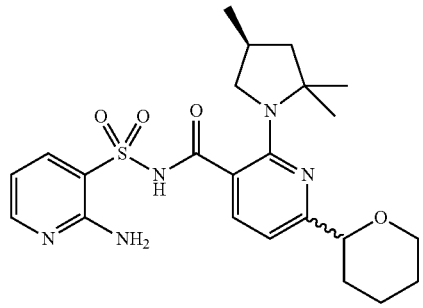 [SMILES: C[C@@H]1CN(c2nc(C3CCCCO3)ccc2C(=O)NS(=O)(=O)c2cccnc2N)C(C)(C)C1] | 2675 |
| 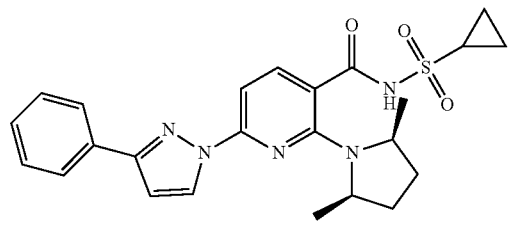 [SMILES: C[C@@H]1CC[C@H](C)N1c1nc(-n2ccc(-c3ccccc3)n2)ccc1C(=O)NS(=O)(=O)C1CC1] | 2676 |
| 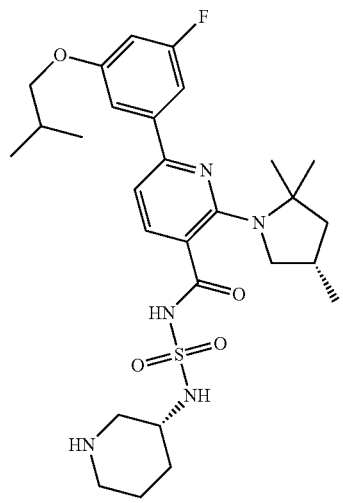 [SMILES: CC(C)COc1cc(F)cc(-c2ccc(C(=O)NS(=O)(=O)N[C@@H]3CCCNC3)c(N3C[C@@H](C)CC3(C)C)n2)c1] | 2677 |
| 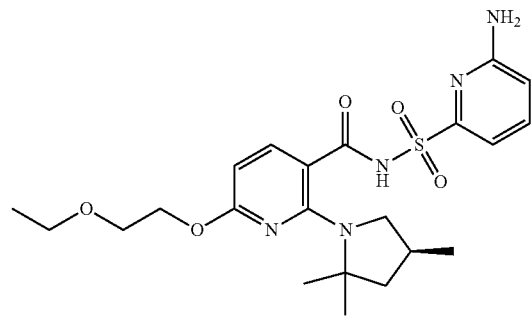 [SMILES: CCOCCOc1ccc(C(=O)NS(=O)(=O)c2cccc(N)n2)c(N2C[C@@H](C)CC2(C)C)n1] | 2678 |

TABLE 1-continued
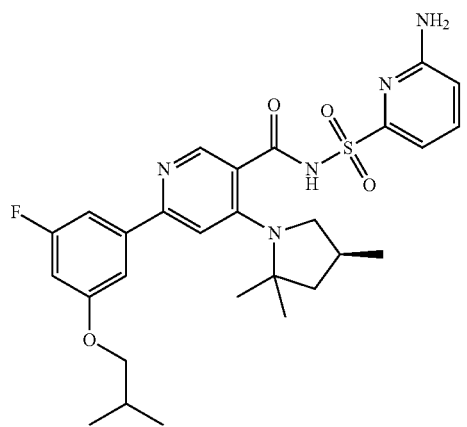 [SMILES: CC(C)COc1cc(F)cc(-c2cc(N3C[C@@H](C)CC3(C)C)c(C(=O)NS(=O)(=O)c3cccc(N)n3)cn2)c1]
2679
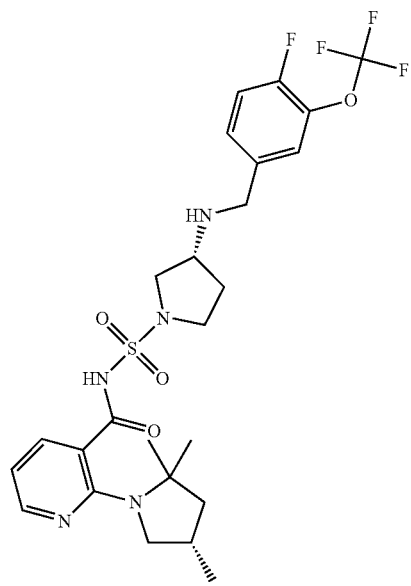 [SMILES: C[C@@H]1CN(c2ncccc2C(=O)NS(=O)(=O)N2CC[C@@H](NCc3ccc(F)c(OC(F)(F)F)c3)C2)C(C)(C)C1]
2680
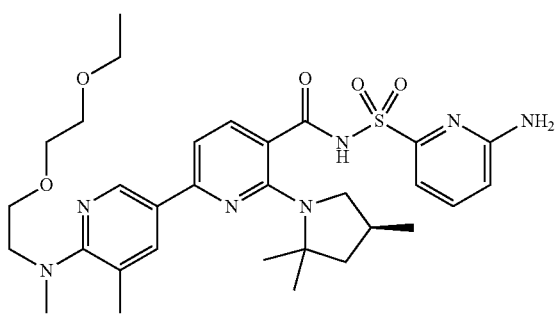 [SMILES: CCOCCOCCN(C)c1ncc(-c2ccc(C(=O)NS(=O)(=O)c3cccc(N)n3)c(N3C[C@@H](C)CC3(C)C)n2)cc1C]
2681
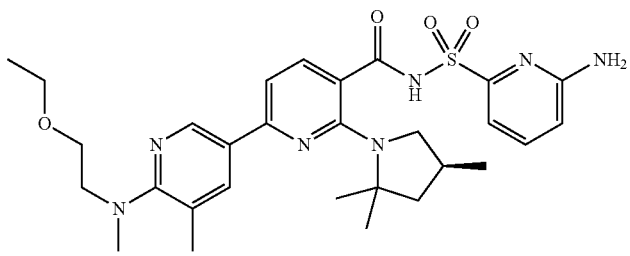 [SMILES: CCOCCN(C)c1ncc(-c2ccc(C(=O)NS(=O)(=O)c3cccc(N)n3)c(N3C[C@@H](C)CC3(C)C)n2)cc1C]
2682

TABLE 1-continued
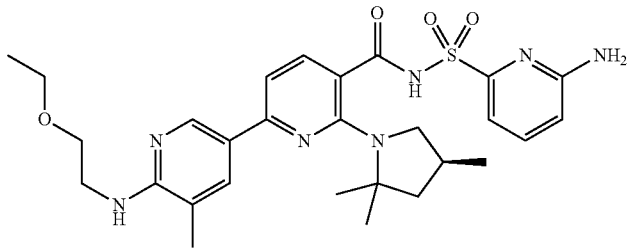 [SMILES: CCOCCNc1ncc(-c2ccc(C(=O)NS(=O)(=O)c3cccc(N)n3)c(N3C[C@@H](C)CC3(C)C)n2)cc1C]
2683
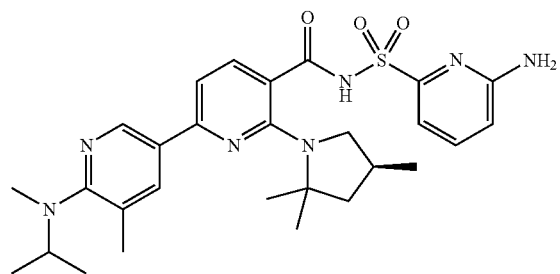 [SMILES: Cc1cc(-c2ccc(C(=O)NS(=O)(=O)c3cccc(N)n3)c(N3C[C@@H](C)CC3(C)C)n2)cnc1N(C)C(C)C]
2684
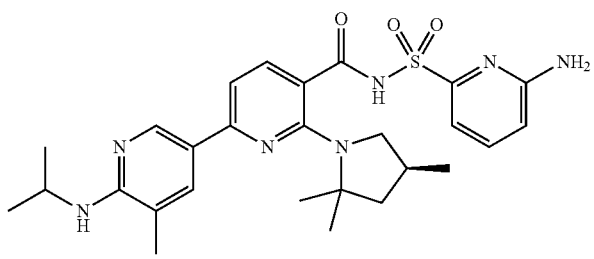 [SMILES: Cc1cc(-c2ccc(C(=O)NS(=O)(=O)c3cccc(N)n3)c(N3C[C@@H](C)CC3(C)C)n2)cnc1NC(C)C]
2685
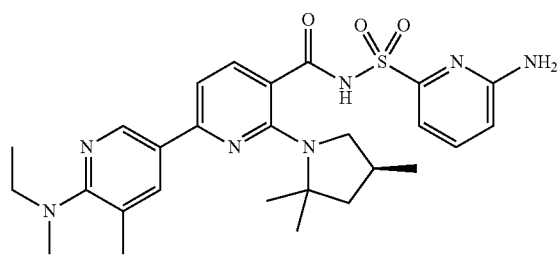 [SMILES: CCN(C)c1ncc(-c2ccc(C(=O)NS(=O)(=O)c3cccc(N)n3)c(N3C[C@@H](C)CC3(C)C)n2)cc1C]
2686
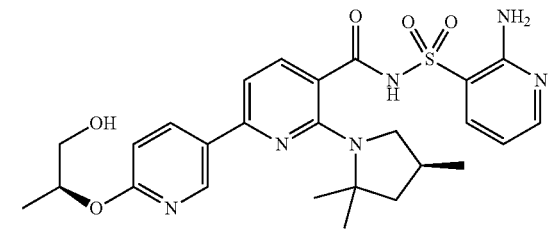 [SMILES: C[C@@H]1CN(c2nc(-c3ccc(O[C@@H](C)CO)nc3)ccc2C(=O)NS(=O)(=O)c2cccnc2N)C(C)(C)C1]
2687
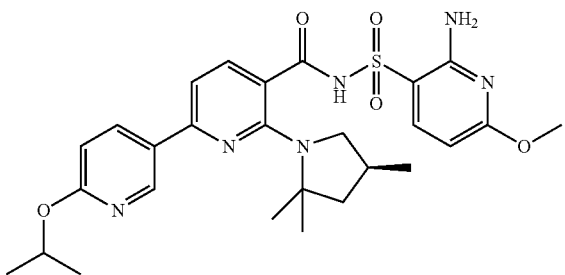 [SMILES: COc1ccc(S(=O)(=O)NC(=O)c2ccc(-c3ccc(OC(C)C)nc3)nc2N2C[C@@H](C)CC2(C)C)c(N)n1]
2688

TABLE 1-continued
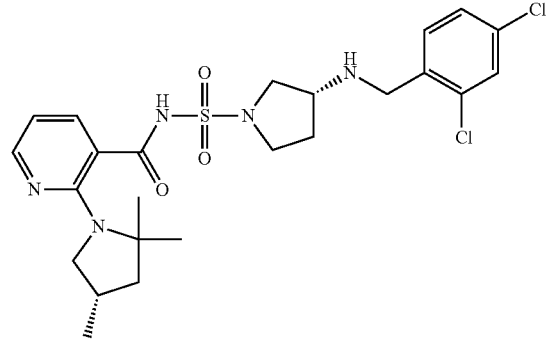 [SMILES: C[C@@H]1CN(c2ncccc2C(=O)NS(=O)(=O)N2CC[C@@H](NCc3ccc(Cl)cc3Cl)C2)C(C)(C)C1] 2689
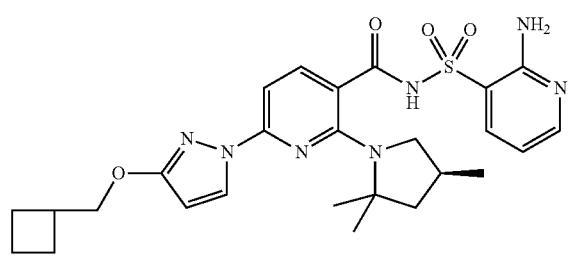 [SMILES: C[C@@H]1CN(c2nc(-n3ccc(OCC4CCC4)n3)ccc2C(=O)NS(=O)(=O)c2cccnc2N)C(C)(C)C1] 2690
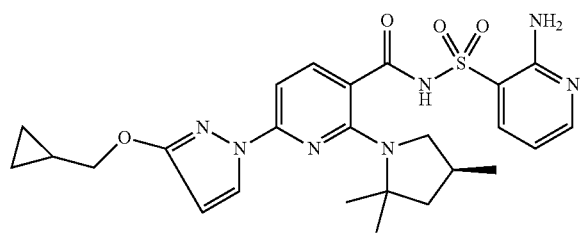 [SMILES: C[C@@H]1CN(c2nc(-n3ccc(OCC4CC4)n3)ccc2C(=O)NS(=O)(=O)c2cccnc2N)C(C)(C)C1] 2691
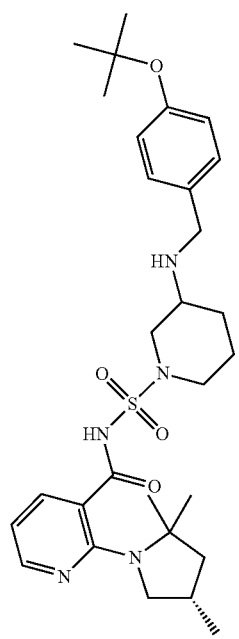 [SMILES: C[C@@H]1CN(c2ncccc2C(=O)NS(=O)(=O)N2CCCC(NCc3ccc(OC(C)(C)C)cc3)C2)C(C)(C)C1] 2692

TABLE 1-continued
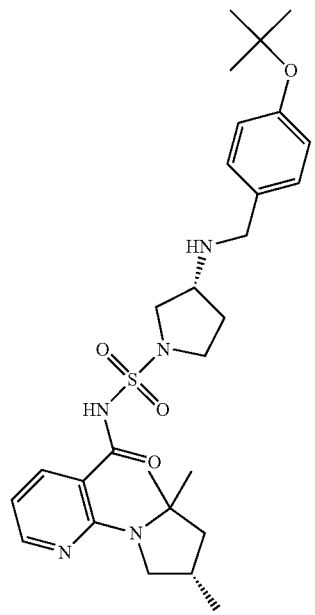 [SMILES: C[C@@H]1CN(c2ncccc2C(=O)NS(=O)(=O)N2CC[C@@H](NCc3ccc(OC(C)(C)C)cc3)C2)C(C)(C)C1]
2693
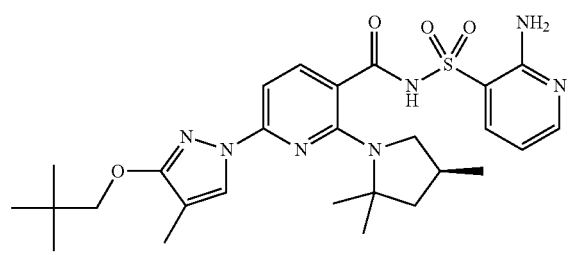 [SMILES: Cc1cn(-c2ccc(C(=O)NS(=O)(=O)c3cccnc3N)c(N3C[C@@H](C)CC3(C)C)n2)nc1OCC(C)(C)C]
2694
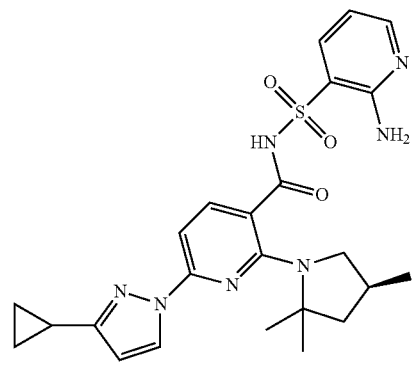 [SMILES: C[C@@H]1CN(c2nc(-n3ccc(C4CC4)n3)ccc2C(=O)NS(=O)(=O)c2cccnc2N)C(C)(C)C1]
2695
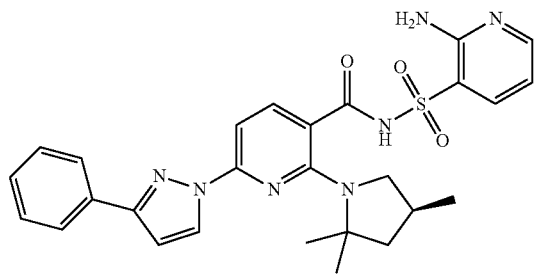 [SMILES: C[C@@H]1CN(c2nc(-n3ccc(-c4ccccc4)n3)ccc2C(=O)NS(=O)(=O)c2cccnc2N)C(C)(C)C1]
2696

TABLE 1-continued
| | |
|---|---|
| 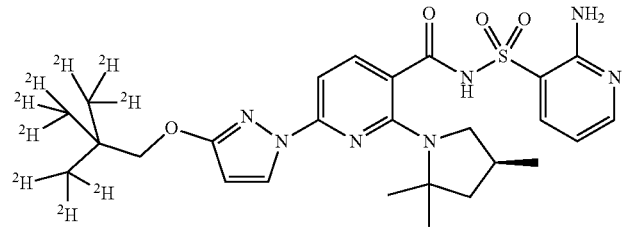 [SMILES: [2H]C([2H])([2H])C(COc1ccn(-c2ccc(C(=O)NS(=O)(=O)c3cccnc3N)c(N3C[C@@H](C)CC3(C)C)n2)n1)(C([2H])([2H])[2H])C([2H])([2H])[2H]] | 2697 |
| 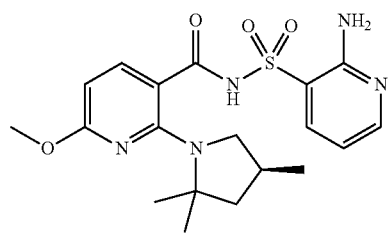 [SMILES: COc1ccc(C(=O)NS(=O)(=O)c2cccnc2N)c(N2C[C@@H](C)CC2(C)C)n1] | 2698 |
| 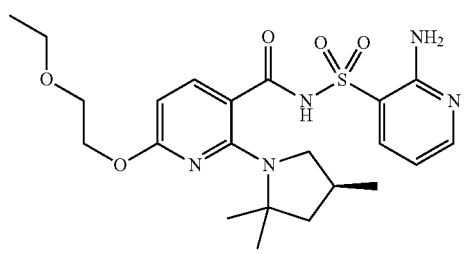 [SMILES: CCOCCOc1ccc(C(=O)NS(=O)(=O)c2cccnc2N)c(N2C[C@@H](C)CC2(C)C)n1] | 2699 |
| 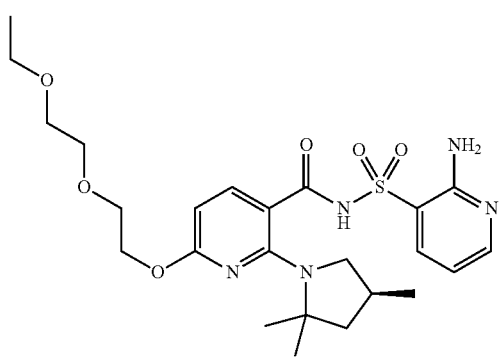 [SMILES: CCOCCOCCOc1ccc(C(=O)NS(=O)(=O)c2cccnc2N)c(N2C[C@@H](C)CC2(C)C)n1] | 2700 |
| 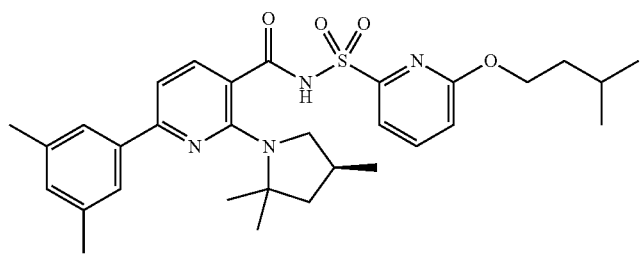 [SMILES: Cc1cc(C)cc(-c2ccc(C(=O)NS(=O)(=O)c3cccc(OCCC(C)C)n3)c(N3C[C@@H](C)CC3(C)C)n2)c1] | 2701 |

TABLE 1-continued
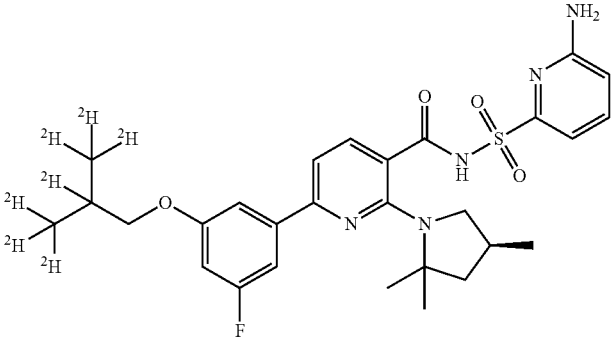 [SMILES: [2H]C([2H])([2H])C([2H])(COc1cc(F)cc(-c2ccc(C(=O)NS(=O)(=O)c3cccc(N)n3)c(N3C[C@@H](C)CC3(C)C)n2)c1)C([2H])([2H])[2H]]
2702
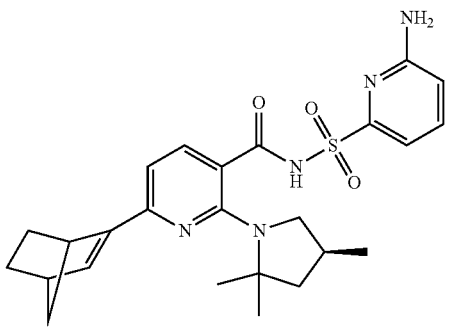 [SMILES: C[C@@H]1CN(c2nc(C3=CC4CCC3C4)ccc2C(=O)NS(=O)(=O)c2cccc(N)n2)C(C)(C)C1]
2703
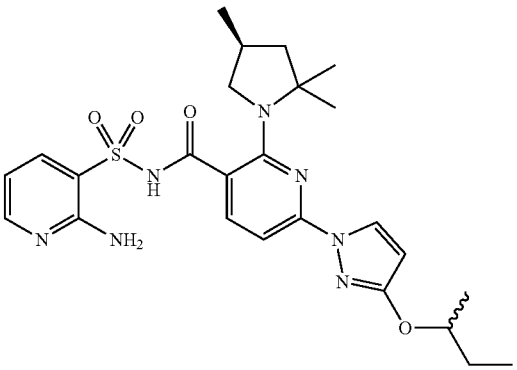 [SMILES: CCC(C)Oc1ccn(-c2ccc(C(=O)NS(=O)(=O)c3cccnc3N)c(N3C[C@@H](C)CC3(C)C)n2)n1]
2704
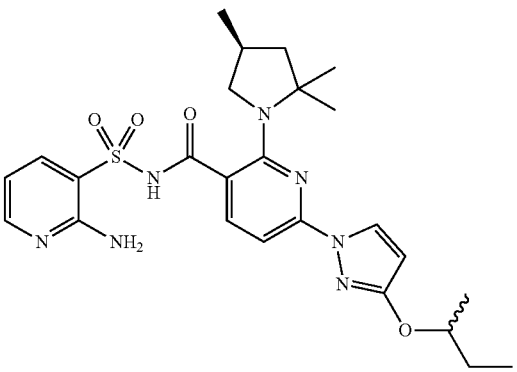 [SMILES: CCC(C)Oc1ccn(-c2ccc(C(=O)NS(=O)(=O)c3cccnc3N)c(N3C[C@@H](C)CC3(C)C)n2)n1]
2705

US 12,168,009 B2
TABLE 1-continued
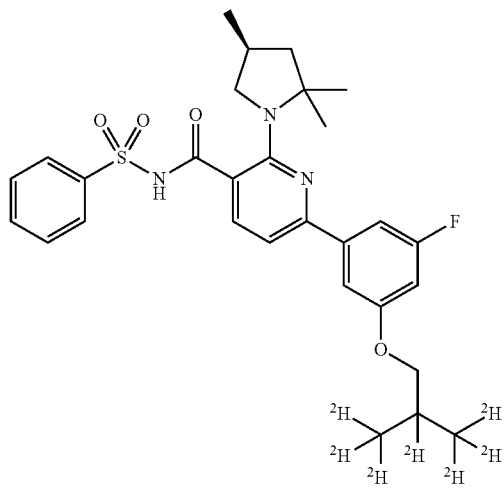 [SMILES: [2H]C([2H])([2H])C([2H])(COc1cc(F)cc(-c2ccc(C(=O)NS(=O)(=O)c3ccccc3)c(N3C[C@@H](C)CC3(C)C)n2)c1)C([2H])([2H])[2H]]
2706
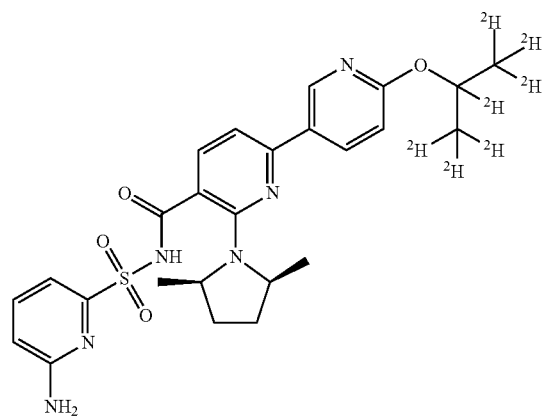 [SMILES: [2H]C([2H])([2H])C([2H])(Oc1ccc(-c2ccc(C(=O)NS(=O)(=O)c3cccc(N)n3)c(N3[C@H](C)CC[C@@H]3C)n2)cn1)C([2H])([2H])[2H]]
2707
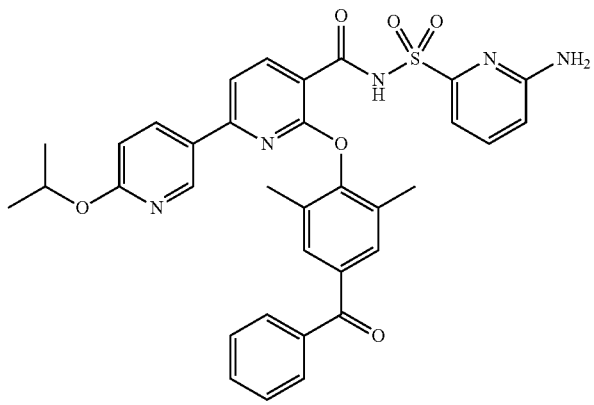 [SMILES: Cc1cc(C(=O)c2ccccc2)cc(C)c1Oc1nc(-c2ccc(OC(C)C)nc2)ccc1C(=O)NS(=O)(=O)c1cccc(N)n1]
2708
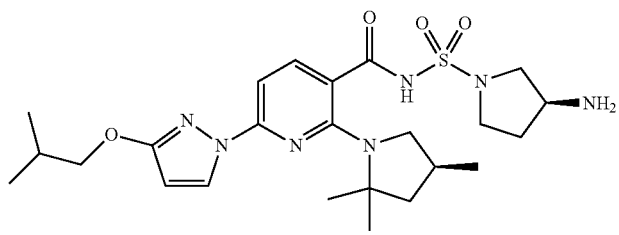 [SMILES: CC(C)COc1ccn(-c2ccc(C(=O)NS(=O)(=O)N3CC[C@H](N)C3)c(N3C[C@@H](C)CC3(C)C)n2)n1]
2709

TABLE 1-continued
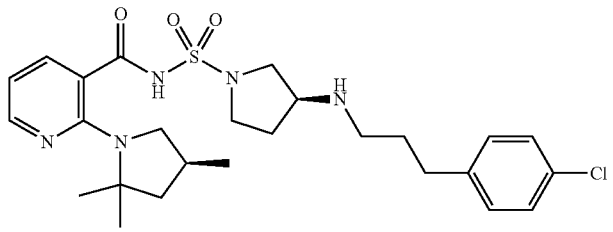 [SMILES: C[C@@H]1CN(c2ncccc2C(=O)NS(=O)(=O)N2CC[C@H](NCCCc3ccc(Cl)cc3)C2)C(C)(C)C1] 2710
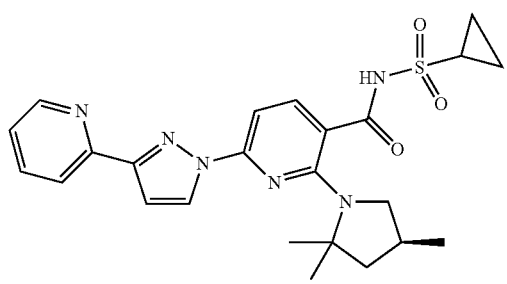 [SMILES: C[C@@H]1CN(c2nc(-n3ccc(-c4ccccn4)n3)ccc2C(=O)NS(=O)(=O)C2CC2)C(C)(C)C1] 2711
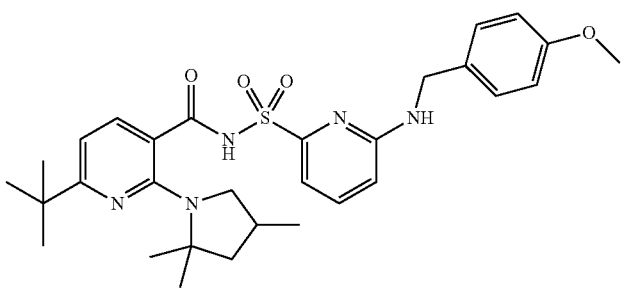 [SMILES: COc1ccc(CNc2cccc(S(=O)(=O)NC(=O)c3ccc(C(C)(C)C)nc3N3CC(C)CC3(C)C)n2)cc1] 2712
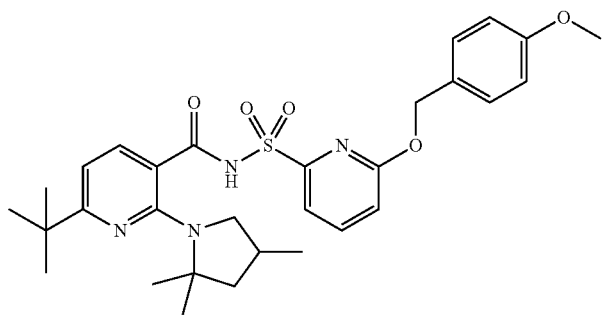 [SMILES: COc1ccc(COc2cccc(S(=O)(=O)NC(=O)c3ccc(C(C)(C)C)nc3N3CC(C)CC3(C)C)n2)cc1] 2713
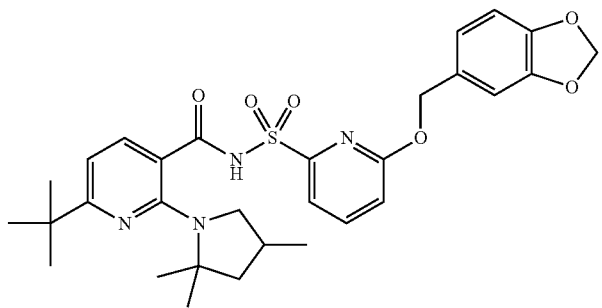 [SMILES: CC1CN(c2nc(C(C)(C)C)ccc2C(=O)NS(=O)(=O)c2cccc(OCc3ccc4c(c3)OCO4)n2)C(C)(C)C1] 2714

TABLE 1-continued
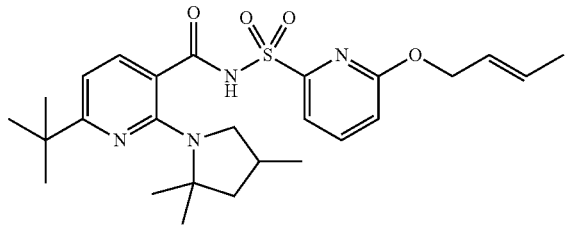 [SMILES: C/C=C/COc1cccc(S(=O)(=O)NC(=O)c2ccc(C(C)(C)C)nc2N2CC(C)CC2(C)C)n1] 2715
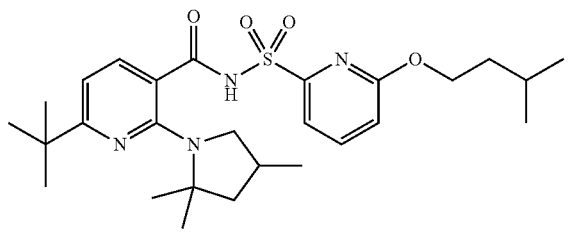 [SMILES: CC(C)CCOc1cccc(S(=O)(=O)NC(=O)c2ccc(C(C)(C)C)nc2N2CC(C)CC2(C)C)n1] 2716
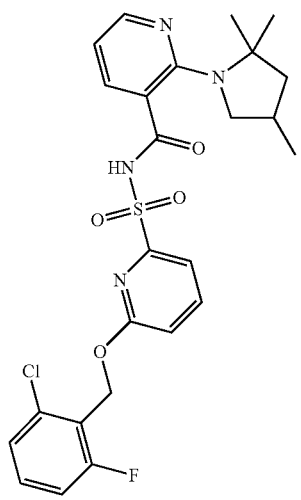 [SMILES: CC1CN(c2ncccc2C(=O)NS(=O)(=O)c2cccc(OCc3c(F)cccc3Cl)n2)C(C)(C)C1] 2717
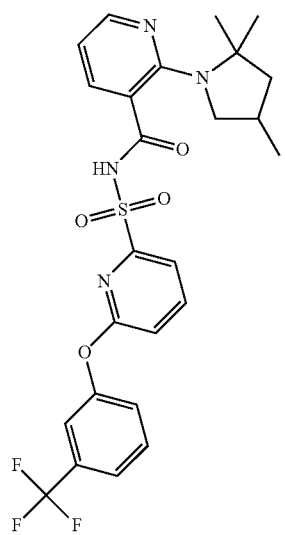 [SMILES: CC1CN(c2ncccc2C(=O)NS(=O)(=O)c2cccc(Oc3cccc(C(F)(F)F)c3)n2)C(C)(C)C1] 2718

TABLE 1-continued
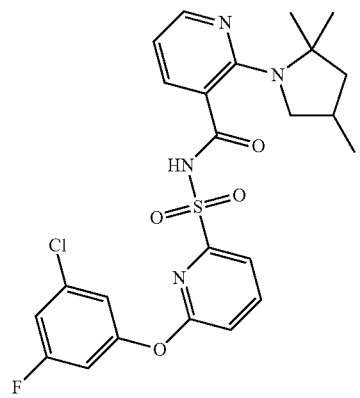 [SMILES: CC1CN(c2ncccc2C(=O)NS(=O)(=O)c2cccc(Oc3cc(F)cc(Cl)c3)n2)C(C)(C)C1] 2719
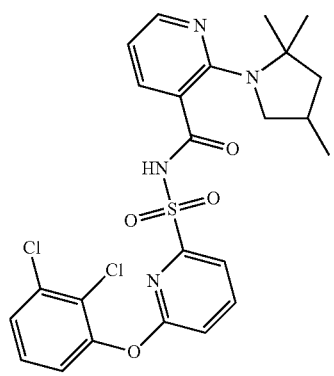 [SMILES: CC1CN(c2ncccc2C(=O)NS(=O)(=O)c2cccc(Oc3cccc(Cl)c3Cl)n2)C(C)(C)C1] 2720
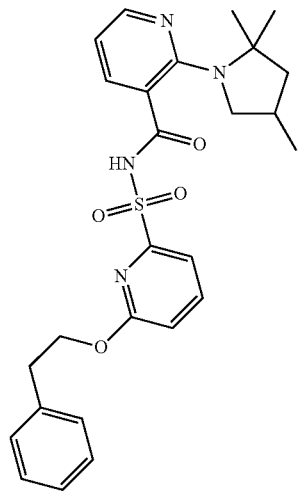 [SMILES: CC1CN(c2ncccc2C(=O)NS(=O)(=O)c2cccc(OCCc3ccccc3)n2)C(C)(C)C1] 2721

TABLE 1-continued
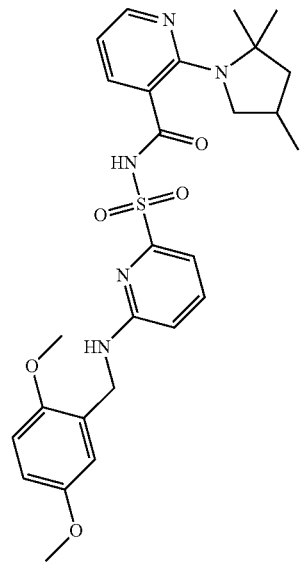 [SMILES: COc1ccc(OC)c(CNc2cccc(S(=O)(=O)NC(=O)c3cccnc3N3CC(C)CC3(C)C)n2)c1]
2722
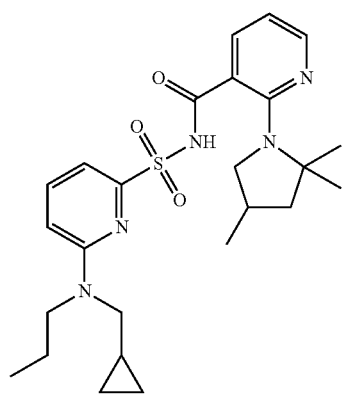 [SMILES: CCCN(CC1CC1)c1cccc(S(=O)(=O)NC(=O)c2cccnc2N2CC(C)CC2(C)C)n1]
2723
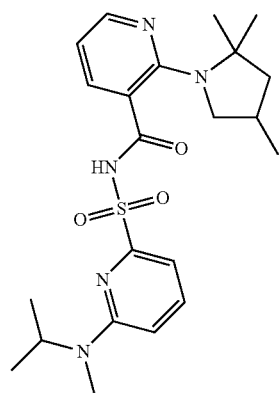 [SMILES: CC1CN(c2ncccc2C(=O)NS(=O)(=O)c2cccc(N(C)C(C)C)n2)C(C)(C)C1]
2724

TABLE 1-continued
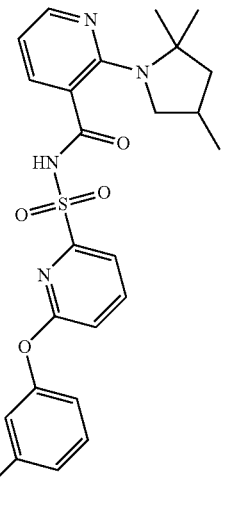
2725
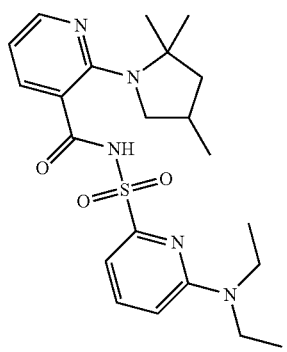 [SMILES: CCN(CC)c1cccc(S(=O)(=O)NC(=O)c2cccnc2N2CC(C)CC2(C)C)n1]
2726
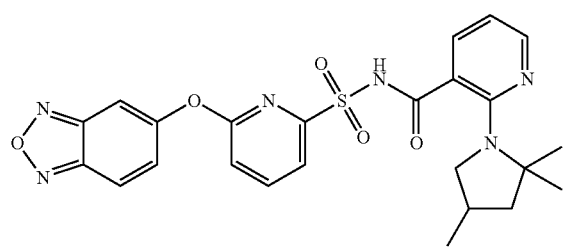 [SMILES: CC1CN(c2ncccc2C(=O)NS(=O)(=O)c2cccc(Oc3ccc4nonc4c3)n2)C(C)(C)C1]
2727
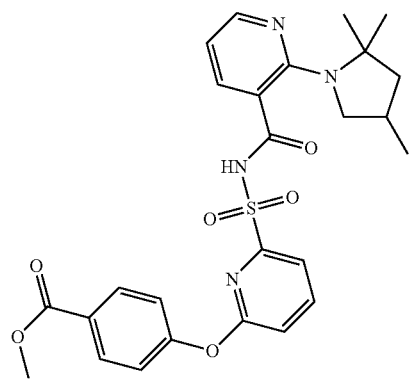 [SMILES: COC(=O)c1ccc(Oc2cccc(S(=O)(=O)NC(=O)c3cccnc3N3CC(C)CC3(C)C)n2)cc1]
2728

TABLE 1-continued
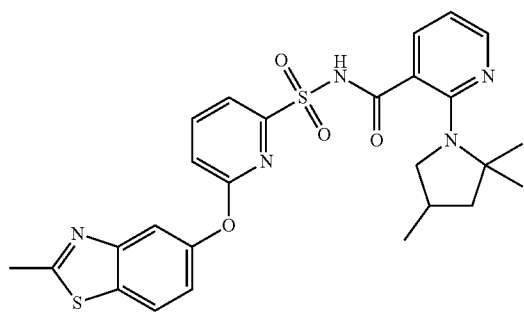
2729
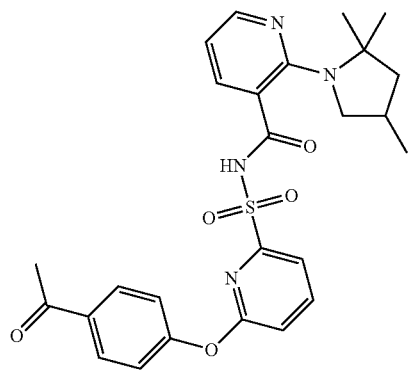 [SMILES: CC(=O)c1ccc(Oc2cccc(S(=O)(=O)NC(=O)c3cccnc3N3CC(C)CC3(C)C)n2)cc1]
2730
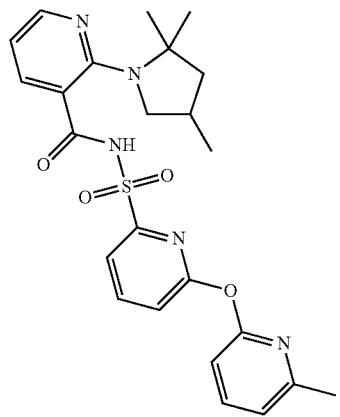 [SMILES: Cc1cccc(Oc2cccc(S(=O)(=O)NC(=O)c3cccnc3N3CC(C)CC3(C)C)n2)n1]
2731
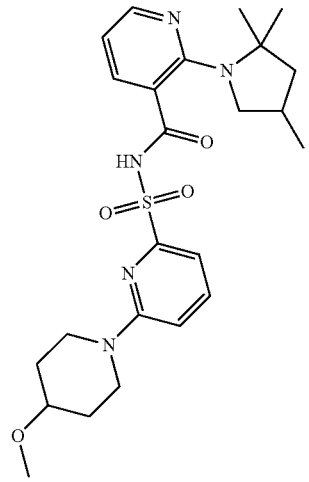 [SMILES: COC1CCN(c2cccc(S(=O)(=O)NC(=O)c3cccnc3N3CC(C)CC3(C)C)n2)CC1]
2732

TABLE 1-continued
| | |
|---|---|
| 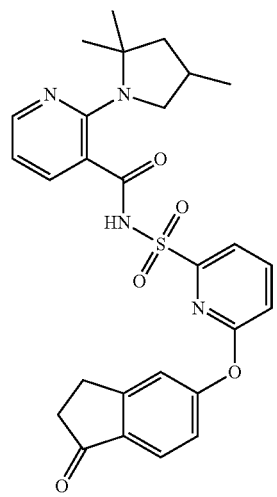 [SMILES: CC1CN(c2ncccc2C(=O)NS(=O)(=O)c2cccc(Oc3ccc4c(c3)CCC4=O)n2)C(C)(C)C1] | 2733 |
| 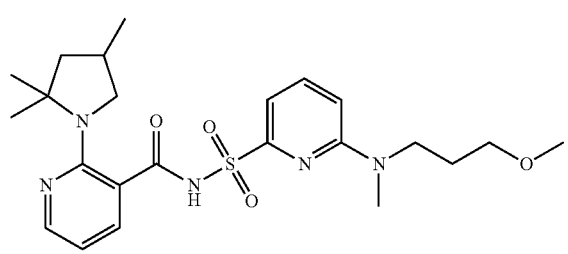 | 2734 |
| 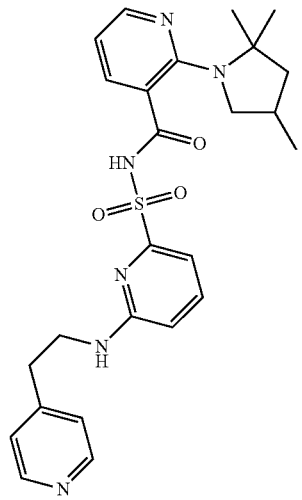 [SMILES: CC1CN(c2ncccc2C(=O)NS(=O)(=O)c2cccc(NCCc3ccncc3)n2)C(C)(C)C1] | 2735 |
| 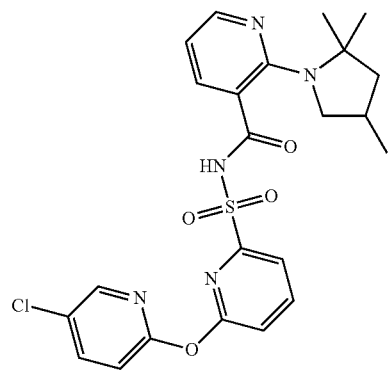 [SMILES: CC1CN(c2ncccc2C(=O)NS(=O)(=O)c2cccc(Oc3ccc(Cl)cn3)n2)C(C)(C)C1] | 2736 |

TABLE 1-continued
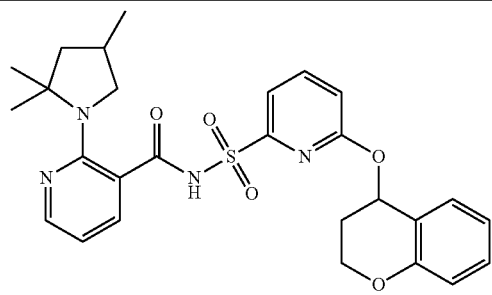
2737
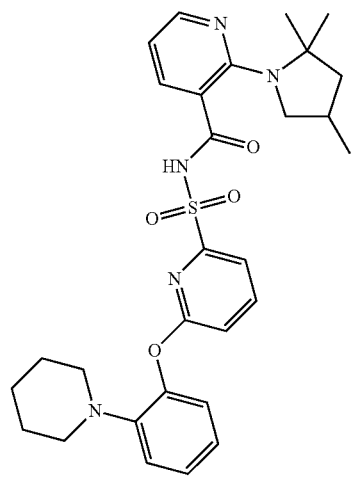 [SMILES: CC1CN(c2ncccc2C(=O)NS(=O)(=O)c2cccc(Oc3ccccc3N3CCCCC3)n2)C(C)(C)C1]
2738
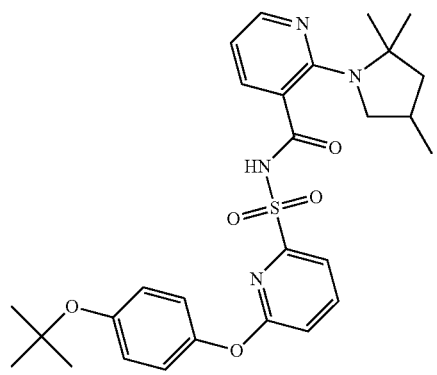 [SMILES: CC1CN(c2ncccc2C(=O)NS(=O)(=O)c2cccc(Oc3ccc(OC(C)(C)C)cc3)n2)C(C)(C)C1]
2739
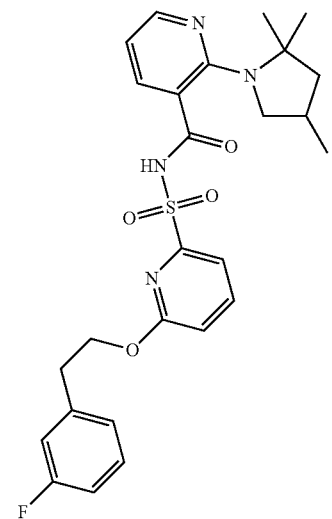 [SMILES: CC1CN(c2ncccc2C(=O)NS(=O)(=O)c2cccc(OCCc3cccc(F)c3)n2)C(C)(C)C1]
2740

TABLE 1-continued
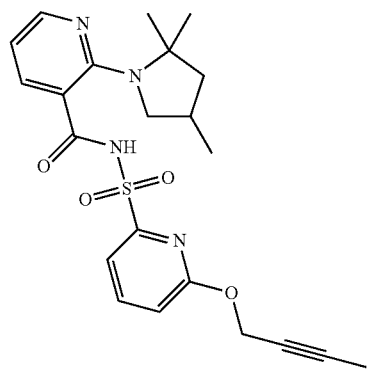 [SMILES: CC#CCOc1cccc(S(=O)(=O)NC(=O)c2cccnc2N2CC(C)CC2(C)C)n1] 2741
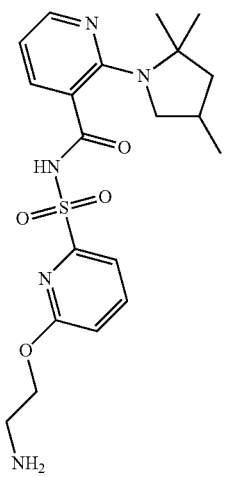 [SMILES: CC1CN(c2ncccc2C(=O)NS(=O)(=O)c2cccc(OCCN)n2)C(C)(C)C1] 2742
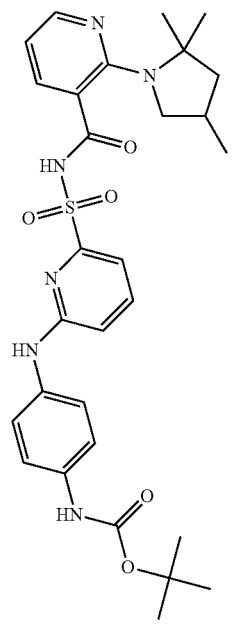 [SMILES: CC1CN(c2ncccc2C(=O)NS(=O)(=O)c2cccc(Nc3ccc(NC(=O)OC(C)(C)C)cc3)n2)C(C)(C)C1] 2743

TABLE 1-continued
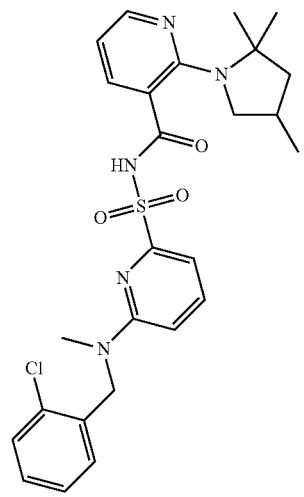 [SMILES: CC1CN(c2ncccc2C(=O)NS(=O)(=O)c2cccc(N(C)Cc3ccccc3Cl)n2)C(C)(C)C1]
2744
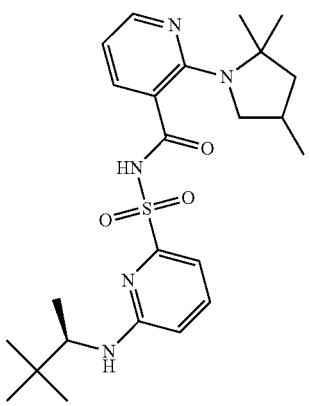 [SMILES: CC1CN(c2ncccc2C(=O)NS(=O)(=O)c2cccc(N[C@H](C)C(C)(C)C)n2)C(C)(C)C1]
2745
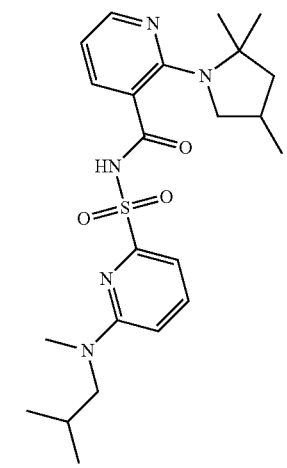 [SMILES: CC(C)CN(C)c1cccc(S(=O)(=O)NC(=O)c2cccnc2N2CC(C)CC2(C)C)n1]
2746

TABLE 1-continued

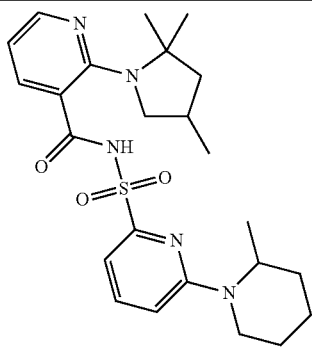

2747

In one embodiment, the present invention features any of the below numerated embodiments.

1. In one embodiment, the present invention features a compound of formula I:

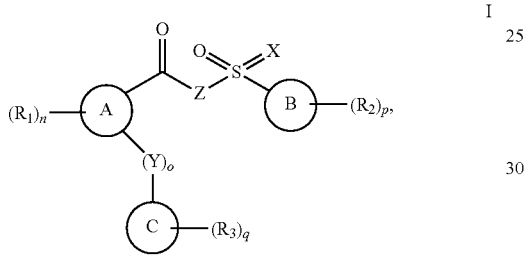

or pharmaceutically acceptable salt thereof, wherein, independently for each occurrence:

Ring A is a C6-C10 mono- or bicyclic aryl ring, or C5-C10 mono- or bicyclic heteroaryl or heterocyclic ring wherein up to 4 carbon atoms may be replaced by O, S, N, or NR;

Ring B is a C6-C10 aryl ring or C5-C10 heteroaryl or heterocyclic ring wherein up to 4 carbon atoms may be replaced by O, S, N, or NR;

Ring C is a C6-C10 mono- or bicyclic aryl ring, C4-C10 mono- or bicyclic heteroaryl or heterocyclic ring wherein anywhere from 1 to 4 carbon atoms may be replaced by N, O, or S, or a C3-C10 mono- or bicyclic cycloalkyl ring;

X is O or NR;

Y is $CR_2$, O, S, SO, $SO_2$, or NR;

Z is NR or $CR_2$;

$R_1$ is halo, CN, C1-C6 alkyl or fluoroalkyl, C1-C6 alkoxy or fluoroalkoxy, (C1-C8 alkyl)-$R_4$ wherein up to three $CH_2$ units may be replaced with O, CO, S, SO, $SO_2$ or NR; C6-C10 mono- or bicyclic aryl, C5-C10 mono- or bicyclic heteroaryl or heterocyclic ring wherein up to 4 carbon atoms may be replaced with O, S, N, or NR; or C3-C8 cycloalkyl, all four of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced with O, S, or NR; or a (C1-C8 alkyl)-$R_4$ wherein up to three $CH_2$ units may be replaced with O, CO, S, SO, $SO_2$ or NR; or two $R_1$ along with the atoms to which they are attached form a C5-C8 cyclic or heterocyclic ring wherein up to 2 carbon atoms may be replaced with O, S, or NR;

$R_2$ is halo, OH, amino, azide, CN, C1-C6 alkyl or fluoroalkyl, C1-C6 alkoxy or fluoroalkoxy, C6-C10 mono- or bicyclic aryl, C5-C10 mono- or bicyclic heteroaryl or heterocyclic ring wherein up to 4 carbon atoms may be replaced with O, S, N, or NR, C3-C8 cycloalkyl; or a (C1-C8 alkyl)-$R_4$ wherein up to three $CH_2$ units may be replaced with O, CO, S, SO, $SO_2$ or NR;

$R_3$ is halo, CN, $CO_2R$, C1-C6 alkyl, alkene, alkyne, or fluoroalkyl; C1-C6 alkoxy, cycloalkoxy, or fluoroalkoxy; C6-C10 mono- or bicyclic aryl or C5-C10 mono- or bicyclic heteroaryl wherein up to 4 carbon atoms may be replaced by O, S, N, or NR, both of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced by O, S, or NR; or or a (C1-C8 alkyl)-$R_4$ wherein up to three $CH_2$ units may be replaced with O, CO, S, SO, $SO_2$ or NR; or two $R_3$ may form a $=CH_2$ or $=O$ group;

$R_4$ is H, $CF_3$, $CO_2R$, OH, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR; $N(R)_2$, NRCOR, $CON(R)_2$, CN, halo, or $SO_2R$;

R is H, OH, C1-C6 alkyl, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR;

n is 0, 1, 2 or 3;

o is 0, 1, 2, or 3;

p is 0, 1, 2, or 3; and q is 0, 1, 2, 3, 4, or 5;

provided that the moieties containing ring B and ring C are substituted at adjacent positions on ring A.

2. In another embodiment, the present invention features the compound of embodiment 1, wherein ring A is a pyridyl, indole, indoline, isoindoline, pyrazole, pyrimidine, phenyl, quinoline, 5,6,7,8-tetrahydroquinoline, 1,2,3,4-tetrahydroisoquinoline, pyrrolidine, aza-indole, pyrrole, oxazole, pyrazine, triazole, benzimidazole, indazole, or imidazole ring.

3. In another embodiment, the present invention features the compound of embodiment 1 or 2, wherein ring A is selected from

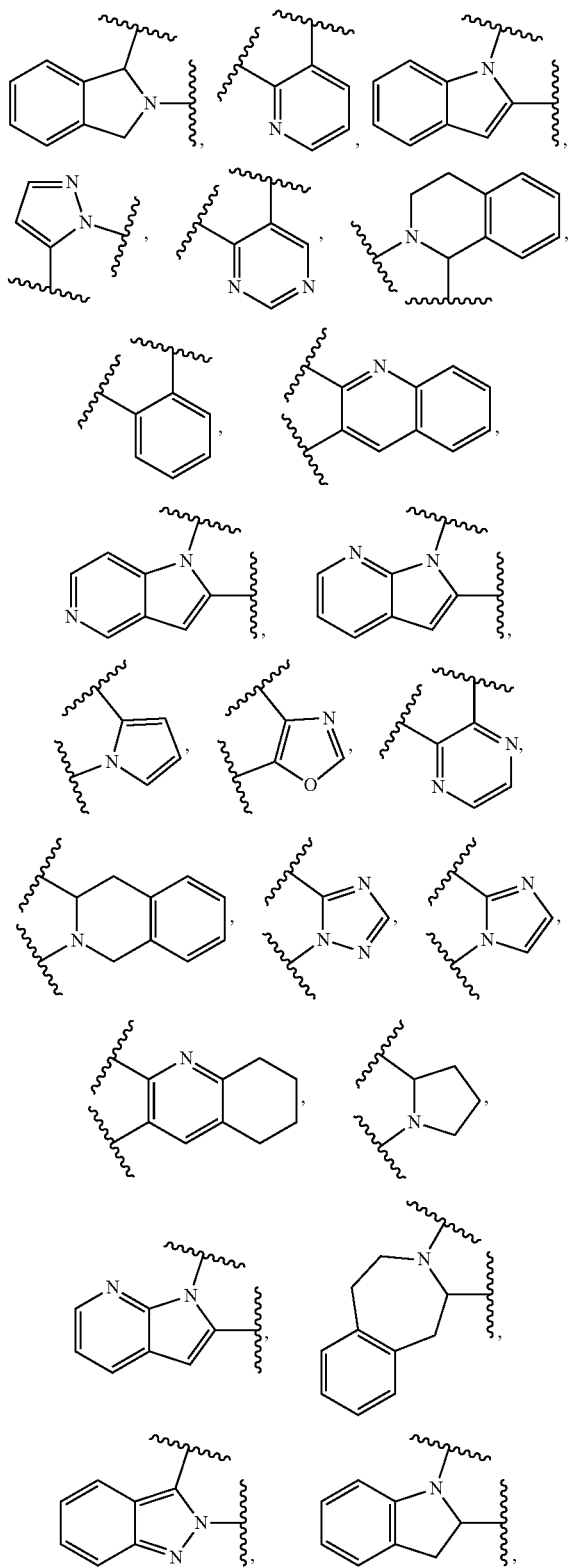

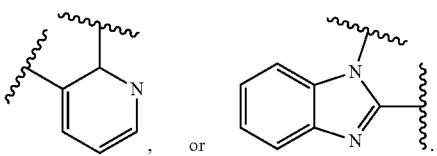 [SMILES: *C1=CC=CNC1* ; *c1nc2ccccc2n1*]

4. In another embodiment, the present invention features the compound of any of embodiments 1 to 3, wherein ring B is phenyl, pyridyl, pyridine-2 (1H)-one, pyrazole, indole, thiophene, dihydrobenzofuran, pyrazine, indazole, thiazole, pyridine-4 (1H)-one, pyrrolidinone, or quinoline.

5. In another embodiment, the present invention features the compound of any of embodiments 1 to 4, wherein ring B is selected from

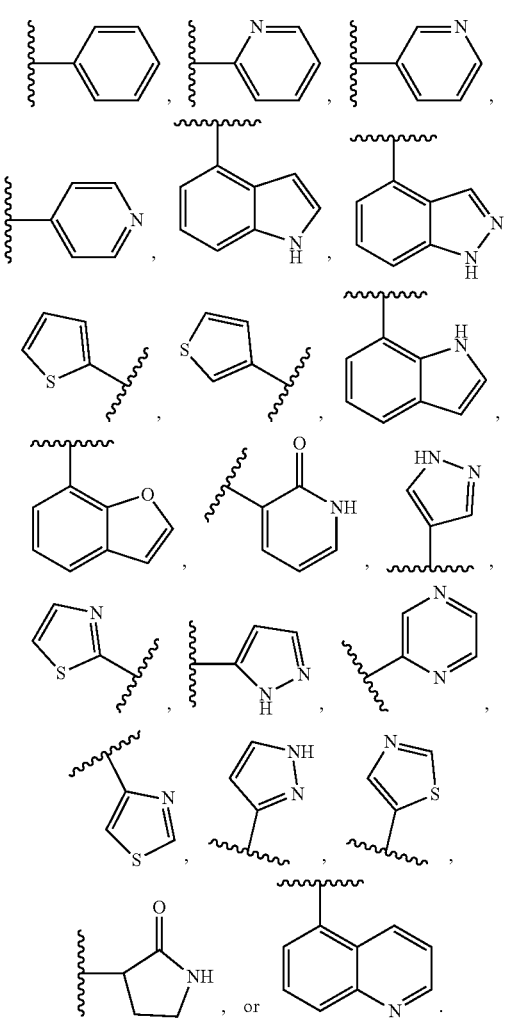

6. In another embodiment, the present invention features the compound of any of embodiments 1 to 5, wherein ring C is phenyl, indole, cycloalkyl, pyridyl, pyrrolidine, naphthalene, piperidine, azetidine, or dihydroindene.

7. In another embodiment, the present invention features the compound of any of embodiments 1 to 6, wherein ring C is

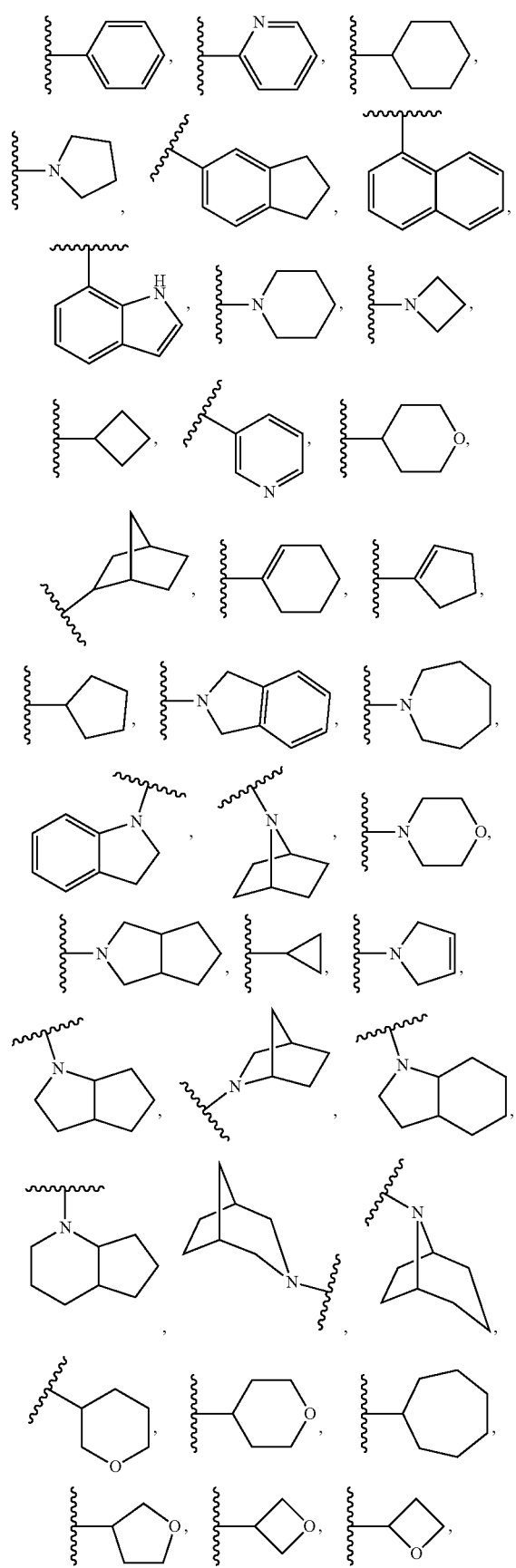

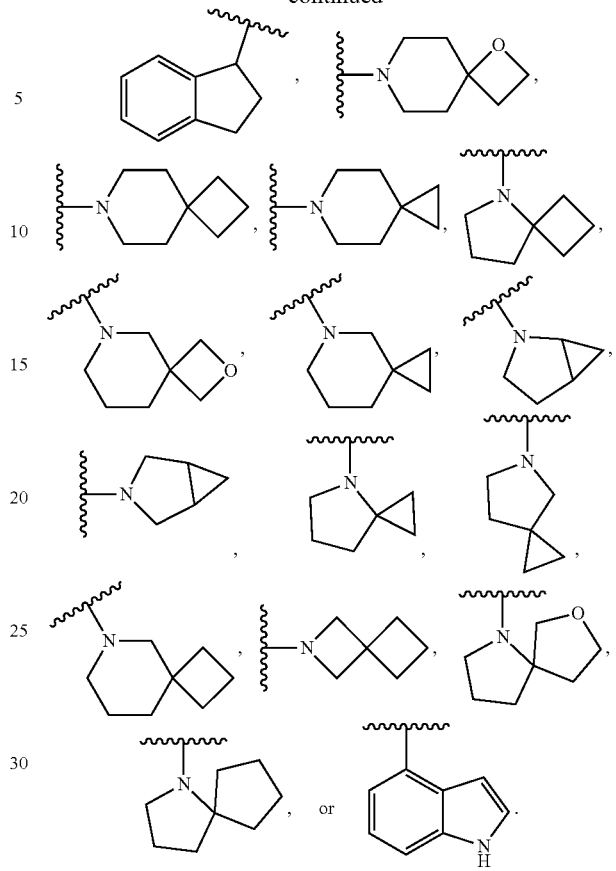

8. In another embodiment, the present invention features the compound of any of embodiments 1 to 7, wherein Y is O.

9. In another embodiment, the present invention features the compound of any of embodiments 1 to 7, wherein Y is $CH_2$.

10. In another embodiment, the present invention features the compound of any of embodiments 1 to 7, wherein Y is CH(C1-C6 alkyl).

11. In another embodiment, the present invention features the compound of any of embodiments 1 to 7, wherein Y is $CH(CH_3)$.

12. In another embodiment, the present invention features the compound of any of embodiments 1 to 7, wherein Y is $CH(CH_2CH_3)$.

13. In another embodiment, the present invention features the compound of any of embodiments 1 to 7, wherein Y is N(C1-C6 alkyl).

14. In another embodiment, the present invention features the compound of any of embodiments 1 to 7, wherein Y is $N(CH_3)$.

15. In another embodiment, the present invention features the compound of any of embodiments 1 to 14, wherein $R_1$ is halo, CN, C1-C6 alkyl, C1-C6 alkoxy, C3-C8 cycloalkyl, or a phenyl, pyridyl, pyrimidine, indole, aza-indole, azetidine, or thiophene ring, wherein all rings may be substituted with halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C5-C10 heteroaryl, C5-C10 heterocycloalkyl, or a (C1-C8 alkyl)-$R_4$ wherein up to three $CH_2$ units may be replaced with O, CO, S, SO, $SO_2$ or NR.

16. In another embodiment, the present invention features the compound of any of embodiments 1 to 15, wherein $R_1$ is selected from $CH_3$, Cl, F, CN, $OCH_3$, $CF_3$, $CH_2CH_3$, tBu, $CH(CH_3)_2$,
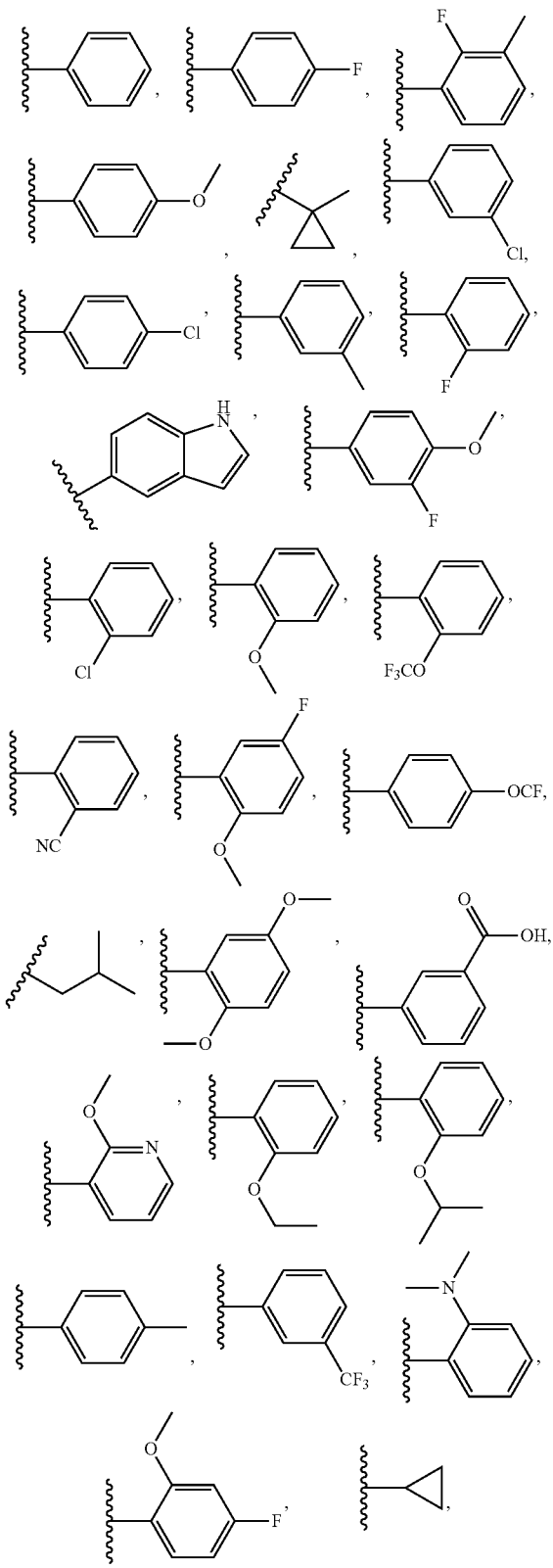
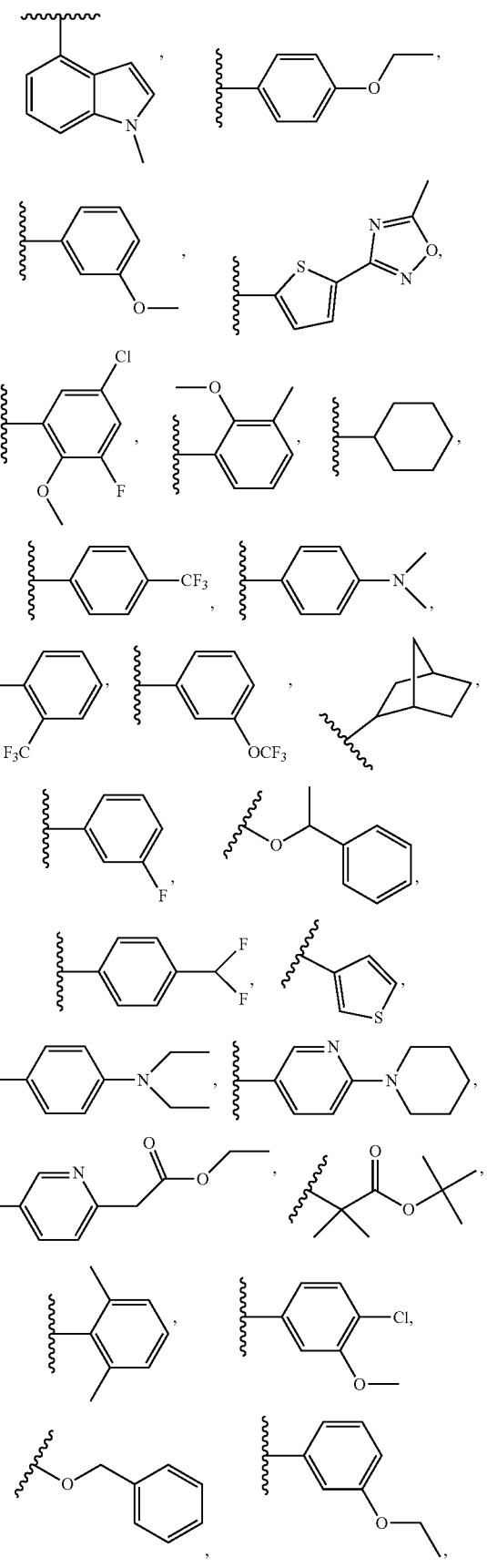

1691
-continued
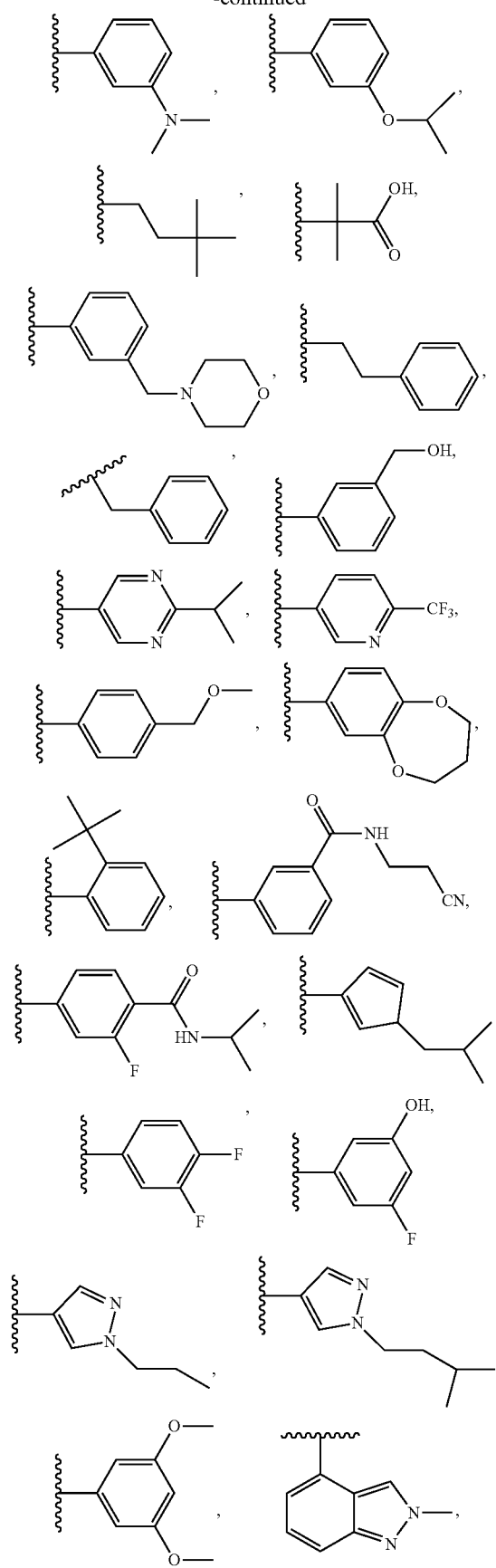
1692
-continued
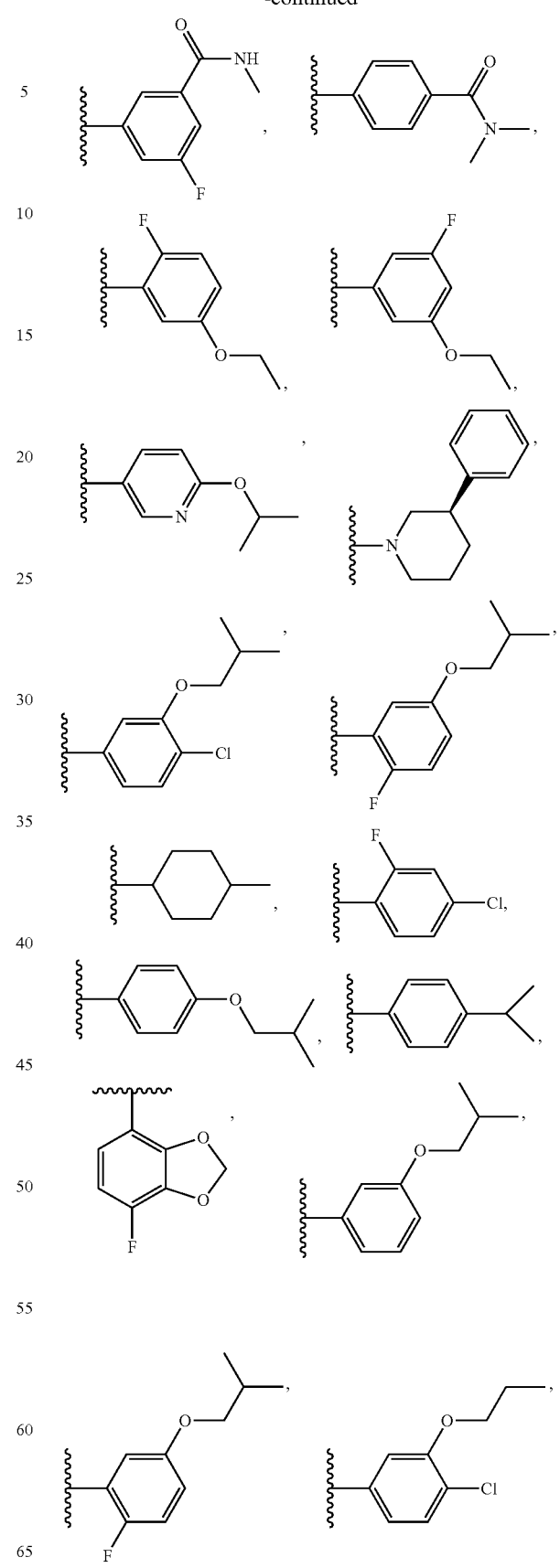

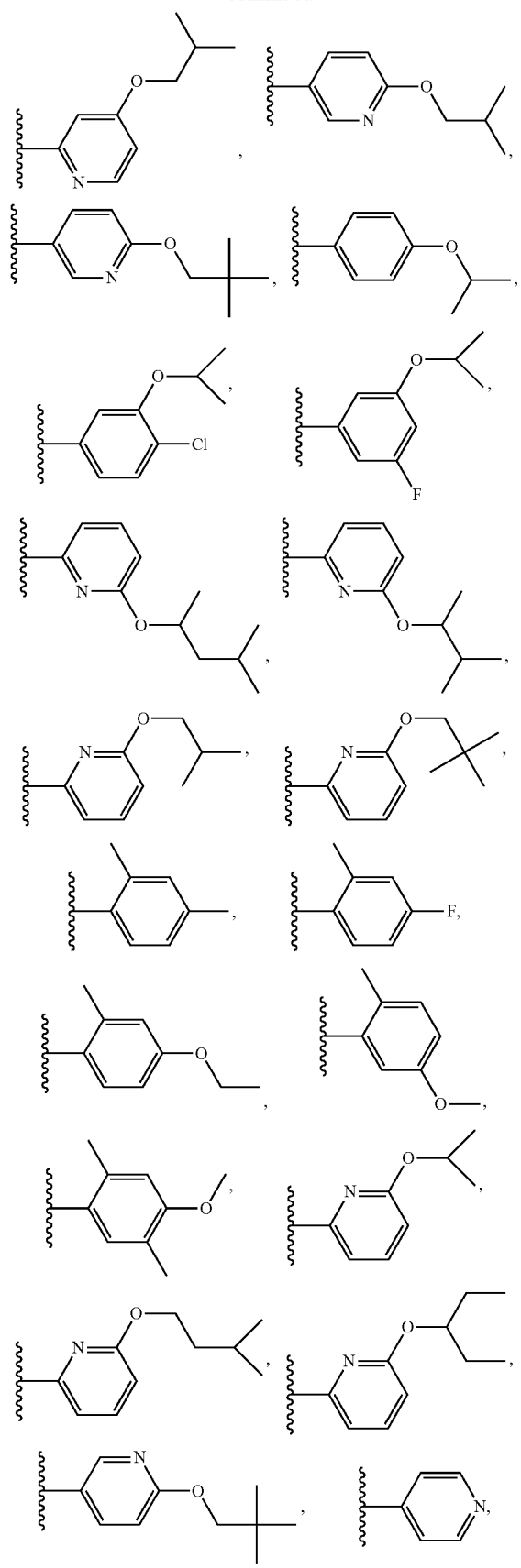

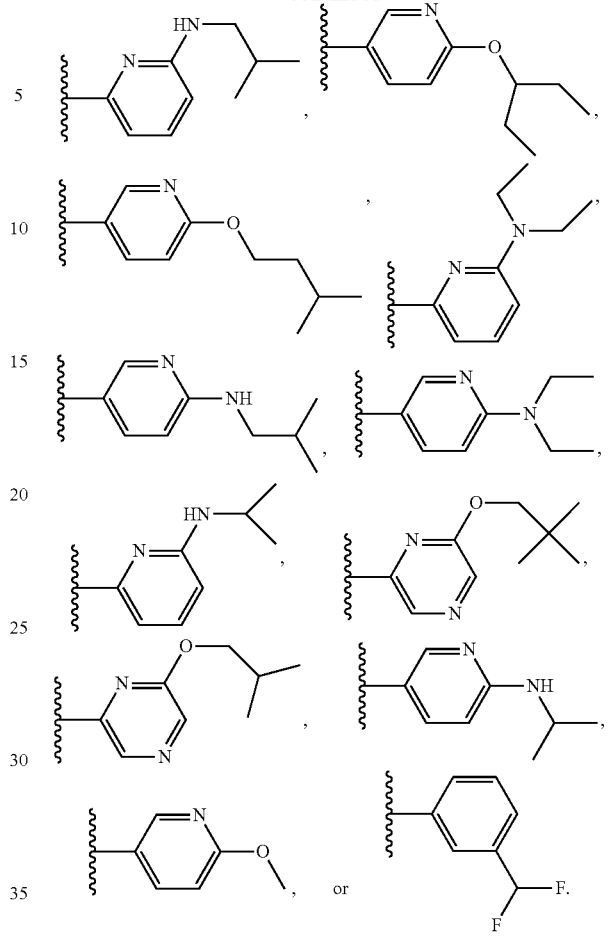

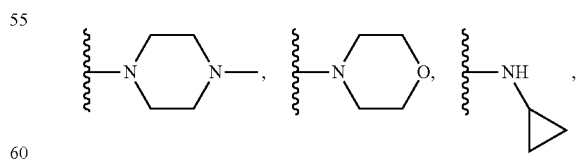

17. In another embodiment, the present invention features the compound of any of embodiments 1 to 16, wherein $R_2$ is selected from halo, OH, CN, azide, amino, C1-C6 alkyl or fluoroalkyl, C1-C6 alkoxy or fluoroalkoxy, C5-C10 mono- or bicyclic heterocyclic ring wherein up to 4 carbon atoms may be replaced with O, S, N, or NR; or a (C1-C8 alkyl)-$R_4$ wherein up to three $CH_2$ units may be replaced with O, CO, S, SO, $SO_2$ or NR.

18. In another embodiment, the present invention features the compound of any of embodiments 1 to 17, wherein $R_2$ is selected from Cl, F, OH, CN, $N_3$, $NH_2$, $NH(CH_3)$, $N(CH_3)_2$, $CH_3$, $CH_2OH$, $CH_2CH_3$, $CH(CH_3)_2$, $CHF_2$, $OCH_3$, $OCF_3$, $OCHF_2$, $OCH(CH_3)_2$, $C(O)CH_3$, $CH_2CH_2OH$, $CH_2NH_2$, $NH(CH_2)_2OH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$, 19. In another embodiment, the present invention features the compound of any of embodiments 1 to 18, wherein $R_3$ is selected from halo, CN, C1-C6 alkyl or fluoroalkyl, C1-C6 alkoxy, or C5-C10 mono- or bicyclic heteroaryl or heterocycloalkyl wherein up to 4 carbon atoms may be replaced by O, S, N, or NR.

20. In another embodiment, the present invention features the compound of any of embodiments 1 to 19, wherein $R_3$ is selected from Cl, F, CN, $CH_3$, $OCH_3$, $CF_3$, $CH_2CH_3$, $CH_2CF_3$, $CH_2CH_2CH_3$, $OCH_2CH_3$, $CH_2OCH_3$, $CH(CH_3)_2$, CCH, $CO_2CH_3$, tBu, $=CH_2$, $=O$,

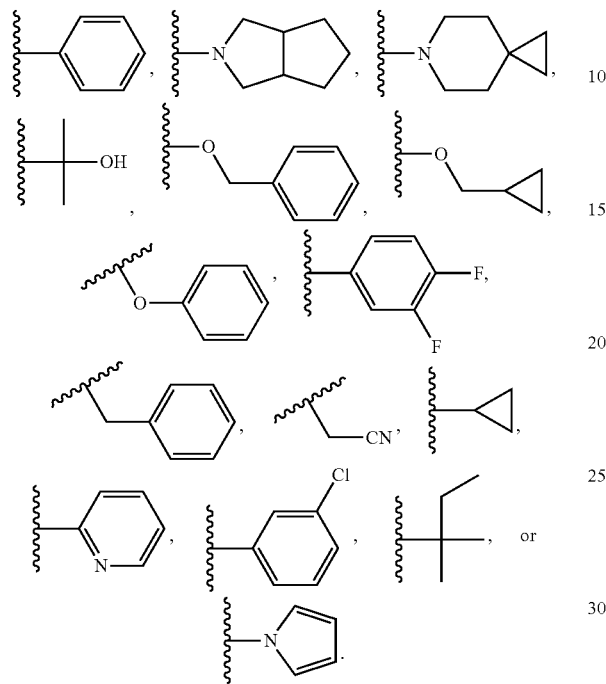

21. In another embodiment, the present invention features the compound of any of embodiments 1 to 20, wherein o is 0.

22. In another embodiment, the present invention features the compound of any of embodiments 1 to 20, wherein o is 1.

23. In another embodiment, the present invention features the compound of any of embodiments 1 to 20, wherein o is 2.

24. In another embodiment, the present invention features the compound of any of embodiments 1 to 23, wherein n is 0.

25. In another embodiment, the present invention features the compound of any of embodiments 1 to 23, wherein n is 1.

26. In another embodiment, the present invention features the compound of any of embodiments 1 to 23, wherein n is 2.

27. In another embodiment, the present invention features the compound of any of embodiments 1 to 26, wherein p is 0.

28. In another embodiment, the present invention features the compound of any of embodiments 1 to 26, wherein p is 1.

29. In another embodiment, the present invention features the compound of any of embodiments 1 to 26, wherein p is 2.

30. In another embodiment, the present invention features the compound of embodiment 1, wherein the compound is of formula Ia:

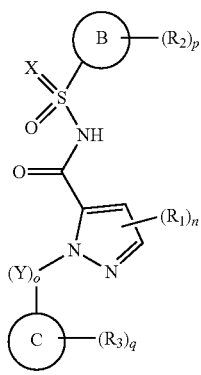

or pharmaceutically acceptable salt thereof, wherein, independently for each occurrence:

Ring B is a C6-C10 aryl ring or C5-C10 heteroaryl or heterocyclic ring wherein up to 4 carbon atoms may be replaced by O, S, N, or NR;

Ring C is a C6-C10 mono- or bicyclic aryl ring, C5-C10 mono- or bicyclic heteroaryl or heterocyclic ring wherein anywhere from 1 to 4 carbon atoms may be replaced by N, O, or S, or a C3-C10 mono- or bicyclic cycloalkyl ring;

X is O or NR;

Y is $CR_2$, O, S, SO, $SO_2$, or NR;

$R_1$ is halo, CN, C1-C6 alkyl or fluoroalkyl, C1-C6 alkoxy or fluoroalkoxy, (C1-C8 alkyl)-$R_4$ wherein up to three $CH_2$ units may be replaced with O, CO, S, SO, $SO_2$ or NR; C6-C10 mono- or bicyclic aryl, C5-C10 mono- or bicyclic heteroaryl or heterocyclic ring wherein up to 4 carbon atoms may be replaced with O, S, N, or NR; or C3-C8 cycloalkyl, all four of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced with O, S, or NR; or a (C1-C8 alkyl)-$R_4$ wherein up to three $CH_2$ units may be replaced with O, CO, S, SO, $SO_2$ or NR; or two $R_1$ along with the atoms to which they are attached form a C5-C8 cyclic or heterocyclic ring wherein up to 2 carbon atoms may be replaced with O, S, or NR;

$R_2$ is halo, OH, amino, azide, CN, C1-C6 alkyl or fluoroalkyl, C1-C6 alkoxy or fluoroalkoxy, C6-C10 mono- or bicyclic aryl, C5-C10 mono- or bicyclic heteroaryl or heterocyclic ring wherein up to 4 carbon atoms may be replaced with O, S, N, or NR, C3-C8 cycloalkyl; or a (C1-C8 alkyl)-$R_4$ wherein up to three $CH_2$ units may be replaced with O, CO, S, SO, $SO_2$ or NR;

$R_3$ is halo, CN, $CO_2R$, C1-C6 alkyl, alkene, alkyne, or fluoroalkyl; C1-C6 alkoxy, cycloalkoxy, or fluoroalkoxy; C6-C10 mono- or bicyclic aryl or C5-C10 mono- or bicyclic heteroaryl wherein up to 4 carbon atoms may be replaced by O, S, N, or NR, both of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced by O, S, or NR; or or a (C1-C8 alkyl)-$R_4$ wherein up to three CH$_2$ units may be replaced with O, CO, S, SO, SO$_2$ or NR; or two R$_3$ may form a =CH$_2$ or =O group;

R$_4$ is H, CF$_3$, CO$_2$R, OH, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR; N(R)$_2$, NRCOR, CON(R)$_2$, CN, halo, or SO$_2$R;

R is H, OH, C1-C6 alkyl, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR;

n is 0, 1, 2 or 3;
o is 0, 1, 2, or 3;
p is 0, 1, 2, or 3; and
q is 0, 1, 2, 3, 4, or 5.

31. In another embodiment, the present invention features a compound of embodiment 30, wherein ring B is phenyl, pyridyl, pyridine-2 (1H)-one, pyrazole, indole, thiophene, dihydrobenzofuran, pyrazine, indazole, thiazole, pyridine-4 (1H)-one, pyrrolidinone, or quinoline.

32. In another embodiment, the present invention features a compound of embodiment 30 or 31, wherein ring B is selected from 33. In another embodiment, the present invention features a compound of any of embodiments 30 to 32, wherein ring C is phenyl, indole, cycloalkyl, pyridyl, pyrrolidine, naphthalene, piperidine, or dihydroindene.

34. In another embodiment, the present invention features a compound of any of embodiments 30 to 33, wherein ring C is

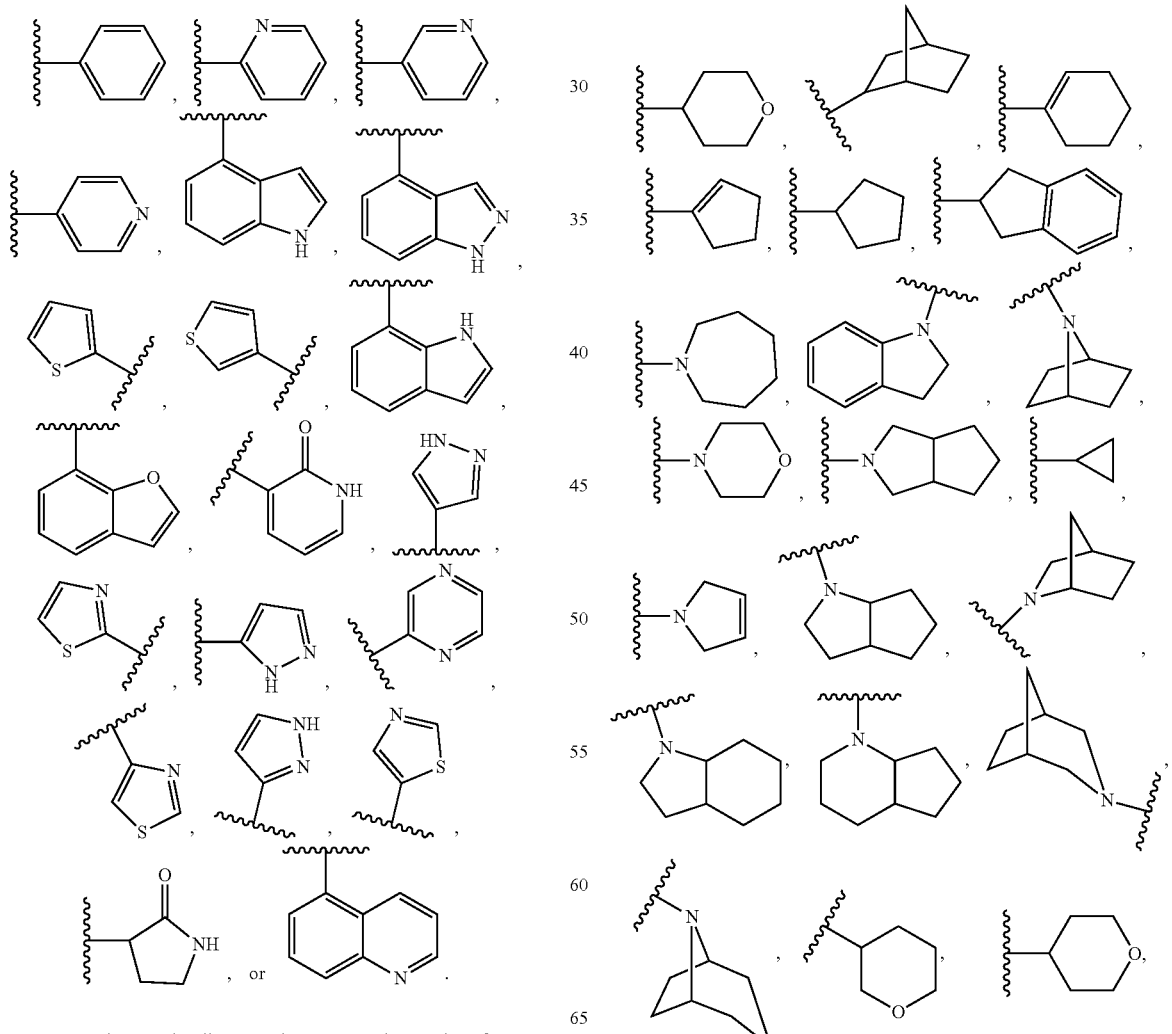

-continued

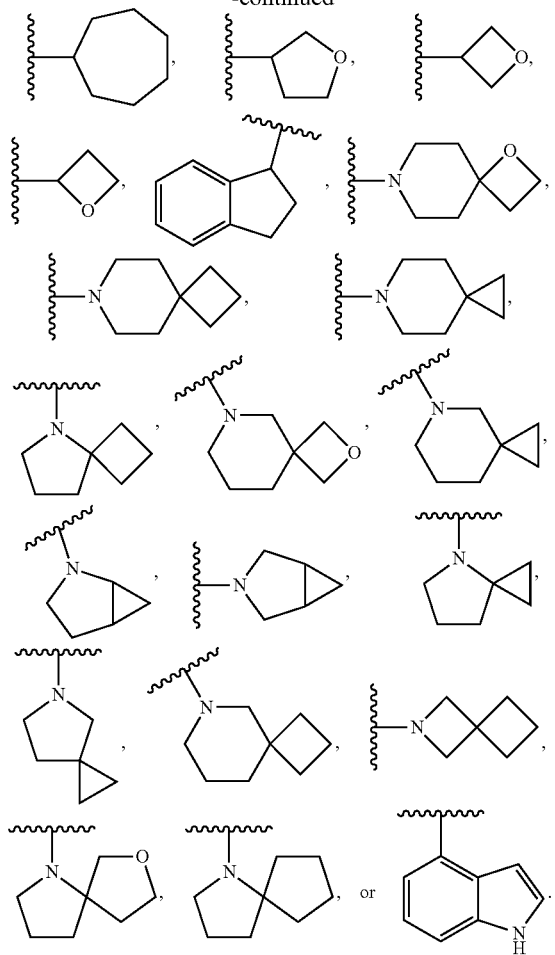

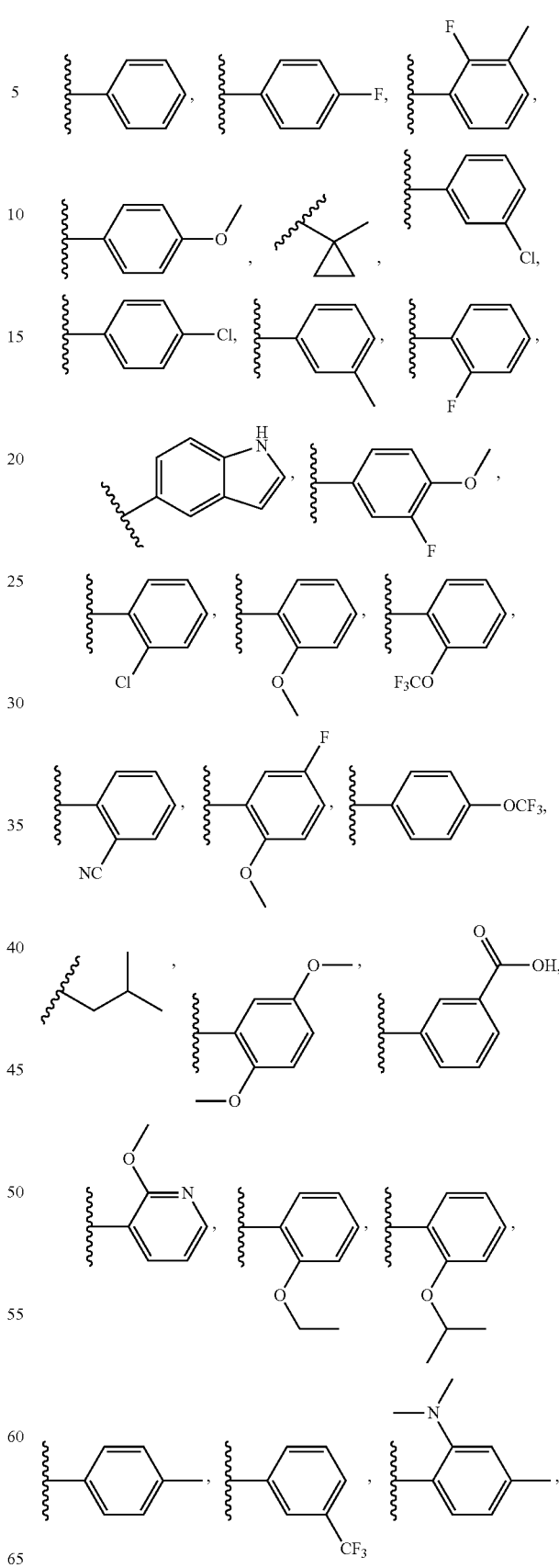

35. In another embodiment, the present invention features a compound of any of embodiments 30 to 34, wherein Y is O.

36. In another embodiment, the present invention features a compound of any of embodiments 30 to 34, wherein Y is $CH_2$.

37. In another embodiment, the present invention features a compound of any of embodiments 30 to 34, wherein Y is CH(C1-C6 alkyl).

38. The compound of claim 30, wherein Y is $CH(CH_3)$.

39. In another embodiment, the present invention features a compound of any of embodiments 30 to 34, wherein Y is $CH(CH_2CH_3)$.

40. In another embodiment, the present invention features a compound of any of embodiments 30 to 39, wherein $R_1$ is halo, CN, C1-C6 alkyl, C1-C6 alkoxy, C3-C8 cycloalkyl, or a phenyl, pyridyl, pyrimidine, indole, aza-indole, or thiophene ring, wherein all rings may be substituted with halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C5-C10 heteroaryl, C5-C10 heterocycloalkyl, or a (C1-C8 alkyl)-$R_4$ wherein up to three $CH_2$ units may be replaced with O, CO, S, SO, $SO_2$ or NR.

41. In another embodiment, the present invention features a compound of any of embodiments 30 to 40, wherein $R_1$ is selected from $CH_3$, Cl, F, CN, $OCH_3$, $CF_3$, $CH_2CH_3$, tBu, $CH(CH_3)_2$,

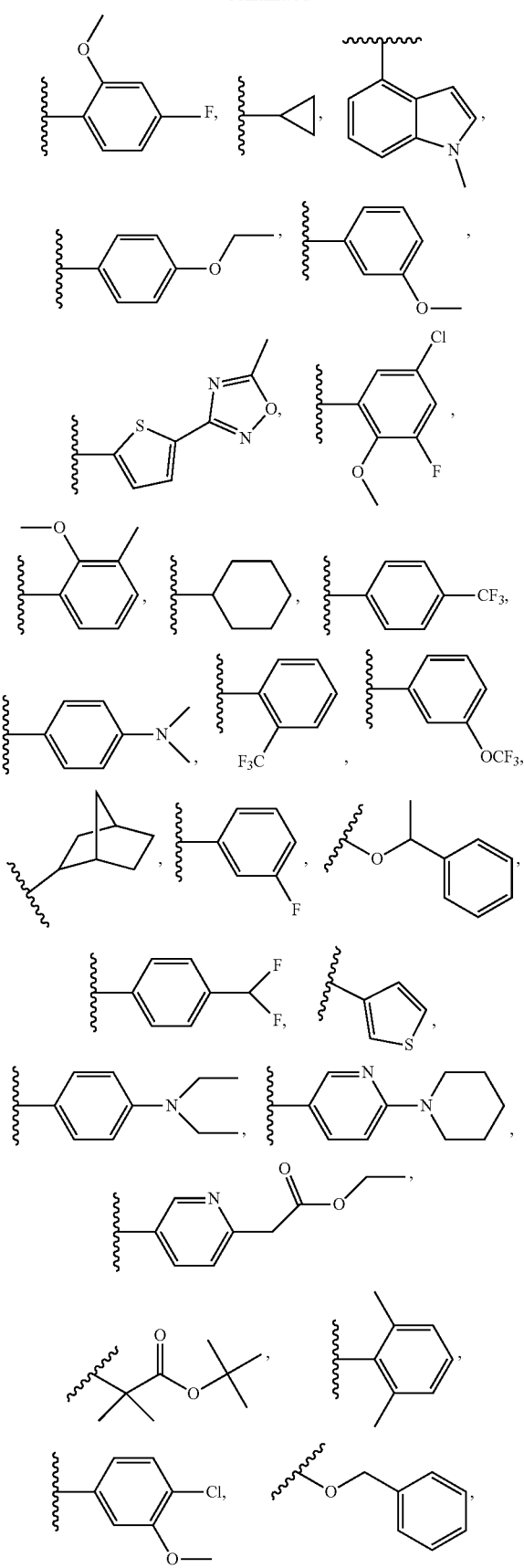
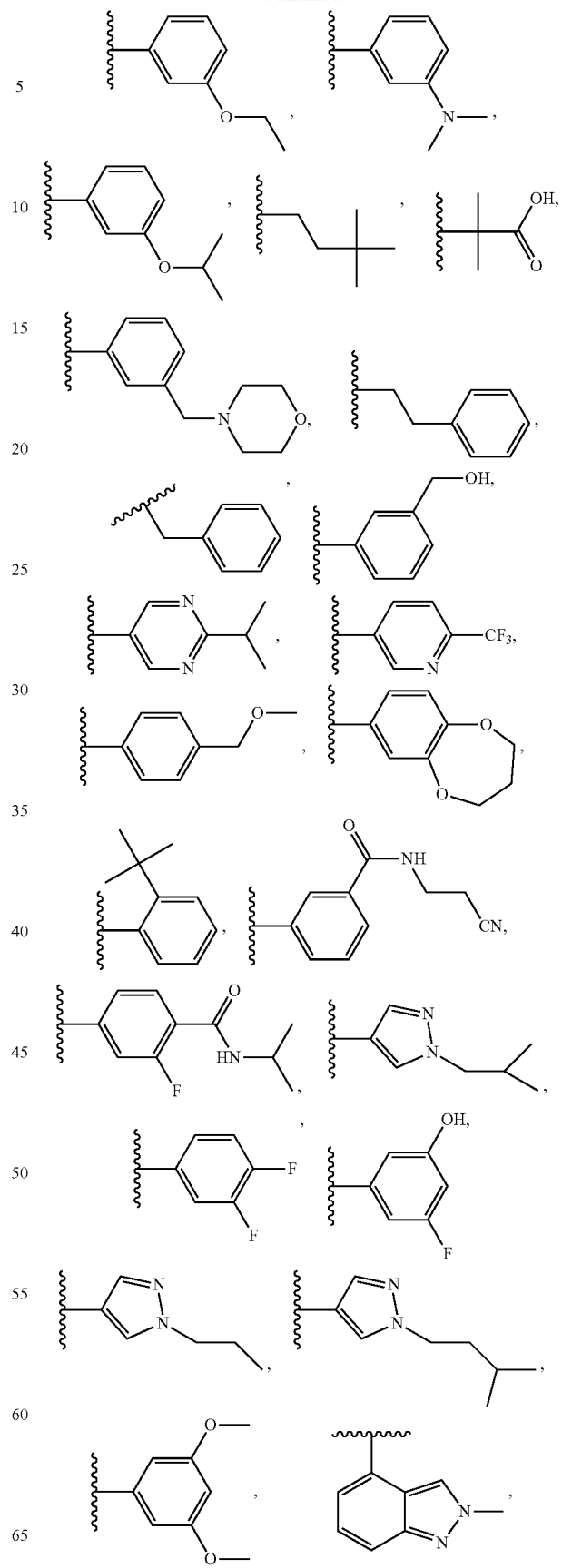

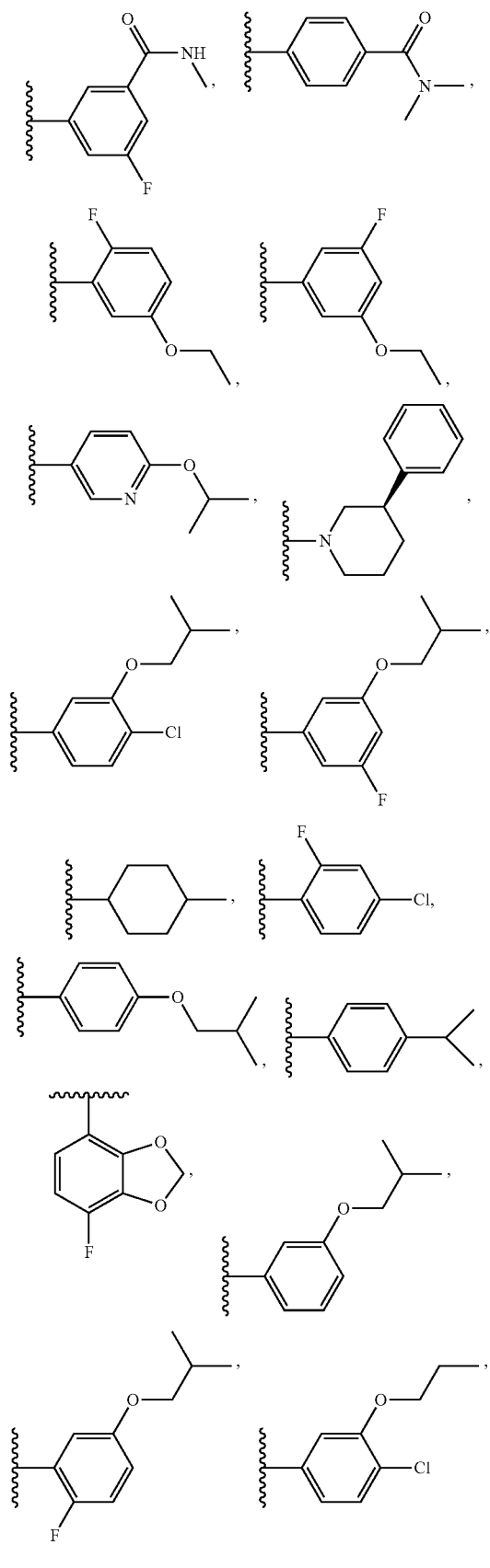
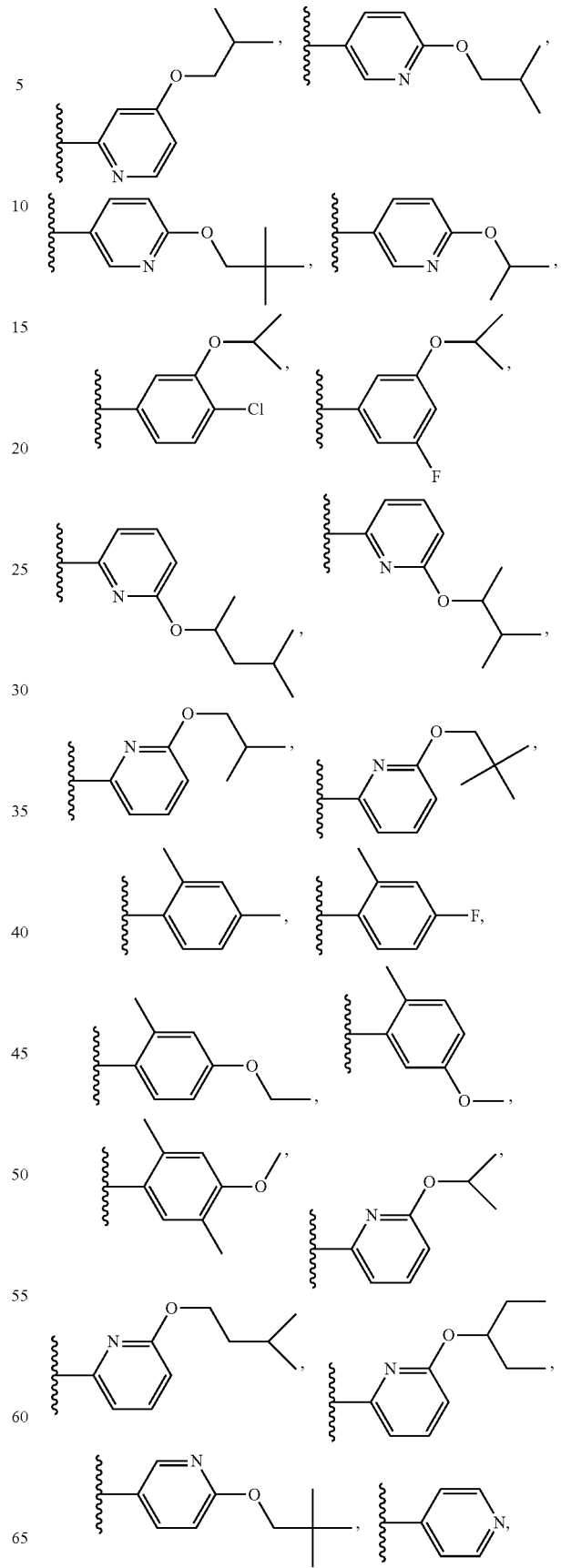

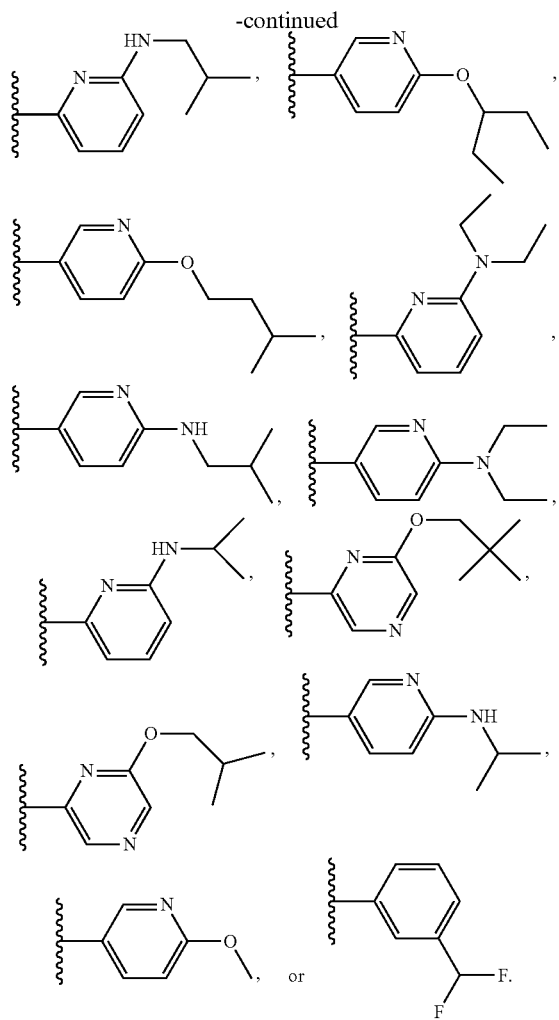

42. In another embodiment, the present invention features a compound of any of embodiments 30 to 41, wherein $R_2$ is selected from halo, OH, CN, azide, amino, C1-C6 alkyl or fluoroalkyl, C1-C6 alkoxy or fluoroalkoxy, C5-C10 mono- or bicyclic heterocyclic ring wherein up to 4 carbon atoms may be replaced with O, S, N, or NR; or a (C1-C8 alkyl)-$R_4$ wherein up to three $CH_2$ units may be replaced with O, CO, S, SO, $SO_2$ or NR.

43. In another embodiment, the present invention features a compound of any of embodiments 30 to 42, wherein $R_2$ is selected from Cl, F, OH, CN, $N_3$, $NH_2$, $NH(CH_3)$, $N(CH_3)_2$, $CH_3$, $CH_2OH$, $CH_2CH_3$, $CH(CH_3)_2$, $CHF_2$, $OCH_3$, $OCF_3$, $OCHF_2$, $OCH(CH_3)_2$, $C(O)CH_3$, $CH_2CH_2OH$, $CH_2NH_2$, $NH(CH_2)_2OH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

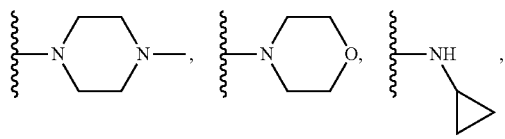

or $CO_2H$.

44. In another embodiment, the present invention features a compound of any of embodiments 30 to 43, wherein $R_3$ is selected from halo, CN, C1-C6 alkyl or fluoroalkyl, C1-C6 alkoxy, or C5-C10 mono- or bicyclic heteroaryl wherein up to 4 carbon atoms may be replaced by O, S, N, or NR.

45. In another embodiment, the present invention features a compound of any of embodiments 30 to 44, wherein $R_3$ is selected from Cl, F, CN, $CH_3$, $OCH_3$, $CF_3$, $CH_2CH_3$, $CH_2CF_3$, $CH_2CH_2CH_3$, $OCH_2CH_3$, $CH_2OCH_3$, $CH(CH_3)_2$, CCH, $CO_2CH_3$, tBu, $CH_2$, =O,

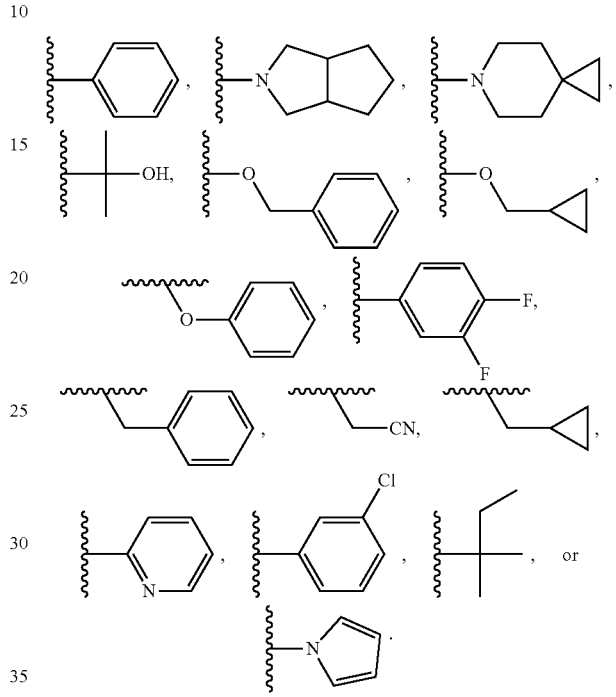

46. In another embodiment, the present invention features a compound of any of embodiments 30 to 45, wherein o is 0.

47. In another embodiment, the present invention features a compound of any of embodiments 30 to 45, wherein o is 1.

48. In another embodiment, the present invention features a compound of any of embodiments 30 to 47, wherein n is 0.

49. In another embodiment, the present invention features a compound of any of embodiments 30 to 47, wherein n is 1.

50. In another embodiment, the present invention features a compound of any of embodiments 30 to 47, wherein n is 2.

51. In another embodiment, the present invention features a compound of any of embodiments 30 to 50, wherein p is 0.

52. In another embodiment, the present invention features a compound of any of embodiments 30 to 50, wherein p is 1.

53. In another embodiment, the present invention features a compound of any of embodiments 30 to 50, wherein p is 2.

54. In another embodiment, the present invention features a compound of any of embodiments 30 to 53, wherein ring B is phenyl.

55. In another embodiment, the present invention features a compound of any of embodiments 30 to 54, wherein ring B and ring C are phenyl.

56. In another embodiment, the present invention features a compound of embodiment 1, wherein the compound is of formula Ib:

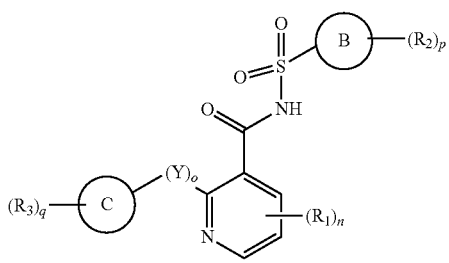

Ib or pharmaceutically acceptable salt thereof, wherein, independently for each occurrence:

Ring B is a C6-C10 aryl ring or C5-C10 heteroaryl or heterocyclic ring wherein up to 4 carbon atoms may be replaced by O, S, N, or NR;

Ring C is a C6-C10 mono- or bicyclic aryl ring, C5-C10 mono- or bicyclic heteroaryl or heterocyclic ring wherein anywhere from 1 to 4 carbon atoms may be replaced by N, O, or S, or a C3-C10 mono- or bicyclic cycloalkyl ring;

Y is $CR_2$, O, S, SO, $SO_2$, or NR;

$R_1$ is halo, CN, C1-C6 alkyl or fluoroalkyl, C1-C6 alkoxy or fluoroalkoxy, (C1-C8 alkyl)-$R_4$ wherein up to three $CH_2$ units may be replaced with O, CO, S, SO, $SO_2$ or NR; C6-C10 mono- or bicyclic aryl, C5-C10 mono- or bicyclic heteroaryl or heterocyclic ring wherein up to 4 carbon atoms may be replaced with O, S, N, or NR; or C3-C8 cycloalkyl, all four of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced with O, S, or NR; or a (C1-C8 alkyl)-$R_4$ wherein up to three $CH_2$ units may be replaced with O, CO, S, SO, $SO_2$ or NR; or two $R_1$ along with the atoms to which they are attached form a C5-C8 cyclic or heterocyclic ring wherein up to 2 carbon atoms may be replaced with O, S, or NR;

$R_2$ is halo, OH, amino, azide, CN, C1-C6 alkyl or fluoroalkyl, C1-C6 alkoxy or fluoroalkoxy, C6-C10 mono- or bicyclic aryl, C5-C10 mono- or bicyclic heteroaryl or heterocyclic ring wherein up to 4 carbon atoms may be replaced with O, S, N, or NR, C3-C8 cycloalkyl; or a (C1-C8 alkyl)-$R_4$ wherein up to three $CH_2$ units may be replaced with O, CO, S, SO, $SO_2$ or NR;

$R_3$ is halo, CN, $CO_2R$, C1-C6 alkyl, alkene, alkyne, or fluoroalkyl; C1-C6 alkoxy, cycloalkoxy, or fluoroalkoxy; C6-C10 mono- or bicyclic aryl or C5-C10 mono- or bicyclic heteroaryl wherein up to 4 carbon atoms may be replaced by O, S, N, or NR, both of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced by O, S, or NR; or or a (C1-C8 alkyl)-$R_4$ wherein up to three $CH_2$ units may be replaced with O, CO, S, SO, $SO_2$ or NR; or two $R_3$ may form a $=CH_2$ or $=O$ group;

$R_4$ is H, $CF_3$, $CO_2R$, OH, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR; $N(R)_2$, NRCOR, $CON(R)_2$, CN, halo, or $SO_2R$;

R is H, OH, C1-C6 alkyl, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR;

n is 0, 1, 2 or 3;

o is 0, 1, 2, or 3;

p is 0, 1, 2, or 3; and q is 0, 1, 2, 3, 4, or 5.

57. In another embodiment, the present invention features a compound of embodiment 56, wherein ring B is phenyl, pyridyl, pyridine-2 (1H)-one, pyrazole, indole, thiophene, dihydrobenzofuran, pyrazine, indazole, thiazole, pyridine-4 (1H)-one, pyrrolidinone, or quinoline.

58. In another embodiment, the present invention features a compound of embodiment 56 or 57, wherein ring B is selected from

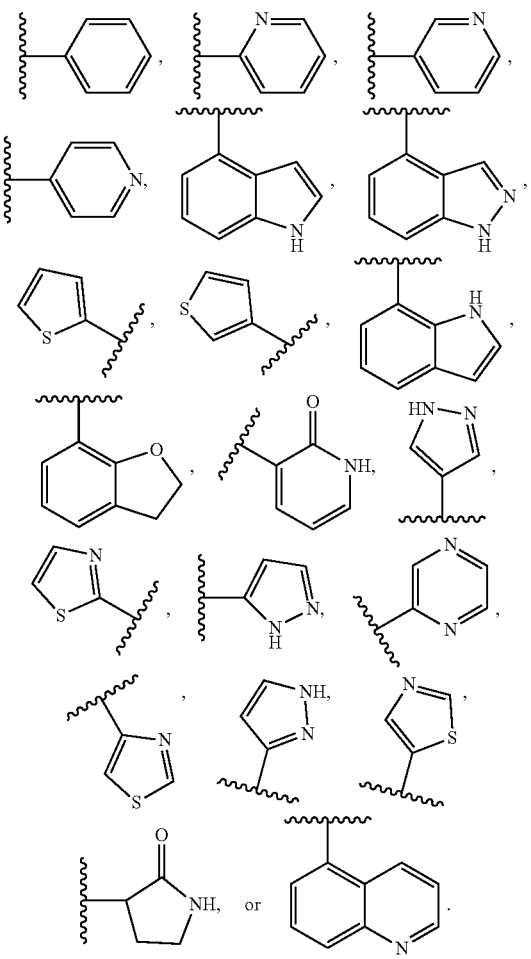

59. In another embodiment, the present invention features a compound of any one of embodiments 56 to 58, wherein ring C is phenyl, indole, cycloalkyl, pyridyl, pyrrolidine, naphthalene, or dihydroindene.

60. In another embodiment, the present invention features a compound of any one of embodiments 56 to 59, wherein ring C is

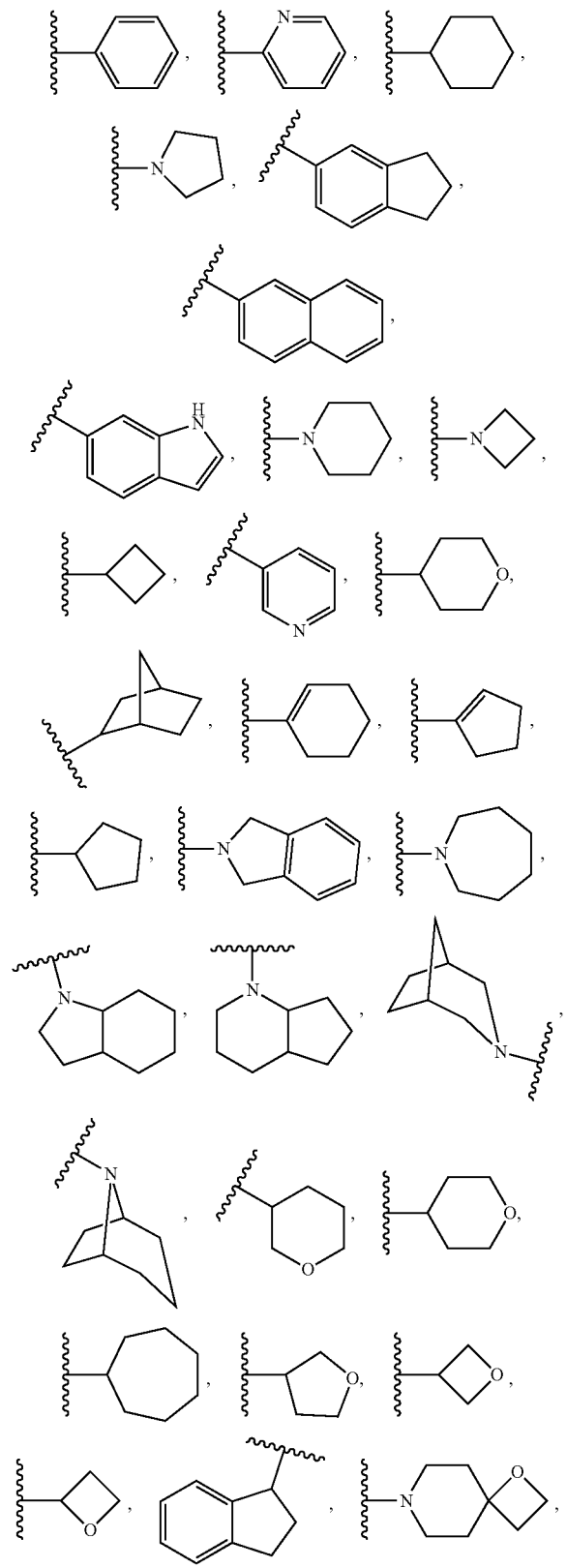

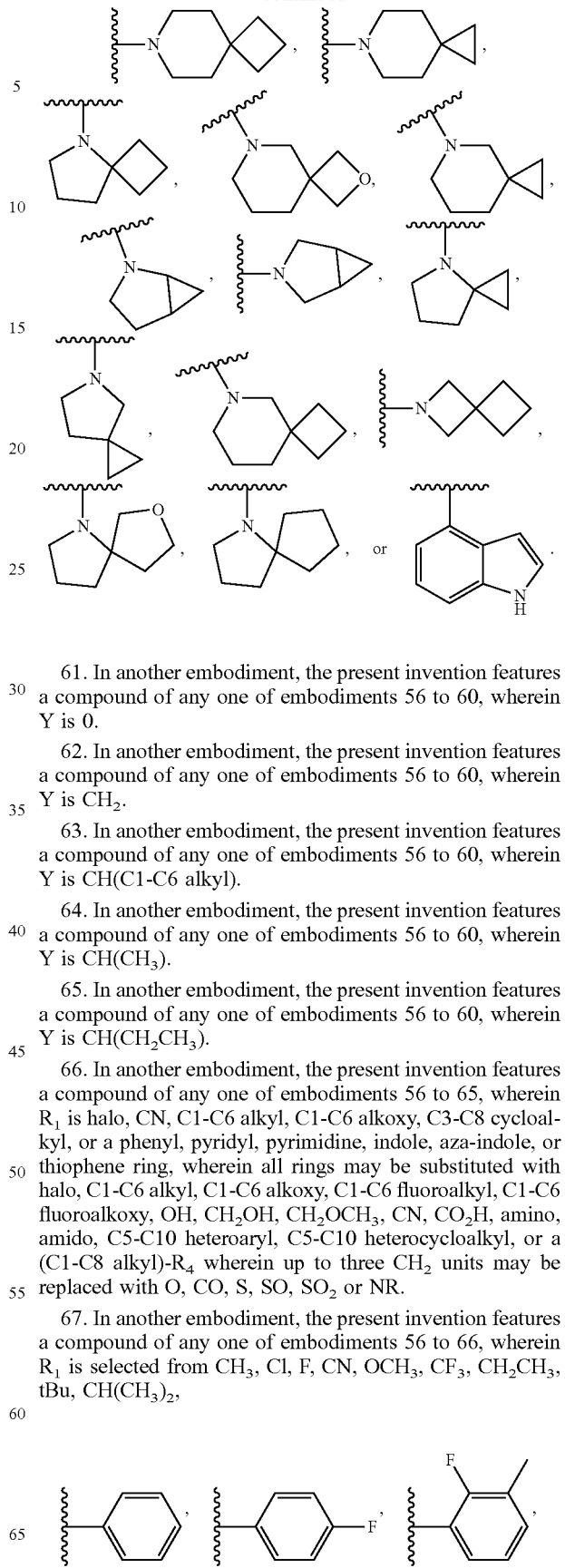

61. In another embodiment, the present invention features a compound of any one of embodiments 56 to 60, wherein Y is O.

62. In another embodiment, the present invention features a compound of any one of embodiments 56 to 60, wherein Y is $CH_2$.

63. In another embodiment, the present invention features a compound of any one of embodiments 56 to 60, wherein Y is CH(C1-C6 alkyl).

64. In another embodiment, the present invention features a compound of any one of embodiments 56 to 60, wherein Y is $CH(CH_3)$.

65. In another embodiment, the present invention features a compound of any one of embodiments 56 to 60, wherein Y is $CH(CH_2CH_3)$.

66. In another embodiment, the present invention features a compound of any one of embodiments 56 to 65, wherein $R_1$ is halo, CN, C1-C6 alkyl, C1-C6 alkoxy, C3-C8 cycloalkyl, or a phenyl, pyridyl, pyrimidine, indole, aza-indole, or thiophene ring, wherein all rings may be substituted with halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C5-C10 heteroaryl, C5-C10 heterocycloalkyl, or a (C1-C8 alkyl)-$R_4$ wherein up to three $CH_2$ units may be replaced with O, CO, S, SO, $SO_2$ or NR.

67. In another embodiment, the present invention features a compound of any one of embodiments 56 to 66, wherein $R_1$ is selected from $CH_3$, Cl, F, CN, $OCH_3$, $CF_3$, $CH_2CH_3$, tBu, $CH(CH_3)_2$,

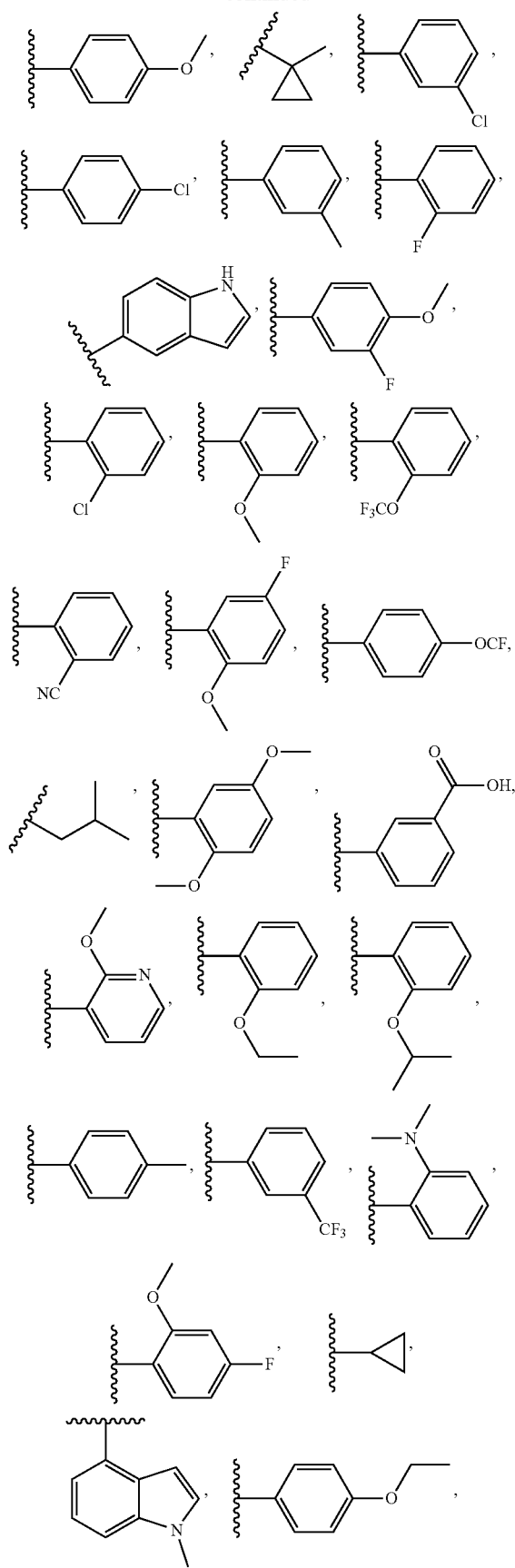
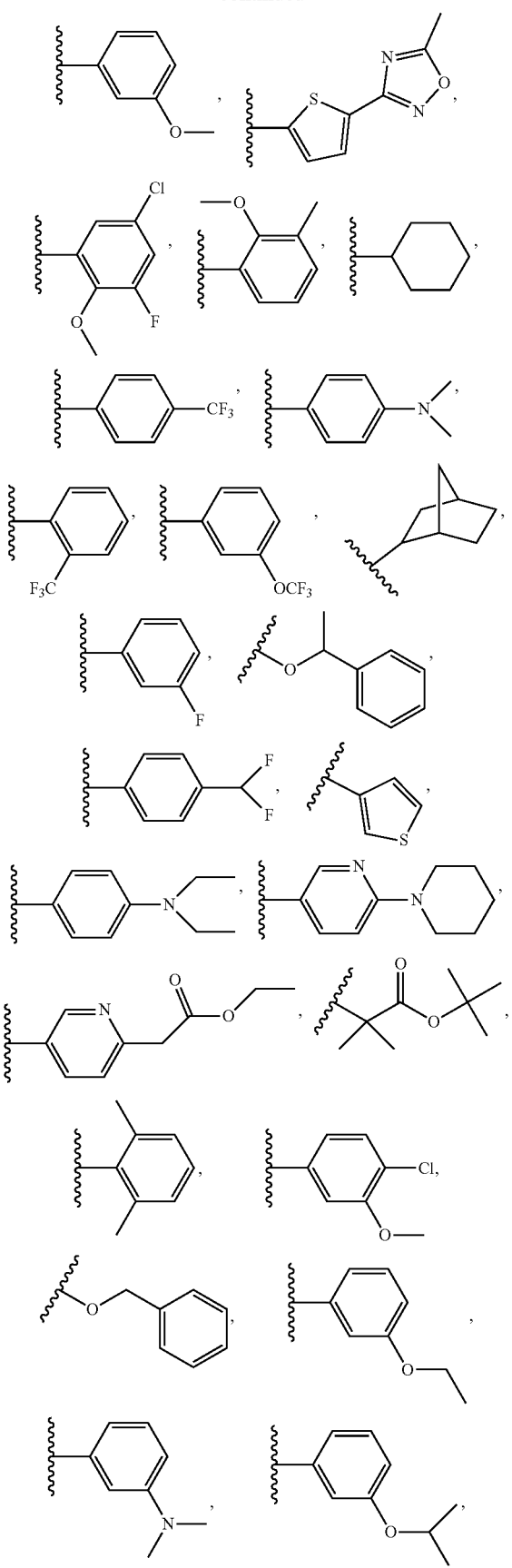

1713
-continued
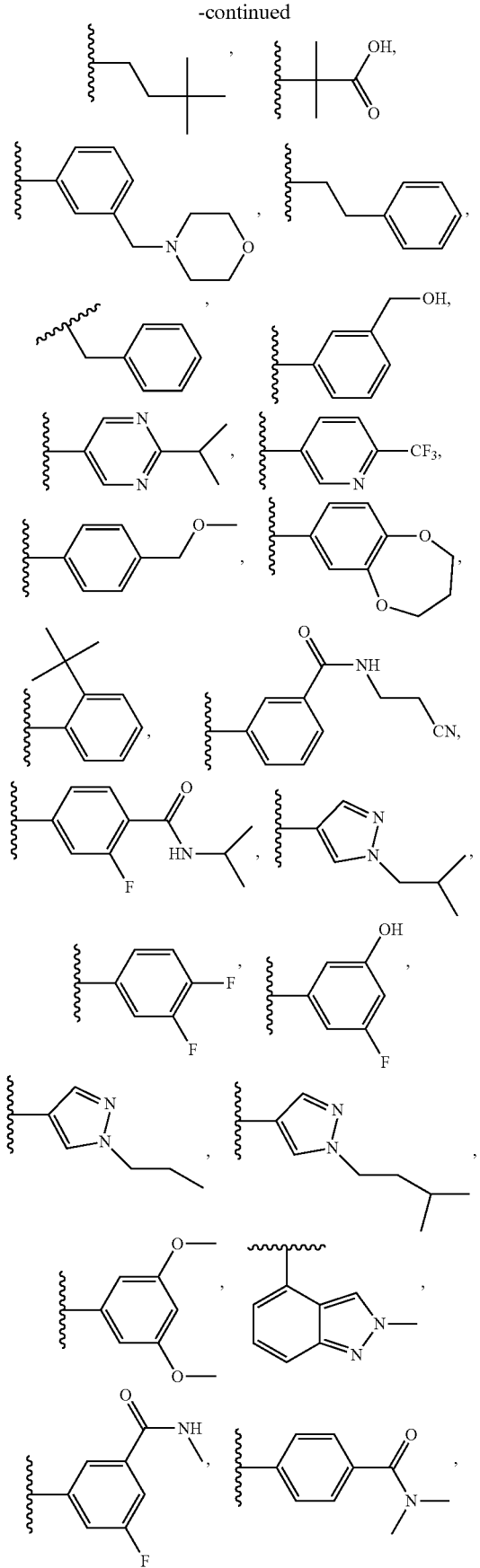
1714
-continued
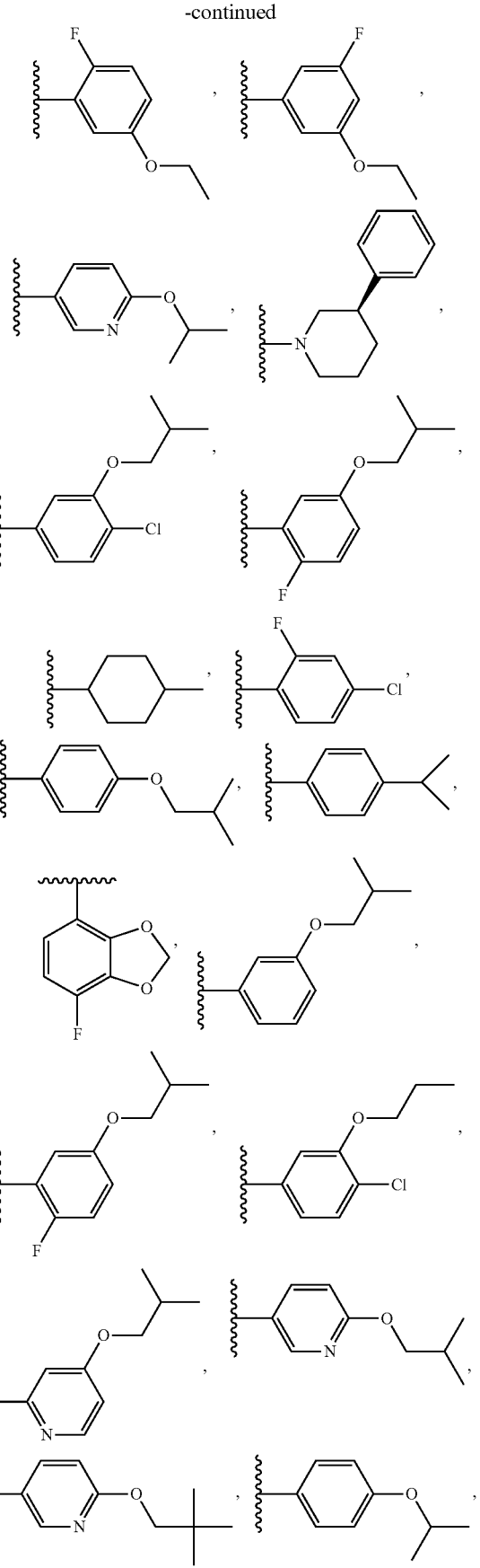

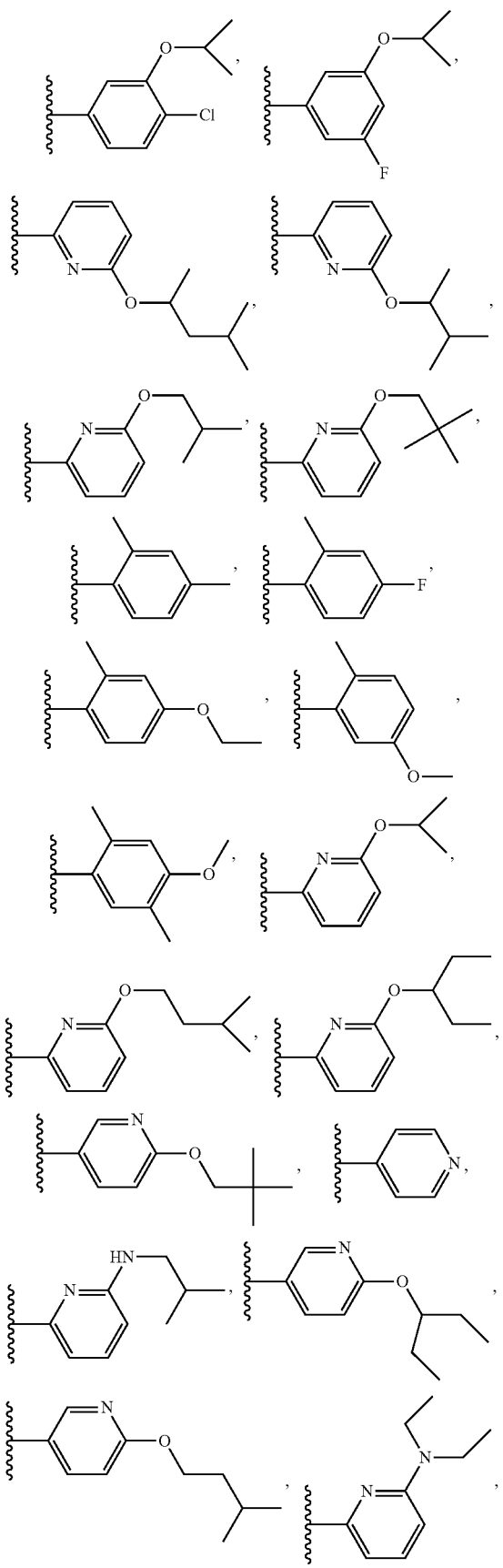

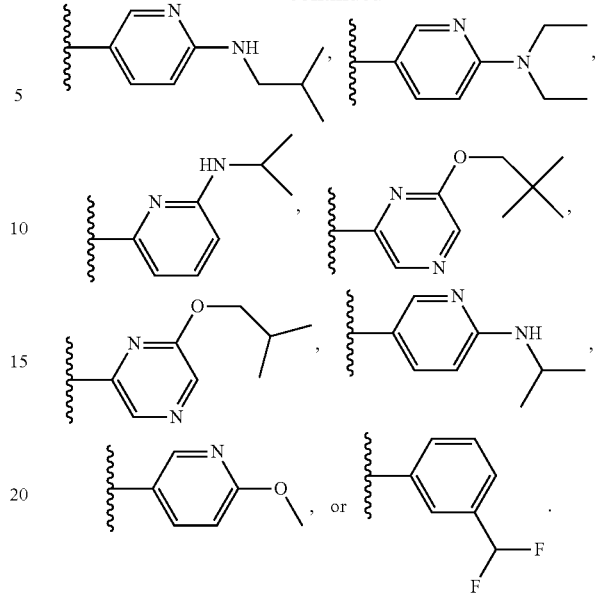

68. In another embodiment, the present invention features a compound of any one of embodiments 56 to 67, wherein $R_2$ is selected from halo, OH, CN, azide, amino, C1-C6 alkyl or fluoroalkyl, C1-C6 alkoxy or fluoroalkoxy, C5-C10 mono- or bicyclic heterocyclic ring wherein up to 4 carbon atoms may be replaced with O, S, N, or NR; or a (C1-C8 alkyl)-$R_4$ wherein up to three $CH_2$ units may be replaced with O, CO, S, SO, $SO_2$ or NR.

69. In another embodiment, the present invention features a compound of any one of embodiments 56 to 68, wherein $R_2$ is selected from Cl, F, OH, CN, $N_3$, $NH_2$, $NH(CH_3)$, $N(CH_3)_2$, $CH_3$, $CH_2OH$, $CH_2CH_3$, $CH(CH_3)_2$, $CHF_2$, $OCH_3$, $OCF_3$, $OCHF_2$, $OCH(CH_3)_2$, $C(O)CH_3$, $CH_2CH_2OH$, $CH_2NH_2$, $NH(CH_2)_2OH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

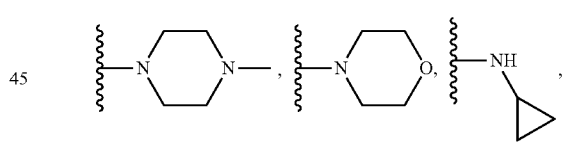

or $CO_2H$.

70. In another embodiment, the present invention features a compound of any one of embodiments 56 to 69, wherein $R_3$ is selected from halo, CN, C1-C6 alkyl or fluoroalkyl, C1-C6 alkoxy, or C5-C10 mono- or bicyclic heteroaryl wherein up to 4 carbon atoms may be replaced by O, S, N, or NR.

71. In another embodiment, the present invention features a compound of any one of embodiments 56 to 70, wherein $R_3$ is selected from Cl, F, CN, $CH_3$, $OCH_3$, $CF_3$, $CH_2CH_3$, $CH_2CF_3$, $CH_2CH_2CH_3$, $OCH_2CH_3$, $CH_2OCH_3$, $CH(CH_3)_2$, CCH, $CO_2CH_3$, tBu, $=CH_2$, $=O$,

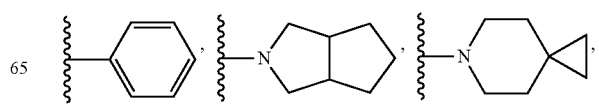

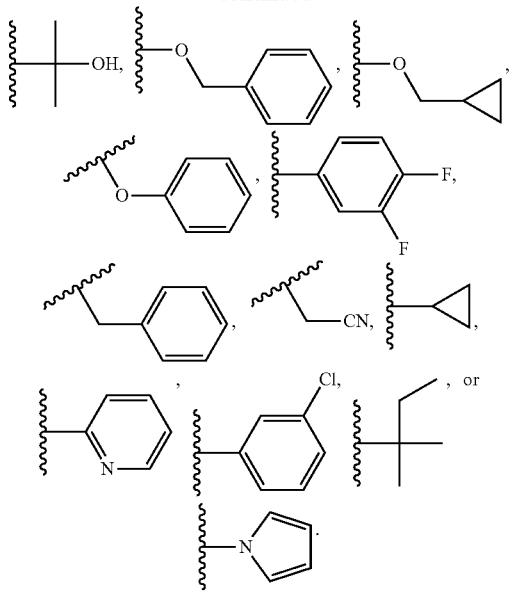

72. In another embodiment, the present invention features a compound of any one of embodiments 56 to 71, wherein o is 0.

73. In another embodiment, the present invention features a compound of any one of embodiments 56 to 71, wherein o is 1.

74. In another embodiment, the present invention features a compound of any one of embodiments 56 to 71, wherein o is 2.

75. In another embodiment, the present invention features a compound of any one of embodiments 56 to 74, wherein n is 0.

76. In another embodiment, the present invention features a compound of any one of embodiments 56 to 74, wherein n is 1.

77. In another embodiment, the present invention features a compound of any one of embodiments 56 to 74, wherein n is 2.

78. In another embodiment, the present invention features a compound of any one of embodiments 56 to 77, wherein p is 0.

79. In another embodiment, the present invention features a compound of any one of embodiments 56 to 77, wherein p is 1.

80. In another embodiment, the present invention features a compound of any one of embodiments 56 to 77, wherein p is 2.

81. In another embodiment, the present invention features a compound of any one of embodiments 56 to 80, wherein ring B is pyridyl.

82. In another embodiment, the present invention features a compound of any one of embodiments 56 to 81, wherein ring B is phenyl.

83. In another embodiment, the present invention features a compound of any one of embodiments 56 to 82, wherein ring B and ring C are phenyl.

84. In another embodiment, the present invention features a compound of embodiment 1, wherein the compound is of formula Ic:

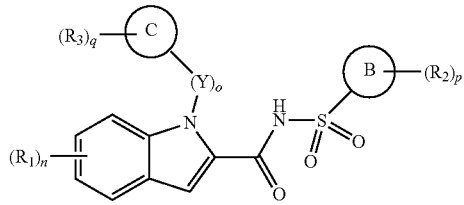

Ic or pharmaceutically acceptable salt thereof, wherein, independently for each occurrence:

Ring B is a C6-C10 aryl ring or C5-C10 heteroaryl or heterocyclic ring wherein up to 4 carbon atoms may be replaced by O, S, N, or NR;

Ring C is a C6-C10 mono- or bicyclic aryl ring, C5-C10 mono- or bicyclic heteroaryl or heterocyclic ring wherein anywhere from 1 to 4 carbon atoms may be replaced by N, O, or S, or a C3-C10 mono- or bicyclic cycloalkyl ring;

Y is $CR_2$, O, S, SO, $SO_2$, or NR;

$R_1$ is halo, CN, C1-C6 alkyl or fluoroalkyl, C1-C6 alkoxy or fluoroalkoxy, (C1-C8 alkyl)-$R_4$ wherein up to three $CH_2$ units may be replaced with O, CO, S, SO, $SO_2$ or NR; C6-C10 mono- or bicyclic aryl, C5-C10 mono- or bicyclic heteroaryl or heterocyclic ring wherein up to 4 carbon atoms may be replaced with O, S, N, or NR; or C3-C8 cycloalkyl, all four of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced with O, S, or NR; or a (C1-C8 alkyl)-$R_4$ wherein up to three $CH_2$ units may be replaced with O, CO, S, SO, $SO_2$ or NR; or two $R_1$ along with the atoms to which they are attached form a C5-C8 cyclic or heterocyclic ring wherein up to 2 carbon atoms may be replaced with O, S, or NR;

$R_2$ is halo, OH, amino, azide, CN, C1-C6 alkyl or fluoroalkyl, C1-C6 alkoxy or fluoroalkoxy, C6-C10 mono- or bicyclic aryl, C5-C10 mono- or bicyclic heteroaryl or heterocyclic ring wherein up to 4 carbon atoms may be replaced with O, S, N, or NR, C3-C8 cycloalkyl; or a (C1-C8 alkyl)-$R_4$ wherein up to three $CH_2$ units may be replaced with O, CO, S, SO, $SO_2$ or NR;

$R_3$ is halo, CN, $CO_2R$, C1-C6 alkyl, alkene, alkyne, or fluoroalkyl; C1-C6 alkoxy, cycloalkoxy, or fluoroalkoxy; C6-C10 mono- or bicyclic aryl or C5-C10 mono- or bicyclic heteroaryl wherein up to 4 carbon atoms may be replaced by O, S, N, or NR, both of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced by O, S, or NR; or or a (C1-C8 alkyl)-$R_4$ wherein up to three $CH_2$ units may be replaced with O, CO, S, SO, $SO_2$ or NR; or two $R_3$ may form a $=CH_2$ or $=O$ group;

$R_4$ is H, $CF_3$, $CO_2R$, OH, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR; $N(R)_2$, NRCOR, $CON(R)_2$, CN, halo, or $SO_2R$;

R is H, OH, C1-C6 alkyl, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR;

n is 0, 1, 2 or 3;

o is 0, 1, 2, or 3;

p is 0, 1, 2, or 3; and q is 0, 1, 2, 3, 4, or 5.

85. In another embodiment, the present invention features a compound of embodiment 84, wherein ring B is phenyl, pyridyl, pyridine-2 (1H)-one, pyrazole, indole, thiophene, dihydrobenzofuran, pyrazine, indazole, thiazole, pyridine-4 (1H)-one, pyrrolidinone, or quinoline.

86. In another embodiment, the present invention features a compound of embodiment 84 or 85, wherein ring B is selected from

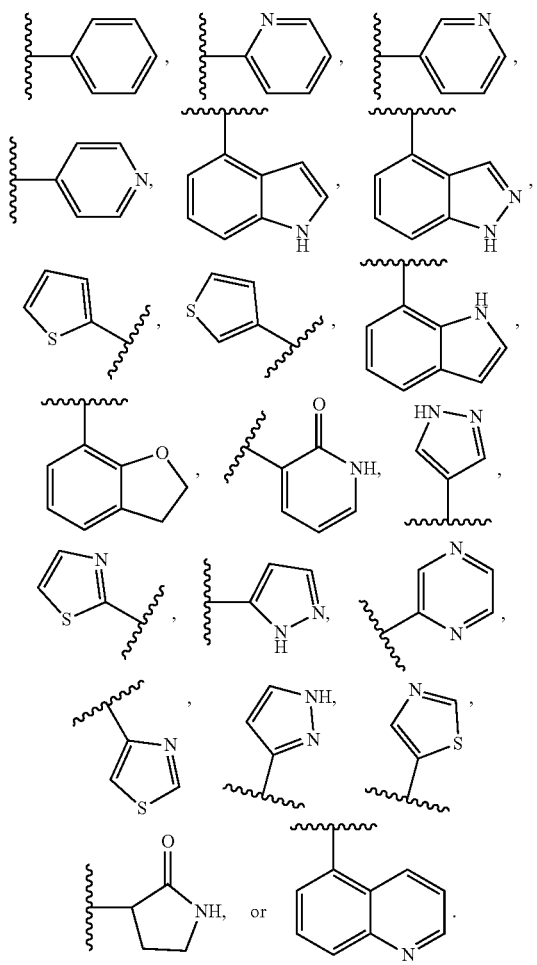

87. In another embodiment, the present invention features a compound of any one of embodiments 84 to 86, wherein ring C is phenyl, indole, cycloalkyl, pyridyl, pyrrolidine, naphthalene, or dihydroindene.

88. In another embodiment, the present invention features a compound of any one of embodiments 84 to 87, wherein ring C is

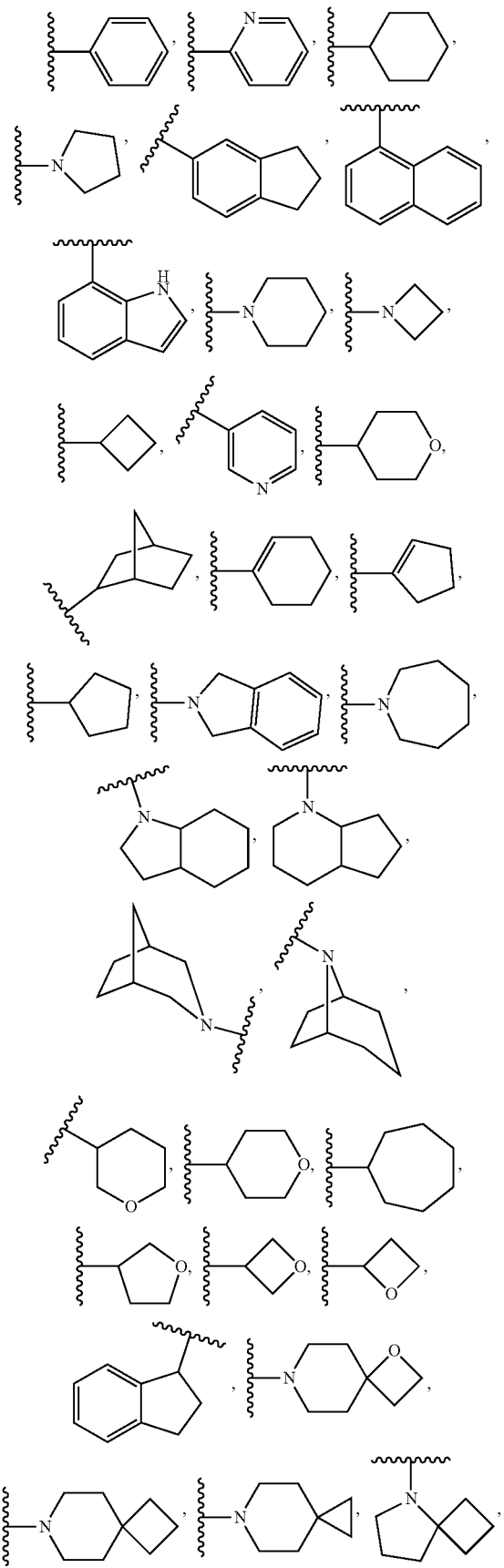

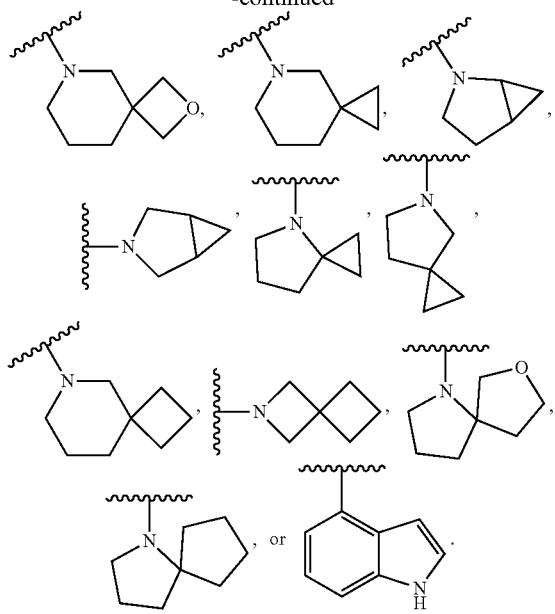

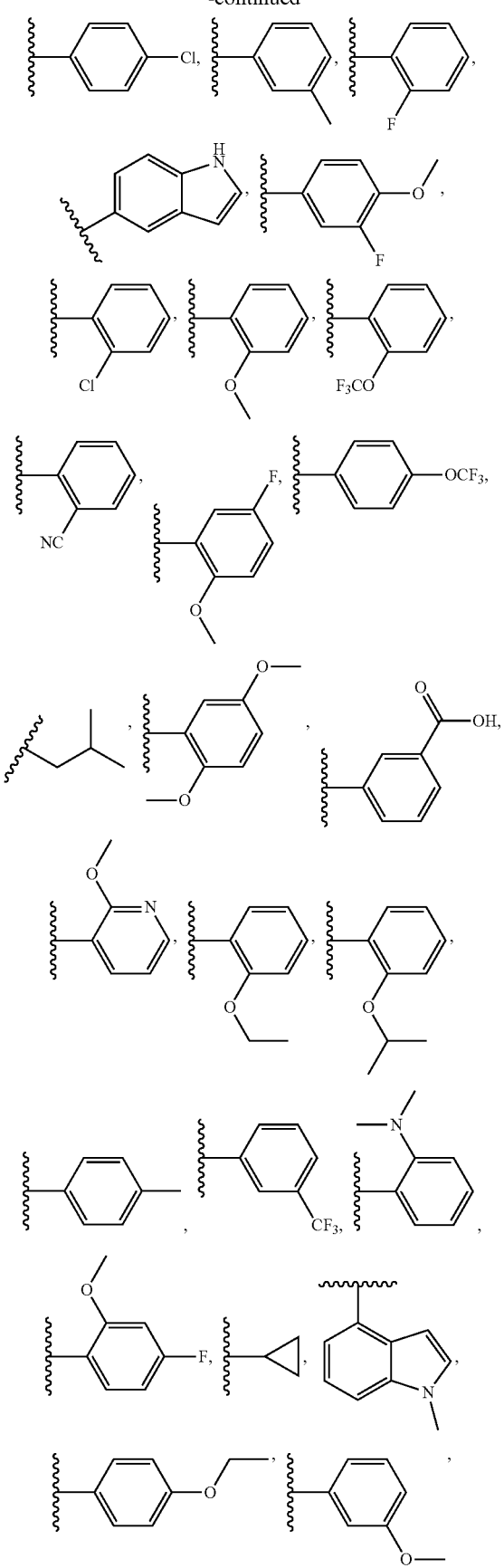

89. In another embodiment, the present invention features a compound of any one of embodiments 84 to 88, wherein Y is O.

90. In another embodiment, the present invention features a compound of any one of embodiments 84 to 88, wherein Y is $CH_2$.

91. In another embodiment, the present invention features a compound of any one of embodiments 84 to 88, wherein Y is CH(C1-C6 alkyl).

92. In another embodiment, the present invention features a compound of any one of embodiments 84 to 88, wherein Y is $CH(CH_3)$.

93. In another embodiment, the present invention features a compound of any one of embodiments 84 to 88, wherein Y is $CH(CH_2CH_3)$.

94. In another embodiment, the present invention features a compound of any one of embodiments 84 to 93, wherein $R_1$ is halo, CN, C1-C6 alkyl, C1-C6 alkoxy, C3-C8 cycloalkyl, or a phenyl, pyridyl, pyrimidine, indole, aza-indole, or thiophene ring, wherein all rings may be substituted with halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C5-C10 heteroaryl, C5-C10 heterocycloalkyl, or a (C1-C8 alkyl)-$R_4$ wherein up to three $CH_2$ units may be replaced with O, CO, S, SO, $SO_2$ or NR.

95. In another embodiment, the present invention features a compound of any one of embodiments 84 to 94, wherein $R_1$ is selected from $CH_3$, Cl, F, CN, $OCH_3$, $CF_3$, $CH_2CH_3$, tBu, $CH(CH_3)_2$,

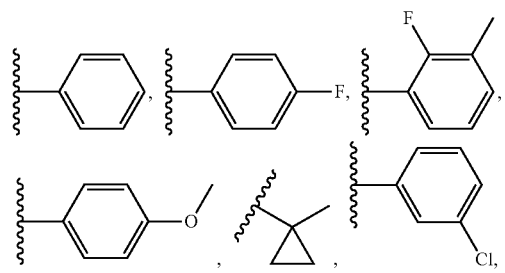

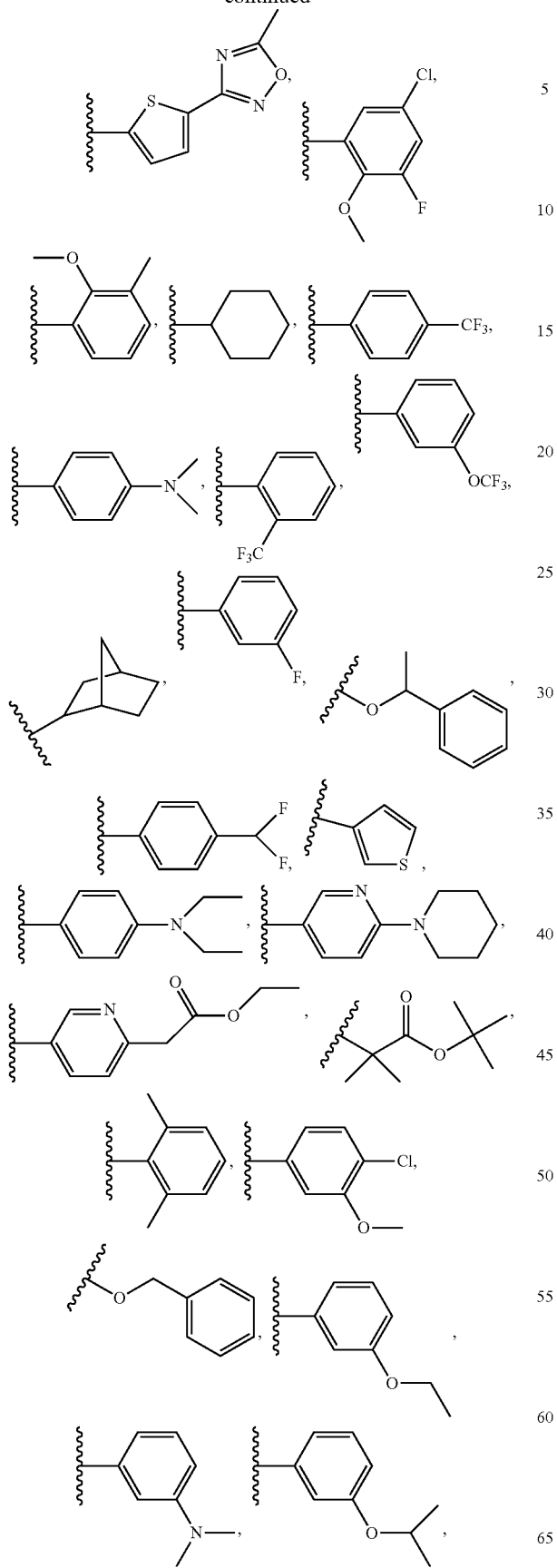
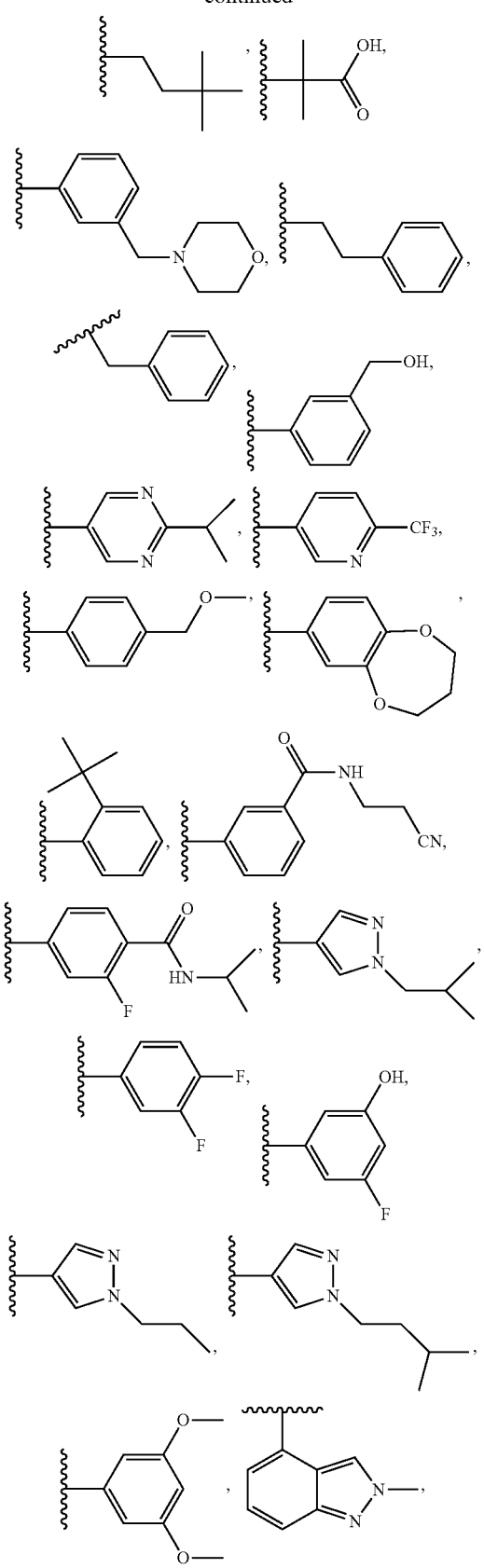

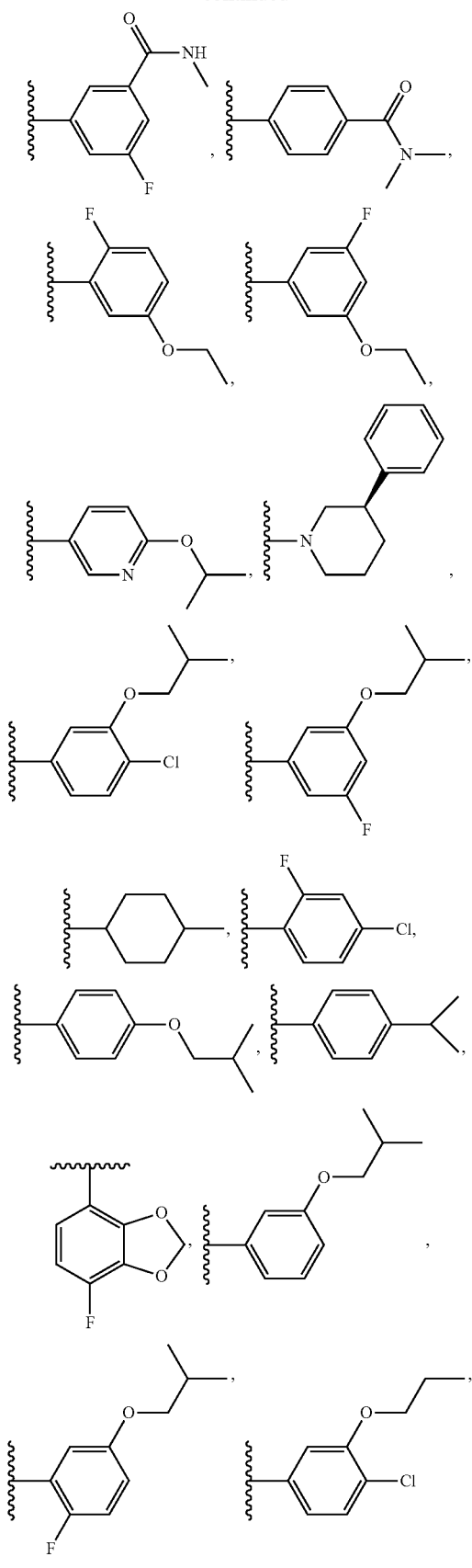
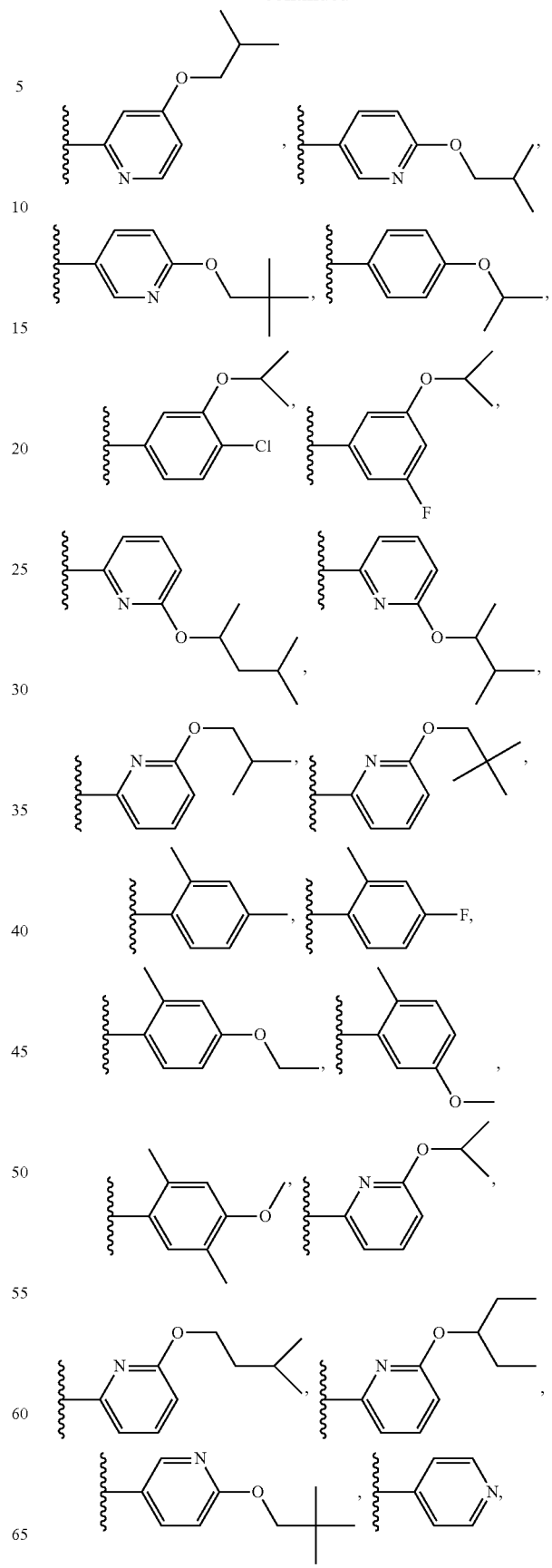

-continued

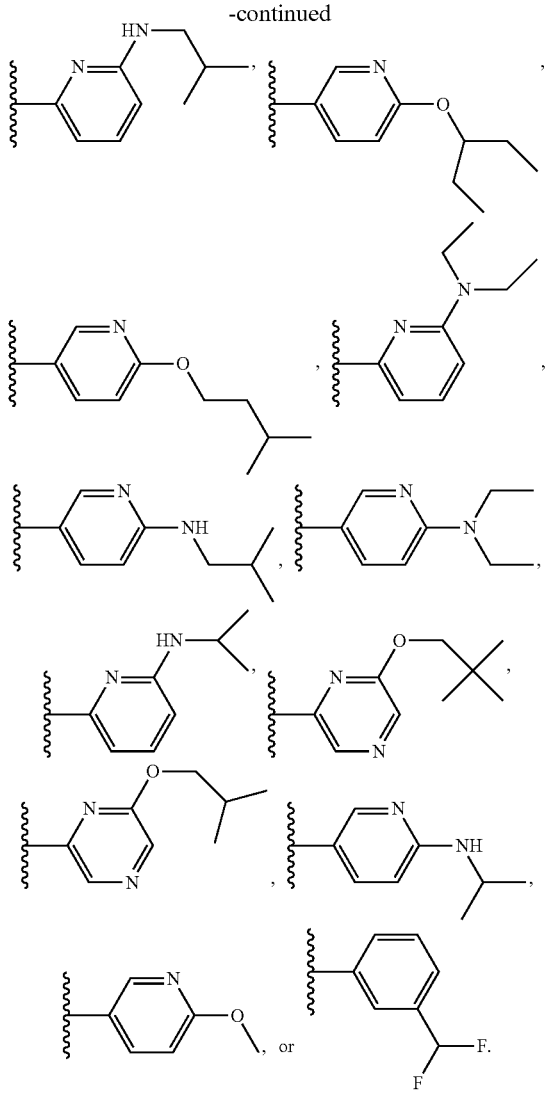

96. In another embodiment, the present invention features a compound of any one of embodiments 84 to 95, wherein $R_2$ is selected from halo, OH, CN, azide, amino, C1-C6 alkyl or fluoroalkyl, C1-C6 alkoxy or fluoroalkoxy, C5-C10 mono- or bicyclic heterocyclic ring wherein up to 4 carbon atoms may be replaced with O, S, N, or NR; or a (C1-C8 alkyl)-$R_4$ wherein up to three $CH_2$ units may be replaced with O, CO, S, SO, $SO_2$ or NR.

97. In another embodiment, the present invention features a compound of any one of embodiments 84 to 96, wherein $R_2$ is selected from Cl, F, OH, CN, $N_3$, $NH_2$, $NH(CH_3)$, $N(CH_3)_2$, $CH_3$, $CH_2OH$, $CH_2CH_3$, $CH(CH_3)_2$, $CHF_2$, $OCH_3$, $OCF_3$, $OCHF_2$, $OCH(CH_3)_2$, $C(O)CH_3$, $CH_2CH_2OH$, $CH_2NH_2$, $NH(CH_2)_2OH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

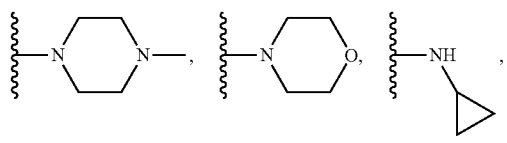

98. In another embodiment, the present invention features a compound of any one of embodiments 84 to 97, wherein $R_3$ is selected from halo, CN, C1-C6 alkyl or fluoroalkyl, C1-C6 alkoxy, or C5-C10 mono- or bicyclic heteroaryl wherein up to 4 carbon atoms may be replaced by O, S, N, or NR.

99. In another embodiment, the present invention features a compound of any one of embodiments 84 to 98, wherein $R_3$ is selected from Cl, F, CN, $CH_3$, $OCH_3$, $CF_3$, $CH_2CH_3$,

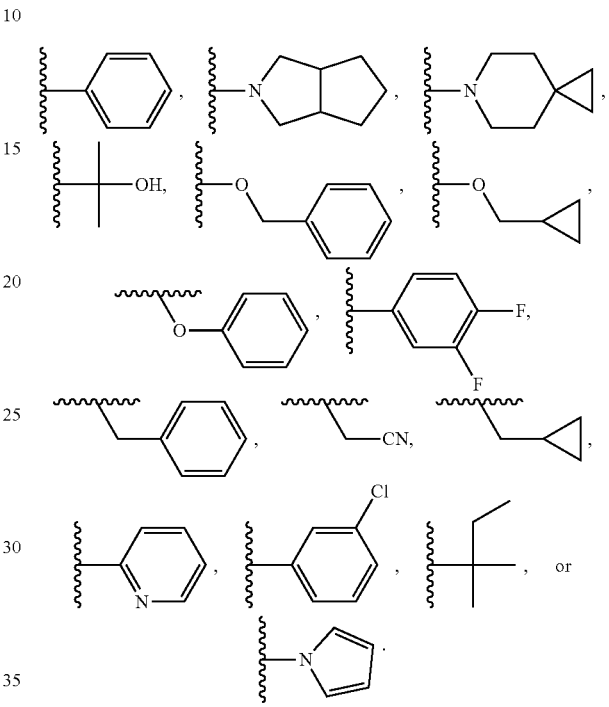

100. In another embodiment, the present invention features a compound of any one of embodiments 84 to 99, wherein o is 0.

101. In another embodiment, the present invention features a compound of any one of embodiments 84 to 99, wherein o is 1.

102. In another embodiment, the present invention features a compound of any one of embodiments 84 to 99, wherein o is 2.

103. In another embodiment, the present invention features a compound of any one of embodiments 84 to 102, wherein n is 0.

104. In another embodiment, the present invention features a compound of any one of embodiments 84 to 102, wherein n is 1.

105. In another embodiment, the present invention features a compound of any one of embodiments 84 to 102, wherein n is 2.

106. In another embodiment, the present invention features a compound of any one of embodiments 84 to 105, wherein p is 0.

107. In another embodiment, the present invention features a compound of any one of embodiments 84 to 105, wherein p is 1.

108. In another embodiment, the present invention features a compound of any one of embodiments 84 to 105, wherein p is 2.

109. In another embodiment, the present invention features a compound of any one of embodiments 84 to 108, wherein ring B is phenyl.

110. In another embodiment, the present invention features a compound of any one of embodiments 84 to 109, wherein ring C is phenyl.

111. In another embodiment, the present invention features a compound of any one of embodiments 84 to 110, wherein ring B and ring C are phenyl.

112. In another embodiment, the present invention features a compound of embodiment 1, wherein the compound is of formula Id:

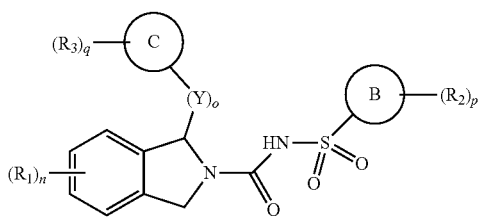

Id or pharmaceutically acceptable salt thereof, wherein, independently for each occurrence:
- Ring B is a C6-C10 aryl ring or C5-C10 heteroaryl or heterocyclic ring wherein up to 4 carbon atoms may be replaced by O, S, N, or NR;
- Ring C is a C6-C10 mono- or bicyclic aryl ring, C5-C10 mono- or bicyclic heteroaryl or heterocyclic ring wherein anywhere from 1 to 4 carbon atoms may be replaced by N, O, or S, or a C3-C10 mono- or bicyclic cycloalkyl ring;
- Y is $CR_2$, O, S, SO, $SO_2$, or NR;
- $R_1$ is halo, CN, C1-C6 alkyl or fluoroalkyl, C1-C6 alkoxy or fluoroalkoxy, (C1-C8 alkyl)-$R_4$ wherein up to three $CH_2$ units may be replaced with O, CO, S, SO, $SO_2$ or NR; C6-C10 mono- or bicyclic aryl, C5-C10 mono- or bicyclic heteroaryl or heterocyclic ring wherein up to 4 carbon atoms may be replaced with O, S, N, or NR; or C3-C8 cycloalkyl, all four of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced with O, S, or NR; or a (C1-C8 alkyl)-$R_4$ wherein up to three $CH_2$ units may be replaced with O, CO, S, SO, $SO_2$ or NR; or two $R_1$ along with the atoms to which they are attached form a C5-C8 cyclic or heterocyclic ring wherein up to 2 carbon atoms may be replaced with O, S, or NR;
- $R_2$ is halo, OH, amino, azide, CN, C1-C6 alkyl or fluoroalkyl, C1-C6 alkoxy or fluoroalkoxy, C6-C10 mono- or bicyclic aryl, C5-C10 mono- or bicyclic heteroaryl or heterocyclic ring wherein up to 4 carbon atoms may be replaced with O, S, N, or NR, C3-C8 cycloalkyl; or a (C1-C8 alkyl)-$R_4$ wherein up to three $CH_2$ units may be replaced with O, CO, S, SO, $SO_2$ or NR;
- $R_3$ is halo, CN, $CO_2R$, C1-C6 alkyl, alkene, alkyne, or fluoroalkyl; C1-C6 alkoxy, cycloalkoxy, or fluoroalkoxy; C6-C10 mono- or bicyclic aryl or C5-C10 mono- or bicyclic heteroaryl wherein up to 4 carbon atoms may be replaced by O, S, N, or NR, both of which may be substituted with halo, C1-C6 alkyl or fluoroalkyl, C1-C6 alkoxy or fluoroalkoxy, CN, $CO_2H$, amino, C5-C10 mono- or bicyclic heteroaryl wherein up to 4 carbon atoms may be replaced by O, S, N, or NR; C5-C10 mono- or bicyclic heterocycloalkyl wherein up to 4 carbon atoms may be replaced by O, S, or NR; or a (C1-C8 alkyl)-$R_4$ wherein up to three $CH_2$ units may be replaced with O, CO, S, SO, $SO_2$ or NR; or two $R_3$ may form a $=CH_2$ or $=O$ group;
- $R_4$ is H, $CF_3$, $CO_2R$, OH, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR; $N(R)_2$, NRCOR, $CON(R)_2$, CN, halo, or $SO_2R$;
- R is H, OH, C1-C6 alkyl, C6-C10 mono- or bicyclic aryl, C5-C10 mono- or bicyclic heteroaryl wherein up to 4 carbon atoms may be replaced by O, S, N, or NR; C3-C8 cycloalkyl or heterocycloalkyl wherein up to 4 carbon atoms may be replaced with O, S, or NR;
- n is 0, 1, 2 or 3;
- o is 0, 1, 2, or 3;
- p is 0, 1, 2, or 3; and
- q is 0, 1, 2, 3, 4, or 5.

113. In another embodiment, the present invention features a compound of embodiment 112, wherein ring B is phenyl, pyridyl, pyridine-2 (1H)-one, pyrazole, indole, thiophene, dihydrobenzofuran, pyrazine, indazole, thiazole, pyridine-4 (1H)-one, pyrrolidinone, or quinoline.

114. In another embodiment, the present invention features a compound of embodiment 112 or 113, wherein ring B is selected from

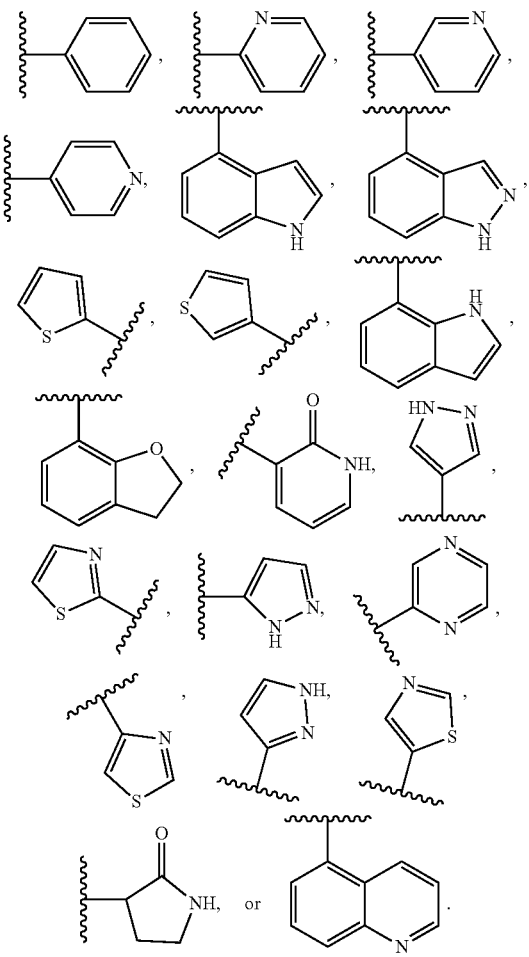

115. In another embodiment, the present invention features a compound of any one of embodiments 112 to 114, wherein ring C is phenyl, indole, cycloalkyl, pyridyl, pyrrolidine, naphthalene, or dihydroindene.

116. In another embodiment, the present invention features a compound of any one of embodiments 112 to 115, wherein ring C is

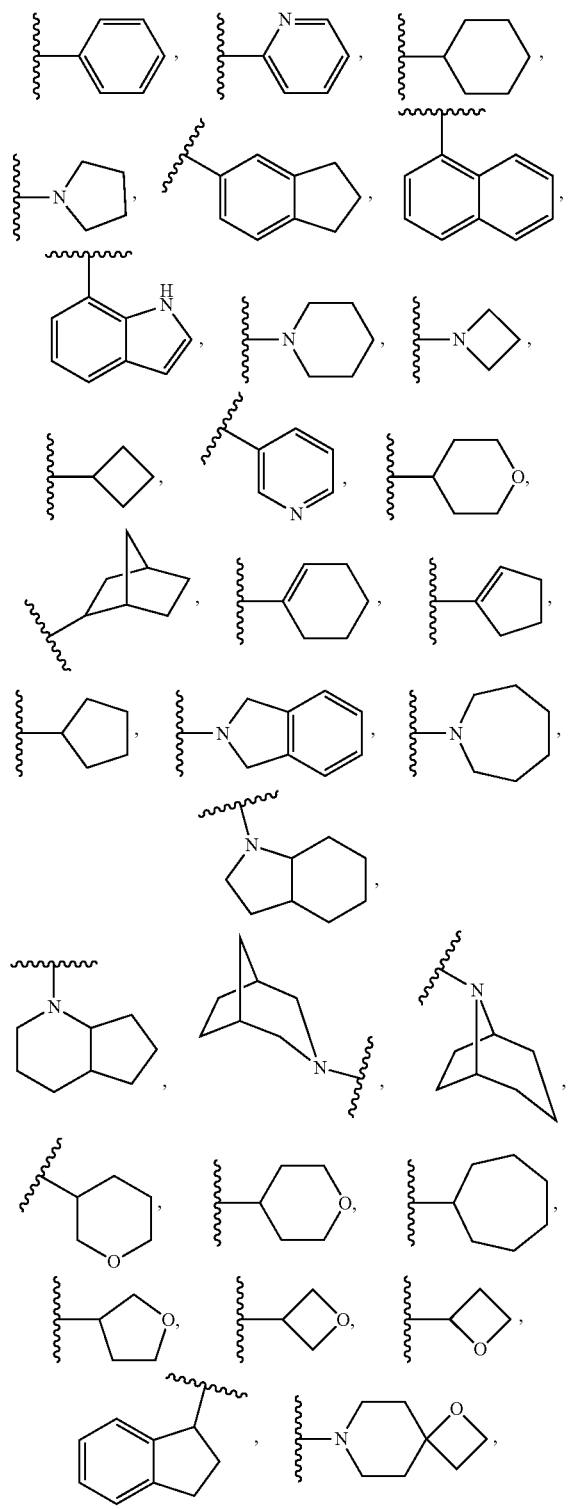

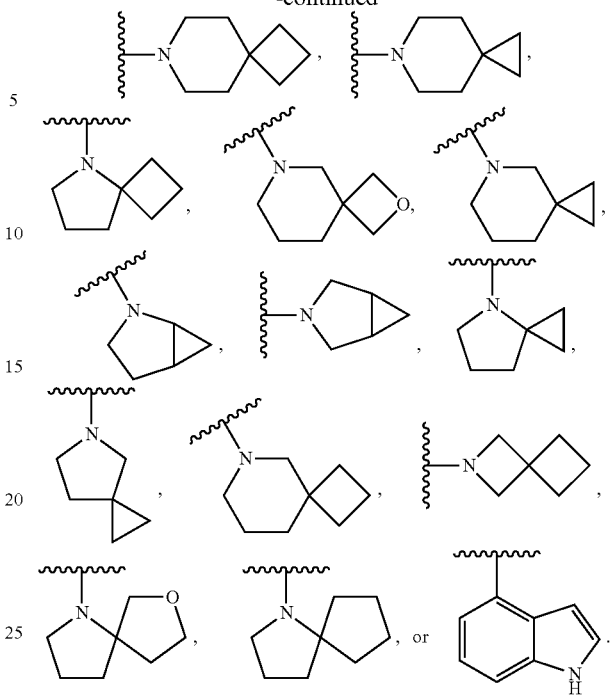

117. In another embodiment, the present invention features a compound of any one of embodiments 112 to 116, wherein Y is O.

118. In another embodiment, the present invention features a compound of any one of embodiments 112 to 116, wherein Y is $CH_2$.

119. In another embodiment, the present invention features a compound of any one of embodiments 112 to 116, wherein Y is CH(C1-C6 alkyl).

120. In another embodiment, the present invention features a compound of any one of embodiments 112 to 116, wherein Y is $CH(CH_3)$.

121. In another embodiment, the present invention features a compound of any one of embodiments 112 to 116, wherein Y is $CH(CH_2CH_3)$.

122. In another embodiment, the present invention features a compound of any one of embodiments 112 to 121, wherein $R_1$ is halo, CN, C1-C6 alkyl, C1-C6 alkoxy, C3-C8 cycloalkyl, or a phenyl, pyridyl, pyrimidine, indole, azaindole, or thiophene ring, wherein all rings may be substituted with halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C5-C10 heteroaryl, C5-C10 heterocycloalkyl, or a (C1-C8 alkyl)-$R_4$ wherein up to three $CH_2$ units may be replaced with 0, CO, S, SO, $SO_2$ or NR.

123. In another embodiment, the present invention features a compound of any one of embodiments 112 to 122, wherein $R_1$ is selected from $CH_3$, Cl, F, CN, $OCH_3$, $CF_3$, $CH_2CH_3$, tBu, $CH(CH_3)_2$,

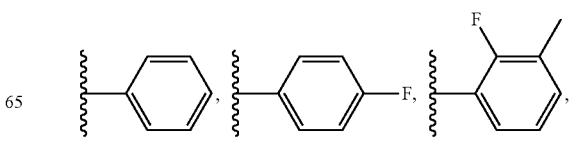

1733
-continued
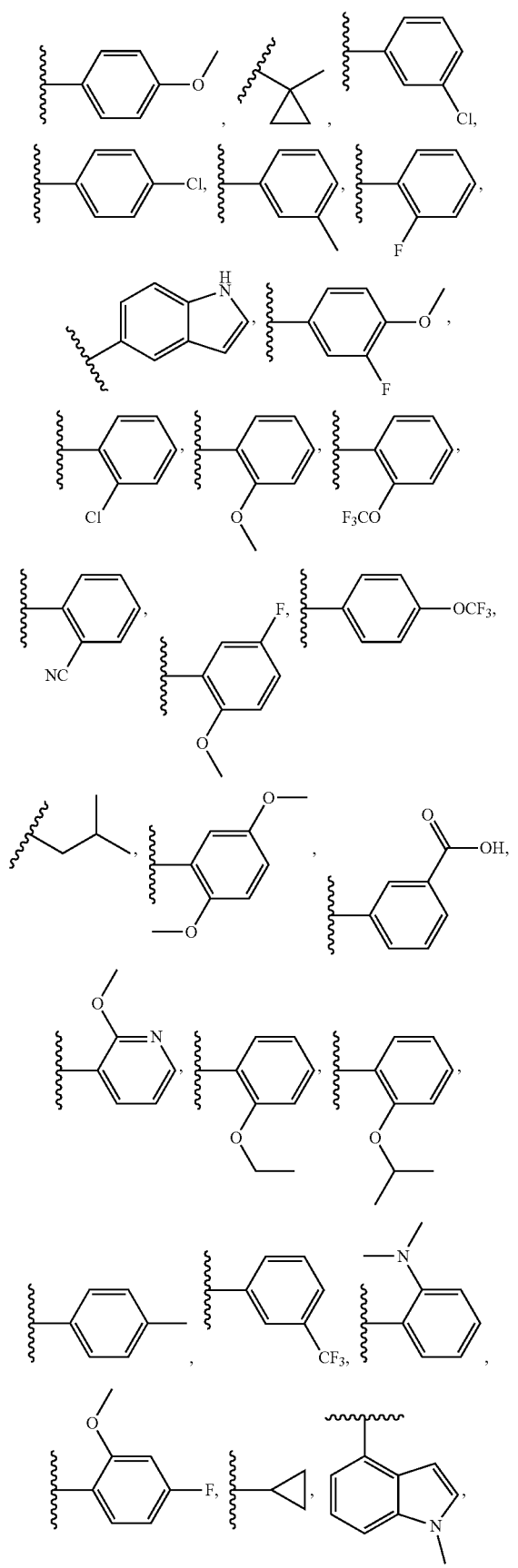
1734
-continued
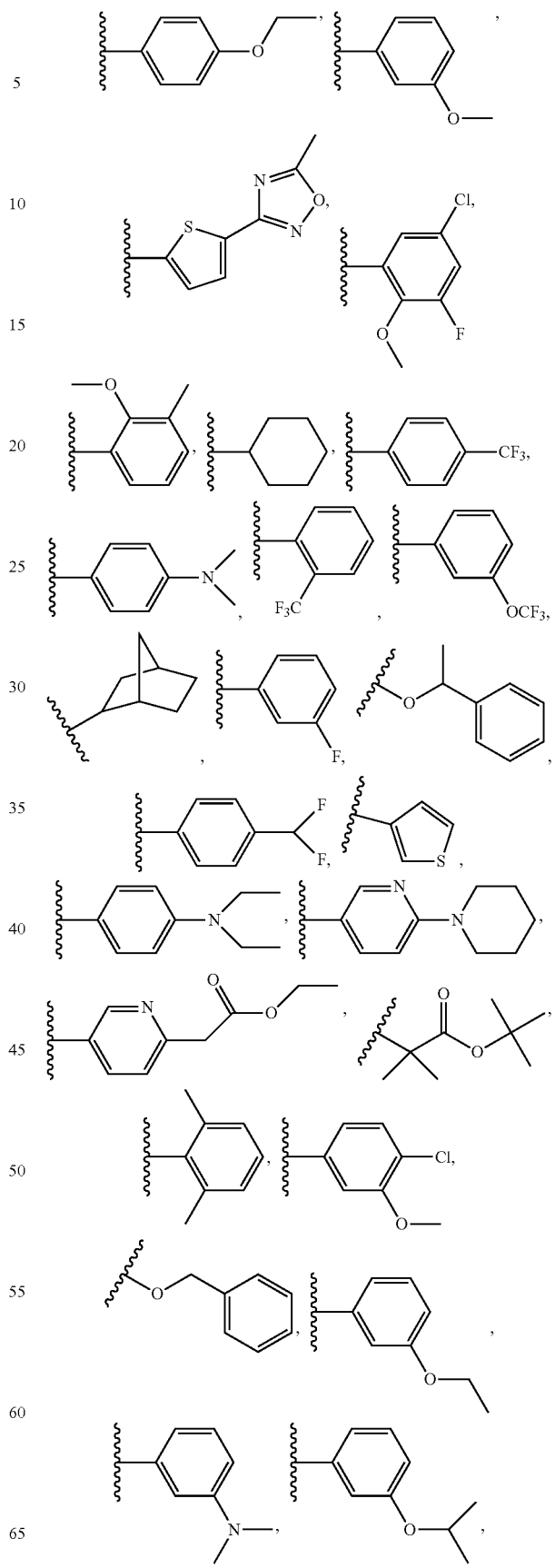

1735
-continued
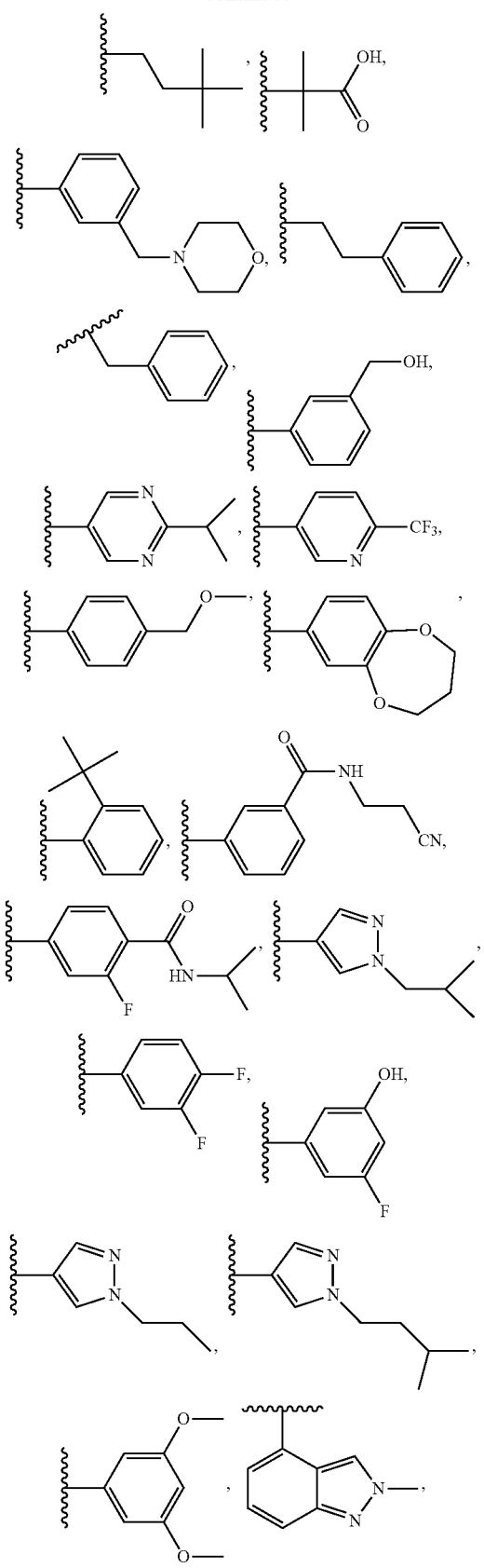
1736
-continued
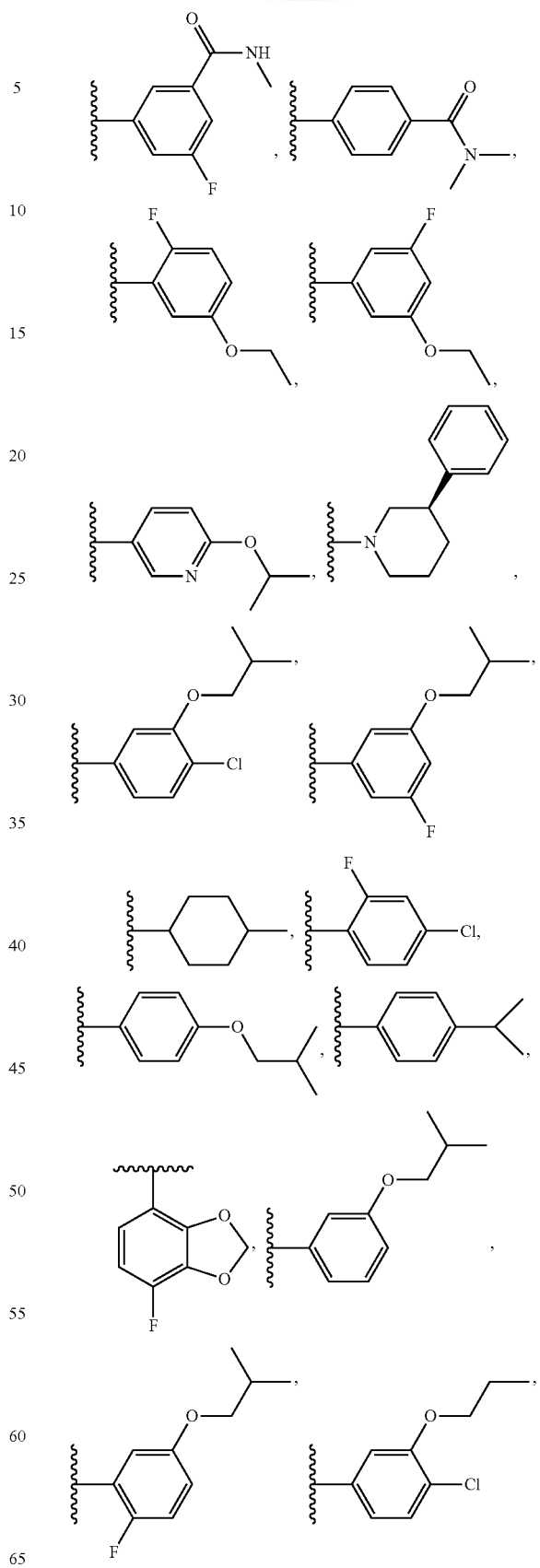

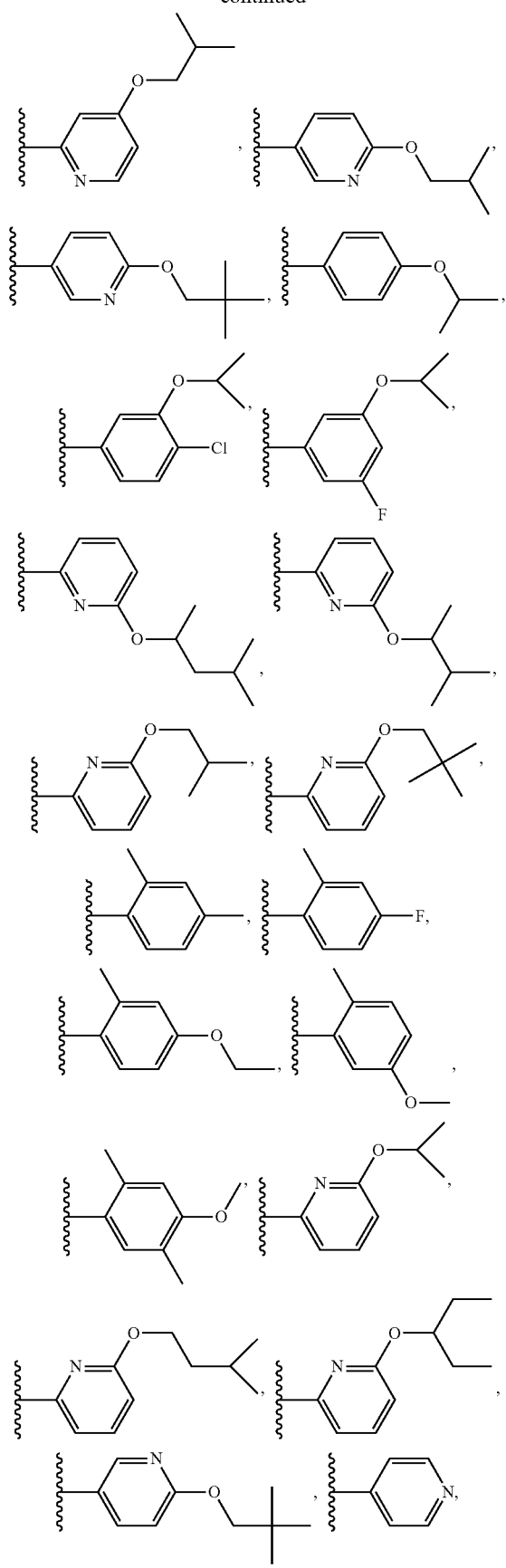
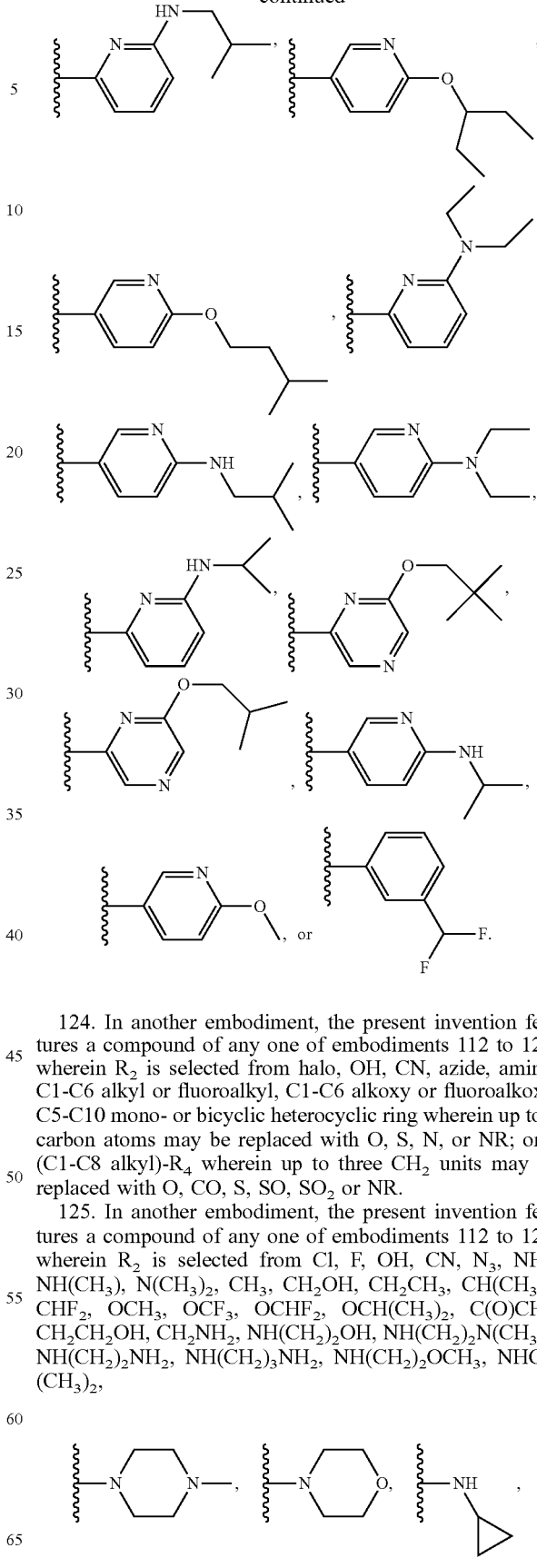

124. In another embodiment, the present invention features a compound of any one of embodiments 112 to 123, wherein $R_2$ is selected from halo, OH, CN, azide, amino, C1-C6 alkyl or fluoroalkyl, C1-C6 alkoxy or fluoroalkoxy, C5-C10 mono- or bicyclic heterocyclic ring wherein up to 4 carbon atoms may be replaced with O, S, N, or NR; or a (C1-C8 alkyl)-$R_4$ wherein up to three $CH_2$ units may be replaced with O, CO, S, SO, $SO_2$ or NR.

125. In another embodiment, the present invention features a compound of any one of embodiments 112 to 124, wherein $R_2$ is selected from Cl, F, OH, CN, $N_3$, $NH_2$, $NH(CH_3)$, $N(CH_3)_2$, $CH_3$, $CH_2OH$, $CH_2CH_3$, $CH(CH_3)_2$, $CHF_2$, $OCH_3$, $OCF_3$, $OCHF_2$, $OCH(CH_3)_2$, $C(O)CH_3$, $CH_2CH_2OH$, $CH_2NH_2$, $NH(CH_2)_2OH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$, or $CO_2H$.

126. In another embodiment, the present invention features a compound of any one of embodiments 112 to 125, wherein $R_3$ is selected from halo, CN, C1-C6 alkyl or fluoroalkyl, C1-C6 alkoxy, or C5-C10 mono- or bicyclic heteroaryl wherein up to 4 carbon atoms may be replaced by O, S, N, or NR.

127. In another embodiment, the present invention features a compound of any one of embodiments 112 to 126, wherein $R_3$ is selected from Cl, F, CN, $CH_3$, $OCH_3$, $CF_3$, $CH_2CH_3$, $CH_2CF_3$, $CH_2CH_2CH_3$, $OCH_2CH_3$, $CH_2OCH_3$, $CH(CH_3)_2$, CCH, $CO_2CH_3$, tBu, $=CH_2$, $=O$,

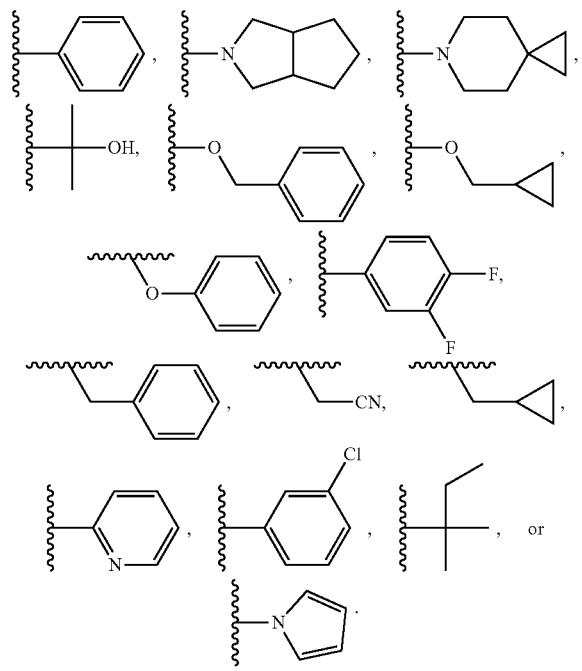

128. In another embodiment, the present invention features a compound of any one of embodiments 112 to 127, wherein o is 0.

129. In another embodiment, the present invention features a compound of any one of embodiments 112 to 127, wherein o is 1.

130. In another embodiment, the present invention features a compound of any one of embodiments 112 to 127, wherein o is 2.

131. In another embodiment, the present invention features a compound of any one of embodiments 112 to 130, wherein n is 0.

132. In another embodiment, the present invention features a compound of any one of embodiments 112 to 130, wherein n is 1.

133. In another embodiment, the present invention features a compound of any one of embodiments 112 to 130, wherein n is 2.

134. In another embodiment, the present invention features a compound of any one of embodiments 112 to 133, wherein p is 0.

135. In another embodiment, the present invention features a compound of any one of embodiments 112 to 133, wherein p is 1.

136. In another embodiment, the present invention features a compound of any one of embodiments 112 to 133, wherein p is 2.

137. In another embodiment, the present invention features a compound of any one of embodiments 112 to 136, wherein ring B is phenyl.

138. In another embodiment, the present invention features a compound of any one of embodiments 112 to 137, wherein ring B is pyridyl.

139. In another embodiment, the present invention features a compound of any one of embodiments 112 to 138, wherein ring C is phenyl.

140. In another embodiment, the present invention features a compound of any one of embodiments 112 to 139, wherein ring B and ring C are phenyl.

141. In another embodiment, the present invention features a compound of any one of embodiments 112 to 140, wherein ring B is pyridyl and ring C is phenyl.

142. In another embodiment, the present invention features a compound of embodiment 1, wherein the compound is selected from Table 1.

143. In another embodiment, the present invention features a pharmaceutical composition comprising the compound of any one of embodiments 1 to 142 and a pharmaceutically acceptable carrier.

144. In another embodiment, the present invention features the pharmaceutical composition of embodiment 143, further comprising one or more additional therapeutic agent(s).

145. In another embodiment, the present invention features the pharmaceutical composition of embodiment 144, wherein the additional therapeutic agent is selected from a mucolytic agent, bronchodialator, an antibiotic, an anti-infective agent, a CFTR modulator, or an anti-inflammatory agent.

146. In another embodiment, the present invention features the pharmaceutical composition of embodiment 144, wherein the additional therapeutic agent is a CFTR modulator.

147. In another embodiment, the present invention features the pharmaceutical composition of embodiment 144, wherein the additional therapeutic agent is a CFTR corrector.

148. In another embodiment, the present invention features the pharmaceutical composition of embodiment 144, wherein the additional therapeutic agent is

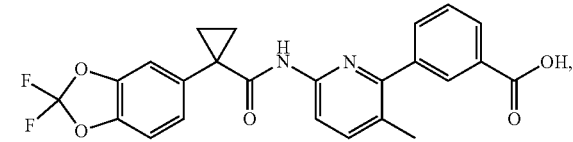 [SMILES: Cc1ccc(NC(=O)C2(c3ccc4c(c3)OC(F)(F)O4)CC2)nc1-c1cccc(C(=O)O)c1]

or pharmaceutically acceptable salt thereof.

149. In another embodiment, the present invention features the pharmaceutical composition of embodiment 144, wherein the additional therapeutic agent is

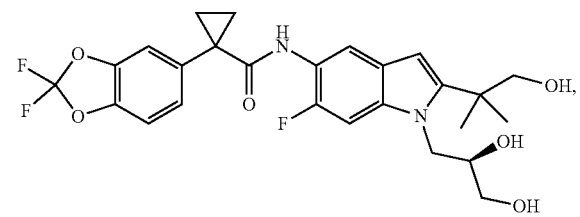 [SMILES: CC(C)(CO)c1cc2cc(NC(=O)C3(c4ccc5c(c4)OC(F)(F)O5)CC3)c(F)cc2n1C[C@@H](O)CO]

or pharmaceutically acceptable salt thereof.

150. In another embodiment, the present invention features the pharmaceutical composition of embodiment 144, wherein the additional therapeutic agent is

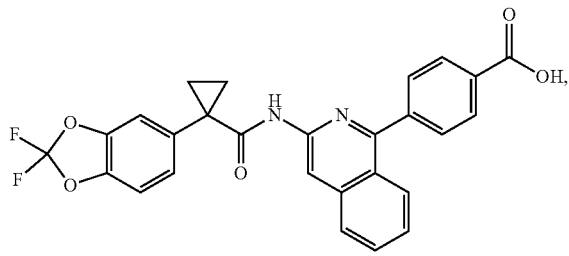 [SMILES: O=C(O)c1ccc(-c2nc(NC(=O)C3(c4ccc5c(c4)OC(F)(F)O5)CC3)cc3ccccc23)cc1]

or pharmaceutically acceptable salt thereof.

151. In another embodiment, the present invention features the pharmaceutical composition of embodiment 144, wherein the additional therapeutic agent is a CFTR potentiator.

152. In another embodiment, the present invention features the pharmaceutical composition of embodiment 144, wherein the additional therapeutic agent is

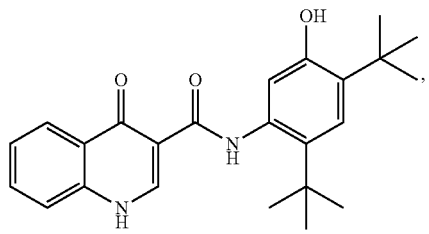 [SMILES: CC(C)(C)c1cc(C(C)(C)C)c(NC(=O)c2c[nH]c3ccccc3c2=O)cc1O]

or pharmaceutically acceptable salt thereof.

153. In another embodiment, the present invention features the pharmaceutical composition of embodiment 144, wherein the additional therapeutic agents are a CFTR corrector and a CFTR potentiator.

154. In another embodiment, the present invention features the pharmaceutical composition of embodiment 144, wherein the additional therapeutic agents are

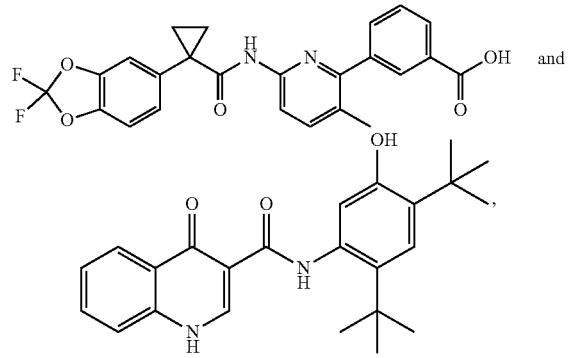

or pharmaceutically acceptable salts thereof.

155. In another embodiment, the present invention features the pharmaceutical composition of embodiment 144, wherein the additional therapeutic agents are

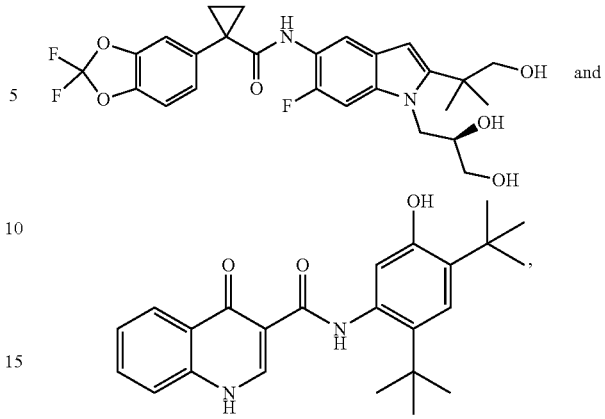

or pharmaceutically acceptable salts thereof.

156. In another embodiment, the present invention features the pharmaceutical composition of embodiment 144, wherein the additional therapeutic agents are

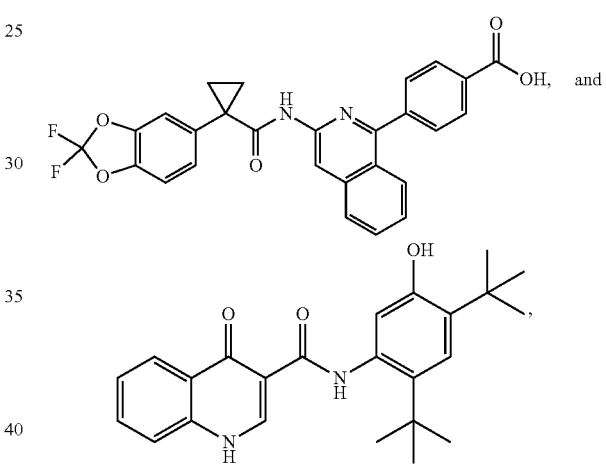

or pharmaceutically acceptable salts thereof.

157. In another embodiment, the present invention features a method of treating cystic fibrosis in a patient comprising administering to the patient an effective amount of the compound of any one of embodiments 1 to 142 or the pharmaceutical composition of any one of embodiments 143 to 156.

158. In another embodiment, the present invention features the method of embodiment 157, further comprising administering to the patient one or more additional therapeutic agent(s) prior to, concurrent with, or subsequent to the compound of any one of embodiments 1 to 137 or the pharmaceutical composition of any one of embodiments 138 to 151.

159. In another embodiment, the present invention features the method of embodiment 158, wherein the additional therapeutic agent is selected from a mucolytic agent, bronchodialator, an antibiotic, an anti-infective agent, a CFTR modulator, or an anti-inflammatory agent.

160. In another embodiment, the present invention features the method of embodiment 158, wherein the additional therapeutic agent is a CFTR modulator.

161. In another embodiment, the present invention features the method of embodiment 158, wherein the additional therapeutic agent is a CFTR corrector.

162. In another embodiment, the present invention features the method of embodiment 158, wherein the additional therapeutic agent is

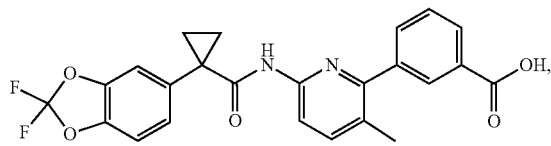 [SMILES: Cc1ccc(NC(=O)C2(c3ccc4c(c3)OC(F)(F)O4)CC2)nc1-c1cccc(C(=O)O)c1]

or a pharmaceutically acceptable salt thereof.

163. In another embodiment, the present invention features the method of embodiment 158, wherein the additional therapeutic agent is

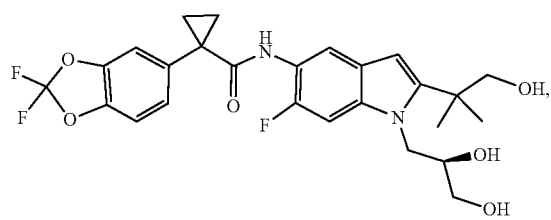 [SMILES: CC(C)(CO)c1cc2cc(NC(=O)C3(c4ccc5c(c4)OC(F)(F)O5)CC3)c(F)cc2n1C[C@@H](O)CO]

or a pharmaceutically acceptable salt thereof.

164. In another embodiment, the present invention features the method of embodiment 158, wherein the additional therapeutic agent is

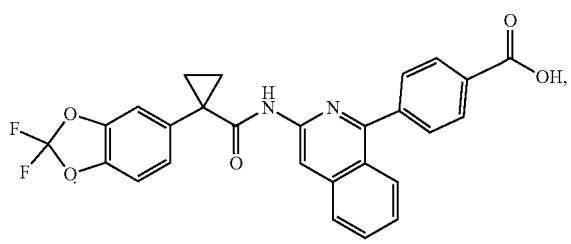

or a pharmaceutically acceptable salt thereof.

165. In another embodiment, the present invention features the method of embodiment 158, wherein the additional therapeutic agent is a CFTR potentiator.

166. In another embodiment, the present invention features the method of embodiment 158, wherein the additional therapeutic agent is

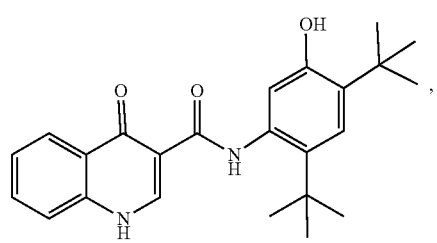 [SMILES: CC(C)(C)c1cc(C(C)(C)C)c(NC(=O)c2c[nH]c3ccccc3c2=O)cc1O]

or a pharmaceutically acceptable salt thereof.

167. In another embodiment, the present invention features the method of any one of embodiments 157 to 166, wherein the patient is homozygous in the F508del CFTR mutation.

168. In another embodiment, the present invention features the method of any one of embodiments 157 to 166, wherein the patient is heterozygous in the F508del CFTR mutation.

169. In another embodiment, the present invention features a kit comprising the compound of any one of embodiments 1 to 142 or the pharmaceutical composition of any one of embodiments 143 to 156, and instructions for use thereof.

170. In another embodiment, the present invention features the kit of embodiment 169, further comprising one or more additional therapeutic agent(s).

171. In another embodiment, the present invention features the kit of embodiment 170, wherein the additional therapeutic agent is selected from a mucolytic agent, bronchodialator, an antibiotic, an anti-infective agent, a CFTR modulator, or an anti-inflammatory agent.

172. In another embodiment, the present invention features the kit of embodiment 170, wherein the additional therapeutic agent is a CFTR modulator.

173. In another embodiment, the present invention features the kit of embodiment 170, wherein the additional therapeutic agent is a CFTR corrector.

174. In another embodiment, the present invention features the kit of embodiment 170, wherein the additional therapeutic agent is

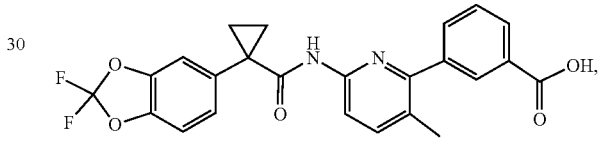

or a pharmaceutically acceptable salt thereof.

175. In another embodiment, the present invention features the kit of embodiment 170, wherein the additional therapeutic agent is

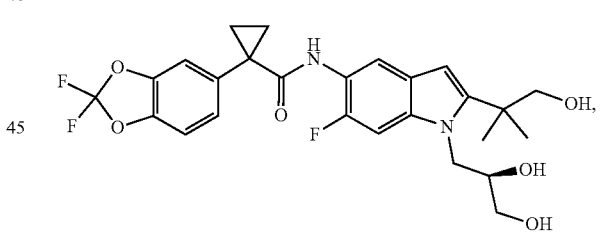

or a pharmaceutically acceptable salt thereof.

176. In another embodiment, the present invention features the kit of embodiment 170, wherein the additional therapeutic agent is

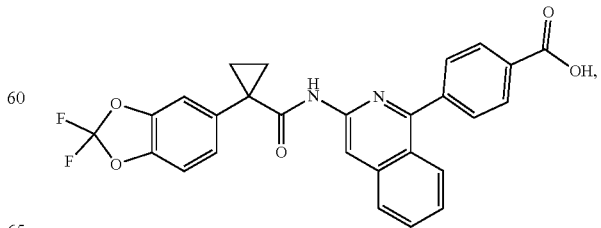

or a pharmaceutically acceptable salt thereof.

177. In another embodiment, the present invention features the kit of embodiment 170, wherein the additional therapeutic agent is a CFTR potentiator.

178. In another embodiment, the present invention features the kit of embodiment 170, wherein the additional therapeutic agent is

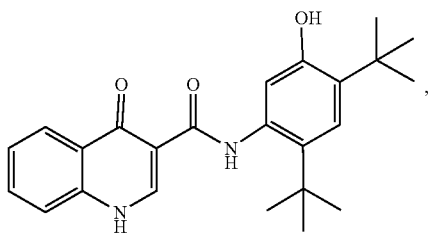 [SMILES: CC(C)(C)c1cc(C(C)(C)C)c(NC(=O)c2c[nH]c3ccccc3c2=O)cc1O]

or a pharmaceutically acceptable salt thereof.

179. In another embodiment, the present invention features the kit of embodiment 170, wherein the additional therapeutic agents are a CFTR corrector and a CFTR potentiator.

180. In another embodiment, the present invention features the kit of embodiment 170, wherein the additional therapeutic agents are

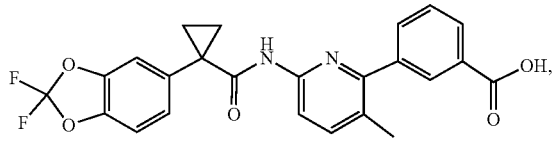 [SMILES: Cc1ccc(NC(=O)C2(c3ccc4c(c3)OC(F)(F)O4)CC2)nc1-c1cccc(C(=O)O)c1]

and

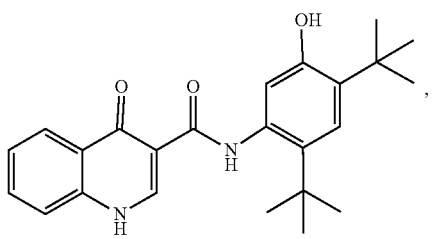 [SMILES: CC(C)(C)c1cc(C(C)(C)C)c(NC(=O)c2c[nH]c3ccccc3c2=O)cc1O]

or pharmaceutically acceptable salts thereof.

181. In another embodiment, the present invention features the kit of embodiment 170, wherein the additional therapeutic agents are

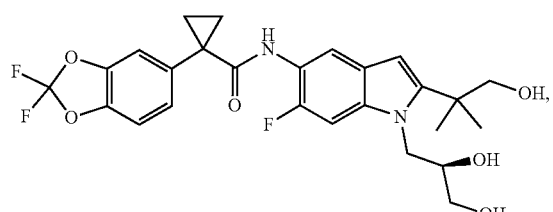

and

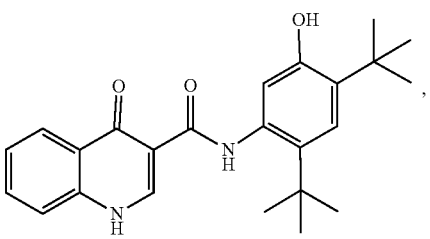 [SMILES: CC(C)(C)c1cc(C(C)(C)C)c(NC(=O)c2c[nH]c3ccccc3c2=O)cc1O]

or pharmaceutically acceptable salts thereof.

182. In another embodiment, the present invention features the kit of embodiment 170, wherein the additional therapeutic agents are

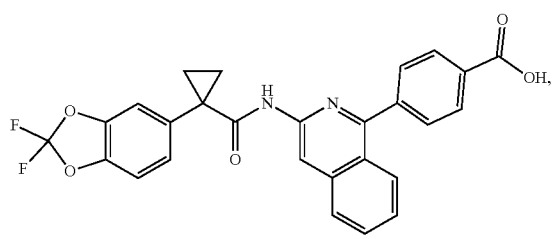 [SMILES: O=C(O)c1ccc(-c2nc(NC(=O)C3(c4ccc5c(c4)OC(F)(F)O5)CC3)cc3ccccc23)cc1]

and

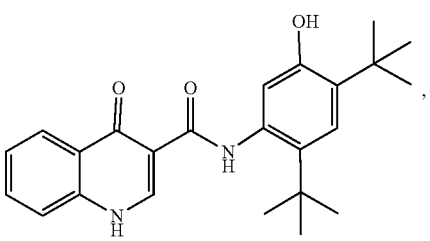 [SMILES: CC(C)(C)c1cc(C(C)(C)C)c(NC(=O)c2c[nH]c3ccccc3c2=O)cc1O]

or pharmaceutically acceptable salts thereof.

183. In another embodiment, the present invention features the kit of any one of embodiments 169 to 182, wherein the compound of any one of embodiments 1 to 142 or the pharmaceutical composition of any one of embodiments 143 to 156 and the one or more additional therapeutic agent(s) are in separate containers.

184. In another embodiment, the present invention features the kit of any one of embodiments 169 to 182, wherein the compound of any one of embodiments 1 to 142 or the pharmaceutical composition of any one of embodiments 143 to 156 and the one or more additional therapeutic agent(s) are in the same container.

185. In another embodiment, the present invention features the kit of embodiment 183 or 184, wherein the container is a bottle, vial, or blister pack, or combination thereof.

Methods of Preparing Compounds of Formula I

Compounds of the invention may be prepared by known methods and as illustrated in Schemes I-XX1. Ring A, B, C and R, $R_1$, $R_2$, $R_3$, $R_4$, X, Y, Z and n, o, p, q are as defined in the Specification unless noted otherwise below for each individual scheme.

Scheme I

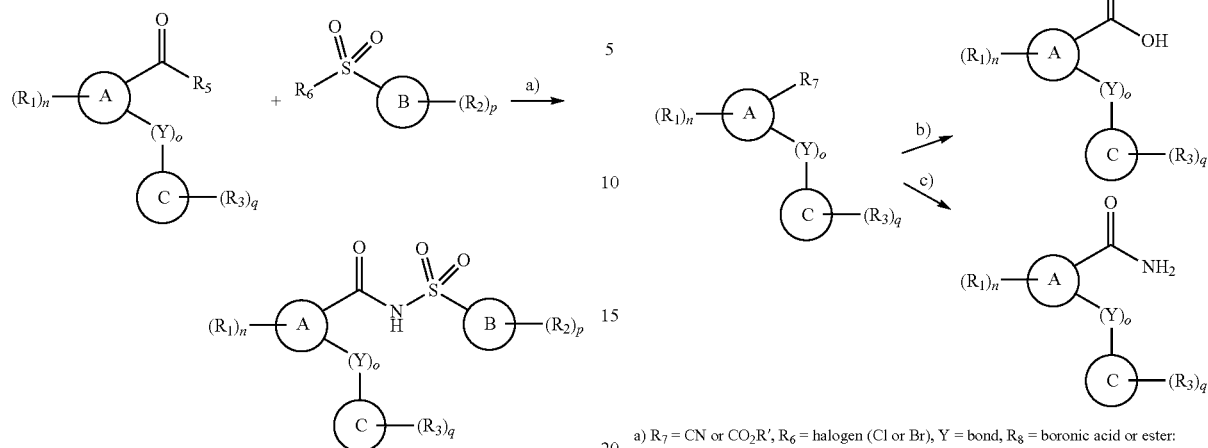

a) $R_5$ = OH, $R_6$ = $NH_2$: HATU, $Et_3N$ or $(i\text{-}Pr)_2NEt$ or $K_2CO_3$ or $Na_2CO_3$, DMF or $CH_2Cl_2$ or NMP; $R_5$ = OH, $R_6$ = $NH_2$: $SOCl_2$, $CH_2Cl_2$ and DMF (catalytic amount), then $Et_3N$, $CH_2Cl_2$; $R_5$ = $NH_2$, $R_6$ = Cl: NaH or $Cs_2CO_3$, DMF or THF; or pyridine, $CH_2Cl_2$.

a) $R_7$ = CN or $CO_2R'$, $R_6$ = halogen (Cl or Br), Y = bond, $R_8$ = boronic acid or ester: $Pd(dppf)Cl_2 \cdot CH_2Cl_2$, $NaHCO_3$ or $Na_2CO_3$, water, DMA or DME; Y = O or N(R'), $R_8$ = H: NaH or $Cs_2CO_3$ or KHMDS; DMF or DMSO or dioxane or DMF/THF; Y = O, $R_8$ = H: $Cu(OTf)_2$, $Cs_2CO_3$, toluene; Y = C(R')(R''), $R_8$ = ZnBr: $Pd(dppf)Cl_2 \cdot CH_2Cl_2$ or $Pd(PPh_3)_4$ and $Pd(OAc)_2$ and $tBu_3P \cdot HBF_4$, THF; Y = C(R')(R''), $R_8$ = Cl or Br: $K_2CO_3$ or KOH, DMF or i-PrOH. b) KOH or NaOH or LiOH, water, i-PrOH or EtOH or MeOH; or HCl in AcOH. c) $H_2O_2$, NaOH, EtOH; or KOH, EtOH.

Scheme II

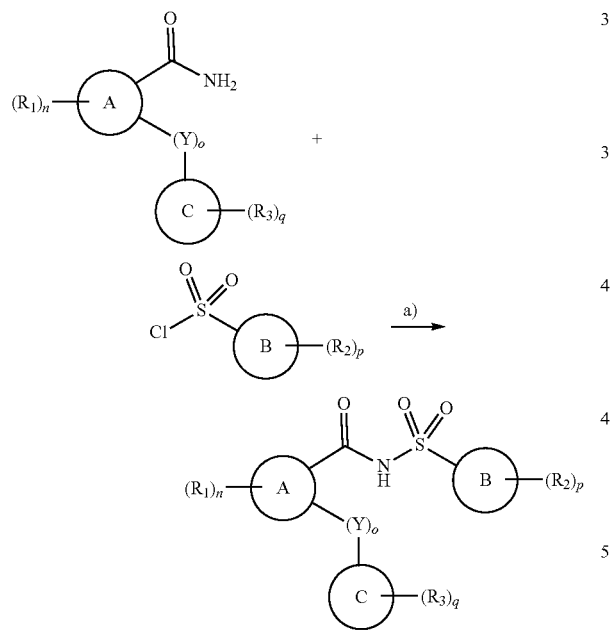

a) NaH or $Cs_2CO_3$, DMF or THF; or pyridine, $CH_2Cl_2$.

Scheme IV

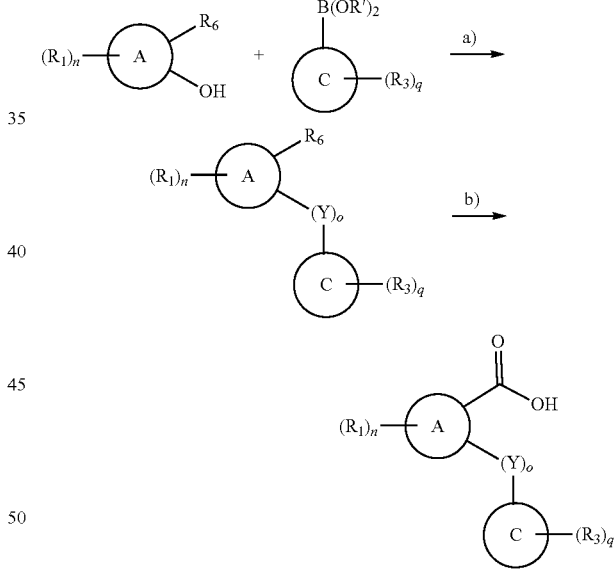

a) $R_6$ = Br, CN or $CO_2R''$: $Cu(OAc)_2$, pyridine, DCE; b) $R_6$ = Br or is absent: n-BuLi, THF, $CO_2$.

Scheme III

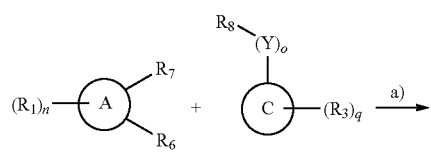

Scheme V

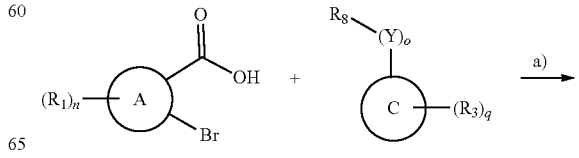

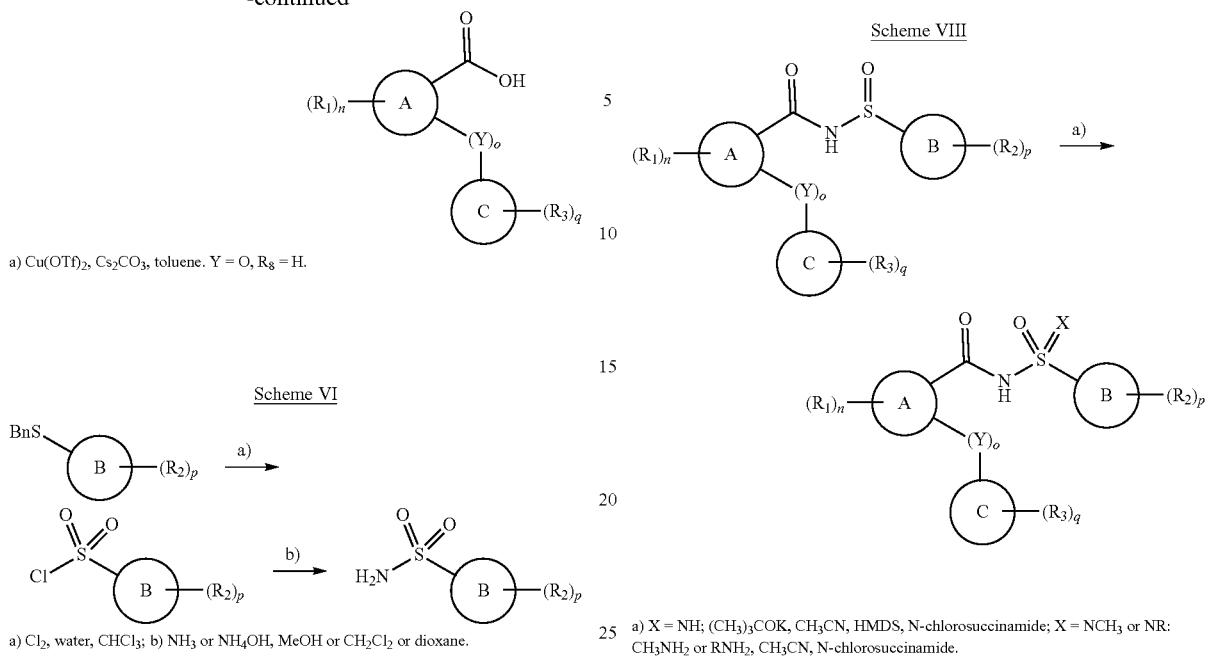

a) Cu(OTf)$_2$, Cs$_2$CO$_3$, toluene. Y = O, R$_8$ = H.

Scheme VI a) Cl$_2$, water, CHCl$_3$; b) NH$_3$ or NH$_4$OH, MeOH or CH$_2$Cl$_2$ or dioxane.

Scheme VIII a) X = NH; (CH$_3$)$_3$COK, CH$_3$CN, HMDS, N-chlorosuccinamide; X = NCH$_3$ or NR: CH$_3$NH$_2$ or RNH$_2$, CH$_3$CN, N-chlorosuccinamide.

Scheme VII

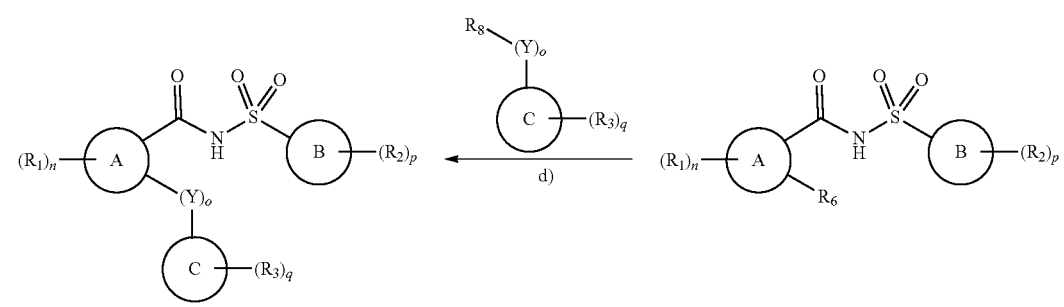

a) R$_6$ = halogen (Cl), R$_8$ = B(OR″)$_2$, R$_9$ = a protecting group (tert-butyl) or when R$_8$ is absent R$_1$ = moiety containing N: EtOH, toluene, water, Na$_2$CO$_3$, Pd(PPh$_3$)$_4$ or NaH and DMF; b) TFA, CH$_2$Cl$_2$; c) CDI, NaH, DMF; d) C = moiety containing N, Y and R$_8$ are absent or R$_8$ = NHR, NH$_2$ or NRR: K$_2$CO$_3$, DMSO or CsF, K$_2$CO$_3$, DMSO.

Scheme IX

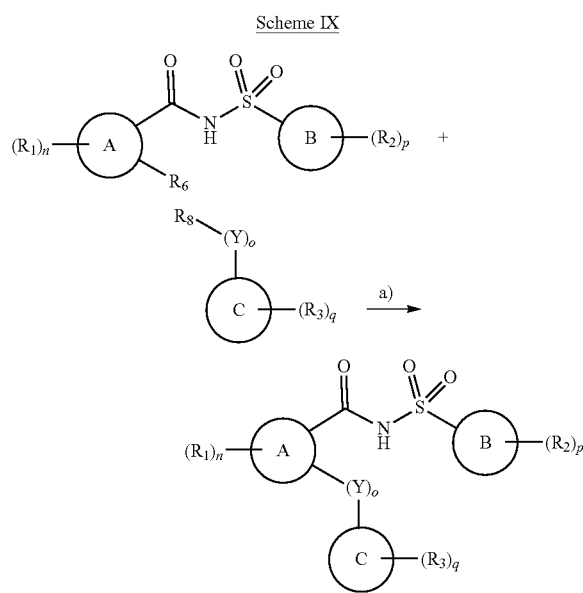

a) $R_6$ = halogen (Cl), Y = bond, $R_8$ = B(OR")$_2$: Pd(PPh$_3$)$_4$ or Pd(dppf)Cl$_2$*CH$_2$Cl$_2$, Na$_2$CO$_3$, DMF, water or dioxane or DMA.

Scheme X

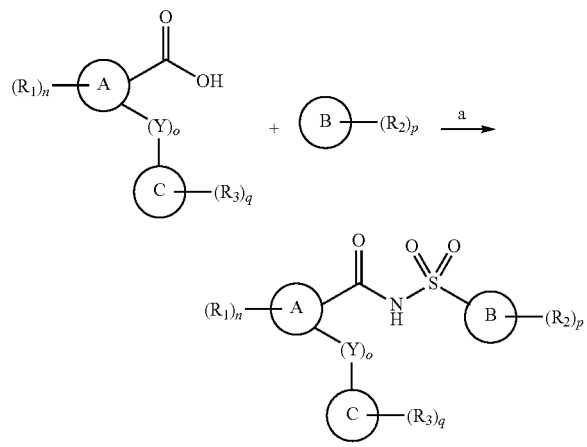

a) CSI, CH$_2$Cl$_2$, 45 min, then Et$_3$N, B = moiety containing N.

Scheme XI

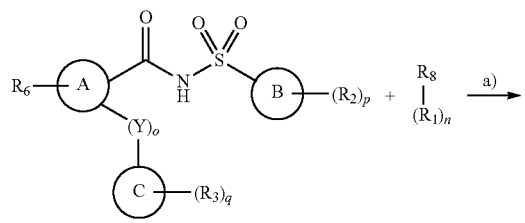

-continued

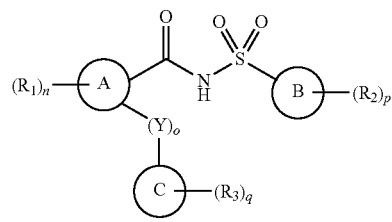

a) $R_6$ = halogen (Cl), Y = bond or Y = O, $R_8$ = B(OR")$_2$: Pd(PPh$_3$)$_4$, Na$_2$CO$_3$, K$_2$CO$_3$ or K$_3$PO$_4$, DMF; $R_6$ = halogen (Cl), Y = bond, $R_8$ = H: CsF, DMSO, then $R_1$ = moiety containing N; $R_6$ = B(OR")$_2$, Y = C(R') (R"), $R_8$ = halogen (Br): Pd(dppf)Cl$_2$*CH$_2$Cl$_2$, K$_2$CO$_3$, DMF; $R_6$ = halogen (Cl), $R_8$ = H or $R_8$ is absent, $R_1$ = moiety containing N: trans-diaminocyclohexane, DMF, CuI; $R_6$ = halogen (Cl), Y = bond, $R_8$ = B(OR")$_2$, $R_1$ = moiety containing C3-C8 cycloalkyl optionally substituted: PEPPSI™-IPr catalyst, K$_2$CO$_3$, dioxane.

Scheme XII a) $R_6$ = halogen (F, Cl), Y = bond or Y = O, $R_2$ = NH$_2$, p = 1, X = O: NH$_4$OH; $R_6$ = NO$_2$, Y = O, $R_2$ = NH$_2$, p = 1, X = O: CH$_3$COOH, Zn; $R_6$ = OMe, Y = C(R'), (R"), $R_2$ is = O, p = 1, X = O: CH$_3$COOH or dioxane, HBr or HCl: $R_6$ = NO$_2$, $R_2$ = NH$_2$, p = 1, X = NH: MeOH, Pd/C; $R_6$ = aldehyde, X = O, Y = C(R') (R"), $R_2$ = hydroxyalkyl: NaBH$_4$, MeOH.

Scheme XIII

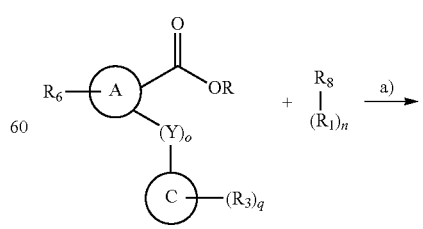

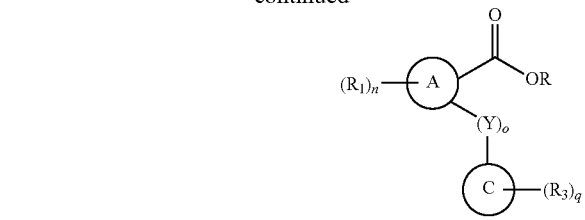

a) R = alkyl or H, $R_6$ = halogen (Cl), $R_8$ = $NH_2$ or OH, Y = O: DMA or NaH and DMF;
R = alkyl, $R_6$ = halogen (Cl), $R_8$ = alkyne; DMF, $Et_3N$, $PdCl_2(PPh_3)_2$, CuI, $PPh_3$;
R = alkyl, $R_6$ = halogen (Cl), Y = O, $R_8$ = ZnBr: Pd(dppf) $Cl_2*CH_2Cl_2$, then aq. sat. sol. of EDTA disodium salt and sat. aq. sol of $NH_4Cl$.

Scheme XIV

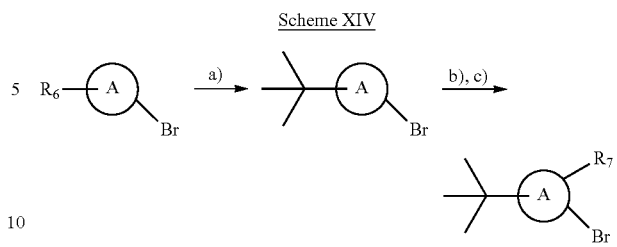

a) $R_6$ = halogen (I): $(CH_3)_3$CMgCl, CuCN, THF; b) 3-chlorobenzoperoxoic acid $C_2CH_2$ c) $R_7$ = CN: TMSCN, $Et_3N$, $CH_3CN$.

Scheme XV

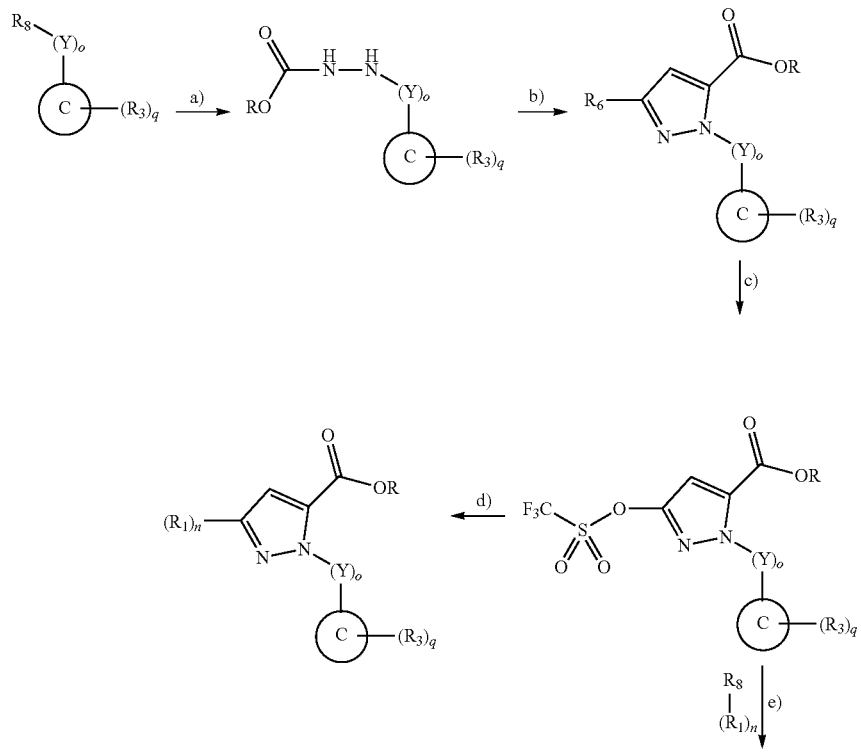

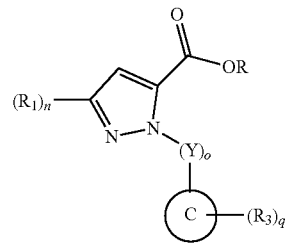

a) $R_8$ = Cl, Y = C(R')(R''), o = 1, R = alkyl (e.g., methyl): methyl N-aminocarbamate, $K_2CO_3$, DMF; b) $R_6$ = OH: dimetyl but -2-ynedioate, MeOH then NaOMe c) Pyridine, toluene triflic anhydride; d) $R_1$ = boronic ester: Bis(pinacolato)diboron, KOAc, dioxane, Pd(dppf)$Cl_2*CH_2Cl_2$, DPPF e) Y = C(R')(R''), o = 1, R = alkyl (e.g., methyl): $R_8$ = boronic acid, $K_2CO_3$, dioxane, Pd(dppf)$Cl_2*CH_2Cl_2$.

Scheme XVI

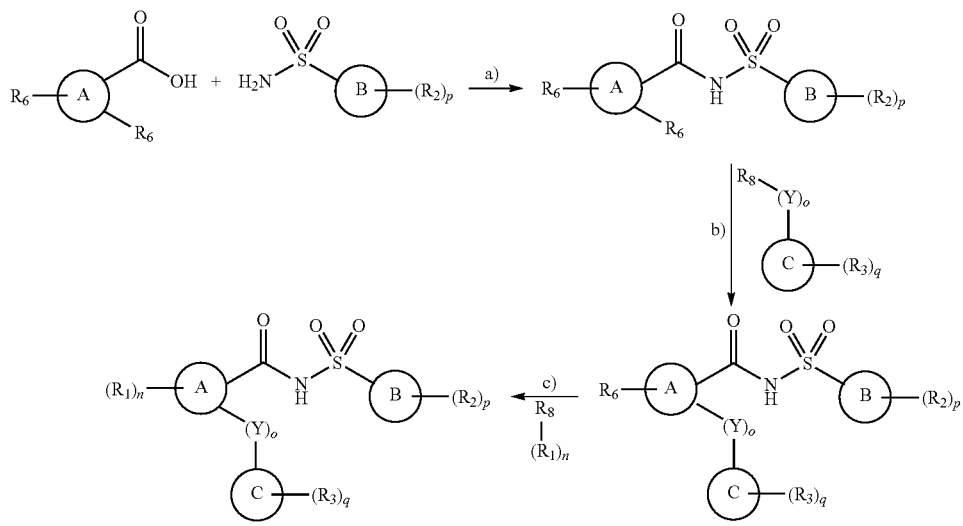

a) $R_6$ = halogen (Cl): CDI, NaH, DMF b) $R_8$ is absent, Y or o = 0: C = moiety containing N or $R_8$ = B(OR″)$_2$, Y or o = 0: $K_2CO_3$, DMSO or $Na_2CO_3$, DMF water, PD(PPh$_3$)$_4$, c) $R_8$ = B(OR″)$_2$, Pd(PPh$_3$)$_4$, $K_2CO_3$, DMF or $R_8$ is absent: $R_1$ = moiety containing N, n = 1: CsF, DMSO.

Scheme XVII

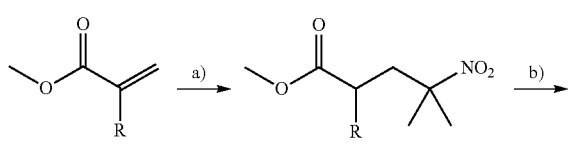

-continued

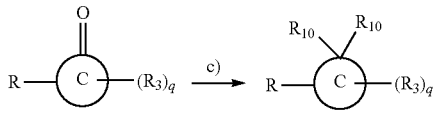

a) R = alkyl (methyl, ethyl): 2-nitropropane, dioxane, benzyltrimethylammonium hydroxide b) $R_3$ = gem-dimethyl group, q = 1, C = moiety containing N: NiCl$_2$ 6 H$_2$O, water, MeOH, NaBH$_4$; c) $R_{10}$ = H or D; LiAlH$_4$, THF or LiAlD$_4$, THF.

Scheme XVIII

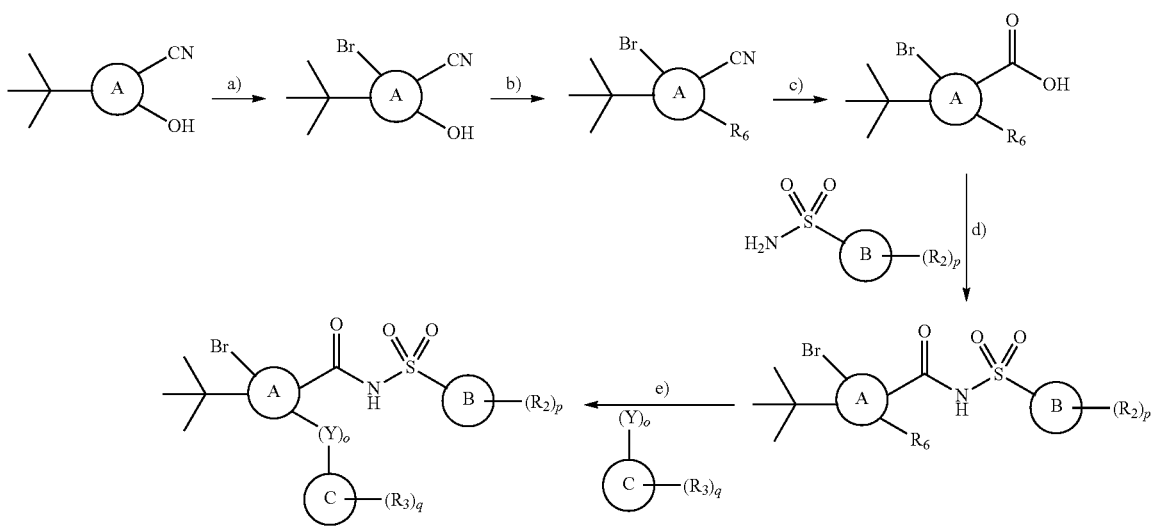

a) NBS, DCE; b) $R_6$ = Cl: POCl$_3$, PCl$_5$; c) $R_6$ = Cl: KOH, water, i-PrOH; d) CDI and DMF, then a mixture containing the desired silfonoamide and NaH in DMF; e) C = moiety containing N, Y or o = 0: $K_2CO_3$, DMSO.

Scheme XIX

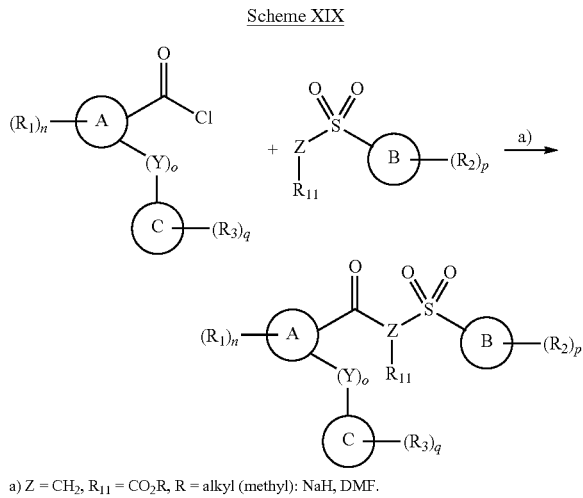

a) Z = CH$_2$, R$_{11}$ = CO$_2$R, R = alkyl (methyl): NaH, DMF.

Scheme XX

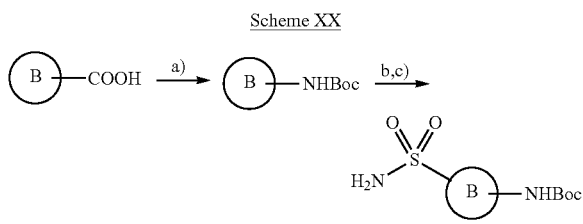

a) Et$_3$N, (CH$_3$)$_3$COH, DPPA; b) MTBE, (CH$_3$)$_2$CHMgCl in THF, then SO$_2$; c) CH$_3$COONa, H$_2$NOSO$_3$H.

Scheme XXI

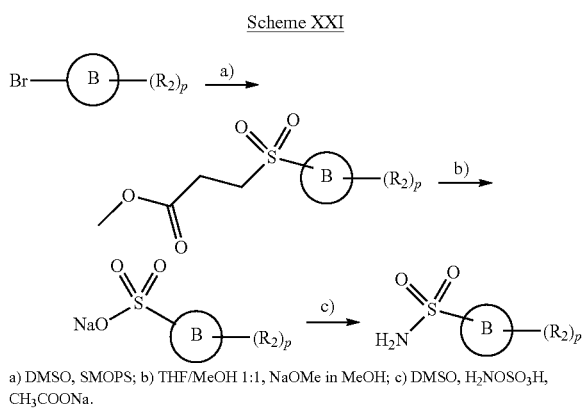

a) DMSO, SMOPS; b) THF/MeOH 1:1, NaOMe in MeOH; c) DMSO, H$_2$NOSO$_3$H, CH$_3$COONa.

Pharmaceutically Acceptable Salts and Prodrugs of Compounds of Formulas I-Id

It will also be appreciated that certain compounds of the compositions of the present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutical Compositions

Pharmaceutically Acceptable Vehicle, Adjuvant, or Carrier

In one aspect, the present invention features a pharmaceutical composition comprising a compound of formula I or pharmaceutically acceptable salt or prodrug thereof, and a pharmaceutically acceptable vehicle, adjuvant, or carrier.

As described above, the pharmaceutical compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: *The Science and Practice of Pharmacy*, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Additional Therapeutic Agent(s)

In another embodiment, the pharmaceutical compositions of the present invention further comprise one or more additional therapeutic agent(s). In one embodiment, the additional therapeutic agent is a CFTR modulator. In one embodiment, the additional therapeutic agent is a CFTR corrector. In one embodiment, the additional therapeutic agent is a CFTR potentiator. In another embodiment, the pharmaceutical composition comprises a compound of formula I and one or more of the following additional therapeutic agents.

In another embodiment, the additional therapeutic agent is selected from:

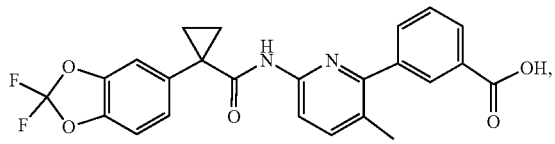 [SMILES: Cc1ccc(NC(=O)C2(c3ccc4c(c3)OC(F)(F)O4)CC2)nc1-c1cccc(C(=O)O)c1]

3-(6-(1-(2,2-difluorobenzo[d][1,3]dioxol-5-yl) cyclopropanecarboxamido)-3-methylpyridin-2-yl)benzoic acid, or pharmaceutically acceptable salt thereof;

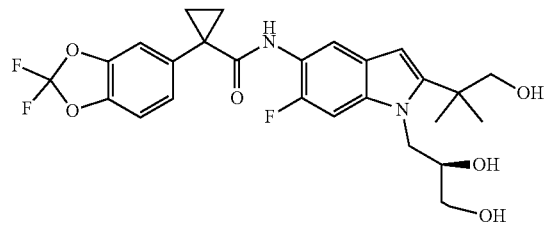 [SMILES: CC(C)(CO)c1cc2cc(NC(=O)C3(c4ccc5c(c4)OC(F)(F)O5)CC3)c(F)cc2n1C[C@@H](O)CCO]

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or a pharmaceutically acceptable salt thereof; or

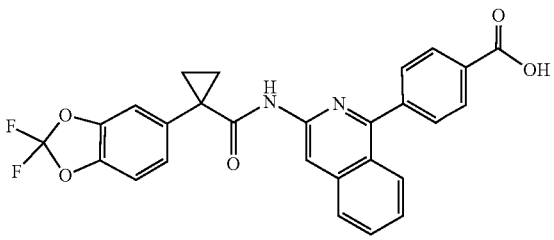 [SMILES: O=C(O)C1=CCC=C(c2nc(NC(=O)C3(c4ccc5c(c4)OC(F)(F)O5)CC3)cc3ccccc23)C=C1]

4-(3-(1-(2,2-difluorobenzo[d][1,3]dioxol-5-yl)cyclopropanecarboxamido) isoquinolin-1-yl)benzoic acid, or pharmaceutically acceptable salt thereof.

In another embodiment, the pharmaceutical composition of the present invention comprises a compound of formula I, or pharmaceutically acceptable salt thereof and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a compound of Table 1, or pharmaceutically acceptable salt thereof and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a compound of formula I, or pharmaceutically acceptable salt thereof and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a compound of Table 1, or pharmaceutically acceptable salt thereof and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a compound of formula I, or pharmaceutically acceptable salt thereof and 4-(3-(1-(2,2-difluorobenzo[d][1,3]dioxol-5-yl)cyclopropanecarboxamido) isoquinolin-1-yl)benzoic acid, or pharmaceutically acceptable salt thereof.

In another embodiment, the pharmaceutical composition of the present invention comprises a compound of Table 1, or pharmaceutically acceptable salt thereof and 4-(3-(1-(2, 2-difluorobenzo[d][1,3]dioxol-5-yl)cyclopropanecarboxamido) isoquinolin-1-yl)benzoic acid, or pharmaceutically acceptable salt thereof.

In another embodiment, the pharmaceutical composition of the present invention comprises a compound of formula I, or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises a compound of Table 1, or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(6-isopropoxy-3-pyridyl)-2-[-3-phenyl-1-piperidyl]pyridine-3-carboxamide (Compound 233), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(4-chloro-3-isobutoxy-phenyl)-2-(2,4,6-trimethylphenoxy)pyridine-3-carboxamide (Compound 238), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-(3-fluoro-5-isobutoxy-phenyl)-N-(1H-pyrazol-3-ylsulfonyl)-2-(2,4,6-trimethylphenoxy)pyridine-3-carboxamide (Compound 318), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-tert-butyl-2-(2,4,6-trimethylphenoxy)pyridine-3-carboxamide (Compound 228), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(3-fluoro-5-isobutoxy-phenyl)-2-(2,4,6-trimethylphenoxy)pyridine-3-carboxamide (Compound 196), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(6-isopropoxy-3-pyridyl)pyridine-3-carboxamide (Compound 337), or pharmaceutically acceptable salt thereof; and a compound selected from 3-(6-(1-(2,2-difluorobenzo[d][1,3] dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 368), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-8,8-dimethyl-2-(2,4,6-trimethylphenoxy)-6,7-dihydro-5H-quinoline-3-carboxamide (Compound 182), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-(benzenesulfonyl)-6-(3-fluoro-5-isobutoxy-phenyl)-2-[(4S)-2,2,4-trimethylpyrrolidin-1-yl]pyridine-3-carboxamide (Compound 1356), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(4-methylcyclohexyl)-2-(2,4,6-trimethylphenoxy)pyridine-3-carboxamide (Compound 172), or pharmaceutically acceptable salt thereof; and a compound selected from 3-(6-(1-(2,2-difluorobenzo[d][1,3]dioxol-5-yl)-cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-2-(2,6-dimethylphenoxy)-6-(3-fluoro-5-isobutoxy-phenyl)pyridine-3-carboxamide (Compound 639), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-(p-tolyl)-N-(1H-pyrazol-3-ylsulfonyl)-2-(2,4,6-trimethylphenoxy)pyridine-3-carboxamide (Compound 300), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (Compound 1660), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(4-chlorophenyl)-2-(2,4,6-trimethylphenoxy)pyridine-3-carboxamide (Compound 234), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-tert-butyl-N-[[6-(methylamino)-2-pyridyl]sulfonyl]-2-(2,4,6-trimethylphenoxy)pyridine-3-carboxamide (Compound 262), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191), or pharmaceutically acceptable salt thereof; and a compound selected from 3-(6-(1-(2,2-difluorobenzo[d][1,3] dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(4-chloro-2-fluoro-phenyl)-2-(2,4,6-trimethylphenoxy)pyridine-3-carboxamide (Compound 207), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(4-isobutoxyphenyl)-2-(2,4,6-trimethylphenoxy)pyridine-3-carboxamide (Compound 320), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-2-(2,3-dimethyl-1-piperidyl)-6-(6-isopropoxy-3-pyridyl)pyridine-3-carboxamide (Compound 353), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(3-fluoro-5-isobutoxy-phenyl)pyridine-3-carboxamide (Compound 171), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(6-isopropoxy-3-pyridyl)-2-(3-isopropyl-1-piperidyl)pyridine-3-carboxamide (Compound 114), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(6-isopropoxy-3-pyridyl)-2-(3-methyl-1-piperidyl)pyridine-3-carboxamide (Compound 321), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-2-(2,4-dimethylphenoxy)-8,8-dimethyl-6,7-dihydro-5H-quinoline-3-carboxamide (Compound 15), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-(4-aminothiazol-2-yl)sulfonyl-6-tert-butyl-2-(2,4,6-trimethylphenoxy)pyridine-3-carboxamide (Compound 265), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(4-isopropylphenyl)-2-(2,4,6-trimethylphenoxy)pyridine-3-carboxamide (Compound 164), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-tert-butyl-N-(1H-pyrazol-5-ylsulfonyl)-2-(2,4,6-trimethylphenoxy)pyridine-3-carboxamide (Compound 214), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(7-fluoro-1,3-benzodioxol-4-yl)-2-(2,4,6-trimethylphenoxy)pyridine-3-carboxamide (Compound 345), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(3-isobutoxyphenyl)-2-(2,4,6-trimethylphenoxy)pyridine-3-carboxamide (Compound 8), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)

cyclopropanecarboxamido) isoquinolin-1-yl)benzoic acid, or pharmaceutically acceptable salts thereof.

In another embodiment, the pharmaceutical composition of the present invention comprises N-(3-aminophenyl)sulfonyl-5-tert-butyl-2-[(2,4,6-trimethylphenyl)methyl]pyrazole-3-carboxamide (Compound 110), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(4-chloro-3-isopropoxy-phenyl)-2-(2,4,6-trimethylphenoxy)pyridine-3-carboxamide (Compound 281), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-6-(2-fluoro-5-isobutoxy-phenyl)-2-(2,4,6-trimethylphenoxy)pyridine-3-carboxamide (Compound 351), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-(3-aminopyrazin-2-yl)sulfonyl-8,8-dimethyl-2-(4-methyl-1-piperidyl)-6,7-dihydro-5H-quinoline-3-carboxamide (Compound 197), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-(4-chloro-3-isobutoxy-phenyl)-N-[(2-oxo-1H-pyridin-3-yl)sulfonyl]-2-(2,4,6-trimethylphenoxy)pyridine-3-carboxamide (Compound 136), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 2-(2,5-dimethylpyrrolidin-1-yl)-6-(3-fluoro-5-isobutoxy-phenyl)-N-[(2-oxo-1H-pyridin-3-yl)sulfonyl]pyridine-3-carboxamide (Compound 307), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-(2-fluoro-5-isobutoxy-phenyl)-N-[(2-oxo-1H-pyridin-3-yl)sulfonyl]-2-(2,4,6-trimethylphenoxy)pyridine-3-carboxamide (Compound 279), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-(4-chloro-3-propoxy-phenyl)-N-[(2-oxo-1H-pyridin-3-yl)sulfonyl]-2-(2,4,6-trimethylphenoxy)pyridine-3-carboxamide (Compound 72), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises 6-(3-isobutoxyphenyl)-N-[(2-oxo-1H-pyridin-3-yl)sulfonyl]-2-(2,4,6-trimethylphenoxy)pyridine-3-carboxamide (Compound 125), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-(benzenesulfonyl)-5-tert-butyl-2-[(2,4,6-trimethylphenyl)methyl]pyrazole-3-carboxamide (Compound 45), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-(3-aminophenyl)sulfonyl-4-isopropyl-2-[(2,4,6-trimethylphenyl)methyl]isoindoline-1-carboxamide (Compound 299), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present invention comprises N-[(2-methoxy-3-pyridyl)sulfonyl]-6-(1-methylcyclopropyl)-2-(2,4,6-trimethylphenoxy)pyridine-3-carboxamide (Compound 365), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present invention comprises N-[(6-amino-2-pyridyl)sulfonyl]-2-(2,2-dimethylpyrrolidin-1-yl)-6-(3-fluoro-5-isobutoxy-phenyl)pyridine-3-carboxamide (Compound 361), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In one embodiment, the above recited pharmaceutical compositions contain a pharmaceutically acceptable prodrug of the compound of the present invention.

In another embodiment, the pharmaceutical composition of the present invention comprises a compound of formula I, or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a compound of Table 1, or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-[-3-phenyl-1-piperidyl]pyridine-3-carboxamide (Compound 233), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(4-chloro-3-isobutoxy-phenyl)-2-(2,4,6-trimethylphenoxy)pyridine-3-carboxamide (Compound 238), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-(3-fluoro-5-isobutoxyphenyl)-N-(1H-pyrazol-3-ylsulfonyl)-2-(2,4,6-trimethylphenoxy)pyridine-3-carboxamide (Compound 318), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-tert-butyl-2-(2,4,6-trimethylphenoxy)pyridine-3-carboxamide (Compound 228), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(3-fluoro-5-isobutoxy-phenyl)-2-(2,4,6-trimethylphenoxy)pyridine-3-carboxamide (Compound 196), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(6-isopropoxy-3-pyridyl)pyridine-3-carboxamide (Compound 337), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 368), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-8,8-dimethyl-2-(2,4,6-trimethylphenoxy)-6,7-dihydro-5H-quinoline-3-carboxamide (Compound 182), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-(benzenesulfonyl)-6-(3-fluoro-5-isobutoxy-phenyl)-2-[(4S)-2,2,4-trimethylpyrrolidin-1-yl]pyridine-3-carboxamide (Compound 1356), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(4-methylcyclohexyl)-2-(2,4,6-trimethylphenoxy)pyridine-3-carboxamide (Compound 172), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-2-(2,6-dimethylphenoxy)-6-(3-fluoro-5-isobutoxy-phenyl)pyridine-3-carboxamide (Compound 639), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-(p-tolyl)-N-(1H-pyrazol-3-ylsulfonyl)-2-(2,4,6-trimethylphenoxy)pyridine-3-carboxamide (Compound 300), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (Compound 1660), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(4-chlorophenyl)-2-(2,4,6-trimethylphenoxy)pyridine-3-carboxamide (Compound 234), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-tert-butyl-N-[[6-(methylamino)-2-pyridyl]sulfonyl]-2-(2,4,6-trimethylphenoxy)pyridine-3-carboxamide (Compound 262), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(4-chloro-2-fluoro-phenyl)-2-(2,4,6-trimethylphenoxy)pyridine-3-carboxamide (Compound 207), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(4-isobutoxyphenyl)-2-(2,4,6-trimethylphenoxy)pyridine-3-carboxamide (Compound 320), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-2-(2,3-dimethyl-1-piperidyl)-6-(6-isopropoxy-3-pyridyl)pyridine-3-carboxamide (Compound 353), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(3-fluoro-5-isobutoxy-phenyl)pyridine-3-carboxamide (Compound 171), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-(3-isopropyl-1-piperidyl)pyridine-3-carboxamide (Compound 114), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-(3-methyl-1-piperidyl)pyridine-3-carboxamide (Compound 321), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-2-(2,4-dimethylphenoxy)-8,8-dimethyl-6,7-dihydro-5H-quinoline-3-carboxamide (Compound 15), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-(4-aminothiazol-2-yl)sulfonyl-6-tert-butyl-2-(2,4,6-trimethylphenoxy)pyridine-3-carboxamide (Compound 265), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(4-isopropylphenyl)-2-(2,4,6-trimethylphenoxy)pyridine-3-carboxamide (Compound 164), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-tert-butyl-N-(1H-pyrazol-5-ylsulfonyl)-2-(2,4,6-trimethylphenoxy)pyridine-3-carboxamide (Compound 214), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(7-fluoro-1,3-benzodioxol-4-yl)-2-(2,4,6-trimethylphenoxy)pyridine-3-carboxamide (Compound 345), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(3-isobutoxyphenyl)-2-(2,4,6-trimethylphenoxy)pyridine-3-carboxamide (Compound 8), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-(3-aminophenyl)sulfonyl-5-tert-butyl-2-[(2,4,6-trimethylphenyl)methyl]pyrazole-3-carboxamide (Compound 110), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(4-chloro-3-isopropoxy-phenyl)-2-(2,4,6-trimethylphenoxy)pyridine-3-carboxamide (Compound 281), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-6-(2-fluoro-5-isobutoxy-phenyl)-2-(2,4,6-trimethylphenoxy)pyridine-3-carboxamide (Compound 351), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-(3-aminopyrazin-2-yl)sulfonyl-8,8-dimethyl-2-(4-methyl-1-piperidyl)-6,7-dihydro-5H-quinoline-3-carboxamide (Compound 197), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-(4-chloro-3-isobutoxy-phenyl)-N-[(2-oxo-1H-pyridin-3-yl)sulfonyl]-2-(2,4,6-trimethylphenoxy)pyridine-3-carboxamide (Compound 136), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 2-(2,5-dimethylpyrrolidin-1-yl)-6-(3-fluoro-5-isobutoxy-phenyl)-N-[(2-oxo-1H-pyridin-3-yl)sulfonyl]pyridine-3-carboxamide (Compound 307), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-(2-fluoro-5-isobutoxy-phenyl)-N-[(2-oxo-1H-pyridin-3-yl)sulfonyl]-2-(2,4,6-trimethylphenoxy)pyridine-3-carboxamide (Compound 279), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-(4-chloro-3-propoxy-phenyl)-N-[(2-oxo-1H-pyridin-3-yl)sulfonyl]-2-(2,4,6-trimethylphenoxy)pyridine-3-carboxamide (Compound 72), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises 6-(3-isobutoxyphenyl)-N-[(2-oxo-1H-pyridin-3-yl)sulfonyl]-2-(2,4,6-trimethylphenoxy)pyridine-3-carboxamide (Compound 125), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-(benzenesulfonyl)-5-tert-butyl-2-[(2,4,6-trimethylphenyl)methyl]pyrazole-3-carboxamide (Compound 45), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-(3-aminophenyl)sulfonyl-4-isopropyl-2-[(2,4,6-trimethylphenyl)methyl]isoindoline-1-carboxamide (Compound 299), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(2-methoxy-3-pyridyl)sulfonyl]-6-(1-methylcyclopropyl)-2-(2,4,6-trimethylphenoxy)pyridine-3-carboxamide (Compound 365), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises N-[(6-amino-2-pyridyl)sulfonyl]-2-(2,2-dimethylpyrrolidin-1-yl)-6-(3-fluoro-5-isobutoxy-phenyl)pyridine-3-carboxamide (Compound 361), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In one embodiment, the above recited pharmaceutical compositions contain a pharmaceutically acceptable prodrug of the compound of the present invention.

In another embodiment, the pharmaceutical composition of the present invention comprises a compound of formula I, or pharmaceutically acceptable salt thereof; and (R)-1-(2, 2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises a compound of Table 1, or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-[-3-phenyl-1-piperidyl]pyridine-3-carboxamide (Compound 233), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(4-chloro-3-isobutoxy-phenyl)-2-(2,4,6-trimethylphenoxy)pyridine-3-carboxamide (Compound 238), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-(3-fluoro-5-isobutoxy-phenyl)-N-(1H-pyrazol-3-ylsulfonyl)-2-(2,4,6-trimethylphenoxy)pyridine-3-carboxamide (Compound 318), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-tert-butyl-2-(2,4,6-trimethylphenoxy)pyridine-3-carboxamide (Compound 228), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(3-fluoro-5-isobutoxy-phenyl)-2-(2,4,6-trimethylphenoxy)pyridine-3-carboxamide (Compound 196), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(6-isopropoxy-3-pyridyl)pyridine-3-carboxamide (Compound 337), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 368), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-8,8-dimethyl-2-(2,4,6-trimethylphenoxy)-6,7-dihydro-5H-quinoline-3-carboxamide (Compound 182), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-(benzenesulfonyl)-6-(3-fluoro-5-isobutoxy-phenyl)-2-[(4S)-2,2,4-trimethylpyrrolidin-1-yl]pyridine-3-carboxamide (Compound 1356), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(4-methylcyclohexyl)-2-(2,4,6-trimethylphenoxy)pyridine-3-carboxamide (Compound 172), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-2-(2,6-dimethylphenoxy)-6-(3-fluoro-5-isobutoxy-phenyl)pyridine-3-carboxamide (Compound 639), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-(p-tolyl)-N-(1H-pyrazol-3-ylsulfonyl)-2-(2,4,6-trimethylphenoxy)pyridine-3-carboxamide (Compound 300), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (Compound 1660), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(4-chlorophenyl)-2-(2,4,6-trimethylphenoxy)pyridine-3-carboxamide (Compound 234), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-tert-butyl-N-[[6-(methylamino)-2-pyridyl]sulfonyl]-2-(2,4,6-trimethylphenoxy)pyridine-3-carboxamide (Compound 262), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(4-chloro-2-fluoro-phenyl)-2-(2,4,6-trimethylphenoxy)pyridine-3-carboxamide (Compound 207), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(4-isobutoxyphenyl)-2-(2,4,6-trimethylphenoxy)pyridine-3-carboxamide (Compound 320), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-2-(2,3-dimethyl-1-piperidyl)-6-(6-isopropoxy-3-pyridyl)pyridine-3-carboxamide (Compound 353), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(3-fluoro-5-isobutoxy-phenyl)pyridine-3-carboxamide (Compound 171), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-(3-isopropyl-1-piperidyl)pyridine-3-carboxamide (Compound 114), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-(3-methyl-1-piperidyl)pyridine-3-carboxamide (Compound 321), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-2-(2,4-dimethylphenoxy)-8,8-dimethyl-6,7-dihydro-5H-quinoline-3-carboxamide (Compound 15), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-(4-aminothiazol-2-yl)sulfonyl-6-tert-butyl-2-(2,4,6-trimethylphenoxy)pyridine-3-carboxamide (Compound 265), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(4-isopropylphenyl)-2-(2,4,6-trimethylphenoxy)pyridine-3-carboxamide (Compound 164), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-tert-butyl-N-(1H-pyrazol-5-ylsulfonyl)-2-(2,4,6-trimethylphenoxy)pyridine-3-carboxamide (Compound 214), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(7-fluoro-1,3-benzodioxol-4-yl)-2-(2,4,6-trimethylphenoxy)pyridine-3-carboxamide (Compound 345), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(3-isobutoxyphenyl)-2-(2,4,6-trimethylphenoxy)pyridine-3-carboxamide (Compound 8), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-(3-aminophenyl)sulfonyl-5-tert-butyl-2-[(2,4,6-trimethylphenyl)methyl]pyrazole-3-carboxamide (Compound 110), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(4-chloro-3-isopropoxy-phenyl)-2-(2,4,6-trimethylphenoxy)pyridine-3-carboxamide (Compound 281), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-6-(2-fluoro-5-isobutoxy-phenyl)-2-(2,4,6-trimethylphenoxy)pyridine-3-carboxamide (Compound 351), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-(3-aminopyrazin-2-yl)sulfonyl-8,8-dimethyl-2-(4-methyl-1-piperidyl)-6,7-dihydro-5H-quinoline-3-carboxamide (Compound 197), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-(4-chloro-3-isobutoxy-phenyl)-N-[(2-oxo-1H-pyridin-3-yl)sulfonyl]-2-(2,4,6-trimethylphenoxy)pyridine-3-carboxamide (Compound 136), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 2-(2,5-dimethylpyrrolidin-1-yl)-6-(3-fluoro-5-isobutoxy-phenyl)-N-[(2-oxo-1H-pyridin-3-yl)sulfonyl]pyridine-3-carboxamide (Compound 307), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-(2-fluoro-5-isobutoxy-phenyl)-N-[(2-oxo-1H-pyridin-3-yl)sulfonyl]-2-(2,4,6-trimethylphenoxy)pyridine-3-carboxamide (Compound 279), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-(4-chloro-3-propoxy-phenyl)-N-[(2-oxo-1H-pyridin-3-yl)sulfonyl]-2-(2,4,6-trimethylphenoxy)pyridine-3-carboxamide (Compound 72), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises 6-(3-isobutoxyphenyl)-N-[(2-oxo-1H-pyridin-3-yl)sulfonyl]-2-(2,4,6-trimethylphenoxy)pyridine-3-carboxamide (Compound 125), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-(benzenesulfonyl)-5-tert-butyl-2-[(2,4,6-trimethylphenyl)methyl]pyrazole-3-carboxamide (Compound 45), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-(3-aminophenyl)sulfonyl-4-isopropyl-2-[(2,4,6-trimethylphenyl)methyl]isoindoline-1-carboxamide (Compound 299), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(2-methoxy-3-pyridyl)sulfonyl]-6-(1-methylcyclopropyl)-2-(2,4,6-trimethylphenoxy)pyridine-3-carboxamide (Compound 365), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present invention comprises N-[(6-amino-2-pyridyl)sulfonyl]-2-(2,2-dimethylpyrrolidin-1-yl)-6-(3-fluoro-5-isobutoxy-phenyl)pyridine-3-carboxamide (Compound 361), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the above recited pharmaceutical compositions contain a pharmaceutically acceptable prodrug of the compound of the present invention.

In another embodiment, the pharmaceutical composition of the present invention comprises a compound of formula I, or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises a compound of Table 1, or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-[-3-phenyl-1-piperidyl]pyridine-3-carboxamide (Compound 233), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(4-chloro-3-isobutoxy-phenyl)-2-(2,4,6-trimethylphenoxy)pyridine-3-carboxamide (Compound 238), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-(3-fluoro-5-isobutoxyphenyl)-N-(1H-pyrazol-3-ylsulfonyl)-2-(2,4,6-trimethylphenoxy)pyridine-3-carboxamide (Compound 318), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-tert-butyl-2-(2,4,6-trimethylphenoxy)pyridine-3-carboxamide (Compound 228), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(3-fluoro-5-isobutoxy-phenyl)-2-(2,4,6-trimethylphenoxy)pyridine-3-carboxamide-(Compound 196), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(6-isopropoxy-3-pyridyl)pyridine-3-carboxamide (Compound 337), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 368), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-8,8-dimethyl-2-(2,4,6-trimethylphenoxy)-6,7-dihydro-5H-quinoline-3-carboxamide (Compound 182), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-(benzenesulfonyl)-6-(3-fluoro-5-isobutoxy-phenyl)-2-[(4S)-2,2,4-trimethylpyrrolidin-1-yl]pyridine-3-carboxamide (Compound 1356), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(4-methylcyclohexyl)-2-(2,4,6-trimethylphenoxy)pyridine-3-carboxamide (Compound 172), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-2-(2,6-dimethylphenoxy)-6-(3-fluoro-5-isobutoxy-phenyl)pyridine-3-carboxamide (Compound 639), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-(p-tolyl)-N-(1H-pyrazol-3-ylsulfonyl)-2-(2,4,6-trimethylphenoxy)pyridine-3-carboxamide (Compound 300), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (Compound 1660), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(4-chlorophenyl)-2-(2,4,6-trimethylphenoxy)pyridine-3-carboxamide (Compound 234), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-tert-butyl-N-[[6-(methylamino)-2-pyridyl]sulfonyl]-2-(2,4,6-trimethylphenoxy)pyridine-3-carboxamide (Compound 262), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(4-chloro-2-fluoro-phenyl)-2-(2,4,6-trimethylphenoxy)pyridine-3-carboxamide (Compound 207), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(4-isobutoxyphenyl)-2-(2,4,6-trimethylphenoxy)pyridine-3-carboxamide (Compound 320), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-2-(2,3-dimethyl-1-piperidyl)-6-(6-isopropoxy-3-pyridyl)pyridine-3-carboxamide (Compound 353), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-2-[(2S,5R)-2,5-dimethylpyrrolidin-1-yl]-6-(3-fluoro-5-isobutoxy-phenyl)pyridine-3-carboxamide (Compound 171), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-(3-isopropyl-1-piperidyl)pyridine-3-carboxamide (Compound 114), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(6-isopropoxy-3-pyridyl)-2-(3-methyl-1-piperidyl)pyridine-3-carboxamide (Compound 321), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-2-(2,4-dimethylphenoxy)-8,8-dimethyl-6,7-dihydro-5H-quinoline-3-carboxamide (Compound 15), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-(4-aminothiazol-2-yl)sulfonyl-6-tert-butyl-2-(2,4,6-trimethylphenoxy)pyridine-3-carboxamide (Compound 265), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(4-isopropylphenyl)-2-(2,4,6-trimethylphenoxy)pyridine-3-carboxamide (Compound 164), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-tert-butyl-N-(1H-pyrazol-5-ylsulfonyl)-2-(2,4,6-trimethylphenoxy)pyridine-3-carboxamide (Compound 214), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(7-fluoro-1,3-benzodioxol-4-yl)-2-(2,4,6-trimethylphenoxy)pyridine-3-carboxamide (Compound 345), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(3-isobutoxyphenyl)-2-(2,4,6-trimethylphenoxy)pyridine-3-carboxamide (Compound 8), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-(3-aminophenyl)sulfonyl-5-tert-butyl-2-[(2,4,6-trimethylphenyl)methyl]pyrazole-3-carboxamide (Compound 110), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(4-chloro-3-isopropoxy-phenyl)-2-(2,4,6-trimethylphenoxy)pyridine-3-carboxamide (Compound 281), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-6-(2-fluoro-5-isobutoxy-phenyl)-2-(2,4,6-trimethylphenoxy)pyridine-3-carboxamide (Compound 351), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-(3-aminopyrazin-2-yl)sulfonyl-8,8-dimethyl-2-(4-methyl-1-piperidyl)-6,7-dihydro-5H-quinoline-3-carboxamide (Compound 197), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-(4-chloro-3-isobutoxy-phenyl)-N-[(2-oxo-1H-pyridin-3-yl)sulfonyl]-2-(2,4,6-trimethylphenoxy)pyridine-3-carboxamide (Compound 136), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 2-(2,5-dimethylpyrrolidin-1-yl)-6-(3-fluoro-5-isobutoxy-phenyl)-N-[(2-oxo-1H-pyridin-3-yl)sulfonyl]pyridine-3-carboxamide (Compound 307), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-(2-fluoro-5-isobutoxy-phenyl)-N-[(2-oxo-1H-pyridin-3-yl)sulfonyl]-2-(2,4,6-trimethylphenoxy)pyridine-3-carboxamide (Compound 279), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-(4-chloro-3-propoxy-phenyl)-N-[(2-oxo-1H-pyridin-3-yl)sulfonyl]-2-(2,4,6-trimethylphenoxy)pyridine-3-carboxamide (Compound 72), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises 6-(3-isobutoxyphenyl)-N-[(2-oxo-1H-pyridin-3-yl)sulfonyl]-2-(2,4,6-trimethylphenoxy)pyridine-3-carboxamide (Compound 125), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-(benzenesulfonyl)-5-tert-butyl-2-[(2,4,6-trimethylphenyl)methyl]pyrazole-3-carboxamide (Compound 45), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-(3-aminophenyl)sulfonyl-4-isopropyl-2-[(2,4,6-trimethylphenyl)methyl]isoindoline-1-carboxamide (Compound 299), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(2-methoxy-3-pyridyl)sulfonyl]-6-(1-methylcyclopropyl)-2-(2,4,6-trimethylphenoxy)pyridine-3-carboxamide (Compound 365), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present invention comprises N-[(6-amino-2-pyridyl)sulfonyl]-2-(2,2-dimethylpyrrolidin-1-yl)-6-(3-fluoro-5-isobutoxy-phenyl)pyridine-3-carboxamide (Compound 361), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the above recited pharmaceutical compositions contain a pharmaceutically acceptable prodrug of the compound of the present invention.

In another embodiment, the additional therapeutic agent is selected from the following table:

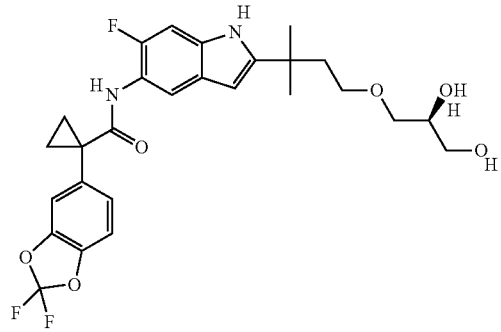

1

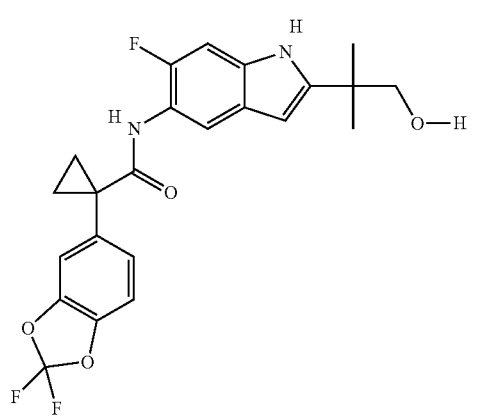

2

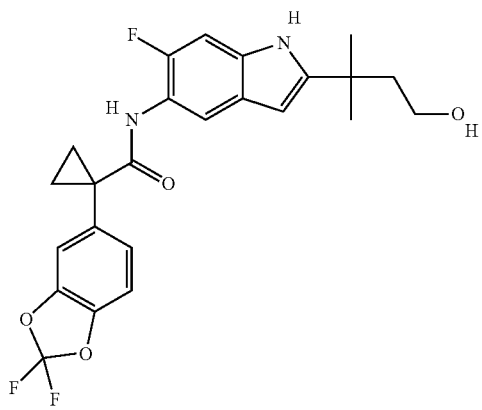

3

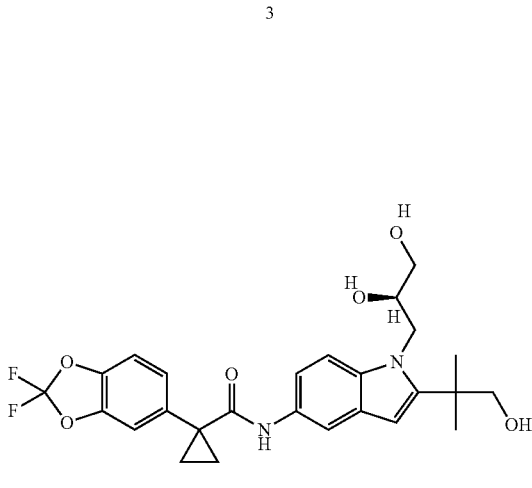

4

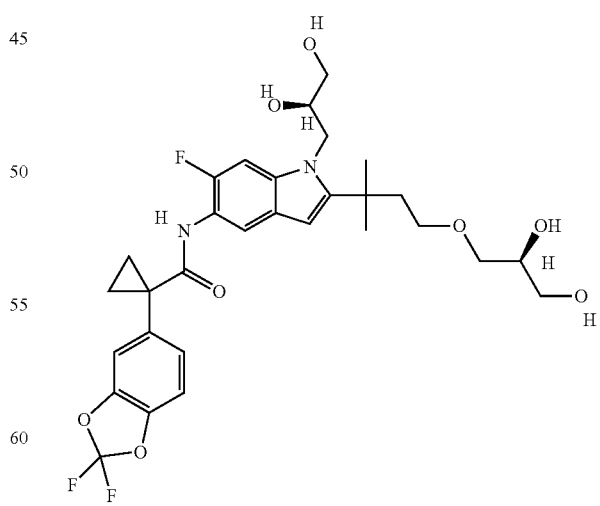

5

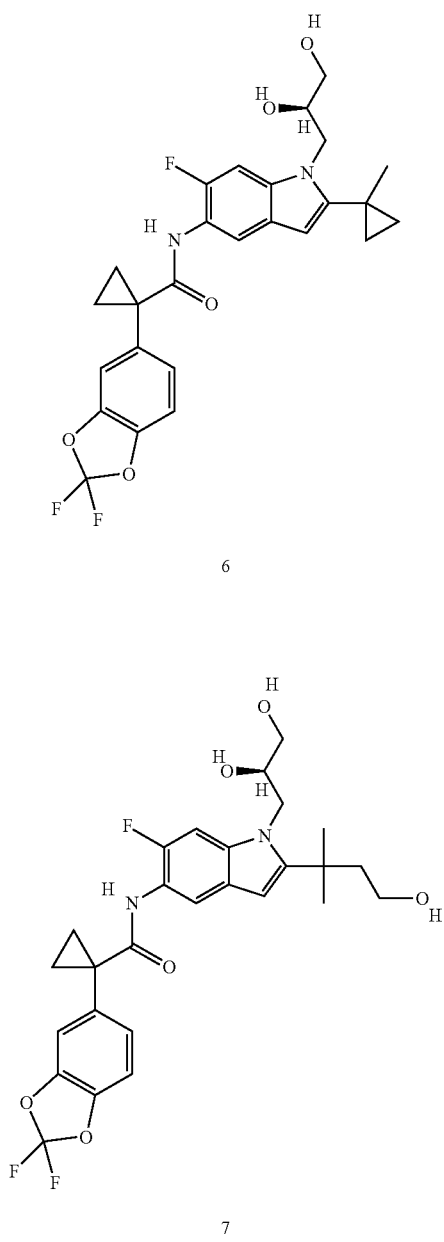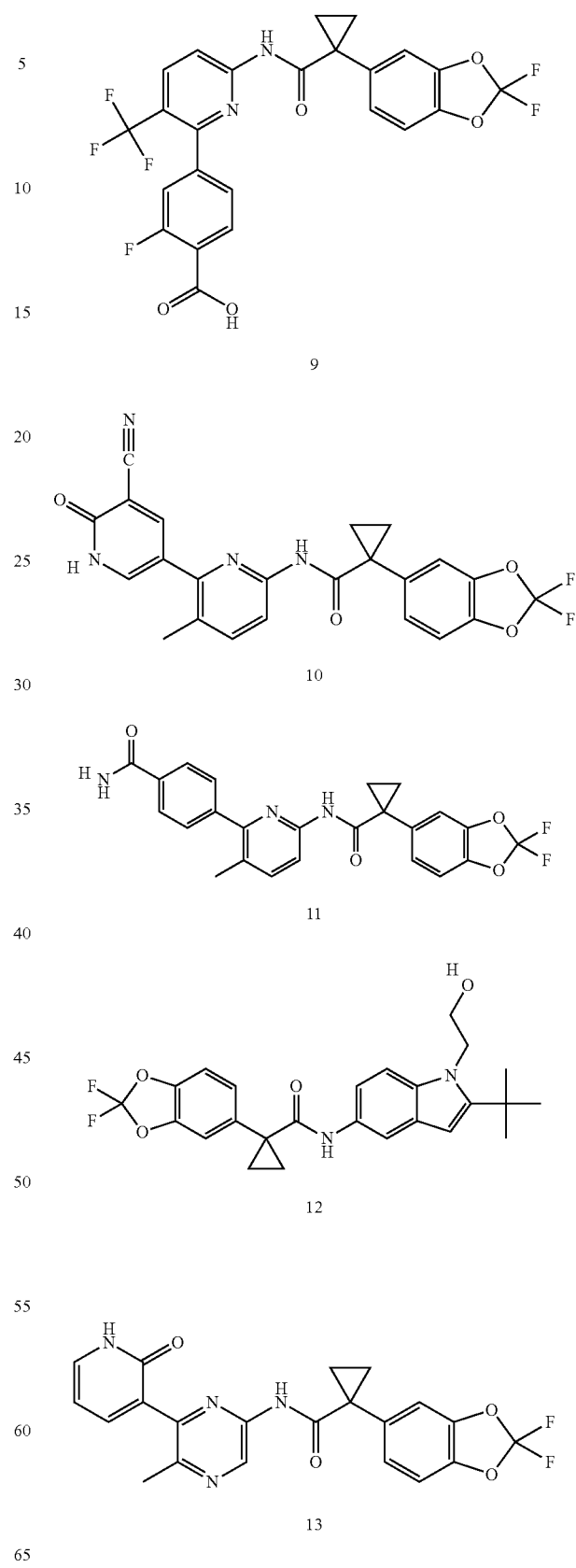

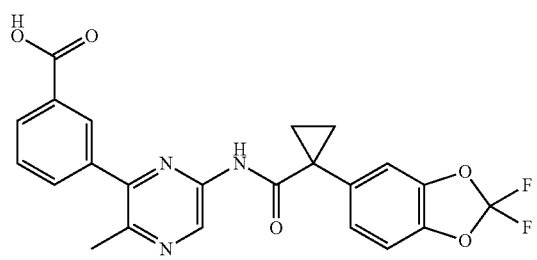 [SMILES: Cc1ncc(NC(=O)C2(c3ccc4c(c3)OC(F)(F)O4)CC2)nc1-c1cccc(C(=O)O)c1]

14

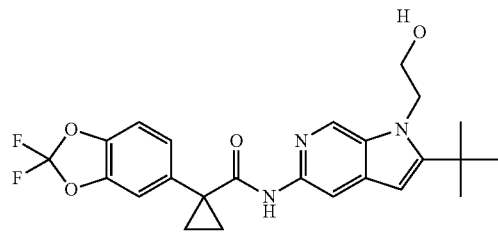

15

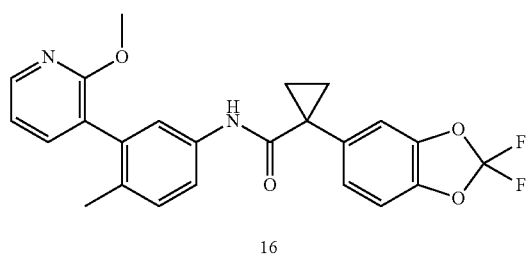

16

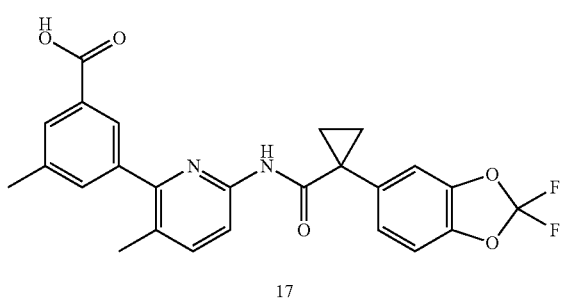

17

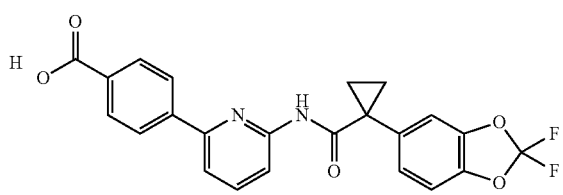

18

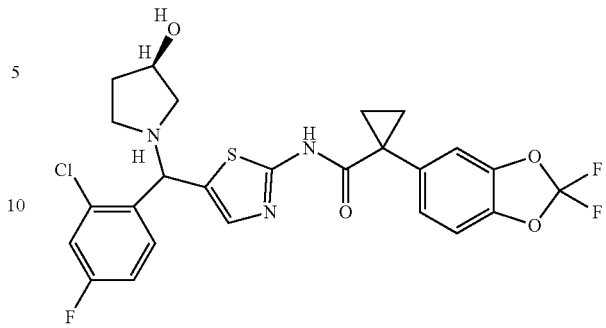

19

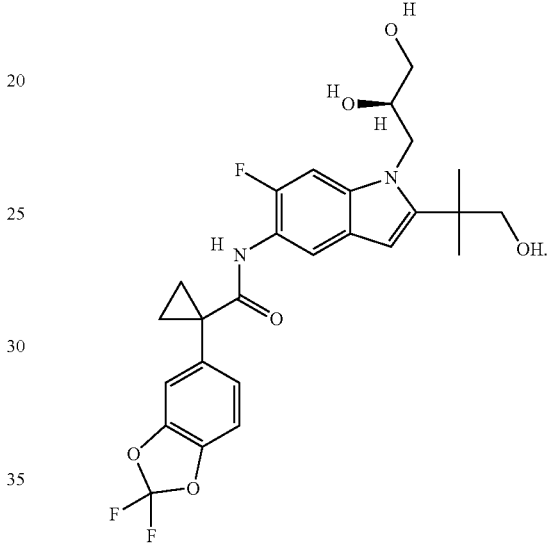

20

In one embodiment, the additional therapeutic agent is selected from the following table:

Compounds disclosed in U.S. Pat. No. 7,407,976
(Col 13, ln 35-col 66, ln 67; Compounds
1-100 in Table 1 at col 67, ln 1-col 127, ln 42)
Compounds disclosed in U.S. Pat. No. 7,645,789
(Col 16, ln 52-col 50, ln 22; Compounds
1-322 in Table 1 at col 50, in 24-col 167, ln 42)
Compounds disclosedin U.S. Pat. No. 7,659,268
(Col 16, ln 20-col 70, ln 52; Compounds
1-528 in Table 1 at col 70, ln 53-col 331, ln 34)
Compounds disclosed in U.S. Pat. No. 7,671,221
(Col 16, ln 12-col 54, ln 48; Compounds
1-1216 in Table 1 at col 54, ln 49-col 699, ln 27)
Compounds disclosed in U.S. Pat. No. 7,691,902
(Col 16, ln 11-col 54, ln 29; Compounds
1-959 in Table 1 at col 54, ln 29-col 683, ln 44)
Compounds disclosed in U.S. Pat. No. 7,741,321
(Col 16, ln 25-col 72, ln 17; Compounds
1-422 in Table 1 at col 72, ln 20-col 279, ln 15)
Compounds disclosed in U.S. Pat. No. 7,754,739
(Col 16, ln 1-col 22, ln 47; Compounds
1-2 in Table 1 at col 18, ln 26-65)
Compounds disclosed in U.S. Pat. No. 7,776,905
(Col 16, ln 23-col 38, ln 40; Compounds
1-306 in Table 1 at col 38, ln 45-col 96, ln 40)
Compounds disclosed in U.S. Pat. No. 7,973,169
(Col 9, ln 16-col 40, ln 40; Compounds
1-289 in Table 1 at col. 40, ln 41-col 289, ln 39)

-continued

Compounds disclosed in U.S. Pat. No. 7,977,322 (Col 6, ln 26-col 37, ln 47; Compounds 1-498 in Table 1 at col 37, ln 50-col 141, ln 40) Compounds disclosed in U.S. Pat. No. 7,999,113 (Col 6, ln 13-col 10, ln 67; Compounds 1-13 in Table 1 at col 11, ln 5-col 13, ln 65) Compounds disclosed in U.S. Pat. No. 8,227,615 (Col 6, ln 10-col 29, ln 66; Compounds 1-78 in Table 1 at col 30, ln 1-col 46, ln 48) Compounds disclosed in U.S. Pat. No. 8,299,099 (Col 6, ln 10-col 34, ln 18; Compounds 1-47 in Table 1 at col 34, ln 20-col 42, ln 35) Compounds disclosed in U.S. Published Application No. 2006-0052358 (Paragraphs [0034]-[0056]; [0077]-[0240]; Compounds 1-320 in Table 1 at paragraph [0241]) Compounds disclosed in U.S. Published Application No. 2009-0143381 (Paragraphs [0102]-[0263]; Compounds 1-28 in Table 1 at paragraph [0264]) Compounds disclosed in U.S. Published Application No. 2009-0170905 (Paragraphs [0012]-[0013]; [0030]-[0051]) Compounds disclosed in U.S. Published Application No. 2009-0253736 (Paragraphs [0031]-[0162]; Compounds 1-15 in Table 1 at paragraph [0163]) Compounds disclosed in U.S. Published Application No. 2011-0263654 (Paragraphs [0012]-[0013]; [0066]-[0141]) Compounds disclosed in U.S. Published Application No. 2011-0251253 (Paragraphs [0012]-[0013]; [0054]-[0079]) Compounds disclosed in PCT application WO2008141119 (Paragraphs [0100]-[0339]; Compounds 1-117 in Table 1 at paragraph [0340]) Compounds disclosed in U.S. Application No. 11/047,361 Compounds disclosed in U.S. Published Application No. 2013-0116238 (Paragraphs [0028]-[0044]; [0117]-[0128]), or combinations thereof.

In another embodiment, the additional therapeutic agent is selected from

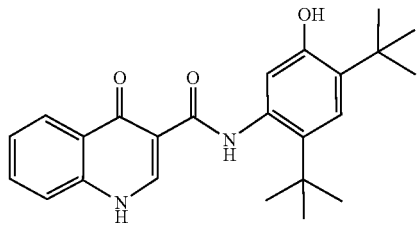 [SMILES: CC(C)(C)c1cc(C(C)(C)C)c(NC(=O)c2c[nH]c3ccccc3c2=O)cc1O]

N-(5-hydroxy-2,4-ditert-butyl-phenyl)-4-oxo-1H-quinoline-3-carboxamide, or pharmaceutically acceptable salt thereof; or

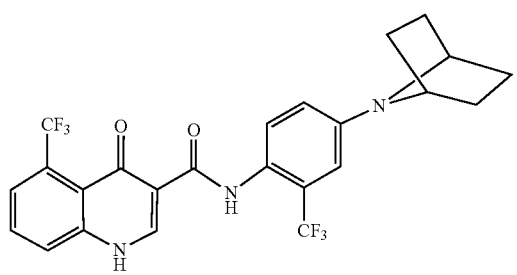

N-(4-(7-azabicyclo[2.21]heptan-7-yl)-2-(trifluoromethyl) phenyl)-4-oxo-5-(trifluoromethyl)-1,4-dihydroquinoline-3-carboxamide, or pharmaceutically acceptable salt thereof.

In another embodiment, the invention features a pharmaceutical composition comprising a) a compound of formula I; b) a compound selected from 3-(6-(1-(2,2-difluorobenzo [d][1,3]dioxol-5-yl) cyclopropanecarboxamido)-3-methylpyridin-2-yl)benzoic acid, (R)-1-(2,2-difluorobenzo[d][1, 3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d] [1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the invention features a pharmaceutical composition comprising a) a compound of Table 1; b) a compound selected from 3-(6-(1-(2,2-difluorobenzo[d] [1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d] [1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the above recited pharmaceutical compositions contain a pharmaceutically acceptable prodrug of the compound of the present invention.

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; and c) N-(5-hydroxy-2,4-ditert-butyl-phenyl)-4-oxo-1H-quinoline-3-carboxamide.

In another embodiment, the invention features a pharmaceutical composition comprising a) a compound of Table 1; b) 3-(6-(1-(2,2-difluorobenzo[d][1,3]dioxol-5-yl) cyclopropanecarboxamido)-3-methylpyridin-2-yl)benzoic acid; and c) N-(5-hydroxy-2,4-ditert-butyl-phenyl)-4-oxo-1H-quinoline-3-carboxamide.

In another embodiment, the invention features a pharmaceutical composition comprising a) a compound of formula I; b) (R)-1-(2,2-difluorobenzo[d][1,3]dioxol-5-yl)-N-(1-(2, 3-dihydroxypropyl)-6-fluoro-2-(1-hydroxy-2-methylpropan-2-yl)-1H-indol-5-yl)cyclopropanecarboxamide; and c) N-(5-hydroxy-2,4-ditert-butyl-phenyl)-4-oxo-1H-quinoline-3-carboxamide.

In another embodiment, the invention features a pharmaceutical composition comprising a) a compound of Table 1; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) N-(5-hydroxy-2,4-ditert-butyl-phenyl)-4-oxo-1H-quinoline-3-carboxamide.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; and c) N-(5-hydroxy-2,4-ditert-butyl-phenyl)-4-oxo-1H-quinoline-3-carboxamide.

In another embodiment, the invention features a pharmaceutical composition comprising a) a compound of Table 1; b) 4-(3-(1-(2,2-difluorobenzo[d][1,3]dioxol-5-yl)cyclopropanecarboxamido) isoquinolin-1-yl)benzoic acid; and c) N-(5-hydroxy-2,4-ditert-butyl-phenyl)-4-oxo-1H-quinoline-3-carboxamide.

In another embodiment, the above recited pharmaceutical compositions contain a pharmaceutically acceptable prodrug of the compound of the present invention.

In another embodiment, the additional therapeutic agent is selected from the following table:

| |
|---|
| Compounds disclosed in U.S. Published Application No. 2005-0113423 (Paragraph [00146]; Compounds IA-1-IA-136 and Compounds I-1-I-21 in Tables 1 and 2 at paragraphs [0391]-[0392]) |
| Compounds disclosed in U.S. Published Application No. 2005-0059687 (Paragraphs [00100]-[00101]; Compounds 1-405 in Table 1 at paragraph [0169]) |
| Compounds 1-108 disclosed in U.S. Pat. No. 7,598,412 (Col 22, ln 14-col 79, ln 20;Table 1) |
| Compounds 1-485 disclosed in U.S. Pat. No. 7,495,103 (Col 51, ln 1-col 63, ln 43; Table 1) |
| Compounds 1-718 disclosed in U.S. Pat. No. 8,354,427 (Col 51, ln 3-col 71, ln 46; Table 1) |
| Compounds 1-233 disclosed in U.S. Published Application No. 2007-0105833 (Paragraph [00145]; Table 1) |
| Compounds 1-26 disclosed in U.S. Pat. No. 8,242,149 (Col 46, ln 47-col 57, ln 37; Table 1) |
| Compounds 1-18 disclosed in U.S. Pat. No. 8,314,256 (Col 21, ln 1-col 26, ln 19) |
| Compounds 1-14 disclosed in U.S. Pat. No. 8,399,479 (Col 36, ln 20-col 38, ln 40; Table 1) |
| Compounds 1-18 disclosed in U.S. Pat. No. 8,188,283 (Col 38, ln 43-col 43, ln 36; Table 1) |
| Compounds 1-16 disclosed in U.S. Published Application No. 2010-0249180 (Paragraph [0173]; Table 1) |
| Compounds 1-19 disclosed in U.S. Published Application No. 2011-0008259 (Paragraph [0172]; Table 1) |
| Compounds 1-129 disclosed in U.S. Pat. No. 8,367,660 (Col 57, ln 31-col 81, ln 24; Table1) |

In another embodiment, the invention features a pharmaceutical composition comprising a) a compound of formula I; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the invention features a pharmaceutical composition comprising a) a compound of Table 1; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the above recited pharmaceutical compositions contain a pharmaceutically acceptable prodrug of the compound of the present invention.

In another embodiment, the invention features a pharmaceutical composition comprising a) a compound of formula I; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamide); and UCCF-152 (3-[2-(benzyloxy)phenyl]-5-(chloromethyl)isoxazole).

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; and c) N-(5-hydroxy-2,4-ditert-butyl-phenyl)-4-oxo-1H-quinoline-3-carboxamide.

In another embodiment, the invention features a pharmaceutical composition comprising a) a compound of Table 1; b) 3-(6-(1-(2,2-difluorobenzo[d][1,3]dioxol-5-yl) cyclopropanecarboxamido)-3-methylpyridin-2-yl)benzoic acid; and c) N-(5-hydroxy-2,4-ditert-butyl-phenyl)-4-oxo-1H-quinoline-3-carboxamide.

In another embodiment, the invention features a pharmaceutical composition comprising a) a compound of formula I; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) N-(5-hydroxy-2,4-ditert-butyl-phenyl)-4-oxo-1H-quinoline-3-carboxamide.

In another embodiment, the invention features a pharmaceutical composition comprising a) a compound of Table 1; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) N-(5-hydroxy-2,4-ditert-butyl-phenyl)-4-oxo-1H-quinoline-3-carboxamide.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; and c) N-(5-hydroxy-2,4-ditert-butyl-phenyl)-4-oxo-1H-quinoline-3-carboxamide.

In another embodiment, the invention features a pharmaceutical composition comprising a) a compound of Table 1; b) 4-(3-(1-(2,2-difluorobenzo[d][1,3]dioxol-5-yl)cyclopropanecarboxamido) isoquinolin-1-yl)benzoic acid; and c) N-(5-hydroxy-2,4-ditert-butyl-phenyl)-4-oxo-1H-quinoline-3-carboxamide.

In another embodiment, the above recited pharmaceutical compositions contain a pharmaceutically acceptable prodrug of the compound of the present invention.

In another embodiment, the pharmaceutical composition of the present invention comprises a) N-[(6-amino-2-pyridyl)sulfonyl]-6-(6-isopropoxy-3-pyridyl)-2-[-3-phenyl-1-piperidyl]pyridine-3-carboxamide (Compound 233), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c)

3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(4-chloro-3-isobutoxy-phenyl)-2-(2,4,6-trimethylphenoxy)pyridine-3-carboxamide (Compound 238), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-(3-fluoro-5-isobutoxy-phenyl)-N-(1H-pyrazol-3-ylsulfonyl)-2-(2,4,6-trimethylphenoxy)pyridine-3-carboxamide (Compound 318), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-tert-butyl-2-(2,4,6-trimethylphenoxy)pyridine-3-carboxamide (Compound 228), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(3-fluoro-5-isobutoxy-phenyl)-2-(2,4,6-trimethylphenoxy)pyridine-3-carboxamide (Compound 196), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-2-[(2S,5R)-2,5-dimethylpyrrolidin-1-yl]-6-(6-isopropoxy-3-pyridyl)pyridine-3-carboxamide (Compound 337), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 368), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-8,8-dimethyl-2-(2,4,6-trimethylphenoxy)-6,7-dihydro-5H-quinoline-3-carboxamide (Compound 182), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-(benzenesulfonyl)-6-(3-fluoro-5-isobutoxy-phenyl)-2-[(4S)-2,2,4-trimethylpyrrolidin-1-yl]pyridine-3-carboxamide (Compound 1356), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(4-methylcyclohexyl)-2-(2,4,6-trimethylphenoxy)pyridine-3-carboxamide (Compound 172), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-2-(2,6-dimethylphenoxy)-6-(3-fluoro-5-isobutoxy-phenyl)pyridine-3-carboxamide (Compound 639), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-(p-tolyl)-N-(1H-pyrazol-3-ylsulfonyl)-2-(2,4,6-trimethylphenoxy)pyridine-3-carboxamide (Compound 300), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (Compound 1660), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(4-chlorophenyl)-2-(2,4,6-trimethylphenoxy)pyridine-3-carboxamide (Compound 234), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-tert-butyl-N-[[6-(methylamino)-2-pyridyl]sulfonyl]-2-(2,4,6-trimethylphenoxy)pyridine-3-carboxamide (Compound 262), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxdl-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(4-chloro-2-fluoro-phenyl)-2-(2,4,6-trimethylphenoxy)pyridine-3-carboxamide (Compound 207), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(4-isobutoxyphenyl)-2-(2,4,6-trimethylphenoxy)pyridine-3-carboxamide (Compound 320), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-2-(2,3-dimethyl-1-piperidyl)-6-(6-isopropoxy-3-pyridyl)pyridine-3-carboxamide (Compound 353), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-2-[(2S,5R)-2,5-dimethylpyrrolidin-1-yl]-6-(3-fluoro-5-isobutoxy-phenyl)pyridine-3-carboxamide (Compound 171), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(6-isopropoxy-3-pyridyl)-2-(3-isopropyl-1-piperidyl)pyridine-3-carboxamide (Compound 114), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(6-isopropoxy-3-pyridyl)-2-(3-methyl-1-piperidyl)pyridine-3-carboxamide (Compound 321), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-2-(2,4-dimethylphenoxy)-8,8-dimethyl-6,7-dihydro-5H-quinoline-3-carboxamide (Compound 15), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-(4-aminothiazol-2-yl)sulfonyl-6-tert-butyl-2-(2,4,6-trimethylphenoxy)pyridine-3-carboxamide (Compound 265), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(4-isopropylphenyl)-2-(2,4,6-trimethylphenoxy)pyridine-3-carboxamide (Compound 164), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-tert-butyl-N-(1H-pyrazol-5-ylsulfonyl)-2-(2,4,6-trimethylphenoxy)pyridine-3-carboxamide (Compound 214), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(7-fluoro-1,3-benzodioxol-4-yl)-2-(2,4, 6-trimethylphenoxy)pyridine-3-carboxamide (Compound 345), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(3-isobutoxyphenyl)-2-(2,4,6-trimethylphenoxy)pyridine-3-carboxamide (Compound 8), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-(3-aminophenyl)sulfonyl-5-tert-butyl-2-[(2,4,6-trimethylphenyl)methyl]pyrazole-3-carboxamide (Compound 110), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(4-chloro-3-isopropoxy-phenyl)-2-(2,4,6-trimethylphenoxy)pyridine-3-carboxamide (Compound 281), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-6-(2-fluoro-5-isobutoxy-phenyl)-2-(2,4,6-trimethylphenoxy)pyridine-3-carboxamide (Compound 351), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-(3-aminopyrazin-2-yl)sulfonyl-8,8-dimethyl-2-(4-methyl-1-piperidyl)-6,7-dihydro-5H-quinoline-3-carboxamide (Compound 197), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-(4-chloro-3-isobutoxy-phenyl)-N-[(2-oxo-1H-pyridin-3-yl)sulfonyl]-2-(2,4,6-trimethylphenoxy)pyridine-3-carboxamide (Compound 136), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 2-(2,5-dimethylpyrrolidin-1-yl)-6-(3-fluoro-5-isobutoxy-phenyl)-N-[(2-oxo-1H-pyridin-3-yl)sulfonyl]pyridine-3-carboxamide (Compound 307), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-(2-fluoro-5-isobutoxy-phenyl)-N-[(2-oxo-1H-pyridin-3-yl)sulfonyl]-2-(2,4,6-trimethylphenoxy)pyridine-3-carboxamide (Compound 279), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-(4-chloro-3-propoxy-phenyl)-N-[(2-oxo-1H-pyridin-3-yl)sulfonyl]-2-(2,4,6-trimethylphenoxy)pyridine-3-carboxamide (Compound 72), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) 6-(3-isobutoxyphenyl)-N-[(2-oxo-1H-pyridin-3-yl)sulfonyl]-2-(2,4,6-trimethylphenoxy)pyridine-3-carboxamide (Compound 125), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-(benzenesulfonyl)-5-tert-butyl-2-[(2,4,6-trimethylphenyl)methyl]pyrazole-3-carboxamide (Compound 45), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-(3-aminophenyl)sulfonyl-4-isopropyl-2-[(2,4,6-trimethylphenyl)methyl]isoindoline-1-carboxamide (Compound 299), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(2-methoxy-3-pyridyl)sulfonyl]-6-(1-methylcyclopropyl)-2-(2,4,6-trimethylphenoxy)pyridine-3-carboxamide (Compound 365), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c)

3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a) N-[(6-amino-2-pyridyl)sulfonyl]-2-(2,2-dimethylpyrrolidin-1-yl)-6-(3-fluoro-5-isobutoxy-phenyl)pyridine-3-carboxamide (Compound 361), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the above recited pharmaceutical compositions contain a pharmaceutically acceptable prodrug of the compound of the present invention.

In another embodiment, the pharmaceutical composition of the present invention comprises a) N-[(6-amino-2-pyridyl)sulfonyl]-6-(6-isopropoxy-3-pyridyl)-2-[-3-phenyl-1-piperidyl]pyridine-3-carboxamide (Compound 233), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(4-chloro-3-isobutoxy-phenyl)-2-(2,4,6-trimethylphenoxy)pyridine-3-carboxamide (Compound 238), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-(3-fluoro-5-isobutoxy-phenyl)-N-(1H-pyrazol-3-ylsulfonyl)-2-(2,4,6-trimethylphenoxy)pyridine-3-carboxamide (Compound 318), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-tert-butyl-2-(2,4,6-trimethylphenoxy)pyridine-3-carboxamide (Compound 228), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(3-fluoro-5-isobutoxy-phenyl)-2-(2,4,6-trimethylphenoxy)pyridine-3-carboxamide (Compound 196), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-2-[(2S,5R)-2,5-dimethylpyrrolidin-1-yl]-6-(6-isopropoxy-3-pyridyl)pyridine-3-carboxamide (Compound 337), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 368), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or pharmaceutically acceptable salt thereof.

In another embodiment, the pharmaceutical composition of the present invention comprises a) N-[(6-amino-2-pyridyl)sulfonyl]-8,8-dimethyl-2-(2,4,6-trimethylphenoxy)-6,7-dihydro-5H-quinoline-3-carboxamide (Compound 182), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-(benzenesulfonyl)-6-(3-fluoro-5-isobutoxy-phenyl)-2-[(4S)-2,2,4-trimethylpyrrolidin-1-yl]pyridine-3-carboxamide (Compound 1356), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(4-methylcyclohexyl)-2-(2,4,6-trimethylphenoxy)pyridine-3-carboxamide (Compound 172), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-2-(2,6-dimethylphenoxy)-6-(3-fluoro-5-isobutoxy-phenyl)pyridine-3-carboxamide (Compound 639), or pharmaceutically acceptable salt thereof; b) N-(5-hydroxy-2,4-ditert-butyl-phenyl)-4-oxo-1H-quinoline-3-carboxamide, or pharmaceutically acceptable salt thereof;

and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-(p-tolyl)-N-(1H-pyrazol-3-ylsulfonyl)-2-(2,4,6-trimethylphenoxy)pyridine-3-carboxamide (Compound 300), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (Compound 1660), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(4-chlorophenyl)-2-(2,4,6-trimethylphenoxy)pyridine-3-carboxamide (Compound 234), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-tert-butyl-N-[[6-(methylamino)-2-pyridyl]sulfonyl]-2-(2,4,6-trimethylphenoxy)pyridine-3-carboxamide (Compound 262), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(4-chloro-2-fluoro-phenyl)-2-(2,4,6-trimethylphenoxy)pyridine-3-carboxamide (Compound 207), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(4-isobutoxyphenyl)-2-(2,4,6-trimethylphenoxy)pyridine-3-carboxamide (Compound 320), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-2-(2,3-dimethyl-1-piperidyl)-6-(6-isopropoxy-3-pyridyl)pyridine-3-carboxamide (Compound 353), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-2-[(2S,5R)-2,5-dimethylpyrrolidin-1-yl]-6-(3-fluoro-5-isobutoxy-phenyl)pyridine-3-carboxamide (Compound 171), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(6-isopropoxy-3-pyridyl)-2-(3-isopropyl-1-piperidyl)pyridine-3-carboxamide (Compound 114), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(6-isopropoxy-3-pyridyl)-2-(3-methyl-1-piperidyl)pyridine-3-carboxamide (Compound 321), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c)

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-2-(2,4-dimethylphenoxy)-8,8-dimethyl-6,7-dihydro-5H-quinoline-3-carboxamide (Compound 15), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-(4-aminothiazol-2-yl)sulfonyl-6-tert-butyl-2-(2,4,6-trimethylphenoxy)pyridine-3-carboxamide (Compound 265), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(4-isopropylphenyl)-2-(2,4,6-trimethylphenoxy)pyridine-3-carboxamide (Compound 164), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-tert-butyl-N-(1H-pyrazol-5-ylsulfonyl)-2-(2,4,6-trimethylphenoxy)pyridine-3-carboxamide (Compound 214), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(7-fluoro-1,3-benzodioxol-4-yl)-2-(2,4,6-trimethylphenoxy)pyridine-3-carboxamide (Compound 345), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(3-isobutoxyphenyl)-2-(2,4,6-trimethylphenoxy)pyridine-3-carboxamide (Compound 8), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-(3-aminophenyl)sulfonyl-5-tert-butyl-2-[(2,4,6-trimethylphenyl)methyl]pyrazole-3-carboxamide (Compound 110), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(4-chloro-3-isopropoxy-phenyl)-2-(2,4,6-trimethylphenoxy)pyridine-3-carboxamide (Compound 281), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-6-(2-fluoro-5-isobutoxy-phenyl)-2-(2,4,6-trimethylphenoxy)pyridine-3-carboxamide (Compound 351), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-(3-aminopyrazin-2-yl)sulfonyl-8,8-dimethyl-2-(4-methyl-1-piperidyl)-6,7-dihydro-5H-quinoline-3-carboxamide (Compound 197), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-(4-chloro-3-isobutoxy-phenyl)-N-[(2-oxo-1H-pyridin-3-yl)sulfonyl]-2-(2,4,6-trimethylphenoxy)pyridine-3-carboxamide (Compound 136), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 2-(2,5-dimethylpyrrolidin-1-yl)-6-(3-fluoro-5-isobutoxy-phenyl)-N-[(2-oxo-1H-pyridin-3-yl)sulfonyl]pyridine-3-carboxamide (Compound 307), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-(2-fluoro-5-isobutoxy-phenyl)-N-[(2-oxo-1H-pyridin-3-yl)sulfonyl]-2-(2,4,6-trimethylphenoxy)pyridine-3-carboxamide (Compound 279), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-(4-chloro-3-propoxy-phenyl)-N-[(2-oxo-1H-pyridin-3-yl)sulfonyl]-2-(2,4,6-trimethylphenoxy)pyridine-3-carboxamide (Compound 72), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) 6-(3-isobutoxyphenyl)-N-[(2-oxo-1H-pyridin-3-yl)sulfonyl]-2-(2,4,6-trimethylphenoxy)pyridine-3-carboxamide (Compound 125), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-(benzenesulfonyl)-5-tert-butyl-2-[(2,4,6-trimethylphenyl)methyl]pyrazole-3-carboxamide (Compound 45), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-(3-aminophenyl)sulfonyl-4-isopropyl-2-[(2,4,6-trimethylphenyl)methyl]isoindoline-1-carboxamide (Compound 299), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(2-methoxy-3-pyridyl)sulfonyl]-6-(1-methylcyclopropyl)-2-(2,4,6-trimethylphenoxy)pyridine-3-carboxamide (Compound 365), or pharmaceutically acceptable salt thereof; b) N-(5-hydroxy-2,4-ditert-butyl-phenyl)-4-oxo-1H-quinoline-3-carboxamide, or pharmaceutically-acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a) N-[(6-amino-2-pyridyl)sulfonyl]-2-(2,2-dimethylpyrrolidin-1-yl)-6-(3-fluoro-5-isobutoxy-phenyl)pyridine-3-carboxamide (Compound 361), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the above recited pharmaceutical compositions contain a pharmaceutically acceptable prodrug of the compound of the present invention.

In another embodiment, the present invention features a pharmaceutical composition comprising a) a compound of formula I; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) an additional CFTR corrector.

In another embodiment, the present invention features a pharmaceutical composition comprising a) a compound of Table 1; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) an additional CFTR corrector.

In another embodiment, the above recited pharmaceutical composition contain a pharmaceutically acceptable prodrug of the compound of the present invention.

In another embodiment, the additional CFTR corrector from above is (N-(2-(5-chloro-2-methoxy-phenylamino)-4'-methyl-[4,5']bithiazolyl-2'-yl)-benzamide (corr-4a). In another embodiment, the additional CFTR corrector is a compound disclosed in published International Patent Application WO2014081820, incorporated herein in its entirety by reference.

In another embodiment, the present invention features a pharmaceutical composition comprising a) a compound of formula I; b) N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide; and a CFTR corrector selected from (N-(2-(5-chloro-2-methoxy-phenylamino)-4'-methyl-[4,5']bithiazolyl-2'-yl)-benzamide (corr-4a), a compound disclosed in published International Patent Application WO2014081820, incorporated herein in its entirety by reference, a compound disclosed in Published International Patent Application No. WO2014086687, or a compound disclosed in U.S. Pat. No. 8,247,436 or 8,476,269; U.S. patent application Ser. No. 13/923,349; or Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the present invention features a pharmaceutical composition comprising a) a compound of formula I; b) a compound selected from certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamide); and UCCF-152 (3-[2-(benzyloxy)phenyl]-5-(chloromethyl)isoxazole); and c) a CFTR corrector selected from (N-(2-(5-chloro-2-methoxyphenylamino)-4'-methyl-[4,5']bithiazolyl-2'-yl)-benzamide (corr-4a), a compound disclosed in published International Patent Application WO2014081820, incorporated herein in its entirety by reference, or a compound disclosed in U.S. Pat. No. 8,247,436 or 8,476,269; U.S. patent application Ser. No. 13/923,349; or Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the present invention features the pharmaceutical composition described above comprising a) a compound of formula-I; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or 4-(3-(1-(2,2-difluorobenzo[d][1,3]dioxol-5-yl)cyclopropanecarboxamido) isoquinolin-1-yl)benzoic acid; and c) an additional CFTR corrector, such as those, for example, specifically listed above; and further comprising d) a CFTR potentiator.

In another embodiment, the CFTR potentiator from above is N-(5-hydroxy-2,4-ditert-butyl-phenyl)-4-oxo-1H-quinoline-3-carboxamide or N-(4-(7-azabicyclo[2.2.1]heptan-7-yl)-2-(trifluoromethyl)phenyl)-4-oxo-5-(trifluoromethyl)-1,4-dihydroquinoline-3-carboxamide. In another embodiment, the CFTR potentiator from above is N-(5-hydroxy-2,4-ditert-butyl-phenyl)-4-oxo-1H-quinoline-3-carboxamide.

In another embodiment, the CFTR potentiator from above is selected from certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamide); and UCCF-152 (3-[2-(benzyloxy)phenyl]-5-(chloromethyl)isoxazole).

In one embodiment, the additional therapeutic agent is selected from a compound disclosed in Published International Patent Application No. WO2014078842 or WO2012158885, or in United States Published Application No. US20140073667; all published international patent applications and published US patent application are hereby incorporated in their entirety by reference.

In one embodiment, the additional therapeutic agent is selected from a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference.

In one embodiment, the additional therapeutic agent is selected from a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In one embodiment, the additional therapeutic agent is selected from a compound disclosed in WO2014210159 or WO2014152213; all published international patent applications are hereby incorporated in their entirety by reference.

In one embodiment, the additional therapeutic agent is selected from a compound disclosed in Published International Patent Application No.: WO2014210159 or WO2014152213; all published international patent applications are hereby incorporated in their entirety by reference.

In one embodiment, the additional therapeutic agent is selected from a compound disclosed in Published International Patent Application No.: WO2015003083, WO2015007517, WO2015007519, or WO2015007516; all published international patent applications are hereby incorporated in their entirety by reference.

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; and c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the invention features a pharmaceutical composition comprising a) a compound of formula I; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; and c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the invention features a pharmaceutical composition comprising a) a compound of formula I; b) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and c) N-(5-hydroxy-2,4-ditert-butyl-phenyl)-4-oxo-1H-quinoline-3-carboxamide.

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and d) N-(5-hydroxy-2,4-ditert-butyl-phenyl)-4-oxo-1H-quinoline-3-carboxamide.

In another embodiment, the invention features a pharmaceutical composition comprising a) a compound of formula I; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and d) N-(5-hydroxy-2,4-ditert-butyl-phenyl)-4-oxo-1H-quinoline-3-carboxamide.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and d) N-(5-hydroxy-2,4-ditert-butyl-phenyl)-4-oxo-1H-quinoline-3-carboxamide.

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; and c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference.

In another embodiment, the invention features a pharmaceutical composition comprising a) a compound of formula I; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; and c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference.

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference; and d) N-(5-hydroxy-2,4-ditert-butyl-phenyl)-4-oxo-1H-quinoline-3-carboxamide.

In another embodiment, the invention features a pharmaceutical composition comprising a) a compound of formula I; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference; and d) N-(5-hydroxy-2,4-ditert-butyl-phenyl)-4-oxo-1H-quinoline-3-carboxamide.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference; and d) N-(5-hydroxy-2,4-ditert-butyl-phenyl)-4-oxo-1H-quinoline-3-carboxamide.

In another embodiment, the additional therapeutic agent is a compound disclosed in Published International Patent Application No. WO2014099673 hereby incorporated in its entirety by reference, including but not limited to the following compounds:

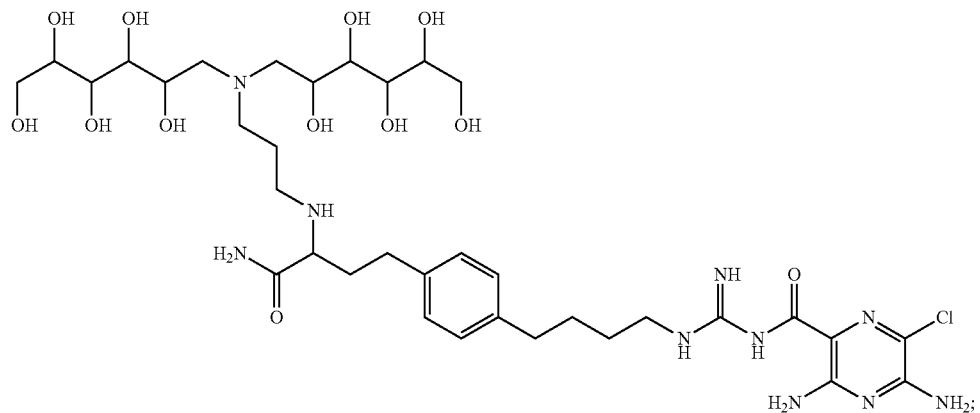
P-1
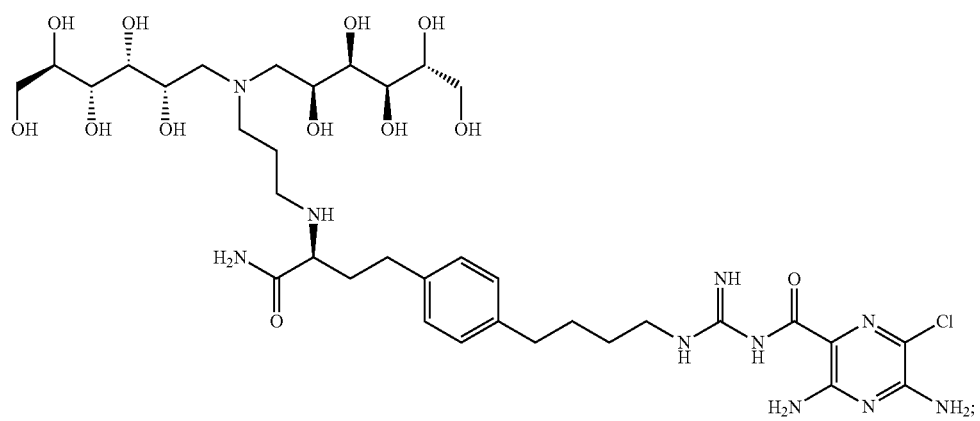
P-2
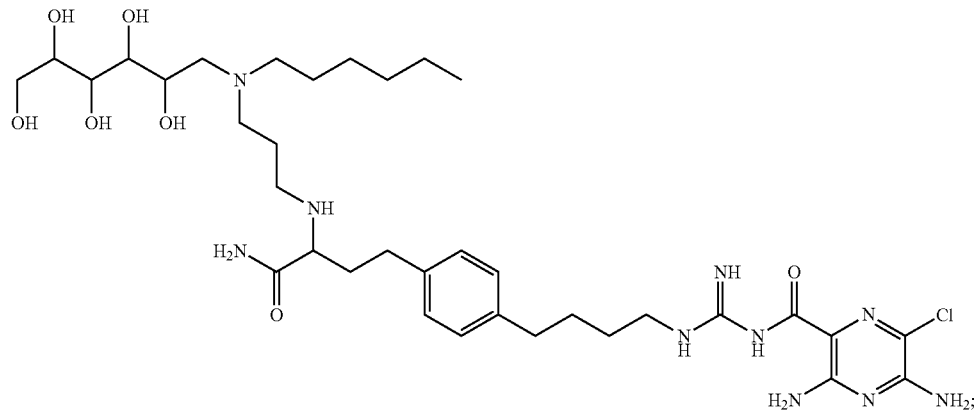
P-3
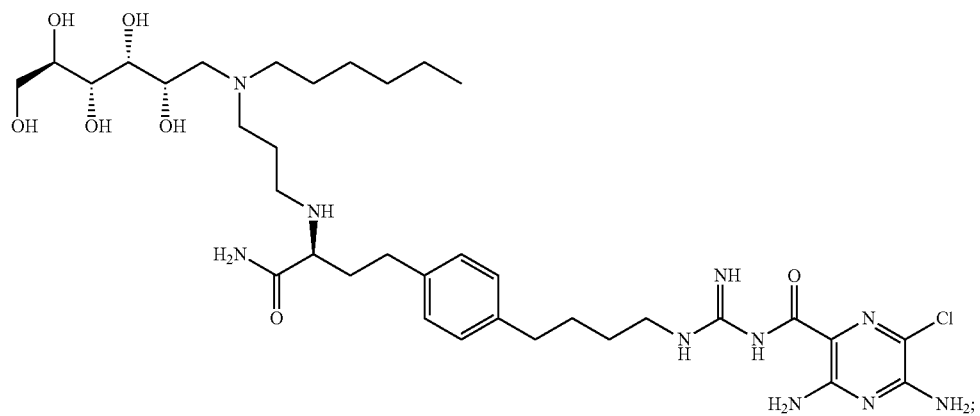
P-4

P-5
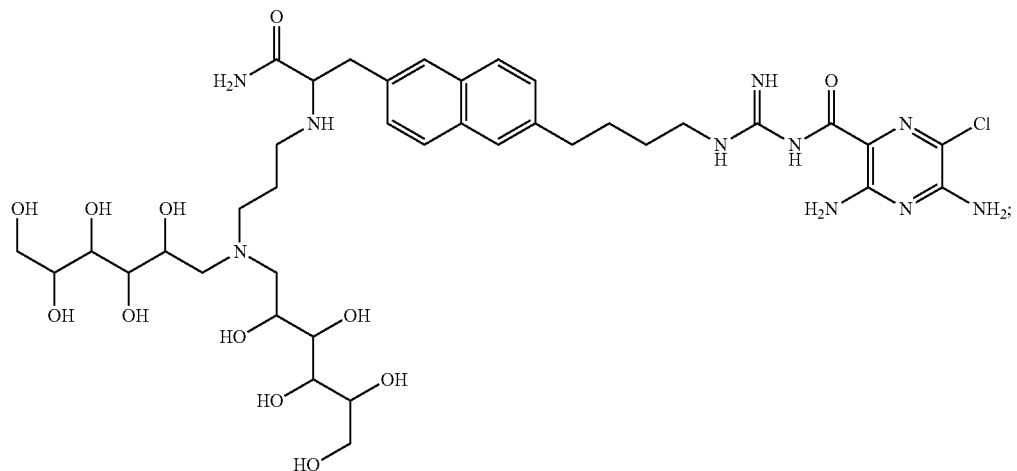
P-6
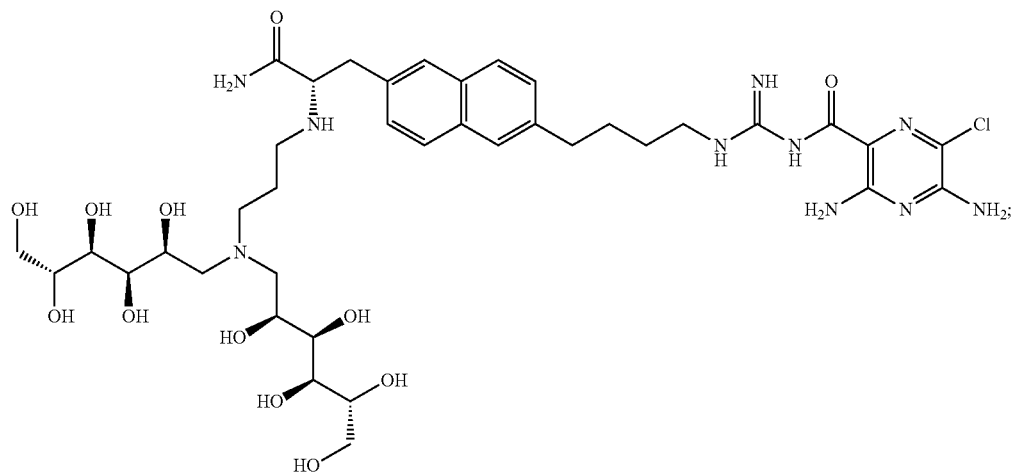
P-7
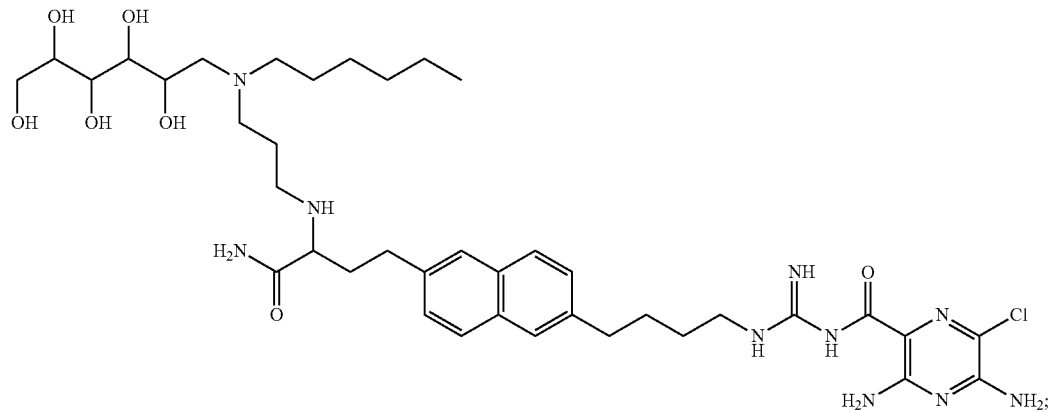

P-8
P-9
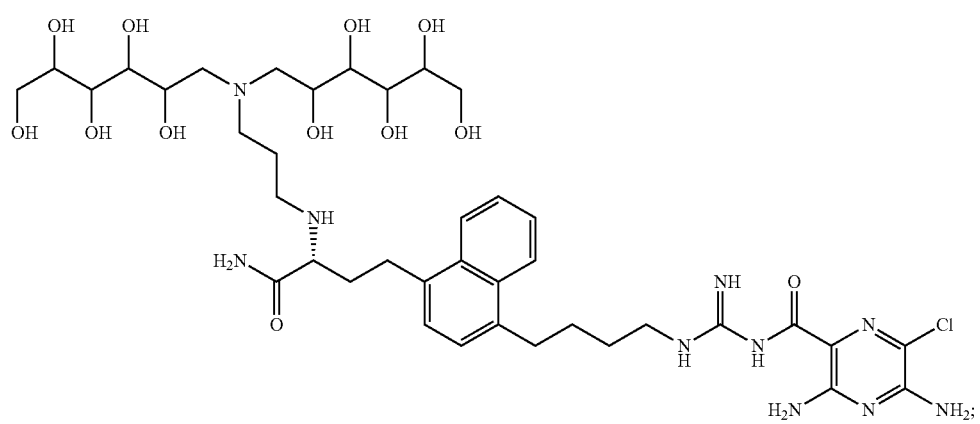
P-10
P-11
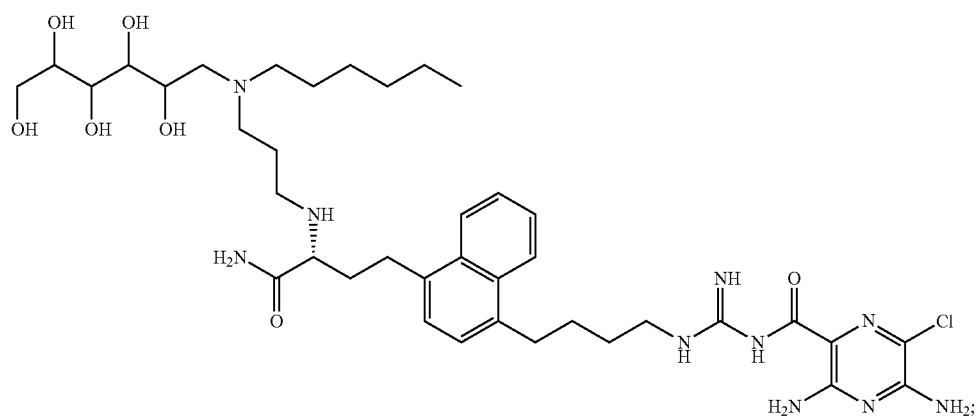

-continued
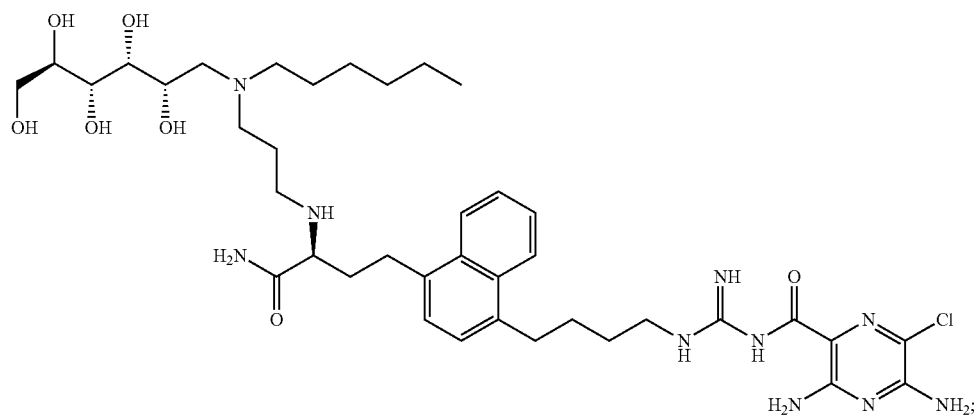
P-12
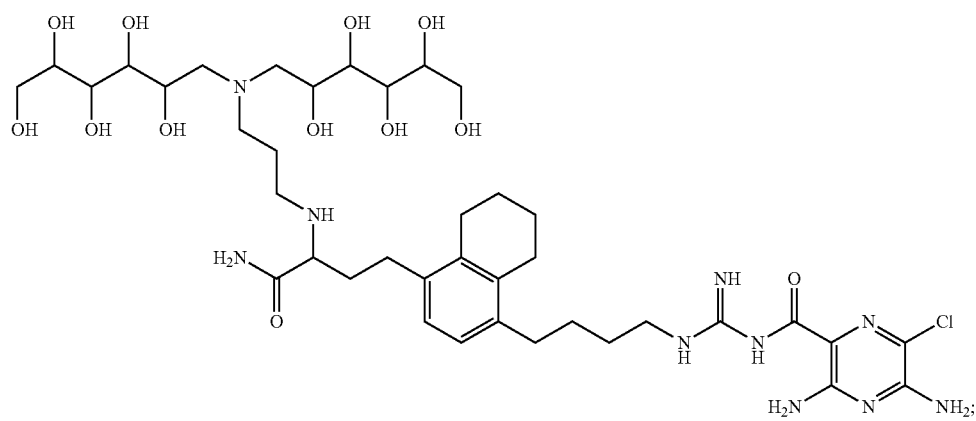
P-13
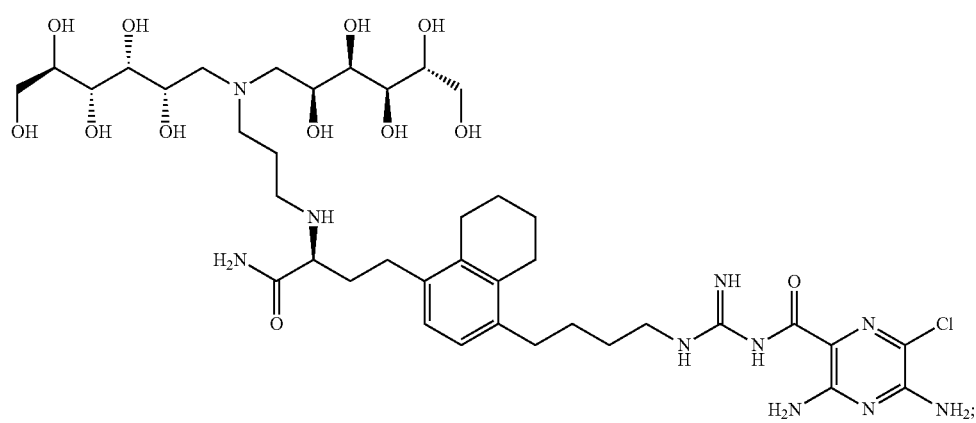
P-14
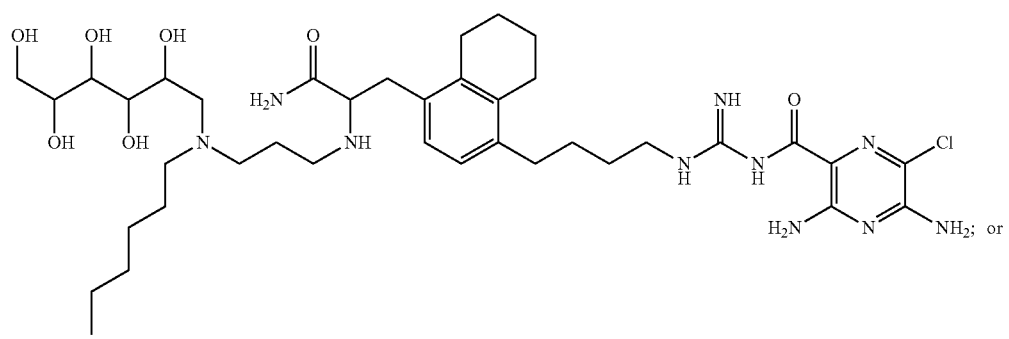
P-15

-continued

P-16

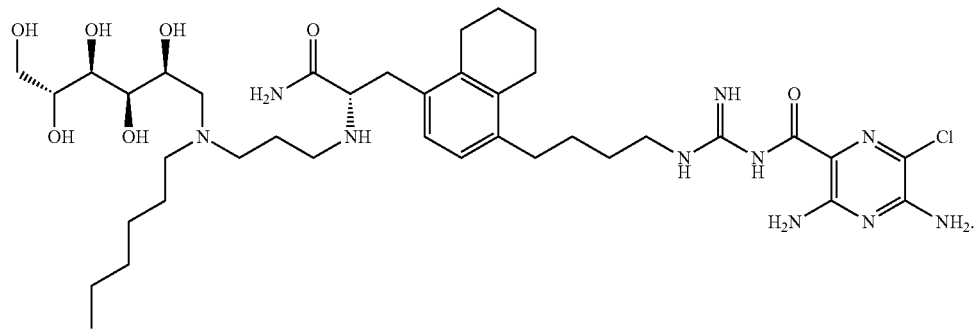

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; and c) a compound selected from P-1 to P-16 disclosed above.

In another embodiment, the invention features a pharmaceutical composition comprising a) a compound of Table 1; b) 3-(6-(1-(2,2-difluorobenzo[d][1,3]dioxol-5-yl) cyclopropanecarboxamido)-3-methylpyridin-2-yl)benzoic acid; and c) a compound selected from P-1 to P-16 disclosed above.

In another embodiment, the invention features a pharmaceutical composition comprising a) a compound of formula I; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) a compound selected from P-1 to P-16 disclosed above.

In another embodiment, the invention features a pharmaceutical composition comprising a) a compound of Table 1; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) a compound selected from P-1 to P-16 disclosed above.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; and c) a compound selected from P-1 to P-16 disclosed above.

In another embodiment, the invention features a pharmaceutical composition comprising a) a compound of Table 1; b) 4-(3-(1-(2,2-difluorobenzo[d][1,3]dioxol-5-yl)cyclopropanecarboxamido) isoquinolin-1-yl)benzoic acid; and c) a compound selected from P-1 to P-16 disclosed above.

In another embodiment, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; c) a compound selected from P-1 to P-16 disclosed above; and d) N-(5-hydroxy-2,4-ditert-butyl-phenyl)-4-oxo-1H-quinoline-3-carboxamide.

In another embodiment, the invention features a pharmaceutical composition comprising a) a compound of Table 1; b) 3-(6-(1-(2,2-difluorobenzo[d][1,3]dioxol-5-yl) cyclopropanecarboxamido)-3-methylpyridin-2-yl)benzoic acid; c) a compound selected from P-1 to P-16 disclosed above; and d) N-(5-hydroxy-2,4-ditert-butyl-phenyl)-4-oxo-1H-quinoline-3-carboxamide.

In another embodiment, the invention features a pharmaceutical composition comprising a) a compound of formula I; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; c) a compound selected from P-1 to P-16 disclosed above; and d) N-(5-hydroxy-2,4-ditert-butyl-phenyl)-4-oxo-1H-quinoline-3-carboxamide.

In another embodiment, the invention features a pharmaceutical composition comprising a) a compound of formula I; b) 4-(3-(1-(2,2-difluorobenzo[d][1,3]dioxol-5-yl)cyclopropanecarboxamido) isoquinolin-1-yl)benzoic acid; c) a compound selected from P-1 to P-16 disclosed above; and d) N-(5-hydroxy-2,4-ditert-butyl-phenyl)-4-oxo-1H-quinoline-3-carboxamide.

In another embodiment, the above recited pharmaceutical compositions contain a pharmaceutically acceptable prodrug of the compound of the present invention.

In some embodiments, the invention features a pharmaceutical composition comprising a) a compound of formula I; and b) a compound disclosed in U.S. Pat. No. 8,865,902. In some embodiments, the invention features a pharmaceutical composition comprising a) a compound of Table 1; and b) a compound disclosed in U.S. Pat. No. 8,865,902. In another embodiment, the compound disclosed in U.S. Pat. No. 8,865,902 has the following structure:

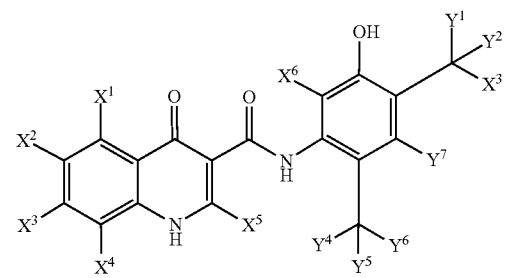

wherein the compound disclosed in U.S. Pat. No. 8,865,902 is any one of the compounds of the following table:

| $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|
| D | D | D | D | D | D | D | $CD_3$ | $CD_3$ | $CD_3$ | $CD_3$ | $CD_3$ | $CD_3$ |
| H | H | H | H | D | H | H | $CD_3$ | $CD_3$ | $CD_3$ | $CD_3$ | $CD_3$ | $CD_3$ |
| H | H | H | H | D | H | H | $CD_3$ | $CD_3$ | $CD_3$ | $CH_3$ | $CH_3$ | $CH_3$ |
| H | H | H | H | D | H | H | $CH_3$ | $CH_3$ | $CH_3$ | $CD_3$ | $CD_3$ | $CD_3$ |
| H | H | H | H | D | H | H | $CH_3$ | $CH_3$ | $CH_3$ | $CH_3$ | $CH_3$ | $CH_3$ |
| H | H | H | H | H | H | H | $CD_3$ | $CD_3$ | $CD_3$ | $CD_3$ | $CD_3$ | $CD_3$ |
| H | H | H | H | H | H | H | $CD_3$ | $CD_3$ | $CD_3$ | $CH_3$ | $CH_3$ | $CH_3$ |
| H | H | H | H | H | H | H | $CH_3$ | $CH_3$ | $CH_3$ | $CD_3$ | $CD_3$ | $CD_3$. |

1823

In another embodiment, the compound disclosed in U.S. Pat. No. 8,865,902 is any one of the compounds of the following table:

| $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|
| H | H | H | H | H | D | D | $CD_3$ | $CD_3$ | $CD_3$ | $CD_3$ | $CD_3$ | $CD_3$ |
| H | H | H | H | D | D | D | $CD_3$ | $CD_3$ | $CD_3$ | $CD_3$ | $CD_3$ | $CD_3$ |
| H | H | H | H | D | D | D | $CD_3$ | $CD_3$ | $CD_3$ | $CH_3$ | $CH_3$ | $CH_3$ |
| H | H | H | H | D | D | D | $CH_3$ | $CH_3$ | $CH_3$ | $CD_3$ | $CD_3$ | $CD_3$ |
| H | H | H | H | D | D | D | $CH_3$ | $CH_3$ | $CH_3$ | $CH_3$ | $CH_3$ | $CH_3$ |
| H | H | H | H | H | D | D | $CD_3$ | $CD_3$ | $CD_3$ | $CH_3$ | $CH_3$ | $CH_3$ |
| H | H | H | H | H | D | D | $CH_3$ | $CH_3$ | $CH_3$ | $CD_3$ | $CD_3$ | $CD_3$ |
| D | D | D | D | D | D | D | $CH_3$ | $CH_3$ | $CH_3$ | $CH_3$ | $CH_3$ | $CH_3$ |
| D | D | D | D | D | D | D | $CH_3$ | $CH_3$ | $CH_3$ | $CD_3$ | $CD_3$ | $CD_3$ |
| D | D | D | D | D | H | H | $CD_3$ | $CD_3$ | $CD_3$ | $CH_3$ | $CH_3$ | $CH_3$ |
| D | D | D | D | D | H | H | $CD_3$ | $CD_3$ | $CD_3$ | $CD_3$ | $CD_3$ | $CD_3$ |
| H | H | H | H | H | H | D | $CD_3$ | $CD_3$ | $CD_3$ | $CD_3$ | $CD_3$ | $CD_3$ |
| H | H | H | H | H | H | D | $CH_3$ | $CH_3$ | $CH_3$ | $CD_3$ | $CD_3$ | $CD_3$ |
| H | H | H | H | H | H | D | $CH_3$ | $CH_3$ | $CH_3$ | $CD_3$ | $CD_3$ | $CD_3$ |
| H | H | H | H | H | D | H | $CD_3$ | $CD_3$ | $CD_3$ | $CD_3$ | $CD_3$ | $CD_3$ |
| H | H | H | H | H | D | H | $CH_3$ | $CH_3$ | $CH_3$ | $CD_3$ | $CD_3$ | $CD_3$ |
| H | H | H | H | D | H | H | $CH_3$ | $CH_3$ | $CH_3$ | $CD_3$ | $CD_3$ | $CD_3$ |

In another embodiment, the compound disclosed in U.S. Pat. No. 8,865,902 is any one of the compounds of the following table:

| $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|
| D | D | D | D | D | H | H | $CD_3$ | $CD_3$ | $CD_3$ | $CD_3$ | $CD_3$ | $CD_3$ |
| D | D | D | D | D | D | D | $CH_3$ | $CH_3$ | $CH_3$ | $CH_3$ | $CH_3$ | $CH_3$ |
| D | D | D | D | D | H | H | $CH_3$ | $CH_3$ | $CH_3$ | $CH_3$ | $CH_3$ | $CH_3$ |
| D | D | D | D | H | D | D | $CD_3$ | $CD_3$ | $CD_3$ | $CD_3$ | $CD_3$ | $CD_3$ |
| D | D | D | D | H | H | H | $CD_3$ | $CD_3$ | $CD_3$ | $CD_3$ | $CD_3$ | $CD_3$ |
| D | D | D | D | H | D | D | $CH_3$ | $CH_3$ | $CH_3$ | $CH_3$ | $CH_3$ | $CH_3$ |
| D | D | D | D | H | H | H | $CH_3$ | $CH_3$ | $CH_3$ | $CH_3$ | $CH_3$ | $CH_3$ |
| H | H | H | H | H | D | D | $CH_3$ | $CH_3$ | $CH_3$ | $CH_3$ | $CH_3$ | $CD_3$ |

In some embodiments, the invention features a pharmaceutical composition comprising a) a compound of formula I; and b) the compound:

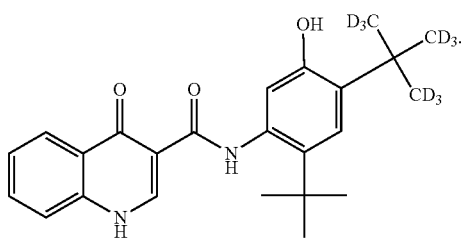 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the invention features a pharmaceutical composition comprising a) a compound of Table 1; and b) the compound:

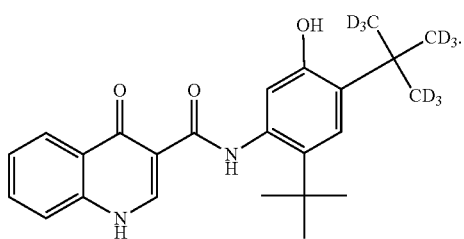 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the invention features a pharmaceutical composition comprising a) a compound of formula I; b) 3-(6-(1-(2,2-difluorobenzo[d][1,3]dioxol-5-yl) cyclopropanecarboxamido)-3-methylpyridin-2-yl)benzoic acid; and c) the compound:

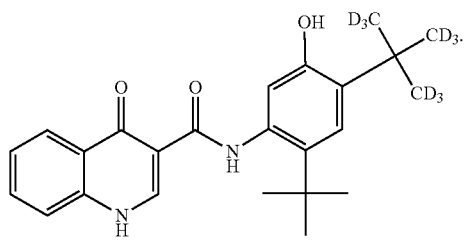 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the invention features a pharmaceutical composition comprising a) a compound of Table 1; b) 3-(6-(1-(2,2-difluorobenzo[d][1,3]dioxol-5-yl) cyclopropanecarboxamido)-3-methylpyridin-2-yl)benzoic acid; and c) the compound:

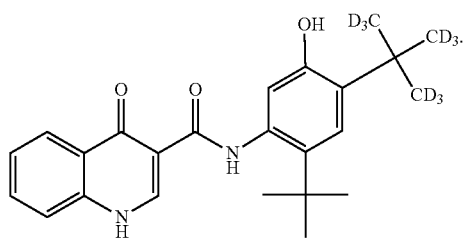 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the invention features a pharmaceutical composition comprising a) a compound selected from Compound 233, Compound 238, Compound 318, Compound 228, Compound 196, Compound 337, Compound 368, Compound 182, Compound 1356, Compound 172, Compound 639, Compound 300, Compound 1660, Compound 234, Compound 1975, Compound 262, Compound 2191, Compound 207, Compound 320, Compound 353, Compound 171, Compound 114, Compound 321, Compound 15, Compound 265, Compound 164, Compound 214, Compound 345, Compound 8, Compound 110, Compound 281, Compound 351, Compound 197, Compound 136, Compound 307, Compound 279, Compound 72, Compound 125, Compound 45, Compound 299, Compound 365, or Compound 361; b) 3-(6-(1-(2,2-difluorobenzo[d][1,3]dioxol-5-yl) cyclopropanecarboxamido)-3-methylpyridin-2-yl)benzoic acid; and c) the compound:

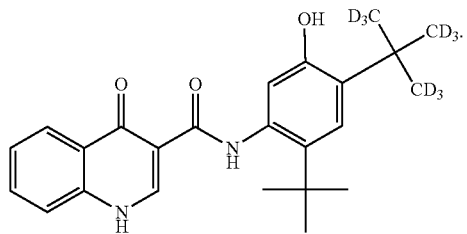 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the invention features a pharmaceutical composition comprising a) a compound of formula I; b) (R)-1-(2,2-difluorobenzo[d][1,3]dioxol-5-yl)-N-(1-(2, 3-dihydroxypropyl)-6-fluoro-2-(1-hydroxy-2-methylpropan-2-yl)-1H-indol-5-yl)cyclopropanecarboxamide; and c) the compound:

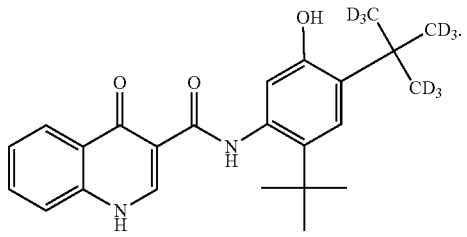 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the invention features a pharmaceutical composition comprising a) a compound of Table 1; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) the compound:

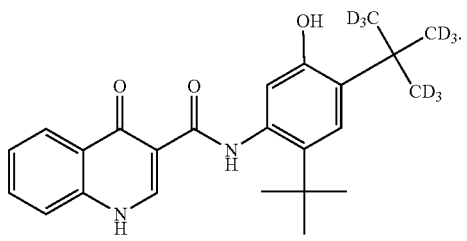 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the invention features a pharmaceutical composition comprising a) a compound selected from Compound 233, Compound 238, Compound 318, Compound 228, Compound 196, Compound 337, Compound 368, Compound 182, Compound 1356, Compound 172, Compound 639, Compound 300, Compound 1660, Compound 234, Compound 1975, Compound 262, Compound 2191, Compound 207, Compound 320, Compound 353, Compound 171, Compound 114, Compound 321, Compound 15, Compound 265, Compound 164, Compound 214, Compound 345, Compound 8, Compound 110, Compound 281, Compound 351, Compound 197, Compound 136, Compound 307, Compound 279, Compound 72, Compound 125, Compound 45, Compound 299, Compound 365, or Compound 361; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) the compound:

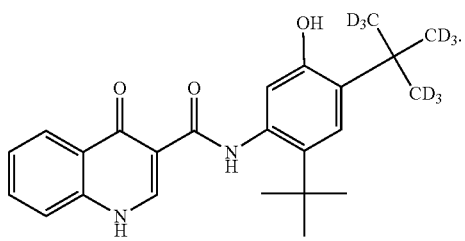 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In another embodiment, the above recited pharmaceutical compositions contain a pharmaceutically acceptable prodrug of the compound of the present invention.

In one embodiment, any of the below therapeutic agents can be used alone with a compound of formula I or Id, or in combination with any of the above described pharmaceutical compositions, or as a component in any of the above described pharmaceutical compositions.

In one embodiment, the additional therapeutic agent is selected from a mucolytic agent, bronchodialator, an antibiotic, an anti-infective agent, a CFTR modulator, or an anti-inflammatory agent.

In one embodiment, any of the below therapeutic agents, which predominantly treat the symptoms a CFTR mediated disease, such as cystic fibrosis, rather than its underlying cause, can be used alone with a compound of formula I, or in combination with any of the above described pharmaceutical compositions, or as a component in any of the above described pharmaceutical compositions.

In one embodiment, the additional therapeutic agent is an antibiotic. Exemplary antibiotics useful herein include tobramycin, including tobramycin inhaled powder (TIP), azithromycin, cayston, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional therapeutic agent is a mucolyte. Exemplary mucolytes useful herein includes Pulmozyme®.

In another embodiment, the additional therapeutic agent is a bronchodialator. Exemplary bronchodialtors include albuterol, metaprotenerol sulfate, pirbuterol acetate, salmeterol, or tetrabuline sulfate.

In another embodiment, the additional therapeutic agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl] [[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional therapeutic agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional therapeutic agent is a compound that augments or induces CFTR activity other than a compound of formula I. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), and cobiprostone (7-{(2R, 4aR, 5R, 7aR)-2-[(3S)-1,1-difluoro-3-methylpentyl]-2-hydroxy-6-oxooctahydrocyclopenta[b]pyran-5-yl}heptanoic acid).

In another embodiment, the additional therapeutic agent is a nutritional agent. Exemplary nutritional agents include pancrelipase (pancreating enzyme replacement), including Pancrease®, Pancreacarb®, Ultrase®, or Creon®, Liprotomase® (formerly Trizytek@), Aquadeks®, or glutathione inhalation. In one embodiment, the additional nutritional agent is pancrelipase.

In another embodiment, the additional therapeutic agent is a compound selected from gentamicin, curcumin, cyclophosphamide, 4-phenylbutyrate, miglustat, felodipine, nimodipine, Philoxin B, geniestein, Apigenin, cAMP/cGMP augmenters or inducers such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In other embodiments, the additional therapeutic agent is a compound disclosed in WO 2004028480, WO 2004110352, WO 2005094374, WO 2005120497, or WO 2006101740, incorporated herein in their entirety by reference. In another embodiment, the additional agent is a benzo[c]quinolizinium derivative that exhibits CFTR inducing or augmenting activity or a benzopyran derivative that exhibits CFTR inducing or augmenting activity. In another embodiment, the additional agent is a compound disclosed in U.S. Pat. Nos. 7,202,262, 6,992,096, US20060148864, US20060148863, US20060035943, US20050164973, WO2006110483, WO2006044456, WO2006044682, WO2006044505, WO2006044503, WO2006044502, or WO2004091502, incorporated herein in their entirety by reference. In another embodiment, the additional agent is a compound disclosed in WO2004080972, WO2004111014, WO2005035514, WO2005049018, WO2006099256, WO2006127588, or WO2007044560, incorporated herein in their entirety by reference.

In another embodiment, the additional therapeutic agent is a compound disclosed in WO2014180562 or US20140274933, incorporated herein in their entirety by reference.

In another embodiment, the additional therapeutic agent is selected from the categories ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, or SYK-Inhibitors, or double or triple combinations thereof.

In another embodiment, the additional therapeutic agent is an ENaC inhibitor selected from 3-amino-6-(4-fluoro-phenyl)-5-trifluoromethyl-pyridine-2-carboxylic acid (3,3,3-trifluoro-2-hydroxy-2-methyl-propyl)-amide;
5-amino-6'-methyl-3-trifluoromethyl-[2,3]bipyridinyl-6-carboxylic acid (3,3,3-trifluoro-2-hydroxy-2-methyl-propyl)-amide;
3-amino-6-cyclopropyl-N-(3,3,3-trifluoro-2-hydroxy-2-methylpropyl)-5-(trifluoromethyl)picolinamide; 3-amino-6-methoxy-N-(3,3,3-trifluoro-2-hydroxy-2-(trifluoromethyl)propyl)-5-(trifluoro methyl)picolinamide;
3-amino-6-(4-fluoro-phenyl)-5-trifluoromethyl-pyridine-2-carboxylic acid ((S)-3,3,3-trifluoro-2-hydroxy-2-methyl-propyl)-amide;
3-amino-6-methoxy-5-trifluoromethyl-pyridine-2-carboxylic acid((S-3,3,3-trifluoro-2-hydroxy-2-methyl-propyl)-amide;
3-amino-6-methoxy-5-trifluoromethyl-pyridine-2-carboxylic acid ((R)-3,3,3-trifluoro-2-hydroxy-2-methyl-propyl)-amide;
3-amino-6-(2,4-dichloro-phenyl)-5-trifluoromethyl-pyridine-2-carboxylic acid ((S)-3,3,3-trifluoro-2-hydroxy-2-methyl-propyl)-amide;
3-amino-6-(2,4-dichloro-phenyl)-5-trifluoromethyl-pyridine-2-carboxylic acid ((R)-3,3,3-trifluoro-2-hydroxy-2-methyl-propyl)-amide;
3-amino-6-(4-fluoro-phenyl)-5-trifluoromethyl-pyridine-2-carboxylic acid (2-hydroxy-2-methyl-propyl)-amide;
3-amino-5,6-bis-trifluoromethyl-pyridine-2-carboxylic acid ((S)-3,3,3-trifluoro-2-hydroxy-2-methyl-propyl)-amide;
3-amino-5,6-bis-trifluoromethyl-pyridine-2-carboxylic acid ((R)-3,3,3-trifluoro-2-hydroxy-2-methyl-propyl)-amide;
(S)-3-amino-6-ethoxy-N-(3,3,3-trifluoro-2-hydroxy-2-methylpropyl)-5-(trifluoro methyl)picolinamide;
3-amino-6-methoxy-5-trifluoromethyl-pyridine-2-carboxylic acid ((S)-3,3,3-trifluoro-2-hydroxy-2-methyl-propyl)-amide;
3-amino-6-methoxy-5-trifluoromethyl-pyridine-2-carboxylic acid ((R)-3,3,3-trifluoro-2-hydroxy-2-methyl-propyl)-amide;
3-amino-6-(4-fluoro-phenyl)-5-trifluoromethyl-pyridine-2-carboxylic acid (3,3,3-trifluoro-2-hydroxy-2-methyl-propyl)-amide;
3-amino-5,6-bis-trifluoromethyl-pyridine-2-carboxylic acid ((S)-3,3,3-trifluoro-2-hydroxy-2-methyl-propyl)-amide;
3-amino-5,6-bis-trifluoromethyl-pyridine-2-carboxylic acid ((R)-3,3,3-trifluoro-2-hydroxy-2-methyl-propyl)-amide,
or pharmaceutically acceptable salts thereof.

In another embodiment, the additional agent is a compound disclosed in U.S. Pat. No. 8,247,436 and International PCT Publication WO 2011113894, incorporated herein in their entirety by reference.

In another embodiment, the additional therapeutic agent is a betamimetic selected from Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and
1-(2-chloro-4-hydroxyphenyl)-t-butylaminoethanole;
(–)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate;
3-(4-{6-[2-Hydroxy-2-(4-hydroxy-3-hydroxymethyl-phenyl)-ethylamino]-hexyl-oxy}-butyl)-benzyl-sulfonamide;
5-[2-(5,6-Diethyl-indan-2-ylamino)-1-hydroxy-ethyl]-8-hydroxy-1H-quinoline-2-one;
4-Hydroxy-7-[2-{[2-{[3-(2-phenylethoxy)propyl]sulphonyl}ethyl]-amino}ethy-1]-2 (3H)-benzothiazolone;
1-(2-Fluoro-4-hydroxyphenyl)-2-[4-(1-benzimidazolyl)-2-methyl-2-butylamino]ethanol;
1-[3-(4-Methoxybenzyl-amino)-4-hydroxyphenyl]-2-[4-(1-benzimidazolyl)-2-m-ethyl-2-butylamino]ethanol;
1-[2H-5-hydroxy-3-oxo-4H-1,4-benzoxazin-8-yl]-2-[3-(4-N,N-dimethylaminoph-enyl)-2-methyl-2-propylamino]ethanol;
1-[2H-5-hydroxy-3-oxo-4H-1,4-benzoxazin-8-yl]-2-[3-(4-methoxyphenyl)-2-methyl-2-propylamino]ethanol;
1-[2H-5-hydroxy-3-oxo-4H-1,4-benzoxazin-8-yl]-2-[3-(4-n-butyloxyphenyl)-2-methyl-2-propylamino]ethanol;
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol;
5-Hydroxy-8-(1-hydroxy-2-isopropylaminobutyl)-2H-1,4-benzoxazin-3-(4H)-one;
1-(4-Amino-3-chloro-5-trifluormethylphenyl)-2-tert-butylamino)ethanol;
6-Hydroxy-8-{1-hydroxy-2-[2-(4-methoxy-phenyl)-1,1-dimethyl-ethylamino]-ethyl}-4H-benzo[1,4]oxazin-3-one;
6-Hydroxy-8-{1-hydroxy-2-[2-(4-phenoxy-acetic acid ethylester)-1,1-dimethyl-ethylamino]-ethyl}-4H-benzo[1,4]oxazin-3-one;

6-Hydroxy-8-{1-hydroxy-2-[2-(4-phenoxy-acetic acid)-1,1-dimethyl-ethylamino]-ethyl}-4H-benzo[1,4]oxazin-3-one;
8-{2-[1,1-Dimethyl-2-(2,4,6-trimethylphenyl)-ethylamino]-1-hydroxy-ethyl}-6-hydroxy-4H-benzo[1,4]oxazin-3-one;
6-Hydroxy-8-{1-hydroxy-2-[2-(4-hydroxy-phenyl)-1,1-dimethyl-ethylamino]-ethyl}-4H-benzo[1,4]oxazin-3-one;
6-Hydroxy-8-{1-hydroxy-2-[2-(4-isopropyl-phenyl)-1,1-dimethyl-ethylamino]-ethyl}-4H-benzo[1,4]oxazin-3-one;
8-{2-[2-(4-Ethyl-phenyl)-1,1-dimethyl-ethylamino]-1-hydroxy-ethyl}-6-hydroxy-4H-benzo[1,4]oxazin-3-one;
8-{2-[2-(4-Ethoxy-phenyl)-1,1-dimethyl-ethylamino]-1-hydroxy-ethyl}-6-hydroxy-4H-benzo[1,4]oxazin-3-one;
4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid;
8-{2-[2-(3,4-Difluorphenyl)-1,1-dimethyl-ethylamino]-1-hydroxy-ethyl}-6-hydroxy-4H-benzo[1,4]oxazin-3-one;
1-(4-Ethoxy-carbonylamino-3-cyano-5-fluorophenyl)-2-(tert-butylamino)ethanol;
N-[2-Hydroxy-5-(1-hydroxy-2-{2-[4-(2-hydroxy-2-phenyl-ethylamino)-phenyl]-ethylamino}-ethyl)-phenyl]-formamide;
8-Hydroxy-5-(1-hydroxy-2-{2-[4-(6-methoxy-biphenyl-3-ylamino)-phenyl]-ethylamino}-ethyl)-1H-quinolin-2-one;
8-Hydroxy-5-[1-hydroxy-2-(6-phenethylamino-hexylamino)-ethyl]-1H-quinolin-2-one;
5-[2-(2-{4-[4-(2-Amino-2-methyl-propoxy)-phenylamino]-phenyl}-ethylamino)-1-hydroxy-ethyl]-8-hydroxy-1H-quinolin-2-one;
[3-(4-{6-[2-Hydroxy-2-(4-hydroxy-3-hydroxymethyl-phenyl)-ethylamino]hexyl-oxy}-butyl)-5-methyl-phenyl]-urea;
4-(2-{6-[2-(2,6-Dichloro-benzyloxy)-ethoxy]-hexylamino}-1-hydroxy-ethyl)-2-hydroxymethyl-phenole;
3-(4-{6-[2-Hydroxy-2-(4-hydroxy-3-hydroxymethyl-phenyl)-ethylamino]-hexyl-oxy}-butyl)-benzenesulfonamide;
3-(3-{7-[2-Hydroxy-2-(4-hydroxy-3-hydroxymethyl-phenyl)-ethylamino]-heptyloxy}-propyl)-benzenesulfonamide;
4-(2-{6-[4-(3-Cyclopentanesulfonyl-phenyl)-butoxy]-hexylamino}-1-hydroxy-ethyl)-2-hydroxymethyl-phenole;
N-Adamantan-2-yl-2-(3-{2-[2-hydroxy-2-(4-hydroxy-3-hydroxymethyl-phenyl)-ethylamino]-propyl}-phenyl)-acetamide;
(R,S)-4-(2-{[6-(2,2-Difluoro-4-phenylbutoxy)hexyl]amino}-1-hydroxy-ethyl)-2-(hydroxymethyl)phenol;
(R,S)-4-(2-{[6-(2,2-Difluoro-2-phenylethoxy)hexyl]amino}-1-hydroxy-ethyl)-2-(hydroxymethyl)phenol;
(R,S)-4-(2-{[4,4-Difluoro-6-(4-phenylbutoxy)hexyl]amino}-1-hydroxy-ethyl)-2-(hydroxy-methyl)phenol;
(R,S)-4-(2-{[6-(4,4-Difluoro-4-phenylbutoxy)hexyl]amino}-1-hydroxy-ethyl)-2-(hydroxymethyl)phenol;
(R,S)-5-(2-{[6-(2,2-Difluoro-2-phenylethoxy)hexyl]amino}-1-hydroxy-ethyl)-8-hydroxyquinolin-2 (1H)-one;
(R,S)-[2-({6-[2,2-Difluoro-2-(3-methylphenyl)ethoxy]hexyl}amino)-1-hydroxyethyl]-2-(hydroxymethyl)phenol;
4-(1R)-2-{[6-(2,2-Difluoro-2-phenylethoxy)hexyl]amino}-1-hydroxyethyl)-2-(hydroxymethyl)phenol;
(R,S)-2-(Hydroxymethyl)-4-(1-hydroxy-2-{[4,4,515-tetrafluoro-6-(3-phenylpropoxy)-hexyl]amino}ethyl)phenol;
(R,S)-[5-(2-{[6-(2,2-Difluoro-2-phenylethoxy)hexyl]amino}-1-hydroxy-ethyl-)-2-hydroxy-phenyl]formamide;
(R,S)-4-[2-({6-[2-(3-Bromophenyl)-2,2-difluoroethoxy]hexyl}amino)-1-hydroxyethyl]-2-(hydroxymethyl)phenol;
(R,S)—N-[3-(1,1-Difluoro-2-{[6-({2-hydroxy-2-[4-hydroxy-3-(hydroxymethyl)-phenyl]-ethyl}amino)hexyl]oxy}ethyl)phenyl]urea;
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione;
(R,S)-4-[2-({6-[2,2-difluoro-2-(3-methoxyphenyl)ethoxy]hexyl}amino)-1-hydroxyethyl]-2-(hydroxymethyl)phenol;
5-((1R)-2-{[6-(2,2-difluoro-2-phenylethoxy)hexyl]amino}-1-hydroxyethyl)-8-hydroxyquinolin-2 (1H)-one;
4-((1R)-2-{[4,4-Difluoro-6-(4-phenylbutoxy)hexyl]amino}-1-hydroxy-ethyl)-2-(hydroxymethyl)phenol;
(R,S)-4-(2-{[6-(3,3-Difluoro-3-phenylpropoxy)hexyl]amino}-1-hydroxy-ethyl-)-2-(hydroxymethyl)phenol;
(R,S)-(2-{[6-(2,2-Difluoro-2-phenylethoxy)-4,4-difluoro-hexyl]amino}-1-hydroxyethyl)-2-(hydroxymethyl)phenol;
(R,S)-4-(2-{[6-(2,2-difluoro-3-phenylpropoxy)hexyl]amino}-1-hydroxyethyl)-2-(hydroxy-methyl)phenol;
3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide;
N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide;
7-[2-(2-{3-[2-(2-Chloro-phenyl)-ethylamino]-propylsulfanyl}-ethylamino)-1-hydroxy-ethyl]-4-hydroxy-3H-benzothiazol-2-one; or
7-[(1R)-2-(2-{3-[2-(2-Chloro-phenyl)-ethylamino]-propylsulfanyl}-ethylamino)-1-hydroxyethyl]-4-hydroxy-3H-benzothiazol-2-one; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is an anticholinergic selected from Tiotropium salts, preferably the bromide salt, Oxitropium salts, preferably the bromide salt, Flutropium salts, preferably the bromide salt, Ipratropium salts, preferably the bromide salt, Aclidinium salts, preferably the bromide salt, Glycopyrronium salts, preferably the bromide salt, Trospium salts, preferably the chloride salt, Tolterodin. From the above mentioned salts the pharmaceutically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among
2,2-Diphenylpropionic acid tropenole ester-methobromide;
2,2-Diphenylpropionic acid scopine ester-methobromide;
2-Fluor-2,2-Diphenylacetic acid scopine ester-methobromide;
2-Fluor-2,2-Diphenylacetic acid tropenole ester-methobromide;

3,3',4,4'-Tetrafluorbenzil acid tropenole ester-methobromide;
3,3',4,4'-Tetrafluorbenzil acid scopine ester-methobromide;
4,4'-Difluorbenzil acid tropenole ester-methobromide;
4,4'-Difluorbenzil acid scopine ester-methobromide;
3,3'-Difluorbenzil acid tropenole ester-methobromide;
3,3'-Difluorbenzil acid scopine ester-methobromide;
9-Hydroxy-fluorene-9-carbon acid tropenole ester-methobromide;
9-Fluor-fluorene-9-carbon acid tropenole ester-methobromide;
9-Hydroxy-fluorene-9-carbon acid scopine ester-methobromide;
9-Fluor-fluorene-9-carbon acid scopine ester methobromide;
9-Methyl-fluorene-9-carbon acid tropenole estermethobromide;
9-Methyl-fluorene-9-carbon acid scopine estermethobromide;
Benzil acid cyclopropyl tropine ester-methobromide;
2,2-Diphenylpropionic acid cyclopropyl tropine ester-methobromide;
9-Hydroxy-xanthene-9-carbon acid cyclopropyl tropine ester-methobromide;
9-Methyl-fluorene-9-carbon acid cyclopropyl tropine ester-methobromide;
9-Methyl-xanthene-9-carbon acid cyclopropyl tropine ester-methobromide;
9-Hydroxy-fluorene-9-carbon acid cyclopropyl tropine ester-methobromide;
4,4'-Difluorbenzil acid methylester cyclopropyl tropine ester-methobromide;
9-Hydroxy-xanthene-9-carbon acid tropenole ester-methobromide;
9-Hydroxy-xanthene-9-carbon acid scopine ester methobromide;
9-Methyl-xanthene-9-carbon acid tropenole ester-methobromide;
9-Methyl-xanthene-9-carbon acid scopine estermethobromide;
9-Ethyl-xanthene-9-carbon acid tropenole ester methobromide;
9-Difluormethyl-xanthene-9-carbon acid tropenole ester-methobromide; or
9-Hydroxymethyl-xanthene-9-carbon acid scopine ester methobromide.

In one embodiment, the additional therapeutic agent is a corticosteroid selected from Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tipredane,
{20R-16alpha,17alpha-[butylidenebis(oxy)]-6alpha,9alpha-difluoro-11beta-hydroxy-17beta-(methylthio)androsta-4-en-3-one};
9-fluoro-11beta,17,21-trihydroxy-16alpha-methylpregna-1,4-diene-3,20-dione 21-cyclohexanecarboxylate 17-cyclopropanecarboxylate;
16,17-butylidenedioxy-6,9-difluoro-11-hydroxy-17-(methylthio)androst-4-en-3-one;
Flunisolide-21-[4'-(nitrooxymethyl)benzoate];
6,9-Difluoro-17-[(2-furanylcarbonyl)oxy]-11-hydroxy-16-methyl-3-oxo-androsta-1,4-dien-17-carbothion acid (S)-fluoromethylester;
6,9-Difluoro-11-hydroxy-16-methyl-3-oxo-17-propionyloxy-androsta-1,4-dien-17-carbothion acid (S)-(2-oxo-tetrahydro-furan-3S-yl)ester; or 6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester; optionally in racemic form, as enantiomers, diastereomeres or as pharmaceutically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

In one embodiment, the additional therapeutic agent is a PDE4-inhibitor selected from Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste;
5-[(N-(2,5-dichloro-3-pyridinyl)-carboxamide]-8-methoxyquinoline;
5-[N-(3,5-dichloro-1-oxido-4-pyridinyl)-carboxamide]-8-methoxy-2-(trifluo-romethyl)-quinoline;
N-(3,5-dichloropyrid-4-yl)-[1-(4-fluorobenzyl)-5-hydroxyindole-3-yl]glyoxyl acid amide);
9-[(2-fluorophenyl)methyl]-N-methyl-2-(trifluoromethyl)-9H-purine-6-amine;
4-[(2R)-2-[3-(cyclopentyloxy)-4-methoxyphenyl]-2-phenylethyl]-pyridine;
N-[(3R)-3,4,6,7-tetrahydro-9-methyl-4-oxo-1-phenylpyrrolo[3,2,1-jk-][1,4]benzodiazepin-3-yl]-4-Pyridinecarboxamide;
4-[6,7-diethoxy-2,3-bis(hydroxymethyl)-1-naphthalenyl]-1-(2-methoxyethyl)-2 (1H)-pyridinone;
2-[4-[6,7-diethoxy-2,3-bis(hydroxymethyl)-1-naphthalenyl]-2-pyridinyl]-4-(3-pyridinyl)-1 (2H)-Phthalazinone;
(3-(3-cyclopenyloxy-4-methoxybenzyl)-6-ethylamino-8-isopropyl-3H-purine;
beta-[3-(cyclopentyloxy)-4-methoxyphenyl]-1,3-dihydro-1,3-dioxo-2H-isoindole-2-propanamide;
9-ethyl-2-methoxy-7-methyl-5-propyl-imidazo[1,5-a]pyrido[3,2-e]pyrazin-6(-5H)-one;
5-[3-(cyclopentyloxy)-4-methoxyphenyl]-3-[(3-methylphenyl)methyl](3S,5S)-2-piperidinone;
4-[1-[3,4-bis(difluoromethoxy)phenyl]-2-(3-methyl-1-oxido-4-pyridinyl)ethyl]-alpha,alpha-bis(trifluoromethyl)-Benzenemethanol;
N-(3,5-Dichloro-1-oxo-pyridine-4-yl)-4-difluoromethoxy-3-cyclopropylmethoxy-benzamide;
(−)p-[(4aR*,10bS*)-9-Ethoxy-1,2,3,4,4a,10b-hexahydro-8-methoxy-2-methyl-benzo[s][1,6]naphthyridin-6-yl]-N,N-diisopropylbenzamide;
(R)-(+)-1-(4-Bromobenzyl)-4-[(3-cyclopentyloxy)-4-methoxyphenyl]-2-pyrrolidone;
3-(Cyclopentyloxy-4-methoxyphenyl)-1-(4-N'—[N-2-cyano-S-methyl-isothioureido]-benzyl)-2-pyrrolidone;
cis[4-Cyano-4-(3-cyclopentyloxy-4-methoxyphenyl)cyclohexan-1-carbon acid];
2-Carbomethoxy-4-cyano-4-(3-cyclopropylmethoxy-4-difluoromethoxyphenyl)-cyclohexan-1-one;
cis[4-Cyano-4-(3-cyclopropylmethoxy-4-difluoromethoxyphenyl)cyclohexan-1-ol];
(R)-(+)-Ethyl[4-(3-cyclopentyloxy-4-methoxyphenyl)pyrrolidine-2-yliden]acetate;
(S)-(−)-Ethyl[4-(3-cyclopentyloxy-4-methoxyphenyl)pyrrolidine-2-yliden]acetate;
9-Cyclopentyl-5,6-dihydro-7-ethyl-3-(2-thienyl)-9H-pyrazolo[3,4-c]-1,2,4-triazolo[4,3-a]pyridine; or
9-Cyclopentyl-5,6-dihydro-7-ethyl-3-(tert-butyl)-9H-pyrazolo[3,4-c]-1,2,4-triazolo[4,3-a]pyridine; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is a LTD4-antagonist selected from Montelukast, Pranlukast, Zafirlukast, Masikulast, L-733321 (see compound 2ab of D. Guay et al, Bioorg. Med. Chem. Lett. 8 (1998) 453-458);

(E)-8-[2-[4-[4-(4-Fluorophenyl)butoxy]phenyl]ethenyl]-2-(1H-tetrazole-5-yl)-4H-1-benzopyran-4-one;

4-[6-Acetyl-3-[3-(4-acetyl-3-hydroxy-2-propylphenylthio) propoxy]-2-propyl-phenoxy]-butyric acid;

1-(((R)-(3-(2-(6,7-Difluoro-2-quinolinyl)ethenyl)phenyl)-3-(2-(2-hydroxy-2-propyl)phenyl)thio)methylcyclopropane-acetic acid;

1-(((1(R)-3 (3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid; or

[2-[[2-(4-tert-Butyl-2-thiazolyl)-5-benzofuranyl]oxymethyl]phenyl]acetic acid; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

In one embodiment, the additional therapeutic agent is an EGFR-inhibitor selected from Cetuximab, Trastuzumab, Panitumumab Gefitinib, Canertinib, Erlotinib, Mab ICR-62;

4-[(3-Chlor-4-fluorophenyl)amino]-6-{[4-(morpholine-4-yl)-1-oxo-2-butene-1-yl]amino}-7-cyclopropylmethoxy-quinazoline;

4-[(3-Chlor-4-fluorophenyl)amino]-6-{[4-(N,N-diethyl-amino)-1-oxo-2-butene-1-yl]amino}-7-cyclopropyl-methoxy-quinazoline;

4-[(3-Chlor-4-fluorophenyl)amino]-6-{[4-(N,N-dimethyl-amino)-1-oxo-2-butene-1-yl]amino}-7-cyclopropyl-methoxy-quinazoline;

4-[(R)-(1-Phenyl-ethyl)amino]-6-{[4-(morpholine-4-yl)-1-oxo-2-butene-1-yl-]amino}-7-cyclopentyloxy-quinazoline;

4-[(3-Chlor-4-fluorophenyl)amino]-6-{[4-((R)-6-methyl-2-oxo-morpholine-4-yl)-1-oxo-2-butene-1-yl]amino}-7-cyclopropylmethoxy-quinazoline;

4-[(3-Chlor-4-fluorophenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline;

4-[(3-Chlor-4-fluorophenyl)amino]-6-{[4-((R)-2-methoxymethyl-6-oxo-morpholine-4-yl)-1-oxo-2-butene-1-yl]amino}-7-cyclopropylmethoxy-quinazoline;

4-[(3-Chlor-4-fluorophenyl)amino]-6-[2-((S)-6-methyl-2-oxo-morpholine-4-yl)-ethoxy]-7-methoxy-quinazoline;

4-[(3-Chlor-4-fluorophenyl)amino]-6-({4-[N-(2-methoxy-ethyl)-N-methyl-amino]-1-oxo-2-butene-1-yl}amino)-7-cyclopropylmethoxy-quinazoline;

4-[(3-Chlor-4-fluorophenyl)amino]-6-{[4-(N,N-dimethyl-amino)-1-oxo-2-butene-1-yl]amino}-7-cyclopentyloxy-quinazoline;

4-[(R)-(1-Phenyl-ethyl)amino]-6-{[4-(N,N-bis-(2-methoxy-ethyl)-amino]-1-oxo-2-butene-1-yl]amino}-7-cyclopropylmethoxy-quinazoline;

4-[(R)-(1-Phenyl-ethyl)amino]-6-({4-[N-(2-methoxy-ethyl)-N-ethyl-amino]-1-oxo-2-butene-1-yl}amino)-7-cyclopropylmethoxy-quinazoline;

4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline;

4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline;

4-[(3-Chlor-4-fluorophenyl)amino]-6-{[4-(N,N-dimethyl-amino)-1-oxo-2-butene-1-yl]amino}-7-((R)-tetrahydrofuran-3-yloxy)-quinazoline;

4-[(3-Chlor-4-fluorophenyl)amino]-6-{[4-(N,N-dimethyl-amino)-1-oxo-2-butene-1-yl]amino}-7-((S)-tetrahydrofuran-3-yloxy)-quinazoline;

4-[(3-Chlor-4-fluorophenyl)amino]-6-({4-[N-(2-methoxy-ethyl)-N-methyl-amino]-1-oxo-2-butene-1-yl}amino)-7-cyclopentyloxy-quinazoline;

4-[(3-Chlor-4-fluorophenyl)amino]-6-{[4-(N-cyclopropyl-N-methyl-amino)-1-oxo-2-butene-1-yl]amino}-7-cyclopentyloxy-quinazoline;

4-[(3-Chlor-4-fluorophenyl)amino]-6-{[4-(N,N-dimethyl-amino)-1-oxo-2-butene-1-yl]amino}-7-[(R)-(tetrahydrofuran-2-yl)methoxy]-quinazoline;

4-[(3-Chlor-4-fluorophenyl)amino]-6-{[4-(N,N-dimethyl-amino)-1-oxo-2-butene-1-yl]amino}-7-[(S)-(tetrahydrofuran-2-yl)methoxy]-quinazoline;

4-[(3-Ethinyl-phenyl)amino]-6,7-bis-(2-methoxy-ethoxy)-quinazoline;

4-[(3-Chlor-4-fluorophenyl)amino]-7-[3-(morpholine-4-yl)-propyloxy]-6-[(vinylcarbonyl)amino]-quinazoline;

4-[(R)-(1-Phenyl-ethyl)amino]-6-(4-hydroxy-phenyl)-7H-pyrrolo[2,3-d]pyrimidine;

3-Cyano-4-[(3-chlor-4-fluorophenyl)amino]-6-{[4-(N,N-dimethylamino)-1-oxo-2-butene-1-yl]amino}-7-ethoxy-quinoline;

4-{[3-Chlor-4-(3-fluor-benzyloxy)-phenyl]amino}-6-(5-{[(2-methansulfonyl-ethyl)amino]methyl}-furan-2-yl)quinazoline;

4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline;

4-[(3-Chlor-4-fluorophenyl)amino]-6-{[4-(morpholine-4-yl)-1-oxo-2-butene-1-yl]amino}-7-[(tetrahydrofuran-2-yl)methoxy]-quinazoline;

4-[(3-Chlor-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline;

4-[(3-Ethinyl-phenyl)amino]-6-{[4-(5,5-dimethyl-2-oxo-morpholine-4-yl)-1-oxo-2-butene-1-yl]amino}-quinazoline;

4-[(3-Chlor-4-fluorophenyl)amino]-6-[2-(2,2-dimethyl-6-oxo-morpholine-4-yl)-ethoxy]-7-methoxy-quinazoline;

4-[(3-Chlor-4-fluorophenyl)amino]-6-[2-(2,2-dimethyl-6-oxo-morpholine-4-yl)-ethoxy]-7-[(R)-(tetrahydrofuran-2-yl)methoxy]-quinazoline;

4-[(3-Chlor-4-fluorophenyl)amino]-7-[2-(2,2-dimethyl-6-oxo-morpholine-4-yl)-ethoxy]-6-[(S)-(tetrahydrofuran-2-yl)methoxy]-quinazoline;

4-[(3-Chlor-4-fluorophenyl)amino]-6-{2-[4-(2-oxo-morpholine-4-yl)-piperidin-1-yl]-ethoxy}-7-methoxy-quinazoline;

4-[(3-Chlor-4-fluorophenyl)amino]-6-[1-(tert-butyloxycarbonyl)-piperidine-4-yloxy]-7-methoxy-quinazoline;

4-[(3-Chlor-4-fluorophenyl)amino]-6-(trans-4-amino-cyclohexane-1-yloxy)-7-methoxy-quinazoline;
4-[(3-Chlor-4-fluorophenyl)amino]-6-(trans-4-methansulfonylamino-cyclohexane-1-yloxy)-7-methoxy-quinazoline;
4-[(3-Chlor-4-fluorophenyl)amino]-6-(tetrahydropyran-3-yloxy)-7-methoxy-quinazoline;
4-[(3-Chlor-4-fluorophenyl)amino]-6-(1-methyl-piperidine-4-yloxy)-7-methoxy-quinazoline;
4-[(3-Chlor-4-fluorophenyl)amino]-6-{1-[(morpholine-4-yl)carbonyl]-piperidine-4-yloxy}-7-methoxy-quinazoline;
4-[(3-Chlor-4-fluorophenyl)amino]-6-{1-[(methoxymethyl)carbonyl]-piperidine-4-yloxy}-7-methoxy-quinazoline;
4-[(3-Chlor-4-fluorophenyl)amino]-6-(piperidine-3-yloxy)-7-methoxy-quinazoline;
4-[(3-Chlor-4-fluorophenyl)amino]-6-[1-(2-acetylamino-ethyl)-piperidine-4-yloxy]-7-methoxy-quinazoline;
4-[(3-Chlor-4-fluorophenyl)amino]-6-(tetrahydropyran-4-yloxy)-7-ethoxy-quinazoline;
4-[(3-Chlor-4-fluorophenyl)amino]-6-((S)-tetrahydrofuran-3-yloxy)-7-hydroxy-quinazoline;
4-[(3-Chlor-4-fluorophenyl)amino]-6-(tetrahydropyran-4-yloxy)-7-(2-methoxy-ethoxy)-quinazoline;
4-[(3-Chlor-4-fluorophenyl)amino]-6-{trans-4-[(dimethylamino)sulfonylamino]-cyclohexane-1-yloxy}-7-methoxy-quinazoline;
4-[(3-Chlor-4-fluorophenyl)amino]-6-{trans-4-[(morpholine-4-yl)carbonylamino]-cyclohexane-1-yloxy}-7-methoxy-quinazoline;
4-[(3-Chlor-4-fluorophenyl)amino]-6-{trans-4-[(morpholine-4-yl)sulfonylamino]-cyclohexane-1-yloxy}-7-methoxy-quinazoline;
4-[(3-Chlor-4-fluorophenyl)amino]-6-(tetrahydropyran-4-yloxy)-7-(2-acetyl-amino-ethoxy)-quinazoline;
4-[(3-Chlor-4-fluorophenyl)amino]-6-(tetrahydropyran-4-yloxy)-7-(2-methane-sulfonylamino-ethoxy)-quinazoline;
4-[(3-Chlor-4-fluorophenyl)amino]-6-{1-[(piperidine-1-yl)carbonyl]-piperidine-4-yloxy}-7-methoxy-quinazoline;
4-[(3-Chlor-4-fluorophenyl)amino]-6-(1-aminocarbonylmethyl-piperidine-4-yloxy)-7-methoxy-quinazoline;
4-[(3-Chlor-4-fluorophenyl)amino]-6-(cis-4-{N-[(tetrahydropyran-4-yl)carbonyl]-N-methyl-amino}-cyclohexane-1-yloxy)-7-methoxy-quinazoline;
4-[(3-Chlor-4-fluorophenyl)amino]-6-(cis-4-{N-[(morpholine-4-yl)carbonyl]-N-methyl-amino}-cyclohexane-1-yloxy)-7-methoxy-quinazoline;
4-[(3-Chlor-4-fluorophenyl)amino]-6-(cis-4-{N-[(morpholine-4-yl)sulfonyl]-N-methyl-amino}-cyclohexane-1-yloxy)-7-methoxy-quinazoline;
4-[(3-Chlor-4-fluorophenyl)amino]-6-(trans-4-ethansulfonylamino-cyclohexane-1-yloxy)-7-methoxy-quinazoline;
4-[(3-Chlor-4-fluorophenyl)amino]-6-(1-methansulfonyl-piperidine-4-yloxy)-7-ethoxy-quinazoline;
4-[(3-Chlor-4-fluorophenyl)amino]-6-(1-methansulfonyl-piperidine-4-yloxy)-7-(2-methoxy-ethoxy)-quinazoline;
4-[(3-Chlor-4-fluorophenyl)amino]-6-[1-(2-methoxy-acetyl)-piperidine-4-yl-oxy]-7-(2-methoxy-ethoxy)-quinazoline;
4-[(3-Chlor-4-fluorophenyl)amino]-6-(cis-4-acetylamino-cyclohexane-1-yloxy)-7-methoxy-quinazoline;
4-[(3-Ethinyl-phenyl)amino]-6-[1-(tert-butyloxycarbonyl)-piperidine-4-yloxy]-7-methoxy-quinazoline;
4-[(3-Ethinyl-phenyl)amino]-6-(tetrahydropyran-4-yloxy]-7-methoxy-quinazoline;
4-[(3-Chlor-4-fluorophenyl)amino]-6-(cis-4-{N-[(piperidine-1-yl)carbonyl]-N-methyl-amino}-cyclohexane-1-yloxy)-7-methoxy-quinazoline;
4-[(3-Chlor-4-fluorophenyl)amino]-6-(cis-4-{N-[(4-methyl-piperazine-1-yl)-carbonyl]-N-methyl-amino}-cyclohexane-1-yloxy)-7-methoxy-quinazoline;
4-[(3-Chlor-4-fluorophenyl)amino]-6-{cis-4-[(morpholine-4-yl)carbonylamino-cyclohexane-1-yloxy}-7-methoxy-quinazoline;
4-[(3-Chlor-4-fluorophenyl)amino]-6-{1-[2-(2-oxopyrrolidine-1-yl)ethyl]-piperidine-4-yloxy}-7-methoxy-quinazoline;
4-[(3-Chlor-4-fluorophenyl)amino]-6-{1-[(morpholine-4-yl)carbonyl]-piperidine-4-yloxy}-7-(2-methoxy-ethoxy)-quinazoline;
4-[(3-Ethinyl-phenyl)amino]-6-(1-acetyl-piperidine-4-yloxy)-7-methoxy-quinazoline;
4-[(3-Ethinyl-phenyl)amino]-6-(1-methyl-piperidine-4-yloxy)-7-methoxy-quinazoline;
4-[(3-Ethinyl-phenyl)amino]-6-(1-methansulfonyl-piperidine-4-yloxy)-7-methoxy-quinazoline;
4-[(3-Chlor-4-fluorophenyl)amino]-6-(1-methyl-piperidine-4-yloxy)-7-(2-methoxy-ethoxy)-quinazoline;
4-[(3-Chlor-4-fluorophenyl)amino]-6-(1-isopropyloxycarbonyl-piperidine-4-yloxy)-7-methoxy-quinazoline;
4-[(3-Chlor-4-fluorophenyl)amino]-6-(cis-4-methylamino-cyclohexane-1-yloxy)-7-methoxy-chinazoline;
4-[(3-Chlor-4-fluorophenyl)amino]-6-{cis-4-[N-(2-methoxy-acetyl)-N-methyl-amino]-cyclohexane-1-yloxy}-7-methoxy-quinazoline;
4-[(3-Ethinyl-phenyl)amino]-6-(piperidine-4-yloxy)-7-methoxy-quinazoline;
4-[(3-Ethinyl-phenyl)amino]-6-[1-(2-methoxy-acetyl)-piperidine-4-yloxy]-7-methoxy-quinazoline;
4-[(3-Ethinyl-phenyl)amino]-6-{1-[(morpholine-4-yl)carbonyl]-piperidine-4-yloxy}-7-methoxy-quinazoline;
4-[(3-Chlor-4-fluorophenyl)amino]-6-{1-[cis-2,6-dimethyl-morpholine-4-yl)-carbonyl]-piperidine-4-yloxy}-7-methoxy-quinazoline;
4-[(3-Chlor-4-fluorophenyl)amino]-6-{1-[(2-methyl-morpholine-4-yl)carbonyl]-piperidine-4-yloxy}-7-methoxy-quinazoline;
4-[(3-Chlor-4-fluorophenyl)amino]-6-{1-[(S,S)-(2-oxa-5-aza-bicyclo[2.2.1]-hept-5-yl)carbonyl]-piperidine-4-yloxy}-7-methoxy-quinazoline;
4-[(3-Chlor-4-fluorophenyl)amino]-6-{1-[(N-methyl-N-2-methoxyethyl-amino)-carbonyl]-piperidine-4-yloxy}-7-methoxy-quinazoline;
4-[(3-Chlor-4-fluorophenyl)amino]-6-(1-ethyl-piperidine-4-yloxy)-7-methoxy-quinazoline;
4-[(3-Chlor-4-fluorophenyl)amino]-6-{1-[(2-methoxyethyl)carbonyl]-piperidine-4-yloxy}-7-methoxy-quinazoline;
4-[(3-Chlor-4-fluorophenyl)amino]-6-{1-[(3-methoxypropyl-amino)-carbonyl]-piperidine-4-yloxy}-7-methoxy-quinazoline;
4-[(3-Chlor-4-fluorophenyl)amino]-6-[cis-4-(N-methansulfonyl-N-methyl-amino)-cyclohexane-1-yloxy]-7-methoxy-quinazoline;
4-[(3-Chlor-4-fluorophenyl)amino]-6-[cis-4-(N-acetyl-N-methyl-amino)-cyclohexane-1-yloxy]-7-methoxy-quinazoline;
4-[(3-Chlor-4-fluorophenyl)amino]-6-(trans-4-methyl-amino-cyclohexane-1-yloxy)-7-methoxy-quinazoline;
4-[(3-Chlor-4-fluorophenyl)amino]-6-[trans-4-(N-methansulfonyl-N-methyl-amino)-cyclohexane-1-yloxy]-7-methoxy-quinazoline;

4-[(3-Chlor-4-fluorophenyl)amino]-6-(trans-4-dimethyl-amino-cyclohexane-1-yloxy)-7-methoxy-quinazoline;

4-[(3-Chlor-4-fluorophenyl)amino]-6-(trans-4-{N-[(morpholine-4-yl)carbonyl]-N-methyl-amino}-cyclohexane-1-yloxy)-7-methoxy-quinazoline;

4-[(3-Chlor-4-fluorophenyl)amino]-6-[2-(2,2-dimethyl-6-oxo-morpholine-4-yl)-ethoxy]-7-[(S)-(tetrahydrofuran-2-yl)methoxy]-quinazoline;

4-[(3-Chlor-4-fluorophenyl)amino]-6-(1-methansulfonyl-piperidine-4-yloxy)-7-methoxy-quinazoline; or 4-[(3-Chlor-4-fluorophenyl)amino]-6-(1-cyano-piperidine-4-yloxy)-7-methoxy-quinazoline; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In another embodiment, the additional therapeutic agent is a dopamine antagonist selected from Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In another embodiment, the additional therapeutic agent is an antiallergic agent selected from Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is an MAP kinase inhibitor selected from Bentamapimod, Doramapimod, 5-Carbamoylindole, 6-[(aminocarbonyl)(2,6-difluorophenyl)amino]-2-(2,4-difluorophenyl)-3-pyridine carboxamide, alpha-[2-[[2-(3-pyridinyl)ethyl]amino]-4-pyrimidinyl]-2-benzothiazole acetonitrile, 9,12-Epoxy-1H-diindolo[1,2,3-fg:3',2',1'-kl]pyrrolo[3,4-i][1,6]benzodiazocine-10-Carboxylic acid, or 4-[3-(4-chlorophenyl)-5-(1-methyl-4-piperidinyl)-1H-pyrazole-4-yl]-pyrimidine, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is an MRP4-Inhibitor selected from N-Acetyl-dinitrophenyl-Cysteine, cGMP, Cholate, Diclofenac, Dehydroepiandrosterone 3-glucuronide, Dehydroepiandrosterone 3-sulphate, Dilazep, Dinitrophenyl-S-glutathione, Estradiol 17-beta-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycolithocholic acid sulphate, Ibuprofen, Indomethacin, Indoprofen, Ketoprofen, Lithocholic acid sulphate, Methotrexate, (E)-3-[[[3-[2-(7-Chloro-2-quinolinyl)ethenyl]phenyl]-[3-dimethylamino)-3-oxopropyl]thio]methyl]thio]-propanoic acid, alpha-Naphthyl-beta-D-glucuronide, Nitrobenzyl mercaptopurine riboside, Probenecid, Valspodar, Sildenafil, Sulfinpyrazone, Taurochenodeoxycholate, Taurocholate, Taurodeoxycholate, Taurolithocholate, Taurolithocholic acid sulphate, Topotecan, Trequinsin, Zaprinast or Dipyridamol, optionally in racemic form, as enantiomers, diastereomers or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic is an iNOS-Inhibitor selected from S-(2-Aminoethyl)isothiourea, Aminoguanidine, 2-Aminomethylpyridine, 5,6-dihydro-6-methyl-4H-1,3-thiazine-2-amine (AMT), L-Canavanin, 2-Iminopiperidine, S-Isopropylisothiourea, S-Methylisothiourea, S-Ethylisothiourea, S-Methylthiocitrulline, S-Ethylthiocitrulline, L-NA ($N^{\omega}$-Nitro-L-arginin), L-NAME ($N^{\omega}$-Nitro-L-argininmethylester), L-NMMA ($N^{\omega}$-Monomethyl-L-arginin), L-NIO ($N^{\omega}$-Iminoethyl-L-ornithin), L-NIL ($N^{\omega}$-iminoethyl-lysin), (S)-6-Acetimidoylamino-2-amino-hexanoic acid (1H-tetrazole-5-yl)-amide;

N-[[3-(aminomethyl)phenyl]methyl]-ethanimidamide;

(S)-4-(2-acetimidoylamino-ethylsulfanyl)-2-amino-buturic acid;

2-[2-(4-Methoxy-pyridine-2-yl)-ethyl]-3H-imidazo[4,5-b]pyridine;

2-((R)-3-amino-1-phenyl-propoxy)-4-chlor-5-fluorbenzonitrile;

2-((1R,3S)-3-amino-4-hydroxy-1-thiazole-5-yl-butylsulfanyl)-6-trifluoromethyl-nicotinonitrile;

2-((1R,3S)-3-amino-4-hydroxy-1-thiazole-5-yl-butylsulfanyl)-4-chlor-benzonitrile;

2-((1R,3S)-3-amino-4-hydroxy-1-thiazole-5-yl-butylsulfanyl)-5-chlor-benzonitrile;

(2S,4R)-2-amino-4-(2-chlor-5-trifluoromethyl-phenylsulfanyl)-4-thiazole-5-yl-butane-1-ol;

2-((1R,3S)-3-amino-4-hydroxy-1-thiazole-5-yl-butylsulfanyl)-5-chlor-nicotinonitrile;

4-((S)-3-amino-4-hydroxy-1-phenyl-butylsulfanyl)-6-methoxy-nicotinonitrile; or substituted 3-phenyl-3,4-dihydro-1-isoquinolinamine as for instance 1S,5S,6R)-7-Chlor-5-methyl-2-aza-bicyclo[4.1.0]hept-2-ene-3-ylamin (4R,5R)-5-Ethyl-4-methyl-thiazolidine-2-ylideneamine, (1S,5S,6R)-7-Chlor-5-methyl-2-aza-bicyclo[4.1.0]hept-2-ene-3-ylamin, (4R,5R)-5-Ethyl-4-methyl-thiazolidine-2-ylideneamine, (4R,5R)-5-Ethyl-4-methyl-selenazolidine-2-ylideneamine, 4-Aminotetrahydrobiopterine, (E)-3-(4-Chlor-phenyl)-N-(1-{2-oxo-2-[4-(6-trifluormethyl-pyrimidine-4-yloxy)-piperidine-1-yl]-ethylcarbamoyl}-2-pyridine-2-yl-ethyl)-acrylamide, 3-(2,4-Difluor-phenyl)-6-[2-(4-imidazole-1-ylmethyl-phenoxy)-ethoxy]-2-phenyl-pyridine, 3-{[(Benzo[1,3]dioxol-5-ylmethyl)-carbamoyl]-methyl}-4-(2-imidazole-1-ylpyrimidine-4-yl)-piperazine-1-carbon acid methylester, or (R)-1-(2-imidazole-1-yl-6-methyl-pyrimidine-4-yl)-pyrrolidine-2-carbon acid (2-benzo[1,3]dioxol-5-yl-ethyl)-amide, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples of preferred iNOS-Inhibitors which may be mentioned include antisense-Oligonucleotide, especially those antisense-Oligonucleotide binding iNOS-coding nucleic acids, examples therefore are disclosed in WO 01/52902, incorporated herein by reference in its entirety.

In another embodiment, the additional therapeutic agent is a SYK-inhibitor selected from 2-[(2-aminoethyl)amino]-4-[(3-bromophenyl)amino]-5-pyrimidinecarboxamide;
2-[[7-(3,4-dimethoxyphenyl)imidazo[1,2-c]pyrimidine-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;
N-[3-bromo-7-(4-methoxyphenyl)-1,6-naphthyridine-5-yl]-1,3-propanediamine;
7-(4-methoxyphenyl)-N-methyl-1,6-naphthyridine-5-amine;
N-[7-(4-methoxyphenyl)-1,6-naphthyridine-5-yl]-1,3-propanediamine;
N-[7-(2-thienyl)-1,6-naphthyridine-5-yl-1,3-propanediamine;
N-[7-[4-(dimethylamino)phenyl]-1,6-naphthyridine-5-yl]-1,2-ethanediamine;
N-[7-(4-methoxyphenyl)-2-(trifluoromethyl)-1,6-naphthyridine-5-yl]-1,3-propanediamine;
N-[7-(4-methoxyphenyl)-3-phenyl-1,6-naphthyridine-5-yl]-1,3-propanediamine;
N-(7-phenyl-1,6-naphthyridine-5-yl)-1,3-propanediamine;
N-[7-(3-fluorophenyl)-1,6-naphthyridine-5-yl]-1,3-propanediamine;
N-[7-(3-chlorophenyl)-1,6-naphthyridine-5-yl]-1,3-propanediamine;
N-[7-[3-(trifluoromethoxy)phenyl]-1,6-naphthyridine-5yl]-1,3-propanediamine;
N-[7-(4-fluorophenyl)-1,6-naphthyridine-5-yl]-1,3-propanediamine;
N-[7-(4-fluorophenyl)-1,6-naphthyridine-5-yl]-1,3-propanediamine;
N-[7-(4-chlorophenyl)-1,6-naphthyridine-5-yl]-1,3-propanediamine;
N-[7-(4'-methyl[1,1'-biphenyl]-4-yl)-1,6-naphthyridine-1,3-propane-diamine;
N-[7-[4-(dimethylamino)phenyl]-1,6-naphthyridine-5-yl]-1,3-propanediamine;
N-[7-[4-(diethylamino)phenyl]-1,6-naphthyridine-5-yl]-1,3-propane-diamine;
N-[7-[4-(4-morpholinyl)phenyl]-1,6-naphthyridine-5-yl]-1,3-propanediamine;
N-[7-[4-[[2-(dimethylamino)ethyl]methylamino]phenyl]-1,6-naphthyridine-5-yl]-1,3-propanediamine;
N-[7-(4-bromophenyl)-1,6-naphthyridine-5-yl]-1,3-propanediamine;
N-[7-(4-methylphenyl)-1,6-naphthyridine-5-yl]-1,3-propanediamine;
N-[7-[4-(methylthio)phenyl]-1,6-naphthyridine-5-yl]-1,3-propanediamine;
N-[7-[4-(1-methylethyl)phenyl]-1,6-naphthyridine-5-yl]-1,3-propanediamine;
7-[4-(dimethylamino)phenyl]-N-methyl-1,6-naphthyridine-5-amine;
7-[4-(dimethylamino)phenyl]-N,N-dimethyl-1,6-naphthyridine-5-amine;
N-[7-[4-(dimethylamino)phenyl]-1,6-naphthyridine-5-yl]-1,4-butanediamine;
N-[7-[4-(dimethylamino)phenyl]-1,6-naphthyridine-5-yl]-1,5-pentanediamine;
3-[[7-[4-(dimethylamino)phenyl]-1,6-naphthyridine-5-yl]oxy]-1-propanole;
4-[5-(4-aminobutoxy)-1,6-naphthyridine-7-yl]-N,N-dimethyl-benzenamine;
4-[[7-[4-(dimethylamino)phenyl]-1,6-naphthyridine-5-yl]amino]-1-butanole;
N-[7-[4-(dimethylamino)phenyl]-1,6-naphthyridine-5-yl]-N-methyl-1,3-propanediamine;
N-[7-[4-(dimethylamino)phenyl]-1,6-naphthyridine-5-yl]-N'-methyl-1,3-propanediamine;
N-[7-[4-(dimethylamino)phenyl]-1,6-naphthyridine-5-yl]-N,N'-dimethyl-1,3-propanediamine;
1-amino-3-[[7-[4-(dimethylamino)phenyl]-1,6-naphthyridine-5-yl]amino]-2-propanole;
N-[7-[4-(dimethylamino)phenyl]-1,6-naphthyridine-5-yl]-2,2-dimethyl-1,3-propanediamine;
7-[4-(dimethylamino)phenyl]-N-(3-pyridinylmethyl)-1,6-naphthyridine-5-amine;
N-[(2-aminophenyl)methyl]-7-[4-(dimethylamino)phenyl]-1,6-naphthyridine-5-amine;
N-[7-[6-(dimethylamino)[1,1'-biphenyl]-3-yl]-1,6-naphthyridine-5-yl]-1,3-propanediamine;
N-[7-[3-chloro-4-(diethylamino)phenyl]-1,6-naphthyridine-5-yl]-1,3-propanediamine;
N-[7-[4-(dimethylamino)-3-methoxyphenyl]-1,6-naphthyridine-5-yl]-1,3-propanediamine;
N-[7-[4-(diethylamino)phenyl]-3-methyl-1,6-naphthyridine-5-yl]-1,3-propanediamine;
N-[7-(3'-fluoro[1,1'-biphenyl]-3-yl)-1,6-naphthyridine-5-yl]-1,2-ethanediamine;
N-[7-(4-methoxyphenyl)-1,6-naphthyridine-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trimethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro[1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;
1-amino-3-[[7-(3,4,5-trimethoxyphenyl)-1,6-naphthyridine-5-yl]amino]-2-propanole;

1-amino-3-[[7-(4-bromophenyl)-1,6-naphthyridine-5-yl]amino]-2-propanole;
N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]-ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;
N-[7-[4-(dimethylamino)phenyl]-1,6-naphthyridine-5-yl]-1,3-cyclohexane diamine;
N,N-dimethyl-4-[5-(1-piperazinyl)-1,6-naphthyridine-7-yl]-benzenamine;
4-[5-(2-methoxyethoxy)-1,6-naphthyridine-7-yl]-N,N-dimethyl-benzeneamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]-N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamine;
N-[7-[4-(dimethylamino)phenyl]-1,6-naphthyridine-5-yl]-1,2-cyclohexanediamine, (1R,2S)-rel-;
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl],3-propanediamine;
N-[7-(3'-methoxy[1,1'-biphenyl]-4-yl)-1,6-naphthyridine-5-yl]-1,3-propane-diamine;
N-[7-(3'-fluoro[1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]-N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-[3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexanediamine;
4-[[7-[4-[[2-(dimethylamino)ethyl]methylamino]phenyl]-1,6-naphthyridine-5-yl]oxy]-cyclohexanole;
N-[7-[3-bromo-4-(4-morpholinyl)phenyl]-1,6-naphthyridine-5-yl]-1,3-propane-diamine;
N,N-dimethyl-4-[5-(4-methyl-1-piperazinyl)-1,6-naphthyridine-7-yl]-benzenamine;
4-[[7-[4-[[3-(dimethylamino)propyl]methylamino]phenyl]-1,6-naphthyridine-5-yl]oxy]-cyclohexanole;
N-[7-[4-[[2-(dimethylamino)ethyl]methylamino]phenyl]-1,6-naphthyridine-5-yl]-1,4-butanediamine; or
[3-[[5-[(3-aminopropyl)amino]-7-(4-methoxyphenyl)-1,6-naphthyridine-2-yl]-amino]propyl]-carbamic acid-1,1-dimethylethyl ester, optionally in racemic form, as enantiomers, diastereomers or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In another embodiment, the additional therapeutic agent is an agent that inhibits the interaction between CAL (also known as CFTR-associated ligand) and mutant CFTR proteins. In one embodiment, the agent that inhibits interaction between CAL and mutant CFTR proteins is a peptide or peptidomimetic (e.g., 6 to 20 residues in length). In another embodiment, the agent that inhibits interaction between CAL and mutant CFTR proteins is a peptide or peptidomimetic disclosed in US Published Patent Application No. US2014/0100155 A1, incorporated herein by reference in its entirety.

In another embodiment, the above recited pharmaceutical compositions contain a pharmaceutically acceptable prodrug of the compound of the present invention.

In one aspect, the pharmaceutical compositions of the invention can be administered to a patient once daily or about every twenty four hours. Alternatively, the pharmaceutical compositions of the invention can be administered to a patient twice daily. Alternatively, the pharmaceutical composition of the invention can be administered about every twelve hours. These pharmaceutical compositions are administered as oral formulations containing about 25 mg, 50 mg, 100 mg, 125 mg, 150 mg, 200 mg, 250 mg, 300 mg, or 400 mg of a compound of Formula I. In this aspect, the pharmaceutical compositions further comprise a filler; a disintegrant; a surfactant; a binder; or a lubricant, or combinations thereof.

It will also be appreciated that the pharmaceutical compositions of the invention, including the pharmaceutical compositions comprising combinations described previously, can be employed in combination therapies; that is, the compositions can be administered concurrently with, prior to, or subsequent to, one or more other desired therapeutic agents or medical procedures.

These combinations are useful for treating the diseases described herein including cystic fibrosis. These combinations are also useful in the kits described herein.

The amount of additional therapeutic agent present in or with the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Therapeutic Uses of the Compounds of Formula I-Ij and Pharmaceutical Compositions Thereof In one aspect, the invention also provides a method of treating, lessening the severity of, or symptomatically treating a disease in a patient, the method comprising administering an effective amount of the pharmaceutical composition of the invention to the patient, preferably a mammal, wherein the disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency and Type 1 hereditary angioedema, lipid processing deficiencies (such as familial hypercholesterolemia, Type 1 chylomicronemia, and abetalipoproteinemia), lysosomal storage diseases (such as I-cell disease/pseudo-Hurler), mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases (such as Alzheimer's disease, Parkinson's disease, amyotrophic lateral sclerosis, progressive supranuclear palsy, and Pick's disease), several polyglutamine neurological disorders (such as Huntington's, spinocerebellar ataxia type I, spinal and bulbar muscular atrophy, dentatorubral pallidoluysian atrophy, and myotonic dystrophy), spongiform encephalopathies (such as hereditary Creutzfeldt-Jakob disease (due to prion protein processing defect)), Fabry disease, Gerstmann-Straussler-Scheinker syndrome, COPD, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, epilepsy, lysosomal storage disease, Angelman syndrome, and Primary Ciliary Dyskinesia (PCD), a term for inherited disorders of the structure and/or function of cilia, including PCD with situs *inversus* (also known as Kartagener syndrome), PCD without situs *inversus* and ciliary aplasia.

In another embodiment, the method of treating, lessening the severity of, or symptomatically treating a disease in a patient of the invention comprises administering an effective amount of the pharmaceutical composition of the invention, provided that in formula I and the attendant definitions: i) when ring A is indole, n is not zero and rings B and C are aryl unsubstituted by $CF_3$ or halo; ii) when ring A is pyrazole, n is not zero; iii) when ring A is pyridyl, ring B and ring C moieties are substituted at the 2- and 3-positions of the pyridyl ring, interchangeably; and iv) when ring A is imidazole, the ring B moiety is substituted at the 2-position of the imidazole ring.

In one aspect, the invention also provides a method of treating, lessening the severity of, or symptomatically treating a disease in a patient comprising administering an effective amount of the pharmaceutical composition or tablet of the invention to the patient, preferably a mammal, wherein the disease is selected from generalized epilepsy with ferbrile seizures plus (GEFS+), general epilepsy with ferbile and aferbrile seizures, myotonia, paramyotonia congenital, potassium-aggravated myotonia, hyperkalemic periodic paralysis, LQTS, LQTS/Brugada syndrome, autosomal-dominant LQTS with deafness, autosomal-recessive LQTS, LQTS with dysmorphic features, congenital and acquired LQTS, Timothy syndrome, persistent hyperinsulinemic hypolglycemia of infancy, dilated cardiomyopathy, autosomal-dominant LQTS, Dent disease, Osteopetrosis, Bartter syndrome type III, central core disease, malignant hyperthermia, and catecholaminergic polymorphic tachycardia.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation N1303K, A1507, or R560T.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation G551D. In another embodiment, the patient is homozygous in G551D. In another embodiment, the patient is heterozygous in G551D. In another embodiment, the patient is heterozygous in G551D, wherein the other CFTR genetic mutation is any one of F508del, G542X, N1303K, W1282X, R117H, R553X, 1717-1G→A, 621+1G→T, 2789+5G→A, 3849+10kbC→T, R1162X, G85E, 3120+1G→A, A1507, 1898+1G→A, 3659delC, R347P, R560T, R334W, A455E, 2184delA, or 711+1G→T. In another embodiment, the patient is heterozygous in G551D, wherein the other CFTR genetic mutation is F508del. In another embodiment, the patient is heterozygous in G551D, wherein the other CFTR genetic mutation is R117H.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation F508del. In another embodiment, the patient is homozygous in F508del. In another embodiment, the patient is heterozygous in F508del. In another embodiment, the patient is heterozygous in F508del, wherein the other CFTR genetic mutation is any one of G551D, G542X, N1303K, W1282X, R117H, R553X, 1717-1G→A, 621+1G→T, 2789+5G→A, 3849+10kbC→T, R₁ 162X, G85E, 3120+1G→A, A1507, 1898+1G→A, 3659delC, R347P, R560T, R334W, A455E, 2184delA, or 711+1G→T. In another embodiment, the patient is heterozygous in F508del, wherein the other CFTR genetic mutation is G551D. In another embodiment, the patient is heterozygous in F508del, wherein the other CFTR genetic mutation is R117H.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R. In one embodiment of this aspect, the invention provides a method of treating CFTR comprising administering Compound 1 to a patient possessing a human CFTR mutation selected from G178R, G551S, G970R, G1244E, S1255P, G1349D, S549N, S549R and S1251N. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 1811+1.6kbA→G, 2789+5G→A, 3272-26A→G and 3849+10kbC→T. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R, and a human CFTR mutation selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R and S1251N, and a human CFTR mutation selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R, and a human CFTR mutation selected from F508del, R117H, and G551D. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H, and a human CFTR mutation selected from F508del, R117H, and G551D. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-LG→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 1811+1.6kbA→G, 2789+5G→A, 3272-26A→G and 3849+10kbC→T, and a human CFTR mutation selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G, and a human CFTR mutation selected from F508del, R117H.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R and S1251N. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D10E, D1270N and D1152H. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 1811+1.6kbA→G, 2789+5G→A, 3272-26A→G and 3849+10kbC→T. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D, and one or more human CFTR mutations selected from F508del, R117H, and G551D.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R, and one or more human CFTR mutations selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R and S1251N, and one or more human CFTR mutations selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R, and one or more human CFTR mutations selected from F508del, R117H, and G551D. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H, and one or more human CFTR mutations selected from F508del, R117H, and G551D. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and one or more human CFTR mutations selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 1811+1.6kbA→G, 2789+5G→A, 3272-26A→G and 3849+10kbC→T, and one or more human CFTR mutations selected from F508del, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G, and one or more human CFTR mutations selected from F508del, R117H, and G551D.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation selected from FIG. 1.

In certain embodiments, the composition of the present invention is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, F508del, as well as other mutations such as the G551D mutation, or the R117H mutation. In certain embodiments, compositions of the present invention are useful for treating, lessening the severity of, or symptomatically treating cystic fibrosis in patients who exhibit little to no residual CFTR activity. In certain embodiments, compositions of the present invention are useful for treating, lessening the severity of, or symptomatically treating cystic fibrosis in patients who exhibit little to no residual CFTR activity in the apical membrane of respiratory epithelia.

In another embodiment, the compositions of the present invention are useful for treating or lessening the severity of cystic fibrosis in patients who exhibit residual CFTR activity using pharmacological methods. In another embodiment, the compositions of the present invention are useful for treating or lessening the severity of cystic fibrosis in patients who have residual CFTR activity using gene therapy. Such methods increase the amount of CFTR present at the cell surface, thereby inducing a hitherto absent CFTR activity in a patient or augmenting the existing level of residual CFTR activity in a patient.

In one embodiment, the compositions of the present invention are useful for treating or lessening the severity of cystic fibrosis in patients within certain genotypes exhibiting residual CFTR activity, e.g., Class I mutations (not synthesized), class II mutation (misfolding), class III mutations (impaired regulation or gating), class IV mutations (altered conductance), or class V mutations (reduced synthesis).

In one embodiment, compositions of the present invention are useful for treating, lessening the severity of, or symptomatically treating cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic sufficiency.

In one embodiment, the compositions of the present invention are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In one embodiment, the compositions of the present invention are useful for treating, lessening the severity of, or symptomatically treating patients diagnosed with pancreatic sufficiency, idiopathic pancreatitis and congenital bilateral absence of the vas deferens, or mild lung disease wherein the patient has wild type CFTR.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymyositis/dermatomyositis. Defective protein trafficking is believed to cause the disease, for which treatment options are limited. Augmenters or inducers of CFTR activity may hydrate the various organs afflicted by the disease and help to elevate the associated symptoms.

In one embodiment, the invention relates to a method of augmenting or inducing anion channel activity in vitro or in vivo, comprising contacting the channel with a composition of the present invention. In another embodiment, the anion channel is a chloride channel or a bicarbonate channel. In another embodiment, the anion channel is a chloride channel.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In recent years a number of attempts have been made to treat cystic fibrosis using gene therapy. Gene therapy is the insertion, alteration, or removal of genes within an individual's cells and biological tissues to treat disease. It is a technique for correcting defective genes that are responsible for disease development. The most common form of gene therapy involves the insertion of functional genes into an unspecified genomic location in order to replace a mutated gene, but other forms involve directly correcting the mutation or modifying normal gene that enables a viral infection. Although the technology is still in its infancy, it has been used with some success.

Cystic fibrosis is a good candidate for gene therapy as it is primarily caused by mutations in a single gene. A normal copy of the gene could be delivered to patients via topical delivery to the lung, not requiring invasive techniques or surgery. A gene complementation approach would also directly target the cause of the disease and could correct many aspects of the complex lung pathology.

Soon after the cloning of the CFTR gene, proof-of-principle was established when the Cl-conductance defect was corrected after delivery of a functional copy of human wild-type CFTR DNA to cells isolated from cystic fibrosis patients. To date, a number of trials for cystic fibrosis gene therapy have been tested in humans. These early studies were concerned mainly with safety issues.

In one embodiment, the invention features a method of treating cystic fibrosis comprising administering to the patient a compound of formula I to Id in conjunction with gene therapy. The gene therapy can be as disclosed in Internation Published Patent Application No. WO2013061091, incorporated herein in its entirety by reference. Administration may be prior, concomitant, or subsequent administration of a compound of formula I-Id, or any of the pharmaceutical compositions of the present invention.

In another embodiment, the gene therapy features administering to the patient 1 mL to less than 10 mLs of a complex of (i) a non-viral CpG dinucleotide-free plasmid comprising nucleic acid encoding a CFTR polypeptide operatively linked to hCEF1 promoter, wherein the plasmid is at a concentration of 2 mg/mL to 3 mg/mL, and (ii) GL67A lipid mixture at a concentration of 10 mg/mL to 20 mg/mL.

In one embodiment, gene therapy is administered to a patient with cystic fibrosis prior, concomitant, or subsequent administration of a pharmaceutical composition comprising (i) a compound of formula I-Id and (ii) 3-(6-(1-(2,2-difluorobenzo[d][1,3]dioxol-5-yl) cyclopropanecarboxamido)-3-methylpyridin-2-yl)benzoic acid.

In one embodiment, gene therapy is administered to a patient with cystic fibrosis prior, concomitant, or subsequent administration of a pharmaceutical composition comprising (i) a compound of formula I-Id and (ii) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In one embodiment, gene therapy is administered to a patient with cystic fibrosis prior, concomitant, or subsequent administration of a pharmaceutical composition comprising (i) a compound of formula I-Id and (ii) 4-(3-(1-(2,2-difluorobenzo[d][1,3]dioxol-5-yl)cyclopropanecarboxamido) isoquinolin-1-yl)benzoic acid.

In one embodiment, gene therapy is administered to a patient with cystic fibrosis prior, concomitant, or subsequent administration of a pharmaceutical composition comprising (i) a compound of formula I-Id; (ii) 3-(6-(1-(2,2-difluorobenzo[d][1,3]dioxol-5-yl) cyclopropanecarboxamido)-3-methylpyridin-2-yl)benzoic acid; and (iii) N-(5-hydroxy-2,4-ditert-butyl-phenyl)-4-oxo-1H-quinoline-3-carboxamide.

In one embodiment, gene therapy is administered to a patient with cystic fibrosis prior, concomitant, or subsequent administration of a pharmaceutical composition comprising (i) a compound of formula I-Id; (ii) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide; and (iii) N-(5-hydroxy-2,4-ditert-butyl-phenyl)-4-oxo-1H-quinoline-3-carboxamide.

In one embodiment, gene therapy is administered to a patient with cystic fibrosis prior, concomitant, or subsequent administration of a pharmaceutical composition comprising (i) a compound of formula I-Id; (ii) 4-(3-(1-(2,2-difluorobenzo[d][1,3]dioxol-5-yl)cyclopropanecarboxamido) isoquinolin-1-yl)benzoic acid; and (iii) N-(5-hydroxy-2,4-ditert-butyl-phenyl)-4-oxo-1H-quinoline-3-carboxamide.

Kits

In another aspect, the present invention features a kit comprising a compound and/or pharmaceutical composition of the present invention and instructions for use thereof.

In another embodiment, the kits of the present invention further comprise one or more additional therapeutic agent (s). In another embodiment, the additional therapeutic agent is selected from a mucolytic agent, bronchodialator, an antibiotic, an anti-infective agent, a CFTR modulator, or an anti-inflammatory agent. In another embodiment, the additional therapeutic agent is a CFTR modulator. In another embodiment, the additional therapeutic agent is a CFTR corrector.

In another embodiment, the additional therapeutic agent is

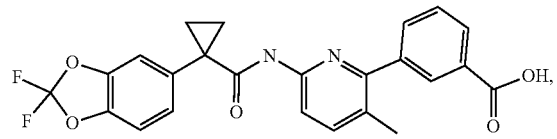

or a pharmaceutically acceptable salt thereof.

In another embodiment, the additional therapeutic agent is

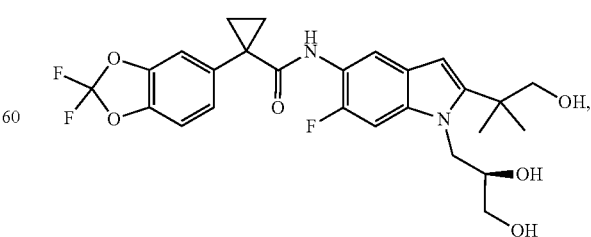

or a pharmaceutically acceptable salt thereof.

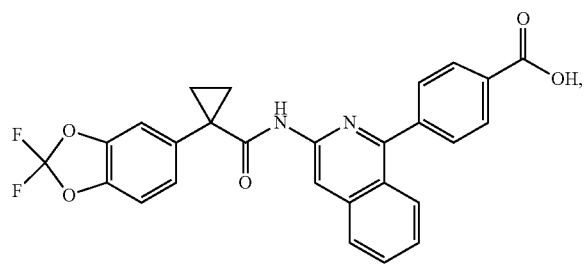 [SMILES: O=C(O)c1ccc(-c2nc(NC(=O)C3(c4ccc5c(c4)OC(F)(F)O5)CC3)cc3ccccc23)cc1]

or a pharmaceutically acceptable salt thereof.

In another embodiment, the additional therapeutic agent is a CFTR potentiator.

In another embodiment, the additional therapeutic agent is

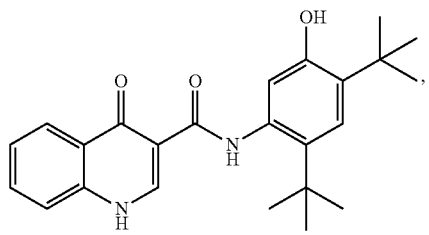 [SMILES: CC(C)(C)c1cc(C(C)(C)C)c(NC(=O)c2c[nH]c3ccccc3c2=O)cc1O]

or a pharmaceutically acceptable salt thereof.

In another embodiment, the additional therapeutic agents are a CFTR corrector and a CFTR potentiator.

In another embodiment, the additional therapeutic agents are

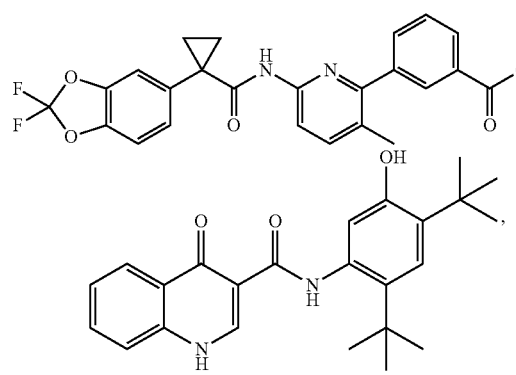

or pharmaceutically acceptable salts thereof.

In another embodiment, the additional therapeutic agents are

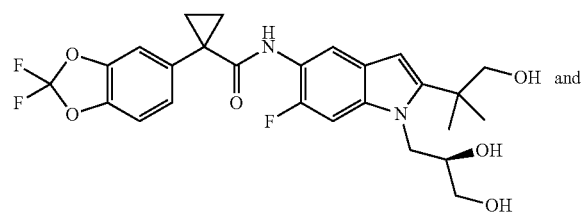

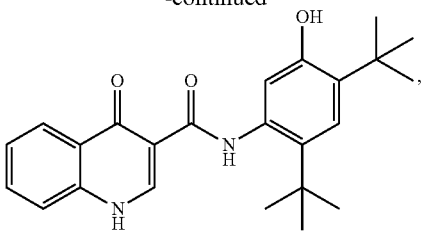

or pharmaceutically acceptable salts thereof.

In another embodiment, the additional therapeutic agents are

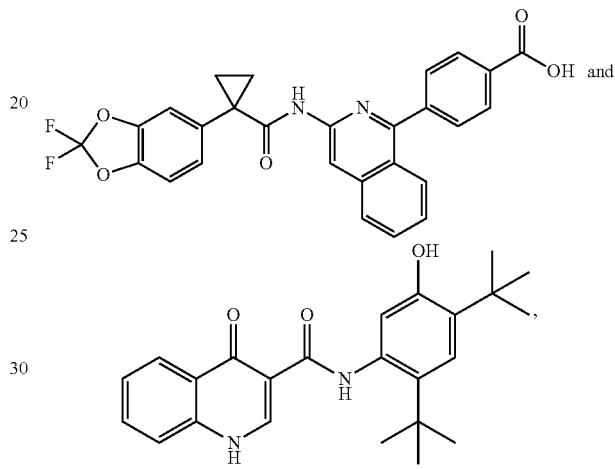

or pharmaceutically acceptable salts thereof.

In another embodiment, the kits of the present invention are drawn to kits wherein the compounds or the pharmaceutical compositions of the present invention and the one or more additional therapeutic agent(s) are in separate containers.

In another embodiment, the kits of the present invention are drawn to kits wherein the compounds or the pharmaceutical compositions of the present invention and the one or more additional therapeutic agent(s) are in the same container.

In another embodiment, the container is a bottle, vial, or blister pack, or combination thereof.

Anywhere in the present application where a name of a compound may not correctly describe the structure of the compound, the structure supersedes the name and governs.

EXAMPLES

Preparation 1: N-(3-aminophenyl)sulfonyl-6-tert-butyl-2-(2,4,6-trimethylphenyl)pyridine-3-carboxamide (Compound 26)

Step 1: 6-tert-butyl-2-chloro-pyridine-3-carbonitrile

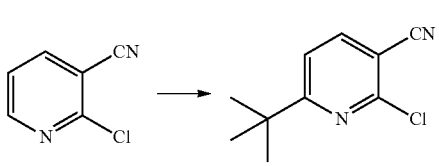

2,2-Dimethylpropanoic acid (50. mL, 870 mmol), 2-chloropyridine-3-carbonitrile (30 g, 220 mmol) and AgNO$_3$ (9.2 g, 54 mmol) were suspended in 10% aq. H$_2$SO$_4$ (300 mL). A solution of ammonium peroxydisulfate (91 g, 430 mmol) and water (480 mL) was added to the mixture dropwise through an addition funnel. The mixture was stirred at room temperature overnight. The pH of reaction mixture was adjusted to ~8-9 with 30% NH$_4$OH (~250 mL) and the mixture was extracted with ethyl acetate (3×300 mL). The combined organic layers were washed with brine, dried over sodium sulfate, and concentrated. The residue was subjected to silica gel column chromatography (0-25% ethyl acetate/hexanes) to give 6-tert-butyl-2-chloro-pyridine-3-carbonitrile (37 g, 83%) as a clear oil which solidified upon standing. $^1$H NMR (400 MHz, CDCl$_3$) δ 7.83 (d, J=8.1 Hz, 1H), 7.30 (d, J=8.1 Hz, 1H), 1.29 (s, 9H). ESI-MS m/z calc. 194.1, found 195.0 (M+1)$^+$; Retention time: 1.66 min (3 min run).

Step 2: 6-tert-butyl-2-(2,4,6-trimethylphenyl)pyridine-3-carbonitrile

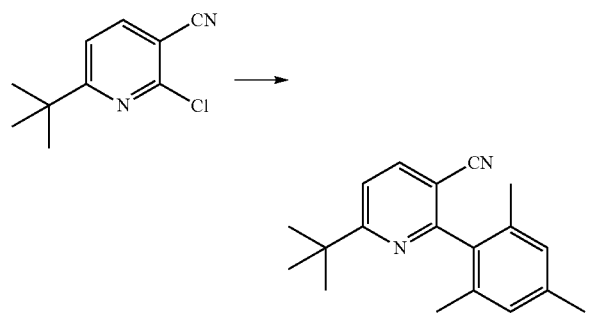

A mixture of 6-tert-butyl-2-chloro-pyridine-3-carbonitrile (400. mg, 2.06 mmol), (2,4,6-trimethylphenyl)boronic acid (506 mg, 3.08 mmol), Pd(dppf)$_2$Cl$_2$*CH$_2$Cl$_2$ (75 mg, 0.10 mmol), NaHCO$_3$ (173 mg, 2.06 mmol) and DME (2 mL) was heated at 120° C. in a microwave reactor for 30 min. The mixture was partitioned between CH$_2$Cl$_2$ and water. The layers were separated and the aqueous layer was extracted with CH$_2$Cl$_2$ (2×). The combined organics were dried over sodium sulfate, filtered and concentrated. The residue was subjected to silica gel column chromatography (0-20% ethyl acetate/hexanes) to give 6-tert-butyl-2-(2,4,6-trimethylphenyl)pyridine-3-carbonitrile (225 mg, 39%). ESI-MS m/z calc. 278.2, found 279.4 (M+1)$^+$; Retention time: 0.84 min (3 min run).

Step 3: 6-tert-butyl-2-(2,4,6-trimethylphenyl)pyridine-3-carboxylic acid

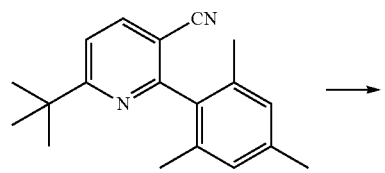

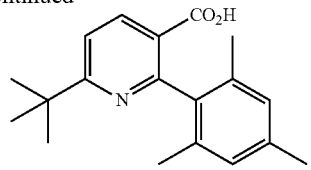

A mixture of 6-tert-butyl-2-(2,4,6-trimethylphenyl)pyridine-3-carbonitrile (225 mg, 0.808 mmol), KOH (2.0 mL of 4.0 M, 8.0 mmol) and EtOH (2.3 mL) was heated at 90° C. for 2.5 d. The mixture was acidified with conc. HCl to ~pH 2 before it was concentrated under reduced pressure. The residue was subjected to preparatory-HPLC (10-99% acetonitrile/water with 0.05 mM HCl) to give 6-tert-butyl-2-(2,4,6-trimethylphenyl)pyridine-3-carboxylic acid (40 mg, 17%) as a white solid. ESI-MS m/z calc. 297.2, found 298.4 (M+1)$^+$; Retention time: 1.77 min (3 min run).

Step 4: N-(3-aminophenyl)sulfonyl-6-tert-butyl-2-(2,4,6-trimethylphenyl)pyridine-3-carboxamide (Compound 26)

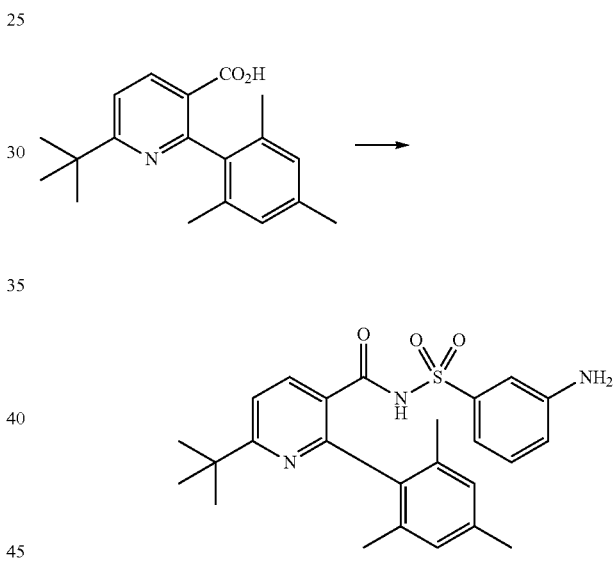

Sodium (3-nitrophenyl)sulfonylazanide (60. mg, 0.27 mmol) was added to a mixture of 6-tert-butyl-2-(2,4,6-trimethylphenyl)pyridine-3-carboxylic acid (40. mg, 0.13 mmol), N-[(dimethylamino)-1H-1,2,3-triazolo-[4,5-b]pyridin-1-ylmethylene]-N-methylmethanaminium hexafluorophosphate N-oxide (51 mg, 0.13 mmol) and N,N-dimethylformamide (800.0 µL) at room temperature. The mixture was allowed to stir at 70° C. overnight before it was filtered and subjected to preparatory-HPLC (10-99% acetonitrile/water with 0.05% HCl) to give the nitro intermediate, 6-tert-butyl-N-(3-nitrophenyl)sulfonyl-2-(2,4,6-trimethylphenyl)pyridine-3-carboxamide. The nitro intermediate was taken up in acetic acid (1 mL) before Zn (8.8 mg, 0.13 mmol) was added. The mixture was stirred at room temperature for 30 min before it was filtered. The filtrate was subjected to preparatory-HPLC (10-99% acetonitrile/water with 0.05 mM HCl) to give N-(3-aminophenyl)sulfonyl-6-tert-butyl-2-(2,4,6-trimethylphenyl)pyridine-3-carboxamide (Compound 26) (13 mg, 22%). ESI-MS m/z calc. 451.2, found 452.5 (M+1)$^+$; Retention time: 1.81 min (3 min run).

Preparation 2: N-(3-aminophenyl)sulfonyl-6-tert-butyl-2-(4-chlorophenyl)pyridine-3-carboxamide (Compound 223)

Step 1:
6-tert-butyl-2-chloro-pyridine-3-carboxamide

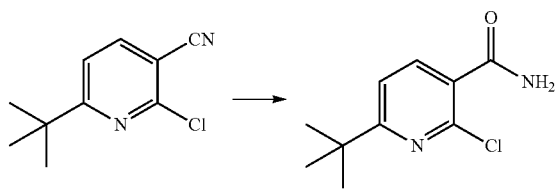

To a mixture of 6-tert-butyl-2-chloro-pyridine-3-carbonitrile (6.81 g, 35.0 mmol) and NaOH (38.5 mL of 1.0 M, 38.5 mmol) in EtOH (175 mL) was slowly added hydrogen peroxide (19.9 mL of 30% w/v, 175 mmol). The reaction mixture was stirred at room temperature for 45 min. before additional hydrogen peroxide (19.9 mL of 30% w/v, 175 mmol) was added. After 1 h, the mixture was slowly quenched with saturated sodium bisulfite solution, diluted with water, and extracted with ethyl acetate. The combined extracts were washed with water, dried over sodium sulfate, and evaporated to give 6-tert-butyl-2-chloro-pyridine-3-carboxamide (7.21 g, 97%) as a white solid. ESI-MS m/z calc. 212.1, found 212.9 $(M+1)^+$; Retention time: 0.46 min (1 min run).

Step 2: 6-tert-butyl-2-chloro-N-(3-nitrophenyl)sulfonyl-pyridine-3-carboxamide

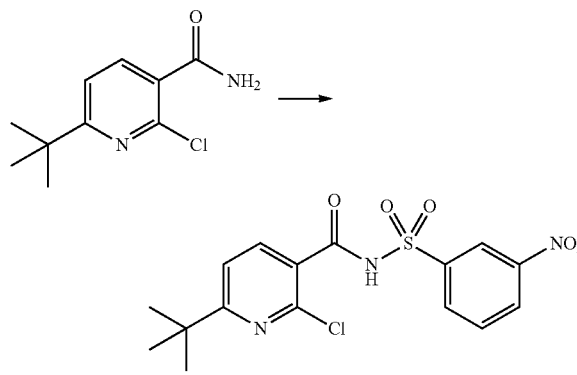

To a solution of 6-(tert-butyl)-2-chloronicotinamide (3.19 g, 15.0 mmol) and 3-nitrobenzenesulfonyl chloride (3.32 g, 15.0 mmol) in THF (100.0 mL) was slowly added NaH (1.80 g, 60%, w/w, 45.0 mmol) in portions. The mixture was allowed to stir for 2 h at room temperature before it was quenched with saturated aqueous ammonium chloride solution. The mixture was extracted with ethyl acetate (3×). The combined extracts were washed with water, dried over sodium sulfate, and evaporated. The residue was taken up in diethyl ether. The solids were filtered, washed with diethyl ether, and dried under vacuum. The filtrate was evaporated and the residue was purified by silica gel chromatography (1-11% methanol/CH$_2$Cl$_2$). The two batches (solid from ether and product from column) were combined to give 6-(tert-butyl)-2-chloro-N-((3-nitrophenyl)sulfonyl)nicotinamide (3.56 g, 60%) as light yellow solid. ESI-MS m/z calc. 397.1, found 398.0 $(M+1)^+$; Retention time: 0.66 min (1 min run).

Step 3: N-(3-aminophenyl)sulfonyl-6-tert-butyl-2-chloro-pyridine-3-carboxamide

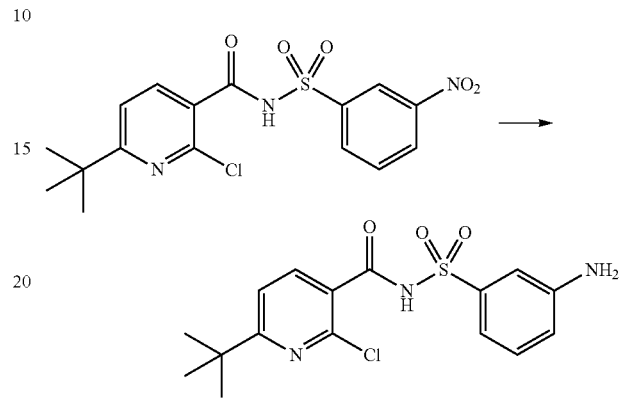

To a solution of 6-(tert-butyl)-2-chloro-N-((3-nitrophenyl)sulfonyl)nicotinamide (1.40 g, 3.52 mmol) in glacial acetic acid (140 mL) was added zinc (5.76 g, 88.0 mmol). The reaction mixture was allowed to stir at room temperature for 1 h before it was filtered and concentrated under reduced pressure. The crude product was subjected silica gel column chromatography (0-5% methanol/CH$_2$Cl$_2$) to provide N-(3-aminophenyl)sulfonyl-6-tert-butyl-2-chloro-pyridine-3-carboxamide (1.12 g, 87%) as an orange sticky foam. ESI-MS m/z calc. 367.1, found 368.6 $(M+1)^+$; Retention time: 1.09 min (3 min run).

Step 4: N-(3-aminophenyl)sulfonyl-6-tert-butyl-2-(4-chlorophenyl)pyridine-3-carboxamide (Compound 223)

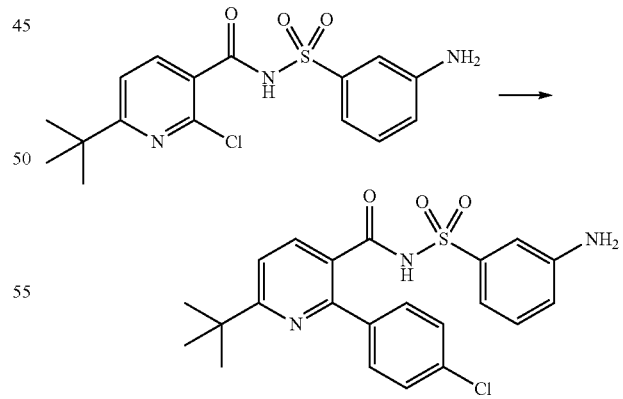

To (4-chlorophenyl)boronic acid (26 mg, 0.16 mmol) was added a solution of N-(3-aminophenyl)sulfonyl-6-tert-butyl-2-chloro-pyridine-3-carboxamide (50. mg, 0.14 mmol) in DMA (0.5 mL). Na$_2$CO$_3$ (136 µL, 2.0 M, 0.27 mmol) and dichloro[1,1'-bis(diphenylphosphino)ferrocene]palladium (II) dichloromethane adduct (5 mg, 0.007 mmol) were added and the vessel was sealed under nitrogen gas and heated under microwave irradiation at 120° C. for 20 minutes. The reaction mixture was cooled to room temperature, filtered and subjected to preparatory-HPLC (10-99% water/CH$_3$CN with 0.05 mM HCl) to give N-(3-aminophenyl)sulfonyl-6-tert-butyl-2-(4-chlorophenyl)pyridine-3-carboxamide (Compound 223) (15 mg, 25%). ESI-MS m/z calc. 443.1, found 444.1 (M+1)$^+$; Retention time: 1.81 min (3 min run).

The following compounds were synthesized using the procedures described herein:

N-(3-aminophenyl)sulfonyl-6-tert-butyl-2-(4-tert-butylphenyl)pyridine-3-carboxamide (Compound 252),
N-(3-aminophenyl)sulfonyl-8,8-dimethyl-2-phenyl-6,7-dihydro-5H-quinoline-3-carboxamide (Compound 685),
(3-aminophenyl)sulfonyl-[8,8-dimethyl-2-(p-tolyl)-6,7-dihydro-5H-quinoline-3-carbonyl]azanide (Compound 1231),
N-(4-aminophenyl)sulfonyl-6-tert-butyl-2-(cyclohexen-1-yl)pyridine-3-carboxamide (Compound 880),
N-(4-aminophenyl)sulfonyl-8,8-dimethyl-2-phenyl-6,7-dihydro-5H-quinoline-3-carboxamide (Compound 1190),
N-[(6-amino-2-pyridyl)sulfonyl]-6-tert-butyl-2-(4-fluorophenyl)pyridine-3-carboxamide (Compound 417),
N-(3-aminophenyl)sulfonyl-6-tert-butyl-2-indan-5-yl-pyridine-3-carboxamide (Compound 308),
N-(3-aminophenyl)sulfonyl-6-tert-butyl-2-(3,4-dimethylphenyl)pyridine-3-carboxamide (Compound 274),
N-(3-aminophenyl)sulfonyl-6-tert-butyl-2-(3-tert-butylphenyl)pyridine-3-carboxamide (Compound 229),
N-(3-aminophenyl)sulfonyl-6-tert-butyl-2-(3,5-dimethylphenyl)pyridine-3-carboxamide (Compound 52),
N-(3-aminophenyl)sulfonyl-6-tert-butyl-2-(4-isopropylphenyl)pyridine-3-carboxamide (Compound 314),
N-(3-aminophenyl)sulfonyl-6-tert-butyl-2-(4-ethylphenyl)pyridine-3-carboxamide (Compound 359),
N-(3-aminophenyl)sulfonyl-6-tert-butyl-2-[4-(trifluoromethyl)phenyl]pyridine-3-carboxamide (Compound 129),
N-(3-aminophenyl)sulfonyl-6-tert-butyl-2-(3-fluoro-5-methyl-phenyl)pyridine-3-carboxamide (Compound 237),
N-(3-aminophenyl)sulfonyl-6-tert-butyl-2-(p-tolyl)pyridine-3-carboxamide (Compound 301),
N-(3-aminophenyl)sulfonyl-6-tert-butyl-2-(4-fluoro-3-methyl-phenyl)pyridine-3-carboxamide (Compound 177),
N-(3-aminophenyl)sulfonyl-6-tert-butyl-2-(3-fluoro-4-methyl-phenyl)pyridine-3-carboxamide (Compound 349),
N-(3-aminophenyl)sulfonyl-6-tert-butyl-2-(2,4-dimethylphenyl)pyridine-3-carboxamide (Compound 5),
N-(3-aminophenyl)sulfonyl-6-tert-butyl-2-(m-tolyl)pyridine-3-carboxamide (Compound 282),
N-(3-aminophenyl)sulfonyl-6-tert-butyl-2-(4-fluorophenyl)pyridine-3-carboxamide (Compound 46),
N-(3-aminophenyl)sulfonyl-6-tert-butyl-2-(2-fluoro-5-methyl-phenyl)pyridine-3-carboxamide (Compound 1350) (Compound 1350),
N-(3-aminophenyl)sulfonyl-6-tert-butyl-2-(3,4-difluorophenyl)pyridine-3-carboxamide (Compound 1217),
N-(3-aminophenyl)sulfonyl-6-tert-butyl-2-(o-tolyl)pyridine-3-carboxamide (Compound 1036),
N-(3-aminophenyl)sulfonyl-6-tert-butyl-2-(4-methoxyphenyl)pyridine-3-carboxamide (Compound 550),
N-(3-aminophenyl)sulfonyl-6-tert-butyl-2-(2-fluoro-4-methyl-phenyl)pyridine-3-carboxamide (Compound 1331),
N-(3-aminophenyl)sulfonyl-6-tert-butyl-2-phenyl-pyridine-3-carboxamide (Compound 542), and
N-(3-aminophenyl)sulfonyl-6-tert-butyl-2-(3,4-difluorophenyl)pyridine-3-carboxamide (Compound 1217).

Preparation 3: N-(benzenesulfonyl)-6-tert-butyl-2-(p-tolyl)pyridine-3-carboxamide (Compound 74)

Step 1: 6-tert-butyl-2-chloro-pyridine-3-carboxylic acid

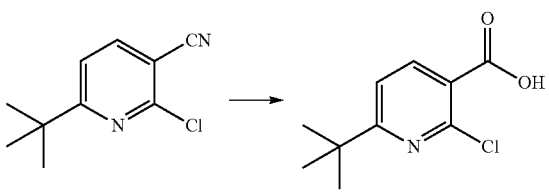

A solution of KOH (8.65 g, 154 mmol) in water (25 mL) was added to a solution of 6-tert-butyl-2-chloro-pyridine-3-carbonitrile (5.00 g, 25.7 mmol) in isopropanol (25 mL). The reaction mixture was allowed to stir at 90° C. overnight. After cooling to room temperature, the reaction mixture was diluted with ethyl acetate (75 mL) and was extracted with aqueous NaOH (1 N, 3×75 mL). The combined aqueous layers were acidified to pH 3 with the addition of aqueous HCl (1 N, 200 mL) and were extracted with ethyl acetate (2×75 mL). The combined organic layers were dried over sodium sulfate, filtered and concentrated to give 6-tert-butyl-2-chloro-pyridine-3-carboxylic acid (5.25 g, 96%) as a yellow solid. ESI-MS m/z calc. 213.1, found 214.4 (M+1)$^+$; Retention time: 1.09 min (3 min run). $^1$H NMR (400 MHz, CDCl$_3$) δ 10.39 (s, 1H), 8.26 (d, J=8.1 Hz, 1H), 7.36 (d, J=8.1 Hz, 1H), 1.38 (s, 9H).

Step 2: 6-tert-butyl-2-(p-tolyl)pyridine-3-carboxylic acid

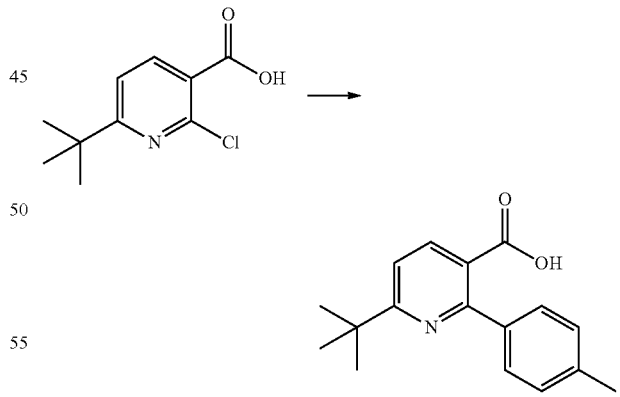

6-tert-Butyl-2-chloro-pyridine-3-carboxylic acid (1.35 g, 6.32 mmol) and p-tolylboronic acid (1.03 g, 7.58 mmol) were suspended in DMA (14 mL). Aqueous sodium carbonate (6.3 mL of 2.0 M, 13 mmol) was added followed by dichloro[1,1'-bis(diphenylphosphino)ferrocene]palladium (II) dichloromethane adduct (231 mg, 0.312 mmol). The reaction vessel was sealed under nitrogen and heated to 140° C. for 1.5 h in a microwave reactor. The reaction mixture was diluted with ethyl acetate (50 mL) and was washed with aqueous NaOH (1 M, 4×50 mL). The combined aqueous layers were acidified to pH 3 with 1 N HCl and then extracted with ethyl acetate (5×50 mL). The organic layers were combined, dried over sodium sulfate, filtered, and concentrated under reduced pressure. The residue was subjected to silica gel column chromatography (0-30% ethyl acetate/hexane) to give 6-tert-butyl-2-(p-tolyl)pyridine-3-carboxylic acid (740 mg, 43%) as a white solid. ESI-MS m/z calc. 269.1, found 270.5 (M+1)$^+$; Retention time: 1.53 min (3 min run).

The following compounds can be synthesized using the procedures described above: 8,8-dimethyl-2-(p-tolyl)-5,6,7,8-tetrahydroquinoline-3-carboxylic acid.

Step 3: N-(benzenesulfonyl)-6-tert-butyl-2-(p-tolyl) pyridine-3-carboxamide (Compound 74)

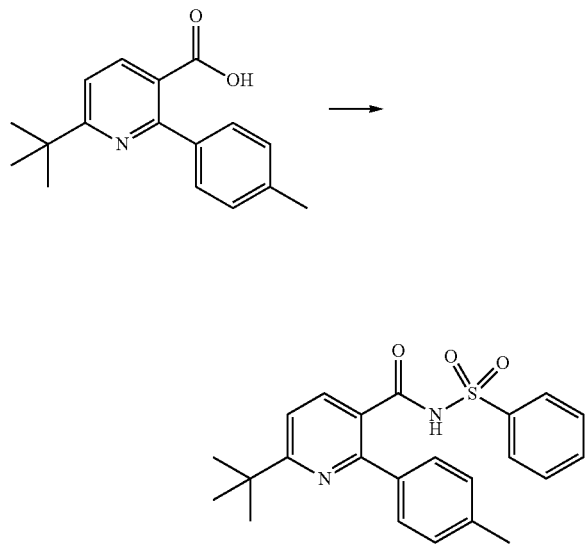

To benzenesulfonamide (23 mg, 0.14 mmol) was added 6-tert-butyl-2-(p-tolyl)pyridine-3-carboxylic acid (35 mg, 0.13 mmol) in N,N-dimethylformamide (400 μL). A solution of N-[(dimethylamino)-1H-1,2,3-triazolo-[4,5-b]pyridin-1-ylmethylene]-N-methylmethanaminium hexafluorophosphate N-oxide (54 mg, 0.14 mmol) in N,N-dimethylformamide (125 μL) was added followed by solid potassium carbonate (54 mg, 0.39 mmol). The reaction mixture was allowed to stir at 80° C. for 1 h. Additional N-[(dimethylamino)-1H-1,2,3-triazolo-[4,5-b]pyridin-1-ylmethylene]-N-methylmethanaminium hexafluorophosphate N-oxide (0.5 eq) was added and the reaction mixture was allowed to stir overnight at 80° C. The mixture was cooled, filtered and subjected to preparatory-HPLC (10-99% water/acetonitrile with 0.05 mM HCl) to give N-(benzenesulfonyl)-6-tert-butyl-2-(p-tolyl)pyridine-3-carboxamide (Compound 74) (28 mg, 53%). ESI-MS m/z calc. 408.2, found 409.3 (M+1)$^+$; Retention time: 1.93 min (3 min run).

The following compounds can be synthesized using the procedures described herein:

6-tert-butyl-N-(3-ethylphenyl)sulfonyl-2-(p-tolyl)pyridine-3-carboxamide (Compound 50), 6-tert-butyl-N-(3-methoxyphenyl)sulfonyl-2-(p-tolyl)pyridine-3-carboxamide (Compound 327), 6-tert-butyl-N-(4-methoxyphenyl)sulfonyl-2-(p-tolyl)pyridine-3-carboxamide (Compound 206), 6-tert-butyl-N-(4-cyanophenyl)sulfonyl-2-(p-tolyl)pyridine-3-carboxamide (Compound 288), 6-tert-butyl-2-(p-tolyl)-N-(2-pyridylsulfonyl)pyridine-3-carboxamide (Compound 407), 6-tert-butyl-2-(p-tolyl)-N-(1H-pyrazol-5-ylsulfonyl)pyridine-3-carboxamide (Compound 632), 6-tert-butyl-N-[(5-methyl-2-pyridyl)sulfonyl]-2-(p-tolyl)pyridine-3-carboxamide (Compound 1355), 6-tert-butyl-N-(2-cyanophenyl)sulfonyl-2-(p-tolyl)pyridine-3-carboxamide (Compound 623), 6-tert-butyl-N-(2-methoxyphenyl)sulfonyl-2-(p-tolyl)pyridine-3-carboxamide (Compound 1124), N-(4-aminophenyl)sulfonyl-8,8-dimethyl-2-(p-tolyl)-6,7-dihydro-5H-quinoline-3-carboxamide (Compound 1307), 6-tert-butyl-N-(2-hydroxyphenyl)sulfonyl-2-(p-tolyl)pyridine-3-carboxamide (Compound 1175), N-[(6-amino-2-pyridyl)sulfonyl]-8,8-dimethyl-2-(p-tolyl)-6,7-dihydro-5H-quinoline-3-carboxamide (Compound 444), 8,8-dimethyl-2-(p-tolyl)-N-(1H-pyrazol-5-ylsulfonyl)-6,7-dihydro-5H-quinoline-3-carboxamide (Compound 1292), 6-tert-butyl-N-(4-hydroxyphenyl)sulfonyl-2-(p-tolyl)pyridine-3-carboxamide (Compound 809), 6-tert-butyl-N-(3-hydroxyphenyl)sulfonyl-2-(p-tolyl)pyridine-3-carboxamide (Compound 1265), 6-tert-butyl-N-[(6-methoxy-3-pyridyl)sulfonyl]-2-(p-tolyl)pyridine-3-carboxamide (Compound 512), N-[(6-amino-3-pyridyl)sulfonyl]-8,8-dimethyl-2-(p-tolyl)-6,7-dihydro-5H-quinoline-3-carboxamide (Compound 635), 6-(3-fluoro-5-isopropoxy-phenyl)-2-(p-tolyl)-N-(1H-pyrazol-5-ylsulfonyl)pyridine-3-carboxamide (Compound 849), N-[(6-amino-2-pyridyl)sulfonyl]-6-(3-fluoro-5-isopropoxyphenyl)-2-(p-tolyl)pyridine-3-carboxamide (Compound 722), 6-(3-fluoro-5-isopropoxy-phenyl)-N-[(2-methoxy-3-pyridyl)sulfonyl]-2-(p-tolyl)pyridine-3-carboxamide (Compound 798), 6-tert-butyl-N-(1H-pyrazol-4-ylsulfonyl)-2-(2,4,6-trimethylphenoxy)pyridine-3-carboxamide (Compound 401), 6-(4-fluorophenyl)-N-(1H-pyrazol-3-ylsulfonyl)-2-(2,4,6-trimethylphenoxy)pyridine-3-carboxamide (Compound 518), N-[(2-methoxy-3-pyridyl)sulfonyl]-8,8-dimethyl-2-(2,4,6-trimethylphenoxy)-6,7-dihydro-5H-quinoline-3-carboxamide (Compound 423), 6-tert-butyl-N-[[6-(difluoromethyl)-2-pyridyl]sulfonyl]-2-(2,4,6-trimethylphenoxy)pyridine-3-carboxamide (Compound 501), N-[(2-methoxy-3-pyridyl)sulfonyl]-2,6-bis(p-tolyl)pyridine-3-carboxamide (Compound 524), 6-(6-methoxy-5-methyl-3-pyridyl)-N-[(2-methoxy-3-pyridyl)sulfonyl]-2-(p-tolyl)pyridine-3-carboxamide (Compound 861), 6-tert-butyl-N-[(6-methoxy-2-pyridyl)sulfonyl]-2-(p-tolyl)pyridine-3-carboxamide (Compound 75), and N-(4-aminophenyl)sulfonyl-6-tert-butyl-2-(p-tolyl)pyridine-3-carboxamide (Compound 297).

Preparation 4: N-[(6-amino-2-pyridyl)sulfonyl]-6-tert-butyl-2-(p-tolyl)pyridine-3-carboxamide (Compound 58)

Step 1: 6-tert-butyl-N-[(6-fluoro-2-pyridyl)sulfonyl]-2-(p-tolyl)pyridine-3-carboxamide

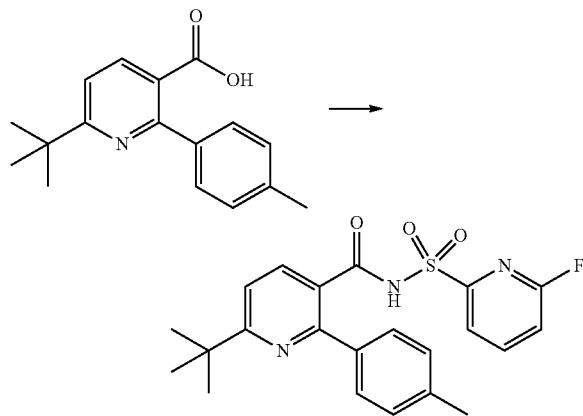

N,N-diisopropyl ethyl amine (104 µL, 0.5940 mmol) was added to a mixture of 6-tert-butyl-2-(p-tolyl)pyridine-3-carboxylic acid (80. mg, 0.30 mmol), 6-fluoropyridine-2-sulfonamide (58 mg, 0.33 mmol), N-[(dimethylamino)-1H-1,2,3-triazolo-[4,5-b]pyridin-1-ylmethylene]-N-methylmethanaminium hexafluorophosphate N-oxide (136 mg, 0.356 mmol) and N,N-dimethylformamide (800 µL) at room temperature. The mixture was heated at 70° C. overnight before it was cooled. The mixture was partitioned between ethyl acetate and 1N HCl. The layers were separated and the aqueous layer was extracted with ethyl acetate (3×). The combined organics were washed with brine, dried over sodium sulfate, filtered, and concentrated. The residue was subjected to silica gel column chromatography (0-20% ethyl acetate/hexanes) to give 6-tert-butyl-N-[(6-fluoro-2-pyridyl)sulfonyl]-2-(p-tolyl)pyridine-3-carboxamide (66 mg, 38%) as a yellowish solid. ESI-MS m/z calc. 427.1, found 428.4 (M+1)+; Retention time: 0.7 min (1 min run).

Step 2: N-[(6-amino-2-pyridyl)sulfonyl]-6-tert-butyl-2-(p-tolyl)pyridine-3-carboxamide (Compound 58)

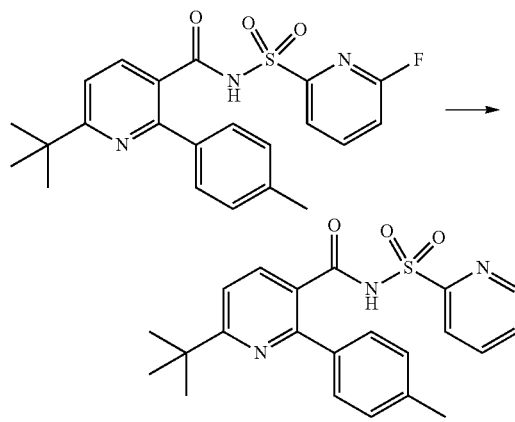

A mixture of 6-tert-butyl-N-[(6-fluoro-2-pyridyl)sulfonyl]-2-(p-tolyl)pyridine-3-carboxamide (55 mg, 0.13 mmol) and NH$_4$OH (30%, 860 µL) was heated at 150° C. for 30 min in a microwave reactor. The mixture was concentrated and the residue was subjected to preparatory-HPLC (10-99% acetonitrile/water with 0.05 mM HCl) to give N-[(6-amino-2-pyridyl)sulfonyl]-6-tert-butyl-2-(p-tolyl)pyridine-3-carboxamide (Compound 58) (17 mg, 31%). ESI-MS m/z calc. 424.2, found 425.4 (M+1)+; Retention time: 1.63 min (3 min run).

The following compounds can be synthesized using the procedures described herein:

N-[(6-amino-2-pyridyl)sulfonyl]-6-tert-butyl-2-(m-tolyl)pyridine-3-carboxamide (Compound 31), N-[(6-amino-2-pyridyl)sulfonyl]-6-tert-butyl-2-(cyclopenten-1-yl)pyridine-3-carboxamide (Compound 529), N-[(6-amino-2-pyridyl)sulfonyl]-6-tert-butyl-2-(cyclohexen-1-yl)pyridine-3-carboxamide (Compound 478), N-[(6-amino-2-pyridyl)sulfonyl]-6-(4-ethoxyphenyl)-2-(p-tolyl)pyridine-3-carboxamide (Compound 409), N-[(6-amino-2-pyridyl)sulfonyl]-6-tert-butyl-2-(4-fluorophenyl)pyridine-3-carboxamide (Compound 417), and N-[(6-amino-2-pyridyl)sulfonyl]-6-tert-butyl-2-phenylpyridine-3-carboxamide (Compound 334).

Preparation 5: 6-phenethyl-2-(2,4,6-trimethylphenoxy)pyridine-3-carboxylic acid

Step 1: methyl 6-chloro-2-(2,4,6-trimethylphenoxy)pyridine-3-carboxylate

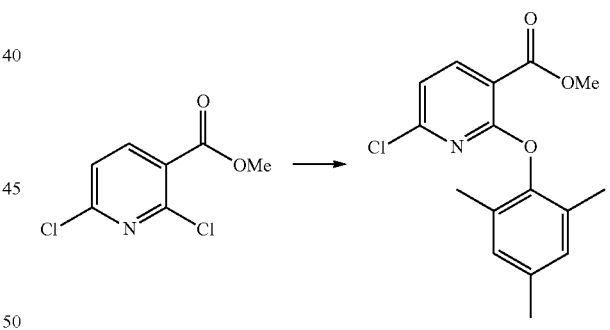

NaH (60%, 2.13 g, 53.3 mmol) was added to a solution of 2,4,6-trimethylphenol (6.60 g, 48.5 mmol) and N,N-dimethylformamide (150 mL) at 0° C. The mixture was stirred for 15 min before a solution of methyl 2,6-dichloronicotinate (10.0 g, 48.5 mmol) in N,N-dimethylformamide (20 mL) was added dropwise. The mixture was allowed to stir for 1 h at room temperature before water was added. The mixture was extracted with ethyl acetate (2×). The combined extracts were washed with water and brine, dried over sodium sulfate, filtered and concentrated. The residue was subjected to silica gel column chromatography (0-50% CH$_2$Cl$_2$/hexanes) to give methyl 6-chloro-2-(2,4,6-trimethylphenoxy)pyridine-3-carboxylate (3.58 g, 24%). ESI-MS m/z calc. 305.1, found 306.2 (M+1)+; Retention time: 0.87 min (1 min run).

Step 2: methyl 6-phenethyl-2-(2,4,6-trimethylphenoxy)pyridine-3-carboxylate

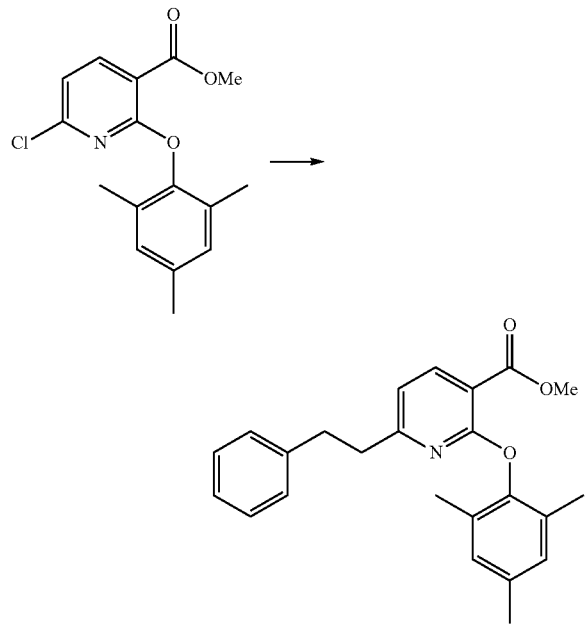

Bromo-(2-phenylethyl)zinc (3.9 mL of 0.5 M, 2.0 mmol) and dichloro[1,1'-bis(diphenylphosphino)ferrocene]palladium (II) dichloromethane adduct (36 mg, 0.049 mmol) were stirred at room temperature under an atmosphere of nitrogen for 20 min. Methyl 6-chloro-2-(2,4,6-trimethylphenoxy)pyridine-3-carboxylate (150 mg, 0.49 mmol) was added to the reaction mixture and it was then heated at 150° C. for 10 minutes in a microwave reactor. A saturated aqueous solution of ethylenediaminetetraacetic acid disodium salt (2 mL) and a saturated aqueous solution of ammonium chloride were added to the reaction mixture. After stirring for 30 minutes, the layers were separated and the aqueous layer was extracted with dichloromethane. The combined organic layers were evaporated to dryness and the residue was subjected to preparatory-HPLC (20-80% acetonitrile/water with 5 mM HCl) to yield methyl 6-(2-phenylethyl)-2-(2,4,6-trimethylphenoxy)pyridine-3-carboxylate (56 mg, 31%). ESI-MS m/z calc. 375.2, found 376.4 (M+1)$^+$; Retention time: 0.87 min (1 min run).

Step 3: 6-phenethyl-2-(2,4,6-trimethylphenoxy)pyridine-3-carboxylic acid

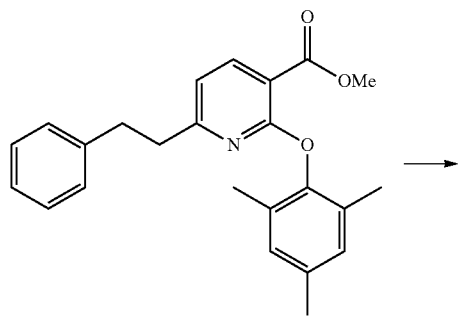

Methyl 6-(2-phenylethyl)-2-(2,4,6-trimethylphenoxy)pyridine-3-carboxylate (56 mg, 0.15 mmol) was dissolved in methanol (5 mL). NaOH (245 µL of 4.0 M, 0.98 mmol) was added and the mixture was stirred at room temperature overnight. The solvent was removed and the pH of the residue was adjusted to—3 with 1N HCl. The precipitate was filtered, washed with water and dried to give 6-phenethyl-2-(2,4,6-trimethylphenoxy)pyridine-3-carboxylic acid (21 mg, 36%). ESI-MS m/z calc. 361.2, found 362.5 (M+1)$^+$; Retention time: 0.77 min (1 min run).

The following compound can be synthesized using the procedures described herein: 6-benzyl-2-(2,4,6-trimethylphenoxy)pyridine-3-carboxylic acid.

Preparation 6: N-[(6-amino-2-pyridyl)sulfonyl]-6-tert-butyl-2-(2,4,6-trimethylphenoxy)pyridine-3-carboxamide (Compound 228)

Step 1: 6-tert-butyl-2-(2,4,6-trimethylphenoxy)pyridine-3-carbonitrile

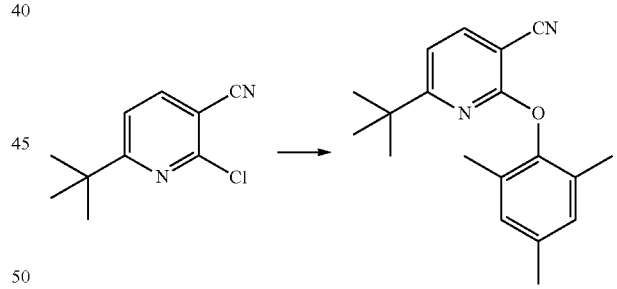

6-tert-Butyl-2-chloro-pyridine-3-carbonitrile (5.00 g, 25.7 mmol), 2,4,6-trimethylphenol (3.50 g, 25.7 mmol), K$_2$CO$_3$ (3.91 g, 28.3 mmol) and N,N-dimethylformamide (10 mL) were added to a 40 mL vial. The mixture was stirred overnight at 95° C. The reaction mixture was diluted with H$_2$O (10 mL) and was extracted with ethyl acetate (3×20 mL). The combined organic layers were washed with brine, dried over sodium sulfate and concentrated. The residue was subjected to silica gel column chromatography (0-20% ethyl acetate/hexanes) to give 6-tert-butyl-2-(2,4,6-trimethylphenoxy)pyridine-3-carbonitrile (6.70 g, 84%) as a white solid. ESI-MS m/z calc. 294.2, found 295.2 (M+1)$^+$; Retention time: 2.31 min (3 min run). $^1$H NMR (400 MHz, DMSO) δ 8.31 (d, J=8.0 Hz, 1H), 7.25 (d, J=7.9 Hz, 1H), 6.96 (s, 2H), 2.27 (s, 3H), 2.00 (s, 6H), 1.07 (s, 9H).

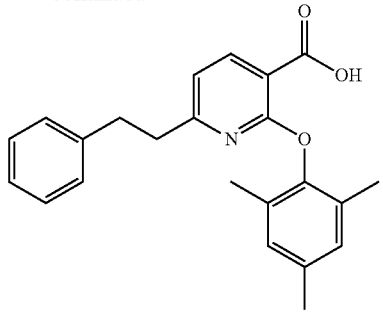

Step 2: 6-tert-butyl-2-(2,4,6-trimethylphenoxy)pyridine-3-carboxylic acid

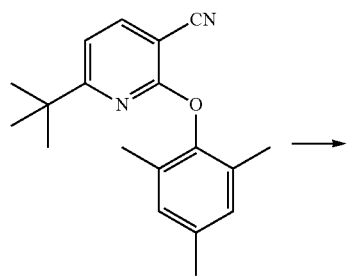

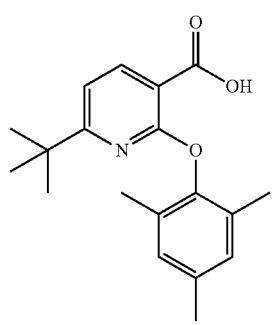

A mixture of 6-tert-butyl-2-(2,4,6-trimethylphenoxy)pyridine-3-carbonitrile (4.50 g, 15.3 mmol), KOH (5.15 g, 91.7 mmol), EtOH (135 mL) and H$_2$O (32 mL) was heated at 90° C. overnight. Additional KOH (2.00 g, 35.6 mmol) was added and the mixture was heated at 90° C. overnight. The mixture was cooled to room temperature, concentrated and acidified to pH ~2 with 2N HCl. The solids were collected via filtration and were placed in a vacuum oven at 50° C. overnight to give 6-tert-butyl-2-(2,4,6-trimethylphenoxy)pyridine-3-carboxylic acid (4.64 g, 96%). $^1$H NMR (400 MHz, DMSO) δ 8.14 (d, J=7.8 Hz, 1H), 7.08 (d, J=7.8 Hz, 1H), 6.91 (s, 2H), 2.26 (s, 3H), 1.97 (s, 6H), 1.04 (s, 9H).

Step 3: 6-tert-butyl-N-[(6-fluoro-2-pyridyl)sulfonyl]-2-(2,4,6-trimethylphenoxy)pyridine-3-carboxamide

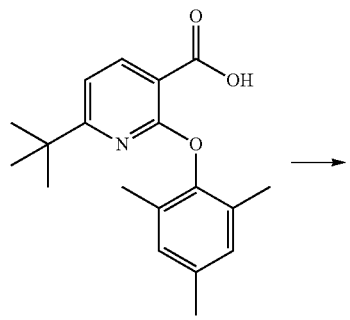

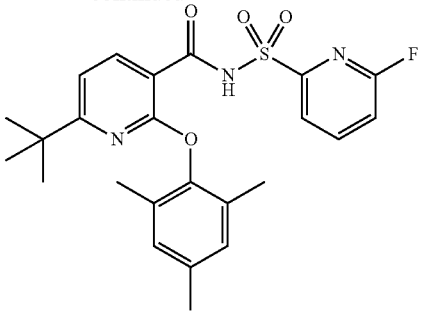

N-ethyl-N-isopropylpropan-2-amine (560 μL, 3.19 mmol) was added to a mixture of 6-tert-butyl-2-(2,4,6-trimethylphenoxy)pyridine-3-carboxylic acid (500. mg, 1.56 mmol), 6-fluoropyridine-2-sulfonamide (309 mg, 1.76 mmol), N-[(dimethylamino)-1H-1,2,3-triazolo-[4,5-b]pyridin-1-ylmethylene]-N-methylmethanaminium hexafluorophosphate N-oxide (728 mg, 1.91 mmol) and N,N-dimethylformamide (5 mL) at room temperature. The mixture was heated at 70° C. overnight before it was cooled. The mixture was partitioned between ethyl acetate and 1N HCl. The layers were separated and the aqueous layer was extracted with ethyl acetate (3×). The combined organics were washed with brine, dried over sodium sulfate, filtered and concentrated. The residue was subjected to silica gel column chromatography (0-20% ethyl acetate/hexanes), then a second purification by silica gel column chromatography (0-10% ethyl acetate/hexanes) to give 6-tert-butyl-N-[(6-fluoro-2-pyridyl)sulfonyl]-2-(2,4,6-trimethylphenoxy)pyridine-3-carboxamide (230 mg, 23%) as a white solid. ESI-MS m/z calc. 471.2, found 472.4 (M+1)$^+$; Retention time: 2.32 min (3 min run).

Step 4: N-[(6-amino-2-pyridyl)sulfonyl]-6-tert-butyl-2-(2,4,6-trimethylphenoxy)pyridine-3-carboxamide (Compound 228)

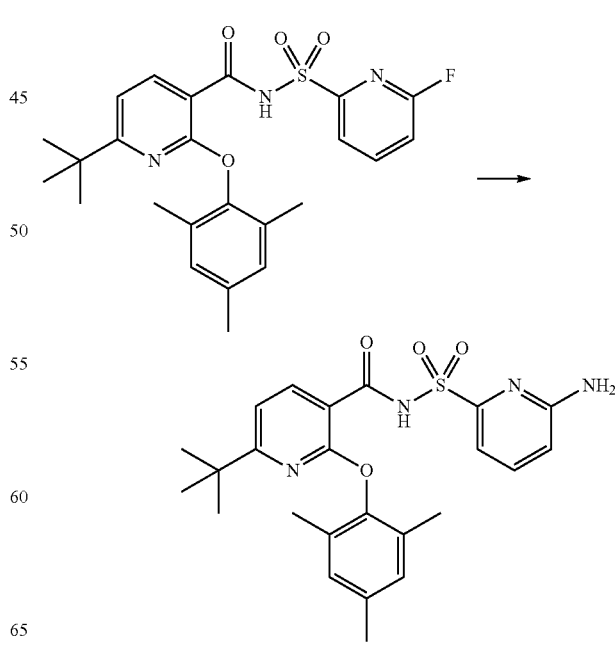

6-tert-Butyl-N-[(6-fluoro-2-pyridyl)sulfonyl]-2-(2,4,6-trimethylphenoxy)pyridine-3-carboxamide (77 mg, 0.16 mmol) was dissolved in ammonium hydroxide (10 mL of 30% w/w) and irradiated in the microwave reactor for 1 h at 150° C. The mixture was evaporated and the crude material was purified by preparatory-HPLC (10-99% acetonitrile/water with 5 μM HCl). The material was further purified by silica gel chromatography (0-100% ethyl acetate/hexanes) to give N-[(6-amino-2-pyridyl)sulfonyl]-6-tert-butyl-2-(2,4,6-trimethylphenoxy)pyridine-3-carboxamide (Compound 228) (27 mg, 35%). $^1$H NMR (400 MHz, DMSO) δ 12.10 (s, 1H), 8.01 (d, J=7.8 Hz, 1H), 7.67-7.58 (m, 1H), 7.20 (d, J=7.3 Hz, 1H), 7.11 (d, J=7.9 Hz, 1H), 6.90 (s, 2H), 6.69 (d, J=8.6 Hz, 1H), 6.49 (s, 2H), 2.26 (s, 3H), 1.97 (s, 6H), 1.05 (s, 9H). ESI-MS m/z calc. 468.2, found 469.3 (M+1)$^+$; Retention time: 2.11 min (3 min run).

The following compounds can be synthesized using the procedures described herein:

6-tert-butyl-N-(1H-indol-4-ylsulfonyl)-2-(2,4,6-trimethylphenoxy)pyridine-3-carboxamide (Compound 275), N-(benzenesulfonyl)-6-tert-butyl-2-(2-isopropylphenoxy)pyridine-3-carboxamide (Compound 147), 6-tert-butyl-N-[[6-(dimethylamino)-2-pyridyl]sulfonyl]-2-(2,4,6-trimethylphenoxy)pyridine-3-carboxamide (Compound 468), N-[(6-amino-2-pyridyl)sulfonyl]-6-(1,1,2,2,2-pentafluoroethyl)-2-(2,4,6-trimethylphenoxy)pyridine-3-carboxamide (Compound 853), N-(4-aminophenyl)sulfonyl-6-(1-methylcyclopropyl)-2-(2,4,6-trimethylphenoxy)pyridine-3-carboxamide (Compound 1297), N-(2-aminothiazol-4-yl)sulfonyl-6-tert-butyl-2-(2,4,6-trimethylphenoxy)pyridine-3-carboxamide (Compound 1294), N-[(6-amino-2-pyridyl)sulfonyl]-6-(1-methylcyclopropyl)-2-(2,4,6-trimethylphenoxy)pyridine-3-carboxamide (Compound 1310), N-[(6-amino-2-pyridyl)sulfonyl]-5-(1-methylcyclopropyl)-2-(2,4,6-trimethylphenoxy)pyridine-3-carboxamide (Compound 854), N-(3-aminophenyl)sulfonyl-6-(1-methylcyclopropyl)-2-(2,4,6-trimethylphenoxy)pyridine-3-carboxamide (Compound 826), 6-(3-fluoro-5-isopropoxy-phenyl)-N-(1H-pyrazol-3-ylsulfonyl)-2-(2,4,6-trimethylphenoxy)pyridine-3-carboxamide (Compound 914), N-[(6-amino-2-pyridyl)sulfonyl]-6-prop-1-ynyl-2-(2,4,6-trimethylphenoxy)pyridine-3-carboxamide (Compound 1172), 6-tert-butyl-N-(2-methylpyrazol-3-yl)sulfonyl-2-(2,4,6-trimethylphenoxy)pyridine-3-carboxamide (Compound 911), N-[(6-amino-2-pyridyl)sulfonyl]-5,6-dimethyl-2-(2,4,6-trimethylphenoxy)pyridine-3-carboxamide (Compound 841), N-[[6-(2-hydroxyethylamino)-2-pyridyl]sulfonyl]-6-phenyl-2-(2,4,6-trimethylphenoxy)pyridine-3-carboxamide (Compound 595), N-[[6-(dimethylamino)-2-pyridyl]sulfonyl]-6-phenyl-2-(2,4,6-trimethylphenoxy)pyridine-3-carboxamide (Compound 869), N-[[6-(2-aminoethylamino)-2-pyridyl]sulfonyl]-6-phenyl-2-(2,4,6-trimethylphenoxy)pyridine-3-carboxamide (Compound 1027), N-[[6-(methylamino)-2-pyridyl]sulfonyl]-6-phenyl-2-(2,4,6-trimethylphenoxy)pyridine-3-carboxamide (Compound 1032), N-[[6-(2-dimethylaminoethylamino)-2-pyridyl]sulfonyl]-6-phenyl-2-(2,4,6-trimethylphenoxy)pyridine-3-carboxamide (Compound 1122), N-[(6-cyano-2-pyridyl)sulfonyl]-6-(3-fluoro-5-isobutoxy-phenyl)-2-(2,4,6-trimethylphenoxy)pyridine-3-carboxamide (Compound 771), N-[(6-amino-2-pyridyl)sulfonyl]-4-methyl-6-phenyl-2-(2,4,6-trimethylphenoxy)pyridine-3-carboxamide (Compound 1102), 6-tert-butyl-N-[[6-(2-hydroxyethylamino)-2-pyridyl]sulfonyl]-2-(2,4,6-trimethylphenoxy)pyridine-3-carboxamide (Compound 916), 6-tert-butyl-N-[[6-(2-dimethylaminoethylamino)-2-pyridyl]sulfonyl]-2-(2,4,6-trimethylphenoxy)pyridine-3-carboxamide (Compound 947), 6-[[6-(3-fluoro-5-isobutoxy-phenyl)-2-(2,4,6-trimethylphenoxy)pyridine-3-carbonyl]sulfamoyl]pyridine-2-carboxylic acid (Compound 461), 6-(3-fluoro-5-isobutoxy-phenyl)-N-[[6-(hydroxymethyl)-2-pyridyl]sulfonyl]-2-(4-methyl-1-piperidyl)pyridine-3-carboxamide (Compound 1340), N-[[6-(2-aminoethylamino)-2-pyridyl]sulfonyl]-6-tert-butyl-2-(2,4,6-trimethylphenoxy)pyridine-3-carboxamide (Compound 1054), N-[(6-amino-2-pyridyl)sulfonyl]-6-methyl-2-(2,4,6-trimethylphenoxy)pyridine-3-carboxamide (Compound 1137), N-(2-azidophenyl)sulfonyl-6-tert-butyl-2-(2,4,6-trimethylphenoxy)pyridine-3-carboxamide, 6-methyl-N-(1H-pyrazol-5-ylsulfonyl)-2-(2,4,6-trimethylphenoxy)pyridine-3-carboxamide (Compound 670), N-[(6-amino-2-pyridyl)sulfonyl]-5-phenethyl-2-(2,4,6-trimethylphenoxy)pyridine-3-carboxamide (Compound 1253), N-[(6-amino-2-pyridyl)sulfonyl]-6-[1-(trifluoromethyl)cyclopropyl]-2-(2,4,6-trimethylphenoxy)pyridine-3-carboxamide (Compound 621), N-[(6-amino-2-pyridyl)sulfonyl]-5-benzyl-2-(2,4,6-trimethylphenoxy)pyridine-3-carboxamide (Compound 1233), N-[[6-(isopropylamino)-2-pyridyl]sulfonyl]-6-methyl-2-(2,4,6-trimethylphenoxy)pyridine-3-carboxamide (Compound 482), N-[[6-(2-methoxyethylamino)-2-pyridyl]sulfonyl]-6-methyl-2-(2,4,6-trimethylphenoxy)pyridine-3-carboxamide (compound 372), N-[(6-amino-2-pyridyl)sulfonyl]-8,8-dimethyl-2-(2,4,6-trimethylphenoxy)-6,7-dihydro-5H-quinoline-3-carboxamide (Compound 182), N-(benzenesulfonyl)-6-tert-butyl-2-(2,4,6-trimethylphenoxy)pyridine-3-carboxamide (Compound 341), 6-tert-butyl-N-[3-(methylamino)phenyl]sulfonyl-2-(2,4,6-trimethylphenoxy)pyridine-3-carboxamide (Compound 289), 6-tert-butyl-N-[3-(dimethylamino)phenyl]sulfonyl-2-(2,4,6-trimethylphenoxy)pyridine-3-carboxamide (Compound 311), 6-tert-butyl-N-(2-cyanophenyl)sulfonyl-2-(2,4,6-trimethylphenoxy)pyridine-3-carboxamide (Compound 78), N-(benzenesulfonyl)-6-tert-butyl-2-(1-methylindol-7-yl)oxy-pyridine-3-carboxamide (Compound 326), 6-tert-butyl-N-(1-methylindol-4-yl)sulfonyl-2-(2,4,6-trimethylphenoxy)pyridine-3-carboxamide (Compound 146), N-[(6-amino-5-fluoro-2-pyridyl)sulfonyl]-6-tert-butyl-2-(2,4,6-trimethylphenoxy)pyridine-3-carboxamide, 6-tert-butyl-N-[(6-methoxy-2-pyridyl)sulfonyl]-2-(2,4,6-trimethylphenoxy)pyridine-3-carboxamide (Compound 34), 6-tert-butyl-N-(4-pyridylsulfonyl)-2-(2,4,6-trimethylphenoxy)pyridine-3-carboxamide (Compound 117),
N-[(2-amino-3-pyridyl)sulfonyl]-6-tert-butyl-2-(2,4,6-trimethylphenoxy)pyridine-3-carboxamide (Compound 235),
N-[(6-amino-2-pyridyl)sulfonyl]-2-(2,4-dimethylphenoxy)-6-(3-fluoro-5-isobutoxy-phenyl)pyridine-3-carboxamide (Compound 590),
N-[(6-amino-2-pyridyl)sulfonyl]-6-(3-fluoro-5-isobutoxy-phenyl)-2-(2-methylphenoxy)pyridine-3-carboxamide (Compound 778),
6-tert-butyl-N-(2-methoxyphenyl)sulfonyl-2-(2,4,6-trimethylphenoxy)pyridine-3-carboxamide (Compound 115),
6-tert-butyl-N-[(2-methoxy-3-pyridyl)sulfonyl]-2-(2,4,6-trimethylphenoxy)pyridine-3-carboxamide (Compound 191),
6-tert-butyl-N-(2-pyridylsulfonyl)-2-(2,4,6-trimethylphenoxy)pyridine-3-carboxamide (Compound 222),
N-[(2-amino-4-pyridyl)sulfonyl]-6-tert-butyl-2-(2,4,6-trimethylphenoxy)pyridine-3-carboxamide (Compound 283),
6=tert-butyl-N-[(2-methoxy-4-pyridyl)sulfonyl]-2-(2,4,6-trimethylphenoxy)pyridine-3-carboxamide (Compound 217),
6-tert-butyl-N-(3-pyridylsulfonyl)-2-(2,4,6-trimethylphenoxy)pyridine-3-carboxamide (Compound 330),
6-tert-butyl-N-(3-methoxyphenyl)sulfonyl-2-(2,4,6-trimethylphenoxy)pyridine-3-carboxamide (Compound 56),
N-(benzenesulfonyl)-6-(trifluoromethyl)-2-(2,4,6-trimethylphenoxy)pyridine-3-carboxamide (Compound 244),
6-tert-butyl-N-[(3-methoxy-2-pyridyl)sulfonyl]-2-(2,4,6-trimethylphenoxy)pyridine-3-carboxamide (Compound 92),
N-(benzenesulfonyl)-2-benzyloxy-6-tert-butyl-pyridine-3-carboxamide (Compound 130),
6-tert-butyl-2-(2,4-dimethylphenoxy)-N-[(2-methoxy-3-pyridyl)sulfonyl]pyridine-3-carboxamide (Compound 89),
N-[(6-amino-2-pyridyl)sulfonyl]-6-tert-butyl-2-(2,4-dimethylphenoxy)pyridine-3-carboxamide (Compound 204),
N-(4-aminophenyl)sulfonyl-6-tert-butyl-2-(2,4,6-trimethylphenoxy)pyridine-3-carboxamide (Compound 11),
N-(3-aminophenyl)sulfonyl-6-tert-butyl-2-(1-phenylethoxy)pyridine-3-carboxamide (Compound 219),
N-[(6-amino-2-pyridyl)sulfonyl]-2-(2,4,6-trimethylphenoxy)-5,6,7,8-tetrahydroquinoline-3-carboxamide (Compound 285),
N-[(5-amino-3-pyridyl)sulfonyl]-6-tert-butyl-2-(2,4,6-trimethylphenoxy)pyridine-3-carboxamide (Compound 163),
N-(3-aminophenyl)sulfonyl-6-tert-butyl-2-(2-methylphenoxy)pyridine-3-carboxamide (Compound 296),
N-(3-aminophenyl)sulfonyl-6-tert-butyl-2-(4-cyano-2,6-dimethyl-phenoxy)pyridine-3-carboxamide (Compound 111),
N-(3-aminophenyl)sulfonyl-6-tert-butyl-2-(2,4-dimethylphenoxy)pyridine-3-carboxamide (Compound 251),
N-[(6-amino-2-pyridyl)sulfonyl]-2-(2,3-dimethylcyclopentoxy)-6-(3-fluoro-5-isobutoxy-phenyl)pyridine-3-carboxamide (Compound 503),
N-(benzenesulfonyl)-6-tert-butyl-2-(3-methoxyphenoxy)pyridine-3-carboxamide (Compound 101),
6-tert-butyl-N-[(6-oxo-1H-pyridin-2-yl)sulfonyl]-2-(2,4,6-trimethylphenoxy)pyridine-3-carboxamide (Compound 305),
N-(3-aminophenyl)sulfonyl-6-tert-butyl-2-(2-cyano-4,6-dimethyl-phenoxy)pyridine-3-carboxamide (Compound 221),
N-(3-aminophenyl)sulfonyl-2-(2,6-dimethylphenoxy)-6-(trifluoromethyl)pyridine-3-carboxamide (Compound 243),
N-(3-aminophenyl)sulfonyl-6-(trifluoromethyl)-2-(2,4,6-trimethylphenoxy)pyridine-3-carboxamide (Compound 96),
6-tert-butyl-N-[(4-oxo-1H-pyridin-3-yl)sulfonyl]-2-(2,4,6-trimethylphenoxy)pyridine-3-carboxamide (Compound 107),
N-(benzenesulfonyl)-6-tert-butyl-2-(2-pyridylmethoxy)pyridine-3-carboxamide (Compound 154),
6-tert-butyl-N-[(2-oxo-1H-pyridin-4-yl)sulfonyl]-2-(2,4,6-trimethylphenoxy)pyridine-3-carboxamide (Compound 113),
6-tert-butyl-2-(2,4-dimethylphenoxy)-N-[(2-hydroxy-3-pyridyl)sulfonyl]pyridine-3-carboxamide,
N-[(6-amino-2-pyridyl)sulfonyl]-6-(trifluoromethyl)-2-(2,4,6-trimethylphenoxy)pyridine-3-carboxamide (Compound 175),
N-[(6-amino-2-pyridyl)sulfonyl]-2-(2,6-dimethylphenoxy)-6-(trifluoromethyl)pyridine-3-carboxamide (Compound 246),
N-[(6-amino-2-pyridyl)sulfonyl]-6-cyclopropyl-4-(trifluoromethyl)-2-(2,4,6-trimethylphenoxy)pyridine-3-carboxamide (Compound 54),
N-(3-aminophenyl)sulfonyl-6-tert-butyl-2-phenoxy-pyridine-3-carboxamide (Compound 272),
N-(3-aminophenyl)sulfonyl-6-methyl-2-(2,4,6-trimethylphenoxy)pyridine-3-carboxamide (Compound 13),
N-[(6-amino-2-pyridyl)sulfonyl]-6-(3-fluoro-5-isobutoxy-phenyl)-2-(3-methylcyclopentoxy)pyridine-3-carboxamide (Compound 452),
N-[(6-amino-2-pyridyl)sulfonyl]-6-(3-fluoro-5-isobutoxy-phenyl)-2-phenoxy-pyridine-3-carboxamide (Compound 376),
N-[(6-amino-2-pyridyl)sulfonyl]-6-(3-fluoro-5-isobutoxy-phenyl)-2-[1-(3-fluorophenyl)ethoxy]pyridine-3-carboxamide (Compound 562),
N-[(6-amino-2-pyridyl)sulfonyl]-2-[(3-ethyloxetan-3-yl)methoxy]-6-(3-fluoro-5-isobutoxy-phenyl)pyridine-3-carboxamide (Compound 618),
N-[[6-(3-aminopropylamino)-2-pyridyl]sulfonyl]-6-methyl-2-(2,4,6-trimethylphenoxy)pyridine-3-carboxamide (Compound 982),
N-[[6-(cyclopropylamino)-2-pyridyl]sulfonyl]-6-methyl-2-(2,4,6-trimethylphenoxy)pyridine-3-carboxamide (Compound 594),
6-methyl-N-[[6-(methylamino)-2-pyridyl]sulfonyl]-2-(2,4,6-trimethylphenoxy)pyridine-3-carboxamide (Compound 646),
N-[[6-(2-aminoethylamino)-2-pyridyl]sulfonyl]-6-methyl-2-(2,4,6-trimethylphenoxy)pyridine-3-carboxamide (Compound 792),
6-methyl-N-[(6-morpholino-2-pyridyl)sulfonyl]-2-(2,4,6-trimethylphenoxy)pyridine-3-carboxamide (Compound 883),
6-methyl-N-[[6-(4-methylpiperazin-1-yl)-2-pyridyl]sulfonyl]-2-(2,4,6-trimethylphenoxy)pyridine-3-carboxamide (Compound 1018),
N-[[6-(dimethylamino)-2-pyridyl]sulfonyl]-6-methyl-2-(2,4,6-trimethylphenoxy)pyridine-3-carboxamide (Compound 1250),
2-(2,4-dimethylphenoxy)-N-[(2-methoxy-3-pyridyl)sulfonyl]-8,8-dimethyl-6,7-dihydro-5H-quinoline-3-carboxamide (Compound 1347), 2-(2,4-dimethylphenoxy)-8,8-dimethyl-N-(1H-pyrazol-3-ylsulfonyl)-6,7-dihydro-5H-quinoline-3-carboxamide (Compound 1246),
6-tert-butyl-N-[(2-methoxy-6-methyl-3-pyridyl)sulfonyl]-2-(2,4,6-trimethylphenoxy)pyridine-3-carboxamide (Compound 1153),
8,8-dimethyl-N-(1H-pyrazol-5-ylsulfonyl)-2-(2,4,6-trimethylphenoxy)-6,7-dihydro-5H-quinoline-3-carboxamide (Compound 715),
N-[(6-amino-2-pyridyl)sulfonyl]-6-(3-fluoro-5-isobutoxy-phenyl)-2-(oxetan-2-ylmethoxy)pyridine-3-carboxamide (Compound 640),
N-[(6-amino-2-pyridyl)sulfonyl]-6-tert-butyl-2-(cyclohexoxy)pyridine-3-carboxamide (Compound 649),
2-(2,6-dimethylphenoxy)-6-(3-fluoro-5-isobutoxy-phenyl)-N-(1H-pyrazol-5-ylsulfonyl)pyridine-3-carboxamide (Compound 671),
6-(3-fluoro-5-isobutoxy-phenyl)-2-phenoxy-N-(1H-pyrazol-5-ylsulfonyl)pyridine-3-carboxamide (Compound 679),
N-[(6-amino-2-pyridyl)sulfonyl]-6-(3-fluoro-5-isobutoxy-phenyl)-2-tetrahydropyran-3-yloxy-pyridine-3-carboxamide (Compound 706),
6-(3-fluoro-5-isobutoxy-phenyl)-2-(2-methylphenoxy)-N-(1H-pyrazol-5-ylsulfonyl)pyridine-3-carboxamide (Compound 738),
6-(3-fluoro-5-isobutoxy-phenyl)-2-(4-methylphenoxy)-N-(1H-pyrazol-5-ylsulfonyl)pyridine-3-carboxamide (Compound 758),
N-[(6-amino-2-pyridyl)sulfonyl]-6-tert-butyl-2-(2-cyano-4,6-dimethyl-phenoxy)pyridine-3-carboxamide (Compound 767),
N-[(6-amino-2-pyridyl)sulfonyl]-2-[(2,2-difluorocyclopropyl)methoxy]-6-(3-fluoro-5-isobutoxy-phenyl)pyridine-3-carboxamide (Compound 769),
N-[(6-amino-2-pyridyl)sulfonyl]-6-(3-fluoro-5-isobutoxy-phenyl)-2-[1-(o-tolyl)ethoxy]pyridine-3-carboxamide (Compound 782),
N-[(6-amino-2-pyridyl)sulfonyl]-6-(3-fluoro-5-isobutoxy-phenyl)-2-[(3-methyloxetan-3-yl)methoxy]pyridine-3-carboxamide (Compound 824),
N-[(6-amino-2-pyridyl)sulfonyl]-6-tert-butyl-2-(2,4-difluorophenoxy)pyridine-3-carboxamide (Compound 829),
N-[(6-amino-2-pyridyl)sulfonyl]-6-(3-fluoro-5-isobutoxy-phenyl)-2-[1-(4-fluorophenyl)ethoxy]pyridine-3-carboxamide (Compound 867),
N-[(6-amino-2-pyridyl)sulfonyl]-6-(3-fluoro-5-isobutoxy-phenyl)-2-(oxetan-3-yloxy)pyridine-3-carboxamide (Compound 872),
N-[(6-amino-2-pyridyl)sulfonyl]-6-(3-fluoro-5-isobutoxy-phenyl)-2-(1-phenylethoxy)pyridine-3-carboxamide (Compound 874),
N-[(6-amino-2-pyridyl)sulfonyl]-2-[(2,2-dimethylcyclopropyl)methoxy]-6-(3-fluoro-5-isobutoxy-phenyl)pyridine-3-carboxamide (Compound 894),
N-[(6-amino-2-pyridyl)sulfonyl]-6-(3-fluoro-5-isobutoxy-phenyl)-2-(tetrahydropyran-4-ylmethoxy)pyridine-3-carboxamide (Compound 933),
N-[(6-amino-2-pyridyl)sulfonyl]-2-(4,4-difluorocyclohexoxy)-6-(3-fluoro-5-isobutoxy-phenyl)pyridine-3-carboxamide (Compound 961),
N-[(6-amino-2-pyridyl)sulfonyl]-6-(3-fluoro-5-isobutoxy-phenyl)-2-(1-methyl-2-phenyl-ethoxy)pyridine-3-carboxamide (Compound 967),
N-[(6-amino-2-pyridyl)sulfonyl]-2-(2,6-dimethylcyclohexoxy)-6-(3-fluoro-5-isobutoxy-phenyl)pyridine-3-carboxamide (Compound 978),
N-[(6-amino-2-pyridyl)sulfonyl]-6-tert-butyl-2-(2-isopropylphenoxy)pyridine-3-carboxamide (Compound 1031),
N-[(6-amino-2-pyridyl)sulfonyl]-6-tert-butyl-2-(1-phenylpropoxy)pyridine-3-carboxamide (Compound 1045),
N-[(6-amino-2-pyridyl)sulfonyl]-6-tert-butyl-2-phenoxypyridine-3-carboxamide (Compound 1046),
N-[(6-amino-2-pyridyl)sulfonyl]-6-(3-fluoro-5-isobutoxy-phenyl)-2-[(3-fluorooxetan-3-yl)methoxy]pyridine-3-carboxamide (Compound 1053),
N-[(6-amino-2-pyridyl)sulfonyl]-6-(3-fluoro-5-isobutoxy-phenyl)-2-(1-phenylpropoxy)pyridine-3-carboxamide (Compound 1068),
N-[(6-amino-2-pyridyl)sulfonyl]-6-tert-butyl-2-(1-methyl-indol-7-yl)oxy-pyridine-3-carboxamide (Compound 1071),
N-[(6-amino-2-pyridyl)sulfonyl]-2-[[(1R,5S)-3-bicyclo[3.1.0]hexanyl]oxy]-6-(3-fluoro-5-isobutoxy-phenyl)pyridine-3-carboxamide (Compound 1077),
N-[(6-amino-2-pyridyl)sulfonyl]-6-tert-butyl-2-(4-cyano-2,6-dimethyl-phenoxy)pyridine-3-carboxamide (Compound 1089),
N-[(6-amino-2-pyridyl)sulfonyl]-6-tert-butyl-2-(4-fluoro-2-methyl-phenoxy)pyridine-3-carboxamide (Compound 1104),
N-[(6-amino-2-pyridyl)sulfonyl]-6-(3-fluoro-5-isobutoxy-phenyl)-2-(2-methylcyclohexoxy)pyridine-3-carboxamide (Compound 1108),
N-[(6-amino-2-pyridyl)sulfonyl]-6-tert-butyl-2-(cyclobutoxy)pyridine-3-carboxamide (Compound 1154),
N-[(6-amino-2-pyridyl)sulfonyl]-2-(1-cyclopropylethoxy)-6-(3-fluoro-5-isobutoxy-phenyl)pyridine-3-carboxamide (Compound 1165),
N-[(6-amino-2-pyridyl)sulfonyl]-6-(3-fluoro-5-isobutoxy-phenyl)-2-[(1R,2R,4S)-norbornan-2-yl]oxy-pyridine-3-carboxamide (Compound 1216),
N-[(6-amino-2-pyridyl)sulfonyl]-6-(3-fluoro-5-isobutoxy-phenyl)-2-norbornan-2-yloxy-pyridine-3-carboxamide (Compound 1227),
N-[(6-amino-2-pyridyl)sulfonyl]-2-(cyclopropylmethoxy)-6-(3-fluoro-5-isobutoxy-phenyl)pyridine-3-carboxamide (Compound 1229),
N-[(6-amino-2-pyridyl)sulfonyl]-2-(1-cyclobutylethoxy)-6-(3-fluoro-5-isobutoxy-phenyl)pyridine-3-carboxamide (Compound 1238),
N-[(6-amino-2-pyridyl)sulfonyl]-6-tert-butyl-2-(2,6-dimethylphenoxy)pyridine-3-carboxamide (Compound 1243),
N-[(6-amino-2-pyridyl)sulfonyl]-2-(cycloheptoxy)-6-(3-fluoro-5-isobutoxy-phenyl)pyridine-3-carboxamide (Compound 1263),
N-[(6-amino-2-pyridyl)sulfonyl]-6-tert-butyl-2-(1-methyl-2-phenyl-ethoxy)pyridine-3-carboxamide (Compound 1314),
N-[(6-amino-2-pyridyl)sulfonyl]-6-tert-butyl-2-(2-methylphenoxy)pyridine-3-carboxamide (Compound 1318),
N-[(6-amino-2-pyridyl)sulfonyl]-6-(3-fluoro-5-isobutoxy-phenyl)-2-tetrahydropyran-4-yloxy-pyridine-3-carboxamide (Compound 1324),
N-[(6-amino-2-pyridyl)sulfonyl]-6-tert-butyl-2-norbornan-2-yloxy-pyridine-3-carboxamide (Compound 1349),
N-[(6-amino-2-pyridyl)sulfonyl]-7,7-dimethyl-2-(2,4,6-trimethylphenoxy)-6,8-dihydro-5H-quinoline-3-carboxamide (Compound 665),
N-[(6-amino-2-pyridyl)sulfonyl]-2-(2,5-dimethylcyclopentoxy)-6-(3-fluoro-5-isobutoxy-phenyl)pyridine-3-carboxamide (Compound 416), N-[(6-amino-2-pyridyl)sulfonyl]-6-(3-fluoro-5-isobutoxyphenyl)-2-tetrahydrofuran-3-yloxy-pyridine-3-carboxamide (Compound 433), N-[(6-amino-2-pyridyl)sulfonyl]-6-(3-fluoro-5-isobutoxyphenyl)-2-(4-methylcyclohexoxy)pyridine-3-carboxamide (Compound 438), N-[(6-amino-2-pyridyl)sulfonyl]-6-tert-butyl-2-[(4S)-2,2,4-trimethylpyrrolidin-1-yl]pyridine-3-carboxamide (Compound 985), N-[(6-amino-2-pyridyl)sulfonyl]-6-tert-butyl-2-(2,2,4-trimethylpyrrolidin-1-yl)pyridine-3-carboxamide (Compound 1461), 3-[[6-tert-butyl-2-(2,4,6-trimethylphenoxy)pyridine-3-carbonyl]sulfamoyl]benzoic acid (Compound 205), N-(3-aminophenyl)sulfonyl-6-phenyl-2-(2,4,6-trimethylphenoxy)pyridine-3-carboxamide (Compound 231), N-[(6-amino-2-pyridyl)sulfonyl]-6-phenethyl-2-(2,4,6-trimethylphenoxy)pyridine-3-carboxamide (Compound 268), N-[(6-amino-2-pyridyl)sulfonyl]-6-benzyl-2-(2,4,6-trimethylphenoxy)pyridine-3-carboxamide (Compound 1), N-(benzenesulfonyl)-2-(2,4,6-trimethylphenoxy)quinoline-3-carboxamide (Compound 215), N-[(6-amino-2-pyridyl)sulfonyl]-8-methyl-2-(2,4,6-trimethylphenoxy)quinoline-3-carboxamide (Compound 70), N-[(6-amino-2-pyridyl)sulfonyl]-2-(2,4,6-trimethylphenoxy)quinoline-3-carboxamide (Compound 91), N-(3-aminophenyl)sulfonyl-2-(2,4,6-trimethylphenoxy)quinoline-3-carboxamide (Compound 260), N-(4-pyridylsulfonyl)-2-(2,4,6-trimethylphenoxy)quinoline-3-carboxamide (Compound 240), 6-tert-butyl-N-(1H-pyrazol-5-ylsulfonyl)-2-(2,4,6-trimethylphenoxy)pyridine-3-carboxamide (Compound 214), 6-tert-butyl-N-[[6-(methylamino)-2-pyridyl]sulfonyl]-2-(2,4,6-trimethylphenoxy)pyridine-3-carboxamide (Compound 262), and N-[(6-amino-2-pyridyl)sulfonyl]-2-(2,4-dimethylphenoxy)-8,8-dimethyl-6,7-dihydro-5H-quinoline-3-carboxamide (Compound 15).

Preparation 7: 6-tert-butyl-N-(2-hydroxyphenyl)sulfonyl-2-(2,4,6-trimethylphenoxy)pyridine-3-carboxamide (Compound 131)

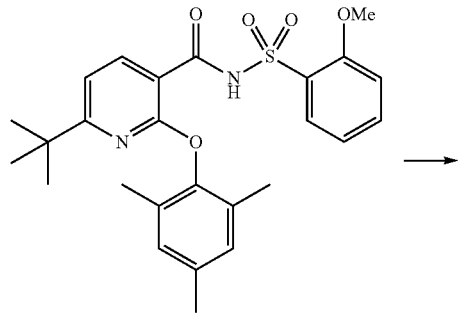

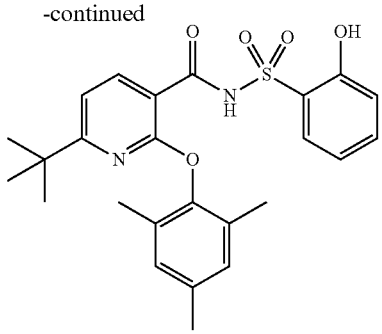

6-tert-Butyl-N-(2-methoxyphenyl)sulfonyl-2-(2,4,6-trimethylphenoxy)pyridine-3-carboxamide (Compound 115) (99 mg, 0.21 mmol) was taken-up in $CH_2Cl_2$ (10 mL). The mixture was cooled to −78° C. before $BBr_3$ (1.0 mL, 1M, 1.0 mmol) was added slowly. The mixture allowed to warm to room temperature overnight. The reaction mixture was diluted with saturated $NaHCO_3$ (10 mL) and was extracted with ethyl acetate (2×5 mL). The organic layers were dried over sodium sulfate and concentrated. The residue was subjected to preparatory-HPLC (20-80% acetonitrile/water with 5 mM HCl) to give 6-tert-butyl-N-(2-hydroxyphenyl)sulfonyl-2-(2,4,6-trimethylphenoxy)pyridine-3-carboxamide (Compound 131) (63 mg, 66%). $^1$H NMR (400 MHz, DMSO) δ 11.66 (s, 1H), 11.04 (s, 1H), 8.05 (d, J=7.8 Hz, 1H), 7.83 (d, J=7.9 Hz, 1H), 7.52 (s, 1H), 7.16 (d, J=7.9 Hz, 1H), 7.02 (s, 2H), 6.93 (s, 2H), 2.26 (s, 3H), 1.98 (s, 6H), 1.04 (s, 9H). ESI-MS m/z calc. 468.2, found 469.0 (M+1)$^+$; Retention time: 2.16 min (3 min run).

The following compound can be synthesized using the procedures described herein:

6-tert-butyl-N-(3-hydroxyphenyl)sulfonyl-2-(2,4,6-trimethylphenoxy)pyridine-3-carboxamide (Compound 47) and 6-(3-fluoro-5-isobutoxy-phenyl)-N-(3-hydroxyphenyl)sulfonyl-2-(2,2,4-trimethylpyrrolidin-1-yl)pyridine-3-carboxamide (Compound 395).

Preparation 8: 6-tert-butyl-2-(1-phenylethyl)pyridine-3-carboxylic acid

Step 1: 6-tert-butyl-2-(1-phenylethyl)pyridine-3-carbonitrile

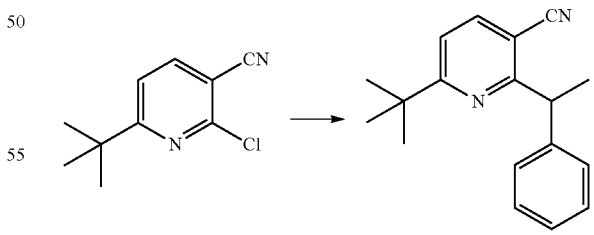

A mixture of bromo(1-phenylethyl)zinc (4.1 mL of 0.5 M, 2.1 mmol) and dichloro[1,1'-bis(diphenylphosphino)ferrocene]palladium (II) dichloromethane adduct (38 mg, 0.051 mmol) was stirred at room temperature under an atmosphere of nitrogen for 20 min. 6-tert-Butyl-2-chloro-pyridine-3-carbonitrile (100 mg, 0.51 mmol) was added and the reaction mixture was heated at 150° C. for 10 min in a microwave reactor. The mixture was concentrated and the residue was subjected to silica gel column chromatography (0-20% ethyl acetate/hexanes) to give 6-tert-butyl-2-(1-phenylethyl) pyridine-3-carbonitrile (120 mg, 80.%). ESI-MS m/z calc. 264.2, found 265.4 (M+1)$^+$; Retention time: 2.28 min (3 min run).

Step 2: 6-tert-butyl-2-(1-phenylethyl)pyridine-3-carboxylic acid

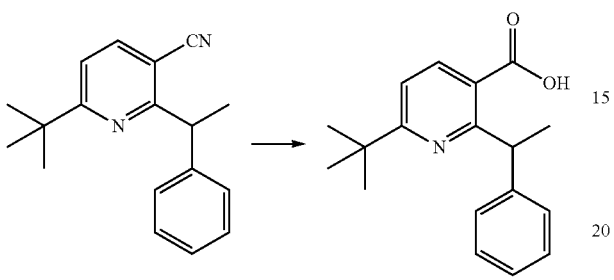

A mixture of 6-tert-butyl-2-(1-phenylethyl)pyridine-3-carbonitrile (120 mg, 0.45 mmol), KOH (1.1 mL of 4.0 M, 4.4 mmol) and EtOH (1.2 mL) was heated at 90° C. overnight. The mixture was concentrated and conc. HCl was added to the residue. The solids were collected and washed with water. The solids were placed in a vacuum oven at 60° C. overnight to give a 1:1 mixture of 6-tert-butyl-2-(1-phenylethyl)pyridine-3-carboxylic acid [ESI-MS m/z calc. 283.2, found 284.3 (M+1)$^+$; Retention time: 0.78 min (1 min run)] and 6-tert-butyl-2-(1-phenylethyl)pyridine-3-carboxamide [ESI-MS m/z calc. 282.2, found 283.4 (M+1)$^+$; Retention time: 0.69 min (1 min run)].

The following compound can be synthesized using the procedures described herein:
6-tert-butyl-2-[(2,4,6-trimethylphenyl)methyl]pyridine-3-carboxylic acid,
N-(3-aminophenyl)sulfonyl-6-tert-butyl-2-(1-phenylethyl) pyridine-3-carboxamide (Compound 271), and
N-(3-aminophenyl)sulfonyl-6-tert-butyl-2-[(2,4,6-trimethylphenyl)methyl]pyridine-3-carboxamide (Compound 346).

Preparation 9: 6-tert-butyl-3-[(2,4,6-trimethylphenyl)methyl]pyridine-2-carboxylic acid Step 1: 5-bromo-2-tert-butylpyridine

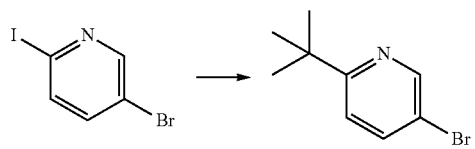

tert-Butylmagnesium chloride (60 mL of a 1.0 N solution in THF, 60 mmol) was slowly added to a greenish suspension of CuCN (2.7 g, 30 mmol) in THF (60 mL) cooled to −78° C. and the resulting gray mixture was stirred at −78° C. for 1 h. A solution of 5-bromo-2-iodopyridine (4.3 g, 15 mmol) in THF (10 mL) was then added. The reaction mixture was stirred at −78° C. for 1 h then at 0° C. for 3 h before being allowed to warm up gradually to room temperature overnight. Ammonium hydroxide (80 mL of 20%) was added and the resulting mixture was filtered and washed with ethyl acetate (100 mL). The filtrate was washed with brine (40 mL), dried over MgSO$_4$, filtered and concentrated under reduced pressure. The residue was purified by silica gel chromatography (0-10% ethyl acetate/heptanes) to afford 5-bromo-2-tert-butylpyridine (2.2 g, 68%; contains 20% heptanes) as a colorless oil. H NMR (300 MHz, CDCl$_3$) δ 1.43 (s, 9H), 7.23 (dd, J=8.5, 0.9 Hz, 1H), 7.71 (dd, J=8.5, 2.3 Hz, 1H), 8.60 (d, J=2.3 Hz, 1H). [M+H]$^+$=214.0.

Step 2: 5-bromo-2-tert-butylpyridine-N-oxide

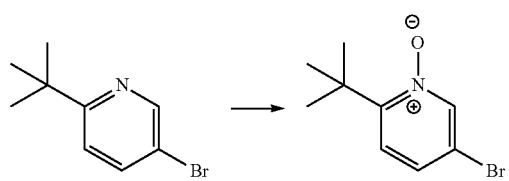

3-Chlorobenzoperoxoic acid (4.40 g of 77% grade, 17.9 mmol) was added to a solution of 5-bromo-2-tert-butylpyridine (3.70 g, 13.8 mmol) in dichloromehtane (45 mL). The reaction mixture was stirred at room temperature overnight. Ca(OH)$_2$ (4.1 g, 44 mmol) was added and the resulting mixture was then stirred at room temperature for 30 min before being filtered through a pad of Celite. The filtrate was concentrated under reduced pressure and the residue was purified by silica gel chromatography (0-50% ethyl acetate/heptanes) to afford 5-bromo-2-tert-butylpyridine-N-oxide (2.7 g, 85%) as a white solid. $^1$H NMR (300 MHz, CDCl$_3$) δ 1.48 (s, 9H), 7.19 (d, J=8.8 Hz, 1H), 7.31 (dd, J=8.8, 1.8 Hz, 1H), 8.33 (d, J=1.8 Hz, 11H). [M+H]$^+$=230.0.

Step 3: 6-tert-butylpyridine-2-carbonitrile

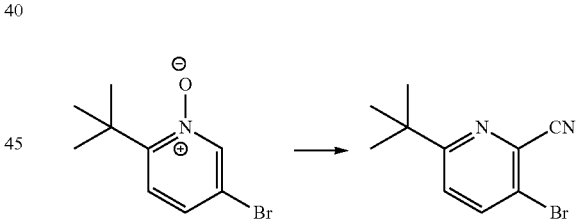

Trimethylsilanecarbonitrile (8.8 mL, 70 mmol) and Et$_3$N (7.4 mL, 53 mmol) were added to a solution of 5-bromo-2-tert-butylpyridine-N-oxide (2.7 g, 12 mmol) in acetonitrile (20 mL) at room temperature. The reaction mixture was then heated at 100° C. overnight. Additional trimethylsilanecarbonitrile (2.4 mL, 19 mmol) and Et$_3$N (2.1 mL, 15 mmol) were added and the reaction mixture was heated at reflux again overnight. Most of the acetonitrile was removed under reduced pressure and the residue was dissolved in ethyl acetate (100 mL). The organic layer was washed with a saturated aqueous solution of NaHCO$_3$ (20 mL), brine (20 mL), dried over MgSO$_4$, filtered and concentrated under reduced pressure. The residue was purified by silica gel chromatography (0-15% ethyl acetate/heptanes) to afford 3-bromo-6-tert-butylpyridine-2-carbonitrile (2.6 g, 93%) as a colorless oil. $^1$H NMR (300 MHz, CDCl$_3$) δ 1.34 (s, 9H), 7.42 (d, J=8.5 Hz, 1H), 7.89 (d, J=8.5 Hz, 1H). [M+H]$^+$=238.9.

Step 4: 6-tert-butyl-3-[(2,4,6-trimethylphenyl)methyl]pyridine-2-carbonitrile

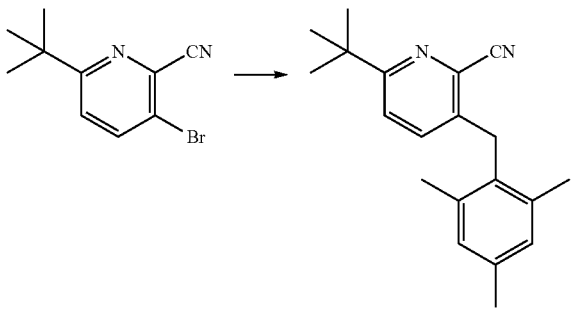 [SMILES: CC(C)(C)c1ccc(Br)c(C#N)n1 ; Cc1cc(C)c(Cc2ccc(C(C)(C)C)nc2C#N)c(C)c1]

Tetrakis(triphenylphosphine)palladium(0) (530 mg, 0.46 mmol) was added to a solution of 3-bromo-6-tert-butylpyridine-2-carbonitrile (1.1 g, 4.6 mmol) in THF (12 mL) in a sealed tube. The mixture was evacuated and backfilled with nitrogen three times, then a stock solution of (2,4,6-trimethylphenyl)methylzinc bromide (9.2 mL of a 1.0 M solution in THF, 9.2 mmol) was added at room temperature. The orange solution was stirred at 60° C. overnight. The reaction mixture was quenched with 5% citric acid (20 mL) and the resulting mixture was extracted with ethyl acetate (2×40 mL). The combined organic layers were washed with water (2×15 mL), brine (15 mL), dried over MgSO$_4$, filtered and concentrated under reduced pressure. The residue was purified by silica gel chromatography (5-30% ethyl acetate/heptanes) to afford 6-tert-butyl-3-[(2,4,6-trimethylphenyl)methyl]pyridine-2-carbonitrile (1.2 g, 89%) as a white solid. $^1$H NMR (300 MHz, CDCl$_3$) δ 1.32 (s, 9H), 2.17 (s, 6H), 2.30 (s, 3H), 4.17 (s, 2H), 6.91 (s, 2H), 6.97 (d, J=8.5 Hz, 1H), 7.32 (d, J=8.5 Hz, 1H). [M+H]$^+$=293.2.

Step 5: 6-tert-butyl-3-[(2,4,6-trimethylphenyl)methyl]pyridine-2-carboxylic acid

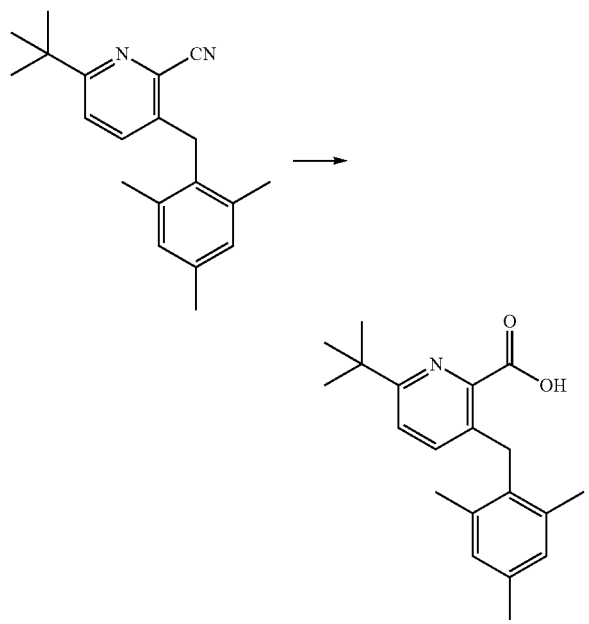

6-tert-Butyl-3-[(2,4,6-trimethylphenyl)methyl]pyridine-2-carbonitrile (900. mg, 3.08 mmol) was dissolved in acetic acid (8 mL). Concentrated HCl (8 mL) was added and the reaction mixture was stirred at 120° C. for 3 d. Additional acetic acid (2 mL) and concentrated HCl (2 mL) were added and the reaction mixture was stirred at 120° C. for another 24 h. Most of the acetic acid was removed under reduced pressure and the resulting heterogeneous mixture was basified with 25% aqueous NaOH to a pH of about 8-10. An aqueous solution of 5% citric acid (20 mL) was then added and the aqueous layer was extracted with methyl tert-butyl ether (2×50 mL). The combined organic layers were washed with water (2×20 mL), brine (20 mL), dried over MgSO$_4$, filtered and concentrated under reduced pressure. The residue was purified by silica gel chromatography (0-50% ethyl acetate/heptanes) to afford 6-tert-butyl-3-[(2,4,6-trimethylphenyl)methyl]pyridine-2-carboxylic acid (660 mg, 68.8%) as a white solid. $^1$H NMR (300 MHz, CDCl$_3$) δ 1.36 (s, 9H), 2.12 (s, 6H), 2.31 (s, 3H), 4.57 (s, 2H), 6.91 (s, 2H), 7.07 (d, J=8.2 Hz, 1H), 7.39 (d, J=8.2 Hz, 1H), 12.25 (br s, 1H). [M+H]$^+$=312.2.

The following compounds can be synthesized using the procedures described herein: N-(benzenesulfonyl)-6-tert-butyl-3-[(2,4,6-trimethylphenyl)methyl]pyridine-2-carboxamide (Compound 22), and N-(3-aminophenyl)sulfonyl-6-tert-butyl-3-[(2,4,6-trimethylphenyl)methyl]pyridine-2-carboxamide (Compound 313).

Preparation 10: 6-tert-butyl-3-(2,4,6-trimethylphenoxy)pyridine-2-carboxylic acid

Step 1: 6-tert-butyl-3-(2,4,6-trimethylphenoxy)pyridine-2-carbonitrile

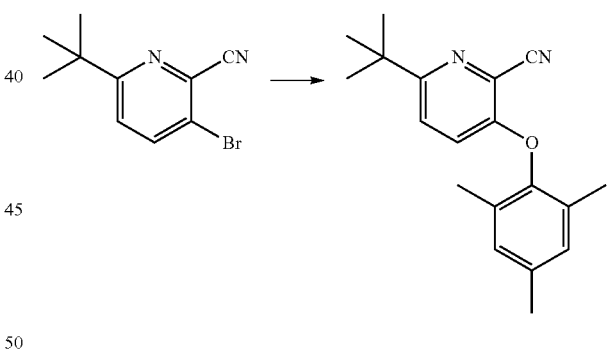

A mixture of 3-bromo-6-tert-butylpyridine-2-carbonitrile (1.0 g, 4.2 mmol), 2,4,6-trimethylphenol (0.57 g, 4.2 mmol) and Cs$_2$CO$_3$ (2.0 g, 6.3 mmol) in DMSO (8 mL) was heated at 100° C. overnight. Once cooled to room temperature, ethyl acetate (70 mL) was added and the organic layer was washed with water (2×20 mL), brine (20 mL), dried over MgSO$_4$, filtered and concentrated under reduced pressure. The residue was purified by silica gel chromatography, (0-30% ethyl acetate/heptanes to afford 6-tert-butyl-3-(2,4,6-trimethylphenoxy)pyridine-2-carbonitrile (1.0 g, 81%) as a white solid. $^1$H NMR (300 MHz, CDCl$_3$) δ 1.33 (s, 9H), 2.08 (s, 6H), 2.30 (s, 3H), 6.73 (d, J=9.1 Hz, 1H), 6.92 (s, 2H), 7.32 (d, J=8.8 Hz, 1H). [M+H]$^+$=295.1.

1883

Step 2: 6-tert-butyl-3-(2,4,6-trimethylphenoxy)pyridine-2-carboxylic acid

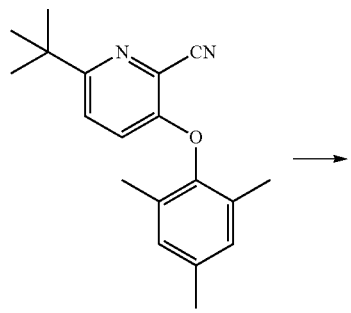

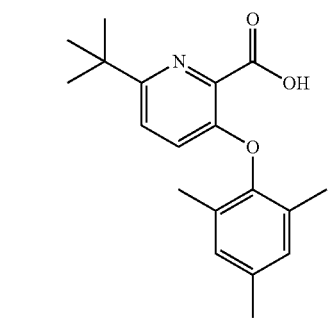

6-tert-Butyl-3-(2,4,6-trimethylphenoxy)pyridine-2-carbonitrile (700 mg, 2.38 mmol) was dissolved in acetic acid (9 mL). Concentrated HCl (9 mL) was added and the reaction mixture was heated at 120° C. for 2 d. Once cooled to room temperature, the reaction mixture was concentrated to dryness under reduced pressure. The residue was suspended in water (20 mL) and 2N NaOH (3 mL) was added to provide a clear aqueous solution. The aqueous layer was washed with methyl tert-butyl ether (2×10 mL), acidified by the addition of 5% citric acid (20 mL) and the resulting mixture was extracted with ethyl acetate (2×50 mL). The combined organic layers were washed with water (2×20 mL), brine (20 mL), dried over MgSO$_4$, filtered and concentrated under reduced pressure. The residue was triturated with heptanes (10 mL) at 0° C. to afford 6-tert-butyl-3-(2,4,6-trimethylphenoxy)pyridine-2-carboxylic acid (574 mg, 77%) as an off-white solid. $^1$H NMR (300 MHz, CDCl$_3$) δ 1.37 (s, 9H), 2.08 (s, 6H), 2.30 (s, 3H), 6.89-6.92 (m, 3H), 7.42 (d, J=8.9 Hz, 1H), 11.68 (br s, 1H). [M+H]$^+$=314.2.

The following compounds can be synthesized using the procedures described herein: N-(3-aminophenyl)sulfonyl-6-tert-butyl-3-(2,4,6-trimethylphenoxy)pyridine-2-carboxamide (Compound 106) and N-(benzenesulfonyl)-6-tert-butyl-3-(2,4,6-trimethylphenoxy)pyridine-2-carboxamide (Compound 350).

1884

Preparation 11: N-(3-aminophenyl)sulfonyl-5-cyano-6-methyl-2-(2,4,6-trimethylphenoxy)pyridine-3-carboxamide (Compound 124)

Step 1: ethyl 5-cyano-6-methyl-2-(2,4,6-trimethylphenoxy)pyridine-3-carboxylate

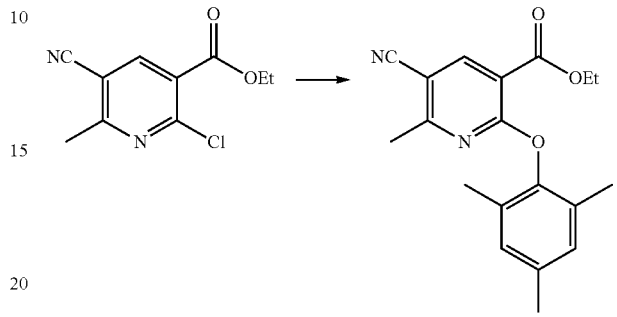

Ethyl 2-chloro-5-cyano-6-methyl-pyridine-3-carboxylate (518 mg, 2.31 mmol), 2,4,6-trimethylphenol (377 mg, 2.77 mmol), and cesium carbonate (1.50 g, 4.61 mmol) were combined in N,N-dimethylformamide (5 mL) and heated at 90° C. for 1 h. The reaction mixture was cooled and partitioned between ethyl acetate and 1N HCl. The organics were separated, washed with brine, dried over sodium sulfate and evaporated to give ethyl 5-cyano-6-methyl-2-(2,4,6-trimethylphenoxy)pyridine-3-carboxylate. ESI-MS m/z calc. 324.2, found 325.2 (M+1)$^+$; Retention time: 0.77 min (1 min run).

Step 2: 5-cyano-6-methyl-2-(2,4,6-trimethylphenoxy)pyridine-3-carboxylic acid

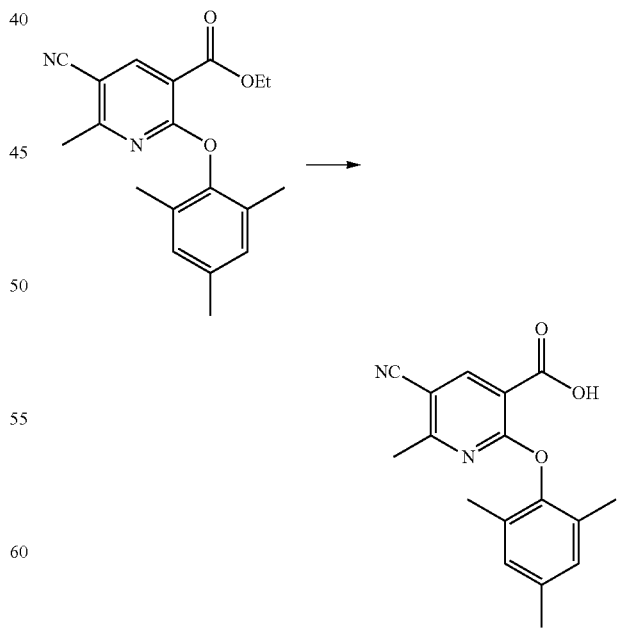

Crude ethyl 5-cyano-6-methyl-2-(2,4,6-trimethylphenoxy)pyridine-3-carboxylate was dissolved in methanol (12 mL) before NaOH (12 mL of 1.0 M, 12 mmol) was added.

The mixture was heated at 70° C. for 3 h. The mixture was cooled and made acidic by the addition of 1 N HCl. The resulting precipitate was collected by filtration. The solid was further dried to give 5-cyano-6-methyl-2-(2,4,6-trimethylphenoxy)pyridine-3-carboxylic acid (500 mg, 73% for 2 steps). ESI-MS m/z calc. 296.1, found 297.4 (M+1)$^+$; Retention time: 0.63 min (1 min run).

Step 3: 5-cyano-6-methyl-N-(3-nitrophenyl)sulfonyl-2-(2,4,6-trimethylphenoxy)pyridine-3-carboxamide

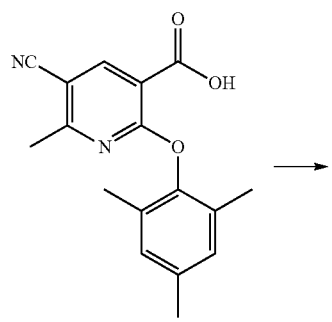

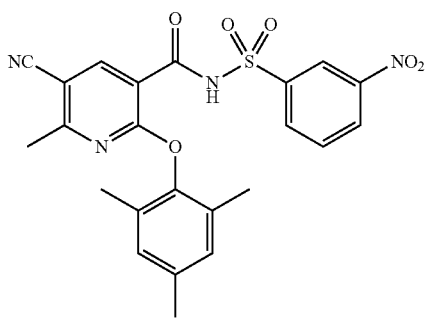

5-Cyano-6-methyl-2-(2,4,6-trimethylphenoxy)pyridine-3-carboxylic acid (65 mg, 0.22 mmol), [(3-nitrophenyl)sulfonylamino]sodium (98 mg, 0.44 mmol), N-[(dimethylamino)-1H-1,2,3-triazolo-[4,5-b]pyridin-1-ylmethylene]-N-methylmethanaminium hexafluorophosphate N-oxide (170 mg, 0.44 mmol) and N,N-dimethylformamide (1 mL) were combined and the mixture was stirred at room temperature for 1 h. The reaction mixture was diluted with water (1 mL) and was extracted with ethyl acetate (2×5 mL). The organic layers were dried over sodium sulfate, filtered and concentrated. The residue was subjected to preparatory-HPLC (20-80% acetonitrile/water with 5 mM HCl) to give 5-cyano-6-methyl-N-(3-nitrophenyl)sulfonyl-2-(2,4,6-trimethylphenoxy)pyridine-3-carboxamide. ESI-MS m/z calc. 480.1, found 481.5 (M+1)$^+$; Retention time: 0.73 min (1 min run).

Step 4: N-(3-aminophenyl)sulfonyl-5-cyano-6-methyl-2-(2,4,6-trimethylphenoxy)pyridine-3-carboxamide (Compound 124)

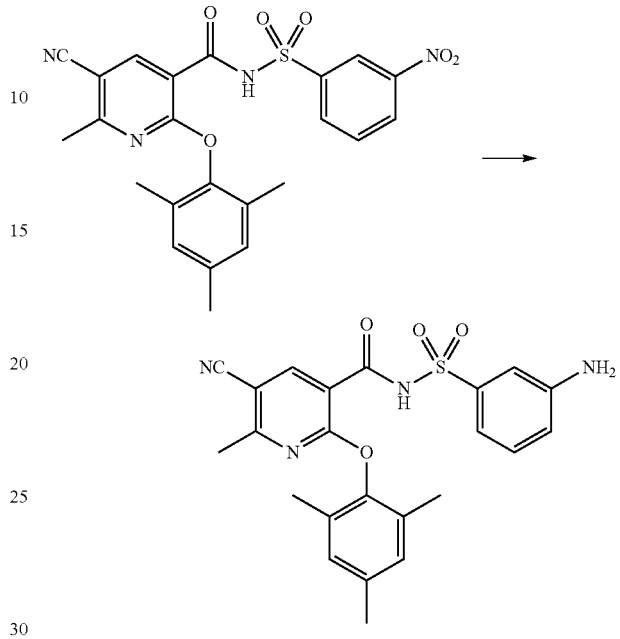

5-Cyano-6-methyl-N-(3-nitrophenyl)sulfonyl-2-(2,4,6-trimethylphenoxy)pyridine-3-carboxamide (from step 3) was dissolved in methanol (10 mL) before 10% Pd/C (12 mg, 0.011 mmol) was added. The mixture was stirred under a balloon of hydrogen at room temperature for 2 h. The mixture was filtered and concentrated. The residue was subjected to preparatory-HPLC (25-75% acetonitrile/water with 5 mM HCl) to give N-(3-aminophenyl)sulfonyl-5-cyano-6-methyl-2-(2,4,6-trimethylphenoxy)pyridine-3-carboxamide (Compound 124) (15 mg, 15% for 2 steps). ESI-MS m/z calc. 450.1, found 451.0 (M+1)$^+$; Retention time: 1.68 min (3 min run).

Preparation 12: N-(2-aminophenyl)sulfonyl-6-tert-butyl-2-(2,4,6-trimethylphenoxy)pyridine-3-carboxamide (Compound 322)

Step 1: 6-tert-butyl-N-(2-nitrophenyl)sulfonyl-2-(2,4,6-trimethylphenoxy)pyridine-3-carboxamide

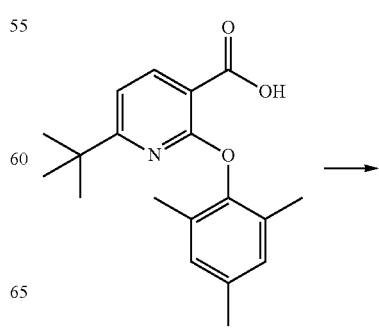

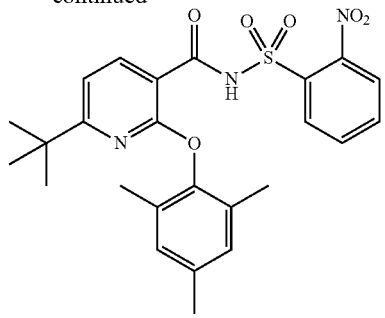

6-tert-Butyl-2-(2,4,6-trimethylphenoxy)pyridine-3-carboxylic acid (50. mg, 0.16 mmol), 2-nitrobenzenesulfonamide (32 mg, 0.16 mmol), N-[(dimethylamino)-1H-1,2,3-triazolo-[4,5-b]pyridin-1-ylmethylene]-N-methylmethanaminium hexafluorophosphate N-oxide (91 mg, 0.24 mmol), ethyldiisopropylamine (56 µL, 0.32 mmol) and NMP (1 mL) were combined. The mixture was heated at 75° C. for 16 h before it was cooled to room temperature. The reaction mixture was diluted with water (1 mL) and extracted with ethyl acetate (2×5 mL). The combined organic layers were dried over sodium sulfate, filtered and concentrated. The residue was subjected to preparatory-HPLC (30-90% acetonitrile/water with 5 mM HC) to give 6-tert-butyl-N-(2-nitrophenyl)sulfonyl-2-(2,4,6-trimethylphenoxy)pyridine-3-carboxamide. ESI-MS m/z calc. 497.2, found 498.4 (M+1)⁺; Retention time: 0.89 min (1 min run).

Step 2: N-(2-aminophenyl)sulfonyl-6-tert-butyl-2-(2,4,6-trimethylphenoxy)pyridine-3-carboxamide (Compound 322)

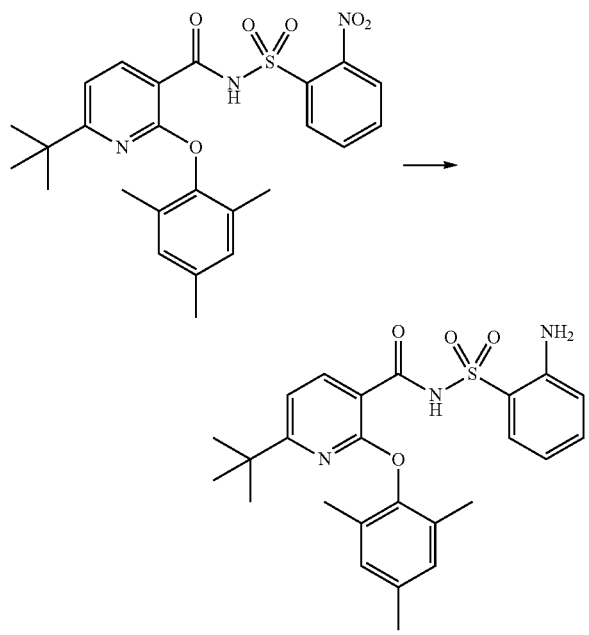

6-tert-Butyl-N-(2-nitrophenyl)sulfonyl-2-(2,4,6-trimethylphenoxy)pyridine-3-carboxamide (23 mg, 0.046 mmol) was dissolved in EtOH (5 mL) before 10% Pd/C (2 mg, 0.02 mmol) was added. The mixture was stirred under a balloon of hydrogen at room temperature for 2 h. The mixture was filtered and the filtrate was concentrated. The residue was subjected to preparatory-HPLC (20-80% acetonitrile/water with 5 mM HCl) to give N-(2-aminophenyl)sulfonyl-6-tert-butyl-2-(2,4,6-trimethylphenoxy)pyridine-3-carboxamide (Compound 322) (4.8 mg, 33%). ¹H NMR (400 MHz, DMSO) δ 8.06 (s, 1H), 7.74 (s, 1H), 7.36 (s, 1H), 7.20 (s, 1H), 6.99 (s, 2H), 6.87 (s, 1H), 6.72 (s, 1H), 2.34 (s, 3H), 2.04 (s, 6H), 1.33 (s, 2H), 1.13 (s, 9H). ESI-MS m/z calc. 467.2, found 468.0 (M+1)⁺; Retention time: 2.25 min (3 min run).

The following compounds can be synthesized using the procedures described herein: N-(3-aminophenyl)sulfonyl-6-tert-butyl-2-(2,6-dimethylphenoxy)pyridine-3-carboxamide (Compound 286), N-(4-aminophenyl)sulfonyl-6-tert-butyl-2-cyclohexyl-pyridine-3-carboxamide (Compound 537), N-(3-aminophenyl)sulfonyl-6-tert-butyl-2-(2,4,6-trimethylphenoxy)pyridine-3-carboxamide (Compound 294) and N-(3-amino-1-methyl-pyrazol-4-yl)sulfonyl-6-tert-butyl-2-(2,4,6-trimethylphenoxy)pyridine-3-carboxamide (Compound 41).

Preparation 13: 6-tert-butyl-N-[(2-oxo-1H-pyridin-3-yl)sulfonyl]-2-(2,4,6-trimethylphenoxy)pyridine-3-carboxamide (Compound 51)

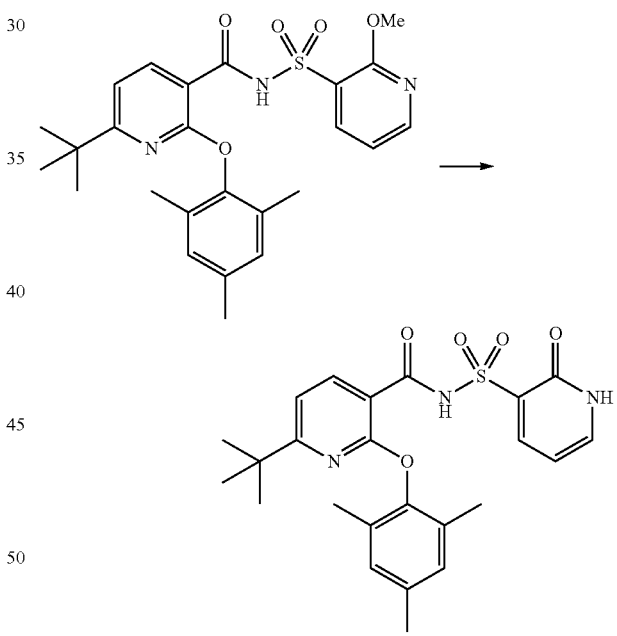

6-tert-butyl-N-[(2-methoxy-3-pyridyl)sulfonyl]-2-(2,4,6-trimethylphenoxy)pyridine-3-carboxamide (Compound 191) (45 mg, 0.093 mmol) was dissolved in dioxane (1 mL) before aq HCl (0.5 mL of 4.0 M, 2.0 mmol) was added. The reaction mixture was heated at 90° C. for 1 h before it was cooled and concentrated. The residue was subjected to preparatory-HPLC (20-80% acetonitrile/water with 5 µM HCl) to give 6-tert-butyl-N-[(2-oxo-1H-pyridin-3-yl)sulfonyl]-2-(2,4,6-trimethylphenoxy)pyridine-3-carboxamide (Compound 51) (19 mg, 20.%). ¹H NMR (400 MHz, DMSO) δ 12.57 (s, 1H), 11.83 (s, 1H), 8.27 (dd, J=7.3, 2.1 Hz, 1H), 8.07 (d, J=7.8 Hz, 1H), 7.83 (d, J=6.3 Hz, 1H), 7.16 (d, J=7.9 Hz, 1H), 6.93 (s, 2H), 6.46 (t, J=6.8 Hz, 1H), 2.27

(s, 3H), 1.99 (s, 6H), 1.05 (s, 9H). ESI-MS m/z calc. 469.2, found 470.3 (M+1)+; Retention time: 1.95 min (3 min run).

The following compound can be synthesized using the procedures described herein:

6-tert-butyl-2-(2,4-dimethylphenoxy)-N-[(2-oxo-1H-pyridin-3-yl)sulfonyl]pyridine-3-carboxamide (Compound 55), 7,7-dimethyl-N-[(2-oxo-1H-pyridin-3-yl)sulfonyl]-2-(2,4,6-trimethylphenoxy)-6,8-dihydro-5H-quinoline-3-carboxamide (Compound 1199), 2-(2,4-dimethylphenoxy)-8,8-dimethyl-N-[(2-oxo-1H-pyridin-3-yl)sulfonyl]-6,7-dihydro-5H-quinoline-3-carboxamide (Compound 634), 8,8-dimethyl-N-[(2-oxo-1H-pyridin-3-yl)sulfonyl]-2-(2,4,6-trimethylphenoxy)-6,7-dihydro-5H-quinoline-3-carboxamide (Compound 899), 6-(1-methylcyclopropyl)-N-[(2-oxo-1H-pyridin-3-yl)sulfonyl]-2-(2,4,6-trimethylphenoxy)pyridine-3-carboxamide (Compound 1226), 6-tert-butyl-N-[(4-methyl-2-oxo-1H-pyridin-3-yl)sulfonyl]-2-(2,4,6-trimethylphenoxy)pyridine-3-carboxamide (Compound 1311), 6-(4-ethoxy-3-fluoro-phenyl)-N-[(2-oxo-1H-pyridin-3-yl)sulfonyl]-2-(2,4,6-trimethylphenoxy)pyridine-3-carboxamide (Compound 901), 6-(4-methylcyclohexyl)-N-[(2-oxo-1H-pyridin-3-yl)sulfonyl]-2-(2,4,6-trimethylphenoxy)pyridine-3-carboxamide (Compound 743), 6-(4,4-dimethylcyclohexyl)-N-[(2-oxo-1H-pyridin-3-yl)sulfonyl]-2-(2,4,6-trimethylphenoxy)pyridine-3-carboxamide (Compound 1091), 6-(4,4-difluorocyclohexyl)-N-[(2-oxo-1H-pyridin-3-yl)sulfonyl]-2-(2,4,6-trimethylphenoxy)pyridine-3-carboxamide (Compound 1329), and 6-cyclohexyl-N-[(2-oxo-1H-pyridin-3-yl)sulfonyl]-2-(2,4,6-trimethylphenoxy)pyridine-3-carboxamide (Compound 1357).

Preparation 14: 6-Fluoropyridine-2-sulfonamide

Step 1: 2-(Benzylthio)-6-fluoropyridine

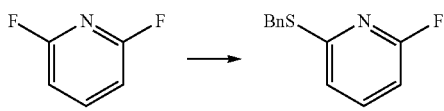

To a solution of BnSH (18.1 g, 146 mmol) in THF (1.12 L) was added 60% NaH (6.60 g, 165 mmol) portionwise over 10 minutes. The reaction mixture was stirred at room temperature for 15 minutes after which time a solution of 2,6-difluoropyridine (13.7 mL, 150. mmol) in THF (100 mL) was added dropwise over 10 minutes. The resulting clear solution was stirred at room temperature for 2 h. The reaction mixture was quenched with H$_2$O (250 mL) and the resultant mixture was extracted with Et$_2$O (800 mL). The organic layer was washed with H$_2$O (400 mL) and brine (250 mL), dried over Na$_2$SO$_4$ and concentrated to dryness. The residue was purified by silica gel column chromatography (100% hexanes followed by a gradient of 1-10% ethyl acetate in hexanes) to give 2-(benzylthio)-6-fluoropyridine (32.0 g, 100%). $^1$H NMR (CDCl$_3$, 250 MHz) δ 7.56 (q, J=8.0 Hz, 1H), 7.43-7.40 (m, 2H), 7.39-7.21 (m, 3H), 7.03 (dd, J=7.5, 2.3 Hz, 1H), 6.60 (dd, J=7.8, 2.5 Hz, 11H), 4.41 (s, 2H).

Step 2: 6-Fluoropyridine-2-sulfonyl chloride

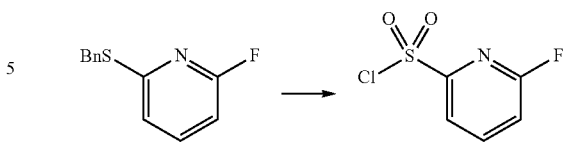

2-(Benzylthio)-6-fluoropyridine (32.0 g, 146 mmol) was dissolved in CHCl$_3$ (500 mL) and H$_2$O (400 mL) was added. Chlorine was slowly bubbled through the reaction mixture for 2 h. (Note: a 30% aq. NaOH trap (1-1.5 L) was used, followed by a sat. aq. Na$_2$S203 (1-1.5 L) trap to neutralize the excess C12). The reaction mixture became warm during the addition and a yellow suspension formed. The reaction was carefully quenched (exothermic and foaming) with a solution of Na$_2$S205 (200 g) in H$_2$O (450 mL). The layers were separated and the aqueous layer was extracted once with CHCl$_3$ (200 mL). The organic layers were combined and washed with H$_2$O (300 mL), dried over Na$_2$SO$_4$ and concentrated to dryness to afford impure 6-fluoropyridine-2-sulfonyl chloride as a brownish oil. This material was used as such in the next step.

Step 3: 6-Fluoropyridine-2-sulfonamide

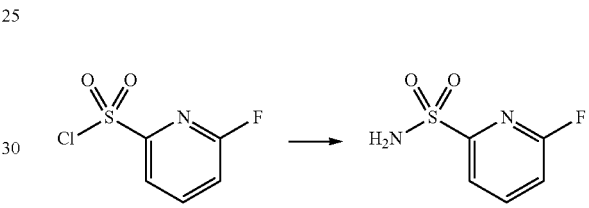

Crude 6-fluoropyridine-2-sulfonyl chloride (from step 2) was dissolved in CH$_2$C2 (1 L) and the solution was cooled to −78° C. Ammonia was bubbled through the solution for 25 min. The mixture was stirred for 1 h at room temperature and the precipitated product was removed by filtration and washed with CH$_2$Cl$_2$ (2×). The filtrate and washings were combined and concentrated to −50 mL and filtered; the solid was washed with CH$_2$Cl$_2$/hexanes (50/50 mL) and dried to afford 6-fluoropyridine-2-sulfonamide (12.0 g, 46% yield, purity ~90%) as a grey solid. $^1$H NMR (DMSO, 250 MHz) δ 8.27 (q, J=8.0 Hz, 1H), 7.88 (dd, J=7.5, 2.1 Hz, 1H), 7.66 (s, 2H), 7.48 (dd, J=8.0, 2.4 Hz, 1H).

Preparation 15: N-[(6-amino-2-pyridyl)sulfonyl]-6-(3-ethoxy-5-fluoro-phenyl)-2-(2,4,6-trimethylphenoxy)pyridine-3-carboxamide (Compound 1255)

Step 1: 6-chloro-2-(2,4,6-trimethylphenoxy)pyridine-3-carboxylic acid

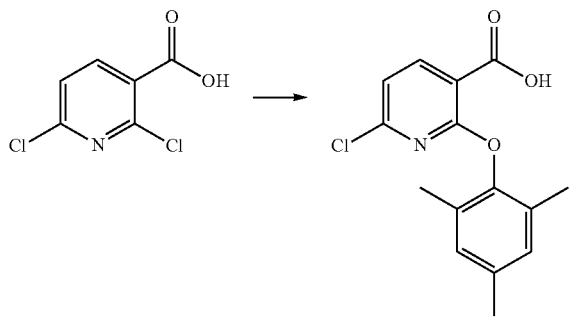 [SMILES: O=C(O)c1ccc(Cl)nc1Cl ; Cc1cc(C)c(Oc2nc(Cl)ccc2C(=O)O)c(C)c1]

To a solution of 2,4,6-trimethylphenol (13.6 g, 100 mmol) in N,N-dimethylformamide (300 mL) at 0-5° C., was carefully added NaH solid (60% in mineral oil, 8.80 g, 220 mmol). After the resultant suspension was stirred at the same temperature for 15 min, solid 2,6-dichloronicotinic acid (19.2 g, 100 mmol) was added. The reaction mixture was stirred at room temperature for 20 min and then at 80° C. overnight. The mixture was cooled to room temperature before it was poured into a cold NaHSO$_4$ solution (24.0 g in 200 mL water). The resultant suspension was stirred at room temperature for 30 min. The precipitate was collected by filtration, washed with water, followed by Et$_2$O/hexanes (200/500 mL), and dried at 40° C. under vacuum to give 6-chloro-2-(2,4,6-trimethylphenoxy)pyridine-3-carboxylic acid as a brownish solid (19.2 g, 66%). $^1$H NMR (400 MHz, DMSO) δ 13.38 (s, 1H), 8.28 (d, J=7.9 Hz, 1H), 7.27 (d, J=7.9 Hz, 1H), 6.94 (d, J=1.1 Hz, 2H), 2.27 (s, 3H), 1.99 (s, 6H). ESI-MS m/z calc. 291.1, found 292.0 (M+1)$^+$; Retention time: 2.34 min (3 min run).

Step 2: 6-chloro-N-[(6-fluoro-2-pyridyl)sulfonyl]-2-(2,4,6-trimethylphenoxy)pyridine-3-carboxamide

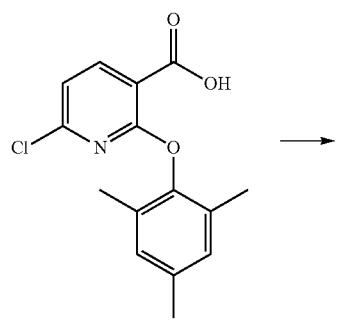

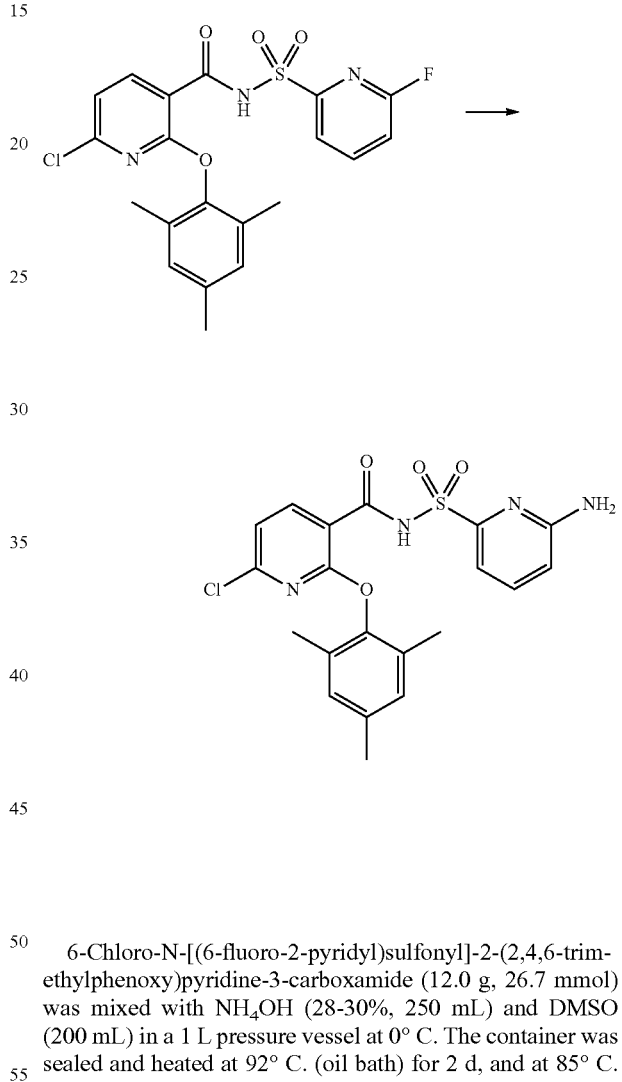

6-Chloro-2-(2,4,6-trimethylphenoxy)pyridine-3-carboxylic acid (23.7 g, 81.4 mmol) was added to a mixture of N-[(dimethylamino)-1H-1,2,3-triazolo-[4,5-b]pyridin-1-yl-methylene]-N-methylmethanaminium hexafluorophosphate N-oxide (35.0 g, 92.1 mmol), 6-fluoropyridine-2-sulfonamide (16.5 g, 93.8 mmol) and ethyldiisopropylamine (36 mL) in N,N-dimethylformamide (400 mL) at 5° C. The resulted mixture was stirred at room temperature overnight before it was quenched with 1 N HCl (150 mL). The mixture was diluted with water (450 mL) and the resultant solids were collected by filtration and washed with water (500 mL), methanol (200 mL) and Et$_2$O (400 mL). The solid was purified by silica gel column chromatography (0-4% methanol/CH$_2$Cl$_2$) to afford 6-chloro-N-[(6-fluoro-2-pyridyl)sulfonyl]-2-(2,4,6-trimethylphenoxy)pyridine-3-carboxamide as a white solid (22.2 g, 60%). $^1$H NMR (CDCl$_3$, 250 MHz) δ 8.36 (dd, J=15.7, 7.5 Hz, 1H), 8.14 (d, J=7.5 Hz, 1H), 8.08 (d, J=8.0 Hz, 1H), 7.58 (d, J=8.2 Hz, 1H), 7.29 (d, J=7.8 Hz, 1H), 6.91 (s, 2H), 2.25 (s, 3H), 1.94 (s, 6H).

Step 3: N-[(6-amino-2-pyridyl)sulfonyl]-6-chloro-2-(2,4,6-trimethylphenoxy)pyridine-3-carboxamide 6-Chloro-N-[(6-fluoro-2-pyridyl)sulfonyl]-2-(2,4,6-trimethylphenoxy)pyridine-3-carboxamide (12.0 g, 26.7 mmol) was mixed with NH$_4$OH (28-30%, 250 mL) and DMSO (200 mL) in a 1 L pressure vessel at 0° C. The container was sealed and heated at 92° C. (oil bath) for 2 d, and at 85° C. for another 2 d. Solvents (water and DMSO) were removed and the residue was suspended in a mixture solvent of CH$_2$Cl$_2$/ethyl acetate/methanol (25/25/25 mL). The suspension was sonicated at room temperature for 15 min and was filtered. The solids were washed with CH$_2$Cl$_2$/ethyl acetate/methanol (10/10/10 mL) and dried to give N-[(6-amino-2-pyridyl)sulfonyl]-6-chloro-2-(2,4,6-trimethylphenoxy)pyridine-3-carboxamide as a white solid (6.8 g, 57%). $^1$H NMR (CDCl$_3$, 250 MHz) δ 8.10 (d, J=7.8 Hz, 1H), 7.64 (t, J=7.8 Hz, 1H), 7.27 (d, J=8.0 Hz, 1H), 7.21 (d, J=7.2 Hz, 1H), 6.92 (s, 2H), 6.71 (d, J=8.5 Hz, 1H), 6.60 (br, s, 2H), 2.26 (s, 3H), 1.98 (s, 6H).

Step 4: N-[(6-amino-2-pyridyl)sulfonyl]-6-(3-ethoxy-5-fluoro-phenyl)-2-(2,4,6-trimethylphenoxy)pyridine-3-carboxamide (Compound 1255)

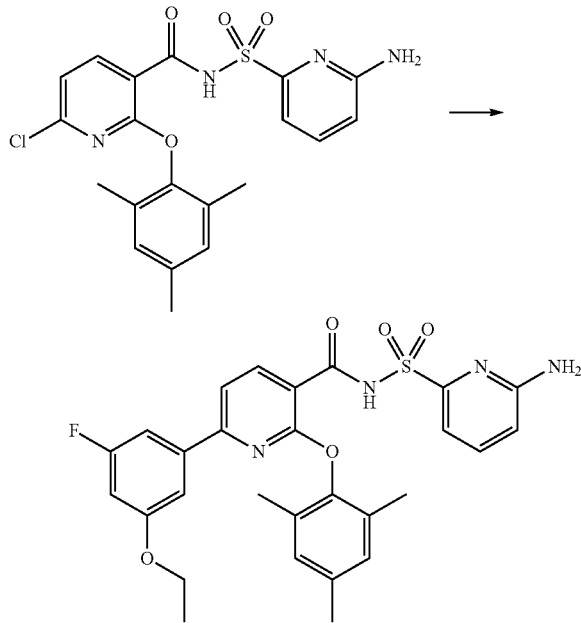

A vial containing a mixture of N-((6-aminopyridin-2-yl)sulfonyl)-6-chloro-2-(mesityloxy)-nicotinamide (30. mg, 0.067 mmol), 3-ethoxy-5-fluoro-benzeneboronic acid (25 mg, 0.13 mmol), Pd(PPh₃)₄ (5.0 mg), K₃PO₄ (2.0 M, 0.13 mL) and N,N-dimethylformamide (0.6 mL) was flushed with nitrogen and sealed. The mixture was then heated at 80° C. overnight before it was cooled and diluted with DMSO (0.3 mL). The mixture was subjected to preparatory-HPLC (30-90% acetonitrile/water with 5 µM HCl) to give N-[(6-amino-2-pyridyl)sulfonyl]-6-(3-ethoxy-5-fluoro-phenyl)-2-(2,4,6-trimethylphenoxy)pyridine-3-carboxamide (Compound 1255) (20 mg, 54%). ESI-MS m/z calc. 550.2, found 551.5 (M+1)⁺; Retention time: 3.15 min (5 min run).

The following compounds can be synthesized using the procedures described herein:

N-[(6-amino-2-pyridyl)sulfonyl]-6-(2-tert-butylphenyl)-2-(2,4,6-trimethylphenoxy)pyridine-3-carboxamide (Compound 364),
N-[(6-amino-2-pyridyl)sulfonyl]-6-cyclopropyl-2-(2,4,6-trimethylphenoxy)pyridine-3-carboxamide (Compound 1050),
N-[(6-amino-2-pyridyl)sulfonyl]-6-(3,4-dimethylphenyl)-2-(2,4,6-trimethylphenoxy)pyridine-3-carboxamide (Compound 399),
N-[(6-amino-2-pyridyl)sulfonyl]-2-(2,6-dimethylphenoxy)-6-(3-fluoro-5-isobutoxy-phenyl)pyridine-3-carboxamide (Compound 639),
N-[(6-amino-2-pyridyl)sulfonyl]-4-(3-fluoro-5-isobutoxy-phenyl)-2-(2,4,6-trimethylphenoxy)benzamide (Compound 1549),
N-[(6-amino-2-pyridyl)sulfonyl]-2-(2,4,6-trimethylphenoxy)-6-vinyl-pyridine-3-carboxamide (Compound 430),
N-[(6-amino-2-pyridyl)sulfonyl]-6-(3-fluoro-5-hydroxy-phenyl)-2-(2,4,6-trimethylphenoxy)pyridine-3-carboxamide (Compound 505),
N-[(6-amino-2-pyridyl)sulfonyl]-6-(6-methyl-3-pyridyl)-2-(2,4,6-trimethylphenoxy)pyridine-3-carboxamide (Compound 513),
N-[(6-amino-2-pyridyl)sulfonyl]-6-(3-fluoro-4-pyridyl)-2-(2,4,6-trimethylphenoxy)pyridine-3-carboxamide (Compound 514),
N-[(6-amino-2-pyridyl)sulfonyl]-6-(2-methylindazol-4-yl)-2-(2,4,6-trimethylphenoxy)pyridine-3-carboxamide (Compound 451),
N-[[6-(aminomethyl)-2-pyridyl]sulfonyl]-6-(3-fluoro-5-isobutoxy-phenyl)-2-(2,4,6-trimethylphenoxy)pyridine-3-carboxamide (Compound 871),
N-[(6-amino-2-pyridyl)sulfonyl]-6-[2-methyl-5-(trifluoromethyl)pyrazol-3-yl]-2-(2,4,6-trimethylphenoxy)pyridine-3-carboxamide (Compound 457),
N-[(6-amino-2-pyridyl)sulfonyl]-6-(2-fluorophenyl)-2-(2,4,6-trimethylphenoxy)pyridine-3-carboxamide (Compound 463),
N-[(6-amino-2-pyridyl)sulfonyl]-5-(3-fluoro-5-isobutoxy-phenyl)-3-(2,4,6-trimethylphenoxy)pyridine-2-carboxamide (Compound 1456),
N-[(6-amino-2-pyridyl)sulfonyl]-6-(1-propylpyrazol-4-yl)-2-(2,4,6-trimethylphenoxy)pyridine-3-carboxamide (Compound 469),
N-[(6-amino-2-pyridyl)sulfonyl]-6-(4,4-dimethylcyclohexyl)-2-(2,4,6-trimethylphenoxy)pyridine-3-carboxamide (Compound 538),
N-[(6-amino-2-pyridyl)sulfonyl]-6-(4,4-difluorocyclohexyl)-2-(2,4,6-trimethylphenoxy)pyridine-3-carboxamide (Compound 783),
N-[(6-amino-2-pyridyl)sulfonyl]-6-ethyl-2-(2,4,6-trimethylphenoxy)pyridine-3-carboxamide (Compound 963),
N-[(6-amino-2-pyridyl)sulfonyl]-6-isopropyl-2-(2,4,6-trimethylphenoxy)pyridine-3-carboxamide (Compound 1232),
N-[(6-amino-2-pyridyl)sulfonyl]-6-cyclopentyl-2-(2,4,6-trimethylphenoxy)pyridine-3-carboxamide (Compound 1280),
N-[(6-amino-2-pyridyl)sulfonyl]-6-(3-methoxypropyl)-2-(2,4,6-trimethylphenoxy)pyridine-3-carboxamide (Compound 791),
N-[(6-amino-2-pyridyl)sulfonyl]-6-pentyl-2-(2,4,6-trimethylphenoxy)pyridine-3-carboxamide (Compound 862),
N-[(6-amino-2-pyridyl)sulfonyl]-6-(2-ethoxyethyl)-2-(2,4,6-trimethylphenoxy)pyridine-3-carboxamide (Compound 929),
N-[(6-amino-2-pyridyl)sulfonyl]-6-cyclohexyl-2-(2,4,6-trimethylphenoxy)pyridine-3-carboxamide (Compound 1131),
N-[(6-amino-2-pyridyl)sulfonyl]-6-[2-(1-piperidyl)pyrimidin-5-yl]-2-(2,4,6-trimethylphenoxy)pyridine-3-carboxamide (Compound 475),
N-[(6-amino-2-pyridyl)sulfonyl]-6-(3-methoxy-4-methylphenyl)-2-(2,4,6-trimethylphenoxy)pyridine-3-carboxamide (Compound 375),
N-[(6-amino-2-pyridyl)sulfonyl]-6-(5-fluoro-2-methoxy-3-pyridyl)-2-(2,4,6-trimethylphenoxy)pyridine-3-carboxamide (Compound 387),
N-[(6-amino-2-pyridyl)sulfonyl]-6-(2,4-difluorophenyl)-2-(2,4,6-trimethylphenoxy)pyridine-3-carboxamide (Compound 439),
N-[(6-amino-2-pyridyl)sulfonyl]-6-(2-hydroxy-3-methylphenyl)-2-(2,4,6-trimethylphenoxy)pyridine-3-carboxamide (Compound 450),
N-[(6-amino-2-pyridyl)sulfonyl]-6-[3-(morpholinomethyl)phenyl]-2-(2,4,6-trimethylphenoxy)pyridine-3-carboxamide (Compound 465), N-[(6-amino-2-pyridyl)sulfonyl]-6-(2-methoxy-3-methyl-phenyl)-2-(2,4,6-trimethylphenoxy)pyridine-3-carboxamide (Compound 477), N-[(6-amino-2-pyridyl)sulfonyl]-6-(3-fluoro-2-methoxyphenyl)-2-(2,4,6-trimethylphenoxy)pyridine-3-carboxamide (Compound 396), N-[(6-amino-2-pyridyl)sulfonyl]-6-(4-isopropoxyphenyl)-2-(2,4,6-trimethylphenoxy)pyridine-3-carboxamide (Compound 436), 6-(2-fluoro-4-methoxy-phenyl)-N-(1H-pyrazol-3-ylsulfonyl)-2-(2,4,6-trimethylphenoxy)pyridine-3-carboxamide (Compound 374), 6-[2-methyl-5-(trifluoromethyl)pyrazol-3-yl]-N-(1H-pyrazol-3-ylsulfonyl)-2-(2,4,6-trimethylphenoxy)pyridine-3-carboxamide (Compound 391), 6-(4-fluoro-2-methoxy-phenyl)-N-(1H-pyrazol-3-ylsulfonyl)-2-(2,4,6-trimethylphenoxy)pyridine-3-carboxamide (Compound 405), N-[(6-amino-2-pyridyl)sulfonyl]-2-(2,4-dimethylphenoxy)-6-(1-isobutylpyrazol-4-yl)pyridine-3-carboxamide (Compound 381), 6-(4-isopropoxyphenyl)-N-[(2-oxo-1H-pyridin-3-yl)sulfonyl]-2-(2,4,6-trimethylphenoxy)pyridine-3-carboxamide (Compound 494), 6-(1,3-benzodioxol-4-yl)-N-[(2-oxo-1H-pyridin-3-yl)sulfonyl]-2-(2,4,6-trimethylphenoxy)pyridine-3-carboxamide (Compound 525), N-[(6-amino-2-pyridyl)sulfonyl]-6-(4-fluorophenyl)-2-(2,4,6-trimethylphenoxy)pyridine-3-carboxamide (Compound 93), N-[(6-amino-2-pyridyl)sulfonyl]-6-(1-methylindol-4-yl)-2-(2,4,6-trimethylphenoxy)pyridine-3-carboxamide (Compound 386), N-[(6-amino-2-pyridyl)sulfonyl]-6-[3-(cyanomethyl)phenyl]-2-(2,4,6-trimethylphenoxy)pyridine-3-carboxamide (Compound 388), N-[(6-amino-2-pyridyl)sulfonyl]-6-(3-methoxyphenyl)-2-(2,4,6-trimethylphenoxy)pyridine-3-carboxamide (Compound 413), N-[(6-amino-2-pyridyl)sulfonyl]-6-(2-methoxypyrimidin-5-yl)-2-(2,4,6-trimethylphenoxy)pyridine-3-carboxamide (Compound 449), N-[(6-amino-2-pyridyl)sulfonyl]-6-(6-methoxy-3-pyridyl)-2-(2,4,6-trimethylphenoxy)pyridine-3-carboxamide (Compound 531), N-[(6-amino-2-pyridyl)sulfonyl]-6-[3-fluoro-4-(isopropylcarbamoyl)phenyl]-2-(2,4,6-trimethylphenoxy)pyridine-3-carboxamide (Compound 543), N-[(6-amino-2-pyridyl)sulfonyl]-6-(5-ethoxy-2-fluoro-phenyl)-2-(2,4,6-trimethylphenoxy)pyridine-3-carboxamide (Compound 599), N-[(6-amino-2-pyridyl)sulfonyl]-6-(2,6-dimethoxy-4-methyl-phenyl)-2-(2,4,6-trimethylphenoxy)pyridine-3-carboxamide (Compound 629), N-[(6-amino-2-pyridyl)sulfonyl]-6-[4-(cyanomethyl)phenyl]-2-(2,4,6-trimethylphenoxy)pyridine-3-carboxamide (Compound 638), N-[(6-amino-2-pyridyl)sulfonyl]-6-(2-fluoro-3-methoxyphenyl)-2-(2,4,6-trimethylphenoxy)pyridine-3-carboxamide (Compound 661), N-[(6-amino-2-pyridyl)sulfonyl]-6-(m-tolyl)-2-(2,4,6-trimethylphenoxy)pyridine-3-carboxamide (Compound 672), N-[(6-amino-2-pyridyl)sulfonyl]-6-(2,3-dihydro-1,4-benzodioxin-6-yl)-2-(2,4,6-trimethylphenoxy)pyridine-3-carboxamide (Compound 673), N-[(6-amino-2-pyridyl)sulfonyl]-6-(3-fluoro-5-methoxyphenyl)-2-(2,4,6-trimethylphenoxy)pyridine-3-carboxamide (Compound 682), N-[(6-amino-2-pyridyl)sulfonyl]-6-[3-(1-piperidylmethyl)phenyl]-2-(2,4,6-trimethylphenoxy)pyridine-3-carboxamide (Compound 686), N-[(6-amino-2-pyridyl)sulfonyl]-6-[2-(2,2,2-trifluoroethoxy)-3-pyridyl]-2-(2,4,6-trimethylphenoxy)pyridine-3-carboxamide (Compound 697), N-[(6-amino-2-pyridyl)sulfonyl]-6-(5-fluoro-2-methoxyphenyl)-2-(2,4,6-trimethylphenoxy)pyridine-3-carboxamide (Compound 700), N-[(6-amino-2-pyridyl)sulfonyl]-6-(3,4-difluorophenyl)-2-(2,4,6-trimethylphenoxy)pyridine-3-carboxamide (Compound 725), N-[(6-amino-2-pyridyl)sulfonyl]-6-[2-fluoro-5-(hydroxymethyl)phenyl]-2-(2,4,6-trimethylphenoxy)pyridine-3-carboxamide (Compound 727), N-[(6-amino-2-pyridyl)sulfonyl]-6-tetrahydropyran-4-yl-2-(2,4,6-trimethylphenoxy)pyridine-3-carboxamide (Compound 748), N-[(6-amino-2-pyridyl)sulfonyl]-6-(4-hydroxy-3-methoxyphenyl)-2-(2,4,6-trimethylphenoxy)pyridine-3-carboxamide (Compound 768), N-[(6-amino-2-pyridyl)sulfonyl]-6-[6-(dimethylamino)-3-pyridyl]-2-(2,4,6-trimethylphenoxy)pyridine-3-carboxamide (Compound 787), 6-[3-(aminomethyl)phenyl]-N-[(6-amino-2-pyridyl)sulfonyl]-2-(2,4,6-trimethylphenoxy)pyridine-3-carboxamide (Compound 801), N-[(6-amino-2-pyridyl)sulfonyl]-6-(2,5-difluorophenyl)-2-(2,4,6-trimethylphenoxy)pyridine-3-carboxamide (Compound 803), N-[(6-amino-2-pyridyl)sulfonyl]-6-[4-(morpholinomethyl)phenyl]-2-(2,4,6-trimethylphenoxy)pyridine-3-carboxamide (Compound 810), N-[(6-amino-2-pyridyl)sulfonyl]-6-(3,5-dimethoxyphenyl)-2-(2,4,6-trimethylphenoxy)pyridine-3-carboxamide (Compound 828), N-[(6-amino-2-pyridyl)sulfonyl]-6-(4-fluoro-2-methoxyphenyl)-2-(2,4,6-trimethylphenoxy)pyridine-3-carboxamide (Compound 830), N-[(6-amino-2-pyridyl)sulfonyl]-6-(4-methyl-2-pyridyl)-2-(2,4,6-trimethylphenoxy)pyridine-3-carboxamide (Compound 1272), N-[(6-amino-2-pyridyl)sulfonyl]-6-(6-methyl-2-pyridyl)-2-(2,4,6-trimethylphenoxy)pyridine-3-carboxamide (Compound 730), N-[(6-amino-2-pyridyl)sulfonyl]-6-(5-methyl-2-pyridyl)-2-(2,4,6-trimethylphenoxy)pyridine-3-carboxamide (Compound 1290), N-[(6-amino-2-pyridyl)sulfonyl]-6-(4-ethoxy-2-fluoro-phenyl)-2-(2,4,6-trimethylphenoxy)pyridine-3-carboxamide (Compound 602), 6-(6-methoxy-5-methyl-3-pyridyl)-N-(1H-pyrazol-3-ylsulfonyl)-2-(2,4,6-trimethylphenoxy)pyridine-3-carboxamide (Compound 1044), 2-(2,4-dimethylphenoxy)-6-(p-tolyl)-N-(1H-pyrazol-3-ylsulfonyl)pyridine-3-carboxamide (Compound 610), 2-(2,4-dimethylphenoxy)-6-(6-methoxy-5-methyl-3-pyridyl)-N-(1H-pyrazol-3-ylsulfonyl)pyridine-3-carboxamide (Compound 892), 2-(2,4-dimethylphenoxy)-6-(3-fluoro-5-isopropoxy-phenyl)-N-(1H-pyrazol-3-ylsulfonyl)pyridine-3-carboxamide (Compound 1213), 2-(2,4-dimethylphenoxy)-6-(4-ethoxyphenyl)-N-(1H-pyrazol-3-ylsulfonyl)pyridine-3-carboxamide (Compound 813), N-[(6-amino-2-pyridyl)sulfonyl]-6-(4-chloro-3-propoxyphenyl)-2-(2,4,6-trimethylphenoxy)pyridine-3-carboxamide (Compound 535), N-[(6-amino-2-pyridyl)sulfonyl]-6-(3-fluoro-2-hydroxyphenyl)-2-(2,4,6-trimethylphenoxy)pyridine-3-carboxamide (Compound 866), N-[(6-amino-2-pyridyl)sulfonyl]-2-(2,4-dimethylphenoxy)-6-(4-ethoxyphenyl)pyridine-3-carboxamide (Compound 641), N-[(6-amino-2-pyridyl)sulfonyl]-2-(2,4-dimethylphenoxy)-6-(3-fluoro-5-isopropoxy-phenyl)pyridine-3-carboxamide (Compound 1150), N-[(6-amino-2-pyridyl)sulfonyl]-2-(2,4-dimethylphenoxy)-6-(p-tolyl)pyridine-3-carboxamide (Compound 1015), N-[(6-amino-2-pyridyl)sulfonyl]-6-(3-ethylphenyl)-2-(2,4,6-trimethylphenoxy)pyridine-3-carboxamide (Compound 1118), N-[(6-amino-2-pyridyl)sulfonyl]-6-(3-isopropylphenyl)-2-(2,4,6-trimethylphenoxy)pyridine-3-carboxamide (Compound 1016), N-[(6-amino-2-pyridyl)sulfonyl]-6-[3-(trifluoromethyl)phenyl]-2-(2,4,6-trimethylphenoxy)pyridine-3-carboxamide (Compound 709), (Compound 709)

N-[(6-amino-2-pyridyl)sulfonyl]-6-(4-ethylphenyl)-2-(2,4,6-trimethylphenoxy)pyridine-3-carboxamide (Compound 900), N-[(6-amino-2-pyridyl)sulfonyl]-6-[4-(trifluoromethyl)phenyl]-2-(2,4,6-trimethylphenoxy)pyridine-3-carboxamide (Compound 548), N-[(6-amino-2-pyridyl)sulfonyl]-2-(2,4-dimethylphenoxy)-6-(6-methoxy-5-methyl-3-pyridyl)pyridine-3-carboxamide (Compound 533), N-[(6-amino-2-pyridyl)sulfonyl]-6-(3-chloro-2-methoxy-4-pyridyl)-2-(2,4,6-trimethylphenoxy)pyridine-3-carboxamide (Compound 1284), N-[(6-amino-2-pyridyl)sulfonyl]-6-(6-methoxy-2-pyridyl)-2-(2,4,6-trimethylphenoxy)pyridine-3-carboxamide (Compound 1034), N-[(6-amino-2-pyridyl)sulfonyl]-6-(6-ethoxy-2-pyridyl)-2-(2,4,6-trimethylphenoxy)pyridine-3-carboxamide (Compound 1133), N-[(6-amino-2-pyridyl)sulfonyl]-6-(3-fluoro-5-isopropoxy-phenyl)-2-(2,4,6-trimethylphenoxy)pyridine-3-carboxamide (Compound 1138), N-[(6-amino-2-pyridyl)sulfonyl]-6-(5-fluoro-2-methoxy-4-pyridyl)-2-(2,4,6-trimethylphenoxy)pyridine-3-carboxamide (Compound 1277), N-[(6-amino-2-pyridyl)sulfonyl]-6-(3-ethoxy-4-methoxyphenyl)-2-(2,4,6-trimethylphenoxy)pyridine-3-carboxamide (Compound 860), N-[(6-amino-2-pyridyl)sulfonyl]-6-(2-isopropylpyrazol-3-yl)-2-(2,4,6-trimethylphenoxy)pyridine-3-carboxamide (Compound 1317), N-[(6-amino-2-pyridyl)sulfonyl]-6-(3-hydroxy-4-methylphenyl)-2-(2,4,6-trimethylphenoxy)pyridine-3-carboxamide (Compound 793), N-[(6-amino-2-pyridyl)sulfonyl]-6-(4-propoxyphenyl)-2-(2,4,6-trimethylphenoxy)pyridine-3-carboxamide (Compound 996), N-[(6-amino-2-pyridyl)sulfonyl]-6-(4-ethoxy-3-methoxyphenyl)-2-(2,4,6-trimethylphenoxy)pyridine-3-carboxamide (Compound 1268), N-[(6-amino-2-pyridyl)sulfonyl]-6-(2-chlorophenyl)-2-(2,4,6-trimethylphenoxy)pyridine-3-carboxamide (Compound 1221), N-[(6-amino-2-pyridyl)sulfonyl]-6-(3,4-dihydro-2H-pyran-6-yl)-2-(2,4,6-trimethylphenoxy)pyridine-3-carboxamide (Compound 937), N-[(6-amino-2-pyridyl)sulfonyl]-6-(3-fluoro-4-methyl-phenyl)-2-(2,4,6-trimethylphenoxy)pyridine-3-carboxamide (Compound 1000), N-[(6-amino-2-pyridyl)sulfonyl]-6-(cyclopenten-1-yl)-2-(2,4,6-trimethylphenoxy)pyridine-3-carboxamide (Compound 1330), N-[(6-amino-2-pyridyl)sulfonyl]-6-(4-chloro-2-methoxyphenyl)-2-(2,4,6-trimethylphenoxy)pyridine-3-carboxamide (Compound 897), (Compound 897)

N-[(6-amino-2-pyridyl)sulfonyl]-6-(2-fluoro-4-methyl-phenyl)-2-(2,4,6-trimethylphenoxy)pyridine-3-carboxamide (Compound 875), N-[(6-amino-2-pyridyl)sulfonyl]-6-isopropenyl-2-(2,4,6-trimethylphenoxy)pyridine-3-carboxamide (Compound 1211), N-[(6-amino-2-pyridyl)sulfonyl]-6-(5-chloro-2-methoxy-3-pyridyl)-2-(2,4,6-trimethylphenoxy)pyridine-3-carboxamide (Compound 993), 6-(1-isobutylpyrazol-4-yl)-N-(1H-pyrazol-3-ylsulfonyl)-2-(2,4,6-trimethylphenoxy)pyridine-3-carboxamide (Compound 577), N-[(6-amino-2-pyridyl)sulfonyl]-6-(2-pyridyl)-2-(2,4,6-trimethylphenoxy)pyridine-3-carboxamide (Compound 1278), N-(1H-pyrazol-3-ylsulfonyl)-6-(2-pyridyl)-2-(2,4,6-trimethylphenoxy)pyridine-3-carboxamide (Compound 1353), 6-(3-ethoxy-5-fluoro-phenyl)-N-(1H-pyrazol-3-ylsulfonyl)-2-(2,4,6-trimethylphenoxy)pyridine-3-carboxamide (Compound 585), N-[(6-amino-2-pyridyl)sulfonyl]-6-(6-isopropoxy-3-pyridyl)-2-(2,4,6-trimethylphenoxy)pyridine-3-carboxamide (Compound 1163), N-[(6-amino-2-pyridyl)sulfonyl]-6-(2-methoxyphenyl)-2-(2,4,6-trimethylphenoxy)pyridine-3-carboxamide (Compound 1173), N-[(6-amino-2-pyridyl)sulfonyl]-6-(3-chlorophenyl)-2-(2,4,6-trimethylphenoxy)pyridine-3-carboxamide (Compound 1295), N-[(6-amino-2-pyridyl)sulfonyl]-6-(3-fluorophenyl)-2-(2,4,6-trimethylphenoxy)pyridine-3-carboxamide (Compound 570), N-[(6-amino-2-pyridyl)sulfonyl]-6-(4-fluoro-2-hydroxyphenyl)-2-(2,4,6-trimethylphenoxy)pyridine-3-carboxamide (Compound 622), N-[(6-amino-2-pyridyl)sulfonyl]-6-(3,6-dihydro-2H-pyran-4-yl)-2-(2,4,6-trimethylphenoxy)pyridine-3-carboxamide (Compound 976), N-[(6-amino-2-pyridyl)sulfonyl]-6-(3,5-difluorophenyl)-2-(2,4,6-trimethylphenoxy)pyridine-3-carboxamide (Compound 1325), N-[(6-amino-2-pyridyl)sulfonyl]-6-(2,4-dimethoxyphenyl)-2-(2,4,6-trimethylphenoxy)pyridine-3-carboxamide (Compound 950), N-[(6-amino-2-pyridyl)sulfonyl]-6-[1-methyl-3-(trifluoromethyl)pyrazol-4-yl]-2-(2,4,6-trimethylphenoxy)pyridine-3-carboxamide (Compound 812), N-[(6-amino-2-pyridyl)sulfonyl]-6-(5-chloro-6-methoxy-3-pyridyl)-2-(2,4,6-trimethylphenoxy)pyridine-3-carboxamide (Compound 1332), N-[(6-amino-2-pyridyl)sulfonyl]-6-(2,6-dimethoxy-3-pyridyl)-2-(2,4,6-trimethylphenoxy)pyridine-3-carboxamide (Compound 754), N-[(6-amino-2-pyridyl)sulfonyl]-6-(2-isopropoxy-3-pyridyl)-2-(2,4,6-trimethylphenoxy)pyridine-3-carboxamide (Compound 909), N-[(6-amino-2-pyridyl)sulfonyl]-6-[3-(trifluoromethyl)-1H-pyrazol-4-yl]-2-(2,4,6-trimethylphenoxy)pyridine-3-carboxamide (Compound 582), N-[(6-amino-2-pyridyl)sulfonyl]-6-[4-(dimethylaminomethyl)phenyl]-2-(2,4,6-trimethylphenoxy)pyridine-3-carboxamide (Compound 962), N-[(6-amino-2-pyridyl)sulfonyl]-6-(5-cyano-2-methoxyphenyl)-2-(2,4,6-trimethylphenoxy)pyridine-3-carboxamide (Compound 1111), N-[(6-amino-2-pyridyl)sulfonyl]-6-(5-fluoro-6-methoxy-3-pyridyl)-2-(2,4,6-trimethylphenoxy)pyridine-3-carboxamide (Compound 612), N-[(6-amino-2-pyridyl)sulfonyl]-6-(2-ethoxypyrimidin-5-yl)-2-(2,4,6-trimethylphenoxy)pyridine-3-carboxamide (Compound 1130), N-[(6-amino-2-pyridyl)sulfonyl]-6-(6-methoxy-5-methyl-3-pyridyl)-2-(2,4,6-trimethylphenoxy)pyridine-3-carboxamide (Compound 705), N-[(6-amino-2-pyridyl)sulfonyl]-6-(6-methoxy-2-methyl-3-pyridyl)-2-(2,4,6-trimethylphenoxy)pyridine-3-carboxamide (Compound 1212), N-[(6-amino-2-pyridyl)sulfonyl]-6-(2-ethoxy-3-pyridyl)-2-(2,4,6-trimethylphenoxy)pyridine-3-carboxamide (Compound 718), N-[(6-amino-2-pyridyl)sulfonyl]-6-(1,3-benzodioxol-4-yl)-2-(2,4,6-trimethylphenoxy)pyridine-3-carboxamide (Compound 974), N-[(6-amino-2-pyridyl)sulfonyl]-6-(1,3-benzodioxol-5-yl)-2-(2,4,6-trimethylphenoxy)pyridine-3-carboxamide (Compound 1207), N-[(6-amino-2-pyridyl)sulfonyl]-6-(4-benzyloxy-2-fluorophenyl)-2-(2,4,6-trimethylphenoxy)pyridine-3-carboxamide (Compound 1113), N-[(6-amino-2-pyridyl)sulfonyl]-6-(5-fluoro-2-hydroxyphenyl)-2-(2,4,6-trimethylphenoxy)pyridine-3-carboxamide (Compound 1409), N-[(6-amino-2-pyridyl)sulfonyl]-6-(1-isopropylpyrazol-4-yl)-2-(2,4,6-trimethylphenoxy)pyridine-3-carboxamide (Compound 808), N-[(6-amino-2-pyridyl)sulfonyl]-6-(5-methoxy-3-pyridyl)-2-(2,4,6-trimethylphenoxy)pyridine-3-carboxamide (Compound 1115), N-[(6-amino-2-pyridyl)sulfonyl]-6-(1-ethylpyrazol-4-yl)-2-(2,4,6-trimethylphenoxy)pyridine-3-carboxamide (Compound 1312), N-[(6-amino-2-pyridyl)sulfonyl]-6-(1,5-dimethylpyrazol-4-yl)-2-(2,4,6-trimethylphenoxy)pyridine-3-carboxamide (Compound 584), 6-phenyl-N-(1H-pyrazol-5-ylsulfonyl)-2-(2,4,6-trimethylphenoxy)pyridine-3-carboxamide (Compound 784), 6-(4-methoxyphenyl)-N-(1H-pyrazol-3-ylsulfonyl)-2-(2,4,6-trimethylphenoxy)pyridine-3-carboxamide (Compound 1033), N-[(2-methoxy-3-pyridyl)sulfonyl]-6-phenyl-2-(2,4,6-trimethylphenoxy)pyridine-3-carboxamide (Compound 939), N-[(6-amino-2-pyridyl)sulfonyl]-6-(1H-indazol-5-yl)-2-(2,4,6-trimethylphenoxy)pyridine-3-carboxamide (Compound 856), N-[(6-amino-2-pyridyl)sulfonyl]-6-(3-cyanophenyl)-2-(2,4,6-trimethylphenoxy)pyridine-3-carboxamide (Compound 886), N-[(6-amino-2-pyridyl)sulfonyl]-6-(4-fluoro-3-methoxyphenyl)-2-(2,4,6-trimethylphenoxy)pyridine-3-carboxamide (Compound 919), N-[(6-amino-2-pyridyl)sulfonyl]-6-(2-fluoro-6-methoxyphenyl)-2-(2,4,6-trimethylphenoxy)pyridine-3-carboxamide (Compound 920), N-[(6-amino-2-pyridyl)sulfonyl]-6-(4-cyano-3-methoxyphenyl)-2-(2,4,6-trimethylphenoxy)pyridine-3-carboxamide (Compound 923), N-[(6-amino-2-pyridyl)sulfonyl]-6-(2,5-dimethylpyrazol-3-yl)-2-(2,4,6-trimethylphenoxy)pyridine-3-carboxamide (Compound 938), N-[(6-amino-2-pyridyl)sulfonyl]-6-(2-fluoro-4-methoxyphenyl)-2-(2,4,6-trimethylphenoxy)pyridine-3-carboxamide (Compound 956), N-[(6-amino-2-pyridyl)sulfonyl]-6-(1H-indol-4-yl)-2-(2,4,6-trimethylphenoxy)pyridine-3-carboxamide (Compound 977), N-[(6-amino-2-pyridyl)sulfonyl]-6-(2,5-difluoro-4-methoxy-phenyl)-2-(2,4,6-trimethylphenoxy)pyridine-3-carboxamide (Compound 984), N-[(6-amino-2-pyridyl)sulfonyl]-6-(p-tolyl)-2-(2,4,6-trimethylphenoxy)pyridine-3-carboxamide (Compound 1035), N-[(6-amino-2-pyridyl)sulfonyl]-6-(2,3-dihydrobenzofuran-5-yl)-2-(2,4,6-trimethylphenoxy)pyridine-3-carboxamide (Compound 1084), N-[(6-amino-2-pyridyl)sulfonyl]-6-(1-methylindol-6-yl)-2-(2,4,6-trimethylphenoxy)pyridine-3-carboxamide (Compound 1056), N-[(6-amino-2-pyridyl)sulfonyl]-6-(2-methylpyrazol-3-yl)-2-(2,4,6-trimethylphenoxy)pyridine-3-carboxamide (Compound 1057), N-[(6-amino-2-pyridyl)sulfonyl]-6-(o-tolyl)-2-(2,4,6-trimethylphenoxy)pyridine-3-carboxamide (Compound 1120), N-[(6-amino-2-pyridyl)sulfonyl]-6-[2-(cyclopropylamino)pyrimidin-5-yl]-2-(2,4,6-trimethylphenoxy)pyridine-3-carboxamide (Compound 1126), N-[(6-amino-2-pyridyl)sulfonyl]-6-[2-(dimethylamino)pyrimidin-5-yl]-2-(2,4,6-trimethylphenoxy)pyridine-3-carboxamide (Compound 1139), N-[(6-amino-2-pyridyl)sulfonyl]-6-(3-fluoro-4-methoxyphenyl)-2-(2,4,6-trimethylphenoxy)pyridine-3-carboxamide (Compound 1140), N-[(6-amino-2-pyridyl)sulfonyl]-6-(3,4-dimethoxyphenyl)-2-(2,4,6-trimethylphenoxy)pyridine-3-carboxamide (Compound 1146), N-[(6-amino-2-pyridyl)sulfonyl]-6-[4-(1-hydroxy-1-methyl-ethyl)phenyl]-2-(2,4,6-trimethylphenoxy)pyridine-3-carboxamide (Compound 1147), N-[(6-amino-2-pyridyl)sulfonyl]-6-(1-isobutylpyrazol-4-yl)-2-(2,4,6-trimethylphenoxy)pyridine-3-carboxamide (Compound 1177), N-[(6-amino-2-pyridyl)sulfonyl]-6-(2-fluoro-5-methoxyphenyl)-2-(2,4,6-trimethylphenoxy)pyridine-3-carboxamide (Compound 1178), N-[(6-amino-2-pyridyl)sulfonyl]-6-(6-ethoxy-3-pyridyl)-2-(2,4,6-trimethylphenoxy)pyridine-3-carboxamide (Compound 1185), N-[(6-amino-2-pyridyl)sulfonyl]-6-(4-hydroxy-2-methyl-phenyl)-2-(2,4,6-trimethylphenoxy)pyridine-3-carboxamide (Compound 1204), N-[(6-amino-2-pyridyl)sulfonyl]-6-(2,5-dimethoxyphenyl)-2-(2,4,6-trimethylphenoxy)pyridine-3-carboxamide (Compound 1225), 6-[4-(aminomethyl)phenyl]-N-[(6-amino-2-pyridyl)sulfonyl]-2-(2,4,6-trimethylphenoxy)pyridine-3-carboxamide (Compound 1228), N-[(6-amino-2-pyridyl)sulfonyl]-6-(2,3-difluorophenyl)-2-(2,4,6-trimethylphenoxy)pyridine-3-carboxamide (Compound 1244), N-[(6-amino-2-pyridyl)sulfonyl]-6-(3-hydroxy-4-methoxyphenyl)-2-(2,4,6-trimethylphenoxy)pyridine-3-carboxamide (Compound 1251), N-[(6-amino-2-pyridyl)sulfonyl]-6-(3-ethoxy-5-fluoro-phenyl)-2-(2,4,6-trimethylphenoxy)pyridine-3-carboxamide (Compound 1255), N-[(6-amino-2-pyridyl)sulfonyl]-6-(2-pyrrolidin-1-ylpyrimidin-5-yl)-2-(2,4,6-trimethylphenoxy)pyridine-3-carboxamide (Compound 1275), N-[(6-amino-2-pyridyl)sulfonyl]-6-(1-methylindazol-5-yl)-2-(2,4,6-trimethylphenoxy)pyridine-3-carboxamide (Compound 1276), N-[(6-amino-2-pyridyl)sulfonyl]-6-(2-methylindazol-6-yl)-2-(2,4,6-trimethylphenoxy)pyridine-3-carboxamide (Compound 1299), N-[(6-amino-2-pyridyl)sulfonyl]-6-(2-methoxy-5-methylphenyl)-2-(2,4,6-trimethylphenoxy)pyridine-3-carboxamide (Compound 1320), N-[(6-amino-2-pyridyl)sulfonyl]-6-(2,6-dimethoxyphenyl)-2-(2,4,6-trimethylphenoxy)pyridine-3-carboxamide (Compound 1326), N-[(6-amino-2-pyridyl)sulfonyl]-6-(1-isopentylpyrazol-4-yl)-2-(2,4,6-trimethylphenoxy)pyridine-3-carboxamide (Compound 1336), N-[(6-amino-2-pyridyl)sulfonyl]-6-(4-ethoxyphenyl)-2-(2,4,6-trimethylphenoxy)pyridine-3-carboxamide (Compound 1337), N-[(6-amino-2-pyridyl)sulfonyl]-6-(4-hydroxyphenyl)-2-(2,4,6-trimethylphenoxy)pyridine-3-carboxamide (Compound 1344), N-[(6-amino-2-pyridyl)sulfonyl]-6-[3-(hydroxymethyl)phenyl]-2-(2,4,6-trimethylphenoxy)pyridine-3-carboxamide (Compound 786), N-[(6-amino-2-pyridyl)sulfonyl]-6-(3-hydroxyphenyl)-2-(2,4,6-trimethylphenoxy)pyridine-3-carboxamide (Compound 908), N-[(6-amino-2-pyridyl)sulfonyl]-6-[4-(hydroxymethyl)phenyl]-2-(2,4,6-trimethylphenoxy)pyridine-3-carboxamide (Compound 1183), N-[(6-amino-2-pyridyl)sulfonyl]-6-(2,3-dimethoxyphenyl)-2-(2,4,6-trimethylphenoxy)pyridine-3-carboxamide (Compound 485), N-[(6-amino-2-pyridyl)sulfonyl]-6-(2,4-dimethoxypyrimidin-5-yl)-2-(2,4,6-trimethylphenoxy)pyridine-3-carboxamide (Compound 499), N-[(6-amino-2-pyridyl)sulfonyl]-6-phenyl-2-(2,4,6-trimethylphenoxy)pyridine-3-carboxamide (Compound 203), N-[(6-amino-2-pyridyl)sulfonyl]-6-(4-methoxyphenyl)-2-(2,4,6-trimethylphenoxy)pyridine-3-carboxamide (Compound 17), N-[(6-amino-2-pyridyl)sulfonyl]-6-(3-ethoxyphenyl)-2-(2,4,6-trimethylphenoxy)pyridine-3-carboxamide (Compound 61), N-[(6-amino-2-pyridyl)sulfonyl]-6-(2,6-dimethylphenyl)-2-(2,4,6-trimethylphenoxy)pyridine-3-carboxamide (Compound 97), N-[(6-amino-2-pyridyl)sulfonyl]-6-(2-ethoxyphenyl)-2-(2,4,6-trimethylphenoxy)pyridine-3-carboxamide (Compound 250), N-[(6-amino-2-pyridyl)sulfonyl]-6-(3-furyl)-2-(2,4,6-trimethylphenoxy)pyridine-3-carboxamide (Compound 284), N-[(6-amino-2-pyridyl)sulfonyl]-6-[6-(trifluoromethyl)-3-pyridyl]-2-(2,4,6-trimethylphenoxy)pyridine-3-carboxamide (Compound 132), N-[(6-amino-2-pyridyl)sulfonyl]-6-(4-cyanophenyl)-2-(2,4,6-trimethylphenoxy)pyridine-3-carboxamide (Compound 216), N-[(6-amino-2-pyridyl)sulfonyl]-6-(3,4-dihydro-2H-1,5-benzodioxepin-7-yl)-2-(2,4,6-trimethylphenoxy)pyridine-3-carboxamide (Compound 14), N-[(6-amino-2-pyridyl)sulfonyl]-6-[4-(methoxymethyl)phenyl]-2-(2,4,6-trimethylphenoxy)pyridine-3-carboxamide (Compound 66), N-[(6-amino-2-pyridyl)sulfonyl]-2-(2,4-dimethylphenoxy)-6-phenyl-pyridine-3-carboxamide (Compound 340), N-[(6-amino-2-pyridyl)sulfonyl]-6-[3-(methoxymethyl)phenyl]-2-(2,4,6-trimethylphenoxy)pyridine-3-carboxamide (Compound 69), N-[(6-amino-2-pyridyl)sulfonyl]-6-(2-isopropylpyrimidin-5-yl)-2-(2,4,6-trimethylphenoxy)pyridine-3-carboxamide (Compound 64), N-[(6-amino-2-pyridyl)sulfonyl]-6-(6-methyl-3-pyridyl)-2-(2,4,6-trimethylphenoxy)pyridine-3-carboxamide (Compound 513), N-[(6-amino-2-pyridyl)sulfonyl]-6-[3-(hydroxymethyl)phenyl]-2-(2,4,6-trimethylphenoxy)pyridine-3-carboxamide (Compound 786), N-[(6-amino-2-pyridyl)sulfonyl]-6-(3-hydroxyphenyl)-2-(2,4,6-trimethylphenoxy)pyridine-3-carboxamide (Compound 908), N-[(6-amino-2-pyridyl)sulfonyl]-6-[4-(hydroxymethyl)phenyl]-2-(2,4,6-trimethylphenoxy)pyridine-3-carboxamide (Compound 1183), N-[(6-amino-2-pyridyl)sulfonyl]-6-(5-ethoxy-2-fluoro-phenyl)-2-(2,4,6=trimethylphenoxy)pyridine-3-carboxamide (Compound 599), N-[(6-amino-2-pyridyl)sulfonyl]-6-[4-(dimethylcarbamoyl)phenyl]-2-(2,4,6-trimethylphenoxy)pyridine-3-carboxamide, N-[(6-amino-2-pyridyl)sulfonyl]-6-[3-fluoro-5-(methylcarbamoyl)phenyl]-2-(2,4,6-trimethylphenoxy)pyridine-3-carboxamide, N-[(6-amino-2-pyridyl)sulfonyl]-6-(2-methylindazol-4-yl)-2-(2,4,6-trimethylphenoxy)pyridine-3-carboxamide (Compound 451), N-[(6-amino-2-pyridyl)sulfonyl]-6-(3,5-dimethoxyphenyl)-2-(2,4,6-trimethylphenoxy)pyridine-3-carboxamide (Compound 828), N-[(6-amino-2-pyridyl)sulfonyl]-6-(2,5-dimethoxyphenyl)-2-(2,4,6-trimethylphenoxy)pyridine-3-carboxamide (Compound 1225), N-[(6-amino-2-pyridyl)sulfonyl]-6-(1-isopentylpyrazol-4-yl)-2-(2,4,6-trimethylphenoxy)pyridine-3-carboxamide (Compound 1336), N-[(6-amino-2-pyridyl)sulfonyl]-6-(1-propylpyrazol-4-yl)-2-(2,4,6-trimethylphenoxy)pyridine-3-carboxamide (Compound 469), N-[(6-amino-2-pyridyl)sulfonyl]-6-(3-fluoro-5-hydroxy-phenyl)-2-(2,4,6-trimethylphenoxy)pyridine-3-carboxamide (Compound 505), N-[(6-amino-2-pyridyl)sulfonyl]-6-(1-isobutylpyrazol-4-yl)-2-(2,4,6-trimethylphenoxy)pyridine-3-carboxamide (Compound 1177), N-[(6-amino-2-pyridyl)sulfonyl]-6-(3,4-difluorophenyl)-2-(2,4,6-trimethylphenoxy)pyridine-3-carboxamide (Compound 725), N-[(6-amino-2-pyridyl)sulfonyl]-6-[3-(2-cyanoethylcarbamoyl)phenyl]-2-(2,4,6-trimethylphenoxy)pyridine-3-carboxamide, N-[(6-amino-2-pyridyl)sulfonyl]-6-[3-fluoro-4-(isopropylcarbamoyl)phenyl]-2-(2,4,6-trimethylphenoxy)pyridine-3-carboxamide (Compound 543), N-[(6-amino-2-pyridyl)sulfonyl]-6-(3-fluoro-5-isobutoxyphenyl)-2-(1-methyl-2-tetrahydropyran-4-yl-ethoxy)pyridine-3-carboxamide (Compound 1361), N-[(6-amino-2-pyridyl)sulfonyl]-2-(1,1-dimethyl-2-phenylethoxy)-6-(3-fluoro-5-isobutoxy-phenyl)pyridine-3-carboxamide (Compound 1365), N-[(6-amino-2-pyridyl)sulfonyl]-2-(1-cyclopentylethoxy)-6-(3-fluoro-5-isobutoxy-phenyl)pyridine-3-carboxamide (Compound 1374), N-[(6-amino-2-pyridyl)sulfonyl]-2-(cyclohexylmethoxy)-6-(3-fluoro-5-isobutoxy-phenyl)pyridine-3-carboxamide (Compound 1395), N-[(6-amino-2-pyridyl)sulfonyl]-6-(3-fluoro-5-isobutoxyphenyl)-2-(2-methylcyclobutoxy)pyridine-3-carboxamide (Compound 406), N-[(6-amino-2-pyridyl)sulfonyl]-2-(2-cyclobutylethoxy)-6-(3-fluoro-5-isobutoxy-phenyl)pyridine-3-carboxamide (Compound 1418), N-[(6-amino-2-pyridyl)sulfonyl]-6-(3-fluoro-5-isobutoxyphenyl)-2-phenethyloxy-pyridine-3-carboxamide (Compound 1426), N-[(6-amino-2-pyridyl)sulfonyl]-6-(3-fluoro-5-isobutoxyphenyl)-2-[1-(3-pyridyl)ethoxy]pyridine-3-carboxamide (Compound 1434), N-[(6-amino-2-pyridyl)sulfonyl]-2-(2-cyclopentylethoxy)-6-(3-fluoro-5-isobutoxy-phenyl)pyridine-3-carboxamide (Compound 1440), N-[(6-amino-2-pyridyl)sulfonyl]-2-(cyclopropoxy)-6-(3-fluoro-5-isobutoxy-phenyl)pyridine-3-carboxamide (Compound 1446), N-[(6-amino-2-pyridyl)sulfonyl]-2-(cyclopentylmethoxy)-6-(3-fluoro-5-isobutoxy-phenyl)pyridine-3-carboxamide (Compound 1450), N-[(6-amino-2-pyridyl)sulfonyl]-2-(cyclopentoxy)-6-(3-fluoro-5-isobutoxy-phenyl)pyridine-3-carboxamide (Compound 1451), N-[(6-amino-2-pyridyl)sulfonyl]-2-(3,3-difluorocyclobutoxy)-6-(3-fluoro-5-isobutoxy-phenyl)pyridine-3-carboxamide (Compound 1458), N-[(6-amino-2-pyridyl)sulfonyl]-6-(3-fluoro-5-isobutoxyphenyl)-2-[(3S)-tetrahydrofuran-3-yl]oxy-pyridine-3-carboxamide (Compound 1464), N-[(6-amino-2-pyridyl)sulfonyl]-2-(2-cyclohexylethoxy)-6-(3-fluoro-5-isobutoxy-phenyl)pyridine-3-carboxamide (Compound 1465), N-[(6-amino-2-pyridyl)sulfonyl]-2-(cyclohexoxy)-6-(3-fluoro-5-isobutoxy-phenyl)pyridine-3-carboxamide (Compound 1477), N-[(6-amino-2-pyridyl)sulfonyl]-2-(1-benzylcyclobutoxy)-6-(3-fluoro-5-isobutoxy-phenyl)pyridine-3-carboxamide (Compound 1479), N-[(6-amino-2-pyridyl)sulfonyl]-6-(3-fluoro-5-isobutoxyphenyl)-2-(tetrahydrofuran-3-ylmethoxy)pyridine-3-carboxamide (Compound 1499), N-[(6-amino-2-pyridyl)sulfonyl]-2-(2-cyclopropylcyclobutoxy)-6-(3-fluoro-5-isobutoxy-phenyl)pyridine-3-carboxamide (Compound 1530), N-[(6-amino-2-pyridyl)sulfonyl]-2-(3-benzyloxycyclobutoxy)-6-(3-fluoro-5-isobutoxy-phenyl)pyridine-3-carboxamide (Compound 1559), N-[(6-amino-2-pyridyl)sulfonyl]-6-(3-fluoro-5-isobutoxyphenyl)-2-(tetrahydropyran-2-ylmethoxy)pyridine-3-carboxamide (Compound 1570), N-[(6-amino-2-pyridyl)sulfonyl]-2-[(2,4-dimethyl-3-pyridyl)oxy]-6-(3-fluoro-5-isobutoxy-phenyl)pyridine-3-carboxamide (Compound 1574), N-[(6-amino-2-pyridyl)sulfonyl]-6-(3-fluoro-5-isobutoxyphenyl)-2-(2-tetrahydropyran-4-ylethoxy)pyridine-3-carboxamide (Compound 1579), N-[(6-amino-2-pyridyl)sulfonyl]-2-(cyclobutoxy)-6-(3-fluoro-5-isobutoxy-phenyl)pyridine-3-carboxamide (Compound 1580), N-[(6-amino-2-pyridyl)sulfonyl]-6-(3-fluoro-5-isobutoxyphenyl)-2-[(3R)-tetrahydrofuran-3-yl]oxy-pyridine-3-carboxamide (Compound 1592), N-[(6-amino-2-pyridyl)sulfonyl]-6-(3-fluoro-5-isobutoxyphenyl)-2-(2-tetrahydrofuran-2-ylethoxy)pyridine-3-carboxamide (Compound 1604), N-[(6-amino-2-pyridyl)sulfonyl]-6-(3-fluoro-5-isobutoxyphenyl)-2-[2-(4-pyridyl)ethoxy]pyridine-3-carboxamide (compound 1605), N-[(6-amino-2-pyridyl)sulfonyl]-6-(3-fluoro-5-isobutoxyphenyl)-2-(2-methoxycyclohexoxy)pyridine-3-carboxamide (Compound 1622), N-[(6-amino-2-pyridyl)sulfonyl]-6-(3-fluoro-5-isobutoxyphenyl)-2-[2-(2-pyridyl)ethoxy]pyridine-3-carboxamide (Compound 1625), N-[(6-amino-2-pyridyl)sulfonyl]-2-(2,2-dimethylcyclopentoxy)-6-(3-fluoro-5-isobutoxy-phenyl)pyridine-3-carboxamide (Compound 1629), N-[(6-amino-2-pyridyl)sulfonyl]-2-[1-(2,2-dimethylcyclopropyl)propoxy]-6-(3-fluoro-5-isobutoxy-phenyl)pyridine-3-carboxamide (Compound 1639), N-[(6-amino-2-pyridyl)sulfonyl]-6-(3-fluoro-5-isobutoxyphenyl)-2-(1-methylcyclobutoxy)pyridine-3-carboxamide (Compound 1644), N-[(6-amino-2-pyridyl)sulfonyl]-6-(3-fluoro-5-isobutoxyphenyl)-2-[2-(3-pyridyl)ethoxy]pyridine-3-carboxamide (Compound 1654), N-[(6-amino-2-pyridyl)sulfonyl]-6-(3-fluoro-5-isobutoxyphenyl)-2-(tetrahydrofuran-2-ylmethoxy)pyridine-3-carboxamide (Compound 1661), N-[(6-amino-2-pyridyl)sulfonyl]-6-(3-fluoro-5-isobutoxyphenyl)-2-[(1-methylcyclopropyl)methoxy]pyridine-3-carboxamide (Compound 1668), N-[(6-amino-2-pyridyl)sulfonyl]-6-(3-fluoro-5-isobutoxyphenyl)-2-(2-tetrahydropyran-2-ylethoxy)pyridine-3-carboxamide (Compound 1680), N-[(6-amino-2-pyridyl)sulfonyl]-2-(2-cyclopropylethoxy)-6-(3-fluoro-5-isobutoxy-phenyl)pyridine-3-carboxamide (Compound 1685), N-[(6-amino-2-pyridyl)sulfonyl]-6-(3-isobutoxyphenyl)-2-(2,4,6-trimethylphenoxy)pyridine-3-carboxamide (Compound 8), N-[(6-amino-2-pyridyl)sulfonyl]-6-(2,6-dimethylphenyl)-2-(2,4,6-trimethylphenoxy)pyridine-3-carboxamide (Compound 97), N-[(6-amino-2-pyridyl)sulfonyl]-6-(4-ethoxy-3-fluoro-phenyl)-2-(2,4,6-trimethylphenoxy)pyridine-3-carboxamide (Compound 161), N-[(6-amino-2-pyridyl)sulfonyl]-6-(4-isopropylphenyl)-2-(2,4,6-trimethylphenoxy)pyridine-3-carboxamide (Compound 164), N-[(6-amino-2-pyridyl)sulfonyl]-6-(3-fluoro-5-isobutoxyphenyl)-2-(2,4,6-trimethylphenoxy)pyridine-3-carboxamide (Compound 196), N-[(6-amino-2-pyridyl)sulfonyl]-6-(4-chloro-2-fluoro-phenyl)-2-(2,4,6-trimethylphenoxy)pyridine-3-carboxamide (Compound 207),
N-[(6-amino-2-pyridyl)sulfonyl]-6-(4-chlorophenyl)-2-(2,4,6-trimethylphenoxy)pyridine-3-carboxamide (Compound 234),
N-[(6-amino-2-pyridyl)sulfonyl]-6-(4-chloro-3-isobutoxyphenyl)-2-(2,4,6-trimethylphenoxy)pyridine-3-carboxamide (Compound 238),
N-[(6-amino-2-pyridyl)sulfonyl]-6-(4-chloro-3-isopropoxyphenyl)-2-(2,4,6-trimethylphenoxy)pyridine-3-carboxamide (Compound 281),
N-[(6-amino-2-pyridyl)sulfonyl]-6-(4-isobutoxyphenyl)-2-(2,4,6-trimethylphenoxy)pyridine-3-carboxamide (Compound 320),
N-[(6-amino-2-pyridyl)sulfonyl]-6-(7-fluoro-1,3-benzodioxol-4-yl)-2-(2,4,6-trimethylphenoxy)pyridine-3-carboxamide (Compound 345),
N-[(6-amino-2-pyridyl)sulfonyl]-6-(2-fluoro-5-isobutoxyphenyl)-2-(2,4,6-trimethylphenoxy)pyridine-3-carboxamide (Compound 351),
N-[(6-amino-2-pyridyl)sulfonyl]-6-(4-methylcyclohexyl)-2-(2,4,6-trimethylphenoxy)pyridine-3-carboxamide (Compound 172),
6-(p-tolyl)-N-(1H-pyrazol-3-ylsulfonyl)-2-(2,4,6-trimethylphenoxy)pyridine-3-carboxamide (Compound 300),
6-(3-fluoro-5-isobutoxy-phenyl)-N-(1H-pyrazol-3-ylsulfonyl)-2-(2,4,6-trimethylphenoxy)pyridine-3-carboxamide (Compound 318), and
6-(4-ethoxyphenyl)-N-(1H-pyrazol-3-ylsulfonyl)-2-(2,4,6-trimethylphenoxy)pyridine-3-carboxamide (Compound 190).

Preparation 16: N-(3-aminophenyl)sulfonyl-5-phenyl-2-(2,4,6-trimethylphenoxy)pyridine-3-carboxamide (Compound 1321)

Step 1: methyl 5-bromo-2-(2,4,6-trimethylphenoxy)pyridine-3-carboxylate

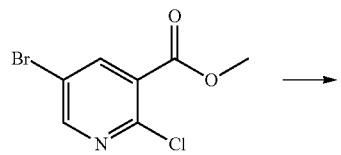

2,4,6-Trimethylphenol (2.68 g, 19.7 mmol) and 60% NaH (870 mg, 22 mmol) were combined in an anhydrous mixture of N,N-dimethylformamide (24 mL) and THF (2.4 mL). The reaction mixture was stirred at room temperature for 15 minutes under an atmosphere of nitrogen. Methyl 5-bromo-2-chloro-pyridine-3-carboxylate (4.93 g, 19.7 mmol) was added and the reaction mixture was heated at 60° C. for 1 h. The reaction mixture was then allowed to cool to room temperature. The reaction mixture was diluted with water and was extracted with ethyl acetate. The ethyl acetate layer was washed three times with water and then was concentrated under reduced pressure. The residue was subjected to silica gel column chromatography (0-50% ethyl acetate/hexanes) to yield methyl 5-bromo-2-(2,4,6-trimethylphenoxy)pyridine-3-carboxylate (5.50 g, 73%) as a faint yellow solid. ESI-MS m/z calc. 349.0, found 350.3 (M+1)+; Retention time: 2.09 min (3 min run).

Step 2: methyl 5-bromo-2-(2,4,6-trimethylphenoxy)pyridine-3-carboxylate

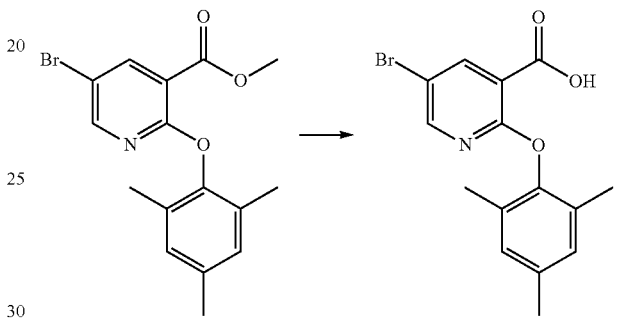

Methyl 5-bromo-2-(2,4,6-trimethylphenoxy)pyridine-3-carboxylate (2.60 g, 6.76 mmol) was combined in a mixture of methanol (12.95 mL) and water (17.27 mL) containing sodium hydroxide (810 mg, 20.3 mmol). The resulting suspension was heated at 60° C. for 3 h. The reaction mixture was cooled to room temperature and was made acidic with 6 M hydrochloric acid. The resulting precipitate was filtered, washed with water and dried in a vacuum oven at 60° C. overnight to yield 5-bromo-2-(2,4,6-trimethylphenoxy)pyridine-3-carboxylic acid (2.24 g, 98%) as a white solid. ESI-MS m/z calc. 335.0, found 338.2 (M+1)+; Retention time: 1.75 min (3 min run).

Step 3: methyl 5-bromo-2-(2,4,6-trimethylphenoxy)pyridine-3-carboxylate

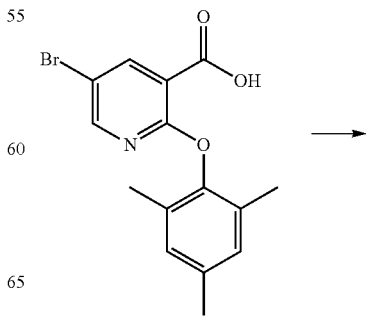

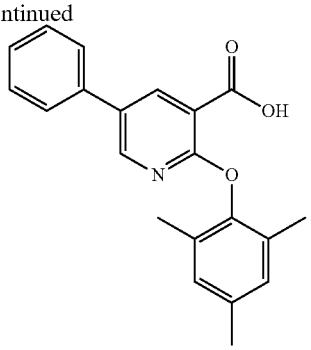

5-Bromo-2-(2,4,6-trimethylphenoxy)pyridine-3-carboxylic acid (89 mg, 0.26 mmol), phenylboronic acid (39 mg, 0.32 mmol), Pd(PPh$_3$)$_4$ (31 mg, 0.026 mmol), and K$_2$CO$_3$ (530 μL of 2.0 M, 1.1 mmol) were combined in DME (2.5 mL). The reaction mixture was briefly sparged with nitrogen, capped, and heated at 80° C. for 2 h. The reaction mixture was allowed to cool to room temperature and the layers were separated. The organic layer was subjected to preparatory-HPLC (1-99% acetonitrile/water with 5 μM HCl) to give 5-phenyl-2-(2,4,6-trimethylphenoxy)pyridine-3-carboxylic acid (54 mg, 61%) as a white solid. ESI-MS m/z calc. 333.1, found 334.4 (M+1)$^+$; Retention time: 0.72 min (1 min run).

Step 4: N-(3-nitrophenyl)sulfonyl-5-phenyl-2-(2,4,6-trimethylphenoxy)-pyridine-3-carboxamide

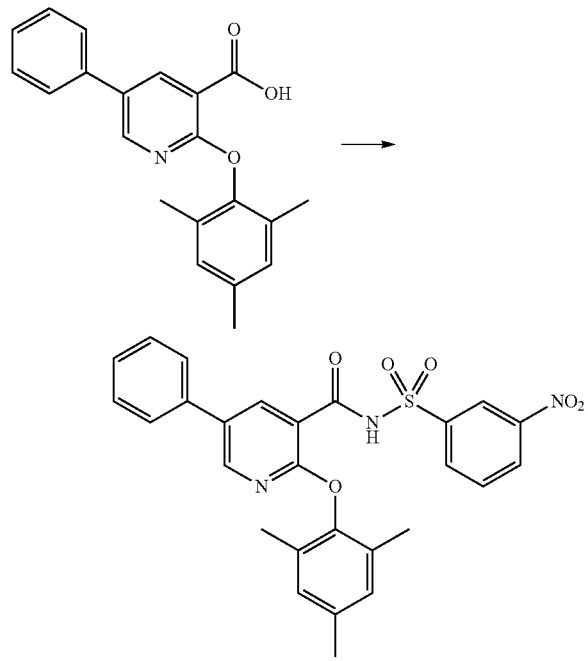

5-Phenyl-2-(2,4,6-trimethylphenoxy)pyridine-3-carboxylic acid (54 mg, 0.16 mmol), (3-nitrophenyl)sulfonylazanide sodium (73 mg, 0.32 mmol), N-[(dimethylamino)-1H-1,2,3-triazolo-[4,5-b]pyridin-1-ylmethylene]-N-methylmethanaminium hexafluorophosphate N-oxide (62 mg, 0.16 mmol) and N,N-dimethylformamide (1 mL) were combined. The reaction mixture was stirred at room temperature for 72 h. The crude mixture was subjected to preparatory-HPLC (1-99% acetonitrile/water with 5 μM HCl) to give N-(3-nitrophenyl)sulfonyl-5-phenyl-2-(2,4,6-trimethylphenoxy)pyridine-3-carboxamide (51 mg, 61%) as a white solid. ESI-MS m/z calc. 517.1, found 518.5 (M+1)$^+$; Retention time: 2.04 min (3 min run).

Step 5: N-(3-aminophenyl)sulfonyl-5-phenyl-2-(2,4,6-trimethylphenoxy)-pyridine-3-carboxamide

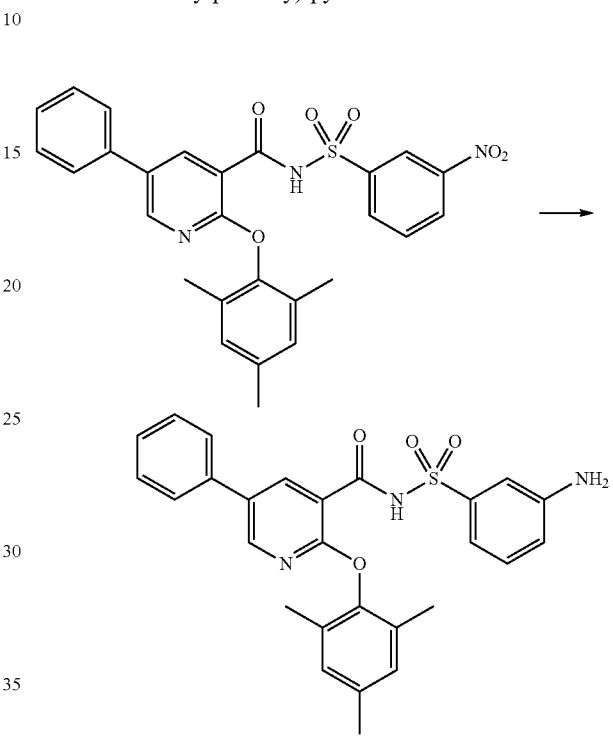

N-(3-nitrophenyl)sulfonyl-5-phenyl-2-(2,4,6-trimethylphenoxy)pyridine-3-carboxamide (51 mg, 0.099 mmol) was suspended in acetic acid (2 mL) containing zinc (10 mg, 0.15 mmol). The reaction mixture was heated at 65° C. for 30 min. The hot reaction mixture was filtered and then allowed to cool to room temperature. The mixture was concentrated and the residue was subjected to preparatory-HPLC (1-99% acetonitrile/water with 5 mM HCl) to give N-(3-aminophenyl)sulfonyl-5-phenyl-2-(2,4,6-trimethylphenoxy)pyridine-3-carboxamide (Compound 1321) (18 mg, 38%) as a white solid. ESI-MS m/z calc. 487.2, found 488.5 (M+1)$^+$; Retention time: 2.74 min (3 min run).

The following compound can be synthesized using the procedures described herein:
N-[(6-amino-2-pyridyl)sulfonyl]-5-(2-propylphenyl)-2-(2,4,6-trimethylphenoxy)pyridine-3-carboxamide (Compound 429),
N-[(6-amino-2-pyridyl)sulfonyl]-5-(2-isopropylphenyl)-2-(2,4,6-trimethylphenoxy)pyridine-3-carboxamide (Compound 865),
N-[(6-amino-2-pyridyl)sulfonyl]-5-(2-tert-butylphenyl)-2-(2,4,6-trimethylphenoxy)pyridine-3-carboxamide (Compound 868),
N-(3-aminophenyl)sulfonyl-6-tert-butyl-4-methoxy-2-(2,4,6-trimethylphenoxy)pyridine-3-carboxamide (Compound 959),
N-[(6-amino-2-pyridyl)sulfonyl]-5-(o-tolyl)-2-(2,4,6-trimethylphenoxy)pyridine-3-carboxamide (Compound 817), and N-[(6-amino-2-pyridyl)sulfonyl]-5-(2-ethylphenyl)-2-(2,4,6-trimethylphenoxy)pyridine-3-carboxamide (Compound 945).

Preparation 17: N-(3-aminophenyl)sulfonyl-6-tert-butyl-2-(N,2-dimethylanilino)pyridine-3-carboxamide (Compound 193)

Step 1: 6-tert-butyl-2-(N,2-dimethylanilino)pyridine-3-carbonitrile

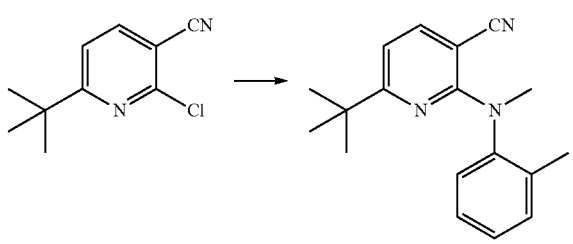 [SMILES: CC(C)(C)c1ccc(C#N)c(Cl)n1 ; Cc1ccccc1N(C)c1nc(C(C)(C)C)ccc1C#N]

A mixture of 6-tert-butyl-2-chloro-pyridine-3-carbonitrile (100. mg, 0.514 mmol), N,2-dimethylaniline (76 μL, 0.62 mmol), KHMDS (1.2 mL of 0.5 M, 0.62 mmol) and dioxane (1.5 mL) was heated at 100° C. for 20 min. The mixture was partitioned between ethyl acetate and 1N HCl. The layers were separated and the aqueous layer was extracted with ethyl acetate (3×). The combined organics were washed with brine, dried over magnesium sulfate, filtered and concentrated. The residue was subjected to silica gel column chromatography (0-25% ethyl acetate/hexanes) to give 6-tert-butyl-2-(N,2-dimethylanilino)pyridine-3-carbonitrile (40 mg, 26%). ESI-MS m/z calc. 279.2, found 280.4 (M+1)$^+$; Retention time: 2.28 min (3 min run).

Step 2: 6-tert-butyl-2-(N,2-dimethylanilino)pyridine-3-carboxamide

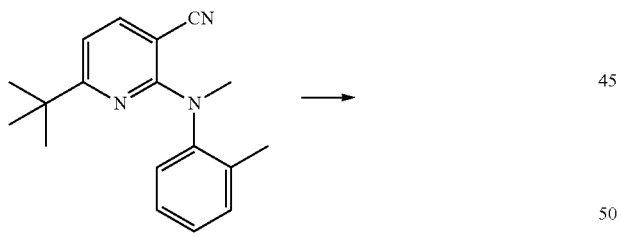

A mixture of 6-tert-butyl-2-(N,2-dimethylanilino)pyridine-3-carbonitrile (40 mg, 0.14 mmol) and KOH (340 μL of 4.0 M, 1.4 mmol) in EtOH (1.2 mL) was heated at 90° C. overnight. The mixture was concentrated, acidified with 2N HCl and the solids were collected to give an off-white solid. The solids were placed in a vacuum oven at 55° C. overnight to give 6-tert-butyl-2-(N,2-dimethylanilino)pyridine-3-carboxamide (40 mg, 30%) as an off-white solid. ESI-MS m/z calc. 297.2, found 298.4 (M+1)$^+$; Retention time: 0.68 min (1 min run).

Step 3: 6-tert-butyl-2-(N,2-dimethylanilino)-N-(3-nitrophenyl)sulfonyl-pyridine-3-carboxamide

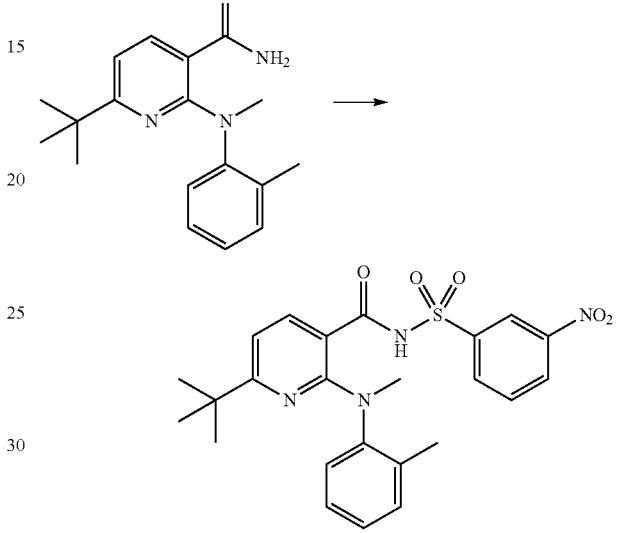

Sodium hydride (16 mg, 60%, 0.40 mmol) was added to a mixture of 6-tert-butyl-2-(N,2-dimethylanilino)pyridine-3-carboxamide (40. mg, 0.13 mmol) and N,N-dimethylformamide (1 mL). The mixture was allowed to stir for 15 min before 3-nitrobenzenesulfonyl chloride (45 mg, 0.20 mmol) was added. The mixture was allowed to stir for 1H before adding two drops of methsanol. The mixture was filtered and subjected to preparatory-HPLC (10-99% acetonitrile/water with 0.05 mM HCl) to give 6-tert-butyl-2-(N,2-dimethylanilino)-N-(3-nitrophenyl)sulfonyl-pyridine-3-carboxamide. ESI-MS m/z calc. 482.2, found 483.3 (M+1)$^+$; Retention time: 0.82 min (1 min run).

Step 4: N-(3-aminophenyl)sulfonyl-6-tert-butyl-2-(N,2-dimethylanilino)pyridine-3-carboxamide (Compound 193)

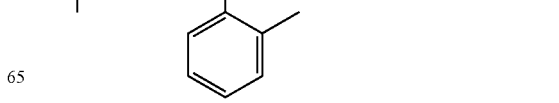

-continued

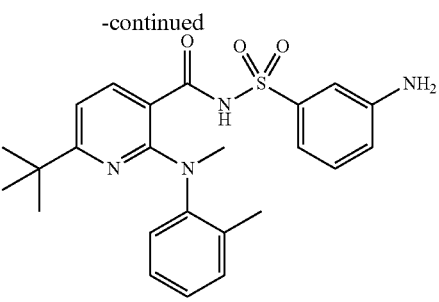

Zinc (9.0 mg, 0.13 mmol) was added to a mixture of 6-tert-butyl-2-(N,2-dimethylanilino)-N-(3-nitrophenyl)sulfonyl-pyridine-3-carboxamide and acetic acid (1 mL) at room temperature. The mixture was allowed to stir for 20 min before it was filtered and subjected to preparatory-HPLC (10-99% acetonitrile/water with 0.05 mMHCl) to give N-(3-aminophenyl)sulfonyl-6-tert-butyl-2-(N,2-dimethylanilino)pyridine-3-carboxamide (Compound 193) (1.2 mg, 2% for 2 steps). ESI-MS m/z calc. 452.2, found 453.3 (M+1)$^+$; Retention time: 1.90 minutes (3 min run).

The following compound can be synthesized using the procedures described herein: N-(3-aminophenyl)sulfonyl-6-tert-butyl-2-(N-methylanilino)pyridine-3-carboxamide (Compound 85).

Preparation 18: N-(3-aminophenyl)sulfonyl-5-tert-butyl-2-[(2,4,6-trimethylphenyl)methyl]pyrazole-3-carboxamide (Compound 110)

Step 1: ethyl 5-tert-butyl-2-[(2,4,6-trimethylphenyl)methyl]pyrazole-3-carboxylate

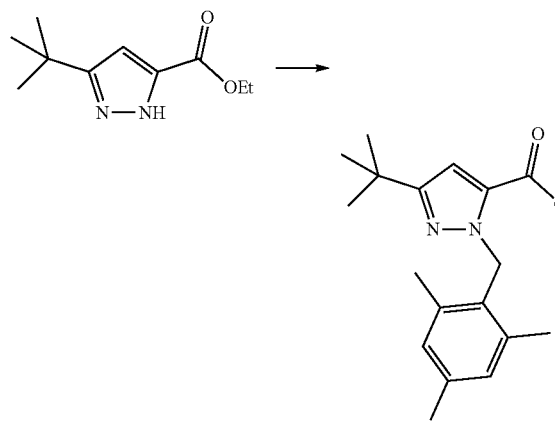

To a mixture of ethyl 5-tert-butyl-4H-pyrazole-3-carboxylate (500. mg, 2.55 mmol) and N,N-dimethylformamide (5 mL) was added 2-(bromomethyl)-1,3,5-trimethyl-benzene (543 mg, 2.55 mmol) and K$_2$CO$_3$ (704 mg, 5.10 mmol). The reaction mixture was heated at 80° C. overnight. Additional 2-(bromomethyl)-1,3,5-trimethyl-benzene (200 mg, 1.02 mmol) and K$_2$CO$_3$ (704 mg, 5.10 mmol) were added and the mixture was heated at 80° C. for another 18 h. The mixture was cooled to room temperature before water (20 mL) was added. The mixture was extracted with ethyl acetate (2×50 mL). The combined organic layers were dried over sodium sulfate, filtered and concentrated. The residue was subjected to silica gel column chromatography (0-50% ethyl acetate/hexanes) to give ethyl 5-tert-butyl-2-[(2,4,6-trimethylphenyl)methyl]pyrazole-3-carboxylate (642 mg, 77%). ESI-MS m/z calc. 328.2, found 329.4 (M+1)$^+$; Retention time: 0.99 min (1 min run).

Step 2: 5-tert-butyl-2-[(2,4,6-trimethylphenyl)methyl]pyrazole-3-carboxylic acid

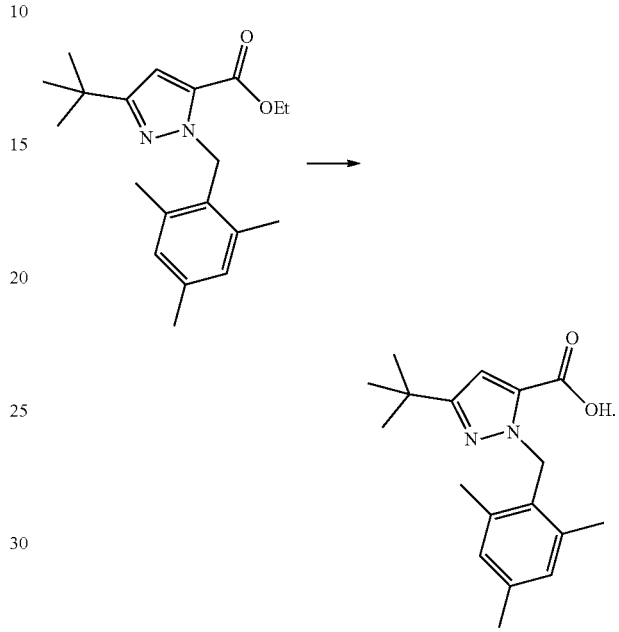

Ethyl 5-tert-butyl-2-[(2,4,6-trimethylphenyl)methyl]pyrazole-3-carboxylate (5.00 g, 15.2 mmol) and NaOH (4.87 g, 122 mmol) were combined in a THF (20 mL) and water (20 mL). The mixture was heated at 60° C. for 3 h. The reaction mixture was made acidic by the addition of 6 M HCl and was extracted with ethyl acetate. The organics were washed with brine, dried over sodium sulfate and evaporated to give 5-tert-butyl-2-[(2,4,6-trimethylphenyl)-methyl]pyrazole-3-carboxylic acid (4.38 g, 96%). $^1$H NMR (400 MHz, DMSO) δ 13.23 (s, 1H), 6.83 (s, 2H), 6.68 (s, 1H), 5.64 (s, 2H), 2.24 (s, 6H), 2.21 (s, 3H), 1.15 (s, 9H). ESI-MS m/z calc. 300.2, found 301.4 (M+1)$^+$; Retention time: 2.21 min (3 min run).

Step 3: 5-tert-butyl-N-(3-nitrophenyl)sulfonyl-2-[(2,4,6-trimethylphenyl) methyl]pyrazole-3-carboxamide

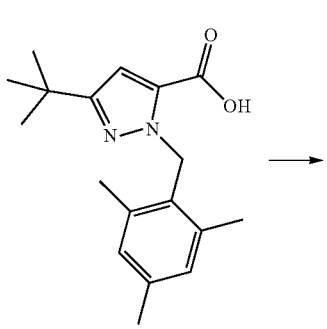

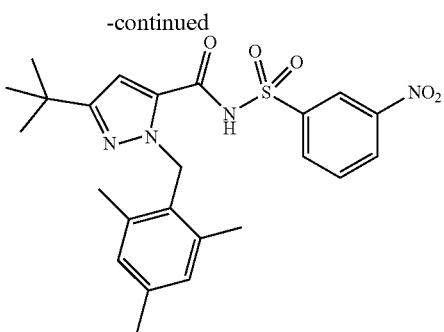

5-tert-Butyl-2-[(2,4,6-trimethylphenyl)methyl]pyrazole-3-carboxylic acid (108 mg, 0.356 mmol), 3-nitrobenzenesulfonamide (109 mg, 0.539 mmol), N-[(dimethylamino)-1H-1,2,3-triazolo-[4,5-b]pyridin-1-ylmethylene]-N-methylmethanaminium hexafluorophosphate N-oxide (137 mg, 0.356 mmol), and triethylamine (100 µL, 0.719 mmol) were combined in N,N-dimethylformamide (2.3 mL) and heated at 60° C. for 16 h. The reaction mixture was filtered and subjected to preparatory-HPLC (10-99% acetonitrile/water with 0.05 mMHCl) to give 5-tert-butyl-N-(3-nitrophenyl)sulfonyl-2-[(2,4,6-trimethylphenyl)-methyl]pyrazole-3-carboxamide (105 mg, 60.9%). ESI-MS m/z calc. 484.2, found 485.3 (M+1)⁺; Retention time: 2.27 min (3 min run).

4: N-(3-aminophenyl)sulfonyl-5-tert-butyl-2-[(2,4,6-trimethylphenyl)methyl]-pyrazole-3-carboxamide

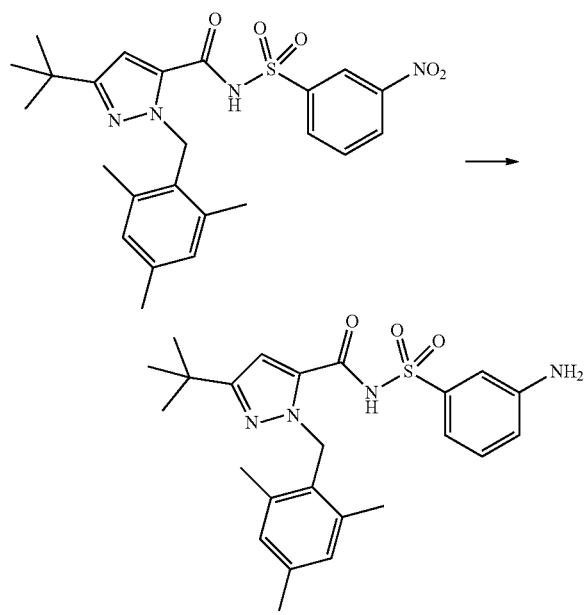

5-tert-Butyl-N-(3-nitrophenyl)sulfonyl-2-[(2,4,6-trimethylphenyl)methyl]-pyrazole-3-carboxamide (105 mg, 0.217 mmol) was dissolved in methanol (9 mL) with Pd/C (38 mg, 0.036 mmol) under a balloon of hydrogen and the mixture was stirred for 30 min. The reaction mixture was filtered, evaporated, and the residue was purified by LC/MS utilizing a gradient of 10-99% acetonitrile in 5 mM aqueous HCl to yield N-(3-aminophenyl)sulfonyl-5-tert-butyl-2-[(2,4,6-trimethylphenyl)methyl]pyrazole-3-carboxamide (Compound 110) (72 mg, 44%). ¹H NMR (400 MHz, DMSO) δ 7.26 (t, J=7.9 Hz, 1H), 7.21 (t, J=2.0 Hz, 1H), 7.12-7.06 (m, 1H), 7.01 (s, 1H), 6.89-6.83 (m, 1H), 6.77 (s, 2H), 5.45 (s, 2H), 2.17 (s, 3H), 2.11 (s, 6H), 1.14 (s, 9H). ESI-MS m/z calc. 454.2, found 455.4 (M+1)⁺; Retention time: 2.06 min (3 min run).

The following compounds can be synthesized using the procedures described herein:
3-(tert-butyl)-1-(1-mesitylethyl)-N-(phenylsulfonyl)-1H-pyrazole-5-carboxamide (Compound 201),
N-(3-aminophenyl)sulfonyl-3-tert-butyl-1-[(2,4,6-trimethylphenyl)methyl]pyrazole-4-carboxamide,
3-(tert-butyl)-1-(2-fluoro-5-(trifluoromethyl)benzyl)-N-(phenylsulfonyl)-1H-pyrazole-5-carboxamide (Compound 35),
3-(tert-butyl)-N-((3-(dimethylamino)phenyl)sulfonyl)-1-(2,4,6-trimethylbenzyl)-1H-pyrazole-5-carboxamide (Compound 270),
N-((3-aminophenyl)sulfonyl)-3-(tert-butyl)-1-(2,4,6-trichlorobenzyl)-1H-pyrazole-5-carboxamide (Compound 303),
3-(tert-butyl)-1-(2,6-dimethylbenzyl)-N-((1-methyl-1H-indol-4-yl)sulfonyl)-1H-pyrazole-5-carboxamide (Compound 210),
N-((3-aminophenyl)sulfonyl)-3-(tert-butyl)-1-(4-(tert-butyl)-2,6-dimethylbenzyl)-1H-pyrazole-5-carboxamide (Compound 156),
3-(4-(difluoromethyl)phenyl)-1-(2,6-dimethylbenzyl)-N-(phenylsulfonyl)-1H-pyrazole-5-carboxamide (Compound 119),
N-(3-aminophenyl)sulfonyl-5-tert-butyl-4-methoxy-2-[(2,4,6-trimethylphenyl)methyl]pyrazole-3-carboxamide (Compound 1305),
N-((3-aminophenyl)sulfonyl)-3-(tert-butyl)-1-(2-chloro-6-(trifluoromethyl)benzyl)-1H-pyrazole-5-carboxamide (Compound 189),
3-(tert-butyl)-N-((3-(dimethylamino)-2-methylphenyl)sulfonyl)-1-(2,4,6-trimethylbenzyl)-1H-pyrazole-5-carboxamide (Compound 104),
N-((3-amino-2-methylphenyl)sulfonyl)-3-(tert-butyl)-1-(2,4,6-trimethylbenzyl)-1H-pyrazole-5-carboxamide (Compound 123),
3-(tert-butyl)-N-((1-methyl-1H-indol-7-yl)sulfonyl)-1-(2-methyl-3-(trifluoromethyl)benzyl)-1H-pyrazole-5-carboxamide (Compound 276),
3-(tert-butyl)-N-(m-tolylsulfonyl)-1-(2,4,6-trimethylbenzyl)-1H-pyrazole-5-carboxamide (Compound 80),
N-((3-amino-4-fluorophenyl)sulfonyl)-3-(tert-butyl)-1-(2,6-dimethylbenzyl)-1H-pyrazole-5-carboxamide (Compound 150),
3-(tert-butyl)-N-(quinolin-5-ylsulfonyl)-1-(2,4,6-trimethylbenzyl)-1H-pyrazole-5-carboxamide (Compound 352),
N-((3-aminophenyl)sulfonyl)-3-(tert-butyl)-1-(2,3,5,6-tetramethylbenzyl)-1H-pyrazole-5-carboxamide (Compound 317),
3-(tert-butyl)-1-(2,6-dimethylbenzyl)-N-(thiophen-2-ylsulfonyl)-1H-pyrazole-5-carboxamide (Compound 77),
3-(tert-butyl)-N-(phenylsulfonyl)-1-(2,4,6-trichlorobenzyl)-1H-pyrazole-5-carboxamide (Compound 145),
3-(tert-butyl)-1-(2,6-dimethylbenzyl)-N-((2-methoxy-3-methylphenyl)sulfonyl)-1H-pyrazole-5-carboxamide (Compound 59),
N-(3-aminophenyl)sulfonyl-5-tert-butyl-2-[2-(2,4,6-trimethylphenyl)ethyl]pyrazole-3-carboxamide (Compound 7),
3-(tert-butyl)-N-(phenylsulfonyl)-1-(2,4,6-trimethylbenzyl)-1H-pyrazole-5-carboxamide, 3-(tert-butyl)-1-(naphthalen-1-ylmethyl)-N-(phenylsulfonyl)-1H-pyrazole-5-carboxamide (Compound 328),
3-(tert-butyl)-N-((3-(methylamino)phenyl)sulfonyl)-1-(2,4,6-trimethylbenzyl)-1H-pyrazole-5-carboxamide (Compound 249),
3-(tert-butyl)-N-((1-(2-hydroxyethyl)-1H-indol-4-yl)sulfonyl)-1-(2,4,6-trimethylbenzyl)-1H-pyrazole-5-carboxamide (Compound 188),
N-((3-aminophenyl)sulfonyl)-3-(tert-butyl)-4-methyl-1-(2,4,6-trimethylbenzyl)-1H-pyrazole-5-carboxamide (Compound 20),
3-(tert-butyl)-1-(2,6-dimethylbenzyl)-N-((2-fluorophenyl)sulfonyl)-1H-pyrazole-5-carboxamide (Compound 57),
3-(tert-butyl)-N-((2-cyanophenyl)sulfonyl)-1-(2,4,6-trimethylbenzyl)-1H-pyrazole-5-carboxamide (Compound 266),
3-(tert-butyl)-N-((3-hydroxyphenyl)sulfonyl)-1-(2,4,6-trimethylbenzyl)-1H-pyrazole-5-carboxamide (Compound 84),
3-(tert-butyl)-1-(2,6-dimethylbenzyl)-N-(phenylsulfonyl)-1H-pyrazole-5-carboxamide (Compound 257),
N-((3-amino-4-methylphenyl)sulfonyl)-3-(tert-butyl)-1-(2,6-dimethylbenzyl)-1H-pyrazole-5-carboxamide (Compound 312),
1-(3-(1H-pyrrol-1-yl)benzyl)-3-(tert-butyl)-N-(phenylsulfonyl)-1H-pyrazole-5-carboxamide (Compound 108),
3-(tert-butyl)-1-(5-fluoro-2-(trifluoromethyl)benzyl)-N-(phenylsulfonyl)-1H-pyrazole-5-carboxamide (Compound 3),
N-((3-acetylphenyl)sulfonyl)-3-(tert-butyl)-1-(2,4,6-trimethylbenzyl)-1H-pyrazole-5-carboxamide (Compound 332),
N-((1H-indol-4-yl)sulfonyl)-3-(tert-butyl)-1-(2-methyl-3-(trifluoromethyl)benzyl)-1H-pyrazole-5-carboxamide (Compound 60),
3-(tert-butyl)-N-((2,6-difluorophenyl)sulfonyl)-1-(2,6-dimethylbenzyl)-1H-pyrazole-5-carboxamide (Compound 170),
N-((4-aminophenyl)sulfonyl)-3-(tert-butyl)-1-(2,6-dimethylbenzyl)-1H-pyrazole-5-carboxamide (Compound 81),
N-((3-aminophenyl)sulfonyl)-3-(tert-butyl)-1-(2-fluoro-6-(trifluoromethyl)benzyl)-1H-pyrazole-5-carboxamide (Compound 239),
N-((3-aminophenyl)sulfonyl)-3-(tert-butyl)-1-(1-(o-tolyl)ethyl)-1H-pyrazole-5-carboxamide (Compound 342),
N-((6-aminopyridin-2-yl)sulfonyl)-3-(tert-butyl)-4-methyl-1-(2,4,6-trimethylbenzyl)-1H-pyrazole-5-carboxamide (Compound 356),
N-((2-aminophenyl)sulfonyl)-3-(tert-butyl)-1-(2,6-dimethylbenzyl)-1H-pyrazole-5-carboxamide,
N-((3-aminophenyl)sulfonyl)-3-(tert-butyl)-1-(1-cyclohexylethyl)-1H-pyrazole-5-carboxamide (Compound 287),
N-((3-aminophenyl)sulfonyl)-3-(tert-butyl)-1-(1-phenylpropyl)-1H-pyrazole-5-carboxamide (Compound 165),
3-(tert-butyl)-N-((4-hydroxyphenyl)sulfonyl)-1-(2,4,6-trimethylbenzyl)-1H-pyrazole-5-carboxamide (Compound 269),
N-((3-aminophenyl)sulfonyl)-3-(1-methylcyclopropyl)-1-(2,4,6-trimethylbenzyl)-1H-pyrazole-5-carboxamide (Compound 158),
3-(tert-butyl)-1-(2-methyl-3-(trifluoromethyl)benzyl)-N-(phenylsulfonyl)-1H-pyrazole-5-carboxamide (Compound 98),
N-((3-aminophenyl)sulfonyl)-3-(tert-butyl)-1-(2,6-dimethylbenzyl)-1H-pyrazole-5-carboxamide (Compound 185),
N-((3-aminophenyl)sulfonyl)-3-isobutyl-1-(2,4,6-trimethylbenzyl)-1H-pyrazole-5-carboxamide (Compound 167),
3-(tert-butyl)-N-((2,3-dihydrobenzofuran-7-yl)sulfonyl)-1-(2,6-dimethylbenzyl)-1H-pyrazole-5-carboxamide (Compound 211),
N-((6-aminopyridin-2-yl)sulfonyl)-3-(tert-butyl)-1-(2,4,6-trimethylbenzyl)-1H-pyrazole-5-carboxamide (Compound 173),
3-(tert-butyl)-1-(2-methoxyphenethyl)-N-(phenylsulfonyl)-1H-pyrazole-5-carboxamide (Compound 157),
N-((1H-indazol-4-yl)sulfonyl)-3-(tert-butyl)-1-(2,6-dimethylbenzyl)-1H-pyrazole-5-carboxamide (Compound 86),
N-(benzenesulfonyl)-5-tert-butyl-2-[(1-methylindol-4-yl)methyl]pyrazole-3-carboxamide (Compound 245),
3-(tert-butyl)-N-((3-methoxypyridin-2-yl)sulfonyl)-1-(2,4,6-trimethylbenzyl)-1H-pyrazole-5-carboxamide (Compound 44),
N-((3-aminophenyl)sulfonyl)-3-(tert-butyl)-1-(naphthalen-1-ylmethyl)-1H-pyrazole-5-carboxamide (Compound 295),
N-((3-aminophenyl)sulfonyl)-3-(tert-butyl)-1-((1-methyl-1H-indol-7-yl)methyl)-1H-pyrazole-5-carboxamide,
3-(tert-butyl)-1-(2,6-dimethylbenzyl)-N-((2-(methylamino)pyridin-4-yl)sulfonyl)-1H-pyrazole-5-carboxamide,
5-tert-butyl-2-[(2,6-dimethylphenyl)methyl]-N-(2-methoxyphenyl)sulfonyl-pyrazole-3-carboxamide (Compound 1551),
1-((1H-indol-7-yl)methyl)-N-((3-aminophenyl)sulfonyl)-3-(tert-butyl)-1H-pyrazole-5-carboxamide,
N-[(2-amino-3-pyridyl)sulfonyl]-5-tert-butyl-2-[(2,4,6-trimethylphenyl)methyl]pyrazole-3-carboxamide (Compound 1106),
N-((3-aminophenyl)sulfonyl)-3-(tert-butyl)-1-((1-methylcyclohexyl)methyl)-1H-pyrazole-5-carboxamide,
N-(4-aminophenyl)sulfonyl-5-tert-butyl-2-[(2,4,6-trimethylphenyl)methyl]pyrazole-3-carboxamide (Compound 1653),
3-(tert-butyl)-1-(4-(tert-butyl)-2,6-dimethylbenzyl)-N-(phenylsulfonyl)-1H-pyrazole-5-carboxamide,
3-(tert-butyl)-N-((3-ethylphenyl)sulfonyl)-1-(2,4,6-trimethylbenzyl)-1H-pyrazole-5-carboxamide,
3-(tert-butyl)-N-((3-chlorophenyl)sulfonyl)-1-(2,4,6-trimethylbenzyl)-1H-pyrazole-5-carboxamide,
N-(3-aminophenyl)sulfonyl-5-tert-butyl-2-(1-phenylethyl)pyrazole-3-carboxamide (Compound 799),
N-((3-aminophenyl)sulfonyl)-3-isopropyl-1-(2,4,6-trimethylbenzyl)-1H-pyrazole-5-carboxamide,
5-tert-butyl-2-[(2,6-dimethylphenyl)methyl]-N-[3-(2-methylpyrimidin-4-yl)phenyl]sulfonyl-pyrazole-3-carboxamide (Compound 1496),
N-((3-aminophenyl)sulfonyl)-3-(tert-butyl)-1-(2,4-dichlorobenzyl)-1H-pyrazole-5-carboxamide,
3-(tert-butyl)-N-((3-fluorophenyl)sulfonyl)-1-(2,4,6-trimethylbenzyl)-1H-pyrazole-5-carboxamide,
3-(tert-butyl)-N-((2-methoxyphenyl)sulfonyl)-1-(2,4,6-trimethylbenzyl)-1H-pyrazole-5-carboxamide,
3-(tert-butyl)-N-((3-cyanophenyl)sulfonyl)-1-(2,4,6-trimethylbenzyl)-1H-pyrazole-5-carboxamide,
N-((4-aminophenyl)sulfonyl)-3-(tert-butyl)-1-(2,4,6-trimethylbenzyl)-1H-pyrazole-5-carboxamide,
N-((2-aminophenyl)sulfonyl)-3-(tert-butyl)-1-(2,4,6-trimethylbenzyl)-1H-pyrazole-5-carboxamide,
3-(tert-butyl)-N-(pyridin-4-ylsulfonyl)-1-(2,4,6-trimethylbenzyl)-1H-pyrazole-5-carboxamide,
3-(tert-butyl)-N-((3-methoxyphenyl)sulfonyl)-1-(2,4,6-trimethylbenzyl)-1H-pyrazole-5-carboxamide, N-((3-aminophenyl)sulfonyl)-3-(tert-butyl)-1-(2,4-dimethylbenzyl)-1H-pyrazole-5-carboxamide, 5-tert-butyl-N-(1H-indol-4-ylsulfonyl)-2-[(2,4,6-trimethylphenyl)methyl]pyrazole-3-carboxamide (Compound 180), 3-(tert-butyl)-1-(5-methyl-2-(trifluoromethyl)benzyl)-N-(phenylsulfonyl)-1H-pyrazole-5-carboxamide (Compound 304), N-((3-aminophenyl)sulfonyl)-1-(2,4,6-trimethylbenzyl)-1H-benzo[d]imidazole-2-carboxamide (Compound 71), N-(3-aminophenyl)sulfonyl-5-tert-butyl-2-[(1-methylindol-4-yl)methyl]pyrazole-3-carboxamide (Compound 927), 5-tert-butyl-N-[(2-methoxy-3-pyridyl)sulfonyl]-2-[(2,4,6-trimethylphenyl)methyl]pyrazole-3-carboxamide (Compound 759), 5-tert-butyl-2-[(2,6-dimethylphenyl)methyl]-N-(3-thienylsulfonyl)pyrazole-3-carboxamide (Compound 603), N-(2-aminophenyl)sulfonyl-5-tert-butyl-2-[(2,6-dimethylphenyl)methyl]pyrazole-3-carboxamide (Compound 88), 5-tert-butyl-2-[(2,6-dimethylphenyl)methyl]-N-(1H-indol-7-ylsulfonyl)pyrazole-3-carboxamide (Compound 1358), N-(3-aminophenyl)sulfonyl-5-tert-butyl-2-(1H-indol-7-yl-methyl)pyrazole-3-carboxamide (Compound 1256), N-(3-aminophenyl)sulfonyl-5-tert-butyl-2-[(1-methylindol-7-yl)methyl]pyrazole-3-carboxamide (Compound 755), 5-tert-butyl-2-[(2,6-dimethylphenyl)methyl]-N-[[2-(methylamino)-4-pyridyl]sulfonyl]pyrazole-3-carboxamide (Compound 821), N-(3-aminophenyl)sulfonyl-5-tert-butyl-2-[(1-methylcyclohexyl)methyl]pyrazole-3-carboxamide (Compound 1152), N-(benzenesulfonyl)-5-tert-butyl-2-[(4-tert-butyl-2,6-dimethyl-phenyl)methyl]pyrazole-3-carboxamide (Compound 443), N-(3-aminophenyl)sulfonyl-5-tert-butyl-2-[(1R)-1-phenylethyl]pyrazole-3-carboxamide (Compound 540), N-[(2-amino-3-pyridyl)sulfonyl]-5-tert-butyl-2-[(2,4,6-trimethylphenyl)methyl]pyrazole-3-carboxamide, 5-tert-butyl-2-[(2,6-dimethylphenyl)methyl]-N-(3-thienylsulfonyl)pyrazole-3-carboxamide (Compound 603), 5-tert-butyl-N-[(2-methoxy-3-pyridyl)sulfonyl]-2-[(2,4,6-trimethylphenyl)methyl]pyrazole-3-carboxamide (Compound 759), 5-tert-butyl-2-[(2,6-dimethylphenyl)methyl]-N-(2-furylsulfonyl)pyrazole-3-carboxamide (Compound 1468), N-[4-(aminomethyl)phenyl]sulfonyl-5-tert-butyl-2-[(2,4,6-trimethylphenyl)methyl]pyrazole-3-carboxamide (Compound 1670), 5-tert-butyl-N-(4-pyridylsulfonyl)-2-[(2,4,6-trimethylphenyl)methyl]pyrazole-3-carboxamide (Compound 1585), N-(3-aminophenyl)sulfonyl-5-tert-butyl-2-[(2,4-dichlorophenyl)methyl]pyrazole-3-carboxamide (Compound 797), 5-tert-butyl-N-(3-ethylphenyl)sulfonyl-2-[(2,4,6-trimethylphenyl)methyl]pyrazole-3-carboxamide (Compound 823), N-(3-aminophenyl)sulfonyl-5-tert-butyl-2-(1-phenylethyl)pyrazole-3-carboxamide, 5-tert-butyl-N-(3-chlorophenyl)sulfonyl-2-[(2,4,6-trimethylphenyl)methyl]pyrazole-3-carboxamide (Compound 472), N-(2-aminophenyl)sulfonyl-5-tert-butyl-2-[(2,4,6-trimethylphenyl)methyl]pyrazole-3-carboxamide (Compound 1167), N-(3-aminophenyl)sulfonyl-5-isopropyl-2-[(2,4,6-trimethylphenyl)methyl]pyrazole-3-carboxamide (Compound 566), N-(1H-pyrazol-3-ylsulfonyl)-3-[(2,4,6-trimethylphenyl)methyl]-1,2,4,5-tetrahydro-3-benzazepine-4-carboxamide (Compound 628), N-[(2-oxo-1H-pyridin-3-yl)sulfonyl]-3-[(2,4,6-trimethylphenyl)methyl]-1,2,4,5-tetrahydro-3-benzazepine-4-carboxamide (Compound 662), N-[(6-morpholino-2-pyridyl)sulfonyl]-3-[(2,4,6-trimethylphenyl)methyl]-1,2,4,5-tetrahydro-3-benzazepine-4-carboxamide (Compound 669), N-[[6-(methylamino)-2-pyridyl]sulfonyl]-3-[(2,4,6-trimethylphenyl)methyl]-1,2,4,5-tetrahydro-3-benzazepine-4-carboxamide (Compound 747), N-[[6-(2-hydroxyethylamino)-2-pyridyl]sulfonyl]-3-[(2,4,6-trimethylphenyl)methyl]-1,2,4,5-tetrahydro-3-benzazepine-4-carboxamide (Compound 838), N-[(2-methoxy-3-pyridyl)sulfonyl]-3-[(2,4,6-trimethylphenyl)methyl]-1,2,4,5-tetrahydro-3-benzazepine-4-carboxamide (Compound 876), N-[(6-methoxy-2-pyridyl)sulfonyl]-3-[(2,4,6-trimethylphenyl)methyl]-1,2,4,5-tetrahydro-3-benzazepine-4-carboxamide (Compound 948), N-(benzenesulfonyl)-3-[(2,4,6-trimethylphenyl)methyl]-1,2,4,5-tetrahydro-3-benzazepine-4-carboxamide (Compound 1039), N-[(6-amino-2-pyridyl)sulfonyl]-3-[(2,4,6-trimethylphenyl)methyl]-1,2,4,5-tetrahydro-3-benzazepine-4-carboxamide (Compound 1055), N-(2-pyridylsulfonyl)-3-[(2,4,6-trimethylphenyl)methyl]-1,2,4,5-tetrahydro-3-benzazepine-4-carboxamide (Compound 1093), N-(3-aminophenyl)sulfonyl-5-tert-butyl-2-[(1-methylindol-4-yl)methyl]pyrazole-3-carboxamide (Compound 927), and N-(benzenesulfonyl)-5-tert-butyl-2-[(2,4,6-trimethylphenyl)methyl]pyrazole-3-carboxamide (Compound 45).

Preparation 19: 5-tert-butyl-N-[3-(hydroxymethyl)phenyl]sulfonyl-2-[(2,4,6-trimethylphenyl)methyl]pyrazole-3-carboxamide (Compound 39)

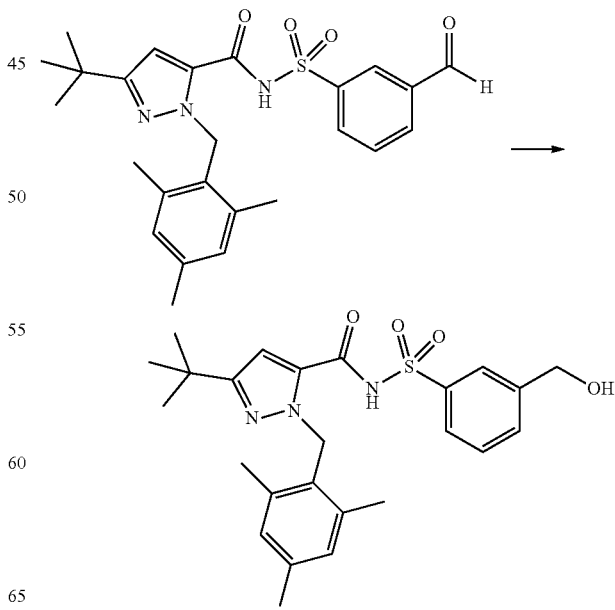

A solution of 3-(tert-Butyl)-N-((3-formylphenyl)sulfonyl)-1-(2,4,6-trimethylbenzyl)-1H-pyrazole-5-carboxamide (prepared following procedures described herein, 50 mg, 0.11 mmol) and anhydrous methanol (5 mL) was cooled to 0° C. The mixture was purged with nitrogen before adding sodium borohydride (7.6 mg, 0.20 mmol). The mixture was allowed to warm to room temperature and was stirred overnight. The reaction mixture was again cooled to 0° C. before adding additional sodium borohydride (7.6 mg, 0.20 mmol). The mixture was warmed to room temperature and was allowed to stir for 4 h. Solvents were removed and the crude residue was taken up in DMSO and subjected to preparatory-HPLC (10-99% acetonitrile/water with 0.05 mM HCl) to give 5-tert-butyl-N-[3-(hydroxymethyl)phenyl]sulfonyl-2-[(2,4,6-trimethylphenyl)methyl]pyrazole-3-carboxamide (Compound 39) (28 mg, 56%). $^1$H NMR (400 MHz, DMSO) δ 12.51 (s, 1H), 7.99 (s, 1H), 7.87 (d, J=7.7 Hz, 1H), 7.63 (dt, J=15.3, 7.7 Hz, 2H), 7.01 (s, 1H), 6.75 (s, 2H), 5.42 (s, 2H), 4.63 (s, 2H), 2.16 (s, 3H), 2.07 (d, J=6.4 Hz, 6H), 1.14 (s, 9H). ESI-MS m/z calc. 469.2, found 470.0 $(M+1)^+$; Retention time: 2.12 min (3 min run).

Preparation 20: N-(benzenesulfonyl)-2-[(2,6-dimethylphenyl)methyl]-5-(2-methoxyphenyl)pyrazole-3-carboxamide (Compound 347)

Step 1: methyl N-[(2,6-dimethylphenyl)methylamino]carbamate

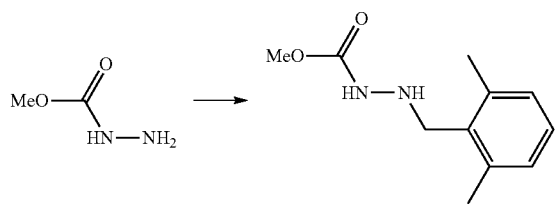

2-(Chloromethyl)-1,3-dimethyl-benzene (25.0 g, 162 mmol), methyl N-aminocarbamate (29.1 g, 323 mmol) and K$_2$CO$_3$ (33.5 g, 243 mmol) were combined in N,N-dimethylformamide (150 mL) and heated at 80° C. for 2 h. The reaction mixture was concentrated and the crude material was partitioned between ethyl acetate and water. The organics were separated, washed with brine and dried over sodium sulfate. The mixture was filtered and the filtrate was concentrated. The residue was subjected to silica gel column chromatography (0-60% ethyl acetate/hexanes) to give methyl N-[(2,6-dimethylphenyl)methylamino]carbamate (18.0 g, 53%). ESI-MS m/z calc. 208.3, found 209.2 $(M+1)^+$; Retention time: 0.41 min (1 min run).

Step 2: methyl 2-[(2,6-dimethylphenyl)methyl]-5-hydroxy-pyrazole-3-carboxylate

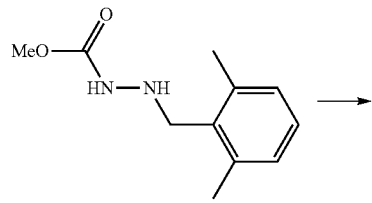

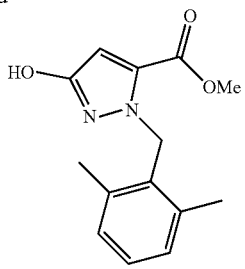

Methyl N-[(2,6-dimethylphenyl)methylamino]carbamate (18.0 g, 86.4 mmol) was suspended in methanol (126 mL) and dimethyl but-2-ynedioate (10.6 mL, 86.4 mmol) was added. The reaction mixture was stirred at reflux for 2 h and was then cooled to room temperature. Sodium methoxide (20.5 mL of 25% w/v, 95.1 mmol) was added and the reaction mixture was again heated at reflux. After 1 h, the mixture was cooled to room temperature and was added drop-wise to a flask containing 1M aq. HCl (300 mL) in an ice water bath. The resulting precipitate was collected by vacuum filtration. The solids were dissolved in CH$_2$Cl2 and the excess water was separated and the organic layer was dried over sodium sulfate and evaporated to give methyl 2-[(2,6-dimethylphenyl)methyl]-5-hydroxy-pyrazole-3-carboxylate (21.6 g, 96%). $^1$H NMR (400 MHz, DMSO) δ 10.05 (s, 1H), 7.10 (dd, J=8.4, 6.5 Hz, 1H), 7.02 (d, J=7.5 Hz, 2H), 6.06 (s, 1H), 5.57 (s, 2H), 3.85 (s, 3H), 2.24 (s, 6H). ESI-MS m/z calc. 260.1, found 261.4 $(M+1)^+$; Retention time: 0.57 min (1 min run).

Step 3: 2-[(2,6-dimethylphenyl)methyl]-5-(trifluoromethylsulfonyloxy)-pyrazole-3-carboxylate

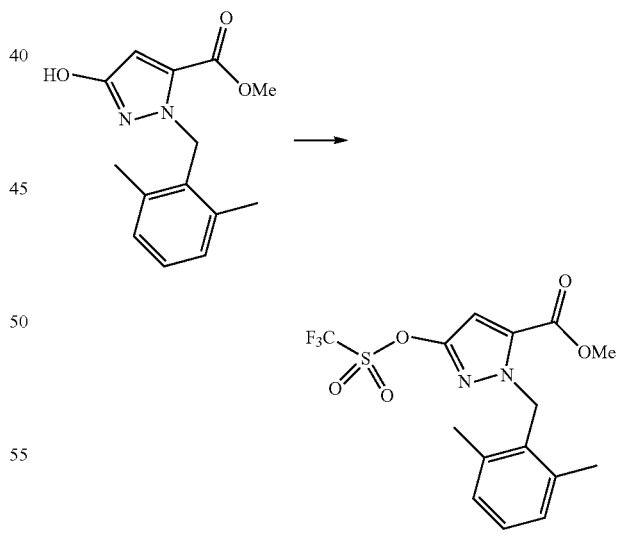

Methyl 2-[(2,6-dimethylphenyl)methyl]-5-hydroxy-pyrazole-3-carboxylate (8.40 g, 32.3 mmol) and pyridine (3.13 mL, 38.7 mmol) were combined in toluene (84.00 mL) and cooled in a salt water/ice bath. Triflic anhydride (5.98 mL, 35.5 mmol) was added drop-wise keeping the temperature below 0° C. After the addition was complete, the reaction mixture was warmed to room temperature and stirred for 1 h. The reaction mixture was quenched with water (30 mL)

and the layers were separated. The aqueous layer was extracted with toluene (1×40 mL). The organics were combined and washed with water (40 mL), dried over sodium sulfate, filtered and evaporated to give methyl 2-[(2,6-dimethylphenyl)methyl]-5-(trifluoromethylsulfonyloxy)-pyrazole-3-carboxylate (12.4 g, 98%) ESI-MS m/z calc. 392.1, found 393.2 (M+1)⁺; Retention time: 0.82 min (1 min run).

Step 4: 2-[(2,6-dimethylphenyl)methyl]-5-(4,4,5,5-tetramethyl-1,3,2-dioxaborolan-2-yl)pyrazole-3-carboxylate

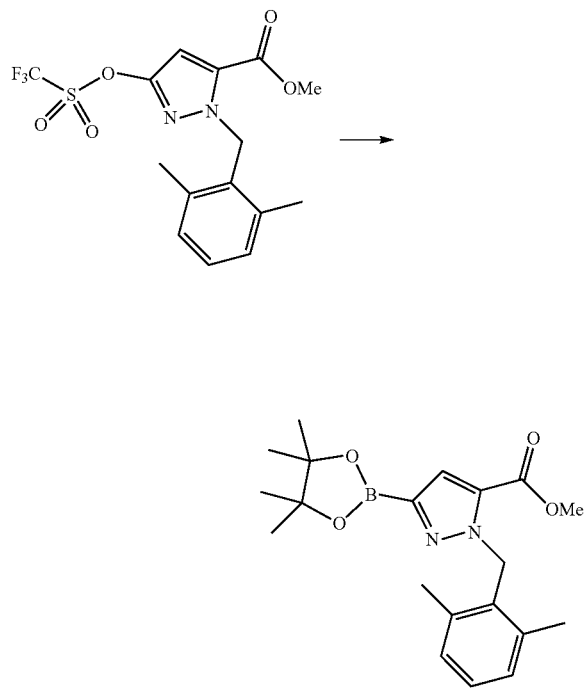

A suspension of methyl 2-[(2,6-dimethylphenyl)methyl]-5-(trifluoromethylsulfonyloxy)pyrazole-3-carboxylate (12.1 g, 30.7 mmol), 4,4,5,5-tetramethyl-2-(4,4,5,5-tetramethyl-1,3,2-dioxaborolan-2-yl)-1,3,2-dioxaborolane (8.59 g, 33.8 mmol) and KOAc (9.05 g, 92.2 mmol) in dioxane (240 mL) was degassed for 10 min. Dichloro[1,1'-bis(diphenylphosphino)ferrocene]palladium (II) dichloromethane adduct (1.26 g, 1.54 mmol) and 1,1'-bis(diphenylphosphino)ferrocene (852 mg, 1.54 mmol) were added and the reaction was degassed for an additional 10 min. The reaction mixture was heated at 100° C. for 4 h. The mixture was concentrated to ~100 mL total volume and was diluted with toluene (250 mL) and water (100 mL). The mixture was filtered through a pad of Celite to remove small black particulates. The organics were separated, washed with water (100 mL) and dried over sodium sulfate. The organics were filtered through a plug of silica (100 g) and the silica was washed with another 1 L of toluene. The toluene was evaporated to give methyl 2-[(2,6-dimethylphenyl)methyl]-5-(4,4,5,5-tetramethyl-1,3,2-dioxaborolan-2-yl)pyrazole-3-carboxylate (10.6 g, 93%). ¹H NMR (400 MHz, Chloroform-d) δ 7.27 (s, 1H), 7.09 (dd, J=8.2, 6.7 Hz, 1H), 7.00 (d, J=7.4 Hz, 2H), 5.86 (s, 2H), 3.81 (s, 3H), 2.25 (s, 6H), 1.32 (s, 12H).

Step 5: 2-[(2,6-dimethylphenyl)methyl]-5-(4,4,5,5-tetramethyl-1,3,2-dioxaborolan-2-yl)pyrazole-3-carboxylic acid

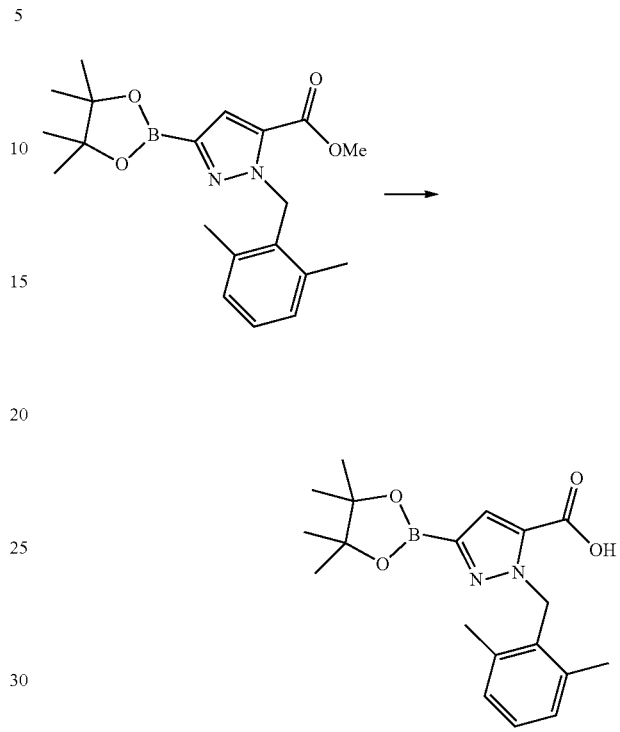

Methyl 2-[(2,6-dimethylphenyl)methyl]-5-(4,4,5,5-tetramethyl-1,3,2-dioxaborolan-2-yl)pyrazole-3-carboxylate (7.00 g, 14.2 mmol) was dissolved in THF (53 mL) and NaOH (43 mL of 1.0 M, 43 mmol). The reaction mixture was heated at 60° C. for 2 h and was concentrated. The resulting solid was partitioned between ethyl acetate and a 1 N HCl solution. The organics were separated, washed with brine, dried over sodium sulfate and evaporated to give 2-[(2,6-dimethylphenyl)methyl]-5-(4,4,5,5-tetramethyl-1,3,2-dioxaborolan-2-yl)pyrazole-3-carboxylic acid (5.5 g, 98%). ¹H NMR (400 MHz, DMSO) δ 13.44 (s, 1H), 7.13 (dd, J=8.3, 6.6 Hz, 1H), 7.07-7.02 (m, 3H), 5.81 (s, 2H), 2.23 (s, 6H), 1.24 (s, 12H). ESI-MS m/z calc. 356.2, found 275.4 (M+1)⁺; Retention time: 0.42 min (1 min run). Note: found mass is [-pinacol+H].

Step 6: N-(benzenesulfonyl)-2-[(2,6-dimethylphenyl)methyl]-5-(4,4,5,5-tetramethyl-1,3,2-dioxaborolan-2-yl)pyrazole-3-carboxamide

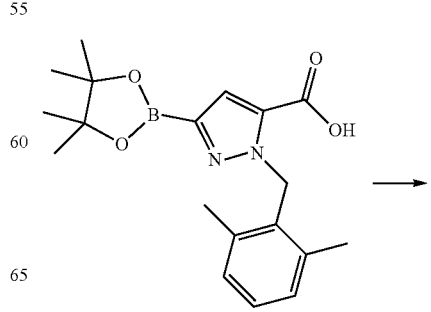

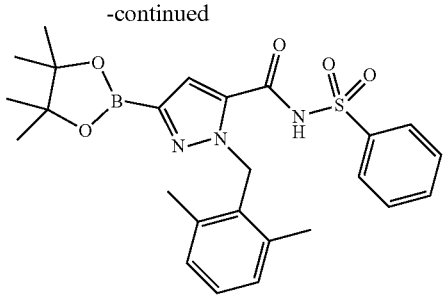

2-[(2,6-Dimethylphenyl)methyl]-5-(4,4,5,5-tetramethyl-1,3,2-dioxaborolan-2-yl)pyrazole-3-carboxylic acid (4.14 g, 11.6 mmol), N-[(dimethylamino)-1H-1,2,3-triazolo-[4,5-b]pyridin-1-ylmethylene]-N-methylmethanaminium hexafluorophosphate N-oxide (4.42 g, 11.6 mmol) and ethyldiisopropylamine (6.07 mL, 34.9 mmol) were combined in $CH_2Cl_2$ (116 mL). Benzenesulfonamide (2.19 g, 13.9 mmol) was added and the reaction mixture was stirred for 16 h before it was diluted with $CH_2Cl_2$ and washed with 1N HCl. The organics were further washed with brine, dried over sodium sulfate, filtered and evaporated. The crude material was purified by silica gel chromatography (0-100% ethyl acetate/hexanes) to give N-(benzenesulfonyl)-2-[(2,6-dimethylphenyl)methyl]-5-(4,4,5,5-tetramethyl-1,3,2-dioxaborolan-2-yl)pyrazole-3-carboxamide (4.14 g, 72%). ESI-MS m/z calc. 495.2, found 414.4 $(M+1)^+$; Retention time: 0.68 min (1 min run). Note: found mass is minus the pinacol ester.

Step 7: N-(benzenesulfonyl)-2-[(2,6-dimethylphenyl)methyl]-5-(2-methoxyphenyl)pyrazole-3-carboxamide (Compound 347)

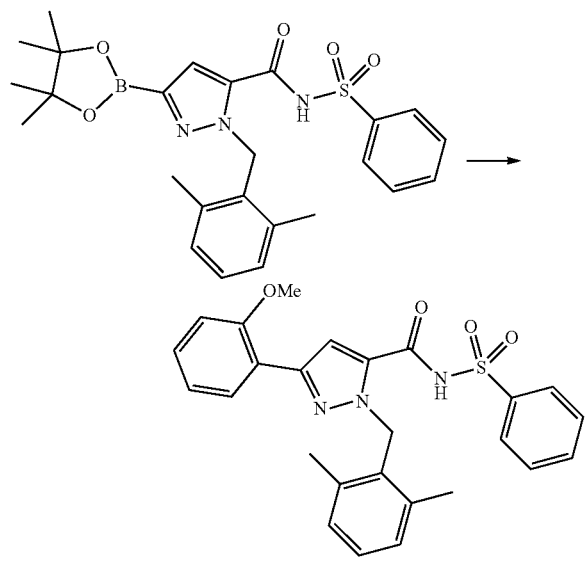

N-(Benzenesulfonyl)-2-[(2,6-dimethylphenyl)methyl]-5-(4,4,5,5-tetramethyl-1,3,2-dioxaborolan-2-yl)pyrazole-3-carboxamide (50 mg, 0.10 mmol), 1-bromo-2-methoxybenzene (19 mg, 0.10 mmol), dichloro[1,1'-bis(diphenylphosphino)ferrocene]palladium (II) dichloromethane adduct (4 mg, 0.005 mmol), and 2M aq. $K_2CO_3$ (0.20 mL, 0.40 mmol) were combined in N,N-dimethylformamide (0.6 mL) and heated at 70° C. for 2 h. The reaction mixture was cooled, filtered and subjected to preparatory-HPLC (10-99% acetonitrile/water with 0.05 mMHCl) to give N-(benzenesulfonyl)-2-[(2,6-dimethylphenyl)methyl]-5-(2-methoxyphenyl)pyrazole-3-carboxamide (Compound 347). ESI-MS m/z calc. 475.2, found 476.3 $(M+1)^+$; Retention time: 2.08 min (3 min run).

The following compounds can be synthesized using the procedures described herein:

N-(benzenesulfonyl)-2-[(2,6-dimethylphenyl)methyl]-5-[2-(trifluoromethoxy)phenyl]pyrazole-3-carboxamide (Compound 149), N-(benzenesulfonyl)-5-(4-chloro-3-methoxy-phenyl)-2-[(2,6-dimethylphenyl)methyl]pyrazole-3-carboxamide (Compound 37), N-(benzenesulfonyl)-2-[(2,6-dimethylphenyl)methyl]-5-(3-isopropoxyphenyl)pyrazole-3-carboxamide (Compound 133), N-(benzenesulfonyl)-2-[(2,6-dimethylphenyl)methyl]-5-[3-(trifluoromethoxy)phenyl]pyrazole-3-carboxamide (Compound 225), N-(benzenesulfonyl)-2-[(2,6-dimethylphenyl)methyl]-5-[4-(trifluoromethyl)phenyl]pyrazole-3-carboxamide (Compound 316), N-(benzenesulfonyl)-5-[3-(difluoromethyl)phenyl]-2-[(2,6-dimethylphenyl)methyl]pyrazole-3-carboxamide (Compound 315), N-(benzenesulfonyl)-5-(2,4-dimethoxyphenyl)-2-[(2,6-dimethylphenyl)methyl]pyrazole-3-carboxamide (Compound 135), N-(benzenesulfonyl)-2-[(2,6-dimethylphenyl)methyl]-5-(1-methylindol-4-yl)pyrazole-3-carboxamide (Compound 363), N-(3-aminophenyl)sulfonyl-5-(2,6-dimethylphenyl)-2-[(2,4,6-trimethylphenyl)methyl]pyrazole-3-carboxamide (Compound 209), N-(benzenesulfonyl)-2-[(2,6-dimethylphenyl)methyl]-5-(m-tolyl)pyrazole-3-carboxamide (Compound 202), N-(3-aminophenyl)sulfonyl-5-(2-fluoro-3-methyl-phenyl)-2-[(2,4,6-trimethylphenyl)methyl]pyrazole-3-carboxamide, N-(3-aminophenyl)sulfonyl-5-phenyl-2-[(2,4,6-trimethylphenyl)methyl]pyrazole-3-carboxamide (Compound 367), N-(benzenesulfonyl)-5-[3-(dimethylamino)phenyl]-2-[(2,6-dimethylphenyl)methyl]pyrazole-3-carboxamide (Compound 178), N-(benzenesulfonyl)-5-[4-(diethylamino)phenyl]-2-[(2,6-dimethylphenyl)methyl]pyrazole-3-carboxamide (Compound 162), N-(benzenesulfonyl)-2-[(2,6-dimethylphenyl)methyl]-5-(4-fluorophenyl)pyrazole-3-carboxamide (Compound 333), N-(benzenesulfonyl)-2-[(2,6-dimethylphenyl)methyl]-5-(3-methoxyphenyl)pyrazole-3-carboxamide (Compound 176), N-(benzenesulfonyl)-5-(4-dimethylaminophenyl)-2-[(2,6-dimethylphenyl)methyl]pyrazole-3-carboxamide (Compound 76), N-(benzenesulfonyl)-5-(2-cyanophenyl)-2-[(2,6-dimethylphenyl)methyl]pyrazole-3-carboxamide (Compound 99), N-(benzenesulfonyl)-2-[(2,6-dimethylphenyl)methyl]-5-(3-fluoro-4-methoxy-phenyl)pyrazole-3-carboxamide (Compound 43), N-(benzenesulfonyl)-2-[(2,6-dimethylphenyl)methyl]-5-(4-methoxyphenyl)pyrazole-3-carboxamide (Compound 49), N-(benzenesulfonyl)-2-[(2,6-dimethylphenyl)methyl]-5-[3-(trifluoromethyl)phenyl]pyrazole-3-carboxamide (Compound 220),
N-(benzenesulfonyl)-5-(3-chlorophenyl)-2-[(2,6-dimethylphenyl)methyl]pyrazole-3-carboxamide (Compound 83),
N-(benzenesulfonyl)-5-(2-chlorophenyl)-2-[(2,6-dimethylphenyl)methyl]pyrazole-3-carboxamide (Compound 339),
N-(benzenesulfonyl)-5-(2,5-dimethoxyphenyl)-2-[(2,6-dimethylphenyl)methyl]pyrazole-3-carboxamide (Compound 100),
N-(benzenesulfonyl)-2-[(2,6-dimethylphenyl)methyl]-5-[4-(trifluoromethoxy)phenyl]pyrazole-3-carboxamide (Compound 159),
ethyl 2-[4-[5-(benzenesulfonylcarbamoyl)-1-[(2,6-dimethylphenyl)methyl]pyrazol-3-yl]phenyl]acetate (Compound 21),
N-(benzenesulfonyl)-2-[(2,6-dimethylphenyl)methyl]-5-[5-(5-methyl-1,2,4-oxadiazol-3-yl)-2-thienyl]pyrazole-3-carboxamide (Compound 151),
N-(benzenesulfonyl)-2-[(2,6-dimethylphenyl)methyl]-5-(2-ethoxyphenyl)pyrazole-3-carboxamide (Compound 152),
N-(3-aminophenyl)sulfonyl-5-(2-methoxy-3-methyl-phenyl)-2-[(2,4,6-trimethylphenyl)methyl]pyrazole-3-carboxamide (Compound 208),
N-(benzenesulfonyl)-2-[(2,6-dimethylphenyl)methyl]-5-(2-fluorophenyl)pyrazole-3-carboxamide (Compound 109),
N-(benzenesulfonyl)-2-[(2,6-dimethylphenyl)methyl]-5-(2-isopropoxyphenyl)pyrazole-3-carboxamide (Compound 277),
N-(benzenesulfonyl)-5-(4-chlorophenyl)-2-[(2,6-dimethylphenyl)methyl]pyrazole-3-carboxamide (Compound 28),
N-(benzenesulfonyl)-2-[(2,6-dimethylphenyl)methyl]-5-(4-ethoxyphenyl)pyrazole-3-carboxamide (Compound 29),
N-(benzenesulfonyl)-2-[(2,6-dimethylphenyl)methyl]-5-(3-ethoxyphenyl)pyrazole-3-carboxamide (Compound 280),
N-(3-aminophenyl)sulfonyl-5-(2-methoxyphenyl)-2-(1-phenylethyl)pyrazole-3-carboxamide (Compound 40),
N-(benzenesulfonyl)-2-[(2,6-dimethylphenyl)methyl]-5-(5-fluoro-2-methoxy-phenyl)pyrazole-3-carboxamide,
N-(benzenesulfonyl)-2-[(2,6-dimethylphenyl)methyl]-5-[2-(trifluoromethyl)phenyl]pyrazole-3-carboxamide (Compound 369),
N-(benzenesulfonyl)-2-[(2,6-dimethylphenyl)methyl]-5-(p-tolyl)pyrazole-3-carboxamide (Compound 199),
N-(benzenesulfonyl)-5-[2-(dimethylamino)phenyl]-2-[(2,6-dimethylphenyl)methyl]pyrazole-3-carboxamide (Compound 128),
N-(benzenesulfonyl)-2-[(2,6-dimethylphenyl)methyl]-5-(3-fluorophenyl)pyrazole-3-carboxamide (Compound 166),
N-(benzenesulfonyl)-2-[(2,6-dimethylphenyl)methyl]-5-(1-methylindol-5-yl)pyrazole-3-carboxamide (Compound 263),
N-(benzenesulfonyl)-2-[(2,6-dimethylphenyl)methyl]-5-[6-(1-piperidyl)-3-pyridyl]pyrazole-3-carboxamide (Compound 329),
N-(benzenesulfonyl)-2-[(2,6-dimethylphenyl)methyl]-5-(4-fluoro-2-methoxy-phenyl)pyrazole-3-carboxamide (Compound 155),
N-(benzenesulfonyl)-2-[(2,6-dimethylphenyl)methyl]-5-[3-(morpholinomethyl)phenyl]pyrazole-3-carboxamide (Compound 302),
N-(3-aminophenyl)sulfonyl-5-(2-methoxy-3-pyridyl)-2-[(2,4,6-trimethylphenyl)methyl]pyrazole-3-carboxamide (Compound 122),
N-(benzenesulfonyl)-2-[(2,6-dimethylphenyl)methyl]-5-(3-thienyl)pyrazole-3-carboxamide (Compound 357),
N-(3-aminophenyl)sulfonyl-5-(4-methoxyphenyl)-2-(1-phenylethyl)pyrazole-3-carboxamide (Compound 1024),
3-[5-(benzenesulfonylcarbamoyl)-1-[(2,6-dimethylphenyl)methyl]pyrazol-3-yl]benzoic acid (Compound 343),
N-(benzenesulfonyl)-5-(3-tert-butoxyphenyl)-2-[(2,6-dimethylphenyl)methyl]pyrazole-3-carboxamide (Compound 744),
N-(benzenesulfonyl)-5-(4H-1,3-benzodioxin-7-yl)-2-[(2,6-dimethylphenyl)methyl]pyrazole-3-carboxamide (Compound 1621),
N-(benzenesulfonyl)-5-[2-(dimethylamino)pyrimidin-5-yl]-2-[(2,6-dimethylphenyl)methyl]pyrazole-3-carboxamide (Compound 1678),
N-(benzenesulfonyl)-5-(5-chloro-3-fluoro-2-methoxy-phenyl)-2-[(2,6-dimethylphenyl)methyl]pyrazole-3-carboxamide,
N-(benzenesulfonyl)-5-(5-chloro-3-fluoro-2-methoxy-phenyl)-2-[(2,6-dimethylphenyl)methyl]pyrazole-3-carboxamide (Compound 379),
N-(benzenesulfonyl)-5-(3-tert-butoxyphenyl)-2-[(2,6-dimethylphenyl)methyl]pyrazole-3-carboxamide (Compound 744),
N-(benzenesulfonyl)-2-[(2,6-dimethylphenyl)methyl]-5-(4-isopropoxyphenyl)pyrazole-3-carboxamide (Compound 1478),
N-(benzenesulfonyl)-2-[(2,6-dimethylphenyl)methyl]-5-(4-oxochromen-3-yl)pyrazole-3-carboxamide (Compound 1501),
N-(3-aminophenyl)sulfonyl-5-(4-methoxyphenyl)-2-(1-phenylethyl)pyrazole-3-carboxamide (Compound 1024)
N-(3-aminophenyl)sulfonyl-5-(2-fluoro-3-methyl-phenyl)-2-[(2,4,6-trimethylphenyl)methyl]pyrazole-3-carboxamide (Compound 293), and.
N-(benzenesulfonyl)-2-[(2,6-dimethylphenyl)methyl]-5-(5-fluoro-2-methoxy-phenyl)pyrazole-3-carboxamide (Compound 27).

Preparation 21: 5-Benzyloxy-2-[(2,4,6-trimethylphenyl)methyl]pyrazole-3-carboxylic acid Step 1: methyl 3-(benzyloxy)-1-(2,6-dimethylbenzyl)-1H-pyrazole-5-carboxylate

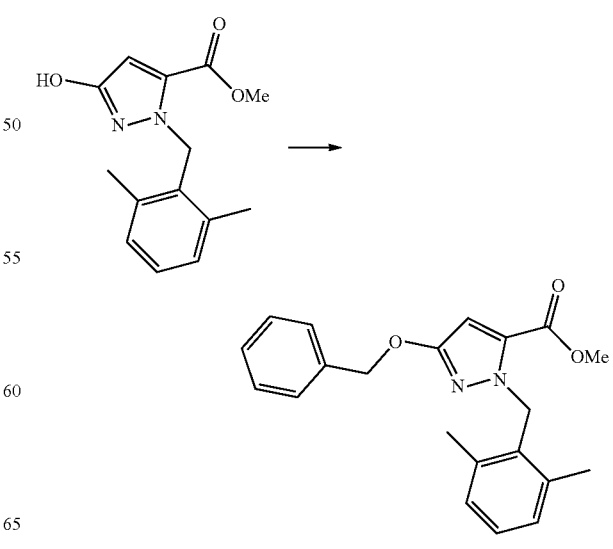

To a solution of methyl 5-hydroxy-2-[(2,4,6-trimethylphenyl)methyl]pyrazole-3-carboxylate (250 mg, 0.911 mmol) and K₂CO₃ (315 mg, 2.28 mmol) in N,N-dimethylformamide (5 mL) was added benzyl bromide (130 µL, 1.09 mmol) and the reaction mixture was stirred at room temperature for 16 h. The mixture was concentrated and the resulting solids were partitioned between ethyl acetate and water. The organics were separated, washed with brine, dried over sodium sulfate and evaporated to give methyl 3-(benzyloxy)-1-(2,6-dimethylbenzyl)-1H-pyrazole-5-carboxylate. ESI-MS m/z calc. 364.2, found 365.4 (M+1)⁺; Retention time: 0.90 min (1 min run).

Step 2: 5-benzyloxy-2-[(2,4,6-trimethylphenyl)methyl]pyrazole-3-carboxylic acid

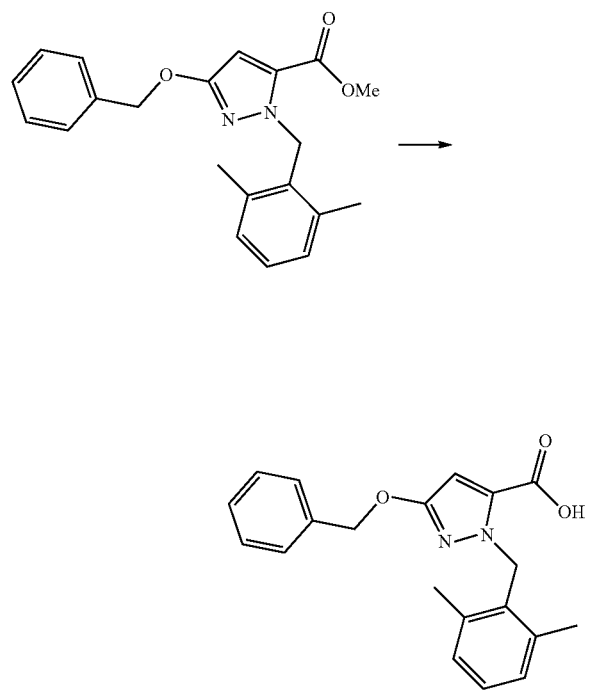

Methyl 3-(benzyloxy)-1-(2,6-dimethylbenzyl)-1H-pyrazole-5-carboxylate (from step 1) was dissolved in methanol (3 mL) before 1N NaOH (3 mL) was added. The reaction mixture was heated for 2 h at 60° C. and concentrated. The crude mixture was partitioned between ethyl acetate and 1 N HCl. The organics were separated, washed with brine, dried over sodium sulfate, and evaporated to yield 5-benzyloxy-2-[(2,4,6-trimethylphenyl)methyl]pyrazole-3-carboxylic acid (295 mg, 92% for 2 steps) ESI-MS m/z calc. 350.2, found 351.4 (M+1)⁺; Retention time: 0.79 min (1 min run).

The following compound can be synthesized using the procedures described herein:

3-(1-phenylethoxy)-1-(2,4,6-trimethylbenzyl)-1H-pyrazole-5-carboxylic acid,

N-(3-aminophenyl)sulfonyl-5-benzyloxy-2-[(2,4,6-trimethylphenyl)methyl]pyrazole-3-carboxamide (Compound 42), and N-(3-aminophenyl)sulfonyl-5-(1-phenylethoxy)-2-[(2,4,6-trimethylphenyl)methyl]pyrazole-3-carboxamide (Compound 278).

Preparation 22: N-(3-aminophenyl)sulfonyl-5-(3,3-dimethylbutyl)-2-[(2,6-dimethylphenyl)methyl]pyrazole-3-carboxamide (Compound 323)

Step 1: 5-[(E)-3,3-dimethylbut-1-enyl]-2-[(2,6-dimethylphenyl)methyl]pyrazole-3-carboxylate

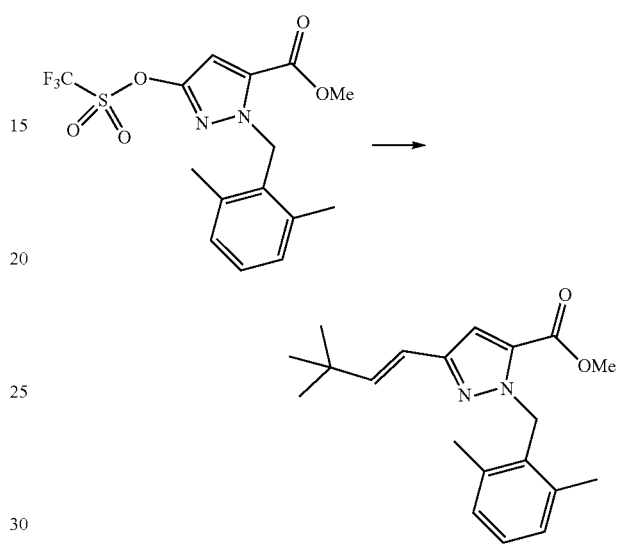

Methyl 2-[(2,6-dimethylphenyl)methyl]-5-(trifluoromethylsulfonyloxy)pyrazole-3-carboxylate (500. mg, 1.27 mmol), [(E)-3,3-dimethylbut-1-enyl]boronic acid (196 mg, 1.53 mmol), dichloro[1,1'-bis(diphenylphosphino)ferrocene]palladium (II) dichloromethane (52 mg, 0.064 mmol), and 2M K₂CO₃ (1.9 mL of 2.0 M, 3.8 mmol) were combined in dioxane (10 mL) and irradiated in a microwave reactor for 30 min at 120° C. The reaction mixture was diluted with ethyl acetate and was filtered through a pad of Celite. The filtrate was washed with water, brine, dried over sodium sulfate and concentrated. The crude material was purified by silica gel column chromatography (0-60% ethyl acetate/hexanes) to give methyl 5-[(E)-3,3-dimethylbut-1-enyl]-2-[(2,6-dimethylphenyl)methyl]pyrazole-3-carboxylate (300. mg, 72%) ESI-MS m/z calc. 326.2, found 327.5 (M+1)⁺; Retention time: 0.94 min (1 min run).

Step 2: 5-[(E)-3,3-dimethylbut-1-enyl]-2-[(2,6-dimethylphenyl)methyl]pyrazole-3-carboxylate

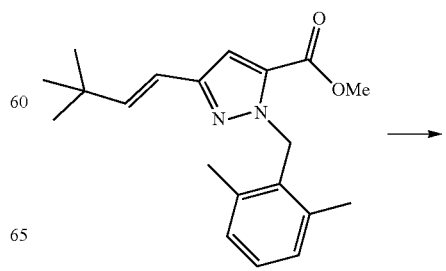

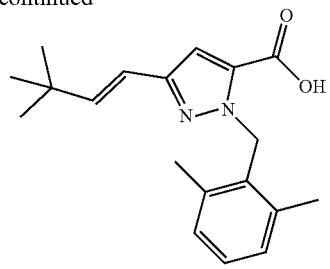

Methyl 5-[(E)-3,3-dimethylbut-1-enyl]-2-[(2,6-dimethylphenyl)methyl]pyrazole-3-carboxylate (300. mg, 0.919 mmol) was dissolved in THF (3 mL) before adding NaOH (3.0 mL of 1.0 M, 3.0 mmol). The reaction mixture was heated for 2 h at 60° C. and then concentrated. The resulting solid was partitioned between ethyl acetate and an aqueous solution of 1 N HCl. The organics were separated, washed with brine, dried over sodium sulfate and concentrated to give 5-[(E)-3,3-dimethylbut-1-enyl]-2-[(2,6-dimethylphenyl)methyl]pyrazole-3-carboxylic acid (198 mg, 69%). ESI-MS m/z calc. 312.2, found 313.5 (M+1)$^+$; Retention time: 0.77 min (1 min run).

Step 3: (E)-3-(3,3-dimethylbut-1-en-1-yl)-N-((3-nitrophenyl)sulfonyl)-1-(2,4,6-trimethylbenzyl)-1H-pyrazole-5-carboxamide

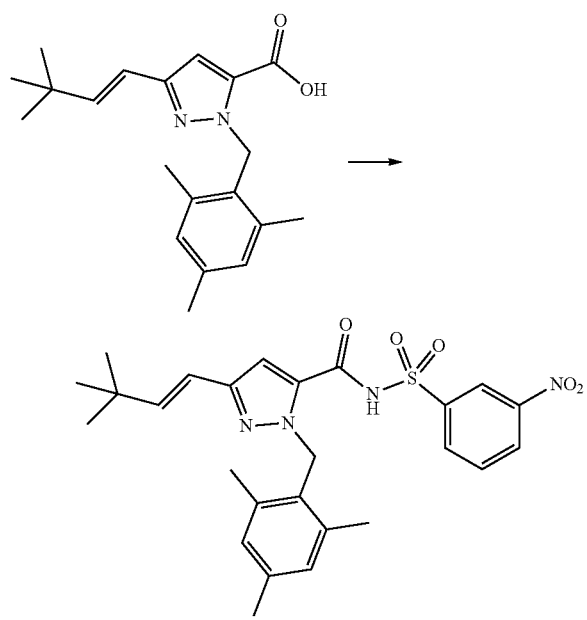

5-[(E)-3,3-dimethylbut-1-enyl]-2-[(2,6-dimethylphenyl)methyl]pyrazole-3-carboxylic acid (50. mg, 0.16 mmol), 3-nitrobenzenesulfonamide (32 mg, 0.16 mmol), N-[(dimethylamino)-1H-1,2,3-triazolo-[4,5-b]pyridin-1-ylmethylene]-N-methylmethanaminium hexafluorophosphate N-oxide (61 mg, 0.16 mmol), and ethyldiisopropylamine (84 µL, 0.48 mmol) were combined in N,N-dimethylformamide (1 mL) and stirred at room temperature for 16 h. The reaction mixture was filtered and subjected to preparatory-HPLC (10-99% acetonitrile/water with 0.05 mMHCl) to give (E)-3-(3,3-dimethylbut-1-en-1-yl)-N-((3-nitrophenyl)sulfonyl)- 1-(2,4,6-trimethylbenzyl)-1H-pyrazole-5-carboxamide (23 mg, 29%). ESI-MS m/z calc. 496.2, found 497.2+; Retention time: 0.85 min (1 min run).

Step 4: N-(3-aminophenyl)sulfonyl-5-(3,3-dimethylbutyl)-2-[(2,6-dimethylphenyl)methyl]pyrazole-3-carboxamide (Compound 323)

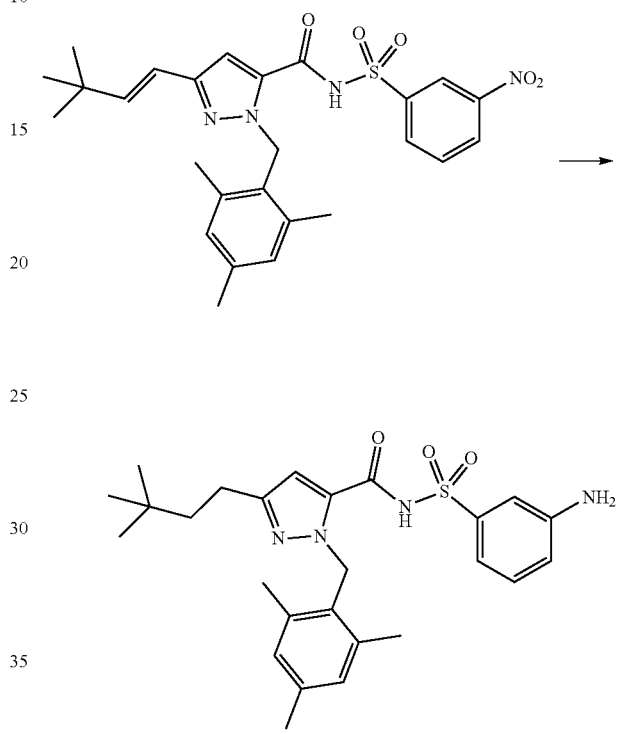

A mixture of (E)-3-(3,3-dimethylbut-1-en-1-yl)-N-((3-nitrophenyl)sulfonyl)-1-(2,4,6-trimethylbenzyl)-1H-pyrazole-5-carboxamide (23 mg, 0.046 mmol), methanol (2 mL) and 10% Pd/C (17 mg, 0.016 mmol) at room temperature was placed under a balloon of hydrogen The mixture was stirred for 30 min before it was filtered. The filtrate was subjected to preparatory-HPLC (10-99% acetonitrile/water with 0.05 mM HCl) to give N-(3-aminophenyl)sulfonyl-5-(3,3-dimethylbutyl)-2-[(2,6-dimethylphenyl)methyl]pyrazole-3-carboxamide (Compound 323) (4.0 mg, 17%). ESI-MS m/z calc. 468.2, found 469.0 (M+1)$^+$; Retention time: 2.11 min (3 min run).

The following compounds can be synthesized using the procedures described herein:
N-(3-aminophenyl)sulfonyl-2-[(2,6-dimethylphenyl)methyl]-5-norbornan-2-yl-pyrazole-3-carboxamide (Compound 370),
N-[(6-amino-2-pyridyl)sulfonyl]-7-ethyl-2-[(2,4,6-trimethylphenyl)methyl]indazole-3-carboxamide (Compound 1086), and
N-(3-aminophenyl)sulfonyl-5-cyclopentyl-2-[(2,6-dimethylphenyl)methyl]pyrazole-3-carboxamide (Compound 105).

Preparation 23: 1-tert-butyl-3-[(2,4,6-trimethylphenyl)methyl]-1H-pyrazole-4-carboxylic acid Step 1: (E)-1-tert-butyl-2-[2-(2,4,6-trimethylphenyl)ethylidene]hydrazine

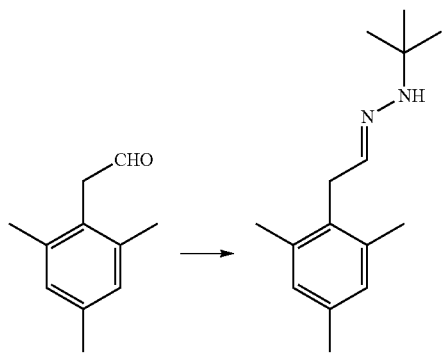

Acetic acid (0.2 mL) was added to a mixture of 2-(2,4,6-trimethylphenyl)acetaldehyde (0.80 g, 4.9 mmol) and t-butylhydrazine hydrochloride (0.73 g, 4.9 mmol) in methanol (10 mL). The mixture was stirred at room temperature for 24 h. The reaction mixture was concentrated under reduced pressure and the residue was treated with ether (20 mL) to give a precipitate which was collected by filtration. The solid was suspended in ethyl acetate (150 mL), the pH adjusted to >7 by adding saturated NaHCO$_3$, the organic layer washed with brine, dried over Na$_2$SO$_4$, filtered and concentrated under reduced pressure to afford (E)-1-tert-butyl-2-[2-(2,4,6-trimethylphenyl)ethylidene]hydrazine (0.80 g, 70.%) as a yellow oil. $^1$H NMR (300 MHz, DMSO-d$_6$) δ 1.22 (s, 9H), 2.18 (s, 3H), 2.23 (s, 6H), 3.68 (d, J=5.2 Hz, 2H), 6.85 (s, 2H), 8.24 (t, J=5.2 Hz, 1H), 11.39 (br s, 1H). ESI-MS m/z calc. 232.2, found 233.2 (M+1)$^+$; Retention time: 1.75 min (5 min run).

Step 2: ethyl 1-tert-butyl-3-[(2,4,6-trimethylphenyl)methyl]-1H-pyrazole-4-carboxylate

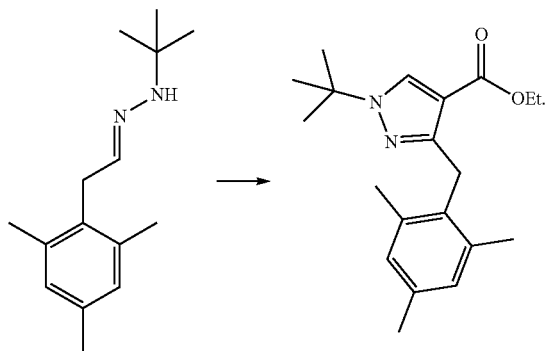 [SMILES: Cc1cc(C)c(C/C=N/NC(C)(C)C)c(C)c1 ; CCOC(=O)c1cn(C(C)(C)C)nc1Cc1c(C)cc(C)cc1C]

A mixture of (E)-1-tert-butyl-2-[2-(2,4,6-trimethylphenyl)ethylidene]hydrazine (0.86 g, 3.7 mmol) and ethylpropiolate (0.44 g, 4.5 mmol) in acetonitrile (3 mL) and acetic acid (3 mL) was stirred at room temperature for 2 d. The reaction mixture was concentrated under reduced pressure and the residue was taken up with ethyl acetate (100 mL) before it was washed with saturated NaHCO$_3$, brine, dried over Na$_2$SO$_4$, filtered and concentrated under reduced pressure. The residue was purified by flash chromatography on silica gel, eluting with 30% ethyl acetate in heptane to afford ethyl 1-tert-butyl-3-[(2,4,6-trimethylphenyl)methyl]-1H-pyrazole-4-carboxylate (0.40 g, 33%) as a yellow solid. ESI-MS m/z calc. 328.2, found 329.2 (M+1)$^+$; Retention time: 2.92 min (5 min run).

Step 4: 1-tert-butyl-3-[(2,4,6-trimethylphenyl)methyl]-1H-pyrazole-4-carboxylic acid

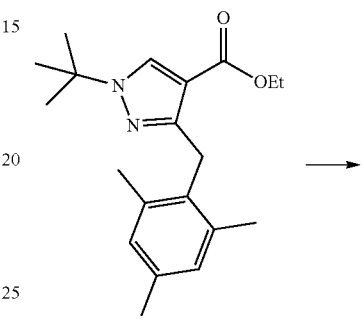

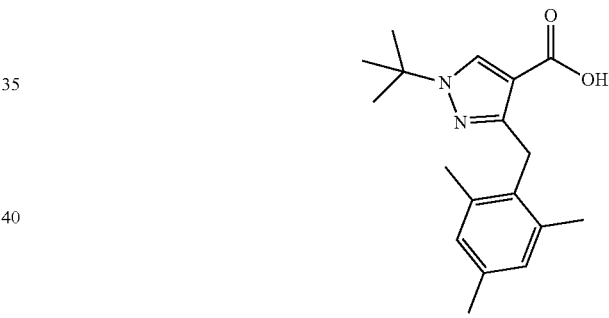

A mixture of ethyl 1-tert-butyl-3-[(2,4,6-trimethylphenyl)methyl]-1H-pyrazole-4-carboxylate (0.34 g, 1.0 mmol) and LiOH·H$_2$O (0.22 g, 5.2 mmol) in methanol (4 mL) and water (4 mL) was heated at reflux for 3 h. The reaction mixture was concentrated under reduced pressure and the pH of the aqueous layer adjusted to ~3 with 5% citric acid. The aqueous layer was extracted with ethyl acetate (150 mL), washed with brine, dried over Na$_2$SO$_4$, filtered and concentrated under reduced pressure. The residue was purified by C18 column chromatography, eluting at 80% methanol in water to afford 1-tert-butyl-3-[(2,4,6-trimethylphenyl)methyl]-1H-pyrazole-4-carboxylic acid (0.23 g, 74%) as a yellow solid. ESI-MS m/z calc. 300.2, found 301.2 (M+1)$^+$; Retention time: 2.41 min (5 min run).

The following compounds can be synthesized using the procedures described herein:

N-(benzenesulfonyl)-1-tert-butyl-3-[(2,4,6-trimethylphenyl)methyl]pyrazole-4-carboxamide (Compound 63) and N-(3-aminophenyl)sulfonyl-1-tert-butyl-3-[(2,4,6-trimethylphenyl)methyl]pyrazole-4-carboxamide (Compound 324).

Preparation 24: 1-tert-Butyl-4-[(2,4,6-trimethylphenyl)methyl]-1H-pyrazole-3-carboxylic acid Step 1:
4-bromo-1-tert-butyl-1H-pyrazole-3-carboxylic acid

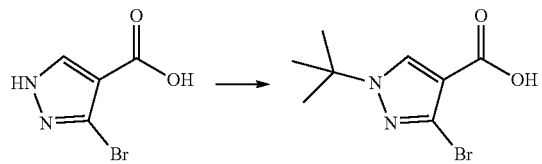

Concentrated sulfuric acid (0.24 mL, 4.3 mmol) was added to a suspension of 4-bromo-1H-pyrazole-3-carboxylic acid (860 mg, 4.3 mmol) in t-BuOH (2.1 mL, 22 mmol). The reaction mixture was stirred at 100° C. for 2 h. Most of the solvent evaporated during the heating and a white solid remained in the flask. After cooling to room temperature, the pH was adjusted to ~4 by adding saturated aq. NaHCO$_3$. The aqueous layer was extracted with ethyl acetate (2×40 mL). The combined organic layers were washed with brine (20 mL), dried over MgSO$_4$, filtered and concentrated under reduced pressure to afford 4-bromo-1-tert-butyl-1H-pyrazole-3-carboxylic acid (1.0 g, 89%) as a white solid. $^1$H NMR (300 MHz, DMSO) δ 1.52 (s, 9H), 8.23 (s, 1H), 12.92 (br s, 1H).

Step 2: methyl 4-bromo-1-tert-butyl-1H-pyrazole-3-carboxylate

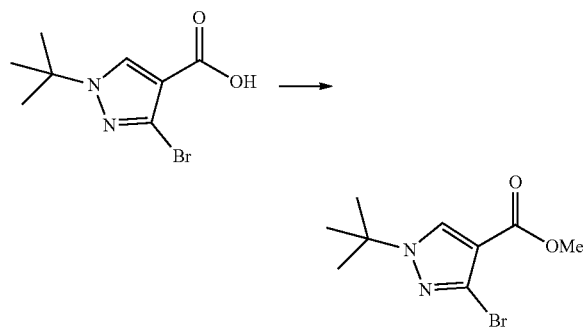

Potassium carbonate (1.1 g, 8.0 mmol) and iodomethane (0.3 mL, 4.8 mmol) were added to a solution of 4-bromo-1-tert-butyl-1H-pyrazole-3-carboxylic acid (980 mg, 4.0 mmol) in N,N-dimethylformamide (6 mL). The reaction mixture was stirred at room temperature overnight. A 5% citric acid solution (20 mL) was added and the aqueous layer was extracted with ethyl acetate (60 mL). The organic layer was washed with water (2×15 mL), brine (15 mL), dried over MgSO$_4$, filtered and concentrated under reduced pressure. The residue was purified by silica gel column chromatography (0-30% ethyl acetate/hexanes) to afford methyl 4-bromo-1-tert-butyl-1H-pyrazole-3-carboxylate (1.1 g, quantitative) as a colorless oil. $^1$H NMR (300 MHz, CDCl$_3$) δ 1.57 (s, 9H), 3.94 (s, 3H), 7.61 (s, 1H).

Step 3: methyl 1-tert-butyl-4-[(2,4,6-trimethylphenyl)methyl]-1H-pyrazole-3-carboxylate

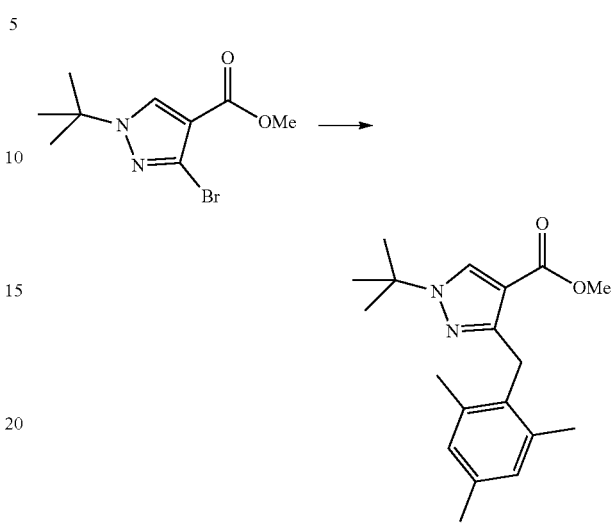

Palladium acetate (45 mg, 0.20 mmol) and $^t$Bu$_3$P.HBF4 (120 mg, 0.40 mmol) were added to a solution of methyl 4-bromo-1-tert-butyl-1H-pyrazole-3-carboxylate (1.1 g, 4.2 mmol) in tetrahydrofuran (10 mL) in a sealed tube. The reaction vessel was evacuated and backfilled with nitrogen three times. A solution of freshly prepared (2,4,6-trimethylphenyl)methyl zinc bromide (8.0 mL of a 1.0 M solution in THF, 8.0 mmol) was added at room temperature. The orange-red solution was stirred at room temperature overnight. The resulting black reaction mixture was quenched with 5% citric acid solution (20 mL) and extracted with ethyl acetate (2×40 mL). The combined organic layers were washed with water (2×15 mL), brine (15 mL), dried over MgSO$_4$, filtered and concentrated under reduced pressure. The residue was purified by silica gel column chromatography (5 to 30% ethyl acetate/hexanes) to give methyl 1-tert-butyl-4-[(2,4,6-trimethylphenyl)methyl]-1H-pyrazole-3-carboxylate (1.1 g, 87%) as a white solid. $^1$H NMR (300 MHz, CDCl$_3$) δ 1.47 (s, 9H), 2.19 (s, 6H), 2.29 (s, 3H), 3.96 (s, 3H), 4.05 (s, 2H), 6.67 (s, 1H), 6.87 (s, 2H).

Step 4: 1-tert-butyl-4-[(2,4,6-trimethylphenyl)methyl]-1H-pyrazole-3-carboxylic acid

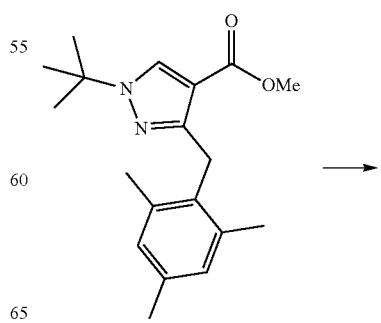

-continued

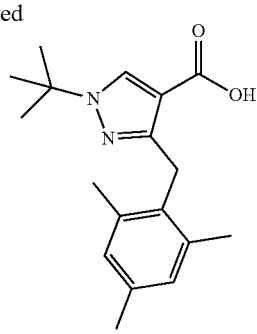

A mixture of 1-tert-butyl-4-[(2,4,6-trimethylphenyl)methyl]-1H-pyrazole-3-carboxylate (1.00 g, 3.18 mmol), LiOH·H₂O (667 mg, 15.5 mmol), THF (10 mL) and water (10 mL) was stirred in a sealed tube at 60° C. for 4 h. The mixture was acidified by adding 5% citric acid (30 mL) and was extracted with ethyl acetate (2×30 mL). The combined organic layers were washed with water (2×15 mL), brine (15 mL), dried over MgSO₄, filtered and concentrated under reduced pressure. The residue was triturated with a mixture of methyl tert-butyl ether (2 mL) and heptanes (2 mL) to afford 1-tert-butyl-4-[(2,4,6-trimethylphenyl)methyl]-1H-pyrazole-3-carboxylic (769 mg, 81%) as a white solid. ¹H NMR (300 MHz, DMSO) δ 1.41 (s, 9H), 2.14 (s, 6H), 2.21 (s, 3H), 3.94 (s, 2H), 6.80 (s, 1H), 6.84 (s, 2H), 12.60 (s, 1H).

The following compound can be synthesized using the procedures described herein:
N-(3-aminophenyl)sulfonyl-1-tert-butyl-4-[(2,4,6-trimethylphenyl)methyl]pyrazole-3-carboxamide (Compound 366).

Preparation 25: 1-tert-butyl-3-(2,4,6-trimethylphenoxy)-1H-pyrazole-4-carboxylic acid Step 1: 1-tert-butyl-1H-pyrazol-3-ol

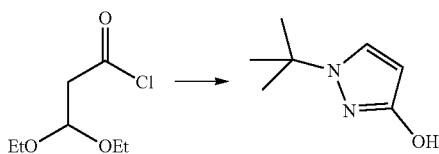

tert-Butylhydrazine hydrochloride (3.03 g, 24.3 mmol) was added to pyridine (30 mL) and the mixture was stirred for 1 h at room temperature. The mixture containing insoluble material was cooled to 5° C. then 3,3-diethoxypropanoyl chloride (3.27 g, 24.3 mmol) was added dropwise. The mixture was then was heated at 80° C. for 48 h before it was cooled to room temperature. The mixture was diluted with ethyl acetate and the organic phase was washed with 5% aq. NaHCO₃ and brine before it was dried over anhydrous Na₂SO₄. The solids were filtered off and the solvent was removed under reduced pressure. The residue was purified by silica gel column chromatography (5-50% ethyl acetate/heptanes) to give a solid which was triturated in heptanes (1×10 mL), filtered and dried to afford 1-tert-butyl-1H-pyrazol-3-ol (1.38 g, 44%) as an off-white solid. ¹H NMR (300 MHz, CDCl₃) δ 1.54 (s, 9H), 5.57 (d, J=2.2 Hz, 1H), 7.24 (d, J=2.2 Hz, 1H), 12.11 (br. s, 1H). ESI-MS m/z calc. 140.1, found 141.2 (M+1)⁺; Retention time: 1.12 min (5 min run).

Step 2: 4-bromo-1-tert-butyl-1H-pyrazol-3-ol

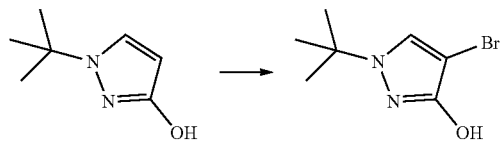

To 1-tert-butyl-1H-pyrazol-3-ol (1.30 g, 9.27 mmol) in dichloromethane (20 mL) was added NaHCO₃ (0.97 g, 11. mmol). The mixture was cooled to 0° C. and a solution of bromine (1.56 g, 9.74 mmol) in dichloromethane (10 mL) was added dropwise. The mixture was stirred for 60 min at 0-10° C. before it was diluted with ethyl acetate. The organic phase was washed with 5% NaHCO₃, 1% Na₂S₂O₃, 5% NaHCO₃, brine and dried over anhydrous Na₂SO₄. The solid was filtered off and the solvent was removed under reduced pressure to afford 4-bromo-1-tert-butyl-1H-pyrazol-3-ol (1.87 g, 92% yield) as an off-white solid. ¹H NMR (300 MHz, CDCl₃) δ 1.53 (s, 9H), 7.31 (s, 1H), 11.58 (br. s, 1H). ESI-MS m/z calc. 218.0, found 219.1/221.1 (M+1)⁺; Retention time: 1.52 min (5 min run).

Step 3: 4-bromo-1-tert-butyl-3-(2,4,6-trimethylphenoxy)-1H-pyrazole

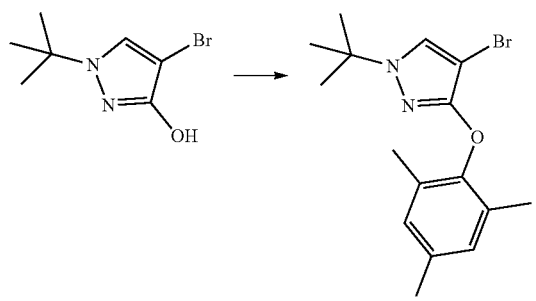 [SMILES: CC(C)(C)n1cc(Br)c(O)n1 ; Cc1cc(C)c(Oc2nn(C(C)(C)C)cc2Br)c(C)c1]

1-2-Dichloroethane (125 mL) was added to flame-dried 4 Å molecular sieves (4.81 g) and air was bubbled through the mixture for 15 minutes. 4-Bromo-1-tert-butyl-1H-pyrazol-3-ol (1.75 g, 7.99 mmol) was added followed by 2,4,6-trimethylphenylboronic acid (3.27 g, 20.0 mmol), pyridine (1.94 mL, 24.0 mmol) and copper (II) acetate (2.18 g, 12.0 mmol). The reaction mixture was stirred under an air atmosphere for 72 h at room temperature before being diluted with ethyl acetate. The organic phase was washed with 10% NH₄OH, brine and dried over anhydrous Na₂SO₄. The solid was filtered off and the solvent was removed under reduced pressure. The residue was purified by silica gel column chromatography (5-75% dichloromethane/heptanes) to afford 4-bromo-1-tert-butyl-3-(2,4,6-trimethylphenoxy)-1H-pyrazole (1.35 g, 50%) as pale yellow solid. ¹H NMR (300 MHz, CDCl₃) δ 1.41 (s, 9H), 2.15 (s, 6H), 2.27 (s, 3H), 6.83 (s, 2H), 7.34 (s, 1H). ESI-MS m/z calc. 336.1, found 337.1/339.1 (M+1)⁺; Retention time: 2.54 min (5 min run).

Step 4: 1-tert-butyl-3-(2,4,6-trimethylphenoxy)-1H-pyrazole-4-carboxylic acid

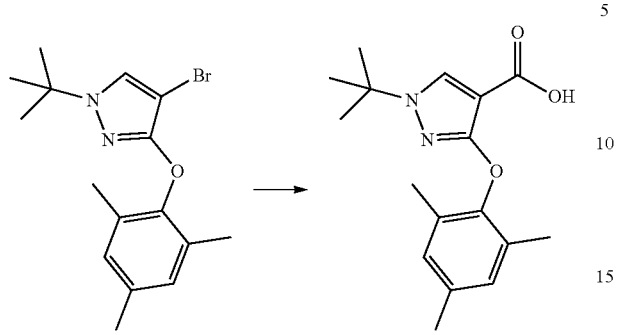

To a solution of 4-bromo-1-tert-butyl-3-(2,4,6-trimethylphenoxy)-1H-pyrazole (1.00 g, 2.96 mmol) in THF (8 mL) cooled at −78° C. was added dropwise a 2.5 M solution of n-buthyllithium in hexanes (1.36 mL, 3.41 mmol). The mixture was stirred for 30 minutes at −78° C. and then $CO_2$ was bubbled through the solution for 45 min after which a chunk of dry ice was added to the reaction mixture. The reaction mixture was allowed to warm from −78° C. to −60° C. over 3 h. The reaction mixture was quenched by the addition of water (5 mL) at 0° C. before it was diluted with ethyl acetate (50 mL). Citric acid (5%, aq.) was added under stirring to obtain pH of 4. The mixture was extracted with ethyl acetate. The combined organic extracts were washed with 5% aq. citric acid, 3% HCl, $H_2O$ and brine and dried over anhydrous $Na_2SO_4$. The solid was filtered off and the solvent was removed under reduced pressure. The residue was triturated twice in heptanes/methyl tert-butyl ether (8 mL/0.5 mL) then purified by silica gel column chromatography 0-20% methanol/dichloromethane) to afford 1-tert-butyl-3-(2,4,6-trimethylphenoxy)-1H-pyrazole-4-carboxylic acid (480 mg, 53% yield) as white solid. $^1$H NMR (300 MHz, $CDCl_3$) δ 1.42 (s, 9H), 2.15 (s, 6H), 2.28 (s, 3H), 6.85 (s, 2H), 7.91 (s, 1H). ESI-MS m/z calc. 302.2, found 303.2 (M+1)$^+$; Retention time: 3.94 min (5 min run).

The following compounds can be synthesized using the procedures described herein:
N-[(6-amino-2-pyridyl)sulfonyl]-1-tert-butyl-3-(2,4,6-trimethylphenoxy)pyrazole-4-carboxamide (Compound 256) and N-(3-aminophenyl)sulfonyl-1-tert-butyl-3-(2,4,6-trimethylphenoxy)pyrazole-4-carboxamide (Compound 325).

Preparation 26: N-(3-aminophenyl)sulfonyl-6-cyano-1-[(2,4,6-trimethylphenyl)methyl]indole-2-carboxamide (Compound 1082)

Step 1: methyl 6-cyano-1-(2,4,6-trimethylbenzyl)-1H-indole-2-carboxylate

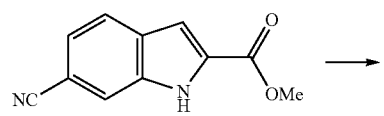

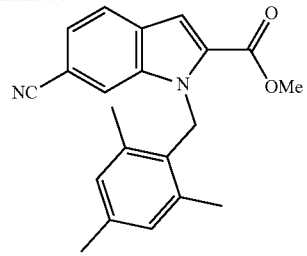

Methyl 6-cyano-1H-indole-2-carboxylate (467 mg, 2.33 mmol) was dissolved in N,N-dimethylformamide (25 mL) and cooled in an ice bath. NaH (60%, 112 mg, 2.80 mmol) was added and the reaction mixture was stirred for 10 min. 2-(Chloromethyl)-1,3,5-trimethyl-benzene (472 mg, 2.80 mmol) was added and the reaction mixture was allowed to warm to room temperature and was stirred for 12 h. The reaction mixture was poured into ice water and was made acidic with the addition of 1 N HCl. The resulting precipitate was collected to give methyl 6-cyano-1-(2,4,6-trimethylbenzyl)-1H-indole-2-carboxylate. ESI-MS m/z calc. 332.2, found 333.2 (M+1)$^+$; Retention time: 0.81 min (1 min run).

Step 2: 6-cyano-1-[(2,4,6-trimethylphenyl)methyl]indole-2-carboxylic acid

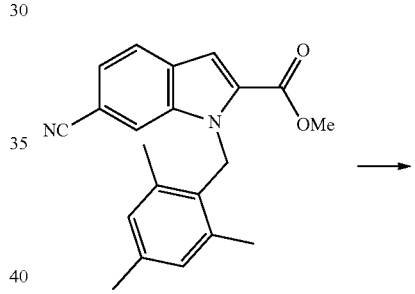

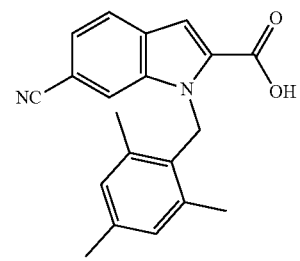

Methyl 6-cyano-1-(2,4,6-trimethylbenzyl)-1H-indole-2-carboxylate (from step 1) was stirred in a mixture of methanol (20 mL), THF (10 mL) and NaOH (9.34 mL of 1.0 M, 9.34 mmol) for 30 min. The reaction mixture was cooled in an ice bath and was acidified with 6 M HCl to a pH of 1. The mixture was extracted with ethyl acetate. The organics were washed with brine, dried over sodium sulfate and evaporated to give 6-cyano-1-[(2,4,6-trimethylphenyl)methyl]indole-2-carboxylic acid (740 mg, 99% over two steps). ESI-MS m/z calc. 318.1, found 319.2 (M+1)$^+$; Retention time: 0.68 min (1 min run).

1939

Step 3: 6-cyano-N-((3-nitrophenyl)sulfonyl)-1-(2,4,6-trimethylbenzyl)-1H-indole-2-carboxamide

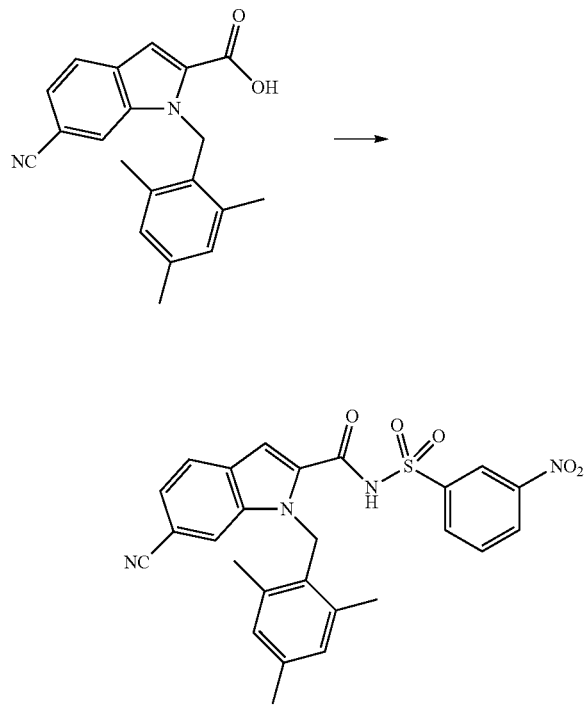 [SMILES: Cc1cc(C)c(Cn2c(C(=O)O)cc3ccc(C#N)cc32)c(C)c1 ; Cc1cc(C)c(Cn2c(C(=O)NS(=O)(=O)c3cccc([N+](=O)[O-])c3)cc3ccc(C#N)cc32)c(C)c1]

6-Cyano-1-[(2,4,6-trimethylphenyl)methyl]indole-2-carboxylic acid (35 mg, 0.11 mmol), (3-nitrophenyl)sulfonylazanide sodium (37 mg, 0.16 mmol), N-[(dimethylamino)-1H-1,2,3-triazolo-[4,5-b]pyridin-1-ylmethylene]-N-methylmethanaminium hexafluorophosphate N-oxide (42 mg, 0.11 mmol), and K$_2$CO$_3$ (46 mg, 0.33 mmol) were combined in N,N-dimethylformamide (1 mL). The reaction mixture was heated at 60° C. for 2 h and was concentrated. The crude material was subjected to preparatory-HPLC (10-99% acetonitrile/water with 0.05 mM HCl) to give 6-cyano-N-((3-nitrophenyl)sulfonyl)-1-(2,4,6-trimethylbenzyl)-1H-indole-2-carboxamide. ESI-MS m/z calc. 502.1, found 503.2 (M+1)$^+$; Retention time: 0.75 min (1 min run).

Step 4: N-(3-aminophenyl)sulfonyl-6-cyano-1-[(2,4,6-trimethylphenyl)methyl]indole-2-carboxamide (Compound 1082)

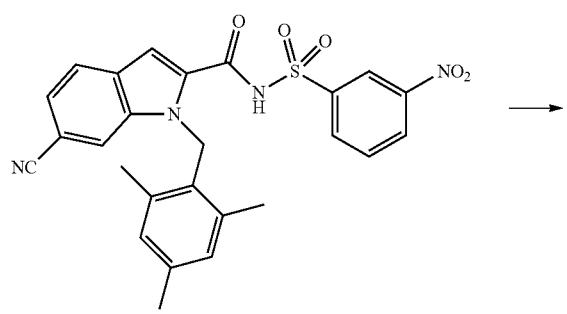

1940

-continued

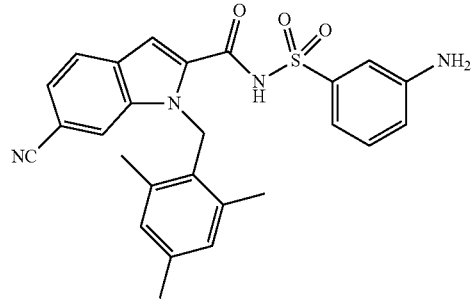

6-Cyano-N-((3-nitrophenyl)sulfonyl)-1-(2,4,6-trimethylbenzyl)-1H-indole-2-carboxamide (from step 3) was mixed with methanol (2 mL) and 10% Pd/C (12 mg, 0.011 mmol) under a balloon of hydrogen. After 1 h, the reaction mixture was filtered and the filtrate was concentrated. The residue was subjected to preparatory-HPLC (10-99% acetonitrile/water with 0.05 mMHCl) to give N-(3-aminophenyl)sulfonyl-6-cyano-1-[(2,4,6-trimethylphenyl)methyl]indole-2-carboxamide (Compound 1082) (6.8 mg, 13% over two steps) ESI-MS m/z calc. 472.2, found 473.2 (M+1)$^+$; Retention time: 1.71 min (3 min run).

The following compounds can be synthesized using the procedures described herein:

N-(benzenesulfonyl)-6-chloro-1-[(2,4,6-trimethylphenyl)methyl]indole-2-carboxamide (Compound 10), N-(benzenesulfonyl)-5-methoxy-1-[(2,4,6-trimethylphenyl)methyl]indole-2-carboxamide (Compound 241), N-(benzenesulfonyl)-4-chloro-1-[(2,4,6-trimethylphenyl)methyl]indole-2-carboxamide (Compound 127), N-(benzenesulfonyl)-4-fluoro-1-(1-phenylethyl)indole-2-carboxamide (Compound 160), N-(benzenesulfonyl)-6-methyl-1-[(2,4,6-trimethylphenyl)methyl]indole-2-carboxamide (Compound 12), N-(benzenesulfonyl)-5-chloro-1-[(2,4,6-trimethylphenyl)methyl]indole-2-carboxamide (Compound 137), N-(benzenesulfonyl)-4-fluoro-1-[(2,4,6-trimethylphenyl)methyl]indole-2-carboxamide (Compound 87), N-(benzenesulfonyl)-5-methyl-1-[(2,4,6-trimethylphenyl)methyl]indole-2-carboxamide (Compound 248), N-(benzenesulfonyl)-4-methyl-1-[(2,4,6-trimethylphenyl)methyl]indole-2-carboxamide (Compound 143), N-(benzenesulfonyl)-7-methyl-1-[(2,4,6-trimethylphenyl)methyl]indole-2-carboxamide (Compound 354), N-(benzenesulfonyl)-5-fluoro-1-[(2,4,6-trimethylphenyl)methyl]indole-2-carboxamide (Compound 33), N-(3-aminophenyl)sulfonyl-4-chloro-1-[(2,4,6-trimethylphenyl)methyl]indole-2-carboxamide (Compound 362), N-(3-aminophenyl)sulfonyl-4-methoxy-1-[(2,4,6-trimethylphenyl)methyl]indole-2-carboxamide (Compound 120), N-[(6-amino-2-pyridyl)sulfonyl]-5-ethyl-1-[(2,4,6-trimethylphenyl)methyl]indole-2-carboxamide (Compound 179), N-(benzenesulfonyl)-1-[(2,4,6-trimethylphenyl)methyl]indole-2-carboxamide (Compound 264), N-(benzenesulfonyl)-1-[(2,6-dimethylphenyl)methyl]-4-methoxy-indole-2-carboxamide (Compound 290), N-(benzenesulfonyl)-4-methoxy-1-[(2,4,6-trimethylphenyl)methyl]indole-2-carboxamide (Compound 348), N-(3-aminophenyl)sulfonyl-5-chloro-1-[(2,4,6-trimethylphenyl)methyl]indole-2-carboxamide (Compound 344), N-(3-aminophenyl)sulfonyl-5-methyl-1-[(2,4,6-trimethylphenyl)methyl]indole-2-carboxamide (Compound 259),
N-(3-aminophenyl)sulfonyl-6-chloro-1-[(2,4,6-trimethylphenyl)methyl]indole-2-carboxamide (Compound 9),
N-(3-aminophenyl)sulfonyl-6-fluoro-1-[(2,4,6-trimethylphenyl)methyl]indole-2-carboxamide (Compound 142),
N-(benzenesulfonyl)-6-fluoro-1-[(2,4,6-trimethylphenyl)methyl]indole-2-carboxamide (Compound 212),
N-(3-aminophenyl)sulfonyl-4-fluoro-1-(1-phenylethyl)indole-2-carboxamide (Compound 186),
N-(3-aminophenyl)sulfonyl-4-methyl-1-[(2,4,6-trimethylphenyl)methyl]indole-2-carboxamide (Compound 144),
N-(3-aminophenyl)sulfonyl-1-[(2,6-dimethylphenyl)methyl]-4-methoxy-indole-2-carboxamide (Compound 168),
N-(3-aminophenyl)sulfonyl-4-fluoro-1-[(2,4,6-trimethylphenyl)methyl]indole-2-carboxamide (Compound 181),
N-(3-methoxyphenyl)sulfonyl-1-[(2,4,6-trimethylphenyl)methyl]indole-2-carboxamide (Compound 335),
N-(3-aminophenyl)sulfonyl-7-methyl-1-[(2,4,6-trimethylphenyl)methyl]indole-2-carboxamide (Compound 194),
N-(3-aminophenyl)sulfonyl-5-methoxy-1-[(2,4,6-trimethylphenyl)methyl]indole-2-carboxamide (Compound 336),
N-(2-methoxyphenyl)sulfonyl-1-[(2,4,6-trimethylphenyl)methyl]indole-2-carboxamide (Compound 183),
N-[(6-methoxy-2-pyridyl)sulfonyl]-1-[(2,4,6-trimethylphenyl)methyl]indole-2-carboxamide (Compound 253),
N-(3-aminophenyl)sulfonyl-5-fluoro-1-[(2,4,6-trimethylphenyl)methyl]indole-2-carboxamide (Compound 153),
N-(3-aminophenyl)sulfonyl-6-methyl-1-[(2,4,6-trimethylphenyl)methyl]indole-2-carboxamide (Compound 62),
N-(benzenesulfonyl)-3-methyl-1-[(2,4,6-trimethylphenyl)methyl]indole-2-carboxamide (Compound 232),
N-(3-aminophenyl)sulfonyl-1-[(2,4,6-trimethylphenyl)methyl]indole-2-carboxamide (Compound 148),
N-(2-hydroxyphenyl)sulfonyl-1-[(2,4,6-trimethylphenyl)methyl]indole-2-carboxamide (Compound 112),
N-(benzenesulfonyl)-5,6-dimethoxy-1-[(2,4,6-trimethylphenyl)methyl]indole-2-carboxamide (Compound 198),
N-(4-aminophenyl)sulfonyl-1-[(2,4,6-trimethylphenyl)methyl]indole-2-carboxamide (Compound 134),
N-(benzenesulfonyl)-1-[(2,6-dimethylphenyl)methyl]indole-2-carboxamide (Compound 2),
N-(3-aminophenyl)sulfonyl-4-cyano-1-[(2,4,6-trimethylphenyl)methyl]indole-2-carboxamide (Compound 306),
N-[(2-methoxy-3-pyridyl)sulfonyl]-5-methyl-1-[(2,4,6-trimethylphenyl)methyl]indole-2-carboxamide (Compound 267),
4-fluoro-1-(1-phenylethyl)-N-(4-pyridylsulfonyl)indole-2-carboxamide (Compound 192),
N-[(2-methoxy-3-pyridyl)sulfonyl]-1-[(2,4,6-trimethylphenyl)methyl]indole-2-carboxamide (Compound 18),
N-(3-aminophenyl)sulfonyl-1-[(2,6-dimethylphenyl)methyl]indole-2-carboxamide (Compound 331),
N-(2-pyridylsulfonyl)-1-[(2,4,6-trimethylphenyl)methyl]indole-2-carboxamide (Compound 247),
N-(2-cyanophenyl)sulfonyl-1-[(2,4,6-trimethylphenyl)methyl]indole-2-carboxamide (Compound 358),
4-chloro-N-(4-pyridylsulfonyl)-1-[(2,4,6-trimethylphenyl)methyl]indole-2-carboxamide (Compound 82),
6-methyl-N-(4-pyridylsulfonyl)-1-[(2,4,6-trimethylphenyl)methyl]indole-2-carboxamide (Compound 38),
4-methoxy-N-(4-pyridylsulfonyl)-1-[(2,4,6-trimethylphenyl)methyl]indole-2-carboxamide (Compound 36),
4-fluoro-N-(4-pyridylsulfonyl)-1-[(2,4,6-trimethylphenyl)methyl]indole-2-carboxamide (Compound 298),
N-(4-pyridylsulfonyl)-1-[(2,4,6-trimethylphenyl)methyl]indole-2-carboxamide (Compound 227),
5-methyl-N-(4-pyridylsulfonyl)-1-[(2,4,6-trimethylphenyl)methyl]indole-2-carboxamide (Compound 25),
N-(3-aminophenyl)sulfonyl-3-methyl-1-[(2,4,6-trimethylphenyl)methyl]indole-2-carboxamide (Compound 118),
N-(3-aminophenyl)sulfonyl-1-[(2,6-dimethylphenyl)methyl]-6-methoxy-indole-2-carboxamide (Compound 116),
N-[(3-methoxy-2-pyridyl)sulfonyl]-1-[(2,4,6-trimethylphenyl)methyl]indole-2-carboxamide (Compound 258),
5-chloro-N-(4-pyridylsulfonyl)-1-[(2,4,6-trimethylphenyl)methyl]indole-2-carboxamide (Compound 65),
6-chloro-N-(4-pyridylsulfonyl)-1-[(2,4,6-trimethylphenyl)methyl]indole-2-carboxamide (Compound 24),
N-[(6-amino-2-pyridyl)sulfonyl]-1-[(4-cyano-2,6-dimethylphenyl)methyl]-5-methyl-indole-2-carboxamide (Compound 67),
N-[(4-amino-2-pyridyl)sulfonyl]-1-[(2,4,6-trimethylphenyl)methyl]indole-2-carboxamide (Compound 23),
N-(3-aminophenyl)sulfonyl-5-cyano-1-[(2,4,6-trimethylphenyl)methyl]indole-2-carboxamide (Compound 291),
N-(3-aminophenyl)sulfonyl-5,6-dimethoxy-1-[(2,4,6-trimethylphenyl)methyl]indole-2-carboxamide (Compound 598),
N-(3-aminophenyl)sulfonyl-6-cyano-1-[(2,4,6-trimethylphenyl)methyl]indole-2-carboxamide (Compound 1082),
N-[(2-amino-4-pyridyl)sulfonyl]-1-[(2,4,6-trimethylphenyl)methyl]indole-2-carboxamide (Compound 627),
N-[(6-amino-2-pyridyl)sulfonyl]-5-isopropyl-1-[(2,4,6-trimethylphenyl)methyl]indole-2-carboxamide (Compound 404),
N-[(6-amino-2-pyridyl)sulfonyl]-5-methyl-1-(p-tolyl)indole-2-carboxamide (Compound 653),
N-(3-aminophenyl)sulfonyl-5,6-dimethoxy-1-[(2,4,6-trimethylphenyl)methyl]indole-2-carboxamide (Compound 598),
N-(benzenesulfonyl)-1-[(2,6-dimethylphenyl)methyl]pyrrolo[2,3-b]pyridine-2-carboxamide (Compound 1291),
N-[(2-amino-4-pyridyl)sulfonyl]-1-[(2,4,6-trimethylphenyl)methyl]indole-2-carboxamide (Compound 627),
(2R)—N-[(6-amino-2-pyridyl)sulfonyl]-1-[(2,4,6-trimethylphenyl)methyl]indoline-2-carboxamide (Compound 462),
(2R)—N-(benzenesulfonyl)-1-[(2,4,6-trimethylphenyl)methyl]indoline-2-carboxamide (Compound 918),
N-[(6-amino-2-pyridyl)sulfonyl]-5-propyl-1-[(2,4,6-trimethylphenyl)methyl]indole-2-carboxamide (Compound 1158),
N-[(6-amino-2-pyridyl)sulfonyl]-5-ethyl-1-[(2,4,6-trimethylphenyl)methyl]pyrrolo[2,3-b]pyridine-2-carboxamide (Compound 816),
N-(3-aminophenyl)sulfonyl-1-[(2,4,6-trimethylphenyl)methyl]pyrrolo[2,3-b]pyridine-2-carboxamide (Compound 184), and
N-(benzenesulfonyl)-1-[(2,6-dimethylphenyl)methyl]pyrrolo[2,3-b]pyridine-2-carboxamide (Compound 1291).

Preparation 27: 4-methoxy-1-[(2,4,6-trimethylphenyl)methyl]pyrrolo[3,2-c]pyridine-2-carboxylic acid Step 1: methyl 4-chloro-1-[(2,4,6-trimethylphenyl)methyl]pyrrolo[3,2-c]pyridine-2-carboxylate

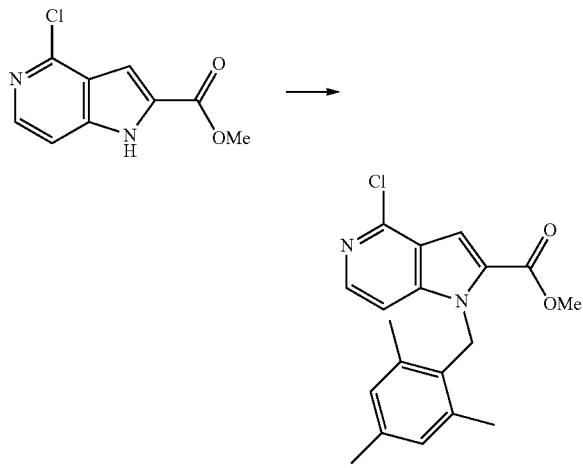

NaH (60%, 62 mg, 1.5 mmol) was added to a mixture of methyl 4-chloro-1H-pyrrolo[3,2-c]pyridine-2-carboxylate (250. mg, 1.19 mmol) and N,N-dimethylformamide (5 mL) at 0° C. The mixture was allowed to stir for 15 min at 0° C. before a solution of 2-(chloromethyl)-1,3,5-trimethyl-benzene (260. mg, 1.54 mmol) in N,N-dimethylformamide (1 mL) was added dropwise. The mixture was allowed to stir for 1H at room temperature, then 4 h at 60° C. The mixture was partitioned between 1N HCl and ethyl acetate. The layers were separated and the aqueous layer was extracted with ethyl acetate (3×). The combined organic layers were washed with brine (2×), dried over magnesium sulfate, filtered and concentrated under reduced pressure. The clear residue was subjected to silica gel column chromatography (0-20% ethyl acetate/hexanes) to give methyl 4-chloro-1-[(2,4,6-trimethylphenyl)methyl]pyrrolo[3,2-c]pyridine-2-carboxylate (370 mg, 91%). ESI-MS m/z calc. 342.1, found 343.4 (M+1)⁺; Retention time: 2.09 min (3 min run).

Step 2: methyl 4-methoxy-1-[(2,4,6-trimethylphenyl)methyl]pyrrolo[3,2-c]pyridine-2-carboxylate

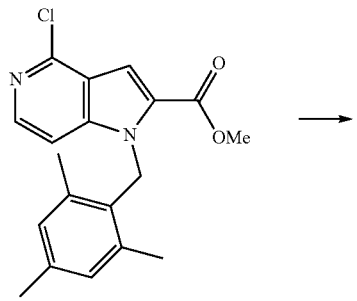

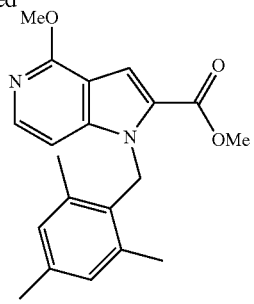

A mixture of methyl 4-chloro-1-[(2,4,6-trimethylphenyl)methyl]pyrrolo[3,2-c]pyridine-2-carboxylate (130. mg, 0.379 mmol) and NaOMe (7.6 mL of 0.50 M, 3.8 mmol) was heated at 110° C. for 30 min in the microwave. The mixture was concentrated to give methyl 4-methoxy-1-[(2,4,6-trimethylphenyl)methyl]pyrrolo[3,2-c]pyridine-2-carboxylate (56 mg, 15%) as a white solid. ESI-MS m/z calc. 338.2, found 339.4 (M+1)⁺; Retention time: 0.64 min (1 min run).

Step 3: 4-methoxy-1-[(2,4,6-trimethylphenyl)methyl]pyrrolo[3,2-c]pyridine-2-carboxylic acid

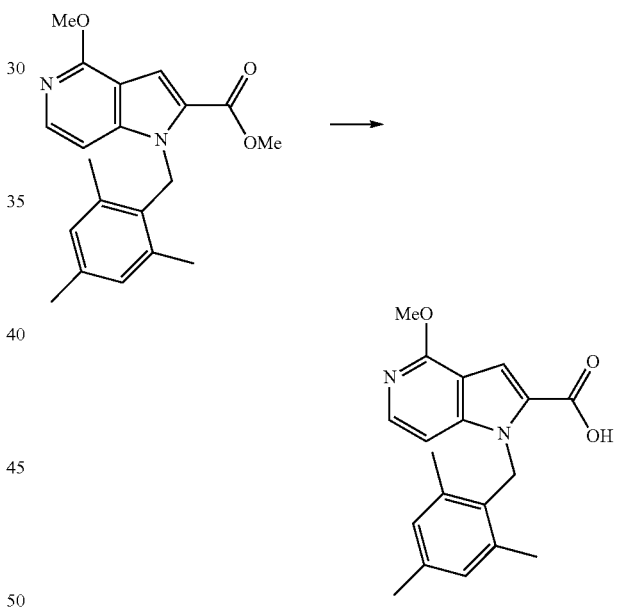

Lithium hydroxide (160 μL of 2.0 M, 0.32 mmol) was added to a mixture of methyl 4-methoxy-1-[(2,4,6-trimethylphenyl)methyl]pyrrolo[3,2-c]pyridine-2-carboxylate (50. mg, 0.15 mmol) and EtOH (1 mL) at room temperature. The mixture was allowed to stir at room temperature overnight. The mixture was concentrated and the residue was partitioned between 1N HCl and CH₂Cl₂. The layers were separated and the aqueous layer was extracted with CH₂Cl₂ (3×). The combined organics were washed with brine, dried over magnesium sulfate, filtered and concentrated. The residue was taken up in N,N-dimethylformamide and subjected to preparatory-HPLC (10-99% acetonitrile/water with 0.05 mM HCl) to give 4-methoxy-1-[(2,4,6-trimethylphenyl)methyl]pyrrolo[3,2-c]pyridine-2-carboxylic acid (39 mg, 81%) as a white solid. ESI-MS m/z calc. 324.2, found 325.4 (M+1)⁺; Retention time: 0.52 min (1 min run).

The following compound can be synthesized using the procedures described herein:
N-(3-aminophenyl)sulfonyl-4-methoxy-1-[(2,4,6-trimethylphenyl)methyl]pyrrolo[3,2-c]pyridine-2-carboxamide (Compound 943) and
N-[(6-amino-2-pyridyl)sulfonyl]-4-methoxy-1-[(2,4,6-trimethylphenyl)methyl]pyrrolo[2,3-b]pyridine-2-carboxamide (Compound 539)

Preparation 28: 2-[(2,4,6-trimethylphenyl)methyl]isoindoline-1-carboxylic acid hydrochloride

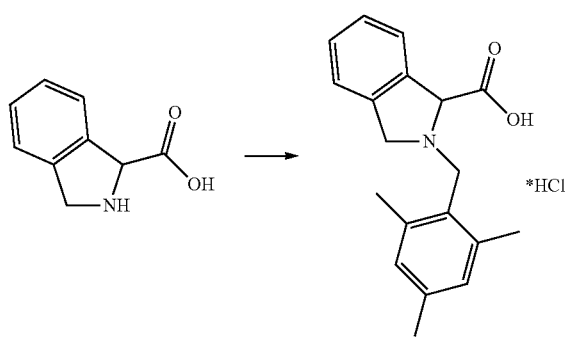 [SMILES: O=C(O)C1NCc2ccccc21 ; Cc1cc(C)c(CN2Cc3ccccc3C2C(=O)O)c(C)c1]

A suspension of isoindoline-1-carboxylic acid (100 mg, 0.613 mmol) and KOH (103 mg, 1.84 mmol) in isopropanol (600 µL) was stirred until a solution was formed. 2-(Chloromethyl)-1,3,5-trimethyl-benzene (114 mg, 0.674 mmol) was added and the reaction mixture was stirred for 3 h. The mixture was concentrated and the residue was subjected to preparatory-HPLC (10-99% acetonitrile/water with 0.05 mM HCl) to give 2-[(2,4,6-trimethylphenyl)methyl]isoindoline-1-carboxylic acid hydrochloride (99 mg, 49%). $^1$H NMR (400 MHz, DMSO) δ 7.39-7.33 (m, 1H), 7.34-7.25 (m, 3H), 6.87 (s, 2H), 4.97 (s, 1H), 4.34-3.94 (m, 4H), 2.40 (s, 6H), 2.23 (s, 3H). ESI-MS m/z calc. 295.2, found 296.2 (M+1)$^+$; Retention time: 0.43 min (1 min run).

The following compounds can be synthesized using the procedures described herein:
N-(3-aminophenyl)sulfonyl-2-[(2,4,6-trimethylphenyl)methyl]isoindoline-1-carboxamide (Compound 90),
N-(4-pyridylsulfonyl)-2-[(2,4,6-trimethylphenyl)methyl]isoindoline-1-carboxamide (Compound 94),
N-[(6-amino-2-pyridyl)sulfonyl]-2-[(2,4,6-trimethylphenyl)methyl]isoindoline-1-carboxamide (Compound 73),
N-(3-methoxyphenyl)sulfonyl-2-[(2,4,6-trimethylphenyl)methyl]isoindoline-1-carboxamide (Compound 16),
N-(benzenesulfonyl)-2-[(2,4,6-trimethylphenyl)methyl]isoindoline-1-carboxamide (Compound 6),
N-(3-hydroxyphenyl)sulfonyl-2-[(2,4,6-trimethylphenyl)methyl]isoindoline-1-carboxamide (Compound 254),
N-[(6-methoxy-2-pyridyl)sulfonyl]-2-[(2,4,6-trimethylphenyl)methyl]isoindoline-1-carboxamide (Compound 174),
N-[(6-oxo-1H-pyridin-2-yl)sulfonyl]-2-[(2,4,6-trimethylphenyl)methyl]isoindoline-1-carboxamide (Compound 319),
N-[(2-methoxy-3-pyridyl)sulfonyl]-2-[(2,4,6-trimethylphenyl)methyl]isoindoline-1-carboxamide (Compound 218),
N-(2-methoxyphenyl)sulfonyl-2-[(2,4,6-trimethylphenyl)methyl]isoindoline-1-carboxamide (Compound 79),
N-(2-pyridylsulfonyl)-2-[(2,4,6-trimethylphenyl)methyl]isoindoline-1-carboxamide (Compound 48),
N-[(6-methoxy-3-pyridyl)sulfonyl]-2-[(2,4,6-trimethylphenyl)methyl]isoindoline-1-carboxamide (Compound 200),
N-(3-aminophenyl)sulfonyl-2-(1-phenylethyl)isoindoline-1-carboxamide (Compound 187),
N-(4-aminophenyl)sulfonyl-2-[(2,4,6-trimethylphenyl)methyl]isoindoline-1-carboxamide (Compound 121),
N-[(4-amino-2-pyridyl)sulfonyl]-2-[(2,4,6-trimethylphenyl)methyl]isoindoline-1-carboxamide (Compound 32),
N-(2-aminophenyl)sulfonyl-2-[(2,4,6-trimethylphenyl)methyl]isoindoline-1-carboxamide (Compound 230),
N-[(6-amino-2-pyridyl)sulfonyl]-5-methyl-2-[(2,4,6-trimethylphenyl)methyl]-3,4-dihydro-1H-isoquinoline-3-carboxamide (Compound 95),
N-(3-aminophenyl)sulfonyl-2-[(2,4,6-trimethylphenyl)methyl]-3,4-dihydro-1H-isoquinoline-3-carboxamide (Compound 213),
N-[(6-amino-2-pyridyl)sulfonyl]-2-[1-(2,4,6-trimethylphenyl)ethyl]isoindoline-1-carboxamide (Compound 1186),
N-(benzenesulfonyl)-1-[(2,4,6-trimethylphenyl)methyl]-2,3,4,5-tetrahydro-1-benzazepine-2-carboxamide (Compound 604),
N-[(6-amino-2-pyridyl)sulfonyl]-1-methyl-2-[(2,4,6-trimethylphenyl)methyl]isoindoline-1-carboxamide (Compound 895),
N-[(3-hydroxy-2-pyridyl)sulfonyl]-1-methyl-2-[(2,4,6-trimethylphenyl)methyl]isoindoline-1-carboxamide (Compound 377),
N-[(6-amino-2-pyridyl)sulfonyl]-4-ethoxy-2-[(2-fluoro-6-methyl-phenyl)methyl]-1-methyl-isoindoline-1-carboxamide (Compound 1392),
N-(3-amino-4-propyl-phenyl)sulfonyl-4-ethoxy-1-methyl-2-[(2,4,6-trimethylphenyl)methyl]isoindoline-1-carboxamide (Compound 1367),
N-(3-amino-4-isopropyl-phenyl)sulfonyl-4-ethoxy-1-methyl-2-[(2,4,6-trimethylphenyl)methyl]isoindoline-1-carboxamide (Compound 1562),
N-(3-amino-4-ethyl-phenyl)sulfonyl-4-ethoxy-1-methyl-2-[(2,4,6-trimethylphenyl)methyl]isoindoline-1-carboxamide (Compound 1584),
N-[(6-amino-2-pyridyl)sulfonyl]-4-ethoxy-1-methyl-2-(o-tolylmethyl)isoindoline-1-carboxamide (Compound 1408) 4-ethoxy-N-indolin-5-ylsulfonyl-1-methyl-2-[(2,4,6-trimethylphenyl)methyl]isoindoline-1-carboxamide (Compound 1422)
N-(2-aminophenyl)sulfonyl-4-ethoxy-1-methyl-2-[(2,4,6-trimethylphenyl)methyl]isoindoline-1-carboxamide (Compound 1457)
N-(4-aminophenyl)sulfonyl-4-ethoxy-1-methyl-2-[(2,4,6-trimethylphenyl)methyl]isoindoline-1-carboxamide (Compound 1480) 4-ethoxy-1-methyl-N-[[6-[(2,2,2-trifluoroacetyl)amino]-2-pyridyl]sulfonyl]-2-[(2,4,6-trimethylphenyl)methyl]isoindoline-1-carboxamide (Compound 1616)
N-[(6-acetamido-2-pyridyl)sulfonyl]-4-ethoxy-1-methyl-2-[(2,4,6-trimethylphenyl)methyl]isoindoline-1-carboxamide (Compound 1415)
N-[(6-amino-3-pyridyl)sulfonyl]-4-ethoxy-1-methyl-2-[(2,4,6-trimethylphenyl)methyl]isoindoline-1-carboxamide (Compound 1413)
4-ethoxy-N-(2-hydroxyphenyl)sulfonyl-1-methyl-2-[(2,4,6-trimethylphenyl)methyl]isoindoline-1-carboxamide (Compound 1509)
4-ethoxy-N-(4-hydroxyphenyl)sulfonyl-1-methyl-2-[(2,4,6-trimethylphenyl)methyl]isoindoline-1-carboxamide (Compound 1453)

4-ethoxy-1-methyl-N-(3-pyridylsulfonyl)-2-[(2,4,6-trimethylphenyl)methyl]isoindoline-1-carboxamide (Compound 1669)

N-[(6-amino-5-chloro-2-pyridyl)sulfonyl]-4-ethoxy-1-methyl-2-[(2,4,6-trimethylphenyl)methyl]isoindoline-1-carboxamide (Compound 1596) 4-ethoxy-N-(3-methoxyphenyl)sulfonyl-1-methyl-2-[(2,4,6-trimethylphenyl)methyl]isoindoline-1-carboxamide (Compound 1470)

N-[(6-amino-2-pyridyl)sulfonyl]-4-ethoxy-2-[(3-fluoro-5-isobutoxy-phenyl)methyl]-1-methyl-isoindoline-1-carboxamide (Compound 1681)

4-ethoxy-1-methyl-N-thiazol-5-ylsulfonyl-2-[(2,4,6-trimethylphenyl)methyl]isoindoline-1-carboxamide (Compound 1606)

4-ethoxy-N-(1H-indol-6-ylsulfonyl)-1-methyl-2-[(2,4,6-trimethylphenyl)methyl]isoindoline-1-carboxamide (Compound 1393)

N-[[6-(difluoromethyl)-2-pyridyl]sulfonyl]-4-ethoxy-1-methyl-2-[(2,4,6-trimethylphenyl)methyl]isoindoline-1-carboxamide (Compound 1597)

4-ethoxy-N-[(3-hydroxy-2-pyridyl)sulfonyl]-1-methyl-2-[(2,4,6-trimethylphenyl)methyl]isoindoline-1-carboxamide (Compound 1642) (Compound 377)

4-ethoxy-1-methyl-N-thiazol-4-ylsulfonyl-2-[(2,4,6-trimethylphenyl)methyl]isoindoline-1-carboxamide (Compound 1542)

4-ethoxy-1-methyl-N-(4-pyridylsulfonyl)-2-[(2,4,6-trimethylphenyl)methyl]isoindoline-1-carboxamide (Compound 1449)

4-ethoxy-N-(1H-indol-4-ylsulfonyl)-1-methyl-2-[(2,4,6-trimethylphenyl)methyl]isoindoline-1-carboxamide (Compound 1666)

N-(2-acetamidothiazol-5-yl)sulfonyl-4-ethoxy-1-methyl-2-[(2,4,6-trimethylphenyl)methyl]isoindoline-1-carboxamide (Compound 1555)

4-ethoxy-N-(3-fluoro-2-methoxy-phenyl)sulfonyl-1-methyl-2-[(2,4,6-trimethylphenyl)methyl]isoindoline-1-carboxamide (Compound 1403)

4-ethoxy-1-methyl-N-(2-pyridylsulfonyl)-2-[(2,4,6-trimethylphenyl)methyl]isoindoline-1-carboxamide (Compound 1474)

4-ethoxy-1-methyl-N-thiazol-2-ylsulfonyl-2-[(2,4,6-trimethylphenyl)methyl]isoindoline-1-carboxamide (Compound 1546)

4-ethoxy-N-(3-fluorophenyl)sulfonyl-1-methyl-2-[(2,4,6-trimethylphenyl)methyl]isoindoline-1-carboxamide (Compound 1425)

N-[(2-amino-3-pyridyl)sulfonyl]-4-ethoxy-1-methyl-2-[(2,4,6-trimethylphenyl)methyl]isoindoline-1-carboxamide (Compound 1591)

N-[(6-amino-2-pyridyl)sulfonyl]-4-ethoxy-2-[(6-isopropoxy-3-pyridyl)methyl]-1-methyl-isoindoline-1-carboxamide (Compound 1662)

N-[(6-amino-2-pyridyl)sulfonyl]-2-[(2,6-dimethylphenyl)methyl]-4-ethoxy-1-methyl-isoindoline-1-carboxamide (Compound 1498)

2-[(2,6-dimethylphenyl)methyl]-4-ethoxy-N-[(6-fluoro-2-pyridyl)sulfonyl]-1-methyl-isoindoline-1-carboxamide (Compound 1676)

N-[(6-amino-2-pyridyl)sulfonyl]-2-[(6-chloro-3-pyridyl)methyl]-4-ethoxy-1-methyl-isoindoline-1-carboxamide (Compound 1565)

N-(benzenesulfonyl)-4-ethoxy-1-methyl-2-[(2,4,6-trimethylphenyl)methyl]isoindoline-1-carboxamide (Compound 1539)

N-(3-aminophenyl)sulfonyl-4-ethoxy-1-methyl-2-[(2,4,6-trimethylphenyl)methyl]isoindoline-1-carboxamide (Compound 1454)

N-[(6-amino-2-pyridyl)sulfonyl]-4-ethoxy-2-[(4-isopropylphenyl)methyl]-1-methyl-isoindoline-1-carboxamide (Compound 1576)

4-ethoxy-N-[(6-fluoro-2-pyridyl)sulfonyl]-2-[(4-isopropylphenyl)methyl]-1-methyl-isoindoline-1-carboxamide (Compound 1655)

N-[(6-amino-2-pyridyl)sulfonyl]-4-ethoxy-2-[(4-fluorophenyl)methyl]-1-methyl-isoindoline-1-carboxamide (Compound 1433)

4-ethoxy-2-[(4-fluorophenyl)methyl]-N-[(6-fluoro-2-pyridyl)sulfonyl]-1-methyl-isoindoline-1-carboxamide (Compound 1583)

N-[(6-amino-2-pyridyl)sulfonyl]-4-ethoxy-2-[(3-fluoro-5-methoxy-phenyl)methyl]-1-methyl-isoindoline-1-carboxamide (Compound 1421) 4-ethoxy-2-[(3-fluoro-5-methoxy-phenyl)methyl]-N-[(6-fluoro-2-pyridyl)sulfonyl]-1-methyl-isoindoline-1-carboxamide (Compound 1428)

(1S)—N-[(6-amino-2-pyridyl)sulfonyl]-4-ethoxy-1-methyl-2-[(2,4,6-trimethylphenyl)methyl]isoindoline-1-carboxamide (Compound 1372) (Compound 1346)

(1R)—N-[(6-amino-2-pyridyl)sulfonyl]-4-ethoxy-1-methyl-2-[(2,4,6-trimethylphenyl)methyl]isoindoline-1-carboxamide (Compound 1582) (Compound 1346)

(1S)-4-ethoxy-1-methyl-N-[(2-oxo-1H-pyridin-3-yl)sulfonyl]-2-[(2,4,6-trimethylphenyl)methyl]isoindoline-1-carboxamide (Compound 1541) (Compound 1237) (Compound 410)

(1R)-4-ethoxy-1-methyl-N-[(2-oxo-1H-pyridin-3-yl)sulfonyl]-2-[(2,4,6-trimethylphenyl)methyl]isoindoline-1-carboxamide (Compound 1476) (Compound 1237) (Compound 410)

N-(3-amino-4-chloro-phenyl)sulfonyl-4-ethoxy-1-methyl-2-[(2,4,6-trimethylphenyl)methyl]isoindoline-1-carboxamide (Compound 1587)

N-(3-amino-4-fluoro-phenyl)sulfonyl-4-ethoxy-1-methyl-2-[(2,4,6-trimethylphenyl)methyl]isoindoline-1-carboxamide (Compound 1394)

N-(3-aminopyrazin-2-yl)sulfonyl-1-methyl-2-[(2,4,6-trimethylphenyl)methyl]isoindoline-1-carboxamide (Compound 480), 1-methyl-N-[(2-oxo-1H-pyridin-3-yl)sulfonyl]-2-[(2,4,6-trimethylphenyl)methyl]isoindoline-1-carboxamide (Compound 1237), N-(3-aminophenyl)sulfonyl-1-methyl-2-[(2,4,6-trimethylphenyl)methyl]isoindoline-1-carboxamide (Compound 1273), N-(benzenesulfonyl)-1-methyl-2-[(2,4,6-trimethylphenyl)methyl]isoindoline-1-carboxamide (Compound 873), 1-methyl-N-(1H-pyrazol-5-ylsulfonyl)-2-[(2,4,6-trimethylphenyl)methyl]isoindoline-1-carboxamide (Compound 378), N-[(6-amino-2-pyridyl)sulfonyl]-1-methyl-2-(o-tolylmethyl)isoindoline-1-carboxamide (Compound 666), N-[(2-methoxy-3-pyridyl)sulfonyl]-1-methyl-2-[(2,4,6-trimethylphenyl)methyl]isoindoline-1-carboxamide (Compound 765), N-[(6-amino-2-pyridyl)sulfonyl]-2-[(2,6-dimethylphenyl)methyl]-1-methyl-isoindoline-1-carboxamide (Compound 790), N-[(3-methoxy-2-pyridyl)sulfonyl]-1-methyl-2-[(2,4,6-trimethylphenyl)methyl]isoindoline-1-carboxamide (Compound 825), N-[(6-amino-2-pyridyl)sulfonyl]-2-[(2,4-dimethylphenyl)methyl]-1-methyl-isoindoline-1-carboxamide (Compound 1058), N-[(2-methoxy-3-pyridyl)sulfonyl]-3,3-dimethyl-2-[(2,4,6-trimethylphenyl)methyl]isoindoline-1-carboxamide (Compound 1235), 4-ethoxy-1-methyl-N-[(2-oxo-1H-pyridin-3-yl)sulfonyl]-2-[(2,4,6-trimethylphenyl)methyl]isoindoline-1-carboxamide (Compound 1237) (Compound 410), N-[(6-amino-2-pyridyl)sulfonyl]-7-methoxy-1-methyl-2-[(2,4,6-trimethylphenyl)methyl]isoindoline-1-carboxamide (Compound 1075), N-[(6-amino-2-pyridyl)sulfonyl]-6-methoxy-1-methyl-2-[(2,4,6-trimethylphenyl)methyl]isoindoline-1-carboxamide (Compound 474), N-[(6-amino-2-pyridyl)sulfonyl]-4-methoxy-1-methyl-2-[(2,4,6-trimethylphenyl)methyl]isoindoline-1-carboxamide (Compound 1161), N-[(6-amino-2-pyridyl)sulfonyl]-5-methoxy-1-methyl-2-[(2,4,6-trimethylphenyl)methyl]isoindoline-1-carboxamide (Compound 406), 4-ethoxy-N-[(2-methoxy-3-pyridyl)sulfonyl]-1-methyl-2-[(2,4,6-trimethylphenyl)methyl]isoindoline-1-carboxamide (Compound 765) (Compound 648), N-[(6-amino-2-pyridyl)sulfonyl]-4-ethoxy-1-methyl-2-[(2,4,6-trimethylphenyl)methyl]isoindoline-1-carboxamide (Compound 1346), N-(3-amino-4-methyl-phenyl)sulfonyl-3,3-dimethyl-2-[(2,4,6-trimethylphenyl)methyl]isoindoline-1-carboxamide (Compound 448), N-(5-amino-2-methyl-phenyl)sulfonyl-3,3-dimethyl-2-[(2,4,6-trimethylphenyl)methyl]isoindoline-1-carboxamide (Compound 840), N-[(6-amino-2-pyridyl)sulfonyl]-7-hydroxy-1-methyl-2-[(2,4,6-trimethylphenyl)methyl]isoindoline-1-carboxamide (Compound 394), N-[(6-amino-2-pyridyl)sulfonyl]-6-hydroxy-1-methyl-2-[(2,4,6-trimethylphenyl)methyl]isoindoline-1-carboxamide (Compound 885), N-[(6-amino-2-pyridyl)sulfonyl]-4-hydroxy-1-methyl-2-[(2,4,6-trimethylphenyl)methyl]isoindoline-1-carboxamide (Compound 1338), N-[(2-oxo-1H-pyridin-3-yl)sulfonyl]-2-[(2,4,6-trimethylphenyl)methyl]-1,3,4,5-tetrahydro-2-benzazepine-3-carboxamide (Compound 855), N-[(2-methoxy-3-pyridyl)sulfonyl]-2-[(2,4,6-trimethylphenyl)methyl]-1,3,4,5-tetrahydro-2-benzazepine-3-carboxamide (Compound 1342), N-[(6-amino-2-pyridyl)sulfonyl]-2-[(2,4,6-trimethylphenyl)methyl]-1,3,4,5-tetrahydro-2-benzazepine-3-carboxamide (Compound 690), 3,3-dimethyl-N-[(2-oxo-1H-pyridin-3-yl)sulfonyl]-2-[(2,4,6-trimethylphenyl)methyl]isoindoline-1-carboxamide (Compound 1085), N-[(6-amino-2-pyridyl)sulfonyl]-3,3-dimethyl-2-[(2,4,6-trimethylphenyl)methyl]isoindoline-1-carboxamide (Compound 1101), N-(benzenesulfonyl)-2-[(2,4,6-trimethylphenyl)methyl]-1,3,4,5-tetrahydro-2-benzazepine-1-carboxamide (Compound 674), N-[(6-amino-2-pyridyl)sulfonyl]-2-[(2,4,6-trimethylphenyl)methyl]-1,3,4,5-tetrahydro-2-benzazepine-1-carboxamide (Compound 696), N-(3-aminophenyl)sulfonyl-2-[(2,4,6-trimethylphenyl)methyl]-3,4-dihydro-1H-isoquinoline-1-carboxamide (Compound 309), and (2S,4R)—N-[(6-amino-2-pyridyl)sulfonyl]-4-phenyl-1-[(2,4,6-trimethylphenyl)methyl]pyrrolidine-2-carboxamide.

Preparation 29: 4-isopropyl-N-[(2-oxo-1H-pyridin-3-yl)sulfonyl]-2-[(2,4,6-trimethylphenyl)methyl]isoindoline-1-carboxamide (Compound 103)

Step 1: 2,6-dibromobenzaldehyde

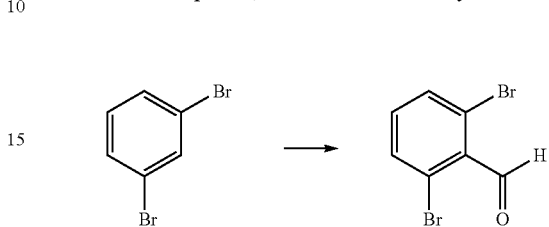

To a solution of iPr$_2$NH (21.2 mL, 150 mmol) in THF (180 mL) at 0° C. was slowly added n-BuLi (1.6 M, 94 mL, 150 mmol). The reaction mixture was stirred at 0° C. for 30 min and then cooled to −78° C. 1,3-Dibromobenzene (17.6 g, 74.6 mmol) in THF (80 mL) was slowly added over 20 min. The mixture was stirred at −78° C. for 30 min and N,N-dimethylformamide (11.6 mL, 150 mmol) was added. The mixture was stirred for 1 h, then treated with H$_2$SO$_4$ (2.5 M, 350 mL), and extracted with ethyl acetate/Et$_2$O (50/50, 3×300 mL). The combined extract were dried over MgSO$_4$ and filtered. The filtrate was concentrated to give 2,6-dibromobenzaldehyde (17.6 g, 89%). $^1$H NMR (250 MHz, CDCl$_3$) δ 10.3 (s, 1H), 7.65 (d, J=8.0 Hz, 2H), 7.23 (t, J=8.1 Hz, 1H).

Step 2: methyl (2,6-dibromobenzyl)glycinate

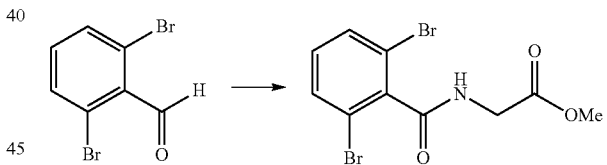

To a solution of glycine methyl ester hydrochloride (21.0 g, 167 mmol), 2,6-dibromobenzaldehyde (16.9 g, 64.4 mmol) and triethylamine (21.0 mL, 142 mmol) in dichloroethane (380 mL) were added acetic acid (8.40 mL, 145 mmol) and NaBH(OAc)$_3$ (33.5 g, 158 mmol). The mixture was stirred at room temperature under an argon atmosphere for 20 h. Additional glycine methyl ester hydrochloride (8.10 g, 64.4 mmol), triethylamine (9.52 g, 64.4 mmol), acetic acid (3.73 mL, 64.4 mmol) and NaBH(OAc)$_3$ (13.7 g, 64.4 mmol) were added and the reaction mixture was stirred for another 10 h. The reaction mixture was quenched by adding 1N NaOH, and the product was extracted with dichloromethane. The organic extracts were washed with brine, dried over sodium sulfate, filtered, and the solvent was removed in vacuo. The residue was purified by a plug filtration through a silica gel pad (0-50% ethyl acetate/hexanes to give methyl methyl (2,6-dibromobenzyl)glycinate (13.3 g, 62%) as an oil. $^1$H NMR (CDCl$_3$, 250 MHz) δ 7.52 (d, J=8.0 Hz, 2H), 6.98 (t, J=8.0, 1H), 4.20 (s, 2H), 3.70 (s, 3H), 3.50 (s, 2H).

Step 3: methyl N-(2,6-dibromobenzyl)-N-(2,4,6-trimethylbenzyl)glycinate

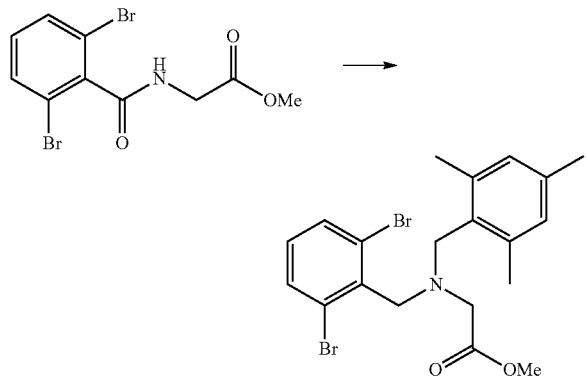

A mixture of methyl (2,6-dibromobenzyl)glycinate (13.3 g, 39.5 mmol), 2,4,6-trimethylbenzyl bromide (7.32 g, 43.4 mmol), $K_2CO_3$ (12.0 g, 86.8 mmol), and LiI (300 mg) in acetonitrile (300 mL) was stirred at 60° C. for 24 h. The reaction mixture was filtered and the filtrate was concentrated. The residue was purified by silica gel column chromatography (0-20% ethyl acetate/hexanes) to give methyl N-(2,6-dibromobenzyl)-N-(2,4,6-trimethylbenzyl)glycinate (18.0 g, 97%) as an oil which solidified on standing. $^1$H NMR (CDCl$_3$, 250 MHz) δ 7.54 (d, J=7.8 Hz, 2H), 7.00 (t, J=8.0, 1H), 6.79 (s, 2H), 4.34 (s, 2H), 4.04 (s, 2H), 3.71 (s, 3H), 3.50 (s, 2H), 2.23 (s, 3H), 2.18 (s, 6H).

Step 4: methyl 4-bromo-2-(2,4,6-trimethylbenzyl)isoindoline-1-carboxylate

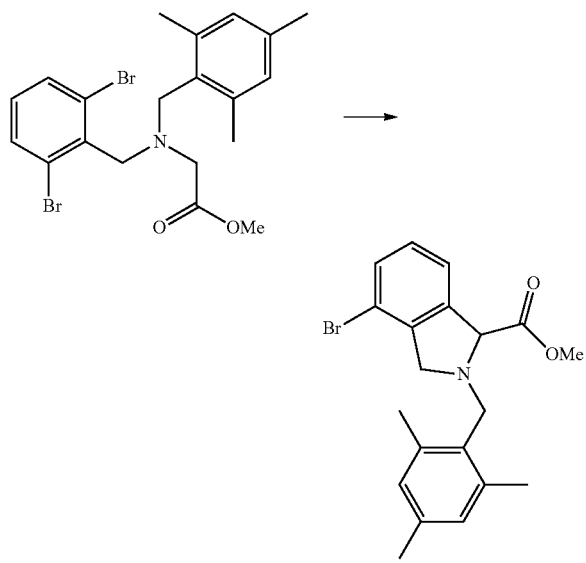

A mixture of methyl N-(2,6-dibromobenzyl)-N-(2,4,6-trimethylbenzyl)glycinate (16.0 g, 34.1 mmol), $Cs_2CO_3$ (33.3 g, 102 mmol) and Pd(PPh$_3$)$_4$ (2.0 g, 1.7 mmol) in THF (200 mL) was stirred at 110° C. in a sealed vessel for 60 h. Some THF (~50 mL) was removed by flushing with N2 before $Cs_2CO_3$ (6.5 g, 20 mmol) and Pd(PPh$_3$)$_4$ (400 mg, 0.34 mmol) were added. The reaction mixture was stirred at 110° C. for 24 h. The mixture was poured into water and was extracted with Et$_2$O. The organic extracts were washed with brine, dried over sodium sulfate, filtered and concentrated. The residue was purified by silica gel column chromatography (5-20% CH$_2$Cl$_2$/hexanes) to give methyl 4-bromo-2-(2,4,6-trimethylbenzyl)isoindoline-1-carboxylate (2.9 g, 22%). MS: 389 [M+1]$^+$.

Step 5: 4-bromo-2-(2,4,6-trimethylbenzyl)isoindoline-1-carboxylic Acid Hydrochloride

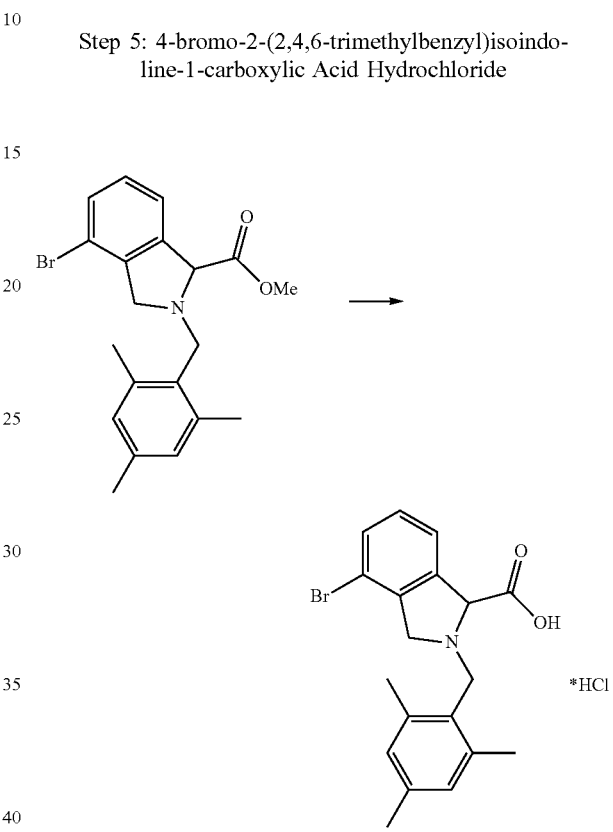

Methyl 4-bromo-2-(2,4,6-trimethylbenzyl)isoindoline-1-carboxylate (2.9 g, 7.4 mmol) was combined in a mixture of methanol (45 mL) and water (20 mL) containing sodium hydroxide (900. mg, 22.5 mmol). The resulting suspension was heated at 80° C. for 1 h. The reaction mixture was concentrated to remove the methanol. Water (50 mL) was added and the mixture was extracted with Et$_2$O. The aqueous phase was adjusted to pH ~2 with 6N HCl and was then extracted with CH$_2$Cl$_2$. The extract was dried over Na$_2$SO$_4$, filtered and concentrated. The residue was purified by silica gel column chromatography (0-5% methanol/CH$_2$Cl$_2$) and then subjected to preparatory-HPLC (10-100% acetonitrile/water with 0.05 mM trifluoroacetic acid) to give the desired product as the trifluoroacetic acid salt. The material was dissolved in methanol (30 mL) and was treated with HCl (1M, 10 mL). The mixture was then concentrated to dryness. The solid was suspended in CH$_2$Cl$_2$ (15 mL), sonicated for 10 min and filtered. The solid was washed with Et$_2$O and hexanes, and dried to give 4-bromo-2-(2,4,6-trimethylbenzyl)isoindoline-1-carboxylic acid hydrochloric acid (1.5 g, 49%). $^1$H NMR (DMSO, 250 MHz) δ 7.65 (d, J=7.8 Hz, 1H), 7.51 (d, J=7.8, 1H), 7.39 (m, 1H), 6.95 (s, 2H), 5.87 (s, 1H), 4.68 (s, 2H), 4.52 (d, J=10.8 Hz, 1H), 4.30 (d, J=10.8 Hz, 1H), 2.46 (s, 6H), 2.26 (s, 3H). MS: 375 [M+1]$^+$.

Step 6: 4-isopropenyl-2-[(2,4,6-trimethylphenyl)methyl]isoindoline-1-carboxylic Acid Hydrochloride

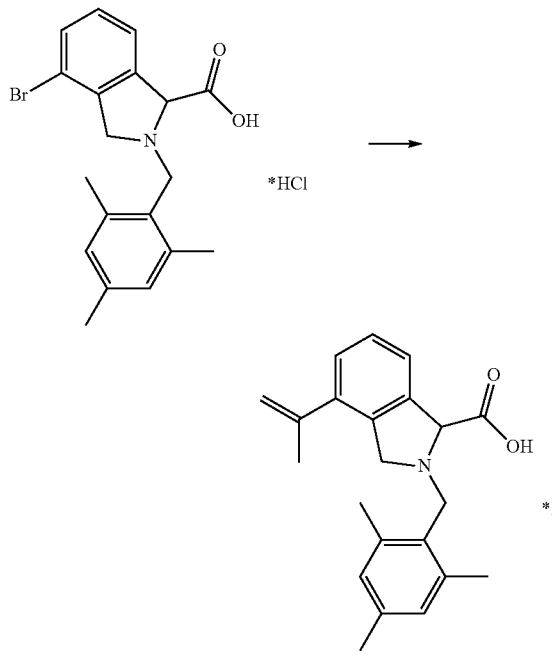

4-Bromo-2-[(2,4,6-trimethylphenyl)methyl]isoindoline-1-carboxylic acid hydrochloride (374 mg, 0.914 mmol), 2-isopropenyl-4,4,5,5-tetramethyl-1,3,2-dioxaborolane (269 mg, 1.60 mmol) and cesium carbonate (652 mg, 2.00 mmol) in dioxane (9 mL) and water (900 µL) was degassed with a stream of nitrogen for 1 min before adding dichloro[1,1'-bis(diphenylphosphino)ferrocene]palladium (II) dichloromethane adduct (73 mg, 0.10 mmol). The reaction mixture was degassed with a stream of nitrogen for 1 min and the mixture was stirred at 120° C. for 2 h. The reaction mixture was filtered and subjected to preparatory-HPLC (10-99% acetonitrile/water with 0.05 mM HCl) to give 4-isopropenyl-2-[(2,4,6-trimethylphenyl)methyl]isoindoline-1-carboxylic acid hydrochloric acid (180 mg, 48%). ESI-MS m/z calc. 335.2, found 336.2 (M+1)$^+$; Retention time: 0.53 min (1 min run).

Step 7: 4-isopropyl-2-[(2,4,6-trimethylphenyl)methyl]isoindoline-1-carboxylic acid hydrochloride

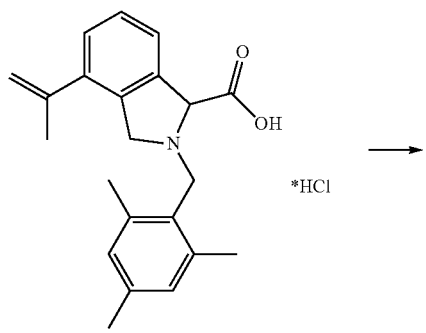

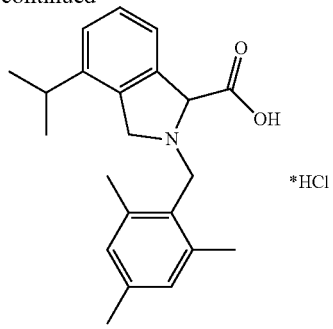

A mixture of 4-(prop-1-en-2-yl)-2-(2,4,6-trimethylbenzyl)isoindoline-1-carboxylic acid hydrochloride (43 mg, 0.12 mmol) and 10% palladium on carbon (5 mg, 0.005 mmol) in methanol (3 mL) was stirred under an atmosphere of hydrogen for 5 h. The reaction mixture was filtered and subjected to preparatory-HPLC (10-99% acetonitrile/water with 0.05 mM HCl) to give 4-isopropyl-2-[(2,4,6-trimethylphenyl)methyl]isoindoline-1-carboxylic acid hydrochloride (28 mg, 65%) as a colorless solid. ESI-MS m/z calc. 337.2, found 338.2 (M+1)$^+$; Retention time: 0.55 min (1 min run).

Step 8: 4-isopropyl-N-[(2-methoxy-3-pyridyl)sulfonyl]-2-[(2,4,6-trimethylphenyl)methyl]isoindoline-1-carboxamide (Compound 218)

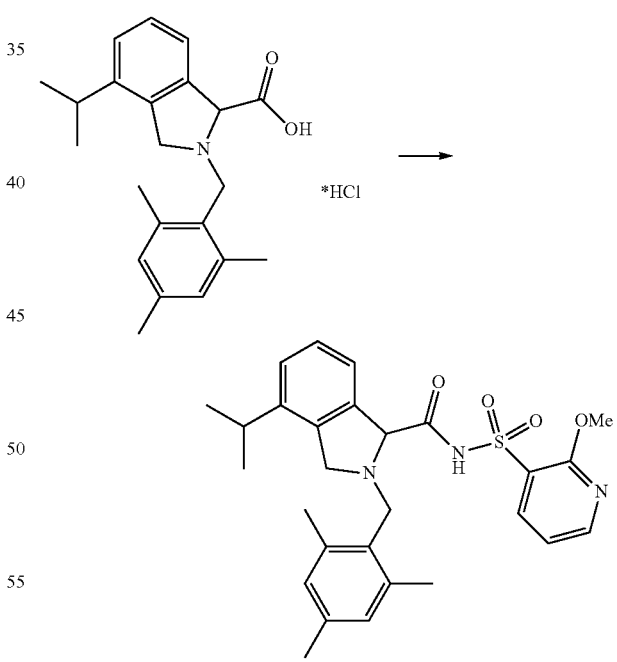

A mixture of 4-isopropyl-2-(2,4,6-trimethylbenzyl)isoindoline-1-carboxylic acid hydrochloride (28 mg, 0.075 mmol) and sodium carbonate (24 mg, 0.22 mmol) in N,N-dimethylformamide (1 mL) was degassed with a stream of nitrogen for 1 min before adding N-[(dimethylamino)-1H-1,2,3-triazolo-[4,5-b]pyridin-1-ylmethylene]-N-methyl-methanaminium hexafluorophosphate N-oxide (34 mg, 0.090 mmol). The mixture was degassed for 1 min and 2-methoxypyridine-3-sulfonamide (21 mg, 0.11 mmol) was added to the reaction mixture. The mixture was degassed for 1 min before it was stirred at room temperature for 17 h. The reaction mixture was filtered and subjected to preparatory-HPLC (10-99% acetonitrile/water with 0.05 mM HCl) to give 4-isopropyl-N-[(2-methoxy-3-pyridyl)sulfonyl]-2-[(2,4,6-trimethylphenyl)methyl]isoindoline-1-carboxamide (Compound 218) (16 mg, 42%). ESI-MS m/z calc. 507.2, found 508.4 (M+1)$^+$; Retention time: 0.68 min (1 min run).

Step 9: 4-isopropyl-N-[(2-oxo-1H-pyridin-3-yl)sulfonyl]-2-[(2,4,6-trimethylphenyl)methyl]isoindoline-1-carboxamide (Compound 103)

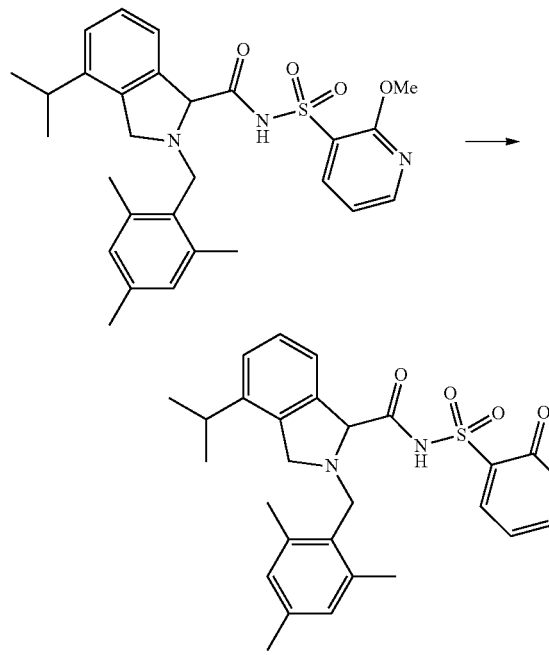

A mixture of 4-isopropyl-N-((2-methoxypyridin-3-yl)sulfonyl)-2-(2,4,6-trimethylbenzyl)isoindoline-1-carboxamide (16 mg, 0.032 mmol) in acetic acid (1 mL) and HBr (46 μL of 33% w/v, 0.19 mmol) (in acetic acid) was stirred at 50° C. for 1 h. The solvent was evaporated and the residue was subjected to preparatory-HPLC (10-99% acetonitrile/water with 0.05 mM HCl) to give 4-isopropyl-N-[(2-oxo-1H-pyridin-3-yl)sulfonyl]-2-[(2,4,6-trimethylphenyl)methyl]isoindoline-1-carboxamide (Compound 103) (12 mg, 69%). ESI-MS m/z calc. 493.2, found 494.3 (M+1)$^+$; Retention time: 1.44 min (3 min run).

The following compounds can be synthesized using the procedures described herein:
N-(3-aminophenyl)sulfonyl-4-ethyl-2-[(2,4,6-trimethylphenyl)methyl]isoindoline-1-carboxamide (Compound 30),
N-[(2-oxo-1H-pyridin-3-yl)sulfonyl]-4-phenyl-2-[(2,4,6-trimethylphenyl)methyl]isoindoline-1-carboxamide (Compound 508),
N-[(2-methoxy-3-pyridyl)sulfonyl]-4-phenyl-2-[(2,4,6-trimethylphenyl)methyl]isoindoline-1-carboxamide (Compound 427),
N-[(6-amino-2-pyridyl)sulfonyl]-4-phenyl-2-[(2,4,6-trimethylphenyl)methyl]isoindoline-1-carboxamide (Compound 554), and
N-(3-aminophenyl)sulfonyl-4-isopropyl-2-[(2,4,6-trimethylphenyl)methyl]isoindoline-1-carboxamide (Compound 299).

Preparation 30: 2-(tert-butyl)-4-(mesityloxy)pyrimidine-5-carboxylic acid

Step 1: ethyl 2-(tert-butyl)-4-hydroxypyrimidine-5-carboxylate

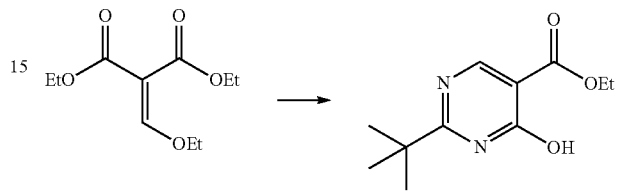

In EtOH (40 mL) was placed t-butylcarbamidine hydrochloride (3.71 g, 27.2 mmol). A solution of NaOEt (21% in EtOH, 8.80 g, 27.2 mmol) was added and the resulting mixture was stirred 15 min at room temperature. Diethyl ethoxymethylenemalonate (5.87 g, 27.2 mmol) was added and the reaction mixture was stirred at room temperature overnight. The reaction mixture was heated at reflux for 1 h and then the solvent was removed. The residue was dissolved in water (100 mL) and the pH adjusted to 3-4 with NaHSO$_4$ (1M). The solid was collected by filtration, washed with water (50 mL) and dried. The filtrate and washings were combined and extracted with ethyl acetate (2×150 mL). The combined extracts were dried over Na$_2$SO$_4$, filtered and concentrated. The residue plus the solid collected during filtration were subjected to column chromatography on silica gel, eluted with CH$_2$Cl$_2$/hexanes/methanol (50/50/0 to 45/45/10) to afford ethyl 2-(tert-butyl)-4-hydroxypyrimidine-5-carboxylate (2.85 g, 60%). $^1$H NMR (250 MHz, CDCl$_3$) δ 8.74 (s, 1H), 4.36 (q, J=7.3 Hz, 2H), 1.43 (s, 9H), 1.37 (t, J=7.2 Hz, 3H).

Step 2: ethyl 2-(tert-butyl)-4-chloropyrimidine-5-carboxylate

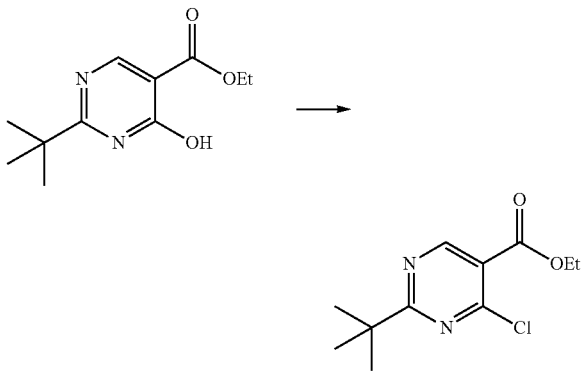

At 0° C., Et$_3$N (1.1 mL) was added to POCl$_3$ (32 mL), followed by the addition of ethyl 2-tert-butyl-4-hydroxypyrimidine-5-carboxylate (3.70 g, 16.5 mmol). The mixture was stirred at 40° C. for 1 h and the excess POCl$_3$ was removed under vacuum. The residue was carefully poured into ice (400 mL) and was extracted with $CH_2Cl_2$. The extract was washed with $NaHCO_3$ and water, dried over $Na_2SO_4$, filtered and concentrated. The crude material was subjected to silica gel column chromatography (10-90% $CH_2Cl_2$/hexanes) to afford ethyl 2-(tert-butyl)-4-chloropyrimidine-5-carboxylate (3.8 g, 95%) as a liquid. $(M+1)^+$ =243.4.

Step 3: 2-tert-butyl-4-(2,4,6-trimethylphenoxy)pyrimidine-5-carboxylate

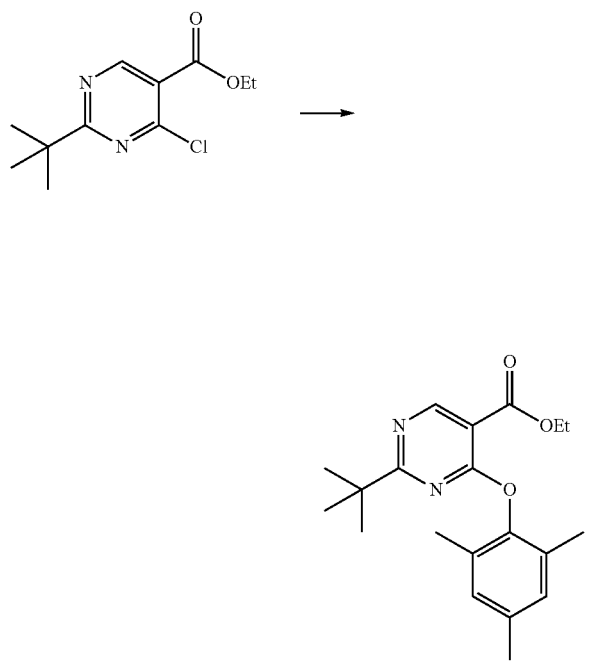

2,4,6-Trimethylphenol (2.10 g, 15.4 mmol) and sodium hydride (60%, 690 mg, 17.3 mmol) were combined in an anhydrous mixture of N,N-dimethylformamide (20 mL) and tetrahydrofuran (2 mL). The reaction mixture was stirred at room temperature for 15 min under an atmosphere of nitrogen. Ethyl 2-tert-butyl-4-chloropyrimidine-5-carboxylate (3.80 g, 15.7 mmol) was added and the reaction mixture was heated at 60° C. for 1 h. The reaction mixture was then allowed to cool to room temperature. The reaction mixture was diluted with water and extracted with ethyl acetate. The ethyl acetate layer was washed three times with water, dried over sodium sulfate, filtered and concentrated. The crude material was purified by silica gel column chromatography (0-30% ethyl acetate/hexanes) to yield ethyl 2-tert-butyl-4-(2,4,6-trimethylphenoxy)pyrimidine-5-carboxylate (3.1 g, 58%) as a liquid. ESI-MS m/z 351 $(M+1)^+$; H NMR (250 MHz, $CDCl_3$) δ 9.07 (s, 1H), 6.88 (s, 2H), 4.43 (q, J=7.2 Hz, 2H), 2.30 (s, 3H), 2.21 (s, 6H), 1.40 (t, J=7.2 Hz, 3H), 1.17 (s, 9H).

Step 4: 2-tert-butyl-4-(2,4,6-trimethylphenoxy)pyrimidine-5-carboxylic acid

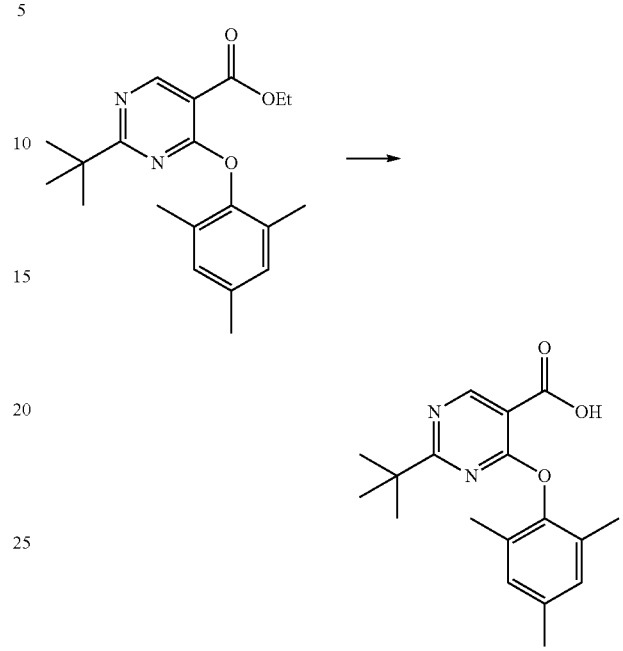

Ethyl 2-tert-butyl-4-(2,4,6-trimethylphenoxy)pyrimidine-5-carboxylate (3.1 g, 9.1 mmol) was combined in a mixture of methanol (25 mL) and water (30 mL) containing sodium hydroxide (1.2 g, 30 mmol). The resulting suspension was heated at 60° C. for 3 h. The reaction mixture was cooled to room temperature and was made acidic with 6M hydrochloric acid. The resulting precipitate was filtered, washed with water and dried to yield 2-tert-butyl-4-(2,4,6-trimethylphenoxy)pyrimidine-5-carboxylic acid (2.2 g, 77%) as a white solid. ESI-MS m/z 315 $(M+1)^+$; $^1$H NMR (250 MHz, DMSO) δ 9.01 (s, 1H), 6.95 (s, 2H), 2.27 (s, 3H), 1.98 (s, 6H), 1.11 (s, 9H).

The following compound can be synthesized using the procedures described herein:
N-(3-aminophenyl)sulfonyl-2-tert-butyl-4-(2,4,6-trimethylphenoxy)pyrimidine-5-carboxamide (Compound 68).

Preparation 31: 4-tert-butyl-1-[(2,4,6-trimethylphenyl)methyl]-1H-imidazole-2-carboxylic acid Step 1: 4-tert-butyl-1H-imidazole

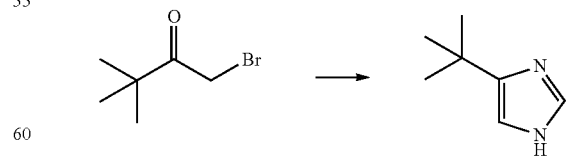

A mixture of 1-bromo-3,3-dimethylbutan-2-one (2.00 g, 11.2 mmol) in formamide (10 mL) was heated between 160-180° C. in a sealed tube equipped with a safety pressure release mechanism for 5 h. The mixture was cooled to room temperature and was poured into 10% aqueous sodium bicarbonate (30 mL). The solution was extracted with dichloromethane (2×30 mL). The combined organic layers were washed with 10% potassium carbonate, brine, dried over Na$_2$SO$_4$, filtered and concentrated under reduced pressure to provide 4-tert-butyl-1H-imidazole (1.37 g, 99%) as an oil. $^1$H NMR (300 MHz, CDCl$_3$) δ 1.31 (s, 9H), 6.76 (s, 1H), 7.56 (s, 1H), 9.63 (br.s., 1H).

Step 2: 4-tert-butyl-1-[(2,4,6-trimethylphenyl)methyl]-1H-imidazole

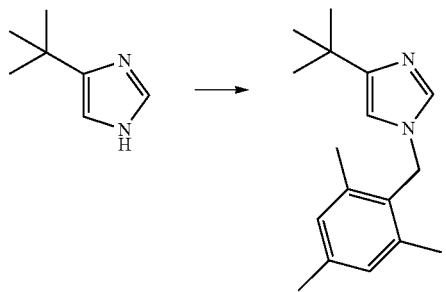

To 4-tert-butyl-1H-imidazole (1.37 g, 11.0 mmol) and cesium carbonate (7.20 g, 22.0 mmol) in acetonitrile (24 mL) was added 2-(bromomethyl)-1,3,5-trimethyl benzene (1.58 g, 9.38 mmol). The resulting suspension was stirred at room temperature overnight. Heptane (10 mL) was added to the reaction mixture before it was filtered through a pad of silica and washed with a 1:1 mixture of ethyl acetate:heptane. The eluent was concentrated to provide 4-tert-butyl-1-[(2,4,6-trimethylphenyl)methyl]-1H-imidazole (1.47 g, 52%) as an oil. $^1$H NMR (300 MHz, DMSO) δ 1.15 (s, 9H), 2.26 (s, 6H), 2.29 (s, 3H), 5.02 (s, 2H), 6.43 (s, 1H), 6.90 (s, 2H), 7.23 (s, 1H).

Step 3: 4-tert-butyl-1-[(2,4,6-trimethylphenyl)methyl]-1H-imidazole-2-carboxylic acid

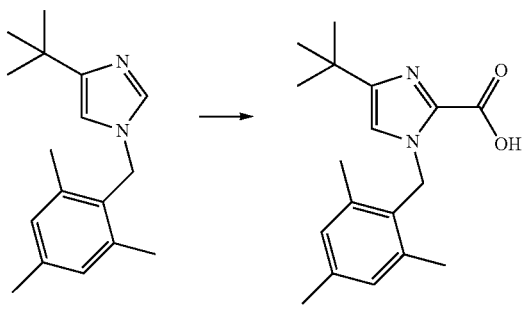 [SMILES: Cc1cc(C)c(Cn2cnc(C(C)(C)C)c2)c(C)c1 ; Cc1cc(C)c(Cn2cc(C(C)(C)C)nc2C(=O)O)c(C)c1]

To a solution of 4-tert-butyl-1-[(2,4,6-trimethylphenyl)methyl]-1H-imidazole (1.40 g, 5.46 mmol) in anhydrous THF (40 mL) was added n-BuLi (2.5 M, 2.62 mL, 6.55 mmol) at −78° C. The reaction mixture was stirred at −78° C. for 1H. A piece of dry ice was added in one portion at −78° C. The solution was stirred for 20 min at −78° C., and then the reaction mixture was allowed to reach to room temperature and was stirred under a CO$_2$ atmosphere for 2 h. The mixture was quenched with water (50 mL) and 1N HCl (7 ml) and then stirred for 10 min. The mixture was extracted with ethyl acetate (100 mL). The organic layer was separated from the aqueous phase and then concentrated under reduced pressure. The residue was triturated with CH$_2$Cl$_2$, concentrated, and then triturated again with methyl tert-butyl ether. The solid was washed with methyl tert-butyl ether and dried under reduced pressure to provide 4-tert-butyl-1-[(2,4,6-trimethylphenyl)methyl]-1H-imidazole (588 mg, 34%) as a white solid. $^1$H NMR (300 MHz, CDCl$_3$) δ 1.23 (s, 9H), 2.16 (s, 6H), 2.22 (s, 3H), 5.76 (s, 2H), 6.27 (s, 1H), 6.91 (s, 2H).

The following compound can be synthesized using the procedures described herein:
N-(3-aminophenyl)sulfonyl-4-tert-butyl-1-[(2,4,6-trimethylphenyl)methyl]imidazole-2-carboxamide (Compound 255).

Preparation 32: 4,4-dimethyl-2-[(2,4,6-trimethylphenyl)methyl]-1,3-dihydroisoquinoline-1-carboxylic acid Step 1: methyl (2-methyl-2-phenylpropyl)carbamate

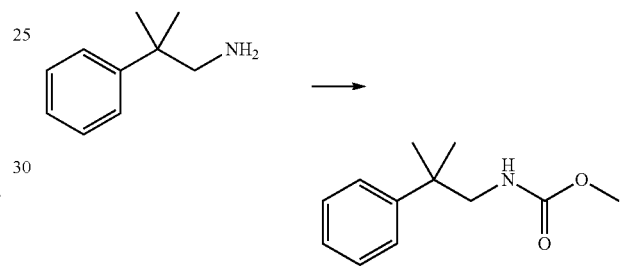

Methyl carbonochloridate (518 μL, 6.70 mmol) was added to a solution of 2-methyl-2-phenyl-propan-1-amine (1.00 g, 6.70 mmol) and pyridine (813 μL, 10.1 mmol) in CH$_2$Cl$_2$ (25 mL) at 0° C. The mixture was allowed to stir at room temperature for 1 h before it was quenched with 1N HCl. The mixture was washed with 1N HCl (2×25 mL), brine, dried over sodium sulfate, filtered and concentrated to give methyl (2-methyl-2-phenylpropyl)carbamate (911 mg, 66%). ESI-MS m/z calc. 207.1, found 208.4 (M+1)$^+$; Retention time: 0.54 min (1 min run).

Step 2: 2-methoxycarbonyl-4,4-dimethyl-1,3-dihydroisoquinoline-1-carboxylic acid

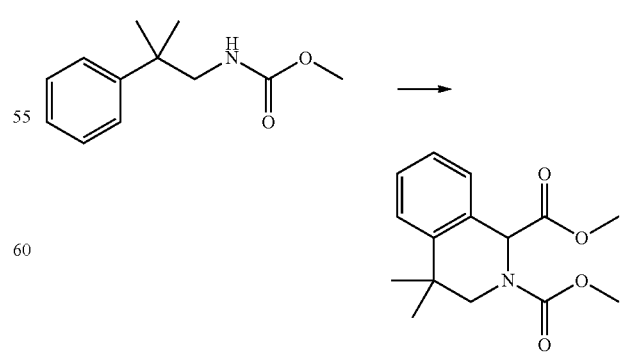

Methyl (2-methyl-2-phenylpropyl)carbamate (911 mg, 4.40 mmol) was suspended in acetic acid (15 mL) and H₂SO₄ (5 mL). The mixture was cooled to 0° C. before oxaldehydic acid hydrate (679 mg, 7.37 mmol) was added. The reaction mixture was allowed to warm to room temperature over 1H and was stirred at room temperature for an additional 2 h. The reaction mixture was poured over ice which and the mixture was extracted with ethyl acetate (3×50 mL). The combined organic layers were washed with brine, dried over sodium sulfate, filtered and concentrated to give 2-(methoxycarbonyl)-4,4-dimethyl-1,2,3,4-tetrahydroisoquinoline-1-carboxylic acid (1.1 g, 79%) as a white solid. ¹H NMR (400 MHz, CDCl₃) δ 7.55 (s, 1H), 7.45-7.17 (m, 3H), 5.66 (d, J=35.8 Hz, 1H), 3.90 (d, J=94.9 Hz, 4H), 3.33 (s, 1H), 1.28 (d, J=51.5 Hz, 6H). ESI-MS m/z calc. 263.1, found 264.0 (M+1)⁺; Retention time: 1.27 min (3 min run).

Step 3: 4,4-dimethyl-2,3-dihydro-1H-isoquinoline-1-carboxylic acid

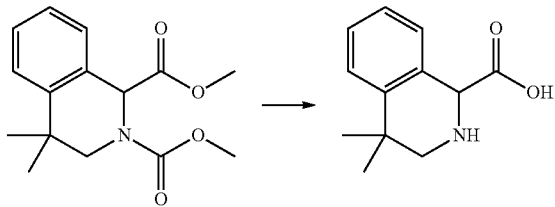

Iodo(trimethyl)silane (254 µL, 1.78 mmol) was added to 2-methoxycarbonyl-4,4-dimethyl-1,3-dihydroisoquinoline-1-carboxylic acid (412 mg, 1.49 mmol) in chloroform (10 mL). The mixture was heated at 65° C. for 2 h. Additional iodo(trimethyl)silane (254 µL, 1.78 mmol) was added and the reaction mixture was heated at 65° C. for 2 h. The reaction mixture was concentrated and the residue was subjected to preparatory-HPLC (10-99% acetonitrile/water with 0.05 mM HCl) to give 4,4-dimethyl-2,3-dihydro-1H-isoquinoline-1-carboxylic acid (261 mg, 85%). ESI-MS m/z calc. 205.1, found 206.4 (M+1)⁺; Retention time: 0.27 min (1 min run).

Step 4: 4,4-dimethyl-2-[(2,4,6-trimethylphenyl)methyl]-1,3-dihydroisoquinoline-1-carboxylic acid

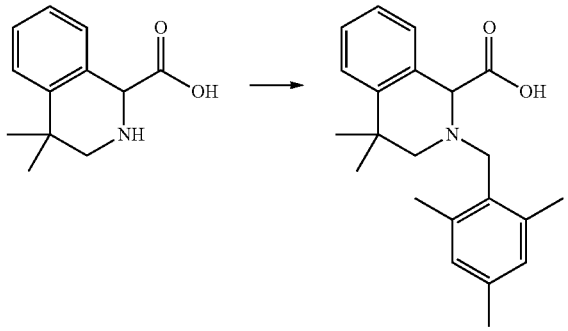

A suspension of 4,4-dimethyl-2,3-dihydro-1H-isoquinoline-1-carboxylic acid (260 mg, 1.27 mmol) and KOH (213 mg, 3.80 mmol) in isopropanol (1.6 mL) was stirred at room temperature for 20 min. 2-(Chloromethyl)-1,3,5-trimethylbenzene (235 mg, 1.39 mmol) was added and the reaction mixture was stirred for 3 h. The mixture was concentrated and the residue was subjected to preparatory-HPLC (10-99% acetonitrile/water with 0.05 mM HCL) to give 4,4-dimethyl-2-(2,4,6-trimethylbenzyl)-1,2,3,4-tetrahydroisoquinoline-1-carboxylic acid. ESI-MS m/z calc. 337.2, found 338.0 (M+1)⁺; Retention time: 1.42 min (3 min run).

The following compound can be synthesized using the procedures described herein: N-[(6-amino-2-pyridyl)sulfonyl]-4,4-dimethyl-2-[(2,4,6-trimethylphenyl)methyl]-1,3-dihydroisoquinoline-1-carboxamide (Compound 140).

Preparation 33:
4-tert-butyl-2-(2,4,6-trimethylphenoxy)benzoic acid

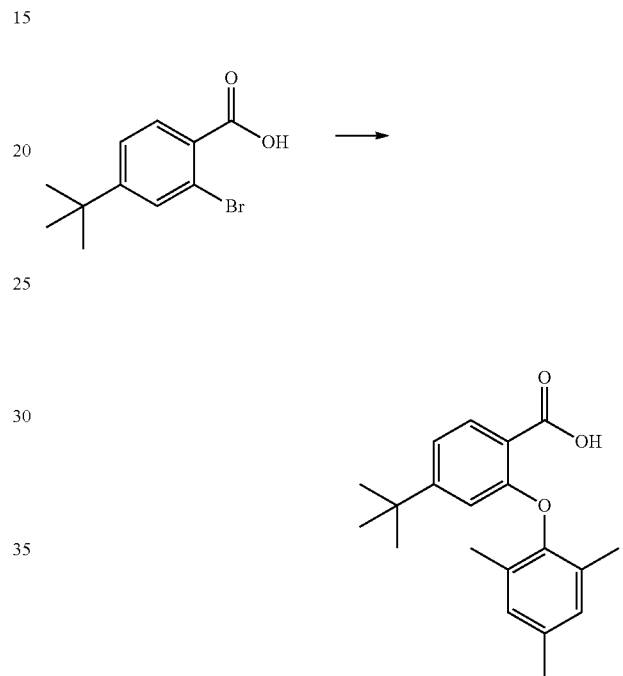

A mixture of 2-bromo-4-tert-butyl-benzoic acid (500 mg, 1.95 mmol), 2,4,6-trimethylphenol (397 mg, 2.92 mmol), Cs₂CO₃ (1.27 g, 3.89 mmol), Cu(OTf)₂ (49 mg, 0.097 mmol) and toluene (10 mL) was combined in a microwave vial before it was sealed and heated at 125° C. for 4 h. The mixture was cooled to room temperature and was partitioned between ethyl acetate (50 mL) and water (50 mL). The layers were separated and the aqueous layer was made acid by the addition of 1N HCl. The aqueous layer was extracted with ethyl acetate (2×30 mL). The combined organics were dried over magnesium sulfate, filtered and concentrated. The residue was subjected to silica gel column chromatography (0-3% methanol/CH₂Cl2) to give 4-tert-butyl-2-(2,4,6-trimethylphenoxy)benzoic acid (250 mg, 39%) as a white solid. ESI-MS m/z calc. 312.2, found 313.4 (M+1)⁺; Retention time: 2.14 min (3 min run). ¹H NMR (400 MHz, DMSO) δ 12.66 (s, 1H), 7.73 (d, J=8.2 Hz, 1H), 7.07 (dd, J=8.2, 1.8 Hz, 1H), 6.99 (s, 2H), 6.35 (d, J=1.7 Hz, 1H), 2.28 (s, 3H), 2.01 (s, 6H), 1.10 (s, 9H).

The following compounds can be synthesized using the procedures described herein: N-(3-aminophenyl)sulfonyl-4-tert-butyl-2-(2,4,6-trimethylphenoxy)benzamide (Compound 224) and N-[(6-amino-2-pyridyl)sulfonyl]-4-tert-butyl-2-(2,4,6-trimethylphenoxy)benzamide (Compound 102).

Preparation 34: 4-tert-butyl-1-[(2,4,6-trimethylphenyl)methyl]-1H-pyrrole-2-carboxylic acid

Step 1: ethyl 5-tert-butyl-2-[(2,4,6-trimethylphenyl)methyl]pyrazole-3-carboxylate

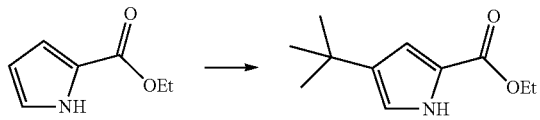

To a solution of gallium trichloride (4.00 g, 22.7 mmol) in carbon disulfide (30 mL) at room temperature were added ethyl pyrrole-2-carboxylate (2.87 g, 20.6 mmol) and 2-chloro-2-methylpropane (2.50 mL, 23.0 mmol). The mixture was then heated at reflux for 45 min. The reaction mixture was cooled to room temperature and was poured onto a mixture of ice and 1N HCl. The aqueous layer was extracted with dichloromethane. The organic layer was washed with saturated $NaHCO_3$, dried over $Na_2SO_4$, filtered and concentrated under reduced pressure. The residue was purified by silica gel chromatography (0-10% ethyl acetate/heptanes) to afford 4-tert-butyl-1H-pyrrole-2-carboxylate (260 mg, 7%), ethyl 5-tert-butyl-1H-pyrrole-2-carboxylate (2.1 g, 52%) and ethyl 3,5-di-tert-butyl-1H-pyrrole-2-carboxylate (352 mg, 7%) each isolated as white solids. Ethyl 4-tert-butyl-1H-pyrrole-2-carboxylate: $^1$H NMR (300 MHz, $CDCl_3$) δ 1.25 (s, 9H), 1.35 (t, J=7.1 Hz, 3H), 4.30 (q, J=7.1 Hz, 2H), 6.76 (dd, J=2.7, 1.8 Hz, 1H), 6.85 (dd, J=2.3, 1.9 Hz, 1H), 8.83 (br. s, 1H).

Step 2: ethyl 4-tert-butyl-1-[(2,4,6-trimethylphenyl)methyl]-1H-pyrrole-2-carboxylate

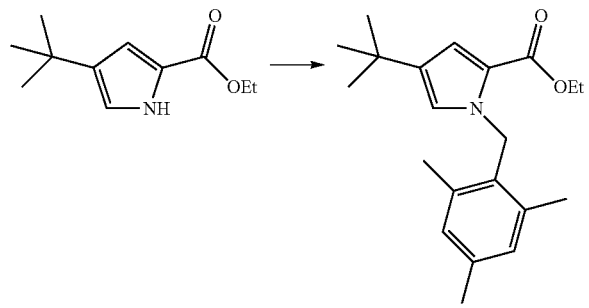 [SMILES: CCOC(=O)c1cc(C(C)(C)C)c[nH]1 ; CCOC(=O)c1cc(C(C)(C)C)cn1Cc1c(C)cc(C)cc1C]

Sodium hydride (24 mg as a 60% dispersion in mineral oil, 0.60 mmol) was added to a solution of ethyl 4-tert-butyl-1H-pyrrole-2-carboxylate (0.10 g, 0.51 mmol) in N,N-dimethylformamide (3 mL) at 0° C. The mixture was allowed to stir at 0° C. for 5 min before it was stirred at room temperature for 30 min. 2,4,6-Trimethylbenzyl bromide (0.12 g, 0.55 mmol) was added portion-wise and the mixture was stirred at room temperature for 20 h. The reaction mixture was quenched at 0° C. with aqueous saturated $NH_4Cl$ (4 mL). The mixture was extracted with ethyl acetate (80 mL) and the organic layer was washed with brine (2×30 mL) and water (30 mL), dried over $Na_2SO_4$, filtered and concentrated under reduced pressure. The residue was purified by silica gel chromatography (0-15% ethyl acetate/heptanes) to afford 4-tert-butyl-1-[(2,4,6-trimethylphenyl)methyl]-1H-pyrrole-2-carboxylate (161 mg, 98%) as a white solid. $^1$H NMR (300 MHz, $CDCl_3$) δ 1.12 (s, 9H), 1.38 (t, J=7.1 Hz, 3H), 2.20 (s, 6H), 2.31 (s, 3H), 4.31 (q, J=7.1 Hz, 2H), 5.47 (s, 2H), 6.11 (d, J=2.1 Hz, 1H), 6.91 (s, 2H), 6.92 (d, J=2.1, 1H).

Step 3: 4-tert-butyl-1-[(2,4,6-trimethylphenyl)methyl]-1H-pyrrole-2-carboxylic acid

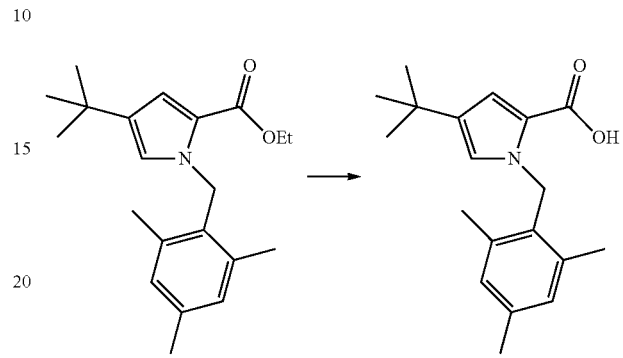

To a solution of ethyl 4-tert-butyl-1-[(2,4,6-trimethylphenyl)methyl]-1H-pyrrole-2-carboxylate (97 mg, 0.29 mmol) in methanol (6.3 mL) at room temperature was added a 1.0 N solution of NaOH (5.5 mL) and the mixture was heated at reflux for 4 hours. The mixture was cooled at room temperature and diluted with water (40 mL). The pH was adjusted to 4-5 using 1.0 N HCl and the aqueous layer was extracted with ethyl acetate (120 mL). The organic layer was washed with water (2×40 mL), dried over $Na_2SO_4$, filtered and concentrated under reduced pressure. The solid was triturated with diethyl ether to provide 4-tert-butyl-1-[(2,4,6-trimethylphenyl)methyl]-1H-pyrrole-2-carboxylic acid (74 mg, 84%) as a white solid. $^1$H NMR (300 MHz, $CDCl_3$) δ 1.12 (s, 9H), 2.21 (s, 6H), 2.32 (s, 3H), 5.47 (s, 2H), 6.18 (d, J=2.0 Hz, 1H), 6.91 (s, 2H), 7.06 (d, J=2.0 Hz, 1H).

The following compounds can be synthesized using the procedures described herein: N-(benzenesulfonyl)-4-tert-butyl-1-[(2,4,6-trimethylphenyl)methyl]pyrrole-2-carboxamide (Compound 242) and N-(3-aminophenyl)sulfonyl-4-tert-butyl-1-[(2,4,6-trimethylphenyl)methyl]pyrrole-2-carboxamide (Compound 195).

Preparation 35: 2-(tert-butyl)-5-(2,4,6-trimethylbenzyl)oxazole-4-carboxylic acid

Step 1: ethyl 2-hydroxy-2-pivalamidoacetate

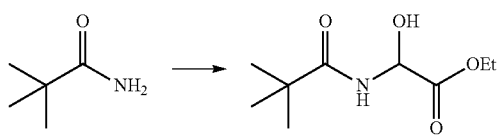

Acetic acid (2.61 g, 44.5 mmol) was added to a suspension of trimethylacetamide (9.00 g, 89.1 mmol) and ethyl glyoxylate (50% in toluene, 27.6 g, 133 mmol) in THF (60 mL). The mixture was heated at reflux for 16 h before it was cooled and concentrated to dryness. The residue was treated with heptanes and diethyl ether (10:1 ratio, 110 mL) to give a precipitate which was removed by filtration. The filtrate was concentrated to afford ethyl 2-hydroxy-2-pivalamidoacetate (16.8 g) as a colorless oil. ¹H NMR (300 MHz, CDCl₃) δ 1.22 (s, 9H), 2.27-1.35 (m, 3H), 3.63-3.75 (m, 1H), 4.20-4.36 (m, 2H), 5.50-5.60 (m, 1H), 6.65 (br s, 1H). LC-MS analysis: (M+1)⁺=204.1.

Step 2: ethyl 2-chloro-2-pivalamidoacetate

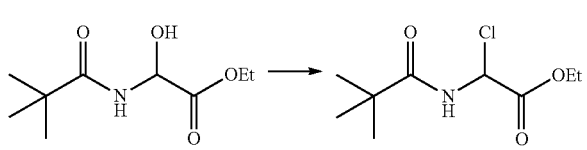

Thionyl chloride (28.6 g, 242 mmol) was added to a solution of ethyl 2-hydroxy-2-pivalamidoacetate (18.6 g, 80.8 mmol) and N,N-dimethylformamide (1 mL) in CH₂Cl₂ (100 mL) at 0° C. The mixture was stirred at room temperature for 16 h before it was concentrated to dryness to afford ethyl 2-chloro-2-pivalamidoacetate (20 g, 64%) as a yellow oil. ¹H NMR (300 MHz, CDCl₃) δ 1.27 (s, 9H), 1.29-1.37 (m, 3H), 4.20-4.36 (m, 2H), 6.25 (d, J=9.8, 1H), 6.85 (br s, 11H).

Step 3: ethyl 5-amino-2-(tert-butyl)oxazole-4-carboxylate

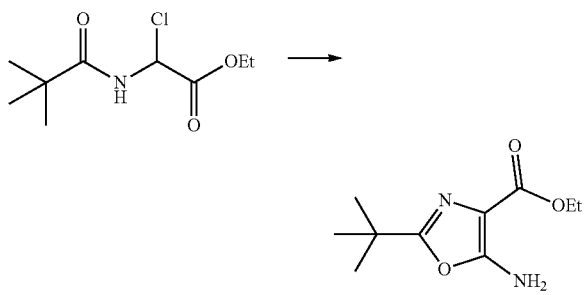

Diethylaluminum cyanide (1N in toluene, 76.6 mL, 76.7 mmol) was added to a solution of ethyl 2-chloro-2-(2,2-dimethylpropanamido)acetate (11.3 g, 2.71 mmol) in THF (110 mL) at 0° C. The mixture was stirred at room temperature for 16 h before sat. aqueous NH₄Cl (4 mL) was added to the reaction mixture. The mixture was filtered through Celite and the filtrate was extracted with ethyl acetate (200 mL). The organic layer was washed with brine, dried over Na₂SO₄, filtrated and concentrated. The residue was purified by silica gel column chromatography (50% ethyl acetate/heptane) to afford ethyl 5-amino-2-tert-butyl-1,3-oxazole-4-carboxylate (3.21 g, 30%) as a yellow solid. ¹H NMR (300 MHz, CDCl₃) δ 1.32 (s, 9H), 1.33-1.38 (m, 3H), 4.28-4.38 (m, 2H), 5.42 (br s, 2H). LC-MS analysis: [M+H]⁺=213.1.

Step 4: ethyl 5-bromo-2-(tert-butyl)oxazole-4-carboxylate

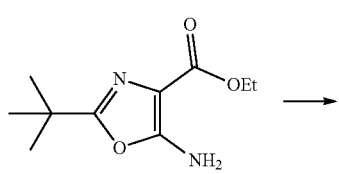

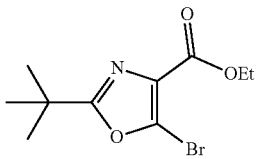

A mixture of ethyl 5-amino-2-tert-butyl-1,3-oxazole-4-carboxylate (1.50 g, 7.06 mmol) and CuBr₂ (1.59 g, 7.12 mmol) in acetonitrile (25 mL) was stirred at room temperature for 1 h followed by addition of tert-butyl nitrite (0.94 g, 9.2 mmol). The mixture was stirred at room temperature for 1 h, and then heated at 65° C. for 2.5 h. Brine was added to the reaction mixture and it was extracted with diethyl ether (200 mL). The organic layer was washed by brine spiked with a few drops of 1N HCl, dried over Na₂SO₄, filtrated and concentrated. The residue was purified by silica gel column chromatography (15% ethyl acetate/hexanes) to afford ethyl 5-bromo-2-tert-butyl-1,3-oxazole-4-carboxylate (1.31 g, 56%) as a yellow oil. ¹H NMR (300 MHz, CDCl₃) δ 1.19-1.23 (m, 3H), 1.25 (s, 9H), 4.38 (q, J=6.8 Hz, 2H). LC-MS analysis: (M+1)⁺=276.0.

Step 5: ethyl 2-(tert-butyl)-5-(2,4,6-trimethylbenzyl)oxazole-4-carboxylate

A mixture of ethyl 5-bromo-2-tert-butyl-1,3-oxazole-4-carboxylate (1.15 g, 4.18 mmol), Pd(OAc)₂ (0.09 g, 0.4 mmol) and tBuP-HBF₄ (0.24 g, 0.83 mmol) in THF (10 mL) was evacuated and back-filled with N2 three times. The mixture was cooled to 0° C. and (2,4,6-trimethylbenzyl)zinc(II) bromide (1M in THF, 8.36 mL, 8.36 mmol) was added slowly. The mixture was allowed to warm to room temperature and it was stirred for 16 h. The mixture was concentrated and the residue was subjected to silica gel column chromatography (15% ethyl acetate/heptanes) to afford ethyl 2-tert-butyl-5-[(2,4,6-trimethylphenyl)methyl]-1,3-oxazole-4-carboxylate (0.48 g, 31%) as yellow oil. ¹H NMR (300 MHz, CDCl₃) δ 1.27 (s, 9H), 1.41 (t, J=6.9 Hz, 3H), 2.25 (s, 3H), 2.31 (s, 6H), 4.35 (s, 2H), 4.42 (q, J=7.2 Hz, 2H), 6.85 (s, 2H). LC-MS analysis: (M+1)⁺=300.2.

Step 6: 2-(tert-butyl)-5-(2,4,6-trimethylbenzyl)oxazole-4-carboxylic acid

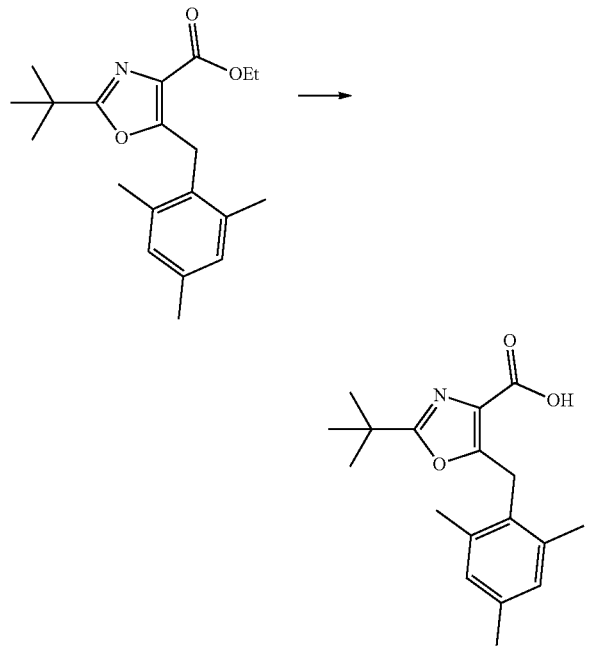

A mixture of ethyl 2-tert-butyl-5-[(2,4,6-trimethylphenyl)methyl]-1,3-oxazole-4-carboxylate (0.48 g, 1.5 mmol) and LiOH·H$_2$O (0.30 g, 7.3 mmol) in THF (4 mL) and water (4 mL) was stirred at room temperature for 16 h. The mixture was diluted with ethyl acetate (150 mL) the the pH was adjusted ~4 using 5% citric acid. The organic layer was washed with brine, dried over Na$_2$SO$_4$, filtrated and concentrated. The residue was triturated with diethyl ether and hexanes (8:1, 9 mL) to give 2-tert-butyl-5-[(2,4,6-trimethylphenyl)methyl]-1,3-oxazole-4-carboxylic acid (0.33 g, 75%) as a white solid. $^1$H NMR (300 MHz, CDCl$_3$) δ 1.28 (s, 9H), 2.25 (s, 3H), 2.33 (s, 6H), 4.37 (s, 2H), 6.85 (s, 2H). LC-MS analysis: (M+1)$^+$=302.2.

The following compound can be synthesized using the procedures described herein: N-(3-aminophenyl)sulfonyl-2-tert-butyl-5-[(2,4,6-trimethylphenyl)methyl]oxazole-4-carboxamide (Compound 360).

Preparation 36: lithium 3-tert-butyl-1-[(2,4,6-trimethylphenyl)methyl]-1H-1,2,4-triazole-5-carboxylate

Step 1: 2,2-dimethyl-N'-[(1E)-2,4,6-trimethylphenyl)methylidene]-propanehydrazide

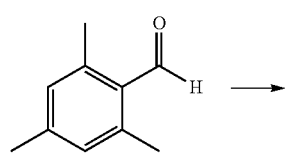

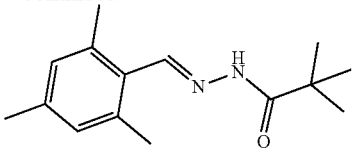

To a solution of 2,4,6-trimethylbenzaldehyde (2.96 g, 20.0 mmol) in 1,2-dichloroethane (16 mL) at room temperature was added 2,2-dimethylpropionic acid hydrazide (2.32 g, 20.0 mmol) and the mixture was stirred for 2 h at room temperature during which time a white precipitate formed. Diethyl ether (30 mL) was added to facilitate precipitation and stirring was continued for 1 h. Filtration over a fritted funnel, followed by washing of the solids with diethyl ether (30 mL) and drying under high vacuum afforded 2,2-dimethyl-N'-[(1E)-2,4,6-trimethylphenyl)methylidene]propanehydrazide (4.33 g, 88%) as a white solid. $^1$H NMR (300 MHz, CDCl$_3$) δ 1.33 (s, 9H), 2.28 (s, 3H), 2.45 (s, 6H), 6.87 (s, 2H), 8.52 (br. s, 1H), 8.61 (br. s, 1H). (M+1)$^+$=247.2.

Step 2: 2,2-dimethyl-N'-[(2,4,6-trimethylphenyl)methyl]-propanehydrazide

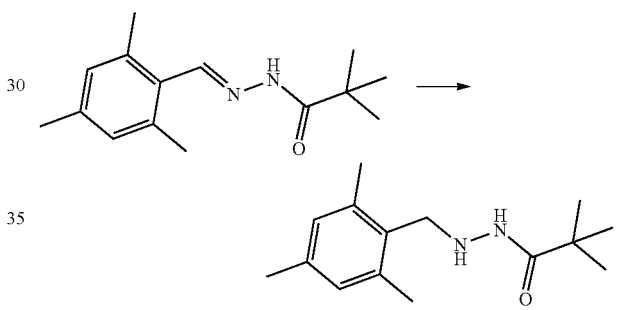

To a solution of 2,2-dimethyl-N'-[(1E)-2,4,6-trimethylphenyl)methylidene]-propanehydrazide (4.33 g, 17.6 mmol) in methanol (90 mL) was added 10% palladium on carbon (dry basis, 230 mg, 0.21 mmol). The reaction mixture was purged with hydrogen (3 cycles of vacuum/hydrogen) then stirred at room temperature for 2 h under an atmosphere of hydrogen. The reaction mixture was filtered over Celite, washed with methanol and concentrated under reduced pressure. The residue was purified by silica gel column chromatography (0-35% ethyl acetate/heptanes) to afford 2,2-dimethyl-N'-[(2,4,6-trimethylphenyl)methyl]propanehydrazide (3.76 g, 86%) as a white solid. $^1$H NMR (300 MHz, CDCl$_3$) δ 1.20 (s, 9H), 2.26 (s, 3H), 2.43 (s, 6H), 3.97 (s, 2H), 4.59 (br. s, 1H), 6.86 (s, 2H), 7.14 (br. s, 1H). (M+1)$^+$=249.2.

Step 3: ethyl 3-tert-butyl-1-[(2,4,6-trimethylphenyl)methyl]-1H-1,2,4-triazole-5-carboxylate

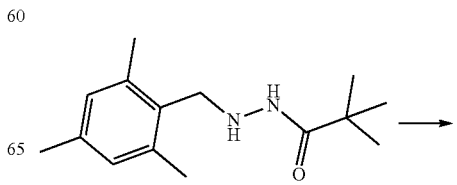

-continued

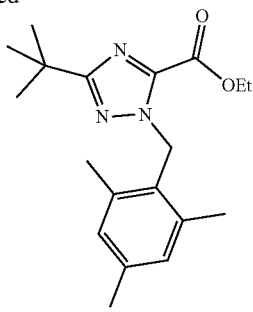

Triethyloxonium tetrafluoroborate (3.42 g, 18.0 mmol) was added portion-wise to a solution of ethyl thiooxamate (2.28 g, 17.1 mmol) in CH$_2$Cl$_2$ (35 mL). The resulting mixture was stirred at room temperature for 20 h. The mixture was then cooled to 0° C., and a solution of 2,2-dimethyl-N'-[(2,4,6-trimethylphenyl)methyl]propanehydrazide (4.48 g, 18.0 mmol) and triethylamine (2.5 mL, 18 mmol) in CH$_2$Cl$_2$ (20 mL) was added slowly, followed by an additional portion of triethylamine (1.3 mL, 9.0 mmol). The reaction mixture was then heated at reflux for 20 h. The crude mixture was concentrated under reduced pressure and the resulting yellow oil was purified by silica gel column chromatography (0-40% ethyl acetate/heptanes) to afford a solid. Reverse phase chromatographic separation with mixtures of 40% to 95% CH$_3$CN in water containing 0.1% formic acid afforded ethyl 3-tert-butyl-1-[(2,4,6-trimethylphenyl)methyl]-1H-1,2,4-triazole-5-carboxylate (620 mg, 11%) as a white solid. $^1$H NMR (300 MHz, CDCl$_3$) δ 1.29 (s, 91H), 1.43 (t, J=7.1 Hz, 3H), 2.27 (s, 3H), 2.31 (s, 6H), 4.49 (q, J=7.1 Hz, 2H), 5.71 (s, 2H), 6.86 (s, 2H). (M+1)$^+$ =330.2.

Step 4: lithium 3-tert-butyl-1-[(2,4,6-trimethylphenyl)methyl]-1H-1,2,4-triazole-5-carboxylate

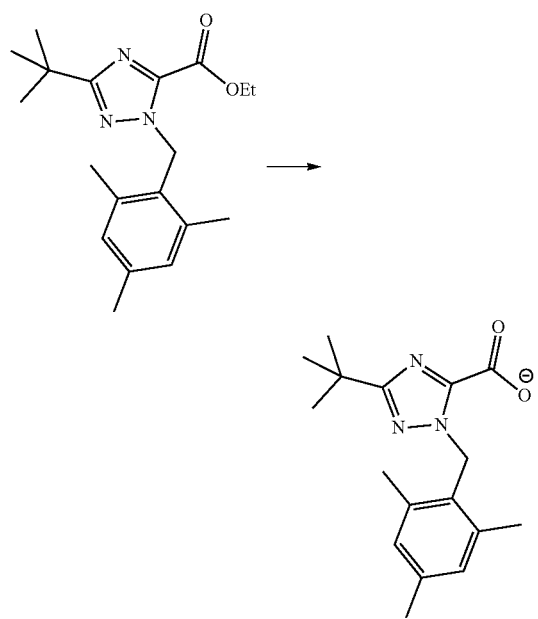

To a flask containing ethyl 3-tert-butyl-1-[(2,4,6-trimethylphenyl)methyl]-1H-1,2,4-triazole-5-carboxylate (110 mg, 0.33 mmol) and LiOH monohydrate (17 mg, 0.40 mmol) were successively added THF (2 mL) and water (1 mL) followed by one drop of methanol. The mixture was stirred at room temperature for 1 h. The volatiles (mostly THF and methanol) were removed under reduced pressure, then the mixture was frozen in a dry-ice/acetone bath and freeze-dried to afford lithium 3-tert-butyl-1-[(2,4,6-trimethylphenyl)methyl]-1H-1,2,4-triazole-5-carboxylate (98 mg, 95%) as a white solid. $^1$H NMR (300 MHz, CD$_3$OD) δ 1.24 (s, 9H), 2.24 (s, 3H), 2.33 (s, 6H), 5.73 (s, 2H), 6.82 (s, 2H).

The following compound can be synthesized using the procedures described herein:

N-(3-aminophenyl)sulfonyl-5-tert-butyl-2-[(2,4,6-trimethylphenyl)methyl]-1,2,4-triazole-3-carboxamide (Compound 261).

Preparation 37:
5-(tert-butyl)-3-(mesityloxy)pyrazine-2-carboxylic acid

Step 1: 3,3-dimethylbutane-1,2-diamine dihydrochloride

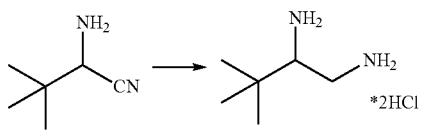

A mixture of 2-amino-3,3-dimethyl-butyronitrile hydrochloride (2.94 g, 20.0 mmol), HCl (sat. in EtOH, 10 mL), PtO$_2$ (600 mg) and methanol (200 mL) at room temperature was treated with hydrogen (50 psi) for 18 h. The reaction mixture was filtered through a pad of Celite and the filtrate was evaporated to give 3,3-dimethylbutane-1,2-diamine dihydrochloride as a white solid (3.9 g, 79%).

Step 2: ethyl 5-(tert-butyl)-3-hydroxypyrazine-2-carboxylate

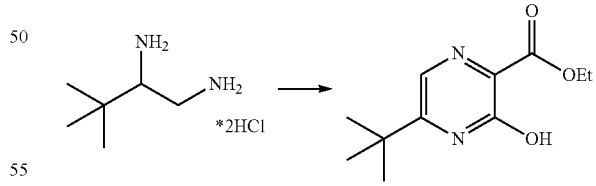

A mixture of 3,3-Dimethyl-butane-1,2-diamine dihydrochloride (3.9 g, 21 mmol), 2-oxo-malonic acid diethyl ester (3.45 mL, 22.7 mmol), Et$_3$N (5.8 mL, 41 mmol) and EtOH (400 mL) was heated at reflux for 20 h. All volatiles were removed and the residue was subjected to silica gel column chromatography (0-30% ethyl acetate/hexanes) (0/100 to 30/70) to give ethyl 5-(tert-butyl)-3-hydroxypyrazine-2-carboxylate (0.59 g, 13%) as a sticky oil, which solidified on standing. $^1$H NMR (250 MHz, CDCl$_3$) δ 8.36 (s, 1H), 4.55 (q, J=7.2 Hz, 2H), 1.49 (t, J=7.2 Hz, 3H), 1.41 (s, 9H).

Step 3: ethyl 5-(tert-butyl)-3-chloropyrazine-2-carboxylate

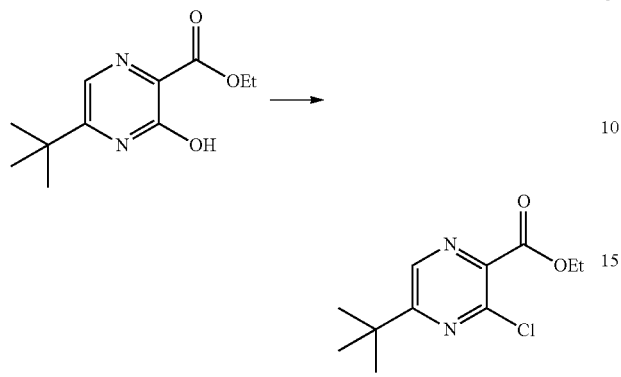

A mixture of ethyl 5-(tert-butyl)-3-hydroxypyrazine-2-carboxylate (590. mg, 2.63 mmol) and POCl₃ (10 mL) was heated at reflux for 5 h. The excess POCl₃ was removed under reduced pressure and the residue was partitioned between ethyl acetate and aq. NaHCO₃ (pH adjusted to ~6 by addition of sodium carbonate). The organic phase was separated, dried over Na₂SO₄, filtered and concentrated. The crude material was purified by silica gel column chromatography (0-30% ethyl acetate/hexanes) to give ethyl 5-(tert-butyl)-3-chloropyrazine-2-carboxylate (90 mg, 14%). ¹H NMR (250 MHz, CDCl₃) δ 8.59 (s, 1H), 4.49 (q, J=7.2 Hz, 2H), 1.44 (t, J=7.2 Hz, 3H), 1.40 (s, 9H).

Step 4: 5-tert-butyl-3-(2,4,6-trimethylphenoxy)pyrazine-2-carboxylic acid

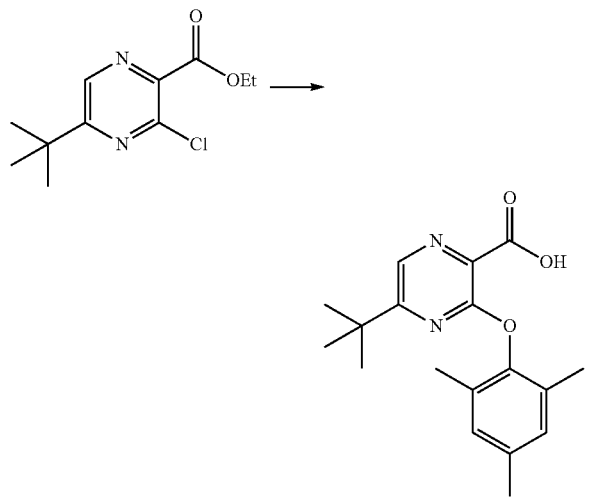

2,4,6-Trimethylphenol (51 mg, 0.38 mmol) and sodium hydride (18 mg, 0.45 mmol) were combined in anhydrous N,N-dimethylformamide (3 mL). The reaction mixture was stirred at room temperature for 15 min under an atmosphere of nitrogen. Ethyl 5-tert-butyl-3-chloro-pyrazine-2-carboxylate (90. mg, 0.37 mmol) in tetrahydrofuran (1 mL) was then added and the reaction mixture was heated at 60° C. for 1 h. To this mixture was added water (1 mL) and NaOH (120 mg). The resulted mixture was stirred at 70° C. for 1 h and was cooled to room temperature. The mixture was treated with HCl (1 M) to pH 3 and the mixture was extracted with ethyl acetate (3×). The combined extracts were concentrated to about 1 mL (N,N-dimethylformamide present). The residue was subjected to preparatory-HPLC (10-99% acetonitrile/water with 0.05 mM HCl) to give 5-tert-butyl-3-(2,4,6-trimethylphenoxy)pyrazine-2-carboxylic acid (55 mg, 47%). ¹HNMR (250 MHz, DMSO) δ 8.41 (s, 1H), 6.94 (s, 2H), 2.26 (s, 3H), 1.97 (s, 6H), 1.11 (s, 9H).

The following compound can be synthesized using the procedures described herein: N-(3-aminophenyl)sulfonyl-5-tert-butyl-3-(2,4,6-trimethylphenoxy)pyrazine-2-carboxamide (Compound 141).

Preparation 38:
5-(tert-butyl)-3-(mesityloxy)pyrazine-2-carboxylic acid

Step 1: ethyl 6-(tert-butyl)-4-chloronicotinate

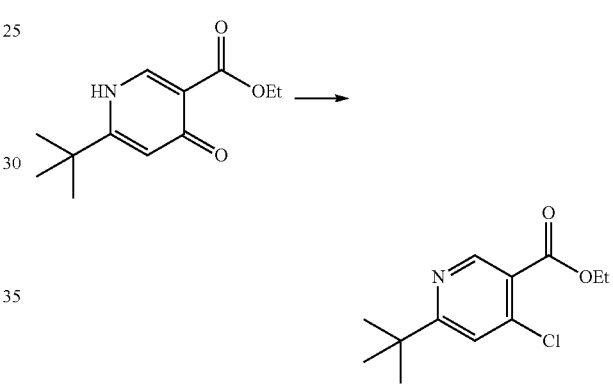

A solution of ethyl 6-tert-butyl-1,4-dihydro-4-oxopyridine-3-carboxylate (1.0 g, 4.5 mmol) and phosphorus oxychloride (10 mL) was heated at 110° C. for 1.5 h. The reaction solution was cooled to room temperature and was concentrated under reduced pressure. The residue was cooled to 0° C. before water (20 mL) and enough saturated aqueous NaHCO₃ were carefully added to bring the mixture to pH ~8. The mixture was extracted with ethyl acetate (3×). The combined organics were dried over MgSO₄, filtered, and concentrated under vacuum to give ethyl 6-(tert-butyl)-4-chloronicotinate (0.80 g, 73%) as a brown oil. ¹H NMR (CDCl₃, 250 MHz) δ 8.99 (s, 1H), 7.40 (s, 1H), 4.41 (m, 2H), 1.36 (m, 12H). LC-MS: (M+1)⁺=242.2.

Step 2: 6-tert-butyl-4-(2,4,6-trimethylphenoxy)pyridine-3-carboxylate

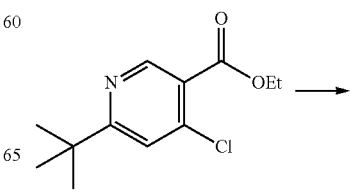

-continued

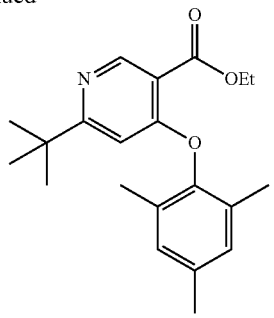

To a solution of 2,4,6-trimethylphenol (0.43 g, 3.1 mmol) in N,N-dimethylformamide (4 mL) and THF (1 mL) was added slowly 60% NaH (0.15 g, 3.9 mmol). The mixture was stirred at room temperature for 25 min before ethyl ethyl 6-(tert-butyl)-4-chloronicotinate (0.74 g, 3.1 mmol) was added. The reaction mixture was stirred at 60° C. for 1 h before it was cooled to room temperature and quenched by adding water. The mixture was extracted with ethyl acetate (3×). The combined organic extracts were concentrated and the residue was purified by silica gel column chromatography (0-20% ethyl acetate/hexanes) to afford ethyl 6-tert-butyl-4-(2,4,6-trimethylphenoxy)pyridine-3-carboxylate (0.45 g, 43%) as a light yellow oil. LC-MS: (M+1)$^+$=341.9.

Step 3: 6-tert-butyl-4-(2,4,6-trimethylphenoxy)pyridine-3-carboxylic acid

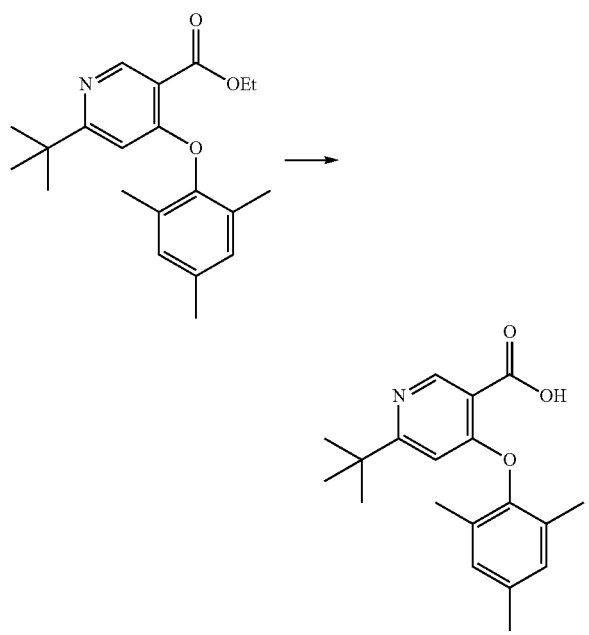

A solution of 6-(tert-butyl)-4-(mesityloxy)nicotinate (0.74 g, 2.2 mmol) and sodium hydroxide (0.21 g, 5.2 mmol) in EtOH (2 mL) and water (1 mL) was stirred at room temperature for 3 h. The reaction was concentrated and the residue was acidified with concentrated HCl to about pH 3. The crude material was purified by silica gel column chromatography (ethyl acetate) to give 6-tert-butyl-4-(2,4,6-trimethylphenoxy)pyridine-3-carboxylic acid (0.38 g, 55%) as a white solid. $^1$H NMR (CDCl$_3$, 250 MHz) δ 9.22 (s, 1H), 6.96 (s, 2H), 6.24 (s, 1H), 2.34 (s, 3H), 2.09 (s, 6H), 1.22 (s, 9H). LC-MS: (M+1)$^+$=314.1.

The following compound can be synthesized using the procedures described herein: N-(3-aminophenyl)sulfonyl-6-tert-butyl-4-(2,4,6-trimethylphenoxy)pyridine-3-carboxamide (Compound 338).

Preparation 39: N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 368) and N-[(6-amino-2-pyridyl)sulfonyl]-6-(3-fluoro-5-isobutoxy-phenyl)-2-[(4R)-2,2,4-trimethylpyrrolidin-1-yl]pyridine-3-carboxamide (Compound 1289)

Step 1: tert-butyl 2-chloro-6-(3-fluoro-5-isobutoxy-phenyl)pyridine-3-carboxylate

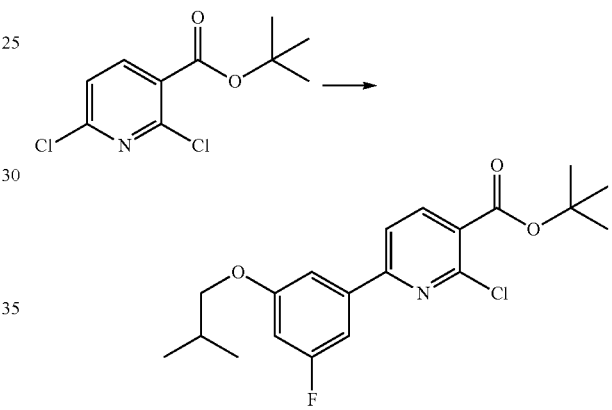

tert-Butyl 2,6-dichloropyridine-3-carboxylate (15.0 g, 60.5 mmol) and (3-fluoro-5-isobutoxy-phenyl)boronic acid (13.46 g, 63.48 mmol) were combined and fully dissolved in ethanol (150 mL) and toluene (150 mL). A suspension of sodium carbonate (19.23 g, 181.4 mmol) in water (30 mL) was added. Tetrakis(triphenylphosphine)palladium (0) (2.096 g, 1.814 mmol) was added under nitrogen. The reaction mixture was allowed to stir at 60° C. for 16 hours. Volatiles were removed under reduced pressure. The remaining solids were partitioned between water (100 mL) and ethyl acetate (100 mL). The organic layer was washed with brine (1×100 mL), dried over sodium sulfate, filtered and concentrated under reduced pressure. The material was subjected silica gel column chromatography on a 330 gram silica gel column, 0 to 20% ethyl acetate in hexanes gradient. The material was repurified on a 220 gram silica gel column, isocratic 100% hexane for 10 minutes, then a 0 to 5% ethyl acetate in hexanes gradient to yield tert-butyl 2-chloro-6-(3-fluoro-5-isobutoxy-phenyl)pyridine-3-carboxylate (18.87 g, 49.68 mmol, 82.2%) was obtained as a colorless oil. $^1$H NMR (400 MHz, DMSO-d$_6$) δ 8.24 (d, J=8.0 Hz, 1H), 8.16 (d, J=8.1 Hz, 1H), 7.48 (dd, J=9.4, 2.0 Hz, 2H), 6.99 (dt, J=10.8, 2.2 Hz, 1H), 3.86 (d, J=6.5 Hz, 2H), 2.05 (dt, J=13.3, 6.6 Hz, 1H), 1.57 (d, J=9.3 Hz, 9H), 1.00 (t, J=5.5 Hz, 6H). ESI-MS m/z calc. 379.13504, found 380.2 (M+1)$^+$; Retention time: 2.57 minutes.

Step 2: 2-chloro-6-(3-fluoro-5-isobutoxy-phenyl) pyridine-3-carboxylic acid

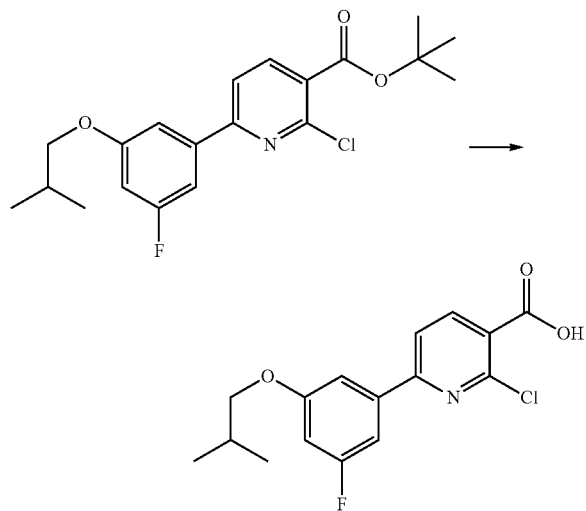

tert-Butyl 2-chloro-6-(3-fluoro-5-isobutoxy-phenyl)pyridine-3-carboxylate (18.57 g, 48.89 mmol) was dissolved in dichloromethane (200 mL). Trifluoroacetic acid (60 mL, 780 mmol) was added and the reaction mixture was allowed to stir at room temperature for 1 hour. The reaction mixture was stirred at 40° C. for 2 hours. The reaction mixture was concentrated under reduced pressure and taken up in ethyl acetate (100 mL). It was washed with a saturated aqueous sodium bicarbonate solution (1×100 mL) and brine (1×100 mL), dried over sodium sulfate, filtered and concentrated under reduced pressure. The crude product was suspended in ethyl acetate (75 mL) and washed with aqueous HCl (1 N, 1×75 mL). The organic layer was dried over sodium sulfate, filtered and concentrated under reduced pressure. The remaining solid (17.7 g) was stirred as a slurry in dichloromethane (35 mL) at 40° C. for 30 minutes. After cooling to room temperature, the remaining slurry was filtered, and then rinsed with cold dichloromethane to give 2-chloro-6-(3-fluoro-5-isobutoxy-phenyl)pyridine-3-carboxylic acid (11.35 g, 35.06 mmol, 72%) as a white solid. $^1$H NMR (400 MHz, DMSO-$d_6$) δ 13.76 (s, 1H), 8.31 (d, J=8.0 Hz, 1H), 8.17 (d, J=8.1 Hz, 1H), 7.54-7.47 (m, 2H), 7.00 (dt, J=10.8, 2.3 Hz, 1H), 3.87 (d, J=6.5 Hz, 2H), 2.05 (dt, J=13.3, 6.6 Hz, 1H), 1.01 (d, J=6.7 Hz, 6H). ESI-MS m/z calc. 323.1, found 324.1 (M+1)$^+$; Retention time: 1.96 minutes.

Step 3: N-[(6-amino-2-pyridyl)sulfonyl]-2-chloro-6-(3-fluoro-5-isobutoxy-phenyl)pyridine-3-carboxamide

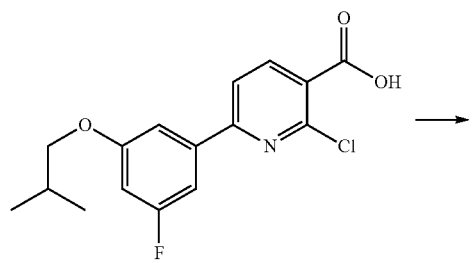

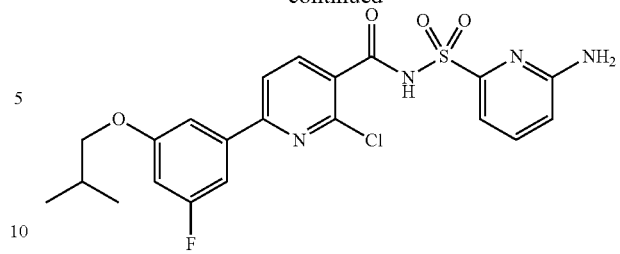

2-Chloro-6-(3-fluoro-5-isobutoxy-phenyl)pyridine-3-carboxylic acid (3.00 g, 9.27 mmol) was dissolved in N,N-dimethylformamide (30.00 mL), and 1,1'-carbonyldiimidazole (2.254 g, 13.90 mmol) was added to the solution. The solution was allowed to stir at 65° C. for 1 hour. In a separate flask, sodium hydride (444.8 mg, 11.12 mmol) was added to a solution of 6-aminopyridine-2-sulfonamide (1.926 g, 11.12 mmol) in N,N-dimethylformamide (15.00 mL). This mixture was stirred for one hour before being added to the prior reaction mixture. The final reaction mixture was stirred at 65° C. for 15 minutes. Volatiles were removed under reduced pressure. The remaining oil was taken up in ethyl acetate and washed with aqueous HCl (1 N, 1×75 mL) and brine (3×75 mL). The organic layer was dried over sodium sulfate, filtered and concentrated under reduced pressure. The remaining white solid (4.7 g) was fully dissolved in isopropanol (120 mL) in an 85° C. water bath. The colorless solution was allowed to slowly cool to room temperature with slow stirring over 16 hours. The crystalline solids that had formed were collected by vacuum filtration, and then rinsed with cold isopropanol (50 mL). Upon drying, N-[(6-amino-2-pyridyl)sulfonyl]-2-chloro-6-(3-fluoro-5-isobutoxy-phenyl)pyridine-3-carboxamide (3.24 g, 6.765 mmol, 73%) was obtained as a white solid. $^1$H NMR (400 MHz, DMSO-$d_6$) δ 12.78 (s, 1H), 8.15 (d, J=8.0 Hz, 1H), 8.09 (d, J=7.9 Hz, 1H), 7.73-7.63 (m, 1H), 7.49 (dd, J=8.6, 1.9 Hz, 2H), 7.21 (d, J=7.3 Hz, 1H), 6.99 (dt, J=10.7, 2.2 Hz, 1H), 6.74 (d, J=8.4 Hz, 1H), 6.64 (s, 2H), 3.86 (d, J=6.5 Hz, 2H), 2.05 (dp, J=13.3, 6.5 Hz, 1H), 1.02 (dd, J=12.7, 6.4 Hz, 6H).

Step 4: N-[(6-amino-2-pyridyl)sulfonyl]-6-(3-fluoro-5-isobutoxy-phenyl)-2-[(4R)-2,2,4-trimethylpyrrolidin-1-yl]pyridine-3-carboxamide (Compound 1289) and N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide

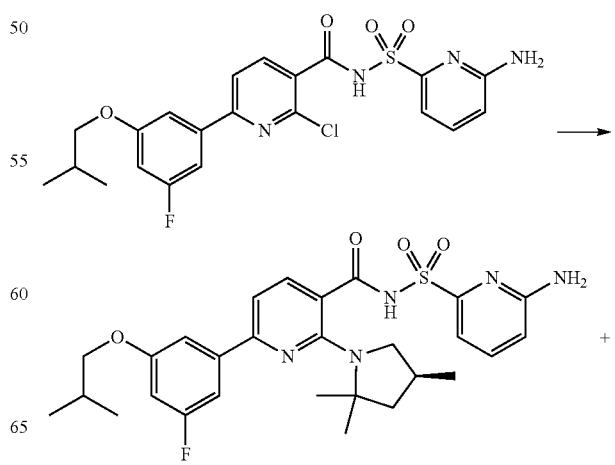

-continued

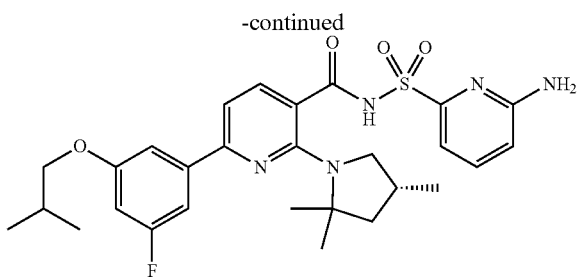

N-[(6-Amino-2-pyridyl)sulfonyl]-2-chloro-6-(3-fluoro-5-isobutoxy-phenyl)pyridine-3-carboxamide (309 mg, 0.645 mmol) was dissolved in dimethylsulfoxide (3.708 mL) and potassium carbonate (445.9 mg, 3.226 mmol) was slowly added, followed by 2,2,4-trimethylpyrrolidine (146.0 mg, 1.290 mmol). The reaction mixture was sealed and heated at 150° C. for 72 hours. The reaction was cooled down, diluted with water (50 mL), extracted 3 times with 50 mL portions of ethyl acetate, washed with brine, dried over sodium sulfate, filtered and evaporated to dryness. The crude material was dissolved in 2 mL of dichloromethane and purified by on silica gel using a gradient of 0 to 80% ethyl acetate in hexanes. The stereoisomers were separated using supercritical fluid chromatography on a ChiralPak AD-H (250×4.6 mm), 5 μm column using 25% isopropanol with 1.0% diethylamine in $CO_2$ at a flow rate of 3.0 mL/min. The separated enationmers were separately concentrated, diluted with ethyl acetate (3 mL) and washed with 1N aqueous hydrochloric acid. The organic layers were dried over sodium sulfate, filtered, and evaporated to dryness to give the pure compounds as pale yellow solids.

The first compound to eluet from the SFC conditions given above gave N-[(6-amino-2-pyridyl)sulfonyl]-6-(3-fluoro-5-isobutoxy-phenyl)-2-[(4R)-2,2,4-trimethylpyrrolidin-1-yl]pyridine-3-carboxamide (Compound 1289) (Hydrochloric Acid (1)) $^1$H NMR (400 MHz, DMSO-$d_6$) δ 12.47 (s, 1H), 7.78 (d, J=8.0 Hz, 1H), 7.69-7.57 (m, 1H), 7.56-7.46 (m, 1H), 7.41 (dt, J=10.1, 1.8 Hz, 1H), 7.26 (d, J=8.0 Hz, 1H), 7.21 (d, J=7.2 Hz, 1H), 6.89 (dt, J=10.7, 2.3 Hz, 1H), 6.69 (d, J=8.3 Hz, 1H), 3.83 (d, J=6.7 Hz, 2H), 2.61 (dq, J=9.7, 4.9 Hz, 2H), 2.24 (d, J=15.8 Hz, 1H), 2.06 (dq, J=13.3, 6.7 Hz, 1H), 1.93-1.82 (m, 1H), 1.61 (s, 3H), 1.59 (s, 3H), 1.48-1.33 (m, 1H), 1.32-1.20 (m, 2H), 0.99 (d, J=6.6 Hz, 6H), 0.88 (d, J=6.2 Hz, 3H). ESI-MS m/z calc. 555.2, found 556.4 (M+1)$^+$; Retention time: 2.76 minutes.

The second compound to eluet from the SFC conditions described above gave N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Hydrochloric Acid (1)) $^1$H NMR (400 MHz, Chloroform-d) δ 15.49 (s, 1H), 8.49 (d, J=8.2 Hz, 1H), 7.75-7.56 (m, 3H), 7.34 (t, J=1.8 Hz, 1H), 7.30 (dt, J=9.4, 1.9 Hz, 1H), 6.75-6.66 (m, 2H), 3.95 (s, 1H), 3.78 (d, J=6.5 Hz, 2H), 3.42 (s, 1H), 2.88-2.74 (m, 1H), 2.23 (dd, J=12.5, 8.0 Hz, 1H), 2.17-2.08 (m, 1H), 1.98-1.87 (m, 1H), 1.55 (s, 3H), 1.39 (s, 3H), 1.31 (d, J=6.7 Hz, 3H), 1.05 (d, J=6.7 Hz, 6H). ESI-MS m/z calc. 555.2, found 556.4 (M+1)$^+$; Retention time: 2.77 minutes. Absolute stereochemistry was confirmed by X-ray crystallography.

The following compound can be synthesized using the procedures described herein:
N-[(6-amino-2-pyridyl)sulfonyl]-6-(6-isopropoxy-3-pyridyl)-2-(3-isopropyl-1-piperidyl)pyridine-3-carboxamide (Compound 114), N-[(6-amino-2-pyridyl)sulfonyl]-2-[(4S)-2,2,4-trimethylpyrrolidin-1-yl]pyridine-3-carboxamide (Compound 946),
N-[(6-amino-4-methyl-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 1472),
N-[(6-amino-2-pyridyl)sulfonyl]-6-(3-fluoro-5-isobutoxy-phenyl)-2-(4-phenylbutoxy)pyridine-3-carboxamide (Compound 1686),
N-[(6-amino-2-pyridyl)sulfonyl]-2-[1-(1-naphthyl)ethylamino]pyridine-3-carboxamide (Compound 1769),
N-[(6-amino-2-pyridyl)sulfonyl]-2-[2-(o-tolyl)azepan-1-yl]pyridine-3-carboxamide (Compound 1772),
N-[(6-amino-2-pyridyl)sulfonyl]-2-[3-(cyclopropylmethyl)-2,2-dimethyl-pyrrolidin-1-yl]pyridine-3-carboxamide (Compound 1794),
N-[(6-amino-2-pyridyl)sulfonyl]-2-(3-benzyl-2,2-dimethyl-pyrrolidin-1-yl)pyridine-3-carboxamide (Compound 2275),
N-[(6-amino-2-pyridyl)sulfonyl]-2-[1-[2-(trifluoromethyl)phenyl]ethoxy]pyridine-3-carboxamide (Compound 2501),
N-[(6-amino-2-pyridyl)sulfonyl]-2-[2-(1,3-benzoxazol-2-yl)phenoxy]pyridine-3-carboxamide (Compound 2544),
N-[(6-amino-2-pyridyl)sulfonyl]-2-[(2-cyclohexylcyclohexyl)amino]pyridine-3-carboxamide (Compound 2599),
N-[(6-amino-2-pyridyl)sulfonyl]-2-(3-phenyl-1-piperidyl)pyridine-3-carboxamide (Compound 2615),
6-(3-fluoro-5-isobutoxy-phenyl)-N-[(6-methoxy-4-methyl-2-pyridyl)sulfonyl]-2-[(4S)-2,2,4-trimethylpyrrolidin-1-yl]pyridine-3-carboxamide (Compound 1482),
6-(3-fluoro-5-isobutoxy-phenyl)-N-tetrahydrofuran-3-ylsulfonyl-2-[(4S)-2,2,4-trimethylpyrrolidin-1-yl]pyridine-3-carboxamide (Compound 1640),
N-cyclopropylsulfonyl-6-(3-fluoro-5-isobutoxy-phenyl)-2-[(4S)-2,2,4-trimethylpyrrolidin-1-yl]pyridine-3-carboxamide (Compound 1525),
N-[(6-amino-2-pyridyl)sulfonyl]-2-[(2S,5R)-2,5-dimethylpyrrolidin-1-yl]-6-(3-fluoro-5-isobutoxy-phenyl)-4-methoxy-pyridine-3-carboxamide (Compound 1254),
N-[(6-amino-2-pyridyl)sulfonyl]-2-[(2S,5R)-2,5-dimethylpyrrolidin-1-yl]-6-(3-fluoro-5-isobutoxy-phenyl)pyridine-3-carboxamide (Compound 171),
N-[(6-Amino-2-pyridyl)sulfonyl]-2-[(2S,5R)-2,5-dimethylpyrrolidin-1-yl]-6-(6-isopropoxy-3-pyridyl)pyridine-3-carboxamide,
N-[(6-amino-2-pyridyl)sulfonyl]-6-(6-isopropoxy-3-pyridyl)-2-[(3R)-3-phenyl-1-piperidyl]pyridine-3-carboxamide (Compound 233),
2-(2,5-dimethylpyrrolidin-1-yl)-6-(3-fluoro-5-isobutoxy-phenyl)-N-[(2-oxo-1H-pyridin-3-yl)sulfonyl]pyridine-3-carboxamide (Compound 307),
N-[(6-amino-2-pyridyl)sulfonyl]-6-(6-isopropoxy-3-pyridyl)-2-(3-methyl-1-piperidyl)pyridine-3-carboxamide (Compound 321),
N-[(6-amino-2-pyridyl)sulfonyl]-6-tert-butyl-2-[(2,4-dimethyl-3-pyridyl)oxy]pyridine-3-carboxamide (Compound 460),
N-[(6-amino-2-pyridyl)sulfonyl]-2-(2,3-dimethyl-1-piperidyl)-6-(6-isopropoxy-3-pyridyl)pyridine-3-carboxamide (Compound 353),
6-(3-fluoro-5-isobutoxy-phenyl)-2-(1-piperidyl)-N-(1H-pyrazol-5-ylsulfonyl)pyridine-3-carboxamide (Compound 355),
N-[(6-amino-2-pyridyl)sulfonyl]-6-(6-isopropoxy-3-pyridyl)-2-[(2R)-2-methylpyrrolidin-1-yl]pyridine-3-carboxamide (Compound 1354), N-[(6-amino-2-pyridyl)sulfonyl]-6-(6-isopropoxy-3-pyridyl)-2-(3,3,4-trimethyl-1-piperidyl)pyridine-3-carboxamide (Compound 435), 6-(4-ethoxyphenyl)-2-(4-methyl-1-piperidyl)-N-(1H-pyrazol-5-ylsulfonyl)pyridine-3-carboxamide (Compound 445), N-[(6-amino-2-pyridyl)sulfonyl]-2-[(2R,3R)-2,3-dimethylpyrrolidin-1-yl]-6-(6-isopropoxy-3-pyridyl)pyridine-3-carboxamide (Compound 441), N-[(6-amino-2-pyridyl)sulfonyl]-6-(3-fluoro-5-isobutoxyphenyl)-2-[4-(4-pyridyl)butoxy]pyridine-3-carboxamide (Compound 1687), N-[(6-amino-2-pyridyl)sulfonyl]-2-(2,2-dimethyl-4-oxopyrrolidin-1-yl)-6-(3-fluoro-5-isobutoxy-phenyl)-1,2-dihydropyridine-3-carboxamide, N-[(6-amino-2-pyridyl)sulfonyl]-2-(2,2-dimethyl-3-oxopyrrolidin-1-yl)-6-(3-fluoro-5-isobutoxy-phenyl)-1,2-dihydropyridine-3-carboxamide, N-[(6-amino-2-pyridyl)sulfonyl]-6-(3-fluoro-5-isobutoxyphenyl)-2-[4-(3-pyridyl)butoxy]pyridine-3-carboxamide (Compound 1690), N-[(6-amino-2-pyridyl)sulfonyl]-6-(3-fluoro-5-isobutoxyphenyl)-2-[4-(2-pyridyl)butoxy]pyridine-3-carboxamide (Compound 1688), N-[(6-amino-2-pyridyl)sulfonyl]-6-(3-fluoro-5-isobutoxyphenyl)-2-(3-pyrazol-1-ylpropoxy)pyridine-3-carboxamide (Compound 1692), N-[(6-amino-2-pyridyl)sulfonyl]-6-(3-fluoro-5-isobutoxyphenyl)-2-(3-phenylbutoxy)pyridine-3-carboxamide (Compound 1689), N-[(6-amino-2-pyridyl)sulfonyl]-6-(3-fluoro-5-isobutoxyphenyl)-2-[3-(2-pyridyl)propoxy]pyridine-3-carboxamide (Compound 1693), N-[(6-amino-2-pyridyl)sulfonyl]-6-(3-fluoro-5-isobutoxyphenyl)-2-[3-(3-pyridyl)propoxy]pyridine-3-carboxamide (Compound 1691), N-[(6-amino-2-pyridyl)sulfonyl]-6-(3-fluoro-5-isobutoxyphenyl)-2-(3-phenylpropoxy)pyridine-3-carboxamide (Compound 1694), N-[(6-amino-2-pyridyl)sulfonyl]-6-(6-isopropoxy-3-pyridyl)-2-(2,2,3-trimethylpyrrolidin-1-yl)pyridine-3-carboxamide (Compound 464), N-[(6-amino-2-pyridyl)sulfonyl]-2-[(1R,4S)-3-azabicyclo[2.2.1]heptan-3-yl]-6-(6-isopropoxy-3-pyridyl)pyridine-3-carboxamide (Compound 476), N-[(6-amino-2-pyridyl)sulfonyl]-6-(6-isopropoxy-3-pyridyl)-2-[3-(2-pyridyl)-1-piperidyl]pyridine-3-carboxamide (Compound 489), N-[(6-amino-2-pyridyl)sulfonyl]-6-(trifluoromethyl)-2-[(4S)-2,2,4-trimethylpyrrolidin-1-yl]pyridine-3-carboxamide (Compound 1556), N-[(6-amino-2-pyridyl)sulfonyl]-2-(2,2,4,4-tetramethylpyrrolidin-1-yl)-6-(trifluoromethyl)pyridine-3-carboxamide (Compound 1635), N-[(6-amino-2-pyridyl)sulfonyl]-5-(trifluoromethyl)-2-[(4S)-2,2,4-trimethylpyrrolidin-1-yl]pyridine-3-carboxamide (Compound 1550), N-[(6-amino-2-pyridyl)sulfonyl]-6-methyl-2-[(4S)-2,2,4-trimethylpyrrolidin-1-yl]pyridine-3-carboxamide (Compound 1420), N-[(6-amino-2-pyridyl)sulfonyl]-6-methoxy-2-[(4S)-2,2,4-trimethylpyrrolidin-1-yl]pyridine-3-carboxamide (Compound 1536), N-[(6-amino-2-pyridyl)sulfonyl]-5-fluoro-2-[(4S)-2,2,4-trimethylpyrrolidin-1-yl]pyridine-3-carboxamide (Compound 1607), N-[(6-amino-2-pyridyl)sulfonyl]-2-[(4S)-2,2,4-trimethylpyrrolidin-1-yl]-6,7-dihydro-5H-cyclopenta[b]pyridine-3-carboxamide (Compound 1386), N-[(6-amino-2-pyridyl)sulfonyl]-2-[cyclopropylmethyl(propyl)amino]-6-(6-isopropoxy-3-pyridyl)pyridine-3-carboxamide (Compound 500), N-[(6-amino-2-pyridyl)sulfonyl]-6-(6-isopropoxy-3-pyridyl)-2-(2-methyl-4-phenyl-pyrrolidin-1-yl)pyridine-3-carboxamide (Compound 502), N-[(6-amino-2-pyridyl)sulfonyl]-6-(6-isopropoxy-3-pyridyl)-2-(2-phenylpyrrolidin-1-yl)pyridine-3-carboxamide (Compound 509), N-[(6-amino-2-pyridyl)sulfonyl]-6-(6-isopropoxy-3-pyridyl)-2-(3,3,5-trimethyl-1-piperidyl)pyridine-3-carboxamide (Compound 520), N-[(6-amino-2-pyridyl)sulfonyl]-2-(3-azabicyclo[2.2.1]heptan-3-yl)-6-(6-isopropoxy-3-pyridyl)pyridine-3-carboxamide (Compound 521), N-[(6-amino-2-pyridyl)sulfonyl]-6-(6-isopropoxy-3-pyridyl)-2-(3-propyl-1-piperidyl)pyridine-3-carboxamide (Compound 522), N-[(6-amino-2-pyridyl)sulfonyl]-6-(3-fluoro-5-isobutoxyphenyl)-2-[(2R,4S)-4-fluoro-2-methyl-pyrrolidin-1-yl]pyridine-3-carboxamide (Compound 1362)

N-[(6-amino-2-pyridyl)sulfonyl]-6-(6-isopropoxy-3-pyridyl)-2-[(3S)-2,2,3-trimethylpyrrolidin-1-yl]pyridine-3-carboxamide (Compound 557), N-[(6-amino-2-pyridyl)sulfonyl]-2-[3-(3,4-difluorophenyl)-1-piperidyl]-6-(6-isopropoxy-3-pyridyl)pyridine-3-carboxamide (Compound 558), N-[(6-amino-2-pyridyl)sulfonyl]-6-(6-isopropoxy-3-pyridyl)-2-(1-piperidyl)pyridine-3-carboxamide (Compound 567), N-[(6-amino-2-pyridyl)sulfonyl]-6-(6-isopropoxy-3-pyridyl)-2-[2-(methoxymethyl)-1-piperidyl]pyridine-3-carboxamide (Compound 574), N-[(6-amino-2-pyridyl)sulfonyl]-2-(6-azaspiro[2.5]octan-6-yl)-6-(6-isopropoxy-3-pyridyl)pyridine-3-carboxamide (Compound 578), N-[(6-amino-2-pyridyl)sulfonyl]-2-indolin-1-yl-6-(6-isopropoxy-3-pyridyl)pyridine-3-carboxamide (Compound 588), N-[(6-amino-2-pyridyl)sulfonyl]-2-(2,2,4,4-tetramethylpyrrolidin-1-yl)-5-(trifluoromethyl)pyridine-3-carboxamide (Compound 1638), N-[(6-amino-2-pyridyl)sulfonyl]-2-(2,2,4,4-tetramethylpyrrolidin-1-yl)-4-(trifluoromethyl)pyridine-3-carboxamide (Compound 1658), N-[(6-amino-2-pyridyl)sulfonyl]-2-(6,6-dimethyl-3-azabicyclo[3.1.0]hexan-3-yl)-6-(6-isopropoxy-3-pyridyl)pyridine-3-carboxamide (Compound 596), N-[(6-amino-5-hydroxy-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 1563), N-[(6-amino-5-hydroxy-2-pyridyl)sulfonyl]-2-[(2S,5R)-2,5-dimethylpyrrolidin-1-yl]-6-(6-isopropoxy-3-pyridyl)pyridine-3-carboxamide (Compound 1375), N-[(6-amino-5-benzyloxy-2-pyridyl)sulfonyl]-2-[(2S,5R)-2,5-dimethylpyrrolidin-1-yl]-6-(6-isopropoxy-3-pyridyl)pyridine-3-carboxamide (Compound 1588), N-[(2-amino-3-pyridyl)sulfonyl]-6-(6-isopropoxy-3-pyridyl)-2-[(4S)-2,2,4-trimethylpyrrolidin-1-yl]pyridine-3-carboxamide, N-[(2-amino-3-pyridyl)sulfonyl]-6-(3-fluoro-5-isobutoxyphenyl)-2-[(4S)-2,2,4-trimethylpyrrolidin-1-yl]pyridine-3-carboxamide (Compound 1593), N-[(2-amino-3-pyridyl)sulfonyl]-6-(3-fluoro-5-isobutoxy-phenyl)-2-[(4R)-2,2,4-trimethylpyrrolidin-1-yl]pyridine-3-carboxamide (Compound 1444), N-[(6-amino-2-pyridyl)sulfonyl]-2-(2-tert-butylpyrrolidin-1-yl)-6-(6-isopropoxy-3-pyridyl)pyridine-3-carboxamide (Compound 597), N-[(6-amino-2-pyridyl)sulfonyl]-2-(2,5-dimethyl-3-phenyl-pyrrolidin-1-yl)-6-(6-isopropoxy-3-pyridyl)pyridine-3-carboxamide (Compound 601), N-[(6-amino-2-pyridyl)sulfonyl]-6-(6-isopropoxy-3-pyridyl)-2-[4-(methoxymethyl)-1-piperidyl]pyridine-3-carboxamide (Compound 606), N-[(6-amino-2-pyridyl)sulfonyl]-2-(4-ethyl-1-piperidyl)-6-(6-isopropoxy-3-pyridyl)pyridine-3-carboxamide (Compound 619), N-[(6-amino-2-pyridyl)sulfonyl]-6-(6-isopropoxy-3-pyridyl)-2-(2-methyl-3-phenyl-pyrrolidin-1-yl)pyridine-3-carboxamide (Compound 625), N-[(6-amino-5-benzyloxy-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 1429), N-[(6-amino-2-pyridyl)sulfonyl]-2-(3-benzylpyrrolidin-1-yl)-6-(6-isopropoxy-3-pyridyl)pyridine-3-carboxamide (Compound 647), N-[(6-amino-2-pyridyl)sulfonyl]-6-(6-isopropoxy-3-pyridyl)-2-[3-(2,2,2-trifluoroethyl)-1-piperidyl]pyridine-3-carboxamide (Compound 656), N-[(6-amino-2-pyridyl)sulfonyl]-2-(3-benzyl-2-methyl-pyrrolidin-1-yl)-6-(6-isopropoxy-3-pyridyl)pyridine-3-carboxamide (Compound 658), N-[(6-amino-2-pyridyl)sulfonyl]-6-(6-isopropoxy-3-pyridyl)-2-(2-methyl-2,3,3a,4,5,6,7,7a-octahydroindol-1-yl)pyridine-3-carboxamide (Compound 675), N-[(6-amino-2-pyridyl)sulfonyl]-2-(3-azabicyclo[3.1.1]heptan-3-yl)-6-tert-butyl-pyridine-3-carboxamide (Compound 1401), 6-(3-fluoro-5-isobutoxy-phenyl)-N-[(6-methoxy-2-pyridyl)sulfonyl]-2-[(4S)-2,2,4-trimethylpyrrolidin-1-yl]pyridine-3-carboxamide (Compound 1483), N-[(6-amino-2-pyridyl)sulfonyl]-6-(3-fluoro-5-isobutoxy-phenyl)-2-[2-(3-methyldiazirin-3-yl)ethyl-prop-2-ynyl-amino]pyridine-3-carboxamide, N-[(6-amino-2-pyridyl)sulfonyl]-2-[(2S,5S)-2,5-dimethylpyrrolidin-1-yl]-6-(6-isopropoxy-3-pyridyl)pyridine-3-carboxamide (Compound 687), N-[(6-amino-2-pyridyl)sulfonyl]-2-(2,4-dimethylpyrrolidin-1-yl)-6-(6-isopropoxy-3-pyridyl)pyridine-3-carboxamide (Compound 689), 6-(3-fluoro-5-isobutoxy-phenyl)-N-(3-methoxyphenyl)sulfonyl-2-[(4S)-2,2,4-trimethylpyrrolidin-1-yl]pyridine-3-carboxamide (Compound 1452), N-(benzenesulfonyl)-6-(3-fluoro-5-isobutoxy-phenyl)-2-[(4R)-2,2,4-trimethylpyrrolidin-1-yl]pyridine-3-carboxamide (Compound 1396), N-[(6-amino-2-pyridyl)sulfonyl]-2-(7-azaspiro[2.5]octan-7-yl)-6-(6-isopropoxy-3-pyridyl)pyridine-3-carboxamide (Compound 703), N-[(6-amino-2-pyridyl)sulfonyl]-6-(6-isopropoxy-3-pyridyl)-2-(2-isopropylpyrrolidin-1-yl)pyridine-3-carboxamide (Compound 724), N-[(6-amino-2-pyridyl)sulfonyl]-6-(6-isopropoxy-3-pyridyl)-2-(3-oxa-7-azaspiro[3.5]nonan-7-yl)pyridine-3-carboxamide (Compound 729), N-[(6-amino-2-pyridyl)sulfonyl]-6-(6-isopropoxy-3-pyridyl)-2-(2-phenyl-1-piperidyl)pyridine-3-carboxamide (Compound 731), 2-(3,3a,4,5,6,6a-hexahydro-2H-cyclopenta[b]pyrrol-1-yl)-N-[(6-amino-2-pyridyl)sulfonyl]-6-(6-isopropoxy-3-pyridyl)pyridine-3-carboxamide (Compound 732), N-[(6-amino-2-pyridyl)sulfonyl]-2-(7-azaspiro[3.5]nonan-7-yl)-6-(6-isopropoxy-3-pyridyl)pyridine-3-carboxamide (Compound 733), N-[(6-amino-2-pyridyl)sulfonyl]-6-(6-isopropoxy-3-pyridyl)-2-(4-methyl-1-piperidyl)pyridine-3-carboxamide (Compound 736), N-[(6-amino-2-pyridyl)sulfonyl]-2-[cyclopropylmethyl(methyl)amino]-6-(6-isopropoxy-3-pyridyl)pyridine-3-carboxamide (Compound 740), N-[(6-amino-2-pyridyl)sulfonyl]-6-(6-isopropoxy-3-pyridyl)-2-(4-phenyl-1-piperidyl)pyridine-3-carboxamide (Compound 742), N-[(6-amino-2-pyridyl)sulfonyl]-2-(3-fluoro-1-piperidyl)-6-(6-isopropoxy-3-pyridyl)pyridine-3-carboxamide (Compound 745), N-[(6-amino-2-pyridyl)sulfonyl]-6-(6-isopropoxy-3-pyridyl)-2-[(3R)-3-methyl-1-piperidyl]pyridine-3-carboxamide (Compound 757), N-[(6-amino-2-pyridyl)sulfonyl]-2-[(2R,3S)-2,3-dimethylpyrrolidin-1-yl]-6-(6-isopropoxy-3-pyridyl)pyridine-3-carboxamide (Compound 764), N-[(6-amino-2-pyridyl)sulfonyl]-6-(6-isopropoxy-3-pyridyl)-2-(1-phenylethylamino)pyridine-3-carboxamide (Compound 766), 6-(3-fluoro-5-isobutoxy-phenyl)-N-(3-methoxyphenyl)sulfonyl-2-(2,2,4-trimethylpyrrolidin-1-yl)pyridine-3-carboxamide (Compound 1171), 6-(3-fluoro-5-isobutoxy-phenyl)-N-[(6-oxo-1H-pyridin-2-yl)sulfonyl]-2-(2,2,4-trimethylpyrrolidin-1-yl)pyridine-3-carboxamide (Compound 1308), N-(3-aminophenyl)sulfonyl-6-(3-fluoro-5-isobutoxy-phenyl)-2-(2,2,4-trimethylpyrrolidin-1-yl)pyridine-3-carboxamide (Compound 1184), N-(benzenesulfonyl)-6-(3-fluoro-5-isobutoxy-phenyl)-2-(2,2,4-trimethylpyrrolidin-1-yl)pyridine-3-carboxamide (Compound 620), 6-(3-fluoro-5-isobutoxy-phenyl)-N-(2-pyridylsulfonyl)-2-(2,2,4-trimethylpyrrolidin-1-yl)pyridine-3-carboxamide (Compound 1063), N-(3-aminophenyl)sulfonyl-2-(4,4-dimethyl-1-piperidyl)-6-(3-fluoro-5-isobutoxy-phenyl)pyridine-3-carboxamide (Compound 1014), 2-(4,4-dimethyl-1-piperidyl)-6-(3-fluoro-5-isobutoxy-phenyl)-N-(3-methoxyphenyl)sulfonyl-pyridine-3-carboxamide (Compound 510), N-(benzenesulfonyl)-2-(4,4-dimethyl-1-piperidyl)-6-(3-fluoro-5-isobutoxy-phenyl)pyridine-3-carboxamide (Compound 583), 6-(3-fluoro-5-isobutoxy-phenyl)-N-[(6-methoxy-2-pyridyl)sulfonyl]-2-(2,2,4-trimethylpyrrolidin-1-yl)pyridine-3-carboxamide (Compound 2430), 2-(4,4-dimethyl-1-piperidyl)-6-(3-fluoro-5-isobutoxy-phenyl)-N-[(6-oxo-1H-pyridin-2-yl)sulfonyl]pyridine-3-carboxamide (Compound 775), 2-(4,4-dimethyl-1-piperidyl)-6-(3-fluoro-5-isobutoxy-phenyl)-N-(2-pyridylsulfonyl)pyridine-3-carboxamide (Compound 1069), 2-(4,4-dimethyl-1-piperidyl)-6-(3-fluoro-5-isobutoxy-phenyl)-N-[(6-methoxy-2-pyridyl)sulfonyl]pyridine-3-carboxamide (Compound 1090), N-[(6-amino-2-pyridyl)sulfonyl]-6-(6-isopropoxy-3-pyridyl)-2-[(4S)-2,2,4-trimethylpyrrolidin-1-yl]pyridine-3-carboxamide (Compound 811), N-[(6-amino-2-pyridyl)sulfonyl]-6-(6-isopropoxy-3-pyridyl)-2-spiro[1H-isobenzofuran-3,4'-piperidine]-1'-yl-pyridine-3-carboxamide (Compound 818),
N-[(6-amino-2-pyridyl)sulfonyl]-2-(2,2-dimethylpyrrolidin-1-yl)-6-(6-isopropoxy-3-pyridyl)pyridine-3-carboxamide (Compound 834),
N-[(6-amino-2-pyridyl)sulfonyl]-6-(6-isopropoxy-3-pyridyl)-2-[(3S)-3-methyl-1-piperidyl]pyridine-3-carboxamide (Compound 836),
N-[(6-amino-2-pyridyl)sulfonyl]-2-[3-(cyclopropylmethoxy)-1-piperidyl]-6-(6-isopropoxy-3-pyridyl)pyridine-3-carboxamide (Compound 858),
N-[(6-amino-2-pyridyl)sulfonyl]-6-(6-isopropoxy-3-pyridyl)-2-[(3S)-3-phenyl-1-piperidyl]pyridine-3-carboxamide (Compound 864),
N-[(6-amino-2-pyridyl)sulfonyl]-2-[4-(cyclopropylmethoxy)-1-piperidyl]-6-(6-isopropoxy-3-pyridyl)pyridine-3-carboxamide (Compound 884),
N-[(6-amino-2-pyridyl)sulfonyl]-2-(4,4-difluoro-1-piperidyl)-6-(6-isopropoxy-3-pyridyl)pyridine-3-carboxamide (Compound 889),
N-[(6-amino-2-pyridyl)sulfonyl]-2-(7-azabicyclo[2.2.1]heptan-7-yl)-6-(6-isopropoxy-3-pyridyl)pyridine-3-carboxamide (Compound 903),
N-[(6-amino-2-pyridyl)sulfonyl]-2-(4-fluoro-1-piperidyl)-6-(6-isopropoxy-3-pyridyl)pyridine-3-carboxamide (Compound 913),
N-[(6-amino-2-pyridyl)sulfonyl]-6-(6-isopropoxy-3-pyridyl)-2-(2,2,4,4-tetramethylpyrrolidin-1-yl)pyridine-3-carboxamide (Compound 915),
N-[(6-amino-2-pyridyl)sulfonyl]-2-[(1S,4R)-3-azabicyclo[2.2.1]heptan-3-yl]-6-(6-isopropoxy-3-pyridyl)pyridine-3-carboxamide (Compound 921),
N-[(6-amino-2-pyridyl)sulfonyl]-6-(6-isopropoxy-3-pyridyl)-2-(2,3,5-trimethylpyrrolidin-1-yl)pyridine-3-carboxamide (Compound 925),
N-[(6-amino-2-pyridyl)sulfonyl]-2-(2-cyclopropylpyrrolidin-1-yl)-6-(6-isopropoxy-3-pyridyl)pyridine-3-carboxamide (Compound 928),
N-[(6-amino-2-pyridyl)sulfonyl]-2-(indan-1-ylamino)-6-(6-isopropoxy-3-pyridyl)pyridine-3-carboxamide (Compound 935),
N-[(6-amino-2-pyridyl)sulfonyl]-2-(azepan-1-yl)-6-(6-isopropoxy-3-pyridyl)pyridine-3-carboxamide (Compound 940),
N-[(6-amino-2-pyridyl)sulfonyl]-6-(6-isopropoxy-3-pyridyl)-2-[(4R)-2,2,4-trimethylpyrrolidin-1-yl]pyridine-3-carboxamide (Compound 949),
N-[(6-amino-2-pyridyl)sulfonyl]-2-(3-ethynyl-1-piperidyl)-6-(6-isopropoxy-3-pyridyl)pyridine-3-carboxamide (Compound 954),
N-[(6-amino-2-pyridyl)sulfonyl]-2-(3-ethoxy-1-piperidyl)-6-(6-isopropoxy-3-pyridyl)pyridine-3-carboxamide (Compound 960),
N-[(6-amino-2-pyridyl)sulfonyl]-2-(3,3-diethyl-1-piperidyl)-6-(6-isopropoxy-3-pyridyl)pyridine-3-carboxamide (Compound 971),
N-[(6-amino-2-pyridyl)sulfonyl]-2-(3,4-dimethyl-1-piperidyl)-6-(6-isopropoxy-3-pyridyl)pyridine-3-carboxamide (Compound 979),
N-[(6-amino-2-pyridyl)sulfonyl]-2-(8-azaspiro[3.4]octan-8-yl)-6-(6-isopropoxy-3-pyridyl)pyridine-3-carboxamide (Compound 987),
N-[(6-amino-2-pyridyl)sulfonyl]-6-(6-isopropoxy-3-pyridyl)-2-[(3R)-2,2,3-trimethylpyrrolidin-1-yl]pyridine-3-carboxamide (Compound 992),
N-[(6-amino-2-pyridyl)sulfonyl]-2-(2-benzylpyrrolidin-1-yl)-6-(6-isopropoxy-3-pyridyl)pyridine-3-carboxamide (Compound 994),
N-[(6-amino-2-pyridyl)sulfonyl]-2-(4-benzyloxy-1-piperidyl)-6-(6-isopropoxy-3-pyridyl)pyridine-3-carboxamide (Compound 1012),
N-[(6-amino-2-pyridyl)sulfonyl]-2-(3-ethyl-1-piperidyl)-6-(6-isopropoxy-3-pyridyl)pyridine-3-carboxamide (Compound 1023),
N-[(6-amino-2-pyridyl)sulfonyl]-2-[cyclopentyl(methyl)amino]-6-(6-isopropoxy-3-pyridyl)pyridine-3-carboxamide (Compound 1025),
N-[(6-amino-2-pyridyl)sulfonyl]-2-(benzylamino)-6-(6-isopropoxy-3-pyridyl)pyridine-3-carboxamide (Compound 1026),
N-[(6-amino-2-pyridyl)sulfonyl]-6-(6-isopropoxy-3-pyridyl)-2-(2,2,5-trimethylpyrrolidin-1-yl)pyridine-3-carboxamide (Compound 1040),
N-[(6-amino-2-pyridyl)sulfonyl]-6-(6-isopropoxy-3-pyridyl)-2-[4-(trifluoromethyl)-1-piperidyl]pyridine-3-carboxamide (Compound 1043),
N-[(6-amino-2-pyridyl)sulfonyl]-2-isoindolin-2-yl-6-(6-isopropoxy-3-pyridyl)pyridine-3-carboxamide (Compound 1072),
N-[(6-amino-2-pyridyl)sulfonyl]-6-(6-isopropoxy-3-pyridyl)-2-(4-phenoxy-1-piperidyl)pyridine-3-carboxamide (Compound 1080),
N-[(6-amino-2-pyridyl)sulfonyl]-6-(6-isopropoxy-3-pyridyl)-2-[(3S)-3-methylpyrrolidin-1-yl]pyridine-3-carboxamide (Compound 1081),
N-[(6-amino-2-pyridyl)sulfonyl]-2-(2-ethylpyrrolidin-1-yl)-6-(6-isopropoxy-3-pyridyl)pyridine-3-carboxamide (Compound 1087),
N-[(6-amino-2-pyridyl)sulfonyl]-6-(6-isopropoxy-3-pyridyl)-2-(3-phenoxypyrrolidin-1-yl)pyridine-3-carboxamide (Compound 1092),
2-(3,3a,4,5,6,6a-hexahydro-1H-cyclopenta[c]pyrrol-2-yl)-N-[(6-amino-2-pyridyl)sulfonyl]-6-(6-isopropoxy-3-pyridyl)pyridine-3-carboxamide (Compound 1107),
N-[(6-amino-2-pyridyl)sulfonyl]-6-(6-isopropoxy-3-pyridyl)-2-(3-phenylpyrrolidin-1-yl)pyridine-3-carboxamide (Compound 1112),
N-[(6-amino-2-pyridyl)sulfonyl]-6-(6-isopropoxy-3-pyridyl)-2-[3-(methoxymethyl)-1-piperidyl]pyridine-3-carboxamide (Compound 1116),
N-[(6-amino-2-pyridyl)sulfonyl]-2-(3-cyclopropyl-1-piperidyl)-6-(6-isopropoxy-3-pyridyl)pyridine-3-carboxamide (Compound 1132),
N-[(6-amino-2-pyridyl)sulfonyl]-2-(4,4-dimethyl-1-piperidyl)-6-(6-isopropoxy-3-pyridyl)pyridine-3-carboxamide (Compound 1134),
N-[(6-amino-2-pyridyl)sulfonyl]-2-[(3S,5S)-3,5-dimethyl-1-piperidyl]-6-(6-isopropoxy-3-pyridyl)pyridine-3-carboxamide (Compound 1136),
N-[(6-amino-2-pyridyl)sulfonyl]-2-[(3R,5S)-3,5-dimethyl-1-piperidyl]-6-(6-isopropoxy-3-pyridyl)pyridine-3-carboxamide (Compound 1145),
N-[(6-amino-2-pyridyl)sulfonyl]-6-(6-isopropoxy-3-pyridyl)-2-(2-methyl-1-piperidyl)pyridine-3-carboxamide (Compound 1182),
N-[(6-amino-2-pyridyl)sulfonyl]-2-[(2R,5R)-2,5-dimethylpyrrolidin-1-yl]-6-(6-isopropoxy-3-pyridyl)pyridine-3-carboxamide (Compound 1198),
N-[(6-amino-2-pyridyl)sulfonyl]-2-(3-tert-butylpyrrolidin-1-yl)-6-(6-isopropoxy-3-pyridyl)pyridine-3-carboxamide (Compound 1206), N-[(6-amino-2-pyridyl)sulfonyl]-6-(6-isopropoxy-3-pyridyl)-2-[(3R)-3-phenyl-1-piperidyl]pyridine-3-carboxamide, N-[(6-amino-2-pyridyl)sulfonyl]-2-(4-ethoxy-1-piperidyl)-6-(6-isopropoxy-3-pyridyl)pyridine-3-carboxamide (Compound 1214), N-[(6-amino-2-pyridyl)sulfonyl]-6-(6-isopropoxy-3-pyridyl)-2-[(2R)-2-(trifluoromethyl)pyrrolidin-1-yl]pyridine-3-carboxamide (Compound 1230), N-[(6-amino-2-pyridyl)sulfonyl]-6-(6-isopropoxy-3-pyridyl)-2-(2,2,4-trimethylpyrrolidin-1-yl)pyridine-3-carboxamide (Compound 1247), N-[(6-amino-2-pyridyl)sulfonyl]-6-(6-isopropoxy-3-pyridyl)-2-[(2S)-2-(trifluoromethyl)pyrrolidin-1-yl]pyridine-3-carboxamide (Compound 1248), N-[(6-amino-2-pyridyl)sulfonyl]-6-(6-isopropoxy-3-pyridyl)-2-(2-methylpyrrolidin-1-yl)pyridine-3-carboxamide (Compound 1271), N-[(6-amino-2-pyridyl)sulfonyl]-6-(6-isopropoxy-3-pyridyl)-2-[3-(trifluoromethyl)-1-piperidyl]pyridine-3-carboxamide (Compound 1274), N-[(6-amino-2-pyridyl)sulfonyl]-2-(3,3-dimethyl-1-piperidyl)-6-(6-isopropoxy-3-pyridyl)pyridine-3-carboxamide (Compound 1283), N-[(6-amino-2-pyridyl)sulfonyl]-6-(6-isopropoxy-3-pyridyl)-2-[(3R)-3-methylpyrrolidin-1-yl]pyridine-3-carboxamide (Compound 1322), N-[(6-amino-2-pyridyl)sulfonyl]-6-(6-isopropoxy-3-pyridyl)-2-(2,3,3-trimethylpyrrolidin-1-yl)pyridine-3-carboxamide (Compound 1327), N-[(6-amino-2-pyridyl)sulfonyl]-2-[3-(3-chlorophenyl)-1-piperidyl]-6-(6-isopropoxy-3-pyridyl)pyridine-3-carboxamide (Compound 1339), N-[(6-amino-2-pyridyl)sulfonyl]-2-(3-ethyl-3-methyl-1-piperidyl)-6-(6-isopropoxy-3-pyridyl)pyridine-3-carboxamide (Compound 1341), N-[(6-amino-2-pyridyl)sulfonyl]-2-(7-azaspiro[2.4]heptan-7-yl)-6-(3-fluoro-5-isobutoxy-phenyl)pyridine-3-carboxamide (Compound 1333), N-[(6-amino-2-pyridyl)sulfonyl]-2-[(3R,5S)-3,5-dimethyl-1-piperidyl]-6-(3-fluoro-5-isobutoxy-phenyl)pyridine-3-carboxamide (Compound 371), N-[(6-amino-2-pyridyl)sulfonyl]-6-(3-fluoro-5-isobutoxy-phenyl)-2-(1-piperidyl)pyridine-3-carboxamide (Compound 380), 2-(3,3a,4,5,6,6a-hexahydro-2H-cyclopenta[b]pyrrol-1-yl)-N-[(6-amino-2-pyridyl)sulfonyl]-6-(3-fluoro-5-isobutoxy-phenyl)pyridine-3-carboxamide (Compound 383), methyl (2S)-1-[3-[(6-amino-2-pyridyl)sulfonylcarbamoyl]-6-(3-fluoro-5-isobutoxy-phenyl)-2-pyridyl]pyrrolidine-2-carboxylate (Compound 385), N-[(6-amino-2-pyridyl)sulfonyl]-6-(3-fluoro-5-isobutoxy-phenyl)-2-[(2R)-2-(trifluoromethyl)pyrrolidin-1-yl]pyridine-3-carboxamide (Compound 398), N-[(6-amino-2-pyridyl)sulfonyl]-6-(3-fluoro-5-isobutoxy-phenyl)-2-[(3R)-3-methyl-1-piperidyl]pyridine-3-carboxamide (Compound 408), N-[(6-amino-2-pyridyl)sulfonyl]-2-(azepan-1-yl)-6-(3-fluoro-5-isobutoxy-phenyl)pyridine-3-carboxamide (Compound 418), N-[(6-amino-2-pyridyl)sulfonyl]-6-(3-fluoro-5-isobutoxy-phenyl)-2-[3-(methoxymethyl)-1-piperidyl]pyridine-3-carboxamide (Compound 419), N-[(6-amino-2-pyridyl)sulfonyl]-2-(7-azabicyclo[2.2.1]heptan-7-yl)-6-(3-fluoro-5-isobutoxy-phenyl)pyridine-3-carboxamide (Compound 420), N-[(6-amino-2-pyridyl)sulfonyl]-6-(3-fluoro-5-isobutoxy-phenyl)-2-[(2S)-2-methylpyrrolidin-1-yl]pyridine-3-carboxamide (Compound 421), N-[(6-amino-2-pyridyl)sulfonyl]-6-(3-fluoro-5-isobutoxy-phenyl)-2-(8-oxa-4-azaspiro[4.4]nonan-4-yl)pyridine-3-carboxamide (Compound 424), N-[(6-amino-2-pyridyl)sulfonyl]-6-(3-fluoro-5-isobutoxy-phenyl)-2-(2-methyl-1-piperidyl)pyridine-3-carboxamide (Compound 425), N-[(6-amino-2-pyridyl)sulfonyl]-6-(3-fluoro-5-isobutoxy-phenyl)-2-[(2R)-2-phenylpyrrolidin-1-yl]pyridine-3-carboxamide (Compound 447), N-[(6-amino-2-pyridyl)sulfonyl]-2-(2,5-dihydropyrrol-1-yl)-6-(3-fluoro-5-isobutoxy-phenyl)pyridine-3-carboxamide (Compound 453), N-[(6-amino-2-pyridyl)sulfonyl]-2-[(2S,5S)-2,5-dimethylpyrrolidin-1-yl]-6-(3-fluoro-5-isobutoxy-phenyl)pyridine-3-carboxamide (Compound 458), N-[(6-amino-2-pyridyl)sulfonyl]-2-(3-benzylpyrrolidin-1-yl)-6-(3-fluoro-5-isobutoxy-phenyl)pyridine-3-carboxamide (Compound 473), N-[(6-amino-2-pyridyl)sulfonyl]-6-(3-fluoro-5-isobutoxy-phenyl)-2-(2-methylpyrrolidin-1-yl)pyridine-3-carboxamide (Compound 479), N-[(6-amino-2-pyridyl)sulfonyl]-6-(3-fluoro-5-isobutoxy-phenyl)-2-(2-methyl-4-phenyl-pyrrolidin-1-yl)pyridine-3-carboxamide (Compound 488), N-[(6-amino-2-pyridyl)sulfonyl]-6-(3-fluoro-5-isobutoxy-phenyl)-2-[4-(trifluoromethyl)-3-azabicyclo[3.1.0]hexan-3-yl]pyridine-3-carboxamide (Compound 490), N-[(6-amino-2-pyridyl)sulfonyl]-2-[2-(1,1-dimethylpropyl)pyrrolidin-1-yl]-6-(3-fluoro-5-isobutoxy-phenyl)pyridine-3-carboxamide (Compound 493), N-[(6-amino-2-pyridyl)sulfonyl]-6-(3-fluoro-5-isobutoxy-phenyl)-2-(2,2,5-trimethylpyrrolidin-1-yl)pyridine-3-carboxamide (Compound 496), N-[(6-amino-2-pyridyl)sulfonyl]-2-[1-cyclopropylethyl(methyl)amino]-6-(3-fluoro-5-isobutoxy-phenyl)pyridine-3-carboxamide (Compound 516), N-[(6-amino-2-pyridyl)sulfonyl]-2-(6-azaspiro[3.3]heptan-6-yl)-6-(3-fluoro-5-isobutoxy-phenyl)pyridine-3-carboxamide (Compound 527), N-[(6-amino-2-pyridyl)sulfonyl]-2-(3-ethyl-3-methyl-1-piperidyl)-6-(3-fluoro-5-isobutoxy-phenyl)pyridine-3-carboxamide (Compound 530), N-[(6-amino-2-pyridyl)sulfonyl]-6-(3-fluoro-5-isobutoxy-phenyl)-2-[(3S)-2,2,3-trimethylpyrrolidin-1-yl]pyridine-3-carboxamide (Compound 547), N-[(6-amino-2-pyridyl)sulfonyl]-6-(3-fluoro-5-isobutoxy-phenyl)-2-(2,2,4-trimethylpyrrolidin-1-yl)pyridine-3-carboxamide (Compound 555), N-[(6-amino-2-pyridyl)sulfonyl]-6-(3-fluoro-5-isobutoxy-phenyl)-2-(3,3,5-trimethyl-1-piperidyl)pyridine-3-carboxamide (Compound 560), N-[(6-amino-2-pyridyl)sulfonyl]-6-(3-fluoro-5-isobutoxy-phenyl)-2-(3,3,4-trimethyl-1-piperidyl)pyridine-3-carboxamide (Compound 575), N-[(6-amino-2-pyridyl)sulfonyl]-2-[(1R,5S)-3-azabicyclo[3.2.1]octan-3-yl]-6-(3-fluoro-5-isobutoxy-phenyl)pyridine-3-carboxamide (Compound 581), N-[(6-amino-2-pyridyl)sulfonyl]-2-(2,4-dimethylpyrrolidin-1-yl)-6-(3-fluoro-5-isobutoxy-phenyl)pyridine-3-carboxamide (Compound 587), N-[(6-amino-2-pyridyl)sulfonyl]-6-(3-fluoro-5-isobutoxy-phenyl)-2-pyrrolidin-1-yl-pyridine-3-carboxamide (Compound 592), N-[(6-amino-2-pyridyl)sulfonyl]-2-(2-cyclopropylpyrrolidin-1-yl)-6-(3-fluoro-5-isobutoxy-phenyl)pyridine-3-carboxamide (Compound 593), N-[(6-amino-2-pyridyl)sulfonyl]-2-(6,6-dimethyl-3-azabicyclo[3.1.0]hexan-3-yl)-6-(3-fluoro-5-isobutoxy-phenyl)pyridine-3-carboxamide (Compound 609), N-[(6-amino-2-pyridyl)sulfonyl]-2-(3-tert-butylpyrrolidin-1-yl)-6-(3-fluoro-5-isobutoxy-phenyl)pyridine-3-carboxamide (Compound 611), N-[(6-amino-2-pyridyl)sulfonyl]-2-(2-tert-butylpyrrolidin-1-yl)-6-(3-fluoro-5-isobutoxy-phenyl)pyridine-3-carboxamide (Compound 613), N-[(6-amino-2-pyridyl)sulfonyl]-2-(4-ethyl-1-piperidyl)-6-(3-fluoro-5-isobutoxy-phenyl)pyridine-3-carboxamide (Compound 615), N-[(6-amino-2-pyridyl)sulfonyl]-6-(3-fluoro-5-isobutoxy-phenyl)-2-[(3R)-3-phenyl-1-piperidyl]pyridine-3-carboxamide (Compound 651), N-[(6-amino-2-pyridyl)sulfonyl]-2-(3-cyclopropyl-1-piperidyl)-6-(3-fluoro-5-isobutoxy-phenyl)pyridine-3-carboxamide (Compound 655), N-[(6-amino-2-pyridyl)sulfonyl]-6-(3-fluoro-5-isobutoxy-phenyl)-2-[(3R)-2,2,3-trimethylpyrrolidin-1-yl]pyridine-3-carboxamide (Compound 657), N-[(6-amino-2-pyridyl)sulfonyl]-6-(3-fluoro-5-isobutoxy-phenyl)-2-[2-(2-pyridyl)pyrrolidin-1-yl]pyridine-3-carboxamide (Compound 659), N-[(6-amino-2-pyridyl)sulfonyl]-2-(2-benzyl-2-methyl-pyrrolidin-1-yl)-6-(3-fluoro-5-isobutoxy-phenyl)pyridine-3-carboxamide (Compound 663), N-[(6-amino-2-pyridyl)sulfonyl]-6-(3-fluoro-5-isobutoxy-phenyl)-2-[(3S)-3-methylpyrrolidin-1-yl]pyridine-3-carboxamide (Compound 678), N-[(6-amino-2-pyridyl)sulfonyl]-2-(3-azabicyclo[2.2.1]heptan-3-yl)-6-(3-fluoro-5-isobutoxy-phenyl)pyridine-3-carboxamide (Compound 680), N-[(6-amino-2-pyridyl)sulfonyl]-2-[cyclobutyl(methyl)amino]-6-(3-fluoro-5-isobutoxy-phenyl)pyridine-3-carboxamide. (Compound 683), N-[(6-amino-2-pyridyl)sulfonyl]-6-(3-fluoro-5-isobutoxy-phenyl)-2-[(3S)-3-phenyl-1-piperidyl]pyridine-3-carboxamide (Compound 684), N-[(6-amino-2-pyridyl)sulfonyl]-6-(3-fluoro-5-isobutoxy-phenyl)-2-[(2R)-2-methylpyrrolidin-1-yl]pyridine-3-carboxamide (Compound 694), N-[(6-amino-2-pyridyl)sulfonyl]-2-(2,5-dimethyl-3-phenyl-pyrrolidin-1-yl)-6-(3-fluoro-5-isobutoxy-phenyl)pyridine-3-carboxamide (Compound 711), N-[(6-amino-2-pyridyl)sulfonyl]-6-(3-fluoro-5-isobutoxy-phenyl)-2-[(2S)-2-(methoxymethyl)pyrrolidin-1-yl]pyridine-3-carboxamide (Compound 719), N-[(6-amino-2-pyridyl)sulfonyl]-2-(2,3-dimethylpyrrolidin-1-yl)-6-(3-fluoro-5-isobutoxy-phenyl)pyridine-3-carboxamide (Compound 720), N-[(6-amino-2-pyridyl)sulfonyl]-6-(3-fluoro-5-isobutoxy-phenyl)-2-(3-methyl-1-piperidyl)pyridine-3-carboxamide (Compound 735), N-[(6-amino-2-pyridyl)sulfonyl]-2-[(2R,5R)-2,5-dimethylpyrrolidin-1-yl]-6-(3-fluoro-5-isobutoxy-phenyl)pyridine-3-carboxamide (Compound 751), N-[(6-amino-2-pyridyl)sulfonyl]-2-(2-benzylpyrrolidin-1-yl)-6-(3-fluoro-5-isobutoxy-phenyl)pyridine-3-carboxamide (Compound 772), N-[(6-amino-2-pyridyl)sulfonyl]-2-[2,2-dimethyl-3-(trifluoromethyl)pyrrolidin-1-yl]-6-(3-fluoro-5-isobutoxy-phenyl)pyridine-3-carboxamide (Compound 780), N-[(6-amino-2-pyridyl)sulfonyl]-2-(2,3-dimethyl-1-piperidyl)-6-(3-fluoro-5-isobutoxy-phenyl)pyridine-3-carboxamide (Compound 837), N-[(6-amino-2-pyridyl)sulfonyl]-2-(8-azaspiro[3.4]octan-8-yl)-6-(3-fluoro-5-isobutoxy-phenyl)pyridine-3-carboxamide (Compound 845), N-[(6-amino-2-pyridyl)sulfonyl]-6-(3-fluoro-5-isobutoxy-phenyl)-2-(2,2,4,4-tetramethylpyrrolidin-1-yl)pyridine-3-carboxamide (Compound 850), 2-(3,3a,4,5,6,6a-hexahydro-1H-cyclopenta[c]pyrrol-2-yl)-N-[(6-amino-2-pyridyl)sulfonyl]-6-(3-fluoro-5-isobutoxy-phenyl)pyridine-3-carboxamide (Compound 857), N-[(6-amino-2-pyridyl)sulfonyl]-6-(3-fluoro-5-isobutoxy-phenyl)-2-(2-phenylpyrrolidin-1-yl)pyridine-3-carboxamide (Compound 859), N-[(6-amino-2-pyridyl)sulfonyl]-2-[cyclopropylmethyl(propyl)amino]-6-(3-fluoro-5-isobutoxy-phenyl)pyridine-3-carboxamide (Compound 881), N-[(6-amino-2-pyridyl)sulfonyl]-2-(3,3-dimethyl-1-piperidyl)-6-(3-fluoro-5-isobutoxy-phenyl)pyridine-3-carboxamide (Compound 887), N-[(6-amino-2-pyridyl)sulfonyl]-2-(4-azabicyclo[3.1.0]hexan-4-yl)-6-(3-fluoro-5-isobutoxy-phenyl)pyridine-3-carboxamide (Compound 906), N-[(6-amino-2-pyridyl)sulfonyl]-2-[(1S,4R)-3-azabicyclo[2.2.1]heptan-3-yl]-6-(3-fluoro-5-isobutoxy-phenyl)pyridine-3-carboxamide (Compound 924), N-[(6-amino-2-pyridyl)sulfonyl]-2-(9-azaspiro[4.4]nonan-9-yl)-6-(3-fluoro-5-isobutoxy-phenyl)pyridine-3-carboxamide (Compound 926), N-[(6-amino-2-pyridyl)sulfonyl]-2-(3-ethylpyrrolidin-1-yl)-6-(3-fluoro-5-isobutoxy-phenyl)pyridine-3-carboxamide (Compound 931), N-[(6-amino-2-pyridyl)sulfonyl]-2-[(1R,5S)-8-azabicyclo[3.2.1]octan-8-yl]-6-(3-fluoro-5-isobutoxy-phenyl)pyridine-3-carboxamide (Compound 934), N-[(6-amino-2-pyridyl)sulfonyl]-2-(7-azaspiro[2.5]octan-7-yl)-6-(3-fluoro-5-isobutoxy-phenyl)pyridine-3-carboxamide (Compound 953), N-[(6-amino-2-pyridyl)sulfonyl]-2-(3-benzyl-2-methyl-pyrrolidin-1-yl)-6-(3-fluoro-5-isobutoxy-phenyl)pyridine-3-carboxamide (Compound 969), N-[(6-amino-2-pyridyl)sulfonyl]-2-(6-azaspiro[2.5]octan-6-yl)-6-(3-fluoro-5-isobutoxy-phenyl)pyridine-3-carboxamide (Compound 973), N-[(6-amino-2-pyridyl)sulfonyl]-6-(3-fluoro-5-isobutoxy-phenyl)-2-(4-methyl-1-piperidyl)pyridine-3-carboxamide (Compound 991), N-[(6-amino-2-pyridyl)sulfonyl]-2-(2,2-dimethyl-1-piperidyl)-6-(3-fluoro-5-isobutoxy-phenyl)pyridine-3-carboxamide (Compound 1004), N-[(6-amino-2-pyridyl)sulfonyl]-6-(3-fluoro-5-isobutoxy-phenyl)-2-[methyl-[(1-methylcyclopropyl)methyl]amino]pyridine-3-carboxamide (Compound 1009), N-[(6-amino-2-pyridyl)sulfonyl]-2-[cyclopropylmethyl(methyl)amino]-6-(3-fluoro-5-isobutoxy-phenyl)pyridine-3-carboxamide (Compound 1010), N-[(6-amino-2-pyridyl)sulfonyl]-2-(3,5-dimethyl-1-piperidyl)-6-(3-fluoro-5-isobutoxy-phenyl)pyridine-3-carboxamide (Compound 1013), N-[(6-amino-2-pyridyl)sulfonyl]-6-(3-fluoro-5-isobutoxy-phenyl)-2-[(3R)-3-methylpyrrolidin-1-yl]pyridine-3-carboxamide (Compound 1051), N-[(6-amino-2-pyridyl)sulfonyl]-2-(6-azaspiro[2.4]heptan-6-yl)-6-(3-fluoro-5-isobutoxy-phenyl)pyridine-3-carboxamide (Compound 1061), N-[(6-amino-2-pyridyl)sulfonyl]-6-(3-fluoro-5-isobutoxy-phenyl)-2-[(2R)-2,3,3-trimethylpyrrolidin-1-yl]pyridine-3-carboxamide (Compound 1065), N-[(6-amino-2-pyridyl)sulfonyl]-2-(2,2-dimethyl-4-oxo-pyrrolidin-1-yl)-6-(3-fluoro-5-isobutoxy-phenyl)-1,2-dihydropyridine-3-carboxamide, N-[(6-amino-2-pyridyl)sulfonyl]-2-[(2S)-2-tert-butylpyrrolidin-1-yl]-6-(3-fluoro-5-isobutoxy-phenyl)pyridine-3-carboxamide (Compound 1097), N-[(6-amino-2-pyridyl)sulfonyl]-6-(3-fluoro-5-isobutoxy-phenyl)-2-(3-isopropyl-1-piperidyl)pyridine-3-carboxamide (Compound 1098), N-[(6-amino-2-pyridyl)sulfonyl]-2-[cyclopropyl(methyl)amino]-6-(3-fluoro-5-isobutoxy-phenyl)pyridine-3-carboxamide (Compound 1117), N-[(6-amino-2-pyridyl)sulfonyl]-6-(3-fluoro-5-isobutoxy-phenyl)-2-(2,2,3-trimethylpyrrolidin-1-yl)pyridine-3-carboxamide (Compound 1121), N-[(6-amino-2-pyridyl)sulfonyl]-6-(3-fluoro-5-isobutoxy-phenyl)-2-[(2S)-2,3,3-trimethylpyrrolidin-1-yl]pyridine-3-carboxamide (Compound 1144), N-[(6-amino-2-pyridyl)sulfonyl]-6-(3-fluoro-5-isobutoxy-phenyl)-2-[(2R)-2-(methoxymethyl)pyrrolidin-1-yl]pyridine-3-carboxamide (Compound 1149), N-[(6-amino-2-pyridyl)sulfonyl]-6-(3-fluoro-5-isobutoxy-phenyl)-2-(2,3,3-trimethylpyrrolidin-1-yl)pyridine-3-carboxamide (Compound 1156), N-[(6-amino-2-pyridyl)sulfonyl]-2-[cyclopropylmethyl(isopropyl)amino]-6-(3-fluoro-5-isobutoxy-phenyl)pyridine-3-carboxamide (Compound 1157), N-[(6-amino-2-pyridyl)sulfonyl]-6-(3-fluoro-5-isobutoxy-phenyl)-2-(4-methylene-1-piperidyl)pyridine-3-carboxamide (Compound 1162), N-[(6-amino-2-pyridyl)sulfonyl]-6-(3-fluoro-5-isobutoxy-phenyl)-2-[(5R)-2,2,5-trimethylpyrrolidin-1-yl]pyridine-3-carboxamide (Compound 1166), N-[(6-amino-2-pyridyl)sulfonyl]-2-[(2R)-2-tert-butylpyrrolidin-1-yl]-6-(3-fluoro-5-isobutoxy-phenyl)pyridine-3-carboxamide (Compound 1170), N-[(6-amino-2-pyridyl)sulfonyl]-2-[(1R,4S)-3-azabicyclo[2.2.1]heptan-3-yl]-6-(3-fluoro-5-isobutoxy-phenyl)pyridine-3-carboxamide (Compound 1180), N-[(6-amino-2-pyridyl)sulfonyl]-2-(2,2-dimethyl-3-oxo-pyrrolidin-1-yl)-6-(3-fluoro-5-isobutoxy-phenyl)-1,2-dihydropyridine-3-carboxamide, N-[(6-amino-2-pyridyl)sulfonyl]-6-(3-fluoro-5-isobutoxy-phenyl)-2-[(3S)-3-methyl-1-piperidyl]pyridine-3-carboxamide (Compound 1193), N-[(6-amino-2-pyridyl)sulfonyl]-2-[1-(3-chlorophenyl)ethyl-methyl-amino]-6-(3-fluoro-5-isobutoxy-phenyl)pyridine-3-carboxamide (Compound 1205), N-[(6-amino-2-pyridyl)sulfonyl]-2-[(3S,5S)-3,5-dimethyl-1-piperidyl]-6-(3-fluoro-5-isobutoxy-phenyl)pyridine-3-carboxamide (Compound 1210), N-[(6-amino-2-pyridyl)sulfonyl]-2-(2-ethylpyrrolidin-1-yl)-6-(3-fluoro-5-isobutoxy-phenyl)pyridine-3-carboxamide (Compound 1218), N-[(6-amino-2-pyridyl)sulfonyl]-2-(2-ethyl-5-methyl-pyrrolidin-1-yl)-6-(3-fluoro-5-isobutoxy-phenyl)pyridine-3-carboxamide (Compound 1222), N-[(6-amino-2-pyridyl)sulfonyl]-6-(3-fluoro-5-isobutoxy-phenyl)-2-[(5S)-2,2,5-trimethylpyrrolidin-1-yl]pyridine-3-carboxamide (Compound 1241), N-[(6-amino-2-pyridyl)sulfonyl]-6-(3-fluoro-5-isobutoxy-phenyl)-2-(2-isopropylpyrrolidin-1-yl)pyridine-3-carboxamide (Compound 1258), N-[(6-amino-2-pyridyl)sulfonyl]-6-(3-fluoro-5-isobutoxy-phenyl)-2-[(2S)-2-phenylpyrrolidin-1-yl]pyridine-3-carboxamide (Compound 1260), N-[(6-amino-2-pyridyl)sulfonyl]-2-(8-azaspiro[3.5]nonan-8-yl)-6-(3-fluoro-5-isobutoxy-phenyl)pyridine-3-carboxamide (Compound 1264), N-[(6-amino-2-pyridyl)sulfonyl]-2-(3,3-dimethylmorpholin-4-yl)-6-(3-fluoro-5-isobutoxy-phenyl)pyridine-3-carboxamide (Compound 1267), N-[(6-amino-2-pyridyl)sulfonyl]-2-(4,4-dimethyl-1-piperidyl)-6-(3-fluoro-5-isobutoxy-phenyl)pyridine-3-carboxamide (Compound 1279), N-[(6-amino-2-pyridyl)sulfonyl]-6-(3-fluoro-5-isobutoxy-phenyl)-2-[(4R)-2,2,4-trimethylpyrrolidin-1-yl]pyridine-3-carboxamide (Compound 1289), N-[(6-amino-2-pyridyl)sulfonyl]-2-(7-azaspiro[3.5]nonan-7-yl)-6-(3-fluoro-5-isobutoxy-phenyl)pyridine-3-carboxamide (Compound 1303), N-[(6-amino-2-pyridyl)sulfonyl]-6-(3-fluoro-5-isobutoxy-phenyl)-2-[(2S)-2-(trifluoromethyl)pyrrolidin-1-yl]pyridine-3-carboxamide (Compound 1304), 2-(2,3,4,4a,5,6,7,7a-octahydrocyclopenta[b]pyridin-1-yl)-N-[(6-amino-2-pyridyl)sulfonyl]-6-(3-fluoro-5-isobutoxy-phenyl)pyridine-3-carboxamide (Compound 1313), N-[(6-amino-2-pyridyl)sulfonyl]-6-(3-fluoro-5-isobutoxy-phenyl)-2-(2-methyl-3-phenyl-pyrrolidin-1-yl)pyridine-3-carboxamide (Compound 1319) N-[(6-amino-2-pyridyl)sulfonyl]-2-(7-azaspiro[2.4]heptan-7-yl)-6-(3-fluoro-5-isobutoxy-phenyl)pyridine-3-carboxamide (Compound 1333), N-[(6-amino-2-pyridyl)sulfonyl]-2-[(3R,5S)-3,5-dimethyl-1-piperidyl]-6-(3-fluoro-5-isobutoxy-phenyl)pyridine-3-carboxamide (Compound 371), N-[(6-amino-2-pyridyl)sulfonyl]-6-(3-fluoro-5-isobutoxy-phenyl)-2-(1-piperidyl)pyridine-3-carboxamide (Compound 380), 2-(3,3a,4,5,6,6a-hexahydro-2H-cyclopenta[b]pyrrol-1-yl)-N-[(6-amino-2-pyridyl)sulfonyl]-6-(3-fluoro-5-isobutoxy-phenyl)pyridine-3-carboxamide (Compound 383), methyl (2S)-1-[3-[(6-amino-2-pyridyl)sulfonylcarbamoyl]-6-(3-fluoro-5-isobutoxy-phenyl)-2-pyridyl]pyrrolidine-2-carboxylate (Compound 385), N-[(6-amino-2-pyridyl)sulfonyl]-6-(3-fluoro-5-isobutoxy-phenyl)-2-[(2R)-2-(trifluoromethyl)pyrrolidin-1-yl]pyridine-3-carboxamide (Compound 398), N-[(6-amino-2-pyridyl)sulfonyl]-6-(3-fluoro-5-isobutoxy-phenyl)-2-[(3R)-3-methyl-1-piperidyl]pyridine-3-carboxamide (Compound 408), N-[(6-amino-2-pyridyl)sulfonyl]-2-(azepan-1-yl)-6-(3-fluoro-5-isobutoxy-phenyl)pyridine-3-carboxamide (Compound 418), N-[(6-amino-2-pyridyl)sulfonyl]-6-(3-fluoro-5-isobutoxy-phenyl)-2-[3-(methoxymethyl)-1-piperidyl]pyridine-3-carboxamide (Compound 419), N-[(6-amino-2-pyridyl)sulfonyl]-2-(7-azabicyclo[2.2.1]heptan-7-yl)-6-(3-fluoro-5-isobutoxy-phenyl)pyridine-3-carboxamide (Compound 420), N-[(6-amino-2-pyridyl)sulfonyl]-6-(3-fluoro-5-isobutoxy-phenyl)-2-[(2S)-2-methylpyrrolidin-1-yl]pyridine-3-carboxamide (Compound 421), N-[(6-amino-2-pyridyl)sulfonyl]-6-(3-fluoro-5-isobutoxy-phenyl)-2-(8-oxa-4-azaspiro[4.4]nonan-4-yl)pyridine-3-carboxamide (Compound 424), N-[(6-amino-2-pyridyl)sulfonyl]-6-(3-fluoro-5-isobutoxy-phenyl)-2-(2-methyl-1-piperidyl)pyridine-3-carboxamide (Compound 425), N-[(6-amino-2-pyridyl)sulfonyl]-6-(3-fluoro-5-isobutoxy-phenyl)-2-[(2R)-2-phenylpyrrolidin-1-yl]pyridine-3-carboxamide (Compound 447),
N-[(6-amino-2-pyridyl)sulfonyl]-2-(2,5-dihydropyrrol-1-yl)-6-(3-fluoro-5-isobutoxy-phenyl)pyridine-3-carboxamide (Compound 453),
N-[(6-amino-2-pyridyl)sulfonyl]-2-[(2S,5S)-2,5-dimethylpyrrolidin-1-yl]-6-(3-fluoro-5-isobutoxy-phenyl)pyridine-3-carboxamide (Compound 458),
N-[(6-amino-2-pyridyl)sulfonyl]-2-(3-benzylpyrrolidin-1-yl)-6-(3-fluoro-5-isobutoxy-phenyl)pyridine-3-carboxamide (Compound 473),
N-[(6-amino-2-pyridyl)sulfonyl]-6-(3-fluoro-5-isobutoxy-phenyl)-2-(2-methylpyrrolidin-1-yl)pyridine-3-carboxamide (Compound 479),
N-[(6-amino-2-pyridyl)sulfonyl]-6-(3-fluoro-5-isobutoxy-phenyl)-2-(2-methyl-4-phenyl-pyrrolidin-1-yl)pyridine-3-carboxamide (Compound 488),
N-[(6-amino-2-pyridyl)sulfonyl]-6-(3-fluoro-5-isobutoxy-phenyl)-2-[4-(trifluoromethyl)-3-azabicyclo[3.1.0]hexan-3-yl]pyridine-3-carboxamide (Compound 490),
N-[(6-amino-2-pyridyl)sulfonyl]-2-[2-(1,1-dimethylpropyl)pyrrolidin-1-yl]-6-(3-fluoro-5-isobutoxy-phenyl)pyridine-3-carboxamide (Compound 493),
N-[(6-amino-2-pyridyl)sulfonyl]-6-(3-fluoro-5-isobutoxy-phenyl)-2-(2,2,5-trimethylpyrrolidin-1-yl)pyridine-3-carboxamide (Compound 496),
N-[(6-amino-2-pyridyl)sulfonyl]-2-[1-cyclopropylethyl(methyl)amino]-6-(3-fluoro-5-isobutoxy-phenyl)pyridine-3-carboxamide (Compound 516),
N-[(6-amino-2-pyridyl)sulfonyl]-2-(6-azaspiro[3.3]heptan-6-yl)-6-(3-fluoro-5-isobutoxy-phenyl)pyridine-3-carboxamide (Compound 527),
N-[(6-amino-2-pyridyl)sulfonyl]-2-(3-ethyl-3-methyl-1-piperidyl)-6-(3-fluoro-5-isobutoxy-phenyl)pyridine-3-carboxamide (Compound 530),
N-[(6-amino-2-pyridyl)sulfonyl]-6-(3-fluoro-5-isobutoxy-phenyl)-2-[(3S)-2,2,3-trimethylpyrrolidin-1-yl]pyridine-3-carboxamide (Compound 547),
N-[(6-amino-2-pyridyl)sulfonyl]-6-(3-fluoro-5-isobutoxy-phenyl)-2-(2,2,4-trimethylpyrrolidin-1-yl)pyridine-3-carboxamide (Compound 555),
N-[(6-amino-2-pyridyl)sulfonyl]-6-(3-fluoro-5-isobutoxy-phenyl)-2-(3,3,5-trimethyl-1-piperidyl)pyridine-3-carboxamide (Compound 560),
N-[(6-amino-2-pyridyl)sulfonyl]-6-(3-fluoro-5-isobutoxy-phenyl)-2-(3,3,4-trimethyl-1-piperidyl)pyridine-3-carboxamide (Compound 575),
N-[(6-amino-2-pyridyl)sulfonyl]-2-[(1R,5S)-3-azabicyclo[3.2.1]octan-3-yl]-6-(3-fluoro-5-isobutoxy-phenyl)pyridine-3-carboxamide (Compound 581),
N-[(6-amino-2-pyridyl)sulfonyl]-2-(2,4-dimethylpyrrolidin-1-yl)-6-(3-fluoro-5-isobutoxy-phenyl)pyridine-3-carboxamide (Compound 587),
N-[(6-amino-2-pyridyl)sulfonyl]-6-(3-fluoro-5-isobutoxy-phenyl)-2-pyrrolidin-1-yl-pyridine-3-carboxamide (Compound 592),
N-[(6-amino-2-pyridyl)sulfonyl]-2-(2-cyclopropylpyrrolidin-1-yl)-6-(3-fluoro-5-isobutoxy-phenyl)pyridine-3-carboxamide (Compound 593),
N-[(6-amino-2-pyridyl)sulfonyl]-2-(6,6-dimethyl-3-azabicyclo[3.1.0]hexan-3-yl)-6-(3-fluoro-5-isobutoxy-phenyl)pyridine-3-carboxamide (Compound 609),
N-[(6-amino-2-pyridyl)sulfonyl]-2-(3-tert-butylpyrrolidin-1-yl)-6-(3-fluoro-5-isobutoxy-phenyl)pyridine-3-carboxamide (Compound 611),
N-[(6-amino-2-pyridyl)sulfonyl]-2-(2-tert-butylpyrrolidin-1-yl)-6-(3-fluoro-5-isobutoxy-phenyl)pyridine-3-carboxamide (Compound 613),
N-[(6-amino-2-pyridyl)sulfonyl]-2-(4-ethyl-1-piperidyl)-6-(3-fluoro-5-isobutoxy-phenyl)pyridine-3-carboxamide (Compound 615),
N-[(6-amino-2-pyridyl)sulfonyl]-6-(3-fluoro-5-isobutoxy-phenyl)-2-[(3R)-3-phenyl-1-piperidyl]pyridine-3-carboxamide (Compound 651),
N-[(6-amino-2-pyridyl)sulfonyl]-2-(3-cyclopropyl-1-piperidyl)-6-(3-fluoro-5-isobutoxy-phenyl)pyridine-3-carboxamide (Compound 655),
N-[(6-amino-2-pyridyl)sulfonyl]-6-(3-fluoro-5-isobutoxy-phenyl)-2-[(3R)-2,2,3-trimethylpyrrolidin-1-yl]pyridine-3-carboxamide (Compound 657),
N-[(6-amino-2-pyridyl)sulfonyl]-6-(3-fluoro-5-isobutoxy-phenyl)-2-[2-(2-pyridyl)pyrrolidin-1-yl]pyridine-3-carboxamide (Compound 659),
N-[(6-amino-2-pyridyl)sulfonyl]-2-(2-benzyl-2-methyl-pyrrolidin-1-yl)-6-(3-fluoro-5-isobutoxy-phenyl)pyridine-3-carboxamide (Compound 663),
N-[(6-amino-2-pyridyl)sulfonyl]-6-(3-fluoro-5-isobutoxy-phenyl)-2-[(3S)-3-methylpyrrolidin-1-yl]pyridine-3-carboxamide (Compound 678),
N-[(6-amino-2-pyridyl)sulfonyl]-2-(3-azabicyclo[2.2.1]heptan-3-yl)-6-(3-fluoro-5-isobutoxy-phenyl)pyridine-3-carboxamide (Compound 680),
N-[(6-amino-2-pyridyl)sulfonyl]-2-[cyclobutyl(methyl)amino]-6-(3-fluoro-5-isobutoxy-phenyl)pyridine-3-carboxamide (Compound 683),
N-[(6-amino-2-pyridyl)sulfonyl]-6-(3-fluoro-5-isobutoxy-phenyl)-2-[(3S)-3-phenyl-1-piperidyl]pyridine-3-carboxamide (Compound 684),
N-[(6-amino-2-pyridyl)sulfonyl]-6-(3-fluoro-5-isobutoxy-phenyl)-2-[(2R)-2-methylpyrrolidin-1-yl]pyridine-3-carboxamide (Compound 694),
N-[(6-amino-2-pyridyl)sulfonyl]-2-(2,5-dimethyl-3-phenyl-pyrrolidin-1-yl)-6-(3-fluoro-5-isobutoxy-phenyl)pyridine-3-carboxamide (Compound 711),
N-[(6-amino-2-pyridyl)sulfonyl]-6-(3-fluoro-5-isobutoxy-phenyl)-2-[(2S)-2-(methoxymethyl)pyrrolidin-1-yl]pyridine-3-carboxamide (Compound 719),
N-[(6-amino-2-pyridyl)sulfonyl]-2-(2,3-dimethylpyrrolidin-1-yl)-6-(3-fluoro-5-isobutoxy-phenyl)pyridine-3-carboxamide (Compound 720),
N-[(6-amino-2-pyridyl)sulfonyl]-6-(3-fluoro-5-isobutoxy-phenyl)-2-(3-methyl-1-piperidyl)pyridine-3-carboxamide (Compound 735),
N-[(6-amino-2-pyridyl)sulfonyl]-2-[(2R,5R)-2,5-dimethylpyrrolidin-1-yl]-6-(3-fluoro-5-isobutoxy-phenyl)pyridine-3-carboxamide (Compound 751),
N-[(6-amino-2-pyridyl)sulfonyl]-2-(2-benzylpyrrolidin-1-yl)-6-(3-fluoro-5-isobutoxy-phenyl)pyridine-3-carboxamide (Compound 772),
N-[(6-amino-2-pyridyl)sulfonyl]-2-[2,2-dimethyl-3-(trifluoromethyl)pyrrolidin-1-yl]-6-(3-fluoro-5-isobutoxy-phenyl)pyridine-3-carboxamide (Compound 780),
N-[(6-amino-2-pyridyl)sulfonyl]-2-(2,3-dimethyl-1-piperidyl)-6-(3-fluoro-5-isobutoxy-phenyl)pyridine-3-carboxamide (Compound 837),
N-[(6-amino-2-pyridyl)sulfonyl]-2-(8-azaspiro[3.4]octan-8-yl)-6-(3-fluoro-5-isobutoxy-phenyl)pyridine-3-carboxamide (Compound 845),
N-[(6-amino-2-pyridyl)sulfonyl]-6-(3-fluoro-5-isobutoxy-phenyl)-2-(2,2,4,4-tetramethylpyrrolidin-1-yl)pyridine-3-carboxamide (Compound 850), 2-(3,3a,4,5,6,6a-hexahydro-1H-cyclopenta[c]pyrrol-2-yl)-N-[(6-amino-2-pyridyl)sulfonyl]-6-(3-fluoro-5-isobutoxy-phenyl)pyridine-3-carboxamide (Compound 857), N-[(6-amino-2-pyridyl)sulfonyl]-6-(3-fluoro-5-isobutoxy-phenyl)-2-(2-phenylpyrrolidin-1-yl)pyridine-3-carboxamide (Compound 859), N-[(6-amino-2-pyridyl)sulfonyl]-2-[cyclopropylmethyl(propyl)amino]-6-(3-fluoro-5-isobutoxy-phenyl)pyridine-3-carboxamide (Compound 881), N-[(6-amino-2-pyridyl)sulfonyl]-2-(3,3-dimethyl-1-piperidyl)-6-(3-fluoro-5-isobutoxy-phenyl)pyridine-3-carboxamide (Compound 887), N-[(6-amino-2-pyridyl)sulfonyl]-2-(4-azabicyclo[3.1.0]hexan-4-yl)-6-(3-fluoro-5-isobutoxy-phenyl)pyridine-3-carboxamide (Compound 906), N-[(6-amino-2-pyridyl)sulfonyl]-2-[(1S,4R)-3-azabicyclo[2.2.1]heptan-3-yl]-6-(3-fluoro-5-isobutoxy-phenyl)pyridine-3-carboxamide (Compound 924), N-[(6-amino-2-pyridyl)sulfonyl]-2-(9-azaspiro[4.4]nonan-9-yl)-6-(3-fluoro-5-isobutoxy-phenyl)pyridine-3-carboxamide (Compound 926), N-[(6-amino-2-pyridyl)sulfonyl]-2-(3-ethylpyrrolidin-1-yl)-6-(3-fluoro-5-isobutoxy-phenyl)pyridine-3-carboxamide (Compound 931), N-[(6-amino-2-pyridyl)sulfonyl]-2-[(1R,5S)-8-azabicyclo[3.2.1]octan-8-yl]-6-(3-fluoro-5-isobutoxy-phenyl)pyridine-3-carboxamide (Compound 934), N-[(6-amino-2-pyridyl)sulfonyl]-2-(7-azaspiro[2.5]octan-7-yl)-6-(3-fluoro-5-isobutoxy-phenyl)pyridine-3-carboxamide (Compound 953), N-[(6-amina-2-pyridyl)sulfonyl]-2-(3-benzyl-2-methyl-pyrrolidin-1-yl)-6-(3-fluoro-5-isobutoxy-phenyl)pyridine-3-carboxamide (Compound 969), N-[(6-amino-2-pyridyl)sulfonyl]-2-(6-azaspiro[2.5]octan-6-yl)-6-(3-fluoro-5-isobutoxy-phenyl)pyridine-3-carboxamide (Compound 973), N-[(6-amino-2-pyridyl)sulfonyl]-6-(3-fluoro-5-isobutoxy-phenyl)-2-(4-methyl-1-piperidyl)pyridine-3-carboxamide (Compound 991), N-[(6-amino-2-pyridyl)sulfonyl]-2-(2,2-dimethyl-1-piperidyl)-6-(3-fluoro-5-isobutoxy-phenyl)pyridine-3-carboxamide (Compound 1004), N-[(6-amino-2-pyridyl)sulfonyl]-6-(3-fluoro-5-isobutoxy-phenyl)-2-[methyl-[(1-methylcyclopropyl)methyl]amino]pyridine-3-carboxamide (Compound 1009), N-[(6-amino-2-pyridyl)sulfonyl]-2-[cyclopropylmethyl(methyl)amino]-6-(3-fluoro-5-isobutoxy-phenyl)pyridine-3-carboxamide (Compound 1010), N-[(6-amino-2-pyridyl)sulfonyl]-2-(3,5-dimethyl-1-piperidyl)-6-(3-fluoro-5-isobutoxy-phenyl)pyridine-3-carboxamide (Compound 1013), N-[(6-amino-2-pyridyl)sulfonyl]-6-(3-fluoro-5-isobutoxy-phenyl)-2-[(3R)-3-methylpyrrolidin-1-yl]pyridine-3-carboxamide (Compound 1051), N-[(6-amino-2-pyridyl)sulfonyl]-2-(6-azaspiro[2.4]heptan-6-yl)-6-(3-fluoro-5-isobutoxy-phenyl)pyridine-3-carboxamide (Compound 1061), N-[(6-amino-2-pyridyl)sulfonyl]-6-(3-fluoro-5-isobutoxy-phenyl)-2-[(2R)-2,3,3-trimethylpyrrolidin-1-yl]pyridine-3-carboxamide (Compound 1065), N-[(6-amino-2-pyridyl)sulfonyl]-2-(2,2-dimethyl-4-oxo-pyrrolidin-1-yl)-6-(3-fluoro-5-isobutoxy-phenyl)-1,2-dihydropyridine-3-carboxamide, N-[(6-amino-2-pyridyl)sulfonyl]-2-[(2S)-2-tert-butylpyrrolidin-1-yl]-6-(3-fluoro-5-isobutoxy-phenyl)pyridine-3-carboxamide (Compound 1097), N-[(6-amino-2-pyridyl)sulfonyl]-6-(3-fluoro-5-isobutoxy-phenyl)-2-(3-isopropyl-1-piperidyl)pyridine-3-carboxamide (Compound 1098), N-[(6-amino-2-pyridyl)sulfonyl]-2-[cyclopropyl(methyl)amino]-6-(3-fluoro-5-isobutoxy-phenyl)pyridine-3-carboxamide (Compound 1117), N-[(6-amino-2-pyridyl)sulfonyl]-6-(3-fluoro-5-isobutoxy-phenyl)-2-(2,2,3-trimethylpyrrolidin-1-yl)pyridine-3-carboxamide (Compound 1121), N-[(6-amino-2-pyridyl)sulfonyl]-6-(3-fluoro-5-isobutoxy-phenyl)-2-[(2S)-2,3,3-trimethylpyrrolidin-1-yl]pyridine-3-carboxamide (Compound 1144), N-[(6-amino-2-pyridyl)sulfonyl]-6-(3-fluoro-5-isobutoxy-phenyl)-2-[(2R)-2-(methoxymethyl)pyrrolidin-1-yl]pyridine-3-carboxamide (Compound 1149), N-[(6-amino-2-pyridyl)sulfonyl]-6-(3-fluoro-5-isobutoxy-phenyl)-2-(2,3,3-trimethylpyrrolidin-1-yl)pyridine-3-carboxamide (Compound 1156), N-[(6-amino-2-pyridyl)sulfonyl]-2-[cyclopropylmethyl(isopropyl)amino]-6-(3-fluoro-5-isobutoxy-phenyl)pyridine-3-carboxamide (Compound 1157), N-[(6-amino-2-pyridyl)sulfonyl]-6-(3-fluoro-5-isobutoxy-phenyl)-2-(4-methylene-1-piperidyl)pyridine-3-carboxamide (Compound 1162), N-[(6-amino-2-pyridyl)sulfonyl]-6-(3-fluoro-5-isobutoxy-phenyl)-2-[(5R)-2,2,5-trimethylpyrrolidin-1-yl]pyridine-3-carboxamide (Compound 1166), N-[(6-amino-2-pyridyl)sulfonyl]-2-[(2R)-2-tert-butylpyrrolidin-1-yl]-6-(3-fluoro-5-isobutoxy-phenyl)pyridine-3-carboxamide (Compound 1170), N-[(6-amino-2-pyridyl)sulfonyl]-2-[(1R,4S)-3-azabicyclo[2.2.1]heptan-3-yl]-6-(3-fluoro-5-isobutoxy-phenyl)pyridine-3-carboxamide (Compound 1180), N-[(6-amino-2-pyridyl)sulfonyl]-2-(2,2-dimethyl-3-oxo-pyrrolidin-1-yl)-6-(3-fluoro-5-isobutoxy-phenyl)-1,2-dihydropyridine-3-carboxamide, N-[(6-amino-2-pyridyl)sulfonyl]-6-(3-fluoro-5-isobutoxy-phenyl)-2-[(3S)-3-methyl-1-piperidyl]pyridine-3-carboxamide (Compound 1193), N-[(6-amino-2-pyridyl)sulfonyl]-2-[1-(3-chlorophenyl)ethyl-methyl-amino]-6-(3-fluoro-5-isobutoxy-phenyl)pyridine-3-carboxamide (Compound 1205), N-[(6-amino-2-pyridyl)sulfonyl]-2-[(3S,5S)-3,5-dimethyl-1-piperidyl]-6-(3-fluoro-5-isobutoxy-phenyl)pyridine-3-carboxamide (Compound 1210), N-[(6-amino-2-pyridyl)sulfonyl]-2-(2-ethylpyrrolidin-1-yl)-6-(3-fluoro-5-isobutoxy-phenyl)pyridine-3-carboxamide (Compound 1218), N-[(6-amino-2-pyridyl)sulfonyl]-2-(2-ethyl-5-methyl-pyrrolidin-1-yl)-6-(3-fluoro-5-isobutoxy-phenyl)pyridine-3-carboxamide (Compound 1222), N-[(6-amino-2-pyridyl)sulfonyl]-6-(3-fluoro-5-isobutoxy-phenyl)-2-[(5S)-2,2,5-trimethylpyrrolidin-1-yl]pyridine-3-carboxamide (Compound 1241), N-[(6-amino-2-pyridyl)sulfonyl]-6-(3-fluoro-5-isobutoxy-phenyl)-2-(2-isopropylpyrrolidin-1-yl)pyridine-3-carboxamide (Compound 1258), N-[(6-amino-2-pyridyl)sulfonyl]-6-(3-fluoro-5-isobutoxy-phenyl)-2-[(2S)-2-phenylpyrrolidin-1-yl]pyridine-3-carboxamide (Compound 1260), N-[(6-amino-2-pyridyl)sulfonyl]-2-(8-azaspiro[3.5]nonan-8-yl)-6-(3-fluoro-5-isobutoxy-phenyl)pyridine-3-carboxamide (Compound 1264), N-[(6-amino-2-pyridyl)sulfonyl]-2-(3,3-dimethylmorpholin-4-yl)-6-(3-fluoro-5-isobutoxy-phenyl)pyridine-3-carboxamide (Compound 1267), N-[(6-amino-2-pyridyl)sulfonyl]-2-(4,4-dimethyl-1-piperidyl)-6-(3-fluoro-5-isobutoxy-phenyl)pyridine-3-carboxamide (Compound 1279), N-[(6-amino-2-pyridyl)sulfonyl]-6-(3-fluoro-5-isobutoxy-phenyl)-2-[(4R)-2,2,4-trimethylpyrrolidin-1-yl]pyridine-3-carboxamide (Compound 1289), N-[(6-amino-2-pyridyl)sulfonyl]-2-(7-azaspiro[3.5]nonan-7-yl)-6-(3-fluoro-5-isobutoxy-phenyl)pyridine-3-carboxamide (Compound 1303), N-[(6-amino-2-pyridyl)sulfonyl]-6-(3-fluoro-5-isobutoxy-phenyl)-2-[(2S)-2-(trifluoromethyl)pyrrolidin-1-yl]pyridine-3-carboxamide (Compound 1304), 2-(2,3,4,4a,5,6,7,7a-octahydrocyclopenta[b]pyridin-1-yl)-N-[(6-amino-2-pyridyl)sulfonyl]-6-(3-fluoro-5-isobutoxy-phenyl)pyridine-3-carboxamide (Compound 1313), N-[(6-amino-2-pyridyl)sulfonyl]-6-(3-fluoro-5-isobutoxy-phenyl)-2-(2-methyl-3-phenyl-pyrrolidin-1-yl)pyridine-3-carboxamide (Compound 1319), N-[(6-amino-2-pyridyl)sulfonyl]-2-(4-methyl-1-piperidyl)-6-(p-tolyl)pyridine-3-carboxamide (Compound 802), N-[(6-amino-2-pyridyl)sulfonyl]-6-(6-methoxy-5-methyl-3-pyridyl)-2-(4-methyl-1-piperidyl)pyridine-3-carboxamide (Compound 863), N-[(6-amino-2-pyridyl)sulfonyl]-6-(4-ethoxyphenyl)-2-(4-methyl-1-piperidyl)pyridine-3-carboxamide (Compound 910), 6-(3-fluoro-5-isopropoxy-phenyl)-2-(4-methyl-1-piperidyl)-N-(1H-pyrazol-3-ylsulfonyl)pyridine-3-carboxamide (Compound 1042), N-[(6-amino-2-pyridyl)sulfonyl]-2-(7-azaspiro[2.4]heptan-7-yl)-6-(3-fluoro-5-isobutoxy-phenyl)pyridine-3-carboxamide (Compound 1333), N-[(6-amino-2-pyridyl)sulfonyl]-2-[(3R,5S)-3,5-dimethyl-1-piperidyl]-6-(3-fluoro-5-isobutoxy-phenyl)pyridine-3-carboxamide (Compound 371), N-[(6-amino-2-pyridyl)sulfonyl]-6-(3-fluoro-5-isobutoxy-phenyl)-2-(1-piperidyl)pyridine-3-carboxamide (Compound 380), 2-(3,3a,4,5,6,6a-hexahydro-2H-cyclopenta[b]pyrrol-1-yl)-N-[(6-amino-2-pyridyl)sulfonyl]-6-(3-fluoro-5-isobutoxy-phenyl)pyridine-3-carboxamide (Compound 383), methyl (2S)-1-[3-[(6-amino-2-pyridyl)sulfonylcarbamoyl]-6-(3-fluoro-5-isobutoxy-phenyl)-2-pyridyl]pyrrolidine-2-carboxylate (Compound 385), N-[(6-amino-2-pyridyl)sulfonyl]-6-(3-fluoro-5-isobutoxy-phenyl)-2-[(2R)-2-(trifluoromethyl)pyrrolidin-1-yl]pyridine-3-carboxamide (Compound 398), N-[(6-amino-2-pyridyl)sulfonyl]-6-(3-fluoro-5-isobutoxy-phenyl)-2-[(3R)-3-methyl-1-piperidyl]pyridine-3-carboxamide (Compound 408), N-[(6-amino-2-pyridyl)sulfonyl]-2-(azepan-1-yl)-6-(3-fluoro-5-isobutoxy-phenyl)pyridine-3-carboxamide (Compound 418), N-[(6-amino-2-pyridyl)sulfonyl]-6-(3-fluoro-5-isobutoxy-phenyl)-2-[3-(methoxymethyl)-1-piperidyl]pyridine-3-carboxamide (Compound 419), N-[(6-amino-2-pyridyl)sulfonyl]-2-(7-azabicyclo[2.2.1]heptan-7-yl)-6-(3-fluoro-5-isobutoxy-phenyl)pyridine-3-carboxamide (Compound 420), N-[(6-amino-2-pyridyl)sulfonyl]-6-(3-fluoro-5-isobutoxy-phenyl)-2-[(2S)-2-methylpyrrolidin-1-yl]pyridine-3-carboxamide (Compound 421), N-[(6-amino-2-pyridyl)sulfonyl]-6-(3-fluoro-5-isobutoxy-phenyl)-2-(8-oxa-4-azaspiro[4.4]nonan-4-yl)pyridine-3-carboxamide (Compound 424), N-[(6-amino-2-pyridyl)sulfonyl]-6-(3-fluoro-5-isobutoxy-phenyl)-2-(2-methyl-1-piperidyl)pyridine-3-carboxamide (Compound 425), N-[(6-amino-2-pyridyl)sulfonyl]-6-(3-fluoro-5-isobutoxy-phenyl)-2-[(2R)-2-phenylpyrrolidin-1-yl]pyridine-3-carboxamide (Compound 447), N-[(6-amino-2-pyridyl)sulfonyl]-2-(2,5-dihydropyrrol-1-yl)-6-(3-fluoro-5-isobutoxy-phenyl)pyridine-3-carboxamide (Compound 453), N-[(6-amino-2-pyridyl)sulfonyl]-2-[(2S,5S)-2,5-dimethylpyrrolidin-1-yl]-6-(3-fluoro-5-isobutoxy-phenyl)pyridine-3-carboxamide (Compound 458), N-[(6-amino-2-pyridyl)sulfonyl]-2-(3-benzylpyrrolidin-1-yl)-6-(3-fluoro-5-isobutoxy-phenyl)pyridine-3-carboxamide (Compound 473), N-[(6-amino-2-pyridyl)sulfonyl]-6-(3-fluoro-5-isobutoxy-phenyl)-2-(2-methylpyrrolidin-1-yl)pyridine-3-carboxamide (Compound 479), N-[(6-amino-2-pyridyl)sulfonyl]-6-(3-fluoro-5-isobutoxy-phenyl)-2-(2-methyl-4-phenyl-pyrrolidin-1-yl)pyridine-3-carboxamide (Compound 488), N-[(6-amino-2-pyridyl)sulfonyl]-6-(3-fluoro-5-isobutoxy-phenyl)-2-[4-(trifluoromethyl)-3-azabicyclo[3.1.0]hexan-3-yl]pyridine-3-carboxamide (Compound 490), N-[(6-amino-2-pyridyl)sulfonyl]-2-[2-(1,1-dimethylpropyl)pyrrolidin-1-yl]-6-(3-fluoro-5-isobutoxy-phenyl)pyridine-3-carboxamide (Compound 493), N-[(6-amino-2-pyridyl)sulfonyl]-6-(3-fluoro-5-isobutoxy-phenyl)-2-(2,2,5-trimethylpyrrolidin-1-yl)pyridine-3-carboxamide (Compound 496), N-[(6-amino-2-pyridyl)sulfonyl]-2-[1-cyclopropylethyl(methyl)amino]-6-(3-fluoro-5-isobutoxy-phenyl)pyridine-3-carboxamide (Compound 516), N-[(6-amino-2-pyridyl)sulfonyl]-2-(6-azaspiro[3.3]heptan-6-yl)-6-(3-fluoro-5-isobutoxy-phenyl)pyridine-3-carboxamide (Compound 527), N-[(6-amino-2-pyridyl)sulfonyl]-2-(3-ethyl-3-methyl-1-piperidyl)-6-(3-fluoro-5-isobutoxy-phenyl)pyridine-3-carboxamide (Compound 530), N-[(6-amino-2-pyridyl)sulfonyl]-6-(3-fluoro-5-isobutoxy-phenyl)-2-[(3S)-2,2,3-trimethylpyrrolidin-1-yl]pyridine-3-carboxamide (Compound 547), N-[(6-amino-2-pyridyl)sulfonyl]-6-(3-fluoro-5-isobutoxy-phenyl)-2-(2,2,4-trimethylpyrrolidin-1-yl)pyridine-3-carboxamide (Compound 555), N-[(6-amino-2-pyridyl)sulfonyl]-6-(3-fluoro-5-isobutoxy-phenyl)-2-(3,3,5-trimethyl-1-piperidyl)pyridine-3-carboxamide (Compound 560), N-[(6-amino-2-pyridyl)sulfonyl]-6-(3-fluoro-5-isobutoxy-phenyl)-2-(3,3,4-trimethyl-1-piperidyl)pyridine-3-carboxamide (Compound 575), N-[(6-amino-2-pyridyl)sulfonyl]-2-[(1R,5S)-3-azabicyclo[3.2.1]octan-3-yl]-6-(3-fluoro-5-isobutoxy-phenyl)pyridine-3-carboxamide (Compound 581), N-[(6-amino-2-pyridyl)sulfonyl]-2-(2,4-dimethylpyrrolidin-1-yl)-6-(3-fluoro-5-isobutoxy-phenyl)pyridine-3-carboxamide (Compound 587), N-[(6-amino-2-pyridyl)sulfonyl]-6-(3-fluoro-5-isobutoxy-phenyl)-2-pyrrolidin-1-yl-pyridine-3-carboxamide (Compound 592), N-[(6-amino-2-pyridyl)sulfonyl]-2-(2-cyclopropylpyrrolidin-1-yl)-6-(3-fluoro-5-isobutoxy-phenyl)pyridine-3-carboxamide (Compound 593), N-[(6-amino-2-pyridyl)sulfonyl]-2-(6,6-dimethyl-3-azabicyclo[3.1.0]hexan-3-yl)-6-(3-fluoro-5-isobutoxy-phenyl)pyridine-3-carboxamide (Compound 609), N-[(6-amino-2-pyridyl)sulfonyl]-2-(3-tert-butylpyrrolidin-1-yl)-6-(3-fluoro-5-isobutoxy-phenyl)pyridine-3-carboxamide (Compound 611),
N-[(6-amino-2-pyridyl)sulfonyl]-2-(2-tert-butylpyrrolidin-1-yl)-6-(3-fluoro-5-isobutoxy-phenyl)pyridine-3-carboxamide (Compound 613),
N-[(6-amino-2-pyridyl)sulfonyl]-2-(4-ethyl-1-piperidyl)-6-(3-fluoro-5-isobutoxy-phenyl)pyridine-3-carboxamide (Compound 615),
N-[(6-amino-2-pyridyl)sulfonyl]-6-(3-fluoro-5-isobutoxy-phenyl)-2-[(3R)-3-phenyl-1-piperidyl]pyridine-3-carboxamide (Compound 651),
N-[(6-amino-2-pyridyl)sulfonyl]-2-(3-cyclopropyl-1-piperidyl)-6-(3-fluoro-5-isobutoxy-phenyl)pyridine-3-carboxamide (Compound 655),
N-[(6-amino-2-pyridyl)sulfonyl]-6-(3-fluoro-5-isobutoxy-phenyl)-2-[(3R)-2,2,3-trimethylpyrrolidin-1-yl]pyridine-3-carboxamide (Compound 657),
N-[(6-amino-2-pyridyl)sulfonyl]-6-(3-fluoro-5-isobutoxy-phenyl)-2-[2-(2-pyridyl)pyrrolidin-1-yl]pyridine-3-carboxamide (Compound 659),
N-[(6-amino-2-pyridyl)sulfonyl]-2-(2-benzyl-2-methyl-pyrrolidin-1-yl)-6-(3-fluoro-5-isobutoxy-phenyl)pyridine-3-carboxamide (Compound 663),
N-[(6-amino-2-pyridyl)sulfonyl]-6-(3-fluoro-5-isobutoxy-phenyl)-2-[(3S)-3-methylpyrrolidin-1-yl]pyridine-3-carboxamide (Compound 678),
N-[(6-amino-2-pyridyl)sulfonyl]-2-(3-azabicyclo[2.2.1]heptan-3-yl)-6-(3-fluoro-5-isobutoxy-phenyl)pyridine-3-carboxamide (Compound 680),
N-[(6-amino-2-pyridyl)sulfonyl]-2-[cyclobutyl(methyl)amino]-6-(3-fluoro-5-isobutoxy-phenyl)pyridine-3-carboxamide (Compound 683),
N-[(6-amino-2-pyridyl)sulfonyl]-6-(3-fluoro-5-isobutoxy-phenyl)-2-[(3S)-3-phenyl-1-piperidyl]pyridine-3-carboxamide (Compound 684),
N-[(6-amino-2-pyridyl)sulfonyl]-6-(3-fluoro-5-isobutoxy-phenyl)-2-[(2R)-2-methylpyrrolidin-1-yl]pyridine-3-carboxamide (Compound 694),
N-[(6-amino-2-pyridyl)sulfonyl]-2-(2,5-dimethyl-3-phenyl-pyrrolidin-1-yl)-6-(3-fluoro-5-isobutoxy-phenyl)pyridine-3-carboxamide (Compound 711),
N-[(6-amino-2-pyridyl)sulfonyl]-6-(3-fluoro-5-isobutoxy-phenyl)-2-[(2S)-2-(methoxymethyl)pyrrolidin-1-yl]pyridine-3-carboxamide (Compound 719),
N-[(6-amino-2-pyridyl)sulfonyl]-2-(2,3-dimethylpyrrolidin-1-yl)-6-(3-fluoro-5-isobutoxy-phenyl)pyridine-3-carboxamide (Compound 720),
N-[(6-amino-2-pyridyl)sulfonyl]-6-(3-fluoro-5-isobutoxy-phenyl)-2-(3-methyl-1-piperidyl)pyridine-3-carboxamide (Compound 735),
N-[(6-amino-2-pyridyl)sulfonyl]-2-[(2R,5R)-2,5-dimethylpyrrolidin-1-yl]-6-(3-fluoro-5-isobutoxy-phenyl)pyridine-3-carboxamide (Compound 751),
N-[(6-amino-2-pyridyl)sulfonyl]-2-(2-benzylpyrrolidin-1-yl)-6-(3-fluoro-5-isobutoxy-phenyl)pyridine-3-carboxamide (Compound 772),
N-[(6-amino-2-pyridyl)sulfonyl]-2-[2,2-dimethyl-3-(trifluoromethyl)pyrrolidin-1-yl]-6-(3-fluoro-5-isobutoxy-phenyl)pyridine-3-carboxamide (Compound 780),
N-[(6-amino-2-pyridyl)sulfonyl]-2-(2,3-dimethyl-1-piperidyl)-6-(3-fluoro-5-isobutoxy-phenyl)pyridine-3-carboxamide (Compound 837),
N-[(6-amino-2-pyridyl)sulfonyl]-2-(8-azaspiro[3.4]octan-8-yl)-6-(3-fluoro-5-isobutoxy-phenyl)pyridine-3-carboxamide (Compound 845),
N-[(6-amino-2-pyridyl)sulfonyl]-6-(3-fluoro-5-isobutoxy-phenyl)-2-(2,2,4,4-tetramethylpyrrolidin-1-yl)pyridine-3-carboxamide (Compound 850),
2-(3,3a,4,5,6,6a-hexahydro-1H-cyclopenta[c]pyrrol-2-yl)-N-[(6-amino-2-pyridyl)sulfonyl]-6-(3-fluoro-5-isobutoxy-phenyl)pyridine-3-carboxamide (Compound 857),
N-[(6-amino-2-pyridyl)sulfonyl]-6-(3-fluoro-5-isobutoxy-phenyl)-2-(2-phenylpyrrolidin-1-yl)pyridine-3-carboxamide (Compound 859),
N-[(6-amino-2-pyridyl)sulfonyl]-2-[cyclopropylmethyl(propyl)amino]-6-(3-fluoro-5-isobutoxy-phenyl)pyridine-3-carboxamide (Compound 881),
N-[(6-amino-2-pyridyl)sulfonyl]-2-(3,3-dimethyl-1-piperidyl)-6-(3-fluoro-5-isobutoxy-phenyl)pyridine-3-carboxamide (Compound 887),
N-[(6-amino-2-pyridyl)sulfonyl]-2-(4-azabicyclo[3.1.0]hexan-4-yl)-6-(3-fluoro-5-isobutoxy-phenyl)pyridine-3-carboxamide (Compound 906),
N-[(6-amino-2-pyridyl)sulfonyl]-2-[(1S,4R)-3-azabicyclo[2.2.1]heptan-3-yl]-6-(3-fluoro-5-isobutoxy-phenyl)pyridine-3-carboxamide (Compound 924),
N-[(6-amino-2-pyridyl)sulfonyl]-2-(9-azaspiro[4.4]nonan-9-yl)-6-(3-fluoro-5-isobutoxy-phenyl)pyridine-3-carboxamide (Compound 926),
N-[(6-amino-2-pyridyl)sulfonyl]-2-(3-ethylpyrrolidin-1-yl)-6-(3-fluoro-5-isobutoxy-phenyl)pyridine-3-carboxamide (Compound 931),
N-[(6-amino-2-pyridyl)sulfonyl]-2-[(1R,5S)-8-azabicyclo[3.2.1]octan-8-yl]-6-(3-fluoro-5-isobutoxy-phenyl)pyridine-3-carboxamide (Compound 934),
N-[(6-amino-2-pyridyl)sulfonyl]-2-(7-azaspiro[2.5]octan-7-yl)-6-(3-fluoro-5-isobutoxy-phenyl)pyridine-3-carboxamide (Compound 953),
N-[(6-amino-2-pyridyl)sulfonyl]-2-(3-benzyl-2-methyl-pyrrolidin-1-yl)-6-(3-fluoro-5-isobutoxy-phenyl)pyridine-3-carboxamide (Compound 969),
N-[(6-amino-2-pyridyl)sulfonyl]-2-(6-azaspiro[2.5]octan-6-yl)-6-(3-fluoro-5-isobutoxy-phenyl)pyridine-3-carboxamide (Compound 973),
N-[(6-amino-2-pyridyl)sulfonyl]-6-(3-fluoro-5-isobutoxy-phenyl)-2-(4-methyl-1-piperidyl)pyridine-3-carboxamide (Compound 991),
N-[(6-amino-2-pyridyl)sulfonyl]-2-(2,2-dimethyl-1-piperidyl)-6-(3-fluoro-5-isobutoxy-phenyl)pyridine-3-carboxamide (Compound 1004),
N-[(6-amino-2-pyridyl)sulfonyl]-6-(3-fluoro-5-isobutoxy-phenyl)-2-[methyl-[(1-methylcyclopropyl)methyl]amino]pyridine-3-carboxamide (Compound 1009),
N-[(6-amino-2-pyridyl)sulfonyl]-2-[cyclopropylmethyl(methyl)amino]-6-(3-fluoro-5-isobutoxy-phenyl)pyridine-3-carboxamide (Compound 1010),
N-[(6-amino-2-pyridyl)sulfonyl]-2-(3,5-dimethyl-1-piperidyl)-6-(3-fluoro-5-isobutoxy-phenyl)pyridine-3-carboxamide (Compound 1013),
N-[(6-amino-2-pyridyl)sulfonyl]-6-(3-fluoro-5-isobutoxy-phenyl)-2-[(3R)-3-methylpyrrolidin-1-yl]pyridine-3-carboxamide (Compound 1051),
N-[(6-amino-2-pyridyl)sulfonyl]-2-(6-azaspiro[2.4]heptan-6-yl)-6-(3-fluoro-5-isobutoxy-phenyl)pyridine-3-carboxamide (Compound 1061),
N-[(6-amino-2-pyridyl)sulfonyl]-6-(3-fluoro-5-isobutoxy-phenyl)-2-[(2R)-2,3,3-trimethylpyrrolidin-1-yl]pyridine-3-carboxamide (Compound 1065),
N-[(6-amino-2-pyridyl)sulfonyl]-2-(2,2-dimethyl-4-oxo-pyrrolidin-1-yl)-6-(3-fluoro-5-isobutoxy-phenyl)-1,2-dihydropyridine-3-carboxamide, N-[(6-amino-2-pyridyl)sulfonyl]-2-[(2S)-2-tert-butylpyrrolidin-1-yl]-6-(3-fluoro-5-isobutoxy-phenyl)pyridine-3-carboxamide (Compound 1097), N-[(6-amino-2-pyridyl)sulfonyl]-6-(3-fluoro-5-isobutoxy-phenyl)-2-(3-isopropyl-1-piperidyl)pyridine-3-carboxamide (Compound 1098), N-[(6-amino-2-pyridyl)sulfonyl]-2-[cyclopropyl(methyl)amino]-6-(3-fluoro-5-isobutoxy-phenyl)pyridine-3-carboxamide (Compound 1117), N-[(6-amino-2-pyridyl)sulfonyl]-6-(3-fluoro-5-isobutoxy-phenyl)-2-(2,2,3-trimethylpyrrolidin-1-yl)pyridine-3-carboxamide (Compound 1121), N-[(6-amino-2-pyridyl)sulfonyl]-6-(3-fluoro-5-isobutoxy-phenyl)-2-[(2S)-2,3,3-trimethylpyrrolidin-1-yl]pyridine-3-carboxamide (Compound 1144), N-[(6-amino-2-pyridyl)sulfonyl]-6-(3-fluoro-5-isobutoxy-phenyl)-2-[(2R)-2-(methoxymethyl)pyrrolidin-1-yl]pyridine-3-carboxamide (Compound 1149), N-[(6-amino-2-pyridyl)sulfonyl]-6-(3-fluoro-5-isobutoxy-phenyl)-2-(2,3,3-trimethylpyrrolidin-1-yl)pyridine-3-carboxamide (Compound 1156), N-[(6-amino-2-pyridyl)sulfonyl]-2-[cyclopropylmethyl(isopropyl)amino]-6-(3-fluoro-5-isobutoxy-phenyl)pyridine-3-carboxamide (Compound 1157), N-[(6-amino-2-pyridyl)sulfonyl]-6-(3-fluoro-5-isobutoxy-phenyl)-2-(4-methylene-1-piperidyl)pyridine-3-carboxamide (Compound 1162), N-[(6-amino-2-pyridyl)sulfonyl]-6-(3-fluoro-5-isobutoxy-phenyl)-2-[(5R)-2,2,5-trimethylpyrrolidin-1-yl]pyridine-3-carboxamide (Compound 1166), N-[(6-amino-2-pyridyl)sulfonyl]-2-[(2R)-2-tert-butylpyrrolidin-1-yl]-6-(3-fluoro-5-isobutoxy-phenyl)pyridine-3-carboxamide (Compound 1170), N-[(6-amino-2-pyridyl)sulfonyl]-2-[(1R,4S)-3-azabicyclo[2.2.1]heptan-3-yl]-6-(3-fluoro-5-isobutoxy-phenyl)pyridine-3-carboxamide (Compound 1180), N-[(6-amino-2-pyridyl)sulfonyl]-2-(2,2-dimethyl-3-oxo-pyrrolidin-1-yl)-6-(3-fluoro-5-isobutoxy-phenyl)-1,2-dihydropyridine-3-carboxamide, N-[(6-amino-2-pyridyl)sulfonyl]-6-(3-fluoro-5-isobutoxy-phenyl)-2-[(3S)-3-methyl-1-piperidyl]pyridine-3-carboxamide (Compound 1193), N-[(6-amino-2-pyridyl)sulfonyl]-2-[1-(3-chlorophenyl)ethyl-methyl-amino]-6-(3-fluoro-5-isobutoxy-phenyl)pyridine-3-carboxamide (Compound 1205), N-[(6-amino-2-pyridyl)sulfonyl]-2-[(3S,5S)-3,5-dimethyl-1-piperidyl]-6-(3-fluoro-5-isobutoxy-phenyl)pyridine-3-carboxamide (Compound 1210), N-[(6-amino-2-pyridyl)sulfonyl]-2-(2-ethylpyrrolidin-1-yl)-6-(3-fluoro-5-isobutoxy-phenyl)pyridine-3-carboxamide (Compound 1218), N-[(6-amino-2-pyridyl)sulfonyl]-2-(2-ethyl-5-methyl-pyrrolidin-1-yl)-6-(3-fluoro-5-isobutoxy-phenyl)pyridine-3-carboxamide (Compound 1222), N-[(6-amino-2-pyridyl)sulfonyl]-6-(3-fluoro-5-isobutoxy-phenyl)-2-[(5S)-2,2,5-trimethylpyrrolidin-1-yl]pyridine-3-carboxamide (Compound 1241), N-[(6-amino-2-pyridyl)sulfonyl]-6-(3-fluoro-5-isobutoxy-phenyl)-2-(2-isopropylpyrrolidin-1-yl)pyridine-3-carboxamide (Compound 1258), N-[(6-amino-2-pyridyl)sulfonyl]-6-(3-fluoro-5-isobutoxy-phenyl)-2-[(2S)-2-phenylpyrrolidin-1-yl]pyridine-3-carboxamide (Compound 1260), N-[(6-amino-2-pyridyl)sulfonyl]-2-(8-azaspiro[3.5]nonan-8-yl)-6-(3-fluoro-5-isobutoxy-phenyl)pyridine-3-carboxamide (Compound 1264), N-[(6-amino-2-pyridyl)sulfonyl]-2-(3,3-dimethylmorpholin-4-yl)-6-(3-fluoro-5-isobutoxy-phenyl)pyridine-3-carboxamide (Compound 1267), N-[(6-amino-2-pyridyl)sulfonyl]-2-(4,4-dimethyl-1-piperidyl)-6-(3-fluoro-5-isobutoxy-phenyl)pyridine-3-carboxamide (Compound 1279), N-[(6-amino-2-pyridyl)sulfonyl]-6-(3-fluoro-5-isobutoxy-phenyl)-2-[(4R)-2,2,4-trimethylpyrrolidin-1-yl]pyridine-3-carboxamide (Compound 1289), N-[(6-amino-2-pyridyl)sulfonyl]-2-(7-azaspiro[3.5]nonan-7-yl)-6-(3-fluoro-5-isobutoxy-phenyl)pyridine-3-carboxamide (Compound 1303), N-[(6-amino-2-pyridyl)sulfonyl]-6-(3-fluoro-5-isobutoxy-phenyl)-2-[(2S)-2-(trifluoromethyl)pyrrolidin-1-yl]pyridine-3-carboxamide (Compound 1304), 2-(2,3,4,4a,5,6,7,7a-octahydrocyclopenta[b]pyridin-1-yl)-N-[(6-amino-2-pyridyl)sulfonyl]-6-(3-fluoro-5-isobutoxy-phenyl)pyridine-3-carboxamide (Compound 1313), N-[(6-amino-2-pyridyl)sulfonyl]-6-(3-fluoro-5-isobutoxy-phenyl)-2-(2-methyl-3-phenyl-pyrrolidin-1-yl)pyridine-3-carboxamide (Compound 1319), 2-(2,5-dimethyl-3-phenyl-pyrrolidin-1-yl)-6-(3-fluoro-5-isobutoxy-phenyl)-N-(1H-pyrazol-5-ylsulfonyl)pyridine-3-carboxamide (Compound 1348), 2-[(3,3-difluorocyclobutyl)methylamino]-6-(3-fluoro-5-isobutoxy-phenyl)-N-(1H-pyrazol-5-ylsulfonyl)pyridine-3-carboxamide (Compound 393), 2-[(2S,5R)-2,5-dimethylpyrrolidin-1-yl]-6-(3-fluoro-5-isobutoxy-phenyl)-N-(1H-pyrazol-5-ylsulfonyl)pyridine-3-carboxamide (Compound 415), 6-(3-fluoro-5-isobutoxy-phenyl)-N-(1H-pyrazol-5-ylsulfonyl)-2-[4-(trifluoromethyl)-1-piperidyl]pyridine-3-carboxamide (Compound 426), 2-(3-ethynyl-1-piperidyl)-6-(3-fluoro-5-isobutoxy-phenyl)-N-(1H-pyrazol-5-ylsulfonyl)pyridine-3-carboxamide (Compound 431), 6-(3-fluoro-5-isobutoxy-phenyl)-2-(2-methyl-1-piperidyl)-N-(1H-pyrazol-5-ylsulfonyl)pyridine-3-carboxamide (Compound 442), 6-(3-fluoro-5-isobutoxy-phenyl)-2-(3-isopropyl-1-piperidyl)-N-(1H-pyrazol-5-ylsulfonyi)pyridine-3-carboxamide (Compound 498), 6-(3-fluoro-5-isobutoxy-phenyl)-N-(1H-pyrazol-5-ylsulfonyl)-2-spiro[1H-isobenzofuran-3,4'-piperidine]-1'-yl-pyridine-3-carboxamide (Compound 506), 6-(3-fluoro-5-isobutoxy-phenyl)-2-(2-oxa-8-azaspiro[3.5]nonan-8-yl)-N-(1H-pyrazol-5-ylsulfonyl)pyridine-3-carboxamide (Compound 519), 2-(3,4-dimethyl-1-piperidyl)-6-(3-fluoro-5-isobutoxy-phenyl)-N-(1H-pyrazol-5-ylsulfonyl)pyridine-3-carboxamide (Compound 528), 6-(3-fluoro-5-isobutoxy-phenyl)-2-(4-isopropyl-1-piperidyl)-N-(1H-pyrazol-5-ylsulfonyl)pyridine-3-carboxamide (Compound 553), 2-[4-(cyanomethyl)-1-piperidyl]-6-(3-fluoro-5-isobutoxy-phenyl)-N-(1H-pyrazol-5-ylsulfonyl)pyridine-3-carboxamide (Compound 556), 2-(3,3-difluoropyrrolidin-1-yl)-6-(3-fluoro-5-isobutoxy-phenyl)-N-(1H-pyrazol-5-ylsulfonyl)pyridine-3-carboxamide (Compound 565), 2-(2-ethylpyrrolidin-1-yl)-6-(3-fluoro-5-isobutoxy-phenyl)-N-(1H-pyrazol-5-ylsulfonyl)pyridine-3-carboxamide (Compound 591), 2-[(3R,5S)-3,5-dimethyl-1-piperidyl]-6-(3-fluoro-5-isobutoxy-phenyl)-N-(1H-pyrazol-5-ylsulfonyl)pyridine-3-carboxamide (Compound 642), 6-(3-fluoro-5-isobutoxy-phenyl)-2-[(3R)-3-methyl-1-piperidyl]-N-(1H-pyrazol-5-ylsulfonyl)pyridine-3-carboxamide (Compound 668), 6-(3-fluoro-5-isobutoxy-phenyl)-N-(1H-pyrazol-5-ylsulfonyl)-2-[3-(2-pyridyl)-1-piperidyl]pyridine-3-carboxamide (Compound 677), 6-(3-fluoro-5-isobutoxy-phenyl)-2-[(2S)-2-phenylpyrrolidin-1-yl]-N-(1H-pyrazol-5-ylsulfonyl)pyridine-3-carboxamide (Compound 716), 6-(3-fluoro-5-isobutoxy-phenyl)-2-(4-fluoro-1-piperidyl)-N-(1H-pyrazol-5-ylsulfonyl)pyridine-3-carboxamide (Compound 728), 2-(azepan-1-yl)-6-(3-fluoro-5-isobutoxy-phenyl)-N-(1H-pyrazol-5-ylsulfonyl)pyridine-3-carboxamide (Compound 734), 6-(3-fluoro-5-isobutoxy-phenyl)-2-indolin-1-yl-N-(1H-pyrazol-5-ylsulfonyl)pyridine-3-carboxamide (Compound 739), 6-(3-fluoro-5-isobutoxy-phenyl)-2-(3-methoxy-1-piperidyl)-N-(1H-pyrazol-5-ylsulfonyl)pyridine-3-carboxamide (Compound 749), 6-(3-fluoro-5-isobutoxy-phenyl)-2-(3-methyl-1-piperidyl)-N-(1H-pyrazol-5-ylsulfonyl)pyridine-3-carboxamide (Compound 756), 6-(3-fluoro-5-isobutoxy-phenyl)-2-(4-methoxy-4-methyl-1-piperidyl)-N-(1H-pyrazol-5-ylsulfonyl)pyridine-3-carboxamide (Compound 774), 2-(3-ethoxy-1-piperidyl)-6-(3-fluoro-5-isobutoxy-phenyl)-N-(1H-pyrazol-5-ylsulfonyl)pyridine-3-carboxamide (Compound 843), 6-(3-fluoro-5-isobutoxy-phenyl)-2-(3-fluoro-1-piperidyl)-N-(1H-pyrazol-5-ylsulfonyl)pyridine-3-carboxamide (Compound 878), 6-(3-fluoro-5-isobutoxy-phenyl)-N-(1H-pyrazol-5-ylsulfonyl)-2-(2,2,4-trimethylpyrrolidin-1-yl)pyridine-3-carboxamide (Compound 904), 6-(3-fluoro-5-isobutoxy-phenyl)-N-(1H-pyrazol-5-ylsulfonyl)-2-[3-(trifluoromethyl)-1-piperidyl]pyridine-3-carboxamide (Compound 907), 6-(3-fluoro-5-isobutoxy-phenyl)-2-[(3S)-3-phenyl-1-piperidyl]-N-(1H-pyrazol-5-ylsulfonyl)pyridine-3-carboxamide (Compound 912), 2-[(3R,5R)-3,5-dimethyl-1-piperidyl]-6-(3-fluoro-5-isobutoxy-phenyl)-N-(1H-pyrazol-5-ylsulfonyl)pyridine-3-carboxamide (Compound 942), 2-(7-azaspiro[3.5]nonan-7-yl)-6-(3-fluoro-5-isobutoxy-phenyl)-N-(1H-pyrazol-5-ylsulfonyl)pyridine-3-carboxamide (Compound 944), 6-(3-fluoro-5-isobutoxy-phenyl)-N-(1H-pyrazol-5-ylsulfonyl)-2-(2,3,3-trimethylpyrrolidin-1-yl)pyridine-3-carboxamide (Compound 952), 6-(3-fluoro-5-isobutoxy-phenyl)-2-[4-(methoxymethyl)-1-piperidyl]-N-(1H-pyrazol-5-ylsulfonyl)pyridine-3-carboxamide (Compound 975), 6-(3-fluoro-5-isobutoxy-phenyl)-2-isoindolin-2-yl-N-(1H-pyrazol-5-ylsulfonyl)pyridine-3-carboxamide (Compound 981), 6-(3-fluoro-5-isobutoxy-phenyl)-N-(1H-pyrazol-5-ylsulfonyl)-2-(2,2,3-trimethylpyrrolidin-1-yl)pyridine-3-carboxamide (Compound 997), 2-(3,3-dimethyl-1-piperidyl)-6-(3-fluoro-5-isobutoxy-phenyl)-N-(1H-pyrazol-5-ylsulfonyl)pyridine-3-carboxamide (Compound 1005), 2-(4,4-difluoro-1-piperidyl)-6-(3-fluoro-5-isobutoxy-phenyl)-N-(1H-pyrazol-5-ylsulfonyl)pyridine-3-carboxamide (Compound 1006), 6-(3-fluoro-5-isobutoxy-phenyl)-2-[3-(methoxymethyl)-1-piperidyl]-N-(1H-pyrazol-5-ylsulfonyl)pyridine-3-carboxamide (Compound 1028), 2-(4-ethyl-1-piperidyl)-6-(3-fluoro-5-isobutoxy-phenyl)-N-(1H-pyrazol-5-ylsulfonyl)pyridine-3-carboxamide (Compound 1030), 6-(3-fluoro-5-isobutoxy-phenyl)-N-(1H-pyrazol-5-ylsulfonyl)-2-[(4S)-2,2,4-trimethylpyrrolidin-1-yl]pyridine-3-carboxamide (Compound 1041), 6-(3-fluoro-5-isobutoxy-phenyl)-2-[(2R)-2-phenylpyrrolidin-1-yl]-N-(1H-pyrazol-5-ylsulfonyl)pyridine-3-carboxamide (Compound 1060), 6-(3-fluoro-5-isobutoxy-phenyl)-2-(4-methyl-1-piperidyl)-N-(1H-pyrazol-5-ylsulfonyl)pyridine-3-carboxamide (Compound 1083), 2-[4-(cyclopropylmethoxy)-1-piperidyl]-6-(3-fluoro-5-isobutoxy-phenyl)-N-(1H-pyrazol-5-ylsulfonyl)pyridine-3-carboxamide (Compound 1088), 2-(4,4-dimethyl-1-piperidyl)-6-(3-fluoro-5-isobutoxy-phenyl)-N-(1H-pyrazol-5-ylsulfonyl)pyridine-3-carboxamide (Compound 1110), 2-(2,6-dimethylmorpholin-4-yl)-6-(3-fluoro-5-isobutoxy-phenyl)-N-(1H-pyrazol-5-ylsulfonyl)pyridine-3-carboxamide (Compound 1119), 2-(6-azaspiro[2.5]octan-6-yl)-6-(3-fluoro-5-isobutoxy-phenyl)-N-(1H-pyrazol-5-ylsulfonyl)pyridine-3-carboxamide (Compound 1127), 6-(3-fluoro-5-isobutoxy-phenyl)-2-(2-methylpyrrolidin-1-yl)-N-(1H-pyrazol-5-ylsulfonyl)pyridine-3-carboxamide (Compound 1142), 2-(4-ethoxy-1-piperidyl)-6-(3-fluoro-5-isobutoxy-phenyl)-N-(1H-pyrazol-5-ylsulfonyl)pyridine-3-carboxamide (Compound 1155), 2-(2,3-dimethyl-1-piperidyl)-6-(3-fluoro-5-isobutoxy-phenyl)-N-(1H-pyrazol-5-ylsulfonyl)pyridine-3-carboxamide (Compound 1169), 6-(3-fluoro-5-isobutoxy-phenyl)-N-(1H-pyrazol-5-ylsulfonyl)-2-(3,3,4-trimethyl-1-piperidyl)pyridine-3-carboxamide (Compound 1174), 6-(3-fluoro-5-isobutoxy-phenyl)-N-(1H-pyrazol-5-ylsulfonyl)-2-[(4R)-2,2,4-trimethylpyrrolidin-1-yl]pyridine-3-carboxamide (Compound 1176), 6-(3-fluoro-5-isobutoxy-phenyl)-2-(4-methoxy-1-piperidyl)-N-(1H-pyrazol-5-ylsulfonyl)pyridine-3-carboxamide (Compound 1245), 2-(2-benzylpyrrolidin-1-yl)-6-(3-fluoro-5-isobutoxy-phenyl)-N-(1H-pyrazol-5-ylsulfonyl)pyridine-3-carboxamide (Compound 1257), 6-(3-fluoro-5-isobutoxy-phenyl)-N-(1H-pyrazol-5-ylsulfonyl)-2-[[3-(trifluoromethyl)cyclohexyl]amino]pyridine-3-carboxamide (Compound 1281), 2-(8-azaspiro[3.4]octan-8-yl)-6-(3-fluoro-5-isobutoxy-phenyl)-N-(1H-pyrazol-5-ylsulfonyl)pyridine-3-carboxamide (Compound 1282), 6-(6-isopropoxy-3-pyridyl)-N-(1H-pyrazol-5-ylsulfonyl)-2-(2,2,4-trimethylpyrrolidin-1-yl)pyridine-3-carboxamide (Compound 1352), 2-(3-cyclopropyl-1-piperidyl)-6-(3-fluoro-5-isobutoxy-phenyl)-N-(1H-pyrazol-5-ylsulfonyl)pyridine-3-carboxamide (Compound 1286), 2-(2,2-dimethylpyrrolidin-1-yl)-6-(3-fluoro-5-isobutoxy-phenyl)-N-(1H-pyrazol-5-ylsulfonyl)pyridine-3-carboxamide (Compound 1302), 6-(3-fluoro-5-isobutoxy-phenyl)-2-(4-phenyl-1-piperidyl)-N-(1H-pyrazol-5-ylsulfonyl)pyridine-3-carboxamide (Compound 1315), N-[(6-amino-2-pyridyl)sulfonyl]-6-(3-fluoro-5-isopropoxy-phenyl)-2-(4-methyl-1-piperidyl)pyridine-3-carboxamide (Compound 600), N-[(6-amino-2-pyridyl)sulfonyl]-6-(3-fluoro-5-isopropoxy-phenyl)-2-(2,2,4-trimethylpyrrolidin-1-yl)pyridine-3-carboxamide (Compound 972), N-[(6-amino-2-pyridyl)sulfonyl]-2-[(2S,5R)-2,5-dimethylpyrrolidin-1-yl]-6-(3-fluoro-5-isopropoxy-phenyl)pyridine-3-carboxamide (Compound 1123), N-(4-aminophenyl)sulfonyl-6-tert-butyl-2-(1-piperidyl)pyridine-3-carboxamide (Compound 753), N-(4-aminophenyl)sulfonyl-2-(benzylamino)-6-tert-butyl-pyridine-3-carboxamide (Compound 1064), N-(4-aminophenyl)sulfonyl-6-tert-butyl-2-(4-methoxy-1-piperidyl)pyridine-3-carboxamide (Compound 1298), N-(4-aminophenyl)sulfonyl-6-tert-butyl-2-[(4-methyltetrahydropyran-4-yl)methylamino]pyridine-3-carboxamide (Compound 752), N-(4-aminophenyl)sulfonyl-6-tert-butyl-2-(4-methyl-1-piperidyl)pyridine-3-carboxamide (Compound 1037), N-[(6-amino-2-pyridyl)sulfonyl]-6-tert-butyl-2-(4-methyl-1-piperidyl)pyridine-3-carboxamide (Compound 794), N-[(6-amino-2-pyridyl)sulfonyl]-6-tert-butyl-2-(3,3-dimethylbutoxy)pyridine-3-carboxamide, N-[(6-amino-2-pyridyl)sulfonyl]-6-tert-butyl-2-(3-methyl-1-piperidyl)pyridine-3-carboxamide (Compound 1008), N-[(6-amino-2-pyridyl)sulfonyl]-6-tert-butyl-2-[4-(methoxymethyl)-1-piperidyl]pyridine-3-carboxamide (Compound 986), N-[(6-amino-2-pyridyl)sulfonyl]-6-tert-butyl-2-(3,5-dimethyl-1-piperidyl)pyridine-3-carboxamide (Compound 617), N-[(6-amino-2-pyridyl)sulfonyl]-6-tert-butyl-2-[4-(1-hydroxy-1-methyl-ethyl)-1-piperidyl]pyridine-3-carboxamide (Compound 1038), N-[(6-amino-2-pyridyl)sulfonyl]-6-tert-butyl-2-(4-methoxy-1-piperidyl)pyridine-3-carboxamide (Compound 1164), N-[(6-amino-2-pyridyl)sulfonyl]-6-tert-butyl-2-(4-ethoxy-1-piperidyl)pyridine-3-carboxamide (Compound 1200), 2-[(4-methyltetrahydropyran-4-yl)methylamino]-6-(p-tolyl)-N-(1H-pyrazol-3-ylsulfonyl)pyridine-3-carboxamide (Compound 879)

N-[(6-amino-2-pyridyl)sulfonyl]-2-[(4-methyltetrahydropyran-4-yl)methylamino]-6-(p-tolyl)pyridine-3-carboxamide (Compound 1196), N-[(6-amino-2-pyridyl)sulfonyl]-6-tert-butyl-2-[(2S,5R)-2,5-dimethylpyrrolidin-1-yl]pyridine-3-carboxamide (Compound 373), N-[(6-amino-2-pyridyl)sulfonyl]-6-tert-butyl-2-[(3S)-3-phenyl-1-piperidyl]pyridine-3-carboxamide (Compound 1261), N-[(2-amino-3-pyridyl)sulfonyl]-2-[(2S,5R)-2,5-dimethylpyrrolidin-1-yl]-6-(6-isopropoxy-3-pyridyl)pyridine-3-carboxamide (Compound 1316), N-[(2-amino-3-pyridyl)sulfonyl]-6-(6-isopropoxy-3-pyridyl)-2-[(4R)-2,2,4-trimethylpyrrolidin-1-yl]pyridine-3-carboxamide (Compound 1240), N-[(2-amino-3-pyridyl)sulfonyl]-2-[(2S,5R)-2,5-dimethylpyrrolidin-1-yl]-6-(3-fluoro-5-isobutoxy-phenyl)pyridine-3-carboxamide (Compound 1159), N-[(6-amino-2-pyridyl)sulfonyl]-6-methyl-2-[(3S)-3-phenyl-1-piperidyl]pyridine-3-carboxamide (Compound 532), N-[(6-amino-2-pyridyl)sulfonyl]-6-tert-butyl-2-[(3R)-3-phenyl-1-piperidyl]pyridine-3-carboxamide (Compound 626), 2-[(2S,5R)-2,5-dimethylpyrrolidin-1-yl]-6-(6-isopropoxy-3-pyridyl)-N-(1H-pyrazol-5-ylsulfonyl)pyridine-3-carboxamide (Compound 1074), 6-(6-isopropoxy-3-pyridyl)-2-[(3R)-3-phenyl-1-piperidyl]-N-(1H-pyrazol-5-ylsulfonyl)pyridine-3-carboxamide (Compound 741), 6-(6-isopropoxy-3-pyridyl)-2-[(3S)-3-phenyl-1-piperidyl]-N-(1H-pyrazol-5-ylsulfonyl)pyridine-3-carboxamide (Compound 776), 2-[(3R,5S)-3,5-dimethyl-1-piperidyl]-6-(6-isopropoxy-3-pyridyl)-N-(1H-pyrazol-5-ylsulfonyl)pyridine-3-carboxamide (Compound 446), 2-[(3R,5R)-3,5-dimethyl-1-piperidyl]-6-(6-isopropoxy-3-pyridyl)-N-(1H-pyrazol-5-ylsulfonyl)pyridine-3-carboxamide (Compound 990), 6-(6-isopropoxy-3-pyridyl)-2-(4-methyl-1-piperidyl)-N-(1H-pyrazol-5-ylsulfonyl)pyridine-3-carboxamide (Compound 534), N-(benzenesulfonyl)-6-(3-fluoro-5-isobutoxy-phenyl)-2-[(4S)-2,2,4-trimethylpyrrolidin-1-yl]pyridine-3-carboxamide, N-[(6-amino-2-pyridyl)sulfonyl]-2-(3-azabicyclo[2.2.2]octan-3-yl)-6-(3-fluoro-5-isobutoxy-phenyl)pyridine-3-carboxamide (Compound 1657), N-[(6-amino-2-pyridyl)sulfonyl]-2-[(3S)-2,2-dideuterio-3,5,5-trimethyl-pyrrolidin-1-yl]-6-(3-fluoro-5-isobutoxy-phenyl)pyridine-3-carboxamide (Compound 1400), N-[(6-amino-2-pyridyl)sulfonyl]-2-(3-azabicyclo[3.1.1]heptan-3-yl)-6-(3-fluoro-5-isobutoxy-phenyl)pyridine-3-carboxamide (Compound 1529), N-[(6-amino-2-pyridyl)sulfonyl]-6-(3-fluoro-5-isobutoxy-phenyl)-2-(2,5,5-trimethylmorpholin-4-yl)pyridine-3-carboxamide (Compound 1548), N-[(6-amino-2-pyridyl)sulfonyl]-2-(5,7-dimethylindolin-1-yl)-6-(3-fluoro-5-isobutoxy-phenyl)pyridine-3-carboxamide (Compound 1572), N-[(6-amino-2-pyridyl)sulfonyl]-2-[(4R)-4-ethyl-2,2-dimethyl-pyrrolidin-1-yl]-6-(3-fluoro-5-isobutoxy-phenyl)pyridine-3-carboxamide (Compound 1611), N-[(6-amino-2-pyridyl)sulfonyl]-2-[(4S)-4-ethyl-2,2-dimethyl-pyrrolidin-1-yl]-6-(3-fluoro-5-isobutoxy-phenyl)pyridine-3-carboxamide (Compound 1612), N-[(6-amino-2-pyridyl)sulfonyl]-6-(3-fluoro-5-isobutoxy-phenyl)-2-(2,2,5,5-tetramethylmorpholin-4-yl)pyridine-3-carboxamide (Compound 1675), N-[(6-amino-2-pyridyl)sulfonyl]-2-(3,5-diisopropylpyrazol-1-yl)-6-(3-fluoro-5-isobutoxy-phenyl)pyridine-3-carboxamide (Compound 1387), N-[(6-amino-2-pyridyl)sulfonyl]-2-(3,3-difluoroazetidin-1-yl)-6-(3-fluoro-5-isobutoxy-phenyl)pyridine-3-carboxamide (Compound 2155), N-[(6-amino-2-pyridyl)sulfonyl]-6-(3-fluoro-5-isobutoxy-phenyl)-2-(2-methylazetidin-1-yl)pyridine-3-carboxamide (Compound 1840), N-[(6-amino-2-pyridyl)sulfonyl]-2-(3-fluoroazetidin-1-yl)-6-(3-fluoro-5-isobutoxy-phenyl)pyridine-3-carboxamide (Compound 2128), N-[(6-amino-2-pyridyl)sulfonyl]-2-(6,6-dimethyl-7-azaspiro[3.4]octan-7-yl)-6-(3-fluoro-5-isobutoxy-phenyl)pyridine-3-carboxamide (Compound 2589), N-[(6-amino-2-pyridyl)sulfonyl]-2-(5-azabicyclo[4.1.0]heptan-5-yl)-6-(3-fluoro-5-isobutoxy-phenyl)pyridine-3-carboxamide (Compound 2376), N-[(6-amino-2-pyridyl)sulfonyl]-6-(3-fluoro-5-isobutoxy-phenyl)-2-(6-methyl-3-azabicyclo[3.1.1]heptan-3-yl)pyridine-3-carboxamide (Compound 2224), N-[(6-amino-2-pyridyl)sulfonyl]-6-(3-fluoro-5-isobutoxy-phenyl)-2-[[1-(2-hydroxy-2-methyl-propyl)cyclopropyl]methylamino]pyridine-3-carboxamide (Compound 1723), N-[(6-amino-2-pyridyl)sulfonyl]-6-(3-fluoro-5-isobutoxy-phenyl)-2-(6-methyl-8-azaspiro[3.4]octan-8-yl)pyridine-3-carboxamide (Compound 2552), N-[(6-amino-2-pyridyl)sulfonyl]-2-(2,2-dimethylazetidin-1-yl)-6-(3-fluoro-5-isobutoxy-phenyl)pyridine-3-carboxamide (Compound 1928), N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Isomer 1) (Compound 2178) (Isomer 2) (Compound 2062) (Isomer 3) (Compound 1863) (Isomer 4), N-[(6-amino-2-pyridyl)sulfonyl]-2-(2,5-dimethyl-1-piperidyl)-6-(3-fluoro-5-isobutoxy-phenyl)pyridine-3-carboxamide (Compound 2451) (Isomer 1) (Compound 1993) (Isomer 2) (Compound 1864) (Isomer 3) (Compound 1855) (Isomer 4), N-[(6-amino-2-pyridyl)sulfonyl]-6-(3-fluoro-5-isobutoxy-phenyl)-2-(4-hydroxy-1-piperidyl)pyridine-3-carboxamide (Compound 2323), N-[(6-amino-2-pyridyl)sulfonyl]-2-[cyclohexylmethyl(methyl)amino]-6-(3-fluoro-5-isobutoxy-phenyl)pyridine-3-carboxamide (Compound 2289), N-[(6-amino-2-pyridyl)sulfonyl]-6-(3-fluoro-5-isobutoxy-phenyl)-2-(2,2,5-trimethyl-1-piperidyl)pyridine-3-carboxamide (Compound 1995), N-[(6-amino-2-pyridyl)sulfonyl]-6-(3-fluoro-5-isobutoxy-phenyl)-2-(4-isopropyl-2,2-dimethyl-pyrrolidin-1-yl)pyridine-3-carboxamide (Compound 2201), N-[(6-amino-2-pyridyl)sulfonyl]-6-(3-fluoro-5-isobutoxy-phenyl)-2-BLAHyl-pyridine-3-carboxamide (Compound 1821), N-[(6-amino-2-pyridyl)sulfonyl]-6-(3-fluoro-5-isobutoxy-phenyl)-2-(5-methyl-7-azaspiro[2.4]heptan-7-yl)pyridine-3-carboxamide (Compound 1754), N-[(6-amino-2-pyridyl)sulfonyl]-2-(4-tert-butyl-2,2-dimethyl-pyrrolidin-1-yl)-6-(3-fluoro-5-isobutoxy-phenyl)pyridine-3-carboxamide (Compound 2538), tert-butyl (2R)-1-[3-[(6-amino-2-pyridyl)sulfonylcarbamoyl]-6-(3-fluoro-5-isobutoxy-phenyl)-2-pyridyl]pyrrolidine-2-carboxylate (Compound 2216), tert-butyl (2S)-1-[3-[(6-amino-2-pyridyl)sulfonylcarbamoyl]-6-(3-fluoro-5-isobutoxy-phenyl)-2-pyridyl]pyrrolidine-2-carboxylate (Compound 2204), N-[(6-amino-2-pyridyl)sulfonyl]-6-(3-fluoro-5-isobutoxy-phenyl)-2-(2,2,4-trimethyl-1-piperidyl)pyridine-3-carboxamide (Compound 2581), N-[(6-amino-2-pyridyl)sulfonyl]-2-(4,4-difluoro-2,2-dimethyl-pyrrolidin-1-yl)-6-(3-fluoro-5-isobutoxy-phenyl)pyridine-3-carboxamide (Compound 2631), N-[(6-amino-2-pyridyl)sulfonyl]-2-(5,5-dimethyl-6-azaspiro[2.4]heptan-6-yl)-6-(3-fluoro-5-isobutoxy-phenyl)pyridine-3-carboxamide (Compound 1746), N-[(6-amino-2-pyridyl)sulfonyl]-6-(3-fluoro-5-isobutoxy-phenyl)-2-(3-methylazetidin-1-yl)pyridine-3-carboxamide (Compound 2117), N-[(6-amino-2-pyridyl)sulfonyl]-2-[2,2-dimethyl-4-(trifluoromethyl)pyrrolidin-1-yl]-6-(3-fluoro-5-isobutoxy-phenyl)pyridine-3-carboxamide (Compound 1788), N-[(6-amino-2-pyridyl)sulfonyl]-6-(3-fluoro-5-isobutoxy-phenyl)-2-[2-methyl-5-(trifluoromethyl)-1-piperidyl]pyridine-3-carboxamide (Compound 1835), N-[(6-amino-2-pyridyl)sulfonyl]-2-(3,5-dimethylazepan-1-yl)-6-(3-fluoro-5-isobutoxy-phenyl)pyridine-3-carboxamide (Compound 2479), N-[(6-amino-2-pyridyl)sulfonyl]-2-(4,4-dimethylazepan-1-yl)-6-(3-fluoro-5-isobutoxy-phenyl)pyridine-3-carboxamide (Compound 2171), N-[(6-amino-2-pyridyl)sulfonyl]-2-(3,3-dimethylazepan-1-yl)-6-(3-fluoro-5-isobutoxy-phenyl)pyridine-3-carboxamide (Compound 1901), N-[(6-amino-2-pyridyl)sulfonyl]-2-(cyclohexylmethylamino)-6-(3-fluoro-5-isobutoxy-phenyl)pyridine-3-carboxamide (Compound 2375), N-[(6-amino-2-pyridyl)sulfonyl]-6-tert-butyl-2-(1-piperidyl)pyridine-3-carboxamide (Compound 571), and N-[(6-amino-2-pyridyl)sulfonyl]-2-(2,2-dimethylpyrrolidin-1-yl)-6-(3-fluoro-5-isobutoxy-phenyl)pyridine-3-carboxamide (Compound 361).

Preparation 40: 2-(Benzenesulfonyl)-3-[5-tert-butyl-2-[(2,6-dimethylphenyl)methyl]pyrazol-3-yl]-3-oxo-propanoate (Compound 4)

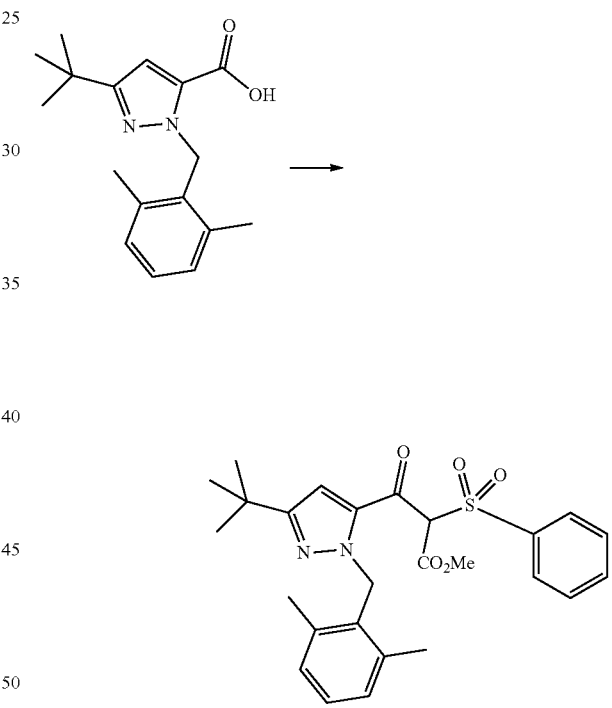

5-tert-Butyl-2-[(2,6-dimethylphenyl)methyl]pyrazole-3-carboxylic acid (100 mg, 0.35 mmol) was dissolved in thionyl chloride (26 μL, 0.35 mmol) and a drop of N,N-dimethylformamide was added. The mixture was stirred for 1 h and evaporated to give the acid chloride.

A mixture of the acid chloride (40 mg, 0.13 mmol), methyl 2-(benzenesulfonyl)acetate (28 mg, 0.13 mmol) and NaH (60%, 5.3 mg, 0.13 mmol) in N,N-dimethylformamide (1 mL) were stirred at room temperature for 15 min. The mixture was filtered and purified by reverse-phase preparatory-HPLC (10-99% $CH_3CN/H_2O$, HCl modifier) to give 2-(benzenesulfonyl)-3-[5-tert-butyl-2-[(2,6-dimethylphenyl)methyl]pyrazol-3-yl]-3-oxo-propanoate (Compound 4). ESI-MS m/z calc. 482.6, found 483.4 $(M+1)^+$; Retention time: 2.41 min (3 min run).

2007

Preparation 41: 6-(3-isoButoxyphenyl)-N-[(2-oxo-1H-pyridin-3-yl)sulfonyl]-2-(2,4,6-trimethylphenoxy)pyridine-3-carboxamide (Compound 125)

Step 1: 6-chloro-N-[(2-methoxy-3-pyridyl)sulfonyl]-2-(2,4,6-trimethylphenoxy)pyridine-3-carboxamide

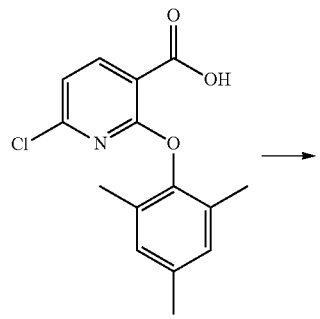

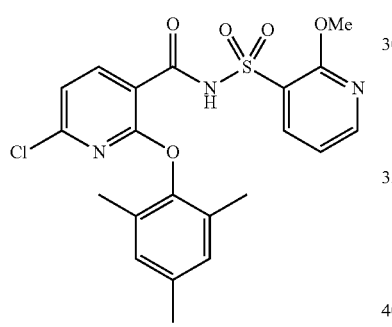

6-Chloro-2-(2,4,6-trimethylphenoxy)pyridine-3-carboxylic acid (5.09 g, 17.5 mmol) was dissolved in thionyl chloride (6.36 mL, 87.3 mmol), $CH_2Cl2$ (1 mL) and N,N-dimethylformamide (one drop). The reaction mixture was stirred for 30 min before it was concentrated to give the acid chloride.

The acid chloride was dissolved in $CH_2Cl2$ (1 mL) and was added to solution of 2-methoxypyridine-3-sulfonamide (3.69 g, 17.5 mmol) in $CH_2Cl2$ (1 mL) containing triethylamine (7.30 mL, 52.4 mmol) at 0° C. The mixture was allowed to stir at room temperature overnight before it was diluted with $CH_2Cl_2$ and washed with 1N HCl, saturated $NaHCO_3$, and then brine. The organic layer was dried over sodium sulfate and concentrated to give 6-chloro-N-[(2-methoxy-3-pyridyl)sulfonyl]-2-(2,4,6-trimethylphenoxy)pyridine-3-carboxamide (6.20 g, 77%) ESI-MS m/z calc. 461.1, found 462.2 (M+1)$^+$; Retention time: 0.74 min (1 min run).

2008

Step 2: 6-chloro-N-[(2-oxo-1H-pyridin-3-yl)sulfonyl]-2-(2,4,6-trimethylphenoxy)pyridine-3-carboxamide

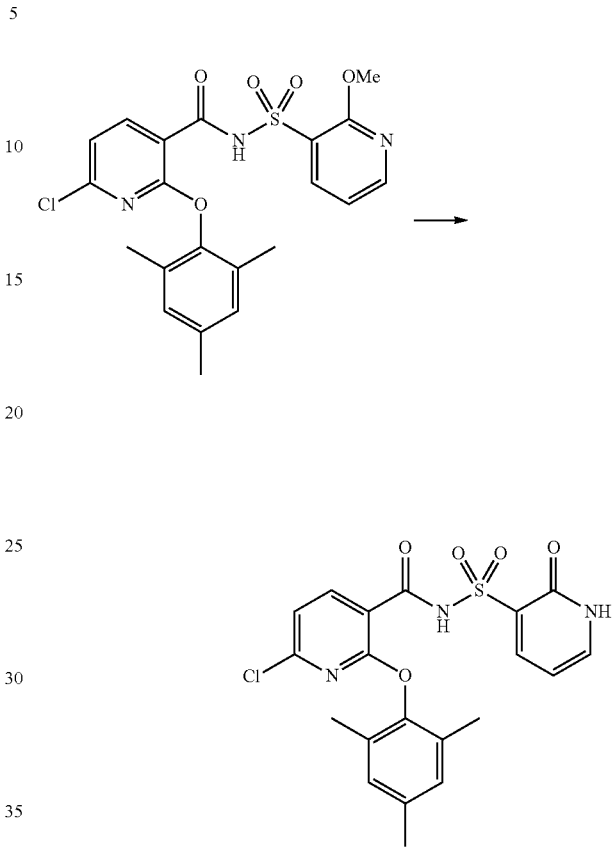

A mixture of 6-chloro-N-[(2-methoxy-3-pyridyl)sulfonyl]-2-(2,4,6-trimethylphenoxy)pyridine-3-carboxamide (500 mg, 1.08 mmol), 1,4-dioxane (10 mL) and HCl (2.71 mL of 4 M, 10.8 mmol) was heated at 90° C. for 3.5 h. The volatiles were removed to give 6-chloro-N-[(2-oxo-1H-pyridin-3-yl)sulfonyl]-2-(2,4,6-trimethylphenoxy)pyridine-3-carboxamide (372 mg, 77%) ESI-MS m/z calc. 447.1, found 448.2 (M+1)$^+$; Retention time: 0.63 min (1 min run).

Step 3: 6-(3-isoButoxyphenyl)-N-[(2-oxo-1H-pyridin-3-yl)sulfonyl]-2-(2,4,6-trimethylphenoxy)pyridine-3-carboxamide (Compound 125)

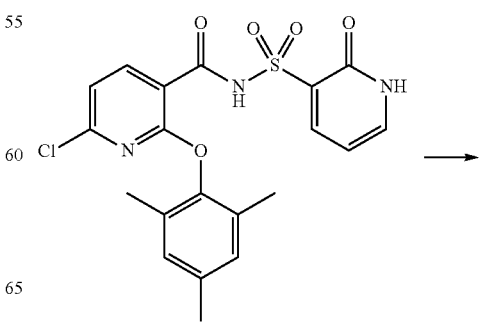

-continued

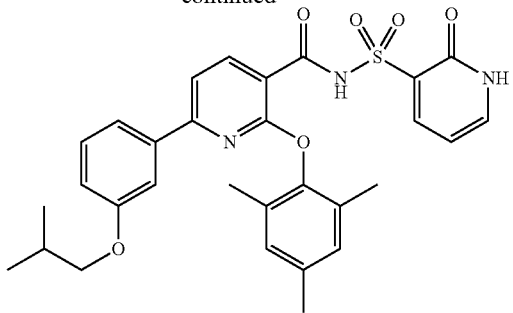

A mixture of 6-chloro-N-[(2-oxo-1H-pyridin-3-yl)sulfonyl]-2-(2,4,6-trimethylphenoxy)pyridine-3-carboxamide (56 mmol, 0.10 mmol), 3-isobutoxyphenyl boronic acid (39 mg, 0.2 mmol), Pd(PPh$_3$)$_4$ (7 mg, 0.006 mmol), K$_2$CO$_3$ (2 M, 200 µL, 0.4 mmol) and N,N-dimethylformamide (1 mL) was flushed with nitrogen and sealed. The mixture was then stirred at 80° C. for 18 h. The resultant solid was diluted with water and filtered. Then solid was taken up in ethyl acetate, filtered and concentrated to give 6-(3-isobutoxyphenyl)-N-[(2-oxo-1H-pyridin-3-yl)sulfonyl]-2-(2,4,6-trimethylphenoxy)pyridine-3-carboxamide (Compound 125). ESI-MS m/z calc. 561.2, found 562.2 (M+1)$^+$; Retention time: 2.23 min (3 min run).

The following compound can be synthesized using the procedures described herein:
6-(4-chloro-3-propoxy-phenyl)-N-[(2-oxo-1H-pyridin-3-yl)sulfonyl]-2-(2,4,6-trimethylphenoxy)pyridine-3-carboxamide (Compound 72),
2-(2,4-dimethylphenoxy)-6-(4-ethoxyphenyl)-N-[(2-oxo-1H-pyridin-3-yl)sulfonyl]pyridine-3-carboxamide (Compound 517),
6-(4-chloro-3-isobutoxy-phenyl)-N-[(2-oxo-1H-pyridin-3-yl)sulfonyl]-2-(2,4,6-trimethylphenoxy)pyridine-3-carboxamide (Compound 136),
6-(2,5-difluorophenyl)-N-[(2-oxo-1H-pyridin-3-yl)sulfonyl]-2-(2,4,6-trimethylphenoxy)pyridine-3-carboxamide (Compound 545),
6-(3,4-difluorophenyl)-N-[(2-oxo-1H-pyridin-3-yl)sulfonyl]-2-(2,4,6-trimethylphenoxy)pyridine-3-carboxamide (Compound 546),
6-(2-fluoro-5-propoxy-phenyl)-N-[(2-oxo-1H-pyridin-3-yl)sulfonyl]-2-(2,4,6-trimethylphenoxy)pyridine-3-carboxamide (Compound 552),
6-(4-fluorophenyl)-N-[(2-oxo-1H-pyridin-3-yl)sulfonyl]-2-(2,4,6-trimethylphenoxy)pyridine-3-carboxamide (Compound 561),
6-(4,4-dimethylcyclohexen-1-yl)-N-[(2-oxo-1H-pyridin-3-yl)sulfonyl]-2-(2,4,6-trimethylphenoxy)pyridine-3-carboxamide (Compound 573),
6-(4-chlorophenyl)-N-[(2-oxo-1H-pyridin-3-yl)sulfonyl]-2-(2,4,6-trimethylphenoxy)pyridine-3-carboxamide (Compound 579),
6-(3-fluoro-5-isobutoxy-phenyl)-N-(1H-indol-4-ylsulfonyl)-2-(2,2,4-trimethylpyrrolidin-1-yl)pyridine-3-carboxamide (Compound 549),
2-(4,4-dimethyl-1-piperidyl)-6-(3-fluoro-5-isobutoxy-phenyl)-N-(3-hydroxyphenyl)sulfonyl-pyridine-3-carboxamide (Compound 1309),
2-(4,4-dimethyl-1-piperidyl)-6-(3-fluoro-5-isobutoxy-phenyl)-N-(1H-indol-4-ylsulfonyl)pyridine-3-carboxamide (Compound 1323),
N-[(6-amino-2-pyridyl)sulfonyl]-2-[(2S,5R)-2,5-dimethylpyrrolidin-1-yl]-6-(6-methoxy-3-pyridyl)pyridine-3-carboxamide (Compound 726),
N-[(6-amino-2-pyridyl)sulfonyl]-6-(3,5-dimethoxyphenyl)-2-[(4S)-2,2,4-trimethylpyrrolidin-1-yl]pyridine-3-carboxamide (Compound 1471),
isopropyl 4-[5-[(6-amino-2-pyridyl)sulfonylcarbamoyl]-6-(2,4,6-trimethylphenoxy)-2-pyridyl]-3,6-dihydro-2H-pyridine-1-carboxylate (Compound 1366),
N-[(6-amino-2-pyridyl)sulfonyl]-6-(4-ethylcyclohexen-1-yl)-2-(2,4,6-trimethylphenoxy)pyridine-3-carboxamide (Compound 1370),
N-[(6-amino-2-pyridyl)sulfonyl]-6-(1-benzyl-3,6-dihydro-2H-pyridin-4-yl)-2-(2,4,6-trimethylphenoxy)pyridine-3-carboxamide (Compound 1389),
N-[(6-amino-2-pyridyl)sulfonyl]-6-(1,2-dimethylprop-1-enyl)-2-(2,4,6-trimethylphenoxy)pyridine-3-carboxamide (Compound 1390),
N-[(6-amino-2-pyridyl)sulfonyl]-6-[4-(trifluoromethyl)cyclohexen-1-yl]-2-(2,4,6-trimethylphenoxy)pyridine-3-carboxamide (Compound 1402),
N-[(6-amino-2-pyridyl)sulfonyl]-6-(4,7,7-trimethyl-3-bicyclo[2.2.1]hept-2-enyl)-2-(2,4,6-trimethylphenoxy)pyridine-3-carboxamide (Compound 1410),
N-[(6-amino-2-pyridyl)sulfonyl]-6-(2,3-dihydrofuran-4-yl)-2-(2,4,6-trimethylphenoxy)pyridine-3-carboxamide (Compound 1412),
ethyl 4-[5-[(6-amino-2-pyridyl)sulfonylcarbamoyl]-6-(2,4,6-trimethylphenoxy)-2-pyridyl]cyclohex-3-ene-1-carboxylate (Compound 1432),
N-[(6-amino-2-pyridyl)sulfonyl]-6-(1,4-dioxaspiro[4.5]dec-8-en-9-yl)-2-(2,4,6-trimethylphenoxy)pyridine-3-carboxamide (Compound 1437),
N-[(6-amino-2-pyridyl)sulfonyl]-6-(6,6-dimethyl-2,3-dihydropyran-4-yl)-2-(2,4,6-trimethylphenoxy)pyridine-3-carboxamide (Compound 1460),
N-[(6-amino-2-pyridyl)sulfonyl]-6-(cyclohepten-1-yl)-2-(2,4,6-trimethylphenoxy)pyridine-3-carboxamide (Compound 1513),
N-[(6-amino-2-pyridyl)sulfonyl]-6-(3-bicyclo[2.2.1]hept-2-enyl)-2-(2,4,6-trimethylphenoxy)pyridine-3-carboxamide (Compound 1518),
N-[(6-amino-2-pyridyl)sulfonyl]-6-(5,5-dimethyl-3-oxo-cyclohexen-1-yl)-2-(2,4,6-trimethylphenoxy)pyridine-3-carboxamide (Compound 1528),
N-[(6-amino-2-pyridyl)sulfonyl]-6-(5,5-dimethyl-2-oxo-cyclohexyl)-2-(2,4,6-trimethylphenoxy)pyridine-3-carboxamide (Compound 1427),
N-[(6-amino-2-pyridyl)sulfonyl]-6-cycloheptyl-2-(2,4,6-trimethylphenoxy)pyridine-3-carboxamide (Compound 1376).
N-[(6-amino-2-pyridyl)sulfonyl]-6-(2,2-dimethyltetrahydropyran-4-yl)-2-(2,4,6-trimethylphenoxy)pyridine-3-carboxamide (Compound 1466),
N-[(6-amino-2-pyridyl)sulfonyl]-6-(4-ethylcyclohexyl)-2-(2,4,6-trimethylphenoxy)pyridine-3-carboxamide (Compound 1475),
N-[(6-amino-2-pyridyl)sulfonyl]-6-(1,2-dimethylpropyl)-2-(2,4,6-trimethylphenoxy)pyridine-3-carboxamide (Compound 1486),
N-[(6-amino-2-pyridyl)sulfonyl]-6-(3,3-dimethyl-5-oxo-cyclohexyl)-2-(2,4,6-trimethylphenoxy)pyridine-3-carboxamide (Compound 1492),
N-[(6-amino-2-pyridyl)sulfonyl]-6-(3,6-dihydro-2H-thiopyran-4-yl)-2-(2,4,6-trimethylphenoxy)pyridine-3-carboxamide (Compound 1517), N-[(6-amino-2-pyridyl)sulfonyl]-6-[4-(trifluoromethyl)cyclohexyl]-2-(2,4,6-trimethylphenoxy)pyridine-3-carboxamide (Compound 1519), N-[(6-amino-2-pyridyl)sulfonyl]-6-(4-isopropylcyclohexen-1-yl)-2-(2,4,6-trimethylphenoxy)pyridine-3-carboxamide (Compound 1630), 6-(4-acetylcyclohexyl)-N-[(6-amino-2-pyridyl)sulfonyl]-2-(2,4,6-trimethylphenoxy)pyridine-3-carboxamide (Compound 1631), N-[(6-amino-2-pyridyl)sulfonyl]-6-(1,7,7-trimethylnorbornan-2-yl)-2-(2,4,6-trimethylphenoxy)pyridine-3-carboxamide (Compound 1650), N-[(6-amino-2-pyridyl)sulfonyl]-6-[1-(2-methylpropanoyl)-3,6-dihydro-2H-pyridin-4-yl]-2-(2,4,6-trimethylphenoxy)pyridine-3-carboxamide (Compound 1540), N-[(6-amino-2-pyridyl)sulfonyl]-6-(1,4-dioxaspiro[4.5]dec-8-en-8-yl)-2-(2,4,6-trimethylphenoxy)pyridine-3-carboxamide (Compound 1558), N-[(6-amino-2-pyridyl)sulfonyl]-6-(3,3-dimethyl-6-oxo-cyclohexen-1-yl)-2-(2,4,6-trimethylphenoxy)pyridine-3-carboxamide (Compound 1598), N-[(6-amino-2-pyridyl)sulfonyl]-6-(2,2,5,5-tetramethyl-3-furyl)-2-(2,4,6-trimethylphenoxy)pyridine-3-carboxamide (Compound 1609), 6-(4-acetylcyclohexen-1-yl)-N-[(6-amino-2-pyridyl)sulfonyl]-2-(2,4,6-trimethylphenoxy)pyridine-3-carboxamide (Compound 1615), N-[(6-amino-2-pyridyl)sulfonyl]-6-(1,2,3,6-tetrahydropyridin-4-yl)-2-(2,4,6-trimethylphenoxy)pyridine-3-carboxamide (Compound 1643), 6-(1-acetyl-3,6-dihydro-2H-pyridin-4-yl)-N-[(6-amino-2-pyridyl)sulfonyl]-2-(2,4,6-trimethylphenoxy)pyridine-3-carboxamide (Compound 1649), N-[(6-amino-2-pyridyl)sulfonyl]-6-[3-isopropoxy-5-(trifluoromethyl)phenyl]-2-[(4S)-2,2,4-trimethylpyrrolidin-1-yl]pyridine-3-carboxamide (Compound 1674), N-[(6-amino-2-pyridyl)sulfonyl]-6-(3-ethoxy-5-methylphenyl)-2-[(4S)-2,2,4-trimethylpyrrolidin-1-yl]pyridine-3-carboxamide (Compound 1488), N-[(6-amino-2-pyridyl)sulfonyl]-6-[3-ethoxy-5-(trifluoromethyl)phenyl]-2-[(4S)-2,2,4-trimethylpyrrolidin-1-yl]pyridine-3-carboxamide (Compound 1569), N-[(6-amino-2-pyridyl)sulfonyl]-6-(3-isopropoxy-5-methyl-phenyl)-2-[(4S)-2,2,4-trimethylpyrrolidin-1-yl]pyridine-3-carboxamide (Compound 1671), N-[(6-amino-2-pyridyl)sulfonyl]-6-(3-isobutoxy-5-methylphenyl)-2-[(4S)-2,2,4-trimethylpyrrolidin-1-yl]pyridine-3-carboxamide (Compound 1646), N-(2-azidophenyl)sulfonyl-2-[(2S,5R)-2,5-dimethylpyrrolidin-1-yl]-6-(3-fluoro-5-isobutoxy-phenyl)pyridine-3-carboxamide, N-(2-azidophenyl)sulfonyl-2-[(2S,5R)-2,5-dimethylpyrrolidin-1-yl]-6-(6-isopropoxy-3-pyridyl)pyridine-3-carboxamide, N-[(6-amino-2-pyridyl)sulfonyl]-6-cyclohexyl-2-[(2S,5R)-2,5-dimethylpyrrolidin-1-yl]pyridine-3-carboxamide (Compound 704), 6-(4-fluoro-2-methoxy-phenyl)-N-[(2-oxo-1H-pyridin-3-yl)sulfonyl]-2-(2,4,6-trimethylphenoxy)pyridine-3-carboxamide (Compound 608), 6-(4-fluoro-3-methoxy-phenyl)-N-[(2-oxo-1H-pyridin-3-yl)sulfonyl]-2-(2,4,6-trimethylphenoxy)pyridine-3-carboxamide (Compound 624), 6-(3-fluoro-5-isopropoxy-phenyl)-N-[(2-oxo-1H-pyridin-3-yl)sulfonyl]-2-(2,4,6-trimethylphenoxy)pyridine-3-carboxamide (Compound 645), 6-(3-fluoro-5-methoxy-phenyl)-N-[(2-oxo-1H-pyridin-3-yl)sulfonyl]-2-(2,4,6-trimethylphenoxy)pyridine-3-carboxamide (Compound 652), N-[(2-oxo-1H-pyridin-3-yl)sulfonyl]-6-phenyl-2-(2,4,6-trimethylphenoxy)pyridine-3-carboxamide (Compound 654), 6-(2-fluoro-5-methoxy-phenyl)-N-[(2-oxo-1H-pyridin-3-yl)sulfonyl]-2-(2,4,6-trimethylphenoxy)pyridine-3-carboxamide (Compound 762), 6-(2-fluoro-3-isobutoxy-phenyl)-N-[(2-oxo-1H-pyridin-3-yl)sulfonyl]-2-(2,4,6-trimethylphenoxy)pyridine-3-carboxamide (Compound 804), 6-(3,5-difluorophenyl)-N-[(2-oxo-1H-pyridin-3-yl)sulfonyl]-2-(2,4,6-trimethylphenoxy)pyridine-3-carboxamide (Compound 815), 6-(4-ethylphenyl)-N-[(2-oxo-1H-pyridin-3-yl)sulfonyl]-2-(2,4,6-trimethylphenoxy)pyridine-3-carboxamide (Compound 831), 6-(3-ethoxy-5-fluoro-phenyl)-N-[(2-oxo-1H-pyridin-3-yl)sulfonyl]-2-(2,4,6-trimethylphenoxy)pyridine-3-carboxamide (Compound 835), 6-(2-fluoro-4-methoxy-phenyl)-N-[(2-oxo-1H-pyridin-3-yl)sulfonyl]-2-(2,4,6-trimethylphenoxy)pyridine-3-carboxamide (Compound 839), 6-(2-chlorophenyl)-N-[(2-oxo-1H-pyridin-3-yl)sulfonyl]-2-(2,4,6-trimethylphenoxy)pyridine-3-carboxamide (Compound 877), 6-(cyclohexen-1-yl)-N-[(2-oxo-1H-pyridin-3-yl)sulfonyl]-2-(2,4,6-trimethylphenoxy)pyridine-3-carboxamide (Compound 8.82), 6-(2,5-dimethoxyphenyl)-N-[(2-oxo-1H-pyridin-3-yl)sulfonyl]-2-(2,4,6-trimethylphenoxy)pyridine-3-carboxamide (Compound 888), 6-(3-ethoxy-4-fluoro-phenyl)-N-[(2-oxo-1H-pyridin-3-yl)sulfonyl]-2-(2,4,6-trimethylphenoxy)pyridine-3-carboxamide (Compound 917), 6-(6-methoxy-5-methyl-3-pyridyl)-N-[(2-oxo-1H-pyridin-3-yl)sulfonyl]-2-(2,4,6-trimethylphenoxy)pyridine-3-carboxamide (Compound 930), 6-(6-ethoxy-3-pyridyl)-N-[(2-oxo-1H-pyridin-3-yl)sulfonyl]-2-(2,4,6-trimethylphenoxy)pyridine-3-carboxamide (Compound 932), 6-(1-methylindol-6-yl)-N-[(2-oxo-1H-pyridin-3-yl)sulfonyl]-2-(2,4,6-trimethylphenoxy)pyridine-3-carboxamide (Compound 936), 6-(2-chloro-3-propoxy-phenyl)-N-[(2-oxo-1H-pyridin-3-yl)sulfonyl]-2-(2,4,6-trimethylphenoxy)pyridine-3-carboxamide (Compound 955), 6-(3-butoxy-2-chloro-phenyl)-N-[(2-oxo-1H-pyridin-3-yl)sulfonyl]-2-(2,4,6-trimethylphenoxy)pyridine-3-carboxamide (Compound 964), 6-(4-methoxyphenyl)-N-[(2-oxo-1H-pyridin-3-yl)sulfonyl]-2-(2,4,6-trimethylphenoxy)pyridine-3-carboxamide (Compound 980), 6-(3-chloro-4-propoxy-phenyl)-N-[(2-oxo-1H-pyridin-3-yl)sulfonyl]-2-(2,4,6-trimethylphenoxy)pyridine-3-carboxamide (Compound 999).

6-(4-isopropylphenyl)-N-[(2-oxo-1H-pyridin-3-yl)sulfonyl]-2-(2,4,6-trimethylphenoxy)pyridine-3-carboxamide (Compound 1002), 6-[4-(cyclopropylmethoxy)phenyl]-N-[(2-oxo-1H-pyridin-3-yl)sulfonyl]-2-(2,4,6-trimethylphenoxy)pyridine-3-carboxamide (Compound 1007), 6-(3-fluoro-4-propoxy-phenyl)-N-[(2-oxo-1H-pyridin-3-yl)sulfonyl]-2-(2,4,6-trimethylphenoxy)pyridine-3-carboxamide (Compound 1022), 6-(4-methylcyclohexen-1-yl)-N-[(2-oxo-1H-pyridin-3-yl) sulfonyl]-2-(2,4,6-trimethylphenoxy)pyridine-3-carboxamide (Compound 1052), 6-(4-isobutoxyphenyl)-N-[(2-oxo-1H-pyridin-3-yl)sulfonyl]-2-(2,4,6-trimethylphenoxy)pyridine-3-carboxamide (Compound 1079);

6-(3-chlorophenyl)-N-[(2-oxo-1H-pyridin-3-yl)sulfonyl]-2-(2,4,6-triinethylphenoxy)pyridine-3-carboxamide (Compound 1095), 6-[3-(cyclopropylmethoxy)phenyl]-N-[(2-oxo-1H-pyridin-3-yl)sulfonyl]-2-(2,4,6-trimethylphenoxy)pyridine-3-carboxamide (Compound 1105), 2-(2,4-dimethylphenoxy)-N-[(2-oxo-1H-pyridin-3-yl)sulfonyl]-6-(p-tolyl)pyridine-3-carboxamide (Compound 1129), N-[(2-oxo-1H-pyridin-3-yl)sulfonyl]-6-(3-propoxyphenyl)-2-(2,4,6-trimethylphenoxy)pyridine-3-carboxamide (Compound 1143), 6-(5-fluoro-2-methoxy-phenyl)-N-[(2-oxo-1H-pyridin-3-yl) sulfonyl]-2-(2,4,6-trimethylphenoxy)pyridine-3-carboxamide (Compound 1151), 6-(4-ethoxyphenyl)-N-[(2-oxo-1H-pyridin-3-yl)sulfonyl]-2-(2,4,6-trimethylphenoxy)pyridine-3-carboxamide (Compound 1179), 6-(4-butoxy-3-fluoro-phenyl)-N-[(2-oxo-1H-pyridin-3-yl) sulfonyl]-2-(2,4,6-trimethylphenoxy)pyridine-3-carboxamide (Compound 1187), 6-(3-isopropoxyphenyl)-N-[(2-oxo-1H-pyridin-3-yl)sulfonyl]-2-(2,4,6-trimethylphenoxy)pyridine-3-carboxamide (Compound 1188), 6-(2-chloro-5-isobutoxy-phenyl)-N-[(2-oxo-1H-pyridin-3-yl)sulfonyl]-2-(2,4,6-trimethylphenoxy)pyridine-3-carboxamide (Compound 1201), N-[(2-oxo-1H-pyridin-3-yl)sulfonyl]-6-(4-propoxyphenyl)-2-(2,4,6-trimethylphenoxy)pyridine-3-carboxamide (Compound 1202), 6-(2,3-difluorophenyl)-N-[(2-oxo-1H-pyridin-3-yl)sulfonyl]-2-(2,4,6-trimethylphenoxy)pyridine-3-carboxamide (Compound 1296), N-[(2-oxo-1H-pyridin-3-yl)sulfonyl]-6-(p-tolyl)-2-(2,4,6-trimethylphenoxy)pyridine-3-carboxamide (Compound 1300), 6-(5-ethoxy-2-fluoro-phenyl)-N-[(2-oxo-1H-pyridin-3-yl) sulfonyl]-2-(2,4,6-trimethylphenoxy)pyridine-3-carboxamide (Compound 1301), 6-(3-fluoro-5-isobutoxy-phenyl)-N-[(2-oxo-1H-pyridin-3-yl)sulfonyl]-2-(2,4,6-trimethylphenoxy)pyridine-3-carboxamide (Compound 169), 2-[(2R,5S)-2,5-dimethylpyrrolidin-1-yl]-N-[(2-oxo-1H-pyridin-3-yl)sulfonyl]-6-(p-tolyl)pyridine-3-carboxamide (Compound 392), 6-(6-isopropoxy-3-pyridyl)-N-[(2-oxo-1H-pyridin-3-yl) sulfonyl]-2-[(4R)-2,2,4-trimethylpyrrolidin-1-yl]pyridine-3-carboxamide (Compound 403), 2-[(2S,5R)-2,5-dimethylpyrrolidin-1-yl]-6-(3-fluoro-5-isopropoxy-phenyl)-N-[(2-oxo-1H-pyridin-3-yl)sulfonyl] pyridine-3-carboxamide (Compound 487), 6-(3-fluoro-5-isobutoxy-phenyl)-N-[(2-oxo-1H-pyridin-3-yl)sulfonyl]-2-[(4S)-2,2,4-trimethylpyrrolidin-1-yl]pyridine-3-carboxamide (Compound 492), 6-(6-isopropoxy-3-pyridyl)-N-[(2-oxo-1H-pyridin-3-yl) sulfonyl]-2-[(4S)-2,2,4-trimethylpyrrolidin-1-yl]pyridine-3-carboxamide (Compound 497), 2-[(2S,5R)-2,5-dimethylpyrrolidin-1-yl]-6-(3-isobutoxyphenyl)-N-[(2-oxo-1H-pyridin-3-yl)sulfonyl]pyridine-3-carboxamide (Compound 511), 6-[3-(cyclopropylmethoxy)-5-fluoro-phenyl]-2-[(2S,5R)-2,5-dimethylpyrrolidin-1-yl]-N-[(2-oxo-1H-pyridin-3-yl) sulfonyl]pyridine-3-carboxamide (Compound 541), 6-[3-(2,2-dimethylpropoxy)-5-fluoro-phenyl]-2-[(2S,5R)-2,5-dimethylpyrrolidin-1-yl]-N-[(2-oxo-1H-pyridin-3-yl) sulfonyl]pyridine-3-carboxamide (Compound 572), 2-[(2S,5R)-2,5-dimethylpyrrolidin-1-yl]-6-(4-isopropylphenyl)-N-[(2-oxo-1H-pyridin-3-yl)sulfonyl]pyridine-3-carboxamide (Compound 589), 6-(3-fluoro-5-isobutoxy-phenyl)-N-[(2-oxo-1H-pyridin-3-yl)sulfonyl]-2-[(4R)-2,2,4-trimethylpyrrolidin-1-yl]pyridine-3-carboxamide (Compound 605), 2-[(2S,5R)-2,5-dimethylpyrrolidin-1-yl]-N-[(2-oxo-1H-pyridin-3-yl)sulfonyl]-6-phenyl-pyridine-3-carboxamide (Compound 660), 6-[3-(cyclopropylmethoxy)-5-fluoro-phenyl]-2-(4-methyl-1-piperidyl)-N-[(2-oxo-1H-pyridin-3-yl)sulfonyl]pyridine-3-carboxamide (Compound 664), 2-[(2S,5R)-2,5-dimethylpyrrolidin-1-yl]-6-(3-fluoro-5-isopentyloxy-phenyl)-N-[(2-oxo-1H-pyridin-3-yl)sulfonyl] pyridine-3-carboxamide (Compound 688), 2-[(2S,5R)-2,5-dimethylpyrrolidin-1-yl]-6-(2-fluoro-5-isobutoxy-phenyl)-N-[(2-oxo-1H-pyridin-3-yl)sulfonyl] pyridine-3-carboxamide (Compound 721), 6-(3-fluoro-5-isopropoxy-phenyl)-2-(4-methyl-1-piperidyl)-N-[(2-oxo-1H-pyridin-3-yl)sulfonyl]pyridine-3-carboxamide (Compound 737), 6-(4-chlorophenyl)-2-[(2S,5R)-2,5-dimethylpyrrolidin-1-yl]-N-[(2-oxo-1H-pyridin-3-yl)sulfonyl]pyridine-3-carboxamide (Compound 760), 2-[(2S,5R)-2,5-dimethylpyrrolidin-1-yl]-6-(6-isopropoxy-3-pyridyl)-N-[(2-oxo-1H-pyridin-3-yl)sulfonyl]pyridine-3-carboxamide (Compound 770), 2-[(2S,5R)-2,5-dimethylpyrrolidin-1-yl]-6-(6-methoxy-2-pyridyl)-N-[(2-oxo-1H-pyridin-3-yl)sulfonyl]pyridine-3-carboxamide (Compound 781), 2-[(2S,5R)-2,5-dimethylpyrrolidin-1-yl]-6-(4-isobutoxyphenyl)-N-[(2-oxo-1H-pyridin-3-yl)sulfonyl]pyridine-3-carboxamide (Compound 891), 6-(4-chloro-3-isobutoxy-phenyl)-2-[(2S,5R)-2,5-dimethylpyrrolidin-1-yl]-N-[(2-oxo-1H-pyridin-3-yl)sulfonyl] pyridine-3-carboxamide (Compound 902), 6-[3-(cyclobutylmethoxy)-5-fluoro-phenyl]-2-[(2S,5R)-2,5-dimethylpyrrolidin-1-yl]-N-[(2-oxo-1H-pyridin-3-yl) sulfonyl]pyridine-3-carboxamide (Compound 922), 6-(4-chloro-3-isobutoxy-phenyl)-2-(4-methyl-1-piperidyl)-N-[(2-oxo-1H-pyridin-3-yl)sulfonyl]pyridine-3-carboxamide (Compound 941), 6-(3-isobutoxyphenyl)-2-(4-methyl-1-piperidyl)-N-[(2-oxo-1H-pyridin-3-yl)sulfonyl]pyridine-3-carboxamide (Compound 958), 6-(4-chloro-3-isopropoxy-phenyl)-2-[(2S,5R)-2,5-dimethylpyrrolidin-1-yl]-N-[(2-oxo-1H-pyridin-3-yl)sulfonyl] pyridine-3-carboxamide (Compound 1001), 6-(4-isobutoxyphenyl)-2-(4-methyl-1-piperidyl)-N-[(2-oxo-1H-pyridin-3-yl)sulfonyl]pyridine-3-carboxamide (Compound 1017), 2-[(2R,5S)-2,5-dimethylpyrrolidin-1-yl]-6-(3-ethoxy-5-fluoro-phenyl)-N-[(2-oxo-1H-pyridin-3-yl)sulfonyl]pyridine-3-carboxamide (Compound 1096), 8,8-dimethyl-2-(4-methyl-1-piperidyl)-N-[(2-oxo-1H-pyridin-3-yl)sulfonyl]-6,7-dihydro-5H-quinoline-3-carboxamide (Compound 1195), 6-(4-chloro-3-propoxy-phenyl)-2-[(2R,5S)-2,5-dimethylpyrrolidin-1-yl]-N-[(2-oxo-1H-pyridin-3-yl)sulfonyl] pyridine-3-carboxamide (Compound 1293), 6-(3-fluoro-5-isobutoxy-phenyl)-N-[(2-oxo-1H-pyridin-3-yl)sulfonyl]-2-[(3S)-3-phenyl-1-piperidyl]pyridine-3-carboxamide (Compound 481), 6-(2-methoxy-5-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2530), 6-(3-ethoxyphenyl)-N-[(2-oxo-1H-pyridin-3-yl)sulfonyl]-2-[(4S)-2,2,4-trimethylpyrrolidin-1-yl]pyridine-3-carboxamide (Compound 2235), 6-(4-methoxy-2-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2469), 6-(4-ethoxyphenyl)-N-[(2-oxo-1H-pyridin-3-yl)sulfonyl]-2-[(4S)-2,2,4-trimethylpyrrolidin-1-yl]pyridine-3-carboxamide (Compound 2207), 6-(2-methoxy-3-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 1880), 6-isobutyl-N-[(2-oxo-1H-pyridin-3-yl)sulfonyl]-2-[(4S)-2,2,4-trimethylpyrrolidin-1-yl]pyridine-3-carboxamide (Compound 2467), 6-(3-methoxy-4-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2440), 6-(3-isopropoxyphenyl)-N-[(2-oxo-1H-pyridin-3-yl)sulfonyl]-2-[(4S)-2,2,4-trimethylpyrrolidin-1-yl]pyridine-3-carboxamide (Compound 2549), 6-(4-isopropoxyphenyl)-N-[(2-oxo-1H-pyridin-3-yl)sulfonyl]-2-[(4S)-2,2,4-trimethylpyrrolidin-1-yl]pyridine-3-carboxamide (Compound 1774), 6-(2-isobutoxyphenyl)-N-[(2-oxo-1H-pyridin-3-yl)sulfonyl]-2-[(4S)-2,2,4-trimethylpyrrolidin-1-yl]pyridine-3-carboxamide (Compound 2629), 6-(3-fluoro-4-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2219), 6-(3-isobutoxyphenyl)-N-[(2-oxo-1H-pyridin-3-yl)sulfonyl]-2-[(4S)-2,2,4-trimethylpyrrolidin-1-yl]pyridine-3-carboxamide (Compound 2267), 6-(2-fluoro-6-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2422), 6-(4-isobutoxyphenyl)-N-[(2-oxo-1H-pyridin-3-yl)sulfonyl]-2-[(4S)-2,2,4-trimethylpyrrolidin-1-yl]pyridine-3-carboxamide (Compound 2153), 6-(2-fluoro-3-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2222), 6-(5-fluoro-2-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1830), N-[(2-oxo-1H-pyridin-3-yl)sulfonyl]-6-[3-(trifluoromethoxy)phenyl]-2-[(4S)-2,2,4-trimethylpyrrolidin-1-yl]pyridine-3-carboxamide (Compound 1934), 6-(2-fluoro-5-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2606), N-[(2-oxo-1H-pyridin-3-yl)sulfonyl]-6-[4-(trifluoromethoxy)phenyl]-2-[(4S)-2,2,4-trimethylpyrrolidin-1-yl]pyridine-3-carboxamide (Compound 2234), 6-(4-fluoro-2-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2356), 6-(3-fluoro-5-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2527), N-[(2-oxo-1H-pyridin-3-yl)sulfonyl]-6-[3-(trifluoromethyl)phenyl]-2-[(4S)-2,2,4-trimethylpyrrolidin-1-yl]pyridine-3-carboxamide (Compound 2144), 6-(2-fluoro-4-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1858), 6-(3-fluoro-2-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1779), 6-(4-fluoro-3-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1780), 6-(2-naphthyl)-N-[(2-oxo-1H-pyridin-3-yl)sulfonyl]-2-[(4S)-2,2,4-trimethylpyrrolidin-1-yl]pyridine-3-carboxamide (Compound 1803), 6-(1-naphthyl)-N-[(2-oxo-1H-pyridin-3-yl)sulfonyl]-2-[(4S)-2,2,4-trimethylpyrrolidin-1-yl]pyridine-3-carboxamide (Compound 2007), 6-(2,4-dimethylphenyl)-N-[(2-oxo-1H-pyridin-3-yl)sulfonyl]-2-[(4S)-2,2,4-trimethylpyrrolidin-1-yl]pyridine-3-carboxamide (Compound 2037), N-[(2-oxo-1H-pyridin-3-yl)sulfonyl]-6-(2,3,5-trifluorophenyl)-2-[(4S)-2,2,4-trimethylpyrrolidin-1-yl]pyridine-3-carboxamide (Compound 1837), N-[(2-oxo-1H-pyridin-3-yl)sulfonyl]-6-(2,4,5-trifluorophenyl)-2-[(4S)-2,2,4-trimethylpyrrolidin-1-yl]pyridine-3-carboxamide (Compound 1981), 6-(2,3-dihydro-1,4-benzodioxin-6-yl)-N-[(2-oxo-1H-pyridin-3-yl)sulfonyl]-2-[(4S)-2,2,4-trimethylpyrrolidin-1-yl]pyridine-3-carboxamide (Compound 2516), 6-(2-hydroxy-3-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2300), 6-(3-ethoxy-5-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2512), 6-(2,3-dimethylphenyl)-N-[(2-oxo-1H-pyridin-3-yl)sulfonyl]-2-[(4S)-2,2,4-trimethylpyrrolidin-1-yl]pyridine-3-carboxamide (Compound 2073), 6-(2-hydroxy-5-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2174), 6-(5-fluoro-2-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2067), 6-(2-ethoxy-5-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2410), 6-(4-methoxy-2,6-dimethyl-phenyl)-N-[(2-oxo-1H-pyridin-3-yl)sulfonyl]-2-[(4S)-2,2,4-trimethylpyrrolidin-1-yl]pyridine-3-carboxamide (Compound 2575), 6-[3-(hydroxymethyl)-5-methoxy-phenyl]-N-[(2-oxo-1H-pyridin-3-yl)sulfonyl]-2-[(4S)-2,2,4-trimethylpyrrolidin-1-yl]pyridine-3-carboxamide (Compound 2247), 6-(2,3-dimethoxyphenyl)-N-[(2-oxo-1H-pyridin-3-yl)sulfonyl]-2-[(4S)-2,2,4-trimethylpyrrolidin-1-yl]pyridine-3-carboxamide (Compound 1786), 6-(2,5-dimethoxyphenyl)-N-[(2-oxo-1H-pyridin-3-yl)sulfonyl]-2-[(4S)-2,2,4-trimethylpyrrolidin-1-yl]pyridine-3-carboxamide (Compound 1752), 6-(2-hydroxy-4-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2148), 6-(3,5-dimethoxyphenyl)-N-[(2-oxo-1H-pyridin-3-yl)sulfonyl]-2-[(4S)-2,2,4-trimethylpyrrolidin-1-yl]pyridine-3-carboxamide (Compound 1878), 6-(2-ethoxy-5-fluoro-phenyl)-N-[(2-oxo-1H-pyridin-3-yl)sulfonyl]-2-[(4S)-2,2,4-trimethylpyrrolidin-1-yl]pyridine-3-carboxamide (Compound 2051),
6-(5-ethoxy-2-fluoro-phenyl)-N-[(2-oxo-1H-pyridin-3-yl)sulfonyl]-2-[(4S)-2,2,4-trimethylpyrrolidin-1-yl]pyridine-3-carboxamide (Compound 2138),
6-(3-ethoxy-2-fluoro-phenyl)-N-[(2-oxo-1H-pyridin-3-yl)sulfonyl]-2-[(4S)-2,2,4-trimethylpyrrolidin-1-yl]pyridine-3-carboxamide (Compound 1802),
6-(2-ethoxy-4-fluoro-phenyl)-N-[(2-oxo-1H-pyridin-3-yl)sulfonyl]-2-[(4S)-2,2,4-trimethylpyrrolidin-1-yl]pyridine-3-carboxamide (Compound 1867),
6-(3,5-dimethylphenyl)-N-[(2-oxo-1H-pyridin-3-yl)sulfonyl]-2-[(4S)-2,2,4-trimethylpyrrolidin-1-yl]pyridine-3-carboxamide (Compound 2626),
6-(3-ethoxy-5-fluoro-phenyl)-N-[(2-oxo-1H-pyridin-3-yl)sulfonyl]-2-[(4S)-2,2,4-trimethylpyrrolidin-1-yl]pyridine-3-carboxamide (Compound 2278),
6-(3-ethoxy-4-fluoro-phenyl)-N-[(2-oxo-1H-pyridin-3-yl)sulfonyl]-2-[(4S)-2,2,4-trimethylpyrrolidin-1-yl]pyridine-3-carboxamide (Compound 2459),
6-(3,4-dimethylphenyl)-N-[(2-oxo-1H-pyridin-3-yl)sulfonyl]-2-[(4S)-2,2,4-trimethylpyrrolidin-1-yl]pyridine-3-carboxamide (Compound 2154),
6-(4-methyl-1-naphthyl)-N-[(2-oxo-1H-pyridin-3-yl)sulfonyl]-2-[(4S)-2,2,4-trimethylpyrrolidin-1-yl]pyridine-3-carboxamide (Compound 1811),
6-(2-isopropylphenyl)-N-[(2-oxo-1H-pyridin-3-yl)sulfonyl]-2-[(4S)-2,2,4-trimethylpyrrolidin-1-yl]pyridine-3-carboxamide (Compound 2635),
6-(4,5-difluoro-2-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1904),
6-(3,5-difluoro-2-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2496),
6-(2,3-difluoro-4-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 2567),
6-(3,5-difluoro-4-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1801),
6-(3,4-difluoro-5-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1914),
6-(2,5-difluoro-4-methoxy-phenyl)-N-[(2-oxo-1H-pyridin-3-yl)sulfonyl]-2-[(4S)-2,2,4-trimethylpyrrolidin-1-yl]pyridine-3-carboxamide (Compound 1913),
6-(4-hydroxy-3,5-dimethyl-phenyl)-N-[(2-oxo-1H-pyridin-3-yl)sulfonyl]-2-[(4S)-2,2,4-trimethylpyrrolidin-1-yl]pyridine-3-carboxamide (Compound 2556),
6-(1H-indol-5-yl)-N-[(2-oxo-1H-pyridin-3-yl)sulfonyl]-2-[(4S)-2,2,4-trimethylpyrrolidin-1-yl]pyridine-3-carboxamide (Compound 1982),
6-(1H-indol-4-yl)-N-[(2-oxo-1H-pyridin-3-yl)sulfonyl]-2-[(4S)-2,2,4-trimethylpyrrolidin-1-yl]pyridine-3-carboxamide (Compound 2636),
6-(6-ethoxy-4-methyl-2-pyridyl)-N-[(2-oxo-1H-pyridin-3-yl)sulfonyl]-2-[(4S)-2,2,4-trimethylpyrrolidin-1-yl]pyridine-3-carboxamide (Compound 1745),
6-(3-fluoro-4-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2084),
6-(2-fluoro-4-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2000),
6-(3-fluoro-2-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2491),
6-(2-chlorophenyl)-N-[(2-oxo-1H-pyridin-3-yl)sulfonyl]-2-[(4S)-2,2,4-trimethylpyrrolidin-1-yl]pyridine-3-carboxamide (Compound 1784),
6-(3-fluoro-5-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2348),
6-(2-fluoro-5-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 1946),
6-(3-chlorophenyl)-N-[(2-oxo-1H-pyridin-3-yl)sulfonyl]-2-[(4S)-2,2,4-trimethylpyrrolidin-1-yl]pyridine-3-carboxamide (Compound 1791),
6-(3,4-difluorophenyl)-N-[(2-oxo-1H-pyridin-3-yl)sulfonyl]-2-[(4S)-2,2,4-trimethylpyrrolidin-1-yl]pyridine-3-carboxamide (Compound 2284),
6-(4-chlorophenyl)-N-[(2-oxo-1H-pyridin-3-yl)sulfonyl]-2-[(4S)-2,2,4-trimethylpyrrolidin-1-yl]pyridine-3-carboxamide (Compound 2028),
6-(2,4-difluorophenyl)-N-[(2-oxo-1H-pyridin-3-yl)sulfonyl]-2-[(4S)-2,2,4-trimethylpyrrolidin-1-yl]pyridine-3-carboxamide (Compound 2159),
6-(2,3-difluorophenyl)-N-[(2-oxo-1H-pyridin-3-yl)sulfonyl]-2-[(4S)-2,2,4-trimethylpyrrolidin-1-yl]pyridine-3-carboxamide (Compound 2162),
6-(3,5-difluorophenyl)-N-[(2-oxo-1H-pyridin-3-yl)sulfonyl]-2-[(4S)-2,2,4-trimethylpyrrolidin-1-yl]pyridine-3-carboxamide (Compound 2652),
6-(2,5-difluorophenyl)-N-[(2-oxo-1H-pyridin-3-yl)sulfonyl]-2-[(4S)-2,2,4-trimethylpyrrolidin-1-yl]pyridine-3-carboxamide (Compound 1954),
6-(2-fluorophenyl)-N-[(2-oxo-1H-pyridin-3-yl)sulfonyl]-2-[(4S)-2,2,4-trimethylpyrrolidin-1-yl]pyridine-3-carboxamide (Compound 2542),
6-(2-isopropoxyphenyl)-N-[(2-oxo-1H-pyridin-3-yl)sulfonyl]-2-[(4S)-2,2,4-trimethylpyrrolidin-1-yl]pyridine-3-carboxamide (Compound 2541),
6-(3-cyanophenyl)-N-[(2-oxo-1H-pyridin-3-yl)sulfonyl]-2-[(4S)-2,2,4-trimethylpyrrolidin-1-yl]pyridine-3-carboxamide (Compound 2185),
6-(3-fluorophenyl)-N-[(2-oxo-1H-pyridin-3-yl)sulfonyl]-2-[(4S)-2,2,4-trimethylpyrrolidin-1-yl]pyridine-3-carboxamide (Compound 1925),
6-(4-fluorophenyl)-N-[(2-oxo-1H-pyridin-3-yl)sulfonyl]-2-[(4S)-2,2,4-trimethylpyrrolidin-1-yl]pyridine-3-carboxamide (Compound 1807),
N-[(2-oxo-1H-pyridin-3-yl)sulfonyl]-6-[2-(trifluoromethyl)phenyl]-2-[(4S)-2,2,4-trimethylpyrrolidin-1-yl]pyridine-3-carboxamide (Compound 1960),
6-(2-methoxy-3-pyridyl)-N-[(2-oxo-1H-pyridin-3-yl)sulfonyl]-2-[(4S)-2,2,4-trimethylpyrrolidin-1-yl]pyridine-3-carboxamide (Compound 2454),
N-[(2-oxo-1H-pyridin-3-yl)sulfonyl]-6-[4-(trifluoromethyl)cyclohexyl]-2-[(4S)-2,2,4-trimethylpyrrolidin-1-yl]pyridine-3-carboxamide (Compound 2315),
N-[(2-oxo-1H-pyridin-3-yl)sulfonyl]-6-[4-(trifluoromethyl)cyclohexyl]-2-[(4S)-2,2,4-trimethylpyrrolidin-1-yl]pyridine-3-carboxamide (Compound 1710),
6-(2,5-dimethylphenyl)-N-[(2-oxo-1H-pyridin-3-yl)sulfonyl]-2-[(4S)-2,2,4-trimethylpyrrolidin-1-yl]pyridine-3-carboxamide (Compound 1990),
6-(o-tolyl)-N-[(2-oxo-1H-pyridin-3-yl)sulfonyl]-2-[(4S)-2,2,4-trimethylpyrrolidin-1-yl]pyridine-3-carboxamide (Compound 2176), 6-(4-fluoro-3-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2456), 6-(5-fluoro-6-methoxy-3-pyridyl)-N-[(2-oxo-1H-pyridin-3-yl)sulfonyl]-2-[(4S)-2,2,4-trimethylpyrrolidin-1-yl]pyridine-3-carboxamide (Compound 2444), 6-(6-methoxy-2-pyridyl)-N-[(2-oxo-1H-pyridin-3-yl)sulfonyl]-2-[(4S)-2,2,4-trimethylpyrrolidin-1-yl]pyridine-3-carboxamide (Compound 2101), 6-(2,6-dimethoxy-3-pyridyl)-N-[(2-oxo-1H-pyridin-3-yl)sulfonyl]-2-[(4S)-2,2,4-trimethylpyrrolidin-1-yl]pyridine-3-carboxamide (Compound 1853), 6-(3-isopropylphenyl)-N-[(2-oxo-1H-pyridin-3-yl)sulfonyl]-2-[(4S)-2,2,4-trimethylpyrrolidin-1-yl]pyridine-3-carboxamide (Compound 2498), 6-(4-isopropylphenyl)-N-[(2-oxo-1H-pyridin-3-yl)sulfonyl]-2-[(4S)-2,2,4-trimethylpyrrolidin-1-yl]pyridine-3-carboxamide (Compound 2483), 6-(5-fluoro-2-hydroxy-phenyl)-N-[(2-oxo-1H-pyridin-3-yl)sulfonyl]-2-[(4S)-2,2,4-trimethylpyrrolidin-1-yl]pyridine-3-carboxamide (Compound 2295), 6-(2-methoxyphenyl)-N-[(2-oxo-1H-pyridin-3-yl)sulfonyl]-2-[(4S)-2,2,4-trimethylpyrrolidin-1-yl]pyridine-3-carboxamide (Compound 2485), 6-(2,3-dihydrobenzofuran-7-yl)-N-[(2-oxo-1H-pyridin-3-yl)sulfonyl]-2-[(4S)-2,2,4-trimethylpyrrolidin-1-yl]pyridine-3-carboxamide (Compound 2583), 6-(4-methoxy-3-methyl-phenyl)-N-[(2-oxo-1H-pyridin-3-yl)sulfonyl]-2-[(4S)-2,2,4-trimethylpyrrolidin-1-yl]pyridine-3-carboxamide (Compound 2369), 6-(2-ethoxyphenyl)-N-[(2-oxo-1H-pyridin-3-yl)sulfonyl]-2-[(4S)-2,2,4-trimethylpyrrolidin-1-yl]pyridine-3-carboxamide (Compound 1848), 6-(3-fluoro-5-isobutoxy-phenyl)-2-(4-methyl-1-piperidyl)-N-[(2-oxo-1H-pyridin-3-yl)sulfonyl]pyridine-3-carboxamide (Compound 422), and 6-(2-fluoro-5-isobutoxy-phenyl)-N-[(2-oxo-1H-pyridin-3-yl)sulfonyl]-2-(2,4,6-trimethylphenoxy)pyridine-3-carboxamide (Compound 279).

Preparation 42: N-(3-aminopyrazin-2-yl)sulfonyl-8,8-dimethyl-2-(4-methyl-1-piperidyl)-6,7-dihydro-5H-quinoline-3-carboxamide (Compound 197)

Step 1: 8,8-dimethyl-2-(4-methyl-1-piperidyl)-6,7-dihydro-5H-quinoline-3-carbonitrile

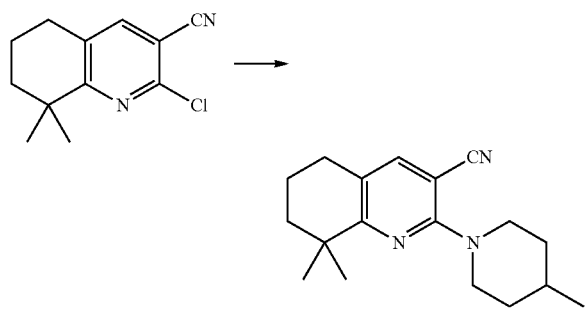

A mixture of 2-chloro-8,8-dimethyl-6,7-dihydro-5H-quinoline-3-carbonitrile (1.00 g, 4.51 mmol) and 4-methylpiperidine (4.29 mL, 36.3 mmol) was stirred at 100° C. for 1 h. The reaction mixture was diluted with water and was extracted with ethyl acetate (3×). The combined extracts were washed with water, dried over sodium sulfate, and evaporated. The residue was purified by silica gel chromatography with 0-5% ethyl acetate in hexanes to give 8,8-dimethyl-2-(4-methylpiperidin-1-yl)-5,6,7,8-tetrahydroquinoline-3-carbonitrile (1.00 g, 78%) as a colorless oil. ESI-MS m/z calc. 283.2, found 284.3 (M+1)⁺; Retention time: 0.94 min (1 min run).

Step 2: 8,8-dimethyl-2-(4-methyl-1-piperidyl)-6,7-dihydro-5H-quinoline-3-carboxylic acid

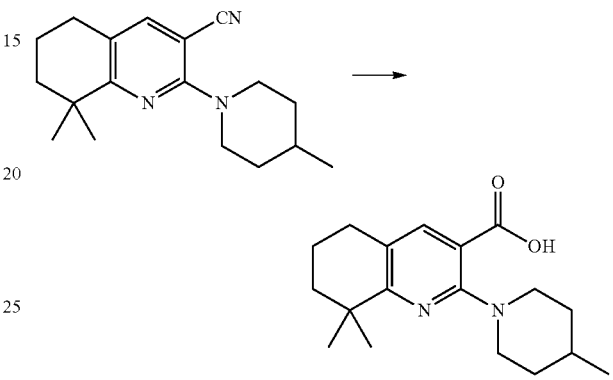

A solution of 8,8-dimethyl-2-(4-methylpiperidin-1-yl)-5,6,7,8-tetrahydroquinoline-3-carbonitrile (0.80 g, 2.8 mmol) and KOH (1.6 g, 28 mmol) in ethanol (5.6 mL) was heated at reflux for 4 d. The reaction mixture was neutralized with 1 M HCl, and the solids were filtered, washed with water, and dried under vacuum to give 8,8-dimethyl-2-(4-methylpiperidin-1-yl)-5,6,7,8-tetrahydroquinoline-3-carboxylic acid (0.71 g, 83%) as a tan solid. ESI-MS m/z calc. 302.2, found 303.3 (M+1)⁺; Retention time: 0.58 min (1 min run).

Step 3: N-(3-chloropyrazin-2-yl)sulfonyl-8,8-dimethyl-2-(4-methyl-1-piperidyl)-6,7-dihydro-5H-quinoline-3-carboxamide

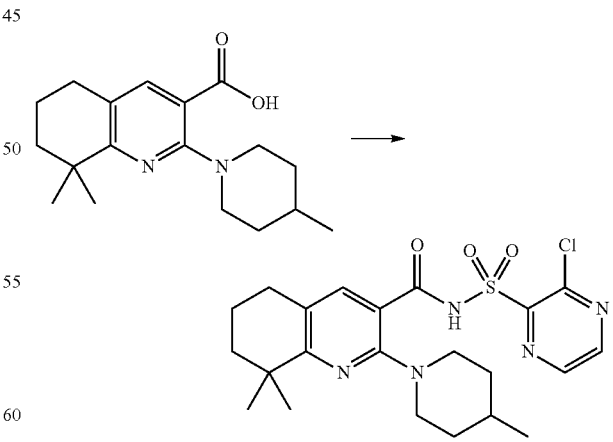

A solution of 8,8-dimethyl-2-(4-methylpiperidin-1-yl)-5,6,7,8-tetrahydroquinoline-3-carboxylic acid (0.11 g, 0.36 mmol), N-[(dimethylamino)-1H-1,2,3-triazolo-[4,5-b]pyridin-1-ylmethylene]-N-methylmethanaminium hexafluorophosphate N-oxide (170 mg, 0.44 mmol) and sodium carbonate (77 mg, 0.73 mmol) in N,N-dimethylformamide (1.8 mL) was stirred for 5 min before 3-chloropyrazine-2-sulfonamide (110 mg, 0.55 mmol) was added. The reaction mixture was stirred for 20 h, filtered, and subjected to preparatory-HPLC (1-99% CH$_3$CN/water) to give N-(3-chloropyrazin-2-yl)sulfonyl-8,8-dimethyl-2-(4-methyl-1-piperidyl)-6,7-dihydro-5H-quinoline-3-carboxamide (75 mg, 43%). ESI-MS m/z calc. 477.2, found 478.3 (M+1)$^+$; Retention time: 0.65 min (1 min run).

Step 4: N-(3-Aminopyrazin-2-yl)sulfonyl-8,8-dimethyl-2-(4-methyl-1-piperidyl)-6,7-dihydro-5H-quinoline-3-carboxamide

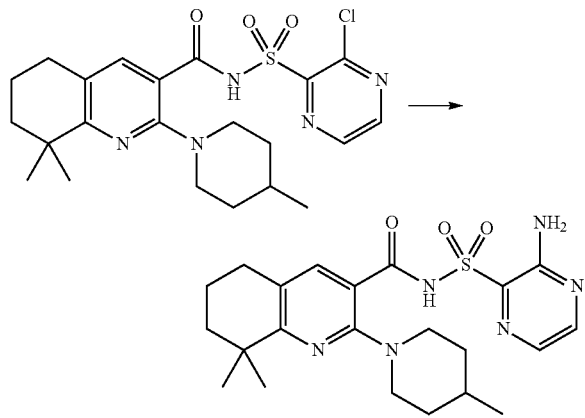

N-(3-Chloropyrazin-2-yl)sulfonyl-8,8-dimethyl-2-(4-methyl-1-piperidyl)-6,7-dihydro-5H-quinoline-3-carboxamide (35 mg, 0.073 mmol) and ammonium hydroxide (1 mL, 26 mmol) was heated in a sealed vial in an microwave reactor at 120° C. for 20 min. The reaction mixture was concentrated, the residue was taken up in DMSO and subjected to preparatory-HPLC (1-99% CH$_3$CN/water) to give N-(3-aminopyrazin-2-yl)sulfonyl-8,8-dimethyl-2-(4-methyl-1-piperidyl)-6,7-dihydro-5H-quinoline-3-carboxamide (Compound 197) (8.7 mg, 26%). ESI-MS m/z calc. 458.2, found 459.3 (M+1)$^+$; Retention time: 1.67 min (3 min run).

The following compound can be synthesized using the procedures described herein:

N-(3-aminopyrazin-2-yl)sulfonyl-8,8-dimethyl-2-(p-tolyl)-6,7-dihydro-5H-quinoline-3-carboxamide (Compound 707), N-(3-aminopyrazin-2-yl)sulfonyl-6-(4-ethoxyphenyl)-2-(p-tolyl)pyridine-3-carboxamide (Compound 819), N-(3-aminopyrazin-2-yl)sulfonyl-6-(3-fluoro-5-isopropoxy-phenyl)-2-(p-tolyl)pyridine-3-carboxamide (Compound 1351), N-(3-aminopyrazin-2-yl)sulfonyl-2,6-bis(p-tolyl)pyridine-3-carboxamide (Compound 820), N-(3-aminopyrazin-2-yl)sulfonyl-8,8-dimethyl-2-(p-tolyl)-6,7-dihydro-5H-quinoline-3-carboxamide (Compound 707), N-(3-aminopyrazin-2-yl)sulfonyl-2-(2,4-dimethylphenoxy)-6-(4-ethoxyphenyl)pyridine-3-carboxamide (Compound 434), N-[(6-amino-3-pyridyl)sulfonyl]-6-tert-butyl-2-(p-tolyl)pyridine-3-carboxamide (Compound 702), N-(6-aminopyrazin-2-yl)sulfonyl-6-(3-fluoro-5-isobutoxy-phenyl)-2-(2,4,6-trimethylphenoxy)pyridine-3-carboxamide (Compound 586), N-(3-aminopyrazin-2-yl)sulfonyl-8,8-dimethyl-2-(2,4,6-trimethylphenoxy)-6,7-dihydro-5H-quinoline-3-carboxamide (Compound 1223), N-(3-aminopyrazin-2-yl)sulfonyl-2-(2,4-dimethylphenoxy)-8,8-dimethyl-6,7-dihydro-5H-quinoline-3-carboxamide (Compound 1239), N-(3-aminopyrazin-2-yl)sulfonyl-6-tert-butyl-2-(2,4,6-trimethylphenoxy)pyridine-3-carboxamide (Compound 1208), N-(3-aminopyrazin-2-yl)sulfonyl-2-(2,4-dimethylphenoxy)-6-(3-fluoro-5-isopropoxy-phenyl)pyridine-3-carboxamide (Compound 559), N-(3-aminopyrazin-2-yl)sulfonyl-2-(2,4-dimethylphenoxy)-6-(p-tolyl)pyridine-3-carboxamide (Compound 607), N-(3-aminopyrazin-2-yl)sulfonyl-2-(2,4-dimethylphenoxy)-6-(1-isobutylpyrazol-4-yl)pyridine-3-carboxamide (Compound 713), N-(3-aminopyrazin-2-yl)sulfonyl-2-(2,4-dimethylphenoxy)-6-(6-methoxy-5-methyl-3-pyridyl)pyridine-3-carboxamide (Compound 893), N-(3-aminopyrazin-2-yl)sulfonyl-6-(3-fluoro-5-isopropoxy-phenyl)-2-(2,4,6-trimethylphenoxy)pyridine-3-carboxamide (Compound 989), N-(3-aminopyrazin-2-yl)sulfonyl-6-(4-ethoxyphenyl)-2-(2,4,6-trimethylphenoxy)pyridine-3-carboxamide (Compound 1019), N-(3-aminopyrazin-2-yl)sulfonyl-6-(p-tolyl)-2-(2,4,6-trimethylphenoxy)pyridine-3-carboxamide (Compound 1047), N-(3-aminopyrazin-2-yl)sulfonyl-6-(1-isobutylpyrazol-4-yl)-2-(2,4,6-trimethylphenoxy)pyridine-3-carboxamide (Compound 1103), N-(3-aminopyrazin-2-yl)sulfonyl-6-(6-methoxy-5-methyl-3-pyridyl)-2-(2,4,6-trimethylphenoxy)pyridine-3-carboxamide (Compound 1249), N-(3-aminopyrazin-2-yl)sulfonyl-2-[(4-methyltetrahydropyran-4-yl)methylamino]-6-(p-tolyl)pyridine-3-carboxamide (Compound 1066), N-(3-aminopyrazin-2-yl)sulfonyl-6-(4-ethoxyphenyl)-2-[(4-methyltetrahydropyran-4-yl)methylamino]pyridine-3-carboxamide (Compound 1203), N-(3-aminopyrazin-2-yl)sulfonyl-6-(1-isobutylpyrazol-4-yl)-2-(4-methyl-1-piperidyl)pyridine-3-carboxamide (Compound 1288), N-(3-aminopyrazin-2-yl)sulfonyl-6-(6-methoxy-5-methyl-3-pyridyl)-2-(4-methyl-1-piperidyl)pyridine-3-carboxamide (Compound 1191), N-(3-aminopyrazin-2-yl)sulfonyl-2-(4-methyl-1-piperidyl)-6-(p-tolyl)pyridine-3-carboxamide (Compound 1084).

N-(3-aminopyrazin-2-yl)sulfonyl-6-(3-fluoro-5-isopropoxy-phenyl)-2-(4-methyl-1-piperidyl)pyridine-3-carboxamide (Compound 699), N-(3-aminopyrazin-2-yl)sulfonyl-6-(4-ethoxyphenyl)-2-(4-methyl-1-piperidyl)pyridine-3-carboxamide (Compound 507), 8,8-dimethyl-2-(4-methyl-1-piperidyl)-N-(1H-pyrazol-5-ylsulfonyl)-6,7-dihydro-5H-quinoline-3-carboxamide (Compound 800), N-[(6-amino-2-pyridyl)sulfonyl]-8,8-dimethyl-2-(4-methyl-1-piperidyl)-6,7-dihydro-5H-quinoline-3-carboxamide (Compound 750), and N-[(2-amino-3-pyridyl)sulfonyl]-6-tert-butyl-2-(p-tolyl)pyridine-3-carboxamide (Compound 636).

Preparation 43: N-[(3-Aminophenyl)sulfonimidoyl]-6-tert-butyl-2-(2,4,6-trimethylphenoxy)pyridine-3-carboxamide (Compound 292)

Step 1: Sodium 3-nitrobenzene-1-sulfinate

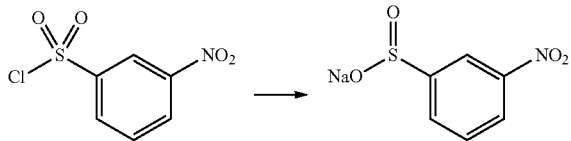

To a colorless solution of sodium sulfite (6.26 g, 49.6 mmol) in water (50 mL) at 80° C., were added 3-nitrobenzenesulfonyl chloride (5.00 g, 22.6 mmol) and sodium carbonate (4.30 g, 40.6 mmol). The reaction mixture was stirred at 80° C. for 2 h. The reaction mixture was concentrated under reduced pressure. The residue was suspended in ethanol (45 mL) and heated at 80° C. for 1H. The reaction mixture was cooled to room temperature and filtered to remove most of the salts. The filtrate was concentrated under reduced pressure to give sodium 3-nitrobenzene-1-sulfinate (4.20 g, 89% yield, containing some salts). $^1$H NMR (300 MHz, CDCl$_3$) δ 7.68 (t, J=7.8 Hz, 1H), 8.02 (dt, J=7.7, 1.4 Hz, 1H), 8.21-8.28 (m, 1H), 8.47-8.51 (m, 1H). [M+H]$^+$=188.0.

Step 2: methyl 3-nitrobenzene-1-sulfinate

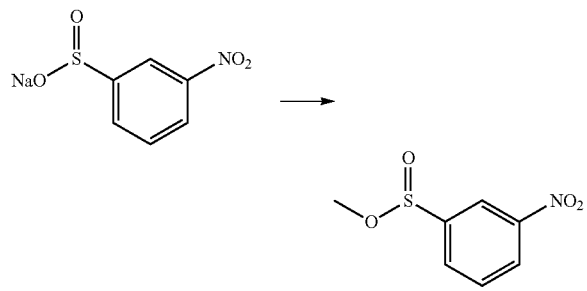

Thionyl chloride (3.27 mL, 45.0 mmol) was added to a solution of sodium 3-nitrobenzene-1-sulfinate (3.14 g, 15.0 mmol) in dichloromethane (21 mL) at 0° C. After 20 minutes at 0° C., the reaction mixture was allowed to warm to room temperature and stirred for 3 h. The reaction mixture was concentrated and dried under vacuum to give a residue (3.08 g, 15 mmol). To the residue was added dichloromethane (5 mL) and methanol (100 mL) at 0° C. After 10 minutes at this temperature, triethylamine (6.27 mL, 45.0 mmol) was added and the mixture was stirred at room temperature overnight. The mixture was concentrated under reduced pressure. The residue was dissolved in dichloromethane (50 mL), washed with water (25 mL), brine (25 mL), dried over anhydrous sodium sulfate and concentrated to give methyl 3-nitrobenzene-1-sulfinate (1.40 g, 46% yield). $^1$H NMR (300 MHz, CDCl$_3$) δ 3.52 (s, 3H), 7.71 (t, J=7.8 Hz, 1H), 7.98 (dt, J=7.7, 1.4 Hz, 1H), 8.21-8.28 (m, 1H), 8.47-8.51 (m, 1H). [M+H]$^+$=202.0.

Step 3: 6-tert-butyl-N-(3-nitrobenzenesulfinyl)-2-(2,4,6-trimethylphenoxy)-pyridine-3-carboxamide

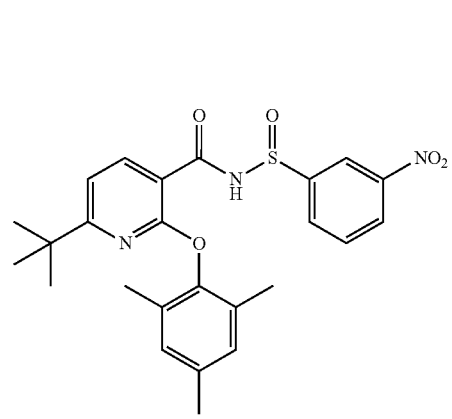

To a solution methyl 3-nitrobenzene-1-sulfinate (1.35 g, 6:70 mmol) in dimethylformamide (8.0 mL) was added methyl 3-nitrobenzene-1-sulfinate (697 mg, 2.68 mmol), followed by cesium carbonate (2.18 g, 6.69 mmol). The mixture was stirred overnight at 60° C. The mixture was diluted with ethyl acetate (60 mL), washed with water (30 mL), brine (30 mL), dried over anhydrous sodium sulfate, filtered, and concentrated. The crude material was purified by chromatography on silica gel, eluting with 10-20% ethyl acetate in heptane to give 6-tert-butyl-N-(3-nitrobenzenesulfinyl)-2-(2,4,6-trimethylphenoxy)-pyridine-3-carboxamide (725 mg, impure). This material was used in the next step without further purification. [M+H]$^+$=482.1.

Step 4: 6-tert-butyl-N-[imino(3-nitrophenyl)oxo-λ$^6$-sulfanyl]-2-(2,4,6-trimethyl-phenoxy)pyridine-3-carboxamide

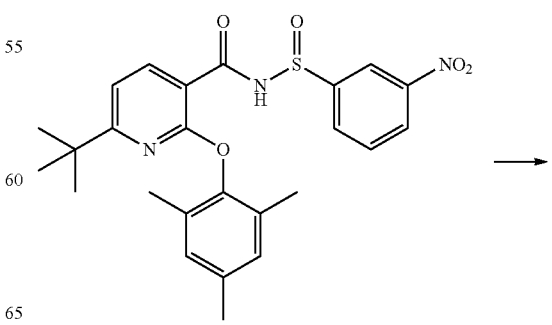

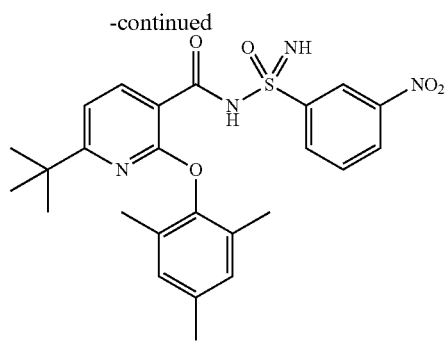

To a solution of 6-tert-butyl-N-(3-nitrobenzenesulfinyl)-2-(2,4,6-trimethylphenoxy)-pyridine-3-carboxamide (724 mg, 1.50 mmol) and potassium tert-butoxide (337 mg, 3.00 mmol) in acetonitrile (7.5 mL) was added hexamethyldisilazane (0.94 mL, 4.5 mmol), followed by N-chlorosuccinimide (0.60 g, 4.5 mmol). After stirring for 15 min, additional hexamethyldisilazane (0.94 mL, 4.5 mmol), followed by N-chlorosuccinimide (0.60 g, 4.5 mmol) were added. The mixture was stirred until TLC indicated completion. The mixture was concentrated and the residue was purified by flash chromatography, eluting with 20-50% ethyl acetate in heptane to give 6-tert-butyl-N-[imino(3-nitrophenyl)oxo-$\lambda^6$-sulfanyl]-2-(2,4,6-trimethyl-phenoxy)pyridine-3-carboxamide (95 mg, 3% over two steps). $^1$H NMR (300 MHz, CDCl$_3$) δ 1.07 (s, 9H), 2.03 (s, 6H), 2.30 (s, 3H), 6.87 (s, 2H), 6.98 (d, J=8.0 Hz, 1H), 7.74 (t, J=8.2 Hz, 1H), 8.30 (d, J=8.0 Hz, 1H), 8.41-8.53 (m, 2H), 8.95 (s, 1H). [M+H]$^+$=497.2.

Step 5: N-[(3-aminophenyl)sulfonimidoyl]-6-tert-butyl-2-(2,4,6-trimethylphenoxy)pyridine-3-carboxamide

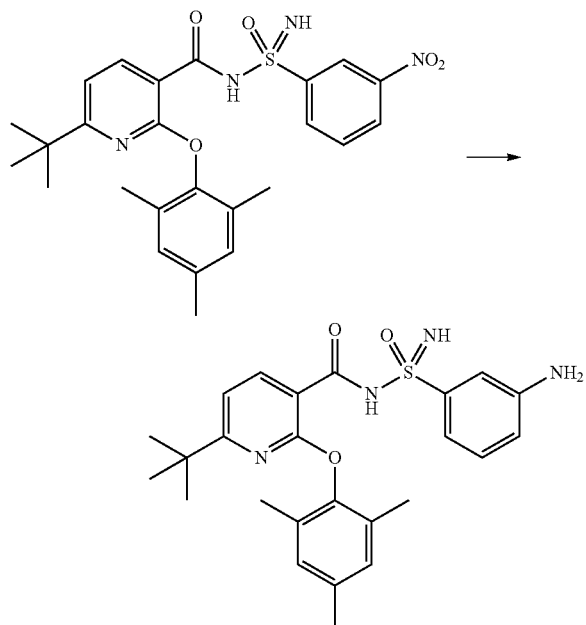

To a solution of 6-tert-butyl-N-[imino(3-nitrophenyl)oxo-$\lambda^6$-sulfanyl]-2-(2,4,6-trimethyl-phenoxy)pyridine-3-carboxamide (90 mg, 0.18 mmol) in methanol (2.6 mL) was added 10% Pd/C (19 mg, 0.018 mmol) and the mixture was stirred at room temperature for 3 h. The solvent was removed under vacuum and the crude material was purified by flash chromatography eluting with 20-50% ethyl acetate/heptane to give N-[(3-aminophenyl)sulfonimidoyl]-6-tert-butyl-2-(2,4,6-trimethylphenoxy)pyridine-3-carboxamide (52 mg, 62% yield). $^1$H NMR (300 MHz, CDCl$_3$) δ 1.01 (s, 9H), 1.92 (s, 6H), 2.22 (s, 3H), 5.57 (br. s, 2H), 6.73 (d, J=8.1 Hz, 1H), 6.85 (s, 2H), 6.97-7.07 (m, 2H), 7.11-7.20 (m, 2H), 7.56 (br. s, 2H), 8.09 (d, J=7.8 Hz, 1H). [M+H]$^+$=467.2.

Step 6: N-[(3-aminophenyl)sulfonimidoyl]-6-tert-butyl-2-(2,4,6-trimethylphenoxy)pyridine-3-carboxamide (Compound 19 and Compound 53)

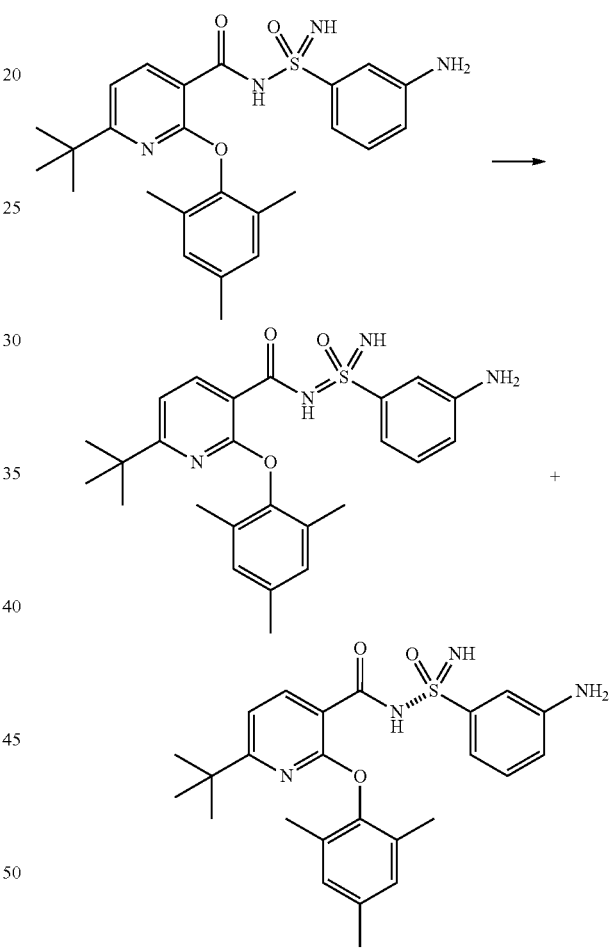

N-[(3-Aminophenyl)sulfonimidoyl]-6-tert-butyl-2-(2,4,6-trimethylphenoxy)pyridine-3-carboxamide (30 mg, 0.064 mmol) was taken up in methanol (1.8 mL) and CH$_2$C2 (0.4 mL). The solution was subjected to chiral SFC (30 μL injections; column: Chiralpak AS-H (250×10 mm), 5 μm; mobile phase: 25% methanol w/20 mM NH$_3$, 75% CO$_2$; flow: 10 mL/min) to give N-[(3-aminophenyl)sulfonimidoyl]-6-tert-butyl-2-(2,4,6-trimethylphenoxy)-pyridine-3-carboxamide [peak 1, enantiomer 1, 97.9% ee, $^1$H NMR (400 MHz, Chloroform-d) δ 8.27 (d, J=7.9 Hz, 1H), 7.49-7.36 (m, 2H), 7.22 (t, J=7.9 Hz, 1H), 6.92 (d, J=7.8 Hz, 1H), 6.87-6.75 (m, 3H), 3.89 (s, 2H), 2.29 (s, 3H), 2.02 (s, 6H), 1.06 (s, 9H)] and N-[(3-aminophenyl)sulfonimidoyl]-6-tertbutyl-2-(2,4,6-trimethylphenoxy)pyridine-3-carboxamide [peak 2, enantiomer 2, 96% ee, $^1$H NMR (400 MHz, Chloroform-d) δ 8.27 (d, J=7.9 Hz, 1H), 7.49-7.33 (m, 2H), 7.23 (t, J=7.9 Hz, 1H), 6.92 (d, J=7.9 Hz, 1H), 6.88-6.74 (m, 3H), 3.89 (s, 2H), 2.29 (s, 3H), 2.02 (s, 6H), 1.06 (s, 9H)].

The following compounds can be prepared using the procedures described herein:

N—[S-(3-aminophenyl)-N-methyl-sulfonimidoyl]-6-tert-butyl-2-(2,4,6-trimethylphenoxy)pyridine-3-carboxamide (Compound 568), N-(3-aminophenyl)sulfonyl-5-tert-butyl-2-[1-phenylethyl]pyrazole-3-carboxamide can be separated to give N-(3-aminophenyl)sulfonyl-5-tert-butyl-2-[(1S)-1-phenyl-ethyl]pyrazole-3-carboxamide (Compound 138) and N-(3-aminophenyl)sulfonyl-5-tert-butyl-2-[(1R)-1-phe-nylethyl]pyrazole-3-carboxamide (Compound 540) using Chiralcel OJ-H (250×10 mm), 5 μm column;

N-(3-aminophenyl)sulfonyl-2-[(2,4,6-trimethylphenyl)methyl]isoindoline-1-carboxamide can be separated to give (1S)—N-(3-aminophenyl)sulfonyl-2-[(2,4,6-trim-ethylphenyl)methyl]isoindoline-1-carboxamide (Compound 126) (Compound 126) and (1R)—N-(3-aminophe-nyl)sulfonyl-2-[(2,4,6-trimethylphenyl)methyl]isoindoline-1-carboxamide (Compound 310) using Chiralpak AD-H (250×10 mm), 5 μm column.

Preparation 44: N-[(6-Amino-3-fluoro-2-pyridyl)sulfonyl]-6-tert-butyl-2-(2,4,6-trimethylphenoxy)pyridine-3-carboxamide (Compound 226)

Step 1: 2-(benzylthio)-3,6-difluoropyridine

To a solution of 2,3,6-trifluoropyridine (532 mg, 4.00 mmol) and phenylmethanethiol (470 μL, 4.00 mmol) in THF (20 mL) was added NaH (60%, 176 mg, 4.40 mmol) in portions. After 1 h, the mixture was quenched with saturated aqueous ammonium chloride and extracted with ethyl acetate (3×). The combined extracts were washed with water, dried over sodium sulfate, and evaporated. The residue was purified by silica gel chromatography with 0-20% ethyl acetate in hexanes to give 2-(benzylthio)-3,6-difluo-ropyridine (0.63 g, 66%) as a colorless oil. ESI-MS m/z calc. 237.0, found 237.9 (M+1)$^+$; Retention time: 0.72 min (1 min run).

Step 2: 3,6-difluoropyridine-2-sulfonyl chloride

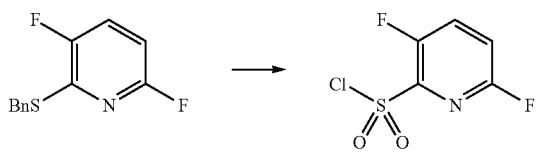

Chlorine was bubbled through a vigorously stirred solution of 2-(benzylthio)-3,6-difluoropyridine (0.27 g, 1.1 mmol) in chloroform and water for min, and the reaction mixture was stirred for 1 h. Chlorine was bubbled through the mixture for another 15 min, and the reaction mixture was stirred for 2 h. The reaction mixture was quenched with saturated aqueous sodium metabisulfite solution and extracted with dichloromethane (3×). The combined extracts were washed with water, dried over sodium sulfate, and evaporated to give crude 3,6-difluoropyridine-2-sulfonyl chloride (50% pure, 0.49 g) as a colorless oil. ESI-MS m/z calc. 213.0, found 213.8 (M+1)$^+$; Retention time: 0.47 min (1 min run).

Step 3: 3,6-difluoropyridine-2-sulfonamide

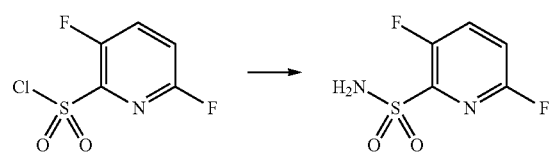 [SMILES: O=S(=O)(Cl)c1nc(F)ccc1F ; NS(=O)(=O)c1nc(F)ccc1F]

A solution of 5,6-difluoropyridine-2-sulfonyl chloride (0.35 g, 1.6 mmol) in dioxane (4 mL) was cooled in an ice bath before ammonia (6.6 mL of 0.5 M in dioxane, 3.3 mmol) was added. The reaction was stirred for 3 h and the solvent was evaporated. The residue was purified by silica gel chromatography with 0-50% ethyl acetate in hexanes to give 3,6-difluoropyridine-2-sulfonamide (72 mg, 23%) as a colorless solid. ESI-MS m/z calc. 194.0, found 194.8 (M+1)$^+$; Retention time: 0.15 min (1 min run).

Step 4: 6-tert-butyl-N-[(3,6-difluoro-2-pyridyl)sulfonyl]-2-(2,4,6-trimethylphenoxy)pyridine-3-carboxamide

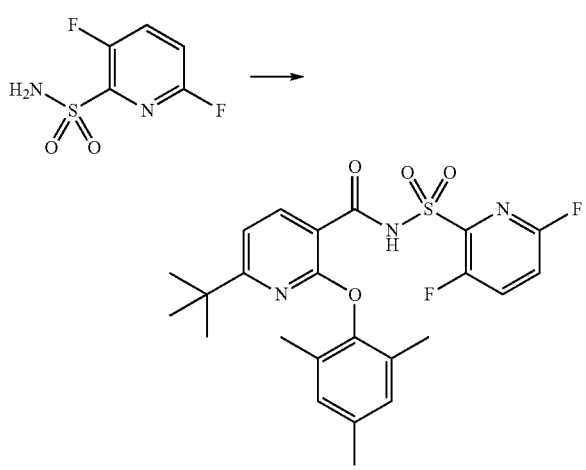

A solution of 6-tert-butyl-2-(2,4,6-trimethylphenoxy)pyridine-3-carboxylic acid (107 mg, 0.340 mmol), 3,6-difluoropyridine-2-sulfonamide (66 mg, 0.34 mmol), N-[(di-methylamino)-1H-1,2,3-triazolo-[4,5-b]pyridin-1-ylmethylene]-N-methylmethanaminium hexafluorophosphate N-oxide (194 mg, 0.510 mmol) and sodium carbonate (72 mg, 0.68 mmol) in N,N-dimethylfor-mamide (2 mL) was stirred at room temperature for 18 h. The reaction was diluted with water and extracted with ethyl acetate (3×). The combined extracts were washed with water, dried over sodium sulfate, and evaporated. The residue was purified by silica gel chromatography with 0-5% methanol in dichloromethane to give 6-(tert-butyl)-N-((3,6-difluoropyridin-2-yl)sulfonyl)-2-(mesityloxy)nicotinamide (33 mg, 18%) as a colorless solid. ESI-MS m/z calc. 489.2, found-490.2 (M+1)⁺; Retention time: 0.85 min (1 min run).

Step 5: N-[(6-amino-3-fluoro-2-pyridyl)sulfonyl]-6-tert-butyl-2-(2,4,6-trimethylphenoxy)pyridine-3-carboxamide

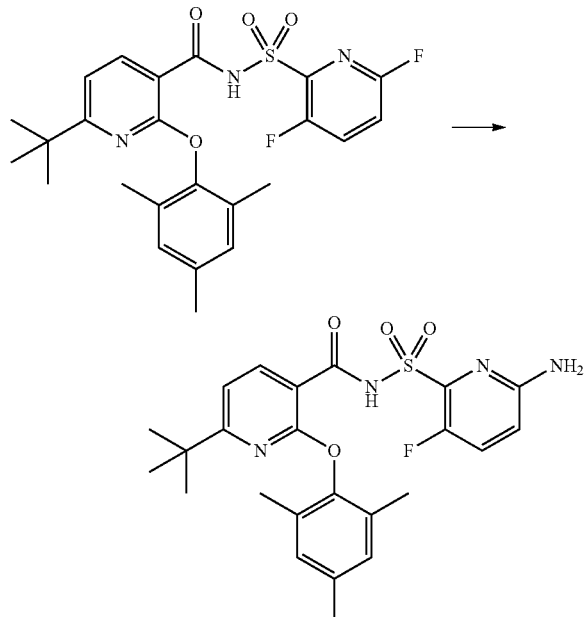

A mixture of 6-tert-butyl-N-[(5,6-difluoro-2-pyridyl)sulfonyl]-2-(2,4,6-trimethylphenoxy)pyridine-3-carboxamide (15 mg, 0.028 mmol) and ammonium hydroxide (1.0 mL of 30% w/v, 8.6 mmol) was heated in a sealed vessel in a microwave reactor at 130° C. for 30 min and 150° C. for 60 min. The solvent was evaporated and the residue was subjected to preparatory-HPLC (30%-99% acetonitrile/water (5 mM HCl)) to give N-[(6-amino-3-fluoro-2-pyridyl)sulfonyl]-6-tert-butyl-2-(2,4,6-trimethylphenoxy)pyridine-3-carboxamide (0.7 mg, 5%). ESI-MS m/z calc. 486.2, found 487.3 (M+1)⁺; Retention time: 2.15 min (3 min run).

Preparation 45: (2S,4R)—N-[(6-Amino-2-pyridyl)sulfonyl]-4-phenyl-1-[(2,4,6-trimethylphenyl)methyl]pyrrolidine-2-carboxamide (Compound 236)

Step 1: (2S,4R)-4-phenylpyrrolidine-2-carboxylic acid trifluoroacetic acid salt

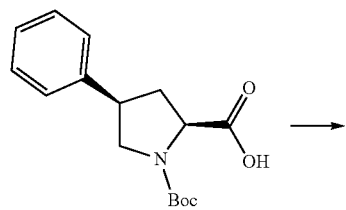

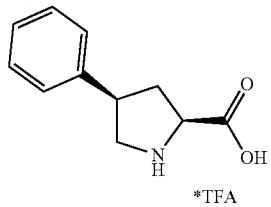

(2S,4R)-1-(Boc)-4-Phenylpyrrolidine-2-carboxylic acid (1.01 g, 3.47 mmol) was dissolved in trifluoroacetic acid (20 ml) and was stirred for 1 hour at room temperature. The reaction mixture was concentrated under reduced pressure and the resulting residue was left under high vacuum for 18 h. The residue was triturated in a minimal amount of diethyl ether and placed in an ultrasound bath for 1 hour, filtered and then dried under high vacuum to provide (2S,4R)-4-phenylpyrrolidine-2-carboxylic acid trifluoroacetic acid salt (999 mg, 99%) as solid. [M+H]⁺=192.2. ¹H NMR (300 MHz, CDCl₃) δ 1.94-2.11 (m, 1H), 2.61-2.75 (m, 1H), 3.09-3.22 (m, 1H), 3.42-3.59 (m, 1H), 3.59-3.73 (m, 1H), 4.35-4.48 (m, 1H), 7.15-7.40 (m, 5H), 8.52-10.23 (br. s, 2H).

Step 2: (2S,4R)-4-phenyl-1-[(2,4,6-trimethylphenyl)methyl]pyrrolidine-2-carboxylic acid

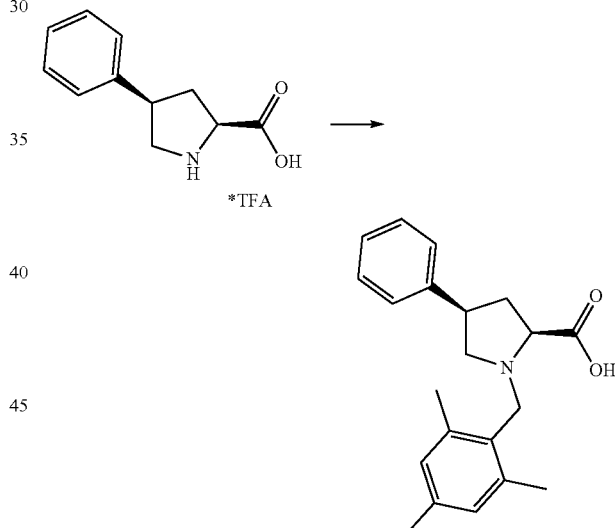

(2S-4R)-4-Phenylpyrrolidine-2-carboxylic acid trifluoroacetic acid salts (999 mg, 3.47 mmol) and potassium hydroxide (1.17 g, 20.8 mmol) were dissolved in isopropanol (25 mL) and heated at 40° C. A solution of 2-(bromomethyl)-1,3,5-trimethylbenzene (849 mg, 3.99 mmol) in isopropanol (20 mL) was added over 60 min via a syringe. The reaction was stirred for additional 2 h at this temperature. The reaction mixture was treated with concentrated HCl until the pH was between 3 and 4. The resulting solid was filtered off and the filtrate was concentrated under reduced pressure. The resultant solid was dissolved in dichloromethane and was purified on silica gel (0-10% methanol in ethyl acetate). Upon dilution of the residue with dichloromethane, the silica was filtered off and the filtrate was concentrated under reduced pressure to provide (2S-4R)-4-phenyl-1-[(2,4,6-trimethylphenyl)methyl]pyrrolidine-2-carboxylic acid (1.1 g, 98%) as a solid. [M+H]⁺=324.2. ¹H NMR (300 MHz, CDCl₃) δ 2.22 (s, 3H), 2.27-2.34 (m, 1H), 2.38 (s, 6H), 2.59-2.94 (m, 1H), 2.96-3.30 (m, 1H), 3.36 (t, J=11.2 Hz, 1H), 3.47-3.80 (m, 1H), 4.05 (m, 1H), 4.20 (d, J=13.4 Hz, 1H), 4.35 (d, J=13.4 Hz, 1H), 6.83 (s, 2H), 7.05-7.33 (m, 5H).

Step 3: (2S,4R)—N-[(6-fluoro-2-pyridyl)sulfonyl]-4-phenyl-1-[(2,4,6-trimethylphenyl)methyl]pyrrolidine-2-carboxamide

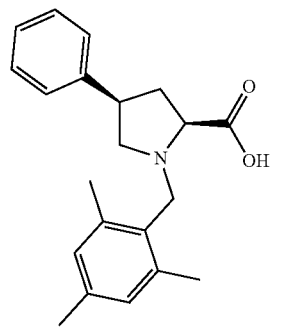

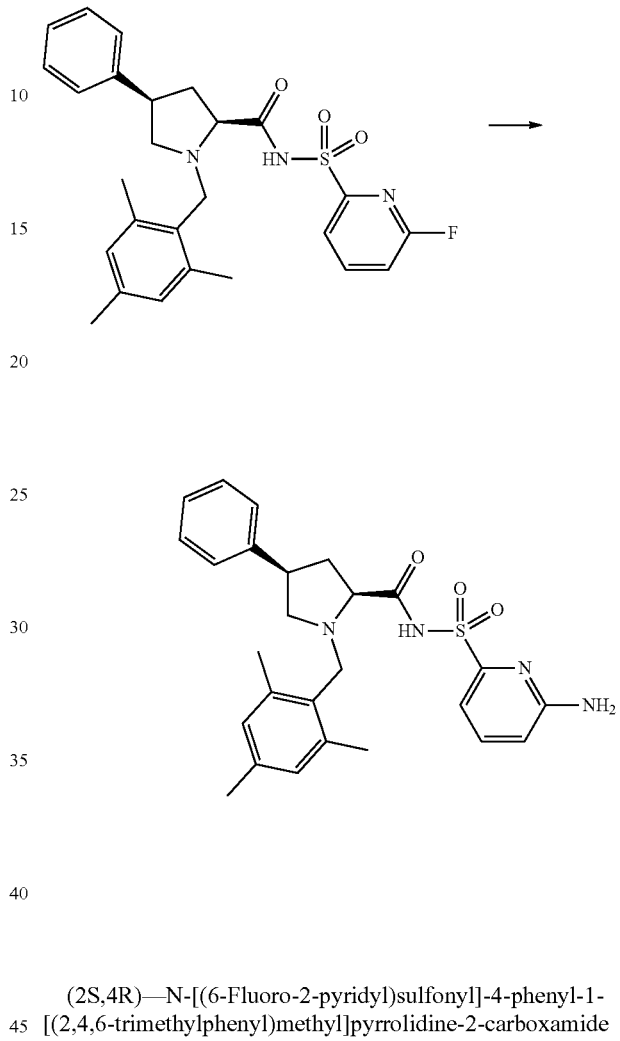

(2S,4R)-4-Phenyl-1-[(2,4,6-trimethylphenyl)methyl]pyrrolidine-2-carboxylic acid (75 mg, 0.23 mmol), 6-fluoropyridine-2-sulfonamide (192 mg, 1.09 mmol), N-[(dimethylamino)-1H-1,2,3-triazolo-[4,5-b]pyridin-1-ylmethylene]-N-methylmethanaminium hexafluorophosphate N-oxide (497 mg, 1.31 mmol), and ethyldiisopropylamine (380 µL, 2.18 mmol) were combined in N,N-dimethylformamide (1.440 mL) and heated at 60° C. for 16 h. The reaction mixture was diluted with water (1 mL) and was extracted with ethyl acetate (2×5 mL). The organic layers were dried over sodium sulfate, filtered and concentrated. The residue was subjected to preparatory-HPLC utilizing a gradient of 30-90% acetonitrile in 5 mM aq HCl to give (2S,4R)—N-[(6-fluoro-2-pyridyl)sulfonyl]-4-phenyl-1-[(2,4,6-trimethylphenyl)methyl]pyrrolidine-2-carboxamide. ¹H NMR (400 MHz, DMSO) δ 9.18 (s, 1H), 8.16 (d, J=7.8 Hz, 1H), 7.85 (d, J=9.1 Hz, 1H), 7.30 (s, 7H), 6.88 (s, 2H), 4.40 (s, 2H), 4.24 (s, 1H), 3.81 (s, 1H), 3.33-3.21 (m, 2H), 2.76 (s, 1H), 2.37 (s, 6H), 2.21 (s, 3H), 2.00 (s, 1H).

Step 4: (2S,4R)—N-[(6-amino-2-pyridyl)sulfonyl]-4-phenyl-1-[(2,4,6-trimethylphenyl)methyl]pyrrolidine-2-carboxamide (2S,4R)—N-[(6-Fluoro-2-pyridyl)sulfonyl]-4-phenyl-1-[(2,4,6-trimethylphenyl)methyl]pyrrolidine-2-carboxamide (from step 3) was suspended in NH₄OH (2 mL of 30% w/v, 17 mmol). The mixture was heated in a microwave at 150° C. The reaction mixture was concentrated, redissolved in DMSO and subjected to preparatory-HPLC utilizing a gradient of 1-60% acetonitrile in 5 mM aq HCl to give (2S,4R)—N-[(6-amino-2-pyridyl)sulfonyl]-4-phenyl-1-[(2,4,6-trimethylphenyl)methyl]pyrrolidine-2-carboxamide (Compound 236) (7.5 mg, 7% over two steps). ¹H NMR (400 MHz, MeOD) δ 7.84 (s, 1H), 7.33 (s, 7H), 6.99 (d, J=8.7 Hz, 1H), 6.90 (s, 2H), 4.60 (d, J=35.7 Hz, 2H), 4.41 (s, 1H), 3.98 (s, 1H), 3.76 (s, 1H), 3.67-3.55 (m, 1H), 2.90 (dt, J=12.8, 6.3 Hz, 1H), 2.41 (d, J=14.1 Hz, 7H), 2.24 (s, 4H). ESI-MS m/z calc. 478.2, found 479.0 (M+1)⁺; Retention time: 1.41 min (3 min run).

The following compounds can be synthesized using the procedures described herein: (2R,4S)—N-[(6-amino-2-pyridyl)sulfonyl]-4-phenyl-1-[(2,4,6-trimethylphenyl)methyl]pyrrolidine-2-carboxamide (Compound 467) and (2S,4S)—N-[(6-amino-2-pyridyl)sulfonyl]-4-phenyl-1-[(2,4,6-trimethylphenyl)methyl]pyrrolidine-2-carboxamide (Compound 870)

Preparation 46: N-(4-Aminothiazol-2-yl)sulfonyl-6-tert-butyl-2-(2,4,6-trimethylphenoxy)pyridine-3-carboxamide (Compound 265)

Step 1: tert-butyl thiazol-4-ylcarbamate

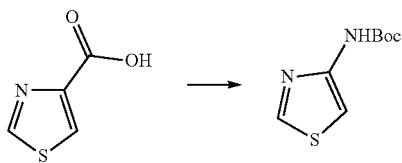 [SMILES: O=C(O)c1cscn1 ; CC(C)(C)OC(=O)Nc1cscn1]

A mixture of thiazole-4-carboxylic acid (8.16 g, 63.2 mmol) and triethylamine (9.7 mL, 70 mmol) in tert-butanol (320 mL) was treated with diphenyl phosphoryl azide (15 mL, 70 mmol) and heated gradually in an oil bath to 100° C. and stirred for 17 h. Once cooled, the crude reaction mixture was concentrated under reduced pressure to remove most of the volatiles. The residue was transferred to a 1.0-L separatory funnel with ethyl acetate (300 mL) and the organic layer was washed with water (2×200 mL) and brine (2×100 mL). The organic layer was then dried over anhydrous sodium sulfate, filtered and concentrated under reduced pressure. The residue was purified silica gel chromatography, eluting from 0% to 50% ethyl acetate in heptanes. The resultant gummy solid was triturated with heptanes, filtered, washed with heptanes and dried under high vacuum to afford tert-butyl thiazol-4-ylcarbamate (3.42 g, 27%) as a white solid. $^1$H NMR (300 MHz, CDCl$_3$) δ 1.54 (s, 9H), 7.30 (br. s, 1H), 8.33 (br. s, 1H), 8.58 (d, J=2.3 Hz, 1H). [M-C$_4$H$_8$+H]$^+$=145.1.

Step 2: tert-butyl N-(2-sulfamoyl-1,3-thiazol-4-yl)carbamate

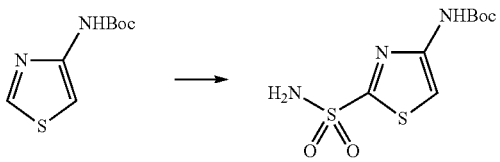 [SMILES: CC(C)(C)OC(=O)Nc1cscn1 ; CC(C)(C)OC(=O)Nc1csc(S(N)(=O)=O)n1]

A solution of tert-butyl thiazol-4-ylcarbamate (1.50 g, 7.49 mmol) in methyl tert-butyl ether (35 mL) was cooled in an ice bath and treated slowly with iso-propylmagnesium chloride (11 mL of a 2.0 M solution in THF, 22 mmol). A voluminous white solid appeared. After 20 minutes in the ice bath, sulfur dioxide was gently bubbled into the reaction mixture for 5 minutes then the reaction mixture was stirred at room temperature for 1 h. The crude reaction mixture was concentrated under reduced pressure to remove most of the volatiles and the solid obtained was suspended in water (80 mL) and cooled in an ice bath. Sodium acetate (3.40 g, 41.5 mmol) and hydroxylamine-O-sulfonic acid (3.39 g, 30.0 mmol) were successively added. The ice-bath was removed and the reaction was left to stir at room temperature for 45 h. The reaction mixture was transferred to a separatory funnel and the aqueous layer was extracted with ethyl acetate (2×50 mL). The combined organic layers were washed with 5% aqueous sodium bicarbonate (30 mL), brine (30 mL), dried over anhydrous sodium sulfate, filtered and concentrated under reduced pressure. The residue was purified by silica gel chromatography, eluting from 0% to 75% ethyl acetate in heptanes, to provide 1.2 g of a solid that was contaminated with iso-propylsulfonamide. The solid was dissolved in methanol (3 mL) and water (2 mL) was added dropwise with stirring. The precipitate was filtered, washed with water and dried under high vacuum to afford tert-butyl N-(2-sulfamoyl-1,3-thiazol-4-yl)carbamate (0.90 g, 43%) as a white solid. $^1$H NMR (300 MHz, DMSO-d$_6$) δ 1.46 (s, 9H), 7.56 (s, 2H), 9.12 (s, 1H), 9.24 (s, 1H). [M-C$_4$H$_8$+H]$^+$=224.0.

Step 3: N-[2-[[6-tert-Butyl-2-(2,4,6-trimethylphenoxy)pyridine-3-carbonyl]sulfamoyl]thiazol-4-yl]carbamate

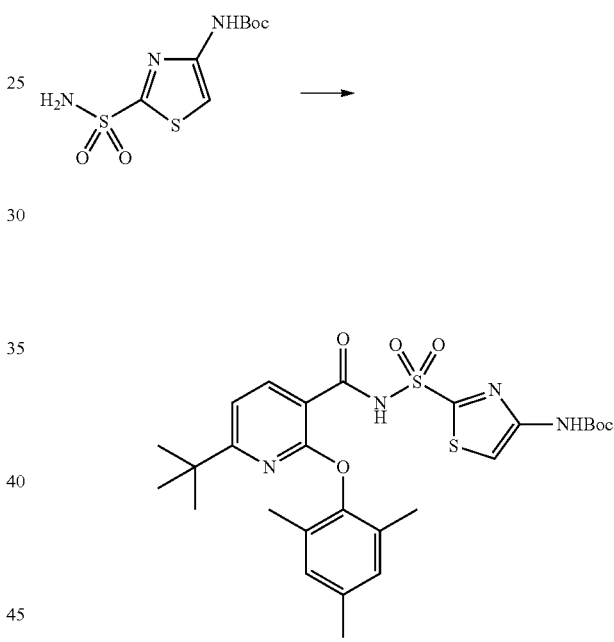

K$_2$CO$_3$ (45 mg, 0.35 mmol) was added to a mixture of 6-tert-butyl-2-(2,4,6-trimethylphenoxy)pyridine-3-carboxylic acid (44 mg, 0.14 mmol), tert-butyl N-(2-sulfamoylthiazol-4-yl)carbamate (39 mg, 0.14 mmol), N-[(dimethylamino)-1H-1,2,3-triazolo-[4,5-b]pyridin-1-ylmethylene]-N-methylmethanaminium hexafluorophosphate N-oxide (64 mg, 0.17 mmol) and N,N-dimethylformamide (1 mL) at room temperature. The mixture was stirred at 60° C. for 3 h before it was cooled to room temperature. The mixture was partitioned between ethyl acetate and 1N HCl. The layers were separated and the aqueous layer was extracted with ethyl acetate (2×). The combined organics were washed with brine, dried over magnesium sulfate, filtered and concentrated. The residue was subjected to silica gel column chromatography (0-50% ethyl acetate/hexanes), then subjected to preparatory-HPLC(10-99% acetonitrile/water with 0.05 mM HCl) to give tert-butyl N-[2-[[6-tert-butyl-2-(2,4,6-trimethylphenoxy)pyridine-3-carbonyl]sulfamoyl]thiazol-4-yl]carbamate as a white solid. ESI-MS m/z calc. 574.2, found 575.4 (M+1)$^+$; Retention time: 2.48 min (3 min run).

2035

Step 4: N-(4-Aminothiazol-2-yl)sulfonyl-6-tert-butyl-2-(2,4,6-trimethylphenoxy)pyridine-3-carboxamide

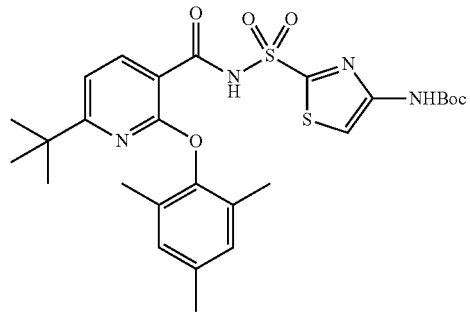

Trifluoroacetic acid (11 µL, 0.14 mmol) was added to a mixture of tert-butyl N-[2-[[6-tert-butyl-2-(2,4,6-trimethylphenoxy)pyridine-3-carbonyl]sulfamoyl]thiazol-4-yl]carbamate (from step 3) and $CH_2Cl_2$ (5 mL) at room temperature. The mixture was allowed to stir for 1H before it was concentrated under reduced pressure. The residue was subjected to preparatory-HPLC(10-99% acetonitrile/water with 0.05 mM HCl) to give N-(4-aminothiazol-2-yl)sulfonyl-6-tert-butyl-2-(2,4,6-trimethylphenoxy)pyridine-3-carboxamide (Compound 265). ESI-MS m/z calc. 474.1, found 475.5 $(M+1)^+$; Retention time: 2.11 min (3 min run). $^1H$ NMR (400 MHz, DMSO-$d_6$) δ 11.96 (s, 1H), 9.07 (s, 1H), 8.00 (d, J=7.8 Hz, 1H), 7.13 (d, J=7.8 Hz, 1H), 6.91 (s, 2H), 6.81 (s, 2H), 2.25 (s, 3H), 1.96 (s, 6H), 1.04 (s, 9H).

The following compounds can be prepared using the procedures described herein: N-(4-aminothiazol-2-yl)sulfonyl-6-(3-fluoro-5-isobutoxy-phenyl)-2-(2,2,4-trimethylpyrrolidin-1-yl)pyridine-3-carboxamide (Compound 842) and N-(4-aminothiazol-2-yl)sulfonyl-2-(4,4-dimethyl-1-piperidyl)-6-(3-fluoro-5-isobutoxy-phenyl)pyridine-3-carboxamide (Compound 1168)

2036

Preparation 47: N-[(6-Amino-2-pyridyl)sulfonyl]-6-(tert-butylamino)-2-(2,4,6-trimethylphenoxy)pyridine-3-carboxamide (Compound 273)

Step 1: methyl 6-(tert-butylamino)-2-(mesityloxy)pyridine-3-carboxylate

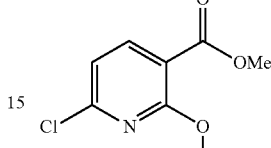

A mixture of methyl 6-chloro-2-(mesityloxy)pyridine-3-carboxylate (170 mg, 0.58 mmol) and t-butylamine (4.0 mL, 38 mmol) in 500 mL dimethylacetamide was heated in a microwave at 150° C. for 4 h. The crude mixture was purified by silica gel column chromatography eluting with a gradient of 0-40% ethyl acetate/hexanes to afford methyl 6-(tert-butylamino)-2-(mesityloxy)pyridine-3-carboxylate (76 mg, 38% yield) as an orange solid. LC-MS: $(M+H)^+$ =342.5.

Step 2: 6-(tert-butylamino)-2-(mesityloxy)pyridine-3-carboxylic acid

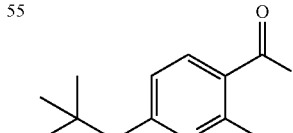

-continued

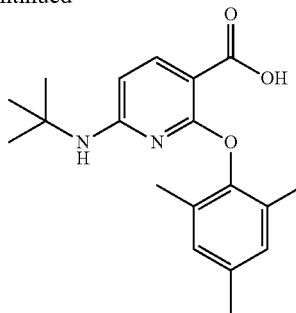

A mixture of methyl 6-(tert-butylamino)-2-(mesityloxy) pyridine-3-carboxylate (76 mg, 0.22 mmol) and sodium hydroxide (14 mg, 0.34 mmol) in methanol (1.0 mL), THF (1.0 mL), and water (0.50 mL) was heated at 60° C. for 7 h. A few drops of concentrated HCl were added, solid formed, everything was rotary evaporated, and dried under vacuum to give crude 6-(tert-butylamino)-2-(mesityloxy)pyridine-3-carboxylic acid (98 mg) as a white solid. LC-MS: (M+H)$^+$=329.3.

Step 3: 6-(tert-butylamino)-2-(mesityloxy)-N-((6-nitropyridin-2-yl)sulfonyl)nicotinamide

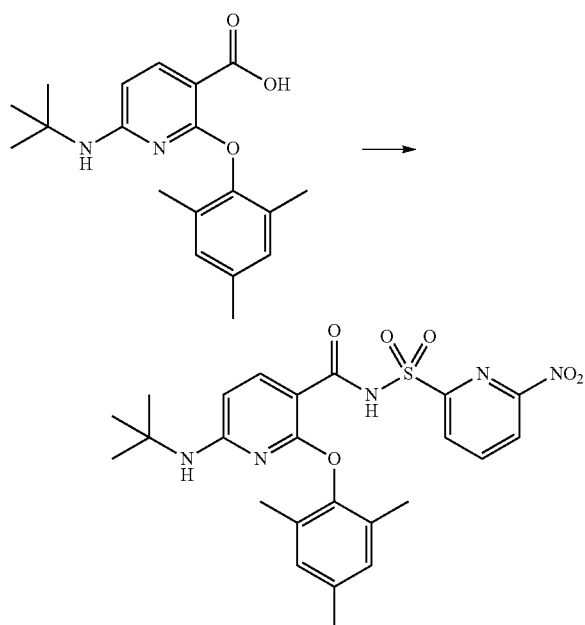

A mixture of crude 6-(tert-butylamino)-2-(mesityloxy) pyridine-3-carboxylic acid (0.22 mmol), 6-nitropyridine-2-sulfonamide (58 mg, 0.29 mmol), N-[(dimethylamino)-1H-1,2,3-triazolo-[4,5-b]pyridin-1-ylmethylene]-N-methylmethanaminium hexafluorophosphate N-oxide (0.12 g, 0.33 mmol), ethyldiisopropylamine (0.16 mL, 0.92 mmol) and N,N-dimethylformamide (1 mL) was stirred in a capped vial at 70° C. for 6 h and then at room temperature for 18 h. LC-MS at that point showed mostly the activated acid. An additional 70 mg of 6-nitropyridine-2-sulfonamide and 0.080 mL of ethyldiisopropylamine were added. The mixture was stirred at 70° C. for 4 h and the crude was purified twice by silica gel column chromatography eluting with a gradient of 0-20% methanol/dichloromethane to give 6-(tert-butylamino)-2-(mesityloxy)-N-((6-nitropyridin-2-yl)sulfonyl)nicotinamide (34 mg, 30% yield) as a light yellow solid. LC-MS: (M+H)$^+$=514.5.

Step 4: N-[(6-amino-2-pyridyl)sulfonyl]-6-(tert-butylamino)-2-(2,4,6-trimethylphenoxy)pyridine-3-carboxamide

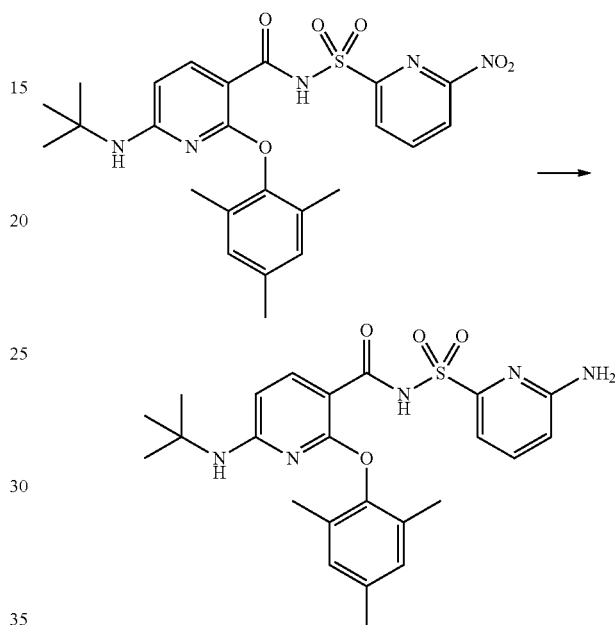

A mixture of 6-(tert-butylamino)-2-(mesityloxy)-N-((6-nitropyridin-2-yl)sulfonyl)nicotinamide (34 mg, 0.064 mmol) and iron metal (48 mg, 0.86 mmol) in THF (0.7 mL), EtOH (0.35 mL), conc. HCl (0.06 mL) and water (0.06 mL) was heated at 60° C. for 50 min. The mixture was filtered hot and was washed with methanol. The filtrate was rotary evaporated to give 120 mg of crude material which was purified by reverse phase HPLC to give N-[(6-amino-2-pyridyl)sulfonyl]-6-(tert-butylamino)-2-(2,4,6-trimethylphenoxy)pyridine-3-carboxamide (Compound 273) (7.2 mg, 23%). LC-MS: (M+H)$^+$=484.5.

Preparation 48:
6-(tert-butoxy)-2-(mesityloxy)nicotinic acid

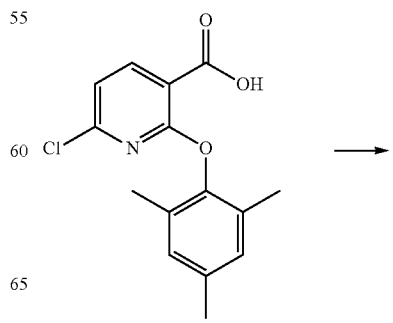

-continued

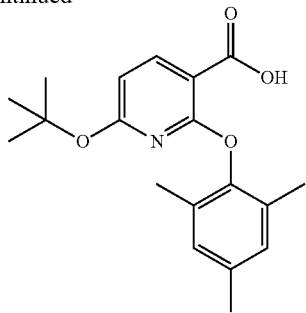

To a solution of t-butanol (0.70 mL, 7.3 mmol, 11 eq) in 1.0 mL of N,N-dimethylformamide was added portion-wise 60% NaH (320 mg, 8.0 mmol, 12 eq). After bubbling stopped, about 10 min, 6-chloro-2-(mesityloxy)pyridine-3-carboxylic acid 7 (0.20 g, 0.69 mmol, 1.0 eq) was added to the reaction mixture. The mixture was heated in a capped vial at 100° C. for 22 hr. After cooling to room temperature, a couple of drops of concentrated hydrochloric acid was added and the reaction mixture was evaporated to dryness. The crude material was purified by column chromatography using 25 g of silica gel and eluting with a gradient of 0-30% methanol in dichlormethane over 15 minutes. The product-containing fractions were combined and concentrated to afford 6-tert-butoxy-2-(mesityloxy)pyridine-3-carboxylic acid (109 mg, 48% yield) as a light yellow solid. LC-MS: $(M+H)^+=330.1$.

The following compound can be synthesized using the procedures described herein:

N-[(6-amino-2-pyridyl)sulfonyl]-6-(isopropylamino)-2-(2,4,6-trimethylphenoxy)pyridine-3-carboxamide (Compound 650), N-[(6-amino-2-pyridyl)sulfonyl]-6-(2-methylpyrrolidin-1-yl)-2-(2,4,6-trimethylphenoxy)pyridine-3-carboxamide (Compound 1553), N-[(6-amino-2-pyridyl)sulfonyl]-6-pyrrolidin-1-yl-2-(2,4,6-trimethylphenoxy)pyridine-3-carboxamide (Compound 746), N-[(6-amino-2-pyridyl)sulfonyl]-6-(1-piperidyl)-2-(2,4,6-trimethylphenoxy)pyridine-3-carboxamide (Compound 785), N-[(6-amino-2-pyridyl)sulfonyl]-6-morpholino-2-(2,4,6-trimethylphenoxy)pyridine-3-carboxamide (Compound 966), N-[(6-amino-2-pyridyl)sulfonyl]-6-(methylamino)-2-(2,4,6-trimethylphenoxy)pyridine-3-carboxamide (Compound 983), N-[(6-amino-2-pyridyl)sulfonyl]-6-(ethylamino)-2-(2,4,6-trimethylphenoxy)pyridine-3-carboxamide (Compound 1128), N-[(6-amino-2-pyridyl)sulfonyl]-6-(dimethylamino)-2-(2,4,6-trimethylphenoxy)pyridine-3-carboxamide (Compound 1306), N-[(6-amino-2-pyridyl)sulfonyl]-6-ethoxy-2-(2,4,6-trimethylphenoxy)pyridine-3-carboxamide (Compound 637), N-[(6-amino-2-pyridyl)sulfonyl]-6-methoxy-2-(2,4,6-trimethylphenoxy)pyridine-3-carboxamide (Compound 806), N-[(6-amino-2-pyridyl)sulfonyl]-8,8-dimethyl-2-(2,4,6-trimethylphenoxy)-5,7-dihydropyrano[4,3-b]pyridine-3-carboxamide (Compound 714), N-[(6-amino-2-pyridyl)sulfonyl]-6-[isobutyl(methyl)amino]-5-methyl-2-(2,4,6-trimethylphenoxy)pyridine-3-carboxamide (Compound 1416), N-[(6-amino-2-pyridyl)sulfonyl]-6-[(2R,5S)-2,5-dimethylpyrrolidin-1-yl]-2-(2,4,6-trimethylphenoxy)pyridine-3-carboxamide (Compound 1494), N-[(6-amino-2-pyridyl)sulfonyl]-5-methyl-6-(2-methylpyrrolidin-1-yl)-2-(2,4,6-trimethylphenoxy)pyridine-3-carboxamide (Compound 1516), N-[(6-amino-2-pyridyl)sulfonyl]-5-fluoro-2,6-bis[(4S)-2,2,4-trimethylpyrrolidin-1-yl]pyridine-3-carboxamide (Compound 1673), N-[(6-amino-2-pyridyl)sulfonyl]-6-isopropoxy-2-[(4S)-2,2,4-trimethylpyrrolidin-1-yl]pyridine-3-carboxamide (Compound 1573), N-[(6-amino-2-pyridyl)sulfonyl]-6-[(2R,5S)-2,5-dimethylpyrrolidin-1-yl]-5-methyl-2-(2,4,6-trimethylphenoxy)pyridine-3-carboxamide (Compound 1589), N-[(6-amino-2-pyridyl)sulfonyl]-6-isopropoxy-2-(2,4,6-trimethylphenoxy)pyridine-3-carboxamide (Compound 968), and N-[(6-amino-2-pyridyl)sulfonyl]-6-tert-butoxy-2-(2,4,6-trimethylphenoxy)pyridine-3-carboxamide (Compound 1070).

Preparation 49: N-[(6-amino-2-pyridyl)sulfonyl]-6-tert-butyl-2-cyclopentyl-pyridine-3-carboxamide (Compound 1219)

Step 1: 6-(tert-Butyl)-2-(cyclohex-1-en-1-yl)-N-((6-fluoropyridin-2-yl)sulfonyl)nicotinamide

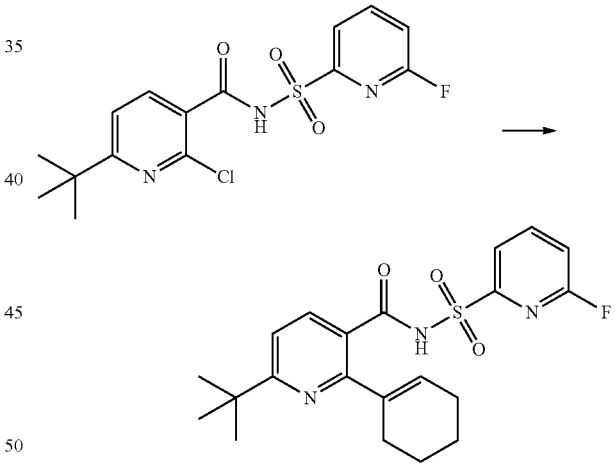

6-tert-butyl-2-chloro-N-[(6-fluoro-2-pyridyl)sulfonyl]pyridine-3-carboxamide (75 mg, 0.20 mmol), 1-cyclohexenylboronic acid (25.41 mg, 0.2017 mmol), sodium carbonate (201.7 µL of 2 M, 0.4034 mmol), dichloro[1,1'-bis(diphenylphosphino)ferrocene]palladium (II) dichloromethane adduct (7.376 mg, 0.01008 mmol) in dioxane (900.0 µL) were added to a microwave reactor vial. The vial was purged with nitrogen, capped and heated to 120° C. for 30 minutes in a microwave reactor. The reaction mixture was diluted with water and extracted with ethyl acetate (2×10 mL). The organic layers were dried over sodium sulfate, concentrated, and purified by HPLC utilizing a gradient of 0-70% acetonitrile in 5 mM aq HCl to give the product (19.7 mg, 23%) ESI-MS m/z calc. 417.5, found 418.4 $(M+1)^+$; Retention time: 0.64 min (1 min run).

2041

Step 2: 6-(tert-butyl)-2-cyclohexyl-N-((6-fluoropyridin-2-yl)sulfonyl)nicotinamide

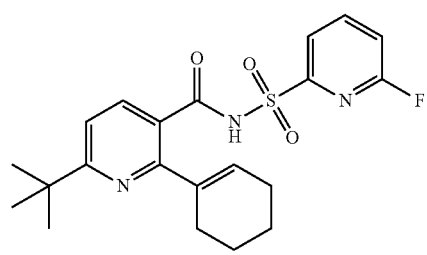

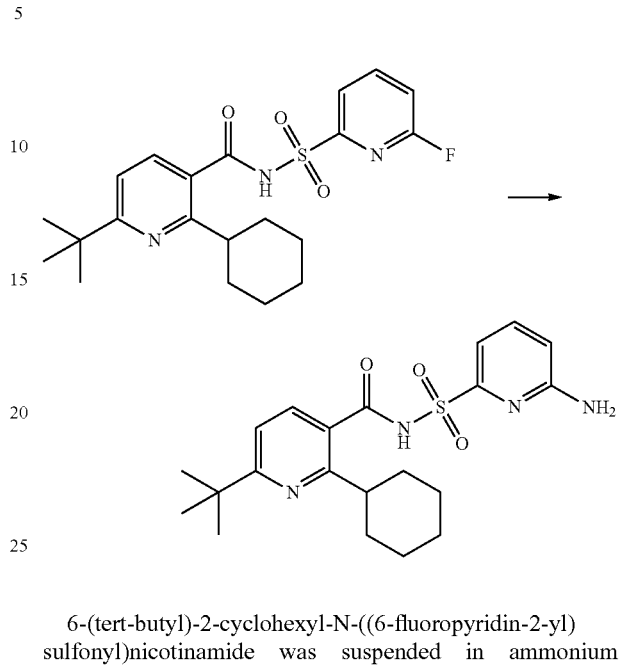

6-(tert-Butyl)-2-(cyclohex-1-en-1-yl)-N-((6-fluoropyridin-2-yl)sulfonyl)nicotinamide (19.7 mg, 0.047 mmol) was dissolved in methanol (10 mL) and palladium on carbon (12.64 mg, 0.01188 mmol) was added. The mixture was stirred under a hydrogen balloon at room temperature for 16 hours. The crude material was filtered, concentrated, and purified by HPLC utilizing a gradient of 20-80% acetonitrile in 5 mM aq HCl to give 6-(tert-butyl)-2-cyclohexyl-N-((6-fluoropyridin-2-yl)sulfonyl)nicotinamide.

The following compound can be synthesized using the procedures described herein:

N-(4-aminophenyl)sulfonyl-6-tert-butyl-2-cyclopentyl-pyridine-3-carboxamide (Compound 1003), N-[(6-amino-2-pyridyl)sulfonyl]-6-(3-fluoro-5-isobutoxyphenyl)-2-(3,3,5,5-tetramethylcyclopenten-1-yl)pyridine-3-carboxamide (Compound 1502), N-[(6-amino-2-pyridyl)sulfonyl]-6-(3-fluoro-5-isobutoxyphenyl)-2-[4-(trifluoromethyl)cyclohexen-1-yl]pyridine-3-carboxamide (Compound 1667), N-[(6-amino-2-pyridyl)sulfonyl]-6-(3-fluoro-5-isobutoxyphenyl)-2-(2,2,6,6-tetramethyl-3H-pyran-4-yl)pyridine-3-carboxamide (Compound 1368), N-[(6-amino-2-pyridyl)sulfonyl]-2-(4,4-dimethylcyclohexen-1-yl)-6-(3-fluoro-5-isobutoxy-phenyl)pyridine-3-carboxamide (Compound 1493), and N-[(6-amino-2-pyridyl)sulfonyl]-6-(3-fluoro-5-isobutoxyphenyl)-2-(2,2,5,5-tetramethyl-3-furyl)pyridine-3-carboxamide (Compound 1531).

2042

Step 3: N-[(6-amino-2-pyridyl)sulfonyl]-6-tert-butyl-2-cyclohexyl-pyridine-3-carboxamide (Compound 411)

6-(tert-butyl)-2-cyclohexyl-N-((6-fluoropyridin-2-yl)sulfonyl)nicotinamide was suspended in ammonium hydroxide (1 mL of 28% w/v, 8.56 mmol). The mixture was stirred in a microwave reactor for 0.5 h at 150° C. The reaction mixture was concentrated, redissolved in DMSO and purified by HPLC utilizing a gradient of 10-65% acetonitrile in 5 mM aq HCl to give N-[(6-amino-2-pyridyl)sulfonyl]-6-tert-butyl-2-(cyclohexen-1-yl)pyridine-3-carboxamide $^1$H NMR (400 MHz, MeOD) δ 8.56 (d, J=8.4 Hz, 1H), 7.98 (d, J=8.4 Hz, 1H), 7.87 (s, 1H), 7.43 (d, J=7.2 Hz, 1H), 7.03 (d, J=8.7 Hz, 1H), 6.08 (s, 1H), 2.31 (s, 2H), 2.20 (s, 2H), 1.69 (d, J=17.3 Hz, 4H), 1.53 (s, 9H). ESI-MS m/z calc. 414.17255, found 415.0 (M+1)$^+$; Retention time: 1.48 minutes.

The following compound can be synthesized using the procedures described herein: N-[(6-amino-2-pyridyl)sulfonyl]-6-tert-butyl-2-cyclopentyl-pyridine-3-carboxamide (Compound 1219).

Preparation 50: 6-tert-butyl-N-[(1-methyl-2-oxo-3-pyridyl)sulfonyl]-2-(2,4,6-trimethylphenoxy)pyridine-3-carboxamide (Compound 667)

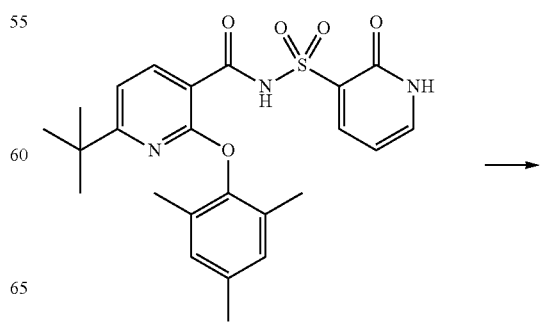

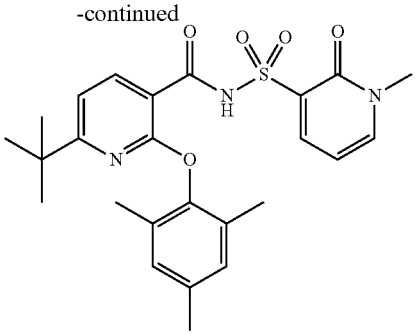

6-tert-butyl-N-[(2-oxo-1H-pyridin-3-yl)sulfonyl]-2-(2,4,6-trimethylphenoxy)pyridine-3-carboxamide (28 mg, 0.060 mmol) was dissolved in N,N-dimethylformamide with potassium carbonate (24.72 mg, 0.1789 mmol) and a solution of iodomethane (8.464 mg, 3.712 μL, 0.05963 mmol) was added dropwise. The solution was stirred for 4 h at room temperature. The reaction mixture was filtered and purified by LC/MS utilizing a gradient of 10-99% acetonitrile in 5 mM aq HCl to yield 6-tert-butyl-N-[(1-methyl-2-oxo-3-pyridyl)sulfonyl]-2-(2,4,6-trimethylphenoxy)pyridine-3-carboxamide (Compound 667) (2 mg, 0.004 mmol, 7%) ESI-MS m/z calc. 483.1828, found 484.3 (M+1)$^+$; Retention time: 2.13 minutes.

Preparation 51: methyl 2-(mesityloxy)-6-(prop-1-yn-1-yl)nicotinate

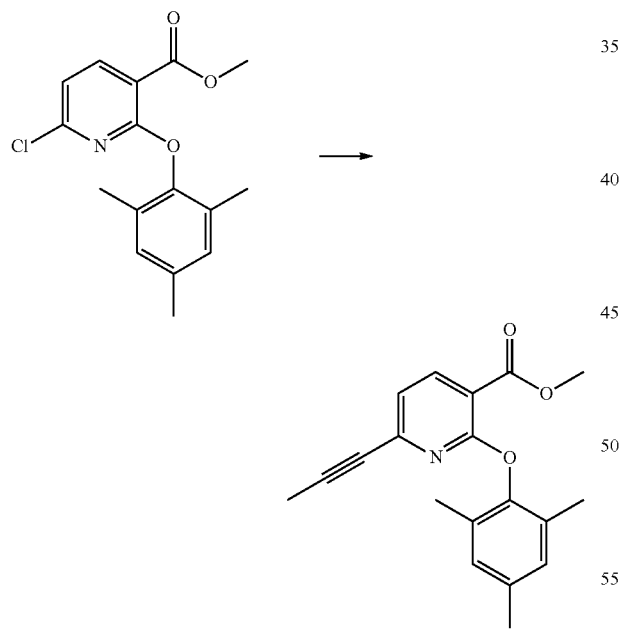

Prop-1-yne (25.78 μL, 0.4543 mmol) was bubbled through a solution of N,N-dimethylformamide (2 mL) and triethylamine (409.6 μL, 2.939 mmol) and then added to a mixture of methyl 6-chloro-2-(2,4,6-trimethylphenoxy)pyridine-3-carboxylate (150. mg, 0.491 mmol), dichloropalladium; triphenylphosphane (34.44 mg, 0.04907 mmol), copper (I) iodide (14.02 mg, 0.07362 mmol) and triphenyl phosphine (17.05 μL, 0.07359 mmol) in deoxygenated N,N-dimethylformamide (2 mL) under continous nitorgen flow. The resulting solution was purged with propyne and capped. The reaction was then stirred at 105° C. for 16 hours. The cooled mixture was diluted with ethyl acetate and passed through a plug of celite, washing with ethyl acetate (10 mL). Water (7.5 mL) was added to the filtrate and the layers were separated. The aqueous layer was extracted with ethyl acetate (2×10 mL). The combined organic extracts were washed with a saturated aqueous solution of sodium chloride (10 mL) and dried over sodium sulfate. After filtration the solvent was removed under reduced pressure to give a dark brown residue. The residue was purified by column chromatography on silica gel eluting 0-100% ethyl acetate in hexanes to yield methyl 6-prop-1-ynyl-2-(2,4,6-trimethylphenoxy)pyridine-3-carboxylate (102.4 mg, 0.331 mmol, 72.9%) ESI-MS m/z calc. 309.1365, found 310.2 (M+1)$^+$; Retention time: 0.76 minutes.

Preparation 52: N-[(6-amino-2-pyridyl)sulfonyl]-6-[3-(trifluoromethyl)pyrazol-1-yl]-2-(2,4,6-trimethylphenoxy)pyridine-3-carboxamide (Compound 676)

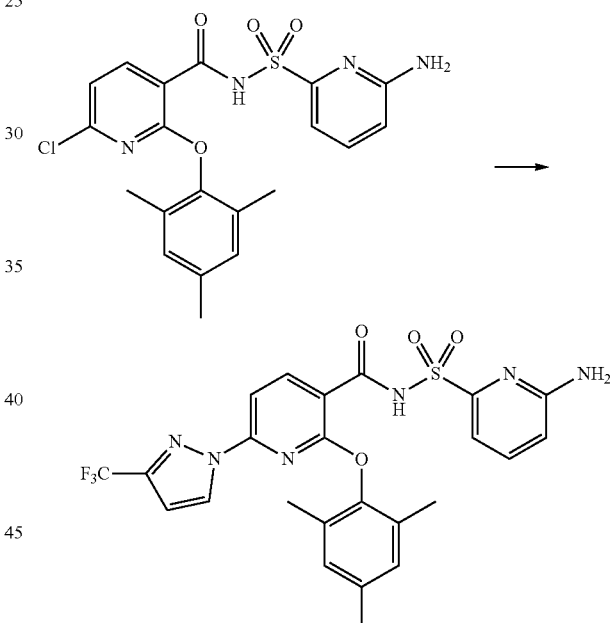

N-[(6-amino-2-pyridyl)sulfonyl]-6-chloro-2-(2,4,6-trimethylphenoxy)pyridine-3-carboxamide (30. mg, 0.067 mmol), 5-(trifluoromethyl)-1H-pyrazole (27.41 mg, 0.2014 mmol), potassium carbonate (19.49 mg, 0.1410 mmol) and trans-diaminocyclohexane (1.534 mg, 1.613 μL, 0.01343 mmol) were combined in N,N-dimethylformamide. At this point copper(I) iodide (0.6393 mg, 0.003357 mmol) was added and the reaction was heated at 150° C. in the microwave for 2 hours. The reaction was filtered and purified by LC/MS utilizing a gradient of 10-99% acetonitrile in 5 mM aq HCl to yield N-[(6-amino-2-pyridyl)sulfonyl]-6-[3-(trifluoromethyl)pyrazol-1-yl]-2-(2,4,6-trimethylphenoxy)pyridine-3-carboxamide (Compound 676) (8 mg, 0.01 mmol, 20%) $^1$H NMR (400 MHz, DMSO-d$_6$) δ 12.54 (s, 1H), 8.32 (d, J=8.1 Hz, 1H), 7.85 (dd, J=2.6, 1.1 Hz, 1H), 7.69-7.62 (m, 2H), 7.22 (dd, J=7.4, 0.8 Hz, 1H), 6.99 (d, J=2.6 Hz, 1H), 6.97 (s, 2H), 6.72 (d, J=8.4 Hz, 1H), 6.56 (s, 2H), 2.28

(s, 3H), 2.03 (s, 6H). ESI-MS m/z calc. 546.1297, found 547.2 (M+1)⁺; Retention time: 2.1 minutes.

The following compound can be synthesized using the procedures described herein:

N-[(6-amino-2-pyridyl)sulfonyl]-6-pyrazol-1-yl-2-(2,4,6-trimethylphenoxy)pyridine-3-carboxamide (Compound 564), N-[(6-amino-2-pyridyl)sulfonyl]-6-[5-methyl-3-(trifluoromethyl)pyrazol-1-yl]-2-(2,4,6-trimethylphenoxy)pyridine-3-carboxamide (Compound 633), N-[(6-amino-2-pyridyl)sulfonyl]-6-[4-(trifluoromethyl)pyrazol-1-yl]-2-(2,4,6-trimethylphenoxy)pyridine-3-carboxamide (Compound 691), and N-[(6-amino-2-pyridyl)sulfonyl]-6-(4-methylpyrazol-1-yl)-2-(2,4,6-trimethylphenoxy)pyridine-3-carboxamide (Compound 1220).

Preparation 53: methyl 2-(mesityloxy)-6-(1-methylcyclopropyl)nicotinate

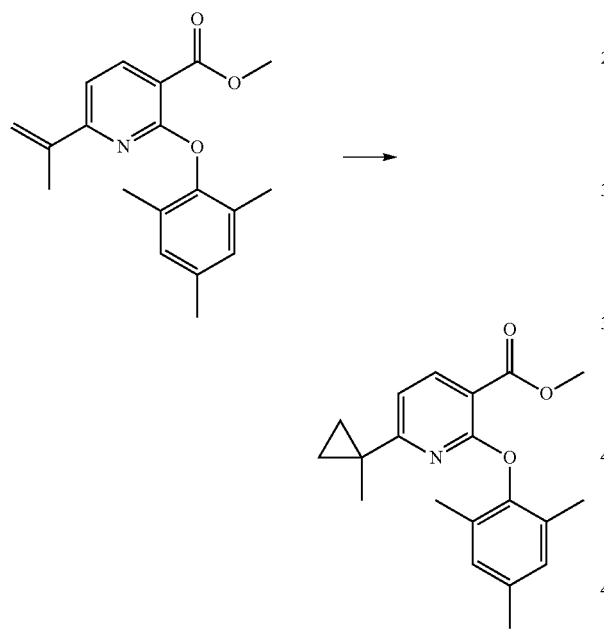

In a microwave vial, trimethylsulfoxonium iodide (5.2 g, 23 mmol), was suspended in anhydrous DMSO (26 mL) under nitrogen. Sodium hydride 60% in oil (1.0 g, 26 mmol) was added and the resulting solution was left stirring 10 min. at room temperature. Methyl 6-(prop-1-en-2-yl)-2-(2,4,6-trimethylphenoxy)pyridine-3-carboxylate (2.6 g, 8.4 mmol) was added dissolved in anhydrous THF (8 mL) and left stirring at room temperature 18 hours. The reaction mixture was partitioned between water (100 mL) and ethyl acetate (3×100 mL), separated, then the organic phase was concentrated under reduced pressure and the resulting residue was purified on silica gel using 0 to 10% ethyl acetate in heptane which provided the desired product methyl 6-(1-methylcyclopropyl)-2-(2,4,6-trimethylphenoxy)pyridine-3-carboxylate (1.59 g, 58%) as a oil. ESI-MS m/z calc. 325.2, found 326.2 (M+1)⁺; ¹H NMR (300 MHz, CDCl₃) ppm: 0.60 (m, 2H), 0.84 (m, 2H), 1.36 (s, 3H), 2.01 (s, 6H), 2.28 (s, 3H), 3.92 (s, 3H), 6.83 (s, 2H), 6.96 (d, J=7.9 Hz, 1H), 8.16 (d, J=7.9 Hz, 1H).

Preparation 54: ethyl 2-(mesityloxy)-6-(1-(trifluoromethyl)cyclopropyl)nicotinate Step 1: ethyl 2-(mesityloxy)-6-(3-(trifluoromethyl)-4,5-dihydro-3H-pyrazol-3-yl)nicotinate

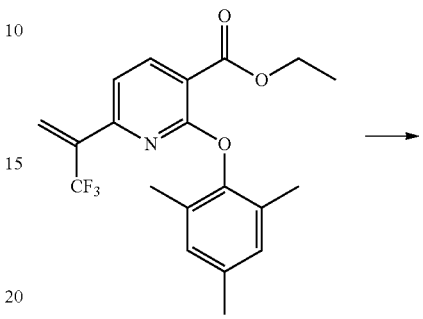

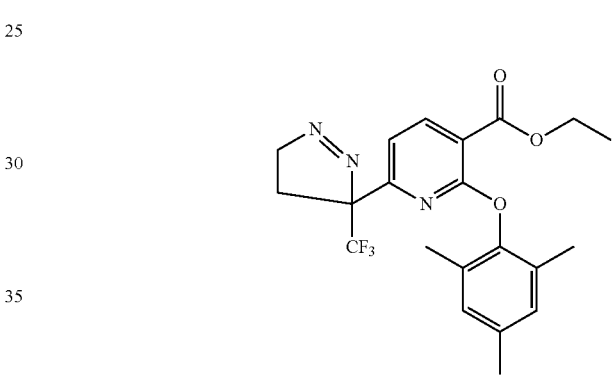

Preparation of a solution of diazomethane in ethyl ether: N-nitriso-N-methylurea (1.87 g, 15.8 mmol) was added to a biphasic mixture of 40% aqueous KOH (6.7 mL) and diethyl ether (20 mL) cooled in an ice-bath. The mixture was stirred in the ice-bath for 20 min (turns yellow), and then cooled in a dry-ice/acetone bath. Once the aqueous layer was frozen, the ether layer was decanted and the yellow solution was kept under nitrogen until ready to use.

The above solution of diazomethane (15.8 mmol) was added dropwise to a solution of ethyl 6-(3,3,3-trifluoroprop-1-en-2-yl)-2-(2,4,6-trimethylphenoxy)pyridine-3-carboxylate (1.5 g, 3.95 mmol) in ethyl ether (20 mL) at 0° C. The yellow color of the diazomethane spontaneously disappeared upon addition. The reaction was stirred at 0° C. for 30 min, and TLC showed starting material was completely consumed. Acetic acid (1 mL) was added to quench excess the diazomethane until it turns colorless and bubbles evolution ceased. The mixture was then diluted with ethyl acetate (50 mL), washed with saturated aqueous sodium bicarbonate (20 mL), brine (20 mL), dried over anhydrous sodium sulfate and concentrated to give ethyl 2-(mesityloxy)-6-(3-(trifluoromethyl)-4,5-dihydro-3H-pyrazol-3-yl)nicotinate as a pale yellow oil (1.7 g). ¹H NMR (300 MHz, CDCl₃) ppm, 1.40 (t, J=6.9 Hz, 3H), 1.68-1.92 (m, 2H), 1.98 (br s, 6H), 2.31 (s, 3H), 3.90-4.10 (m, 1H), 4.43 (q, J=6.9 Hz, 2H), 4.64 (ddd, J=18.1, 9.5, 4.2 Hz, 1H), 6.87 (s, 2H), 7.57 (d, J=7.8 Hz, 1H), 8.31 (d, J=7.8 Hz, 1H). LCMS: [M+H]⁺=422.2.

Step 2: ethyl 2-(mesityloxy)-6-(1-(trifluoromethyl)cyclopropyl)nicotinate

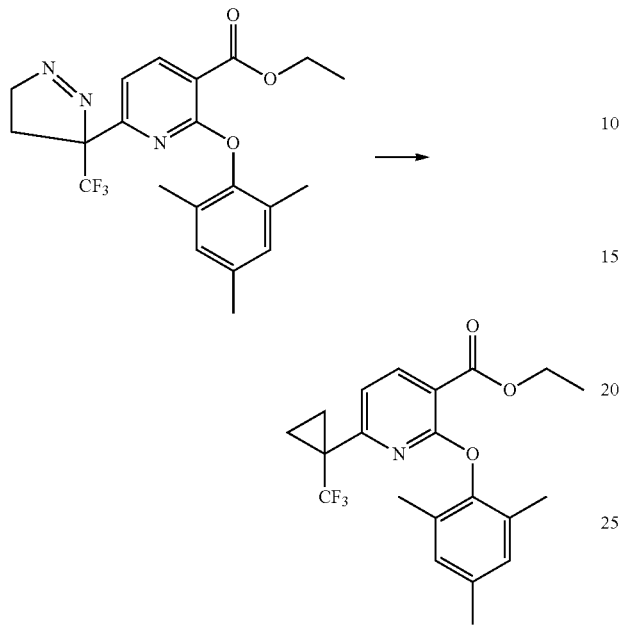

Ethyl 2-(mesityloxy)-6-(3-(trifluoromethyl)-4,5-dihydro-3H-pyrazol-3-yl)nicotinate (1.7 g, crude, 3.9 mmol) was dissolved in m-xylene (25 mL). The solution was gently refluxed for 2 hours. TLC shows reaction complete. The solvent was removed and the residue was purified by silica gel chromatography, eluting with a mixture of ethyl acetate and heptanes (0-10%), to afford 1.6 g, crude (quantitative yield). as an unseparable mixture (1:1) of ethyl 6-[1-(trifluoromethyl)cyclopropyl]-2-(2,4,6-trimethylphenoxy)pyridine-3-carboxylate, and ethyl 6-[-1,1,1-trifluorobut-2-en-2-yl]-2-(2,4,6-trimethylphenoxy)pyridine-3-carboxylate (undefined stereochemistry of the olefin). In order to remove the alkene, the mixture of 6-[1-(trifluoromethyl)cyclopropyl]-2-(2,4,6-trimethylphenoxy)pyridine-3-carboxylate and ethyl 6-[(2Z or 2E)-1,1,1-trifluorobut-2-en-2-yl]-2-(2,4,6-trimethylphenoxy)pyridine-3-carboxylate (1.5 g, 3.81 mmol, 1:1) was dissolved in tert-butanol (5 mL). Water (3 mL) was added followed by citric acid (549 mg, 2.86 mmol) and potassium osmium(VI) oxide dehydrate (1.4 mg). Finally, 4-methylmorpholine N-oxide monohydrate (568 mg, 4.2 mmol) was added. The mixture was stirred at room temperature overnight. LCMS shows 50% conversion. Potassium osmium(VI) oxide dehydrate (1.4 mg) was added and the reaction was continued stirred until HPLC showed reaction was complete (approximately 40 hours). The reaction was concentrated to remove most of the tert-butanol. The resulting aqueous mixture was diluted with ethyl acetate (60 mL) and washed with water (10 mL), brine (10 mL), dried over anhydrous sodium sulfate and concentrated under reduced pressure. The residue was purified by silica gel chromatography, eluting with a mixture of ethyl acetate and heptanes (0-10% then 50%), to afford ethyl 6-[1-(trifluoromethyl)cyclopropyl]-2-(2,4,6-trimethylphenoxy)pyridine-3-carboxylate (600 mg, 40%) as a white solid. $^1$H NMR (300 MHz, CDCl$_3$) ppm 0.96-1.05 (m, 2H), 1.15-1.23 (m, 2H), 1.39 (t, J=7.2 Hz, 3H), 2.01 (s, 6H), 2.29 (s, 3H), 4.41 (q, J=7.2 Hz, 2H), 6.85 (s, 2H), 7.25 (d, J=8.2 Hz, 1H), 8.21 (d, J=8.2 Hz, 1H). LCMS: [M+H]$^+$=394.0.

Preparation 55: ethyl 2-(mesityloxy)-6-(perfluoroethyl)nicotinate

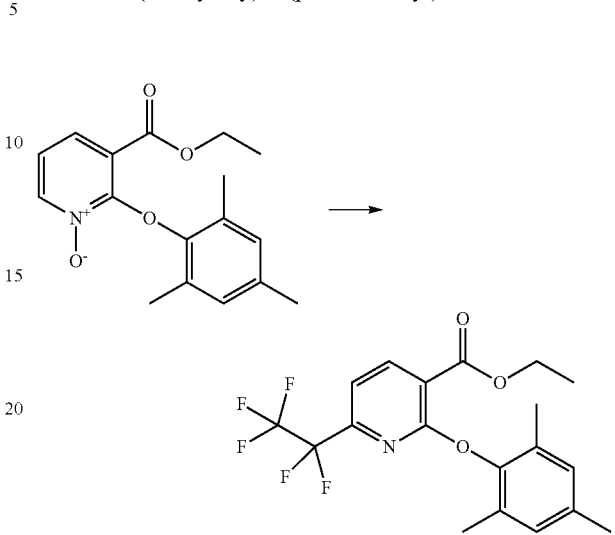

In a sealed tube, 3-(ethoxycarbonyl)-2-(mesityloxy)pyridine 1-oxide (1.85 g, 6.14 mmol) was dissolved in anhydrous tetrahydrofuran (18.5 mL) with flame dried (under high vacuum) cesium fluoride (93 mg, 0.05 mmol) then trimethyl(pentafluoroethyl)silane (3.53 g, 18.4 mmol) was added at 0° C. and the reaction mixture was stirred at room temperature under nitrogen for 5 days. Distilled water (10 mL) and ethyl acetate (50 mL) were added to the crude material. The organic phase was separated, dried over anhydrous sodium sulfate, filtered and concentrated under reduced pressure. The resulting residue was purified on silica gel using 0-10% ethyl acetate in heptane to provide ethyl 6-(pentafluoroethyl)-2-(2,4,6-trimethylphenoxy)pyridine-3-carboxylate (480 mg, 25%) as an oil. [M+H]$^+$=404.1 $^1$H NMR (300 MHz, CDCl$_3$) ppm: 1.41 (t, J=7.1 Hz, 3H), 2.03 (s, 6H), 2.29 (s, 3H), 4.45 (q, J=7.1 Hz, 2H), 6.87 (s, 2H), 7.39 (d, J=7.7 Hz, 1H), 8.36 (d, J=7.8 Hz, 1H).

Preparation 56: tert-butyl (4-sulfamoylthiazol-2-yl)carbamate

Step 1: Lithium (tert-butoxycarbonyl)(4-sulfinatothiazol-2-yl)amide

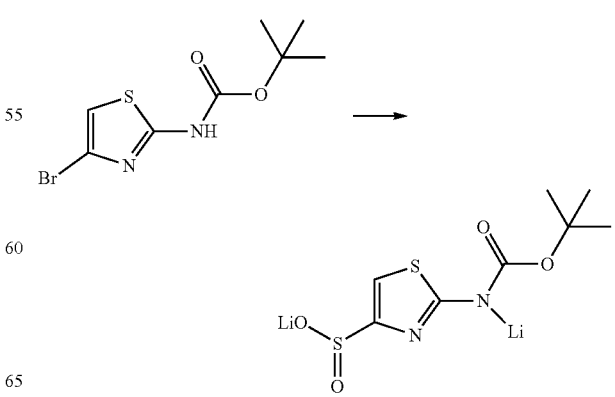

Methyllithium (0.70 mL, 1.6 M in diethyl ether, 1.1 mmol) was added to a solution of tert-butyl N-(4-bromo-1,3-thiazol-2-yl)carbamate (279 mg, 1.00 mmol) in anhydrous tetrahydrofuran (2 mL) and anhydrous diethyl ether (2 mL) at −78° C. After 5 min, tert-butyl lithium (1.2 mL, 1.7 M in pentane, 2 mmol) was added at −78° C. A light yellow suspension was formed. After 20 min, sulfur dioxide (gas) was bubbled into the reaction at −78° C. for 5 min. A yellow clear solution was obtained. The reaction was allowed to slowly warm up to room temperature and stirred overnight. The reaction mixture was concentrated to dryness and the residue was triturated with diethyl ether (10 mL) to afford a light yellow solid (390 mg), which is a mixture of lithium (tert-butoxycarbonyl)(4-sulfinatothiazol-2-yl)amide and lithium bromide. $[M+Na]^+=287.0$.

Step 2: tert-butyl (4-sulfamoylthiazol-2-yl)carbamate

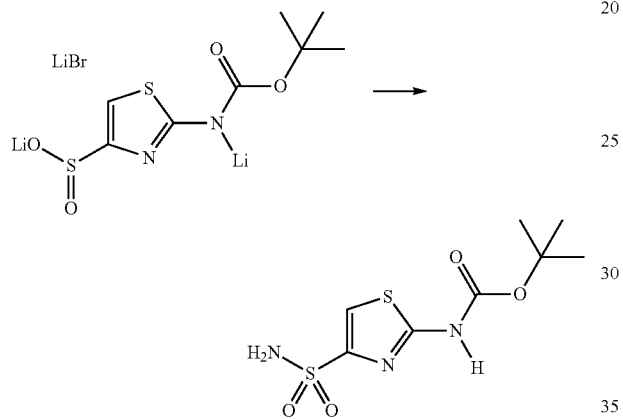

Hydroxylamine-O-sulfonic acid (147 mg, 1.2 mmol) was added to a solution of lithium 2-{[(tert-butoxy)carbonyl]amino}-1,3-thiazole-4-sulfinate (330 mg, containing lithium bromide, 0.91 mmol) and sodium acetate (148 mg, 1.8 mmol) in water (4 mL) at 0° C. The reaction was stirred at room temperature for 2 hours. Copious amounts of solids precipitated out. HPLC showed complete conversion. The mixture was stirred at 0° C. for 5 min. The solid was filtered off, washed with cold water (1 mL) and dried under high vacuum to afford tert-butyl N-(4-carbamoyl-1,3-thiazol-2-yl)carbamate (130 mg, 51%) as a white solid. $^1$H NMR (300 MHz, DMSO-$d_6$) δ 1.49 (s, 9H), 7.43 (s, 2H), 7.67 (s, 1H), 11.84 (br. s, 1H). $[M+Na]^+=302.0$.

Preparation 57: tert-butyl ((6-sulfamoylpyridin-2-yl)methyl)carbamate

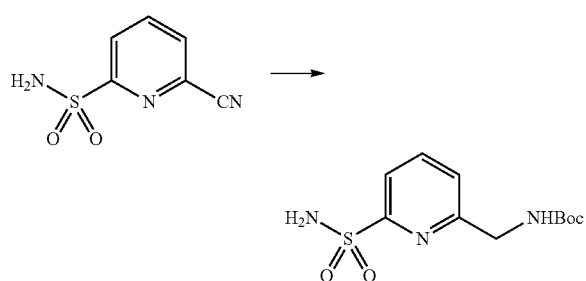

A solution of 6-cyanopyridine-2-sulfonamide (1.00 g, 5.46 mmol) in methanol (25 mL) and ammonia (5 mL of a 7.0 N solution in methanol, 35 mmol) was treated with a spatula of Raney-Nickel (2800, slurry in water). The flask was purged three times with hydrogen then left to stir at room temperature under one atmosphere of hydrogen for 18 hours. The crude reaction mixture was filtered over a pad of celite, washed with methanol, and concentrated under reduced pressure. The residue was taken up in dichloromethane (25 mL) and treated successively with triethylamine (1.52 mL, 10.9 mmol) and di-tert-butyl dicarbonate (1.55 g, 7.10 mmol). After about 1 hour, tetrahydrofuran (10 mL) was added in an attempt to help solubilize the reaction mixture. After another hour, the reaction was concentrated under reduced pressure, transferred to a 250-mL separatory funnel with water (50 mL) and extracted with ethyl acetate (3×50 mL). The combined organic layers were washed with brine (50 mL), dried over anhydrous sodium sulfate, filtered, and concentrated under reduced pressure. The residue was purified on 40 g of silica gel utilizing a gradient from 50% to 100% ethyl acetate in heptanes to afford tert-butyl ((6-sulfamoylpyridin-2-yl)methyl)carbamate (217 mg, 14%) as a white solid. $^1$H NMR (300 MHz, Acetone-$d_6$) ppm 1.43 (s, 9H), 4.43 (d, J=6.0 Hz, 2H), 6.48-6.77 (m, 3H), 7.58 (d, J=7.8 Hz, 1H), 7.83 (d, J=7.8 Hz, 1H), 7.97-8.10 (m, 1H). $[M+Na]^+=310.1$.

Preparation 58: N-(2-aminothiazol-5-yl)sulfonyl-6-tert-butyl-2-(2,4,6-trimethylphenoxy)pyridine-3-carboxamide (Compound 1148)

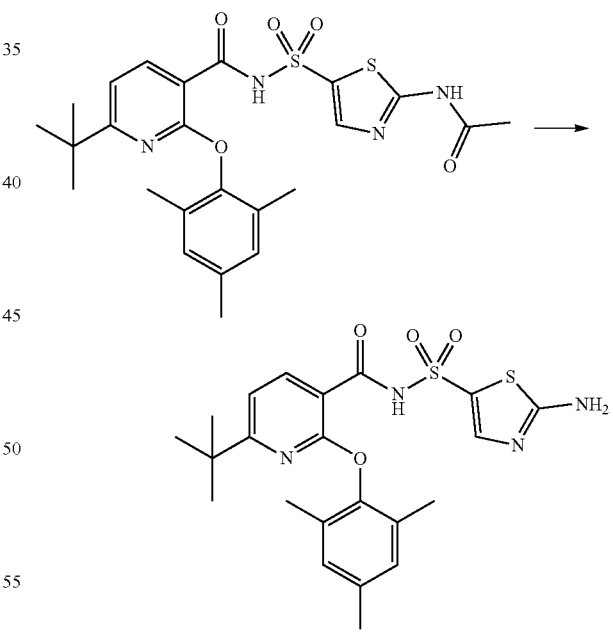

In a 4 mL vial a solution of N-(2-acetamidothiazol-5-yl)sulfonyl-6-tert-butyl-2-(2,4,6-trimethylphenoxy)pyridine-3-carboxamide (14.6 mg, 0.0269 mmol) and aqueous hydrochloric acid (268.5 µL of 4 M, 1.074 mmol) in dioxane (277.4 µL) was stirred at 90° C. for 1 hour. The reaction mixture was cooled and purified directly by reverse-phase preparative chromatography utilizing a C18 column and a gradient of 30-99 acetonitrile in water containing 5 mM hydrochloric acid to afford N-(2-aminothiazol-5-yl)sulfonyl-6-tert-butyl-2-(2,4,6-trimethylphenoxy)pyridine-3-carboxamide (Compound 1148) (5.9 mg, 0.012 mmol, 45%) as a white solid. $^1$H NMR (400 MHz, DMSO) δ 12.10 (s, 1H), 8.02 (s, 2H), 7.95 (d, J=7.8 Hz, 1H), 7.67 (s, 1H), 7.12 (d, J=7.8 Hz, 1H), 6.90 (s, 2H), 2.25 (s, 3H), 1.97 (s, 7H), 1.04 (s, 10H). ESI-MS m/z calc. 474.1, found 475.2 (M+1)$^+$; Retention time: 2.11 minutes.

Preparation 59: 6-(tert-butyl)-2-(mesityloxy)-4-methoxy-N-((3-nitrophenyl)sulfonyl)nicotinamide

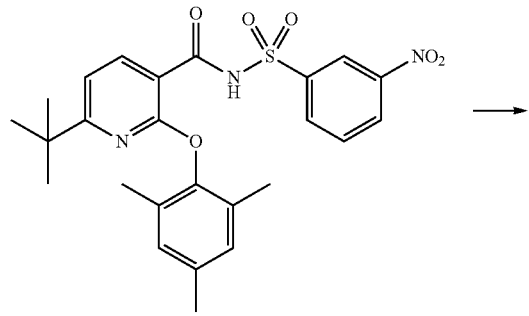

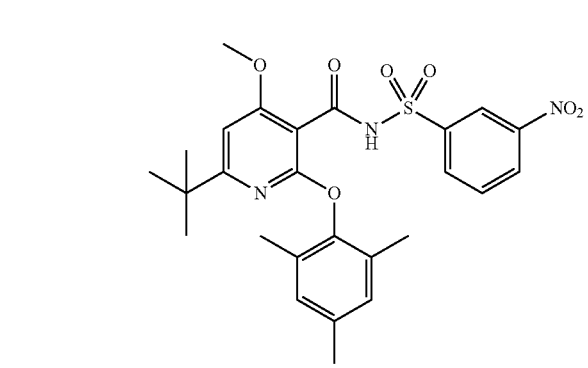

In a 10 mL microwave vessel was added 6-tert-butyl-N-(3-nitrophenyl)sulfonyl-2-(2,4,6-trimethylphenoxy)pyridine-3-carboxamide (85 mg, 0.17 mmol) dissolved in anhydrous methanol (684.1 mg, 864.9 µL, 21.35 mmol) and xylene (850.0 µL) and to it was added diacetoxypalladium (3.835 mg, 0.01708 mmol), (diacetoxyiodo)benzene (165.0 mg, 0.5124 mmol), and 4 Angstrom molecular sieves. The mixture was heated in an oil bath to 100° C. for 18 hours. A second aliquot of diacetoxypalladium (3.835 mg, 0.01708 mmol) was added and the reaction mixture heated in an oil bath to 100° C. for an additional 48 hours. The mixture was allowed to cool and the mixture was filtered and the resulting solution was purified by reverse-phase preparative chromatography utilizing a C18 column and a gradient of 30-99 acetonitrile in water containing 5 mM hydrochloric acid to afford 6-tert-butyl-4-methoxy-N-(3-nitrophenyl)sulfonyl-2-(2,4,6-trimethylphenoxy)pyridine-3-carboxamide (20.7 mg, 0.0388 mmol, 23%). $^1$H NMR (400 MHz, DMSO) δ 12.89 (s, 1H), 8.61 (t, J=2.0 Hz, 1H), 8.49 (d, J=8.2 Hz, 1H), 8.36 (d, J=8.1 Hz, 1H), 7.92 (t, J=8.1 Hz, 1H), 6.82 (s, 2H), 6.72 (s, 1H), 3.84 (s, 3H), 2.22 (s, 3H), 1.86 (s, 6H), 1.03 (s, 10H). ESI-MS m/z calc. 527.1726, found 528.2 (M+1)$^+$; Retention time: 2.2 minutes.

Preparation 60: 2-chloro-8,8-dimethyl-7,8-dihydro-5H-pyrano[4,3-b]pyridine-3-carbonitrile Step 1: 5-(hydroxymethylene)-3,3-dimethyltetrahydro-4H-pyran-4-one

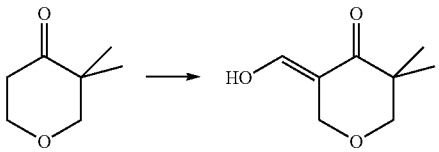

To a solution of 3,3-dimethyltetrahydropyran-4-one (1.8 g, 14 mmol) in ether (50 mL) was added ethyl formate (1.040 g, 1.134 mL, 14.04 mmol). The mixture was cooled to 0° C. Sodium ethoxide (1.051 g, 15.44 mmol) was added at 0° C. The mixture was allowed to warm to room temperature, stirred overngiht and then evaporated to dryness. The crude material was used directly in next step without further purification.

Step 2: 2-hydroxy-8,8-dimethyl-7,8-dihydro-5H-pyrano[4,3-b]pyridine-3-carbonitrile

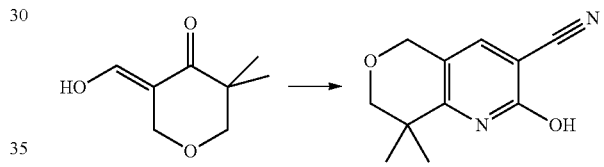

To a suspension of 5-(hydroxymethylene)-3,3-dimethyl-tetrahydropyran-4-one (2.2 g, 14 mmol) in pyridine (100 mL) was added 2-cyanoacetamide (1.177 g, 14.00 mmol). The mixture was heated at reflux overnight. The reaction mixture was evaporated to dryness and the residue was partitioned between ethyl acetate and water. The aqueous layer was extracted the times with ethyl acetate, and then three times with a 2:1 mixture of dichloromethane and isopropanol. The combined organic layers were washed with brine, dried over magnesium sulfate, filtered, and evaporated to dryness. The residue was washed with methanol to yield the product (205 mg, 1.00 mmol, 7.1%). $^1$H NMR (400 MHz, Chloroform-d) δ 7.55 (s, 1H), 4.54 (s, 2H), 3.61 (s, 2H), 3.49 (s, 1H), 1.42 (s, 6H).

Step 3: 2-chloro-8,8-dimethyl-7,8-dihydro-5H-pyrano[4,3-b]pyridine-3-carbonitrile

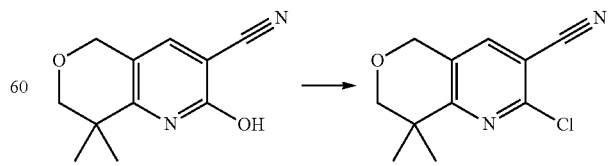

A mixture of 2-hydroxy-8,8-dimethyl-7,8-dihydro-5H-pyrano[4,3-b]pyridine-3-carbonitrile (240. mg, 1.17 mmol) in phosphorous oxychloride (2.5 mL, 26.82 mmol) was heated to 105° C. for 6 hours. The reaction mixture was evaporated to dryness. The residue was added dropwise to water, and then extracted three times with ethyl acetate. The combined organic layers were washed with brine, dried over magnesium sulfate, filtered, and concentrated to dryness. The crude material was purified by silica gel column chromatography (0-10% ethyl acetate in hexanes) to provide 2-chloro-8,8-dimethyl-7,8-dihydro-5H-pyrano[4,3-b]pyridine-3-carbonitrile (240. mg, 1.08 mmol, 92.3%) as a yellow solid. $^1$H NMR (400 MHz, Chloroform-d) δ 7.57 (s, 1H), 4.78 (d, J=0.9 Hz, 2H), 3.71 (s, 2H), 1.33 (s, 6H).

Preparation 61: 6-(tert-butyl)-2-(mesityloxy)-N—(N-methyl-3-nitrophenylsulfonimidoyl)nicotinamide

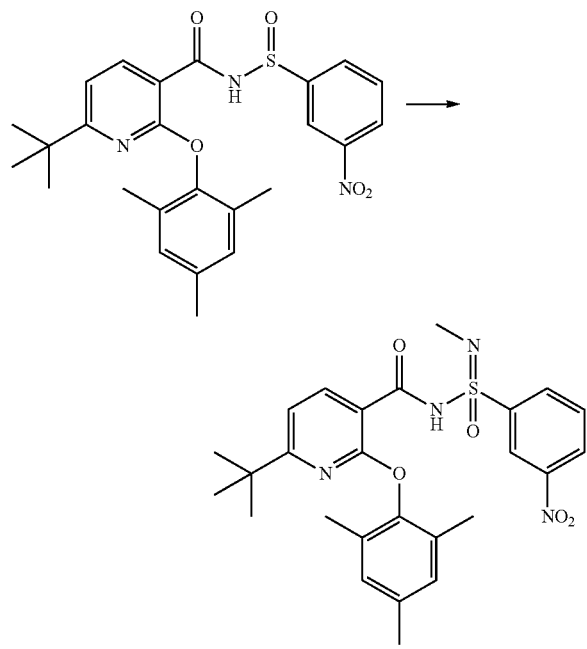

To a solution of rac-6-tert-butyl-N-(3-nitrobenzenesulfinyl)-2-(2,4,6-trimethylphenoxy)pyridine-3-carboxamide (253 mg, 0.525 mmol) in acetonitrile (4.1 mL) was added N-chlorosuccinimide (217 mg, 1.63 mmol) at 0° C. The mixture was then stirred at room temperature until no more starting material was left (about 1 hour). Methylamine (0.79 mL of a 2.0 M solution in THF, 1.6 mmol) was added to the reaction at 0° C. and the mixture was stirred for 1 hour at room temperature and then quenched by the addition of water (3 mL). The mixture was extracted with ethyl acetate (2×10 mL), the organic layers were combined, dried over sodium sulfate, filtered, and concentrated under reduced pressure. The residue was purified on 25 g of silica gel utilizing a gradient of 0% to 45% ethyl acetate in heptanes to afford 6-(tert-butyl)-2-(mesityloxy)-N—(N-methyl-3-nitrophenylsulfonimidoyl)nicotinamide (170 mg, 63% yield) as a white solid. $^1$H NMR (300 MHz, CDCl$_3$) ppm 1.06 (s, 9H), 2.02 (s, 6H), 2.28 (s, 3H), 2.78 (s, 3H), 6.83 (s, 2H), 6.91 (d, J=7.8 Hz, 1H), 7.74 (t, J=8.0 Hz, 1H), 8.24 (d, J=8.0 Hz, 1H), 8.38 (d, J=8.3 Hz, 1H), 8.45 (d, J=7.7 Hz, 1H), 8.83-8.87 (m, 1H). [M+H]$^+$=511.1.

Preparation 62: N-[(6-amino-2-pyridyl)sulfonyl]-6-(5-methoxy-2-methyl-phenyl)-2-(2,2,4-trimethylpyrrolidin-1-yl)pyridine-3-carboxamide (Compound, 470)

Step 1: N-((6-aminopyridin-2-yl)sulfonyl)-2,6-dichloronicotinamide

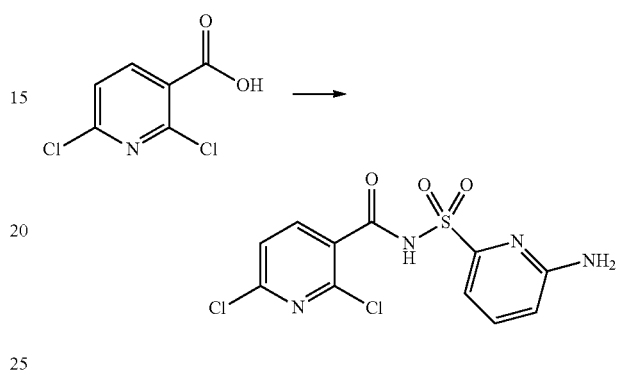

2,6-dichloro-pyridine-3-carboxylic acid (20.2 g, 105 mmol) was dissolved in N,N-dimethylformamide (200 mL) and stirred under nitrogen and CDI (25.5 g, 158 mmol) was added in one portion. The reaction was warmed to 65° C. and heated for 1 h. In a separate vessel, 6-aminopyridine-2-sulfonamide (18.2 g, 105 mmol) was dissolved in N,N-dimethylformamide (100 mL) under nitrogen and NaH (4.40 g, 60%, 110 mmol) was added in portions to mitigate gas evolution and the reaction was stirred for 1 h. The two reactions were combined in one portion at 65° C. The reaction was stirred for 30 min and evaporated to remove most of N,N-dimethylformamide. The residue was poured over ice and made acidic (pH=−3) by the addition of 6M HCl. Solid was collected by filtration and washed with water (100 mL) and methanol (30 mL) and combined to the following crude material after dried. The filtrate and washing were combined and extracted with ethyl acetate (3×500 mL). The organics were washed once with brine (500 mL), dried over sodium sulfate and evaporated. The crude material was suspended in a mixture solvent of dichloromethane/ethyl acetate/methanol (30/30/30 mL), the suspension sonicated for 30 min, and filtered. The solid washed with ether (2×150 mL) and dried to give 19.8 g white solid (54%). The filtrate was further concentrated to afford 6.0 g (16%) of product. LCMS: 347 [M+H]$^+$; $^1$H NMR (DMSO-d$_6$, 250 MHz): 8.11 (d, J=7.5 Hz, 1H), 7.80-7.55 (m, 2H), 7.19 (d, J=7.2 Hz, 1H), 6.75 (d, J=8.5 Hz, 1H), 6.71 (s, 2H) ppm Step 2: N-((6-aminopyridin-2-yl)sulfonyl)-6-chloro-2-(2,2,4-trimethylpyrrolidin-1-yl)nicotinamide

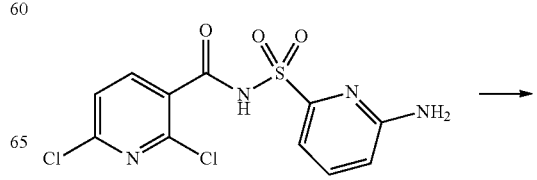

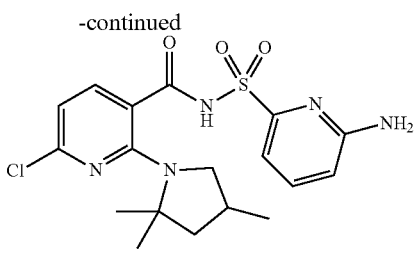

N-[(6-amino-2-pyridyl)sulfonyl]-2,6-dichloro-pyridine-3-carboxamide (1.02 g, 2.94 mmol), 2,2,4-trimethylpyrrolidine (Hydrochloric Acid (1)) (1.319 g, 8.814 mmol), and potassium carbonate (2.030 g, 14.69 mmol) were combined in dimethylsulfoxide (8.160 mL) and heated at 100° C. for 16 h. The reaction was diluted with water and the pH was adjusted to 7. The aqueous mixture was extracted with ethyl acetate (3×100 mL). The organics were combined, washed with brine, dried over sodium sulfate and evaporated. The crude material was purified by silica gel chromatography eluting with 0-100% ethyl acetate in hexanes to yield N-[(6-amino-2-pyridyl)sulfonyl]-6-chloro-2-(2,2,4-trimethylpyrrolidin-1-yl)pyridine-3-carboxamide (700. mg, 1.65 mmol, 56.2%) ESI-MS m/z calc. 423.1132, found 424.2 $(M+1)^+$; Retention time: 0.63 minutes.

Step 3

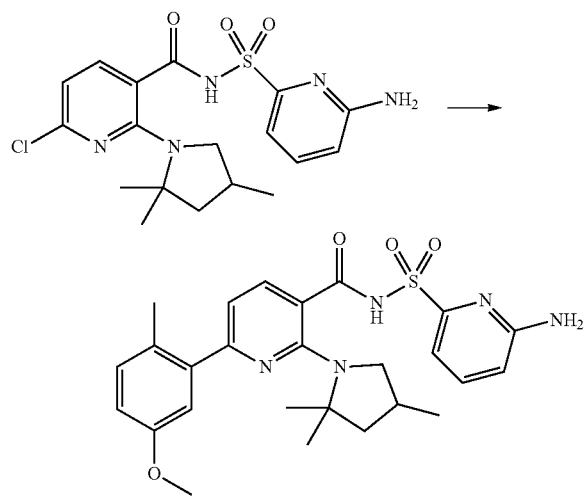

N-[(6-amino-2-pyridyl)sulfonyl]-6-chloro-2-(2,2,4-trimethylpyrrolidin-1-yl)pyridine-3-carboxamide (42 mg, 0.10 mmol), (5-methoxy-2-methyl-phenyl)boronic acid (25 mg, 0.15 mmol), tetrakis(triphenylphosphine)palladium (0) (11 mg, 0.010 mmol), and 2M aqueous potassium carbonate (0.2 mL, 4 mmol) were combined in N,N-dimethylformamide (1 mL) and irradiated in the microwave reactor for 20 min at 120° C. The reaction was filtered and purified by LC/MS utilizing a gradient of 10-99% acetonitrile in 5 mM aq HCl to yield N-[(6-amino-2-pyridyl)sulfonyl]-6-(5-methoxy-2-methyl-phenyl)-2-(2,2,4-trimethylpyrrolidin-1-yl)pyridine-3-carboxamide (Compound 470) as a hydrochloric acid salt (12 mg, 0.022 mmol, 22%). ESI-MS m/z calc. 509.21, found 510.5 $(M+1)^+$; Retention time: 1.42 minutes.

The following compound can be synthesized using the procedures described herein:

N-[(6-amino-2-pyridyl)sulfonyl]-6-(o-tolyl)-2-(2,2,4-trimethylpyrrolidin-1-yl)pyridine-3-carboxamide (Compound 761), N-(benzenesulfonyl)-6-(3-fluoro-5-hydroxy-phenyl)-2-[(4S)-2,2,4-trimethylpyrrolidin-1-yl]pyridine-3-carboxamide (Compound 1538), N-[(6-amino-2-pyridyl)sulfonyl]-6-cyclopropyl-2-[(4S)-2,2,4-trimethylpyrrolidin-1-yl]pyridine-3-carboxamide (Compound 1627), N-[(6-amino-2-pyridyl)sulfonyl]-6-(3-fluoro-5-hydroxy-phenyl)-2-[(4S)-2,2,4-trimethylpyrrolidin-1-yl]pyridine-3-carboxamide (Compound 1636)

N-[(6-amino-2-pyridyl)sulfonyl]-6-(4-isopropylphenyl)-2-[(4S)-2,2,4-trimethylpyrrolidin-1-yl]pyridine-3-carboxamide (Compound 630), N-[(6-amino-2-pyridyl)sulfonyl]-6-(4-isopropylphenyl)-2-[(4R)-2,2,4-trimethylpyrrolidin-1-yl]pyridine-3-carboxamide (Compound 890), N-[(6-amino-2-pyridyl)sulfonyl]-6-chloro-2-[(4S)-2,2,4-trimethylpyrrolidin-1-yl]pyridine-3-carboxamide (Compound 852), N-[(6-amino-2-pyridyl)sulfonyl]-2-[(4S)-2,2,4-trimethylpyrrolidin-1-yl]pyridine-3-carboxamide (Compound 946), N-[(6-amino-2-pyridyl)sulfonyl]-6-(2,4-dimethylphenyl)-2-(2,2,4-trimethylpyrrolidin-1-yl)pyridine-3-carboxamide (Compound 614), tert-butyl 5-[5-[(6-amino-2-pyridyl)sulfonylcarbamoyl]-6-[(4S)-2,2,4-trimethylpyrrolidin-1-yl]-2-pyridyl]-3,6-dihydro-2H-pyridine-1-carboxylate (Compound 1371), N-[(6-amino-2-pyridyl)sulfonyl]-3-[(2S,5R)-2,5-dimethylpyrrolidin-1-yl]-5-(6-isopropoxy-3-pyridyl)pyrazine-2-carboxamide (Compound 1651), N-[(6-amino-2-pyridyl)sulfonyl]-5-(3-fluoro-5-isobutoxyphenyl)-3-[(4S)-2,2,4-trimethylpyrrolidin-1-yl]pyrazine-2-carboxamide (Compound 1526), N-[(6-amino-2-pyridyl)sulfonyl]-6-norbornan-2-yl-2-[(4S)-2,2,4-trimethylpyrrolidin-1-yl]pyridine-3-carboxamide (Compound 1378), N-[(6-amino-2-pyridyl)sulfonyl]-6-isopropenyl-2-[(4S)-2,2,4-trimethylpyrrolidin-1-yl]pyridine-3-carboxamide (Compound 1423), N-[(6-amino-2-pyridyl)sulfonyl]-6-(6,6-dimethyl-2,3-dihydropyran-4-yl)-2-[(4S)-2,2,4-trimethylpyrrolidin-1-yl]pyridine-3-carboxamide (Compound 1369), N-[(6-amino-2-pyridyl)sulfonyl]-6-(3,4-dihydro-2H-pyran-6-yl)-2-[(4S)-2,2,4-trimethylpyrrolidin-1-yl]pyridine-3-carboxamide (Compound 1438), N-[(6-amino-2-pyridyl)sulfonyl]-6-(2,3-dihydrofuran-4-yl)-2-[(4S)-2,2,4-trimethylpyrrolidin-1-yl]pyridine-3-carboxamide (Compound 1455), N-[(6-amino-2-pyridyl)sulfonyl]-6-(1,2-dimethylpropyl)-2-[(4S)-2,2,4-trimethylpyrrolidin-1-yl]pyridine-3-carboxamide (Compound 1489), N-[(6-amino-2-pyridyl)sulfonyl]-6-tetrahydropyran-2-yl-2-[(4S)-2,2,4-trimethylpyrrolidin-1-yl]pyridine-3-carboxamide (Compound 1500), N-[(2-oxo-1H-pyridin-3-yl)sulfonyl]-6-tetrahydropyran-2-yl-2-[(4S)-2,2,4-trimethylpyrrolidin-1-yl]pyridine-3-carboxamide (Compound 1503), N-[(6-amino-2-pyridyl)sulfonyl]-6-(1,2-dimethylprop-1-enyl)-2-[(4S)-2,2,4-trimethylpyrrolidin-1-yl]pyridine-3-carboxamide (Compound 1510), N-[(6-amino-2-pyridyl)sulfonyl]-6-(3,4-dihydro-2H-pyran-5-yl)-2-[(4S)-2,2,4-trimethylpyrrolidin-1-yl]pyridine-3-carboxamide (Compound 1524), N-[(6-amino-2-pyridyl)sulfonyl]-6-tetrahydrofuran-3-yl-2-[(4S)-2,2,4-trimethylpyrrolidin-1-yl]pyridine-3-carboxamide (Compound 1534), N-[(6-amino-2-pyridyl)sulfonyl]-6-tetrahydropyran-3-yl-2-[(4S)-2,2,4-trimethylpyrrolidin-1-yl]pyridine-3-carboxamide (Compound 1632), 6-(1-acetyl-4-piperidyl)-N-[(6-amino-2-pyridyl)sulfonyl]-2-[(4S)-2,2,4-trimethylpyrrolidin-1-yl]pyridine-3-carboxamide (Compound 1634) (Compound 946), N-[(6-amino-2-pyridyl)sulfonyl]-6-[4-(trifluoromethyl)cyclohexen-1-yl]-2-[(4S)-2,2,4-trimethylpyrrolidin-1-yl]pyridine-3-carboxamide (Compound 1664), N-[(6-amino-2-pyridyl)sulfonyl]-6-(2-cyclopropylethyl)-2-[(4S)-2,2,4-trimethylpyrrolidin-1-yl]pyridine-3-carboxamide (Compound 1677), N-[(6-amino-2-pyridyl)sulfonyl]-6-[4-(trifluoromethyl)cyclohexyl]-2-[(4S)-2,2,4-trimethylpyrrolidin-1-yl]pyridine-3-carboxamide (Compound 1672), N-[(6-amino-2-pyridyl)sulfonyl]-6-(2-hydroxy-5,5-dimethyl-cyclohexyl)-2-[(4S)-2,2,4-trimethylpyrrolidin-1-yl]pyridine-3-carboxamide (Compound 1439), N-[(6-amino-2-pyridyl)sulfonyl]-6-(3,3-dimethyl-6-oxo-cyclohexen-1-yl)-2-[(4S)-2,2,4-trimethylpyrrolidin-1-yl]pyridine-3-carboxamide (Compound 1462), N-[(6-amino-2-pyridyl)sulfonyl]-6-isopropyl-2-[(4S)-2,2,4-trimethylpyrrolidin-1-yl]pyridine-3-carboxamide (Compound 1505), N-[(6-amino-2-pyridyl)sulfonyl]-6-ethyl-2-[(4S)-2,2,4-trimethylpyrrolidin-1-yl]pyridine-3-carboxamide (Compound 1507), N-[(6-amino-2-pyridyl)sulfonyl]-6-(3,6-dihydro-2H-pyran-4-yl)-2-[(4S)-2,2,4-trimethylpyrrolidin-1-yl]pyridine-3-carboxamide (Compound 1594), N-[(6-amino-2-pyridyl)sulfonyl]-6-tetrahydropyran-4-yl-2-[(4S)-2,2,4-trimethylpyrrolidin-1-yl]pyridine-3-carboxamide (Compound 1595), N-[(6-amino-2-pyridyl)sulfonyl]-6-isobutyl-2-[(4S)-2,2,4-trimethylpyrrolidin-1-yl]pyridine-3-carboxamide (Compound 1599), tert-butyl 4-[5-[(6-amino-2-pyridyl)sulfonylcarbamoyl]-6-[(4S)-2,2,4-trimethylpyrrolidin-1-yl]-2-pyridyl]-3,6-dihydro-2H-pyridine-1-carboxylate (Compound 1624), N-[(6-amino-2-pyridyl)sulfonyl]-6-(2-methylprop-1-enyl)-2-[(4S)-2,2,4-trimethylpyrrolidin-1-yl]pyridine-3-carboxamide (Compound 1683), tert-butyl 4-[5-[(6-amino-2-pyridyl)sulfonylcarbamoyl]-6-[(4S)-2,2,4-trimethylpyrrolidin-1-yl]-2-pyridyl]-2,3-dihydropyrrole-1-carboxylate (Compound 1684), N-[(6-amino-2-pyridyl)sulfonyl]-6-(4-fluoro-2-methyl-phenyl)-2-(2,2,4-trimethylpyrrolidin-1-yl)pyridine-3-carboxamide (Compound 822), N-[(6-amino-2-pyridyl)sulfonyl]-6-phenyl-2-(2,2,4-trimethylpyrrolidin-1-yl)pyridine-3-carboxamide (Compound 1334), N-[(6-amino-2-pyridyl)sulfonyl]-6-(4-fluorophenyl)-2-(2,2,4-trimethylpyrrolidin-1-yl)pyridine-3-carboxamide (Compound 712), N-[(6-amino-2-pyridyl)sulfonyl]-6-(3-ethoxy-5-fluoro-phenyl)-2-(2,2,4-trimethylpyrrolidin-1-yl)pyridine-3-carboxamide (Compound 1099), N-[(6-amino-2-pyridyl)sulfonyl]-6-(p-tolyl)-2-(2,2,4-trimethylpyrrolidin-1-yl)pyridine-3-carboxamide (Compound 456), N-[(6-amino-2-pyridyl)sulfonyl]-6-(3-isobutoxyphenyl)-2-(2,2,4-trimethylpyrrolidin-1-yl)pyridine-3-carboxamide (Compound 695), N-[(6-amino-2-pyridyl)sulfonyl]-6-(2-fluoro-5-isobutoxyphenyl)-2-(2,2,4-trimethylpyrrolidin-1-yl)pyridine-3-carboxamide (Compound 1194), N-[(6-amino-2-pyridyl)sulfonyl]-6-(4-chloro-3-propoxyphenyl)-2-(2,2,4-trimethylpyrrolidin-1-yl)pyridine-3-carboxamide (Compound 644), N-[(6-amino-2-pyridyl)sulfonyl]-6-(4-chloro-3-isobutoxyphenyl)-2-(2,2,4-trimethylpyrrolidin-1-yl)pyridine-3-carboxamide (Compound 1021), N-[(6-amino-2-pyridyl)sulfonyl]-6-(4-isobutoxyphenyl)-2-(2,2,4-trimethylpyrrolidin-1-yl)pyridine-3-carboxamide (Compound 440), N-[(6-amino-2-pyridyl)sulfonyl]-6-(4-isopropylphenyl)-2-(2,2,4-trimethylpyrrolidin-1-yl)pyridine-3-carboxamide (Compound 693), N-[(6-amino-2-pyridyl)sulfonyl]-6-(4-chloro-3-isopropoxyphenyl)-2-(2,2,4-trimethylpyrrolidin-1-yl)pyridine-3-carboxamide (Compound 504), N-[(6-amino-2-pyridyl)sulfonyl]-6-(4-isopropoxyphenyl)-2-(2,2,4-trimethylpyrrolidin-1-yl)pyridine-3-carboxamide (Compound 1020), N-[(6-amino-2-pyridyl)sulfonyl]-6-(4-chlorophenyl)-2-(2,2,4-trimethylpyrrolidin-1-yl)pyridine-3-carboxamide (Compound 1100), N-[(6-amino-2-pyridyl)sulfonyl]-6-(4-isopropylphenyl)-2-(4-methyl-1-piperidyl)pyridine-3-carboxamide (Compound 847), N-[(6-amino-2-pyridyl)sulfonyl]-6-(2-fluoro-5-isobutoxyphenyl)-2-(4-methyl-1-piperidyl)pyridine-3-carboxamide (Compound 1109), N-[(6-amino-2-pyridyl)sulfonyl]-6-(4-isobutoxyphenyl)-2-(4-methyl-1-piperidyl)pyridine-3-carboxamide (Compound 1094), N-[(6-amino-2-pyridyl)sulfonyl]-6-(4-chloro-3-isobutoxyphenyl)-2-(4-methyl-1-piperidyl)pyridine-3-carboxamide (Compound 1266), N-[(6-amino-2-pyridyl)sulfonyl]-6-(4-chloro-3-propoxyphenyl)-2-(4-methyl-1-piperidyl)pyridine-3-carboxamide (Compound 692), N-[(6-amino-2-pyridyl)sulfonyl]-6-(3-isobutoxyphenyl)-2-(4-methyl-1-piperidyl)pyridine-3-carboxamide (Compound 777), N-[(6-amino-2-pyridyl)sulfonyl]-2-[(2S,5R)-2,5-dimethylpyrrolidin-1-yl]-6-phenyl-pyridine-3-carboxamide (Compound 805), N-[(6-amino-2-pyridyl)sulfonyl]-2-[(2S,5R)-2,5-dimethylpyrrolidin-1-yl]-6-(4-fluorophenyl)pyridine-3-carboxamide (Compound 1029), N-[(6-amino-2-pyridyl)sulfonyl]-2-[(2S,5R)-2,5-dimethylpyrrolidin-1-yl]-6-(4-methoxyphenyl)pyridine-3-carboxamide (Compound 1215), N-[(6-amino-2-pyridyl)sulfonyl]-2-[(2R,5S)-2,5-dimethylpyrrolidin-1-yl]-6-(3-ethoxy-5-fluoro-phenyl)pyridine-3-carboxamide (Compound 551), N-[(6-amino-2-pyridyl)sulfonyl]-6-(4-chlorophenyl)-2-[(2S,5R)-2,5-dimethylpyrrolidin-1-yl]pyridine-3-carboxamide (Compound 459), N-[(6-amino-2-pyridyl)sulfonyl]-6-(4-chloro-3-isobutoxyphenyl)-2-[(2S,5R)-2,5-dimethylpyrrolidin-1-yl]pyridine-3-carboxamide (Compound 1197), N-[(6-amino-2-pyridyl)sulfonyl]-2-[(2S,5R)-2,5-dimethylpyrrolidin-1-yl]-6-(4-isobutoxyphenyl)pyridine-3-carboxamide (Compound 563), N-[(6-amino-2-pyridyl)sulfonyl]-2-[(2S,5R)-2,5-dimethylpyrrolidin-1-yl]-6-(4-isopropylphenyl)pyridine-3-carboxamide (Compound 1343), N-[(6-amino-2-pyridyl)sulfonyl]-6-(4-chloro-3-isopropoxy-phenyl)-2-[(2S,5R)-2,5-dimethylpyrrolidin-1-yl]pyridine-3-carboxamide (Compound 788), N-[(6-amino-2-pyridyl)sulfonyl]-6-(4-chloro-3-propoxy-phenyl)-2-[(2R,5S)-2,5-dimethylpyrrolidin-1-yl]pyridine-3-carboxamide (Compound 773), N-[(6-amino-2-pyridyl)sulfonyl]-2-[(2S,5R)-2,5-dimethylpyrrolidin-1-yl]-6-(2-fluoro-5-isobutoxy-phenyl)pyridine-3-carboxamide (Compound 807), N-[(6-amino-2-pyridyl)sulfonyl]-2-[(2S,5R)-2,5-dimethylpyrrolidin-1-yl]-6-(3-isobutoxyphenyl)pyridine-3-carboxamide (Compound 957), N-[(6-amino-2-pyridyl)sulfonyl]-2-[(2S,5R)-2,5-dimethylpyrrolidin-1-yl]-6-(6-methoxy-2-pyridyl)pyridine-3-carboxamide (Compound 1141), N-[(6-amino-2-pyridyl)sulfonyl]-2-[(2R,5S)-2,5-dimethylpyrrolidin-1-yl]-6-(p-tolyl)pyridine-3-carboxamide (Compound 1078), N-[(3S)-3-aminopyrrolidin-1-yl]sulfonyl-6-(4-fluoro-3-methyl-phenyl)-2-[(4S)-2,2,4-trimethylpyrrolidin-1-yl]pyridine-3-carboxamide (Compound 2472), N-[(3S)-3-aminopyrrolidin-1-yl]sulfonyl-6-(3-fluoro-4-methyl-phenyl)-2-[(4S)-2,2,4-trimethylpyrrolidin-1-yl]pyridine-3-carboxamide (Compound 2587), N-[(3S)-3-aminopyrrolidin-1-yl]sulfonyl-6-(2-fluoro-4-methyl-phenyl)-2-[(4S)-2,2,4-trimethylpyrrolidin-1-yl]pyridine-3-carboxamide (Compound 1967), N-[(3S)-3-aminopyrrolidin-1-yl]sulfonyl-6-(3-fluoro-2-methyl-phenyl)-2-[(4S)-2,2,4-trimethylpyrrolidin-1-yl]pyridine-3-carboxamide (Compound 2199), N-[(3S)-3-aminopyrrolidin-1-yl]sulfonyl-6-(m-tolyl)-2-[(4S)-2,2,4-trimethylpyrrolidin-1-yl]pyridine-3-carboxamide (Compound 2339), N-[(3S)-3-aminopyrrolidin-1-yl]sulfonyl-6-(3-fluoro-5-methyl-phenyl)-2-[(4S)-2,2,4-trimethylpyrrolidin-1-yl]pyridine-3-carboxamide (Compound 1819), N-[(3S)-3-aminopyrrolidin-1-yl]sulfonyl-6-(2-fluoro-5-methyl-phenyl)-2-[(4S)-2,2,4-trimethylpyrrolidin-1-yl]pyridine-3-carboxamide (Compound 2016), N-[(3S)-3-aminopyrrolidin-1-yl]sulfonyl-6-(2-methoxyphenyl)-2-[(4S)-2,2,4-trimethylpyrrolidin-1-yl]pyridine-3-carboxamide (Compound 2666), N-[(3S)-3-aminopyrrolidin-1-yl]sulfonyl-6-(3-methoxyphenyl)-2-[(4S)-2,2,4-trimethylpyrrolidin-1-yl]pyridine-3-carboxamide (Compound 2240), N-[(3S)-3-aminopyrrolidin-1-yl]sulfonyl-6-(3,4-difluoro-phenyl)-2-[(4S)-2,2,4-trimethylpyrrolidin-1-yl]pyridine-3-carboxamide (Compound 2229), N-[(3S)-3-aminopyrrolidin-1-yl]sulfonyl-6-(4-methoxyphenyl)-2-[(4S)-2,2,4-trimethylpyrrolidin-1-yl]pyridine-3-carboxamide (Compound 2327), N-[(3S)-3-aminopyrrolidin-1-yl]sulfonyl-6-(2,4-difluoro-phenyl)-2-[(4S)-2,2,4-trimethylpyrrolidin-1-yl]pyridine-3-carboxamide (Compound 1947), N-[(3S)-3-aminopyrrolidin-1-yl]sulfonyl-6-(2-ethoxyphenyl)-2-[(4S)-2,2,4-trimethylpyrrolidin-1-yl]pyridine-3-carboxamide (Compound 2050), N-[(3 S)-3-aminopyrrolidin-1-yl]sulfonyl-6-(2,3-difluoro-phenyl)-2-[(4S)-2,2,4-trimethylpyrrolidin-1-yl]pyridine-3-carboxamide (Compound 2110), N-[(3S)-3-aminopyrrolidin-1-yl]sulfonyl-6-(3-ethoxyphenyl)-2-[(4S)-2,2,4-trimethylpyrrolidin-1-yl]pyridine-3-carboxamide (Compound 2570), N-[(3S)-3-aminopyrrolidin-1-yl]sulfonyl-6-(3,5-difluoro-phenyl)-2-[(4S)-2,2,4-trimethylpyrrolidin-1-yl]pyridine-3-carboxamide (Compound 1716), N-[(3S)-3-aminopyrrolidin-1-yl]sulfonyl-6-(4-ethoxyphenyl)-2-[(4S)-2,2,4-trimethylpyrrolidin-1-yl]pyridine-3-carboxamide (Compound 2525), N-[(3S)-3-aminopyrrolidin-1-yl]sulfonyl-6-(2,5-difluoro-phenyl)-2-[(4S)-2,2,4-trimethylpyrrolidin-1-yl]pyridine-3-carboxamide (Compound 2489), N-[(3S)-3-aminopyrrolidin-1-yl]sulfonyl-6-(2-isopropoxy-phenyl)-2-[(4S)-2,2,4-trimethylpyrrolidin-1-yl]pyridine-3-carboxamide (Compound 1897), N-[(3S)-3-aminopyrrolidin-1-yl]sulfonyl-6-(3-isopropoxy-phenyl)-2-[(4S)-2,2,4-trimethylpyrrolidin-1-yl]pyridine-3-carboxamide (Compound 2156), N-[(3S)-3-aminopyrrolidin-1-yl]sulfonyl-6-(4-isopropoxy-phenyl)-2-[(4S)-2,2,4-trimethylpyrrolidin-1-yl]pyridine-3-carboxamide (Compound 2120), N-[(3S)-3-aminopyrrolidin-1-yl]sulfonyl-6-[2-(trifluoromethoxy)phenyl]-2-[(4S)-2,2,4-trimethylpyrrolidin-1-yl]pyridine-3-carboxamide (Compound 2070), N-[(3S)-3-aminopyrrolidin-1-yl]sulfonyl-6-phenyl-2-[(4S)-2,2,4-trimethylpyrrolidin-1-yl]pyridine-3-carboxamide (Compound 1725), N-[(3S)-3-aminopyrrolidin-1-yl]sulfonyl-6-[3-(trifluoromethoxy)phenyl]-2-[(4S)-2,2,4-trimethylpyrrolidin-1-yl]pyridine-3-carboxamide (Compound 2029), N-[(3S)-3-aminopyrrolidin-1-yl]sulfonyl-6-(2-fluorophenyl)-2-[(4S)-2,2,4-trimethylpyrrolidin-1-yl]pyridine-3-carboxamide (Compound 2045), N-[(3S)-3-aminopyrrolidin-1-yl]sulfonyl-6-[4-(trifluoromethoxy)phenyl]-2-[(4S)-2,2,4-trimethylpyrrolidin-1-yl]pyridine-3-carboxamide (Compound 1763), N-[(3S)-3-aminopyrrolidin-1-yl]sulfonyl-6-(3-fluorophenyl)-2-[(4S)-2,2,4-trimethylpyrrolidin-1-yl]pyridine-3-carboxamide (Compound 2414), N-[(3S)-3-aminopyrrolidin-1-yl]sulfonyl-6-[3-(trifluoromethyl)phenyl]-2-[(4S)-2,2,4-trimethylpyrrolidin-1-yl]pyridine-3-carboxamide (Compound 2220), N-[(3S)-3-aminopyrrolidin-1-yl]sulfonyl-6-[4-(trifluoromethyl)phenyl]-2-[(4S)-2,2,4-trimethylpyrrolidin-1-yl]pyridine-3-carboxamide (Compound 1900), N-[(3S)-3-aminopyrrolidin-1-yl]sulfonyl-6-(3,5-dimethylphenyl)-2-[(4S)-2,2,4-trimethylpyrrolidin-1-yl]pyridine-3-carboxamide (Compound 1839), N-[(3S)-3-aminopyrrolidin-1-yl]sulfonyl-6-(3,4-dimethylphenyl)-2-[(4S)-2,2,4-trimethylpyrrolidin-1-yl]pyridine-3-carboxamide (Compound 2605), N-[(3S)-3-aminopyrrolidin-1-yl]sulfonyl-6-(2,3-dimethylphenyl)-2-[(4S)-2,2,4-trimethylpyrrolidin-1-yl]pyridine-3-carboxamide (Compound 2225), N-[(3S)-3-aminopyrrolidin-1-yl]sulfonyl-6-(2,5-dimethylphenyl)-2-[(4S)-2,2,4-trimethylpyrrolidin-1-yl]pyridine-3-carboxamide (Compound 1736), N-[(3S)-3-aminopyrrolidin-1-yl]sulfonyl-6-(5-fluoro-2-methyl-phenyl)-2-[(4S)-2,2,4-trimethylpyrrolidin-1-yl]pyridine-3-carboxamide (Compound 2490), 2-[(2R,5S)-2,5-dimethylpyrrolidin-1-yl]-6-(3-ethoxy-5-fluoro-phenyl)-N-(1H-pyrazol-5-ylsulfonyl)pyridine-3-carboxamide (Compound 382), 2-[(2S,5R)-2,5-dimethylpyrrolidin-1-yl]-6-(3-isobutoxy-phenyl)-N-(1H-pyrazol-5-ylsulfonyl)pyridine-3-carboxamide (Compound 710), 2-[(2S,5R)-2,5-dimethylpyrrolidin-1-yl]-6-(2-fluoro-5-isobutoxy-phenyl)-N-(1H-pyrazol-5-ylsulfonyl)pyridine-3-carboxamide (Compound 681), 6-(4-chloro-3-propoxy-phenyl)-2-[(2R,5S)-2,5-dimethylpyrrolidin-1-yl]-N-(1H-pyrazol-5-ylsulfonyl)pyridine-3-carboxamide (Compound 832), 6-(4-chloro-3-isobutoxy-phenyl)-2-[(2S,5R)-2,5-dimethylpyrrolidin-1-yl]-N-(1H-pyrazol-5-ylsulfonyl)pyridine-3-carboxamide (Compound 1234), 2-[(2S,5R)-2,5-dimethylpyrrolidin-1-yl]-6-(6-methoxy-2-pyridyl)-N-(1H-pyrazol-5-ylsulfonyl)pyridine-3-carboxamide (Compound 1236), 6-(4-chloro-3-isopropoxy-phenyl)-2-[(2S,5R)-2,5-dimethylpyrrolidin-1-yl]-N-(1H-pyrazol-5-ylsulfonyl)pyridine-3-carboxamide (Compound 701), 2-[(2S,5R)-2,5-dimethylpyrrolidin-1-yl]-6-(3-fluoro-5-isopropoxy-phenyl)-N-(1H-pyrazol-5-ylsulfonyl)pyridine-3-carboxamide (Compound 1285), 2-[(2S,5R)-2,5-dimethylpyrrolidin-1-yl]-6-(4-isobutoxyphenyl)-N-(1H-pyrazol-5-ylsulfonyl)pyridine-3-carboxamide (Compound 1335), 2-[(2S,5R)-2,5-dimethylpyrrolidin-1-yl]-6-(4-isopropylphenyl)-N-(1H-pyrazol-5-ylsulfonyl)pyridine-3-carboxamide (Compound 414), N-[(6-amino-2-pyridyl)sulfonyl]-6-(3-fluoro-5-isobutoxyphenyl)-5-methyl-2-(2,2,4-trimethylpyrrolidin-1-yl)pyridine-3-carboxamide (Compound 1269), N-[(6-amino-2-pyridyl)sulfonyl]-6-(6-isopropoxy-3-pyridyl)-5-methyl-2-(2,2,4-trimethylpyrrolidin-1-yl)pyridine-3-carboxamide (Compound 995), N-[(6-amino-2-pyridyl)sulfonyl]-6-(4-ethoxyphenyl)-5-methyl-2-(2,2,4-trimethylpyrrolidin-1-yl)pyridine-3-carboxamide (Compound 455), N-[(6-amino-2-pyridyl)sulfonyl]-6-(3-methoxyphenyl)-5-methyl-2-(2,2,4-trimethylpyrrolidin-1-yl)pyridine-3-carboxamide (Compound 833), N-[(6-amino-2-pyridyl)sulfonyl]-6-(4-fluorophenyl)-5-methyl-2-(2,2,4-trimethylpyrrolidin-1-yl)pyridine-3-carboxamide (Compound 763), N-[(6-amino-2-pyridyl)sulfonyl]-2-[(2R,5S)-2,5-dimethylpyrrolidin-1-yl]-6-(3-fluoro-5-isobutoxy-phenyl)-5-methyl-pyridine-3-carboxamide (Compound 483), N-[(6-amino-2-pyridyl)sulfonyl]-2-[(2R,5S)-2,5-dimethylpyrrolidin-1-yl]-6-(6-isopropoxy-3-pyridyl)-5-methyl-pyridine-3-carboxamide (Compound 486), N-[(6-amino-2-pyridyl)sulfonyl]-6-(5-methoxy-2-methylphenyl)-5-methyl-2-(2,2,4-trimethylpyrrolidin-1-yl)pyridine-3-carboxamide (Compound 1287), N-[(6-amino-2-pyridyl)sulfonyl]-2-[(2S,5R)-2,5-dimethylpyrrolidin-1-yl]-6-(3-fluoro-5-isobutoxy-phenyl)-4-methoxy-pyridine-3-carboxamide (Compound 1254), N-[(6-amino-2-pyridyl)sulfonyl]-6-(4-pyridyl)-2-(2,2,4-trimethylpyrrolidin-1-yl)pyridine-3-carboxamide (Compound 643), N-[(6-amino-2-pyridyl)sulfonyl]-6-(6-isopropyl-3-pyridyl)-2-(2,2,4-trimethylpyrrolidin-1-yl)pyridine-3-carboxamide (Compound 896), N-[(6-amino-2-pyridyl)sulfonyl]-6-(2-isopropyl-4-pyridyl)-2-(2,2,4-trimethylpyrrolidin-1-yl)pyridine-3-carboxamide (Compound 1262), N-[(6-amino-2-pyridyl)sulfonyl]-6-(1-isopropylpyrazol-4-yl)-2-(2,2,4-trimethylpyrrolidin-1-yl)pyridine-3-carboxamide (Compound 1067), N-[(6-amino-2-pyridyl)sulfonyl]-6-(1-isobutylpyrazol-4-yl)-2-(2,2,4-trimethylpyrrolidin-1-yl)pyridine-3-carboxamide (Compound 631), N-[(6-amino-2-pyridyl)sulfonyl]-6-(2-isopropylpyrazol-3-yl)-2-(2,2,4-trimethylpyrrolidin-1-yl)pyridine-3-carboxamide (Compound 1242), N-[(6-amino-2-pyridyl)sulfonyl]-6-[2-[isobutyl(methyl)amino]-4-pyridyl]-2-(2,2,4-trimethylpyrrolidin-1-yl)pyridine-3-carboxamide (Compound 898), N-[(6-amino-2-pyridyl)sulfonyl]-6-(6-ethoxypyrazin-2-yl)-2-(2,2,4-trimethylpyrrolidin-1-yl)pyridine-3-carboxamide (Compound 1252), N-[(6-amino-2-pyridyl)sulfonyl]-6-(5-isopropoxypyrazin-2-yl)-2-(2,2,4-trimethylpyrrolidin-1-yl)pyridine-3-carboxamide (Compound 965)

N-[(6-amino-2-pyridyl)sulfonyl]-6-(2-isopropoxypyrimidin-5-yl)-2-(2,2,4-trimethylpyrrolidin-1-yl)pyridine-3-carboxamide (Compound 844), N-[(6-amino-2-pyridyl)sulfonyl]-6-(6-isobutoxy-2-methyl-3-pyridyl)-2-(2,2,4-trimethylpyrrolidin-1-yl)pyridine-3-carboxamide (Compound 616), N-[(6-amino-2-pyridyl)sulfonyl]-6-[3-fluoro-5-(2-hydroxy-2-methyl-propoxy)phenyl]-2-[(4S)-2,2,4-trimethylpyrrolidin-1-yl]pyridine-3-carboxamide (Compound 1424), N-(benzenesulfonyl)-6-[3-fluoro-5-(3-hydroxy-2-methylpropoxy)phenyl]-2-[(4S)-2,2,4-trimethylpyrrolidin-1-yl]pyridine-3-carboxamide (Compound 1515), N-[(6-amino-2-pyridyl)sulfonyl]-6-[3-fluoro-5-(3-hydroxy-2-methyl-propoxy)phenyl]-2-[(4S)-2,2,4-trimethylpyrrolidin-1-yl]pyridine-3-carboxamide (Compound 1567), N-(benzenesulfonyl)-6-[3-fluoro-5-(2-hydroxy-2-methylpropoxy)phenyl]-2-[(4S)-2,2,4-trimethylpyrrolidin-1-yl]pyridine-3-carboxamide (Compound 1581), N-[(6-amino-2-pyridyl)sulfonyl]-2-[(2S,5R)-2,5-dimethylpyrrolidin-1-yl]-6-(5-isopropoxy-3-pyridyl)pyridine-3-carboxamide (Compound 400), N-[(6-amino-2-pyridyl)sulfonyl]-6-[5-(cyclopentoxy)-3-pyridyl]-2-[(2S,5R)-2,5-dimethylpyrrolidin-1-yl]pyridine-3-carboxamide (Compound 495), N-[(6-amino-2-pyridyl)sulfonyl]-6-(2-methoxy-3-pyridyl)-2-(2,2,4-trimethylpyrrolidin-1-yl)pyridine-3-carboxamide (Compound 526), N-[(6-amino-2-pyridyl)sulfonyl]-2-[(2S,5R)-2,5-dimethylpyrrolidin-1-yl]-6-(5-isobutoxy-3-pyridyl)pyridine-3-carboxamide (Compound 1224), N-[(6-amino-2-pyridyl)sulfonyl]-6-[(E)-2-cyclopropylvinyl]-2-[(4S)-2,2,4-trimethylpyrrolidin-1-yl]pyridine-3-carboxamide (Compound 1379), N-[(2-amino-3-pyridyl)sulfonyl]-6-(2,3-difluorophenyl)-2-[(4S)-2,2,4-trimethylpyrrolidin-1-yl]pyridine-3-carboxamide (Compound 2291), N-[(2-amino-3-pyridyl)sulfonyl]-6-(3-ethoxyphenyl)-2-[(4S)-2,2,4-trimethylpyrrolidin-1-yl]pyridine-3-carboxamide (Compound 1822), N-[(2-amino-3-pyridyl)sulfonyl]-6-(2,5-difluorophenyl)-2-[(4S)-2,2,4-trimethylpyrrolidin-1-yl]pyridine-3-carboxamide (Compound 2105), N-[(2-amino-3-pyridyl)sulfonyl]-6-(4-ethoxy-3-fluoro-phenyl)-2-[(4S)-2,2,4-trimethylpyrrolidin-1-yl]pyridine-3-carboxamide (Compound 2403), N-[(2-amino-3-pyridyl)sulfonyl]-6-(2,4-dimethylphenyl)-2-[(4S)-2,2,4-trimethylpyrrolidin-1-yl]pyridine-3-carboxamide (Compound 1871), N-[(2-amino-3-pyridyl)sulfonyl]-6-(2-fluoro-5-methyl-phenyl)-2-[(4S)-2,2,4-trimethylpyrrolidin-1-yl]pyridine-3-carboxamide (Compound 2205), N-[(2-amino-3-pyridyl)sulfonyl]-6-(2-isopropoxyphenyl)-2-[(4S)-2,2,4-trimethylpyrrolidin-1-yl]pyridine-3-carboxamide (Compound 2623), N-[(2-amino-3-pyridyl)sulfonyl]-6-(5-ethoxy-2-fluoro-phenyl)-2-[(4S)-2,2,4-trimethylpyrrolidin-1-yl]pyridine-3-carboxamide (Compound 2149), N-[(2-amino-3-pyridyl)sulfonyl]-6-(3-ethoxy-2-fluoro-phenyl)-2-[(4S)-2,2,4-trimethylpyrrolidin-1-yl]pyridine-3-carboxamide (Compound 1847), N-[(2-amino-3-pyridyl)sulfonyl]-6-(2-ethoxy-4-fluoro-phenyl)-2-[(4S)-2,2,4-trimethylpyrrolidin-1-yl]pyridine-3-carboxamide (Compound 1808),
N-[(2-amino-3-pyridyl)sulfonyl]-6-(3-ethoxy-5-fluoro-phenyl)-2-[(4S)-2,2,4-trimethylpyrrolidin-1-yl]pyridine-3-carboxamide (Compound 2018),
N-[(2-amino-3-pyridyl)sulfonyl]-6-(3-ethoxy-4-fluoro-phenyl)-2-[(4S)-2,2,4-trimethylpyrrolidin-1-yl]pyridine-3-carboxamide (Compound 2665),
N-[(2-amino-3-pyridyl)sulfonyl]-6-(3-chlorophenyl)-2-[(4S)-2,2,4-trimethylpyrrolidin-1-yl]pyridine-3-carboxamide (Compound 2183),
N-[(2-amino-3-pyridyl)sulfonyl]-6-(4-methyl-1-naphthyl)-2-[(4S)-2,2,4-trimethylpyrrolidin-1-yl]pyridine-3-carboxamide (Compound 2126),
N-[(2-amino-3-pyridyl)sulfonyl]-6-[2-(trifluoromethoxy)phenyl]-2-[(4S)-2,2,4-trimethylpyrrolidin-1-yl]pyridine-3-carboxamide (Compound 2539),
N-[(2-amino-3-pyridyl)sulfonyl]-6-[3-(trifluoromethoxy)phenyl]-2-[(4S)-2,2,4-trimethylpyrrolidin-1-yl]pyridine-3-carboxamide (Compound 2245),
N-[(2-amino-3-pyridyl)sulfonyl]-6-[4-(trifluoromethoxy)phenyl]-2-[(4S)-2,2,4-trimethylpyrrolidin-1-yl]pyridine-3-carboxamide (Compound 2223),
N-[(2-amino-3-pyridyl)sulfonyl]-6-[2-(trifluoromethyl)phenyl]-2-[(4S)-2,2,4-trimethylpyrrolidin-1-yl]pyridine-3-carboxamide (Compound 2040),
N-[(2-amino-3-pyridyl)sulfonyl]-6-(4,5-difluoro-2-methoxy-phenyl)-2-[(4S)-2,2,4-trimethylpyrrolidin-1-yl]pyridine-3-carboxamide (Compound 2334),
N-[(2-amino-3-pyridyl)sulfonyl]-6-[3-(trifluoromethyl)phenyl]-2-[(4S)-2,2,4-trimethylpyrrolidin-1-yl]pyridine-3-carboxamide (Compound 2593),
N-[(2-amino-3-pyridyl)sulfonyl]-6-(3,5-difluoro-2-methoxy-phenyl)-2-[(4S)-2,2,4-trimethylpyrrolidin-1-yl]pyridine-3-carboxamide (Compound 2006),
N-[(2-amino-3-pyridyl)sulfonyl]-6-(o-tolyl)-2-[(4S)-2,2,4-trimethylpyrrolidin-1-yl]pyridine-3-carboxamide (Compound 1766),
N-[(2-amino-3-pyridyl)sulfonyl]-6-[4-(trifluoromethyl)phenyl]-2-[(4S)-2,2,4-trimethylpyrrolidin-1-yl]pyridine-3-carboxamide (Compound 2048),
N-[(2-amino-3-pyridyl)sulfonyl]-6-(2,3-difluoro-4-methoxy-phenyl)-2-[(4S)-2,2,4-trimethylpyrrolidin-1-yl]pyridine-3-carboxamide (Compound 2302),
N-[(2-amino-3-pyridyl)sulfonyl]-6-(3,5-difluoro-4-methoxy-phenyl)-2-[(4S)-2,2,4-trimethylpyrrolidin-1-yl]pyridine-3-carboxamide (Compound 2457),
N-[(2-amino-3-pyridyl)sulfonyl]-6-(3,4-difluoro-5-methoxy-phenyl)-2-[(4S)-2,2,4-trimethylpyrrolidin-1-yl]pyridine-3-carboxamide (Compound 1998),
N-[(2-amino-3-pyridyl)sulfonyl]-6-(4-methoxy-2,3-dimethyl-phenyl)-2-[(4S)-2,2,4-trimethylpyrrolidin-1-yl]pyridine-3-carboxamide (Compound 2450),
N-[(2-amino-3-pyridyl)sulfonyl]-6-(2,4-difluorophenyl)-2-[(4S)-2,2,4-trimethylpyrrolidin-1-yl]pyridine-3-carboxamide (Compound 2447),
N-[(2-amino-3-pyridyl)sulfonyl]-6-(3-methoxyphenyl)-2-[(4S)-2,2,4-trimethylpyrrolidin-1-yl]pyridine-3-carboxamide (Compound 2164),
N-[(2-amino-3-pyridyl)sulfonyl]-6-(1H-indol-6-yl)-2-[(4S)-2,2,4-trimethylpyrrolidin-1-yl]pyridine-3-carboxamide (Compound 2054),
N-[(2-amino-3-pyridyl)sulfonyl]-6-(3-ethoxy-5-methyl-phenyl)-2-[(4S)-2,2,4-trimethylpyrrolidin-1-yl]pyridine-3-carboxamide (Compound 2241),
N-[(2-amino-3-pyridyl)sulfonyl]-6-(1-methylindol-6-yl)-2-[(4S)-2,2,4-trimethylpyrrolidin-1-yl]pyridine-3-carboxamide (Compound 2401),
N-[(2-amino-3-pyridyl)sulfonyl]-6-(2-cyanophenyl)-2-[(4S)-2,2,4-trimethylpyrrolidin-1-yl]pyridine-3-carboxamide (Compound 2437),
tert-butyl 2-[5-[(2-amino-3-pyridyl)sulfonylcarbamoyl]-6-[(4S)-2,2,4-trimethylpyrrolidin-1-yl]-2-pyridyl]indole-1-carboxylate (Compound 2657),
N-[(2-amino-3-pyridyl)sulfonyl]-6-(2-fluorophenyl)-2-[(4S)-2,2,4-trimethylpyrrolidin-1-yl]pyridine-3-carboxamide (Compound 1790),
N-[(2-amino-3-pyridyl)sulfonyl]-6-(4-ethoxyphenyl)-2-[(4S)-2,2,4-trimethylpyrrolidin-1-yl]pyridine-3-carboxamide (Compound 1945),
N-[(2-amino-3-pyridyl)sulfonyl]-6-(3-fluorophenyl)-2-[(4S)-2,2,4-trimethylpyrrolidin-1-yl]pyridine-3-carboxamide (Compound 1873),
N-[(2-amino-3-pyridyl)sulfonyl]-6-(3-cyanophenyl)-2-[(4S)-2,2,4-trimethylpyrrolidin-1-yl]pyridine-3-carboxamide (Compound 1824),
N-[(2-amino-3-pyridyl)sulfonyl]-6-(4-fluorophenyl)-2-[(4S)-2,2,4-trimethylpyrrolidin-1-yl]pyridine-3-carboxamide (Compound 2435),
N-[(2-amino-3-pyridyl)sulfonyl]-6-(4-cyanophenyl)-2-[(4S)-2,2,4-trimethylpyrrolidin-1-yl]pyridine-3-carboxamide (Compound 2096),
N-[(2-amino-3-pyridyl)sulfonyl]-6-(2-hydroxy-4-methyl-phenyl)-2-[(4S)-2,2,4-trimethylpyrrolidin-1-yl]pyridine-3-carboxamide (Compound 1731),
N-[(2-amino-3-pyridyl)sulfonyl]-6-(3-fluoro-2-hydroxy-phenyl)-2-[(4S)-2,2,4-trimethylpyrrolidin-1-yl]pyridine-3-carboxamide (Compound 2446),
N-[(2-amino-3-pyridyl)sulfonyl]-6-(1H-pyrrolo[2,3-b]pyridin-5-yl)-2-[(4S)-2,2,4-trimethylpyrrolidin-1-yl]pyridine-3-carboxamide (Compound 1714),
N-[(2-amino-3-pyridyl)sulfonyl]-6-(1-isopropylpyrazol-4-yl)-2-[(4S)-2,2,4-trimethylpyrrolidin-1-yl]pyridine-3-carboxamide (Compound 2290),
N-[(2-amino-3-pyridyl)sulfonyl]-6-(4-methoxy-2,6-dimethyl-phenyl)-2-[(4S)-2,2,4-trimethylpyrrolidin-1-yl]pyridine-3-carboxamide (Compound 2607),
N-[(2-amino-3-pyridyl)sulfonyl]-6-(1-isobutylpyrazol-4-yl)-2-[(4S)-2,2,4-trimethylpyrrolidin-1-yl]pyridine-3-carboxamide (Compound 2231),
N-[(2-amino-3-pyridyl)sulfonyl]-6-(6-methoxy-3-pyridyl)-2-[(4S)-2,2,4-trimethylpyrrolidin-1-yl]pyridine-3-carboxamide (Compound 2244),
N-[(2-amino-3-pyridyl)sulfonyl]-6-(2-methoxy-3-pyridyl)-2-[(4S)-2,2,4-trimethylpyrrolidin-1-yl]pyridine-3-carboxamide (Compound 1980),
N-[(2-amino-3-pyridyl)sulfonyl]-6-(2-methoxy-4-pyridyl)-2-[(4S)-2,2,4-trimethylpyrrolidin-1-yl]pyridine-3-carboxamide (Compound 2646),
N-[(2-amino-3-pyridyl)sulfonyl]-6-[6-(dimethylamino)-3-pyridyl]-2-[(4S)-2,2,4-trimethylpyrrolidin-1-yl]pyridine-3-carboxamide (Compound 2319),
N-[(2-amino-3-pyridyl)sulfonyl]-6-(6-methoxy-2-methyl-3-pyridyl)-2-[(4S)-2,2,4-trimethylpyrrolidin-1-yl]pyridine-3-carboxamide (Compound 1866),
N-[(2-amino-3-pyridyl)sulfonyl]-6-[3-(hydroxymethyl)-5-methoxy-phenyl]-2-[(4S)-2,2,4-trimethylpyrrolidin-1-yl]pyridine-3-carboxamide (Compound 2065),
N-[(2-amino-3-pyridyl)sulfonyl]-6-(6-methoxy-5-methyl-3-pyridyl)-2-[(4S)-2,2,4-trimethylpyrrolidin-1-yl]pyridine-3-carboxamide (Compound 2564), N-[(2-amino-3-pyridyl)sulfonyl]-6-(4-isoquinolyl)-2-[(4S)-2,2,4-trimethylpyrrolidin-1-yl]pyridine-3-carboxamide (Compound 2418),
N-[(2-amino-3-pyridyl)sulfonyl]-6-(5-fluoro-6-methoxy-3-pyridyl)-2-[(4S)-2,2,4-trimethylpyrrolidin-1-yl]pyridine-3-carboxamide (Compound 2628),
N-[(2-amino-3-pyridyl)sulfonyl]-6-(3,4-difluorophenyl)-2-[(4S)-2,2,4-trimethylpyrrolidin-1-yl]pyridine-3-carboxamide (Compound 1854),
N-[(2-amino-3-pyridyl)sulfonyl]-6-(6-methoxy-2-pyridyl)-2-[(4S)-2,2,4-trimethylpyrrolidin-1-yl]pyridine-3-carboxamide (Compound 2268),
N-[(2-amino-3-pyridyl)sulfonyl]-6-(2,6-dimethoxy-3-pyridyl)-2-[(4S)-2,2,4-trimethylpyrrolidin-1-yl]pyridine-3-carboxamide (Compound 2091),
N-[(2-amino-3-pyridyl)sulfonyl]-6-(3,5-difluorophenyl)-2-[(4S)-2,2,4-trimethylpyrrolidin-1-yl]pyridine-3-carboxamide (Compound 2272),
N-[(2-amino-3-pyridyl)sulfonyl]-6-(2,3-dimethylphenyl)-2-[(4S)-2,2,4-trimethylpyrrolidin-1-yl]pyridine-3-carboxamide (Compound 1713),
N-[(2-amino-3-pyridyl)sulfonyl]-6-(4-chlorophenyl)-2-[(4S)-2,2,4-trimethylpyrrolidin-1-yl]pyridine-3-carboxamide (Compound 2367),
N-[(2-amino-3-pyridyl)sulfonyl]-6-(3,5-dimethylisoxazol-4-yl)-2-[(4S)-2,2,4-trimethylpyrrolidin-1-yl]pyridine-3-carboxamide (Compound 2215),
N-[(2-amino-3-pyridyl)sulfonyl]-6-(4-hydroxy-2-methylphenyl)-2-[(4S)-2,2,4-trimethylpyrrolidin-1-yl]pyridine-3-carboxamide (Compound 1999),
N-[(2-amino-3-pyridyl)sulfonyl]-6-[4-(difluoromethyl)phenyl]-2-[(4S)-2,2,4-trimethylpyrrolidin-1-yl]pyridine-3-carboxamide (Compound 2644),
N-[(2-amino-3-pyridyl)sulfonyl]-6-(m-tolyl)-2-[(4S)-2,2,4-trimethylpyrrolidin-1-yl]pyridine-3-carboxamide (Compound 1829),
N-[(2-amino-3-pyridyl)sulfonyl]-6-(p-tolyl)-2-[(4S)-2,2,4-trimethylpyrrolidin-1-yl]pyridine-3-carboxamide (Compound 2132),
N-[(2-amino-3-pyridyl)sulfonyl]-6-(4-fluoro-2-hydroxyphenyl)-2-[(4S)-2,2,4-trimethylpyrrolidin-1-yl]pyridine-3-carboxamide (Compound 2653),
N-[(2-amino-3-pyridyl)sulfonyl]-6-(5-fluoro-2-hydroxyphenyl)-2-[(4S)-2,2,4-trimethylpyrrolidin-1-yl]pyridine-3-carboxamide (Compound 2046),
N-[(2-amino-3-pyridyl)sulfonyl]-6-(3-fluoro-5-hydroxyphenyl)-2-[(4S)-2,2,4-trimethylpyrrolidin-1-yl]pyridine-3-carboxamide (Compound 2349),
N-[(2-amino-3-pyridyl)sulfonyl]-6-(2,5-dimethylphenyl)-2-[(4S)-2,2,4-trimethylpyrrolidin-1-yl]pyridine-3-carboxamide (Compound 1951),
N-[(2-amino-3-pyridyl)sulfonyl]-6-(2,3-dihydrobenzofuran-7-yl)-2-[(4S)-2,2,4-trimethylpyrrolidin-1-yl]pyridine-3-carboxamide (Compound 2163),
N-[(2-amino-3-pyridyl)sulfonyl]-6-(4-methoxy-3-methylphenyl)-2-[(4S)-2,2,4-trimethylpyrrolidin-1-yl]pyridine-3-carboxamide (Compound 1747),
N-[(2-amino-3-pyridyl)sulfonyl]-6-(2-hydroxy-3-methylphenyl)-2-[(4S)-2,2,4-trimethylpyrrolidin-1-yl]pyridine-3-carboxamide (Compound 2592),
N-[(2-amino-3-pyridyl)sulfonyl]-6-(2-hydroxy-5-methylphenyl)-2-[(4S)-2,2,4-trimethylpyrrolidin-1-yl]pyridine-3-carboxamide (Compound 2426),
N-[(2-amino-3-pyridyl)sulfonyl]-6-(2-methoxy-3-methylphenyl)-2-[(4S)-2,2,4-trimethylpyrrolidin-1-yl]pyridine-3-carboxamide (Compound 2380),
N-[(2-amino-3-pyridyl)sulfonyl]-6-[3-(hydroxymethyl)phenyl]-2-[(4S)-2,2,4-trimethylpyrrolidin-1-yl]pyridine-3-carboxamide (Compound 1738),
N-[(2-amino-3-pyridyl)sulfonyl]-6-(3-methoxy-4-methylphenyl)-2-[(4S)-2,2,4-trimethylpyrrolidin-1-yl]pyridine-3-carboxamide (Compound 2379),
N-[(2-amino-3-pyridyl)sulfonyl]-6-(5-fluoro-2-methylphenyl)-2-[(4S)-2,2,4-trimethylpyrrolidin-1-yl]pyridine-3-carboxamide (Compound 2660),
N-[(2-amino-3-pyridyl)sulfonyl]-6-(2-hydroxy-3-methoxyphenyl)-2-[(4S)-2,2,4-trimethylpyrrolidin-1-yl]pyridine-3-carboxamide (Compound 2158),
N-[(2-amino-3-pyridyl)sulfonyl]-6-(2-methoxy-5-methylphenyl)-2-[(4S)-2,2,4-trimethylpyrrolidin-1-yl]pyridine-3-carboxamide (Compound 2413),
N-[(2-amino-3-pyridyl)sulfonyl]-6-(3-fluoro-4-methoxyphenyl)-2-[(4S)-2,2,4-trimethylpyrrolidin-1-yl]pyridine-3-carboxamide (Compound 1851),
N-[(2-amino-3-pyridyl)sulfonyl]-6-isobutyl-2-[(4S)-2,2,4-trimethylpyrrolidin-1-yl]pyridine-3-carboxamide (Compound 2150),
N-[(2-amino-3-pyridyl)sulfonyl]-6-(2-fluoro-6-methoxyphenyl)-2-[(4S)-2,2,4-trimethylpyrrolidin-1-yl]pyridine-3-carboxamide (Compound 2033),
N-[(2-amino-3-pyridyl)sulfonyl]-6-(2-fluoro-3-methoxyphenyl)-2-[(4S)-2,2,4-trimethylpyrrolidin-1-yl]pyridine-3-carboxamide (Compound 2562),
N-[(2-amino-3-pyridyl)sulfonyl]-6-(3,4-dimethoxyphenyl)-2-[(4S)-2,2,4-trimethylpyrrolidin-1-yl]pyridine-3-carboxamide (Compound 2664),
N-[(2-amino-3-pyridyl)sulfonyl]-6-(5-fluoro-2-methoxyphenyl)-2-[(4S)-2,2,4-trimethylpyrrolidin-1-yl]pyridine-3-carboxamide (Compound 2189),
N-[(2-amino-3-pyridyl)sulfonyl]-6-(4-fluoro-3-methylphenyl)-2-[(4S)-2,2,4-trimethylpyrrolidin-1-yl]pyridine-3-carboxamide (Compound 2052),
N-[(2-amino-3-pyridyl)sulfonyl]-6-(2-fluoro-5-methoxyphenyl)-2-[(4S)-2,2,4-trimethylpyrrolidin-1-yl]pyridine-3-carboxamide (Compound 2474),
N-[(2-amino-3-pyridyl)sulfonyl]-6-(4-fluoro-2-methoxyphenyl)-2-[(4S)-2,2,4-trimethylpyrrolidin-1-yl]pyridine-3-carboxamide (Compound 2482),
N-[(2-amino-3-pyridyl)sulfonyl]-6-(3-fluoro-5-methoxyphenyl)-2-[(4S)-2,2,4-trimethylpyrrolidin-1-yl]pyridine-3-carboxamide (Compound 1869),
N-[(2-amino-3-pyridyl)sulfonyl]-6-(2-fluoro-4-methoxyphenyl)-2-[(4S)-2,2,4-trimethylpyrrolidin-1-yl]pyridine-3-carboxamide (Compound 1818),
N-[(2-amino-3-pyridyl)sulfonyl]-6-(3-fluoro-2-methoxyphenyl)-2-[(4S)-2,2,4-trimethylpyrrolidin-1-yl]pyridine-3-carboxamide (Compound 2355),
N-[(2-amino-3-pyridyl)sulfonyl]-6-[4-(hydroxymethyl)phenyl]-2-[(4S)-2,2,4-trimethylpyrrolidin-1-yl]pyridine-3-carboxamide (Compound 2590),
N-[(2-amino-3-pyridyl)sulfonyl]-6-(4-fluoro-3-methoxyphenyl)-2-[(4S)-2,2,4-trimethylpyrrolidin-1-yl]pyridine-3-carboxamide (Compound 2124),
N-[(2-amino-3-pyridyl)sulfonyl]-6-(3-fluoro-4-methylphenyl)-2-[(4S)-2,2,4-trimethylpyrrolidin-1-yl]pyridine-3-carboxamide (Compound 2345),
N-[(2-amino-3-pyridyl)sulfonyl]-6-(2-naphthyl)-2-[(4S)-2,2,4-trimethylpyrrolidin-1-yl]pyridine-3-carboxamide (Compound 2280),
N-[(2-amino-3-pyridyl)sulfonyl]-6-(1-naphthyl)-2-[(4S)-2,2,4-trimethylpyrrolidin-1-yl]pyridine-3-carboxamide (Compound 1857), N-[(2-amino-3-pyridyl)sulfonyl]-6-phenyl-2-[(4S)-2,2,4-trimethylpyrrolidin-1-yl]pyridine-3-carboxamide (Compound 1958),
N-[(2-amino-3-pyridyl)sulfonyl]-6-(2-chlorophenyl)-2-[(4S)-2,2,4-trimethylpyrrolidin-1-yl]pyridine-3-carboxamide (Compound 2066),
N-[(2-amino-3-pyridyl)sulfonyl]-6-(3,5-dimethylphenyl)-2-[(4S)-2,2,4-trimethylpyrrolidin-1-yl]pyridine-3-carboxamide (Compound 2127),
N-[(2-amino-3-pyridyl)sulfonyl]-6-(2,4,5-trifluorophenyl)-2-[(4S)-2,2,4-trimethylpyrrolidin-1-yl]pyridine-3-carboxamide (Compound 2035),
N-[(2-amino-3-pyridyl)sulfonyl]-6-(2-fluoro-4-methyl-phenyl)-2-[(4S)-2,2,4-trimethylpyrrolidin-1-yl]pyridine-3-carboxamide (Compound 2613),
N-[(2-amino-3-pyridyl)sulfonyl]-6-(2,3-dihydro-1,4-benzodioxin-6-yl)-2-[(4S)-2,2,4-trimethylpyrrolidin-1-yl]pyridine-3-carboxamide (Compound 2522),
N-[(2-amino-3-pyridyl)sulfonyl]-6-(2-isopropylphenyl)-2-[(4S)-2,2,4-trimethylpyrrolidin-1-yl]pyridine-3-carboxamide (Compound 2172),
N-[(2-amino-3-pyridyl)sulfonyl]-6-(4-methoxyphenyl)-2-[(4S)-2,2,4-trimethylpyrrolidin-1-yl]pyridine-3-carboxamide (Compound 2667),
N-[(2-amino-3-pyridyl)sulfonyl]-6-(2-ethoxy-5-methylphenyl)-2-[(4S)-2,2,4-trimethylpyrrolidin-1-yl]pyridine-3-carboxamide (Compound 1964),
N-[(2-amino-3-pyridyl)sulfonyl]-6-(3-isopropoxyphenyl)-2-[(4S)-2,2,4-trimethylpyrrolidin-1-yl]pyridine-3-carboxamide (Compound 2515),
N-[(2-amino-3-pyridyl)sulfonyl]-6-(3,4-dimethylphenyl)-2-[(4S)-2,2,4-trimethylpyrrolidin-1-yl]pyridine-3-carboxamide (Compound 2017),
N-[(2-amino-3-pyridyl)sulfonyl]-6-(4-isopropoxyphenyl)-2-[(4S)-2,2,4-trimethylpyrrolidin-1-yl]pyridine-3-carboxamide (Compound 1903),
N-[(2-amino-3-pyridyl)sulfonyl]-6-(3-fluoro-2-methyl-phenyl)-2-[(4S)-2,2,4-trimethylpyrrolidin-1-yl]pyridine-3-carboxamide (Compound 1944),
N-[(2-amino-3-pyridyl)sulfonyl]-6-(2-isobutoxyphenyl)-2-[(4S)-2,2,4-trimethylpyrrolidin-1-yl]pyridine-3-carboxamide (Compound 2448),
N-[(2-amino-3-pyridyl)sulfonyl]-6-(3-isopropylphenyl)-2-[(4S)-2,2,4-trimethylpyrrolidin-1-yl]pyridine-3-carboxamide (Compound 1991),
N-[(2-amino-3-pyridyl)sulfonyl]-6-(2,6-dimethoxyphenyl)-2-[(4S)-2,2,4-trimethylpyrrolidin-1-yl]pyridine-3-carboxamide (Compound 1994),
N-[(2-amino-3-pyridyl)sulfonyl]-6-(4-isopropylphenyl)-2-[(4S)-2,2,4-trimethylpyrrolidin-1-yl]pyridine-3-carboxamide (Compound 2368),
N-[(2-amino-3-pyridyl)sulfonyl]-6-(2,3-dimethoxyphenyl)-2-[(4S)-2,2,4-trimethylpyrrolidin-1-yl]pyridine-3-carboxamide (Compound 2436),
N-[(2-amino-3-pyridyl)sulfonyl]-6-(2-hydroxyphenyl)-2-[(4S)-2,2,4-trimethylpyrrolidin-1-yl]pyridine-3-carboxamide (Compound 2257),
N-[(2-amino-3-pyridyl)sulfonyl]-6-(2,5-dimethoxyphenyl)-2-[(4S)-2,2,4-trimethylpyrrolidin-1-yl]pyridine-3-carboxamide (Compound 2195),
N-[(2-amino-3-pyridyl)sulfonyl]-6-(3-hydroxyphenyl)-2-[(4S)-2,2,4-trimethylpyrrolidin-1-yl]pyridine-3-carboxamide (Compound 1820),
N-[(2-amino-3-pyridyl)sulfonyl]-6-[2-(hydroxymethyl)phenyl]-2-[(4S)-2,2,4-trimethylpyrrolidin-1-yl]pyridine-3-carboxamide (Compound 1706),
N-[(2-amino-3-pyridyl)sulfonyl]-6-(4-hydroxyphenyl)-2-[(4S)-2,2,4-trimethylpyrrolidin-1-yl]pyridine-3-carboxamide (Compound 1712),
N-[(2-amino-3-pyridyl)sulfonyl]-6-(2,4-dimethoxyphenyl)-2-[(4S)-2,2,4-trimethylpyrrolidin-1-yl]pyridine-3-carboxamide (Compound 1705),
N-[(2-amino-3-pyridyl)sulfonyl]-6-(3-fluoro-5-methyl-phenyl)-2-[(4S)-2,2,4-trimethylpyrrolidin-1-yl]pyridine-3-carboxamide (Compound 2505),
N-[(2-amino-3-pyridyl)sulfonyl]-6-(2-methoxyphenyl)-2-[(4S)-2,2,4-trimethylpyrrolidin-1-yl]pyridine-3-carboxamide (Compound 1962),
N-[(2-amino-3-pyridyl)sulfonyl]-6-(3,5-dimethoxyphenyl)-2-[(4S)-2,2,4-trimethylpyrrolidin-1-yl]pyridine-3-carboxamide (Compound 1825),
N-[(2-amino-3-pyridyl)sulfonyl]-6-(4-methoxy-2-methyl-phenyl)-2-[(4S)-2,2,4-trimethylpyrrolidin-1-yl]pyridine-3-carboxamide (Compound 2494),
N-[(2-amino-3-pyridyl)sulfonyl]-6-[2-(hydroxymethyl)-4-methoxy-phenyl]-2-[(4S)-2,2,4-trimethylpyrrolidin-1-yl]pyridine-3-carboxamide (Compound 1707),
N-[(2-amino-3-pyridyl)sulfonyl]-6-(2,4-dimethoxypyrimidin-5-yl)-2-[(4S)-2,2,4-trimethylpyrrolidin-1-yl]pyridine-3-carboxamide (Compound 2008),
N-[(6-amino-2-pyridyl)sulfonyl]-6-(4-fluoro-3-methyl-phenyl)-2-[(4S)-2,2,4-trimethylpyrrolidin-1-yl]pyridine-3-carboxamide (Compound 1930),
N-[(6-amino-2-pyridyl)sulfonyl]-6-(3-fluoro-4-methyl-phenyl)-2-[(4S)-2,2,4-trimethylpyrrolidin-1-yl]pyridine-3-carboxamide (Compound 1922),
N-[(6-amino-2-pyridyl)sulfonyl]-6-(4-ethoxy-2,5-dimethyl-phenyl)-2-[(4S)-2,2,4-trimethylpyrrolidin-1-yl]pyridine-3-carboxamide (Compound 2227),
N-[(6-amino-2-pyridyl)sulfonyl]-6-(2-fluoro-4-methyl-phenyl)-2-[(4S)-2,2,4-trimethylpyrrolidin-1-yl]pyridine-3-carboxamide (Compound 1910),
N-[(6-amino-2-pyridyl)sulfonyl]-6-(3-fluoro-2-methyl-phenyl)-2-[(4S)-2,2,4-trimethylpyrrolidin-1-yl]pyridine-3-carboxamide (Compound 2616),
N-[(6-amino-2-pyridyl)sulfonyl]-6-(4-isopropoxypyrazol-1-yl)-2-[(4S)-2,2,4-trimethylpyrrolidin-1-yl]pyridine-3-carboxamide (Compound 2658),
N-[(6-amino-2-pyridyl)sulfonyl]-6-(3-fluoro-5-methyl-phenyl)-2-[(4S)-2,2,4-trimethylpyrrolidin-1-yl]pyridine-3-carboxamide (Compound 2638),
N-[(6-amino-2-pyridyl)sulfonyl]-6-(2,2-difluoro-1,3-benzodioxol-5-yl)-2-[(4S)-2,2,4-trimethylpyrrolidin-1-yl]pyridine-3-carboxamide (Compound 2104),
N-[(6-amino-2-pyridyl)sulfonyl]-6-(3-hydroxy-5-methyl-phenyl)-2-[(4S)-2,2,4-trimethylpyrrolidin-1-yl]pyridine-3-carboxamide (Compound 2232),
N-[(6-amino-2-pyridyl)sulfonyl]-6-(2,4-difluorophenyl)-2-[(4S)-2,2,4-trimethylpyrrolidin-1-yl]pyridine-3-carboxamide (Compound 2372),
N-[(6-amino-2-pyridyl)sulfonyl]-6-(3,5-difluorophenyl)-2-[(4S)-2,2,4-trimethylpyrrolidin-1-yl]pyridine-3-carboxamide (Compound 2236),
N-[(6-amino-2-pyridyl)sulfonyl]-6-(2-hydroxy-3-methyl-phenyl)-2-[(4S)-2,2,4-trimethylpyrrolidin-1-yl]pyridine-3-carboxamide (Compound 2203),
N-[(6-amino-2-pyridyl)sulfonyl]-6-(2-hydroxy-5-methyl-phenyl)-2-[(4S)-2,2,4-trimethylpyrrolidin-1-yl]pyridine-3-carboxamide (Compound 2034),
N-[(6-amino-2-pyridyl)sulfonyl]-6-(3-fluorophenyl)-2-[(4S)-2,2,4-trimethylpyrrolidin-1-yl]pyridine-3-carboxamide (Compound 2566), N-[(6-amino-2-pyridyl)sulfonyl]-6-(3-fluoro-2-hydroxy-phenyl)-2-[(4S)-2,2,4-trimethylpyrrolidin-1-yl]pyridine-3-carboxamide (Compound 2386), N-[(6-amino-2-pyridyl)sulfonyl]-6-(2-hydroxyphenyl)-2-[(4S)-2,2,4-trimethylpyrrolidin-1-yl]pyridine-3-carboxamide (Compound 2555), N-[(6-amino-2-pyridyl)sulfonyl]-6-(2-hydroxy-4-methyl-phenyl)-2-[(4S)-2,2,4-trimethylpyrrolidin-1-yl]pyridine-3-carboxamide (Compound 2043), N-[(6-amino-2-pyridyl)sulfonyl]-6-(3,4-difluorophenyl)-2-[(4S)-2,2,4-trimethylpyrrolidin-1-yl]pyridine-3-carboxamide (Compound 2559), N-[(6-amino-2-pyridyl)sulfonyl]-6-(3-isobutoxyphenyl)-2-[(4S)-2,2,4-trimethylpyrrolidin-1-yl]pyridine-3-carboxamide (Compound 1969), N-[(6-amino-2-pyridyl)sulfonyl]-6-[4-(trifluoromethoxy)phenyl]-2-[(4S)-2,2,4-trimethylpyrrolidin-1-yl]pyridine-3-carboxamide (Compound 1785), N-[(6-amino-2-pyridyl)sulfonyl]-6-(3,5-difluoro-4-isopropoxy-phenyl)-2-[(4S)-2,2,4-trimethylpyrrolidin-1-yl]pyridine-3-carboxamide (Compound 2608), N-[(6-amino-2-pyridyl)sulfonyl]-6-(3-ethoxy-4,5-dimethyl-phenyl)-2-[(4S)-2,2,4-trimethylpyrrolidin-1-yl]pyridine-3-carboxamide (Compound 1931), N-[(6-amino-2-pyridyl)sulfonyl]-6-[3-(trifluoromethyl)phenyl]-2-[(4S)-2,2,4-trimethylpyrrolidin-1-yl]pyridine-3-carboxamide (Compound 2392), N-[(6-amino-2-pyridyl)sulfonyl]-6-(3,5-dimethylphenyl)-2-[(4S)-2,2,4-trimethylpyrrolidin-1-yl]pyridine-3-carboxamide (Compound 1771), N-[(6-amino-2-pyridyl)sulfonyl]-6-(5-methyl-2-propoxy-phenyl)-2-[(4S)-2,2,4-trimethylpyrrolidin-1-yl]pyridine-3-carboxamide (Compound 2085), N-[(6-amino-2-pyridyl)sulfonyl]-6-[4-(trifluoromethyl)phenyl]-2-[(4S)-2,2,4-trimethylpyrrolidin-1-yl]pyridine-3-carboxamide (Compound 2296), N-[(6-amino-2-pyridyl)sulfonyl]-6-(2,3-dimethylphenyl)-2-[(4S)-2,2,4-trimethylpyrrolidin-1-yl]pyridine-3-carboxamide (Compound 2287), N-[(6-amino-2-pyridyl)sulfonyl]-6-(1-isobutylpyrazol-3-yl)-2-[(4S)-2,2,4-trimethylpyrrolidin-1-yl]pyridine-3-carboxamide (Compound 2114), N-[(6-amino-2-pyridyl)sulfonyl]-6-[3-(trifluoromethoxy)phenyl]-2-[(4S)-2,2,4-trimethylpyrrolidin-1-yl]pyridine-3-carboxamide (Compound 2366), N-[(6-amino-2-pyridyl)sulfonyl]-6-[4-(difluoromethoxy)-3-methyl-phenyl]-2-[(4S)-2,2,4-trimethylpyrrolidin-1-yl]pyridine-3-carboxamide (Compound 2543), N-[(6-amino-2-pyridyl)sulfonyl]-6-(5-fluoro-2-methyl-phenyl)-2-[(4S)-2,2,4-trimethylpyrrolidin-1-yl]pyridine-3-carboxamide (Compound 2394), N-[(6-amino-2-pyridyl)sulfonyl]-6-(4-ethoxy-2-methyl-phenyl)-2-(2,2,4-trimethylpyrrolidin-1-yl)pyridine-3-carboxamide (Compound 536), and N-[(6-amino-2-pyridyl)sulfonyl]-6-(4-methoxy-2,5-dimethyl-phenyl)-2-(2,2,4-trimethylpyrrolidin-1-yl)pyridine-3-carboxamide (Compound 1259).

Preparation 63: N-[(6-amino-2-pyridyl)sulfonyl]-6-[6-(cyclopropylmethoxy)-3-pyridyl]-2-[(2S,5R)-2,5-dimethylpyrrolidin-1-yl]pyridine-3-carboxamide (Compound 789)

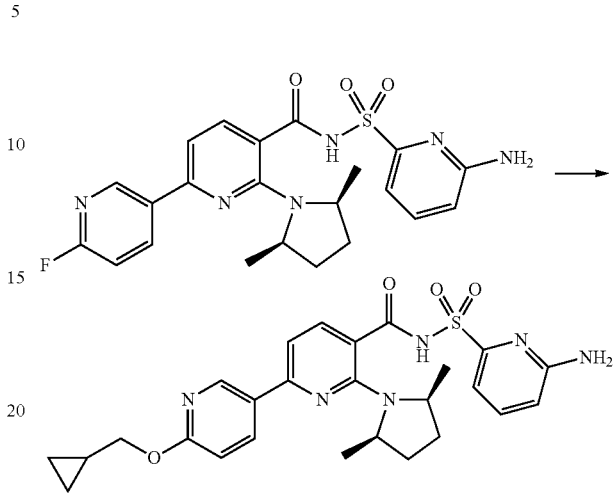

N-[(6-amino-2-pyridyl)sulfonyl]-2-[(2S,5R)-2,5-dimethylpyrrolidin-1-yl]-6-(6-fluoro-3-pyridyl)pyridine-3-carboxamide (50. mg, 0.11 mmol) and cyclopropylmethanol (77 mg, 1.1 mmol) were combined in DMSO (1 mL), cooled down to 0° C. and NaH (12.75 mg, 0.5315 mmol) was added to the reaction mixture. The mixture was heated to 90° C. for 3 h. The reaction mixture was filtered and then purified using a reverse phase HPLC-MS method using a Luna C18 column (50×21.2 mm, 5 µm particle size) sold by Phenomenex (pn: 00B-4252-P0-AX), and a dual gradient run from 1-99% mobile phase B over 15.0 minutes. Mobile phase A=H$_2$O (containing 5 mM HCl). Mobile phase B=CH$_3$CN. Flow rate=35 mL/min, injection volume=950 µL, and column temperature=25° C. The UV absorption at 254 nm is used to collect fractions. The desired fractions were collected, neutralized with 20 mL of NaHCO$_3$, extracted with ethyl acetate, washed with brine, dried over sodium sulfate, filtered, and concentrated to give N-[(6-amino-2-pyridyl)sulfonyl]-6-[6-(cyclopropylmethoxy)-3-pyridyl]-2-[(2S,5R)-2,5-dimethylpyrrolidin-1-yl]pyridine-3-carboxamide (Compound 789) (24 mg, 0.046-mmol, 42%). 1H NMR (400 MHz, DMSO-d$_6$) δ 8.78 (d, J=2.4 Hz, 1H), 8.28 (dd, J=8.7, 2.5 Hz, 1H), 7.60-7.42 (m, 2H), 7.01 (bs, 2H), 6.87 (d, J=8.7 Hz, 1H), 6.51 (d, J=8.6 Hz, 1H), 6.23 (bs, 2H), 4.23 (s, 2H), 4.13 (d, J=7.1 Hz, 2H), 1.86 (bs, 2H), 1.56 (bs, 2H), 1.25 (dddd, J=11.9, 7.3, 5.4, 2.6 Hz, 1H), 1.04 (d, J=6.1 Hz, 6H), 0.59-0.49 (m, 2H), 0.36-0.26 (m, 2H). ESI-MS m/z calc. 522.2049, found 523.3 (M+1)$^+$; Retention time: 1.96 minutes The following compound can be synthesized using the procedures described herein:

N-[(6-amino-2-pyridyl)sulfonyl]-6-[6-(2,2-dimethylpropoxy)-3-pyridyl]-2-[(2S,5R)-2,5-dimethylpyrrolidin-1-yl]pyridine-3-carboxamide (Compound 1270), N-[(6-amino-2-pyridyl)sulfonyl]-6-(6-isobutoxy-4-methyl-2-pyridyl)-2-[(4S)-2,2,4-trimethylpyrrolidin-1-yl]pyridine-3-carboxamide (Compound 1656), N-[(6-amino-2-pyridyl)sulfonyl]-6-(6-ethoxy-4-methyl-2-pyridyl)-2-[(4S)-2,2,4-trimethylpyrrolidin-1-yl]pyridine-3-carboxamide (Compound 1512), N-[(6-amino-2-pyridyl)sulfonyl]-6-(6-isopropoxy-4-methyl-2-pyridyl)-2-[(4S)-2,2,4-trimethylpyrrolidin-1-yl]pyridine-3-carboxamide (Compound 1637), N-[(6-amino-2-pyridyl)sulfonyl]-6-[6-(difluoromethoxy)-3-pyridyl]-2-[(2S,5R)-2,5-dimethylpyrrolidin-1-yl]pyridine-3-carboxamide (Compound 1679),
N-[(6-amino-2-pyridyl)sulfonyl]-2-[(2R,5S)-2,5-dimethylpyrrolidin-1-yl]-6-(6-isobutoxy-2-methyl-3-pyridyl)pyridine-3-carboxamide (Compound 1537),
N-[(6-amino-2-pyridyl)sulfonyl]-6-[6-[2-(2-ethoxyethoxy)ethyl-methyl-amino]-5-methyl-3-pyridyl]-2-[(4S)-2,2,4-trimethylpyrrolidin-1-yl]pyridine-3-carboxamide (Compound 2684),
N-[(6-amino-2-pyridyl)sulfonyl]-6-[6-[2-ethoxyethyl(methyl)amino]-5-methyl-3-pyridyl]-2-[(4S)-2,2,4-trimethylpyrrolidin-1-yl]pyridine-3-carboxamide (Compound 2685),
N-[(6-amino-2-pyridyl)sulfonyl]-6-[6-(2-ethoxyethylamino)-5-methyl-3-pyridyl]-2-[(4S)-2,2,4-trimethylpyrrolidin-1-yl]pyridine-3-carboxamide (Compound 2686),
N-[(6-amino-2-pyridyl)sulfonyl]-2-[(2R,5S)-2,5-dimethylpyrrolidin-1-yl]-6-(6-isopropoxy-2-methyl-3-pyridyl)pyridine-3-carboxamide (Compound 1623),
N-[(6-amino-2-pyridyl)sulfonyl]-2-[(2R,5S)-2,5-dimethylpyrrolidin-1-yl]-6-(6-isopropoxy-4-methyl-3-pyridyl)pyridine-3-carboxamide (Compound 1514),
N-[(6-amino-2-pyridyl)sulfonyl]-2-[(2S,5R)-2,5-dimethylpyrrolidin-1-yl]-6-[6-(isobutylamino)-3-pyridyl]pyridine-3-carboxamide (Compound 1398),
N-[(6-amino-2-pyridyl)sulfonyl]-6-[6-[[(1S)-1,3-dimethylbutyl]amino]-3-pyridyl]-2-[(2S,5R)-2,5-dimethylpyrrolidin-1-yl]pyridine-3-carboxamide (Compound 1463),
N-[(6-amino-2-pyridyl)sulfonyl]-2-[(2S,5R)-2,5-dimethylpyrrolidin-1-yl]-6-[6-[isobutyl(methyl)amino]-3-pyridyl]pyridine-3-carboxamide (Compound 1506),
N-[(6-amino-2-pyridyl)sulfonyl]-2-[(2R,5S)-2,5-dimethylpyrrolidin-1-yl]-6-[6-(1-ethylpropylamino)-3-pyridyl]pyridine-3-carboxamide (Compound 1397),
N-[(6-amino-2-pyridyl)sulfonyl]-6-[6-[[(1S)-1,2-dimethylpropyl]amino]-3-pyridyl]-2-[(2S,5R)-2,5-dimethylpyrrolidin-1-yl]pyridine-3-carboxamide (Compound 1399),
N-[(6-amino-2-pyridyl)sulfonyl]-6-[6-[isopropyl(methyl)amino]-5-methyl-3-pyridyl]-2-[(4S)-2,2,4-trimethylpyrrolidin-1-yl]pyridine-3-carboxamide (Compound 2687),
N-[(6-amino-2-pyridyl)sulfonyl]-6-[6-(isopropylamino)-5-methyl-3-pyridyl]-2-[(4S)-2,2,4-trimethylpyrrolidin-1-yl]pyridine-3-carboxamide (Compound 2688),
N-[(6-amino-2-pyridyl)sulfonyl]-6-[6-[ethyl(methyl)amino]-5-methyl-3-pyridyl]-2-[(4S)-2,2,4-trimethylpyrrolidin-1-yl]pyridine-3-carboxamide (Compound 2689),
N-[(6-amino-2-pyridyl)sulfonyl]-6-[6-[[(1R)-1,2-dimethylpropyl]amino]-3-pyridyl]-2-[(2S,5R)-2,5-dimethylpyrrolidin-1-yl]pyridine-3-carboxamide (Compound 1442),
N-[(6-amino-2-pyridyl)sulfonyl]-6-[6-[[(1R)-1,3-dimethylbutyl]amino]-3-pyridyl]-2-[(2S,5R)-2,5-dimethylpyrrolidin-1-yl]pyridine-3-carboxamide (Compound 1527),
N-[(6-amino-2-pyridyl)sulfonyl]-2-[(2S,5R)-2,5-dimethylpyrrolidin-1-yl]-6-(4-isobutoxy-2-pyridyl)pyridine-3-carboxamide (Compound 389),
N-[(6-amino-2-pyridyl)sulfonyl]-6-(6-isobutoxy-2-pyridyl)-2-(2,2,4-trimethylpyrrolidin-1-yl)pyridine-3-carboxamide (Compound 397),
methyl 2-[[5-[5-[(6-amino-2-pyridyl)sulfonylcarbamoyl]-6-[(2S,5R)-2,5-dimethylpyrrolidin-1-yl]-2-pyridyl]-2-pyridyl]oxy]propanoate (Compound 723),
N-[(6-amino-2-pyridyl)sulfonyl]-6-(6-isobutoxypyrazin-2-yl)-2-[(4S)-2,2,4-trimethylpyrrolidin-1-yl]pyridine-3-carboxamide (Compound 1523),
N-[(6-amino-2-pyridyl)sulfonyl]-6-[6-[isobutyl(methyl)amino]-3-pyridyl]-2-(2,2,4-trimethylpyrrolidin-1-yl)pyridine-3-carboxamide (Compound 412),
N-[(6-amino-2-pyridyl)sulfonyl]-2-[(2S,5R)-2,5-dimethylpyrrolidin-1-yl]-6-(6-isobutoxy-2-pyridyl)pyridine-3-carboxamide (Compound 432),
N-[(6-amino-2-pyridyl)sulfonyl]-6-[6-(isopropylamino)-3-pyridyl]-2-(2,2,4-trimethylpyrrolidin-1-yl)pyridine-3-carboxamide (Compound 437),
N-[(6-amino-2-pyridyl)sulfonyl]-6-(6-isobutoxy-3-pyridyl)-2-(2,2,4-trimethylpyrrolidin-1-yl)pyridine-3-carboxamide (Compound 471),
N-[(6-amino-2-pyridyl)sulfonyl]-2-[(2S,5R)-2,5-dimethylpyrrolidin-1-yl]-6-(6-isobutoxy-3-pyridyl)pyridine-3-carboxamide (Compound 544),
N-[(6-amino-2-pyridyl)sulfonyl]-6-[6-(isobutylamino)-3-pyridyl]-2-(2,2,4-trimethylpyrrolidin-1-yl)pyridine-3-carboxamide (Compound 569),
N-[(6-amino-2-pyridyl)sulfonyl]-6-[6-(1-ethylpropoxy)-2-pyridyl]-2-(2,2,4-trimethylpyrrolidin-1-yl)pyridine-3-carboxamide (Compound 580),
N-[(6-amino-2-pyridyl)sulfonyl]-6-(6-isopropoxy-2-pyridyl)-2-(2,2,4-trimethylpyrrolidin-1-yl)pyridine-3-carboxamide (Compound 708),
N-[(6-amino-2-pyridyl)sulfonyl]-6-[6-(1,2-dimethylpropoxy)-2-pyridyl]-2-(2,2-dimethylpyrrolidin-1-yl)pyridine-3-carboxamide (Compound 717),
N-[(6-amino-2-pyridyl)sulfonyl]-6-[6-(2,2-dimethylpropoxy)pyrazin-2-yl]-2-(2,2,4-trimethylpyrrolidin-1-yl)pyridine-3-carboxamide (Compound 779),
N-[(6-amino-2-pyridyl)sulfonyl]-6-[6-(diethylamino)-3-pyridyl]-2-(2,2,4-trimethylpyrrolidin-1-yl)pyridine-3-carboxamide (Compound 796),
N-[(6-amino-2-pyridyl)sulfonyl]-6-(6-isopropoxy-2-methyl-3-pyridyl)-2-(2,2,4-trimethylpyrrolidin-1-yl)pyridine-3-carboxamide (Compound 814),
N-[(6-amino-2-pyridyl)sulfonyl]-6-[6-[isobutyl(methyl)amino]-2-methyl-3-pyridyl]-2-(2,2,4-trimethylpyrrolidin-1-yl)pyridine-3-carboxamide (Compound 827),
N-[(6-amino-2-pyridyl)sulfonyl]-6-[6-(1,3-dimethylbutoxy)-2-pyridyl]-2-(2,2-dimethylpyrrolidin-1-yl)pyridine-3-carboxamide (Compound 846),
N-[(6-amino-2-pyridyl)sulfonyl]-6-(6-isopentyloxy-3-pyridyl)-2-(2,2,4-trimethylpyrrolidin-1-yl)pyridine-3-carboxamide (Compound 848),
N-[(6-amino-2-pyridyl)sulfonyl]-6-(6-isobutoxy-4-methyl-3-pyridyl)-2-(2,2,4-trimethylpyrrolidin-1-yl)pyridine-3-carboxamide (Compound 851),
N-[(6-amino-2-pyridyl)sulfonyl]-6-(6-isopropoxy-4-methyl-3-pyridyl)-2-(2,2,4-trimethylpyrrolidin-1-yl)pyridine-3-carboxamide (Compound 905),
N-[(6-amino-2-pyridyl)sulfonyl]-6-[6-(isopropylamino)-2-pyridyl]-2-(2,2,4-trimethylpyrrolidin-1-yl)pyridine-3-carboxamide (Compound 951),
N-[(6-amino-2-pyridyl)sulfonyl]-6-(6-isobutoxypyrazin-2-yl)-2-(2,2,4-trimethylpyrrolidin-1-yl)pyridine-3-carboxamide (Compound 988),
N-[(6-amino-2-pyridyl)sulfonyl]-2-(2,2-dimethylpyrrolidin-1-yl)-6-(6-isobutoxy-2-pyridyl)pyridine-3-carboxamide (Compound 1011),
N-[(6-amino-2-pyridyl)sulfonyl]-6-[6-(isobutylamino)-2-pyridyl]-2-(2,2,4-trimethylpyrrolidin-1-yl)pyridine-3-carboxamide (Compound 1059),
N-[(6-amino-2-pyridyl)sulfonyl]-6-[6-(2,2-dimethylpropoxy)-2-pyridyl]-2-(2,2,4-trimethylpyrrolidin-1-yl)pyridine-3-carboxamide (Compound 1062), N-[(6-amino-2-pyridyl)sulfonyl]-6-[6-(1-ethylpropoxy)-3-pyridyl]-2-(2,2,4-trimethylpyrrolidin-1-yl)pyridine-3-carboxamide (Compound 1076), N-[(6-amino-2-pyridyl)sulfonyl]-6-(6-isopentyloxy-2-pyridyl)-2-(2,2,4-trimethylpyrrolidin-1-yl)pyridine-3-carboxamide (Compound 1135), N-[(6-amino-2-pyridyl)sulfonyl]-6-[6-(2,2-dimethylpropoxy)-4-methyl-3-pyridyl]-2-(2,2,4-trimethylpyrrolidin-1-yl)pyridine-3-carboxamide (Compound 1160), N-[(6-amino-2-pyridyl)sulfonyl]-6-[6-(2,2-dimethylpropoxy)-3-pyridyl]-2-(2,2,4-trimethylpyrrolidin-1-yl)pyridine-3-carboxamide (Compound 1181), N-[(6-amino-2-pyridyl)sulfonyl]-6-[6-(2,2-dimethylpropoxy)-2-pyridyl]-2-(2,2-dimethylpyrrolidin-1-yl)pyridine-3-carboxamide (Compound 1328), N-[(6-amino-2-pyridyl)sulfonyl]-6-[6-(diethylamino)-2-pyridyl]-2-(2,2,4-trimethylpyrrolidin-1-yl)pyridine-3-carboxamide (Compound 1345), N-[(6-amino-2-pyridyl)sulfonyl]-6-[2-(1,3-dimethylbutoxy)-4-pyridyl]-2-(2,2,4-trimethylpyrrolidin-1-yl)pyridine-3-carboxamide (Compound 384), N-[(6-amino-2-pyridyl)sulfonyl]-6-[2-(isobutylamino)-4-pyridyl]-2-(2,2,4-trimethylpyrrolidin-1-yl)pyridine-3-carboxamide (Compound 523), N-[(6-amino-2-pyridyl)sulfonyl]-6-(2-propoxy-4-pyridyl)-2-(2,2,4-trimethylpyrrolidin-1-yl)pyridine-3-carboxamide (Compound 491), N-[(6-amino-2-pyridyl)sulfonyl]-6-(2-isobutoxy-4-pyridyl)-2-(2,2,4-trimethylpyrrolidin-1-yl)pyridine-3-carboxamide (Compound 1192), N-[(6-amino-2-pyridyl)sulfonyl]-6-(2-isopropoxy-4-pyridyl)-2-(2,2,4-trimethylpyrrolidin-1-yl)pyridine-3-carboxamide (Compound 402), N-[(6-amino-2-pyridyl)sulfonyl]-6-(2-isobutoxy-4-pyridyl)-2-[(4S)-2,2,4-trimethylpyrrolidin-1-yl]pyridine-3-carboxamide (Compound 1618), N-[(6-amino-2-pyridyl)sulfonyl]-6-[6-(2,2-dimethylpropoxy)-3-methyl-2-pyridyl]-2-(2,2,4-trimethylpyrrolidin-1-yl)pyridine-3-carboxamide (Compound 1645), N-[(6-amino-2-pyridyl)sulfonyl]-6-(6-isobutoxy-3-methyl-2-pyridyl)-2-(2,2,4-trimethylpyrrolidin-1-yl)pyridine-3-carboxamide (Compound 1659), N-[(6-amino-2-pyridyl)sulfonyl]-6-[6-(2,2-dimethylpropoxy)-2-pyridyl]-2-[(4S)-2,2,4-trimethylpyrrolidin-1-yl]pyridine-3-carboxamide (Compound 1663), N-[(6-amino-2-pyridyl)sulfonyl]-6-[6-(2,2-dimethylpropoxy)-5-methyl-2-pyridyl]-2-(2,2,4-trimethylpyrrolidin-1-yl)pyridine-3-carboxamide (Compound 1610), N-[(6-amino-2-pyridyl)sulfonyl]-6-(6-ethoxy-5-methyl-2-pyridyl)-2-(2,2,4-trimethylpyrrolidin-1-yl)pyridine-3-carboxamide (Compound 1363), N-[(6-amino-2-pyridyl)sulfonyl]-6-[6-(diethylamino)-3-methyl-2-pyridyl]-2-(2,2,4-trimethylpyrrolidin-1-yl)pyridine-3-carboxamide (Compound 1383), N-[(6-amino-2-pyridyl)sulfonyl]-6-[6-(isobutylamino)-3-methyl-2-pyridyl]-2-(2,2,4-trimethylpyrrolidin-1-yl)pyridine-3-carboxamide (Compound 1417), N-[(6-amino-2-pyridyl)sulfonyl]-6-[6-(2,2-dimethylpropoxy)-3-pyridyl]-2-[(4S)-2,2,4-trimethylpyrrolidin-1-yl]pyridine-3-carboxamide (Compound 1504), N-[(6-amino-2-pyridyl)sulfonyl]-6-[6-(cyclobutoxy)-3-pyridyl]-2-[(2S,5R)-2,5-dimethylpyrrolidin-1-yl]pyridine-3-carboxamide (Compound 428), N-[(6-amino-2-pyridyl)sulfonyl]-2-[(2S,5R)-2,5-dimethylpyrrolidin-1-yl]-6-[6-(2-hydroxy-1-methyl-ethoxy)-3-pyridyl]pyridine-3-carboxamide (Compound 998), N-[(6-amino-2-pyridyl)sulfonyl]-6-[6-[(1R)-2-benzyloxy-1-methyl-ethoxy]-3-pyridyl]-2-[(2S,5R)-2,5-dimethylpyrrolidin-1-yl]pyridine-3-carboxamide (Compound 576), N-[(6-amino-2-pyridyl)sulfonyl]-6-(6-ethoxy-5-methyl-3-pyridyl)-2-[(4S)-2,2,4-trimethylpyrrolidin-1-yl]pyridine-3-carboxamide (Compound 1727), N-[(6-amino-2-pyridyl)sulfonyl]-6-[6-(diethylamino)-5-methyl-3-pyridyl]-2-[(4S)-2,2,4-trimethylpyrrolidin-1-yl]pyridine-3-carboxamide (Compound 1915), N-[(6-amino-2-pyridyl)sulfonyl]-6-[6-[2-[2-(2-azidoethoxy)ethoxy]ethoxy]-5-methyl-3-pyridyl]-2-[(4S)-2,2,4-trimethylpyrrolidin-1-yl]pyridine-3-carboxamide, N-[(6-amino-2-pyridyl)sulfonyl]-6-(6-isobutoxy-5-methyl-3-pyridyl)-2-[(4S)-2,2,4-trimethylpyrrolidin-1-yl]pyridine-3-carboxamide (Compound 1741), N-[(6-amino-2-pyridyl)sulfonyl]-6-[6-[isobutyl(methyl)amino]-5-methyl-3-pyridyl]-2-[(4S)-2,2,4-trimethylpyrrolidin-1-yl]pyridine-3-carboxamide (Compound 2279), N-[(6-amino-2-pyridyl)sulfonyl]-6-[5-methyl-6-[(1R)-1-methylpropoxy]-3-pyridyl]-2-[(4S)-2,2,4-trimethylpyrrolidin-1-yl]pyridine-3-carboxamide (Compound 2576), N-[(6-amino-2-pyridyl)sulfonyl]-6-(6-isopropoxy-5-methyl-3-pyridyl)-2-[(4S)-2,2,4-trimethylpyrrolidin-1-yl]pyridine-3-carboxamide (Compound 2170), N-[(6-amino-2-pyridyl)sulfonyl]-6-[6-[2-(2-ethoxyethoxy)ethoxy]-5-methyl-3-pyridyl]-2-[(4S)-2,2,4-trimethylpyrrolidin-1-yl]pyridine-3-carboxamide (Compound 1715), N-[(6-amino-2-pyridyl)sulfonyl]-6-[5-methyl-6-[(1S)-1-methylpropoxy]-3-pyridyl]-2-[(4S)-2,2,4-trimethylpyrrolidin-1-yl]pyridine-3-carboxamide (Compound 1728), N-[(6-amino-2-pyridyl)sulfonyl]-6-[6-[2-[2-(2-isopropoxyethoxy)ethoxy]ethoxy]-5-methyl-3-pyridyl]-2-[(4S)-2,2,4-trimethylpyrrolidin-1-yl]pyridine-3-carboxamide (Compound 1787), N-[(6-amino-2-pyridyl)sulfonyl]-6-[6-[2-(3-but-3-ynyldiazirin-3-yl)ethoxy]-5-methyl-3-pyridyl]-2-[(4S)-2,2,4-trimethylpyrrolidin-1-yl]pyridine-3-carboxamide, N-[(6-amino-2-pyridyl)sulfonyl]-6-[6-(2-ethoxyethoxy)-5-methyl-3-pyridyl]-2-[(4S)-2,2,4-trimethylpyrrolidin-1-yl]pyridine-3-carboxamide (Compound 2404), N-[(6-amino-2-pyridyl)sulfonyl]-6-[6-(2-isopropoxyethoxy)-5-methyl-3-pyridyl]-2-[(4S)-2,2,4-trimethylpyrrolidin-1-yl]pyridine-3-carboxamide (Compound 1973), N-[(6-amino-2-pyridyl)sulfonyl]-6-[6-(2-methoxyethoxy)-5-methyl-3-pyridyl]-2-[(4S)-2,2,4-trimethylpyrrolidin-1-yl]pyridine-3-carboxamide (Compound 2582), N-[(6-amino-2-pyridyl)sulfonyl]-6-[2-(2-ethoxyethoxy)-6-methyl-4-pyridyl]-2-[(4S)-2,2,4-trimethylpyrrolidin-1-yl]pyridine-3-carboxamide (Compound 1948), N-[(6-amino-2-pyridyl)sulfonyl]-6-[2-(2-isopropoxyethoxy)-6-methyl-4-pyridyl]-2-[(4S)-2,2,4-trimethylpyrrolidin-1-yl]pyridine-3-carboxamide (Compound 2079), N-[(6-amino-2-pyridyl)sulfonyl]-6-[2-(diethylamino)-6-methyl-4-pyridyl]-2-[(4S)-2,2,4-trimethylpyrrolidin-1-yl]pyridine-3-carboxamide (Compound 1739), N-[(6-amino-2-pyridyl)sulfonyl]-6-(2-isobutoxy-6-methyl-4-pyridyl)-2-[(4S)-2,2,4-trimethylpyrrolidin-1-yl]pyridine-3-carboxamide (Compound 2010), N-[(6-amino-2-pyridyl)sulfonyl]-6-[2-[2-(2-ethoxyethoxy)ethoxy]-6-methyl-4-pyridyl]-2-[(4S)-2,2,4-trimethylpyrrolidin-1-yl]pyridine-3-carboxamide (Compound 1812), N-[(6-amino-2-pyridyl)sulfonyl]-6-(2-ethoxy-6-methyl-4-pyridyl)-2-[(4S)-2,2,4-trimethylpyrrolidin-1-yl]pyridine-3-carboxamide (Compound 2364), N-[(6-amino-2-pyridyl)sulfonyl]-6-(2-isopropoxy-6-methyl-4-pyridyl)-2-[(4S)-2,2,4-trimethylpyrrolidin-1-yl]pyridine-3-carboxamide (Compound 2306),
N-[(6-amino-2-pyridyl)sulfonyl]-6-(2-methoxy-6-methyl-4-pyridyl)-2-[(4S)-2,2,4-trimethylpyrrolidin-1-yl]pyridine-3-carboxamide (Compound 1748),
N-[(2-amino-3-pyridyl)sulfonyl]-6-(6-isopropoxy-5-methyl-3-pyridyl)-2-[(4S)-2,2,4-trimethylpyrrolidin-1-yl]pyridine-3-carboxamide (Compound 1702),
N-[(2-amino-3-pyridyl)sulfonyl]-6-[6-(2-ethoxyethoxy)-5-methyl-3-pyridyl]-2-[(4S)-2,2,4-trimethylpyrrolidin-1-yl]pyridine-3-carboxamide (Compound 2497),
N-[(2-amino-3-pyridyl)sulfonyl]-6-(6-ethoxy-5-methyl-3-pyridyl)-2-[(4S)-2,2,4-trimethylpyrrolidin-1-yl]pyridine-3-carboxamide (Compound 2651),
N-[(2-amino-3-pyridyl)sulfonyl]-6-[6-[2-(2-ethoxyethoxy)ethoxy]-5-methyl-3-pyridyl]-2-[(4S)-2,2,4-trimethylpyrrolidin-1-yl]pyridine-3-carboxamide (Compound 1783),
N-[(2-amino-3-pyridyl)sulfonyl]-6-[6-(2-isopropoxyethoxy)-5-methyl-3-pyridyl]-2-[(4S)-2,2,4-trimethylpyrrolidin-1-yl]pyridine-3-carboxamide (Compound 1695),
N-[(6-amino-2-pyridyl)sulfonyl]-2-[(2S,5R)-2,5-dimethylpyrrolidin-1-yl]-6-[6-[(1-methylcyclopropyl)methoxy]-3-pyridyl]pyridine-3-carboxamide (Compound 454), and
N-[(6-amino-2-pyridyl)sulfonyl]-6-[6-(cyclopropoxy)-3-pyridyl]-2-[(2S,5R)-2,5-dimethylpyrrolidin-1-yl]pyridine-3-carboxamide (Compound 1125).

Preparation 64: 1-Methyl-2-[(2,4,6-trimethylphenyl)methyl]isoindoline-1-carboxylic acid Step 1: 2-Benzyl 1-(tert-butyl) 1-methylisoindoline-1,2-dicarboxylate

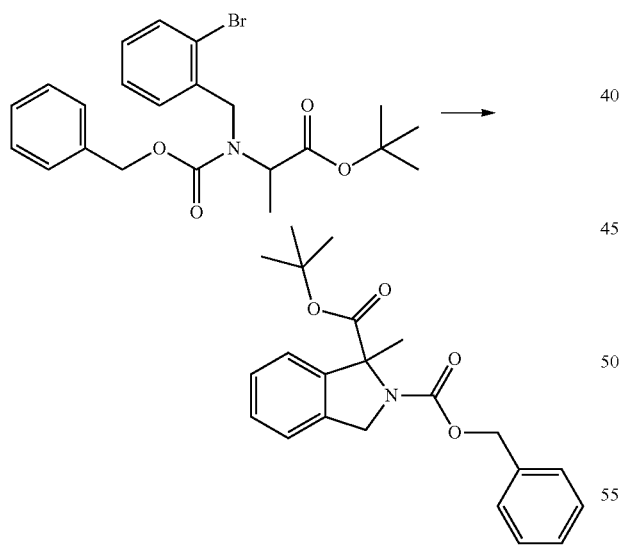

A solution of tert-butyl 2-[benzyloxycarbonyl-[(2-bromophenyl)methyl]amino]propanoate (2.69 g, 6.00 mmol) in dioxane (30 mL) was purged with nitrogen for 2 minutes. 2-(2-Diphenylphosphanylphenyl)-N,N-dimethyl-aniline (228.9 mg, 0.6000 mmol) was added under nitrogen followed by the addition of tris(dibenzylideneacetone)dipalladium(0) (274.7 mg, 0.3000 mmol). Lithium tert-butoxide (960.7 mg, 12.00 mmol) was added to the reaction mixture. The mixture was heated to 90° C. for 16 hours, diluted with ethyl acetate and filtered. The residue was purified by silica gel column chromatography (0-10% ethyl acetate in hexanes) to provide 2-benzyl 1-(tert-butyl) 1-methylisoindoline-1,2-dicarboxylate (1.4 g, 3.8 mmol, 63%). ESI-MS m/z calc. 367.17834, found 368.4 (M+1)$^+$; Retention time: 2.75 minutes.

Step 2: tert-butyl 1-methylisoindoline-1-carboxylate

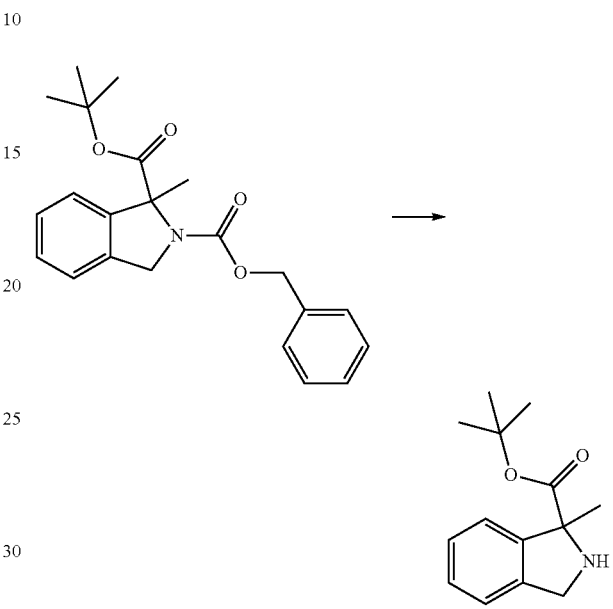

A solution of 2-benzyl 1-(tert-butyl) 1-methylisoindoline-1,2-dicarboxylate (718 mg, 1.95 mmol) in methanol (50 mL) was purged with nitrogen for 2 minutes. Palladium on carbon (10% w/w, 104.0 mg, 0.09770 mmol) was added and the mixture was placed under an atmosphere of hydrogen for 16 hours. The catalyst was removed via filtration through celite and the filtrate was concentrated to dryness to provide tert-butyl 1-methylisoindoline-1-carboxylate (400. mg, 1.71 mmol, 87.7%). The crude material was used directly in next step without further purification.

Step 3: 1-methyl-2-[(2,4,6-trimethylphenyl)methyl]isoindoline-1-carboxylic acid

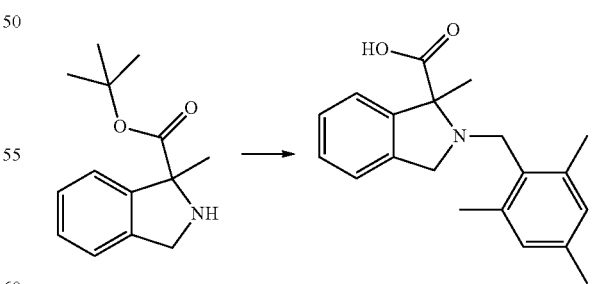

To a solution of tert-butyl 1-methylisoindoline-1-carboxylate (1.5 g, 6.4 mmol) in acetonitrile (75.00 mL) was added 2-(chloromethyl)-1,3,5-trimethyl-benzene (1.084 g, 6.429 mmol) and cesium carbonate (4.190 g, 12.86 mmol). The mixture was heated at 90° C. overnight, and then partitioned between ethyl acetate and water. The aqueous layer was extracted with ethyl acetate. The combined organic layers were washed with brine, dried over magnesium sulate, filtered, and concentrated to dryness. The crude material was purified by silica column chromatography utilizing a gradient of 0-5% ethyl acetate in hexanes to provide tert-butyl 1-methyl-2-[(2,4,6-trimethylphenyl)methyl]isoindoline-1-carboxylate. This material was then dissolved in dioxane (3.2 mL) and hydrochloric acid in dioxane (5 mL of 4 M, 20.00 mmol) was added to the mixture. The mixture was stirred for 16 hours at room temperature. The mixture was then stirred at 70° C. for 1 hour. The reaction mixture was cooled to room temperature, the precipitate was filtered and washed with dioxane to give an off-white solid. 1-methyl-2-[(2,4,6-trimethylphenyl)methyl]isoindoline-1-carboxylic acid (0.98 g, 3.2 mmol, 49%) ESI-MS m/z calc. 309.17288, found 310.5 (M+1)$^+$; Retention time: 1.18 minutes (3 min run).

Preparation 65: Ethyl 5-methyl-1-(p-tolyl)-1H-indole-2-carboxylate

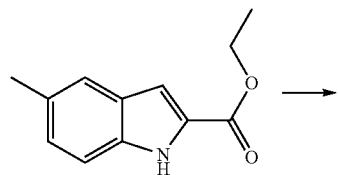

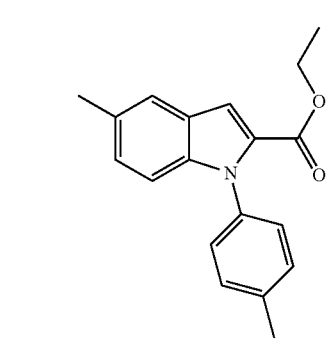

A mixture of ethyl 5-methyl-1H-indole-2-carboxylate (2.032 g, 10.00 mmol), 1-iodo-4-methyl-benzene (2.180 g, 10.00 mmol), iodocopper (95.22 mg, 0.5000 mmol), N1,N2-dimethylcyclohexane-1,2-diamine (284.5 mg, 315.4 µL, 2.000 mmol), and potassium phosphate (4.458 g, 21.00 mmol) in toluene (50.00 mL) was heated to reflux for 22 hours. The cooled reaciton was filtered and evaporated. The green residue was purified by silica gel chromatography with 0-15% ethyl acetate in hexanes to give ethyl 5-methyl-1-(p-tolyl)-1H-indole-2-carboxylate (1.43 g, 4.875 mmol, 48.74%) as a colorless oil. ESI-MS m/z calc. 293.14, found 294.2 (M+1)$^+$; Retention time: 0.83 minutes (1 minute run).

Preparation 66: N-[(6-amino-2-pyridyl)sulfonyl]-5-bromo-2-[(2S,5R)-2,5-dimethylpyrrolidin-1-yl]-6-(6-isopropoxy-3-pyridyl)pyridine-3-carboxamide (Compound 390)

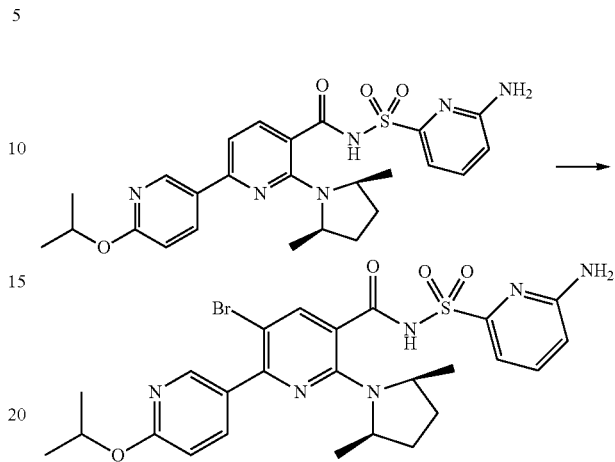

N-[(6-amino-2-pyridyl)sulfonyl]-2-[(2S,5R)-2,5-dimethylpyrrolidin-1-yl]-6-(6-isopropoxy-3-pyridyl)pyridine-3-carboxamide (147.4 mg, 0.2887 mmol) in acetic acid (1.5 mL) was treated with bromine (69.20 mg, 22.31 µL, 0.4330 mmol) and stirred at room temperature for 1 hour. The resulting yellow suspension was diluted with water (20 mL), quenched to pH 2-3 by addition of saturated aqueous sodium bicarbonate and extracted with dichloromethane. The crude material was purified by chromatography over silica gel (12 g) with a linear gradient of 0 to 5% methanol in dichloromethane to give N-[(6-amino-2-pyridyl)sulfonyl]-5-bromo-2-[(2S,5R)-2,5-dimethylpyrrolidin-1-yl]-6-(6-isopropoxy-3-pyridyl)pyridine-3-carboxamide (Compound 390) (90. mg, 0.14 mmol, 50.%) as a yellow foam. $^1$H NMR (400 MHz, DMSO-d$_6$) δ 12.80 (s, 1H), 8.52 (dd, J=2.5, 0.7 Hz, 1H), 8.02 (dd, J=8.7, 2.5 Hz, 1H), 7.85 (s, 1H), 7.64 (t, J=7.8 Hz, 1H), 7.23 (d, J=7.2 Hz, 1H), 6.83 (dd, J=8.6, 0.7 Hz, 1H), 6.72 (d, J=8.4 Hz, 1H), 6.51 (s, 2H), 5.32 (p, J=6.2 Hz, 1H), 3.95 (s, 2H), 1.97-1.82 (m, 2H), 1.64 (dd, J=8.9, 5.3 Hz, 2H), 1.33 (d, J=6.2 Hz, 6H), 1.04 (d, J=6.1 Hz, 6H). ESI-MS m/z calc. 588.1154, found 589.0 (M+1)$^+$; Retention time: 2.25 minutes.

Preparation 67: 3-(tert-butyl)-4-methoxy-1-(2,4,6-trimethylbenzyl)-1H-pyrazole-5-carboxylic acid Step 1: 3-(tert-butyl)-N-(2,3,5,6-tetrafluoro-4-(trifluoromethyl)phenyl)-1-(2,4,6-trimethylbenzyl)-1H-pyrazole-5-carboxamide

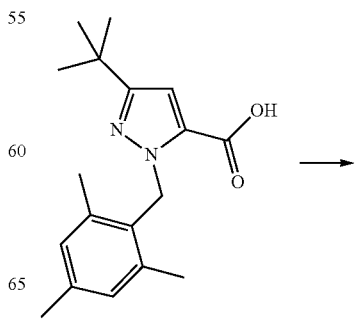

2079

-continued

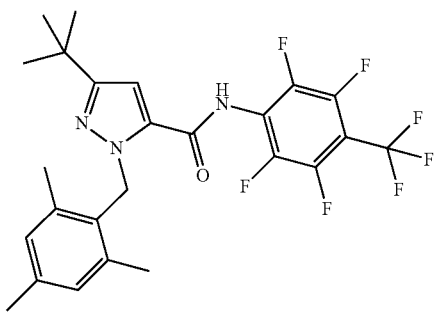

In a 20 mL sealed flask containing 5-tert-butyl-2-[(2,4,6-trimethylphenyl)methyl]pyrazole-3-carboxylic acid 1 (500. mg, 1.66 mmol) was added N-methylpyrrolidinone (5.000 mL) and diisopropylamine (537.7 mg, 724.7 µL, 4.160 mmol) followed by a propylphosphonic anhydride solution (2.118 mL of 50% w/v, 3.328 mmol) and 2,3,5,6-tetrafluoro-4-(trifluoromethyl)aniline (426.5 mg, 1.830 mmol) and the resulting mixture was stirred at 80° C. for 16 hours. The material was diluted with ethyl acetate (10 mL), washed with water and the organic layer was extracted. The organic layer was washed twice with a saturated aqueous solution of sodium bicarbonate, followed by brine. The material was dried over anhydrous sodium sulfate, filtered, and concentrated under vacuum. The resulting crude material was adsorbed to celite and purified by silica gel column chromatography ((40 g) using a gradient of 0 to 50% ethyl acetate) to afford 5-tert-butyl-N-[2,3,5,6-tetrafluoro-4-(trifluoromethyl)phenyl]-2-[(2,4,6-trimethylphenyl)methyl]pyrazole-3-carboxamide (748 mg, 1.44 mmol, 86.4%). ESI-MS m/z calc. 515.1808, found 516.2 (M+1)+; Retention time: 2.58 minutes. $^1$H NMR (400 MHz, DMSO) δ 10.92 (s, 1H), 7.01 (s, 1H), 6.83 (s, 2H), 5.64 (s, 2H), 2.27 (s, 6H), 2.21 (s, 3H), 1.20 (s, 9H).

Step 2: 3-(tert-butyl)-4-methoxy-N-(2,3,5,6-tetrafluoro-4-(trifluoromethyl)phenyl)-1-(2,4,6-trimethylbenzyl)-1H-pyrazole-5-carboxamide

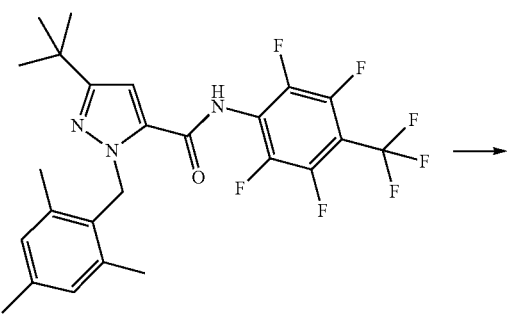

2080

-continued

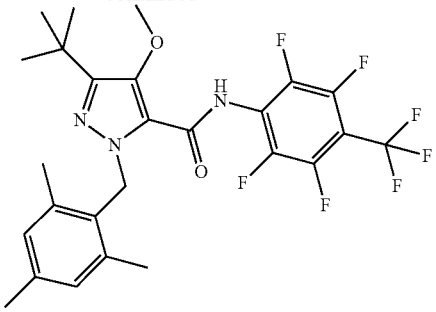

5-tert-Butyl-N-[2,3,5,6-tetrafluoro-4-(trifluoromethyl)phenyl]-2-[(2,4,6-trimethylphenyl)methyl]pyrazole-3-carboxamide (200. mg, 0.388 mmol), anhydrous methanol (1.554 g, 1.965 mL, 48.50 mmol), xylene (2.000 mL), diacetoxypalladium (8.711 mg, 0.03880 mmol), (diacetoxyiodo)benzene (374.9 mg, 1.164 mmol), and 4 Å molecular sieves were combined in a capped 10 mL vial. The mixture was heated in an oil bath to 100° C. for 40 hours. The mixture was allowed to cool was diluted with water, extracted three times with dichloromethane (10 mL), and the combined organics were washed with a saturated aqueous sodium bicarbonate solution and then a saturated aqueous solution of sodium chloride. The organic layer was dried over sodium sulfate and then purified by silica gel column chromatography (24 g) utilizing a gradient of 0 to 50% ethyl acetate in hexanes to afford 5-tert-butyl-4-methoxy-N-[2,3,5,6-tetrafluoro-4-(trifluoromethyl)phenyl]-2-[(2,4,6-trimethylphenyl)methyl]pyrazole-3-carboxamide (161 mg, 0.295 mmol, 76.1%) as an off-white solid. ESI-MS m/z calc. 545.19135, found 546.2 (M+1)+; Retention time: 2.4 minutes. $^1$H NMR (400 MHz, DMSO) δ 10.76 (s, 1H), 6.83 (s, 2H), 5.39 (s, 2H), 3.79 (s, 3H), 2.28 (s, 6H), 2.20 (s, 3H), 1.25 (s, 9H).

Step 3: Methyl 3-(tert-butyl)-4-methoxy-1-(2,4,6-trimethylbenzyl)-1H-pyrazole-5-carboxylate

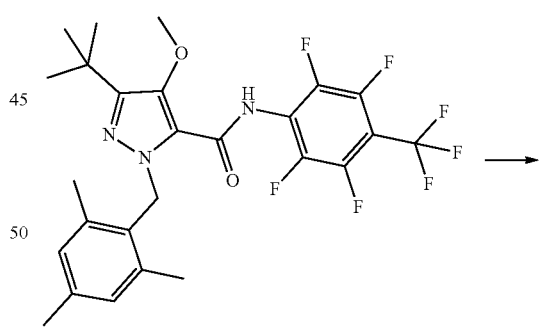

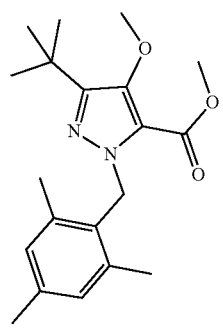

5-tert-butyl-4-methoxy-N-[2,3,5,6-tetrafluoro-4-(trifluoromethyl)phenyl]-2-[(2,4,6-trimethylphenyl)methyl]pyrazole-3-carboxamide (161 mg, 0.295 mmol) was dissolved in anhydrous tetrahydrofuran (3.220 mL) and to the mixture was added (bis(trimethylsilyl)amino)lithium (442.7 μL of 1 M in tetrahydrofuran, 0.4427 mmol) at 0° C. and the resulting mixture was allowed to stir for 10 minutes. Then methyl chloroformate (83.66 mg, 68.41 μL, 0.8853 mmol) was added and the reaction mixture was allowed to stir for one hour, and then concentrated under reduced pressure. The residue was redissolved in anhydrous tetrahydrofuran (3.220 mL) and then the mixture was cooled to 0° C. in an ice water bath. Sodium methoxide (319.0 μL of 25% w/v in methanol, 1.476 mmol) was added and the reaction mixture was stirred for 10 minutes. The mixture was diluted with water, extracted three times with ethyl acetate (10 mL) and the combined organics were washed with brine. The mixture was dried over sodium sulfate, and then purified by reverse-phase preparative chromatography utilizing a gradient from 10 to 99% acetonitrile in water containing 5 mM aqueous hydrochloric acid to yield methyl 3-(tert-butyl)-4-methoxy-1-(2,4,6-trimethylbenzyl)-1H-pyrazole-5-carboxylate (25.8 mg, 0.0749 mmol, 25.4%) as an off-white solid. ESI-MS m/z calc. 344.21, found 345.2 $(M+1)^+$; Retention time: 1.92 minutes.

Step 4: 3-(tert-butyl)-4-methoxy-1-(2,4,6-trimethylbenzyl)-1H-pyrazole-5-carboxylic acid

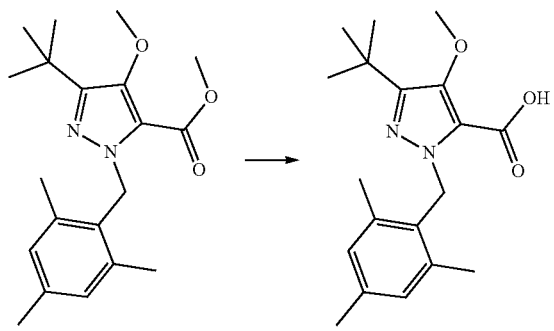 [SMILES: COC(=O)c1c(OC)c(C(C)(C)C)nn1Cc1c(C)cc(C)cc1C ; COc1c(C(C)(C)C)nn(Cc2c(C)cc(C)cc2C)c1C(=O)O]

To methyl 3-(tert-butyl)-4-methoxy-1-(2,4,6-trimethylbenzyl)-1H-pyrazole-5-carboxylate (30. mg, 0.087 mmol) in anhydrous tetrahydrofuran (600.0 μL) was added sodium hydroxide (108.9 μL of 4 M, 0.4355 mmol), the mixture was heated to 70°, C and stirred for 3 hours. The mixture was allowed to cool and then it was purified directly by reverse-phase preparative chromatography utilizing a gradient from 10 to 99% acetonitrile in water containing 5 mM aqueous hydrochloric acid to yield 3-(tert-butyl)-4-methoxy-1-(2,4,6-trimethylbenzyl)-1H-pyrazole-5-carboxylic acid (27.3 mg, 0.0826 mmol, 95%) as an off-white solid. ESI-MS m/z calc. 330.19434, found 331.2 $(M+1)^+$; Retention time: 2.08 minutes.

Preparation 68: N-[amino-(6-amino-2-pyridyl)-oxo-$\lambda^6$-sulfanylidene]-6-tert-butyl-2-(2,4,6-trimethylphenoxy)pyridine-3-carboxamide (Compound 1602) (Compound 1481) (Compound 515)

Step 1: 2-fluoro-6-[(6-fluoropyridin-2-yl)disulfanyl]pyridine

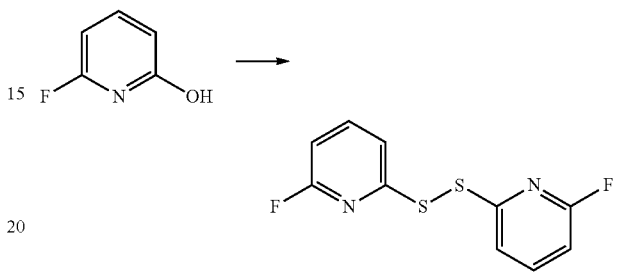

A mixture of 2-fluoro-6-hydroxypyridine (1.13 g, 10.0 mmol) and phosphorus pentasulfide (4.44 g, 20.0 mmol) in toluene (50 mL) was refluxed for 18 hours. Once cooled, the flask was placed in an ice bath and quenched with water (50 mL) and then basified to a pH of about 8-9 with 25% NaOH. The mixture was filtered over celite to remove some solids that were still present and washed with water (50 mL) and ethyl acetate (200 mL). The biphasic mixture was transferred to a 1.0-L separatory funnel, extracted and the layers were separated. The aqueous layer was extracted again with ethyl acetate (100 mL), and the organic layers were then combined, washed with brine, dried over anhydrous sodium sulfate, filtered and concentrated under reduced pressure. The residue was purified by silica-gel column chromatography, eluting from 0% to 10% ethyl acetate in heptanes to afford 2-fluoro-6-[(6-fluoropyridin-2-yl)disulfanyl]pyridine (304 mg, 23.7% yield) as a colorless oil. $^1$H NMR (300 MHz, CDCl$_3$): ppm 6.75 (ddd, J=8.0, 2.7, 0.5 Hz, 1H), 7.49 (ddd, J=7.7, 2.1, 0.6 Hz, 1H), 7.72 (q, J=7.9 Hz, 1H). $[M+H]^+$=257.0.

Step 2: 6-tert-butyl-N-[(6-fluoropyridin-2-yl)sulfinyl]-2-(2,4,6-trimethylphenoxy)pyridine-3-carboxamide

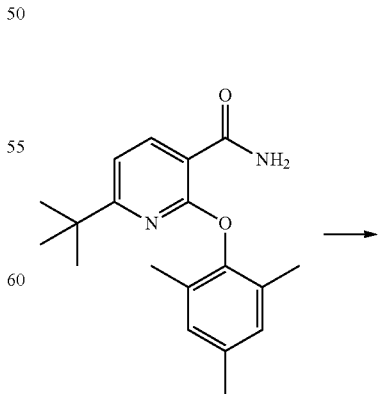

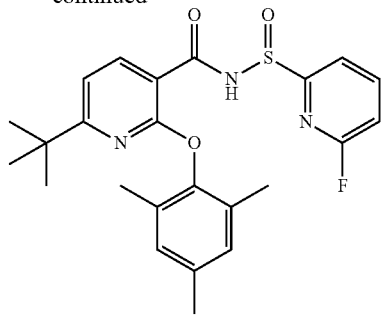

To a solution of 2-fluoro-6-[(6-fluoropyridin-2-yl)disulfanyl]pyridine (744 mg, 2.90 mmol) and 6-tert-butyl-2-(2,4,6-trimethylphenoxy)pyridine-3-carboxamide (906 mg, 2.90 mmol) in pyridine (10 mL) and acetonitrile (10 mL) was added bromine (0.172 mL, 3.36 mmol) dropwise at 0° C. After complete addition, the mixture was stirred at room temperature overnight. Additional bromine (0.087 mL, 1.7 mmol) was added at room temperature and the mixture was stirred for an additional hour. Solvent was then removed under reduced pressure and pyridine was further co-evaporated with toluene (10 mL) two times under reduced pressure. The residue was purified by silica gel column chromatography (24 g) column, eluting from 0% to 25% ethyl acetate in heptane to afford 6-tert-butyl-N-[(6-fluoropyridin-2-yl)sulfinyl]-2-(2,4,6-trimethylphenoxy)pyridine-3-carboxamide (850 mg, 64% yield) as an off-white solid. $^1$H NMR (300 MHz, CDCl$_3$): ppm 1.08 (s, 9H), 2.00 (s, 6H), 2.29 (s, 3H), 6.86 (s, 2H), 7.03-7.89 (m, 1H), 7.12 (d, J=8.0, 1H), 7.99-8.11 (m, 2H), 8.53 (d, J=8.0 Hz, 1H). $^{19}$F NMR (282 MHz, CDCl$_3$): ppm −64.8 (s, 1 F). [M+H]$^+$=456.1.

Step 3: 6-(tert-butyl)-N-(6-fluoropyridine-2-sulfonimidoyl)-2-(mesityloxy)nicotinamide

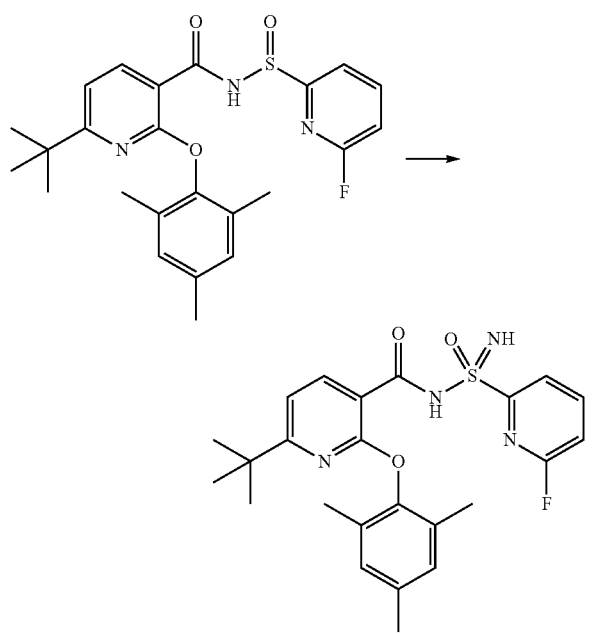

To a solution of 6-tert-butyl-N-[(6-fluoropyridin-2-yl)sulfinyl]-2-(2,4,6-trimethylphenoxy)pyridine-3-carboxamide (419 mg, 0.920 mmol) in dichloromethane (10 mL) was added tert-butyl hypochlorite (94.8 µL, 0.87 mmol) at 0° C. The mixture was stirred at this temperature for 2 days. The solvent was then removed under reduced pressure at below 21° C. The crude product was used directly in the next step without further purification. The residue was dissolved in acetonitrile (11 mL) then hexamethyldisilazane (1.09 mL, 5.22 mmol) was added at 0° C. The mixture was stirred for 1 hour at room temperature then quenched by the addition of water (3 mL). The mixture was extracted with ethyl acetate (2×20 mL), dried over sodium sulfate, filtered, and concentrated under reduced pressure. The residue was purified by silica gel column chromatography column (24 g), eluting from 0% to 5% methanol in dichloromethane, to afford 6-(tert-butyl)-N-(6-fluoropyridine-2-sulfonimidoyl)-2-(mesityloxy)nicotinamide (286 mg, 70% yield) as a white solid. $^1$H NMR (300 MHz, CDCl$_3$): ppm 1.08 (s, 9H), 2.03 (s, 6H), 2.29 (s, 3H), 6.84 (s, 2H), 6.97 (d, J=8.0 Hz, 1H), 7.16 (ddd, J=8.0, 2.6, 0.8 Hz, 1H), 7.94-8.11 (m, 2H), 8.35 (d, J=8.0 Hz, 1H). $^{19}$F NMR (282 MHz, CDCl$_3$): ppm −64.1 (s, 1 F). [M+H]$^+$=471.1.

Step 4: 6-(tert-butyl)-N-(6-((2,4-dimethoxybenzyl)amino)pyridine-2-sulfonimidoyl)-2-(mesityloxy)nicotinamide

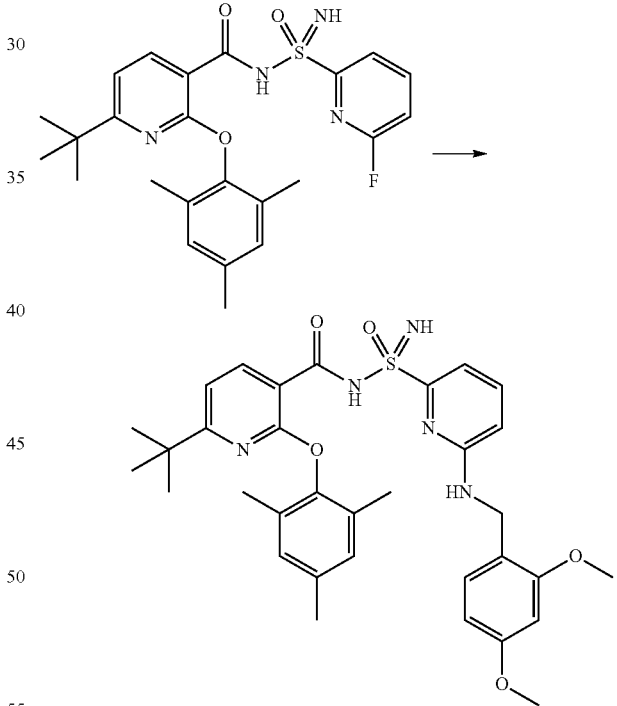

A mixture of 6-(tert-butyl)-N-(6-((2,4-dimethoxybenzyl)amino)pyridine-2-sulfonimidoyl)-2-(mesityloxy)nicotinamide (400. mg, 0.850 mmol), 2,4-dimethoxybenzylamine (0.25 mL, 1.7 mmol) and triethylamine (0.24 mL, 1.7 mmol) in dimethylsulfoxide (10 mL) was stirred at 100° C. overnight. After completion, the mixture was diluted with ethyl acetate (20 mL), washed with brine (2×10 mL), dried over sodium sulfate, filtered, and concentrated under reduced pressure. The residue was purified by reverse-phase column chromatography on a 25 g column, eluting from 0% to 100% acetonitrile in water containing 0.1% formic acid to afford 6-(tert-butyl)-N-(6-((2,4-dimethoxybenzyl)amino)pyridine-2-sulfonimidoyl)-2-(mesityloxy)nicotinamide (426 mg, 81.1% yield) as a yellow foam. ¹H NMR (300 MHz, CDCl₃): ppm 1.07 (s, 9H), 2.03 (s, 6H), 2.27 (s, 3H), 3.77 (s, 3H), 3.82 (s, 3H), 4.42 (s, 2H), 5.18-5.35 (br. s., 1H), 6.36 (dd, J=8.3, 2.3 Hz, 1H), 6.45 (d, J=2.3 Hz, 1H), 6.52 (d, J=8.3 Hz, 1H), 6.81 (s, 2H), 6.94 (d, J=7.9 Hz, 1H), 7.18 (d, J=8.3 Hz, 1H), 7.28 (d; J=7.4 Hz, 1H), 7.45 (dd, J=8.5, 7.4 Hz, 1H), 8.38 (d, J=7.9 Hz, 1H). [M+H]⁺=618.2.

Step 5: N-(6-aminopyridine-2-sulfonimidoyl)-6-(tert-butyl)-2-(mesityloxy)nicotinamide

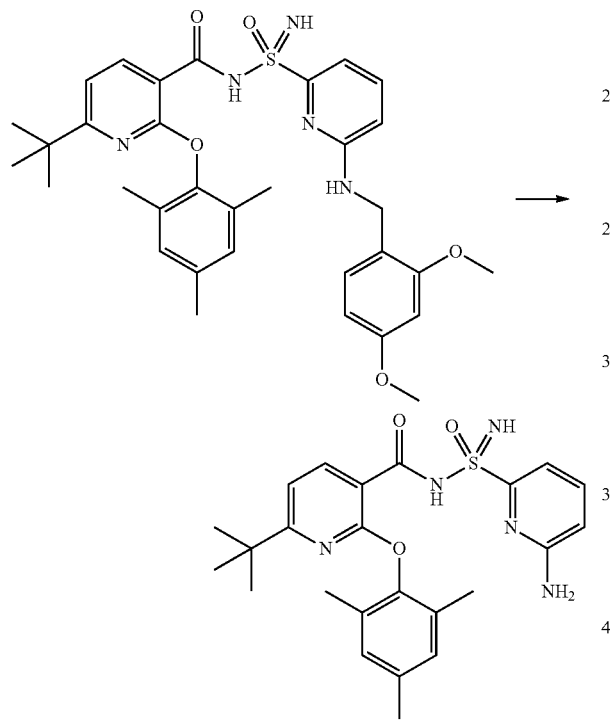

To a stirred solution of N-[amino(6-{[(2,4-dimethoxyphenyl)methyl]amino}pyridin-2-yl)oxo-λ⁶-sulfanylidene]-6-tert-butyl-2-(2,4,6-trimethylphenoxy)pyridine-3-carbdxamide (420 mg, 0.68 mmol) in dichloromethane (50 mL) was added trifluoroacetic acid (12 mL) and the mixture was stirred until LCMS indicated completion. The reaction mixture was diluted with dichloromethane (20 mL) and water (20 mL) and the pH was adjusted to greater than 6 by adding solid NaHCO₃. The mixture was extracted with dichloromethane (2×20 mL) and the combined organic layers were dried over sodium sulfate, filtered and concentrated under reduced pressure. The residue was purified by reverse-phase column chromatography on a 25 g column, eluting from 0% to 100% acetonitrile in water containing 0.1% formic acid to afford N-(6-aminopyridine-2-sulfonimidoyl)-6-(tert-butyl)-2-(mesityloxy)nicotinamide (90. mg, 28% yield) as a white solid. ¹H NMR (300 MHz, CDCl₃+5 drops of DMSO-d₆) ppm 0.96 (s, 9H), 1.90 (s, 6H), 2.17 (s, 3H), 5.78 (br. s., 2H), 6.59 (d, J=8.2 Hz, 1H), 6.71 (s, 2H), 6.82 (d, J=7.8 Hz, 1H), 7.19-7.31 (m, 3H), 7.36-7.47 (m, 1H), 8.15 (d, J=7.8 Hz, 1H). [M+H]⁺=468.1.

Step 6: N—[(S)-amino(6-aminopyridin-2-yl)oxo-λ⁶-sulfanylidene]-6-tert-butyl-2-(2,4,6-trimethylphenoxy)pyridine-3-carboxamide and N—[(R)-amino (6-aminopyridin-2-yl)oxo-λ⁶-sulfanylidene]-6-tert-butyl-2-(2,4,6-trimethylphenoxy)pyridine-3-carboxamide

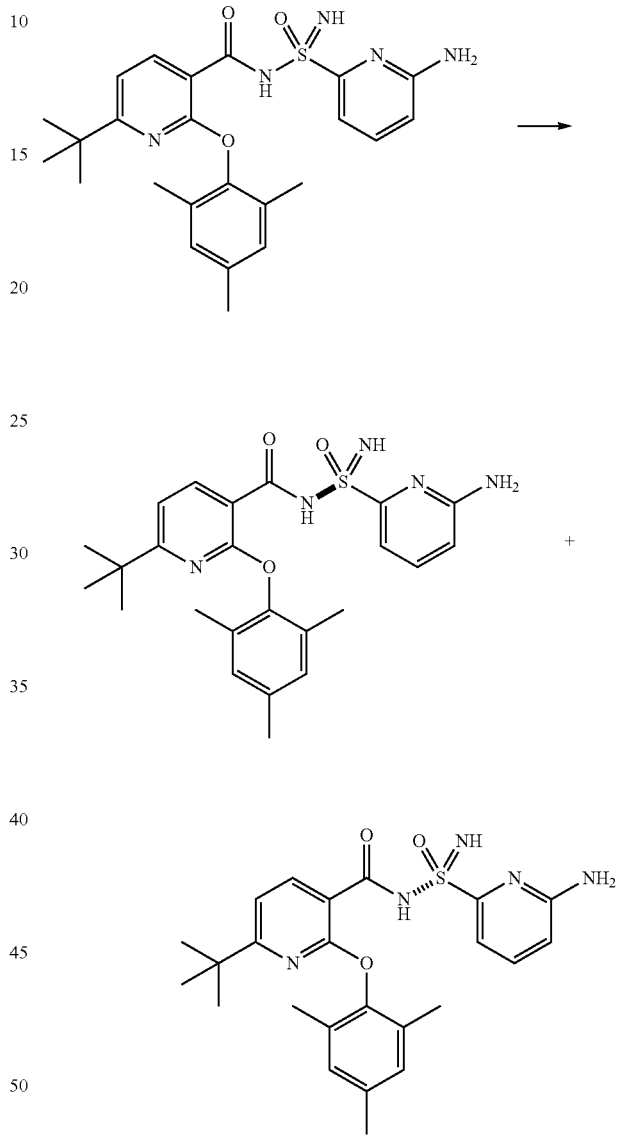

N-(6-aminopyridine-2-sulfonimidoyl)-6-(tert-butyl)-2-(mesityloxy)nicotinamide was dissolved in a methanol and dimethylsulfoxide mixture (4:1 (v/v)) to an approximate concentration of 16 mg/mL. The solution was subjected to chiral SFC (70 μL injections; column: Chiralpak OD-H (250×21.2 mm), 5 μm; mobile phase: 20% methanol, 80% CO₂; flow: 10.0 mL/min) to give N—[(S)-amino-pyridin-2-yl)oxo-λ⁶-sulfanylidene]-6-tert-butyl-2-(2,4,6-trimethylphenoxy)pyridine-3-carboxamide (peak 1, enantiomer 1, 98% ee), and N—[(R)-amino(6-aminopyridin-2-yl)oxo-λ⁶-sulfanylidene]-6-tert-butyl-2-(2,4,6-trimethylphenoxy)pyridine-3-carboxamide (peak 2, enantiomer 2, 97.3% ee). Absolute stereochemistry is inknown.

Preparation 69: (R)-1-(2,4,6-trimethylbenzyl)indoline-2-carboxylic acid

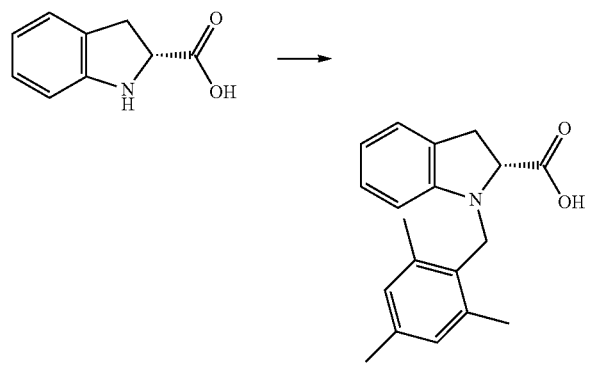

A suspension of (R)-indoline-2-carboxylic acid (300. mg, 1.84 mmol) and potassium hydroxide (309.5 mg, 5.517 mmol) was stirred in isopropanol (2.010 mL) for 20 minutes. The reaction mixture was stirred for 20 minutes and was treated with 2-(chloromethyl)-1,3,5-trimethyl-benzene (341.2 mg, 2.023 mmol). The reaction mixture was stirred overnight. The reaction mixture was diluted with ethyl acetate and water. The mixture was extracted with ethyl acetate and the aqueous layer was acidified to pH 5 and extracted again with ethyl acetate. The combined organics were washed with water, brine, dried over sodium sulfate, filtered and concentrated to yield (R)-1-(2,4,6-trimethylbenzyl)indoline-2-carboxylic acid (220. mg, 0.745 mmol, 40.5%) as a white solid. ESI-MS m/z calc. 295.15723, found 296.5 (M+1)$^+$; Retention time: 1.79 minutes.

Preparation 70: tert-butyl 2,3,4,5-tetrahydro-1H-1-benzazepine-2-carboxylate

Step 1: 3-(2-bromophenyl)propan-1-ol

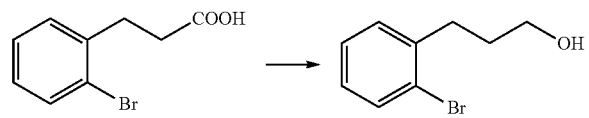 [SMILES: O=C(O)CCc1ccccc1Br ; OCCCc1ccccc1Br]

A solution of 3-(2-bromophenyl)propanoic acid (1.0 g, 4.4 mmol) in anhydrous tetrahydrofuran (5.0 mL) was treated with borane-tetrahydrofuran complex in tetrahydrofuran (1.0 M, 7.0 mL, 7.0 mmol) at 0° C. over a period of 15 minutes. The mixture was stirred at 0° C. for an additional 1 hour. After completion, the residual borane was quenched by the cautious addition of water (1 mL) and the solvent was removed under vacuum. The resulting residue was dissolved in ether (20 mL) and the organic layer was washed with water (20 mL), brine (20 mL), dried over sodium sulfate, filtered, and concentrated under pressure to afford 3-(2-bromophenyl)propan-1-ol as a colorless oil (938 mg, quantitative yield). This compound was used in the following step without further purification.

Step 2: Synthesis of 1-bromo-2-(3-bromopropyl)benzene

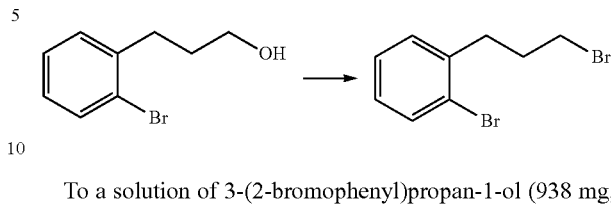

To a solution of 3-(2-bromophenyl)propan-1-ol (938 mg, 4.36 mmol) and triphenylphosphine (2.29 g, 8.72 mmol) in anhydrous dichloromethane (25 mL) was added N-bromosuccinimide (1.63 g, 9.16 mmol) at 0° C. and the mixture was stirred at room temperature for 2 hours. After completion, the reaction was quenched by the addition of water (20 mL) and the organic layer was separated and dried over sodium sulfate, filtered and concentrated under pressure. The residue was purified by silica gel chromatography (40 g), eluting from 0% to 10% ethyl acetate in heptanes to afford 1-bromo-2-(3-bromopropyl)benzene as a yellow oil (830 mg, 68.5% yield). $^1$H NMR (300 MHz, CDCl$_3$) ppm 2.13-2.24 (m, 2H), 2.90 (t, J=7.7 Hz, 2H), 3.43 (t, J=6.5 Hz, 2H), 7.04-7.12 (m, 1H), 7.20-7.28 (m, 2H), 7.54 (d, J=7.7 Hz, 1H). [M+H]$^+$=279.1.

Step 3: tert-butyl 2-amino-5-(2-bromophenyl)pentanoate

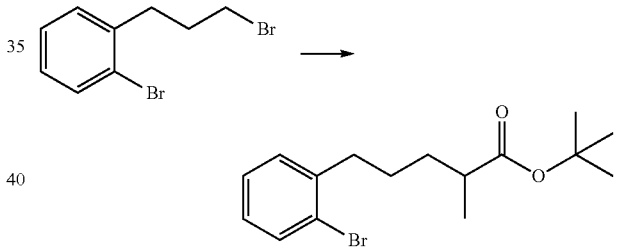

To a suspension of potassium hydroxide (1.27 g, 22.6 mmol) in dimethylsulfoxide (10 mL) cooled in a cold water bath was added N-(diphenylmethylene)glycine tert-butyl ester (2.23 g, 7.55 mmol). Then, 1-bromo-2-(3-bromopropyl)benzene (938 mg, 4.36 mmol) in dimethyl sulfoxide (10 mL) was added dropwise and the mixture was stirred at room temperature for 1 hour. After completion, the mixture was diluted with ethyl acetate (100 mL) and the solution was filtered. The mixture was washed with water (3×50 mL), brine, dried over sodium sulfate, filtered, and concentrated under reduced pressure. After drying under high vacuum, the residue was dissolved in tetrahydrofuran (78 mL). To this solution was added 1 N HCl (75.7 mL, 75.7 mmol) dropwise at 0° C. and the mixture was stirred at this temperature for an additional 2 hours. The resulting mixture was then neutralized by addition of solid sodium bicarbonate and extracted with dichloromethane (100 mL). The organic layer was dried over sodium sulfate, filtered and concentrated under pressure. The residue was purified by silica gel chromatography (80 g) eluting from 0% to 10% ethyl acetate in heptanes to afford tert-butyl 2-amino-5-(2-bromophenyl)pentanoate as a yellow oil (2.21 g, 86.4% yield over two steps). $^1$H NMR (300 MHz, CDCl$_3$) ppm 1.45 (s, 9H), 1.60-1.81 (m, 2H), 2.70-2.78 (m, 2H), 3.33-3.39 (m, 2H), 7.00-7.09 (m, 1H), 7.18-7.24 (m, 2H), 7.51 (d, J=8.1 Hz, 1H). [M+H]⁺=328.1.

Step 4: tert-butyl 2,3,4,5-tetrahydro-1H-1-benzazepine-2-carboxylate

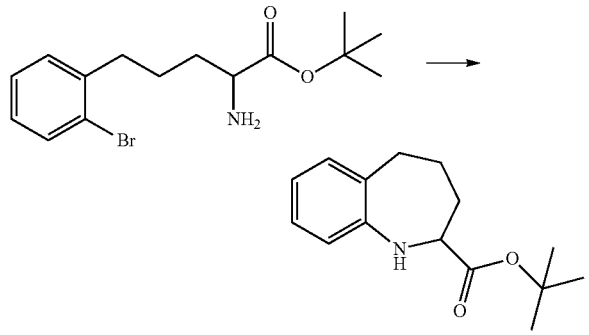

A mixture of tert-butyl 2-amino-5-(2-bromophenyl)pentanoate (1.7 g, 5.2 mmol), palladium acetate (116 mg, 0.518 mmol), triphenylphosphine (408 mg, 1.55 mmol), and cesium carbonate (3.4 g, 10. mmol) in toluene (80 mL) was stirred at 110° C. overnight. After completion, the mixture was diluted with ethyl acetate (100 mL) and washed with water (50 mL), brine (50 mL), dried over sodium sulfate, filtered, and concentrated under reduced pressure. The residue was purified by silica gel chromatography (80 g) eluting from 0% to 20% ethyl acetate in heptanes to afford tert-butyl 2,3,4,5-tetrahydro-1H-1-benzazepine-2-carboxylate as a yellow oil (527 mg, 41.0%). ¹H NMR (300 MHz, CDCl₃) ppm 1.46-1.57 (m, 10H), 1.66-1.82 (m, 1H), 1.94-2.08 (m, 1H), 2.24-2.36 (m, 1H), 2.65-2.77 (m, 1H), 2.78-2.91 (m, 1H), 3.44 (dd, J=10.7, 2.3 Hz, 1H), 4.50 (br. s, 1H), 6.79-6.88 (m, 2H), 7.01-7.11 (m, 2H). [M+H]⁺=248.2

Preparation 71: 5-ethyl-1-[(2,4,6-trimethylphenyl)methyl]pyrrolo[2,3-b]pyridine-2-carboxylate

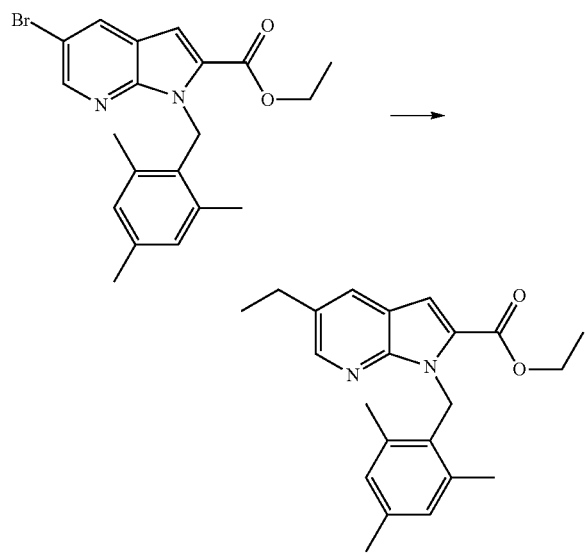

A solution of methyl 5-bromo-1-[(2,4,6-trimethylphenyl)methyl]pyrrolo[2,3-b]pyridine-2-carboxylate (150. mg, 0.387 mmol), 1,2-dimethoxyethane (1.35 mL) 4,4,5,5-tetramethyl-2-vinyl-1,3,2-dioxaborolane (119.3 mg, 0.7746 mmol), and potassium carbonate (187.4 mg, 1.356 mmol) in 1,2-dimethoxyethane (1.35 mL) and water (0.45 mL) was degassed and put under nitrogen. The reaction mixture was treated with tetrakis(triphenylphosphine)palladium (0) (44.75 mg, 0.03873 mmol) and irradiated in a microwave reactor at 120° C. for 30 minutes. The mixture was diluted with water and extracted three times with ethyl acetate. The combined organics were washed with brine, dried over sodium sulfate, filtered, and concentrated under reduced pressure. The resulting crude methyl 1-[(2,4,6-trimethylphenyl)methyl]-5-vinyl-pyrrolo[2,3-b]pyridine-2-carboxylate was dissolved in methanol (12.45 mL) and put under a nitrogen atmosphere before being treated with wet 10% palladium on carbon (41.22 mg, 0.03873 mmol). The mixture was evacuated and put under a hydrogen atmosphere for 16 hours. The reaction mixture was put under a nitrogen atmosphere and filtered through celite to afford the crude product which was purified on 12 g of silica gel utilizing a gradient of 0-40% ethyl acetate in hexanes to yield methyl 5-ethyl-1-[(2,4,6-trimethylphenyl)methyl]pyrrolo[2,3-b]pyridine-2-carboxylate ESI-MS m/z calc. 336.18378, found 337.5 (M+1)⁺; Retention time: 2.24 minutes.

Preparation 72

Step 1: Synthesis of 2-(2-bromophenyl)propan-2-amine

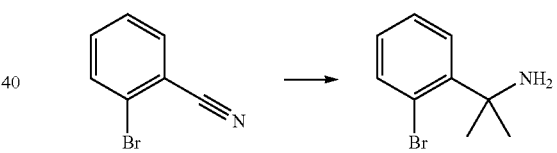

Methylmagnesium bromide (54.9 mL, 164.8 mmol, 3M in diethyl ether) was added to a solution of 2-bromobenzonitrile (10.0 g, 54.9 mmol) in diethyl ether (200 mL) and the reaction mixture was stirred at room temperature under nitrogen. After 30 minutes, titanium isopropoxide (16.3 mL, 54.9 mmol) was added and resulting mixture was refluxed overnight. Once cooled to 0° C., 2N NaOH (400 mL) was added and resulting mixture was stirred at room temperature for 30 minutes. The solution was diluted with saturated aqueous sodium bicarbonate (400 mL), extracted using methyl tert-butyl ether (3×200 mL). The organic layers were combined and concentrated under reduced pressure. The residue was dissolved in 1N hydrochloric acid (75 mL) and washed with methyl tert-butyl ether (150 mL). The aqueous layer was basified to pH 10-11 using 2N sodium hydroxide and the resulting solution was extracted with methyl tert-butyl ether (3×200 mL). The organic layers were combined, dried over anhydrous sodium sulfate and concentrated under reduced pressure to afford 2-(2-bromophenyl)propan-2-amine (9.0 g, 77% yield) as orange oil. ¹H NMR (300 MHz, CDCl₃): ppm 1.66 (s, 6H), 7.02-7.10 (m, 1H), 7.13-7.43 (m, 1H), 7.55-7.61 (m, 2H). [M+H]⁺=214.0.

Step 2: Synthesis of tert-butyl 2-{[2-(2-bromophenyl)propan-2-yl]amino}acetate

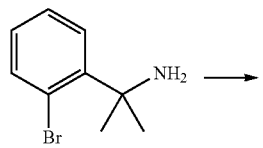

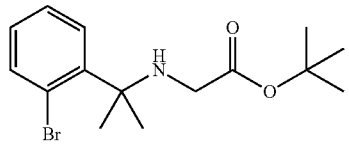

tert-Butyl 2-bromoacetate (6.24 mL, 42.2 mmol) was slowly added to a solution of 2-(2-bromophenyl)propan-2-amine (9.04 g, 42.22 mmol) and potassium carbonate (14.6 g, 105.6 mmol) in dry tetrahydrofuran (100 mL) at 0° C. and reaction mixture was stirred at 50-55° C. for 16 hours. Once cooled to room temperature, reaction mixture was diluted with brine (100 mL) and extracted using ethyl acetate (3×100 mL). The organic layers were combined, dried over anhydrous magnesium sulfate, and concentrated under reduced pressure. The residue was purified by silica gel chromatography, eluting from 0% to 20% ethyl acetate in heptanes to afford tert-butyl 2-{[2-(2-bromophenyl)propan-2-yl]amino}acetate (4.5 g, 32% yield) as a yellow oil. $^1$H NMR (300 MHz, CDCl$_3$) ppm 1.43 (s, 9H), 1.63 (s, 6H), 2.94 (s, 2H), 7.09 (dt, J=7.6, 1.7 Hz, 1H), 7.22-7.31 (m, 1H), 7.43 (dd, J=7.9, 1.6 Hz, 1H), 7.58 (dd, J=7.9, 1.4 Hz, 1H). [M+H]$^+$=328.1.

Step 3: tert-butyl 2-{[(benzyloxy)carbonyl][2-(2-bromophenyl)propan-2-yl]amino}acetate

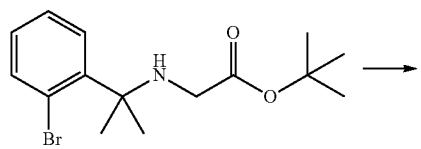

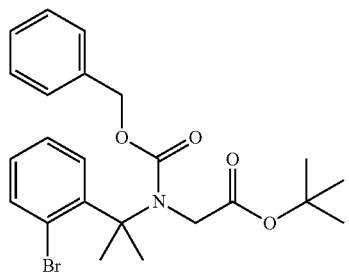

Diisopropylethylamine (5.48 mL, 31.4 mmol) was added to a solution of tert-butyl 2-{[2-(2-bromophenyl)propan-2-yl]amino}acetate (4.48 g, 13.7 mmol) in dichloromethane (50 mL) and solution was cooled to 0° C. Benzyl chloroformate (3.51 mL, 24.6 mmol) was added dropwise at 0° C. and reaction mixture was stirred at room temperature overnight. The reaction mixture was diluted with dichloromethane (50 mL) and washed with 5% aqueous citric acid (2×50 mL) and brine (50 mL). The organic layer was dried over anhydrous magnesium sulfate and concentrated under reduced pressure. The residue was purified by silica gel chromatography, eluting from 0% to 10% ethyl acetate in heptane to afford tert-butyl 2-{[(benzyloxy)carbonyl][2-(2-bromophenyl)propan-2-yl]amino}acetate (4.2 g, 67% yield) as a yellow oil. $^1$H NMR (300 MHz, CDCl$_3$): ppm 1.41 (s, 6H), 1.55 (s, 3H), 1.78 (s, 2H), 1.84 (s, 4H), 4.21 (s, 1.3H), 4.32 (s, 0.7H), 4.83 (s, 0.7H), 4.99 (s, 1.3H), 6.70-7.62 (m, 9H). [M+H]$^+$=484.1.

Step 4: 2-benzyl 1-tert-butyl 3,3-dimethyl-2,3-dihydro-1H-isoindole-1,2-dicarboxylate

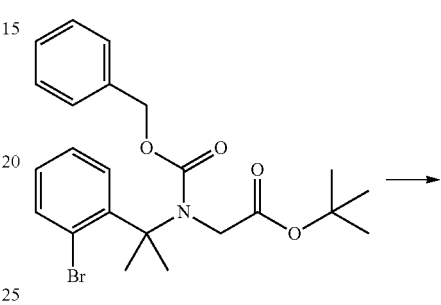

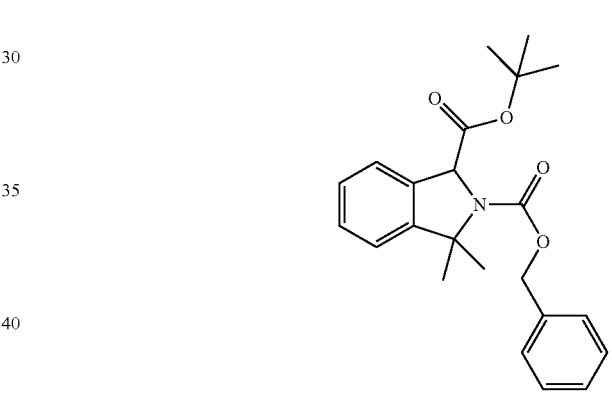

Tris(dibenzylideneacetone)dipalladium(0) (87 mg, 0.10 mmol), 2'-(diphenylphosphino)-N,N'-dimethyl-(1,1'-biphenyl)-2-amine (PhDavePhos) (73 mg, 0.19 mmol) and lithium tert-butoxide (0.31 g, 3.81 mmol) were added in order to a solution of tert-butyl 2-{[(benzyloxy)carbonyl][2-(2-bromophenyl)propan-2-yl]amino}acetate (0.88 g, 1.90 mmol) in dioxane (10 mL) previously degased and purged with nitrogen. The reaction mixture was stirred at 90° C. overnight. Once cooled at room temperature, the reaction mixture was diluted with ethyl acetate (20 mL), filtered and concentrated under reduced pressure. The residue was purified by silica gel chromatography, eluting from 0% to 10% ethyl acetate in heptane to afford 2-benzyl 1-tert-butyl 3,3-dimethyl-2,3-dihydro-1H-isoindole-1,2-dicarboxylate (0.31 g, 43% yield) as an orange oil. $^1$H NMR (300 MHz, CDCl$_3$): ppm 1.31 (s, 6H), 1.45 (s, 3H), 1.65 (s, 1H), 1.73 (s, 1H), 1.76 (s, 2H), 1.81 (s, 2H), 5.11-5.47 (m, 3H), 7.12-7.48 (m, 9H). [M+Na]$^+$=404.2.

Preparation 73: 6-hydroxy-1-methyl-N-((6-nitropyridin-2-yl)sulfonyl)-2-(2,4,6-trimethylbenzyl)isoindoline-1-carboxamide

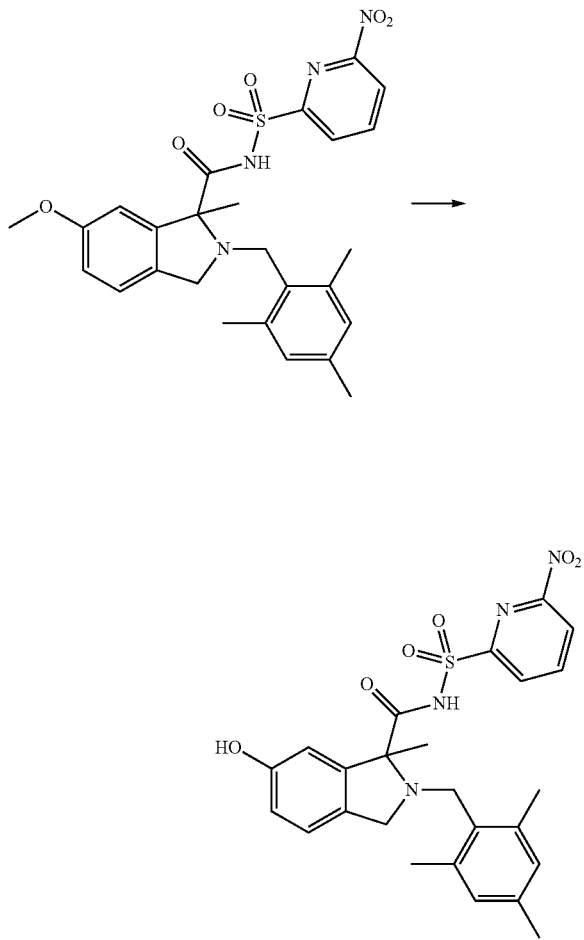

Under an atmosphere of nitrogen, 6-methoxy-1-methyl-N-[(6-nitro-2-pyridyl)sulfonyl]-2-[(2,4,6-trimethylphenyl)methyl]isoindoline-1-carboxamide (333 mg, 0.635 mmol) was dissolved in dichloromethane (30 mL). The mixture was cooled to −78° C., and tribromoborane (5.046 g, 1.904 mL of 1 M, 1.904 mmol) was added to the reaction mixture dropwise. The mixture was slowly warmed to room temperature and stirred for 16 hours. The reaction mixture was added to approximately 50 mL of ice. The layers were separated, and the aqueous layer was extracted with dichloromethane (3×5 mL). The combined organic layers were dried over sodium sulfate, concentrated, and purified on a column of silica gel utilizing a gradient of 0 to 100% ethyl acetate in hexanes to yield 6-hydroxy-1-methyl-N-[(6-nitro-2-pyridyl)sulfonyl]-2-[(2,4,6-trimethylphenyl)methyl]isoindoline-1-carboxamide (90.7 mg, 0.178 mmol, 28.0%) ESI-MS m/z calc. 510.15732, found 511.5 (M+1)+; Retention time: 0.56 minutes

Preparation 74: tert-butyl 2,3,4,5-tetrahydro-1H-benzo[c]azepine-3-carboxylate

Step 1: 3,4-dihydro-1H-2-benzopyran-1-one

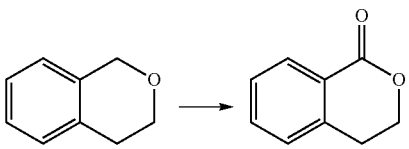 [SMILES: c1ccc2c(c1)CCOC2 ; O=C1OCCc2ccccc21]

To a solution of isochroman (15.0 g, 112 mmol) in dichloromethane (1.4 L) stirred at room temperature was added, over 15 minutes, a homogeneous mixture of potassium permanganate (106 g, 672 mmol) and manganese dioxide (58.0 g, 672 mmol), prepared by grinding potassium permanganate and then mixing with manganese dioxide using a pestle and mortar. The suspension was vigorously stirred for 4 days at room temperature, and then filtered through a pad of Celite. The filtrate was concentrated and the residue was purified by silica chromatography, eluting with a mixture of heptanes and ethyl acetate (0 to 20%) to provide 3,4-dihydro-1H-2-benzopyran-1-one (8.2 g, 49% yield) as a colorless oil. $^1$H NMR (CDCl$_3$, 300 MHz) ppm 3.06 (t, J=6.0 Hz, 2H), 4.52 (t, J=6.0 Hz, 2H), 7.20-7.30 (m, 1H), 7.38 (t, J=7.6 Hz, 1H), 7.53 (t, J=7.6 Hz, 1H), 8.06 (d, J=7.6 Hz, 1H).

Step 2: ethyl 2-(2-bromoethyl)benzoate

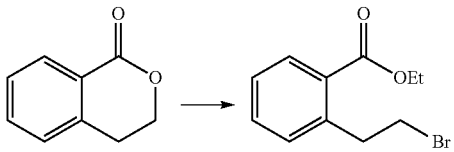 [SMILES: O=C1OCCc2ccccc21 ; CCOC(=O)c1ccccc1CCBr]

Phosphorus tribromide (1.05 mL, 11.0 mmol) and bromine (0.62 mL, 12 mmol) were slowly added to a solution of 3,4-dihydro-1H-2-benzopyran-1-one (1.5 g, 10. mmol) in carbon tetrachloride (15 mL) cooled in an ice-water bath. The mixture was then stirred at room temperature for 16 hours. The resulting orange suspension was stirred at 60° C. for 3 hours. The red mixture was then cooled down and ethanol (10 mL) was slowly added at 0° C. (exothermic!). The reaction mixture (orange solution) was stirred for one hour. The reaction mixture was partitioned between dichloromethane (50 mL) and water (20 mL). The organic phase was separated and washed with brine (10 mL), dried over sodium sulfate and concentrated under reduced pressure. The residue was purified by silica chromatography, eluting with a mixture of ethyl acetate and heptanes (0 to 10%) to afford ethyl 2-(2-bromoethyl)benzoate (2.0 g, 78% yield) as a pale yellow oil. $^1$H NMR (300 MHz, CDCl$_3$) ppm 1.41 (t, J=6.9 Hz, 3H), 3.50 (t, J=6.9 Hz, 2H), 3.64 (t, J=6.9 Hz, 2H), 4.38 (q, J=6.9 Hz, 2H), 7.27-7.39 (m, 2H), 7.45 (t, J=7.5 Hz, 1H), 7.96 (d, J=7.5 Hz, 1H).

Step 3: ethyl 2-(3-amino-4-ethoxy-4-oxobutyl)benzoate

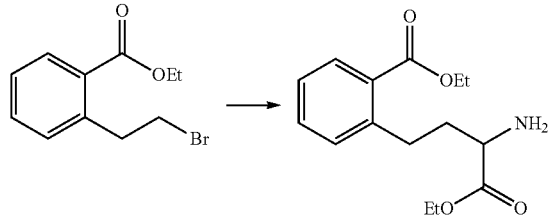 [SMILES: CCOC(=O)c1ccccc1CCBr ; CCOC(=O)c1ccccc1CCC(N)C(=O)OCC]

The reaction was run in two separate batches.

N-(Diphenylmethylene)glycine ethyl ester (4.17 g, 15.6 mmol) was added to a suspension of finely powdered potassium hydroxide (2.63 g, 46.8 mmol) in dimethylsulfoxide (20 ml) cooled with an ice-water bath (an orange mixture was obtained). Then ethyl 2-(2-bromoethyl)benzoate (4.0 g, 15.6 mmol) was added dropwise. The reaction was stirred at room temperature for 60 minutes and then diluted with ethyl acetate (150 mL). The solution was decanted into a separation funnel and the solid (KOH) was discarded. The organic phase was washed with water (3×50 mL) brine, dried over anhydrous Na$_2$SO$_4$ and concentrated under reduced pressure. The second batch was run in a similar way: ethyl 2-(2-bromoethyl) benzoate (9.3 g, 36.1 mmol), N-(diphenylmethylene)glycine ethyl ester (9.65 g, 36.1 mmol), potassium hydroxide (6.08 g, 108.3 mmol) and dimethylsulfoxide (50 mL).

The crude products of the two batches were combined (19 g) and dissolved in tetrahydrofuran (50 mL). The solution was cooled with an ice-water bath and 1 N HCl aqueous solution (60 mL) was added. The mixture was stirred at room temperature for 30 minutes. Water (50 mL) and ethyl acetate (50 mL) were added, the biphasic mixture was extracted and the two phases were separated. The aqueous phase was then basified with 2 N NaOH aqueous solution (30 mL) at 0° C. and the resulting aqueous solution was extracted with ethyl acetate (2×50 mL). The organic layers were combined, washed with brine (20 mL), dried over anhydrous Na$_2$SO$_4$ and concentrated under reduced pressure. The residue was purified with silica chromatography, eluting with a mixture of methanol and dichloromethane (0-7%) to give ethyl 2-(3-amino-4-ethoxy-4-oxobutyl)benzoate (6.6 g, 46% yield) as a yellow oil. $^1$H NMR (300 MHz, CDCl$_3$) 1.27 (t, J=7.1 Hz, 3H), 1.41 (t, J=7.1 Hz, 3H), 1.75-1.93 (m, 1H), 1.97-2.14 (m, 1H), 2.95-3.15 (m, 2H), 3.42-3.54 (m, 1H), 4.17 (q, J=7.1 Hz, 2H), 4.35 (q, J=7.1 Hz, 2H), 7.20-7.30 (m, 2H), 7.41 (t, J=7.5 Hz, 1H), 7.88 (d, J=7.5 Hz, 1H). LCMS: [M+H]$^+$=280.2.

Step 4: Synthesis of ethyl 1-oxo-2,3,4,5-tetrahydro-1H-2-benzazepine-3-carboxylate

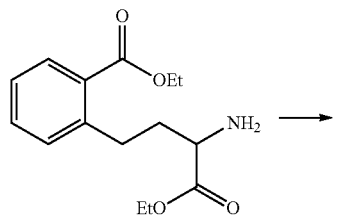

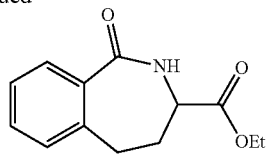

Sodium metal (823 mg, 35.8 mmol) was added to anhydrous ethanol (270 mL, dried with 3 Å molecular sieves) in a flask at room temperature. The mixture was stirred at room temperature until all the sodium had disappeared. Then a solution of ethyl 2-(3-amino-4-ethoxy-4-oxobutyl)benzoate (5.0 g, 18 mmol) in anhydrous ethanol (30 mL) was added at room temperature. The reaction was stirred at room temperature for two days and then cooled with an ice-water bath. Thionyl chloride (10 mL) was slowly added (reacts violently) and the reaction was refluxed for 2 hours. The solvent was removed under reduced pressure and the residue was taken up into ethyl acetate (100 mL), washed with saturated aqueous sodium bicarbonate (30 mL), brine, dried over Na$_2$SO$_4$ and concentrated under reduced pressure. The residue was purified by silica chromatography, eluting with a mixture of ethyl acetate and heptanes (10 to 100%) to afford ethyl 1-oxo-2,3,4,5-tetrahydro-1H-2-benzazepine-3-carboxylate (2.9 g, 69% yield) as a yellow oil. $^1$H NMR (300 MHz, CDCl$_3$) ppm 1.24 (t, J=6.7 Hz, 3H), 2.07-2.25 (m, 1H), 2.26-2.43 (m, 1H), 2.70-2.84 (m, 1H), 2.89-3.08 (m, 1H), 3.80-3.95 (m, 1H), 4.20 (q, J=6.7 Hz, 2H), 6.69 (s, 1H), 7.20 (d, J=7.2 Hz, 1H), 7.33 (t, J=7.2 Hz, 1H), 7.41 (t, J=7.2 Hz, 1H), 7.70 (d, J=7.2 Hz, 1H). LCMS: [M+H]$^+$=234.1.

Step 5: tert-butyl 1-oxo-2,3,4,5-tetrahydro-1H-2-benzazepine-3-carboxylate

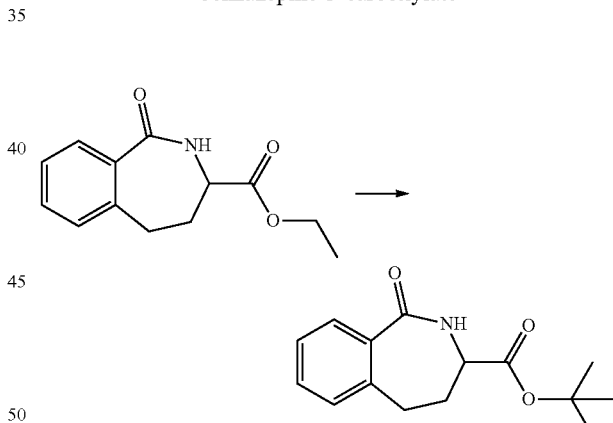

Butyl lithium (17.4 mL of 2.5 M in hexanes, 43.4 mmol) was added to a solution of anhydrous tert-butanol (4.7 mL, 50. mmol, distilled and then dried over potassium carbonate) in anhydrous tetrahydrofuran (40 mL) at -78° C. in a pressure tube under nitrogen. The mixture was stirred at room temperature for 10 min, then a solution of ethyl 1-oxo-2,3,4,5-tetrahydro-1H-2-benzazepine-3-carboxylate (2.9 g, 12 mmol) in anhydrous tetrahydrofuran (10 mL) was added and the mixture was stirred at 30° C. overnight. Volatiles were removed under reduced pressure and the residue was taken up into a mixture of water (40 mL) and dichloromethane (100 mL). The two phases were separated and the organic phase was dried over anhydrous Na$_2$SO$_4$ and concentrated under reduced pressure. The residue was purified by silica chromatography, eluting with a mixture of ethyl acetate and heptanes (0 to 30%) to give tert-butyl 1-oxo-2,3,4,5-tetrahydro-1H-2-benzazepine-3-carboxylate (1.4 g, 43% yield) as a white solid. ¹H NMR (300 MHz, CDCl₃) ppm 1.44 (s, 9H), 1.99-2.23 (m, 1H), 2.32 (tt, J=12.7, 6.3 Hz, 1H), 2.77 (dd, J=13.7, 6.3 Hz, 1H), 2.89-3.11 (m, 1H), 3.68-3.88 (m, 1H), 6.64 (br. s., 1H), 7.21 (d, J=7.3 Hz, 1H), 7.29-7.49 (m, 2H), 7.71 (d, J=7.5 Hz, 1H). [M+H]⁺=262.1.

Step 6: tert-butyl 1-methoxy-4,5-dihydro-1H-2-benzazepine-3-carboxylate

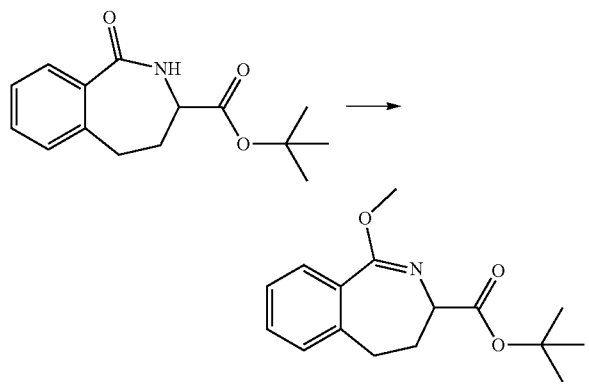

The reaction was run in two identical batches. 4 Å molecular sieves were added to a sealed tube. The tube was flame-dried under vacuum and then flushed with nitrogen. After the tube was cooled to room temperature, tert-butyl 1-oxo-2,3,4,5-tetrahydro-1H-2-benzazepine-3-carboxylate (522 mg, 2.00 mmol) was added followed by anhydrous dichloromethane (9 mL) and trimethyloxonium tetrafluoroborate (296 mg, 2.00 mmol). The mixture was stirred at 30° C. for 16 hours. The mixture was quenched with a saturated aqueous sodium bicarbonate solution (30 mL). The resulting mixture was extracted with ethyl acetate (2×40 mL). The organic phases were combined and washed with brine (20 mL), dried over anhydrous Na₂SO₄ and concentrated under reduced pressure. The residue of the two batches were combined and purified by silica chromatography, eluting with a mixture of ethyl acetate and heptanes (0 to 30%) to provide tert-butyl 1-methoxy-4,5-dihydro-3H-2-benzazepine-3-carboxylate (900. mg, 3.27 mmol, 81.7% yield) as a colorless oil. ¹H NMR (300 MHz, CDCl₃) ppm 1.43 (s, 9H), 2.33-2.49 (m, 2H), 2.58-2.70 (m, 2H), 3.50 (dd, J=11.0, 7.2 Hz, 1H), 3.96 (s, 3H), 7.20-7.28 (m, 1H), 7.30-7.40 (m, 2H), 7.41-7.47 (m, 1H). LCMS: [M+H]⁺=276.1.

Step 7: tert-butyl 2,3,4,5-tetrahydro-1H-2-benzazepine-3-carboxylate

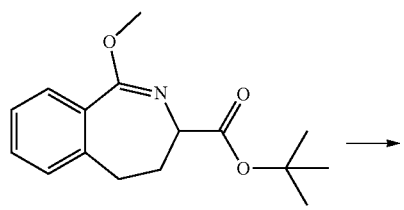

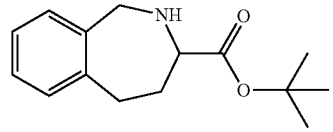

Sodium cyanoborohydride (821 mg, 13.1 mmol) was added to a solution of tert-butyl 1-methoxy-4,5-dihydro-3H-2-benzazepine-3-carboxylate (900. mg, 3.27 mmol) in acetic acid (3 mL) at 0° C. The mixture was stirred at room temperature for 2 hours. The mixture was diluted with ethyl acetate (40 mL) and cooled with an ice-water bath. An aqueous solution of NaOH (25% w/v) was slowly added to adjust the pH to about 8. The two phases were separated and the aqueous phase was extracted with ethyl acetate (40 mL). The organic phases were combined, washed with brine (10 mL), dried over anhydrous Na₂SO₄ and concentrated under reduced pressure. The residue was purified by silica chromatography, eluting with a mixture of ethyl acetate and dichloromethane (0 to 50%) to give tert-butyl 2,3,4,5-tetrahydro-1H-2-benzazepine-3-carboxylate (610. mg, 2.47 mmol, 75.5% yield) as a yellow oil. ¹H NMR (300 MHz, CDCl₃) ppm 1.46 (s, 9H), 1.53-1.66 (m, 1H), 2.17-2.37 (m, 1H), 2.79-2.99 (m, 1H), 2.99-3.18 (m, 1H), 3.65 (dd, J=10.6, 2.9 Hz, 1H), 3.93 (d, J=15.1 Hz, 1H), 3.97 (d, J=15.1 Hz, 1H), 7.06-7.21 (m, 4H). [M+H]⁺=248.1.

Preparation 75: 1-[(4-methoxyphenyl)methyl]-2-oxopyrrolidine-3-sulfonamide

Step 1: 2,4-dibromo-N-[(4-methoxyphenyl)methyl]butanamide

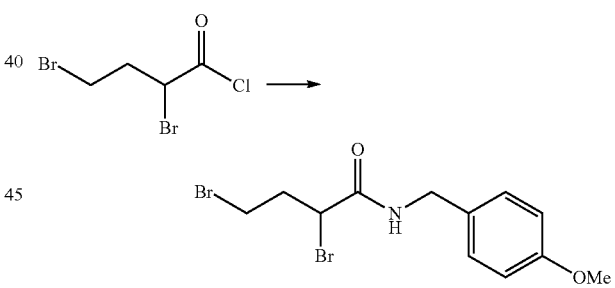

To a solution of 2,4-dibromobutanoyl chloride (5.00 g, 18.9 mmol) in dichloromethane (250 mL) at 0° C. was added triethylamine (2.38 g, 23.6 mmol) followed by 4-methoxybenzylamine (2.59 g, 18.9 mmol) and the mixture was stirred at 0° C. for 2 hours. The reaction was then poured at 0° C. into a solution of 5% citric acid (80 mL) at pH=3-4 and diluted with dichloromethane (100 mL) and water (50 mL). The organic layer was separated and the aqueous player was extracted again with dichloromethane (50 mL). The combined organic layer was dried over Na₂SO₄, filtered and concentrated under reduced pressure to afford crude 2,4-dibromo-N-[(4-methoxyphenyl)methyl]butanamide (7.09 g, 103%) as a brown solid. ¹H NMR (300 MHz, CDCl₃) ppm 2.41-2.55 (m, 1H), 2.64-2.84 (m, 1H), 3.52-3.61 (m, 2H), 3.80 (s, 3H), 4.36-4.44 (m, 2H), 4.55 (dd, J=9.0, 4.8 Hz, 1H), 6.54 (br. s, 1H), 6.85-6.91 (m, 2H), 7.19-7.23 (m, 2H). [M+H]⁺=366.0.

Step 2: 3-bromo-1-[(4-methoxyphenyl)methyl]pyrrolidin-2-one

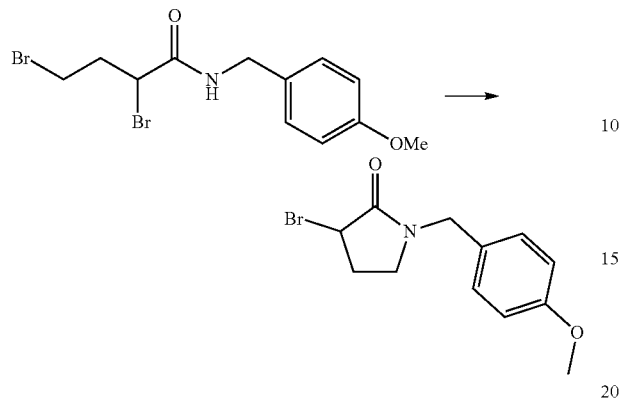

To a solution of 2,4-dibromo-N-[(4-methoxyphenyl)methyl]butanamide (3.25 g, 8.90 mmol) in tetrahydrofuran (120 mL) and N,N-dimethylformamide (12 mL) was added sodium hydride (427 mg of 60% dispersion in mineral oil, 17.8 mmol) portionwise at 0° C. and the mixture was stirred at room temperature for 2.5 hours. The reaction mixture was cooled again to 0° C. and quenched carefully with an aqueous 5% citric acid solution (10 mL). The volatiles were then removed under reduced pressure. The reaction mixture was diluted with water and dichloromethane and the aqueous layer was extracted twice with dichloromethane. The combined organic layers were dried over $Na_2SO_4$, filtered, concentrated under reduced pressure and co-evaporated with heptanes as a co-solvent (twice) to afford crude 3-bromo-1-[(4-methoxyphenyl)methyl]pyrrolidin-2-one (2.5 g, 99%) as a pale yellow oil. $^1$H NMR (300 MHz, $CDCl_3$) ppm 2.22-2.32 (m, 1H), 2.47-2.60 (m, 1H), 3.14-3.21 (m, 1H), 3.35-3.44 (m, 1H), 3.80 (s, 3H), 4.33-4.52 (m, 3H), 6.84-6.87 (m, 2H), 7.15-7.20 (m, 2H). [M+H]$^+$=284.0.

Step 3: methyl 3-({1-[(4-methoxyphenyl)methyl]-2-oxopyrrolidin-3-yl}sulfonyl)propanoate

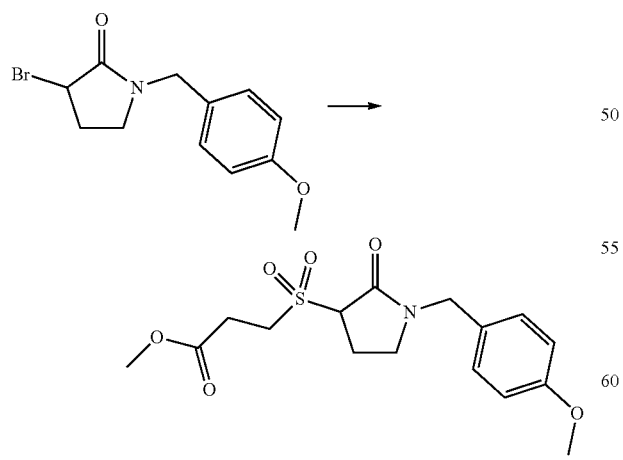

To a solution of 3-bromo-1-[(4-methoxyphenyl)methyl]pyrrolidin-2-one (2.50 g, 8.80 mmol) in dimethylsulfoxide (50 mL) was added sodium 1-methyl 3-sulfinopropanoate (1.53 g, 8.80 mmol) and the reaction was stirred at room temperature for three days. The solution was diluted with water (400 mL) and extracted with dichloromethane (2×250 mL). The combined organic layer was washed with water (150 mL), brine (100 mL), dried over $Na_2SO_4$, filtered and concentrated under reduced pressure to afford crude methyl 3-({1-[(4-methoxyphenyl)methyl]-2-oxopyrrolidin-3-yl}sulfonyl)propanoate (2.5 g, 80.% yield). $^1$H NMR (300 MHz, $CDCl_3$) ppm 2.31-2.45 (m, 1H), 2.65-2.75 (m, 1H), 2.85-3.05 (m, 2H), 3.26 (dt, J=9.4, 3.8 Hz, 1H), 3.41-3.50 (m, 1H), 3.74 (s, 3H), 3.79 (s, 3H), 3.77-3.92 (m, 2H), 4.01 (dd, J=10.2, 4.6 Hz, 1H), 4.44 (s, 2H), 6.87 (d, J=8.6 Hz, 2H), 7.16 (d, J=8.5 Hz, 2H). [M+H]$^+$=356.1.

Step 4: sodium 1-[(4-methoxyphenyl)methyl]-2-oxopyrrolidine-3-sulfinate

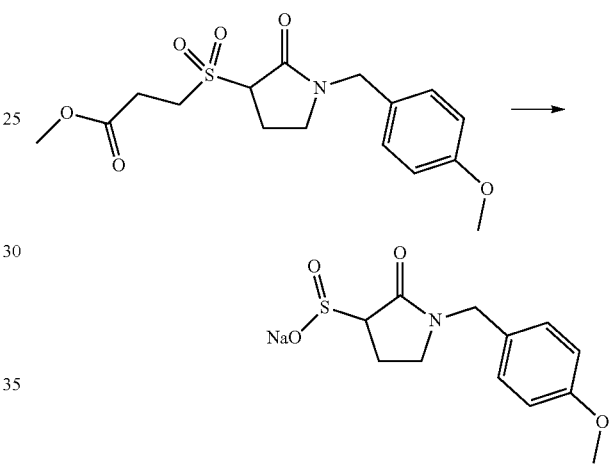

To a solution of methyl 3-({1-[(4-methoxyphenyl)methyl]-2-oxopyrrolidin-3-yl}sulfonyl)propanoate (2.50 g, 7.03 mmol) in a 1:1 (v/v) mixture of tetrahydrofuran and methanol (40 mL) was added sodium methoxide (3.39 mL of 25 wt. % in methanol, 14.8 mmol) and the reaction was stirred at room temperature for 4 hours. The reaction mixture was then concentrated under reduced pressure to remove the methyl acrylate and kept under reduced pressure to provide crude sodium 1-[(4-methoxyphenyl)methyl]-2-oxopyrrolidine-3-sulfinate that was used directly in the next step without further purification [M+H]$^+$=270.0 (sulfinic acid).

Step 5: Synthesis of 1-[(4-methoxyphenyl)methyl]-2-oxopyrrolidine-3-sulfonamide

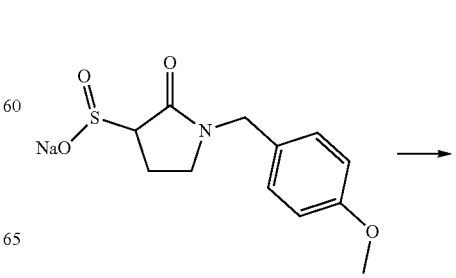

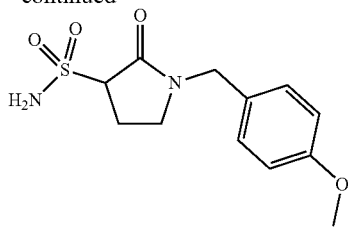

To a solution of crude sodium 1-[(4-methoxyphenyl)methyl]-2-oxopyrrolidine-3-sulfinate (2.05 g, 7.03 mmol) in dimethylsulfoxide (20 ml) was added a solution of hydroxylamine-O-sulfonic acid (3.98 g, 35.2 mmol) and sodium acetate (2.19 g, 26.7 mmol) in water (7 mL) at 0° C. The reaction was stirred for 16 hours at room temperature then diluted with ethyl acetate and water. The aqueous layer was extracted with ethyl acetate (2×100 mL). The combined organic layer was washed with brine (75 mL), dried over $Na_2SO_4$, filtered and concentrated under reduced pressure. The crude material was purified by silica-gel chromatography using 0% to 10% methanol in dichloromethane (containing 1% $NH_4OH$) to afford 1-[(4-methoxyphenyl)methyl]-2-oxopyrrolidine-3-sulfonamide (1.3 g, 63% yield) as a pale brown solid. $^1H$ NMR (300 MHz, $CDCl_3$) ppm 2.29-2.73 (m, 2H), 3.14-3.34 (m, 1H), 3.34-3.51 (m, 1H), 3.80 (s, 3H), 3.89-4.11 (m, 1H), 4.30-4.61 (m, 2H), 5.25 (br. s., 2H), 6.75-6.98 (m, 2H), 7.10-7.22 (m, 2H). $[M+H]^+=285.1$.

Preparation 76: 6-(3-fluoro-5-isobutoxy-phenyl)-N-(2-oxopyrrolidin-3-yl)sulfonyl-2-(2,2,4-trimethylpyrrolidin-1-yl)pyridine-3-carboxamide (Compound 466)

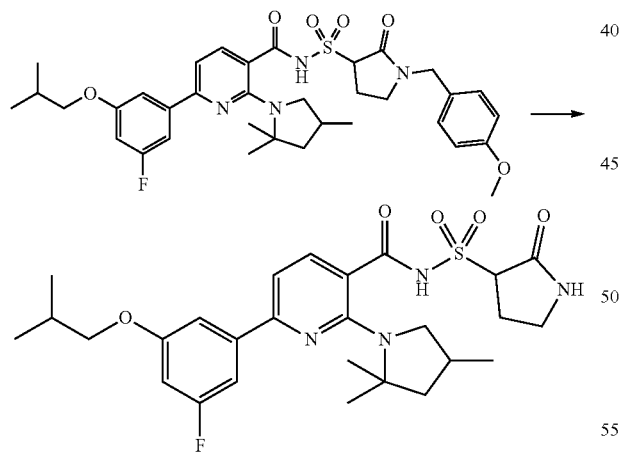

6-(3-fluoro-5-isobutoxy-phenyl)-N-[1-[(4-methoxyphenyl)methyl]-2-oxo-pyrrolidin-3-yl]sulfonyl-2-(2,2,4-trimethylpyrrolidin-1-yl)pyridine-3-carboxamide (32.7 mg, 0.0490 mmol) was dissolved in a mixture of trifluoroacetic acid (0.9319 mL) and dichloromethane (0.9319 mL). Trifluoromethanesulfonic acid (25.75 mg, 15.18 µL, 0.1716 mmol) was then added and the mixture and stirred at ambient temperature for 20 hours. The reaction mixture was concentrated, then diluted with dimethylsulfoxide and purified by reverese-phase chromatography utilizing a C18 column and a gradient of 1-99% acetonitrile in 5 mM aq HCl to yield 6-(3-fluoro-5-isobutoxy-phenyl)-N-(2-oxopyrrolidin-3-yl)sulfonyl-2-(2,2,4-trimethylpyrrolidin-1-yl)pyridine-3-carboxamide (Compound 466) $^1H$ NMR (400 MHz, DMSO-$d_6$) δ 8.27 (d, J=19.3 Hz, 1H), 7.94 (d, J=8.0 Hz, 1H), 7.72 (d, J=8.0 Hz, 1H), 7.51 (s, 1H), 7.43 (d, J=10.1 Hz, 1H), 7.28 (dd, J=14.4, 8.0 Hz, 1H), 6.90 (dt, J=10.6, 2.3 Hz, 1H), 4.61-4.44 (m, 1H), 3.84 (d, J=6.7 Hz, 2H), 3.40-2.86 (m, 4H), 2.16-1.91 (m, 2H), 1.71-1.60 (m, 7H), 1.60-1.49 (m, 1H), 1.16 (s, 1H), 1.06-0.96 (m, 10H). ESI-MS m/z calc. 546.2312, found 547.3 $(M+1)^+$; Retention time: 1.87 minutes Preparation 77: 5-isopropyl-1-(2,4,6-trimethylbenzyl)-1H-indole-2-carboxylic acid and 5-propyl-1-(2,4,6-trimethylbenzyl)-1H-indole-2-carboxylic acid

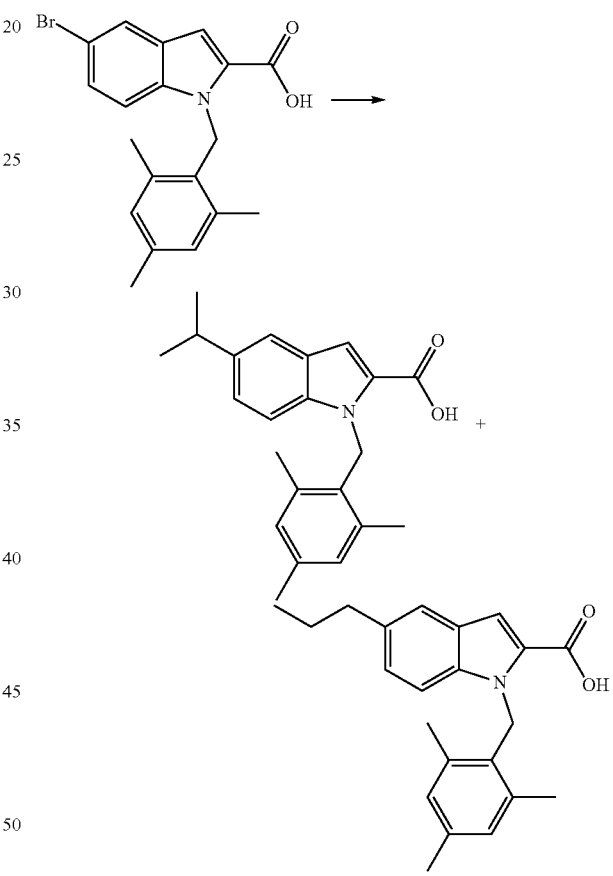

Step 1: 5-bromo-1-[(2,4,6-trimethylphenyl)methyl]indole-2-carboxylic acid (0.7000 g, 1.880 mmol), [1,1'-Bis(diphenylphosphino)ferrocene]dichloropalladium(II), complex with dichloromethane (68.78 mg, 0.09400 mmol), aqueous sodium carbonate (1.880 mL of 2 M, 3.760 mmol), and 2-isopropenyl-4,4,5,5-tetramethyl-1,3,2-dioxaborolane (315.9 mg, 1.880 mmol) in dioxane (5 mL) were added to a microwave reactor vial. The vial was purged with nitrogen, capped and heated to 120° C. for 45 minutes in a microwave reactor. The reaction mixture was diluted with water and extracted with ethyl acetate (2×10 mL). The organic layers were dried over sodium sulfate, concentrated, and purified by reverse-phase chromatography utilizing a C18 column and a gradient of 30-90% acetonitrile in 5 mM aq HCl to give a mixture of products which could not be separated under these specific condition. This material was dissolved in methanol (10 mL) and palladium on carbon (20.01 mg, 0.01880 mmol) was added to the reaction mixture The mixture was stirred under an atmosphere of hydrogen for 4 hours. The mixture of crude products was filtered, through a pad of silica gel with 100 mL of 15% methanol in dichloromethane and used for the next step without further manipulation. ESI-MS m/z calc. 335.19, found 336.5 (M+1)$^+$; Retention time: 0.84 minutes.

Preparation 78: (4R)-2,2,4-trimethylpyrrolidine

Step 1: Methyl 2,4-dimethyl-4-nitropentanoate

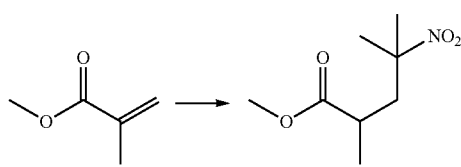

A 1-L three-necked flask was fitted with a dropping funnel, and a thermometer. A solution of 2-nitropropane (178 g, 2.00 mol) in dioxane (100 mL) and a 40% aqueous solution of benzyltrimethylammonium hydroxide (Triton B, 20.0 mL, 420. mmol) were added to the flask. The flask was heated to 70° C. in an oil bath and methyl methacrylate (200. g, 212.3 mL, 2.00 mol) was added via a dropping funnel over 45 minutes. The temperature rose to about 100° C. during the addition then dropped to ~ 90° C. The mixture was then heated at 100° C. for 4 hours. The reaction mixture was cooled to room temperature and 1 N hydrochloric acid (80 mL) was added. Water (500 mL) and diethyl ether (1000 mL) were added to the reaction flask. The mixture was poured into a separatory funnel and organic layer was washed with water (2×400 mL), brine (400 mL), dried over anhydrous sodium sulfate, filtered and concentrated under reduced pressure to give a yellow liquid. The product was distilled through a short path distillation apparatus to give a pale yellow liquid (356 g, 94%) (oil bath temperature 150° C., an oil pump, collecting temperature 100 to 108° C.). $^1$H NMR (CDCl$_3$, 250 MHz): δ 3.67 (s, 3H), 2.55-2.35 (m, 2H), 2.10-1.90 (m, 1H), 1.58 (s, 3H), 1.53 (s, 3H), 1.18 (d, J=6.5 Hz, 3H).

Step 2: (R)-3,5,5-trimethylpyrrolidin-2-one and (S)-3,5,5-trimethylpyrrolidin-2-one

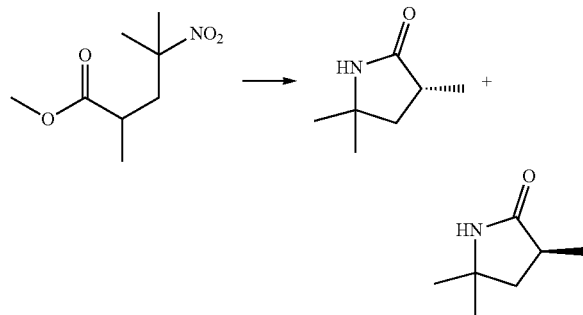

A solution of methyl 2,4-dimethyl-4-nitro-pentanoate (100. g, 528.5 mmol), nickel(II) chloride hexahydrate (25.12 g, 105.7 mmol), water (28.57 g, 28.57 mL, 1.586 mol) and methanol (1.200 L) was cooled to 0 to 5° C. Sodium borohydride (49.98 g, 1.321 mol) was slowly added to the reaction mixture while maintaining the reaction temperature below 20° C. The addition was exothermic with steady and prolonged gas generation. The reaction mixture was allowed to stand for 14 days. A solution of potassium carbonate (146.1 g, 1.057 mol) in water (1.000 L) was slowly added to the reaction mixture. The reaction mixture was then filtered through a pad of celite. The pad was then washed with three 100 mL portions of methanol. The reaction mixture was then concentrated under reduced pressure to remove the methanol. Methyl tert-butyl ether (1 L) was added. The layers were separated and the aqueous layer was extracted twice with 400 mL portions of methyl tert-butyl ether. The combined organic layers were dried over sodium sulfate, filtered, and evaporated to dryness. This material was then portioned between methyl tert-butyl ether and an aqueous solution of sodium chloride. The organic layer was separated, dried over magnesium sulfate, filtered, and then evaporated to dryness to yield 41.5 g (61.7%) of an off-white solid. The stereoisomers were separated using supercritical fluid chromatography on a ChiralPak AS-H (250×4.6 mm), 5 m column using 10% methanol in CO$_2$ at a flow rate of 3.0 mL/min.

Step 3: (4R)-2,2,4-trimethylpyrrolidine

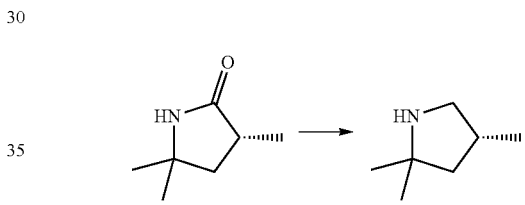

A solution of (3R)-3,5,5-trimethylpyrrolidin-2-one (20.0 g, 157 mmol) in tetrahydrofuran (200.0 mL) was cooled to 0 to 5° C. Lithium aluminum hydride (8.006 g, 236.0 mmol) was added in portions over 10 minutes while maintain the temperature of the reaction mixture below 20° C. The addition was somewhat exothermic and degassing was observed. The suspension was heated to reflux for 9.5 hours. After cooling to room temperature an additional portion of lithium aluminum hydride (1.601 g, 1.746 mL, 47.19 mmol) was added to the reaction mixture. The mixture was then heated to reflux for 2.5 hours. The reaction mixture was cooled to 7° C. and an aqueous solution of sodium sulfate (27.93 mL of 20% w/v, 39.32 mmol) was slowly added to the reaction mixture. The reaction mixture was then diluted with 200 mL of methyl tert-butyl ether and filtered through a pad of celite. The filtrate was dried over sodium sulfate, filtered, and concentrated at ambient pressure to remove the ethers. The crude material was purified by distillation (28° C./50 torr) to afford 10. g (56%) of a colorless liquid. 1H NMR (400 MHz, Chloroform-d) δ 3.11 (dd, J=10.8, 7.3 Hz, 1H), 2.51 (dd, J=10.9, 8.1 Hz, 1H), 2.32-2.15 (m, 1H), 1.80 (dd, J=12.4, 8.1 Hz, 1H), 1.65 (s, 1H), 1.19 (s, 3H), 1.17-1.08 (m, 4H), 1.01 (d, J=6.8 Hz, 3H). The absolute stereochemistry was determined by X-ray crystallography of the (2R)-2-(2-chlorophenyl)-2-hydroxy-acetic acid salt.

The following compounds can be synthesized using the procedures described herein
(S)-4-ethyl-2,2-dimethylpyrrolidine, and
(R)-4-ethyl-2,2-dimethylpyrrolidine The following compounds can be synthesized using the procedures described herein using lithium aluminum dueterohydride:
(S)-2,2,4-trimethylpyrrolidine-5,5-d₂ and,
(R)-2,2,4-trimethylpyrrolidine-5,5-d₂

Preparation 79: 3-Isobutoxy-1H-pyrazole

Step 1: 1-(3-isobutoxy-1H-pyrazol-1-yl)ethan-1-one

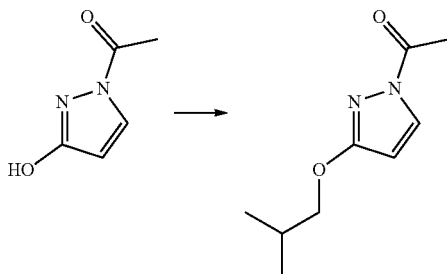

A 4 mL vial was charged with 1-(3-hydroxypyrazol-1-yl)ethanone (100. mg, 0.793 mmol), potassium carbonate (164.3 mg, 1.189 mmol) and anhydrous DMF (1.000 mL). 1-bromo-2-methyl-propane (119.5 mg, 94.84 μL, 0.8722 mmol) was added, the vial was capped and the mixture was stirred at room temperature for 16 hours. The reaction was stirred at 80° C. for one hour. The mixture was diluted with ethyl acetate (50 ml) and water (25 mL) and the two phases were separated. The aqueous phase (pH=9-10) was further extracted with ethyl acetate (20 mL). The combined extracts were dried over sodium sulfate and the solvents evaporated to give 100 mg of a crude, oil. The product was dissolved in dichloromethane and purified by flash chromatography on silica gel (4 g column) using a gradient of ethyl acetate (0 to 50% over 15 minutes) in hexanes. The pure fractions were combined and the solvents removed under reduced pressure to provide 1-(3-isobutoxypyrazol-1-yl)ethanone (78 mg, 0.43 mmol, 54%) as a colorless oil.

ESI-MS m/z calc. 182.10553, found 183.2 (M+1)⁺; Retention time: 1.34 minutes. ¹H NMR (400 MHz, Chloroform-d) δ 8.05 (d, J=3.0 Hz, 1H), 5.96 (d, J=3.0 Hz, 1H), 3.99 (d, J=6.6 Hz, 2H), 2.58 (s, 3H), 2.09 (dp, J=13.4, 6.7 Hz, 1H), 1.01 (d, J=6.7 Hz, 6H).

Step 2: 3-Isobutoxy-1H-pyrazole

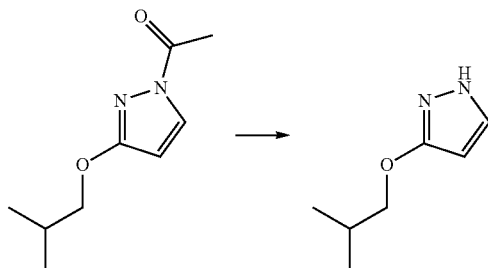

1-(3-Isobutoxy-1H-pyrazol-1-yl)ethan-1-one (72 mg, 0.40 mmol) was treated with methanol (1 mL) and NaOH (65.85 μL of 6 M, 0.3951 mmol) at room temperature for 1 hour. The volatiles were removed under reduced pressure. The residue was taken up in ethyl acetate (25 mL) and brine (20 mL) and two phases were separated. The aqueous phase was further extracted with ethyl acetate (20 mL) and the combined extracts were dried over sodium sulfate. After evaporation of the solvent, 3-isobutoxy-1H-pyrazole (55 mg, 0.39 mmol, 99%) was isolated as a colorless viscous oil. ESI-MS m/z calc. 140.09496, found 141.2 (M+1)⁺; Retention time: 0.86 minutes. ¹H NMR (400 MHz, Chloroform-d) δ 7.34 (d, J=2.4 Hz, 1H), 5.71 (d, J=2.5 Hz, 1H), 3.90 (d, J=6.6 Hz, 2H), 2.08 (dq, J=13.3, 6.7 Hz, 1H), 1.00 (d, J=6.7 Hz, 6H).

The following compounds can be synthesized using the procedures described herein 3-isobutoxy-5-methyl-1H-pyrazole, 4-isobutoxy-1H-pyrazole, and 3-isobutoxy-4-methyl-1H-pyrazole Preparation 80: N-[(6-amino-2-pyridyl)sulfonyl]-6-(3-isobutoxypyrazol-1-yl)-2-[(4S)-2,2,4-trimethylpyrrolidin-1-yl]pyridine-3-carboxamide (Compound 1620)

Step 1: tert-Butyl 2-chloro-6-(3-isobutoxypyrazol-1-yl)pyridine-3-carboxylate

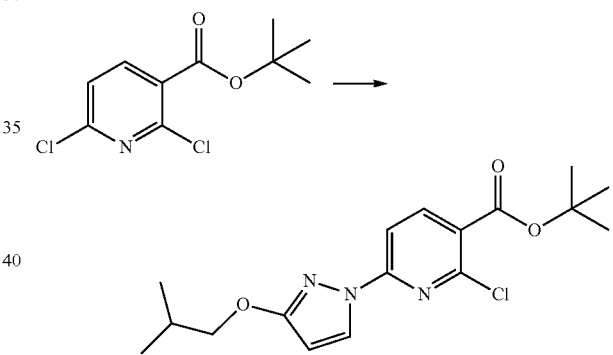

A 4 mL vial was charged under nitrogen with with 3-isobutoxy-1H-pyrazole (131.5 mg, 0.9383 mmol) and anhydrous DMF (1 mL). Sodium hydride (37.48 mg, 0.9370 mmol, 60% in mineral oil) was added and the mixture was stirred until gas evolution stopped. tert-Butyl 2,6-dichloropyridine-3-carboxylate (155 mg, 0.625 mmol) was added. The vial was capped and the mixture was stirred at 100° C. for 4 hours. LCMS showed the presence of two mono addition isomers (ratio approx. 60:40) and a major product being a double addition product. The reaction mixture was diluted with ethyl acetate (30 mL) and water (20 mL) and the two phases were separated. The aqueous phase was further extracted with ethyl acetate (25 mL). The combined extracts were dried over sodium sulfate and the solvent removed under reduced pressure to give 247 mg of crude solid. The residue was dissolved in dichloromethane and subjected to flash chromatography on silica gel (40 g column) using a gradient of ethyl acetate (0 to 20% over 20 minutes) in hexanes to yield tert-butyl 2-chloro-6-(3-isobutoxypyrazol-1-yl)pyridine-3-carboxylate (58 mg, 0.1649 mmol, 26.39%) (off-white solid). ESI-MS m/z calc. 351.13498, found 352.4 (M+1)⁺; Retention time: 2.25 minutes.

Step 2: N-[(6-amino-2-pyridyl)sulfonyl]-2-chloro-6-(3-isobutoxypyrazol-1-yl)pyridine-3-carboxamide

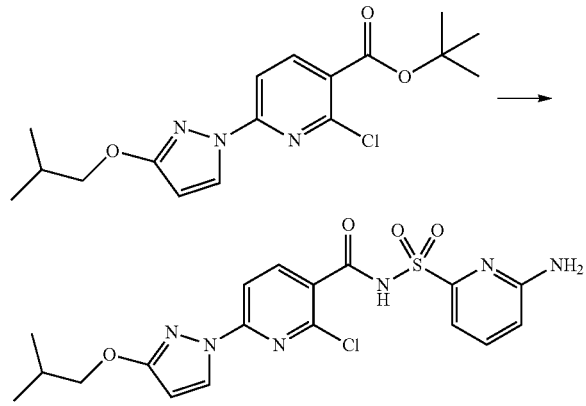

A 100 mL round bottom flask containing tert-butyl 2-chloro-6-(3-isobutoxypyrazol-1-yl)pyridine-3-carboxylate (58 mg, 0.16 mmol) was treated with dichloromethane (600 µL) and trifluoroacetic acid (180 µL, 2.336 mmol). The mixture was stirred at 45° C. for 1.5 hours. The volatiles were removed under reduced pressure to give a white solid. Anhydrous DMF (500 µL) was then added to the 100 mL flask containing the acid under an atmosphere of nitrogen and the mixture was stirred at 40° C. 1,1'-Carbonyldiimidazole (32.09 mg, 0.1979 mmol) was added and the mixture was stirred at 40° C. for 1 hour. A separate 4 mL vial under nitrogen was charged with 6-aminopyridine-2-sulfonamide (34.27 mg, 0.1979 mmol) and anhydrous DMF (500 µL). NaH (7.915 mg, 0.1979 mmol, 60% oil dispersion) was added. After gas evolution had stopped, the vial was capped and it was stirred at 40° C. for 1 hour. This mixture was added to the first flask and the mixture was stirred at room temperature for 2 hours. The reaction was quenched with ice and water an neutralized with acetic acid (148.6 mg, 140.7 µL, 2.474 mmol, final pH=4). The resulting white solid was filtered, washed with water and dried under reduced pressure. N-[(6-amino-2-pyridyl)sulfonyl]-2-chloro-6-(3-isobutoxypyrazol-1-yl)pyridine-3-carboxamide (57 mg, 0.13 mmol, 77%) was isolated as a white solid. ESI-MS m/z calc. 450.0877, found 451.3 (M+1)⁺; Retention time: 1.54 minutes Step 3: N-[(6-amino-2-pyridyl)sulfonyl]-6-(3-isobutoxypyrazo-1-yl)-2-[(4S)-2,2,4-trimethylpyrrolidin-1-yl]pyridine-3-carboxamide (Compound 1620)

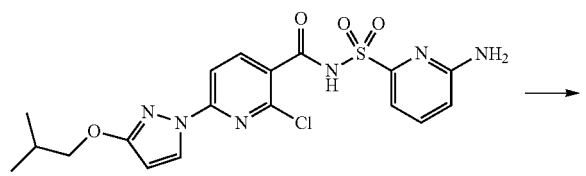

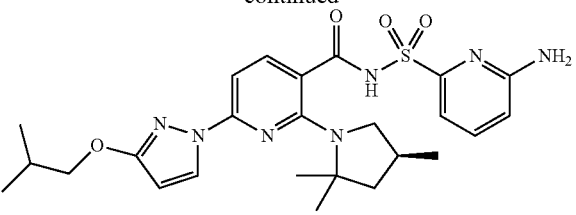

A 4 mL vial was charged under nitrogen with N-[(6-amino-2-pyridyl)sulfonyl]-2-chloro-6-(3-isobutoxypyrazol-1-yl)pyridine-3-carboxamide (57 mg, 0.13 mmol), CsF (96.00 mg, 0.6320 mmol), potassium carbonate (87.35 mg, 0.6320 mmol), (4S)-2,2,4-trimethylpyrrolidine (47.64 mg, 0.3792 mmol) and anhydrous dimethylsulfoxide (200 µL). The vial was capped and the contents were stirred at 150° C. for 4 hours. The mixture was diluted with water (200 uL), N-methylpyrrolidinone (600 uL) and the mixture was filtered. The compound was purified by reverse phase preparative HPLC using a gradient of acetonitrile in water (1 to 99% over 15 minutes) in 5 mM aqueous ammonium formate. The pure fractions were combined, a few drops of brine was added and the organic solvents were removed under reduced pressure. The solid that crashed out was extracted with dichloromethane (3×20 mL). The combined extracts were dried over sodium sulfate, filtered, and the solvents were removed under reduced pressure to give 28 mg of material that still contained an impurity. The material was purified a second time by preparative HPLC using a gradient of acetonitrile in water (1 to 99% over 15 minutes) in 5 mM aqueous hydrochloric acid. The product was isolated using the same extraction procedure. After concentration of the dichloromethane, a solid was obtained by adding hexanes. Evaporation of the solvents gave N-[(6-amino-2-pyridyl)sulfonyl]-6-(3-isobutoxypyrazol-1-yl)-2-[(4S)-2,2,4-trimethylpyrrolidin-1-yl]pyridine-3-carboxamide (Compound 1620) (18 mg, 0.03394 mmol, 26.86%) as an off-white solid. ESI-MS m/z calc. 527.23145, found 528.5 (M+1)⁺; Retention time: 1.77 minutes. ¹H NMR (400 MHz, Chloroform-d) δ 13.87 (broad s, 1H), 8.29 (d, J=8.0 Hz, 1H) 8.21 (d, J=2.9 Hz, 1H), 7.65-7.58 (m, 2H), 7.52 (d, J=8.5 Hz, 1H), 6.65 (p, J=3.8 Hz, 1H), 5.95 (d, J=2.8 Hz, 1H), 4.80 (broad s, 2H), 4.02 (d, J=6.6 Hz, 2H), 3.52-3.41 (m, 1H), 3.15 (dd, J=10.5, 8.1 Hz, 1H), 2.69-2.50 (m, 1H), 2.18-2.02 (m, 2H), 1.72 (dd, J=12.3, 9.7 Hz, 1H), 1.45 (s, 3H), 1.39 (s, 3H), 1.19 (d, J=6.6 Hz, 3H), 1.02 (d, J=6.7 Hz, 6H).

The following compounds can be synthesized using the procedures described herein N-[(6-amino-2-pyridyl)sulfonyl]-6-(3-isobutoxy-5-methyl-pyrazol-1-yl)-2-[(4S)-2,2,4-trimethylpyrrolidin-1-yl] pyridine-3-carboxamide (Compound 1407), N-[(2-amino-3-pyridyl)sulfonyl]-6-[3-(cyclobutylmethoxy) pyrazol-1-yl]-2-[(4S)-2,2,4-trimethylpyrrolidin-1-yl] pyridine-3-carboxamide (Compound 2694), N-[(2-amino-3-pyridyl)sulfonyl]-6-[3-(cyclopropyl-methoxy)pyrazol-1-yl]-2-[(4S)-2,2,4-trimethylpyrrolidin-1-yl]pyridine-3-carboxamide (Compound 2695), N-[(2-amino-3-pyridyl)sulfonyl]-6-[3-(2,2-dimethyl-propoxy)-4-methyl-pyrazol-1-yl]-2-[(4S)-2,2,4-trimethylpyrrolidin-1-yl]pyridine-3-carboxamide (Compound 2699), N-[(6-amino-2-pyridyl)sulfonyl]-6-(3-isobutylpyrazol-1-yl)-2-[(4S)-2,2,4-trimethylpyrrolidin-1-yl]pyridine-3-carboxamide (Compound 1411), N-[(6-amino-2-pyridyl)sulfonyl]-6-(5-isobutylpyrazol-1-yl)-2-[(4S)-2,2,4-trimethylpyrrolidin-1-yl]pyridine-3-carboxamide (Compound 1431),
N-[(6-amino-2-pyridyl)sulfonyl]-6-(4-isobutoxypyrazol-1-yl)-2-[(4S)-2,2,4-trimethylpyrrolidin-1-yl]pyridine-3-carboxamide (Compound 1443),
N-[(6-amino-2-pyridyl)sulfonyl]-6-(3-ethoxy-5-methylpyrazol-1-yl)-2-[(4S)-2,2,4-trimethylpyrrolidin-1-yl]pyridine-3-carboxamide (Compound 1473), and
N-[(6-amino-2-pyridyl)sulfonyl]-6-(3-isobutoxy-4-methylpyrazol-1-yl)-2-[(4S)-2,2,4-trimethylpyrrolidin-1-yl]pyridine-3-carboxamide (Compound 1532)

Preparation 81: N-[(6-amino-2-pyridyl)sulfonyl]-6-tert-butyl-5-(3,4-dihydro-2H-pyran-5-yl)-2-(2,2,4-trimethylpyrrolidin-1-yl)pyridine-3-carboxamide (Compound 1487)

Step 1: 5-bromo-6-tert-butyl-2-hydroxypyridine-3-carbonitrile

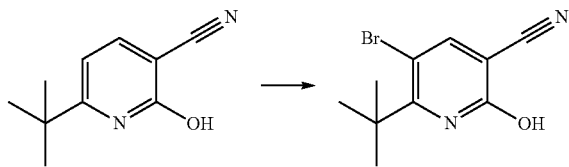

N-Bromosuccinimide (10.3 g, 57.9 mmol) was added to 6-tert-butyl-2-hydroxypyridine-3-carbonitrile (6.8 g, 38.6 mmol) in 1,2-dichloroethane (50 mL) and the reaction mixture was refluxed for 3 h. Water was added and extracted twice with dichloromethane (2×50 mL). The organic phase was washed with water, dried with anhydrous sodium sulfate and concentrated under reduced pressure. The residue was purified by flash chromatography (100% dichloromethane to 10% methanol/90% dichloromethane) to provide 5-bromo-6-tert-butyl-2-hydroxypyridine-3-carbonitrile in 65% yield (6.4 g) as a white solid. $^1$H NMR (300 MHz, DMSO-d$_6$) ppm 1.43 (s, 9H), 8.36 (s, 1H). [M+H]$^+$=255.0, 257.0.

Step 2: 5-bromo-6-tert-butyl-2-chloropyridine-3-carbonitrile

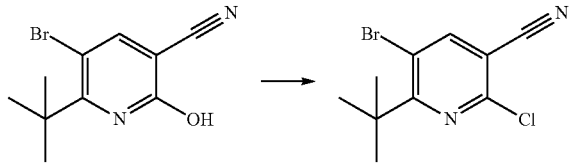

Phosphorus oxychloride (30.3 mL, 325 mmol) and phosphorus pentachloride (20.3 g, 97.6 mmol) were added to 5-bromo-6-tert-butyl-2-hydroxypyridine-3-carbonitrile (8.30 g, 32.5 mmol) and the reaction mixture was refluxed for 2 days. The reaction mixture was cooled to room temperature and concentrated under reduced pressure. Water was added to the residue, extracted 3 times with ethyl acetate (75-mL portions), washed with brine (75 mL), dried with anhydrous sodium sulfate, filtered and concentrated under reduced pressure. The residue was purified by flash chromatography (100% heptanes to 50% ethyl acetate/50% heptanes) to provide 5-bromo-6-tert-butyl-2-chloroxypyridine-3-carbonitrile in 39% yield (3.5 g) as an off-white solid. $^1$H NMR (300 MHz, CDCl$_3$) ppm 1.52 (s, 9H), 8.08 (s, 1H). [M+H]$^+$=273.0, 275.0.

Step 3: 5-bromo-6-tert-butyl-2-chloropyridine-3-carboxylic acid

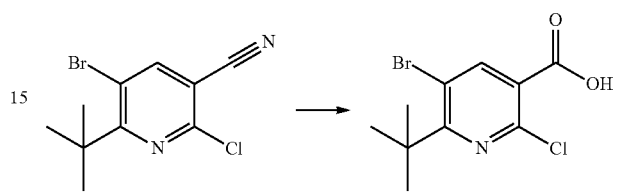

Potassium hydroxyde (4.3 g, 77 mmol) in water (15 mL) was added to 5-bromo-6-tert-butyl-2-chloroxypyridine-3-carbonitrile in 2-propanol (15 mL) and the reaction mixture was heated at 90° C. for 16 hours. Ethyl acetate (50 mL) was added and extracted 3 times with 1N sodium hydroxide (3×50 mL). The aqueous phase was acidified to pH ~4 with 10% hydrochloric acid and the aqueous phase was extracted 3 times with ethyl acetate (3×75 mL), and washed with brine (100 mL). The desired compound was present in all organic phases so they were combined, dried with anhydrous sodium sulfate, filtered and concentrated under reduced pressure. The crude compound was purified by reverse phase chromatography (methanol/water, 0 to 100%) to afford 5-bromo-6-tert-butyl-2-chloropyridine-3-carboxylic acid (2.3 g, 61% yield) as an off-white solid. $^1$H NMR (300 MHz, CDCl$_3$) ppm 1.53 (s, 9H), 8.46 (s, 1H). [M+H]$^+$=292.0, 294.0.

Step 4: N-[(6-amino-2-pyridyl)sulfonyl]-5-bromo-6-tert-butyl-2-chloro-pyridine-3-carboxamide

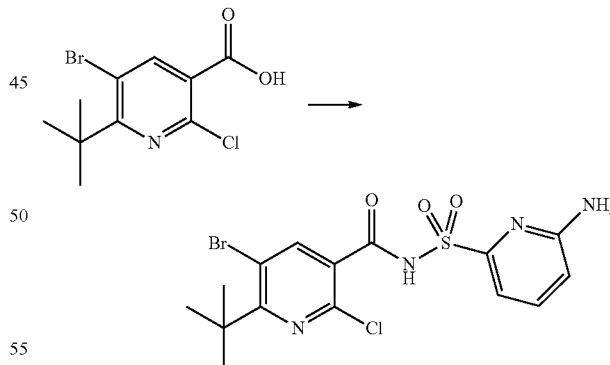

To a stirred solution of 5-bromo-6-tert-butyl-2-chloro-pyridine-3-carboxylic acid (500.0 mg, 1.709 mmol) in dry DMF (3.5 mL) in a 50 mL round-bottom flask was added 1,1'-carbonyldiimidazole (346.3 mg, 2.136 mmol) in one portion under nitrogen at ambient temperature. The reaction was warmed to 45° C. and stirred for 1.5 h. In a separate 50 mL round-bottom flask, 6-aminopyridine-2-sulfonamide (369.9 mg, 2.136 mmol) was dissolved in dry DMF (2.5 mL) under nitrogen and sodium hydride (60% in mineral oil) (85.43 mg, 2.136 mmol) was added in portions to mitigate gas evolution at ambient temperature. The heterogeneous mixture was warmed to 40° C. and stirred for 1 hour. This mixture was added to the stirred activated acid mixture in one portion at 45° C. Heating was stopped and the reaction was stirred for an additional hour. The reaction mixture from was slowly (over 2 minutes) added to ice-cold water (50 mL) in a 100 mL round-bottom flask, and placed in an ice bath. Then acetic acid (528.5 mg, 500.5 µL, 8.801 mmol) was added and the mixture stirred vigorously for 10 minutes and the solids were filtered and washed with water (3×20 mL). The solids were slurried in hexanes (20 mL) and filtered. The solid was further and dried to furnish desired coupled product as white solid. N-[(6-amino-2-pyridyl)sulfonyl]-5-bromo-6-tert-butyl-2-chloro-pyridine-3-carboxamide (585 mg, 1.31 mmol, 76.5%) $^1$H NMR (400 MHz, DMSO-d$_6$) δ 8.87 (s, 1H), 8.15 (s, 1H), 7.60 (d, J=1.5 Hz, 1H), 7.54 (t, J=7.8 Hz, 1H), 7.09 (d, J=7.3 Hz, 1H), 6.58 (d, J=8.3 Hz, 1H), 6.35 (s, 2H), 1.46 (s, 9H) ESI-MS m/z calc. 445.9815, found 449.2 (M+1)$^+$; Retention time: 1.52 minutes Step 5: N-[(6-amino-2-pyridyl)sulfonyl]-5-bromo-6-tert-butyl-2-(2,2,4-trimethylpyrrolidin-1-yl)pyridine-3-carboxamide (Compound 1628)

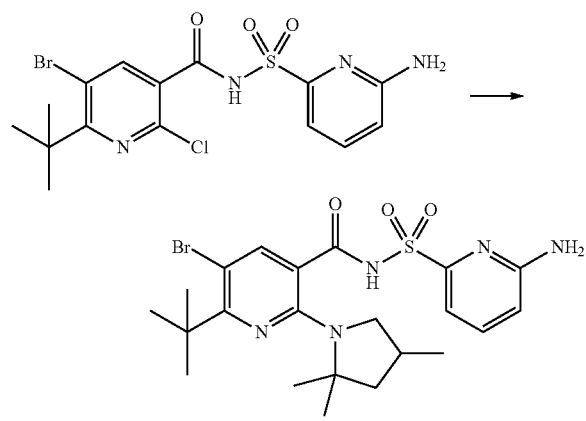

2,2,4-Trimethylpyrrolidine (252.9 mg, 2.234 mmol) and potassium carbonate (617.5 mg, 4.468 mmol) were added to a solution of N-[(6-amino-2-pyridyl)sulfonyl]-5-bromo-6-tert-butyl-2-chloro-pyridine-3-carboxamide (500.0 mg, 1.117 mmol) in anhydrous DMSO (4.0 mL) in a 20 mL reaction vial. The vial was capped under a nitrogen atmosphere and heated in a pre-heated oil bath at 145° C. for 24 h. The reaction vessel was removed and allowed to cool to ambient temperature. The reaction mixture was poured onto a mixture of ice and water (50 mL) with stirring. The resulting reaction mixture was then adjusted to a pH of about 6.0 with 1 M aqueous HCl. The mixture was vigorously stirred for 15 minutes. The solid was filtered, washed with water (4×20 mL), and dried under vacuum to yield the desired product as white solid. N-[(6-amino-2-pyridyl)sulfonyl]-5-bromo-6-tert-butyl-2-(2,2,4-trimethylpyrrolidin-1-yl)pyridine-3-carboxamide (Compound 1628) (495 mg, 0.944 mmol, 84.5%) $^1$H NMR (400 MHz, DMSO-d$_6$) δ 12.49 (s, 1H), 8.52 (s, 1H), 7.70 (s, 1H), 7.49 (s, 1H), 7.07 (d, J=7.2 Hz, 1H), 6.53 (s, 1H), 6.20 (s, 2H), 3.37 (dd, J=11.6, 8.2 Hz, 1H), 2.77 (dd, J=11.6, 8.9 Hz, 1H), 2.16 (dt, J=12.5, 6.4 Hz, 1H), 1.99 (dd, J=12.9, 7.6 Hz, 1H), 1.81 (dd, J=11.8, 5.5 Hz, 1H), 1.51 (s, 3H), 1.48 (s, 3H), 1.44 (s, 9H), 0.87 (d, J=6.3 Hz, 3H). ESI-MS m/z calc. 523.12524, found 526.1 (M+1)$^+$; Retention time: 1.43 minutes Step 6: N-[(6-amino-2-pyridyl)sulfonyl]-6-tert-butyl-5-(3,4-dihydro-2H-pyran-5-yl)-2-(2,2,4-trimethylpyrrolidin-1-yl)pyridine-3-carboxamide (Compound 1487)

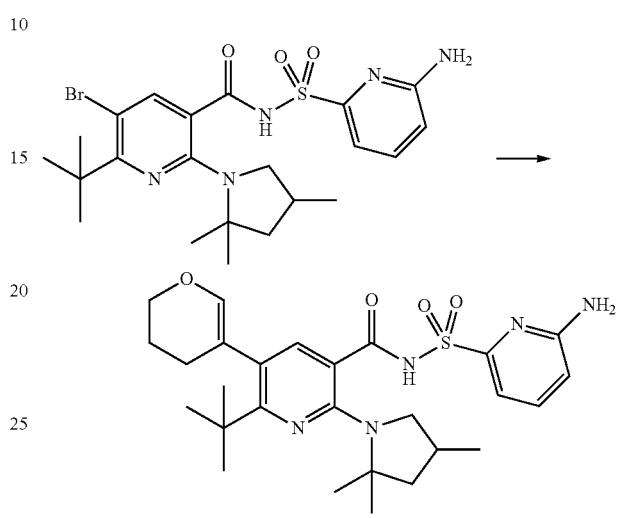

A 4 mL vial was charged with a stir bar, N-[(6-amino-2-pyridyl)sulfonyl]-5-bromo-6-tert-butyl-2-(2,2,4-trimethylpyrrolidin-1-yl)pyridine-3-carboxamide (Compound 1628) (29 mg, 0.055 mmol) and vinylboronic acid 34.85 mg, 0.1659 mmol). Then DMF (0.5 mL) and water (0.1 mL) were added, followed by potassium carbonate (30.57 mg, 0.2212 mmol). Nitrogen was bubbled through the vial for 1 min. Then tetrakis(triphenylphosphine)palladium (0) (6.389 mg, 0.005529 mmol) was added and nitrogen was bubbled through the solution for another 1 min, sealed with a screw cap under nitrogen and heated at 130° C. (external temperature) for 13 h. The reaction mixture was filtered through a syringe filter disc, and purified by reverse phase HPLC utilizing a gradient of 10 to 99 percent acetonitrile in water containing 5 mM HCl to yield N-[(6-amino-2-pyridyl)sulfonyl]-6-tert-butyl-5-(3,4-dihydro-2H-pyran-5-yl)-2-(2,2,4-trimethylpyrrolidin-1-yl)pyridine-3-carboxamide (Compound 1487) (3.3 mg, 0.0058 mmol, 11%) as the hydrochloric acid salt. ESI-MS m/z calc. 527.26, found 528.3 (M+1)$^+$; Retention time: 1.21 minutes The following compounds can be synthesized using the procedures described herein N-[(6-amino-2-pyridyl)sulfonyl]-6-tert-butyl-5-[4-(trifluoromethyl)cyclohexen-1-yl]-2-[(4S)-2,2,4-trimethylpyrrolidin-1-yl]pyridine-3-carboxamide (Compound 1380), N-[(6-amino-2-pyridyl)sulfonyl]-6-tert-butyl-5-[(E)-3,3-dimethylbut-1-enyl]-2-[(4S)-2,2,4-trimethylpyrrolidin-1-yl]pyridine-3-carboxamide (Compound 1613), N-[(6-amino-2-pyridyl)sulfonyl]-6-tert-butyl-5-[(E)-2-cyclohexylvinyl]-2-[(4S)-2,2,4-trimethylpyrrolidin-1-yl]pyridine-3-carboxamide (Compound 1484), N-[(6-amino-2-pyridyl)sulfonyl]-6-tert-butyl-5-[(E)-hex-1-enyl]-2-[(4S)-2,2,4-trimethylpyrrolidin-1-yl]pyridine-3-carboxamide (Compound 1377), N-[(6-amino-2-pyridyl)sulfonyl]-6-tert-butyl-5-[(E)-5-methylhex-1-enyl]-2-[(4S)-2,2,4-trimethylpyrrolidin-1-yl]pyridine-3-carboxamide (Compound 1682), N-[(6-amino-2-pyridyl)sulfonyl]-6-tert-butyl-5-[(E)-2-cyclopentylvinyl]-2-[(4S)-2,2,4-trimethylpyrrolidin-1-yl]pyridine-3-carboxamide (Compound 1633), N-[(6-amino-2-pyridyl)sulfonyl]-6-tert-butyl-5-[(E)-2-[4-(trifluoromethyl)phenyl]vinyl]-2-[(4S)-2,2,4-trimethylpyrrolidin-1-yl]pyridine-3-carboxamide (Compound 1566), (E)-3-[5-[(6-amino-2-pyridyl)sulfonylcarbamoyl]-2-tert-butyl-6-[(4S)-2,2,4-trimethylpyrrolidin-1-yl]-3-pyridyl]prop-2-enoic acid (Compound 1547), N-[(6-amino-2-pyridyl)sulfonyl]-5-(3-bicyclo[2.2.1]hept-2-enyl)-6-tert-butyl-2-(2,2,4-trimethylpyrrolidin-1-yl)pyridine-3-carboxamide, N-[(6-amino-2-pyridyl)sulfonyl]-6-tert-butyl-5-phenyl-2-(2,2,4-trimethylpyrrolidin-1-yl)pyridine-3-carboxamide (Compound 1364), N-[(6-amino-2-pyridyl)sulfonyl]-5-phenyl-2-(2,2,4-trimethylpyrrolidin-1-yl)pyridine-3-carboxamide (Compound 1384), N-[(6-amino-2-pyridyl)sulfonyl]-5-(4,7,7-trimethyl-3-bicyclo[2.2.1]hept-2-enyl)-2-(2,2,4-trimethylpyrrolidin-1-yl)pyridine-3-carboxamide (Compound 1544), N-[(6-amino-2-pyridyl)sulfonyl]-5-[(E)-2-cyclopropylvinyl]-2-(2,2,4-trimethylpyrrolidin-1-yl)pyridine-3-carboxamide (Compound 1571), N-[(6-amino-2-pyridyl)sulfonyl]-5-(1,2-dimethylprop-1-enyl)-2-(2,2,4-trimethylpyrrolidin-1-yl)pyridine-3-carboxamide (Compound 1590), N-[(6-amino-2-pyridyl)sulfonyl]-5-[(E)-2-(4-methoxyphenyl)vinyl]-2-(2,2,4-trimethylpyrrolidin-1-yl)pyridine-3-carboxamide, N-[(6-amino-2-pyridyl)sulfonyl]-6-tert-butyl-5-[(E)-pent-1-enyl]-2-(2,2,4-trimethylpyrrolidin-1-yl)pyridine-3-carboxamide, N-[(6-amino-2-pyridyl)sulfonyl]-5-(3-bicyclo[2.2.1]hept-2-enyl)-6-tert-butyl-2-(2,2,4-trimethylpyrrolidin-1-yl)pyridine-3-carboxamide, ethyl (E)-3-[5-[(6-amino-2-pyridyl)sulfonylcarbamoyl]-2-tert-butyl-6-(2,2,4-trimethylpyrrolidin-1-yl)-3-pyridyl]prop-2-enoate, N-[(6-amino-2-pyridyl)sulfonyl]-6-tert-butyl-5-[(E)-2-ethoxyvinyl]-2-(2,2,4-trimethylpyrrolidin-1-yl)pyridine-3-carboxamide, N-[(6-amino-2-pyridyl)sulfonyl]-6-tert-butyl-2-(2,2,4-trimethylpyrrolidin-1-yl)-5-vinyl-pyridine-3-carboxamide, N-[(6-amino-2-pyridyl)sulfonyl]-6-tert-butyl-5-[(E)-2-cyclopropylvinyl]-2-(2,2,4-trimethylpyrrolidin-1-yl)pyridine-3-carboxamide, N-[(6-amino-2-pyridyl)sulfonyl]-6-tert-butyl-5-[(E)-pent-1-enyl]-2-(2,2,4-trimethylpyrrolidin-1-yl)pyridine-3-carboxamide, N-[(6-amino-2-pyridyl)sulfonyl]-6-tert-butyl-5-[(E)-2-(4-methoxyphenyl)vinyl]-2-(2,2,4-trimethylpyrrolidin-1-yl)pyridine-3-carboxamide, N-[(6-amino-2-pyridyl)sulfonyl]-6-tert-butyl-5-[(E)-2-cyclopropylvinyl]-2-(2,2,4-trimethylpyrrolidin-1-yl)pyridine-3-carboxamide, N-[(6-amino-2-pyridyl)sulfonyl]-6-tert-butyl-2-(2,2,4-trimethylpyrrolidin-1-yl)-5-vinyl-pyridine-3-carboxamide, N-[(6-amino-2-pyridyl)sulfonyl]-6-tert-butyl-5-[(E)-2-ethoxyvinyl]-2-(2,2,4-trimethylpyrrolidin-1-yl)pyridine-3-carboxamide, ethyl (E)-3-[5-[(6-amino-2-pyridyl)sulfonylcarbamoyl]-2-tert-butyl-6-(2,2,4-trimethylpyrrolidin-1-yl)-3-pyridyl]prop-2-enoate, N-[(6-amino-2-pyridyl)sulfonyl]-6-tert-butyl-5-(2-methylprop-1-enyl)-2-(2,2,4-trimethylpyrrolidin-1-yl)pyridine-3-carboxamide (Compound 1561), benzyl 4-[5-[(6-amino-2-pyridyl)sulfonylcarbamoyl]-2-tert-butyl-6-(2,2,4-trimethylpyrrolidin-1-yl)-3-pyridyl]-3,6-dihydro-2H-pyridine-1-carboxylate (Compound 1404), tert-butyl 3-[5-[(6-amino-2-pyridyl)sulfonylcarbamoyl]-2-tert-butyl-6-(2,2,4-trimethylpyrrolidin-1-yl)-3-pyridyl]-8-azabicyclo[3.2.1]oct-3-ene-8-carboxylate (Compound 1388), 5-(4-acetylcyclohexen-1-yl)-N-[(6-amino-2-pyridyl)sulfonyl]-6-tert-butyl-2-(2,2,4-trimethylpyrrolidin-1-yl)pyridine-3-carboxamide (Compound 1461), N-[(6-amino-2-pyridyl)sulfonyl]-6-tert-butyl-5-(1,4-dioxaspiro[4.5]dec-8-en-8-yl)-2-(2,2,4-trimethylpyrrolidin-1-yl)pyridine-3-carboxamide (Compound 1459), N-[(6-amino-2-pyridyl)sulfonyl]-5-bromo-6-tert-butyl-2-(2,2,4-trimethylpyrrolidin-1-yl)pyridine-3-carboxamide (Compound 1628), N-[(6-amino-2-pyridyl)sulfonyl]-6-tert-butyl-5-(2,2,6,6-tetramethyl-3H-pyran-4-yl)-2-(2,2,4-trimethylpyrrolidin-1-yl)pyridine-3-carboxamide (Compound 1647), N-[(6-amino-2-pyridyl)sulfonyl]-6-tert-butyl-5-(4,7,7-trimethyl-3-bicyclo[2.2.1]hept-2-enyl)-2-(2,2,4-trimethylpyrrolidin-1-yl)pyridine-3-carboxamide (Compound 1578), N-[(6-amino-2-pyridyl)sulfonyl]-6-tert-butyl-5-(3,4-dihydro-2H-pyran-6-yl)-2-(2,2,4-trimethylpyrrolidin-1-yl)pyridine-3-carboxamide (Compound 1485), N-[(6-amino-2-pyridyl)sulfonyl]-6-tert-butyl-5-(5,5-dimethyl-3-oxo-cyclohexen-1-yl)-2-(2,2,4-trimethylpyrrolidin-1-yl)pyridine-3-carboxamide (Compound 1405), N-[(6-amino-2-pyridyl)sulfonyl]-6-tert-butyl-5-(1,4-dioxaspiro[4.5]dec-8-en-9-yl)-2-(2,2,4-trimethylpyrrolidin-1-yl)pyridine-3-carboxamide (Compound 1469), tert-butyl 4-[5-[(6-amino-2-pyridyl)sulfonylcarbamoyl]-2-tert-butyl-6-(2,2,4-trimethylpyrrolidin-1-yl)-3-pyridyl]-3,6-dihydro-2H-pyridine-1-carboxylate (Compound 1522), N-[(6-amino-2-pyridyl)sulfonyl]-6-tert-butyl-5-(1-methyl-3,6-dihydro-2H-pyridin-4-yl)-2-(2,2,4-trimethylpyrrolidin-1-yl)pyridine-3-carboxamide (Compound 1382), 4-[5-[(6-amino-2-pyridyl)sulfonylcarbamoyl]-2-tert-butyl-6-(2,2,4-trimethylpyrrolidin-1-yl)-3-pyridyl]cyclohex-3-ene-1-carboxylic acid (Compound 1381), N-[(6-amino-2-pyridyl)sulfonyl]-6-tert-butyl-5-cyano-2-(2,2,4-trimethylpyrrolidin-1-yl)pyridine-3-carboxamide (Compound 1419), N-[(6-amino-2-pyridyl)sulfonyl]-6-tert-butyl-5-(3,6-dihydro-2H-pyran-4-yl)-2-(2,2,4-trimethylpyrrolidin-1-yl)pyridine-3-carboxamide (Compound 1495), N-[(6-amino-2-pyridyl)sulfonyl]-5-(3-methoxy-5-methylphenyl)-2-(2,2,4-trimethylpyrrolidin-1-yl)pyridine-3-carboxamide (Compound 2499), N-[(6-amino-2-pyridyl)sulfonyl]-5-[(E)-hex-1-enyl]-2-(2,2,4-trimethylpyrrolidin-1-yl)pyridine-3-carboxamide (Compound 1916), N-[(6-amino-2-pyridyl)sulfonyl]-5-(3-isobutoxy-5-methylphenyl)-2-(2,2,4-trimethylpyrrolidin-1-yl)pyridine-3-carboxamide (Compound 2558), N-[(6-amino-2-pyridyl)sulfonyl]-5-[2-(trifluoromethyl)phenyl]-2-(2,2,4-trimethylpyrrolidin-1-yl)pyridine-3-carboxamide (Compound 1921), N-[(6-amino-2-pyridyl)sulfonyl]-5-(3-chlorophenyl)-2-(2,2,4-trimethylpyrrolidin-1-yl)pyridine-3-carboxamide (Compound 2429), N-[(6-amino-2-pyridyl)sulfonyl]-5-(3-cyanophenyl)-2-(2,2,4-trimethylpyrrolidin-1-yl)pyridine-3-carboxamide (Compound 1849), N-[(6-amino-2-pyridyl)sulfonyl]-5-(4-methoxyphenyl)-2-(2,2,4-trimethylpyrrolidin-1-yl)pyridine-3-carboxamide (Compound 1792),
N-[(6-amino-2-pyridyl)sulfonyl]-5-(3-tert-butyl-5-methyl-phenyl)-2-(2,2,4-trimethylpyrrolidin-1-yl)pyridine-3-carboxamide (Compound 2322),
N-[(6-amino-2-pyridyl)sulfonyl]-5-[4-[1-(hydroxymethyl)cyclopropyl]phenyl]-2-(2,2,4-trimethylpyrrolidin-1-yl)pyridine-3-carboxamide (Compound 2112),
N-[(6-amino-2-pyridyl)sulfonyl]-5-(4-tert-butylphenyl)-2-(2,2,4-trimethylpyrrolidin-1-yl)pyridine-3-carboxamide (Compound 2463),
ethyl 3-[5-[(6-amino-2-pyridyl)sulfonylcarbamoyl]-6-(2,2,4-trimethylpyrrolidin-1-yl)-3-pyridyl]-4-methoxy-benzoate (Compound 2134),
N-[(6-amino-2-pyridyl)sulfonyl]-5-(4-chlorophenyl)-2-(2,2,4-trimethylpyrrolidin-1-yl)pyridine-3-carboxamide (Compound 2399),
N-[(6-amino-2-pyridyl)sulfonyl]-5-(3-chloro-5-methoxy-phenyl)-2-(2,2,4-trimethylpyrrolidin-1-yl)pyridine-3-carboxamide (Compound 2545),
N-[(6-amino-2-pyridyl)sulfonyl]-5-(2-methoxyphenyl)-2-(2,2,4-trimethylpyrrolidin-1-yl)pyridine-3-carboxamide (Compound 1735),
N-[(6-amino-2-pyridyl)sulfonyl]-5-(4-cyanophenyl)-2-(2,2,4-trimethylpyrrolidin-1-yl)pyridine-3-carboxamide (Compound 2304),
N-[(6-amino-2-pyridyl)sulfonyl]-5-(4-isopropylphenyl)-2-(2,2,4-trimethylpyrrolidin-1-yl)pyridine-3-carboxamide (Compound 1809),
N-[(6-amino-2-pyridyl)sulfonyl]-5-(2-isopropoxyphenyl)-2-(2,2,4-trimethylpyrrolidin-1-yl)pyridine-3-carboxamide (Compound 2283),
N-[(6-amino-2-pyridyl)sulfonyl]-5-[3-(2-methoxyethoxymethyl)phenyl]-2-(2,2,4-trimethylpyrrolidin-1-yl)pyridine-3-carboxamide (Compound 1943),
N-[(6-amino-2-pyridyl)sulfonyl]-5-(3-isobutoxyphenyl)-2-(2,2,4-trimethylpyrrolidin-1-yl)pyridine-3-carboxamide (Compound 2089),
N-[(6-amino-2-pyridyl)sulfonyl]-5-(4-isobutylphenyl)-2-(2,2,4-trimethylpyrrolidin-1-yl)pyridine-3-carboxamide (Compound 2395),
N-[(6-amino-2-pyridyl)sulfonyl]-5-(1H-indazol-4-yl)-2-(2,2,4-trimethylpyrrolidin-1-yl)pyridine-3-carboxamide (Compound 2157),
N-[(6-amino-2-pyridyl)sulfonyl]-5-[4-(1-hydroxy-1-methyl-ethyl)phenyl]-2-(2,2,4-trimethylpyrrolidin-1-yl)pyridine-3-carboxamide (Compound 2547),
N-[(6-amino-2-pyridyl)sulfonyl]-5-[(E)-2-[4-(trifluoromethyl)phenyl]vinyl]-2-(2,2,4-trimethylpyrrolidin-1-yl)pyridine-3-carboxamide (Compound 2014),
N-[(6-amino-2-pyridyl)sulfonyl]-5-[3-(cyclopentoxy)phenyl]-2-(2,2,4-trimethylpyrrolidin-1-yl)pyridine-3-carboxamide (Compound 1918),
N-[(6-amino-2-pyridyl)sulfonyl]-5-(6-ethoxy-3-pyridyl)-2-(2,2,4-trimethylpyrrolidin-1-yl)pyridine-3-carboxamide (Compound 2384),
N-[(6-amino-2-pyridyl)sulfonyl]-5-(o-tolyl)-2-(2,2,4-trimethylpyrrolidin-1-yl)pyridine-3-carboxamide (Compound 1701),
N-[(6-amino-2-pyridyl)sulfonyl]-5-[4-(1-cyano-1-methyl-ethyl)phenyl]-2-(2,2,4-trimethylpyrrolidin-1-yl)pyridine-3-carboxamide (Compound 2521),
N-[(6-amino-2-pyridyl)sulfonyl]-5-(6-methoxy-3-pyridyl)-2-(2,2,4-trimethylpyrrolidin-1-yl)pyridine-3-carboxamide (Compound 1886),
N-[(6-amino-2-pyridyl)sulfonyl]-5-[3-(cyclopentoxy)-5-methyl-phenyl]-2-(2,2,4-trimethylpyrrolidin-1-yl)pyridine-3-carboxamide (Compound 2313),
N-[(6-amino-2-pyridyl)sulfonyl]-5-(4-dimethylaminophenyl)-2-(2,2,4-trimethylpyrrolidin-1-yl)pyridine-3-carboxamide (Compound 2288),
N-[(6-amino-2-pyridyl)sulfonyl]-5-(1-isobutylpyrazol-3-yl)-2-(2,2,4-trimethylpyrrolidin-1-yl)pyridine-3-carboxamide (Compound 2303),
N-[(6-amino-2-pyridyl)sulfonyl]-5-(4-methoxycyclohexen-1-yl)-2-(2,2,4-trimethylpyrrolidin-1-yl)pyridine-3-carboxamide (Compound 1920),
N-[(6-amino-2-pyridyl)sulfonyl]-5-(2-cyanophenyl)-2-(2,2,4-trimethylpyrrolidin-1-yl)pyridine-3-carboxamide (Compound 2584),
N-[(6-amino-2-pyridyl)sulfonyl]-5-(3-chloro-5-methyl-phenyl)-2-(2,2,4-trimethylpyrrolidin-1-yl)pyridine-3-carboxamide (Compound 1963),
N-[(6-amino-2-pyridyl)sulfonyl]-5-[4-(trifluoromethoxy)phenyl]-2-(2,2,4-trimethylpyrrolidin-1-yl)pyridine-3-carboxamide (Compound 2649),
N-[(6-amino-2-pyridyl)sulfonyl]-5-(2-ethoxyphenyl)-2-(2,2,4-trimethylpyrrolidin-1-yl)pyridine-3-carboxamide (Compound 2557),
N-[(6-amino-2-pyridyl)sulfonyl]-5-(3,5-dimethylphenyl)-2-(2,2,4-trimethylpyrrolidin-1-yl)pyridine-3-carboxamide (Compound 2093),
tert-butyl 4-[5-[(6-amino-2-pyridyl)sulfonylcarbamoyl]-6-(2,2,4-trimethylpyrrolidin-1-yl)-3-pyridyl]-3,6-dihydro-2H-pyridine-1-carboxylate (Compound 2129),
N-[(6-amino-2-pyridyl)sulfonyl]-5-(4-methylcyclohexen-1-yl)-2-(2,2,4-trimethylpyrrolidin-1-yl)pyridine-3-carboxamide (Compound 2361),
N-[(6-amino-2-pyridyl)sulfonyl]-5-(3-isopentyloxyphenyl)-2-(2,2,4-trimethylpyrrolidin-1-yl)pyridine-3-carboxamide (Compound 1894),
N-[(6-amino-2-pyridyl)sulfonyl]-5-[3-(trifluoromethyl)phenyl]-2-(2,2,4-trimethylpyrrolidin-1-yl)pyridine-3-carboxamide (Compound 1950),
N-[(6-amino-2-pyridyl)sulfonyl]-5-[(E)-5-methylhex-1-enyl]-2-(2,2,4-trimethylpyrrolidin-1-yl)pyridine-3-carboxamide (Compound 2647),
N-[(6-amino-2-pyridyl)sulfonyl]-5-(6-methoxy-2-pyridyl)-2-(2,2,4-trimethylpyrrolidin-1-yl)pyridine-3-carboxamide (Compound 1861),
N-[(6-amino-2-pyridyl)sulfonyl]-5-[3-isopropoxy-5-(trifluoromethyl)phenyl]-2-(2,2,4-trimethylpyrrolidin-1-yl)pyridine-3-carboxamide (Compound 1815),
N-[(6-amino-2-pyridyl)sulfonyl]-5-(3-fluoro-5-methoxy-phenyl)-2-(2,2,4-trimethylpyrrolidin-1-yl)pyridine-3-carboxamide (Compound 2431),
N-[(6-amino-2-pyridyl)sulfonyl]-5-(1,1,4,4,7-pentamethyl-tetralin-6-yl)-2-(2,2,4-trimethylpyrrolidin-1-yl)pyridine-3-carboxamide (Compound 1759),
N-[(6-amino-2-pyridyl)sulfonyl]-5-(3-isopropoxy-5-methyl-phenyl)-2-(2,2,4-trimethylpyrrolidin-1-yl)pyridine-3-carboxamide (Compound 1889),
N-[(6-amino-2-pyridyl)sulfonyl]-5-(3,5-dichlorophenyl)-2-(2,2,4-trimethylpyrrolidin-1-yl)pyridine-3-carboxamide (Compound 1721),
N-[(6-amino-2-pyridyl)sulfonyl]-5-(2-isobutoxyphenyl)-2-(2,2,4-trimethylpyrrolidin-1-yl)pyridine-3-carboxamide (Compound 1979),
N-[(6-amino-2-pyridyl)sulfonyl]-5-(5-benzyloxy-2-methyl-phenyl)-2-(2,2,4-trimethylpyrrolidin-1-yl)pyridine-3-carboxamide (Compound 2588), N-[(6-amino-2-pyridyl)sulfonyl]-5-(3-isopropoxyphenyl)-2-(2,2,4-trimethylpyrrolidin-1-yl)pyridine-3-carboxamide (Compound 1804),
N-[(6-amino-2-pyridyl)sulfonyl]-5-(3,5-difluorophenyl)-2-(2,2,4-trimethylpyrrolidin-1-yl)pyridine-3-carboxamide (Compound 2259),
N-[(6-amino-2-pyridyl)sulfonyl]-5-[4-(hydroxymethyl)phenyl]-2-(2,2,4-trimethylpyrrolidin-1-yl)pyridine-3-carboxamide (Compound 2088),
N-[(6-amino-2-pyridyl)sulfonyl]-5-[4-(trifluoromethyl)cyclohexen-1-yl]-2-(2,2,4-trimethylpyrrolidin-1-yl)pyridine-3-carboxamide (Compound 2510),
N-[(6-amino-2-pyridyl)sulfonyl]-5-(m-tolyl)-2-(2,2,4-trimethylpyrrolidin-1-yl)pyridine-3-carboxamide (Compound 2184),
N-[(6-amino-2-pyridyl)sulfonyl]-5-(2-chlorophenyl)-2-(2,2,4-trimethylpyrrolidin-1-yl)pyridine-3-carboxamide (Compound 2312),
N-[(6-amino-2-pyridyl)sulfonyl]-5-[4-(trifluoromethyl)phenyl]-2-(2,2,4-trimethylpyrrolidin-1-yl)pyridine-3-carboxamide (Compound 2337),
N-[(6-amino-2-pyridyl)sulfonyl]-5-(2-chloro-5-isopropoxyphenyl)-2-(2,2,4-trimethylpyrrolidin-1-yl)pyridine-3-carboxamide (Compound 2210),
N-[(6-amino-2-pyridyl)sulfonyl]-5-(3-methoxyphenyl)-2-(2,2,4-trimethylpyrrolidin-1-yl)pyridine-3-carboxamide (Compound 2031),
N-[(6-amino-2-pyridyl)sulfonyl]-5-(3-tert-butylphenyl)-2-(2,2,4-trimethylpyrrolidin-1-yl)pyridine-3-carboxamide (Compound 2180),
N-[(6-amino-2-pyridyl)sulfonyl]-5-[(E)-2-(4-methoxyphenyl)vinyl]-2-(2,2,4-trimethylpyrrolidin-1-yl)pyridine-3-carboxamide (Compound 1726),
N-[(6-amino-2-pyridyl)sulfonyl]-5-(3-bicyclo[2.2.1]hept-2-enyl)-2-(2,2,4-trimethylpyrrolidin-1-yl)pyridine-3-carboxamide (Compound 1888),
N-[(6-amino-2-pyridyl)sulfonyl]-5-(3-ethoxy-5-methylphenyl)-2-(2,2,4-trimethylpyrrolidin-1-yl)pyridine-3-carboxamide (Compound 1843),
N-[(6-amino-2-pyridyl)sulfonyl]-5-(3-methyl-4-propoxyphenyl)-2-(2,2,4-trimethylpyrrolidin-1-yl)pyridine-3-carboxamide (Compound 2095),
N-[(6-amino-2-pyridyl)sulfonyl]-5-[(E)-2-cyclohexylvinyl]-2-(2,2,4-trimethylpyrrolidin-1-yl)pyridine-3-carboxamide (Compound 2063),
N-[(6-amino-2-pyridyl)sulfonyl]-6-tert-butyl-5-(cyclohexen-1-yl)-2-(2,2,4-trimethylpyrrolidin-1-yl)pyridine-3-carboxamide (Compound 1601), and
N-[(6-amino-2-pyridyl)sulfonyl]-6-tert-butyl-5-(1-methylpyrazol-4-yl)-2-(2,2,4-trimethylpyrrolidin-1-yl)pyridine-3-carboxamide (Compound 1441)

Preparation 82: tert-butyl N-[1-[[6-(3-fluoro-5-isobutoxy-phenyl)-2-(2,2,4-trimethylpyrrolidin-1-yl)pyridine-3-carbonyl]sulfamoyl]-3-methyl-3-piperidyl]carbamate (Compound 1520)

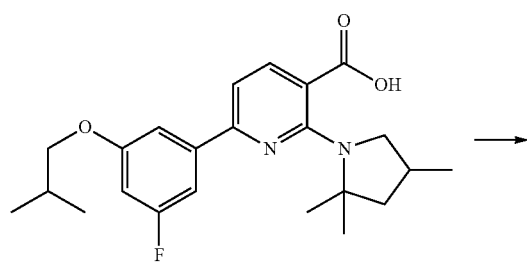

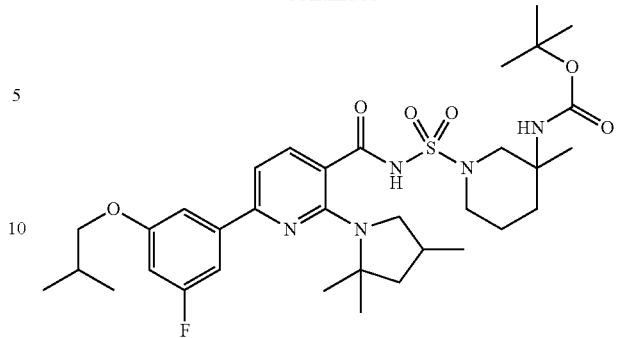

A solution of 6-(3-fluoro-5-isobutoxy-phenyl)-2-(2,2,4-trimethylpyrrolidin-1-yl)pyridine-3-carboxylic acid (40.45 mg, 0.1000 mmol) and chlorosulfonyl isocyanate (16.98 mg, 10.44 µL, 0.1200 mmol) in dichloromethane (1.000 mL) was stirred for 45 minutes. Triethylamine (15.18 mg, 20.91 µL, 0.1500 mmol) and tert-butyl-N-(3-methyl-3-piperidyl)carbamate (32.15 mg, 0.1500 mmol) were added, and the reaction was stirred for three days. The reaction was purified by silica gel chromatography with 0-5% methanol in dichloromethane to give tert-butyl (1-(N-(6-(3-fluoro-5-isobutoxyphenyl)-2-(2,2,4-trimethylpyrrolidin-1-yl)nicotinoyl)sulfamoyl)-3-methylpiperidin-3-yl)carbamate (34 mg, 0.050 mmol, 50.%) as a colorless solid.

The following compounds can be synthesized using the procedures described herein N-[(3R)-3-aminopyrrolidin-1-yl]sulfonyl-6-(3-fluoro-5-isobutoxy-phenyl)-2-[(4S)-2,2,4-trimethylpyrrolidin-1-yl]pyridine-3-carboxamide (Compound 1360),
N-(3-acetamidopyrrolidin-1-yl)sulfonyl-6-(3-fluoro-5-isobutoxy-phenyl)-2-(2,2,4-trimethylpyrrolidin-1-yl)pyridine-3-carboxamide (Compound 1391),
N-[[3-(dimethylamino)-1-piperidyl]sulfonyl]-6-(3-fluoro-5-isobutoxy-phenyl)-2-(2,2,4-trimethylpyrrolidin-1-yl)pyridine-3-carboxamide (Compound 1414),
N-[[(3S)-3-amino-1-piperidyl]sulfonyl]-6-(3-fluoro-5-isobutoxy-phenyl)-2-[(4S)-2,2,4-trimethylpyrrolidin-1-yl]pyridine-3-carboxamide (Compound 1435),
N-[(3-amino-3-methyl-1-piperidyl)sulfonyl]-6-(3-fluoro-5-isobutoxy-phenyl)-2-(2,2,4-trimethylpyrrolidin-1-yl)pyridine-3-carboxamide (Compound 1445),
N-[(3-amino-1-piperidyl)sulfonyl]-6-(3-fluoro-5-isobutoxy-phenyl)-2-(2,2,4-trimethylpyrrolidin-1-yl)pyridine-3-carboxamide (Compound 1447)
N-(3-aminopyrrolidin-1-yl)sulfonyl-6-(3-fluoro-5-isobutoxy-phenyl)-2-(2,2,4-trimethylpyrrolidin-1-yl)pyridine-3-carboxamide (Compound 1467),
6-(3-fluoro-5-isobutoxy-phenyl)-N-[[3-(methylamino)-1-piperidyl]sulfonyl]-2-(2,2,4-trimethylpyrrolidin-1-yl)pyridine-3-carboxamide (Compound 1508),
N-[(5-amino-3-azabicyclo[3.1.0]hexan-3-yl)sulfonyl]-6-(3-fluoro-5-isobutoxy-phenyl)-2-[(4S)-2,2,4-trimethylpyrrolidin-1-yl]pyridine-3-carboxamide (Compound 1521),
N-[3-[acetyl(methyl)amino]pyrrolidin-1-yl]sulfonyl-6-(3-fluoro-5-isobutoxy-phenyl)-2-(2,2,4-trimethylpyrrolidin-1-yl)pyridine-3-carboxamide (Compound 1533),
6-(3-fluoro-5-isobutoxy-phenyl)-N-[(3-methoxy-1-piperidyl)sulfonyl]-2-[(4S)-2,2,4-trimethylpyrrolidin-1-yl]pyridine-3-carboxamide (Compound 1545),
6-(3-fluoro-5-isobutoxy-phenyl)-N-[3-(methylamino)pyrrolidin-1-yl]sulfonyl-2-(2,2,4-trimethylpyrrolidin-1-yl)pyridine-3-carboxamide (Compound 1554), N-[(3S)-3-aminopyrrolidin-1-yl]sulfonyl-6-(3-fluoro-5-isobutoxy-phenyl)-2-[(4S)-2,2,4-trimethylpyrrolidin-1-yl]pyridine-3-carboxamide (Compound 1557), 6-(3-fluoro-5-isobutoxy-phenyl)-N-(3-methylsulfonylpyrrolidin-1-yl)sulfonyl-2-[(4S)-2,2,4-trimethylpyrrolidin-1-yl]pyridine-3-carboxamide (Compound 1560), N-[(3-acetamido-1-piperidyl)sulfonyl]-6-(3-fluoro-5-isobutoxy-phenyl)-2-(2,2,4-trimethylpyrrolidin-1-yl)pyridine-3-carboxamide (Compound 1586), 6-(3-fluoro-5-isobutoxy-phenyl)-N-[[3-(methanesulfonamido)-1-piperidyl]sulfonyl]-2-(2,2,4-trimethylpyrrolidin-1-yl)pyridine-3-carboxamide (Compound 1600), 6-(3-fluoro-5-isobutoxy-phenyl)-N-[(3-hydroxy-1-piperidyl)sulfonyl]-2-[(4S)-2,2,4-trimethylpyrrolidin-1-yl]pyridine-3-carboxamide (Compound 1608), N-[[(3R)-3-amino-1-piperidyl]sulfonyl]-6-(3-fluoro-5-isobutoxy-phenyl)-2-[(4S)-2,2,4-trimethylpyrrolidin-1-yl]pyridine-3-carboxamide (Compound 1614), 6-(3-fluoro-5-isobutoxy-phenyl)-N-pyrrolidin-1-ylsulfonyl-2-[(4S)-2,2,4-trimethylpyrrolidin-1-yl]pyridine-3-carboxamide (Compound 1619), and 6-(3-fluoro-5-isobutoxy-phenyl)-N-(3-hydroxypyrrolidin-1-yl)sulfonyl-2-[(4S)-2,2,4-trimethylpyrrolidin-1-yl]pyridine-3-carboxamide (Compound 1648), 6-(3-fluoro-5-isobutoxy-phenyl)-N-(3-hydroxy-3-methyl-azetidin-1-yl)sulfonyl-2-[(4S)-2,2,4-trimethylpyrrolidin-1-yl]pyridine-3-carboxamide (Compound 2398), 6-(3-fluoro-5-isobutoxy-phenyl)-N-(2-pyridylsulfamoyl)-2-[(4S)-2,2,4-trimethylpyrrolidin-1-yl]pyridine-3-carboxamide, 6-(3-fluoro-5-isobutoxy-phenyl)-N-[[(4S)-2-oxa-5-azabicyclo[2.2.1]heptan-5-yl]sulfonyl]-2-[(4S)-2,2,4-trimethylpyrrolidin-1-yl]pyridine-3-carboxamide (Compound 1789), 6-(3-fluoro-5-isobutoxy-phenyl)-N-[[(3R)-3-piperidyl]sulfamoyl]-2-[(4S)-2,2,4-trimethylpyrrolidin-1-yl]pyridine-3-carboxamide (Compound 2677), N-[(6-amino-2-pyridyl)sulfamoyl]-6-(3-fluoro-5-isobutoxy-phenyl)-2-[(4S)-2,2,4-trimethylpyrrolidin-1-yl]pyridine-3-carboxamide, 6-(3-fluoro-5-isobutoxy-phenyl)-N-(3-pyridylsulfamoyl)-2-[(4S)-2,2,4-trimethylpyrrolidin-1-yl]pyridine-3-carboxamide (Compound 1448), 6-(3-fluoro-5-isobutoxy-phenyl)-N-[(2-methoxy-3-pyridyl)sulfamoyl]-2-[(4S)-2,2,4-trimethylpyrrolidin-1-yl]pyridine-3-carboxamide (Compound 1359), 6-(3-fluoro-5-isobutoxy-phenyl)-N-[[(1R,4R)-2-oxa-5-azabicyclo[2.2.1]heptan-5-yl]sulfonyl]-2-[(4S)-2,2,4-trimethylpyrrolidin-1-yl]pyridine-3-carboxamide (Compound 2347), N-(3,3-difluoropyrrolidin-1-yl)sulfonyl-6-(3-fluoro-5-isobutoxy-phenyl)-2-[(4S)-2,2,4-trimethylpyrrolidin-1-yl]pyridine-3-carboxamide (Compound 1956), 6-(3-fluoro-5-isobutoxy-phenyl)-N-[(3,3,3-trifluoro-2-hydroxy-2-methyl-propyl)sulfamoyl]-2-[(4S)-2,2,4-trimethylpyrrolidin-1-yl]pyridine-3-carboxamide, N-(3,8-diazabicyclo[3.2.1]octan-3-ylsulfonyl)-6-(3-fluoro-5-isobutoxy-phenyl)-2-[(4S)-2,2,4-trimethylpyrrolidin-1-yl]pyridine-3-carboxamide (Compound 2237), 6-(3-fluoro-5-isobutoxy-phenyl)-N-[(3R)-3-hydroxypyrrolidin-1-yl]sulfonyl-2-[(4S)-2,2,4-trimethylpyrrolidin-1-yl]pyridine-3-carboxamide (Compound 2427), N-[(3R,4R)-3,4-dihydroxypyrrolidin-1-yl]sulfonyl-6-(3-fluoro-5-isobutoxy-phenyl)-2-[(4S)-2,2,4-trimethylpyrrolidin-1-yl]pyridine-3-carboxamide (Compound 2534), 6-(3-fluoro-5-isobutoxy-phenyl)-N-[[(3S)-pyrrolidin-3-yl]sulfamoyl]-2-[(4S)-2,2,4-trimethylpyrrolidin-1-yl]pyridine-3-carboxamide (Compound 1935), N-[(5-amino-3,3-difluoro-1-piperidyl)sulfonyl]-6-(3-fluoro-5-isobutoxy-phenyl)-2-[(4S)-2,2,4-trimethylpyrrolidin-1-yl]pyridine-3-carboxamide (Compound 2209), 6-(3-fluoro-5-isobutoxy-phenyl)-N-[(6-methoxy-2-pyridyl)sulfamoyl]-2-[(4S)-2,2,4-trimethylpyrrolidin-1-yl]pyridine-3-carboxamide, 6-(3-fluoro-5-isobutoxy-phenyl)-N-[[(3R)-pyrrolidin-3-yl]sulfamoyl]-2-[(4S)-2,2,4-trimethylpyrrolidin-1-yl]pyridine-3-carboxamide, 6-(3-fluoro-5-isobutoxy-phenyl)-N-[(3S)-3-fluoropyrrolidin-1-yl]sulfonyl-2-[(4S)-2,2,4-trimethylpyrrolidin-1-yl]pyridine-3-carboxamide (Compound 2228), 6-(3-fluoro-5-isobutoxy-phenyl)-N-[(3R)-3-methoxypyrrolidin-1-yl]sulfonyl-2-[(4S)-2,2,4-trimethylpyrrolidin-1-yl]pyridine-3-carboxamide (Compound 1893), N-[(3,3-difluoro-5-hydroxy-1-piperidyl)sulfonyl]-6-(3-fluoro-5-isobutoxy-phenyl)-2-[(4S)-2,2,4-trimethylpyrrolidin-1-yl]pyridine-3-carboxamide (Compound 2508), 6-(3-fluoro-5-isobutoxy-phenyl)-N-[[(3S)-3-piperidyl]sulfamoyl]-2-[(4S)-2,2,4-trimethylpyrrolidin-1-yl]pyridine-3-carboxamide, N-[(3R)-3-aminopyrrolidin-1-yl]sulfonyl-2-(2-benzyl-2-methyl-pyrrolidin-1-yl)-6-(3-fluoro-5-isobutoxy-phenyl)pyridine-3-carboxamide (Compound 2325) (Isomer 1, R or S stereoisomer)

N-[(3R)-3-aminopyrrolidin-1-yl]sulfonyl-6-(3-fluoro-5-isobutoxy-phenyl)-2-(2-phenylpyrrolidin-1-yl)pyridine-3-carboxamide (Compound 2477) (Isomer 2, R or S stereoisomer)

Preparation 83: 1-[3-fluoro-5-(4,4,5,5-tetramethyl-1,3,2-dioxaborolan-2-yl)phenoxy]-2-methyl-propan-2-ol Step 1: 1-(3-bromo-5-fluoro-phenoxy)-2-methyl-propan-2-ol

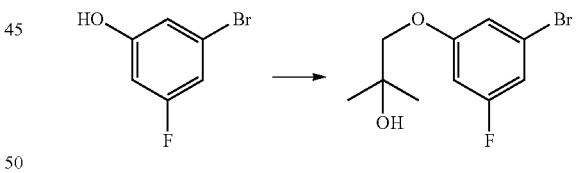

To 3-bromo-5-fluoro-phenol (9.0 g, 47 mmol), and 1-chloro-2-methyl-propan-2-ol (5.116 g, 47.12 mmol), aqueous sodium hydroxide (37.69 g, 94.24 mmol) was added and the reaction mixture was heated at 120° C. for 5 days in a pressure vessel. The reaction was cooled and then extracted three times with ethyl acetate. The combined organic layer was dried over sodium sulfate, filtered, and the solvent was evaporated under reduced pressure. The crude product was purified on 220 g of silica gel utilizing a gradient of 0 to 10% ethyl acetate in dichloromethane. The impure product was repurified on 220 g of gold silica gel utilizing a gradient of 0 to 10% ethyl acetate in dichloromethane to yield 1-(3-bromo-5-fluoro-phenoxy)-2-methyl-propan-2-ol (4.75 g, 18.0 mmol, 38%). ESI-MS m/z calc. 262.00046, found 263.0 (M+1)+; Retention time: 1.57 minutes (3 min run).

Step 2: 1-[3-Fluoro-5-(4,4,5,5-tetramethyl-1,3,2-dioxaborolan-2-yl)phenoxy]-2-methyl-propan-2-ol

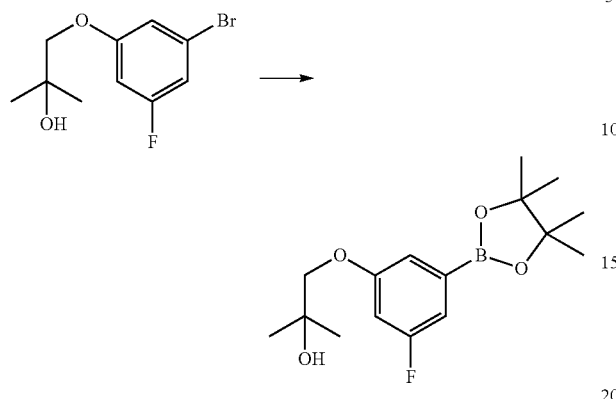

To 1-(3-bromo-5-fluoro-phenoxy)-2-methyl-propan-2-ol (5.250 g, 19.95 mmol) and 4,4,5,5-tetramethyl-2-(4,4,5,5-tetramethyl-1,3,2-dioxaborolan-2-yl)-1,3,2-dioxaborolane (7.598 g, 29.92 mmol) in a flask was added potassium acetate (4.894 g, 49.87 mmol) and [1,1'-Bis(diphenylphosphino)ferrocene]palladium(II) dichloride dichloromethane adduct (729.9 mg, 0.9975 mmol) followed by dioxane (32.58 mL). The suspension was degassed for 10 minutes by sparging with nitrogen and then the reaction was heated in an oil bath at 85° C. for 3 h. The reaction was diluted with ethyl acetate, filtered, and concentrated. The crude product was purified on 330 g of silica gel utilizing a gradient of 0 to 50% ethyl acetate in hexane to yield 1-[3-fluoro-5-(4,4,5,5-tetramethyl-1,3,2-dioxaborolan-2-yl)phenoxy]-2-methyl-propan-2-ol (5.23 g, 16.86 mmol, 84.52%). The product was not pure and it was used in the next step without further purification. ESI-MS m/z calc. 310.17517, found 311.5 (M+1)$^+$; Retention time: 1.895 minutes (3 min run).

Preparation 84: 3-[3-fluoro-5-(4,4,5,5-tetramethyl-1,3,2-dioxaborolan-2-yl)phenoxy]-2-methyl-propan-1-ol Step 1: 3-(3-bromo-5-fluoro-phenoxy)-2-methyl-propan-1-ol

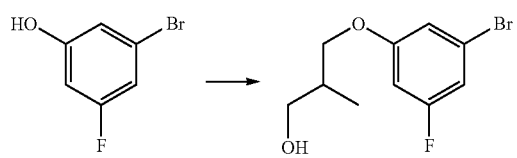

To a stirred solution of 3-bromo-5-fluoro-phenol (2.270 g, 11.88 mmol), 2-methylpropane-1,3-diol (1.071 g, 11.88 mmol) and triphenylphosphane (3.428 g, 3.028 mL, 13.07 mmol) in tetrahydrofuran (71.82 mL) at 0° C. was added diisopropyl azodicarboxylate (2.643 g, 2.532 mL, 13.07 mmol). The ice bath was removed and the reaction was stirred at 55° C. for 18 h. The reaction was diluted with ethylacetate and washed twice with sodium bicarbonate and twice with brine. The organic layer was dried over sodium sulfate, filtered and the solvent was evaporated under reduced pressure. The crude product was purified on 220 g of silica gel utilizing a gradient of 0 to 15% ethyl acetate in dichloromethane to yield 3-(3-bromo-5-fluoro-phenoxy)-2-methyl-propan-1-ol (1.73 g, 6.57 mmol, 55.3%) as a colorless liquid. $^1$H NMR (400 MHz, DMSO-d$_6$) δ 7.09-7.03 (m, 1H), 7.03-6.98 (m, 1H), 6.87 (dt, J=11.2, 2.3 Hz, 1H), 4.57 (t, J=5.3 Hz, 1H), 3.97 (dd, J=9.5, 5.9 Hz, 1H), 3.85 (dd, J=9.5, 6.3 Hz, 1H), 3.48-3.34 (m, 2H), 2.05-1.84 (m, 1H), 0.94 (d, J=6.8 Hz, 3H). ESI-MS m/z calc. 262.00046, found 265.0 (M+1)$^+$; Retention time: 1.58 minutes (3 min run).

Step 2: 3-[3-fluoro-5-(4,4,5,5-tetramethyl-1,3,2-dioxaborolan-2-yl)phenoxy]-2-methyl-propan-1-ol

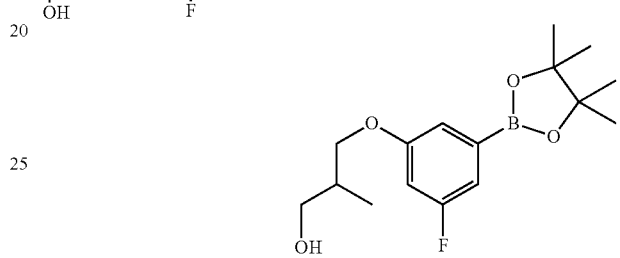

To 3-(3-bromo-5-fluoro-phenoxy)-2-methyl-propan-1-ol (1.7 g, 6.5 mmol) and 4,4,5,5-tetramethyl-2-(4,4,5,5-tetramethyl-1,3,2-dioxaborolan-2-yl)-1,3,2-dioxaborolane (2.461 g, 9.692 mmol) in a flask was potassium acetate (1.585 g, 16.15 mmol) and [1,1'-Bis(diphenylphosphino)ferrocene]palladium(II) dichloride dichloromethane adduct (236.3 mg, 0.3230 mmol) followed by dioxane (10.55 mL). The suspension was degassed for 10 min by bubbling nitrogen through the reaction mixture and then the reaction was heated in an oil bath at 85° C. for 2.5 h. The reaction was diluted with ethyl acetate, filtered, and concentrated. The crude product was purified on 220 g of silica gel utilizing a gradient of 0 to 50% ethyl acetate in hexane to yield 3-[3-fluoro-5-(4,4,5,5-tetramethyl-1,3,2-dioxaborolan-2-yl)phenoxy]-2-methyl-propan-1-ol (1.77 g, 5.71 mmol, 88%) as an orange viscous liquid. The product contained some impurity. It was used in the next step without further purification. ESI-MS m/z calc. 310.17517, found 311.2 (M+1)$^+$; Retention time: 1.81 minutes (3 min run).

Preparation 85: 5-(Benzyloxy)-6-nitropyridine-2-sulfonamide

Step 1: 3-Benzyloxy-6-bromo-2-nitro-pyridine

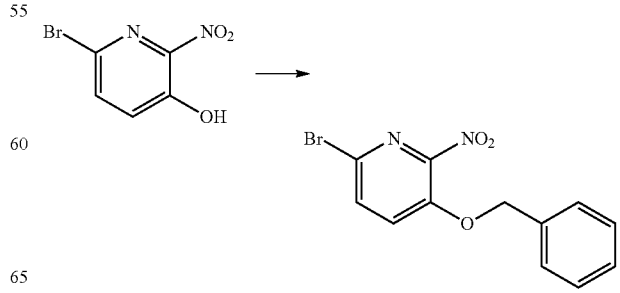

To a solution of 6-bromo-2-nitro-pyridin-3-ol (1.36 g, 6.21 mmol) in N,N-dimethylformamide (15 mL) was added potassium carbonate (1.717 g, 12.42 mmol) followed by the addition of bromomethylbenzene (1.115 g, 775.4 µL, 6.520 mmol). The mixture was heated at 60° C. overnight, and partitioned between ethyl acetate and water. The aqueous layer was extracted with ethyl acetate three times. The combined organic layers were washed three times with water, brine, dried over magnesium sulfate, filtered, and concentrated to dryness. The crude material was suspended in hexane, collected via filtration and air dried to provide 3-benzyloxy-6-bromo-2-nitro-pyridine (1.61 g, 5.21 mmol, 83.8%) as a yellow solid. $^1$H NMR (400 MHz, Chloroform-d) δ 7.60 (d, J=8.7 Hz, 1H), 7.45-7.29 (m, 6H), 5.25 (s, 2H).

Step 2: Methyl 3-[(5-benzyloxy-6-nitro-2-pyridyl)sulfonyl]propanoate

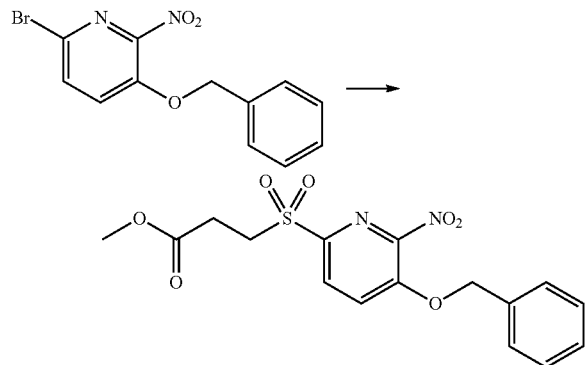

A mixture of 3-benzyloxy-6-bromo-2-nitro-pyridine (585 mg, 1.89 mmol) and (3-methoxy-3-oxo-propyl)sulfinyloxysodium (329.5 mg, 1.892 mmol) in dimethylsulfoxide (5 mL) was purged with nitrogen for 2 minutes. Iodocopper (720.7 mg, 3.784 mmol) was added to the reaction mixture. The mixture was heated at 80° C. overnight, partitioned between ethyl acetate and a saturated aqueous solution of ammonium chloride. The resulting precipitate was removed by filtration and washed with ethyl acetate. The aqueous layer was extracted three times with ethyl acetate. The combined organic layers were washed three times with water, brine, dried over magnesium sulfate, filtered and concentrated to dryness. The crude material was purified by column chromatography (40-60% ethyl acetate in hexanes) to provide methyl 3-[(5-benzyloxy-6-nitro-2-pyridyl)sulfonyl]propanoate (210. mg, 0.552 mmol, 29.2%) as a pale yellow solid. $^1$H NMR (400 MHz, Chloroform-d) δ 8.20 (d, J=8.6 Hz, 1H), 7.68 (d, J=8.7 Hz, 1H), 7.50-7.31 (m, 5H), 5.35 (s, 2H), 3.75-3.63 (m, 5H), 2.87 (t, J=7.5 Hz, 2H).

Step 3: 5-(Benzyloxy)-6-nitropyridine-2-sulfonamide

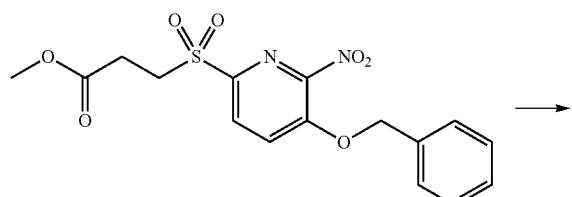

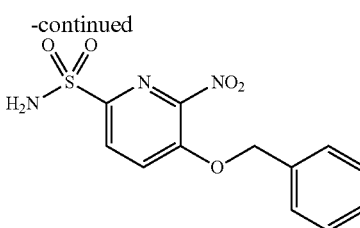

Tetrahydrofuran (10 mL) was added to a suspension of methyl 3-[(5-benzyloxy-6-nitro-2-pyridyl)sulfonyl]propanoate (1.141 g, 3.000 mmol) in methanol (20 mL). The resulting solution was cooled to 0° C. Sodium methoxide (6.000 mL of 0.5 M in methanol, 3.000 mmol) was added in a dropwise manner. The mixture was stirred at room temperature for 15 minutes. The mixture was evaporated to dryness to provide a light brown solid. This solid was then suspended in dichloromethane (30 mL) and N-chlorosuccinimide (400.6 mg, 3.000 mmol) was added to the reaction mixture. The mixture was stirred at room temperature for 10 minutes. The reaction was recharged with N-chlorosuccinimide (80.12 mg, 0.6000 mmol). The mixture turned clear. The mixture was stirred at room temperature for 5 minutes. The resulting solution was added to ammonia (36 mL of 0.5 M, 18.00 mmol) at 0° C. The mixture was stirred at room temperature for 30 minutes, and then partitioned between dichloromethane and water. The aqueous layer was extracted three times with dichloromethane. The combined organic layers were washed with brine, dried over magnesium sulfate, filtered, and concentrated to dryness to provide a yellow solid (342 mg). The crude material was used directly in next step without further purification. ESI-MS m/z calc. 309.04, found 310.3 (M+1)$^+$; Retention time: 1.10 minutes (3 min run).

Preparation 86: N-[(6-amino-2-pyridyl)sulfonyl]-3-fluoro-4-(3-fluoro-5-isobutoxy-phenyl)-2-(2,2,4-trimethylpyrrolidin-1-yl)benzamide (Compound 1497)

Step 1: N-[(6-amino-2-pyridyl)sulfonyl]-4-bromo-2,3-difluoro-benzamide

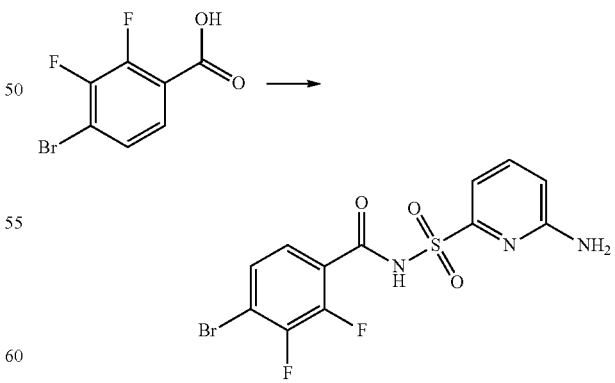

To 4-bromo-2,3-difluoro-benzoic acid (2.66 g, 11.2 mmol) in N, N-dimethylformamide (2.3 mL) was added at room temperature di(imidazol-1-yl)methanone (2.7 g, 17 mmol) and reaction was heated at 65° C. for 1 hour. Separately to 6-aminopyridine-2-sulfonamide (2.4 g, 14.0 mmol) in N,N-dimethylformamide (2 mL) was added sodium hydride (561 mg, 14.0 mmol) at 0° C. and stirred for 10 minutes for 1 hour. The reaction was cooled back to 0° C. and the adduct from above was added and the reaction was heated at 65° C. for 1.5 hours. The reaction was cooled to room temperature and diluted with ethyl acetate and washed with a brine solution. The organics were separated, dried and concentrated to give a residue which was purified with silica gel eluting with 0 to 100% ethyl acetate in hexanes to give N-[(6-amino-2-pyridyl)sulfonyl]-4-bromo-2,3-difluoro-benzamide (3.8 g, 9.7 mmol, 86%) as product. ESI-MS m/z calc 390.94, found 392.0 (M+1)$^+$; Retention time: 1.1 minutes (3 min run)

Step 2: N-[(6-amino-2-pyridyl)sulfonyl]-2,3-difluoro-4-(3-fluoro-5-isobutoxy-phenyl)benzamide

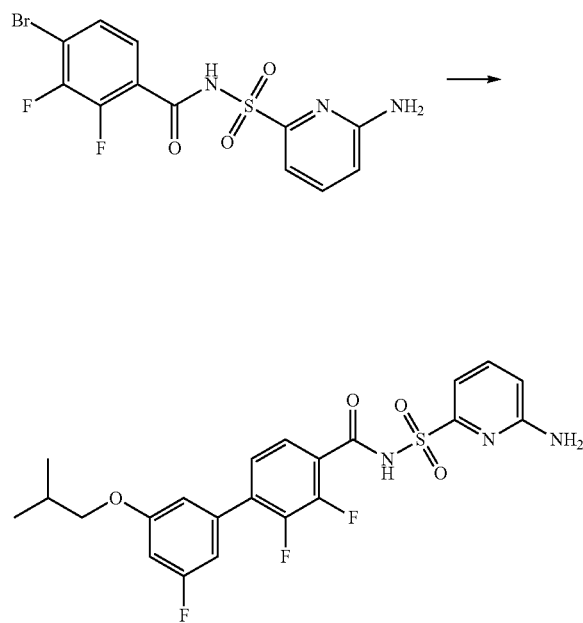

To mixture of N-[(6-amino-2-pyridyl)sulfonyl]-4-bromo-2,3-difluoro-benzamide (700. mg, 1.79 mmol), (3-fluoro-5-isobutoxy-phenyl)boronic acid (568 mg, 2.68 mmol), and potassium carbonate (740 mg, 5.4 mmol) in a vial was added [1,1'-bis(diphenylphosphino)ferrocene]palladium(II) dichloride (130.6 mg, 0.1785 mmol) and N,N-dimethylformamide (4.8 mL) and water (1.2 mL) and the reaction mixture was stirred under nitrogen at 100° C. for 16 hours. The reaction mixture was cooled, filtered over pad of celite and the filtrate was diluted with ethyl acetate and a brine solution. The organics were separated, dried over sodium sulfate, and concentrated to give a residue which was purified with silica gel using 5 to 100% ethyl acetate in dichloromethane to give N-[(6-amino-2-pyridyl)sulfonyl]-2,3-difluoro-4-(3-fluoro-5-isobutoxy-phenyl)benzamide (174 mg, 0.363 mmol, 20.3%) $^1$H NMR (400 MHz, Methanol-d$_4$) δ 7.64-7.53 (m, 2H), 7.29 (d, J=7.4 Hz, 1H), 7.25-7.18 (m, 1H), 6.90 (d, J=2.7 Hz, 1H), 6.88-6.81 (m, 1H), 6.73 (dt, J=10.8, 2.3 Hz, 1H), 6.64 (d, J=8.3 Hz, 1H), 3.79 (d, J=6.4 Hz, 2H), 2.07 (hept, J=6.7 Hz, 1H), 1.04 (d, J=6.7 Hz, 6H). ESI-MS m/z calc 479.11, found 480.2 (M+1)$^+$; LCMS retention time: 1.8 minutes (3 min run).

Step 3: N-[(6-amino-2-pyridyl)sulfonyl]-3-fluoro-4-(3-fluoro-5-isobutoxy-phenyl)-2-(2,2,4-trimethylpyrrolidin-1-yl)benzamide (Compound 1497)

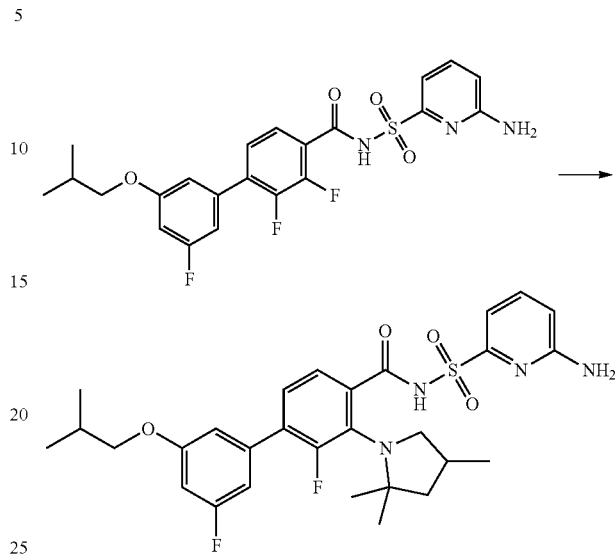

To mixture of 2,2,4-trimethylpyrrolidine (35.41 mg, 0.3128 mmol) and N-[(6-amino-2-pyridyl)sulfonyl]-2,3-difluoro-4-(3-fluoro-5-isobutoxy-phenyl)benzamide (30.00 mg, 0.06257 mmol) was added 1-methylpyrrolidin-2-one (0.3 mL) and the reaction mixture was heated 190° C. for 2 hours. The reaction mixture was cooled and purified by reverse phase HPLC utilizing a gradient of 10 to 99 percent acetonitrile in water containing 5 mM ammonium formate to yield N-[(6-amino-2-pyridyl)sulfonyl]-3-fluoro-4-(3-fluoro-5-isobutoxy-phenyl)-2-(2,2,4-trimethylpyrrolidin-1-yl)benzamide (Compound 1497) (7.6 mg, 0.013 mmol, 4.2%) $^1$H NMR (400 MHz, Methanol-d$_4$) δ 8.03 (dd, J=8.3, 1.2 Hz, 1H), 7.68 (dd, J=8.5, 7.3 Hz, 1H), 7.59 (dd, J=8.3, 7.1 Hz, 1H), 7.38 (dd, J=7.4, 0.8 Hz, 1H), 6.93-6.82 (m, 2H), 6.82-6.74 (m, 2H), 3.92 (t, J=9.4 Hz, 1H), 3.79 (d, J=6.4 Hz, 2H), 2.84-2.72 (m, 1H), 2.23 (dd, J=12.6, 7.3 Hz, 1H), 2.12-2.02 (m, 1H), 1.87 (t, J=11.7 Hz, 1H), 1.38 (s, 3H), 1.24 (d, J=6.6 Hz, 6H), 1.04 (d, J=6.7 Hz, 6H). ESI-MS m/z calc. 572.23, found 573.1 (M+1)$^+$; LCMS retention time: 1.77 minutes (3 min run).

Preparation 87: N-[(6-amino-2-pyridyl)sulfonyl]-5-chloro-6-(3-fluoro-5-isobutoxy-phenyl)-2-[(4S)-2,2,4-trimethylpyrrolidin-1-yl]pyridine-3-carboxamide (Compound 1641)

N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (56.79 mg, 0.1022 mmol) and N-chlorosuccinimide (13.65 mg, 0.1022 mmol) in dichloromethane (400 μL) was stirred at reflux overnight. The dichloromethane was evaporated under a stream of nitrogen, and the residue was dissolved in dimethyl sulfoxide and purified by preparative HPLC chromatography utilizing a gradient of 10 to 99 percent acetonitrile in water to give N-[(6-amino-2-pyridyl)sulfonyl]-5-chloro-6-(3-fluoro-5-isobutoxy-phenyl)-2-[(4S)-2,2,4-trimethylpyrrolidin-1-yl]pyridine-3-carboxamide (Compound 1641) (18 mg, 0.030 mmol, 29.5%) $^1$H NMR (400 MHz, DMSO-d$_6$). 12.59 (s, 1H), 7.80 (s, 1H), 7.64 (dd, J=8.4, 7.3 Hz, 1H), 7.27-7.18 (m, 1H), 7.10-6.99

(m, 2H), 6.93 (dt, J=11.0, 2.3 Hz, 1H), 6.70 (dd, J=8.4, 0.8 Hz, 1H), 6.54 (s, 2H), 3.80 (d, J=6.6 Hz, 2H), 2.65-2.53 (m, 2H), 2.22 (dt, J=11.5, 5.9 Hz, 1H), 2.08-1.96 (m, 1H), 1.84 (dd, J=12.0, 5.6 Hz, 1H), 1.57-1.33 (m, 7H), 0.97 (d, J=6.7 Hz, 6H), 0.86 (d, J=6.3 Hz, 3H). ESI-MS m/z calc. 589.19257, found 590.0 (M+1)$^+$; Retention time: 3.06 minutes.

Preparation 88: N-[(6-amino-2-pyridyl)sulfonyl]-5-chloro-2-[(4S)-2,2,4-trimethylpyrrolidin-1-yl]pyridine-3-carboxamide (Compound 1603)

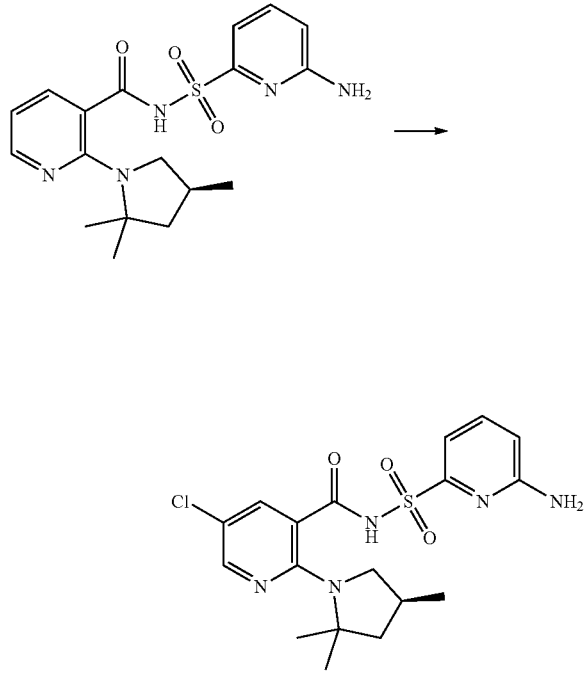 [SMILES: C[C@@H]1CN(c2ncccc2C(=O)NS(=O)(=O)c2cccc(N)n2)C(C)(C)C1 ; C[C@@H]1CN(c2ncc(Cl)cc2C(=O)NS(=O)(=O)c2cccc(N)n2)C(C)(C)C1]

N-[(6-amino-2-pyridyl)sulfonyl]-2-[(4S)-2,2,4-trimethylpyrrolidin-1-yl]pyridine-3-carboxamide (Compound 946) (40.0 mg, 0.102 mmol) and N-chlorosuccinimide (13.65 mg, 0.1022 mmol) in dichloromethane (400 µL) was stirred at reflux for 3 days. The reaction mixture was directly purified by chromatography over silica gel (4 g) with a linear gradient of 0 to 5% methanol in dichloromethane to give N-[(6-amino-2-pyridyl)sulfonyl]-5-chloro-2-[(4S)-2,2,4-trimethylpyrrolidin-1-yl]pyridine-3-carboxamide (Compound 1603) (25 mg, 0.058 mmol, 57%) $^1$H NMR (400 MHz, DMSO-d$_6$) δ 12.54 (s, 1H), 8.27-8.00 (m, 1H), 7.72-7.54 (m, 2H), 7.18 (d, J=7.2 Hz, 1H), 6.66 (d, J=8.4 Hz, 1H), 6.50 (s, 2H), 2.55 (s, 2H), 2.17 (dq, J=13.0, 7.1, 6.7 Hz, 1H), 1.83 (dd, J=11.8, 5.6 Hz, 1H), 1.47 (d, J=7.1 Hz, 6H), 1.37 (t, J=12.1 Hz, 1H), 0.85 (d, J=6.3 Hz, 3H). ESI-MS m/z calc. 423.1132, found 424.0 (M+1)$^+$; Retention time: 1.75 minutes.

Preparation 89: N-[(6-acetamido-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 1652)

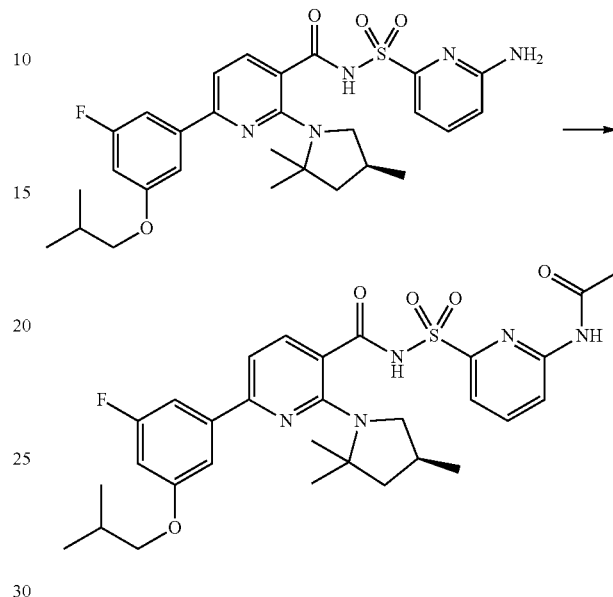

N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (56.78 mg, 0.1022 mmol) in pyridine (161.7 mg, 165.3 µL, 2.044 mmol) was treated with acetic anhydride (104.3 mg, 96.40 µL, 1.022 mmol) and heated to 45° C. for 2.5 hours. The reaction mixture was diluted with a 9:1 (v/v) mixture of dimethyl sulfoxide in water and purified by preparative HPLC chromatography to give N-[(6-acetamido-2-pyridyl)sulfonyl]-6-(3-fluoro-5-isobutoxy-phenyl)-2-[(4S)-2,2,4-trimethylpyrrolidin-1-yl]pyridine-3-carboxamide (Compound 1652) (22 mg, 0.036 mmol, 35%) $^1$H NMR (400 MHz, DMSO-d$_6$) δ 12.68 (s, 1H), 10.87 (s, 1H), 8.35 (d, J=8.4 Hz, 1H), 8.17-8.05 (m, 1H), 7.88-7.80 (m, 2H), 7.51-7.45 (m, 1H), 7.42 (ddd, J=10.2, 2.4, 1.3 Hz, 1H), 7.30 (d, J=8.0 Hz, 1H), 6.90 (dt, J=10.7, 2.3 Hz, 1H), 3.83 (d, J=6.6 Hz, 2H), 2.60 (dd, J=10.2, 7.2 Hz, 1H), 2.52 (d, J=5.3 Hz, 1H), 2.14 (s, 4H), 2.07-2.00 (m, 1H), 1.87 (dd, J=11.8, 5.6 Hz, 1H), 1.59 (d, J=6.0 Hz, 6H), 1.41 (t, J=12.1 Hz, 1H), 0.99 (d, J=6.7 Hz, 6H), 0.77 (d, J=6.3 Hz, 3H). ESI-MS m/z calc. 597.2421, found 598.0 (M+1)$^+$; Retention time: 2.83 minutes.

Preparation 90: N-((6-aminopyridin-2-yl)sulfonyl)-6-chloro-2-(3-fluoro-5-isobutoxyphenyl)nicotinamide

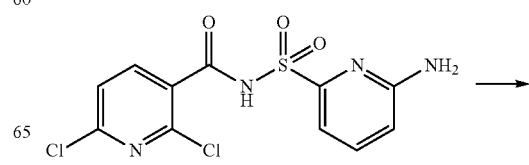

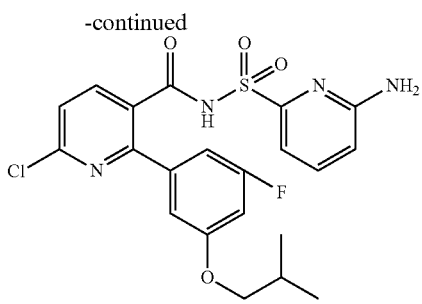

A mixture of N-((6-aminopyridin-2-yl)sulfonyl)-2,6-dichloronicotinamide (2.6 g, 7.4 mmol) and 2-(3-fluoro-5-isobutoxyphenyl)-4,4,5,5-tetramethyl-1,3,2-dioxaborolane (2.3 g, 7.7 mmol) in 12 mL of N,N-dimethylformamide and 3 mL of water was heated under nitrogen to 70° C. for 30 minutes and then tetrakis(triphenylphosphine)palladium(0) (0.20 g, 0.17 mmol) and sodium carbonate (4.8 g, 45 mmol) were added to the reaction mixture. The mixture was stirred at 70° C. for 18 hours and then purified by silica gel chromatography eluting with a gradient of 40 to 100% ethyl acetate in hexanes. The product was further purified on reverse phase HPLC and a white solid was isolated as N-((6-aminopyridin-2-yl)sulfonyl)-6-chloro-2-(3-fluoro-5-isobutoxyphenyl)nicotinamide (0.37 g, 0.77 mmol, 14%). $^1$H NMR (DMSO-$d_6$, 250 MHz): δ 8.03 (d, J=8.3 Hz, 1H), 7.62 (m, 2H), 7.11 (d, J=7.3 Hz, 1H), 6.93 (m, 2H), 6.81 (d, J=9.3 Hz, 1H), 6.73 (d, J=8.5 Hz, 1H), 3.87 (d, J=6.5 Hz, 2H), 2.02 (m, 1H), 1.00 (d, J=6.5 Hz, 6H) ppm. LC-MS: (M+H)$^+$=479.1

Preparation 91: N-((6-aminopyridin-2-yl)sulfonyl)-6-chloro-6'-isopropoxy-[2,3'-bipyridine]-3-carboxamide

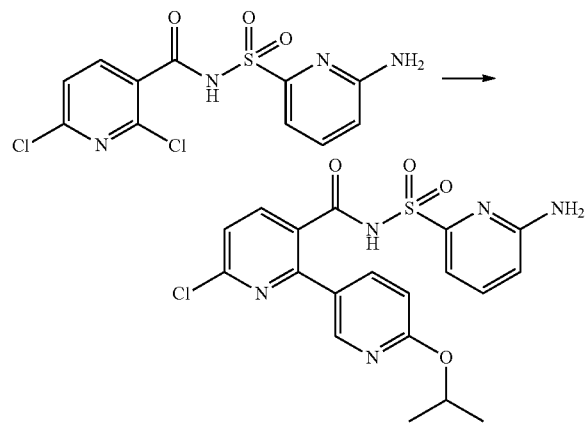

A mixture of the sulfonamide N-((6-aminopyridin-2-yl)sulfonyl)-2,6-dichloronicotinamide (2.1 g, 6.0 mmol) and 2-isopropoxy-5-(4,4,5,5-tetramethyl-1,3,2-dioxaborolan-2-yl)pyridine (1.7 g, 6.6 mmol) in 12 mL of N,N-dimethylformamide and 3 mL of water was heated under nitrogen at 70° C. for 20 minutes and added tetrakis(triphenylphosphine)palladium(0) (0.15 g, 0.13 mmol) and sodium carbonate (1.9 g, 18 mmol). The reaction mixture was stirred at 70° C. for 19 hours. The reaction mixture was evaporated to dryness, and the crude product was purified by silica gel chromatography utilizing a gradient of 40 to 100% ethyl acetate in hexanes. The product was further purified on reverse phase HPLC and a white solid was isolated as N-((6-aminopyridin-2-yl)sulfonyl)-6-chloro-6'-isopropoxy-[2,3'-bipyridine]-3-carboxamide (0.72 g, 1.6 mmol, 27%). $^1$H NMR (DMSO-$d_6$, 250 MHz): δ 8.33 (s, 1H), 8.06 (d, J=8.0 Hz, 1H), 7.64 (m, 3H), 7.15 (d, J=7.3 Hz, 1H), 6.93 (m, 2H), 6.80 (d, J=7.3 Hz, 1H), 6.69 (d, J=8.8 Hz, 1H), 5.27 (m, 1H), 1.32 (d, J=6.3 Hz, 6H) ppm.

Preparation 92: N-[(6-amino-2-pyridyl)sulfonyl]-2-(6-isopropoxy-3-pyridyl)-6-[(4S)-2,2,4-trimethylpyrrolidin-1-yl]pyridine-3-carboxamide (Compound 1436)

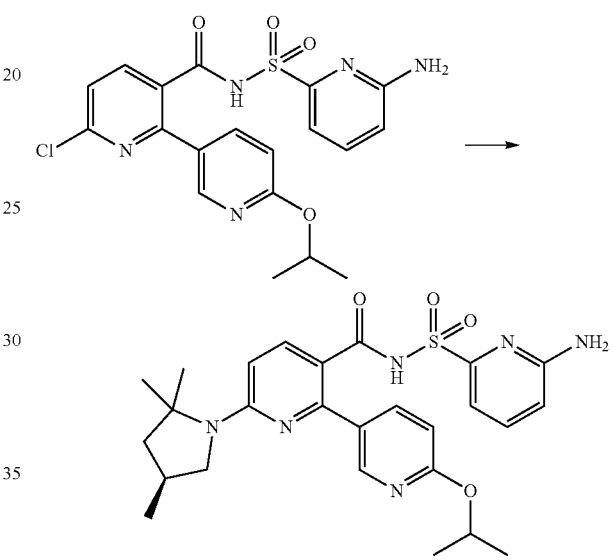

N-((6-aminopyridin-2-yl)sulfonyl)-6-chloro-6'-isopropoxy-[2,3'-bipyridine]-3-carboxamide (0.050 g, 0.11 mmol) and cesium floride (0.085 g, 0.56 mmol) were combined in dimethyl sulfoxide (0.5 mL). The reaction mixture was stirred at 150° C. for 16 hours. (4S)-2,2,4-trimethylpyrrolidine (0.0379 g, 0.335 mmol) was added to the reaction mixture and the mixture was stirred at 150° C. for 10 hours. The crude product was purified by reverse phase HPLC utilizing a gradient of 10 to 99% acetonitrile in water to yield N-[(6-amino-2-pyridyl)sulfonyl]-2-(6-isopropoxy-3-pyridyl)-6-[(4S)-2,2,4-trimethylpyrrolidin-1-yl]pyridine-3-carboxamide (Compound 1436) (0.0026 g, 0.0050 mmol, 4.5%). ESI-MS m/z calc. 424.2, found 525.3 (M+1)$^+$; Retention time: 1.89 minutes.

The following compounds can be synthesized using the procedures described herein N-[(6-amino-2-pyridyl)sulfonyl]-2-(3-fluoro-5-isobutoxyphenyl)-6-[(4S)-2,2,4-trimethylpyrrolidin-1-yl]pyridine-3-carboxamide (Compound 1409), N-[(6-amino-2-pyridyl)sulfonyl]-2-(3-fluoro-5-isobutoxyphenyl)-6-[(4R)-2,2,4-trimethylpyrrolidin-1-yl]pyridine-3-carboxamide (Compound 1385), N-[(6-amino-2-pyridyl)sulfonyl]-2-(6-isopropoxy-3-pyridyl)-6-[(4R)-2,2,4-trimethylpyrrolidin-1-yl]pyridine-3-carboxamide (Compound 1491).

Preparation 93: N-[(6-amino-2-pyridyl)sulfonyl]-6-cyano-2-[(4S)-2,2,4-trimethylpyrrolidin-1-yl]pyridine-3-carboxamide (Compound 1564)

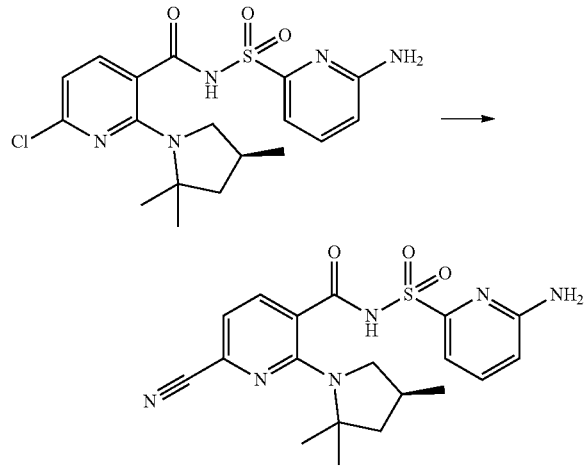

[(2-Di-tert-butylphosphino-2',4',6'-triisopropyl-1,1'-biphenyl)-2-(2'-amino-1,1'-biphenyl)] palladium(II) methanesulfonate (4.186 mg, 0.005270 mmol), di-tert-butyl-[2-(2,4,6-triisopropylphenyl)phenyl]phosphane (2.238 mg, 0.005270 mmol), Potassium hexacyanoferrate(II) trihydrate (22.26 mg, 0.05270 mmol), and N-[(6-amino-2-pyridyl)sulfonyl]-6-chloro-2-[(4S)-2,2,4-trimethylpyrrolidin-1-yl]pyridine-3-carboxamide (Compound 852) (44.7 mg, 0.1054 mmol) were added to a vial and the vial was purged with nitrogen. Deoxygenated dioxane (500 µL) and a solution of potassium carbonate (263.6 µL of 0.05 M, 0.01318 mmol) was added to reaction mixture, the head space was purged with nitorgen and the sealed vial was stirred at 100° C. for 1 hour. The crude product was purified by reverse phase HPLC utilizing a gradient of 10 to 99% acetonitrile in water to yield N-[(6-amino-2-pyridyl)sulfonyl]-6-cyano-2-[(4S)-2,2,4-trimethylpyrrolidin-1-yl]pyridine-3-carboxamide (Compound 1564) (1.8 mg, 0.0043 mmol, 4.1%) ESI-MS m/z calc. 414.1474, found 415.2 (M+1)$^+$; Retention time: 1.49 minutes.

Preparation 94: N-[(6-amino-2-pyridyl)sulfonyl]-2-[(2S,5R)-2,5-dimethylpyrrolidin-1-yl]-6-(3-fluoro-5-isobutoxy-phenyl)-4-hydroxy-pyridine-3-carboxamide (Compound 1430)

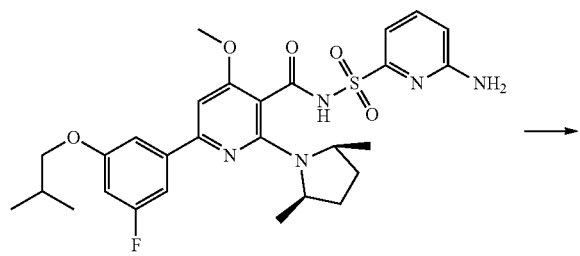

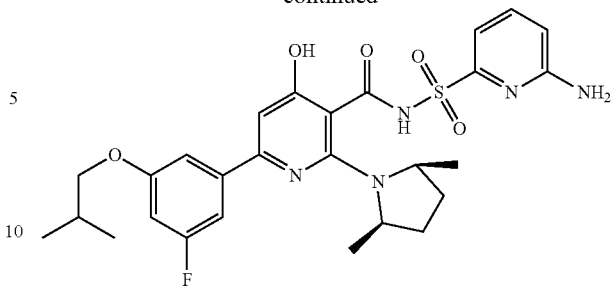

In a nitrogen purged flask, N-[(6-amino-2-pyridyl)sulfonyl]-2-[(2S,5R)-2,5-dimethylpyrrolidin-1-yl]-6-(3-fluoro-5-isobutoxy-phenyl)-4-methoxy-pyridine-3-carboxamide (Compound 1254) (17.5 mg, 0.0306 mmol) was dissolved in dichloromethane (1.577 mL). The mixture was cooled to −78° C., and tribromoborane (811.2 mg, 306.1 µL of 1 M, 0.3061 mmol) was added to the reaction mixture in a dropwise manner. The mixture was slowly warmed to room temperature. The mixture was stirred overnight at ambient temperature. The reaction mixture was added to ice (~5 mL). The layers were separated, and the aqueous layer was extracted with dichloromethane. The combined organic layers were dried over sodium sulfate, concentrated, and purified by reverse phase HPLC utilizing a gradient of 1-99% acetonitrile in 5 mM aqueous hydrochloric acid. The compound was further puried on silica gel using dichloromethane as the eluent to yield N-[(6-amino-2-pyridyl)sulfonyl]-2-[(2S,5R)-2,5-dimethylpyrrolidin-1-yl]-6-(3-fluoro-5-isobutoxy-phenyl)-4-hydroxy-pyridine-3-carboxamide (Compound 1430) (3.2 mg, 0.0057 mmol, 19%) as an off-white solid. ESI-MS m/z calc. 557.2108, found 558.3 (M+1)*, Retention time: 1.84 minutes.

Preparation 95: 4-Bromo-2-(mesityloxy)benzoic acid

Step 1: 4-Bromo-2-(mesityloxy)benzonitrile

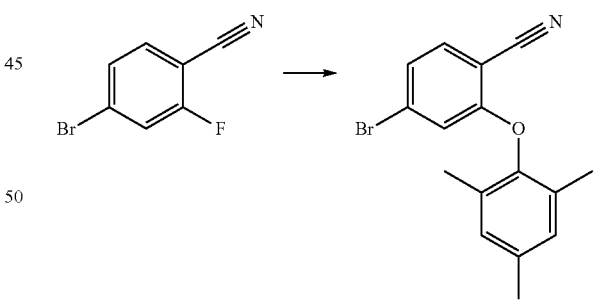

A mixture of 4-bromo-2-fluoro-benzonitrile (1.2 g, 6.0 mmol), 2,4,6-trimethylphenol (780 mg, 6.1 mmol), potassium carbonate (2.50 g, 18.1 mmol), and dimethylsulfoxide (9.0 mL) were microwave irradiated at 140° C. for 2 hours. Water (20 mL) was added and the resulting mixture was stirred for 5 minutes. The resulting suspension was filtered and the solid was washed with water and dried under vacuum at 50° C. for 16 hours to yield 4-bromo-2-(mesityloxy)benzonitrile (1.8 g, 95%) as a brown solid. $^1$H NMR (CDCl$_3$, 250 MHz): 7.50 (d, J=8.2 Hz, 1H), 7.20 (d, J=8.2 Hz, 1H), 6.94 (s, 2H), 6.61 (s, 1H), 2.33 (s, 3H), 2.10 (s, 6H) ppm.

Step 2: 4-Bromo-2-(mesityloxy)benzoic acid

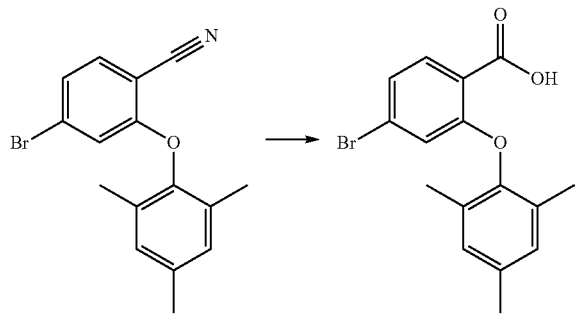 [SMILES: Cc1cc(C)c(Oc2cc(Br)ccc2C#N)c(C)c1 ; Cc1cc(C)c(Oc2cc(Br)ccc2C(=O)O)c(C)c1]

4-bromo-2-(mesityloxy)benzonitrile (1.8 g, 9.0 mmol) was suspended in ethanol (6 mL) and water (12 mL), containing sodium hydroxide (3.0 g, 75 mmol). The mixture was stirred at 90° C. for 16 hours. Hydrochloric acid (6M, 13 mL) was added to the reaction mixture followed by water (20 mL) and the suspension was stirred for 10 minutes, filtered, and washed with water and then hexanes to yield 4-bromo-2-(mesityloxy)benzoic acid as an off-white solid (1.7 g, 5.1 mmol, 57%). $^1$H NMR (DMSO-$d_6$, 250 MHz): 7.74 (d, J=8.2 Hz, 1H), 7.28 (d, J=8.2 Hz, 1H), 7.01 (s, 2H), 6.41 (s, 1H), 2.28 (s, 3H), 2.02 (s, 6H) ppm.

Preparation 96: 6-Methoxy-4-methylpyridine-2-sulfonamide

Step 1: 2-Benzylsulfanyl-6-chloro-4-methylpyridine

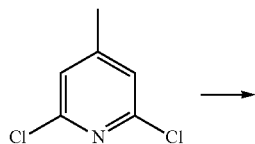

2,6-Dichloro-4-methyl-pyridine (4.74 g, 29.3 mmol) was dissolved in tetrahydrofuran (47.40 mL) with phenylmethanethiol (3.634 g, 3.435 mL, 29.26 mmol) and 2-methylpropan-2-olate (Sodium Ion (1)) (29.26 mL of 2 M, 58.52 mmol) was added to the reaction mixture. The reaction was stirred for 16 hours and partitioned between water and ethyl acetate. The organics were separated, washed with brine, dried over sodium sulfate and evaporated. The crude material was used without further purification. 2-Benzylsulfanyl-6-chloro-4-methyl-pyridine (6.91 g, 27.7 mmol, 94.5%) ESI-MS m/z calc. 249.0379, found 250.0 (M+1)$^+$; Retention time: 0.78 minutes.

Step 2: 6-Chloro-4-methylpyridine-2-sulfonamide

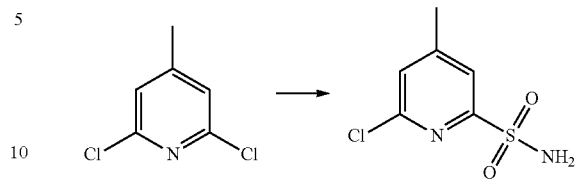

A biphasic mixture of 2-benzylsulfanyl-6-chloro-4-methyl-pyridine (6.87 g, 27.5 mmol) in dichloromethane (41.22 mL), water (13.74 mL), and aqueous hydrochloric acid (2.751 mL of 1 M, 2.751 mmol) was cooled in a salt water ice bath. (Note: Aqueous hydrochloric acid is added to avoid an otherwise delayed exotherm upon the chlorine addition). Chlorine (7.800 g, 110.0 mmol) was bubbled through the solution (3 times at 2 minute intervals) over an hour. The reaction was stirred at 0° C. After 1.5 hours (reaction monitored by UPLC) the reaction was added dropwise to an ice bath cooled solution of ammonium hydroxide (41.32 mL of 28% w/v, 330.1 mmol). The reaction was warmed to room temperature and stirred for 15 minutes. The reaction mixture was partitioned between ethyl acetate (60 mL) and water (20 mL). The organics were separated, and the aqueous layer was extracted twice with ethyl acetate (60 mL portions). The organics were combined, washed with brine, dried over sodium sulfate and evaporated. The resulting solid was triturated with dichloromethane (30 mL) and filtered. The solid was washed with minimal dichloromethane to give 6-chloro-4-methyl-pyridine-2-sulfonamide as an off white solid (3.18 g, 15.4 mmol, 56.0%) $^1$H NMR (400 MHz, DMSO-$d_6$) δ 7.78 (dd, J=1.3, 0.7 Hz, 1H), 7.66-7.63 (m, 1H), 7.59 (s, 2H), 2.45 (s, 3H). ESI-MS m/z calc. 205.99167, found 206.9 (M+1)$^+$; Retention time: 0.3 minutes.

Step 3: 6-Methoxy-4-methylpyridine-2-sulfonamide

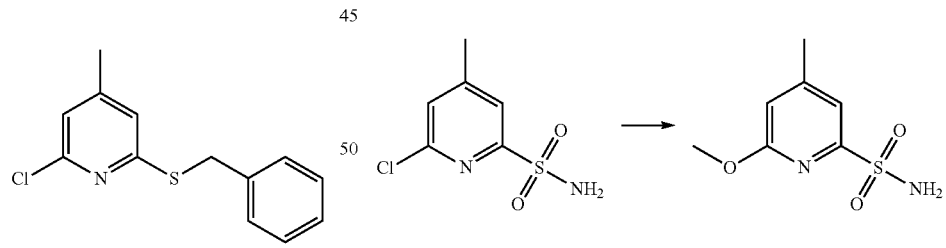

6-Chloro-4-methylpyridine-2-sulfonamide (500. mg, 2.42 mmol) was dissolved in sodium methoxide in methanol (2.537 g, 2.615 mL of 25% w/v, 12.10 mmol) and heated at 65° C. After 1 hour, all starting material was gone and two products had formed. The reaction mixture was partitioned between ethyl acetate and a saturated aqueous ammonium chloride solution. The organics were separated, washed with water, brine, dried over sodium sulfate and evaporated to dryness. The crude product was purified by silica gel chromatography eluting with 0 to 100% ethyl acetate in hexanes to give 6-methoxy-4-methylpyridine-2-sulfonamide (126 mg, 0.623 mmol, 25.7%) ESI-MS m/z calc. 202.04121, found 203.0 (M+1)$^+$; Retention time: 0.32 minutes.

Preparation 97: 6-Amino-4-methylpyridine-2-sulfonamide

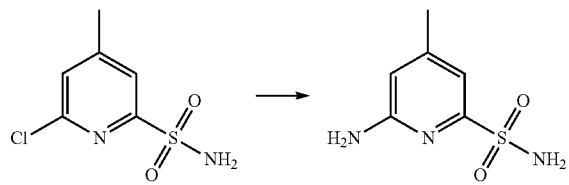

6-Chloro-4-methylpyridine-2-sulfonamide (500. mg, 2.42 mmol) was dissolved in aqueous ammonium hydroxide (3.029 mL of 28% w/v, 24.20 mmol) and irradiated in a microwave reactor for 1 hour at 150° C. The reaction was evaporated and the solid was washed with water and methanol to remove excess ammonium hydroxide. The resulting solid was a mixture of product and starting material. The mixture was taken on to the next step without further purification. 6-amino-4-methylpyridine-2-sulfonamide (200. mg, 1.07 mmol, 44.2%) ESI-MS m/z calc. 187.04155, found 188.0 (M+1)$^+$; Retention time: 0.21 minutes.

Preparation 98: 4,4,5,5-Tetramethyl-2-(3,3,5,5-tetramethylcyclopenten-1-yl)-1,3,2-dioxaborolane

Step 1: 3,3,5-trimethyl-5-trimethylstannyl-cyclohexanone

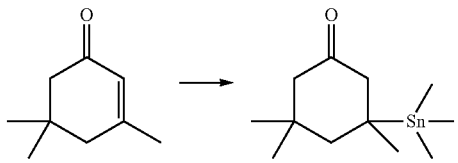

To a stirring solution of trimethyl(trimethylstannyl)stannane (3.555 g, 2.250 mL, 10.85 mmol) in tetrahydrofuran (50 mL) at −20° C. was added methyllithium (4.964 g, 6.781 mL of 1.6 M, 10.85 mmol) and the mixture was stirred at −20° C. for 15 minutes. Next the 3,5,5-trimethylcyclohex-2-en-1-one (1.00 g, 7.24 mmol) was slowly added and the reaction mixture was warmed to 0° C., stirred 30 minutes, and then quenched with methanol (695.6 mg, 879.4 µL, 21.71 mmol). The reaction mixture was warmed to room temperature and diluted with water then extracted twice with diethyl ether. The combined organic layers were dried (sodium sulfate), filtered and concentrated to a yellow oil which was purified by silica gel chromatography using 100% hexanes as eluent followed by 100% dichloromethane as eluent to yield 3,3,5-trimethyl-5-trimethylstannyl-cyclohexanone (2.01 g, 6.63 mmol, 91.7%) as a clear oil. $^1$H NMR (400 MHz, CDCl$_3$) δ 2.59-2.45 (m, 1H), 2.21-2.12 (m, 3H), 1.92 (d, J=14.2 Hz, 1H), 1.59 (d, J=14.2 Hz, 1H), 1.28 (s, 3H), 1.07 (s, 3H), 1.00 (s, 3H), 0.13 (d, J=1.1 Hz, 1H), 0.07 (s, 9H), 0.01 (d, J=1.1 Hz, 11H).

Step 2: 2,2,4,4-Tetramethylcyclopentanone

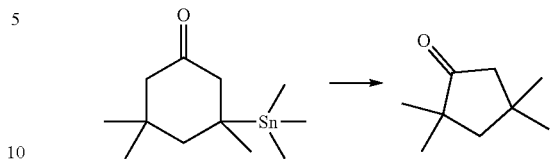

To a stirring solution of 3,3,5-trimethyl-5-trimethylstannyl-cyclohexanone (4.17 g, 13.8 mmol) in the dichloromethane (79.23 mL) under a nitrogen atmosphere at 0° C. was added (dropwise) tetrachlorotitanium (2.610 g, 2.183 mL, 13.76 mmol) giving a dark brown color on addition. Upon completion of addition the reaction mixture was a brown suspension which was stirred 20 minutes at 0° C. and then quenched by the addition of a solution of saturated aqueous sodium bicarbonate (Caution: Gas evolution, reaction became biphasic with a purple suspension as the aqueous layer). The resulting mixture was extracted twice with dichloromethane, dried (magnesium sulfate), filtered and carefully concentrated to a clear oil. Purified by silica gel chromatography eluting with 100% giving 2,2,4,4-tetramethylcyclopentanone (1.67 g, 11.9 mmol, 86.6%) as a clear oil.

Step 3: 4,4,5,5-Tetramethyl-2-(3,3,5,5-tetramethylcyclopenten-1-yl)-1,3,2-dioxaborolane

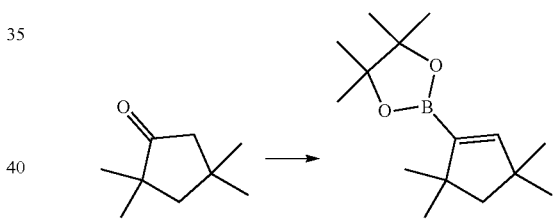

To 2,2,4,4-tetramethylcyclopentanone (1.67 g, 11.9 mmol) was added tetrahydrofuran (16.70 mL) and the reaction was chilled to −78° C. The reaction was stirred for 10 minutes and lithium bis(trimethylsilyl)amide (14.29 mL of 1 M, 14.29 mmol) was added dropwise and the reaction was allowed to stir at −78° C. for 1 hour. 1,1,1-Trifluoro-N-phenyl-N-(trifluoromethylsulfonyl)methanesulfonamide (5.105 g, 14.29 mmol) dissolved in tetrahydrofuran (12.5 mL) was added dropwise and the reaction was allowed to warm to room temperature and stir 16 hours. The reaction was quenched with a saturated aqueous solution of sodium chloride and extracted with ethyl acetate. The organic layer was dried over sodium sulfate and evaporated to an orange syrup. The crude orange syrup was added to a mixture of bis(pinacol)diboron (4.535 g, 17.86 mmol), [1,1'-bis(diphenylphosphino)ferrocene]dichloropalladium(II), complex with dichloromethane (871.5 mg, 1.191 mmol) and potassium acetate (3.507 g, 35.73 mmol) in dimethylformamide (16.70 mL). The reaction was purged with nitrogen and heated to 65° C. for 16 hours. The reaction was quenched with a saturated aqueous solution of sodium chloride and extracted with ethyl acetate. The organic layer was dried over sodium sulfate and evaporated to dryness. The crude product was purified by silica gel chromatography using a gradient from 100% hexanes to 40% ethyl acetate in hexanes giving 4,4,5,5-tetramethyl-2-(3,3,5,5-tetramethylcyclopenten-1-yl)-1,3,2-dioxaborolane (651 mg, 2.60 mmol, 21.8%) as a white solid.

Preparation 99: N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2492) (Isomer 1) (Compound 2374) (Isomer 2)

Step 1: ethyl 2-chloro-6-(3-fluoro-5-isobutoxy-phenyl)pyridine-3-carboxylate

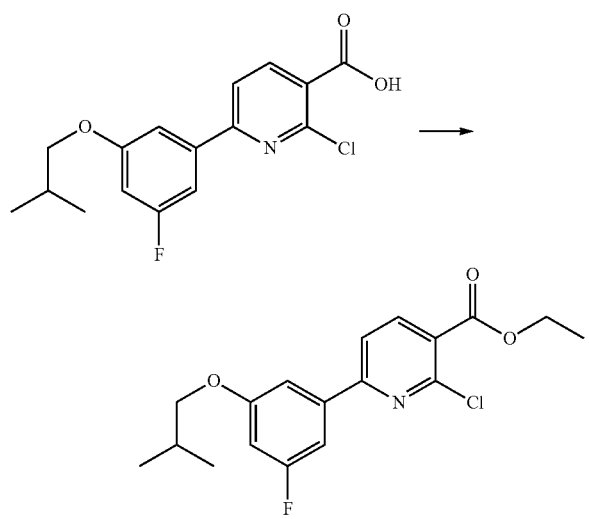

2-Chloro-6-(3-fluoro-5-isobutoxy-phenyl)pyridine-3-carboxylic acid (5.077 g, 15.53 mmol) was dissolved in ethyl alcohol (50.26 mL) and thionyl chloride (2.218 g, 1.360 mL, 18.64 mmol) was added dropwise. The resulting solution was slowly heated to 76° C. (reflux) and stirred at 76° C. for 5 hours. The brownish solution was concentrated to remove solvent. The crude residue was redissolved in ethyl acetate and extracted with saturated aqueous sodium bicarbonate. The aqueous phase was extracted twice with ethyl acetate. The combined organic layers were extracted with saturated aqueous brine, dried over sodium sulfate, concentrated and purified by silica gel chromatography using a gradient from 100% hexanes to 100% ethyl acetate giving ethyl 2-chloro-6-(3-fluoro-5-isobutoxy-phenyl)pyridine-3-carboxylate (3.64 g, 10.3 mmol, 66.6%) as a white solid.

Step 2: Ethyl 6-(3-fluoro-5-isobutoxy-phenyl)-2-(3,3,5,5-tetramethylcyclopenten-1-yl)pyridine-3-carboxylate

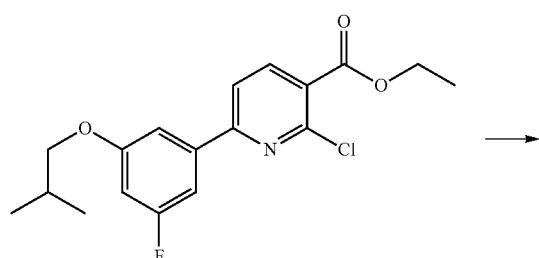

-continued

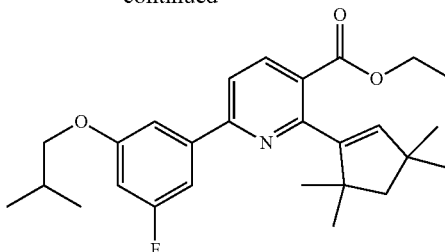

A mixture of ethyl 2-chloro-6-(3-fluoro-5-isobutoxy-phenyl)pyridine-3-carboxylate (841.8 mg, 2.393 mmol), 4,4,5,5-tetramethyl-2-(3,3,5,5-tetramethylcyclopenten-1-yl)-1,3,2-dioxaborolane (598.7 mg, 2.393 mmol), [1,1'-bis(diphenylphosphino)ferrocene]dichloropalladium(II), complex with dichloromethane (525.3 mg, 0.7179 mmol), and sodium carbonate (760.9 mg, 7.179 mmol) in dioxane (10.77 mL) and water (1.196 mL) was heated in a sealed vessel at 150° C. for 16 hours. The reaction was filtered and the solids were washed with ethyl acetate. The extract was evaporated and the residue was purified by silica gel chromatography using a gradient from 100% hexanes to 25% ethyl acetate in hexanes to give ethyl 6-(3-fluoro-5-isobutoxy-phenyl)-2-(3,3,5,5-tetramethylcyclopenten-1-yl)pyridine-3-carboxylate (460.3 mg, 1.047 mmol, 43.75%) as a light yellow solid.

Step 3: 6-(3-Fluoro-5-isobutoxy-phenyl)-2-(3,3,5,5-tetramethylcyclopenten-1-yl)pyridine-3-carboxylic acid

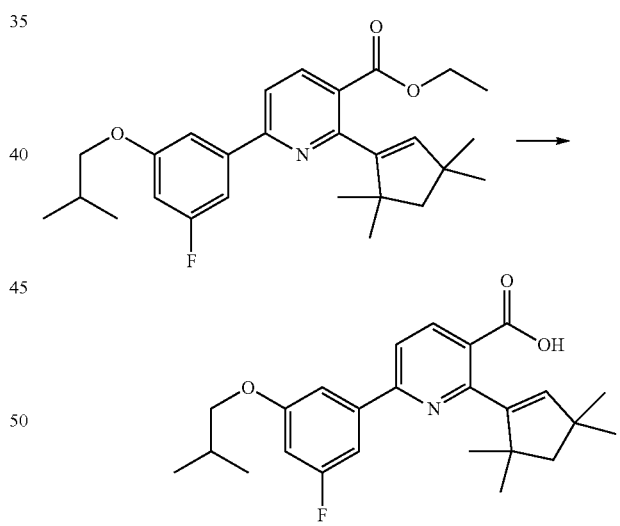

A solution of ethyl 6-(3-fluoro-5-isobutoxy-phenyl)-2-(3,3,5,5-tetramethylcyclopenten-1-yl)pyridine-3-carboxylate (460.3 mg, 1.047 mmol) and sodium hydroxide (2.617 mL of 1 M, 2.617 mmol) in tetrahydrofuran (2.606 mL) and water (2.606 mL) was stirred at 50° C. for 6.5 hours. The reaction was cooled to room temperature and then neutralized with 1M hydrochloric acid and extracted twice with ethyl acetate. The combined extracts were dried over sodium sulfate and evaporated to give 6-(3-fluoro-5-isobutoxy-phenyl)-2-(3,3,5,5-tetramethylcyclopenten-1-yl)pyridine-3-carboxylic acid (389.1 mg, 0.9455 mmol, 90.32%) as yellow needles.

Step 4: 6-(3-Fluoro-5-isobutoxy-phenyl)-2-(2,2,4,4-tetramethylcyclopentyl)pyridine-3-carboxylic acid

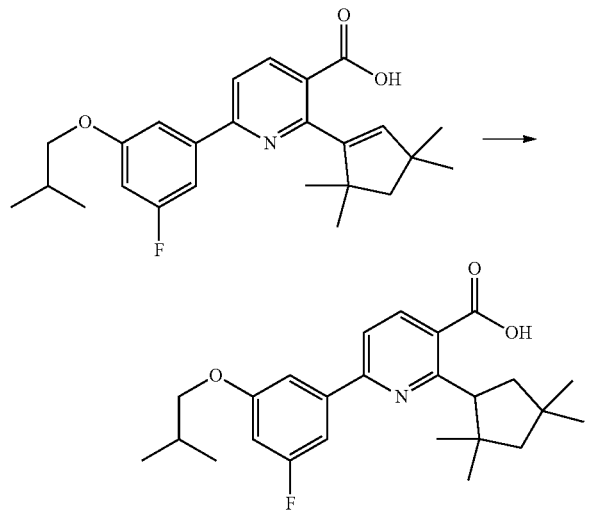

A mixture of 6-(3-fluoro-5-isobutoxy-phenyl)-2-(3,3,5,5-tetramethylcyclopenten-1-yl)pyridine-3-carboxylic acid (389.1 mg, 0.9455 mmol), palladium hydroxide (79.67 mg, 0.5673 mmol) and ammonium formate (1.192 g, 18.91 mmol) in ethanol (10 mL) were combined in a microwave vial and heated to 85° C. for 3 hours. The reaction mixture was cooled to room temperature, uncapped, ammonium formate (1.192 g, 18.91 mmol) and palladium hydroxide (79.67 mg, 0.5673 mmol) were added, nitrogen was bubbled through the solution for 2 minutes, and the vial was capped and returned to the microwave reactor at 8.5° C. for 4 additional hours. The reaction was filtered through celite eluting with methanol and concentrated under reduced pressure. The mixture was then diluted with 1N aqueous hydrochloric acid and washed with twice with ethyl acetate. The organic layers were combined, dried (sodium sulfate), filtered and concentrated to a clear oil with some white solid present. The crude material was purified by silica gel chromatography using a gradient from 100% dichloromethane to 20% methanol in dichloromethane followed by 20% methanol in ethyl acetate giving 6-(3-fluoro-5-isobutoxy-phenyl)-2-(2,2,4,4-tetramethylcyclopentyl)pyridine-3-carboxylic acid (52.3 mg, 0.126 mmol, 13.4%) as a white solid.

Step 5: N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2492) (Isomer 1) (Compound 2374) (Isomer 2)

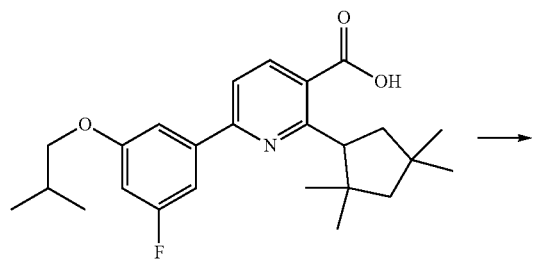

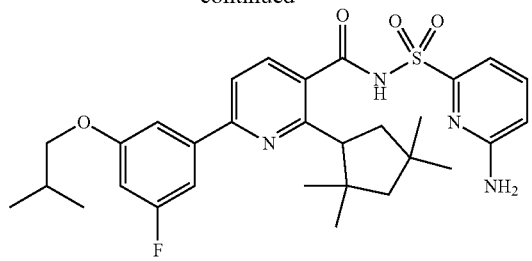

A solution of 6-(3-fluoro-5-isobutoxy-phenyl)-2-(2,2,4,4-tetramethylcyclopentyl)pyridine-3-carboxylic acid (52.0 mg, 0.126 mmol) and carbonyl diimidazole (30.58 mg, 0.1886 mmol) in dimethylformamide (0.5 mL) was stirred at 45° C. for 90 minutes. A separate solution of 6-aminopyridine-2-sulfonamide (43.54 mg, 0.2514 mmol) and sodium hydride (10.06 mg, 0.2514 mmol) in dimethylformamide (0.5 mL) which was stirred at 45° C. for 45 minutes was then added and the resulting mixture was stirred at 45° C. for 2 hours. The reaction was filtered and purified using a reverse phase HPLC-MS method using a Luna C18 (2) column (75×30 mm, 5 μm particle size) sold by Phenomenex (pn: 00C-4252-U0-AX), and a dual gradient run from 1 to 99% mobile phase B over 15.0 minutes (mobile phase A=H$_2$O (5 mM HCl), mobile phase B=acetonitrile, flow rate=50 mL/min, injection volume=950 μL and column temperature=25° C.) giving N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2492) (Isomer 1) (Compound 2374) (Isomer 2) hydrochloride (51 mg, 0.084 mmol, 67%) as an off-white solid $^1$H NMR (400 MHz, DMSO-d$_6$) δ 12.63 (s, 1H), 7.91 (dd, J=20.4, 8.2 Hz, 2H), 7.66 (t, J=7.9 Hz, 1H), 7.57 (s, 1H), 7.51 (d, J=9.8 Hz, 1H), 7.25 (d, J=7.3 Hz, 1H), 6.93 (d, J=10.7 Hz, 1H), 6.73 (d, J=8.4 Hz, 1H), 6.51 (s, 2H), 3.86 (d, J=6.6 Hz, 2H), 3.58 (dd, J=12.2, 6.5 Hz, 1H), 2.55 (d, J=12.3 Hz, 1H), 2.06 (dt, J=13.2, 6.6 Hz, 1H), 1.63 (dd, J=12.4, 6.4 Hz, 1H), 1.50 (d, J=13.0 Hz, 1H), 1.39 (d, J=12.9 Hz, 1H), 1.15 (s, 3H), 1.08-0.93 (m, 9H), 0.80 (s, 3H), 0.69 (s, 3H). ESI-MS m/z calc. 568.25195, found 569.3 (M+1)$^+$; Retention time: 2.4 minutes.

Preparation 100: 4,4,5,5-tetramethyl-2-[((5S)-3,3,5-trimethylcyclohexen-1-yl]-1,3,2-dioxaborolane

Step 1: (5R)-3,3,5-Trimethylcyclohexanone

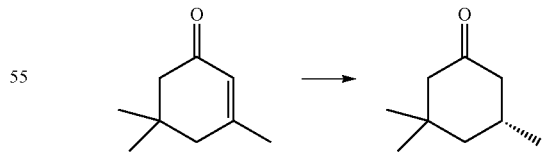

To a round bottom flask purged with nitrogen was added copper (II) acetate (14.53 mg, 0.08000 mmol), [(4S)-4-[5-bis(3,5-ditert-butyl-4-methoxy-phenyl)phosphanyl-1,3-benzodioxol-4-yl]-4,5,6,7-tetrahydro-1,3-benzodioxol-5-yl]-bis(3,5-ditert-butyl-4-methoxy-phenyl)phosphane (47.34 mg, 0.04000 mmol), and toluene (27.64 mL). The reaction was stirred at room temperature for 90 minutes. Polymethylhydrosiloxane (4.8 mL) was added and the reaction was allowed to stir at room temperature for 30 minutes. 3,5,5-Trimethylcyclohex-2-en-1-one (5.528 g, 6.009 mL, 40.00 mmol) was then added dropwise and the reaction was allowed to stir for 90 minutes at room temperature. The reaction was poured into a solution of 3M sodium hydroxide and allowed to stir vigorously for 2 hours. The crude reaction was extracted with ethyl acetate and dried over sodium sulfate. The solvent was removed and the crude product was taken onto the next step without further purification to give (5R)-3,3,5-trimethylcyclohexanone (5.1 g, 36 mmol, 91%) ESI-MS m/z calc. 140.12012, found 141.2 (M+1)⁺; Retention time: 1.44 minutes was a pale oil.

Step 2: 4,4,5,5-tetramethyl-2-[(5S)-3,3,5-trimethyl-cyclohexen-1-yl]-1,3,2-dioxaborolane

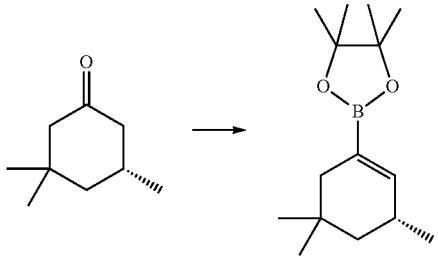

To crude (5R)-3,3,5-trimethylcyclohexanone (2.85 g, 20.3 mmol) was added tetrahydrofuran (28.50 mL) and the reaction was chilled to −78° C. The reaction was stirred for 10 minutes and lithium bis(trimethylsilyl)amide (24.38 mL of 1 M, 24.38 mmol) was added dropwise and the reaction was allowed to stir at −78° C. for 1 hour. 1,1,1-Trifluoro-N-phenyl-N-(trifluoromethylsulfonyl)methanesulfonamide (8.710 g, 24.38 mmol) dissolved in tetrahydrofuran (20 mL) was added dropwise and the reaction was allowed to warm to room temperature and stir for 16 hours. The reaction was quenched with brine and extracted with ethyl acetate. The organic layer was dried over sodium sulfate and evaporated to a yellow oil. The crude vinyl triflate was used in the next step without further purification. The crude vinyl triflate was added to a mixture of bis(pinacol)diboron (7.740 g, 30.48 mmol), bis(diphenylphosphino)ferrocene]dichloropalladium(II), complex with dichloromethane (1.487 g, 2.032 mmol), potassium acetate (5.983 g, 60.96 mmol) in N,N-dimethylformamide (28.50 mL). The reaction was purged with nitrogen and heated to 65° C. for 16 hours. The reaction was quenched with brine and extracted with ethyl acetate. The organic layer was dried over sodium sulfate and evaporated. The crude product was purified by silica gel chromatography utilizing a gradient of 0 to 40% ethyl acetate in hexanes to yield 4,4,5,5-tetramethyl-2-[(5S)-3,3,5-trimethylcyclohexen-1-yl]-1,3,2-dioxaborolane (2.2 g, 8.8 mmol, 43%) as a mixture of regioisomers ESI-MS m/z calc. 250.2104, found 251.6 (M+1)⁺; Retention time: 2.17 minutes Preparation 101: N-[(6-amino-2-pyridyl)sulfonyl]-6-[(1S,2S)-2-(methoxymethyl)cyclopropyl]-2-[(4S)-2,2,4-trimethylpyrrolidin-1-yl]pyridine-3-carboxamide (Compound 1575)

Step 1: N-[(6-amino-2-pyridyl)sulfonyl]-6-[(1S,2S)-2-(methoxymethyl)cyclopropyl]-2-[(4S)-2,2,4-trimethylpyrrolidin-1-yl]pyridine-3-carboxamide (Compound 1575) and N-[(6-amino-2-pyridyl)sulfonyl]-6-[(1R,2R)-2-(methoxymethyl)cyclopropyl]-2-[(4S)-2,2,4-trimethylpyrrolidin-1-yl]pyridine-3-carboxamide

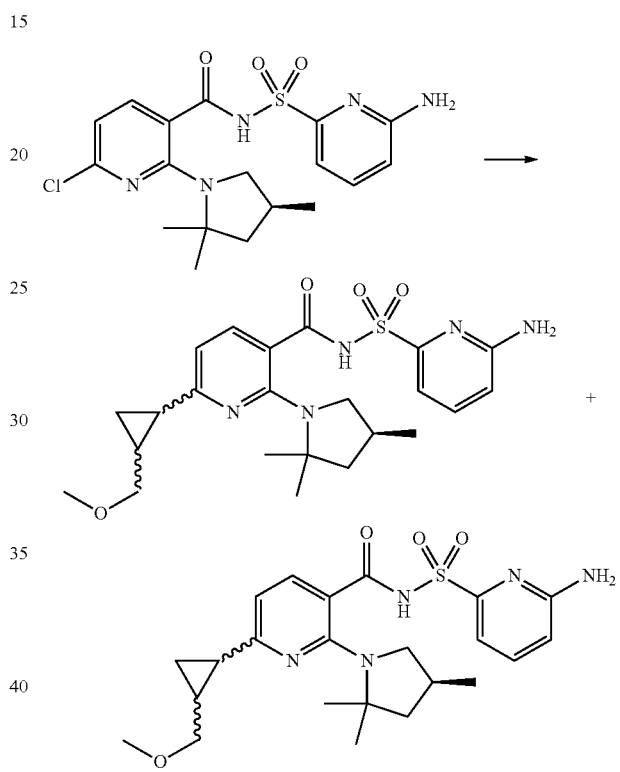

To a microwave vial was added N-[(6-amino-2-pyridyl)sulfonyl]-6-chloro-2-[(4S)-2,2,4-trimethylpyrrolidin-1-yl]pyridine-3-carboxamide (Compound 852) trifluoroacetic acid salt (100 mg, 0.186 mmol), [1,3-Bis(2,6-Diisopropylphenyl)imidazol-2-ylidene](3-chloropyridyl)palladium(II) dichloride (6.3 mg, 0.0093 mmol) and dioxane (600 μL). The reaction was purged with nitrogen for 2 minutes and trans 2-[(1S,2S)-2-(methoxymethyl)cyclopropyl]-4,4,5,5-tetramethyl-1,3,2-dioxaborolane (68.99 mg, 0.325 mmol) was added followed by an aqueous 2M solution of potassium carbonate (279 μL of 2 M, 0.558 mmol). Then the reaction was irradiated to 120° C. over 16 hours in the microwave reactor. The reaction mixture was allowed to cool, filtered and then purified directly by reverse-phase preparative chromatography utilizing a C18 column and HPLC-MS method 1 to 99 acetonitrile in water containing 5 mM hydrochloric acid to afford two compounds. Compound 1 (2.26 mg, 0.0044 mmol, 2.39%) ESI-MS m/z calc. 473.2097, found 474.2 (M+1)⁺; Retention time: 1.13 minutes. Compound 2 (0.86 mg, 0.0018 mmol, 0.97%) ESI-MS m/z calc. 473.2097, found 474.2 (M+1)⁺; Retention time: 1.26 minutes as a light yellow solid.

Preparation 102: N-[(3S)-3-aminopyrrolidin-1-yl]sulfonyl-6-chloro-2-[(4S)-2,2,4-trimethylpyrrolidin-1-yl]pyridine-3-carboxamide

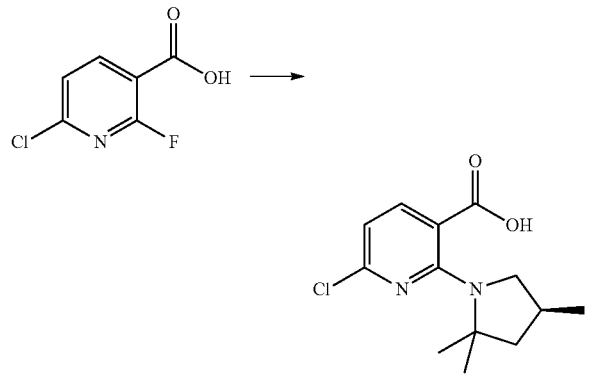

Step 1: 6-chloro-2-[(4S)-2,2,4-trimethylpyrrolidin-1-yl]pyridine-3-carboxylic acid 6-chloro-2-fluoro-pyridine-3-carboxylic acid (1.50 g, 8.545 mmol) and (4S)-2,2,4-trimethylpyrrolidine (Hydrochloric Acid) (1.534 g, 10.25 mmol) were combined in DMSO (4.500 mL). Potassium carbonate (2.362 g, 17.09 mmol) was added. Note: Substantial bubbling was observed upon mixing. The reaction mixture was sealed and heated at 90° C. overnight. The reaction mixture was diluted with EtOAc (50 mL) and washed with aqueous 0.5 N HCl. The organic layer was dried over sodium sulfate, filtered and concentrated under reduced pressure to a yellow oil. To remove any residual solvents, the oil was subjected to a stream of nitrogen gas for 1 hour, resulting in a crystalline solid. The product was used in the next step without further purification. ESI-MS m/z calc. 268.09787, found 269.2 (M+1)+; Retention time: 1.49 minutes Step 2: tert-butyl N-[(3S)-1-[[6-chloro-2-[(4S)-2,2,4-trimethylpyrrolidin-1-yl]pyridine-3-carbonyl]sulfamoyl]pyrrolidin-3-yl]carbamate 6-chloro-2-[(4S)-2,2,4-trimethylpyrrolidin-1-yl]pyridine-3-carboxylic acid (1.61 g, 5.99 mmol) was dissolved in dichloromethane (8 mL), warmed to 40° C. and N-(oxomethylene)sulfamoyl chloride (1.017 g, 625.5 µL, 7.189 mmol) was added. Note: Substantial bubbling was observed during addition. After 3 minutes of stirring at 40° C., additional dichloromethane (10 mL) was added followed by tert-butyl N-[(3S)-pyrrolidin-3-yl]carbamate (2.80 g, 15.0 mmol). Bubbling was observed. After overnight stirring at 40° C., the reaction mixture was diluted with EtOAc (75 mL) and washed with water and brine. The organic layer was dried over sodium sulfate, filtered and concentrated under reduced pressure. The product was isolated by silica gel column chromatography: 0 to 40% EtOAc/hexane gradient on a 80 gram silica gel column. tert-butyl N-[(3S)-1-[[6-chloro-2-[(4S)-2,2,4-trimethylpyrrolidin-1-yl]pyridine-3-carbonyl]sulfamoyl]pyrrolidin-3-yl]carbamate (965 mg, 1.87 mmol, 31.2%) was obtained as a lightly brown foaming solid. $^1$H NMR (400 MHz, DMSO-$d_6$) δ 11.92 (s, 1H), 7.62 (d, J=7.9 Hz, 1H), 7.18 (s, 1H), 6.61 (d, J=7.9 Hz, 1H), 3.96 (s, 1H), 3.65-3.45 (m, 3H), 3.14 (dd, J=9.7, 5.9 Hz, 1H), 3.03 (t, J=10.3 Hz, 1H), 2.97-2.85 (m, 1H), 2.33 (s, 1H), 2.04 (dd, J=12.7, 5.7 Hz, 1H), 1.92 (dd, J=11.4, 5.1 Hz, 1H), 1.78 (dd, J=12.6, 6.9 Hz, 1H), 1.54 (d, J=6.1 Hz, 6H), 1.38 (s, 9H), 1.01 (d, J=6.3 Hz, 3H), 0.83 (s, 1H). ESI-MS m/z calc. 515.1969, found 516.4 (M+1)+; Retention time: 0.77 minutes.

Step 3: N-[(3S)-3-aminopyrrolidin-1-yl]sulfonyl-6-chloro-2-[(4S)-2,2,4-trimethylpyrrolidin-1-yl]pyridine-3-carboxamide

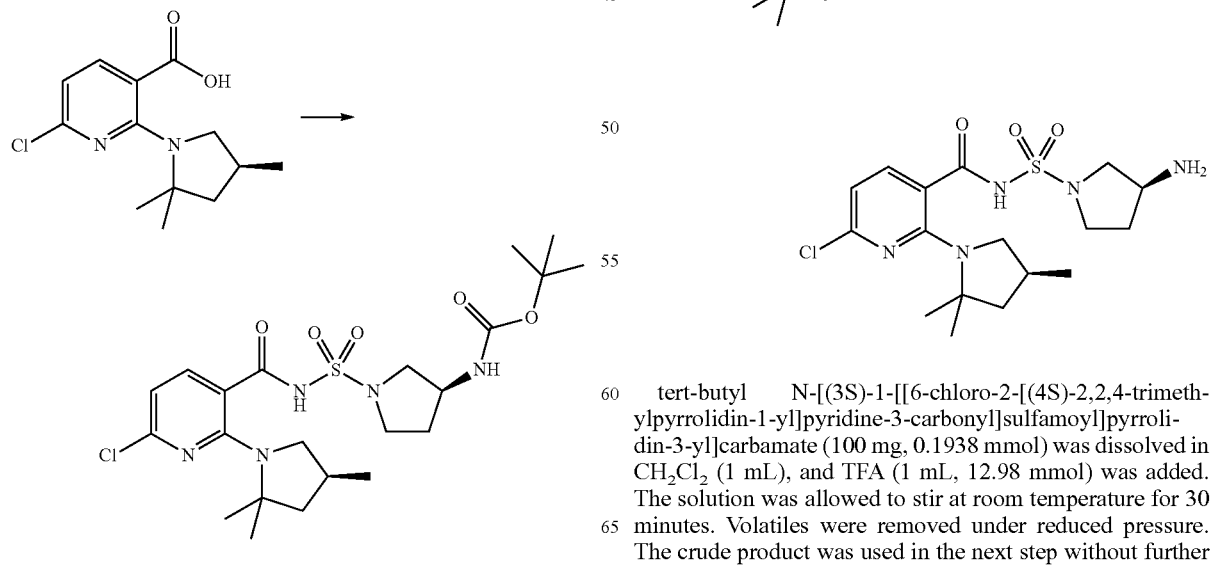

tert-butyl N-[(3S)-1-[[6-chloro-2-[(4S)-2,2,4-trimethylpyrrolidin-1-yl]pyridine-3-carbonyl]sulfamoyl]pyrrolidin-3-yl]carbamate (100 mg, 0.1938 mmol) was dissolved in CH$_2$Cl$_2$ (1 mL), and TFA (1 mL, 12.98 mmol) was added. The solution was allowed to stir at room temperature for 30 minutes. Volatiles were removed under reduced pressure. The crude product was used in the next step without further purification.

Preparation 103: N-[(6-amino-2-pyridyl)sulfonyl]-6-[1-(tert-butylcarbamoyl)-3,6-dihydro-2H-pyridin-5-yl]-2-[(4S)-2,2,4-trimethylpyrrolidin-1-yl]pyridine-3-carboxamide (Compound 2568)

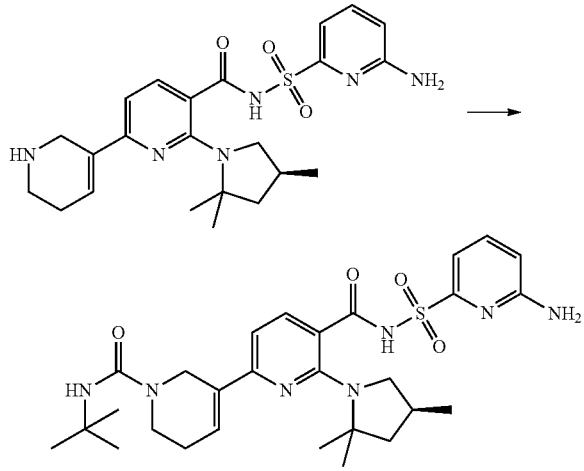

To a stirred solution of N-[(6-amino-2-pyridyl)sulfonyl]-6-(1,2,3,6-tetrahydropyridin-5-yl)-2-[(4S)-2,2,4-trimethylpyrrolidin-1-yl]pyridine-3-carboxamide (Hydrochloric Acid (2)) (27 mg, 0.037 mmol) in anhydrous dichloromethane (1.0 mL), triethyl amine (50 μL, 0.3587 mmol) and 2-isocyanato-2-methyl-propane (8.0 mg, 0.081 mmol) were added at 0° C. under nitrogen. The yellow solution was stirred at ambient temperature for 2 hours. The volatiles were removed under reduced pressure and the residue was purified by reverse-phase HPLC to furnish N-[(6-amino-2-pyridyl)sulfonyl]-6-[1-(tert-butylcarbamoyl)-3,6-dihydro-2H-pyridin-5-yl]-2-[(4S)-2,2,4-trimethylpyrrolidin-1-yl]pyridine-3-carboxamide (Compound 2568) (Hydrochloric Acid (1)) (9.2 mg, 0.015 mmol, 41%) ESI-MS m/z calc. 569.27844, found 570.4 (M+1)$^+$; Retention time: 1.3 minutes The following compounds can be synthesized using the procedures described herein N-[(6-amino-2-pyridyl)sulfonyl]-6-tert-butyl-5-[1-(cyclohexylcarbamoyl)-3,6-dihydro-2H-pyridin-4-yl]-2-[(4S)-2,2,4-trimethylpyrrolidin-1-yl]pyridine-3-carboxamide (Compound 2520)

Preparation 104: N-[(6-amino-2-pyridyl)sulfonyl]-6-[1-(2,2-dimethylbutanoyl)-3,6-dihydro-2H-pyridin-5-yl]-2-[(4S)-2,2,4-trimethylpyrrolidin-1-yl]pyridine-3-carboxamide (Compound 2612)

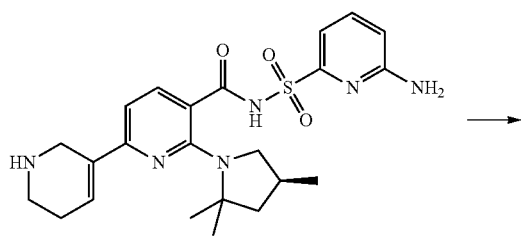

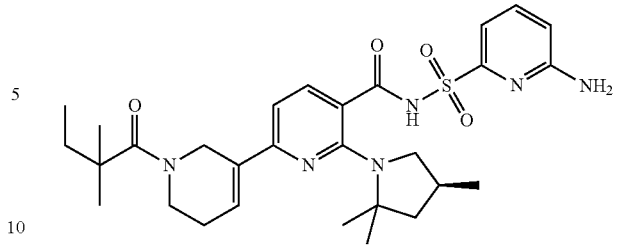

To a stirred solution of N-[(6-amino-2-pyridyl)sulfonyl]-6-(1,2,3,6-tetrahydropyridin-5-yl)-2-[(4S)-2,2,4-trimethylpyrrolidin-1-yl]pyridine-3-carboxamide (Hydrochloric Acid (2)) (27 mg, 0.037 mmol) in anhydrous dichloromethane (1.0 mL), triethyl amine (50. μL, 0.36 mmol) and 2,2-dimethylbutanoyl chloride (11 mg, 0.082 mmol) were added at 0° C. under nitrogen. The yellow solution was stirred at ambient temperature for 2 hours. The volatiles were removed under reduced pressure and the residue was purified from reverse-phase HPLC to furnish N-[(6-amino-2-pyridyl)sulfonyl]-6-[1-(2,2-dimethylbutanoyl)-3,6-dihydro-2H-pyridin-5-yl]-2-[(4S)-2,2,4-trimethylpyrrolidin-1-yl]pyridine-3-carboxamide (Compound 2612) (Hydrochloric Acid (1)) (6.7 mg, 0.011 mmol, 27%) ESI-MS m/z calc. 568.2832, found 569.7 (M+1)$^+$; Retention time: 1.44 minutes The following compounds can be synthesized using the procedures described herein N-[(6-amino-2-pyridyl)sulfonyl]-6-[1-(3-chlorobenzoyl)-3,6-dihydro-2H-pyridin-5-yl]-2-[(4S)-2,2,4-trimethylpyrrolidin-1-yl]pyridine-3-carboxamide (Compound 1984), N-[(6-amino-2-pyridyl)sulfonyl]-6-[1-(1-piperidylsulfonyl)-3,6-dihydro-2H-pyridin-5-yl]-2-[(4S)-2,2,4-trimethylpyrrolidin-1-yl]pyridine-3-carboxamide (Compound 1942), N-[[6-[(2-phenylacetyl)amino]-2-pyridyl]sulfonyl]-6-[1-(2-phenylacetyl)-3,6-dihydro-2H-pyridin-5-yl]-2-[(4S)-2,2,4-trimethylpyrrolidin-1-yl]pyridine-3-carboxamide (Compound 2243), isopropyl N-[6-[[6-(1,2,3,6-tetrahydropyridin-5-yl)-2-[(4S)-2,2,4-trimethylpyrrolidin-1-yl]pyridine-3-carbonyl]sulfamoyl]-2-pyridyl]carbamate (Compound 2624), isopropyl 5-[5-[(6-amino-2-pyridyl)sulfonylcarbamoyl]-6-[(4S)-2,2,4-trimethylpyrrolidin-1-yl]-2-pyridyl]-3,6-dihydro-2H-pyridine-1-carboxylate (Compound 2622), N-[(6-amino-2-pyridyl)sulfonyl]-6-[1-(3,3-dimethylbutanoyl)-3,6-dihydro-2H-pyridin-5-yl]-2-[(4S)-2,2,4-trimethylpyrrolidin-1-yl]pyridine-3-carboxamide (Compound 2650), N-[(6-amino-2-pyridyl)sulfonyl]-6-tert-butyl-5-[1-(2-cyclohexylacetyl)-3,6-dihydro-2H-pyridin-4-yl]-2-[(4S)-2,2,4-trimethylpyrrolidin-1-yl]pyridine-3-carboxamide (Compound 2596), isopropyl 4-[5-[(6-amino-2-pyridyl)sulfonylcarbamoyl]-2-tert-butyl-6-[(4S)-2,2,4-trimethylpyrrolidin-1-yl]-3-pyridyl]-3,6-dihydro-2H-pyridine-1-carboxylate (Compound 2027), N-[(6-amino-2-pyridyl)sulfonyl]-6-tert-butyl-5-[1-(2-phenylacetyl)-3,6-dihydro-2H-pyridin-4-yl]-2-[(4S)-2,2,4-trimethylpyrrolidin-1-yl]pyridine-3-carboxamide (Compound 2417), N-[(6-amino-2-pyridyl)sulfonyl]-6-tert-butyl-5-[1-(3,3-dimethylbutanoyl)-3,6-dihydro-2H-pyridin-4-yl]-2-[(4S)-2,2,4-trimethylpyrrolidin-1-yl]pyridine-3-carboxamide (Compound 2344), N-[(6-amino-2-pyridyl)sulfonyl]-6-[1-(2-cyclohexylacetyl)-3,6-dihydro-2H-pyridin-5-yl]-2-[(4S)-2,2,4-trimethylpyrrolidin-1-yl]pyridine-3-carboxamide (Compound 2633) and, N-[(6-amino-2-pyridyl)sulfonyl]-6-(1-isobutylsulfonyl-3,6-dihydro-2H-pyridin-5-yl)-2-[(4S)-2,2,4-trimethylpyrrolidin-1-yl]pyridine-3-carboxamide (Compound 1882)

Preparation 105: N-[(6-amino-2-pyridyl)sulfonyl]-5-fluoro-6-[(3R)-tetrahydrofuran-3-yl]oxy-2-[(4S)-2,2,4-trimethylpyrrolidin-1-yl]pyridine-3-carboxamide (Compound 2281)

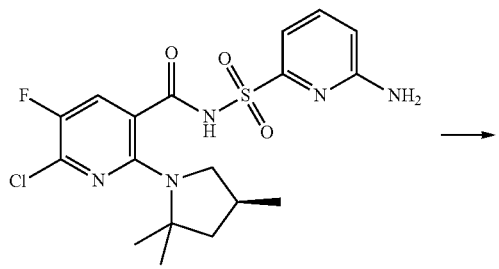

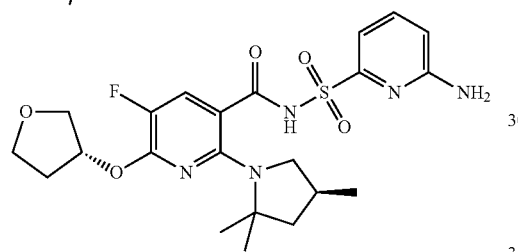

To a 4 mL vial was added NaH (10. mg, 0.25 mmol), (3R)-tetrahydrofuran-3-ol (27.63 mg, 25.19 µL, 0.3136 mmol), and DMSO (800 µL). The mixture was stirred at ambient temperature for 2 minutes. N-[(6-amino-2-pyridyl)sulfonyl]-6-chloro-5-fluoro-2-[(4S)-2,2,4-trimethylpyrrolidin-1-yl]pyridine-3-carboxamide (Hydrochloric Acid (1)) (30. mg, 0.063 mmol) was then added to the vial and the reaction was stirred at 150° C. for 2 hours. The reaction mixture was filtered and purified by preparative HPLC (1-99% acetonitrile over 30 minutes with 5 mM HCl modifier) to give N-[(6-amino-2-pyridyl)sulfonyl]-5-fluoro-6-[(3R)-tetrahydrofuran-3-yl]oxy-2-[(4S)-2,2,4-trimethylpyrrolidin-1-yl]pyridine-3-carboxamide (Compound 2281) (Hydrochloric Acid (1)) (9 mg, 0.02 mmol, 30%) $^1$H NMR (400 MHz, DMSO-$d_6$) δ 12.29 (s, 1H), 7.66-7.57 (m, 2H), 7.17 (d, J=7.3 Hz, 1H), 6.66 (d, J=8.3 Hz, 1H), 6.41 (s, 2H), 5.55-5.48 (m, 1H), 3.94-3.83 (m, 2H), 3.83-3.76 (m, 2H), 2.56 (d, J=10.6 Hz, 1H), 2.44 (t, J=8.7 Hz, 1H), 2.32-2.16 (m, 1H), 2.10-2.02 (m, 1H), 1.84 (dd, J=11.8, 5.6 Hz, 1H), 1.53 (s, 3H), 1.44 (s, 3H), 1.37 (t, J=12.0 Hz, 1H), 0.85 (d, J=6.3 Hz, 3H). ESI-MS m/z calc. 493.1795, found 494.3 (M+1)$^+$; Retention time: 1.08 minutes The following compounds can be synthesized using the procedures described herein N-[(6-amino-2-pyridyl)sulfonyl]-6-[(1R)-1,2-dimethylpropoxy]-5-fluoro-2-[(4S)-2,2,4-trimethylpyrrolidin-1-yl]pyridine-3-carboxamide (Compound 2020), N-[(6-amino-2-pyridyl)sulfonyl]-6-(1-cyclohexylethoxy)-5-fluoro-2-[(4S)-2,2,4-trimethylpyrrolidin-1-yl]pyridine-3-carboxamide (Compound 1730), N-[(6-amino-2-pyridyl)sulfonyl]-5-fluoro-6-[(3S)-tetrahydrofuran-3-yl]oxy-2-[(4S)-2,2,4-trimethylpyrrolidin-1-yl]pyridine-3-carboxamide (Compound 2056), N-[(6-amino-2-pyridyl)sulfonyl]-6-(1-cyclopentylethoxy)-5-fluoro-2-[(4S)-2,2,4-trimethylpyrrolidin-1-yl]pyridine-3-carboxamide (Compound 1966), N-[(6-amino-2-pyridyl)sulfonyl]-5-fluoro-6-(1-tetrahydropyran-4-ylethoxy)-2-[(4S)-2,2,4-trimethylpyrrolidin-1-yl]pyridine-3-carboxamide (Compound 1891), N-[(6-amino-2-pyridyl)sulfonyl]-6-(cyclopentoxy)-5-fluoro-2-[(4S)-2,2,4-trimethylpyrrolidin-1-yl]pyridine-3-carboxamide (Compound 2100), N-[(6-amino-2-pyridyl)sulfonyl]-6-(2,2-dimethylmorpholin-4-yl)-5-fluoro-2-[(4S)-2,2,4-trimethylpyrrolidin-1-yl]pyridine-3-carboxamide (Compound 2586), and N-[(6-amino-2-pyridyl)sulfonyl]-5-fluoro-6-[1-(4-pyridyl)ethoxy]-2-[(4S)-2,2,4-trimethylpyrrolidin-1-yl]pyridine-3-carboxamide (Compound 2212)

Preparation 106: 6-tert-butyl-N-[[6-[(4-methoxyphenyl)methoxy]-2-pyridyl]sulfonyl]-2-(2,2,4-trimethylpyrrolidin-1-yl)pyridine-3-carboxamide (Compound 2724) (Isomer 1) (Compound 2428) (Isomer 2)

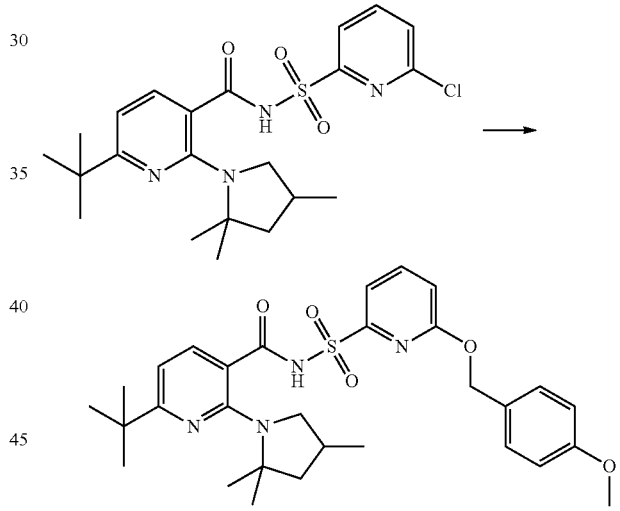

6-(tert-butyl)-N-((6-chloropyridin-2-yl)sulfonyl)-2-(2,2,4-trimethylpyrrolidin-1-yl)nicotinamide (100. mg, 0.215 mmol) and (4-methoxyphenyl)methanol (59.6 mg, 0.431 mmol) were dissolved in anhydrous anhydrous dimethyl sulfoxide (1 mL), and then cesium carbonate (210 mg, 0.645 mmol) was added to the reaction mixture The resulting mixture was heated at 130° C. for 24 hours and cooled to room temperature. Water (10 mL) and aqueous hydrogen chloride solution (1N) was added until pH value of solution was around 2. Reaction solution was extracted with ethyl acetate, and the extract was washed with brine, dried over sodium sulfate and filtered. Solvents were removed under the reduced pressure. The residue obtained was purified by reverse-phase HPLC utilizing a gradient of 0.1% trifluoroacetic acid in water and 0.1% trifluoroacetic acid in acetonitrile. Factions were lyophilized to afford 6-tert-butyl-N-[[6-[(4-methoxyphenyl)methoxy]-2-pyridyl]sulfonyl]-2-(2,2,4-trimethylpyrrolidin-1-yl)pyridine-3-carboxamide (Compound 2724) (Isomer 1) (Compound 2428) (Isomer 2) (35.2 mg, 0.0621 mmol, 28.9%). MS (ESI, m/z): [M+H]$^+$ 567.3.

The following compounds can be synthesized using the procedures described herein N-[[6-[2-(4-fluorophenyl)ethoxy]-2-pyridyl]sulfonyl]-2-(2,2,4-trimethylpyrrolidin-1-yl)pyridine-3-carboxamide (Compound 1704), N-[[6-(3-phenylpyrrolidin-1-yl)-2-pyridyl]sulfonyl]-2-(2,2,4-trimethylpyrrolidin-1-yl)pyridine-3-carboxamide (Compound 1708), N-[[6-[methyl(propyl)amino]-2-pyridyl]sulfonyl]-2-(2,2,4-trimethylpyrrolidin-1-yl)pyridine-3-carboxamide (Compound 1711), N-[[6-[(4-methoxyphenyl)methyl-methyl-amino]-2-pyridyl]sulfonyl]-2-(2,2,4-trimethylpyrrolidin-1-yl)pyridine-3-carboxamide (Compound 1717), N-[(6-tert-butoxy-2-pyridyl)sulfonyl]-2-(2,2,4-trimethylpyrrolidin-1-yl)pyridine-3-carboxamide (Compound 1718), N-[[6-(3-methoxy-5-methyl-phenoxy)-2-pyridyl]sulfonyl]-2-(2,2,4-trimethylpyrrolidin-1-yl)pyridine-3-carboxamide (Compound 1719), N-[[6-(2-cyanophenoxy)-2-pyridyl]sulfonyl]-2-(2,2,4-trimethylpyrrolidin-1-yl)pyridine-3-carboxamide (Compound 1720), N-[[6-(4-isopropylanilino)-2-pyridyl]sulfonyl]-2-(2,2,4-trimethylpyrrolidin-1-yl)pyridine-3-carboxamide (Compound 1722), N-[[6-(4-cyclopentylpiperazin-1-yl)-2-pyridyl]sulfonyl]-2-(2,2,4-trimethylpyrrolidin-1-yl)pyridine-3-carboxamide (Compound 1733), N-[[6-(pyrrolidin-3-ylmethoxy)-2-pyridyl]sulfonyl]-2-(2,2,4-trimethylpyrrolidin-1-yl)pyridine-3-carboxamide (Compound 1734), N-[[6-(4-acetyl-2-methoxy-phenoxy)-2-pyridyl]sulfonyl]-2-(2,2,4-trimethylpyrrolidin-1-yl)pyridine-3-carboxamide (Compound 1744), N-[[6-(3,5-dimethyl-1-piperidyl)-2-pyridyl]sulfonyl]-2-(2,2,4-trimethylpyrrolidin-1-yl)pyridine-3-carboxamide (Compound 1749), N-[[6-(1-naphthyloxy)-2-pyridyl]sulfonyl]-2-(2,2,4-trimethylpyrrolidin-1-yl)pyridine-3-carboxamide (Compound 1751), N-[(6-prop-2-ynoxy-2-pyridyl)sulfonyl]-2-(2,2,4-trimethylpyrrolidin-1-yl)pyridine-3-carboxamide (Compound 1753), N-[[6-(3-phenyl-1-piperidyl)-2-pyridyl]sulfonyl]-2-(2,2,4-trimethylpyrrolidin-1-yl)pyridine-3-carboxamide (Compound 1755), N-[[6-(4-tert-butylanilino)-2-pyridyl]sulfonyl]-2-(2,2,4-trimethylpyrrolidin-1-yl)pyridine-3-carboxamide (Compound 1756), N-[[6-[4-(dimethylamino)anilino]-2-pyridyl]sulfonyl]-2-(2,2,4-trimethylpyrrolidin-1-yl)pyridine-3-carboxamide (Compound 1757), N-[[6-(3,4-dimethoxyphenoxy)-2-pyridyl]sulfonyl]-2-(2,2,4-trimethylpyrrolidin-1-yl)pyridine-3-carboxamide (Compound 1761), N-[[6-(tetrahydrofuran-2-ylmethoxy)-2-pyridyl]sulfonyl]-2-(2,2,4-trimethylpyrrolidin-1-yl)pyridine-3-carboxamide (Compound 1764), N-[[6-(cyclohexylmethoxy)-2-pyridyl]sulfonyl]-2-(2,2,4-trimethylpyrrolidin-1-yl)pyridine-3-carboxamide (Compound 1767), N-[[6-[(2,5-difluorophenyl)methylamino]-2-pyridyl]sulfonyl]-2-(2,2,4-trimethylpyrrolidin-1-yl)pyridine-3-carboxamide (Compound 1770), tert-butyl 4-[6-[[2-(2,2,4-trimethylpyrrolidin-1-yl)pyridine-3-carbonyl]sulfamoyl]-2-pyridyl]piperazine-1-carboxylate (Compound 1773), N-[[6-(1,3-benzothiazol-6-ylamino)-2-pyridyl]sulfonyl]-2-(2,2,4-trimethylpyrrolidin-1-yl)pyridine-3-carboxamide (Compound 1775), N-[[6-(3,4,4a,5,6,7,8,8a-octahydro-2H-quinolin-1-yl)-2-pyridyl]sulfonyl]-2-(2,2,4-trimethylpyrrolidin-1-yl)pyridine-3-carboxamide (Compound 1776), N-[[6-[(5-phenylisoxazol-3-yl)methoxy]-2-pyridyl]sulfonyl]-2-(2,2,4-trimethylpyrrolidin-1-yl)pyridine-3-carboxamide (Compound 1777), N-[[6-[(3-chloro-4-methoxy-phenyl)methoxy]-2-pyridyl]sulfonyl]-2-(2,2,4-trimethylpyrrolidin-1-yl)pyridine-3-carboxamide (Compound 1778), N-[[6-(3-ethynylphenoxy)-2-pyridyl]sulfonyl]-2-(2,2,4-trimethylpyrrolidin-1-yl)pyridine-3-carboxamide (Compound 1782), N-[[6-(2,4,5-trifluoroanilino)-2-pyridyl]sulfonyl]-2-(2,2,4-trimethylpyrrolidin-1-yl)pyridine-3-carboxamide (Compound 1796), N-[[6-[(2-fluorophenyl)methoxy]-2-pyridyl]sulfonyl]-2-(2,2,4-trimethylpyrrolidin-1-yl)pyridine-3-carboxamide (Compound 1798), N-[[6-(2-cyclohexylethoxy)-2-pyridyl]sulfonyl]-2-(2,2,4-trimethylpyrrolidin-1-yl)pyridine-3-carboxamide (Compound 1800), N-[[6-[3-(methoxymethyl)-1-piperidyl]-2-pyridyl]sulfonyl]-2-(2,2,4-trimethylpyrrolidin-1-yl)pyridine-3-carboxamide (Compound 1805), N-[[6-(2,4-dichlorophenoxy)-2-pyridyl]sulfonyl]-2-(2,2,4-trimethylpyrrolidin-1-yl)pyridine-3-carboxamide (Compound 1806), N-[[6-(4-fluorophenoxy)-2-pyridyl]sulfonyl]-2-(2,2,4-trimethylpyrrolidin-1-yl)pyridine-3-carboxamide (Compound 1813), N-[[6-(1,3-benzodioxol-5-ylmethylamino)-2-pyridyl]sulfonyl]-2-(2,2,4-trimethylpyrrolidin-1-yl)pyridine-3-carboxamide (Compound 1814), N-[[6-[4-(2-pyridyl)piperazin-1-yl]-2-pyridyl]sulfonyl]-2-(2,2,4-trimethylpyrrolidin-1-yl)pyridine-3-carboxamide (Compound 1816), N-[[6-(1H-indol-5-ylamino)-2-pyridyl]sulfonyl]-2-(2,2,4-trimethylpyrrolidin-1-yl)pyridine-3-carboxamide (Compound 1823), N-[[6-(8-quinolylamino)-2-pyridyl]sulfonyl]-2-(2,2,4-trimethylpyrrolidin-1-yl)pyridine-3-carboxamide (Compound 1826), N-[[6-[benzyl(methyl)amino]-2-pyridyl]sulfonyl]-2-(2,2,4-trimethylpyrrolidin-1-yl)pyridine-3-carboxamide (Compound 1827), N-[[6-(3-ethoxyphenoxy)-2-pyridyl]sulfonyl]-2-(2,2,4-trimethylpyrrolidin-1-yl)pyridine-3-carboxamide (Compound 1828), N-[[6-(3-chloro-4-fluoro-phenoxy)-2-pyridyl]sulfonyl]-2-(2,2,4-trimethylpyrrolidin-1-yl)pyridine-3-carboxamide (Compound 1831), N-[[6-(1,3,4,9-tetrahydropyrido[3,4-b]indol-2-yl)-2-pyridyl]sulfonyl]-2-(2,2,4-trimethylpyrrolidin-1-yl)pyridine-3-carboxamide (Compound 1833), N-[[6-(cyclopentoxy)-2-pyridyl]sulfonyl]-2-(2,2,4-trimethylpyrrolidin-1-yl)pyridine-3-carboxamide (Compound 1834), N-[(6-isoindolin-2-yl-2-pyridyl)sulfonyl]-2-(2,2,4-trimethylpyrrolidin-1-yl)pyridine-3-carboxamide (Compound 1838), N-[[6-(3-chloroanilino)-2-pyridyl]sulfonyl]-2-(2,2,4-trimethylpyrrolidin-1-yl)pyridine-3-carboxamide (Compound 1841), N-[[6-[(1R)-1-phenylethoxy]-2-pyridyl]sulfonyl]-2-(2,2,4-trimethylpyrrolidin-1-yl)pyridine-3-carboxamide (Compound 1842), N-[[6-[(4-ethyl-2-pyridyl)amino]-2-pyridyl]sulfonyl]-2-(2,2,4-trimethylpyrrolidin-1-yl)pyridine-3-carboxamide (Compound 1862), N-[[6-(thiazol-2-ylmethylamino)-2-pyridyl]sulfonyl]-2-(2,2,4-trimethylpyrrolidin-1-yl)pyridine-3-carboxamide (Compound 1865), N-[[6-[ethyl(2-methoxyethyl)amino]-2-pyridyl]sulfonyl]-2-(2,2,4-trimethylpyrrolidin-1-yl)pyridine-3-carboxamide (Compound 1870), N-[[6-(2-chloroanilino)-2-pyridyl]sulfonyl]-2-(2,2,4-trimethylpyrrolidin-1-yl)pyridine-3-carboxamide (Compound 1872), N-[[6-(3,4-dihydro-2H-pyran-2-ylmethoxy)-2-pyridyl]sulfonyl]-2-(2,2,4-trimethylpyrrolidin-1-yl)pyridine-3-carboxamide (Compound 1874), N-[[6-(7-quinolyloxy)-2-pyridyl]sulfonyl]-2-(2,2,4-trimethylpyrrolidin-1-yl)pyridine-3-carboxamide (Compound 1875), N-[[6-[(1-acetylindolin-5-yl)amino]-2-pyridyl]sulfonyl]-2-(2,2,4-trimethylpyrrolidin-1-yl)pyridine-3-carboxamide (Compound 1877), N-[[6-[3-(N-methylanilino)propylamino]-2-pyridyl]sulfonyl]-2-(2,2,4-trimethylpyrrolidin-1-yl)pyridine-3-carboxamide (Compound 1879), N-[[6-[(E)-but-2-enoxy]-2-pyridyl]sulfonyl]-2-(2,2,4-trimethylpyrrolidin-1-yl)pyridine-3-carboxamide (Compound 1881), N-[[6-(3-methylcyclopentoxy)-2-pyridyl]sulfonyl]-2-(2,2,4-trimethylpyrrolidin-1-yl)pyridine-3-carboxamide (Compound 1884), N-[[6-(p-tolylmethylamino)-2-pyridyl]sulfonyl]-2-(2,2,4-trimethylpyrrolidin-1-yl)pyridine-3-carboxamide (Compound 1892), N-[[6-(2-methylanilino)-2-pyridyl]sulfonyl]-2-(2,2,4-trimethylpyrrolidin-1-yl)pyridine-3-carboxamide (Compound 1898), N-[[6-[(2-chloro-4-fluoro-phenyl)methoxy]-2-pyridyl]sulfonyl]-2-(2,2,4-trimethylpyrrolidin-1-yl)pyridine-3-carboxamide (Compound 1899), N-[[6-(4-isopropylphenoxy)-2-pyridyl]sulfonyl]-2-(2,2,4-trimethylpyrrolidin-1-yl)pyridine-3-carboxamide (Compound 1902), N-[[6-(1-phenylethylamino)-2-pyridyl]sulfonyl]-2-(2,2,4-trimethylpyrrolidin-1-yl)pyridine-3-carboxamide (Compound 1905), N-[[6-(2,3-dichloroanilino)-2-pyridyl]sulfonyl]-2-(2,2,4-trimethylpyrrolidin-1-yl)pyridine-3-carboxamide (Compound 1906), N-[[6-(cyclohexoxy)-2-pyridyl]sulfonyl]-2-(2,2,4-trimethylpyrrolidin-1-yl)pyridine-3-carboxamide (Compound 1908), N-[[6-(indan-5-ylamino)-2-pyridyl]sulfonyl]-2-(2,2,4-trimethylpyrrolidin-1-yl)pyridine-3-carboxamide (Compound 1909), N-[[6-(1-phenylethoxy)-2-pyridyl]sulfonyl]-2-(2,2,4-trimethylpyrrolidin-1-yl)pyridine-3-carboxamide (Compound 1917), N-[[6-(1-cyclohexylethoxy)-2-pyridyl]sulfonyl]-2-(2,2,4-trimethylpyrrolidin-1-yl)pyridine-3-carboxamide (Compound 1919), N-[[6-(4-ethoxyphenoxy)-2-pyridyl]sulfonyl]-2-(2,2,4-trimethylpyrrolidin-1-yl)pyridine-3-carboxamide (Compound 1924), N-[[6-(3-tert-butylphenoxy)-2-pyridyl]sulfonyl]-2-(2,2,4-trimethylpyrrolidin-1-yl)pyridine-3-carboxamide (Compound 1926), N-[[6-[(2,4-dichlorophenyl)methoxy]-2-pyridyl]sulfonyl]-2-(2,2,4-trimethylpyrrolidin-1-yl)pyridine-3-carboxamide (Compound 1929), N-[[6-(azepan-1-yl)-2-pyridyl]sulfonyl]-2-(2,2,4-trimethylpyrrolidin-1-yl)pyridine-3-carboxamide (Compound 1932), N-[[6-(3-isoquinolylamino)-2-pyridyl]sulfonyl]-2-(2,2,4-trimethylpyrrolidin-1-yl)pyridine-3-carboxamide (Compound 1933), N-[[6-(1-methylcyclopentoxy)-2-pyridyl]sulfonyl]-2-(2,2,4-trimethylpyrrolidin-1-yl)pyridine-3-carboxamide (Compound 1936), N-[[6-[4-(1,3-dioxolan-2-ylmethyl)piperazin-1-yl]-2-pyridyl]sulfonyl]-2-(2,2,4-trimethylpyrrolidin-1-yl)pyridine-3-carboxamide (Compound 1937), N-[[6-(benzylamino)-2-pyridyl]sulfonyl]-2-(2,2,4-trimethylpyrrolidin-1-yl)pyridine-3-carboxamide (Compound 1938), N-[[6-(tetrahydropyran-2-ylmethoxy)-2-pyridyl]sulfonyl]-2-(2,2,4-trimethylpyrrolidin-1-yl)pyridine-3-carboxamide (Compound 1939), N-[[6-[(3-methoxyphenyl)methyl-methyl-amino]-2-pyridyl]sulfonyl]-2-(2,2,4-trimethylpyrrolidin-1-yl)pyridine-3-carboxamide (Compound 1940), N-[[6-(2-chloro-5-fluoro-anilino)-2-pyridyl]sulfonyl]-2-(2,2,4-trimethylpyrrolidin-1-yl)pyridine-3-carboxamide (Compound 1941), N-[[6-(3-acetylanilino)-2-pyridyl]sulfonyl]-2-(2,2,4-trimethylpyrrolidin-1-yl)pyridine-3-carboxamide (Compound 1949), N-[[6-[[3-(trifluoromethyl)phenyl]methoxy]-2-pyridyl]sulfonyl]-2-(2,2,4-trimethylpyrrolidin-1-yl)pyridine-3-carboxamide (Compound 1953), N-[(6-tetralin-5-yloxy-2-pyridyl)sulfonyl]-2-(2,2,4-trimethylpyrrolidin-1-yl)pyridine-3-carboxamide (Compound 1955), N-[[6-[(5-chloro-3-pyridyl)oxy]-2-pyridyl]sulfonyl]-2-(2,2,4-trimethylpyrrolidin-1-yl)pyridine-3-carboxamide (Compound 1957), N-[[6-(2-methoxyanilino)-2-pyridyl]sulfonyl]-2-(2,2,4-trimethylpyrrolidin-1-yl)pyridine-3-carboxamide (Compound 1959), N-[[6-[(2-methoxyphenyl)methoxy]-2-pyridyl]sulfonyl]-2-(2,2,4-trimethylpyrrolidin-1-yl)pyridine-3-carboxamide (Compound 1965), N-[[6-[(2,4-dichlorophenyl)methylamino]-2-pyridyl]sulfonyl]-2-(2,2,4-trimethylpyrrolidin-1-yl)pyridine-3-carboxamide (Compound 1968), N-[[6-[(4-tert-butylcyclohexyl)amino]-2-pyridyl]sulfonyl]-2-(2,2,4-trimethylpyrrolidin-1-yl)pyridine-3-carboxamide (Compound 1971), N-[[6-[(3-methoxyphenyl)methoxy]-2-pyridyl]sulfonyl]-2-(2,2,4-trimethylpyrrolidin-1-yl)pyridine-3-carboxamide (Compound 1972), N-[[6-[4-(trifluoromethoxy)anilino]-2-pyridyl]sulfonyl]-2-(2,2,4-trimethylpyrrolidin-1-yl)pyridine-3-carboxamide (Compound 1977), N-[[6-[methyl(phenethyl)amino]-2-pyridyl]sulfonyl]-2-(2,2,4-trimethylpyrrolidin-1-yl)pyridine-3-carboxamide (Compound 1978), N-[[6-[(2-chlorophenyl)methylamino]-2-pyridyl]sulfonyl]-2-(2,2,4-trimethylpyrrolidin-1-yl)pyridine-3-carboxamide (Compound 1983), N-[[6-(4-pentylpiperazin-1-yl)-2-pyridyl]sulfonyl]-2-(2,2,4-trimethylpyrrolidin-1-yl)pyridine-3-carboxamide (Compound 1985), N-[[6-(1,3-dihydrobenzo[de]isoquinolin-2-yl)-2-pyridyl]sulfonyl]-2-(2,2,4-trimethylpyrrolidin-1-yl)pyridine-3-carboxamide (Compound 1986), N-[[6-(4-phenyl-1-piperidyl)-2-pyridyl]sulfonyl]-2-(2,2,4-trimethylpyrrolidin-1-yl)pyridine-3-carboxamide (Compound 1987), N-[[6-(3-methylcyclohexoxy)-2-pyridyl]sulfonyl]-2-(2,2,4-trimethylpyrrolidin-1-yl)pyridine-3-carboxamide (Compound 1988), N-[[6-(2-quinolyloxy)-2-pyridyl]sulfonyl]-2-(2,2,4-trimethylpyrrolidin-1-yl)pyridine-3-carboxamide (Compound 1989), N-[[6-(3-thienylmethoxy)-2-pyridyl]sulfonyl]-2-(2,2,4-trimethylpyrrolidin-1-yl)pyridine-3-carboxamide (Compound 1992), N-[[6-[[(1R)-1-cyclohexylethyl]amino]-2-pyridyl]sulfonyl]-2-(2,2,4-trimethylpyrrolidin-1-yl)pyridine-3-carboxamide (Compound 1996), N-[[6-[(6-methylcyclohex-3-en-1-yl)methoxy]-2-pyridyl]sulfonyl]-2-(2,2,4-trimethylpyrrolidin-1-yl)pyridine-3-carboxamide (Compound 2001), N-[[6-(1H-indol-5-yloxy)-2-pyridyl]sulfonyl]-2-(2,2,4-trimethylpyrrolidin-1-yl)pyridine-3-carboxamide (Compound 2003), N-[[6-(2-thienylmethylamino)-2-pyridyl]sulfonyl]-2-(2,2,4-trimethylpyrrolidin-1-yl)pyridine-3-carboxamide (Compound 2004), N-[[6-[methyl-[2-(3-pyridyl)ethyl]amino]-2-pyridyl]sulfonyl]-2-(2,2,4-trimethylpyrrolidin-1-yl)pyridine-3-carboxamide (Compound 2005), N-[[6-(3,4,4a,5,6,7,8,8a-octahydro-1H-isoquinolin-2-yl)-2-pyridyl]sulfonyl]-2-(2,2,4-trimethylpyrrolidin-1-yl)pyridine-3-carboxamide (Compound 2011), N-[[6-[[3-(dimethylamino)phenyl]methoxy]-2-pyridyl]sulfonyl]-2-(2,2,4-trimethylpyrrolidin-1-yl)pyridine-3-carboxamide (Compound 2012), N-[[6-(1,3-benzodioxol-5-yloxy)-2-pyridyl]sulfonyl]-2-(2,2,4-trimethylpyrrolidin-1-yl)pyridine-3-carboxamide (Compound 2013), N-[[6-(2-fluorophenoxy)-2-pyridyl]sulfonyl]-2-(2,2,4-trimethylpyrrolidin-1-yl)pyridine-3-carboxamide (Compound 2015), N-[[6-(2-cyclohexylpropoxy)-2-pyridyl]sulfonyl]-2-(2,2,4-trimethylpyrrolidin-1-yl)pyridine-3-carboxamide (Compound 2019), N-[[6-(4-phenylanilino)-2-pyridyl]sulfonyl]-2-(2,2,4-trimethylpyrrolidin-1-yl)pyridine-3-carboxamide (Compound 2023), N-[[6-[(2S)-2-(methoxymethyl)pyrrolidin-1-yl]-2-pyridyl]sulfonyl]-2-(2,2,4-trimethylpyrrolidin-1-yl)pyridine-3-carboxamide (Compound 2024), N-[[6-(3,3-dimethylbutoxy)-2-pyridyl]sulfonyl]-2-(2,2,4-trimethylpyrrolidin-1-yl)pyridine-3-carboxamide (Compound 2025), N-[[6-(cyclopentylmethylamino)-2-pyridyl]sulfonyl]-2-(2,2,4-trimethylpyrrolidin-1-yl)pyridine-3-carboxamide (Compound 2026), N-[[6-(3-methyl-1-piperidyl)-2-pyridyl]sulfonyl]-2-(2,2,4-trimethylpyrrolidin-1-yl)pyridine-3-carboxamide (Compound 2030), N-[[6-(tetrahydropyran-4-ylmethoxy)-2-pyridyl]sulfonyl]-2-(2,2,4-trimethylpyrrolidin-1-yl)pyridine-3-carboxamide (Compound 2032), N-[[6-(3,3-dimethylcyclohexoxy)-2-pyridyl]sulfonyl]-2-(2,2,4-trimethylpyrrolidin-1-yl)pyridine-3-carboxamide (Compound 2038), N-[[6-(3,4-dimethoxyanilino)-2-pyridyl]sulfonyl]-2-(2,2,4-trimethylpyrrolidin-1-yl)pyridine-3-carboxamide (Compound 2041), N-[[6-[cyclopropylmethyl(methyl)amino]-2-pyridyl]sulfonyl]-2-(2,2,4-trimethylpyrrolidin-1-yl)pyridine-3-carboxamide (Compound 2044), N-[[6-[1-(1-naphthyl)ethylamino]-2-pyridyl]sulfonyl]-2-(2,2,4-trimethylpyrrolidin-1-yl)pyridine-3-carboxamide (Compound 2049), N-[[6-(cyclopentylamino)-2-pyridyl]sulfonyl]-2-(2,2,4-trimethylpyrrolidin-1-yl)pyridine-3-carboxamide (Compound 2053), N-[[6-[2-(trifluoromethyl)pyrrolidin-1-yl]-2-pyridyl]sulfonyl]-2-(2,2,4-trimethylpyrrolidin-1-yl)pyridine-3-carboxamide (Compound 2055), N-[[6-(1-methylcycloheptoxy)-2-pyridyl]sulfonyl]-2-(2,2,4-trimethylpyrrolidin-1-yl)pyridine-3-carboxamide (Compound 2057), N-[[6-(1,7,7-trimethylnorbornan-2-yl)oxy-2-pyridyl]sulfonyl]-2-(2,2,4-trimethylpyrrolidin-1-yl)pyridine-3-carboxamide (Compound 2059), ethyl 3-[[6-[[2-(2,2,4-trimethylpyrrolidin-1-yl)pyridine-3-carbonyl]sulfamoyl]-2-pyridyl]amino]benzoate (Compound 2060), N-[[6-(3,4-dichlorophenoxy)-2-pyridyl]sulfonyl]-2-(2,2,4-trimethylpyrrolidin-1-yl)pyridine-3-carboxamide (Compound 2061), N-[[6-[(3-chlorophenyl)methylamino]-2-pyridyl]sulfonyl]-2-(2,2,4-trimethylpyrrolidin-1-yl)pyridine-3-carboxamide (Compound 2064), N-[[6-(2-pyridylamino)-2-pyridyl]sulfonyl]-2-(2,2,4-trimethylpyrrolidin-1-yl)pyridine-3-carboxamide (Compound 2068), N-[[6-[2-(4-methoxyphenyl)ethylamino]-2-pyridyl]sulfonyl]-2-(2,2,4-trimethylpyrrolidin-1-yl)pyridine-3-carboxamide (Compound 2072), N-[[6-(5-quinolylamino)-2-pyridyl]sulfonyl]-2-(2,2,4-trimethylpyrrolidin-1-yl)pyridine-3-carboxamide (Compound 2074), N-[(6-isopentyloxy-2-pyridyl)sulfonyl]-2-(2,2,4-trimethylpyrrolidin-1-yl)pyridine-3-carboxamide (Compound 2075), N-[[6-(4-cyanophenoxy)-2-pyridyl]sulfonyl]-2-(2,2,4-trimethylpyrrolidin-1-yl)pyridine-3-carboxamide (Compound 2076), N-[[6-[(3S)-1-benzylpyrrolidin-3-yl]oxy-2-pyridyl]sulfonyl]-2-(2,2,4-trimethylpyrrolidin-1-yl)pyridine-3-carboxamide (Compound 2078), N-[[6-[(4-methyl-2-pyridyl)amino]-2-pyridyl]sulfonyl]-2-(2,2,4-trimethylpyrrolidin-1-yl)pyridine-3-carboxamide (Compound 2082), N-[[6-(2-tert-butylphenoxy)-2-pyridyl]sulfonyl]-2-(2,2,4-trimethylpyrrolidin-1-yl)pyridine-3-carboxamide (Compound 2083), N-[[6-[4-(1-piperidyl)anilino]-2-pyridyl]sulfonyl]-2-(2,2,4-trimethylpyrrolidin-1-yl)pyridine-3-carboxamide (Compound 2087), N-[[6-[(2-methoxyphenyl)methyl-methyl-amino]-2-pyridyl]sulfonyl]-2-(2,2,4-trimethylpyrrolidin-1-yl)pyridine-3-carboxamide (Compound 2090), N-[[6-(2-phenylpyrrolidin-1-yl)-2-pyridyl]sulfonyl]-2-(2,2,4-trimethylpyrrolidin-1-yl)pyridine-3-carboxamide (Compound 2094), N-[[6-(3,4-dihydro-1H-isoquinolin-2-yl)-2-pyridyl]sulfonyl]-2-(2,2,4-trimethylpyrrolidin-1-yl)pyridine-3-carboxamide (Compound 2098), N-[[6-[(2,4-difluorophenyl)methoxy]-2-pyridyl]sulfonyl]-2-(2,2,4-trimethylpyrrolidin-1-yl)pyridine-3-carboxamide (Compound 2099), N-[[6-(4-fluoroanilino)-2-pyridyl]sulfonyl]-2-(2,2,4-trimethylpyrrolidin-1-yl)pyridine-3-carboxamide (Compound 2102), N-[[6-(2,4,6-trifluoroanilino)-2-pyridyl]sulfonyl]-2-(2,2,4-trimethylpyrrolidin-1-yl)pyridine-3-carboxamide (Compound 2106), N-[[6-(4-benzyl-1-piperidyl)-2-pyridyl]sulfonyl]-2-(2,2,4-trimethylpyrrolidin-1-yl)pyridine-3-carboxamide (Compound 2107), N-[[6-(3-isopropylphenoxy)-2-pyridyl]sulfonyl]-2-(2,2,4-trimethylpyrrolidin-1-yl)pyridine-3-carboxamide (Compound 2108), N-[[6-[(1S,2S)-2-methylcyclopentoxy]-2-pyridyl]sulfonyl]-2-(2,2,4-trimethylpyrrolidin-1-yl)pyridine-3-carboxamide (Compound 2109), N-[[6-[(1-phenylpyrazol-4-yl)methoxy]-2-pyridyl]sulfonyl]-2-(2,2,4-trimethylpyrrolidin-1-yl)pyridine-3-carboxamide (Compound 2111), N-[[6-(2,3-dihydro-1,4-benzodioxin-3-ylmethoxy)-2-pyridyl]sulfonyl]-2-(2,2,4-trimethylpyrrolidin-1-yl)pyridine-3-carboxamide (Compound 2115), N-[[6-(3-methylpyrrolidin-1-yl)-2-pyridyl]sulfonyl]-2-(2,2,4-trimethylpyrrolidin-1-yl)pyridine-3-carboxamide (Compound 2116), N-[[6-[(4-pyrazol-1-ylphenyl)methoxy]-2-pyridyl]sulfonyl]-2-(2,2,4-trimethylpyrrolidin-1-yl)pyridine-3-carboxamide (Compound 2118), N-[[6-(4-phenylbutylamino)-2-pyridyl]sulfonyl]-2-(2,2,4-trimethylpyrrolidin-1-yl)pyridine-3-carboxamide (Compound 2119), ethyl 4-[[6-[[2-(2,2,4-trimethylpyrrolidin-1-yl)pyridine-3-carbonyl]sulfamoyl]-2-pyridyl]amino]benzoate (Compound 2122), N-[[6-(3-benzylpyrrolidin-1-yl)-2-pyridyl]sulfonyl]-2-(2,2,4-trimethylpyrrolidin-1-yl)pyridine-3-carboxamide (Compound 2123), N-[[6-(1,1-dimethylbutoxy)-2-pyridyl]sulfonyl]-2-(2,2,4-trimethylpyrrolidin-1-yl)pyridine-3-carboxamide (Compound 2130), N-[[6-(tetrahydrofuran-2-ylmethylamino)-2-pyridyl]sulfonyl]-2-(2,2,4-trimethylpyrrolidin-1-yl)pyridine-3-carboxamide (Compound 2131), N-[[6-(3-methoxypropylamino)-2-pyridyl]sulfonyl]-2-(2,2,4-trimethylpyrrolidin-1-yl)pyridine-3-carboxamide (Compound 2135), N-[[6-(1-naphthylamino)-2-pyridyl]sulfonyl]-2-(2,2,4-trimethylpyrrolidin-1-yl)pyridine-3-carboxamide (Compound 2136), N-[[6-(2-methyl-2-pyrrol-1-yl-propoxy)-2-pyridyl]sulfonyl]-2-(2,2,4-trimethylpyrrolidin-1-yl)pyridine-3-carboxamide (Compound 2137), methyl 6-[[6-[[2-(2,2,4-trimethylpyrrolidin-1-yl)pyridine-3-carbonyl]sulfamoyl]-2-pyridyl]amino]pyridine-3-carboxylate (Compound 2140), N-[[6-(3-tert-butylanilino)-2-pyridyl]sulfonyl]-2-(2,2,4-trimethylpyrrolidin-1-yl)pyridine-3-carboxamide (Compound 2142), N-[[6-[3-(trifluoromethoxy)anilino]-2-pyridyl]sulfonyl]-2-(2,2,4-trimethylpyrrolidin-1-yl)pyridine-3-carboxamide (Compound 2143), N-[[6-(4-chlorophenoxy)-2-pyridyl]sulfonyl]-2-(2,2,4-trimethylpyrrolidin-1-yl)pyridine-3-carboxamide (Compound 2145), N-[[6-[2-(2-thienyl)ethylamino]-2-pyridyl]sulfonyl]-2-(2,2,4-trimethylpyrrolidin-1-yl)pyridine-3-carboxamide (Compound 2146), N-[(6-cyclohex-2-en-1-yloxy-2-pyridyl)sulfonyl]-2-(2,2,4-trimethylpyrrolidin-1-yl)pyridine-3-carboxamide (Compound 2147), N-[[6-(2-naphthylmethoxy)-2-pyridyl]sulfonyl]-2-(2,2,4-trimethylpyrrolidin-1-yl)pyridine-3-carboxamide (Compound 2151), N-[[6-(3-methoxy-1-piperidyl)-2-pyridyl]sulfonyl]-2-(2,2,4-trimethylpyrrolidin-1-yl)pyridine-3-carboxamide (Compound 2152), N-[[6-[(4,6-dimethyl-2-pyridyl)amino]-2-pyridyl]sulfonyl]-2-(2,2,4-trimethylpyrrolidin-1-yl)pyridine-3-carboxamide (Compound 2160), N-[[6-[2-(3-thienyl)ethoxy]-2-pyridyl]sulfonyl]-2-(2,2,4-trimethylpyrrolidin-1-yl)pyridine-3-carboxamide (Compound 2161), N-[[6-(3-chloro-2-fluoro-phenoxy)-2-pyridyl]sulfonyl]-2-(2,2,4-trimethylpyrrolidin-1-yl)pyridine-3-carboxamide (Compound 2165), N-[[6-(3,3-difluoropyrrolidin-1-yl)-2-pyridyl]sulfonyl]-2-(2,2,4-trimethylpyrrolidin-1-yl)pyridine-3-carboxamide (Compound 2166), N-[(6-butoxy-2-pyridyl)sulfonyl]-2-(2,2,4-trimethylpyrrolidin-1-yl)pyridine-3-carboxamide (Compound 2167), N-[[6-[(3-methoxyphenyl)methylamino]-2-pyridyl]sulfonyl]-2-(2,2,4-trimethylpyrrolidin-1-yl)pyridine-3-carboxamide (Compound 2168), N-[[6-(1,3-benzodioxol-5-ylmethoxy)-2-pyridyl]sulfonyl]-2-(2,2,4-trimethylpyrrolidin-1-yl)pyridine-3-carboxamide (Compound 2169), N-[[6-(4-isopropylcyclohexoxy)-2-pyridyl]sulfonyl]-2-(2,2,4-trimethylpyrrolidin-1-yl)pyridine-3-carboxamide (Compound 2173), N-[[6-[4-(4-pyridylmethyl)piperazin-1-yl]-2-pyridyl]sulfonyl]-2-(2,2,4-trimethylpyrrolidin-1-yl)pyridine-3-carboxamide (Compound 2175), N-[[6-(3-chloro-5-cyano-phenoxy)-2-pyridyl]sulfonyl]-2-(2,2,4-trimethylpyrrolidin-1-yl)pyridine-3-carboxamide (Compound 2177), N-[[6-(2,5-dimethoxyanilino)-2-pyridyl]sulfonyl]-2-(2,2,4-trimethylpyrrolidin-1-yl)pyridine-3-carboxamide (Compound 2179), N-[[6-(2-thienylmethoxy)-2-pyridyl]sulfonyl]-2-(2,2,4-trimethylpyrrolidin-1-yl)pyridine-3-carboxamide (Compound 2181), N-[[6-[(4-chloro-2-fluoro-phenyl)methoxy]-2-pyridyl]sulfonyl]-2-(2,2,4-trimethylpyrrolidin-1-yl)pyridine-3-carboxamide (Compound 2182), N-[[6-[(1S)-1-phenylethoxy]-2-pyridyl]sulfonyl]-2-(2,2,4-trimethylpyrrolidin-1-yl)pyridine-3-carboxamide (Compound 2186), N-[[6-[(4-isopropylphenyl)methylamino]-2-pyridyl]sulfonyl]-2-(2,2,4-trimethylpyrrolidin-1-yl)pyridine-3-carboxamide (Compound 2187), N-[[6-(cyclobutylmethoxy)-2-pyridyl]sulfonyl]-2-(2,2,4-trimethylpyrrolidin-1-yl)pyridine-3-carboxamide (Compound 2188), N-[[6-(2,3-dihydro-1,4-benzodioxin-6-ylamino)-2-pyridyl]sulfonyl]-2-(2,2,4-trimethylpyrrolidin-1-yl)pyridine-3-carboxamide (Compound 2190), N-[[6-[(1-methylindol-5-yl)amino]-2-pyridyl]sulfonyl]-2-(2,2,4-trimethylpyrrolidin-1-yl)pyridine-3-carboxamide (Compound 2193), N-[[6-(1-methylbutylamino)-2-pyridyl]sulfonyl]-2-(2,2,4-trimethylpyrrolidin-1-yl)pyridine-3-carboxamide (Compound 2197), N-[[6-[(2-methyl-1,3-benzothiazol-5-yl)amino]-2-pyridyl]sulfonyl]-2-(2,2,4-trimethylpyrrolidin-1-yl)pyridine-3-carboxamide (Compound 2198), N-[[6-(isopropylamino)-2-pyridyl]sulfonyl]-2-(2,2,4-trimethylpyrrolidin-1-yl)pyridine-3-carboxamide (Compound 2200), N-[[6-(cyclooctylamino)-2-pyridyl]sulfonyl]-2-(2,2,4-trimethylpyrrolidin-1-yl)pyridine-3-carboxamide (Compound 2202), N-[[6-(2-phenoxyethylamino)-2-pyridyl]sulfonyl]-2-(2,2,4-trimethylpyrrolidin-1-yl)pyridine-3-carboxamide (Compound 2206), N-[[6-(4-phenylpiperazin-1-yl)-2-pyridyl]sulfonyl]-2-(2,2,4-trimethylpyrrolidin-1-yl)pyridine-3-carboxamide (Compound 2208), N-[(6-decalin-2-yloxy-2-pyridyl)sulfonyl]-2-(2,2,4-trimethylpyrrolidin-1-yl)pyridine-3-carboxamide (Compound 2211), N-[[6-(4-ethoxyanilino)-2-pyridyl]sulfonyl]-2-(2,2,4-trimethylpyrrolidin-1-yl)pyridine-3-carboxamide (Compound 2214), N-[[6-(2,4-dichloroanilino)-2-pyridyl]sulfonyl]-2-(2,2,4-trimethylpyrrolidin-1-yl)pyridine-3-carboxamide (Compound 2217), N-[[6-[(2-methylcyclohexyl)amino]-2-pyridyl]sulfonyl]-2-(2,2,4-trimethylpyrrolidin-1-yl)pyridine-3-carboxamide (Compound 2218), N-[[6-[1-(methoxymethyl)propylamino]-2-pyridyl]sulfonyl]-2-(2,2,4-trimethylpyrrolidin-1-yl)pyridine-3-carboxamide (Compound 2221), N-[[6-[4-(1-methylbutyl)piperazin-1-yl]-2-pyridyl]sulfonyl]-2-(2,2,4-trimethylpyrrolidin-1-yl)pyridine-3-carboxamide (Compound 2226), N-[[6-(2,3-dimethoxyphenoxy)-2-pyridyl]sulfonyl]-2-(2,2,4-trimethylpyrrolidin-1-yl)pyridine-3-carboxamide (Compound 2233), N-[[6-(4-methoxyphenoxy)-2-pyridyl]sulfonyl]-2-(2,2,4-trimethylpyrrolidin-1-yl)pyridine-3-carboxamide (Compound 2239), N-[[6-(1,3-benzodioxol-4-ylmethoxy)-2-pyridyl]sulfonyl]-2-(2,2,4-trimethylpyrrolidin-1-yl)pyridine-3-carboxamide (Compound 2249), N-[[6-(cyclohexylamino)-2-pyridyl]sulfonyl]-2-(2,2,4-trimethylpyrrolidin-1-yl)pyridine-3-carboxamide (Compound 2250), tert-butyl 2-[methyl-[6-[[2-(2,2,4-trimethylpyrrolidin-1-yl)pyridine-3-carbonyl]sulfamoyl]-2-pyridyl]amino]acetate (Compound 2251), N-[[6-(cycloheptoxy)-2-pyridyl]sulfonyl]-2-(2,2,4-trimethylpyrrolidin-1-yl)pyridine-3-carboxamide (Compound 2252), ethyl 4-[[6-[[2-(2,2,4-trimethylpyrrolidin-1-yl)pyridine-3-carbonyl]sulfamoyl]-2-pyridyl]amino]piperidine-1-carboxylate (Compound 2253), N-[[6-(4-pyrazin-2-ylpiperazin-1-yl)-2-pyridyl]sulfonyl]-2-(2,2,4-trimethylpyrrolidin-1-yl)pyridine-3-carboxamide (Compound 2254), N-[(6-indolin-1-yl-2-pyridyl)sulfonyl]-2-(2,2,4-trimethylpyrrolidin-1-yl)pyridine-3-carboxamide (Compound 2255), N-[[6-(6-methoxy-3,4-dihydro-1H-isoquinolin-2-yl)-2-pyridyl]sulfonyl]-2-(2,2,4-trimethylpyrrolidin-1-yl)pyridine-3-carboxamide (Compound 2260), N-[[6-[[2-(trifluoromethyl)phenyl]methoxy]-2-pyridyl]sulfonyl]-2-(2,2,4-trimethylpyrrolidin-1-yl)pyridine-3-carboxamide (Compound 2261), N-[[6-[2-(4-chlorophenyl)ethylamino]-2-pyridyl]sulfonyl]-2-(2,2,4-trimethylpyrrolidin-1-yl)pyridine-3-carboxamide (Compound 2262), N-[[6-[3-(5-methyl-1,2,4-oxadiazol-3-yl)phenoxy]-2-pyridyl]sulfonyl]-2-(2,2,4-trimethylpyrrolidin-1-yl)pyridine-3-carboxamide (Compound 2263), N-[[6-[(3-chlorophenyl)methoxy]-2-pyridyl]sulfonyl]-2-(2,2,4-trimethylpyrrolidin-1-yl)pyridine-3-carboxamide (Compound 2264), N-[[6-(1-naphthylmethoxy)-2-pyridyl]sulfonyl]-2-(2,2,4-trimethylpyrrolidin-1-yl)pyridine-3-carboxamide (Compound 2270), N-[[6-[(2-chlorophenyl)methoxy]-2-pyridyl]sulfonyl]-2-(2,2,4-trimethylpyrrolidin-1-yl)pyridine-3-carboxamide (Compound 2273), N-[[6-(5-isoquinolylamino)-2-pyridyl]sulfonyl]-2-(2,2,4-trimethylpyrrolidin-1-yl)pyridine-3-carboxamide (Compound 2274), N-[[6-(3,5-difluoroanilino)-2-pyridyl]sulfonyl]-2-(2,2,4-trimethylpyrrolidin-1-yl)pyridine-3-carboxamide (Compound 2282), N-[[6-[4-(6-methyl-2-pyridyl)piperazin-1-yl]-2-pyridyl]sulfonyl]-2-(2,2,4-trimethylpyrrolidin-1-yl)pyridine-3-carboxamide (Compound 2285), N-[[6-[(4-tert-butylphenyl)methoxy]-2-pyridyl]sulfonyl]-2-(2,2,4-trimethylpyrrolidin-1-yl)pyridine-3-carboxamide (Compound 2286), N-[[6-[4-(trifluoromethyl)anilino]-2-pyridyl]sulfonyl]-2-(2,2,4-trimethylpyrrolidin-1-yl)pyridine-3-carboxamide (Compound 2292), N-[[6-(3,5-dimethoxyphenoxy)-2-pyridyl]sulfonyl]-2-(2,2,4-trimethylpyrrolidin-1-yl)pyridine-3-carboxamide (Compound 2293), N-[[6-[(6-methyl-2-pyridyl)methoxy]-2-pyridyl]sulfonyl]-2-(2,2,4-trimethylpyrrolidin-1-yl)pyridine-3-carboxamide (Compound 2294), N-[[6-(3-benzyl-1-piperidyl)-2-pyridyl]sulfonyl]-2-(2,2,4-trimethylpyrrolidin-1-yl)pyridine-3-carboxamide (Compound 2297), N-[[6-(2-chlorophenoxy)-2-pyridyl]sulfonyl]-2-(2,2,4-trimethylpyrrolidin-1-yl)pyridine-3-carboxamide (Compound 2298), N-[[6-[(3-cyanophenyl)methoxy]-2-pyridyl]sulfonyl]-2-(2,2,4-trimethylpyrrolidin-1-yl)pyridine-3-carboxamide (Compound 2299), N-[[6-(2-ethylbutylamino)-2-pyridyl]sulfonyl]-2-(2,2,4-trimethylpyrrolidin-1-yl)pyridine-3-carboxamide (Compound 2305), N-[[6-[butyl(methyl)amino]-2-pyridyl]sulfonyl]-2-(2,2,4-trimethylpyrrolidin-1-yl)pyridine-3-carboxamide (Compound 2307), N-[[6-(2-furylmethoxy)-2-pyridyl]sulfonyl]-2-(2,2,4-trimethylpyrrolidin-1-yl)pyridine-3-carboxamide (Compound 2308), N-[[6-(2,6-dimethoxyphenoxy)-2-pyridyl]sulfonyl]-2-(2,2,4-trimethylpyrrolidin-1-yl)pyridine-3-carboxamide (Compound 2309), N-[[6-[(2-methoxyphenyl)methylamino]-2-pyridyl]sulfonyl]-2-(2,2,4-trimethylpyrrolidin-1-yl)pyridine-3-carboxamide (Compound 2310), N-[[6-(4-aminophenoxy)-2-pyridyl]sulfonyl]-2-(2,2,4-trimethylpyrrolidin-1-yl)pyridine-3-carboxamide (Compound 2314), N-[[6-(3-cyano-4-fluoro-anilino)-2-pyridyl]sulfonyl]-2-(2,2,4-trimethylpyrrolidin-1-yl)pyridine-3-carboxamide (Compound 2316), N-[(6-cyclopent-3-en-1-yloxy-2-pyridyl)sulfonyl]-2-(2,2,4-trimethylpyrrolidin-1-yl)pyridine-3-carboxamide (Compound 2317), N-[[6-[[(1R)-1,2-dimethylpropyl]amino]-2-pyridyl]sulfonyl]-2-(2,2,4-trimethylpyrrolidin-1-yl)pyridine-3-carboxamide (Compound 2318), N-[[6-(3-methylphenoxy)-2-pyridyl]sulfonyl]-2-(2,2,4-trimethylpyrrolidin-1-yl)pyridine-3-carboxamide (Compound 2320), (3S)-2-[6-[[2-(2,2,4-trimethylpyrrolidin-1-yl)pyridine-3-carbonyl]sulfamoyl]-2-pyridyl]-3,4-dihydro-1H-isoquinoline-3-carboxylic acid (Compound 2321), N-[[6-(2-methylmorpholin-4-yl)-2-pyridyl]sulfonyl]-2-(2,2,4-trimethylpyrrolidin-1-yl)pyridine-3-carboxamide (Compound 2324), N-[[6-(4-acetylanilino)-2-pyridyl]sulfonyl]-2-(2,2,4-trimethylpyrrolidin-1-yl)pyridine-3-carboxamide (Compound 2328), N-[[6-(2-tetrahydropyran-4-ylethoxy)-2-pyridyl]sulfonyl]-2-(2,2,4-trimethylpyrrolidin-1-yl)pyridine-3-carboxamide (Compound 2329), N-[[6-(4-methyl-1-piperidyl)-2-pyridyl]sulfonyl]-2-(2,2,4-trimethylpyrrolidin-1-yl)pyridine-3-carboxamide (Compound 2330), N-[[6-(3-fluorophenoxy)-2=pyridyl]sulfonyl]-2-(2,2,4-trimethylpyrrolidin-1-yl)pyridine-3-carboxamide (Compound 2332), N-[[6-(8-quinolyloxy)-2-pyridyl]sulfonyl]-2-(2,2,4-trimethylpyrrolidin-1-yl)pyridine-3-carboxamide (Compound 2333), tert-butyl N-[4-[[6-[[2-(2,2,4-trimethylpyrrolidin-1-yl)pyridine-3-carbonyl]sulfamoyl]-2-pyridyl]amino]butyl]carbamate (Compound 2335), N-[[6-(4-methylcyclohexoxy)-2-pyridyl]sulfonyl]-2-(2,2,4-trimethylpyrrolidin-1-yl)pyridine-3-carboxamide (Compound 2336), N-[[6-(1H-indol-4-yloxy)-2-pyridyl]sulfonyl]-2-(2,2,4-trimethylpyrrolidin-1-yl)pyridine-3-carboxamide (Compound 2338), N-[[6-(3,3a,4,5,6,6a-hexahydro-1H-cyclopenta[c]pyrrol-2-yl)-2-pyridyl]sulfonyl]-2-(2,2,4-trimethylpyrrolidin-1-yl)pyridine-3-carboxamide (Compound 2340), N-[[6-(3,4-difluoroanilino)-2-pyridyl]sulfonyl]-2-(2,2,4-trimethylpyrrolidin-1-yl)pyridine-3-carboxamide (Compound 2341), N-[[6-(cyclopropylmethoxy)-2-pyridyl]sulfonyl]-2-(2,2,4-trimethylpyrrolidin-1-yl)pyridine-3-carboxamide (Compound 2342), N-[[6-[2-methoxyethyl(propyl)amino]-2-pyridyl]sulfonyl]-2-(2,2,4-trimethylpyrrolidin-1-yl)pyridine-3-carboxamide (Compound 2343), N-[[6-[isopentyl(methyl)amino]-2-pyridyl]sulfonyl]-2-(2,2,4-trimethylpyrrolidin-1-yl)pyridine-3-carboxamide (Compound 2346), N-[[6-(2,2-difluoroethylamino)-2-pyridyl]sulfonyl]-2-(2,2,4-trimethylpyrrolidin-1-yl)pyridine-3-carboxamide (Compound 2350), N-[[6-(3-isopropoxyanilino)-2-pyridyl]sulfonyl]-2-(2,2,4-trimethylpyrrolidin-1-yl)pyridine-3-carboxamide (Compound 2353), N-[[6-(2-ethoxyethylamino)-2-pyridyl]sulfonyl]-2-(2,2,4-trimethylpyrrolidin-1-yl)pyridine-3-carboxamide (Compound 2354), N-[[6-(3,5-dimethoxyanilino)-2-pyridyl]sulfonyl]-2-(2,2,4-trimethylpyrrolidin-1-yl)pyridine-3-carboxamide (Compound 2357), N-[[6-[2-(2-pyridyl)ethylamino]-2-pyridyl]sulfonyl]-2-(2,2,4-trimethylpyrrolidin-1-yl)pyridine-3-carboxamide (Compound 2359), N-[[6-[[6-(trifluoromethyl)-2-pyridyl]methylamino]-2-pyridyl]sulfonyl]-2-(2,2,4-trimethylpyrrolidin-1-yl)pyridine-3-carboxamide (Compound 2365), N-[[6-(cyclobutoxy)-2-pyridyl]sulfonyl]-2-(2,2,4-trimethylpyrrolidin-1-yl)pyridine-3-carboxamide (Compound 2371), N-[[6-[(3-chlorophenyl)methyl-methyl-amino]-2-pyridyl]sulfonyl]-2-(2,2,4-trimethylpyrrolidin-1-yl)pyridine-3-carboxamide (Compound 2378), N-[[6-[3-(trifluoromethyl)anilino]-2-pyridyl]sulfonyl]-2-(2,2,4-trimethylpyrrolidin-1-yl)pyridine-3-carboxamide (Compound 2381), N-[[6-(3,4-dihydro-2H-quinolin-1-yl)-2-pyridyl]sulfonyl]-2-(2,2,4-trimethylpyrrolidin-1-yl)pyridine-3-carboxamide (Compound 2382), N-[[6-[4-(2-dimethylaminoethyl)-1-piperidyl]-2-pyridyl]sulfonyl]-2-(2,2,4-trimethylpyrrolidin-1-yl)pyridine-3-carboxamide (Compound 2383), N-[[6-(5-chloroindolin-1-yl)-2-pyridyl]sulfonyl]-2-(2,2,4-trimethylpyrrolidin-1-yl)pyridine-3-carboxamide (Compound 2385), N-[[6-(3-acetamidoanilino)-2-pyridyl]sulfonyl]-2-(2,2,4-trimethylpyrrolidin-1-yl)pyridine-3-carboxamide (Compound 2387), N-[[6-(1H-indazol-5-ylamino)-2-pyridyl]sulfonyl]-2-(2,2,4-trimethylpyrrolidin-1-yl)pyridine-3-carboxamide (Compound 2389), N-[[6-[(2,6-dichlorophenyl)methoxy]-2-pyridyl]sulfonyl]-2-(2,2,4-trimethylpyrrolidin-1-yl)pyridine-3-carboxamide (Compound 2390), N-[[6-(m-tolylmethylamino)-2-pyridyl]sulfonyl]-2-(2,2,4-trimethylpyrrolidin-1-yl)pyridine-3-carboxamide (Compound 2391), N-[[6-[(3S)-3-fluoropyrrolidin-1-yl]-2-pyridyl]sulfonyl]-2-(2,2,4-trimethylpyrrolidin-1-yl)pyridine-3-carboxamide (Compound 2393), N-[[6-(tetrahydrofuran-3-ylmethoxy)-2-pyridyl]sulfonyl]-2-(2,2,4-trimethylpyrrolidin-1-yl)pyridine-3-carboxamide (Compound 2396), N-[[6-[2-(trifluoromethyl)anilino]-2-pyridyl]sulfonyl]-2-(2,2,4-trimethylpyrrolidin-1-yl)pyridine-3-carboxamide (Compound 2397), tert-butyl N-methyl-N-[2-[[6-[[2-(2,2,4-trimethylpyrrolidin-1-yl)pyridine-3-carbonyl]sulfamoyl]-2-pyridyl]amino]ethyl]carbamate (Compound 2400), N-[[6-[(3,4-dichlorophenyl)methoxy]-2-pyridyl]sulfonyl]-2-(2,2,4-trimethylpyrrolidin-1-yl)pyridine-3-carboxamide (Compound 2402), N-[[6-[(1-benzylpyrrolidin-3-yl)amino]-2-pyridyl]sulfonyl]-2-(2,2,4-trimethylpyrrolidin-1-yl)pyridine-3-carboxamide (Compound 2407), N-[[6-[1-(2-fluorophenyl)ethoxy]-2-pyridyl]sulfonyl]-2-(2,2,4-trimethylpyrrolidin-1-yl)pyridine-3-carboxamide (Compound 2408), N-[[6-[(3-fluorophenyl)methoxy]-2-pyridyl]sulfonyl]-2-(2,2,4-trimethylpyrrolidin-1-yl)pyridine-3-carboxamide (Compound 2409), N-[[6-(2,2-dimethylpropoxy)-2-pyridyl]sulfonyl]-2-(2,2,4-trimethylpyrrolidin-1-yl)pyridine-3-carboxamide (Compound 2412), N-[[6-[(4-isopropylphenyl)methoxy]-2-pyridyl]sulfonyl]-2-(2,2,4-trimethylpyrrolidin-1-yl)pyridine-3-carboxamide (Compound 2415), N-[[6-[(6-methoxy-2-pyridyl)amino]-2-pyridyl]sulfonyl]-2-(2,2,4-trimethylpyrrolidin-1-yl)pyridine-3-carboxamide (Compound 2420), N-[[6-[(3,5-difluorophenyl)methylamino]-2-pyridyl]sulfonyl]-2-(2,2,4-trimethylpyrrolidin-1-yl)pyridine-3-carboxamide (Compound 2421), N-[[6-(4-hexylpiperazin-1-yl)-2-pyridyl]sulfonyl]-2-(2,2,4-trimethylpyrrolidin-1-yl)pyridine-3-carboxamide (Compound 2423), N-[[6-[(4-methoxyphenyl)methoxy]-2-pyridyl]sulfonyl]-2-(2,2,4-trimethylpyrrolidin-1-yl)pyridine-3-carboxamide (Compound 2428), N-[(6-methoxy-2-pyridyl)sulfonyl]-2-(2,2,4-trimethylpyrrolidin-1-yl)pyridine-3-carboxamide (Compound 2430), N-[[6-(3-acetamidophenoxy)-2-pyridyl]sulfonyl]-2-(2,2,4-trimethylpyrrolidin-1-yl)pyridine-3-carboxamide (Compound 2433), N-[[6-[(1-methylcyclopropyl)methoxy]-2-pyridyl]sulfonyl]-2-(2,2,4-trimethylpyrrolidin-1-yl)pyridine-3-carboxamide (Compound 2434), tert-butyl N-[4-[[6-[[2-(2,2,4-trimethylpyrrolidin-1-yl)pyridine-3-carbonyl]sulfamoyl]-2-pyridyl]amino]cyclohexyl]carbamate (Compound 2439), N-[[6-(4-imidazol-1-ylphenoxy)-2-pyridyl]sulfonyl]-2-(2,2,4-trimethylpyrrolidin-1-yl)pyridine-3-carboxamide (Compound 2441), methyl 1-[6-[[2-(2,2,4-trimethylpyrrolidin-1-yl)pyridine-3-carbonyl]sulfamoyl]-2-pyridyl]piperidine-4-carboxylate (Compound 2442), N-[[6-[3-(dimethylamino)phenoxy]-2-pyridyl]sulfonyl]-2-(2,2,4-trimethylpyrrolidin-1-yl)pyridine-3-carboxamide (Compound 2443), N-[[6-(3-quinolylamino)-2-pyridyl]sulfonyl]-2-(2,2,4-trimethylpyrrolidin-1-yl)pyridine-3-carboxamide (Compound 2449), N-[[6-[2-(4-piperidyl)ethoxy]-2-pyridyl]sulfonyl]-2-(2,2,4-trimethylpyrrolidin-1-yl)pyridine-3-carboxamide (Compound 2452), N-[[6-(4-fluoro-1-piperidyl)-2-pyridyl]sulfonyl]-2-(2,2,4-trimethylpyrrolidin-1-yl)pyridine-3-carboxamide (Compound 2453), N-[[6-(4-methylphenoxy)-2-pyridyl]sulfonyl]-2-(2,2,4-trimethylpyrrolidin-1-yl)pyridine-3-carboxamide (Compound 2460), N-[[6-(3-chlorophenoxy)-2-pyridyl]sulfonyl]-2-(2,2,4-trimethylpyrrolidin-1-yl)pyridine-3-carboxamide (Compound 2461), N-[[6-[(3,5-difluorophenyl)methoxy]-2-pyridyl]sulfonyl]-2-(2,2,4-trimethylpyrrolidin-1-yl)pyridine-3-carboxamide (Compound 2462), N-[(6-morpholino-2-pyridyl)sulfonyl]-2-(2,2,4-trimethylpyrrolidin-1-yl)pyridine-3-carboxamide (Compound 2464), N-[[6-[2-(3-methoxyphenyl)ethylamino]-2-pyridyl]sulfonyl]-2-(2,2,4-trimethylpyrrolidin-1-yl)pyridine-3-carboxamide (Compound 2465), N-[[6-[[6-(trifluoromethyl)-3-pyridyl]amino]-2-pyridyl]sulfonyl]-2-(2,2,4-trimethylpyrrolidin-1-yl)pyridine-3-carboxamide (Compound 2466), N-[[6-[(1R)-1-methyl-2-phenyl-ethoxy]-2-pyridyl]sulfonyl]-2-(2,2,4-trimethylpyrrolidin-1-yl)pyridine-3-carboxamide (Compound 2470), N-[[6-[[6-(trifluoromethyl)-3-pyridyl]methoxy]-2-pyridyl]sulfonyl]-2-(2,2,4-trimethylpyrrolidin-1-yl)pyridine-3-carboxamide (Compound 2476), N-[[6-(3-cyanoanilino)-2-pyridyl]sulfonyl]-2-(2,2,4-trimethylpyrrolidin-1-yl)pyridine-3-carboxamide (Compound 2484), N-[[6-(2-isopropylphenoxy)-2-pyridyl]sulfonyl]-2-(2,2,4-trimethylpyrrolidin-1-yl)pyridine-3-carboxamide (Compound 2486), ethyl 1-[6-[[2-(2,2,4-trimethylpyrrolidin-1-yl)pyridine-3-carbonyl]sulfamoyl]-2-pyridyl]piperidine-4-carboxylate (Compound 2488), methyl 3-[[6-[[2-(2,2,4-trimethylpyrrolidin-1-yl)pyridine-3-carbonyl]sulfamoyl]-2-pyridyl]amino]benzoate (Compound 2493), tert-butyl 3-[[6-[[2-(2,2,4-trimethylpyrrolidin-1-yl)pyridine-3-carbonyl]sulfamoyl]-2-pyridyl]amino]propanoate (Compound 2495), N-[[6-[2-(p-tolyl)ethylamino]-2-pyridyl]sulfonyl]-2-(2,2,4-trimethylpyrrolidin-1-yl)pyridine-3-carboxamide (Compound 2502), N-[[6-(5-chloro-2-methoxy-phenoxy)-2-pyridyl]sulfonyl]-2-(2,2,4-trimethylpyrrolidin-1-yl)pyridine-3-carboxamide (Compound 2503), N-[[6-[4-(2-pyridylmethyl)piperazin-1-yl]-2-pyridyl]sulfonyl]-2-(2,2,4-trimethylpyrrolidin-1-yl)pyridine-3-carboxamide (Compound 2504), methyl 4-[6-[[2-(2,2,4-trimethylpyrrolidin-1-yl)pyridine-3-carbonyl]sulfamoyl]-2-pyridyl]piperazine-1-carboxylate (Compound 2506), N-[[6-(3-furylmethoxy)-2-pyridyl]sulfonyl]-2-(2,2,4-trimethylpyrrolidin-1-yl)pyridine-3-carboxamide (Compound 2507), N-[(6-phenoxy-2-pyridyl)sulfonyl]-2-(2,2,4-trimethylpyrrolidin-1-yl)pyridine-3-carboxamide (Compound 2509), N-[[6-(2,6-difluoroanilino)-2-pyridyl]sulfonyl]-2-(2,2,4-trimethylpyrrolidin-1-yl)pyridine-3-carboxamide (Compound 2513), N-[[6-[3-(dimethylamino)anilino]-2-pyridyl]sulfonyl]-2-(2,2,4-trimethylpyrrolidin-1-yl)pyridine-3-carboxamide (Compound 2517), N-[[6-(7-fluoro-3,4-dihydro-1H-isoquinolin-2-yl)-2-pyridyl]sulfonyl]-2-(2,2,4-trimethylpyrrolidin-1-yl)pyridine-3-carboxamide (Compound 2518), N-[[6-(1-oxotetralin-6-yl)oxy-2-pyridyl]sulfonyl]-2-(2,2,4-trimethylpyrrolidin-1-yl)pyridine-3-carboxamide (Compound 2523), N-[[6-[(4-fluorophenyl)methoxy]-2-pyridyl]sulfonyl]-2-(2,2,4-trimethylpyrrolidin-1-yl)pyridine-3-carboxamide (Compound 2524), N-[[6-(3-ethoxyanilino)-2-pyridyl]sulfonyl]-2-(2,2,4-trimethylpyrrolidin-1-yl)pyridine-3-carboxamide (Compound 2526), N-[(6-propoxy-2-pyridyl)sulfonyl]-2-(2,2,4-trimethylpyrrolidin-1-yl)pyridine-3-carboxamide (Compound 2528), N-[[6-(3-butoxypropylamino)-2-pyridyl]sulfonyl]-2-(2,2,4-trimethylpyrrolidin-1-yl)pyridine-3-carboxamide (Compound 2529), N-[[6-[4-(diethylamino)anilino]-2-pyridyl]sulfonyl]-2-(2,2,4-trimethylpyrrolidin-1-yl)pyridine-3-carboxamide (Compound 2531), N-[[6-[(3,4-difluorophenyl)methoxy]-2-pyridyl]sulfonyl]-2-(2,2,4-trimethylpyrrolidin-1-yl)pyridine-3-carboxamide (Compound 2533), N-[[6-(methylamino)-2-pyridyl]sulfonyl]-2-(2,2,4-trimethylpyrrolidin-1-yl)pyridine-3-carboxamide (Compound 2535), tert-butyl (2R)-1-[6-[[2-(2,2,4-trimethylpyrrolidin-1-yl)pyridine-3-carbonyl]sulfamoyl]-2-pyridyl]pyrrolidine-2-carboxylate (Compound 2536), tert-butyl N-[(3R)-1-[6-[[2-(2,2,4-trimethylpyrrolidin-1-yl)pyridine-3-carbonyl]sulfamoyl]-2-pyridyl]pyrrolidin-3-yl]carbamate (Compound 2537), N-[[6-(4-oxazol-5-ylanilino)-2-pyridyl]sulfonyl]-2-(2,2,4-trimethylpyrrolidin-1-yl)pyridine-3-carboxamide (Compound 2546), N-[[6-[3-(3-methylpyrazol-1-yl)propylamino]-2-pyridyl]sulfonyl]-2-(2,2,4-trimethylpyrrolidin-1-yl)pyridine-3-carboxamide (Compound 2550), N-[[6-(3-methoxyphenoxy)-2-pyridyl]sulfonyl]-2-(2,2,4-trimethylpyrrolidin-1-yl)pyridine-3-carboxamide (Compound 2551), N-[(6-pyrrolidin-1-yl-2-pyridyl)sulfonyl]-2-(2,2,4-trimethylpyrrolidin-1-yl)pyridine-3-carboxamide (Compound 2561), N-[[6-(4-pyrrol-1-ylphenoxy)-2-pyridyl]sulfonyl]-2-(2,2,4-trimethylpyrrolidin-1-yl)pyridine-3-carboxamide (Compound 2563), N-[[6-[4-(1-ethylpropyl)piperazin-1-yl]-2-pyridyl]sulfonyl]-2-(2,2,4-trimethylpyrrolidin-1-yl)pyridine-3-carboxamide (Compound 2565), N-[[6-(3-acetylphenoxy)-2-pyridyl]sulfonyl]-2-(2,2,4-trimethylpyrrolidin-1-yl)pyridine-3-carboxamide (Compound 2569), N-[[6-(3-chloro-4-methoxy-anilino)-2-pyridyl]sulfonyl]-2-(2,2,4-trimethylpyrrolidin-1-yl)pyridine-3-carboxamide (Compound 2571), N-[[6-(3-methylanilino)-2-pyridyl]sulfonyl]-2-(2,2,4-trimethylpyrrolidin-1-yl)pyridine-3-carboxamide (Compound 2572), N-[[6-(cyclopropylamino)-2-pyridyl]sulfonyl]-2-(2,2,4-trimethylpyrrolidin-1-yl)pyridine-3-carboxamide (Compound 2574), N-[[6-[(4-methoxyphenyl)methylamino]-2-pyridyl]sulfonyl]-2-(2,2,4-trimethylpyrrolidin-1-yl)pyridine-3-carboxamide (Compound 2579), N-[[6-(5-fluoroisoindolin-2-yl)-2-pyridyl]sulfonyl]-2-(2,2,4-trimethylpyrrolidin-1-yl)pyridine-3-carboxamide (Compound 2580), N-[[6-[(4-chlorophenyl)methoxy]-2-pyridyl]sulfonyl]-2-(2,2,4-trimethylpyrrolidin-1-yl)pyridine-3-carboxamide (Compound 2585), N-[[6-(2-chloro-5-fluoro-phenoxy)-2-pyridyl]sulfonyl]-2-(2,2,4-trimethylpyrrolidin-1-yl)pyridine-3-carboxamide (Compound 2591), N-[[6-(chroman-3-ylmethoxy)-2-pyridyl]sulfonyl]-2-(2,2,4-trimethylpyrrolidin-1-yl)pyridine-3-carboxamide (Compound 2595), N-[[6-(2-furylmethylamino)-2-pyridyl]sulfonyl]-2-(2,2,4-trimethylpyrrolidin-1-yl)pyridine-3-carboxamide (Compound 2597), N-[[6-(5-chloro-2-fluoro-phenoxy)-2-pyridyl]sulfonyl]-2-(2,2,4-trimethylpyrrolidin-1-yl)pyridine-3-carboxamide (Compound 2598), N-[[6-[(3-pyrrol-1-ylphenyl)methoxy]-2-pyridyl]sulfonyl]-2-(2,2,4-trimethylpyrrolidin-1-yl)pyridine-3-carboxamide (Compound 2600), N-[[6-(4-cyclohexylpiperazin-1-yl)-2-pyridyl]sulfonyl]-2-(2,2,4-trimethylpyrrolidin-1-yl)pyridine-3-carboxamide (Compound 2601), N-[[6-(2-propoxyethylamino)-2-pyridyl]sulfonyl]-2-(2,2,4-trimethylpyrrolidin-1-yl)pyridine-3-carboxamide (Compound 2602), N-[[6-(2-methylpyrrolidin-1-yl)-2-pyridyl]sulfonyl]-2-(2,2,4-trimethylpyrrolidin-1-yl)pyridine-3-carboxamide (Compound 2609), N-[[6-[(4-ethynylphenyl)methoxy]-2-pyridyl]sulfonyl]-2-(2,2,4-trimethylpyrrolidin-1-yl)pyridine-3-carboxamide (Compound 2610), N-[[6-(2-naphthyloxy)-2-pyridyl]sulfonyl]-2-(2,2,4-trimethylpyrrolidin-1-yl)pyridine-3-carboxamide (Compound 2611), N-[(6-ethoxy-2-pyridyl)sulfonyl]-2-(2,2,4-trimethylpyrrolidin-1-yl)pyridine-3-carboxamide (Compound 2617), N-[[6-[[4-(trifluoromethyl)phenyl]methoxy]-2-pyridyl]sulfonyl]-2-(2,2,4-trimethylpyrrolidin-1-yl)pyridine-3-carboxamide (Compound 2618), N-[(6-benzyloxy-2-pyridyl)sulfonyl]-2-(2,2,4-trimethylpyrrolidin-1-yl)pyridine-3-carboxamide (Compound 2619), N-[[6-(4-butyl-1,4-diazepan-1-yl)-2-pyridyl]sulfonyl]-2-(2,2,4-trimethylpyrrolidin-1-yl)pyridine-3-carboxamide (Compound 2620), N-[[6-(4-pyrimidin-2-ylpiperazin-1-yl)-2-pyridyl]sulfonyl]-2-(2,2,4-trimethylpyrrolidin-1-yl)pyridine-3-carboxamide (Compound 2621), N-[[6-[2-(2-fluorophenyl)ethoxy]-2-pyridyl]sulfonyl]-2-(2,2,4-trimethylpyrrolidin-1-yl)pyridine-3-carboxamide (Compound 2625), N-[[6-(4H-1,3-benzodioxin-2-ylmethoxy)-2-pyridyl]sulfonyl]-2-(2,2,4-trimethylpyrrolidin-1-yl)pyridine-3-carboxamide (Compound 2627), N-[[6-(2-cyclopentylethoxy)-2-pyridyl]sulfonyl]-2-(2,2,4-trimethylpyrrolidin-1-yl)pyridine-3-carboxamide (Compound 2630), N-[[6-[2-(2-chlorophenyl)ethylamino]-2-pyridyl]sulfonyl]-2-(2,2,4-trimethylpyrrolidin-1-yl)pyridine-3-carboxamide (Compound 2632), N-[[6-(2-methoxyphenoxy)-2-pyridyl]sulfonyl]-2-(2,2,4-trimethylpyrrolidin-1-yl)pyridine-3-carboxamide (Compound 2637), N-[(6-anilino-2-pyridyl)sulfonyl]-2-(2,2,4-trimethylpyrrolidin-1-yl)pyridine-3-carboxamide (Compound 2639), N-[[6-[(2,3-difluorophenyl)methylamino]-2-pyridyl]sulfonyl]-2-(2,2,4-trimethylpyrrolidin-1-yl)pyridine-3-carboxamide (Compound 2640), N-[[6-[4-(trifluoromethyl)-1-piperidyl]-2-pyridyl]sulfonyl]-2-(2,2,4-trimethylpyrrolidin-1-yl)pyridine-3-carboxamide (Compound 2641), N-[[6-[2-(4-ethoxyphenyl)ethylamino]-2-pyridyl]sulfonyl]-2-(2,2,4-trimethylpyrrolidin-1-yl)pyridine-3-carboxamide (Compound 2642), N-[[6-[(2-methyl-8-quinolyl)oxy]-2-pyridyl]sulfonyl]-2-(2,2,4-trimethylpyrrolidin-1-yl)pyridine-3-carboxamide (Compound 2643), N-[[6-[(5-chloro-2-methoxy-phenyl)methoxy]-2-pyridyl]sulfonyl]-2-(2,2,4-trimethylpyrrolidin-1-yl)pyridine-3-carboxamide (Compound 2645), N-[[6-(3-methylbut-2-enoxy)-2-pyridyl]sulfonyl]-2-(2,2,4-trimethylpyrrolidin-1-yl)pyridine-3-carboxamide (Compound 2648), N-[[6-(2,4,6-trifluorophenoxy)-2-pyridyl]sulfonyl]-2-(2,2,4-trimethylpyrrolidin-1-yl)pyridine-3-carboxamide (Compound 2654), N-[[6-[(5-chloro-2-pyridyl)amino]-2-pyridyl]sulfonyl]-2-(2,2,4-trimethylpyrrolidin-1-yl)pyridine-3-carboxamide (Compound 2656), N-[[6-(2-cyanoanilino)-2-pyridyl]sulfonyl]-2-(2,2,4-trimethylpyrrolidin-1-yl)pyridine-3-carboxamide (Compound 2659), N-[[6-[(5-chloro-2-pyridyl)oxy]-2-pyridyl]sulfonyl]-2-(2,2,4-trimethylpyrrolidin-1-yl)pyridine-3-carboxamide (Compound 2747), N-[[6-[2-(4-pyridyl)ethylamino]-2-pyridyl]sulfonyl]-2-(2,2,4-trimethylpyrrolidin-1-yl)pyridine-3-carboxamide (Compound 2746), N-[[6-(2-aminoethoxy)-2-pyridyl]sulfonyl]-2-(2,2,4-trimethylpyrrolidin-1-yl)pyridine-3-carboxamide (Compound 2754), N-[(6-but-2-ynoxy-2-pyridyl)sulfonyl]-2-(2,2,4-trimethylpyrrolidin-1-yl)pyridine-3-carboxamide (Compound 2753), N-[[6-[3-methoxypropyl(methyl)amino]-2-pyridyl]sulfonyl]-2-(2,2,4-trimethylpyrrolidin-1-yl)pyridine-3-carboxamide (Compound 2745), N-[[6-(4-methoxy-1-piperidyl)-2-pyridyl]sulfonyl]-2-(2,2,4-trimethylpyrrolidin-1-yl)pyridine-3-carboxamide (Compound 2743), N-[[6-(1-oxoindan-5-yl)oxy-2-pyridyl]sulfonyl]-2-(2,2,4-trimethylpyrrolidin-1-yl)pyridine-3-carboxamide (Compound 2744), N-[[6-[(6-methyl-2-pyridyl)oxy]-2-pyridyl]sulfonyl]-2-(2,2,4-trimethylpyrrolidin-1-yl)pyridine-3-carboxamide (Compound 2742), N-[[6-(4-acetylphenoxy)-2-pyridyl]sulfonyl]-2-(2,2,4-trimethylpyrrolidin-1-yl)pyridine-3-carboxamide (Compound 2741), N-[[6-[(2-methyl-1,3-benzothiazol-5-yl)oxy]-2-pyridyl]sulfonyl]-2-(2,2,4-trimethylpyrrolidin-1-yl)pyridine-3-carboxamide (Compound 2740), N-[[6-[[(1R)-1,2,2-trimethylpropyl]amino]-2-pyridyl]sulfonyl]-2-(2,2,4-trimethylpyrrolidin-1-yl)pyridine-3-carboxamide (Compound 2757), methyl 4-[[6-[[2-(2,2,4-trimethylpyrrolidin-1-yl)pyridine-3-carbonyl]sulfamoyl]-2-pyridyl]oxy]benzoate (Compound 2739), N-[[6-(2,1,3-benzoxadiazol-5-yloxy)-2-pyridyl]sulfonyl]-2-(2,2,4-trimethylpyrrolidin-1-yl)pyridine-3-carboxamide (Compound 2738), N-[[6-(4-tert-butoxyphenoxy)-2-pyridyl]sulfonyl]-2-(2,2,4-trimethylpyrrolidin-1-yl)pyridine-3-carboxamide (Compound 2751), N-[[6-[isobutyl(methyl)amino]-2-pyridyl]sulfonyl]-2-(2,2,4-trimethylpyrrolidin-1-yl)pyridine-3-carboxamide (Compound 2758), N-[[6-(diethylamino)-2-pyridyl]sulfonyl]-2-(2,2,4-trimethylpyrrolidin-1-yl)pyridine-3-carboxamide (Compound 2737), N-[[6-(3-cyanophenoxy)-2-pyridyl]sulfonyl]-2-(2,2,4-trimethylpyrrolidin-1-yl)pyridine-3-carboxamide (Compound 2736), N-[[6-[isopropyl(methyl)amino]-2-pyridyl]sulfonyl]-2-(2,2,4-trimethylpyrrolidin-1-yl)pyridine-3-carboxamide (Compound 2735), tert-butyl N-[4-[[6-[[2-(2,2,4-trimethylpyrrolidin-1-yl)pyridine-3-carbonyl]sulfamoyl]-2-pyridyl]amino]phenyl]carbamate (Compound 2755), N-[[6-[2-(3-fluorophenyl)ethoxy]-2-pyridyl]sulfonyl]-2-(2,2,4-trimethylpyrrolidin-1-yl)pyridine-3-carboxamide (Compound 2752), N-[[6-[2-(1-piperidyl)phenoxy]-2-pyridyl]sulfonyl]-2-(2,2,4-trimethylpyrrolidin-1-yl)pyridine-3-carboxamide (Compound 2750), N-[[6-(2-methyl-1-piperidyl)-2-pyridyl]sulfonyl]-2-(2,2,4-trimethylpyrrolidin-1-yl)pyridine-3-carboxamide (Compound 2759), N-[[6-[cyclopropylmethyl(propyl)amino]-2-pyridyl]sulfonyl]-2-(2,2,4-trimethylpyrrolidin-1-yl)pyridine-3-carboxamide (Compound 2734), N-[[6-[(2,5-dimethoxyphenyl)methylamino]-2-pyridyl]sulfonyl]-2-(2,2,4-trimethylpyrrolidin-1-yl)pyridine-3-carboxamide (Compound 2733), N-[(6-phenethyloxy-2-pyridyl)sulfonyl]-2-(2,2,4-trimethylpyrrolidin-1-yl)pyridine-3-carboxamide (Compound 2732), N-[[6-(2,3-dichlorophenoxy)-2-pyridyl]sulfonyl]-2-(2,2,4-trimethylpyrrolidin-1-yl)pyridine-3-carboxamide (Compound 2731), N-[[6-(3-chloro-5-fluoro-phenoxy)-2-pyridyl]sulfonyl]-2-(2,2,4-trimethylpyrrolidin-1-yl)pyridine-3-carboxamide (Compound 2730), N-[[6-[(2-chlorophenyl)methyl-methyl-amino]-2-pyridyl]sulfonyl]-2-(2,2,4-trimethylpyrrolidin-1-yl)pyridine-3-carboxamide (Compound 2756), N-[(6-chroman-4-yloxy-2-pyridyl)sulfonyl]-2-(2,2,4-trimethylpyrrolidin-1-yl)pyridine-3-carboxamide (Compound 2749), N-[[6-[3-(trifluoromethyl)phenoxy]-2-pyridyl]sulfonyl]-2-(2,2,4-trimethylpyrrolidin-1-yl)pyridine-3-carboxamide (Compound 2729), N-[[6-[(2-chloro-6-fluoro-phenyl)methoxy]-2-pyridyl]sulfonyl]-2-(2,2,4-trimethylpyrrolidin-1-yl)pyridine-3-carboxamide (Compound 2728), 6-tert-butyl-N-[(6-isopentyloxy-2-pyridyl)sulfonyl]-2-(2,2,4-trimethylpyrrolidin-1-yl)pyridine-3-carboxamide (Compound 2727), N-[[6-(1,3-benzodioxol-5-ylmethoxy)-2-pyridyl]sulfonyl]-6-tert-butyl-2-(2,2,4-trimethylpyrrolidin-1-yl)pyridine-3-carboxamide (Compound 2725), N-[[6-[(E)-but-2-enoxy]-2-pyridyl]sulfonyl]-6-tert-butyl-2-(2,2,4-trimethylpyrrolidin-1-yl)pyridine-3-carboxamide (Compound 2726), 6-tert-butyl-N-[[6-[(4-methoxyphenyl)methylamino]-2-pyridyl]sulfonyl]-2-(2,2,4-trimethylpyrrolidin-1-yl)pyridine-3-carboxamide (Compound 2723), N-[[6-[(3,4-dimethoxyphenyl)methylamino]-2-pyridyl]sulfonyl]-2-(2,2,4-trimethylpyrrolidin-1-yl)pyridine-3-carboxamide (Compound 2662), and N-[[6-(3,5-dichlorophenoxy)-2-pyridyl]sulfonyl]-2-(2,2,4-trimethylpyrrolidin-1-yl)pyridine-3-carboxamide (Compound 2663)

Preparation 107: N-[(2-oxo-1H-pyridin-3-yl)sulfonyl]-6-phenyl-2-[(4S)-2,2,4-trimethylpyrrolidin-1-yl]pyridine-3-carboxamide (Compound 2445)

Step 1: 2-Methoxypyridine-3-sulfonamide

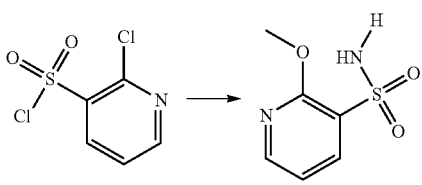

2-Chloropyridine-3-sulfonyl chloride (5.00 g, 23.6 mmol) was dissolved in ammonia in methanol (16.8 mL of 7 M, 117.9 mmol) and the reaction mixture was stirred for 30 minutes. The reaction mixture was concentrated under reduced pressure and dissolved in sodium methoxide (24.9 mL of 25% w/v, 115.1 mmol) and heated to 60° C. over 2 days. The reaction mixture was evaporated and the residue was partitioned between ethyl acetate and 1N HCl. The organics were separated, washed with brine, dried over sodium sulfate and concentrated under reduced pressure. The crude material was purified by silica gel column chromatography eluting with 0-100% ethyl acetate in hexanes to give 2-methoxypyridine-3-sulfonamide (3.12 g, 70%) ESI-MS m/z calc. 188.02556, found 189.0 (M+1)$^+$; Retention time: 0.23 minutes Step 2: 2,6-dichloro-N-[(2-methoxy-3-pyridyl)sulfonyl]pyridine-3-carboxamide

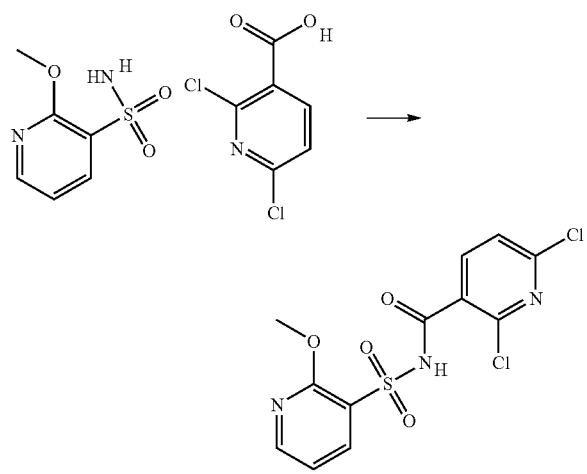

A mixture of 2,6-dichloropyridine-3-carboxylic acid (2.00 g, 10.4 mmol), thionyl chloride (7.45 g, 4.56 mL, 62.5 mmol), and DMF (0.1 mL) was stirred at 45° C. for 5 hours. The reaction was concentrated under reduced pressure, dissolved in dichloromethane (5.30 mL) and slowly added to a solution of 2-methoxypyridine-3-sulfonamide (1.96 g, 10.4 mmol) and triethylamine (3.16 g, 4.36 mL, 31.3 mmol) in dichloromethane (5.30 mL) cooled in an ice bath. The reaction mixture was stirred overnight, then diluted with dichloromethane and washed with 1 M HCl (20 mL×1), water (20 mL), dried over sodium sulfate, and evaporated under reduced pressure. The residue was purified by silica gel column chromatography (0-5% methanol in dichloromethane). The resulting solid was dissolved in dichloromethane and washed with sodium bicarbonate (~pH 5), the organic layers were dried over sodium sulfate and evaporated under reduced pressure to give 2,6-dichloro-N-[(2-methoxy-3-pyridyl)sulfonyl]pyridine-3-carboxamide (3.50 g, 93%) ESI-MS m/z calc. 360.9691, found 362.0 (M+1)$^+$; Retention time: 0.46 minutes.

Step 3: 2,6-dichloro-N-[(2-oxo-1H-pyridin-3-yl)sulfonyl]pyridine-3-carboxamide

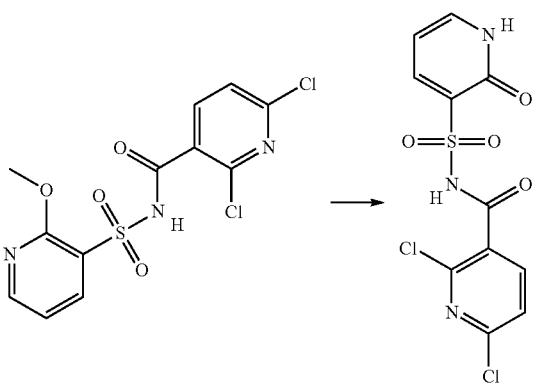

A mixture of 2,6-dichloro-N-[(2-methoxy-3-pyridyl)sulfonyl]pyridine-3-carboxamide (0.76 g, 2.10 mmol) and HCl (5.25 mL of 4 M in dioxane, 21.0 mmol) in dioxane (5 mL) was stirred at 90° C. for 90 minutes. The solvent was evaporated under reduced pressure to give 2,6-dichloro-N-((2-oxo-1,2-dihydropyridin-3-yl)sulfonyl)nicotinamide (0.72 g, 99%) as a tan solid.

Step 4: 6-chloro-N-[(2-oxo-1H-pyridin-3-yl)sulfonyl]-2-[(4S)-2,2,4-trimethylpyrrolidin-1-yl]pyridine-3-carboxamide

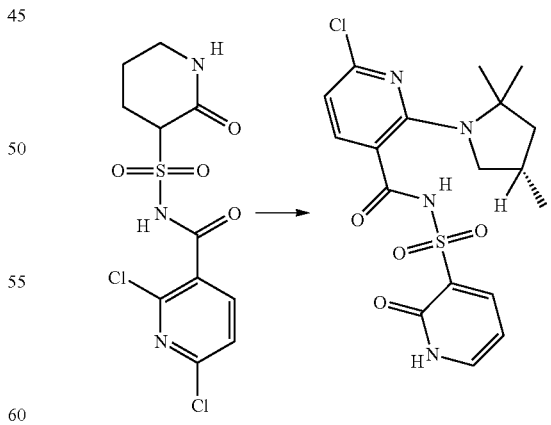

To 2,6-dichloro-N-[(2-oxo-1H-pyridin-3-yl)sulfonyl]pyridine-3-carboxamide (HCl salt) (4.04 g, 10.5 mmol), (4S)-2,2,4-trimethylpyrrolidine (HCl salt) (2.36 g, 15.8 mmol), and K$_2$CO$_3$ (7.26 g, 52.5 mmol) was added DMSO (8.86 mL) and the reaction mixture was heated at 120° C. for 24 h. The reaction mixture was diluted with ethyl acetate and the residual potassium carbonate was filtered. The organics were washed with 0.1 M aqueous HCl (150 mL). The pH of aqueous layer was brought to 5 by the addition of aqueous HCl, and then washed with ethyl acetate. The combined organic layers were washed with brine, dried over sodium sulfate and concentrated under reduced pressure to give 6-chloro-N-[(2-oxo-1H-pyridin-3-yl)sulfonyl]-2-[(4S)-2,2,4-trimethylpyrrolidin-1-yl]pyridine-3-carboxamide (4.15 g, 94%).

Step 5: N-[(2-oxo-1H-pyridin-3-yl)sulfonyl]-6-phenyl-2-[(4S)-2,2,4-trimethylpyrrolidin-1-yl]pyridine-3-carboxamide (Compound 2445)

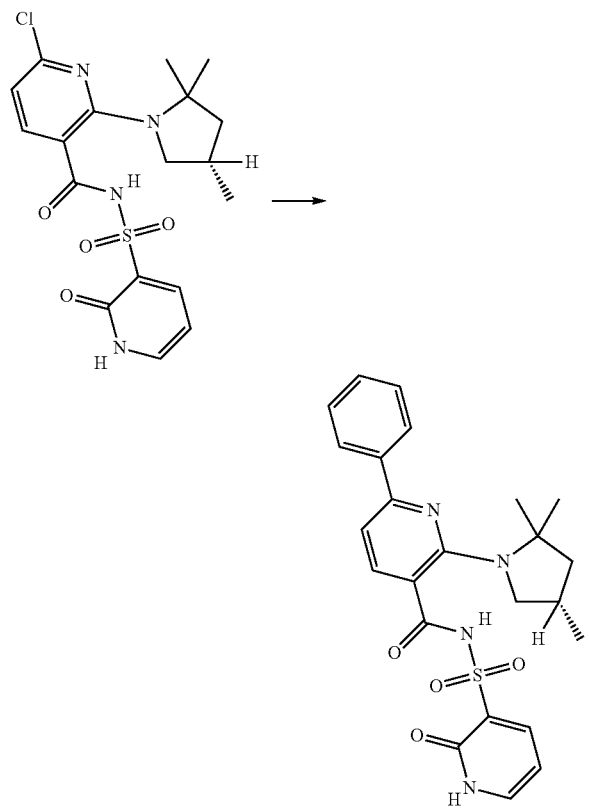

6-chloro-N-[(2-oxo-1H-pyridin-3-yl)sulfonyl]-2-[(4S)-2,2,4-trimethylpyrrolidin-1-yl]pyridine-3-carboxamide (30.0 mg, 0.07 mmol), phenylboronic acid (10.3 mg, 0.08 mmol), [1,3-bis(2,6-diisopropylphenyl)-2H-imidazol-2-yl]-dichloro-(3-chloro-1-pyridyl)palladium (4.80 mg, 0.01 mmol), and 2M $K_2CO_3$ (177 uL, 0.35 mmol) were combined in DMF (1.0 mL) and heated at 120° C. for 16 h. The reaction mixture was filtered and purified by LC/MS utilizing a gradient of 10-99% acetonitrile in 5 mM aq HCl to yield N-[(2-oxo-1H-pyridin-3-yl)sulfonyl]-6-phenyl-2-[(4S)-2,2,4-trimethylpyrrolidin-1-yl]pyridine-3-carboxamide (Compound 2445). ESI-MS m/z 467.4 (M+1)$^+$; Retention time: 1.13 minutes; 1H NMR (400 MHz, DMSO-$d_6$) δ 12.59 (s, 1H), 12.53 (d, J=6.3 Hz, 1H), 8.24 (dd, J=7.2, 2.2 Hz, 1H), 8.08-8.02 (m, 2H), 7.83 (dt, J=6.6, 3.3 Hz, 1H), 7.76 (d, J=8.0 Hz, 1H), 7.54-7.46 (m, 2H), 7.46-7.40 (m, 1H), 7.19 (d, J=8.0 Hz, 1H), 6.45 (t, J=6.8 Hz, 1H), 2.82-2.63 (m, 2H), 2.30-2.18 (m, 1H), 1.89 (dd, J=11.8, 5.5 Hz, 1H), 1.62 (s, 6H), 1.45 (t, J=12.1 Hz, 1H), 0.91 (d, J=6.3 Hz, 3H).

The following compounds can be synthesized using the procedures described herein:

6-(m-tolyl)-N-[(2-oxo-1H-pyridin-3-yl)sulfonyl]-2-[(4S)-2,2,4-trimethylpyrrolidin-1-yl]pyridine-3-carboxamide (Compound 2424), 6-(2-hydroxyphenyl)-N-[(2-oxo-1H-pyridin-3-yl)sulfonyl]-2-[(4S)-2,2,4-trimethylpyrrolidin-1-yl]pyridine-3-carboxamide (Compound 2480), N-[(2-oxo-1H-pyridin-3-yl)sulfonyl]-6-[4-(trifluoromethyl)phenyl]-2-[(4S)-2,2,4-trimethylpyrrolidin-1-yl]pyridine-3-carboxamide (Compound 1799), N-[(2-oxo-1H-pyridin-3-yl)sulfonyl]-6-(p-tolyl)-2-[(4S)-2,2,4-trimethylpyrrolidin-1-yl]pyridine-3-carboxamide (Compound 2438), 6-(3-methoxyphenyl)-N-[(2-oxo-1H-pyridin-3-yl)sulfonyl]-2-[(4S)-2,2,4-trimethylpyrrolidin-1-yl]pyridine-3-carboxamide (Compound 1927), N-[(2-oxo-1H-pyridin-3-yl)sulfonyl]-6-[2-(trifluoromethoxy)phenyl]-2-[(4S)-2,2,4-trimethylpyrrolidin-1-yl]pyridine-3-carboxamide (Compound 2514), 6-[3-(hydroxymethyl)phenyl]-N-[(2-oxo-1H-pyridin-3-yl)sulfonyl]-2-[(4S)-2,2,4-trimethylpyrrolidin-1-yl]pyridine-3-carboxamide (Compound 1997), 6-(4-methoxyphenyl)-N-[(2-oxo-1H-pyridin-3-yl)sulfonyl]-2-[(4S)-2,2,4-trimethylpyrrolidin-1-yl]pyridine-3-carboxamide (Compound 2080), N-(benzenesulfonyl)-6-(6-methoxy-2-pyridyl)-2-[(4S)-2,2,4-trimethylpyrrolidin-1-yl]pyridine-3-carboxamide (Compound 2411), 6-(3-fluoro-5-isobutoxy-phenyl)-N-(3-hydroxyphenyl)sulfonyl-2-[(4S)-2,2,4-trimethylpyrrolidin-1-yl]pyridine-3-carboxamide (Compound 1885), N-(benzenesulfonyl)-6-(2-hydroxy-3-methyl-phenyl)-2-[(4S)-2,2,4-trimethylpyrrolidin-1-yl]pyridine-3-carboxamide (Compound 2133), 6-(3-fluoro-5-isobutoxy-phenyl)-N-(4-hydroxyphenyl)sulfonyl-2-[(4S)-2,2,4-trimethylpyrrolidin-1-yl]pyridine-3-carboxamide (Compound 1750), 6-(3-fluoro-5-isobutoxy-phenyl)-N-(2-hydroxyphenyl)sulfonyl-2-[(4S)-2,2,4-trimethylpyrrolidin-1-yl]pyridine-3-carboxamide (Compound 1836), 6-(3-fluoro-5-isobutoxy-phenyl)-N-(4-methoxyphenyl)sulfonyl-2-[(4S)-2,2,4-trimethylpyrrolidin-1-yl]pyridine-3-carboxamide (Compound 1876), N-(benzenesulfonyl)-6-phenyl-2-[(4S)-2,2,4-trimethylpyrrolidin-1-yl]pyridine-3-carboxamide (Compound 2092), N-(benzenesulfonyl)-2-[(3S)-2,2-dideuterio-3,5,5-trimethyl-pyrrolidin-1-yl]-6-(3-fluoro-5-isobutoxy-phenyl)pyridine-3-carboxamide (Compound 2560), N-[(2-amino-3-pyridyl)sulfonyl]-6-(4-ethoxy-3-methyl-phenyl)-2-[(4S)-2,2,4-trimethylpyrrolidin-1-yl]pyridine-3-carboxamide (Compound 1860), N-[(2-amino-3-pyridyl)sulfonyl]-6-[1-methyl-3-(trifluoromethyl)pyrazol-4-yl]-2-[(4S)-2,2,4-trimethylpyrrolidin-1-yl]pyridine-3-carboxamide (Compound 1740), N-[(2-amino-3-pyridyl)sulfonyl]-6-(1H-indol-5-yl)-2-[(4S)-2,2,4-trimethylpyrrolidin-1-yl]pyridine-3-carboxamide (Compound 2125), N-[(2-amino-3-pyridyl)sulfonyl]-6-[2-(dimethylamino)pyrimidin-5-yl]-2-[(4S)-2,2,4-trimethylpyrrolidin-1-yl]pyridine-3-carboxamide (Compound 2021), N-[(2-amino-3-pyridyl)sulfonyl]-6-(1H-indol-4-yl)-2-[(4S)-2,2,4-trimethylpyrrolidin-1-yl]pyridine-3-carboxamide (Compound 2478), N-[(2-amino-3-pyridyl)sulfonyl]-6-(4-hydroxy-3,5-dimethyl-phenyl)-2-[(4S)-2,2,4-trimethylpyrrolidin-1-yl]pyridine-3-carboxamide (Compound 1923), N-[(2-amino-3-pyridyl)sulfonyl]-6-[2-methyl-5-(trifluoromethyl)pyrazol-3-yl]-2-[(4S)-2,2,4-trimethylpyrrolidin-1-yl]pyridine-3-carboxamide (Compound 2416), N-[(2-amino-3-pyridyl)sulfonyl]-6-(2-ethoxy-6-fluoro-phenyl)-2-[(4S)-2,2,4-trimethylpyrrolidin-1-yl]pyridine-3-carboxamide (Compound 2103), N-[(2-amino-3-pyridyl)sulfonyl]-6-(2-ethoxy-5-fluoro-phenyl)-2-[(4S)-2,2,4-trimethylpyrrolidin-1-yl]pyridine-3-carboxamide (Compound 2071), N-[(2-amino-3-pyridyl)sulfonyl]-6-(6-methyl-3-pyridyl)-2-[(4S)-2,2,4-trimethylpyrrolidin-1-yl]pyridine-3-carboxamide (Compound 2363), N-[(2-amino-3-pyridyl)sulfonyl]-6-(1-methylindol-5-yl)-2-[(4S)-2,2,4-trimethylpyrrolidin-1-yl]pyridine-3-carboxamide (Compound 2352), N-[(2-amino-3-pyridyl)sulfonyl]-6-(1,3,5-trimethylpyrazol-4-yl)-2-[(4S)-2,2,4-trimethylpyrrolidin-1-yl]pyridine-3-carboxamide (Compound 2668), N-[(2-amino-3-pyridyl)sulfonyl]-6-(2,5-difluoro-4-methoxy-phenyl)-2-[(4S)-2,2,4-trimethylpyrrolidin-1-yl]pyridine-3-carboxamide (Compound 2388), N-[(2-amino-3-pyridyl)sulfonyl]-6-(6-hydroxy-2-naphthyl)-2-[(4S)-2,2,4-trimethylpyrrolidin-1-yl]pyridine-3-carboxamide (Compound 2468), N-[(2-amino-3-pyridyl)sulfonyl]-6-(4-hydroxy-3-methoxyphenyl)-2-[(4S)-2,2,4-trimethylpyrrolidin-1-yl]pyridine-3-carboxamide (Compound 2614), N-[(6-amino-2-pyridyl)sulfonyl]-6-(6-methoxy-5-methyl-3-pyridyl)-2-[(4S)-2,2,4-trimethylpyrrolidin-1-yl]pyridine-3-carboxamide (Compound 2086), 6-(3-fluoro-5-isobutoxy-phenyl)-N-(3-pyridylsulfonyl)-2-[(4S)-2,2,4-trimethylpyrrolidin-1-yl]pyridine-3-carboxamide (Compound 2377), 6-(3-fluoro-5-isobutoxy-phenyl)-N-(2-pyridylsulfonyl)-2-[(4S)-2,2,4-trimethylpyrrolidin-1-yl]pyridine-3-carboxamide (Compound 1832), 6-(3,5-dimethylphenyl)-N-[(6-isopentyloxy-2-pyridyl)sulfonyl]-2-[(4S)-2,2,4-trimethylpyrrolidin-1-yl]pyridine-3-carboxamide (Compound 2707) and 2-[(2S,5R)-2,5-dimethylpyrrolidin-1-yl]-6-(3-fluoro-5-isobutoxy-phenyl)-N-[(2-oxo-1H-pyridin-3-yl)sulfonyl]pyridine-3-carboxamide (Compound 307).

Preparation 108: N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191)

Step 1: 1-(3-hydroxypyrazol-1-yl)ethanone

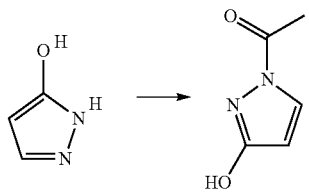

1H-pyrazol-5-ol (1.02 g, 12.1 mmol) and pyridine (5.0 mL, 61.8 mmol) were stirred at 95° C. and a solution of acetic anhydride (1.24 g; 1.14 mL, 12.1 mmol) in pyridine (2.0 mL, 24.7 mmol) was added dropwise over a period of 3 minutes. The reaction mixture was then stirred at 95° C. for an additional 1.5 h. The solvents were removed under reduced pressure and the solid residue was triturated with diethylether (30 mL), filtered, washed with diethylether and dried under high vacuum to give 1-(3-hydroxypyrazol-1-yl)ethanone (1.34 g, 88%) as a yellow solid. ESI-MS m/z calc. 126.04293, found 127.1 (M+1)$^+$; Retention time: 0.3 minutes; 1H NMR (400 MHz, DMSO-d$_6$) δ 10.92 (s, 1H), 8.12 (d, J=2.9 Hz, 1H), 6.00 (d, J=3.0 Hz, 1H), 2.48 (s, 3H).

Step 2: 1-(3-isobutoxypyrazol-1-yl)ethanone

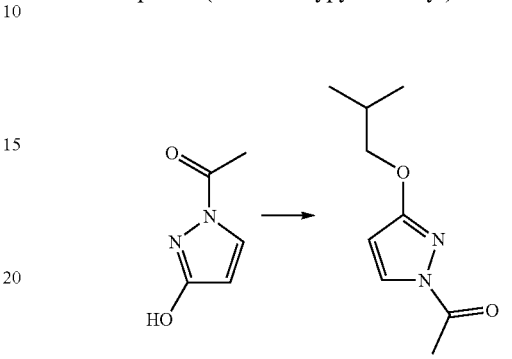

To 1-(3-hydroxypyrazol-1-yl)ethanone (1.25 g, 9.91 mmol), potassium carbonate (2.06 g, 14.9 mmol) and anhydrous DMF (10 mL) under nitrogen atmosphere was added 1-bromo-2-methyl-propane (1.49 g, 1.19 mL, 10.9 mmol). The reaction was stirred at 80° C. for 2 hours. The reaction mixture was diluted with EtOAc (50 ml) and water (25 mL) and two phases were separated. The aqueous phase (pH=9-10) was further extracted with EtOAc (20 mL). The combined extracts were dried over sodium sulfate and the solvents evaporated. The resulting oil was purified by silica gel column chromatography using a gradient of EtOAc (0 to 30%) in hexanes to give 1-(3-isobutoxypyrazol-1-yl)ethanone (1.24 g, 69%) as a colorless oil. ESI-MS m/z calc. 182.10553, found 183.3 (M+1)$^+$; Retention time: 1.35 minutes; 1H NMR (400 MHz, Chloroform-d) δ 8.05 (d, J=3.0 Hz, 1H), 5.96 (d, J=3.0 Hz, 1H), 3.99 (d, J=6.6 Hz, 2H), 2.58 (s, 3H), 2.08 (dq, J=12.9, 6.4 Hz, 1H), 1.01 (d, J=6.7 Hz, 6H).

Step 3: 3-isobutoxy-1H-pyrazole

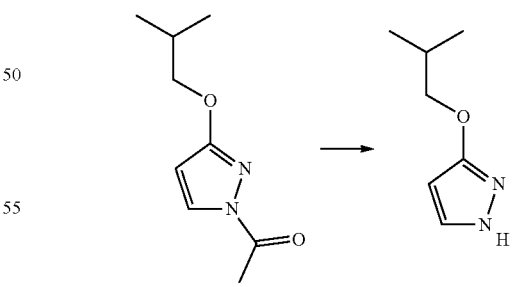

1-(3-isobutoxypyrazol-1-yl)ethanone (1.24 g, 6.82 mmol) was treated with MeOH (20 mL) and NaOH (1.14 mL of 6 M, 6.82 mmol) (6N aqueous) at room temperature for 2 hours. The volatiles were removed under reduced pressure. The residue was taken in EtOAc (25 mL) and brine (20 ml) and two phases were separated. The aqueous phase was further extracted with EtOAc (2×25 mL) and the combined extracts were dried over sodium sulfate and concentrated under reduced pressure to give 3-isobutoxy-1H-pyrazole (955 mg, 99%) as a slightly colored viscous oil. ESI-MS m/z calc. 140.09496, found 141.2 (M+1)+; Retention time: 0.86 minutes; 1H NMR (400 MHz, Chloroform-d) δ 9.25 (very broad s, 1H), 7.35 (d, J=2.5 Hz, 1H), 5.73 (d, J=2.5 Hz, 1H), 3.91 (d, J=6.7 Hz, 2H), 2.15-2.02 (m, 1H), 1.06-0.98 (m, 6H).

Step 4: tert-butyl 2-chloro-6-(3-isobutoxypyrazol-1-yl)pyridine-3-carboxylate

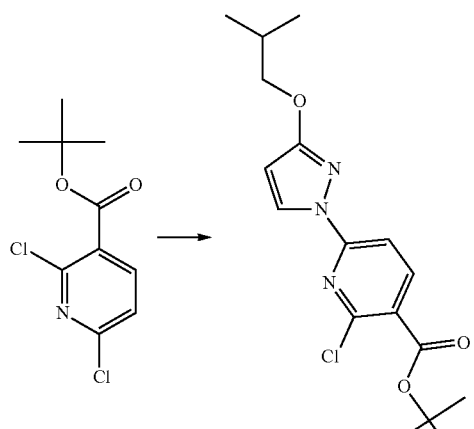

NaH (64 mg, 1.6 mmol) (60% oil suspension) was added to 3-isobutoxy-1H-pyrazole (224 mg, 1.60 mmol) in anhydrous DMF (2 mL). The reaction mixture was stirred until gas evolution stopped. Tert-butyl 2,6-dichloropyridine-3-carboxylate (330 mg, 1.33 mmol) was added and the reaction mixture was stirred at 100° C. under nitrogen for 30 minutes. The reaction mixture was diluted with EtOAc (50 mL) and water+brine (40 mL) and the two phases were separated. The aqueous phase was further extracted with EtOAc (2×30 mL). The combined extracts were dried over sodium sulfate and the solvent removed under reduced pressure to give a residue, which was purified by silica gel column chromatography using a gradient of AcOEt (0 to 20%) in hexanes to give tert-butyl 2-chloro-6-(3-isobutoxypyrazol-1-yl)pyridine-3-carboxylate (235 mg, 50%) as an off-white solid). ESI-MS m/z calc. 351.13498, found 352.2 (M+1)+; Retention time: 2.34 minutes, 1H NMR (400 MHz, Chloroform-d) δ 8.35 (d, J=2.8 Hz, 1H), 8.18 (d, J=8.4 Hz, 1H), 7.70 (d, J=8.4 Hz, 1H), 5.97 (d, J=2.9 Hz, 1H), 4.02 (d, J=6.6 Hz, 2H), 2.12 (dp, J=13.4, 6.7 Hz, 1H), 1.62 (s, 9H), 1.03 (d, J=6.7 Hz, 6H).

Step 5: 2-chloro-6-(3-isobutoxypyrazol-1-yl)pyridine-3-carboxylic acid

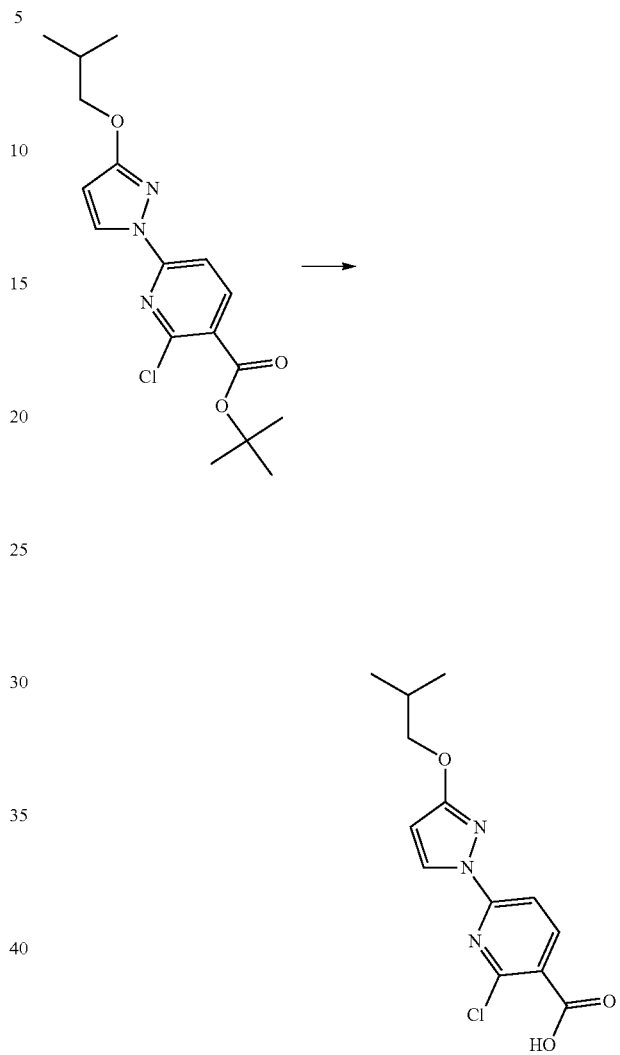

Tert-butyl 2-chloro-6-(3-isobutoxypyrazol-1-yl)pyridine-3-carboxylate (203 mg, 0.57 mmol), DCM (2 mL) and TFA (615 μL, 7.98 mmol) were stirred at 40-45° C. for 3 hours. The volatiles were remove under reduced pressure to give 2-chloro-6-(3-isobutoxypyrazol-1-yl)pyridine-3-carboxylic acid (170 mg, 100%) as a white solid. ESI-MS m/z calc. 295.07236, found 296.3 (M+1)+; Retention time: 1.64 minutes; 1H NMR (400 MHz, DMSO-d6) δ 13.58 (s, 1H), 8.41 (d, J=2.9 Hz, 1H), 8.38 (d, J=8.4 Hz, 1H), 7.73 (d, J=8.4 Hz, 1H), 6.20 (d, J=2.9 Hz, 1H), 4.02 (d, J=6.6 Hz, 2H), 2.06 (hept, J=6.6 Hz, 1H), 0.98 (d, J=6.7 Hz, 6H).

2175

Step 6: N-[(2-amino-3-pyridyl)sulfonyl]-2-chloro-6-(3-isobutoxypyrazol-1-yl)pyridine-3-carboxamide

2176

Step 7: N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191)

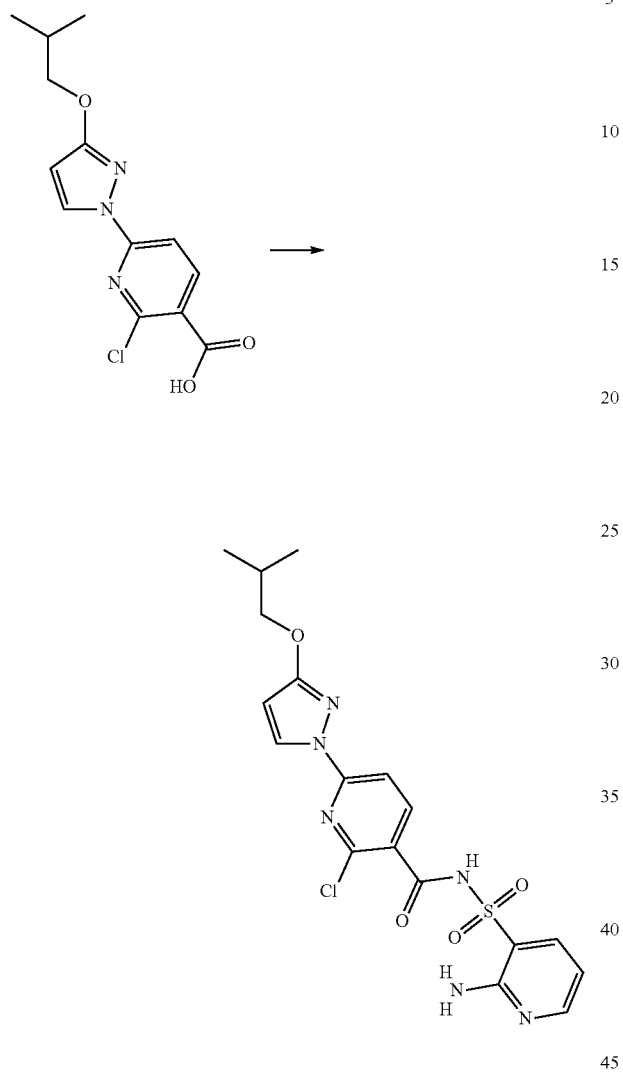

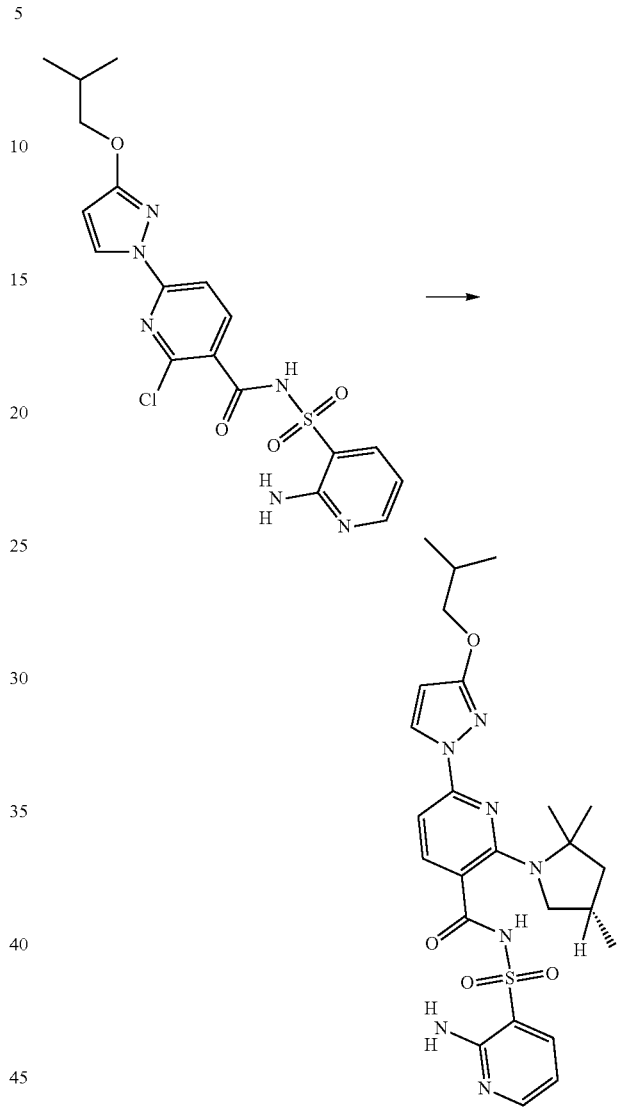

DMF (1.2 mL) was added to 2-chloro-6-(3-isobutoxypyrazol-1-yl)pyridine-3-carboxylic acid (128 mg, 0.43 mmol) and CDI (87 mg, 0.54 mmol) under an atmosphere of nitrogen. The reaction mixture was stirred at 40° C. under nitrogen for 1 hour. 2-aminopyridine-3-sulfonamide (91 mg, 0.53 mmol) was dissolved under nitrogen in anhydrous DMF (1.2 mL) and NaH (21 mg, 0.53 mmol) (60% oil suspension) was added and the reaction mixture was stirred under nitrogen until gas evolution stopped and then stirred at 40° C. for 45 minutes. The two reaction mixtures were combined and stirred at room temperature for 1.5 hours. Water and ice was added, followed by acetic acid (400 µL, 7.03 mmol). The resulting solid was filtered, washed with water and dried to give N-[(2-amino-3-pyridyl)sulfonyl]-2-chloro-6-(3-isobutoxypyrazol-1-yl)pyridine-3-carboxamide (189 mg, 97%) as a white solid. ESI-MS m/z calc. 450.0877, found 451.4 (M+1)$^+$; Retention time: 1.42 minutes.

N-[(2-amino-3-pyridyl)sulfonyl]-2-chloro-6-(3-isobutoxypyrazol-1-yl)pyridine-3-carboxamide (177 mg, 0.39 mmol), (4S)-2,2,4-trimethylpyrrolidine (HCl salt) (237 mg, 1.58 mmol), $K_2CO_3$ (327 mg, 2.37 mmol) and anhydrous DMSO (550 µL) were heated at 150° C. for 6 hours under an atmosphere of nitrogen. The reaction mixture was then cooled and a stirred mixture of water (40 mL) and acetic acid (400 µL, 7.034 mmol) was added dropwise. The resulting yellow solid was filtered and washed with water. The solid was dissolved in dichloromethane and the organic phase was dried over sodium sulfate and concentrated under reduced pressure. The resulting solid was purified by silica gel column chromatography using a gradient of MeOH (0 to 10%) in DCM, followed by purification by reverse phase preparative HPLC using a gradient of MeCN in water (1 to 99% over 15 min) and HCl as a modifier to give N-[(2-amino-3-pyridyl)sulfonyl]-6-(3-isobutoxypyrazol-1-yl)-2-[(4S)-2,2,4-trimethylpyrrolidin-1-yl]pyridine-3-carboxamide (Compound 2191) (77 mg, 36%) as a pale yellow solid.

ESI-MS m/z calc. 527.23145, found 528.3 (M+1)+; Retention time: 1.55 minutes; 1H NMR (400 MHz, DMSO-d6) δ 12.45 (broad s, 1H), 8.28-8.22 (m, 1H), 8.20 (d, J=2.7 Hz, 1H), 8.06-7.99 (m, 1H), 7.84 (d, J=8.3 Hz, 1H), 6.94 (d, J=8.3 Hz, 1H), 6.77 (dd, J=7.7, 4.9 Hz, 1H), 6.69 (br s, 2H), 6.12 (d, J=2.6 Hz, 1H), 3.98 (d, J=6.6 Hz, 2H), 2.45 (d, J=8.6 Hz, 2H), 2.13-2.01 (m, 2H), 1.90-1.79 (m, 1H), 1.55 (s, 3H), 1.53 (s, 3H), 1.38 (t, J=12.1 Hz, 1H), 0.98 (d, J=6.8 Hz, 6H), 0.74 (d, J=6.2 Hz, 3H).

Preparation 109: N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975)

Step 1: 1-[3-(2,2-dimethylpropoxy)pyrazol-1-yl]ethanone

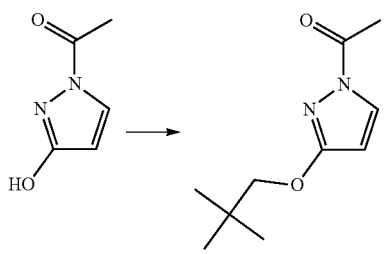

To a suspension of 1-(3-hydroxypyrazol-1-yl)ethanone (1.21 g, 9.60 mmol) in anhydrous THF (20 mL) was added triphenyl phosphine (2.78 g, 10.6 mmol) and 2,2-dimethylpropan-1-ol (846 mg, 9.60 mmol). The reaction mixture was cooled down in an ice-bath under nitrogen. DIAD (2.1 mL, 10.7 mmol) was added dropwise via a syringe over 3 min. The reaction mixture was then stirred under nitrogen warming to room temperature overnight. The reaction mixture was diluted with ethyl acetate (100 mL) and the combined organic phase was washed with aqueous saturated sodium bicarbonate (2×50 mL), brine (50 mL) and dried over sodium sulfate and concentrated under reduced pressure. The residue was purified by silica gel column chromatography using a gradient of ethyl acetate (0 to 30%) in hexanes, to provide 1-[3-(2,2-dimethylpropoxy)pyrazol-1-yl]ethanone (967 mg, 51%) as a yellow solid. ESI-MS m/z calc. 196.12119, found 197.3 (M+1)+; Retention time: 1.62 minutes; 1H NMR (400 MHz, Chloroform-d) δ 8.05 (d, J=3.0 Hz, 1H), 5.97 (d, J=3.0 Hz, 1H), 3.89 (s, 2H), 2.58 (s, 3H), 1.03 (s, 9H).

Step 2: 3-(2,2-dimethylpropoxy)-1H-pyrazole

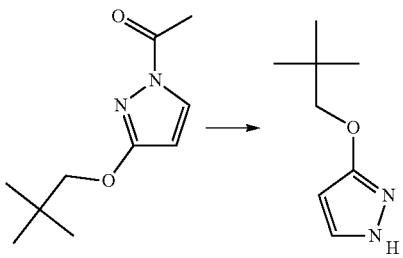

1-[3-(2,2-dimethylpropoxy)pyrazol-1-yl]ethanone (960 mg, 4.89 mmol), MeOH (15 mL) and NaOH (815 µL of 6 M, 4.89 mmol) (6N aqueous) were stirred at room temperature for 21 hours. The volatiles were removed under reduced pressure. The residue was taken in EtOAc (25 mL) and brine (20 ml) and two phases were separated. The aqueous phase was further extracted with EtOAc (2×25 mL) and the combined organic extracts were dried over sodium sulfate and evaporated under reduced pressure to give 3-(2,2-dimethylpropoxy)-1H-pyrazole (719 mg, 95%) as an off-white solid. ESI-MS m/z calc. 154.11061, found 155.3 (M+1)+; Retention time: 1.13 minutes; 1H NMR (400 MHz, Chloroform-d) δ 7.36 (d, J=2.4 Hz, 1H), 5.74 (d, J=2.5 Hz, 1H), 3.81 (s, 2H), 1.02 (s, 9H).

Step 3: Tert-butyl 2-chloro-6-[3-(2,2-dimethylpropoxy)pyrazol-1-yl]pyridine-3-carboxylate

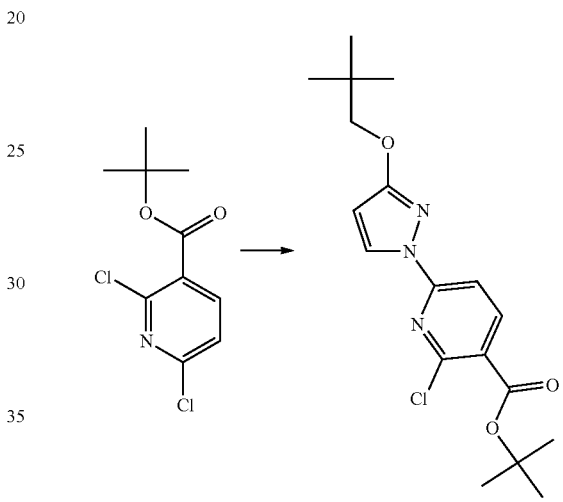

NaH (95 mg, 2.375 mmol) (60% oil suspension) (slight exotherm noticed) was added to 3-(2,2-dimethylpropoxy)-1H-pyrazole (363 mg, 2.35 mmol) in anhydrous DMF (3 mL) and the reaction mixture was stirred until gas evolution stopped. Tert-butyl 2,6-dichloropyridine-3-carboxylate (530 mg, 2.14 mmol) was added portionwise and the reaction mixture was stirred at 100° C. under nitrogen for 1 hour. The reaction mixture was diluted with EtOAc (60 mL) and water+brine (60 mL) and the two phases were separated. The aqueous phase was further extracted with EtOAc (2×30 mL). The combined extracts were dried over sodium sulfate and the solvent removed under reduced pressure. The residue was purified by silica gel column chromatography using a gradient of EtOAc (0 to 20%-over 40 min) in hexanes to give tert-butyl 2-chloro-6-[3-(2,2-dimethylpropoxy)pyrazol-1-yl]pyridine-3-carboxylate (497 mg, 64%) as a yellow solid. ESI-MS m/z calc. 365.1506, found 366.2 (M+1)+; Retention time: 2.44 minutes.

2179

Step 4: 2-chloro-6-[3-(2,2-dimethylpropoxy)pyrazol-1-yl]pyridine-3-carboxylic acid

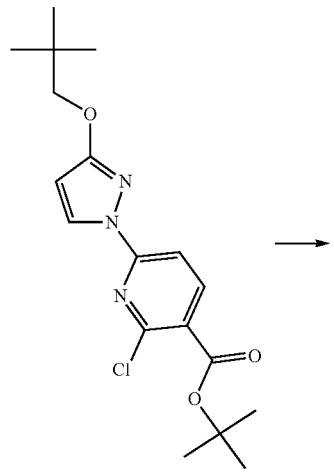

Tert-butyl 2-chloro-6-[3-(2,2-dimethylpropoxy)pyrazol-1-yl]pyridine-3-carboxylate (497 mg, 1.36 mmol), DCM (5 mL) and TFA (1.5 mL, 19.5 mmol) were stirred at 40° C. for 4 hours. The volatiles were removed by evaporation under reduced pressure to give 2-chloro-6-[3-(2,2-dimethylpropoxy)pyrazol-1-yl]pyridine-3-carboxylic acid (413 mg, 98%) as a white solid. ESI-MS m/z calc. 309.088, found 310.1 (M+1)$^+$; Retention time: 1.8 minutes; 1H NMR (400 MHz, DMSO-d$_6$) δ 13.58 (s, 1H), 8.42 (dd, J=2.8, 0.8 Hz, 1H), 8.38 (d, J=8.4 Hz, 1H), 7.74 (d, J=8.5 Hz, 1H), 6.22 (dd, J=2.8, 0.8 Hz, 1H), 3.93 (s, 2H), 1.01 (s, 9H).

2180

Step 5: N-[(2-amino-3-pyridyl)sulfonyl]-2-chloro-6-[3-(2,2-dimethylpropoxy)pyrazol-1-yl]pyridine-3-carboxamide

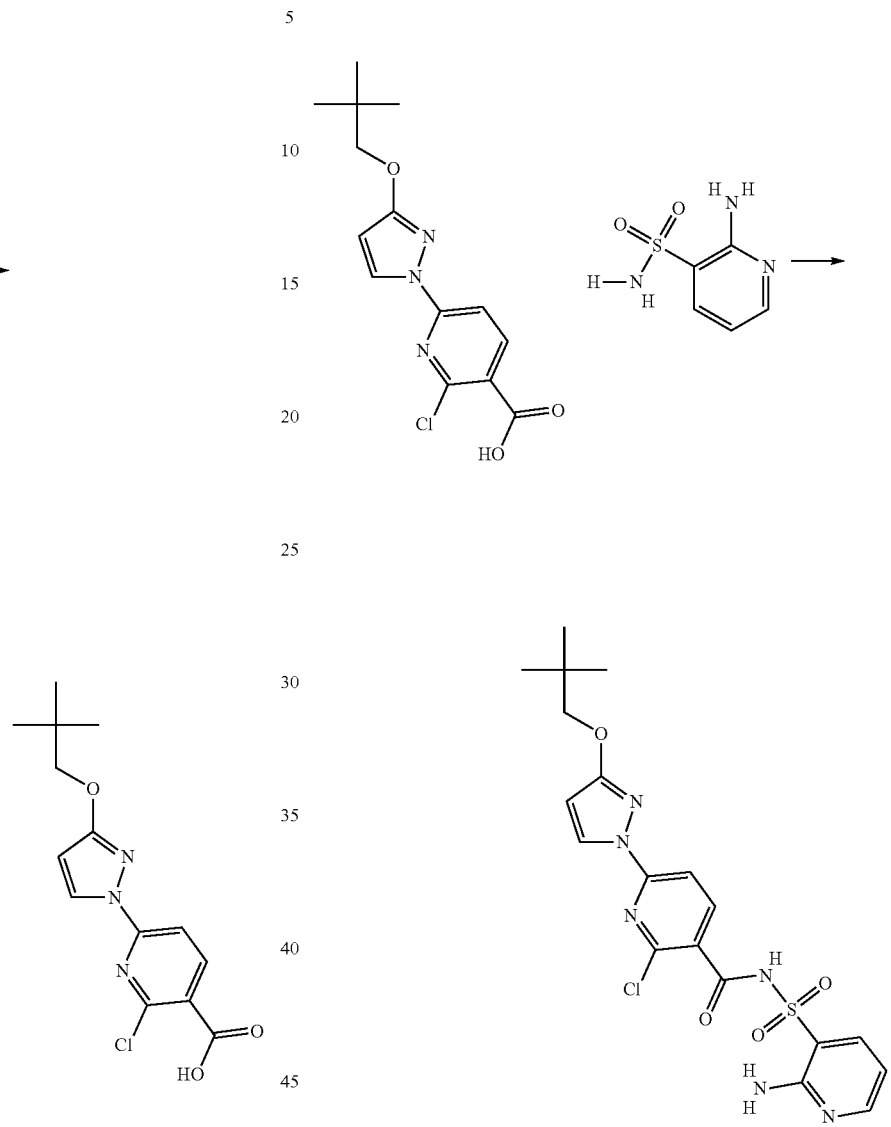

DMF (1 mL) was added to 2-chloro-6-[3-(2,2-dimethylpropoxy)pyrazol-1-yl]pyridine-3-carboxylic acid (105 mg, 0.34 mmol) and CDI (69 mg, 0.43 mmol) and the reaction mixture was stirred at 40° C. under nitrogen for 1 hour. In a separate 4 mL vial, 2-aminopyridine-3-sulfonamide (73 mg, 0.42 mmol) was dissolved under nitrogen in anhydrous DMF (1 mL). NaH (22 mg, 0.55 mmol) (60% oil suspension) was added and the reaction mixture was stirred under nitrogen until gas evolution stopped, then stirred at 40° C. for one hour. The two reaction mixtures were combined and stirred at room temperature for 4 hours. Water and ice was added, followed by acetic acid (400 μL, 7.034 mmol). The resulting solid was filtered, washed with water and dried to give N-[(2-amino-3-pyridyl)sulfonyl]-2-chloro-6-[3-(2,2-dimethylpropoxy)pyrazol-1-yl]pyridine-3-carboxamide (150 mg, 95%) as a white solid. The product was used for the next step without any further purification. ESI-MS m/z calc. 464.10336, found 465.2 (M+1)$^+$; Retention time: 1.5 minutes.

Step 6: N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975)

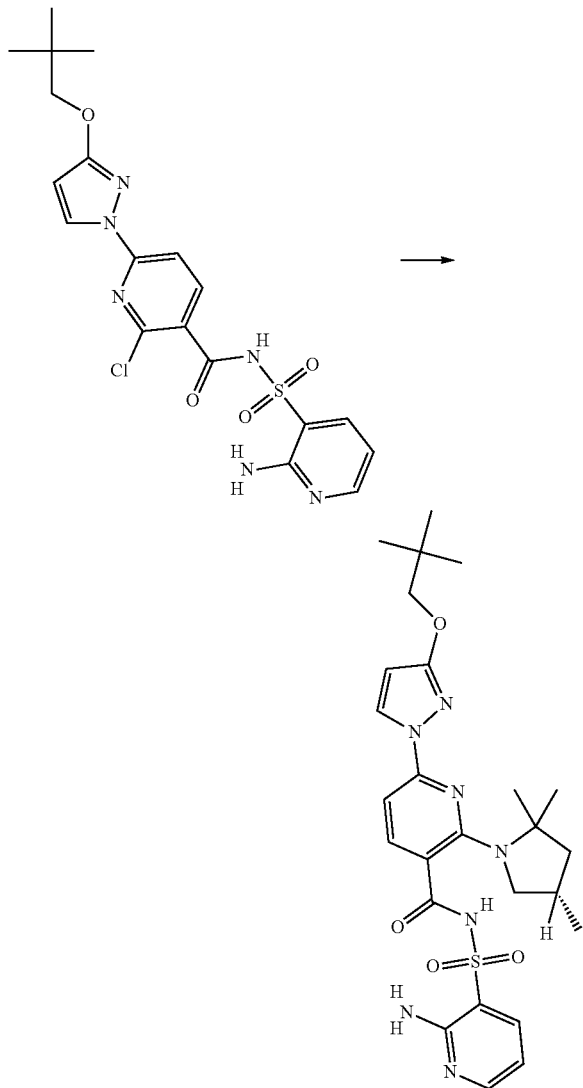

N-[(2-amino-3-pyridyl)sulfonyl]-2-chloro-6-[3-(2,2-dimethylpropoxy)pyrazol-1-yl]pyridine-3-carboxamide (150 mg, 0.32 mmol), (4S)-2,2,4-trimethylpyrrolidine (HCl salt) (195 mg, 1.30 mmol), K$_2$CO$_3$ (274 mg, 1.98 mmol) and anhydrous DMSO (480 μL) were stirred at 150° C. for 7.5 hours under an atmosphere of nitrogen. The reaction mixture was poured into a mixture of water (25 mL) and acetic acid (400 μL, 7.034 mmol) and the resulting yellow solid was separated by filtration. The wet solid was dissolved in DCM, the organic phase was dried over sodium sulfate and the solvents evaporated to give a crude glass, which was purified by silica gel column chromatography using a gradient of MeOH (0 to 10%) in DCM. Evaporation of the solvent gave an off-white solid which was dissolved in MeOH (3 mL) and purified by reverse phase preparative HPLC using a gradient of MeCN in water (1 to 99% over 15 min) and HCl as a modifier (3×950 uL injections) to give N-[(2-amino-3-pyridyl)sulfonyl]-6-[3-(2,2-dimethylpropoxy)pyrazol-1-yl]-2-[(4S)-2,2,4-trimethylpyrrolidin-1-yl]pyridine-3-carboxamide (Compound 1975) (75 mg, 42%) as a tan solid. ESI-MS m/z calc. 541.24713, found 542.3 (M+1)$^+$; Retention time: 1.65 minutes; 1H NMR (400 MHz, DMSO-d$_6$) δ 12.45 (s, 1H), 8.24 (dd, J=4.7, 1.9 Hz, 1H), 8.20 (d, J=2.8 Hz, 1H), 8.03 (dd, J=7.8, 1.9 Hz, 1H), 7.84 (d, J=8.3 Hz, 1H), 6.95 (d, J=8.2 Hz, 1H), 6.77 (dd, J=7.8, 4.8 Hz, 1H), 6.69 (broad s, 2H), 6.14 (d, J=2.7 Hz, 1H), 3.89 (s, 2H), 2.45 (d, J=8.9 Hz, 2H), 2.12 (br s, 1H), 1.85 (dd, J=11.9, 5.4 Hz, 1H), 1.55 (s, 3H), 1.53 (s, 3H), 1.43-1.33 (m, 1H), 1.00 (s, 9H), 0.74 (d, J=6.2 Hz, 3H).

The following compounds can be synthesized using the procedures described herein:

N-[(2-amino-3-pyridyl)sulfonyl]-6-(3-isobutylpyrazol-1-yl)-2-[(4S)-2,2,4-trimethylpyrrolidin-1-yl]pyridine-3-carboxamide (Compound 2036), N-[(2-amino-3-pyridyl)sulfonyl]-6-[4-(2,2-dimethylpropoxy)pyrazol-1-yl]-2-[(4S)-2,2,4-trimethylpyrrolidin-1-yl]pyridine-3-carboxamide (Compound 2406), 6-(3-isopropoxypyrazol-1-yl)-N-[(2-oxo-1H-pyridin-3-yl)sulfonyl]-2-[(4S)-2,2,4-trimethylpyrrolidin-1-yl]pyridine-3-carboxamide (Compound 2360), N-(benzenesulfonyl)-6-(4-isobutoxypyrazol-1-yl)-2-[(4S)-2,2,4-trimethylpyrrolidin-1-yl]pyridine-3-carboxamide (Compound 1912), N-[(2-amino-3-pyridyl)sulfonyl]-6-(3-ethoxy-4-methylpyrazol-1-yl)-2-[(4S)-2,2,4-trimethylpyrrolidin-1-yl]pyridine-3-carboxamide (Compound 2248), N-[(2-amino-3-pyridyl)sulfonyl]-6-[3-(2-ethoxyethoxy)pyrazol-1-yl]-2-[(4S)-2,2,4-trimethylpyrrolidin-1-yl]pyridine-3-carboxamide (Compound 1742), N-[(6-amino-2-pyridyl)sulfonyl]-6-[4-(2,2-dimethylpropoxy)pyrazol-1-yl]-2-[(4S)-2,2,4-trimethylpyrrolidin-1-yl]pyridine-3-carboxamide (Compound 2603), 6-[3-(2,2-dimethylpropoxy)pyrazol-1-yl]-N-[(2-oxo-1H-pyridin-3-yl)sulfonyl]-2-[(4S)-2,2,4-trimethylpyrrolidin-1-yl]pyridine-3-carboxamide (Compound 2578), N-[(2-amino-3-pyridyl)sulfonyl]-6-(4-isobutoxypyrazol-1-yl)-2-[(4S)-2,2,4-trimethylpyrrolidin-1-yl]pyridine-3-carboxamide (Compound 1895), 6-(3-isobutoxy-4-methyl-pyrazol-1-yl)-N-[(2-oxo-1H-pyridin-3-yl)sulfonyl]-2-[(4S)-2,2,4-trimethylpyrrolidin-1-yl]pyridine-3-carboxamide (Compound 1743), N-[(2-amino-3-pyridyl)sulfonyl]-6-(3-isopropoxypyrazol-1-yl)-2-[(4S)-2,2,4-trimethylpyrrolidin-1-yl]pyridine-3-carboxamide (Compound 1844), N-[(2-amino-3-pyridyl)sulfonyl]-6-[3-[(2S)-2-methylbutoxy]pyrazol-1-yl]-2-[(4S)-2,2,4-trimethylpyrrolidin-1-yl]pyridine-3-carboxamide (Compound 2458), N-[(2-amino-3-pyridyl)sulfonyl]-6-(3-sec-butoxypyrazol-1-yl)-2-[(4S)-2,2,4-trimethylpyrrolidin-1-yl]pyridine-3-carboxamide (Compound 1970), N-[(2-amino-3-pyridyl)sulfonyl]-6-[3-(3-hydroxy-2-methyl-propoxy)pyrazol-1-yl]-2-[(4S)-2,2,4-trimethylpyrrolidin-1-yl]pyridine-3-carboxamide (Compound 2192), N-[(6-amino-2-pyridyl)sulfonyl]-6-(3-isopropoxypyrazol-1-yl)-2-[(4S)-2,2,4-trimethylpyrrolidin-1-yl]pyridine-3-carboxamide (Compound 1709), N-[(2-amino-3-pyridyl)sulfonyl]-6-(3-isobutoxy-4-methyl-pyrazol-1-yl)-2-[(4S)-2,2,4-trimethylpyrrolidin-1-yl]pyridine-3-carboxamide (Compound 1758), N-cyclopropylsulfonyl-6-[3-(2,2-dimethylpropoxy)pyrazol-1-yl]-2-[(4S)-2,2,4-trimethylpyrrolidin-1-yl]pyridine-3-carboxamide (Compound 2554), 6-(4-isobutoxypyrazol-1-yl)-N-[(2-oxo-1H-pyridin-3-yl)
sulfonyl]-2-[(4S)-2,2,4-trimethylpyrrolidin-1-yl]pyri-
dine-3-carboxamide (Compound 1760), N-[(2-amino-3-pyridyl)sulfonyl]-6-(3-isobutoxy-5-methyl-
pyrazol-1-yl)-2-[(4S)-2,2,4-trimethylpyrrolidin-1-yl]
pyridine-3-carboxamide (Compound 2238), N-[(2-amino-3-pyridyl)sulfonyl]-6-[3-[2-(2-ethoxyethoxy)
ethoxy]pyrazol-1-yl]-2-[(4S)-2,2,4-trimethylpyrrolidin-
1-yl]pyridine-3-carboxamide (Compound 2326), N-[(2-amino-3-pyridyl)sulfonyl]-6-(3-isobutoxypyrazol-1-
yl)-2-(6-methyl-8-azaspiro[3.4]octan-8-yl)pyridine-3-
carboxamide (Compound 2604) (Isomer 1) (Compound
2481) (Isomer 2) (Compound 2194) (Isomer 3) (Com-
pound 2615) (Isomer 4), N-[(2-amino-3-pyridyl)sulfonyl]-6-[3-[2,3,3,3-tetradeute-
rio-2-(trideuteriomethyl)propoxy]pyrazol-1-yl]-2-[(4S)-
2,2,4-trimethylpyrrolidin-1-yl]pyridine-3-carboxamide
(Compound 1887), 6-(3-ethoxy-4-methyl-pyrazol-1-yl)-N-[(2-oxo-1H-pyridin-
3-yl)sulfonyl]-2-[(4S)-2,2,4-trimethylpyrrolidin-1-yl]
pyridine-3-carboxamide (Compound 1856), 6-(3-isobutoxypyrazol-1-yl)-N-[(2-oxo-1H-pyridin-3-yl)
sulfonyl]-2-[(4S)-2,2,4-trimethylpyrrolidin-1-yl]pyri-
dine-3-carboxamide (Compound 1896), N-[(6amino-2-pyridyl)sulfonyl]-6-[3-(2,2-dimethyl-
propoxy)pyrazol-1-yl]-2-[(4S)-2,2,4-trimethylpyrrolidin-
1-yl]pyridine-3-carboxamide (Compound 1952), N-[(2-amino-3-pyridyl)sulfonyl]-6-[3-[3,3,3-trideuterio-2,
2-bis(trideuteriomethyl)propoxy]pyrazol-1-yl]-2-[(4S)-2,
2,4-trimethylpyrrolidin-1-yl]pyridine-3-carboxamide
(Compound 2703), N-[(2-amino-3-pyridyl)sulfonyl]-6-[3-(1-methylpropoxy)
pyrazol-1-yl]-2-[(4S)-2,2,4-trimethylpyrrolidin-1-yl]
pyridine-3-carboxamide (Compound 2704), N-(benzenesulfonyl)-6-[3-(2,2-dimethylpropoxy)pyrazol-1-
yl]-2-[(4S)-2,2,4-trimethylpyrrolidin-1-yl]pyridine-3-car-
boxamide (Compound 1114), N-[(2-amino-3-pyridyl)sulfonyl]-6-(3-cyclopropylpyrazol-
1-yl)-2-[(4S)-2,2,4-trimethylpyrrolidin-1-yl]pyridine-3-
carboxamide (Compound 2701), N-cyclopropylsulfonyl-2-[(2S,5R)-2,5-dimethylpyrrolidin-
1-yl]-6-(3-phenylpyrazol-1-yl)pyridine-3-carboxamide
(Compound 2676), N-cyclopropylsulfonyl-6-(3-phenylpyrazol-1-yl)-2-[(4S)-2,
2,4-trimethylpyrrolidin-1-yl]pyridine-3-carboxamide
(Compound 2674), N-[(2-amino-3-pyridyl)sulfonyl]-6-(3-phenylpyrazol-1-yl)-
2-[(4S)-2,2,4-trimethylpyrrolidin-1-yl]pyridine-3-car-
boxamide (Compound 2702), N-[(2-amino-3-pyridyl)sulfonyl]-2-[(2S,5R)-2,5-dimeth-
ylpyrrolidin-1-yl]-6-(3-isobutoxypyrazol-1-yl)pyridine-
3-carboxamide (Compound 1732), N-[(3R)-3-aminopyrrolidin-1-yl]sulfonyl-6-(3-isobutoxy-
pyrazol-1-yl)-2-[(4S)-2,2,4-trimethylpyrrolidin-1-yl]
pyridine-3-carboxamide (Compound 2716), N-cyclopropylsulfonyl-6-[3-(2-pyridyl)pyrazol-1-yl]-2-
[(4S)-2,2,4-trimethylpyrrolidin-1-yl]pyridine-3-carbox-
amide (Compound 2718), N-[(2-amino-3-pyridyl)sulfonyl]-6-[3-(2,2-dimethyl-
propoxy)-4-methyl-pyrazol-1-yl]-2-[(4S)-2,2,4-trimeth-
ylpyrrolidin-1-yl]pyridine-3-carboxamide (Compound
2699), N-[(2-amino-3-pyridyl)sulfonyl]-6-[3-(cyclobutylmethoxy)
pyrazol-1-yl]-2-[(4S)-2,2,4-trimethylpyrrolidin-1-yl]
pyridine-3-carboxamide (Compound 2694) and N-[(2-amino-3-pyridyl)sulfonyl]-6-[3-(cyclopropyl-
methoxy)pyrazol-1-yl]-2-[(4S)-2,2,4-trimethylpyrrolidin-
1-yl]pyridine-3-carboxamide (Compound 2695).

Preparation 110: N-[(2-amino-3-pyridyl)sulfonyl]-6-
(3-isobutoxypyrazol-1-yl)-2-(6-methyl-8-azaspiro
[3.4]octan-8-yl)pyridine-3-carboxamide (Compound
2604) (Isomer 1, R or S stereoisomer) and N-[(2-
amino-3-pyridyl)sulfonyl]-6-(3-isobutoxypyrazol-1-
yl)-2-(6-methyl-8-azaspiro[3.4]octan-8-yl)pyridine-
3-carboxamide (Compound 2481) (Isomer 2, R or
S stereoisomer)

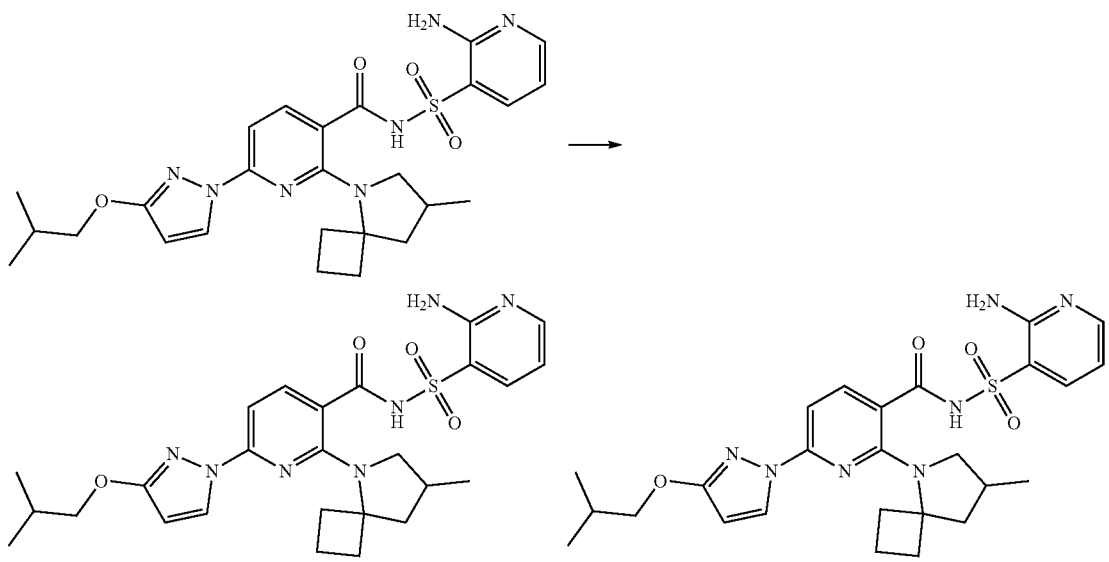

The stereoisomers were separated using supercritical fluid chromatography on a ChiralPak AD-H (250×10 mm), 5 μm column using 30% methanol in CO₂ at a flow rate of 10.0 mL/min. The separated enantiomers were separately concentrated, diluted with ethyl acetate (3 mL) and washed with 1N aqueous hydrochloric acid. The organic layers were dried over sodium sulfate, filtered, and evaporated to dryness to give the pure compounds. SFC Peak 1: N-[(2-amino-3-pyridyl)sulfonyl]-6-(3-isobutoxypyrazol-1-yl)-2-(6-methyl-8-azaspiro[3.4]octan-8-yl)pyridine-3-carboxamide (Compound 2604) (Compound 2481) ESI-MS m/z calc. 539.23145, found 540.2 (M+1)$^+$; Retention time: 1.67 minutes. SFC Peak 2: N-[(2-amino-3-pyridyl)sulfonyl]-6-(3-isobutoxypyrazol-1-yl)-2-(6-methyl-8-azaspiro[3.4]octan-8-yl)pyridine-3-carboxamide (Compound 2604) (Isomer 1, R or S stereoisomer) (Compound 2481) (Isomer 2, R or S stereoisomer) ESI-MS m/z calc. 539.23145, found 540.2 (M+1)$^+$; Retention time: 1.67 minutes.

The following compounds can be synthesized using the procedures described herein:

N-[(2-amino-3-pyridyl)sulfonyl]-6-[3-(2,2-dimethylpropoxy)pyrazol-1-yl]-2-[6-methyl-8-azaspiro[3.4]octan-8-yl]pyridine-3-carboxamide (Compound 2358) (Isomer 1, R or S stereoisomer), followed by SFC column chromatography using ChiralPak AS-H (250×10 mm), 5 μm, using as eluent 38% MeOH (no modifier) in CO₂, N-[(2-amino-3-pyridyl)sulfonyl]-6-[3-[(1-methylpropoxy)pyrazol-1-yl]-2-[(4S)-2,2,4-trimethylpyrrolidin-1-yl]pyridine-3-carboxamide (Compound 2594) (Isomer 2, R or S stereoisomer) using ChiralPak IA (250×4.6 mm), 5 μm; Mobile phase: 25% MeOH:EtOH (50:50; 0.1% TFA) in CO₂.

Preparation 111:
4-(2,2-dimethylpropoxy)-1H-pyrazole

Step 1: tert-butyl 4-hydroxypyrazole-1-carboxylate

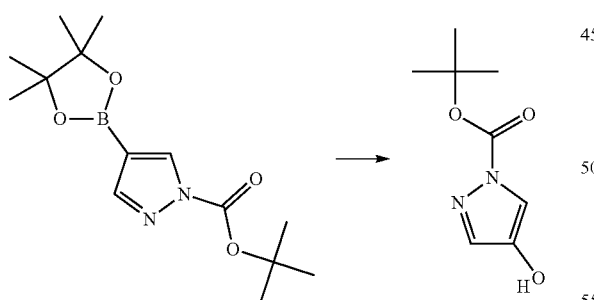

To tert-butyl 4-(4,4,5,5-tetramethyl-1,3,2-dioxaborolan-2-yl)pyrazole-1-carboxylate (25 g, 85 mmol) in THF (170 mL) at 0° C. was added sodium hydroxide (85 mL of 2 M, 170 mmol) followed by hydrogen peroxide (19.27 mL of 30% w/v, 170.0 mmol) and the reaction mixture was stirred at 0° C. for 10 min and RT for 45 min. The reaction mixture was cooled to 0° C. and diluted with DCM and 2 M HCl was added till pH 2 was reached. The organics were separated, dried and concentrated under reduced pressure to give tert-butyl 4-hydroxypyrazole-1-carboxylate (15 g 100%) as yellow solid. ESI-MS m/z calc 184.19, found 185.0 (M+1)$^+$; LCMS retention time (3 min run) 0.63 min.

Step 2: 4-(2,2-dimethylpropoxy)-1H-pyrazole

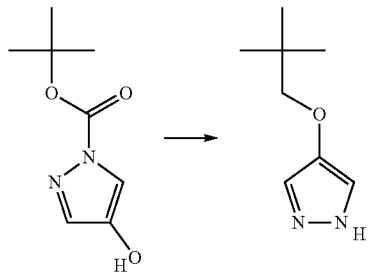

To tert-butyl 4-hydroxypyrazole-1-carboxylate (1000 mg, 5.429 mmol) and Ph₃P (2.136 g, 8.144 mmol) in THF (2.500 mL) was added 2,2-dimethylpropan-1-ol (717.9 mg, 8.144 mmol) at 0° C. To the reaction mixture was added DIAD (1.647 g, 1.578 mL, 8.144 mmol) in THF (2 mL). The reaction mixture was stirred at 60° C. for 16 h, then cooled and diluted with DCM and washed with 6 M HCl solution. The organics were separated, dried and concentrated to give a residue which was purified by silica gel column chromatography using 5-100% EA-hexanes followed by 5-40% EA-DCM to give tert-butyl 4-(2,2-dimethylpropoxy)pyrazole-1-carboxylate (435.5 mg) ESI-MS m/z calc 254.16, found 255.4 (M+1)$^+$; LCMS retention time (3 min run)=1.82 min; 1H NMR (400 MHz, Chloroform-d) δ 7.57 (d, J=1.0 Hz, 1H), 7.51 (d, J=1.0 Hz, 1H), 3.52 (s, 2H), 1.64 (s, 9H), 1.00 (s, 9H). To tert-butyl 4-(2,2-dimethylpropoxy)pyrazole-1-carboxylate (435.5 mg, 1.712 mmol) in DCM (0.2 mL) was added 4M HCl-dixoane (2 mL). After 5 h at RT, the solvent was removed under reduced pressure and the residue was triturated with diethyl ether to give 4-(2,2-dimethylpropoxy)-1H-pyrazole (HCl salt) (210 mg, 20%) ESI-MS m/z calc 154.11, found 155.4 (M+1)$^+$; LCMS retention time (3 min run) 1.13 min.

Preparation 112: 3-isobutoxy-4-methyl-1H-pyrazole

Step 1:
1-(3-hydroxy-4-methyl-pyrazol-1-yl)ethanone

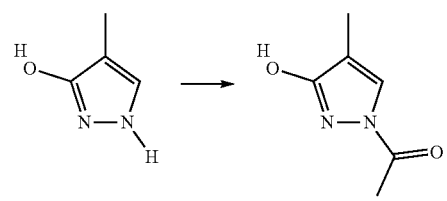

4-methyl-1H-pyrazol-3-ol (1.0 g, 10.2 mmol) and pyridine (4.0 mL, 49.5 mmol) were heated at 95° C. A solution of acetic anhydride (1.0 g, 961.2 μL, 10.2 mmol) in pyridine (1.5 mL, 18.6 mmol) was added dropwise over a period of 2 minutes. The reaction mixture was then stirred at 95° C. for an additional 2 hours. The solvents were removed under reduced pressure and the solid residue was triturated with diethylether (30 mL), filtered, washed with diethylether and dried to give 1-(3-hydroxy-4-methyl-pyrazol-1-yl)ethanone (1.2 g, 86%) as a white solid. ESI-MS m/z calc. 140.05858, found 141.1 (M+1)⁺; Retention time 0.39 minutes; 1H NMR (400 MHz, DMSO-d₆) δ 10.99 (s, 1H), 7.92 (q, J=1.1 Hz, 1H), 2.43 (s, 3H), 1.88 (d, J=1.2 Hz, 3H).

Step 2:
1-(3-isobutoxy-4-methyl-pyrazol-1-yl)ethanone

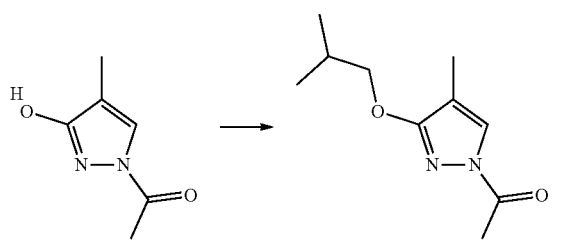

1-Bromo-2-methyl-propane (658 mg, 522 μL, 4.80 mmol) was added to 1-(3-hydroxy-4-methyl-pyrazol-1-yl)ethanone (612 mg, 4.37 mmol), potassium carbonate (905 mg, 6.55 mmol) and anhydrous DMF (5 mL) under nitrogen atmosphere. The reaction mixture was stirred at 80° C. for 2.5 hours, then diluted with EtOAc (50 ml) and water (25 mL) and two phases were separated. The aqueous phase (pH=9-10) was further extracted with EtOAc (20 mL). The combined extracts were dried over sodium sulfate and the solvents evaporated to give a crude oil. The oil was purified by silica gel column chromatography using a gradient of AcOEt (0 to 30%) in hexanes to provide 1-(3-isobutoxy-4-methyl-pyrazol-1-yl)ethanone (726 mg, 85%) as a colorless liquid. ESI-MS m/z calc. 196.12119, found 197.3 (M+1)⁺; Retention time: 1.57 minutes; 1H NMR (400 MHz, Chloroform-d) δ 7.82 (s, 1H), 4.01 (d, J=6.6 Hz, 2H), 2.53 (s, 3H), 2.10 (sep, J=6.7 Hz, 1H), 1.95 (d, J=1.0 Hz, 3H), 1.01 (d, J=6.7 Hz, 6H).

Step 3: 3-isobutoxy-4-methyl-1H-pyrazole

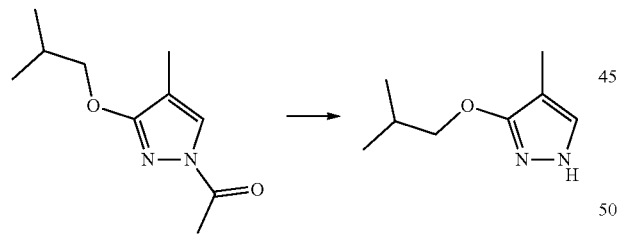

1-(3-isobutoxy-4-methyl-pyrazol-1-yl)ethanone (726 mg, 3.70 mmol) was treated with MeOH (10 mL) and NaOH (617 μL of 6 M, 3.70 mmol) (6N aqueous) at room temperature for 2 hours. The volatiles were removed under reduced pressure. The residue was taken in EtOAc (25 mL) and brine (20 ml) and two phases were separated. The aqueous phase was further extracted with EtOAc (2×25 mL) and the combined extracts were dried over sodium sulfate. After evaporation of the solvent, 3-isobutoxy-4-methyl-1H-pyrazole (564 mg, 99%) was isolated as a slightly colored viscous oil. ESI-MS m/z calc. 154.11061, found 155.0 (M+1)⁺; Retention time: 1.17 minutes; 1H NMR (400 MHz, Chloroform-d) δ 8.83 (broad s, 1H), 7.16-7.09 (m, 1H), 3.95 (d, J=6.7 Hz, 2H), 2.09 (m, 1H), 1.95 (d, J=0.9 Hz, 3H), 1.01 (d, J=6.7 Hz, 6H).

The following compounds can be prepared following the procedures described herein:

3-(2-ethoxyethoxy)-1H-pyrazole, (S)-3-(2-methylbutoxy)-1H-pyrazole, 3-(sec-butoxy)-1H-pyrazole, 3-((1H-pyrazol-5-yl)oxy)-2-methylpropan-1-ol, 5-isopropoxy-1H-pyrazole, 5-isobutoxy-3-methyl-1H-pyrazole, 3-(2-(2-ethoxyethoxy)ethoxy)-1H-pyrazole and 3-(2-(methyl-d₃)propoxy-2,3,3,3-d₄)-1H-pyrazole Preparation 113: N-[(6-amino-2-pyridyl)sulfonyl]-3-fluoro-4-(3-fluoro-5-isobutoxy-phenyl)-2-[(4AS)-2,2,4-trimethylpyrrolidin-1-yl]benzamide (Compound 2634)

Step 1: N-[(6-amino-2-pyridyl)sulfonyl]-4-bromo-2,3-difluoro-benzamide

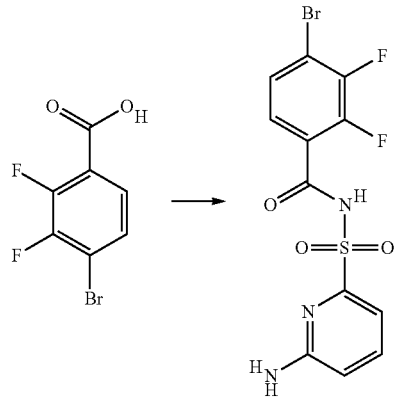

To 4-bromo-2,3-difluoro-benzoic acid (2.66 g, 11.2 mmol) in DMF (2.30 mL) was added at RT di(imidazol-1-yl)methanone (2.73 g, 16.8 mmol) and reaction mixture was heated at 65° C. for 1 h. Separately to 6-aminopyridine-2-sulfonamide (2.43 g, 14.0 mmol) in DMF (2 mL) was added sodium hydride (561 mg, 14.0 mmol) at 0° C. and stirred for 10 min and RT for 1 h. The reaction mixture was cooled back to 0° C. and the CDI adduct was added and reaction mixture was heated at 65° C. for 1.5 h, then cooled to RT and diluted with ethyl acetate and washed with brine solution. The organics were separated, dried and concentrated under reduced pressure to give a residue which was purified by silica gel column chromatography eluting with 0-100% ethyl acetate-hexanes to give N-[(6-amino-2-pyridyl)sulfonyl]-4-bromo-2,3-difluoro-benzamide (3.80 g, 986%). ESI-MS m/z calc 390.94, found 394.2 (M+4)⁺; LCMS retention time (3 min run) 1.13 min.

2189

Step 2: N-[(6-amino-2-pyridyl)sulfonyl]-2,3-difluoro-4-(3-fluoro-5-isobutoxy-phenyl)benzamide

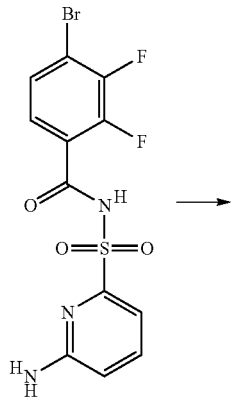

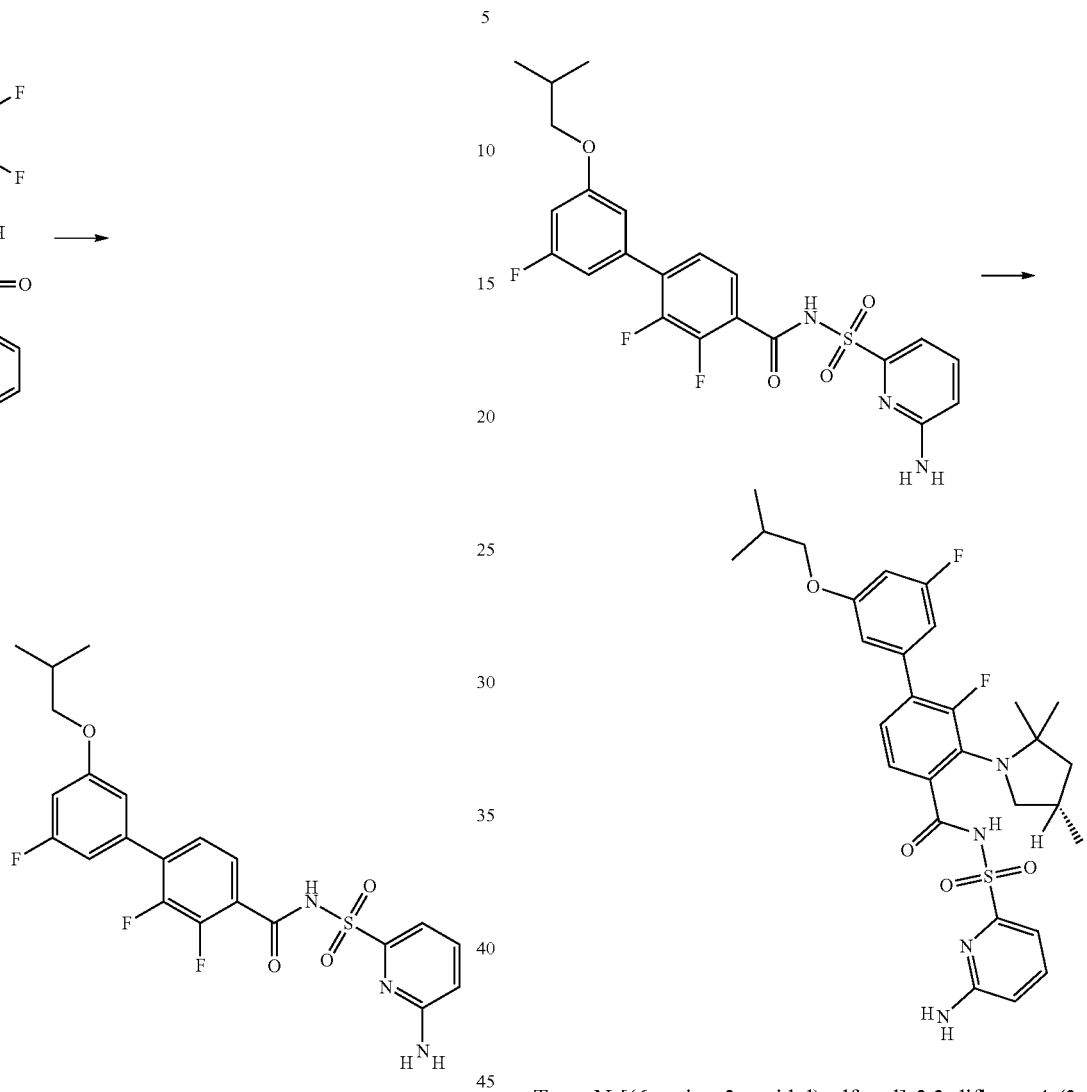

To mixture of N-[(6-amino-2-pyridyl)sulfonyl]-4-bromo-2,3-difluoro-benzamide (1.3 g, 3.3 mmol) and (3-fluoro-5-isobutoxy-phenyl)boronic acid (1.1 g, 5.0 mmol) and K$_2$CO$_3$ (1.4 g, 9.9 mmol) was added cyclopentyl(diphenyl)phosphane; dichloropalladium; iron (243 mg, 0.33 mmol) and DMF (8.8 mL) and water (2.2 mL) and the reaction mixture was stirred under nitrogen at 100° C. for 16 h. The reaction mixture was cooled, filtered over pad of Celite and filtrate was diluted with ethyl acetate and brine solution. The organics were separated, dried and concentrated to give a residue which was purified by silica gel column chromatography using 5-100% ethyl acetate-DCM as eluent to give N-[(6-amino-2-pyridyl)sulfonyl]-2,3-difluoro-4-(3-fluoro-5-isobutoxy-phenyl)benzamide (356 mg, 22%). 1H NMR (400 MHz, Methanol-d$_4$) δ 7.64-7.53 (m, 2H), 7.29 (d, J=7.4 Hz, 1H), 7.25-7.18 (m, 1H), 6.90 (d, J=2.7 Hz, 1H), 6.88-6.81 (m, 1H), 6.73 (dt, J=10.8, 2.3 Hz, 1H), 6.64 (d, J=8.3 Hz, 1H), 3.79 (d, J=6.4 Hz, 2H), 2.07 (hept, J=6.7 Hz, 1H), 1.04 (d, J=6.7 Hz, 6H); ESI-MS m/z calc 479.11, found 480.2 (M+1)$^+$; LCMS retention time (3 min run) 1.78 min.

2190

Step 3: N-[(6-amino-2-pyridyl)sulfonyl]-3-fluoro-4-(3-fluoro-5-isobutoxy-phenyl)-2-[(4S)-2,2,4-trimethylpyrrolidin-1-yl]benzamide (Compound 2634)

To N-[(6-amino-2-pyridyl)sulfonyl]-2,3-difluoro-4-(3-fluoro-5-isobutoxy-phenyl)benzamide (356 mg, 0.74 mmol) and K$_2$CO$_3$ (277 mg, 2.00 mmol) in NMP (650 l) was added (4S)-2,2,4-trimethylpyrrolidine (HCl salt) (150 mg, 1.00 mmol) and the reaction mixture was stirred at 195° C. for 5 h, then cooled and filtered and diluted with EtOAc and brine solution. The organics were separated, dried and concentrated under reduced pressure to give a residue which was purified using silica gel column chromatography using 0-15% MeOH-DCM to give N-[(6-amino-2-pyridyl)sulfonyl]-3-fluoro-4-(3-fluoro-5-isobutoxy-phenyl)-2-[(4S)-2,2,4-trimethylpyrrolidin-1-yl]benzamide (Compound 2634) (42 mg, 2%) 1H NMR (400 MHz, Methanol-d$_4$) δ 7.69 (s, 1H), 7.32 (t, J=7.9 Hz, 1H), 7.26 (s, 1H), 7.08 (dd, J=7.3, 0.8 Hz, 1H), 6.62-6.51 (m, 2H), 6.44 (dd, J=19.3, 9.7 Hz, 2H), 3.58 (s, 1H), 3.49 (d, J=6.4 Hz, 2H), 2.52 (t, J=0.8 Hz, 1H), 2.45 (s, 1H), 1.90 (s, 1H), 1.82-1.69 (m, 2H), 1.53 (s, 1H), 1.04 (s, 3H), 0.92 (s, 6H), 0.74 (d, J=6.7 Hz, 6H). ESI-MS m/z calc 572.2, found 573.3 (M+1)$^+$; LCMS retention time (3 min run) 1.91 min.

Preparation 114: N-[(6-amino-5-hydroxy-2-pyridyl)sulfonyl]-2-(2,6-dimethylphenoxy)-6-(3-fluoro-5-isobutoxy-phenyl)pyridine-3-carboxamide (Compound 2331)

Step 1: 6-bromo-2-nitro-pyridin-3-ol

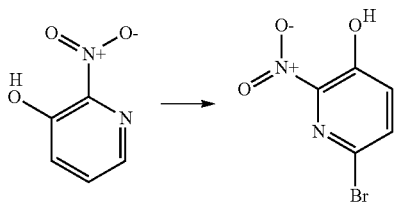

A solution of phenyl trimethyl ammonium tribromide (8.45 g, 22.3 mmol) in THF (68 mL) was added dropwise to a stirred solution of 2-nitropyridin-3-ol (3.00 g, 21.4 mmol) and triethylamine (4.33 g, 5.97 mL, 42.8 mmol) in THF (91 mL) at −40° C. The addition was done over a period of 5 minutes and the reaction mixture was kept at −40° C. for 1 h. 1N HCl and aq. Na$_2$S2O3 were added and the aq. phase was extracted with dichloromethane. The combined organic phase was washed with brine, dried over MgSO$_4$, filtered and the filtrate evaporated under reduced pressure. The residue was purified by silica gel column chromatography eluted with 30 to 100% EtOAc/Hexanes to afford the title compound as a yellow solid.

Step 2: 3-benzyloxy-6-bromo-2-nitro-pyridine

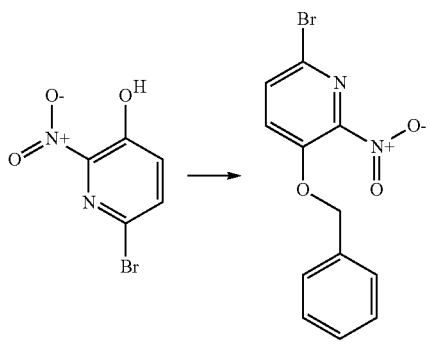

To a solution of 6-bromo-2-nitro-pyridin-3-ol (5.04 g, 23.0 mmol) in DMF (40 mL) was added potassium carbonate (6.36 g, 46.0 mmol) followed by the addition of bromomethylbenzene (4.13 g, 2.87 mL, 24.2 mmol). The reaction mixture was heated at 60° C. overnight, then partitioned between EtOAc and water. The aqueous layer was extracted with EtOAc (3×). The combined organic layers were washed with water (3×), brine, dried over MgSO$_4$, filtered and concentrated under reduced pressure. The crude material was suspended in hexane, collected via filtration and air dried to provide 3-benzyloxy-6-bromo-2-nitro-pyridine (6.22 g, 87%) as a yellow solid.

Step 3: methyl 3-[(5-benzyloxy-6-nitro-2-pyridyl)sulfonyl]propanoate

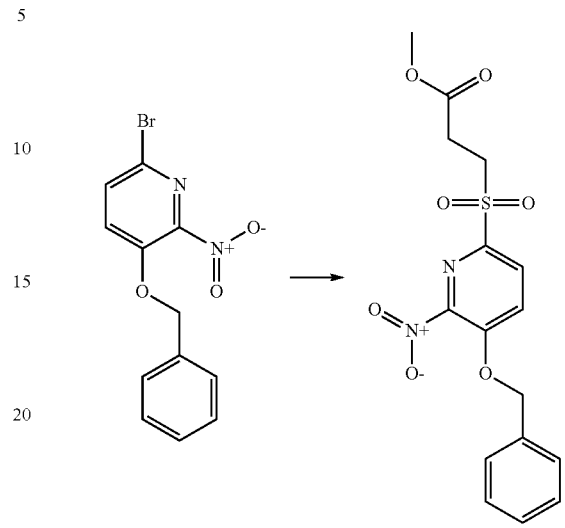

A mixture of 3-benzyloxy-6-bromo-2-nitro-pyridine (6.21 g, 20.1 mmol) and (3-methoxy-3-oxo-propyl)sulfinyloxysodium (3.50 g, 20.1 mmol) in DMSO (50 mL) was purged with nitrogen for 2 minutes. Iodocopper (7.66 g, 40.2 mmol) was added. The reaction mixture was heated at 80° C. for 24 h, then partitioned between EtOAc and sat. NH$_4$Cl. The resulting precipitate was removed via filtration and washed with EtOAc. The aqueous layer was extracted with EtOAc (3×). The combined organic layers were washed with water (3×), brine, dried over MgSO$_4$, filtered and concentrated under reduced pressure. The crude material was purified by silica gel column chromatography (40-60% EtOAc-Hex) to provide methyl 3-[(5-benzyloxy-6-nitro-2-pyridyl)sulfonyl]propanoate (2.50 g, 33%) as a brown solid.

Step 4: 5-benzyloxy-6-nitro-pyridine-2-sulfinate

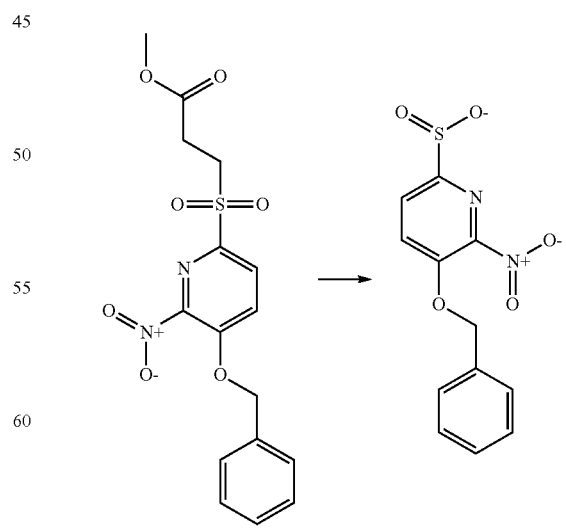

THF (1 mL) was added to a suspension of methyl 3-[(5-benzyloxy-6-nitro-2-pyridyl)sulfonyl]propanoate (76 mg, 0.2 mmol) in MeOH (2 mL). Sodium methoxide (400 μL of 0.5 M, 0.2 mmol) (in MeOH) was added dropwise. The reaction mixture was stirred at room temperature for 30 minutes, then evaporated under reduced pressure to provide a light brown solid. The crude material was used directly in next step without further purification.

Step 5: 5-benzyloxy-6-nitro-pyridine-2-sulfonamide

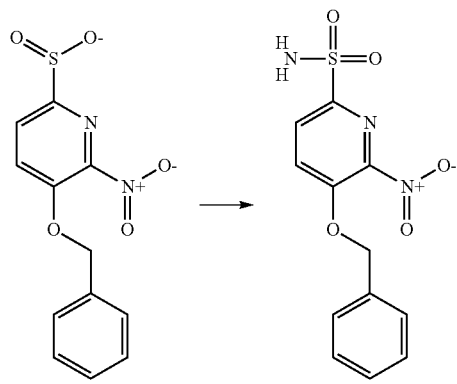

To a solution of amino hydrogen sulfate (3.68 g, 32.5 mmol) and sodium acetate (5.32 g, 65.0 mmol) in water (40 mL) was added 5-benzyloxy-6-nitro-pyridine-2-sulfinate (sodium salt) (2.06 g, 6.5 mmol) in MeOH (25 mL). The reaction mixture was stirred at room temperature overnight, then partitioned between water and EtOAc. The aqueous layer was extracted with EtOAc (3×). The combined organic layers were washed with brine, dried over MgSO₄, filtered and concentrated under reduced pressure to provide 5-benzyloxy-6-nitro-pyridine-2-sulfonamide (1.10 g, 55%) as a crude material. The crude material (light yellow solid) was used directly in next step without further purification.

Step 6: N-[(5-benzyloxy-6-nitro-2-pyridyl)sulfonyl]-2-(2,6-dimethylphenoxy)-6-(3-fluoro-5-isobutoxy-phenyl)pyridine-3-carboxamide

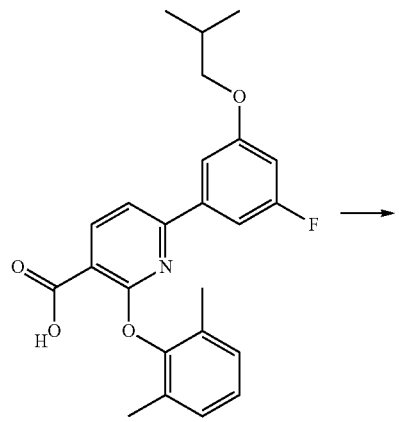

-continued

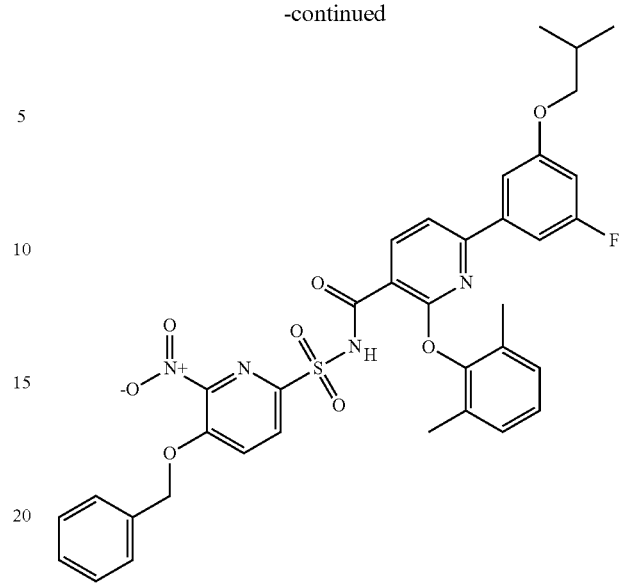

To a mixture of 5-benzyloxy-6-nitro-pyridine-2-sulfonamide (155 mg, 0.50 mmol), 2-(2,6-dimethylphenoxy)-6-(3-fluoro-5-isobutoxy-phenyl)pyridine-3-carboxylic acid (248 mg, 0.60 mmol) and HATU (228 mg, 0.60 mmol) in DMF (10 mL) was added potassium carbonate (207 mg, 1.50 mmol). The reaction mixture was heated at 60° C. for 7 h, partitioned between EtOAc and water. The aqueous layer was extracted with EtOAc (3×). The combined organic layers were washed with water (3×), brine, dried over MgSO₄, filtered and concentrated under reduced pressure. The crude material was purified by silica gel column chromatography (20-40% EtOAc-Hex) to provide N-[(5-benzyloxy-6-nitro-2-pyridyl)sulfonyl]-2-(2,6-dimethylphenoxy)-6-(3-fluoro-5-isobutoxy-phenyl)pyridine-3-carboxamide (220 mg, 63%) as a yellow solid.

Step 7: N-[(6-amino-5-benzyloxy-2-pyridyl)sulfonyl]-2-(2,6-dimethylphenoxy)-6-(3-fluoro-5-isobutoxy-phenyl)pyridine-3-carboxamide (Compound 1762)

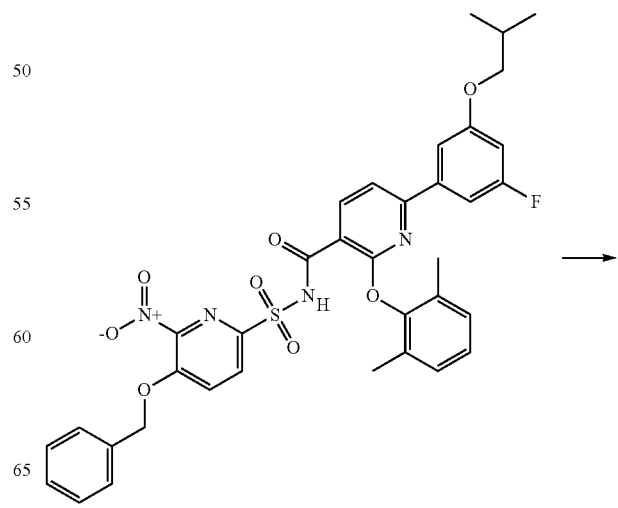

-continued

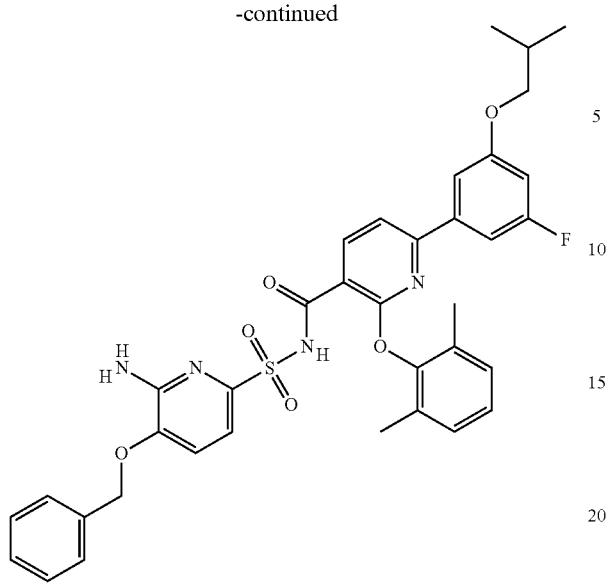

To a solution of N-[(5-benzyloxy-6-nitro-2-pyridyl)sulfonyl]-2-(2,6-dimethylphenoxy)-6-(3-fluoro-5-isobutoxy-phenyl)pyridine-3-carboxamide (215 mg, 0.31 mmol) in dioxane (4 mL) and ethanol (2 mL) was added Fe (171 mg, 3.07 mmol) and HCl (511 µL of 6 M, 3.07 mmol). The reaction mixture was heated at 65° C. for 30 min. The iron was removed and the precipitate was collected via filtration. The filtrate was concentrated to dryness, dissolved in DMSO, filtered and purified by preparative HPLC to provide N-[(6-amino-5-benzyloxy-2-pyridyl)sulfonyl]-2-(2,6-dimethylphenoxy)-6-(3-fluoro-5-isobutoxy-phenyl)pyridine-3-carboxamide (Compound 1762) (25 mg, 12%) 1H NMR (400 MHz, DMSO-d$_6$) δ 12.23 (s, 1H), 8.13 (d, J=7.8 Hz, 1H), 7.81 (d, J=7.9 Hz, 1H), 7.57-7.46 (m, 2H), 7.45-7.23 (m, 5H), 7.23-7.04 (m, 5H), 6.83 (dt, J=10.9, 2.3 Hz, 1H), 6.33 (s, 2H), 5.24 (s, 2H), 3.61 (d, J=6.6 Hz, 2H), 2.05 (s, 6H), 1.98 (dt, J=13.4, 6.7 Hz, 1H), 0.96 (d, J=6.6 Hz, 6H). ESI-MS m/z calc. 670.22614, found 670.0 (M+1)$^+$; Retention time: 3.6 minutes.

Step 8: N-[(6-amino-5-hydroxy-2-pyridyl)sulfonyl]-2-(2,6-dimethylphenoxy)-6-(3-fluoro-5-isobutoxy-phenyl)pyridine-3-carboxamide (Compound 2331)

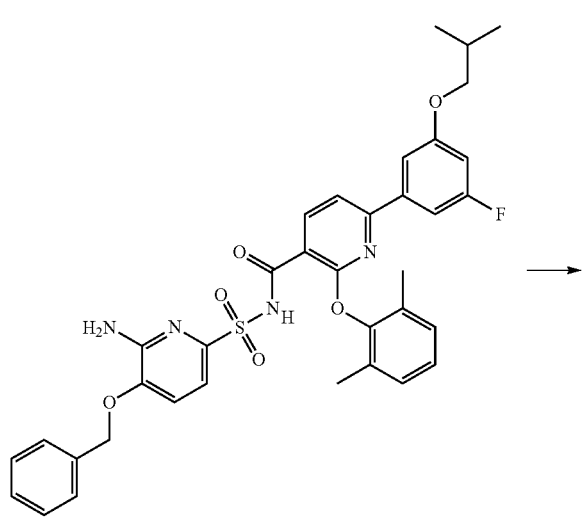

-continued

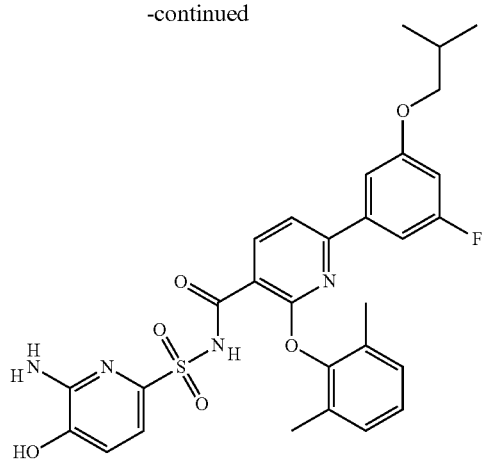

To a suspension of N-[(6-amino-5-benzyloxy-2-pyridyl)sulfonyl]-2-(2,6-dimethylphenoxy)-6-(3-fluoro-5-isobutoxy-phenyl)pyridine-3-carboxamide (Compound 1762) (21 mg, 0.03 mmol) in MeOH (20 mL) was added EtOAc (1 mL). The solution was purged with nitrogen for 2 min. Pd (3. mg, 0.003 mmol) was added. The reaction mixture was stirred under an atmosphere of hydrogen at room temperature overnight. The Pd catalyst was removed via filtration. The filtrate was concentrated to dryness. The residue was re-dissolved in DMSO and purified by preparative HPLC to provide N-[(6-amino-5-hydroxy-2-pyridyl)sulfonyl]-2-(2,6-dimethylphenoxy)-6-(3-fluoro-5-isobutoxy-phenyl)pyridine-3-carboxamide (Compound 2331) (5.0 mg, 24%). ESI-MS m/z calc. 580.1792, found 580.0 (M+1)$^+$; Retention time: 3.15 minutes.

Preparation 115: N-[(6-amino-2-pyridyl)sulfonyl]-2-(3-fluoro-5-isobutoxy-phenyl)-4-[(4S)-2,2,4-trimethylpyrrolidin-1-yl]pyrimidine-5-carboxamide (Compound 2121)

Step 1: 2,4-dichloro-N-((6-nitropyridin-2-yl)sulfonyl)pyrimidine-5-carboxamide

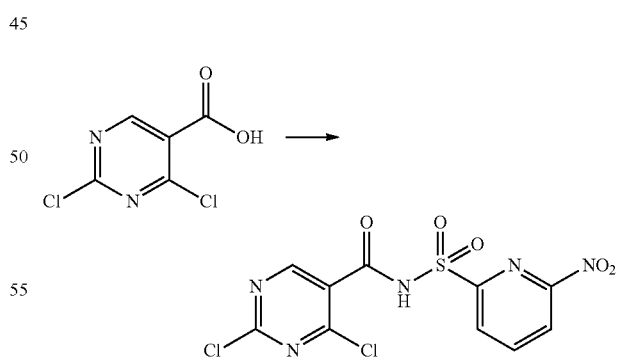

A solution of 2,4-dichloropyrimidine-5-carboxylic acid (4.56 g, 23.8 mmol) in thionylchloride (30 mL) was refluxed for 1 hour, and evaporated to remove thionylchloride. The residue was dissolved in dichloromethane (50 mL), and 6-nitropyridine-2-sulfonamide (5.14 g, 23.7 mmol) was carefully added followed by trimethylamine (10 mL). The reaction mixture was stirred at room temperature for 30 min and concentrated. The crude material was purified by chromatography on silica gel, eluted with 30-100% of ethyl acetate in hexanes, to give the desired product (9.1 g, 100%).

Step 2: N-((6-aminopyridin-2-yl)sulfonyl)-2,4-dichloropyrimidine-5-carboxamide

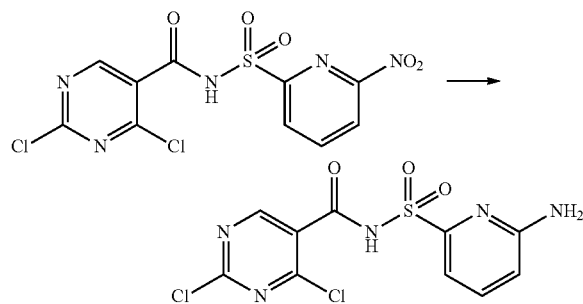

A mixture of 2,4-dichloro-N-((6-nitropyridin-2-yl)sulfonyl)pyrimidine-5-carboxamide (1.7 g, 4.5 mmol, 1.0 eq) and iron (2.6 g, 47 mmol, 10 eq) in HCl (1.9 mL 23 mmol, 5.1 eq), ethanol (6 mL), tetrahydrofuran (6 mL), and water (0.90 mL) was heated at 60° C. for 1 hour. The reaction mixture was filtered through celite and washed with methanol and ethyl acetate. The filtrate was concentrated under reduced pressure to give the desired compound (1.7 g, 100%) LC-MS: (M+H)$^+$=348.0.

Step 3: (S)—N-((6-aminopyridin-2-yl)sulfonyl)-2-chloro-4-(2,2,4-trimethylpyrrolidin-1-yl)pyrimidine-5-carboxamide

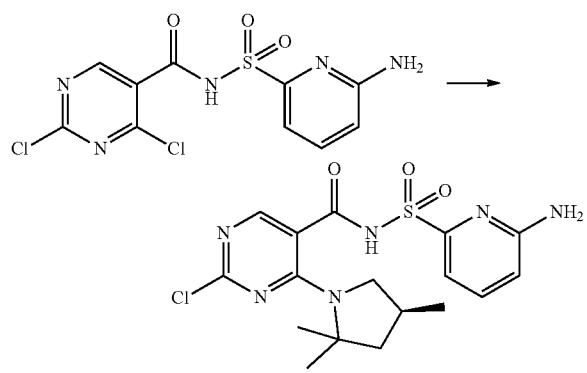

A mixture of N-((6-aminopyridin-2-yl)sulfonyl)-2,4-dichloropyrimidine-5-carboxamide (0.60 g, 1.7 mmol, 1.0 eq), (S)-2,2,4-trimethylpyrrolidine hydrochloride (0.26 g, 1.8 mmol, 1.0 eq), and potassium carbonate (0.96 g, 7.0 mmol, 4.0 eq) in 4.0 mL of dimethylsulfoxide was heated in a capped vial at 125° C. for 20 hours. The reaction mixture was purified chromatography on silica gel, and eluting with a gradient of 0-80% of methanol in ethyl acetate to give (S)—N-((6-aminopyridin-2-yl)sulfonyl)-2-chloro-4-(2,2,4-trimethylpyrrolidin-1-yl)pyrimidine-5-carboxamide as a brown solid (0.22 g, 30% yield). $^1$H NMR (DMSO-d$_6$, 250 MHz): δ 8.04 (m, 1H), 7.48 (t, J=7.3 Hz, 1H), 7.04 (d, J=7.0 Hz, 1H), 6.51 (d, J=8.3 Hz, 1H), 6.25 (s, br, 2H), 2.99 (m, 1H), 2.84 (m, 1H), 2.14 (m, 1H), 1.84 (m, 1H), 1.50 (s, 3H), 1.47 (s, 3H), 1.38 (i, 1H), 0.85 (d, J=6.3 Hz, 3H) ppm. LC-MS: (M+H)$^+$=424.9.

Step 4: N-[(6-amino-2-pyridyl)sulfonyl]-2-(3-fluoro-5-isobutoxy-phenyl)-4-[(4S)-2,2,4-trimethylpyrrolidin-1-yl]pyrimidine-5-carboxamide (Compound 2121)

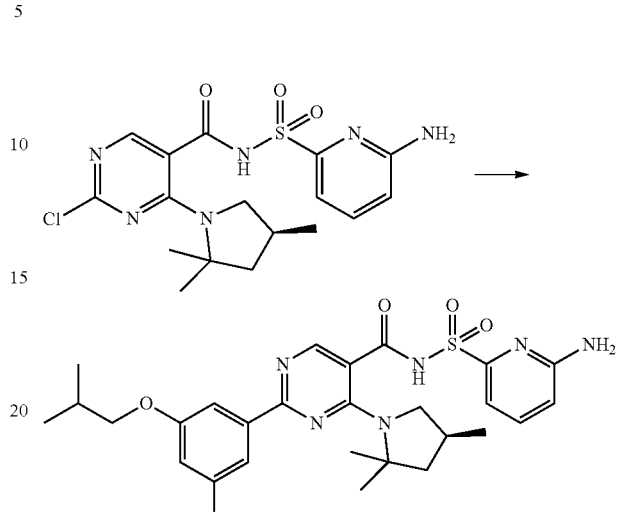

To N-[(6-amino-2-pyridyl)sulfonyl]-2-chloro-4-[(4S)-2,2,4-trimethylpyrrolidin-1-yl]pyrimidine-5-carboxamide (70 mg, 0.1647 mmol), cyclopentyl(diphenyl)phosphane; dichloropalladium; iron (12.05 mg, 0.01647 mmol), and dioxane (840.0 µL) was added (3-fluoro-5-isobutoxy-phenyl)boronic acid (69.84 mg, 0.3294 mmol), followed by sodium carbonate (247.0 µL of 2 M, 0.4941 mmol) under an atmosphere of nitrogen. The reaction mixture was irradiated at 120° C. in the microwave for 1 hour. The reaction mixture was filtered and then purified directly by reverse-phase preparative chromatography utilizing a C18 column and HPLC-MS method 10-99 A1B1 (Acetonitrile-Water+5 molar HCl, 30 min method) to afford as a tan solid, N-[(6-amino-2-pyridyl)sulfonyl]-2-(3-fluoro-5-isobutoxy-phenyl)-4-[(4S)-2,2,4-trimethylpyrrolidin-1-yl]pyrimidine-5-carboxamide (Compound 2121) (14 mg, 15%) ESI-MS m/z calc. 556.2268, found 557.2 (M+1)$^+$; Retention time: 1.71 minutes. 1H NMR (400 MHz, DMSO) δ 8.53 (s, 1H), 7.73 (s, 3H), 7.70-7.63 (m, 1H), 7.59 (d, J=9.7 Hz, 1H), 7.21 (d, J=7.2 Hz, 1H), 7.07 (d, J=10.6 Hz, 1H), 6.73 (d, J=8.4 Hz, 1H), 3.86 (d, J=6.6 Hz, 2H), 2.86-2.74 (m, 1H), 2.69 (t, J=10.9 Hz, 1H), 2.34-2.18 (m, 1H), 2.13-1.99 (m, 1H), 1.95 (dd, J=11.9, 5.5 Hz, 1H), 1.63 (d, J=23.9 Hz, 6H), 1.50 (t, J=12.2 Hz, 1H), 0.99 (d, J=6.7 Hz, 6H), 0.90 (d, J=6.3 Hz, 3H).

Preparation 116: N-[(6-amino-2-pyridyl)sulfonyl]-6-tert-butyl-2-(2,2-dimethyl-3-tetrahydropyran-4-yl-pyrrolidin-1-yl)pyridine-3-carboxamide (Compound 2425) (Compound 2266) (racemic mixture)

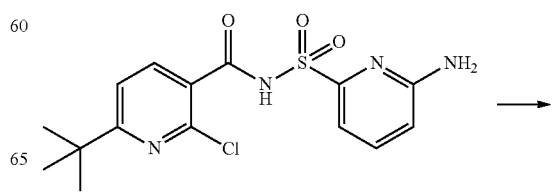

2199

-continued

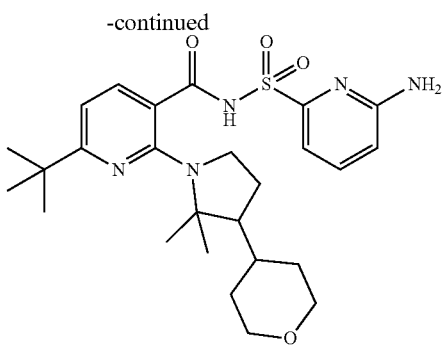

In a 5 mL microwave vial was combined the N-[(6-amino-2-pyridyl)sulfonyl]-6-tert-butyl-2-chloro-pyridine-3-carboxamide (85 mg, 0.2305 mmol) and fluorocesium (175.0 mg, 42.53 μL, 1.152 mmol) in DMSO (510.0 μL) followed by $K_2CO_3$ (318.6 mg, 2.305 mmol) and 2,2-dimethyl-3-tetrahydropyran-4-yl-pyrrolidine (169.0 mg, 0.9220 mmol). The vial was capped and heated to 150° C. in an oil bath for 16 hours. Additional fluorocesium (175.0 mg, 42.53 μL, 1.152 mmol), $K_2CO_3$ (318.6 mg, 2.305 mmol) and 2,2-dimethyl-3-tetrahydropyran-4-yl-pyrrolidine (169.0 mg, 0.9220 mmol) was added and heated to 165° C. for 16 additional hours. The reaction mixture was filtered and then purified directly by reverse-phase preparative chromatography utilizing a C18 column and HPLC-MS method 10-99% acetonitrile-water+5 mmolar HCl to afford N-[(6-amino-2-pyridyl)sulfonyl]-6-tert-butyl-2-(2,2-dimethyl-3-tetrahydropyran-4-yl-pyrrolidin-1-yl)pyridine-3-carboxamide (Compound 2425) (Compound 2266) (80 mg, 66%) as a light yellow solid, ESI-MS m/z calc. 515.25665, found 516.2 $(M+1)^+$; Retention time: 1.31 minutes. 1H NMR (400 MHz, DMSO) δ 12.47 (s, 1H), 7.70-7.52 (m, 2H), 7.17 (dd, J=7.3, 0.5 Hz, 1H), 6.78-6.59 (m, 2H), 5.14 (s, 2H), 3.84 (d, J=3.5 Hz, 2H), 3.30 (d, J=10.7 Hz, 2H), 2.84 (t, J=10.0 Hz, 1H), 2.68-2.55 (m, 1H), 2.07 (s, 4H), 1.87-1.73 (m, 1H), 1.65 (dd, J=30.6, 10.5 Hz, 2H), 1.55 (d, J=8.6 Hz, 6H), 1.49 (s, 3H), 1.28 (d, J=6.6 Hz, 10H). The stereoisomers were separated using supercritical fluid chromatography on a ChiralPak AS-H (250×10 mm), 5 μm column using 12% MeOH in $CO_2$ at a flow rate of 10.0 mL/min. The separated enantiomers were separately concentrated to dryness to give the pure compounds.

The following compounds can be prepared in the manner described herein:

N-[(6-amino-2-pyridyl)sulfonyl]-6-tert-butyl-2-(3-cyclopropyl-2,2-dimethyl-pyrrolidin-1-yl)pyridine-3-carboxamide (Compound 2577) (Isomer 1, R or S stereoisomer) (Compound 2022) (Isomer 2, R or S stereoisomer), N-[(6-amino-2-pyridyl)sulfonyl]-6-tert-butyl-2-[3-(cyclopropylmethyl)-2,2-dimethyl-pyrrolidin-1-yl]pyridine-3-carboxamide (Compound 2242), N-[(6-amino-2-pyridyl)sulfonyl]-2-(3-benzyl-2,2-dimethyl-pyrrolidin-1-yl)-6-tert-butyl-pyridine-3-carboxamide (Compound 1852), N-[(6-amino-2-pyridyl)sulfonyl]-6-tert-butyl-2-(3-cyclopropyl-2,2-dimethyl-pyrrolidin-1-yl)pyridine-3-carboxamide (Compound 2577) (Isomer 1, R or S stereoisomer) (Compound 2022) (Isomer 2, R or S stereoisomer), N-[(6-amino-2-pyridyl)sulfonyl]-6-tert-butyl-2-(2,2-dimethyl-3-tetrahydropyran-4-yl-pyrrolidin-1-yl)pyridine-3-carboxamide (Compound 2425) (Isomer 1, R or S stereoisomer) (Compound 2266) (Isomer 2, R or S stereoisomer),

2200

6-tert-butyl-N-[(2-oxo-1H-pyridin-3-yl)sulfonyl]-2-[(4S)-2,2,4-trimethylpyrrolidin-1-yl]pyridine-3-carboxamide (Compound 1765)

Preparation 117: N-[(6-amino-2-pyridyl)sulfonyl]-6-tert-butyl-5-(2-cyclopentyl-1,2-dihydroxyethyl)-2-[(4S)-2,2,4-trimethylpyrrolidin-1-yl]pyridine-3-carboxamide (Isomer 1, R or S stereoisomer) and N-[(6-amino-2-pyridyl)sulfonyl]-6-tert-butyl-5-(2-cyclopentyl-1,2-dihydroxyethyl)-2-[(4S)-2,2,4-trimethylpyrrolidin-1-yl]pyridine-3-carboxamide (Isomer 2, R or S stereoisomer)

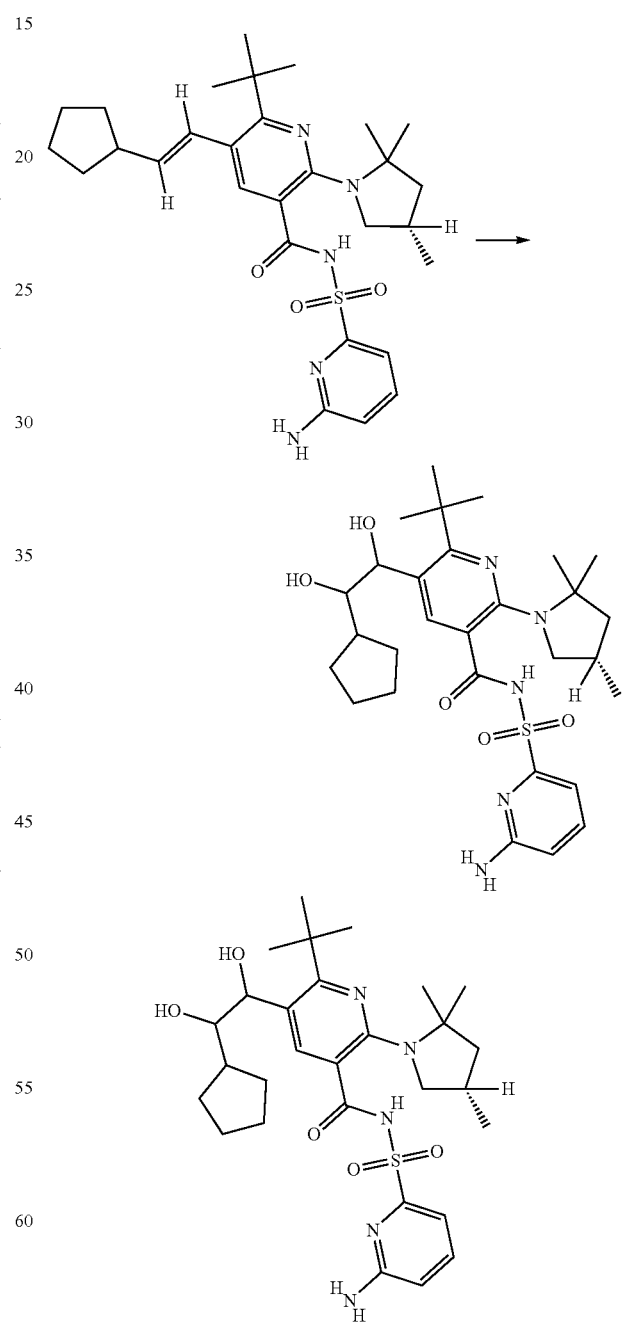

To a solution of N-[(6-amino-2-pyridyl)sulfonyl]-6-tert-butyl-5-[(E)-2-cyclopentylvinyl]-2-[(4S)-2,2,4-trimethylpyrrolidin-1-yl]pyridine-3-carboxamide (Compound 1633) (8 mg, 0.01 mmol) in acetone (1.0 mL) and water (0.5 mL), were added 4-methylmorpholine N-oxide (16 mg, 0.14 mmol) and osmium tetroxide (15 μL of 2.5% w/v, 0.001 mmol), in that order, and the reaction mixture was stirred under air at ambient temperature. After 2 h, the reaction mixture turned to a clear solution, and was concentrated to a light yellow paste. The paste was dissolved in DMSO (1 mL) and purified by reverse-phase HPLC-MS method to furnish the two diastereomeric diols as white solids. Isomer 1: N-[(6-amino-2-pyridyl)sulfonyl]-6-tert-butyl-5-(2-cyclopentyl-1,2-dihydroxy-ethyl-2-[(4S)-2,2,4-trimethylpyrrolidin-1-yl]pyridine-3-carboxamide (HCl salt) (2 mg, 23%) ESI-MS m/z calc. 573.29846, found 574.4 (M+1)$^+$; Retention time: 1.51 minutes; Isomer 2: N-[(6-amino-2-pyridyl)sulfonyl]-6-tert-butyl-5-(2-cyclopentyl-1,2-dihydroxy-ethyl-2-[(4S)-2,2,4-trimethylpyrrolidin-1-yl]pyridine-3-carboxamide (HCl salt) (4 mg, 47%) ESI-MS m/z calc. 573.29846, found 574.4 (M+1)$^+$; Retention time: 1.55 minutes The following compounds can be prepared in the manner as described herein:
N-[(6-amino-2-pyridyl)sulfonyl]-6-tert-butyl-5-(2-cyclopentyl-1,2-dihydroxyethyl)-2-[(4S)-2,2,4-trimethylpyrrolidin-1-yl]pyridine-3-carboxamide (Compound 2661) (Isomer 1),
N-[(6-amino-2-pyridyl)sulfonyl]-6-tert-butyl-5-(1,2-dihydroxy-3,3-dimethylbutyl-2-[(4S)-2,2,4-trimethylpyrrolidin-1-yl]pyridine-3-carboxamide (Compound 2069) (Isomer 2),
N-[(6-amino-2-pyridyl)sulfonyl]-6-tert-butyl-5-(2-cyclohexyl-1,2-dihydroxyethyl-2-[(4S)-2,2,4-trimethylpyrrolidin-1-yl]pyridine-3-carboxamide (isomer 1),
N-[(6-amino-2-pyridyl)sulfonyl]-6-tert-butyl-5-(2-cyclohexyl-1,2-dihydroxyethyl-2-[(4S)-2,2,4-trimethylpyrrolidin-1-yl]pyridine-3-carboxamide (isomer 2), Preparation 118: 6-methoxy-N-[(2-oxo-1H-pyridin-3-yl)sulfonyl]-2-[(4S)-2,2,4-trimethylpyrrolidin-1-yl]quinoline-3-carboxamide (Compound 2419)

Step 1: 2-chloro-6-methoxy-N-[(2-oxo-1H-pyridin-3-yl)sulfonyl]quinoline-3-carboxamide

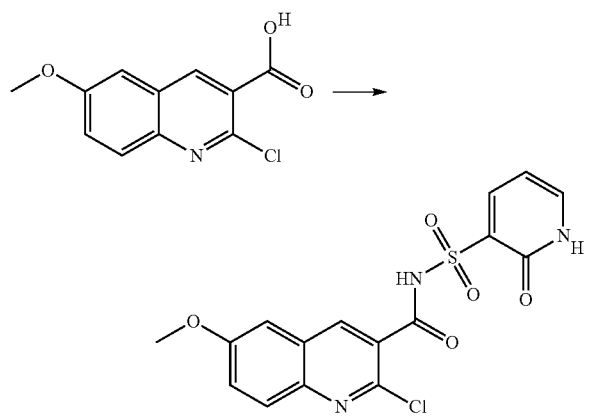

2-Chloroquinoline-3-carboxylic acid (62 mg, 0.3 mmol) and CDI (73 mg, 0.5 mmol) were combined in DMF (2 mL) and stirred at 40° C. for 2 hours. In a separate vial, NaH (15 mg, 0.4 mmol) was added to 2-methoxypyridine-3-sulfonamide (71 mg, 0.4 mmol) in DMF (1 mL). The solutions were combined and stirred overnight at ambient temperature. The reaction mixture was taken up in EtOAc and washed with HCl (1 N, 1×5 mL). The aqueous layer was back washed with EtOAc (2×10 mL), the combined organic layers were washed with brine (1×10 mL) and dried over sodium sulfate, filtered and concentrated under reduced pressure. The solid was dissolved in 1,4-dioxane (2 mL) with 4M HCl (750 uL, 4.0 mmol) and heated to 90° C. for 2 hours. The reaction mixture was cooled, the solvent was removed under reduced pressure to yield a solid, which was triturated with ethyl acetate to give the desired compound (89 mg, 79%). ESI-MS m/z 394.2 (M+1)+, retention time 0.39 minutes.

Step 2: 6-methoxy-N-[(2-oxo-1H-pyridin-3-yl)sulfonyl]-2-[(4S)-2,2,4-trimethylpyrrolidin-1-yl]quinoline-3-carboxamide (Compound 2419) (Compound 2405)

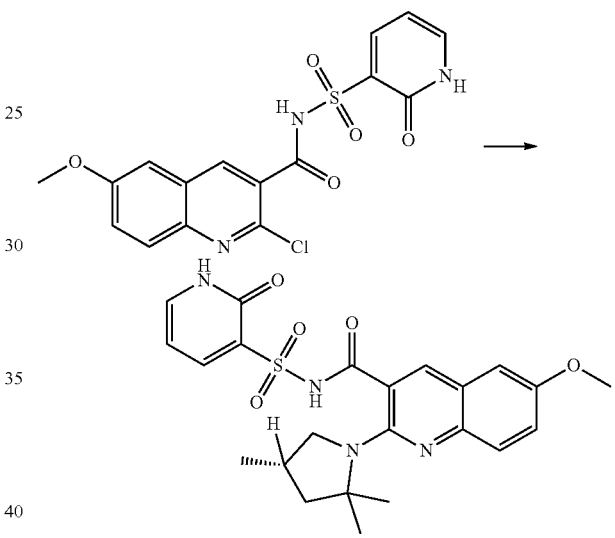

2-Chloro-N-methylsulfonyl-quinoline-3-carboxamide (40 mg, 0.1 mmol), potassium carbonate (69 mg, 0.5 mmol), and (4S)-2,2,4-trimethylpyrrolidine (HCl salt) (30 mg, 0.2 mmol) was suspended in DMSO (1 mL). The reaction was heated at 120° C. for 2 days, then cooled, diluted with DMSO-methanol, filtered, and then purified via reverse phase HPLC-MS method using a dual gradient run from 1-99% mobile phase B over 15.0 minutes (mobile phase A=H$_2$O (5 mM TFA), mobile phase B acetonitrile) to give the desired compound (8 mg, 17%). ESI-MS m/z 471.3 (M+1)*, retention time 1.19 minutes.

The following compounds can be synthesized using the procedures described herein:
6-methyl-N-[(2-oxo-1H-pyridin-3-yl)sulfonyl]-2-[(4S)-2,2,4-trimethylpyrrolidin-1-yl]quinoline-3-carboxamide (Compound 2471),
N-[(6-amino-2-pyridyl)sulfonyl]-7-methyl-2-[(4S)-2,2,4-trimethylpyrrolidin-1-yl]quinoline-3-carboxamide (Compound 2519),
N-[(6-amino-2-pyridyl)sulfonyl]-6-methoxy-2-[(4S)-2,2,4-trimethylpyrrolidin-1-yl]quinoline-3-carboxamide (Compound 2196),
N-[(6-amino-2-pyridyl)sulfonyl]-6-methyl-2-[(4S)-2,2,4-trimethylpyrrolidin-1-yl]quinoline-3-carboxamide (Compound 2548), N-[(2-oxo-1H-pyridin-3-yl)sulfonyl]-2-[(4S)-2,2,4-trimethylpyrrolidin-1-yl]quinoline-3-carboxamide (Compound 2405), N-[(6-amino-2-pyridyl)sulfonyl]-2-[(4S)-2,2,4-trimethylpyrrolidin-1-yl]quinoline-3-carboxamide (Compound 2265) and N-[(2-methoxy-3-pyridyl)sulfonyl]-7-methyl-2-[(4S)-2,2,4-trimethylpyrrolidin-1-yl]quinoline-3-carboxamide (Compound 1859)

Preparation 119: N-[(6-amino-2-pyridyl)sulfonyl]-5-fluoro-6-isopropoxy-2-(2,2,4-trimethylpyrrolidin-1-yl)pyridine-3-carboxamide (Compound 2230)

Step 1: N-[(6-amino-2-pyridyl)sulfonyl]-2,6-dichloro-5-fluoro-pyridine-3-carboxamide

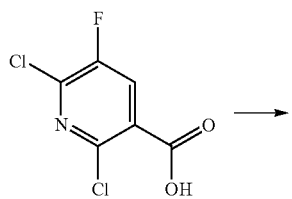

Step 2: N-[(6-amino-2-pyridyl)sulfonyl]-6-chloro-5-fluoro-2-(2,2,4-trimethylpyrrolidin-1-yl)pyridine-3-carboxamide

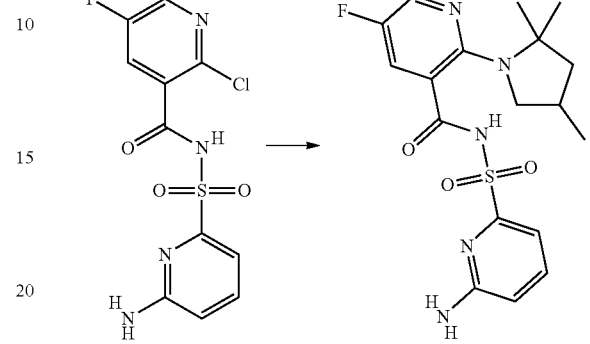

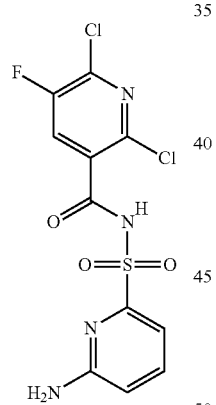

2,6-Dichloro-5-fluoro-pyridine-3-carboxylic acid (5.0 g, 23.8 mmol), CDI (6.8 g, 41.9 mmol) and DMF (30 mL) were stirred at 60° C. for 50 min. In a separate flask, 6-aminopyridine-2-sulfonamide (5.2 g, 29.8 mmol), NaH (1.2 g, 29.8 mmol), and DMF (25 mL). The reaction mixture was stirred at 60° C. for 1 hour. The contents containing 6-aminopyridine-2-sulfonamide was added dropwise to the activated acid at room temperature. The reaction mixture was stirred for 16 hours at room temperature. The reaction mixture was then placed in an ice bath, diluted with water (300 mL), and adjusted pH to 2. The resulting slurry was vigorously stirred for 30 min. The precipitate was filtered, washed with water (50 ML×3) and hexanes (50 mL×3), and dried in vacuo to furnish N-[(6-amino-2-pyridyl)sulfonyl]-2,6-dichloro-5-fluoro-pyridine-3-carboxamide (6.9 g, 79%).

To a solution of N-[(6-amino-2-pyridyl)sulfonyl]-2,6-dichloro-5-fluoro-pyridine-3-carboxamide (1.0 g, 2.7 mmol) in DMSO (8 mL) was added 2,2,4-trimethylpyrrolidine (HCl salt) (820 mg, 5.5 mmol) and K$_2$CO$_3$ (2.3 g, 16.4 mmol). The reaction was stirred at 150° C. for 16 hours. The reaction mixture was filtered and purified via prep HPLC (1-99% ACN, 15 min, HCl modifier) to afford N-[(6-amino-2-pyridyl)sulfonyl]-6-chloro-5-fluoro-2-(2,2,4-trimethylpyrrolidin-1-yl)pyridine-3-carboxamide (HCl salt) (200 mg, 30%).

Step 3: N-[(6-amino-2-pyridyl)sulfonyl]-5-fluoro-6-isopropoxy-2-(2,2,4-trimethylpyrrolidin-1-yl)pyridine-3-carboxamide (Compound 2230)

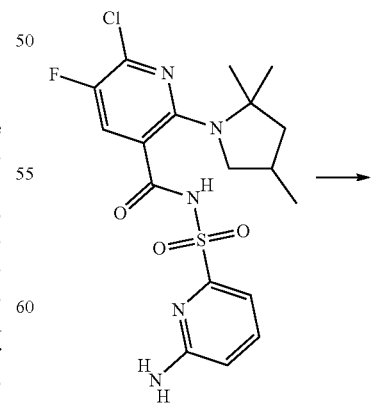

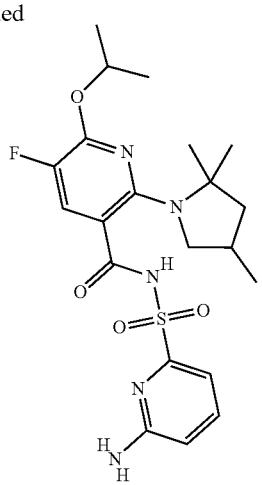

N-[(6-amino-2-pyridyl)sulfonyl]-6-chloro-5-fluoro-2-(2,2,4-trimethylpyrrolidin-1-yl)pyridine-3-carboxamide (HCl salt) (50 mg, 0.10 mmol), isopropanol (31 mg, 40 μL, 0.52 mmol), NaH (10 mg, 0.24 mmol), and DMSO (1 mL). The reaction mixture was stirred at 150° C. for 2 hours. The reaction mixture was then filtered and purified via prep HPLC (1-99% ACN, 15 min, HCL modifier) to yield N-[(6-amino-2-pyridyl)sulfonyl]-5-fluoro-6-isopropoxy-2-(2,2,4-trimethylpyrrolidin-1-yl)pyridine-3-carboxamide (Compound 2230) (HCl salt) (13 mg, 23%) 1H NMR (400 MHz, DMSO-d$_6$) δ 12.26 (s, 1H), 7.66-7.55 (m, 2H), 7.17 (dd, J=7.3, 0.7 Hz, 1H), 6.66 (dd, J=8.4, 0.8 Hz, 1H), 6.41 (s, 2H), 5.26 (p, J=6.1 Hz, 1H), 2.60-2.51 (m, 11H), 2.49-2.40 (m, 1H), 2.33 (p, J=1.8 Hz, OH), 2.20 (s, 1H), 1.84 (dd, J=11.8, 5.6 Hz, 1H), 1.51 (s, 3H), 1.45 (s, 3H), 1.43-1.30 (m, 4H), 1.29 (d, J=6.2 Hz, 3H), 0.85 (d, J=6.3 Hz, 3H). ESI-MS m/z calc. 465.1846, found 466.3 (M+1)$^+$; Retention time: 1.38 minutes.

The following compounds can be synthesized using the procedures described herein:
N-[(6-amino-2-pyridyl)sulfonyl]-6-(1-cyclopropylethoxy)-5-fluoro-2-(2,2,4-trimethylpyrrolidin-1-yl)pyridine-3-carboxamide (Compound 2373) and
N-[(6-amino-2-pyridyl)sulfonyl]-6-(1,2-dimethylpropoxy)-5-fluoro-2-(2,2,4-trimethylpyrrolidin-1-yl)pyridine-3-carboxamide (Compound 1810)

Preparation 120: N-[(3R)-3-aminopyrrolidin-1-yl]sulfonyl-6-(3-fluoro-5-isobutoxy-phenyl)-2-(p-tolyl)pyridine-3-carboxamide (Compound 2276)

Step 1: 2-chloro-6-(3-fluoro-5-isobutoxy-phenyl)pyridine-3-carboxylic acid

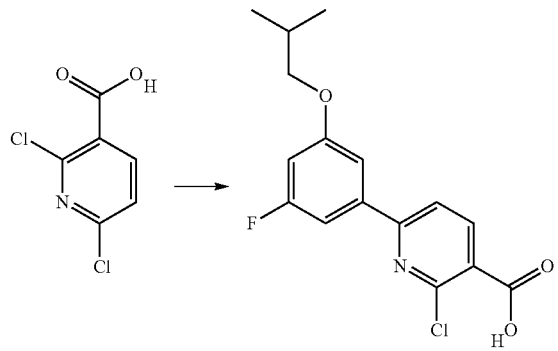

2,6-Dichloropyridine-3-carboxylic acid (1.000 g, 4.861 mmol) in IPA (30 mL), K$_2$CO$_3$ (6.075 mL of 2 M, 12.15 mmol) and dichloropalladium; triphenylphosphane (341.2 mg, 0.4861 mmol) was added. The reaction mixture was heated to 80° C. under an atmosphere of nitrogen and (3-fluoro-5-isobutoxy-phenyl)boronic acid (1.082 g, 5.104 mmol) in IPA (30 mL) was added slowly over 1 hour. The reaction mixture was heated for a further 4 h. The reaction mixture was cooled, 6 M HCl (2 mL) was added and then pH adjusted to 2-3 with additional 6 M HCl. The organic phase was collected, dried over sodium sulfate and concentrated under reduced pressure. The residue was purified by revere phase column chromatography using 10-80% ACN in Water (with TFA modifier) to give the desired compound. ESI-MS m/z 324.0 (M+1)$^+$; Retention time: 1.0 minutes.

Step 2: 6-(3-fluoro-5-isobutoxy-phenyl)-2-(p-tolyl)pyridine-3-carboxylic acid

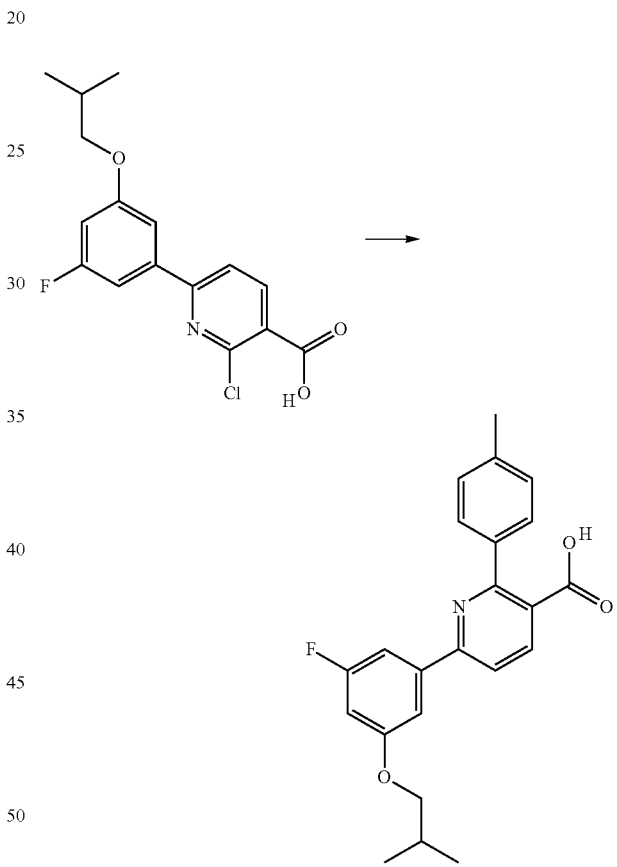

A mixture of 2-chloro-6-(3-fluoro-5-isobutoxy-phenyl)pyridine-3-carboxylic acid (324 mg, 1.00 mmol), p-tolylboronic acid (272 mg, 2.00 mmol), K$_2$CO$_3$ (415 mg, 3.00 mmol), and tetrakis(triphenylphosphine)palladium (0) (116 mg, 0.10 mmol) in DMF (10 mL) was degassed under a stream of nitrogen and stirred at 120° C. for 16 hours. A further aliquot of tetrakis(triphenylphosphine)palladium (0) (116 mg, 0.10 mmol) was added, and the reaction mixture was stirred at 150° C. for 17 hours. The reaction mixture was diluted with water, adjusted to pH 5 with 1 M HCl, and extracted with ethyl acetate. The combined extracts were washed with brine, dried over sodium sulfate, and evaporated under reduced pressure. The residue was purified by silica gel chromatography using 0-5% methanol in dichloromethane as eluent to give 6-(3-fluoro-5-isobutoxy-phenyl)-2-(p-tolyl)pyridine-3-carboxylic acid (314 mg, 83%).

Step 3: N-[(3R)-3-aminopyrrolidin-1-yl]sulfonyl-6-(3-fluoro-5-isobutoxy-phenyl)-2-(p-tolyl)pyridine-3-carboxamide (Compound 2276)

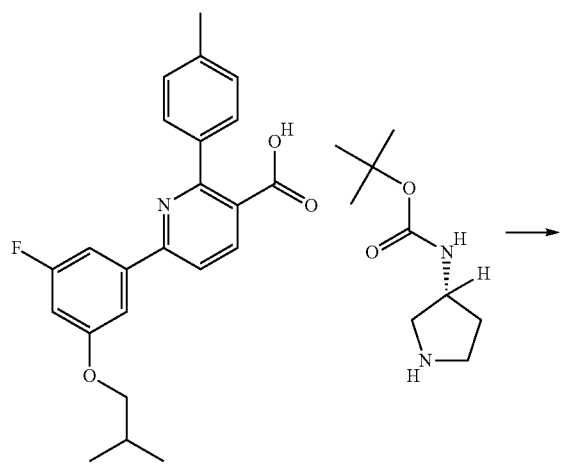

A solution of 6-(3-fluoro-5-isobutoxyphenyl)-2-(p-tolyl) nicotinic acid (38 mg, 0.1 mmol) and N-(oxomethylene) sulfamoyl chloride (17 mg, 10 µL, 0.1 mmol) in dichloromethane (1 mL) was stirred for an hour, then tert-butyl N-[(3R)-pyrrolidin-3-yl]carbamate (28 mg, 0.2 mmol) and triethylamine (15 mg, 21 µL, 0.2 mmol) were added. After 17 hours, HCl (200 µL of 4 M, 0.8 mmol) (in dioxane) was added, and the reaction mixture was stirred for two hours. The reaction mixture was filtered and purified using a reverse phase HPLC-MS method using a Luna C18 (2) column (75×30 mm, 5 µm particle size) and a dual gradient run from 1-99% mobile phase B over 15.0 minutes (mobile phase A=$H_2O$ (5 mM HCl), mobile phase B=$CH_3CN$. Flow rate=50 mL/min, and column temperature=25° C.) to give the desired compound. ESI-MS m/z 527.4 (M+1)$^+$; Retention time: 1.62 minutes.

Preparation 121: N-[(2-acetamido-3-pyridyl)sulfonyl]-6-(6-isopropoxy-3-pyridyl)-2-[(4S)-2,2,4-trimethylpyrrolidin-1-yl]pyridine-3-carboxamide (Compound 1976)

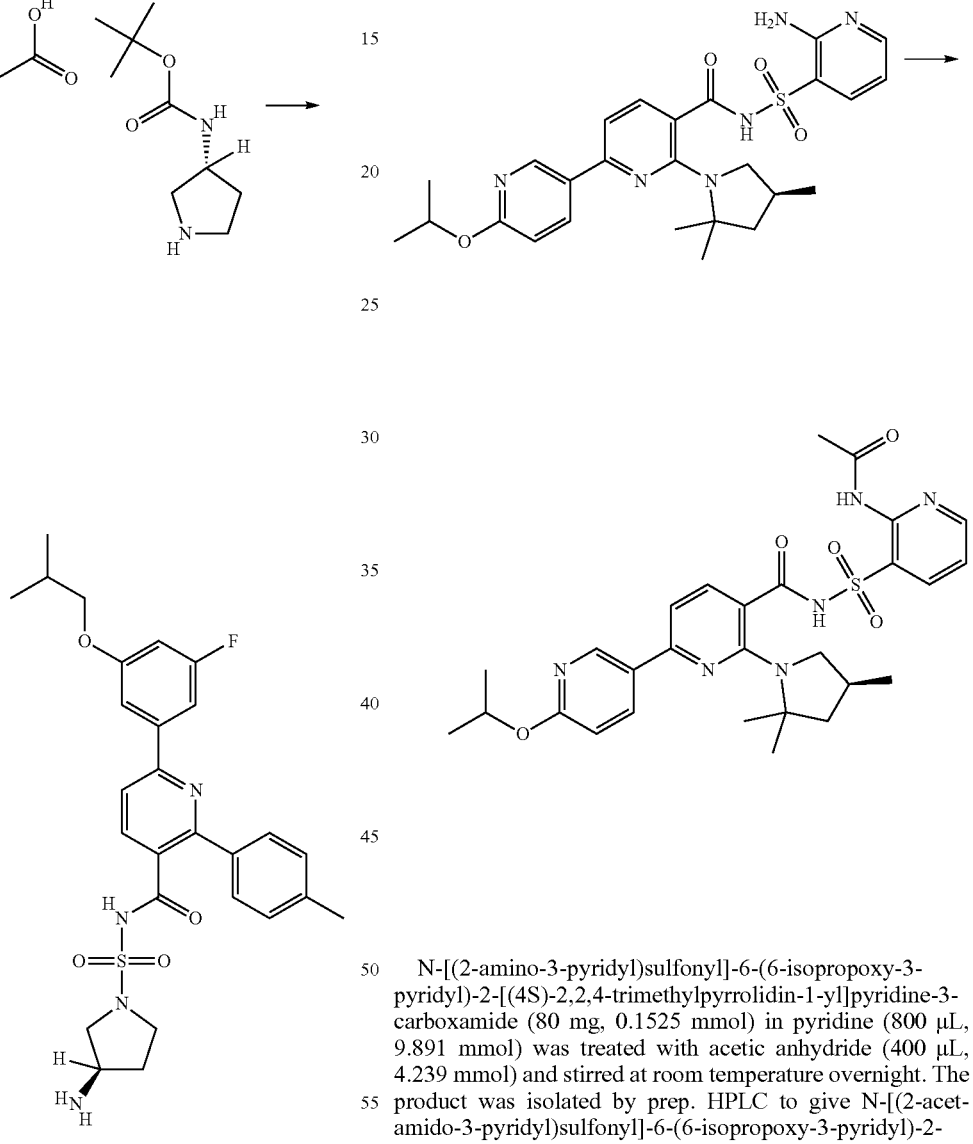

N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (80 mg, 0.1525 mmol) in pyridine (800 µL, 9.891 mmol) was treated with acetic anhydride (400 µL, 4.239 mmol) and stirred at room temperature overnight. The product was isolated by prep. HPLC to give N-[(2-acetamido-3-pyridyl)sulfonyl]-6-(6-isopropoxy-3-pyridyl)-2-[(4S)-2,2,4-trimethylpyrrolidin-1-yl]pyridine-3-carboxamide (Compound 1976) (HCl salt) (20 mg, 21%) 1H NMR (400 MHz, DMSO-$d_6$) δ 8.85 (s, 1H), 8.67 (d, J=4.7 Hz, 1H), 8.43 (d, J=7.9 Hz, 1H), 8.30 (d, J=9.0 Hz, 1H), 7.84 (d, J=8.0 Hz, 1H), 7.53-7.42 (m, 1H), 7.28 (d, J=8.0 Hz, 1H), 6.87 (d, J=8.7 Hz, 1H), 5.31 (p, J=6.3 Hz, 1H), 2.41 (s, 2H), 2.25 (s, 3H), 2.18 (dt, J=16.2, 7.6 Hz, 1H), 1.88 (dd, J=12.1, 5.8 Hz, 1H), 1.55 (d, J=4.4 Hz, 6H), 1.42 (t, J=12.0 Hz, 1H), 1.31 (d, J=6.1 Hz, 6H), 0.74 (d, J=6.3 Hz, 3H). ESI-MS m/z calc. 566.23114, found 567.0 (M+1)$^+$; Retention time: 2.19 minutes.

Preparation 122: N-[(2-amino-3-pyridyl)sulfonyl]-6-(6-ethoxy-4-methyl-2-pyridyl)-2-[(4S)-2,2,4-trimethylpyrrolidin-1-yl]pyridine-3-carboxamide (Compound 2256)

Step 1: 2-chloro-6-(6-fluoro-4-methyl-2-pyridyl)pyridine-3-carboxylic acid

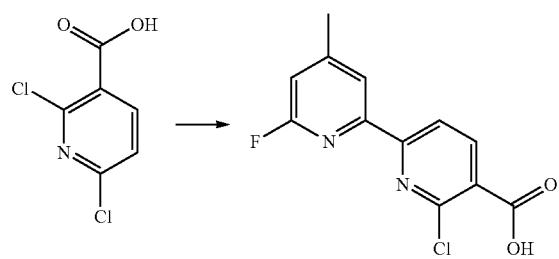 [SMILES: O=C(O)c1ccc(Cl)nc1Cl ; Cc1cc(F)nc(-c2ccc(C(=O)O)c(Cl)n2)c1]

2,6-Dichloronicotinic acid (661 mg, 3.44 mmol), (6-fluoro-4-methyl-2-pyridyl)boronic acid (560 mg, 3.62 mmol), $K_2CO_3$ (4.13 mL of 2 M, 8.26 mmol) in IPA (20 mL) was added $Pd(PPh_3)_2Cl_2$ (48.3 mg, 0.07 mmol). The reaction mixture was placed under an atmosphere of nitrogen and heated to 80° C. for 10 h. The reaction mixture was filtered, the solvent was evaporated under reduced pressure and the crude mixture was purified by reverse phase column chromatography using 10-80% acetonitrile in water (TFA modifier) to give the desired compound. ESI-MS m/z 267.0 (M+1)$^+$; Retention time: 0.82 minutes.

Step 2: 2-chloro-6-(6-ethoxy-4-methyl-2-pyridyl)pyridine-3-carboxylic acid

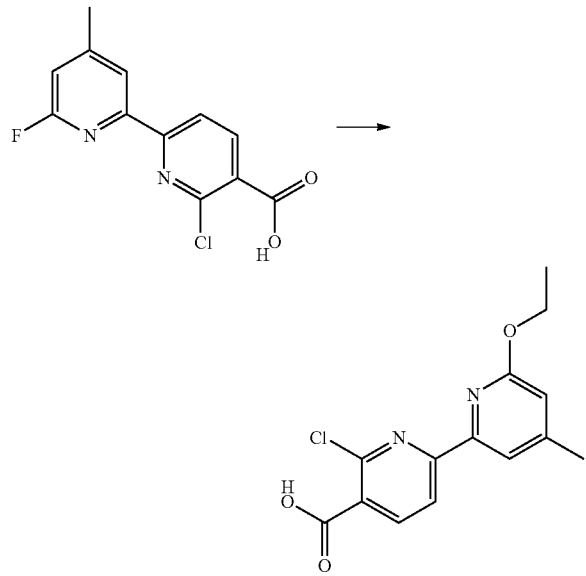

2-chloro-6-(6-fluoro-4-methyl-2-pyridyl)pyridine-3-carboxylic acid (4.2 g, 15 mmol) was dissolved into a solution of sodium ethoxide (25 mL of 21% w/v, 79 mmol) in ethanol. The reaction mixture was heated to 75° C. and stirred for 3 hours. The reaction mixture was diluted with EtOAc (75 mL) and washed with water (1×75 mL) with some brine (20 mL). The aqueous layer was extracted with EtOAc (1×75 mL). The organic layers were combined, dried over sodium sulfate, filtered and concentrated under reduced pressure to give an orange solid. The solid was redissolved in EtOAc (75 mL) and aqueous NaOH solution (1 M, 75 mL). The aqueous layer was isolated and acidified to pH 2, extracted with EtOAc (2×75 mL). The final organic layers were dried over sodium sulfate, filtered and concentrated under reduced pressure. The obtained solid was purified by silica gel column chromatography column, using 0-10% MeOH/DCM as eluent to give 2-chloro-6-(6-ethoxy-4-methyl-2-pyridyl)pyridine-3-carboxylic acid (1.17 g, 25%) as a white solid. ESI-MS m/z calc. 292.06146, found 293.1 (M+1)$^+$; Retention time: 1.72 minutes.

Step 3: N-[(2-amino-3-pyridyl)sulfonyl]-2-chloro-6-(6-ethoxy-4-methyl-2-pyridyl)pyridine-3-carboxamide

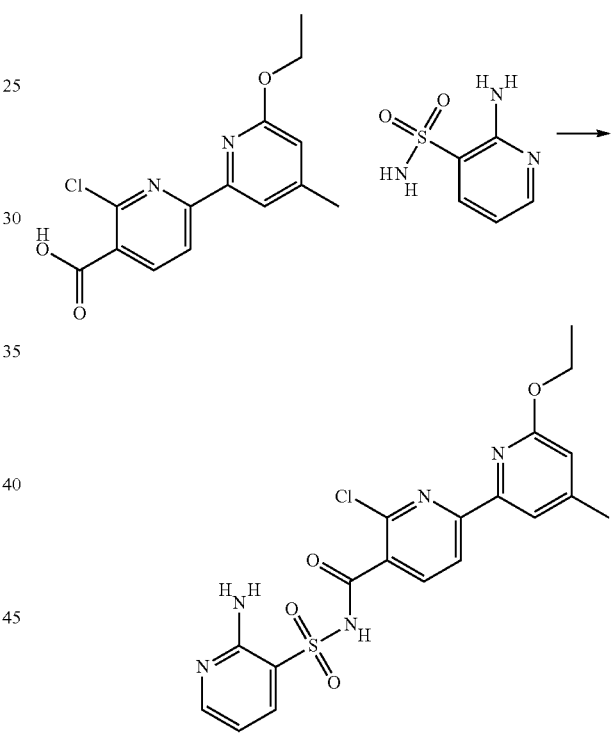

2-chloro-6-(6-ethoxy-4-methyl-2-pyridyl)pyridine-3-carboxylic acid (200 mg, 0.68 mg) was dissolved in DMF (2.5 mL). CDI (123 mg, 0.75 mmol) was added, and the reaction mixture was allowed to stir at 60° C. for 1 hour. In a separate flask, sulfonamide was dissolved in DMF (600 μL), and NaH (34 mg, 0.85 mmol) was added and the reaction mixture was stirred for 45 minutes at room temperature. The activated carboxylic acid mixture was then added to the deprotonated sulfonamide. The final reaction mixture was stirred at 60° C. overnight. After cooling to room temperature, the reaction mixture was diluted with EtOAc (50 mL) and washed with water (1×50 mL) and brine (2×75 mL). The organic layer was dried over sodium sulfate, filtered and concentrated under reduced pressure to give the desired compound (297 mg, 97%). ESI-MS m/z 448.0 (M+1)$^+$; Retention time: 0.53 minutes.

Step 4: N-[(2-amino-3-pyridyl)sulfonyl]-6-(6-ethoxy-4-methyl-2-pyridyl)-2-[(4S)-2,2,4-trimethylpyrrolidin-1-yl]pyridine-3-carboxamide (Compound 2256)

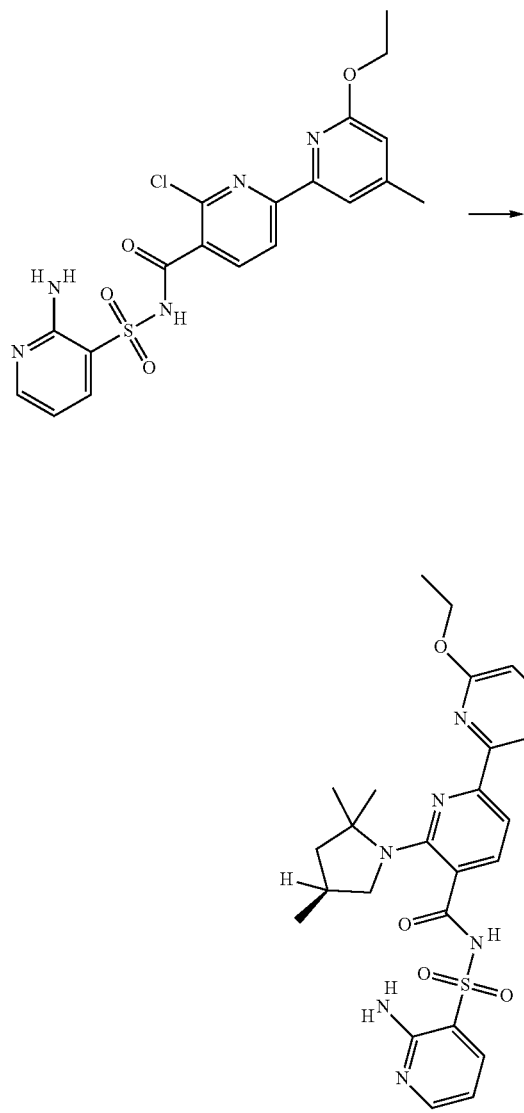

2-chloro-6-(6-ethoxy-4-methyl-2-pyridyl)-N-methyl-sulfonyl-pyridine-3-carboxamide (60 mg, 0.13 mmol) and (4S)-2,2,4-trimethylpyrrolidine (free base, 45 mg, 0.4 mmol) were combined in DMSO (100 µL). Potassium carbonate (55 mg, 0.4 mmol) was added and the reaction mixture was heated overnight at 140° C., then 165° C. for 3 hours. The reaction mixture was purified using a reverse phase HPLC method using a Luna C18 (2) column (50×21.2 mm, 5 m particle size) and a dual gradient run from 10-99% mobile phase B over 15.0 minutes (mobile phase A=water (de-ionized, no acid modifier), mobile phase B=acetonitrile) to give the desired compound. ESI-MS m/z 525.3 (M+1)$^+$; Retention time: 1.57 minutes.

Preparation 123: N-[(2-amino-3-pyridyl)sulfonyl]-6-[6-(diethylamino)-2-pyridyl]-2-[(4S)-2,2,4-trimethylpyrrolidin-1-yl]pyridine-3-carboxamide (Compound 1845)

Step 1: N-[(2-amino-3-pyridyl)sulfonyl]-6-(6-fluoro-2-pyridyl)-2-[(4S)-2,2,4-trimethylpyrrolidin-1-yl]pyridine-3-carboxamide

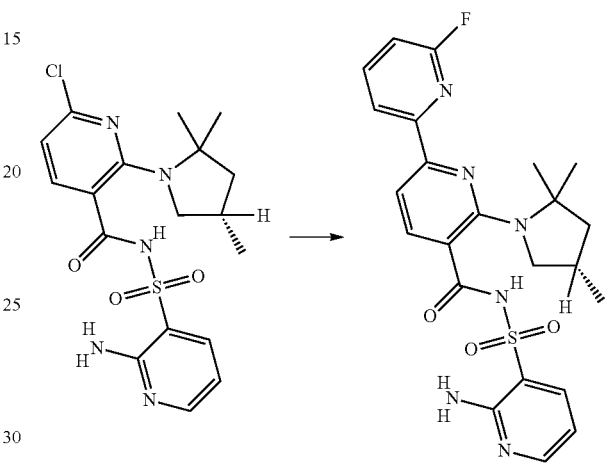

A mixture of N-[(2-amino-3-pyridyl)sulfonyl]-6-chloro-2-[(4S)-2,2,4-trimethylpyrrolidin-1-yl]pyridine-3-carboxamide (0.12 g, 0.28 mmol), (6-fluoro-2-pyridyl)boronic acid (0.06 g, 0.42 mmol), [1,1'-bis(diphenylphosphino)ferrocene]dichloropalladium(II), complex with dichloromethane (0.02 g, 0.02 mmol), and Na$_2$CO$_3$ (0.09 g, 0.85 mmol) in DMF (2.2 mL) and water (566 µL) was degassed under a stream of nitrogen and stirred at 100° C. for 20 hours. The reaction mixture was diluted with water and extracted with ethyl acetate. The combined extracts were washed with brine, dried over sodium sulfate, and evaporated under reduced pressure. The residue was purified by silica gel column chromatography using 0-5% methanol in dichloromethane as eluent to give N-[(2-amino-3-pyridyl)sulfonyl]-6-(6-fluoro-2-pyridyl)-2-[(4S)-2,2,4-trimethylpyrrolidin-1-yl]pyridine-3-carboxamide (0.11 g, 80%) as yellow solid.

Step 2: N-[(2-amino-3-pyridyl)sulfonyl]-6-[6-(diethylamino)-2-pyridyl]-2-[(4S)-2,2,4-trimethylpyrrolidin-1-yl]pyridine-3-carboxamide (Compound 1845)

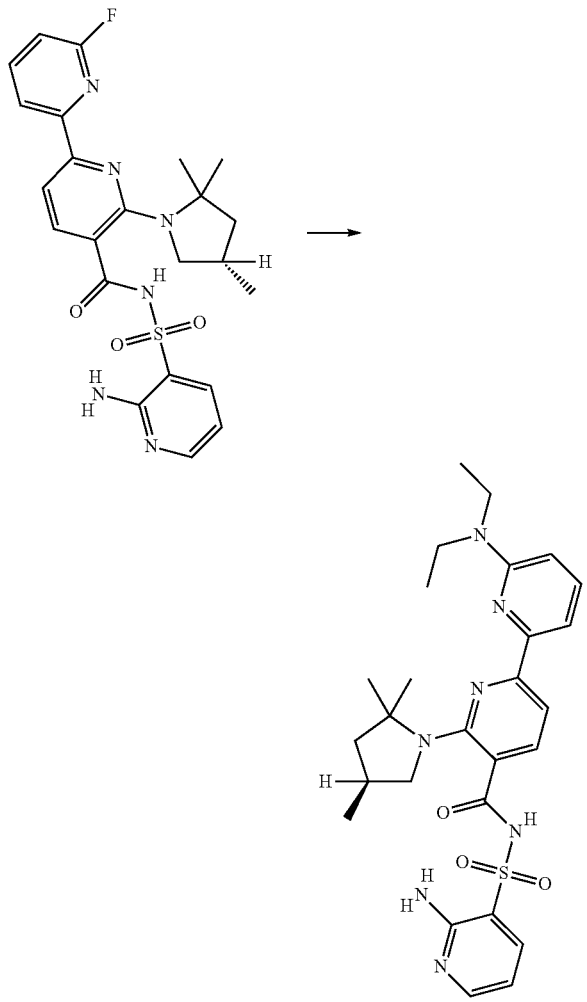

A solution of N-[(2-amino-3-pyridyl)sulfonyl]-6-(6-fluoro-2-pyridyl)-2-[(4S)-2,2,4-trimethylpyrrolidin-1-yl]pyridine-3-carboxamide (30 mg, 0.06 mmol) and diethylamine (1 mL, 9.67 mmol) was stirred in a sealed vessel at 120° C. for 17 hours, then 150° C. for 22 hours. The diethylamine was removed under vacuum, and the residue was purified using a reverse phase HPLC-MS method using a Luna C18 (2) column (75×30 mm, 5 μm particle size) and a dual gradient run from 25-75% mobile phase B over 15.0 minutes (mobile phase A=$H_2O$ (5 mM HCl), mobile phase B=$CH_3CN$) to give the desired compound. ESI-MS m/z 483.5 (M+1)$^+$; Retention time: 0.88 minutes The following compounds can be synthesized using the procedures described herein N-[(2-amino-3-pyridyl)sulfonyl]-6-[6-(2,2-dimethylpropylamino)-2-pyridyl]-2-[(4S)-2,2,4-trimethylpyrrolidin-1-yl]pyridine-3-carboxamide (Compound 2500), N-[(6-amino-2-pyridyl)sulfonyl]-6-[6-(diethylamino)-5-methyl-2-pyridyl]-2-(2,2,4-trimethylpyrrolidin-1-yl)pyridine-3-carboxamide (Compound 1907), N-[(6-amino-2-pyridyl)sulfonyl]-6-[6-(isobutylamino)-5-methyl-2-pyridyl]-2-(2,2,4-trimethylpyrrolidin-1-yl)pyridine-3-carboxamide (Compound 2362), N-[(6-amino-2-pyridyl)sulfonyl]-6-[6-(diethylamino)-4-methyl-2-pyridyl]-2-[(4S)-2,2,4-trimethylpyrrolidin-1-yl]pyridine-3-carboxamide (Compound 2002), 6-(6-ethoxy-4-methyl-2-pyridyl)-N-(1H-pyrazol-3-ylsulfonyl)-2-[(4S)-2,2,4-trimethylpyrrolidin-1-yl]pyridine-3-carboxamide (Compound 2487), N-[(6-amino-2-pyridyl)sulfonyl]-6-[6-[2-(2-ethoxyethoxy)ethoxy]-4-methyl-2-pyridyl]-2-[(4S)-2,2,4-trimethylpyrrolidin-1-yl]pyridine-3-carboxamide (Compound 1696), N-[(6-amino-2-pyridyl)sulfonyl]-6-[6-(2-isopropoxyethoxy)-4-methyl-2-pyridyl]-2-[(4S)-2,2,4-trimethylpyrrolidin-1-yl]pyridine-3-carboxamide (Compound 1703), N-[(6-amino-2-pyridyl)sulfonyl]-6-[6-(2-ethoxyethoxy)-4-methyl-2-pyridyl]-2-[(4S)-2,2,4-trimethylpyrrolidin-1-yl]pyridine-3-carboxamide (Compound 1700), N-[(6-amino-2-pyridyl)sulfonyl]-6-[6-[isopropyl(methyl)amino]-5-methyl-3-pyridyl]-2-[(4S)-2,2,4-trimethylpyrrolidin-1-yl]pyridine-3-carboxamide (Compound 2687), N-[(6-amino-2-pyridyl)sulfonyl]-6-[6-(isopropylamino)-5-methyl-3-pyridyl]-2-[(4S)-2,2,4-trimethylpyrrolidin-1-yl]pyridine-3-carboxamide (Compound 2688)

N-[(6-amino-2-pyridyl)sulfonyl]-6-[6-[ethyl(methyl)amino]-5-methyl-3-pyridyl]-2-[(4S)-2,2,4-trimethylpyrrolidin-1-yl]pyridine-3-carboxamide (Compound 2689), N-[(6-amino-2-pyridyl)sulfonyl]-6-[6-[2-ethoxyethyl(methyl)amino]-5-methyl-3-pyridyl]-2-[(4S)-2,2,4-trimethylpyrrolidin-1-yl]pyridine-3-carboxamide (Compound 2685), N-[(6-amino-2-pyridyl)sulfonyl]-6-[6-[2-(2-ethoxyethoxy)ethyl-methyl-amino]-5-methyl-3-pyridyl]-2-[(4S)-2,2,4-trimethylpyrrolidin-1-yl]pyridine-3-carboxamide (Compound 2684) and N-[(6-amino-2-pyridyl)sulfonyl]-6-[6-(2-ethoxyethylamino)-5-methyl-3-pyridyl]-2-[(4S)-2,2,4-trimethylpyrrolidin-1-yl]pyridine-3-carboxamide (Compound 2686).

Preparation 124: N-(benzenesulfonyl)-6-(6-ethoxy-4-methyl-2-pyridyl)-2-(2,4,6-trimethylphenoxy)pyridine-3-carboxamide (Compound 2455)

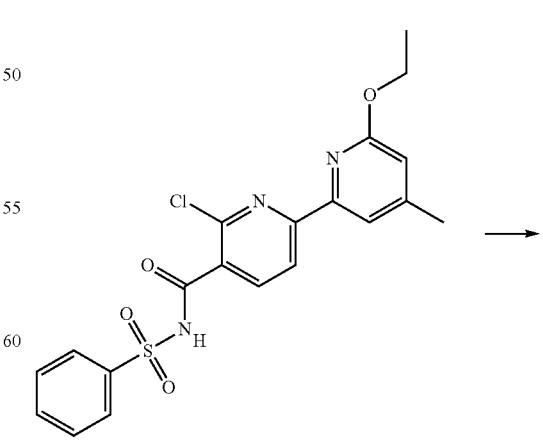

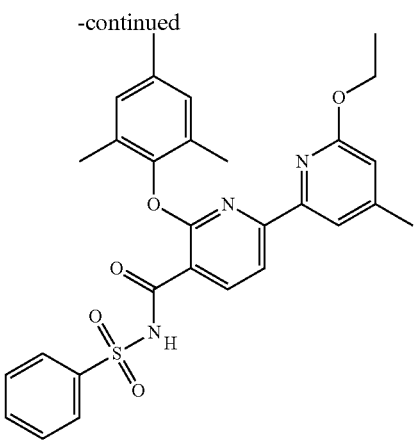

N-[(2-amino-3-pyridyl)sulfonyl]-2-chloro-6-(6-ethoxy-4-methyl-2-pyridyl)pyridine-3-carboxamide (50 mg, 0.1 mmol) and 2,4,6-trimethyl-phenol (45 mg, 0.3 mmol) were dissolved in DMSO (175 µL) and dioxane (175 µL). Sodium hydride (13 mg, 0.3 mmol) was added and the reaction mixture was heated under microwave irradiation at 150° C. for 20 minutes. The reaction mixture was purified using a reverse phase HPLC method using a Luna C18 (2) column (50×21.2 mm, 5 µm particle size) and a dual gradient run from 10-99% mobile phase B over 15.0 minutes (mobile phase A=water (de-ionized, no acid modifier), mobile phase B=acetonitrile) to give N-(benzenesulfonyl)-6-(6-ethoxy-4-methyl-2-pyridyl)-2-(2,4,6-trimethylphenoxy)pyridine-3-carboxamide (Compound 2455). ESI-MS m/z 532.5 (M+1)⁺; Retention time: 2.52 minutes.

The following compounds can be synthesized using the procedures described herein:

N-[(6-amino-2-pyridyl)sulfonyl]-6-(6-ethoxy-4-methyl-2-pyridyl)-2-(2,4,6-trimethylphenoxy)pyridine-3-carboxamide (Compound 2511), N-[(2-amino-3-pyridyl)sulfonyl]-6-(6-ethoxy-4-methyl-2-pyridyl)-2-(2,4,6-trimethylphenoxy)pyridine-3-carboxamide (Compound 1795), 6-(6-ethoxy-4-methyl-2-pyridyl)-N-(1H-pyrazol-3-ylsulfonyl)-2-(2,4,6-trimethylphenoxy)pyridine-3-carboxamide (Compound 2301) and 6-(6-ethoxy-4-methyl-2-pyridyl)-N-[(2-oxo-1H-pyridin-3-yl)sulfonyl]-2-(2,4,6-trimethylphenoxy)pyridine-3-carboxamide (Compound 1768).

Preparation 125: N-[(2-amino-3-pyridyl)sulfonyl]-6-tetrahydropyran-2-yl-2-[(4S)-2,2,4-trimethylpyrrolidin-1-yl]pyridine-3-carboxamide (Compound 1697)

Step 1: N-[(2-amino-3-pyridyl)sulfonyl]-2,6-dichloro-pyridine-3-carboxamide

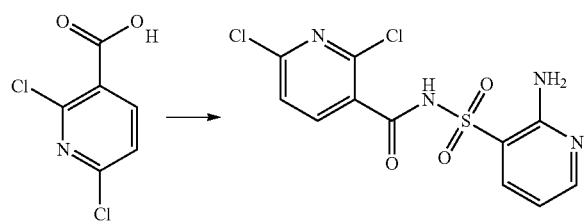

2,6-dichloropyridine-3-carboxylic acid (1.5 g, 7.8 mmol) and CDI (1.9 g, 11.7 mmol) in DMF (17 mL) was stirred at 60° C. In a separate vial, 2-aminopyridine-3-sulfonamide (1.7 g, 9.8 mmol) and NaH (0.4 g, 9.8 mmol) in DMF (8 mL) was stirred at ambient temperature. The two reaction mixtures were combined and stirred overnight at room temperature. The reaction mixture was taken up in EtOAc and washed with HCl (1 N, 1×25 mL) and the aqueous layer was washed with EtOAc (4×20 mL). The combined organic layers were washed with brine (1×15 mL) and dried over sodium sulfate, filtered, and concentrated under reduced pressure. The resulting solid that crashed was washed with ethyl acetate and the mother liquor was concentrated, the residue was washed with ethyl acetate and hexanes to obtain N-[(2-amino-3-pyridyl)sulfonyl]-2,6-dichloro-pyridine-3-carboxamide (2.5 g, 94%) as a white solid. 1H NMR (400 MHz, DMSO-$d_6$) δ 8.28-8.12 (m, 2H), 8.07 (d, J=8.0 Hz, 1H), 7.62 (d, J=8.0 Hz, 1H), 6.87 (dd, J=7.7, 5.4 Hz, 1H).

Step 2: N-[(2-amino-3-pyridyl)sulfonyl]-6-chloro-2-[(4S)-2,2,4-trimethylpyrrolidin-1-yl]pyridine-3-carboxamide

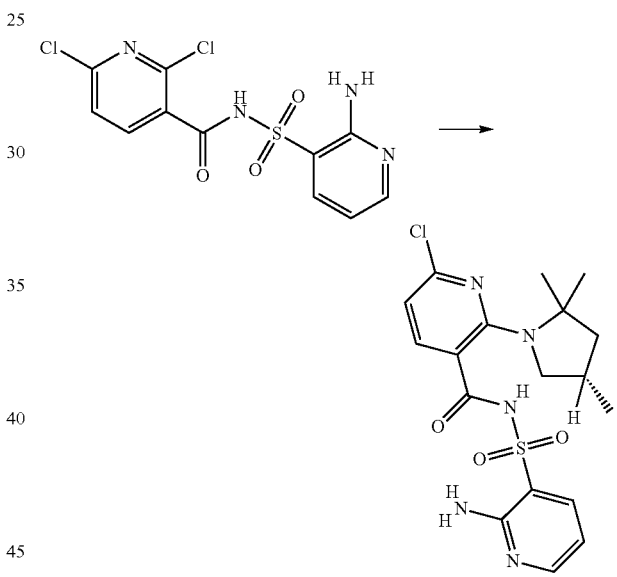

DMSO (17 mL) was added to N-[(2-amino-3-pyridyl)sulfonyl]-2,6-dichloro-pyridine-3-carboxamide (2.1 g, 6.0 mmol), (4S)-2,2,4-trimethylpyrrolidine (HCl salt) (1.1 g, 7.3 mmol), and potassium carbonate (3.3 g, 24 mmol). The reaction mixture was sealed and stirred at 120° C. for 2 days. The reaction mixture was allowed to cool and then diluted with ethyl acetate (40 mL) and water (60 mL). To the aqueous layer, aq HCl was added to pH 7 and then washed with ethyl acetate (5×50 mL). The combined organic layers were concentrated to half volume then washed with brine and dried over sodium sulfate, filtered and evaporated under reduced pressure to give N-[(2-amino-3-pyridyl)sulfonyl]-6-chloro-2-[(4S)-2,2,4-trimethylpyrrolidin-1-yl]pyridine-3-carboxamide (2.5 g, 100%) as a yellow powder. 1H NMR (400 MHz, DMSO-$d_6$) δ 8.26 (dd, J=4.8, 1.8 Hz, 1H), 8.06 (dd, J=7.9, 1.8 Hz, 1H), 7.71 (d, J=7.9 Hz, 1H), 6.79 (dd, J=7.9, 4.8 Hz, 1H), 6.64 (d, J=7.9 Hz, 1H), 2.46-2.34 (m, 2H), 2.19-2.03 (m, 1H), 1.82 (dd, J=12.1, 5.6 Hz, 1H), 1.47 (d, J=3.3 Hz, 6H), 1.36 (t, J=12.2 Hz, 1H), 0.74 (d, J=6.3 Hz, 3H).

Step 3: N-[(2-amino-3-pyridyl)sulfonyl]-6-(3,4-dihydro-2H-pyran-6-yl)-2-[(4S)-2,2,4-trimethylpyrrolidin-1-yl]pyridine-3-carboxamide (Compound 1699)

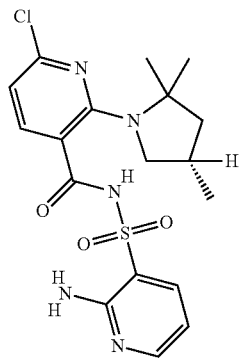

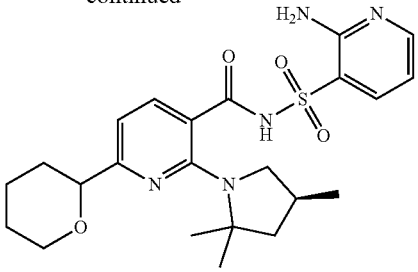

N-[(2-amino-3-pyridyl)sulfonyl]-6-chloro-2-[(4S)-2,2,4-trimethylpyrrolidin-1-yl]pyridine-3-carboxamide (32 mg, 0.08 mmol), 2-(3,4-dihydro-2H-pyran-6-yl)-4,4,5,5-tetramethyl-1,3,2-dioxaborolane (19 mg, 0.09 mmol), and 1,3-bis(2,6-diisopropylphenyl)-4,5-dihydroimidazole; 3-chloropyridine; dichloropalladium (3 mg, 0.005 mmol, 5 mol %) was dissolved in EtOH (600 µL) and solution of potassium carbonate (150 µL, 2M) was added. The reaction mixture was heated at 120° C. for 16 hours under an atmosphere of nitrogen. The reaction mixture was cooled, filtered and purified via LC/MS utilizing a gradient of 25-75% acetonitrile in 5 mM aq HCl. Sodium carbonate was added to collected fractions (pH 7-8) and the solvents were removed to dryness to yield the desired compound. ESI-MS m/z 472.3 (M+1)⁺; Retention time: 1.18 minutes Step 4: N-[(2-amino-3-pyridyl)sulfonyl]-6-tetrahydropyran-2-yl-2-[(4S)-2,2,4-trimethylpyrrolidin-1-yl]pyridine-3-carboxamide (Compound 2351)

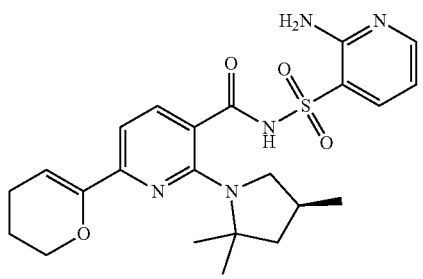

To N-[(2-amino-3-pyridyl)sulfonyl]-6-(3,4-dihydro-2H-pyran-6-yl)-2-[(4S)-2,2,4-trimethylpyrrolidin-1-yl]pyridine-3-carboxamide (Compound 1699) (37 mg, 0.08 mmol) in EtOH (3 mL), palladium on carbon (8 mg, 0.008 mmol, 10w/w %) was added. The reaction mixture was stirred under an atmosphere of hydrogen 16 hours at ambient temperature. The reaction mixture was filtered and evaporated to dryness, dissolved in DMSO-methanol and purified via reverse phase HPLC-MS method using a dual gradient run from 1-99% mobile phase B over 15.0 minutes. Mobile phase A=H₂O (5 mM TFA) Mobile phase B=acetonitrile to yield N-[(2-amino-3-pyridyl)sulfonyl]-6-tetrahydropyran-2-yl-2-[(4S)-2,2,4-trimethylpyrrolidin-1-yl]pyridine-3-carboxamide (Compound 2351). ESI-MS m/z 474.4 (M+1)⁺; Retention time: 1.15 minutes.

The following compounds can be synthesized using the procedures described herein:

N-[(2-amino-3-pyridyl)sulfonyl]-6-(1,2-dimethylpropyl)-2-[(4S)-2,2,4-trimethylpyrrolidin-1-yl]pyridine-3-carboxamide (Compound 1911)

N-[(2-amino-3-pyridyl)sulfonyl]-6-(5,5-dimethyl-2-oxo-cyclohexyl)-2-[(4S)-2,2,4-trimethylpyrrolidin-1-yl]pyridine-3-carboxamide (Compound 1793)

N-[(2-amino-3-pyridyl)sulfonyl]-6-norbornan-2-yl-2-[(4S)-2,2,4-trimethylpyrrolidin-1-yl]pyridine-3-carboxamide (Compound 2097)

N-[(2-amino-3-pyridyl)sulfonyl]-6-tetrahydropyran-4-yl-2-[(4S)-2,2,4-trimethylpyrrolidin-1-yl]pyridine-3-carboxamide (Compound 1850)

N-[(2-amino-3-pyridyl)sulfonyl]-6-(2-cyclopropylethyl)-2-[(4S)-2,2,4-trimethylpyrrolidin-1-yl]pyridine-3-carboxamide (Compound 2553)

N-[(2-amino-3-pyridyl)sulfonyl]-6-(2-hydroxy-5,5-dimethyl-cyclohexyl)-2-[(4S)-2,2,4-trimethylpyrrolidin-1-yl]pyridine-3-carboxamide (Compound 2047)

N-(benzenesulfonyl)-6-tetrahydropyran-2-yl-2-[(4S)-2,2,4-trimethylpyrrolidin-1-yl]pyridine-3-carboxamide (Compound 1868)

N-(benzenesulfonyl)-6-isobutyl-2-[(4S)-2,2,4-trimethylpyrrolidin-1-yl]pyridine-3-carboxamide (Compound 2246)

N-(benzenesulfonyl)-6-tetrahydrofuran-3-yl-2-[(4S)-2,2,4-trimethylpyrrolidin-1-yl]pyridine-3-carboxamide (Compound 2277)

N-[(2-amino-3-pyridyl)sulfonyl]-6-tetrahydropyran-3-yl-2-[(4S)-2,2,4-trimethylpyrrolidin-1-yl]pyridine-3-carboxamide (Compound 2311)

N-[(6-amino-2-pyridyl)sulfonyl]-6-(3-bicyclo[2.2.1]hept-2-enyl)-2-[(4S)-2,2,4-trimethylpyrrolidin-1-yl]pyridine-3-carboxamide (Compound 2709)

N-[(2-amino-3-pyridyl)sulfonyl]-6-[4-(trifluoromethyl)cyclohexyl]-2-[(4S)-2,2,4-trimethylpyrrolidin-1-yl]pyridine-3-carboxamide (Compound 2077) (Isomer 1, cis or trans stereoisomer)

N-[(2-amino-3-pyridyl)sulfonyl]-6-[4-(trifluoromethyl)cyclohexyl]-2-[(4S)-2,2,4-trimethylpyrrolidin-1-yl]pyridine-3-carboxamide (Compound 2432) (Isomer 2, cis or trans stereoisomer).

Preparation 126: N-[(2-amino-3-pyridyl)sulfonyl]-6-tetrahydropyran-2-yl-2-[(4S)-2,2,4-trimethylpyrrolidin-1-yl]pyridine-3-carboxamide (Compound 2351) (Isomer 1, RS or SS stereoisomer) and N-[(2-amino-3-pyridyl)sulfonyl]-6-tetrahydropyran-2-yl-2-[(4S)-2,2,4-trimethylpyrrolidin-1-yl]pyridine-3-carboxamide (Compound 2351) (Isomer 2, RS or SS stereoisomer)

N-[(2-amino-3-pyridyl)sulfonyl]-6-[2-tetrahydropyran-2-yl]-2-[(4S)-2,2,4-trimethylpyrrolidin-1-yl]pyridine-3-carboxamide (Compound 2672) (Isomer 1, RS or SS stereoisomer) and
N-[(2-amino-3-pyridyl)sulfonyl]-6-[2-tetrahydropyran-2-yl]-2-[(4S)-2,2,4-trimethylpyrrolidin-1-yl]pyridine-3-carboxamide (Compound 2675) (Isomer 2, RS or SS stereoisomer).

Preparation 127: N-[(6-amino-2-pyridyl)sulfonyl]-6-tert-butyl-2-(3-cyclopropyl-2,2-dimethyl-pyrrolidin-1-yl)pyridine-3-carboxamide (Compound 2577) (Compound 2022) (Isomer 1, R or S stereoisomer) and N-[(6-amino-2-pyridyl)sulfonyl]-6-tert-butyl-2-(3-cyclopropyl-2,2-dimethyl-pyrrolidin-1-yl)pyridine-3-carboxamide (Compound 2577) (Compound 2022) (Isomer 2, R or S stereoisomer)

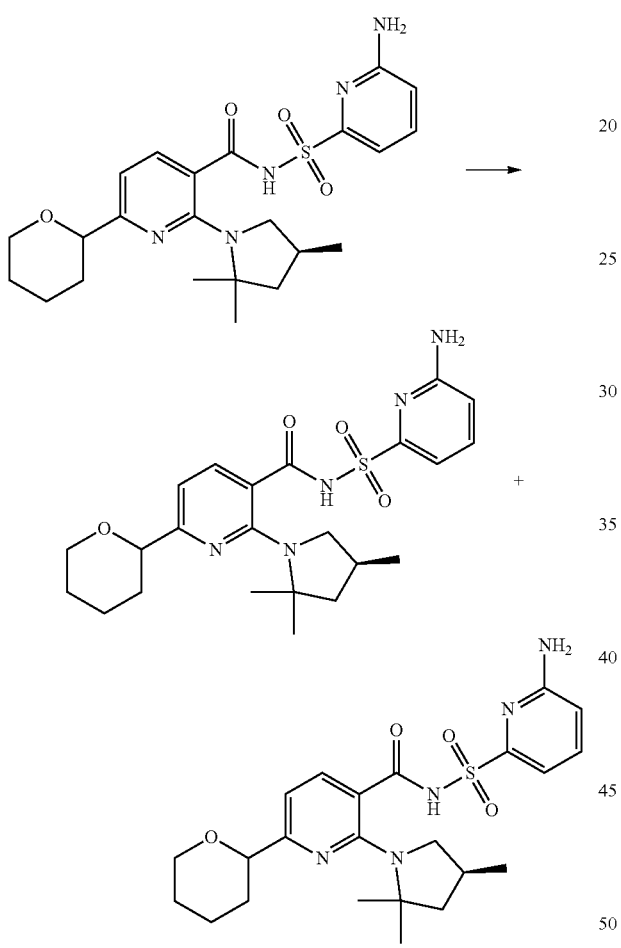

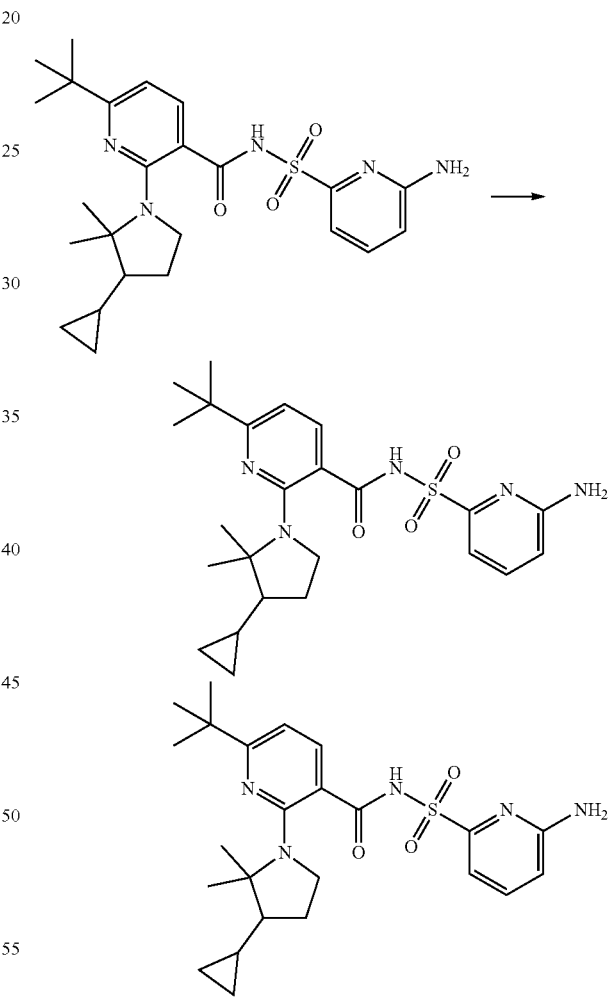

The stereoisomers were separated using supercritical fluid chromatography on a Phenomenex LUX-4 (250×10 mm), 5 µm column using 48% EtOH/IPA (50/50) in $CO_2$ at a flow rate of 10.0 mL/min. The separated enantiomers were separately concentrated to dryness to give the pure compounds. SFC Peak 1: N-[(2-amino-3-pyridyl)sulfonyl]-6-tetrahydropyran-2-yl-2-[(4S)-2,2,4-trimethylpyrrolidin-1-yl]pyridine-3-carboxamide (Compound 2351) ESI-MS m/z 474.4 (M+1)$^+$; Retention time: 1.15 minutes. SFC Peak 2: N-[(2-amino-3-pyridyl)sulfonyl]-6-tetrahydropyran-2-yl-2-[(4S)-2,2,4-trimethylpyrrolidin-1-yl]pyridine-3-carboxamide (Compound 2351) ESI-MS m/z 474.4 (M+1)$^+$; Retention time: 1.15 minutes.

The following compounds can be synthesized using the procedures described herein:

The stereoisomers were separated using supercritical fluid chromatography on a ChiralPak AD-H (250×10 mm), 5 m column using 22% EtOH/MeOH (90:10, 20 mM $NH_3$) in $CO_2$ at a flow rate of 10.0 mL/min. The separated enantiomers were separately concentrated, diluted with ethyl acetate (3 mL) and washed with 1N aqueous hydrochloric acid. The organic layers were dried over sodium sulfate, filtered, and evaporated to dryness to give the pure compounds. SFC Peak 1: N-[(6-amino-2-pyridyl)sulfonyl]-6-tert-butyl-2-(3- cyclopropyl-2,2-dimethyl-pyrrolidin-1-yl)pyridine-3-carboxamide (Compound 2577) (Compound 2022) 1H NMR (400 MHz, DMSO) δ 12.35 (s, 1H), 7.59 (d, J=7.7 Hz, 2H), 7.14 (d, J=6.7 Hz, 1H), 6.73-6.58 (m, 2H), 6.43 (s, 2H), 2.79 (s, 1H), 2.62 (s, 1H), 1.80-1.59 (m, 2H), 1.56 (s, 3H), 1.51 (s, 3H), 1.27 (s, 9H), 1.13-1.03 (m, 1H), 0.71-0.58 (m, 1H), 0.56-0.46 (m, 1H), 0.46-0.33 (m, 1H), 0.24 (td, J=9.2, 5.0 Hz, 1H), 0.12-0.01 (m, 1H). SFC Peak 2: N-[(6-amino-2-pyridyl)sulfonyl]-6-tert-butyl-2-(3-cyclopropyl-2,2-dimethyl-pyrrolidin-1-yl)pyridine-3-carboxamide (Compound 2577) (Compound 2022) 1H NMR (400 MHz, DMSO) δ 12.35 (s, 1H), 7.58 (d, J=7.1 Hz, 2H), 7.14 (d, J=7.1 Hz, 1H), 6.77-6.56 (m, 2H), 6.42 (s, 2H), 2.79 (s, 1H), 2.66 (dd, J=12.3, 10.5 Hz, 1H), 1.69 (d, J=20.9 Hz, 2H), 1.56 (s, 3H), 1.51 (s, 3H), 1.27 (s, 9H), 1.17-1.05 (m, 1H), 0.73-0.63 (m, 1H), 0.58-0.47 (m, 1H), 0.40 (dd, J=8.2, 3.9 Hz, 1H), 0.24 (dd, J=9.0, 4.1 Hz, 1H), 0.07 (dd, J=9.0, 4.0 Hz, 1H).

Preparation 128: N-[(6-amino-2-pyridyl)sulfonyl]-6-tert-butyl-2-(2,2-dimethyl-3-tetrahydropyran-4-yl-pyrrolidin-1-yl)pyridine-3-carboxamide (Compound 2425) (Compound 2266) (Isomer 1, R or S stereoisomer) and N-[(6-amino-2-pyridyl)sulfonyl]-6-tert-butyl-2-(2,2-dimethyl-3-tetrahydropyran-4-yl-pyrrolidin-1-yl)pyridine-3-carboxamide (Compound 2425) (Compound 2266) (Isomer 2, R or S stereoisomer)

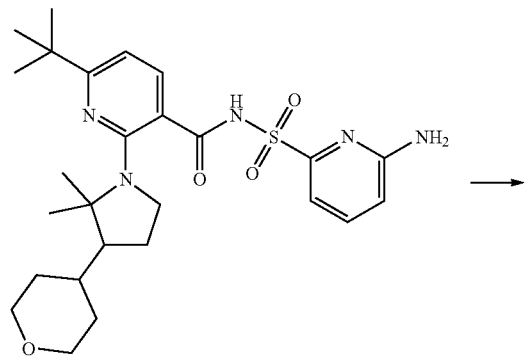

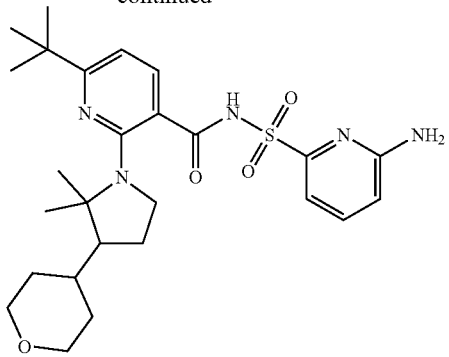

The stereoisomers were separated using supercritical fluid chromatography on a ChiralPak AD-H (250×10 mm), 5 μm column using 12% MeOH in $CO_2$ at a flow rate of 10.0 mL/min. The separated enantiomers were separately concentrated, diluted with ethyl acetate (3 mL) and washed with 1N aqueous hydrochloric acid. The organic layers were dried over sodium sulfate, filtered, and evaporated to dryness to give the pure compounds. SFC Peak 1: N-[(6-amino-2-pyridyl)sulfonyl]-6-tert-butyl-2-(2,2-dimethyl-3-tetrahydropyran-4-yl-pyrrolidin-1-yl)pyridine-3-carboxamide (Compound 2425) (Compound 2266) ESI-MS m/z calc. 515.25665, found 516.2 (M+1)$^+$; Retention time: 1.31 minutes. SFC Peak 2: N-[(6-amino-2-pyridyl)sulfonyl]-6-tert-butyl-2-(2,2-dimethyl-3-tetrahydropyran-4-yl-pyrrolidin-1-yl)pyridine-3-carboxamide (Compound 2425) (Compound 2266) ESI-MS m/z calc. 515.25665, found 516.2 (M+1)$^+$; Retention time: 1.31 minutes. 1H NMR (400 MHz, DMSO) δ 12.48 (s, 1H), 7.70-7.52 (m, 2H), 7.17 (dd, J=7.3, 0.5 Hz, 1H), 6.70 (dd, J=9.7, 8.5 Hz, 2H), 5.19 (s, 2H), 3.84 (td, J=11.1, 3.7 Hz, 2H), 3.38-3.18 (m, 2H), 2.84 (t, J=10.0 Hz, 1H), 2.68-2.55 (m, 1H), 2.07 (s, 4H), 1.81 (t, J=6.4 Hz, 1H), 1.65 (dd, J=30.6, 10.5 Hz, 2H), 1.55 (d, J=8.6 Hz, 6H), 1.49 (s, 3H), 1.28 (d, J=6.6 Hz, 10H).

Preparation 129: N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Isomer 1) (Compound 2178) (Isomer 2) (Compound 2062) (Isomer 3) (Compound 1863) (Isomer 4)

Step 1: N-[(6-amino-2-pyridyl)sulfonyl]-2-chloro-6-(3-fluoro-5-isobutoxy-phenyl)pyridine-3-carboxamide

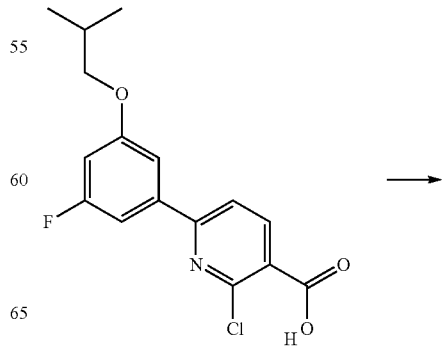

2223
-continued

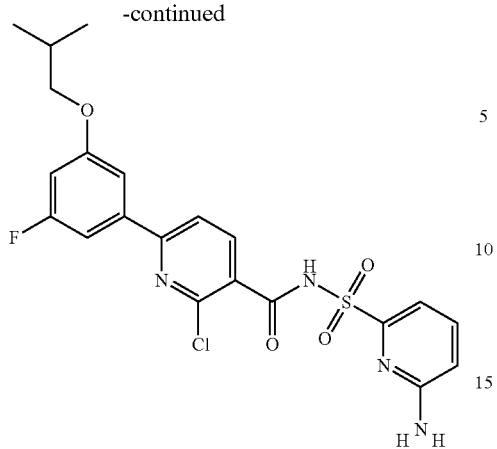

2-chloro-6-(3-fluoro-5-isobutoxy-phenyl)pyridine-3-carboxylic acid (3.91 g, 9.66 mmol) was dissolved in DMF (31 mL) was stirred under nitrogen and CDI (2.35 g, 14.5 mmol) was added in one portion. The reaction mixture was warmed to 65° C. and heated for 1 h. Meanwhile in a separate vessel, 6-aminopyridine-2-sulfonamide (2.09 g, 12.1 mmol) was slurried in DMF (15 mL) under nitrogen and NaH (483 mg, 12.1 mmol) added portionwise to mitigate gas evolution and the reaction was stirred for 1 h. The two reactions were combined in one portion at 65° C. The reaction was stirred for 15 min and evaporated. The reaction mixture was poured over ice and acidified (ph=4) by the addition of 6M HCl. The resulting mixture was extracted with ethyl acetate (1 L). The organics were washed with brine (2×500 mL), dried over sodium sulfate and evaporated under reduced pressure. The crude material was purified by silica gel column chromatography eluting with 0-100% ethyl acetate in hexanes to give N-[(6-amino-2-pyridyl)sulfonyl]-2-chloro-6-(3-fluoro-5-isobutoxy-phenyl)pyridine-3-carboxamide (4.02 g, 887%) ESI-MS m/z calc. 478.08777, found 479.1 (M+1)+; Retention time: 0.7 minutes.

Step 2: N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Compound 2178) (Compound 2062) (Compound 1863)

2224
-continued

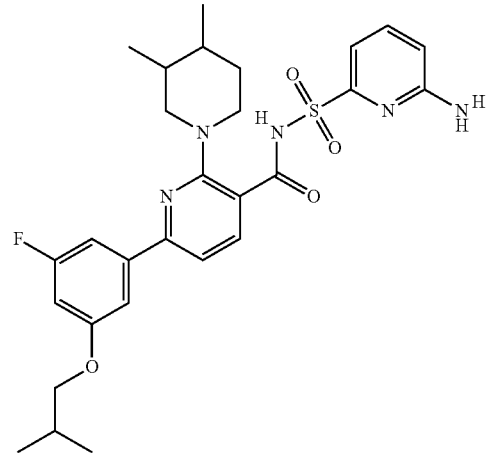

N-[(6-amino-2-pyridyl)sulfonyl]-2-chloro-6-(3-fluoro-5-isobutoxy-phenyl)pyridine-3-carboxamide (100 mg, 0.21 mmol) and fluorocesium (156 mg, 38.5 μL, 1.04 mmol) in DMSO (600 μL) followed by K$_2$CO$_3$ (289 mg, 2.09 mmol) and 3,4-dimethylpiperidine (118 mg, 1.04 mmol). The reaction mixture was sealed and heated to 150° C. overnight, then 165° C. for 6 hours. The reaction mixture was filtered and then purified directly by reverse-phase HPLC-MS using 10-99% Acetonitrile-Water+5 mmolar HCl as eluent to afford N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Compound 2178) (Compound 2062) (Compound 1863) (86 mg, 74%), as a light yellow solid ESI-MS m/z calc. 555.23157, found 556.2 (M+1)+; Retention time: 2.0 minutes. 1H NMR (400 MHz, DMSO) δ 12.66 (s, 1H), 7.81 (d, J=7.9 Hz, 1H), 7.65 (t, J=7.8 Hz, 1H), 7.50-7.41 (m, 3H), 7.22 (d, J=7.3 Hz, 1H), 6.91 (d, J=10.9 Hz, 1H), 6.72 (d, J=8.4 Hz, 1H), 6.47 (s, 1H), 3.85 (d, J=6.5 Hz, 2H), 3.51 (d, J=8.5 Hz, 1H), 3.40 (d, J=12.8 Hz, 1H), 3.13 (d, J=11.8 Hz, 1H), 2.97 (d, J=6.0 Hz, 1H), 2.06 (d, J=9.3 Hz, 1H), 1.89-1.72 (m, 2H), 1.42 (s, 2H), 1.00 (d, J=6.7 Hz, 6H), 0.87 (d, J=6.6 Hz, 3H), 0.77 (d, J=6.6 Hz, 3H Step 3: N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Compound 2178) (Compound 2062) (Compound 1863) (Isomers 1-4, RR, RS, SS, or SR stereoisomer)

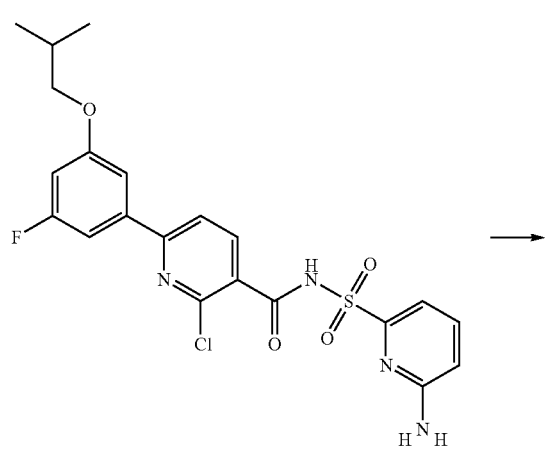

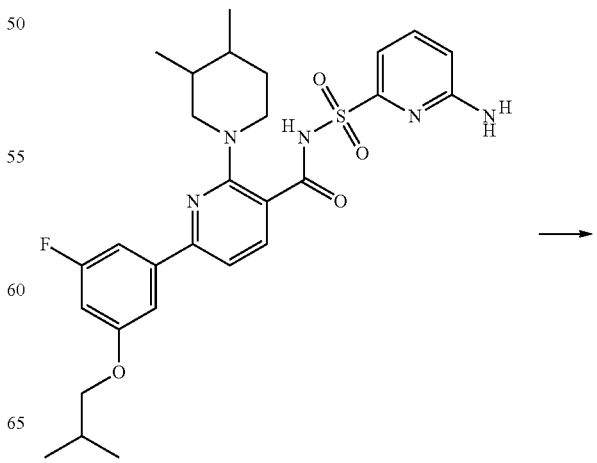

2225
-continued

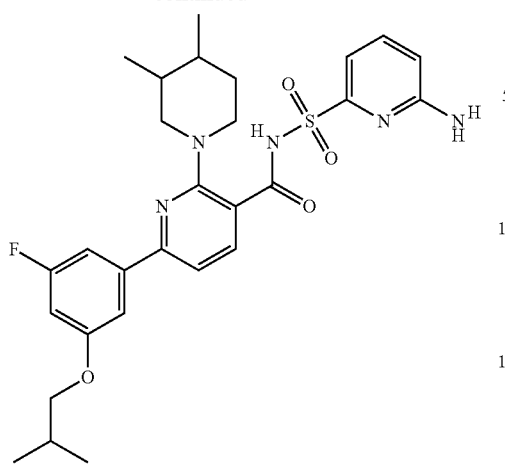

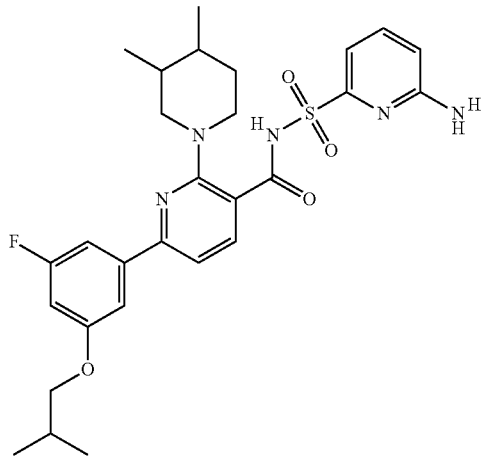

2226
-continued

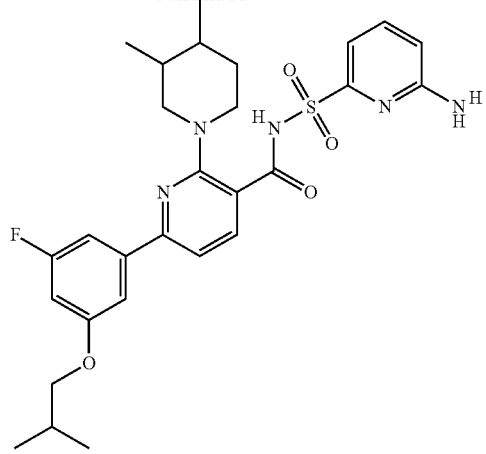

The stereoisomers were separated using supercritical fluid chromatography on a ChiralCel OZ-H (250×10 mm), 5 m column using 25% MeOH:EtOH 50:50 in $CO_2$ at a flow rate of 10.0 mL/min. The separated enantiomers were separately concentrated to give the pure compound. SFC Peak 1: N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Compound 2178) (Compound 2062) (Compound 1863) ESI-MS m/z calc. 555.23157, found 556.2 (M+1)$^+$; Retention time: 2.02 minutes. SFC Peak 2 (N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Compound 2178) (Compound 2062) (Compound 1863) ESI-MS m/z calc. 555.23157, found 556.2 (M+1)$^+$; Retention time: 2.01 minutes. SFC Peak 3 N-[(6-amino-2-pyridyl)sulfonyl]-2-(3,4-dimethyl-1-piperidyl)-6-(3-fluoro-5-isobutoxy-phenyl)pyridine-3-carboxamide (Compound 2532) (Compound 2178) (Compound 2062) (Compound 1863) ESI-MS m/z calc. 555.23157, found 556.2 (M+1)$^+$; Retention time: 1.96 minutes. SFC Peak 4 ESI-MS m/z calc. 555.23157, found 556.2 (M+1)$^+$; Retention time: 1.96 minutes. 1H NMR (400 MHz, DMSO) δ 12.66 (s, 1H), 7.79 (d, J=7.8 Hz, 1H), 7.63 (t, J=10.7 Hz, 1H), 7.45 (d, J=11.6 Hz, 3H), 7.20 (d, J=6.5 Hz, 1H), 6.90 (d, J=10.7 Hz, 1H), 6.70 (d, J=7.1 Hz, 1H), 6.44 (s, 2H), 3.84 (d, J=6.5 Hz, 2H), 3.50 (s, 1H), 3.38 (s; 1H), 3.12 (d, J=13.0 Hz, 1H), 2.96 (s, 1H), 2.08-1.98 (m, 1H), 1.80 (s, 2H), 1.41-1.37 (m, 1H), 1.30-1.22 (m, 1H), 1.00 (d, J=6.7 Hz, 7H), 0.86 (d, J=6.5 Hz, 4H), 0.76 (d, J=6.6 Hz, 3H).

The following compounds can be synthesized using the procedures described herein:

N-[(6-amino-2-pyridyl)sulfonyl]-2-(2,5-dimethyl-1-piperidyl)-6-(3-fluoro-5-isobutoxy-phenyl)pyridine-3-carboxamide (Compound 2451) (Compound 1993) (Compound 1864) (Compound 1855) (Isomers 1-4, stereoisomers RR, RS, SS, SR), using as SFC ChiralCel OZ-H (250×10 mm), 5 μm column and eluent 25% MeOH (20 mM NH$_3$) in $CO_2$ N-[(6-amino-2-pyridyl)sulfonyl]-6-(3-fluoro-5-isobutoxyphenyl)-2-(6-methyl-8-azaspiro[3.4]octaN-8-yl)pyridine-3-carboxamide (Compound 2552) (Isomer 1, R or S stereoisomer) (Compound 2269) (Isomer 2, R or S stereoisomer), using as SFC ChiralPak IA (250×10 mm), 5 μm column and eluent 22% EtOH (0.1% TFA) in $CO_2$ N-[(6-amino-2-pyridyl)sulfonyl]-2-(2-ethyl-2,4-dimethylpyrrolidin-1-yl)-6-(3-fluoro-5-isobutoxy-phenyl)pyri-

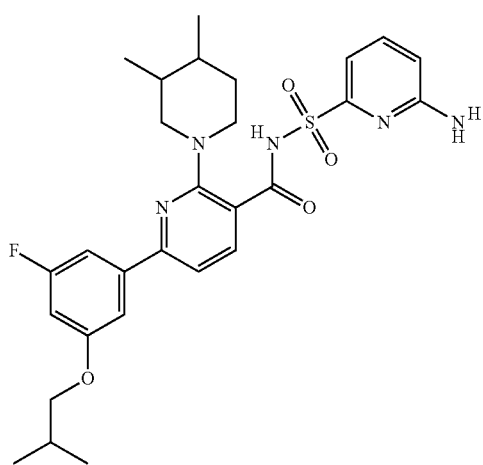

dine-3-carboxamide (Compound 2213) (Compound 2058) (Compound 1817) (Compound 1729) (Isomers 1-4, stereoisomers RR, RS, SS, SR), using as SFC ChiralCel OZ-H (250×10 mm), 5 μm column and eluent 22% IPA:EtOH 50:50 in CO₂

N-[(6-amino-2-pyridyl)sulfonyl]-2-(2,2-dimethyl-4-(trifluoromethyl)pyrrolidin-1-yl)-6-(3-fluoro-5-isobutoxy-phenyl)pyridine-3-carboxamide (Compound 2271) (Isomer 1, R or S stereoisomer) using as SFC ChiralCel OZ-H (250×10 mm), 5 μm column and eluent 25% MeOH:EtOH (50:50) in CO₂.

Preparation 130: N-[(6-amino-2-pyridyl)sulfonyl]-6-(3-fluoro-5-isobutoxy-phenyl)-5-iodo-2-[(4S)-2,2,4-trimethylpyrrolidin-1-yl]pyridine-3-carboxamide (Compound 2009)

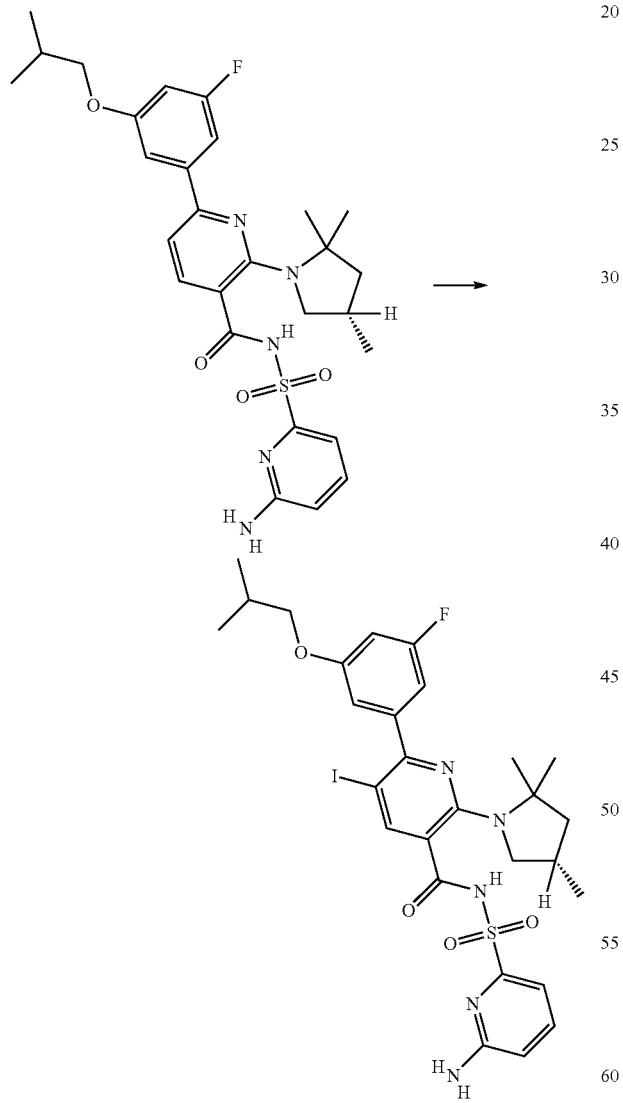

N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (100 mg, 0.18 mmol) was dissolved in CH₂Cl2 (700 μL) and was treated with 1-iodopyrrolidine-2,5-dione (44 mg, 0.19 mmol). The reaction mixture was allowed to stir at 40° C. for 30 minutes. The volatiles were evaporated under a slow stream of nitrogen gas. The remaining residue was redissolved in DMSO, filtered and purified by reverse-phase HPLC using a Luna C18 (2) column (50×21.2 mm, 5 μm particle size) and a dual gradient run from 30-99% mobile phase B over 15.0 minutes (mobile phase A=water (de-ionized, no acid modifier), mobile phase B=acetonitrile) to give the desired compound. ESI-MS m/z calc. 681.1282, found 682.2 (M+1)⁺; Retention time: 2.26 minutes.

Preparation 131: N-[(6-amino-2-pyridyl)sulfonyl]-6-(3-fluoro-5-isobutoxy-phenyl)-N-methyl-2-[(4S)-2,2,4-trimethylpyrrolidin-1-yl]pyridine-3-carboxamide (Compound 2258)

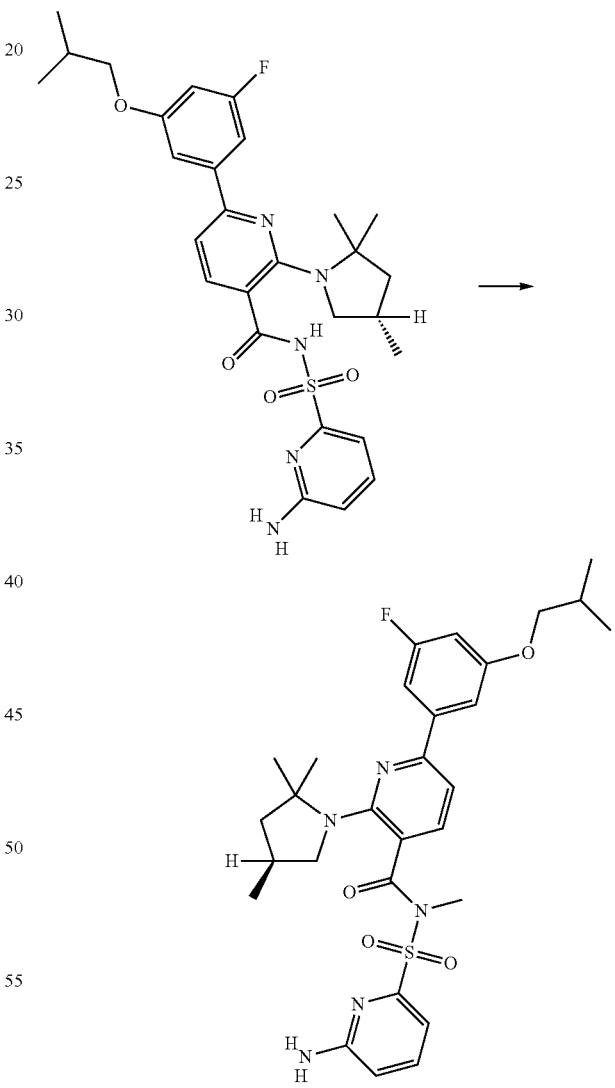

N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (500 mg, 0.90 mmol) in DMF (5 mL) was treated with Cs₂CO₃ (352 mg, 1.1 mmol) and the reaction mixture was stirred for 0.5 h at room temperature, then cooled in an ice bath and treated with MeI (141 mg, 61 μL, 1.0 mmol). The reaction mixture was stirred overnight at room temperature. The suspension was added to water (25 ml), stirred at room temperature for 1 h and the suspension was filtered and washed with water. The solid was purified by silica gel column chromatography using as dichloromethane as eluent to give N-[(6-amino-2-pyridyl)sulfonyl]-6-(3-fluoro-5-isobutoxy-phenyl)-N-methyl-2-[(4S)-2,2,4-trimethylpyrrolidin-1-yl]pyridine-3-carboxamide (Compound 2258) (315 mg, 61%). ESI-MS m/z 570.0 (M+1)$^+$; Retention time: 3.4 minutes; 1H NMR (400 MHz, DMSO-d$_6$) δ 7.67-7.54 (i, 2H), 7.49 (t, J=1.8 Hz, 1H), 7.40 (dt, J=10.2, 1.8 Hz, 1H), 7.23 (d, J=8.0 Hz, 1H), 7.06 (d, J=7.3 Hz, 1H), 6.89 (dt, J 10.7, 2.3 Hz, 1H), 6.70 (d, J=8.4 Hz, 1H), 6.64 (s, 2H), 3.84 (d, J=6.7 Hz, 2H), 3.43 (s, 3H), 2.82 (s, 1H), 2.64 (s, 1H), 2.34-2.22 (m, 1H), 2.05 (hept, J 6.6 Hz, 1H), 1.91 (dd, J=11.9, 5.7 Hz, 1H), 1.62 (d, J=4.4 Hz, 6H), 1.46 (t, J=12.1 Hz, 1H), 0.99 (d, J=6.7 Hz, 6H), 0.94 (d, J=6.3 Hz, 3H)

Preparation 132: N-[(6-amino-2-pyridyl)sulfonyl]-2-(2,6-dimethylphenoxy)-6-[3-fluoro-5-(2-hydroxy-2-methyl-propoxy)phenyl]pyridine-3-carboxamide (Compound 1890)

Step 1: 1-[3-fluoro-5-(4,4,5,5-tetramethyl-1,3,2-dioxaborolan-2-yl)phenoxy]-2-methyl-propan-2-ol

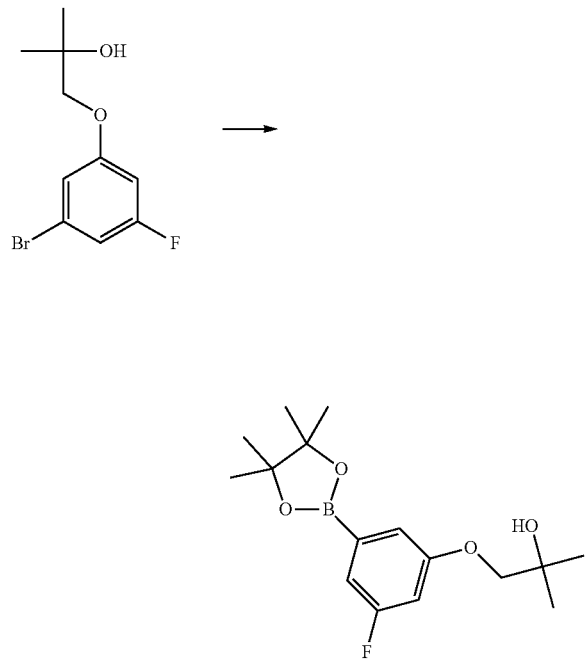

To a suspension of 1-(3-bromo-5-fluoro-phenoxy)-2-methyl-propan-2-ol (25.0 g, 95 mmol), Bis(pinacolato)diboron (26.5 g, 105 mmol), and KOAc (18.7 g, 190 mmol) in dioxane (375 mL) under an atmosphere of nitrogen was added Pd(dppf)Cl$_2$·DCM (768 mg, 1.0 mmol) and the reaction mixture was heated to 103° C. for 2 hours, cooled and stirred overnight at room temperature. The reaction mixture was filtered through Florisil and the filtrate was concentrated under reduced pressure to afford a yellow oil. The oil was purified by silica gel column chromatography eluted with EtOAc/heptane (10-20% EtOAc) to afford 1-[3-fluoro-5-(4,4,5,5-tetramethyl-1,3,2-dioxaborolan-2-yl)phenoxy]-2-methyl-propan-2-ol (12.6 g (86%) as pale yellow liquid.

Step 2: N-[(6-amino-2-pyridyl)sulfonyl]-2-(2,6-dimethylphenoxy)-6-[3-fluoro-5-(2-hydroxy-2-methyl-propoxy)phenyl]pyridine-3-carboxamide (Compound 1890)

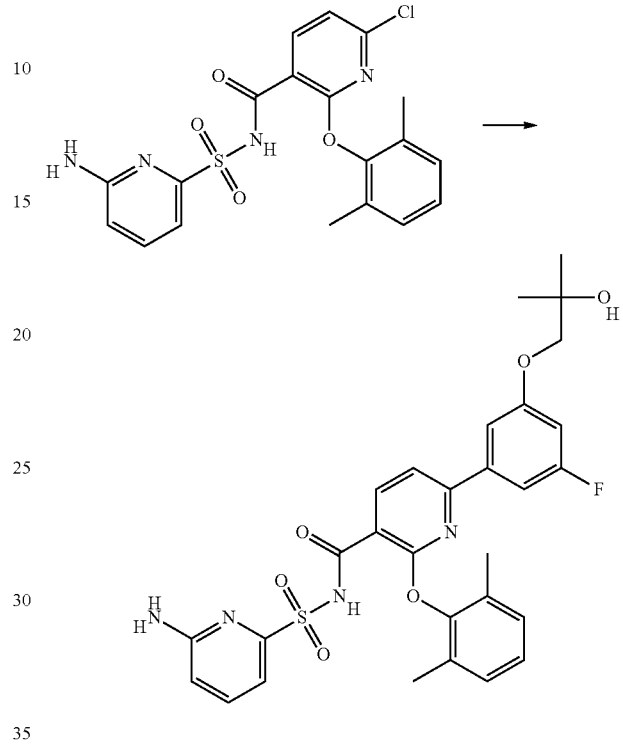

N-[(6-amino-2-pyridyl)sulfonyl]-6-chloro-2-(2,6-dimethylphenoxy)pyridine-3-carboxamide (140 mg, 0.32 mmol), 1-[3-fluoro-5-(4,4,5,5-tetramethyl-1,3,2-dioxaborolan-2-yl)phenoxy]-2-methyl-propan-2-ol (215 mg, 0.69 mmol), potassium carbonate (647 μL of 2 M, 1.29 mmol), and 1,3-bis(2,6-diisopropylphenyl)-4,5-dihydroimidazole; 3-chloropyridine; dichloropalladium (PEPPSI-IPr) (11 mg, 0.02 mmol) were combined in ethanol (3 mL) and the reaction mixture was heated at 80° C. for 21 h. The reaction mixture was cooled to 40° C., glacial AcOH (0.20 mL) was added, filtered and the filtrate evaporated under reduced pressure. The residue was dissolved in DMSO (3 mL), filtered and purified using a reverse phase HPLC-MS method using a Luna C18 (2) column (75×30 mm, 5 m particle size) and a dual gradient run from 10-99% mobile phase B over 30.0 minutes (mobile phase A=H$_2$O (5 mM HCl), mobile phase B=CH$_3$CN) to give N-[(6-amino-2-pyridyl)sulfonyl]-2-(2,6-dimethylphenoxy)-6-[3-fluoro-5-(2-hydroxy-2-methyl-propoxy)phenyl]pyridine-3-carboxamide (Compound 1890) (HCl salt) (80 mg, 40%) 1H NMR (400 MHz, DMSO-d$_6$) δ 12.39 (s, 1H), 8.16 (d, J=7.8 Hz, 1H), 7.84 (d, J=7.9 Hz, 1H), 7.66 (t, J=7.9 Hz, 1H), 7.24 (d, J=7.3 Hz, 1H), 7.21-7.14 (m, 4H), 7.14-7.07 (m, 1H), 6.84 (dt, J=10.6, 2.3 Hz, 1H), 6.72 (d, J=8.4 Hz, 1H), 6.54 (s, 2H), 4.61 (s, 1H), 3.61 (s, 2H), 2.07 (s, 1H), 2.06 (s, 6H), 1.19 (s, 6H). ESI-MS m/z calc. 580.1792, found 581.2 (M+1)$^+$; Retention time: 1.76 minutes.

The following compound can be synthesized using the procedures described herein:
N-[(6-amino-2-pyridyl)sulfonyl]-2-(2,6-dimethylphenoxy)-6-[3-fluoro-5-(3-hydroxy-2-methyl-propoxy)phenyl]pyridine-3-carboxamide (Compound 1797)

Preparation 133: N-[(6-amino-2-pyridyl)sulfonyl]-6-(3-fluoro-5-isobutoxy-phenyl)-2-(3,5,5-trimethylcyclopenten-1-yl)pyridine-3-carboxamide (Compound 2081) (Isomer 1, R or S stereoisomer) (Compound 2039) (Isomer 2, R or S stereoisomer)

Step 1: Ethyl 2-chloro-6-(3-fluoro-5-isobutoxy-phenyl)pyridine-3-carboxylate

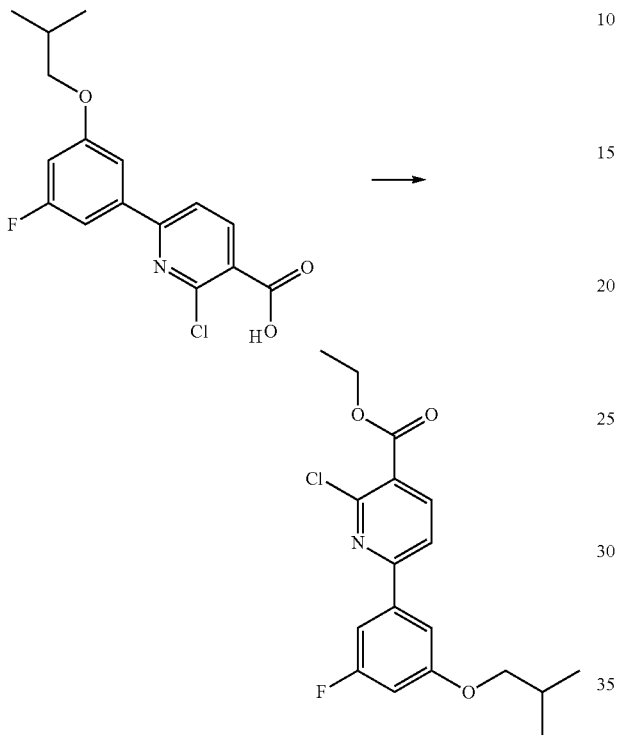

To a solution of 2-chloro-6-(3-fluoro-5-isobutoxy-phenyl)pyridine-3-carboxylic acid (1.3 g, 4.0 mmol) in ethanol (40 mL) was slowly added thionyl chloride (1.0 g, 584 µL, 8.0 mmol) and the reaction mixture was stirred at reflux for six hours. The solvent was evaporated under reduced pressure to give ethyl 2-chloro-6-(3-fluoro-5-isobutoxy-phenyl)pyridine-3-carboxylate (1.3 g, 95%) as a colorless solid.

Step 2: Ethyl 6-(3-fluoro-5-isobutoxy-phenyl)-2-(3,5,5-trimethylcyclopenten-1-yl)pyridine-3-carboxylate

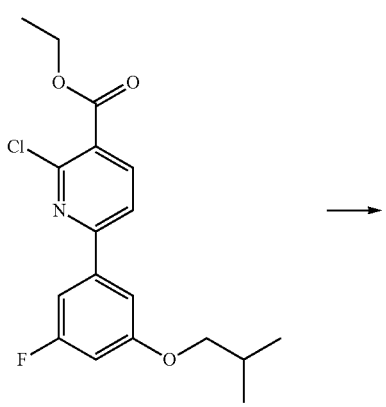

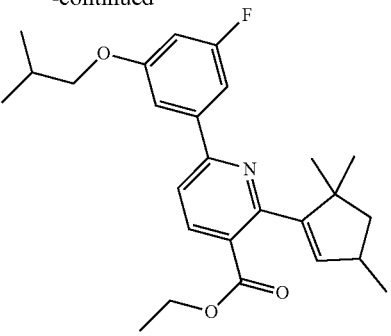

A mixture of ethyl 2-chloro-6-(3-fluoro-5-isobutoxy-phenyl)pyridine-3-carboxylate (700 mg, 1.99 mmol), 4,4,5,5-tetramethyl-2-(3,5,5-trimethylcyclopenten-1-yl)-1,3,2-dioxaborolane (517 mg, 2.19 mmol), 1,1'-bis(diphenylphosphino)ferrocene-palladium dichloride (437 mg, 0.60 mmol), and Na$_2$CO$_3$ (633 mg, 5.97 mmol) in dioxane (9 mL) and water (1 mL) was heated in a sealed vessel at 150° C. for 16 hours. The reaction mixture was filtered, and the solids were washed with EtOAc. The combined organics were evaporated, and the residue was purified by silica gel column chromatography using a gradient of 100% hexanes to 20% EtOAc in hexanes to afford ethyl 6-(3-fluoro-5-isobutoxy-phenyl)-2-(3,5,5-trimethylcyclopenten-1-yl)pyridine-3-carboxylate (97 mg, 11%) as a white solid. ESI-MS m/z calc. 425.23663, found 426.2 (M+1)$^+$; Retention time: 2.4 minutes.

Step 3: 6-(3-fluoro-5-isobutoxy-phenyl)-2-(3,5,5-trimethylcyclopenten-1-yl)pyridine-3-carboxylic acid

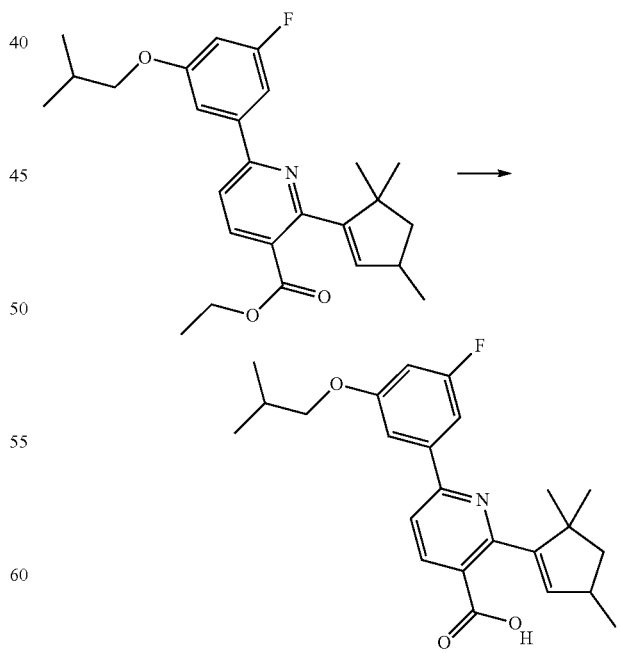

To a solution of ethyl 6-(3-fluoro-5-isobutoxy-phenyl)-2-(3,5,5-trimethylcyclopenten-1-yl)pyridine-3-carboxylate (92 mg, 0.2 mmol) in THF (520 µL) was added NaOH (650

μL of 1 M, 0.6 mmol) and then MeOH (520 μL) and the reaction mixture was heated to 50° C. for 4 hrs. The reaction mixture was neutralized with 1 M HCl (3.0 mL) and extracted with EtOAc (10 mL×2). The combined extracts were dried over Na$_2$SO$_4$ and evaporated under reduced pressure to give 6-(3-fluoro-5-isobutoxy-phenyl)-2-(3,5,5-trimethylcyclopenten-1-yl)pyridine-3-carboxylic acid (77 mg, 90%) as a light yellow solid. ESI-MS m/z calc. 397.20532, found 398.2 (M+1)$^+$; Retention time: 1.92 minutes; 1H NMR (400 MHz, DMSO) δ 13.11 (s, 1H), 7.98 (s, 2H), 7.56 (s, 1H), 7.49 (d, J=9.9 Hz, 1H), 6.93 (d, J=10.7 Hz, 1H), 5.67 (s, 1H), 3.85 (d, J=6.6 Hz, 2H), 2.87 (dd, J=14.1, 7.0 Hz, 1H), 2.13-1.98 (m, 2H), 1.46-1.38 (m, 4H), 1.24 (s, 4H), 1.08 (d, J=6.9 Hz, 3H), 0.99 (d, J=6.7 Hz, 6H).

Step 4: N-[(6-amino-2-pyridyl)sulfonyl]-6-(3-fluoro-5-isobutoxy-phenyl)-2-(3,5,5-trimethylcyclopenten-1-yl)pyridine-3-carboxamide (Compound 2081) (Compound 2039)

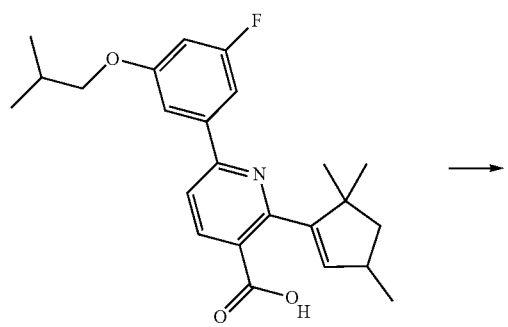

6-(3-fluoro-5-isobutoxy-phenyl)-2-(3,5,5-trimethylcyclopenten-1-yl)pyridine-3-carboxylic acid (74 mg, 0.19 mmol) and CDI (45 mg, 0.28 mmol) were mixed in DMF (740 μL) under and atmosphere of nitrogen and the reaction mixture was heated to 45° C. for 45 minutes. In a separate vial, 6-aminopyridine-2-sulfonamide (80.62 mg, 0.4655 mmol) and NaH (18 mg, 0.46 mmol) were mixed slowly in DMF (370.0 μL) and mixture was heated to 45° C. for 45 minutes. The 6-aminopyridine-2-sulfonamide reaction mixture was added to the activated acid and the reaction mixture was heated at 50° C. for 16 h. The reaction mixture was filtered and then purified directly by reverse-phase preparative chromatography utilizing a C18 column and HPLC-MS method 10-99% mobile phase B (mobile phase A=water (de-ionized, no acid modifier), mobile phase B=acetonitrile) to afford N-[(6-amino-2-pyridyl)sulfonyl]-6-(3-fluoro-5-isobutoxy-phenyl)-2-(3,5,5-trimethylcyclopenten-1-yl)pyridine-3-carboxamide (Compound 2081) (Compound 2039) (64 mg, 62%) as an off-white solid, ESI-MS m/z calc. 552.22064, found 553.4 (M+1)$^+$; Retention time: 2.25 minutes; 1H NMR (400 MHz, DMSO) δ 12.55 (s, 1H), 7.96 (d, J=8.2 Hz, 1H), 7.86 (d, J=8.2 Hz, 1H), 7.68-7.60 (m, 1H), 7.56 (s, 1H), 7.49 (d, J=9.6 Hz, 1H), 7.20 (d, J=7.3 Hz, 1H), 7.01-6.84 (m, 1H), 6.72 (d, J=8.4 Hz, 1H), 6.55 (s, 2H), 5.62 (d, J=1.7 Hz, 1H), 3.85 (d, J=6.6 Hz, 2H), 2.66 (ddd, J=14.3, 7.4, 1.8 Hz, 1H), 2.03 (dd, J=13.2, 6.6 Hz, 1H), 1.95 (dd, J=12.1, 7.5 Hz, 1H), 1.38-1.28 (m, 4H), 1.25 (s, 3H), 0.99 (d, J=6.7 Hz, 6H), 0.93 (d, J=6.9 Hz, 3H).

Step 5: N-[(6-amino-2-pyridyl)sulfonyl]-6-(3-fluoro-5-isobutoxy-phenyl)-2-(3,5,5-trimethylcyclopenten-1-yl)pyridine-3-carboxamide (Compound 2081) (Isomer 1, R or S stereoisomer) and N-[(6-amino-2-pyridyl)sulfonyl]-6-(3-fluoro-5-isobutoxy-phenyl)-2-(3,5,5-trimethylcyclopenten-1-yl)pyridine-3-carboxamide (Compound 2039) (Isomer 2, R or S stereoisomer)

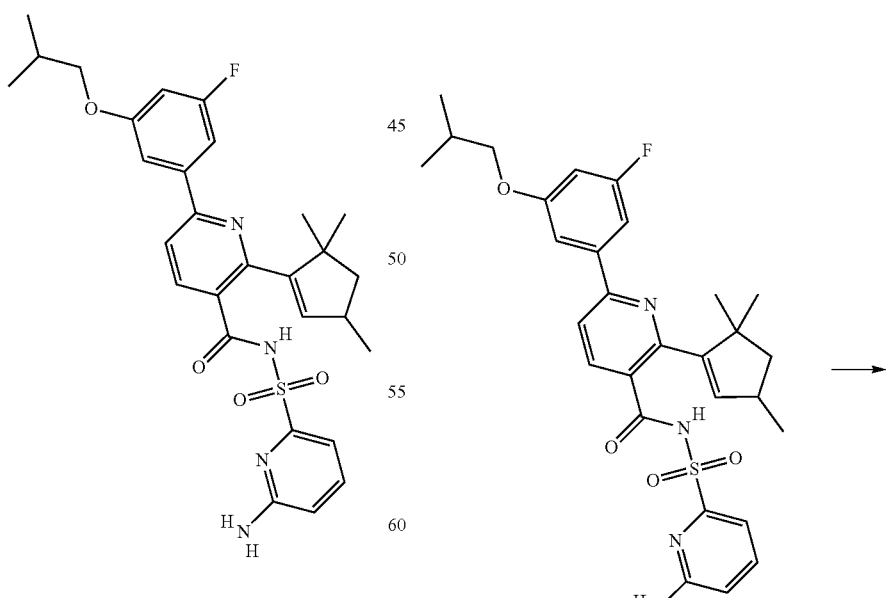

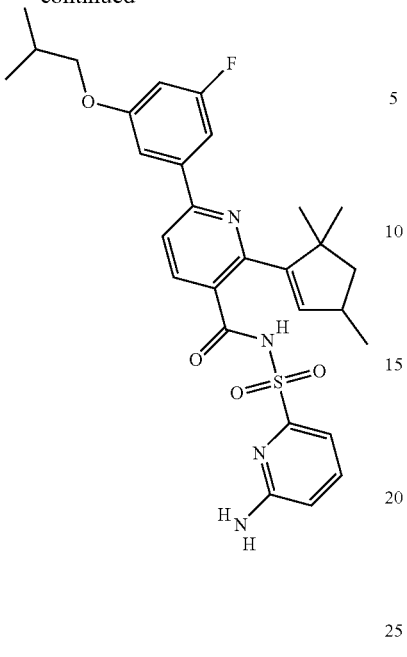

The stereoisomers were separated using supercritical fluid chromatography on a ChiralCel AD-H (250×10 mm), 5 μm column using 20% EtOH (0.1% TFA) in CO₂ at a flow rate of 10.0 mL/min. The separated enantiomers were separately concentrated to give the pure compound. SFC Peak 1: N-[(6-amino-2-pyridyl)sulfonyl]-6-(3-fluoro-5-isobutoxy-phenyl)-2-(3,5,5-trimethylcyclopenten-1-yl)pyridine-3-carboxamide (Compound 2081) (Isomer 1, R or S stereoisomer) ESI-MS m/z calc. 552.22064, found 553.2 (M+1)⁺; Retention time: 2.26 minutes. SFC Peak 2 N-[(6-amino-2-pyridyl)sulfonyl]-6-(3-fluoro-5-isobutoxy-phenyl)-2-(3,5,5-trimethylcyclopenten-1-yl)pyridine-3-carboxamide (Compound 2039) (Isomer 2, R or S stereoisomer) ESI-MS m/z calc. 552.22064, found 553.2 (M+1)⁺; Retention time: 2.26 minutes.

Preparation 134: N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2492) (Isomer 1, R or S stereoisomer) (Compound 2374) (Isomer 2, R or S stereoisomer)

Step 1: 6-(3-fluoro-5-isobutoxy-phenyl)-2-(2,2,4,4-tetramethylcyclopentyl)pyridine-3-carboxylic acid

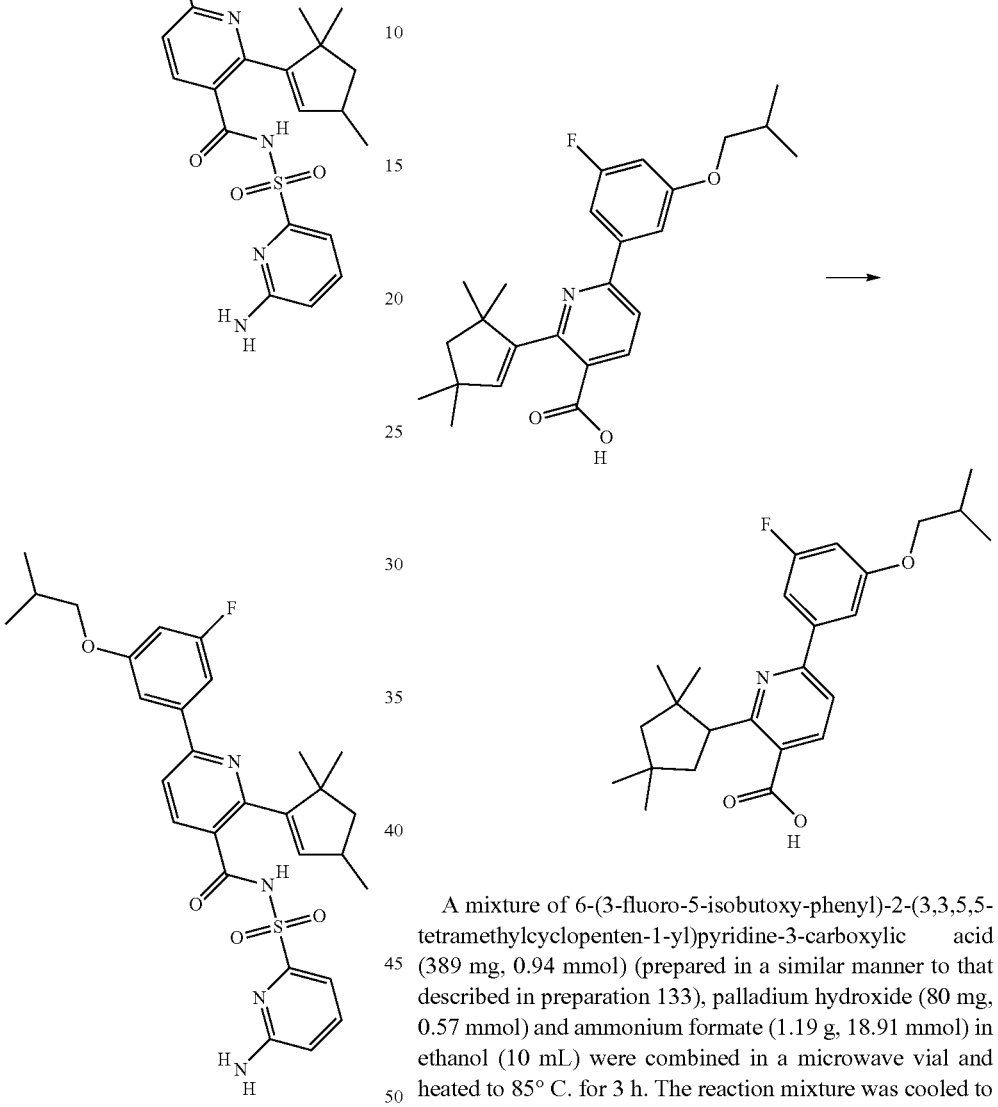

A mixture of 6-(3-fluoro-5-isobutoxy-phenyl)-2-(3,3,5,5-tetramethylcyclopenten-1-yl)pyridine-3-carboxylic acid (389 mg, 0.94 mmol) (prepared in a similar manner to that described in preparation 133), palladium hydroxide (80 mg, 0.57 mmol) and ammonium formate (1.19 g, 18.91 mmol) in ethanol (10 mL) were combined in a microwave vial and heated to 85° C. for 3 h. The reaction mixture was cooled to room temperature and a further aliquot of ammonium formate (1.19 g, 18.91 mmol) and palladium hydroxide (80 mg, 0.57 mmol) was added, and irradiated under microwave conditions at 85° C. for 4 h. The reaction mixture was filtered over celite, washed with methanol and the filtrate concentrated under reduced pressure, then diluted with 1N HCl and washed with ethyl acetate (2×). The combined organic layers were dried over sodium sulfate, filtered and concentrated under reduced pressure to a clear oil. The oil was purified by silica gel column chromatography using a gradient from 100% dichloromethane to 20% methanol in dichloromethane followed by 20% methanol in ethyl acetate to give 6-(3-fluoro-5-isobutoxy-phenyl)-2-(2,2,4,4-tetramethylcyclopentyl)pyridine-3-carboxylic acid (52 mg, 13%) as a white solid.

Step 2: N-[(6-amino-2-pyridyl)sulfonyl]-6-(3-fluoro-5-isobutoxy-phenyl)-2-(2,2,4,4-tetramethyl-cyclopentyl)pyridine-3-carboxamide (Compound 2492) (Compound 2374)

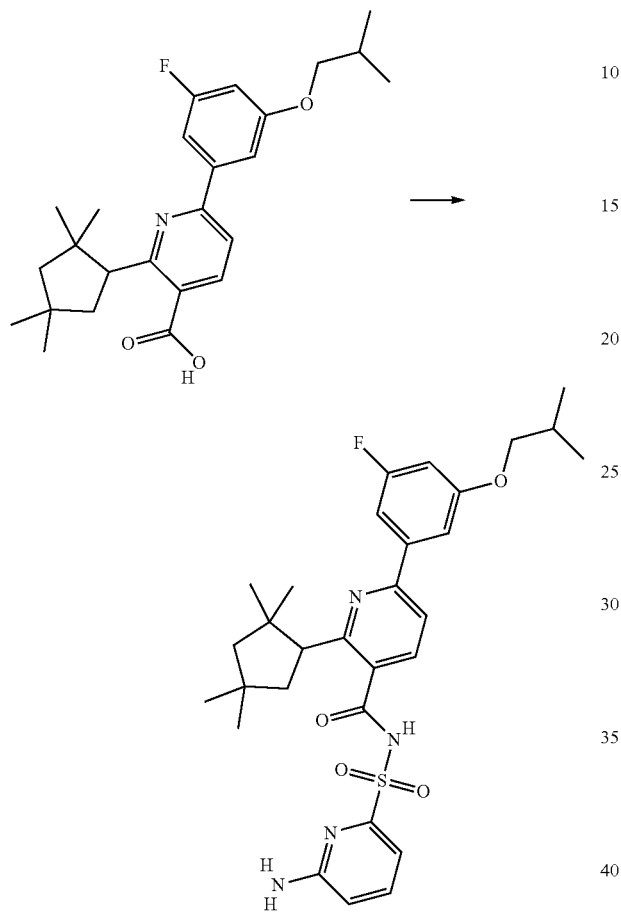

Step 3: N-[(6-amino-2-pyridyl)sulfonyl]-6-(3-fluoro-5-isobutoxy-phenyl)-2-(2,2,4,4-tetramethyl-cyclopentyl)pyridine-3-carboxamide (Compound 2492) (Isomer 1, R or S stereoisomer) and N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2374) (Isomer 2, R or S stereoisomer)

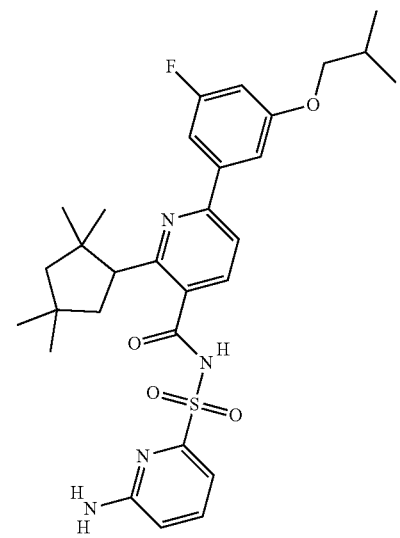

A solution of 6-(3-fluoro-5-isobutoxy-phenyl)-2-(2,2,4,4-tetramethylcyclopentyl)pyridine-3-carboxylic acid (52 mg, 0.13 mmol) and carbonyl diimidazole (31 mg, 0.19 mmol) in dimethylformamide (0.5 mL) was stirred at 45° C. for 90 minutes. A separate solution of 6-aminopyridine-2-sulfonamide (44 mg, 0.25 mmol) and sodium hydride (10 mg, 0.25 mmol) in dimethylformamide (0.5 mL) was stirred at 45° C. for 45 minutes was then added to the activated acid and the resulting mixture was stirred at 45° C. for 2 h. The reaction mixture was filtered and purified using a reverse phase HPLC-MS method using a Luna C18 (2) column (75×30 mm, 5 μm particle size) and a dual gradient run from 1-99% mobile phase B over 15.0 minutes (mobile phase A=H$_2$O (5 mM HCl), mobile phase B=acetonitrile) to give N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2492) (Compound 2374) (HCl salt) (51 mg, 67%) as an off-white solid. 1H NMR (400 MHz, DMSO) δ 12.63 (s, 1H), 7.91 (dd, J=20.4, 8.2 Hz, 2H), 7.66 (t, J=7.9 Hz, 1H), 7.57 (s, 1H), 7.51 (d, J=9.8 Hz, 1H), 7.25 (d, J=7.3 Hz, 1H), 6.93 (d, J=10.7 Hz, 1H), 6.73 (d, J=8.4 Hz, 1H), 6.51 (s, 2H), 3.86 (d, J=6.6 Hz, 2H), 3.58 (dd, J=12.2, 6.5 Hz, 11H), 2.55 (d, J=12.3 Hz, 11H), 2.06 (dt, J=13.2, 6.6 Hz, 1H), 1.63 (dd, J=12.4, 6.4 Hz, 1H), 1.50 (d, J=13.0 Hz, 1H), 1.39 (d, J=12.9 Hz, 1H), 1.15 (s, 3H), 1.08-0.93 (m, 9H), 0.80 (s, 3H), 0.69 (s, 3H). ESI-MS m/z calc. 568.25195, found 569.3 (M+1)$^+$; Retention time: 2.4 minutes.

2239
-continued

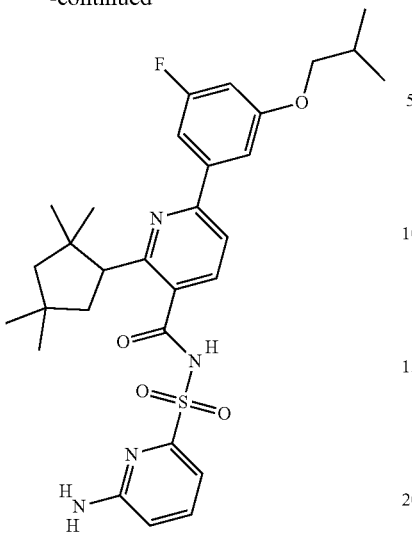

The stereoisomers were separated using supercritical fluid chromatography on a Chiralpak IC (250×10 mm), 5 μm column using 17% EtOH (DeNat)+0.1% TFA in CO$_2$ at a flow rate of 10.0 mL/min. The separated enantiomers were separately concentrated to give the pure compound. SFC Peak 1: N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2492) (Compound 2374) ESI-MS m/z calc. 568.25195, found 569.3 (M+1)$^+$; Retention time: 2.4 minutes. 1H NMR (400 MHz, MeOD) δ 7.87 (d, J=8.2 Hz, 1H), 7.76 (d, J=8.2 Hz, 1H), 7.70 (dd, J=8.3, 7.4 Hz, 1H), 7.54 (s, 1H), 7.46-7.38 (m, 2H), 6.83 (d, J=8.4 Hz, 1H), 6.75 (dt, J=10.5, 2.3 Hz, 1H), 3.82 (d, J=6.5 Hz, 2H), 3.67 (dd, J=12.3, 6.4 Hz, 1H), 2.66 (t, J=12.5 Hz, 1H), 2.11 (dt, J=13.3, 6.7 Hz, 1H), 1.69 (dd, J=12.6, 6.3 Hz, 1H), 1.49 (dd, J=38.8, 13.1 Hz, 2H), 1.18 (d, J=5.6 Hz, 3H), 1.10-1.00 (m, 9H), 0.81 (s, 3H), 0.75 (s, 3H). SFC Peak 2: N-[(6-amino-2-pyridyl)sulfonyl]-6-(3-fluoro-5-isobutoxy-phenyl)-2-(2,2,4,4-tetramethylcyclopentyl)pyridine-3-carboxamide (Compound 2492) (Compound 2374). ESI-MS m/z calc. 568.25195, found 569.3 (M+1)$^+$; Retention time: 2.4 minutes. 1H NMR (400 MHz, MeOD) δ 7.87 (d, J=8.2 Hz, 1H), 7.76 (d, J=8.2 Hz, 1H), 7.70 (dd, J=8.3, 7.4 Hz, 11H), 7.54 (s, 1H), 7.46-7.38 (m, 2H), 6.83 (d, J=8.4 Hz, 1H), 6.75 (dt, J=10.5, 2.3 Hz, 1H), 3.82 (d, J=6.5 Hz, 2H), 3.67 (dd, J=12.3, 6.4 Hz, 1H), 2.66 (t, J=12.5 Hz, 1H), 2.11 (dt, J=13.3, 6.7 Hz, 1H), 1.69 (dd, J=12.6, 6.3 Hz, 1H), 1.49 (dd, J=38.8, 13.1 Hz, 2H), 1.18 (d, J=5.6 Hz, 3H), 1.10-1.00 (m, 9H), 0.81 (s, 3H), 0.75 (s, 3H).

2240

Preparation 135: 6-(4-chloro-3-propoxy-phenyl)-2-[(2R,5S)-2,5-dimethylpyrrolidin-1-yl]-N-[[6-(pent-4-ynoylamino)-2-pyridyl]sulfonyl]pyridine-3-carboxamide (Compound 2540)

Step 1: N-[(6-amino-2-pyridyl)sulfonyl]-6-chloro-2-[(2R,5S)-2,5-dimethylpyrrolidin-1-yl]pyridine-3-

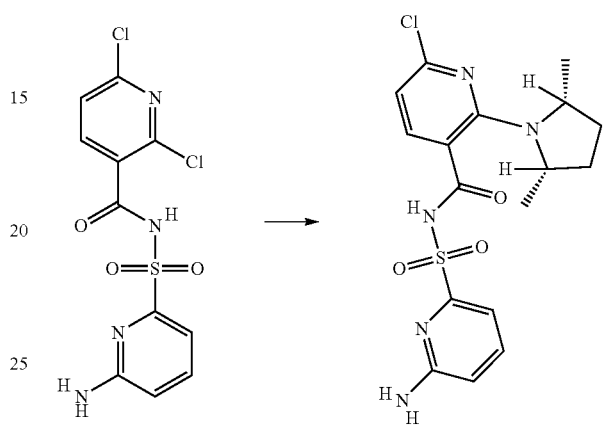

N-[(6-amino-2-pyridyl)sulfonyl]-2,6-dichloro-pyridine-3-carboxamide (2.0 g, 5.8 mmol) and (2R,5S)-2,5-dimethylpyrrolidine (0.7 g, 7.2 mmol) in DMSO (10 mL) was treated with K$_2$CO$_3$ (2.4 g, 17 mmol) and heated at 120° C. under stirring for 3 h. The reaction mixture was cooled down and carefully added to cold mixture of HCl (2.881 mL of 12 M, 35 mmol) and water (50 mL) forming a white foam. The reaction mixture was allowed to stir at room temperature for 30 min, filtered and the white solid was triturated with IPA (100 mL) to give the desired compound.

Step 2: N-[(6-amino-2-pyridyl)sulfonyl]-6-(4-chloro-3-propoxy-phenyl)-2-[(2R,5S)-2,5-dimethylpyrrolidin-1-yl]pyridine-3-carboxamide (Compound 773)

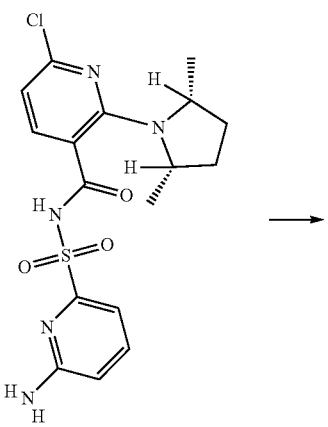

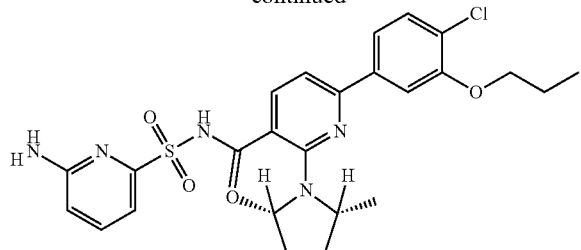

N-[(6-amino-2-pyridyl)sulfonyl]-6-chloro-2-[(2S,5R)-2,5-dimethylpyrrolidin-1-yl]pyridine-3-carboxamide (62 mg, 0.15 mmol), (4-chloro-3-propoxy-phenyl)boronic acid (48 mg, 0.23 mmol), tetrakis(triphenylphosphine)palladium (0) (10 mg, 0.009 mmol), potassium carbonate (300 μL, 2 M, 0.40 mmol) and DMF (1.7 mL) were heated at 100° C. overnight. The reaction mixture was filtered and purified by reverse phase HPLC utilizing a gradient of 1-99% acetonitrile in 5 mM aq HCl. ESI-MS m/z 544.3 (M+1)⁺; Retention time: 1.7 minutes; 1H NMR (400 MHz, DMSO-d₆) 12.98 (s, 1H), 7.83 (d, J=1.9 Hz, 1H), 7.81 (d, J=8.0 Hz, 1H), 7.70-7.61 (m, 2H), 7.52 (d, J=8.3 Hz, 1H), 7.37 (d, J=7.9 Hz, 1H), 7.23 (dd, J=7.3, 0.8 Hz, 1H), 6.72 (d, 1H), 6.48 (s, 2H), 4.13 (t, J=6.5 Hz, 2H), 4.09-3.97 (m; 2H), 2.05-1.91 (m, 2H), 1.81 (h, J=7.2 Hz, 2H), 1.74-1.61 (m, 2H), 1.10 (d, J=6.2 Hz, 6H), 1.03 (t, J=7.4 Hz, 3H).

Step 3: 6-(4-chloro-3-propoxy-phenyl)-2-[(2R,5S)-2,5-dimethylpyrrolidin-1-yl]l-N-[[6-(pent-4-ynoylamino)-2-pyridyl]sulfonyl]pyridine-3-carboxamide (Compound 2540)

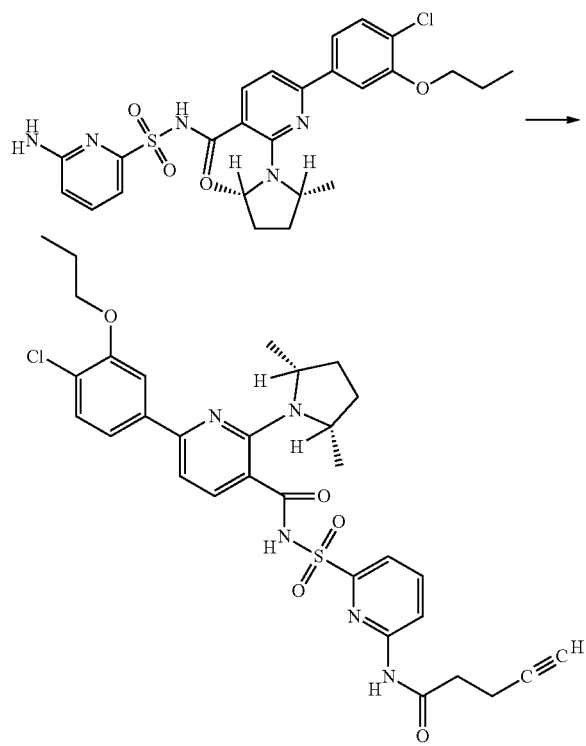

N-[(6-amino-2-pyridyl)sulfonyl]-6-(4-chloro-3-propoxyphenyl)-2-[(2R,5S)-2,5-dimethylpyrrolidin-1-yl]pyridine-3-carboxamide (Compound 773) (10 mg, 0.02 mmol) in DCM (2 mL) at 0° C. was added triethylamine (11 mg, 15 μL, 0.11 mmol) and pent-4-ynoyl chloride (4 mg, 0.04 mmol). The reaction mixture was then stirred at 0° C. for 5 minutes, then at rt for 2 h. The reaction mixture was evaporated under reduced pressure and the crude mixture was purified by reverse phase HPLC using 10-100% ACN in Water (TFA modifier). The salt was neutralized with SPE-CO₃H cartridge, eluted with MeOH/DCM to give the desired compound. ESI-MS m/z 624.3 (M+1)⁺; Retention time: 0.9 minutes; 1H NMR (300 MHz, CDCl₃) δ 8.73 (d, J=8.2 Hz, 1H), 8.28 (d, J=8.1 Hz, 1H), 8.04 (t, J=7.9 Hz, 1H), 7.98-7.89 (m, 2H), 7.56 (dd, J=8.2, 1.9 Hz, 1H), 7.51 (d, J=2.4 Hz, 2H), 4.21 (d, J=6.1 Hz, 2H), 4.10 (t, J=6.4 Hz, 2H), 2.73 (t, J=6.9 Hz, 2H), 2.64-2.47 (m, 4H), 2.11 (d, J=2.8 Hz, 2H), 2.00-1.85 (m, 4H), 1.34 (d, J=6.6 Hz, 6H), 1.25 (s, 6H), 1.11 (t, J=7.4 Hz, 5H), 0.93-0.79 (m, 3H).

Preparation 136: N-[4-[3-(4-chlorophenyl)propyl]piperazin-1-yl]sulfonyl-2-[(4S)-2,2,4-trimethylpyrrolidin-1-yl]pyridine-3-carboxamide (Compound 2141)

Step 1: 2-[(4S)-2,2,4-trimethylpyrrolidin-1-yl]pyridine-3-carboxylic acid

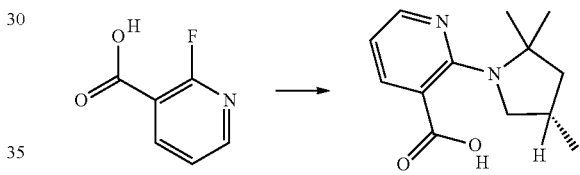

A mixture of 2-fluoropyridine-3-carboxylic acid (71 mg, 0.5 mmol), (4S)-2,2,4-trimethylpyrrolidine (HCl salt) (150 mg, 1.0 mmol), potassium carbonate (207 mg, 1.5 mmol), and cesium fluoride (152 mg, 1.0 mmol) in DMSO (500 μL) was stirred at 130° C. for six hours. The reaction mixture was diluted with water, adjusted to pH 4 with 1 M HCl, and extracted with ethyl acetate. The combined extracts were washed with brine, dried over sodium sulfate, and evaporated under reduced pressure. The residue was purified using reverse phase HPLC-MS using a Luna C18 (2) column (75×30 mm, 5 μm particle size) and a dual gradient run from 1-70% mobile phase B over 15.0 minutes (mobile phase A=H₂O (5 mM HCl). mobile phase B=CH₃CN) to give the desired compound.

2243

Step 2: benzyl 4-[[2-[(4S)-2,2,4-trimethylpyrrolidin-1-yl]pyridine-3-carbonyl]sulfamoyl]piperazine-1-carboxylate

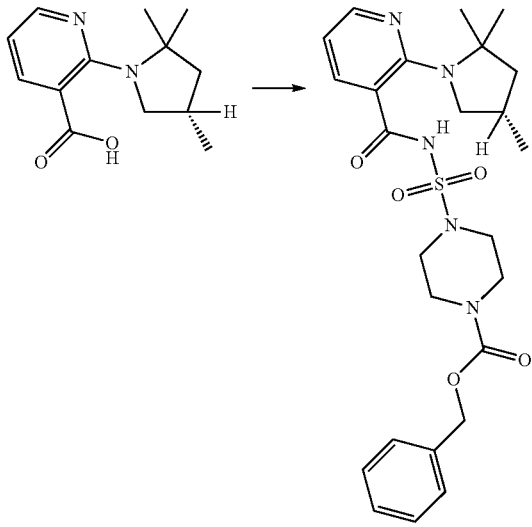

A solution of (S)-2-(2,2,4-trimethylpyrrolidin-1-yl)nicotinic acid (117 mg, 0.5 mmol) and chlorosulfonyl isocyanate (85 mg, 52 µL, 0.6 mmol) in dichloromethane (3 mL) was stirred for 30 minutes, and was slowly added to a solution of benzyl piperazine-1-carboxylate (110 mg, 96 µL, 0.5 mmol) and pyridine (59 mg, 60 µL, 0.8 mmol) in dichloromethane (2 mL). The reaction mixture was stirred for two hours, evaporated under reduced pressure and purified by silica gel column chromatography with 0-5% methanol in dichloromethane as eluent to give benzyl (S)-4-(N-(2-(2,2,4-trimethylpyrrolidin-1-yl)nicotinoyl)sulfamoyl)piperazine-1-carboxylate (35 mg, 13%) as a colorless oil. ESI-MS m/z 516.6 (M+1)$^+$; Retention time: 1.65 minutes.

Step 3: N-piperazin-1-ylsulfonyl-2-[(4S)-2,2,4-trimethylpyrrolidin-1-yl]pyridine-3-carboxamide

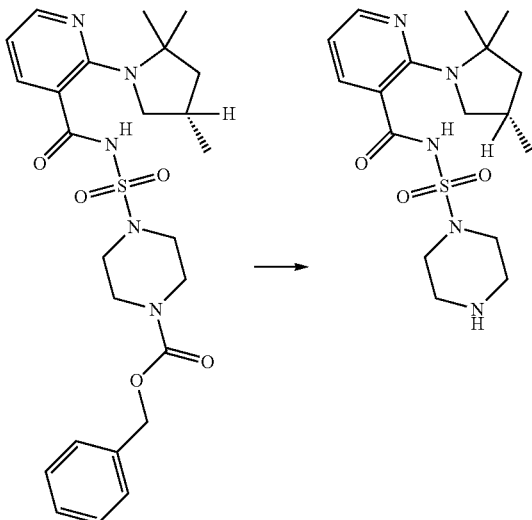

2244

A mixture of benzyl (S)-4-(N-(2-(2,2,4-trimethylpyrrolidin-1-yl)nicotinoyl)sulfamoyl)piperazine-1-carboxylate (0.22 g, 0.43 mmol) and palladium on carbon (20 mg, 0.02 mmol) in methanol (2 mL) was stirred under a hydrogen atmosphere for 16 hours. The reaction mixture was filtered and evaporated to give (S)—N-(piperazin-1-ylsulfonyl)-2-(2,2,4-trimethylpyrrolidin-1-yl)nicotinamide (0.13 g, 80%) as a colorless solid.

Step 4: N-[4-[3-(4-chlorophenyl)propyl]piperazin-1-yl]sulfonyl-2-[(4S)-2,2,4-trimethylpyrrolidin-1-yl]pyridine-3-carboxamide (Compound 2141)

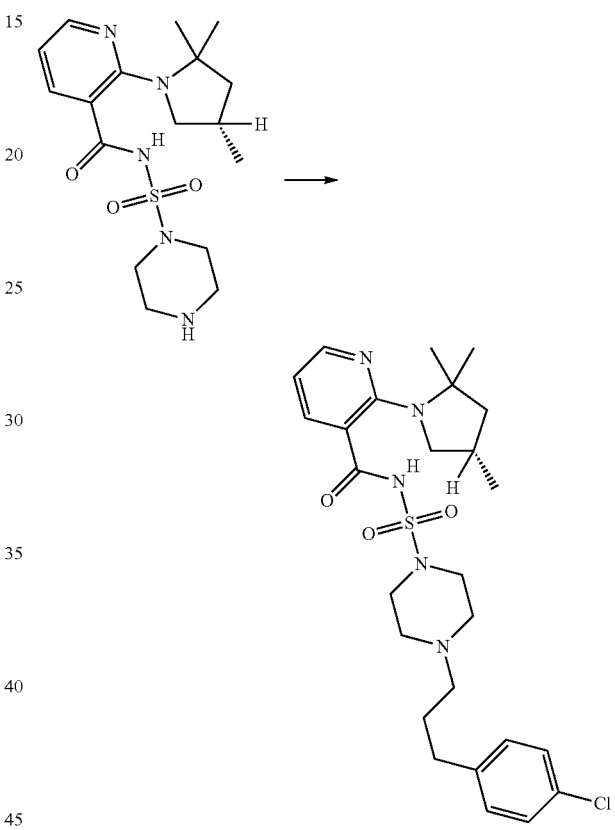

A solution of (S)—N-(piperazin-1-ylsulfonyl)-2-(2,2,4-trimethylpyrrolidin-1-yl)nicotinamide (30 mg, 0.08 mmol) and 3-(4-chlorophenyl)propanal (14 mg, 0.08 mmol) in 1,2-dichloroethane (800 µL) was stirred for five minutes, and sodium triacetoxyborohydride (33 mg, 0.16 mmol) was added. The reaction mixture was stirred for 16 hours, diluted with methanol, filtered, and purified using a reverse phase HPLC-MS method using a Luna C18 (2) column (75×30 mm, 5 µm particle size) and a dual gradient run from 1-99% mobile phase B over 15.0 minutes (mobile phase A=H$_2$O (5 mM HCl), mobile phase B=CH$_3$CN) to give the desired compound. ESI-MS m/z 534.6 (M+1)$^+$; Retention time: 1.23 minutes.

The following compounds can be synthesized using the procedures described herein:
N-[(3R)-3-[(4-tert-butoxyphenyl)methylamino]pyrrolidin-1-yl]sulfonyl-2-[(4S)-2,2,4-trimethylpyrrolidin-1-yl]pyridine-3-carboxamide (Compound 2698),
N-[[3-[(4-tert-butoxyphenyl)methylamino]-1-piperidyl]sulfonyl]-2-[(4S)-2,2,4-trimethylpyrrolidin-1-yl]pyridine-3-carboxamide (Compound 2697), N-[(3R)-3-[[4-fluoro-3-(trifluoromethoxy)phenyl]methyl-amino]pyrrolidin-1-yl]sulfonyl-2-[(4S)-2,2,4-trimeth-ylpyrrolidin-1-yl]pyridine-3-carboxamide (Compound 2681), N-[(3R)-3-[3-(4-chlorophenyl)propylamino]pyrrolidin-1-yl]sulfonyl-2-[(4S)-2,2,4-trimethylpyrrolidin-1-yl]pyridine-3-carboxamide (Compound 2717) and N-[(3R)-3-[(2,4-dichlorophenyl)methylamino]pyrrolidin-1-yl]sulfonyl-2-[(4S)-2,2,4-trimethylpyrrolidin-1-yl]pyridine-3-carboxamide (Compound 2693)

Preparation 137: 6-(3-fluoro-5-isobutoxy-phenyl)-N-(3-piperidylsulfonyl)-2-[(4S)-2,2,4-trimethylpyrrolidin-1-yl]pyridine-3-carboxamide (Compound 2655)

Step 1: 6-(3-fluoro-5-isobutoxy-phenyl)-2-[(4S)-2,2,4-trimethylpyrrolidin-1-yl]pyridine-3-carboxylic acid

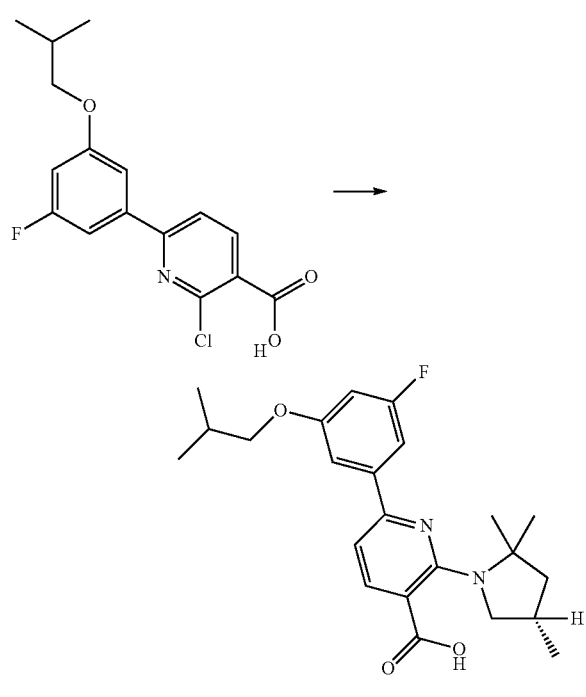

A mixture of 2-chloro-6-(3-fluoro-5-isobutoxy-phenyl)pyridine-3-carboxylic acid (1.5 g, 3.6 mmol), (4S)-2,2,4-trimethylpyrrolidine (HCl salt) (0.8 g, 5.8 mmol), K₂CO₃ (1.6 g, 11.6 mmol), and CsF (1.1 g, 7.5 mmol) in DMSO (5 mL) was stirred at 130° C. for two days. The reaction mixture was diluted with water, adjusted to pH 4 with 1 M HCl, and extracted with ethyl acetate. The combined extracts were washed with brine, dried over sodium sulfate, and evaporated under reduced pressure. The residue was purified by silica gel chromatography with 0-6% methanol in dichloromethane to give 6-(3-fluoro-5-isobutoxy-phenyl)-2-[(4S)-2,2,4-trimethylpyrrolidin-1-yl]pyridine-3-carboxylic acid (1.2 g, 82%) as a tan foam. ESI-MS m/z calc. 400.21622, found 401.0 (M+1)⁺; Retention time: 1.92 minutes (3 min).

Step 2: 6-(3-fluoro-5-isobutoxy-phenyl)-2-[(4S)-2,2,4-trimethylpyrrolidin-1-yl]pyridine-3-carboxamide

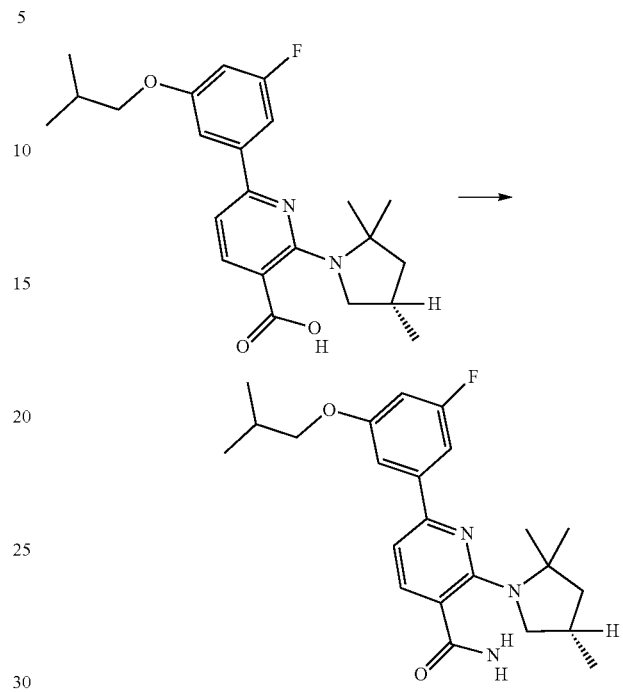

A solution of 6-(3-fluoro-5-isobutoxy-phenyl)-2-[(4S)-2,2,4-trimethylpyrrolidin-1-yl]pyridine-3-carboxylic acid (120 mg, 0.3 mmol) and CDI (73 mg, 0.5 mmol) in DMF (1.5 mL) was stirred at 45° C. for 30 minutes, and ammonium hydroxide (525 µL of 30% w/v, 4.5 mmol) was added. The reaction mixture was stirred at 45° C. for three days, diluted with water, and extracted with ethyl acetate. The combined extracts were washed with brine, dried over sodium sulfate, and evaporated under reduced pressure. The residue was purified by silica gel column chromatography with 0-5% methanol in dichloromethane to give 6-(3-fluoro-5-isobutoxy-phenyl)-2-[(4S)-2,2,4-trimethylpyrrolidin-1-yl]pyridine-3-carboxamide (82 mg, 68%). ESI-MS m/z 400.5 (M+1)⁺; Retention time: 1.78 minutes (3 min).

Step 3: 6-(3-fluoro-5-isobutoxy-phenyl)-N-(3-piperidylsulfonyl)-2-[(4S)-2,2,4-trimethylpyrrolidin-1-yl]pyridine-3-carboxamide (Compound 2655)

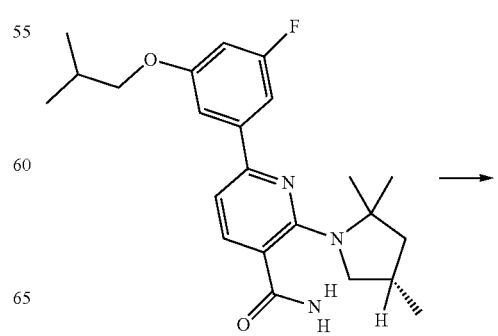

2247
-continued

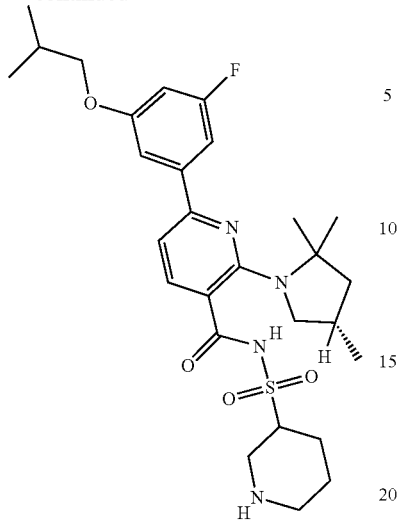

A solution of 6-(3-fluoro-5-isobutoxy-phenyl)-2-[(4S)-2,2,4-trimethylpyrrolidin-1-yl]pyridine-3-carboxamide (32 mg, 0.1 mmol) and NaH (5 mg, 0.1 mmol) in DMF (800 μL) was stirred for 30 minutes, and benzyl 3-chlorosulfonylpiperidine-1-carboxylate (51 mg, 0.2 mmol) was added. The reaction mixture was stirred for 16 hours. The reaction was filtered and purified using a reverse phase HPLC-MS method using a Luna C18 (2) column (75×30 mm, 5 m particle size) and a dual gradient run from 1-99% mobile phase B over 15.0 minutes (mobile phase A=H₂O (5 mM HCl), mobile phase B=CH₃CN). The intermediate and palladium (10 mg, 0.01 mmol) (10% on ca-bon) in MeOH was stirred under a hydrogen atmosphere for 17 hours. The reaction was filtered and purified using a reverse phase HPLC-MS method using a Luna C18 (2) column (75×30 mm, 5 m particle size) and a dual gradient run from 1-99% mobile phase B over 15.0 minutes (mobile phase A=H₂O (5 mM HCl), mobile phase B=CH₃CN) to give the desired compound. ESI-MS m/z 547.6 (M+1)⁺; Retention time: 1.65 minutes (3 min)

The following compounds can be synthesized using the procedures described herein:

6-(3-fluoro-5-isobutoxy-phenyl)-N-pyrrolidin-3-ylsulfonyl-2-[(4S)-2,2,4-trimethylpyrrolidin-1-yl]pyridine-3-carboxamide (Compound 2042), N-cyclopentylsulfonyl-6-(3-fluoro-5-isobutoxy-phenyl)-2-[(4S)-2,2,4-trimethylpyrrolidin-1-yl]pyridine-3-carboxamide (Compound-2113), 6-(3-fluoro-5-isobutoxy-phenyl)-N-[[(3R)-3-piperidyl]sulfamoyl]-2-[(4S)-2,2,4-trimethylpyrrolidin-1-yl]pyridine-3-carboxamide (Compound 2677), 6-(3-fluoro-5-isobutoxy-phenyl)-N-(3-pyridylsulfamoyl)-2-[(4S)-2,2,4-trimethylpyrrolidin-1-yl]pyridine-3-carboxamide (Compound 1448) and 6-(3-fluoro-5-isobutoxy-phenyl)-N-[(2-methoxy-3-pyridyl)sulfamoyl]-2-[(4S)-2,2,4-trimethylpyrrolidin-1-yl]pyridine-3-carboxamide (Compound 1359).

2248

Preparation 138: N-[(6-amino-2-pyridyl)sulfonyl]-5-fluoro-6-(3-fluoro-5-isobutoxy-phenyl)-2-[(4S)-2,2,4-trimethylpyrrolidin-1-yl]pyridine-3-carboxamide (Compound 2473)

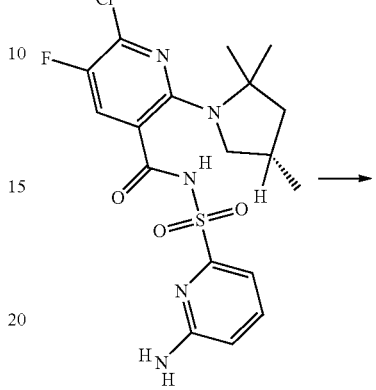

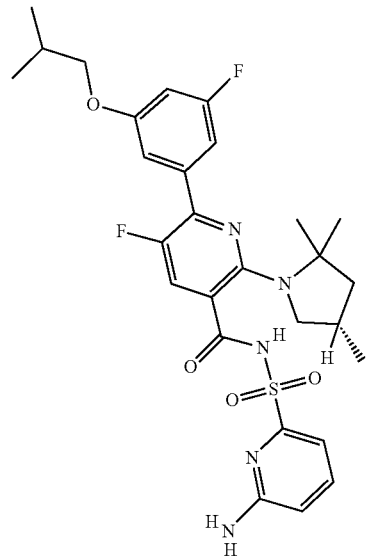

(3-fluoro-5-isobutoxy-phenyl)boronic acid (5 mg, 0.02 mmol), N-[(6-amino-2-pyridyl)sulfonyl]-6-chloro-5-fluoro-2-[(4S)-2,2,4-trimethylpyrrolidin-1-yl]pyridine-3-carboxamide (10 mg, 0.02 mmol), 1,3-bis(2,6-diisopropylphenyl)-4,5-dihydroimidazole; 3-chloropyridine; dichloropalladium (3 mg, 0.005 mmol) and K₂CO₃ (3 mg, 0.02 mmol) were combined in N-propanol (0.5 mL). The reaction mixture was heated to 90° C. for 16 h under an atmosphere of nitrogen. The reaction mixture was filtered and purified by reverse phase HPLC using 1-99% ACN in water (0.05% HCl modifier) over 15 minutes to give the desired compound as a pale solid. 1H NMR (400 MHz, DMSO-d₆) δ 12.62 (s, 1H), 7.73 (d, J=11.2 Hz, 1H), 7.36 (s, 1H), 7.24 (dd, J=15.0, 8.6 Hz, 2H), 6.96 (dt, J=10.9, 2.5 Hz, 1H), 6.70 (d, J=8.3 Hz, 1H), 6.53 (s, 1H), 3.82 (d, J=6.6 Hz, 2H), 2.59 (p, J=10.2 Hz, 2H), 2.22 (s, 1H), 2.07-1.98 (m, 1H), 1.87 (dd, J=12.0, 5.7 Hz, 1H), 1.54 (d, J=6.6 Hz, 6H), 1.41 (t, J=12.1 Hz, 1H), 0.98 (d, J=6.7 Hz, 6H), 0.87 (d, J=6.3 Hz, 3H). 1H NMR (400 MHz, DMSO-d₆) δ 12.62 (s, 1H), 7.73 (d, J=11.2 Hz, 1H), 7.36 (s, 1H), 7.24 (dd, J=15.0, 8.6 Hz, 2H), 6.96 (dt, J=10.9, 2.5 Hz, 1H), 6.70 (d, J=8.3 Hz, 1H), 6.53 (s, 1H), 3.82 (d, J=6.6 Hz, 2H), 2.59 (p, J=10.2 Hz, 2H), 2.22 (s, 1H), 2.07-1.98 (m, 1H), 1.87 (dd, J=12.0, 5.7 Hz, 1H), 1.54 (d, J=6.6 Hz, 6H), 1.41 (t, J=12.1 Hz, 1H), 0.98 (d, J=6.7 Hz, 6H), 0.87 (d, J=6.3 Hz, 3H).

Preparation 139: N-[(3R)-3-aminopyrrolidin-1-yl]sulfonyl-6-(3-fluoro-5-isobutoxy-phenyl)-2-(2-phenylpyrrolidin-1-yl)pyridine-3-carboxamide (Compound 2477)

Step 1: 6-(3-fluoro-5-isobutoxy-phenyl)-2-(2-phenylpyrrolidin-1-yl)pyridine-3-carboxylic acid

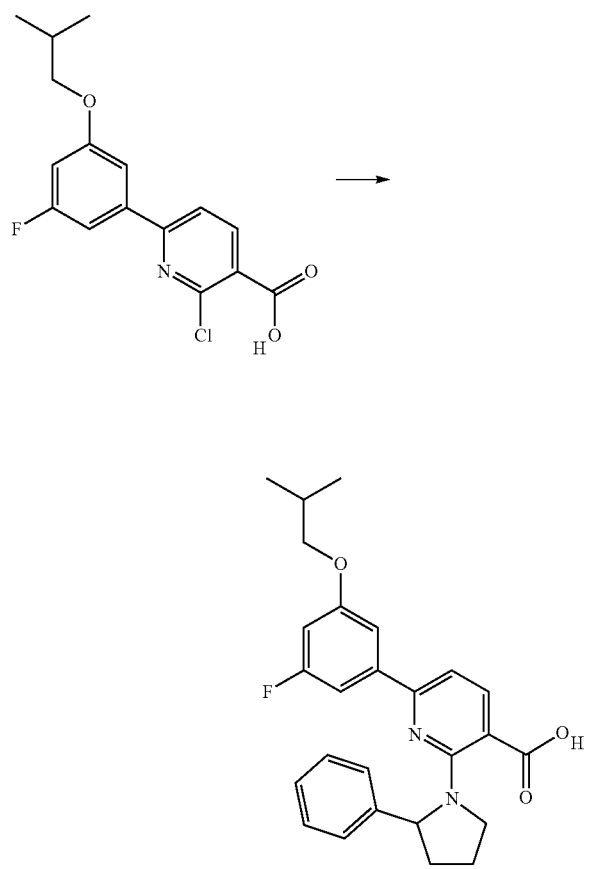

Step 2: N-[(3R)-3-aminopyrrolidin-1-yl]sulfonyl-6-(3-fluoro-5-isobutoxy-phenyl)-2-(2-phenylpyrrolidin-1-yl)pyridine-3-carboxamide (Compound 2477)

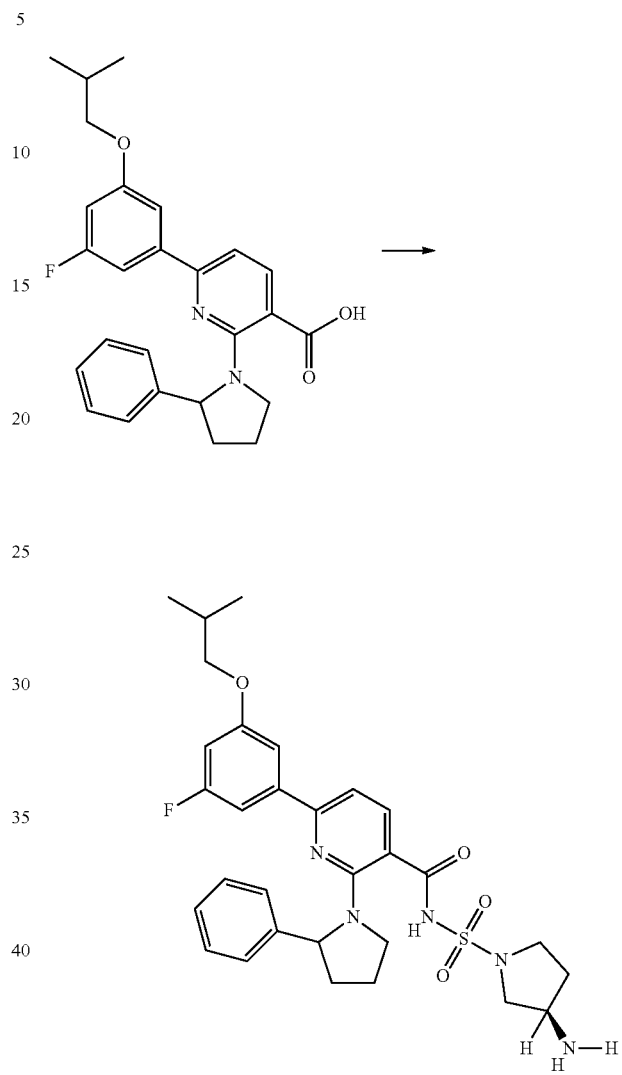

A mixture of 2-chloro-6-(3-fluoro-5-isobutoxy-phenyl)pyridine-3-carboxylic acid (227 mg, 0.7 mmol), 2-phenylpyrrolidine (206 mg, 1.4 mmol), CsF (213 mg, 1.4 mmol), and K$_2$CO$_3$ (194 mg, 1.4 mmol) in DMSO (3.5 mL) was stirred at 120° C. for 16 hours. The reaction mixture was diluted with water, adjusted to pH 4 with 1 M HCl, and extracted with ethyl acetate (2×). The combined extracts were washed with brine, dried over sodium sulfate, and evaporated under reduced pressure. The residue was purified by silica gel column chromatography with 0-5% methanol in dichloromethane to give 6-(3-fluoro-5-isobutoxy-phenyl)-2-(2-phenylpyrrolidin-1-yl)pyridine-3-carboxylic acid (190 mg, 62%). ESI-MS m/z 435.5 (M+1)$^+$; Retention time: 0.9 minutes (3 min).

A solution of 6-(3-fluoro-5-isobutoxy-phenyl)-2-(2-phenylpyrrolidin-1-yl)pyridine-3-carboxylic acid (43 mg, 0.1 mmol) and chlorosulfonyl isocyanate (11 uL, 0.1 mmol) in dichloromethane was stirred for 30 minutes, and tert-butyl N-[(3R)-pyrrolidin-3-yl]carbamate (27 mg, 0.2 mmol) and triethylamine (21 uL, 0.2 mmol) were added. The reaction mixture was stirred for 16 hours, and HCl (4M in dioxane) (200 uL, 0.8 mmol) was added. After stirring for four hours, the solvent was removed under reduced pressure, and the residue was purified using a reverse phase HPLC-MS method using a Luna C18 (2) column (75×30 mm, 5 m particle size) and a dual gradient run from 1-99% mobile phase B over 15.0 minutes (mobile phase A=H$_2$O (5 mM HCl), mobile phase B=CH$_3$CN) to give N-[(3R)-3-aminopyrrolidin-1-yl]sulfonyl-6-(3-fluoro-5-isobutoxy-phenyl)-2-(2-phenylpyrrolidin-1-yl)pyridine-3-carboxamide (Compound 2477) (9 mg, 16%). ESI-MS m/z 582.6 (M+1)$^+$; Retention time: 1.82 minutes (3 min).

The following compound can be synthesized using the procedures described herein:
N-[(3R)-3-aminopyrrolidin-1-yl]sulfonyl-2-(2-benzyl-2-methyl-pyrrolidin-1-yl)-6-(3-fluoro-5-isobutoxy-phenyl)pyridine-3-carboxamide (Compound 2325)

Preparation 140: 3-(cyclopropylmethyl)-2,2-dimethyl-pyrrolidine

Step 1: 1-benzyl-3-(cyclopropylmethyl)pyrrolidin-2-one

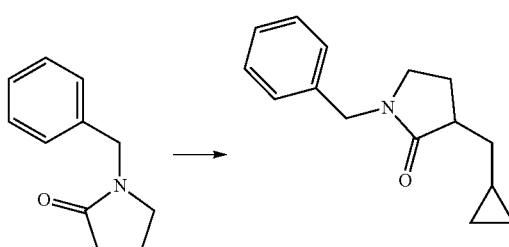

1-Benzylpyrrolidin-2-one (5.0 g, 28.6 mmol) was dissolved in THF (100 mL) and cooled to −78° C. n-BuLi (2.5M, 13.7 mL, 34.3 mmol) was added dropwise at −78° C. and the reaction mixture was stirred at −78° C. for 30 minutes. (Bromo-methyl)cyclopropane (4.6 g, 34.3 mmol) was added and stirring continued at −78° C. for 30 minutes. The reaction mixture was allowed to reach RT slowly overnight. The mixture was quenched with sat. aq. NH$_4$Cl and extracted with EtOAc (2×). The combined organic layers were washed with brine, dried over Na$_2$SO$_4$ and concentrated under reduced pressure. The residue was purified by silica gel column chromatography (heptanes/EtOAc 2:1) affording 1-benzyl-3-(cyclopropylmethyl)-pyrrolidin-2-one (3.9 g, 60%) as a colorless oil. 1H NMR (CDCl$_3$, 300 MHz): 0.05 (m, 2H); 0.43 (m, 2H); 0.74 (m, 1H); 1.22 (m, 1H); 1.68 (m, 1H); 1.76 (m, 1H); 2.21 (m, 1H); 2.55 (m, 1-H); 3.08 (m, 2H); 4.43 (q, 2H); 7.24 (m, 5H).

Step 2: 1-benzyl-3-(cyclopropylmethyl)-2,2-dimethyl-pyrrolidine

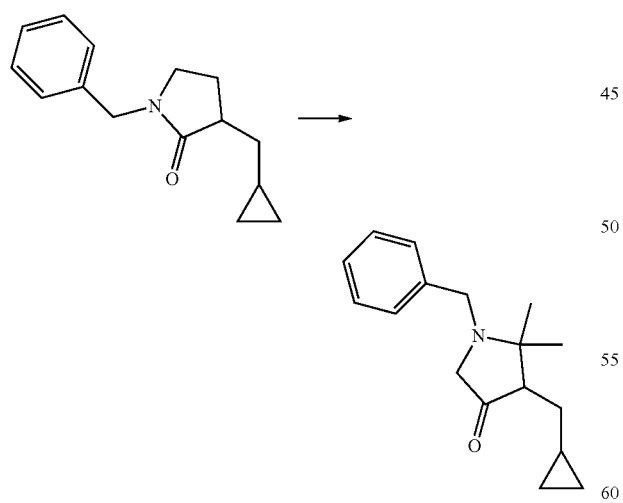

ZrCl$_4$ (3.96 g, 17.0 mmol) was added to THF (100 mL) at −10° C. and the reaction mixture was stirred for 30 minutes. 1-Benzyl-3-(cyclopropylmethyl)pyrrolidin-2-one (3.95 g, 17.0 mmol) was added as a solution in THF (10 mL). The reaction mixture was stirred for 10 minutes, then MeMgBr (3.0 M, 34 mL, 102 mmol) was added dropwise at 0° C. The reaction mixture was allowed to reach RT overnight. It was quenched at 0° C. with 30% aq. NaOH (20 mL) and stirred for 10 min. Water (100 mL) was added and the reaction mixture was extracted with CH$_2$Cl2 (2×). The combined organic layers were washed with brine, dried over Na$_2$SO$_4$ and concentrated under reduced pressure. The residue was purified by silica gel column chromatography (heptanes/EtOAc 4:1) affording 1-benzyl-3-(cyclopropylmethyl)-2,2-dimethylpyrrolidine (2.0 g, 48%) as a colorless oil. 1H NMR (CDCl$_3$, 300 MHz): −0.03 (m, 1H); 0.07 (m, 1H); 0.42 (m, 2H); 0.66 (m, 1H); 0.76 (s, 3H); 1.12 (s, 3H); 1.19 (m, 2H); 1.39 (m, 1H); 1.90 (m, 1H); 2.03 (m, 11H); 2.32 (m, 1H); 2.85 (m, 1H); 3.20 (d, 1H); 3.87 (d, 1H); 7.25 (m, 5H).

Step 3: 3-(cyclopropylmethyl)-2,2-dimethyl-pyrrolidine

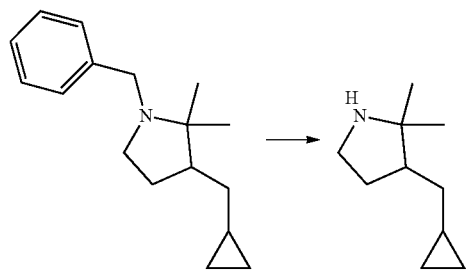

1-Benzyl-3-(cyclopropylmethyl)-2,2-dimethylpyrrolidine (2.0 g, 8.2 mmol) was dissolved in MeOH (100 mL) and conc. HCl (5 mL) was added. Pd/C (400 mg) was added and the reaction mixture was stirred over the weekend under 5 bars of H$_2$. The reaction mixture was filtered over Celite and concentrated under reduced pressure affording 3-(cyclopropylmethyl)-2,2-dimethyl-pyrrolidine hydrochloride (1.3 g, 84%) as an off-white solid. 1H NMR (CD$_3$OD, 300 MHz): 0.07 (m, 1H); 0.13 (m, 1H); 0.47 (m, 2H); 0.72 (m, 1H); 1.17 (s, 3H); 1.19 (m, 1H); 1.34 (m, 1H); 1.43 (s, 3H); 1.83 (m, 1H); 2.01 (m, 1H); 2.38 (m, 1H); 3.26 (m, 2H). ESI-MS m/z calc. 153.15175, found 154.0 (M+1)$^+$.

Preparation 141: N-(benzenesulfonyl)-6-(3-fluoro-5-isobutoxy-phenyl)-2-[(4S)-2,2,4-trimethylpyrrolidin-1-yl]pyridine-3-carboxamide

Step 1: N-(benzenesulfonyl)-2-chloro-6-(3-fluoro-5-isobutoxy-phenyl)pyridine-3-carboxamide

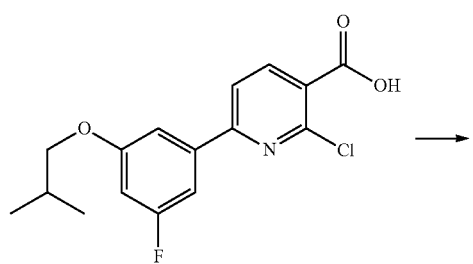

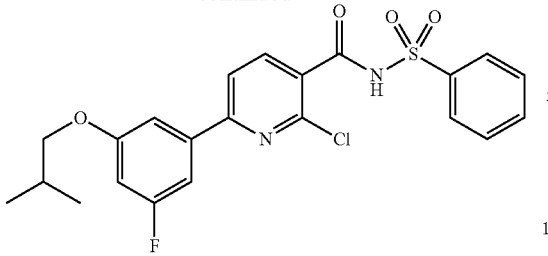

To a solution of the 2-chloro-6-(3-fluoro-5-isobutoxy-phenyl)pyridine-3-carboxylic acid (10.0 g, 30.89 mmol) in DMF (30.0 mL) at ambient temperature in a round bottom flask was slowly added carbonyldiimidazole (5.510 g, 33.98 mmol) portionwise and the mixture stirred for 100 min. Meanwhile to benzenesulfonamide (6.069 g, 38.61 mmol) in DMF (30.0 mL) (homogenous solution) in another round bottom flask was added NaHMDS in THF (38.61 mL of 1.0 M, 38.61 mmol) portionwise via syringe over 30-45 min and on completion of addition the mixture was stirred a further 30 min. The mixture containing the activated acid was then added to the mixture containing the deprotonated sulfonamide and the combined mixture was stirred 1 h. The reaction was cooled with a 0° C. bath and quenched by addition of 12N aqueous HCl (11.58 mL) in portions over 2-3 minutes resulting in precipitated solids. Transferred the reaction mixture to a separatory funnel and ethyl acetate (100.0 mL) was added. Added 1N aqueous HCl (20.0 mL) giving a pH=2-3 then separated the layers and washed the organic layer with 5:1 water/saturated aqueous brine (120.0 mL), saturated aqueous brine (1×50 mL, 1×30 mL), dried (sodium sulfate), filtered and concentrated under reduced pressure to a clear light yellow oil that was concentrated from isopropanol several more times resulting in precipitation of a solid. The solid was slurried overnight in isopropanol then filtered and washed the solid with heptane (50 mL) and dried in vacuo giving N-(benzenesulfonyl)-2-chloro-6-(3-fluoro-5-isobutoxy-phenyl)pyridine-3-carboxamide (10.22 g, 22.08 mmol, 71.47%) as a white solid. $^1$H NMR (400 MHz, DMSO) δ 12.85 (s, 1H), 8.15 (d, J=8.0 Hz, 1H), 8.09 (d, J=8.0 Hz, 1H), 8.02 (dd, J=5.3, 3.3 Hz, 2H), 7.76 (d, J=7.4 Hz, 1H), 7.69 (t, J=7.6 Hz, 2H), 7.51-7.43 (m, 2H), 6.99 (dd, J=10.8, 2.3 Hz, 1H), 3.85 (d, J=6.5 Hz, 2H), 2.04 (dt, J=13.3, 6.6 Hz, 1H), 1.00 (d, J=6.7 Hz, 6H). ESI-MS m/z calc. 462.08163, found 463.19 (M+1)$^+$; Retention time: 2.93 minutes [5 minute method].

Step 2: N-(benzenesulfonyl)-6-(3-fluoro-5-isobutoxy-phenyl)-2-[(4S)-2,2,4-trimethylpyrrolidin-1-yl]pyridine-3-carboxamide

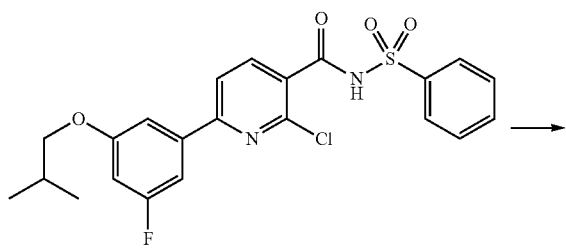

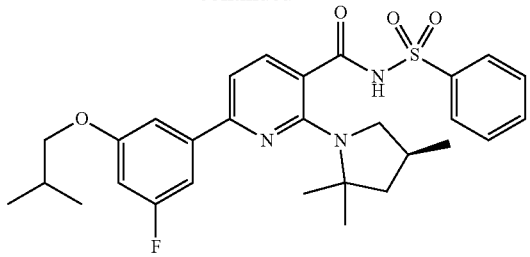

To a round bottom flask outfitted with a reflux condenser was added N-(benzenesulfonyl)-2-chloro-6-(3-fluoro-5-isobutoxy-phenyl)pyridine-3-carboxamide (10.0 g, 21.60 mmol) and NMP (40 mL) and stirring was commenced. Warmed to 50° C. and began portionwise addition of potassium carbonate (5.970 g, 43.20 mmol) followed by (4S)-2,2,4-trimethylpyrrolidine (4.890 g, 43.20 mmol) in one portion. After stirring for 10 min, heated the mixture to 125° C. for 65 h, then cooled to 10° C. and added 1N aqueous HCl (50.0 mL, 50.00 mmol) in portions to give pH 1-2 and a precipitated solid. Added ethyl acetate (100.0 mL) to dissolve solid and diluted the aqueous layer with water (50.0 mL) and stirred for 10 min. The mixture was transferred to a separatory funnel and layers were allowed to separate. Added aqueous 1N HCl dropwise until all solids were dissolved. Separated the layers and the aqueous layer was back extracted with ethyl acetate (50.00 mL) followed by combination of the organic layers. To the combined organic layers was added water (50.00 mL) giving an emulsion which was clarified by the addition of 1N aqueous HCl (25.00 mL). Separated the layers then the organic layer was washed with saturated aqueous brine (50.00 mL), dried over Na$_2$SO$_4$, filtered through celite and rinsed with ethyl acetate (30.00 mL). The filtrate was concentrated under reduced pressure and the residue was purified by silica gel chromatography using a gradient from 100% hexanes to 50% EtOAc giving a light amber oil which was evaporated from isopropanol several times under reduced pressure providing N-(benzenesulfonyl)-6-(3-fluoro-5-isobutoxy-phenyl)-2-[(4S)-2,2,4-trimethylpyrrolidin-1-yl]pyridine-3-carboxamide (9.73 g, 18.03 mmol, 83.5%) as a yellow solid. $^1$H NMR (400 MHz, DMSO-d$_6$) δ 12.57 (s, 1H), 8.16-7.88 (m, 2H), 7.82-7.57 (m, 4H), 7.47 (t, J=1.8 Hz, 1H), 7.40 (dt, J=9.9, 2.0 Hz, 1H), 7.27 (d, J=8.1 Hz, 1H), 6.89 (dt, J=10.8, 2.3 Hz, 1H), 3.83 (d, J=6.6 Hz, 2H), 2.48-2.28 (m, 2H), 2.07 (dtt, J=26.6, 13.4, 6.4 Hz, 2H), 1.83 (dd, J=11.9, 5.5 Hz, 1H), 1.57 (d, J=17.3 Hz, 6H), 1.38 (t, J=12.1 Hz, 1H), 1.04 (d, J=6.1 Hz, 1H), 0.98 (d, J=6.7 Hz, 6H), 0.66 (d, J=6.3 Hz, 3H). ESI-MS m/z calc. 539.2254, found 540.0 (M+1)$^+$; Retention time: 3.25 minutes [5 minute method].

Preparation 142: N-[(2-amino-3-pyridyl)sulfonyl]-6-(6-isopropoxy-3-pyridyl)-2-[(4S)-2,2,4-trimethylpyrrolidin-1-yl]pyridine-3-carboxamide

Step 1: Ethyl 2-chloro-6-(6-isopropoxy-3-pyridyl)pyridine-3-carboxylate

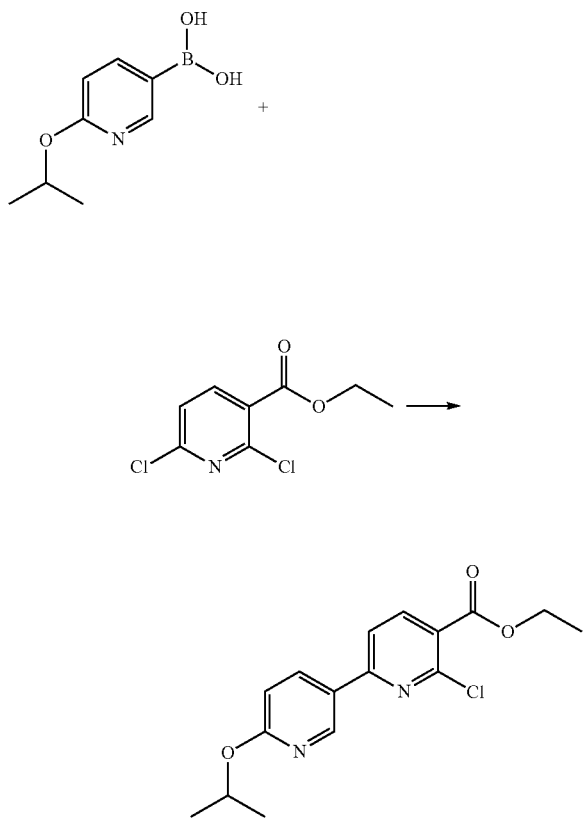

Ethyl 2,6-dichloropyridine-3-carboxylate (7.00 g, 31.81 mmol) and (6-isopropoxy-3-pyridyl)boronic acid (5.04 g, 27.85 mmol) were combined and dissolved in ethanol (50.40 mL) and toluene (50.40 mL). A suspension of sodium carbonate (10.12 g, 95.47 mmol) in water (10.08 mL) was added. Under nitrogen, tetrakis(triphenylphosphine)palladium (1.103 g, 0.9547 mmol) was added. The reaction mixture was allowed to warm to 80° C. and stirred for 2 h. The volatiles were removed under reduced pressure. The remaining solids were partitioned between water (75 mL) and ethyl acetate (75 mL). The organic layer was washed with saturated aqueous sodium chloride solution (1×75 mL), dried over sodium sulfate, filtered and concentrated under reduced pressure. The material was subjected to silica gel column chromatography using a gradient from 100% hexanes to 5% ethyl acetate in hexanes. Ethyl 2-chloro-6-(6-isopropoxy-3-pyridyl)pyridine-3-carboxylate (3.95 g, 12.07 mmol, 43.33%) was obtained as a clear colorless oil. $^1$H NMR (400 MHz, DMSO) δ 8.91 (s, 1H), 8.37 (dd, J=8.7, 2.3 Hz, 1H), 8.30 (d, J=8.1 Hz, 1H), 8.10 (d, J=8.1 Hz, 1H), 6.89 (d, J=8.7 Hz, 1H), 5.34 (dt, J=12.3, 6.1 Hz, 1H), 4.36 (q, J=7.1 Hz, 2H), 2.51 (d, J=1.7 Hz, 1H), 1.42-1.30 (m, 9H). ESI-MS m/z calc. 320.09277, found 321.2 (M+1)$^+$; Retention time: 0.72 minutes.

Step 2: 2-chloro-6-(6-isopropoxy-3-pyridyl)pyridine-3-carboxylic acid

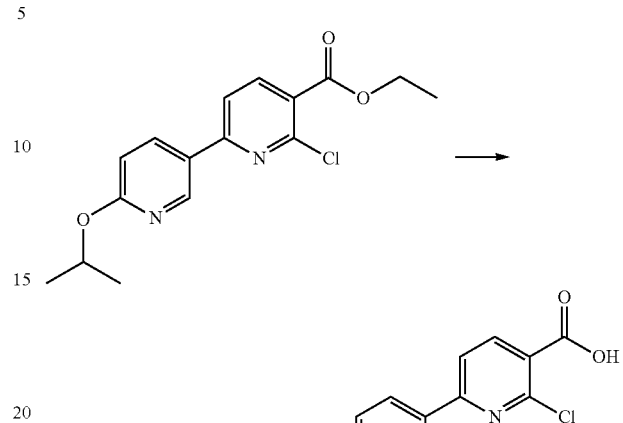

A solution of sodium hydroxide (2.594 g, 64.85 mmol) in water (20.80 mL) was added to a solution of ethyl 2-chloro-6-(6-isopropoxy-3-pyridyl)pyridine-3-carboxylate (4.16 g, 12.97 mmol) in isopropanol (20.8 mL) stirring at 90° C. The reaction mixture was stirred at 90° C. for 30 min. After cooling to room temperature, the reaction mixture was diluted with ethyl acetate (75 mL) and extracted with saturated aqueous sodium bicarbonate (1×75 mL) and aqueous NaOH (1 N, 5×50 mL). The aqueous layers were combined and acidified to pH=1 with the addition of aqueous 6 N HCl. The white precipitate that formed was collected by vacuum filtration and rinsed with aqueous 1 N HCl to provide 2-chloro-6-(6-isopropoxy-3-pyridyl)pyridine-3-carboxylic acid (4.2446 g, 12.89 mmol, 99.43%) as a white solid. ESI-MS m/z calc. 292.06146, found 293.1 (M+1)$^+$; Retention time: 0.59 minutes.

Step 3: 2-aminopyridine-3-sulfonamide

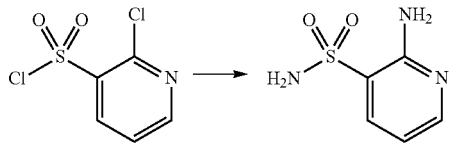 [SMILES: O=S(=O)(Cl)c1cccnc1Cl ; Nc1ncccc1S(N)(=O)=O]

Ammonium hydroxide (590.3 mL of 28% w/v, 4.716 mol) was stirred and cooled in an ice bath. 2-chloropyridine-3-sulfonyl chloride (50 g, 235.8 mmol) was dissolved in dichloromethane (150 mL) and added dropwise to the stirred ammonia solution to maintain a temperature between 5-12° C. On completion of addition, the mixture was stirred 1 h. Stirring was halted and the resulting layers were separated. Concentrated the aqueous layer under vacuum to remove ammonia resulting in a white solid precipitate which was collected by filtration and washed with water. The material was dissolved in ammonium hydroxide (236.1 mL of 28% w/v, 1.886 mol) and heated in a pressure vessel at 100° C. overnight then reaction temperature was increased to 150°

C. and stirred overnight. The mixture was cooled to room temperature resulting in a precipitate then concentrated under vacuum to remove ammonia resulting in a white solid precipitate which was collected by filtration and washed with methyl tert-butyl ether (100 mL) to give 2-aminopyridine-3-sulfonamide (25.73 g, 148.6 mmol, 63.00%) ESI-MS m/z calc. 173.0259, found 174.0 (M+1)⁺.

Step 4: N-[(2-amino-3-pyridyl)sulfonyl]-2-chloro-6-(6-isopropoxy-3-pyridyl)pyridine-3-carboxamide

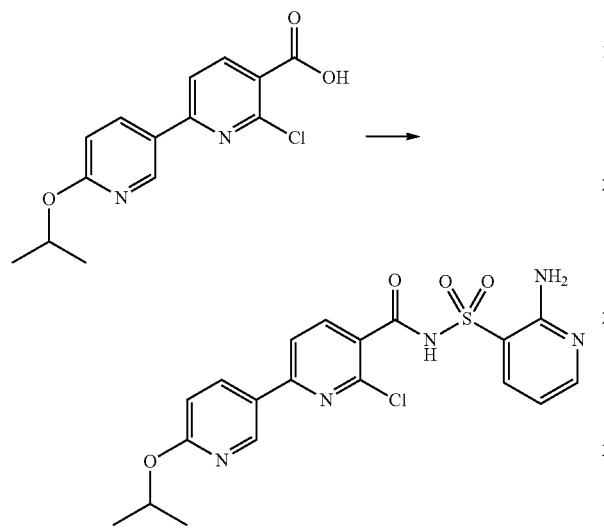

To a solution of 2-aminopyridine-3-sulfonamide (4.068 g, 23.49 mmol) in DMF (38.50 mL) (homogenous solution) in a round bottom flask was added NaH (939.5 mg, 23.49 mmol) portionwise giving an off-white thick slurry and a slight exotherm from 20° C. to 32° C. during addition. The mixture was stirred at ambient temperature for 30 min. Meanwhile, to a solution of 2-chloro-6-(6-isopropoxy-3-pyridyl)pyridine-3-carboxylic acid (5.5 g, 18.79 mmol) in DMF (38.50 mL) at ambient temperature in another round bottom flask was slowly added carbonyldiimidazole (3.352 g, 20.67 mmol) portionwise and the mixture stirred for 20 min over which time it became a light yellow homogenous solution which was then added to the reaction mixture containing the deprotonated sulfonamide. During the addition the mixture stayed homogenous with a slight exotherm to 31° C. The combined mixture was stirred at ambient temperature affording a dark orange homogenous mixture and after 5 min was slowly added to chilled HCl (93.95 mL of 1 M, 93.95 mmol) (slightly exothermic) giving a pH of ~1. The mixture afforded a precipitate and the slurry was stirred for 60 min at ambient temperature. The mixture was then filtered and the solid was washed three times with 50 mL of water. The solid was then washed three times with 50 mL of isopropanol giving an off-white solid that was air dried for 1 h. The solid was next slurried in 50 mL of isopropanol and the precipitate was filtered and washed three times with 5 mL of isopropanol. The off-white solid obtained was air dried for 2 h, then in vacuo at 45° C. for 48 h giving N-[(2-amino-3-pyridyl)sulfonyl]-2-chloro-6-(6-isopropoxy-3-pyridyl)pyridine-3-carboxamide (8.0 g, 17.86 mmol, 95.06%) ¹H NMR (400 MHz, DMSO-d₆) δ 8.87 (d, J=2.5 Hz, 1H), 8.33 (dd, J=8.7, 2.6 Hz, 1H), 8.24 (dd, J=5.1, 1.8 Hz, 1H), 8.13-8.00 (m, 3H), 6.96 (s, 2H), 6.88 (d, J=8.7 Hz, 1H), 6.83 (dd, J=7.8, 5.0 Hz, 1H), 5.33 (hept, J=6.3 Hz, 1H), 1.32 (d, J=6.2 Hz, 6H). ESI-MS m/z calc. 447.0768, found 448.18 (M+1)⁺; Retention time: 1.55 minutes.

Step 5: N-[(2-amino-3-pyridyl)sulfonyl]-6-(6-isopropoxy-3-pyridyl)-2-[(4S)-2,2,4-trimethylpyrrolidin-1-yl]pyridine-3-carboxamide

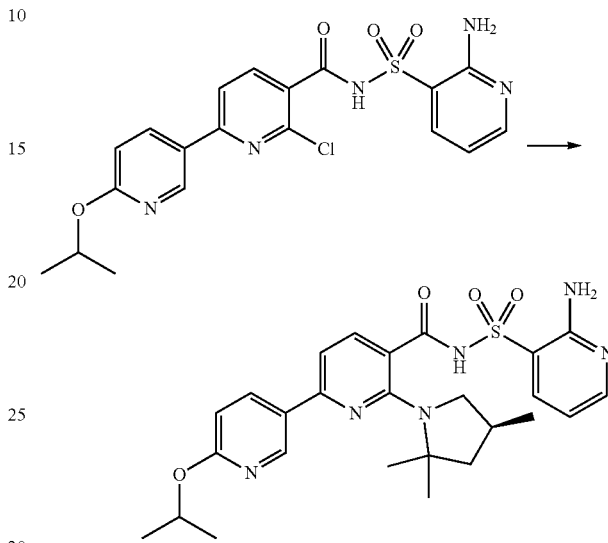

A vial equipped with magnetic stir bar was charged with N-[(2-amino-3-pyridyl)sulfonyl]-2-chloro-6-(6-isopropoxy-3-pyridyl)pyridine-3-carboxamide (147.8 mg, 0.330 mmol), (4S)-2,2,4-trimethylpyrrolidine (74.71 mg, 0.660 mmol) and potassium carbonate (228.0 mg, 1.65 mmol) in DMSO (739 µL). The vial was sealed and stirred at 120° C. for 16 hours then at 140° C. for 30 hours. The reaction mixture was cooled, diluted with minimal DMSO and methanol and filtered. The filtrate was purified directly using a reverse phase HPLC-MS method using a Luna C18 (2) column (75×30 mm, 5 µm particle size) sold by Phenomenex (pn: 00C-4252-U0-AX), and a dual gradient run from 1-99% mobile phase B over 15.0 minutes (mobile phase A=H₂O (5 mM HCl), mobile phase B=CH₃CN, flow rate=50 mL/min, injection volume=950 µL and column temperature=25° C.) giving N-[(2-amino-3-pyridyl)sulfonyl]-6-(6-isopropoxy-3-pyridyl)-2-[(4S)-2,2,4-trimethylpyrrolidin-1-yl]pyridine-3-carboxamide (25.2 mg, 0.048 mmol, 14.6%). ¹H NMR (400 MHz, DMSO) δ 12.49 (s, 1H), 8.84 (d, J=2.4 Hz, 1H), 8.31-8.27 (m, 1H), 8.25 (dd, J=7.4, 4.4 Hz, 1H), 8.03 (dd, J=7.9, 1.7 Hz, 1H), 7.75 (d, J=8.0 Hz, 1H), 7.20 (d, J=8.0 Hz, 1H), 6.86 (d, J=8.7 Hz, 1H), 6.77 (dd, J=7.8, 4.8 Hz, 1H), 6.69 (s, 2H), 5.37-5.26 (m, 1H), 2.52 (s, 1H), 2.14 (s, 1H), 1.85 (dd, J=11.9, 5.5 Hz, 1H), 1.58 (d, J=10.7 Hz, 6H), 1.39 (t, J=12.1 Hz, 1H), 1.31 (d, J=6.2 Hz, 6H), 1.26 (d, J=13.3 Hz, 1H), 0.86 (t, J=6.9 Hz, 1H), 0.76 (d, J=6.3 Hz, 3H). ESI-MS m/z calc. 524.2206, found 525.3 (M+1)⁺; Retention time: 1.38 minutes.

The following compounds can be synthesized using the procedures described herein:
N-[(2-amino-6-methoxy-3-pyridyl)sulfonyl]-6-(6-isopropoxy-3-pyridyl)-2-[(4S)-2,2,4-trimethylpyrrolidin-1-yl]pyridine-3-carboxamide (Compound 2692),
N-[(2-amino-3-pyridyl)sulfonyl]-2-[(4S)-3,3-dideuterio-2,2-dimethyl-4-(trideuteriomethyl)pyrrolidin-1-yl]-6-(6-isopropoxy-3-pyridyl)pyridine-3-carboxamide (Compound 1543) and

2259

N-[(6-amino-2-pyridyl)sulfonyl]-2-[(2R,5S)-2,5-dimethylpyrrolidin-1-yl]-6-[6-[1,2,2,2-tetradeuterio-1-(trideuteriomethyl)ethoxy]-3-pyridyl]pyridine-3-carboxamide (Compound 2714)

Preparation 143: 6-[3-(2,2-dimethylpropoxy)pyrazol-1-yl]-N-[[6-(1-piperidyl)-2-pyridyl]sulfonyl]-2-[(4S)-2,2,4-trimethylpyrrolidin-1-yl]pyridine-3-carboxamide (Compound 484)

Step 1: 6-(1-piperidyl)pyridine-2-sulfonamide

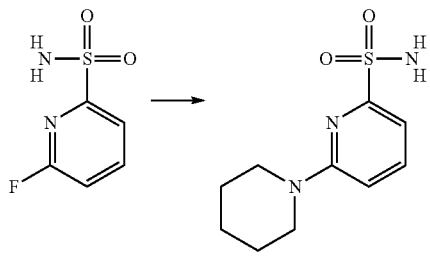

To 6-fluoro-2-pyridinesulfonamide (215 mg, 1.220 mmol) was added piperidine (312 mg, 362 µL, 3.66 mmol) and the reaction mixture was heated at 90° C. for 2.5 hours. The reaction mixture was cooled and resulting solid was dried. $^1$H NMR (400 MHz, DMSO-d$_6$) δ 7.66 (dd, J=8.8, 7.2 Hz, 1H), 7.03 (d, J=7.2 Hz, 1H), 6.98 (d, J=8.6 Hz, 1H), 2.75 (d, J=5.5 Hz, 3H), 1.61 (p, J=3.4, 2.9 Hz, 2H), 1.54 (dd, J=7.0, 3.9 Hz, 3H), 1.49 (s, 4H). ESI-MS m/z found 242.2 (M+1)$^+$; Retention time: 0.45 minutes.

Step 2: 2-chloro-6-(3-(neopentyloxy)-1H-pyrazol-1-yl)-N-((6-(piperidin-1-yl)pyridin-2-yl)sulfonyl)nicotinamide

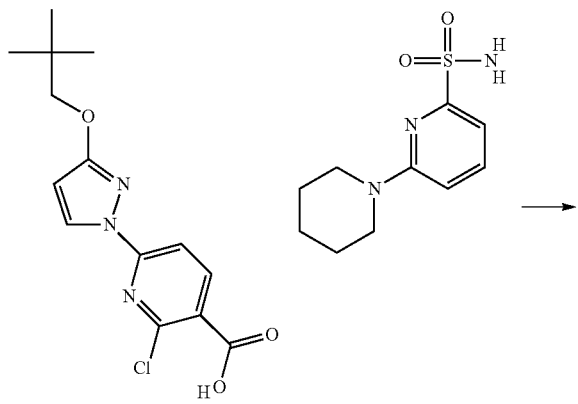

2260

-continued

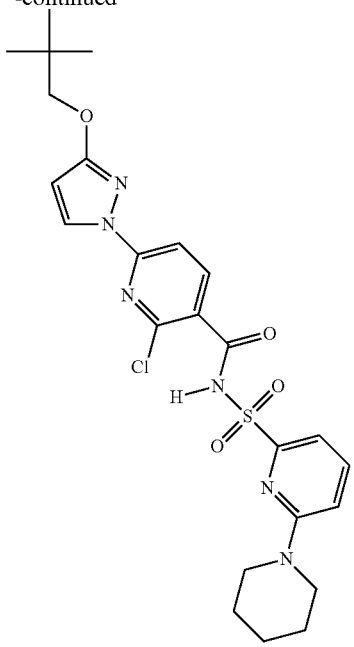

To 2-chloro-6-[3-(2,2-dimethylpropoxy)pyrazol-1-yl]pyridine-3-carboxylic acid (100 mg, 0.323 mmol) in DMF (0.6 mL) at room temperature was added carbonyl diimidazole (78.5 mg, 0.484 mmol) and the reaction mixture was stirred for 40 minutes. Separately 6-(1-piperidyl)pyridine-2-sulfonamide (93.5 mg, 0.387 mmol) in DMF (0.6 mL) was cooled to 0° C. and treated with sodium hydride (15.5 mg, 0.387 mmol) and stirred for 10 min and then at room temperature for 30 min. The reaction mixtures were then combined and stirred at room temperature for 30 min. The reaction mixture was cooled to 0° C. and acetic acid (194 mg, 184 µL, 3.23 mmol) was added followed by HCL (269 µL of 6 M, 1.61 mmol) and the reaction mixture was diluted with EtOAc (5 mL) and the layers were separated. The organics were dried and concentrated under reduced pressure to give a residue which was purified by silica gel column chromatography and eluted with 0-14% MeOH-DCM to give 2-chloro-6-[3-(2,2-dimethylpropoxy)pyrazol-1-yl]-N-[[6-(1-piperidyl)-2-pyridyl]sulfonyl]pyridine-3-carboxamide (158 mg, 82%) ESI-MS m/z found 533.2 (M+1)$^+$; Retention time: 0.89 minutes (1 min); 1H NMR (400 MHz, DMSO-d$_6$) δ 8.44-8.38 (m, 1H), 8.05 (d, J=8.3 Hz, 1H), 7.95 (s, 1H), 7.79-7.70 (m, 2H), 7.23 (d, J=7.2 Hz, 1H), 7.12 (d, J=8.7 Hz, 1H), 6.22 (t, J=2.5 Hz, 1H), 3.93 (d, J=1.2 Hz, 2H), 3.59 (t, J=5.4 Hz, 3H), 1.66-1.58 (m, 2H), 1.53 (td, J=10.2, 4.8 Hz, 3H), 1.00 (s, 911).

Step 3: 6-[3-(2,2-dimethylpropoxy)pyrazol-1-yl]-N-[[6-(1-piperidyl)-2-pyridyl]sulfonyl]-2-[(4S)-2,2,4-trimethylpyrrolidin-1-yl]pyridine-3-carboxamide (Compound 484)

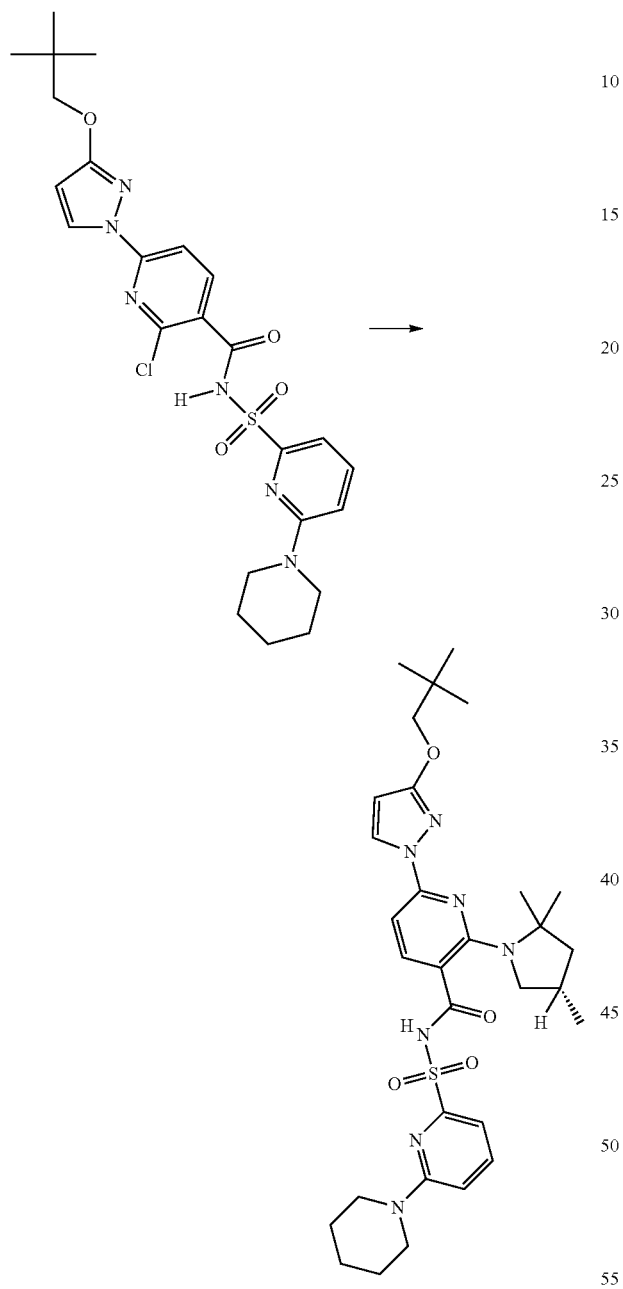

A mixture of 2-chloro-6-[3-(2,2-dimethylpropoxy)pyrazol-1-yl]-N-[[6-(1-piperidyl)-2-pyridyl]sulfonyl]pyridine-3-carboxamide (140 mg, 0.223 mmol), potassium carbonate (185 mg, 1.34 mmol) and (4S)-2,2,4-trimethylpyrrolidine (HCl salt) (75 mg, 0.501 mmol) in DMSO (744 L) was heated at 150° C. for 5 h. The reaction mixture was cooled, diluted with EtOAc and the aqueous and organic layers were separated. The organics were washed with brine, dried, concentrated under reduced pressure and the resulting residue was purified by silica gel column chromatography eluting with 0-15% MeOH-DCM to give 6-[3-(2,2-dimethylpropoxy)pyrazol-1-yl]-N-[[6-(1-piperidyl)-2-pyridyl]sulfonyl]-2-[(4S)-2,2,4-trimethylpyrrolidin-1-yl]pyridine-3-carboxamide (Compound 484) (38 mg, 28%). ESI-MS m/z calc 609.31, found 610.1 (M+1)$^+$; retention time 2.1 min (3 min run); 1H NMR (400 MHz, Methanol-d$_4$) δ 8.25 (d, J=2.8 Hz, 1H), 7.88 (d, J=8.3 Hz, 1H), 7.69 (dd, J=8.7, 7.2 Hz, 1H), 7.31 (d, J=7.2 Hz, 1H), 6.98 (dd, J=8.5, 6.5 Hz, 2H), 5.99 (d, J=2.8 Hz, 1H), 3.90 (s, 2H), 3.63 (q, J=6.1, 5.3 Hz, 4H), 2.80-2.66 (m, 2H), 2.26 (d, J=10.4 Hz, 1H), 1.90 (dd, J=11.9, 5.6 Hz, 1H), 1.68 (q, J=5.1, 4.7 Hz, 2H), 1.61 (d, J=5.3 Hz, 10H), 1.47 (t, J=12.2 Hz, 1H), 1.04 (s, 9H), 0.88 (d, J=6.3 Hz, 3H).

The following compound can be synthesized using the procedures described herein: 6-[3-(2,2-dimethylpropoxy)pyrazol-1-yl]-N-[[2-(1-piperidyl)-3-pyridyl]sulfonyl]-2-[(4S)-2,2,4-trimethylpyrrolidin-1-yl]pyridine-3-carboxamide (Compound 2670)

Preparation 144: N-[(6-amino-2-pyridyl)sulfonyl]-3-(3-fluoro-5-isobutoxy-phenyl)-5-[(4S)-2,2,4-trimethylpyrrolidin-1-yl]pyrazine-2-carboxamide (Compound 2673)

Step 1: 3,5-dichloro-N-[(6-nitro-2-pyridyl)sulfonyl]pyrazine-2-carboxamide

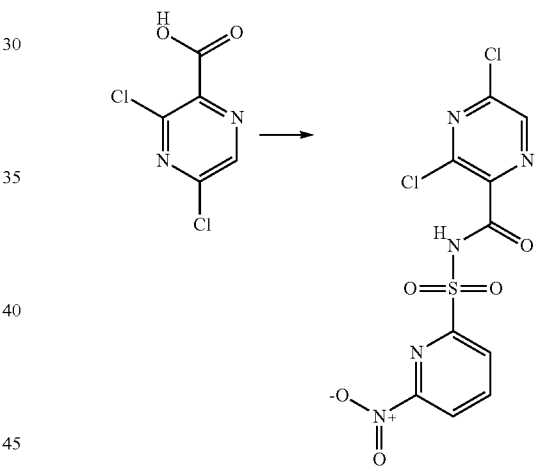

To a stirred heterogeneous mixture of 3,5-dichloropyrazine-2-carboxylic acid (2.21 g, 11.5 mmol) in anhydrous CH$_2$Cl$_2$ (20 mL), thionyl chloride (7.5 mL, 103 mmol) was added under an atmosphere of nitrogen, followed by anhydrous DMF (30 mg, 0.41 mmol) and the reaction mixture was stirred at room temperature for 1 hour. The reaction mixture was evaporated, dissolved in CH$_2$Cl$_2$ (40 mL) and added dropwise to a solution of 6-nitropyridine-2-sulfonamide (2.32 g, 11.5 mmol) with triethylamine (8.5 mL, 61.0 mmol) at 0° C., stirred overnight (24 h) while allowing to warm to ambient temperature. The reaction mixture was concentrated under reduced pressure. The residue was partitioned between CH$_2$Cl$_2$ (10 mL) and ice-water (200 mL) and acidified with 2 M HCl to pH about 4.0. The resulting solid was filtered, the layers separated and the aqueous layer was extract with CH$_2$Cl$_2$ (3×50 mL). The combined organics were washed sequentially with 1N HCl, saturated sodium chloride solution then dried over sodium sulfate, filtered and evaporated under reduced pressure. The crude material was purified by triturating with dichloromethane (10 mL), filtration and drying to give 3,5-dichloro-N-[(6-nitro-2-pyridyl)sulfonyl]pyrazine-2-carboxamide (2.90 g, 67%) as a white solid. ESI-MS m/z calc. 376.93884, found 378.0 (M+1)⁺; Retention time: 0.6 minutes.

Step 2: N-[(6-amino-2-pyridyl)sulfonyl]-3,5-dichloro-pyrazine-2-carboxamide

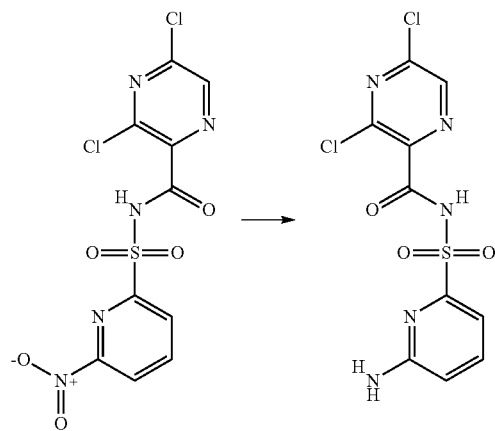

To a solution of 3,5-dichloro-N-[(6-nitro-2-pyridyl)sulfonyl]pyrazine-2-carboxamide (830 mg, 2.20 mmol) in THF (8 mL) and EtOH (4 mL), iron (Fe) powder (613 mg, 11.0 mmol) was added, followed by HCl (6 N) (1.8 mL of 6.0 M, 10.80 mmol). The reaction mixture was heated at 60° C. for 15 min. After cooling to room temperature, the reaction mixture was filtered and the filtrate was concentrated under reduced pressure. The residue was diluted with EtOAc (50 mL) and washed with NaOH (4 mL, 1 N). The layers were filtered again and the aqueous layer was acidified to pH 2 with the addition of 1 N HCl (aq) and extracted with EtOAc (2×50 mL). The organic layer was dried over sodium sulfate, filtered and concentrated under reduced pressure. The crude material was purified from by silica gel column chromatography using 0-20% MeOH in CH₂Cl2 as eluent to give N-[(6-amino-2-pyridyl)sulfonyl]-3,5-dichloro-pyrazine-2-carboxamide (404 mg, 53%) ESI-MS m/z calc. 346.96466, found 348.0 (M+1)⁺; Retention time: 0.53 minutes.

Step 3: N-[(6-amino-2-pyridyl)sulfonyl]-5-chloro-3-[(4S)-2,2,4-trimethylpyrrolidin-1-yl]pyrazine-2-carboxamide and (S)—N-((6-aminopyridin-2-yl)sulfonyl)-3-chloro-5-(2,2,4-trimethylpyrrolidin-1-yl)pyrazine-2-carboxamide

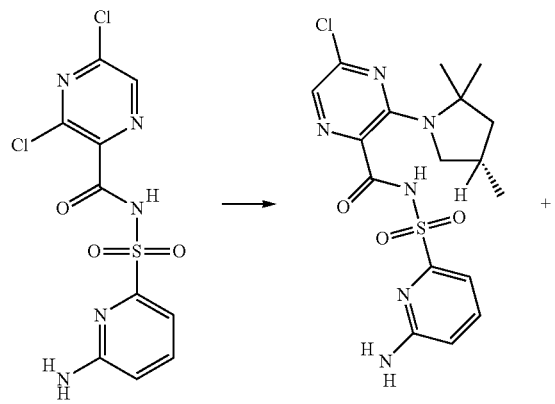

-continued

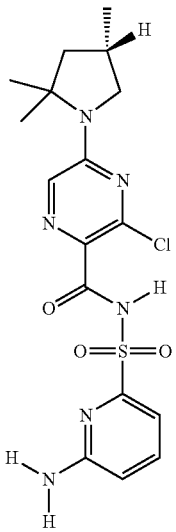

To a solution of N-[(6-amino-2-pyridyl)sulfonyl]-3,5-dichloro-pyrazine-2-carboxamide (36 mg, 0.10 mmol) in DMSO (142 µL), DIEA (90 µL, 0.52 mmol) and (4S)-2,2,4-trimethylpyrrolidine (32 mg, 0.26 mmol) was added. The reaction mixture was stirred for 6 hours at 85° C. The cooled reaction was purified via reverse phase HPLC-MS method using a dual gradient run from 15-99% mobile phase B over 15.0 minutes (mobile phase A=H₂O (5 mM HCl), mobile phase B=acetonitrile) to yield a mixture of N-[(6-amino-2-pyridyl)sulfonyl]-5-chloro-3-[(4S)-2,2,4-trimethylpyrrolidin-1-yl]pyrazine-2-carboxamide and (S)—N-((6-amino-pyridin-2-yl)sulfonyl)-3-chloro-5-(2,2,4-trimethylpyrrolidin-1-yl)pyrazine-2-carboxamide (28 mg, 64%) ESI-MS m/z calc. 424.10843, found 425.2 (M+1)⁺.

Step 4: N-[(6-amino-2-pyridyl)sulfonyl]-3-(3-fluoro-5-isobutoxy-phenyl)-5-[(4S)-2,2,4-trimethylpyrrolidin-1-yl]pyrazine-2-carboxamide (Compound 2673)

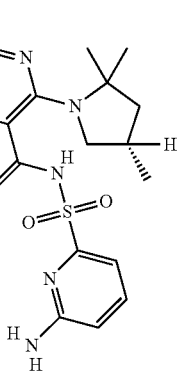

-continued

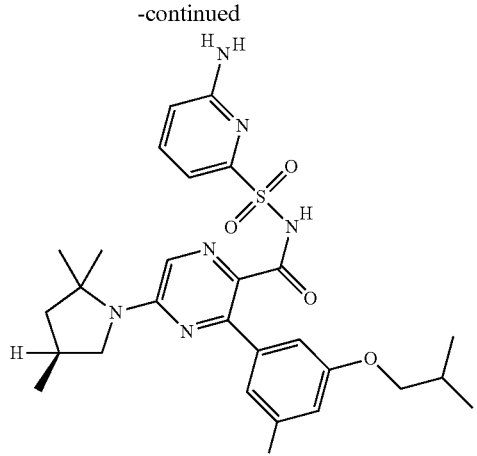

To a solution of N-[(6-amino-2-pyridyl)sulfonyl]-5-chloro-3-[(4S)-2,2,4-trimethylpyrrolidin-1-yl]pyrazine-2-carboxamide (S)—N-((6-aminopyridin-2-yl)sulfonyl)-3-chloro-5-(2,2,4-trimethylpyrrolidin-1-yl)pyrazine-2-carboxamide (60 mg, 0.14 mmol) and (3-fluoro-5-isobutoxy-phenyl)boronic acid (60 mg, 0.28 mmol) in dioxane (3.0 mL) were added H$_2$O (1.0 mL), K$_2$CO$_3$ (78 mg, 0.56 mmol) and bis(2-diphenylphosphanylcyclopenta-2,4-dien-1-yl)iron; dichloropalladium [Cl$_2$Pd(dppf)·CH$_2$Cl$_2$] (8 mg, 0.011 mmol). Nitrogen was bubbled for 5 min and the reaction mixture was sealed and stirred at 120° C. under microwave radiation for 30 min. The reaction mixture was allowed to cool to ambient temperature, filtered through a and purified via reverse phase HPLC-MS (using a Luna C18 (2) column (75×30 mm, 5 μm particle size) and a dual gradient run from 30-99% mobile phase B over 30.0 minutes; mobile phase A=H$_2$O (5 mM HCl), mobile phase B=CH$_3$CN) to furnish N-[(6-amino-2-pyridyl)sulfonyl]-3-(3-fluoro-5-isobutoxy-phenyl)-5-[(4S)-2,2,4-trimethylpyrrolidin-1-yl]pyrazine-2-carboxamide (Compound 2673) (5.7 mg, 6%) as off-white solid. 1H NMR (400 MHz, DMSO-d$_6$) δ 11.58 (s, 1H), 7.89 (s, 1H), 7.62-7.53 (m, 1H), 7.11 (d, J=7.3 Hz, 1H), 6.88-6.79 (m, 2H), 6.75-6.69 (m, 1H), 6.66 (d, J=8.3 Hz, 1H), 6.52 (s, 2H), 3.83 (t, J=9.1 Hz, 11H), 3.74 (d, J=6.5 Hz, 2H), 3.12 (t, J=10.4 Hz, 1H), 2.47-2.35 (m, 1H), 2.02 (dd, J=12.8, 6.3 Hz, 2H), 1.61 (d, J=12.2 Hz, 1H), 1.56 (s, 3H), 1.45 (s, 3H), 1.10 (d, J=6.4 Hz, 3H), 0.96 (d, J=6.8 Hz, 6H). ESI-MS m/z calc. 556.2268, found 557.4 (M+1)$^+$; Retention time: 2.15 minutes.

Preparation 145: N-[(6-amino-2-pyridyl)sulfonyl]-6-(3-fluoro-5-isobutoxy-phenyl)-4-[(4S)-2,2,4-trimethylpyrrolidin-1-yl]pyridine-3-carboxamide (Compound 2679)

Step 1: 4-chloro-6-(3-fluoro-5-isobutoxy-phenyl)pyridine-3-carboxylic acid

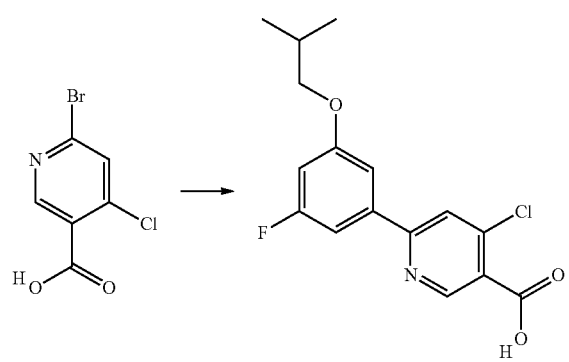

To 6-bromo-4-chloro-pyridine-3-carboxylic acid (205 mg, 0.865 mmol), (3-fluoro-5-isobutoxy-phenyl)boronic acid (184 mg, 0.865 mmol), and palladium; triphenylphosphane (30.0 mg, 0.0260 mmol) in dioxane (4 mL) was added solution of potassium carbonate (1.73 mL of 2 M, 3.46 mmol) under an atmosphere of nitrogen and the reaction mixture was stirred at 80° C. for 10 h. The reaction mixture was concentrated under reduced pressure, partitioned between water (15 mL) and EtOAc (15 mL). The aqueous layer was acidified with HCl and washed with EtOAc (3×15 mL). The combined organic layers was washed with brine (1×25 mL), dried over sodium sulfate, filtered and concentrated under reduced pressure. The solid obtained was washed with hexanes to give 4-chloro-6-(3-fluoro-5-isobutoxy-phenyl)pyridine-3-carboxylic acid (232 mg, 83%) as a tan solid. ESI-MS m/z calc. 323.07245, found 324.1 (M+1)$^+$; Retention time: 0.74 minutes.

Step 2: 4-chloro-6-(3-fluoro-5-isobutoxy-phenyl)-N-[(6-nitro-2-pyridyl)sulfonyl]pyridine-3-carboxamide

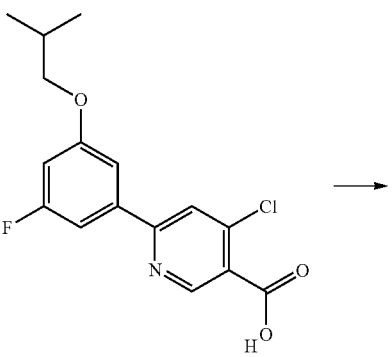

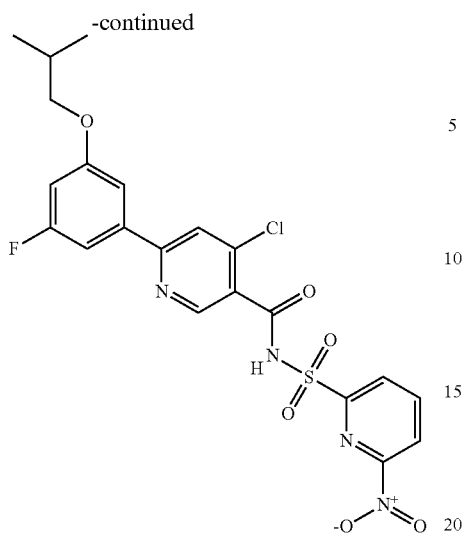

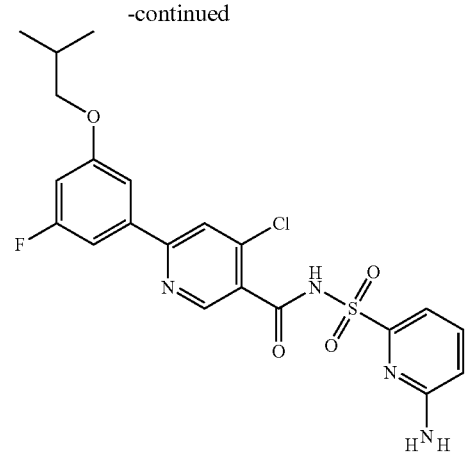

4-chloro-6-(3-fluoro-5-isobutoxy-phenyl)pyridine-3-carboxylic acid (104 mg, 0.32 mmol) and SOCl₂ (190 mg, 116 µL, 1.60 mmol) with a drop of DMF was stirred at ambient temperature for 30 minutes. The volatiles were removed under reduced pressure. In another flask, 6-nitropyridine-2-sulfonamide (65 mg, 0.32 mmol) and TEA (97 mg, 134 µL, 0.96 mmol) in DCM (1.2 mL) was cooled in an ice-water bath. A solution of the acid chloride generated in DCM was added slowly. The reaction mixture was stirred in ice-water bath and allowed to reach room temperature. The reaction mixture was diluted with DCM, washed with 1N HCl, saturated NaHCO₃, and brine. The organics were separated and dried over sodium sulfate and evaporated under reduced pressure to give 4-chloro-6-(3-fluoro-5-isobutoxy-phenyl)-N-[(6-nitro-2-pyridyl)sulfonyl]pyridine-3-carboxamide (157 mg, 97%) ESI-MS m/z calc. 508.06195, found 509.1 (M+1)⁺; Retention time: 0.74 minutes.

4-chloro-6-(3-fluoro-5-isobutoxy-phenyl)-N-[(6-nitro-2-pyridyl)sulfonyl]pyridine-3-carboxamide (123 mg, 0.242 mmol) was dissolved in THF (615 µL) and EtOH (615 µL). Powdered Fe (135 mg, 2.42 mmol) with HCl (80.6 µL of 6 M, 0.483 mmol) was added. The reaction mixture was heated at 65° C. for 10 min. After cooling to room temperature, the reaction mixture was filtered, the filtrate was diluted with EtOAc and washed with NaOH (4 mL, 1 N). The layers were filtered again and aqueous layer was acidified to pH 2 with the addition of aqueous HCl and extracted with EtOAc (1×8 mL). The organic layer was dried over sodium sulfate, filtered and concentrated under reduced pressure to give N-[(6-amino-2-pyridyl)sulfonyl]-4-chloro-6-(3-fluoro-5-isobutoxy-phenyl)pyridine-3-carboxamide (61 mg, 53%) as a yellow powder. ESI-MS m/z calc. 478.08777, found 479.1 (M+1)⁺; Retention time: 0.69 minutes.

Step 3: N-[(6-amino-2-pyridyl)sulfonyl]-4-chloro-6-(3-fluoro-5-isobutoxy-phenyl)pyridine-3-carboxamide Step 4: N-[(6-amino-2-pyridyl)sulfonyl]-6-(3-fluoro-5-isobutoxy-phenyl)-4-[(4S)-2,2,4-trimethylpyrrolidin-1-yl]pyridine-3-carboxamide (Compound 2679)

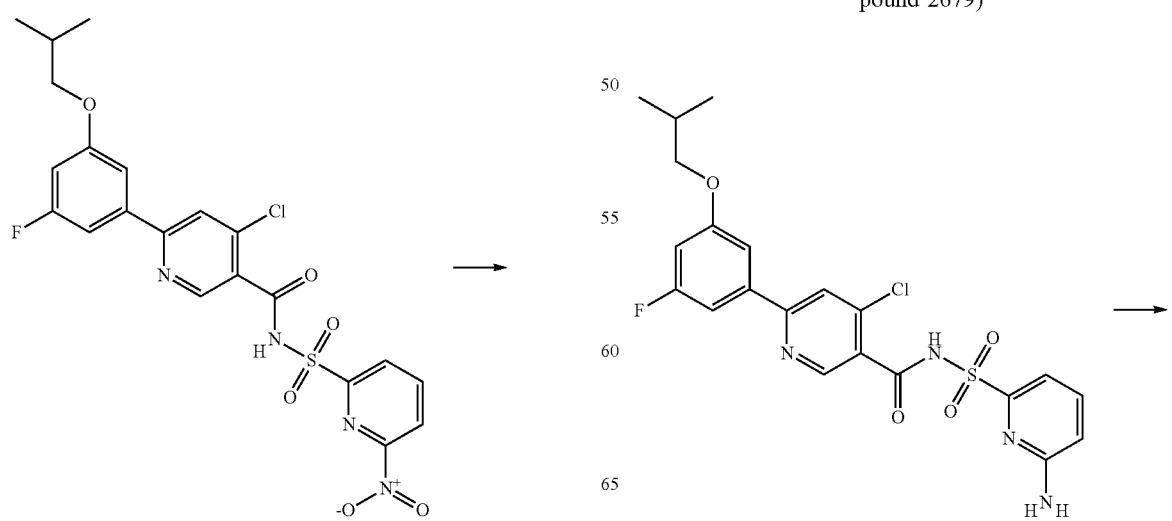

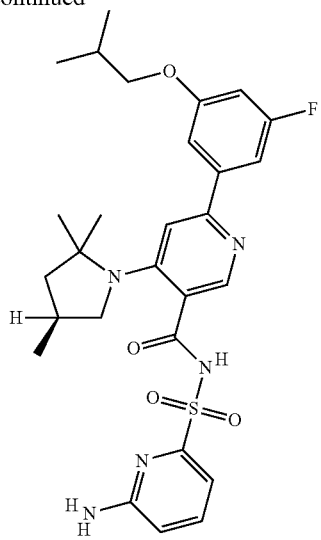

To a solution of N-[(6-amino-2-pyridyl)sulfonyl]-4-chloro-6-(3-fluoro-5-isobutoxy-phenyl)pyridine-3-carboxamide (24 mg, 0.050 mmol) in DMSO (0.1 mL) was added CsF (23 mg, 0.15 mmol) and (4S)-2,2,4-trimethylpyrrolidine (27 mg, 0.15 mmol). The reaction mixture was sealed and stirred at 120° C. overnight. The reaction mixture was cooled, diluted with DMSO and purified via HPLC/MS utilizing a gradient of 1-99% acetonitrile in 5 mM aq HCl to yield N-[(6-amino-2-pyridyl)sulfonyl]-6-(3-fluoro-5-isobutoxy-phenyl)-4-[(4S)-2,2,4-trimethylpyrrolidin-1-yl]pyridine-3-carboxamide (Compound 2679) (5 mg, 19%). ESI-MS m/z calc. 555.23157, found 556.4 (M+1)⁺; Retention time: 1.47 minutes.

Preparation 146: N-[(6-amino-2-pyridyl)sulfonyl]-6-(2-ethoxyethoxy)-2-[(4S)-2,2,4-trimethylpyrrolidin-1-yl]pyridine-3-carboxamide (Compound 2678)

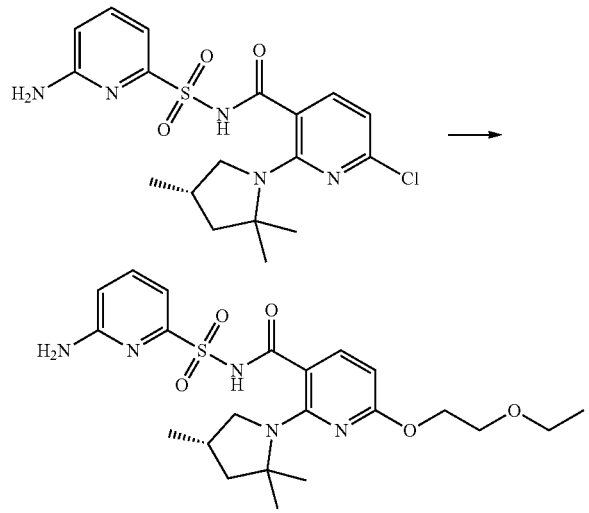

N-[(6-amino-2-pyridyl)sulfonyl]-6-chloro-2-[(4S)-2,2,4-trimethylpyrrolidin-1-yl]pyridine-3-carboxamide (Compound 852) (25 mg, 0.059 mmol), 2-ethoxyethanol (53 mg, 57 µL, 0.59 mmol), NaH (7.0 mg, 0.29 mmol), and scandium (3+) trifluoromethanesulfonate (2.9 mg, 0.0058 mmol) were dissolved in DMSO (0.5 mL) and heated at 120° C. for 8 h. The reaction mixture was partitioned between ethyl acetate and a 1N aq HCl solution. The organics were separated, washed with brine, dried over sodium sulfate and evaporated under reduced pressure. The crude material was purified by silica gel chromatography eluting with 0-100% ethyl acetate in hexanes to give N-[(6-amino-2-pyridyl)sulfonyl]-6-(2-ethoxyethoxy)-2-[(4S)-2,2,4-trimethylpyrrolidin-1-yl]pyridine-3-carboxamide (Compound 2678) (7 mg, 25%) ESI-MS m/z calc. 477.2046, found 478.4 (M+1)*; Retention time: 1.25 minutes.

The following compounds can be synthesized using the procedures described herein:
N-[(2-amino-3-pyridyl)sulfonyl]-6-methoxy-2-[(4S)-2,2,4-trimethylpyrrolidin-1-yl]pyridine-3-carboxamide (Compound 2704),
N-[(2-amino-3-pyridyl)sulfonyl]-6-(2-ethoxyethoxy)-2-[(4S)-2,2,4-trimethylpyrrolidin-1-yl]pyridine-3-carboxamide (Compound 2705) and
N-[(2-amino-3-pyridyl)sulfonyl]-6-[2-(2-ethoxyethoxy)ethoxy]-2-[(4S)-2,2,4-trimethylpyrrolidin-1-yl]pyridine-3-carboxamide (Compound 2706).

Preparation 147: N-[(6-amino-2-pyridyl)sulfonyl]-6-(3-fluoro-5-isobutoxy-phenyl)-2-(4-iodo-2,6-dimethyl-phenoxy)pyridine-3-carboxamide (Compound 2671)

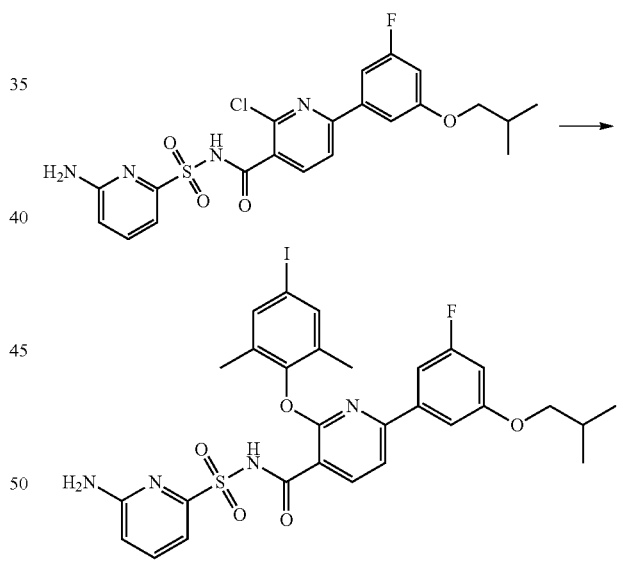

To N-[(6-amino-2-pyridyl)sulfonyl]-2-chloro-6-(3-fluoro-5-isobutoxy-phenyl)pyridine-3-carboxamide (69 mg, 0.14 mmol) and 4-iodo-2,6-dimethyl-phenol (71 mg, 0.29 mmol) in NMP (4 mL) was added NaH (17 mg, 0.43 mmol). The reaction mixture was stirred for 5 min at rt then stirred at 150° C. for 2 h. The reaction mixture was quenched with NH₄Cl soln, the crude mixture purified by reverse phase silica gel column chromatography using 10-100% ACN in Water (TFA modifier) as eluent to give N-[(6-amino-2-pyridyl)sulfonyl]-6-(3-fluoro-5-isobutoxy-phenyl)-2-(4-iodo-2,6-dimethyl-phenoxy)pyridine-3-carboxamide (Compound 2671) (8 mg, 7%). 1H NMR (300 MHz, CDCl₃) δ 8.47 (d, J=8.1 Hz, 1H), 7.76-7.68 (m, 1H), 7.64 (d, J=7.3 Hz, 1H), 7.52 (d, J=8.1 Hz, 1H), 7.47 (s, 2H), 7.04-6.95 (m, 3H), 6.76 (d, J=8.2 Hz, 1H), 6.63 (dt, J=10.3, 2.2 Hz, 11H), 3.56 (t, J=7.0 Hz, 2H), 2.13-2.06 (m, 6H), 1.01 (t, J=6.6 Hz, 6H), 0.85 (t, J=6.7 Hz, 3H), 0.47 (s, 1H). ESI-MS m/z found 691.4 (M+1)+; Retention time: 0.83 minutes The following compounds can be synthesized using the procedures described herein:
N-[(6-amino-2-pyridyl)sulfonyl]-2-(4-benzoyl-2,6-dimethyl-phenoxy)-6-(6-isopropoxy-3-pyridyl)pyridine-3-carboxamide (Compound 2715) and
N-[(6-amino-2-pyridyl)sulfonyl]-2-(4-benzoyl-2,6-dimethyl-phenoxy)-6-(3-fluoro-5-isobutoxy-phenyl)pyridine-3-carboxamide (Compound 2669).

Preparation 148: N-[(6-amino-2-pyridyl)sulfonyl]-2,6-bis(4-benzoyl-2,6-dimethyl-phenoxy)pyridine-3-carboxamide (Compound 970)

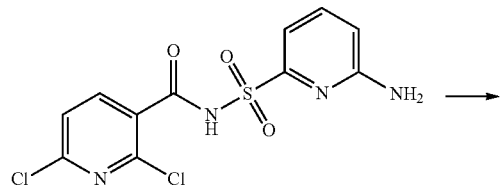

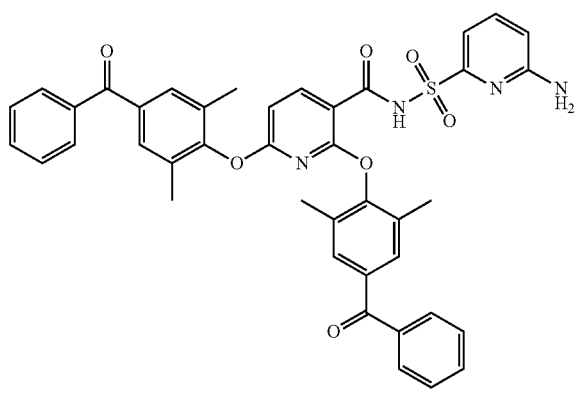

To N-[(6-amino-2-pyridyl)sulfonyl]-2,6-dichloro-pyridine-3-carboxamide (487 mg, 1.40 mmol) in DMF (4 mL) was added (4-hydroxy-3,5-dimethyl-phenyl)-phenyl-methanone (390 mg, 1.57 mmol) and NaH (140.3 mg, 3.508 mmol). The reaction mixture was stirred at rt for 20 min, then 150° C. for 1 hr. The crude mixture purified by reverse phase silica gel column chromatography using 0-80% ACN in Water (TFA modifier) as eluent, then further purified by silica gel column chromatography eluting with 30-100% EtOAc in heptane to give N-[(6-amino-2-pyridyl)sulfonyl]-2,6-bis(4-benzoyl-2,6-dimethyl-phenoxy)pyridine-3-carboxamide (Compound 970) (51 mg, 4%). 1H NMR (300 MHz, DMSO) δ 8.24 (dd, J=15.6, 8.2 Hz, 1H), 7.80-7.66 (m, 1H), 7.66-7.39 (m, 10H), 7.31-7.22 (m, 4H), 7.11 (d, J=7.2 Hz, 1H), 6.74 (t, J=10.3 Hz, 1H), 6.55 (d, J=7.9 Hz, 1H), 6.27 (s, 2H), 1.92 (d, J=1.9 Hz, 12H); ESI-MS m/z found 727.5 (M+1)+; Retention time: 0.68 minutes (4 min run).

Preparation 149: N-[(6-fluoro-2-pyridyl)sulfonyl]-6-phenyl-2-(2,4,6-trimethylphenoxy)pyridine-3-carboxamide (Compound 698)

Step 1: Methyl 6-phenyl-2-(2,4,6-trimethylphenoxy)pyridine-3-carboxylate

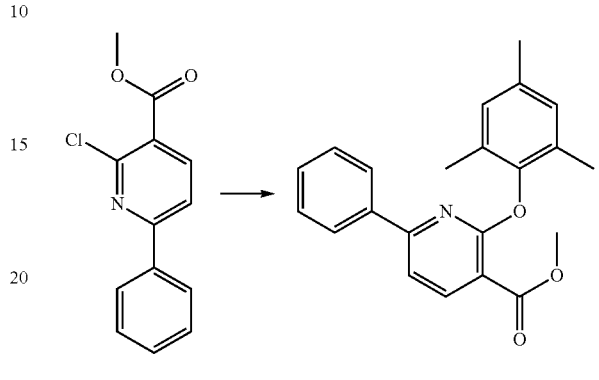

A mixture of methyl 2-chloro-6-phenyl-pyridine-3-carboxylate (224 mg, 0.904 mmol), 2,4,6-trimethylphenol (123 mg, 0.904 mmol), cesium carbonate (295 mg, 0.904 mmol) and DMF (3.14 mL) was heated at 80° C. overnight. The reaction mixture was cooled to room temperature before partitioned between ethyl acetate and 1N HCl. The layers were separated and the aqueous layer was extracted with ethyl acetate (2×). The combined organics were washed with brine, dried over magnesium sulfate, filtered and concentrated under reduced pressure. The residue was subjected to column chromatography (0-25% ethyl acetate/hexanes) to give methyl 6-phenyl-2-(2,4,6-trimethylphenoxy)pyridine-3-carboxylate (250 mg, 71%). ESI-MS m/z calc. 347.15213, found 348.4 (M+1)+; Retention time: 2.28 minutes (3 min run).

Step 2: 6-phenyl-2-(2,4,6-trimethylphenoxy)pyridine-3-carboxylic acid

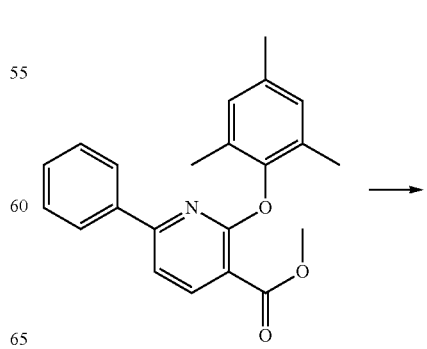

-continued

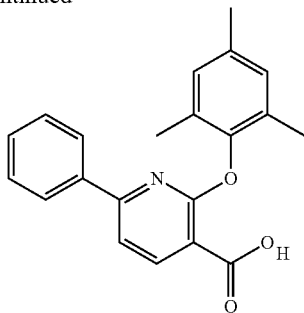

Methyl 6-phenyl-2-(2,4,6-trimethylphenoxy)pyridine-3-carboxylate (562 mg, 1.62 mmol) was dissolved in methanol (8 mL): THF (3 mL) and NaOH (8.09 mL of 1 M, 8.09 mmol) was added. The reaction mixture was heated at 65° C. for 3 h. The reaction mixture was poured over ice and acidified with 6M HCl. The resulting white solid was collected and then dissolved in methanol and evaporated under reduced pressure to give 6-phenyl-2-(2,4,6-trimethylphenoxy)pyridine-3-carboxylic acid (466 mg, 86%) ESI-MS m/z calc. 333.1365, found 334.2 (M+1)$^+$; Retention time: 0.74 minutes.

Step 3: N-[(6-fluoro-2-pyridyl)sulfonyl]-6-phenyl-2-(2,4,6-trimethylphenoxy)pyridine-3-carboxamide (Compound 698)

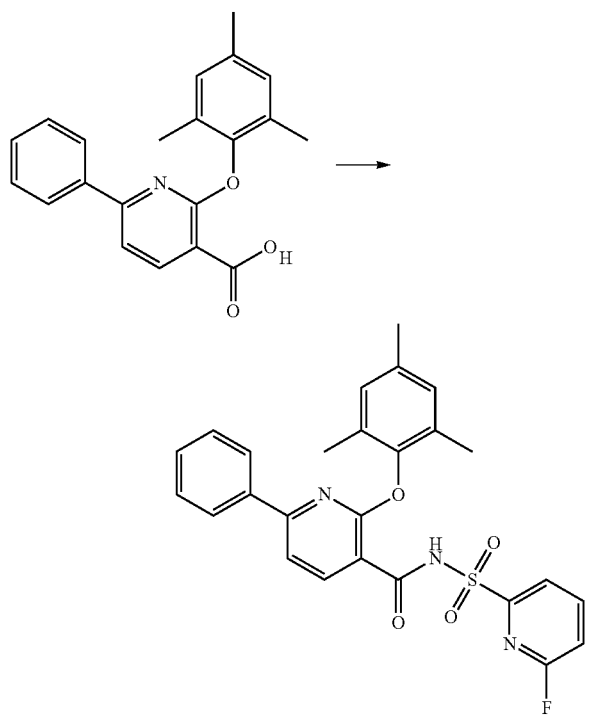

To 6-phenyl-2-(2,4,6-trimethylphenoxy)pyridine-3-carboxylic acid (150 mg, 0.450 mmol), HATU (171 mg, 0.450 mmol), DMF (1.5 mL), and triethylamine (137 mg, 188 µL, 1.35 mmol) was added 6-fluoropyridine-2-sulfonamide (79.3 mg, 0.450 mmol) was added and the reaction mixture was allowed to stir at 65° C. for 1 h. The reaction mixture was filtered and purified via HPLC (1%-99%) ACN:H$_2$O with a 0.1% HCl modifier to give N-[(6-fluoro-2-pyridyl)sulfonyl]-6-phenyl-2-(2,4,6-trimethylphenoxy)pyridine-3-carboxamide (Compound 698) (79 mg, 36%) 1H NMR (400 MHz, DMSO-d$_6$) δ 8.37 (q, J=7.8 Hz, 1H), 8.16 (dd, J=7.5, 2.1 Hz, 1H), 8.12 (d, J=7.8 Hz, 1H), 7.80-7.73 (m, 3H), 7.59 (dd, J=8.3, 2.2 Hz, 1H), 7.41 (ddt, J=5.5, 3.8, 2.2 Hz, 3H), 6.94 (s, 2H), 2.28 (s, 3H), 2.01 (s, 6H). ESI-MS m/z calc. 491.1315, found 492.4 (M+1)$^+$; Retention time: 2.19 minutes.

Preparation 150: (S)-2,2-dimethyl-4-(methyl-d$_3$) pyrrolidine-3,3-d$_2$

Step 1: Methyl-d$_3$ 4-methyl-2-(methyl-d$_3$)-4-nitropentanoate-3,3-d$_2$

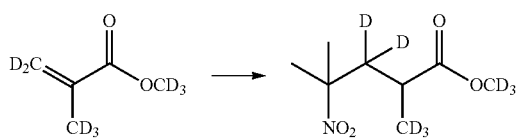

A 500-mL, three-neck round bottom flask equipped with a magnetic stir bar, a nitrogen line and a J-Kern thermocouple with heating mantle was charged with 2-nitropropane (34.3 g, 385 mmol) and d$_8$-methyl methacrylate (50 g, 462 mmol) was stirred at ambient temperature when 1,8-diazabicyclo[5.4.0]undec-7-ene (1.47 g, 9.63 mmol) was added in one portion. The reaction solution exothermed from 20 to ~40° C. and was allowed to stir without heating or cooling for 16 h. The reaction mixture was heated at 80° C. for 4 h. The reaction mixture was diluted with MTBE (170 mL), washed with 1 M HCl (15 mL), dried (MgSO$_4$), filtered and concentrated under reduced pressure to afford methyl-d$_3$ 4-methyl-2-(methyl-d$_3$)-4-nitropentanoate-3,3-d$_2$ as light yellow oil (75 g, 99%), which was used in the next step without further purification.

Step 2: Methyl-d$_3$ (S)-4-methyl-2-(methyl-d$_3$)-4-nitropentanoate-3,3-d$_2$

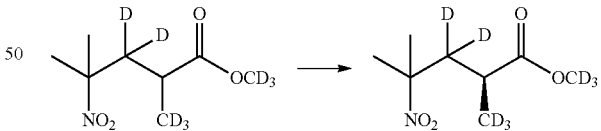

A 5-L, three-neck round bottom flask equipped an overhead mechanical stirrer, a nitrogen line and a J-Kern thermocouple with heating mantle was charged with methyl-d$_3$ 4-methyl-2-(methyl-d$_3$)-4-nitropentanoate-3,3-d$_2$ (75 g, 380 mmol) and pH 7.5 Na-phosphate buffer @ 0.8 M (2000 mL). To this was added lipase from *Rhizomucor miehei* (sigma L4277, palatase from Novozymes) (37.5 mL) and stirred at 30° C. for 25 h. The reaction mixture was extracted twice with MTBE (1 L each time). The combined organics were washed with NaHCO$_3$ (5 vol) twice, brine (5 vol), dried over sodium sulfate and concentrated in vacuo to afford methyl-d$_3$ (S)-4-methyl-2-(methyl-d$_3$)-4-nitropentanoate-3,3-d$_2$ as pale yellow oil (32.5 g, 43% yield).

Step 3: (S)-5,5-dimethyl-3-(methyl-d₃)pyrrolidin-2-one-4,4-d₂

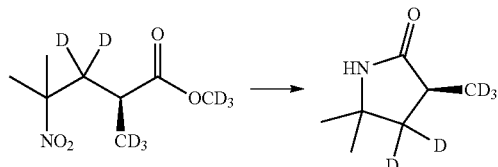

A high-pressure vessel (Parr shaker bottle, 500 mL) was purged with and maintained under N2. The vessel was charged sequentially with DI water-rinsed (3×) damp Raney®2800 Ni (6.1 g), methyl-d₃ (S)-4-methyl-2-(methyl-d₃)-4-nitropentanoate-3,3-d₂ (32.5 g, 165 mmol) and EtOH (290 mL). The vessel was sealed and evacuated/backfilled with N2 (3×). With no stirring, the vessel was then evacuated and backfilled with H₂ (30 psi). The Parr bottle was shaken while heating the reaction mixture at 60° C., and the H₂ pressure was maintained at 30 psi for 8 hours. The vessel was evacuated/backfilled with N2 (3×) and the catalyst/Celite were removed by vacuum filtration (Celite pad; N2 blanket). The flask/filter-pad was washed with EtOH (3×50 mL). The filtrate and washes were combined and concentrated in vacuo to afford (S)-5,5-dimethyl-3-(methyl-d₃)pyrrolidin-2-one-4,4-d₂ (20 g, 92%) as white solid.

Step 4: (S)-2,2-dimethyl-4-(methyl-d₃)pyrrolidine-3,3-d₂

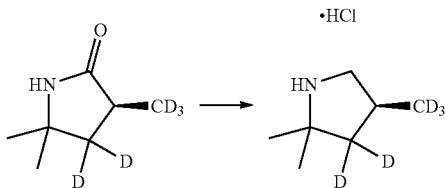

A 1-L, three-neck round bottom flask equipped an overhead mechanical stirrer, a nitrogen line and a J-Kern thermocouple was charged with LAH pellets (7.6 g, 202 mmol) in THF (80 mL). A solution of (S)-5,5-dimethyl-3-(methyl-d₃)pyrrolidin-2-one-4,4-d₂ (20 g, 151 mmol) in THF (120 mL) was added to the suspension over 30 minutes while allowing the reaction temperature to rise to ~60° C. The reaction temperature was increased to near reflux (~68° C.) and maintained for 16 h. The reaction mixture was cooled to below 40° C. and diluted with MTBE (200 mL). The reaction mixture was quenched carefully with drop-wise addition of a saturated aqueous solution of Na₂SO₄ (1 vol) over 2 h. After the addition was completed, the reaction mixture was cooled to RT. The solid was removed by filtration (Celite pad) and washed with EtOAc (4 vol). With external cooling and N2 blanket, the filtrate and washings were combined and treated with drop-wise addition of anhydrous 4 M HCl in dioxane (1 equiv.) while maintaining the temperature below 20° C. After the addition was completed (20 min), the resultant suspension was concentrated under reduced pressure at 45° C. The suspension was backfilled with heptanes (4 vol) twice during concentration. The suspension was cooled to below 30° C. when the solid was collected by filtration under a N2 blanket. The solid was dried under high vacuum at 45° C. to afford (S)-2,2-dimethyl-4-(methyl-d₃)pyrrolidine-3,3-d₂ (17.5 g, 75%) as a white, crystalline solid.

Preparation 151: (6-((propan-2-yl-d₇)oxy)pyridin-3-yl)boronic acid

Step 1: 5-bromo-2-((propan-2-yl-d₇)oxy)pyridine

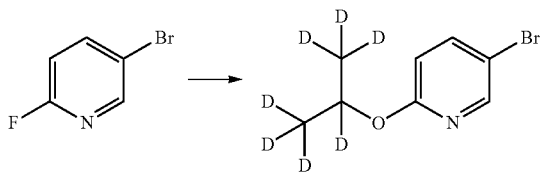 [SMILES: Fc1ccc(Br)cn1 ; [2H]C([2H])([2H])C([2H])(Oc1ccc(Br)cn1)C([2H])([2H])[2H]]

To NaH (245 g, 10.2 mmol) slurried in DMF (7 mL) was added d₇-IPA (610 mg, 9.09 mmol) and the reaction mixture was stirred for 30 min at room temperature. 5-bromo-2-fluoropyridine (1.00 g, 5.68 mmol) was added and the reaction mixture was heated to 120° C. for 2.5 h, then an additional aliquot of NaH (40 mg) and d₇-IPA (0.07 mL) was added. After a further 2 h of heating, the reaction mixture was allowed to cool to room temperature. Water (21 mL), followed by MTBE (14 mL) was added, and after stirring, the layers were separated. The organic layer was washed with water (14 mL), dried over sodium sulfate, filtered and concentrated to give 5-bromo-2-((propan-2-yl-d₇)oxy)pyridine. 1H NMR (400 mHz) δ 8.17 (m, 1H), 7.60 (dd, J=8.8, 2.6 Hz, 1H), 6.58 (dd, J=8.8, 0.7 Hz, 1H).

Step 2: (6-((propan-2-yl-d₇)oxy)pyridin-3-yl)boronic acid

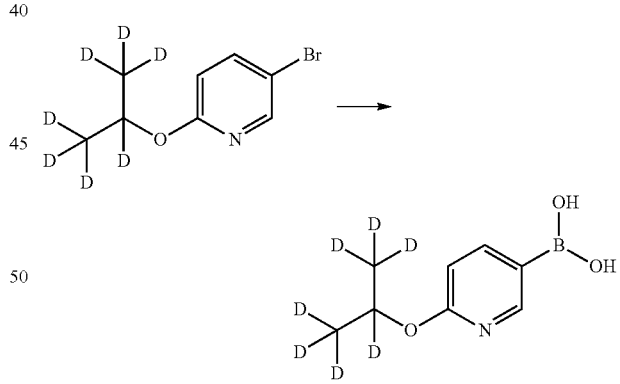

A mixture of 5-bromo-2-[1,2,2,2-tetradeuterio-1-(trideuteriomethyl)ethoxy]pyridine (1.24 g, 5.00 mmol), bis(pinacolato)diboron (1.52 g, 6.00 mmol), KOAc (1.47 g, 15.0 mmol), Pd(OAc)₂ (44.9 mg, 0.20 mmol), X-Phos (119 mg, 0.25 mmol) in 2-MeTHF (11 mL) was heated to 80° C. for 2.5 h under an atmosphere of nitrogen. The reaction mixture was allowed to cool, then water (8 mL) was added and the reaction mixture was filtered through Celite pad washing with 2-MeTHF (2×5 mL). The layers were separated and the organic layer dried over sodium sulfate, filtered, and concentrated under reduced pressure. The crude material was dissolved in 2-MeTHF (12 mL), 10% aq w/v NaOH was added and the reaction mixture was stirred. The layers were separated, the aqueous layer was acidified to pH 5 with conc HCl and stirred with 2-MeTHF (12 mL), then separated, the organic layer dried over sodium sulfate, filtered and concentrated under reduced pressure to give (6-((propan-2-yl-d₇)oxy)pyridin-3-yl)boronic acid.

Preparation 152: N-[(6-amino-2-pyridyl)sulfonyl]-6-[3-fluoro-5-[2,3,3,3-tetradeuterio-2-(trideuteriomethyl)propoxy]phenyl]-2-[(4S)-2,2,4-trimethylpyrrolidin-1-yl]pyridine-3-carboxamide (Compound 2708)

Step 1: 1-bromo-3-fluoro-5-[2,3,3,3-tetradeuterio-2-(trideuteriomethyl)propoxy]benzene

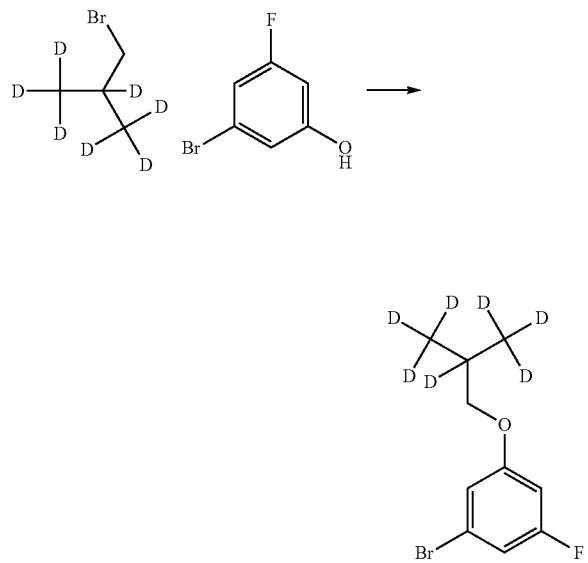

To 3-bromo-5-fluoro-phenol (6.00 g, 31.41 mmol) in DMF (60 mL) was slowly added NaH (1.38 g, 34.55 mmol) and the reaction mixture was stirred at ambient temperature for 15 min. To the mixture was added NaI (1.18 g, 7.85 mmol), followed 2-(bromomethyl)-1,1,1,2,3,3,3-heptadeuterio-propane (5.05 g, 34.55 mmol). The reaction mixture was stirred at 80° C. for 6 h. The reaction mixture was cooled to ambient temperature and slowly quenched with water (120 mL). The reaction mixture was extracted with EtOAc (240 mL) and the organic phase separated. The organic phase was washed with brine, dried over MgSO₄, filtered and concentrated in vacuo. The crude light yellow oil was purified by silica gel column chromatography eluting with 0-100% EtOAc/hexanes to give 1-bromo-3-fluoro-5-[2,3,3,3-tetradeuterio-2-(trideuteriomethyl)propoxy]benzene (6.8 g, 85%). 1H NMR (400 MHz, Chloroform-d) δ 6.90-6.77 (m, 2H), 6.55 (dt, J=10.7, 2.2 Hz, 1H), 3.75-3.61 (m, 2H).

Step 2: 2-[3-fluoro-5-[2,3,3,3-tetradeuterio-2-(trideuteriomethyl)propoxy]phenyl]-4,4,5,5-tetramethyl-1,3,2-dioxaborolane

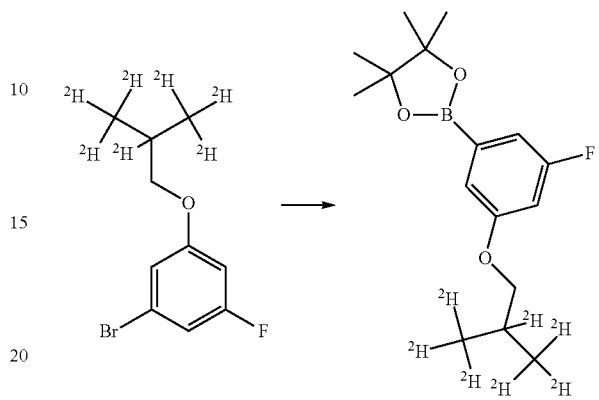

To the 1-bromo-3-fluoro-5-[2,3,3,3-tetradeuteriomethyl)propoxy]benzene (10.8 g, 42.50 mmol) in dioxane (162 mL) was added bis(dipinacolato)diboron (16.2 g, 63.75 mmol) and KOAc (12.5 g, 127.5 mmol) and the reaction mixture was purged with N2 for 20 min. To the reaction mixture was added PdCl₂(dppf)₂·CH₂Cl₂ (1.74 g, 2.13 mmol) and the reaction mixture was heated to 100° C. for 3 h. The reaction mixture was cooled to ambient temperature and filtered through celite and concentrated in vacuo affording a dark oil. The material was purified using silica gel column chromatography eluting with 0-100% EtOAc/hexanes to give 2-[3-fluoro-5-[2,3,3,3-tetradeuterio-2-(trideuteriomethyl)propoxy]phenyl]-4,4,5,5-tetramethyl-1,3,2-dioxaborolane (8.92 g, 70%). 1H NMR (400 MHz, DMSO-d₆) δ 6.99 (dd, J=2.4, 0.8 Hz, 1H), 6.96-6.87 (m, 2H), 3.76 (s, 2H), 1.29 (s, 12H).

Step 3: N-[(6-amino-2-pyridyl)sulfonyl]-6-[3-fluoro-5-[2,3,3,3-tetradeuterio-2-(trideuteriomethyl)propoxy]phenyl]-2-[(4S)-2,2,4-trimethylpyrrolidin-1-yl]pyridine-3-carboxamide (Compound 2708)

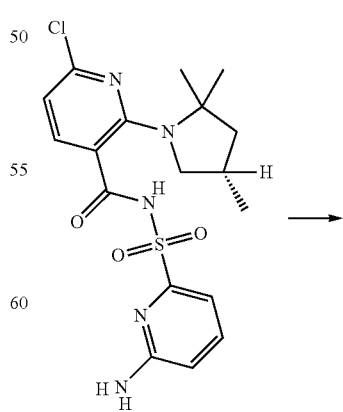

-continued

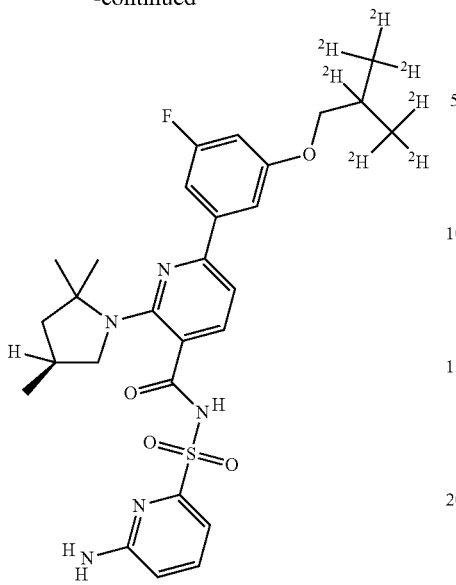

To N-[(6-amino-2-pyridyl)sulfonyl]-6-chloro-2-[(4S)-2,2,4-trimethylpyrrolidin-1-yl]pyridine-3-carboxamide (Compound 852) (1.4 g, 3.3 mmol) in 1-propanol (14 mL) and water (4.2 mL) was slowly added K$_2$CO$_3$ (1.4 g, 9.9 mmol), followed by 1,3-bis(2,6-diisopropylphenyl)imidazolidin-2-ide; 3-chloropyridine; palladium(2+); dichloride (45 mg, 0.06 mmol) and the reaction mixture was heated to 80° C. To the reaction mixture was slowly added 2-[3-fluoro-5-[2,3,3,3-tetradeuterio-2-(trideuteriomethyl)propoxy]phenyl]-4,4,5,5-tetramethyl-1,3,2-dioxaborolane (1.2 g, 4.1 mmol) in 1-propanol (2.8 mL). The reaction mixture was stirred at 80° C. for 19 h. The reaction mixture was cooled to ambient temperature and slowly added to water (80 mL) containing HCl (20 mL of 1 M, 19.8 mmol). The reaction mixture was diluted with EtOAc (100 mL) and the organic phase separated. The organic phase was washed with brine, dried over MgSO$_4$, filtered over celite and concentrated in vacuo. The crude product was purified by silica gel column chromatography eluting with 0-10% MeOH/DCM, then by reverse phase column chromatography eluting with 5-100% ACN/Water to give N-[(6-amino-2-pyridyl)sulfonyl]-6-[3-fluoro-5-[2,3,3,3-tetradeuterio-2-(trideuteriomethyl)propoxy]phenyl]-2-[(4S)-2,2,4-trimethylpyrrolidin-1-yl]pyridine-3-carboxamide (Compound 2708) (495 mg, 27%). 1H NMR (400 MHz, DMSO-d$_6$) δ 12.46 (s, 1H), 7.78 (d, J=8.0 Hz, 1H), 7.63 (dd, J=8.4, 7.3 Hz, 1H), 7.53-7.45 (m, 1H), 7.40 (dt, J=10.0, 2.0 Hz, 1H), 7.26 (d, J=8.0 Hz, 1H), 7.20 (d, J=7.3 Hz, 11H), 6.89 (dt, J=10.7, 2.3 Hz, 1H), 6.68 (d, J=8.4 Hz, 1H), 6.49 (s, 2H), 3.83 (s, 2H), 2.76-2.54 (m, 3H), 2.22 (s, 1H), 1.88 (dd, J=11.9, 5.7 Hz, 1H), 1.60 (d, J=5.7 Hz, 6H), 1.42 (t, J=12.1 Hz, 1H), 0.88 (d, J=6.2 Hz, 3H). ESI-MS m/z calc. 562.2755, found 563.36 (M+1)$^+$; Retention time: 2.73 minutes.

The following compound can be synthesized using the procedures described herein:
N-(benzenesulfonyl)-6-[3-fluoro-5-[2,3,3,3-tetradeuterio-2-(trideuteriomethyl)propoxy]phenyl]-2-[(4S)-2,2,4-trimethylpyrrolidin-1-yl]pyridine-3-carboxamide (Compound 2713).

Preparation 153: 5-tert-butyl-N-(2-cyanophenyl)sulfonyl-2-[(2,4,6-trimethylphenyl)methyl]pyrazole-3-carboxamide (Compound 266)

Step 1: Ethyl 3-(tert-butyl)-1-(2,4,6-trimethylbenzyl)-1H-pyrazole-5-carboxylate

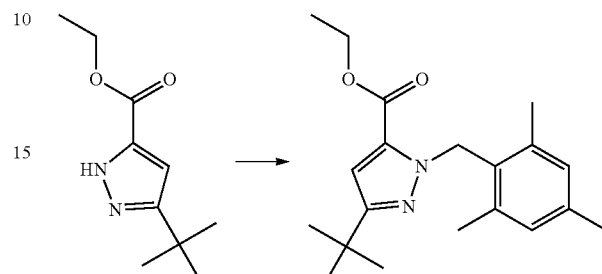

A mixture of ethyl 5-tert-butyl-4H-pyrazole-3-carboxylate (0.5 g, 2.5 mmol), 2-(bromomethyl)-1,3,5-trimethyl-benzene (0.5 g, 2.5 mmol), and K$_2$CO$_3$ (0.7 g, 5.1 mmol) in DMF (5 mL) was heated to 80° C. overnight. A further aliquot of 2-(bromomethyl)-1,3,5-trimethyl-benzene (200 mg) and K$_2$CO$_3$ (0.7 g, 5.1 mmol) were added and the temperature was increased to 85° C. The reaction mixture was heated overnight. The reaction mixture was cooled, water (20 ml) was added and extracted with ethyl acetate (2×50 ml). The organic layers were dried over Na$_2$SO$_4$, concentrated in vacuo, and purified by silica gel column chromatography.

Step 2: 5-tert-butyl-2-[(2,4,6-trimethylphenyl)methyl]pyrazole-3-carboxylic acid

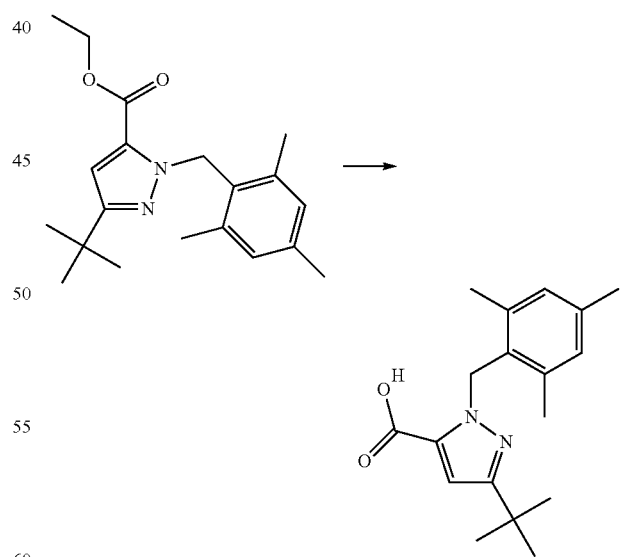

A solution of ethyl 5-tert-butyl-2-[(2,4,6-trimethylphenyl)methyl]pyrazole-3-carboxylate (2.0 g, 6.0 mmol) and sodium hydroxide (1.9 g, 48 mmol) in THF (10 mL) and water (10 mL) was stirred at 60° C. for 17 hours. The reaction mixture was cooled to room temperature and acidified with 1 M hydrochloric acid. The white precipitate was filtered, washed with water, and dried under vacuum to give 5-tert-butyl-2-[(2,4,6-trimethylphenyl)methyl]pyrazole-3-carboxylic acid (1.7 g, 96%) as a white powder. 1H NMR (400 MHz, DMSO) δ 6.92-6.77 (m, 2H), 6.67 (s, 1H), 5.63 (s, 2H), 2.25 (dd, J=23.8, 13.5 Hz, 9H), 1.13 (d, J=10.4 Hz, 9H). ESI-MS m/z calc. 300.18378, found 301.0 (M+1)⁺; Retention time: 2.06 minutes.

Step 3: 5-tert-butyl-N-(2-cyanophenyl)sulfonyl-2-[(2,4,6-trimethylphenyl)methyl]pyrazole-3-carboxamide (Compound 266)

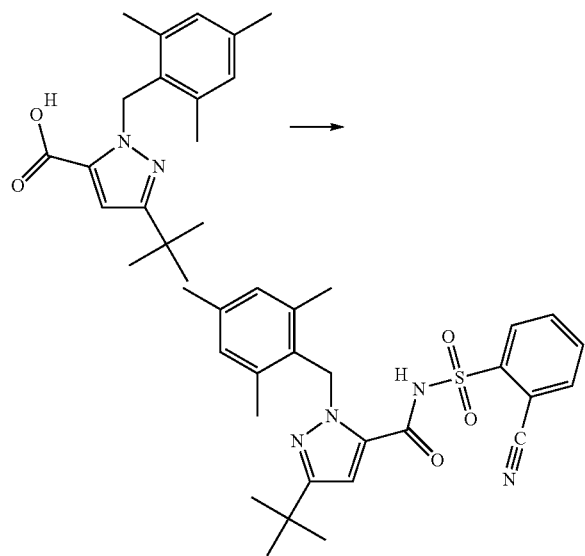

5-tert-butyl-2-[(2,4,6-trimethylphenyl)methyl]pyrazole-3-carboxylic acid (30 mg, 0.1 mmol), 2-cyanobenzenesulfonamide (18 mg, 0.1 mmol), HATU (38 mg, 0.1 mmol) and DIEA (39 mg, 52 µL, 0.3 mmol) were combined in DMF (1.5 mL) and heated at 60° C. for 16 h. The reaction mixture was filtered and purified by HPLC/MS utilizing a gradient of 1-99% acetonitrile in 5 mM aq HCl to yield 5-tert-butyl-N-(2-cyanophenyl)sulfonyl-2-[(2,4,6-trimethylphenyl)methyl]pyrazole-3-carboxamide (Compound 266) (11 mg, 24%) 1H NMR (400 MHz, DMSO-d₆) δ 8.22 (dd, J=7.9, 1.3 Hz, 1H), 8.12 (dd, J=7.6, 1.4 Hz, 1H), 7.97 (td, J=7.8, 1.5 Hz, 1H), 7.90 (td, J=7.6, 1.3 Hz, 1H), 7.00 (s, 1H), 6.74 (s, 2H), 5.43 (s, 2H), 2.17 (s, 3H), 2.06 (s, 6H), 1.16 (s, 9H). ESI-MS m/z calc. 464.1882, found 465.4 (M+1)⁺; Retention time: 2.29 minutes.

The following compounds can be synthesized using the procedures described herein:
N-(benzenesulfonyl)-5-tert-butyl-2-[1-(2,4,6-trimethylphenyl)ethyl]pyrazole-3-carboxamide (Compound 201),
N-(benzenesulfonyl)-5-tert-butyl-2-[[2-fluoro-5-(trifluoromethyl)phenyl]methyl]pyrazole-3-carboxamide (Compound 35),
5-tert-butyl-N-[3-(dimethylamino)phenyl]sulfonyl-2-[(2,4,6-trimethylphenyl)methyl]pyrazole-3-carboxamide (Compound 270),
N-(3-aminophenyl)sulfonyl-5-tert-butyl-2-[(2,4,6-trichlorophenyl)methyl]pyrazole-3-carboxamide (Compound 303),
N-(3-aminophenyl)sulfonyl-5-tert-butyl-2-[(4-tert-butyl-2,6-dimethyl-phenyl)methyl]pyrazole-3-carboxamide (Compound 156),
N-(benzenesulfonyl)-5-[4-(difluoromethyl)phenyl]-2-[(2,6-dimethylphenyl)methyl]pyrazole-3-carboxamide (Compound 119),
N-(3-aminophenyl)sulfonyl-5-tert-butyl-2-[[2-chloro-6-(trifluoromethyl)phenyl]methyl]pyrazole-3-carboxamide (Compound 189),
5-tert-butyl-N-[3-(dimethylamino)-2-methyl-phenyl]sulfonyl-2-[(2,4,6-trimethylphenyl)methyl]pyrazole-3-carboxamide (Compound 104),
N-(3-amino-2-methyl-phenyl)sulfonyl-5-tert-butyl-2-[(2,4,6-trimethylphenyl)methyl]pyrazole-3-carboxamide (Compound 123),
5-tert-butyl-N-(1-methylindol-7-yl)sulfonyl-2-[[2-methyl-3-(trifluoromethyl)phenyl]methyl]pyrazole-3-carboxamide (Compound 276),
5-tert-butyl-N-(m-tolylsulfonyl)-2-[(2,4,6-trimethylphenyl)methyl]pyrazole-3-carboxamide (Compound 80),
5-tert-butyl-N-(5-quinolylsulfonyl)-2-[(2,4,6-trimethylphenyl)methyl]pyrazole-3-carboxamide (Compound 352),
N-(3-aminophenyl)sulfonyl-5-tert-butyl-2-[(2,3,5,6-tetramethylphenyl)methyl]pyrazole-3-carboxamide (Compound 317),
5-tert-butyl-2-[(2,6-dimethylphenyl)methyl]-N-(2-thienylsulfonyl)pyrazole-3-carboxamide (Compound 77),
N-(benzenesulfonyl)-5-tert-butyl-2-[(2,4,6-trichlorophenyl)methyl]pyrazole-3-carboxamide (Compound 145),
5-tert-butyl-2-[(2,6-dimethylphenyl)methyl]-N-(2-methoxy-3-methyl-phenyl)sulfonyl-pyrazole-3-carboxamide (Compound 59),
N-(benzenesulfonyl)-5-tert-butyl-2-(1-naphthylmethyl)pyrazole-3-carboxamide (Compound 328),
5-tert-butyl-N-[3-(methylamino)phenyl]sulfonyl-2-[(2,4,6-trimethylphenyl)methyl]pyrazole-3-carboxamide (Compound 249),
5-tert-butyl-N-[1-(2-hydroxyethyl)indol-4-yl]sulfonyl-2-[(2,4,6-trimethylphenyl)methyl]pyrazole-3-carboxamide (Compound 188),
N-(3-aminophenyl)sulfonyl-5-tert-butyl-4-methyl-2-[(2,4,6-trimethylphenyl)methyl]pyrazole-3-carboxamide (Compound 20),
5-tert-butyl-N-(3-hydroxyphenyl)sulfonyl-2-[(2,4,6-trimethylphenyl)methyl]pyrazole-3-carboxamide (Compound 84),
5-tert-butyl-N-(1-methylimidazol-4-yl)sulfonyl-2-[(2,4,6-trimethylphenyl)methyl]pyrazole-3-carboxamide (Compound 1568),
N-(benzenesulfonyl)-5-tert-butyl-2-[(3-pyrrol-1-ylphenyl)methyl]pyrazole-3-carboxamide (Compound 108),
5-tert-butyl-N-(1H-indol-4-ylsulfonyl)-2-[[2-methyl-3-(trifluoromethyl)phenyl]methyl]pyrazole-3-carboxamide (Compound 60),
N-(3-acetylphenyl)sulfonyl-5-tert-butyl-2-[(2,4,6-trimethylphenyl)methyl]pyrazole-3-carboxamide (Compound 332),
N-(benzenesulfonyl)-5-tert-butyl-2-[[5-methyl-2-(trifluoromethyl)phenyl]methyl]pyrazole-3-carboxamide (Compound 304),
N-(3-aminophenyl)sulfonyl-5-tert-butyl-2-[[2-fluoro-6-(trifluoromethyl)phenyl]methyl]pyrazole-3-carboxamide (Compound 239),
N-(3-aminophenyl)sulfonyl-5-tert-butyl-2-[1-(o-tolyl)ethyl]pyrazole-3-carboxamide (Compound 342),
N-[(6-amino-2-pyridyl)sulfonyl]-5-tert-butyl-4-methyl-2-[(2,4,6-trimethylphenyl)methyl]pyrazole-3-carboxamide (Compound 356),
N-(3-aminophenyl)sulfonyl-5-tert-butyl-2-(1-cyclohexylethyl)pyrazole-3-carboxamide (Compound 287), N-(3-aminophenyl)sulfonyl-5-tert-butyl-2-(1-phenylpropyl)pyrazole-3-carboxamide (Compound 165),
5-tert-butyl-N-(4-hydroxyphenyl)sulfonyl-2-[(2,4,6-trimethylphenyl)methyl]pyrazole-3-carboxamide (Compound 269),
N-(3-aminophenyl)sulfonyl-5-(1-methylcyclopropyl)-2-[(2,4,6-trimethylphenyl)methyl]pyrazole-3-carboxamide (Compound 158),
N-(benzenesulfonyl)-5-tert-butyl-2-[[2-methyl-3-(trifluoromethyl)phenyl]methyl]pyrazole-3-carboxamide (Compound 98),
N-(3-aminophenyl)sulfonyl-5-tert-butyl-2-[(2,6-dimethylphenyl)methyl]pyrazole-3-carboxamide (Compound 185),
N-(3-aminophenyl)sulfonyl-5-isobutyl-2-[(2,4,6-trimethylphenyl)methyl]pyrazole-3-carboxamide (Compound 167),
N-[(6-amino-2-pyridyl)sulfonyl]-5-tert-butyl-2-[(2,4,6-trimethylphenyl)methyl]pyrazole-3-carboxamide (Compound 173),
N-(benzenesulfonyl)-5-tert-butyl-2-[2-(2-methoxyphenyl)ethyl]pyrazole-3-carboxamide (Compound 157),
5-tert-butyl-N-[(3-methoxy-2-pyridyl)sulfonyl]-2-[(2,4,6-trimethylphenyl)methyl]pyrazole-3-carboxamide (Compound 44),
N-(3-aminophenyl)sulfonyl-5-tert-butyl-2-(1-naphthylmethyl)pyrazole-3-carboxamide (Compound 295),
5-tert-butyl-2-[(2,6-dimethylphenyl)methyl]-N-(2-fluorophenyl)sulfonyl-pyrazole-3-carboxamide (Compound 57),
N-(4-aminophenyl)sulfonyl-5-tert-butyl-2-[(2,6-dimethylphenyl)methyl]pyrazole-3-carboxamide (Compound 81),
5-tert-butyl-2-[(2,6-dimethylphenyl)methyl]-N-(1H-indazol-4-ylsulfonyl)pyrazole-3-carboxamide (Compound 86),
N-(3-amino-4-fluoro-phenyl)sulfonyl-5-tert-butyl-2-[(2,6-dimethylphenyl)methyl]pyrazole-3-carboxamide (Compound 150),
5-tert-butyl-N-(2,6-difluorophenyl)sulfonyl-2-[(2,6-dimethylphenyl)methyl]pyrazole-3-carboxamide (Compound 170),
5-tert-butyl-2-[(2,6-dimethylphenyl)methyl]-N-(1-methylindol-4-yl)sulfonyl-pyrazole-3-carboxamide (Compound 210),
5-tert-butyl-N-(2,3-dihydrobenzofuran-7-ylsulfonyl)-2-[(2,6-dimethylphenyl)methyl]pyrazole-3-carboxamide (Compound 211),
N-(benzenesulfonyl)-5-tert-butyl-2-[(2,6-dimethylphenyl)methyl]pyrazole-3-carboxamide (Compound 257),
N-(3-amino-4-methyl-phenyl)sulfonyl-5-tert-butyl-2-[(2,6-dimethylphenyl)methyl]pyrazole-3-carboxamide (Compound 312) and
N-(3-aminophenyl)sulfonyl-1-[(2,4,6-trimethylphenyl)methyl]benzimidazole-2-carboxamide (Compound 71).

Preparation 154:
(3S)-3,5,5-trimethylpyrrolidin-2-one

Step 1: Methyl-2,4-dimethyl-4-nitro-pentanoate

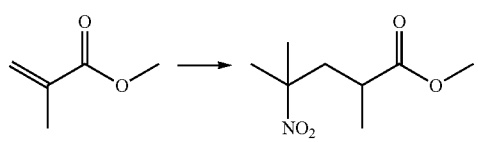

THF (4.5 L) was added to a 20 L glass reactor and stirred under an atmosphere of nitrogen at room temperature. 2-Nitropropane (1.5 kg) and DBU (1.282 kg, 0.5 equiv.) were then charged to the reactor (immediate yellow color observed) and the jacket temperature was increased to 50° C. Once the reactor contents were close to 50° C., methyl methacrylate (1.854 kg, 1.1 equiv.) was added slowly over 100 minutes. The reaction temperature was maintained at or close to 50° C. with reaction completion reached at 21 h. During the course of the reaction, a color change from yellow to deep green was observed. The reaction mixture was concentrated in vacuo then transferred back to the reactor and diluted with MTBE (14 L). 2 M HCl (7.5 L) was added and this was stirred for 5 minutes then allowed to settle. Two clear layers were visible—a lower yellow aqueous phase and an upper green organic phase. The aqueous was removed and the organic was stirred again with 2 M HCl (3 L). After separation, the HCl washes were recombined and stirred with MTBE (3 L) for 5 minutes. The aqueous was removed and all of the organics were combined in the reactor and stirred with water (3 L) for 5 minutes. After separation, the organics were concentrated in vacuo to afford a cloudy green mobile oil which was dried with MgSO$_4$ and filtered to afford racemic methyl-2,4-dimethyl-4-nitro-pentanoate (3.16 kg) as a clear green mobile oil (99% yield). $^1$H NMR (400 MHz, Chloroform-d) δ 3.68 (s, 3H), 2.56-2.35 (m, 2H), 2.11-2.00 (m, 1H), 1.56 (d, J=20.2 Hz, 6H), 1.19 (d, J=6.8 Hz, 3H).

Step 2: Methyl (2S)-2,4-dimethyl-4-nitro-pentanoate

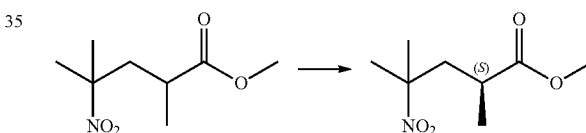

A reaction vessel was set up with methyl 2,4-dimethyl-4-nitro-pentanoate (7 kg, 105.7 mmol) and stirred with 70 L of pH 6.5 K phosphate buffer @ 0.1 M. To this was added 3.5 L lipase (palatase from Novozymes) and stirred at 34° C. for ~43 h. The pH of the reaction was maintained at pH 6.5 by pH Stat dosing K$_2$CO$_3$ (aq. Soln). The reaction mixture was extracted with MTBE (2×5 vol, 1×2 vol). The combined MTBE layers were then washed with 2 M Na$_2$CO$_3$ (4×2.5 vol), water (3 vol) and brine (3 vol). The product was concentrated down to ~10 L in the reactor by distilling off the MTBE and transferred to a large rotary evaporator for final concentration to afford methyl (2S)-2,4-dimethyl-4-nitro-pentanoate as a mobile yellow oil (3072.2 g, 44% yield).

Step 3: (3S)-3,5,5-trimethylpyrrolidin-2-one

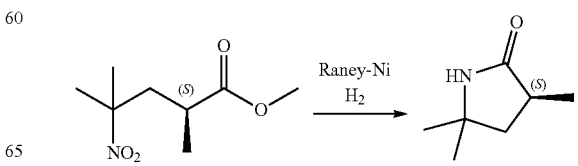

A 20 L Hastelloy reactor vessel, purged with and maintained under N2. The vessel was charged sequentially with DI water-rinsed, damp Raney® Ni (2800 grade, 250 g), methyl (2S)-2,4-dimethyl-4-nitro-pentanoate (1741 g, 9.2 mol) and ethanol (13.9 L, 8 vol). Stirring was commenced at 900 rpm and the reactor flushed with $H_2$ and maintained at ~2.5 bar. After 5 hours, the reaction mixture was filtered to remove Raney nickel and solid cake rinsed with ethanol (3.5 L, 2 vol). The ethanolic solution of product was concentrated in vacuo to reduce to a minimum volume of ethanol (~1.5 volumes), then heptane (2.5 L) was added and the suspension concentrated again to ~1.5 volumes. This was repeated a further 3 times, then the resulting suspension was cooled to 0-5° C. and filtered under suction and washed with heptane (2.5 L). The product was dried on the filter under vacuum for 20 minutes then transferred to drying trays and dried in a vacuum oven at 40° C. overnight (with N2 bleed). This afforded (3S)-3,5,5-trimethylpyrrolidin-2-one as a white crystalline solid (2.042 kg, 87%). $^1$H NMR (400 MHz, Chloroform-d) δ 6.39 (s, 1H), 2.62 (ddq, J=9.9, 8.6, 7.1 Hz, 1H), 2.17 (ddd, J=12.4, 8.6, 0.8 Hz, 1H), 1.56 (dd, J=12.5, 9.9 Hz, 1H), 1.31 (s, 3H), 1.25 (s, 3H), 1.20 (d, J=7.1 Hz, 3H).

Preparation 155: N-((2-aminopyridin-3-yl)sulfonyl)-6'-(((S)-1-hydroxypropan-2-yl)oxy)-6-((S)-2,2,4-trimethylpyrrolidin-1-yl)-[2,3'-bipyridine]-5-carboxamide (Compound 2690)

Step 1: N-[(2-amino-3-pyridyl)sulfonyl]-6-(6-fluoro-2-pyridyl)-2-[(4S)-2,2,4-trimethylpyrrolidin-1-yl]pyridine-3-carboxamide

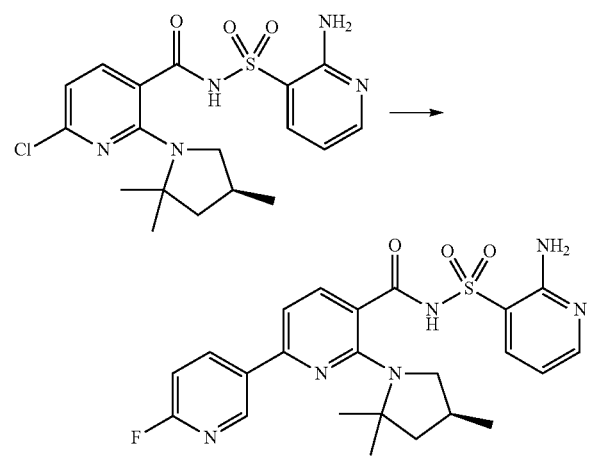

A mixture of N-[(2-amino-3-pyridyl)sulfonyl]-6-chloro-2-[(4S)-2,2,4-trimethylpyrrolidin-1-yl]pyridine-3-carboxamide (3.8 g, 8.96 mmol), (6-fluoro-2-pyridyl)boronic acid (2.00 g, 14.2 mmol), [1,1'-bis(diphenylphosphino)ferrocene]dichloropalladium(II) complex with dichloromethane (1.40 g, 2.32 mmol), and $Na_2CO_3$ (4.00 g, 37.7 mmol) in dimethylformamide (80-mL) and water (20 mL) was degassed under a stream of nitrogen and stirred at 100° C. for 18 hours. (6-Fluoro-2-pyridyl)boronic acid (0.90 g, 6.4 mmol), [1,1'-Bis(diphenylphosphino)ferrocene]dichloropalladium (II) complex with dichloromethane (0.40 g, 0.55 mmol) were added, and the reaction mixture stirred at 100° C. for another day. The reaction mixture was filtered through a pad of Celite and the filtrate was diluted with water (300 mL), adjusted to pH ~7 and extracted with ethyl acetate (5×300 mL). The extract was washed with brine (2×200 mL), dried over $Na_2SO_4$, and concentrated. The residue purified by chromatography on silica gel, eluted with 0-100% ethyl acetate in hexanes, affording yellow foam product (2.2 g, ~85% purity) and starting material (3) (560 mg).

Step 2: N-((2-aminopyridin-3-yl)sulfonyl)-6'-(((S)-1-(benzyloxy)propan-2-yl)oxy)-6-((S)-2,2,4-trimethyl-pyrrolidin-1-yl)-[2,3'-bipyridine]-5-carboxamide

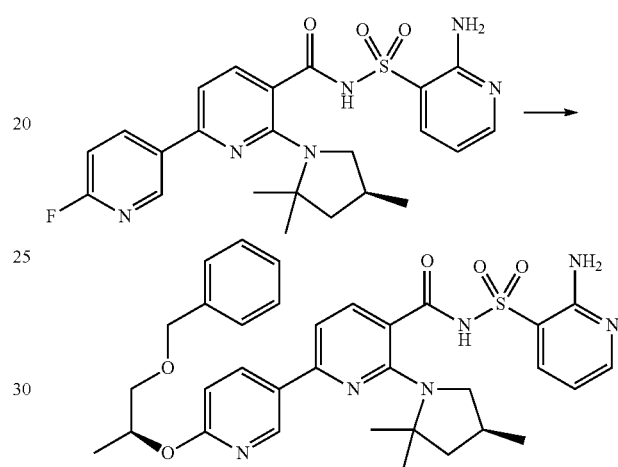

Sodium hydride (44 mg, 1.1 mmol) (60 wt % in mineral oil) was added to a solution of (R)-1-benzyloxy-propan-2-ol (117 mg, 0.7 mmol) in dimethylformamide (2.0 mL). After 5 minutes of stirring at room temperature, N-[(2-amino-3-pyridyl)sulfonyl]-6-(6-fluoro-2-pyridyl)-2-[(4S)-2,2,4-trimethylpyrrolidin-1-yl]pyridine-3-carboxamide (108 mg, 0.18 mmol) was added. The reaction mixture was heated under microwave irradiation at 75° C. for 30 minutes. The reaction mixture was quenched with water (10 mL), adjusted pH 3-4, and extracted with ethyl acetate (2×10 mL). The combined extract was washed with brine (2×5 mL), dried over $Na_2SO_4$ and concentrated under reduced pressure to give N-((2-aminopyridin-3-yl)sulfonyl)-6'-(((S)-1-(benzyloxy)propan-2-yl)oxy)-6-((S)-2,2,4-trimethyl-pyrrolidin-1-yl)-[2,3'-bipyridine]-5-carboxamide. ESI-MS m/z 631 (M+1)$^+$.

Step 3: N-((2-aminopyridin-3-yl)sulfonyl)-6'-(((S)-1-hydroxypropan-2-yl)oxy)-6-((S)-2,2,4-trimethylpyrrolidin-1-yl)-[2,3'-bipyridine]-5-carboxamide (Compound 2690)

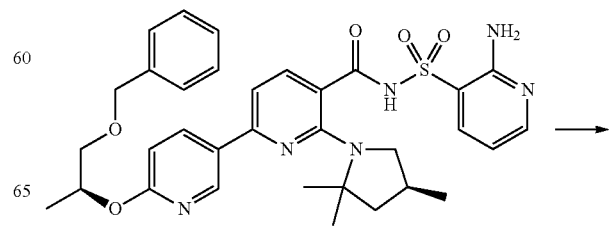

-continued

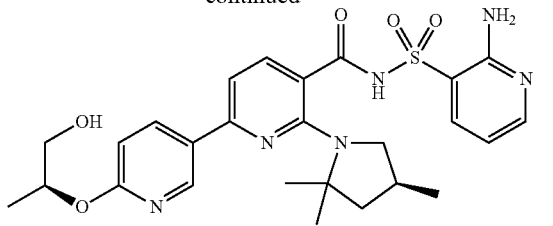

N-((2-aminopyridin-3-yl)sulfonyl)-6'-(((S)-1-(benzyloxy)propan-2-yl)oxy)-6-((S)-2,2,4-trimethyl-pyrrolidin-1-yl)-[2,3'-bipyridine]-5-carboxamide was hydrogenated under 1 atmosphere of hydrogen with Pd/C (10%, 260 mg) in methanol (25 mL) at room temperature. After 4 hours, the catalyst was removed by filtration, evaporated under reduced pressure and purified by silica gel column chromatography (0-10% of methanol in dichloromethane), followed by a further purification by silica gel column chromatography eluted with 0-8% of methanol in a mixture solvent of ethyl acetate and hexanes in a ratio of 50/50 to give N-((2-aminopyridin-3-yl)sulfonyl)-6'-(((S)-1-hydroxypropan-2-yl)oxy)-6-((S)-2,2,4-trimethylpyrrolidin-1-yl)-[2,3'-bipyridine]-5-carboxamide (Compound 2690) (9 mg). ESI-MS m/z 541 (M+1)+.

Preparation 156: Methyl 2-(benzenesulfonyl)-3-[5-tert-butyl-2-[(2,6-dimethylphenyl)methyl]pyrazol-3-yl]-3-oxo-propanoate (Compound 4)

Step 1: 5-tert-butyl-2-[(2,6-dimethylphenyl)methyl]pyrazole-3-carbonyl chloride

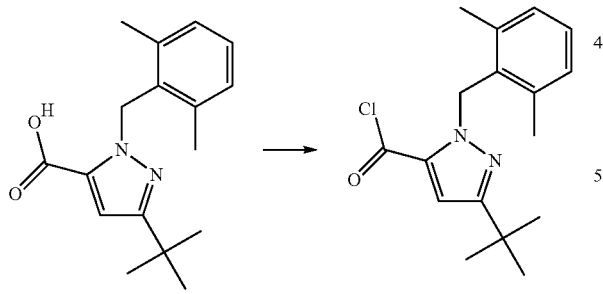

5-tert-butyl-2-[(2,6-dimethylphenyl)methyl]pyrazole-3-carboxylic acid (100 mg, 0.3492 mmol) was dissolved in thionyl chloride (41.54 mg, 25.47 µL, 0.3492 mmol) and a drop of DMF was added. The reaction was stirred for 1 h and evaporated to give the acid chloride, which was used without further purification.

Step 2: Methyl 2-(benzenesulfonyl)-3-[5-tert-butyl-2-[(2,6-dimethylphenyl)methyl]pyrazol-3-yl]-3-oxo-propanoate (Compound 4)

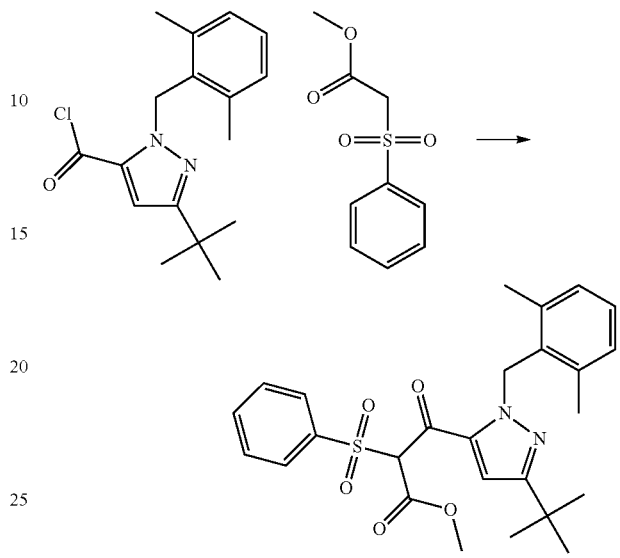

To 5-tert-butyl-2-[(2,6-dimethylphenyl)methyl]pyrazole-3-carbonyl chloride (40 mg, 0.13 mmol), methyl 2-(benzenesulfonyl)acetate (28 mg, 22 uL, 0.13 mmol) and NaH (5 mg, 0.13 mmol) in DMF were stirred at room temperature for 15 minutes. The reactions were filtered and purified by reverse phase LC-MS (10-99% $CH_3CN/H_2O$, HCl modifier) to give methyl 2-(benzenesulfonyl)-3-[5-tert-butyl-2-[(2,6-dimethylphenyl)methyl]pyrazol-3-yl]-3-oxo-propanoate (Compound 4) (18 mg, 28%). ESI-MS m/z 483.4 (M+1)$^+$; Retention time: 2.41 minutes.

Preparation 157: N-[(6-amino-2-pyridyl)sulfonyl]-6-tert-butyl-5-[(E)-2-(4-methoxyphenyl)vinyl]-2-[(4S)-2,2,4-trimethylpyrrolidin-1-yl]pyridine-3-carboxamide (Compound 1535)

Step 1: 5-Iodo-6-tert-butyl-2-hydroxypyridine-3-carbonitrile

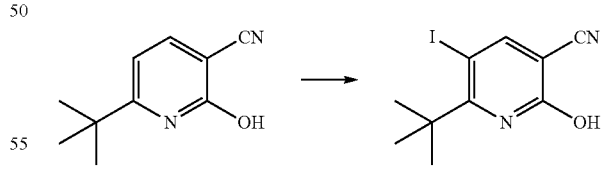

N-Iodosuccinimide (31.9 g, 142 mmol) was added to a solution of 6-tert-butyl-2-hydroxypyridine-3-carbonitrile (10.0 g, 56.8 mmol) in a mixture of 1,2-dichloroethane (120 mL) and trifluoroacetic acid (40 mL) and the reaction mixture was heated at 50° C. overnight. The solution was concentrated under reduced pressure and ethyl acetate (300 mL) was added. The organic layer was washed with 10% sodium thiosulfate solution (300 mL), water (2×200 mL) and brine (150 mL), dried over anhydrous sodium sulfate, filtered and concentrated under reduced pressure. The residue was purified by flash chromatography, eluting from 30% EtOAc in heptanes to 60% EtOAc in heptanes, to provide 5-iodo-6-tert-butyl-2-hydroxypyridine-3-carbonitrile (15.85 g, 92% yield) as a white solid. $^1$H NMR (300 MHz, CDCl$_3$) ppm 1.57 (s, 9H), 8.17 (s, 1H). [M+H]$^+$=303.0.

Step 2: 5-Iodo-6-tert-butyl-2-chloropyridine-3-carbonitrile

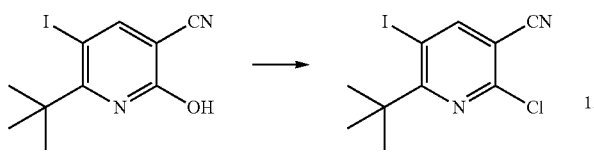

Phosphorus oxychloride (67.0 mL, 718 mmol) and phosphorus pentachloride (44.9 g, 216 mmol) were added to 5-iodo-6-tert-butyl-2-hydroxypyridine-3-carbonitrile (21.7 g, 71.8 mmol) and the reaction mixture was refluxed overnight. The reaction mixture was cooled to room temperature and concentrated under reduced pressure to remove most of the remaining phosphorus oxychloride. Water (caution: exotherm) followed by 50% NaOH solution were added until a pH ~9 was reached and the aqueous layer was extracted with ethyl acetate (3×100 mL). The combined organic layers were washed with brine (100 mL), dried over anhydrous sodium sulfate, filtered and concentrated under reduced pressure to provide 5-iodo-6-tert-butyl-2-chloroxypyridine-3-carbonitrile (17.35 g, 75% yield) as a yellow solid. $^1$H NMR (300 MHz, CDCl$_3$) ppm 1.55 (s, 9H), 8.38 (s, 1H). [M+H]$^+$=320.9.

Step 3: 5-Iodo-6-tert-butyl-2-chloropyridine-3-carboxylic acid

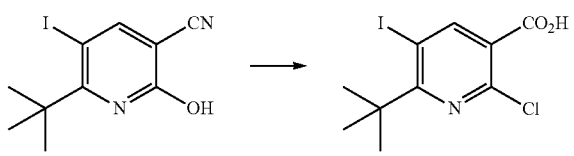

Potassium hydroxide (18.2 g, 325 mmol) in water (60 mL) was added to 5-iodo-6-tert-butyl-2-chloroxypyridine-3-carbonitrile (17.35 g, 54.1 mmol) in 2-propanol (60 mL) and the reaction mixture was heated at 90° C. overnight. Ethyl acetate (50 mL) was added and the organic layer was extracted with 1 N NaOH (3×50 mL). The basic aqueous layers were combined and concentrated under reduced pressure to remove most of the 2-propanol. The remaining aqueous layer was acidified to pH 1-2 with concentrated HCl and extracted with ethyl acetate (3×100 mL). The organic layers were combined, washed with brine (100 mL), dried over anhydrous sodium sulfate, filtered and concentrated under reduced pressure. The residue was purified by reverse-phase chromatography (methanol/water, 0% to 100%) to afford 5-iodo-6-tert-butyl-2-chloropyridine-3-carboxylic acid (8.2 g, 45% yield) as an off-white solid. $^1$H NMR (300 MHz, CDCl$_3$) ppm 1.57 (s, 9H), 8.77 (s, 1H). [M+H]$^+$=339.9.

Step 4: N-[(6-amino-2-pyridyl)sulfonyl]-6-tert-butyl-2-chloro-5-iodo-pyridine-3-carboxamide

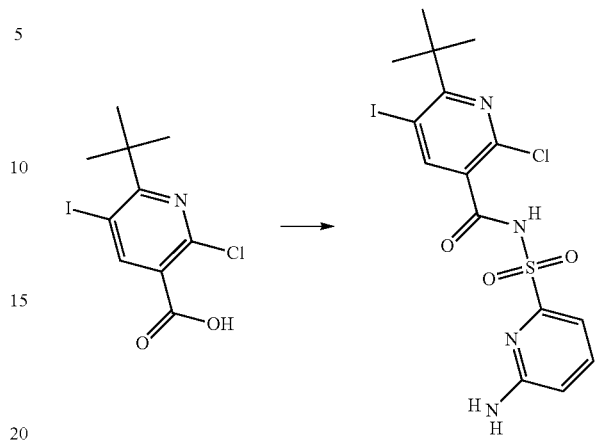

To a stirred solution of 6-tert-butyl-2-chloro-5-iodo-pyridine-3-carboxylic acid (1.57 g, 4.62 mmol) in dry DMF (11.0 mL) added CDI (0.94 g, 5.78 mmol) in one portion under nitrogen at ambient temperature. The reaction was warmed to 45° C. and stirred for 1.5 h. In a separate flask, 6-aminopyridine-2-sulfonamide (1.00 g, 5.78 mmol) was dissolved in dry DMF (9.0 mL) under nitrogen and sodium hydride (60% in mineral oil) (231 mg, 5.78 mmol) was added in portions to mitigate gas evolution at ambient temperature. The heterogeneous mixture was warmed to 40° C. and stirred for 1 hour. This reaction mixture was added to the stirred activated acid mixture in one portion at 45° C. Heat was removed and the reaction was stirred for an additional hour. The reaction mixture was slowly added to ice-cold water (160 mL) then AcOH (1.43 g, 1.35 mL, 23.81 mmol) was added and the reaction mixture was stirred vigorously for 10 mins and the solids were filtered and washed with water (3×20 mL). The solids were slurried in hexanes (50 mL) and filtered. The solid was further dried to furnish N-[(6-amino-2-pyridyl)sulfonyl]-6-tert-butyl-2-chloro-5-iodo-pyridine-3-carboxamide (2.11 g, 92%) as white solid.

Step 5: N-[(6-amino-2-pyridyl)sulfonyl]-6-tert-butyl-5-iodo-2-[(4S)-2,2,4-trimethylpyrrolidin-1-yl]pyridine-3-carboxamide

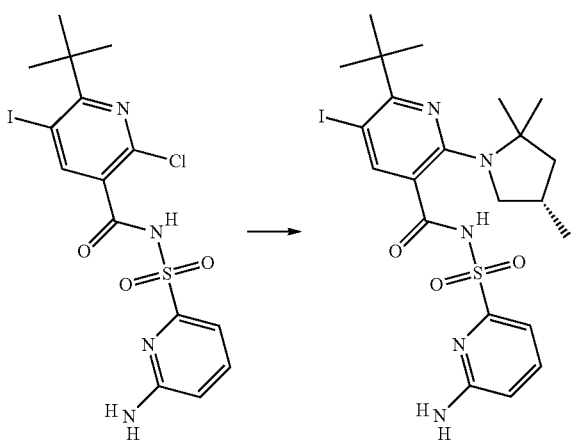

To a solution of N-[(6-amino-2-pyridyl)sulfonyl]-6-tert-butyl-2-chloro-5-iodo-pyridine-3-carboxamide (2.11 g, 4.27 mmol) in anhydrous DMSO (10 mL), (4S)-2,2,4-trimethylpyrrolidine (1.01 g, 8.96 mmol) and K₂CO₃ (2.95 g, 21.32 mmol) were added in that order. The reaction mixture was heated at 150° C. for 18 h under an atmosphere of nitrogen. The reaction mixture was allowed to cool to ambient temperature, then poured onto ice-water (125 mL) with stirring. The pH was adjusted to about 6.0 to 7.0 with the addition of 1 M HCl, the solid was filtered, washed with water (4×20 mL) and dried under vacuum to yield N-[(6-amino-2-pyridyl)sulfonyl]-6-tert-butyl-5-iodo-2-[(4S)-2,2,4-trimethylpyrrolidin-1-yl]pyridine-3-carboxamide (2.15 g, 88%) as off-white solid.

Step 6: N-[(6-amino-2-pyridyl)sulfonyl]-6-tert-butyl-5-[(E)-2-(4-methoxyphenyl)vinyl]-2-[(4S)-2,2,4-trimethylpyrrolidin-1-yl]pyridine-3-carboxamide (Compound 1535)

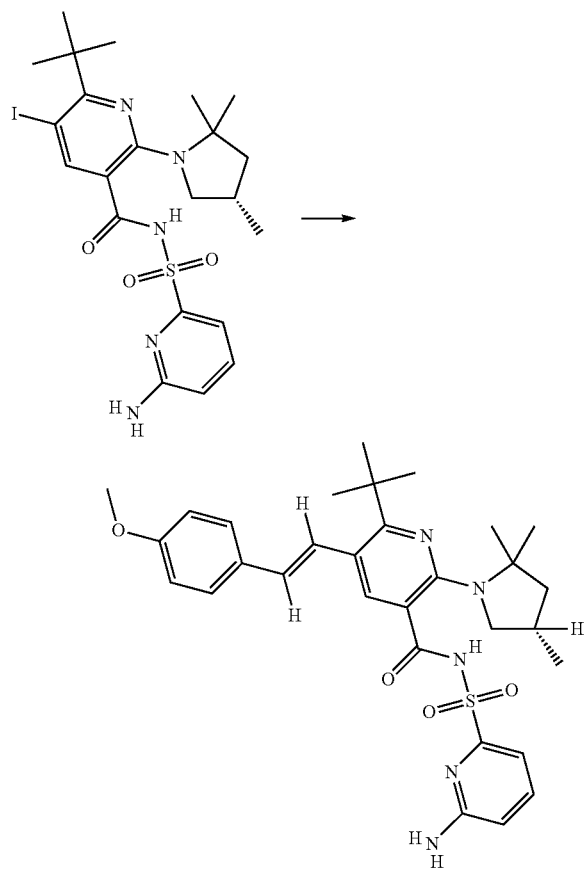

DMF (0.5 mL) and H₂O (0.1 mL) were added to N-[(6-amino-2-pyridyl)sulfonyl]-6-tert-butyl-5-iodo-2-(2,2,4-trimethylpyrrolidin-1-yl)pyridine-3-carboxamide (30 mg, 0.05 mmol) and [(E)-2-(4-methoxyphenyl)vinyl]boronic acid (19 mg, 0.11 mmol), followed by K₂CO₃ (29 mg, 0.21 mmol) under an atmosphere of nitrogen. Then tetrakis(triphenylphosphine)palladium (0) (6 mg, 0.005 mmol) was added, the reaction mixture was sealed under an atmosphere of nitrogen and heated at 130° C. for 13 h. The reaction mixture was allowed to cool to ambient temperature and the product was purified using a reverse phase HPLC-MS method using a Luna C18 (2) column (75×30 mm, 5 m particle size) and a dual gradient run from 10-99% mobile phase B over 30.0 minutes (mobile phase A=H₂O (5 mM HCl), mobile phase B=CH₃CN) to give N-[(6-amino-2-pyridyl)sulfonyl]-6-tert-butyl-5-[(E)-2-(4-methoxyphenyl)vinyl]-2-[(4S)-2,2,4-trimethylpyrrolidin-1-yl]pyridine-3-carboxamide (Compound 1535) (5 mg, 16%). ESI-MS m/z 578.6 (M+1)⁺; Retention time: 1.78 minutes; 1H NMR (400 MHz, Methanol-d₄) δ 8.26 (s, 11H), 7.68 (dd, J=8.5, 3.4 Hz 1H), 7.48 (d, J=8.7 Hz, 2H), 7.43 (d, J=15.9 Hz 1H), 7.37 (d, J=7.3 Hz, 1H), 6.94 (d, J=8.8 Hz, 2H), 6.87 (d, J=15.9 Hz, 1H), 6.77 (d, J=8.4 Hz, 1H), 3.82 (s, 3H), 3.48 (dd, J=10.9, 8.2 Hz, 1H), 3.17 (dd, J=11.1, 9.3 Hz, 1H), 2.69-2.52 (m, 1H), 2.11 (dd, J=12.4, 6.8 Hz, 1H), 1.74 (t, J=11.8 Hz, 1H), 1.54 (s, 3H), 1.49 (s, 9H), 1.46 (s, 3H), 1.13 (d, J=6.5 Hz, 3H).

The following compounds can be synthesized using the procedures described herein:

N-[(6-amino-2-pyridyl)sulfonyl]-5-(3-bicyclo[2.2.1]hept-2-enyl)-6-tert-butyl-2-[(4S)-2,2,4-trimethylpyrrolidin-1-yl]pyridine-3-carboxamide (Compound 1577), N-[(6-amino-2-pyridyl)sulfonyl]-6-tert-butyl-5-[(E)-pent-1-enyl]-2-[(4S)-2,2,4-trimethylpyrrolidin-1-yl]pyridine-3-carboxamide (Compound 1617), N-[(6-amino-2-pyridyl)sulfonyl]-6-tert-butyl-5-[(E)-2-cyclopropylvinyl]-2-[(4S)-2,2,4-trimethylpyrrolidin-1-yl]pyridine-3-carboxamide (Compound 1665), Ethyl (E)-3-[5-[(6-amino-2-pyridyl)sulfonylcarbamoyl]-2-tert-butyl-6-[(4,S)-2,2,4-trimethylpyrrolidin-1-yl]-3-pyridyl]prop-2-enoate (Compound 1490), N-[(6-amino-2-pyridyl)sulfonyl]-6-tert-butyl-2-[(4S)-2,2,4-trimethylpyrrolidin-1-yl]-5-vinyl-pyridine-3-carboxamide (Compound 1373) and N-[(6-amino-2-pyridyl)sulfonyl]-6-tert-butyl-5-[(E)-2-ethoxyvinyl]-2-[(4S)-2,2,4-trimethylpyrrolidin-1-yl]pyridine-3-carboxamide (Compound 1626)

Preparation 158: N-[(6-amino-2-pyridyl)sulfonyl]-6-(3-fluoro-5-isobutoxy-phenyl)-2-(4-phenylbutoxy)pyridine-3-carboxamide (Compound 1686)

Step 1: N-[(6-amino-2-pyridyl)sulfonyl]-2-fluoro-6-(3-fluoro-5-isobutoxy-phenyl)pyridine-3-carboxamide

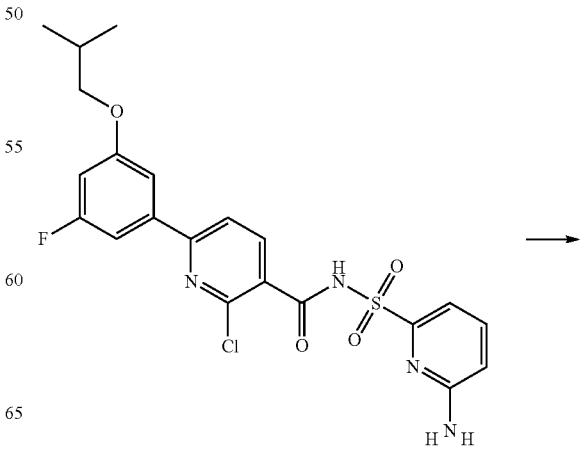

2293
-continued

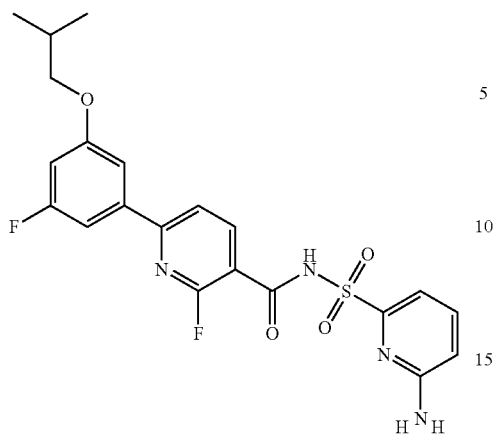

N-[(6-amino-2-pyridyl)sulfonyl]-2-chloro-6-(3-fluoro-5-isobutoxy-phenyl)pyridine-3-carboxamide (300 mg, 0.63 mmol) was dissolved in DMSO (1.2 mL). Cesium fluoride (476 mg, 3.13 mmol) was added. The reaction mixture was sealed and stirred overnight at 150° C. Additional cesium fluoride (100 mg) was added, and the reaction mixture was stirred overnight at 150° C. After cooling to room temperature, the mixture was diluted with EtOAc (75 mL) and washed with diluted aqueous HCl solution (0.1 N, 1×75 mL). The organic layer was dried over sodium sulfate, filtered and concentrated under reduced pressure. The product was used in the next step without further purification. ESI-MS m/z 463.2 (M+1)$^+$; Retention time: 1.83 minutes.

Step 2: N-[(6-amino-2-pyridyl)sulfonyl]-6-(3-fluoro-5-isobutoxy-phenyl)-2-(4-phenylbutoxy)pyridine-3-carboxamide (Compound 1686)

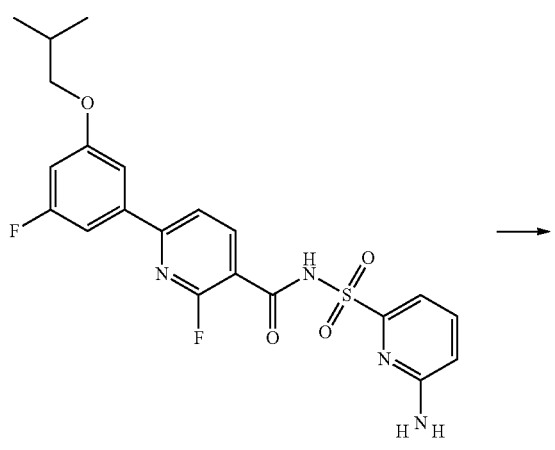

2294
-continued

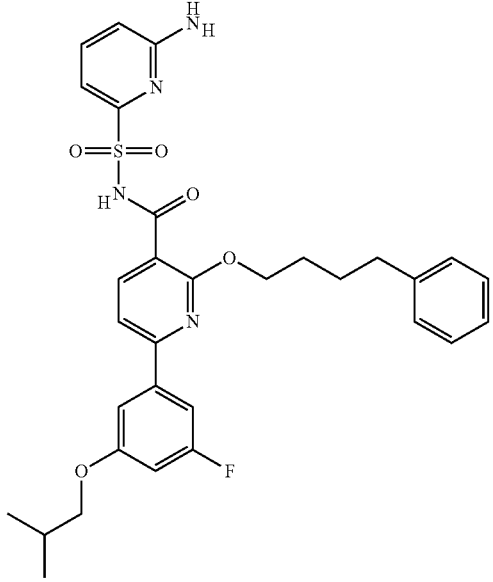

4-phenylbutan-1-ol (23 mg, 0.15 mmol) was dissolved in dioxane (250 μL). Sodium hydride (6 mg, 0.15 mmol) was added, and the reaction mixture was stirred at room temperature for 5 minutes. A solution of N-[(6-amino-2-pyridyl)sulfonyl]-2-fluoro-6-(3-fluoro-5-isobutoxy-phenyl)pyridine-3-carboxamide (35 mg, 0.08 mmol) in DMSO (250 μL) was added. After another 5 minutes of stirring, the reaction mixture was heated under microwave irradiation at 100° C. for 30 minutes, then concentrated under reduced pressure and purified by reverse phase HPLC-MS method using a Luna C18 (2) column (75×30 mm, 5 μm particle size) and a dual gradient run from 1-99% mobile phase B over 15.0 minutes, (mobile phase A=water (5 mM HCl), mobile phase B=acetonitrile) to give N-[(6-amino-2-pyridyl)sulfonyl]-6-(3-fluoro-5-isobutoxy-phenyl)-2-(4-phenylbutoxy)pyridine-3-carboxamide (Compound 1686) (30 mg, 64%). ESI-MS m/z 593.4 (M+1)$^+$; Retention time: 2.47 minutes.

The following compounds can be synthesized using the procedures described herein:

N-[(6-amino-2-pyridyl)sulfonyl]-6-(3-fluoro-5-isobutoxy-phenyl)-2-(3-phenylbutoxy)pyridine-3-carboxamide (Compound 1689), N-[(6-amino-2-pyridyl)sulfonyl]-6-(3-fluoro-5-isobutoxy-phenyl)-2-(3-phenylpropoxy)pyridine-3-carboxamide (Compound 1694), N-[(6-amino-2-pyridyl)sulfonyl]-6-(3-fluoro-5-isobutoxy-phenyl)-2-[4-(3-pyridyl)butoxy]pyridine-3-carboxamide (Compound 1690), N-[(6-amino-2-pyridyl)sulfonyl]-6-(3-fluoro-5-isobutoxy-phenyl)-2-[4-(4-pyridyl)butoxy]pyridine-3-carboxamide (Compound 1687), N-[(6-amino-2-pyridyl)sulfonyl]-6-(3-fluoro-5-isobutoxy-phenyl)-2-[4-(2-pyridyl)butoxy]pyridine-3-carboxamide (Compound 1688), N-[(6-amino-2-pyridyl)sulfonyl]-6-(3-fluoro-5-isobutoxy-phenyl)-2-[3-(2-pyridyl)propoxy]pyridine-3-carboxamide (Compound 1693), N-[(6-amino-2-pyridyl)sulfonyl]-6-(3-fluoro-5-isobutoxy-phenyl)-2-[3-(3-pyridyl)propoxy]pyridine-3-carboxamide (Compound 1691) and N-[(6-amino-2-pyridyl)sulfonyl]-6-(3-fluoro-5-isobutoxy-phenyl)-2-(3-pyrazol-1-ylpropoxy)pyridine-3-carboxamide (Compound 1692).

Preparation 159: N-[(6-amino-2-pyridyl)sulfonyl]-2-(2,2-dimethyl-3-oxo-pyrrolidin-1-yl)-6-(3-fluoro-5-isobutoxy-phenyl)pyridine-3-carboxamide (Compound 1189)

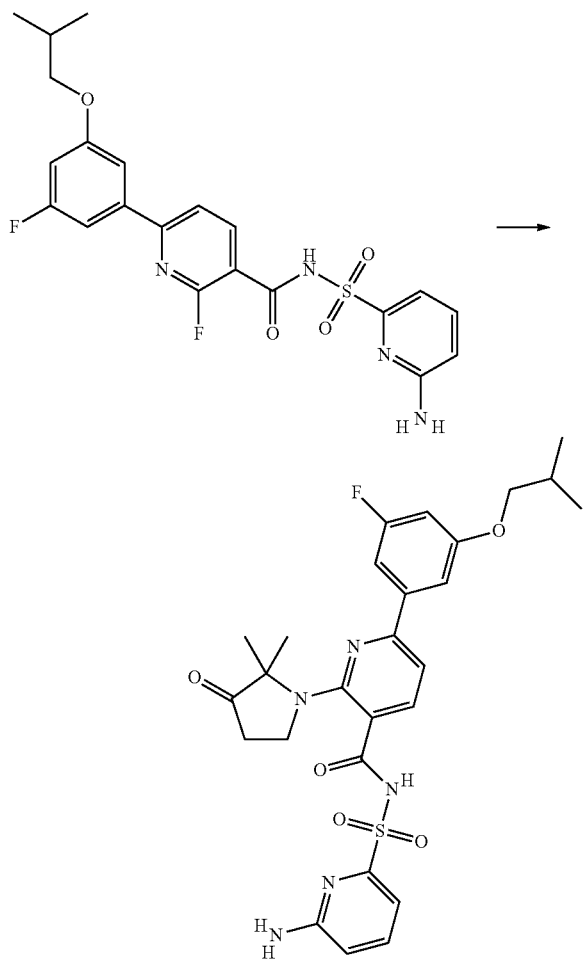

Solid potassium carbonate (90 mg, 0.65 mmol) was added to a suspension of 2,2-dimethylpyrrolidin-3-one (49 mg, 0.32 mmol) in DMSO (250 μL), followed by N-[(6-amino-2-pyridyl)sulfonyl]-2-fluoro-6-(3-fluoro-5-isobutoxy-phenyl)pyridine-3-carboxamide (HCl salt) (50 mg, 0.11 mmol). The reaction mixture was stirred at 150° C. for 3 hours. The reaction mixture was purified using a reverse phase HPLC method using a Luna C18 (2) column (50×21.2 mm, 5 μm particle size) and a dual gradient run from 10-99% mobile phase B over 15.0 minutes (mobile phase A=water (5 mM HCl), mobile phase B=acetonitrile). ESI-MS m/z 556.4 (M+1)+; Retention time: 2.01 minutes.

The following compound can be synthesized using the procedures described herein:

N-[(6-amino-2-pyridyl)sulfonyl]-2-(2,2-dimethyl-4-oxo-pyrrolidin-1-yl)-6-(3-fluoro-5-isobutoxy-phenyl)pyridine-3-carboxamide (Compound 1073).

Preparation 160: 2-(benzenesulfonyl)-1-[5-tert-butyl-2-[(2,4,6-trimethylphenyl)methyl]pyrazol-3-yl]propan-1-one (Compound 139)

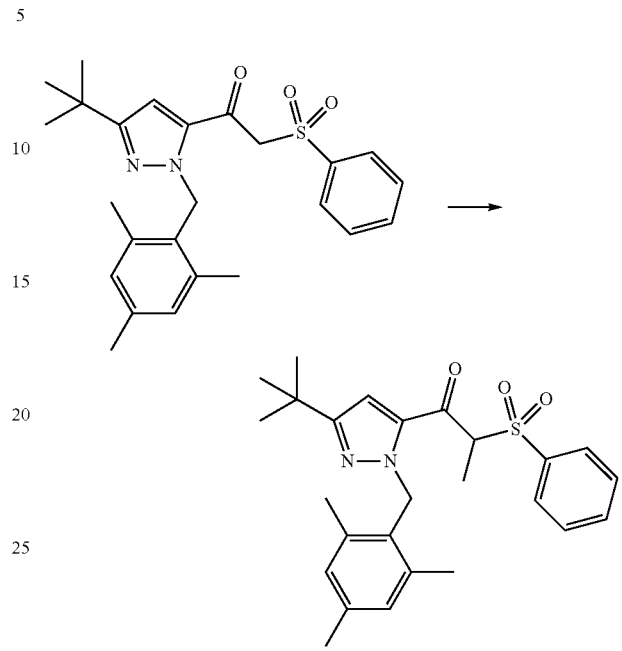

To a solution of 2-(benzenesulfonyl)-1-{3-tert-butyl-1-[(2,4,6-trimethylphenyl)methyl]-1H-pyrazol-5-yl}ethan-1-one (50 mg, 0.11 mmol) in THF (3.0 mL) and DMF (1.0 mL) was added DBU (52 mg, 0.34 mmol) and the mixture was stirred at room temperature for 30 minutes. Iodomethane (40 mg, 0.28 mmol) was then added and the reaction was stirred overnight at room temperature. Analysis of an aliquot by LCMS indicated that only mono-methylation (no bis-methylation) had occurred. The crude reaction mixture was transferred to a separatory funnel with water and extracted twice with diethyl ether. The organic layers were combined, dried over sodium sulfate, filtered and concentrated under reduced pressure to give the crude product. In a separate experiment, a solution of 2-(benzenesulfonyl)-1-{3-tert-butyl-1-[(2,4,6-trimethylphenyl)methyl]-1H-pyrazol-5-yl}ethan-1-one (50 mg, 0.11 mmol) in THF (3.0 mL) and DMF (1.0 mL) was added DBU (52 mg, 0.34 mmol) and the mixture was heated in an oil bath at 80° C. for 10 minutes. Iodomethane (40 mg, 0.28 mmol) was then added, the vial was capped and the reaction was heated in an oil bath at 80° C. overnight. Analysis of an aliquot by LCMS indicated that only mono-methylation (no bis-methylation) had occurred. The crude reaction mixture was transferred to a separatory funnel with water and extracted twice with diethyl ether. The organic layers were combined, dried over sodium sulfate, filtered and concentrated under reduced pressure to give the crude product. Both crude reaction mixtures were combined together and purified by silica-gel column chromatography, eluting with 5% to 20% EtOAc in heptanes, to afford rac 2-(benzenesulfonyl)-1-{3-tert-butyl-1-[(2,4,6-trimethylphenyl)methyl]-1H-pyrazol-5-ylpropan-1-one (64 mg, 60% yield) as a white solid. $^1$H NMR (300 MHz, DMSO-$d_6$) ppm 1.10 (s, 9H), 1.46 (d, J=6.8 Hz, 3H), 2.16 (s, 6H), 2.21 (s, 3H), 5.40-5.53 (m, 3H), 6.83 (s, 2H), 7.15 (s, 1H), 7.55-7.62 (m, 2H), 7.68-7.76 (m, 3H). ESI-MS m/z 453.2 (M+1)+.

Table 2 below recites the analytical data for the compounds of Table 1.

Lengthy table referenced here

US12168009-20241217-T00001

Please refer to the end of the specification for access instructions.

Assays
Protocol 1
Assays for Detecting and Measuring F508del Potentiation Properties of Compounds
Membrane Potential Optical Methods for Assaying F508del Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of F508del, a double-addition HTS assay format was developed. This HTS assay utilizes fluorescent voltage sensing dyes to measure changes in membrane potential on the FLIPR III as a measurement for increase in gating (conductance) of F508del in temperature-corrected F508del NIH 3T3 cells. The driving force for the response is a Cl⁻ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, $CaCl_2$) 2, $MgCl_2$ 1, HEPES 10, pH 7.4 with NaOH.

Chloride-free bath solution: Chloride salts in Bath Solution #1 (above) are substituted with gluconate salts.

Cell Culture

NIH3T3 mouse fibroblasts stably expressing F508del are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for assaying F508del modulation properties of compounds.

Ussing Chamber Assay

Ussing chamber experiments were performed on polarized airway epithelial cells expressing F508del to further characterize the F508del augmenters or inducers identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In Vitro Cell. Dev. Biol. 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for F508del.

HBE grown on Costar® Snapwell™ cell culture inserts were mounted in an Using chamber (Physiologic Instruments, Inc., San Diego, CA), and the transepithelial resistance and short-circuit current in the presence of a basolateral to apical Cl⁻ gradient (Isc) were measured using a voltage-clamp system (Department of Bioengineering, University of Iowa, IA). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$), 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 µM) and all test compounds were added to the apical side of the cell culture inserts. The efficacy of the putative F508del potentiators was compared to that of the known potentiator, genistein.

Patch-Clamp Recordings

Total Cl⁻ current in F508del-NIH3T3 cells was monitored using the perforated-patch recording configuration as previously described (Rae, J., Cooper, K., Gates, P., & Watsky, M. (1991) J. Neurosci. Methods 37, 15-26). Voltage-clamp recordings were performed at 22° C. using an Axopatch 200B patch-clamp amplifier (Axon Instruments Inc., Foster City, CA). The pipette solution contained (in mM) 150 N-methyl-D-glucamine (NMDG)-Cl, 2 $MgCl_2$, 2 $CaCl_2$), 10 EGTA, 10 HEPES, and 240 µg/mL amphotericin-B (pH adjusted to 7.35 with HCl). The extracellular medium contained (in mM) 150 NMDG-Cl, 2 $MgCl_2$, 2 $CaCl_2$), 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate F508del, 10 µM forskolin and 20 µM genistein were added to the bath and the current-voltage relation was monitored every 30 sec.

Identification of Potentiator Compounds

The ability of F508del potentiators to increase the macroscopic F508del Cl⁻ current ($I_{F508del}$) in NIH3T3 cells stably expressing F508del was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing F508del are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected F508del expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and F508del were activated by adding 1 mM Mg-ATP, 75 nM of the catalytic subunit of cAMP-dependent protein kinase (PKA; Promega Corp. Madison, WI), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of F508del activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing F508del are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Protocol 2

Assays for Detecting and Measuring F508del Correction Properties of Compounds

Membrane Potential Optical Methods for Assaying F508del Modulation Properties of Compounds.

The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (S Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, $DiSBAC_2$ (3), and a fluorescent phospholipid, CC2-DMPE, which is attached to the outer leaflet of the plasma membrane and acts as a FRET donor. Changes in membrane potential ($V_m$) cause the negatively charged $DiSBAC_2$ (3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with F508del; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" F508del. The cells were subsequently rinsed 3× with Krebs Ringers solution and loaded with the voltage-sensitive dyes. To activate F508del, 10 μM forskolin and the CFTR potentiator, genistein (20 μM), were added along with Cl⁻-free medium to each well. The addition of Cl⁻-free medium promoted Cl⁻ efflux in response to F508del activation and the resulting membrane depolarization was optically monitored using the FRET-based voltage-sensor dyes.

Identification of Potentiator Compounds

To identify potentiators of F508del, a double-addition HTS assay format was developed. During the first addition, a Cl⁻-free medium with or without test compound was added to each well. After 22 sec, a second addition of Cl⁻-free medium containing 2-10 μM forskolin was added to activate F508del. The extracellular Cl⁻ concentration following both additions was 28 mM, which promoted Cl⁻ efflux in response to F508del activation and the resulting membrane depolarization was optically monitored using the FRET-based voltage-sensor dyes.

Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 (above) are substituted with gluconate salts.

CC2-DMPE: Prepared as a 10 mM stock solution in DMSO and stored at −20° C.

$DiSBAC_2$ (3): Prepared as a 10 mM stock in DMS0 and stored at −20° C.

Cell Culture

NIH3T3 mouse fibroblasts stably expressing F508del are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 $cm^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for Assaying F508del Modulation Properties of Compounds Ussing Chamber Assay Using chamber experiments were performed on polarized epithelial cells expressing F508del to further characterize the F508del augmenters or inducers identified in the optical assays. FRT$^{F508del}$ epithelial cells grown on Costar Snapwell cell culture inserts were mounted in an Ussing chamber (Physiologic Instruments, Inc., San Diego, CA), and the monolayers were continuously short-circuited using a Voltage-clamp System (Department of Bioengineering, University of Iowa, IA, and, Physiologic Instruments, Inc., San Diego, CA). Transepithelial resistance was measured by applying a 2-mV pulse. Under these conditions, the FRT epithelia demonstrated resistances of 4 KSZ/cm² or more. The solutions were maintained at 27° C. and bubbled with air. The electrode offset potential and fluid resistance were corrected using a cell-free insert. Under these conditions, the current reflects the flow of Cl⁻ through F508del expressed in the apical membrane. The Isc was digitally acquired using an MP100A-CE interface and AcqKnowledge software (v3.2.6; BIOPAC Systems, Santa Barbara, CA).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate F508del, forskolin (10 µM) and the PDE inhibitor, IBMX (100 µM), were applied followed by the addition of the CFTR potentiator, genistein (50 µM).

As observed in other cell types, incubation at low temperatures of FRT cells stably expressing F508del increases the functional density of CFTR in the plasma membrane. To determine the activity of correction compounds, the cells were incubated with 10 µM of the test compound for 24 hours at 37° C. and were subsequently washed 3× prior to recording. The cAMP- and genistein-mediated Isc in compound-treated cells was normalized to the 27° C. and 37° C. controls and expressed as percentage activity. Preincubation of the cells with the correction compound significantly increased the cAMP- and genistein-mediated Isc compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 µg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 µM) and all test compounds were added to both sides of the cell culture inserts. The efficacy of the putative F508del potentiators was compared to that of the known potentiator, genistein.

Solutions

Basolateral solution (in mM): NaCl (135), CaCl₂ (1.2), MgCl₂ (1.2), K₂HPO₄ (2.4), KHPO₄ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

Cell Culture

Fisher rat epithelial (FRT) cells expressing F508del (FRT$^{F508del}$) were used for Ussing chamber experiments for the putative F508del augmenters or inducers identified from our optical assays. The cells were cultured on Costar Snapwell cell culture inserts and cultured for five days at 37° C. and 5% CO₂ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the F508del. To determine the activity of corrections compounds, the cells were incubated at 27° C. or 37° C. with and without the compounds for 24 hours.

Whole-Cell Recordings

The macroscopic F508del current ($I_{F508del}$) in temperature- and test compound-corrected NIH3T3 cells stably expressing F508del were monitored using the perforated-patch, whole-cell recording. Briefly, voltage-clamp recordings of $I_{F508del}$ were performed at room temperature using an Axopatch 200B patch-clamp amplifier (Axon Instruments Inc., Foster City, CA). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ (Eci) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

Identification of Correction Compounds

To determine the activity of correction compounds for increasing the density of functional F508del in the plasma membrane, we used the above-described perforated-patch-recording techniques to measure the current density following 24-hr treatment with the correction compounds. To fully activate F508del, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of F508del in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

Identification of Potentiator Compounds

The ability of F508del potentiators to increase the macroscopic F508del Cl⁻ current ($I_{F508del}$) in NIH3T3 cells stably expressing F508del was also investigated using perforated-patch-recording techniques. The potentiators identified from the optical assays evoked a dose-dependent increase in $I_{F508del}$ with similar potency and efficacy observed in the optical assays. In all cells examined, the reversal potential before and during potentiator application was around −30 mV, which is the calculated $E_{Cl}$ (−28 mV).

Solutions

Intracellular solution (in mM): Cs-aspartate (90), CsCl (50), MgCl₂ (1), HEPES (10), and 240 µg/ml amphotericin-B (pH adjusted to 7.35 with CsOH).

Extracellular solution (in mM): N-methyl-D-glucamine (NMDG)-Cl (150), MgCl₂ (2), CaCl₂ (2), HEPES (10) (pH adjusted to 7.35 with HC).

Cell Culture

NIH3T3 mouse fibroblasts stably expressing F508del are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-channel recordings

The single-channel activities of temperature-corrected F508del stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, FL) and had a resistance of 5-8 MΩ when filled with the extracellular solution. The F508del was activated after excision, by adding 1 mM Mg-ATP, and 75 nM of the cAMP-dependent protein kinase, catalytic subunit (PKA; Promega Corp. Madison, WI). After channel activity stabilized, the patch was perifused using a gravity-driven microperfusion system. The inflow was placed adjacent to the patch, resulting in complete solution exchange within 1-2 sec. To maintain F508del activity during the rapid perifusion, the nonspecific phosphatase inhibitor $F^-$ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing 2 active channels. The maximum number of simultaneous openings determined the number of active channels during the course of an experiment. To determine the single-channel current amplitude, the data recorded from 120 sec of F508del activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

Cell Culture

NIH3T3 mouse fibroblasts stably expressing F508del are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

The compounds of formula I are useful as modulators of CFTR activity. Table 3 below illustrates the EC30 and relative efficacy of the compounds of Table 1. In Table 3 below, the following meanings apply. EC30: "+++" means <3 uM; "++" means between 3 uM and 10 uM; "+" means greater than 10 uM.

TABLE 3

| Cmpd. No. | EC30 (μM) |
|---|---|
| 1 | +++ |
| 2 | +++ |
| 3 | +++ |
| 4 | + |
| 5 | ++ |
| 6 | +++ |
| 7 | +++ |
| 8 | +++ |
| 9 | +++ |
| 10 | +++ |
| 11 | +++ |
| 12 | +++ |
| 13 | ++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | ++ |
| 24 | ++ |
| 25 | ++ |
| 26 | ++ |
| 27 | +++ |
| 28 | +++ |
| 29 | +++ |
| 30 | +++ |
| 31 | ++ |
| 32 | ++ |
| 33 | +++ |
| 34 | +++ |
| 35 | +++ |
| 36 | +++ |
| 37 | +++ |
| 38 | +++ |
| 39 | ++ |
| 40 | +++ |
| 41 | +++ |
| 42 | ++ |
| 43 | +++ |
| 44 | ++ |
| 45 | +++ |
| 46 | ++ |
| 47 | +++ |
| 48 | ++ |
| 49 | +++ |
| 50 | +++ |
| 51 | +++ |
| 52 | +++ |
| 53 | +++ |
| 54 | ++ |
| 55 | ++ |
| 56 | +++ |
| 57 | +++ |
| 58 | ++ |
| 59 | +++ |
| 60 | +++ |
| 61 | +++ |
| 62 | +++ |

TABLE 3-continued

| Cmpd. No. | EC30 (μM) |
|---|---|
| 63 | +++ |
| 64 | ++ |
| 65 | ++ |
| 66 | +++ |
| 67 | ++ |
| 68 | +++ |
| 69 | +++ |
| 70 | +++ |
| 71 | +++ |
| 72 | ++ |
| 73 | +++ |
| 74 | +++ |
| 75 | ++ |
| 76 | +++ |
| 77 | +++ |
| 78 | +++ |
| 79 | ++ |
| 80 | +++ |
| 81 | +++ |
| 82 | +++ |
| 83 | +++ |
| 84 | +++ |
| 85 | ++ |
| 86 | ++ |
| 87 | +++ |
| 88 | +++ |
| 89 | +++ |
| 90 | +++ |
| 91 | ++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | +++ |
| 112 | +++ |
| 113 | ++ |
| 114 | +++ |
| 115 | +++ |
| 116 | ++ |
| 117 | +++ |
| 118 | ++ |
| 119 | +++ |
| 120 | +++ |
| 121 | ++ |
| 122 | ++ |
| 123 | +++ |
| 124 | ++ |
| 125 | ++ |
| 126 | +++ |
| 127 | +++ |
| 128 | +++ |
| 129 | ++ |
| 130 | +++ |
| 131 | +++ |
| 132 | +++ |
| 133 | +++ |
| 134 | +++ |
| 135 | +++ |
| 136 | +++ |
| 137 | +++ |
| 138 | ++ |
| 139 | +++ |
| 140 | +++ |
| 141 | +++ |
| 142 | +++ |
| 143 | +++ |
| 144 | +++ |
| 145 | +++ |
| 146 | +++ |
| 147 | +++ |
| 148 | +++ |
| 149 | +++ |
| 150 | +++ |
| 151 | +++ |
| 152 | +++ |
| 153 | +++ |
| 154 | +++ |
| 155 | ++ |
| 156 | +++ |
| 157 | ++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | ++ |
| 168 | +++ |
| 169 | +++ |
| 170 | +++ |
| 171 | +++ |
| 172 | +++ |
| 173 | ++ |
| 174 | ++ |
| 175 | ++ |
| 176 | +++ |
| 177 | ++ |
| 178 | +++ |
| 179 | +++ |
| 180 | +++ |
| 181 | +++ |
| 182 | +++ |
| 183 | +++ |
| 184 | ++ |
| 185 | +++ |
| 186 | +++ |
| 187 | ++ |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |
| 197 | +++ |
| 198 | +++ |
| 199 | +++ |
| 200 | ++ |
| 201 | +++ |
| 202 | +++ |
| 203 | +++ |
| 204 | +++ |
| 205 | ++ |
| 206 | +++ |
| 207 | +++ |
| 208 | +++ |
| 209 | +++ |
| 210 | +++ |
| 211 | ++ |
| 212 | +++ |
| 213 | +++ |
| 214 | +++ |
| 215 | +++ |
| 216 | +++ |

TABLE 3-continued

| Cmpd. No. | EC30 (µM) |
|---|---|
| 217 | +++ |
| 218 | ++ |
| 219 | +++ |
| 220 | +++ |
| 221 | +++ |
| 222 | +++ |
| 223 | +++ |
| 224 | +++ |
| 225 | +++ |
| 226 | +++ |
| 227 | ++ |
| 228 | +++ |
| 229 | +++ |
| 230 | ++ |
| 231 | +++ |
| 232 | +++ |
| 233 | +++ |
| 234 | +++ |
| 235 | +++ |
| 236 | ++ |
| 237 | ++ |
| 238 | +++ |
| 239 | +++ |
| 240 | ++ |
| 241 | +++ |
| 242 | +++ |
| 243 | +++ |
| 244 | +++ |
| 245 | ++ |
| 246 | ++ |
| 247 | +++ |
| 248 | +++ |
| 249 | +++ |
| 250 | +++ |
| 251 | +++ |
| 252 | +++ |
| 253 | +++ |
| 254 | ++ |
| 255 | +++ |
| 256 | +++ |
| 257 | +++ |
| 258 | ++ |
| 259 | +++ |
| 260 | ++ |
| 261 | +++ |
| 262 | +++ |
| 263 | +++ |
| 264 | +++ |
| 265 | +++ |
| 266 | +++ |
| 267 | +++ |
| 268 | +++ |
| 269 | +++ |
| 270 | +++ |
| 271 | +++ |
| 272 | ++ |
| 273 | +++ |
| 274 | +++ |
| 275 | +++ |
| 276 | +++ |
| 277 | +++ |
| 278 | ++ |
| 279 | +++ |
| 280 | +++ |
| 281 | +++ |
| 282 | ++ |
| 283 | +++ |
| 284 | +++ |
| 285 | +++ |
| 286 | +++ |
| 287 | +++ |
| 288 | +++ |
| 289 | +++ |
| 290 | +++ |
| 291 | ++ |
| 292 | +++ |
| 293 | +++ |

TABLE 3-continued

| Cmpd. No. | EC30 (µM) |
|---|---|
| 294 | +++ |
| 295 | ++ |
| 296 | +++ |
| 297 | ++ |
| 298 | ++ |
| 299 | +++ |
| 300 | +++ |
| 301 | ++ |
| 302 | ++ |
| 303 | +++ |
| 304 | +++ |
| 305 | +++ |
| 306 | +++ |
| 307 | +++ |
| 308 | +++ |
| 309 | +++ |
| 310 | +++ |
| 311 | +++ |
| 312 | +++ |
| 313 | +++ |
| 314 | +++ |
| 315 | +++ |
| 316 | +++ |
| 317 | +++ |
| 318 | +++ |
| 319 | ++ |
| 320 | +++ |
| 321 | +++ |
| 322 | +++ |
| 323 | +++ |
| 324 | ++ |
| 325 | +++ |
| 326 | +++ |
| 327 | +++ |
| 328 | +++ |
| 329 | +++ |
| 330 | +++ |
| 331 | +++ |
| 332 | +++ |
| 333 | +++ |
| 334 | ++ |
| 335 | +++ |
| 336 | +++ |
| 337 | +++ |
| 338 | +++ |
| 339 | +++ |
| 340 | +++ |
| 341 | +++ |
| 342 | +++ |
| 343 | +++ |
| 344 | +++ |
| 345 | +++ |
| 346 | +++ |
| 347 | +++ |
| 348 | +++ |
| 349 | ++ |
| 350 | +++ |
| 351 | +++ |
| 352 | +++ |
| 353 | +++ |
| 354 | +++ |
| 355 | +++ |
| 356 | +++ |
| 357 | ++ |
| 358 | +++ |
| 359 | +++ |
| 360 | +++ |
| 361 | +++ |
| 362 | +++ |
| 363 | +++ |
| 364 | +++ |
| 365 | +++ |
| 366 | +++ |
| 367 | +++ |
| 368 | +++ |
| 369 | +++ |
| 370 | +++ |

TABLE 3-continued

| Cmpd. No. | EC30 (µM) |
|---|---|
| 371 | +++ |
| 372 | ++ |
| 373 | ++ |
| 374 | +++ |
| 375 | +++ |
| 376 | +++ |
| 377 | +++ |
| 378 | +++ |
| 379 | +++ |
| 380 | +++ |
| 381 | ++ |
| 382 | +++ |
| 383 | +++ |
| 384 | +++ |
| 385 | +++ |
| 386 | +++ |
| 387 | +++ |
| 388 | ++ |
| 389 | +++ |
| 390 | +++ |
| 391 | + |
| 392 | ++ |
| 393 | ++ |
| 394 | +++ |
| 395 | +++ |
| 396 | +++ |
| 397 | +++ |
| 398 | +++ |
| 399 | +++ |
| 400 | ++ |
| 401 | +++ |
| 402 | +++ |
| 403 | ++ |
| 404 | +++ |
| 405 | +++ |
| 406 | +++ |
| 407 | ++ |
| 408 | +++ |
| 409 | + |
| 410 | +++ |
| 411 | +++ |
| 412 | +++ |
| 413 | +++ |
| 414 | +++ |
| 415 | +++ |
| 416 | +++ |
| 417 | ++ |
| 418 | +++ |
| 419 | +++ |
| 420 | +++ |
| 421 | +++ |
| 422 | +++ |
| 423 | +++ |
| 424 | +++ |
| 425 | +++ |
| 426 | +++ |
| 427 | +++ |
| 428 | +++ |
| 429 | +++ |
| 430 | +++ |
| 431 | ++ |
| 432 | +++ |
| 433 | +++ |
| 434 | +++ |
| 435 | +++ |
| 436 | +++ |
| 437 | +++ |
| 438 | +++ |
| 439 | +++ |
| 440 | +++ |
| 441 | +++ |
| 442 | +++ |
| 443 | + |
| 444 | ++ |
| 445 | + |
| 446 | +++ |
| 447 | +++ |
| 448 | +++ |
| 449 | + |
| 450 | +++ |
| 451 | ++ |
| 452 | +++ |
| 453 | +++ |
| 454 | +++ |
| 455 | +++ |
| 456 | +++ |
| 457 | +++ |
| 458 | +++ |
| 459 | +++ |
| 460 | ++ |
| 461 | ++ |
| 462 | +++ |
| 463 | ++ |
| 464 | +++ |
| 465 | ++ |
| 466 | +++ |
| 467 | ++ |
| 468 | +++ |
| 469 | ++ |
| 470 | +++ |
| 471 | +++ |
| 472 | + |
| 473 | +++ |
| 474 | +++ |
| 475 | +++ |
| 476 | ++ |
| 477 | +++ |
| 478 | ++ |
| 479 | +++ |
| 480 | +++ |
| 481 | +++ |
| 482 | +++ |
| 483 | +++ |
| 484 | |
| 485 | +++ |
| 486 | ++ |
| 487 | ++ |
| 488 | +++ |
| 489 | +++ |
| 490 | +++ |
| 491 | +++ |
| 492 | +++ |
| 493 | +++ |
| 494 | +++ |
| 495 | ++ |
| 496 | +++ |
| 497 | +++ |
| 498 | +++ |
| 499 | ++ |
| 500 | +++ |
| 501 | +++ |
| 502 | +++ |
| 503 | +++ |
| 504 | +++ |
| 505 | ++ |
| 506 | +++ |
| 507 | +++ |
| 508 | ++ |
| 509 | +++ |
| 510 | +++ |
| 511 | +++ |
| 512 | ++ |
| 513 | ++ |
| 514 | + |
| 515 | +++ |
| 516 | +++ |
| 517 | ++ |
| 518 | +++ |
| 519 | ++ |
| 520 | +++ |
| 521 | ++ |
| 522 | +++ |
| 523 | +++ |
| 524 | ++ |

TABLE 3-continued

| Cmpd. No. | EC30 (μM) |
|---|---|
| 525 | ++ |
| 526 | +++ |
| 527 | +++ |
| 528 | +++ |
| 529 | ++ |
| 530 | +++ |
| 531 | +++ |
| 532 | ++ |
| 533 | +++ |
| 534 | ++ |
| 535 | +++ |
| 536 | +++ |
| 537 | +++ |
| 538 | +++ |
| 539 | + |
| 540 | + |
| 541 | +++ |
| 542 | +++ |
| 543 | ++ |
| 544 | +++ |
| 545 | ++ |
| 546 | ++ |
| 547 | +++ |
| 548 | +++ |
| 549 | +++ |
| 550 | ++ |
| 551 | +++ |
| 552 | ++ |
| 553 | +++ |
| 554 | +++ |
| 555 | +++ |
| 556 | + |
| 557 | +++ |
| 558 | +++ |
| 559 | +++ |
| 560 | +++ |
| 561 | +++ |
| 562 | +++ |
| 563 | +++ |
| 564 | ++ |
| 565 | + |
| 566 | + |
| 567 | ++ |
| 568 | +++ |
| 569 | +++ |
| 570 | +++ |
| 571 | ++ |
| 572 | +++ |
| 573 | +++ |
| 574 | ++ |
| 575 | +++ |
| 576 | +++ |
| 577 | ++ |
| 578 | +++ |
| 579 | +++ |
| 580 | +++ |
| 581 | +++ |
| 582 | ++ |
| 583 | +++ |
| 584 | ++ |
| 585 | +++ |
| 586 | +++ |
| 587 | +++ |
| 588 | ++ |
| 589 | +++ |
| 590 | +++ |
| 591 | +++ |
| 592 | +++ |
| 593 | +++ |
| 594 | ++ |
| 595 | +++ |
| 596 | ++ |
| 597 | +++ |
| 598 | ++ |
| 599 | +++ |
| 600 | +++ |
| 601 | +++ |

TABLE 3-continued

| Cmpd. No. | EC30 (μM) |
|---|---|
| 602 | +++ |
| 603 | +++ |
| 604 | +++ |
| 605 | +++ |
| 606 | ++ |
| 607 | +++ |
| 608 | ++ |
| 609 | +++ |
| 610 | +++ |
| 611 | +++ |
| 612 | +++ |
| 613 | +++ |
| 614 | +++ |
| 615 | +++ |
| 616 | +++ |
| 617 | +++ |
| 618 | ++ |
| 619 | +++ |
| 620 | +++ |
| 621 | +++ |
| 622 | +++ |
| 623 | ++ |
| 624 | ++ |
| 625 | +++ |
| 626 | +++ |
| 627 | + |
| 628 | +++ |
| 629 | +++ |
| 630 | +++ |
| 631 | +++ |
| 632 | ++ |
| 633 | +++ |
| 634 | +++ |
| 635 | + |
| 636 | ++ |
| 637 | ++ |
| 638 | ++ |
| 639 | +++ |
| 640 | ++ |
| 641 | +++ |
| 642 | +++ |
| 643 | ++ |
| 644 | +++ |
| 645 | ++ |
| 646 | ++ |
| 647 | +++ |
| 648 | +++ |
| 649 | ++ |
| 650 | ++ |
| 651 | +++ |
| 652 | ++ |
| 653 | + |
| 654 | +++ |
| 655 | +++ |
| 656 | +++ |
| 657 | +++ |
| 658 | +++ |
| 659 | ++ |
| 660 | + |
| 661 | +++ |
| 662 | + |
| 663 | +++ |
| 664 | +++ |
| 665 | +++ |
| 666 | ++ |
| 667 | +++ |
| 668 | +++ |
| 669 | +++ |
| 670 | ++ |
| 671 | +++ |
| 672 | +++ |
| 673 | +++ |
| 674 | +++ |
| 675 | +++ |
| 676 | +++ |
| 677 | ++ |
| 678 | +++ |

TABLE 3-continued

| Cmpd. No. | EC30 (µM) |
| --- | --- |
| 679 | +++ |
| 680 | +++ |
| 681 | +++ |
| 682 | +++ |
| 683 | +++ |
| 684 | +++ |
| 685 | +++ |
| 686 | +++ |
| 687 | ++ |
| 688 | +++ |
| 689 | +++ |
| 690 | ++ |
| 691 | +++ |
| 692 | +++ |
| 693 | +++ |
| 694 | +++ |
| 695 | +++ |
| 696 | +++ |
| 697 | +++ |
| 698 | |
| 699 | +++ |
| 700 | +++ |
| 701 | +++ |
| 702 | ++ |
| 703 | +++ |
| 704 | ++ |
| 705 | +++ |
| 706 | +++ |
| 707 | + |
| 708 | +++ |
| 709 | +++ |
| 710 | +++ |
| 711 | +++ |
| 712 | +++ |
| 713 | ++ |
| 714 | +++ |
| 715 | +++ |
| 716 | +++ |
| 717 | +++ |
| 718 | +++ |
| 719 | +++ |
| 720 | +++ |
| 721 | ++ |
| 722 | + |
| 723 | ++ |
| 724 | +++ |
| 725 | +++ |
| 726 | ++ |
| 727 | + |
| 728 | ++ |
| 729 | ++ |
| 730 | +++ |
| 731 | +++ |
| 732 | +++ |
| 733 | +++ |
| 734 | +++ |
| 735 | +++ |
| 736 | +++ |
| 737 | +++ |
| 738 | +++ |
| 739 | ++ |
| 740 | ++ |
| 741 | +++ |
| 742 | +++ |
| 743 | +++ |
| 744 | +++ |
| 745 | ++ |
| 746 | +++ |
| 747 | +++ |
| 748 | ++ |
| 749 | +++ |
| 750 | +++ |
| 751 | +++ |
| 752 | ++ |
| 753 | ++ |
| 754 | +++ |
| 755 | ++ |
| 756 | +++ |
| 757 | +++ |
| 758 | ++ |
| 759 | +++ |
| 760 | ++ |
| 761 | +++ |
| 762 | ++ |
| 763 | +++ |
| 764 | +++ |
| 765 | ++ |
| 766 | ++ |
| 767 | +++ |
| 768 | ++ |
| 769 | +++ |
| 770 | ++ |
| 771 | +++ |
| 772 | +++ |
| 773 | +++ |
| 774 | +++ |
| 775 | +++ |
| 776 | +++ |
| 777 | +++ |
| 778 | +++ |
| 779 | +++ |
| 780 | +++ |
| 781 | + |
| 782 | +++ |
| 783 | +++ |
| 784 | +++ |
| 785 | +++ |
| 786 | + |
| 787 | +++ |
| 788 | +++ |
| 789 | +++ |
| 790 | +++ |
| 791 | ++ |
| 792 | ++ |
| 793 | +++ |
| 794 | +++ |
| 795 | +++ |
| 796 | +++ |
| 797 | + |
| 798 | +++ |
| 799 | + |
| 800 | ++ |
| 801 | + |
| 802 | +++ |
| 803 | +++ |
| 804 | +++ |
| 805 | +++ |
| 806 | ++ |
| 807 | +++ |
| 808 | ++ |
| 809 | ++ |
| 810 | ++ |
| 811 | +++ |
| 812 | ++ |
| 813 | +++ |
| 814 | +++ |
| 815 | ++ |
| 816 | ++ |
| 817 | +++ |
| 818 | +++ |
| 819 | + |
| 820 | + |
| 821 | ++ |
| 822 | +++ |
| 823 | + |
| 824 | ++ |
| 825 | ++ |
| 826 | +++ |
| 827 | +++ |
| 828 | +++ |
| 829 | +++ |
| 830 | +++ |
| 831 | +++ |
| 832 | +++ |

TABLE 3-continued

| Cmpd. No. | EC30 (μM) |
|---|---|
| 833 | +++ |
| 834 | +++ |
| 835 | ++ |
| 836 | ++ |
| 837 | +++ |
| 838 | ++ |
| 839 | ++ |
| 840 | +++ |
| 841 | +++ |
| 842 | +++ |
| 843 | ++ |
| 844 | ++ |
| 845 | +++ |
| 846 | +++ |
| 847 | +++ |
| 848 | +++ |
| 849 | + |
| 850 | +++ |
| 851 | +++ |
| 852 | ++ |
| 853 | +++ |
| 854 | ++ |
| 855 | + |
| 856 | ++ |
| 857 | +++ |
| 858 | ++ |
| 859 | +++ |
| 860 | ++ |
| 861 | ++ |
| 862 | +++ |
| 863 | ++ |
| 864 | +++ |
| 865 | +++ |
| 866 | +++ |
| 867 | +++ |
| 868 | +++ |
| 869 | +++ |
| 870 | ++ |
| 871 | +++ |
| 872 | ++ |
| 873 | +++ |
| 874 | +++ |
| 875 | +++ |
| 876 | +++ |
| 877 | +++ |
| 878 | ++ |
| 879 | + |
| 880 | ++ |
| 881 | +++ |
| 882 | +++ |
| 883 | ++ |
| 884 | ++ |
| 885 | ++ |
| 886 | +++ |
| 887 | +++ |
| 888 | ++ |
| 889 | ++ |
| 890 | +++ |
| 891 | +++ |
| 892 | ++ |
| 893 | +++ |
| 894 | +++ |
| 895 | +++ |
| 896 | +++ |
| 897 | +++ |
| 898 | +++ |
| 899 | +++ |
| 900 | +++ |
| 901 | ++ |
| 902 | +++ |
| 903 | ++ |
| 904 | +++ |
| 905 | +++ |
| 906 | +++ |
| 907 | +++ |
| 908 | + |
| 909 | +++ |

TABLE 3-continued

| Cmpd. No. | EC30 (μM) |
|---|---|
| 910 | +++ |
| 911 | +++ |
| 912 | +++ |
| 913 | ++ |
| 914 | +++ |
| 915 | +++ |
| 916 | +++ |
| 917 | ++ |
| 918 | +++ |
| 919 | +++ |
| 920 | +++ |
| 921 | ++ |
| 922 | +++ |
| 923 | +++ |
| 924 | +++ |
| 925 | +++ |
| 926 | +++ |
| 927 | ++ |
| 928 | +++ |
| 929 | ++ |
| 930 | ++ |
| 931 | +++ |
| 932 | + |
| 933 | +++ |
| 934 | +++ |
| 935 | ++ |
| 936 | ++ |
| 937 | +++ |
| 938 | ++ |
| 939 | +++ |
| 940 | +++ |
| 941 | +++ |
| 942 | +++ |
| 943 | + |
| 944 | +++ |
| 945 | +++ |
| 946 | ++ |
| 947 | +++ |
| 948 | +++ |
| 949 | +++ |
| 950 | +++ |
| 951 | +++ |
| 952 | +++ |
| 953 | +++ |
| 954 | +++ |
| 955 | ++ |
| 956 | +++ |
| 957 | +++ |
| 958 | +++ |
| 959 | +++ |
| 960 | ++ |
| 961 | +++ |
| 962 | ++ |
| 963 | ++ |
| 964 | +++ |
| 965 | +++ |
| 966 | + |
| 967 | +++ |
| 968 | +++ |
| 969 | +++ |
| 970 | |
| 971 | +++ |
| 972 | +++ |
| 973 | +++ |
| 974 | +++ |
| 975 | ++ |
| 976 | ++ |
| 977 | ++ |
| 978 | +++ |
| 979 | +++ |
| 980 | ++ |
| 981 | ++ |
| 982 | ++ |
| 983 | ++ |
| 984 | +++ |
| 985 | +++ |
| 986 | ++ |

TABLE 3-continued

| Cmpd. No. | EC30 (μM) |
|---|---|
| 987 | +++ |
| 988 | +++ |
| 989 | +++ |
| 990 | +++ |
| 991 | +++ |
| 992 | +++ |
| 993 | +++ |
| 994 | +++ |
| 995 | +++ |
| 996 | +++ |
| 997 | ++ |
| 998 | ++ |
| 999 | ++ |
| 1000 | +++ |
| 1001 | ++ |
| 1002 | +++ |
| 1003 | + |
| 1004 | +++ |
| 1005 | +++ |
| 1006 | +++ |
| 1007 | +++ |
| 1008 | +++ |
| 1009 | +++ |
| 1010 | +++ |
| 1011 | +++ |
| 1012 | +++ |
| 1013 | +++ |
| 1014 | +++ |
| 1015 | +++ |
| 1016 | +++ |
| 1017 | ++ |
| 1018 | ++ |
| 1019 | +++ |
| 1020 | +++ |
| 1021 | +++ |
| 1022 | ++ |
| 1023 | +++ |
| 1024 | ++ |
| 1025 | +++ |
| 1026 | ++ |
| 1027 | ++ |
| 1028 | ++ |
| 1029 | ++ |
| 1030 | +++ |
| 1031 | +++ |
| 1032 | +++ |
| 1033 | +++ |
| 1034 | +++ |
| 1035 | +++ |
| 1036 | + |
| 1037 | ++ |
| 1038 | ++ |
| 1039 | +++ |
| 1040 | +++ |
| 1041 | +++ |
| 1042 | +++ |
| 1043 | +++ |
| 1044 | +++ |
| 1045 | ++ |
| 1046 | ++ |
| 1047 | +++ |
| 1048 | +++ |
| 1049 | +++ |
| 1050 | ++ |
| 1051 | +++ |
| 1052 | +++ |
| 1053 | ++ |
| 1054 | +++ |
| 1055 | ++ |
| 1056 | +++ |
| 1057 | + |
| 1058 | +++ |
| 1059 | +++ |
| 1060 | +++ |
| 1061 | +++ |
| 1062 | +++ |
| 1063 | +++ |
| 1064 | +++ |
| 1065 | +++ |
| 1066 | ++ |
| 1067 | +++ |
| 1068 | +++ |
| 1069 | +++ |
| 1070 | +++ |
| 1071 | +++ |
| 1072 | ++ |
| 1073 | + |
| 1074 | ++ |
| 1075 | +++ |
| 1076 | +++ |
| 1077 | +++ |
| 1078 | ++ |
| 1079 | +++ |
| 1080 | +++ |
| 1081 | ++ |
| 1082 | + |
| 1083 | +++ |
| 1084 | ++ |
| 1085 | +++ |
| 1086 | ++ |
| 1087 | +++ |
| 1088 | +++ |
| 1089 | +++ |
| 1090 | +++ |
| 1091 | +++ |
| 1092 | ++ |
| 1093 | ++ |
| 1094 | +++ |
| 1095 | ++ |
| 1096 | ++ |
| 1097 | +++ |
| 1098 | +++ |
| 1099 | +++ |
| 1100 | +++ |
| 1101 | +++ |
| 1102 | +++ |
| 1103 | +++ |
| 1104 | +++ |
| 1105 | + |
| 1106 | + |
| 1107 | +++ |
| 1108 | +++ |
| 1109 | ++ |
| 1110 | +++ |
| 1111 | +++ |
| 1112 | ++ |
| 1113 | +++ |
| 1114 | |
| 1115 | + |
| 1116 | ++ |
| 1117 | +++ |
| 1118 | +++ |
| 1119 | ++ |
| 1120 | +++ |
| 1121 | +++ |
| 1122 | ++ |
| 1123 | +++ |
| 1124 | +++ |
| 1125 | ++ |
| 1126 | + |
| 1127 | +++ |
| 1128 | ++ |
| 1129 | ++ |
| 1130 | ++ |
| 1131 | +++ |
| 1132 | +++ |
| 1133 | +++ |
| 1134 | +++ |
| 1135 | +++ |
| 1136 | +++ |
| 1137 | ++ |
| 1138 | +++ |
| 1139 | +++ |
| 1140 | +++ |

TABLE 3-continued

| Cmpd. No. | EC30 (µM) |
|---|---|
| 1141 | ++ |
| 1142 | ++ |
| 1143 | ++ |
| 1144 | +++ |
| 1145 | +++ |
| 1146 | ++ |
| 1147 | ++ |
| 1148 | +++ |
| 1149 | +++ |
| 1150 | +++ |
| 1151 | ++ |
| 1152 | + |
| 1153 | +++ |
| 1154 | ++ |
| 1155 | ++ |
| 1156 | +++ |
| 1157 | +++ |
| 1158 | +++ |
| 1159 | +++ |
| 1160 | +++ |
| 1161 | +++ |
| 1162 | +++ |
| 1163 | +++ |
| 1164 | ++ |
| 1165 | ++ |
| 1166 | +++ |
| 1167 | +++ |
| 1168 | +++ |
| 1169 | ++ |
| 1170 | +++ |
| 1171 | +++ |
| 1172 | ++ |
| 1173 | +++ |
| 1174 | +++ |
| 1175 | +++ |
| 1176 | +++ |
| 1177 | ++ |
| 1178 | +++ |
| 1179 | ++ |
| 1180 | +++ |
| 1181 | +++ |
| 1182 | ++ |
| 1183 | + |
| 1184 | +++ |
| 1185 | +++ |
| 1186 | +++ |
| 1187 | +++ |
| 1188 | +++ |
| 1189 | +++ |
| 1190 | +++ |
| 1191 | ++ |
| 1192 | +++ |
| 1193 | +++ |
| 1194 | +++ |
| 1195 | + |
| 1196 | ++ |
| 1197 | +++ |
| 1198 | +++ |
| 1199 | ++ |
| 1200 | ++ |
| 1201 | +++ |
| 1202 | +++ |
| 1203 | + |
| 1204 | + |
| 1205 | +++ |
| 1206 | ++ |
| 1207 | +++ |
| 1208 | +++ |
| 1209 | +++ |
| 1210 | +++ |
| 1211 | ++ |
| 1212 | +++ |
| 1213 | ++ |
| 1214 | ++ |
| 1215 | ++ |
| 1216 | +++ |
| 1217 | + |
| 1218 | +++ |
| 1219 | ++ |
| 1220 | +++ |
| 1221 | +++ |
| 1222 | +++ |
| 1223 | +++ |
| 1224 | ++ |
| 1225 | +++ |
| 1226 | +++ |
| 1227 | +++ |
| 1228 | ++ |
| 1229 | +++ |
| 1230 | ++ |
| 1231 | +++ |
| 1232 | +++ |
| 1233 | ++ |
| 1234 | +++ |
| 1235 | +++ |
| 1236 | ++ |
| 1237 | ++ |
| 1238 | +++ |
| 1239 | +++ |
| 1240 | +++ |
| 1241 | +++ |
| 1242 | +++ |
| 1243 | +++ |
| 1244 | +++ |
| 1245 | + |
| 1246 | +++ |
| 1247 | +++ |
| 1248 | +++ |
| 1249 | +++ |
| 1250 | +++ |
| 1251 | ++ |
| 1252 | +++ |
| 1253 | ++ |
| 1254 | +++ |
| 1255 | +++ |
| 1256 | ++ |
| 1257 | ++ |
| 1258 | +++ |
| 1259 | +++ |
| 1260 | +++ |
| 1261 | +++ |
| 1262 | ++ |
| 1263 | +++ |
| 1264 | +++ |
| 1265 | ++ |
| 1266 | +++ |
| 1267 | +++ |
| 1268 | +++ |
| 1269 | +++ |
| 1270 | +++ |
| 1271 | +++ |
| 1272 | +++ |
| 1273 | +++ |
| 1274 | +++ |
| 1275 | +++ |
| 1276 | ++ |
| 1277 | +++ |
| 1278 | + |
| 1279 | +++ |
| 1280 | +++ |
| 1281 | ++ |
| 1282 | +++ |
| 1283 | +++ |
| 1284 | +++ |
| 1285 | +++ |
| 1286 | +++ |
| 1287 | +++ |
| 1288 | ++ |
| 1289 | +++ |
| 1290 | +++ |
| 1291 | ++ |
| 1292 | + |
| 1293 | ++ |
| 1294 | +++ |

TABLE 3-continued

| Cmpd. No. | EC30 (μM) |
|---|---|
| 1295 | +++ |
| 1296 | + |
| 1297 | +++ |
| 1298 | ++ |
| 1299 | ++ |
| 1300 | +++ |
| 1301 | ++ |
| 1302 | ++ |
| 1303 | +++ |
| 1304 | +++ |
| 1305 | +++ |
| 1306 | +++ |
| 1307 | ++ |
| 1308 | +++ |
| 1309 | +++ |
| 1310 | +++ |
| 1311 | +++ |
| 1312 | ++ |
| 1313 | +++ |
| 1314 | +++ |
| 1315 | +++ |
| 1316 | +++ |
| 1317 | +++ |
| 1318 | +++ |
| 1319 | +++ |
| 1320 | +++ |
| 1321 | ++ |
| 1322 | ++ |
| 1323 | + |
| 1324 | +++ |
| 1325 | +++ |
| 1326 | ++ |
| 1327 | +++ |
| 1328 | +++ |
| 1329 | ++ |
| 1330 | +++ |
| 1331 | + |
| 1332 | +++ |
| 1333 | +++ |
| 1334 | +++ |
| 1335 | +++ |
| 1336 | +++ |
| 1337 | +++ |
| 1338 | ++ |
| 1339 | +++ |
| 1340 | +++ |
| 1341 | +++ |
| 1342 | +++ |
| 1343 | +++ |
| 1344 | ++ |
| 1345 | +++ |
| 1346 | +++ |
| 1347 | +++ |
| 1348 | +++ |
| 1349 | +++ |
| 1350 | + |
| 1351 | ++ |
| 1352 | +++ |
| 1353 | + |
| 1354 | +++ |
| 1355 | ++ |
| 1356 | +++ |
| 1357 | +++ |
| 1358 | +++ |
| 1359 | |
| 1360 | +++ |
| 1361 | +++ |
| 1362 | +++ |
| 1363 | +++ |
| 1364 | +++ |
| 1365 | +++ |
| 1366 | +++ |
| 1367 | +++ |
| 1368 | +++ |
| 1369 | +++ |
| 1370 | +++ |
| 1371 | +++ |

TABLE 3-continued

| Cmpd. No. | EC30 (μM) |
|---|---|
| 1372 | +++ |
| 1373 | +++ |
| 1374 | +++ |
| 1375 | ++ |
| 1376 | +++ |
| 1377 | +++ |
| 1378 | +++ |
| 1379 | +++ |
| 1380 | +++ |
| 1381 | ++ |
| 1382 | + |
| 1383 | +++ |
| 1384 | +++ |
| 1385 | +++ |
| 1386 | ++ |
| 1387 | +++ |
| 1388 | +++ |
| 1389 | +++ |
| 1390 | +++ |
| 1391 | +++ |
| 1392 | +++ |
| 1393 | +++ |
| 1394 | +++ |
| 1395 | +++ |
| 1396 | +++ |
| 1397 | +++ |
| 1398 | ++ |
| 1399 | +++ |
| 1400 | +++ |
| 1401 | +++ |
| 1402 | +++ |
| 1403 | +++ |
| 1404 | +++ |
| 1405 | +++ |
| 1406 | +++ |
| 1407 | +++ |
| 1408 | +++ |
| 1409 | +++ |
| 1410 | +++ |
| 1411 | +++ |
| 1412 | +++ |
| 1413 | +++ |
| 1414 | +++ |
| 1415 | +++ |
| 1416 | +++ |
| 1417 | ++ |
| 1418 | +++ |
| 1419 | +++ |
| 1420 | ++ |
| 1421 | +++ |
| 1422 | +++ |
| 1423 | +++ |
| 1424 | +++ |
| 1425 | +++ |
| 1426 | +++ |
| 1427 | +++ |
| 1428 | +++ |
| 1429 | +++ |
| 1430 | +++ |
| 1431 | +++ |
| 1432 | +++ |
| 1433 | ++ |
| 1434 | +++ |
| 1435 | +++ |
| 1436 | ++ |
| 1437 | ++ |
| 1438 | +++ |
| 1439 | ++ |
| 1440 | +++ |
| 1441 | ++ |
| 1442 | +++ |
| 1443 | +++ |
| 1444 | +++ |
| 1445 | +++ |
| 1446 | +++ |
| 1447 | +++ |
| 1448 | |

TABLE 3-continued

| Cmpd. No. | EC30 (µM) |
|---|---|
| 1449 | +++ |
| 1450 | +++ |
| 1451 | +++ |
| 1452 | +++ |
| 1453 | +++ |
| 1454 | +++ |
| 1455 | +++ |
| 1456 | +++ |
| 1457 | +++ |
| 1458 | +++ |
| 1459 | +++ |
| 1460 | +++ |
| 1461 | +++ |
| 1462 | +++ |
| 1463 | +++ |
| 1464 | +++ |
| 1465 | +++ |
| 1466 | ++ |
| 1467 | +++ |
| 1468 | +++ |
| 1469 | ++ |
| 1470 | +++ |
| 1471 | +++ |
| 1472 | +++ |
| 1473 | +++ |
| 1474 | +++ |
| 1475 | +++ |
| 1476 | +++ |
| 1477 | +++ |
| 1478 | +++ |
| 1479 | +++ |
| 1480 | +++ |
| 1481 | +++ |
| 1482 | +++ |
| 1483 | +++ |
| 1484 | +++ |
| 1485 | +++ |
| 1486 | +++ |
| 1487 | +++ |
| 1488 | +++ |
| 1489 | +++ |
| 1490 | +++ |
| 1491 | ++ |
| 1492 | ++ |
| 1493 | +++ |
| 1494 | +++ |
| 1495 | +++ |
| 1496 | +++ |
| 1497 | +++ |
| 1498 | +++ |
| 1499 | ++ |
| 1500 | +++ |
| 1501 | +++ |
| 1502 | +++ |
| 1503 | ++ |
| 1504 | +++ |
| 1505 | +++ |
| 1506 | +++ |
| 1507 | ++ |
| 1508 | +++ |
| 1509 | +++ |
| 1510 | +++ |
| 1511 | +++ |
| 1512 | +++ |
| 1513 | +++ |
| 1514 | +++ |
| 1515 | +++ |
| 1516 | +++ |
| 1517 | +++ |
| 1518 | +++ |
| 1519 | +++ |
| 1520 | +++ |
| 1521 | +++ |
| 1522 | +++ |
| 1523 | +++ |
| 1524 | +++ |
| 1525 | +++ |
| 1526 | +++ |
| 1527 | +++ |
| 1528 | ++ |
| 1529 | +++ |
| 1530 | +++ |
| 1531 | ++ |
| 1532 | +++ |
| 1533 | +++ |
| 1534 | ++ |
| 1535 | +++ |
| 1536 | ++ |
| 1537 | +++ |
| 1538 | + |
| 1539 | +++ |
| 1540 | + |
| 1541 | +++ |
| 1542 | +++ |
| 1543 | |
| 1544 | +++ |
| 1545 | +++ |
| 1546 | +++ |
| 1547 | ++ |
| 1548 | +++ |
| 1549 | +++ |
| 1550 | ++ |
| 1551 | +++ |
| 1552 | +++ |
| 1553 | +++ |
| 1554 | +++ |
| 1555 | +++ |
| 1556 | +++ |
| 1557 | +++ |
| 1558 | ++ |
| 1559 | +++ |
| 1560 | +++ |
| 1561 | +++ |
| 1562 | +++ |
| 1563 | +++ |
| 1564 | ++ |
| 1565 | + |
| 1566 | +++ |
| 1567 | +++ |
| 1568 | +++ |
| 1569 | +++ |
| 1570 | +++ |
| 1571 | +++ |
| 1572 | +++ |
| 1573 | +++ |
| 1574 | ++ |
| 1575 | ++ |
| 1576 | +++ |
| 1577 | +++ |
| 1578 | +++ |
| 1579 | +++ |
| 1580 | +++ |
| 1581 | +++ |
| 1582 | +++ |
| 1583 | ++ |
| 1584 | +++ |
| 1585 | +++ |
| 1586 | +++ |
| 1587 | +++ |
| 1588 | +++ |
| 1589 | +++ |
| 1590 | +++ |
| 1591 | +++ |
| 1592 | +++ |
| 1593 | +++ |
| 1594 | +++ |
| 1595 | +++ |
| 1596 | +++ |
| 1597 | +++ |
| 1598 | +++ |
| 1599 | +++ |
| 1600 | +++ |
| 1601 | +++ |
| 1602 | +++ |

TABLE 3-continued

| Cmpd. No. | EC30 (µM) |
|---|---|
| 1603 | ++ |
| 1604 | +++ |
| 1605 | +++ |
| 1606 | +++ |
| 1607 | ++ |
| 1608 | +++ |
| 1609 | +++ |
| 1610 | +++ |
| 1611 | +++ |
| 1612 | +++ |
| 1613 | +++ |
| 1614 | +++ |
| 1615 | +++ |
| 1616 | +++ |
| 1617 | +++ |
| 1618 | +++ |
| 1619 | +++ |
| 1620 | +++ |
| 1621 | +++ |
| 1622 | +++ |
| 1623 | +++ |
| 1624 | +++ |
| 1625 | ++ |
| 1626 | +++ |
| 1627 | +++ |
| 1628 | +++ |
| 1629 | +++ |
| 1630 | +++ |
| 1631 | ++ |
| 1632 | ++ |
| 1633 | +++ |
| 1634 | ++ |
| 1635 | +++ |
| 1636 | ++ |
| 1637 | +++ |
| 1638 | +++ |
| 1639 | +++ |
| 1640 | +++ |
| 1641 | +++ |
| 1642 | +++ |
| 1643 | ++ |
| 1644 | +++ |
| 1645 | +++ |
| 1646 | +++ |
| 1647 | +++ |
| 1648 | +++ |
| 1649 | ++ |
| 1650 | +++ |
| 1651 | ++ |
| 1652 | +++ |
| 1653 | +++ |
| 1654 | +++ |
| 1655 | +++ |
| 1656 | +++ |
| 1657 | +++ |
| 1658 | ++ |
| 1659 | +++ |
| 1660 | +++ |
| 1661 | +++ |
| 1662 | ++ |
| 1663 | +++ |
| 1664 | +++ |
| 1665 | +++ |
| 1666 | +++ |
| 1667 | ++ |
| 1668 | +++ |
| 1669 | +++ |
| 1670 | ++ |
| 1671 | +++ |
| 1672 | +++ |
| 1673 | +++ |
| 1674 | +++ |
| 1675 | ++ |
| 1676 | +++ |
| 1677 | +++ |
| 1678 | + |
| 1679 | +++ |
| 1680 | +++ |
| 1681 | +++ |
| 1682 | +++ |
| 1683 | +++ |
| 1684 | +++ |
| 1685 | +++ |
| 1686 | +++ |
| 1687 | +++ |
| 1688 | +++ |
| 1689 | +++ |
| 1690 | +++ |
| 1691 | ++ |
| 1692 | ++ |
| 1693 | +++ |
| 1694 | +++ |
| 1695 | +++ |
| 1696 | +++ |
| 1697 | +++ |
| 1698 | +++ |
| 1699 | +++ |
| 1700 | +++ |
| 1701 | +++ |
| 1702 | +++ |
| 1703 | +++ |
| 1704 | +++ |
| 1705 | +++ |
| 1706 | ++ |
| 1707 | ++ |
| 1708 | +++ |
| 1709 | +++ |
| 1710 | +++ |
| 1711 | +++ |
| 1712 | +++ |
| 1713 | +++ |
| 1714 | ++ |
| 1715 | +++ |
| 1716 | ++ |
| 1717 | +++ |
| 1718 | +++ |
| 1719 | +++ |
| 1720 | +++ |
| 1721 | +++ |
| 1722 | +++ |
| 1723 | +++ |
| 1724 | +++ |
| 1725 | ++ |
| 1726 | +++ |
| 1727 | +++ |
| 1728 | +++ |
| 1729 | +++ |
| 1730 | +++ |
| 1731 | +++ |
| 1732 | |
| 1733 | ++ |
| 1734 | +++ |
| 1735 | +++ |
| 1736 | ++ |
| 1737 | +++ |
| 1738 | +++ |
| 1739 | +++ |
| 1740 | +++ |
| 1741 | +++ |
| 1742 | +++ |
| 1743 | +++ |
| 1744 | ++ |
| 1745 | +++ |
| 1746 | +++ |
| 1747 | +++ |
| 1748 | +++ |
| 1749 | +++ |
| 1750 | +++ |
| 1751 | +++ |
| 1752 | ++ |
| 1753 | ++ |
| 1754 | +++ |
| 1755 | ++ |
| 1756 | +++ |

TABLE 3-continued

| Cmpd. No. | EC30 (μM) |
|---|---|
| 1757 | +++ |
| 1758 | +++ |
| 1759 | +++ |
| 1760 | ++ |
| 1761 | ++ |
| 1762 | +++ |
| 1763 | +++ |
| 1764 | ++ |
| 1765 | +++ |
| 1766 | +++ |
| 1767 | +++ |
| 1768 | ++ |
| 1769 | ++ |
| 1770 | +++ |
| 1771 | +++ |
| 1772 | ++ |
| 1773 | +++ |
| 1774 | +++ |
| 1775 | +++ |
| 1776 | +++ |
| 1777 | +++ |
| 1778 | +++ |
| 1779 | +++ |
| 1780 | ++ |
| 1781 | +++ |
| 1782 | +++ |
| 1783 | +++ |
| 1784 | +++ |
| 1785 | +++ |
| 1786 | ++ |
| 1787 | ++ |
| 1788 | +++ |
| 1789 | +++ |
| 1790 | +++ |
| 1791 | +++ |
| 1792 | +++ |
| 1793 | +++ |
| 1794 | ++ |
| 1795 | +++ |
| 1796 | +++ |
| 1797 | +++ |
| 1798 | +++ |
| 1799 | +++ |
| 1800 | +++ |
| 1801 | +++ |
| 1802 | +++ |
| 1803 | +++ |
| 1804 | +++ |
| 1805 | ++ |
| 1806 | +++ |
| 1807 | +++ |
| 1808 | +++ |
| 1809 | +++ |
| 1810 | +++ |
| 1811 | +++ |
| 1812 | ++ |
| 1813 | +++ |
| 1814 | +++ |
| 1815 | +++ |
| 1816 | +++ |
| 1817 | +++ |
| 1818 | +++ |
| 1819 | ++ |
| 1820 | ++ |
| 1821 | +++ |
| 1822 | +++ |
| 1823 | +++ |
| 1824 | +++ |
| 1825 | +++ |
| 1826 | +++ |
| 1827 | +++ |
| 1828 | +++ |
| 1829 | +++ |
| 1830 | +++ |
| 1831 | +++ |
| 1832 | +++ |
| 1833 | +++ |

TABLE 3-continued

| Cmpd. No. | EC30 (μM) |
|---|---|
| 1834 | +++ |
| 1835 | +++ |
| 1836 | +++ |
| 1837 | +++ |
| 1838 | +++ |
| 1839 | +++ |
| 1840 | +++ |
| 1841 | +++ |
| 1842 | +++ |
| 1843 | +++ |
| 1844 | +++ |
| 1845 | +++ |
| 1846 | +++ |
| 1847 | +++ |
| 1848 | +++ |
| 1849 | ++ |
| 1850 | +++ |
| 1851 | +++ |
| 1852 | +++ |
| 1853 | ++ |
| 1854 | +++ |
| 1855 | +++ |
| 1856 | +++ |
| 1857 | +++ |
| 1858 | ++ |
| 1859 | +++ |
| 1860 | +++ |
| 1861 | +++ |
| 1862 | +++ |
| 1863 | +++ |
| 1864 | +++ |
| 1865 | ++ |
| 1866 | +++ |
| 1867 | +++ |
| 1868 | +++ |
| 1869 | +++ |
| 1870 | ++ |
| 1871 | +++ |
| 1872 | +++ |
| 1873 | +++ |
| 1874 | +++ |
| 1875 | ++ |
| 1876 | +++ |
| 1877 | ++ |
| 1878 | ++ |
| 1879 | +++ |
| 1880 | ++ |
| 1881 | +++ |
| 1882 | + |
| 1883 | +++ |
| 1884 | +++ |
| 1885 | +++ |
| 1886 | ++ |
| 1887 | +++ |
| 1888 | ++ |
| 1889 | +++ |
| 1890 | ++ |
| 1891 | +++ |
| 1892 | +++ |
| 1893 | +++ |
| 1894 | +++ |
| 1895 | +++ |
| 1896 | +++ |
| 1897 | +++ |
| 1898 | ++ |
| 1899 | +++ |
| 1900 | ++ |
| 1901 | +++ |
| 1902 | +++ |
| 1903 | +++ |
| 1904 | +++ |
| 1905 | +++ |
| 1906 | +++ |
| 1907 | +++ |
| 1908 | +++ |
| 1909 | +++ |
| 1910 | +++ |

TABLE 3-continued

| Cmpd. No. | EC30 (μM) |
|---|---|
| 1911 | +++ |
| 1912 | +++ |
| 1913 | +++ |
| 1914 | +++ |
| 1915 | +++ |
| 1916 | +++ |
| 1917 | +++ |
| 1918 | +++ |
| 1919 | +++ |
| 1920 | ++ |
| 1921 | +++ |
| 1922 | +++ |
| 1923 | ++ |
| 1924 | +++ |
| 1925 | +++ |
| 1926 | +++ |
| 1927 | +++ |
| 1928 | ++ |
| 1929 | +++ |
| 1930 | +++ |
| 1931 | +++ |
| 1932 | +++ |
| 1933 | +++ |
| 1934 | +++ |
| 1935 | +++ |
| 1936 | +++ |
| 1937 | ++ |
| 1938 | +++ |
| 1939 | ++ |
| 1940 | +++ |
| 1941 | +++ |
| 1942 | ++ |
| 1943 | ++ |
| 1944 | +++ |
| 1945 | +++ |
| 1946 | +++ |
| 1947 | ++ |
| 1948 | +++ |
| 1949 | +++ |
| 1950 | +++ |
| 1951 | +++ |
| 1952 | +++ |
| 1953 | +++ |
| 1954 | +++ |
| 1955 | +++ |
| 1956 | +++ |
| 1957 | ++ |
| 1958 | +++ |
| 1959 | +++ |
| 1960 | +++ |
| 1961 | +++ |
| 1962 | +++ |
| 1963 | +++ |
| 1964 | +++ |
| 1965 | +++ |
| 1966 | +++ |
| 1967 | ++ |
| 1968 | +++ |
| 1969 | +++ |
| 1970 | +++ |
| 1971 | +++ |
| 1972 | +++ |
| 1973 | +++ |
| 1974 | +++ |
| 1975 | +++ |
| 1976 | +++ |
| 1977 | +++ |
| 1978 | +++ |
| 1979 | +++ |
| 1980 | +++ |
| 1981 | +++ |
| 1982 | ++ |
| 1983 | +++ |
| 1984 | ++ |
| 1985 | ++ |
| 1986 | +++ |
| 1987 | +++ |
| 1988 | +++ |
| 1989 | +++ |
| 1990 | +++ |
| 1991 | +++ |
| 1992 | +++ |
| 1993 | +++ |
| 1994 | +++ |
| 1995 | +++ |
| 1996 | +++ |
| 1997 | ++ |
| 1998 | +++ |
| 1999 | ++ |
| 2000 | +++ |
| 2001 | +++ |
| 2002 | +++ |
| 2003 | +++ |
| 2004 | +++ |
| 2005 | ++ |
| 2006 | +++ |
| 2007 | +++ |
| 2008 | ++ |
| 2009 | +++ |
| 2010 | +++ |
| 2011 | +++ |
| 2012 | +++ |
| 2013 | +++ |
| 2014 | +++ |
| 2015 | +++ |
| 2016 | ++ |
| 2017 | +++ |
| 2018 | +++ |
| 2019 | +++ |
| 2020 | +++ |
| 2021 | ++ |
| 2022 | +++ |
| 2023 | +++ |
| 2024 | ++ |
| 2025 | +++ |
| 2026 | +++ |
| 2027 | +++ |
| 2028 | +++ |
| 2029 | +++ |
| 2030 | +++ |
| 2031 | +++ |
| 2032 | ++ |
| 2033 | +++ |
| 2034 | +++ |
| 2035 | +++ |
| 2036 | +++ |
| 2037 | +++ |
| 2038 | +++ |
| 2039 | +++ |
| 2040 | +++ |
| 2041 | +++ |
| 2042 | +++ |
| 2043 | +++ |
| 2044 | +++ |
| 2045 | ++ |
| 2046 | +++ |
| 2047 | ++ |
| 2048 | +++ |
| 2049 | +++ |
| 2050 | +++ |
| 2051 | +++ |
| 2052 | +++ |
| 2053 | +++ |
| 2054 | +++ |
| 2055 | +++ |
| 2056 | ++ |
| 2057 | +++ |
| 2058 | +++ |
| 2059 | +++ |
| 2060 | +++ |
| 2061 | +++ |
| 2062 | +++ |
| 2063 | +++ |
| 2064 | +++ |

TABLE 3-continued

| Cmpd. No. | EC30 (μM) |
|---|---|
| 2065 | +++ |
| 2066 | +++ |
| 2067 | +++ |
| 2068 | +++ |
| 2069 | +++ |
| 2070 | +++ |
| 2071 | +++ |
| 2072 | ++ |
| 2073 | +++ |
| 2074 | ++ |
| 2075 | +++ |
| 2076 | +++ |
| 2077 | +++ |
| 2078 | ++ |
| 2079 | +++ |
| 2080 | ++ |
| 2081 | +++ |
| 2082 | ++ |
| 2083 | +++ |
| 2084 | +++ |
| 2085 | +++ |
| 2086 | +++ |
| 2087 | +++ |
| 2088 | ++ |
| 2089 | +++ |
| 2090 | +++ |
| 2091 | +++ |
| 2092 | +++ |
| 2093 | +++ |
| 2094 | +++ |
| 2095 | +++ |
| 2096 | +++ |
| 2097 | +++ |
| 2098 | +++ |
| 2099 | +++ |
| 2100 | +++ |
| 2101 | +++ |
| 2102 | +++ |
| 2103 | +++ |
| 2104 | +++ |
| 2105 | +++ |
| 2106 | +++ |
| 2107 | +++ |
| 2108 | +++ |
| 2109 | +++ |
| 2110 | + |
| 2111 | +++ |
| 2112 | ++ |
| 2113 | +++ |
| 2114 | +++ |
| 2115 | +++ |
| 2116 | +++ |
| 2117 | +++ |
| 2118 | +++ |
| 2119 | +++ |
| 2120 | +++ |
| 2121 | +++ |
| 2122 | +++ |
| 2123 | +++ |
| 2124 | +++ |
| 2125 | +++ |
| 2126 | +++ |
| 2127 | +++ |
| 2128 | ++ |
| 2129 | +++ |
| 2130 | +++ |
| 2131 | + |
| 2132 | +++ |
| 2133 | +++ |
| 2134 | +++ |
| 2135 | ++ |
| 2136 | +++ |
| 2137 | +++ |
| 2138 | +++ |
| 2139 | +++ |
| 2140 | ++ |
| 2141 | +++ |
| 2142 | +++ |
| 2143 | +++ |
| 2144 | +++ |
| 2145 | +++ |
| 2146 | +++ |
| 2147 | +++ |
| 2148 | ++ |
| 2149 | +++ |
| 2150 | +++ |
| 2151 | +++ |
| 2152 | ++ |
| 2153 | +++ |
| 2154 | +++ |
| 2155 | ++ |
| 2156 | +++ |
| 2157 | + |
| 2158 | ++ |
| 2159 | +++ |
| 2160 | ++ |
| 2161 | +++ |
| 2162 | +++ |
| 2163 | +++ |
| 2164 | +++ |
| 2165 | +++ |
| 2166 | ++ |
| 2167 | +++ |
| 2168 | +++ |
| 2169 | +++ |
| 2170 | +++ |
| 2171 | +++ |
| 2172 | +++ |
| 2173 | +++ |
| 2174 | ++ |
| 2175 | ++ |
| 2176 | +++ |
| 2177 | +++ |
| 2178 | +++ |
| 2179 | +++ |
| 2180 | +++ |
| 2181 | +++ |
| 2182 | +++ |
| 2183 | +++ |
| 2184 | +++ |
| 2185 | ++ |
| 2186 | +++ |
| 2187 | +++ |
| 2188 | +++ |
| 2189 | +++ |
| 2190 | +++ |
| 2191 | +++ |
| 2192 | +++ |
| 2193 | +++ |
| 2194 | +++ |
| 2195 | +++ |
| 2196 | +++ |
| 2197 | +++ |
| 2198 | +++ |
| 2199 | ++ |
| 2200 | ++ |
| 2201 | +++ |
| 2202 | +++ |
| 2203 | +++ |
| 2204 | +++ |
| 2205 | +++ |
| 2206 | +++ |
| 2207 | +++ |
| 2208 | +++ |
| 2209 | +++ |
| 2210 | +++ |
| 2211 | +++ |
| 2212 | ++ |
| 2213 | +++ |
| 2214 | +++ |
| 2215 | ++ |
| 2216 | +++ |
| 2217 | +++ |
| 2218 | +++ |

TABLE 3-continued

| Cmpd. No. | EC30 (μM) |
|---|---|
| 2219 | ++ |
| 2220 | ++ |
| 2221 | ++ |
| 2222 | ++ |
| 2223 | +++ |
| 2224 | +++ |
| 2225 | ++ |
| 2226 | ++ |
| 2227 | +++ |
| 2228 | +++ |
| 2229 | ++ |
| 2230 | +++ |
| 2231 | +++ |
| 2232 | ++ |
| 2233 | +++ |
| 2234 | +++ |
| 2235 | +++ |
| 2236 | +++ |
| 2237 | +++ |
| 2238 | +++ |
| 2239 | +++ |
| 2240 | ++ |
| 2241 | +++ |
| 2242 | +++ |
| 2243 | +++ |
| 2244 | +++ |
| 2245 | +++ |
| 2246 | +++ |
| 2247 | ++ |
| 2248 | +++ |
| 2249 | +++ |
| 2250 | +++ |
| 2251 | +++ |
| 2252 | +++ |
| 2253 | ++ |
| 2254 | ++ |
| 2255 | +++ |
| 2256 | +++ |
| 2257 | +++ |
| 2258 | +++ |
| 2259 | +++ |
| 2260 | +++ |
| 2261 | +++ |
| 2262 | +++ |
| 2263 | +++ |
| 2264 | +++ |
| 2265 | +++ |
| 2266 | +++ |
| 2267 | +++ |
| 2268 | +++ |
| 2269 | +++ |
| 2270 | +++ |
| 2271 | +++ |
| 2272 | +++ |
| 2273 | +++ |
| 2274 | ++ |
| 2275 | ++ |
| 2276 | +++ |
| 2277 | +++ |
| 2278 | +++ |
| 2279 | +++ |
| 2280 | +++ |
| 2281 | ++ |
| 2282 | +++ |
| 2283 | +++ |
| 2284 | +++ |
| 2285 | +++ |
| 2286 | +++ |
| 2287 | +++ |
| 2288 | +++ |
| 2289 | +++ |
| 2290 | ++ |
| 2291 | +++ |
| 2292 | +++ |
| 2293 | +++ |
| 2294 | ++ |
| 2295 | ++ |
| 2296 | +++ |
| 2297 | +++ |
| 2298 | +++ |
| 2299 | +++ |
| 2300 | ++ |
| 2301 | +++ |
| 2302 | +++ |
| 2303 | ++ |
| 2304 | +++ |
| 2305 | +++ |
| 2306 | +++ |
| 2307 | +++ |
| 2308 | +++ |
| 2309 | +++ |
| 2310 | +++ |
| 2311 | +++ |
| 2312 | +++ |
| 2313 | +++ |
| 2314 | ++ |
| 2315 | +++ |
| 2316 | +++ |
| 2317 | +++ |
| 2318 | +++ |
| 2319 | ++ |
| 2320 | +++ |
| 2321 | ++ |
| 2322 | +++ |
| 2323 | ++ |
| 2324 | ++ |
| 2325 | +++ |
| 2326 | +++ |
| 2327 | ++ |
| 2328 | ++ |
| 2329 | +++ |
| 2330 | +++ |
| 2331 | +++ |
| 2332 | +++ |
| 2333 | ++ |
| 2334 | +++ |
| 2335 | ++ |
| 2336 | +++ |
| 2337 | +++ |
| 2338 | +++ |
| 2339 | +++ |
| 2340 | +++ |
| 2341 | +++ |
| 2342 | +++ |
| 2343 | +++ |
| 2344 | +++ |
| 2345 | +++ |
| 2346 | +++ |
| 2347 | +++ |
| 2348 | +++ |
| 2349 | ++ |
| 2350 | ++ |
| 2351 | +++ |
| 2352 | +++ |
| 2353 | +++ |
| 2354 | ++ |
| 2355 | +++ |
| 2356 | +++ |
| 2357 | +++ |
| 2358 | +++ |
| 2359 | ++ |
| 2360 | ++ |
| 2361 | +++ |
| 2362 | +++ |
| 2363 | ++ |
| 2364 | +++ |
| 2365 | +++ |
| 2366 | +++ |
| 2367 | +++ |
| 2368 | +++ |
| 2369 | +++ |
| 2370 | +++ |
| 2371 | +++ |
| 2372 | +++ |

TABLE 3-continued

| Cmpd. No. | EC30 (µM) |
|---|---|
| 2373 | +++ |
| 2374 | +++ |
| 2375 | ++ |
| 2376 | +++ |
| 2377 | +++ |
| 2378 | +++ |
| 2379 | +++ |
| 2380 | +++ |
| 2381 | +++ |
| 2382 | +++ |
| 2383 | ++ |
| 2384 | +++ |
| 2385 | +++ |
| 2386 | +++ |
| 2387 | ++ |
| 2388 | +++ |
| 2389 | ++ |
| 2390 | +++ |
| 2391 | +++ |
| 2392 | +++ |
| 2393 | ++ |
| 2394 | +++ |
| 2395 | +++ |
| 2396 | ++ |
| 2397 | +++ |
| 2398 | +++ |
| 2399 | +++ |
| 2400 | ++ |
| 2401 | +++ |
| 2402 | +++ |
| 2403 | +++ |
| 2404 | +++ |
| 2405 | +++ |
| 2406 | +++ |
| 2407 | ++ |
| 2408 | +++ |
| 2409 | +++ |
| 2410 | +++ |
| 2411 | +++ |
| 2412 | +++ |
| 2413 | +++ |
| 2414 | ++ |
| 2415 | +++ |
| 2416 | +++ |
| 2417 | +++ |
| 2418 | +++ |
| 2419 | ++ |
| 2420 | ++ |
| 2421 | +++ |
| 2422 | ++ |
| 2423 | +++ |
| 2424 | +++ |
| 2425 | +++ |
| 2426 | +++ |
| 2427 | +++ |
| 2428 | +++ |
| 2429 | +++ |
| 2430 | ++ |
| 2431 | +++ |
| 2432 | +++ |
| 2433 | ++ |
| 2434 | +++ |
| 2435 | +++ |
| 2436 | +++ |
| 2437 | +++ |
| 2438 | +++ |
| 2439 | +++ |
| 2440 | +++ |
| 2441 | ++ |
| 2442 | ++ |
| 2443 | +++ |
| 2444 | ++ |
| 2445 | +++ |
| 2446 | +++ |
| 2447 | +++ |
| 2448 | +++ |
| 2449 | +++ |

TABLE 3-continued

| Cmpd. No. | EC30 (µM) |
|---|---|
| 2450 | +++ |
| 2451 | +++ |
| 2452 | +++ |
| 2453 | +++ |
| 2454 | ++ |
| 2455 | +++ |
| 2456 | +++ |
| 2457 | +++ |
| 2458 | +++ |
| 2459 | +++ |
| 2460 | +++ |
| 2461 | +++ |
| 2462 | +++ |
| 2463 | +++ |
| 2464 | ++ |
| 2465 | +++ |
| 2466 | +++ |
| 2467 | +++ |
| 2468 | +++ |
| 2469 | ++ |
| 2470 | +++ |
| 2471 | ++ |
| 2472 | ++ |
| 2473 | +++ |
| 2474 | +++ |
| 2475 | +++ |
| 2476 | +++ |
| 2477 | +++ |
| 2478 | +++ |
| 2479 | +++ |
| 2480 | ++ |
| 2481 | +++ |
| 2482 | +++ |
| 2483 | +++ |
| 2484 | +++ |
| 2485 | +++ |
| 2486 | +++ |
| 2487 | +++ |
| 2488 | +++ |
| 2489 | ++ |
| 2490 | +++ |
| 2491 | +++ |
| 2492 | +++ |
| 2493 | +++ |
| 2494 | +++ |
| 2495 | +++ |
| 2496 | +++ |
| 2497 | +++ |
| 2498 | +++ |
| 2499 | +++ |
| 2500 | +++ |
| 2501 | ++ |
| 2502 | +++ |
| 2503 | +++ |
| 2504 | ++ |
| 2505 | +++ |
| 2506 | ++ |
| 2507 | +++ |
| 2508 | +++ |
| 2509 | +++ |
| 2510 | +++ |
| 2511 | +++ |
| 2512 | +++ |
| 2513 | ++ |
| 2514 | +++ |
| 2515 | +++ |
| 2516 | ++ |
| 2517 | +++ |
| 2518 | +++ |
| 2519 | +++ |
| 2520 | ++ |
| 2521 | +++ |
| 2522 | +++ |
| 2523 | ++ |
| 2524 | +++ |
| 2525 | ++ |
| 2526 | +++ |

TABLE 3-continued

| Cmpd. No. | EC30 (μM) |
|---|---|
| 2527 | +++ |
| 2528 | +++ |
| 2529 | +++ |
| 2530 | +++ |
| 2531 | +++ |
| 2532 | +++ |
| 2533 | +++ |
| 2534 | +++ |
| 2535 | ++ |
| 2536 | +++ |
| 2537 | ++ |
| 2538 | +++ |
| 2539 | +++ |
| 2540 | +++ |
| 2541 | +++ |
| 2542 | +++ |
| 2543 | +++ |
| 2544 | + |
| 2545 | +++ |
| 2546 | +++ |
| 2547 | +++ |
| 2548 | +++ |
| 2549 | +++ |
| 2550 | ++ |
| 2551 | +++ |
| 2552 | +++ |
| 2553 | +++ |
| 2554 | +++ |
| 2555 | +++ |
| 2556 | ++ |
| 2557 | +++ |
| 2558 | +++ |
| 2559 | +++ |
| 2560 | +++ |
| 2561 | +++ |
| 2562 | +++ |
| 2563 | +++ |
| 2564 | +++ |
| 2565 | ++ |
| 2566 | +++ |
| 2567 | +++ |
| 2568 | ++ |
| 2569 | +++ |
| 2570 | ++ |
| 2571 | +++ |
| 2572 | +++ |
| 2573 | +++ |
| 2574 | ++ |
| 2575 | +++ |
| 2576 | +++ |
| 2577 | +++ |
| 2578 | +++ |
| 2579 | +++ |
| 2580 | +++ |
| 2581 | +++ |
| 2582 | +++ |
| 2583 | ++ |
| 2584 | ++ |
| 2585 | +++ |
| 2586 | ++ |
| 2587 | ++ |
| 2588 | +++ |
| 2589 | +++ |
| 2590 | +++ |
| 2591 | +++ |
| 2592 | +++ |
| 2593 | +++ |
| 2594 | +++ |
| 2595 | +++ |
| 2596 | +++ |
| 2597 | ++ |
| 2598 | +++ |
| 2599 | ++ |
| 2600 | +++ |
| 2601 | ++ |
| 2602 | ++ |
| 2603 | +++ |
| 2604 | +++ |
| 2605 | ++ |
| 2606 | +++ |
| 2607 | +++ |
| 2608 | +++ |
| 2609 | +++ |
| 2610 | +++ |
| 2611 | +++ |
| 2612 | ++ |
| 2613 | +++ |
| 2614 | ++ |
| 2615 | ++ |
| 2616 | +++ |
| 2617 | ++ |
| 2618 | +++ |
| 2619 | +++ |
| 2620 | ++ |
| 2621 | ++ |
| 2622 | +++ |
| 2623 | ++ |
| 2624 | ++ |
| 2625 | +++ |
| 2626 | +++ |
| 2627 | +++ |
| 2628 | +++ |
| 2629 | +++ |
| 2630 | +++ |
| 2631 | +++ |
| 2632 | +++ |
| 2633 | ++ |
| 2634 | +++ |
| 2635 | +++ |
| 2636 | + |
| 2637 | +++ |
| 2638 | +++ |
| 2639 | +++ |
| 2640 | +++ |
| 2641 | +++ |
| 2642 | +++ |
| 2643 | +++ |
| 2644 | +++ |
| 2645 | +++ |
| 2646 | +++ |
| 2647 | +++ |
| 2648 | +++ |
| 2649 | +++ |
| 2650 | ++ |
| 2651 | +++ |
| 2652 | +++ |
| 2653 | +++ |
| 2654 | +++ |
| 2655 | +++ |
| 2656 | +++ |
| 2657 | ++ |
| 2658 | ++ |
| 2659 | ++ |
| 2660 | +++ |
| 2661 | +++ |
| 2662 | ++ |
| 2663 | +++ |
| 2664 | +++ |
| 2665 | +++ |
| 2666 | ++ |
| 2667 | +++ |
| 2668 | ++ |
| 2669 | +++ |
| 2670 | +++ |
| 2671 | +++ |
| 2672 | +++ |

TABLE 3-continued

| Cmpd. No. | EC30 (μM) |
|---|---|
| 2673 | +++ |
| 2674 | +++ |
| 2675 | +++ |
| 2676 | +++ |
| 2677 | +++ |
| 2678 | ++ |
| 2679 | ++ |
| 2680 | ++ |
| 2681 | +++ |
| 2682 | +++ |
| 2683 | +++ |
| 2684 | +++ |
| 2685 | +++ |
| 2686 | +++ |
| 2687 | ++ |
| 2688 | +++ |
| 2689 | ++ |
| 2690 | +++ |
| 2691 | +++ |
| 2692 | ++ |
| 2693 | ++ |
| 2694 | +++ |
| 2695 | +++ |
| 2696 | +++ |
| 2697 | +++ |
| 2698 | +++ |
| 2699 | +++ |
| 2700 | +++ |
| 2701 | +++ |
| 2702 | +++ |
| 2703 | +++ |
| 2704 | +++ |
| 2705 | +++ |
| 2706 | +++ |
| 2707 | +++ |
| 2708 | +++ |
| 2709 | +++ |
| 2710 | ++ |
| 2711 | ++ |
| 2712 | +++ |
| 2713 | +++ |
| 2714 | +++ |
| 2715 | +++ |
| 2716 | +++ |
| 2717 | +++ |
| 2718 | +++ |
| 2719 | +++ |
| 2720 | +++ |
| 2721 | +++ |
| 2722 | +++ |
| 2723 | +++ |
| 2724 | +++ |
| 2725 | +++ |
| 2726 | +++ |
| 2727 | +++ |
| 2728 | +++ |
| 2729 | +++ |
| 2730 | ++ |
| 2731 | ++ |
| 2732 | ++ |
| 2733 | ++ |
| 2734 | ++ |
| 2735 | ++ |
| 2736 | ++ |
| 2737 | +++ |
| 2738 | +++ |
| 2739 | +++ |
| 2740 | +++ |
| 2741 | ++ |
| 2742 | ++ |
| 2743 | +++ |
| 2744 | +++ |
| 2745 | +++ |
| 2746 | +++ |
| 2747 | +++ |

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

LENGTHY TABLES

The patent contains a lengthy table section. A copy of the table is available in electronic form from the USPTO web site (https://seqdata.uspto.gov/?pageRequest=docDetail&DocID=US12168009B2). An electronic copy of the table will also be available from the USPTO upon request and payment of the fee set forth in 37 CFR 1.19(b)(3).

The invention claimed is:
1. A compound of formula Ia:

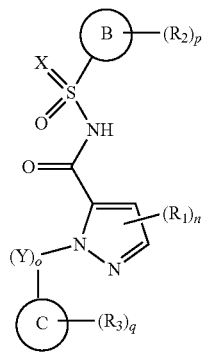

a deuterated derivative thereof, or a pharmaceutically acceptable salt of any of the foregoing, wherein, independently for each occurrence:
Ring B is a C6-C10 aryl ring or C3-C10 heteroaryl or heterocyclic ring wherein anywhere from 1 to 4 ring atoms are independently O, S, N, or NR;
Ring C is a C6-C10 aryl ring, C3-C14 heteroaryl or heterocyclic ring wherein anywhere from 1 to 4 ring atoms are independently N, O, or S, or a C3-C10 cycloalkyl ring;
X is O or NR;
Y is CRR, CO, O, S, SO, $SO_2$, S(O)NH or NR;
$R_1$ is halo; CN; $F_5S$; $SiR_3$; OH; NRR; C1-C6 alkyl; C1-C6 fluoroalkyl; C1-C6 alkoxy; C1-C6 fluoroalkoxy; C2-C6 alkenyl; C2-C6 alkynyl; (C1-C9 alkylene)-$R_4$ wherein up to four $CH_2$ units are independently replaced with O, CO, S, SO, $SO_2$ or NR; C6-C10 aryl; C3-C10 heteroaryl or heterocyclic ring wherein anywhere from 1 to 4 ring atoms are independently O, S, N, or NR; or C3-C10 cycloalkyl;
$R_2$ is halo; OH; NRR; azide; CN; $CO_2R$; C1-C6 alkyl; C1-C6 fluoroalkyl; C1-C6 alkoxy; C1-C6 fluoroalkoxy; C2-C6 alkenyl; C2-C6 alkynyl; C6-C10 aryl; C3-C13 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR; or two $R_2$ may form a $=CH_2$ or $=O$ group;
$R_3$ is halo; CN; $CO_2R$; C1-C6 alkyl; C1-C6 fluoroalkyl; C2-C6 alkenyl; C2-C6 alkynyl; C1-C6 alkoxy; C1-C6 fluoroalkoxy; or C6-C10 aryl; C3-C10 heteroaryl or heterocyclic ring wherein anywhere from 1 to 4 ring atoms are independently O, S, N, or NR; C3-C10 cycloalkyl; or a (C1-C9 alkylene)-$R_4$ wherein up to four $CH_2$ units are independently replaced with O, CO, S, SO, $SO_2$ or NR; or two $R_3$ may form a $=CH_2$ or $=O$ group;
$R_4$ is H; azide; $CF_3$; $CHF_2$; OR; CCH; $CO_2R$; OH; C6-C10 aryl, C3-C10 heteroaryl or heterocycloalkyl wherein anywhere from 1 to 4 ring atoms are independently O, S, N, or NR; C3-C10 cycloalkyl; NRR, NRCOR, CONRR, CN, or $SO_2R$;
R is independently H; OH; $CO_2H$; $CO_2$; C1-C6 alkyl; C1-C6 alkyl; C2-C6 alkenyl; C2-C6 alkynyl; C6-C10 aryl; C3-C10 heteroaryl or heterocycloalkyl wherein anywhere from 1 to 4 ring atoms are independently O, S, N, or NR; or C3-C10 cycloalkyl;
n is 0, 1, 2 or 3;
o is 0, 1, 2, 3, 4, or 5;
p is 0, 1, 2, or 3; and
q is 0, 1, 2, 3, 4, or 5.

2. The compound, deuterated derivative, or salt of claim 1, wherein ring B is phenyl, pyridyl, pyridine-2 (1H)-one, pyrazole, indole, thiophene, dihydrobenzofuran, pyrazine, indazole, thiazole, pyridine-4 (1H)-one, pyrrolidinone, or quinoline.

3. The compound, deuterated derivative, or salt of claim 1, wherein ring B is selected from

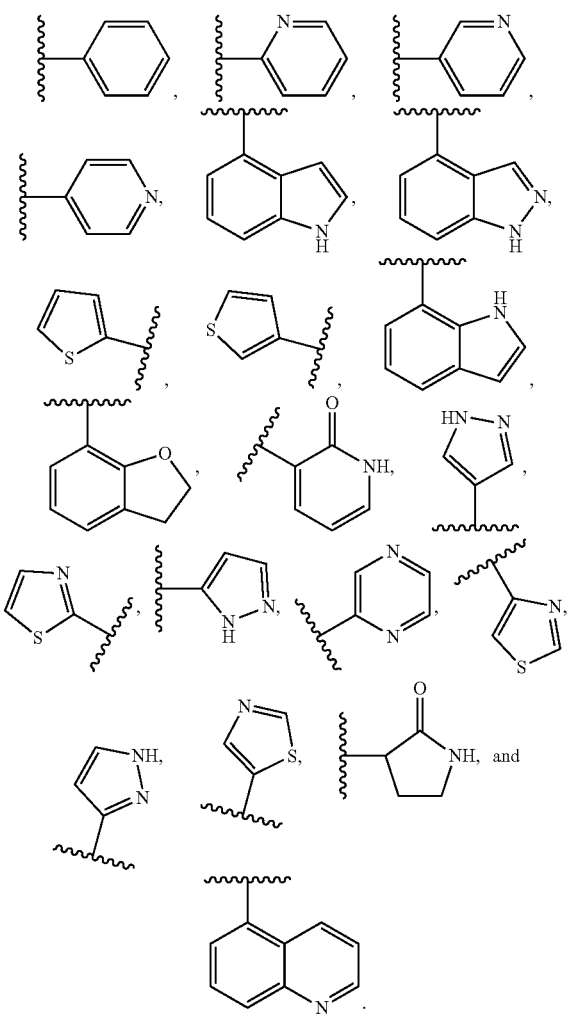

4. The compound, deuterated derivative, or salt of claim 1, wherein ring C is phenyl, indole, cycloalkyl, pyridyl, pyrrolidine, naphthalene, piperidine, or dihydroindene.

5. The compound, deuterated derivative, or salt of claim 1, wherein ring C is

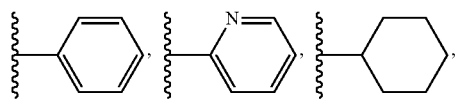

2343
-continued

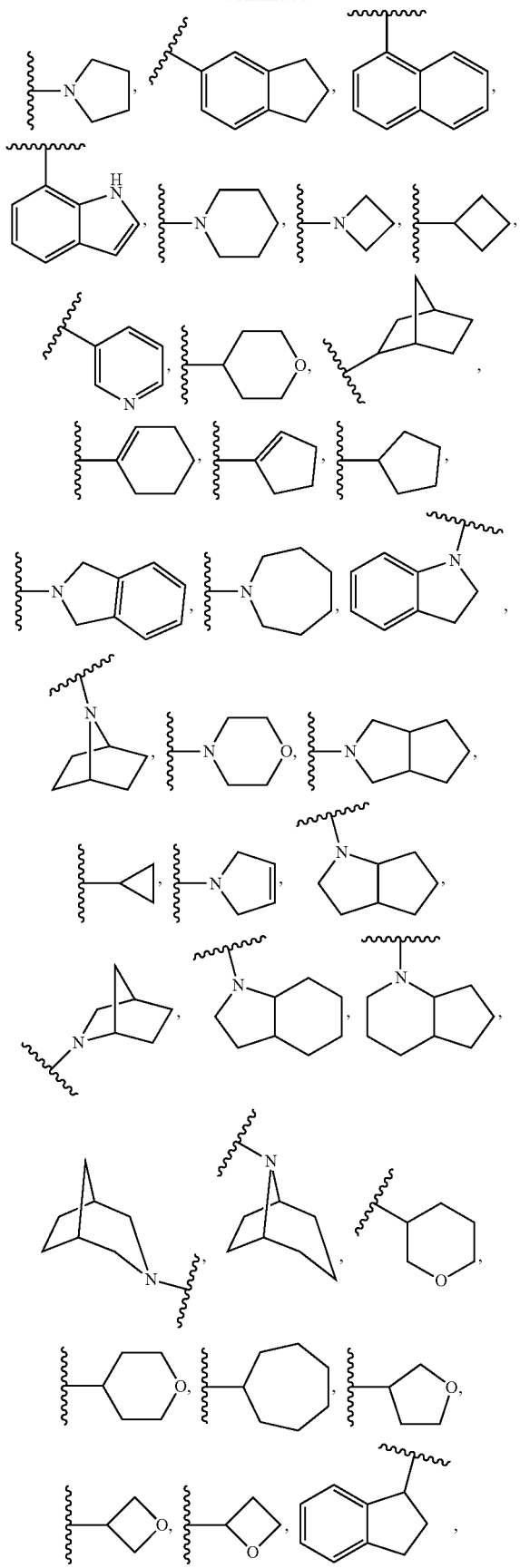

2344
-continued

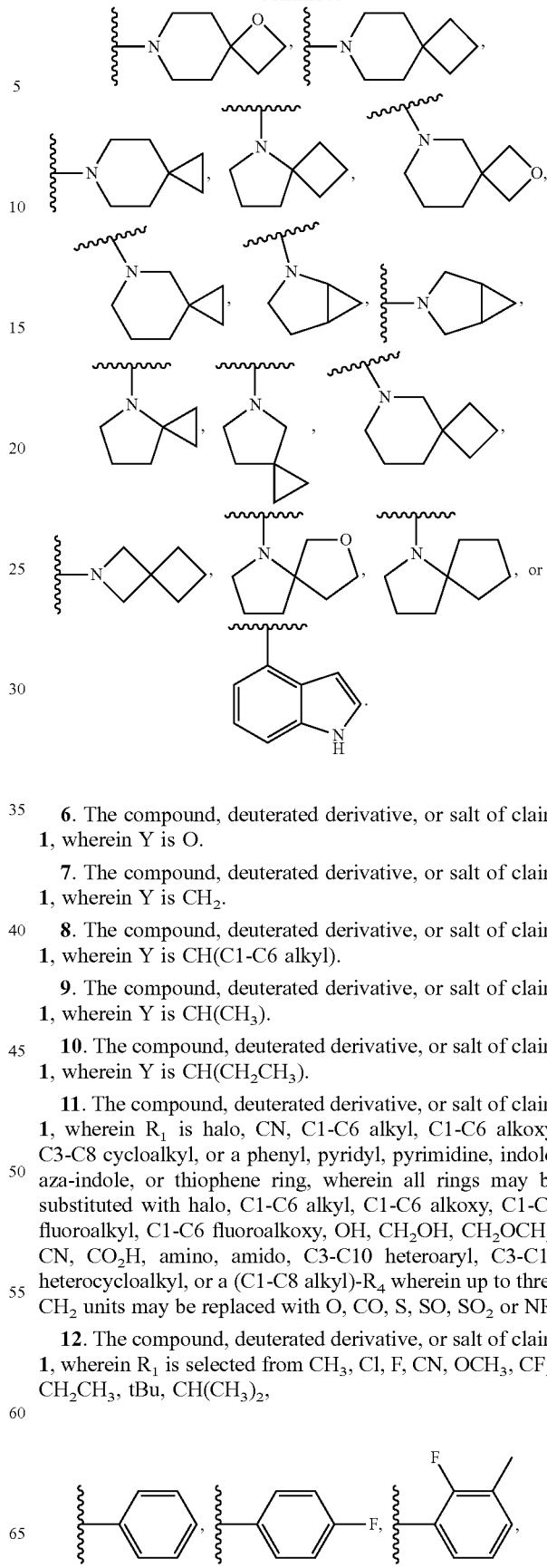

6. The compound, deuterated derivative, or salt of claim 1, wherein Y is O.

7. The compound, deuterated derivative, or salt of claim 1, wherein Y is $CH_2$.

8. The compound, deuterated derivative, or salt of claim 1, wherein Y is CH(C1-C6 alkyl).

9. The compound, deuterated derivative, or salt of claim 1, wherein Y is $CH(CH_3)$.

10. The compound, deuterated derivative, or salt of claim 1, wherein Y is $CH(CH_2CH_3)$.

11. The compound, deuterated derivative, or salt of claim 1, wherein $R_1$ is halo, CN, C1-C6 alkyl, C1-C6 alkoxy, C3-C8 cycloalkyl, or a phenyl, pyridyl, pyrimidine, indole, aza-indole, or thiophene ring, wherein all rings may be substituted with halo, C1-C6 alkyl, C1-C6 alkoxy, C1-C6 fluoroalkyl, C1-C6 fluoroalkoxy, OH, $CH_2OH$, $CH_2OCH_3$, CN, $CO_2H$, amino, amido, C3-C10 heteroaryl, C3-C10 heterocycloalkyl, or a (C1-C8 alkyl)-$R_4$ wherein up to three $CH_2$ units may be replaced with O, CO, S, SO, $SO_2$ or NR.

12. The compound, deuterated derivative, or salt of claim 1, wherein $R_1$ is selected from $CH_3$, Cl, F, CN, $OCH_3$, $CF_3$, $CH_2CH_3$, tBu, $CH(CH_3)_2$,

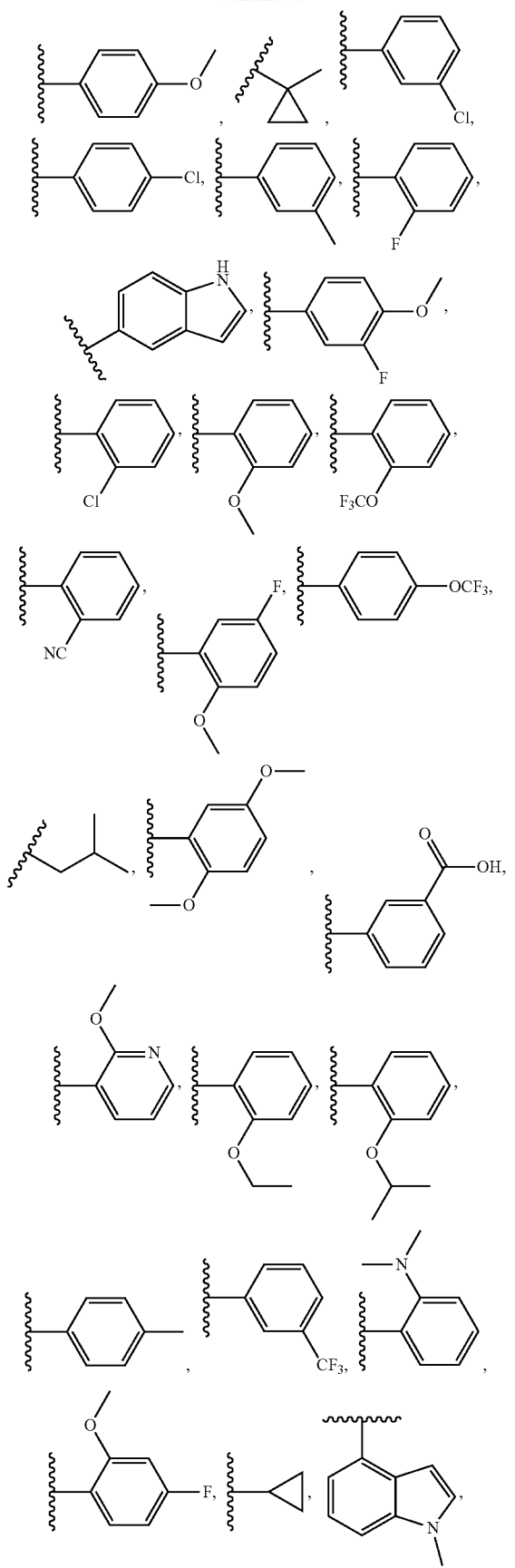
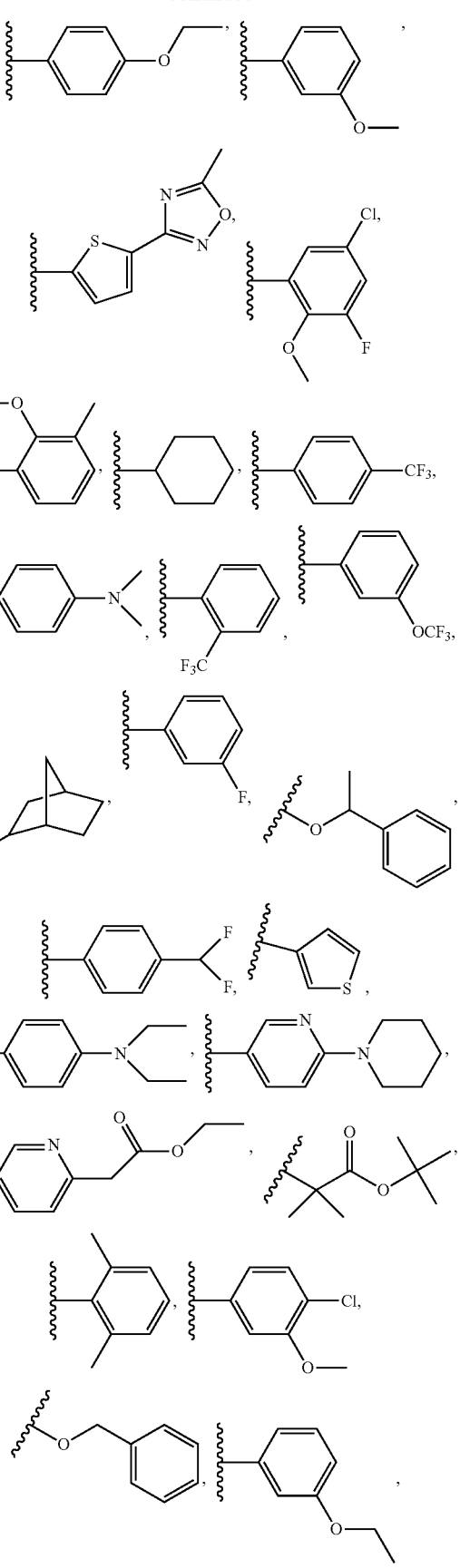

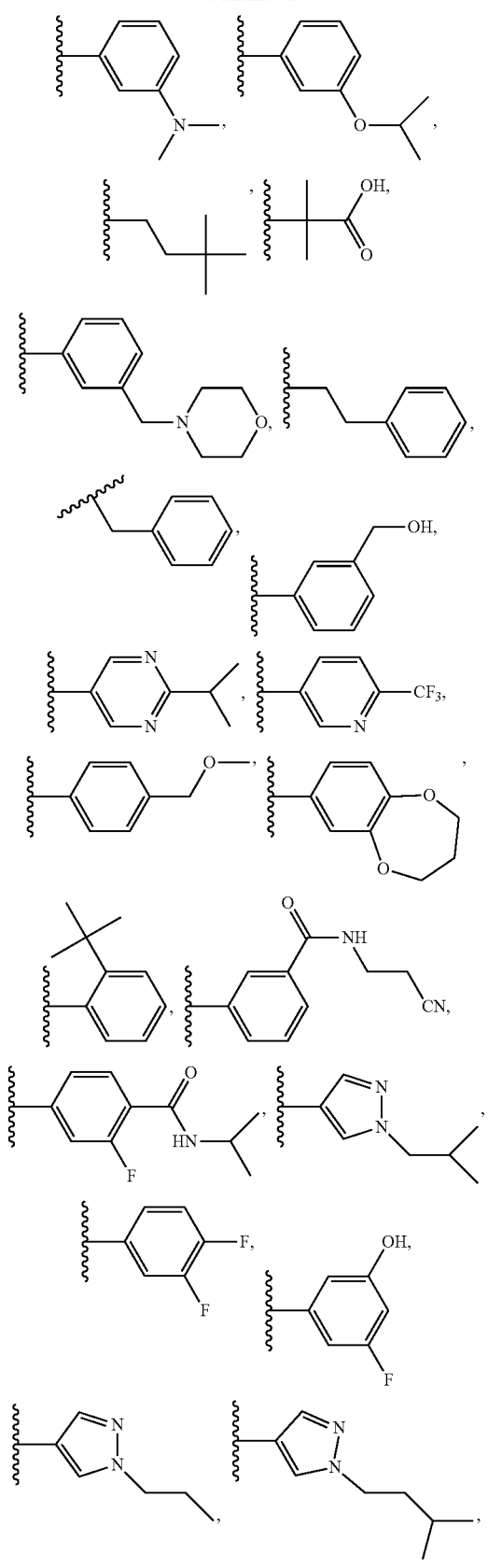
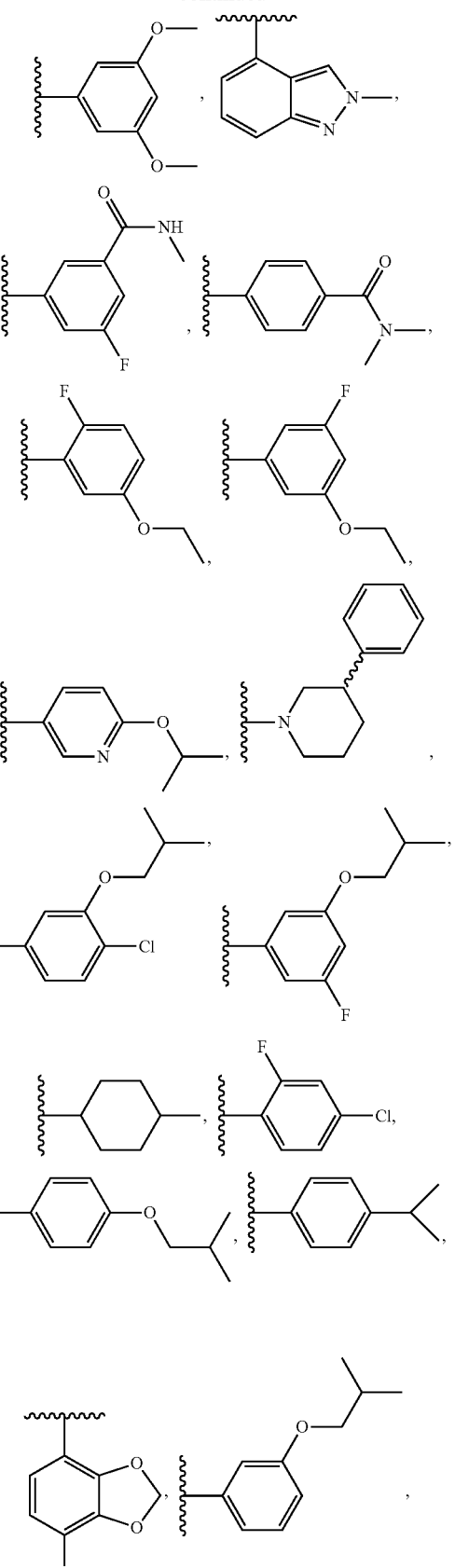

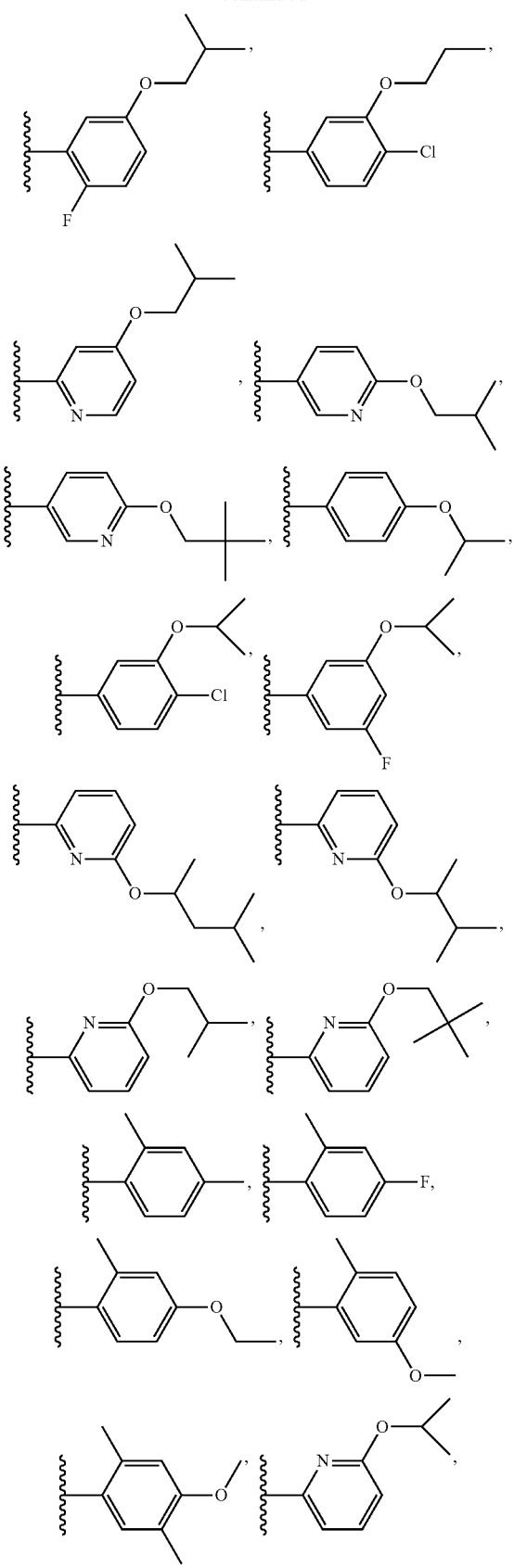
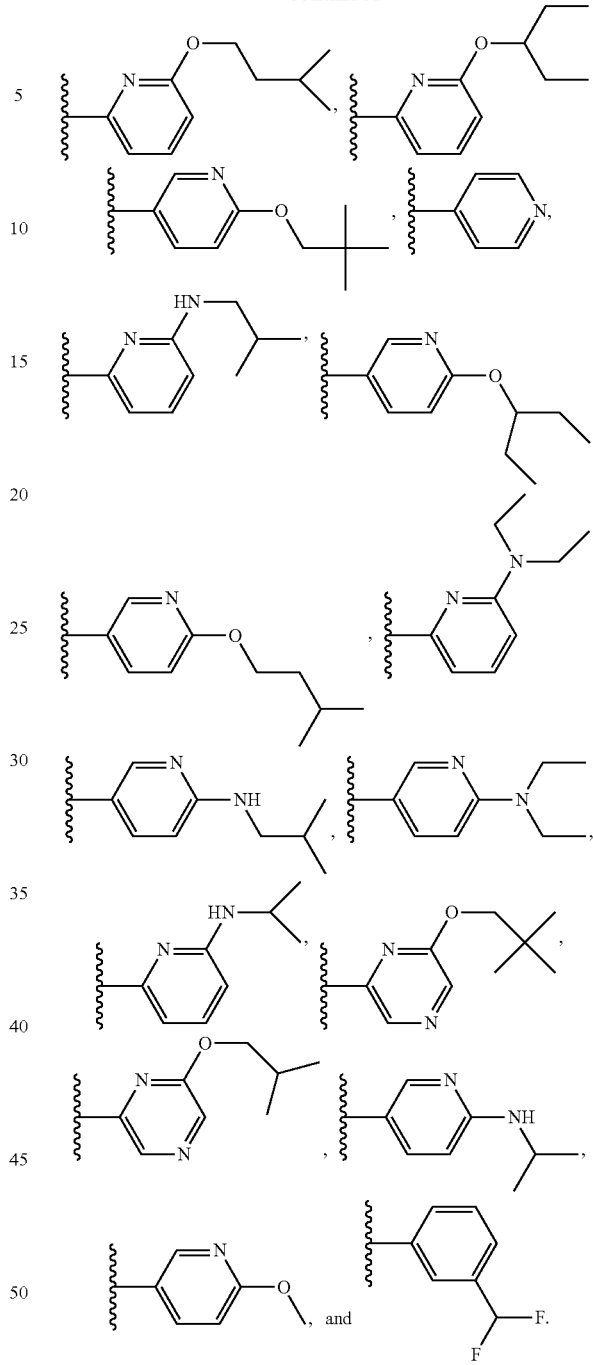

13. The compound, deuterated derivative, or salt of claim 1, wherein R₂ is halo, OH, CN, azide, amino, C1-C6 alkyl, C1-C6 fluoroalkyl, C1-C6 alkoxy, C1-C6 fluoroalkoxy, C3-C10 mono- or bicyclic heterocyclic ring wherein up to 4 carbon atoms may be replaced with O, S, N, or NR; or a (C1-C8 alkyl)-R₄ wherein up to three CH₂ units may be replaced with O, CO, S, SO, SO₂ or NR.

14. The compound, deuterated derivative, or salt of claim 1, wherein R₂ is selected from Cl, F, OH, CN, N₃, NH₂, NH(CH₃), N(CH₃)₂, CH₃, CH₂OH, CH₂CH₃, CH(CH₃)₂, CHF₂, OCH₃, OCF₃, OCHF₂, OCH(CH₃)₂, C(O)CH₃, CH₂CH₂OH, CH₂NH₂, NH(CH₂)₂OH, NH(CH₂)₂N(CH₃)₂, NH(CH₂)₂NH₂, NH(CH₂)₃NH₂, NH(CH₂)₂OCH₃, NHCH(CH₃)₂,

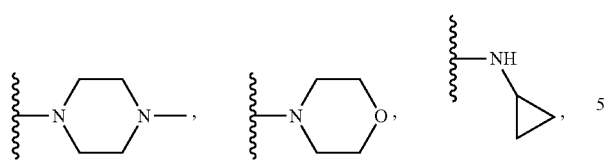

and CO$_2$H.

15. The compound, deuterated derivative, or salt of claim 1, wherein R$_3$ is selected from halo, CN, C1-C6 alkyl, C1-C6 fluoroalkyl, C1-C6 alkoxy, and C3-C10 mono- or bicyclic heteroaryl wherein up to 4 carbon atoms may be replaced by O, S, N, or NR.

16. The compound, deuterated derivative, or salt of claim 1, wherein R$_3$ is selected from Cl, F, CN, CH$_3$, OCH$_3$, CF$_3$, CH$_2$CH$_3$, CH$_2$CF$_3$, CH$_2$CH$_2$CH$_3$, OCH$_2$CH$_3$, CH$_2$OCH$_3$, CH(CH$_3$)$_2$, CCH, CO$_2$CH$_3$, tBu,

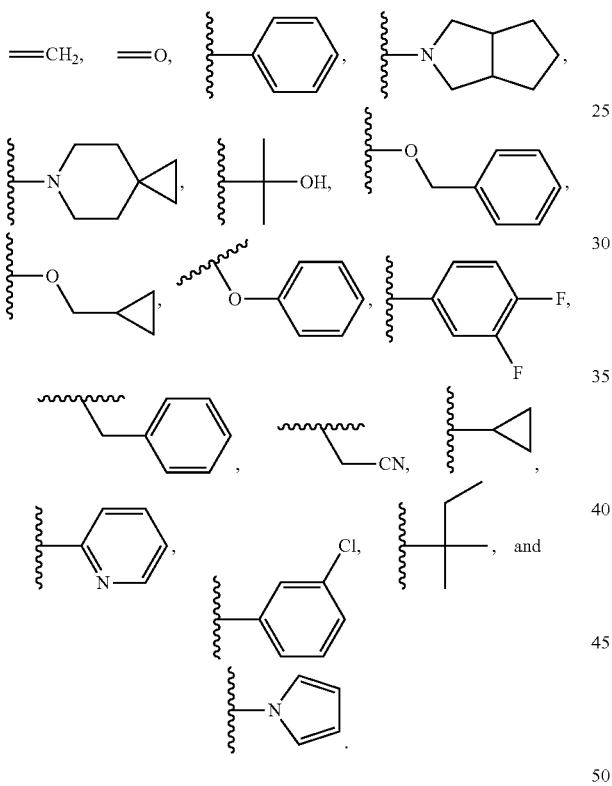

17. The compound, deuterated derivative, or salt of claim 1, wherein o is 0.

18. The compound, deuterated derivative, or salt of claim 1, wherein o is 1.

19. The compound, deuterated derivative, or salt of claim 1, wherein n is 0.

20. The compound, deuterated derivative, or salt of claim 1, wherein n is 1.

21. The compound, deuterated derivative, or salt of claim 1, wherein n is 2.

22. The compound, deuterated derivative, or salt of claim 1, wherein p is 0.

23. The compound, deuterated derivative, or salt of claim 1, wherein p is 1.

24. The compound, deuterated derivative, or salt of claim 1, wherein p is 2.

25. The compound, deuterated derivative, or salt of claim 1, wherein ring B is phenyl.

26. The compound, deuterated derivative, or salt of claim 1, wherein ring B and ring C are phenyl.

27. A compound selected from:

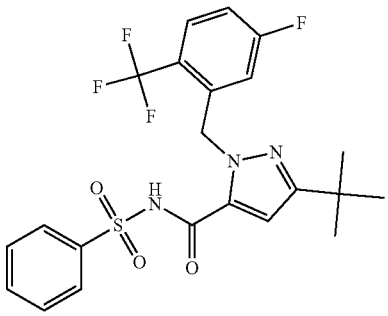

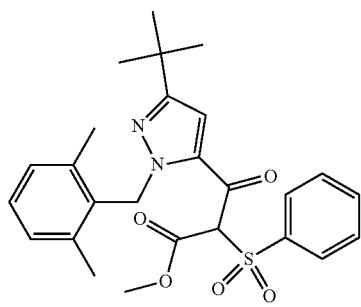

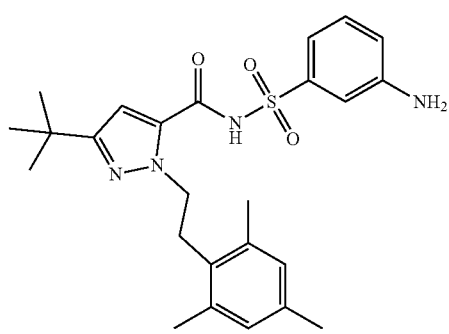

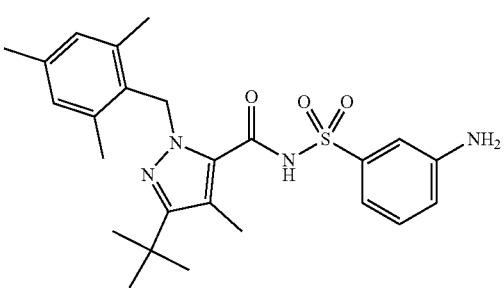

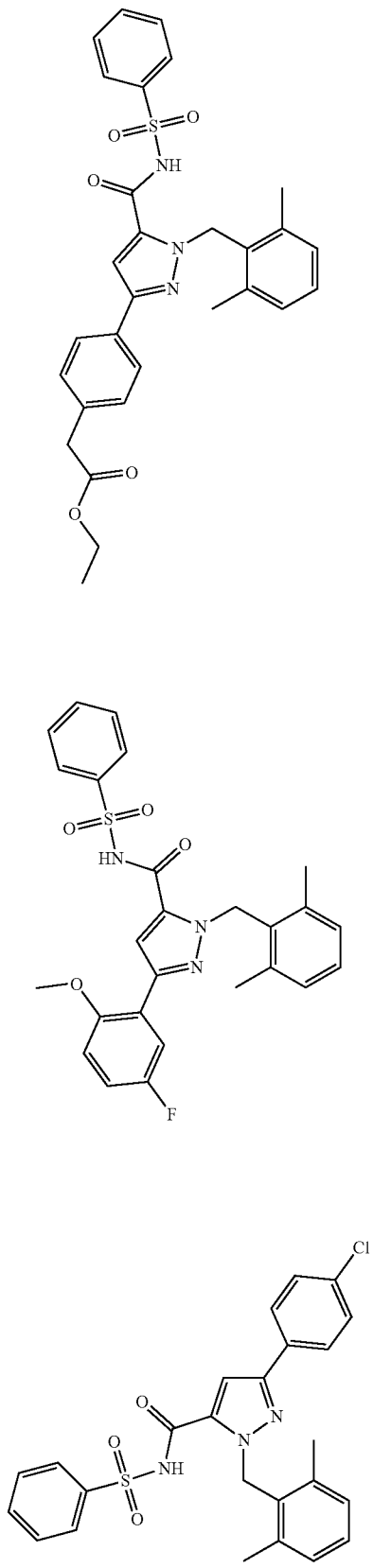
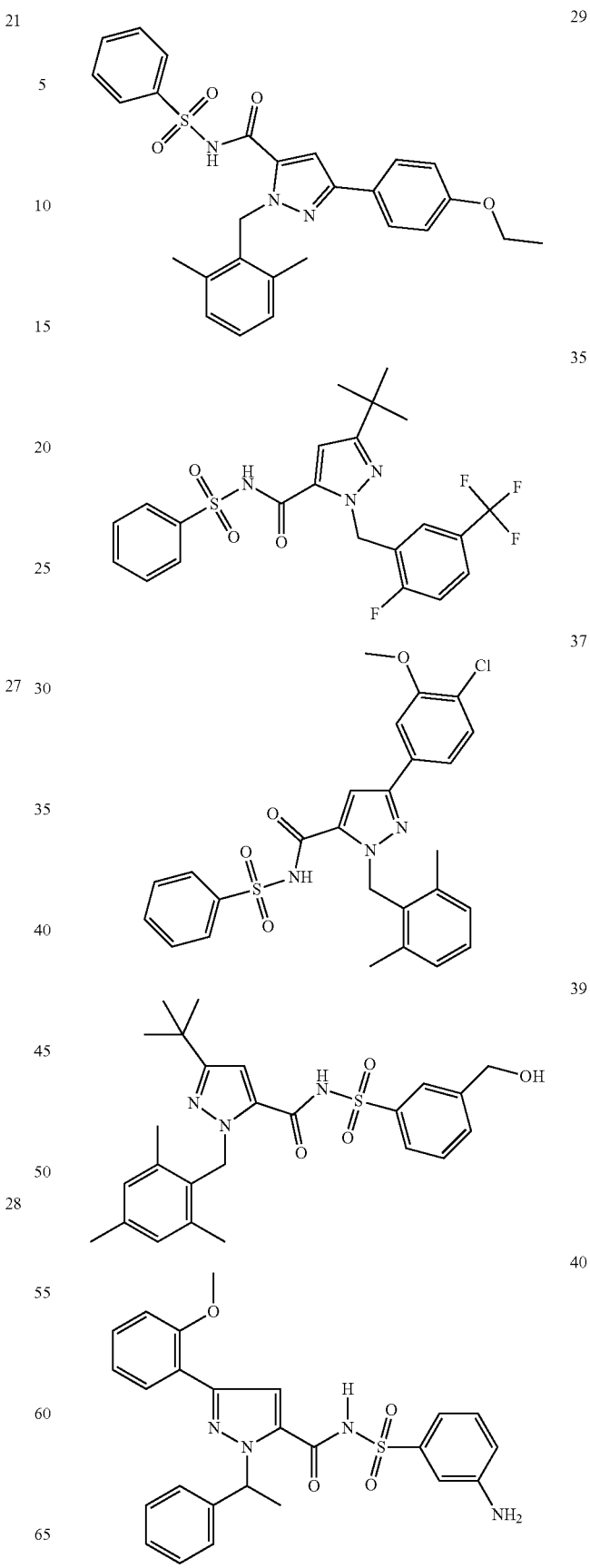

2355
-continued
42
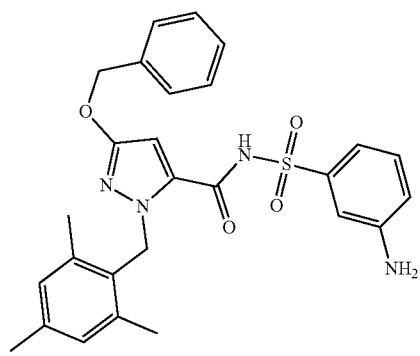
43
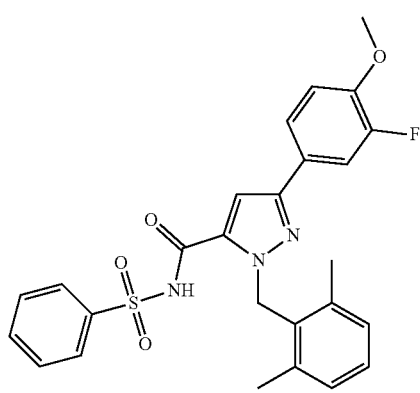
44
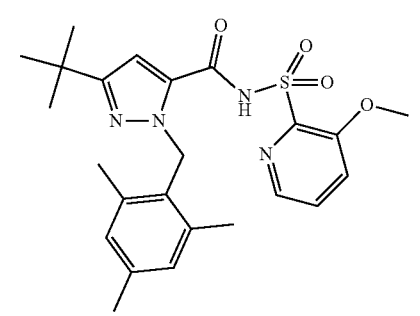
45
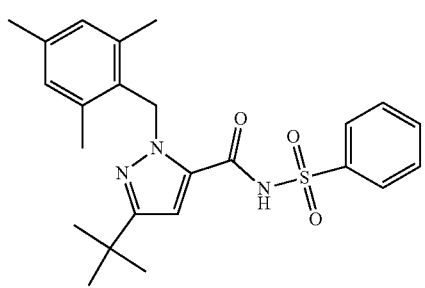
2356
-continued
49
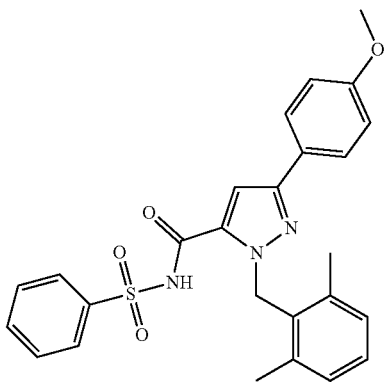
57
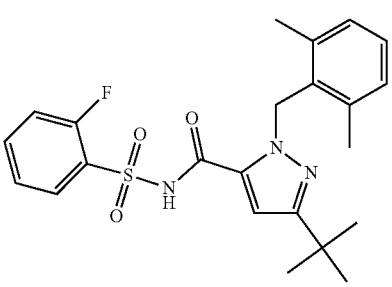
59
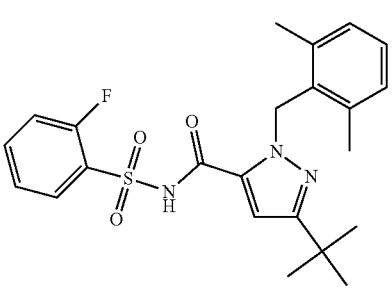
60
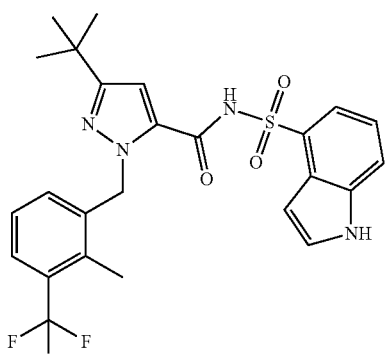
63
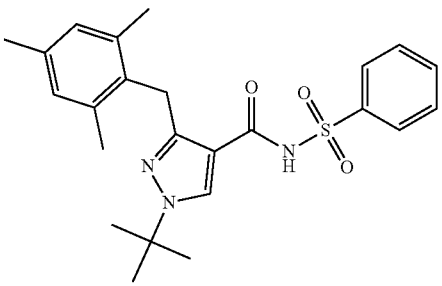

2357
-continued
76
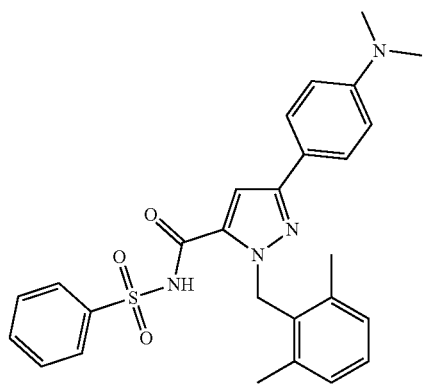
77
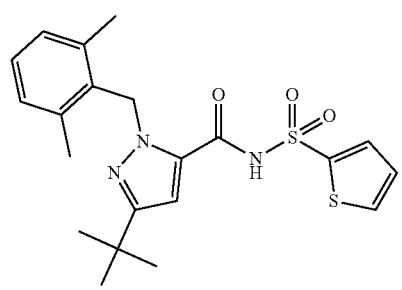
80
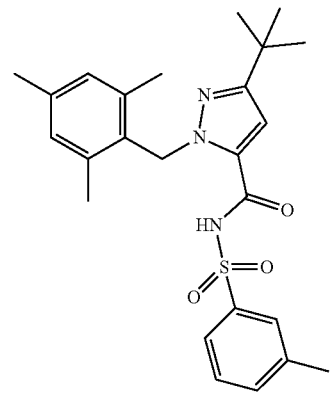
81
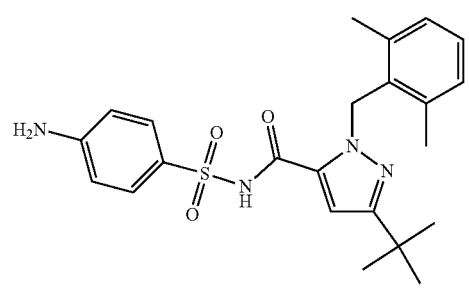
2358
-continued
83
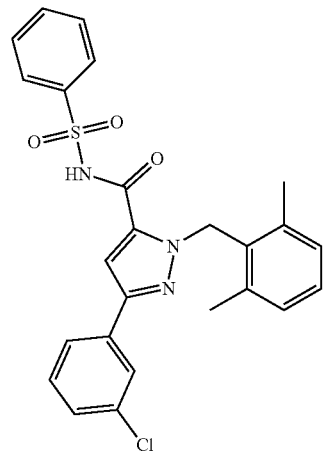
84
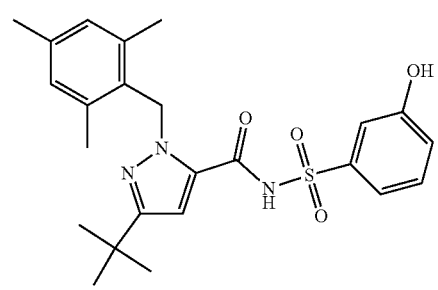
86
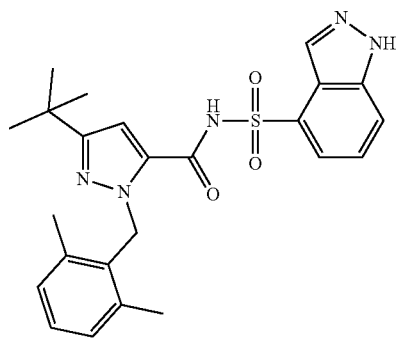
88
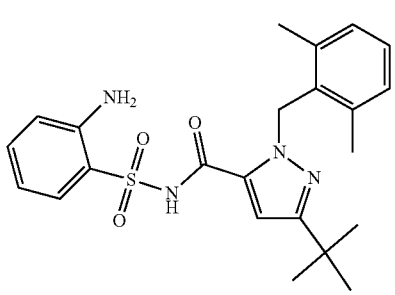

98
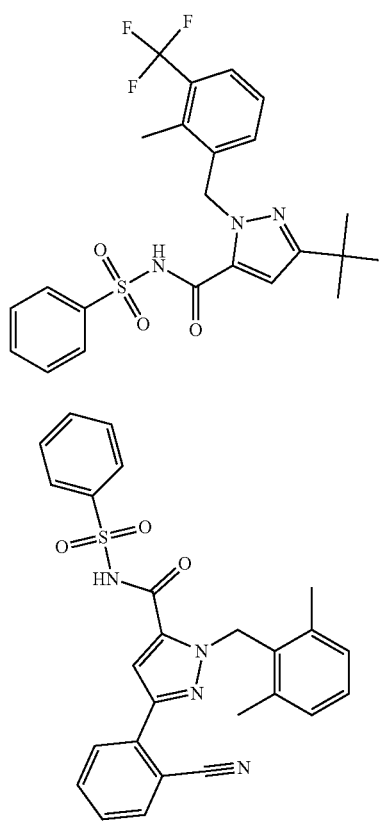
99
100
104
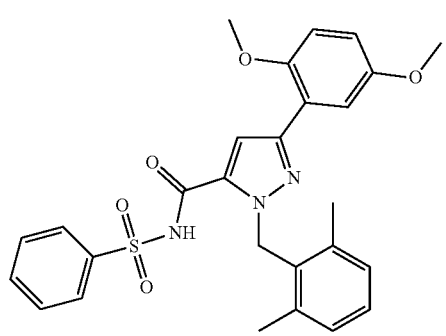
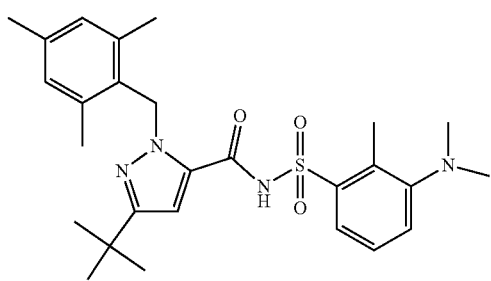
105
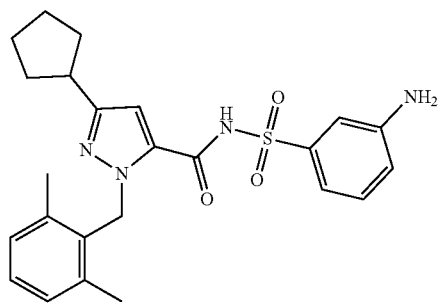
108
109
110
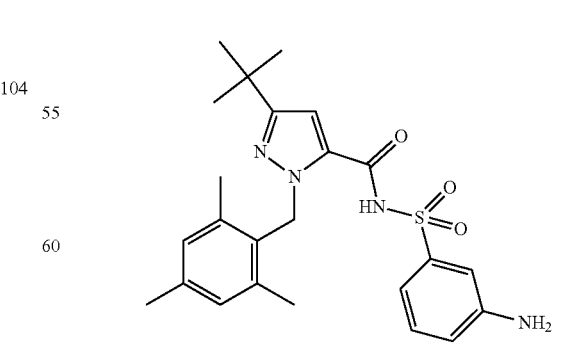

2361
-continued
119
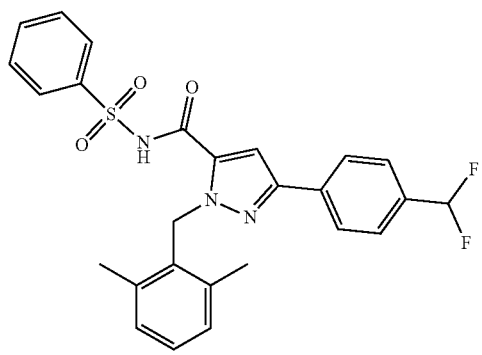
122
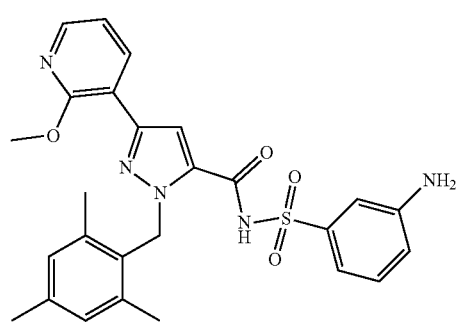
123
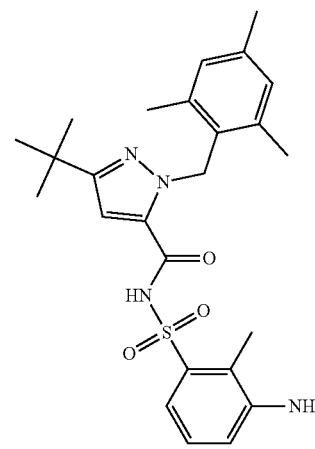
128
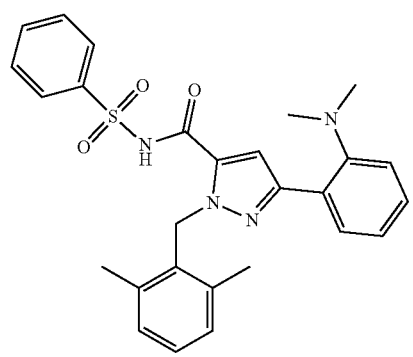
2362
-continued
133
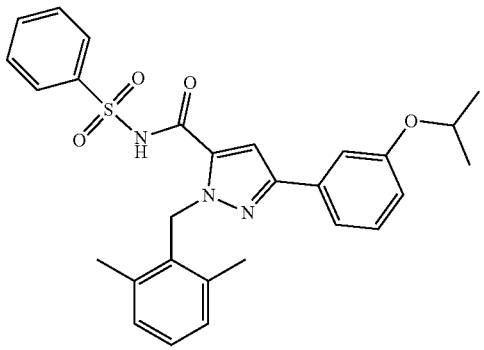
135
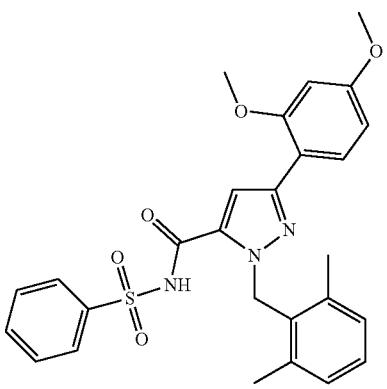
138
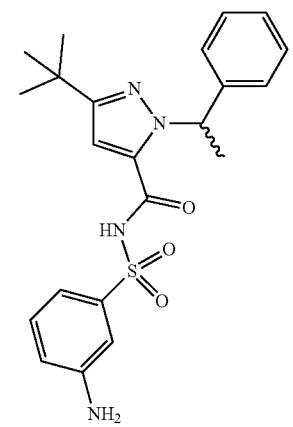
139
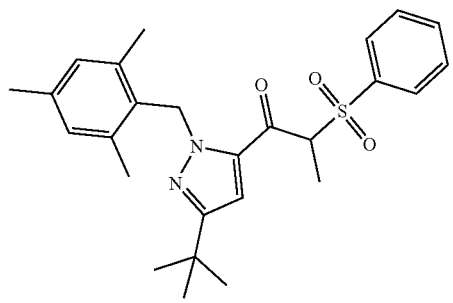

2363
-continued
145
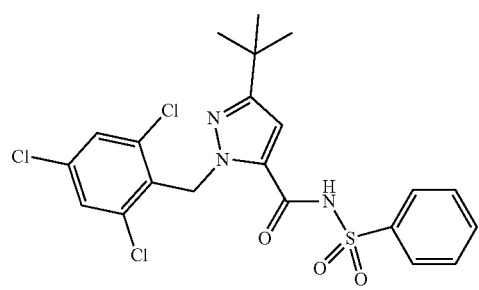
149
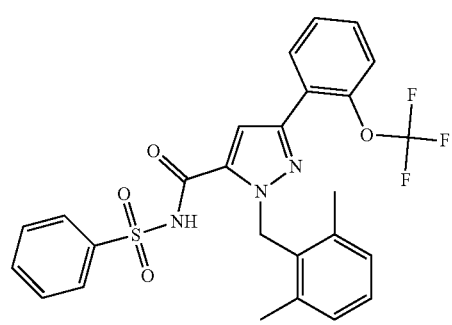
150
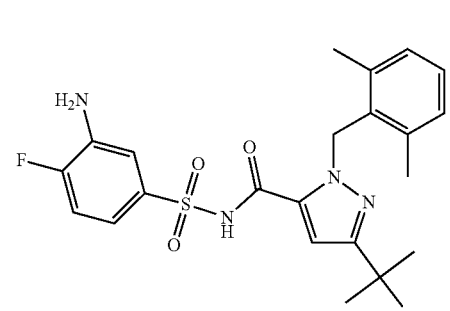
151
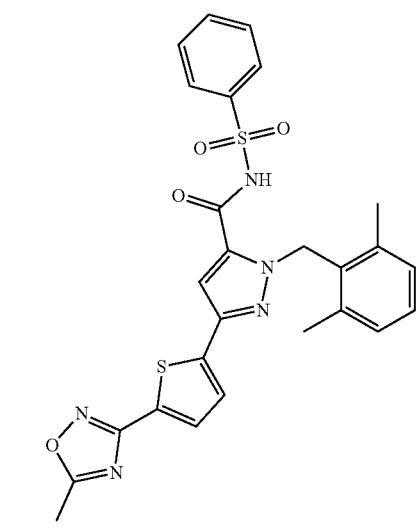
2364
-continued
152
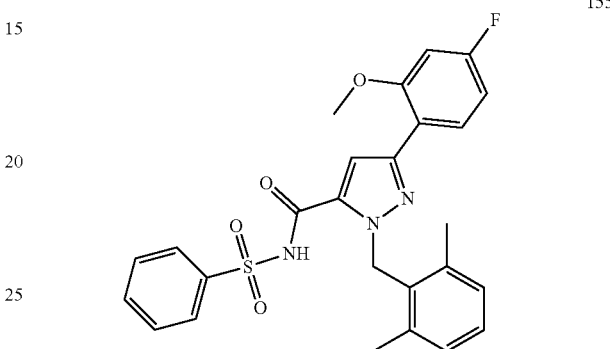
155
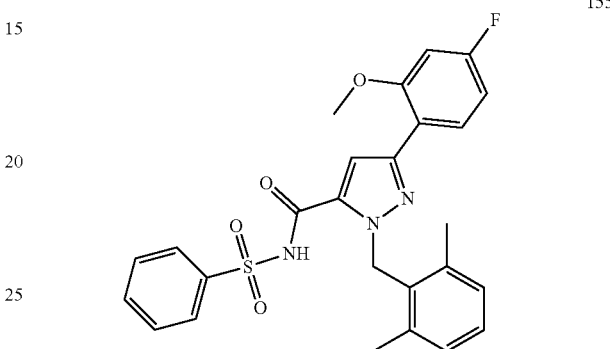
156
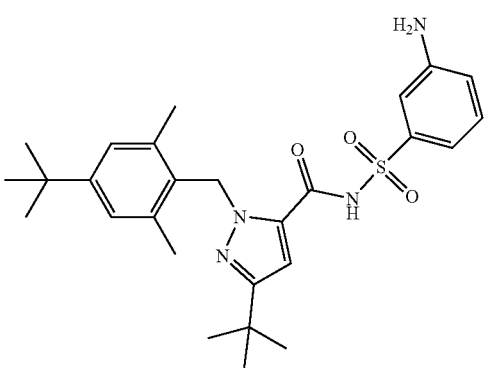
157
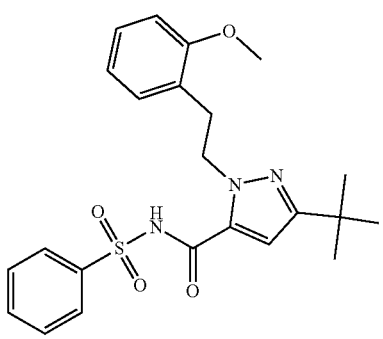

2365
-continued
158
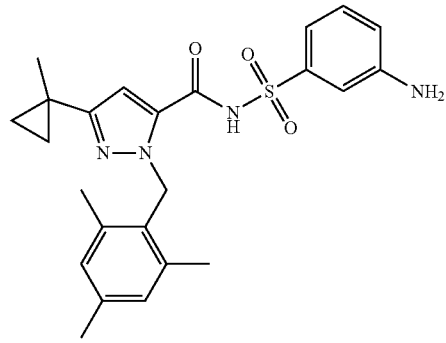
159
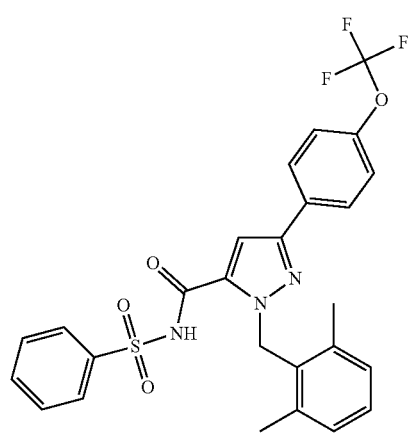
162
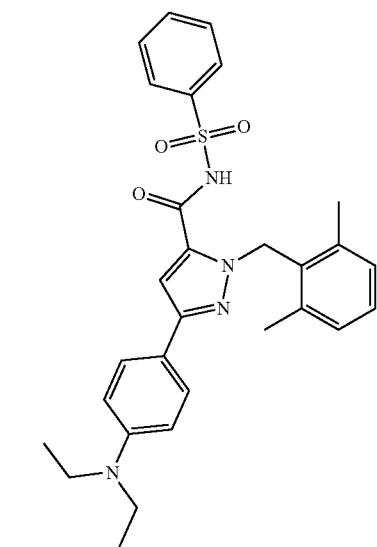
165
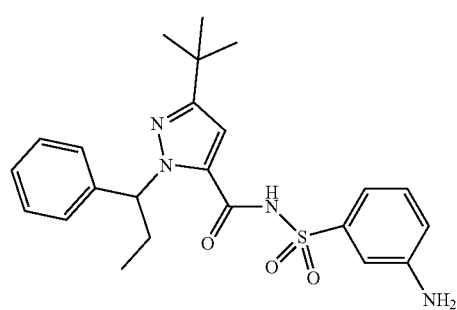
2366
-continued
166
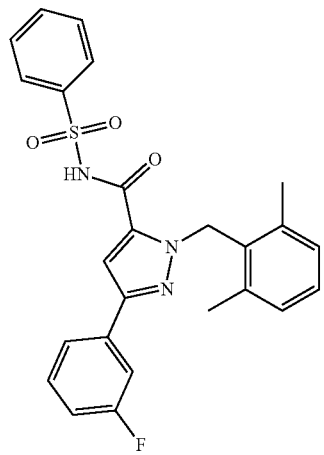
167
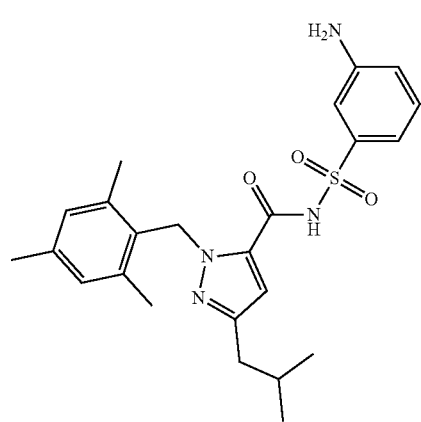
170
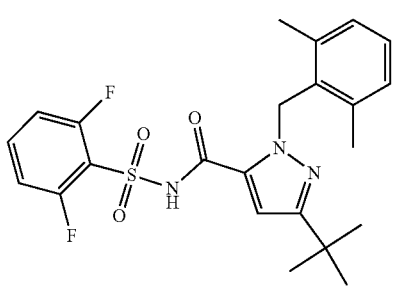
173
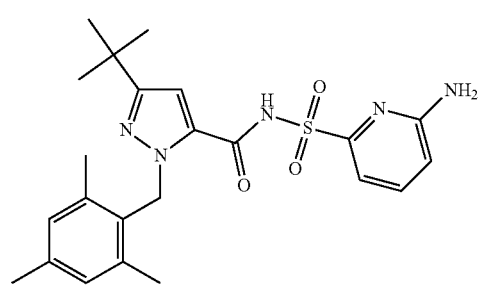

2367
176
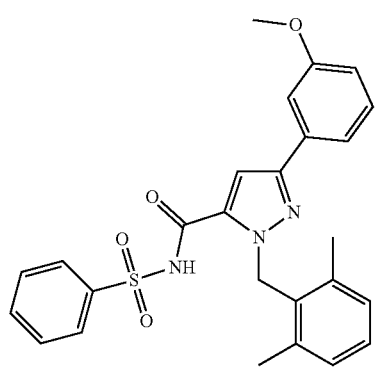
178
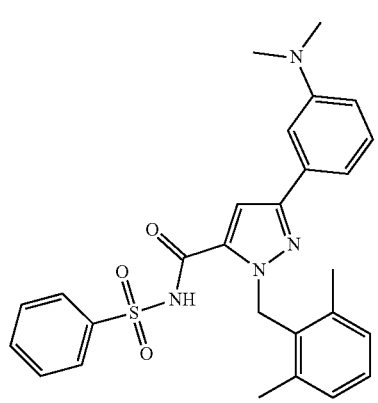
180
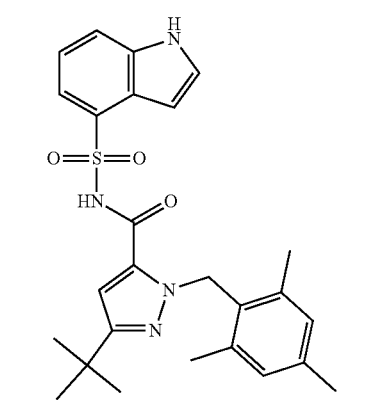
185
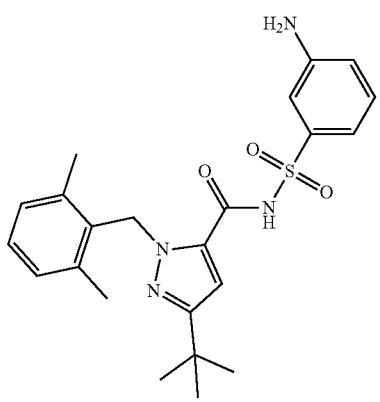
2368
188
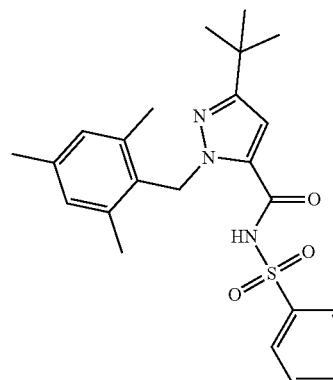
189
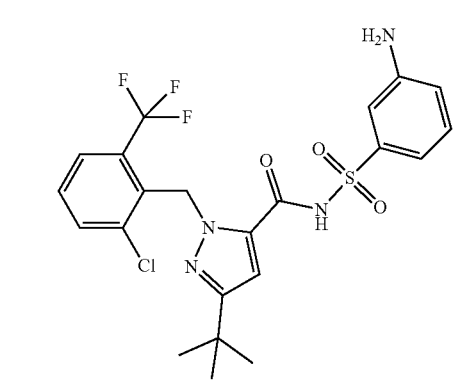
199
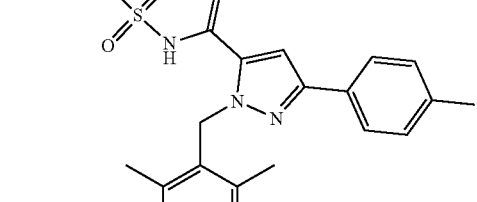
201
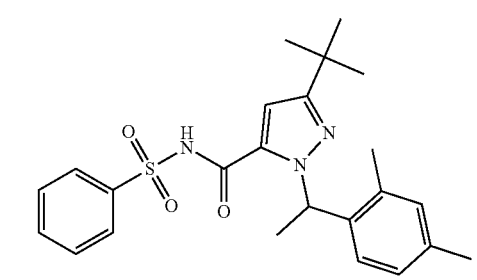

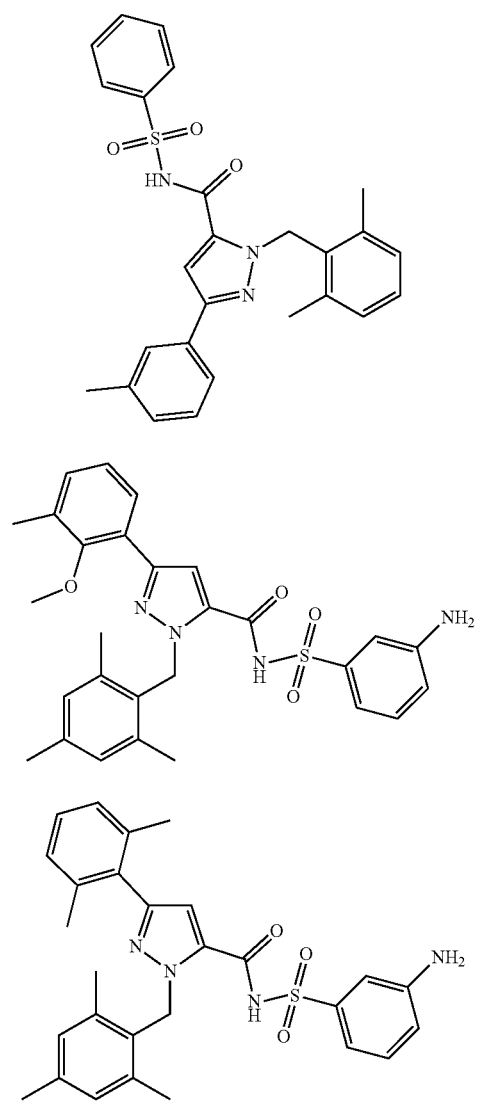
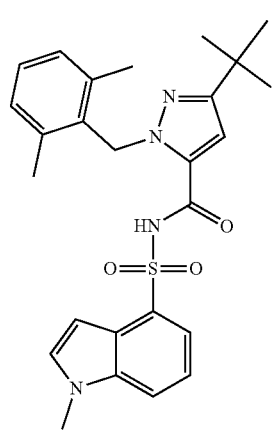
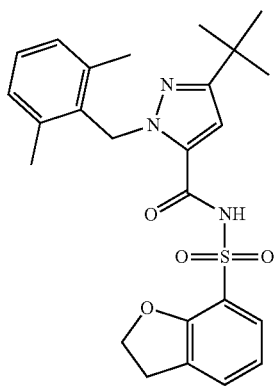
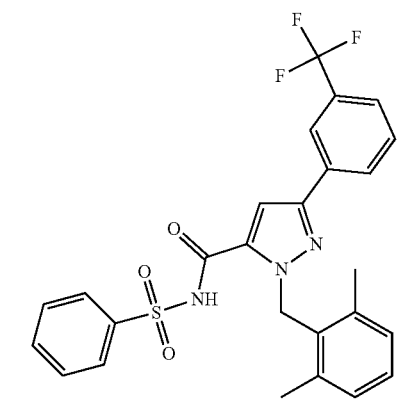
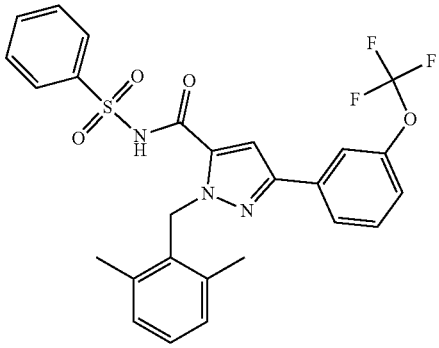
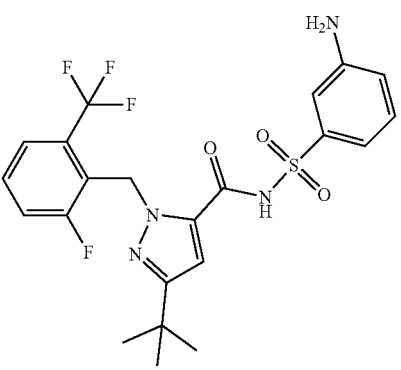

2371
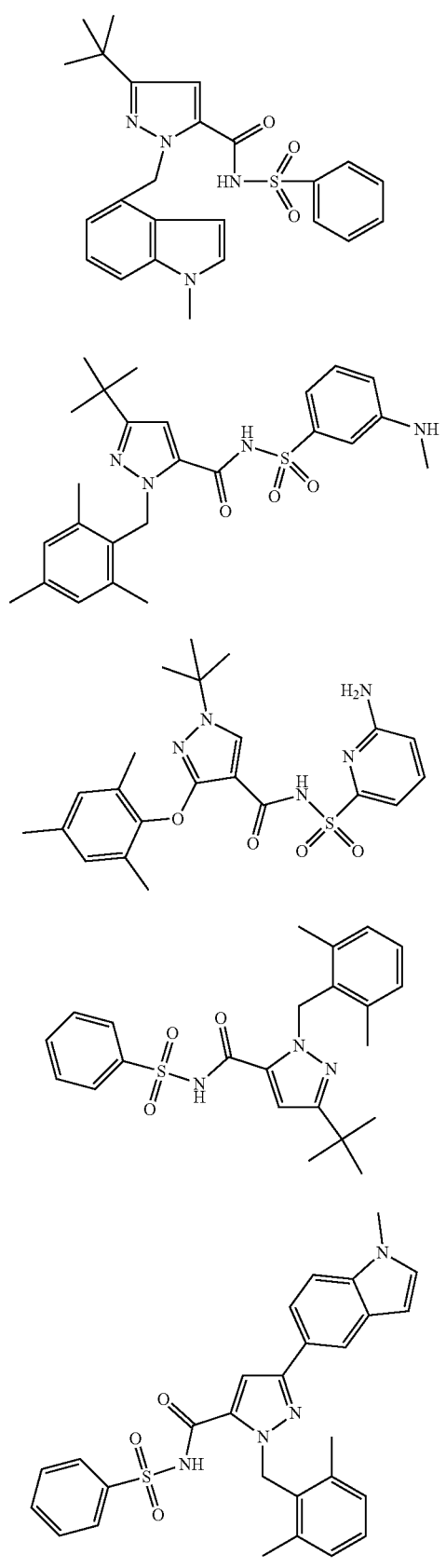
2372
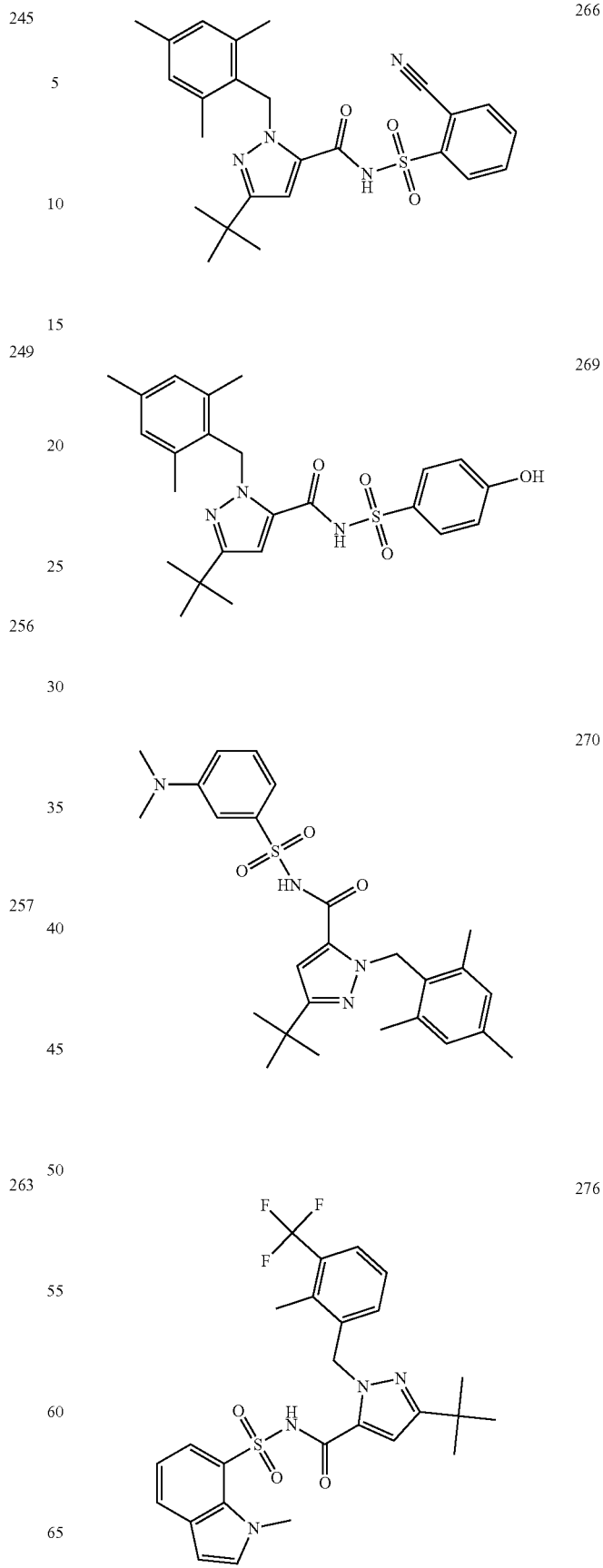

2373
-continued
277
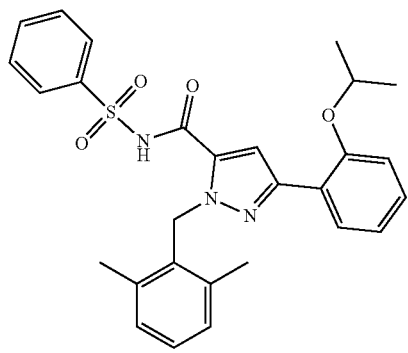
278
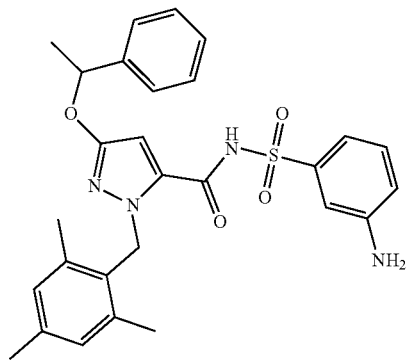
280
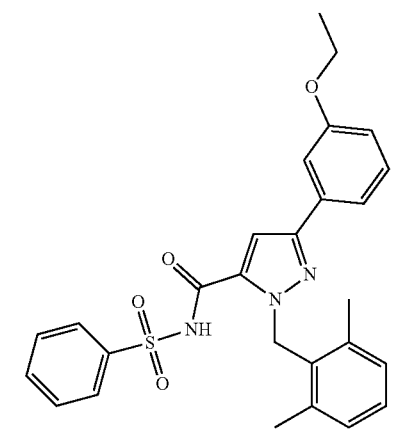
287
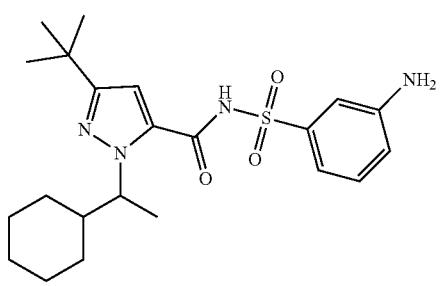
2374
-continued
293
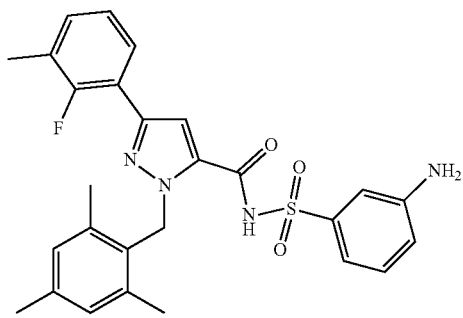
295
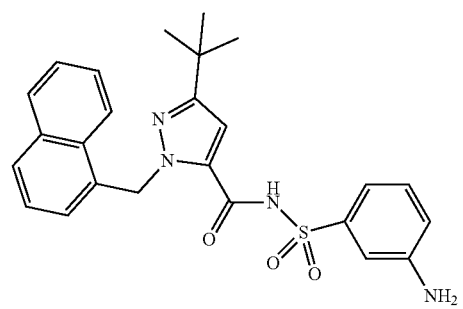
302
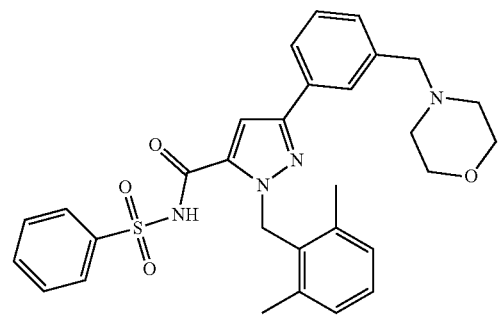
303
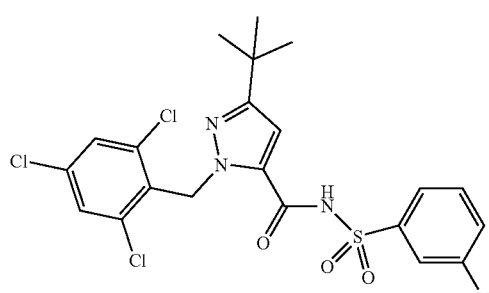
304
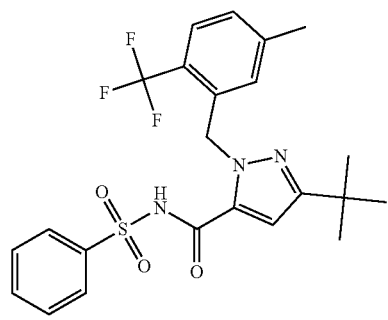

2375
-continued
312
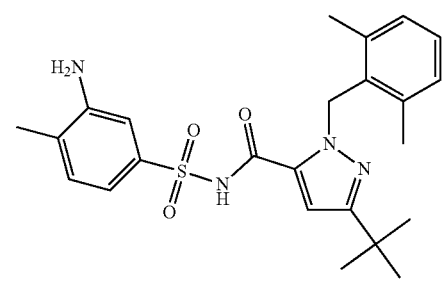
315
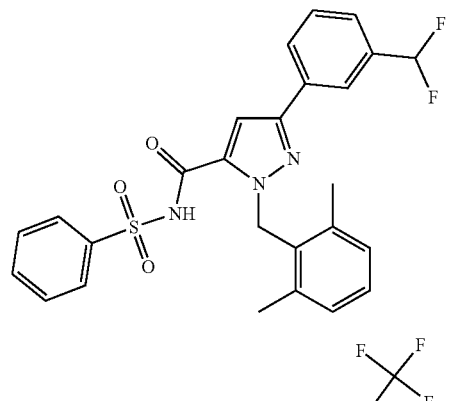
316
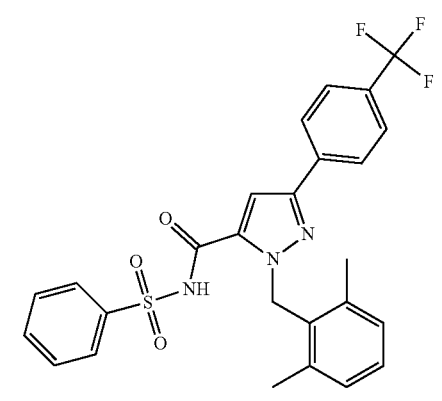
317
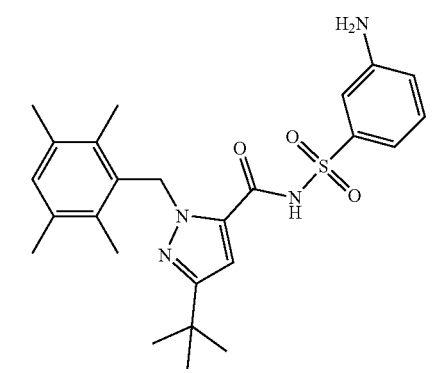
323
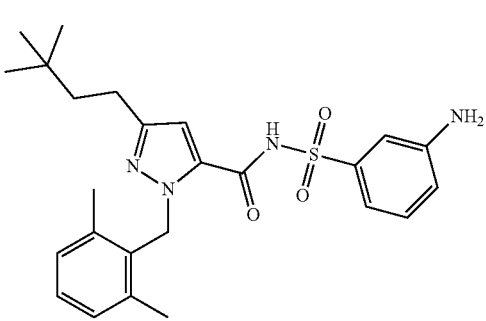
2376
-continued
324
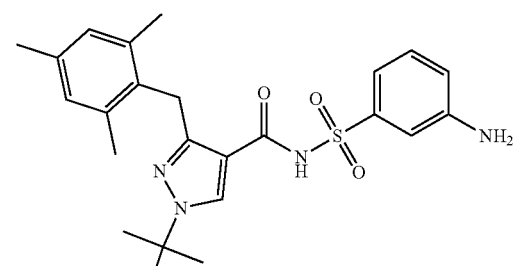
325
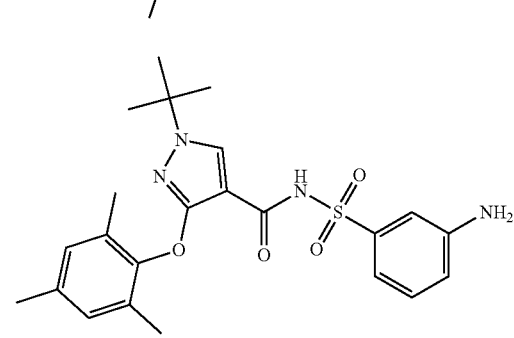
328
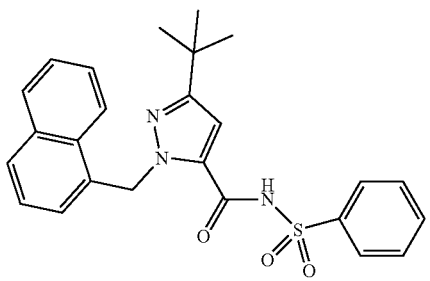
329
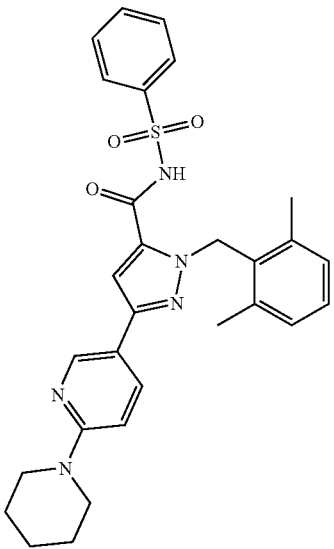

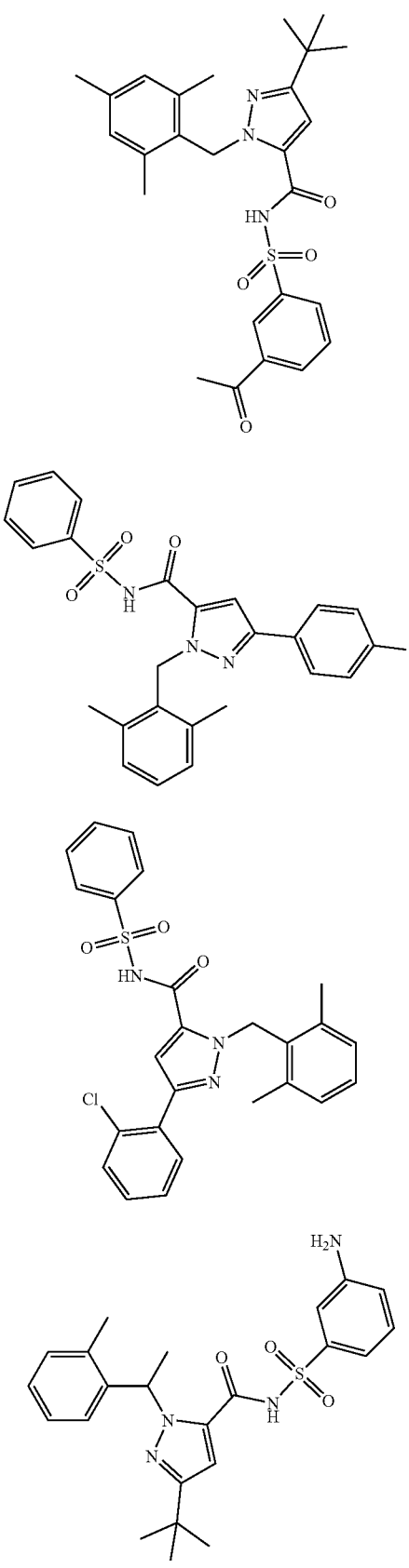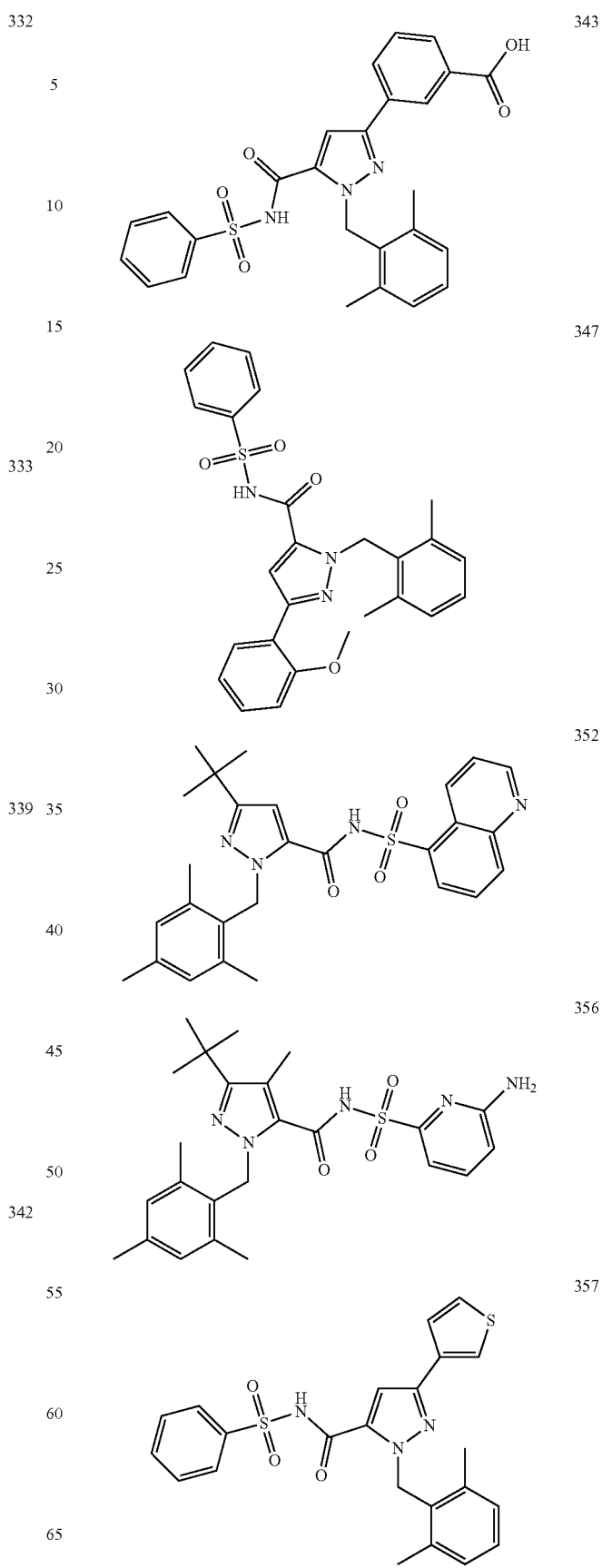

2379
-continued
363
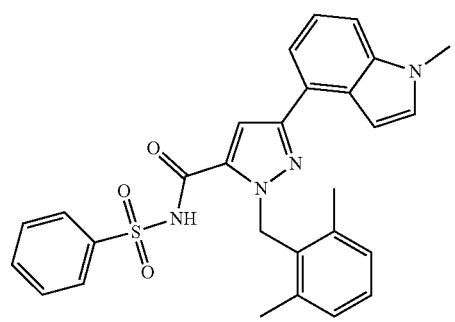
366
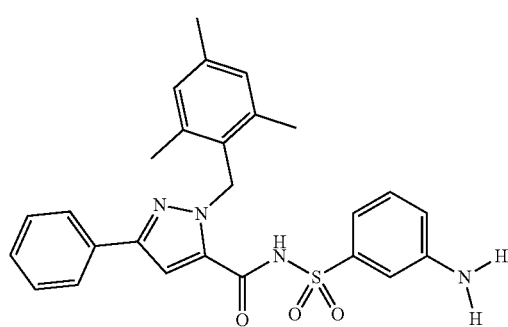
367
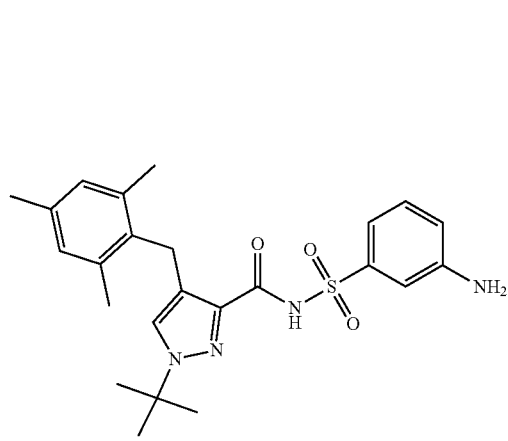
369
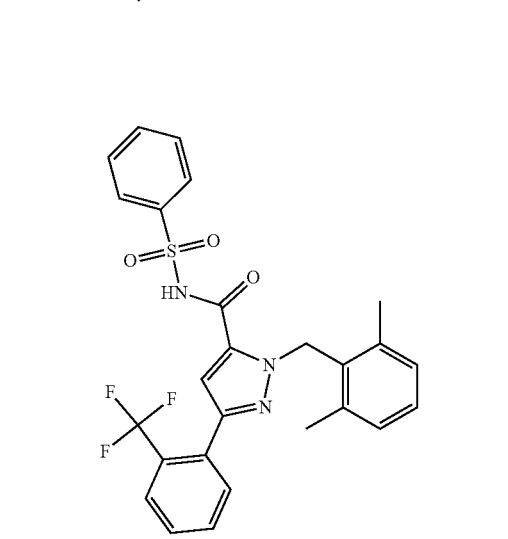
2380
-continued
370
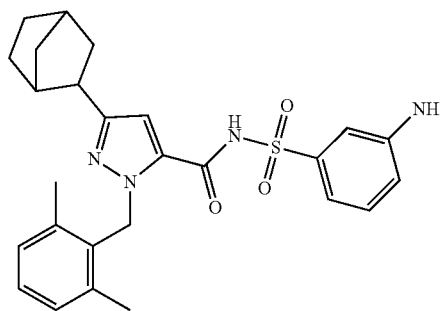
379
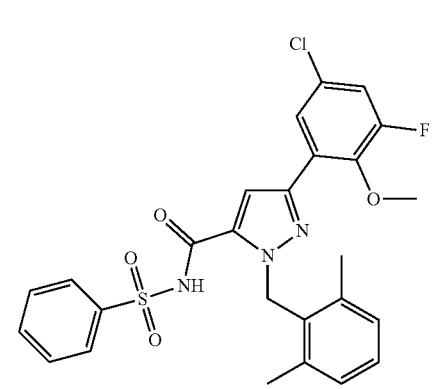
443
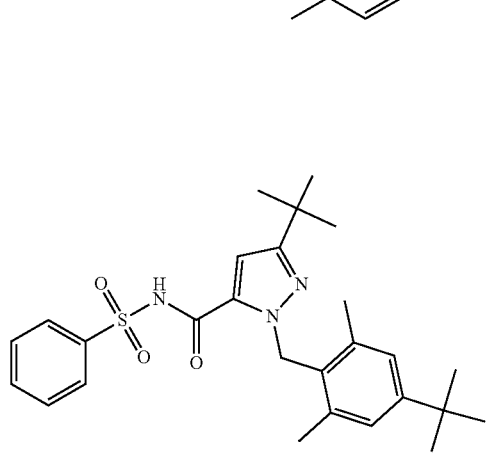
472
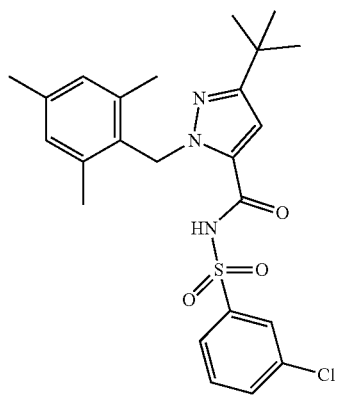

2381
-continued
2382
-continued
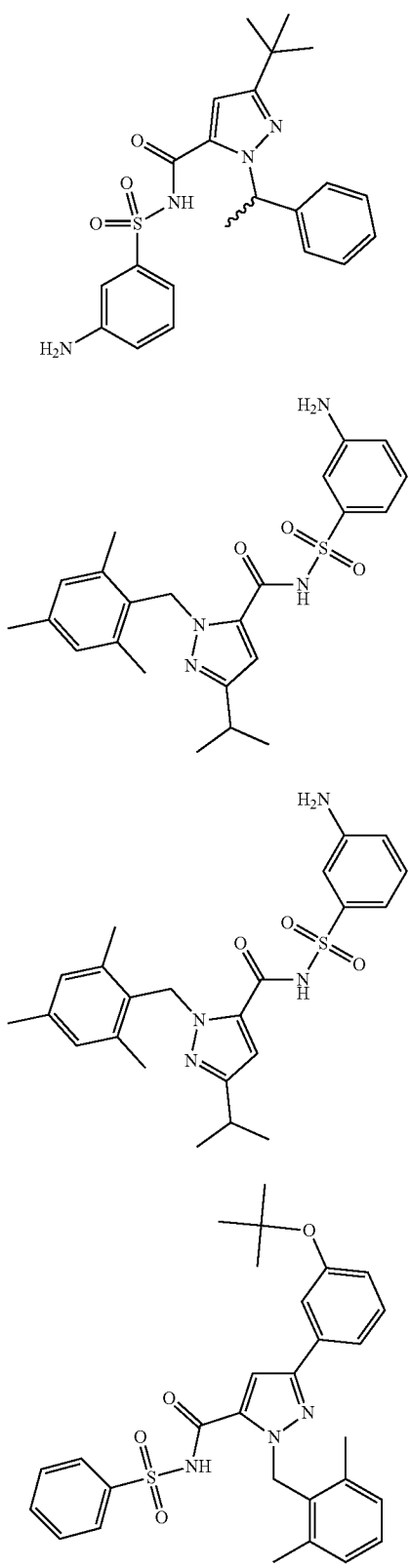
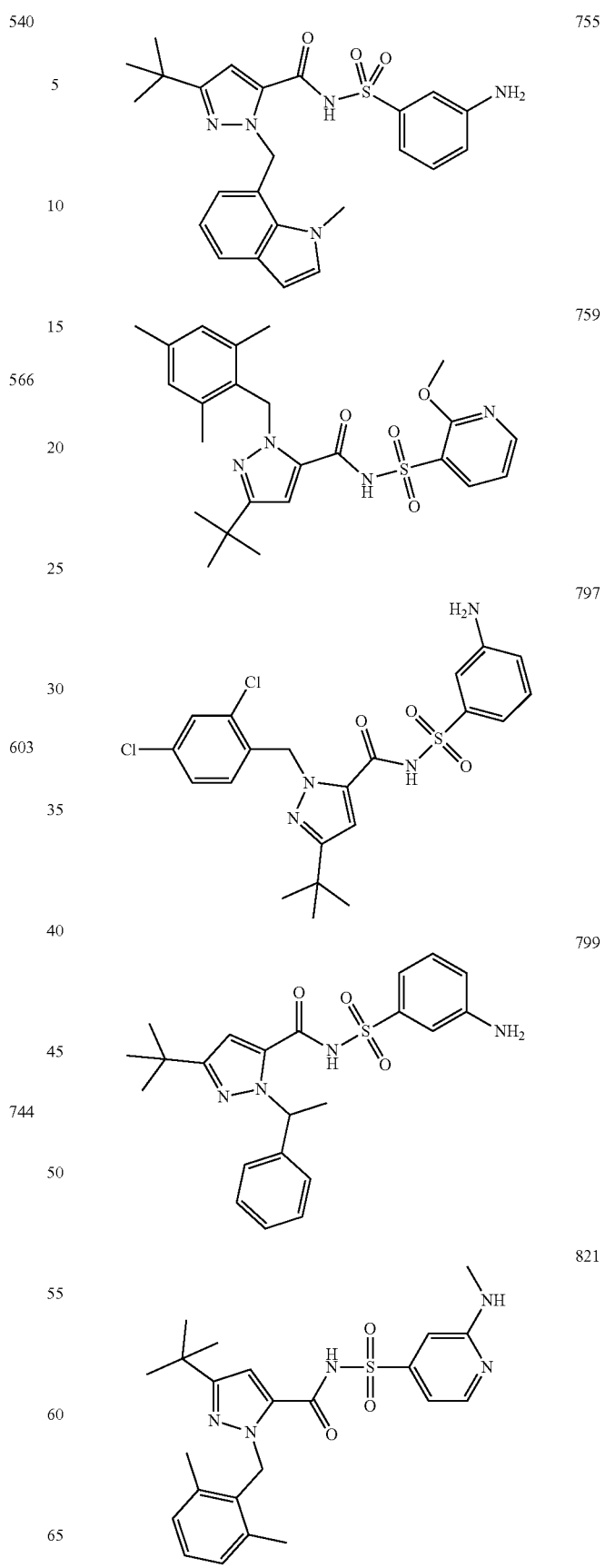

2383
-continued
823
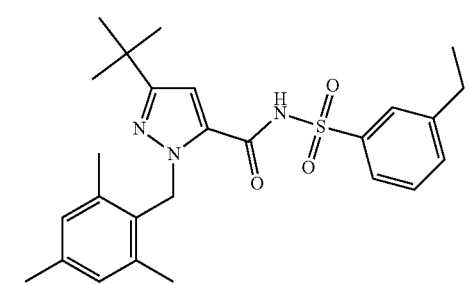
927
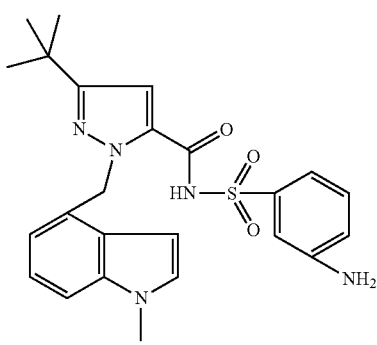
1024
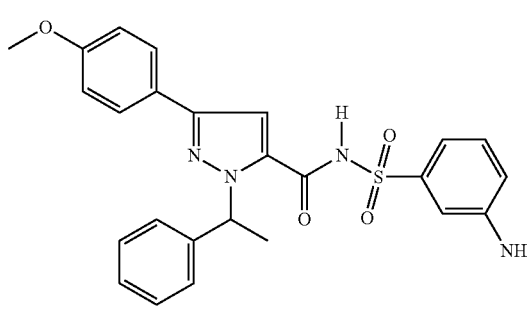
1106
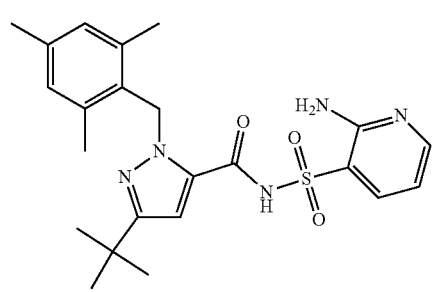
1152
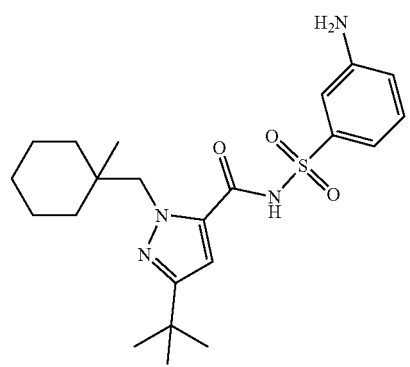
2384
-continued
1167
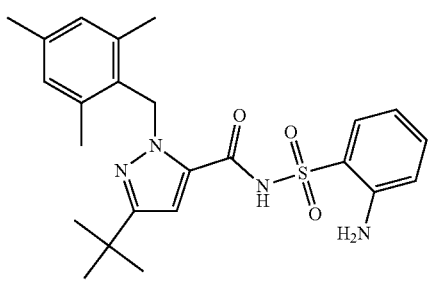
1256
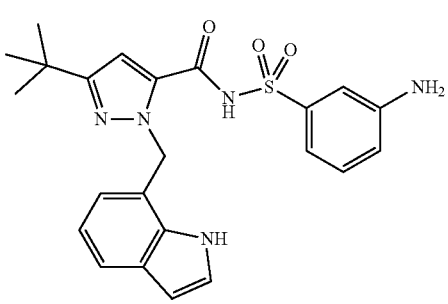
1305
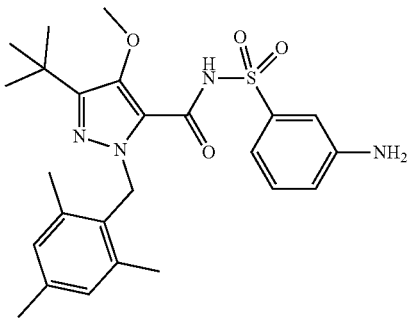
1358
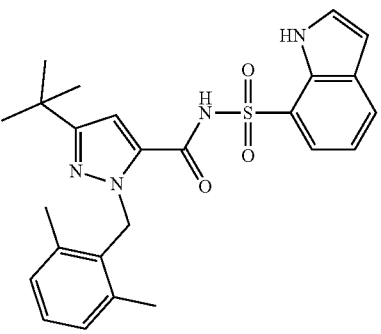
1468
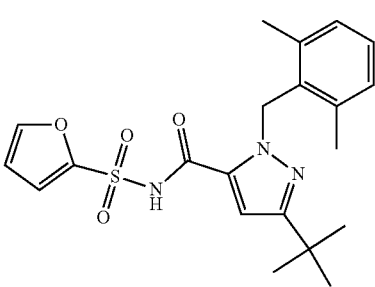

1478
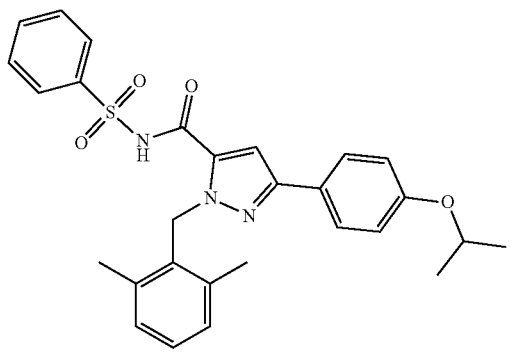
1496
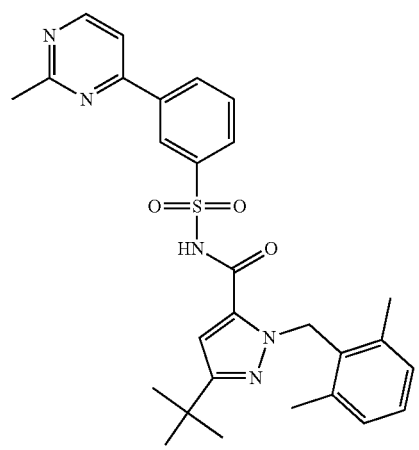
1501
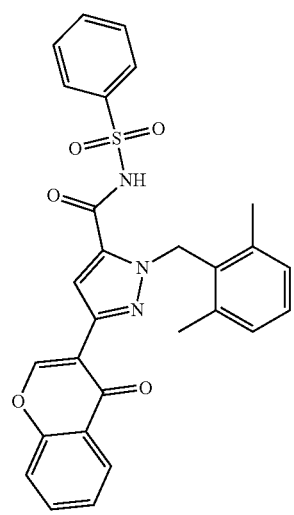
1551
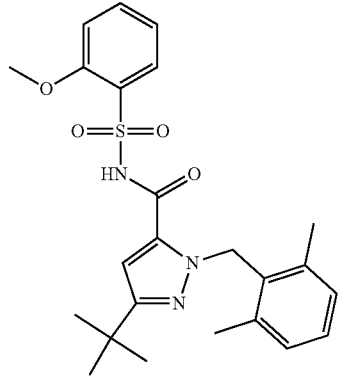
1568
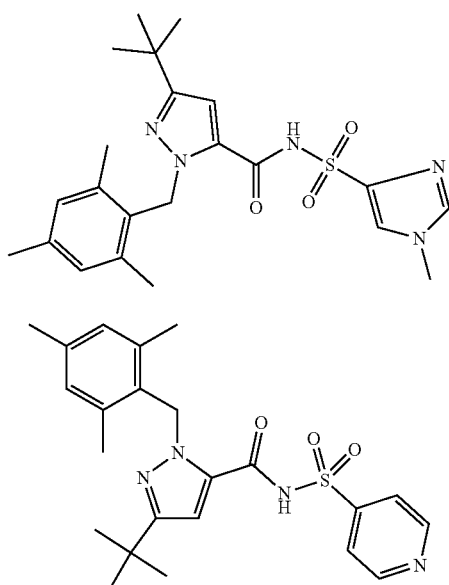
1585
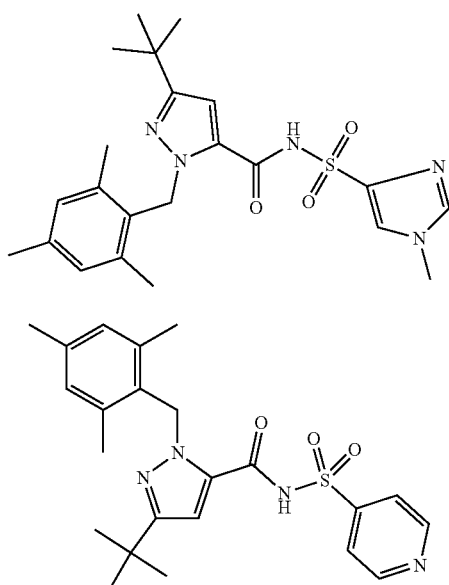
1621
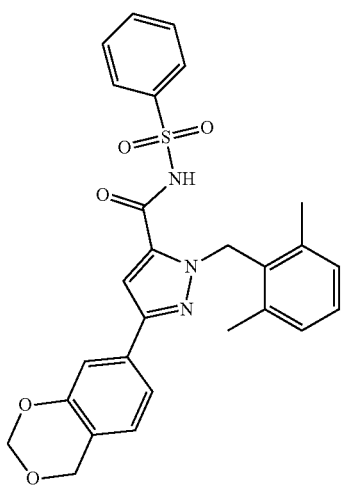

2387

-continued

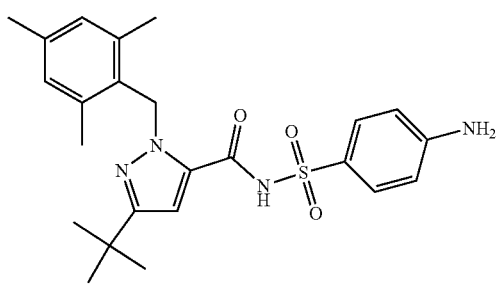
1653

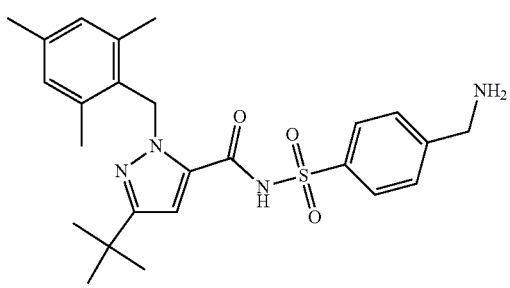
1670

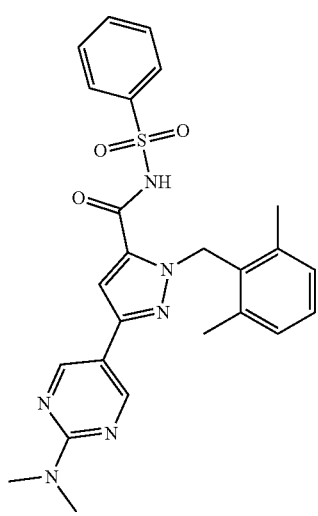
1678 deuterated derivatives thereof, and pharmaceutically acceptable salts of the foregoing.

28. A pharmaceutical composition comprising the compound, deuterated derivative, or salt of claim 1 and a pharmaceutically acceptable carrier.

29. The pharmaceutical composition of claim 28, further comprising one or more additional therapeutic agent(s).

30. The pharmaceutical composition of claim 29, wherein the one or more additional therapeutic agent(s) comprises a CFTR modulator.

31. The pharmaceutical composition of claim 29, wherein the one or more additional therapeutic agent(s) comprises

2388

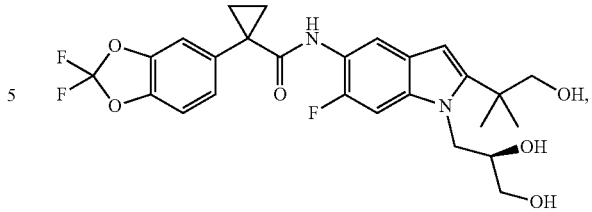

or pharmaceutically acceptable salt thereof.

32. The pharmaceutical composition of claim 29, wherein the one or more additional therapeutic agent(s) comprises

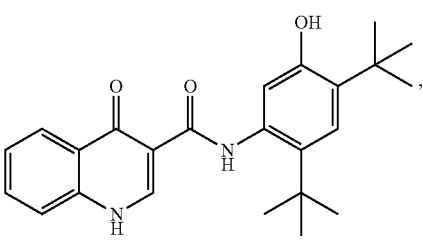 [SMILES: CC(C)(C)c1cc(C(C)(C)C)c(NC(=O)c2c[nH]c3ccccc3c2=O)cc1O]

or pharmaceutically acceptable salt thereof.

33. The pharmaceutical composition of claim 29, wherein the one or more additional therapeutic agent(s) comprises

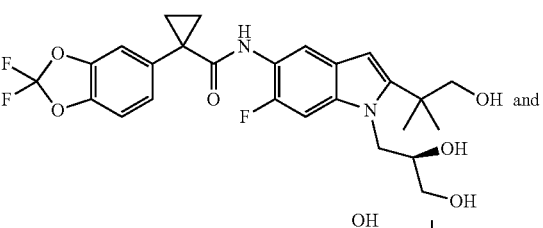
and

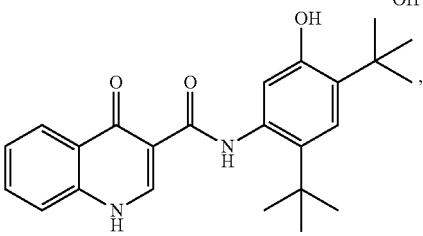

or pharmaceutically acceptable salts thereof.

34. A method of treating cystic fibrosis in a patient comprising administering to the patient an effective amount of the compound, deuterated derivative, or salt of claim 1.

35. The method of claim 34, further comprising administering to the patient one or more additional therapeutic agent(s) prior to, concurrent with, or subsequent to the compound, deuterated derivative, or salt of claim 1.

36. The method of claim 35, wherein the one or more additional therapeutic agent(s) comprises a CFTR modulator.

37. The method of claim 35, wherein the one or more additional therapeutic agent(s) comprises

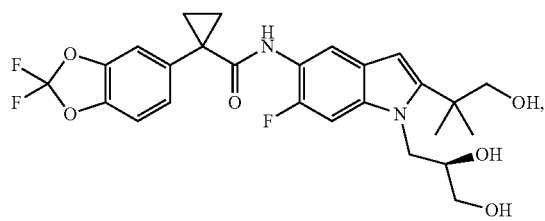 [SMILES: CC(C)(CO)c1cc2cc(NC(=O)C3(c4ccc5c(c4)OC(F)(F)O5)CC3)c(F)cc2n1C[C@@H](O)CO]

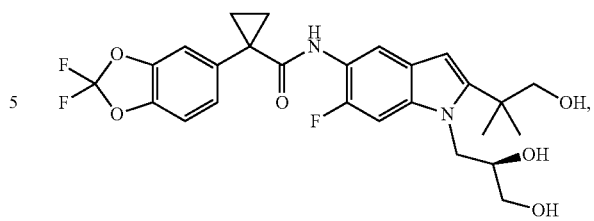

or a pharmaceutically acceptable salt thereof.

45. The method of claim 42, wherein the one or more additional therapeutic agent(s) comprises

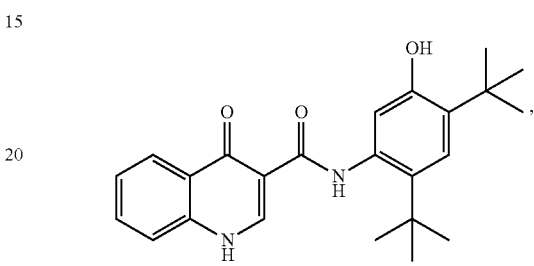

or a pharmaceutically acceptable salt thereof.

38. The method of claim 35, wherein the one or more additional therapeutic agent(s) comprises

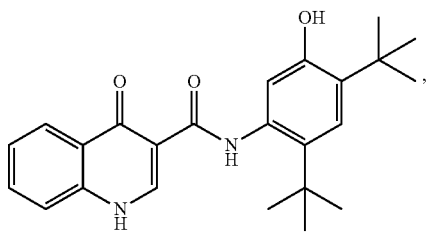 [SMILES: CC(C)(C)c1cc(C(C)(C)C)c(NC(=O)c2c[nH]c3ccccc3c2=O)cc1O]

or a pharmaceutically acceptable salt thereof.

39. The method of claim 34, wherein the patient is homozygous in the ΔF508 CFTR mutation.

40. The method of claim 34, wherein the patient is heterozygous in the ΔF508 CFTR mutation.

41. A method of treating cystic fibrosis in a patient comprising administering to the patient an effective amount of the pharmaceutical composition of claim 28.

42. The method of claim 41, further comprising administering to the patient one or more additional therapeutic agent(s) prior to, concurrent with, or subsequent to the pharmaceutical composition.

43. The method of claim 42, wherein the one or more additional therapeutic agent(s) comprises a CFTR modulator.

44. The method of claim 42, wherein the one or more additional therapeutic agent(s) comprises or a pharmaceutically acceptable salt thereof.

46. The method of claim 42, wherein the one or more additional therapeutic agent(s) comprises

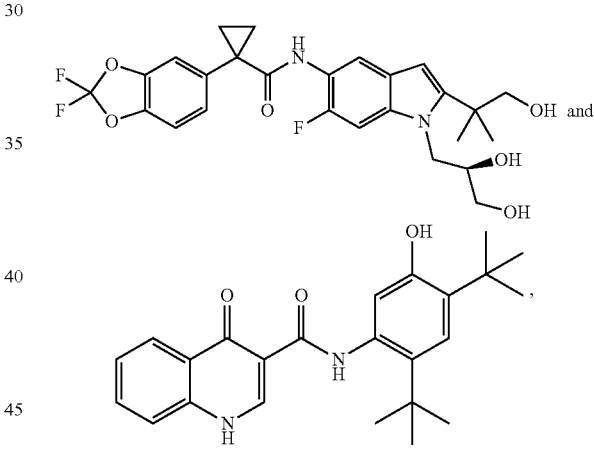

or pharmaceutically acceptable salts thereof.

* * * * *